(12) United States Patent
Ren et al.

(10) Patent No.: US 12,209,102 B2
(45) Date of Patent: Jan. 28, 2025

(54) HETEROCYCLIC COMPOUNDS AND USES THEREOF

(71) Applicant: Kumquat Biosciences Inc., San Diego, CA (US)

(72) Inventors: Pingda Ren, San Diego, CA (US); Liansheng Li, San Diego, CA (US); Baogen Wu, San Diego, CA (US); Xiaoming Li, San Diego, CA (US); Zhiyong Chen, San Diego, CA (US); Siling Zhao, San Diego, CA (US); Yi Liu, San Diego, CA (US); Xiuwen Zhu, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 59 days.

(21) Appl. No.: 18/668,025

(22) Filed: May 17, 2024

(65) Prior Publication Data

US 2024/0425522 A1     Dec. 26, 2024

Related U.S. Application Data

(63) Continuation of application No. PCT/US2023/014983, filed on Mar. 10, 2023.

(60) Provisional application No. 63/415,956, filed on Oct. 13, 2022, provisional application No. 63/415,955, filed on Oct. 13, 2022, provisional application No. 63/322,631, filed on Mar. 22, 2022, provisional application No. 63/322,630, filed on Mar. 22, 2022, provisional application No. 63/319,256, filed on Mar. 11, 2022, provisional application No. 63/319,253, filed on Mar. 11, 2022.

(51) Int. Cl.
| | | |
|---|---|---|
| C07D 519/00 | (2006.01) | |
| A61K 31/519 | (2006.01) | |
| A61K 31/551 | (2006.01) | |
| A61K 31/553 | (2006.01) | |

(52) U.S. Cl.
CPC .......... *C07D 519/00* (2013.01); *A61K 31/519* (2013.01); *A61K 31/551* (2013.01); *A61K 31/553* (2013.01)

(58) Field of Classification Search
CPC .. C07D 519/00; A61K 31/519; A61K 31/551; A61K 31/553
USPC ................................................. 514/211.1
See application file for complete search history.

(56) References Cited

U.S. PATENT DOCUMENTS

2020/0331911 A1    10/2020    Marx et al.

FOREIGN PATENT DOCUMENTS

| | | |
|---|---|---|
| CN | 116332948 A | 6/2023 |
| WO | WO-2013155223 A1 | 10/2013 |
| WO | WO-2015054572 A1 | 4/2015 |
| WO | WO-2017172979 A1 | 10/2017 |
| WO | WO-2018206539 A1 | 11/2018 |
| WO | WO-2018217651 A1 | 11/2018 |
| WO | WO-2019099524 A1 | 5/2019 |
| WO | WO-2019215203 A1 | 11/2019 |
| WO | WO-2020081282 A1 | 4/2020 |
| WO | WO-2020097537 A2 | 5/2020 |
| WO | WO-2020113071 A1 | 6/2020 |
| WO | WO-2021041671 A1 | 3/2021 |
| WO | WO-2021118877 A1 | 6/2021 |
| WO | WO-2022047260 A1 | 3/2022 |
| WO | WO-2022173870 A1 | 8/2022 |
| WO | WO-2022177917 A2 | 8/2022 |
| WO | WO-2022216762 A1 | 10/2022 |
| WO | WO-2023004102 A2 | 1/2023 |
| WO | WO-2023172737 A1 | 9/2023 |
| WO | WO-2023244615 A1 | 12/2023 |
| WO | WO-2024009191 A1 | 1/2024 |
| WO | WO-2024015262 A1 | 1/2024 |
| WO | WO-2024032702 A1 | 2/2024 |
| WO | WO-2024032747 A1 | 2/2024 |
| WO | WO-2024041573 A1 | 2/2024 |
| WO | WO-2024083168 A1 | 4/2024 |
| WO | WO-2024085661 A1 | 4/2024 |
| WO | WO-2024091409 A1 | 5/2024 |
| WO | WO-2024104453 A1 | 5/2024 |

OTHER PUBLICATIONS

Hensbergen et al. An Expedient Synthesis of Oxazepino and Oxazocino Quinazolines. Tetrahedron Letters. 55(46): pp. 6478-6483 (2015).
International Search Report and Written Opinion dated Jun. 16, 2023 for International Application No. PCT/US2023/014983.
McGregor, L.M., et al., "Expanding the Scope of Electrophiles Capable of Targeting K-Ras Oncogenes", Biochemistry, 2017, vol. 56, pp. 3178-3183., Supporting Information pp. S1-S24.
Wang et al. A novel fused heterocyclic system-synthesis of substituted 9,10-dihydro-1,3,4,6,7,10-hexaazacyclohepta[de]naphthalen-8(7H)-ones. Tetrahedron 54(33): pp. 9903-9910 (1998).

*Primary Examiner* — Kahsay Habte

(74) *Attorney, Agent, or Firm* — Wilson Sonsini Goodrich & Rosati

(57) ABSTRACT

The present disclosure provides compounds and pharmaceutically acceptable salts thereof, and methods of using the same. The compounds and methods have a range of utilities as therapeutics, diagnostics, and research tools. In particular, the subject compositions and methods are useful for reducing signaling output of oncogenic proteins.

25 Claims, 1 Drawing Sheet
Specification includes a Sequence Listing.

| | | 1 | | 20 | | 40 | |
|---|---|---|---|---|---|---|---|
| K-Ras (SEQ ID No. 9) | mte----- | ----yklvvv | gaggvgksal | tiqliqnhfv | deydptieds | yrkqvvidge | 49 |
| H-Ras (SEQ ID No. 10) | mte----- | ----yklvvv | gaggvgksal | tiqliqnhfv | deydptieds | yrkqvvidge | 49 |
| N-Ras (SEQ ID No. 11) | mte----- | ----yklvvv | gaggvgksal | tiqliqnhfv | deydptieds | yrkqvvidge | 49 |
| RalA (SEQ ID No. 12) | maankpkgqn | slalhkvimv | gsggvgksal | tiqfmydefv | edyeptkads | yrkkvvldge | 60 |
| RalB (SEQ ID No. 13) | maankskgqs | slalhkvimv | gsiggvgksal | tiqfmydefv | edyeptkads | yrkkvvldge | 60 |

| | | | | 80 | | 100 | | |
|---|---|---|---|---|---|---|---|---|
| K-Ras | tclldildta | gqeeysamrd | qymrtgegfl | cvfainntks | fedihhyreq | ikrvkdsed- | 108 |
| H-Ras | tclldildta | gqeeysamrd | qymrtgegfl | cvfainntks | fedihgyreq | ikrvkdsdd- | 108 |
| N-Ras | tclldildta | gqeeysamrd | qymrtgegfl | cvfainnsks | fadinlyreq | ikrvkdsdd- | 108 |
| RalA | evqidildta | gqedyaairrd | nyfrsgegfl | cvfsitemes | faatadfreq | ilrvk-eden | 119 |
| RalB | evqidildta | gqedyaairrd | nyfrsgegfl | lvfsitehes | ftataefreq | ilrvkaeedk | 120 |

SEQUENCE LISTING

```
Sequence total quantity: 13
SEQ ID NO: 1              moltype = AA  length = 188
FEATURE                   Location/Qualifiers
source                    1..188
                          mol_type = protein
                          organism = Homo sapiens
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL 120
PSRTVDTKQA QDLARSYGIP FIETSAKTRQ GVDDAFYTLV REIRKHKEKM SKDGKKKKKK 180
SKTKCVIM                                                         188

SEQ ID NO: 2              moltype = AA  length = 188
FEATURE                   Location/Qualifiers
source                    1..188
                          mol_type = protein
                          organism = Homo sapiens
SEQUENCE: 2
MTEYKLVVVG ADGVGKSALT IQLIQNHFVD EYDPTIEDSY RKQVVIDGET CLLDILDTAG  60
```

```
QEEYSAMRDQ YMRTGEGFLC VFAINNTKSF EDIHHYREQI KRVKDSEDVP MVLVGNKCDL    120
PSRTVDTKQA QDLARSYGIP FIETSAKTRQ GVDDAFYTLV REIRKHKEKM SKDGKKKKKK    180
SKTKCVIM                                                             188

SEQ ID NO: 3            moltype = AA   length = 188
FEATURE                 Location/Qualifiers
source                  1..188
                        mol_type = protein
                        organism = Homo sapiens
SEQUENCE: 3
MTEYKLVVVG AVGVGKSALT IQLIQNHFVD EYDPTIEDSY RKQVVIDGET CLLDILDTAG     60
QEEYSAMRDQ YMRTGEGFLC VFAINNTKSF EDIHHYREQI KRVKDSEDVP MVLVGNKCDL    120
PSRTVDTKQA QDLARSYGIP FIETSAKTRQ GVDDAFYTLV REIRKHKEKM SKDGKKKKKK    180
SKTKCVIM                                                             188

SEQ ID NO: 4            moltype = AA   length = 188
FEATURE                 Location/Qualifiers
source                  1..188
                        mol_type = protein
                        organism = Homo sapiens
SEQUENCE: 4
MTEYKLVVVG ASGVGKSALT IQLIQNHFVD EYDPTIEDSY RKQVVIDGET CLLDILDTAG     60
QEEYSAMRDQ YMRTGEGFLC VFAINNTKSF EDIHHYREQI KRVKDSEDVP MVLVGNKCDL    120
PSRTVDTKQA QDLARSYGIP FIETSAKTRQ GVDDAFYTLV REIRKHKEKM SKDGKKKKKK    180
SKTKCVIM                                                             188

SEQ ID NO: 5            moltype = AA   length = 189
FEATURE                 Location/Qualifiers
source                  1..189
                        mol_type = protein
                        organism = Homo sapiens
SEQUENCE: 5
MTEYKLVVVG AGGVGKSALT IQLIQNHFVD EYDPTIEDSY RKQVVIDGET CLLDILDTAG     60
QEEYSAMRDQ YMRTGEGFLC VFAINNSKSF ADINLYREQI KRVKDSDDVP MVLVGNKCDL    120
PTRTVDTKQA HELAKSYGIP FIETSAKTRQ GVEDAFYTLV REIRQYRMKK LNSSDDGTQG    180
CMGLPCVVM                                                            189

SEQ ID NO: 6            moltype = AA   length = 189
FEATURE                 Location/Qualifiers
source                  1..189
                        mol_type = protein
                        organism = Homo sapiens
SEQUENCE: 6
MTEYKLVVVG ADGVGKSALT IQLIQNHFVD EYDPTIEDSY RKQVVIDGET CLLDILDTAG     60
QEEYSAMRDQ YMRTGEGFLC VFAINNTKSF EDIHQYREQI KRVKDSDDVP MVLVGNKCDL    120
AARTVESRQA QDLARSYGIP YIETSAKTRQ GVEDAFYTLV REIRQHKLRK LNPPDESGPG    180
CMSCKCVLS                                                            189

SEQ ID NO: 7            moltype = AA   length = 189
FEATURE                 Location/Qualifiers
source                  1..189
                        mol_type = protein
                        organism = Homo sapiens
SEQUENCE: 7
MTEYKLVVVG AGGVGKSALT IQLIQNHFVD EYDPTIEDSY RKQVVIDGET CLLDILDTAG     60
QEEYSAMRDQ YMRTGEGFLC VFAINNTKSF EDIHQYREQI KRVKDSDDVP MVLVGNKCDL    120
AARTVESRQA QDLARSYGIP YIETSAKTRQ GVEDAFYTLV REIRQHKLRK LNPPDESGPG    180
CMSCKCVLS                                                            189

SEQ ID NO: 8            moltype = AA   length = 189
FEATURE                 Location/Qualifiers
source                  1..189
                        mol_type = protein
                        organism = Homo sapiens
SEQUENCE: 8
MTEYKLVVVG ADGVGKSALT IQLIQNHFVD EYDPTIEDSY RKQVVIDGET CLLDILDTAG     60
QEEYSAMRDQ YMRTGEGFLC VFAINNSKSF ADINLYREQI KRVKDSDDVP MVLVGNKCDL    120
PTRTVDTKQA HELAKSYGIP FIETSAKTRQ GVEDAFYTLV REIRQYRMKK LNSSDDGTQG    180
CMGLPCVVM                                                            189

SEQ ID NO: 9            moltype = AA   length = 108
FEATURE                 Location/Qualifiers
source                  1..108
                        mol_type = protein
                        organism = Homo sapiens
SEQUENCE: 9
MTEYKLVVVG AGGVGKSALT IQLIQNHFVD EYDPTIEDSY RKQVVIDGET CLLDILDTAG     60
QEEYSAMRDQ YMRTGEGFLC VFAINNTKSF EDIHHYREQI KRVKDSED               108
```

```
SEQ ID NO: 10            moltype = AA  length = 108
FEATURE                  Location/Qualifiers
source                   1..108
                         mol_type = protein
                         organism = Homo sapiens
SEQUENCE: 10
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHQYREQI KRVKDSDD               108

SEQ ID NO: 11            moltype = AA  length = 108
FEATURE                  Location/Qualifiers
source                   1..108
                         mol_type = protein
                         organism = Homo sapiens
SEQUENCE: 11
MTEYKLVVVG AGGVGKSALT IQLIQNHFVD EYDPTIEDSY RKQVVIDGET CLLDILDTAG    60
QEEYSAMRDQ YMRTGEGFLC VFAINNSKSF ADINLYREQI KRVKDSDD               108

SEQ ID NO: 12            moltype = AA  length = 119
FEATURE                  Location/Qualifiers
source                   1..119
                         mol_type = protein
                         organism = Homo sapiens
SEQUENCE: 12
MAANKPKGQN SLALHKVIMV GSGGVGKSAL TLQFMYDEFV EDYEPTKADS YRKKVVLDGE    60
EVQIDILDTA GQEDYAAIRD NYFRSGEGFL CVFSITEMES FAATADFREQ ILRVKEDEN   119

SEQ ID NO: 13            moltype = AA  length = 120
FEATURE                  Location/Qualifiers
source                   1..120
                         mol_type = protein
                         organism = Homo sapiens
SEQUENCE: 13
MAANKSKGQS SLALHKVIMV GSGGVGKSAL TLQFMYDEFV EDYEPTKADS YRKKVVLDGE    60
EVQIDILDTA GQEDYAAIRD NYFRSGEGFL LVFSITEHES FTATAEFREQ ILRVKAEEDK  120
```

HETEROCYCLIC COMPOUNDS AND USES THEREOF

CROSS-REFERENCE

This application is a continuation of International Application No. PCT/US2023/014983, filed Mar. 10, 2023, which claims the benefit of U.S. Provisional Application No. 63/319,253, filed Mar. 11, 2022; U.S. Provisional Application No. 63/319,256, filed Mar. 11, 2022; U.S. Provisional Application No. 63/322,630, filed Mar. 22, 2022; U.S. Provisional Application No. 63/322,631, filed Mar. 22, 2022; U.S. Provisional Application No. 63/415,955, filed Oct. 13, 2022; and U.S. Provisional Application No. 63/415,956, filed Oct. 13, 2022, each incorporated herein by reference in its entirety.

SEQUENCE LISTING

The instant application contains a Sequence Listing which has been submitted electronically in XML format and is hereby incorporated by reference in its entirety. Said XML copy, created on May 17, 2024, is named 56690_744_301_SL.xml and is 13,993 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations. In particular, mutations in the Kirsten Ras oncogene (K-Ras) gene are one of the most frequent Ras mutations detected in human cancers including lung adenocarcinomas (LUADs) and pancreatic ductal adenocarcinoma (PDAC).

Ras proteins have long been considered "undruggable," due to, in part, high affinity to their substrate Guanosine-5'-triphosphate (GTP) and/or their smooth surfaces without any obvious targeting region. The specific G12C Ras gene mutation has been identified as a druggable target to which a number of G12C specific inhibitors have been developed. However, such therapeutics are still of limited application, as the G12C mutation in Ras exhibits a much lower prevalence rate as compared to other known Ras mutations including G12D and G12V.

SUMMARY

In view of the foregoing, there remains a considerable need for a new design of therapeutics and diagnostics that can specifically target Ras, including wildtype Ras, mutants and/or associated proteins of Ras to reduce Ras signaling output. Of particular interest are inhibitors, including pan Ras inhibitors capable of inhibiting two or more Ras mutant and/or wildtype Ras, as well as mutant-selective inhibitors targeting mutant Ras proteins such as Ras G12D, G12C, G12S, G13D, and/or G12V, for the treatment of Ras-associated diseases (e.g., cancer). Such compositions and methods can be particularly useful for treating a variety of diseases including, but not limited to, cancers and neoplasia conditions. The present disclosure addresses these needs, and provides additional advantages applicable for diagnosis, prognosis, and/or treatment for a wide diversity of diseases.

In an aspect is provided a compound of Formula (I), or a pharmaceutically acceptable salt or solvate thereof:

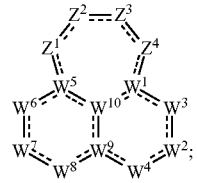

Formula (I)

wherein:

$Z^1$, $Z^2$, $Z^3$, and $Z^4$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O); wherein at least one of $Z^1$, $Z^2$, $Z^3$, and $Z^4$ is $N(R^4)$, $N(R^{11d})$, $C(R^4)$, $C(R^{11d})$, $C(R^4)(R^{11c})$, $C(R^4)(R^4)$, $C(R^{11c})(R^{11d})$, or C(O);

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $N(R^{2a})$, N, $C(R^2)$, $C(R^2)(R^{2a})$, $S(O)_2$, or S(O);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$R^{2a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20b}$;

$W^3$ is $N(R^{3b})$, N, $C(R^3)$, $C(R^3)(R^{3a})$, C(O), $S(O)_2$, or S(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20c}$;

R$^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three R$^{20c}$;

W$^4$ is N or N(R$^{3c}$);

R$^{3c}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20c}$;

W$^5$ is C(R$^5$), C, or N;

R$^5$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three R$^{20d}$;

W$^6$ is N(R$^{6b}$), N, C(R$^6$), C(R$^6$)(R$^{6a}$), C(O), S(O), or S(O)$_2$;

R$^6$ and R$^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20e}$;

R$^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20e}$;

W$^7$ is N(R$^7$), C(R$^7$), or C(R$^7$)(R$^{7a}$);

R$^{7a}$ and each R$^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20f}$, R$^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three R$^{20f}$, R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$, CR$^7$CR$^{7c}$, —OCR$^7$R$^{7c}$—, —N(R$^{7d}$)CR$^7$R$^{7c}$—, —C(O)CR$^7$CR$^{7c}$—, —SCR$^7$R$^{7c}$—, —S(O)$_2$CR$^{7c}$R$^{7c}$—, —S(O)CR$^{7c}$R$^{7c}$—, —P(O)R$^{7d}$CR$^7$CR$^{7c}$—, —CR$^7$CR$^{7c}$CR$^7$R$^{7c}$, —CR$^7$CR$^{7c}$O—, —CR$^7$R$^{7c}$N(R$^{7d}$)—, —CR$^{7c}$R$^{7c}$C(O)—, —CR$^7$CR$^{7c}$S—, —CR$^{7c}$R$^{7c}$S(O)$_2$—, —CR$^7$R$^{7c}$S(O)—, —CR$^7$R$^7$cP(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7d}$N(R$^{7d}$)—, —OC(O)—, —OS(O)$_2$—, —OS(O)—, —OP(O)R$^{7d}$—, —C(O)O—, —S(O)$_2$O—, —S(O)O—, or —P(O)R$^{7d}$O—;

R$^{17}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three R$^{20g}$;

W$^8$ is C(R$^8$), C(R$^8$)(R$^{8a}$), N, N(R$^{8b}$), C(O), S(O), or S(O)$_2$;

R$^8$ and R$^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20h}$, R$^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20h}$, W$^9$ is C(R$^9$), C, or N;

W$^{10}$ is C(R$^9$), C, or N;

each R$^9$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three R$^{20i}$;

R$^4$ is -L$^4$-R$^{4a}$;

L$^4$ is a bond, —O—, —N(R$^{4d}$)—, —C(O)—, —S—, —S(O)$_2$—, —S(O)—, —P(O)R$^{4d}$—, CR$^{4c}$R$^4$, —OCR$^4$R$^{4c}$—, —N(R$^{4d}$)CR$^{4c}$R$^{4c}$—, —C(O)CR$^4$R$^{4c}$—, —SCR$^4$R$^{4c}$—, —S(O)$_2$CR$^{4c}$R$^{4c}$—, —S(O)CR$^4$R$^{4c}$—, —P(O)R$^{4d}$CR$^{4c}$R$^{4c}$—, —CR$^4$R$^4$CR$^4$R$^4$, —CR$^4$R$^{4c}$O—, —CR$^4$R$^4$CN(R$^{4d}$)—, —CR$^4$R$^{4c}$C(O)—, —CR$^4$R$^{4c}$S—, —CR$^{4c}$R$^{4c}$S(O)$_2$—, —CR$^{4c}$R$^{4c}$S(O)—, —CR$^4$R$^4$CP(O)R$^{4d}$—, —N(R$^{4d}$)C(O)—, —N(R$^{4d}$)S(O)$_2$—, —N(R$^{4d}$)S(O)—, —N(R$^{4d}$)P(O)R$^{4d}$—, —C(O)N(R$^{4d}$)—, —S(O)$_2$N(R$^{4d}$)—, —S(O)N(R$^{4d}$)—, —P(O)R$^{4a}$N(R$^{4d}$)—, —OC(O)—, —OS(O)$_2$—, —OS(O)—, —OP(O)R$^{4d}$—, —C(O)O—, —S(O)$_{20}$—, —S(O)O—, or —P(O)R$^{4d}$O—;

each R$^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH2C(O)OR$^{14}$, —OC(O)R$^{14a}$, —N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14a}$, and —N(R$^{14}$)S(O)$_2$R$^{14}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH2C(O)OR$^{14}$, and —OC(O)R$^{14}$a, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four R$^{4b}$;

each R$^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(0)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more R$^{20j}$;

each R$^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three R$^{20k}$;

each R$^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N (R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N (R$^{12}$)(R$^{13}$), —CH$_2$C(O)N(R$^{12}$)(R$^{13}$), —CH$_2$N(R$^{14}$)C (O)R$^{15}$, —CH$_2$S(O)$_2$R$^{15}$, and —CH$_2$S(O)$_2$N(R$^{12}$) (R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, or three R$^{20k}$;

each R$^{12}$ is independently selected from hydrogen, C$_{1-6}$alkyl, C$_{2-6}$alkenyl, C$_{2-6}$alkynyl, C$_{3-10}$cycloalkyl, —C(R$^{12b}$)$_2$-C$_{3-10}$cycloalkyl, C$_{2-9}$heterocycloalkyl, —C(R$^{12b}$)$_2$-C$_{2-9}$heterocycloalkyl, C$_{6-10}$aryl, —C(R$^{12b}$)$_2$-C$_{6-10}$aryl, —C(R$^{12b}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12b}$)$_2$-C$_{3-10}$cycloalkyl, C$_{2-9}$heterocycloalkyl, —C(R$^{12b}$)$_2$-C$_{2-9}$heterocycloalkyl, C$_{6-10}$aryl, —C(R$^{12b}$)$_2$-C$_{6-10}$aryl, —C(R$^{12b}$)$_2$-C$_{1-9}$heteroaryl, and C$_{1-9}$heteroaryl are optionally substituted with one, two, or three R$^{20l}$, R$^{12a}$ is selected from C$_{1-6}$alkyl, C$_{2-6}$alkenyl, C$_{2-6}$alkynyl, C$_{3-10}$cycloalkyl, —C(R$^{12b}$)$_2$-C$_{3-10}$cycloalkyl, C$_{2-9}$heterocycloalkyl, —C(R$^{12b}$)$_2$-C$_{2-9}$heterocycloalkyl, C$_{6-10}$aryl, —C(R$^{12b}$)$_2$-C$_{6-10}$aryl, —C(R$^{12b}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12b}$)$_2$-C$_{3-10}$cycloalkyl, C$_{2-9}$heterocycloalkyl, —C(R$^{12b}$)$_2$-C$_{2-9}$heterocycloalkyl, C$_{6-10}$aryl, —C(R$^{12b}$)$_2$-C$_{6-10}$aryl, —C(R$^{12b}$)$_2$-C$_{1-9}$heteroaryl, and C$_{1-9}$heteroaryl are optionally substituted with one, two, or three R$^{20l}$;

each R$^{12b}$ is independently selected from hydrogen and R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{14}$ is independently selected from hydrogen, C$_{1-6}$alkyl, and C$_{1-6}$haloalkyl;

each R$^{14a}$ is independently selected from C$_{1-6}$alkyl and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20m}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N (R$^{22}$)(R$^{23}$), —OC(O)N(R$^{22}$)(R$^{23}$), —N(R$^{24}$)C(O)N (R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH2C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC (O)N(R$^{22}$)(R$^{23}$), —N(R$^{24}$)C(O)N(R$^{22}$)(R$^{23}$), —N(R$^{24}$) C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl;

each R$^{23}$ is independently selected from H and C$_{1-6}$alkyl;
each R$^{24}$ is independently selected from H and C$_{1-6}$alkyl;
each R$^{25}$ is independently selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and ----- indicates a single or double bond such that all valences are satisfied.

In another aspect is provided a compound of Formula (II), or a pharmaceutically acceptable salt or solvate thereof:

Formula (II)

wherein:
Z$^1$, Z$^2$, and Z$^3$ are each independently selected from N(R$^4$), N(R$^{11c}$), N(R$^{11d}$), N, C(R$^4$), C(R$^{11c}$), C(R$^{11d}$), C(R$^4$)(R$^{11c}$), C(R$^{11c}$)(R$^{11c}$), C(R$^4$)(R$^4$), C(R$^{11c}$)(R$^{11d}$), S, O, and C(O);

Z$^4$ is selected from N(R$^4$), N(R$^{11c}$), N(R$^{11d}$), N, C(R$^4$), C(R$^{11c}$), C(R$^{11d}$), C(R$^4$)(R$^{11c}$), C(R$^{11c}$)(R$^{11c}$), C(R$^4$)(R$^4$), C(R$^{11c}$)(R$^{11d}$), and O;

wherein at least one of Z$^1$, Z$^2$, and Z$^3$ is N(R$^4$), N(R$^{11d}$), C(R$^4$), C(R$^{11d}$), C(R$^4$)(R$^{11c}$), C(R$^4$)(R$^4$), C(R$^{11c}$) (R$^{11d}$), or C(O) or Z$^4$ is N(R$^4$), N(R$^{11d}$), C(R$^4$), C(R$^{11d}$), C(R$^4$)(R$^{11c}$), C(R$^4$)(R$^4$), or C(R$^{11c}$)(R$^{11d}$);

W$^1$ is C(R$^1$), C, or N;
R$^1$ is selected from hydrogen, halogen, —CN, C$_{1-6}$alkyl, C$_{2-6}$alkenyl, C$_{2-6}$alkynyl, —OR$^{12}$, —SR$^{12}$, —N(R$^{12}$) (R$^{13}$), —C(O)OR$^{12}$, —OC(O)N(R$^{12}$)(R$^{13}$), —N(R$^{14}$)C (O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N (R$^{12}$)(R$^{13}$), —C(O)C(O)N(R$^{12}$)(R$^{13}$), —N(R$^{14}$)C(O) R$^{15}$, —S(O)$_2$R$^{15}$, —S(O)$_2$N(R$^{12}$)(R$^{13}$)—, —S(=O) (=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S (O)$_2$N(R$^{12}$)(R$^{13}$), wherein C$_{1-6}$alkyl, C$_{2-6}$alkenyl, and C$_{2-6}$alkynyl are optionally substituted with one, two, or three R$^{20a}$;

$W^2$ is $N(R^{2a})$, N, $C(R^2)$, $C(R^2)(R^{2a})$, C(O), $S(O)_2$, or S(O);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$R^{2a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $N(R^{3b})$, N, $C(R^3)$, $C(R^3)(R^{3a})$, C(O), $S(O)_2$, or S(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is N or $N(R^{3c})$;

$R^{3c}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, C(O), S(O), or $S(O)_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$R^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^7$ is $N(R^7)$, $C(R^7)$, or $C(R^7)(R^{7a})$;

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20f}$, R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$, CR$^7$CR$^{7c}$, —OCR$^7$CR$^{7c}$—, —N(R$^{7d}$)CR$^7$CR$^{7c}$—, —C(O)CR$^7$R$^{7c}$—, —SCR$^7$·R$^{7c}$—, —S(O)$_2$CR$^7$CR$^{7c}$—, —S(O)CR$^{7c}$R$^{7c}$—, —P(O)R$^{7d}$CR$^7$CR$^{7c}$—, —CR$^{7c}$R$^7$CCR$^7$CR$^{7c}$, —CR$^{7c}$R$^{7c}$O—, —CR$^{7c}$R$^{7a}$N(R$^{7d}$)—, —CR$^{7c}$R$^{7c}$C(O)—, —CR$^{7c}$R$^{7c}$S—, —CR$^7$CR$^{7c}$S(O)$_2$—, —CR$^7$CR$^{7c}$S(O)—, —CR$^{7c}$R$^7$cP(O)R$^{7d}$, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^7$ON(R$^{7d}$)—, —OC(O)—, —OS(O)$_2$—, —OS(O)—, —OP(O)R$^{7d}$—, —C(O)O—, —S(O)$_{20}$—, —S(O)O—, or —P(O)R$^{7d}$O—;

R$^{17}$ is selected from C$_{3-10}$cycloalkyl, C$_{2-9}$heterocycloalkyl, C$_{6-10}$aryl, and C$_{1-9}$heteroaryl, wherein C$_{3-10}$cycloalkyl, C$_{2-9}$heterocycloalkyl, C$_{6-10}$aryl, and C$_{1-9}$heteroaryl are optionally substituted with one, two, or three R$^{20g}$;

W$^8$ is C(R$^8$), C(R$^8$)(R$^{8a}$), N, N(R$^{8b}$), C(O), S(O), or S(O)$_2$;

R$^8$ and R$^{8a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl and C$_{1-9}$heteroaryl are optionally substituted with one, two, or three R$^{20h}$, R$^{8b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

W$^{10}$ is C(R$^9$), C, or N;

each R$^9$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three R$^{20i}$, R$^4$ is -L$^4$-R$^{4a}$;

L$^4$ is a bond, —O—, —N(R$^{4d}$)—, —C(O)—, —S—, —S(O)$_2$—, —S(O)—, —P(O)R$^{4d}$—, CR$^4$R$^{4c}$, —OCR$^4$R$^{4c}$—, —N(R$^{4d}$)CR$^4$R$^{4c}$—, —C(O)CR$^{4c}$R$^{4c}$—, —SCR$^4$R$^{4c}$—, —S(O)$_2$CR$^4$R$^{4c}$—, —S(O)CR$^{4c}$R$^{4c}$—, —P(O)R$^{4d}$CR$^4$R$^{4c}$—, —CR$^4$R$^{4c}$CCR$^4$R$^{4c}$, —CR$^{4c}$R$^{4c}$O—, —CR$^{4c}$R$^{4c}$CN(R$^{4d}$)—, —CR$^4$R$^{4c}$CC(O)—, —CR$^{4c}$R$^4$S—, —CR$^{4c}$R$^{4c}$S(O)$_2$—, —CR$^4$R$^{4c}$S(O)—, —CR$^{4c}$R$^4$CP(O)R$^{4d}$—, —N(R$^{4d}$)C(O)—, —N(R$^{4d}$)S(O)$_2$—, —N(R$^{4d}$)S(O)—, —N(R$^{4d}$)P(O)R$^{4d}$—, —C(O)N(R$^{4d}$)—, —S(O)$_2$N(R$^{4d}$)—, —S(O)N(R$^{4d}$)—, —P(O)R$^4$ON(R$^{4d}$)—, —OC(O)—, —OS(O)$_2$—, —OS(O)—, —OP(O)R$^{4d}$—, —C(O)O—, —S(O)$_{20}$—, —S(O)O—, or —P(O)R$^{4d}$O—;

each R$^4$ is independently selected from hydrogen, halogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH2C(O)OR$^{14}$, —OC(O)R$^{14a}$, —N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14a}$, and —N(R$^{14}$)S(O)$_2$R$^{14}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl, are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4d}$ is independently selected from hydrogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH2C(O)OR$^{14}$, and —OC(O)R$^{14a}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl, are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4a}$ is independently selected from C$_{3-10}$cycloalkyl, C$_{2-9}$heterocycloalkyl, C$_{6-10}$aryl, and C$_{1-9}$heteroaryl, wherein C$_{3-10}$cycloalkyl, C$_{2-9}$heterocycloalkyl, C$_{6-10}$aryl, and C$_{1-9}$heteroaryl are optionally substituted with one, two, three, or four R$^{4b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)

$OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, and $-P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from hydrogen, halogen, oxo, $-CN$, $C_{1-6}$alkyl, $C_{2-6}$alkenyl, $C_{2-6}$alkynyl, $C_{1-6}$haloalkyl, $C_{3-12}$cycloalkyl, $-CH_2-C_{3-12}$cycloalkyl, $C_{1-11}$heterocycloalkyl, $-CH_2-C_{1-11}$heterocycloalkyl, $C_{6-10}$aryl, $-CH_2-C_{6-10}$aryl, $-CH_2-C_{1-11}$heteroaryl, $C_{1-11}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, $-CH_2-C_{3-12}$cycloalkyl, $C_{1-11}$heterocycloalkyl, $-CH_2-C_{1-11}$heterocycloalkyl, $C_{6-10}$aryl, $-CH_2-C_{6-10}$aryl, $-CH_2-C_{1-11}$heteroaryl, and $C_{1-11}$heteroaryl are optionally substituted with one, two, or three $R^{20k}$;

each $R^{11d}$ is independently selected from halogen, oxo, $-CN$, $C_{1-6}$alkyl, $C_{2-6}$alkenyl, $C_{2-6}$alkynyl, $C_{1-6}$haloalkyl, $C_{3-12}$cycloalkyl, $-CH_2-C_{3-12}$cycloalkyl, $C_{1-11}$heterocycloalkyl, $-CH_2-C_{1-11}$heterocycloalkyl, $C_{6-10}$aryl, $-CH_2-C_{6-10}$aryl, $-CH_2-C_{1-11}$heteroaryl, $C_{1-11}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, $-CH_2-C_{3-12}$cycloalkyl, $C_{1-11}$heterocycloalkyl, $-CH_2-C_{1-11}$heterocycloalkyl, $C_{6-10}$aryl, $-CH_2-C_{6-10}$aryl, $-CH_2-C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, $-C(R^{12b})_2-C_{3-10}$cycloalkyl, $C_{2-9}$heterocycloalkyl, $-C(R^{12b})_2-C_{2-9}$heterocycloalkyl, $C_{6-10}$aryl, $-C(R^{12b})_2-C_{6-10}$aryl, $-C(R^{12b})_2-C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, $-C(R^{12b})_2-C_{3-10}$cycloalkyl, $C_{2-9}$heterocycloalkyl, $-C(R^{12b})_2-C_{2-9}$heterocycloalkyl, $C_{6-10}$aryl, $-C(R^{12b})_2-C_{6-10}$aryl, $-C(R^{12b})_2-C_{1-9}$heteroaryl, and $C_{1-9}$heteroaryl are optionally substituted with one, two, or three $R^{20l}$;

each $R^{12b}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{14}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, $-CN$, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, $C_{1-9}$heteroaryl, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, $-OCH2C(O)OR^{22}$, and $-OC(O)R^{25}$, wherein $C_{1-6}$alkyl, $C_{2-6}$alkenyl, $C_{2-6}$alkynyl, $C_3$-10cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments is a compound of Formula (II), (IIa), (IIb), (IIc), (IId), (IIe), or (IIf), or a pharmaceutically acceptable salt or solvate thereof, wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$.

In some embodiments, $W^4$ is N. In some embodiments, $W^4$ is $N(R^{3c})$.

In some embodiments, $W^1$ is C. In some embodiments, $W^1$ is $C(R^1)$. In some embodiments, $W^1$ is N.

In some embodiments, $W^5$ is C. In some embodiments, $W^5$ is $C(R^5)$. In some embodiments, $W^5$ is N.

In some embodiments, $W^2$ is $C(R^2)$. In some embodiments, $W^2$ is $C(R^2)(R^{2a})$. In some embodiments, $W^2$ is N. In some embodiments, $W^2$ is $N(R^{2a})$.

In some embodiments, $W^3$ is N. In some embodiments, $W^3$ is $N(R^{3b})$. In some embodiments, $W^3$ is $C(R^3)$. In some embodiments, $W^3$ is $C(R^3)(R^{3a})$. In some embodiments, $W^3$ is C(O).

In some embodiments, $W^6$ is $C(R^6)$. In some embodiments, $W^6$ is $C(R^6)(R^{6a})$. In some embodiments, $W^6$ is N. In some embodiments, $W^6$ is $N(R^6\%)$. In some embodiments, $W^6$ is C(O).

In some embodiments, $W^7$ is $C(R^7)$. In some embodiments, $W^7$ is $C(R^7)(R^{7a})$. In some embodiments, $W^7$ is $N(R^7)$.

In some embodiments, $W^8$ is $C(R^8)$. In some embodiments, $W^8$ is $C(R^8)(R^{8a})$. In some embodiments, $W^8$ is N. In some embodiments, $W^8$ is $N(R^{8b})$. In some embodiments, $W^8$ is C(O).

In some embodiments, $W^9$ is C. In some embodiments, $W^{10}$ is N.

In some embodiments, $W^{10}$ is C. In some embodiments, $W^{10}$ is N.

In some embodiments is a compound of Formula (I) having the structure of Formula (Ia), or a pharmaceutically acceptable salt or solvate thereof:

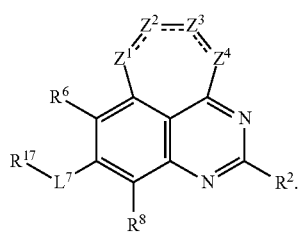

Formula (Ia)

In some embodiments is a compound of Formula (I) having the structure of Formula (Ib), or a pharmaceutically acceptable salt or solvate thereof:

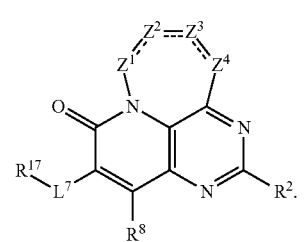

Formula (Ib)

In some embodiments is a compound of Formula (I) having the structure of Formula (Ic), or a pharmaceutically acceptable salt or solvate thereof:

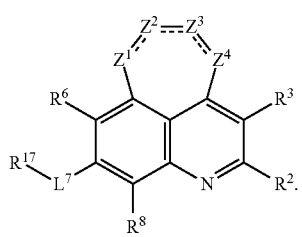

Formula (Ic)

In some embodiments is a compound of Formula (I) having the structure of Formula (Id), or a pharmaceutically acceptable salt or solvate thereof:

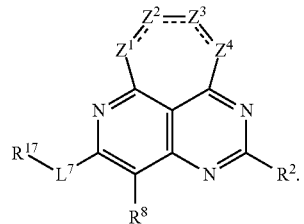

Formula (Id)

In some embodiments is a compound of Formula (I) having the structure of Formula (Ie), or a pharmaceutically acceptable salt or solvate thereof:

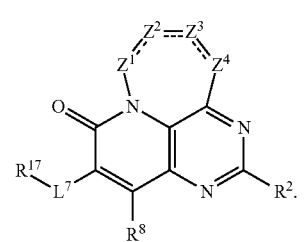

Formula (Ie)

In some embodiments is a compound of Formula (I) having the structure of Formula (If), or a pharmaceutically acceptable salt or solvate thereof:

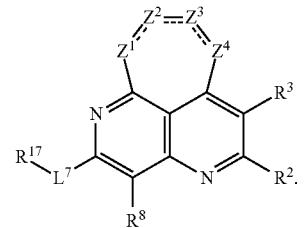

Formula (If)

In some embodiments, $R^2$ is selected from $C_{1-6}$alkyl, $C_{2-6}$alkenyl, $C_2$-calkynyl, $C_{3-10}$cycloalkyl, $C_{2-9}$heterocycloalkyl, $C_{6-10}$aryl, $C_{1-9}$heteroaryl, —$OR^{12a}$, —$SR^{12}$, and —$N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$. In some embodiments, $R^2$ is selected from —$OR^{12a}$, —$SR^{12}$, —$N(R^{12})(R^{13})$, and $C_{1-6}$alkyl optionally substituted with one, two, or three $R^{20b}$. In some embodiments, $R^2$ is selected from

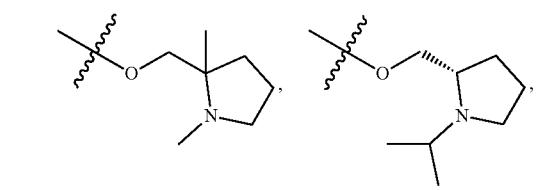

-continued
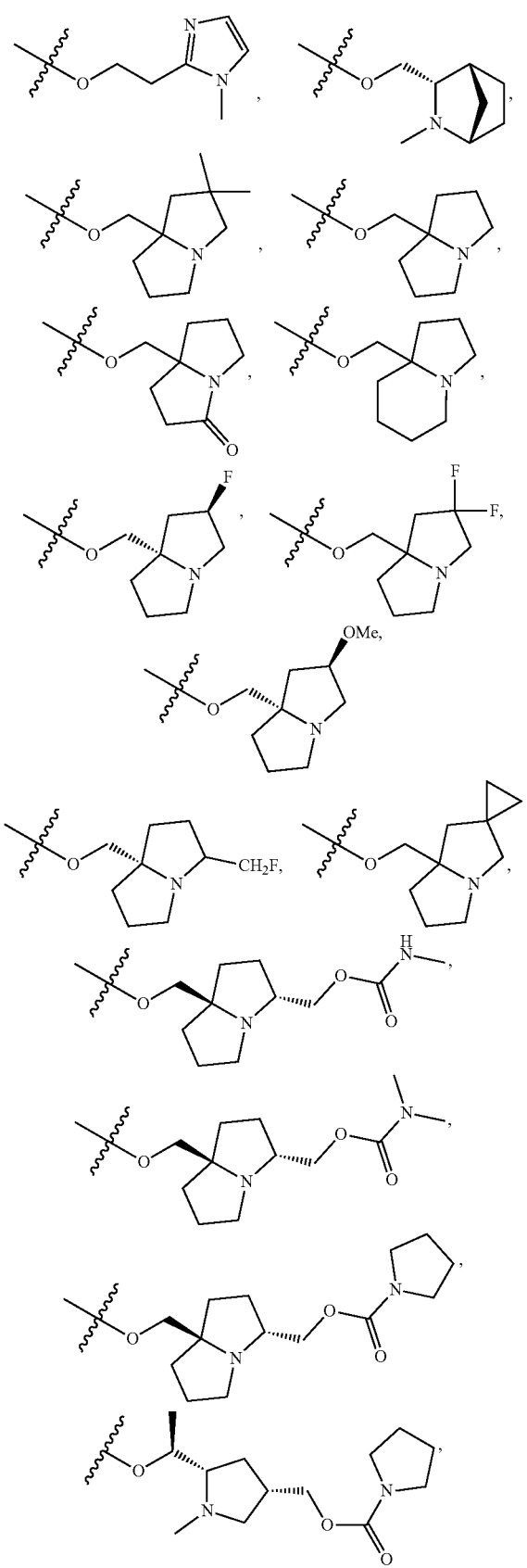
-continued
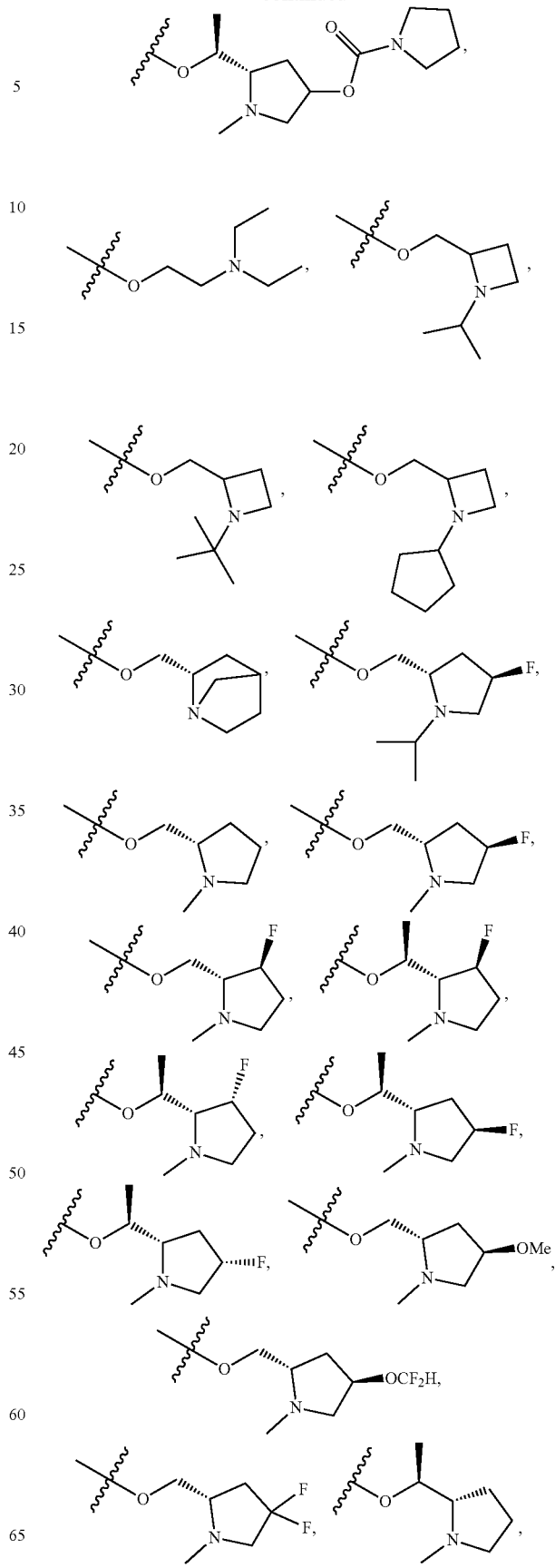

-continued
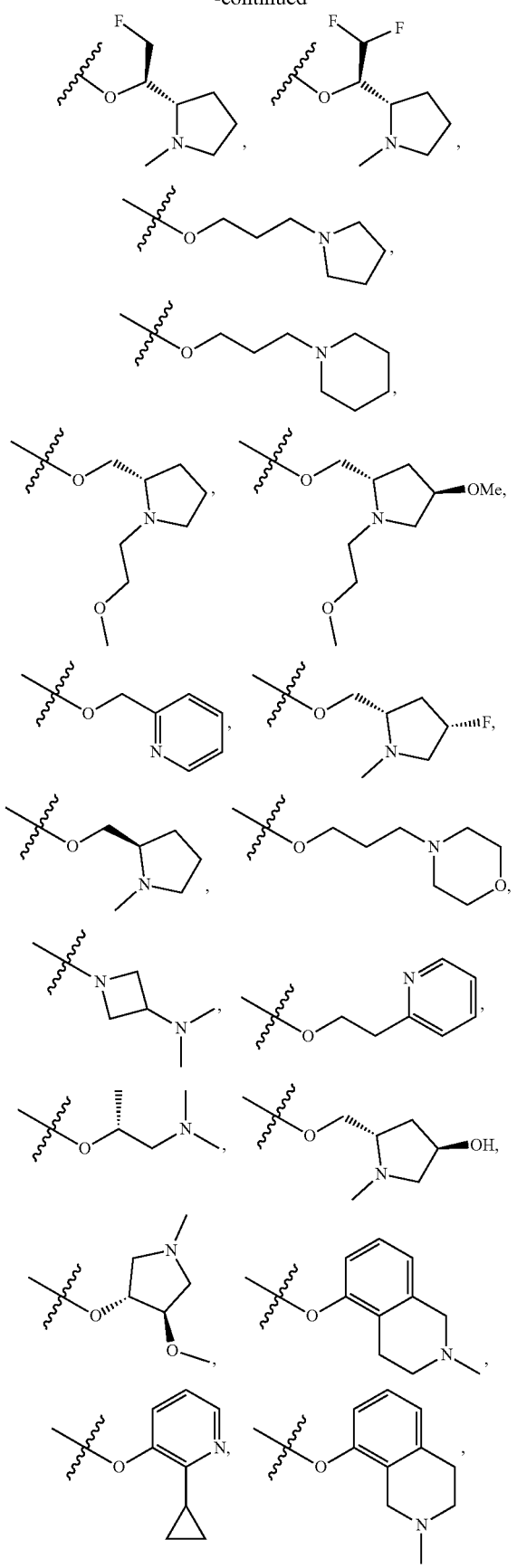
-continued
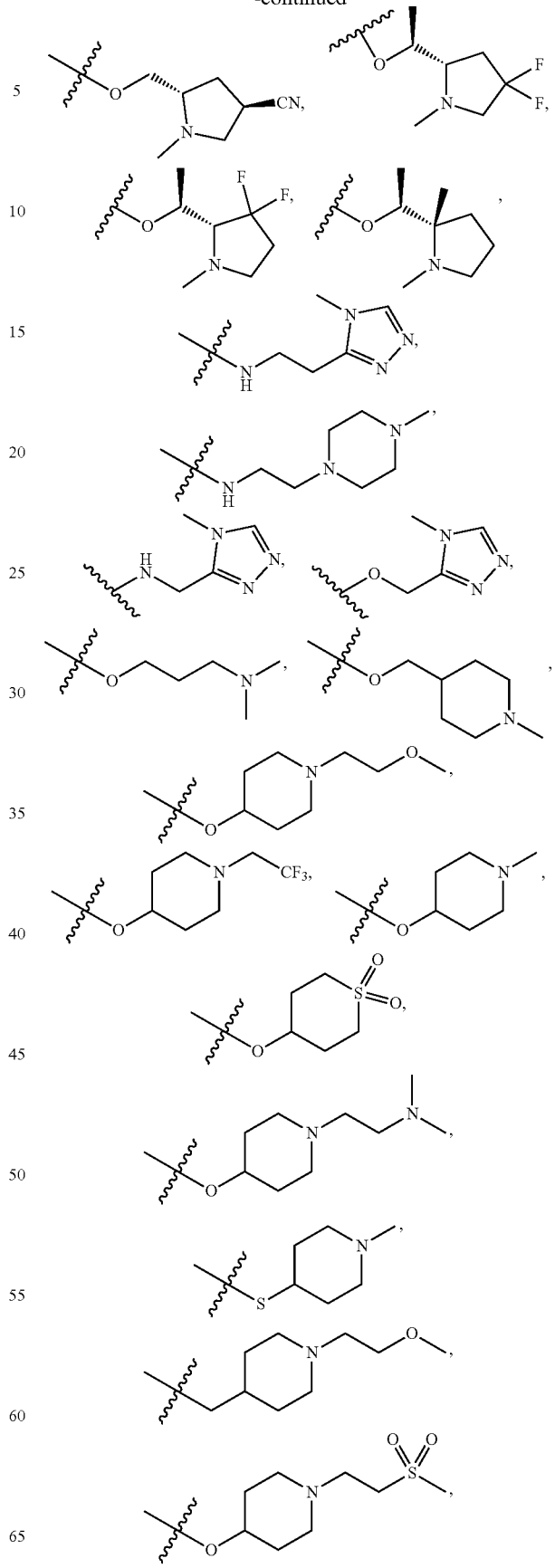

-continued
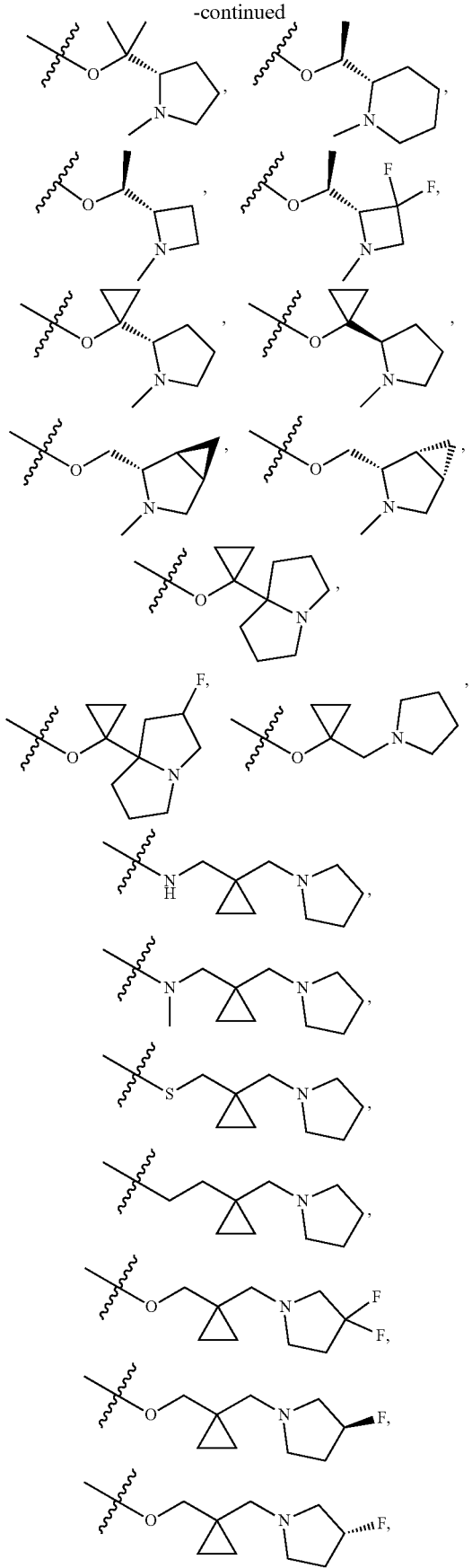
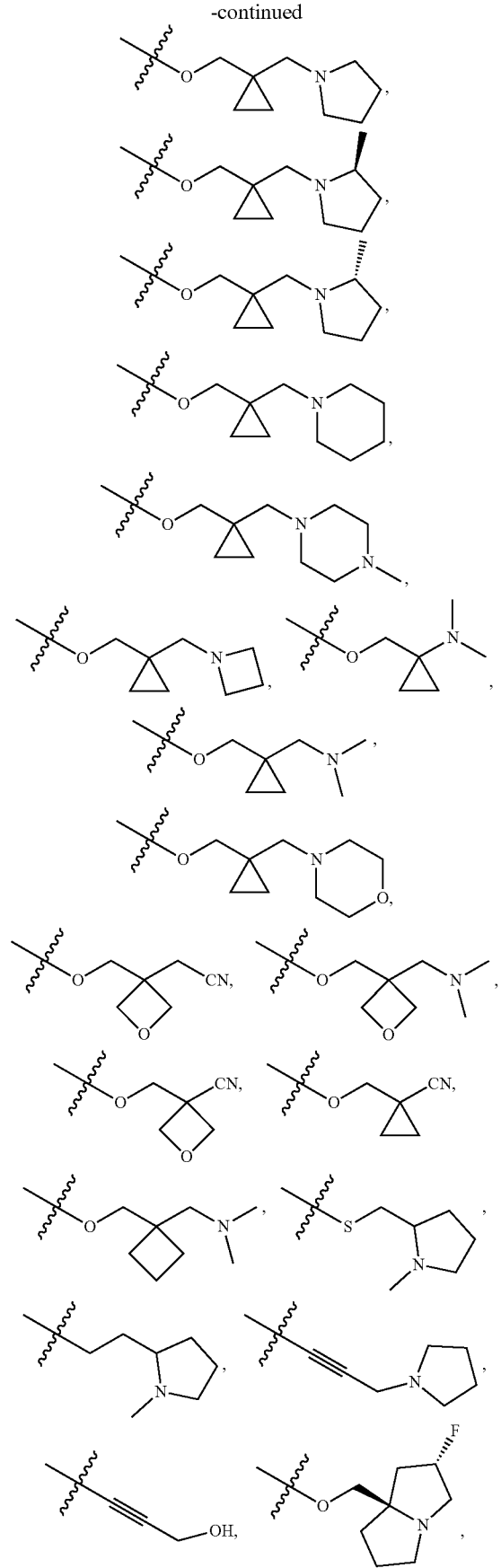

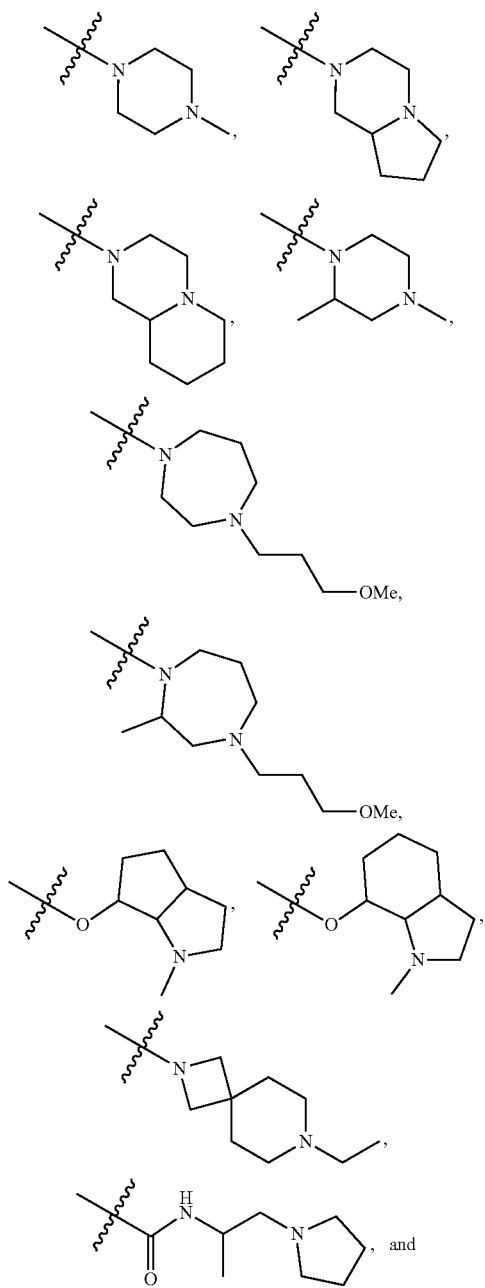

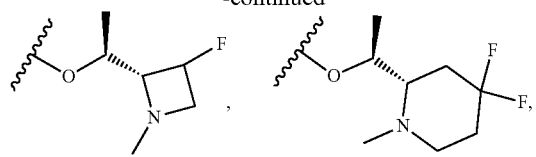

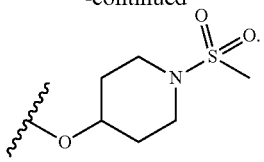

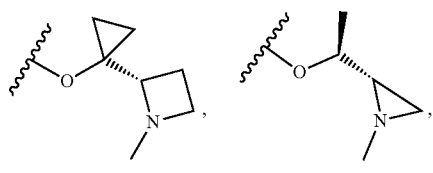

In some embodiments, $R^3$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20c}$. In some embodiments, $R^3$ is selected from hydrogen, halogen, —CN, $C_{1-6}$alkyl, and —$OR^{12}$, wherein $C_{1-6}$alkyl is optionally substituted with one, two, or three $R^{20c}$.

In some embodiments, $R^6$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20c}$. In some embodiments, $R^6$ is selected from hydrogen, halogen, —CN, $C_{1-6}$alkyl, and —$OR^{12}$, wherein $C_{1-6}$alkyl is optionally substituted with one, two, or three $R^{20e}$.

In some embodiments, $R^{17}$ is $C_{3-10}$cycloalkyl optionally substituted with one, two, or three $R^{20g}$. In some embodiments, $R^{17}$ is $C_{2-9}$heterocycloalkyl optionally substituted with one, two, or three $R^{20g}$. In some embodiments, $R^{17}$ is $C_{6-10}$aryl optionally substituted with one, two, or three $R^{20g}$. In some embodiments, $R^{17}$ is $C_{1-9}$heteroaryl optionally substituted with one, two, or three $R^{20g}$.

In some embodiments, $L^7$ is a bond, —O—, —$N(R^{7d})$—, —C(O)—, or $CR^7R^{7c}$. In some embodiments, $L^7$ is a bond.

In some embodiments, $R^{17}$ is selected from:

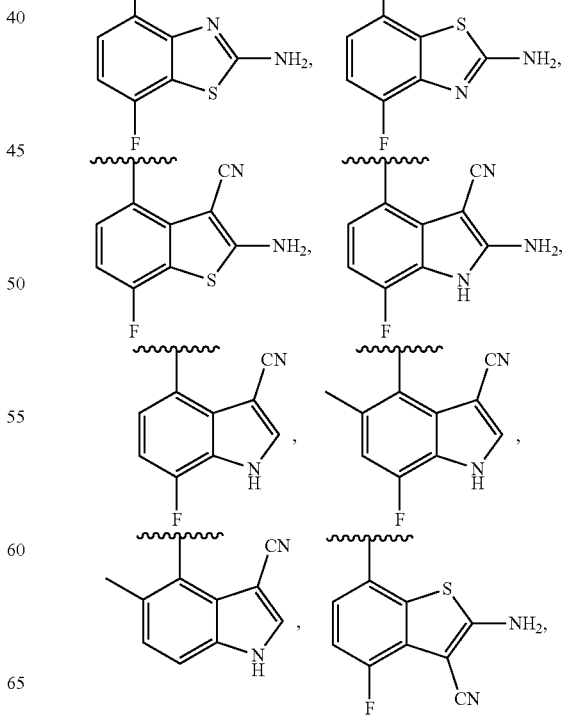

-continued
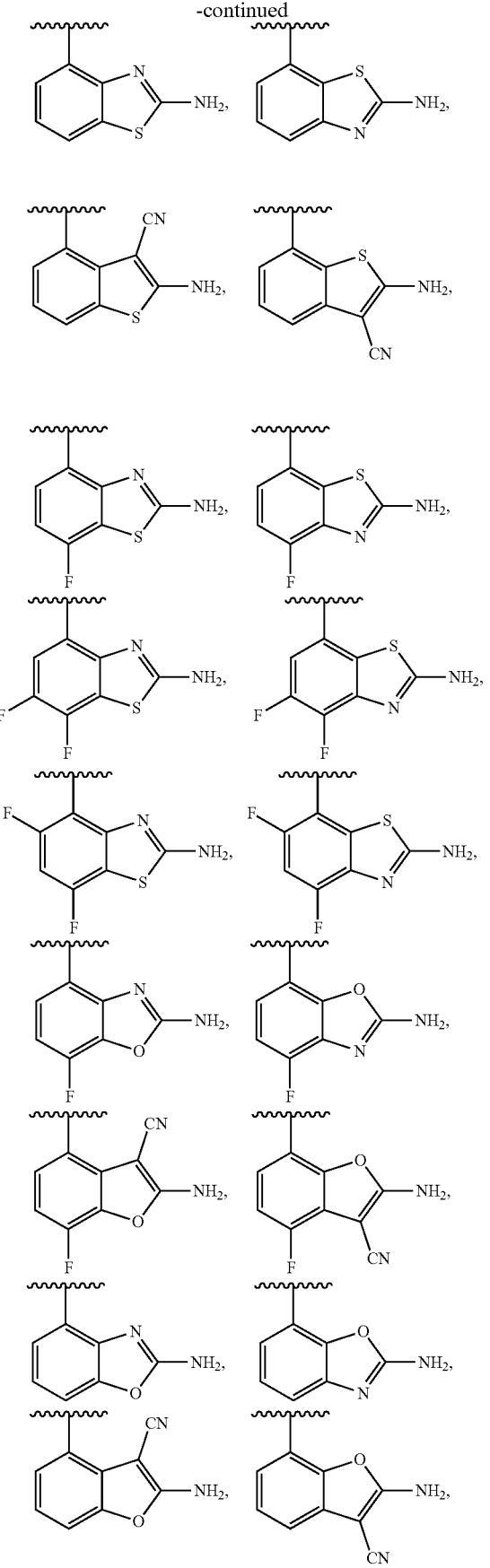
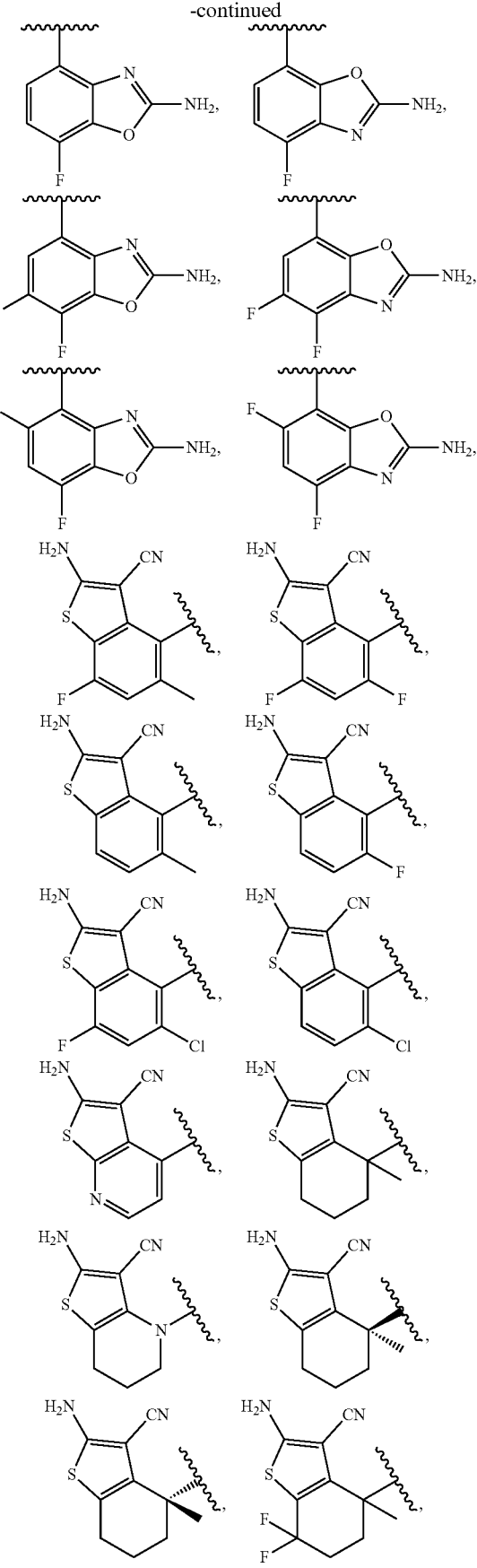

-continued

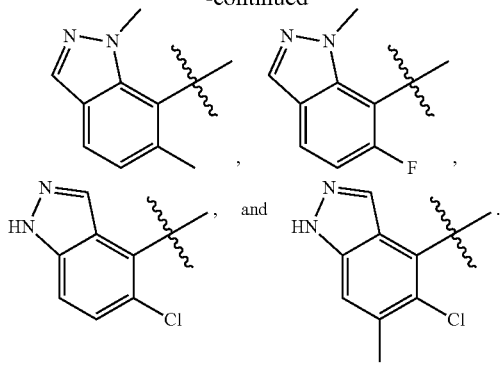

, and

In some embodiments, Ra is selected from hydrogen, halogen, —CN, $C_{1-6}$alkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$)—, wherein $C_{1-6}$alkyl is optionally substituted with one, two, or three R$^{20h}$. In some embodiments, Ra is selected from hydrogen, halogen, —CN, $C_{1-6}$alkyl, and —OR$^{12}$, wherein $C_{1-6}$alkyl is optionally substituted with one, two, or three R$^{20h}$.

In some embodiments, Z$^1$ is O, Z$^3$ is C(R$^{11c}$)(R$^{11c}$), Z$^3$ is C(R$^{11c}$)(R$^{11c}$), and Z$^4$ is N(R$^4$). In some embodiments, Z$^1$ is S, Z$^2$ is C(R$^{11c}$)(R$^{11c}$), Z$^3$ is C(R$^{11c}$)(R$^{11c}$), and Z$^1$ is N(R$^4$). In some embodiments, Z$^4$ is N(R$^{11c}$), Z$^4$ is C(R$^{11c}$)(R$^{119}$), Z$^3$ is C(R$^{11c}$)(R$^{11c}$), and Z$^4$ is N(R$^4$). In some embodiments, Z$^1$ is C(R$^{11c}$)(R$^{11c}$), Z$^2$ is C(R$^{11c}$)(R$^{11c}$), Z$^3$ is C(R$^{11c}$)(R$^{11c}$), and Z$^4$ is N(R$^4$). In some embodiments, Z$^1$ is O, Z$^2$ is C(R$^{11c}$)(R$^{11c}$), Z$^3$ is C(O), and Z$^4$ is N(R$^4$). In some embodiments, Z$^1$ is O, Z$^2$ is C(R$^{11c}$)(R$^{11c}$), Z$^3$ is C(R$^4$)(R$^{11c}$), and Z$^4$ is N(R$^{11c}$). In some embodiments, Z$^1$ is O, Z$^2$ is C(R$^{11c}$)(R$^{11c}$), Z$^3$ is C(R$^{11c}$)(R$^{11c}$), and Z$^4$ is C(R$^4$)(R$^{11c}$). In some embodiments, Z$^1$ is O, Z$^2$ is C(R$^{11c}$)(R$^{11c}$), Z$^3$ is C(R$^4$)(R$^{11c}$), and Z$^4$ is C(R$^{11c}$)(R$^{11c}$). In some embodiments, Z$^1$ is O, Z$^2$ is C(R$^{11c}$)(R$^{11c}$), Z$^3$ is C(R$^4$)(R$^{11c}$), and Z$^4$ is O.

In some embodiments, each R$^{11c}$ is independently selected from hydrogen, halogen, $C_{1-6}$alkyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{6-10}$aryl, —CH$_2$-C$_{1-11}$heteroaryl, and $C_{1-11}$heteroaryl, wherein $C_{1-6}$alkyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{6-10}$aryl, —CH$_2$-C$_{1-11}$heteroaryl, and $C_{1-11}$heteroaryl are optionally substituted with one, two, or three R$^{20k}$. In some embodiments, each R$^{11c}$ is independently selected from hydrogen and $C_{1-6}$alkyl optionally substituted with one, two, or three R$^{20k}$. In some embodiments, each R$^{11c}$ is hydrogen.

In some embodiments, each R$^{4a}$ is $C_{3-10}$cycloalkyl optionally substituted with one, two, three, or four R$^{4b}$. In some embodiments, each R$^{4a}$ is $C_{2-9}$heterocycloalkyl optionally substituted with one, two, three, or four R$^{4b}$. In some embodiments, each R$^{4a}$ is $C_{6-10}$aryl optionally substituted with one, two, three, or four R$^{4b}$. In some embodiments; each R$^{4a}$ is $C_{1-9}$heteroaryl optionally substituted with one, two, three, or four R$^{4b}$. In some embodiments, each R$^{4a}$ is selected from $C_3$-10cycloalkyl, $C_{2-9}$heterocycloalkyl, $C_{6-10}$aryl, and $C_{1-9}$heteroaryl optionally substituted with one, two, three, or four R$^{4b}$.

In some embodiments, L$^4$ is a bond, —O—, —N(R$^{4d}$)—, —C(O)—, or CR$^{4c}$R$^{4c}$. In some embodiments, L$^4$ is a bond.

In an aspect is provided a compound of Formula (A), or a pharmaceutically acceptable salt or solvate thereof:

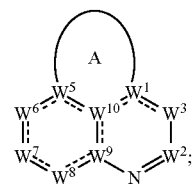

Formula (A)

wherein:
Ring A is a 5-10 membered cycloalkyl or 5-10 membered heterocycloalkyl ring, wherein the 5-10 membered cycloalkyl and 5-10 membered heterocycloalkyl ring are substituted with one or more R$^4$ and optionally substituted with one or more R$^{11c}$;

W$^1$ is C(R$^1$), C, or N;

R$^1$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three R$^{20a}$;

W$^2$ is C(R$^2$);

R$^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20b}$;

W$^3$ is N(R$^{3b}$), N, C(R$^3$), C(R$^3$)(R$^{3a}$), or C(O);

R$^3$ and R$^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20c}$;

R$^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)

($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20c}$;

$W^5$ is C($R^5$), C, or N;

$R^5$ is selected from hydrogen, halogen, —CN, C$_{1-6}$alkyl, C$_{2-6}$alkenyl, C$_{2-6}$alkynyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, and C$_{2-6}$alkynyl are optionally substituted with one, two, or three $R^{20d}$;

$W^6$ is N($R^{6b}$), N, C($R^6$), C($R^6$)($R^{6a}$), C(O), S(O), or S(O)$_2$;

$R^6$ and $R^{6a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20c}$;

$R^{6b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20e}$;

$W^7$ is N($R^7$), C($R^7$), or C($R^7$)($R^{7a}$);

$R^{7a}$ and each $R^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20f}$;

$R^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20f}$;

$R^7$ is -$L^7$-$R^{17}$;

$L^7$ is a bond, —O—, —N($R^{7d}$)—, —C(O)—, —S—, —S(O)$_2$—, —S(O)—, —P(O)$R^{7d}$—, CR$^{7c}$R$^{7c}$, —OCR$^{7c}$R$^{7c}$—, —N($R^{7d}$)CR$^{7c}$R$^{7c}$—, —C(O)CR$^{7c}$R$^{7c}$—, —SCR$^{7c}$R$^{7c}$—, —S(O)$_2$CR$^{7c}$R$^{7c}$—, —S(O)CR$^{7c}$R$^{7c}$—, —P(O)$R^{7d}$CR$^7$R$^{7c}$—, —CR$^{7c}$R$^{7c}$CR$^7$CR$^{7c}$, —CR$^{7c}$RICO—, —CR$^7$R$^{7c}$N($R^{7d}$)—, —CR$^{7c}$R$^{7c}$C(O)—, —CR$^{7c}$R$^{7c}$S—, —CR$^{7c}$R$^{7c}$S(0)$_2$—, —CR$^{7c}$RTCS(O)—, —CR$^7$CR$^7$cP(O)$R^{7d}$, —N($R^{7d}$)C(O)—, —N($R^{7d}$)S(O)$_2$—, —N($R^{7d}$)S(O)—, —N($R^{7d}$)P(O)$R^{7d}$, —C(O)N($R^{7d}$)—, —S(O)$_2$N($R^{7d}$)—, —S(O)N($R^{7d}$)—, —P(O)$R^{7d}$N($R^{7d}$)—, —OC(O)—, —OS(O)$_2$—, —OS(O)—, —OP(O)$R^{7d}$—, —C(O)O—, —S(O)$_{20}$—, —S(O)O—, or —P(O)$R^{7d}$O—;

$R^{17}$ is selected from

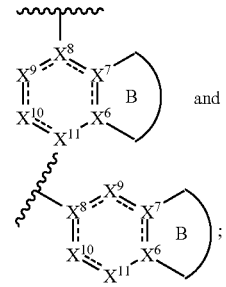

Ring B is a 5- or 6-membered cycloalkyl ring, 5- or 6-membered heterocycloalkyl ring, or 5- or 6-membered heteroaryl ring; wherein the 5- or 6-membered cycloalkyl ring, 5- or 6-membered heterocycloalkyl ring, and 5- or 6-membered heteroaryl ring are optionally substituted with one or more $R^{7c}$;

$X^6$, $X^7$, and $X^8$ are independently C or C($R^{1a}$);

$X^9$, $X^{10}$, and $X^{11}$ are independently C(O), C($R^{1a}$), or C($R^{1a}$)($R^{1b}$);

each $R^{1a}$, $R^{1b}$, and $R^{7c}$ is independently selected from hydrogen, halogen, —CN, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20g}$;

$W^8$ is C($R^8$), C($R^8$)($R^{6a}$), N, N($R^{8b}$), C(O), S(O), or S(O)$_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $W^9$ is $C(R')$, C, or N;

$W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$, $R^4$ is -$L^4$-$R^{4a}$;

each $L^4$ is independently selected from a bond, —O—, —$N(R^{4d})$—, —$C(O)$—, —S—, —$S(O)_2$—, —$S(O)$—, —$P(O)R^{4d}$—, $CR^{4c}R^{4c}$—, —$OCR^{4c}R^{4c}$—, —$N(R^{4d})CR^{4c}R^{4c}$—, —$C(O)CR^{4}R^{4c}$—, —$SCR^{4}R^{4c}$—, —$S(O)_2CRR^{4c}$—, —$S(O)CR^{4}R^{4c}$—, —$P(O)R^{4d}CR^{4}R^{4c}$—, —$CR^{4c}R^{4c}CR^{4}R^{4c}$—, —$CR^{4c}R^{4c}O$—, —$CR^{4c}R^{4c}CN(R^{4d})$—, —$CR^{4}R^{4}CC(O)$—, —$CR^{4}R^{4c}S$—, —$CR^{4c}R^{4c}S(O)_2$—, —$CR^{4c}R^{4}S(O)$—, —$CR^{4}R^{4}$ c$P(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^{4d}N(R^{4d})$—, —$OC(O)$—, —$OS(O)_2$—, —$OS(O)$—, —$OP(O)R^{4d}$—, —$C(O)O$—, —$S(O)_2O$—, —$S(O)O$—, and —$P(O)R^{4d}O$—;

each $R^4$ is independently selected from hydrogen, halogen, —CN, $C_{1-6}$alkyl, $C_{2-6}$alkenyl, $C_{2-6}$alkynyl, $C_1$-haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH2C(O)OR^{14}$, —$OC(O)R^{14a}$, —$N(R^{14})(R^{14})$, —$N(R^{14})C(O)N(R^{14})(R^{14})$, —$N(R^{14})C(O)OR^{14}$, —$N(R^{14})C(O)R^{14a}$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH2C(O)OR^{14}$, and —$OC(O)R^{14}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$OC(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14}a$, —$S(O)_2R^{14}$, —$S(O)_2N(R^{14})(R^{14})$, and —$OC(O)R^{14a}$;

each $R^{4a}$ is independently selected from $C_{2-9}$heterocycloalkyl, wherein $C_{2-9}$heterocycloalkyl is optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(0)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl are optionally substituted with one, two, or three R$^{20l}$;

each R$^{12c}$ is independently selected from hydrogen and R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{14}$ is independently selected from hydrogen, C$_{1-6}$alkyl, and C$_{1-6}$haloalkyl;

each R$^{14a}$ is independently selected from C$_{1-6}$alkyl and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20m}$;

each R$^{20a}$; R$^{20b}$; R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH2C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl;

each R$^{23}$ is independently selected from H and C$_{1-6}$alkyl;
each R$^{24}$ is independently selected from H and C$_{1-6}$alkyl;
each R$^{25}$ is independently selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$ heteroaryl; and ----- indicates a single or double bond such that all valences are satisfied.

In an aspect is provided a compound of Formula (B), or a pharmaceutically acceptable salt or solvate thereof:

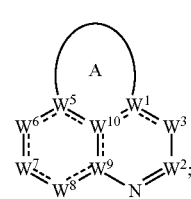

Formula (B)

wherein:
Ring A is a 5-10 membered cycloalkyl or 5-10 membered heterocycloalkyl ring, wherein the 5-10 membered cycloalkyl and 5-10 membered heterocycloalkyl ring are optionally substituted substituted with one or more R$^4$ and optionally substituted with one or more R$^{11c}$;

W$^1$ is C(R$^1$), C, or N;

R$^1$ is selected from hydrogen, halogen, —CN, C$_{1-6}$alkyl, C$_{2-6}$alkenyl, C$_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, and C$_{2-6}$alkynyl are optionally substituted with one, two, or three R$^{20a}$;

W$^2$ is C(R$^2$);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, and C$_{1-9}$heteroaryl are optionally substituted with one, two, or three R$^{20b}$;

W$^3$ is N(R$^{3b}$), N, C(R$^3$), C(R$^3$)(R$^{3a}$), or C(O);

R$^3$ and R$^{3a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-heteroaryl are optionally substituted with one, two, or three R$^{20c}$;

R$^{3b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_1$-heteroaryl, —OR$^{12}$, —SR$^{12}$, —C(O)

OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

W$^5$ is C(R$^5$), C, or N;

R$^5$ is selected from hydrogen, halogen, —CN, C$_{1-6}$alkyl, C$_{2-6}$alkenyl, C$_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, and C$_{2-6}$alkynyl are optionally substituted with one, two, or three R$^{20d}$;

W$^6$ is N(R$^{6b}$), N, C(R$^6$), C(R$^6$)(R$^{6a}$), C(O), S(O), or S(O)$_2$;

R$^6$ and R$^{6a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

R$^{6b}$ is selected from hydrogen, —CN, C$_{1-6}$alkyl, C$_{2-6}$alkenyl, C$_{2-6}$alkynyl, C$_{3-10}$cycloalkyl, C$_2$-heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

W$^7$ is N(R$^7$), C(R$^7$), or C(R$^7$)(R$^{7a}$);

R$^{7a}$ and each R$^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20f}$;

R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl are optionally substituted with one, two, or three R$^{20f}$;

R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$, CR$^7$CR$^{7c}$, —OCR$^7$R$^{7c}$—, —N(R$^{7d}$)CR$^7$CR$^{7c}$—, —C(O)CR$^7$CR$^{7c}$—, —SCR$^7$CR$^{7c}$—, —S(O)$_2$CR$^7$CR$^{7c}$—, —S(O)CR$^7$CR$^{7c}$, —P(O)R$^{7d}$CR$^7$CR$^{7c}$—, —CR$^7$CR$^{7c}$CR$^7$CR$^{7c}$—, —CR$^7$CR$^{7c}$O—, —CR$^7$CR$^{7a}$N(R$^{7d}$)—, —CR$^{7c}$R$^{7c}$C(O)—, —CR$^7$CR$^{7c}$S—, —CR$^7$CR$^{7c}$S(O)$_2$—, —CR$^7$CR$^{7c}$S(O)—, —CR$^7$CR$^7$CP(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7a}$N(R$^{7d}$)—, —OC(O)—, —OS(O)$_2$—, —OS(O)—, —OP(O)R$^{7d}$—, —C(O)O—, —S(O)$_2$O—, —S(O)O—, or —P(O)R$^{7a}$O—;

R$^{17}$ is selected from

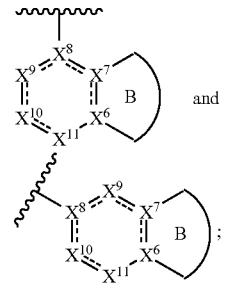

Ring B is a 5- or 6-membered cycloalkyl ring, 5- or 6-membered heterocycloalkyl ring, 5- or 6-membered heteroaryl ring, or 6-membered aryl ring, wherein the 5- or 6-membered cycloalkyl ring, 5- or 6-membered heterocycloalkyl ring, 5- or 6-membered heteroaryl ring, and 6-membered aryl ring are optionally substituted with one or more R$^{7c}$;

X$^6$, X$^7$, and X$^8$ are independently C or C(R$^{1a}$);

X$^9$, X$^{10}$, and X$^{11}$ are independently C(O), C(R$^{1a}$), or C(R$^{1a}$)(R$^{1b}$);

each R$^{1a}$, R$^{1b}$, and R$^{7c}$ is independently selected from hydrogen, halogen, —CN, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, $C_{6-10}$aryl, and $C_{1-9}$heteroaryl are optionally substituted with one, two, or three $R^{20g}$;

$W^8$ is $C(R^8)$, $C(R^8)(R^{8a})$, N, $N(R^{8b})$, $C(O)$, $S(O)$, or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and -$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $W^9$ is $C(R^9)$, C, or N;

$W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$;

$R^4$ is -$L^4$-$R^{4a}$;

each $L^4$ is independently selected from a bond, —O—, —$N(R^{4d})$—, —C(O)—, —S—, —$S(O)_2$—, —S(O)—, —$P(O)R^{4d}$, $CR^4R^{4c}$, —$OCR^4R^{4c}$—, —$N(R^{4d})CR^{4c}R^{4c}$—, —$C(O)CR^4R^{4c}$—, —$SCR^{4c}R^{4c}$—, —$S(O)_2$ $CR^{4c}R^{4c}$—, —$S(O)CR^{4c}R^{4c}$—, —$P(O)R^{4d}CR^{4c}R^{4c}$—, —$CR^4R^4CCR^{4c}R^{4c}$—, —$CR^{4c}R^{4c}O$—, —$CR^{4c}RAN(R^{4d})$—, —$CR^4R^4C(O)$—, —$CR^4R^{4c}S$—, —$CR^4R^{4c}S(O)_2$—, —$CR^4R^{4c}S(O)$—, —$CR^4R^4CP(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^4ON(R^{4d})$—, —OC(O)—, —$OS(O)_2$—, —OS(O)—, —$OP(O)R^{4d}$—, —C(O)O—, —$S(O)_2O$—, —S(O)O—, and —$P(O)R^{4d}O$—;

each $R^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH2C(O)OR^{14}$, —$OC(O)R^{14}a$, —$N(R^{14})(R^{14})$, —$N(R^{14})C(O)N(R^{14})(R^{14})$, —$N(R^{14})C(O)OR^{14}$, —$N(R^{14})C(O)R^{14a}$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH2C(O)OR^{14}$, and —$OC(O)R^{14}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$; —$S(O)_2R^{14}$, —$S(O)_2N(R^{14})(R^{14})$, and —$OC(O)R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(0)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$(O)R^{12}$, —$SR^{12}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-}$ $_{12}$aryl, —CH$_2$-C$_{1-11}$heteroaryl, and C$_{1-11}$heteroaryl are optionally substituted with one, two, or three R$^{20k}$;

each R$^{12}$ is independently selected from hydrogen, C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl are optionally substituted with one, two, or three R$^{20l}$;

each R$^{12c}$ is independently selected from hydrogen and R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{14}$ is independently selected from hydrogen, C$_{1-6}$alkyl, and C$_{1-6}$haloalkyl;

each R$^{14a}$ is independently selected from C$_{1-6}$alkyl and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20m}$;

each R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH2C(O)OR$^{22}$, and —OC(O)R$^{25}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{23}$ is independently selected from H and C$_{1-6}$alkyl;
each R$^{24}$ is independently selected from H and C$_{1-6}$alkyl;

each R$^{25}$ is independently selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and ----- indicates a single or double bond such that all valences are satisfied.

In an aspect is provided a compound of Formula (C), or a pharmaceutically acceptable salt or solvate thereof:

Formula (C)

wherein:

Ring A is a 5-10 membered cycloalkyl or 5-10 membered heterocycloalkyl ring, wherein the 5-10 membered cycloalkyl and 5-10 membered heterocycloalkyl ring are substituted with at least one R$^4$, and wherein the 5-10 membered cycloalkyl and 5-10 membered heterocycloalkyl ring are optionally substituted with one or more R$^{11c}$;

W$^1$ is C(R$^1$), C, or N;

R$^1$ is selected from hydrogen, halogen, —CN, C$_{1-6}$alkyl, C$_{2-6}$alkenyl, C$_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, and C$_{2-6}$alkynyl are optionally substituted with one, two, or three R$^{20a}$;

W$^2$ is C(R$^2$);

R$^2$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

W$^3$ is N(R$^{3b}$), N, C(R$^3$), C(R$^3$)(R$^{3a}$), or C(O);

R$^3$ and R$^{3a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S $(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, C(O), S(O), or $S(O)_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$R^{6b}$ is selected from hydrogen, —CN, $C_{1-6}$alkyl, $C_{2-6}$alkenyl, $C_{2-6}$alkynyl, $C_{3-10}$cycloalkyl, $C_2$—, heterocycloalkyl, $C_{6-10}$aryl, $C_1$—, heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^7$ is $N(R^7)$, $C(R^7)$, or $C(R^7)(R^{7a})$;

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_2$-9 heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three $R^{20f}$;

$R^7$ is -$L^7$-$R^{17}$;

$L^7$ is a bond, —O—, —$N(R^{7d})$—, —$C(O)$—, —S—, —$S(O)_2$—, —$S(O)$—, —$P(O)R^{7d}$—, $CR^{7c}R^{7c}$—, —$OCR^{7c}R^{7c}$—, —$N(R^{7d})CR^{7o}R^{7c}$—, —$C(O)CR^{7c}R^{7c}$—, —$SCR^{7c}R^{7c}$—, —$S(O)_2CR^{7c}R^{7c}$—, —$S(O)CR^{7c}R^{7c}$—, —$P(O)R^{7d}CR^{7c}R^{7c}$—, —$CR^{7c}R^{7c}\&CR^{7c}R^{7c}$, —$CR^{7c}RICO$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^{7c}R^{7c}S(O)$—, —$CR^{7c}R^{7c}P(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —$OC(O)$—, —$OS(O)_2$—, —$OS(O)$—, —$OP(O)R^{7d}$—, —$C(O)O$—, —$S(O)_{20}$—, —$S(O)O$—, or —$P(O)R^{7d}O$—;

$R^{17}$ is selected from $C_{2-9}$heterocycloalkyl and $C_{1-9}$heteroaryl, wherein $C_{2-9}$heterocycloalkyl and $C_{1-9}$heteroaryl are optionally substituted with one, two, or three $R^{20g}$;

$W^8$ is $C(R^8)$, $C(R^8)(R^{8a})$, N, $N(R^{8b})$, C(O), S(O), or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and -$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $W^9$ is $C(R^9)$, C, or N;

$W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$;

$R^4$ is -$L^4$-$R^{4a}$;

$L^4$ is a bond, —O—, —N($R^{4d}$)—, —C(O)—, —S—, —S(O)$_2$—, —S(O)—, —P(O)$R^{4d}$—, $CR^{4c}R^4$, —OC$R^{4c}R^{4c}$—, —N($R^{4d}$)C$R^{4c}R^{4c}$—, —C(O)C$R^4R^{4c}$—, —SC$R^4R^{4c}$—, —S(O)$_2$C$R^4R^{4c}$—, —S(O)C$R^{4c}R^{4c}$—, —P(O)$R^{4d}$C$R^4R^{4c}$—, —C$R^{4c}R^4$CC$R^4R^4$, —C$R^4R^{4c}$O—, —C$R^4R^4$CN($R^{4d}$)—, —C$R^4R^4$CC(O)—, —C$R^{4c}R^{4c}$S—, —C$R^4R^{4c}$S(O)$_2$—, —C$R^{4c}R^{4c}$S(O)—, —C$R^4R^{4c}$CP(O)$R^{4d}$—, —N($R^{4d}$)C(O)—, —N($R^{4d}$)S(O)$_2$—, —N($R^{4d}$)S(O)—, —N($R^{4d}$)P(O)$R^{4d}$—, —C(O)N($R^{4d}$)—, —S(O)$_2$N($R^{4d}$)—, —S(O)N($R^{4d}$)—, —P(O)$R^{4d}$N($R^{4d}$)—, —OC(O)—, —OS(O)$_2$—, —OS(O)—, —OP(O)$R^{4d}$—, —C(O)O—, —S(O)$_2$O—, —S(O)O—, or —P(O)$R^{4d}$O—;

each $R^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —O$R^{14}$, —S$R^{14}$, —C(O)O$R^{14}$, —C(O)N($R^{14}$)($R^{14}$), —C(O)C(O)N($R^{14}$)($R^{14}$), —OC(O)N($R^{14}$)($R^{14}$), —C(O)$R^{14a}$, —S(O)$_2$$R^{14}$, —S(O)$_2$N($R^{14}$)($R^{14}$), —OCH2C(O)O$R^{14}$, —OC(O)$R^{14}$a, —N($R^{14}$)($R^{14}$), —N($R^{14}$)C(O)N($R^{14}$)($R^{14}$), —N($R^{14}$)C(O)O$R^{14}$, —N($R^{14}$)C(O)$R^{14a}$, and —N($R^{14}$)S(O)$_2$$R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{14}$, —S$R^{14}$, —N($R^{14}$)($R^{14}$), —C(O)O$R^{14}$, —C(O)N($R^{14}$)($R^{14}$), —C(O)C(O)N($R^{14}$)($R^{14}$), —OC(O)N($R^{14}$)($R^{14}$), —N($R^{14}$)C(O)N($R^{14}$)($R^{14}$), —N($R^{14}$)C(O)O$R^{14}$, —N($R^{14}$)C(O)$R^{14}$, —N($R^{14}$)S(O)$_2$$R^{14}$, —C(O)$R^{14a}$, —S(O)$_2$$R^{14}$, —S(O)$_2$N($R^{14}$)($R^{14}$), and —OC(O)$R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —O$R^{14}$, —S$R^{14}$, —C(O)O$R^{14}$, —C(O)N($R^{14}$)($R^{14}$), —C(O)C(O)N($R^{14}$)($R^{14}$), —OC(O)N($R^{14}$)($R^{14}$), —C(O)$R^{14a}$, —S(O)$_2$$R^{14}$, —S(O)$_2$N($R^{14}$)($R^{14}$), —OCH2C(O)O$R^{14}$, and —OC(O)$R^{14}$a, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{14}$, —S$R^{14}$, —N($R^{14}$)($R^{14}$), —C(O)O$R^{14}$, —C(O)N($R^{14}$)($R^{14}$), —C(O)C(O)N($R^{14}$)($R^{14}$), —OC(O)N($R^{14}$)($R^{14}$), —N($R^{14}$)C(O)N($R^{14}$)($R^{14}$), —N($R^{14}$)C(O)O$R^{14}$, —N($R^{14}$)C(O)$R^{14}$, —N($R^{14}$)S(O)$_2$$R^{14}$, —C(O)$R^{14}$a, —S(O)$_2$$R^{14}$, —S(O)$_2$N($R^{14}$)($R^{14}$), and —OC(O)$R^{14a}$;

$R^{4a}$ is selected from $C_{3-10}$cycloalkyl, $C_{2-9}$heterocycloalkyl, and $C_{6-10}$aryl, wherein $C_{3-10}$cycloalkyl, $C_{2-9}$heterocycloalkyl, and $C_{6-10}$aryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2$$R^{15}$, —$CH_2$S(O)$_2$N($R^{12}$)($R^{13}$), and —P(=O)($R^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —(O)$R^{12}$, —S$R^{12}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2$$R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_{2-9}$heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_{2-9}$heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl are optionally substituted with one, two, or three $R^{20l}$;

each $R^{12c}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{14}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$; $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH2C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each R$^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each R$^{23}$ is independently selected from H and $C_{1-6}$alkyl;
each R$^{24}$ is independently selected from H and $C_{1-6}$alkyl;
each R$^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments, the compound of Formula (A), or a pharmaceutically acceptable salt or solvate thereof, has the structure of Formula (A-1):

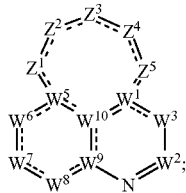

Formula (A-1)

wherein
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); and
Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (B), or a pharmaceutically acceptable salt or solvate thereof, has the structure of Formula (B-1):

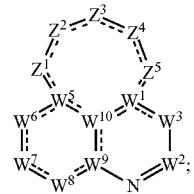

Formula (B-1)

wherein
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); and
Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O).

In some embodiments, the compound of Formula (C), or a pharmaceutically acceptable salt or solvate thereof, has the structure of Formula (C-1):

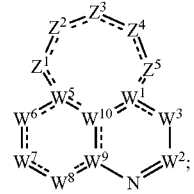

Formula (C-1)

wherein
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); and
Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, W$^1$ is C. In some embodiments, W$^1$ is C(R$^1$). In some embodiments, W$^1$ is N. In some embodiments, W$^5$ is C. In some embodiments, W$^5$ is C(R$^5$). In some embodiments, W$^5$ is N. In some embodiments, W$^2$ is C(R$^2$). In some embodiments, W$^2$ is C(R$^2$)(R$^{2a}$). In some embodiments, W$^2$ is N. In some embodiments, W$^2$ is N(R$^{2a}$). In some embodiments, W$^3$ is N. In some embodiments, W$^3$ is N(R$^{3b}$). In some embodiments, W$^3$ is C(R$^3$). In some embodiments, W$^3$ is C(R$^3$)(R$^{3a}$). In some embodiments, W$^3$ is C(O). In some embodiments, W$^6$ is C(R$^6$). In some embodiments, W$^6$ is C(R$^6$)(R$^{6a}$). In some embodiments, W$^6$ is N. In some embodiments, W$^6$ is N(R$^6$%). In some embodiments, W$^6$ is C(O). In some embodiments, W$^7$ is C(R$^7$). In some embodiments, W$^7$ is C(R$^7$)(R$^{78}$). In some embodiments, W$^7$ is N(R$^7$). In some embodiments, W$^8$ is C(R$^8$). In some embodiments, W$^8$ is C(R$^8$)(R$^{88}$). In some embodiments, W$^8$ is N. In some embodiments, W$^8$ is N(R$^8$%). In some embodiments, W$^8$ is C(O). In some embodiments, W$^{10}$ is C. In some embodiments, W$^{10}$ is N. In some embodiments, W$^{10}$ is C. In some embodiments, W$^{10}$ is N.

In some embodiments, the compound of Formula (A-1), or a pharmaceutically acceptable salt or solvate thereof, has the structure of Formula (A-1a):

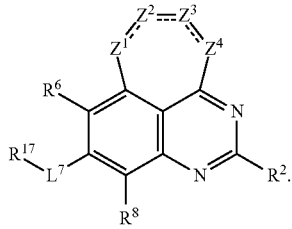

Formula (A-1a)

In some embodiments, the compound of Formula (A-1), or a pharmaceutically acceptable salt or solvate thereof, has the structure of Formula (A-1b):

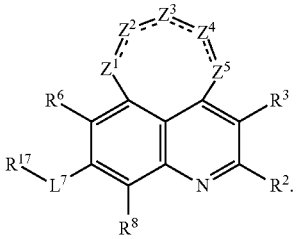

Formula (A-1b)

In some embodiments, the compound of Formula (A-1), or a pharmaceutically acceptable salt or solvate thereof, has the structure of Formula (A-1c):

Formula (A-1c)

In some embodiments, the compound of Formula (A-1), or a pharmaceutically acceptable salt or solvate thereof, has the structure of Formula (A-1d):

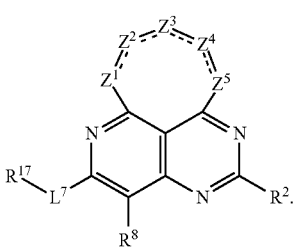

Formula (A-1d)

In some embodiments, the compound of Formula (A-1), or a pharmaceutically acceptable salt or solvate thereof, has the structure of Formula (A-1e):

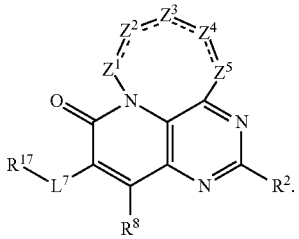

Formula (A-1e)

In some embodiments, the compound of Formula (A-1), or a pharmaceutically acceptable salt or solvate thereof, has the structure of Formula (A-1f):

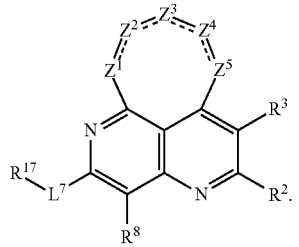

Formula (A-1f)

In some embodiments of the compound of Formula (A), (A-1), (A-1a), (A-1b), (A-1c), (A-1d), (A-1e), or (A-1f), or a pharmaceutically acceptable salt or solvate thereof, $R^{17}$ is

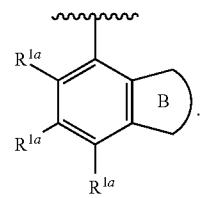

In some embodiments of the compound of Formula (A), (A-1), (A-1a), (A-1b), (A-1c), (A-1d), (A-1e), or (A-1f), or a pharmaceutically acceptable salt or solvate thereof, $R^{17}$ is

In some embodiments of the compound of Formula (A), (A-1), (A-1a), (A-1b), (A-1c), (A-1d), (A-1e), or (A-1f), or a pharmaceutically acceptable salt or solvate thereof, $R^{17}$ is

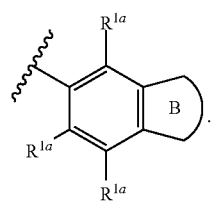

In some embodiments of the compound of Formula (A), (A-1), (A-1a), (A-1b), (A-1c), (A-1d), (A-1e), or (A-1f), or a pharmaceutically acceptable salt or solvate thereof, $R^{17}$ is

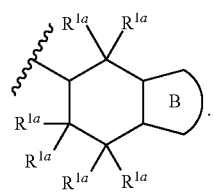

In some embodiments of the compound of Formula (A), (A-1), (A-1a), (A-1b), (A-1c), (A-1d), (A-1e), or (A-1f), or a pharmaceutically acceptable salt or solvate thereof, each $R^{1a}$ is independently selected from hydrogen, halogen, $C_{1-6}$alkyl, and $—OR^{12}$, wherein $C_{1-6}$alkyl is optionally substituted with one, two, or three $R^{20g}$.

In some embodiments of the compound of Formula (A), (A-1), (A-1a), (A-1b), (A-1c), (A-1d), (A-1e), or (A-1f), or a pharmaceutically acceptable salt or solvate thereof, Ring B is a 5- or 6-membered heteroaryl ring optionally substituted with one or more $R^{1c}$.

In some embodiments of the compound of Formula (A), (A-1), (A-1a), (A-1b), (A-1c), (A-1d), (A-1e), or (A-If), or a pharmaceutically acceptable salt or solvate thereof, $R^{17}$ is selected from:

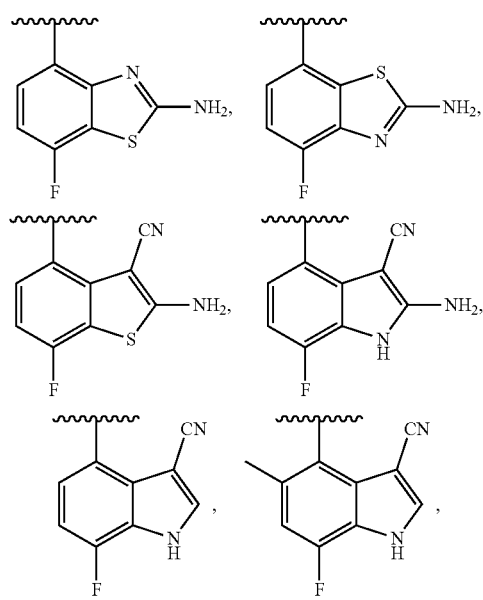

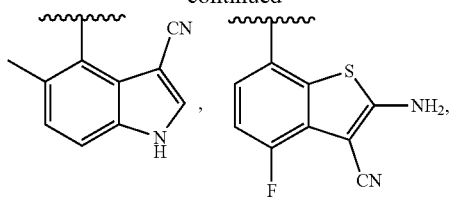

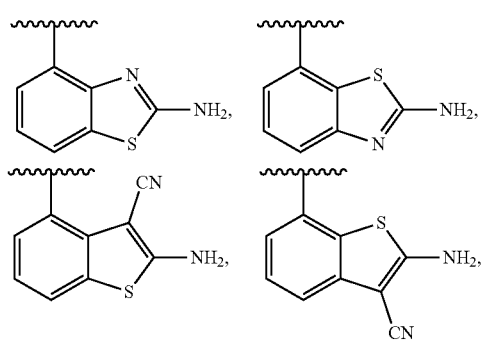

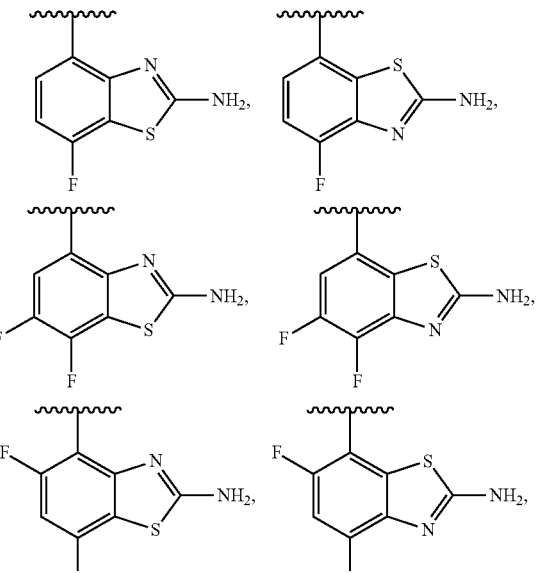

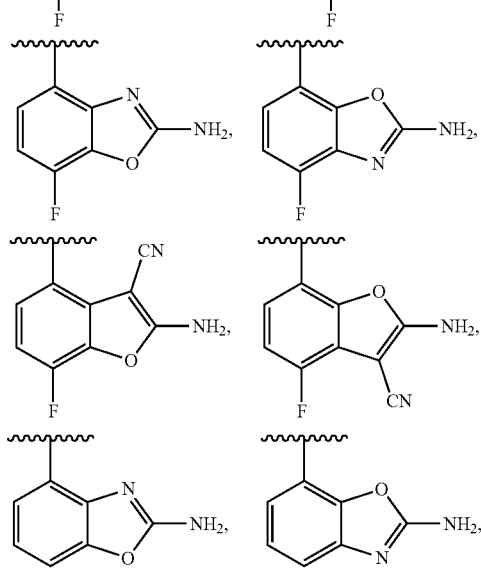

-continued
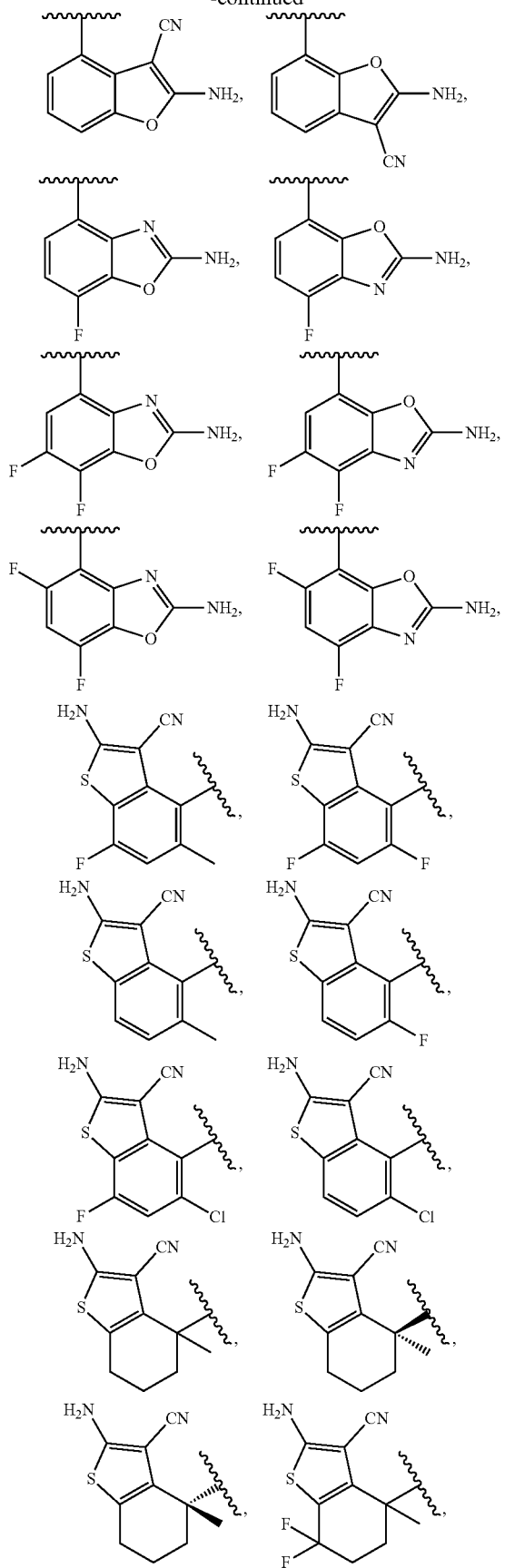
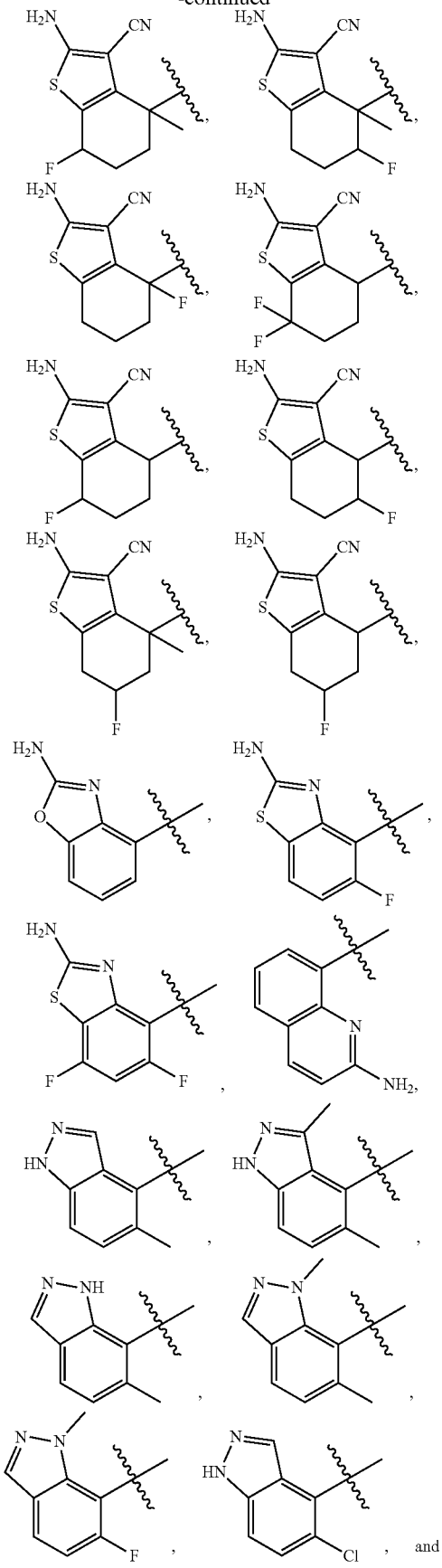

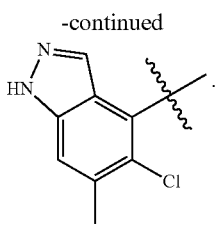

In some embodiments, the compound of Formula (B-1), or a pharmaceutically acceptable salt or solvate thereof, has the structure of Formula (B-1a):

Formula (B-1a)

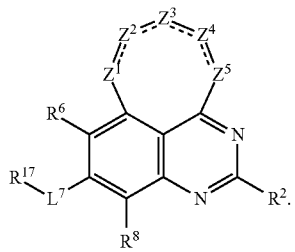

In some embodiments, the compound of Formula (B-1), or a pharmaceutically acceptable salt or solvate thereof, has the structure of Formula (B-1b):

Formula (B-1b)

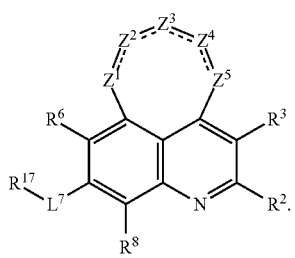

In some embodiments, the compound of Formula (B-1), or a pharmaceutically acceptable salt or solvate thereof, has the structure of Formula (B-1c):

Formula (B-1c)

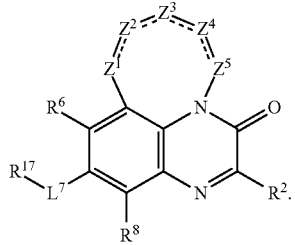

In some embodiments, the compound of Formula (B-1), or a pharmaceutically acceptable salt or solvate thereof, has the structure of Formula B-1d):

Formula (B-1d)

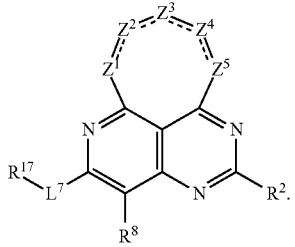

In some embodiments, the compound of Formula (B-1), or a pharmaceutically acceptable salt or solvate thereof, has the structure of Formula (B-1e):

Formula (B-1e)

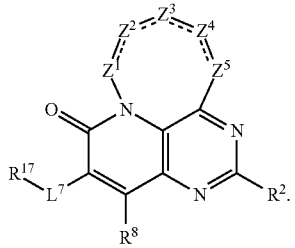

In some embodiments, the compound of Formula (B-1), or a pharmaceutically acceptable salt or solvate thereof, has the structure of Formula (B-1f):

Formula (B-1f)

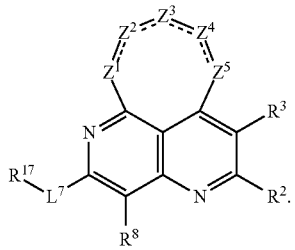

In some embodiments of the compound of Formula (B), (B-1), (B-1a), (B-1b), (B-1c), (B-1d), (B-1e), or (B-1f), or a pharmaceutically acceptable salt or solvate thereof, $R^{17}$ is

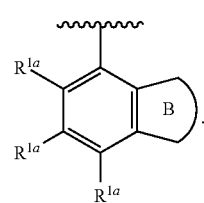

In some embodiments of the compound of Formula (B), (B-1), (B-1a), (B-1b), (B-1c), (B-1d), (B-1e), or (B-1f), or a pharmaceutically acceptable salt or solvate thereof, $R^{17}$ is

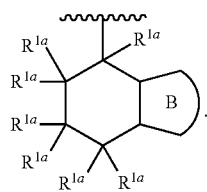

In some embodiments of the compound of Formula (B), (B-1), (B-1a), (B-1b), (B-1c), (B-1d), (B-1e), or (B-1f), or a pharmaceutically acceptable salt or solvate thereof, $R^{17}$ is

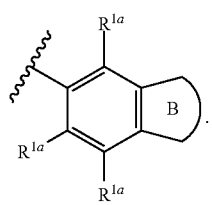

In some embodiments of the compound of Formula (B), (B-1), (B-1a), (B-1b), (B-1c), (B-1d), (B-1e), or (B-1f), or a pharmaceutically acceptable salt or solvate thereof, $R^{17}$ is

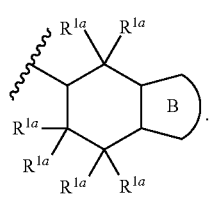

In some embodiments of the compound of Formula (B), (B-1), (B-1a), (B-1b), (B-1c), (B-1d), (B-1e), or (B-1f), or a pharmaceutically acceptable salt or solvate thereof, each $R^{1a}$ is independently selected from hydrogen, halogen, $C_{1-6}$alkyl, and $-OR^{12}$, wherein $C_{1-6}$alkyl is optionally substituted with one, two, or three $R^{20g}$.

In some embodiments of the compound of Formula (B), (B-1), (B-1a), (B-1b), (B-1c), (B-1d), (B-1e), or (B-1f), or a pharmaceutically acceptable salt or solvate thereof, Ring B is a 5- or 6-membered heteroaryl ring optionally substituted with one or more $R^{7c}$. In some embodiments of the compound of Formula (B), (B-1), (B-1a), (B-1b), (B-1c), (B-1d), (B-1e), or (B-1f), or a pharmaceutically acceptable salt or solvate thereof, Ring B is a 6-membered aryl ring optionally substituted with one or more $R^{7c}$.

In some embodiments of the compound of Formula (B), (B-1), (B-1a), (B-1b), (B-1c), (B-1d), (B-1e), or (B-1f), or a pharmaceutically acceptable salt or solvate thereof, $R^{17}$ is selected from:

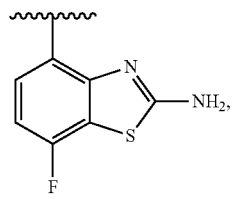 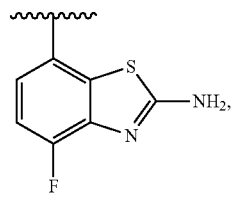

-continued

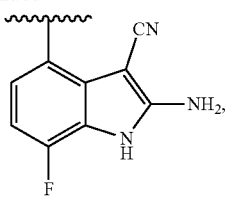

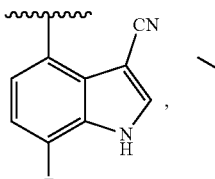 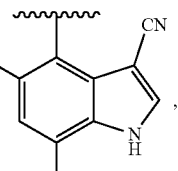

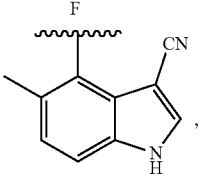 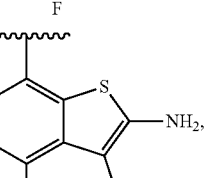

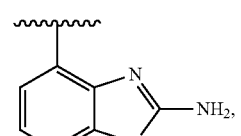 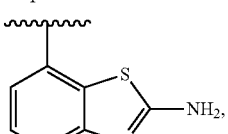

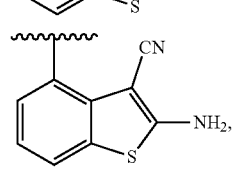 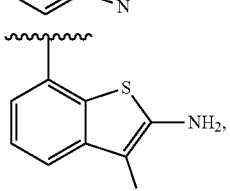

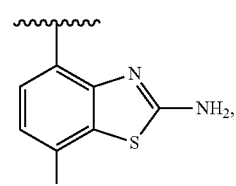 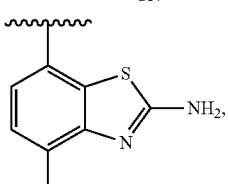

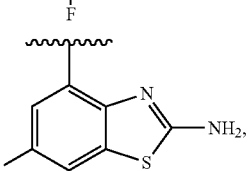 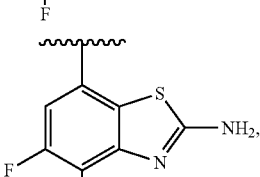

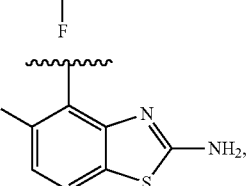 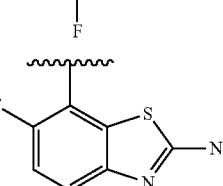

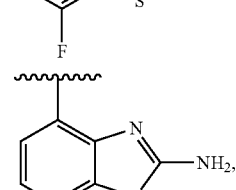 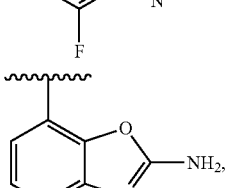

-continued
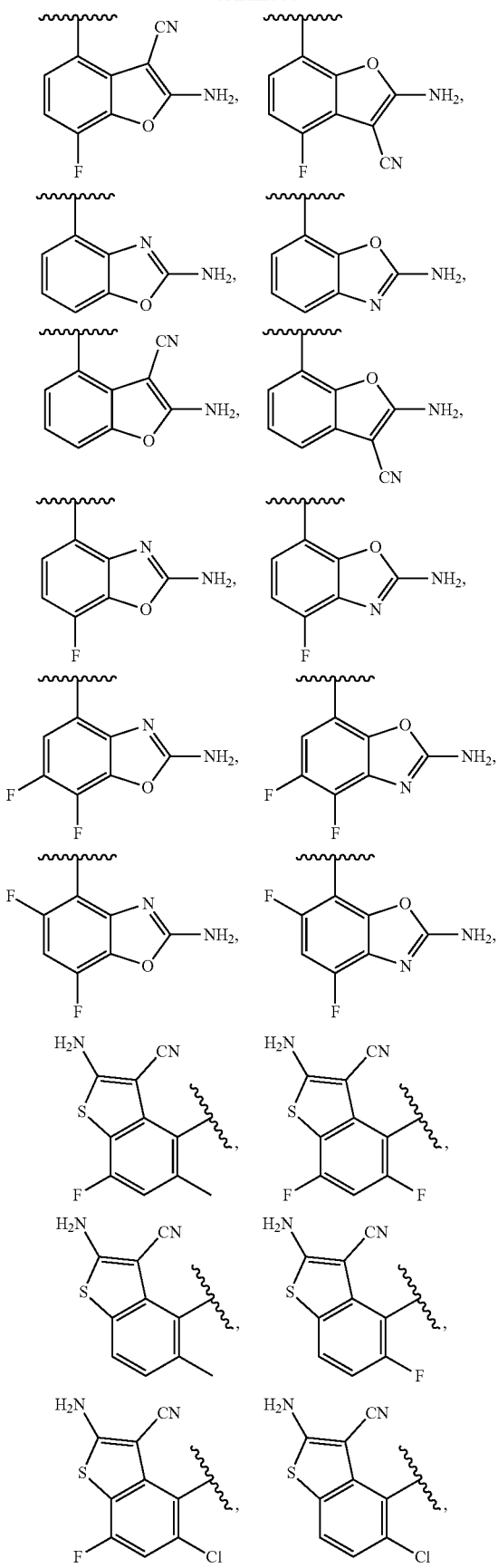
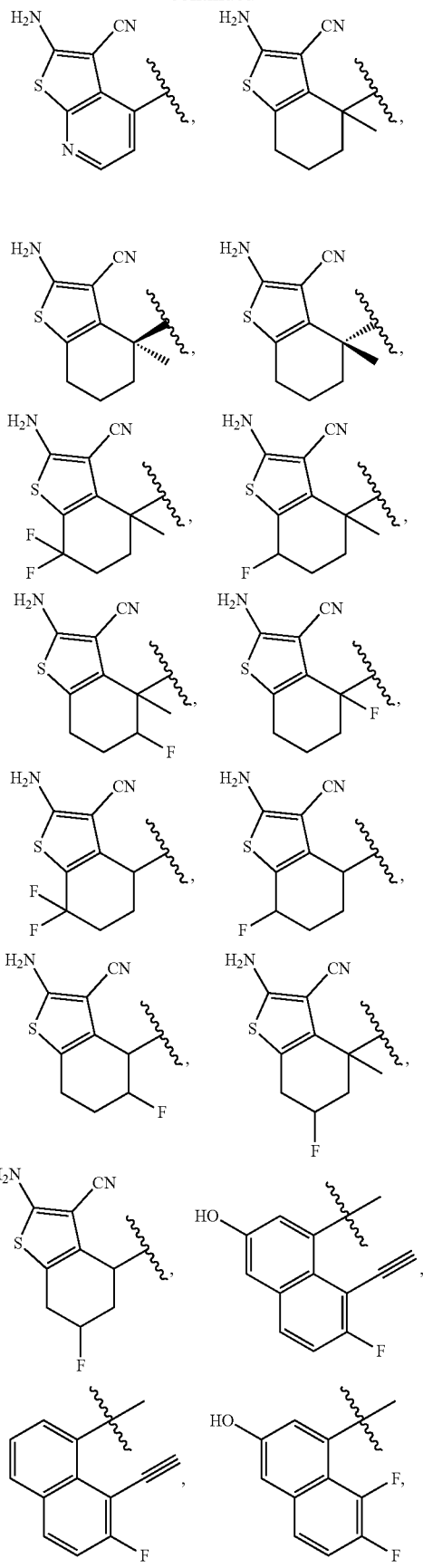

-continued

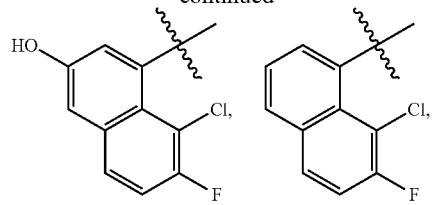

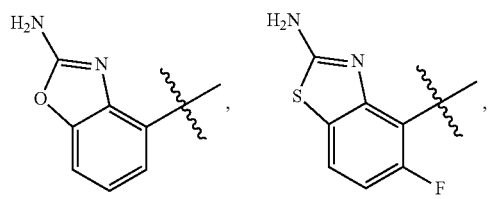

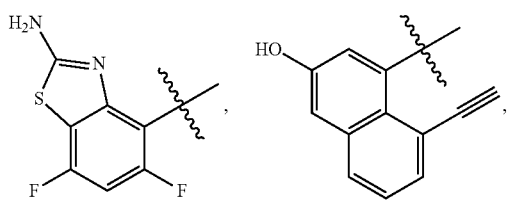

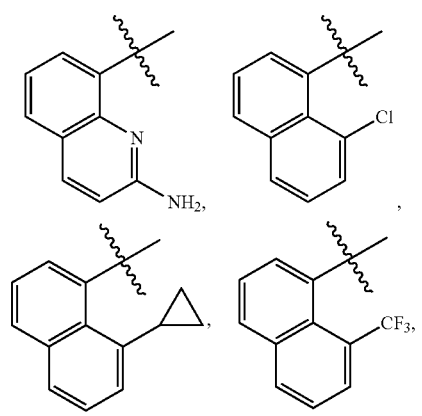

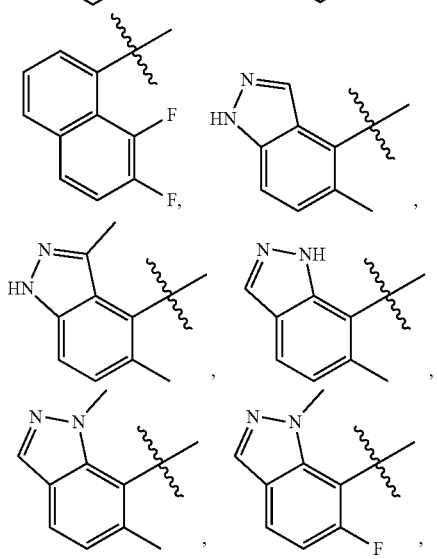

-continued

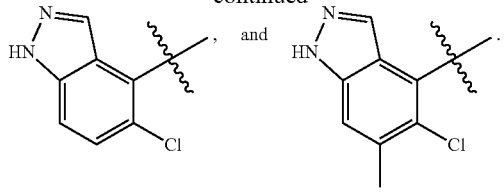

In some embodiments, the compound of Formula (C-1), or a pharmaceutically acceptable salt or solvate thereof, has the structure of Formula (C-1a):

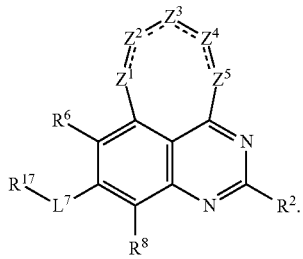

Formula (C-1a)

In some embodiments, the compound of Formula (C-1), or a pharmaceutically acceptable salt or solvate thereof, has the structure of Formula (C-1b):

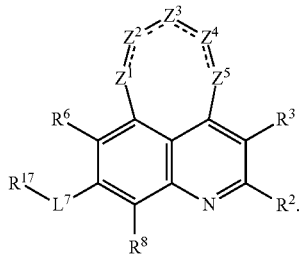

Formula (C-1b)

In some embodiments, the compound of Formula (C-1), or a pharmaceutically acceptable salt or solvate thereof, has the structure of Formula (C-1c):

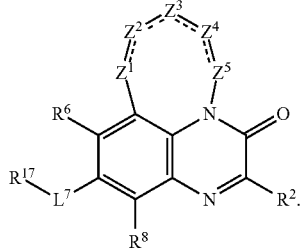

Formula (C-1c)

In some embodiments, the compound of Formula (C-1), or a pharmaceutically acceptable salt or solvate thereof, has the structure of Formula C-1d):

Formula (C-1d)

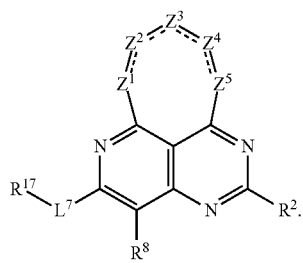

In some embodiments, the compound of Formula (C-1), or a pharmaceutically acceptable salt or solvate thereof, has the structure of Formula (C-1e):

Formula (C-1e)

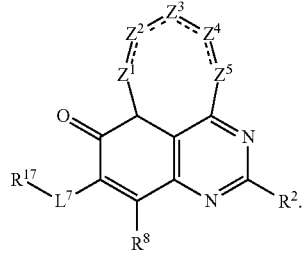

In some embodiments, the compound of Formula (C-1), or a pharmaceutically acceptable salt or solvate thereof, has the structure of Formula (C-1f):

Formula (C-1f)

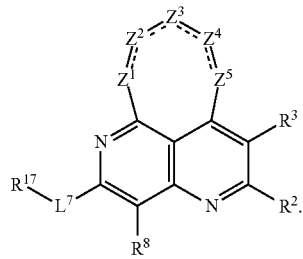

In some embodiments of the compound of Formula (C), (C-1), (C-1a), (C-1b), (C-1c), (C-1d), (C-1e), or (C-1f), or a pharmaceutically acceptable salt or solvate thereof, $R^{17}$ is $C_{2-9}$heterocycloalkyl optionally substituted with one, two, or three $R^{20g}$. In some embodiments of the compound of Formula (C), (C-1), (C-1a), (C-1b), (C-1c), (C-1d), (C-1e), or (C-1f), or a pharmaceutically acceptable salt or solvate thereof, $R^{17}$ is $C_{1-9}$heteroaryl optionally substituted with one, two, or three $R^{20g}$.

In some embodiments of the compound of Formula (C), (C-1), (C-1a), (C-1b), (C-1c), (C-1d), (C-1e), or (C-1f), or a pharmaceutically acceptable salt or solvate thereof, $R^{17}$ is selected from

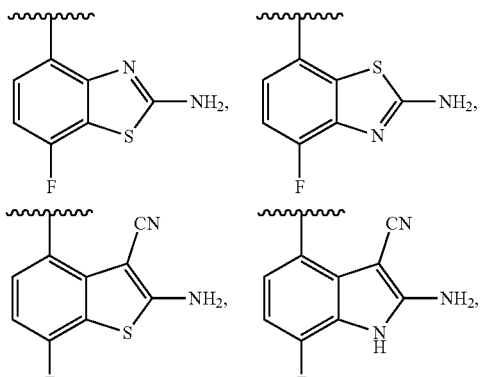

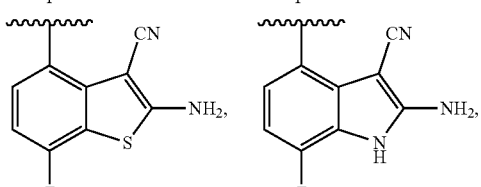

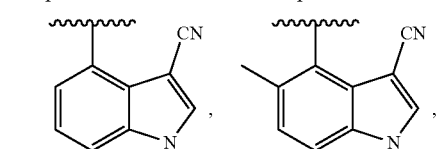

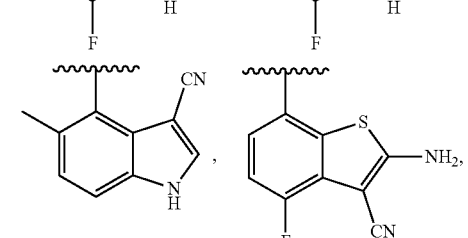

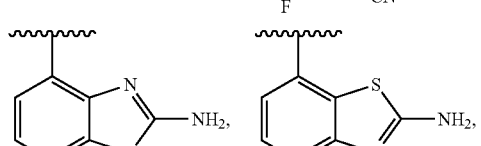

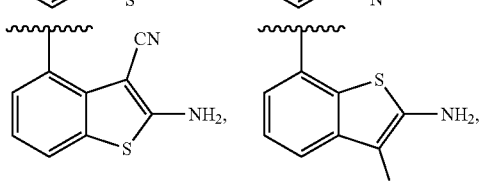

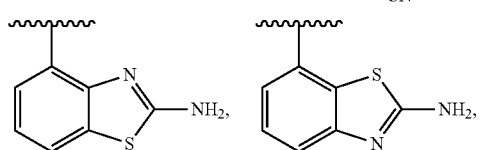

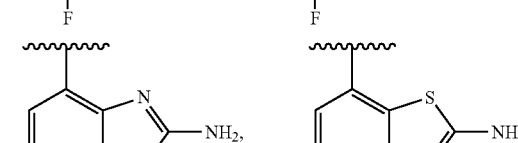

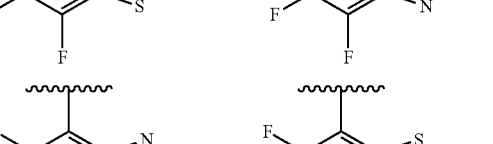

-continued
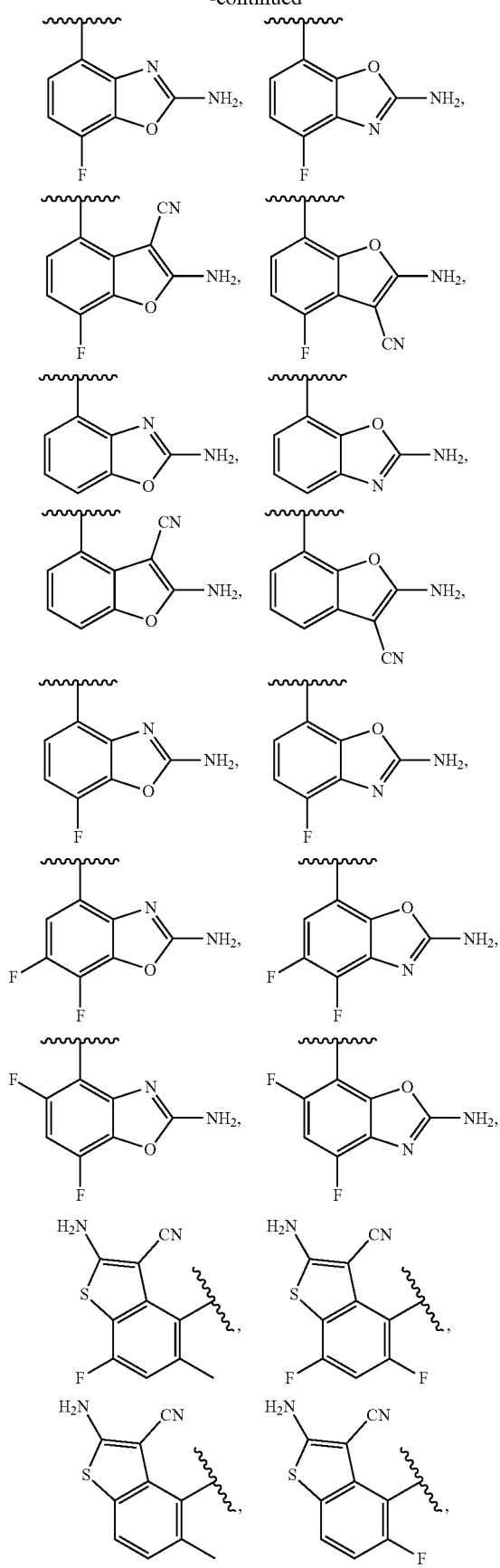
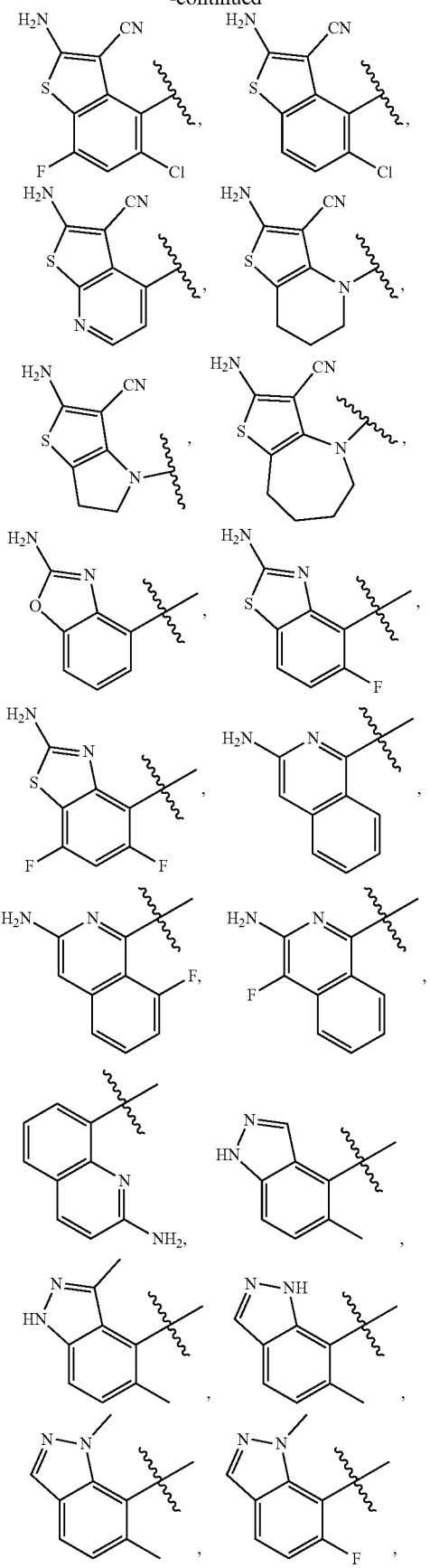

-continued

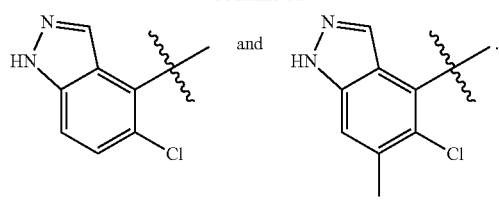
and

In some embodiments, L$^7$ is a bond, —O—, —N(R$^{7d}$)—, —C(O)—, or CR$^{7o}$R$^{7c}$. In some embodiments, L$^7$ is a bond.

In some embodiments, R$^2$ is selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, and —N(H)(R$^{12}$), wherein C$_{1-6}$alkyl, C$_{2-6}$ alkenyl, C$_2$-calkynyl, C$_{3-10}$cycloalkyl, C$_2$-heterocycloalkyl, C$_{6-10}$aryl, and C$_1$-heteroaryl are optionally substituted with one, two, or three R$^{20}$%.

In some embodiments, R$^2$ is selected from —OR$^{12}$, —SR$^{12}$, —N(H)(R$^{12}$), and C$_{1-6}$alkyl optionally substituted with one, two, or three R$^{20b}$.

In some embodiments, R$^2$ is selected from

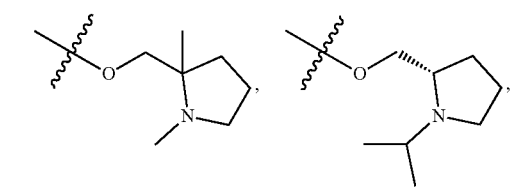

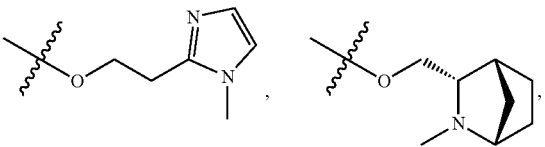

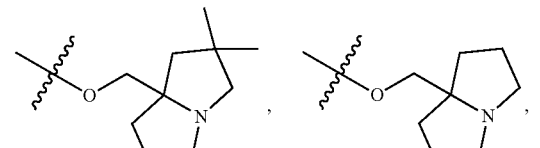

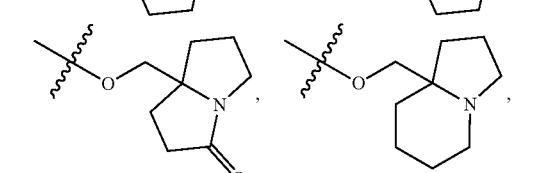

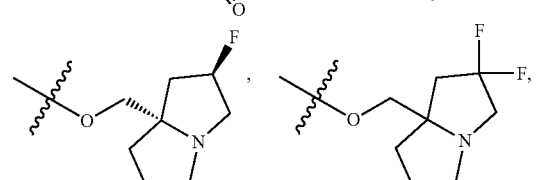

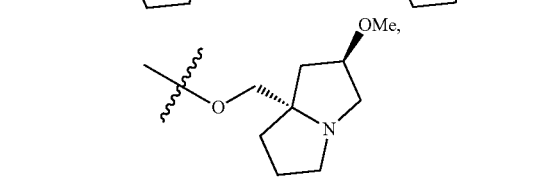

-continued

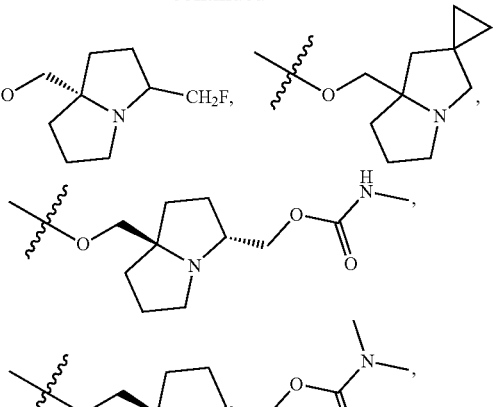

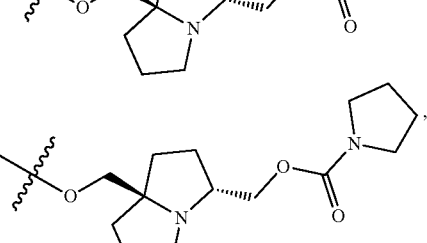

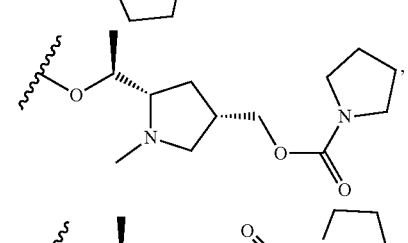

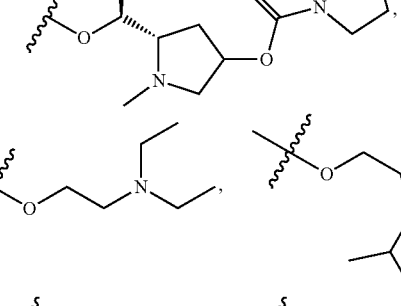

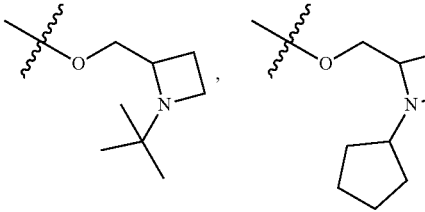

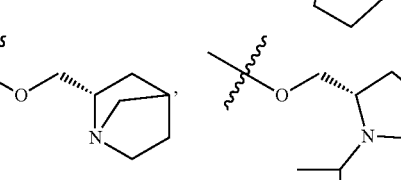

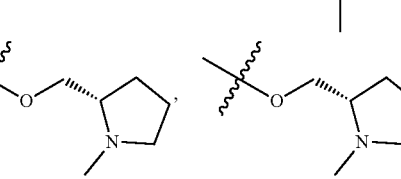

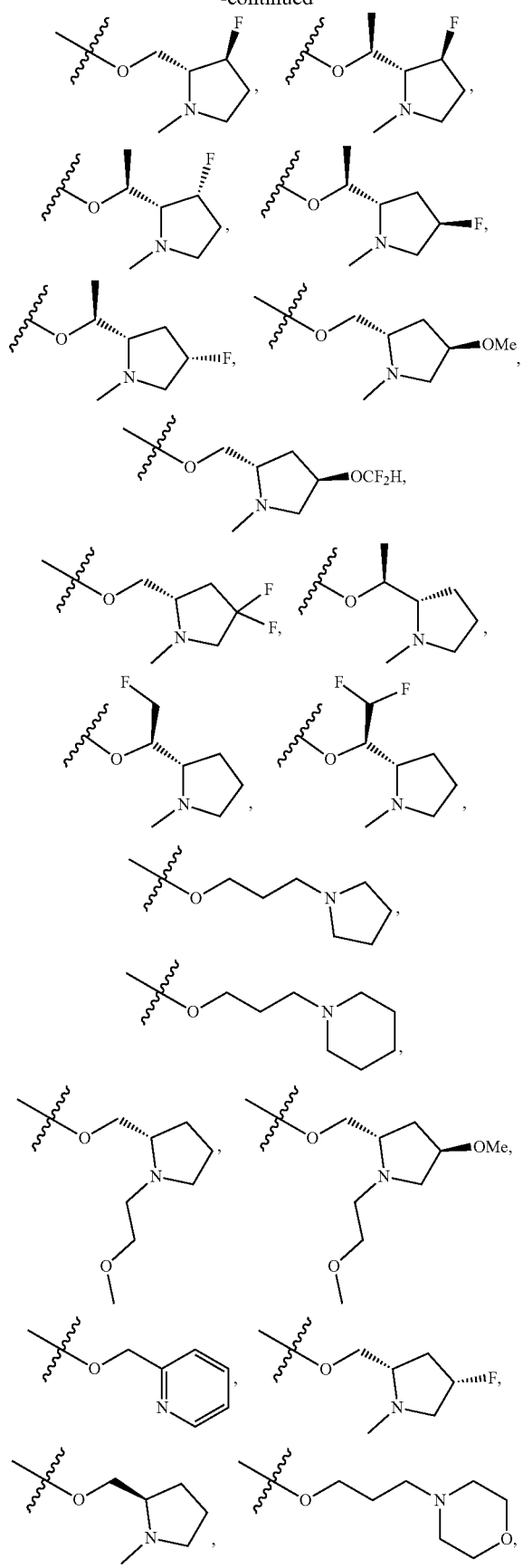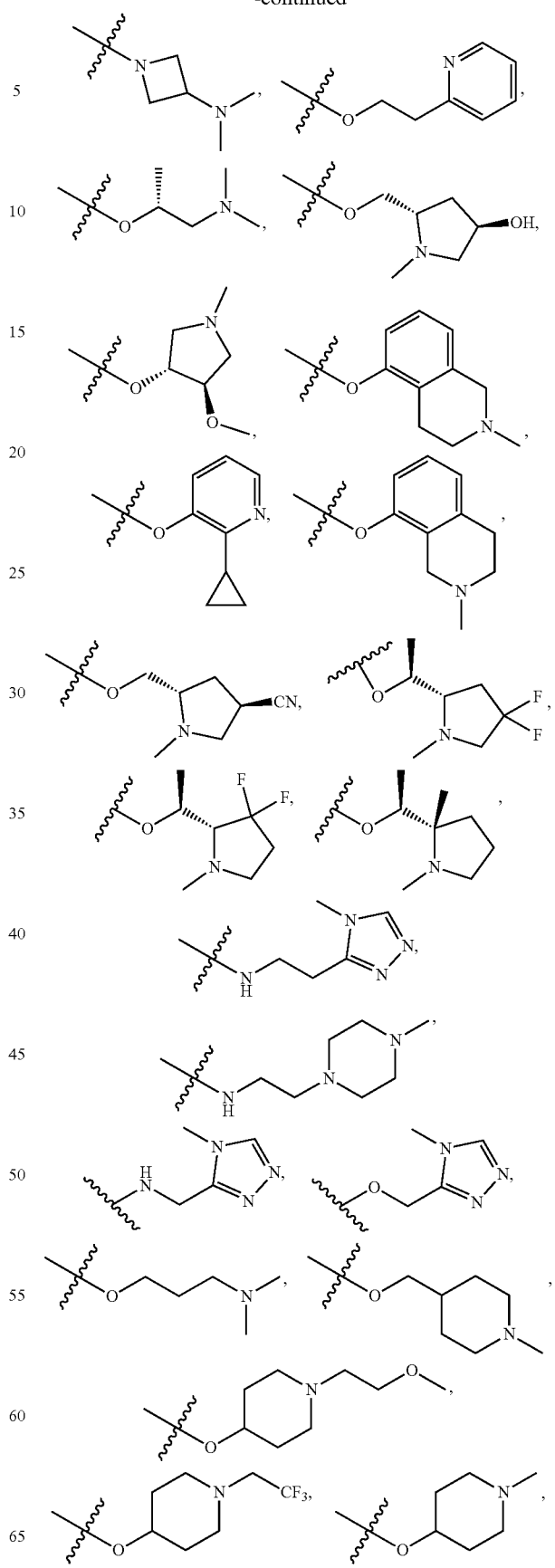

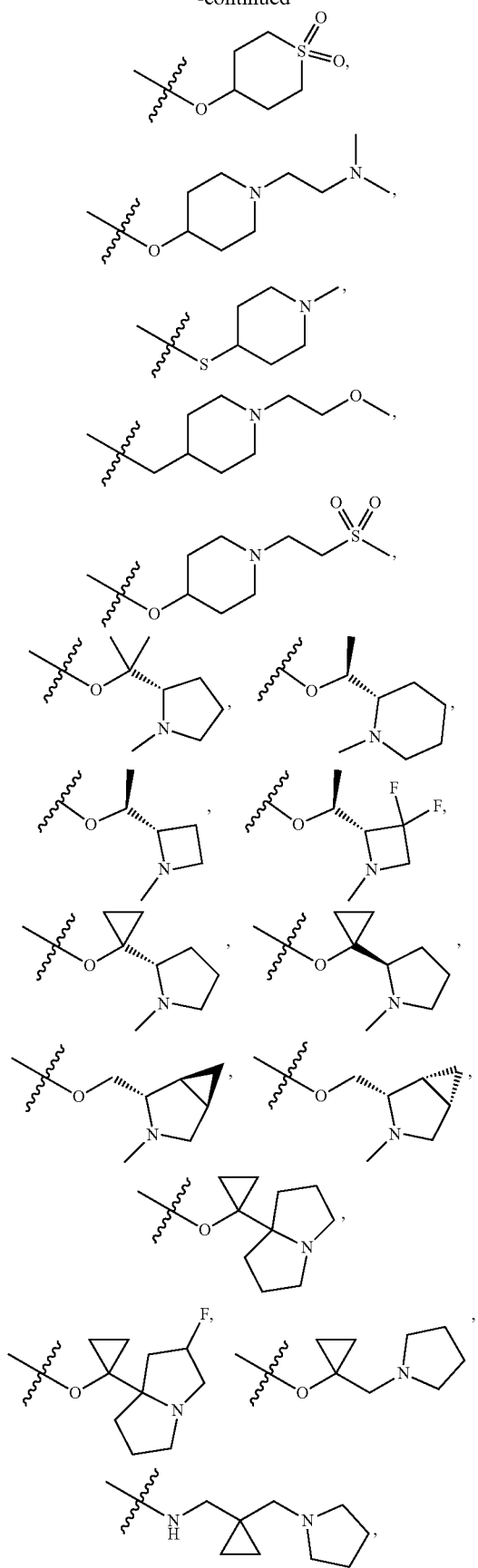
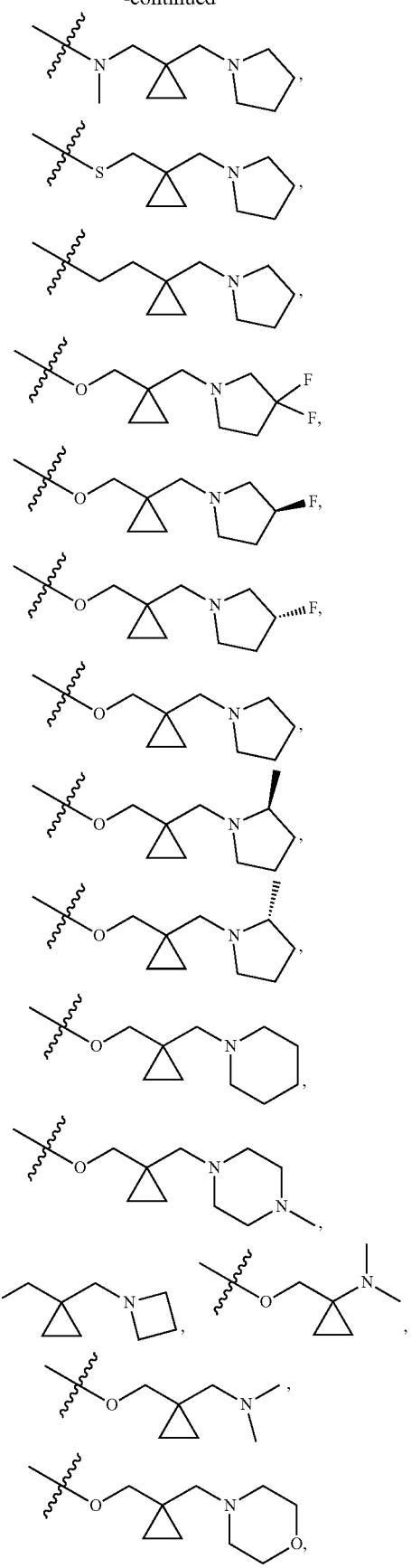

-continued

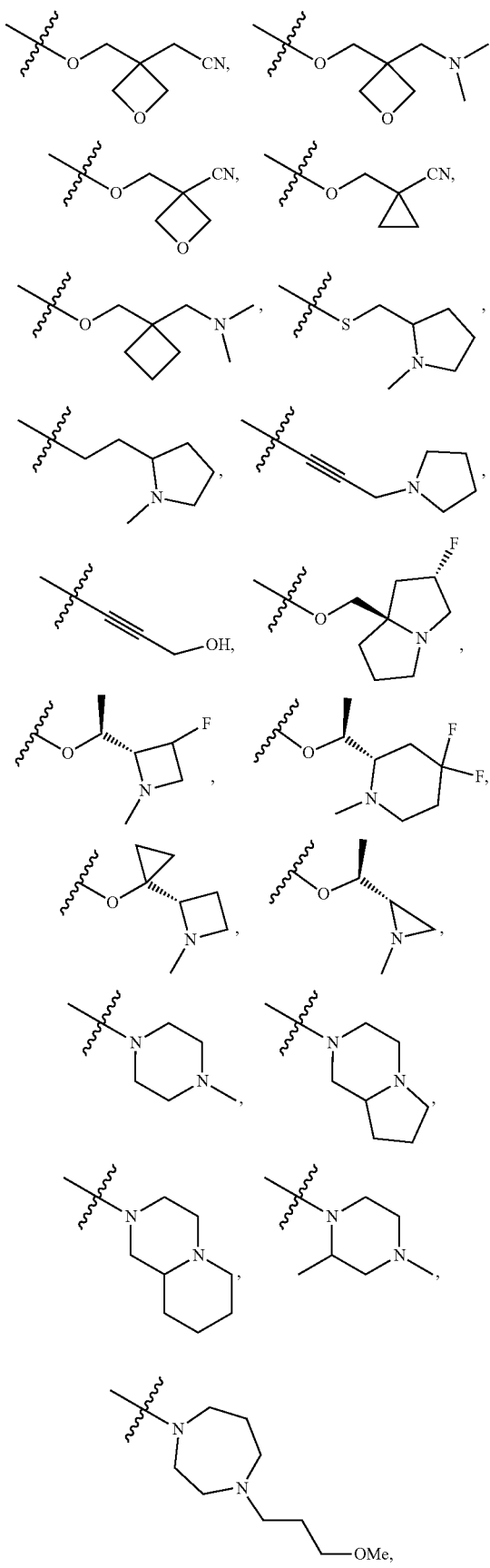

-continued

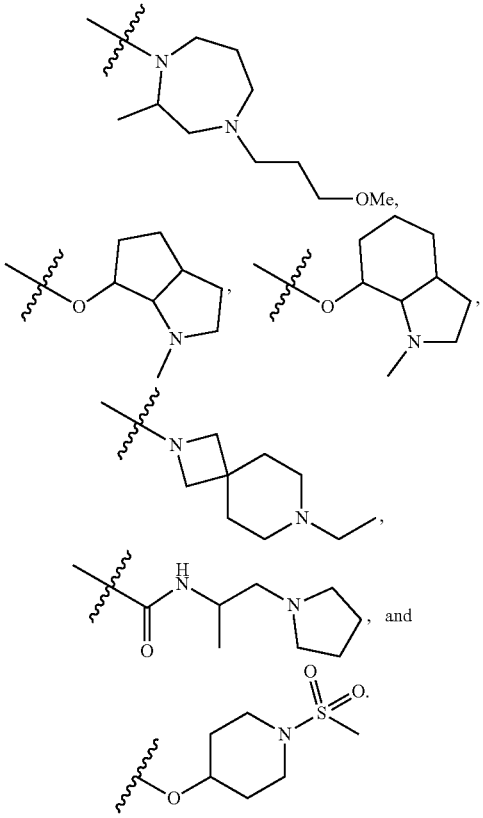

In some embodiments, $R^3$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20c}$. In some embodiments, $R^3$ is selected from hydrogen, halogen, —CN, $C_{1-6}$alkyl, and —$OR^{12}$, wherein $C_{1-6}$alkyl is optionally substituted with one, two, or three $R^{20}$c.

In some embodiments, $R^6$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20b}$. In some embodiments, $R^6$ is selected from hydrogen, halogen, —CN, $C_{1-6}$alkyl, and —$OR^{12}$, wherein $C_{1-6}$alkyl is optionally substituted with one, two, or three $R^{20c}$.

In some embodiments, $R^8$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20h}$.

In some embodiments, $R^8$ is selected from hydrogen, halogen, —CN, $C_{1-6}$alkyl, and —$OR^{12}$, wherein $C_{1-6}$alkyl is optionally substituted with one, two, or three $R^{20h}$.

In some embodiments, $Z^1$ is O, $Z^2$ is $CH_2$, $Z^3$ is $CH_2$, $Z^4$ is $CH_2$, and $Z^5$ is $N(R^4)$. In some embodiments, $Z^1$ is S, $Z^2$ is $CH_2$, $Z^3$ is $CH_2$, $Z^4$ is $CH_2$, and $Z^5$ is $N(R^4)$. In some embodiments, $Z^1$ is $N(H)$, $Z^2$ is $CH_2$, $Z^3$ is $CH_2$, $Z^4$ is $CH_2$, and $Z^5$ is $N(R^4)$. In some embodiments, $Z^1$ is $CH_2$, $Z^2$ is $CH_2$, $Z^3$ is $CH_2$, $Z^4$ is $CH_2$, and $Z^5$ is $N(R^4)$. In some embodiments, $Z^1$ is O, $Z^2$ is $CH_2$, $Z^3$ is $CH_2$, $Z^4$ is $C(R^4)(H)$, and $Z^5$ is O. In some embodiments, $Z^1$ is O, $Z^2$ is $CH_2$, $Z^3$ is $C(R^4)(H)$, $Z^4$ is $CH_2$, and $Z^5$ is O. In some embodiments, $Z^1$ is O, $Z^2$ is C($R^4$)(H), $Z^3$ is CH$_2$, $Z^4$ is CH$_2$, and $Z^5$ is O. In some embodiments, $Z^1$ is O, $Z^2$ is CH$_2$, $Z^3$ is CH$_2$, $Z^4$ is CH$_2$, and $Z^5$ is C($R^4$)(H). In some embodiments, $Z^1$ is O, $Z^2$ is CH$_2$, $Z^3$ is CH$_2$, $Z^4$ is C($R^4$)(H), and $Z^5$ is CH$_2$. In some embodiments, $Z^1$ is O, $Z^2$ is CH$_2$, $Z^3$ is C($R^4$)(H), $Z^4$ is CH$_2$, and $Z^5$ is CH$_2$. In some embodiments, $Z^1$ is O, $Z^2$ is C($R^4$)(H), $Z^3$ is CH$_2$, $Z^4$ is CH$_2$, and $Z^5$ is CH$_2$. In some embodiments, $Z^1$ is O, $Z^2$ is a bond, $Z^3$ is CH$_2$, $Z^4$ is a bond, and $Z^5$ is C($R^4$)(H). In some embodiments, $Z^1$ is O, $Z^2$ is a bond, $Z^3$ is C($R^4$)(H), $Z^4$ is a bond, and $Z^5$ is CH$_2$. In some embodiments, $Z^1$ is N(H), $Z^2$ is a bond, $Z^3$ is CH$_2$, $Z^4$ is a bond, and $Z^5$ is C($R^4$)(H). In some embodiments, $Z^1$ is N(H), $Z^2$ is a bond, $Z^3$ is C($R^4$)(H), $Z^4$ is a bond, and $Z^5$ is CH$_2$. In some embodiments, $Z^1$ is N($R^{11c}$), $Z^2$ is a bond, $Z^3$ is CH$_2$, $Z^4$ is a bond, and $Z^5$ is C($R^4$)(H). In some embodiments, $Z^1$ is N($R^{11c}$), $Z^2$ is a bond, $Z^3$ is C($R^4$)(H), $Z^4$ is a bond, and $Z^5$ is CH$_2$. In some embodiments, $Z^1$ is O, $Z^2$ is a bond, $Z^3$ is CH$_2$, $Z^4$ is a bond, and $Z^5$ is N($R^4$).

In some embodiments, $R^{4a}$ is C$_{3-10}$cycloalkyl optionally substituted with one, two, three, or four $R^{4b}$. In some embodiments, $R^{4a}$ is C$_{2-9}$heterocycloalkyl optionally substituted with one, two, three, or four $R^{4b}$. In some embodiments, $R^{4a}$ is C$_{6-10}$aryl optionally substituted with one, two, three, or four $R^{4b}$. In some embodiments, $R^{4a}$ is C$_{1-9}$heteroaryl optionally substituted with one, two, three, or four $R^{4b}$. In some embodiments, $R^{4a}$ is C$_{3-10}$cycloalkyl, C$_{2-9}$heterocycloalkyl, C$_{6-10}$aryl, or C$_{1-9}$heteroaryl optionally substituted with one, two, three, or four $R^{4b}$.

In some embodiments, $L^4$ is a bond, —O—, —N($R^{4d}$)—, —C(O)—, or CR$^{4c}$R$^{4c}$ In some embodiments, $L^4$ is a bond.

In an aspect is provided a compound having the formula A-L$^{Ab}$-B wherein

A is a monovalent form of a compound described herein;
L$^{AB}$ is a covalent linker bonded to A and B; and
B is a monovalent form of a degradation enhancer.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER$^5$, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR$^5$, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRLACRBN) ubiquitin ligase, XIAP, IAP, KEAP1, DCAF15, RNF114, DCAF16, AhR, SOCS2, KLHL12, UBR$^2$, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L$^3$, UBE2L$^6$, UBE2L$^1$, UBE2L$^2$, UBE2L$^4$, UBE2M, UBE2N, UBE2O, UBE2Q1, UBE2Q2, UBE2R$^1$, UBE2R$^2$, UBE2S, UBE2T, UBE2U, UBE2V1, UBE2V2, UBE2W, UBE2Z, ATG3, BIRC6, and UFC1.

In some embodiments, L$^{AB}$ is -L$^{AB1}$-L$^{AB2}$-L$^{AB}$3-L$^{AB4}$-L$^{AB5}$-;

L$^{AB1}$, L$^{AB2}$, L$^{AB3}$, L$^{AB4}$, and L$^{AB5}$ are independently a bond, —O—, —N($R^{14}$)—, —C(O)—, —N($R^{14}$)C(O)—, —C(O)N($R^{14}$)—, —S—, —S(O)$_2$—, —S(O)—, —S(O)$_2$N($R^{14}$)—, —S(O)N($R^{14}$)—, —N($R^{14}$)S(O)—, —N($R^{14}$)S(O)$_2$—, C$_{1-6}$alkylene, (—O—C$_{1-6}$alkyl)$_z$—, (—C$_{1-6}$alkyl-O)$_z$—, C$_{2-6}$alkenylene, C$_{2-6}$alkynylene, C$_{1-6}$haloalkylene, C$_{3-12}$cycloalkylene, C$_{1-11}$heterocycloalkylene, C$_{6-12}$arylene, or C$_{1-11}$heteroarylene, wherein C$_{1-6}$alkylene, C$_{2-6}$alkenylene, C$_{2-6}$alkynylene, C$_{1-6}$haloalkylene, C$_{3-12}$cycloalkylene, C$_{1-11}$heterocycloalkylene, C$_{6-12}$arylene, or C$_{1-11}$heteroarylene, are optionally substituted with one, two, or three $R^{20l}$, wherein each C$_{1-6}$alkyl of (—O—C$_{1-6}$alkyl), —and (—C$_{1-6}$alkyl-O)$_z$— is optionally substituted with one, two, or three $R^{20l}$;

z is independently an integer from 0 to 10;

each $R^{12}$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three $R^{20l}$;

each $R^{13}$ is independently selected from hydrogen, C$_{1-6}$alkyl, and C$_{1-6}$haloalkyl; or $R^{12}$ and $R^{13}$, together with the nitrogen to which they are attached, form a C$_{2-9}$heterocycloalkyl ring optionally substituted with one, two, or three $R^{20l}$;

each $R^{14}$ is independently selected from hydrogen, C$_{1-6}$alkyl, and C$_{1-6}$haloalkyl;

each $R^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20m}$;

each $R^{20l}$, $R^{20m}$, and $R^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH2C(O)OR$^{22}$, and —OC(O)R$^{25}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl; and each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_1$-heteroaryl.

In some embodiments, $L^{AB}$ is $-(O-C_2alkyl)_z-$ and z is an integer from 1 to 10.

In some embodiments, $L^{AB}$ is $-(C_2alkyl-O-)_z-$ and z is an integer from 1 to 10.

In some embodiments, $L^{AB}$ is $-(CH_2)_{zz1}L^{AB2}(CH_2O)_{zz2}-$, wherein $L^{AB2}$ is a bond, a 5 or 6 membered heterocycloalkylene or heteroarylene, phenylene, $-(C_2-C_4)$alkynylene, $-SO_2$- or $-NH-$; and $zz^1$ and $zz^2$ are independently an integer from 0 to 10.

In some embodiments, $L^{AB}$ is $-(CH_2)_{zz1}(CH_2O)_{zz2}-$, wherein $zz^1$ and $zz^2$ are each independently an integer from 0 to 10.

In some embodiments, $L^{AB}$ is a PEG linker.

In some embodiments, B is a monovalent form of a compound selected from

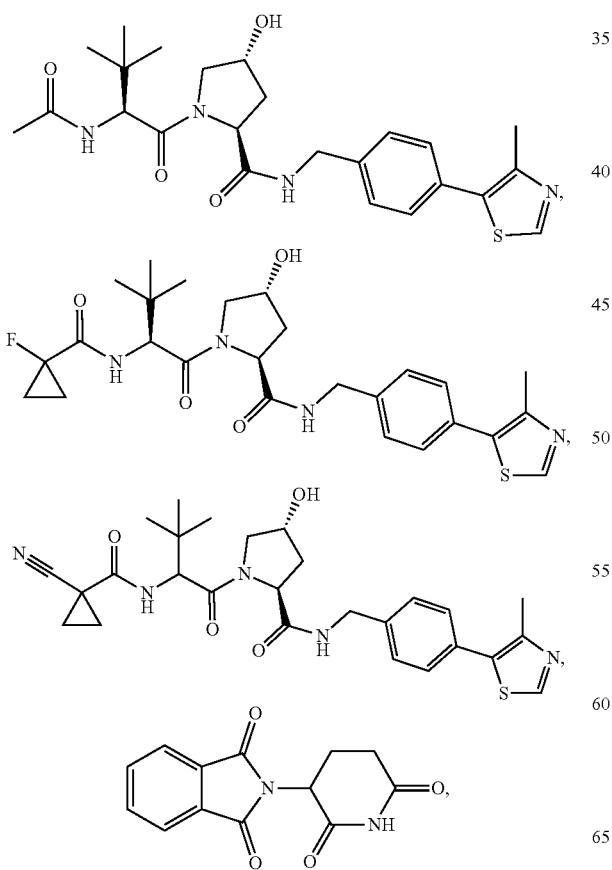

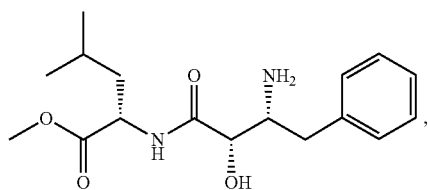

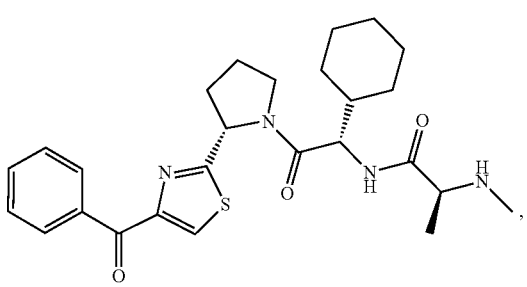

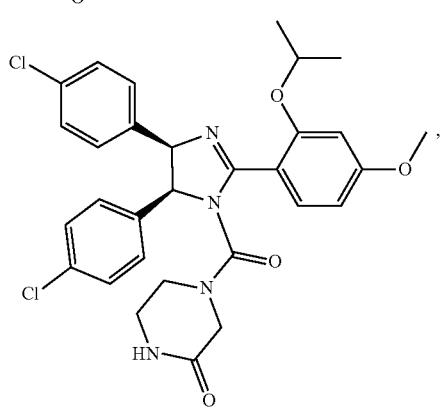

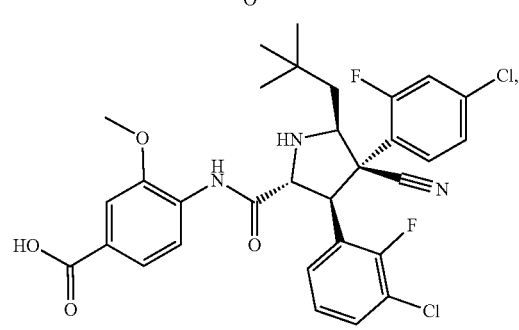

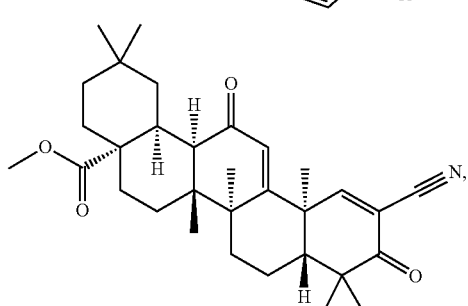

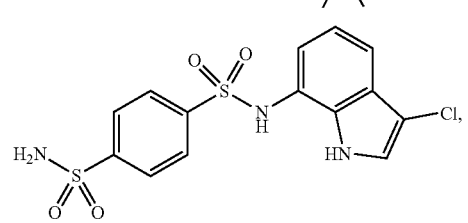

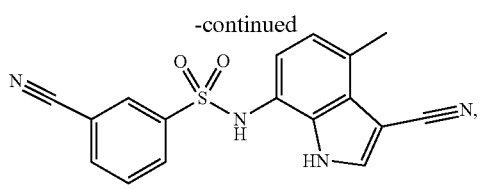

In an aspect is provided a pharmaceutical composition comprising a compound described herein, or a pharmaceutically acceptable salt or solvate thereof, and a pharmaceutically acceptable excipient.

In an aspect is provided a method of treating cancer in a subject in need thereof, comprising administering to the subject a therapeutically effective amount of a compound described herein, or a pharmaceutically acceptable salt or solvate thereof.

In an aspect is provided a method of treating cancer in a subject comprising a Ras mutant protein, the method comprising: inhibiting the Ras mutant protein of said subject by administering to said subject a compound, wherein compound is characterized in that upon contacting the Ras mutant protein, said Ras mutant protein exhibits reduced Ras signaling output.

In some embodiments, the cancer is a solid tumor. In some embodiments, the cancer is a hematological cancer.

In some embodiments of a method described herein, the compound is a compound described herein.

In an aspect is provided a method of modulating signaling output of a Ras protein, comprising contacting a Ras protein with an effective amount of a compound described herein, or a pharmaceutically acceptable salt or solvate thereof, thereby modulating the signaling output of the Ras protein.

In an aspect is provided a method of inhibiting cell growth, comprising administering an effective amount of a compound described herein, or a pharmaceutically acceptable salt or solvate thereof, to a cell expressing a Ras protein, thereby inhibiting growth of said cells.

In some embodiments of the methods described herein, the method comprises administering an additional agent.

In some embodiments, the additional agent comprises (1) an inhibitor of MEK; (2) an inhibitor of epidermal growth factor receptor (EGFR) and/or of mutants thereof; (3) an immunotherapeutic agent; (4) a taxane; (5) an anti-metabolite; (6) an inhibitor of FGFR1 and/or FGFR2 and/or FGFR3 and/or of mutants thereof; (7) a mitotic kinase inhibitor; (8) an anti-angiogenic drug; (9) a topoisomerase inhibitor; (10) a platinum-containing compound; (12) an inhibitor of c-MET and/or of mutants thereof; (13) an inhibitor of BCR-ABL and/or of mutants thereof; (14) an inhibitor of ErbB2 (Her2) and/or of mutants thereof; (15) an inhibitor of AXL and/or of mutants thereof; (16) an inhibitor of NTRK1 and/or of mutants thereof; (17) an inhibitor of RET and/or of mutants thereof; (18) an inhibitor of A-Raf and/or B-Raf and/or C-Raf and/or of mutants thereof; (19) an inhibitor of ERK and/or of mutants thereof; (20) an MDM2 inhibitor; (21) an inhibitor of mTOR; (23) an inhibitor of IGF1/2 and/or of IGF1-R; (24) an inhibitor of CDK9; (25) an inhibitor of farnesyl transferase; (26) an inhibitor of SHIP pathway; (27) an inhibitor of SRC; (28) an inhibitor of JAK; (29) a PARP inhibitor, (31) a ROS1 inhibitor; (32) an inhibitor of SHP pathway, or (33) an inhibitor of Src, FLT3, HDAC, VEGFR, PDGFR, LCK, Bcr-Abl or AKT; (34) an inhibitor of KrasG12C mutant; (35) a SHC inhibitor (e.g., PP2, AID371185); (36) a GAB inhibitor; (38) a PI-3 kinase inhibitor; (39) a MARPK inhibitor; (40) CDK4/6 inhibitor; (41) MAPK inhibitor; (42) SHP2 inhibitor; (43) checkpoint immune blockade agents; (44) or SOS1 inhibitor; or (45) a SOS 2 inhibitor.

In some embodiments, the additional agent comprises an inhibitor of SHP2 selected from RMC-4630, ERAS-601,

TNO155

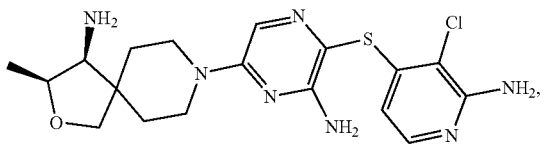

JAB-3068

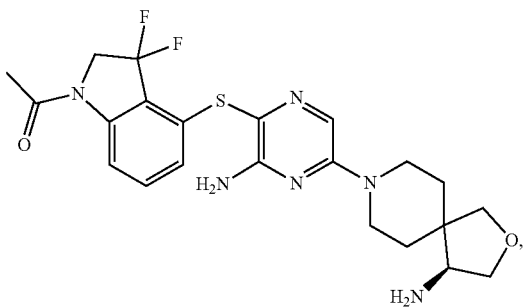

IACS-13909/BBP-398

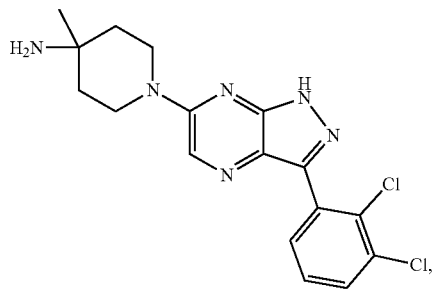

SHP099

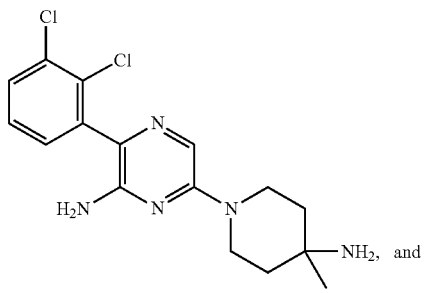

In embodiments, the additional agent comprises an inhibitor of SOS selected from

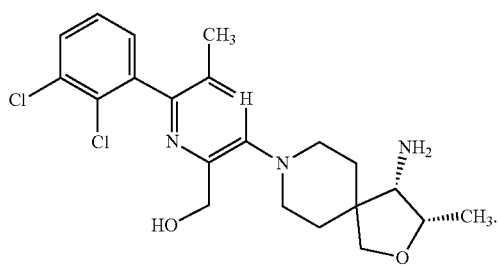
BI-3406

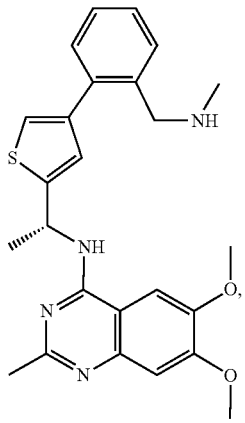
MRTX0902

BAY 293

RMC-5845, and BI-1701963.

In some embodiments, the additional agent comprises an inhibitor of EGFR selected from afatinib, erlotinib, gefitinib, lapatinib, cetuximab panitumumab, osimertinib, olmutinib, and EGF-816. In some embodiments, the additional agent comprises an inhibitor of MEK selected from trametinib, cobimetinib, binimetinib, selumetinib, refametinib, and AZD6244. In some embodiments, the additional agent comprises an inhibitor of ERK selected from ulixertinib, MK-8353, LTT462, AZD0364, SCH772984, BIX02189, LY3214996, and ravoxertinib. In some embodiments, the additional agent comprises an inhibitor of CDK4/6 selected from palbociclib, ribociclib, and abemaciclib. In some embodiments, the additional agent comprises an inhibitor of BRAF selected from sorafenib, vemurafenib, dabrafenib, encorafenib, regorafenib, and GDC-879.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a sequence alignment of various wild type Ras proteins including K-Ras, H-Ras, N-Ras, RalA, and RalB, from top to bottom.

DETAILED DESCRIPTION

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR²: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . . $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 18, 1 to 12, 1 to 10, 1 to 8, or 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. In some embodiments, an alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, —C≡CCH$_3$, —C≡CCH$_2$CH$_3$ and —C≡CCH$_2$CH$_2$CH$_3$. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to a monocyclic aromatic ring wherein each of the atoms forming the ring is a carbon atom (e.g., phenyl) or a polycyclic ring system (e.g., bicyclic or tricyclic) wherein 1) at least one ring is carbocyclic and aromatic, 2) a bond to the remainder of the compound is directly bonded to a carbocyclic aromatic ring of the aryl ring system, and 3) the carbocyclic aromatic ring of the aryl ring system of 2) is not directly bonded (e.g., fused) to a heteroaryl ring in the polycyclic ring system. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group). As used herein, the aryl radical is a monocyclic, bicyclic, or tricyclic ring system. In embodiments, an aryl is a monocyclic ring. In embodiments, an aryl is a fused ring polycyclic system. In embodiments, an aryl is a bridged ring polycyclic system. In some embodiments the aryl is a "fused ring aryl" wherein the aryl ring is fused with a cycloalkyl or a heterocycloalkyl ring. In embodiments, an aryl is a "fused bicyclic" aryl wherein the two rings of the aryl group share one bond.

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

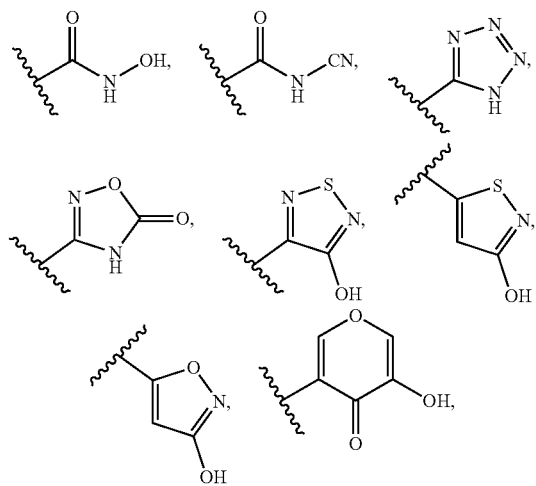

and the like.

The term "cycloalkyl" refers to a monocyclic carbocyclic saturated or partially unsaturated non-aromatic ring or a polycyclic carbocyclic (i.e., does not include heteroatom(s)) ring system (e.g., bicyclic or tricyclic) wherein 1) at least one ring is carbocyclic saturated or partially unsaturated and non-aromatic, 2) a bond to the remainder of the compound is directly bonded to a carbocyclic saturated or partially unsaturated non-aromatic ring of the ring system, and 3) the carbocyclic saturated or partially unsaturated non-aromatic ring of the ring system of 2) is not directly bonded (e.g., fused or spirocyclic) to a heterocycloalkyl ring in the polycyclic ring system. Cycloalkyls may be saturated or partially unsaturated. In some embodiments, a cycloalkyl ring is a spirocyclic cycloalkyl ring. In embodiments, a cycloalkyl is a monocyclic ring. In embodiments, a cycloalkyl is a fused ring polycyclic system. In embodiments, a cycloalkyl is a bridged ring polycyclic system. In embodiments, a cycloalkyl is a spirocyclic polycyclic ring system. In some embodiments, cycloalkyl groups include groups having from 3 to 10 ring atoms. Depending on the structure, a cycloalkyl group can be a monoradical or a diradical (i.e., a cycloalkylene group). In embodiments, a cycloalkyl is a "fused bicyclic" cycloalkyl wherein the two rings of the cycloalkyl group share one bond.

The terms "heteroaryl" or, alternatively, "heteroaromatic" refers to an monocyclic aryl group that includes one or more ring heteroatoms selected from nitrogen, oxygen and sulfur; or a polycyclic ring system (e.g., bicyclic or tricyclic) wherein 1) at least one ring is aromatic and includes one or more heteroatoms selected from nitrogen, oxygen and sulfur and 2) a bond to the remainder of the compound is directly bonded to an aromatic ring including one or more heteroatoms selected from nitrogen, oxygen and sulfur or an aromatic ring directly bonded (e.g., fused) to an aromatic ring including one or more heteroatoms selected from nitrogen, oxygen and sulfur, of the aryl ring system. As used herein, the heteroaryl radical may be a monocyclic, bicyclic, or tricyclic ring system, wherein at least one of the rings in the ring system is fully unsaturated (i.e., aromatic) and includes a heteroatom. In embodiments, a heteroaryl is a monocyclic ring. In embodiments, a heteroaryl is a fused ring polycyclic system. In embodiments, a heteroaryl is a bridged ring polycyclic system. In some embodiments is a "fused ring heteroaryl" wherein the heteroaryl ring is fused with a cycloalkyl, aryl, or heterocycloalkyl ring. An N-containing "heteroaromatic" or "heteroaryl" moiety refers to an aromatic group in which at least one of the skeletal atoms of the ring is a nitrogen atom. Depending on the structure, a heteroaryl group can be a monoradical or a diradical (i.e., a heteroarylene group). In embodiments, a heteroaryl is a "fused bicyclic" heteroaryl wherein the two rings of the heteroaryl group share one bond.

A "heterocycloalkyl" group or "heteroalicyclic" group refers to a cycloalkyl group, wherein at least one skeletal ring atom of a saturated or partially unsaturated non-aromatic ring is a heteroatom selected from nitrogen, oxygen, phosphorus, and sulfur. A heterocycloalkyl refers to a monocyclic saturated or partially unsaturated non-aromatic ring including one or more heteroatoms or a polycyclic ring system (e.g., bicyclic or tricyclic) wherein 1) at least one ring is saturated or partially unsaturated, non-aromatic, and includes one or more heteroatoms and 2) a bond to the remainder of the compound is directly bonded to a ring of the ring system that is a saturated or partially unsaturated and non-aromatic ring that includes one or more heteroatoms or a non-aromatic ring directly bonded (e.g., fused, spiro) to a saturated or partially unsaturated and non-aromatic ring that includes one or more heteroatoms of the ring system. Heterocycloalkyls may be saturated or partially unsaturated. The term heterocycloalkyl also includes all ring forms of the carbohydrates, including but not limited to the monosaccharides, the disaccharides and the oligosaccharides. In some embodiments, a heterocycloalkyl ring is a spirocyclic heterocycloalkyl ring. In embodiments, a heterocycloalkyl is a monocyclic ring. In embodiments, a heterocycloalkyl is a fused ring polycyclic system. In embodiments, a heterocycloalkyl is a bridged ring polycyclic system. In embodiments, a heterocycloalkyl is a spirocyclic polycyclic ring system. Unless otherwise noted, heterocycloalkyls have from 2 to 13 carbons in the ring or ring system. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Depending on the structure, a heterocycloalkyl group can be a monoradical or a diradical (i.e., a heterocycloalkylene group). In embodiments, a heterocycloalkyl is a "fused bicyclic" heterocycloalkyl wherein the two rings of the heterocycloalkyl group share one bond.

The term "halo" or, alternatively, "halogen" means fluoro, chloro, bromo and iodo.

The abbreviations "Fmoc", "Ac", "Bn", "PMB", "Tr", "Ts", "Boc", and "Cbz" are used in accordance with their well understood common meanings in Chemistry and mean the monovalent chemical substituents fluorenylmethyloxycarbonyl, acetyl, benzyl, p-methoxybenzyl, trityl or triphenylmethyl, tosyl, tert-butyloxycarbonyl, and carbobenzyloxy, respectively. The term "monovalent" is used herein in accordance with its well understood meaning in Chemistry and refers to the ability of a substituent to form one covalent bond with another substituent or compound capable of forming a covalent bond. In a related manner, the term "divalent" refers to a substituent or compound capable of forming two covalent bonds, for example a linker capable of covalently connecting two monovalent substituents or compounds.

The term "haloalkyl" refers to an alkyl group that is substituted with one or more halogens. The halogens may the same or they may be different. Non-limiting examples of haloalkyls include —CH$_2$Cl, —CF$_3$, —CHF$_2$, —CH$_2$CF$_3$, —CF$_2$CF$_3$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH═N—OCH$_3$, and —CH═CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "heteroalkylene linker" refers to a divalent alkyl radical where one or more skeletal chain atoms is selected from an atom other than carbon, e.g., oxygen, nitrogen, sulfur, phosphorus, silicon, or combinations thereof. In some embodiments, the heteroatom(s) may be placed at any interior position of the heteroalkyl group. In some embodiments, the heteroatom(s) may be placed at one or both terminal positions of the heteroalkylene linker (i.e., position (s) directly bonded to portion(s) of the molecule other than the heteroalkylene linker). Examples include, but are not limited to, —CH$_2$—O—CH$_2$—, —CH$_2$—CH$_2$—O—CH$_2$—, —CH$_2$—NH—CH$_2$—, —CH$_2$—CH$_2$—NH—CH$_2$—, —CH$_2$—N(CH$_3$)—CH$_2$—, —CH$_2$—CH$_2$—N(CH$_3$)—CH$_2$—, —CH$_2$—S—CH$_2$—CH$_2$—, —CH$_2$—CH$_2$—S(O)—CH$_2$—, —CH$_2$—CH$_2$—S(O)$_2$—CH$_2$—, —CH$_2$—NH—O—CH$_2$—, —CH$_2$—O—Si(CH$_3$)$_2$—, —CH$_2$—CH═N—O—CH$_2$—, and —CH—CH—N(CH$_3$)—CH$_2$—. Examples include, but are not limited to, —CH$_2$—O—, —CH$_2$—CH$_2$—O—, —CH$_2$—NH—, —CH$_2$—CH$_2$—NH—, —CH$_2$—N(CH$_3$)—, —CH$_2$—CH$_2$—N(CH$_3$)—, —CH$_2$—S—, —CH$_2$—CH$_2$—S—, —CH$_2$—CH$_2$—S(O)—, —CH$_2$—CH$_2$—S(O)$_2$—, —CH$_2$—S(O)—, —CH$_2$—S(O)$_2$—, —CH$_2$—CH$_2$—S(O)—, —CH$_2$—CH$_2$—CH$_2$—S(O)$_2$—, —CH$_2$—CH$_2$—CH$_2$—O—, —CH$_2$—CH$_2$—CH$_2$—O—, —CH$_2$—CH$_2$—CH$_2$—S—, —CH$_2$—CH$_2$—CH$_2$—S—, —CH$_2$—CH$_2$—CH$_2$—NH—, —CH$_2$—CH$_2$—CH$_2$—NH—, —CH$_2$—CH$_2$—CH$_2$—N(CH$_3$)—, —CH$_2$—CH$_2$—CH$_2$—N(CH$_3$)—, —CH$_2$—NH—O—, —O—Si(CH$_3$)$_2$—, —CH$_2$—CH═N—O—, and —CH—CH—N(CH$_3$)—. Examples include, but are not limited to, —O—CH$_2$—, —O—CH$_2$—CH$_2$—, —NH—CH$_2$—, —NH—CH$_2$—CH$_2$—, —N(CH$_3$)—CH$_2$—, —N(CH$_3$)—CH$_2$—CH$_2$—, —S—CH$_2$—, —S—CH$_2$—CH$_2$—, —S(O)—CH$_2$—CH$_2$—, —S(O)$_2$—CH$_2$—CH$_2$—, —S(O)—CH$_2$—, —S(O)$_2$—CH$_2$—, —S(O)—CH$_2$—CH$_2$—CH$_2$—, —S(O)$_2$—CH$_2$—CH$_2$—CH$_2$—, —O—CH$_2$—CH$_2$—CH$_2$—, —O—CH$_2$—CH$_2$—CH$_2$—, —S—CH$_2$—CH$_2$—CH$_2$—, —S—CH$_2$—CH$_2$—CH$_2$—, —NH—CH$_2$—CH$_2$—CH$_2$—, —NH—CH$_2$—CH$_2$—CH$_2$—, —N(CH$_3$)—CH$_2$—CH$_2$—, —N(CH$_3$)—CH$_2$—CH$_2$—CH$_2$—, —O—NH—CH$_2$—, —Si(CH$_3$)$_2$—O—, —O—N═CH—CH$_2$—, and —N(CH$_3$)—CH═CH—. In addition, up to two heteroatoms may be consecutive, such as, by way of example, —CH$_2$—NH—O— and —O—Si(CH$_3$)$_2$—. Examples include, but are not limited to, —P(O)(CH$_3$)—CH$_2$—, —P(O)(CH$_3$)—CH$_2$—CH$_2$—, —P(O)(CH$_3$)—CH$_2$—CH$_2$—CH$_2$—, —CH$_2$—P(O)(CH$_3$)—, —CH$_2$—CH$_2$—P(O)(CH$_3$)—, and —CH$_2$—CH$_2$—CH$_2$—P(O)(CH$_3$)—. In addition, up to two heteroatoms may be consecutive, such as, by way of example, —CH$_2$—NH—O— and —O—Si(CH$_3$)$_2$—. A "heteroalkylene linker" may have from 2 to 4 main chain atoms unless specified otherwise.

The term "oxo" refers to the ═O radical.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

The suffix "-di-yl" will be understood to mean the substituent or linker is a divalent substituent or linker.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means, unless otherwise specified, that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N®$_2$), and the protected derivatives thereof. By way of example, an optional substituents may be $L^S R^S$, wherein each $L^S$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^8$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "agent" or "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

The term "in vivo" refers to an event that takes place in a subject's body.

The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (also used interchangeably herein as K-Ras, K-ras, Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof. The terms "mutant Ras" and "Ras mutant," as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, 96, or any combination thereof of Ras of SEQ ID No. 2 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

As used herein, the term "corresponding to" or "corresponds to" as applied to an amino acid residue in a polypeptide sequence refers to the correspondence of such amino acid relative to a reference sequence when optimally aligned (e.g., taking into consideration of gaps, insertions and mismatches; wherein alignment may be primary sequence alignment or three dimensional structural alignment of the folded proteins). For instance, the serine residue in a Ras G12S mutant refers to the serine corresponding to residue 12 of SEQ ID No. 4, which can serve as a reference sequence). For instance, the aspartate residue in a Ras G12D mutant refers to the aspartate corresponding to residue 12 of SEQ ID No. 2, which can serve as a reference sequence. When an amino acid of a mutant Ras protein corresponds to an amino acid position in the WT Ras protein, it will be understood that although the mutant Ras protein amino acid may be a different amino acid (e.g., G12D wherein the wildtype G at position 12 is replaced by an aspartate at position 12 of SEQ ID. No. 1), the mutant amino acid is at the position corresponding to the wildtype amino acid (e.g., of SEQ ID No. 1). In embodiments, a modified Ras mutant protein disclosed herein may comprise truncations at C-terminus, or truncations at the N-terminal end preceding the serine residue. The serine residue in such N-terminal truncated modified mutant is still considered corresponding to position 12 of SEQ ID No. 1. In addition, the aspartate residue at position 12 of SEQ ID No. 2 finds a corresponding residue in SEQ ID Nos. 6 and 8.

"Prodrug" as used herein is meant to indicate a compound that may be converted under physiological conditions or by solvolysis to a biologically active compound described herein. The term "prodrug" refers to a precursor of a biologically active compound that is pharmaceutically acceptable. A prodrug may be inactive when administered to a subject, but is converted in vivo to an active compound, for example, by hydrolysis. The prodrug compound may offer advantages of solubility, tissue compatibility and/or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. A "prodrug" can be any covalently bonded carriers, that release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound.

The term "leaving group" is used herein in accordance with its well understood meaning in Chemistry and refers to an atom or group of atoms which breaks away from the rest of the molecule, taking with it the electron pair which used to be the bond between the leaving group and the rest of the molecule.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In embodiments, the degradation enhancer is capable of binding to an E3 ubiquitin ligase protein or a protein complex comprising an E3 ubiquitin ligase protein. In embodiments, the degradation enhancer is capable of binding to an E2 ubiquitin-conjugating enzyme. In embodiments, the degradation enhancer is capable of binding to a protein complex comprising an E2 ubiquitin-conjugating enzyme and an E3 ubiquitin ligase protein.

Compounds

In some embodiments is provided a compound of Formula (I), or a pharmaceutically acceptable salt or solvate thereof:

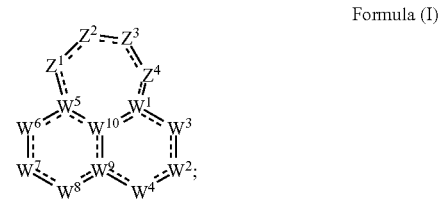

Formula (I)

wherein:

$Z^1$, $Z^2$, $Z^3$, and $Z^4$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O); wherein at least one of $Z^1$, $Z^2$, $Z^3$, and $Z^4$ is $N(R^4)$, $N(R^{11d})$, $C(R^4)$, $C(R^{11d})$, $C(R^4)(R^{11c})$, $C(R^4)(R^4)$, $C(R^{11c})(R^{11d})$, or C(O);

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $N(R^{2a})$, N, $C(R^2)$, $C(R^2)(R^{2a})$, $S(O)_2$, or $S(O)$;

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$R^{2a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N$ $(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$, $W^3$ is $N(R^{3b})$, N, $C(R^3)$, $C(R^3)(R^{3a})$, C(O), $S(O)_2$, or S(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_1$-heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is N or $N(R^{3c})$;

$R^{3c}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, C(O), S(O), or $S(O)_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, and -$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$R^{8b}$ is selected from hydrogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^7$ is $N(R^7)$, $C(R^7)$, or $C(R^7)(R^{7a})$;

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three $R^{20f}$;

$R^7$ is -$L^7$-$R^{17}$;

$L^7$ is a bond, —O—, —$N(R^{7d})$—, —C(O)—, —S—, —$S(O)_2$—, —S(O)—, —$P(O)R^{7d}$—, $CR^7R^{7c}$, —$OCR^7R^{7c}$—, —$N(R^{7d})CR^7R^{7c}$—, —C(O)$CR^{7c}R^{7c}$—, —$SCR^7CR^{7c}$, —$S(O)_2CR^{7c}R^{7c}$—, —$S(O)CR^{7c}R^{7c}$—, —$P(O)R^{7d}CR^7CR^{7c}$—, —$CR^7R^7\&CR^7CR^7$—, —$CR^7RICO$—, —$CR^7CR^7CN(R^{7d})$—, —$CR^{7c}R^{7c}C(O)$—, —$CR^7CR^{7c}S$—, —$CR^7CR^{7c}S(O)_2$—, —$CR^7CR^{7c}S(O)$—, —$CR^{7c}R^7cP(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7d}N(R^{7d})$—, —OC(O)—, —$OS(O)_2$—, —OS(O)—, —$OP(O)R^{7d}$—, —C(O)O—, —$S(O)_2O$—, —S(O)O—, or —$P(O)R^{7d}O$—;

$R^{17}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$W^8$ is $C(R^8)$, $C(R^8)(R^{8a})$, N, $N(R^{8b})$, $C(O)$, $S(O)$, or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $W^9$ is $C(R^9)$, C, or N;

$W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$, $R^4$ is -$L^4$-$R^{4a}$, $L^4$ is a bond, —O—, —$N(R^{4d})$—, —$C(O)$—, —S—, —$S(O)_2$—, —$S(O)$—, —$P(O)R^{4d}$—, —$CR^4R^4$—, —$OCR^4R^4$—, —$N(R^{4d})CR^{4c}R^{4c}$—, —$C(O)CR^4R^{4c}$—, —$SCR^4R^4$—, —$S(O)_2CR^4R^{4c}$—, —$S(O)CR^4R^{4c}$—, —$P(O)R^{4d}CR^4R^{4c}$—, —$CR^4R^4CR^{4c}R^{4c}$—, —$CR^{4c}R^{4c}O$—, —$CR^4R^4CN(R^{4d})$—, —$CR^{4c}R^{4c}CC(O)$—, —$CR^4R*S$—, —$CR^4R^{4c}S(O)_2$—, —$CR^{4c}R^{4c}S(O)$—, —$CR^{4c}R^4P(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^{4d}N(R^{4d})$—, —$OC(O)$—, —$OS(O)_2$—, —$OS(O)$—, —$OP(O)R^{4d}$—, —$C(O)O$—, —$S(O)_{20}$—, —$S(O)O$—, or —$P(O)R^{4d}O$—;

each $R^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH_2C(O)OR^{14}$, —$OC(O)R^{14}a$, —$N(R^{14})(R^{14})$, —$N(R^{14})C(O)N(R^{14})$, —$N(R^{14})C(O)OR^{14}$, —$N(R^{14})C(O)R^{14a}$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_1$-haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH_2C(O)OR^{14}$, and —$OC(O)R^{14}$a, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$; —$S(O)_2R^{14}$, —$S(O)_2N(R^{14})(R^{14})$, and —$OC(O)R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(0)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-

$C_{3-12}$cycloalkyl, $C_1$-11heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl are optionally substituted with one, two, or three $R^{20l}$;

$R^{12a}$ is selected from $C_{1-6}$alkyl, $C_{2-6}$alkenyl, $C_{2-6}$alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl, wherein $C_{1-6}$alkyl, $C_{2-6}$alkenyl, $C_2$-6alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_6$- 10aryl, —$C(R^{12b})_2$-$C_{1-9}$heteroaryl, and $C_{1-9}$heteroaryl are optionally substituted with one, two, or three $R^{20l}$; each $R^{12b}$ is independently selected from hydrogen and $R^{20l}$; each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{14}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$; $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_3$-10cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments, the compound of Formula (I) has the structure of Formula (Ia), or a pharmaceutically acceptable salt or solvate thereof:

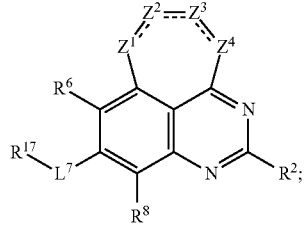

Formula (Ia)

wherein: $Z^1$, $Z^2$, $Z^3$, $Z^4$, $R^2$, $R^6$, RIC, $R^{7d}$, $L^7$, $R^{17}$, $R^8$, $R^4$, $L^4$, $R^{4c}$, $R^{4a}$, $R^{48}$, $R^{4b}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20c}$, $R^{20f}$, $R^{20g}$, $R^{20h}$, $R^{20j}$, $R^{20g}$, $R^{20l}$, $R^{20m}$, $R^{21}$, $R^{22}$, $R^{23}$, $R^{24}$, and $R^{25}$ are as described for Formula (I), including in embodiments of a compound of Formula (I); and ----- indicates a single or double bond such that all valences are satisfied.

In some embodiments, the compound of Formula (I) has the structure of Formula (Ib), or a pharmaceutically acceptable salt or solvate thereof:

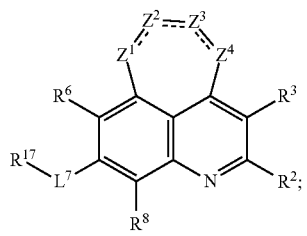

Formula (Ib)

wherein: $Z^1$, $Z^2$, $Z^3$, $Z^4$, $R^2$, $R^3$, $R^6$, $R^{7c}$, $R^{7d}$, $L^7$, $R^{17}$, $R^8$, $R^4$, $L^4$, $R^{4c}$, $R^{4d}$, $R^{4a}$, $R^{4b}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20c}$, $R^{20e}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (I), including in embodiments of a compound of Formula (I); and ----- indicates a single or double bond such that all valences are satisfied.

In some embodiments, the compound of Formula (I) has the structure of Formula (Ic), or a pharmaceutically acceptable salt or solvate thereof:

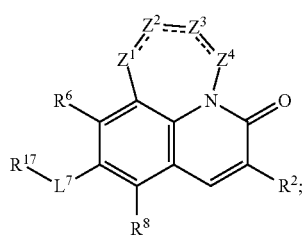

Formula (Ic)

wherein: $Z^1$, $Z^2$, $Z^3$, $Z^4$, $R^2$, $R^6$, $R^{7c}$, $R^{7d}$, $L^7$, $R^{17}$, $R^8$, $R^4$, $L^4$, $R^{4c}$, $R^{4a}$, $R^{4a}$, $R^{4b}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20f}$, $R^{20g}$, $R^{20h}$, $R^{20j}$, $R^{20k}$, $R^{20l}$, $R^{20m}$, $R^{2l}$, $R^{20m}$, $R^{21}$, $R^{22}$, $R^{23}$, $R^{24}$, and $R^{25}$ are as described for Formula (I), including in embodiments of a compound of Formula (I); and ----- indicates a single or double bond such that all valences are satisfied.

In some embodiments, the compound of Formula (I) has the structure of Formula (Id), or a pharmaceutically acceptable salt or solvate thereof:

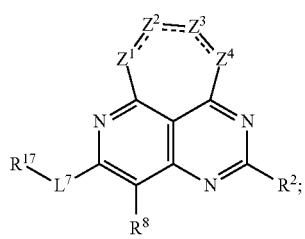

Formula (Id)

wherein: $Z^1$, $Z^2$, $Z^3$, $Z^4$, $R^2$, $R^{7c}$, $R^{7d}$, $L^7$, $R^{17}$, $R^8$, $R^4$, $L^4$, $R^{4c}$, $R^{4a}$, $R^{4a}$, $R^{4b}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20f}$, $R^{20g}$, $R^{20h}$, $R^{20j}$, $R^{20g}$, $R^{20l}$, $R^{20m}$, $R^{21}$, $R^{22}$, $R^{23}$, $R^{24}$, and $R^{25}$ are as described for Formula (I), including in embodiments of a compound of Formula (I); and ----- indicates a single or double bond such that all valences are satisfied.

In some embodiments, the compound of Formula (I) has the structure of Formula (Ie), or a pharmaceutically acceptable salt or solvate thereof:

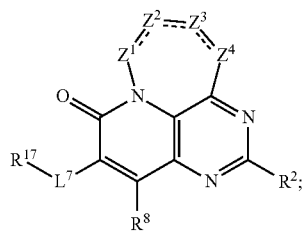

Formula (Ie)

wherein: $Z^1$, $Z^2$, $Z^3$, $Z^4$, $R^2$, $R^{7c}$, $R^{7d}$, $L^7$, $R^{17}$, $R^8$, $R^4$, $L^4$, $R^{4c}$, $R^{4d}$, $R^{4a}$, $R^{4b}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20f}$, $R^{20g}$, $R^{20h}$, $R^{20j}$, $R^{20g}$, $R^{20l}$, $R^{20m}$, $R^{21}$, $R^{22}$, $R^{23}$, $R^{24}$, and $R^{25}$ are as described for Formula (I), including in embodiments of a compound of Formula (I); and ----- indicates a single or double bond such that all valences are satisfied.

In some embodiments, the compound of Formula (I) has the structure of Formula (If), or a pharmaceutically acceptable salt or solvate thereof:

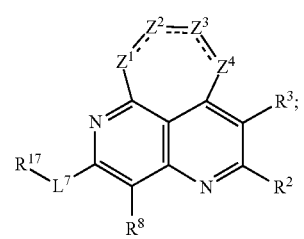

Formula (If)

wherein: $Z^1$, $Z^2$, $Z^3$, $Z^4$, $R^2$, $R^3$, $R^{7c}$, $R^{7d}$, $L^7$, $R^{17}$, $R^8$, $R^4$, $L^4$, $R^{4c}$, $R^{4a}$, $R^{4a}$, $R^{4b}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20c}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (I), including in embodiments of a compound of Formula (I); and ----- indicates a single or double bond such that all valences are satisfied.

In some embodiments is provided a compound of Formula (II), or a pharmaceutically acceptable salt or solvate thereof:

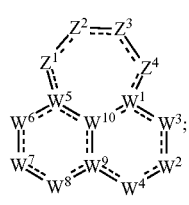

Formula (II)

wherein:

$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, and $Z^3$ is $N(R^4)$, $N(R^{11d})$, $C(R^4)$, $C(R^{11d})$, $C(R^4)(R^{11c})$, $C(R^4)(R^4)$, $C(R^{11c})$ ($R^{11d}$), or C(O) or $Z^4$ is N($R^4$), N($R^{11d}$), C($R^4$), C($R^{11d}$), C($R^4$)($R^{11c}$), C($R^4$)($R^4$), or C($R^{11c}$)($R^{11d}$);

$W^1$ is C($R^1$), C, or N;

$R^1$ is selected from hydrogen, halogen, —CN, $C_{1-6}$alkyl, $C_{2-6}$alkenyl, $C_{2-6}$alkynyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, and $C_{2-6}$alkynyl are optionally substituted with one, two, or three $R^{20a}$;

$W^2$ is N($R^{2a}$), N, C($R^2$), C($R^2$)($R^{2a}$), C(O), S(O)$_2$, or S(O);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$R^{2a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is N($R^{3b}$), N, C($R^3$), C($R^3$)($R^{3a}$), C(O), S(O)$_2$, or S(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and -CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$—, heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^4$ is N or N($R^{3c}$);

$R^{3c}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^5$ is C($R^5$), C, or N;

$R^5$ is selected from hydrogen, halogen, —CN, $C_{1-6}$alkyl, $C_{2-6}$alkenyl, $C_{2-6}$alkynyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, and $C_{2-6}$alkynyl are optionally substituted with one, two, or three $R^{20d}$;

$W^6$ is N($R^{6b}$), N, C($R^6$), C($R^6$)($R^{6a}$), C(O), S(O), or S(O)$_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20e}$;

$R^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20e}$;

$W^7$ is N($R^7$), C($R^7$), or C($R^7$)($R^{7a}$);

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20f}$;

R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl are optionally substituted with one, two, or three R$^{20f}$, R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$—, CR$^7$R$^{7c}$, —OCR$^7$R$^{7c}$—, —N(R$^{7d}$)CR$^7$CR$^{7c}$—, —C(O)CR$^{7c}$R$^{7c}$—, —SCR$^7$R$^{7c}$—, —S(O)$_2$CR$^{7c}$R$^{7c}$—, —S(O)CR$^{7c}$R$^{7c}$—, —P(O)R$^{7d}$CR$^7$CR$^{7c}$—, —CR$^7$CR$^{7c}$CR$^7$CR$^{7c}$, —CR$^{7c}$R$^{7c}$O—, —CR$^{7c}$R$^{7N}$(R$^{7d}$)—, —CR$^7$CR$^{7c}$C(O)—, —CR$^7$CR$^{7c}$S—, —CR$^{7o}$R$^{7c}$S(O)$_2$—, —CR$^7$CR$^{7c}$S(O)—, —CR$^{7o}$R$^7$cP(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7a}$N(R$^{7d}$)—, —OC(O)—, —OS(O)$_2$—, —OS(O)—, —OP(O)R$^{7d}$—, —C(O)O—, —S(O)$_{20}$—, —S(O)O—, or —P(O)R$^{7d}$O—;

R$^{17}$ is selected from C$_{3-10}$cycloalkyl, C$_{2-9}$heterocycloalkyl, C$_{6-10}$aryl, and C$_{1-9}$heteroaryl, wherein C$_{3-10}$cycloalkyl, C$_{2-9}$heterocycloalkyl, C$_{6-10}$aryl, and C$_{1-9}$heteroaryl are optionally substituted with one, two, or three R$^{20g}$;

W$^8$ is C(R$^8$), C(R$^8$)(R$^{8a}$), N, N(R$^{8b}$), C(O), S(O), or S(O)$_2$;

R$^8$ and R$^{8a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$, R$^{8b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$, W$^9$ is C(R$^9$), C, or N;

W$^{10}$ is C(R$^9$), C, or N;

each R$^9$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three R$^{20i}$, R$^4$ is -L$^4$-R$^{4a}$;

L$^4$ is a bond, —O—, —N(R$^{4d}$)—, —C(O)—, —S—, —S(O)$_2$—, —S(O)—, —P(O)R$^{4d}$—, CR$^{4c}$R$^4$, —OCR$^4$R$^{4c}$—, —N(R$^{4d}$)CR$^4$R$^{4c}$—, —C(O)CR$^4$R$^{4c}$—, —SCR$^4$R$^{4c}$—, —S(O)$_2$CR$^4$R$^{4c}$—, —S(O)CR$^4$R$^{4c}$—, —P(O)R$^{4d}$CR$^4$R$^4$—, —CR$^4$R$^4$CCR$^4$R$^4$, —CR*R$^4$O—, —CR$^4$R$^4$CN(R$^{4d}$)—, —CR$^{4c}$R$^4$CC(O)—, —CR$^{4c}$R$^{4c}$S—, —CR$^{4c}$R$^{4S}$(O)$_2$—, —CR$^4$R$^{4c}$S(O)—, —CR$^4$R$^4$P(O)R$^{4d}$—, —N(R$^{4d}$)C(O)—, —N(R$^{4d}$)S(O)$_2$—, —N(R$^{4d}$)S(O)—, —N(R$^{4d}$)P(O)R$^{4d}$—, —C(O)N(R$^{4d}$)—, —S(O)$_2$N(R$^{4d}$)—, —S(O)N(R$^{4d}$)—, —P(O)R$^{4d}$N(R$^{4d}$)—, —OC(O)—, —OS(O)$_2$—, —OS(O)—, —OP(O)R$^{4d}$—, —C(O)O—, —S(O)$_{20}$—, —S(O)O—, or —P(O)R$^{4d}$O—;

each R$^{4c}$ is independently selected from hydrogen, halogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, —OC(O)R$^{14}$a, —N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14a}$, and —N(R$^{14}$)S(O)$_2$R$^{14}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl, are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4d}$ is independently selected from hydrogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, and —OC(O)R$^{14}$a, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl, are optionally substituted with one, two, or three groups independently selected from halogen, oxo, —CN, C$_{1-6}$alkyl, C$_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl are optionally substituted with one, two, or three $R^{20l}$;

each $R^{12b}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{14}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_3$-10cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl; and ----- indicates a single or double bond such that all valences are satisfied.

In some embodiments is a compound of Formula (II), (IIa), (IIb), (IIc), (IId), (IIe), or (IIf), or a pharmaceutically acceptable salt or solvate thereof, wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$.

In some embodiments, the compound of Formula (II) has the structure of Formula (IIa), or a pharmaceutically acceptable salt or solvate thereof:

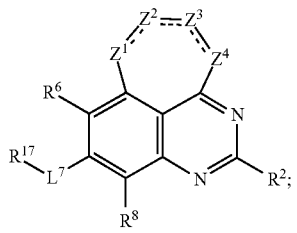

Formula (IIa)

wherein:
$Z^1$, $Z^2$, $Z^3$, $Z^4$, $R^2$, $R^6$, $R^{7c}$, $R^{7d}$, $L^7$, $R^{17}$, $R^8$, $R^4$, $L^4$, $R^{4c}$, $R^{4d}$, $R^{4a}$, $R^{4b}$, $R^{11c}$, $R^{11d}$, $R^{12}$, $R^{12b}$, $R^{13}$, $R^{14}$, $R^{14a}$, $R^{15}$, $R^{20b}$, $R^{20c}$, $R^{20f}$, $R^{20g}$, $R^{20h}$, $R_{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II); and ----- indicates a single or double bond such that all valences are satisfied.

In some embodiments, the compound of Formula (II) has the structure of Formula (IIb), or a pharmaceutically acceptable salt or solvate thereof:

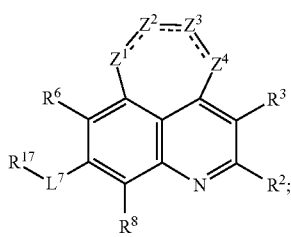

Formula (IIb)

wherein:
$Z^1$, $Z^2$, $Z^3$, $Z^4$, $R^2$, $R^3$, $R^6$, $R^{7c}$, $R^{7d}$, $L^7$, $R^{17}$, $R^8$, $R^4$, $L^4$, $R^{4c}$, $R^{4d}$, $R^{4a}$, $R^{4b}$, $R^{11c}$, $R^{11d}$, $R^{12}$, $R^{12b}$, $R^{13}$, $R^{14}$, $R^{14a}$, $R^{15}$, $R^{20b}$, $R^{20c}$; $R^{20c}$; $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II); and ----- indicates a single or double bond such that all valences are satisfied.

In some embodiments, the compound of Formula (II) has the structure of Formula (IIc), or a pharmaceutically acceptable salt or solvate thereof:

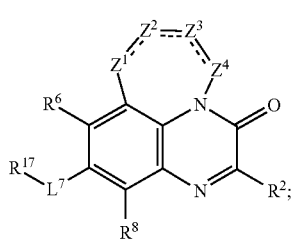

Formula (IIc)

wherein:
$Z^1$, $Z^2$, $Z^3$, $Z^4$, $R^2$, $R^6$, $R^{7c}$, $R^{7d}$, $L^7$, $R^{17}$, $R^8$, $R^4$, $L^4$, $R^{4c}$, Rad, $R^{48}$, $R^{4b}$, $R^{11c}$, $R^{11d}$, $R^{12}$, $R^{120}$, $R^{13}$, $R^{14}$, $R^{14a}$, $R^{15}$, $R^{20b}$, $R^{20e}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II); and ----- indicates a single or double bond such that all valences are satisfied.

In some embodiments, the compound of Formula (II) has the structure of Formula (IId), or a pharmaceutically acceptable salt or solvate thereof:

Formula (IId)

wherein:
$Z^1$, $Z^2$, $Z^3$, $Z^4$, $R^2$, $R^{7c}$, $R^{7d}$, $L^7$, $R^{17}$, $R^8$, $R^4$, $L^4$, $R^{4c}$, $R^{4d}$, $R^{4a}$, $R^{46}$, $R^{11c}$, $R^{11d}$, $R^{12}$, $R^{12b}$, $R^{13}$, $R^{14}$, $R^{14a}$, $R^{15}$, $R^{20b}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II); and ----- indicates a single or double bond such that all valences are satisfied.

In some embodiments, the compound of Formula (II) has the structure of Formula (IIe), or a pharmaceutically acceptable salt or solvate thereof:

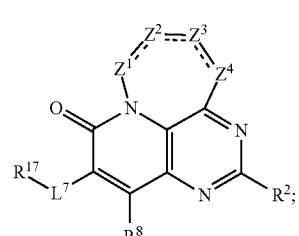

Formula (IIe)

wherein:
$Z^1$, $Z^2$, $Z^3$, $Z^4$, $R^2$, $R^{7c}$, $R^{7d}$, $L^7$, $R^{17}$, $R^8$, $R^4$, $L^4$, $R^{4c}$, $R^{4d}$, $R^{4a}$, $R^{4b}$, $R^{11c}$, $R^{11d}$, $R^{12}$, $R^{126}$, $R^{13}$, $R^{14}$, $R^{14a}$, $R^{15}$, $R^{20b}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II); and ----- indicates a single or double bond such that all valences are satisfied.

In some embodiments, the compound of Formula (II) has the structure of Formula (IIf), or a pharmaceutically acceptable salt or solvate thereof:

111

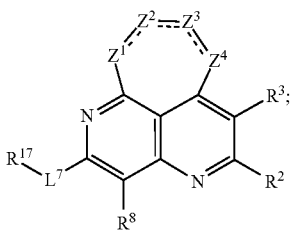

Formula (IIf)

wherein:
$Z^1$, $Z^2$, $Z^3$, $Z^4$, $R^2$, $R^3$, $R^{7c}$, $R^{7d}$, $L^7$, $R^{17}$, $R^8$, $R^4$, $L^4$, $R^{4c}$, $R^{4d}$, $R^{4a}$, $R^{4b}$, $R^{11c}$, $R^{11d}$, $R^{12}$, $R^{12b}$, $R^{13}$, $R^{14}$, $R^{14a}$, $R^{15}$, $R^{20b}$, $R^{20c}$, $R^{20f}$, $R^{20g}$, $R^{20h}$, $R_{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II); and ----- indicates a single or double bond such that all valences are satisfied.

In some embodiments is a compound of Formula (II), (IIa), (IIb), (IIc), (IId), (IIe), or (IIf), or a pharmaceutically acceptable salt or solvate thereof, wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$.

The individual embodiments herein below, or combinations thereof, (e.g., embodiments of $Z^1$, $Z^2$, $Z^3$ or $Z^4$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or a pharmaceutically acceptable salt or solvate thereof. In embodiments of the formulae above, $Z^1$ is $N(R^4)$. In embodiments of the formulae above, $Z^1$ is $N(R^{11c})$. In embodiments of the formulae above, $Z^1$ is $N(R^{11d})$. In embodiments of the formulae above, $Z^1$ is N. In embodiments of the formulae above, $Z^1$ is $C(R^4)$. In embodiments of the formulae above, $Z^1$ is $C(R^{11c})$. In embodiments of the formulae above, $Z^1$ is $C(R^{11d})$. In embodiments of the formulae above, $Z^1$ is $C(R^4)(R^{11c})$. In embodiments of the formulae above, $Z^1$ is $C(R^{11c})(R^{11c})$. In embodiments of the formulae above, $Z^1$ is $C(R^4)(R^4)$. In embodiments of the formulae above, $Z^1$ is $C(R^{11c})(R^{11d})$. In embodiments of the formulae above, $Z^1$ is S. In embodiments of the formulae above, $Z^1$ is O. In embodiments of the formulae above, $Z^1$ is C(O). In embodiments of the formulae above, $Z^2$ is $N(R^4)$. In embodiments of the formulae above, $Z^2$ is $N(R^{11c})$. In embodiments of the formulae above, $Z^2$ is $N(R^{11d})$. In embodiments of the formulae above, $Z^2$ is N. In embodiments of the formulae above, $Z^2$ is $C(R^4)$. In embodiments of the formulae above, $Z^2$ is $C(R^{11c})$. In embodiments of the formulae above, $Z^2$ is $C(R^{11d})$. In embodiments of the formulae above, $Z^2$ is $C(R^4)(R^{11c})$. In embodiments of the formulae above, $Z^2$ is $C(R^{11c})(R^{11c})$. In embodiments of the formulae above, $Z^2$ is $C(R^4)(R^4)$. In embodiments of the formulae above, $Z^2$ is $C(R^{11c})(R^{11d})$. In embodiments of the formulae above, $Z^2$ is S. In embodiments of the formulae above, $Z^2$ is O. In embodiments of the formulae above, $Z^2$ is C(O). In embodiments of the formulae above, $Z^3$ is $N(R^4)$. In embodiments of the formulae above, $Z^3$ is $N(R^{11c})$. In embodiments of the formulae above, $Z^3$ is $N(R^{11d})$. In embodiments of the formulae above, $Z^3$ is N. In embodiments of the formulae above, $Z^3$ is $C(R^4)$. In embodiments of the formulae above, $Z^3$ is $C(R^{11c})$. In embodiments of the formulae above, $Z^3$ is $C(R^{11d})$. In embodiments of the formulae above, $Z^3$ is

112

$C(R^4)(R^{11c})$. In embodiments of the formulae above, $Z^3$ is $C(R^{11c})(R^{11c})$. In embodiments of the formulae above, $Z^3$ is $C(R^4)(R^4)$. In embodiments of the formulae above, $Z^3$ is $C(R^{11c})(R^{11d})$. In embodiments of the formulae above, $Z^3$ is S. In embodiments of the formulae above, $Z^3$ is O. In embodiments of the formulae above, $Z^3$ is C(O). In embodiments of the formulae above, $Z^4$ is $N(R^4)$. In embodiments of the formulae above, $Z^4$ is $N(R^{11c})$. In embodiments of the formulae above, $Z^4$ is $N(R^{11d})$. In embodiments of the formulae above, $Z^4$ is N. In embodiments of the formulae above, $Z^4$ is $C(R^4)$. In embodiments of the formulae above, $Z^4$ is $C(R^{11c})$. In embodiments of the formulae above, $Z^4$ is $C(R^{11d})$. In embodiments of the formulae above, $Z^4$ is $C(R^4)(R^{11c})$. In embodiments of the formulae above, $Z^4$ is $C(R^{11c})(R^{11c})$. In embodiments of the formulae above, $Z^4$ is $C(R^4)(R^4)$. In embodiments of the formulae above, $Z^4$ is $C(R^{11c})(R^{11d})$. In embodiments of the formulae above, $Z^4$ is S. In embodiments of the formulae above, $Z^4$ is O. In embodiments of the formulae above, $Z^4$ is C(O).

In an aspect is provided a compound of Formula (III), or a pharmaceutically acceptable salt or solvate thereof:

Formula (III)

wherein:
$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;

$W^1$, $R^1$, $W^2$, $R^2$, $R^{2a}$, $W^3$, $R^3$, $R^{3a}$, $R^{3b}$, $W^4$, $R^{3c}$, $W^5$, $R^5$, $W^6$, $R^6$, $R^{6a}$, Rob, $W^7$, $R^{7a}$, $R^{7c}$, $R^{7d}$, $R^7$, $L^7$, $R^{17}$, $W^8$, $R^8$, $R^{8a}$, $R^{8b}$, $W^9$, $W^{10}$, $R^3$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, $R^{20m}$, $R^{21}$, $R^{22}$, $R^{23}$, $R^{24}$, and $R^{25}$ are as described for Formula (II), including in embodiments of a compound of Formula (II);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), and —P(=O)($R^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and ----- indicates a single or double bond such that all valences are satisfied.

In some embodiments, the compound of Formula (III) has the structure of Formula (IIIa), or a pharmaceutically acceptable salt or solvate thereof:

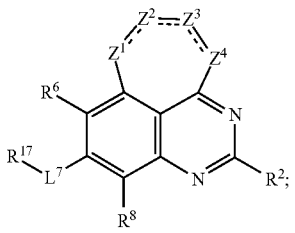

Formula (IIIa)

wherein:

$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;

$R^2$, $R^6$, $R^{7c}$, $R^{7d}$, $L^7$, $R^{17}$, $R^8$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{20b}$, $R^{20e}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IIa), including in embodiments of a compound of Formula (IIa);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)$N(R^{12})(R^{13})$, —$N(R^{14})$C(O)$N(R^{12})(R^{13})$, —$N(R^{14})$C(O)$OR^{15}$, —$N(R^{14})$S(O)$_2R^{15}$, —C(O)$R^{12}$, —S(O)$R^{15}$, —OC(O)$R^{15}$, —C(O)$N(R^{12})(R^{13})$, —C(O)C(O)$N(R^{12})(R^{13})$, —$N(R^{14})$C(O)$R^{12}$, —S(O)$_2R^{15}$, —S(O)$_2N(R^{12})(R^{13})$—, —S(=O)(=NH)$N(R^{12})(R^{13})$, —$CH_2$C(O)$N(R^{12})(R^{13})$, —$CH_2N(R^{14})$C(O)$R^{15}$, —$CH_2$S(O)$_2R^{15}$, —$CH_2$S(O)$_2N(R^{12})(R^{13})$, and —P(=O)$(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and ----- indicates a single or double bond such that all valences are satisfied.

In some embodiments, the compound of Formula (III) has the structure of Formula (IIIb), or a pharmaceutically acceptable salt or solvate thereof:

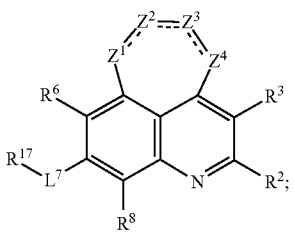

Formula (IIIb)

wherein:

$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;

$R^2$, $R^3$, $R^6$, $R^{7c}$, $R^{7d}$, $L^7$, $R^{17}$, $R^8$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{20b}$, $R^{20c}$, $R^{20c}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IIb), including in embodiments of a compound of Formula (IIb);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)$N(R^{12})(R^{13})$, —$N(R^{14})$C(O)$N(R^{12})(R^{13})$, —$N(R^{14})$C(O)$OR^{15}$, —$N(R^{14})$S(O)$_2R^{15}$, —C(O)$R^{12}$, —S(O)$R^{15}$, —OC(O)$R^{15}$, —C(O)$N(R^{12})(R^{13})$, —C(O)C(O)$N(R^{12})(R^{13})$, —$N(R^{14})$C(O)$R^{12}$, —S(O)$_2R^{15}$, —S(O)$_2N(R^{12})(R^{13})$—, —S(=O)(=NH)$N(R^{12})(R^{13})$, —$CH_2$C(O)$N(R^{12})(R^{13})$, —$CH_2N(R^{14})$C(O)$R^{15}$, —$CH_2$S(O)$_2R^{15}$, —$CH_2$S(O)$_2N(R^{12})(R^{13})$, and —P(=O)$(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and ----- indicates a single or double bond such that all valences are satisfied.

In some embodiments, the compound of Formula (III) has the structure of Formula (IIIc), or a pharmaceutically acceptable salt or solvate thereof:

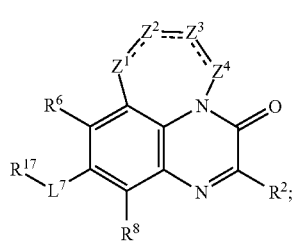

Formula (IIIc)

wherein:

$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;

$R^2$, $R^6$, $R^{7c}$, $R^{7d}$, $L^7$, $R^{17}$, $R^8$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{20b}$, $R^{20b}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IIc), including in embodiments of a compound of Formula (IIc);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and ----- indicates a single or double bond such that all valences are satisfied.

In some embodiments, the compound of Formula (III) has the structure of Formula (IIId), or a pharmaceutically acceptable salt or solvate thereof:

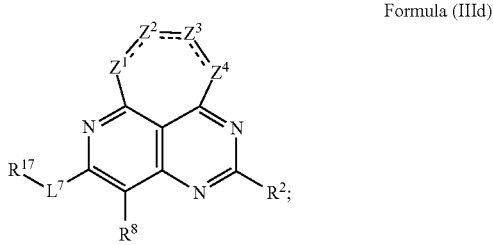

Formula (IIId)

wherein:
$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;

$R^2$, $R^{7c}$, $R^{7d}$, $L^7$, $R^{17}$, $R^8$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{20b}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IId), including in embodiments of a compound of Formula (IId);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and ----- indicates a single or double bond such that all valences are satisfied.

In some embodiments, the compound of Formula (III) has the structure of Formula (IIIe), or a pharmaceutically acceptable salt or solvate thereof:

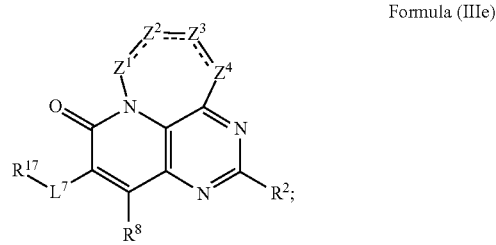

Formula (IIIe)

wherein:
$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);

$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;

wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;

$R^2$, $R^{7c}$, $R^{7d}$, $L^7$, $R^{17}$, $R^8$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{20b}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IIe), including in embodiments of a compound of Formula (IIe);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and ----- indicates a single or double bond such that all valences are satisfied.

In some embodiments, the compound of Formula (III) has the structure of Formula (IIIf), or a pharmaceutically acceptable salt or solvate thereof:

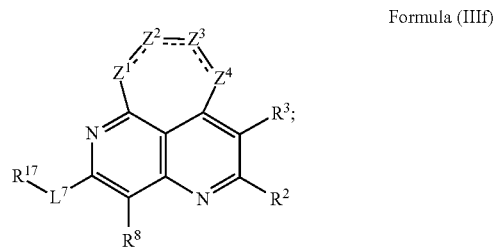

Formula (IIIf)

wherein:
$Z^1$, $Z^2$, and $Z^3$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O);
$Z^4$ is selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, and O;
wherein at least one of $Z^1$, $Z^2$, $Z^3$ and $Z^4$ is $N(R^4)$, $N(R^{11d})$, $C(R^4)$, $C(R^{11d})$, $C(R^4)(R^{11c})$, $C(R^4)(R^4)$, or $C(R^{11c})(R^{11d})$;
$R^2$, $R^3$, $R^{7c}$, $R^{7d}$, $L^7$, $R^{17}$, $R^8$, $R^4$, $L^4$, $R^{4c}$, $R^{4d}$, $R^{4a}$, $R^{11c}$, $R^{11d}$, $R^{12}$, $R^{12b}$, $R^{13}$, $R^{14}$, $R^{14a}$, $R^{15}$, $R^{200}$, $R^{20c}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IIf), including in embodiments of a compound of Formula (IIf);
each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and
----- indicates a single or double bond such that all valences are satisfied.

In an aspect is provided a compound of Formula (IV), or a pharmaceutically acceptable salt or solvate thereof:

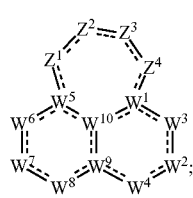

Formula (IV)

wherein:
$Z^1$, $Z^2$, $Z^3$, $Z^4$, $W^1$, $R^1$, $W^2$, $R^2$, $R^{2a}$, $W^3$, $R^3$, $R^{3a}$, $R^{3b}$, $W^4$, $R^{3c}$, $W^5$, $R^5$, $W^6$, $R^6$, $R^{6a}$, $R^{6b}$, $W^7$, $R^{7a}$, $R^{7c}$, $R^{7d}$, $R^7$, $L^7$, $R^{17}$, $W^8$, $R^8$, $R^{8a}$, $R^{8b}$, $W^9$, $W^{10}$, $R^9$, $R^4$, $L^4$, $R^{4C}$, $R^{4d}$, $R^{48}$, $R^{11c}$, $R^{11d}$, $R^{12}$, $R^{12a}$, $R^{12b}$, $R^{13}$, $R^{14}$, $R^{14a}$, $R^{15}$, $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, $R^{20m}$, $R^{21}$, $R^{22}$, $R^{23}$, $R^{24}$, and $R^{25}$ are as described for Formula (I), including in embodiments of a compound of Formula (I);
each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(0)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and
----- indicates a single or double bond such that all valences are satisfied.

In some embodiments, the compound of Formula (IV) has the structure of Formula (IVa), or a pharmaceutically acceptable salt or solvate thereof:

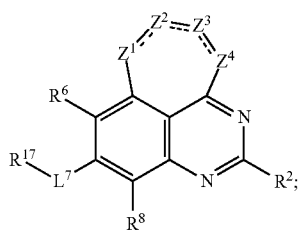

Formula (IVa)

wherein:
$Z^1$, $Z^2$, $Z^3$, $Z^4$, $R^2$, $R^6$, $R^{7c}$, $R^{7d}$, $L^7$, $R^{17}$, $R^8$, $R^4$, $L^4$, $R^{4c}$, $R^{4d}$, $R^{48}$, $R^{11c}$, $R^{11d}$, $R^{12}$, $R^{12a}$, $R^{12b}$, $R^{13}$, $R^{14}$, $R^{14a}$, $R^{15}$, $R^{20b}$, $R^{20e}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (Ia), including in embodiments of a compound of Formula (Ia);
each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(0)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and
----- indicates a single or double bond such that all valences are satisfied.

In some embodiments, the compound of Formula (IV) has the structure of Formula (IVb), or a pharmaceutically acceptable salt or solvate thereof:

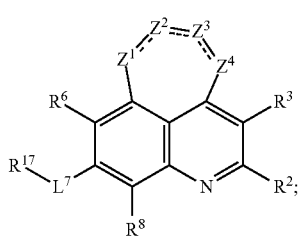

Formula (IVb)

wherein:
$Z^1$, $Z^2$, $Z^3$, $Z^4$, $R^2$, $R^3$, $R^6$, $R^{7c}$, $R^{7d}$, $L^7$, $R^{17}$, $R^8$, $R^4$, $L^4$, $R^{4c}$, $R^{4d}$, $R^{48}$, $R^{11c}$, $R^{11d}$, $R^{12}$, $R^{128}$, $R^{12b}$, $R^{13}$, $R^{14}$, $R^{14a}$, $R^{15}$, $R^{20b}$, $R^{20c}$, $R^{20c}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (Ib), including in embodiments of a compound of Formula (Ib);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more R$^{20j}$; and ----- indicates a single or double bond such that all valences are satisfied.

In some embodiments, the compound of Formula (IV) has the structure of Formula (IVc), or a pharmaceutically acceptable salt or solvate thereof:

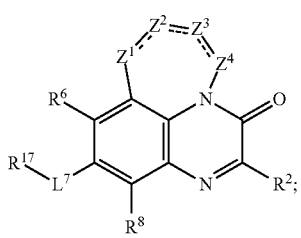

Formula (IVc)

wherein:

Z$^1$, Z$^2$, Z$^3$, Z$^4$, R$^2$, R$^6$, R$^1$, R$^{7d}$, L$^7$, R$^{17}$, R$^8$, R$^4$, L$^4$, R$^{4o}$, R$^{4d}$, R$^{4a}$, R$^{11c}$, R$^{11d}$, R$^{12}$, R$^{12a}$, R$^{12b}$, R$^{13}$, R$^{14}$, R$^{14a}$, R$^{15}$, R$^{20b}$, R$^{20e}$, R$^{20f}$, R$^{20g}$, R$^{20h}$, R$_{20j}$, R$^{20k}$, R$^{20l}$, R$^{20m}$, R$^{21}$, R$^{22}$, R$^{23}$, R$^{24}$, and R$^{25}$ are as described for Formula (Ic), including in embodiments of a compound of Formula (Ic);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more R$^{20j}$; and ----- indicates a single or double bond such that all valences are satisfied.

In some embodiments, the compound of Formula (IV) has the structure of Formula (IVd), or a pharmaceutically acceptable salt or solvate thereof:

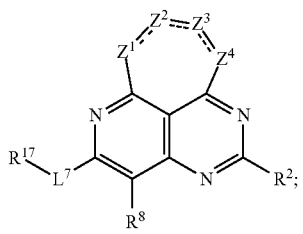

Formula (IVd)

wherein:

Z$^1$, Z$^2$, Z$^3$, Z$^4$, R$^2$, R$^{7c}$, R$^{7d}$, L$^7$, R$^{17}$, R$^8$, R$^4$, L$^4$, R$^{4c}$, R$^{4d}$, R$^{4a}$, R$^{11c}$, R$^{11d}$, R$^{12}$, R$^{12a}$, R$^{12b}$, R$^{13}$, R$^{14}$, R$^{14a}$, R$^{15}$, R$^{20b}$, R$^{20f}$, R$^{20g}$, R$^{20h}$, R$^{20j}$, R$^{20k}$, R$^{20l}$, R$^{20m}$, R$^{21}$, R$^{22}$, R$^{23}$, R$^{24}$, and R$^{25}$ are as described for Formula (Id), including in embodiments of a compound of Formula (Id);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more R$^{20j}$; and ----- indicates a single or double bond such that all valences are satisfied.

In some embodiments, the compound of Formula (IV) has the structure of Formula (IVe), or a pharmaceutically acceptable salt or solvate thereof:

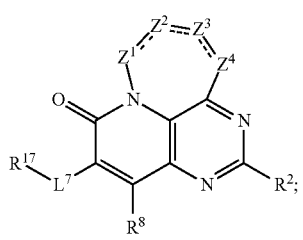

Formula (IVe)

wherein:

Z$^1$, Z$^2$, Z$^3$, Z$^4$, R$^2$, R$^{7c}$, R$^{7d}$, L$^7$, R$^{17}$, R$^8$, R$^4$, L$^4$, R$^{4C}$, R$^{4d}$, R$^{4a}$, R$^{11c}$, R$^{11d}$, R$^{12}$, R$^{12a}$, R$^{12b}$, R$^{13}$, R$^{14}$, R$^{14a}$, R$^{15}$, R$^{20b}$, R$^{20f}$, R$^{20g}$, R$^{20h}$, R$^{20j}$, R$^{20k}$, R$^{20l}$, R$^{20m}$, R$^{21}$, R$^{22}$, R$^{23}$, R$^{24}$, and R$^{25}$ are as described for Formula (Ie), including in embodiments of a compound of Formula (Ie);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, and C$_{1-9}$heteroaryl are optionally substituted with one or more R$^{20j}$; and ----- indicates a single or double bond such that all valences are satisfied.

In some embodiments, the compound of Formula (IV) has the structure of Formula (IVf), or a pharmaceutically acceptable salt or solvate thereof:

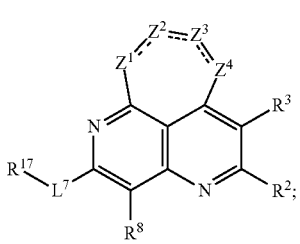

Formula (IVf)

wherein:

Z$^1$, Z$^2$, Z$^3$, Z$^4$, R$^2$, R$^3$, R$^{7c}$, R$^{7d}$, L$^7$, R$^{17}$, R$^8$, R$^4$, L$^4$, R$^{4c}$, R$^{4d}$, R$^{4a}$, R$^{11c}$, R$^{11d}$, R$^{12}$, R$^{12a}$, R$^{12b}$, R$^{13}$, R$^{14}$, R$^{14a}$, R$^{15}$, R$^{20b}$, R$^{20c}$, R$^{20f}$, R$^{20g}$, R$^{20h}$, R$_{20j}$, R$^{20k}$, R$^{20l}$, R$^{20m}$, R$^{21}$, R$^{22}$, R$^{23}$, R$^{24}$, and R$^{25}$ are as described for Formula (If), including in embodiments of a compound of Formula (If);

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, and C$_{1-9}$heteroaryl are optionally substituted with one or more R$^{20j}$; and ----- indicates a single or double bond such that all valences are satisfied.

In an aspect is provided a compound of Formula (XVI), or a pharmaceutically acceptable salt or solvate thereof:

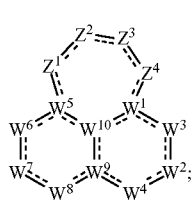

Formula (XVI)

wherein:

Z$^1$, Z$^2$, Z$^3$, Z$^4$, W$^1$, R$^1$, W$^2$, R$^{2a}$, W$^3$, R$^3$, R$^{3a}$, R$^{3b}$, W$^4$, R$^{3c}$, W$^5$, R$^5$, W$^6$, R$^6$, R$^{6a}$, Rob, W$^7$, R$^{7a}$, R$^{7c}$, R$^{7d}$, R$^7$, L$^7$, R$^{17}$, W$^8$, R$^8$, R$^{8a}$, R$^{8b}$, W$^9$, W$^{10}$, R$^9$, R$^4$, L$^4$, R$^{4c}$, R$^{4d}$, R$^{42}$, R$^{12}$, R$^{12b}$, R$^{13}$, R$^{14}$, R$^{14a}$, R$^{15}$, R$^{21}$, R$^{22}$, R$^{23}$, R$^{24}$, and R$^{25}$ are as described for Formula (III), including in embodiments of a compound of Formula (III);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-N(R$^{12}$)(R$^{13}$), —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), =NR$^{21}$, —C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_3$-10cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ----- indicates a single or double bond such that all valences are satisfied.

In some embodiments, the compound of Formula (XVI) has the structure of Formula (XVIa), or a pharmaceutically acceptable salt or solvate thereof:

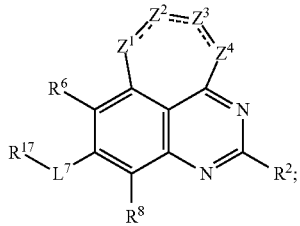

Formula (XVIa)

wherein:
Z$^1$, Z$^2$, Z$^3$, Z$^4$, R$^6$, R$^{7c}$, R$^{7d}$, L$^7$, R$^{17}$, R$^8$, R$^4$, L$^4$, R$^{4c}$, R$^{4d}$, R$^{4a}$, R$^{12}$, R$^{12b}$, R$^{13}$, R$^{14}$, R$^{14a}$; R$^{15}$, R$^{21}$, R$^{22}$, R$^{23}$, R$^{24}$, and R$^{25}$ are as described for Formula (IIIa), including in embodiments of a compound of Formula (IIIa);
R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(—O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$ heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, =C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=OX=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-}$ $_{10}$aryl, —CH$_2$-C$_{1-11}$heteroaryl, and C$_{1-11}$heteroaryl are optionally substituted with one, two, three, four, or five R$^{20k}$;

each R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), =NR$^{21}$, —C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_3$-10cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_1$-heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_3$-10cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ------ indicates a single or double bond such that all valences are satisfied.

In some embodiments, the compound of Formula (XVI) has the structure of Formula (XVIb), or a pharmaceutically acceptable salt or solvate thereof:

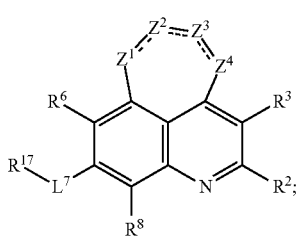

Formula (XVIb)

wherein:
Z$^1$, Z$^2$, Z$^3$, Z$^4$, R$^3$, R$^6$, R$^{7c}$, R$^{7d}$, L$^7$, R$^{17}$, R$^8$, R$^4$, L$^4$, R$^{4c}$, R$^{4d}$, R$^{4a}$, R$^{12}$, R$^{12b}$, R$^{13}$, R$^{14}$, R$^{14a}$, R$^{15}$, R$^{21}$, R$^{22}$, R$^{23}$, R$^{24}$, and R$^{25}$ are as described for Formula (IIIb), including in embodiments of a compound of Formula (IIIb);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_1$-heteroaryl, —OR$^{12}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, =C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$NR^{21}$, —$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_3$-10cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ----- indicates a single or double bond such that all valences are satisfied.

In some embodiments, the compound of Formula (XVI) has the structure of Formula (XVIc), or a pharmaceutically acceptable salt or solvate thereof:

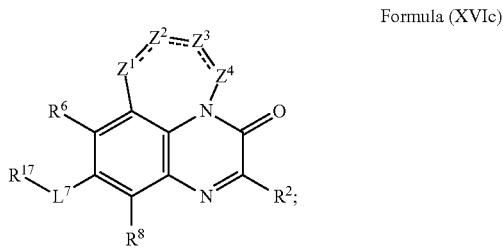

Formula (XVIc)

wherein:
$Z^1$, $Z^2$, $Z^3$, $Z^4$, $R^6$, $R^{7c}$, $R^{7d}$, $L^7$, $R^{17}$, $R^8$, $R^4$, $L^4$, $R^{4c}$, $R^{4d}$, $R^{4a}$, $R^{12}$, $R^{12b}$, $R^{13}$, $R^{14}$, $R^{14a}$; $R^{15}$, $R^{21}$, $R^{22}$, $R^{23}$, $R^{24}$, and $R^{25}$ are as described for Formula (IIIc), including in embodiments of a compound of Formula (IIIc);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, =$C(R^{21b})_2$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, S(=O)(=NH)N(R^{12})(R^{13})$, —($C_{1-6}$alkyl)-$C(O)N(R^{12})(R^{13})$, —($C_{1-6}$alkyl)-$N(R^{12})(R^{13})$, —($C_{1-6}$alkyl)-$OC(O)R^{12}$, —($C_{1-6}$alkyl)-$N(R^{14})C(O)R^{12}$, —($C_{1-6}$alkyl)-$S(O)_2R^{15}$, and —($C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, S(=O)(=NH)N(R^{12})(R^{13})$, —($C_{1-6}$alkyl)-$C(O)N(R^{12})(R^{13})$, —($C_{1-6}$alkyl)-$N(R^{12})(R^{13})$, —($C_{1-6}$alkyl)-$OC(O)R^{12}$, —($C_{1-6}$alkyl)-$N(R^{14})C(O)R^{12}$, —($C_{1-6}$alkyl)-$S(O)_2R^{15}$, and —($C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, =$NR^{21}$, =$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_3$-10cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ------ indicates a single or double bond such that all valences are satisfied.

In some embodiments, the compound of Formula (XVI) has the structure of Formula (XVId), or a pharmaceutically acceptable salt or solvate thereof:

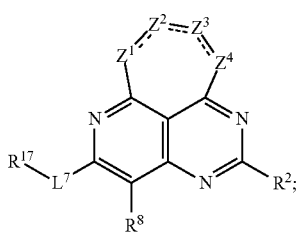

Formula (XVId)

wherein:
$Z^1$, $Z^2$, $Z^3$, $Z^4$, $R^{7c}$, $R^{7d}$, $L^7$, $R^{17}$, $R^8$, $R^4$, $L^4$, $R^{4o}$ C., $R^{4d}$, $R^{4a}$, $R^{4b}$, $R^{12}$, $R^{12b}$, $R^{13}$, $R^{14}$, $R^{14a}$, $R^{15}$, $R^{21}$, $R^{22}$, $R^{23}$, $R^{24}$, and $R^{25}$ are as described for Formula (IIId), including in embodiments of a compound of Formula (IIId);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$N$=$(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$hetero-cycloalkyl, $C_{6-10}$aryl, and $C_{1-9}$heteroaryl are optionally substituted with one, two, or three $R^{20b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, =$C(R^{21b})_2$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=OX(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_2$-heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, =NR$^{21}$, =C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_3$-10cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ----- indicates a single or double bond such that all valences are satisfied.

In some embodiments, the compound of Formula (XVI) has the structure of Formula (XVIe), or a pharmaceutically acceptable salt or solvate thereof:

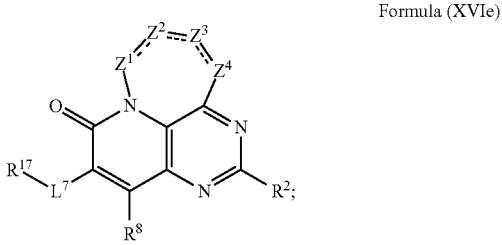

Formula (XVIe)

wherein:
Z$^1$, Z$^2$, Z$^3$, Z$^4$, R$^{7c}$, R$^{7d}$, L$^7$, R$^{17}$, R$^8$, R$^4$, L$^4$, R$^4$, R$^{4d}$, R$^{4a}$, R$^{12}$, R$^{12b}$, R$^{13}$, R$^{14}$, R$^{14a}$; R$^{15}$, R$^{21}$, R$^{22}$, R$^{23}$, R$^{24}$, and R$^{25}$ are as described for Formula (IIIe), including in embodiments of a compound of Formula (IIIe);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$_{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), =NR$^{21}$, —C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)

R²¹, —S(O)₂R²⁵, —S(O)₂N(R²²)(R²³), —OCH₂C(O)OR²², and —OC(O)R²⁵, wherein C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-C₂₋₉heterocycloalkyl, C₆₋₁₀aryl, —CH₂-C₆₋₁₀aryl, —CH₂-C₁₋₉heteroaryl, and C₁₋₉heteroaryl are optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²¹, —N(R²⁴)S(O)₂R²⁵, —C(O)R²¹, —S(O)₂R²⁵, —S(O)₂N(R²²)(R²³), and —OC(O)R²⁵;

R²¹ᵇ is independently selected at each occurrence from hydrogen, halogen, C₁₋₆alkyl, C₁₋₆haloalkyl, C₂₋₆alkenyl, C₂₋₆alkynyl, C₃₋₁₀cycloalkyl, C₂₋₉heterocycloalkyl, C₆₋₁₀aryl, and C₁₋₉heteroaryl, or two R²¹ᵇ are taken together with the carbon atom to which they are attached to form C₃₋₁₀cycloalkyl or C₂₋₉heterocycloalkyl; each of which is optionally substituted with one, two, or three substituents independently selected from halogen, C₁₋₃ alkyl, C₁₋₃ haloalkyl, and —OH; and ----- indicates a single or double bond such that all valences are satisfied.

In some embodiments, the compound of Formula (XVI) has the structure of Formula (XVIf), or a pharmaceutically acceptable salt or solvate thereof:

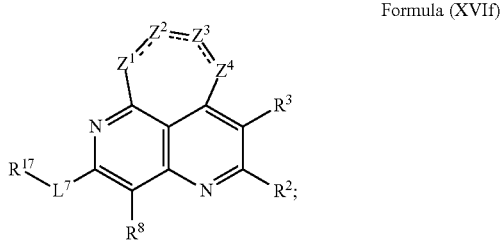

Formula (XVIf)

wherein:
Z¹, Z², Z³, Z⁴, R³, R⁷ᶜ, R⁷ᵈ, L⁷, R¹⁷, R⁸, R⁴, L⁴, R⁴ᶜ, R⁴ᵈ, R⁴ᵃ, R¹², R¹²⁰, R¹³, R¹⁴, R¹⁴ᵃ, R¹⁵, R²¹, R²², R²³, R²⁴, and R²⁵ are as described for Formula (IIIf), including in embodiments of a compound of Formula (IIIf);

R² is selected from halogen, —CN, C₁₋₆alkyl, C₂₋₆alkenyl, C₂₋₆alkynyl, C₃₋₁₀cycloalkyl, C₂₋₉heterocycloalkyl, C₆₋₁₀aryl, C₁₋₉heteroaryl, —OR¹², —SR¹², —N(R¹²)(R¹³), —N=(R¹⁵), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R¹⁴)C(O)R¹⁵, —S(O)₂R¹⁵, —S(O)₂N(R¹²)(R¹³)—, —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein C₁₋₆alkyl, C₂₋₆alkenyl, C₂₋₆alkynyl, C₃₋₁₀cycloalkyl, C₂₋₉heterocycloalkyl, C₆₋₁₀aryl, and C₁—, heteroaryl are optionally substituted with one, two, or three R²⁰ᵇ;

each R⁴ᵇ is independently selected from halogen, oxo, —CN, C₁₋₆alkyl, C₂₋₆alkenyl, C₂₋₆alkynyl, C₃₋₁₂cycloalkyl, C₂₋₁₁heterocycloalkyl, C₆₋₁₀aryl, C₁₋₉heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(R²¹ᵇ)₂, —C(O)R¹², —S(O)R¹⁵, —OC(O)R¹⁵, —C(O)N(R¹²)(R¹³), —C(O)C(O)N(R¹²)(R¹³), —N(R¹⁴)C(O)R¹², —S(O)₂R¹⁵, —S(O)₂N(R¹²)(R¹³)—, —S(=OX=NH)N(R¹²)(R¹³), —CH₂C(O)N(R¹²)(R¹³), —CH₂N(R¹⁴)C(O)R¹², —CH₂S(O)₂R¹⁵, —CH₂S(O)₂N(R¹²)(R¹³), and —P(=O)(R¹²)₂, wherein C₁₋₆alkyl, C₂₋₆alkenyl, C₂₋₆alkynyl, C₃₋₁₂cycloalkyl, C₂₋₁₁heterocycloalkyl, C₆₋₁₀aryl, and C₁₋₉heteroaryl are optionally substituted with one or more R²⁰ʲ;

each R¹¹ᶜ is independently selected from hydrogen, halogen, oxo, —CN, C₁₋₆alkyl, C₂₋₆alkenyl, C₂₋₆alkynyl, C₁₋₆haloalkyl, C₃₋₁₂cycloalkyl, —CH₂-C₃₋₁₂cycloalkyl, C₁₋₁₁heterocycloalkyl, —CH₂-C₁₋₁₁heterocycloalkyl, C₆₋₁₀aryl, —CH₂-C₆₋₁₀aryl, —CH₂-C₁₋₁₁heteroaryl, C₁₋₁₁heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹², —S(O)R¹⁵, —OC(O)R¹⁵, —C(O)N(R¹²)(R¹³), —C(O)C(O)N(R¹²)(R¹³), —N(R¹⁴)C(O)R¹², —S(O)₂R¹⁵, —S(O)₂N(R¹²)(R¹³)—, S(=O)(=NH)N(R¹²)(R¹³), —(C₁₋₆alkyl)-C(O)N(R¹²)(R¹³), —(C₁₋₆alkyl)-N(R¹²)(R¹³), —(C₁₋₆alkyl)-OC(O)R¹², —(C₁₋₆alkyl)-N(R¹⁴)C(O)R¹², —(C₁₋₆alkyl)-S(O)₂R¹⁵, and —(C₁₋₆alkyl)-S(O)₂N(R¹²)(R¹³), wherein C₁₋₆alkyl, C₂₋₆alkenyl, C₂₋₆alkynyl, C₁₋₆haloalkyl, C₃₋₁₂cycloalkyl, —CH₂-C₃₋₁₂cycloalkyl, C₁₋₁₁heterocycloalkyl, —CH₂-C₁₋₁₁heterocycloalkyl, C₆₋₁₀aryl, —CH₂-C₆₋₁₀aryl, —CH₂-C₁₋₁₁heteroaryl, and C₁₋₁₁heteroaryl are optionally substituted with one, two, three, four, or five R²⁰ᵏ;

each R¹¹ᵈ is independently selected from halogen, oxo, —CN, C₁₋₆alkyl, C₂₋₆alkenyl, C₂₋₆alkynyl, C₁₋₆haloalkyl, C₃₋₁₂cycloalkyl, —CH₂-C₃₋₁₂cycloalkyl, C₁₋₁₁heterocycloalkyl, —CH₂-C₁₋₁₁heterocycloalkyl, C₆₋₁₀aryl, —CH₂-C₆₋₁₀aryl, —CH₂-C₁₋₁₁heteroaryl, C₁₋₁₁ heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹², —S(O)R¹⁵, —OC(O)R¹⁵, —C(O)N(R¹²)(R¹³), —C(O)C(O)N(R¹²)(R¹³), —N(R¹⁴)C(O)R¹², —S(O)₂R¹⁵, —S(O)₂N(R¹²)(R¹³)—, S(=O)(=NH)N(R¹²)(R¹³), —(C₁₋₆alkyl)-C(O)N(R¹²)(R¹³), —(C₁₋₆alkyl)-N(R¹²)(R¹³), —(C₁₋₆alkyl)-OC(O)R¹², —(C₁₋₆alkyl)-N(R¹⁴)C(O)R¹², —(C₁₋₆alkyl)-S(O)₂R¹⁵, and —(C₁₋₆alkyl)-S(O)₂N(R¹²)(R¹³), wherein C₁₋₆alkyl, C₂₋₆alkenyl, C₂₋₆alkynyl, C₁₋₆haloalkyl, C₃₋₁₂cycloalkyl, —CH₂-C₃₋₁₂cycloalkyl, C₁₋₁₁heterocycloalkyl, —CH₂-C₁₋₁₁heterocycloalkyl, C₆₋₁₀aryl, —CH₂-C₆₋₁₀aryl, —CH₂-C₁₋₁₁heteroaryl, and C₁₋₁₁heteroaryl are optionally substituted with one, two, three, four, or five R²⁰ᵏ;

each R²⁰ᵃ; R²⁰ᵇ, R²⁰ᶜ; R²⁰ᵈ, R²⁰ᵉ, R²⁰ᶠ, R²⁰ᵍ, R²⁰ʰ, R²⁰ⁱ, R²⁰ʲ, R²⁰ᵏ, R²⁰ˡ, and R²⁰ᵐ is independently selected from halogen, oxo, —CN, C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-C₂₋₉heterocycloalkyl, C₆₋₁₀aryl, —CH₂-C₆₋₁₀aryl, —CH₂-C₁₋₉heteroaryl, C₁₋₉heteroaryl, —OR²¹, —SR²¹, —N(R²²)(R²³), =NR²¹, =C(R²¹ᵇ)₂, —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²¹, —N(R²⁴)S(O)₂R²⁵, —C(O)R²¹, —S(O)₂R²⁵, —S(O)₂N(R²²)(R²³), —OCH₂C(O)OR²², and —OC(O)R²⁵, wherein C₁₋₆alkyl, C₂₋₆alkenyl, C₂₋₆alkynyl, C₃₋₁₀cycloalkyl, —CH₂-C₃₋₁₀cycloalkyl, C₂₋₉heterocycloalkyl, —CH₂-

$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ----- indicates a single or double bond such that all valences are satisfied.

In an aspect is provided a compound of Formula (XVII), or a pharmaceutically acceptable salt or solvate thereof:

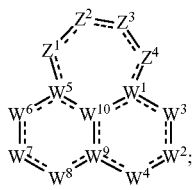

Formula (XVII)

wherein:

$Z^1$, $Z^2$, $Z^3$, $Z^4$, $W^1$, $R^1$, $W^2$, $R^{2a}$, $W^3$, $R^3$, $R^{3a}$, $R^{3b}$, $W^4$, $R^{3c}$, $W^5$, $R^5$, $W^6$, $R^6$, $R^{6a}$, $R^{ob}$, $W^7$, $R^{7a}$, $R^1$, $R^{7d}$, $R^7$, $L^7$, $R^{17}$, $W^8$, $R^8$, $R^{8a}$, $R^{8b}$, $W^9$, $W^{10}$, $R^9$, $R^4$, $L^4$, $R^{4c}$, $R^{4d}$, $R^{4a}$, $R^{12}$, $R^{12a}$, $R^{12b}$, $R^{13}$, $R^{14}$, $R^{14a}$; $R^{15}$, $R^{21}$, $R^{22}$, $R^{23}$, $R^{24}$, and $R^{25}$ are as described for Formula (IV), including in embodiments of a compound of Formula (IV);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12}$, —$N(R^{12})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(R^{21b})_2$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})$ $(R^{13})$—, —$S(=OX(=NH)N(R^{12})(R^{13})$, —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$ heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_1$-6alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, $=NR^{21}$, $=C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two R$^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ------ indicates a single or double bond such that all valences are satisfied.

In some embodiments, the compound of Formula (XVII) has the structure of Formula (XVIIa), or a pharmaceutically acceptable salt or solvate thereof:

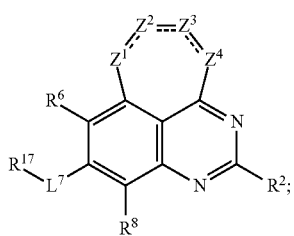

Formula (XVIIa)

wherein:
Z$^1$, Z$^2$, Z$^3$, Z$^4$, R$^6$, R$^{7c}$, R$^{7d}$, L$^7$, R$^{17}$, R$^8$, R$^4$, L$^4$, R$^{4c}$, R$^{4d}$, R$^{4a}$, R$^{12}$, R$^{12a}$, R$^{12b}$, R$^{13}$, R$^{14}$, R$^{14a}$, R$^{15}$, R$^{21}$, R$^{22}$, R$^{23}$, R$^{24}$, and R$^{25}$ are as described for Formula (IVa), including in embodiments of a compound of Formula (IVa);
R$^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$a, —SR$^{12}$, —N(R$^{12}$)(R$^{13}$), —N═(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(═O)(═NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20b}$;

each R$^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(═OX═NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(═O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6}$-10aryl, and $C_{1-9}$heteroaryl are optionally substituted with one or more R$^{20j}$;

each R$^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{6-10}$aryl, —CH$_2$-C$_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(═O)(═NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{6-10}$aryl, —CH$_2$-C$_{1-11}$heteroaryl, and $C_{1-11}$heteroaryl are optionally substituted with one, two, three, four, or five R$^{20k}$;

each R$^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{6-10}$aryl, —CH$_2$-C$_{1-11}$heteroaryl, $C_{1-11}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(═O)(═NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{6-10}$aryl, —CH$_2$-C$_{1-11}$heteroaryl, and $C_{1-11}$heteroaryl are optionally substituted with one, two, three, four, or five R$^{20k}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, $C_{1-9}$heteroaryl, —OR$^{21}$, —SR$^{21}$, —N(R$^{22}$)(R$^{23}$), ═NR$^{21}$, ═C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_3$-10cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC (O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_3$-10cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ------ indicates a single or double bond such that all valences are satisfied.

In some embodiments, the compound of Formula (XVII) has the structure of Formula (XVIIb), or a pharmaceutically acceptable salt or solvate thereof:

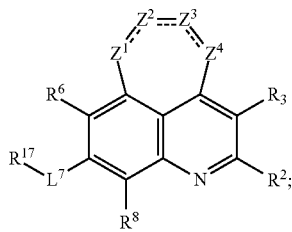

Formula (XVIIb)

wherein:

Z$^1$, Z$^2$, Z$^3$, Z$^4$, R$^3$, R$^6$, R$^{7c}$, R$^{7d}$, L$^7$, R$^{17}$, R$^8$, R$^4$, L$^4$, R$^{4o}$C., R$^{4d}$, R$^{4a}$, R$^{12}$, R$^{12a}$, R$^{12b}$, R$^{13}$, R$^{14}$, R$^{14a}$, R$^{15}$, R$^{21}$, R$^{22}$, R$^{23}$, R$^{24}$, and R$^{25}$ are as described for Formula (IVb), including in embodiments of a compound of Formula (IVb);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$a, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), =NR$^{21}$, =C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)

C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ----- indicates a single or double bond such that all valences are satisfied.

In some embodiments, the compound of Formula (XVII) has the structure of Formula (XVIIc), or a pharmaceutically acceptable salt or solvate thereof:

Formula (XVIIc)

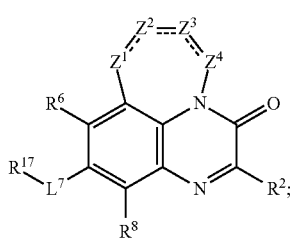

wherein:
Z$^1$, Z$^2$, Z$^3$, Z$^4$, R$^6$, R$^{7c}$, R$^{7d}$, L$^7$, R$^{17}$, R$^8$, R$^4$, L$^4$, R$^{4c}$, R$^{4d}$, R$^{4a}$, R$^{12}$, R$^{128}$, R$^{12b}$, R$^{13}$, R$^{14}$, R$^{14a}$; R$^{15}$, R$^{21}$, R$^{22}$, R$^{23}$, R$^{24}$, and R$^{25}$ are as described for Formula (IVc), including in embodiments of a compound of Formula (IVc);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12a}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), =NR$^{21}$, —C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)

C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ----- indicates a single or double bond such that all valences are satisfied.

In some embodiments, the compound of Formula (XVII) has the structure of Formula (XVIId), or a pharmaceutically acceptable salt or solvate thereof:

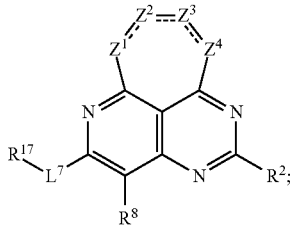

Formula (XVIId)

wherein:
Z$^1$, Z$^2$, Z$^3$, Z$^4$, R$^{7c}$, R$^{7d}$, L$^7$, R$^{17}$, R$^8$, R$^4$, L$^4$, R$^{4c}$, R$^{4d}$, R$^{4a}$, R$^{12}$, R$^{12a}$, R$^{12b}$, R$^{13}$, R$^{14}$, R$^{14a}$, R$^{15}$, R$^{21}$, R$^{22}$, R$^{23}$, R$^{24}$, and R$^{25}$ are as described for Formula (IVd), including in embodiments of a compound of Formula (IVd);

R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12a}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)OR$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, =C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=OX(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —NR$^{21}$, =C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

145

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ----- indicates a single or double bond such that all valences are satisfied.

In some embodiments, the compound of Formula (XVII) has the structure of Formula (XVIIe), or a pharmaceutically acceptable salt or solvate thereof:

Formula (XVIIe)

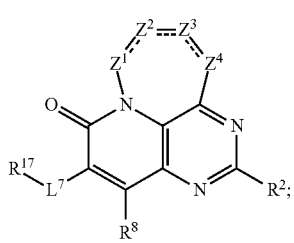

wherein:

$Z^1, Z^2, Z^3, Z^4, R^{7c}, R^{7d}, L^7, R^{17}, R^8, R^4, L^4, R^{4c}, R^{4d}, R^{4B}, R^{12}, R^{12a}, R^{12b}, R^{13}, R^{14}, R^{14a}, R^{15}, R^{21}, R^{22}, R^{23}, R^{24},$ and $R^{25}$ are as described for Formula (IVe), including in embodiments of a compound of Formula (IVe);

$R^2$ is selected from halogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12a}$, —$SR^{12}$, —$N(R^{12})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(R^{21b})_2$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$het-

146 eroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, =$NR^{21}$, =$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; and ----- indicates a single or double bond such that all valences are satisfied.

In some embodiments, the compound of Formula (XVII) has the structure of Formula (XVIIf), or a pharmaceutically acceptable salt or solvate thereof:

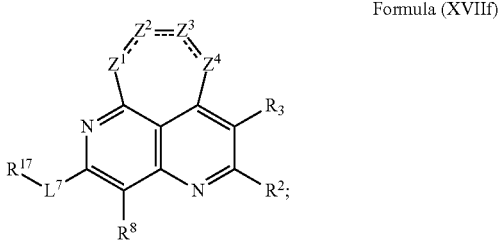

Formula (XVIIf)

wherein:

Z$^1$, Z$^2$, Z$^3$, Z$^4$, R$_3$, R$^{7c}$, R$^{7d}$, L$^7$, R$^{17}$, R$^8$, R$^4$, L$^4$, R$^{4c}$, R$^{4d}$, R$^{4a}$, R$^{12}$, R$^{12a}$, R$^{12b}$, R$^{13}$, R$^{14}$, R$^{14a}$, R$^{15}$, R$^{21}$, R$^{22}$, R$^{23}$, R$^{24}$, and R$^{25}$ are as described for Formula (IVf), including in embodiments of a compound of Formula (IVf);

R$^2$ is selected from halogen, —CN, C$_{1-6}$alkyl, C$_{2-6}$alkenyl, C$_{2-6}$alkynyl, C$_{3-10}$cycloalkyl, C$_2$-heterocycloalkyl, C$_{6-10}$aryl, C$_{1-9}$heteroaryl, —OR$^{12a}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20j}$;

each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), =NR$^{21}$, —C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, $C_{1-3}$ alkyl, $C_{1-3}$ haloalkyl, and —OH; and ----- indicates a single or double bond such that all valences are satisfied.

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), or (XVIIf),

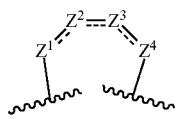

is

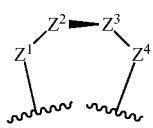

and $Z^1$, $Z^2$, $Z^3$, and $Z^4$ are as described in Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), or (XVIIf), or any embodiment thereof. In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), or (XVIIf),

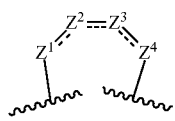

is

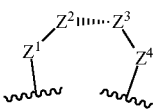

and $Z^1$, $Z^2$, $Z^3$, and $Z^4$ are as described in Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), or (XVIIf), or any embodiment thereof.

The individual embodiments herein below, or combinations thereof, (e.g., embodiments of $Z^1$, $Z^2$, $Z^3$, or $Z^4$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), or (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In some embodiments of the formulae above, or a pharmaceutically acceptable salt or solvate thereof, $Z^1$ is O, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate thereof, $Z^1$ is S, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate thereof, $Z^1$ is $N(R^{11c})$, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate thereof, $Z^1$ is $C(R^{11c})(R^{11c})$, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate thereof, $Z^1$ is O, $Z^2$ is $C(R^{11c})(R^{11c})$, $Z^3$ is $C(O)$, and $Z^4$ is $N(R^4)$. In some embodiments of the formulae above, or a pharmaceutically acceptable salt or solvate thereof, $Z^1$ is O, $Z^2$ is $C(R^{11c})(R^{11c})$, $Z^3$ is $C(R^4)(R^{11c})$, and $Z^4$ is $N(R^{11c})$. In some embodiments of the formulae above, or a pharmaceutically acceptable salt or solvate thereof, $Z^1$ is O, $Z^2$ is $C(R^{11c})(R^{11c})$, $Z^3$ is $C(R^{11c})(R^{11c})$, and $Z^4$ is $C(R^4)(R^{11c})$. In some embodiments of the formulae above, or a pharmaceutically acceptable salt or solvate thereof, $Z^1$ is O, $Z^2$ is $C(R^{11c})(R^{11c})$, $Z^3$ is $C(R^4)(R^{11c})$, and $Z^4$ is $C(R^{11c})(R^{11c})$. In some embodiments of the formulae above, or a pharmaceutically acceptable salt or solvate thereof, $Z^1$ is O, $Z^2$ is $C(R^{11c})(R^{11c})$, $Z^3$ is $C(R^4)(R^{11c})$, and $Z^4$ is O. In some embodiments of the formulae above, or a pharmaceutically acceptable salt or solvate thereof, $Z^1$ is O, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate thereof, $Z^1$ is O, $Z^2$ is $CH_2$, $Z^3$ is $CH_2$, and $Z^4$ is $N(R^4)$. In some embodiments of the formulae above, or a pharmaceutically acceptable salt or solvate thereof, $Z^1$ is O, $Z^2$ is $C(R^{11c})(R^{11c})$, $Z^3$ is $C(R^4)(R^{11c})$, and $Z^4$ is $N(R^{11c})$. In some embodiments of the formulae above, or a pharmaceutically acceptable salt or solvate thereof, $Z^1$ is O, $Z^2$ is $CH_2$, $Z^3$ is $C(R^4)(H)$, and $Z^4$ is $N(H)$. In some embodiments of the formulae above, or a pharmaceutically acceptable salt or solvate thereof, $Z^1$ is O, $Z^2$ is $C(R^{11c})(R^{11c})$, $Z^3$ is $C(R^4)(R^{11c})$, and $Z^4$ is O. In some embodiments of the formulae above, or a pharmaceutically acceptable salt or solvate thereof, $Z^1$ is O, $Z^2$ is $CH_2$, $Z^3$ is $C(R^4)(H)$, and $Z^4$ is O. In some embodiments of the formulae above, or a pharmaceutically acceptable salt or solvate thereof, $Z^1$ is $C(R^{11c})(R^{11c})$, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate solvate thereof, $Z^1$ is $CH_2$, $Z^2$ is $CH_2$, $Z^3$ is $CH_2$, and $Z^4$ is $N(R^4)$. In some embodiments of the formulae above, or a pharmaceutically acceptable salt or solvate thereof, $Z^1$ is $C(R^{11c})(R^{11c})$, $Z^2$ is $C(R^{11c})(R^{11c})$, $Z^3$ is $C(R^4)(R^{11c})$, and $Z^4$ is $N(R^{11c})$. In some embodiments of the formulae above, or a pharmaceutically acceptable salt or solvate thereof, $Z^1$ is $CH_2$, $Z^2$ is $CH_2$, $Z^3$ is $C(R^4)(H)$, and $Z^4$ is $N(H)$. In some embodiments of the formulae above, or a pharmaceutically acceptable salt or solvate thereof, $Z^1$ is $N(R^{11c})$, $Z^2$ is $C(R^{11c})(R^{11c})$, $Z^3$ is $C(R^{11c})(R^{11c})$, and $Z^4$ is $N(R^4)$. In some embodiments of the formulae above, or a pharmaceutically acceptable salt or solvate thereof, $Z^1$ is $N(H)$, $Z^2$ is $CH_2$, $z^3$ is $CH_2$, and $Z^4$ is $N(R^4)$. In some embodiments of the formulae above, or a pharmaceutically acceptable salt or solvate thereof, $Z^1$ is $N(R^{11c})$, $Z^2$ is $C(R^{11c})(R^{11c})$, $Z^3$ is $C(R^4)(R^{11c})$, and $Z^4$ is $N(R^{11c})$. In some embodiments of the formulae above, or a pharmaceutically acceptable salt or solvate thereof, $Z^1$ is $N(H)$, $Z^2$ is $CH_2$, $Z^3$ is $C(R^4)(H)$, and $Z^4$ is $N(H)$. In some embodiments of the formulae above, or a pharmaceutically acceptable salt or solvate thereof, $Z^1$ is O, $Z^2$ is $C(R^{11c})(R^{11c})$, $Z^3$ is $C(O)$, and $Z^4$ is $N(R^4)$. In some embodiments of the formulae above, or a pharmaceutically acceptable salt or solvate thereof, $Z^1$ is O, $Z^2$ is $CH_2$, $Z^3$ is $C(O)$, and $Z^4$ is $N(R^4)$. In some embodiments of the formulae above, or a pharmaceutically acceptable salt or solvate thereof, $Z^1$ is O, $Z^2$ is $C(R^{11c})(R^{11c})$, $Z^3$ is $C(R^{11c})(R^{11c})$, and $Z^4$ is $C(R^4)(R^{11c})$. In some embodiments of the formulae above, or a pharmaceutically acceptable salt or solvate thereof, $Z^1$ is O, $Z^2$ is $CH_2$, $Z^3$ is $CH_2$, and $Z^4$ is $C(R^4)(H)$. In some embodiments of the formulae above, or a pharmaceutically acceptable salt or solvate thereof, $Z^1$ is O, $Z^2$ is $C(R^{11c})(R^{11c})$, $Z^3$ is $C(R^4)(R^{11c})$, and $Z^4$ is $C(R^{11c})(R^{11c})$. In some embodiments of the formulae above, or a pharmaceutically acceptable salt or solvate thereof, $Z^1$ is O, $Z^2$ is $CH_2$, $Z^3$ is $C(R^4)(H)$, and $Z^4$ is $CH_2$.

In embodiments of the formulae above, at least one of $Z^1$, $Z^2$, $Z^3$, and $Z^4$ includes a ring heteroatom (e.g., $N(R^4)$, $N(R^{11c})$, $N(R^{11d})$, N, S, or O). In embodiments of the formulae above, at least two of $Z^1$, $Z^2$, $Z^3$, and $Z^4$ include a ring heteroatom (e.g., $N(R^4)$, $N(R^{11c})$, $N(R^{11d})$, N, S, or O). In embodiments of the formulae above, at least one of $Z^1$, $Z^2$, $Z^3$, and $Z^4$ includes a ring nitrogen (e.g., $N(R^4)$, $N(R^{11c})$, $N(R^{11d})$, or N). In embodiments of the formulae above, at least one of $Z^1$, $Z^2$, $Z^3$, and $Z^4$ includes a ring oxygen.

In embodiments of the formulae above, only one of $Z^1$, $Z^2$, $Z^3$, and $Z^4$ includes a ring heteroatom (e.g., $N(R^4)$, $N(R^{11c})$, $N(R^{11d})$, N, S, or O). In embodiments of the formulae above, only two of $Z^1$, $Z^2$, $Z^3$, and $Z^4$ include a ring heteroatom (e.g., $N(R^4)$, $N(R^{11c})$, $N(R^{11d})$, N, S, or O). In embodiments of the formulae above, only one of $Z^1$, $Z^2$, $Z^3$, and $Z^4$ includes a ring nitrogen (e.g., $N(R^4)$, $N(R^{11c})$, $N(R^{11d})$, or N). In embodiments of the formulae above, only one of $Z^1$, $Z^2$, $Z^3$, and $Z^4$ includes a ring oxygen.

In embodiments of the formulae above, exactly one of $Z^1$, $Z^2$, $Z^3$, and $Z^4$ includes $R^4$ (e.g., $N(R^4)$, $C(R^4)$, $C(R^4)(R^{11c})$, or $C(R^4)(R^4)$). In embodiments of the formulae above, exactly two of $Z^1$, $Z^2$, $Z^3$, and $Z^4$ includes $R^4$ (e.g., $N(R^4)$, $C(R^4)$, $C(R^4)(R^{11c})$, or $C(R^4)(R^4)$).

The individual embodiments herein below, or combinations thereof, (e.g., embodiments of $R^{11c}$, $L^4$, or $R^{4a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In embodiments of the formulae above, each $R^{11c}$ is independently selected from hydrogen, halogen, $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl, wherein $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$. In embodiments of the formulae above, each $R^{11c}$ is independently selected from hydrogen and $C_{1-6}$alkyl optionally substituted with one, two, or three $R^{20k}$. In embodiments of the formulae above, each $R^{11c}$ is independently selected from hydrogen and unsubstituted $C_{1-6}$alkyl. In embodiments of the formulae above, each $R^{11c}$ is hydrogen.

In embodiments of the formulae above, $L^4$ is a bond, —O—, —$N(R^{4d})$—, —$C(O)$—, or $CR^{4}R^{4c}$. In embodiments of the formulae above, $L^4$ is a bond. In embodiments of the formulae above, $L^4$ is-O—. In embodiments of the formulae above, $L^4$ is-$N(R^{4d})$—. In embodiments of the formulae above, $L^4$ is-$N(H)$—. In embodiments of the formulae above, $L^4$ is-$C(O)$—. In embodiments of the formulae above, $L^4$ is $CR^{4}R^{4c}$. In embodiments of the formulae above, $L^4$ is-$CH_2$—.

In embodiments of the formulae above, $R^{4a}$ is $C_{3-10}$cycloalkyl, $C_{2-9}$heterocycloalkyl, $C_{6-10}$aryl, and $C_{1-9}$heteroaryl optionally substituted with one, two, three, or four $R^{4b}$. In embodiments of the formulae above, $R^{4a}$ is $C_{3-10}$cycloalkyl optionally substituted with one, two, three, or four $R^{4b}$. In embodiments of the formulae above, $R^{4a}$ is $C_{2-9}$heterocycloalkyl optionally substituted with one, two, three, or four $R^{4b}$. In embodiments of the formulae above, $R^{4a}$ is $C_{6-10}$aryl optionally substituted with one, two, three, or four $R^{4b}$. In embodiments of the formulae above, each $R^{4a}$ is phenyl optionally substituted with one, two, three, or four $R^{4b}$. In embodiments of the formulae above, $R^{4a}$ is $C_{1-9}$heteroaryl optionally substituted with one, two, three, or four $R^{4b}$.

In an aspect is provided a compound of Formula (A), or a pharmaceutically acceptable salt or solvate thereof:

Formula (A)

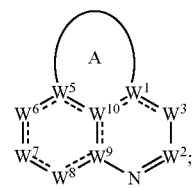

wherein:

Ring A is a 5-10 membered cycloalkyl or 5-10 membered heterocycloalkyl ring, wherein the 5-10 membered cycloalkyl ring and 5-10 membered heterocycloalkyl ring are substituted with one or more $R^4$ and optionally substituted with one or more $R^{11c}$;

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$, $W^2$ is $C(R^2)$;

$R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20b}$;

$W^3$ is $N(R^{3b})$, N, $C(R^3)$, $C(R^3)(R^{3a})$, or $C(O)$;

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(—OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, $C(O)$, $S(O)$, or $S(O)_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

Rob is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$, $W^7$ is $N(R^7)$, $C(R^7)$, or $C(R^7)(R^{7a})$;

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$, $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three $R^{20f}$, $R^7$ is -$L^7$-$R^{17}$;

$L^7$ is a bond, —O—, —N($R^{7d}$)—, —C(O)—, —S—, —S(O)$_2$—, —S(O)—, —P(O)$R^{7d}$—, $CR^7CR^{7c}$, —OCR$^{7c}R^{7c}$—, —N($R^{7d}$)CR$^{7c}R^{7c}$—, —S(O)CR$^{7c}R^{7c}$—, —SCR$^{7c}R^{7c}$—, —S(O)$_2$CR$^{7c}R^{7c}$—, —S(O)CR$^{7c}R^{7c}$—, —P(O)$R^{7d}$CR$^7R^{7c}$—, —CR$^7$CR$^7$&CR$^7$CR$^{7c}$—, —CR$^7R^{7c}$O—, —CR$^7R^{7c}$N($R^{7d}$)—, —CR$^7$CR$^{7c}$C(O)—, —CR$^7R^{7c}$S—, —CR$^{7c}R^{7c}$S(O)$_2$—, —CR$^{7c}R^{7c}$S(O)—, —CR$^7R^7$cP(O)$R^{7d}$—, —N($R^{7d}$)C(O)—, —N($R^{7d}$)S(O)$_2$—, —N($R^{7d}$)S(O)—, —N($R^{7d}$)P(O)$R^{7d}$—, —C(O)N($R^{7d}$)—, —S(O)$_2$N($R^{7d}$)—, —S(O)N($R^{7d}$)—, —P(O)$R^7$ON($R^{7d}$)—, —OC(O)—, —OS(O)$_2$—, —OS(O)—, —OP(O)$R^{7d}$—, —C(O)O—, —S(O)$_{20}$—, —S(O)O—, or —P(O)$R^{7d}$O—;

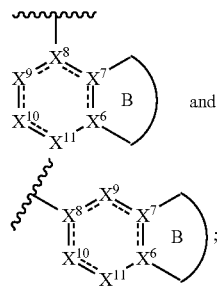

$R^{17}$ is selected from Ring B is a 5- or 6-membered cycloalkyl ring, 5- or 6-membered heterocycloalkyl ring, or 5- or 6-membered heteroaryl ring; wherein the 5- or 6-membered cycloalkyl ring, 5- or 6-membered heterocycloalkyl ring, and 5- or 6-membered heteroaryl ring are optionally substituted with one or more $R^{7c}$;

$X^6$, $X^7$, and $X^8$ are independently C or C($R^{1a}$);

$X^9$, $X^{10}$, and $X^{11}$ are independently C(O), C($R^{1a}$), or C($R^{1a}$)($R^{1b}$);

each $R^{1a}$, $R^{1b}$, and $R^{7c}$ is independently selected from hydrogen, halogen, —CN, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, $C_{1-9}$heteroaryl, —OR$^{12}$, —SR$^{12}$, —N($R^{12}$)($R^{13}$), —C(O)OR$^{12}$, —OC(O)N($R^{12}$)($R^{13}$), —N($R^{14}$)C(O)N($R^{12}$)($R^{13}$), —N($R^{14}$)C(O)OR$^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$W^8$ is C($R^8$), C($R^8$)($R^{6a}$), N, N($R^{8b}$), C(O), S(O), or S(O)$_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N($R^{12}$)($R^{13}$), —C(O)OR$^{12}$, —OC(O)N($R^{12}$)($R^{13}$), —N($R^{14}$)C(O)N($R^{12}$)($R^{13}$), —N($R^{14}$)C(O)OR$^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2R^{15}$, —S(O)$_2$N($R^{12}$)($R^{13}$)—, —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is C($R^9$), C, or N;

$W^{10}$ is C($R^9$), C, or N;

each $R^9$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20i}$, $R^4$ is -$L^4$-$R^{4a}$;

each $L^4$ is independently selected from a bond, —O—, —N($R^{4d}$)—, —C(O)—, —S—, —S(O)$_2$—, —S(O)—, —P(O)$R^{4d}$—, $CR^{4}R^{4C}$, —OCR$^{4}R^{4c}$—, —N($R^{4d}$)CR$^{4c}R^{4c}$—, —C(O)CR$^{4c}R^{4c}$—, —SCR$^4R^4$—, —S(O)$_2$CR$^{4c}R^{4c}$—, —S(O)CR$^{4c}R^{4c}$—, —P(O)$R^{4d}$CR$^4R^4$—, —CR$^4R^4$CR$^4R^4$, —CR$^4R^{4c}$O—, —CR$^{4c}R^4$CN($R^{4d}$)—, —CR$^4R^{4C}$(O)—, —CR$^4R^{4c}$S—, —CR$^{4c}R^{4c}$S(O)$_2$—, —CR$^{4c}R^{4c}$S(O)—, —CR$^4R^4$cP(O)$R^{4d}$—, —N($R^{4d}$)C(O)—, —N($R^{4d}$)S(O)$_2$—, —N($R^{4d}$)S(O)—, —N($R^{4d}$)P(O)$R^{4d}$—, —C(O)N($R^{4d}$)—, —S(O)$_2$N($R^{4d}$)—, —S(O)N($R^{4d}$)—, —P(O)$R^{4a}$N($R^{4d}$)—, —OC(O)—, —OS(O)$_2$—, —OS(O)—, —OP(O)$R^{4d}$—, —C(O)O—, —S(O)$_{20}$—, —S(O)O—, and —P(O)$R^{4d}$O—;

each $R^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N($R^{14}$)($R^{14}$), —C(O)C(O)N($R^{14}$)($R^{14}$), —OC(O)N($R^{14}$)($R^{14}$), —C(O)$R^{14a}$, —S(O)$_2R^{14}$, —S(O)$_2$N($R^{14}$)($R^{14}$), —OCH$_2$C(O)OR$^{14}$, —OC(O)$R^{14}$a, —N($R^{14}$)($R^{14}$), —N($R^{14}$)C(O)N($R^{14}$)($R^{14}$), —N($R^{14}$)C(O)OR$^{14}$, —N($R^{14}$)C(O)$R^{14a}$, and —N($R^{14}$)S(O)$_2R^{14}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N($R^{14}$)($R^{14}$), —C(O)OR$^{14}$, —C(O)N($R^{14}$)($R^{14}$), —C(O)C(O)N($R^{14}$)($R^{14}$), —OC(O)N($R^{14}$)($R^{14}$), —N($R^{14}$)C(O)N($R^{14}$)($R^{14}$), —N($R^{14}$)C(O)OR$^{14}$, —N($R^{14}$)C(O)$R^{14}$, —N($R^{14}$)S(O)$_2R^{14}$, —C(O)$R^{14a}$, —S(O)$_2R^{14}$, —S(O)$_2$N($R^{14}$)($R^{14}$), and —OC(O)$R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)R$^{14}$, and —OC(O)R$^{14}$a, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl, are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4a}$ is independently selected from C$_{2-9}$heterocycloalkyl, wherein C$_{2-9}$heterocycloalkyl, are optionally substituted with one, two, three, or four R$^{4b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, and C$_{1-9}$heteroaryl are optionally substituted with one or more R$^{20j}$;

each R$^{11c}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-12}$aryl, —CH$_2$-C$_{6-12}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-12}$aryl, —CH$_2$-C$_{6-12}$aryl, —CH$_2$-C$_{1-11}$heteroaryl, and C$_{1-11}$heteroaryl are optionally substituted with one, two, or three R$^{20k}$;

each R$^{12}$ is independently selected from hydrogen, C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl are optionally substituted with one, two, or three R$^{20l}$;

each R$^{12c}$ is independently selected from hydrogen and R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{14}$ is independently selected from hydrogen, C$_{1-6}$alkyl, and C$_{1-6}$haloalkyl;

each R$^{14a}$ is independently selected from C$_{1-6}$alkyl and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20m}$;

each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_3$-10cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl;

each R$^{23}$ is independently selected from H and C$_{1-6}$alkyl;

each R$^{24}$ is independently selected from H and C$_{1-6}$alkyl;

each R$^{25}$ is independently selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and ----- indicates a single or double bond such that all valences are satisfied.

In some embodiments, the compound of Formula (A), or a pharmaceutically acceptable salt or solvate thereof, has the structure of Formula (A-1):

Formula (A-1)

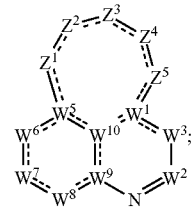

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$W^1$; $R^1$; $W^2$; $R^2$; $W^3$; $R^3$; $R^{3a}$; $R^{3b}$; $W^5$; $R^5$; $W^6$; $R^6$; $R^{6a}$; $R^{6b}$; $W^7$; $R^{7a}$; $R^{7c}$; $R^{7d}$; $R^7$; $L^7$; $R^{17}$; Ring B; $X^6$, $X^7$, $X^8$, $X^9$, $X^{10}$, $X^{11}$, $R^{1a}$, $R^{1b}$, $R^{7c}$; $W^8$; $R^8$; $R^{6a}$, $R^{8b}$; $W^9$; $W^{10}$; $R^9$; $R^4$; $L^4$; $R^{4c}$; $R^{4d}$; $R^{4a}$; $R^{4b}$; $R^{11c}$; $R^{12}$; $R^{12c}$; $R^{13}$; $R^{14}$; $R^{14a}$; $R^{15}$; $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, $R^{20m}$; $R^{21}$; $R^{22}$; $R^{23}$; $R^{24}$; and $R^{25}$ are as described for Formula (A), including in embodiments of a compound of Formula (A); and ----- indicates a single or double bond such that all valences are satisfied.

In some embodiments, the compound of Formula (A) or (A-1), or a pharmaceutically acceptable salt or solvate thereof, has the structure of Formula (A-1a):

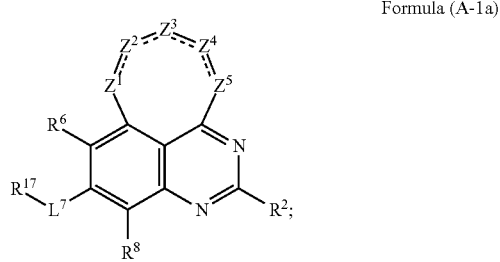

Formula (A-1a)

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$.

$R^2$; $R^6$; $L^7$; $R^{17}$; Ring B; $X^6$; $X^1$, $X^8$; $X^9$, $X^{10}$, $X^{11}$; $R^{1a}$, $R^{1b}$, $R^{7c}$; $R^8$; $R^9$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20c}$; $R^{20g}$, $R^{20h}$, $R^{20i}$, $R^{20j}$, $R^{20k}$, $R^{20l}$, $R^{20m}$; $R^{21}$; $R^{22}$; $R^{23}$; $R^{24}$; and $R^{25}$ are as described for Formula (A), including in embodiments of a compound of Formula (A); and ----- indicates a single or double bond such that all valences are satisfied.

In some embodiments, the compound of Formula (A) or (A-1), or a pharmaceutically acceptable salt or solvate thereof, has the structure of Formula (A-1b):

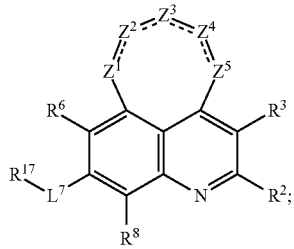

Formula (A-1b)

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^3$; $R^6$; $L^7$; $R^{17}$; Ring B; $X^6$, $X^1$, $X^8$; $X^9$, $X^{10}$, $X^{11}$; $R^{1a}$, $R^{1b}$, $R^{7c}$; $R^8$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$;

$R^{20b}$, $R^{20c}$; $R^{20c}$; $R^{20g}$, $R^{20h}$, $R^{20j}$, $R^{20k}$, $R^{20l}$, $R^{20m}$; $R^{21}$; $R^{22}$; $R^{23}$; $R^{24}$; and $R^{25}$; are as described for Formula (A), including in embodiments of a compound of Formula (A); and ----- indicates a single or double bond such that all valences are satisfied.

In some embodiments, the compound of Formula (A) or (A-1), or a pharmaceutically acceptable salt or solvate thereof, has the structure of Formula (A-1c):

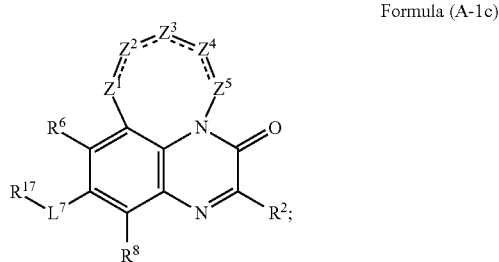

Formula (A-1c)

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^6$; $L^7$; $R^{17}$; Ring B; $X^6$, $X^1$, $X^8$; $X^1$, $X^{10}$, $X^{11}$; $R^{14}$, $R^{1b}$, $R^{7c}$; $R^8$; $R^4$; $L^4$; $R^{4c}$; $R^{4a}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20c}$; $R^{20g}$, $R^{20h}$, $R^{20i}$, $R^{20j}$, $R^{20k}$, $R^{20l}$, $R^{20m}$; $R^{21}$; $R^{22}$; $R^{23}$; $R^{24}$; and $R^{25}$ are as described for Formula (A), including in embodiments of a compound of Formula (A); and indicates a single or double bond such that all valences are satisfied.

In some embodiments, the compound of Formula (A) or (A-1), or a pharmaceutically acceptable salt or solvate thereof, has the structure of Formula (A-1d):

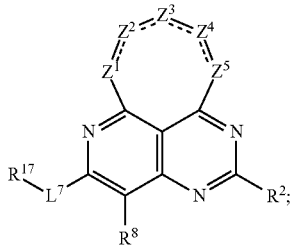

Formula (A-1d)

$Z^1$, $Z^3$, and $Z^5$ are each independently selected from $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O); and $Z^2$ and $Z^4$ are each independently selected from a bond, $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $L^7$; $R^{17}$; Ring B; $X^6$, $X^1$, $X^8$, $X^9$, $X^{10}$, $X^{11}$; $R^{18}$, $R^{1b}$, $R^{7c}$; $R^8$; $R^4$; $L^4$; $R^{4c}$; $R^{4a}$, $R^{48}$, $R^{46}$; $R^{11c}$; $R^{12}$; $R^{12c}$; $R^{13}$; $R^{14}$; $R^{14a}$; $R^{15}$; $R^{20b}$, $R^{20g}$, $R^{20h}$, $R^{20j}$, $R^{20k}$, $R^{20l}$, $R^{20m}$; $R^{21}$; $R^{22}$; $R^{23}$; $R^{24}$; and $R^{25}$ are as described for Formula (A), including in embodiments of a compound of Formula (A); and ----- indicates a single or double bond such that all valences are satisfied.

In some embodiments, the compound of Formula (A) or (A-1), or a pharmaceutically acceptable salt or solvate thereof, has the structure of Formula (A-1e):

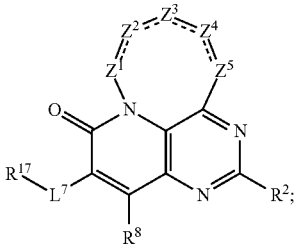

Formula (A-1e)

$Z^1$, $Z^3$, and $Z^5$ are each independently selected from $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O); and $Z^2$ and $Z^4$ are each independently selected from a bond, $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $L^7$; $R^{17}$; Ring B; $X^6$, $X^1$, $X^8$, $X'$, $X^{10}$, $X^{11}$, $R^{14}$, $R^{1b}$, $R^{1c}$; $R^8$; $R^4$; $L^4$; $R^{4c}$; $R^{4d}$, $R^{48}$, $R^{4b}$; $R^{11c}$; $R^{12}$; $R^{12c}$; $R^{13}$; $R^{14}$; $R^{14a}$; $R^{15}$; $R^{20b}$, $R^{20g}$, $R^{20h}$, $R^{20j}$, $R^{20k}$, $R^{20l}$, $R^{20m}$; $R^{21}$; $R^{22}$; $R^{23}$; $R^{24}$; and $R^{25}$ are as described for Formula (A), including in embodiments of a compound of Formula (A); and ----- indicates a single or double bond such that all valences are satisfied.

In some embodiments, the compound of Formula (A) or (A-1), or a pharmaceutically acceptable salt or solvate thereof, has the structure of Formula (A-1f):

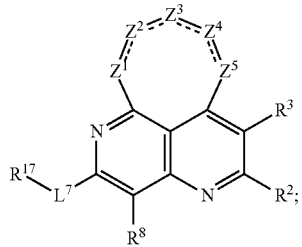

Formula (A-1f)

$Z^1$, $Z^3$, and $Z^5$ are each independently selected from $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O); and $Z^2$ and $Z^4$ are each independently selected from a bond, $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^3$; $L^7$; $R^{17}$; Ring B; $X^6$, $X^7$, $X^8$, $X^9$, $X^{10}$, $X^{11}$; $R^{18}$, $R^{1b}$, $R^{7c}$; $R^8$; $R^4$; LA; $R^{4c}$; $R^{4a}$, $R^{4a}$, $R^{4b}$; $R^{11c}$; $R^{12}$; $R^{12c}$; $R^{13}$; $R^{14}$; $R^{14a}$; $R^{15}$; $R^{20b}$, $R^{20c}$, $R^{20g}$, $R^{20h}$, $R^{20j}$, $R^{20k}$, $R^{20l}$, $R^{20m}$; $R^{21}$; $R^{22}$; $R^{23}$; $R^{24}$; $R^{25}$; and ----- indicates a single or double bond such that all valences are satisfied.

In an aspect is provided a compound of Formula (B), or a pharmaceutically acceptable salt or solvate thereof:

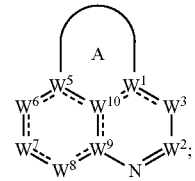

Formula (B)

wherein:

Ring A is a 5-10 membered cycloalkyl or 5-10 membered heterocycloalkyl ring, wherein the 5-10 membered cycloalkyl and 5-10 membered heterocycloalkyl ring are optionally substituted with one or more $R^4$ and optionally substituted with one or more $R^{11c}$;

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S$ $(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $C(R^2)$;

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20b}$;

$W^3$ is $N(R^{3b})$, N, $C(R^3)$, $C(R^3)(R^{3a})$, or C(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_2$—, heterocycloalkyl, $C_{6-10}$aryl, $C_1$-heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, C(O), S(O), or $S(O)_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$R^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20e}$;

$W^7$ is $N(R^7)$, $C(R^7)$, or $C(R^7)(R^{7a})$;

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_2$-9 heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20f}$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three $R^{20f}$;

$R^7$ is -$L^7$-$R^{17}$;

$L^7$ is a bond, —O—, —$N(R^{7d})$—, —C(O)—, —S—, —$S(O)_2$—, —S(O)—, —$P(O)R^{7d}$, $CR^{7o}R^{7c}$, —$OCR^{7c}R^{7c}$—, —$N(R^{7d})CR^{7c}R^{7c}$—, —C(O)$CR^{7o}R^{7c}$—, —$SCR^7R^{7c}$—, —$S(O)_2CR^{7c}R^{7c}$—, —$S(O)CR^{7c}R^{7c}$—, —$P(O)R^{7d}CR^7R^{7c}$—, —$CR^7CR^{7c}CR^7CR^{7c}$—, —$CR^7R^{7c}O$—, —$CR^7R^{7c}N(R^{7d})$—, —$CR^7R^{7c}C(O)$—, —$CR^7R^{7c}S$—, —$CR^7R^{7c}S(O)_2$—, —$CR^7R^{7c}S(O)$—, —$CR^7R^7cP(O)R^{7d}$—, —$N(R^{7d})C(O)$—, —$N(R^{7d})S(O)_2$—, —$N(R^{7d})S(O)$—, —$N(R^{7d})P(O)R^{7d}$—, —C(O)N($R^{7d}$)—, —$S(O)_2N(R^{7d})$—, —$S(O)N(R^{7d})$—, —$P(O)R^{7a}N(R^{7d})$—, —OC(O)—, —$OS(O)_2$—, —OS(O)—, —$OP(O)R^{7d}$—, —C(O)O—, —$S(O)_2O$—, —S(O)O—, or —P(O)$R^{7d}$O—;

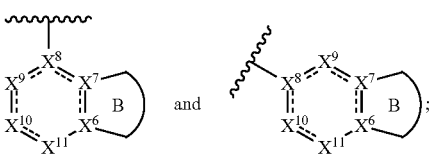

$R^{17}$ is selected from Ring B is a 5- or 6-membered cycloalkyl ring, 5- or 6-membered heterocycloalkyl ring, 5- or 6-membered heteroaryl ring, or 6-membered aryl ring, wherein the 5- or 6-membered cycloalkyl ring, 5- or 6-membered heterocycloalkyl ring, 5- or 6-membered heteroaryl ring, and 6-membered aryl ring are optionally substituted with one or more $R^{7c}$;

$X^6$, $X^7$, and $X^8$ are independently C or $C(R^{1a})$;

$X^9$, $X^{10}$, and $X^{11}$ are independently C(O), $C(R^{1a})$, or $C(R^{1a})(R^{1b})$;

each $R^{1a}$, $R^{1b}$, and $R^{7c}$ is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$W^8$ is $C(R^8)$, $C(R^8)(R^{8a})$, N, $N(R^{8b})$, C(O), S(O), or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $W^9$ is $C(R^9)$, C, or N;

$W^{10}$ is C(R'), C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_1$-heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$;

$R^4$ is -$L^4$-$R^{4a}$;

each $L^4$ is independently selected from a bond, —O—, —$N(R^{4d})$—, —C(O)—, —S—, —$S(O)_2$—, —S(O)—, —$P(O)R^{4d}$, $CR^4R^4$, —$OCR^4R^{4c}$—, —$N(R^{4d})CR^{4c}R^{4c}$—, —$C(O)CR^4R^{4c}$—, —$SCR^4R^{4c}$—, —$S(O)_2$ $CR^4R^{4c}$—, —$S(O)CR^{4c}R^{4c}$—, —$P(O)R^{4d}CR^4R^{4c}$—, —$CR^{4c}R^{4c}CR^{4c}R^{4c}$—, —$CR^4R^{4c}O$—, —$CR^4RN(R^{4d})$—, —$CR^4R^{4c}(O)$—, —$CR^4R^{4c}S$—, —$CR^4R^{4c}S(O)_2$—, —$CR^4R^{4c}S(O)$—, —$CR^4R^4CP(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^4ON(R^{4d})$—, —OC(O)—, —$OS(O)_2$—, —OS(O)—, —OP(O)$R^{4d}$—, —C(O)O—, —$S(O)_{20}$—, —S(O)O—, and —$P(O)R^{4d}O$—;

each $R^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_1$-6haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH_2C(O)OR^{14}$, —$OC(O)R^{14}$a, —$N(R^{14})(R^{14})$, —$N(R^{14})C(O)N(R^{14})(R^{14})$, —$N(R^{14})C(O)OR^{14}$, —$N(R^{14})C(O)R^{14a}$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH_2C(O)OR^{14}$, and —$OC(O)R^{14a}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)$N(R^{12})(R^{13})$, —$N(R^{14})$C(O)$N(R^{12})(R^{13})$, —$N(R^{14})$C(O)$OR^{15}$, —$N(R^{14})S(O)_2R^{15}$, —C(O)$R^{15}$, —S(O)$R^{15}$, —OC(O)$R^{15}$, —C(O)$N(R^{12})(R^{13})$, —C(O)C(O)$N(R^{12})(R^{13})$, —$N(R^{14})$C(O)$R^{15}$, —S(O)$_2R^{15}$, —S(O)$_2N(R^{12})(R^{13})$—, —S(=O)(=NH)$N(R^{12})(R^{13})$, —CH$_2$C(O)$N(R^{12})(R^{13})$, —CH$_2N(R^{14})$C(O)$R^{15}$, —CH$_2$S(O)$_2R^{15}$, —CH$_2$S(O)$_2N(R^{12})(R^{13})$, and —P(=O)$(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-12}$aryl, —CH$_2$-$C_{6-12}$aryl, —CH$_2$-$C_{1-11}$heteroaryl, $C_{1-11}$heteroaryl, —$OR^{12}$, —$SR^{12}$, —$N(R^{12})(R^{13})$, —C(O)$OR^{12}$, —OC(O)$N(R^{12})(R^{13})$, —$N(R^{14})$C(O)N$(R^{12})(R^{13})$, —$N(R^{14})$C(O)$OR^{15}$, —$N(R^{14})S(O)_2R^{15}$, —C(O)$R^{15}$, —S(O)$R^{15}$, —OC(O)$R^{15}$, —C(O)$N(R^{12})(R^{13})$, —C(O)C(O)$N(R^{12})(R^{13})$, —$N(R^{14})$C(O)$R^{15}$, —S(O)$_2R^{15}$, —S(O)$_2N(R^{12})(R^{13})$—, —S(=O)(=NH)$N(R^{12})(R^{13})$, —CH$_2$C(O)$N(R^{12})(R^{13})$, —CH$_2N(R^{14})$C(O)$R^{15}$, —CH$_2$S(O)$_2R^{15}$, and —CH$_2$S(O)$_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-12}$aryl, —CH$_2$-$C_{6-12}$aryl, —CH$_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —C$(R^{12c})_2$-$C_{3-10}$cycloalkyl, $C_{2-9}$heterocycloalkyl, —C$(R^{12c})_2$-$C_{2-9}$heterocycloalkyl, $C_{6-10}$aryl, —C$(R^{12c})_2$-$C_{6-10}$aryl, —C$(R^{12c})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C$(R^{12c})_2$-$C_{3-10}$cycloalkyl, $C_{2-9}$heterocycloalkyl, —C$(R^{12c})_2$-$C_{2-9}$heterocycloalkyl, $C_{6-10}$aryl, —C$(R^{12c})_2$-$C_{6-10}$aryl, —C$(R^{12c})_2$-$C_{1-9}$heteroaryl, and $C_{1-9}$heteroaryl are optionally substituted with one, two, or three $R^{20l}$;

each $R^{12c}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{14}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$; $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —$OR^{21}$, —$SR^{21}$, —$N(R^{22})(R^{23})$, —C(O)$OR^{22}$, —C(O)$N(R^{22})(R^{23})$, —C(O)C(O)N$(R^{22})(R^{23})$, —OC(O)$N(R^{22})(R^{23})$, —$N(R^{24})$C(O)N$(R^{22})(R^{23})$, —$N(R^{24})$C(O)$OR^{25}$, —$N(R^{24})$C(O)$R^{25}$, —$N(R^{24})S(O)_2R^{25}$, —C(O)$R^{25}$, —S(O)$_2R^{25}$, —S(O)$_2$N$(R^{22})(R^{23})$, —OCH$_2$C(O)$OR^{22}$, and —OC(O)$R^{25}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —C(O)$OR^{22}$, —C(O)$N(R^{22})(R^{23})$, —C(O)C(O)$N(R^{22})(R^{23})$, —OC(O)$N(R^{22})(R^{23})$, —$N(R^{24})$C(O)$N(R^{22})(R^{23})$, —$N(R^{24})$C(O)$OR^{25}$, —$N(R^{24})$C(O)$R^{25}$, —$N(R^{24})S(O)_2R^{25}$, —C(O)$R^{25}$, —S(O)$_2R^{25}$, —S(O)$_2N(R^{22})(R^{23})$, and —OC(O)$R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;
each $R^{24}$ is independently selected from H and $C_{1-6}$alkyl;
each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments, the compound of Formula (B), or a pharmaceutically acceptable salt or solvate thereof, has the structure of Formula (B-1):

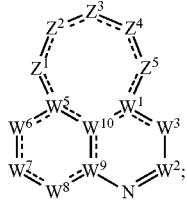

Formula (B-1)

wherein $Z^1$, $Z^3$, and $Z^5$ are each independently selected from $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, CH$_2$, S, O, and C(O);

$Z^2$ and $Z^4$ are each independently selected from a bond, $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, CH$_2$, S, O, and C(O);

$W^1$; $R^1$; $W^2$; $R^2$; $W^3$; $R^3$; $R^{38}$; $R^{3b}$; $W^5$; $R^5$; $W^6$; $R^{6a}$; Rob; $W^7$; $R^{78}$; $R^{7c}$; $R^{7d}$; $R^7$; $L^7$; $R^{17}$; Ring B; $X^6$, $X^1$, $X^8$, $X^9$, $X^{10}$, $X^{11}$, Rla, $R^{1b}$, $R^{7c}$; $W^8$; $R^8$; $R^{88}$; $R^{8b}$; $W^9$; $W^{10}$; $R^9$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$; $R^{20a}$; $R^{20b}$, $R^{20c}$; $R^{20g}$, $R^{20b}$, $R^{20f}$, $R^{20g}$, $R^{20h}$, $R^{20i}$, $R^{20j}$, $R^{20k}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In some embodiments, the compound of Formula (B) or (B-1), or a pharmaceutically acceptable salt or solvate thereof, has the structure of Formula (B-1a):

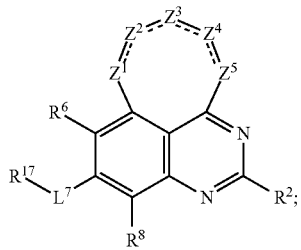

Formula (B-1a)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$R^2$; $R^6$; $L^7$; $R^{17}$; Ring B; $X^6$, $X^7$, $X^8$; $X^9$, $X^{10}$, $X^{11}$; $R^{1a}$, $R^{1b}$, $R^{1c}$; $R^8$; $R^4$; $L^4$; $R^{4c}$; $R^{4a}$; $R^{4B}$; $R^{4b}$; $R^{11c}$; $R^{12}$; $R^{12c}$; $R^{13}$; $R^{14}$; $R^{14a}$; $R^{15}$; $R^{20b}$, $R^{20e}$, $R^{20g}$, $R^{20h}$, $R^{20j}$, $R^{20g}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In some embodiments, the compound of Formula (B) or (B-1), or a pharmaceutically acceptable salt or solvate thereof, has the structure of Formula (B-1b):

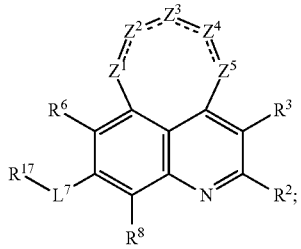

Formula (B-1b)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$R^2$; $R^3$; $R^6$; $L^7$; $R^{17}$; Ring B; $X^6$, $X^7$, $X^8$; $X^9$, $X^{10}$, $X^{11}$; $R^{1a}$, $R^{1b}$, $R^{7c}$; $R^8$; $R^4$; $L^4$; $R^{4c}$; $R^{4a}$; $R^{43}$; $R^{4b}$; $R^{11c}$; $R^{12}$; $R^{12c}$; $R^{13}$; $R^{14}$; $R^{14a}$; $R^{15}$; $R^{20b}$, $R^{20c}$, $R^{20e}$, $R^{20g}$, $R^{20h}$, $R^{20j}$, $R^{20k}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In some embodiments, the compound of Formula (B) or (B-1), or a pharmaceutically acceptable salt or solvate thereof, has the structure of Formula (B-1c):

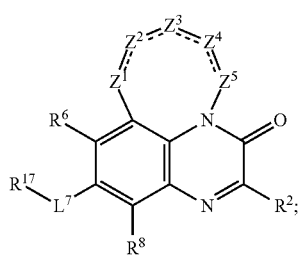

Formula (B-1c)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$R^2$; $R^6$; $L^7$; $R^{17}$; Ring B; $X^6$, $X^1$, $X^8$; $X^9$, $X^{10}$, $X^{11}$; $R^{18}$, $R^{1b}$, $R^{7c}$; $R^8$; $R^4$; $L^4$; $R^4$; $R^{4a}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20e}$, $R^{20g}$, $R^{20h}$, $R^{20j}$, $R^{20k}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In some embodiments, the compound of Formula (B) or (B-1), or a pharmaceutically acceptable salt or solvate thereof, has the structure of Formula B-1d):

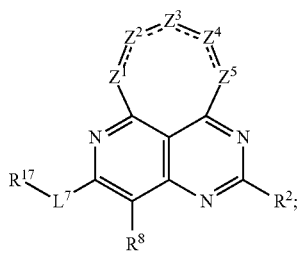

Formula (B-1d)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$R^2$; $L^7$; $R^{17}$; Ring B; $X^6$, $X^7$, $X^8$, $X^9$, $X^{10}$, $X^{11}$; $R^{18}$, $R^{1b}$, $R^{7c}$; $R^8$; $R^4$; $L^4$; $R^{4c}$; $R^{4a}$; $R^{4B}$; $R^{4b}$; $R^{11c}$; $R^{12}$; $R^{12c}$; $R^{13}$; $R^{14}$; $R^{14a}$; $R^{15}$; $R^{20b}$, $R^{20g}$, $R^{20h}$, $R^{20j}$, $R^{20g}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In some embodiments, the compound of Formula (B) or (B-1), or a pharmaceutically acceptable salt or solvate thereof, has the structure of Formula (B-1e):

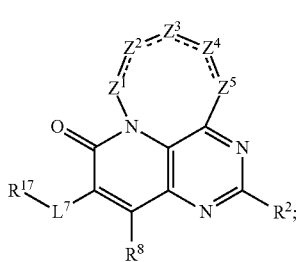

Formula (B-1e)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$R^2$; $L^7$; $R^{17}$; Ring B; $X^6$, $X^7$, $X^8$, $X^9$, $X^{10}$, $X^{11}$; $R^{18}$, $R^{1b}$, $R^{7c}$; $R^8$; $R^4$; $L^4$; $R^{4c}$; $R^{4a}$; $R^{4B}$; $R^{4b}$; $R^{11c}$; $R^{12}$; $R^{12c}$; $R^{13}$; $R^{14}$; $R^{14a}$; $R^{15}$; $R^{20b}$, $R^{20g}$, $R^{20h}$, $R^{20j}$, $R^{20g}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In some embodiments, the compound of Formula (B) or (B-1), or a pharmaceutically acceptable salt or solvate thereof, has the structure of Formula (B-1f):

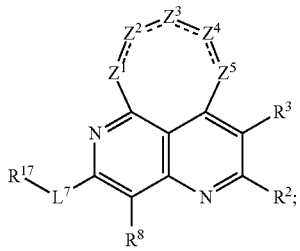

Formula (B-1f)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$R^2$; $R^3$; $L^7$; $R^{17}$; Ring B; $X^6$, $X^1$, $X^8$, $X^9$, $X^{10}$, $X^{11}$; $R^{14}$, $R^{1b}$, $R^{7c}$; $R^8$; $R^4$; $L^4$; $R^4$; $R^{4a}$; $R^{4B}$; $R^{4b}$; $R^{11c}$; $R^{12}$; $R^{12c}$; $R^{13}$; $R^{14}$; $R^{14a}$; $R^{15}$; $R^{20}\%$, $R^{20c}$; $R^{20g}$, $R^{20h}$, $R^{20j}$, $R^{20g}$, $R^{20l}$, $R^{20m}$; $R^{21}$; $R^{22}$; $R^{23}$; $R^{24}$; and $R^{25}$ are as described for Formula (B), including in embodiments of a compound of Formula (B); and ----- indicates a single or double bond such that all valences are satisfied.

In an aspect is provided a compound of Formula (C), or a pharmaceutically acceptable salt or solvate thereof:

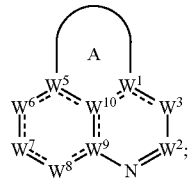

Formula (C)

wherein:

Ring A is a 5-10 membered cycloalkyl or 5-10 membered heterocycloalkyl ring, wherein the 5-10 membered cycloalkyl and 5-10 membered heterocycloalkyl ring are substituted with at least one $R^4$, and wherein the 5-10 membered cycloalkyl and 5-10 membered heterocycloalkyl ring are optionally substituted with one or more $R^{11c}$;

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $C(R^2)$;

$R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$, $W^3$ is $N(R^{3b})$, N, $C(R^3)$, $C(R^3)(R^{3a})$, or $C(O)$;

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

R$^{3b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

W$^5$ is C(R$^5$), C, or N;

R$^5$ is selected from hydrogen, halogen, —CN, C$_{1-6}$alkyl, C$_{2-6}$alkenyl, C$_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, and C$_{2-6}$alkynyl are optionally substituted with one, two, or three R$^{20d}$;

W$^6$ is N(R$^{6b}$), N, C(R$^6$), C(R$^6$)(R$^{6a}$), C(O), S(O), or S(O)$_2$;

R$^6$ and R$^{6a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

R$^{6b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20e}$;

W$^7$ is N(R$^7$), C(R$^7$), or C(R$^7$)(R$^{7a}$);

R$^{7a}$ and each R$^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_2$-9 heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-heteroaryl are optionally substituted with one, two, or three R$^{20f}$;

R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl are optionally substituted with one, two, or three R$^{20f}$;

R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$, CR$^7$R$^{7c}$, —OCR$^{7c}$R$^{7c}$—, —N(R$^{7d}$)CR$^{7c}$R$^{7c}$—, —C(O)CR$^7$R$^{7c}$—, —SCR$^7$R$^{7c}$—, —S(O)$_2$CR$^7$CR$^{7c}$—, —S(O)CR$^{7d}$R$^{7c}$—, —P(O)R$^{7d}$CR$^{7c}$R$^{7c}$—, —CR$^{7c}$R$^{7c}$CCR$^7$CR$^{7c}$, —CR$^7$CR$^{7c}$O—, —CR$^{7c}$R$^{7a}$N(R$^{7d}$)—, —CR$^7$CR$^{7c}$C(O)—, —CR$^{7o}$R$^{7c}$S—, —CR$^{7o}$R$^{7c}$S(O)$_2$—, —CR$^7$CR$^{7c}$S(O)—, —CR$^{7c}$R$^7$cP(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{7d}$)—, —P(O)R$^{7a}$N(R$^{7d}$)—, —OC(O)—, —OS(O)$_2$—, —OS(O)—, —OP(O)R$^{7d}$—, —C(O)O—, —S(O)$_{20}$—, —S(O)O—, or —P(O)R$^{7d}$O—;

R$^{17}$ is selected from C$_{2-9}$heterocycloalkyl and C$_{1-9}$heteroaryl, wherein C$_{2-9}$heterocycloalkyl and C$_{1-9}$heteroaryl are optionally substituted with one, two, or three R$^{20g}$;

W$^8$ is C(R$^8$), C(R$^8$)(R$^{6a}$), N, N(R$^{8b}$), C(O), S(O), or S(O)$_2$;

R$^8$ and R$^{8a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

R$^{8b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$;

W$^9$ is C(R$^9$), C, or N;

W$^{10}$ is C(R'), C, or N;

each R$^9$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three R$^{20i}$, R$^4$ is -L$^4$-R$^{4a}$, L$^4$ is a bond, —O—, —N(R$^{4d}$)—, —C(O)—, —S—, —S(O)$_2$—, —S(O)—, —P(O)R$^{4d}$—, CR$^{4c}$R$^4$, —OCR$^4$R$^{4c}$—, —N(R$^{4d}$)CR$^4$R$^{4c}$—, —C(O) CR$^4$R$^{4c}$—, —SCR$^4$R$^{4c}$—, —S(O)$_2$CR$^4$R$^{4c}$—, —S(O) CR$^4$R$^{4c}$—, —P(O)R$^{4d}$CR$^4$R$^{4c}$—, —CR$^4$R$^4$CCR$^4$R$^4$, —CR$^4$R$^{4c}$O—, —CR$^4$R$^{4N}$(R$^{4d}$)—, —CR$^4$R$^{4c}$C(O)—, —CR$^{4c}$R$^{4c}$S—, —CR$^4$R$^{4c}$S(O)$_2$—, —CR$^{4c}$R$^{4c}$S (O)—, —CR$^4$R$^4$CP(O)R$^{4d}$—, —N(R$^{4d}$)C(O)—, —N(R$^{4d}$)S(O)$_2$—, —N(R$^{4d}$)S(O)—, —N(R$^{4d}$)P(O) R$^{4d}$—, —C(O)N(R$^{4d}$)—, —S(O)$_2$N(R$^{4d}$)—, —S(O)N (R$^{4d}$)—, —P(O)R$^{4d}$N(R$^{4d}$)—, —OC(O)—, —OS(O)$_2$—, —OS(O)—, —OP(O)R$^{4d}$—, —C(O) O—, —S(O)$_{20}$—, —S(O)O—, or —P(O)R$^{4d}$O—;

each R$^4$ is independently selected from hydrogen, halogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O)N(R$^{14}$)(R$^{14}$), —C(O)C(O)N (R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, —OC(O)R$^{14}$a, —N(R$^{14}$)(R$^{14}$), —N(R$^{14}$)C(O)N(R$^{14}$) (R$^{14}$), —N(R$^{14}$)C(O)OR$^{14}$, —N(R$^{14}$)C(O)R$^{14a}$, and —N(R$^{14}$)S(O)$_2$R$^{14}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl, are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{14}$, —SR$^{14}$, —N(R$^{14}$)(R$^{14}$), —C(O) OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S (O)$_2$R$^{14}$, —C(O)R$^{14a}$, —S(O)$_2$R$^{14}$, —S(O)$_2$N(R$^{14}$) (R$^{14}$), and —OC(O)R$^{14a}$;

each R$^{4d}$ is independently selected from hydrogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O) N(R$^{14}$)(R$^{14}$), —C(O)C(O)N(R$^{14}$)(R$^{14}$), —OC(O)N (R$^{14}$)(R$^{14}$), —C(O)R$^{14a}$, —S(O)$_2$R$^{14}$, —S(O)$_2$N(R$^{14}$) (R$^{14}$), —OCH$_2$C(O)OR$^{14}$, and —OC(O)R$^{14}$a, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, and —CH$_2$-C$_{2-9}$heterocycloalkyl , are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

R$^{4a}$ is selected from C$_{3-10}$cycloalkyl, C$_{2-9}$heterocycloalkyl, and C$_{6-10}$aryl, wherein C$_{3-10}$cycloalkyl, C$_{2-9}$heterocycloalkyl, and C$_{6-10}$aryl are optionally substituted with one, two, three, or four R$^{4b}$;

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O) OR$^{12}$, —OC(O)N(R$^{12}$)(R$^{13}$), —N(R$^{14}$)C(O)N(R$^{12}$) (R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O) (=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, and C$_{1-9}$heteroaryl are optionally substituted with one or more R$^{20j}$;

each R$^{11c}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-12}$aryl, —CH$_2$-C$_{6-12}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N (R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$) (R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O) (=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S (O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-12}$aryl, —CH$_2$-C$_{6-12}$aryl, —CH$_2$-C$_{1-11}$heteroaryl, and C$_{1-11}$heteroaryl are optionally substituted with one, two, or three R$^{20k}$;

each R$^{12}$ is independently selected from hydrogen, C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl , —C(R$^{12c}$)$_2$-C$_{2-9}$heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C(R$^{12c}$)$_2$-C$_{3-10}$cycloalkyl, C$_{2-9}$heterocycloalkyl, —C(R$^{12c}$)$_2$-C$_2$-9 heterocycloalkyl, C$_{6-10}$aryl, —C(R$^{12c}$)$_2$-C$_{6-10}$aryl, —C(R$^{12c}$)$_2$-C$_{1-9}$heteroaryl, and C$_{1-9}$heteroaryl are optionally substituted with one, two, or three R$^{20l}$;

each R$^{12c}$ is independently selected from hydrogen and R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{14}$ is independently selected from hydrogen, C$_{1-6}$alkyl, and C$_{1-6}$haloalkyl;

each R$^{14a}$ is independently selected from C$_{1-6}$alkyl and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;
each $R^{24}$ is independently selected from H and $C_{1-6}$alkyl;
each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments, the compound of Formula (C), or a pharmaceutically acceptable salt or solvate thereof, has the structure of Formula (C-1):

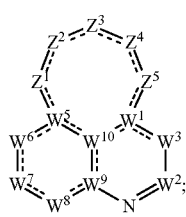

Formula (C-1)

wherein
$Z^1$, $Z^3$, and $Z^5$ are each independently selected from $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

$Z^2$ and $Z^4$ are each independently selected from a bond, $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$W^1$; $R^1$; $W^2$; $R^2$; $W^3$; $R^3$; $R^{3a}$, $R^{3b}$; $W^5$; $R^5$; $W^6$; $R^6$; $R^{6a}$; $R^{6b}$; $W^7$; $R^{7a}$; $R^{7c}$; $R^{7d}$; $R^7$; $L^7$; $R^{17}$; $W^8$; $R^8$; $R^{8a}$; $R^{8b}$; $W^9$; $W^{10}$; $R^9$; $R^4$; $L^4$; $R^4$;

$R^{4d}$; $R^{48}$; $R^{46}$; $R^{11c}$; $R^{12}$; $R^{12c}$; $R^{13}$; $R^{14}$; $R^{14a}$; $R^{15}$; $R^{20a}$; $R^{20b}$, $R^{20c}$; $R^{20d}$, $R^{208}$, $R^{20f}$, $R^{20g}$, $R^{20h}$, $R^{20l}$, $R^{20j}$, $R^{20k}$, $R^{20l}$, $R^{20m}$; $R^{21}$; $R^{22}$;

$R^{23}$; $R^{24}$; and $R^{25}$ are as described for Formula (C), including in embodiments of a compound of Formula (C); and ----- indicates a single or double bond such that all valences are satisfied.

In some embodiments, the compound of Formula (C) or (C-1), or a pharmaceutically acceptable salt or solvate thereof, has the structure of Formula (C-1a):

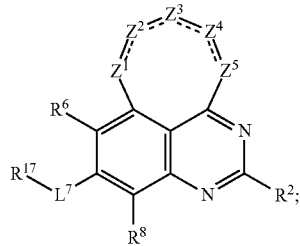

Formula (C-1a)

wherein
$Z^1$, $Z^3$, and $Z^5$ are each independently selected from $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

$Z^2$ and $Z^4$ are each independently selected from a bond, $N(R^4)$, $N(R^{11c})$, N(H), N, $C(R^4)$, $C(R^{11c})$, C(H), $C(R^4)(H)$, $C(R^4)(R^{11c})$, $C(R^{11c})(R^{11c})$, $C(R^4)(R^4)$, $C(R^{11c})(H)$, $CH_2$, S, O, and C(O);

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^6$; $L^7$; $R^{17}$; $R^8$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20e}$, $R^{20g}$, $R^{20h}$, $R^{20j}$, $R^{20k}$, $R^{20l}$, $R^{20m}$; $R^{21}$; $R^{22}$;

$R^{23}$; $R^{24}$; and $R^{25}$ are as described for Formula (C), including in embodiments of a compound of Formula (C); and ----- indicates a single or double bond such that all valences are satisfied.

In some embodiments, the compound of Formula (C) or (C-1), or a pharmaceutically acceptable salt or solvate thereof, has the structure of Formula (C-1b):

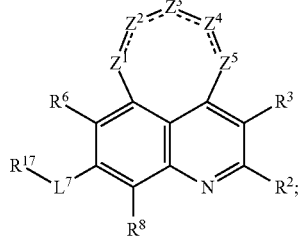

Formula (C-1b)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^3$; $R^6$; $L^7$; $R^{17}$; $R^8$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20c}$; $R^{20e}$; $R^{20g}$, $R^{20h}$, $R^{20j}$, $R^{20k}$, $R^{20l}$, $R^{20m}$;

$R^{21}$; $R^{22}$; $R^{23}$; $R^{24}$; and $R^{25}$ are as described for Formula (C), including in embodiments of a compound of Formula (C); and ----- indicates a single or double bond such that all valences are satisfied.

In some embodiments, the compound of Formula (C) or (C-1), or a pharmaceutically acceptable salt or solvate thereof, has the structure of Formula (C-1c):

Formula (C-1c)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^6$; $L^7$; $R^{17}$; $R^8$; $R^4$; $L^4$; $R^{4c}$; $R^{4a}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20c}$; $R^{20g}$, $R^{20h}$, $R^{20j}$, $R^{20k}$, $R^{20l}$, $R^{20m}$; $R^{21}$; $R^{22}$;

$R^{23}$; $R^{24}$; and $R^{25}$ are as described for Formula (C), including in embodiments of a compound of Formula (C); and ----- indicates a single or double bond such that all valences are satisfied.

In some embodiments, the compound of Formula (C) or (C-1), or a pharmaceutically acceptable salt or solvate thereof, has the structure of Formula C-1d:

Formula (C-1d)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $L^7$; $R^{17}$; $R^8$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$; $R^{20b}$, $R^{20g}$, $R^{20h}$, $R^{20j}$, $R^{20g}$, $R^{20l}$, $R^{20m}$; $R^{21}$; $R^{22}$; $R^{23}$; $R^{24}$;

and $R^{25}$ are as described for Formula (C), including in embodiments of a compound of Formula (C); and ----- indicates a single or double bond such that all valences are satisfied.

In some embodiments, the compound of Formula (C) or (C-1), or a pharmaceutically acceptable salt or solvate thereof, has the structure of Formula (C-1e):

Formula (C-1e)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $L^7$; $R^{17}$; $R^8$; $R^4$; $L^4$; $R^{4c}$; $R^{4a}$; $R^{43}$; $R^{4b}$; $R^{11c}$; $R^{12}$; $R^{12c}$; $R^{13}$; $R^{14}$; $R^{14a}$; $R^{15}$; $R^{20b}$, $R^{20g}$, $R^{20h}$, $R^{20j}$, $R^{20g}$, $R^{20l}$, $R^{20m}$; $R^{21}$; $R^{22}$; $R^{23}$; $R^{24}$;

and $R^{25}$ are as described for Formula (C), including in embodiments of a compound of Formula (C); and ----- indicates a single or double bond such that all valences are satisfied.

In some embodiments, the compound of Formula (C) or (C-1), or a pharmaceutically acceptable salt or solvate thereof, has the structure of Formula (C-1f):

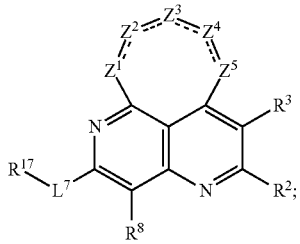

Formula (C-1f)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$;

$R^2$; $R^3$; $L^7$; $R^{17}$; $R^8$; $R^4$; $L^4$; $R^{4c}$; $R^{4d}$; $R^{43}$; $R^{4b}$; $R^{11c}$; $R^{12}$; $R^{12c}$; $R^{13}$; $R^{14}$; $R^{14a}$; $R^{15}$; $R^{20b}$, $R^{20c}$; $R^{20g}$, $R^{20h}$, $R^{20j}$, $R^{20k}$, $R^{20l}$, $R^{20m}$; $R^{21}$; $R^{22}$;

$R^{23}$; $R^{24}$; and $R^{25}$ are as described for Formula (C), including in embodiments of a compound of Formula (C); and ----- indicates a single or double bond such that all valences are satisfied.

The individual embodiments herein below, or combinations thereof, (e.g., embodiments of Ring A) are applicable to compounds of Formula (A), (B), (C), (A'), (B'), (C'), (A"), (B"), or (C"), or a pharmaceutically acceptable salt or solvate thereof.

In embodiments of the formulae above, Ring A is a 5-10 membered cycloalkyl. In embodiments of the formulae above, Ring A is a 5-10 membered cycloalkyl substituted with at least one $R^4$. In embodiments of the formulae above, Ring A is a 5-10 membered cycloalkyl substituted with one $R^4$. In embodiments of the formulae above, Ring A is a 5-10 membered cycloalkyl substituted with two optionally different $R^4$. In embodiments of the formulae above, Ring A is a 5-10 membered cycloalkyl substituted with at least one $R^{11c}$. In embodiments of the formulae above, Ring A is a 5-10 membered cycloalkyl substituted with one $R^{11c}$. In embodiments of the formulae above, Ring A is a 5-10 membered cycloalkyl substituted with two optionally different $R^{11c}$. In embodiments of the formulae above, Ring A is a 5-10 membered cycloalkyl substituted with at least one $R^4$ and substituted with at least one $R^{11c}$. In embodiments of the formulae above, Ring A is a 5-10 membered cycloalkyl substituted with one $R^4$ and substituted with at least one $R^{11c}$. In embodiments of the formulae above, Ring A is a 5-10 membered cycloalkyl substituted with two optionally different $R^4$ and substituted with at least one $R^{11c}$. In embodiments of the formulae above, Ring A is a 5-10 membered cycloalkyl substituted with at least one $R^4$ and substituted with one $R^{11c}$. In embodiments of the formulae above, Ring A is a 5-10 membered cycloalkyl substituted with one $R^4$ and substituted with one $R^{11c}$. In embodiments of the formulae above, Ring A is a 5-10 membered cycloalkyl substituted with two optionally different $R^4$ and substituted with one $R^{11c}$. In embodiments of the formulae above, Ring A is a 5-10 membered cycloalkyl substituted with at least one $R^4$ and substituted with two optionally different $R^{11c}$. In embodiments of the formulae above, Ring A is a 5-10 membered cycloalkyl substituted with one $R^4$ and substituted with two optionally different $R^{11c}$. In embodiments of the formulae above, Ring A is a 5-10 membered cycloalkyl substituted with two optionally different $R^4$ and substituted with two optionally different $R^{11c}$.

In embodiments of the formulae above, Ring A is a 5 membered cycloalkyl. In embodiments of the formulae above, Ring A is a 5 membered cycloalkyl substituted with at least one $R^4$. In embodiments of the formulae above, Ring A is a 5 membered cycloalkyl substituted with one $R^4$. In embodiments of the formulae above, Ring A is a 5 membered cycloalkyl substituted with two optionally different $R^4$. In embodiments of the formulae above, Ring A is a 5 membered cycloalkyl substituted with at least one $R^{11e}$. In embodiments of the formulae above, Ring A is a 5 membered cycloalkyl substituted with one $R^{11c}$. In embodiments of the formulae above, Ring A is a 5 membered cycloalkyl substituted with two optionally different $R^{11c}$. In embodiments of the formulae above, Ring A is a 5 membered cycloalkyl substituted with at least one $R^4$ and substituted with at least one $R^{11c}$. In embodiments of the formulae above, Ring A is a 5 membered cycloalkyl substituted with one $R^4$ and substituted with at least one $R^{11c}$. In embodiments of the formulae above, Ring A is a 5 membered cycloalkyl substituted with two optionally different $R^4$ and substituted with at least one $R^{11c}$. In embodiments of the formulae above, Ring A is a 5 membered cycloalkyl substituted with at least one $R^4$ and substituted with one $R^{11c}$. In embodiments of the formulae above, Ring A is a 5 membered cycloalkyl substituted with one $R^4$ and substituted with one $R^{11c}$. In embodiments of the formulae above, Ring A is a 5 membered cycloalkyl substituted with two optionally different $R^4$ and substituted with one $R^{11c}$. In embodiments of the formulae above, Ring A is a 5 membered cycloalkyl substituted with at least one $R^4$ and substituted with two optionally different $R^{11c}$. In embodiments of the formulae above, Ring A is a 5 membered cycloalkyl substituted with one $R^4$ and substituted with two optionally different $R^{11c}$. In embodiments of the formulae above, Ring A is a 5 membered cycloalkyl substituted with two optionally different $R^4$ and substituted with two optionally different $R^{11c}$.

In embodiments of the formulae above, Ring A is a 6 membered cycloalkyl. In embodiments of the formulae above, Ring A is a 6 membered cycloalkyl substituted with at least one $R^4$. In embodiments of the formulae above, Ring A is a 6 membered cycloalkyl substituted with one $R^4$. In embodiments of the formulae above, Ring A is a 6 membered cycloalkyl substituted with two optionally different $R^4$. In embodiments of the formulae above, Ring A is a 6 membered cycloalkyl substituted with at least one $R^{11c}$. In embodiments of the formulae above, Ring A is a 6 membered cycloalkyl substituted with one $R^{11c}$. In embodiments of the formulae above, Ring A is a 6 membered cycloalkyl substituted with two optionally different $R^{11c}$. In embodiments of the formulae above, Ring A is a 6 membered cycloalkyl substituted with at least one $R^4$ and with at least one $R^{11c}$. In embodiments of the formulae above, Ring A is a 6 membered cycloalkyl substituted with one $R^4$ and substituted with at least one $R^{11c}$. In embodiments of the formulae above, Ring A is a 6 membered cycloalkyl substituted with two optionally different $R^4$ and substituted with at least one $R^{11c}$. In embodiments of the formulae above, Ring A is a 6 membered cycloalkyl substituted with at least one $R^4$ and substituted with one $R^{11c}$. In embodiments of the formulae above, Ring A is a 6 membered cycloalkyl substituted with one $R^4$ and substituted with one $R^{11c}$. In embodiments of the formulae above, Ring A is a 6 membered cycloalkyl substituted with two optionally different $R^4$ and substituted with one $R^{11c}$. In embodiments of the formulae above, Ring A is a 6 membered cycloalkyl substituted with at least one $R^4$ and substituted with two optionally different $R^{11c}$. In embodiments of the formulae above, Ring A is a 6 membered cycloalkyl substituted with one $R^4$ and substituted with two optionally different $R^{11c}$. In embodiments of the formulae above, Ring A is a 6 membered cycloalkyl substituted with two optionally different $R^4$ and substituted with two optionally different $R^{11c}$.

In embodiments of the formulae above, Ring A is a 7 membered cycloalkyl. In embodiments of the formulae above, Ring A is a 7 membered cycloalkyl substituted with at least one $R^4$. In embodiments of the formulae above, Ring A is a 7 membered cycloalkyl substituted with one $R^4$. In embodiments of the formulae above, Ring A is a 7 membered cycloalkyl substituted with two optionally different $R^4$. In embodiments of the formulae above, Ring A is a 7 membered cycloalkyl substituted with at least one $R^{11c}$. In embodiments of the formulae above, Ring A is a 7 membered cycloalkyl substituted with one $R^{11c}$. In embodiments of the formulae above, Ring A is a 7 membered cycloalkyl substituted with two optionally different $R^{11c}$. In embodiments of the formulae above, Ring A is a 7 membered cycloalkyl substituted with at least one $R^4$ and substituted with at least one $R^{11c}$. In embodiments of the formulae above, Ring A is a 7 membered cycloalkyl substituted with one $R^4$ and substituted with at least one $R^{11c}$. In embodiments of the formulae above, Ring A is a 7 membered cycloalkyl substituted with two optionally different $R^4$ and substituted with at least one $R^{11c}$.

In embodiments of the formulae above, Ring A is a 7 membered cycloalkyl substituted with at least one $R^4$ and substituted with one $R^{11c}$. In embodiments of the formulae above, Ring A is a 7 membered cycloalkyl substituted with one $R^4$ and substituted with one R11c. In embodiments of the formulae above, Ring A is a 7 membered cycloalkyl substituted with two optionally different $R^4$ and substituted with one $R^{11c}$. In embodiments of the formulae above, Ring A is a 7 membered cycloalkyl substituted with at least one $R^4$ and substituted with two optionally different $R^{11c}$. In embodiments of the formulae above, Ring A is a 7 membered cycloalkyl substituted with one $R^4$ and substituted with two optionally different $R^{11c}$. In embodiments of the formulae above, Ring A is a 7 membered cycloalkyl substituted with two optionally different $R^4$ and substituted with two optionally different $R^{11c}$.

In embodiments of the formulae above, Ring A is an 8 membered cycloalkyl. In embodiments of the formulae above, Ring A is an 8 membered cycloalkyl substituted with at least one $R^4$. In embodiments of the formulae above, Ring A is an 8 membered cycloalkyl substituted with one $R^4$. In embodiments of the formulae above, Ring A is an 8 membered cycloalkyl substituted with two optionally different $R^4$. In embodiments of the formulae above, Ring A is an 8 membered cycloalkyl substituted with at least one $R^{11c}$. In embodiments of the formulae above, Ring A is an 8 membered cycloalkyl substituted with one $R^{11c}$. In embodiments of the formulae above, Ring A is an 8 membered cycloalkyl substituted with two optionally different $R^{11c}$. In embodiments of the formulae above, Ring A is an 8 membered cycloalkyl substituted with at least one $R^4$ and substituted with at least one $R^{11c}$. In embodiments of the formulae above, Ring A is an 8 membered cycloalkyl substituted with one $R^4$ and substituted with at least one Rllc. In embodiments of the formulae above, Ring A is an 8 membered cycloalkyl substituted with two optionally different $R^4$ and substituted with at least one $R^{11c}$. In embodiments of the formulae above, Ring A is an 8 membered cycloalkyl substituted with at least one $R^4$ and substituted with one $R^{11c}$. In embodiments of the formulae above, Ring A is an 8 membered cycloalkyl substituted with one $R^4$ and substituted with one $R^{11c}$. In embodiments of the formulae above, Ring A is an 8 membered cycloalkyl substituted with two optionally different $R^4$ and substituted with one $R^{11c}$. In embodiments of the formulae above, Ring A is an 8 membered cycloalkyl substituted with at least one $R^4$ and substituted with two optionally different $R^{11c}$. In embodiments of the formulae above, Ring A is an 8 membered cycloalkyl substituted with one $R^4$ and substituted with two optionally different $R^{11c}$. In embodiments of the formulae above, Ring A is an 8 membered cycloalkyl substituted with two optionally different $R^4$ and substituted with two optionally different $R^{11c}$.

In embodiments of the formulae above, Ring A is a 9 membered cycloalkyl. In embodiments of the formulae above, Ring A is a 9 membered cycloalkyl substituted with at least one $R^4$. In embodiments of the formulae above, Ring A is a 9 membered cycloalkyl substituted with one $R^4$. In embodiments of the formulae above, Ring A is a 9 membered cycloalkyl substituted with two optionally different $R^4$. In embodiments of the formulae above, Ring A is a 9 membered cycloalkyl substituted with at least one $R^{11c}$. In embodiments of the formulae above, Ring A is a 9 membered cycloalkyl substituted with one $R^{11c}$. In embodiments of the formulae above, Ring A is a 9 membered cycloalkyl substituted with two optionally different $R^{11c}$. In embodiments of the formulae above, Ring A is a 9 membered cycloalkyl substituted with at least one $R^4$ and substituted with at least one $R^{11c}$. In embodiments of the formulae above, Ring A is a 9 membered cycloalkyl substituted with one $R^4$ and substituted with at least one $R^{11c}$. In embodiments of the formulae above, Ring A is a 9 membered cycloalkyl substituted with two optionally different $R^4$ and substituted with at least one Rllc. In embodiments of the formulae above, Ring A is a 9 membered cycloalkyl substituted with at least one $R^4$ and substituted with one $R^{11c}$. In embodiments of the formulae above, Ring A is a 9 membered cycloalkyl substituted with one $R^4$ and substituted with one $R^{11c}$. In embodiments of the formulae above, Ring A is a 9 membered cycloalkyl substituted with two optionally different $R^4$ and substituted with one $R^{11c}$. In embodiments of the formulae above, Ring A is a 9 membered cycloalkyl substituted with at least one $R^4$ and substituted with two optionally different $R^{11c}$. In embodiments of the formulae above, Ring A is a 9 membered cycloalkyl substituted with one $R^4$ and substituted with two optionally different $R^{11c}$. In embodiments of the formulae above, Ring A is a 9 membered cycloalkyl substituted with two optionally different $R^4$ and substituted with two optionally different $R^{11c}$.

In embodiments of the formulae above, Ring A is a 10 membered cycloalkyl. In embodiments of the formulae above, Ring A is a 10 membered cycloalkyl substituted with at least one $R^4$. In embodiments of the formulae above, Ring A is a 10 membered cycloalkyl substituted with one $R^4$. In embodiments of the formulae above, Ring A is a 10 membered cycloalkyl substituted with two optionally different $R^4$. In embodiments of the formulae above, Ring A is a 10 membered cycloalkyl substituted with at least one $R^{11c}$. In embodiments of the formulae above, Ring A is a 10 membered cycloalkyl substituted with one $R^{11c}$. In embodiments of the formulae above, Ring A is a 10 membered cycloalkyl substituted with two optionally different $R^{11c}$. In embodiments of the formulae above, Ring A is a 10 membered cycloalkyl substituted with at least one $R^4$ and substituted with at least one $R^{11c}$. In embodiments of the formulae above, Ring A is a 10 membered cycloalkyl substituted with one $R^4$ and substituted with at least one R1lc. In embodiments of the formulae above, Ring A is a 10 membered cycloalkyl substituted with two optionally different $R^4$ and substituted with at least one $R^{11c}$. In embodiments of the formulae above, Ring A is a 10 membered cycloalkyl substituted with at least one $R^4$ and substituted with one $R^{11c}$. In embodiments of the formulae above, Ring A is a 10 membered cycloalkyl substituted with one $R^4$ and substituted with one $R^{11c}$. In embodiments of the formulae above, Ring A is a 10 membered cycloalkyl substituted with two optionally different $R^4$ and substituted with one $R^{11c}$. In embodiments of the formulae above, Ring A is a 10 membered cycloalkyl substituted with at least one $R^4$ and substituted with two optionally different $R^{11c}$. In embodiments of the formulae above, Ring A is a 10 membered cycloalkyl substituted with one $R^4$ and substituted with two optionally different $R^{11c}$. In embodiments of the formulae above, Ring A is a 10 membered cycloalkyl substituted with two optionally different $R^4$ and substituted with two optionally different $R^{11c}$.

In embodiments of the formulae above, Ring A is a 8-10 membered cycloalkyl. In embodiments of the formulae above, Ring A is a 8-10 membered cycloalkyl substituted with at least one $R^4$. In embodiments of the formulae above, Ring A is a 8-10 membered cycloalkyl substituted with one $R^4$. In embodiments of the formulae above, Ring A is a 8-10 membered cycloalkyl substituted with two optionally different $R^4$. In embodiments of the formulae above, Ring A is a 8-10 membered cycloalkyl substituted with at least one $R^{11c}$. In embodiments of the formulae above, Ring A is a 8-10 membered cycloalkyl substituted with one $R^{11c}$. In embodiments of the formulae above, Ring A is a 8-10 membered cycloalkyl substituted with two optionally different $R^{11c}$. In embodiments of the formulae above, Ring A is a 8-10 membered cycloalkyl substituted with at least one $R^4$ and substituted with at least one $R^{11c}$. In embodiments of the formulae above, Ring A is a 8-10 membered cycloalkyl substituted with one $R^4$ and substituted with at least one $R^{11c}$. In embodiments of the formulae above, Ring A is a 8-10 membered cycloalkyl substituted with two optionally different $R^4$ and substituted with at least one $R^{11c}$. In embodiments of the formulae above, Ring A is a 8-10 membered cycloalkyl substituted with at least one $R^4$ and substituted with one $R^{11c}$. In embodiments of the formulae above, Ring A is a 8-10 membered cycloalkyl substituted with one $R^4$ and substituted with one $R^{11c}$. In embodiments of the formulae above, Ring A is a 8-10 membered cycloalkyl substituted with two optionally different $R^4$ and substituted with one $R^{11c}$. In embodiments of the formulae above, Ring A is a 8-10 membered cycloalkyl substituted with at least one $R^4$ and substituted with two optionally different $R^{11c}$. In embodiments of the formulae above, Ring A is a 8-10 membered cycloalkyl substituted with one $R^4$ and substituted with two optionally different $R^{11c}$. In embodiments of the formulae above, Ring A is a 8-10 membered cycloalkyl substituted with two optionally different $R^4$ and substituted with two optionally different $R^{11c}$.

In embodiments of the formulae above, Ring A is a 5-10 membered heterocycloalkyl. In embodiments of the formulae above, Ring A is a 5-10 membered heterocycloalkyl substituted with at least one $R^4$. In embodiments of the formulae above, Ring A is a 5-10 membered heterocycloalkyl substituted with one $R^4$. In embodiments of the formulae above, Ring A is a 5-10 membered heterocycloalkyl substituted with two optionally different $R^4$. In embodiments of the formulae above, Ring A is a 5-10 membered heterocycloalkyl substituted with at least one $R^{11c}$. In embodiments of the formulae above, Ring A is a 5-10 membered heterocycloalkyl substituted with one $R^{11c}$. In embodiments of the formulae above, Ring A is a 5-10 membered heterocycloalkyl substituted with two optionally different $R^{11c}$. In embodiments of the formulae above, Ring A is a 5-10 membered heterocycloalkyl substituted with at least one $R^4$ and substituted with at least one $R^{11c}$. In embodiments of the formulae above, Ring A is a 5-10 membered heterocycloalkyl substituted with one $R^4$ and substituted with at least one $R^{11c}$. In embodiments of the formulae above, Ring A is a 5-10 membered heterocycloalkyl substituted with two optionally different $R^4$ and substituted with at least one $R^{11c}$. In embodiments of the formulae above, Ring A is a 5-10 membered heterocycloalkyl substituted with at least one $R^4$ and substituted with one $R^{11c}$. In embodiments of the formulae above, Ring A is a 5-10 membered heterocycloalkyl substituted with one $R^4$ and substituted with one $R^{11c}$. In embodiments of the formulae above, Ring A is a 5-10 membered heterocycloalkyl substituted with two optionally different $R^4$ and substituted with one $R^{11c}$. In embodiments of the formulae above, Ring A is a 5-10 membered heterocycloalkyl substituted with at least one $R^4$ and substituted with two optionally different $R^{11c}$. In embodiments of the formulae above, Ring A is a 5-10 membered heterocycloalkyl substituted with one $R^4$ and substituted with two optionally different $R^{11c}$. In embodiments of the formulae above, Ring A is a 5-10 membered heterocycloalkyl substituted with two optionally different $R^4$ and substituted with two optionally different $R^{11c}$.

In embodiments of the formulae above, Ring A is a 5 membered heterocycloalkyl. In embodiments of the formulae above, Ring A is a 5 membered heterocycloalkyl substituted with at least one $R^4$. In embodiments of the formulae above, Ring A is a 5 membered heterocycloalkyl substituted with one $R^4$. In embodiments of the formulae above, Ring A is a 5 membered heterocycloalkyl substituted with two optionally different $R^4$. In embodiments of the formulae above, Ring A is a 5 membered heterocycloalkyl substituted with at least one $R^{11c}$. In embodiments of the formulae above, Ring A is a 5 membered heterocycloalkyl substituted with one $R^{11c}$. In embodiments of the formulae above, Ring A is a 5 membered heterocycloalkyl substituted with two optionally different $R^{11c}$. In embodiments of the formulae above, Ring A is a 5 membered heterocycloalkyl substituted with at least one $R^4$ and substituted with at least one $R^{11c}$. In embodiments of the formulae above, Ring A is a 5 membered heterocycloalkyl substituted with one $R^4$ and substituted with at least one $R^{11c}$. In embodiments of the formulae above, Ring A is a 5 membered heterocycloalkyl substituted with two optionally different $R^4$ and substituted with at least one $R^{11c}$. In embodiments of the formulae above, Ring A is a 5 membered heterocycloalkyl substituted with at least one $R^4$ and substituted with one $R^{11c}$. In embodiments of the formulae above, Ring A is a 5 membered heterocycloalkyl substituted with one $R^4$ and substituted with one $R^{11c}$. In embodiments of the formulae above, Ring A is a 5 membered heterocycloalkyl substituted with two optionally different $R^4$ and substituted with one $R^{11c}$. In embodiments of the formulae above, Ring A is a 5 membered heterocycloalkyl substituted with at least one $R^4$ and substituted with two optionally different $R^{11c}$. In embodiments of the formulae above, Ring A is a 5 membered heterocycloalkyl substituted with one $R^4$ and substituted with two optionally different $R^{11c}$. In embodiments of the formulae above, Ring A is a 5 membered heterocycloalkyl substituted with two optionally different $R^4$ and substituted with two optionally different $R^{11c}$.

In embodiments of the formulae above, Ring A is a 6 membered heterocycloalkyl. In embodiments of the formulae above, Ring A is a 6 membered heterocycloalkyl substituted with at least one $R^4$. In embodiments of the formulae above, Ring A is a 6 membered heterocycloalkyl substituted with one $R^4$. In embodiments of the formulae above, Ring A is a 6 membered heterocycloalkyl substituted with two optionally different $R^4$. In embodiments of the formulae above, Ring A is a 6 membered heterocycloalkyl substituted with at least one $R^{11c}$. In embodiments of the formulae above, Ring A is a 6 membered heterocycloalkyl substituted with one $R^{11c}$. In embodiments of the formulae above, Ring A is a 6 membered heterocycloalkyl substituted with two optionally different $R^{11c}$. In embodiments of the formulae above, Ring A is a 6 membered heterocycloalkyl substituted with at least one $R^4$ and substituted with at least one $R^{11c}$. In embodiments of the formulae above, Ring A is a 6 membered heterocycloalkyl substituted with one $R^4$ and substituted with at least one $R^{11c}$. In embodiments of the formulae above, Ring A is a 6 membered heterocycloalkyl substituted with two optionally different $R^4$ and substituted with at least one $R^{11c}$. In embodiments of the formulae above, Ring A is a 6 membered heterocycloalkyl substituted with at least one $R^4$ and substituted with one $R^{11c}$. In embodiments of the formulae above, Ring A is a 6 membered heterocycloalkyl substituted with one $R^4$ and substituted with one $R^{11c}$. In embodiments of the formulae above, Ring A is a 6 membered heterocycloalkyl substituted with two optionally different $R^4$ and substituted with one $R^{11c}$. In embodiments of the formulae above, Ring A is a 6 membered heterocycloalkyl substituted with at least one $R^4$ and substituted with two optionally different $R^{11c}$. In embodiments of the formulae above, Ring A is a 6 membered heterocycloalkyl substituted with one $R^4$ and substituted with two optionally different $R^{11c}$. In embodiments of the formulae above, Ring A is a 6 membered heterocycloalkyl substituted with two optionally different $R^4$ and substituted with two optionally different $R^{11c}$.

In embodiments of the formulae above, Ring A is a 7 membered heterocycloalkyl. In embodiments of the formulae above, Ring A is a 6 membered heterocycloalkyl substituted with at least one $R^4$. In embodiments of the formulae above, Ring A is a 7 membered heterocycloalkyl substituted with one $R^4$. In embodiments of the formulae above, Ring A is a 7 membered heterocycloalkyl substituted with two optionally different $R^4$. In embodiments of the formulae above, Ring A is a 7 membered heterocycloalkyl substituted with at least one $R^{11c}$. In embodiments of the formulae above, Ring A is a 7 membered heterocycloalkyl substituted with one $R^{11c}$. In embodiments of the formulae above, Ring A is a 7 membered heterocycloalkyl substituted with two optionally different $R^{11c}$. In embodiments of the formulae above, Ring A is a 7 membered heterocycloalkyl substituted with at least one $R^4$ and substituted with at least one $R^{11c}$. In embodiments of the formulae above, Ring A is a 7 membered heterocycloalkyl substituted with one $R^4$ and substituted with at least one $R^{11c}$. In embodiments of the formulae above, Ring A is a 7 membered heterocycloalkyl substituted with two optionally different $R^4$ and substituted with at least one $R^{11c}$. In embodiments of the formulae above, Ring A is a 7 membered heterocycloalkyl substituted with at least one $R^4$ and substituted with one $R^{11c}$. In embodiments of the formulae above, Ring A is a 7 membered heterocycloalkyl substituted with one $R^4$ and substituted with one $R^{11c}$. In embodiments of the formulae above, Ring A is a 7 membered heterocycloalkyl substituted with two optionally different $R^4$ and substituted with one $R^{11c}$. In embodiments of the formulae above, Ring A is a 7 membered heterocycloalkyl substituted with at least one $R^4$ and substituted with two optionally different $R^{11c}$. In embodiments of the formulae above, Ring A is a 7 membered heterocycloalkyl substituted with one $R^4$ and substituted with two optionally different $R^{11c}$. In embodiments of the formulae above, Ring A is a 7 membered heterocycloalkyl substituted with two optionally different $R^4$ and substituted with two optionally different $R^{11c}$.

In embodiments of the formulae above, Ring A is an 8 membered heterocycloalkyl. In embodiments of the formulae above, Ring A is an 8 membered heterocycloalkyl substituted with at least one $R^4$. In embodiments of the formulae above, Ring A is an 8 membered heterocycloalkyl substituted with one $R^4$. In embodiments of the formulae above, Ring A is an 8 membered heterocycloalkyl substituted with two optionally different $R^4$. In embodiments of the formulae above, Ring A is an 8 membered heterocycloalkyl substituted with at least one $R^{11c}$. In embodiments of the formulae above, Ring A is an 8 membered heterocycloalkyl substituted with one $R^{11c}$. In embodiments of the formulae above, Ring A is an 8 membered heterocycloalkyl substituted with two optionally different $R^{11c}$. In embodiments of the formulae above, Ring A is an 8 membered heterocycloalkyl substituted with at least one $R^4$ and substituted with at least one $R^{11c}$. In embodiments of the formulae above, Ring A is an 8 membered heterocycloalkyl substituted with one $R^4$ and substituted with at least one $R^{11c}$. In embodiments of the formulae above, Ring A is an 8 membered heterocycloalkyl substituted with two optionally different $R^4$ and substituted with at least one $R^{11c}$. In embodiments of the formulae above, Ring A is an 8 membered heterocycloalkyl substituted with at least one $R^4$ and substituted with one $R^{11c}$. In embodiments of the formulae above, Ring A is an 8 membered heterocycloalkyl substituted with one $R^4$ and substituted with one $R^{11c}$. In embodiments of the formulae above, Ring A is an 8 membered heterocycloalkyl substituted with two optionally different $R^4$ and substituted with one $R^{11c}$. In embodiments of the formulae above, Ring A is an 8 membered heterocycloalkyl substituted with at least one $R^4$ and substituted with two optionally different $R^{11c}$. In embodiments of the formulae above, Ring A is an 8 membered heterocycloalkyl substituted with one $R^4$ and substituted with two optionally different $R^{11c}$. In embodiments of the formulae above, Ring A is an 8 membered heterocycloalkyl substituted with two optionally different $R^4$ and substituted with two optionally different $R^{11c}$. In embodiments of the formulae above, Ring A is a 9 membered heterocycloalkyl. In embodiments of the formulae above, Ring A is a 9 membered heterocycloalkyl substituted with at least one $R^4$. In embodiments of the formulae above, Ring A is a 9 membered heterocycloalkyl substituted with one $R^4$. In embodiments of the formulae above, Ring A is a 9 membered heterocycloalkyl substituted with two optionally different $R^4$. In embodiments of the formulae above, Ring A is a 9 membered heterocycloalkyl substituted with at least one $R^{11c}$. In embodiments of the formulae above, Ring A is a 9 membered heterocycloalkyl substituted with one $R^{11c}$. In embodiments of the formulae above, Ring A is a 9 membered heterocycloalkyl substituted with two optionally different $R^{11c}$. In embodiments of the formula above, Ring A is a 9 membered heterocycloalkyl substituted with at least one $R^4$ and substituted with at least one $R^{11c}$. In embodiments of the formulae above, Ring A is a 9 membered heterocycloalkyl substituted with one $R^4$ and substituted with at least one $R^{11c}$. In embodiments of the formulae above, Ring A is a 9 membered heterocycloalkyl substituted with two optionally different $R^4$ and substituted with at least one $R^{11c}$. In embodiments of the formulae above, Ring A is a 9 membered heterocycloalkyl substituted with at least one $R^4$ and substituted with one $R^{11c}$. In embodiments of the formulae above, Ring A is a 9 membered heterocycloalkyl substituted with one $R^4$ and substituted with one $R^{11c}$. In embodiments of the formulae above, Ring A is a 9 membered heterocycloalkyl substituted with two optionally different $R^4$ and substituted with one $R^{11c}$. In embodiments of the formulae above, Ring A is a 9 membered heterocycloalkyl substituted with at least one $R^4$ and substituted with two optionally different $R^{11c}$. In embodiments of the formulae above, Ring A is a 9 membered heterocycloalkyl substituted with one $R^4$ and substituted with two optionally different $R^{11c}$. In embodiments of the formulae above, Ring A is a 9 membered heterocycloalkyl substituted with two optionally different $R^4$ and substituted with two optionally different $R^{11c}$.

In embodiments of the formulae above, Ring A is a 10 membered heterocycloalkyl. In embodiments of the formulae above, Ring A is a 10 membered heterocycloalkyl substituted with at least one $R^4$. In embodiments of the formulae above, Ring A is a 10 membered heterocycloalkyl substituted with one $R^4$. In embodiments of the formulae above, Ring A is a 10 membered heterocycloalkyl substituted with two optionally different $R^4$. In embodiments of the formulae above, Ring A is a 10 membered heterocycloalkyl substituted with at least one $R^{11c}$. In embodiments of the formulae above, Ring A is a 10 membered heterocycloalkyl substituted with one $R^{11c}$. In embodiments of the formulae above, Ring A is a 10 membered heterocycloalkyl substituted with two optionally different $R^{11c}$. In embodiments of the formulae above, Ring A is a 10 membered heterocycloalkyl substituted with at least one $R^4$ and substituted with at least one $R^{11c}$. In embodiments of the formulae above, Ring A is a 10 membered heterocycloalkyl substituted with one $R^4$ and substituted with at least one $R^{11c}$. In embodiments of the formulae above, Ring A is a 10 membered heterocycloalkyl substituted with two optionally different $R^4$ and substituted with at least one $R^{11c}$. In embodiments of the formulae above, Ring A is a 10 membered heterocycloalkyl substituted with at least one $R^4$ and substituted with one $R^{11c}$. In embodiments of the formulae above, Ring A is a 10 membered heterocycloalkyl substituted with one $R^4$ and substituted with one $R^{11c}$. In embodiments of the formulae above, Ring A is a 10 membered heterocycloalkyl substituted with two optionally different $R^4$ and substituted with one $R^{11c}$. In embodiments of the formulae above, Ring A is a 10 membered heterocycloalkyl substituted with at least one $R^4$ and substituted with two optionally different $R^{11c}$. In embodiments of the formulae above, Ring A is a 10 membered heterocycloalkyl substituted with one $R^4$ and substituted with two optionally different $R^{11c}$. In embodiments of the formulae above, Ring A is a 10 membered heterocycloalkyl substituted with two optionally different $R^4$ and substituted with two optionally different $R^{11c}$.

In embodiments of the formulae above, Ring A is a 8-10 membered heterocycloalkyl. In embodiments of the formulae above, Ring A is a 8-10 membered heterocycloalkyl substituted with at least one $R^4$. In embodiments of the formulae above, Ring A is a 8-10 membered heterocycloalkyl substituted with one $R^4$. In embodiments of the formulae above, Ring A is a 8-10 membered heterocycloalkyl substituted with two optionally different $R^4$. In embodiments of the formulae above, Ring A is a 8-10 membered heterocycloalkyl substituted with at least one $R^{11c}$. In embodiments of the formulae above, Ring A is a 8-10 membered heterocycloalkyl substituted with one $R^{11c}$. In embodiments of the formulae above, Ring A is a 8-10 membered heterocycloalkyl substituted with two optionally different $R^{11c}$. In embodiments of the formulae above, Ring A is a 8-10 membered heterocycloalkyl substituted with at least one $R^4$ and substituted with at least one $R^{11c}$. In embodiments of the formulae above, Ring A is a 8-10 membered heterocycloalkyl substituted with one $R^4$ and substituted with at least one $R^{11c}$. In embodiments of the formulae above, Ring A is a 8-10 membered heterocycloalkyl substituted with two optionally different $R^4$ and substituted with at least one $R^{11c}$. In embodiments of the formulae above, Ring A is a 8-10 membered heterocycloalkyl substituted with at least one $R^4$ and substituted with one $R^{11c}$. In embodiments of the formulae above, Ring A is a 8-10 membered heterocycloalkyl substituted with one $R^4$ and substituted with one $R^{11c}$. In embodiments of the formulae above, Ring A is a 8-10 membered heterocycloalkyl substituted with two optionally different $R^4$ and substituted with one $R^{11c}$. In embodiments of the formulae above, Ring A is a 8-10 membered heterocycloalkyl substituted with at least one $R^4$ and substituted with two optionally different $R^{11c}$. In embodiments of the formulae above, Ring A is a 8-10 membered heterocycloalkyl substituted with one $R^4$ and substituted with two optionally different $R^{11c}$. In embodiments of the formulae above, Ring A is a 8-10 membered heterocycloalkyl substituted with two optionally different $R^4$ and substituted with two optionally different $R^{11c}$.

The individual embodiments herein below, or combinations thereof, (e.g., embodiments of $Z^1$, $Z^2$, $Z^3$, $Z^4$, or $Z^5$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $Z^1$ is $N(R^4)$. In embodiments of the formulae above, $Z^1$ is $N(R^{11c})$. In embodiments of the formulae above, $Z^1$ is $N(H)$. In embodiments of the formulae above, $Z^1$ is N. In embodiments of the formulae above, $Z^1$ is $C(R^4)$. In embodiments of the formulae above, $Z^1$ is $C(R^{11c})$. In embodiments of the formulae above, $Z^1$ is $C(H)$. In embodiments of the formulae above, $Z^1$ is $C(R^4)(H)$. In embodiments of the formulae above, $Z^1$ is $C(R^4)(R^{11c})$. In embodiments of the formulae above, $Z^1$ is $C(R^{11c})(R^{11c})$. In embodiments of the formulae above, $Z^1$ is $C(R^4)(R^4)$. In embodiments of the formulae above, $Z^1$ is $C(R^{11c})(H)$. In embodiments of the formulae above, $Z^1$ is $CH_2$. In embodiments of the formulae above, $Z^1$ is S. In embodiments of the formulae above, $Z^1$ is O. In embodiments of the formulae above, $Z^1$ is C(O). In embodiments of the formulae above, $Z^2$ is $N(R^4)$. In embodiments of the formulae above, $Z^2$ is $N(R^{11c})$. In embodiments of the formulae above, $Z^2$ is N(H). In embodiments of the formulae above, $Z^2$ is N. In embodiments of the formulae above, $Z^2$ is $C(R^4)$. In embodiments of the formulae above, $Z^2$ is $C(R^{11c})$. In embodiments of the formulae above, $Z^2$ is C(H). In embodiments of the formulae above, $Z^2$ is $C(R^4)(H)$. In embodiments of the formulae above, $Z^2$ is $C(R^4)(R^{11c})$. In embodiments of the formulae above, $Z^2$ is $C(R^{11c})(R^{11c})$. In embodiments of the formulae above, $Z^2$ is $C(R^4)(R^4)$. In embodiments of the formulae above, $Z^2$ is $C(R^{11c})(H)$. In embodiments of the formulae above, $Z^2$ is $CH_2$. In embodiments of the formulae above, $Z^2$ is S. In embodiments of the formulae above, $Z^2$ is O. In embodiments of the formulae above, $Z^2$ is C(O). In embodiments of the formulae above, $Z^2$ is a bond. In embodiments of the formulae above, $Z^3$ is $N(R^4)$. In embodiments of the formulae above, $Z^3$ is $N(R^{11c})$. In embodiments of the formulae above, $Z^3$ is N(H). In embodiments of the formulae above, $Z^3$ is N. In embodiments of the formulae above, $Z^3$ is $C(R^4)$. In embodiments of the formulae above, $Z^3$ is $C(R^{11c})$. In embodiments of the formulae above, $Z^3$ is C(H). In embodiments of the formulae above, $Z^3$ is $C(R^4)(H)$. In embodiments of the formulae above, $Z^3$ is $C(R^4)(R^{11c})$. In embodiments of the formulae above, $Z^3$ is $C(R^{11c})(R^{11c})$. In embodiments of the formulae above, $Z^3$ is $C(R^4)(R^4)$. In embodiments of the formulae above, $Z^3$ is $C(R^{11c})(H)$. In embodiments of the formulae above, $Z^3$ is $CH_2$. In embodiments of the formulae above, $Z^3$ is S. In embodiments of the formulae above, $Z^3$ is O. In embodiments of the formulae above, $Z^3$ is C(O). In embodiments of the formulae above, $Z^4$ is $N(R^4)$. In embodiments of the formulae above, $Z^4$ is $N(R^{11c})$. In embodiments of the formulae above, $Z^4$ is N(H). In embodiments of the formulae above, $Z^4$ is N. In embodiments of the formulae above, $Z^4$ is $C(R^4)$. In embodiments of the formulae above, $Z^4$ is $C(R^{11c})$. In embodiments of the formulae above, $Z^4$ is C(H). In embodiments of the formulae above, $Z^4$ is $C(R^4)(H)$. In embodiments of the formulae above, $Z^4$ is $C(R^4)(R^{11c})$. In embodiments of the formulae above, $Z^4$ is $C(R^{11c})(R^{11c})$. In embodiments of the formulae above, $Z^4$ is $C(R^4)(R^4)$. In embodiments of the formulae above, $Z^4$ is $C(R^{11c})(H)$. In embodiments of the formulae above, $Z^4$ is $CH_2$. In embodiments of the formulae above, $Z^4$ is S. In embodiments of the formulae above, $Z^4$ is O. In embodiments of the formulae above, $Z^4$ is C(O). In embodiments of the formulae above, $Z^4$ is a bond. In embodiments of the formulae above, $Z^5$ is $N(R^4)$. In embodiments of the formulae above, $Z^5$ is $N(R^{11c})$. In embodiments of the formulae above, $Z^5$ is N(H). In embodiments of the formulae above, $Z^5$ is N. In embodiments of the formulae above, $Z^5$ is $C(R^4)$. In embodiments of the formulae above, $Z^5$ is $C(R^{11c})$. In embodiments of the formulae above, $Z^5$ is C(H). In embodiments of the formulae above, $Z^5$ is $C(R^4)(H)$. In embodiments of the formulae above, $Z^5$ is $C(R^4)(R^{11c})$. In embodiments of the formulae above, $Z^5$ is $C(R^{11c})(R^{11c})$. In embodiments of the formulae above, $Z^5$ is $C(R^4)(R^4)$. In embodiments of the formulae above, $Z^5$ is $C(R^{11c})(H)$. In embodiments of the formulae above, $Z^5$ is $CH_2$. In embodiments of the formulae above, $Z^5$ is S. In embodiments of the formulae above, $Z^5$ is O. In embodiments of the formulae above, $Z^3$ is C(O).

In an aspect is provided a compound of Formula (A'), or a pharmaceutically acceptable salt or solvate thereof:

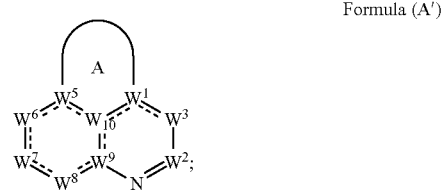

Formula (A')

wherein:
Ring A; $W^1$; $R^1$; $W^2$; $R^2$; $W^3$; $R^3$; $R^{3a}$; $R^{30}$; $W^5$; $R^5$; $W^6$; $R^6$; $R^{6a}$; $R^6$; $W^7$; $R^{7a}$; $R^{7c}$; $R^{7d}$; $R^1$; $L^7$; $R^{17}$; Ring B; $X^6$, $X^7$, $X^8$; $X^9$, $X^{10}$, $X^{11}$;
$R^{1a}$, $R^{1b}$, $R^{1c}$; $W^8$; $R^8$; $R^{8a}$; $R^{8b}$; $W^9$; $W^{10}$; $R^9$; $R^4$; $L^4$; $R^{4o}$ C.; $R^{4d}$; $R^{4a}$; $R^{11c}$; $R^{12}$; $R^{12c}$; $R^{13}$; $R^{14}$; $R^{14a}$; $R^{15}$; $R^{20a}$; $R^{20b}$, $R^{20c}$; $R^{20d}$, $R^{20e}$;
$R^{20f}$, $R^{20g}$, $R^{20h}$, $R^{20i}$, $R^{20j}$, $R^{20k}$, $R^{20l}$, $R^{20m}$; $R^{21}$; $R^{22}$; $R^{23}$; $R^{24}$; and $R^{25}$ are as described for Formula (A), including in embodiments of a compound of Formula (A);
each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{12}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{12}$, —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), and —P(=O)($R^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$; and
----- indicates a single or double bond such that all valences are satisfied.

It will be understood that when an aspect or embodiment (e.g., compound of formula (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f)) of a compound references variables from a different compound formula (e.g., compound of formula (I), (II), (III), (A), (B), or (C)) but does not recite all variables of the aspect or embodiment compound (e.g., aspect or embodiment recites $Z^1, Z^2, Z^3, Z^4$, and $Z^5$, but not $W^1, R^2, R^4, R^{11c}, R^{20k}$, or any other variable) that the unrecited variables of the compound may be any of the recited variable values of the referenced compound formula recited by the aspect or embodiment (e.g., recited variable value of compound of formula (I), (II), (III), (A), (B), or (C), or any embodiment thereof that is also within the scope of the recited aspect or embodiment compound).

In some embodiments, the compound of Formula (A'), or a pharmaceutically acceptable salt or solvate thereof, has the structure of Formula (A'-1):

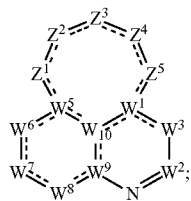

Formula (A'-1)

wherein $Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1, Z^2, Z^3, Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A') or (A'-1), or a pharmaceutically acceptable salt or solvate thereof, has the structure of Formula (A'-1a):

Formula (A'-1a)

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1, Z^2, Z^3, Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A') or (A'-1), or a pharmaceutically acceptable salt or solvate thereof, has the structure of Formula (A'-1b):

Formula (A'-1b)

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1, Z^2, Z^3, Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A') or (A'-1), or a pharmaceutically acceptable salt or solvate thereof, has the structure of Formula (A'-1c):

Formula (A'-1c)

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R\$)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1, Z^2, Z^3, Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A') or (A'-1), or a pharmaceutically acceptable salt or solvate thereof, has the structure of Formula (A'-1d):

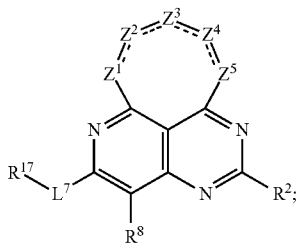

Formula (A'-1d)

Z$^1$, Z$^3$, and Z' are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); and Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

wherein at least one of Z$^1$, Z$^2$, Z$^3$, Z$^4$, and Z$^3$ is N(R$^4$), C(R$^4$), C(R$^4$)(H), C(R$^4$)(R$^{11c}$), or C(R$^4$)(R$^4$).

In some embodiments, the compound of Formula (A') or (A'-1), or a pharmaceutically acceptable salt or solvate thereof, has the structure of Formula (A'-1e):

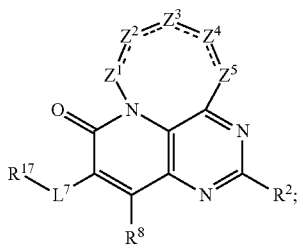

Formula (A'-1e)

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); and Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (A') or (A'-1), or a pharmaceutically acceptable salt or solvate thereof, has the structure of Formula (A'-1f):

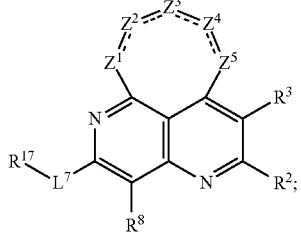

Formula (A'-1f)

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); and Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In an aspect is provided a compound of Formula (B'), or a pharmaceutically acceptable salt or solvate thereof:

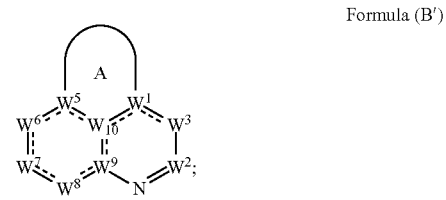

Formula (B')

wherein:
Ring A; W$^1$; R$^1$; W$^2$; R$^2$; W$^3$; R$^3$; R$^{3a}$; R$^{3b}$; W$^5$; R$^5$; W$^6$; R$^6$; R$^6$; R$; W$^7$; R$^{7a}$; R$^{7c}$; R$^{7d}$; R$^1$; L$^7$; R$^{17}$; Ring B; X$^6$; X$^1$, X$^8$; X$^9$, X$^{10}$, X$^{11}$; Ria, R$^{1b}$, R$^{1c}$; W$^8$; R$^8$; R$^{6a}$; R&b; W$^9$; W$^{10}$; R$^9$; R$^4$; L$^4$; R$^{4c}$; Rd; Rds; R$^{11c}$; R$^{12}$, R$^{12c}$; R$^{13}$; R$^{14}$; R$^{14a}$; R$^{15}$; R$^{20a}$; R$^{20b}$, R$^{20c}$; R$^{20d}$, R$^{20e}$, R$^{20f}$, R$^{20g}$, R$^{20h}$, R$^{20i}$, R$^{20j}$, R$^{20k}$, R$^{20l}$, R$^{20m}$; R$^{21}$; R$^{22}$; R$^{23}$; R$^{24}$; and R$^{25}$ are as described for Formula (B), including in embodiments of a compound of Formula (B);

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, and C$_{1-9}$heteroaryl are optionally substituted with one or more R$^{20j}$; and ----- indicates a single or double bond such that all valences are satisfied.

In some embodiments, the compound of Formula (B'), or a pharmaceutically acceptable salt or solvate thereof, has the structure of Formula (B'-1):

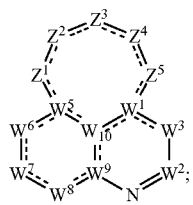

Formula (B'-1)

wherein
Z$^1$, Z$^3$, and Z' are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R*)(R⁴), C(R¹¹ᶜ)(H), CH₂, S, O, and C(O).

In some embodiments, the compound of Formula (B') or (B'-1), or a pharmaceutically acceptable salt or solvate thereof, has the structure of Formula (B'-1a):

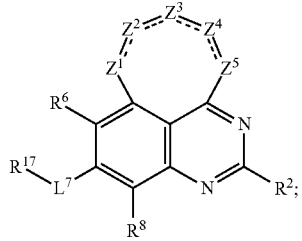

Formula (B'-1a)

wherein

Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

Z² and Zᵃ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O).

In some embodiments, the compound of Formula (B') or (B'-1), or a pharmaceutically acceptable salt or solvate thereof, has the structure of Formula (B'-1b):

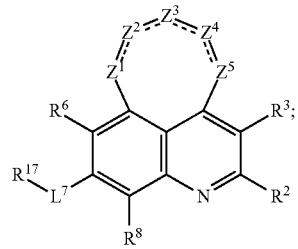

Formula (B'-1b)

wherein

Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

Z² and Z⁴ are each independently selected from a bond, N(R⁴), N(R¹¹ᶜ), N(H), N, C(R⁴), C(R¹¹ᶜ), C(H), C(RA)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O).

In some embodiments, the compound of Formula (B') or (B'-1), or a pharmaceutically acceptable salt or solvate thereof, has the structure of Formula (B'-1c):

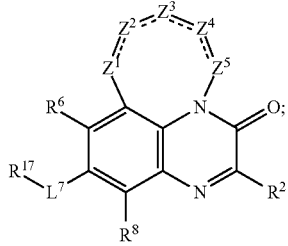

Formula (B'-1c)

wherein

Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O).

In some embodiments, the compound of Formula (B') or (B'-1), or a pharmaceutically acceptable salt or solvate thereof, has the structure of Formula B-1d):

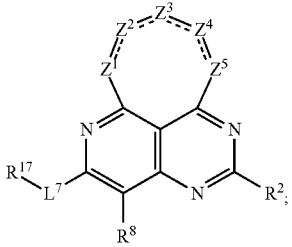

Formula (B'-1d)

wherein

Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O).

In some embodiments, the compound of Formula (B') or (B'-1), or a pharmaceutically acceptable salt or solvate thereof, has the structure of Formula (B'-1e):

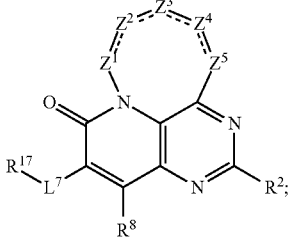

Formula (B'-1e)

wherein

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O).

In some embodiments, the compound of Formula (B') or (B'-1), or a pharmaceutically acceptable salt or solvate thereof, has the structure of Formula (B'-1f):

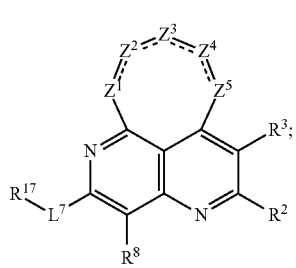

Formula (B'-1f)

wherein

Z$^1$, Z$^3$, and Z' are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O).

In an aspect is provided a compound of Formula (C'), or a pharmaceutically acceptable salt or solvate thereof:

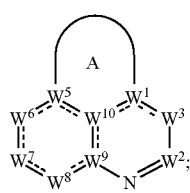

Formula (C')

wherein:

Ring A; W$^1$; R$^1$; W$^2$; R$^2$; W$^3$; R$^3$; R$^{3a}$; R$^{3b}$; W$^5$; R$^5$; W$^6$; R$^6$; R$^{6a}$; R$^{6b}$; W$^7$; R$^7$; R$^{7c}$; R$^{7d}$; R$^7$; L$^7$; R$^{17}$; W$^8$; R$^8$; R$^{8a}$; R&b; W$^9$; W$^{10}$; R$^9$; R$^4$;

L$^4$; R$^{4c}$; R$^{4d}$; R$^{4a}$; R$^{11c}$; R$^{12}$; R$^{12c}$; R$^{13}$; R$^{14}$; R$^{14a}$; R$^{15}$; R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, R$^{20m}$; R$^{21}$; R$^{22}$;

R$^{23}$; R$^{24}$; and R$^{25}$ are as described for Formula (C), including in embodiments of a compound of Formula (C);

each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(═O)(═NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(0)$_2$R$^{15}$, —CH$_2$S(0)$_2$N(R$^{12}$)(R$^{13}$), and —P(═O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, and C$_{1-9}$heteroaryl are optionally substituted with one or more R$^{20}$j; and ----- indicates a single or double bond such that all valences are satisfied.

In some embodiments, the compound of Formula (C'), or a pharmaceutically acceptable salt or solvate thereof, has the structure of Formula (C'-1):

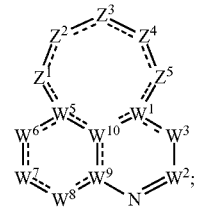

Formula (C'-1)

wherein

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (C') or (C'-1), or a pharmaceutically acceptable salt or solvate thereof, has the structure of Formula (C'-1a):

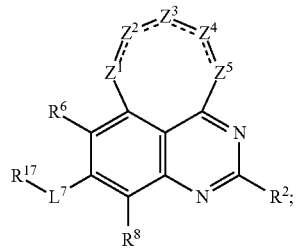

Formula (C'-1a)

wherein

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (C') or (C'-1), or a pharmaceutically acceptable salt or solvate thereof, has the structure of Formula (C'-1b):

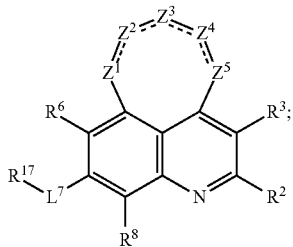

Formula (C'-1b)

wherein
Z¹, Z³, and Z' are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
Z² and Z⁴ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
wherein at least one of Z¹, Z², Z³, Z⁴, and Z⁵ is N($R^4$), C($R^4$), C($R^4$)(H), C($R^4$)($R^{11c}$), or C($R^4$)($R^4$).

In some embodiments, the compound of Formula (C') or (C'-1), or a pharmaceutically acceptable salt or solvate thereof, has the structure of Formula (C'-1c):

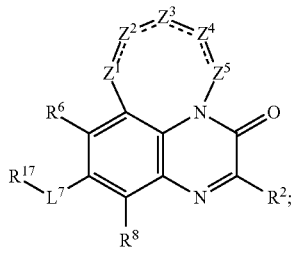

Formula (C'-1c)

wherein
Z¹, Z³, and Z' are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
Z² and Z⁴ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
wherein at least one of Z¹, Z², Z³, Z⁴, and Z⁵ is N($R^4$), C($R^4$), C($R^4$)(H), C($R^4$)($R^{11c}$), or C($R^4$)($R^4$).

In some embodiments, the compound of Formula (C') or (C'-1), or a pharmaceutically acceptable salt or solvate thereof, has the structure of Formula C-1d):

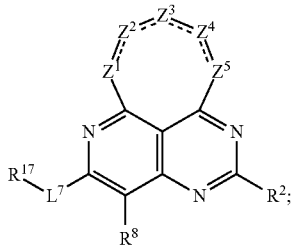

Formula (C'-1d)

wherein
Z¹, Z³, and Z⁵ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
Z² and Z⁴ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
wherein at least one of Z¹, Z², Z³, Z⁴, and Z⁵ is N($R^4$), C($R^4$), C($R^4$)(H), C($R^4$)($R^{11c}$), or C($R^4$)($R^4$).

In some embodiments, the compound of Formula (C') or (C'-1), or a pharmaceutically acceptable salt or solvate thereof, has the structure of Formula (C'-1e):

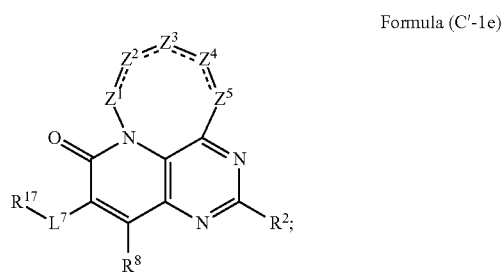

Formula (C'-1e)

wherein
Z¹, Z³, and Z⁵ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
Z² and Z⁴ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
wherein at least one of Z¹, Z², Z³, Z⁴, and Z⁵ is N($R^4$), C($R^4$), C($R^4$)(H), C($R^4$)($R^{11c}$), or C($R^4$)($R^4$).

In some embodiments, the compound of Formula (C') or (C'-1), or a pharmaceutically acceptable salt or solvate thereof, has the structure of Formula (C'-1f):

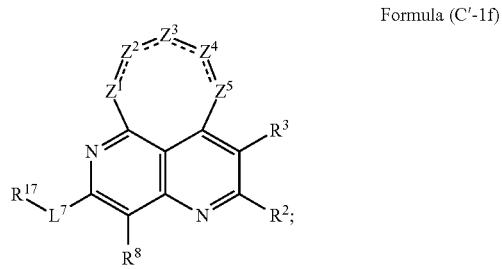

Formula (C'-1f)

wherein
Z¹, Z³, and Z⁵ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
Z² and Z⁴ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
wherein at least one of Z¹, Z², Z³, Z⁴, and Z⁵ is N($R^4$), C($R^4$), C($R^4$)(H), C($R^4$)($R^{11c}$), or C($R^4$)($R^4$).

In an aspect is provided a compound of Formula (A"), or a pharmaceutically acceptable salt or solvate thereof:

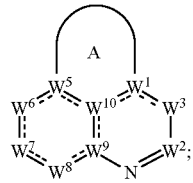

Formula (A")

wherein:
Ring A; $W^1$; $R^1$; $W^2$; $W^3$; $R^3$; $R^{3a}$; $R^{3b}$; $W^5$; $R^5$; $W^6$; $R^6$; $R^{6a}$; $R^0$; $W^7$; $R^{7a}$; $R^{7c}$; $R^{7d}$; $R^7$; $L^7$; $R^{17}$; Ring B; $X^6$, $X^7$, $X^8$; $X^9$, $X^{10}$, $X^{11}$; $R1a$,
$R^{1b}$, $R^{1c}$; $W^8$; $R^8$; $R^{6a}$; $R^{8b}$; $W^9$; $W^{10}$; $R^9$; $R^4$; $L^4$; $R^{4c}$; $R^{4d}$; $R^{4a}$; $R^{12}$; $R^{12c}$; $R^{13}$; $R^{14}$; $R^{14a}$, $R^{15}$; $R^{21}$; $R^{22}$; $R^{23}$; $R^{24}$; and $R^{25}$ are as described for Formula (A), including in embodiments of a compound of Formula (A);
each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, =$C(R^{21b})_2$, —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more $R^{20}j$;
$R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$N=(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{12}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20b}$;
each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$—$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —$(C_{1-6}alkyl)$-OC(O)$R^{12}$, —$(C_{1-6}alkyl)$-$N(R^{12})(R^{13})$, —$(C_{1-6}alkyl)$-C(O)N($R^{12}$)($R^{13}$), —$(C_{1-6}alkyl)$-$N(R^{14})C(O)R^{12}$, —$(C_{1-6}alkyl)$-$S(O)_2R^{15}$, —$(C_{1-6}alkyl)$-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, three, four, or five $R^{20k}$;
each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, =$NR^{21}$, =$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_3$-10cycloalkyl, —$CH_2$-$C_3$-10cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ----- indicates a single or double bond such that all valences are satisfied.

In some embodiments, the compound of Formula (A"), or a pharmaceutically acceptable salt or solvate thereof, has the structure of Formula (A"-1):

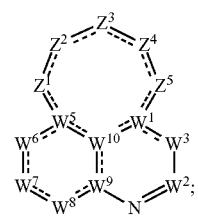

Formula (A"-1)

wherein
$W^1$; $R^1$; $R^2$; $W^2$; $W^3$; $R^3$; $R^{3a}$; $R^{30}$; $W^5$; $R^5$; $W^6$; $R^6$; $R^{6a}$; $R^{6b}$; $W^7$; $R^{7a}$; $R^{7c}$; $R^{7d}$; $R^7$; $L^7$; $R^{17}$; Ring B; $X^6$, $X^1$, $X^8$; $X^9$, $X^{10}$, $X^{11}$; $R^{1a}$, $R^{1b}$,
$R^{7c}$; $W^8$; $R^8$; $R^{8a}$; $R^{8b}$; $W^9$; $W^{10}$; $R^9$; $R^4$; $L^4$; $R^{4c}$; $R^{4d}$; $R^{4a}$; $R^{4b}$; $R^{11c}$; $R^{12}$; $R^{12c}$; $R^{13}$; $R^{14}$; $R^{14a}$; $R^{15}$; $R^{208}$, $R^{20g}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$; $R^{23}$; $R^{24}$; and $R^{25}$ are as described for Formula (A"), including in embodiments of a compound of Formula (A");

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A") or (A"-1), or a pharmaceutically acceptable salt or solvate thereof, has the structure of Formula (A"-1a):

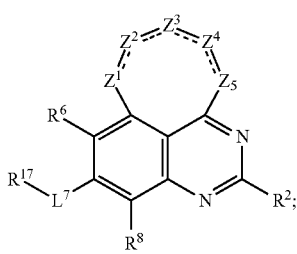

Formula (A"-1a)

$R^2$; $R^6$; $L^7$; $R^{17}$; Ring B; $X^6$, $X^1$, $X^8$, $X^9$, $X^{10}$, $X^{11}$; $R^{14}$, $R^{1b}$, $R^{7c}$; $R^8$; $R^4$; $L^4$; $R^4$; $R^{4d}$, $R^{48}$; $R^{4b}$; $R^{11c}$; $R^{12}$; $R^{12c}$; $R^{13}$; $R^{14}$; $R^{14a}$; $R^{15}$; $R^{20a}$, $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$; $R^{23}$; $R^{24}$; and $R^{25}$ are as described for Formula (A"), including in embodiments of a compound of Formula (A");

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A") or (A"-1), or a pharmaceutically acceptable salt or solvate thereof, has the structure of Formula (A"-1b):

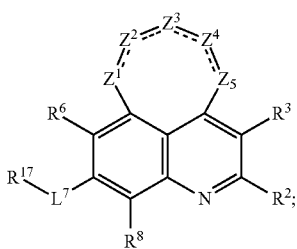

Formula (A"-1b)

$R^2$; $R^3$; $R^6$; $L^7$; $R^{17}$; Ring B; $X^6$, $X^1$, $X^8$, $X^9$, $X^{10}$, $X^{11}$; $R^{18}$, $R^{1b}$, $R^{1c}$; $R^8$; $R^4$; $L^4$; $R^4$; $R^{4a}$; $R^{48}$; $R^{4B}$; $R^{11c}$; $R^{12}$; $R^{12c}$; $R^{13}$; $R^{14}$; $R^{14a}$; $R^{15}$;

$R^{208}$, $R^{20b}$, $R^{20c}$; $R^{20g}$, $R^{208}$, $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$; $R^{23}$; $R^{24}$; and $R^{25}$ are as described for Formula (A"), including in embodiments of a compound of Formula (A");

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A") or (A"-1), or a pharmaceutically acceptable salt or solvate thereof, has the structure of Formula (A"-1c):

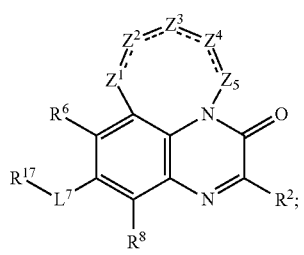

Formula (A"-1c)

$R^2$; $R^6$; $L^7$; $R^{17}$; Ring B; $X^6$, $X^1$, $X^8$, $X^9$, $X^{10}$, $X^{11}$; $R^{18}$, $R^{1b}$, $R^{7c}$; $R^8$; $R^4$; $L^4$; $R^4$; $R^{4d}$, $R^{48}$; $R^{4b}$; $R^{11c}$; $R^{12}$; $R^{12c}$; $R^{13}$; $R^{14}$; $R^{14a}$; $R^{15}$; $R^{208}$, $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$; $R^{23}$; $R^{24}$; and $R^{25}$ are as described for Formula (A"), including in embodiments of a compound of Formula (A");

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$; and $Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, $S$, $O$, and $C(O)$;

wherein at least one of $Z^1$, $Z^2$, $Z^3$, $Z^4$, and $Z^5$ is $N(R^4)$, $C(R^4)$, $C(R^4)(H)$, $C(R^4)(R^{11c})$, or $C(R^4)(R^4)$.

In some embodiments, the compound of Formula (A") or (A"-1), or a pharmaceutically acceptable salt or solvate thereof, has the structure of Formula (A"-1d):

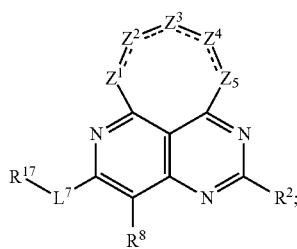

Formula (A"-1d)

$R^2$; $L^7$; $R^{17}$; Ring B; $X^6$, $X^1$, $X^8$, $X^9$, $X^{10}$, $X^{11}$; $R^{1a}$, $R^{1b}$, $R^{1c}$; $R^8$; $R^4$; $L^4$; $R^4$; $R^{4d}$, $R^{48}$; $R^4$; $R^{11c}$; $R^{12}$; $R^{12c}$; $R^{13}$; $R^{14}$; $R^{14a}$; $R^{15}$; $R^{208}$, $R^{20b}$, $R^{20}c$, $R^{20d}$, $R^{20e}$; $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$; $R^{23}$; $R^{24}$; and $R^{25}$ are as described for Formula (A"), including in embodiments of a compound of Formula (A");

$Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), CH$_2$, S, O, and C(O); and $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), CH$_2$, S, O, and C(O);

wherein at least one of $Z^1$, $Z^2$, $Z^3$, $Z^4$, and $Z^5$ is N($R^4$), C($R^4$), C($R^4$)(H), C($R^4$)($R^{11c}$), or C($R^4$)($R^4$).

In some embodiments, the compound of Formula (A") or (A"-1), or a pharmaceutically acceptable salt or solvate thereof, has the structure of Formula (A"-1e):

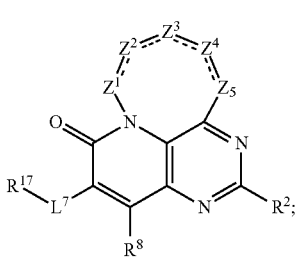

Formula (A"-1e)

$R^2$; $L^7$; $R^{17}$; Ring B; $X^6$, $X^1$, $X^8$; $X^9$, $X^{10}$, $X^{11}$; $R^{18}$, $R^{1b}$, $R^{1c}$; $R^8$; $R^4$; $L^4$; $R^{4c}$; $R^{4d}$; $R^{48}$; $R^{4b}$; $R^{11c}$; $R^{12}$; $R^{12c}$; $R^{13}$; $R^{14}$; $R^{14a}$; $R^{15}$; $R^{208}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$; $R^{23}$; $R^{24}$; and $R^{25}$ are as described for Formula (A"), including in embodiments of a compound of Formula (A");

$Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), CH$_2$, S, O, and C(O); and $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), CH$_2$, S, O, and C(O);

wherein at least one of $Z^1$, $Z^2$, $Z^3$, $Z^4$, and $Z^5$ is N($R^4$), C($R^4$), C($R^4$)(H), C($R^4$)($R^{11c}$), or C($R^4$)($R^4$).

In some embodiments, the compound of Formula (A") or (A"-1), or a pharmaceutically acceptable salt or solvate thereof, has the structure of Formula (A"-1f):

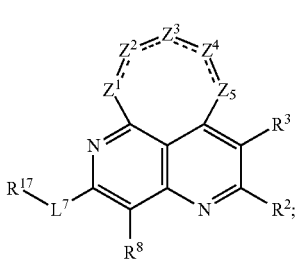

Formula (A"-1f)

$R^2$; $R^3$; $L^7$; $R^{17}$; Ring B; $X^6$, $X^1$, $X^8$; $X^9$, $X^{10}$, $X^{11}$; $R^{14}$, $R^{1b}$, $R^{1c}$; $R^8$; $R^4$; $L^4$; $R^{4c}$; $R^{4a}$; $R^{48}$; $R^{4b}$; $R^{11c}$; $R^{12}$; $R^{12c}$; $R^{13}$; $R^{14}$; $R^{14a}$; $R^{15}$; $R^{208}$, $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, $R^{20m}$, $R^{21}$; $R^{21b}$; $R^{22}$;

$R^{23}$; $R^{24}$; and $R^{25}$ are as described for Formula (A"), including in embodiments of a compound of Formula (A");

$Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), CH$_2$, S, O, and C(O); and $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), CH$_2$, S, O, and C(O);

wherein at least one of $Z^1$, $Z^2$, $Z^3$, $Z^4$, and $Z^5$ is N($R^4$), C($R^4$), C($R^4$)(H), C($R^4$)($R^{11c}$), or C($R^4$)($R^4$).

In an aspect is provided a compound of Formula (B"), or a pharmaceutically acceptable salt or solvate thereof:

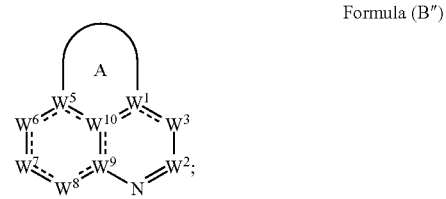

Formula (B")

wherein:

Ring A; $W^1$; $R^1$; $W^2$; $W^3$; $R^3$; $R^{3a}$; $R^{30}$; $W^5$; $R^5$; $W^6$; $R^6$; $R^{6a}$; $R^{6b}$; $W^7$; $R^{7a}$; $R^{7c}$; $R^{7d}$; $R^7$; $L^7$; $R^{17}$; Ring B; $X^6$, $X^1$, $X^8$; $X^9$, $X^{10}$, $X^{11}$; $R^{1a}$,$R^{1b}$, $R^{7c}$; $W^8$; $R^8$; $R^{6a}$; $R^{8b}$; $W^9$; $W^{10}$; $R^9$; $R^4$; $L^4$; $R^{4c}$; $R^{4d}$; $R^{43}$; $R^{12}$; $R^{12c}$; $R^{13}$; $R^{14}$; $R^{14a}$; $R^{15}$; $R^{21}$; $R^{22}$; $R^{23}$; $R^{24}$; and $R^{25}$ are as described for Formula (B), including in embodiments of a compound of Formula (B);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more R$^{20}$j;

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three R$^{20b}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-12}$aryl, —CH$_2$-C$_{6-12}$aryl, —CH$_2$-C$_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=O)(=NH)N(R$^{12}$)(R$^{13}$), —(C$_{1-6}$alkyl)-OC(O)R$^{12}$, —(C$_{1-6}$alkyl)-N(R$^{12}$)(R$^{13}$), —(C$_{1-6}$alkyl)-C(O)N(R$^{12}$)(R$^{13}$), —(C$_{1-6}$alkyl)-N(R$^{14}$)C(O)R$^{12}$, —(C$_{1-6}$alkyl)-S(O)$_2$R$^{15}$, —(C$_{1-6}$alkyl)-S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-12}$aryl, —CH$_2$-C$_{6-12}$aryl, —CH$_2$-C$_{1-11}$heteroaryl, and $C_{1-11}$heteroaryl are optionally substituted with one, two, three, four, or five $R^{20k}$;

each $R^{20a}$; $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, $C_{1-9}$heteroaryl, —OR$^{21}$, —SR$^{21}$, —N(R$^{22}$)(R$^{23}$), =NR$^{21}$, =C(R$^{21b}$)$_2$, —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_3$-10cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{21}$, —N(R$^{24}$)S(O)$_2$R$^{25}$, —C(O)R$^{21}$, —S(O)$_2$R$^{25}$, —S(O)$_2$N(R$^{22}$)(R$^{23}$), and —OC(O)R$^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH; and ----- indicates a single or double bond such that all valences are satisfied.

In some embodiments, the compound of Formula (B″), or a pharmaceutically acceptable salt or solvate thereof, has the structure of Formula (B″-1):

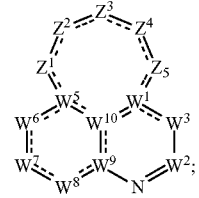

Formula (B″-1)

wherein

W$^1$; R$^1$; R$^2$; W$^2$; W$^3$; R$^3$; R$^{3a}$; R$^{3b}$; W$^5$; R$^5$; W$^6$; R$^6$; R$^{6a}$; R$^{6b}$; W$^7$; R$^{7a}$; R$^{7c}$; R$^{7d}$; R$^7$; L$^7$; R$^{17}$; Ring B; X$^6$, X$^1$, X$^8$; X$^9$, X$^{10}$, X$^{11}$; R$^{1a}$, R$^{1b}$, R$^{7c}$; W$^8$; R$^8$; R$^{6a}$; R$^{8b}$; W$^9$; W$^{10}$; R$^9$; R$^4$; L$^4$; R$^{4c}$; R$^{4d}$; R$^{48}$; R$^{48}$; R$^{11c}$; R$^{12}$; R$^{12c}$; R$^{13}$; R$^{14}$; R$^{14a}$; R$^{15}$; R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, R$^{20m}$ R$^{21}$; R$^{21b}$; R$^{22}$; R$^{23}$; R$^{24}$; and R$^{25}$ are as described for Formula (B″), including in embodiments of a compound of Formula (B″);

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O); Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O).

In some embodiments, the compound of Formula (B″) or (B″-1), or a pharmaceutically acceptable salt or solvate thereof, has the structure of Formula (B″-1a):

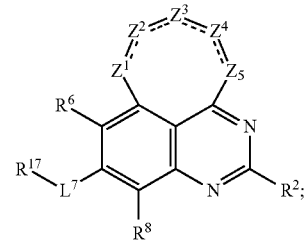

Formula (B″-1a)

wherein

R$^2$; R$^6$; L$^7$; R$^{17}$; Ring B; X$^6$, X$^1$, X$^8$; X$^9$, X$^{10}$, X$^{11}$; R$^{14}$, R$^{1b}$, R$^{7c}$; R$^8$; R$^4$; L$^4$; R$^{4c}$; R$^{4d}$; R$^{48}$; R$^{11c}$; R$^{4b}$; R$^{12}$; R$^{12c}$; R$^{13}$; R$^{14}$; R$^{14a}$; R$^{15}$; R$^{20a}$, R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, R$^{20m}$ R$^{21}$; R$^{21b}$; R$^{22}$; R$^{23}$; R$^{24}$; and R$^{25}$ are as described for Formula (B″), including in embodiments of a compound of Formula (B″);

Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O).

In some embodiments, the compound of Formula (B″) or (B″-1), or a pharmaceutically acceptable salt or solvate thereof, has the structure of Formula (B″-1b):

Formula (B″-1b)

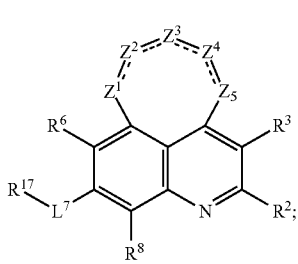

wherein
- $R^2$; $R^3$; $R^6$; $L^7$; $R^{17}$; Ring B; $X^6$, $X^1$, $X^8$, $X^9$, $X^{10}$, $X^{11}$; $R^{1a}$, $R^{1b}$, $R^{7c}$; $R^8$; $R^4$; $L^4$; $R^{4c}$; $R^{4d}$; $R^{48}$; $R^{4b}$; $R^{11c}$; $R^{12}$; $R^{12c}$, $R^{13}$; $R^{14}$; $R^{14a}$; $R^{15}$; $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, $R^{20m}$ $R^{21}$; $R^{216}$; $R^{22}$; $R^{23}$; $R^{24}$; and $R^{25}$ are as described for Formula (B″), including in embodiments of a compound of Formula (B″);
- $Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
- $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O).

In some embodiments, the compound of Formula (B″) or (B″-1), or a pharmaceutically acceptable salt or solvate thereof, has the structure of Formula (B″-1c):

Formula (B″-1c)

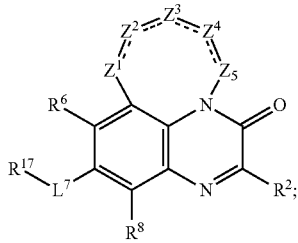

wherein
- $R^2$; $R^6$; $L^7$; $R^{17}$; Ring B; $X^6$, $X^7$, $X^8$, $X^9$, $X^{10}$, $X^{11}$; $R^{18}$, $R^{1b}$, $R^{7c}$; $R^8$; $R^4$; $L^4$; $R^4$; $R^{4a}$; $R^{48}$; $R^{4b}$; $R^{11c}$; $R^{12}$; $R^{12c}$; $R^{13}$; $R^{14}$; $R^{14a}$; $R^{15}$; $R^{20a}$;
- $R^{20g}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, $R^{20m}$ $R^{21}$; $R^{216}$; $R^{22}$; $R^{23}$; $R^{24}$; and $R^{25}$ are as described for Formula (B″), including in embodiments of a compound of Formula (B″);
- $Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
- $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O).

In some embodiments, the compound of Formula (B″) or (B″-1), or a pharmaceutically acceptable salt or solvate thereof, has the structure of Formula B-1d):

Formula (B″-1d)

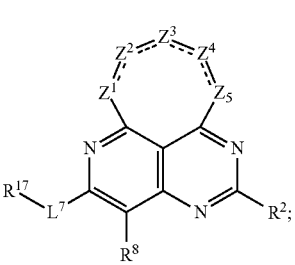

wherein
- $R^2$; $L^7$; $R^{17}$; Ring B; $X^6$, $X^1$, $X^8$, $X^9$, $X^{10}$, $X^{11}$; $R^{14}$, $R^{1b}$, $R^{7c}$; $R^8$; $R^4$; $L^4$; $R^4$; $R^{4a}$; $R^{48}$; $R^{4b}$; $R^{11c}$; $R^{12}$; $R^{12c}$; $R^{13}$; $R^{14}$, $R^{14a}$; $R^{15}$; $R^{208}$, $R^{20b}$,
- $R^{20c}$; $R^{20g}$, $R^{20c}$; $R^{20f}$, $R^{20g}$, $R^{20h}$, $R^{20i}$, $R^{20j}$, $R^{20k}$, $R^{20l}$, $R^{20m}$ $R^{21}$; $R^{21b}$; $R^{22}$; $R^{23}$; $R^{24}$; and $R^{25}$ are as described for Formula (B″), including in embodiments of a compound of Formula (B″);
- $Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
- $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O).

In some embodiments, the compound of Formula (B″) or (B″-1), or a pharmaceutically acceptable salt or solvate thereof, has the structure of Formula (B″-1e):

Formula (B″-1e)

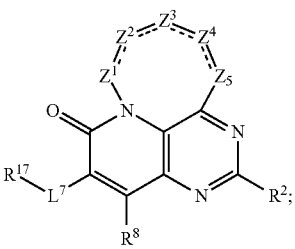

wherein
- $R^2$; $L^7$; $R^{17}$; Ring B; $X^6$, $X^1$, $X^8$, $X'$, $X^{10}$, $X^{11}$; $R^{18}$, $R^{1b}$, $R^{7c}$; $R^8$; $R^4$; $L^4$; $R^4$; $R^{4a}$; $R^{48}$; $R^{46}$; $R^{11c}$; $R^{12}$; $R^{12c}$; $R^{13}$; $R^{14}$, $R^{14a}$; $R^{15}$; $R^{20a}$, $R^{20b}$,
- $R^{20c}$; $R^{20g}$, $R^{20c}$; $R^{20f}$, $R^{20g}$, $R^{20h}$, $R^{20i}$, $R^{20j}$, $R^{20k}$, $R^{20l}$, $R^{20m}$ $R^{21}$; $R^{21b}$; $R^{22}$; $R^{23}$; $R^{24}$; and $R^{25}$ are as described for Formula (B″), including in embodiments of a compound of Formula (B″);
- $Z^1$, $Z^3$, and $Z^5$ are each independently selected from N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O);
- $Z^2$ and $Z^4$ are each independently selected from a bond, N($R^4$), N($R^{11c}$), N(H), N, C($R^4$), C($R^{11c}$), C(H), C($R^4$)(H), C($R^4$)($R^{11c}$), C($R^{11c}$)($R^{11c}$), C($R^4$)($R^4$), C($R^{11c}$)(H), $CH_2$, S, O, and C(O).

In some embodiments, the compound of Formula (B″) or (B″-1), or a pharmaceutically acceptable salt or solvate thereof, has the structure of Formula (B″-1f):

Formula (B″-1f)

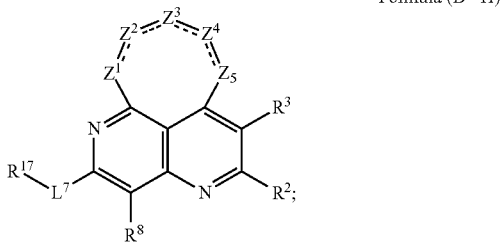

wherein
$R^2$; $R^3$; $L^7$; $R^{17}$; Ring B; $X^6$, $X^1$, $X^8$; $X^9$, $X^{10}$, $X^{11}$; $R^{1a}$, $R^{1b}$, $R^{7c}$; $R^8$; $R^4$; $L^4$; $R^4$; $R^{4d}$, $R^{43}$; $R^{4b}$; $R^{11c}$; $R^{12}$; $R^{12c}$; $R^{13}$; $R^{14}$; $R^{14a}$; $R^{15}$; $R^{20a}$; $R^{20b}$, $R^{20c}$; $R^{20d}$, $R^{20e}$, $R^{20f}$, $R^{20g}$, $R^{20h}$, $R^{20i}$, $R^{20j}$, $R^{20k}$, $R^{20l}$, $R^{20m}$ $R^{21}$; $R^{21b}$; $R^{22}$; $R^{23}$; $R^{24}$; and $R^{25}$ are as described for Formula (B″), including in embodiments of a compound of Formula (B″);

$Z^1$, $Z^3$, and $Z^5$ are each independently selected from $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$;

$Z^2$ and $Z^4$ are each independently selected from a bond, $N(R^4)$, $N(R^{11c})$, $N(H)$, $N$, $C(R^4)$, $C(R^{11c})$, $C(H)$, $C(R^4)(H)$, $C(R^4)(R^{11c})$, $C(R^{11c})(R^{11c})$, $C(R^4)(R^4)$, $C(R^{11c})(H)$, $CH_2$, S, O, and $C(O)$.

In an aspect is provided a compound of Formula (C″), or a pharmaceutically acceptable salt or solvate thereof:

Formula (C″)

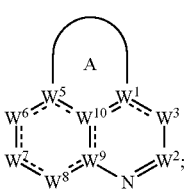

wherein:
Ring A; $W^1$; $R^1$; $W^2$; $W^3$; $R^3$; $R^{3a}$; $R^{3b}$; $W^5$; $R^5$; $W^6$; $R^6$; $R^{6a}$; $R^0$; $W^7$; $R^{7a}$; $R^{7c}$; $R^{7d}$; $R^7$; $L^7$; $R^{17}$; $W^8$; $R^8$; $R^{8a}$; R&b; $W^9$; $W^{10}$; $R^9$; $R^4$; $L^4$;

$R^4$; $R^{4d}$; $R^{4a}$; $R^{12}$; $R^{12o}$; $R^{13}$; $R^{14}$; $R^{14a}$; $R^{15}$; $R^{21}$; $R^{22}$; $R^{23}$; $R^{24}$; and $R^{25}$ are as described for Formula (C), including in embodiments of a compound of Formula (C);

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$C(R^{21b})_2$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —S(—OX—NH)N(R^{12})(R^{13}), —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

$R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —N=($R^{15}$), —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=O)(=NH)N(R^{12})(R^{13})$, —($C_{1-6}$alkyl)-$OC(O)R^{12}$, —($C_{1-6}$alkyl)-$N(R^{12})(R^{13})$, —($C_{1-6}$alkyl)-$C(O)N(R^{12})(R^{13})$, —($C_{1-6}$alkyl)-$N(R^{14})C(O)R^{12}$, —($C_{1-6}$alkyl)-$S(O)_2R^{15}$, —($C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, three, four, or five $R^{20k}$;

each $R^{20a}$; $R^{20g}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$NR^{21}$, —$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_3$-10cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, C$_{1-3}$ alkyl, C$_{1-3}$ haloalkyl, and —OH; and ----- indicates a single or double bond such that all valences are satisfied.

In some embodiments, the compound of Formula (C″), or a pharmaceutically acceptable salt or solvate thereof, has the structure of Formula (C″-1):

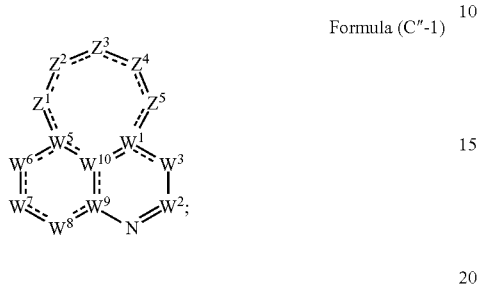

Formula (C″-1)

wherein
W$^1$; R$^1$; R$^2$; W$^3$; R$^3$; R$^{3a}$; R$^{3b}$; W$^5$; R$^5$; W$^6$; R$^6$; R$^{6a}$; R$^{6b}$; W$^7$; R$^{7a}$; R$^{7c}$; R$^{7d}$; R$^7$; L$^7$; R$^{17}$; Ring B; X$^6$, X$^1$, X$^8$, X$^9$, X$^{10}$, X$^{11}$, R$^{1a}$, R$^{1b}$, R$^{7c}$; W$^8$; R$^8$; R$^{8a}$; R&b; W$^9$; W$^{10}$, R$^9$; R$^4$; L$^4$; R$^{4c}$; R$^{4d}$; R$^{4a}$; R$^{4b}$; R$^{11c}$; R$^{12}$; R$^{12c}$; R$^{13}$; R$^{14}$; R$^{14a}$; R$^{15}$; R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, R$^{20m}$, R$^{21}$; R$^{21b}$; R$^{22}$; R$^{23}$; R$^{24}$; and R$^{25}$ are as described for Formula (C″), including in embodiments of a compound of Formula (C″);
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (C″) or (C″-1), or a pharmaceutically acceptable salt or solvate thereof, has the structure of Formula (C″-1a):

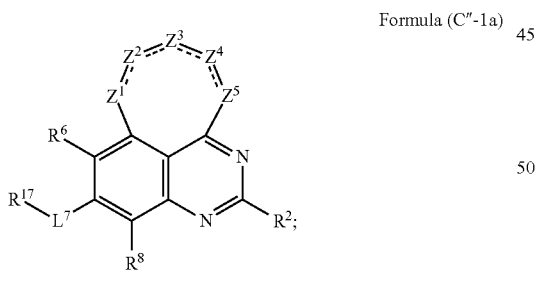

Formula (C″-1a)

wherein
R$^2$; R$^6$; L$^7$; R$^{17}$; Ring B; X$^6$, X$^7$, X$^8$, X$^9$, X$^{10}$, X$^{11}$, R$^{1a}$, R$^{1b}$, R$^{7c}$; R$^8$; R$^4$; L$^4$; R$^4$; R$^{4d}$; R$^{48}$; R$^{4b}$; R$^{11c}$; R$^{12}$; R$^{12c}$; R$^{13}$; R$^{14}$; R$^{14a}$; R$^{15}$; R$^{208}$, R$^{20g}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, R$^{20m}$, R$^{21}$; R$^{21b}$; R$^{22}$; R$^{23}$; R$^{24}$; and R$^{25}$ are as described for Formula (C″), including in embodiments of a compound of Formula (C″);
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (C″) or (C″-1), or a pharmaceutically acceptable salt or solvate thereof, has the structure of Formula (C″-1b):

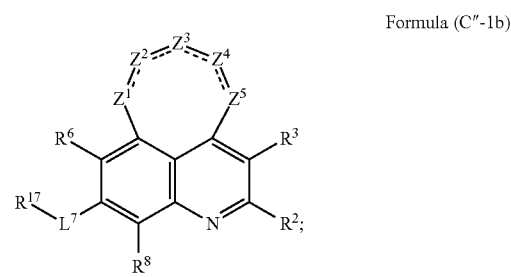

Formula (C″-1b)

wherein
R$^2$; R$^3$; R$^6$; L$^7$; R$^{17}$; Ring B; X$^6$, X$^1$, X$^8$; X$^9$, X$^{10}$, X$^{11}$; R$^{1a}$, R$^{1b}$, R$^{7c}$; R$^8$; R$^4$; L$^4$; R$^{4c}$; R$^{4d}$; R$^{48}$; R$^{4b}$; R$^{11c}$; R$^{12}$; R$^{12c}$; R$^{13}$; R$^{14}$; R$^{14a}$; R$^{15}$; R$^{20a}$, R$^{20b}$, R$^{20c}$, R$^{20g}$, R$^{20b}$, R$^{20f}$, R$^{20g}$, R$^{20h}$, R$^{20i}$, R$^{20j}$, R$^{20g}$, R$^{20l}$, R$^{20m}$, R$^{21}$; R$^{21b}$; R$^{22}$; R$^{23}$; R$^{24}$; and R$^{25}$ are as described for Formula (C″), including in embodiments of a compound of Formula (C″);
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
Z$^2$ and Z$^4$ are each independently selected from a bond, N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);
wherein at least one of Z$^1$, Z$^2$, Z$^3$, Z$^4$, and Z$^5$ is N(R$^4$), C(R$^4$), C(R$^4$)(H), C(R$^4$)(R$^{11c}$), or C(R$^4$)(R$^4$).

In some embodiments, the compound of Formula (C″) or (C″-1), or a pharmaceutically acceptable salt or solvate thereof, has the structure of Formula (C″-1c):

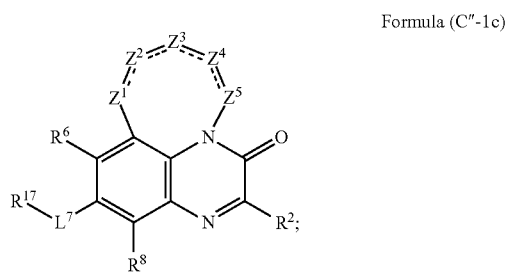

Formula (C″-1c)

wherein
R$^2$; R$^6$; L$^7$; R$^{17}$; Ring B; X$^6$, X$^7$, X$^8$; X$^9$, X$^{10}$, X$^{11}$; R$^{18}$, R$^{1b}$, R$^{7c}$; R$^8$; R$^4$; L$^4$; R$^{4c}$; R$^{4a}$; R$^{48}$; R$^{4b}$; R$^{11c}$; R$^{12}$; R$^{12c}$; R$^{13}$; R$^{14}$; R$^{14a}$; R$^{15}$; R$^{20a}$, R$^{20b}$, R$^{20c}$, R$^{20d}$, R$^{20e}$, R$^{20f}$, R$^{20g}$, R$^{20h}$, R$^{20i}$, R$^{20j}$, R$^{20k}$, R$^{20l}$, R$^{20m}$, R$^{21}$; R$^{21b}$; R$^{22}$; R$^{23}$; R$^{24}$; and R$^{25}$ are as described for Formula (C″), including in embodiments of a compound of Formula (C″);
Z$^1$, Z$^3$, and Z$^5$ are each independently selected from N(R$^4$), N(R$^{11c}$), N(H), N, C(R$^4$), C(R$^{11c}$), C(H), C(R$^4$)(H), C(R$^4$)(R$^{11c}$), C(R$^{11c}$)(R$^{11c}$), C(R$^4$)(R$^4$), C(R$^{11c}$)(H), CH$_2$, S, O, and C(O);

Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

wherein at least one of Z¹, Z², Z³, Z⁴, and Z⁵ is N(R⁴), C(R⁴), C(R⁴)(H), C(R⁴)(R¹¹ᶜ), or C(R⁴)(R⁴).

In some embodiments, the compound of Formula (C″) or (C″-1), or a pharmaceutically acceptable salt or solvate thereof, has the structure of Formula C-1d):

Formula (C″-1d)

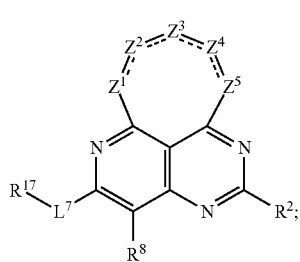

wherein
R²; L⁷; R¹⁷; Ring B; X⁶, X¹, X⁸, X⁹, X¹⁰, X¹¹; R¹ᵃ, R¹ᵇ, R¹ᶜ; R⁸; R⁴; L⁴; R⁴ᶜ; R⁴ᵃ; R⁴ˢ; R⁴ᵇ; R¹¹ᶜ; R¹²; R¹²ᶜ; R¹³; R¹⁴; R¹⁴ᵃ; R¹⁵; R²⁰⁸, R²⁰%, R²⁰ᶜ, R²⁰ᵈ, R²⁰ᵉ, R²⁰ᶠ, R²⁰ᵍ, R²⁰ʰ, R²⁰ⁱ, R²⁰ʲ, R²⁰ᵏ, R²⁰ˡ, R²⁰ᵐ, R²¹; R²¹ᵇ; R²²; R²³; R²⁴; and R²⁵ are as described for Formula (C″), including in embodiments of a compound of Formula (C″);
Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O); Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);
wherein at least one of Z¹, Z², Z³, Z⁴, and Z⁵ is N(R⁴), C(R⁴), C(R⁴)(H), C(R⁴)(R¹¹ᶜ), or C(R⁴)(R⁴).

In some embodiments, the compound of Formula (C″) or (C″-1), or a pharmaceutically acceptable salt or solvate thereof, has the structure of Formula (C″-1e):

Formula (C″-1e)

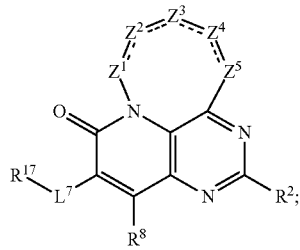

wherein
R²; L⁷; R¹⁷; Ring B; X⁶, X¹, X⁸, X⁹, X¹⁰, X¹¹; R¹ᵇ, R¹ᵇ, R⁷ᶜ; R⁸; R⁴; L⁴; R⁴; R⁴ᵃ; R⁴ˢ; R⁴⁶; R¹¹ᶜ; R¹²; R¹²⁰; R¹³; R¹⁴; R¹⁴ᵃ; R¹⁵; R²⁰⁸, R²⁰ᵇ, R²⁰ᶜ, R²⁰ᵍ, R²⁰ᶜ; R²⁰ᶠ, R²⁰ᵍ, R²⁰ʰ, R²⁰ⁱ, R²⁰ʲ, R²⁰ᵏ, R²⁰ˡ, R²⁰ᵐ; R²¹; R²¹ᵇ; R²²; R²³; R²⁴; and R²⁵ are as described for Formula (C″), including in embodiments of a compound of Formula (C″);
Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);

wherein at least one of Z¹, Z², Z³, Z⁴, and Z⁵ is N(R⁴), C(R⁴), C(R⁴)(H), C(R⁴)(R¹¹ᶜ), or C(R⁴)(R⁴).

In some embodiments, the compound of Formula (C″) or (C″-1), or a pharmaceutically acceptable salt or solvate thereof, has the structure of Formula (C″-1f):

Formula (C″-1f)

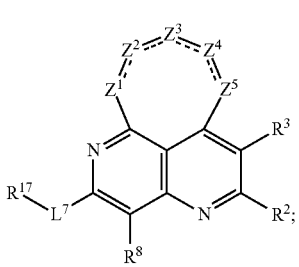

wherein
R²; R³; L⁷; R¹⁷; Ring B; X⁶, X¹, X⁸, X', X¹⁰, X¹¹; R¹ᵃ, R¹ᵇ, R¹ᶜ; R⁸; R⁴; L⁴; R⁴ᶜ; R⁴ᵈ; R⁴ˢ; R⁴ᵇ; R¹¹ᶜ; R¹²; R¹²ᶜ; R¹³; R¹⁴; R¹⁴ᵃ; R¹⁵; R²⁰⁸, R²⁰ᵍ, R²⁰ᶜ, R²⁰ᵍ, R²⁰ᵇ, R²⁰ᶠ, R²⁰ᵍ, R²⁰ʰ, R²⁰ˡ, R²⁰ʲ, R²⁰ᵏ, R²⁰ˡ, R²⁰ᵐ, R²¹; R²¹ᵇ; R²²; R²³; R²⁴; and R²⁵ are as described for Formula (C″), including in embodiments of a compound of Formula (C″);
Z¹, Z³, and Z⁵ are each independently selected from N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);
Z² and Z⁴ are each independently selected from a bond, N(R⁴), N(R¹¹ᶜ), N(H), N, C(R⁴), C(R¹¹ᶜ), C(H), C(R⁴)(H), C(R⁴)(R¹¹ᶜ), C(R¹¹ᶜ)(R¹¹ᶜ), C(R⁴)(R⁴), C(R¹¹ᶜ)(H), CH₂, S, O, and C(O);
wherein at least one of Z¹, Z², Z³, Z⁴, and Z⁵ is N(R⁴), C(R⁴), C(R⁴)(H), C(R⁴)(R¹¹ᶜ), or C(R⁴)(R⁴).

In some embodiments of a compound of Formula (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A″), (B″), (C″), (A″-1), (B″-1), (C″-1), (A″-1a), (B″-1a), (C″-1a), (A″-1b), (B″-1b), (C″-1b), (A″-1c), (B″-1c), (C″-1c), (A″-1d), (B″-1d), (C″-1d), (A″-1e), (B″-1e), (C″-1e), (A″-1f), (B″-1f), or (C″-1f), or any embodiment thereof;

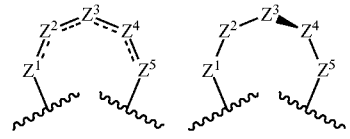

is

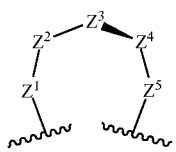

and $Z^1$, $Z^2$, $Z^3$, $Z^4$, and $Z^5$ are as described in Formula (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any embodiment thereof. In some embodiments of a compound of Formula (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any embodiment thereof;

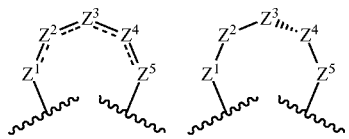

is

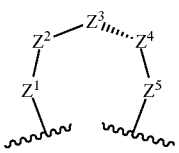

and $Z^1$, $Z^2$, $Z^3$, $Z^4$, and $Z^5$ are as described in Formula (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any embodiment thereof.

The individual embodiments herein below, or combinations thereof, (e.g., embodiments of $Z^1$, $Z^2$, $Z^3$, $Z^4$, or $Z^5$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $Z^1$ is $N(R^4)$. In embodiments of the formulae above, $Z^1$ is $N(R^{11c})$. In embodiments of the formulae above, $Z^1$ is N(H). In embodiments of the formulae above, $Z^1$ is N. In embodiments of the formulae above, $Z^1$ is $C(R^4)$. In embodiments of the formulae above, $Z^1$ is $C(R^{11c})$. In embodiments of the formulae above, $Z^1$ is C(H). In embodiments of the formulae above, $Z^1$ is $C(R^4)(H)$. In embodiments of the formulae above, $Z^1$ is $C(R^4)(R^{11c})$. In embodiments of the formulae above, $Z^1$ is $C(R^{11c})(R^{11c})$. In embodiments of the formulae above, $Z^1$ is $C(R^4)(R^4)$. In embodiments of the formulae above, $Z^1$ is $C(R^{11c})(H)$. In embodiments of the formulae above, $Z^1$ is $CH_2$. In embodiments of the formulae above, $Z^1$ is S. In embodiments of the formulae above, $Z^1$ is O. In embodiments of the formulae above, $Z^1$ is C(O). In embodiments of the formulae above, $Z^2$ is $N(R^4)$. In embodiments of the formulae above, $Z^2$ is $N(R^{11c})$. In embodiments of the formulae above, $Z^2$ is N(H). In embodiments of the formulae above, $Z^2$ is N. In embodiments of the formulae above, $Z^2$ is $C(R^4)$. In embodiments of the formulae above, $Z^2$ is $C(R^{11c})$. In embodiments of the formulae above, $Z^2$ is C(H). In embodiments of the formulae above, $Z^2$ is $C(R^4)(H)$. In embodiments of the formulae above, $Z^2$ is $C(R^4)(R^{11c})$. In embodiments of the formulae above, $Z^2$ is $C(R^{11c})(R^{11c})$. In embodiments of the formulae above, $Z^2$ is $C(R^4)(R^4)$. In embodiments of the formulae above, $Z^2$ is $C(R^{11c})(H)$. In embodiments of the formulae above, $Z^2$ is $CH_2$. In embodiments of the formulae above, $Z^2$ is S. In embodiments of the formulae above, $Z^2$ is O. In embodiments of the formulae above, $Z^2$ is C(O). In embodiments of the formulae above, $Z^2$ is a bond. In embodiments of the formulae above, $Z^3$ is $N(R^4)$. In embodiments of the formulae above, $Z^3$ is $N(R^{11c})$. In embodiments of the formulae above, $Z^3$ is N(H). In embodiments of the formulae above, $Z^3$ is N. In embodiments of the formulae above, $Z^3$ is $C(R^4)$. In embodiments of the formulae above, $Z^3$ is $C(R^{11c})$. In embodiments of the formulae above, $Z^3$ is C(H). In embodiments of the formulae above, $Z^3$ is $C(R^4)(H)$. In embodiments of the formulae above, $Z^3$ is $C(R^4)(R^{11c})$. In embodiments of the formulae above, $Z^3$ is $C(R^{11c})(R^{11c})$. In embodiments of the formulae above, $Z^3$ is $C(R^4)(R^4)$. In embodiments of the formulae above, $Z^3$ is $C(R^{11c})(H)$. In embodiments of the formulae above, $Z^3$ is $CH_2$. In embodiments of the formulae above, $Z^3$ is S. In embodiments of the formulae above, $Z^3$ is O. In embodiments of the formulae above, $Z^3$ is C(O). In embodiments of the formulae above, $Z^4$ is $N(R^4)$. In embodiments of the formulae above, $Z^4$ is $N(R^{11c})$. In embodiments of the formulae above, $Z^4$ is N(H). In embodiments of the formulae above, $Z^4$ is N. In embodiments of the formulae above, $Z^4$ is $C(R^4)$. In embodiments of the formulae above, $Z^4$ is $C(R^{11c})$. In embodiments of the formulae above, $Z^4$ is C(H). In embodiments of the formulae above, $Z^4$ is $C(R^4)(H)$. In embodiments of the formulae above, $Z^4$ is $C(R^4)(R^{11c})$. In embodiments of the formulae above, $Z^4$ is $C(R^{11c})(R^{11c})$. In embodiments of the formulae above, $Z^4$ is $C(R^4)(R^4)$. In embodiments of the formulae above, $Z^4$ is $C(R^{11c})(H)$. In embodiments of the formulae above, $Z^4$ is $CH_2$. In embodiments of the formulae above, $Z^4$ is S. In embodiments of the formulae above, $Z^4$ is O. In embodiments of the formulae above, $Z^4$ is C(O). In embodiments of the formulae above, $Z^4$ is a bond. In embodiments of the formulae above, $Z^5$ is $N(R^4)$. In embodiments of the formulae above, $Z^5$ is $N(R^{11c})$. In embodiments of the formulae above, $Z^5$ is $N(H)$. In embodiments of the formulae above, $Z^5$ is N. In embodiments of the formulae above, $Z^5$ is $C(R^4)$. In embodiments of the formulae above, $Z^5$ is $C(R^{11c})$. In embodiments of the formulae above, $Z^5$ is $C(H)$. In embodiments of the formulae above, $Z^5$ is $C(R^4)(H)$. In embodiments of the formulae above, $Z^5$ is $C(R^4)(R^{11c})$. In embodiments of the formulae above, $Z^5$ is $C(R^{11c})(R^{11c})$. In embodiments of the formulae above, $Z^5$ is $C(R^4)(R^4)$. In embodiments of the formulae above, $Z^5$ is $C(R^{11c})(H)$. In embodiments of the formulae above, $Z^5$ is $CH_2$. In embodiments of the formulae above, $Z^5$ is S. In embodiments of the formulae above, $Z^5$ is O. In embodiments of the formulae above, $Z^5$ is C(O).

The individual embodiments herein below, or combinations thereof, (e.g., embodiments of $Z^1$, $Z^2$, $Z^3$, $Z^4$, and $Z^5$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof.

In embodiments of the formulae above, at least one of $Z^1$, $Z^2$, $Z^3$, $Z^4$, and $Z^5$ includes a ring heteroatom (e.g., $N(R^4)$, $N(R^{11c})$, $N(H)$, N, S, or O). In embodiments of the formulae above, at least two of $Z^1$, $Z^2$, $Z^3$, $Z^4$, and $Z^5$ include a ring heteroatom (e.g., $N(R^4)$, $N(R^{11c})$, $N(H)$, N, S, or O). In embodiments of the formulae above, at least one of $Z^1$, $Z^2$, $Z^3$, $Z^4$, and $Z^5$ includes a ring nitrogen (e.g., $N(R^4)$, $N(R^{11c})$, $N(H)$, or N). In embodiments of the formulae above, at least one of $Z^1$, $Z^2$, $Z^3$, $Z^4$, and $Z^5$ includes a ring oxygen.

In embodiments of the formulae above, only one of $Z^1$, $Z^2$, $Z^3$, $Z^4$, and $Z^5$ includes a ring heteroatom (e.g., $N(R^4)$, $N(R^{11c})$, $N(H)$, N, S, or O). In embodiments of the formulae above, only two of $Z^1$, $Z^2$, $Z^3$, $Z^4$, and $Z^5$ include a ring heteroatom (e.g., $N(R^4)$, $N(R^{11c})$, $N(H)$, N, S, or O). In embodiments of the formulae above, only one of $Z^1$, $Z^2$, $Z^3$, $Z^4$, and $Z^5$ includes a ring nitrogen (e.g., $N(R^4)$, $N(R^{11c})$, $N(H)$, or N). In embodiments of the formulae above, only one of $Z^1$, $Z^2$, $Z^3$, $Z^4$, and $Z^5$ includes a ring oxygen.

In embodiments of the formulae above, exactly one of $Z^1$, $Z^2$, $Z^3$, $Z^4$, and $Z^5$ includes $R^4$ (e.g., $N(R^4)$, $C(R^4)$, $C(R^4)(H)$, $C(R^4)(R^{11c})$, or $C(R^4)(R^4)$). In embodiments of the formulae above, exactly two of $Z^1$, $Z^2$, $Z^3$, $Z^4$, and $Z^5$ includes $R^4$ (e.g., $N(R^4)$, $C(R^4)$, $C(R^4)(H)$, $C(R^4)(R^{11c})$, or $C(R^4)(R^4)$).

The individual embodiments herein below, or combinations thereof, (e.g., embodiments of $W^4$) are applicable to compounds of Formula (I), (II), (III), (IV), (XVI), (XVII), (XIV), (XV), (XVIII), (XIX), (XX), (XXI), (XXII), (XXIII), (XXIV), (XXV), or (XXVI), or a pharmaceutically acceptable salt or solvate thereof, or embodiment formulae thereof. In embodiments of the formulae above, $W^4$ is N. In embodiments of the formulae above, $W^4$ is $N(R^{3c})$. In embodiments of the formulae above, $W^4$ is $N(H)$. In embodiments of the formulae above, $W^4$ is $N(R^{3c})$ and $R^3c$ is $C_{1-6}$alkyl optionally substituted with one, two, or three $R^{20c}$. In embodiments of the formulae above, $W^4$ is $N(R^{3c})$ and $R^3c$ is unsubstituted $C_{1-6}$alkyl.

The individual embodiments herein below, or combinations thereof, (e.g., embodiments of $W^1$, $W^2$, $W^3$, $W^5$, $W^6$, $W^7$, $W^8$, $W^9$, or $W^{10}$) are applicable to compounds of Formula (A), (B), (C), (A-1), (B-1), (C-1), (A'), (B'), (C'), (A'-1), (B'-1), (C'-1), (A"), (B"), (C"), (A"-1), (B"-1), (C"-1), (I), (II), (III), (IV), (XVI), (XVII), (XIV), (XV), (XVIII), (XIX), (XX), (XXI), (XXII), (XXIII), (XXIV), (XXV), or (XXVI), or a pharmaceutically acceptable salt or solvate thereof, or embodiment formulae thereof. In embodiments of the formulae above, $W^1$ is C. In embodiments of the formulae above, $W^1$ is $C(R^1)$. In embodiments of the formulae above, $W^1$ is $C(H)$. In embodiments of the formulae above, $W^1$ is N.

In embodiments of the formulae above, $W^5$ is C. In embodiments of the formulae above, $W^5$ is $C(R^5)$. In embodiments of the formulae above, $W^5$ is $C(H)$. In embodiments of the formulae above, $W^5$ is N.

In embodiments of the formulae above, $W^2$ is $C(R^2)$. In embodiments of the formulae above, $W^2$ is $C(R^2)(R^2a)$. In embodiments of the formulae above, $W^2$ is $C(H)(R^2)$. In embodiments of the formulae above, $W^2$ is N. In embodiments of the formulae above, $W^2$ is $N(R^2a)$. In embodiments of the formulae above, $W^2$ is $S(O)_2$. In embodiments of the formulae above, $W^2$ is $S(O)$. In some embodiments is a compound of Formula (II), (III), or (XVI), or a pharmaceutically acceptable salt or solvate thereof, wherein $W^2$ is C(O).

In embodiments of the formulae above, $W^3$ is N. In embodiments of the formulae above, $W^3$ is $N(R^3b)$. In embodiments of the formulae above, $W^3$ is $N(H)$. In embodiments of the formulae above, $W^3$ is $N(R^3b)$ and $R^{3b}$ is $C_{1-6}$alkyl optionally substituted with one, two, or three $R^{20c}$. In embodiments of the formulae above, $W^3$ is $N(R^3b)$ and $R^{3b}$ is unsubstituted $C_{1-6}$alkyl. In embodiments of the formulae above, $W^3$ is $C(R^3)$. In embodiments of the formulae above, $W^3$ is $C(R^3)(R^3a)$. In embodiments of the formulae above, $W^3$ is $C(H)(R^3)$. In embodiments of the formulae above, $W^3$ is C(O). In embodiments of the formulae above, $W^3$ is C(CN).

In embodiments of the formulae above, $W^6$ is $C(R^6)$. In embodiments of the formulae above, $W^6$ is $C(R^6)(R^{6a})$. In embodiments of the formulae above, $W^6$ is $C(H)(R^6)$. In embodiments of the formulae above, $W^6$ is N. In embodiments of the formulae above, $W^6$ is $N(R^6b)$. In embodiments of the formulae above, $W^6$ is $N(H)$. In embodiments of the formulae above, $W^6$ is $N(R^6\%)$ and $R^{6b}$ is $C_{1-6}$alkyl optionally substituted with one, two, or three $R^{20e}$. In embodiments of the formulae above, $W^6$ is $N(R^6b)$ and Rob is unsubstituted $C_{1-6}$alkyl. In embodiments of the formulae above, $W^6$ is C(O). In embodiments of the formulae above, $W^6$ is $S(O)_2$. In embodiments of the formulae above, $W^6$ is S(O). In embodiments of the formulae above, $W^6$ is C(halogen). In embodiments of the formulae above, $W^6$ is C(Cl).

In embodiments of the formulae above, $W^7$ is $C(R^7)$. In embodiments of the formulae above, $W^7$ is $C(R^7)(R^7a)$. In embodiments of the formulae above, $W^7$ is $C(H)(R^7)$. In embodiments of the formulae above, $W^7$ is $N(R^7)$.

In embodiments of the formulae above, $W^8$ is $C(R^8)$. In embodiments of the formulae above, $W^8$ is $C(R^8)(R^8a)$. In embodiments of the formulae above, $W^8$ is $C(H)(R^8)$. In embodiments of the formulae above, $W^8$ is N. In embodiments of the formulae above, $W^8$ is $N(R^8b)$. In embodiments of the formulae above, $W^8$ is $N(H)$. In embodiments of the formulae above, $W^8$ is $N(R^8b)$ and $R^{8b}$ is $C_{1-6}$alkyl optionally substituted with one, two, or three $R^{20}h$. In embodiments of the formulae above, $W^8$ is $N(R^8b)$ and $R^{8b}$ is unsubstituted $C_{1-6}$alkyl. In embodiments of the formulae above, $W^8$ is C(O). In embodiments of the formulae above, $W^8$ is $S(O)_2$. In embodiments of the formulae above, $W^8$ is S(O). In embodiments of the formulae above, $W^8$ is C(halogen). In embodiments of the formulae above, $W^8$ is C(F).

In embodiments of the formulae above, $W^9$ is C. In embodiments of the formulae above, $W^9$ is C($R^9$). In embodiments of the formulae above, $W^9$ is C(H). In embodiments of the formulae above, $W^9$ is N.

In embodiments of the formulae above, $W^{10}$ is C. In embodiments of the formulae above, $W^{10}$ is C($R^9$). In embodiments of the formulae above, $W^{10}$ is C(H). In embodiments of the formulae above, $W^{10}$ is N.

The individual embodiments herein below, or combinations thereof, (e.g., embodiments of $R^2$) are applicable to compounds of Formula (I), (IV), (XVII), (Ia), (IVa), (XVIIa), (Ib), (IVb), (XVIIb), (Ic), (IVc), (XVIIc), (Id), (IVd), (XVIId), (Ie), (IVe), (XVIIe), (If), (IVf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $R^2$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}a$, $-SR^{12}$, and $-N(R^{12})(R^{13})$, wherein $C_{1-6}$alkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl are optionally substituted with one, two, or three $R^{20\%}$. In embodiments of the formulae above, $R^2$ is selected from $-OR^{12}a$, $-SR^{12}$, $-N(R^{12})(R^{13})$, and $C_{1-6}$alkyl optionally substituted with one, two, or three $R^{20}b$. In embodiments of the formulae above, $R^2$ is-$OR^{12}a$.

The individual embodiments herein below, or combinations thereof, (e.g., embodiments of $R^2$) are applicable to compounds of Formula (II), (III), (XVI), (XVII), (IIa), (IIIa), (XVIa), (XVIIa), (IIb), (IIIb), (XVIb), (XVIIb), (IIc), (IIIc), (XVIc), (XVIIc), (IId), (IIId), (XVId), (XVIId), (IIe), (IIIe), (XVIe), (XVIIe), (IIf), (IIIf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"- 1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $R^2$ is-$SR^{12}$. In embodiments of the formulae above, $R^2$ is $-N(R^{12})(R^{13})$. In embodiments of the formulae above, $R^2$ is-$NH(R^{12})$. In embodiments of the formulae above, $R^2$ is $C_{1-6}$alkyl optionally substituted with one, two, or three $R^{20}b$.
In embodiments of the formulae above, $R^2$ is selected from
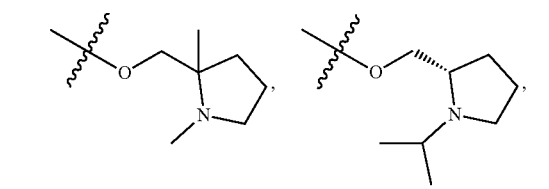
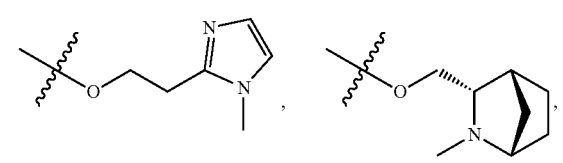
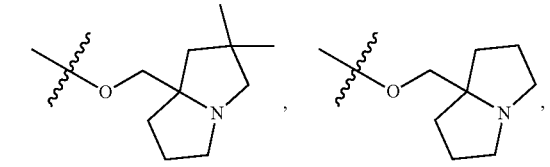
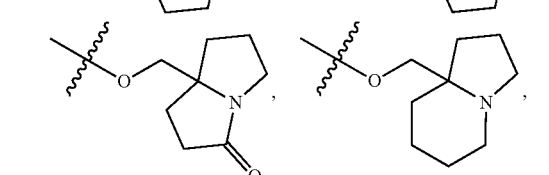
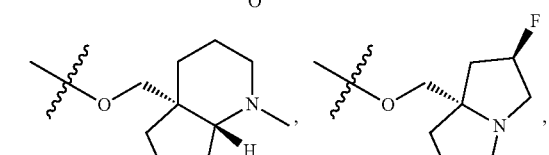
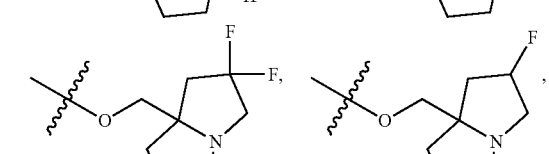
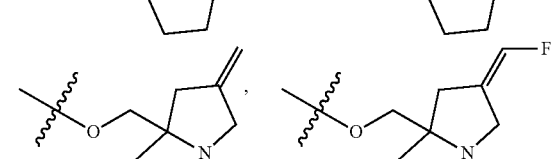
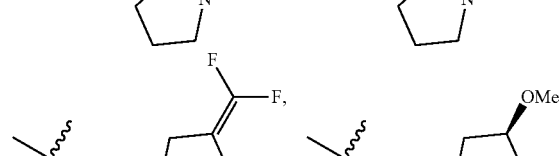
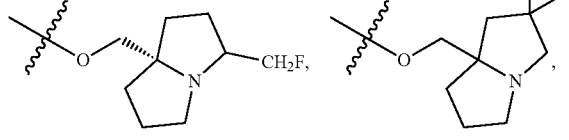
-continued
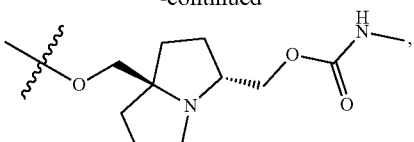
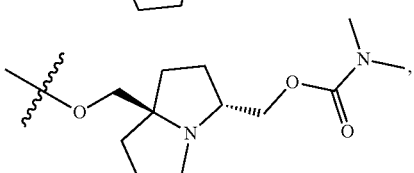
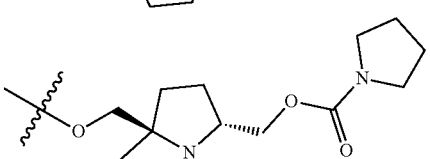
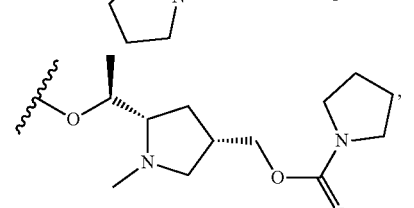
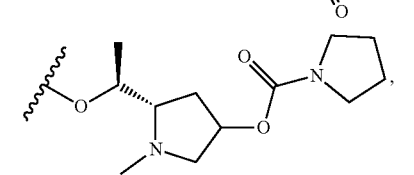
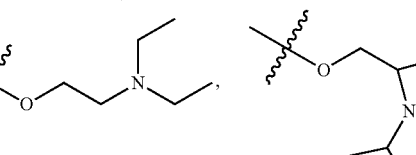
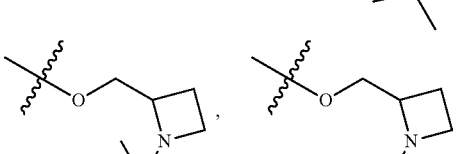
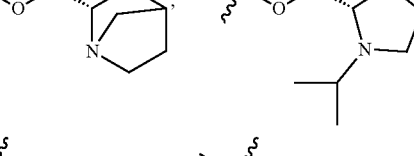
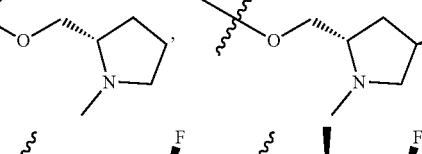
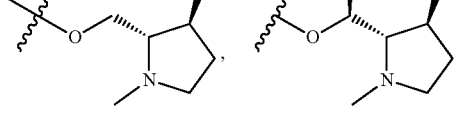

227
-continued
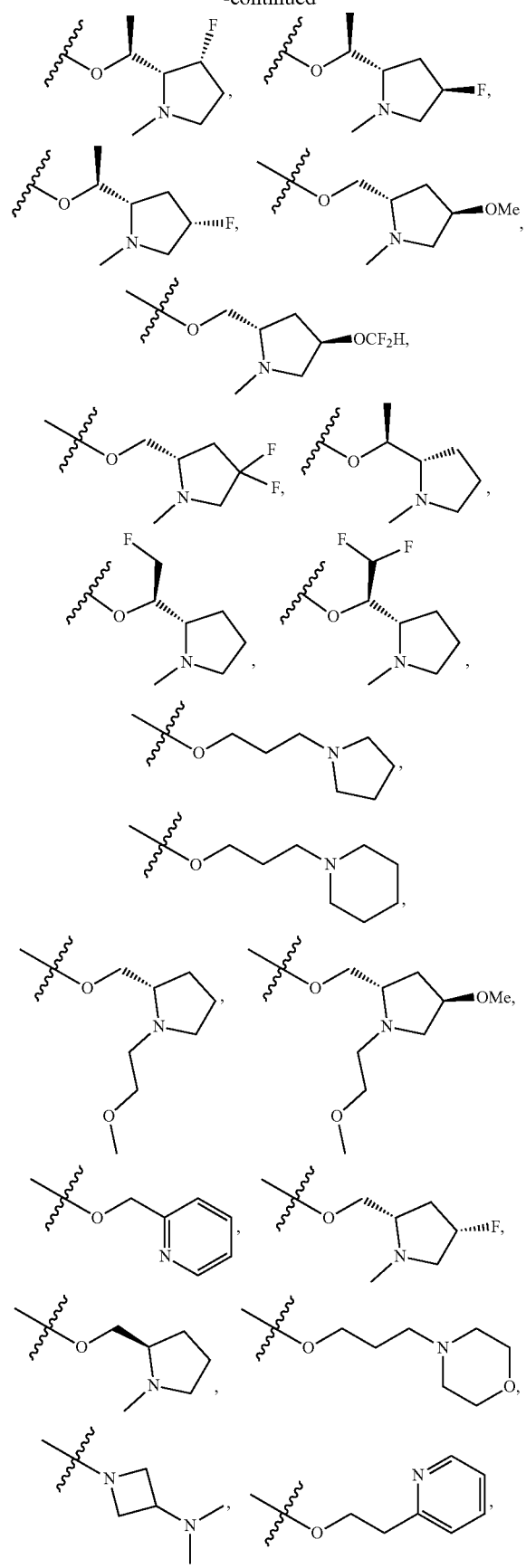
228
-continued
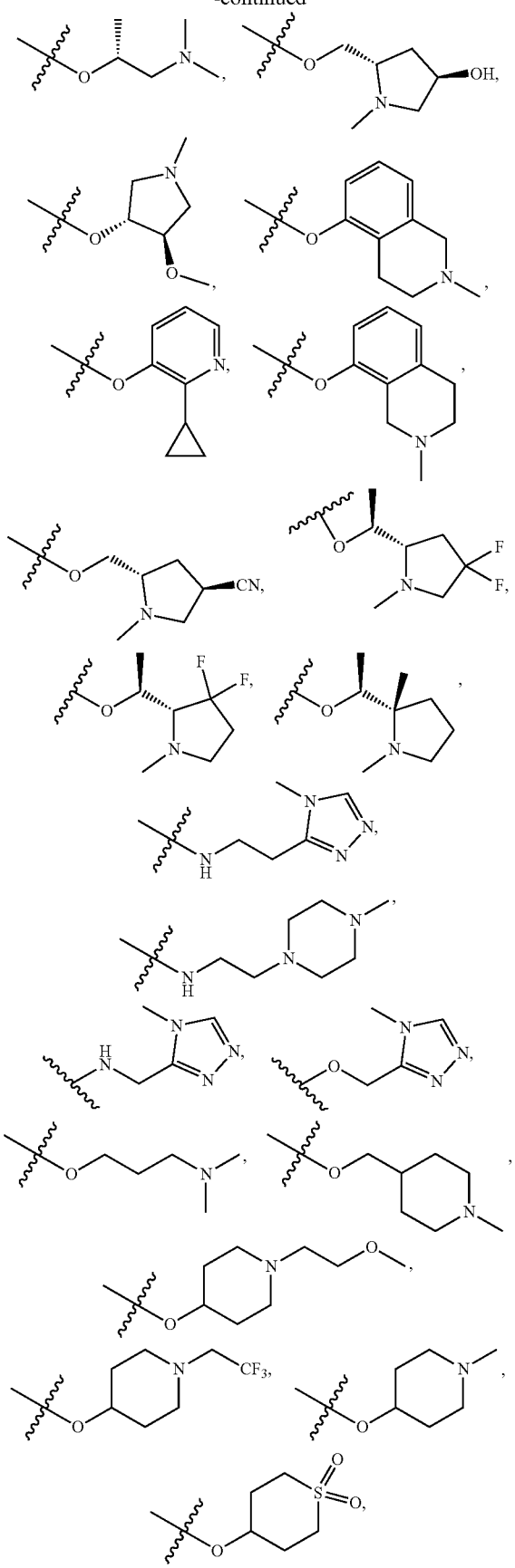

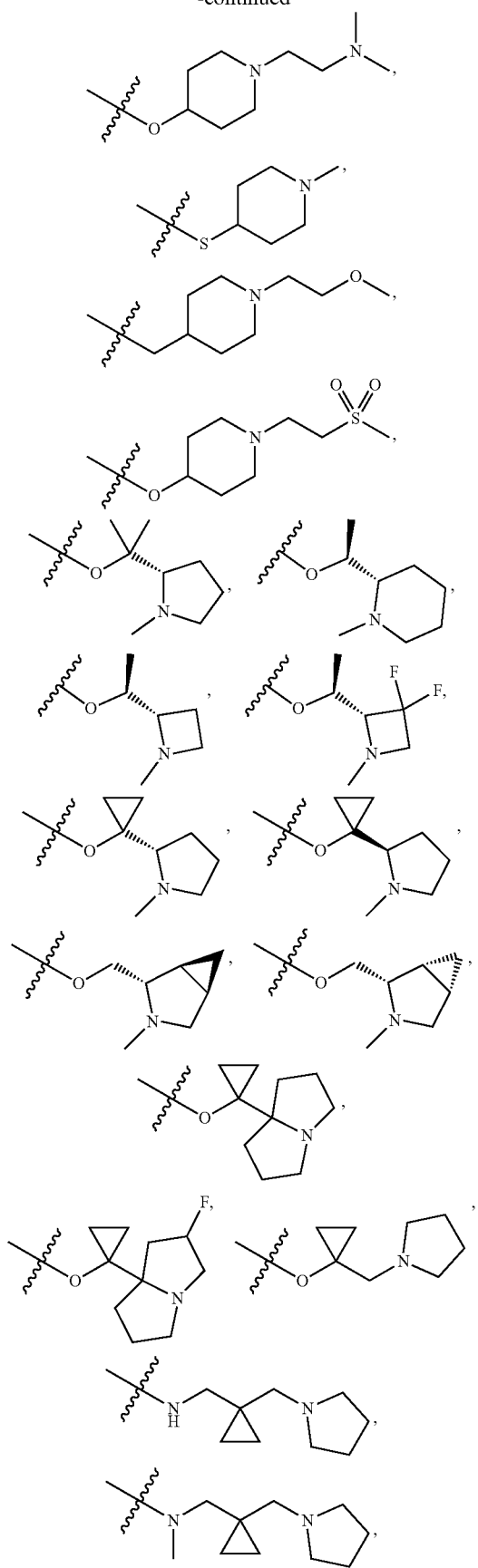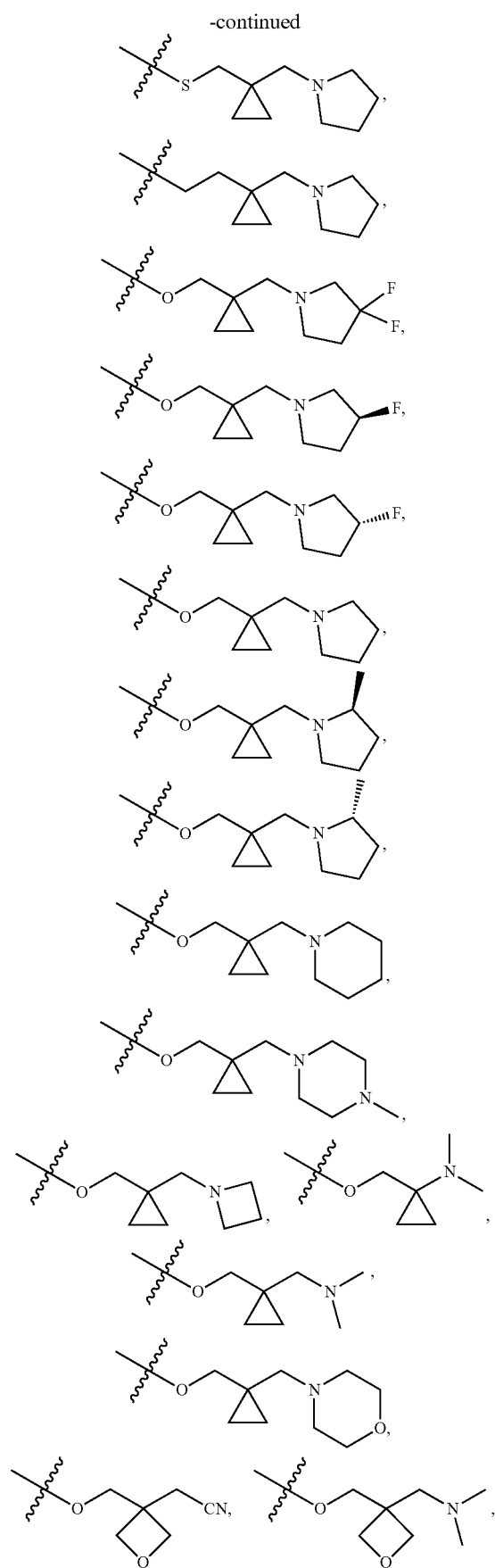

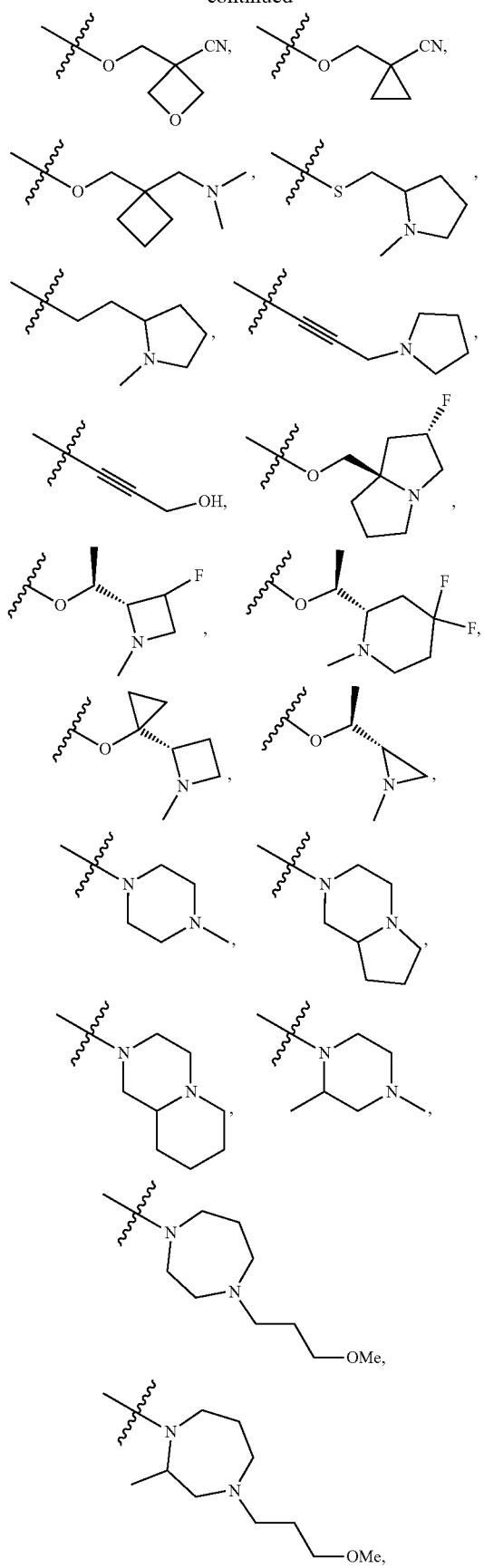
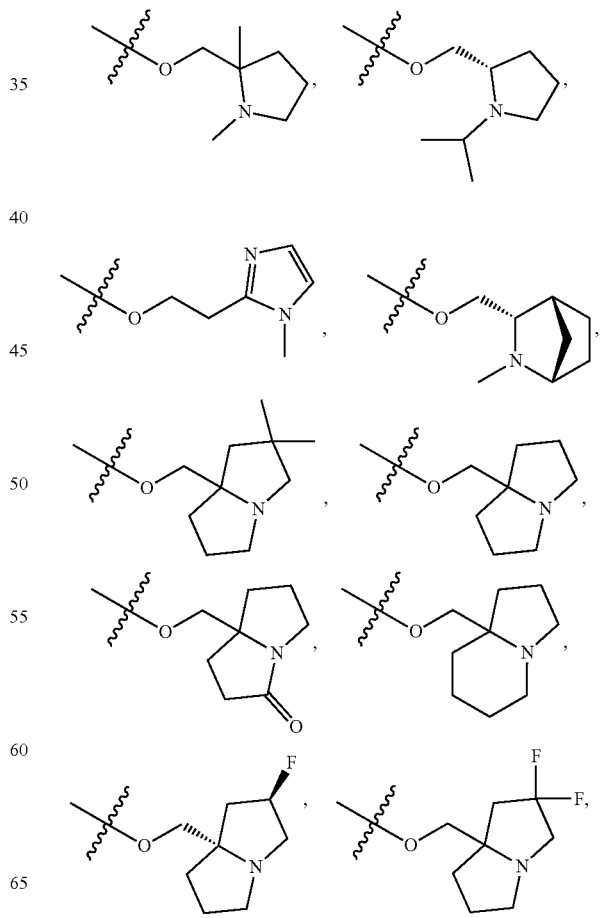
In embodiments of the formulae above, R² is selected from 233
-continued
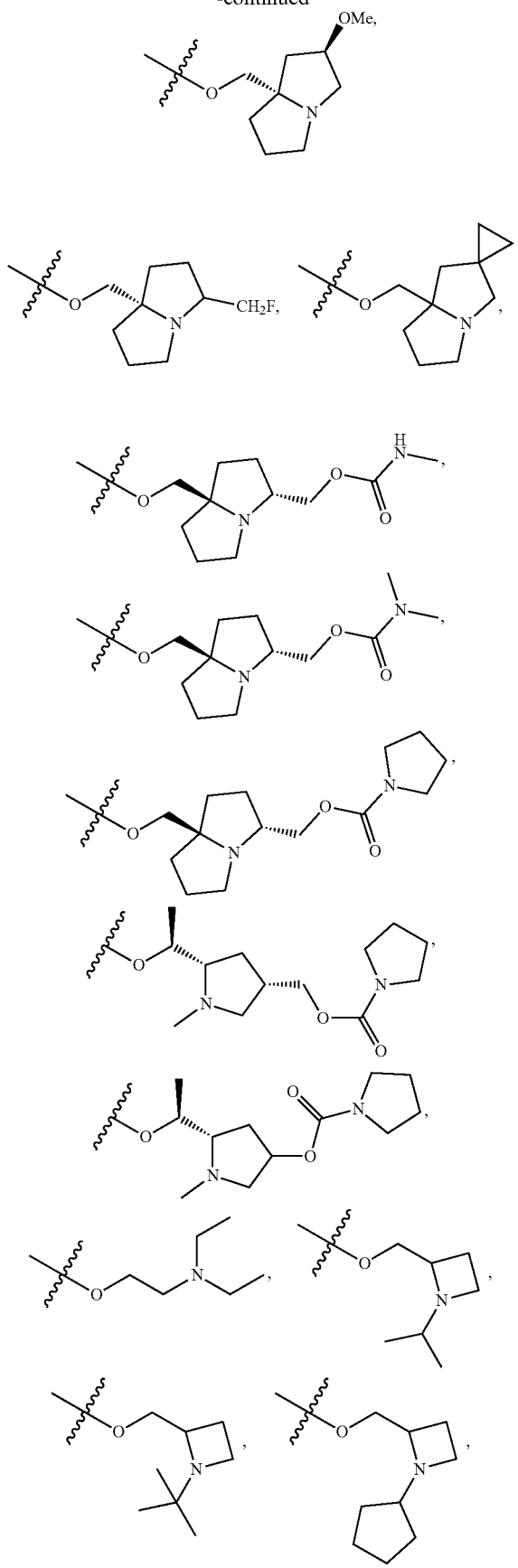
234
-continued
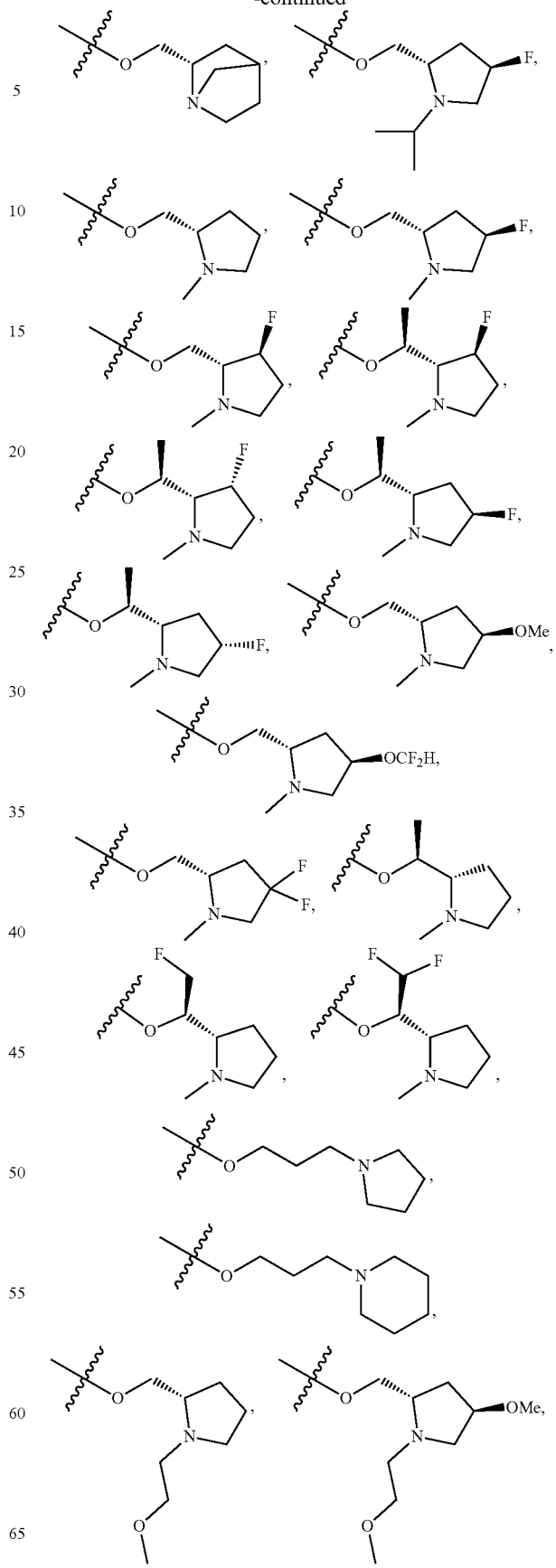

-continued
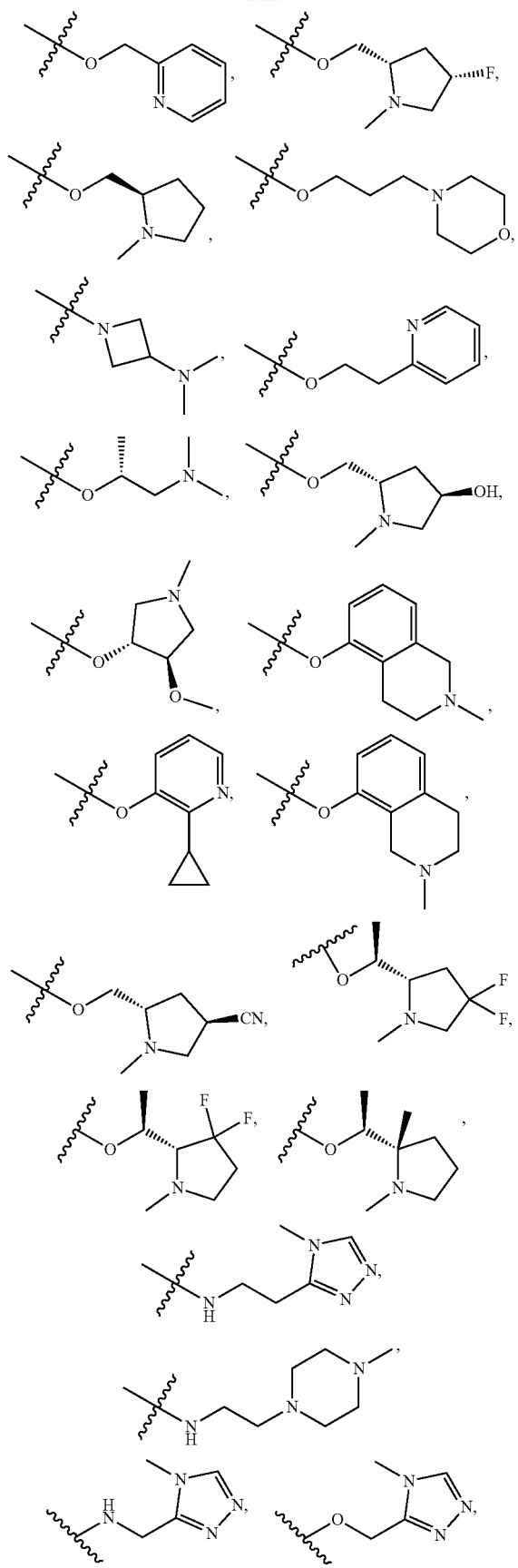
-continued
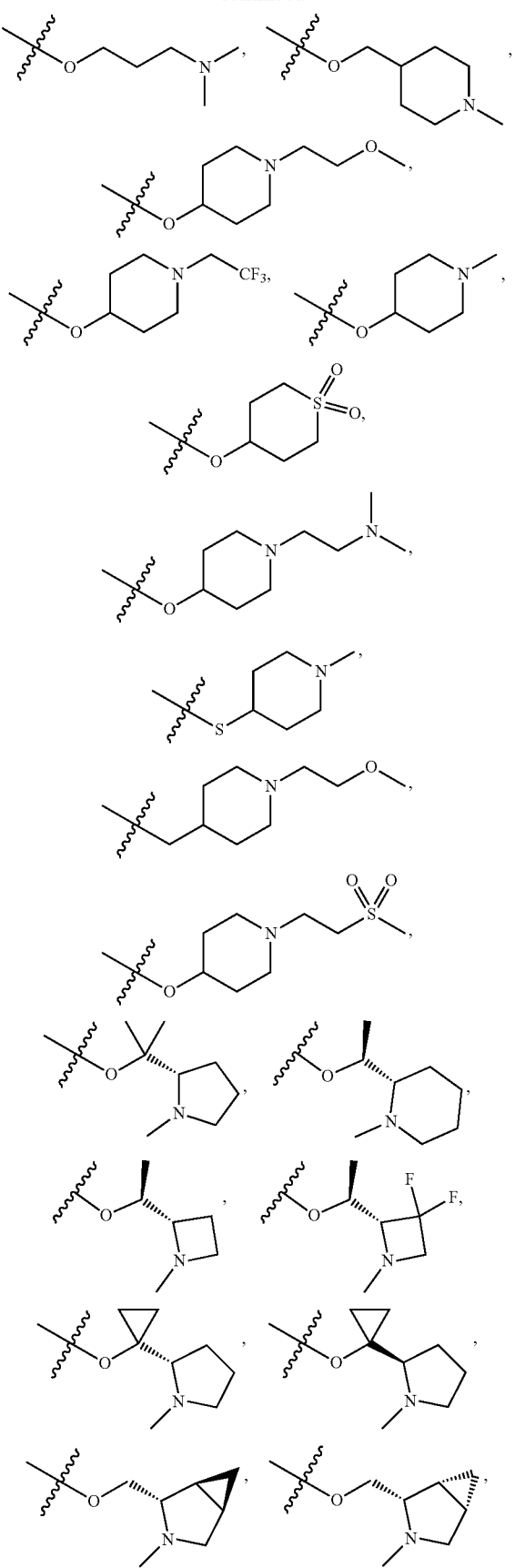

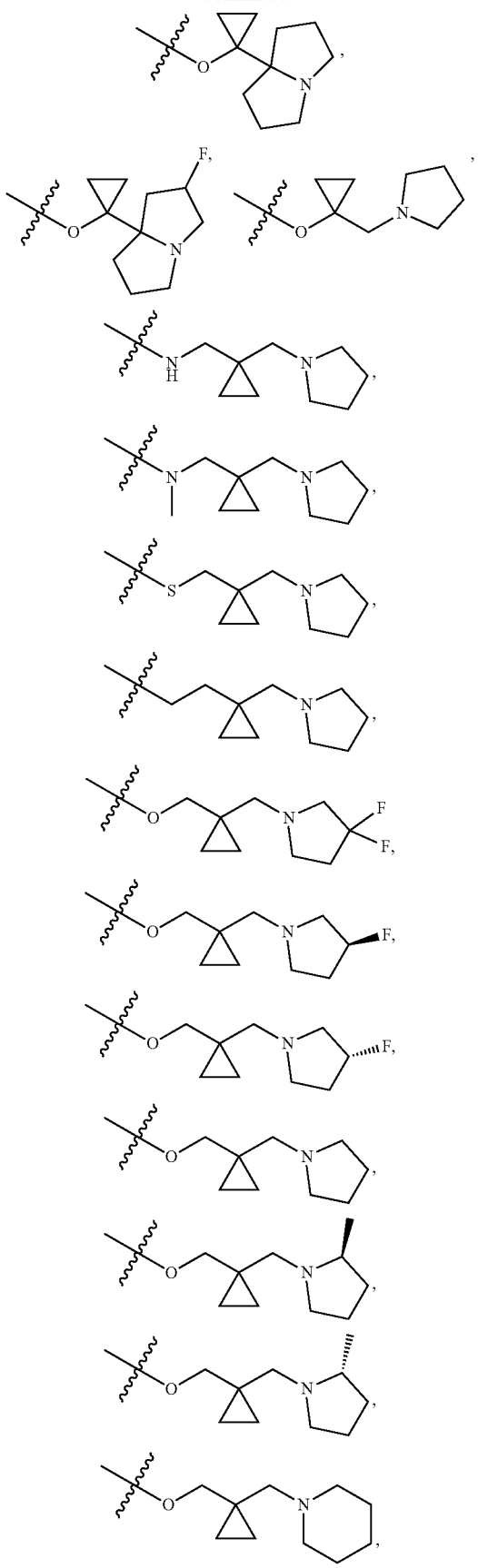
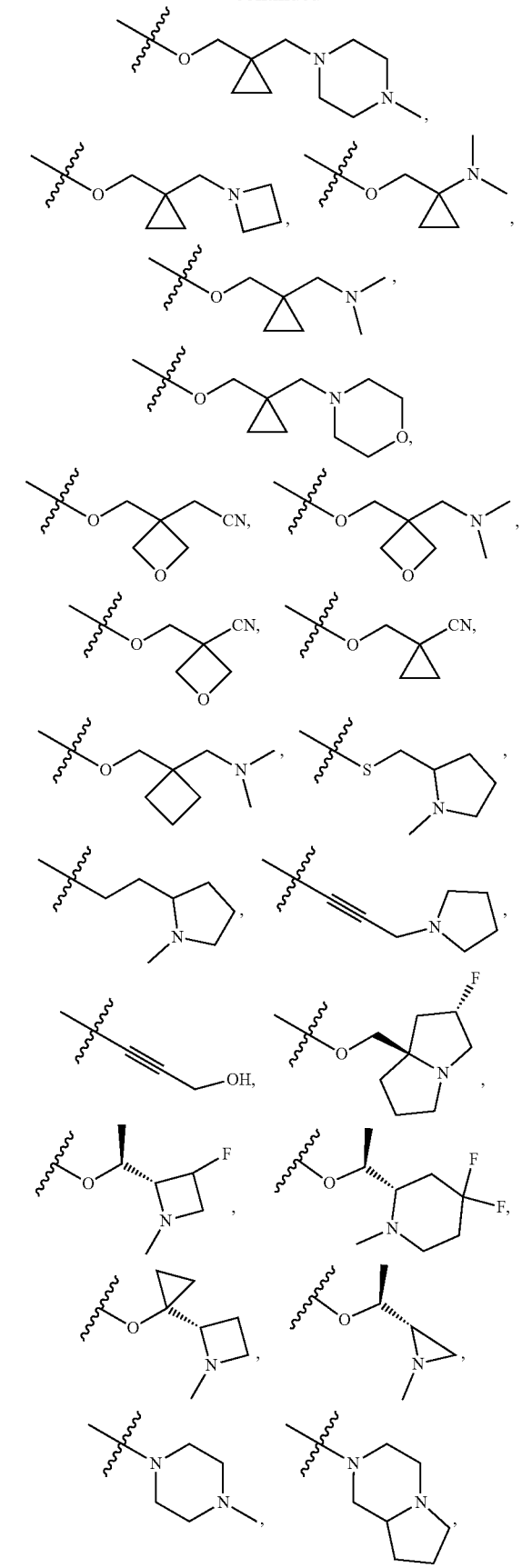

The individual embodiments herein below, or combinations thereof, (e.g., embodiments of R³) are applicable to compounds of Formula (I), (II), (III), (IV), (XVI), (XVII), (Ib), (ITb), (IIIb), (IVb), (XVIb), (XVIIb), (If), (IIf), (IIIf), (IVf), (XVIf), (XVIh), (XVIIf), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1b), (B-1b), (C-1b), (A-1f), (B-1f), (C-1f), (A'), (B'), (C'), (A'-1), (B'-1), (C'-1), (A'-1b), (B'-1b), (C'-1b), (A'-1f), (B'-1f), (C'-1f), (A"), (B"), (C"), (A"-1), (B"-1), (C"-1), (A"-1b), (B"-1b), (C"-1b), (A"-1f), (B"-1f), or (C"-1f), or a pharmaceutically acceptable salt or solvate thereof. In embodiments of the formulae above, R³ is selected from hydrogen, halogen, —CN, C₁₋₆alkyl, —OR¹², —SR¹², —N(R¹²)(R¹³), —C(O)OR¹², —C(O)R¹⁵, —C(O)N(R¹²) (R¹³), —S(O)₂R¹⁵, and —S(O)₂N(R¹²)(R¹³)—, wherein C₁₋₆alkyl is optionally substituted with one, two, or three R²⁰ᶜ. In embodiments of the formulae above, R³ is selected from hydrogen, halogen, —CN, C₁₋₆alkyl, and —OR¹², wherein C₁₋₆alkyl is optionally substituted with one, two, or three R²⁰ᶜ. In embodiments of the formulae above, R³ is hydrogen. In embodiments of the formulae above, R³ is halogen. In embodiments of the formulae above, R³ is-CN. In embodiments of the formulae above, R³ is-OR¹². In embodiments of the formulae above, R³ is C₁₋₆alkyl optionally substituted with one, two, or three R²⁰ᶜ. In embodiments of the formulae above, R³ is unsubstituted C₁₋₆alkyl.

The individual embodiments herein below, or combinations thereof, (e.g., embodiments of R⁶) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIh), (XVIIc), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (A), (B), (C), (A-1), (B-1), (C-1), (A-1a), (B-1a), (C-1a), (A-1b), (B-1b), (C-1b), (A-1c), (B-1c), (C-1c), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), or a pharmaceutically acceptable salt or solvate thereof. In embodiments of the formulae above, R⁶ is selected from hydrogen, halogen, —CN, C₁₋₆alkyl, —OR¹², —SR¹², —N(R¹²)(R¹³), —C(O)OR¹², —C(O)R¹⁵, —C(O)N(R¹²)(R¹³), —S(O)₂R¹⁵, and —S(O)₂N(R¹²) (R¹³)—, wherein C₁₋₆alkyl is optionally substituted with one, two, or three R²⁰ᵉ. In embodiments of the formulae above, R⁶ is selected from hydrogen, halogen, —CN, C₁₋₆alkyl, and —OR¹², wherein C₁₋₆alkyl is optionally substituted with one, two, or three R²⁰ᵉ. In embodiments of the formulae above, R⁶ is hydrogen. In embodiments of the formulae above, R⁶ is halogen. In embodiments of the formulae above, R⁶ is F. In embodiments of the formulae above, R⁶ is C₁. In embodiments of the formulae above, R⁶ is Br. In embodiments of the formulae above, R⁶ is I. In embodiments of the formulae above, R⁶ is-CN. In embodiments of the formulae above, R⁶ is-OR¹². In embodiments of the formulae above, R⁶ is C₁₋₆alkyl optionally substituted with one, two, or three R²⁰ᵉ. In embodiments of the formulae above, R⁶ is unsustituted C₁₋₆alkyl.

The individual embodiments herein below, or combinations thereof, (e.g., embodiments of R⁸, L⁷, R¹⁷, R¹ᵃ, R¹ᶜ, Q³, Q⁴, X⁹, X¹⁰, X¹¹, or X¹²) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIh), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $R^8$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20h}$. In embodiments of the formulae above, $R^8$ is selected from hydrogen, halogen, —CN, $C_{1-6}$alkyl, and —$OR^{12}$, wherein $C_{1-6}$alkyl is optionally substituted with one, two, or three $R^{20h}$. In embodiments of the formulae above, $R^8$ is hydrogen. In embodiments of the formulae above, $R^8$ is halogen. In embodiments of the formulae above, $R^8$ is F. In embodiments of the formulae above, $R^8$ is $C_1$. In embodiments of the formulae above, $R^8$ is Br. In embodiments of the formulae above, $R^8$ is I. In embodiments of the formulae above, $R^8$ is-CN. In embodiments of the formulae above, $R^8$ is-$OR^{12}$. In embodiments of the formulae above, $R^8$ is $C_{1-6}$alkyl optionally substituted with one, two, or three $R^{20h}$. In embodiments of the formulae above, $R^8$ is unsustituted $C_{1-6}$alkyl.

In embodiments of the formulae above, $L^7$ is a bond, —O—, —$N(R^{7d})$—, —$C(O)$—, or $CR^{7c}R^{7c}$. In embodiments of the formulae above, $L^7$ is a bond. In embodiments of the formulae above, $L^7$ is-O—. In embodiments of the formulae above, $L^7$ is-$N(R^{7d})$—. In embodiments of the formulae above, $L^7$ is-N(H)—. In embodiments of the formulae above, $L^7$ is-C(O)—. In embodiments of the formulae above, $L^7$ is $CR^7R^{7c}$. In embodiments of the formulae above, $L^7$ is-$CH_2$—.

In embodiments of the formulae above, $R^{17}$ is $C_{3-10}$cycloalkyl optionally substituted with one, two, or three $R^{20}g$. In embodiments of the formulae above, $R^{17}$ is $C_{2-9}$heterocycloalkyl optionally substituted with one, two, or three $R^{20}g$. In embodiments of the formulae above, $R^{17}$ is $C_{6-10}$aryl optionally substituted with one, two, or three $R^{20}g$. In embodiments of the formulae above, $R^{17}$ is $C_{1-9}$heteroaryl optionally substituted with one, two, or three $R^{20}g$.

In embodiments of the formulae above, $R^{17}$ is selected from:

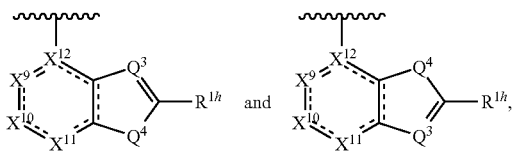

$Q^3$ is N or $C(R^1d)$;
$Q^4$ is O or S;
$X^9$, $X^{10}$, and $X^{11}$ are independently C(O), $C(R^{1a})$, or $C(R^{1a})(R^1b)$;
$X^{12}$ is C, N, or $C(R^1a)$;
each $R^{1a}$, $R^{1b}$, $R^{1d}$, and $R^1h$ is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20z}$;

each $R^{20}z$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}a$, —$SR^{21}a$, —$N(R^{22}a)(R^{23}a)$, —$C(O)OR^{22a}$, —$C(O)N(R^{22}a)(R^{23}a)$, —$C(O)C(O)N(R^{22}a)(R^{23}a)$, —$OC(O)N(R^{22}a)(R^{23}a)$, —$N(R^{24}a)C(O)N(R^{22}a)(R^{23}a)$, —$N(R^{24}a)C(O)OR^{25}a$, —$N(R^{24}a)C(O)R^{25}a$, —$N(R^{24}a)S(O)_2R^{25}a$, —$C(O)R^{25}a$, —$S(O)_2R^{25}a$, —$S(O)_2N(R^{22}a)(R^{23}a)$, —$OCH_2C(O)OR^{22}a$, and —$OC(O)R^{25}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}a$, —$SR^{21}a$, —$N(R^{22}a)(R^{23}a)$, —$C(O)OR^{22a}$, —$C(O)N(R^{22}a)(R^{23}a)$, —$C(O)C(O)N(R^{22}a)(R^{23}a)$, —$OC(O)N(R^{22}a)(R^{23}a)$, —$N(R^{24})C(O)N(R^{22}a)(R^{23}a)$, —$N(R^{24}a)C(O)OR^{25}a$, —$N(R^{24}a)C(O)R^{25}a$, —$N(R^{24}a)S(O)_2R^{25}a$, —$C(O)R^{25}a$, —$S(O)_2R^{25}a$, —$S(O)_2N(R^{22}a)(R^{23}a)$, and —$OC(O)R^{25a}$;

each $R^{21}a$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}a$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}a$ is independently selected from H and $C_{1-6}$alkyl;
each $R^{24}a$ is independently selected from H and $C_{1-6}$alkyl; and each $R^{25}a$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl.

In some embodiments of the formulae above, $Q^3$ is N. In some embodiments of the formulae above, $Q^3$ is $C(R^1d)$. In some embodiments of the formulae above, $Q^4$ is O. In some embodiments of the formulae above, $Q^4$ is S. In some embodiments of the formulae above, $X^9$ is $C(R^{1a})$. In some embodiments of the formulae above, $X^9$ is C(O). In some embodiments of the formulae above, X' is $C(R^{1a})(R^1b)$. In some embodiments of the formulae above, $X^{10}$ is C(O). In some embodiments of the formulae above, $X^{10}$ is $C(R^1a)$. In some embodiments of the formulae above, $X^{10}$ is $C(R^{1a})$ ($R^1b$). In some embodiments of the formulae above, $X^{11}$ is C(O). In some embodiments of the formulae above, $X^{11}$ is $C(R^1a)$. In some embodiments of the formulae above, $X^{11}$ is $C(R^{1a})(R^1b)$. In some embodiments of the formulae above, $X^{12}$ is C. In some embodiments of the formulae above, $X^{12}$ is N. In some embodiments of the formulae above, $X^{12}$ is $C(R^{1a})$.

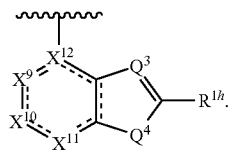

In embodiments of the formulae above, $R^{17}$ is

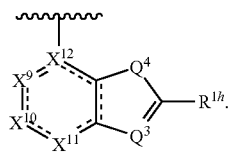

In embodiments of the formulae above, $R^{17}$ is

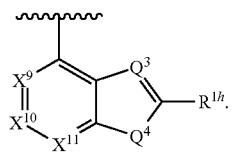

In embodiments of the formulae above, $R^{17}$

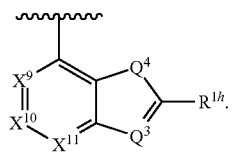

In embodiments of the formulae above, $R^{17}$ is

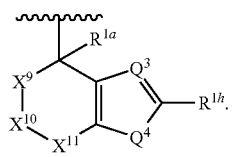

In embodiments of the formulae

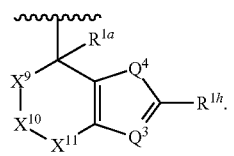

In embodiments of the formulae above, $R^{17}$ is

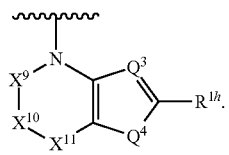

In embodiments of the formulae above, $R^{17}$ is

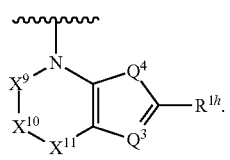

In embodiments of the formulae above, $R^{17}$ is selected from:

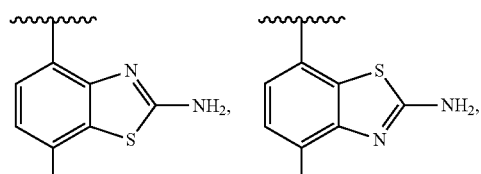
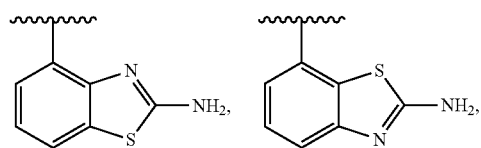

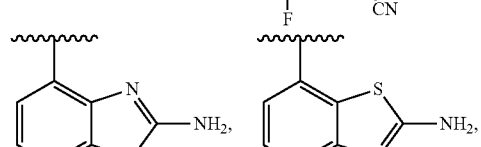

-continued
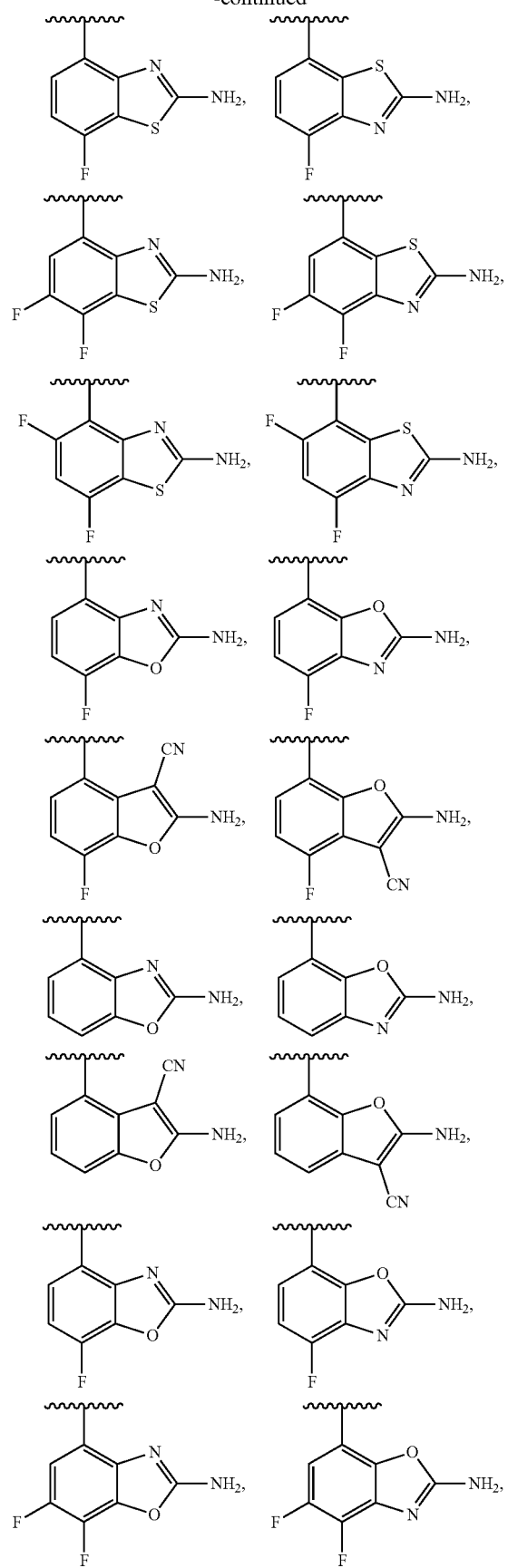
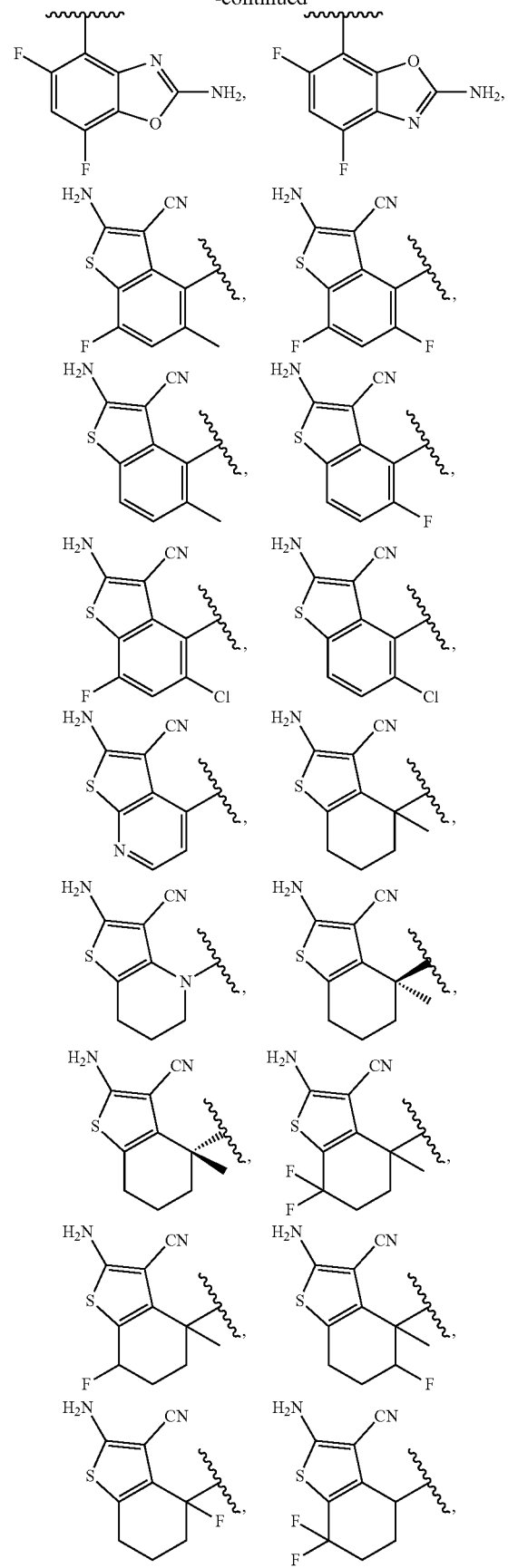

-continued
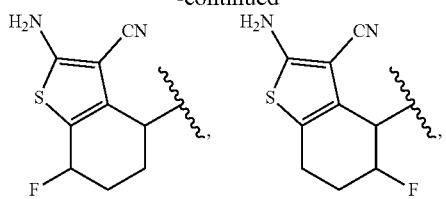
-continued
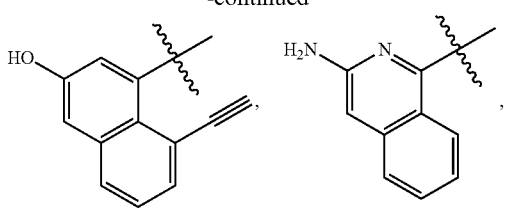

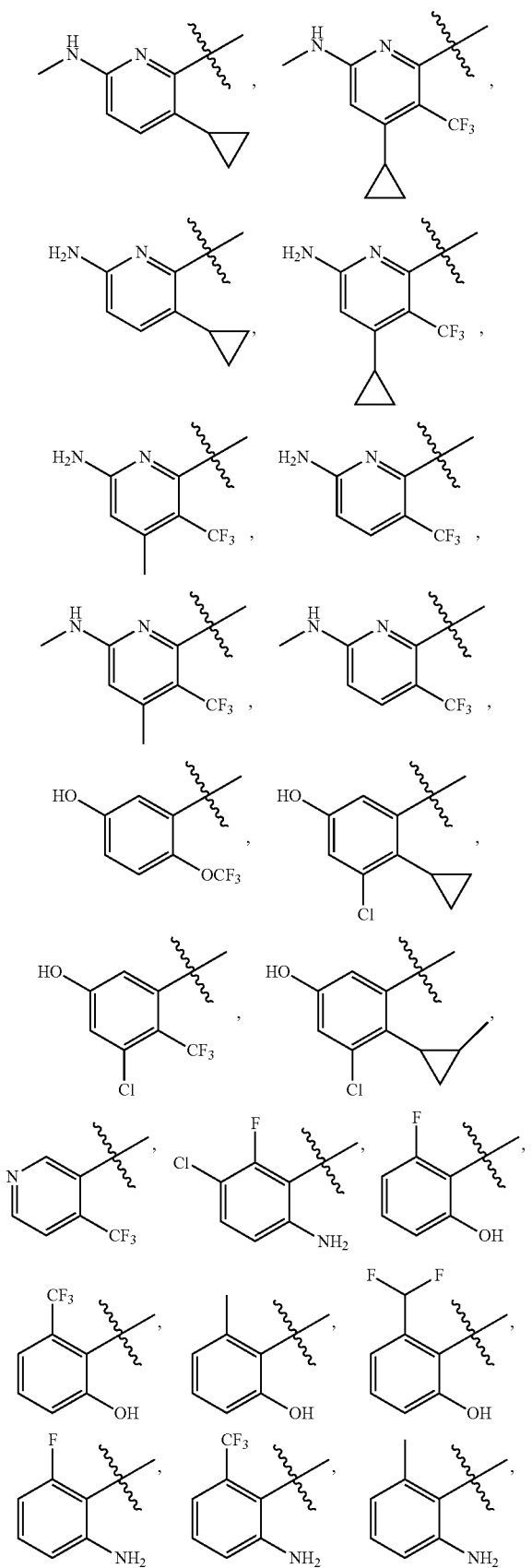
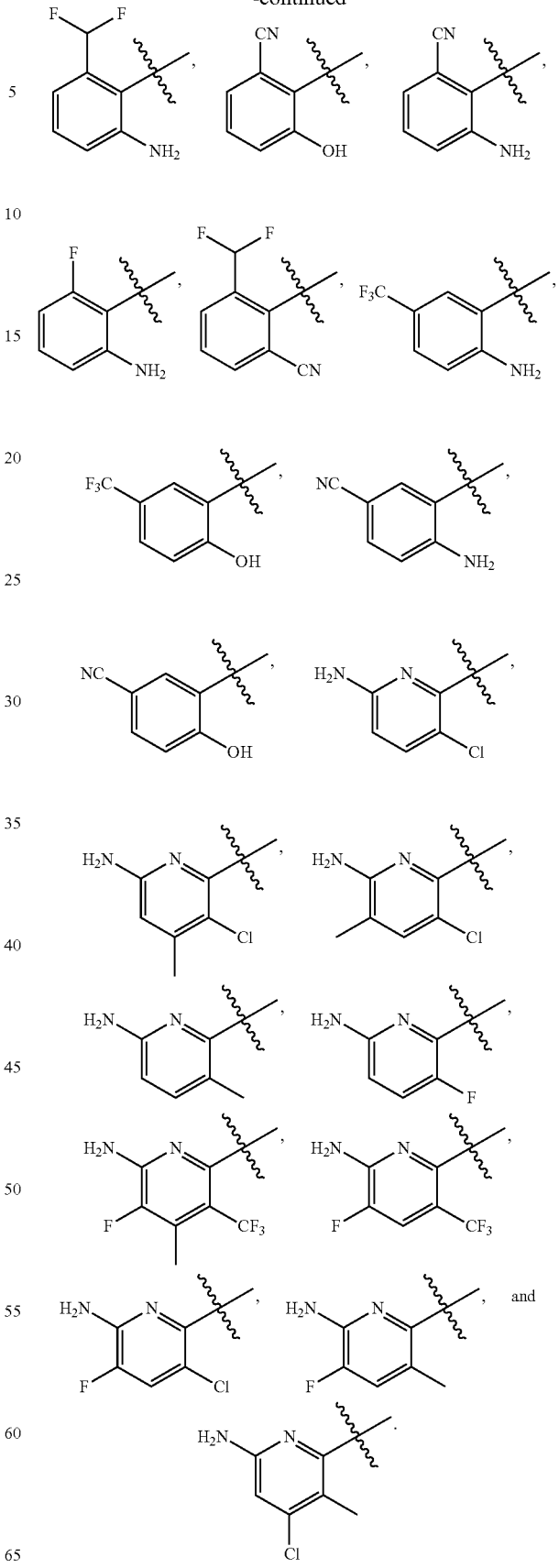

In embodiments of the formulae above, $R^{17}$ is selected from
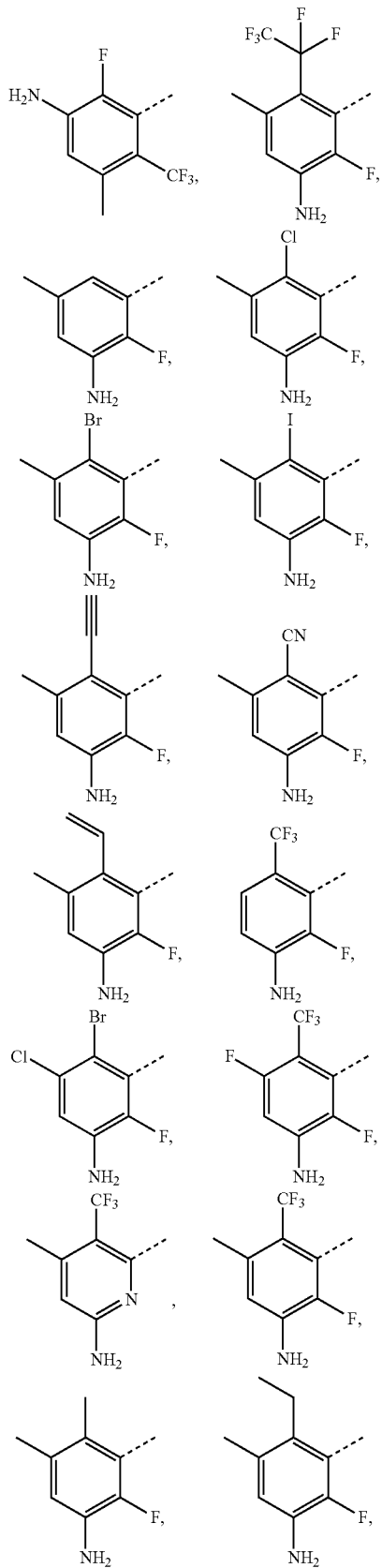
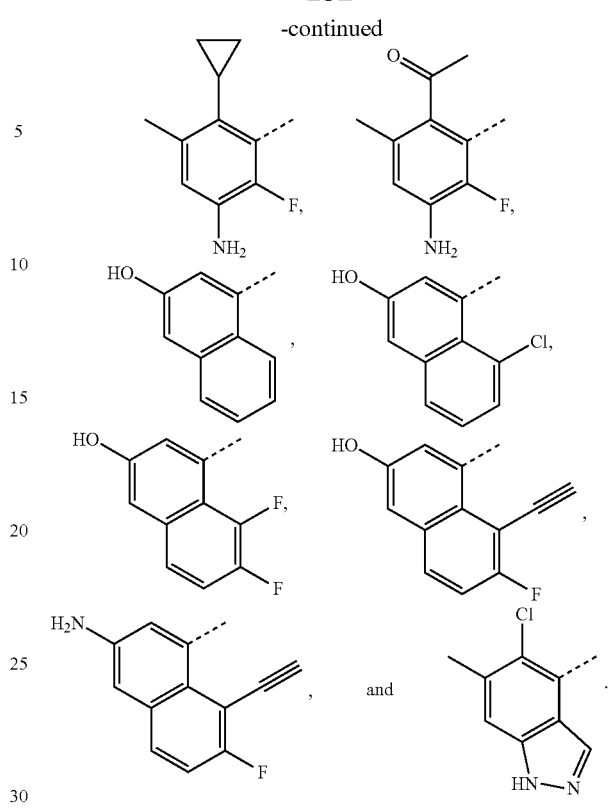
In embodiments of the formulae above, $R^{17}$ is selected from
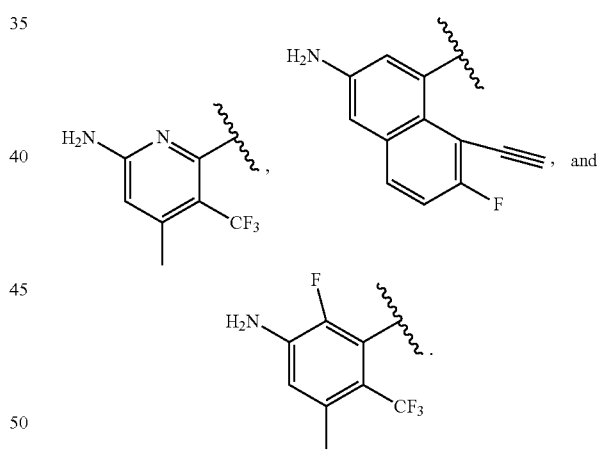
In embodiments of the compounds of the formulae above, $R^{17}$ is selected from
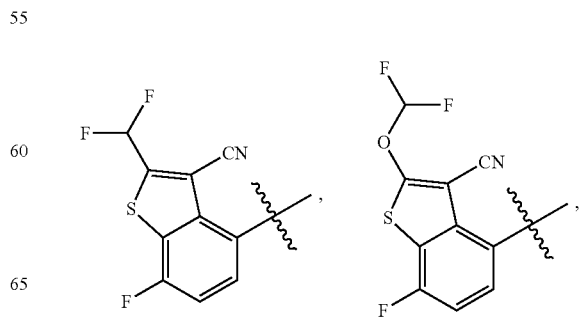

-continued
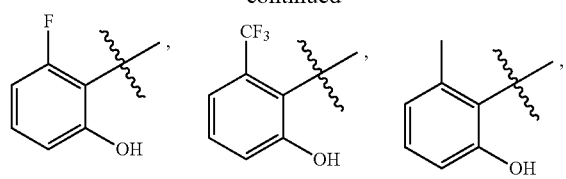
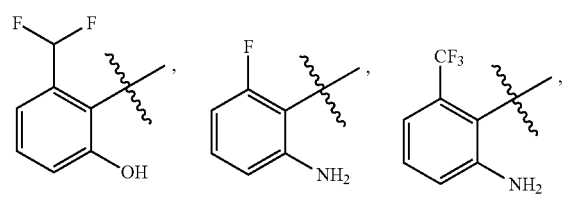
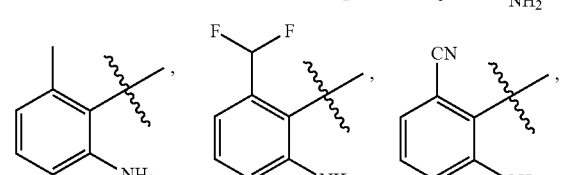
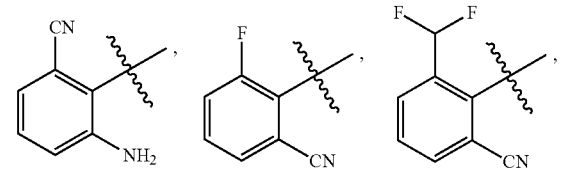
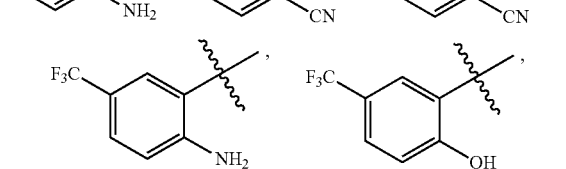
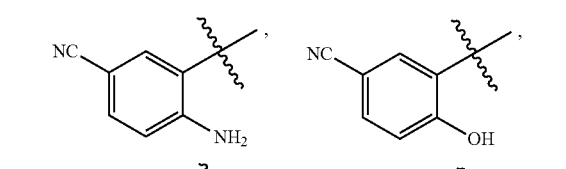
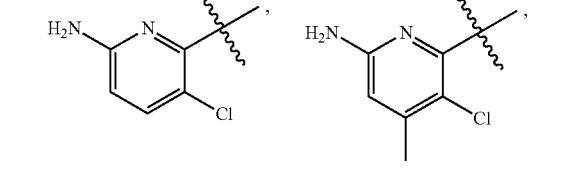
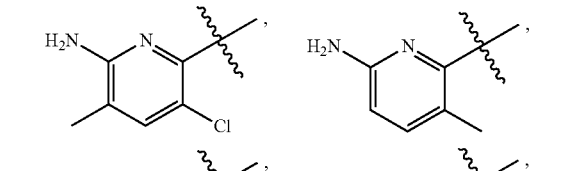
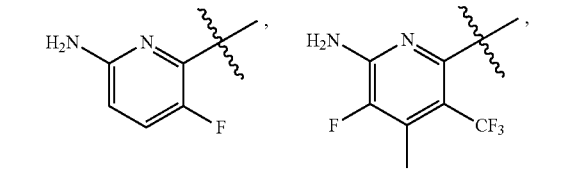
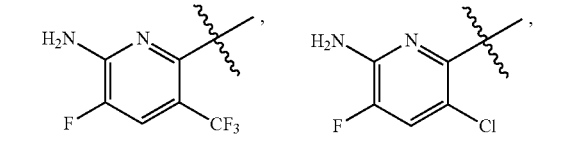
-continued
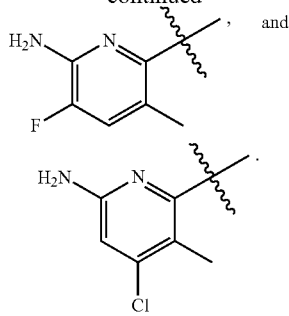
In embodiments of the compounds of the formulae above, $R^{17}$ is selected from
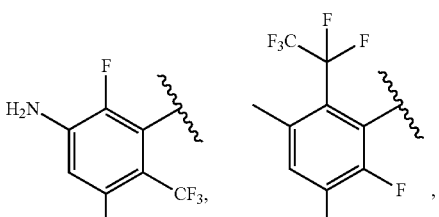
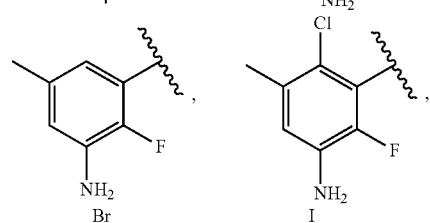
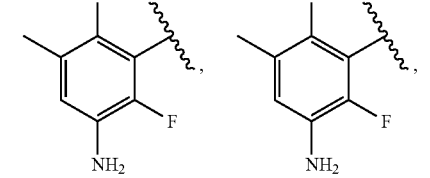
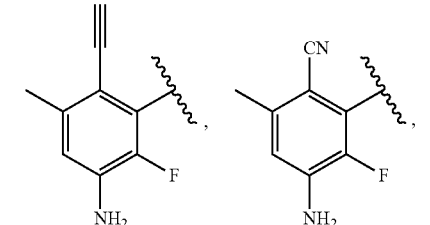
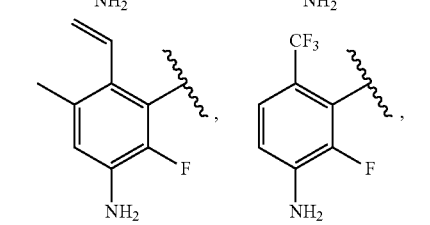
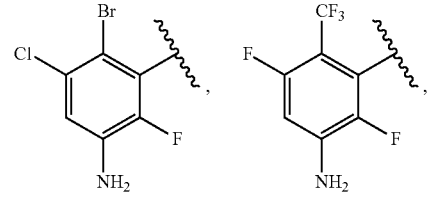

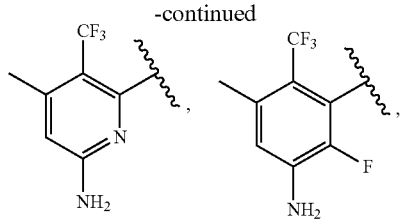
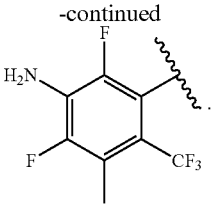
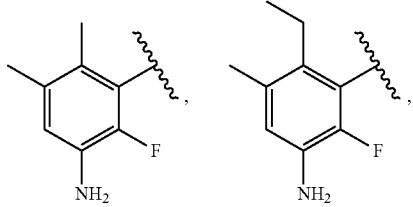
In embodiments of the compounds of the formulae above, $R^{17}$ is selected from
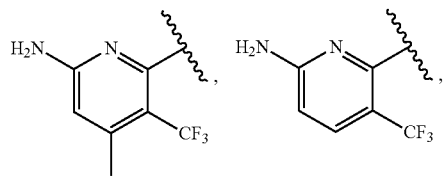
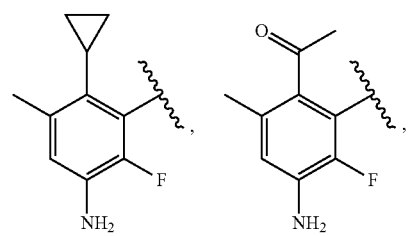
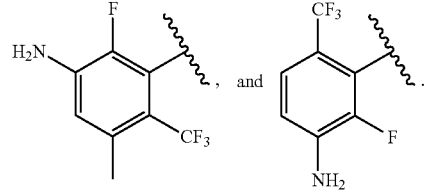
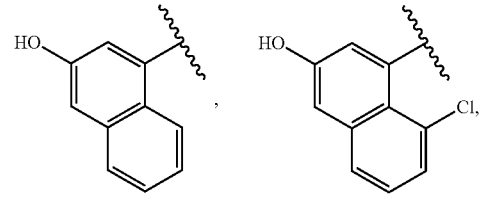
In embodiments of the formulae above, $R^{17}$ is
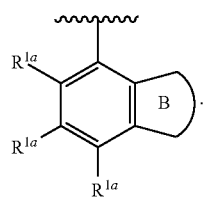
In embodiments of the formulae above, $R^{17}$ is
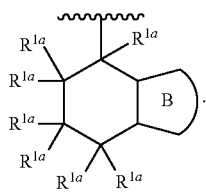
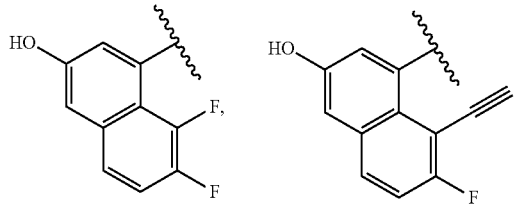
In embodiments of the compounds of the formulae above, $R^{17}$ is selected from
In embodiments of the formulae above, $R^{17}$ is
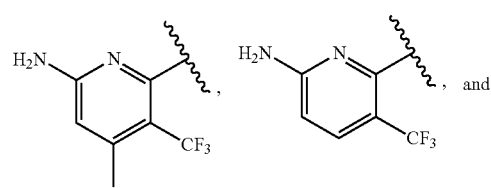
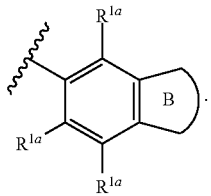

In embodiments of the formulae above, $R^{17}$ is

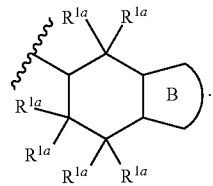

In embodiments of the formulae above, each $R^{1a}$ is independently selected from hydrogen, halogen, $C_{1-6}$alkyl, and $—OR^{12}$, wherein $C_{1-6}$alkyl is optionally substituted with one, two, or three $R^{20}g$. In embodiments of the formulae above, each $R^{1a}$ is independently selected from hydrogen, halogen, $C_{1-6}$alkyl, $—NH_2$, and $—OH$, wherein $C_{1-6}$alkyl is optionally substituted with one, two, or three $R^{20}g$.

In embodiments of the formulae above, Ring B is a 5- or 6-membered heteroaryl ring optionally substituted with one or more $R^{7c}$.

In embodiments of the formulae above, $R^{17}$ is selected from:

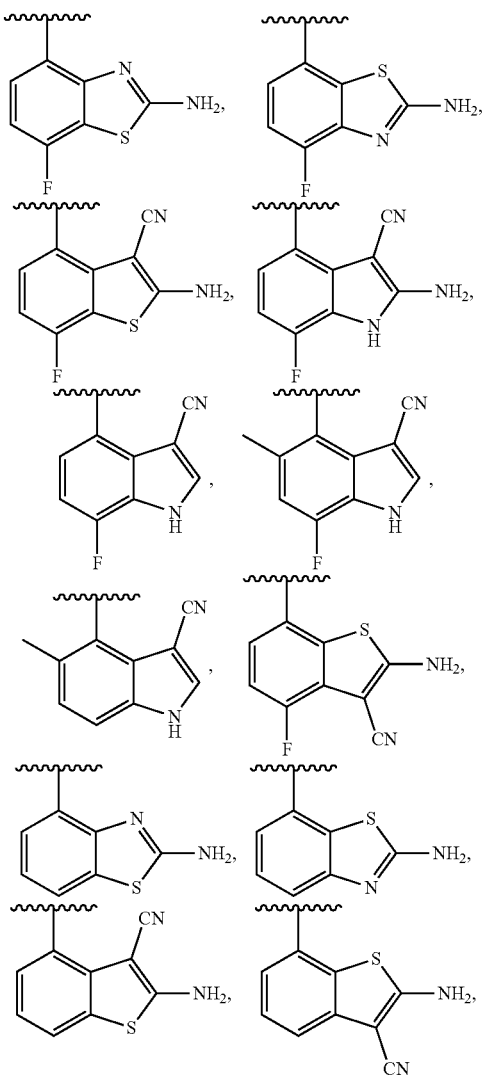

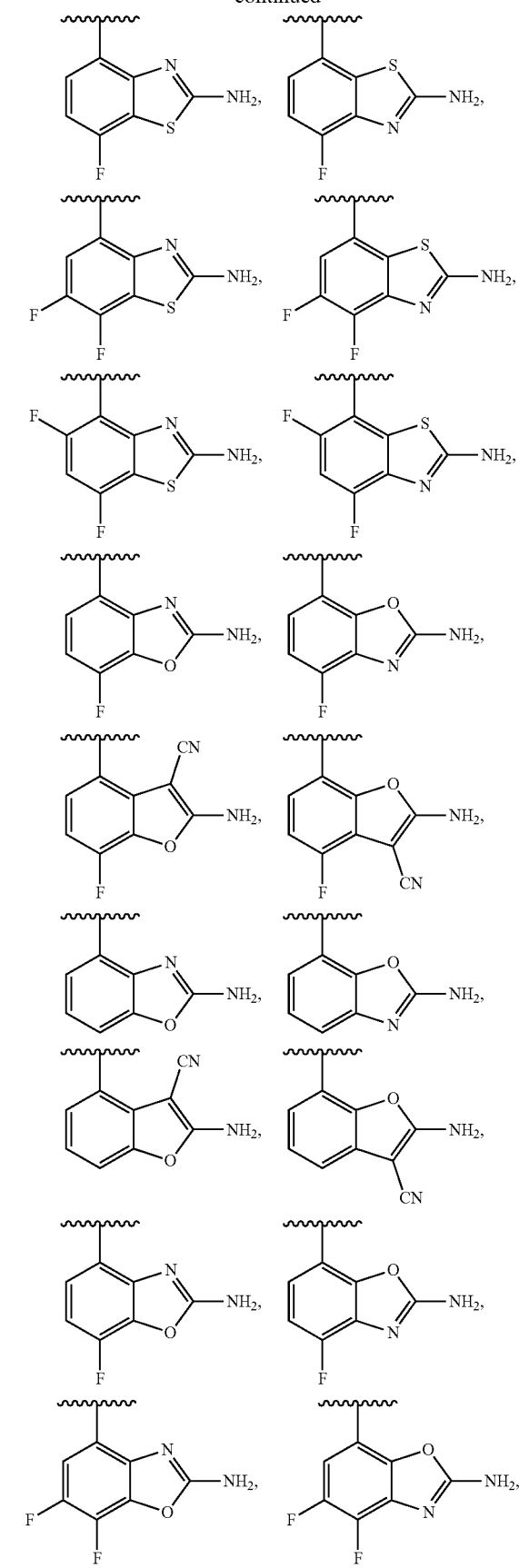

-continued

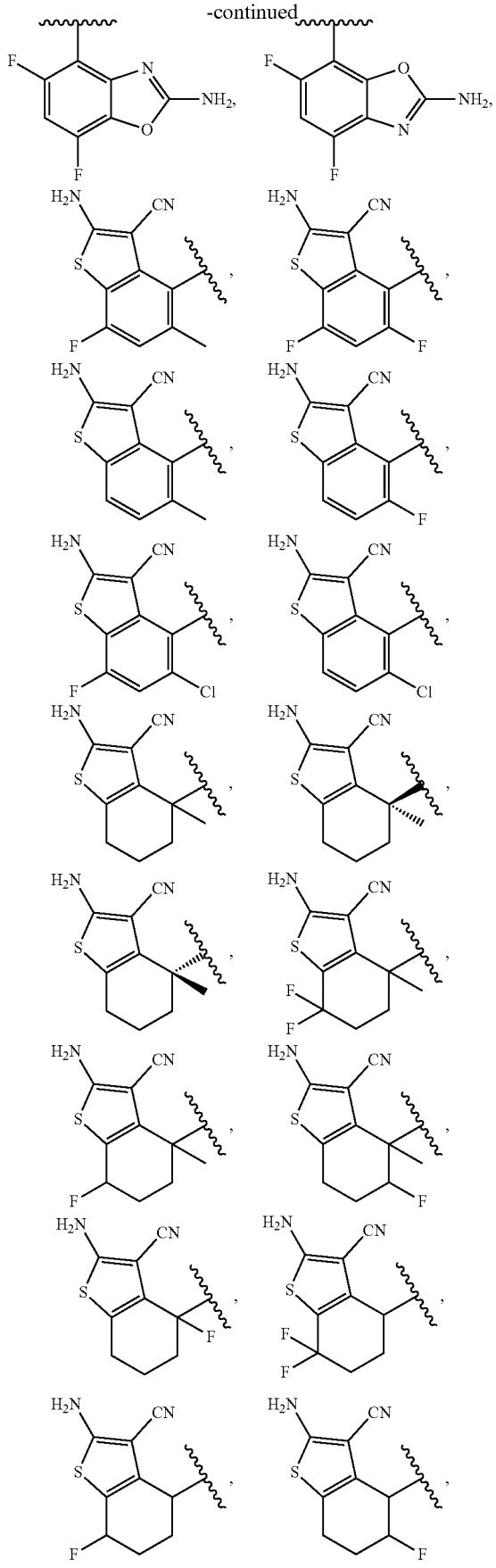

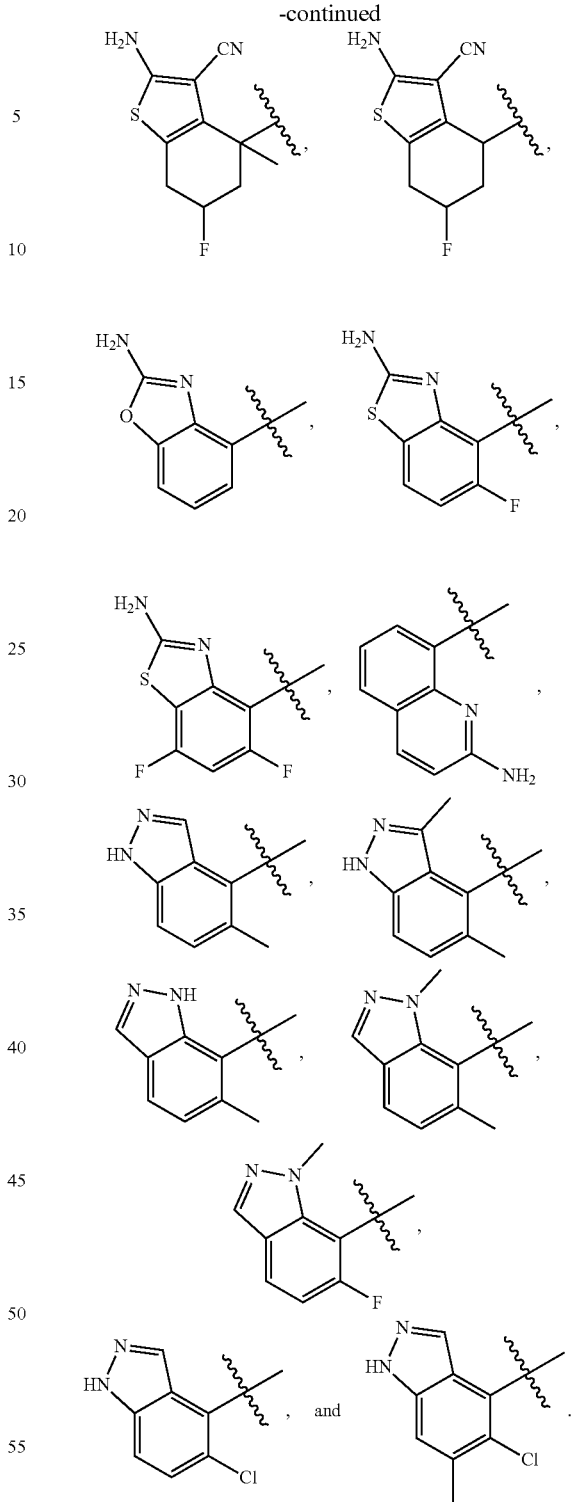

In embodiments of the formulae above, $R^{17}$ is $C_{3-10}$cycloalkyl optionally substituted with one, two, or three $R^{20}g$. In embodiments of the formulae above, $R^{17}$ is $C_{2-9}$heterocycloalkyl optionally substituted with one, two, or three $R^{20}g$. In embodiments of the formulae above, $R^{17}$ is $C_{6-10}$aryl optionally substituted with one, two, or three $R^{20}g$. In embodiments of the formulae above, $R^{17}$ is $C_{1-9}$heteroaryl optionally substituted with one, two, or three $R^{20}g$.

In embodiments of the formulae above, $R^{17}$ is

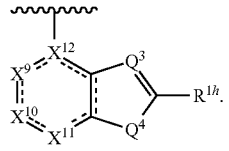

In embodiments of the formulae above, $R^{17}$ is

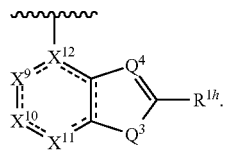

In embodiments of the formulae above, $R^{17}$ is

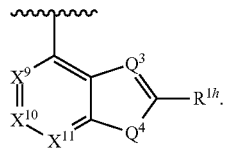

In embodiments of the formulae above, $R^{17}$ is

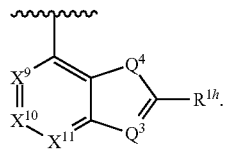

In embodiments of the formulae above, $R^{17}$ is

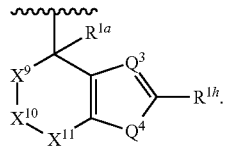

In embodiments of the formulae above, $R^{17}$ is

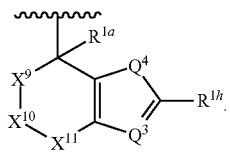

In embodiments of the formulae above, $R^{17}$ is

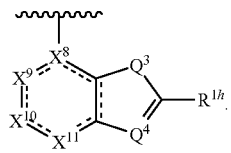

In embodiments of the formulae above, $R^{17}$ is

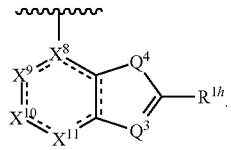

In embodiments of the formulae above, $R^{17}$ is

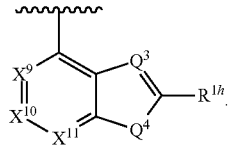

In embodiments of the formulae above, $R^{17}$ is

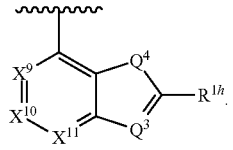

In embodiments of the formulae above, $R^{17}$ is

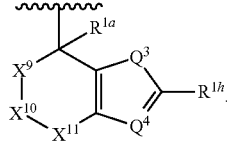

In embodiments of the formulae above, $R^{17}$ is

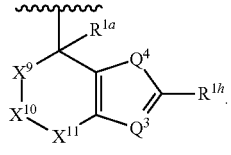

The individual embodiments herein below, or combinations thereof, (e.g., embodiments of $Z^1$, $Z^2$, $Z^3$, $Z^4$, or $Z^5$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C″), (A″-1), (B″-1), (C″-1), (A″-1a), (B″-1a), (C″-1a), (A″-1b), (B″-1b), (C″-1b), (A″-1c), (B″-1c), (C″-1c), (A″-1d), (B″-1d), (C″-1d), (A″-1e), (B″-1e), (C″-1e), (A″-1f), (B″-1f), or (C″-1f), or a pharmaceutically acceptable salt or solvate thereof.

In embodiments of the formulae above, $Z^1$ is O, $Z^2$ is $CH_2$, $Z^3$ is $CH_2$, $Z^4$ is $CH_2$, and $Z^5$ is $N(R^4)$. In embodiments of the formulae above, $Z^1$ is S, $Z^2$ is $CH_2$, $Z^3$ is $CH_2$, $Z^4$ is $CH_2$, and $Z^5$ is $N(R^4)$. In embodiments of the formulae above, $Z^1$ is N(H), $Z^2$ is $CH_2$, $Z^3$ is $CH_2$, $Z^4$ is $CH_2$, and $Z^5$ is $N(R^4)$. In embodiments of the formulae above, $Z^1$ is $CH_2$, $Z^2$ is $CH_2$, $Z^3$ is $CH_2$, $Z^4$ is $CH_2$, and $Z^5$ is $N(R^4)$. In embodiments of the formulae above, $Z^1$ is O, $Z^2$ is $CH_2$, $Z^3$ is $CH_2$, $Z^4$ is $C(R^4)(H)$, and $Z^5$ is O. In embodiments of the formulae above, $Z^1$ is O, $Z^2$ is $CH_2$, $Z^3$ is $C(R^4)(H)$, $Z^4$ is $CH_2$, and $Z^5$ is O. In embodiments of the formulae above, $Z^1$ is O, $Z^2$ is $C(R^4)(H)$, $Z^3$ is $CH_2$, $Z^4$ is $CH_2$, and $Z^5$ is O. In embodiments of the formulae above, $Z^1$ is O, $Z^2$ is $CH_2$, $Z^3$ is $CH_2$, $Z^4$ is $CH_2$, and $Z^5$ is $C(R^4)(H)$. In embodiments of the formulae above, $Z^1$ is O, $Z^2$ is $CH_2$, $Z^3$ is $CH_2$, $Z^4$ is $C(R^4)(H)$, and $Z^5$ is $CH_2$. In embodiments of the formulae above, $Z^1$ is O, $Z^2$ is $CH_2$, $Z^3$ is $C(R^4)(H)$, $Z^4$ is $CH_2$, and $Z^5$ is $CH_2$. In embodiments of the formulae above, $Z^1$ is O, $Z^2$ is $C(R^4)(H)$, $Z^3$ is $CH_2$, $Z^4$ is $CH_2$, and $Z^5$ is $CH_2$. In embodiments of the formulae above, $Z^1$ is O, $Z^2$ is a bond, $Z^3$ is $CH_2$, $Z^4$ is a bond, and $Z^5$ is $C(R^4)(H)$. In embodiments of the formulae above, $Z^1$ is O, $Z^2$ is a bond, $Z^3$ is $C(R^4)(H)$, $Z^4$ is a bond, and $Z^5$ is $CH_2$. In embodiments of the formulae above, $Z^1$ is N(H), $Z^2$ is a bond, $Z^3$ is $CH_2$, $Z^4$ is a bond, and $Z^5$ is $C(R^4)(H)$. In embodiments of the formulae above, $Z^1$ is N(H), $Z^2$ is a bond, $Z^3$ is $C(R^4)(H)$, $Z^4$ is a bond, and $Z^5$ is $CH_2$. In embodiments of the formulae above, $Z^1$ is $N(R^{11c})$, $Z^2$ is a bond, $Z^3$ is $CH_2$, $Z^4$ is a bond, and $Z^5$ is $C(R^4)(H)$. In embodiments of the formulae above, $Z^1$ is $N(R^{11c})$, $Z^2$ is a bond, $Z^3$ is $C(R^4)(H)$, $Z^4$ is a bond, and $Z^5$ is $CH_2$. In embodiments of the formulae above, $Z^1$ is O, $Z^2$ is a bond, $Z^3$ is $CH_2$, $Z^4$ is a bond, and $Z^5$ is $N(R^4)$.

In embodiments of the formulae above, $Z^1$ is $C(R^{11c})(R^{11c})$, $Z^2$ is a bond, $Z^3$ is $C(R^{11c})(R^{11c})$, $Z^4$ is a bond, and $Z^5$ is $N(R^4)$. In embodiments of the formulae above, $Z^1$ is $CH_2$, $Z^2$ is a bond, $Z^3$ is $CH_2$, $Z^4$ is a bond, and $Z^5$ is $N(R^4)$. In embodiments of the formulae above, $Z^1$ is $C(R^{11c})(R^{11c})$, $Z^2$ is a bond, $Z^3$ is $C(R^4)(R^{11c})$, $Z^4$ is a bond, and $Z^5$ is N(H). In embodiments of the formulae above, $Z^1$ is $CH_2$, $Z^2$ is a bond, $Z^3$ is $C(R^4)(H)$, $Z^4$ is a bond, and $Z^5$ is N(H). In embodiments of the formulae above, $Z^1$ is O, $Z^2$ is a bond, $Z^3$ is $C(R^4)(R^{11c})$, $Z^4$ is a bond, and $Z^5$ is $C(R^{11c})(R^{11c})$. In embodiments of the formulae above, $Z^1$ is O, $Z^2$ is a bond, $Z^3$ is $C(R^4)(R^{11c})$, $Z^4$ is a bond, and $Z^5$ is $CH_2$. In embodiments of the formulae above, $Z^1$ is O, $Z^2$ is a bond, $Z^3$ is $C(R^{11c})(R^{11c})$, $Z^4$ is a bond, and $Z^5$ is $C(R^4)(H)$. In embodiments of the formulae above, $Z^1$ is O, $Z^2$ is a bond, $Z^3$ is $CH_2$, $Z^4$ is a bond, and $Z^5$ is $C(R^4)(H)$.

In embodiments of the formulae above, $Z^1$ is O, $Z^2$ is $C(R^{11c})(R^{11c})$, $Z^3$ is $C(R^{11c})(R^{11c})$, $Z^4$ is $C(R^{11c})(R^{11c})$, and $Z^5$ is $N(R^4)$. In embodiments of the formulae above, $Z^1$ is O, $Z^2$ is $CH_2$, $Z^3$ is $CH_2$, $Z^4$ is $CH_2$, and $Z^5$ is $N(R^4)$. In embodiments of the formulae above, $Z^1$ is O, $Z^2$ is $C(R^{11c})(R^{11c})$, $Z^3$ is $C(R^{11c})(R^{11c})$, $Z^4$ is $C(R^4)(R^{11c})$, and $Z^5$ is N(H). In embodiments of the formulae above, $Z^1$ is O, $Z^2$ is $CH_2$, $Z^3$ is $CH_2$, $Z^4$ is $C(R^4)(H)$, and $Z^5$ is N(H). In embodiments of the formulae above, $Z^1$ is O, $Z^2$ is $C(R^{11c})(R^{11c})$, $Z^3$ is $C(R^4)(R^{11c})$, $Z^4$ is $C(R^{11c})(R^{11c})$, and $Z^5$ is N(H). In embodiments of the formulae above, $Z^1$ is O, $Z^2$ is $CH_2$, $Z^3$ is $C(R^4)(H)$, $Z^4$ is $CH_2$, and $Z^5$ is N(H). In embodiments of the formulae above, $Z^1$ is O, $Z^2$ is $CH_2$, $Z^3$ is $CH_2$, $Z^4$ is $C(R^4)(H)$, and $Z^5$ is N(H). In embodiments of the formulae above, $Z^1$ is $C(R^{11c})(R^{11c})$, $Z^2$ is $C(R^{11c})(R^{11c})$, $Z^3$ is $C(R^4)(R^{11c})$, $Z^4$ is $C(R^{11c})(R^{11c})$, and $Z^5$ is N(H). In embodiments of the formulae above, $Z^1$ is $CH_2$, $Z^2$ is $CH_2$, $Z^3$ is $C(R^4)(H)$, $Z^4$ is $CH_2$, and $Z^5$ is N(H). In embodiments of the formulae above, $Z^1$ is $N(R^{11c})$, $Z^2$ is $C(R^{11c})(R^{11c})$, $Z^3$ is $C(R^{11c})(R^{11c})$, $Z^4$ is $C(R^{11c})(R^{11c})$, and $Z^5$ is $N(R^4)$. In embodiments of the formulae above, $Z^1$ is N(H), $Z^2$ is $CH_2$, $Z^3$ is $CH_2$, $Z^4$ is $CH_2$, and $Z^5$ is $N(R^4)$. In embodiments of the formulae above, $Z^1$ is $N(R^{11c})$, $Z^2$ is $C(R^{11c})(R^{11c})$, $Z^3$ is $C(R^{11c})(R^{11c})$, $Z^4$ is $C(R^4)(R^{11c})$, and $Z^5$ is N(H). In embodiments of the formulae above, $Z^1$ is N(H), $Z^2$ is $CH_2$, $Z^3$ is $CH_2$, $Z^4$ is $C(R^4)(H)$, and $Z^5$ is N(H). In embodiments of the formulae above, $Z^1$ is $N(R^{11c})$, $Z^2$ is $C(R^{11c})(R^{11c})$, $Z^3$ is $C(R^4)(R^{11c})$, $Z^4$ is $C(R^{11c})(R^{11c})$, and $Z^5$ is N(H). In embodiments of the formulae above, $Z^1$ is N(H), $Z^2$ is $CH_2$, $Z^3$ is $C(R^4)(H)$, $Z^4$ is $CH_2$, and $Z^5$ is N(H). In embodiments of the formulae above, $Z^1$ is O, $Z^2$ is $C(R^{11c})(R^{11c})$, $Z^3$ is $C(R^{11c})(R^{11c})$, $Z^4$ is $C(R^4)(R^{11c})$, and $Z^5$ is O. In embodiments of the formulae above, $Z^1$ is O, $Z^2$ is $CH_2$, $Z^3$ is $CH_2$, $Z^4$ is $C(R^4)(H)$, and $Z^5$ is O. In embodiments of the formulae above, $Z^1$ is O, $Z^2$ is $C(R^{11c})(R^{11c})$, $Z^3$ is $C(R^4)(R^{11c})$, $Z^4$ is $C(R^{11c})(R^{11c})$, and $Z^5$ is O. In embodiments of the formulae above, $Z^1$ is O, $Z^2$ is $CH_2$, $Z^3$ is $C(R^4)(H)$, $Z^4$ is $CH_2$, and $Z^5$ is O. In embodiments of the formulae above, $Z^1$ is O, $Z^2$ is $C(R^{11c})(R^{11c})$, $Z^3$ is $C(R^{11c})(R^{11c})$, $Z^4$ is $C(R^4)(R^{11c})$, and $Z^5$ is $C(R^{11c})(R^{11c})$. In embodiments of the formulae above, $Z^1$ is O, $Z^2$ is $CH_2$, $Z^3$ is $CH_2$, $Z^4$ is $C(R^4)(H)$, and $Z^5$ is $CH_2$. In embodiments of the formulae above, $Z^1$ is O, $Z^2$ is $C(R^{11c})(R^{11c})$, $Z^3$ is $C(R^4)(R^{11c})$, $Z^4$ is $C(R^{11c})(R^{11c})$, and $Z^5$ is $C(R^{11c})(R^{11c})$. In embodiments of the formulae above, $Z^1$ is O, $Z^2$ is $CH_2$, $Z^3$ is $C(R^4)(H)$, $Z^4$ is $CH_2$, and $Z^5$ is $CH_2$. In embodiments of the formulae above, $Z^1$ is $N(R^{11c})$, $Z^2$ is $C(R^{11c})(R^{11c})$, $Z^3$ is $C(R^{11c})(R^{11c})$, $Z^4$ is $C(R^4)(R^{11c})$, and $Z^5$ is O. In embodiments of the formulae above, $Z^1$ is N(H), $Z^2$ is $CH_2$, $Z^3$ is $CH_2$, $Z^4$ is $C(R^4)(H)$, and $Z^5$ is O. In embodiments of the formulae above, $Z^1$ is $N(R^{11c})$, $Z^2$ is $C(R^{11c})(R^{11c})$, $Z^3$ is $C(R^4)(R^{11c})$, $Z^4$ is $C(R^{11c})(R^{11c})$, and $Z^5$ is O. In embodiments of the formulae above, $Z^1$ is N(H), $Z^2$ is $CH_2$, $Z^3$ is $C(R^4)(H)$, $Z^4$ is $CH_2$, and $Z^5$ is O. In embodiments of the formulae above, $Z^1$ is O, $Z^2$ is $CH(R^{11c})$, $Z^3$ is $CH(R^{11c})$, $Z^4$ is $CH(R^{11c})$, and $Z^5$ is $N(R^4)$. In embodiments of the formulae above, $Z^1$ is O, $Z^2$ is $CH_2$, $Z^3$ is $CH(R^{11c})$, $Z^4$ is $CH(R^{11c})$, and $Z^5$ is $N(R^4)$. In embodiments of the formulae above, $Z^1$ is O, $Z^2$ is $CH(R^{11c})$, $Z^3$ is $CH_2$, $Z^4$ is $CH(R^{11c})$, and $Z^5$ is $N(R^4)$. In embodiments of the formulae above, $Z^1$ is O, $Z^2$ is $CH(R^{11c})$, $Z^3$ is $CH(R^{11c})$, $Z^4$ is $CH_2$, and $Z^5$ is $N(R^4)$. In embodiments of the formulae above, $Z^1$ is O, $Z^2$ is $CH_2$, $Z^3$ is $CH(R^{11c})$, $Z^4$ is $CH_2$, and $Z^5$ is $N(R^4)$. In embodiments of the formulae above, $Z^1$ is O, $Z^2$ is $CH(R^{11c})$, $Z^3$ is $CH_2$, $Z^4$ is $CH_2$, and $Z^5$ is $N(R^4)$. In embodiments of the formulae above, $Z^1$ is O, $Z^2$ is $CH_2$, $Z^3$ is $CH_2$, $Z^4$ is $CH(R^{11c})$, and $Z^5$ is $N(R^4)$. In embodiments of the formulae above, $Z^1$ is O, $Z^2$ is $CH(R^{11c})$, $Z^3$ is $CH(R^{11c})$, $Z^4$ is $CH(R^{11c})$, and $Z^5$ is $N(R^{11c})$. In embodiments of the formulae above, $Z^1$ is O, $Z^2$ is $CH_2$, $Z^3$ is $CH(R^{11c})$, $Z^4$ is $CH(R^{11c})$, and $Z^5$ is $N(R^{11c})$. In embodiments of the formulae above, $Z^1$ is O, $Z^2$ is $CH(R^{11c})$, $Z^3$ is $CH_2$, $Z^4$ is $CH(R^{11c})$, and $Z^5$ is $N(R^{11c})$. In embodiments of the formulae above, $Z^1$ is O, $Z^2$ is $CH(R^{11c})$, $Z^3$ is $CH(R^{11c})$, $Z^4$ is $CH_2$, and $Z^5$ is $N(R^{11c})$. In embodiments of the formulae above, $Z^1$ is O, $Z^2$ is $CH_2$, $Z^3$ is $CH(R^{11c})$, $Z^4$ is $CH_2$, and $Z^5$ is $N(R^{11c})$. In embodiments of the formulae above, $Z^1$ is O, $Z^2$ is $CH(R^{11c})$, $Z^3$ is $CH_2$, $Z^4$ is $CH_2$, and $Z^3$ is $N(R^{11c})$. In embodiments of the formulae above, $Z^1$ is O, $Z^2$ is $CH_2$, $Z^3$ is $CH_2$, $Z^4$ is $CH(R^{11c})$, and $Z^5$ is $N(R^{11c})$.

In embodiments of the formulae above, at least one of $Z^1$, $Z^2$, $Z^3$, $Z^4$, and $Z^5$ includes a ring heteroatom (e.g., $N(R^4)$, $N(R^{11c})$, N(H), N, S, or O). In embodiments of the formulae above, at least two of $Z^1$, $Z^2$, $Z^3$, $Z^4$, and $Z^5$ include a ring heteroatom (e.g., $N(R^4)$, $N(R^{11c})$, N(H), N, S, or O). In embodiments of the formulae above, at least one of $Z^1$, $Z^2$, $Z^3$, $Z^4$, and $Z^5$ includes a ring nitrogen (e.g., $N(R^4)$, $N(R^{11c})$, N(H), or N). In embodiments of the formulae above, at least one of $Z^1$, $Z^2$, $Z^3$, $Z^4$, and $Z^5$ includes a ring oxygen.

In embodiments of the formulae above, only one of $Z^1$, $Z^2$, $Z^3$, $Z^4$, and $Z^5$ includes a ring heteroatom (e.g., $N(R^4)$, $N(R^{11c})$, N(H), N, S, or O). In embodiments of the formulae above, only two of $Z^1$, $Z^2$, $Z^3$, $Z^4$, and $Z^5$ include a ring heteroatom (e.g., $N(R^4)$, $N(R^{11c})$, N(H), N, S, or O). In embodiments of the formulae above, only one of $Z^1$, $Z^2$, $Z^3$, $Z^4$, and $Z^5$ includes a ring nitrogen (e.g., $N(R^4)$, $N(R^{11c})$, N(H), or N). In embodiments of the formulae above, only one of $Z^1$, $Z^2$, $Z^3$, $Z^4$, and $Z^5$ includes a ring oxygen.

In embodiments of the formulae above, exactly one of $Z^1$, $Z^2$, $Z^3$, $Z^4$, and $Z^5$ includes $R^4$ (e.g., $N(R^4)$, $C(R^4)$, $C(R^4)(H)$, $C(R^4)(R^{11c})$, or $C(R^4)(R^4)$). In embodiments of the formulae above, exactly two of $Z^1$, $Z^2$, $Z^3$, $Z^4$, and $Z^5$ includes $R^4$ (e.g., $N(R^4)$, $C(R^4)$, $C(R^4)(H)$, $C(R^4)(R^{11c})$, or $C(R^4)(R^4)$).

The individual embodiments herein below, or combinations thereof, (e.g., embodiments of $R^{11c}$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof.

In embodiments of the formulae above, each $R^{11c}$ is independently selected from hydrogen, halogen, $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl, wherein $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$. In embodiments of the formulae above, each $R^{11c}$ is independently selected from hydrogen and $C_{1-6}$alkyl optionally substituted with one, two, or three $R^{20k}$. In embodiments of the formulae above, each $R^{11c}$ is independently selected from hydrogen and unsubstituted $C_{1-6}$alkyl. In embodiments of the formulae above, each $R^{11c}$ is hydrogen.

The individual embodiments herein below, or combinations thereof, (e.g., embodiments of $R^{11c}$, $L^4$, or $R^{4a}$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof.

In embodiments of the formulae above, $L^4$ is a bond, —O—, —$N(R^{4d})$—, —C(O)—, or $CR^4R^{4c}$. In embodiments of the formulae above, $L^4$ is a bond. In embodiments of the formulae above, $L^4$ is-O—. In embodiments of the formulae above, $L^4$ is-$N(R^{4d})$—. In embodiments of the formulae above, $L^4$ is-N(H)—. In embodiments of the formulae above, $L^4$ is-C(O)—. In embodiments of the formulae above, $L^4$ is $CR^4R^{4c}$. In embodiments of the formulae above, $L^4$ is-$CH_2$—.

In embodiments of the formulae above, $L^4$ is a bond, —O—, —$N(R^{4d})$—, —C(O)—, or $CR^4R^4$In embodiments of the formulae above, $L^4$ is a bond. In embodiments of the formulae above, $L^4$ is-O—. In embodiments of the formulae above, $L^4$ is-$N(R^{4d})$— In embodiments of the formulae above, $L^4$ is-N(H)—. In embodiments of the formulae above, $L^4$ is-C(O)—. In embodiments of the formulae above, $L^4$ is $CR^4R^4$In embodiments of the formulae above, $L^4$ is-$CH_2$—.

In embodiments of the formulae above, $R^{4a}$ is $C_{3-10}$cycloalkyl, $C_{2-9}$heterocycloalkyl, $C_{6-10}$aryl, and $C_{1-9}$heteroaryl optionally substituted with one, two, three, or four $R^4b$. In embodiments of the formulae above, $R^{4a}$ is $C_{3-10}$cycloalkyl optionally substituted with one, two, three, or four $R^4b$. In embodiments of the formulae above, $R^{4a}$ is $C_{2-9}$heterocycloalkyl optionally substituted with one, two, three, or four $R^4b$. In embodiments of the formulae above, $R^{4a}$ is $C_{6-10}$aryl optionally substituted with one, two, three, or four $R^4b$. In embodiments of the formulae above, each $R^{4a}$ is phenyl optionally substituted with one, two, three, or four $R^4b$. In embodiments of the formulae above, $R^{4a}$ is $C_{1-9}$heteroaryl optionally substituted with one, two, three, or four $R^4b$.

In some embodiments is a compound of Formula (A), (A'), or (A"), or a pharmaceutically acceptable salt or solvate thereof, wherein $W^8$ is C(F). In some embodiments is a compound of Formula (A), (A-1), (A-1a), (A-1b), (A-1c), (A-1d), (A-1e), (A-1f), (A'), (A'-1), (A'-1a), (A'-1b), (A'-1c), (A'-1d), (A'-1e), (A'-1f), (A"), (A"-1), (A"-1a), (A"-1b), (A"-1c), (A"-1d), (A"-1e), or (A"-1f), or a pharmaceutically acceptable salt or solvate thereof, wherein $R^2$ is hydrogen. In some embodiments is a compound of Formula (A), (A-1), (A-1a), (A-1b), (A-1c), (A-1d), (A-1e), (A-1f), (A'), (A'-1), (A'-1a), (A'-1b), (A'-1c), (A'-1d), (A'-1e), (A'-1f), (A"), (A"-1), (A"-1a), (A"-1b), (A"-1c), (A"-1d), (A"-1e), or (A"-1f), or a pharmaceutically acceptable salt or solvate thereof, wherein $R^{4a}$ is $C_{2-9}$heterocycloalkyl optionally substituted with one, two, three, or four $R^4$b. In some embodiments is a compound of Formula (A), (A-1), (A-1a), (A-1b), (A-1c), (A-1d), (A-1e), (A-1f), (A'), (A'-1), (A'-1a), (A'-1b), (A'-1c), (A'-1d), (A'-1e), (A'-1f), (A"), (A"-1), (A"-1a), (A"-1b), (A"-1c), (A"-1d), (A"-1e), or (A"-1f), or a pharmaceutically acceptable salt or solvate thereof, wherein $R^{4a}$ is 4-7 membered heterocycloalkyl optionally substituted with one, two, three, or four $R^4$b.

In some embodiments is a compound of Formula (B), (B'), or (B"), or a pharmaceutically acceptable salt or solvate thereof, wherein $W^6$ is C(F).

In some embodiments of the compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, Ring B is a 6-membered aryl ring optionally substituted with one or more $R^{7c}$. In some embodiments is a compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, wherein $R^{4a}$ is $C_{3-10}$cycloalkyl, $C_{2-9}$heterocycloalkyl, $C_{6-10}$aryl, and $C_{1-9}$heteroaryl optionally substituted with one, two, three, or four $R^4$b. In some embodiments is a compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, wherein $R^{4a}$ is $C_{3-10}$cycloalkyl optionally substituted with one, two, three, or four $R^4$b. In some embodiments is a compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, wherein $R^{4a}$ is $C_{2-9}$heterocycloalkyl optionally substituted with one, two, three, or four $R^4$b. In some embodiments is a compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B'), (B'-1), (B'-1a), (B'-1b), (B'-1c), (B'- 1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, wherein $R^{4a}$ is $C_{6-10}$aryl optionally substituted with one, two, three, or four $R^{4b}$. In some embodiments is a compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, wherein each $R^{4a}$ is phenyl optionally substituted with one, two, three, or four $R^4$b. In some embodiments is a compound of Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or a pharmaceutically acceptable salt or solvate thereof, wherein $R^{4a}$ is $C_{1-9}$heteroaryl optionally substituted with one, two, three, or four $R^4$b.

In some embodiments of the compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, Ring B is a 6-membered aryl ring optionally substituted with one or more $R^{7c}$.

In some embodiments of the compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, $R^{17}$ is $C_{2-9}$heterocycloalkyl optionally substituted with one, two, or three $R^{20g}$.

In some embodiments of the compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, $R^{17}$ is $C_{1-9}$heteroaryl optionally substituted with one, two, or three $R^{20}$g.

In some embodiments is a compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, wherein $R^{4a}$ is $C_{3-10}$cycloalkyl, $C_{2-9}$heterocycloalkyl, $C_{6-10}$aryl, and $C_{1-9}$heteroaryl optionally substituted with one, two, three, or four $R^{46}$.

In some embodiments is a compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, wherein $R^{4a}$ is $C_{3-10}$cycloalkyl optionally substituted with one, two, three, or four $R^{4b}$.

In some embodiments is a compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, wherein $R^{4a}$ is $C_{2-9}$heterocycloalkyl optionally substituted with one, two, three, or four $R^{4b}$.

In some embodiments is a compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, wherein $R^{4a}$ is $C_{6-10}$aryl optionally substituted with one, two, three, or four $R^4$b. In some embodiments is a compound of Formula (C), (C-1), (C-1a), (C-1b), (C-1c), (C-1d), (C-1e), (C-1f), (C'), (C'-1), (C'-1a), (C'-1b), (C'-1c), (C'-1d), (C'-1e), (C'-1f), (C"), (C"-1), (C"-1a), (C"-1b), (C"-1c), (C"-1d), (C"-1e), or (C"-1f), or a pharmaceutically acceptable salt or solvate thereof, wherein each $R^{4a}$ is phenyl optionally substituted with one, two, three, or four $R^4$b.

In some embodiments, the compound of Formula (I), (II), (III), (IV), (XVI), or (XVII), has a formula selected from:

(Va)
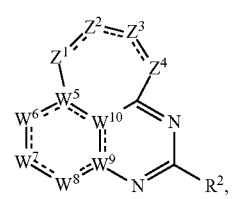

(Vc)
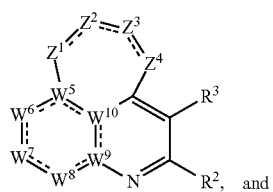

(Ve)
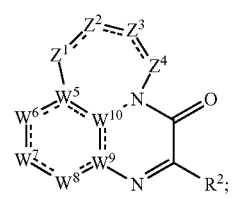

wherein $W^5$, $W^6$, $W^7$, $W^8$, $W^9$, $W^{10}$, $Z^1$, $Z^2$, $Z^3$, $Z^4$, $R^2$, and $R^3$ are as described herein for Formula (I), (II), (III), (IV), (XVI), (XVII), (Ia), (IIa), (IVd), (XVId), (XVIId), (Ie), (IIe), (IIIe), (IVe), (XVIe), (XVIIe), (If), (IIf), (IIIf), (IVf), (XVIf), (XVIh), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (VII)
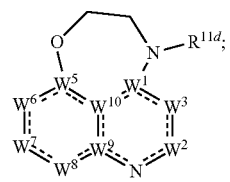

Formula (VIIa)
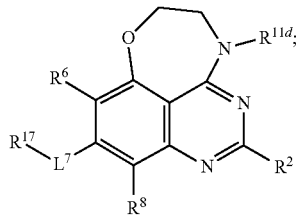

Formula (VIIb)
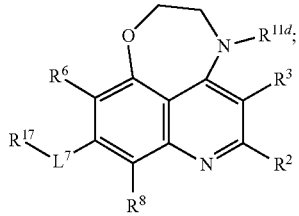

Formula (VIIc)
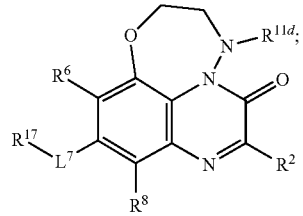

Formula (VIId)
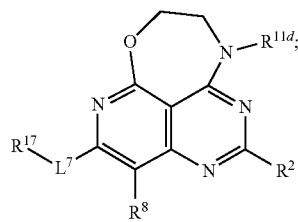

Formula (VIIe)
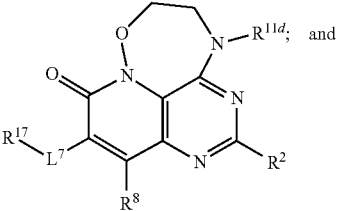

Formula (VIIf)
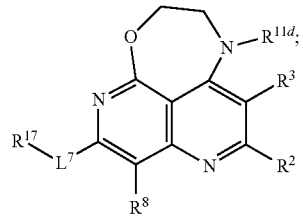

wherein $W^1$, $W^2$, $W^3$, $W^4$, $W^5$, $W^6$, $W^7$, $W^8$, $w''$, $W^{10}$, $R^2$, $R^3$, $R^4$, $R^{6a}$, $R^8$, $L^7$, $R^{17}$, and $R^{11d}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (VIII)
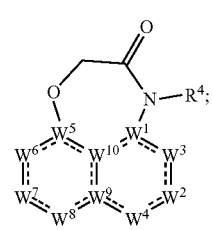

-continued

Formula (VIIIa)
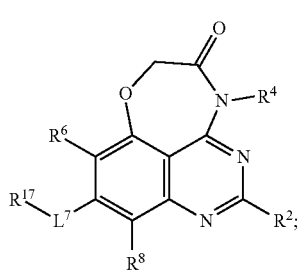

Formula (VIIIb)
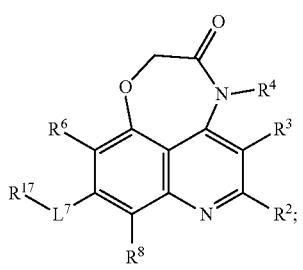

Formula (VIIIc)
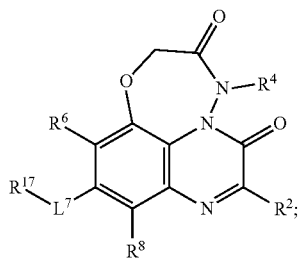

Formula (VIIId)
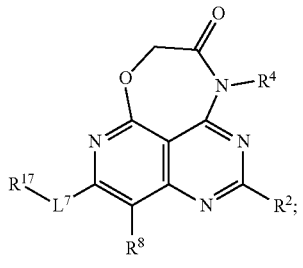

Formula (VIIIe)
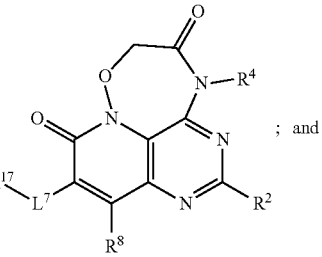
; and

Formula (VIIIf)
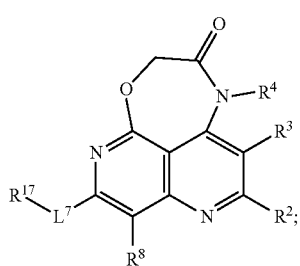

wherein $W^1$, $W^2$, $W^3$, $W^4$, $W^5$, $W^6$, $W^7$, $W^8$, $W^9$, $W^{10}$, $R^2$, $R^3$, $R^1$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (IX)
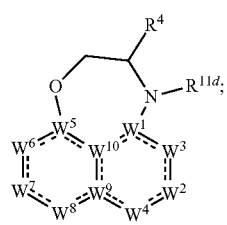

Formula (IXa)
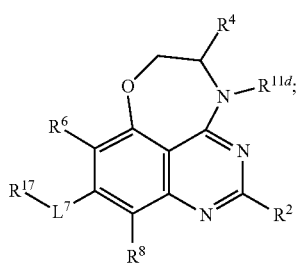

Formula (IXb)
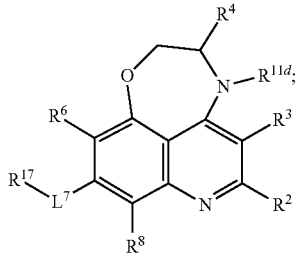

Formula (IXc)
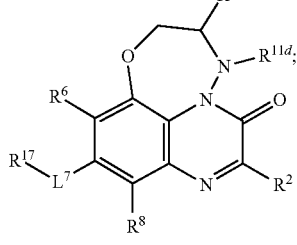

Formula (IXd)
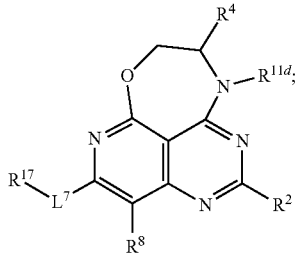

-continued

Formula (IXe)

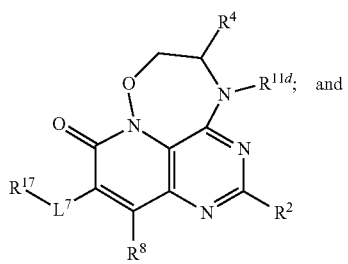

and

Formula (IXf)

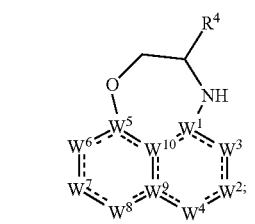

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11d}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (X)

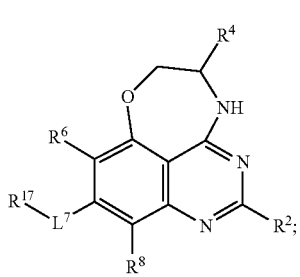

Formula (Xa)

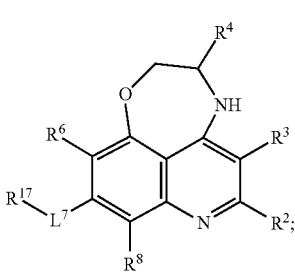

-continued

Formula (Xb)

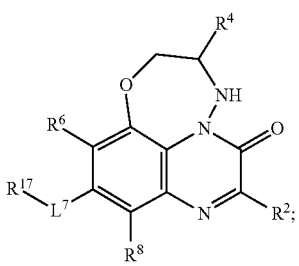

Formula (Xc)

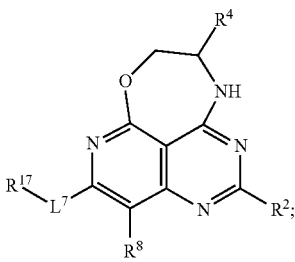

Formula (Xd)

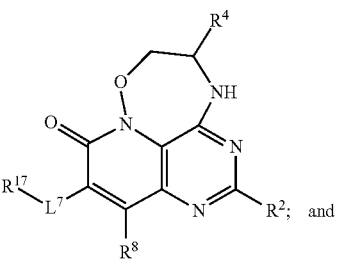

Formula (Xe)

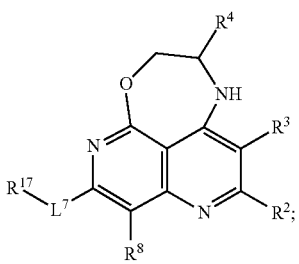

and

Formula (Xf)

wherein $W^1$, $W^2$, $W^3$, $W^4$, $W^5$, $W^6$, $W^7$, $W^8$, $W^9$, $W^{10}$, $R^2$, $R^3$, $R^4$, $R^{6a}$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XI)

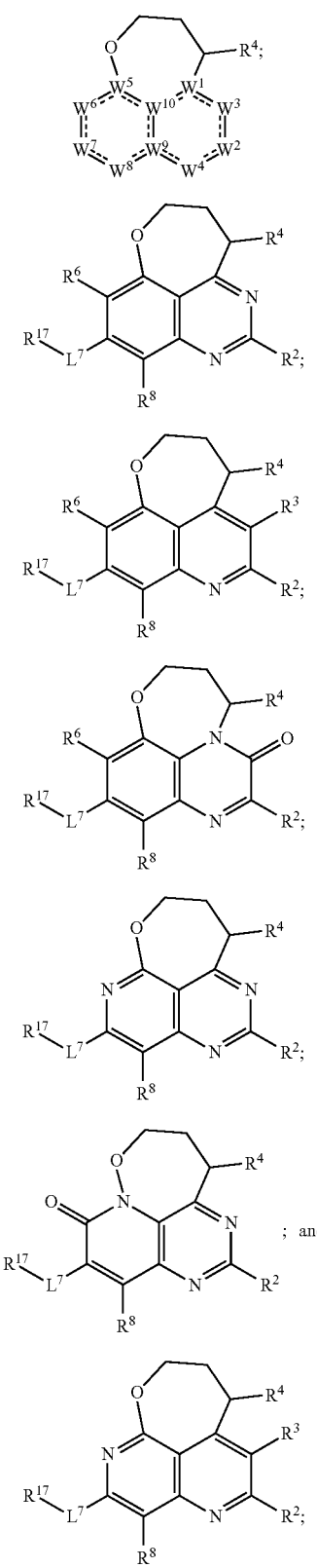

Formula (XIa)

Formula (XIb)

Formula (XIc)

Formula (XId)

Formula (XIe)

; and

Formula (XIf)

wherein $W^1$, $W^2$, $W^3$, $W^4$, $W^5$, $W^6$, $W^7$, $W^8$, $W^9$, $W^{10}$, $R^2$, $R^3$, $R^1$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XII)

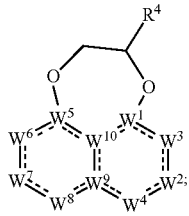

Formula (XIIa)

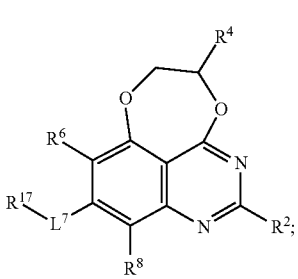

Formula (XIIb)

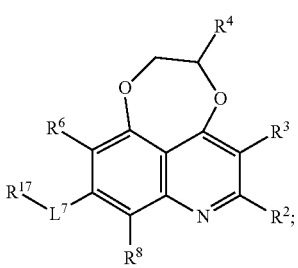

Formula (XIIc)

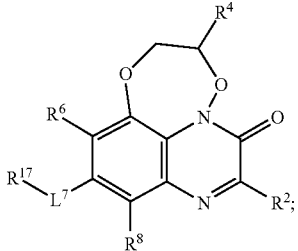

Formula (XIId)

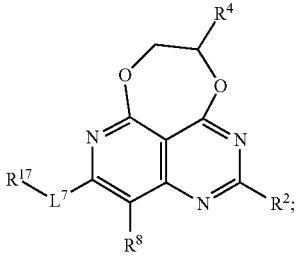

-continued

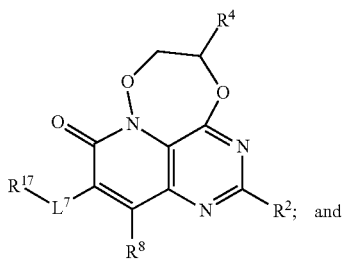
Formula (XIIe)

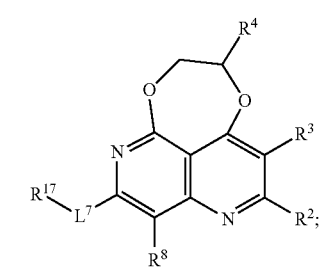
Formula (XIIf)

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

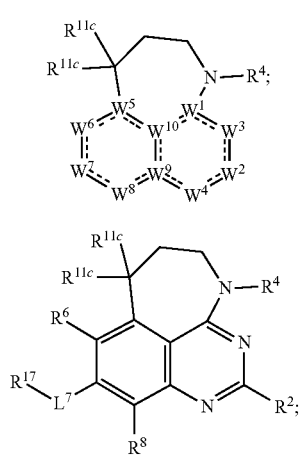
Formula (XIII)

Formula (XIIIa)

Formula (XIIIb)

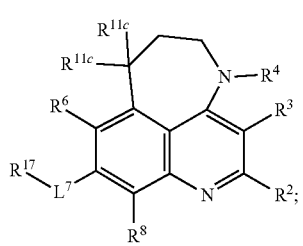

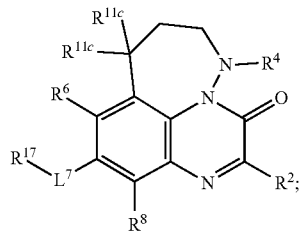
Formula (XIIIc)

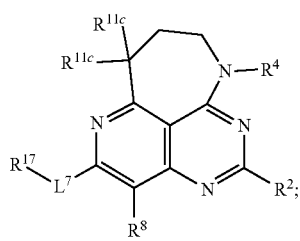
Formula (XIIId)

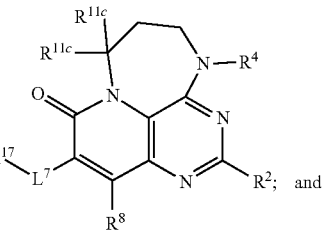
Formula (XIIIe)

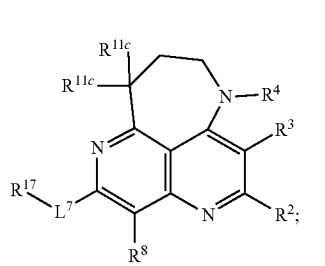
Formula (XIIIf)

wherein $W^1$, $W^2$, $W^3$, $W^4$, $W^5$, $W^6$, $W^7$, $W^8$, $W^9$, $W^{10}$, $R^2$, $R^3$, $R^4$, $R^5$, $R^6$, $R^8$, $L^7$, $R^{17}$, and $R^{11c}$, are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIIe), (IIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

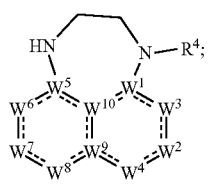
Formula (XIV)

Formula (XIVa)
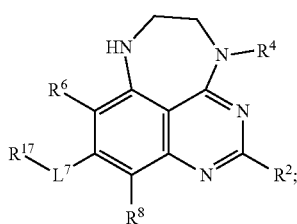

Formula (XIVb)
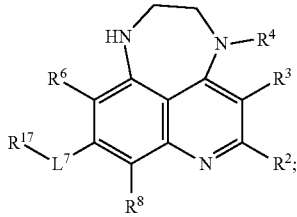

Formula (XIVc)
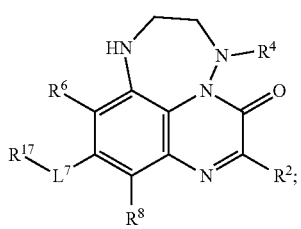

Formula (XIVd)
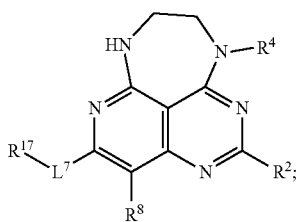

Formula (XIVe)
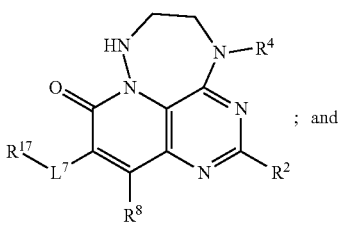

; and

Formula (XIVf)
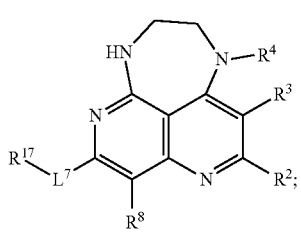

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XV)
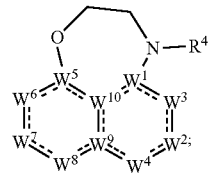

Formula (XVa)
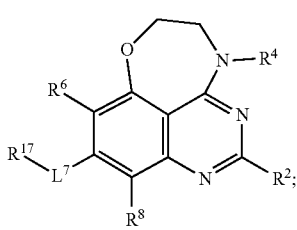

Formula (XVb)
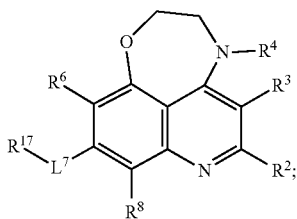

Formula (XVc)
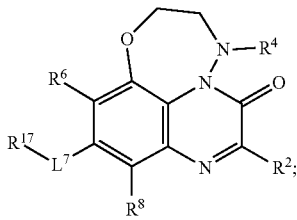

Formula (XVd)
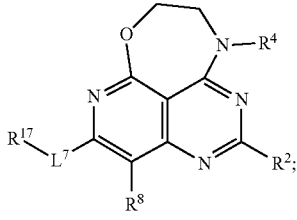

Formula (XVe)
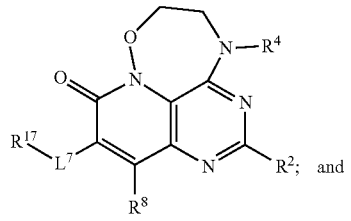

; and

-continued

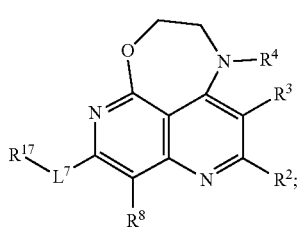
Formula (XVf)

wherein $W^1$, $W^2$, $W^3$, $W^4$, $W^5$, $W^6$, $W'''$, $W^8$, $W^9$, $W^{10}$, $R^2$, $R^3$, $R^4$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), (XVI), or (XVII), or a pharmaceutically acceptable salt or solvate thereof, the compound has a formula selected from:

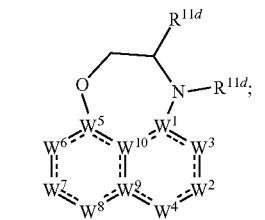
Formula (XVIII)

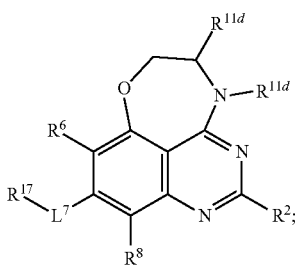
Formula (XVIIIa)

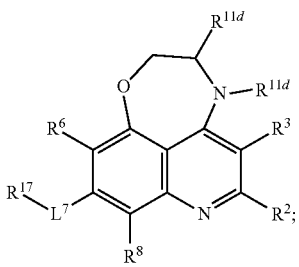
Formula (XVIIIb)

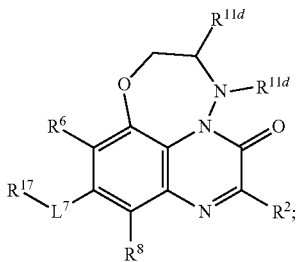
Formula (XVIIIc)

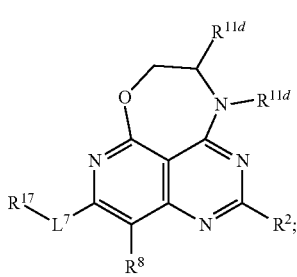
Formula (XVIIId)

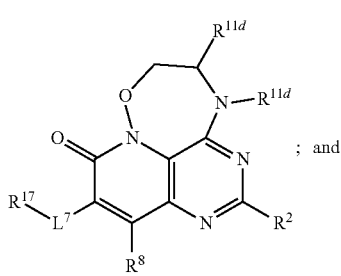
Formula (XVIIIe)

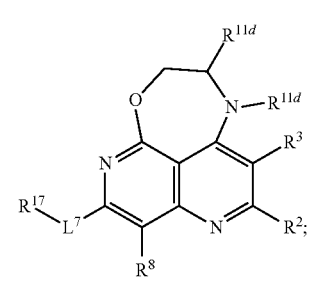
Formula (XVIIIf)

wherein $W^1$, $W^2$, $W^3$, $W^4$, $W^5$, $W^6$, $W^7$, $W^8$, $W^9$, $W^{10}$, $R^2$, $R^3$, $R^{11d}$, $R^6$, RR, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (Id), (IVd), (XVId), (XVIId), (Ie), (IIe), (IIIe), (IVe), (XVIe), (XVIIe), (If), (IIt), (IIt), (IVf), (XVIf), or (XVIIt), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

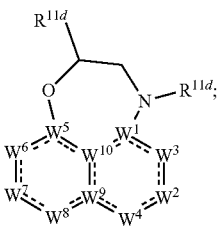
Formula (XIX)

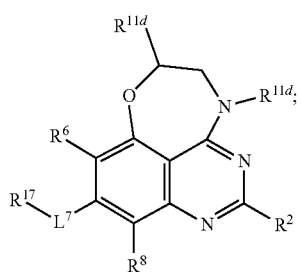

Formula (XIXa)

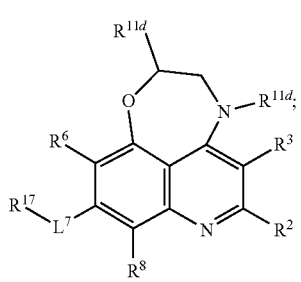

Formula (XIXb)

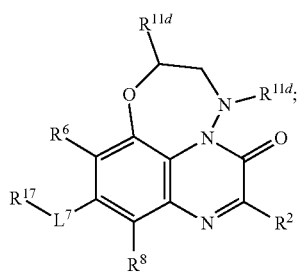

Formula (XIXc)

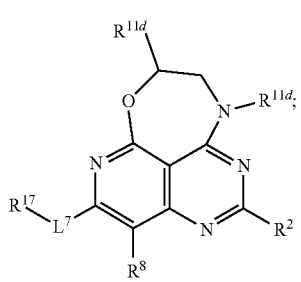

Formula (XIXd)

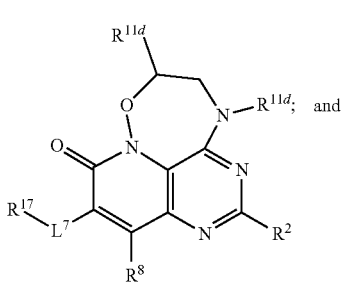

Formula (XIXe)

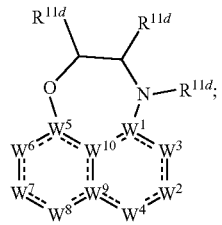

Formula (XIXf)

wherein $W^1$, $W^2$, $W^3$, $W^4$, $W^5$, $W^6$, $W^7$, $W^8$, $W^9$, $W^{10}$, $R^2$, $R^3$, $R^{11d}$, $R^6$, $R^8$, $L^7$, and $R^{17}$ are as described herein for Formula (I), (II), (III), (IV), (XVI), (XVII), (Ia), (IIa), (IVd), (XVId), (XVIId), (Ie), (IIe), (IIIe), (IVe), (XVIe), (XVIIe), (If), (IIf), (IIIf), (IVf), (XVIf), or (XVIIf), or any subformula or embodiments thereof.

In some embodiments of a compound of Formula (I), (II), (III), (IV), (XVI), or (XVII), or a pharmaceutically acceptable salt or solvate thereof, the compound has a formula selected from:

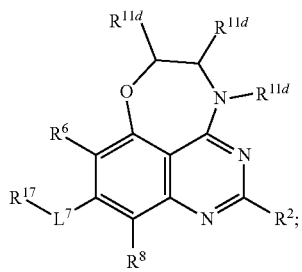

Formula (XX)

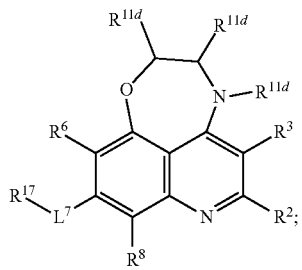

Formula (XXa)

Formula (XXb)

-continued

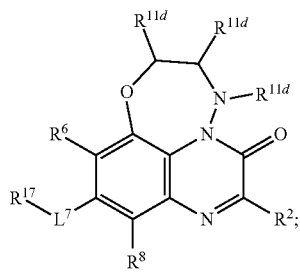

Formula (XXc)

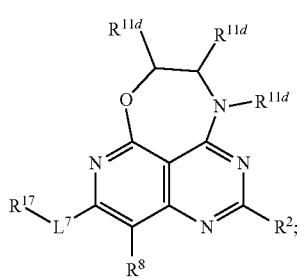

Formula (XXd)

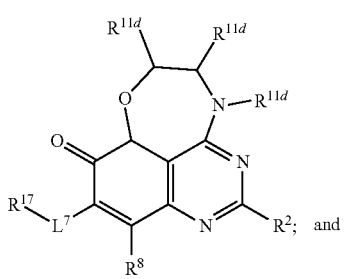

Formula (XXe)

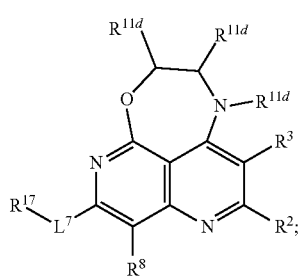

Formula (XXf)

wherein $W^1$, $W^2$, $W^3$, $W^4$, $W^5$, $W^6$, $W^7$, $W^8$, $W^7$, $W^{10}$, $R^2$, $R^3$, $R^{11d}$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

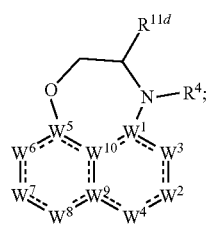

Formula (XXI)

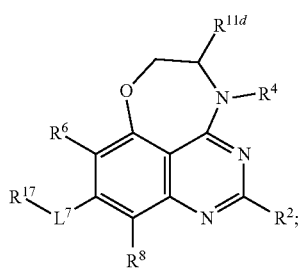

Formula (XXIa)

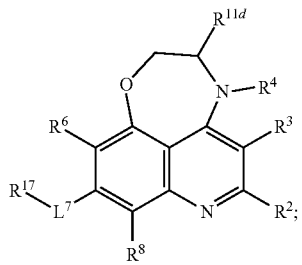

Formula (XXIb)

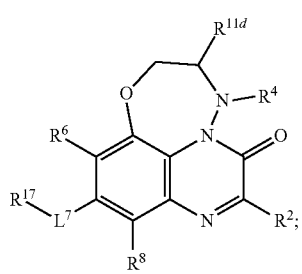

Formula (XXIc)

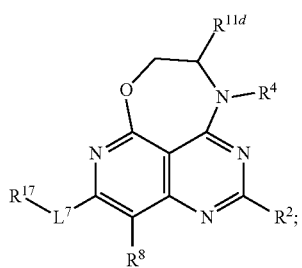

Formula (XXId)

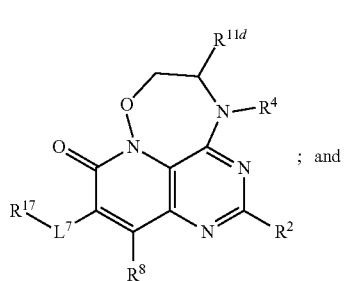

Formula (XXIe)

Formula (XXIf)

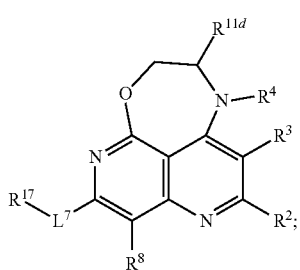

wherein $W^1$, $W^2$, $W^3$, $W^4$, $W^5$, $W^6$, $W^7$, $W^8$, $W^9$, $W^{10}$, $R^2$, $R^3$, $R^4$, $R^{11d}$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XXII)

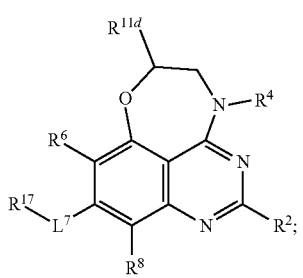

Formula (XXIIa)

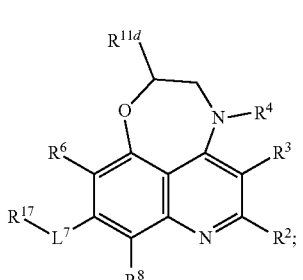

Formula (XXIIb)

(structure shown)

Formula (XXIIc)

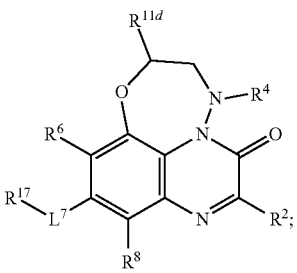

Formula (XXIId)

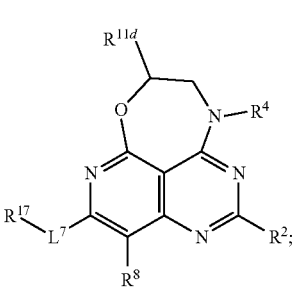

Formula (XXIIe)

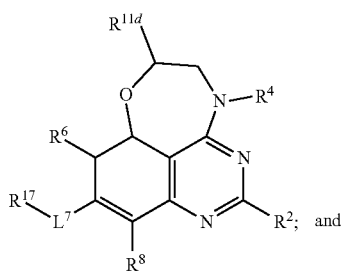

Formula (XXIIf)

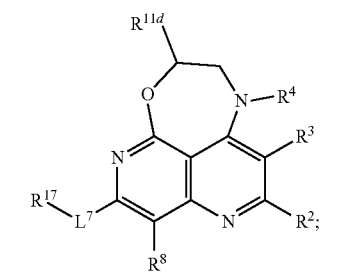

wherein $W^1$, $W^2$, $W^3$, $W^4$, $W^5$, $W^6$, $W^7$, $W^8$, $W^9$, $W^{10}$, $R^2$, $R^3$, $R^4$, $R^{114}$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XXIII)

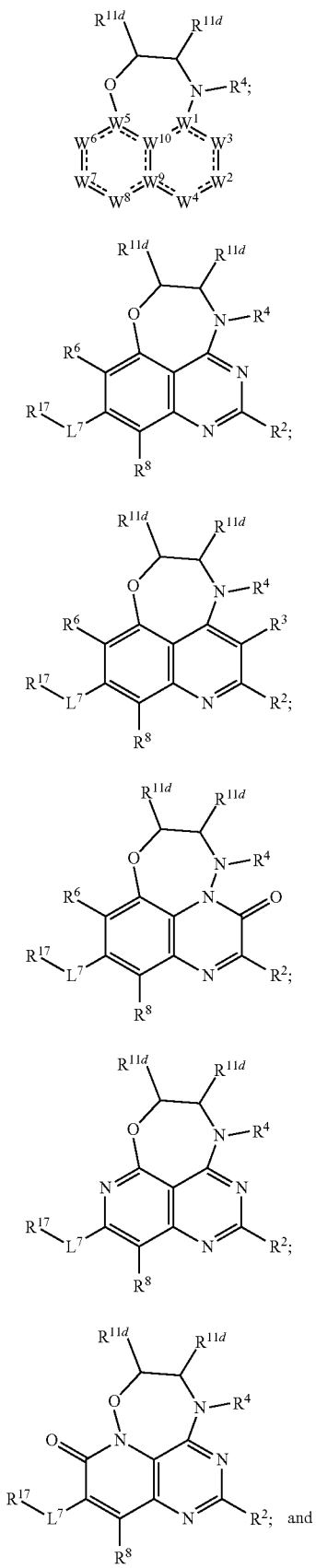

Formula (XXIIIa)

Formula (XXIIIb)

Formula (XXIIIc)

Formula (XXIIId)

Formula (XXIIIe)

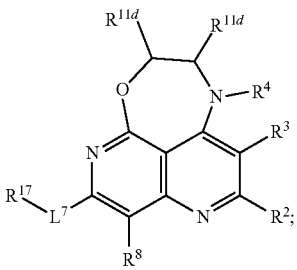

Formula (XXIIIf)

wherein $W^1$, $W^2$, $W^3$, $W^4$, $W^5$, $W^6$, $W^7$, $W^8$, $W^9$, $W^{10}$, $R^2$, $R^3$, $R^4$, $R^{11d}$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

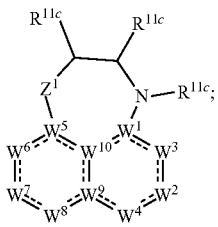

Formula (XXIV)

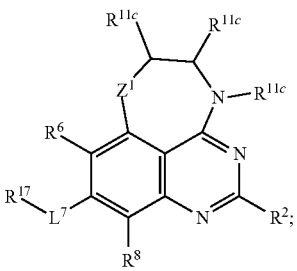

Formula (XXIVa)

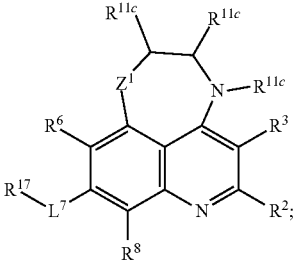

Formula (XXIVb)

-continued

Formula (XXIVc)
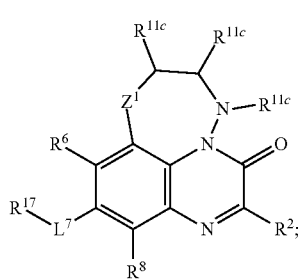

Formula (XXIVd)
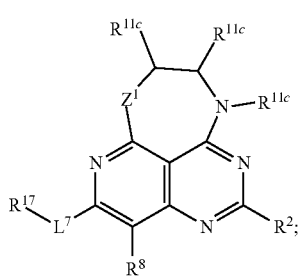

Formula (XXIVe)
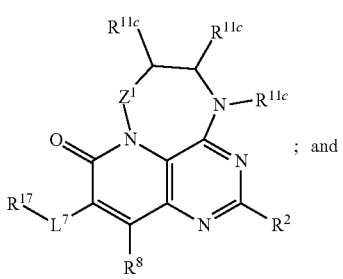

; and

Formula (XXIVf)
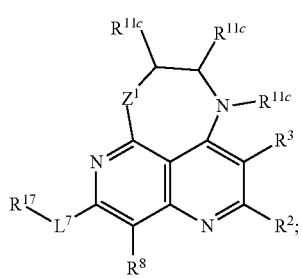

wherein $Z^1$ is selected from $N(R^{11c})$ and O; and $W^1$, $W^2$, $W^3$, $W^4$, $W^5$, $W^6$, $W^7$, $W^8$, w'', $W^{10}$, $R^2$, $R^3$, $R^{11c}$, $R^6$, RR, $L^7$, and $R^{17}$ are as described herein for Formula (I), (II), (I), (IV), (XVI), (XVI), (Ia), (IIa), (IIa), (IVa), (XVIa), (XVIIa), (b), (Ib), (Ib), (IVb), (XVIb), (XVIIb), (Ic), (Ic), (IIIc), (IVc), (XVIc), (XVIc), (Id), (Id), (IIId), (IVd), (XVId), (XVIId), (Ie), (IIe), (IIIc), (IVe), (XVIe), (XVIIe), (If), (IIt), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XXV)
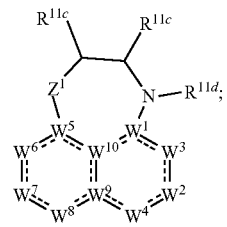

Formula (XXVa)
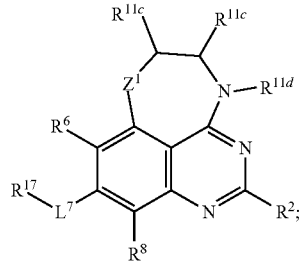

Formula (XXVb)

Formula (XXVc)
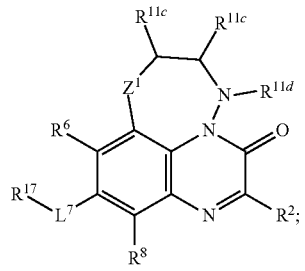

Formula (XXVd)

Formula (XXVe)
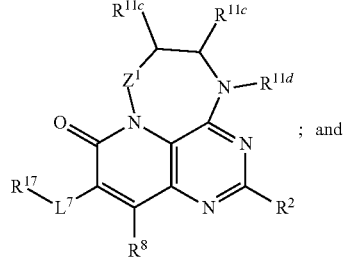

; and

Formula (XXVf)

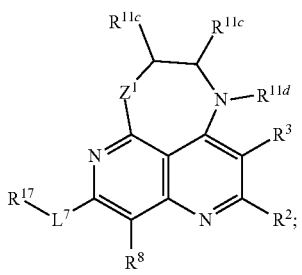

wherein $Z^1$ is selected from $N(R^{11c})$ and O; and $W^1$, $W^2$, $W^3$, $W^4$, $W^5$, $W^6$, $W^7$, $W^8$, $W^9$, $W^{10}$, $R^2$, $R^3$, $R^{11c}$, $R^{11d}$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (I), (II), (III), (IV), (XVI), or (XVII), or a pharmaceutically acceptable salt or solvate thereof, the compound has a formula selected from:

Formula (XXVI)

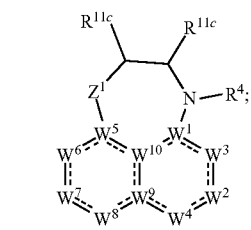

Formula (XXVIa)

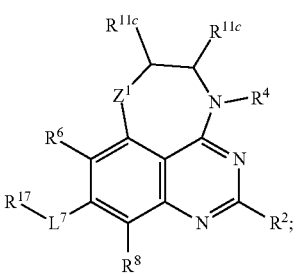

Formula (XXVIb)

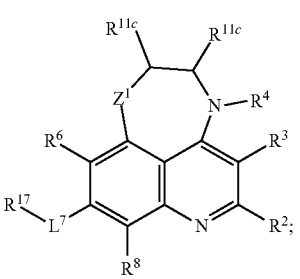

Formula (XXVIc)

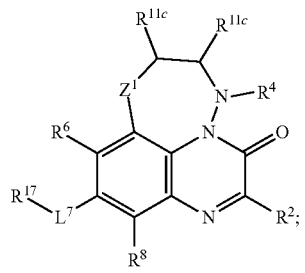

Formula (XXVId)

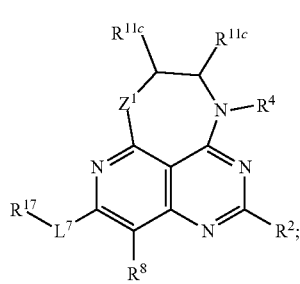

Formula (XXVIe)

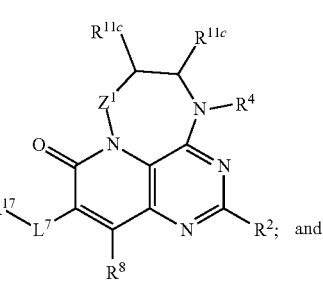

and

Formula (XXVIf)

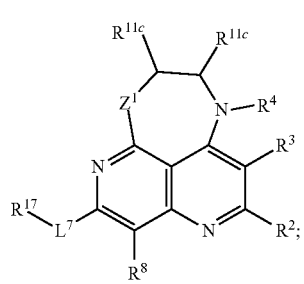

wherein $Z^1$ is selected from $N(R^{11c})$ and O; and $W^1$, $W^2$, $W^3$, $W^4$, $W^5$, $W^6$, $W^7$, $W^8$, w", $W^{10}$, $R^2$, $R^3$, $R^{11c}$, $R^4$, $R^6$, $R^8$, $L^7$, and $R^{17}$ are as described herein for Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), or (XVIIf), or any sub-formula or embodiments thereof.

In some embodiments of a compound of Formula (XVI), or a pharmaceutically acceptable salt or solvate thereof, the compound has the formula:

Formula (XVI)

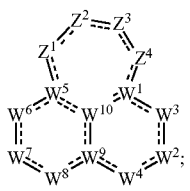

wherein:

$Z^1$, $Z^2$, $Z^3$, $Z^4$, $W^1$, $R^1$, $W^2$, $R^{2a}$, $W^3$, $R^3$, $R^{3a}$, $R^{3b}$, $W^4$, $R^3c$, $W^5$, $R^5$, $W^6$, $R^6$, $R^6a$, Rob, $W^7$, $R^7a$, $R^{7c}$, $R^{7d}$, $R^7$, $L^7$, $W^8$, $R^8$, $R^{6a}$, $R^{8b}$, $W^9$, $W^{10}$, $R^9$, $R^4$, $L^4$, $R^{4c}$, $R^{4d}$, $R^{48}$, $R^{12}$, $R^{12b}$, $R^{13}$, $R^{14}$, $R^{14a}$; $R^{15}$, $R^{21}$, $R^{22}$, $R^{23}$, $R^{24}$, and $R^{25}$ are as described for Formula (III), including in embodiments of a compound of Formula (III);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$N$=$(R^{15})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, =$C(R^{21b})_2$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{12}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_6$-10aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{11}d$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$N(R^{12})(R^{13})$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, three, four, or five $R^{20k}$;

each $R^{20a}$; $R^{20b}$, $R^{20c}$; $R^{20d}$, $R^{20e}$; $R^{20f}$, $R^{20g}$, $R^{20h}$, $R^{20i}$, $R^{20j}$, $R^{20k}$, $R^{20l}$, and $R^{20m}$ are each independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_6$-10aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, =$NR^{21}$, =$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_2$-6alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH;

$R^{17}$ is selected from:

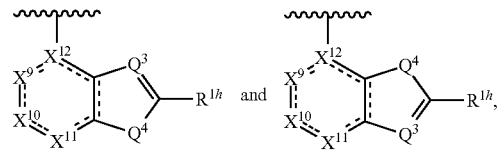

$Q^3$ is $C(R^1d)$;

$Q^4$ is S;

$X^9$, $X^{10}$, and $X^{11}$ are independently C(O), $C(R^{1a})$, or $C(R^{1a})(R^1b)$;

$X^{12}$ is C, N, or $C(R^{1a})$;

each $R^{1a}$, $R^{1b}$, $R^{1d}$, and $R^1h$ are each independently selected from hydrogen, halogen, —CN, $C_{1-6}$alkyl, $C_{1-6}$haloalkyl, $C_{2-6}$alkenyl, $C_2$-6alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{207}$;

each $R^{20}z$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}a$, —$SR^{21}a$, —$N(R^{22}a)(R^{23}a)$, —$C(O)OR^{22}a$, —$C(O)N(R^{22}a)(R^{23}a)$, —$C(O)C(O)N(R^{22}a)(R^{23}a)$, —$OC(O)N(R^{22}a)(R^{23}a)$, —$N(R^{24}a)C(O)N(R^{22}a)(R^{23}a)$, —$N(R^{24}a)C(O)OR^{25}a$, —$N(R^{24}a)C(O)R^{25}a$, —$N(R^{24}a)S(O)_2R^{25}a$, —$C(O)R^{25}a$, —$S(O)_2R^{25}a$, —$S(O)_2N(R^{22}a)(R^{23}a)$, —$OCH_2C(O)OR^{22}a$, and —$OC(O)R^{25}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}a$, —$SR^{21}a$, —$N(R^{22}a)(R^{23}a)$, —$C(O)OR^{22a}$, —$C(O)N(R^{22}a)(R^{23}a)$, —$C(O)C(O)N(R^{22}a)(R^{23}a)$, —$OC(O)N(R^{22}a)(R^{23}a)$, —$N(R^{24})C(O)N(R^{22}a)(R^{23}a)$, —$N(R^{24}a)C(O)OR^{25}a$, —$N(R^{24}a)C(O)R^{25}a$, —$N(R^{24}a)S(O)_2R^{25}a$, —$C(O)R^{25}a$, —$S(O)_2R^{25}a$, —$S(O)_2N(R^{22}a)(R^{23}a)$, and —$OC(O)R^{25a}$;

each $R^{21a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}a$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23a}$ is independently selected from H and $C_{1-6}$alkyl;

each $R^{24}$a is independently selected from H and $C_{1-6}$alkyl;

each $R^{25a}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In embodiment of the compound of the formula above, the compound has the structure of Formula (XVIa), pharmaceutically acceptable salt or solvate thereof:

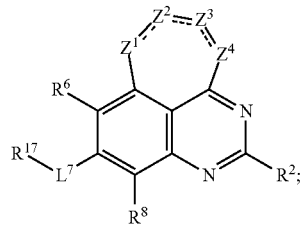

Formula (XVIa)

wherein: $Z^1$, $Z^2$, $Z^3$, $Z^4$, $R^2$, $R^6$, $R^{7c}$, $R^{7d}$, $L^7$, $R^8$, $R^4$, $L^4$, $R^{4c}$, $R^{4a}$, $R^{48}$, $R^{4b}$, $R^{12}$, $R^{120}$, $R^{13}$, $R^{14}$, $R^{14a}$, $R^{15}$, $R^{20b}$, $R^{20e}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IIIa), including in embodiments of a compound of Formula (IIIa). In embodiments of Formula (XVI), the compound has the formula (XVIa) and all variables are as described for Formula (XVI). In embodiment of the compound of the formula above, the compound has the structure of Formula (XVId), pharmaceutically acceptable salt or solvate thereof:

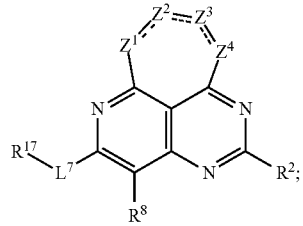

Formula (XVId)

wherein: $Z^1$, $Z^2$, $Z^3$, ZA, $R^2$, $R^{7c}$, $R^{7d}$, $L^7$, $R^8$, $R^4$, $L^4$, $R^4$, $R^{4a}$, $R^{4a}$, $R^4$, $R^{12}$, $R^{120}$, $R^{13}$, $R^{14}$, $R^{14a}$, $R^{15}$, $R^{20b}$, $R^{20f}$, $R^{20g}$, $R^{20h}$, $R^{20j}$, $R^{20g}$, $R^{20l}$, $R^{20m}$, $R^{21}$, $R^{22}$, $R^{23}$, $R^{24}$, and $R^{25}$ are as described for Formula (IIId), including in embodiments of a compound of Formula (IIId). In embodiments of Formula (XVI), the compound has the formula (XVId) and all variables are as described for Formula (XVI). In embodiments of the compounds of the formulae above, or a pharmaceutically acceptable salt or solvate thereof, $R^2$ is selected from hydrogen,

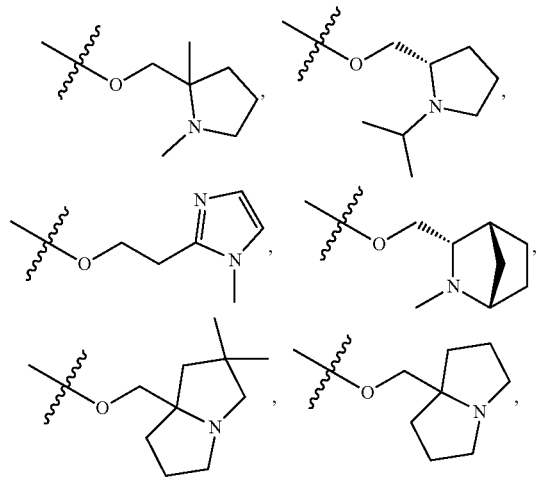

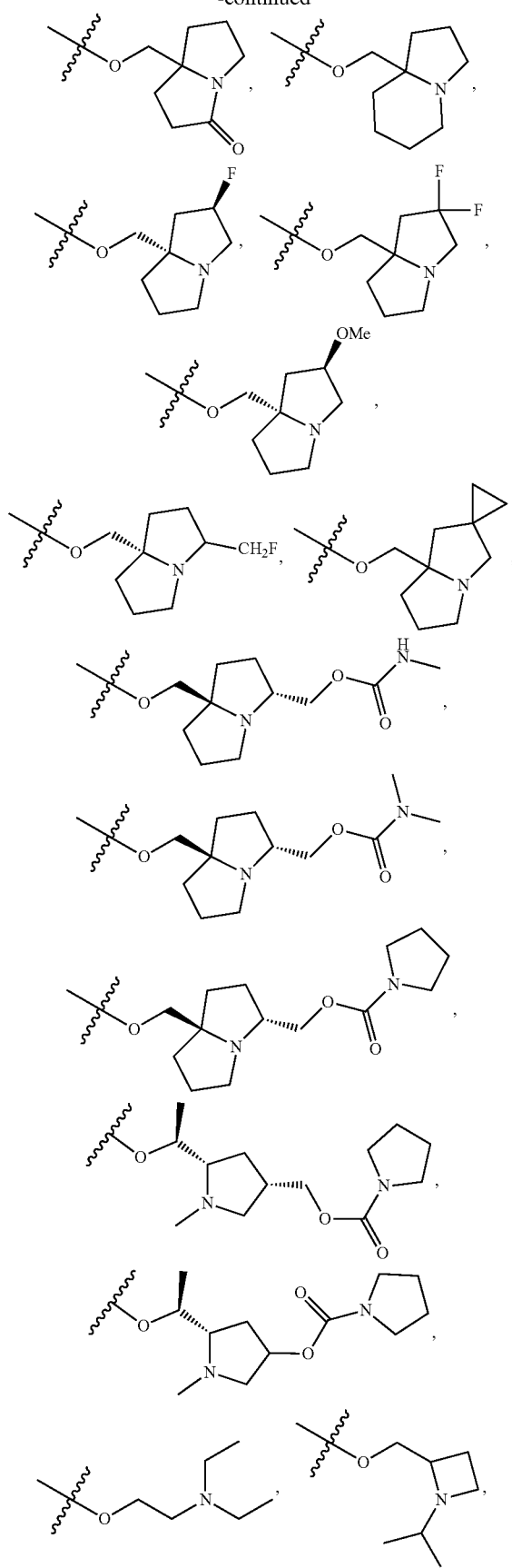
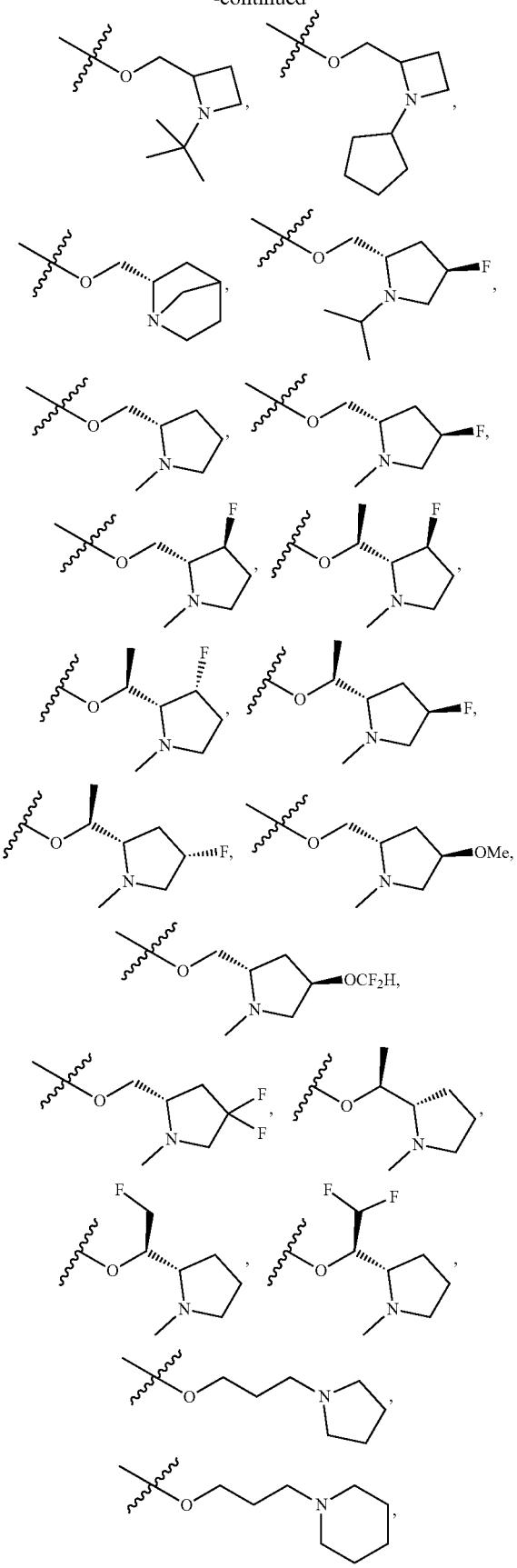

301
-continued
302
-continued
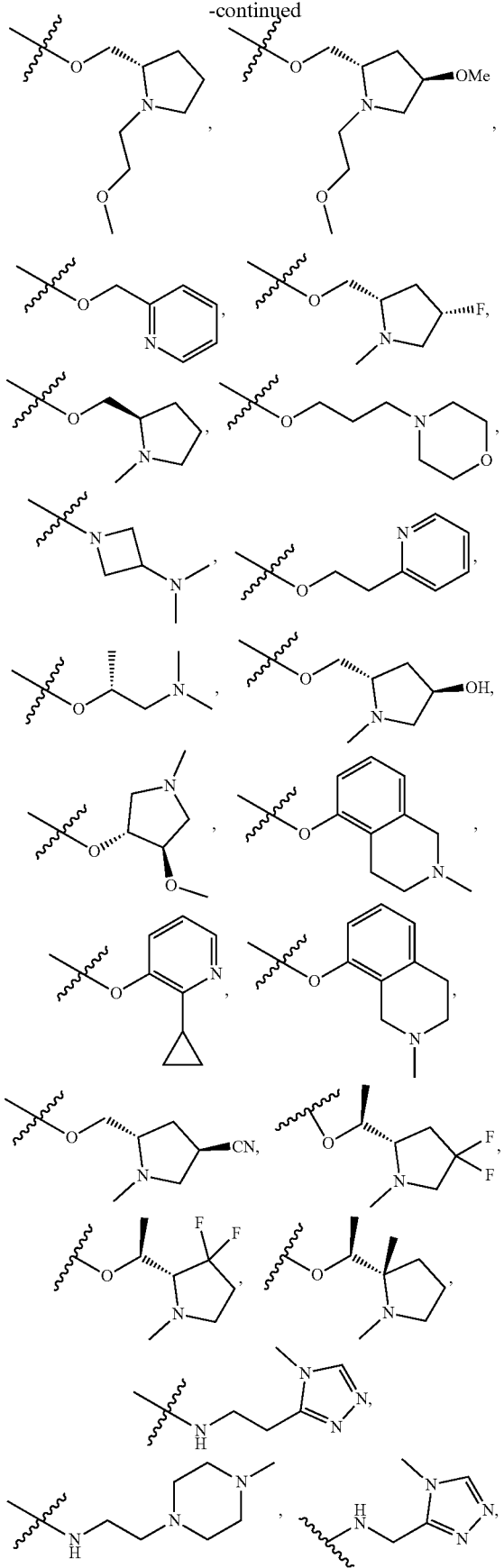
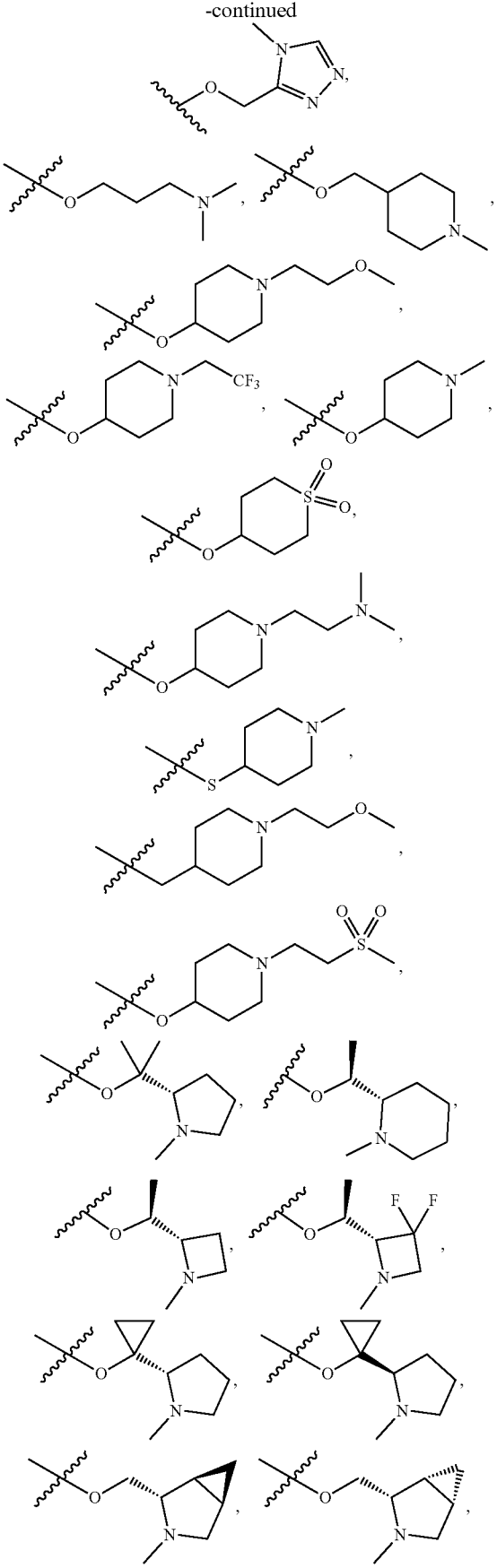

303
-continued
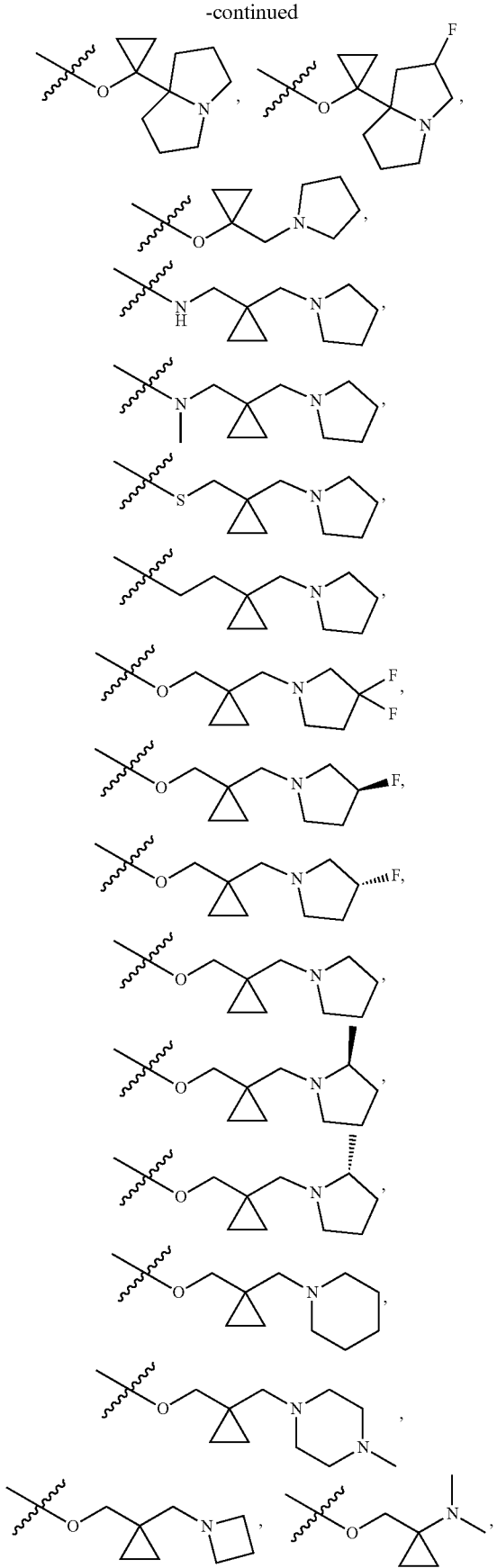
304
-continued
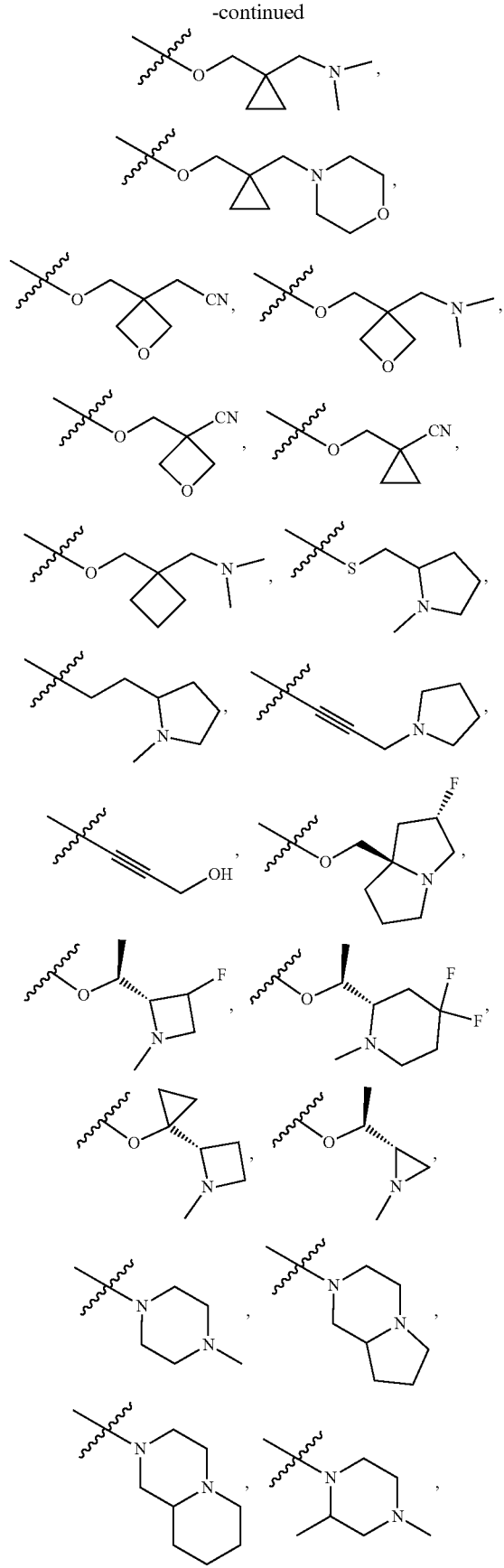

In embodiments of the compounds of the formulae above, or a pharmaceutically acceptable salt or solvate thereof, $R^{17}$ is selected from 307
-continued

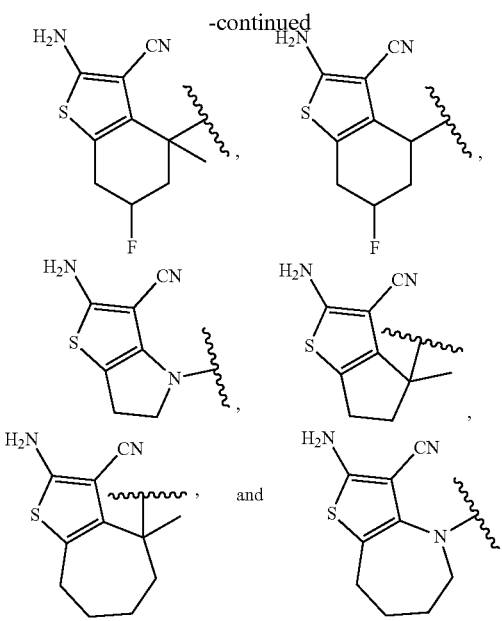

In embodiments of the compounds of the formulae above, or a pharmaceutically acceptable salt or solvate thereof, R$^{17}$ is

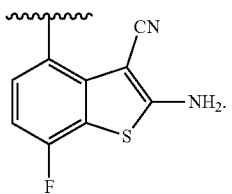

In some embodiments of a compound of Formula (XVII), or a pharmaceutically acceptable salt or solvate thereof, the compound has the formula:

Formula (XVII)

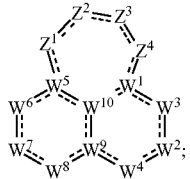

wherein:
Z$^1$, Z$^2$, Z$^3$, Z$^4$, W$^1$, R$^1$, W$^2$, R$^{2a}$, W$^3$, R$^3$, R$^{3a}$, R$^{3b}$, W$^4$, R$^3$c, W$^5$, R$^5$, W$^6$, R$^6$, R$^{6a}$, R$^{6b}$, W$^7$, R$^7$, R$^{7c}$, R$^{7d}$, R$^7$, L$^7$, R$^{17}$, W$^8$, R$^8$, R&8, R$^{8\%}$, W$^9$, W$^{10}$, R$^3$, R$^4$, L$^4$, R$^{4c}$, R$^{4d}$, R$^{4a}$, R$^{12}$, R$^{12a}$, R$^{12b}$, R$^{13}$, R$^{14}$, R$^{14}$, R$^{15}$, R$^{21}$, R$^2$, R$^{23}$, R$^{24}$, and R$^{25}$ are as described for Formula (IV), including in embodiments of a compound of Formula (IV);
R$^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$a, —SR$^{12}$, —N(R$^{12}$)(R$^{13}$), —N=(R$^{15}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N 308
(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;
each R$^{4b}$ is independently selected from halogen, oxo, —CN, C$_{1-6}$alkyl, C$_{2-6}$alkenyl, C$_{2-6}$alkynyl, C$_{3-12}$cycloalkyl, C$_{2-11}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, =C(R$^{21b}$)$_2$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{12}$, —CH$_2$S(O)$_2$R$^{15}$, —CH$_2$S(O)$_2$N(R$^{12}$)(R$^{13}$), and —P(=O)(R$^{12}$)$_2$, wherein C$_{1-6}$alkyl, C$_{2-6}$alkenyl, C$_{2-6}$alkynyl, C$_{3-12}$cycloalkyl, C$_{2-11}$heterocycloalkyl, C$_6$-10aryl, and C$_{1-9}$heteroaryl are optionally substituted with one or more R$^{20}$j;
each R$^{11c}$ is independently selected from hydrogen, halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=OX=NH)N(R$^{12}$)(R$^{13}$), —(C$_{1-6}$alkyl)-C(O)N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four, or five R$^{20k}$;
each R$^{11}$d is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{12}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{12}$, —S(O)$_2$R$^{15}$, —S(O)$_2$N(R$^{12}$)(R$^{13}$)—, S(=O)(=NH)N(R$^{12}$)(R$^{13}$), —(C$_{1-6}$alkyl)-C(O)N(R$^{12}$)(R$^{13}$), —(C$_{1-6}$alkyl)-OC(O)R$^{12}$, —(C$_{1-6}$alkyl)-N(R$^{14}$)C(O)R$^{12}$, —(C$_{1-6}$alkyl)-S(O)$_2$R$^{15}$, and —(C$_{1-6}$alkyl)-S(O)$_2$N(R$^{12}$)(R$^{13}$), wherein C$_{1-6}$alkyl, C$_{2-6}$alkenyl, C$_{2-6}$alkynyl, C$_{1-6}$haloalkyl, C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, three, four or five R$^{20k}$;
each R$^{20a}$; R$^{20b}$, R$^{20c}$; R$^{20d}$, R$^{20e}$; R$^{20f}$, R$^{20g}$, R$^{20h}$, R$^{20i}$, R$^{20j}$, R$^{20k}$, R$^{20l}$, and R$^{20m}$ are each independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, =$NR^{21}$, —$C(R^{21b})_2$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_2$-6alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{21}$, —$N(R^{24})S(O)_2R^{25}$, —$C(O)R^{21}$, —$S(O)_2R^{25}$, —$S(O)_2N(R^{22})(R^{23})$, and —$OC(O)R^{25}$;

$R^{21b}$ is independently selected at each occurrence from hydrogen, halogen, $C_{1-6}$alkyl, $C_{1-6}$haloalkyl, $C_{2-6}$alkenyl, $C_{2-6}$alkynyl, $C_3$-10cycloalkyl, $C_{2-9}$heterocycloalkyl, $C_{6-10}$aryl, and $C_{1-9}$heteroaryl, or two $R^{21b}$ are taken together with the carbon atom to which they are attached to form $C_{3-10}$cycloalkyl or $C_{2-9}$heterocycloalkyl; each of which is optionally substituted with one, two, or three substituents independently selected from halogen, $C_{1-3}$ alkyl, $C_{1-3}$ haloalkyl, and —OH;

$R^{17}$ is selected from:

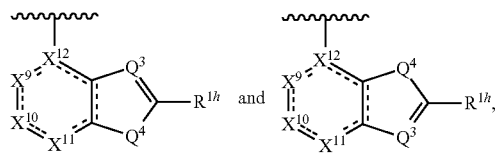

$Q^3$ is $C(R^{14})$;
$Q^4$ is S;
$X^9$, $X^{10}$, and $X^{11}$ are independently $C(O)$, $C(R^{1a})$, or $C(R^{1a})(R^1b)$;
$X^{12}$ is C, N, or $C(R^{1a})$;
each $R^1a$, $R^{1b}$, $R^{1d}$, and $R^1h$ are each independently selected from hydrogen, halogen, —CN, $C_{1-6}$alkyl, $C_{1-6}$haloalkyl, $C_{2-6}$alkenyl, $C_2$-6alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{207}$;

each $R^{207}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}a$, —$SR^{21}a$, —$N(R^{22}a)(R^{23}a)$, —$C(O)OR^{22a}$, —$C(O)N(R^{22}a)(R^{23}a)$, —$C(O)C(O)N(R^{22}a)(R^{23}a)$, —$OC(O)N(R^{22}a)(R^{23}a)$, —$N(R^{24}a)C(O)N(R^{22}a)(R^{23}a)$, —$N(R^{24}a)C(O)OR^{25}a$, —$N(R^{24}a)C(O)R^{25}a$, —$N(R^{24}a)S(O)_2R^{25}a$, —$C(O)R^{25}a$, —$S(O)_2R^{25}a$, —$S(O)_2N(R^{22}a)(R^{23}a)$, —$OCH_2C(O)OR^{22}a$, and —$OC(O)R^{25}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}a$, —$SR^{21}a$, —$N(R^{22}a)(R^{23}a)$, —$C(O)OR^{22a}$, —$C(O)N(R^{22}a)(R^{23}a)$, —$C(O)C(O)N(R^{22}a)(R^{23}a)$, —$OC(O)N(R^{22}a)(R^{23}a)$, —$N(R^{24})C(O)N(R^{22}a)(R^{23}a)$, —$N(R^{24}a)C(O)OR^{25}a$, —$N(R^{24}a)C(O)R^{25a}$, —$N(R^{24}a)S(O)_2R^{25}a$, —$C(O)R^{25}a$, —$S(O)_2R^{25}a$, —$S(O)_2N(R^{22}a)(R^{23}a)$, and —$OC(O)R^{25a}$;

each $R^{21a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}a$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23a}$ is independently selected from H and $C_{1-6}$alkyl;

each $R^{24}a$ is independently selected from H and $C_{1-6}$alkyl;

each $R^{25a}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied. In embodiment of the compound of the formula above, the compound has the structure of Formula (XVIIa), pharmaceutically acceptable salt or solvate thereof:

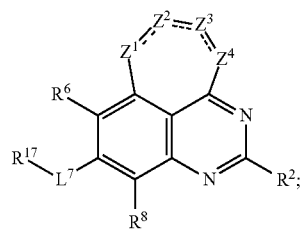

Formula (XVIIa)

wherein: $Z^1$, $Z^2$, $Z^3$, $Z^4$, $R^2$, $R^6$, $R^{7c}$, $R^{7d}$, $L^7$, $R^8$, $R^4$, $L^4$, $R^{4c}$, $R^{4d}$, $R^{4a}$, $R^4b$, $R^{12}$, $R^{12a}$, $R^{120}$, $R^{13}$, $R^{14}$, $R^{14a}$, RIS, $R^{20b}$, $R^{20e}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IVa), including in embodiments of a compound of Formula (IVa). In embodiments of Formula (XVII), the compound has the formula (XVIIa) and all variables are as described for Formula (XVII). In embodiment of the compound of the formula above, the compound has the structure of Formula (XVIId), pharmaceutically acceptable salt or solvate thereof:

Formula (XVIId)

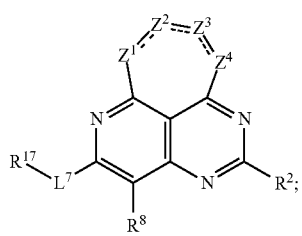

$Z^1$, $Z^1$, $Z^3$, $Z^4$, $R^2$, $R^{7c}$, $R^{7d}$, $L^7$, $R^8$, $R^4$, $L^7$, $R^{4c}$, $R^{4d}$, $R^{4a}$, $R^{4b}$, $R^{12}$, $R^{12a}$, $R^{120}$, $R^{13}$, $R^{14}$, $R^{144}$, $R^{15}$, $R^{20b}$, $R^{20f}$, $R^{20g}$, $R^{20h}$, $R^{20j}$, $R^{20k}$, $R^{20l}$, $R^{20m}$, $R^{21}$, $R^{22}$, $R^{23}$, $R^{24}$, and $R^{25}$ are as described for Formula (IVd), including in embodiments of a compound of Formula (IVd). In embodiments of Formula (XVII), the compound has the formula (XVIId) and all variables are as described for Formula (XVII). In embodiments of the compounds of the formulae above, or a pharmaceutically acceptable salt or solvate thereof, $R^2$ is selected from

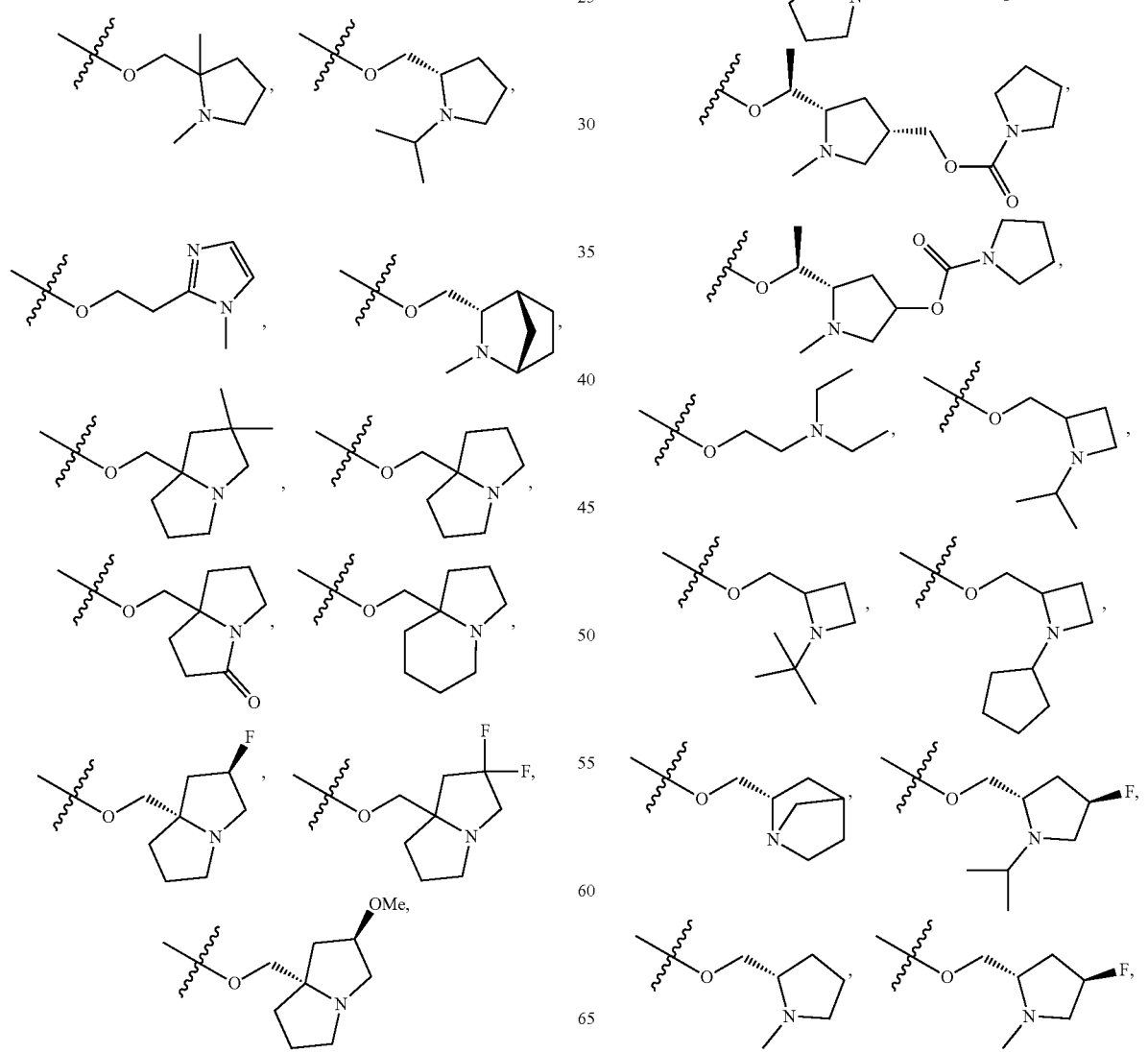

-continued
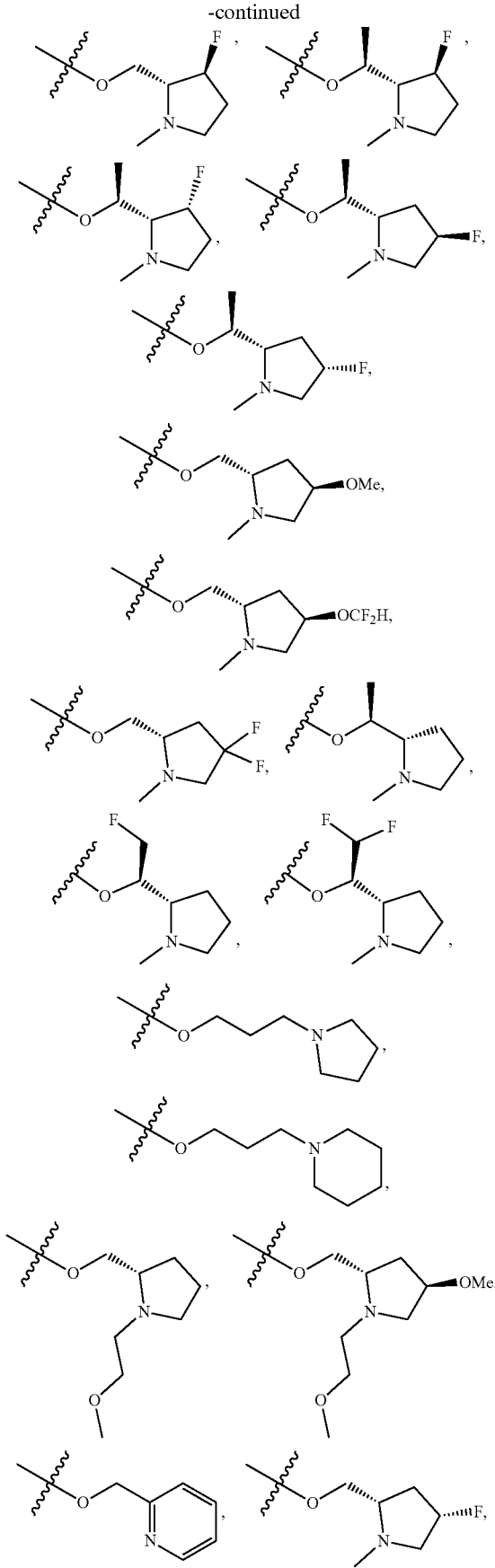
-continued
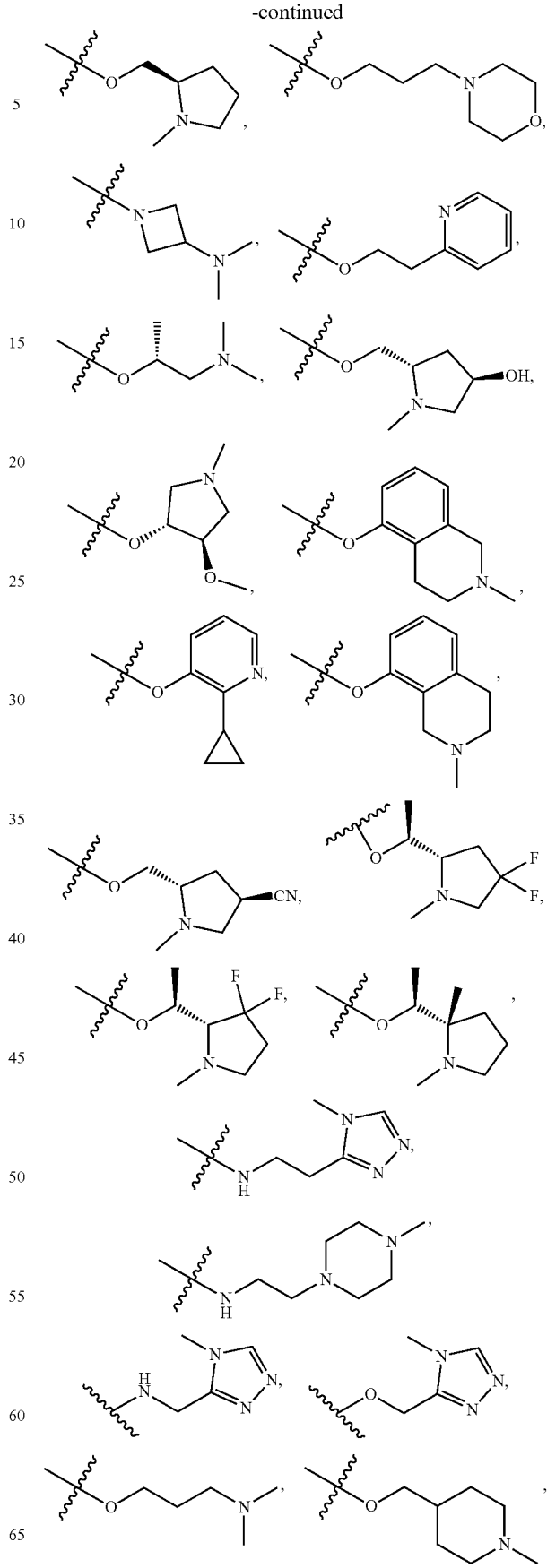

315
-continued
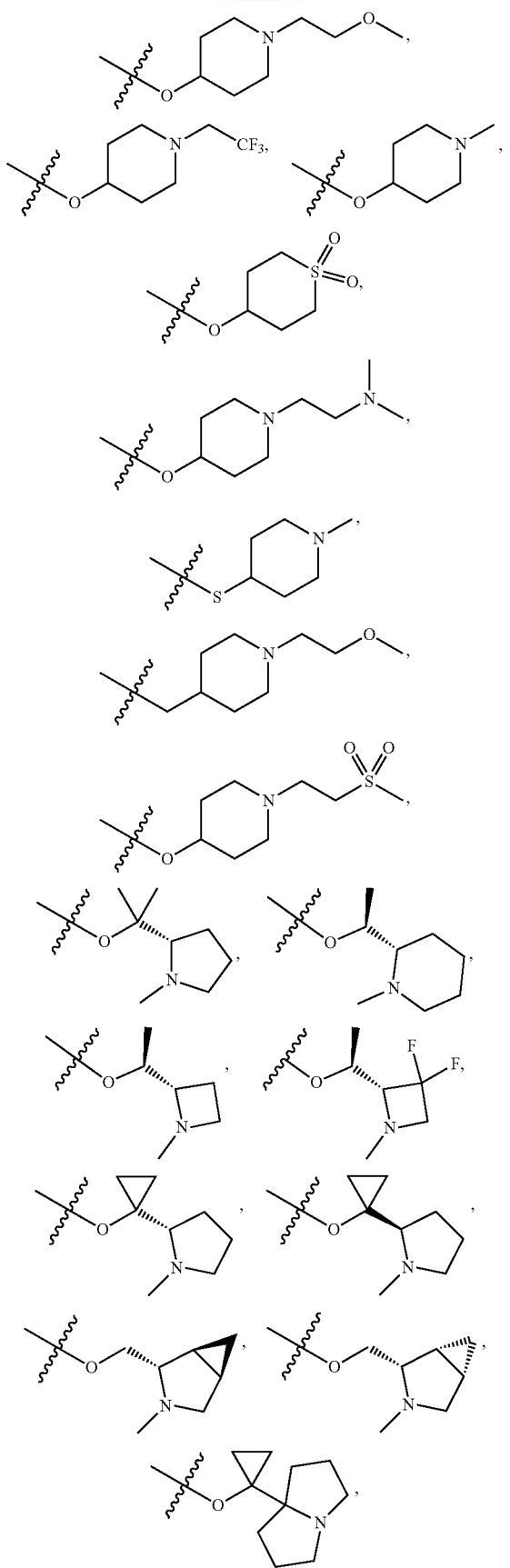
316
-continued
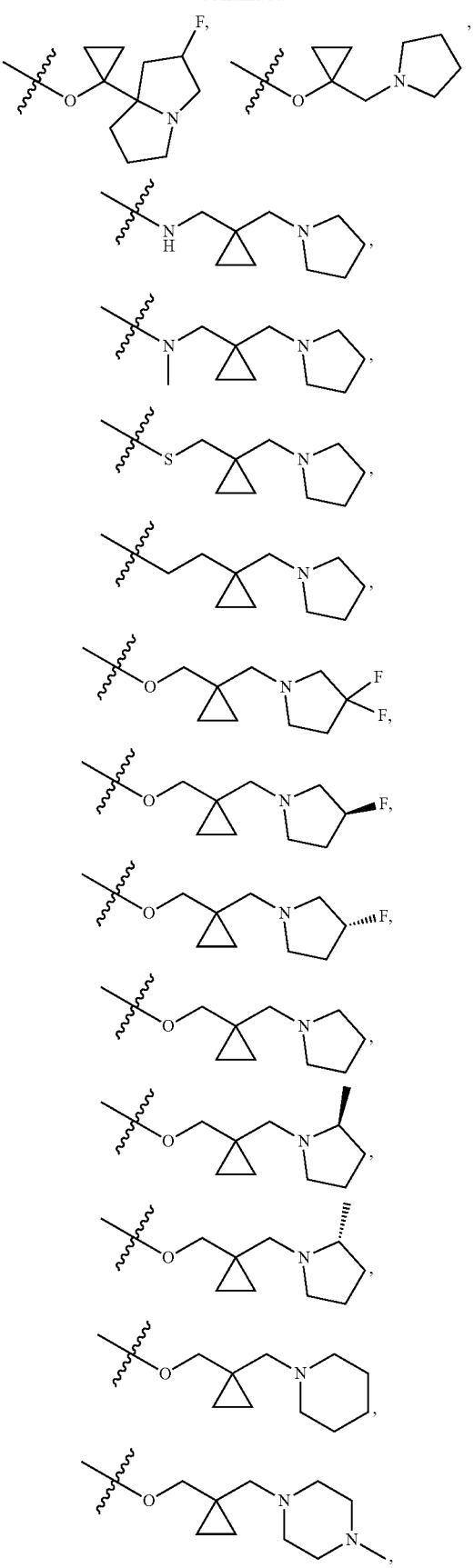

317
-continued
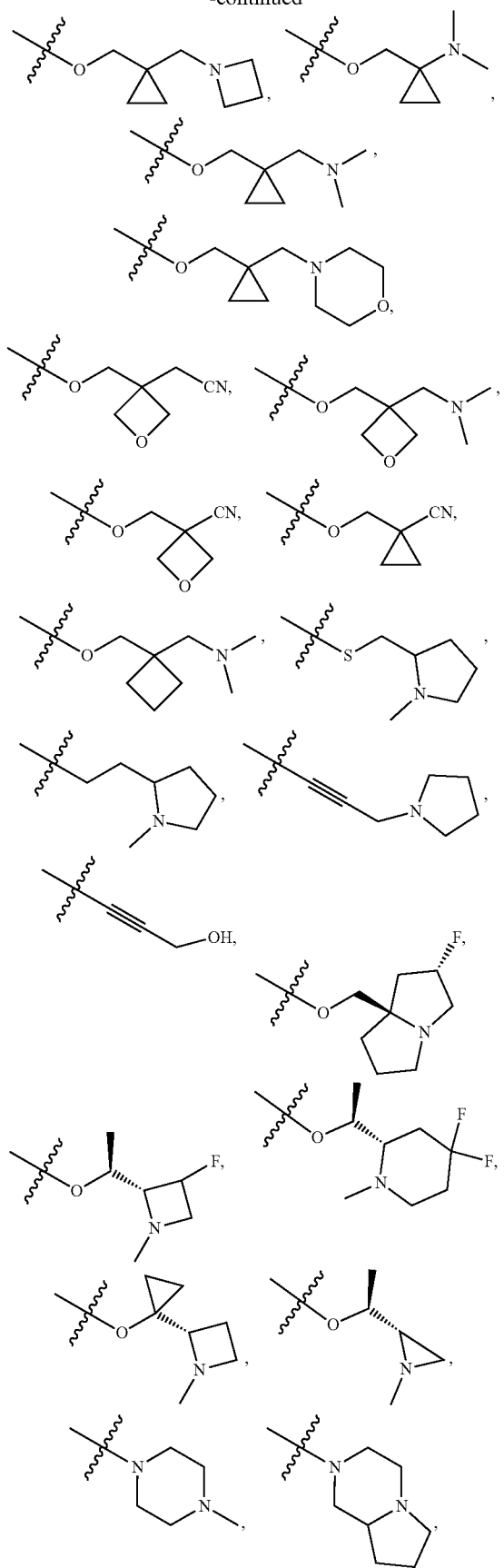
318
-continued
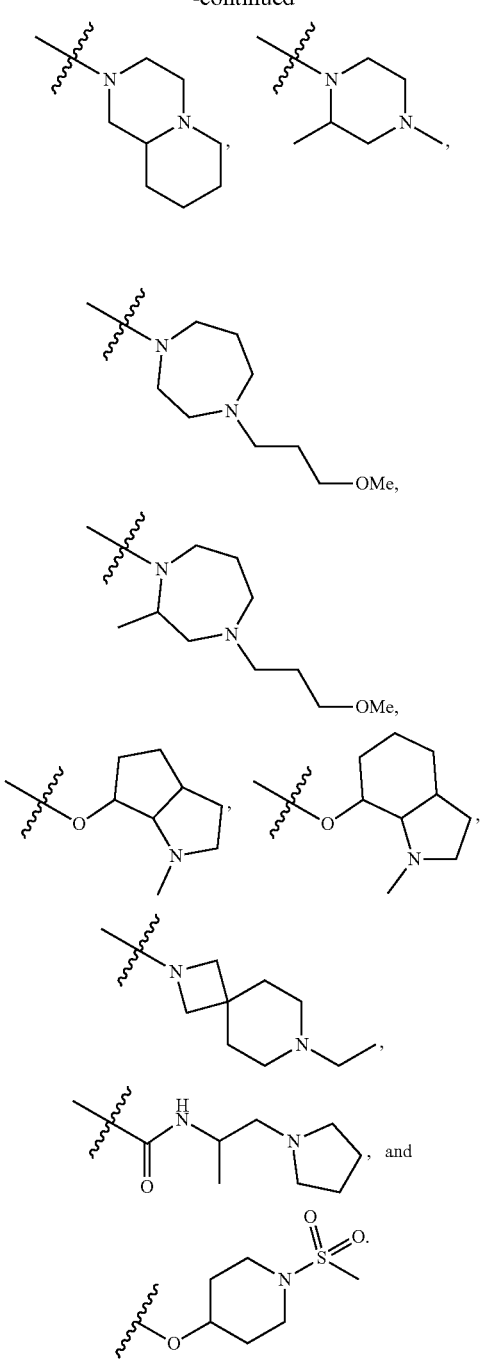
In embodiments of the compounds of the formulae above, or a pharmaceutically acceptable salt or solvate thereof, $R^{17}$ is selected from
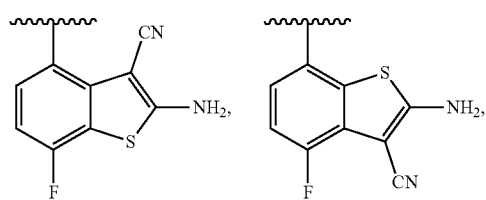

319
-continued

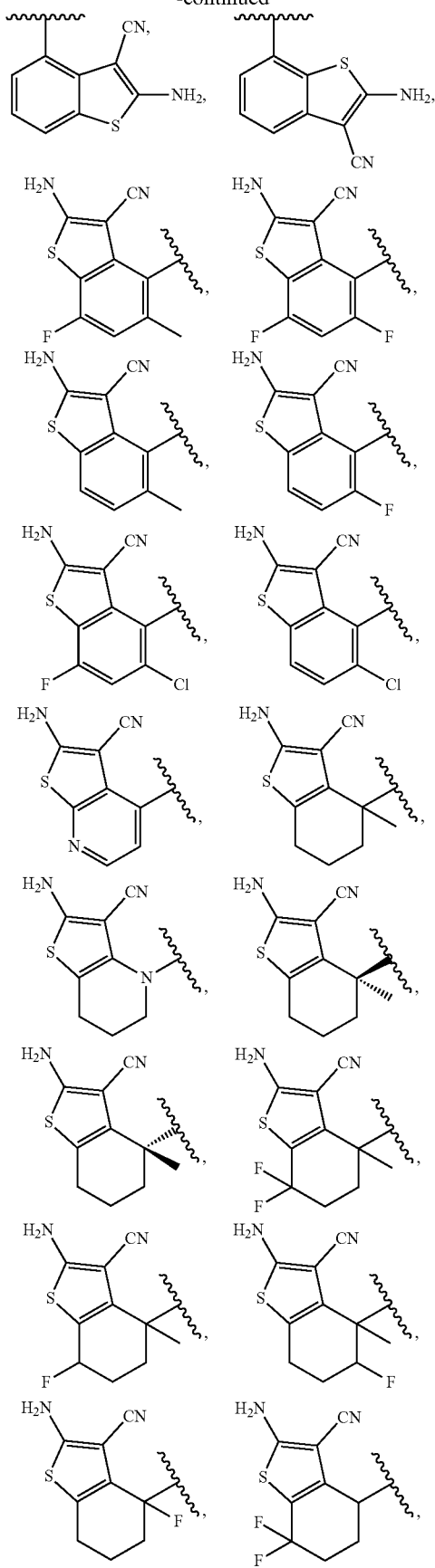

320
-continued

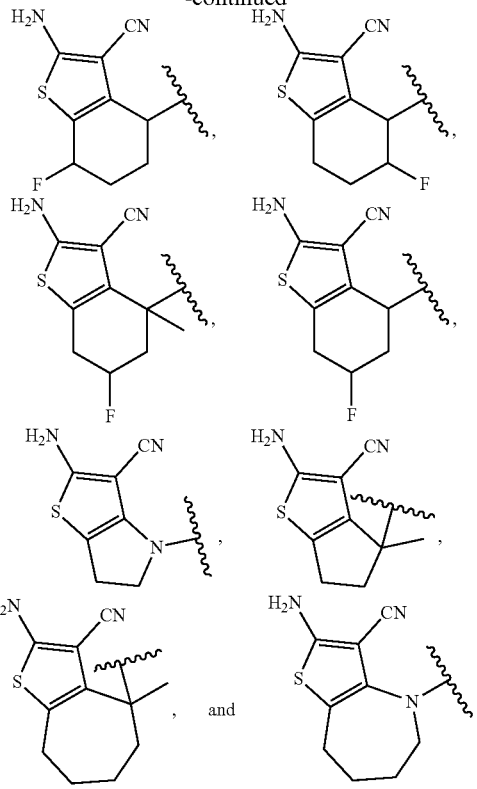

In embodiments of the compounds of the formulae above, or a pharmaceutically acceptable salt or solvate thereof, $R^{17}$ is

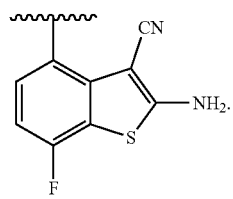 [SMILES: *c1ccc(F)c2sc(N)c(C#N)c12]

In an aspect is provided a compound of Formula (I), or a pharmaceutically acceptable salt or solvate thereof:

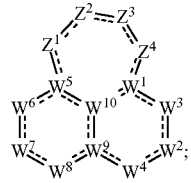

Formula (I)

wherein:
$Z^1$ is O;
$Z^2$ is selected from $C(R^4)(R^{11c})$, $C(R^{11c})(R^{11c})$, $C(R^4)(R^4)$, $C(R^{11c})(R^{11}d)$; and $Z^3$ is selected from $C(R^4)(R^{11c})$, $C(R^{11c})(R^{11c})$, $C(R^4)(R^4)$, $C(R^{11c})(R^{11}d)$; wherein at least one of $Z^2$ and $Z^3$ is $C(R^{11c})(R^{11}d)$;
$Z^4$ is selected from $N(R^4)$, $N(R^{11c})$, and $N(R^{11}d)$;
$W^1$ is $C(R^1)$, C, or N;
$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})$ ($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, and C$_{2-6}$alkynyl are optionally substituted with one, two, or three $R^{20a}$;

$W^2$ is N($R^{2a}$), N, C($R^2$), C($R^2$)($R^{2a}$), S(O)$_2$, or S(O);

$R^2$ is selected from halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12a}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20b}$;

$R^{2a}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20b}$;

$W^3$ is N($R^3$b), N, C($R^3$), C($R^3$)($R^3$a), C(O), S(O)$_2$, or S(O);

$R^3$ and $R^{3a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20c}$;

$R^{3b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$hetero-cycloalkyl, C$_{6-10}$aryl, and C$_{1-9}$heteroaryl are optionally substituted with one, two, or three $R^{20c}$;

$W^4$ is N or N($R^{3c}$);

$R^{3c}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=OX(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20c}$;

$W^5$ is C($R^5$), C, or N;

$R^5$ is selected from hydrogen, halogen, —CN, C$_{1-6}$alkyl, C$_{2-6}$alkenyl, C$_{2-6}$alkynyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, and C$_{2-6}$alkynyl are optionally substituted with one, two, or three $R^{20d}$;

$W^6$ is N($R^6$b), N, C($R^6$), C($R^6$)($R^{6a}$), C(O), S(O), or S(O)$_2$;

$R^6$ and $R^{6a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=OX)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20e}$;

$R^{6b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=OX=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20e}$;

$W^7$ is N($R^7$), C($R^7$), or C($R^7$)($R^{7a}$);

$R^{7a}$ and each $R^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=OX (=NH)N($R^{12}$)($R^{13}$), —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20}f$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6}$-10aryl, and $C_{1-9}$heteroaryl are optionally substituted with one, two, or three $R^{20}f$;

$R^7$ is -$L^7$-$R^{17}$;

$L^7$ is a bond, —O—, —N($R^{7d}$)—, —C(O)—, —S—, —$S(O)_2$—, —S(O)—, —P(O)$R^{7d}$, $CR^7CR^{7c}$, —$OCR^7R^{7c}$—, —$N(R^{7d})CR^7CR^{7c}$—, —$C(O)CR^7CR^{7c}$—, —$SCR^7CR^{7c}$—, —$S(O)_2CR^7CR^{7c}$—, —$S(O)CR^7CR^{7c}$—, —$P(O)R^{7d}CR^7R^{7c}$—, —$CR^7R^1CCR^{7c}R^{7c}$, —$CR^{7c}R^{7c}O$—, —$CR^{7c}R^{7c}N(R^{7d})$—, —$CR^{7c}R^{7c}C(O)$—, —$CR^{7c}R^{7c}S$—, —$CR^{7c}R^{7c}S(O)_2$—, —$CR^7CR^{7c}S(O)$—, —$CR^{7o}R^7cP(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7a}N(R^{7d})$—, —OC(O)—, —$OS(O)_2$—, —OS(O)—, —$OP(O)R^{7d}$—, —C(O)O—, —$S(O)_{20}$—, —S(O)O—, or —$P(O)R^{7a}O$—;

$R^{17}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20}g$;

$W^8$ is $C(R^8)$, $C(R^8)(R^{6a})$, N, $N(R^8b)$, C(O), S(O), or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl , $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$—, heteroaryl are optionally substituted with one, two, or three $R^{20}h$;

$R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$hetero-cycloalkyl, $C_{6-10}$aryl, and $C_{1-9}$heteroaryl are optionally substituted with one, two, or three $R^{20h}$;

$W^9$ is C(R'), C, or N;

$W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$, $R^4$ is -$L^4$-$R^{4n}$;

$L^4$ is a bond, —O—, —$N(R^{4d})$—, —C(O)—, —S—, —$S(O)_2$—, —S(O)—, —$P(O)R^{4d}$—, $CR^4R^4$, —$OCR^4R^{4c}$—, —$N(R^{4d})CR^{4c}R^4$—, —$C(O)CR^4R^{4c}$—, —$SCR^4R^{4c}$—, —$S(O)_2CR^4R^{4c}$—, —$S(O)CR^4R^{4c}$—, —$P(O)R^{4d}CR^4R^{4c}$—, —$CR^4R^4CCR^4R^4$, —$CR^4R^{4c}O$—, —$CR^4R^4CN(R^{4d})$—, —$CR^4R^4CC(O)$—, —$CR^4R^{4c}S$—, —$CR^{4c}S(O)_2$—, —$CR^4R^{4c}S(O)$—, —$CR^4R^4CP(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^{4d}N(R^{4d})$—, —OC(O)—, —$OS(O)_2$—, —OS(O)—, —$OP(O)R^{4d}$—, —C(O)O—, —$S(O)_{20}$—, —S(O)O—, or —$P(O)R^{4d}O$—;

each $R^4$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14}a$, —$S(O)_2R^{14}$, —$S(O)_2N(R^{14})(R^{14})$, —$OCH_2C(O)OR^{14}$, —$OC(O)R^{14}a$, —$N(R^{14})(R^{14})$, —$N(R^{14})C(O)N(R^{14})(R^{14})$, —$N(R^{14})C(O)OR^{14}$, —$N(R^{14})C(O)R^{14}a$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14}a$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14}a$, —$S(O)_2R^{14}$, —$S(O)_2N(R^{14})(R^{14})$, —$OCH_2C(O)OR^{14}$, and —$OC(O)R^{14}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl , are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —N($R^{14}$)C(O)$R^{14}$, —N($R^{14}$)S(O)$_2R^{14}$, —C(O)$R^{14a}$; —S(O)$_2R^{14}$, —S(O)$_2$N($R^{14}$)($R^{14}$), and —OC(O)$R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), and —P(=O)($R^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20}j$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three $R^{20k}$;

each $R^{11}d$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —C($R^{12}$b)$_2$-$C_{3-10}$cycloalkyl, $C_{2-9}$heterocycloalkyl, —C($R^{12}$b)$_2$-$C_{2-9}$heterocycloalkyl, $C_{6-10}$aryl, —C($R^{12}$b)$_2$-$C_{6-10}$aryl, —C($R^{12}$b)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12}$b)$_2$-$C_{3-10}$cycloalkyl, $C_{2-9}$heterocycloalkyl, —C($R^{12}$b)$_2$-$C_{2-9}$heterocycloalkyl, $C_{6-10}$aryl, —C($R^{12}$b)$_2$-$C_{6-10}$aryl, —C($R^{12}$b)$_2$-$C_{1-9}$heteroaryl, and $C_{1-9}$heteroaryl are optionally substituted with one, two, or three $R^{20l}$;

$R^{12}$a is selected from $C_{1-6}$alkyl, $C_{2-6}$alkenyl, $C_{2-6}$alkynyl, $C_{3-10}$cycloalkyl, —C($R^{12}$b)$_2$-$C_{3-10}$cycloalkyl, $C_{2-9}$heterocycloalkyl, —C($R^{12}$b)$_2$-$C_{2-9}$heterocycloalkyl, $C_{6-10}$aryl, —C($R^{12}$b)$_2$-$C_{6-10}$aryl, —C($R^{12}$b)$_2$-$C_{1-9}$heteroaryl, and $C_{1-9}$heteroaryl, wherein $C_{1-6}$alkyl, $C_{2-6}$alkenyl, $C_2$-6alkynyl, $C_{3-10}$cycloalkyl, —C($R^{12}$b)$_2$-$C_{3-10}$cycloalkyl, $C_{2-9}$heterocycloalkyl, —C($R^{12}$b)$_2$-$C_{2-9}$heterocycloalkyl, $C_{6-10}$aryl, —C($R^{126}$)$_2$-$C_6$-10aryl, —C($R^{12}$b)$_2$-$C_{1-9}$heteroaryl, and $C_{1-9}$heteroaryl are optionally substituted with one, two, or three $R^{20l}$;

each $R^{12b}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{14}$ is independently selected from hydrogen, $C_{1-6}$alkyl, and $C_{1-6}$haloalkyl;

each $R^{14}$a is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$; $R^{20b}$, $R^{20c}$; $R^{20d}$, $R^{20e}$, $R^{20f}$, $R^{20g}$, $R^{20h}$, $R^{20i}$, $R^{20j}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), —OCH$_2$C(O)O$R^{22}$, and —OC(O)$R^{25}$, wherein $C_{1-6}$alkyl, $C_{2-6}$alkenyl, $C_{2-6}$alkynyl, $C_{3-10}$cycloalkyl, —CH$_2$-$C_3$-10cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$;

each $R^{20k}$ is independently selected from halogen, oxo, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), —OCH$_2$C(O)O$R^{22}$, and —OC(O)$R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;
each $R^{24}$ is independently selected from H and $C_{1-6}$alkyl;
each $R^{25}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

In some embodiments, the compound of Formula (A), (A'), (A"), (B), (B'), (B"), (C), (C'), or (C") has a formula selected from:

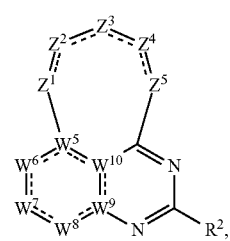
(Da)

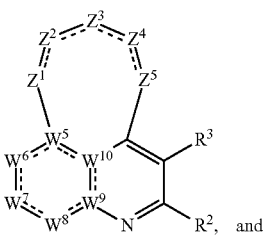
(Dc)

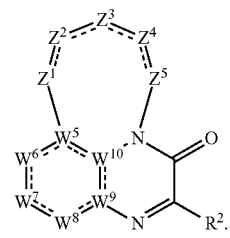
(De)

In some embodiments of a compound of Formula (A), (A'), (A"), (B), (B'), (B"), (C), (C'), or (C"), or a pharmaceutically acceptable salt or solvate thereof, the compound has a formula selected from:

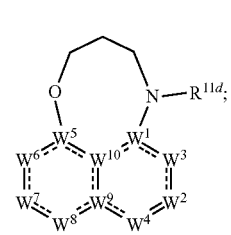
Formula (E)

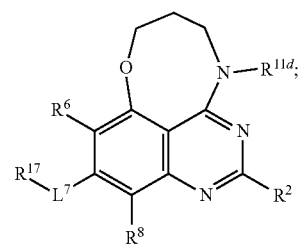
Formula (Ea)

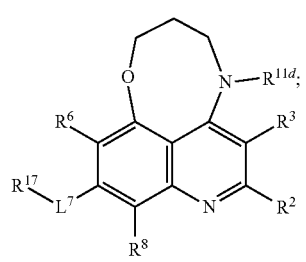
Formula (Eb)

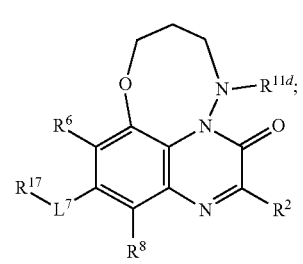
Formula (Ec)

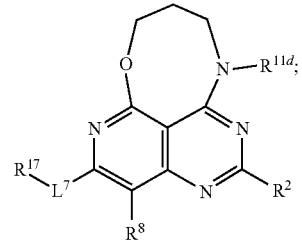
Formula (Ed)

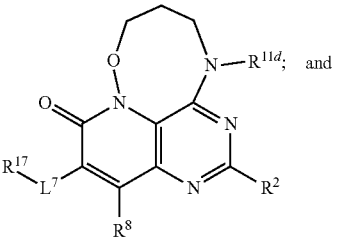
Formula (Ee)

-continued

Formula (Ef)

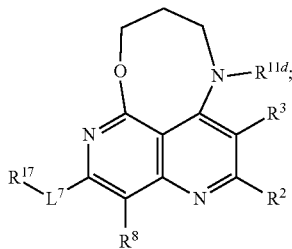

wherein $W^1$, $W^2$, $W^3$, $W^4$, $W^5$, $W^6$, $W^7$, $W^8$, $W^9$, $W^{10}$, $R^2$, $R^4$, $R^6$, $R^8$, $L^7$, $R^{17}$, and $R^{11d}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (F)

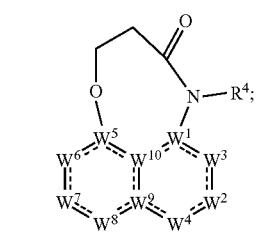

Formula (Fa)

Formula (Fb)

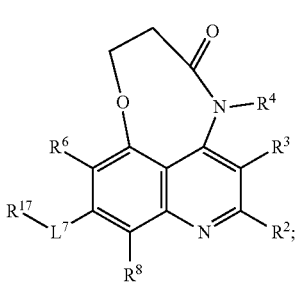

Formula (Fc)

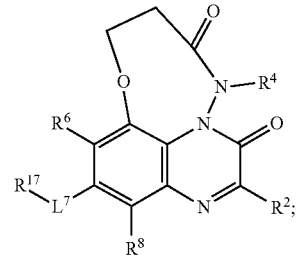

Formula (Fd)


Formula (Fe)


and

Formula (Ff)


wherein $W^1$, $W^2$, $W^3$, $W^4$, $W^5$, $W^6$, $W^7$, $W^5$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"- 1c), (A"-1d), (B"-1d), (C"-1d), (A"-1e), (B"-1e), (C"-1e), (A"-1f), (B"-1f), or (C"-If), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (G)
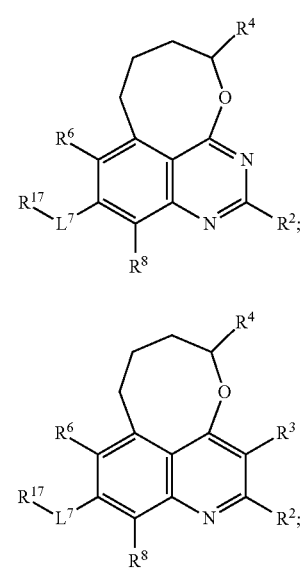

Formula (Ga)
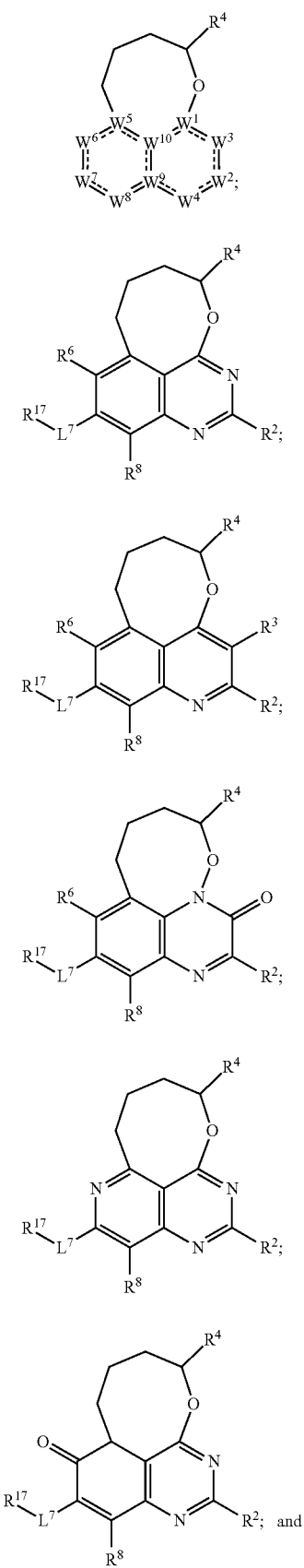

Formula (Gf)
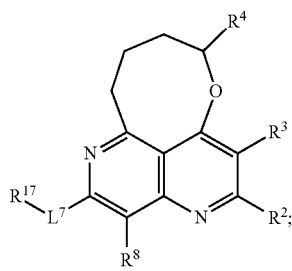

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B""), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (H)
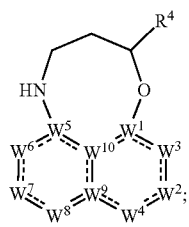

Formula (Ha)

Formula (Hb)
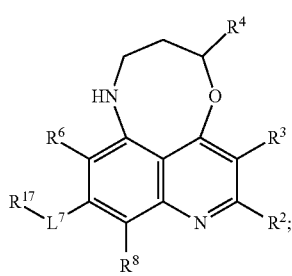

Formula (Hc)
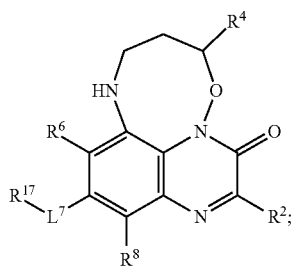

Formula (Hd)
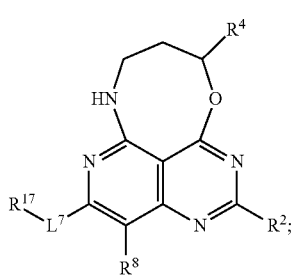

Formula (He)
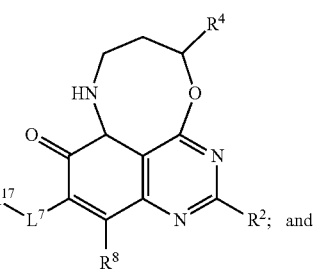

Formula (Hf)
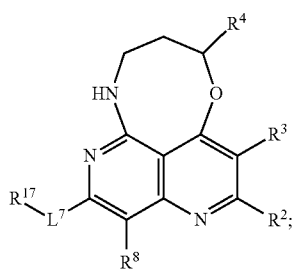

wherein $W^1$, $W^2$, $W^3$, $W^4$, $W^5$, $W^6$, $W^7$, $W^5$, $w''$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''-1c), (B''-1c), (C''-1c), (A''-1d), (B''-1d), (C''-1d), (A''-1e), (B''-1e), (C''-1e), (A''-1f), (B''-1f), or (C''-1f), or any sub-formula or embodiments thereof.

In some embodiments of a compound of Formula (A), (A'), (A''), (B), (B'), (B''), (C), (C'), or (C''), or a pharmaceutically acceptable salt or solvate thereof, the compound has a formula selected from:

Formula (J)
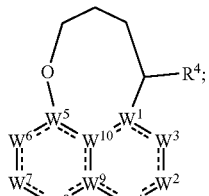

Formula (Ja)
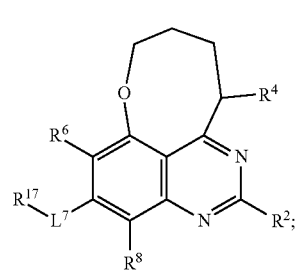

Formula (Jb)
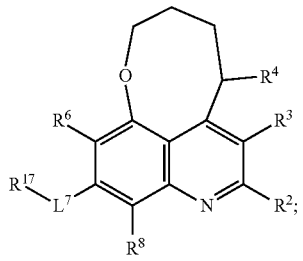

Formula (Jc)
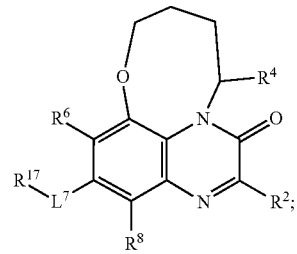

Formula (Jd)
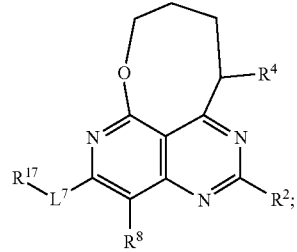

Formula (Je)
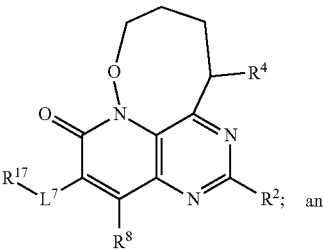

-continued

Formula (Jf)

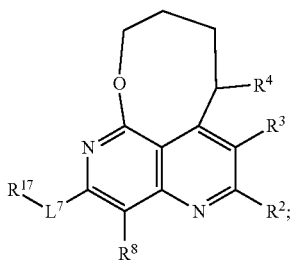

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"- 1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (K)

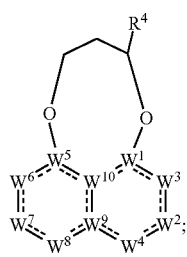

Formula (Ka)

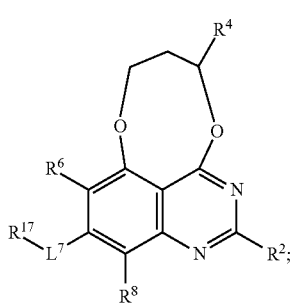

Formula (Kb)

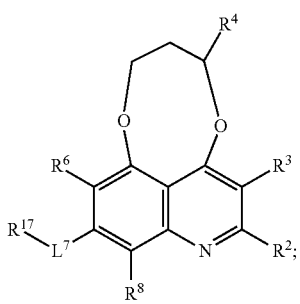

Formula (Kc)

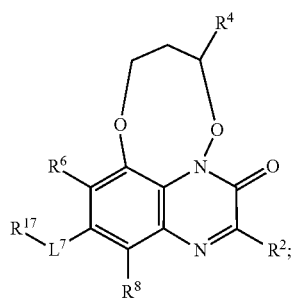

Formula (Kd)

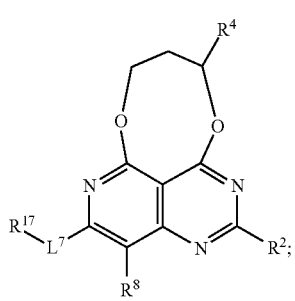

Formula (Ke)

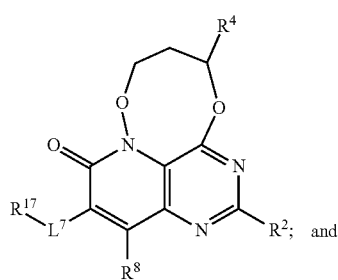

and

Formula (Kf)

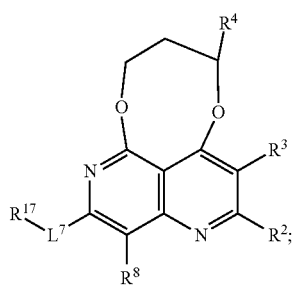

wherein $W^1$, $W^2$, $W^3$, $W^4$, $W^5$, $W^6$, $W^7$, $W^8$, $W^9$, $W^{10}$, $R^2$, $R^3$, $R^1$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (L)

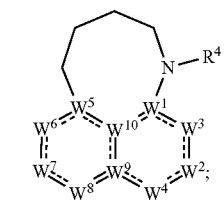

Formula (La)

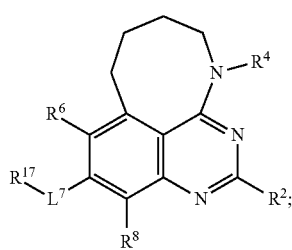

Formula (Lb)

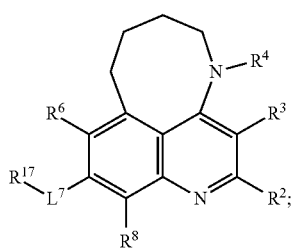

Formula (Lc)

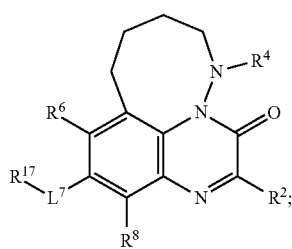

Formula (Ld)

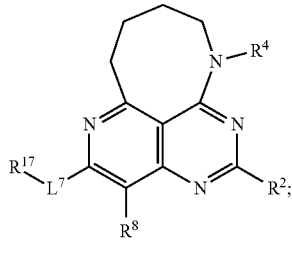

Formula (Le)

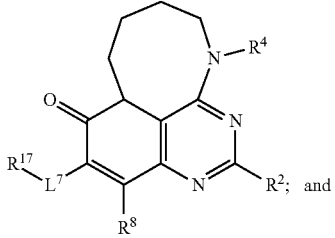
and

Formula (Lf)

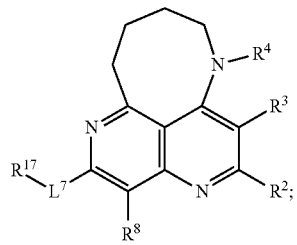

wherein $W^1$, $W^2$, $W^3$, $W^4$, $W^5$, $W^6$, $W^7$, $W^8$, $W^7$, $W^{10}$, $R^2$, $R^3$, $R^1$, $R^6$, $R^8$, $L^7$, $R^{17}$, and $R^{11c}$, are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (M)

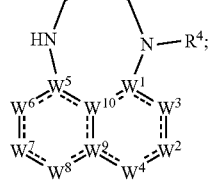

Formula (Ma)


Formula (Mb)

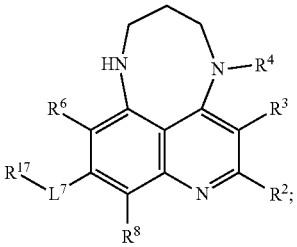

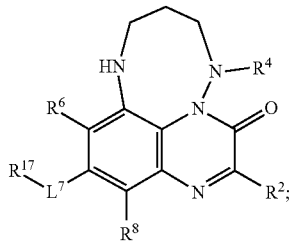
Formula (Mc)

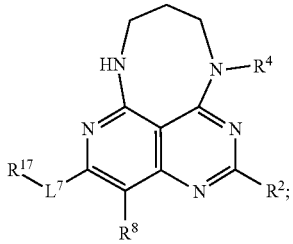
Formula (Md)

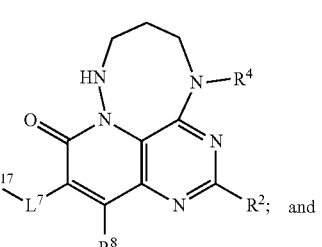
Formula (Me)

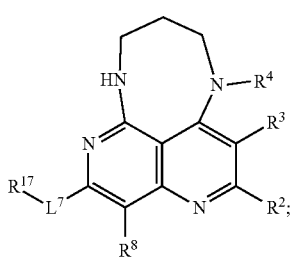
Formula (Mf)

wherein $W^1$, $W^2$, $W^3$, $W^4$, $W^5$, wo, w", $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-If), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any subformula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

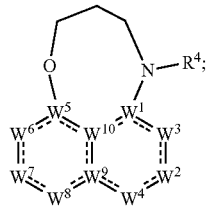
Formula (N)

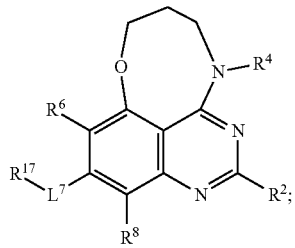
Formula (Na)

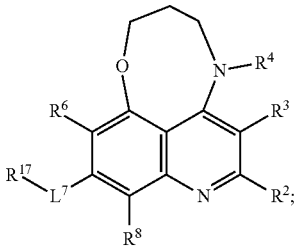
Formula (Nb)

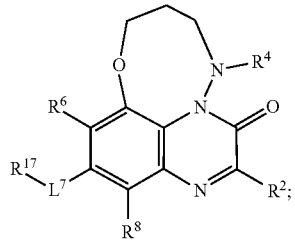
Formula (Nc)

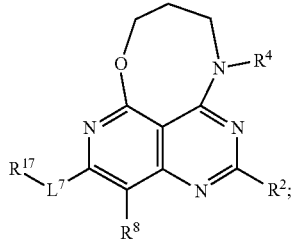
Formula (Nd)

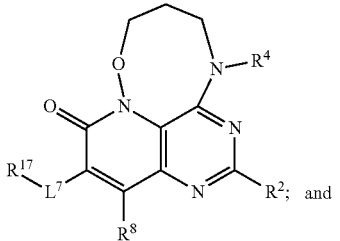
Formula (Ne)

Formula (Nf)

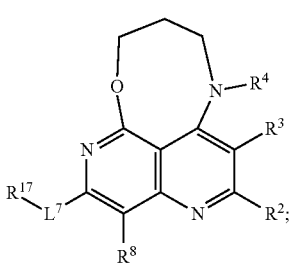

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (O)

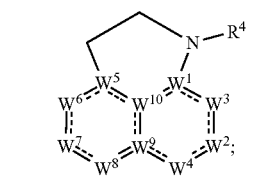

Formula (Oa)

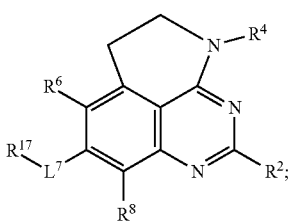

Formula (Ob)

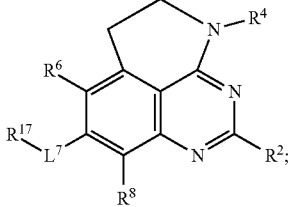

Formula (Oc)

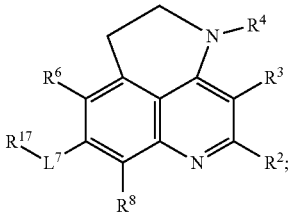

Formula (Od)

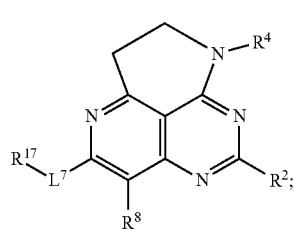

Formula (Oe)

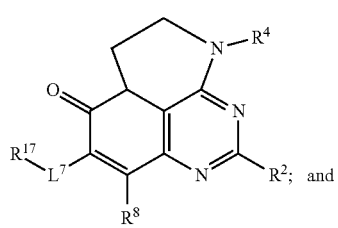

and

Formula (Of)

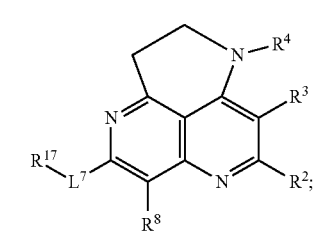

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (P)

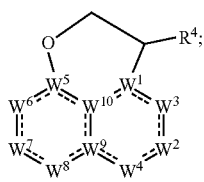

Formula (Pa)

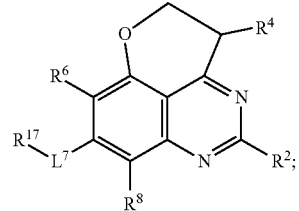

Formula (Pb)
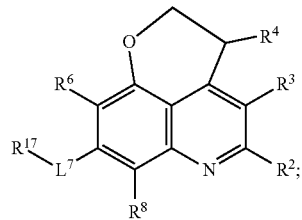

Formula (Pc)
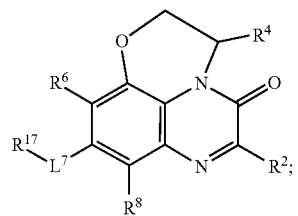

Formula (Pd)
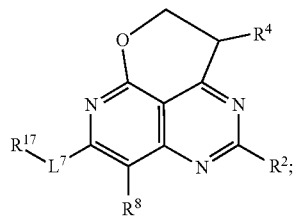

Formula (Pe)
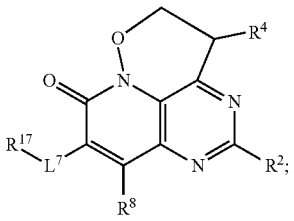

Formula (Pf)
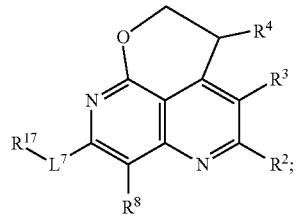

Formula (Q)
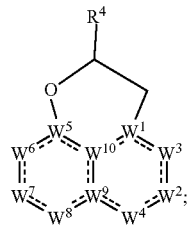

Formula (Qa)
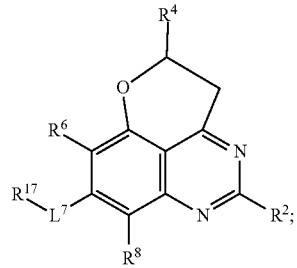

Formula (Qb)
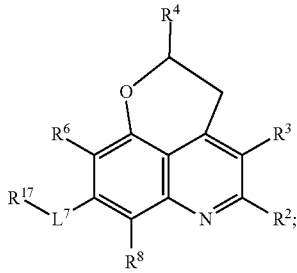

Formula (Qc)
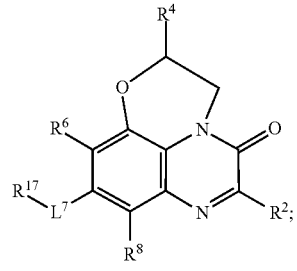

Formula (Qd)
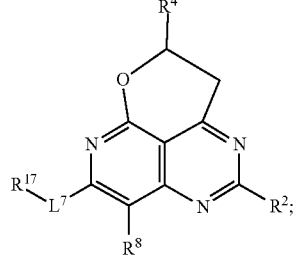

Formula (Qe)
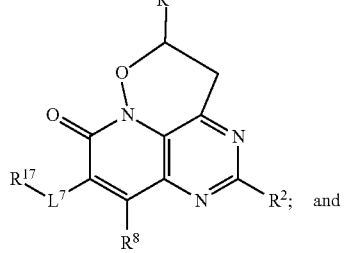

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (Qf)

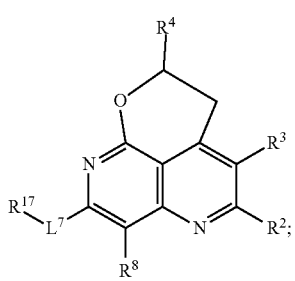

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (R)

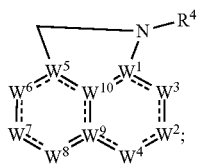

Formula (Ra)

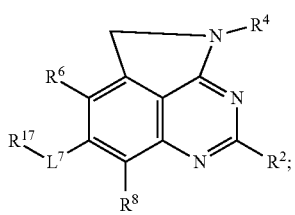

Formula (Rb)

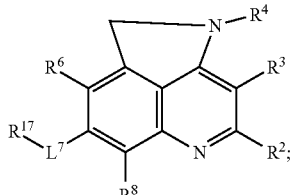

Formula (Rc)

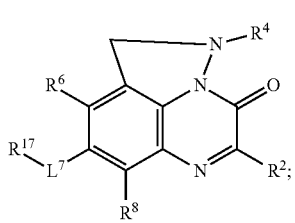

Formula (Rd)

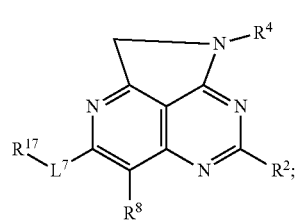

Formula (Re)

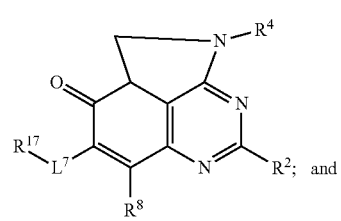

Formula (Rf)

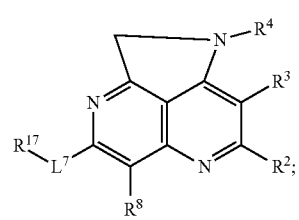

wherein $W^1$, $W^2$, $W^3$, $W^4$, $W^5$, $W^6$, $W^7$, $W^8$, $W^7$, $W^{10}$, $R^2$, $R^3$, $R^4$, $R^6$, $R^8$, $L^7$, and $R^{17}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B""), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (B), (B'), or (B"), or a pharmaceutically acceptable salt or solvate thereof, the compound has a formula selected from:

Formula (S)

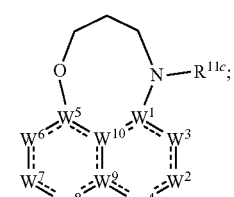

Formula (Sa)

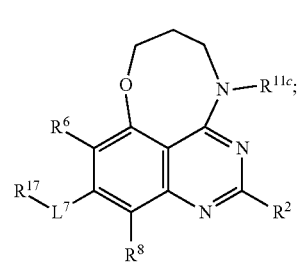

Formula (Sb)

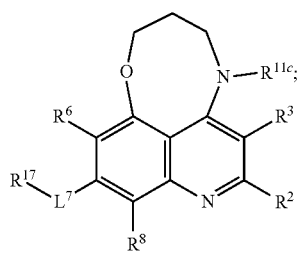

Formula (Sc)

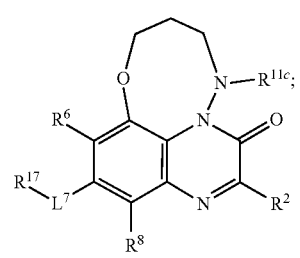

Formula (Sd)

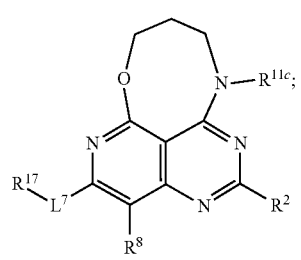

Formula (Se)

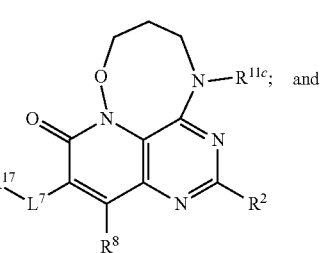

Formula (Sf)

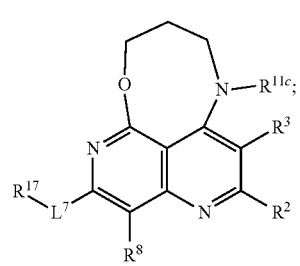

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11c}$ are as described herein for Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or any sub-formula or embodiments thereof.

In some embodiments of a compound of Formula (B), (B'), or (B"), or a pharmaceutically acceptable salt or solvate thereof, the compound has a formula selected from:

Formula (T)

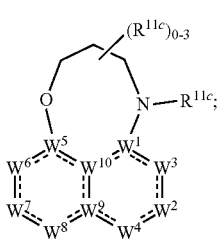

Formula (Ta)

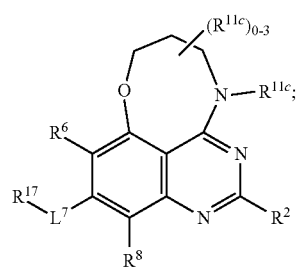

Formula (Tb)

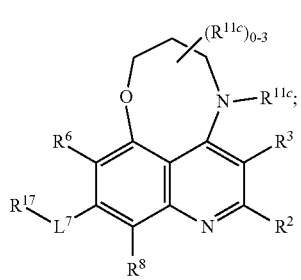

Formula (Tc)

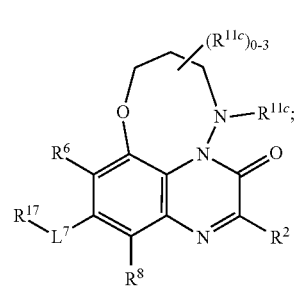

Formula (Td)

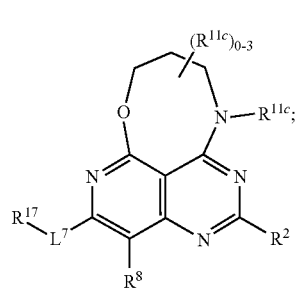

Formula (Te)

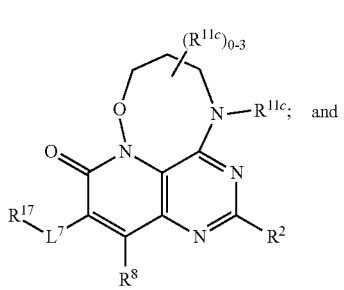

-continued

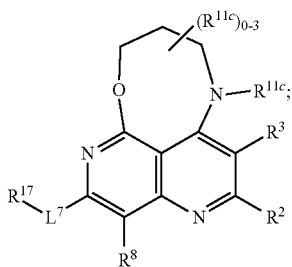

Formula (Tf)

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11c}$ are as described herein for Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or any sub-formula or embodiments thereof.

In some embodiments of a compound of Formula (B), (B'), or (B"), or a pharmaceutically acceptable salt or solvate thereof, the compound has a formula selected from:

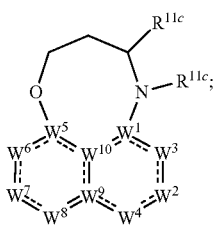

Formula (U)

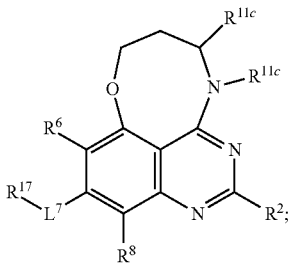

Formula (Ua)

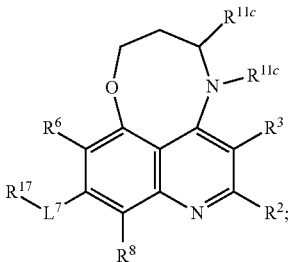

Formula (Ub)

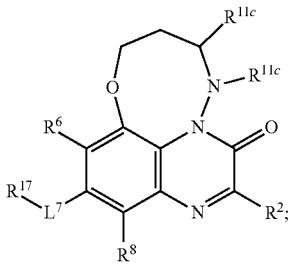

Formula (Uc)

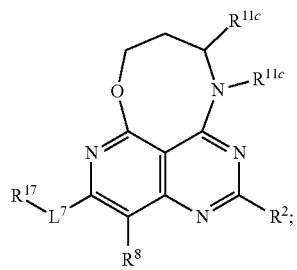

Formula (Ud)

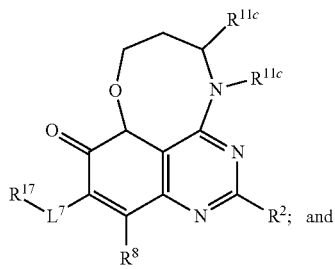

Formula (Ue)

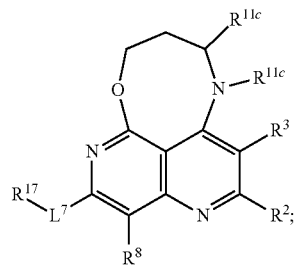

Formula (Uf)

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11c}$ are as described herein for Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or any sub-formula or embodiments thereof.

In some embodiments of a compound of Formula (B), (B'), or (B"), or a pharmaceutically acceptable salt or solvate thereof, the compound has a formula selected from:

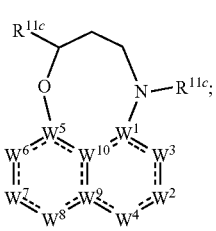

Formula (W)

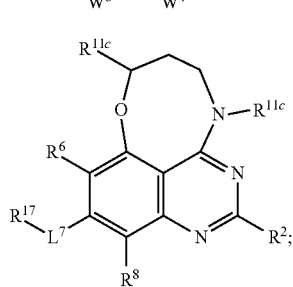

Formula (Wa)

Formula (Wb)
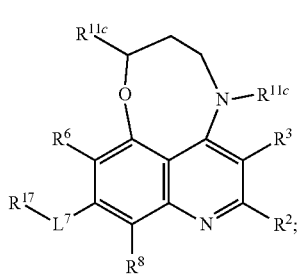

Formula (Wc)
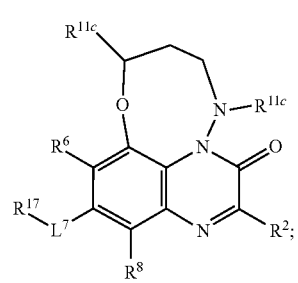

Formula (Wd)
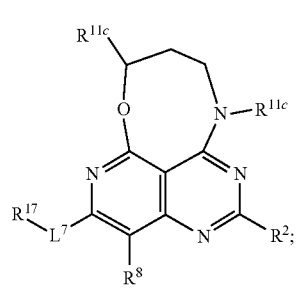

Formula (We)
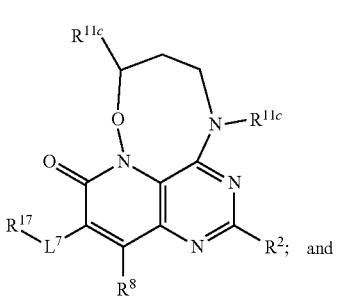

Formula (Wf)
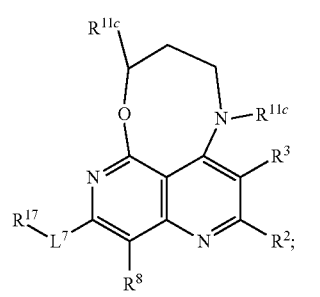

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11c}$ are as described herein for Formula (B), (B-1), (B-1a), (B-1b), (B-1c), (B-1d), (B-1e), (B-1f), (B'), (B'-1), (B'-1a), (B'-1b), (B'-1c), (B'-1d), (B'-1e), (B'-1f), (B"), (B"-1), (B"-1a), (B"-1b), (B"-1c), (B"-1d), (B"-1e), or (B"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (X)
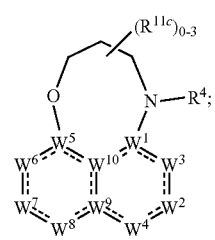

Formula (Xa)
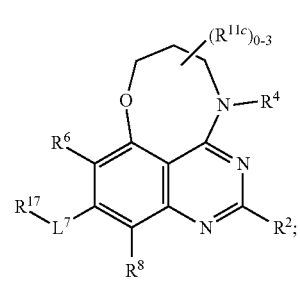

Formula (Xb)
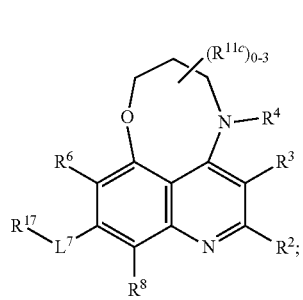

Formula (Xc)
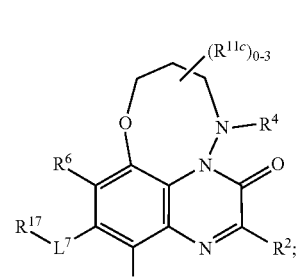

Formula (Xd)
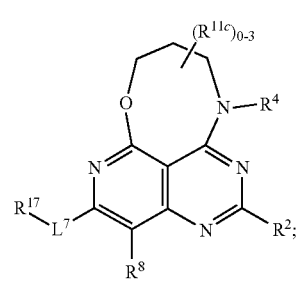

Formula (Xe)

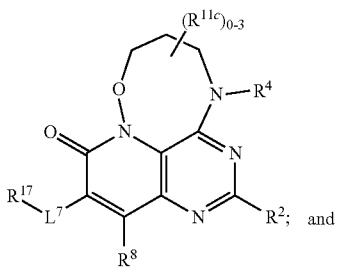

and

Formula (Xf)

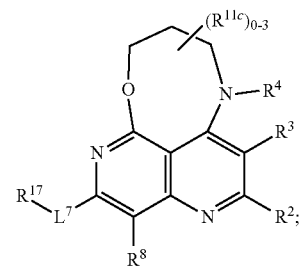

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11c}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

Formula (Y)

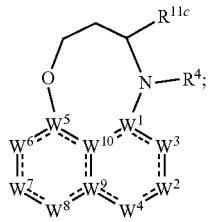

Formula (Ya)

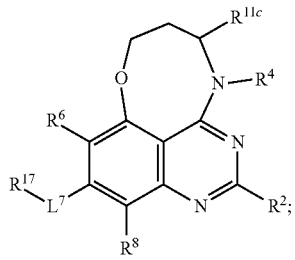

Formula (Yb)

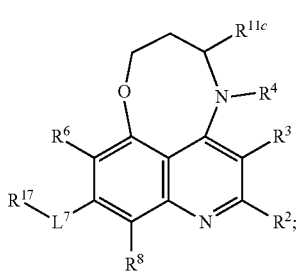

Formula (Yc)

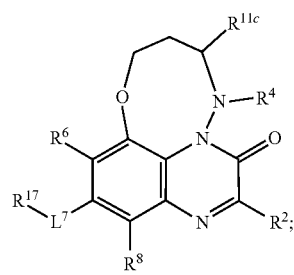

Formula (Yd)

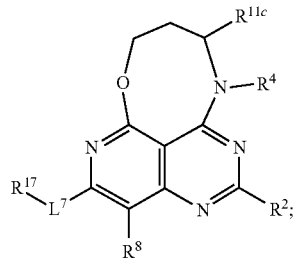

Formula (Ye)

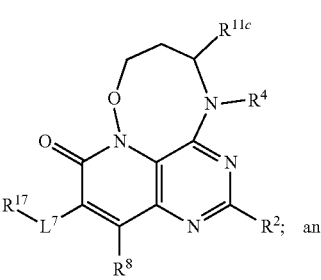

and

Formula (Yf)

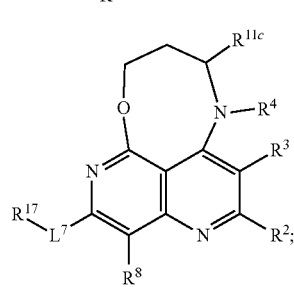

wherein $W^1$, $W^2$, $W^3$, $W^4$, $W^5$, $W^6$, $W^7$, $W^8$, $W^9$, $W^{10}$, $R^2$, $R^3$, $R^1$, $R^6$, $R^8$, $L^7$, $R^{17}$, and $R^{11c}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-

1e), (B"-1e), (C"-1e), (A"-1f), (B"-1f), or (C"-1f), or any sub-formula or embodiments thereof.

In some embodiments of a compound of Formula (A), (A'), (A"), (B), (B'), (B"), (C), (C'), or (C"), or a pharmaceutically acceptable salt or solvate thereof, the compound has a formula selected from:

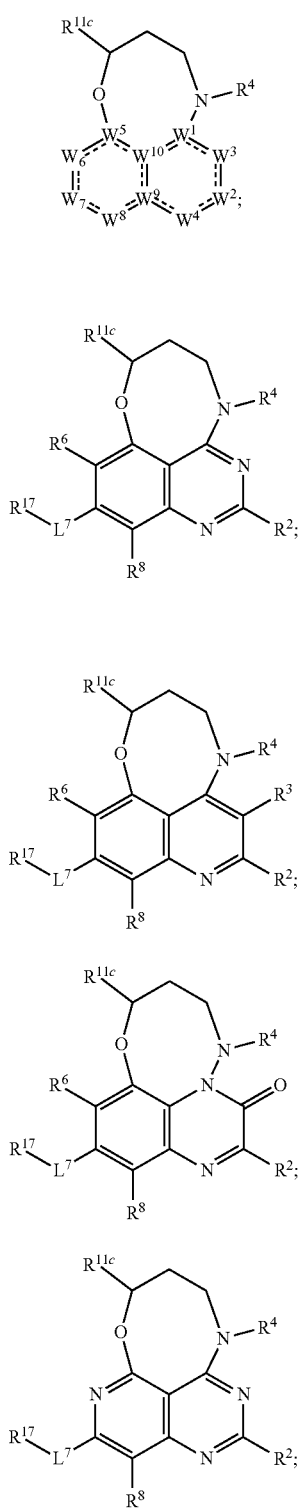

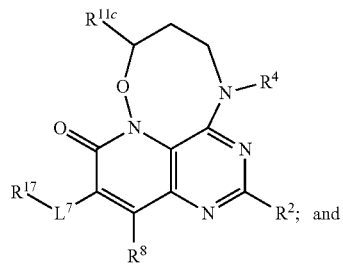

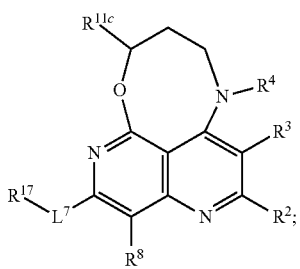

wherein $W^1$, $W^2$, $W^3$, $W^4$, $W^5$, $W^6$, $W^7$, $W^8$, $W^9$, $W^{10}$, $R^2$, $R^3$, $R^4$, $R^6$, $R^8$, $L^7$, $R^{17}$, and $R^{11c}$ are as described herein for Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or any sub-formula or embodiments thereof.

In some embodiments the compound is a compound of Formula (Ta), (Td), (Ua), (Ud), (Wa), (Wd), (Xa), (Xd), (Ya), (Yd), (Za), or (Zd), or a pharmaceutically acceptable salt or solvate thereof, wherein:

$R^2$ is selected from

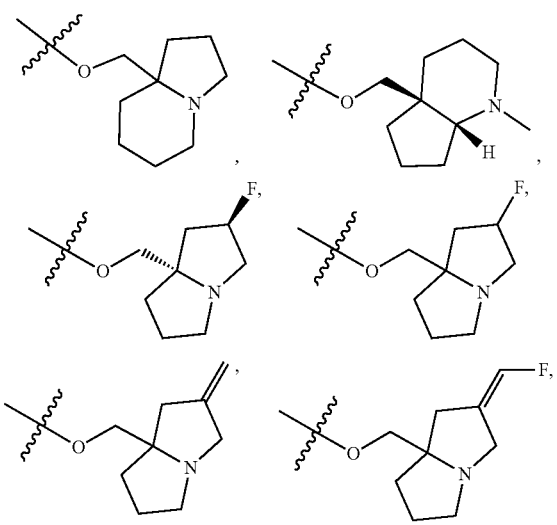

-continued

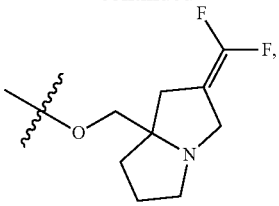

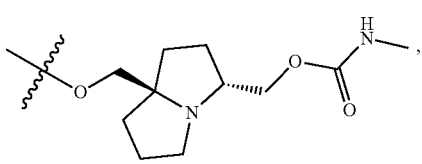

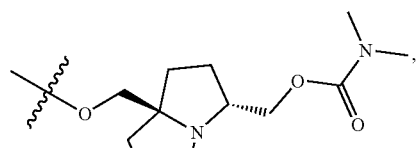

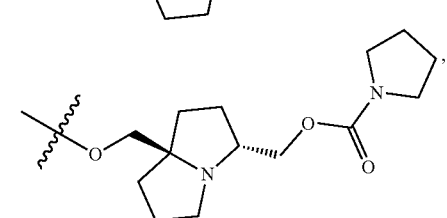

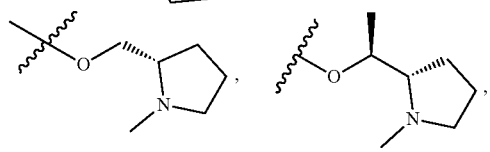

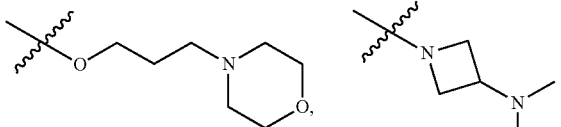

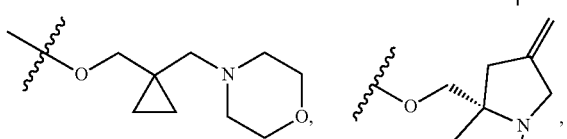

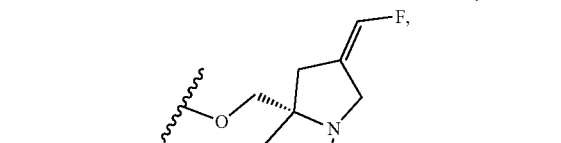

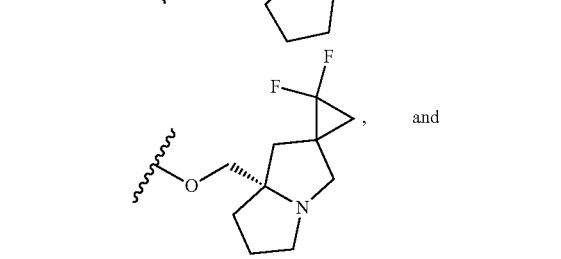
, and

-continued

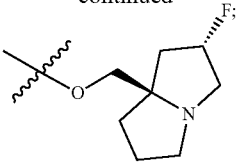

$R^6$ is selected from hydrogen and halogen;
$L^7$ is a bond;
$R^{17}$ is

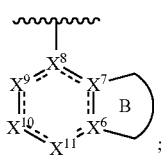
;

Ring B is a 5- or 6-membered heteroaryl ring or 6-membered aryl ring, wherein the 5- or 6-membered heteroaryl ring and 6-membered aryl ring are optionally substituted with one or more $R^{1c}$;
$X^6$, $X^7$, $X^8$, $X^9$, $X^{10}$, and $X^{11}$ are independently $C(R^{1a})$;
each $R^{1a}$ and $R^{1c}$ is independently selected from hydrogen, halogen, —CN, $C_{1-6}$alkyl, $C_{1-6}$haloalkyl, $C_{2-6}$alkynyl, —OH, and —NH$_2$, wherein $C_{1-6}$alkyl and $C_{2-6}$alkynyl are optionally substituted with one, two, or three $R^{20g}$;
$R^8$ is selected from hydrogen and halogen;
$R^4$ is -$L^4$-$R^{4a}$, each $L^4$ is independently selected from a bond and CH$_2$;
each $R^{4a}$ is independently selected from $C_{3-10}$cycloalkyl and $C_{2-9}$heterocycloalkyl, wherein $C_{3-10}$cycloalkyl and $C_{2-9}$heterocycloalkyl are optionally substituted with one, two, three, or four $R^{4b}$;
each $R^{4b}$ is independently selected from halogen, —CN, $C_{1-6}$alkyl, —OR$^{12}$, —N(R$^{12}$)(R$^{13}$), —C(R$^{21b}$)$_2$, —C(O)R$^{12}$, and —C(O)R$^{15}$, wherein $C_{1-6}$alkyl is optionally substituted with one or more $R^{20j}$;
each $R^{11c}$ is independently selected from halogen, —OR$^{12}$, $C_{1-6}$alkyl, $C_{3-12}$cycloalkyl, —CH$_2$-$C_{3-12}$cycloalkyl, $C_{1-11}$heterocycloalkyl, and —CH$_2$-$C_{1-11}$heterocycloalkyl, wherein $C_{1-6}$alkyl, $C_{3-12}$cycloalkyl, —CH$_2$-$C_{3-12}$cycloalkyl, $C_{1-11}$heterocycloalkyl, and —CH$_2$-$C_{1-11}$heterocycloalkyl are optionally substituted with one, two, or three $R^{20k}$;
each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20t}$;
each $R^{13}$ is independently selected from hydrogen and $C_{1-6}$alkyl;
each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20m}$;
each $R^{20j}$ is independently selected from halogen and —CN;
each $R^{20k}$ is independently selected from halogen, —CN, —OR$^{21}$, and —N(R$^{22}$)(R$^{23}$);
each $R^{20t}$ is independently selected from halogen, —CN, $C_{3-10}$cycloalkyl, —OR$^{21}$, and —N(R$^{22}$)(R$^{23}$);
each $R^{20m}$ is independently selected from halogen, —CN, $C_{3-10}$cycloalkyl, —OR$^{21}$, and —N(R$^{22}$)(R$^{23}$);
each $R^{21}$ is independently selected from H and $C_{1-6}$alkyl;

each $R^{22}$ is independently selected from H and $C_{1-6}$alkyl;

each $R^{23}$ is independently selected from H and $C_{1-6}$alkyl; and

----- indicates a single or double bond such that all valences are satisfied. All variables not described in the embodiment immediately above are as described for a compound of formula (Ta), (Td), (Ua), (Ud), (Wa), (Wd), (Xa), (Xd), (Ya), (Yd), (Za), or (Zd), or an embodiment thereof.

In some embodiments the compound is a compound of Formula (Ta), (Td), (Ua), (Ud), (Wa), (Wd), (Xa), (Xd), (Ya), (Yd), (Za), or (Zd), or a pharmaceutically acceptable salt or solvate thereof:

wherein $Y^2$ is selected from

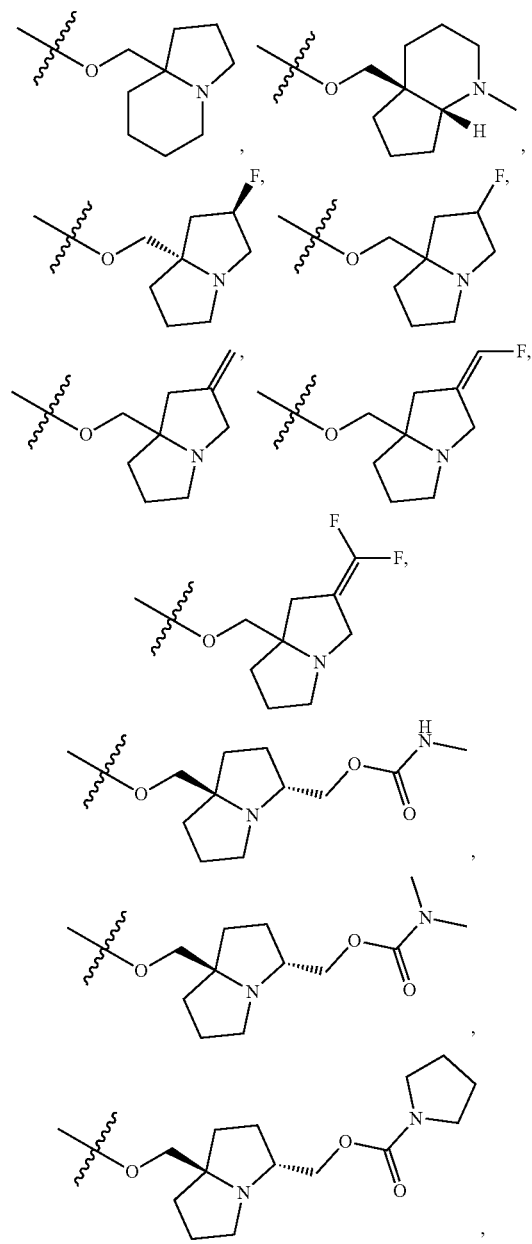

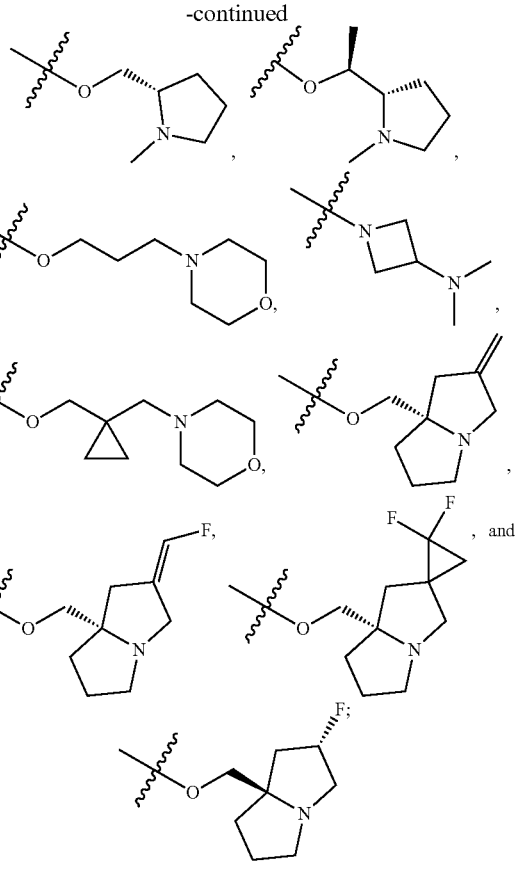

$R^6$ is selected from hydrogen and halogen;

$L^7$ is a bond;

$R^{17}$ is

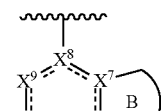

Ring B is a 5- or 6-membered heteroaryl ring or 6-membered aryl ring, wherein the 5- or 6-membered heteroaryl ring and 6-membered aryl ring are optionally substituted with one or more $R^{1c}$;

$X^6$, $X^7$, $X^8$, $X^9$, $X^{10}$, and $X^{11}$ are independently $C(R^{1a})$;

each $R^{1a}$ and $R^{1c}$ is independently selected from hydrogen, halogen, —CN, $C_{1-6}$alkyl, $C_{1-6}$haloalkyl, $C_{2-6}$alkynyl, —OH, and —NH$_2$, wherein $C_{1-6}$alkyl and $C_{2-6}$alkynyl are optionally substituted with one, two, or three $R^{20g}$;

$R^8$ is selected from hydrogen and halogen;

$R^4$ is -$L^4$-$R^{4a}$;

each $L^4$ is independently selected from a bond and $CH_2$;

each $R^{4a}$ is independently selected from $C_{3-10}$cycloalkyl and $C_{2-9}$heterocycloalkyl, wherein $C_{3-10}$cycloalkyl and $C_{2-9}$heterocycloalkyl are optionally substituted with one, two, three, or four $R^{4b}$;

each $R^{4b}$ is independently selected from halogen, —CN, $C_{1-6}$alkyl, —OR$^{12}$, —N(R$^{12}$)(R$^{13}$), —C(R$^{21b}$)$_2$, —C(O)R$^{12}$, and —C(O)R$^{15}$, wherein $C_{1-6}$alkyl is optionally substituted with one or more $R^{20j}$;

each $R^{11c}$ is independently selected from halogen, —$OR^{12}$, $C_{1-6}$alkyl, and $C_{1-11}$heterocycloalkyl, wherein $C_{1-6}$alkyl and $C_{1-11}$heterocycloalkyl are optionally substituted with one, two, or three $R^{20k}$;

each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20t}$;

each $R^{13}$ is independently selected from hydrogen and $C_{1-6}$alkyl;

each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20m}$;

each $R^{20j}$ is independently selected from halogen and —CN;

each $R^{20k}$ is independently selected from halogen, —CN, and —$OR^{21}$;

each $R^{20t}$ is independently selected from halogen, —CN, $C_{3-10}$cycloalkyl, —$OR^{21}$, and —$N(R^{22})(R^{23})$;

each $R^{20m}$ is independently selected from halogen, —CN, $C_{3-10}$cycloalkyl, —$OR^{21}$, and —$N(R^{22})(R^{23})$;

each $R^{21}$ is independently selected from H and $C_{1-6}$alkyl;
each $R^{22}$ is independently selected from H and $C_{1-6}$alkyl;
each $R^{23}$ is independently selected from H and $C_{1-6}$alkyl; and ----- indicates a single or double bond such that all valences are satisfied. All variables not described in the embodiment immediately above are as described for a compound of formula (Ta), (Td), (Ua), (Ud), (Wa), (Wd), (Xa), (Xd), (Ya), (Yd), (Za), or (Zd), or an embodiment thereof.

In some embodiments the compound is a compound of Formula (Ta), (Td), (Ua), (Ud), (Wa), (Wd), (Xa), (Xd), (Ya), (Yd), (Za), or (Zd), or a pharmaceutically acceptable salt or solvate thereof:
wherein
$R^2$ is selected from

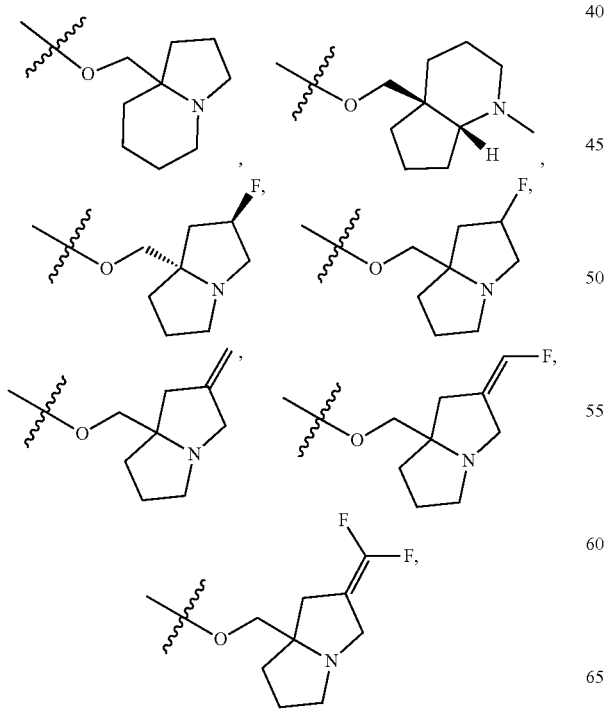

-continued

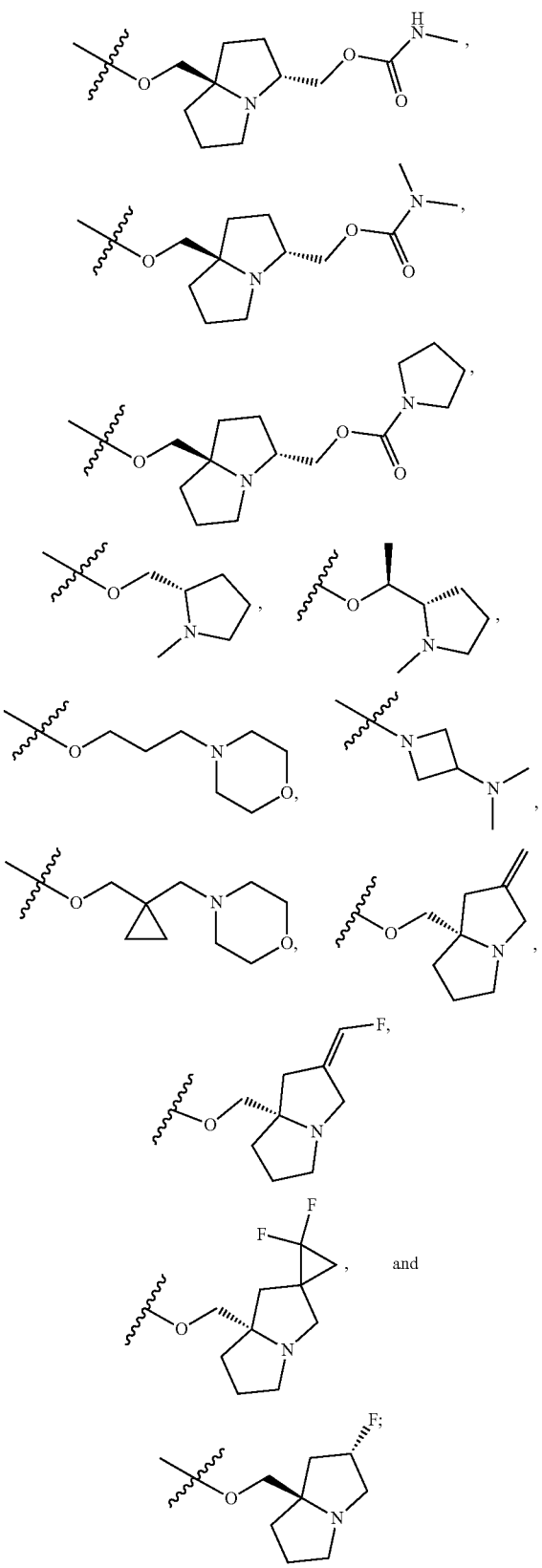

and $R^6$ is selected from hydrogen and halogen;
$L^7$ is a bond;

R[17] selected from

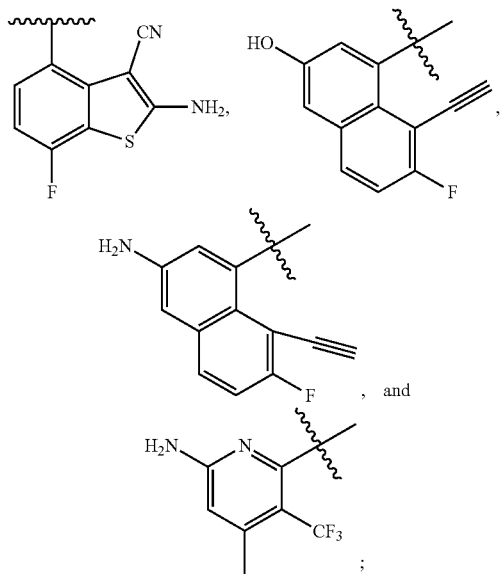

R[8] is selected from hydrogen and halogen;
R[4] is -L[4]-R[4a];
each L[4] is independently selected from a bond, CH$_2$;
each R[4a] is independently selected from C$_{3-10}$cycloalkyl and C$_{2-9}$heterocycloalkyl, wherein C$_{3-10}$cycloalkyl and C$_{2-9}$heterocycloalkyl are optionally substituted with one, two, three, or four R[4b];
each R[4b] is independently selected from halogen, —CN, C$_{1-6}$alkyl, —OR[12], —N(R[12])(R[13]), —C(R[21b])$_2$, —C(O)R[12], and —C(O)R[15], wherein C$_{1-6}$alkyl is optionally substituted with one or more R[20j];
each R[11c] is independently selected from halogen, —OR[12], C$_{1-6}$alkyl, C$_{3-12}$cycloalkyl, —CH$_2$-C$_{3-12}$cycloalkyl, C$_{1-11}$heterocycloalkyl, and —CH$_2$-C$_{1-11}$heterocycloalkyl, wherein C$_{1-6}$alkyl, C$_{3-12}$cycloalkyl, —CH$_2$-C$_{3-12}$cycloalkyl, C$_{1-11}$heterocycloalkyl, and —CH$_2$-C$_{1-11}$heterocycloalkyl are optionally substituted with one, two, or three R[20k];
each R[12] is independently selected from hydrogen, C$_{1-6}$alkyl, and C$_{2-9}$heterocycloalkyl, wherein C$_{1-6}$alkyl, and C$_{2-9}$heterocycloalkyl are optionally substituted with one, two, or three R[20l];
each R[13] is independently selected from hydrogen and C$_{1-6}$alkyl;
each R[15] is independently selected from C$_{1-6}$alkyl and C$_{2-9}$heterocycloalkyl, wherein C$_{1-6}$alkyl and C$_{2-9}$heterocycloalkyl are optionally substituted with one, two, or three R[20m];
each R[20j] is independently selected from halogen and —CN;
each R[20k] is independently selected from halogen, —CN, —OR[21], and —N(R[22])(R[23]);
each R[20l] is independently selected from halogen, —CN, C$_{3-10}$cycloalkyl, —OR[21], and —N(R[22])(R[23]);
each R[20m] is independently selected from halogen, —CN, C$_{3-10}$cycloalkyl, —OR[21], and —N(R[22])(R[23]);
each R[21] is independently selected from H and C$_{1-6}$alkyl;
each R[22] is independently selected from H and C$_{1-6}$alkyl;
each R[23] is independently selected from H and C$_{1-6}$alkyl; and ----- indicates a single or double bond such that all valences are satisfied. All variables not described in the embodiment immediately above are as described for a compound of formula (Ta), (Td), (Ua), (Ud), (Wa), (Wd), (Xa), (Xd), (Ya), (Yd), (Za), or (Zd), or an embodiment thereof.

In some embodiments the compound is a compound of Formula (Ta), (Td), (Ua), (Ud), (Wa), (Wd), (Xa), (Xd), (Ya), (Yd), (Za), or (Zd), or a pharmaceutically acceptable salt or solvate thereof:
wherein
R[2] is selected from

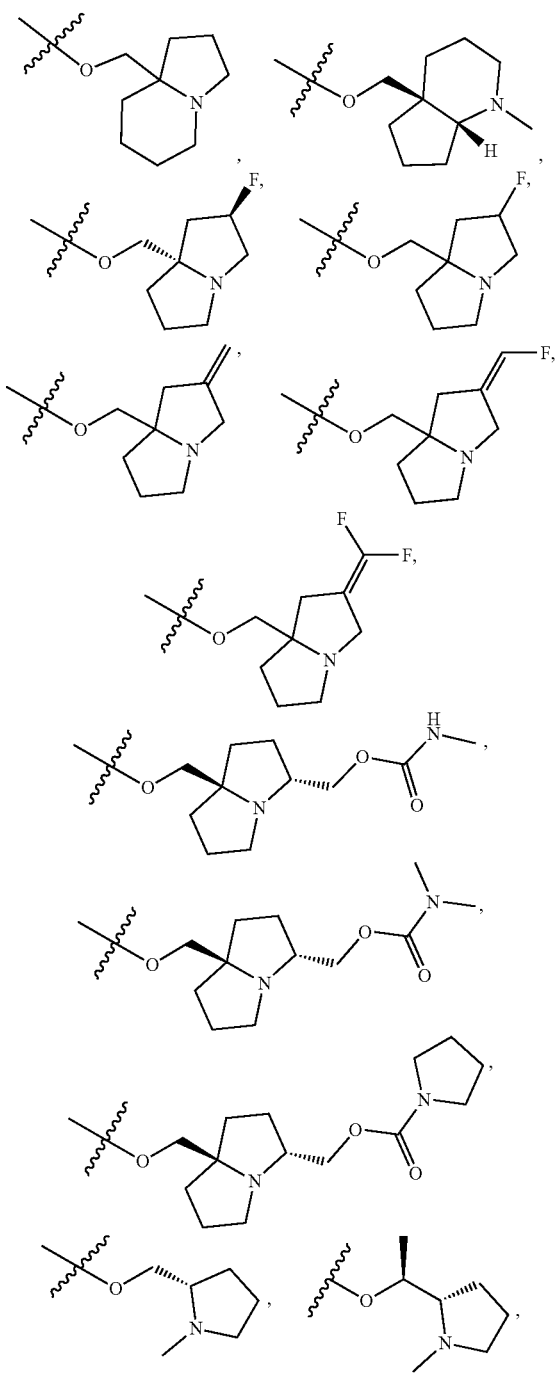

365
-continued

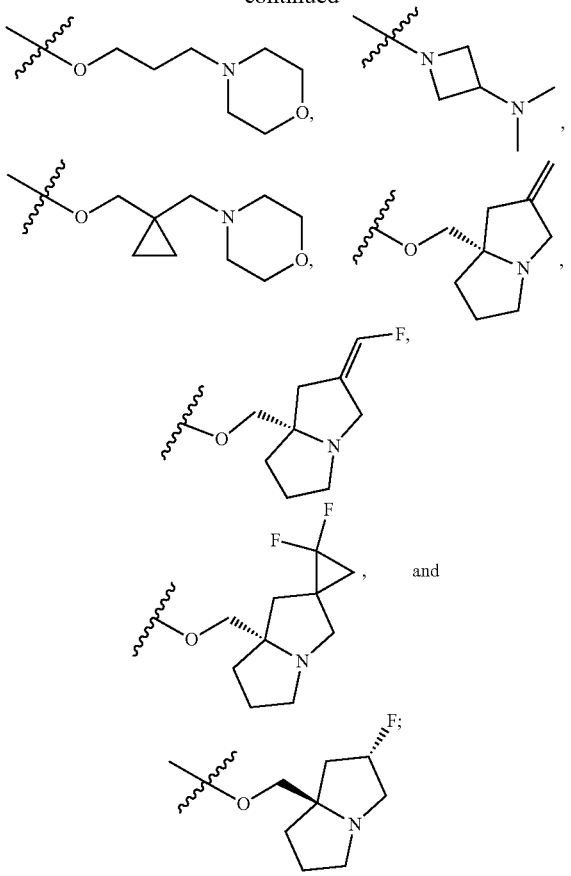

, and $R^6$ is selected from hydrogen and halogen;
$L^7$ is a bond;
$R^{17}$ selected from

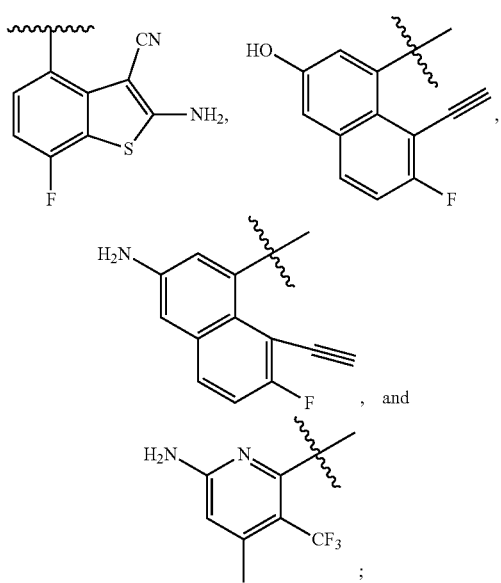

, and $R^8$ is selected from hydrogen and halogen;
$R^4$ is -$L^4$-$R^{4a}$;
each $L^4$ is independently selected from a bond and CH$_2$;

366 each $R^{4a}$ is independently selected from $C_{3-10}$cycloalkyl and $C_{2-9}$heterocycloalkyl, wherein $C_{3-10}$cycloalkyl and $C_{2-9}$heterocycloalkyl are optionally substituted with one, two, three, or four $R^{4b}$;

each $R^{4b}$ is independently selected from halogen, —CN, $C_{1-6}$alkyl, —OR$^{12}$, —N(R$^{12}$)(R$^{13}$), —C(R$^{21b}$)$_2$, —C(O)R$^{12}$, and —C(O)R$^{15}$, wherein $C_{1-6}$alkyl is optionally substituted with one or more $R^{20j}$;

each $R^{11c}$ is independently selected from halogen, —OR$^{12}$, $C_{1-6}$alkyl, and $C_{1-11}$heterocycloalkyl, wherein $C_{1-6}$alkyl and $C_{1-11}$heterocycloalkyl are optionally substituted with one, two, or three $R^{20k}$;

each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20t}$;

each $R^{13}$ is independently selected from hydrogen and $C_{1-6}$alkyl;

each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20m}$;

each $R^{20j}$ is independently selected from halogen and —CN;

each $R^{20k}$ is independently selected from halogen, —CN, and —OR$^{21}$;

each $R^{20t}$ is independently selected from halogen, —CN, $C_{3-10}$cycloalkyl, —OR$^{21}$, and —N(R$^{22}$)(R$^{23}$);

each $R^{20m}$ is independently selected from halogen, —CN, $C_{3-10}$cycloalkyl, —OR$^{21}$, and —N(R$^{22}$)(R$^{23}$);

each $R^{21}$ is independently selected from H and $C_{1-6}$alkyl;
each $R^{22}$ is independently selected from H and $C_{1-6}$alkyl;
each $R^{23}$ is independently selected from H and $C_{1-6}$alkyl; and ----- indicates a single or double bond such that all valences are satisfied. All variables not described in the embodiment immediately above are as described for a compound of formula (Ta), (Td), (Ua), (Ud), (Wa), (Wd), (Xa), (Xd), (Ya), (Yd), (Za), or (Zd), or an embodiment thereof.

In some embodiments the compound is a compound of Formula (Ta), (Td), (Ua), (Ud), (Wa), or (Wd), or a pharmaceutically acceptable salt or solvate thereof:
wherein
$R^6$ and $R^8$ are independently selected from hydrogen and halogen;
$L^7$ is a bond;
$R^{17}$ is selected from:

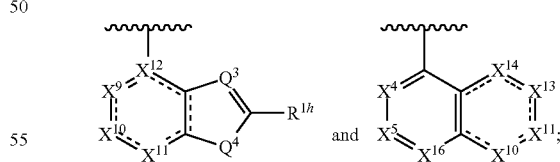

$Q^3$ is N or C(R$^{1d}$); $Q^4$ is S;
$X^4$, $X^5$, and $X^{16}$ are independently selected from C(R$^{1a}$) or N;
$X^9$ is C(R$^{1a}$); $X^{10}$, $X^{11}$, $X^{13}$, and $X^{14}$ are independently C(R$^{1a}$) or N; $X^{12}$ is C;
each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, and —C(O)CH$_3$;

$R^{1d}$ is selected from hydrogen, —CN, $C_{1-4}$alkyl, and $C_{1-4}$haloalkyl;

$R^2$ is selected from

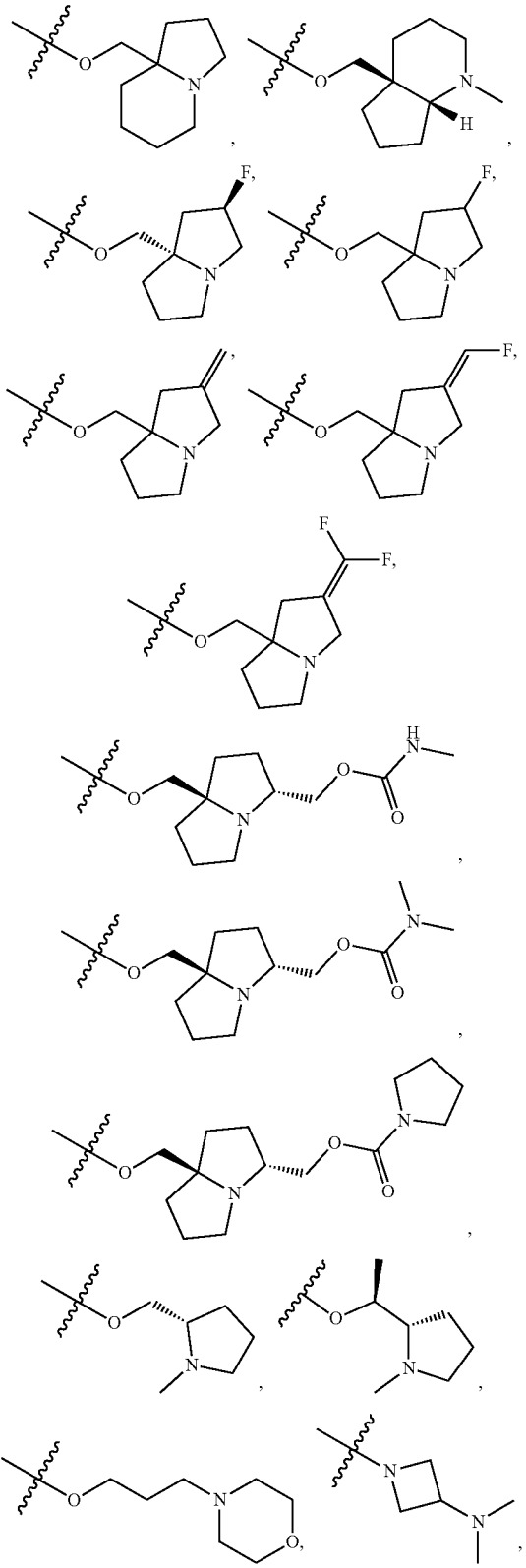

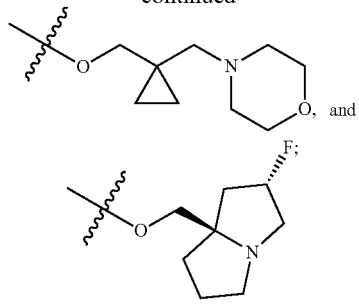

each $R^{11c}$ is independently selected from $C_{1-6}$alkyl, $C_{2-6}$alkenyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{1-11}$heteroaryl, $C_{1-11}$heteroaryl, —(C$_{1-6}$alkyl)-N(R$^{14}$)C(O)R$^{12}$, wherein $C_{1-6}$alkyl, $C_{2-6}$alkenyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{3-10}$cycloalkyl, $C_{2-9}$heterocycloalkyl, —CH$_2$-C$_{2-9}$heterocycloalkyl, wherein $C_{1-6}$alkyl, $C_{3-10}$cycloalkyl, $C_{2-9}$heterocycloalkyl, and —CH$_2$-C$_{2-9}$heterocycloalkyl are optionally substituted with one, two, or three $R^{20t}$;

each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —OR$^{21}$, and —N(R$^{22}$)(R$^{23}$);

each $R^{20t}$ is independently selected from halogen, —OR$^{21}$, and $C_{3-10}$cycloalkyl;

each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl;

each $R^{22}$ is independently selected from H and $C_{1-6}$alkyl;
each $R^{23}$ is independently selected from H and $C_{1-6}$alkyl;
each $R^{24}$ is independently selected from H and $C_{1-6}$alkyl; and each $R^{25}$ is independently selected from $C_{1-6}$alkyl and $C_{3-6}$cycloalkyl. All variables not described in the embodiment immediately above are as described for a compound of formula (Ta), (Td), (Ua), (Ud), (Wa), or (Wd), or an embodiment thereof.

In some embodiments the compound is a compound of Formula (Ta), (Td), (Ua), (Ud), (Wa), or (Wd), or a pharmaceutically acceptable salt or solvate thereof:

wherein $R^6$ and $R^8$ are independently selected from hydrogen and halogen;

$L^7$ is a bond;

$R^{17}$ is selected from:


$Q^3$ is N or $C(R1d)$; $Q^4$ is S;

$X^4$, $X^5$, and $X^{16}$ are independently selected from $C(R^{1a})$ or N;

$X^9$ is $C(R^{1a})$; $X^{10}$, $X^{11}$, $X^{13}$, and $X^{14}$ are independently $C(R^{1a})$ or N; $X^{12}$ is C;

each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, and —C(O)CH$_3$;

$R^{1d}$ is selected from hydrogen, —CN, $C_{1-4}$alkyl, and $C_{1-4}$haloalkyl;

$R^2$ is selected from

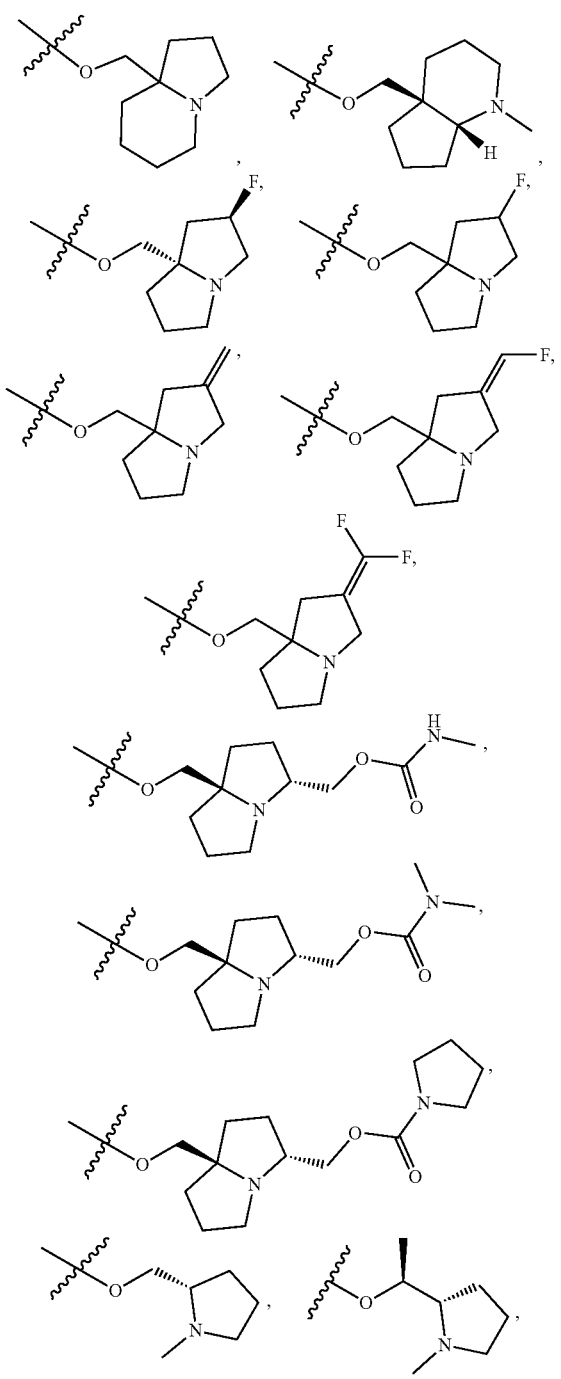

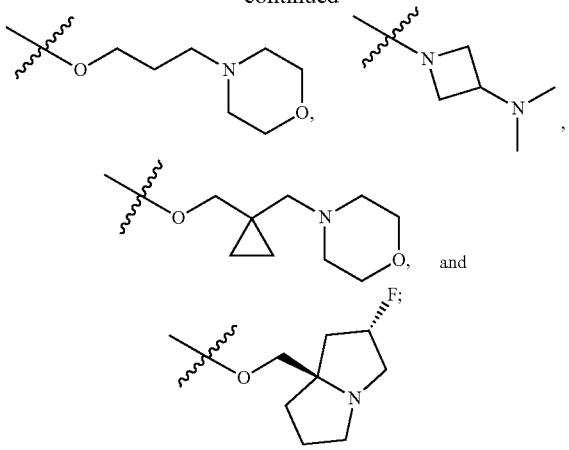

each $R^{11c}$ is independently selected from $C_{1-6}$alkyl, $C_{2-6}$alkenyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{1-11}$heteroaryl, $C_{1-11}$heteroaryl, —(C$_{1-6}$alkyl)-N(R$^{14}$)C(O)R$^{12}$, wherein $C_{1-6}$alkyl, $C_{2-6}$alkenyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{3-10}$cycloalkyl, $C_{2-9}$heterocycloalkyl, —CH$_2$-C$_{2-9}$heterocycloalkyl, wherein $C_{1-6}$alkyl, $C_{3-10}$cycloalkyl, $C_{2-9}$heterocycloalkyl, and —CH$_2$-C$_{2-9}$heterocycloalkyl are optionally substituted with one, two, or three $R^{20l}$;

each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —OR$^{21}$, and —N(R$^{22}$)(R$^{23}$);

each $R^{20l}$ is independently selected from halogen, —OR$^{21}$, and $C_{3-10}$cycloalkyl;

each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl;

each $R^{22}$ is independently selected from H and $C_{1-6}$alkyl;
each $R^{23}$ is independently selected from H and $C_{1-6}$alkyl;
each $R^{24}$ is independently selected from H and $C_{1-6}$alkyl; and each $R^{25}$ is independently selected from $C_{1-6}$alkyl and $C_{3-6}$cycloalkyl. All variables not described in the embodiment immediately above are as described for a compound of formula (Ta), (Td), (Ua), (Ud), (Wa), or (Wd), or an embodiment thereof.

In some embodiments the compound is a compound of Formula (Ta), (Td), (Ua), (Ud), (Wa), or (Wd), or a pharmaceutically acceptable salt or solvate thereof:
wherein
$R^6$ and $R^8$ are independently selected from hydrogen and halogen;
$L^7$ is a bond;

R[17] is selected from:

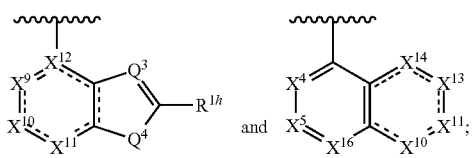

and

Q[3] is N or C(R[1d]); Q[4] is S;

X[4], X[5], and X[16] are independently selected from C(R[1a]) or N;

X[9] is C(R[1a]); X[10], X[11], X[13], and X[14] are independently C(R[1a]) or N; X[12] is C;

each R[1a] and R[1h] is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, —C(O)CH$_3$, —NHC(O)H;

R[1d] is selected from hydrogen, —CN, $C_{1-4}$alkyl, and $C_{1-4}$haloalkyl;

R[2] is selected from

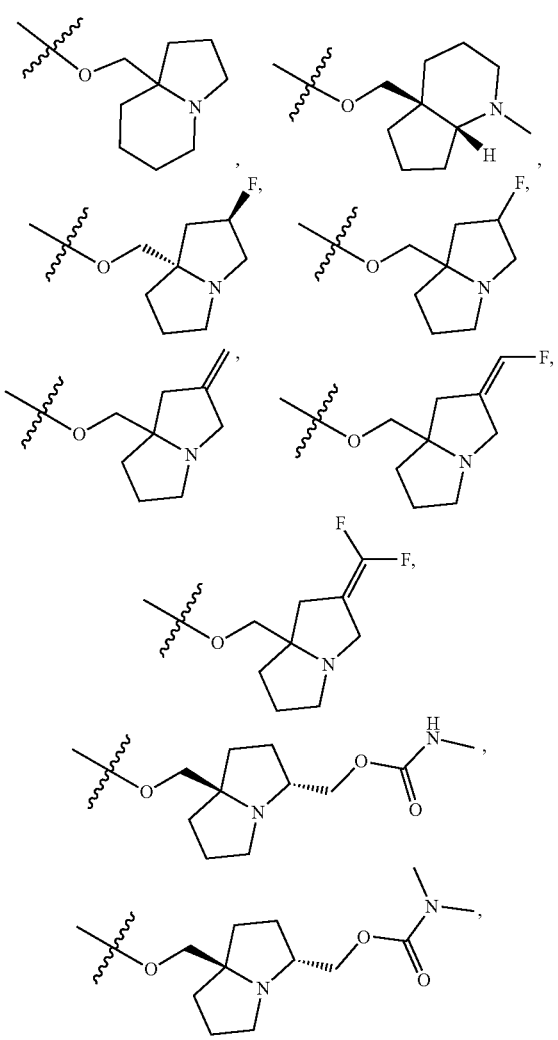

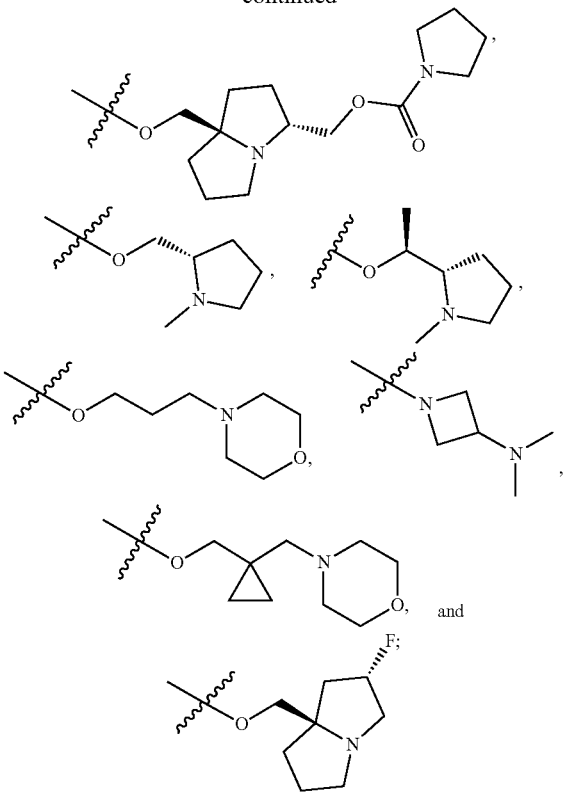

and each R[11c] is independently selected from $C_{1-6}$alkyl, $C_{2-6}$alkenyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{1-11}$heteroaryl, $C_{1-11}$heteroaryl, —($C_{1-6}$alkyl)-N(R[14])C(O)R[12], wherein $C_{1-6}$alkyl, $C_{2-6}$alkenyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{1-11}$heteroaryl, and $C_{1-11}$heteroaryl are optionally substituted with one, two, or three R[20k];

each R[12] is independently selected from hydrogen, $C_{1-6}$alkyl, $C_{3-10}$cycloalkyl, $C_{2-9}$heterocycloalkyl, —CH$_2$-$C_{2-9}$heterocycloalkyl, wherein $C_{1-6}$alkyl, $C_{3-10}$cycloalkyl, $C_{2-9}$heterocycloalkyl, and —CH$_2$-$C_{2-9}$heterocycloalkyl are optionally substituted with one, two, or three R[20t];

each R[20k] is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$ heteroaryl, —OR[21], —N(R[22])(R[23]), —C(O)N(R[22])(R[23]), —N(R[24])C(O)R[21], —C(O)R[21], and —S(O)$_2$R[25], wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —OR[21], and —N(R[22])(R[23]);

each R[20t] is independently selected from halogen, —OR[21], and $C_{3-10}$cycloalkyl;

each R[21] is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl;

each R[22] is independently selected from H and $C_{1-6}$alkyl;

each R[23] is independently selected from H and $C_{1-6}$alkyl;

each R[24] is independently selected from H and $C_{1-6}$alkyl; and each $R^{25}$ is selected from $C_{1-6}$alkyl and $C_{3-6}$cycloalkyl. All variables not described in the embodiment immediately above are as described for a compound of formula (Ta), (Td), (Ua), (Ud), (Wa), or (Wd), or an embodiment thereof.

In some embodiments the compound is a compound of Formula (Ta), (Td), (Ua), (Ud), (Wa), or (Wd), or a pharmaceutically acceptable salt or solvate thereof:

wherein $R^6$ and $R^8$ are independently selected from hydrogen and halogen;

$L^7$ is a bond;

$R^{17}$ is selected from:

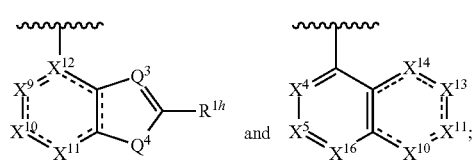

$Q^3$ is N or $C(R^{14})$; $Q^4$ is S;

$X^4$, $X^3$, and $X^{16}$ are independently selected from $C(R^{1a})$ or N;

$X^9$ is $C(R^{1a})$; $X^{10}$, $X^{11}$, $X^{13}$, and $X^{14}$ are independently $C(R^{1a})$ or N; $X^{12}$ is C;

each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, —C(O)CH$_3$, —NHC(O)H;

$R^{1d}$ is selected from hydrogen, —CN, $C_{1-4}$alkyl, and $C_{1-4}$haloalkyl;

$R^2$ is selected from

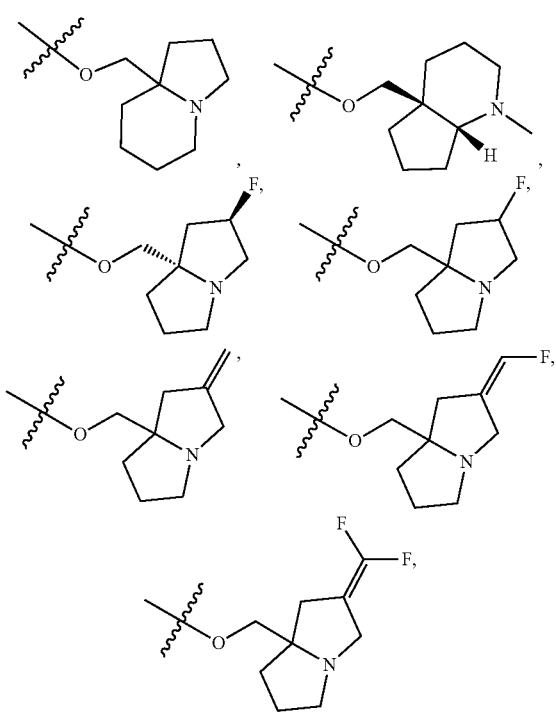

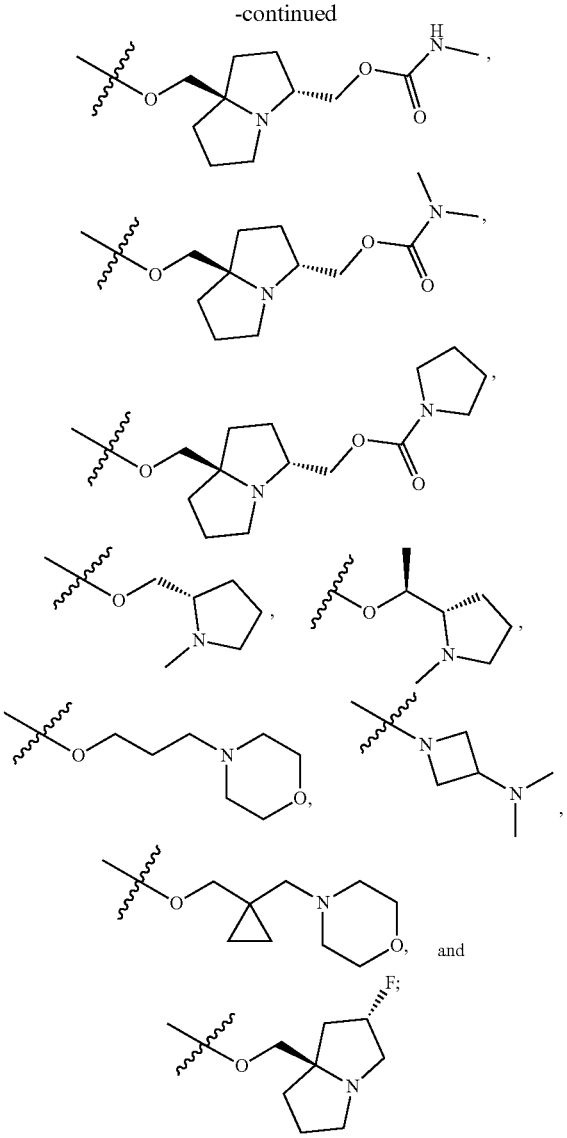

each $R^{11c}$ is independently selected from $C_{1-6}$alkyl, $C_{2-6}$alkenyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{1-11}$heteroaryl, $C_{1-11}$heteroaryl, —(C$_{1-6}$alkyl)-N(R$^{14}$)C(O)R$^{12}$, wherein $C_{1-6}$alkyl, $C_{2-6}$alkenyl, $C_{3-12}$cycloalkyl, —CH$_2$-C$_{3-12}$cycloalkyl, $C_{1-11}$heterocycloalkyl, —CH$_2$-C$_{1-11}$heterocycloalkyl, $C_{6-10}$aryl, —CH$_2$-C$_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{3-10}$cycloalkyl, $C_{2-9}$heterocycloalkyl, —CH$_2$-C$_{2-9}$heterocycloalkyl, wherein $C_{1-6}$alkyl, $C_{3-10}$cycloalkyl, $C_{2-9}$heterocycloalkyl, and —CH$_2$-C$_{2-9}$heterocycloalkyl are optionally substituted with one, two, or three $R^{20r}$;

each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —$OR^{21}$, and —$N(R^{22})(R^{23})$;

each $R^{20t}$ is independently selected from halogen, —$OR^{21}$, and $C_{3-10}$cycloalkyl;

each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl;

each $R^{22}$ is independently selected from H and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is independently selected from $C_{1-6}$alkyl and $C_{3-6}$cycloalkyl. All variables not described in the embodiment immediately above are as described for a compound of formula (Ta), (Td), (Ua), (Ud), (Wa), or (Wd), or an embodiment thereof.

In some embodiments the compound is a compound of Formula (Xa), (Xd), (Ya), (Yd), (Za), or (Zd), or a pharmaceutically acceptable salt or solvate thereof:

wherein $R^6$ and $R^8$ are independently selected from hydrogen and halogen;

$L^7$ is a bond;

$R^{17}$ is selected from:

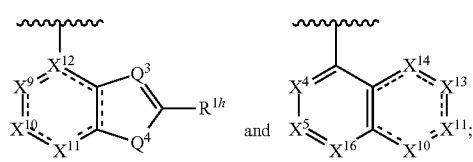

$Q^3$ is N or $C(R1d)$; $Q^4$ is S;

$X^4$, $X^5$, and $X^{16}$ are independently selected from $C(R^{1a})$ or N;

$X^9$ is $C(R^{1a})$; $X^{10}$, $X^{11}$, $X^{13}$, and $X^{14}$ are independently $C(R^{1a})$ or N; $X^{12}$ is C;

each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —$NH_2$, —C(O)OH, —OC(O)$NH_2$, —C(O)$CH_3$, —NHC(O)H;

$R^{1d}$ is selected from hydrogen, —CN, $C_{1-4}$alkyl, and $C_{1-4}$haloalkyl;

$R^2$ is selected from

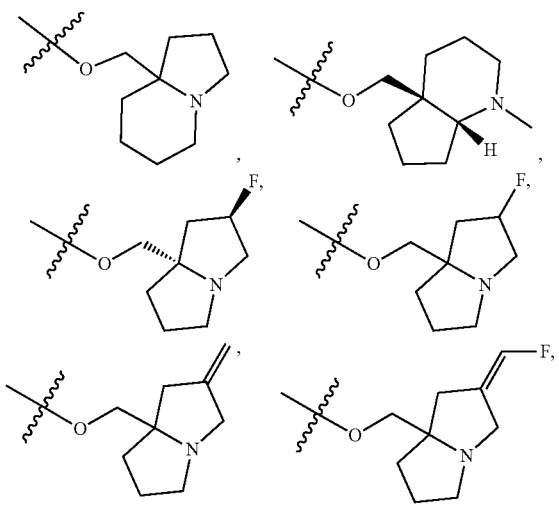

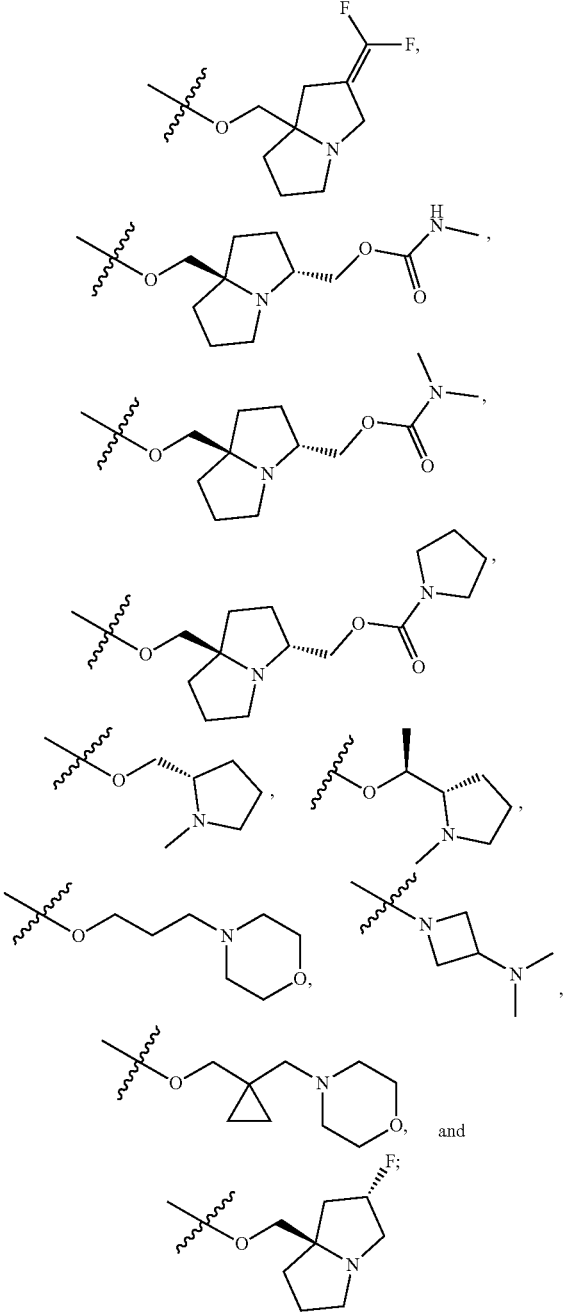

$L^4$ is a bond, —O—, —C(O)—, —S(O)$_2$—, $CR^4R^4$, —$CR^4R^4CR^4R^4$, —$N(R^{4d})C(O)$—, or —C(O)N($R^{4d}$)—;

each $R^{4c}$ is independently selected from hydrogen and $C_{1-6}$alkyl;

each $R^{4d}$ is independently selected from hydrogen and $C_{1-6}$alkyl;

each $R^{4a}$ is independently selected from $C_{3-7}$cycloalkyl, $C_{2-9}$heterocycloalkyl, phenyl, and $C_{1-5}$heteroaryl, wherein $C_{3-6}$cycloalkyl, $C_{2-9}$heterocycloalkyl, phenyl, and $C_{1-5}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{3-12}$cycloalkyl, $C_{2-11}$heterocycloalkyl, —$OR^{12}$, —$N(R^{12})(R^{13})$, =C(R$^{21b}$)$_2$, —C(O)R$^{12}$, —N(R$^{14}$)C(O)R$^{12}$, —S(O)$_2$R$^{15}$, and —C(O)N(R$^{12}$)(R$^{13}$), wherein C$_{1-6}$alkyl, C$_{3-12}$cycloalkyl, and C$_{2-11}$heterocycloalkyl, are optionally substituted with one or more R$^{20j}$;

each R$^{11c}$ is independently selected from C$_{1-6}$alkyl, —CH$_2$-C$_{3-12}$cycloalkyl, —(C$_{1-6}$alkyl)-N(R$^{14}$)C(O)R$^{12}$, wherein C$_{1-6}$alkyl and —CH$_2$-C$_{3-12}$cycloalkyl, are optionally substituted with one, two, or three R$^{20k}$;

each R$^{12}$ is independently selected from hydrogen, C$_{1-6}$alkyl, C$_{2-6}$alkenyl, C$_{3-10}$cycloalkyl, C$_{2-9}$heterocycloalkyl, —CH$_2$-C$_{2-9}$heterocycloalkyl, and C$_{1-9}$heteroaryl, wherein C$_{1-6}$alkyl, C$_{3-10}$cycloalkyl, C$_{2-9}$heterocycloalkyl, —CH$_2$-C$_{2-9}$heterocycloalkyl, and C$_{1-9}$heteroaryl are optionally substituted with one, two, or three R$^{20l}$;

each R$^{13}$ is independently selected from hydrogen and C$_{1-6}$alkyl;

each R$^{14}$ is independently selected from hydrogen, C$_{1-6}$alkyl, and C$_{1-6}$haloalkyl;

each R$^{15}$ is independently selected from C$_{3-10}$cycloalkyl;

each R$^{20j}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkylC$_{2-9}$heterocycloalkyl, C$_{6-10}$aryl, and C$_{1-9}$heteroaryl are optionally substituted with one, two, or three groups independently selected from halogen;

each R$^{20k}$ is independently selected from halogen, —CN, —OR$^{21}$, —N(R$^{22}$)(R$^{23}$), and —N(R$^{24}$)C(O)R$^{21}$;

each R$^{20l}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three groups independently selected from halogen;

each R$^{21}$ is independently selected from H, C$_{1-6}$alkyl, C$_{1-6}$haloalkyl, C$_{3-10}$cycloalkyl, C$_{2-9}$heterocycloalkyl, and C$_{1-9}$heteroaryl;

each R$^{22}$ is independently selected from H and C$_{1-6}$alkyl;
each R$^{23}$ is independently selected from H and C$_{1-6}$alkyl;
each R$^{24}$ is independently selected from H and C$_{1-6}$alkyl; and each R$^{25}$ is independently selected from C$_{1-6}$alkyl, C$_{3-6}$cycloalkyl, and C$_{2-9}$heterocycloalkyl. All variables not described in the embodiment immediately above are as described for a compound of formula (Xa), (Xd), (Ya), (Yd), (Za), or (Zd), or an embodiment thereof.

In some embodiments the compound is a compound of Formula (Xa), (Xd), (Ya), (Yd), (Za), or (Zd), or a pharmaceutically acceptable salt or solvate thereof:
wherein
R$^6$ and R$^8$ are independently selected from hydrogen and halogen;
L$^7$ is a bond;
R$^{17}$ is selected from:

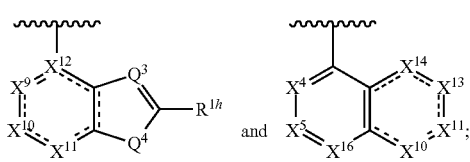

Q$^3$ is N or C(R$^{14}$); Q$^4$ is S;
X$^4$, X$^3$, and X$^{16}$ are independently selected from C(R$^{1a}$) or N;

X$^9$ is C(R$^{1a}$); X$^{10}$, X$^{11}$, X$^{13}$, and X$^{14}$ are independently C(R$^{1a}$) or N; X$^{12}$ is C;

each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;

R$^{1d}$ is selected from hydrogen, —CN, C$_{1-4}$alkyl, and C$_{1-4}$haloalkyl;

R$^2$ is selected from

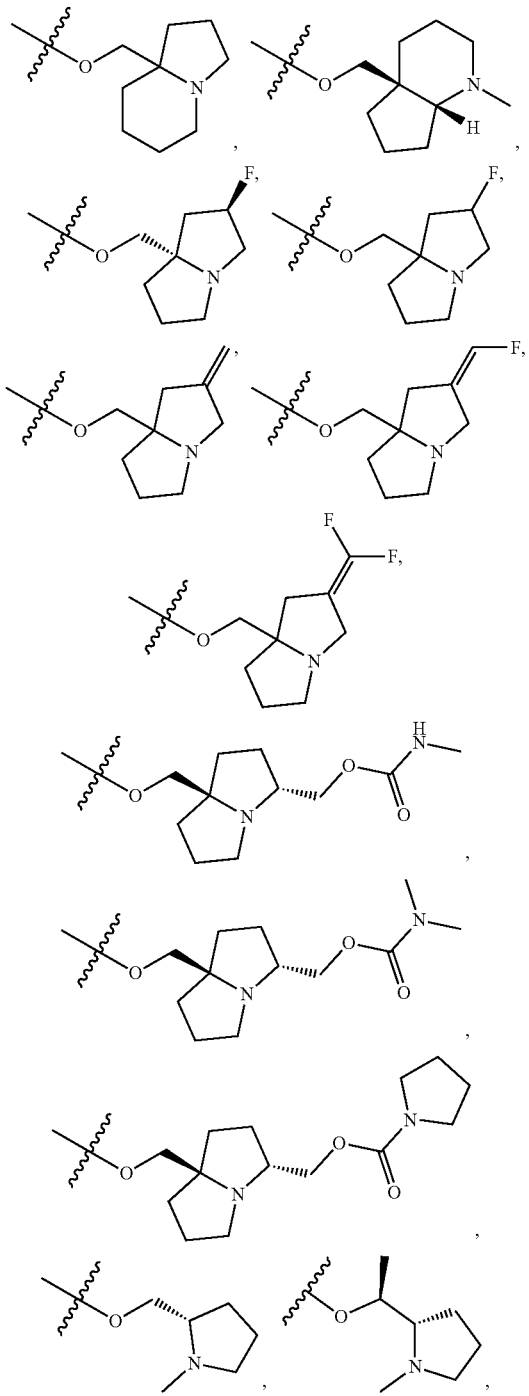

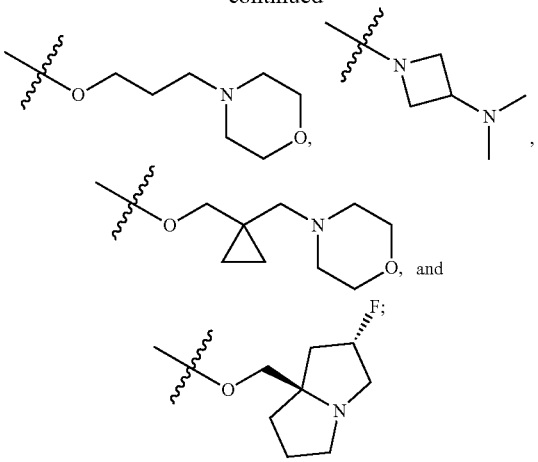

$L^4$ is a bond, —O—, —C(O)—, —S(O)$_2$—, CR$^4$R$^4$, —CR$^4$R$^4$CCR$^4$CR$^{4c}$, —N(R$^{4d}$)C(O)—, or —C(O)N(R$^{4d}$)—;

each R$^{4c}$ is independently selected from hydrogen and C$_{1-6}$alkyl;

each R$^{4d}$ is independently selected from hydrogen and C$_{1-6}$alkyl;

each R$^{4a}$ is independently selected from C$_{3-7}$cycloalkyl, C$_{2-9}$heterocycloalkyl, phenyl, and C$_{1-5}$heteroaryl, wherein C$_{3-6}$cycloalkyl, C$_{2-9}$heterocycloalkyl, phenyl, and C$_{1-5}$heteroaryl are optionally substituted with one, two, three, or four R$^{4b}$;

each R$^{4b}$ is independently selected from halogen, oxo, —CN, C$_{1-6}$alkyl, C$_{2-6}$alkenyl, C$_{3-12}$cycloalkyl, C$_{2-11}$heterocycloalkyl, —OR$^{12}$, —N(R$^{12}$)(R$^{13}$), =C(R$^{21b}$)$_2$, —C(O)R$^{12}$, —N(R$^{14}$)C(O)R$^{12}$, —S(O)$_2$R$^{15}$, and —C(O)N(R$^{12}$)(R$^{13}$), wherein C$_{1-6}$alkyl, C$_{3-12}$cycloalkyl, and C$_{2-11}$heterocycloalkyl, are optionally substituted with one or more R$^{20j}$;

each R$^{11c}$ is independently selected from C$_{1-6}$alkyl, —CH$_2$-C$_{3-12}$cycloalkyl, —(C$_{1-6}$alkyl)-N(R$^{14}$)C(O)R$^{12}$, wherein C$_{1-6}$alkyl and —CH$_2$-C$_{3-12}$cycloalkyl, are optionally substituted with one, two, or three R$^{20k}$;

each R$^{12}$ is independently selected from hydrogen, C$_{1-6}$alkyl, C$_{2-6}$alkenyl, C$_{3-10}$cycloalkyl, C$_{2-9}$heterocycloalkyl, —CH$_2$-C$_{2-9}$heterocycloalkyl, and C$_{1-9}$heteroaryl, wherein C$_{1-6}$alkyl, C$_{3-10}$cycloalkyl, C$_{2-9}$heterocycloalkyl, —CH$_2$-C$_{2-9}$heterocycloalkyl, and C$_1$.heteroaryl are optionally substituted with one, two, or three R$^{20l}$;

each R$^{13}$ is independently selected from hydrogen and C$_{1-6}$alkyl;

each R$^{14}$ is independently selected from hydrogen, C$_{1-6}$alkyl, and C$_{1-6}$haloalkyl;

each R$^{15}$ is independently selected from C$_{3-10}$cycloalkyl;

each R$^{20j}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkylC$_{2-9}$heterocycloalkyl, C$_{6-10}$aryl, and C$_{1-9}$heteroaryl are optionally substituted with one, two, or three groups independently selected from halogen;

each R$^{20k}$ is independently selected from halogen, —CN, —OR$^{21}$, —N(R$^{22}$)(R$^{23}$), and —N(R$^{24}$)C(O)R$^{21}$;

each R$^{20t}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three groups independently selected from halogen;

each R$^{21}$ is independently selected from H, C$_{1-6}$alkyl, C$_{1-6}$haloalkyl, C$_{3-10}$cycloalkyl, C$_{2-9}$heterocycloalkyl, and C$_{1-9}$heteroaryl;

each R$^{22}$ is independently selected from H and C$_{1-6}$alkyl;

each R$^{23}$ is independently selected from H and C$_{1-6}$alkyl;

each R$^{24}$ is independently selected from H and C$_{1-6}$alkyl; and each R$^{25}$ is independently selected from C$_{1-6}$alkyl, C$_{3-6}$cycloalkyl, and C$_{2-9}$heterocycloalkyl. All variables not described in the embodiment immediately above are as described for a compound of formula (Xa), (Xd), (Ya), (Yd), (Za), or (Zd), or an embodiment thereof.

In some embodiments the compound is a compound of Formula (Xa), (Xd), (Ya), (Yd), (Za), or (Zd), or a pharmaceutically acceptable salt or solvate thereof:

wherein

R$^6$ and R$^8$ are independently selected from hydrogen and halogen;

L$^7$ is a bond;

R$^{17}$ is selected from:

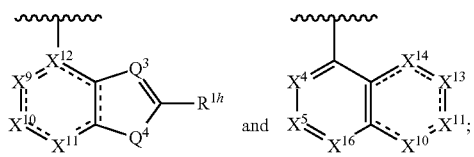

Q$^3$ is N or C(R$^{14}$); Q$^4$ is S;

X$^4$, X$^3$, and X$^{16}$ are independently selected from C(R$^{1a}$) or N;

X$^9$ is C(R$^{1a}$); X$^{10}$, X$^{11}$, X$^{13}$, and X$^{14}$ are independently C(R$^{1a}$) or N; X$^{12}$ is C;

each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;

R$^{1d}$ is selected from hydrogen, —CN, C$_{1-4}$alkyl, and C$_{1-4}$haloalkyl;

R$^2$ is selected from

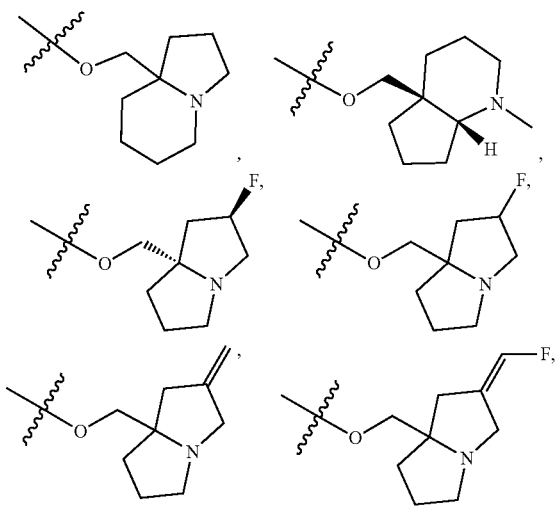

-continued

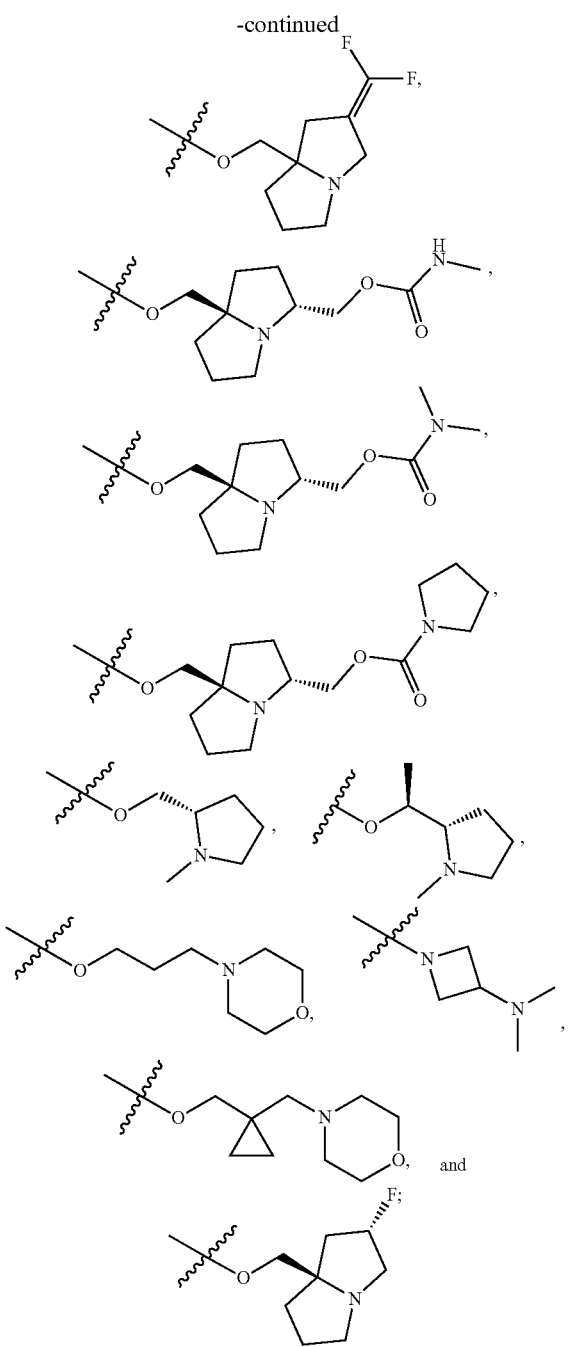

$L^4$ is a bond, —O—, —C(O)—, —S(O)$_2$—, CR$^4$R$^4$, —CR$^4$R$^4$CR$^4$R$^4$, —N(R$^{4d}$)C(O)—, or —C(O)N(R$^{4d}$)—;

each R$^{4c}$ is independently selected from hydrogen and C$_{1-6}$alkyl;

each R$^{4d}$ is independently selected from hydrogen and C$_{1-6}$alkyl;

each R$^{4a}$ is independently selected from C$_{3-7}$cycloalkyl, C$_{2-9}$heterocycloalkyl, phenyl, and C$_{1-5}$heteroaryl, wherein C$_{3-6}$cycloalkyl, C$_{2-9}$heterocycloalkyl, phenyl, and C$_{1-5}$heteroaryl are optionally substituted with one, two, three, or four R$^{4b}$;

each R$^{4b}$ is independently selected from halogen, oxo, —CN, C$_{1-6}$alkyl, C$_{2-6}$alkenyl, C$_{3-12}$cycloalkyl, C$_{2-11}$heterocycloalkyl, —OR$^{12}$, —N(R$^{12}$)(R$^{13}$), =C(R$^{21b}$)$_2$, —C(O)R$^{12}$, —N(R$^{14}$)C(O)R$^{12}$, —S(O)$_2$R$^{15}$, and —C(O)N(R$^{12}$)(R$^{13}$), wherein C$_{1-6}$alkyl, C$_{3-12}$cycloalkyl, and C$_{2-11}$heterocycloalkyl, are optionally substituted with one or more R$^{20j}$;

each R$^{11c}$ is independently selected from C$_{1-6}$alkyl, —CH$_2$-C$_{3-12}$cycloalkyl, —(C$_{1-6}$alkyl)-N(R$^{14}$)C(O)R$^{12}$, wherein C$_{1-6}$alkyl and —CH$_2$-C$_{3-12}$cycloalkyl, are optionally substituted with one, two, or three R$^{20k}$;

each R$^{12}$ is independently selected from hydrogen, C$_{1-6}$alkyl, C$_{2-6}$alkenyl, C$_{3-10}$cycloalkyl, C$_{2-9}$heterocycloalkyl, —CH$_2$-C$_{2-9}$heterocycloalkyl, and C$_{1-9}$heteroaryl, wherein C$_{1-6}$alkyl, C$_{3-10}$cycloalkyl, C$_{2-9}$heterocycloalkyl, —CH$_2$-C$_{2-9}$heterocycloalkyl, and C$_{1-9}$heteroaryl are optionally substituted with one, two, or three R$^{20t}$;

each R$^{13}$ is independently selected from hydrogen and C$_{1-6}$alkyl;

each R$^{14}$ is independently selected from hydrogen, C$_{1-6}$alkyl, and C$_{1-6}$haloalkyl;

each R$^{15}$ is independently selected from C$_{3-10}$cycloalkyl;

each R$^{20j}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkyl C$_{2-9}$heterocycloalkyl, C$_{6-10}$aryl, and C$_{1-9}$heteroaryl are optionally substituted with one, two, or three groups independently selected from halogen;

each R$^{20k}$ is independently selected from halogen, —CN, —OR$^{21}$, —N(R$^{22}$)(R$^{23}$), and —N(R$^{24}$)C(O)R$^{21}$;

each R$^{20t}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three groups independently selected from halogen;

each R$^{21}$ is independently selected from H, C$_{1-6}$alkyl, C$_{1-6}$haloalkyl, C$_{3-10}$cycloalkyl, C$_{2-9}$heterocycloalkyl, and C$_{1-9}$heteroaryl;

each R$^{22}$ is independently selected from H and C$_{1-6}$alkyl;
each R$^{23}$ is independently selected from H and C$_{1-6}$alkyl;
each R$^{24}$ is independently selected from H and C$_{1-6}$alkyl; and each R$^{25}$ is independently selected from C$_{1-6}$alkyl, C$_{3-6}$cycloalkyl, and C$_{2-9}$heterocycloalkyl. All variables not described in the embodiment immediately above are as described for a compound of formula (Xa), (Xd), (Ya), (Yd), (Za), or (Zd), or an embodiment thereof.

In some embodiments the compound is a compound of Formula (Xa), (Xd), (Ya), (Yd), (Za), or (Zd), or a pharmaceutically acceptable salt or solvate thereof:
wherein
R$^6$ and R$^8$ are independently selected from hydrogen and halogen;
L$^7$ is a bond;
R$^{17}$ is selected from:

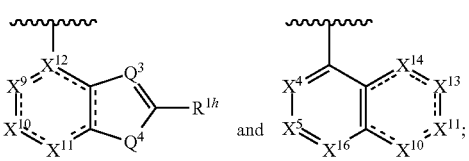

Q$^3$ is N or C(R$^{1d}$); Q$^4$ is S;
X$^4$, X$^5$, and X$^{16}$ are independently selected from C(R$^{1a}$) or N;

$X^9$ is $C(R^{1a})$; $X^{10}$, $X^{11}$, $X^{13}$, and $X^{14}$ are independently $C(R^{1a})$ or N; $X^{12}$ is C;

each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, and —C(O)CH$_3$;

$R^{1D}$ is selected from hydrogen, —CN, $C_{1-4}$alkyl, and $C_{1-4}$haloalkyl;

$R^2$ is selected from

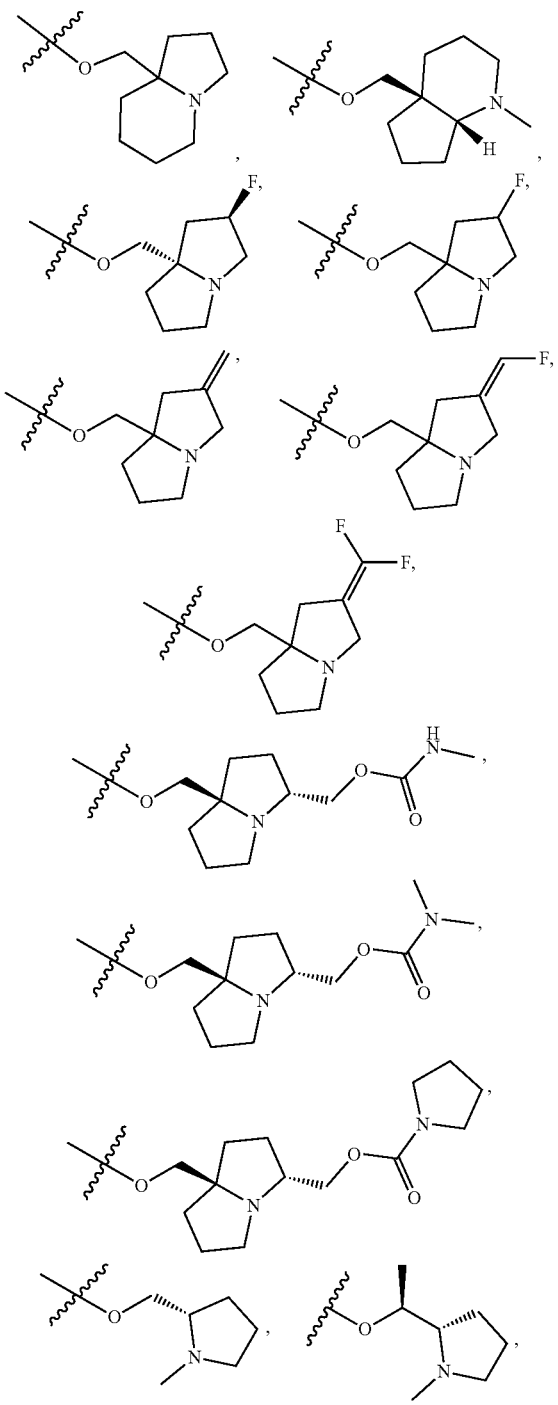

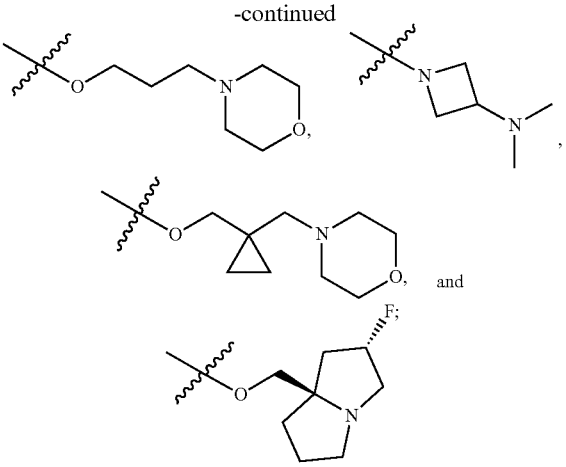

$L^4$ is a bond, $CR^4R^{4c}$;

each $R^4$ is independently selected from hydrogen and $C_{1-6}$alkyl;

each $R^{4a}$ is independently selected from $C_{3-7}$cycloalkyl and $C_{2-9}$heterocycloalkyl, wherein $C_{3-6}$cycloalkyl and $C_{2-9}$heterocycloalkyl are optionally substituted with one, two, three, or four $R^{4b}$;

each $R^{4b}$ is independently selected from halogen, —CN, $C_{1-6}$alkyl, —OR$^{12}$, —N(R$^{12}$)(R$^{13}$), =C(R$^{21b}$)$_2$, and —C(O)R$^{12}$, wherein $C_{1-6}$alkyl is optionally substituted with one or more $R^{20j}$;

each $R^{11c}$ is independently selected from $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, and $C_{1-11}$heteroaryl are optionally substituted with one, two, or three $R^{20k}$;

each $R^{12}$ is independently selected from hydrogen, $C_{1-6}$alkyl, $C_{2-9}$heterocycloalkyl, and —CH$_2$-C$_{2-9}$heterocycloalkyl, wherein $C_{1-6}$alkyl, $C_{2-9}$heterocycloalkyl, and —CH$_2$-C$_{2-9}$heterocycloalkyl are optionally substituted with one, two, or three $R^{20t}$;

each $R^{13}$ is independently selected from hydrogen, $C_{1-6}$alkyl;

each $R^{14}$ is independently selected from hydrogen and $C_{1-6}$alkyl;

each $R^{20j}$ is independently selected from halogen;

each $R^{20k}$ is independently selected from halogen, —CN, $C_{1-6}$alkyl, —OR$^{21}$, —N(R$^{22}$)(R$^{23}$), and —C(O)R$^{21}$, wherein $C_{1-6}$alkyl, is optionally substituted with one, two, or three groups independently selected from halogen, —CN, $C_{1-6}$alkyl, $C_{1-6}$haloalkyl, —OR$^{21}$, —N(R$^{22}$)(R$^{23}$);

each $R^{20t}$ is independently selected from halogen, $C_{3-10}$cycloalkyl, and —N(R$^{22}$)(R$^{23}$);

each $R^{21}$ is independently selected from H and $C_{1-6}$haloalkyl;

each $R^{22}$ is independently selected from H and $C_{1-6}$alkyl; and each $R^{23}$ is independently selected from H and $C_{1-6}$alkyl. All variables not described in the embodiment immediately above are as described for a compound of formula (Xa), (Xd), (Ya), (Yd), (Za), or (Zd), or an embodiment thereof.

In some embodiments the compound is a compound of Formula (Ta), (Td), (Ua), (Ud), (Wa), or (Wd), or a pharmaceutically acceptable salt or solvate thereof:

wherein

R$^6$ and R$^8$ are independently selected from hydrogen and halogen;

L$^7$ is a bond;

R$^{17}$ is selected from:

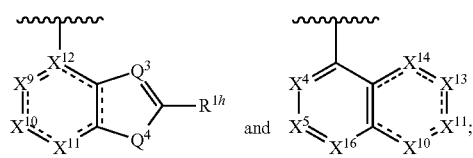

Q$^3$ is N or C(R$^{1d}$); Q$^4$ is S;

X$^4$, X$^5$, and X$^{16}$ are independently selected from C(R$^{1a}$) or N;

X$^9$ is C(R$^{1a}$); X$^{10}$, X$^{11}$, X$^{13}$, and X$^{14}$ are independently C(R$^{1a}$) or N; X$^{12}$ is C;

each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;

R$^{1d}$ is selected from hydrogen, —CN, C$_{1-4}$alkyl, and C$_{1-4}$haloalkyl;

R$^2$ is selected from

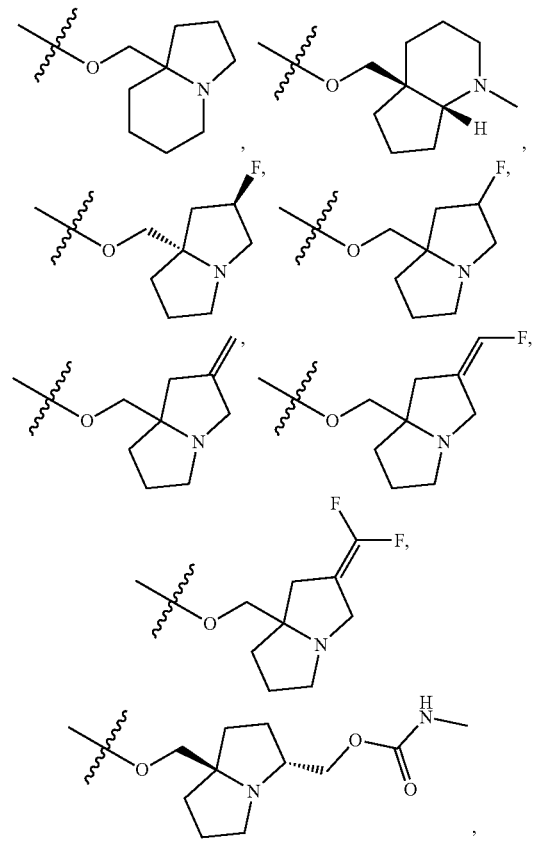

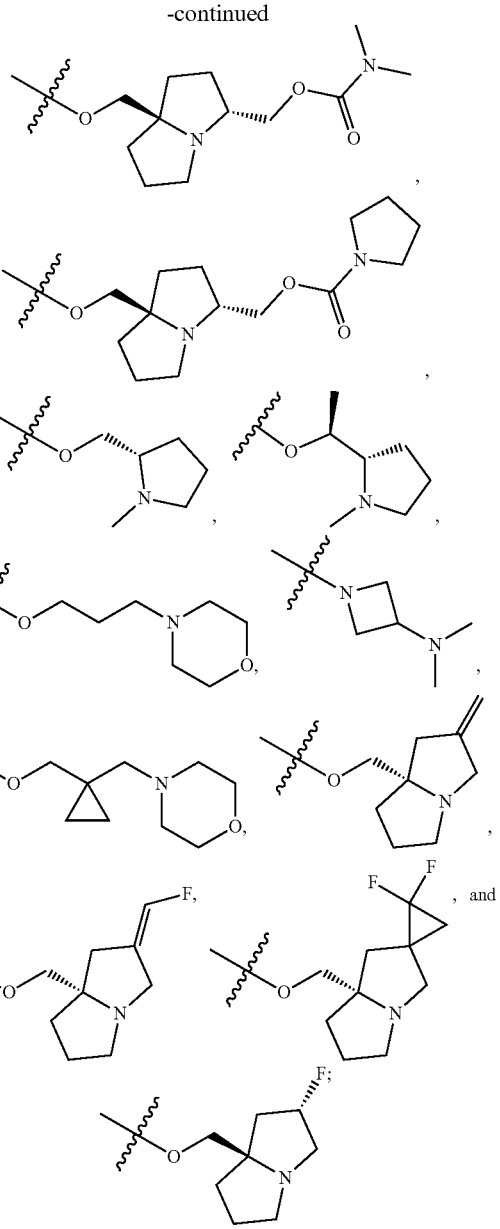

each R$^{11c}$ is independently selected from C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, C$_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, and C$_{1-11}$heteroaryl are optionally substituted with one, two, or three R$^{20k}$;

each R$^{12}$ is independently selected from hydrogen, C$_{1-6}$alkyl, C$_{2-9}$heterocycloalkyl, and —CH$_2$-C$_{2-9}$heterocycloalkyl, wherein C$_{1-6}$alkyl, C$_{2-9}$heterocycloalkyl, and —CH$_2$-C$_{2-9}$heterocycloalkyl are optionally substituted with one, two, or three R$^{20l}$;

each R$^{13}$ is independently selected from hydrogen, C$_{1-6}$alkyl;

each R$^{14}$ is independently selected from hydrogen and C$_{1-6}$alkyl;

each R$^{20j}$ is independently selected from halogen;

each R$^{20k}$ is independently selected from halogen, —CN, C$_{1-6}$alkyl, —OR$^{21}$, —N(R$^{22}$)(R$^{23}$), and —C(O)R$^{21}$, wherein $C_{1-6}$alkyl, is optionally substituted with one, two, or three groups independently selected from halogen, —CN, $C_{1-6}$alkyl, $C_{1-6}$haloalkyl, —OR$^{21}$, —N(R$^{22}$)(R$^{23}$);

each $R^{20t}$ is independently selected from halogen, $C_{3-10}$cycloalkyl, and —N(R$^{22}$)(R$^{23}$);

each $R^{21}$ is independently selected from H and $C_{1-6}$haloalkyl;

each $R^{22}$ is independently selected from H and $C_{1-6}$alkyl; and each $R^{23}$ is independently selected from H and $C_{1-6}$alkyl.

In some embodiments the compound is a compound of Formula (Ta), (Td), (Ua), (Ud), (Wa), or (Wd), or a pharmaceutically acceptable salt or solvate thereof:

$R^6$ and $R^8$ are independently selected from hydrogen and halogen;

$L^7$ is a bond;

$R^{17}$ is selected from $C_{2-9}$heterocycloalkyl, $C_{6-10}$aryl, and $C_{1-9}$heteroaryl, wherein bicyclic $C_{2-9}$heterocycloalkyl, $C_{6-10}$aryl, and $C_{1-9}$heteroaryl are optionally substituted with one, two, three, four, or five $R^{20g}$;

$R^2$ is —O—C(R$^{12b}$)$_2$-C$_{2-9}$heterocycloalkyl optionally substituted with one, two, or three $R^{20t}$;

each $R^{11c}$ is independently selected from $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, and $C_{1-11}$heteroaryl are optionally substituted with one, two, or three $R^{20k}$;

each $R^{12}$ is independently selected from hydrogen, $C_{1-6}$alkyl, $C_{2-9}$heterocycloalkyl, and —CH$_2$-C$_{2-9}$heterocycloalkyl, wherein $C_{1-6}$alkyl, $C_{2-9}$heterocycloalkyl, and —CH$_2$-C$_{2-9}$heterocycloalkyl are optionally substituted with one, two, or three $R^{20t}$;

each $R^{12b}$ is independently selected from hydrogen and $C_{1-6}$alkyl;

each $R^{13}$ is independently selected from hydrogen, $C_{1-6}$alkyl;

each $R^{14}$ is independently selected from hydrogen and $C_{1-6}$alkyl;

each $R^{20j}$ is independently selected from halogen;

each $R^{20g}$ is independently selected from halogen, —CN, $C_{1-6}$alkyl, $C_{2-6}$alkenyl, $C_{2-6}$alkynyl, $C_{3-10}$cycloalkyl, —OR$^{21}$, and —N(R$^{22}$)(R$^{23}$), wherein $C_{1-6}$alkyl, $C_{2-6}$alkenyl, $C_{2-6}$alkynyl, and $C_{3-10}$cycloalkyl are optionally substituted with one, two, or three groups independently selected from halogen, —OR$^{21}$, and —N(R$^{22}$)(R$^{23}$);

each $R^{20t}$ is independently selected from halogen, $C_{1-6}$alkyl, $C_{3-10}$cycloalkyl, $C_{2-9}$heterocycloalkyl, —CH$_2$-C$_{2-9}$heterocycloalkyl, =NR$^{21}$, —N(R$^{22}$)(R$^{23}$), and =C(R$^{21b}$)$_2$, wherein $C_{1-6}$alkyl, $C_{3-10}$cycloalkyl, $C_{2-9}$heterocycloalkyl, and —CH$_2$-C$_{2-9}$heterocycloalkyl, are optionally substituted with one, two, or three groups independently selected from —OC(O)N(R$^{22}$)(R$^{23}$) and —OC(O)R$^{25}$;

each $R^{20k}$ is independently selected from halogen, —CN, $C_{1-6}$alkyl, —OR$^{21}$, —N(R$^{22}$)(R$^{23}$), and —C(O)R$^{21}$, wherein $C_{1-6}$alkyl, is optionally substituted with one, two, or three groups independently selected from halogen, —CN, $C_{1-6}$alkyl, $C_{1-6}$haloalkyl, —OR$^{21}$, —N(R$^{22}$)(R$^{23}$);

each $R^{21}$ is independently selected from H and $C_{1-6}$haloalkyl;

each $R^{21b}$ is independently selected from hydrogen and halogen;

each $R^{22}$ is independently selected from H and $C_{1-6}$alkyl;

each $R^{23}$ is independently selected from H and $C_{1-6}$alkyl.

each $R^{25}$ is independently selected from $C_{2-9}$heterocycloalkyl; and

----- indicates a single or double bond such that all valences are satisfied. All variables not described in the embodiment immediately above are as described for a compound of formula (Ta), (Td), (Ua), (Ud), (Wa), or (Wd), or an embodiment thereof.

In some embodiments the compound is a compound of Formula (Ta), (Td), (Ua), (Ud), (Wa), or (Wd), or a pharmaceutically acceptable salt or solvate thereof:

$R^6$ and $R^8$ are independently selected from hydrogen and halogen;

$L^7$ is a bond;

$R^{17}$ is selected from bicyclic 9-10 membered heterocycloalkyl, phenyl, naphthyl, pyridyl, and bicyclic 9-10 membered heteroaryl, wherein bicyclic 9-10 membered heterocycloalkyl, phenyl, naphthyl, pyridyl, and bicyclic 9-10 membered heteroaryl are optionally substituted with one, two, three, four, or five $R^{20g}$;

$R^2$ is —O—C(R$^{12b}$)$_2$-C$_{2-9}$heterocycloalkyl optionally substituted with one, two, or three $R^{20t}$;

each $R^{11c}$ is independently selected from $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, and $C_{1-11}$heteroaryl are optionally substituted with one, two, or three $R^{20k}$;

each $R^{12}$ is independently selected from hydrogen, $C_{1-6}$alkyl, $C_{2-9}$heterocycloalkyl, and —CH$_2$-C$_{2-9}$heterocycloalkyl, wherein $C_{1-6}$alkyl, $C_{2-9}$heterocycloalkyl, and —CH$_2$-C$_{2-9}$heterocycloalkyl are optionally substituted with one, two, or three $R^{20t}$;

each $R^{12b}$ is independently selected from hydrogen and $C_{1-6}$alkyl;

each $R^{13}$ is independently selected from hydrogen, $C_{1-6}$alkyl;

each $R^{14}$ is independently selected from hydrogen and $C_{1-6}$alkyl;

each $R^{20j}$ is independently selected from halogen;

each $R^{20g}$ is independently selected from halogen, —CN, $C_{1-6}$alkyl, $C_{2-6}$alkenyl, $C_{2-6}$alkynyl, $C_{3-10}$cycloalkyl, —OR$^{21}$, and —N(R$^{22}$)(R$^{23}$), wherein $C_{1-6}$alkyl, $C_{2-6}$alkenyl, $C_{2-6}$alkynyl, and $C_{3-10}$cycloalkyl are optionally substituted with one, two, or three groups independently selected from halogen, —OR$^{21}$, and —N(R$^{22}$)(R$^{23}$);

each $R^{20t}$ is independently selected from halogen, $C_{1-6}$alkyl, $C_{3-10}$cycloalkyl, $C_{2-9}$heterocycloalkyl, —CH$_2$-C$_{2-9}$heterocycloalkyl, =NR$^{21}$, —N(R$^{22}$)(R$^{23}$), and —C(R$^{21b}$)$_2$, wherein $C_{1-6}$alkyl, $C_{3-10}$cycloalkyl, $C_{2-9}$heterocycloalkyl, and —CH$_2$-C$_{2-9}$heterocycloalkyl, are optionally substituted with one, two, or three groups independently selected from —OC(O)N(R$^{22}$)(R$^{23}$) and —OC(O)R$^{25}$;

each $R^{20k}$ is independently selected from halogen, —CN, $C_{1-6}$alkyl, —OR$^{21}$, —N(R$^{22}$)(R$^{23}$), —N(R$^{24}$)S(O)$_2$R$^{25}$, and —C(O)R$^{21}$, wherein $C_{1-6}$alkyl, is optionally substituted with one, two, or three groups independently selected from halogen, —CN, $C_{1-6}$alkyl, $C_{1-6}$haloalkyl, —OR$^{21}$, —N(R$^{22}$)(R$^{23}$);

each $R^{21}$ is independently selected from H and $C_{1-6}$haloalkyl;

each $R^{21b}$ is independently selected from hydrogen and halogen;

each $R^{22}$ is independently selected from H and $C_{1-6}$alkyl;

each $R^{23}$ is independently selected from H and $C_{1-6}$alkyl;

each $R^{24}$ is H;

each $R^{25}$ is independently selected from $C_{2-9}$heterocycloalkyl; and

----- indicates a single or double bond such that all valences are satisfied. All variables not described in the embodiment immediately above are as described for a compound of formula (Ta), (Td), (Ua), (Ud), (Wa), or (Wd), or an embodiment thereof.

In some embodiments the compound is a compound of Formula (Ta), (Td), (Ua), (Ud), (Wa), or (Wd), or a pharmaceutically acceptable salt or solvate thereof:

$R^6$ and $R^8$ are independently selected from hydrogen and halogen;

$L^7$ is a bond;

$R^{17}$ is selected from:

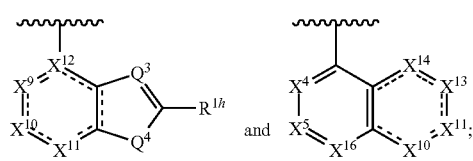

and $Q^3$ is N or $C(R^{14})$; $Q^4$ is S;

$X^4$ and $X^5$ are independently selected from $C(R^{1a})$ or N;

$X^9$ is $C(R^{1a})$; $X^{10}$, $X^{11}$, $X^{13}$, and $X^{14}$ are independently $C(R^{1a})$ or N; $X^{12}$ is C;

each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, and —C(O)CH$_3$;

$R^{1d}$ is selected from hydrogen, —CN, $C_{1-4}$alkyl, and $C_{1-4}$haloalkyl;

$R^2$ is selected from

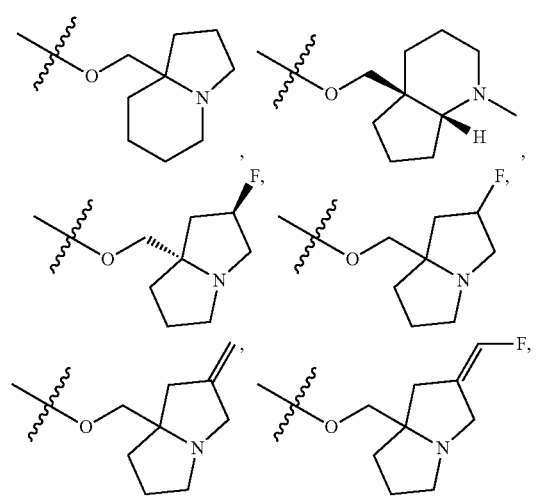

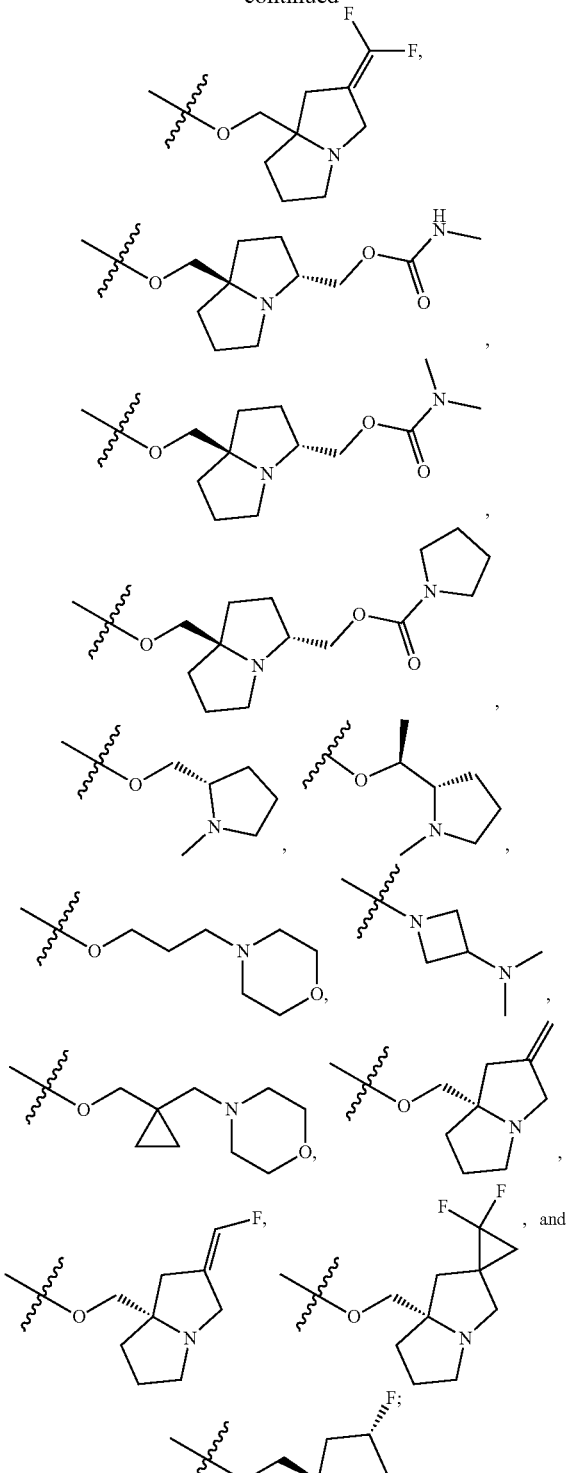

each $R^{11c}$ is independently selected from hydrogen, $C_{1-6}$alkyl, $C_{3-12}$cycloalkyl, —CH$_2$-$C_{3-12}$cycloalkyl, $C_{1-11}$heterocycloalkyl, CH$_2$-$C_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-$C_{3-12}$cycloalkyl, $C_{1-11}$heterocycloalkyl, CH₂-C₁₋₁₁heterocycloalkyl, and C₁₋₁₁heteroaryl are optionally substituted with one, two, or three $R^{20k}$;

each $R^{11d}$ is independently selected from C₁₋₆alkyl, C₃₋₁₂cycloalkyl, —CH₂-C₃₋₁₂cycloalkyl, C₁₋₁₁heterocycloalkyl, CH₂-C₁₋₁₁heterocycloalkyl, C₁₋₁₁heteroaryl, —(C₁₋₆alkyl)-N(R¹⁴)C(O)R¹², and —(C₁₋₆alkyl)-N(R¹²)(R¹³), wherein C₁₋₆alkyl, C₃₋₁₂cycloalkyl, —CH₂-C₃₋₁₂cycloalkyl, C₁₋₁₁heterocycloalkyl, CH₂-C₁₋₁₁heterocycloalkyl, and C₁₋₁₁heteroaryl are optionally substituted with one, two, or three $R^{20k}$;

each $R^{12}$ is independently selected from hydrogen, C₁₋₆alkyl, C₂₋₉heterocycloalkyl, and —CH₂-C₂₋₉heterocycloalkyl, wherein C₁₋₆alkyl, C₂₋₉heterocycloalkyl, and —CH₂-C₂₋₉heterocycloalkyl are optionally substituted with one, two, or three $R^{20l}$;

each $R^{13}$ is independently selected from hydrogen, C₁₋₆alkyl;

each $R^{14}$ is independently selected from hydrogen and C₁₋₆alkyl;

each $R^{20j}$ is independently selected from halogen;

each $R^{20k}$ is independently selected from halogen, —CN, C₁₋₆alkyl, —OR²¹, —N(R²²)(R²³), —N(R²⁴)S(O)₂R²⁵, and —C(O)R²¹, wherein C₁₋₆alkyl, is optionally substituted with one, two, or three groups independently selected from halogen, —CN, C₁₋₆alkyl, C₁₋₆haloalkyl, —OR²¹, —N(R²²)(R²³);

each $R^{20t}$ is independently selected from halogen, C₃₋₁₀cycloalkyl, =NR²¹, and —N(R²²)(R²³);

each $R^{21}$ is independently selected from H and C₁₋₆haloalkyl;

each $R^{22}$ is independently selected from H and C₁₋₆alkyl;

each $R^{23}$ is independently selected from H and C₁₋₆alkyl;

each $R^{24}$ is H; and each $R^{25}$ is C₁₋₆alkyl. All variables not described in the embodiment immediately above are as described for a compound of formula (Ta), (Td), (Ua), (Ud), (Wa), or (Wd), or an embodiment thereof.

In an aspect is provided a compound of Formula (XVI), or a pharmaceutically acceptable salt or solvate thereof:

Formula (XVI)

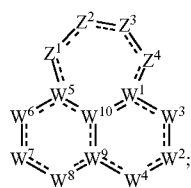

wherein:

Z¹, Z², Z³ Z⁴, W¹, R¹, R², W², R²ᵃ, W³, R³, R³ᵃ, R³ᵇ, W⁴, R³ᶜ, W⁵, R⁵, W⁶, R⁶, R⁶ᵃ, R⁶ᵇ, W⁷, R⁷ᵃ, R⁷ᶜ, R⁷ᵈ, R⁷, L⁷, W⁸, R⁸, R⁸ᵃ, R⁸ᵇ, W⁹, W¹⁰, R⁹, R⁴, L⁴, R⁴ᵇ, R⁴ᶜ, R⁴ᵈ, R⁴ᵃ, R¹¹ᶜ, R¹¹ᵈ, R¹², R¹²ᵇ, R¹³, R¹⁴, R¹⁴ᴮ, R¹⁵, R²⁰ᵃ, R²⁰ᵇ, R²⁰ᶜ, R²⁰ᵈ, R²⁰ᵉ, R²⁰ᶠ, R²⁰ᵍ, R²⁰ʰ, R²⁰ⁱ, R²⁰ʲ, R²⁰ᵏ, R²⁰ˡ, R²⁰ᵐ, R²¹, R²¹ᵇ, R²², R²³, R²⁴, and R²⁵ are as described for Formula (XVI) above, including in embodiments of a compound of Formula (XVI) above;

$R^{17}$ is

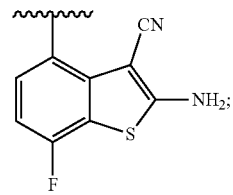 [SMILES: *c1ccc(F)c2sc(N)c(C#N)c12]

and

----- indicates a single or double bond such that all valences are satisfied.

In some embodiments of a compound of Formula (I), (II), (III), (IV), (XVI), or (XVII), or a pharmaceutically acceptable salt or solvate thereof, the compound has a formula selected from:

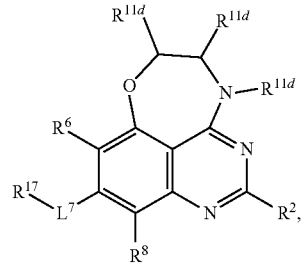

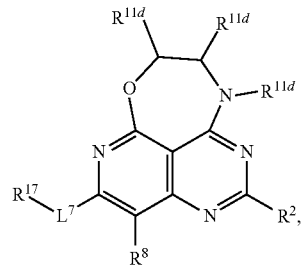

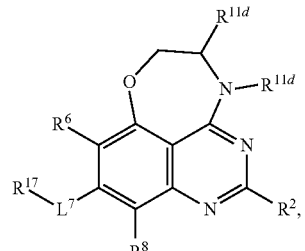

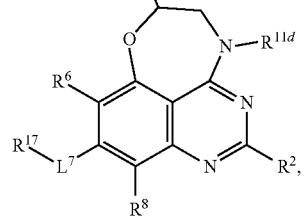

-continued

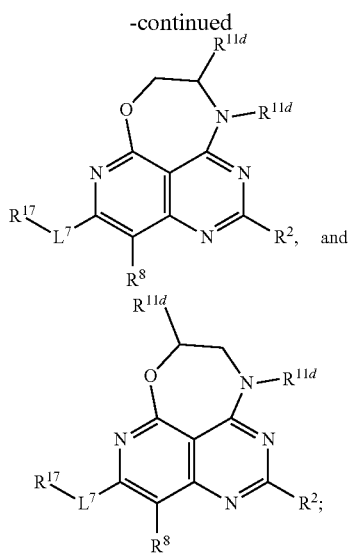

wherein

R⁶ and R⁸ are independently selected from hydrogen and halogen;

L⁷ is a bond;

R¹⁷ is selected from:

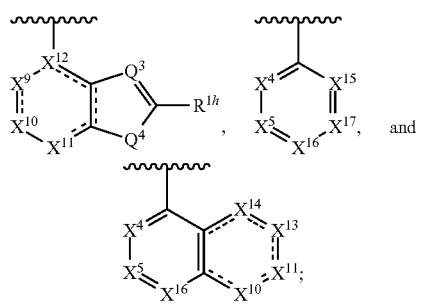

Q³ is N or C(R¹⁴); Q⁴ is S;

X⁴, X³, X¹⁵, X¹⁶, and X¹⁷ are independently selected from C(R¹ᵃ) or N;

X⁹ is C(R¹ᵃ); X¹⁰, X¹¹, X¹³, and X¹⁴ are independently C(R¹⁴) or N; X¹² is C;

each R¹ᵃ and R¹ʰ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_2$-heterocycloalkyl, —OH, —NH₂, —C(O)OH, —OC(O)NH₂, and —C(O)CH₃;

R¹ᵈ is selected from hydrogen, —CN, $C_{1-4}$alkyl, and $C_{1-6}$haloalkyl;

R² is selected from

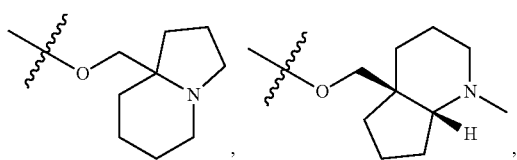

-continued

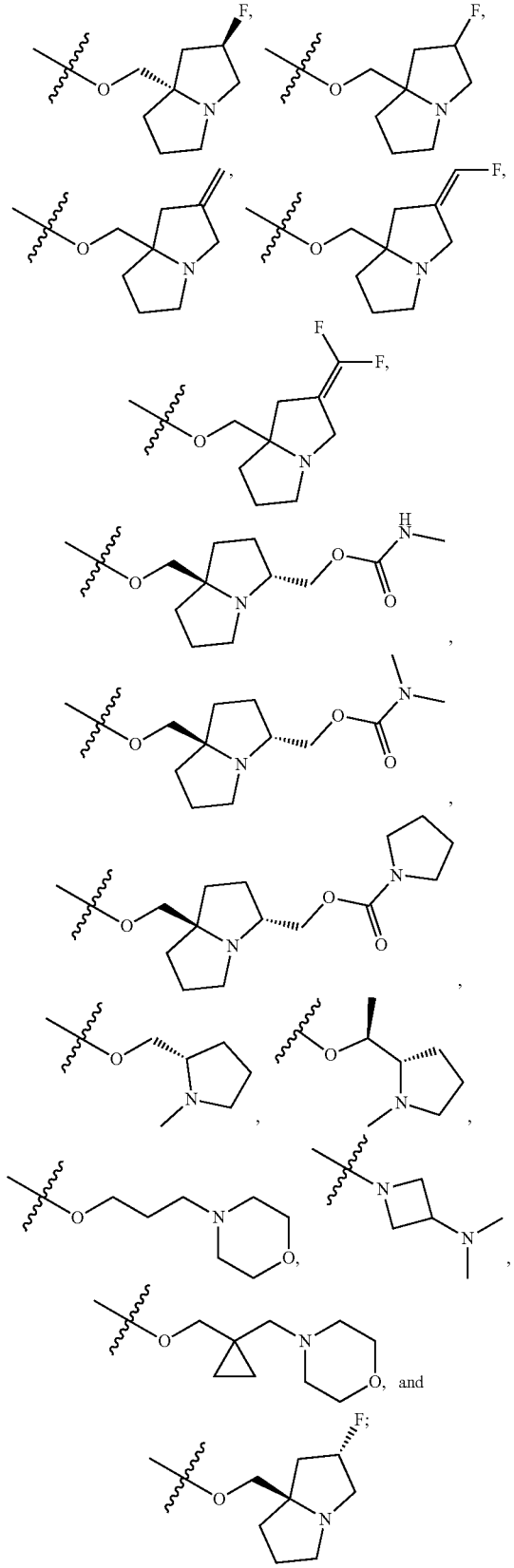

each R¹¹ᵈ is independently selected from $C_{1-6}$alkyl, $C_{2-6}$alkenyl, $C_{2-6}$alkynyl, $C_{3-12}$cycloalkyl, —CH₂-C₃-

12cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, $C_{1-11}$heteroaryl, —$(C_{1-6}$alkyl$)$-$N(R^{14})C(O)R^{12}$, wherein $C_{1-6}$alkyl, $C_{2-6}$alkenyl, $C_{2-6}$alkynyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{3-10}$cycloalkyl, $C_{2-9}$heterocycloalkyl, —$CH_2$-$C_{2-9}$heterocycloalkyl, wherein $C_{1-6}$alkyl, $C_{3-10}$cycloalkyl, $C_{2-9}$heterocycloalkyl, and —$CH_2$-$C_{2-9}$heterocycloalkyl are optionally substituted with one, two, or three $R^{20t}$;

each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{21}$, —$N(R^{22})(R^{23})$, —$C(O)N(R^{22})(R^{23})$, —$N(R^{24})C(O)R^{21}$, —$C(O)R^{21}$, and —$S(O)_2R^{25}$, wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —$OR^{21}$, and —$N(R^{22})(R^{23})$;

each $R^{20t}$ is independently selected from halogen, —$OR^{21}$, and $C_{3-10}$cycloalkyl;

each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl;

each $R^{22}$ is independently selected from H and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is independently selected from $C_{1-6}$alkyl and $C_{3-6}$cycloalkyl.

In some embodiments of a compound of Formula (I), (II), (III), (IV), (XVI), or (XVII), or a pharmaceutically acceptable salt or solvate thereof, the compound has a formula selected from:

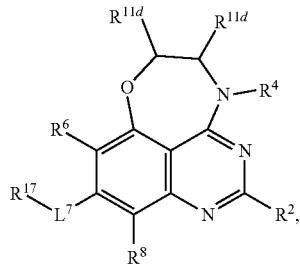

Formula (XXIIIa)

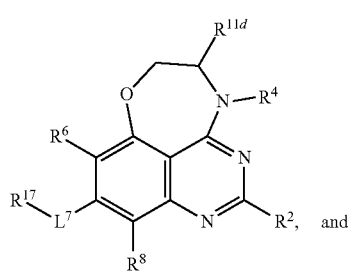

Formula (XXIa)

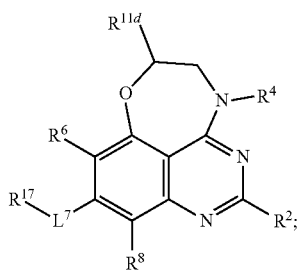

Formula (XXIIa)

wherein
$R^6$ and $R^8$ are independently selected from hydrogen and halogen;
$L^7$ is a bond;
$R^{17}$ is selected from:

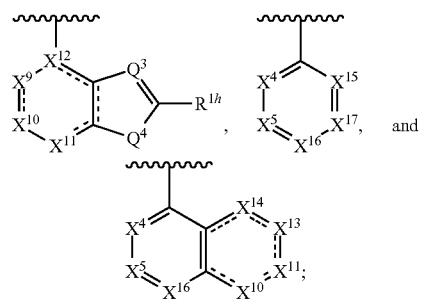

$Q^3$ is N or $C(R^{1d})$; $Q^4$ is S;
$X^4, X^3, X^{15}, X^{16}$, and $X^{17}$ are independently selected from $C(R^{1a})$ or N;
$X^9$ is $C(R^{1a})$; $X^{10}, X^{11}, X^{13}$, and $X^{14}$ are independently $C(R^{1a})$ or N; $X^{12}$ is C;
each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —$NH_2$, —C(O)OH, —OC(O)$NH_2$, and —C(O)$CH_3$;
$R^{1d}$ is selected from hydrogen, —CN, $C_{1-4}$alkyl, $C_{1-4}$haloalkyl, and $C_{3-4}$cycloalkyl;
$R^2$ is selected from

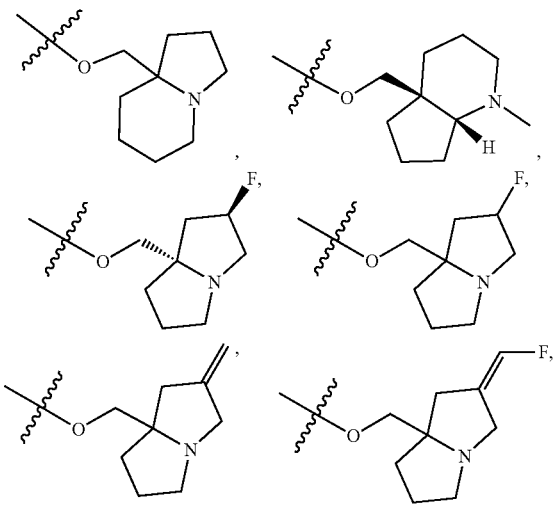

-continued

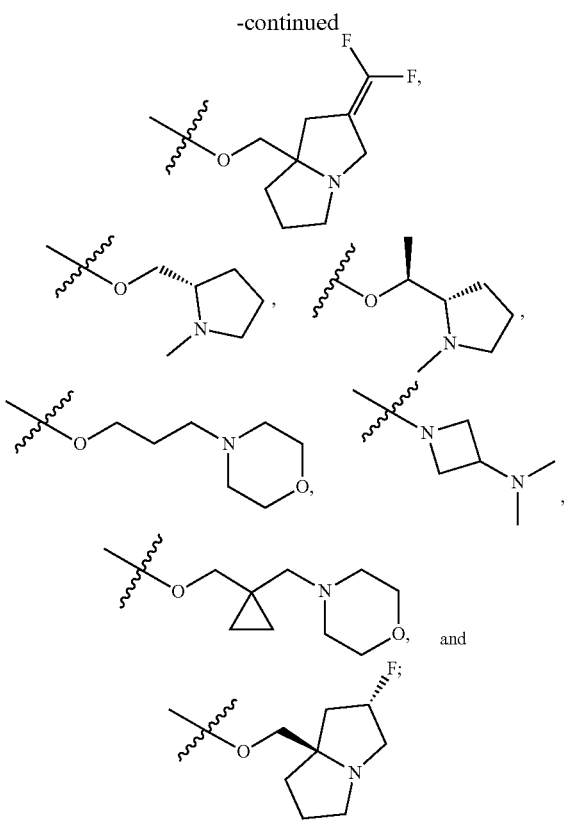

$R^2$ is selected from
$R^4$ is $-L^4-R^{4a}$;
$L^4$ is a bond or $CR^{4c}R^4$;
each $R^{4c}$ is independently selected from hydrogen and $C_{1-3}$alkyl;
each $R^{4a}$ is independently selected from $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl, wherein $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl are optionally substituted with one, two, three, or four $R^{4b}$;
each $R^{4b}$ is independently selected from halogen, oxo, —CN, $C_{1-3}$alkyl, $C_{2-6}$alkenyl, $C_{3-6}$cycloalkyl, $C_{2-11}$heterocycloalkyl, —OR$^{12}$, —N(R$^{12}$)(R$^{13}$), =C(R$^{21b})_2$, —C(O)R$^{12}$, —N(R$^{14}$)C(O)R$^{12}$, —S(O)$_2$R$^{15}$, and —C(O)N(R$^{12}$)(R$^{13}$), wherein $C_{1-6}$alkyl, $C_{3-12}$cycloalkyl, and $C_{2-11}$heterocycloalkyl, are optionally substituted with one or more $R^{20j}$;
each $R^{11d}$ is independently selected from $C_{1-3}$alkyl, $C_{2-3}$alkenyl, $C_{2-3}$alkynyl, $C_{3-4}$cycloalkyl, —CH$_2$-$C_{3-4}$cycloalkyl, 4-6 membered heterocycloalkyl, phenyl, 5 membered heteroaryl, —($C_{1-6}$alkyl)-N(R$^{14}$)C(O)R$^{12}$, wherein $C_{1-3}$alkyl, $C_{2-3}$alkenyl, $C_{2-3}$alkynyl, $C_{3-4}$cycloalkyl, —CH$_2$-$C_{3-4}$cycloalkyl, 4-6 membered heterocycloalkyl, phenyl, and 5 membered heteroaryl are optionally substituted with one, two, or three $R^{20k}$;
each $R^{12}$ is independently selected from hydrogen, $C_{1-3}$alkyl, $C_{2-6}$alkenyl, $C_{3-6}$cycloalkyl, 3-6 membered heterocycloalkyl, —CH$_2$-(3-6 membered heterocycloalkyl), and 5-6 membered heteroaryl, wherein $C_{1-3}$alkyl, $C_{2-6}$alkenyl, $C_{3-6}$cycloalkyl, 3-6 membered heterocycloalkyl, —CH$_2$-(3-6 membered heterocycloalkyl), and 5-6 membered heteroaryl are optionally substituted with one, two, or three $R^{20r}$;
each $R^{13}$ is independently selected from hydrogen and $C_{1-3}$alkyl;
each $R^{14}$ is independently selected from hydrogen, $C_{1-3}$alkyl, and $C_{1-6}$haloalkyl;
each $R^{15}$ is independently selected $C_{3-6}$cycloalkyl;
each $R^{20j}$ is independently selected from halogen, —CN, $C_{1-6}$alkyl, $C_{3-10}$cycloalkyl, $C_{2-9}$heterocycloalkyl, $C_{6-10}$aryl, $C_{1-9}$heteroaryl, —OR$^{21}$, —N(R$^{22}$)(R$^{23}$), and —N(R$^{24}$)C(O)R$^{25}$, wherein $C_{1-6}$alkyl, $C_{3-10}$cycloalkyl $C_{2-9}$heterocycloalkyl, $C_{6-10}$aryl, and $C_{1-9}$heteroaryl are optionally substituted with one, two, or three groups independently selected from halogen;
each $R^{20k}$ is independently selected from oxo, $C_{1-3}$alkyl, $C_{3-4}$cycloalkyl, halogen, —CN, —OR$^{21}$, —N(R$^{22}$)(R$^{23}$), —N(R$^{24}$)S(O)$_2$R$^{25}$, —C(O)R$^{21}$, and —N(R$^{24}$)C(O)R$^{21}$;
each $R^{20r}$ is independently selected from halogen, —CN, $C_{1-3}$alkyl, $C_{3-6}$cycloalkyl, $C_{2-9}$heterocycloalkyl, $C_{6-10}$aryl, $C_{1-9}$heteroaryl, —OR$^{21}$, —N(R$^{22}$)(R$^{23}$), and —N(R$^{24}$)C(O)R$^{25}$, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three groups independently selected from halogen;
each $R^{21}$ is independently selected from H, $C_{1-3}$alkyl, $C_{1-3}$haloalkyl, $C_{3-6}$cycloalkyl, 3-4 membered heterocycloalkyl, and $C_{1-9}$heteroaryl;
each $R^{21b}$ is independently selected from H and halogen;
each $R^{22}$ is independently selected from H and $C_{1-3}$alkyl;
each $R^{23}$ is independently selected from H and $C_{1-3}$alkyl;
each $R^{24}$ is independently selected from H and $C_{1-3}$alkyl; and
each $R^{25}$ is independently selected from $C_{1-3}$alkyl, $C_{3-6}$cycloalkyl, and $C_{2-9}$heterocycloalkyl.

In embodiments of the formula immediately above, each $R^{11d}$ is independently selected from $C_{2-3}$alkenyl, $C_{2-3}$alkynyl, $C_{3-4}$cycloalkyl, —CH$_2$-$C_{3-4}$cycloalkyl, 4-6 membered heterocycloalkyl, phenyl, 5 membered heteroaryl, —($C_{1-6}$alkyl)-N(R$^{14}$)C(O)R$^{12}$, wherein $C_{2-3}$alkenyl, $C_{2-3}$alkynyl, $C_{3-4}$cycloalkyl, —CH$_2$-$C_{3-4}$cycloalkyl, 4-6 membered heterocycloalkyl, phenyl, and 5 membered heteroaryl are optionally substituted with one, two, or three $R^{20k}$;

In some embodiments of a compound of Formula (I), (II), (III), (IV), (XVI), or (XVII), or a pharmaceutically acceptable salt or solvate thereof, the compound has a formula selected from:

Formula (XXIIIa)

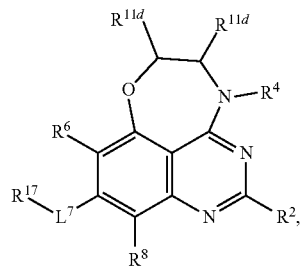

-continued

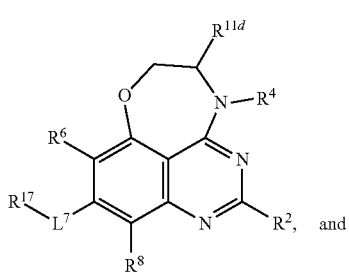

Formula (XXIa)

Formula (XXIIa)

wherein
R⁶ and R⁸ are independently selected from hydrogen and halogen;
L⁷ is a bond;
R¹⁷ is selected from:

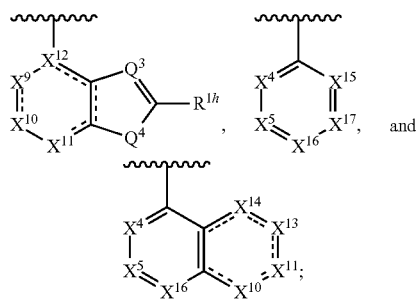

$Q^3$ is N or $C(R^{14})$; $Q^4$ is S;
$X^4, X^5, X^{15}, X^{16}$, and $X^{17}$ are independently selected from $C(R^{1a})$ or N;
$X^9$ is $C(R^{1a})$; $X^{10}, X^{11}, X^{13}$, and $X^{14}$ are independently $C(R^{1a})$ or N; $X^{12}$ is C;
each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH₂, —C(O)OH, —OC(O)NH₂, and —C(O)CH₃;
$R^{1d}$ is selected from hydrogen, —CN, $C_{1-4}$alkyl, $C_{1-4}$haloalkyl, and $C_{3-4}$cycloalkyl;
R² is selected from

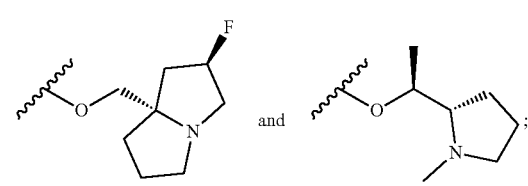

$R^4$ is $-L^4-R^{4a}$;
$L^4$ is a bond or $CR^4R^4$;
each $R^4$ is independently selected from hydrogen and $C_{1-3}$alkyl;
each $R^{4a}$ is independently selected from $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl, wherein $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl are optionally substituted with one, two, three, or four $R^{4b}$;
each $R^{4b}$ is independently selected from halogen, oxo, —CN, $C_{1-3}$alkyl, $C_{3-6}$cycloalkyl, —OR¹², —N(R¹²)(R¹³), =C(R^{21b})_2, —C(O)R¹², —N(R¹⁴)C(O)R¹², —S(O)₂R¹⁵, and —C(O)N(R¹²)(R¹³), wherein $C_{1-3}$alkyl and $C_{3-6}$cycloalkyl are optionally substituted with one or more $R^{20j}$;
each $R^{11d}$ is independently selected from $C_{1-3}$alkyl, $C_{2-3}$alkenyl, $C_{2-3}$alkynyl, $C_{3-4}$cycloalkyl, —CH₂-$C_{3-4}$cycloalkyl, 4-6 membered heterocycloalkyl, phenyl, 5 membered heteroaryl, —($C_{1-6}$alkyl)-N(R¹⁴)C(O)R¹², wherein $C_{1-3}$alkyl, $C_{2-3}$alkenyl, $C_{2-3}$alkynyl, $C_{3-4}$cycloalkyl, —CH₂-$C_{3-4}$cycloalkyl, 4-6 membered heterocycloalkyl, phenyl, and 5 membered heteroaryl are optionally substituted with one, two, or three $R^{20k}$;
each $R^{12}$ is independently selected from hydrogen, $C_{1-3}$alkyl, $C_{3-6}$cycloalkyl, 3-6 membered heterocycloalkyl, —CH₂-(3-6 membered heterocycloalkyl), and 5-6 membered heteroaryl, wherein $C_{1-3}$alkyl, $C_{3-6}$cycloalkyl, 3-6 membered heterocycloalkyl, —CH₂-(3-6 membered heterocycloalkyl), and 5-6 membered heteroaryl are optionally substituted with one, two, or three $R^{20l}$;
each $R^{13}$ is independently selected from hydrogen and $C_{1-3}$alkyl;
each $R^{14}$ is independently selected from hydrogen and $C_{1-3}$alkyl;
each $R^{15}$ is independently selected $C_{3-6}$cycloalkyl;
each $R^{20j}$ is independently selected from halogen and —OR²¹;
each $R^{20k}$ is independently selected from oxo, $C_{1-3}$alkyl, $C_{3-4}$cycloalkyl, halogen, —CN, —OR²¹, —N(R²²)(R²³), —N(R²⁴)S(O)₂R²⁵, —C(O)R²¹, and —N(R²⁴)C(O)R²¹;
each $R^{20l}$ is independently selected from halogen, —CN, $C_{1-3}$alkyl, $C_{3-6}$cycloalkyl, —OR²¹, and —N(R²²)(R²³), wherein $C_{1-3}$alkyl and $C_{3-6}$cycloalkyl are optionally substituted with one, two, or three groups independently selected from halogen;
each $R^{21}$ is independently selected from hydrogen, $C_{1-3}$alkyl, $C_{1-3}$haloalkyl, $C_{3-6}$cycloalkyl, and 3-4 membered heterocycloalkyl;
each $R^{21b}$ is independently selected from hydrogen and halogen;
each $R^{22}$ is independently selected from hydrogen and $C_{1-3}$alkyl;
each $R^{23}$ is independently selected from hydrogen and $C_{1-3}$alkyl;
each $R^{24}$ is independently selected from hydrogen and $C_{1-3}$alkyl; and
each $R^{25}$ is independently selected from $C_{1-3}$alkyl.

In embodiments of the formula immediately above, each $R^{11d}$ is independently selected from $C_{2-3}$alkenyl, $C_{2-3}$alkynyl, $C_{3-4}$cycloalkyl, —CH₂-$C_{3-4}$cycloalkyl, 4-6 membered heterocycloalkyl, phenyl, 5 membered heteroaryl, —(C$_{1-6}$alkyl)-N(R$^{14}$)C(O)R$^{12}$, wherein C$_{2-3}$alkenyl, C$_{2-3}$alkynyl, C$_{3-4}$cycloalkyl, —CH$_2$-C$_{3-4}$cycloalkyl, 4-6 membered heterocycloalkyl, phenyl, and 5 membered heteroaryl are optionally substituted with one, two, or three R$^{20k}$;

In some embodiments of a compound of Formula (I), (II), (III), (IV), (XVI), or (XVII), or a pharmaceutically acceptable salt or solvate thereof, the compound has a formula selected from:

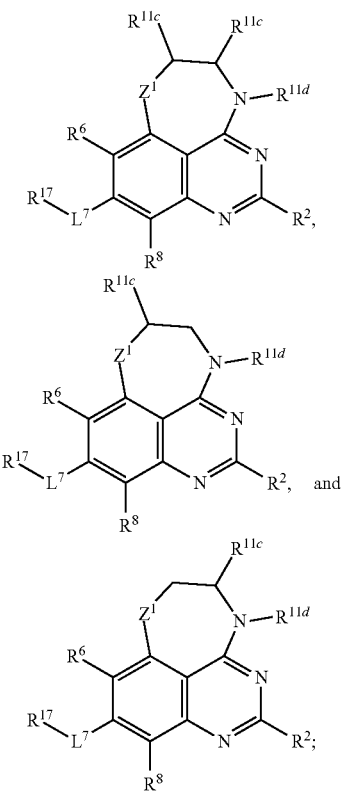

wherein
Z$^1$ is O;
R$^6$ and R$^8$ are independently selected from hydrogen and halogen;
L$^7$ is a bond;
R$^{17}$ is selected from:

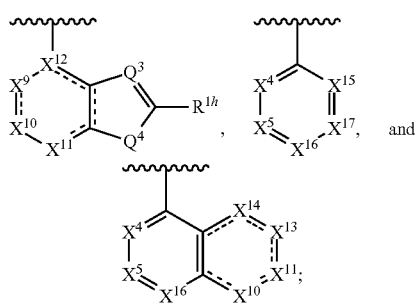

Q$^3$ is N or C(R$^{14}$); Q$^4$ is S;
X$^4$, X$^5$, X$^{15}$, X$^{16}$, and X$^{17}$ are independently selected from C(R$^{1a}$) or N;
X$^9$ is C(R$^{1a}$); X$^{10}$, X$^{11}$, X$^{13}$, and X$^{14}$ are independently C(R$^{1a}$) or N; X$^{12}$ is C;

each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;

R$^{1d}$ is selected from hydrogen, —CN, C$_{1-4}$alkyl, and C$_{1-4}$haloalkyl;

R$^2$ is selected from

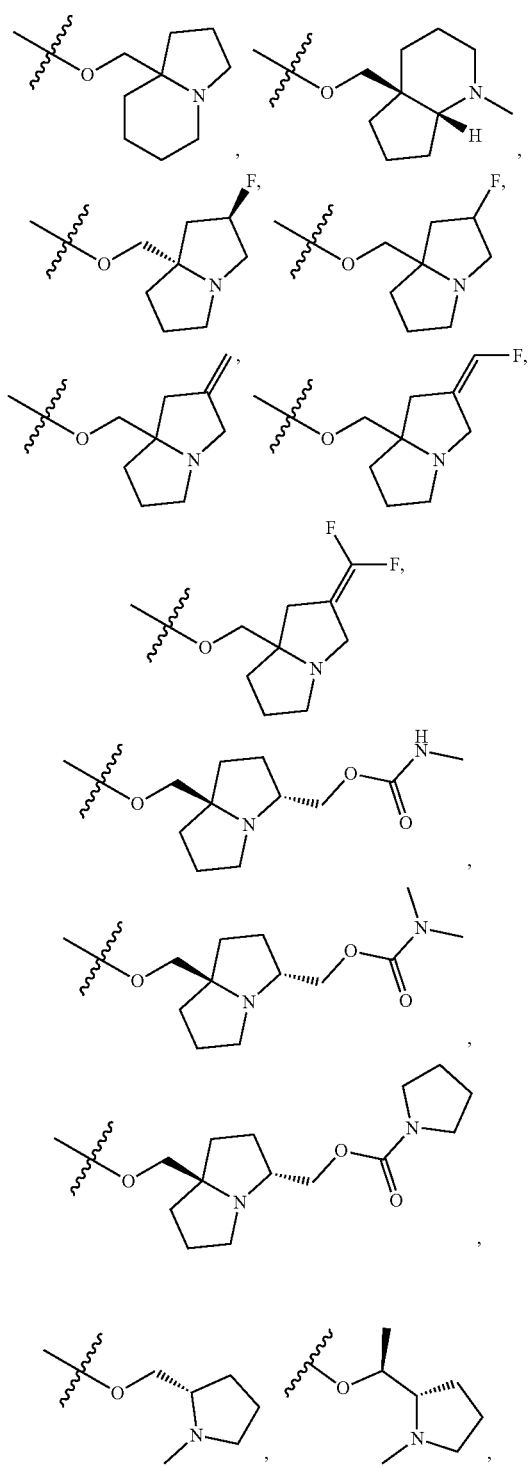

-continued

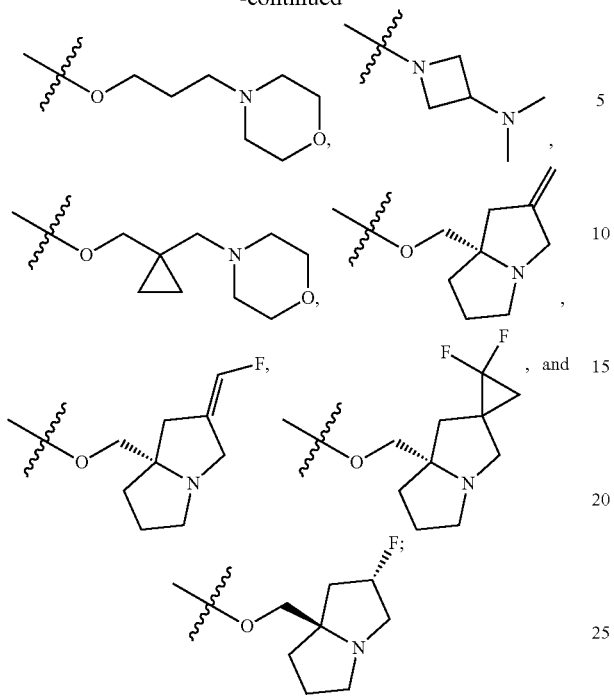

, and each $R^{11c}$ is independently selected from $C_{1-3}$alkyl, $C_{2-3}$alkenyl, $C_{2-3}$alkynyl, $C_{3-4}$cycloalkyl, —CH$_2$-C$_{3-4}$cycloalkyl, 4-6 membered heterocycloalkyl, phenyl, 5 membered heteroaryl, —(C$_{1-6}$alkyl)-N(R$^{14}$)C(O)R$^{12}$, wherein $C_{1-3}$alkyl, $C_{2-3}$alkenyl, $C_{2-3}$alkynyl, $C_{3-4}$cycloalkyl, —CH$_2$-C$_{3-4}$cycloalkyl, 4-6 membered heterocycloalkyl, phenyl, and 5 membered heteroaryl are optionally substituted with one, two, or three $R^{20k}$;

each $R^{11d}$ is independently selected from $C_{1-4}$alkyl, $C_2$-alkenyl, $C_{2-6}$alkynyl, $C_{3-7}$cycloalkyl, —CH$_2$—(C$_{3-7}$cycloalkyl), 4-7 membered monocyclic heterocycloalkyl, —CH$_2$-(4-7 membered monocyclic heterocycloalkyl), 6-9 membered fused heterocycloalkyl, 6-9 membered spirocyclic heterocycloalkyl, 6-8 membered bridged heterocycloalkyl, phenyl, 5-6 membered heteroaryl, —CH$_2$-(5-6 membered heteroaryl), and —(C$_{1-4}$alkyl)-N(R$^{14}$)C(O)R$^{12}$, wherein $C_{1-4}$alkyl, $C_2$-alkenyl, $C_{2-6}$alkynyl, $C_{3-7}$cycloalkyl, —CH$_2$—(C$_{3-7}$cycloalkyl), 4-7 membered monocyclic heterocycloalkyl, —CH$_2$-(4-7 membered monocyclic heterocycloalkyl), 6-9 membered fused heterocycloalkyl, 6-9 membered spirocyclic heterocycloalkyl, 6-8 membered bridged heterocycloalkyl, phenyl, 5-6 membered heteroaryl, and —CH$_2$-(5-6 membered heteroaryl) are optionally substituted with one, two, or three $R^{20k}$;

each $R^{12}$ is independently selected from hydrogen, $C_{1-3}$alkyl, $C_{3-6}$cycloalkyl, 3-6 membered heterocycloalkyl, —CH$_2$-(3-6 membered heterocycloalkyl), and 5-6 membered heteroaryl, wherein $C_{1-3}$alkyl, $C_{3-6}$cycloalkyl, 3-6 membered heterocycloalkyl, —CH$_2$-(3-6 membered heterocycloalkyl), and 5-6 membered heteroaryl are optionally substituted with one, two, or three $R^{201}$;

each $R^{14}$ is independently selected from hydrogen and $C_{1-3}$alkyl;

each $R^{20k}$ is independently selected from halogen, oxo, —CN, $C_{1-3}$alkyl, $C_{3-6}$cycloalkyl, =C(R$^{21b}$)$_2$, —OR$^{21}$, —N(R$^{22}$)(R$^{23}$), —N(R$^{24}$)S(O)$_2$R$^{25}$, —C(O)R$^{21}$, —N(R$^{24}$)C(O)R$^{21}$, S(O)$_2$R$^{25}$, and —C(O)N(R$^{22}$)(R$^{23}$), wherein $C_{1-3}$alkyl and $C_{3-6}$cycloalkyl are optionally substituted with one, two, or three groups independently selected from halogen and —OR$^{21}$;

each $R^{20t}$ is independently selected from halogen, —CN, $C_{1-3}$alkyl, $C_{3-6}$cycloalkyl, —OR$^{21}$, —S(O)$_2$R$^{25}$, and —N(R$^{22}$)(R$^{23}$), wherein $C_{1-3}$alkyl and $C_{3-6}$cycloalkyl are optionally substituted with one, two, or three groups independently selected from halogen;

each $R^{21}$ is independently selected from hydrogen, $C_{1-3}$alkyl, $C_{1-3}$haloalkyl, $C_{3-6}$cycloalkyl, and 3-4 membered heterocycloalkyl;

each $R^{22}$ is independently selected from hydrogen and $C_{1-3}$alkyl;

each $R^{23}$ is independently selected from hydrogen and $C_{1-3}$alkyl;

each $R^{24}$ is independently selected from hydrogen and $C_{1-3}$alkyl; and each $R^{25}$ is independently selected from $C_{1-3}$alkyl.

In embodiments of the formula immediately above, each $R^{11c}$ is independently selected from $C_{2-3}$alkenyl, $C_{2-3}$alkynyl, $C_{3-4}$cycloalkyl, —CH$_2$-C$_{3-4}$cycloalkyl, 4-6 membered heterocycloalkyl, phenyl, 5 membered heteroaryl, —(C$_{1-6}$alkyl)-N(R$^{14}$)C(O)R$^{12}$, wherein $C_{2-3}$alkenyl, $C_{2-3}$alkynyl, $C_{3-4}$cycloalkyl, —CH$_2$-C$_{3-4}$cycloalkyl, 4-6 membered heterocycloalkyl, phenyl, and 5 membered heteroaryl are optionally substituted with one, two, or three $R^{20k}$.

In some embodiments of a compound of Formula (I), (II), (III), (IV), (XVI), or (XVII), or a pharmaceutically acceptable salt or solvate thereof, the compound has a formula selected from:

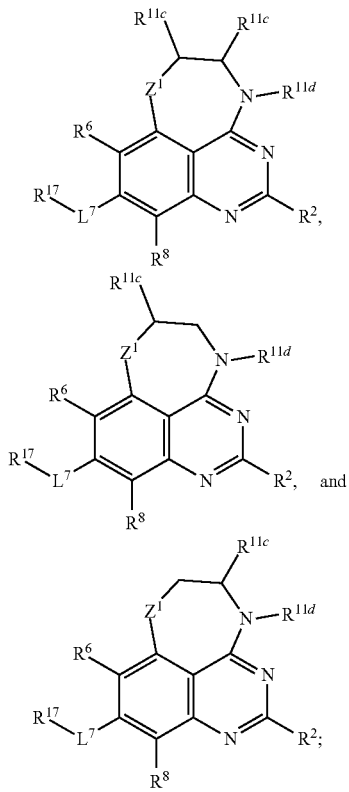

wherein
Z¹ is O;
R⁶ and R⁸ are independently selected from hydrogen and halogen;
L⁷ is a bond;
R¹⁷ is selected from:

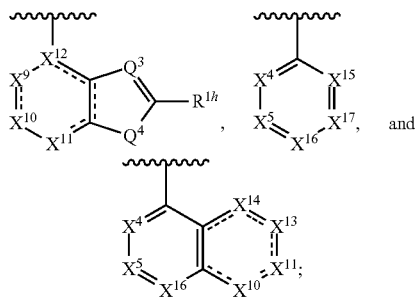

Q³ is N or C(R¹ᵈ); Q⁴ is S;
X⁴, X³, X¹⁵, X¹⁶, and X¹⁷ are independently selected from C(R¹ᵃ) or N;
X⁹ is C(R¹ᵃ); X¹⁰, X¹¹, X¹³, and X¹⁴ are independently C(R¹ᵃ) or N; X¹² is C;
each R¹ᵃ and R¹ʰ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH₂, —C(O)OH, —OC(O)NH₂, and —C(O)CH₃;
R¹ᵈ is selected from hydrogen, —CN, $C_{1-4}$alkyl, and $C_{1-4}$haloalkyl;
R² is selected from

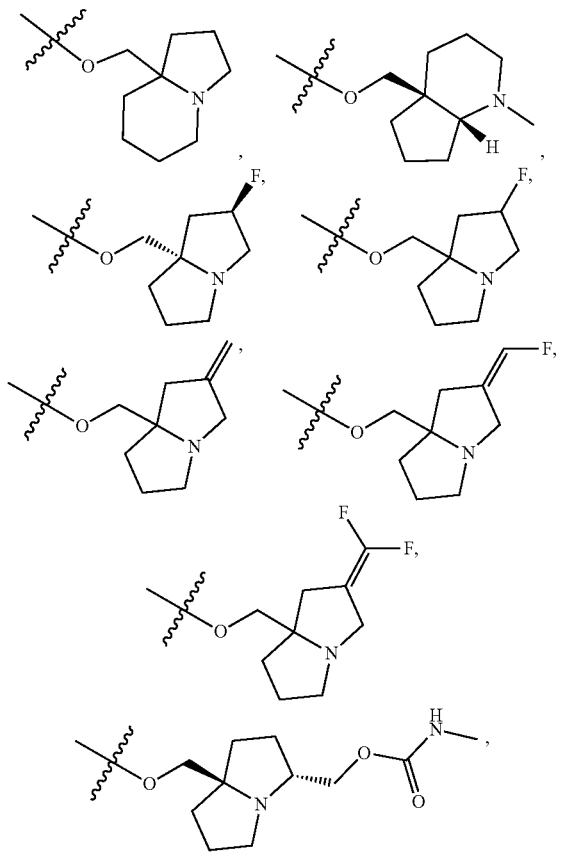

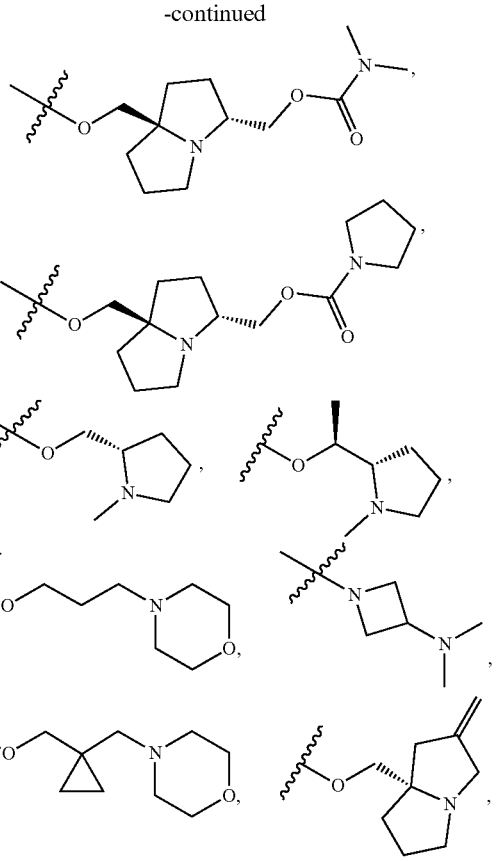

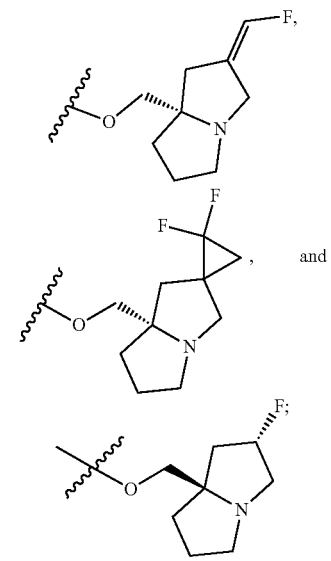

each R¹¹ᶜ is independently selected from $C_{1-3}$alkyl, $C_{2-3}$alkenyl, $C_{2-3}$alkynyl, $C_{3-4}$cycloalkyl, —CH₂-$C_{3-4}$cycloalkyl, 4-6 membered heterocycloalkyl, phenyl, 5 membered heteroaryl, —($C_{1-6}$alkyl)-N(R¹⁴)C(O)R¹², wherein $C_{1-3}$alkyl, $C_{2-3}$alkenyl, $C_{2-3}$alkynyl, $C_{3-4}$cycloalkyl, —CH₂-$C_{3-4}$cycloalkyl, 4-6 membered heterocycloalkyl, phenyl, and 5 membered heteroaryl are optionally substituted with one, two, or three R²⁰ᵏ;
each R¹¹ᵈ is independently selected from $C_{1-4}$alkyl, $C_2$-alkenyl, and —($C_{1-4}$alkyl)-N(R¹⁴)C(O)R¹², wherein $C_{1-4}$alkyl and $C_2$-alkenyl are optionally substituted with one, two, or three R²⁰ᵏ;

each $R^{12}$ is independently selected from hydrogen, $C_{1-3}$alkyl, $C_{3-6}$cycloalkyl, 3-6 membered heterocycloalkyl, —$CH_2$-(3-6 membered heterocycloalkyl), and 5-6 membered heteroaryl, wherein $C_{1-3}$alkyl, $C_{3-6}$cycloalkyl, 3-6 membered heterocycloalkyl, —$CH_2$-(3-6 membered heterocycloalkyl), and 5-6 membered heteroaryl are optionally substituted with one, two, or three $R^{201}$;

each $R^{14}$ is independently selected from hydrogen and $C_{1-3}$alkyl;

each $R^{20k}$ is independently selected from oxo, $C_{1-3}$alkyl, $C_{3-4}$cycloalkyl, halogen, —CN, —$OR^{21}$, —$N(R^{22})(R^{23})$, —$N(R^{24})S(O)_2R^{25}$, —$C(O)R^{21}$, and —$N(R^{24})C(O)R^{21}$;

each $R^{20t}$ is independently selected from halogen, —CN, $C_{1-3}$alkyl, $C_{3-6}$cycloalkyl, —$OR^{21}$, —$S(O)_2R^{25}$, and —$N(R^{22})(R^{23})$, wherein $C_{1-3}$alkyl and $C_{3-6}$cycloalkyl are optionally substituted with one, two, or three groups independently selected from halogen;

each $R^{21}$ is independently selected from hydrogen, $C_{1-3}$alkyl, $C_{1-3}$haloalkyl, $C_{3-6}$cycloalkyl, and 3-4 membered heterocycloalkyl;

each $R^{22}$ is independently selected from hydrogen and $C_{1-3}$alkyl;

each $R^{23}$ is independently selected from hydrogen and $C_{1-3}$alkyl;

each $R^{24}$ is independently selected from hydrogen and $C_{1-3}$alkyl; and each $R^{25}$ is independently selected from $C_{1-3}$alkyl.

In embodiments of the formula immediately above, each $R^{11c}$ is independently selected from $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, 5 membered heteroaryl, —($C_{1-6}$alkyl)-$N(R^{14})C(O)R^{12}$, wherein $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, and 5 membered heteroaryl are optionally substituted with one, two, or three $R^{20k}$;

In some embodiments of a compound of Formula (I), (II), (III), (IV), (XVI), or (XVII), or a pharmaceutically acceptable salt or solvate thereof, the compound has a formula selected from:

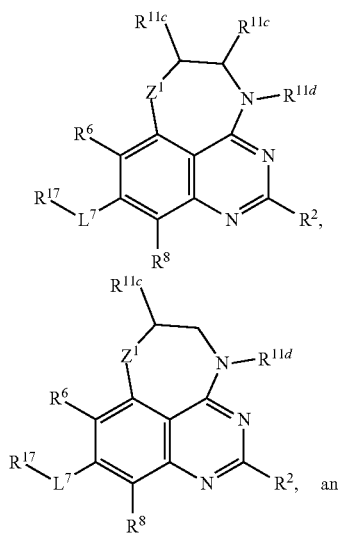

-continued

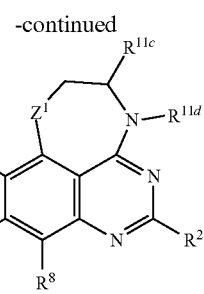

wherein
$Z^1$ is O;
$R^6$ and $R^8$ are independently selected from hydrogen and halogen;
$L^7$ is a bond;
$R^{17}$ is selected from:

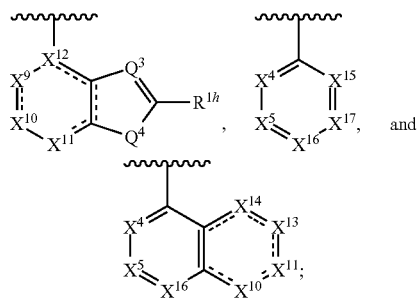

$Q^3$ is N or $C(R^{14})$; $Q^4$ is S;
$X^4$, $X^5$, $X^{15}$, $X^{16}$, and $X^{17}$ are independently selected from $C(R^{1a})$ or N;
$X^9$ is $C(R^{18})$; $X^{10}$, $X^{11}$, $X^{13}$, and $X^{14}$ are independently $C(R^{1a})$ or N; $X^{12}$ is C;
each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —$NH_2$, —$C(O)OH$, —$OC(O)NH_2$, and —$C(O)CH_3$;
$R^{1d}$ is selected from hydrogen, —CN, $C_{1-4}$alkyl, and $C_{1-4}$haloalkyl;
$R^2$ is selected from

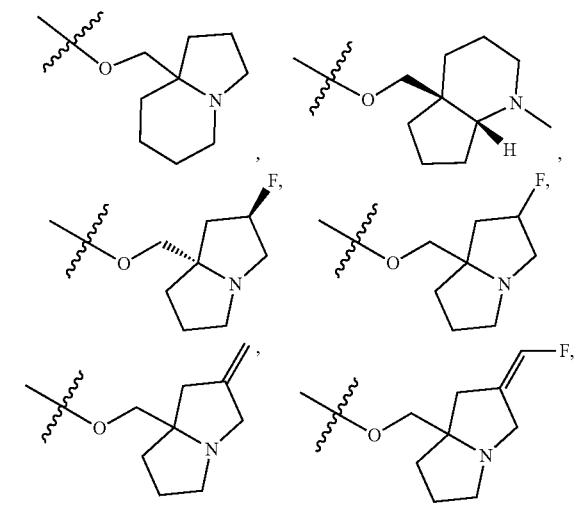

-continued

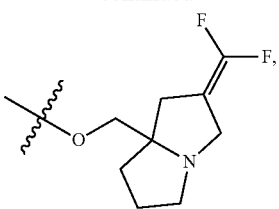

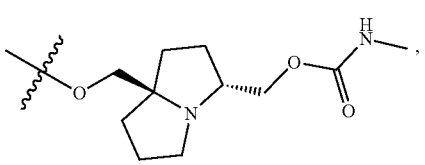

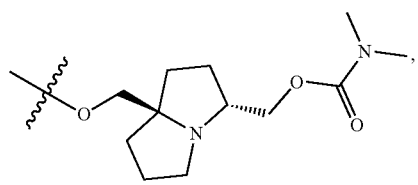

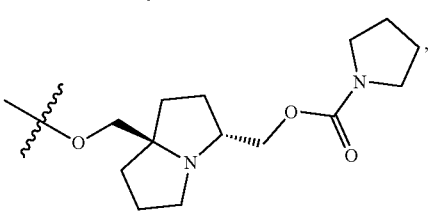

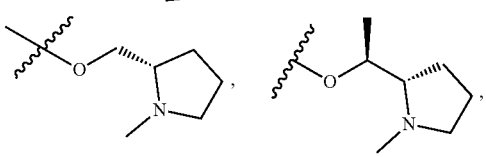

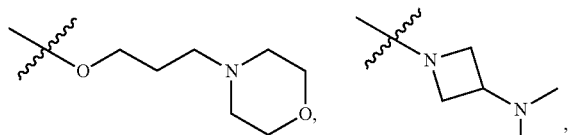

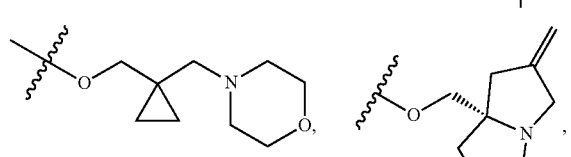

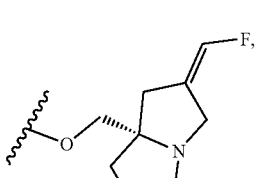

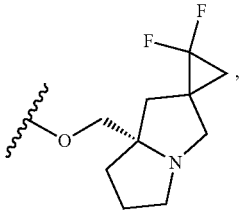

and

-continued

each $R^{11c}$ independently selected from hydrogen, $C_{2-3}$alkenyl, $C_{2-3}$alkynyl, $C_{3-4}$cycloalkyl, —CH$_2$—($C_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl), wherein $C_{2-3}$alkenyl, $C_{2-3}$alkynyl, $C_{3-4}$cycloalkyl, —CH$_2$—($C_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl) are optionally substituted with one, two, or three $R^{20k}$;

each $R^{11d}$ is independently selected from $C_{1-4}$alkyl, $C_{3-4}$cycloalkyl, —CH$_2$-C$_{3-4}$cycloalkyl, and 5-6 membered heterocycloalkyl, wherein $C_{1-4}$alkyl, $C_{3-4}$cycloalkyl, —CH$_2$-C$_{3-4}$cycloalkyl, and 5-6 membered heterocycloalkyl are optionally substituted with one, two, or three $R^{20k}$;

each $R^{20k}$ is independently selected from halogen, —CN, $C_{1-3}$alkyl, —NHC(O)R$^{21}$, and —OR$^{21}$, wherein $C_{1-3}$alkyl is optionally substituted with one, two, or three groups independently selected from halogen and —CN; and each $R^{21}$ is independently selected from H, $C_{1-3}$alkyl, $C_{1-3}$haloalkyl, and 3-4 membered heterocycloalkyl. In embodiments of the formulae above, $R^{11d}$ is independently selected from

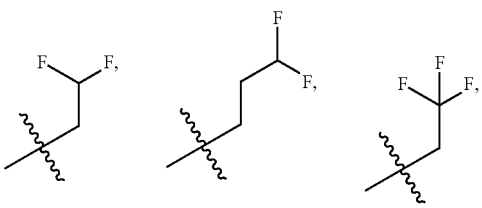

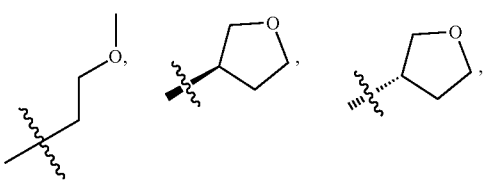

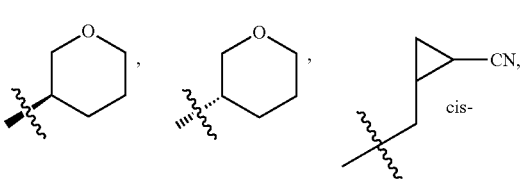

411
-continued
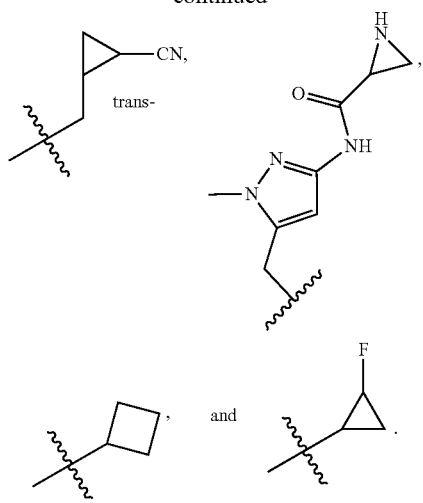
In embodiments of the formulae above, $R^{11c}$ is independently selected from
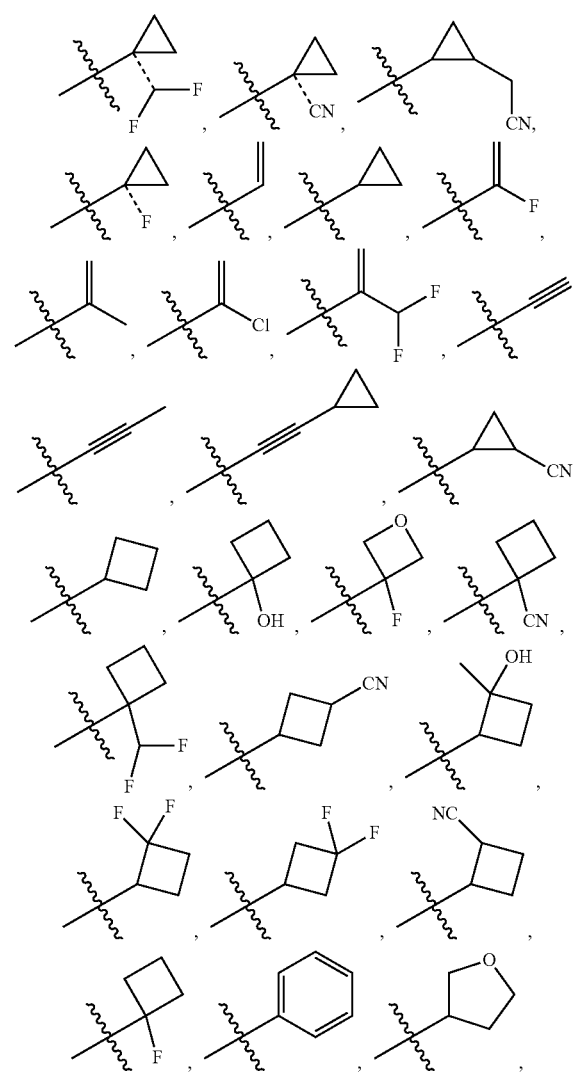
412
-continued
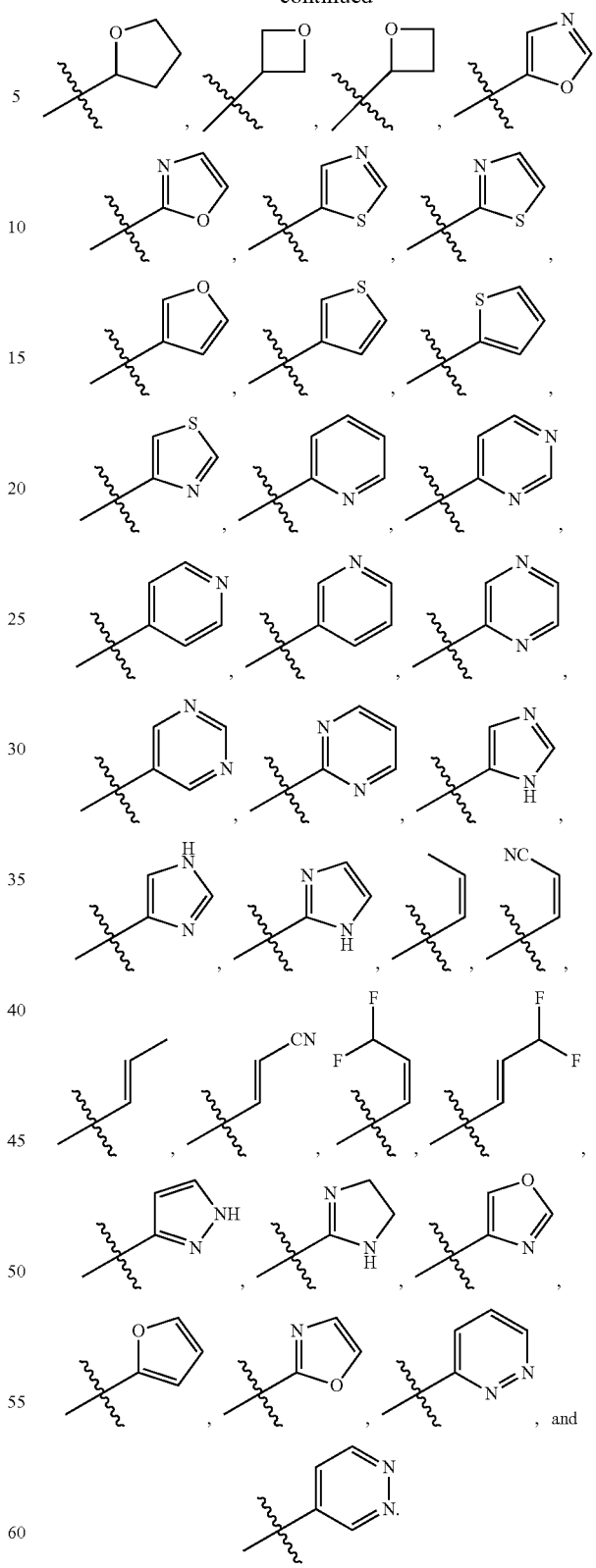
In some embodiments of a compound of Formula (I), (II), (III), (IV), (XVI), or (XVII), or a pharmaceutically acceptable salt or solvate thereof, the compound has a formula selected from:

413
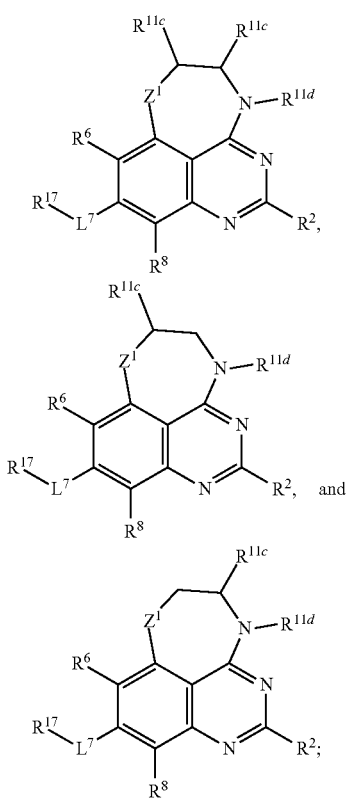
wherein
Z¹ is O;
R⁶ and R⁸ are independently selected from hydrogen and halogen;
L⁷ is a bond;
R¹⁷ is
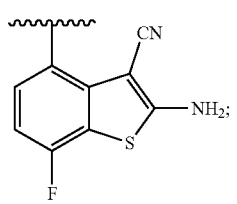 [SMILES: *c1ccc(F)c2sc(N)c(C#N)c12]
R³ is selected from
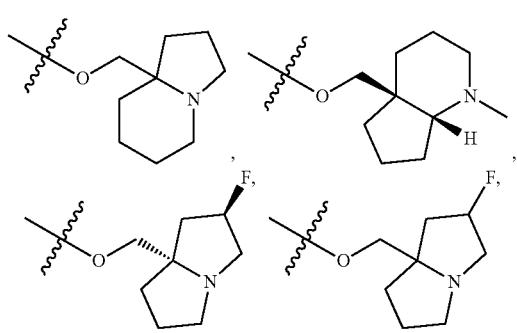
414
-continued
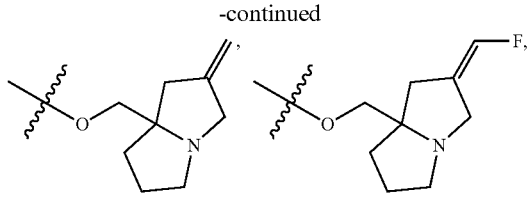
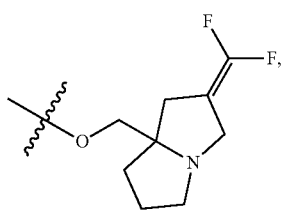
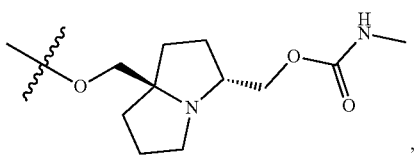
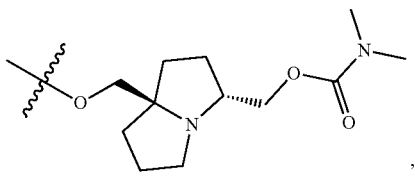
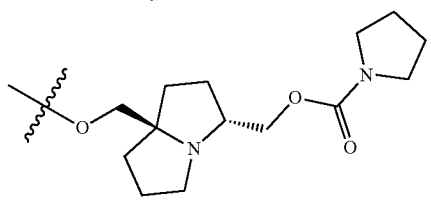
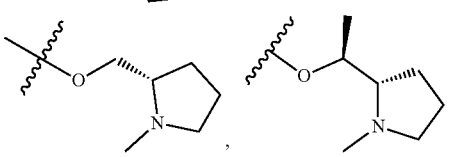
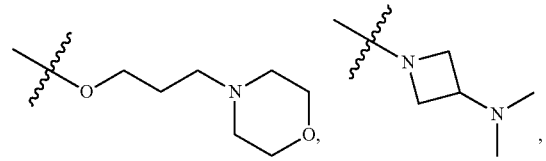
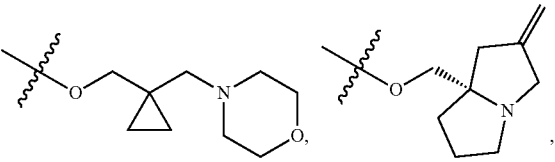
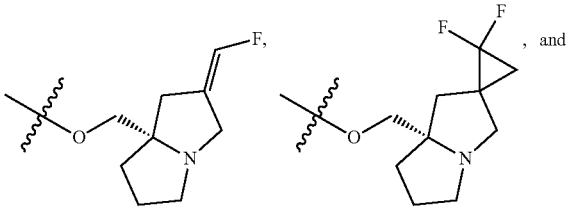

-continued

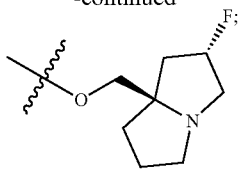

each $R^{11c}$ independently selected from hydrogen, $C_{2-3}$alkenyl, $C_{2-3}$alkynyl, $C_{3-4}$cycloalkyl, 4-5 membered heterocycloalkyl, phenyl, and 5-6 membered heteroaryl, wherein $C_{2-3}$alkenyl, $C_{2-3}$alkynyl, $C_{3-4}$cycloalkyl, 4-5 membered heterocycloalkyl, phenyl, and 5-6 membered heteroaryl are optionally substituted with one, two, or three $R^{20k}$;

each $R^{11d}$ is independently selected from $C_{1-4}$alkyl, $C_{3-4}$cycloalkyl, —CH$_2$-C$_{3-4}$cycloalkyl, and 5-6 membered heterocycloalkyl, wherein $C_{1-4}$alkyl, $C_{3-4}$cycloalkyl, —CH$_2$-C$_{3-4}$cycloalkyl, and 5-6 membered heterocycloalkyl are optionally substituted with one, two, or three $R^{20k}$;

each $R^{20k}$ is independently selected from halogen, —CN, $C_{1-3}$alkyl, —NHC(O)$R^{21}$, and —OR$^{21}$, wherein $C_{1-3}$alkyl is optionally substituted with one, two, or three groups independently selected from halogen and —CN; and each $R^{21}$ is independently selected from H, $C_{1-3}$alkyl, $C_{1-3}$haloalkyl, and 3-4 membered heterocycloalkyl. In embodiments of the formulae above, $R^{11d}$ is independently selected from

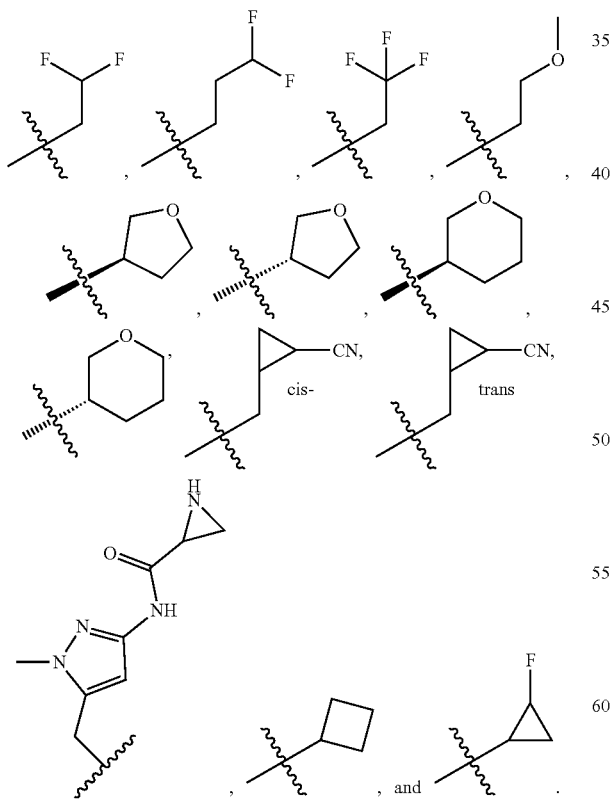

In embodiments of the formulae above, $R^{11c}$ is independently selected from

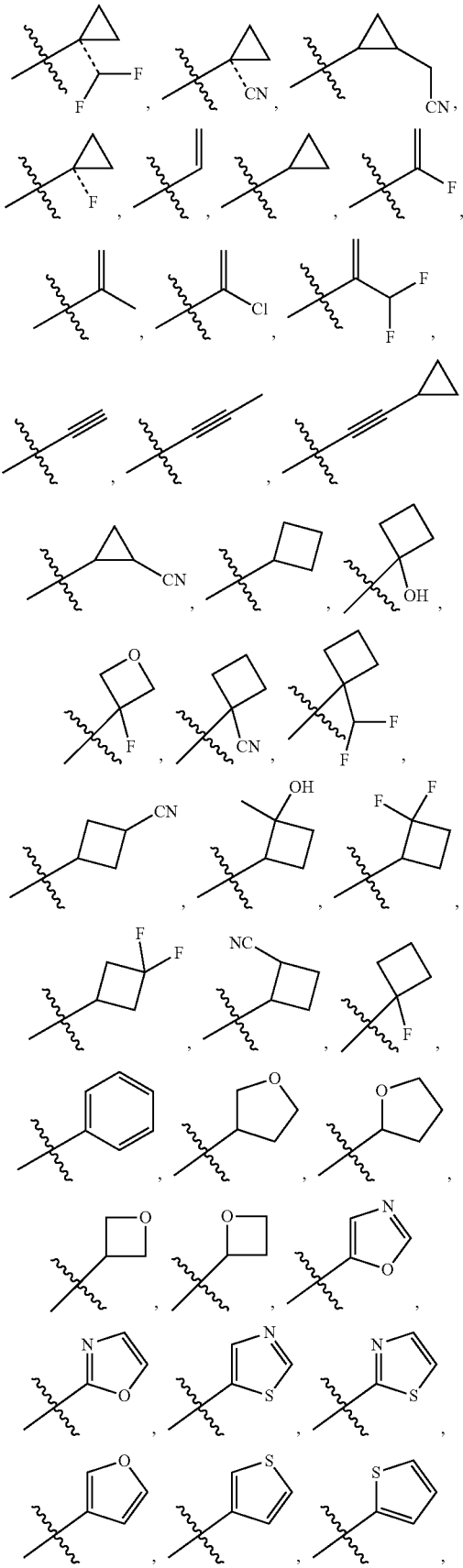

-continued

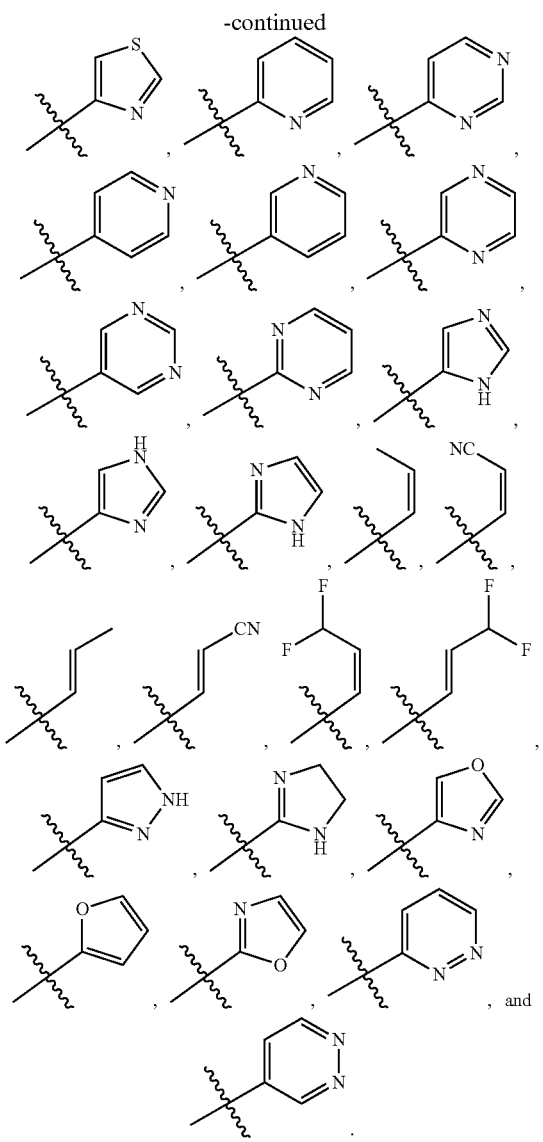

In an aspect is provided a compound of Formula (XVIh), or a pharmaceutically acceptable salt or solvate thereof:

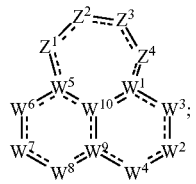

Formula (XVIh)

wherein:
$Z^1$, $Z^2$, $Z^3$ $Z^4$, $W^1$, $R^1$, $R^2$, $W^2$, $R^{2a}$, $W^3$, $R^3$, $R^{3a}$, $R^{3b}$, $W^4$, $R^{3c}$, $W^5$, $R^5$, $W^6$, $R^6$, $R^{6a}$, $R^{6b}$, $W^7$, $R^{7a}$, $R^{7c}$, $R^{7d}$, $R^7$, $L^7$, $R^{17}$, $W^8$, $R^8$, $R^{8a}$, $R^{8b}$, $W^9$, $W^{10}$, R', $R^4$, $L^4$, $R^{4b}$, $R^{4c}$, $R^{4d}$, $R^{4a}$, $R^{12}$, $R^{12b}$, $R^{13}$, $R^{14}$, $R^{148}$, $R^{15}$, $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20t}$, $R^{20m}$, $R^{21}$, $R^{21b}$, $R^{22}$, $R^{23}$, $R^{24}$, and $R^{25}$ are as described for Formula (XVI), including in embodiments of a compound of Formula (XVI);

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_6$-10aryl, —$CH_2$-$C_{1-11}$heteroaryl, $C_{1-11}$heteroaryl, —$OR^{12}$, —$SR^{12}$, —$N(R^{12})(R^{13})$, —$C(R^{12})$=$NO(R^{12})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$S(O)_2R^{15}$, and —$(C_{1-6}$alkyl)-$S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_6$-10aryl, —$CH_2$-$C_{1-11}$heteroaryl, and $C_{1-11}$heteroaryl are optionally substituted with one, two, three, four, or five $R^{20k}$;

each $R^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_6$-10aryl, —$CH_2$-$C_{1-11}$heteroaryl, $C_{1-11}$ heteroaryl, —$OR^{12}$, —$SR^{12}$, —$N(R^{12})(R^{13})$, —$C(R^{12})$—$NO(R^{12})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{12}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{12}$, —$S(O)_2R^{15}$, —$S(O)_2N(R^{12})(R^{13})$—, $S(=O)(=NH)N(R^{12})(R^{13})$, —$(C_{1-6}$alkyl)-$C(O)N(R^{12})(R^{13})$, —$(C_{1-6}$alkyl)-$OC(O)R^{12}$, —$(C_{1-6}$alkyl)-$N(R^{14})C(O)R^{12}$, —$(C_{1-6}$alkyl)-$N(R^{12})(R^{13})$, —$(C_{1-6}$alkyl)-$S(O)_2R^{15}$, and —$(C_{1-6}$alkyl)-$S(O)_2$ $N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_6$-10aryl, —$CH_2$-$C_{1-11}$heteroaryl, and $C_{1-11}$heteroaryl are optionally substituted with one, two, three, four, or five $R^{20k}$; and ----- indicates a single or double bond such that all valences are satisfied. In embodiments of the formulae above, $R^{11c}$ is independently selected from hydrogen,

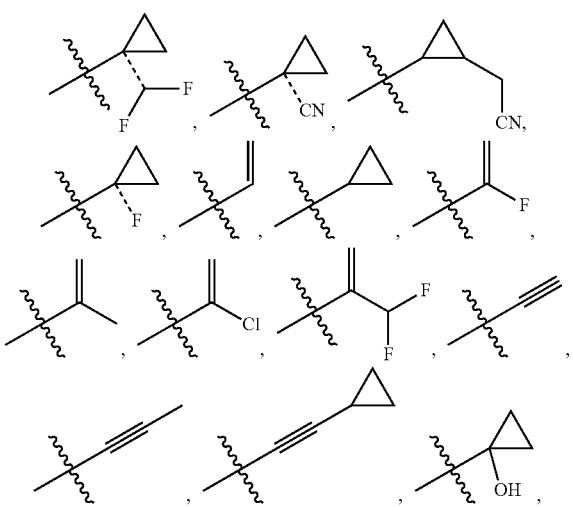

-continued

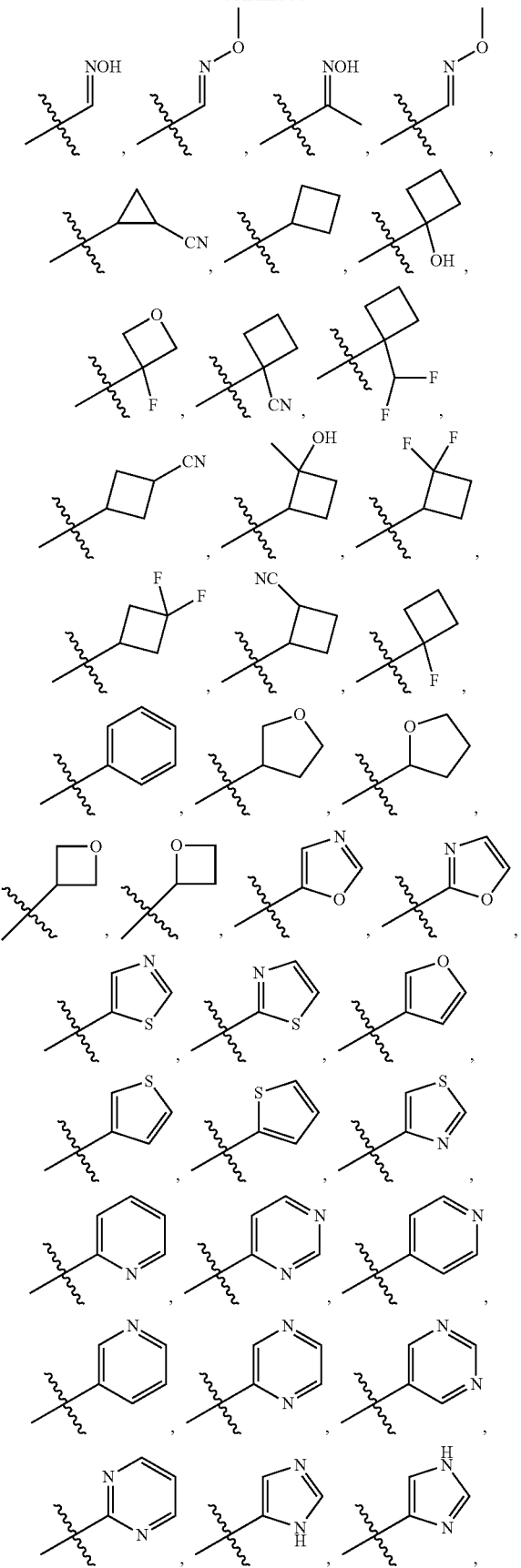

-continued

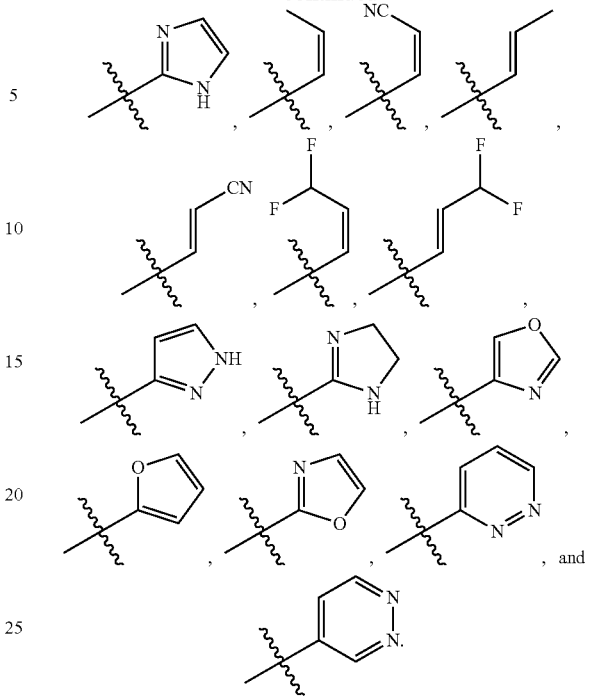

, and

The individual embodiments herein below, or combinations thereof, (e.g., embodiments of $R^{11c}$, $R^{11d}$, or $R^4$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof.

In embodiments of the formulae above, each $R^{11c}$ is independently selected from 421
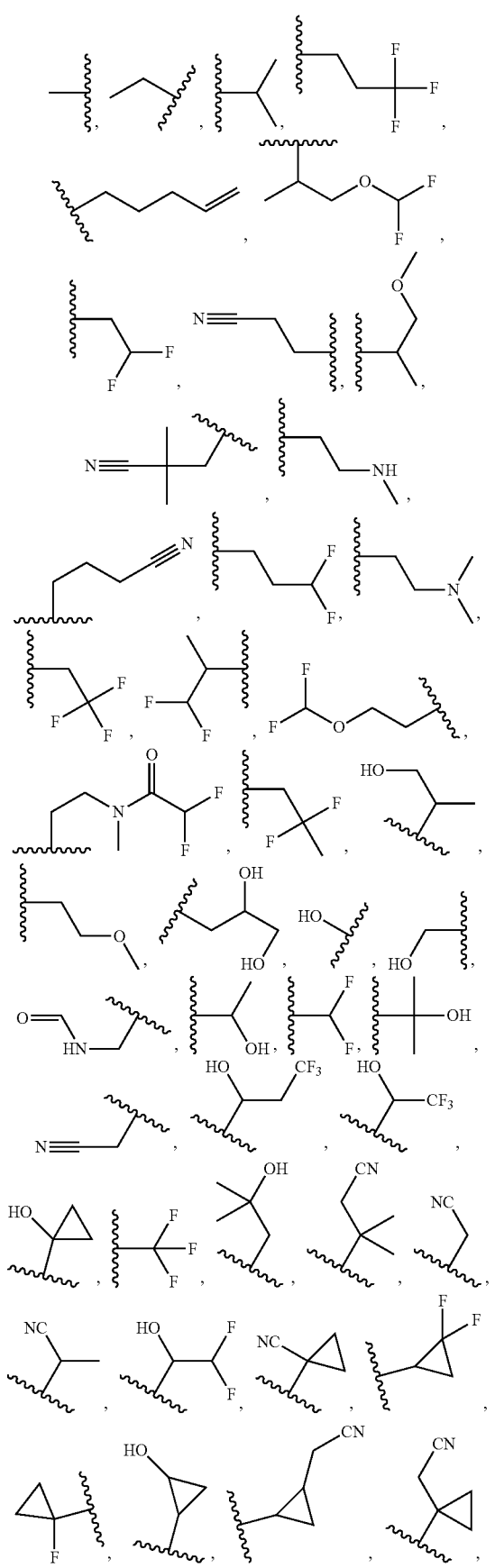
422
-continued
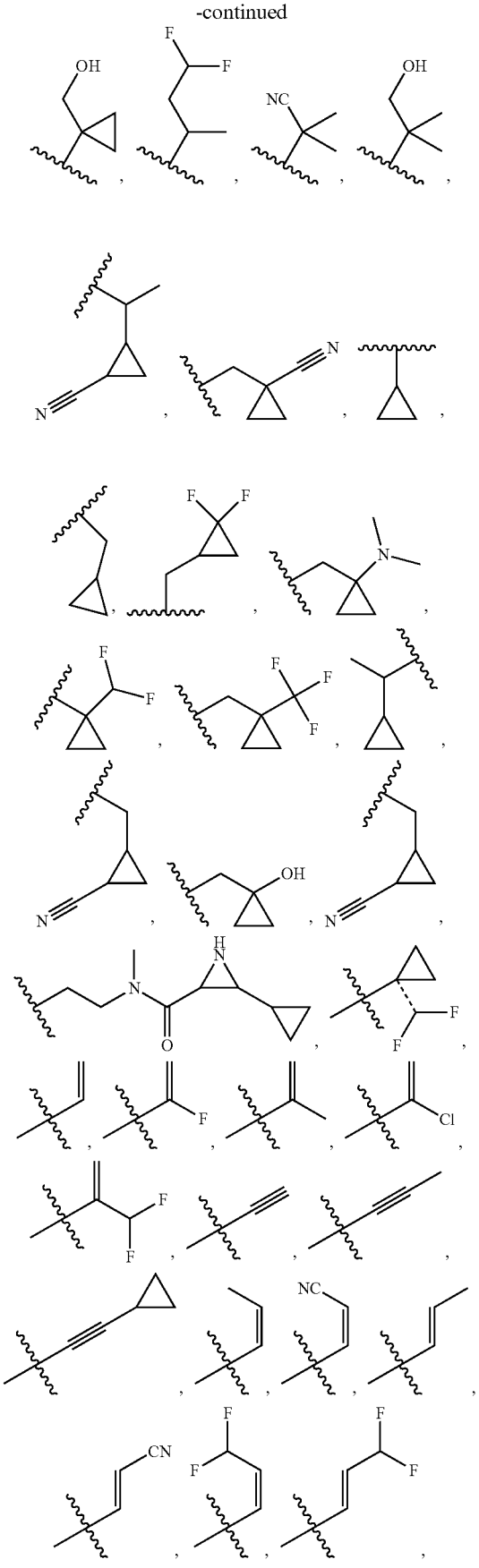

423
-continued
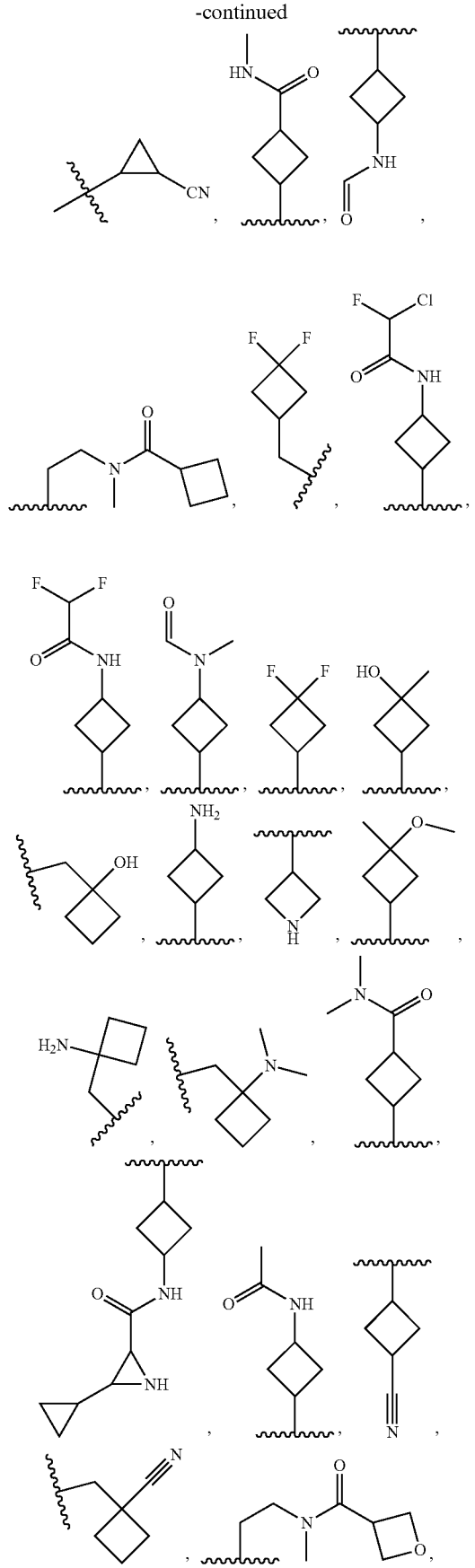
424
-continued
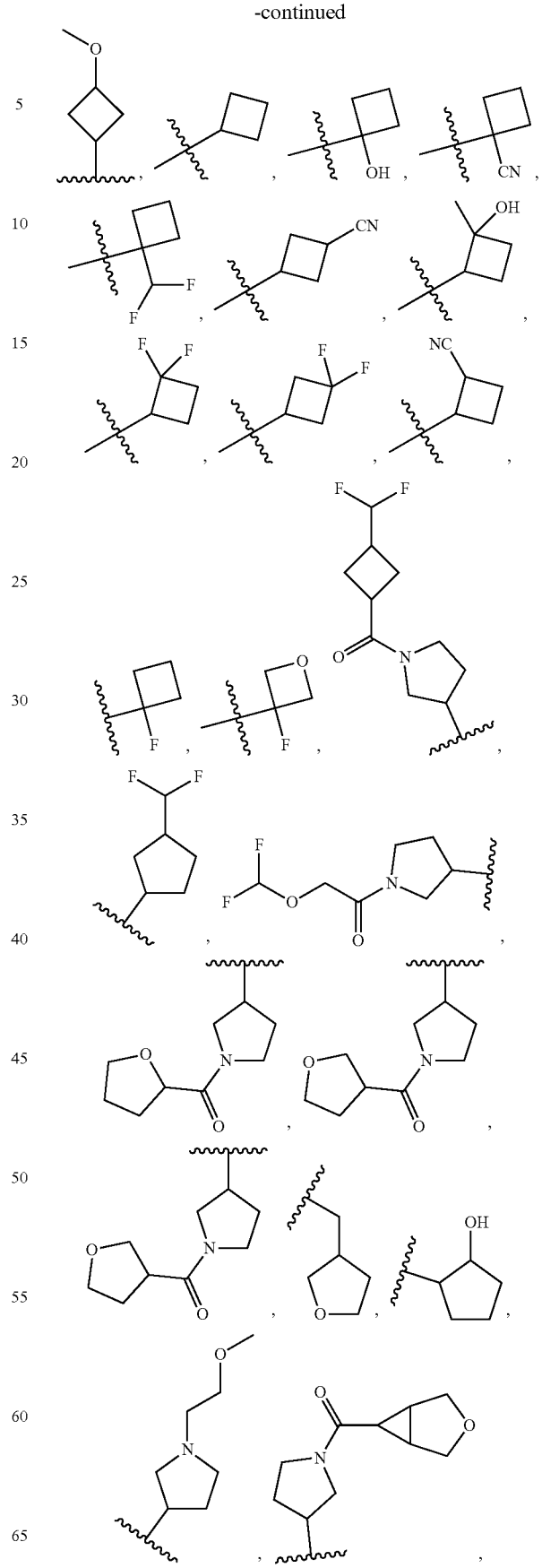

425
-continued
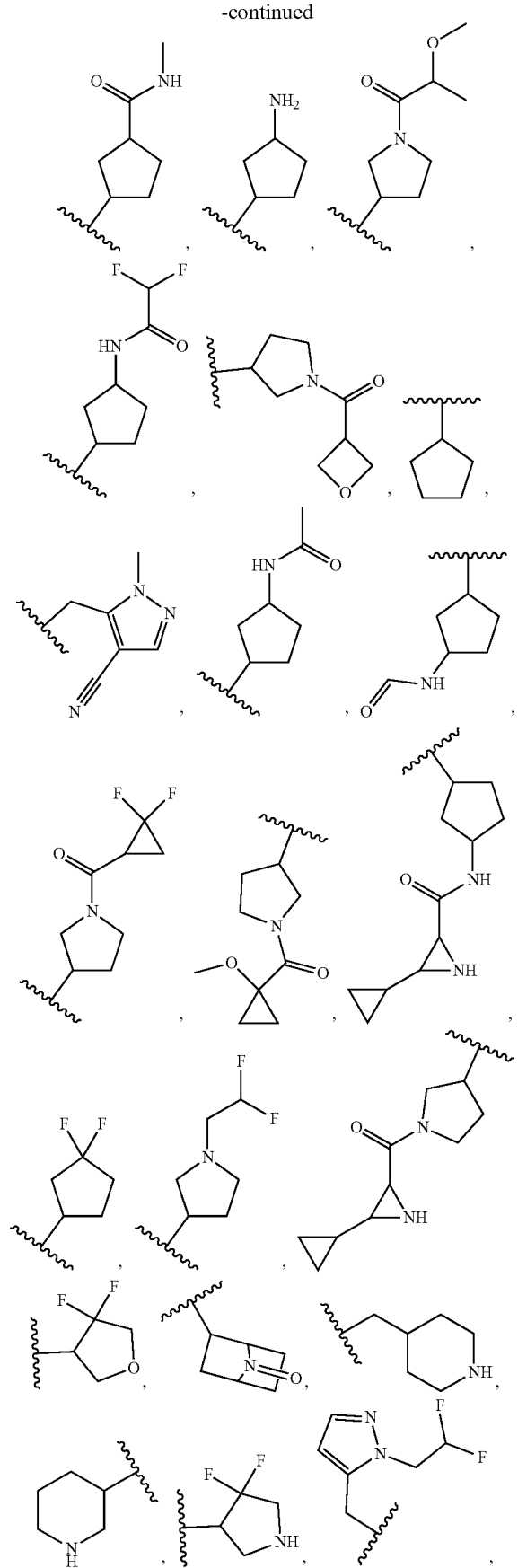
426
-continued
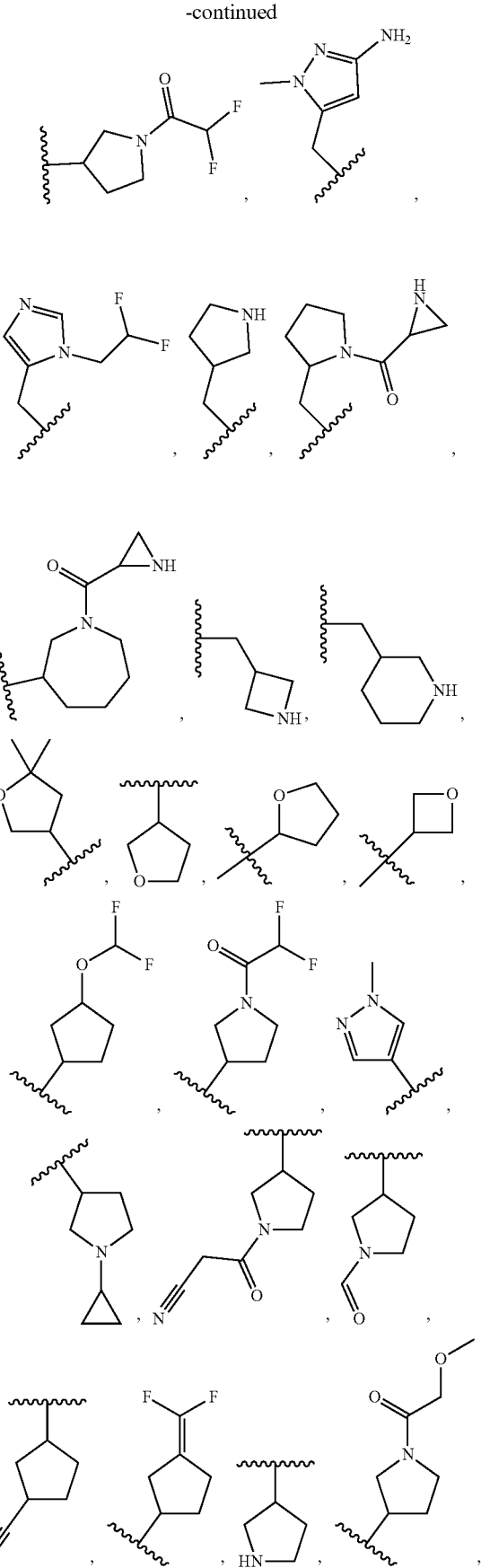

427
-continued
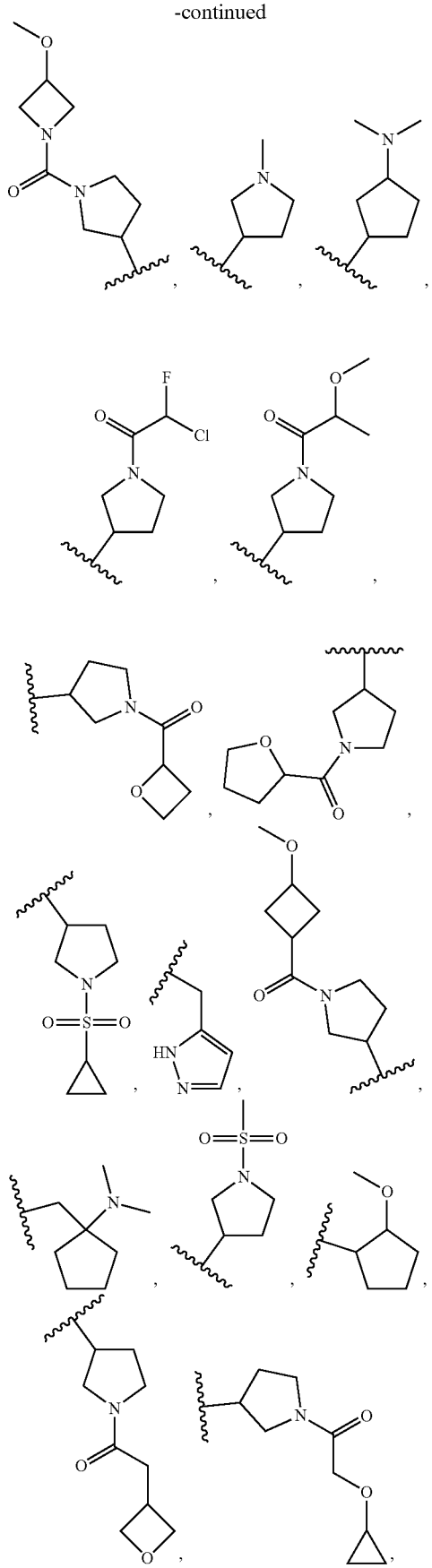
428
-continued
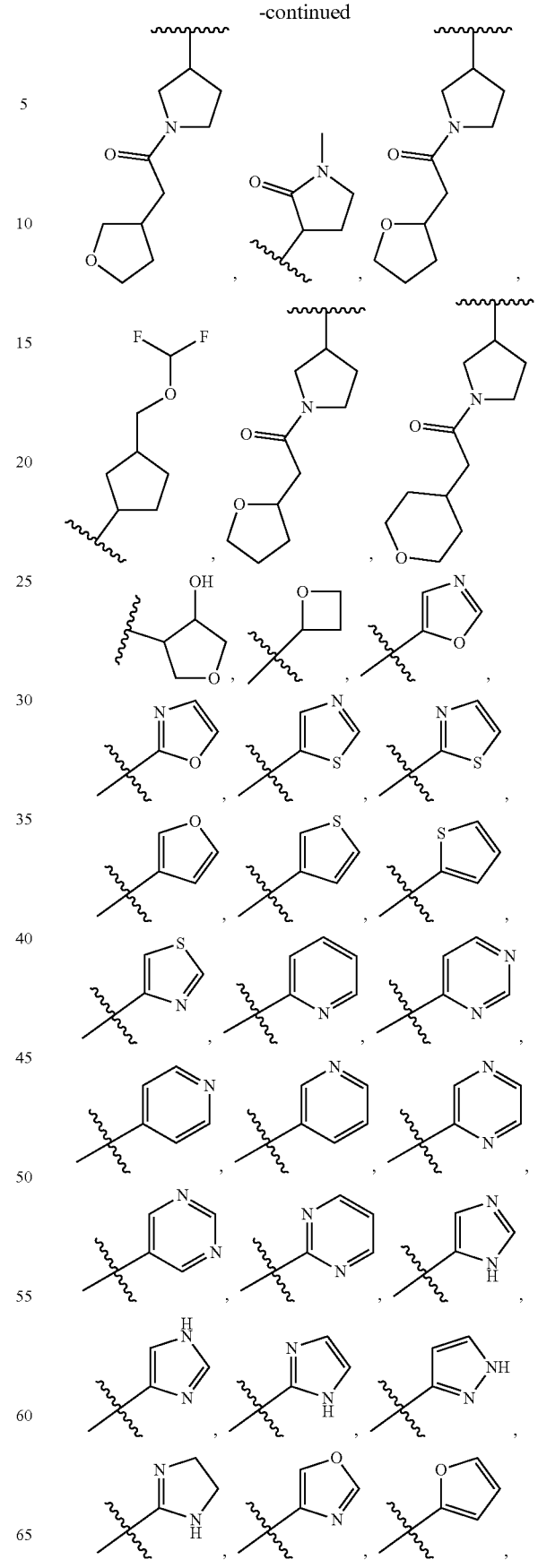

429
-continued
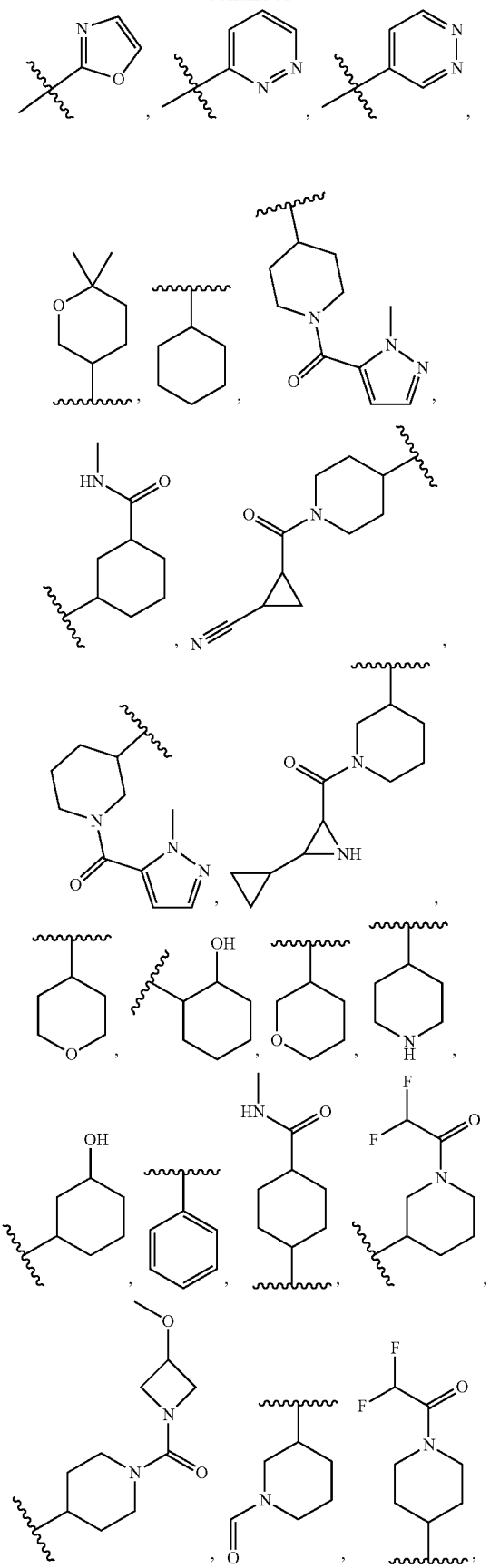
430
-continued
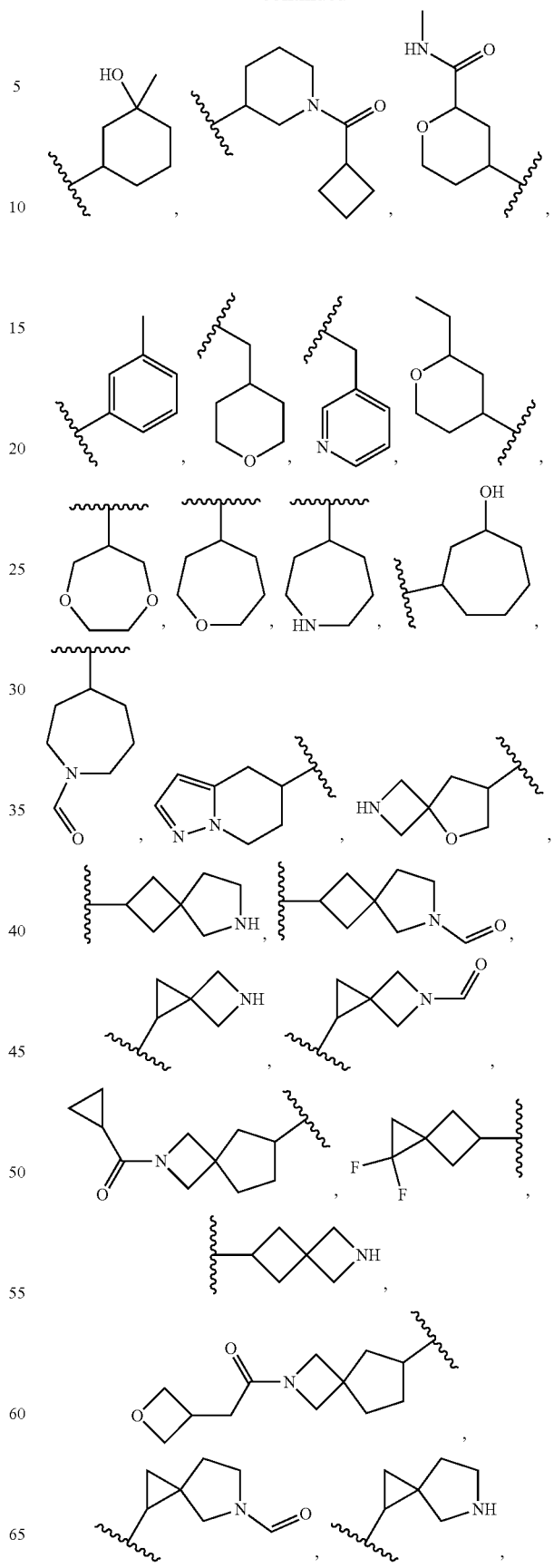

431
-continued
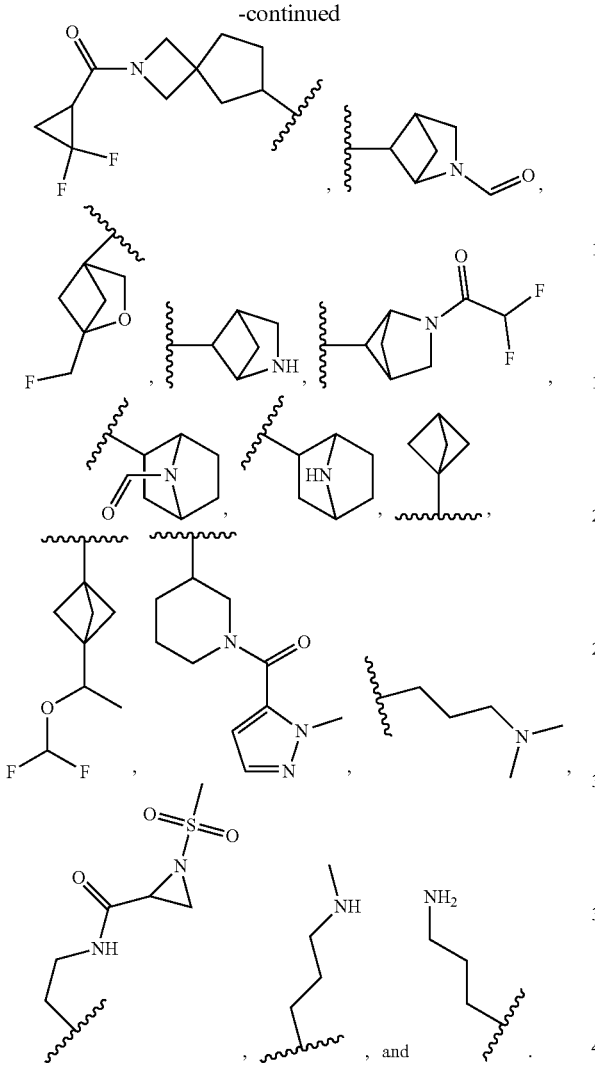
In embodiments of the formulae above, each $R^{11c}$ is independently selected from
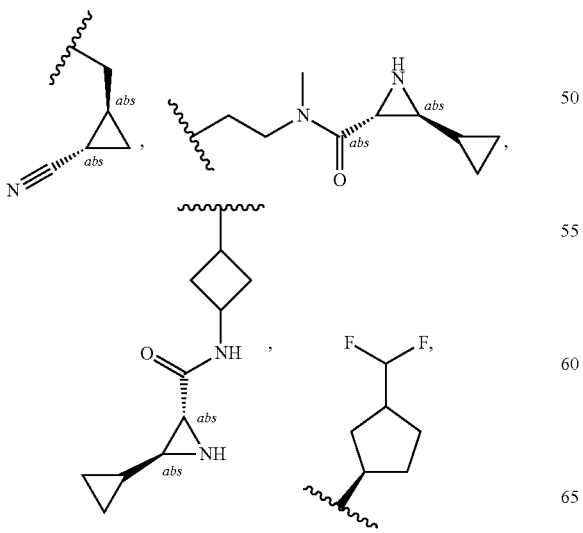
432
-continued
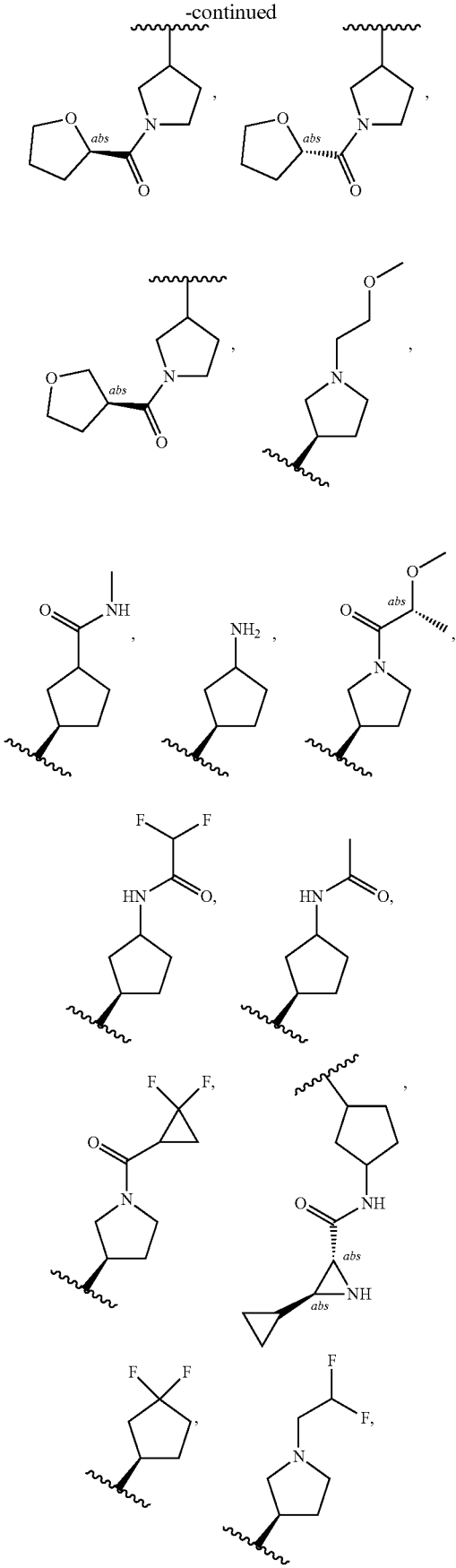

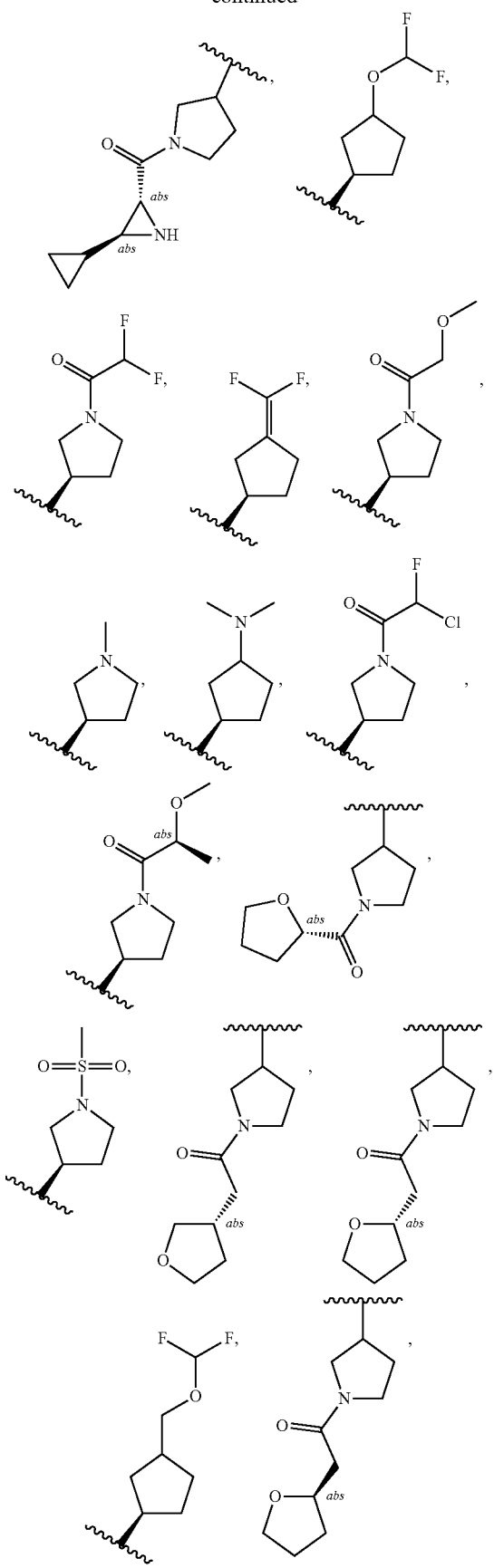
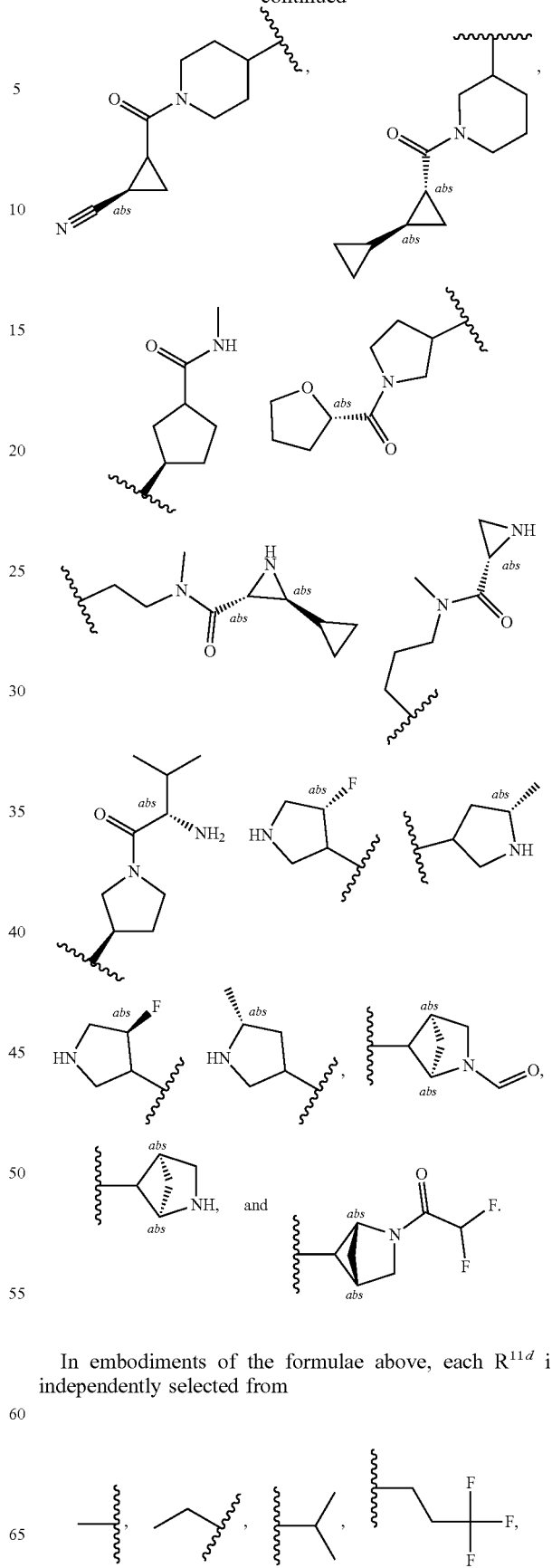
In embodiments of the formulae above, each $R^{11d}$ is independently selected from 435
-continued
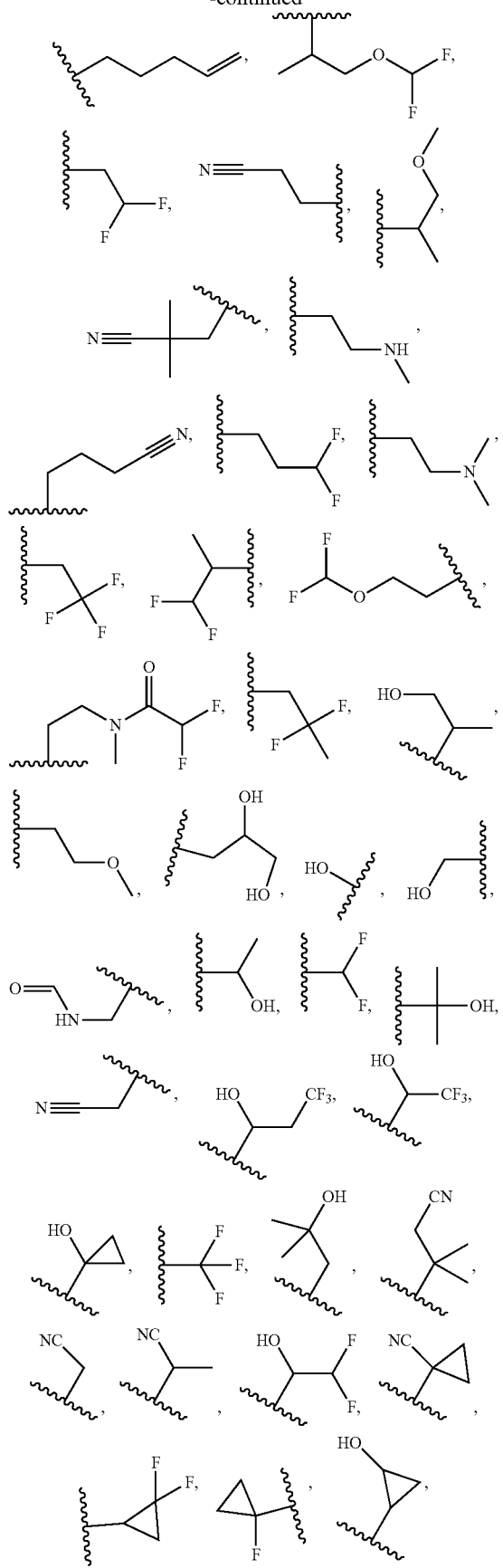
436
-continued
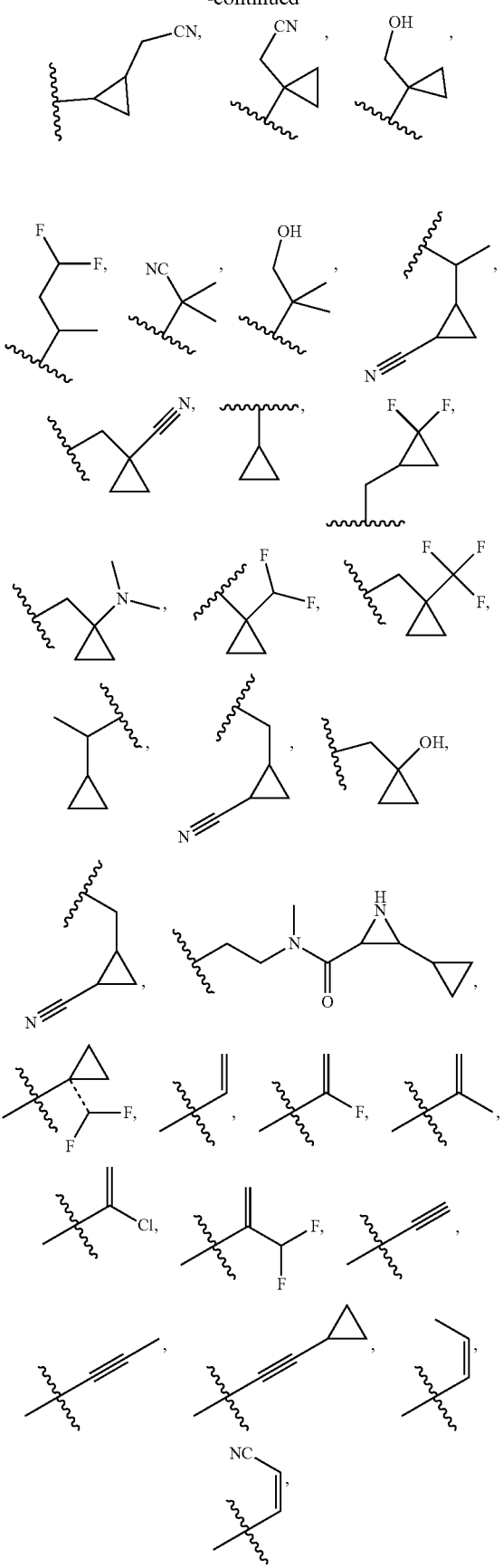

437
-continued
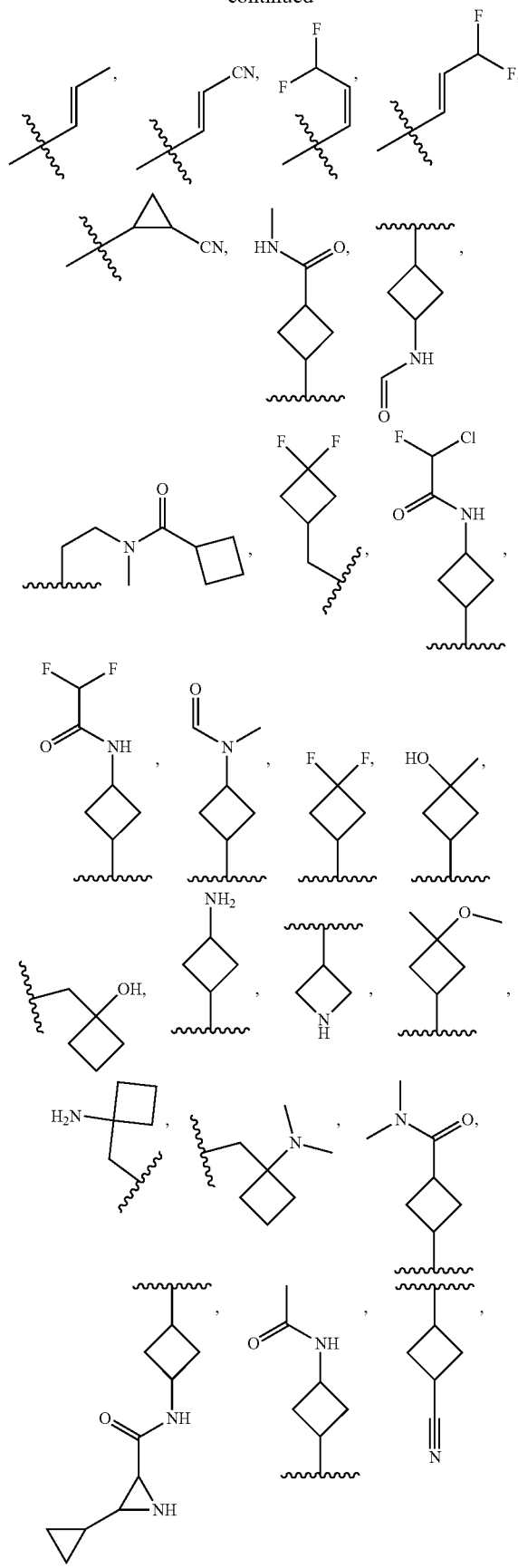
438
-continued
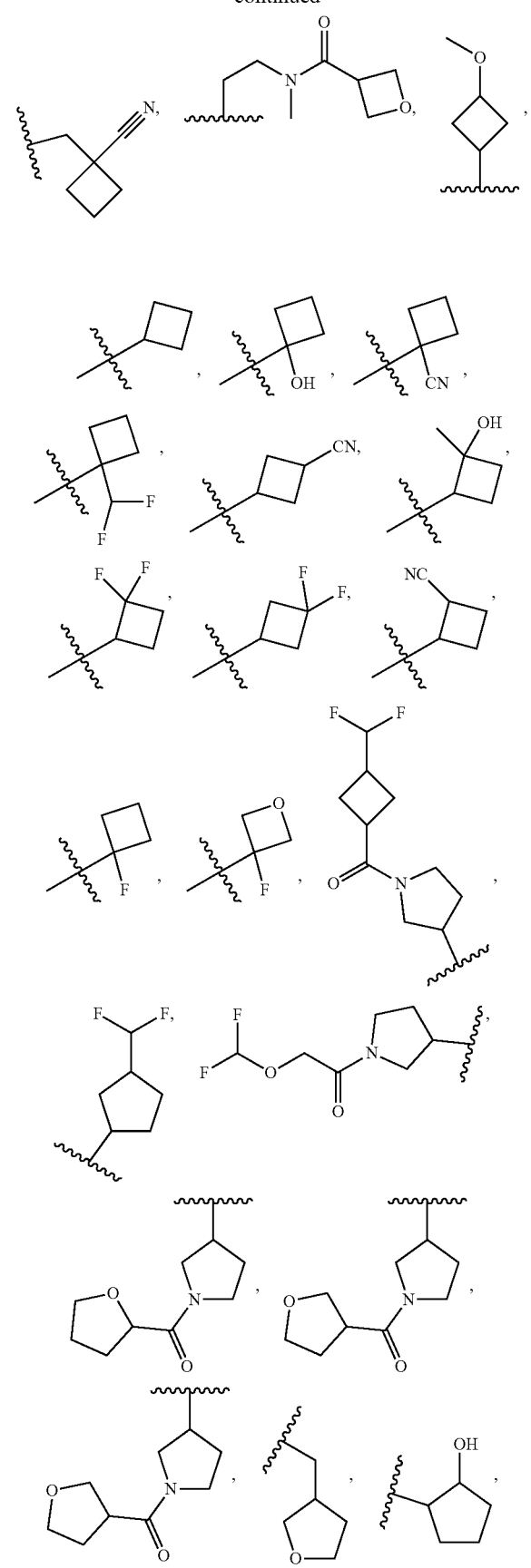

439
-continued
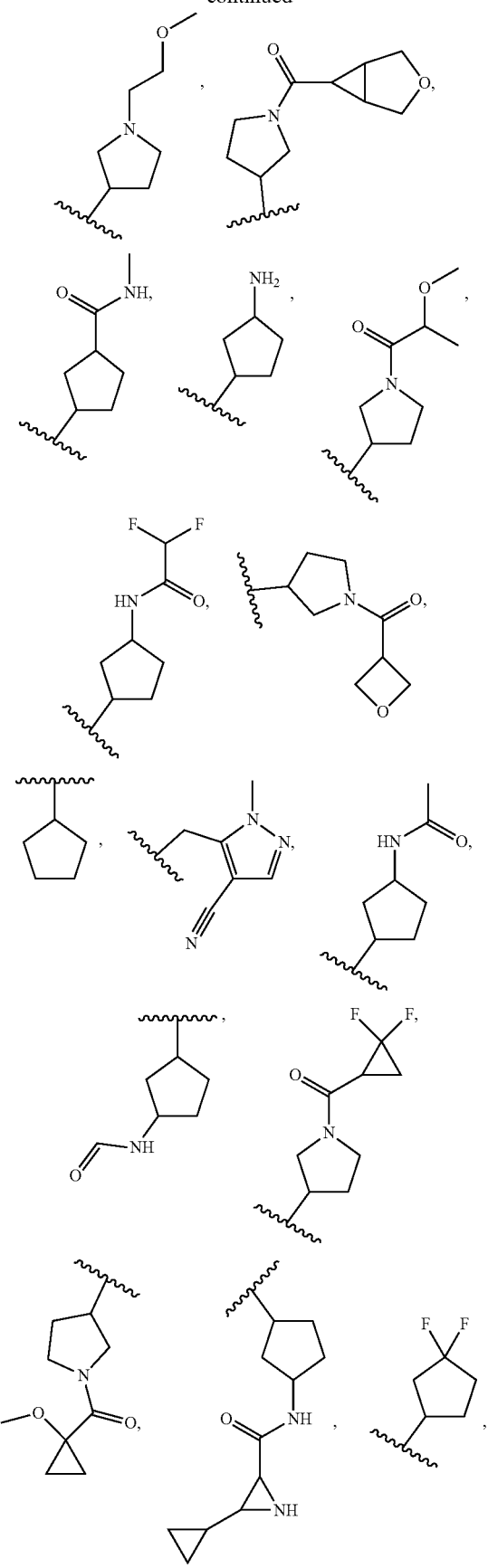
440
-continued
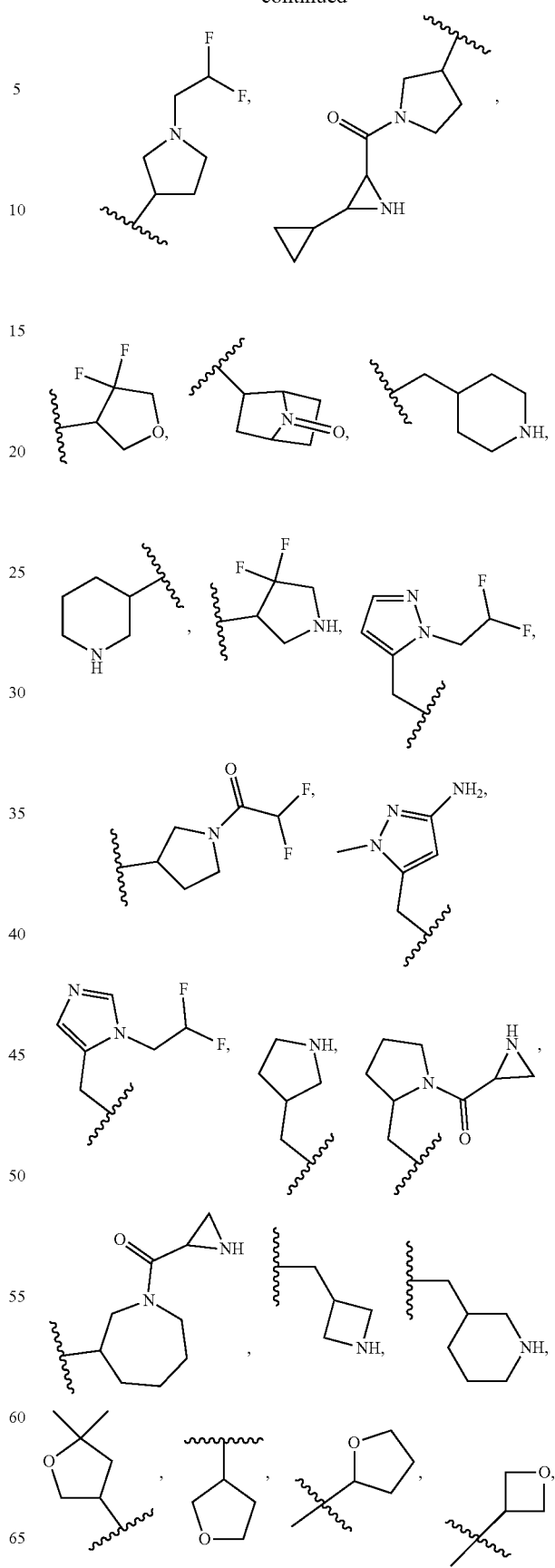

441
-continued
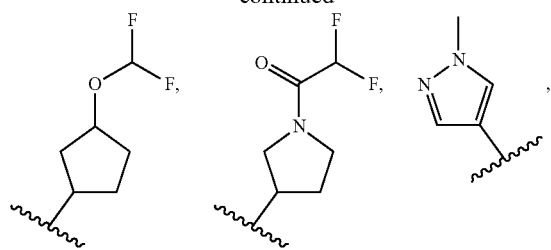
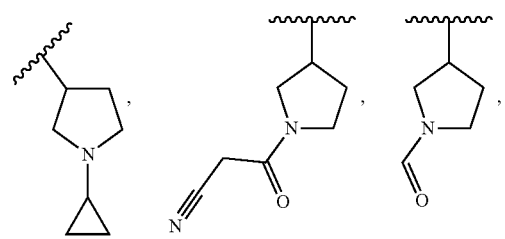
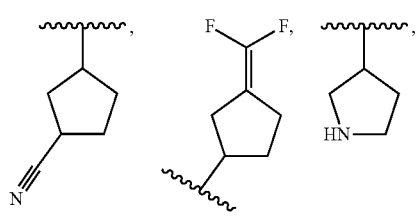
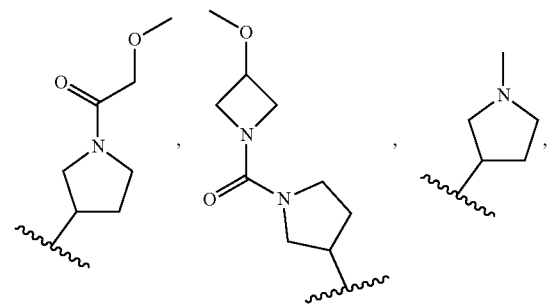
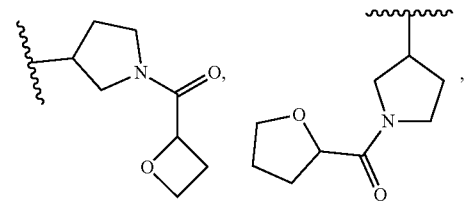
442
-continued
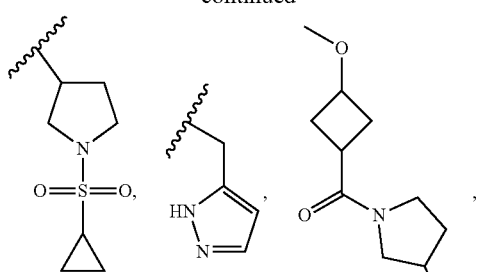
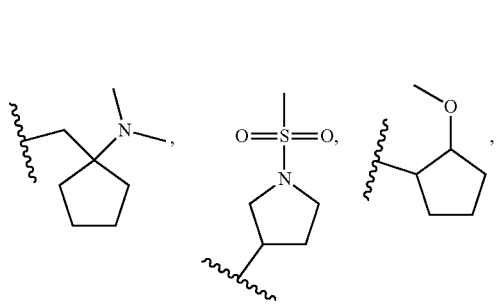
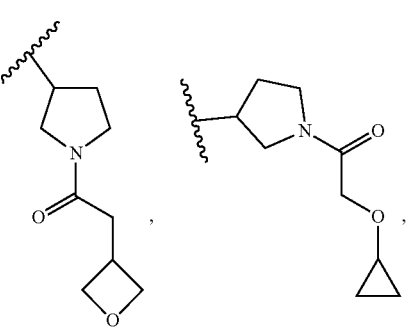
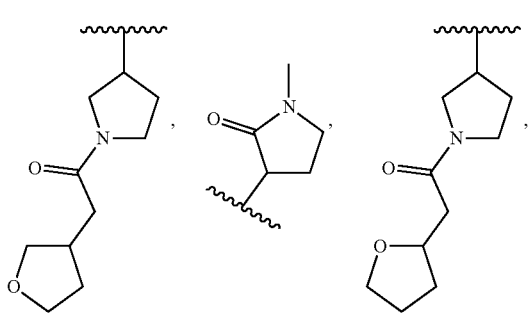
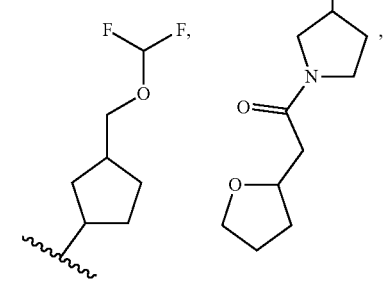

-continued
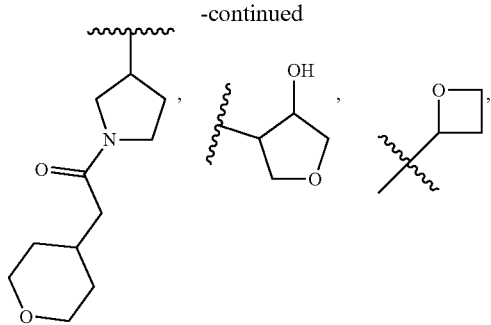
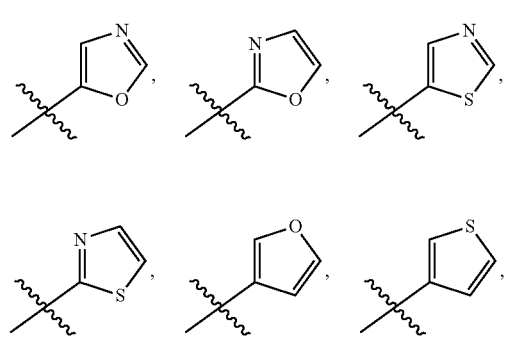
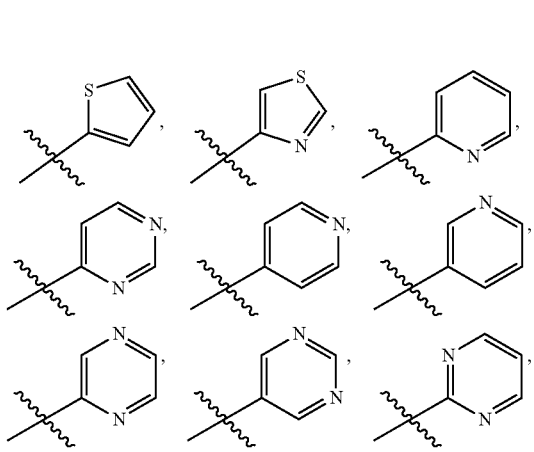
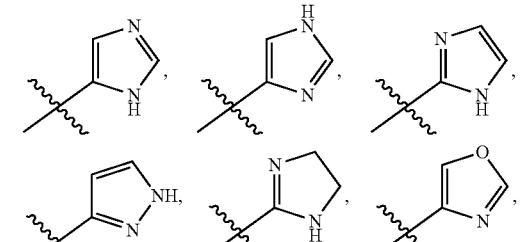
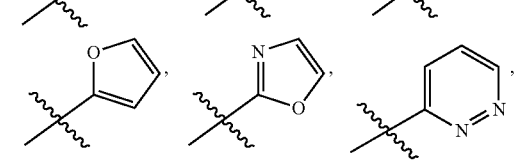
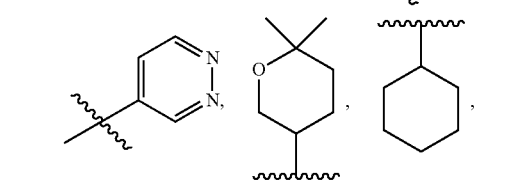
-continued
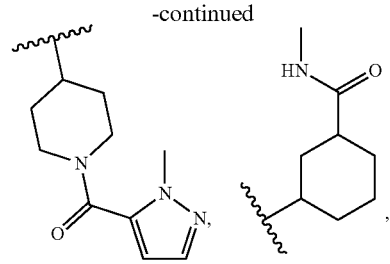
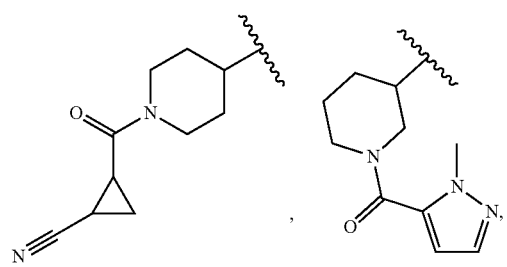
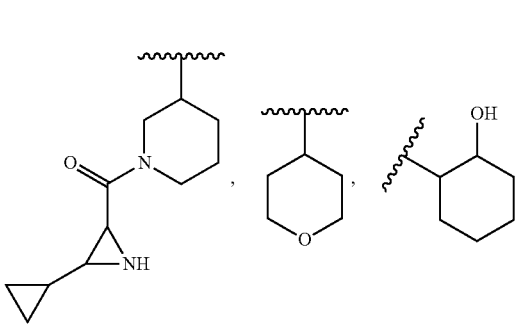
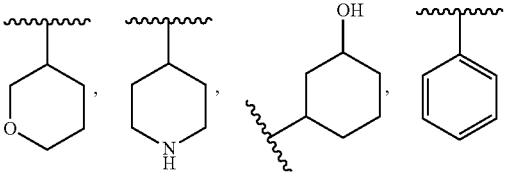
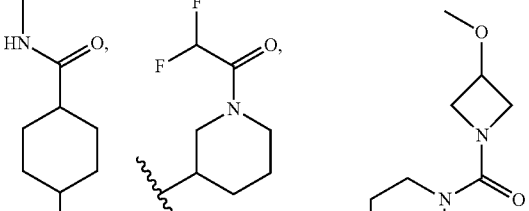
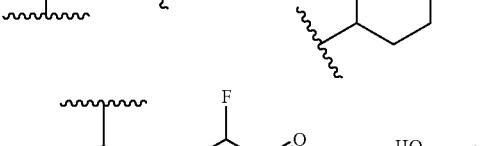
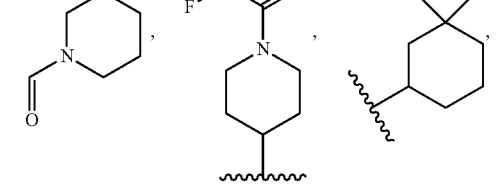

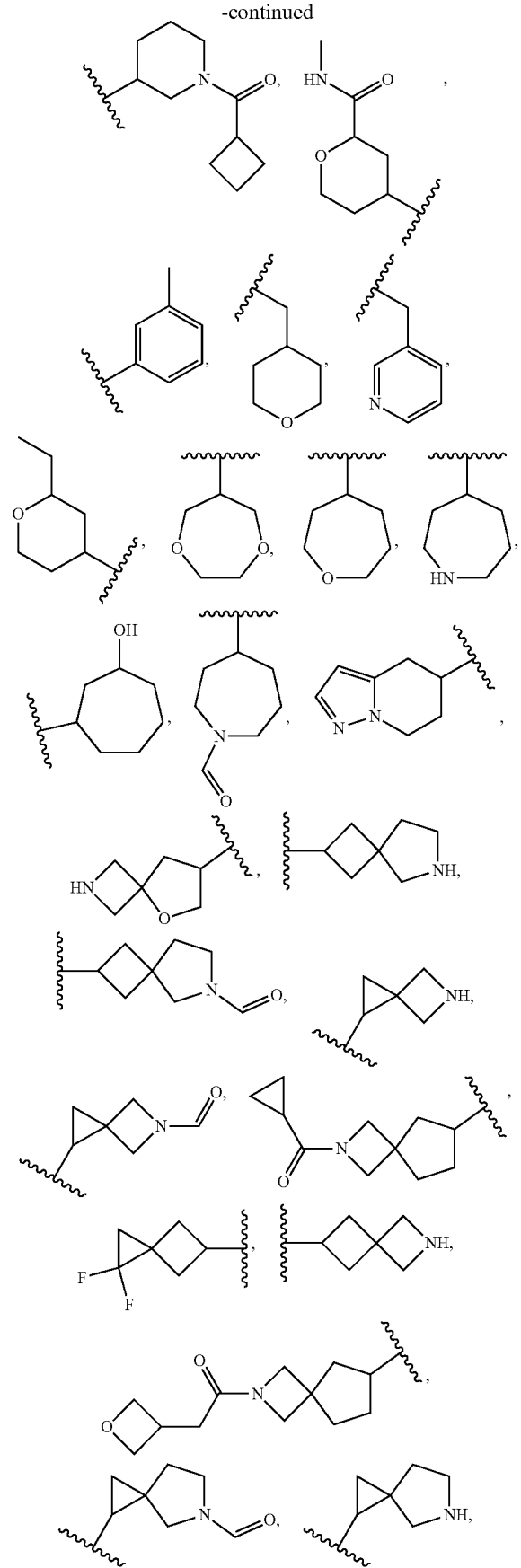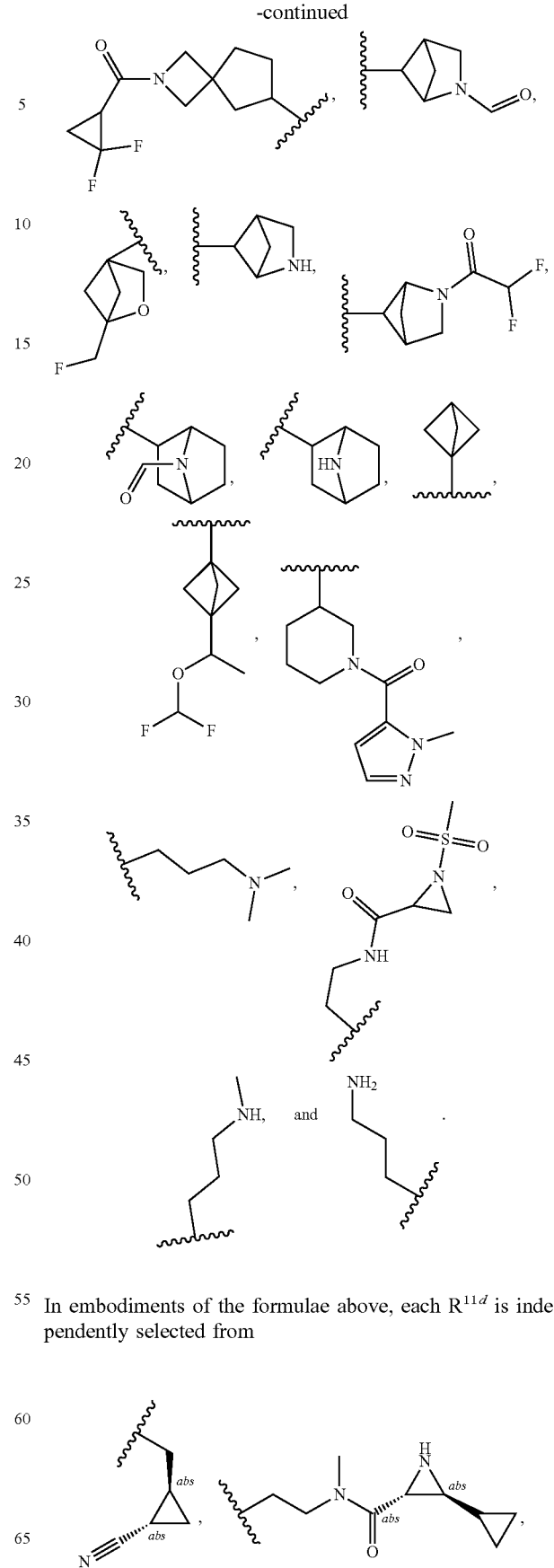
In embodiments of the formulae above, each $R^{11d}$ is independently selected from 447
-continued
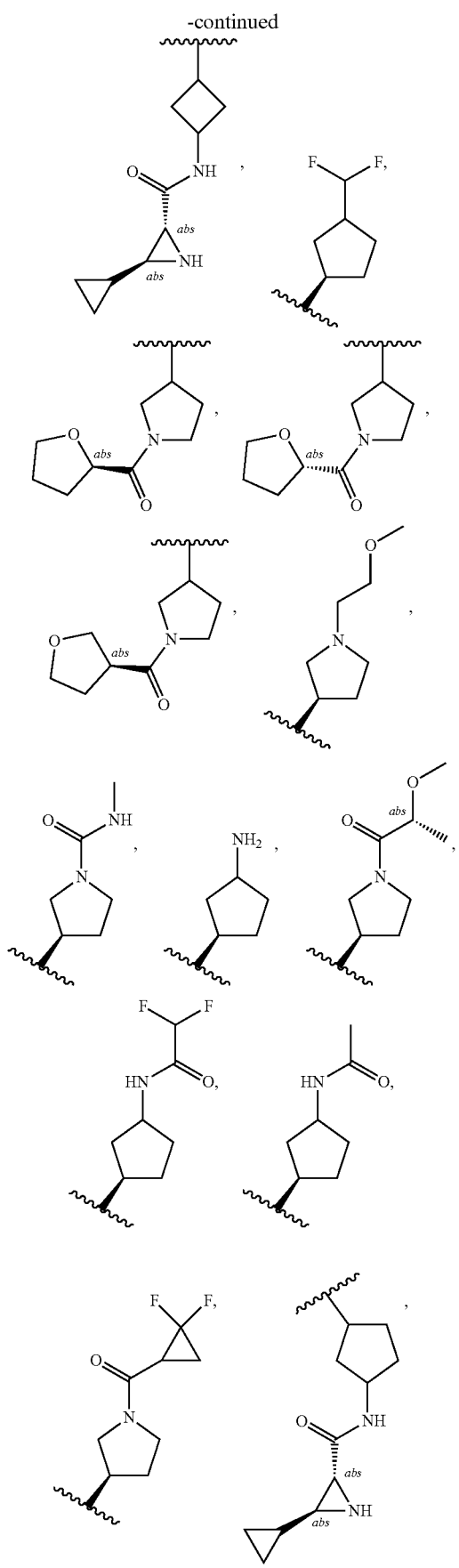
448
-continued
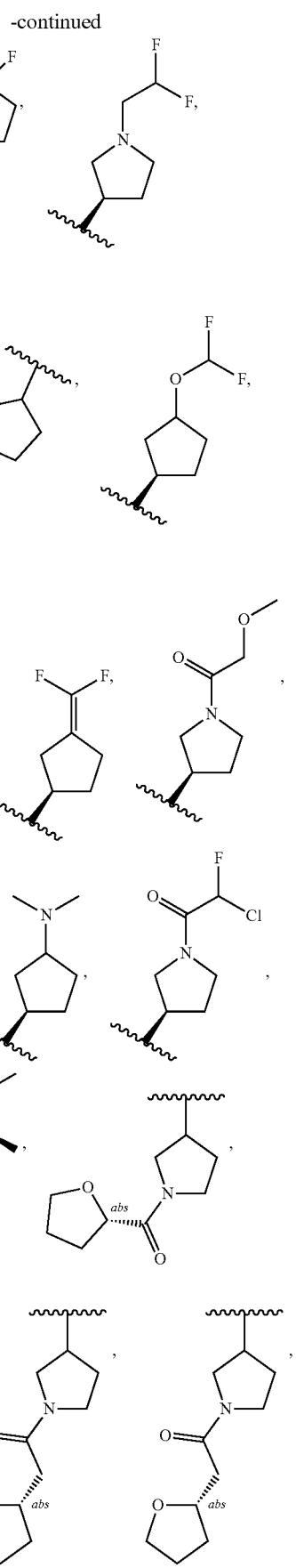

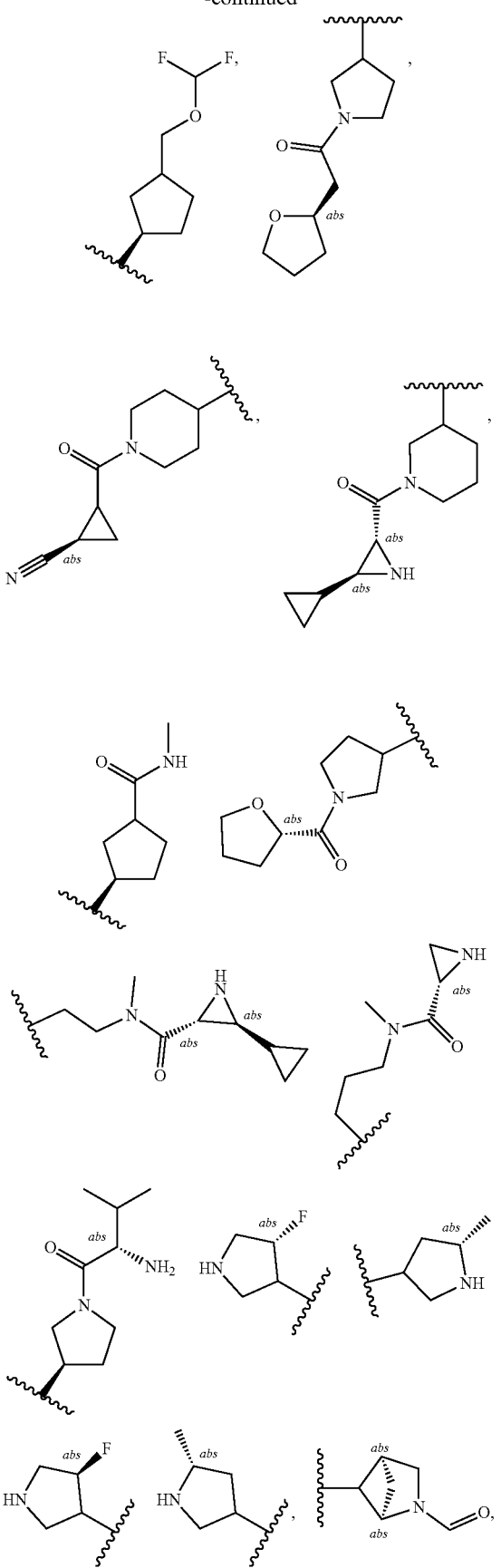
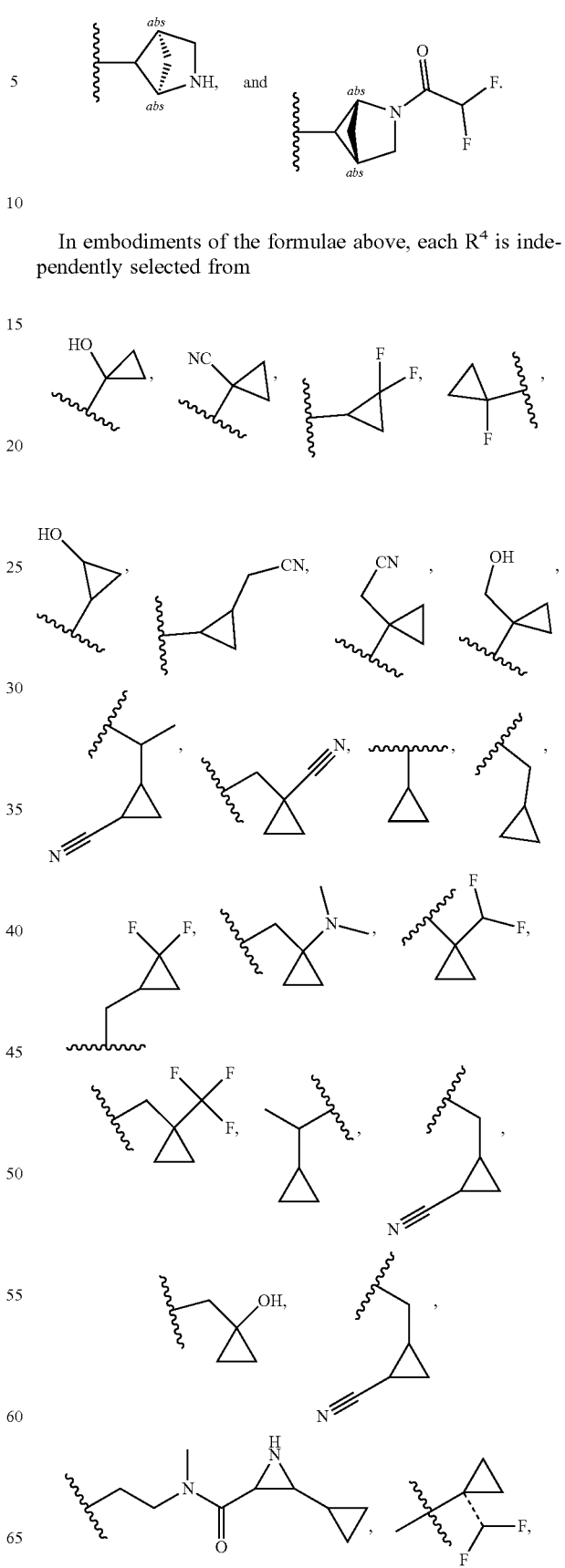
In embodiments of the formulae above, each $R^4$ is independently selected from 451
-continued
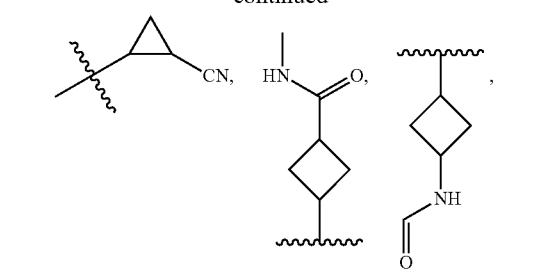
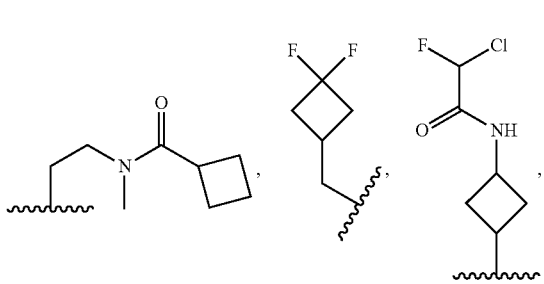
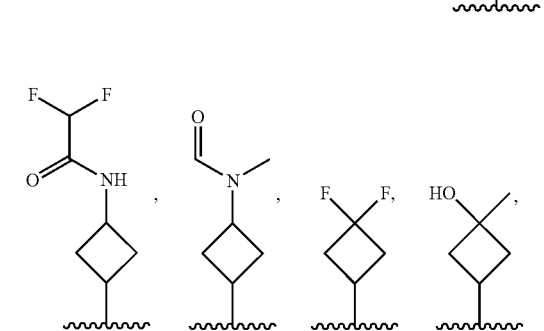
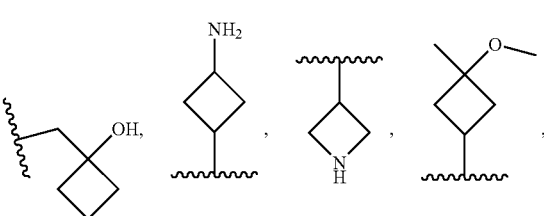
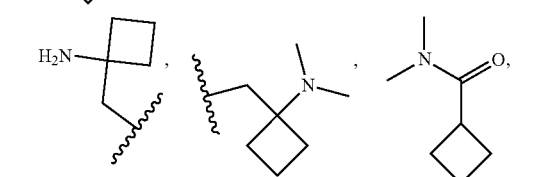
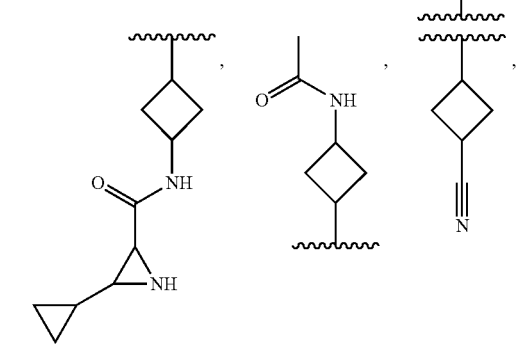
452
-continued
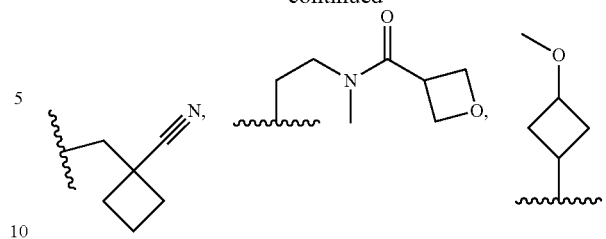
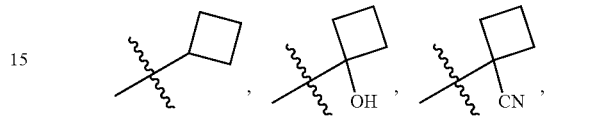
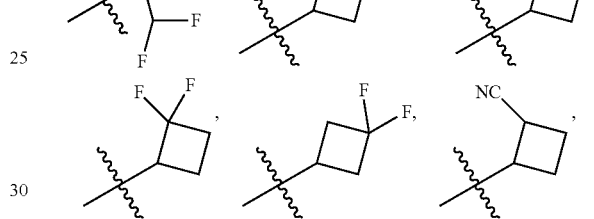
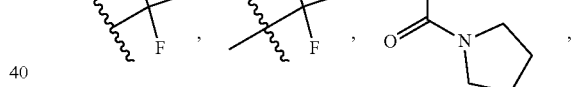
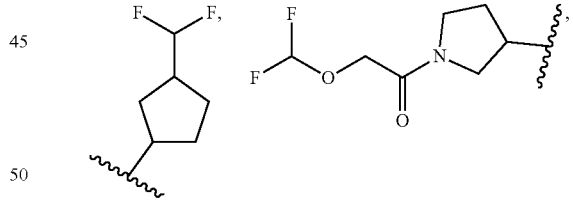
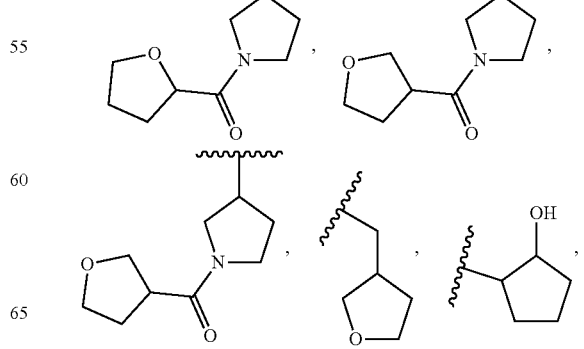

453
-continued
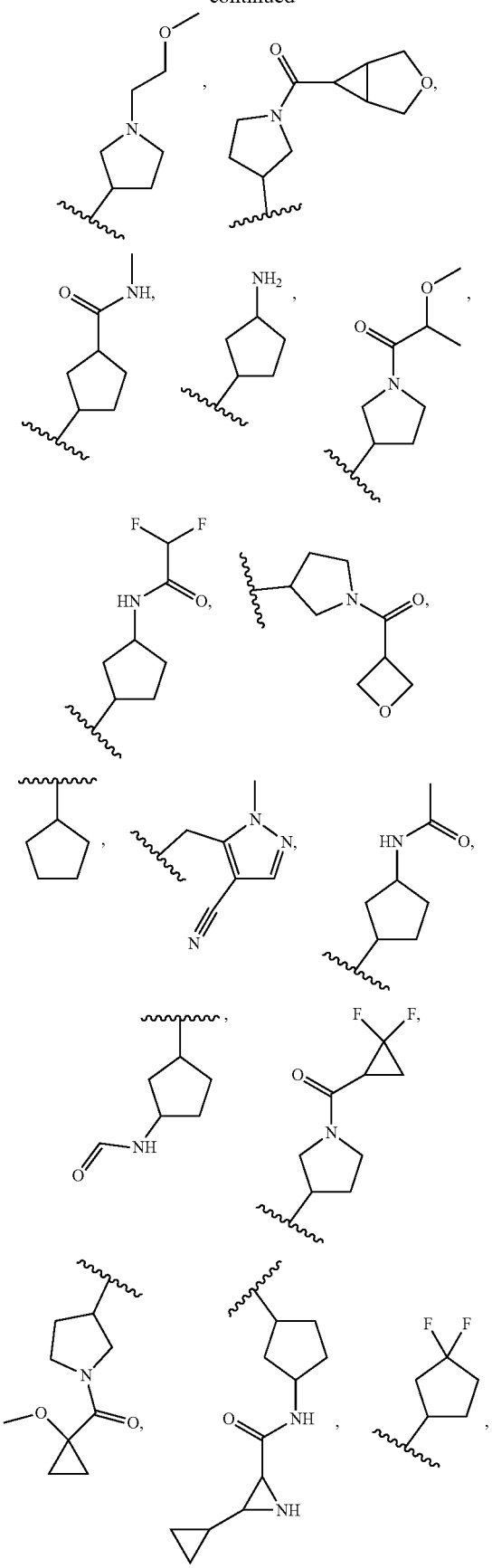
454
-continued
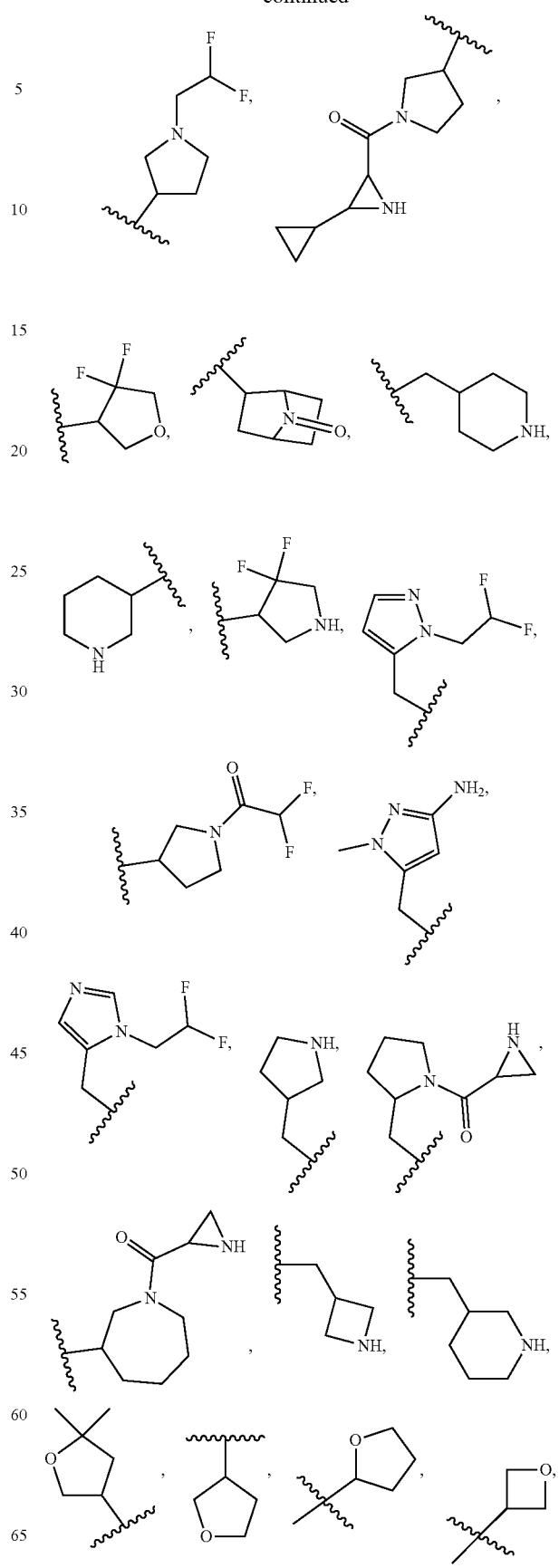

455
-continued
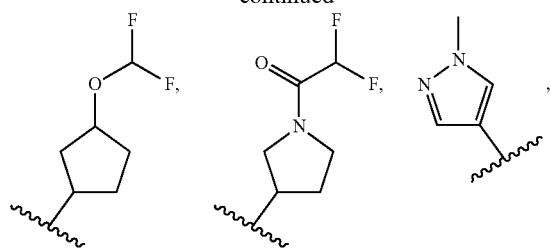
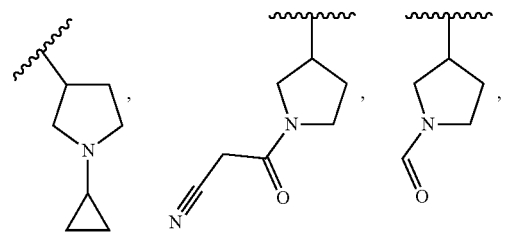
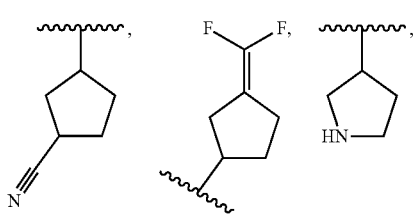
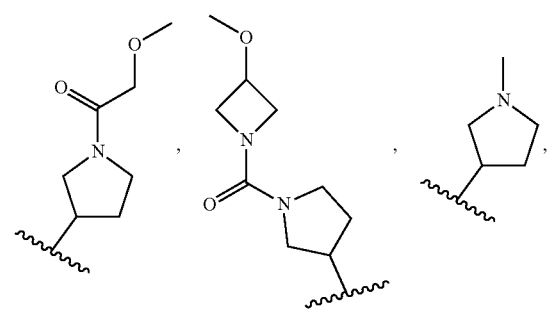
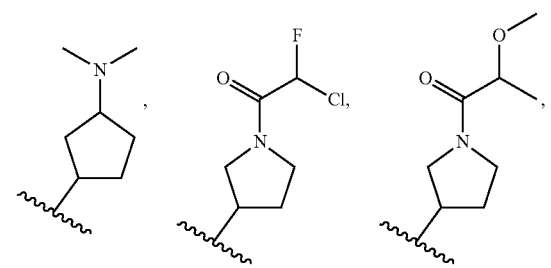
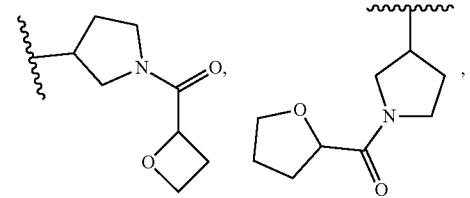
456
-continued
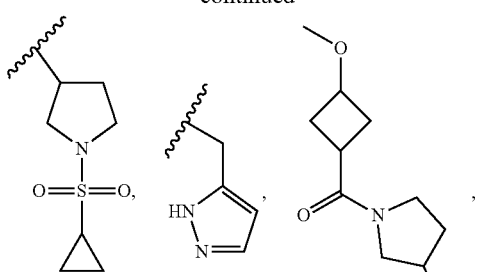
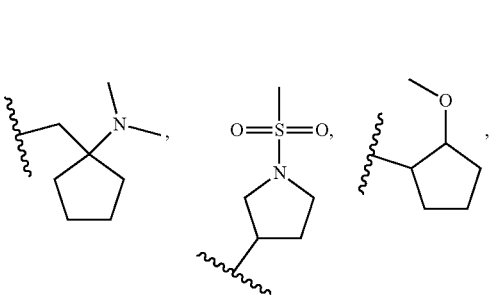
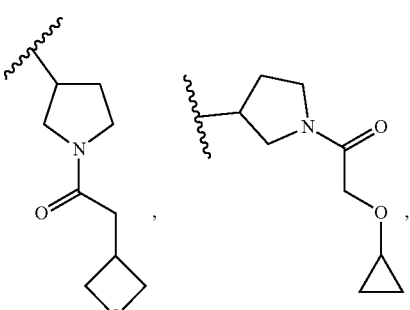
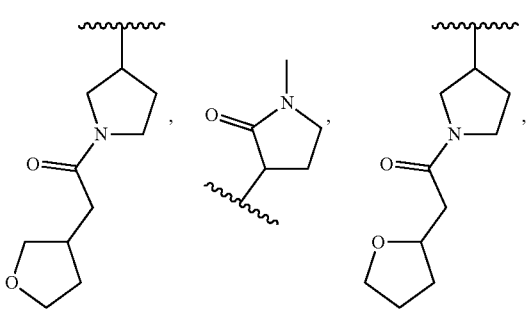
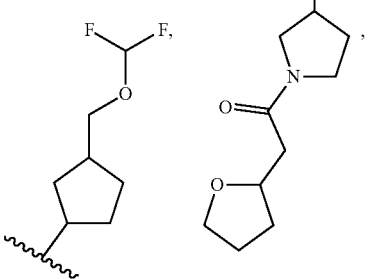

457
-continued
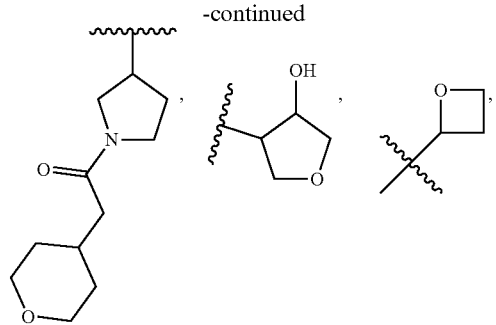
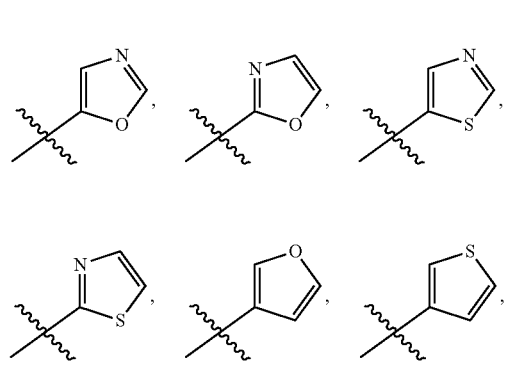
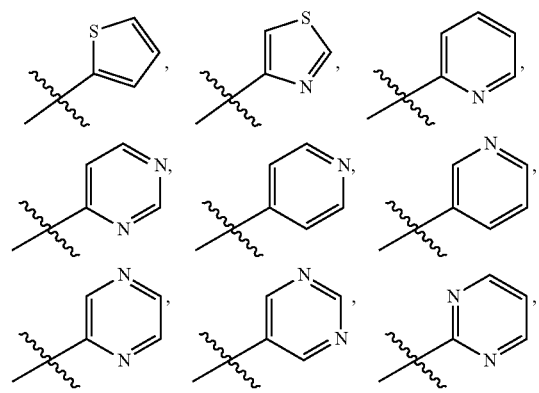
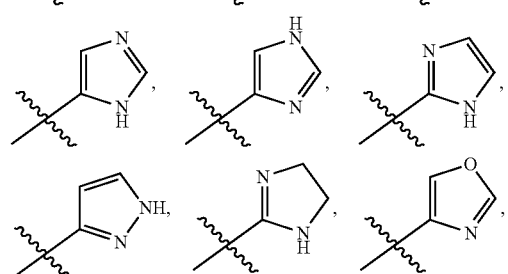
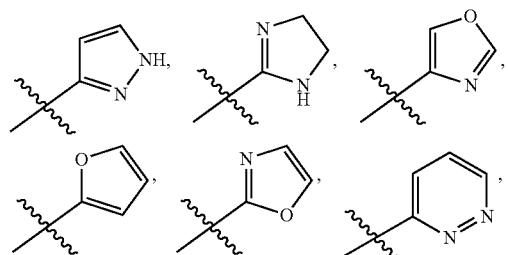
458
-continued
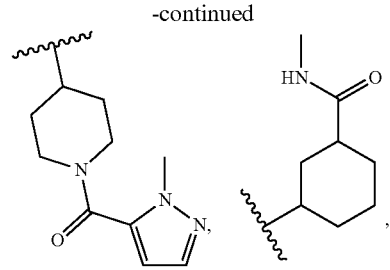
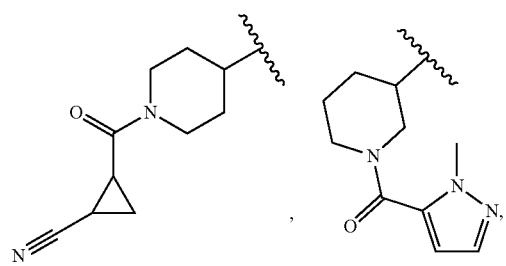
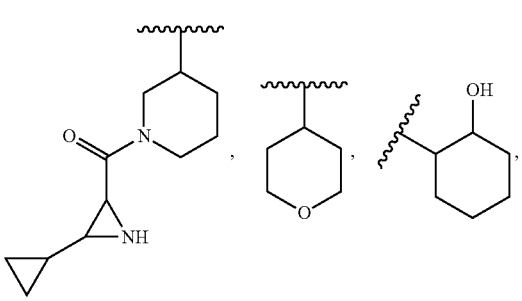
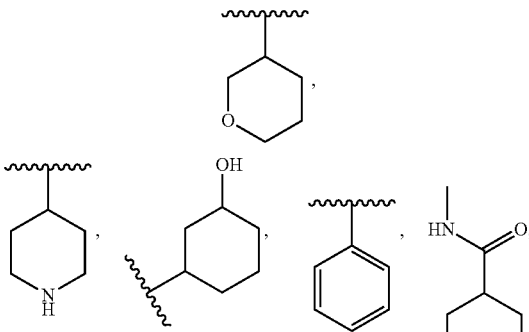
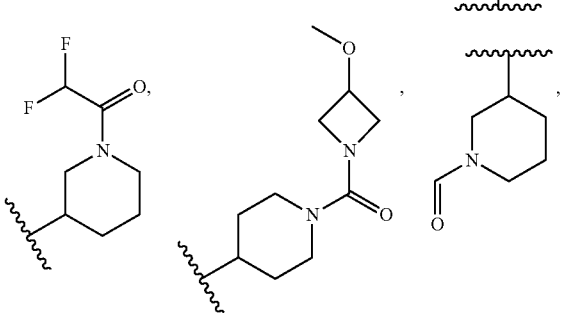

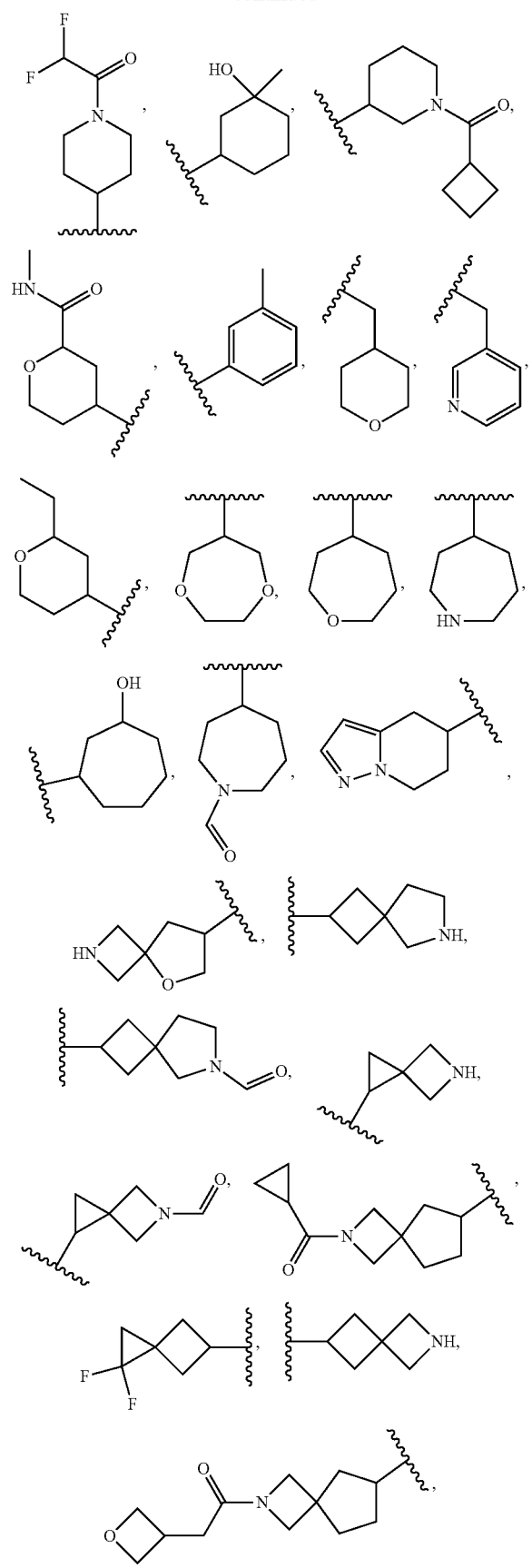
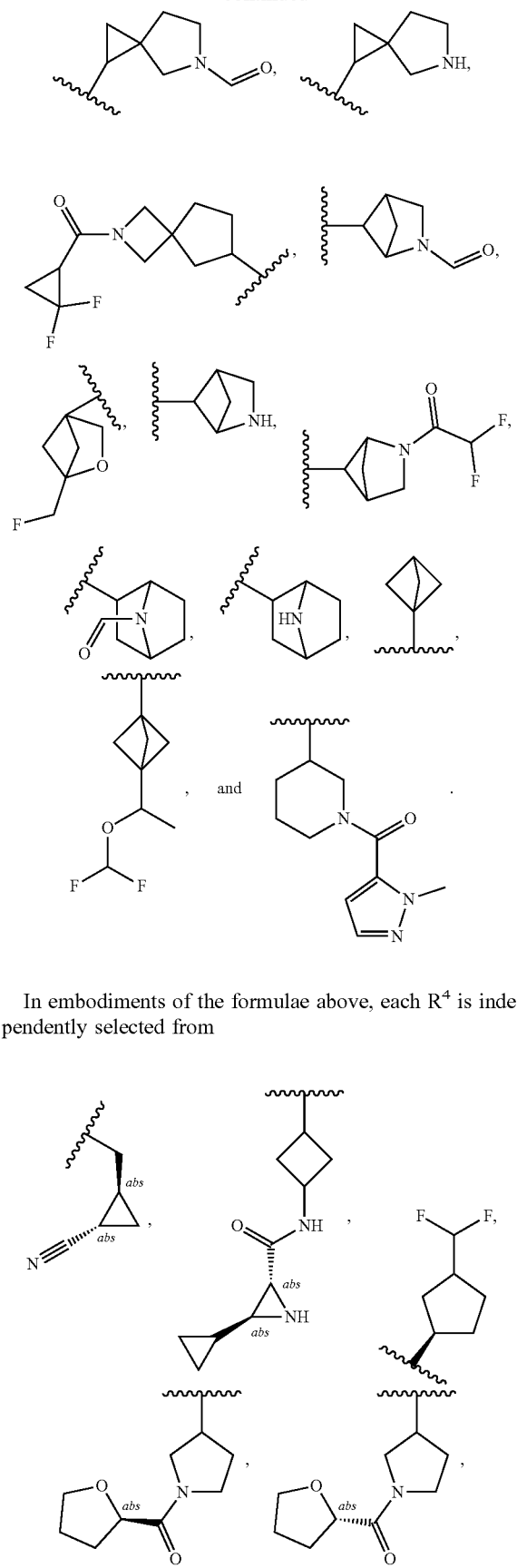
In embodiments of the formulae above, each $R^4$ is independently selected from

461
-continued
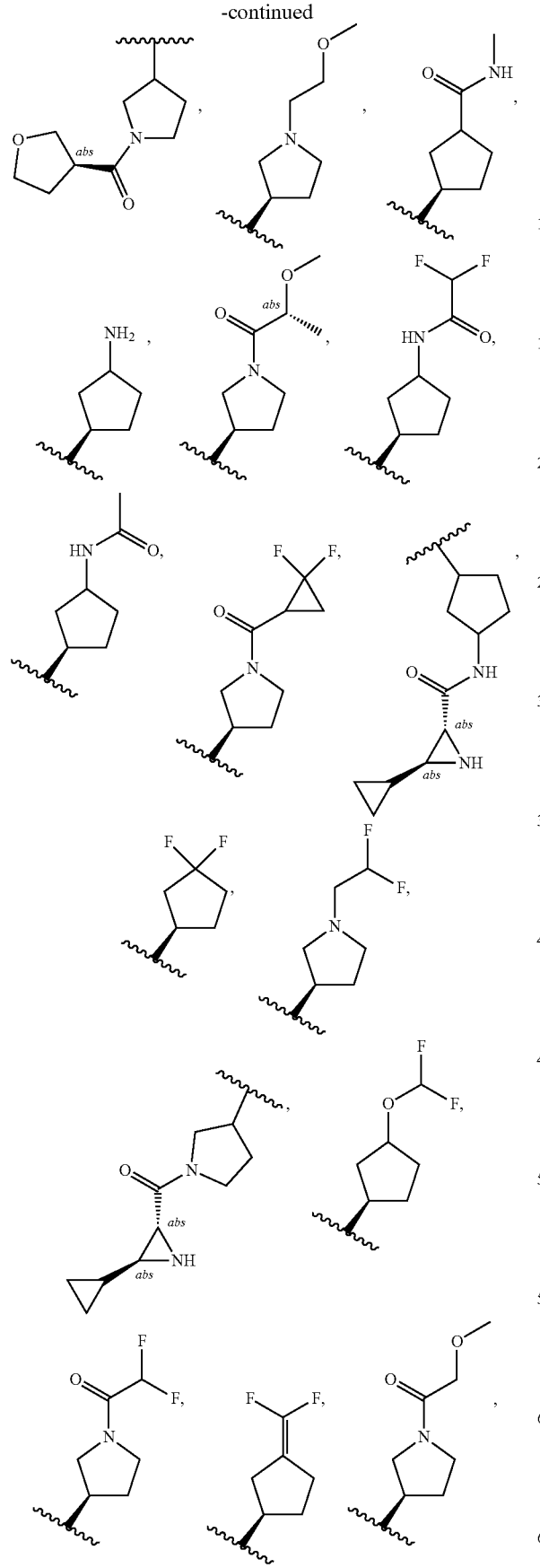
462
-continued
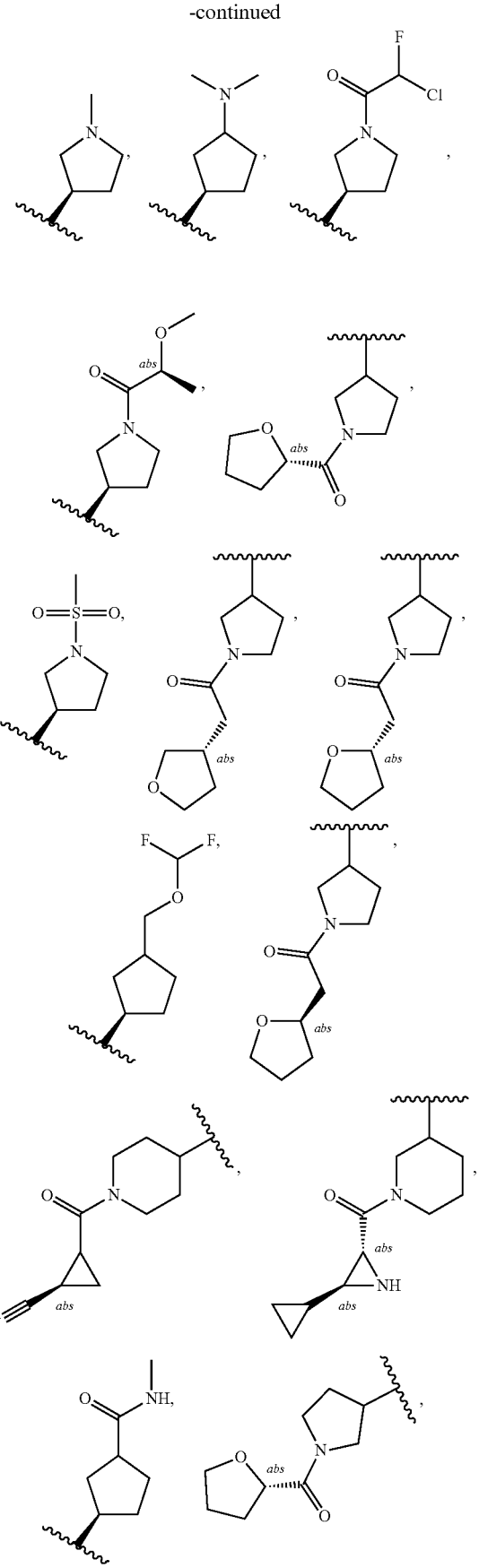

-continued

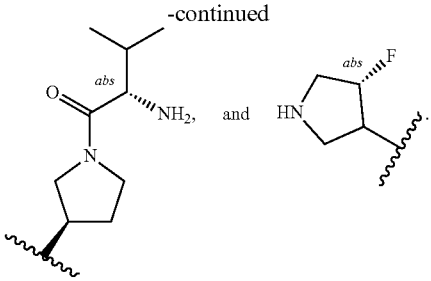

In some embodiments of a compound of Formula (A), (A'), (A''), (B), (B'), (B'''), (C), (C'), or (C''), or a pharmaceutically acceptable salt or solvate thereof, the compound has a formula selected from:

Formula (Ta)

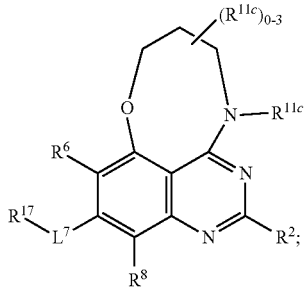

$R^6$ is selected from hydrogen and halogen;
$L^7$ is a bond;

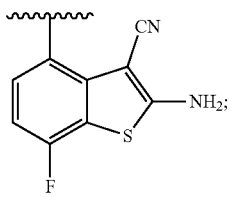 [SMILES: *c1ccc(F)c2sc(N)c(C#N)c12]

$R^{17}$ is

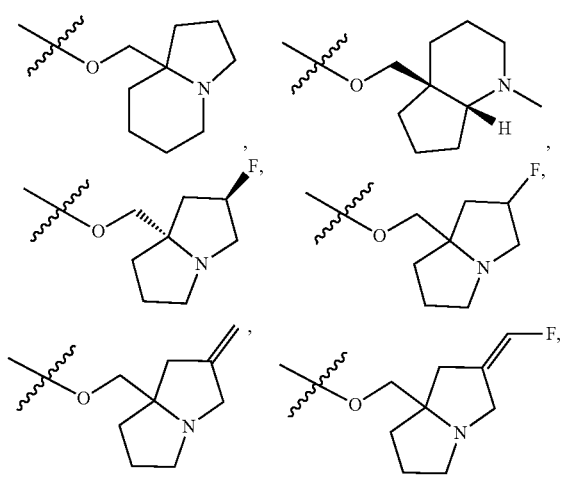

-continued

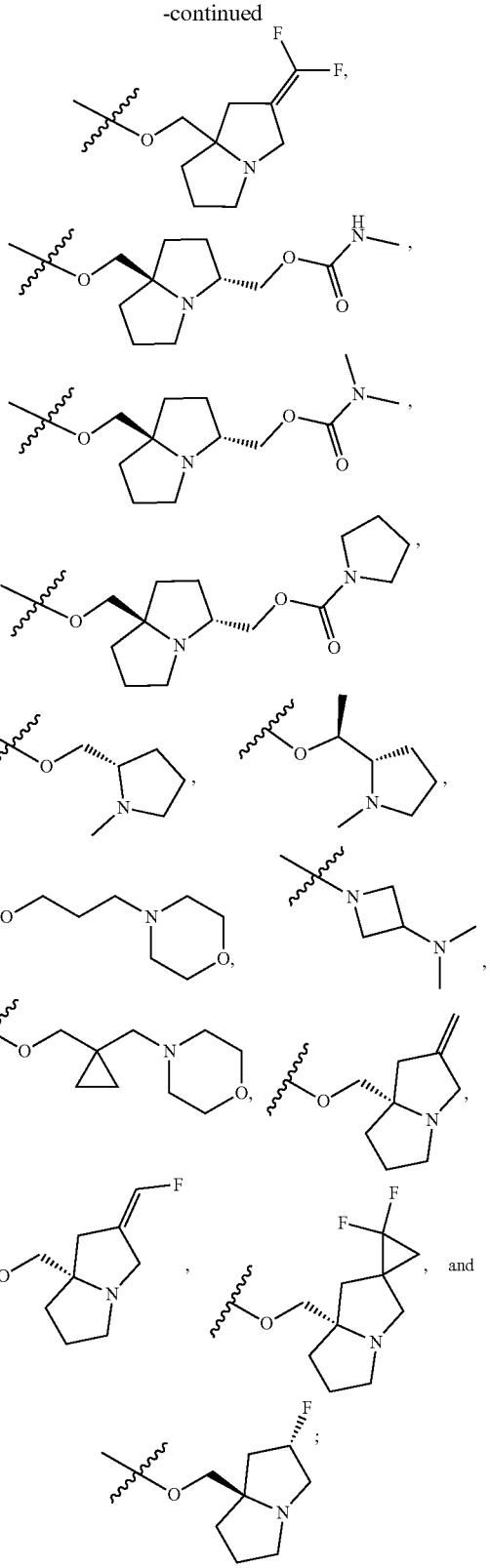

$R^8$ is selected from hydrogen and halogen;
each $R^{11c}$ is independently selected from —$OR^{12}$, $C_{1-3}$alkyl, $C_{3-4}$cycloalkyl, —$CH_2$-$C_{3-4}$cycloalkyl, and 5-6 membered heterocycloalkyl, wherein $C_{1-3}$alkyl,

465

C$_{3-4}$cycloalkyl, —CH$_2$-C$_{3-4}$cycloalkyl, and 5-6 membered heterocycloalkyl are optionally substituted with one, two, or three R$^{20k}$;

each R$^{20k}$ is independently selected from halogen, —N(R$^{22}$)(R$^{23}$), and —OR$^{21}$;

each R$^{12}$ is independently selected from hydrogen, C$_{1-6}$alkyl, and C$_{2-9}$heterocycloalkyl, wherein C$_{1-6}$alkyl, and C$_{2-9}$heterocycloalkyl are optionally substituted with one, two, or three R$^{20l}$;

each R$^{13}$ is independently selected from hydrogen and C$_{1-6}$alkyl;

each R$^{15}$ is independently selected from C$_{1-6}$alkyl and C$_{2-9}$heterocycloalkyl, wherein C$_{1-6}$alkyl and C$_{2-9}$heterocycloalkyl are optionally substituted with one, two, or three R$^{20m}$;

each R$^{20t}$ is independently selected from halogen, —CN, C$_{3-10}$cycloalkyl, —OR$^{21}$, and —N(R$^{22}$)(R$^{23}$);

each R$^{20m}$ is independently selected from halogen, —CN, C$_{3-10}$cycloalkyl, —OR$^{21}$, and —N(R$^{22}$)(R$^{23}$);

each R$^{21}$ is independently selected from H, C$_{1-3}$alkyl, C$_{1-3}$haloalkyl, C$_{3-6}$cycloalkyl, and 3-4 membered heterocycloalkyl;

each R$^{21b}$ is independently selected from H and halogen;

each R$^{22}$ is independently selected from H;

each R$^{23}$ is independently selected from H; and

----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula selected from:

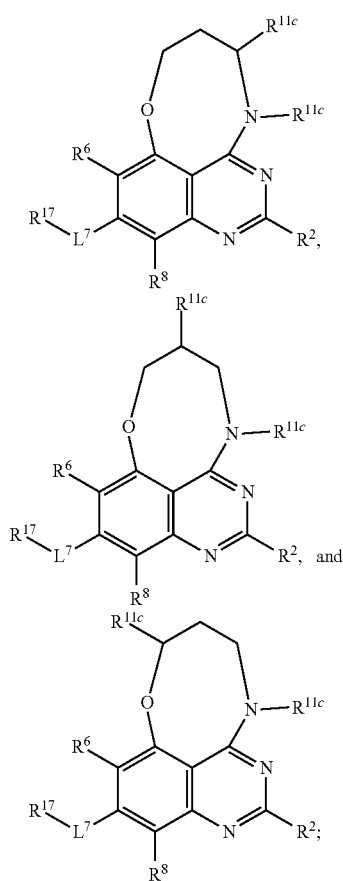

466

R$^6$ is selected from hydrogen and halogen;

L$^7$ is a bond;

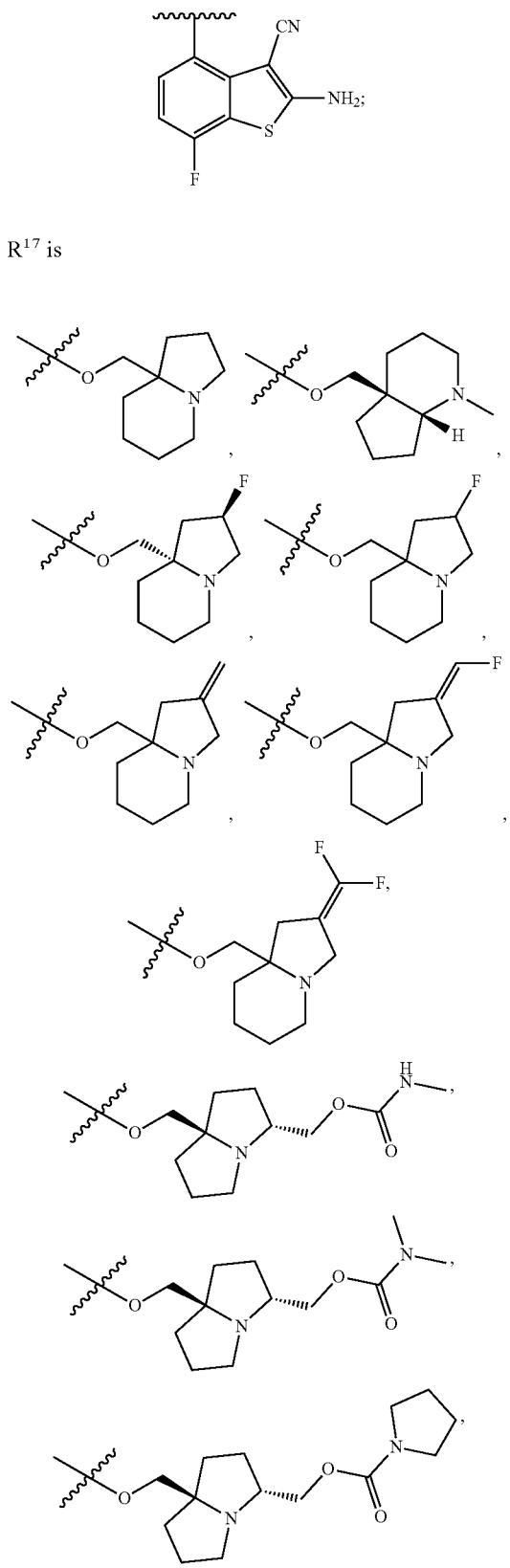

R$^{17}$ is

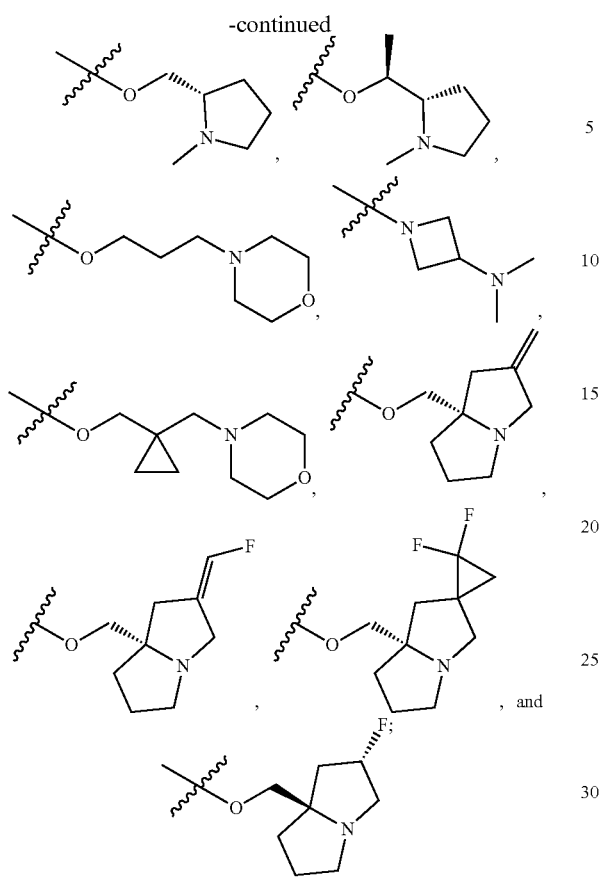
, and $R^2$ is selected from
$R^8$ is selected from hydrogen and halogen;
each $R^{11c}$ is independently selected from —$OR^{12}$, $C_{1-3}$alkyl, $C_{3-4}$cycloalkyl, —$CH_2$-$C_{3-4}$cycloalkyl, and 5-6 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$;
each $R^{20k}$ is independently selected from halogen, —$N(R^{22})(R^{23})$, and —$OR^{21}$;
each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20l}$;
each $R^{13}$ is independently selected from hydrogen and $C_{1-6}$alkyl;
each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20m}$;
each $R^{20t}$ is independently selected from halogen, —CN, $C_{3-10}$cycloalkyl, —$OR^{21}$, and —$N(R^{22})(R^{23})$;
each $R^{20m}$ is independently selected from halogen, —CN, $C_{3-10}$cycloalkyl, —$OR^{21}$, and —$N(R^{22})(R^{23})$;
each $R^{21}$ is independently selected from H, $C_{1-3}$alkyl, $C_{1-3}$haloalkyl, $C_{3-6}$cycloalkyl, and 3-4 membered heterocycloalkyl;
each $R^{21b}$ is independently selected from H and halogen;
each $R^{22}$ is independently selected from H;
each $R^{23}$ is independently selected from H; and
----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula selected from:

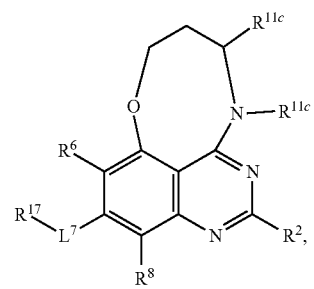

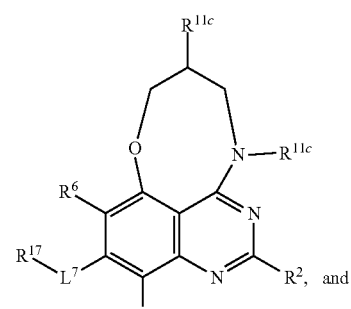
, and

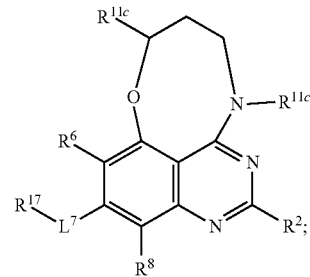

$R^6$ is selected from hydrogen and halogen;
$L^7$ is a bond;

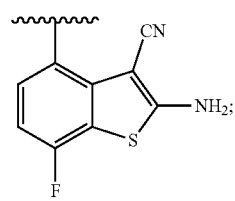 [SMILES: *c1ccc(F)c2sc(N)c(C#N)c12]

$R^{17}$ is

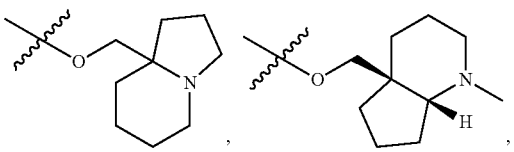
,

469

-continued

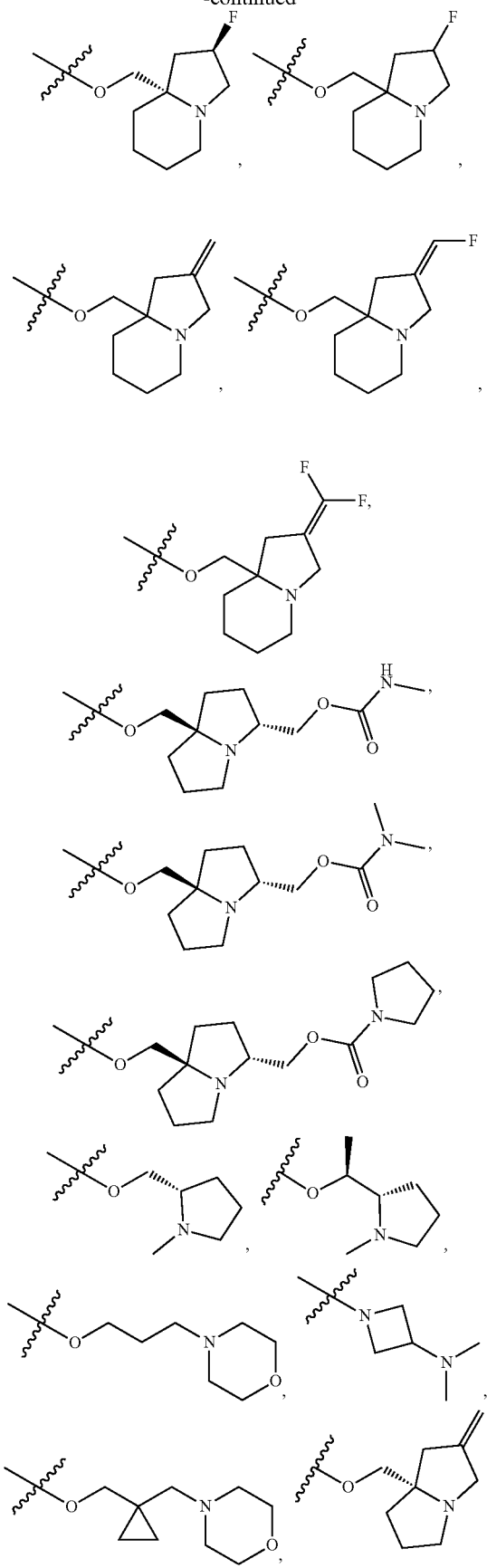

470

-continued

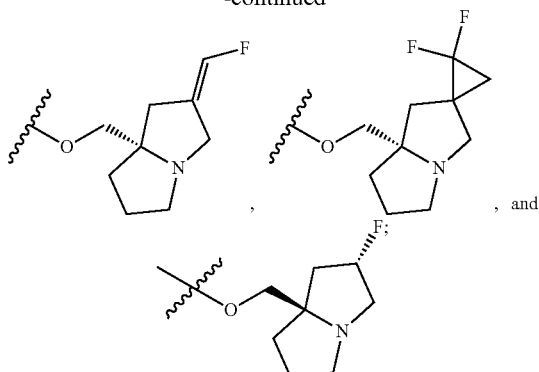

$R^2$ is selected from
$R^8$ is selected from hydrogen and halogen;
each $R^{11c}$ is independently selected from —$OR^{12}$, $C_{1-3}$alkyl, $C_{3-4}$cycloalkyl, —$CH_2$-$C_{3-4}$cycloalkyl, and 5 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$;
each $R^{20k}$ is independently selected from halogen, —$N(R^{22})(R^{23})$, and —$OR^{21}$;
each $R^{12}$ is independently selected from hydrogen;
each $R^{13}$ is independently selected from hydrogen and $C_{1-6}$alkyl;
each $R^{21}$ is independently selected from H and $C_{1-3}$alkyl;
each $R^{22}$ is hydrogen;
each $R^{23}$ is hydrogen; and
----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula

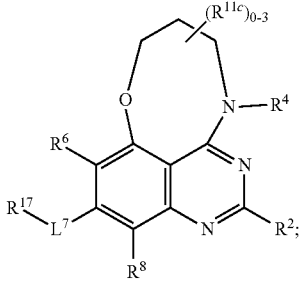

Formula (Xa)

$R^6$ is selected from hydrogen and halogen;
$L^7$ is a bond;
$R^{17}$ is

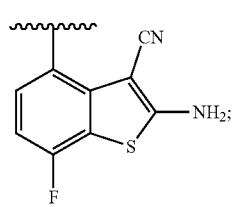 [SMILES: *c1ccc(F)c2sc(N)c(C#N)c12]

$R^2$ is selected from

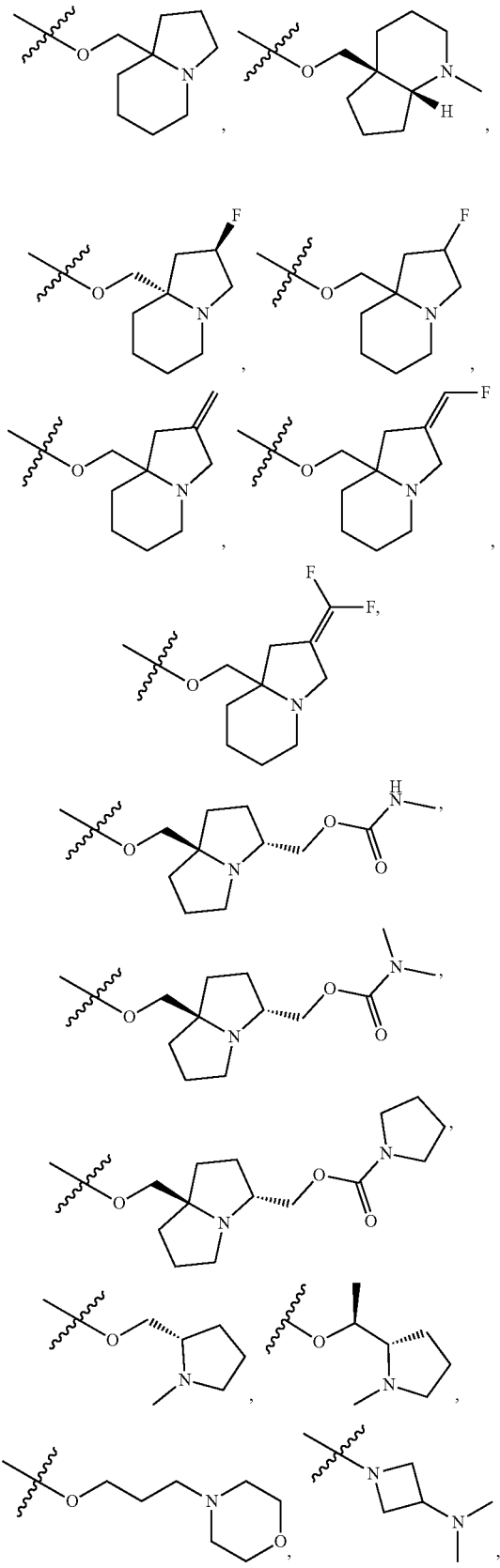

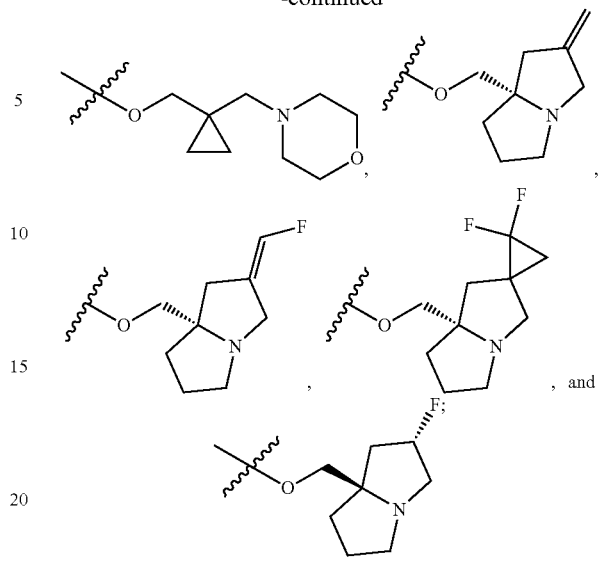

$R^8$ is selected from hydrogen and halogen;

$R^4$ is $-L^4-R^{4a}$;

each $L^4$ is independently selected from a bond and $CR^4R^4$;

each $R^{4c}$ is independently selected from hydrogen and $C_{1-3}$alkyl;

each $R^{4a}$ is independently selected from $C_{3-4}$cycloalkyl and 5-6 membered heterocycloalkyl, wherein $C_{3-4}$cycloalkyl and 5-6 membered heterocycloalkyl are optionally substituted with one, two, three, or four $R^{40}$;

each $R^{4b}$ is independently selected from halogen, oxo, —CN, $C_{1-3}$alkyl, $C_{3-6}$cycloalkyl, —$OR^{12}$, —$N(R^{12})(R^{13})$, =$C(R^{21b})_2$, —$C(O)R^{12}$, —$N(R^{14})C(O)R^{12}$, —$S(O)_2R^{15}$, and —$C(O)N(R^{12})(R^{13})$, wherein $C^{1-3}$alkyl and $C_{3-6}$cycloalkyl are optionally substituted with one or more $R^{20j}$;

each $R^{11c}$ is independently selected from —$OR^{12}$, $C^{1-3}$alkyl, $C_{3-4}$cycloalkyl, —$CH_2$-$C_{3-4}$cycloalkyl, and 5-6 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$;

each $R^{20k}$ is independently selected from halogen, —$N(R^{22})(R^{23})$, and —$OR^{21}$;

each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20l}$;

each $R^{13}$ is independently selected from hydrogen and $C_{1-6}$alkyl;

each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20m}$;

each $R^{20j}$ is independently selected from halogen and —$OR^{21}$;

each $R^{20l}$ is independently selected from halogen, —CN, $C_{3-10}$cycloalkyl, —$OR^{21}$, and —$N(R^{22})(R^{23})$;

each $R^{20m}$ is independently selected from halogen, —CN, $C_{3-10}$cycloalkyl, —$OR^{21}$, and —$N(R^{22})(R^{23})$;

each $R^{21}$ is independently selected from H, $C_{1-3}$alkyl, $C_{1-3}$haloalkyl, $C_{3-6}$cycloalkyl, and 3-4 membered heterocycloalkyl;

each $R^{21b}$ is independently selected from H and halogen;
each $R^{22}$ is independently selected from H;
each $R^{23}$ is independently selected from H; and
----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula selected from:

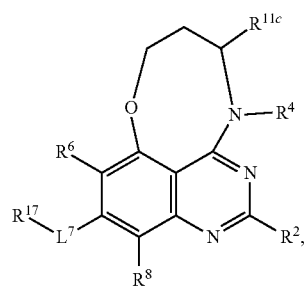

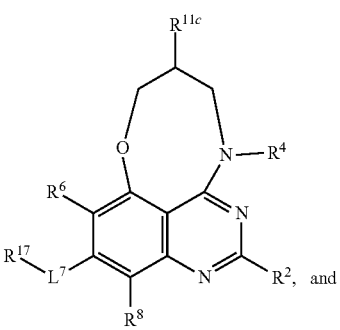

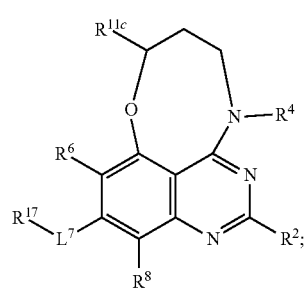

$R^6$ is selected from hydrogen and halogen;
$L^7$ is a bond;

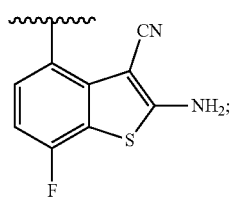 [SMILES: *c1ccc(F)c2sc(N)c(C#N)c12]

$R^{17}$ is

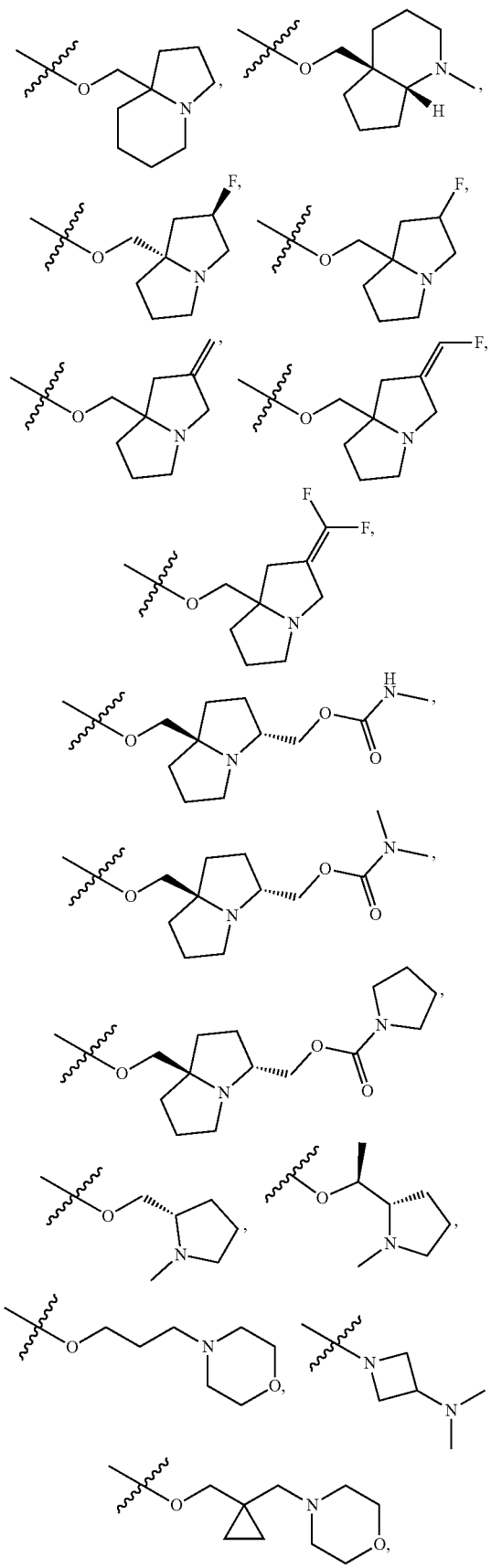

-continued

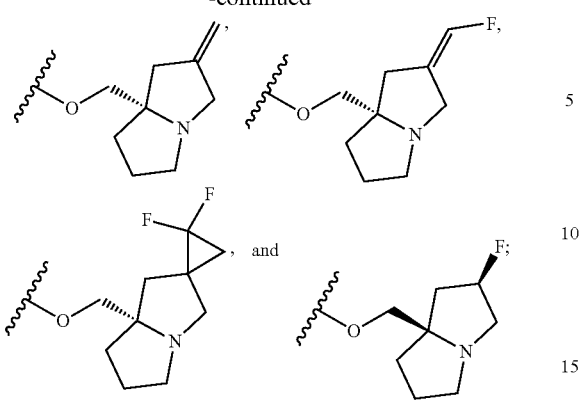

$R^8$ is selected from hydrogen and halogen;
$R^4$ is -$L^4$-$R^{4a}$;
each $L^4$ is independently selected from a bond and $CR^{4c}R^{4c}$;
each $R^{4c}$ is independently selected from hydrogen and $C_{1-3}$alkyl;
each $R^{4a}$ is independently selected from $C_{3-4}$cycloalkyl and 5-6 membered heterocycloalkyl, wherein $C_{3-4}$cycloalkyl and 5-6 membered heterocycloalkyl are optionally substituted with one, two, three, or four $R^{4b}$;
each $R^{4b}$ is independently selected from halogen, oxo, —CN, $C_{1-3}$alkyl, $C_{3-6}$cycloalkyl, —$OR^{12}$, —$N(R^{12})(R^{13})$, —$C(R^{21b})_2$, —$C(O)R^{12}$, —$N(R^{14})C(O)R^{12}$, —$S(O)_2R^{15}$, and —$C(O)N(R^{12})(R^{13})$, wherein $C_{1-3}$alkyl and $C_{3-6}$cycloalkyl are optionally substituted with one or more $R^{20j}$;
each $R^{11c}$ is independently selected from —$OR^{12}$, $C_{1-3}$alkyl, $C_{3-4}$cycloalkyl, —$CH_2$-$C_{3-4}$cycloalkyl, and 5-6 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$;
each $R^{20k}$ is independently selected from halogen, —$N(R^{22})(R^{23})$, and —$OR^{21}$;
each $R^{12}$ is independently selected from hydrogen, $C_{1-6}$alkyl, and $C_{2-9}$heterocycloalkyl, wherein $C_{1-6}$alkyl and $C_{2-9}$heterocycloalkyl are optionally substituted with one, two, or three $R^{20t}$;
each $R^{13}$ is independently selected from hydrogen and $C_{1-6}$alkyl;
each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20m}$;
each $R^{20j}$ is independently selected from halogen and —$OR^{21}$;
each $R^{20t}$ is independently selected from halogen, —CN, $C_{3-10}$cycloalkyl, —$OR^{21}$, and —$N(R^{22})(R^{23})$;
each $R^{20m}$ is independently selected from halogen, —CN, $C_{3-10}$cycloalkyl, —$OR^{21}$, and —$N(R^{22})(R^{23})$;
each $R^{21}$ is independently selected from H, $C_{1-3}$alkyl, $C_{1-3}$haloalkyl, $C_{3-6}$cycloalkyl, and 3-4 membered heterocycloalkyl;
each $R^{21b}$ is independently selected from H and halogen;
each $R^{22}$ is independently selected from H;
each $R^{23}$ is independently selected from H; and
----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula selected from:

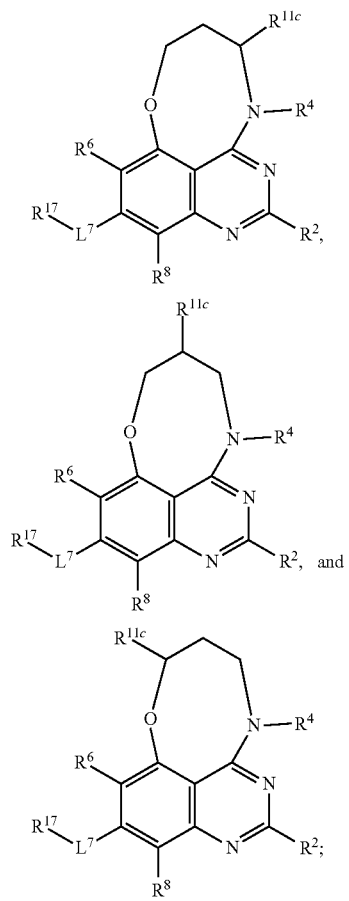

$R^6$ is selected from hydrogen and halogen;
$L^7$ is a bond;
$R^{17}$ is

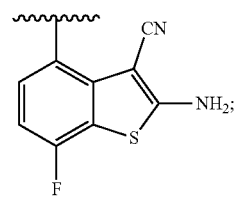 [SMILES: *c1ccc(F)c2sc(N)c(C#N)c12]

$R^2$ is selected from

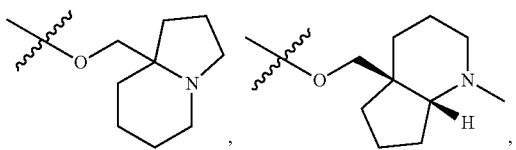

477
-continued

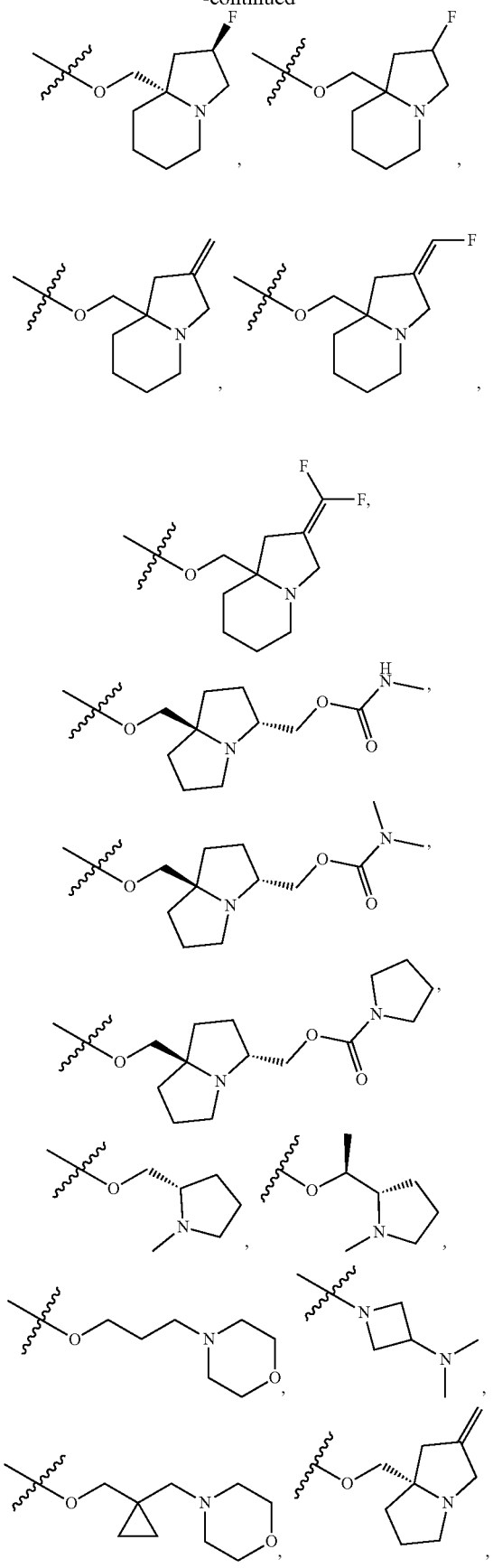

478
-continued

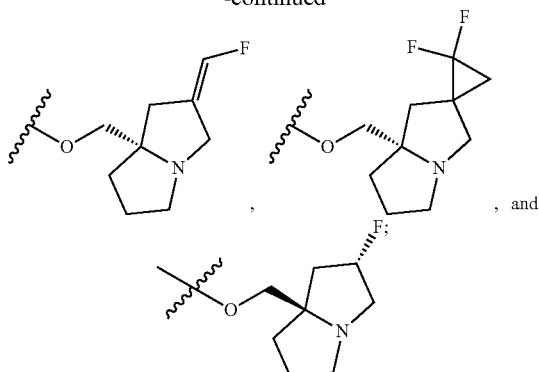

$R^8$ is selected from hydrogen and halogen;
$R^4$ is -$L^4$-$R^{4a}$;
each $L^4$ is independently selected from a bond and $CH_2$;
each $R^{4c}$ is independently selected from hydrogen and $C_{1-3}$alkyl;
each $R^{4a}$ is independently selected from $C_3$-cycloalkyl and 5 membered heterocycloalkyl, wherein $C_3$-cycloalkyl and 5 membered heterocycloalkyl are optionally substituted with one or two R®0;
each $R^{4b}$ is independently selected from halogen, —$OR^{12}$, and —$N(R^{12})(R^{13})$;
each $R^{11c}$ is independently selected from —$OR^{12}$, $C_{1-3}$alkyl, $C_3$cycloalkyl, —$CH_2$-$C_{3-4}$cycloalkyl, and 5 membered heterocycloalkyl, wherein $C_{1-3}$alkyl, $C_3$cycloalkyl, —$CH_2$-$C_3$-cycloalkyl, and 5 membered heterocycloalkyl are optionally substituted with one, two, or three $R^{20k}$.
each $R^{20k}$ is independently selected from halogen, —$N(R^{22})(R^{23})$, and —$OR^{21}$;
each $R^{12}$ is independently selected from hydrogen;
each $R^{13}$ is independently selected from hydrogen;
each $R^{21}$ is independently selected from hydrogen and $C_{1-3}$alkyl;
each $R^{22}$ is hydrogen;
each $R^{23}$ is hydrogen; and
----- indicates a single or double bond such that all valences are satisfied.

In an aspect is provided a compound of Formula (A'''), or a pharmaceutically acceptable salt or solvate thereof:

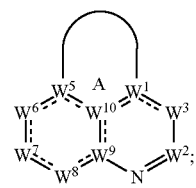

Formula (A''')

wherein:
Ring A; $W^1$; $R^1$; $W^2$; $W^3$; $R^2$, $R^3$; $R^{3a}$; $R^{3b}$; $W^5$; $R^5$; $W^6$; $R^6$; $R^{6a}$; $R^{6b}$; $W^7$; $R^{7a}$; $R^{7c}$; $R^{74}$; $R^7$; $L^7$; $W^8$; $R^8$; $R^{8a}$; $R^{8b}$; $W^9$; $W^{10}$; $R^9$; $R^4$; $L^4$;
$R^{4b}$, $R^{4c}$; $R^{4d}$; $R^{43}$; $R^{11c}$, $R^{12}$; $R^{12c}$; $R^{13}$; $R^{14}$; $R^{14a}$; $R^{15}$; $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$; $R^{20m}$, $R^{21}$;
$R^{21b}$, $R^{22}$; $R^{23}$; $R^{24}$; and $R^{25}$ are as described for Formula (A''), including in embodiments of a compound of Formula (A'');

R¹⁷ is

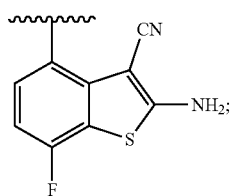 [SMILES: *c1ccc(F)c2sc(N)c(C#N)c12]

and ----- indicates a single or double bond such that all valences are satisfied.

In an aspect is provided a compound of Formula (A″), or a pharmaceutically acceptable salt or solvate thereof:

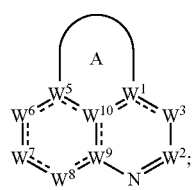

Formula (A″)

wherein:
Ring A; W¹; R¹; W²; W³; R², R³; R³ᵃ; R³ᵇ; W⁵; R⁵; W⁶; R⁶; Roa; R⁶ᵇ; W⁷; R⁷ᵃ; R⁷ᶜ; R⁷⁴; R⁷; L⁷; R¹⁷; W⁸; R⁸; R⁸ᵃ; R⁸ᵇ; W⁹; W¹⁰; R⁹; R⁴;
L⁴; R⁴ᵇ, R⁴ᶜ; R⁴ᵈ; R⁴³; R¹¹ᶜ, R¹²; R¹²ᶜ; R¹³; R¹⁴; R¹⁴ᵇ; R¹⁵; R²⁰ᵃ, R²⁰ᵇ, R²⁰ᶜ, R²⁰ᵈ, R²⁰ᵉ, R²⁰ᶠ, R²⁰ᵍ, R²⁰ʰ, R²⁰ⁱ, R²⁰ʲ, R²⁰ᵏ, R²⁰ˡ, R²⁰ᵐ, R²¹;

R²¹ᵇ, R²², R²³; R²⁴; and R²⁵ are as described for Formula (A″), including in embodiments of a compound of Formula (A″);

each R¹¹ᶜ is independently selected from halogen, oxo, —CN, C₁₋₆alkyl, C₂₋₆alkenyl, C₂₋₆alkynyl, C₁₋₆haloalkyl, C₃₋₁₂cycloalkyl, —CH₂-C₃₋₁₂cycloalkyl, C₁₋₁₁heterocycloalkyl, —CH₂-C₁₋₁₁heterocycloalkyl, C₆₋₁₂aryl, —CH₂-C₆₋12aryl, —CH₂-C₁₋₁₁heteroaryl, C₁₋₁₁ heteroaryl, —OR¹², —SR¹², —N(R¹²)(R¹³), —C(R¹²)=NO(R¹²), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹², —S(O)R¹⁵, —OC(O)R¹⁵, —C(O)N(R¹²)(R¹³), —C(O)C(O)N(R¹²)(R¹³), —N(R¹⁴)C(O)R¹², —S(O)₂R¹⁵, —S(O)₂N(R¹²)(R¹³), —S(=O)(=NH)N(R¹²)(R¹³), —(C₁₋₆alkyl)-OC(O)R¹², —(C₁₋₆alkyl)-N(R¹²)(R¹³), —(C₁₋₆alkyl)-C(O)N(R¹²)(R¹³), —(C₁₋₆alkyl)-N(R¹⁴)C(O)R¹², —(C₁₋₆alkyl)-S(O)₂R¹⁵, —(C₁₋₆alkyl)-S(O)₂N(R¹²)(R¹³), wherein C₁₋₆alkyl, C₂₋₆alkenyl, C₂₋₆alkynyl, C₁₋₆haloalkyl, C₃₋₁₂cycloalkyl, —CH₂-C₃₋₁₂cycloalkyl, C₁₋₁₁heterocycloalkyl, —CH₂-C₁₋₁₁heterocycloalkyl, C₆₋₁₂aryl, —CH₂-C₆-12aryl, —CH₂-C₁₋₁₁heteroaryl, and C₁₋₁₁heteroaryl are optionally substituted with one, two, three, four, or five R²⁰ᵏ; and ----- indicates a single or double bond such that all valences are satisfied. In embodiments of the formulae above, R¹¹⁸ is independently selected from hydrogen,

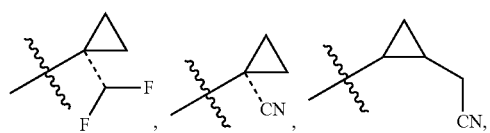

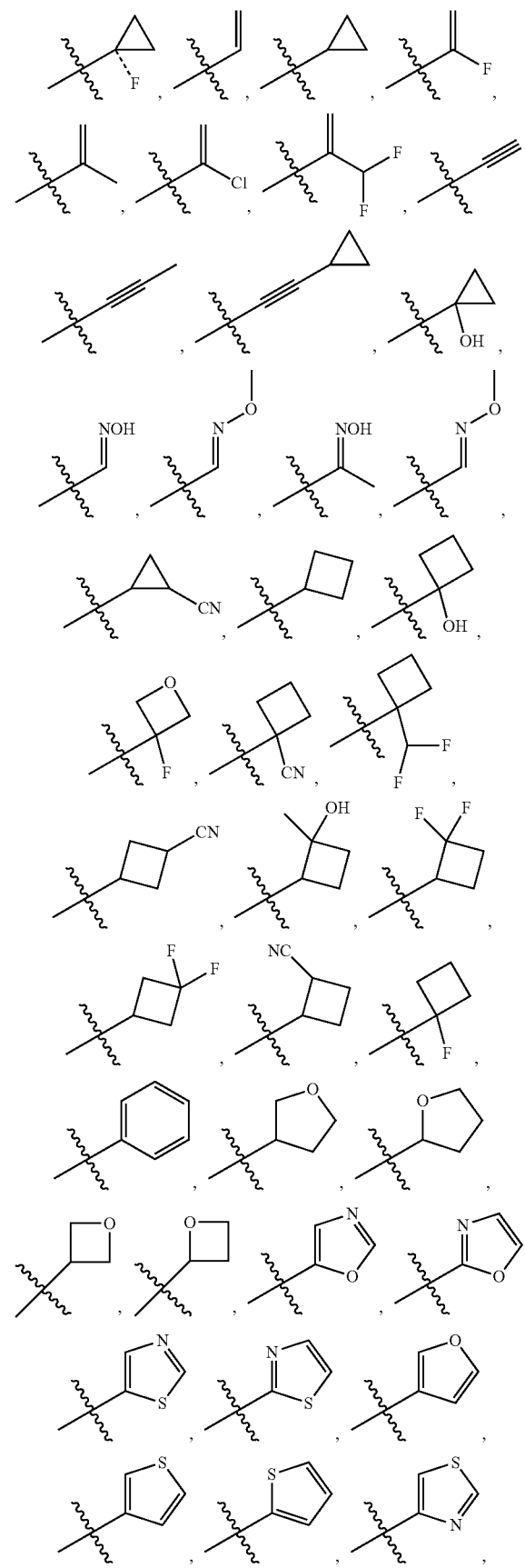

481
-continued
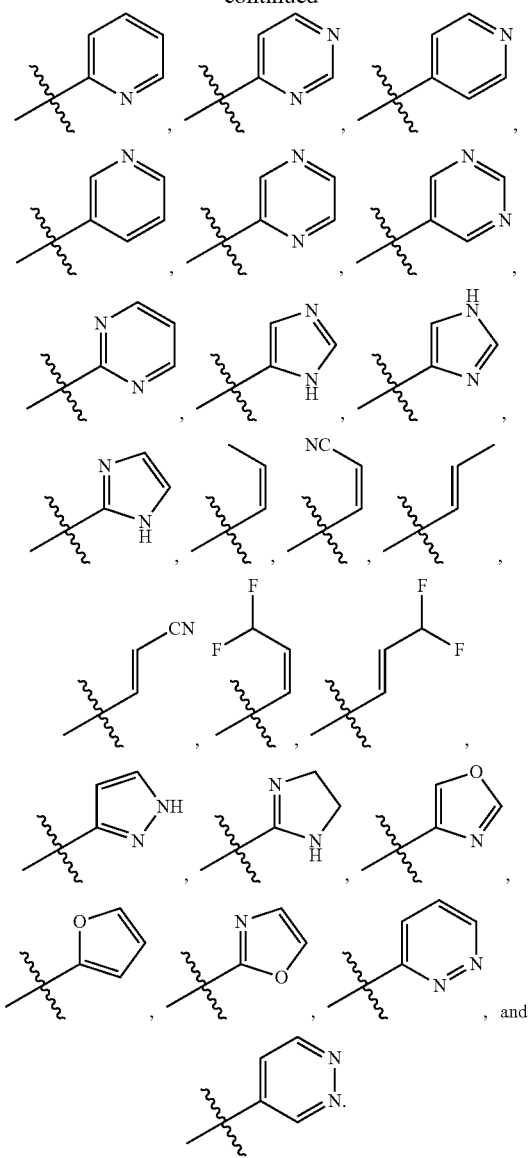
In some embodiments of a compound of Formula (A), (A'), (A''), (B), (B'), (B''), (C), (C'), or (C''), or a pharmaceutically acceptable salt or solvate thereof, the compound has a formula selected from:
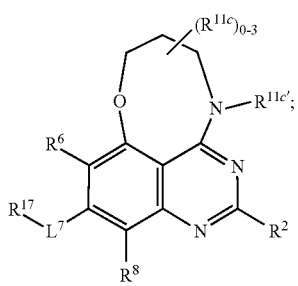
$R^6$ is selected from hydrogen and halogen;
$L^7$ is a bond;
482
$R^{17}$ is
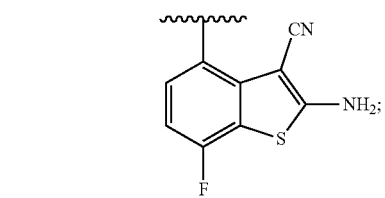 [SMILES: *c1ccc(F)c2sc(N)c(C#N)c12]
$R^2$ is selected from
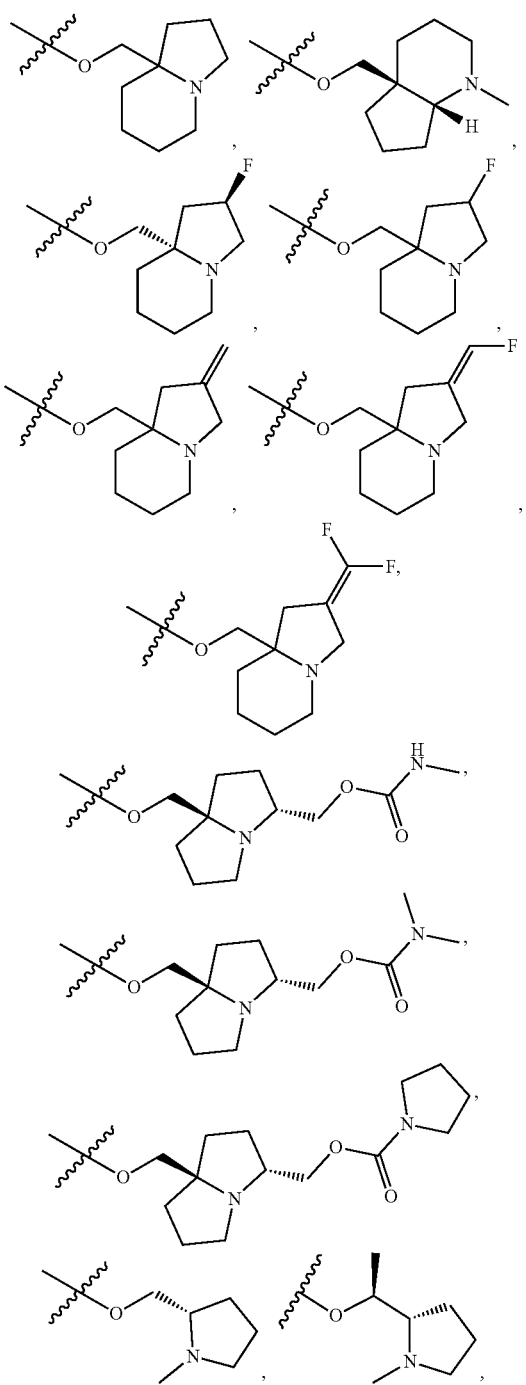

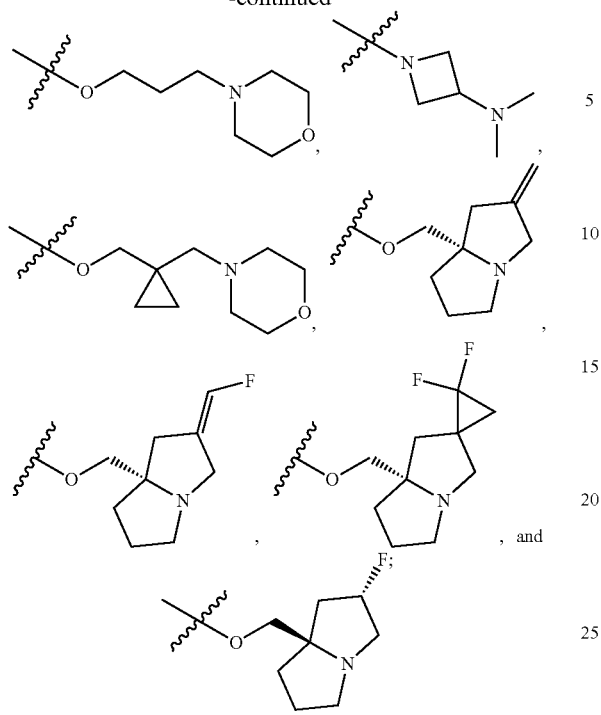

$R^8$ is selected from hydrogen and halogen;

each $R^{11c}$ independently selected from $C_{2-3}$alkenyl, $C_{2-3}$alkynyl, $C_{3-4}$cycloalkyl, —$CH_2$—($C_{3-4}$cycloalkyl), 4-5 membered heterocycloalkyl, —$CH_2$-(4-5 membered heterocycloalkyl), phenyl, —$CH_2$-(phenyl), 5-6 membered heteroaryl, and —$CH_2$-(5-6 membered heteroaryl), wherein $C_{1-4}$alkyl, $C_{2-3}$alkenyl, $C_{2-3}$alkynyl, $C_{3-4}$cycloalkyl, —$CH_2$—($C_{3-4}$cycloalkyl), 4-5 membered heterocycloalkyl, —$CH_2$-(4-5 membered heterocycloalkyl), phenyl, —$CH_2$-(phenyl), 5-6 membered heteroaryl, and —$CH_2$-(5-6 membered heteroaryl) are optionally substituted with one, two, or three $R^{20k}$;

each $R^{11c1}$ independently selected from $C_{1-4}$alkyl, $C_{2-3}$alkenyl, $C_{2-3}$alkynyl, $C_{3-4}$cycloalkyl, —$CH_2$—($C_{3-4}$cycloalkyl), 4-5 membered heterocycloalkyl, —$CH_2$-(4-5 membered heterocycloalkyl), phenyl, —$CH_2$-(phenyl), 5-6 membered heteroaryl, and —$CH_2$-(5-6 membered heteroaryl), wherein $C_{1-4}$alkyl, $C_{2-3}$alkenyl, $C_{2-3}$alkynyl, $C_{3-4}$cycloalkyl, —$CH_2$—($C_{3-4}$cycloalkyl), 4-5 membered heterocycloalkyl, —$CH_2$-(4-5 membered heterocycloalkyl), phenyl, —$CH_2$-(phenyl), 5-6 membered heteroaryl, and —$CH_2$-(5-6 membered heteroaryl) are optionally substituted with one, two, or three $R^{20k}$;

each $R^{20k}$ is independently selected from halogen, —CN, $C_{1-3}$alkyl, —$NH_2$, and —$OR^{21}$, wherein $C_{1-3}$alkyl is optionally substituted with one, two, or three groups independently selected from halogen and —CN; and each $R^{21}$ is independently selected from H, $C_{1-3}$alkyl, and $C_{1-3}$haloalkyl; and ----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula selected from:

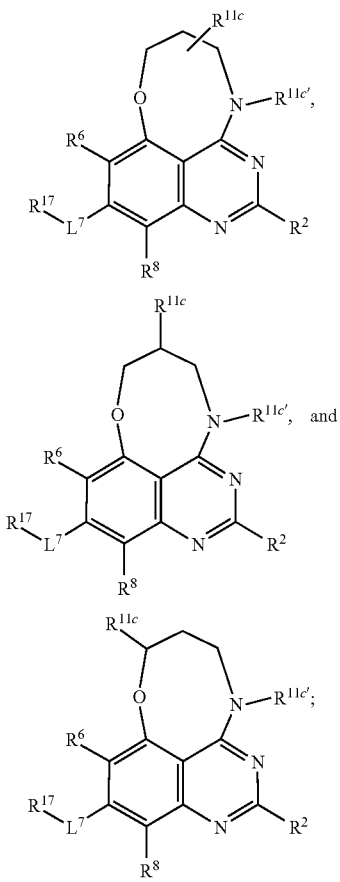

$R^6$ is selected from hydrogen and halogen;
$L^7$ is a bond;

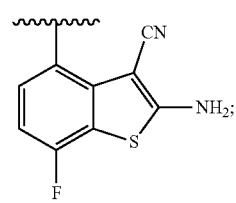 [SMILES: *c1ccc(F)c2sc(N)c(C#N)c12]

$R^{17}$ is

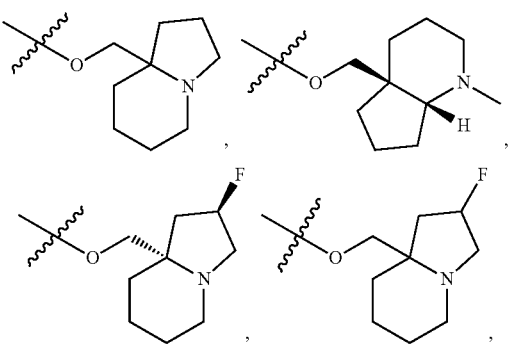

485
-continued

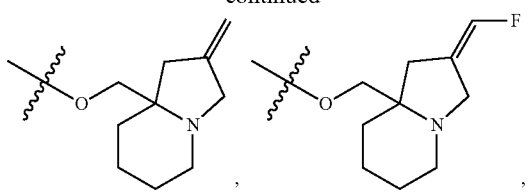

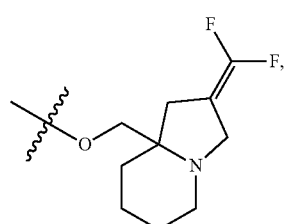

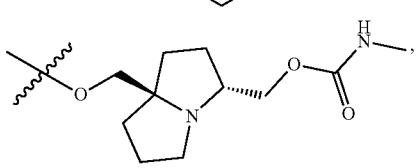

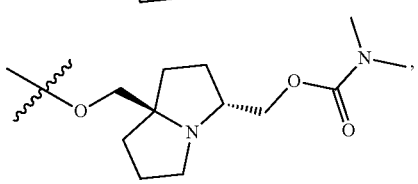

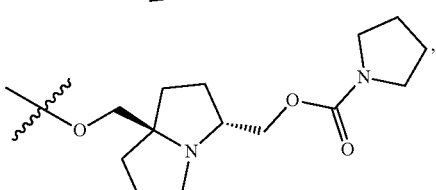

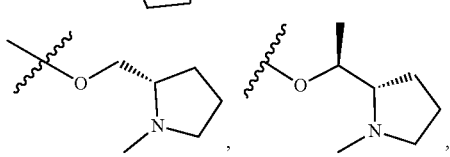

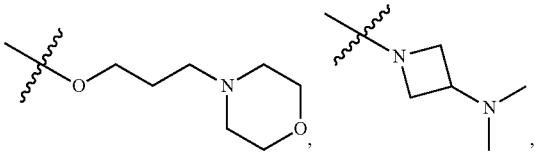

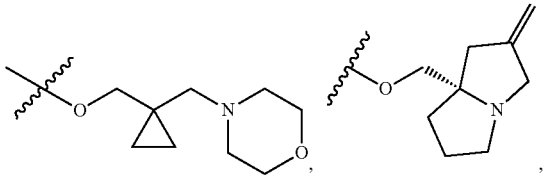

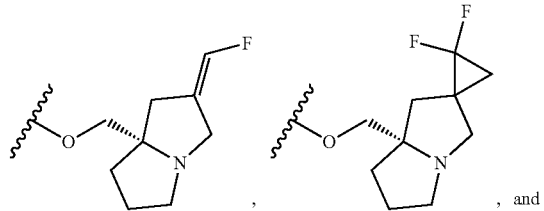
, and

486
-continued

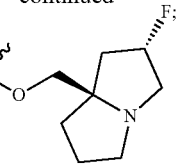

$R^2$ is selected from
$R^8$ is selected from hydrogen and halogen;
each $R^{11c}$ independently selected from $C_{2-3}$alkenyl, $C_{2-3}$alkynyl, $C_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl), wherein $C_{1-4}$alkyl, $C_{2-3}$alkenyl, $C_{2-3}$alkynyl, $C_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl) are optionally substituted with one, two, or three $R^{20k}$;

each $R^{11c'}$ independently selected from $C_{1-4}$alkyl, $C_{2-3}$alkenyl, $C_{2-3}$alkynyl, $C_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl), wherein $C_{1-4}$alkyl, $C_{2-3}$alkenyl, $C_{2-3}$alkynyl, $C_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl) are optionally substituted with one, two, or three $R^{20k}$;

each $R^{20k}$ is independently selected from halogen, —CN, $C_{1-3}$alkyl, —NH$_2$, and —OR$^{21}$, wherein $C_{1-3}$alkyl is optionally substituted with one, two, or three groups independently selected from halogen and —CN; and each $R^{21}$ is independently selected from H, $C_{1-3}$alkyl, and $C_{1-3}$haloalkyl; and ----- indicates a single or double bond such that all valences are satisfied. In embodiments of the formulae above, $R^{11c'}$ is independently selected from

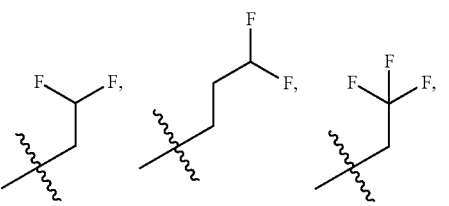

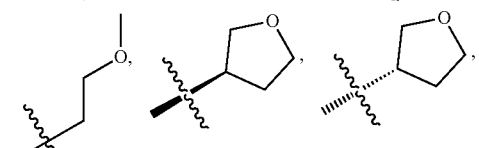

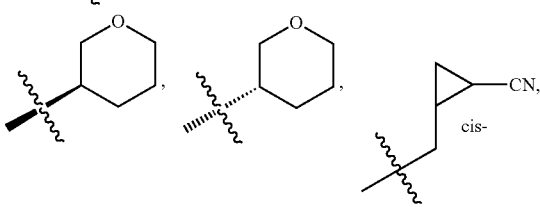

487
-continued
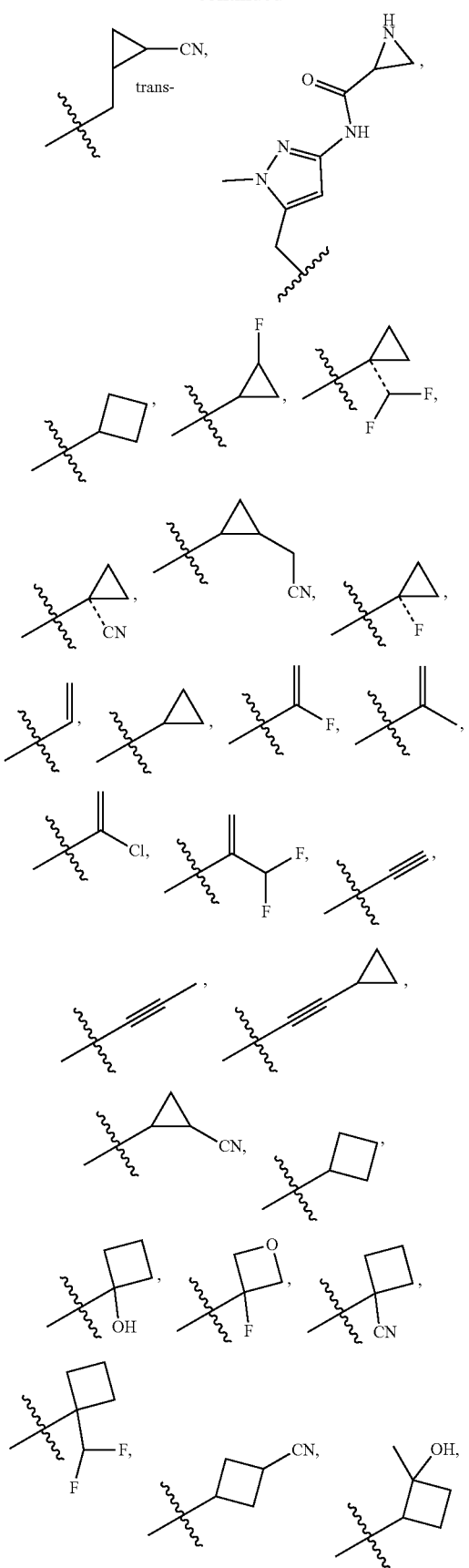
488
-continued
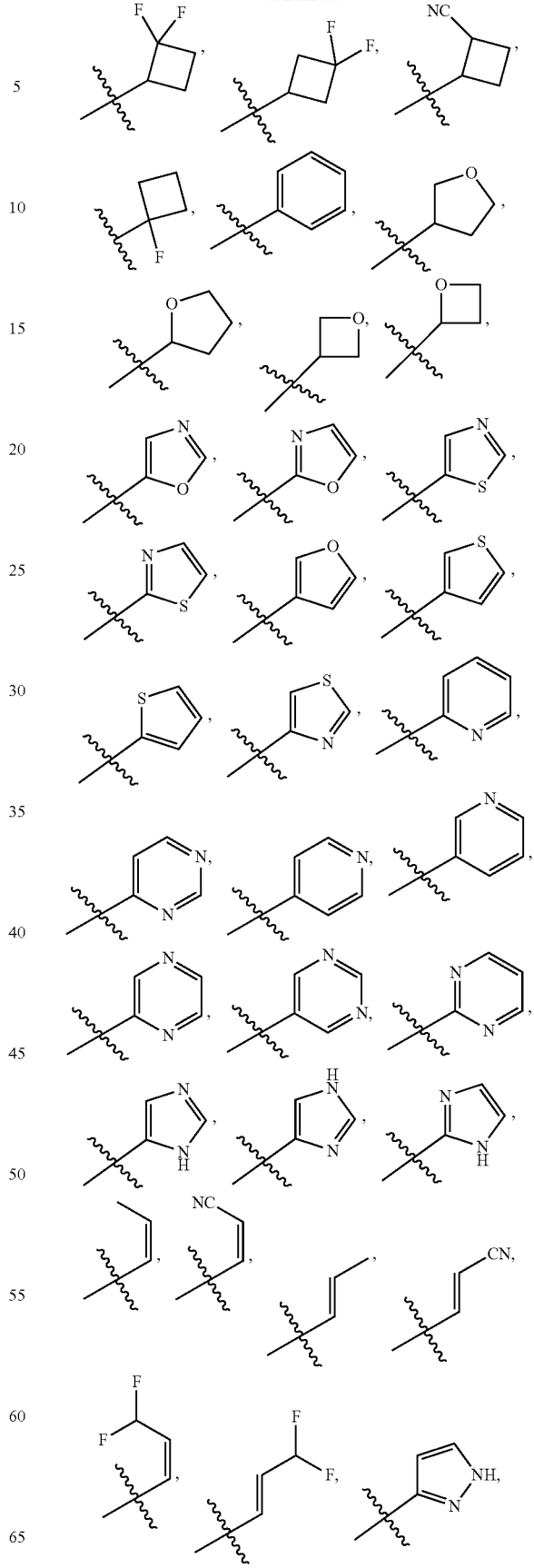

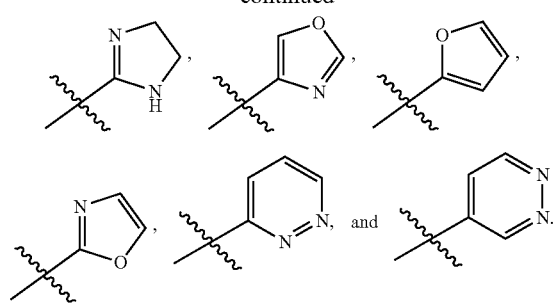
In embodiments of the formulae above, $R^{11c}$ is independently selected from
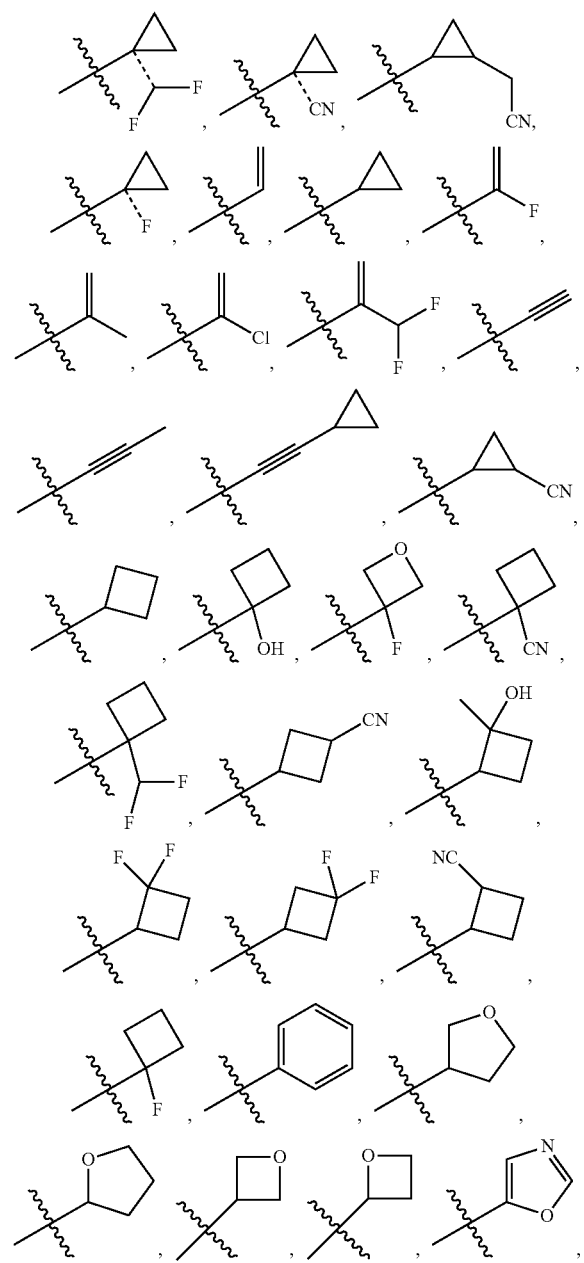
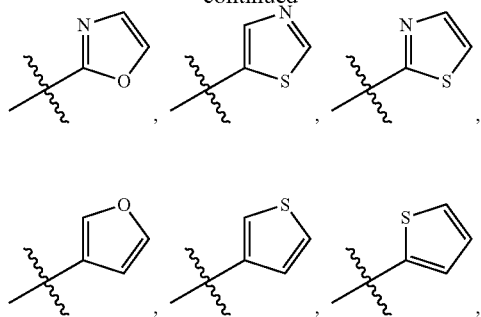
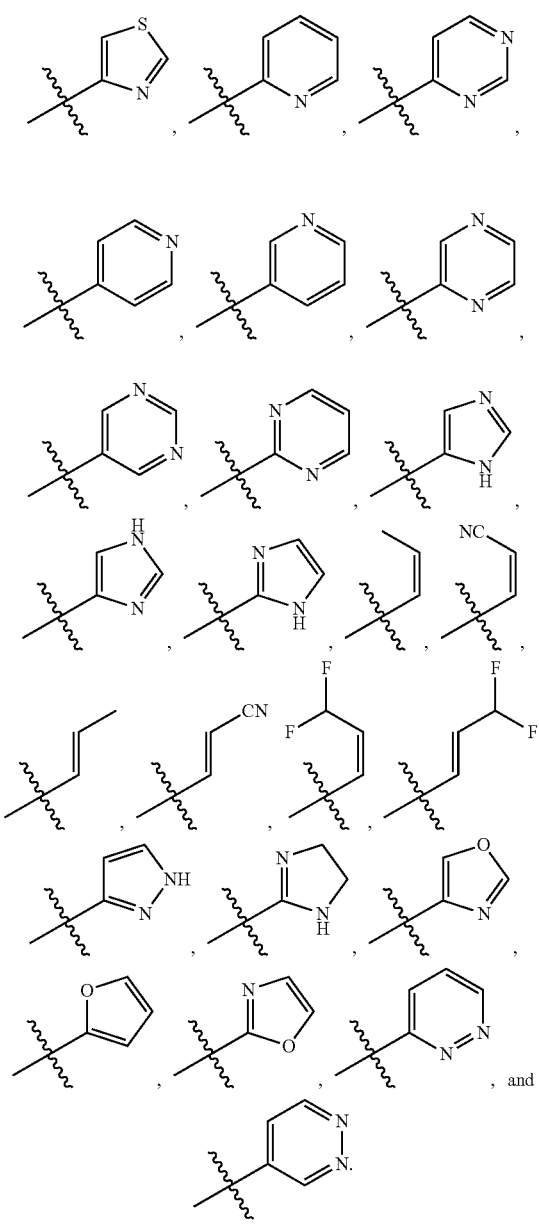
In some embodiments of a compound of Formula (A), (A'), (A''), (B), (B'), (B''), (C), (C'), or (C''), or a pharmaceutically acceptable salt or solvate thereof, the compound has a formula selected from:

491

[Structure with $R^6$, $L^7$, $R^{17}$, $R^8$, $R^2$, and $(R^{11c})_{0-3}$, $N-R^{11c}$]

$R^6$ is selected from hydrogen and halogen;
$L^7$ is a bond;
$R^{17}$ is selected from:

[Three heterocyclic structures with $X^{12}$, $X^9$, $X^{10}$, $X^{11}$, $Q^3$, $Q^4$, $R^{1h}$; and two other ring systems with $X^4$, $X^5$, $X^{15}$, $X^{16}$, $X^{17}$, and $X^4$, $X^{13}$, $X^{14}$, $X^{16}$, $X^{10}$, $X^{11}$]

$Q^3$ is N or $C(R^{1d})$; $Q^4$ is S;
$X^4$, $X^5$, $X^{15}$, $X^{16}$, and $X^{17}$ are independently selected from $C(R^{1a})$ or N;
$X^9$ is $C(R^{1a})$; $X^{10}$, $X^{11}$, $X^{13}$, and $X^{14}$ are independently $C(R^{1a})$ or N; $X^{12}$ is C;
each $R^{1a}$ and $R^{1h}$ is independently selected from hydrogen, halogen, —CN, $C_{1-4}$alkyl, $C^{1-4}$haloalkyl, $C_{2-4}$alkenyl, $C_{2-4}$alkynyl, $C_{3-4}$ cycloalkyl, $C_{2-4}$heterocycloalkyl, —OH, —NH$_2$, —C(O)OH, —OC(O)NH$_2$, and —C(O)CH$_3$;
$R^{1d}$ is selected from hydrogen, —CN, $C_{1-4}$alkyl, and $C_{1-4}$haloalkyl;
$R^2$ is selected from

492

-continued $R^2$ is selected from
$R^8$ is selected from hydrogen and halogen;
each $R^{11c}$ independently selected from $C_{2-3}$alkenyl, $C_{2-3}$alkynyl, $C_{3-4}$cycloalkyl, —CH$_2$—($C_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl), wherein C$_{2-3}$alkenyl, C$_{2-3}$alkynyl, C$_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl) are optionally substituted with one, two, or three R$^{20k}$;

each R$^{20k}$ is independently selected from halogen, —CN, C$_{1-3}$alkyl, —NH$_2$, and —OR$^{21}$, wherein C$^{1-3}$alkyl is optionally substituted with one, two, or three groups independently selected from halogen and —CN; and each R$^{21}$ is independently selected from H, C$_{1-3}$alkyl, and C$_{1-3}$haloalkyl; and ----- indicates a single or double bond such that all valences are satisfied.

In some embodiments of a compound of Formula (A), (A'), (A"), (B), (B'), (B"), (C), (C'), or (C"), or a pharmaceutically acceptable salt or solvate thereof, the compound has a formula selected from:

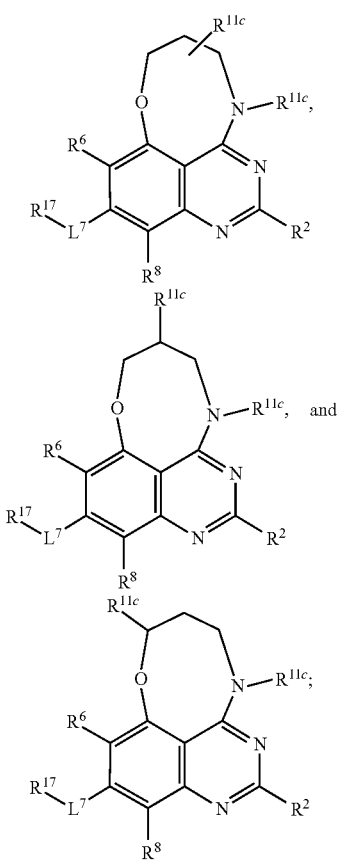

R$^6$ is selected from hydrogen and halogen;
L$^7$ is a bond;
R$^{17}$ is selected from:

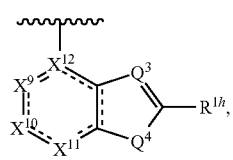

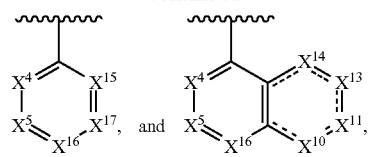

Q$^3$ is N or C(R$^{1d}$); Q$^a$ is S;

X$^4$, X$^3$, X$^{15}$, X$^{16}$, and X$^{17}$ are independently selected from C(R$^{1a}$) or N;

X$^9$ is C(R$^{1a}$); X$^{10}$, X$^{11}$, X$^{13}$, and X$^{14}$ are independently C(R$^{1a}$) or N; X$^{12}$ is C;

each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$ cycloalkyl, C$_{2-4}$heterocycloalkyl, —OH, —NH$_2$, —C(O)OH, —OC(O)NH$_2$, and —C(O)CH$_3$;

R$^{1d}$ is selected from hydrogen, —CN, C$_{1-4}$alkyl, and C$_{1-4}$haloalkyl;

R$^2$ is selected from

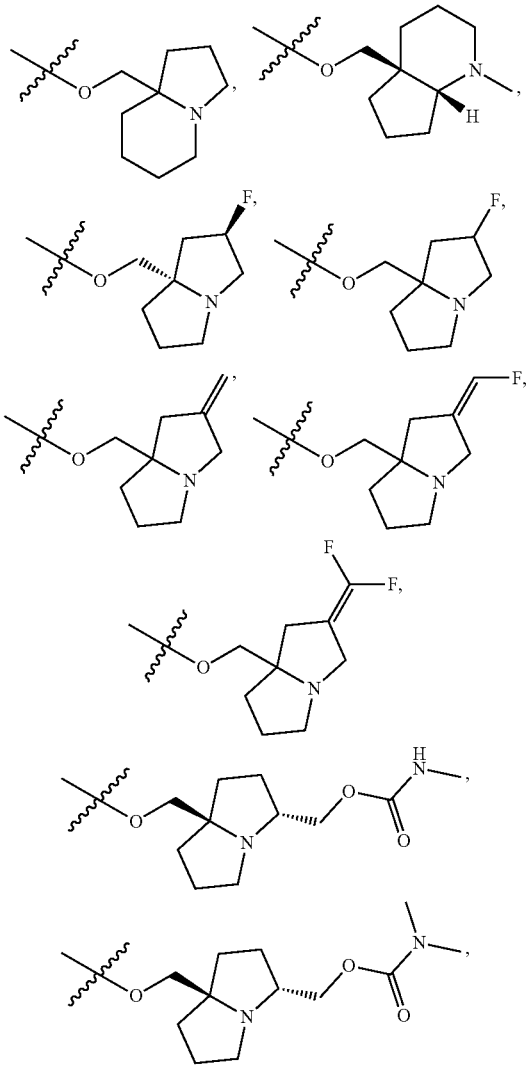

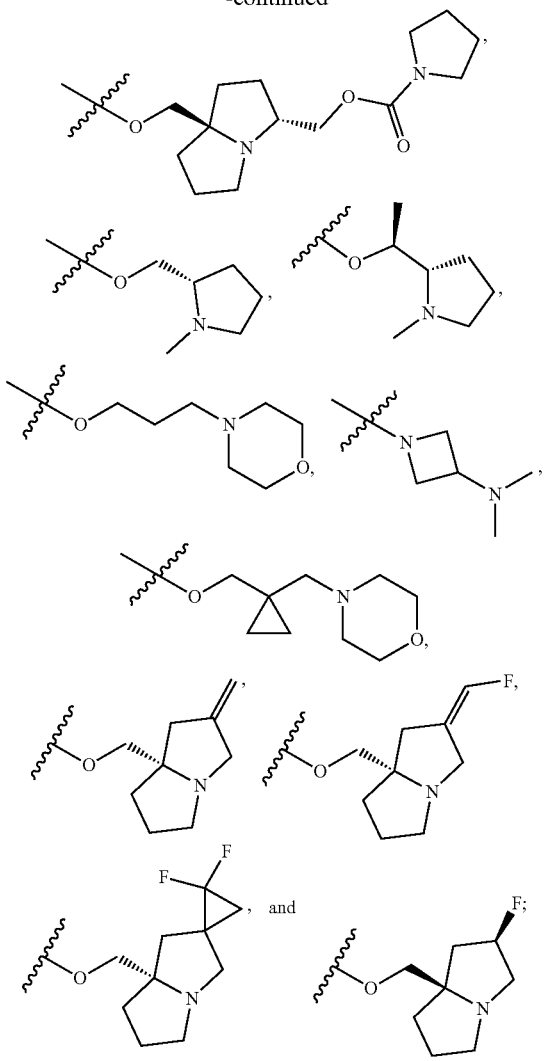

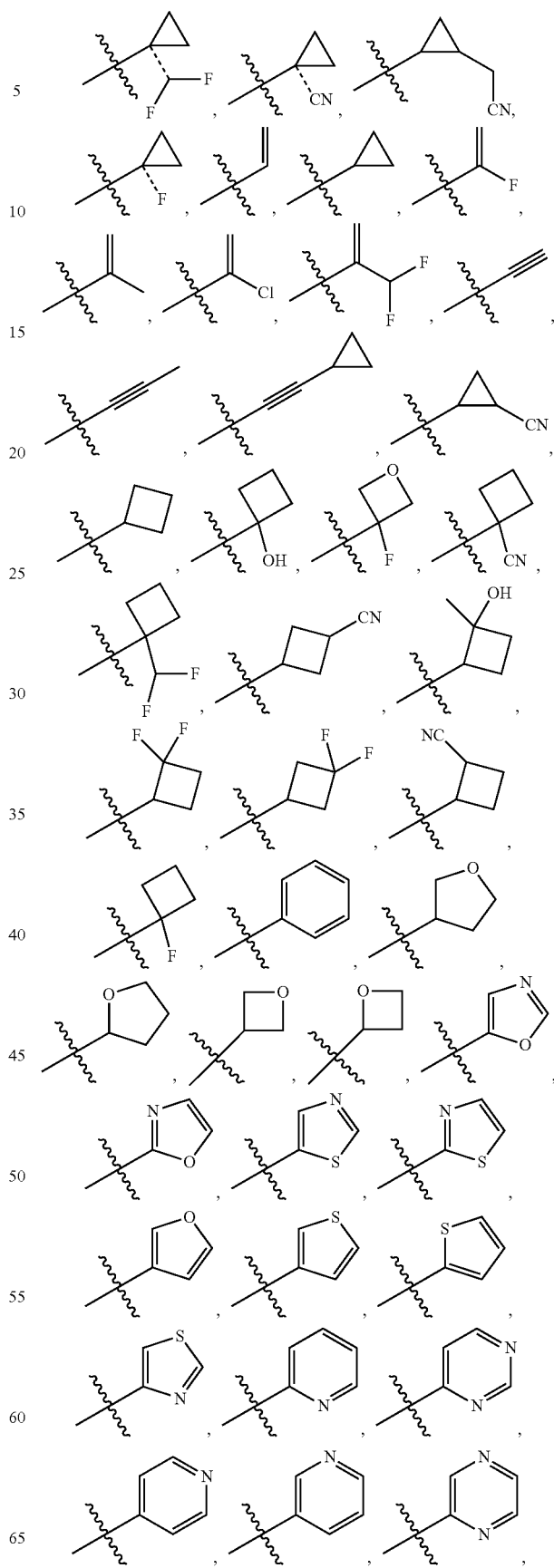

$R^8$ is selected from hydrogen and halogen;

each $R^{11c}$ independently selected from $C_{2-3}$alkenyl, $C_{2-3}$alkynyl, $C_{3-4}$cycloalkyl, —$CH_2$—($C_{3-4}$cycloalkyl), 4-5 membered heterocycloalkyl, —$CH_2$-(4-5 membered heterocycloalkyl), phenyl, —$CH_2$-(phenyl), 5-6 membered heteroaryl, and —$CH_2$-(5-6 membered heteroaryl), wherein $C_{2-3}$alkenyl, $C_{2-3}$alkynyl, $C_{3-4}$cycloalkyl, —$CH_2$—($C_{3-4}$cycloalkyl), 4-5 membered heterocycloalkyl, —$CH_2$-(4-5 membered heterocycloalkyl), phenyl, —$CH_2$-(phenyl), 5-6 membered heteroaryl, and —$CH_2$-(5-6 membered heteroaryl) are optionally substituted with one, two, or three $R^{20k}$;

each $R^{20k}$ is independently selected from halogen, —CN, $C_{1-3}$alkyl, —$NH_2$, and —$OR^{21}$, wherein $C^{1-3}$alkyl is optionally substituted with one, two, or three groups independently selected from halogen and —CN; and each $R^{21}$ is independently selected from H, $C_{1-3}$alkyl, and $C_{1-3}$haloalkyl; and ----- indicates a single or double bond such that all valences are satisfied.

In embodiments of the formulae above, $R^{11c}$ is independently selected from

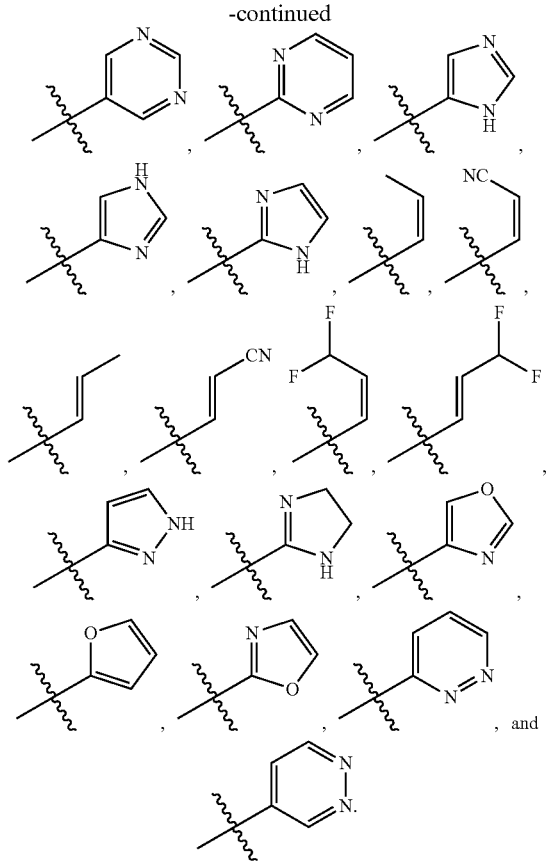

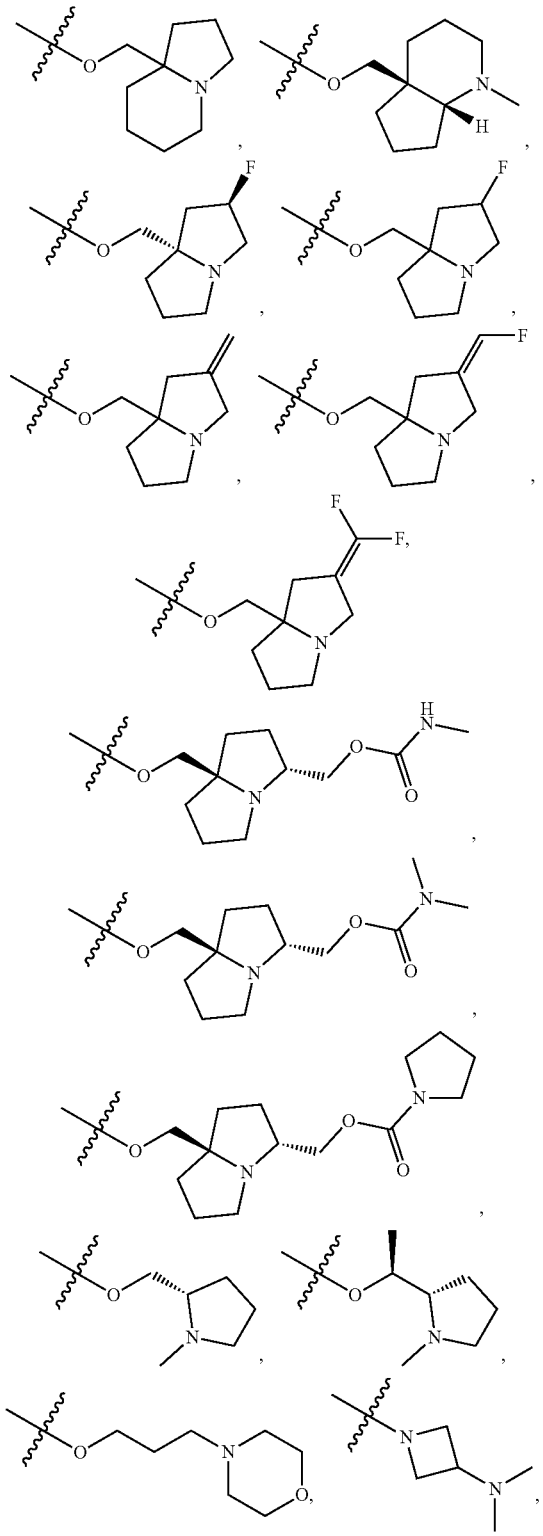

In embodiments of any formulae described herein, $R^{17}$ is

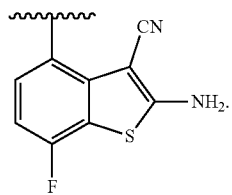 [SMILES: *c1ccc(F)c2sc(N)c(C#N)c12]

In embodiments of any formulae described herein, $R^6$ and $R^8$ are independently selected from hydrogen and halogen; $L^7$ is a

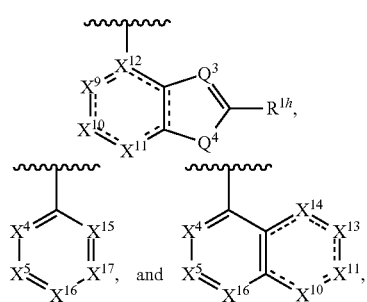

bond, $R^{17}$ is selected from: $Q^3$ is N or $C(R^{1d})$; $Q^4$ is S; $X^4$, $X^5$, $X^{15}$, $X^{16}$, and $X^{17}$ are independently selected from $C(R^{1a})$ or N; $X^9$ is $C(R^{1a})$; $X^{10}$, $X^{11}$, $X^{13}$, and $X^{14}$ are independently $C(R^{1a})$ or N; $X^{12}$ is C;

each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, and —C(O)CH$_3$; $R^{1d}$ is selected from hydrogen, —CN, $C_{1-4}$alkyl, -continued

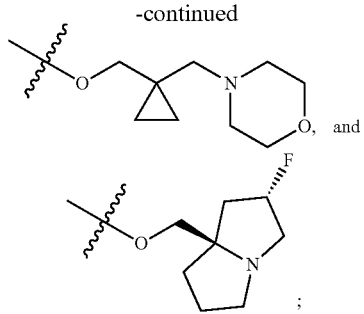
and

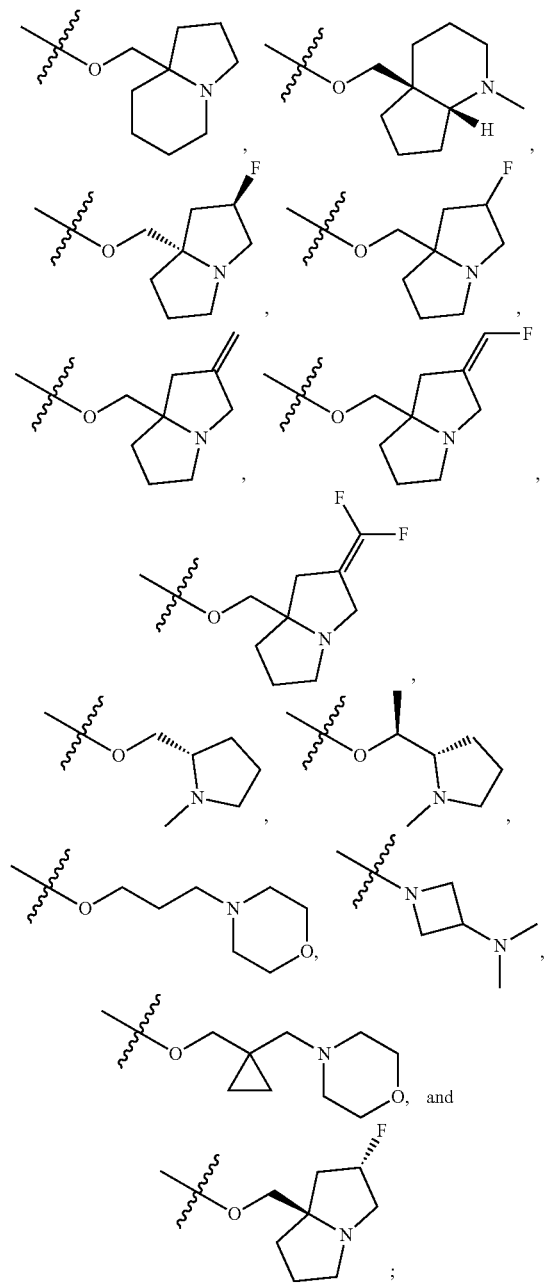

and $C_{1-4}$haloalkyl; $R^2$ is selected from each $R^{11d}$ is independently selected from $C_{1-6}$alkyl, $C_{2-6}$alkenyl, $C_{2-6}$alkynyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, $C_{1-11}$heteroaryl, —$(C_{1-6}$alkyl)-$N(R^{14})C(O)R^{12}$, wherein $C_{1-6}$alkyl, $C_{2-6}$alkenyl, $C_{2-6}$alkynyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, and $C_{1-11}$heteroaryl are optionally substituted with one, two, or three $R^{20k}$; each $R^{12}$ is independently selected from hydrogen, $C_{1-6}$alkyl, $C_{3-10}$ cycloalkyl, $C_{2-9}$heterocycloalkyl, —$CH_2$-$C_{2-9}$heterocycloalkyl, wherein $C_{1-6}$alkyl, $C_{3-10}$cycloalkyl, $C_{2-9}$heterocycloalkyl, and —$CH_2$-$C_{2-9}$heterocycloalkyl are optionally substituted with one, two, or three $R^{20t}$; each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{21}$, —$N(R^{22})(R^{23})$, —$C(O)N(R^{22})(R^{23})$, —$N(R^{24})C(O)R^{21}$, —$C(O)R^{21}$, and —$S(O)_2R^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —$OR^{21}$, and —$N(R^{22})(R^{23})$;

each $R^{20t}$ is independently selected from halogen, —$OR^{21}$, and $C_{3-10}$cycloalkyl; each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl; each $R^{22}$ is independently selected from H and $C_{1-6}$alkyl; each $R^{23}$ is independently selected from H and $C_{1-6}$alkyl; each $R^{24}$ is independently selected from H and $C_{1-6}$alkyl; and each $R^{25}$ is independently selected from $C_{1-6}$alkyl and $C_{3-6}$cycloalkyl.

In embodiments of any formulae described herein, $R^6$ and $R^8$ are independently selected from hydrogen and halogen; $L^7$ is a

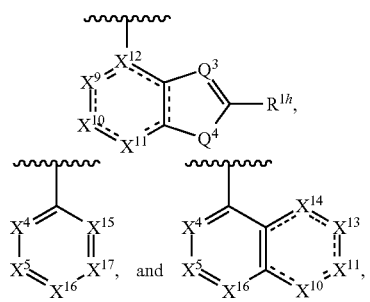

bond; $R^{17}$ is selected from: $Q^3$ is N or $C(R^{14})$; $Q^4$ is S; $X^4$, $X^5$, $X^{15}$, $X^{16}$, and $X^{17}$ are independently selected from $C(R^{1a})$ or N; $X^9$ is $C(R^{1a})$; $X^{10}$, $X^{11}$, $X^{13}$, and $X^{14}$ are independently $C(R^{1a})$ or N; $X^{12}$ is C; each $R^{1a}$ and $R^1h$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —$NH_2$, —$C(O)OH$, —$OC(O)NH_2$, and —$C(O)CH_3$; $R^{1d}$ is selected from hydrogen, —CN, $C_{1-4}$alkyl, $C_{1-4}$haloalkyl, and $C_{3-4}$cycloalkyl; $R^2$ is selected from $R^4$ is -$L^4$-$R^{4a}$, $L^4$ is a bond or $CR^{4c}R^{4c}$; each $R^4$ is independently selected from hydrogen and $C_{1-3}$alkyl; each $R^{4a}$ is independently selected from $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl, wherein $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl are optionally substituted with one, two, three, or four $R^{4b}$; each $R^{4b}$ is independently selected from halogen, oxo, —CN, $C_{1-3}$alkyl, $C_{2-6}$alkenyl, $C_{3-6}$cycloalkyl, $C_{2-11}$heterocycloalkyl, —$OR^{12}$, —$N(R^{12})(R^{13})$, =$C(R^{21}b)_2$, —$C(O)R^{12}$, —$N(R^{14})C(O)R^{12}$, —$S(O)_2R^{15}$, and —$C(O)N(R^{12})(R^{13})$, wherein $C_{1-6}$alkyl, $C_{3-12}$cycloalkyl, and $C_{2-11}$heterocycloalkyl, are optionally substituted with one or more $R^{20}j$; each $R^{11d}$ is independently selected from $C_{1-3}$alkyl, $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, 5 membered heteroaryl, —$(C_{1-6}$alkyl$)$-$N(R^{14})C(O)R^{12}$, wherein $C_{1-3}$alkyl, $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, and 5 membered heteroaryl are optionally substituted with one, two, or three $R^{20k}$; each $R^{12}$ is independently selected from hydrogen, $C_{1-3}$alkyl, $C_{2-6}$alkenyl, $C_{3-6}$cycloalkyl, 3-6 membered heterocycloalkyl, —$CH_2$-(3-6 membered heterocycloalkyl), and 5-6 membered heteroaryl, wherein $C_{1-3}$alkyl, $C_{2-6}$alkenyl, $C_{3-6}$cycloalkyl, 3-6 membered heterocycloalkyl, —$CH_2$-(3-6 membered heterocycloalkyl), and 5-6 membered heteroaryl are optionally substituted with one, two, or three $R^{20l}$; each $R^{13}$ is independently selected from hydrogen and $C_{1-3}$alkyl; each $R^{14}$ is independently selected from hydrogen, $C_{1-3}$alkyl, and $C_1$-haloalkyl; each $R^{15}$ is independently selected $C_{3-6}$cycloalkyl; each $R^{20}j$ is independently selected from halogen, —CN, $C_{1-6}$alkyl, $C_{3-10}$ cycloalkyl, $C_{2-9}$heterocycloalkyl, $C_{6-10}$aryl, $C_{1-9}$heteroaryl, —$OR^{21}$, —$N(R^{22})(R^{23})$, and —$N(R^{24})C(O)R^{25}$, wherein $C_{1-6}$alkyl, $C_{3-10}$cycloalkyl $C_{2-9}$heterocycloalkyl, $C_{6-10}$aryl, and $C_{1-9}$heteroaryl are optionally substituted with one, two, or three groups independently selected from halogen; each $R^{20k}$ is independently selected from oxo, $C_{1-3}$alkyl, $C_{3-4}$cycloalkyl, halogen, —CN, —$OR^{21}$, —$N(R^{22})(R^{23})$, —$N(R^{24})S(O)_2R^{25}$, —$C(O)R^{21}$, and —$N(R^{24})C(O)R^{21}$; each $R^{20t}$ is independently selected from halogen, —CN, $C_{1-3}$alkyl, $C_{3-6}$cycloalkyl, $C_{2-9}$ heterocycloalkyl, $C_{6-10}$aryl, $C_{1-9}$heteroaryl, —$OR^{21}$, —$N(R^{22})(R^{23})$, and —$N(R^{24})C(O)R^{25}$, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three groups independently selected from halogen; each $R^{21}$ is independently selected from H, $C_{1-3}$alkyl, $C_{1-3}$haloalkyl, $C_{3-6}$cycloalkyl, 3-4 membered heterocycloalkyl, and $C_{1-9}$heteroaryl; each $R^{21}b$ is independently selected from H and halogen; each $R^{22}$ is independently selected from H and $C_{1-3}$alkyl; each $R^{23}$ is independently selected from H and $C_{1-3}$alkyl; each $R^{24}$ is independently selected from H and $C_{1-3}$alkyl; and each $R^{25}$ is independently selected from $C_{1-3}$alkyl, $C_{3-6}$cycloalkyl, and $C_{2-9}$heterocycloalkyl. In embodiments of the formula immediately above;

each $R^{11d}$ is independently selected from $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, 5 membered heteroaryl, —$(C_{1-6}$alkyl$)$-$N(R^{14})C(O)R^{12}$, wherein $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, and 5 membered heteroaryl are optionally substituted with one, two, or three $R^{20k}$;

In embodiments of any formulae described herein, $R^6$ and $R^8$ are independently selected from hydrogen and halogen; $L^7$ is a

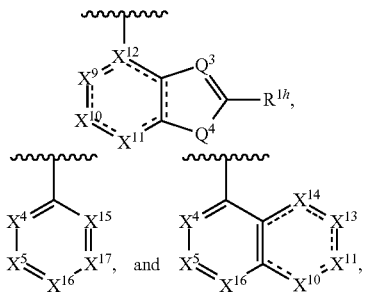

bond; $R^{17}$ is selected from: $Q^3$ is N or $C(R^1d)$; $Q^4$ is S; $X^4$, $X^5$, $X^{15}$, $X^{16}$, and $X^{17}$ are independently selected from $C(R^{1a})$ or N; $X^9$ is $C(R^{1a})$; $X^{10}$, $X^{11}$, $X^{13}$, and $X^{14}$ are independently $C(R^{1a})$ or N; $X^{12}$ is C; each $R^{1a}$ and $R^1h$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —$NH_2$, —$C(O)OH$, —$OC(O)NH_2$, and —$C(O)CH_3$; $R^{1d}$ is selected from hydrogen, —CN, $C_{1-4}$alkyl,

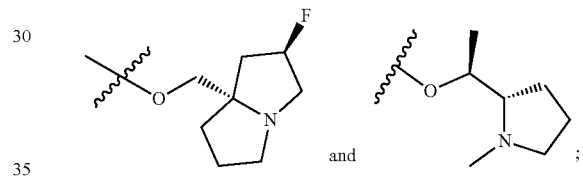

$C_{1-4}$haloalkyl, and $C_{3-4}$cycloalkyl; $R^2$ is selected from; $R^4$ is -$L^4$-$R^{43}$; $L^4$ is a bond or $CR^4R^4$; each $R^{4c}$ is independently selected from hydrogen and $C_{1-3}$alkyl; each $R^{4a}$ is independently selected from $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl, wherein $C_{3-7}$cycloalkyl, 4-7 membered monocyclic heterocycloalkyl, 6-9 membered fused heterocycloalkyl, 6-9 membered spirocyclic heterocycloalkyl, 6-8 membered bridged heterocycloalkyl, phenyl, and 5-6 membered heteroaryl are optionally substituted with one, two, three, or four $R^{4b}$; each $R^{4b}$ is independently selected from halogen, oxo, —CN, $C_{1-3}$alkyl, $C_{3-6}$cycloalkyl, —$OR^{12}$, —$N(R^{12})(R^{13})$, —$C(R^{21}b)_2$, —$C(O)R^{12}$, —$N(R^{14})C(O)R^{12}$, —$S(O)_2R^{15}$, and —$C(O)N(R^{12})(R^{13})$, wherein $C_{1-3}$alkyl and $C_{3-6}$cycloalkyl are optionally substituted with one or more $R^{20}j$; each $R^{11d}$ is independently selected from $C_{1-3}$alkyl, $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, 5 membered heteroaryl, —$(C_{1-6}$alkyl$)$-$N(R^{14})C(O)R^{12}$, wherein $C_{1-3}$alkyl, $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, and 5 membered heteroaryl are optionally substituted with one, two, or three $R^{20k}$; each $R^{12}$ is independently selected from hydrogen, $C_{1-3}$alkyl, $C_{3-6}$cycloalkyl, 3-6 membered heterocycloalkyl, —$CH_2$-(3-6 membered heterocycloalkyl), and 5-6 membered heteroaryl, wherein $C_{1-3}$alkyl, $C_{3-6}$cycloalkyl, 3-6 membered heterocycloalkyl, —$CH_2$-(3-6 membered heterocycloalkyl), and 5-6 membered heteroaryl are optionally substituted with one, two, or three $R^{201}$; each $R^{13}$ is independently selected from hydrogen and $C_{1-3}$alkyl; each $R^{14}$ is independently selected from hydrogen and $C_{1-3}$alkyl; each $R^{15}$ is independently selected $C_{3-6}$cycloalkyl; each $R^{20}j$ is independently selected from halogen and $-OR^{21}$; each $R^{20k}$ is independently selected from oxo, $C_{1-3}$alkyl, $C_{3-4}$cycloalkyl, halogen, $-CN$, $-OR^{21}$, $-N(R^{22})(R^{23})$, $-N(R^{24})S(O)_2R^{25}$, $-C(O)R^{21}$, and $-N(R^{24})C(O)R^{21}$; each $R^{20t}$ is independently selected from halogen, $-CN$, $C_{1-3}$alkyl, $C_{3-6}$cycloalkyl, $-OR^{21}$, and $-N(R^{22})(R^{23})$, wherein $C_{1-3}$alkyl and $C_{3-6}$cycloalkyl are optionally substituted with one, two, or three groups independently selected from halogen; each $R^{21}$ is independently selected from hydrogen, $C_{1-3}$alkyl, $C_{1-3}$haloalkyl, $C_{3-6}$cycloalkyl, and 3-4 membered heterocycloalkyl; each $R^{21}b$ is independently selected from hydrogen and halogen; each $R^{22}$ is independently selected from hydrogen and $C_{1-3}$alkyl; each $R^{23}$ is independently selected from hydrogen and $C_{1-3}$alkyl; each $R^{24}$ is independently selected from hydrogen and $C_{1-3}$alkyl; and each $R^{25}$ is independently selected from $C_{1-3}$alkyl. In embodiments of any formulae described herein, each $R^{11d}$ is independently selected from $C_{2-3}$alkenyl, $C_{2-3}$alkynyl, $C_{3-4}$cycloalkyl, $-CH_2-C_{3-4}$cycloalkyl, 4-6 membered heterocycloalkyl, phenyl, 5 membered heteroaryl, $-(C_{1-6}$alkyl$)-N(R^{14})C(O)R^{12}$, wherein $C_{2-3}$alkenyl, $C_{2-3}$alkynyl, $C_{3-4}$cycloalkyl, $-CH_2-C_{3-4}$cycloalkyl, 4-6 membered heterocycloalkyl, phenyl, and 5 membered heteroaryl are optionally substituted with one, two, or three $R^{20k}$.

In embodiments of any formulae described herein, $Z^1$ is O; $R^6$ and $R^8$ are independently selected from hydrogen and halogen; $L^7$ is a

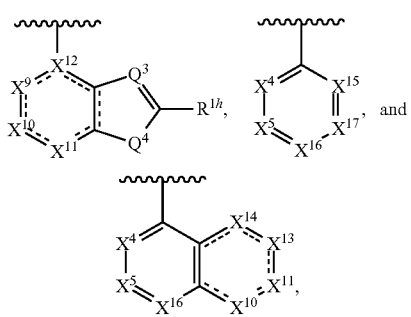

bond; $R^{17}$ is selected from: $Q^3$ is N or $C(R^1d)$; $Q^4$ is S; $X^4$, $X^5$, $X^{15}$, $X^{16}$, and $X^{17}$ are independently selected from $C(R^{1a})$ or N; $X^9$ is $C(R^{1a})$; $X^{10}$, $X^{11}$, $X^{13}$, and $X^{14}$ are independently $C(R^{1a})$ or N; $X^{12}$ is C; each $R^{1a}$ and $R^1h$ is independently selected from hydrogen, halogen, $-CN$, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, $-OH$, $-NH_2$, $-C(O)OH$, $-OC(O)NH_2$, and $-C(O)CH_3$; $R^{1d}$ is selected from hydrogen, $-CN$, $C_{1-4}$alkyl,

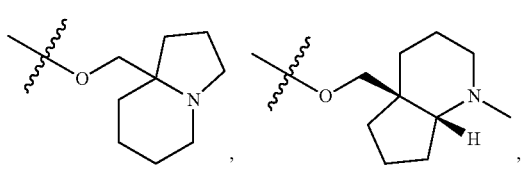

-continued

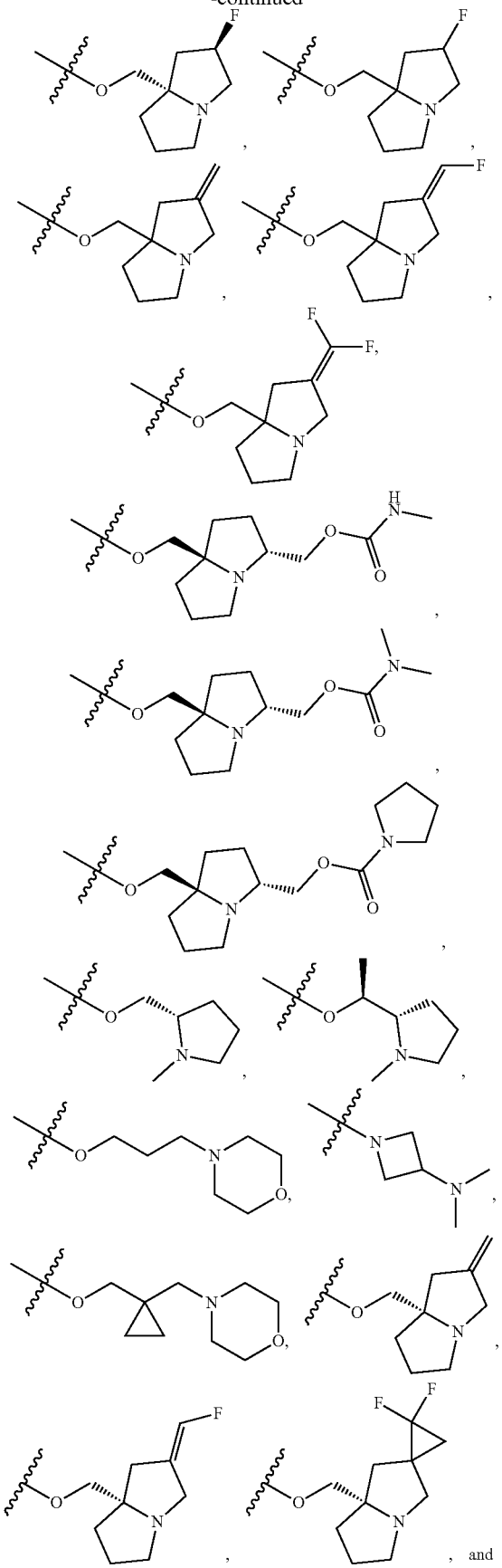

505

-continued

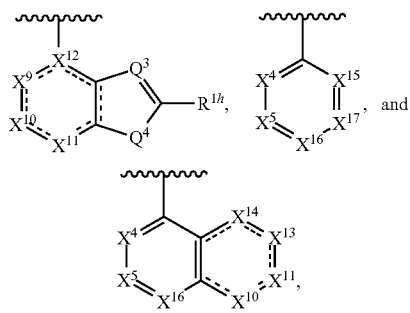

and C$_{1-4}$haloalkyl; R$^2$ is selected from each R$^{11c}$ is independently selected from C$_{1-3}$alkyl, C$_{2-3}$alkenyl, C$_{2-3}$alkynyl, C$_{3-4}$cycloalkyl, —CH$_2$-C$_{3-4}$cycloalkyl, 4-6 membered heterocycloalkyl, phenyl, 5 membered heteroaryl, —(C$_{1-6}$alkyl)-N(R$^{14}$)C(O)R$^{12}$, wherein C$_{1-3}$alkyl, C$_{2-3}$alkenyl, C$_{2-3}$alkynyl, C$_{3-4}$cycloalkyl, —CH$_2$-C$_{3-4}$cycloalkyl, 4-6 membered heterocycloalkyl, phenyl, and 5 membered heteroaryl are optionally substituted with one, two, or three R$^{20k}$; each R$^{11d}$ is independently selected from C$_{1-4}$alkyl, C$_2$-alkenyl, C$_{2-6}$alkynyl, C$_{3-7}$cycloalkyl, —CH$_2$—(C$_{3-7}$cycloalkyl), 4-7 membered monocyclic heterocycloalkyl, —CH$_2$-(4-7 membered monocyclic heterocycloalkyl), 6-9 membered fused heterocycloalkyl, 6-9 membered spirocyclic heterocycloalkyl, 6-8 membered bridged heterocycloalkyl, phenyl, 5-6 membered heteroaryl, —CH$_2$-(5-6 membered heteroaryl), and —(C$_{1-4}$alkyl)-N(R$^{14}$)C(O)R$^{12}$, wherein C$_{1-4}$alkyl, C$_2$-alkenyl, C$_{2-6}$alkynyl, C$_{3-7}$cycloalkyl, —CH$_2$—(C$_{3-7}$cycloalkyl), 4-7 membered monocyclic heterocycloalkyl, —CH$_2$-(4-7 membered monocyclic heterocycloalkyl), 6-9 membered fused heterocycloalkyl, 6-9 membered spirocyclic heterocycloalkyl, 6-8 membered bridged heterocycloalkyl, phenyl, 5-6 membered heteroaryl, and —CH$_2$-(5-6 membered heteroaryl) are optionally substituted with one, two, or three R$^{20k}$; each R$^{12}$ is independently selected from hydrogen, C$_{1-3}$alkyl, C$_{3-6}$cycloalkyl, 3-6 membered heterocycloalkyl, —CH$_2$-(3-6 membered heterocycloalkyl), and 5-6 membered heteroaryl, wherein C$_{1-3}$alkyl, C$_{3-6}$cycloalkyl, 3-6 membered heterocycloalkyl, —CH$_2$-(3-6 membered heterocycloalkyl), and 5-6 membered heteroaryl are optionally substituted with one, two, or three R$^{201}$; each R$^{14}$ is independently selected from hydrogen and C$_{1-3}$alkyl; each R$^{20k}$ is independently selected from halogen, oxo, —CN, C$_{1-3}$alkyl, C$_{3-6}$cycloalkyl, =C(R$^{21}$b)$_2$, —OR$^{21}$, —N(R$^{22}$)(R$^{23}$), —N(R$^{24}$)S(O)$_2$R$^{25}$, —C(O)R$^{21}$, —N(R$^{24}$)C(O)R$^{21}$, S(O)$_2$R$^{25}$, and —C(O)N(R$^{22}$)(R$^{23}$), wherein C$_{1-3}$alkyl and C$_{3-6}$cycloalkyl are optionally substituted with one, two, or three groups independently selected from halogen and —OR$^{21}$;

each R$^{20t}$ is independently selected from halogen, —CN, C$_{1-3}$alkyl, C$_{3-6}$cycloalkyl, —OR$^{21}$, —S(O)$_2$R$^{25}$, and —N(R$^{22}$)(R$^{23}$), wherein C$_{1-3}$alkyl and C$_{3-6}$cycloalkyl are optionally substituted with one, two, or three groups independently selected from halogen; each R$^{21}$ is independently selected from hydrogen, C$_{1-3}$alkyl, C$_{1-3}$haloalkyl, C$_{3-6}$cycloalkyl, and 3-4 membered heterocycloalkyl; each R$^{22}$ is independently selected from hydrogen and C$_{1-3}$alkyl; each R$^{23}$ is independently selected from hydrogen and C$_{1-3}$alkyl; each R$^{24}$ is independently selected from hydrogen and C$_{1-3}$alkyl; and each R$^{25}$ is independently selected from C$_{1-3}$alkyl.

In embodiments of any formulae described herein, each R$^{11c}$ is independently selected from C$_{2-3}$alkenyl, C$_{2-3}$alkynyl, C$_{3-4}$cycloalkyl, —CH$_2$-C$_{3-4}$cycloalkyl, 4-6 membered heterocycloalkyl, phenyl, 5 membered heteroaryl,

506

—(C$_{1-6}$alkyl)-N(R$^{14}$)C(O)R$^{12}$, wherein C$_{2-3}$alkenyl, C$_{2-3}$alkynyl, C$_{3-4}$cycloalkyl, —CH$_2$-C$_{3-4}$cycloalkyl, 4-6 membered heterocycloalkyl, phenyl, and 5 membered heteroaryl are optionally substituted with one, two, or three R$^{20k}$;

In embodiments of any formulae described herein, Z$^1$ is O; R$^6$ and R$^8$ are independently selected from hydrogen and

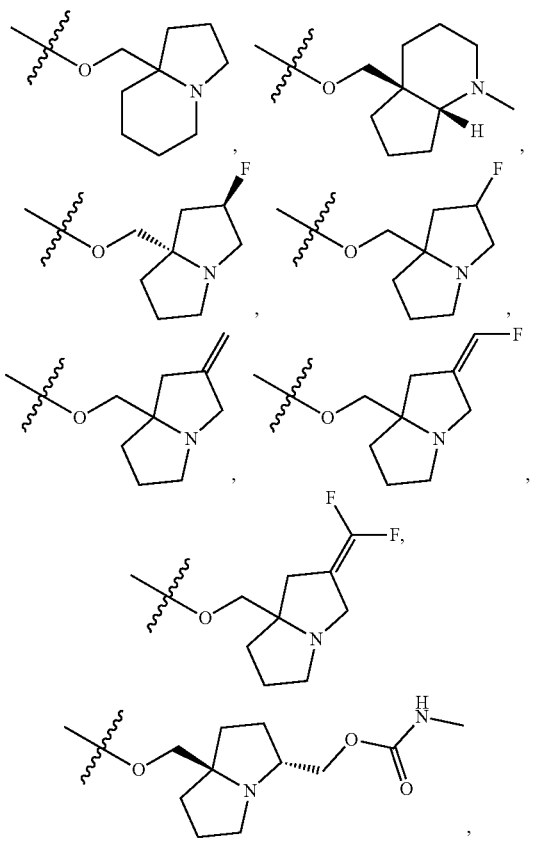

halogen; L$^7$ is a bond; R$^{17}$ is selected from: Q$^3$ is N or C(R$^1$d); Q$^4$ is S;X$^4$, X$^5$, X$^{15}$, X$^{16}$, and X$^{17}$ are independently selected from C(R$^{1a}$) or N;X$^9$ is C(R$^{1a}$); X$^{10}$, X$^{11}$, X$^{13}$, and X$^{14}$ are independently C(R$^{1a}$) or N; X$^{12}$ is C; each R$^{1a}$ and R$^1$h is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$; R$^{1d}$ is selected from hydrogen, —CN,

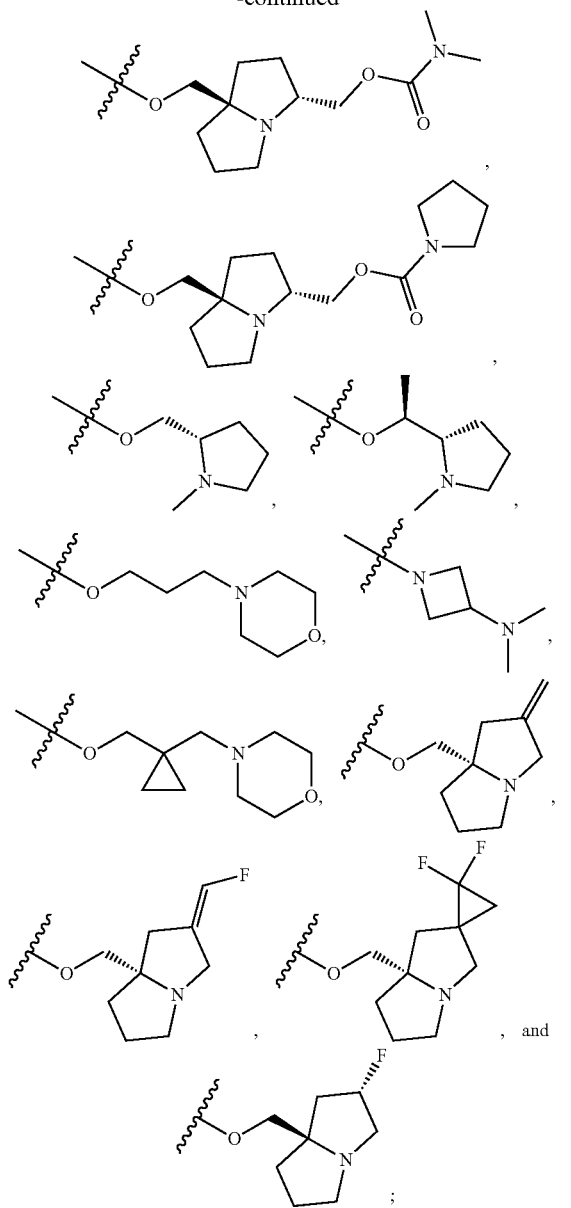

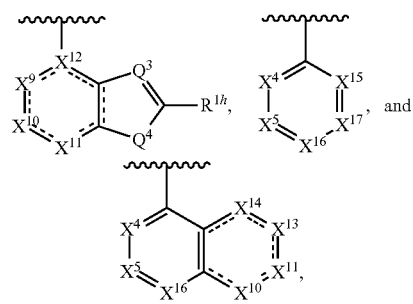

$C_{1-4}$alkyl, and $C_{1-4}$haloalkyl; $R^2$ is selected from
each $R^{11c}$ is independently selected from $C_{1-3}$alkyl, $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, 5 membered heteroaryl, —($C_{1-6}$alkyl)-N($R^{14}$)C(O)$R^{12}$, wherein $C_{1-3}$alkyl, $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, and 5 membered heteroaryl are optionally substituted with one, two, or three $R^{20k}$; each $R^{11d}$ is independently selected from $C_{1-4}$alkyl, $C_2$-alkenyl, and —($C_{1-4}$alkyl)-N($R^{14}$)C(O)$R^{12}$, wherein $C_{1-4}$alkyl and $C_2$-alkenyl are optionally substituted with one, two, or three $R^{20k}$; each $R^{12}$ is independently selected from hydrogen, $C_{1-3}$alkyl, $C_{3-6}$cycloalkyl, 3-6 membered heterocycloalkyl, —$CH_2$-(3-6 membered heterocycloalkyl), and 5-6 membered heteroaryl, wherein $C_{1-3}$alkyl, $C_{3-6}$cycloalkyl, 3-6 membered heterocycloalkyl, —$CH_2$-(3-6 membered heterocycloalkyl), and 5-6 membered heteroaryl are optionally substituted with one, two, or three $R^{201}$; each $R^{14}$ is independently selected from hydrogen and $C_{1-3}$alkyl; each $R^{20k}$ is independently selected from oxo, $C_{1-3}$alkyl, $C_{3-4}$cycloalkyl, halogen, —CN, —$OR^{21}$, —N($R^{22}$)($R^{23}$), —N($R^{24}$)S(O)$_2R^{25}$, —C(O)$R^{21}$, and —N($R^{24}$)C(O)$R^{21}$; each $R^{20r}$ is independently selected from halogen, —CN, $C_{1-3}$alkyl, $C_{3-6}$cycloalkyl, —$OR^{21}$, —S(O)$_2R^{25}$, and —N($R^{22}$)($R^{23}$), wherein $C_{1-3}$alkyl and $C_{3-6}$cycloalkyl are optionally substituted with one, two, or three groups independently selected from halogen; each $R^{21}$ is independently selected from hydrogen, $C_{1-3}$alkyl, $C_{1-3}$haloalkyl, $C_{3-6}$cycloalkyl, and 3-4 membered heterocycloalkyl; each $R^{22}$ is independently selected from hydrogen and $C_{1-3}$alkyl; each $R^{23}$ is independently selected from hydrogen and $C_{1-3}$alkyl; each $R^{24}$ is independently selected from hydrogen and $C_{1-3}$alkyl; and each $R^{25}$ is independently selected from $C_{1-3}$alkyl.

In embodiments of any formulae described herein, each $R^{11c}$ is independently selected from $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, 5 membered heteroaryl, —($C_{1-6}$alkyl)-N($R^{14}$)C(O)$R^{12}$, wherein $C_{2-3}$alkenyl, $C_{2-3}$alkynyl, $C_{3-4}$cycloalkyl, —$CH_2$-$C_{3-4}$cycloalkyl, 4-6 membered heterocycloalkyl, phenyl, and 5 membered heteroaryl are optionally substituted with one, two, or three $R^{20k}$;

In embodiments of any formulae described herein, $Z^1$ is O; $R^6$ and $R^8$ are independently selected from hydrogen and halogen;

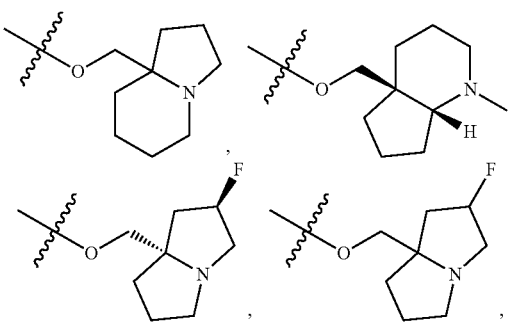

$Q^3$ is N or C($R^1$d); $Q^4$ is S; $X^4$, $X^5$, $X^{15}$, $X^{16}$, and $X^{17}$ are independently selected from C($R^{1a}$) or N; $X^9$ is C($R^{1a}$); $X^{10}$, $X^{11}$, $X^{13}$, and $X^{14}$ are independently C($R^{1a}$) or N; $X^{12}$ is C; each $R^{1a}$ and $R^1$h is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —$NH_2$, —C(O)OH, —OC(O)$NH_2$, and —C(O)$CH_3$; $R^{1d}$ is selected from hydrogen, —CN, $C_{1-4}$alkyl, -continued

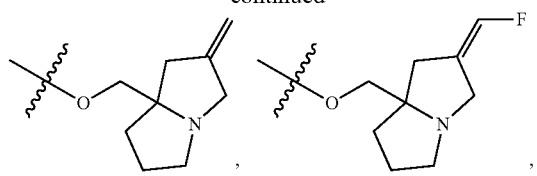

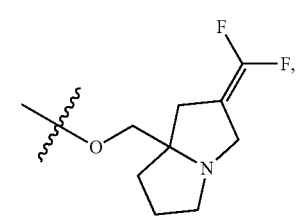

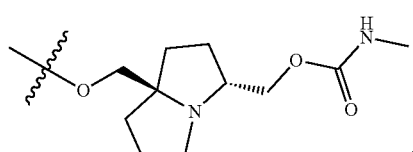

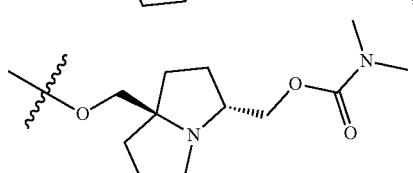

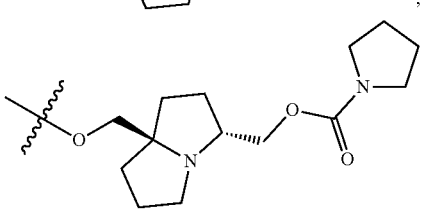

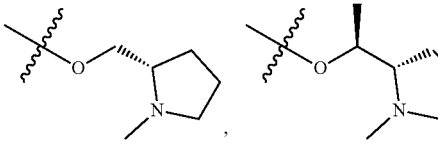

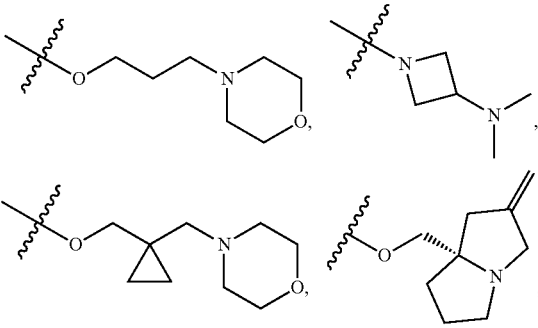

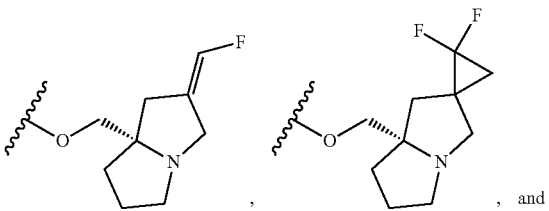, and

-continued

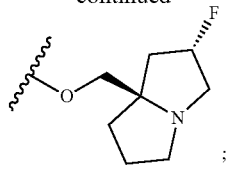;

$L^7$ is a bond; $R^{17}$ is selected from:

and $C_{1-4}$haloalkyl; $R^2$ is selected from each $R^{11c}$ independently selected from hydrogen, $C_{2-3}$alkenyl, $C_{2-3}$alkynyl, $C_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl), wherein $C_{2-3}$alkenyl, $C_{2-3}$alkynyl, $C_{3-4}$cycloalkyl, —CH$_2$—(C$_{3-4}$cycloalkyl), 4-5 membered heterocycloalkyl, —CH$_2$-(4-5 membered heterocycloalkyl), phenyl, —CH$_2$-(phenyl), 5-6 membered heteroaryl, and —CH$_2$-(5-6 membered heteroaryl) are optionally substituted with one, two, or three $R^{20k}$; each $R^{11d}$ is independently selected from $C_{1-4}$alkyl, $C_{3-4}$cycloalkyl, —CH$_2$-C$_{3-4}$cycloalkyl, and 5-6 membered heterocycloalkyl, wherein $C_{1-4}$alkyl, $C_{3-4}$cycloalkyl, —CH$_2$-C$_{3-4}$cycloalkyl, and 5-6 membered heterocycloalkyl are optionally substituted with one, two, or three $R^{20k}$; each $R^{20k}$ is independently selected from halogen, —CN, $C_{1-3}$alkyl, —NHC(O)R$^{21}$, and —OR$^{21}$, wherein $C_{1-3}$alkyl is optionally substituted with one, two, or three groups independently selected from halogen and —CN; and each $R^{21}$ is independently selected from H, $C_{1-3}$alkyl, $C_{1-3}$haloalkyl, and 3-4 membered

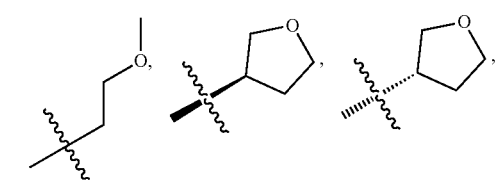

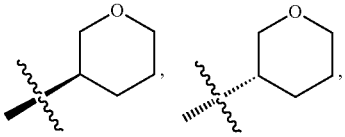

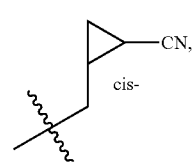

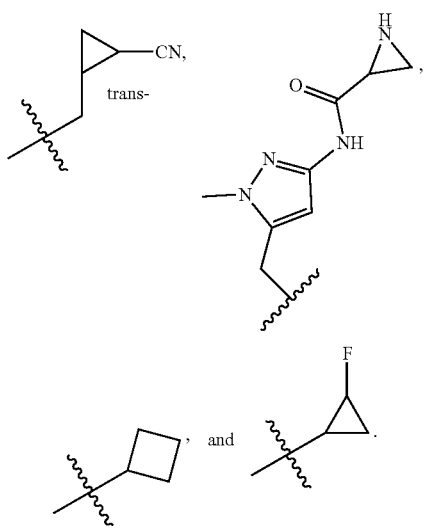
heterocycloalkyl. In embodiments of any formulae described herein, $R^{11d}$ is independently selected from
In embodiments of any formulae described herein, $R^{11c}$ is independently selected from
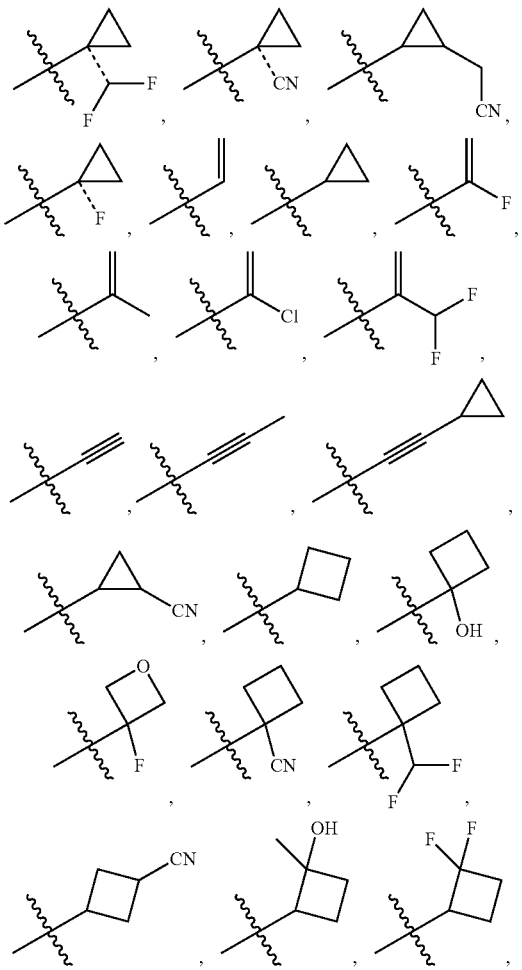
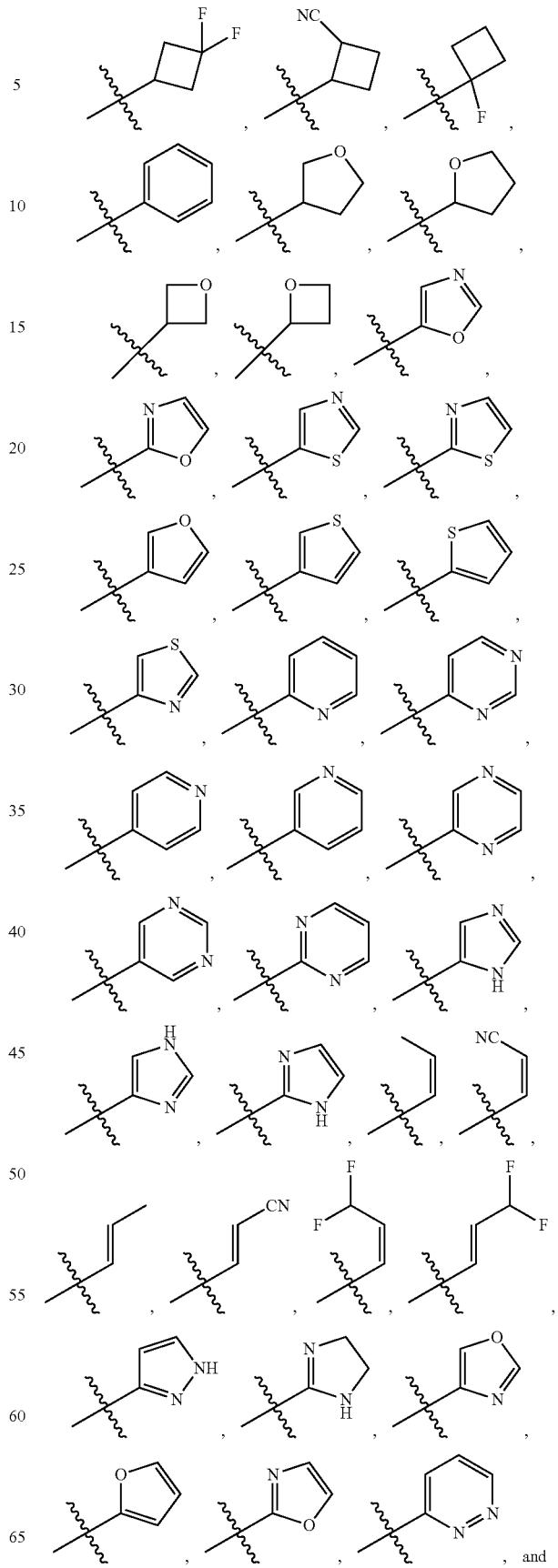
, and

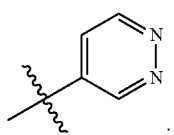

In embodiments of any formulae described herein, $Z^1$ is O; $R^6$ and $R^8$ are independently selected from hydrogen and

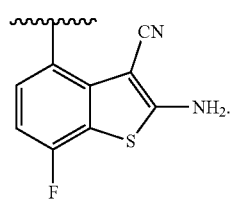 [SMILES: *c1ccc(F)c2sc(N)c(C#N)c12]

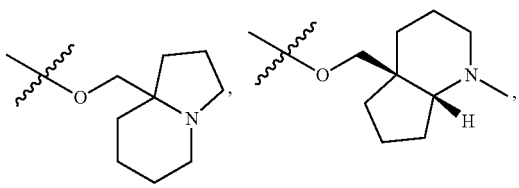

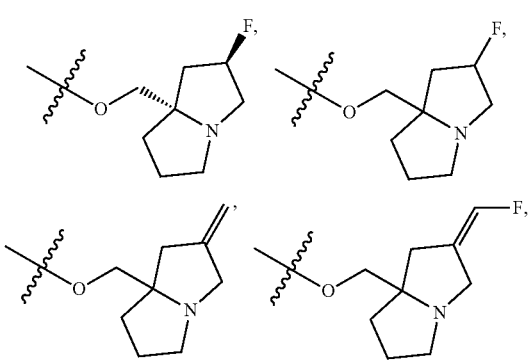

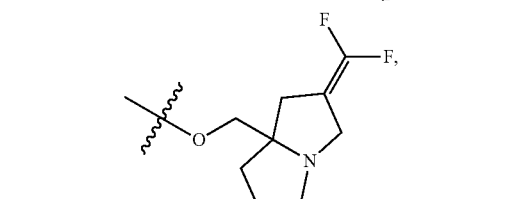

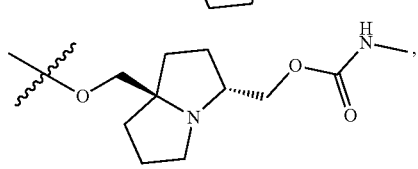

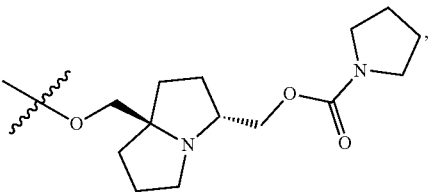

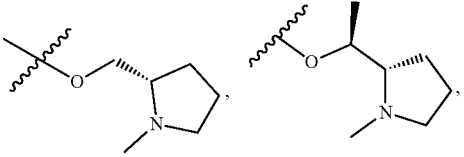

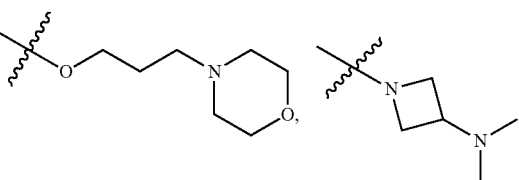

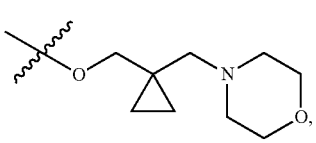

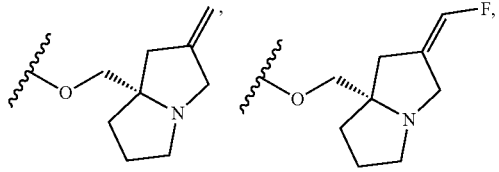

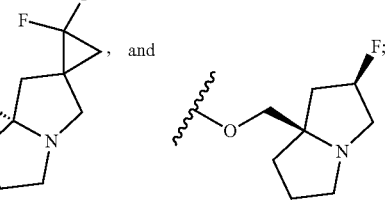

halogen; $L^7$ is a bond; $R^{17}$ is.$R^2$ is selected from ,each $R^{11c}$ independently selected from hydrogen, $C_{2-3}$alkenyl, $C_{2-3}$alkynyl, $C_{3-4}$cycloalkyl, 4-5 membered heterocycloalkyl, phenyl, and 5-6 membered heteroaryl, wherein $C_{2-3}$alkenyl, $C_{2-3}$alkynyl, $C_{3-4}$cycloalkyl, 4-5 membered heterocycloalkyl, phenyl, and 5-6 membered heteroaryl are optionally substituted with one, two, or three $R^{20k}$; each $R^{11d}$ is independently selected from $C_{1-4}$alkyl, $C_{3-4}$cycloalkyl, —$CH_2$-$C_{3-4}$cycloalkyl, and 5-6 membered heterocycloalkyl, wherein $C_{1-4}$alkyl, $C_{3-4}$cycloalkyl, —$CH_2$-$C_{3-4}$cycloalkyl, and 5-6 membered heterocycloalkyl are optionally substituted with one, two, or three $R^{20k}$;each $R^{20k}$ is independently selected from halogen, —CN, $C_{1-3}$alkyl, —NHC(O)$R^{21}$, and —OR$^{21}$, wherein $C_{1-3}$alkyl is optionally substituted with one, two, or three groups independently selected from halogen and —CN; and each $R^{21}$ is independently selected from H, $C_{1-3}$alkyl, $C_{1-3}$haloalkyl, and 3-4 membered heterocycloalkyl. In embodiments of any formulae described herein, $R^{11d}$ is independently selected from

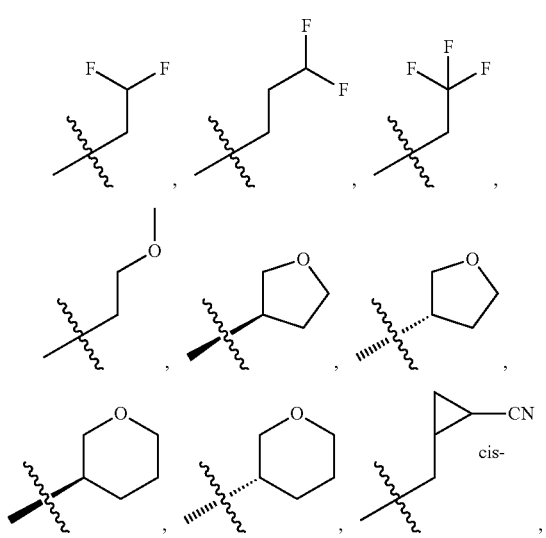
In embodiments of any formulae described herein, $R^{11c}$ is independently selected from
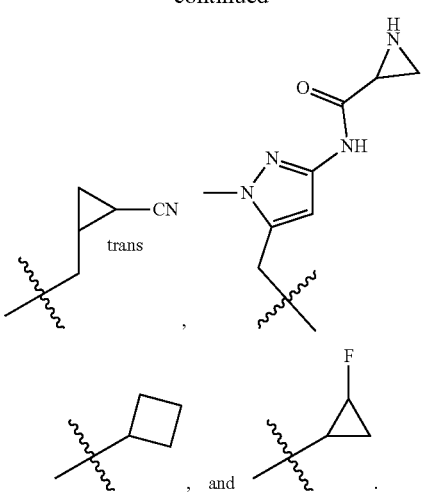
In embodiments of any formulae described herein, $R^{11c}$ is independently selected from 517
-continued
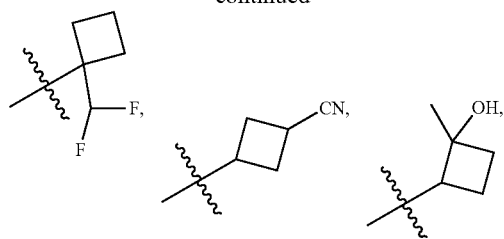
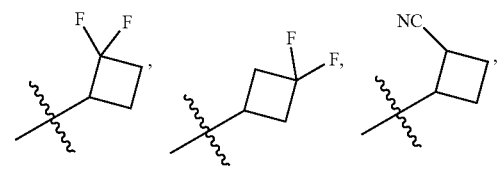
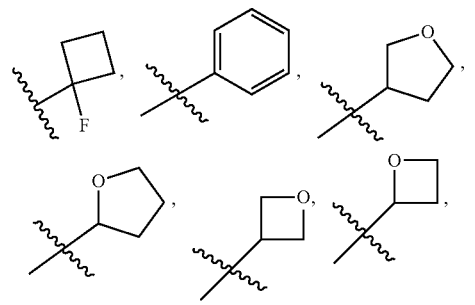
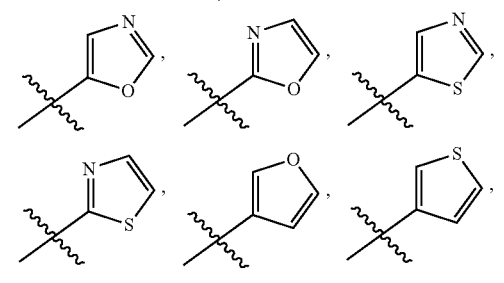
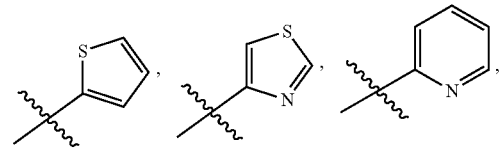
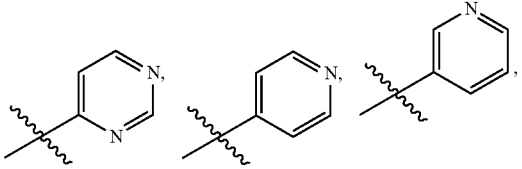
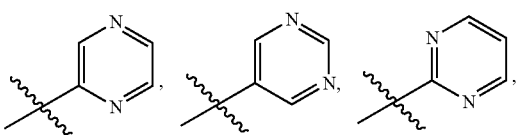
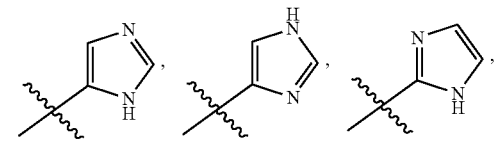
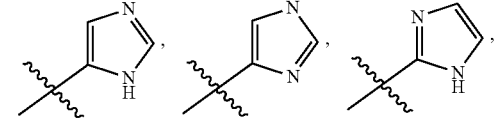
518
-continued
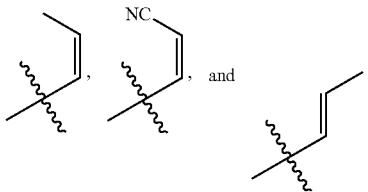, and
In embodiments of any formulae described herein, $R^{11c}$ is independently selected from hydrogen,
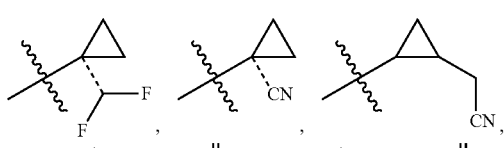
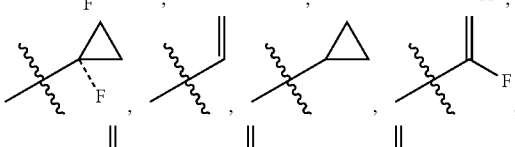
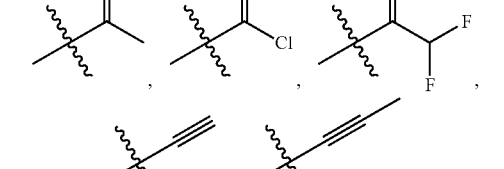
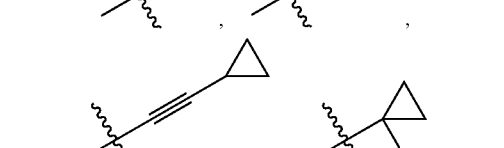
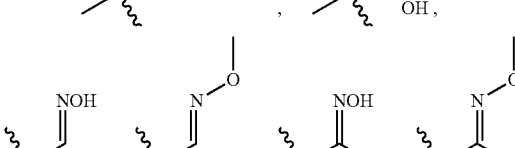
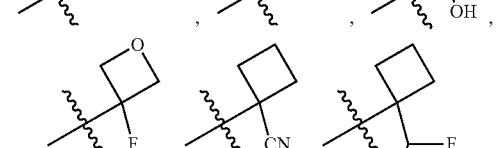
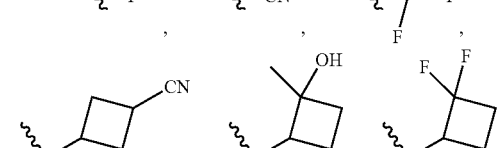
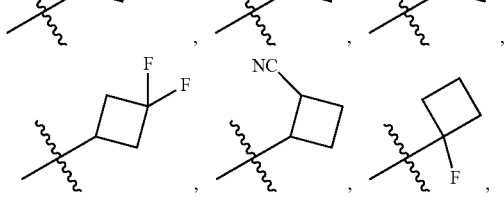
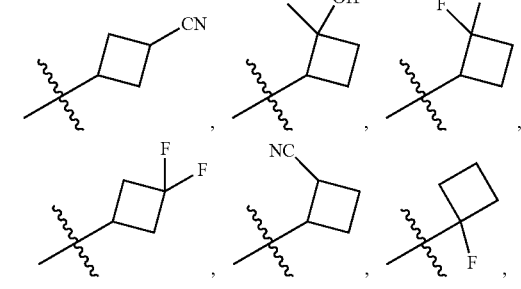

-continued
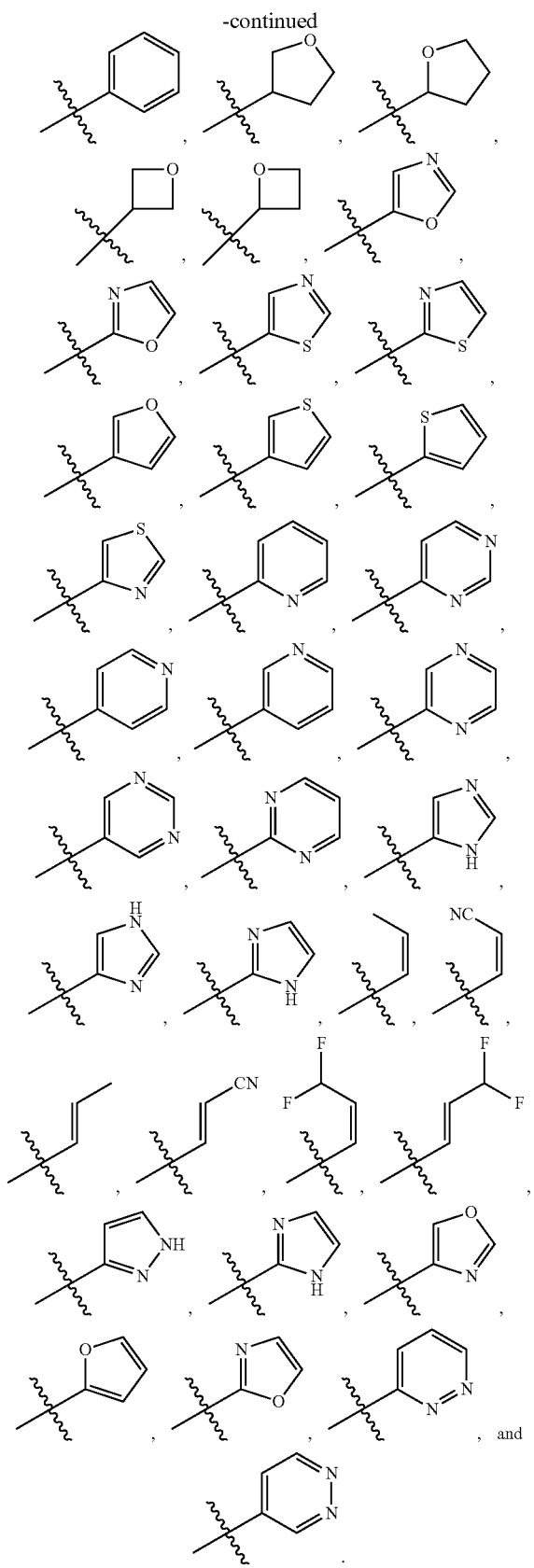
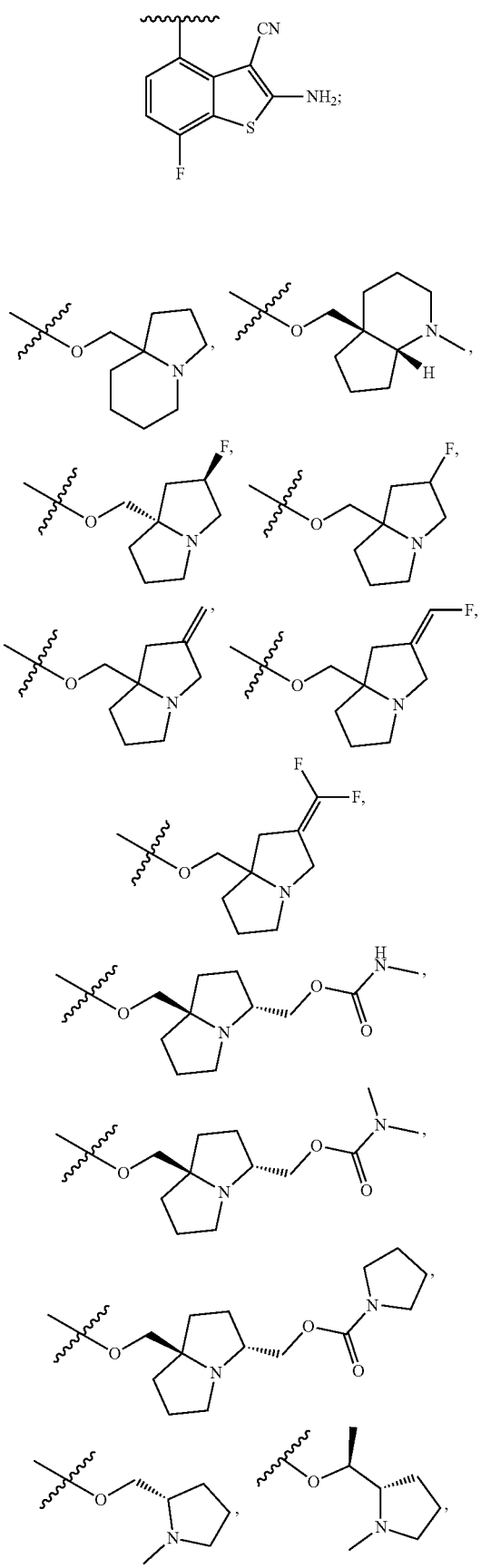
In embodiments of any formulae described herein, R⁶ is selected from hydrogen and halogen; $L^7$ is a bond; $R^{17}$ is

521

-continued

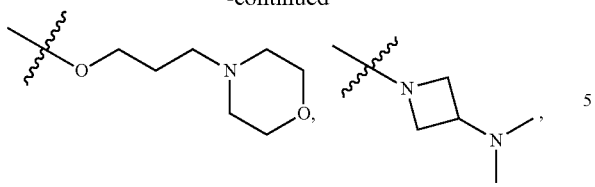

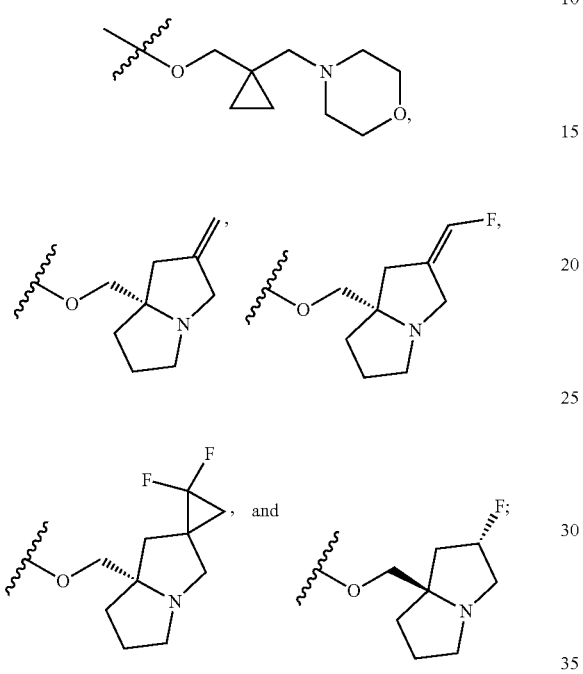

522

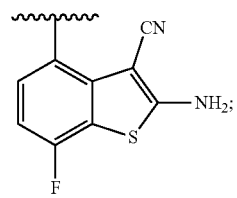 [SMILES: *c1ccc(F)c2sc(N)c(C#N)c12]

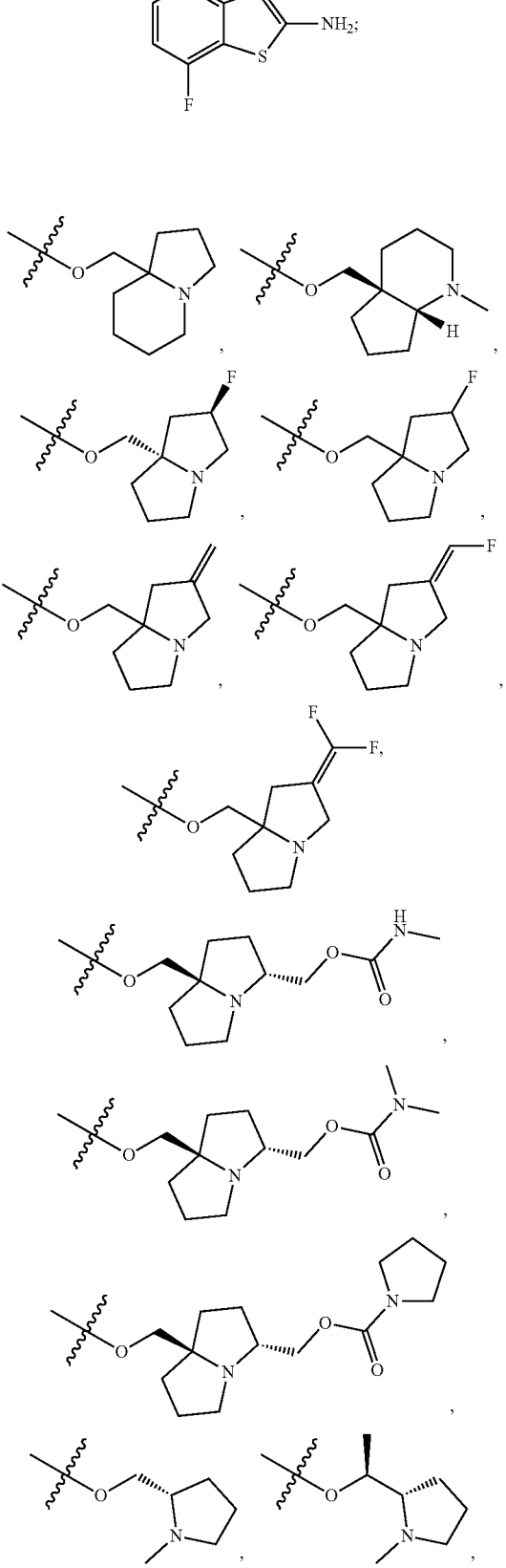

$R^8$ is selected from hydrogen and halogen; each $R^{11c}$ is independently selected from —$OR^{12}$, $C_{1-3}$alkyl, $C_{3-4}$cycloalkyl, —$CH_2$-$C_{3-4}$cycloalkyl, and 5-6 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$; each $R^{20k}$ is independently selected from halogen, —$N(R^{22})(R^{23})$, and —$OR^{21}$; each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20l}$; each $R^{13}$ is independently selected from hydrogen and $C_{1-6}$alkyl; each $R^{15}$ is independently selected from $C_{1-6}$alkyl and $C_{2-9}$heterocycloalkyl, wherein $C_{1-6}$alkyl and $C_2$-heterocycloalkyl are optionally substituted with one, two, or three $R^{20}$m; each $R^{20t}$ is independently selected from halogen, —CN, $C_{3-10}$cycloalkyl, —$OR^{21}$, and —$N(R^{22})(R^{23})$; each $R^{20}$m is independently selected from halogen, —CN, $C_{3-10}$cycloalkyl, —$OR^{21}$, and —$N(R^{22})(R^{23})$; each $R^{21}$ is independently selected from H, $C_{1-3}$alkyl, $C_{1-3}$haloalkyl, $C_{3-6}$cycloalkyl, and 3-4 membered heterocycloalkyl;

each $R^{21}$b is independently selected from H and halogen; each $R^{22}$ is independently selected from H; each $R^{23}$ is independently selected from H; and ----- indicates a single or double bond such that all valences are satisfied.

In embodiments of any formulae described herein, $R^6$ is selected from hydrogen and halogen; $L^7$ is a bond; $R^{17}$ is

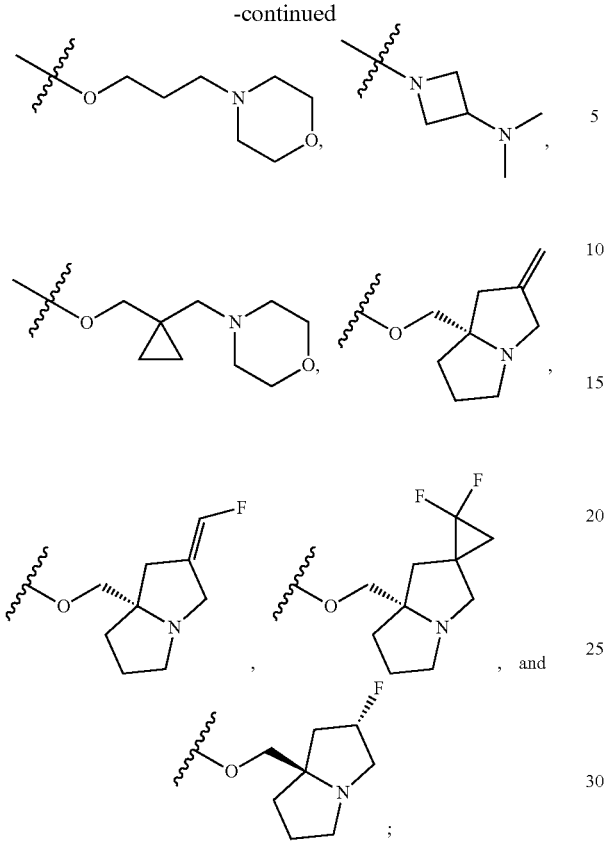

R² is selected from

R⁸ is selected from hydrogen and halogen; each $R^{11c}$ is independently selected from —$OR^{12}$, $C_{1-3}$alkyl, $C_{3-4}$cycloalkyl, —$CH_2$-$C_{3-4}$cycloalkyl, and 5-6 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$; each $R^{20k}$ is independently selected from halogen, —$N(R^{22})(R^{23})$, and —$OR^{21}$; each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20l}$; each $R^{13}$ is independently selected from hydrogen and $C_{1-6}$alkyl; each $R^{15}$ is independently selected from $C_{1-6}$alkyl and $C_{2-9}$heterocycloalkyl, wherein $C_{1-6}$alkyl and $C_2$-heterocycloalkyl are optionally substituted with one, two, or three $R^{20}$m; each $R^{20t}$ is independently selected from halogen, —CN, $C_{3-10}$cycloalkyl, —$OR^{21}$, and —$N(R^{22})(R^{23})$; each $R^{20}$m is independently selected from halogen, —CN, $C_{3-10}$cycloalkyl, —$OR^{21}$, and —$N(R^{22})(R^{23})$; each $R^{21}$ is independently selected from H, $C_{1-3}$alkyl, $C_{1-3}$haloalkyl, $C_{3-6}$cycloalkyl, and 3-4 membered heterocycloalkyl;

each $R^{21}$b is independently selected from H and halogen; each $R^{22}$ is independently selected from H; each $R^{23}$ is independently selected from H; and ----- indicates a single or double bond such that all valences are satisfied.

In embodiments of any formulae described herein, $R^6$ is selected from hydrogen and halogen; $L^7$ is a bond; $R^{17}$ is 525
-continued

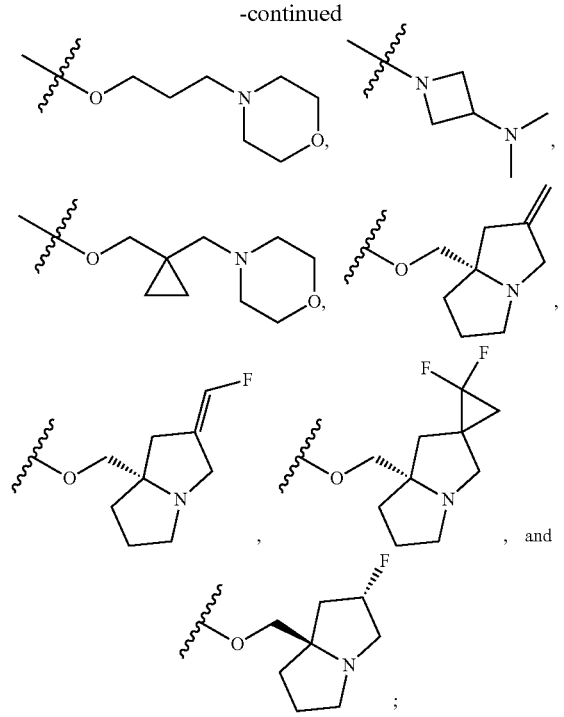

R[2] is selected from

R[8] is selected from hydrogen and halogen; each R[11c] is independently selected from —OR[12], $C_{1-3}$alkyl, $C_{3-4}$cycloalkyl, —CH$_2$-C$_{3-4}$cycloalkyl, and 5 membered heterocycloalkyl, wherein $C_{1-3}$alkyl, $C_{3-4}$cycloalkyl, —CH$_2$-C$_{3-4}$cycloalkyl, and 5-6 membered heterocycloalkyl are optionally substituted with one, two, or three R[20k]; each R[20k] is independently selected from halogen, —N(R[22])(R[23]), and —OR[21]; each R[12] is independently selected from hydrogen; each R[13] is independently selected from hydrogen and $C_{1-6}$alkyl; each R[21] is independently selected from H and $C_{1-3}$alkyl; each R[22] is hydrogen; each R[23] is hydrogen; and ----- indicates a single or double bond such that all valences are satisfied.

In embodiments of any formulae described herein, R[6] is selected from hydrogen and halogen; L[7] is a bond; R[17] is

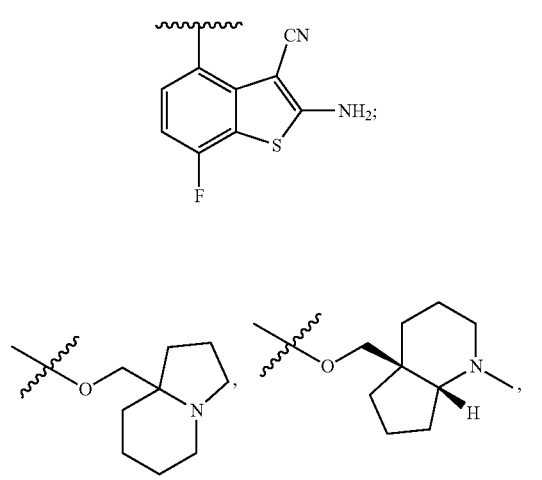

526
-continued

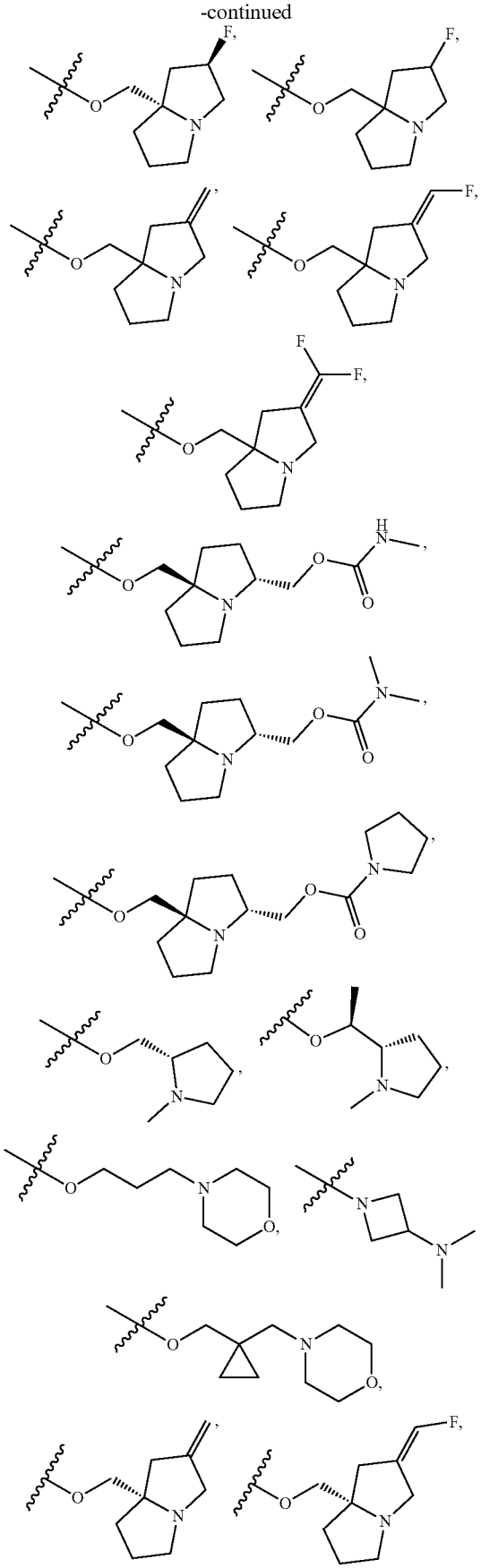

-continued

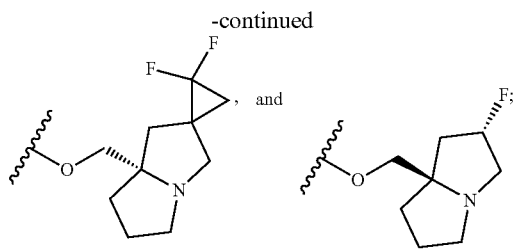

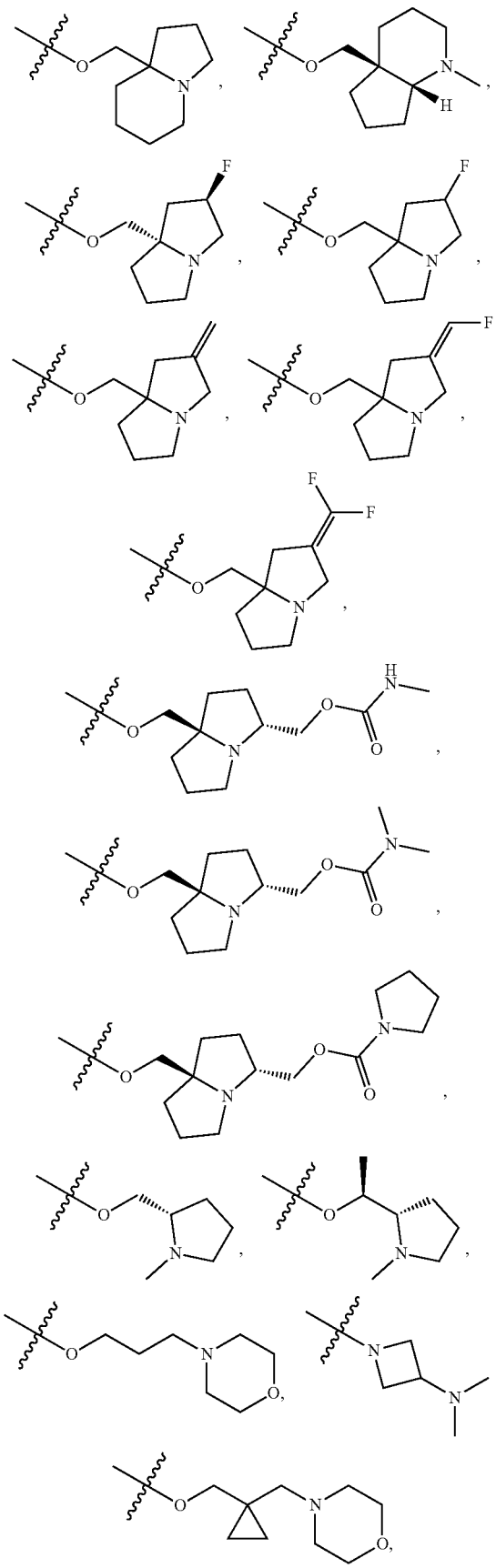

$R^8$ is selected from hydrogen and halogen; $R^4$ is -$L^4$-$R^{4a}$; each $L^4$ is independently selected from a bond and $CR^4R^{4c}$; each $R^{4c}$ is independently selected from hydrogen and $C_{1-3}$alkyl; each $R^{4a}$ is independently selected from $C_{3-4}$cycloalkyl and 5-6 membered heterocycloalkyl, wherein $C_{3-4}$cycloalkyl and 5-6 membered heterocycloalkyl are optionally substituted with one, two, three, or four $R^{4b}$; each $R^{4b}$ is independently selected from halogen, oxo, —CN, $C_{1-3}$alkyl, $C_{3-6}$cycloalkyl, —$OR^{12}$, —$N(R^{12})(R^{13})$, =$C(R^{21}b)_2$, —$C(O)R^{12}$, —$N(R^{14})C(O)R^{12}$, —$S(O)_2R^{15}$, and —$C(O)N(R^{12})(R^{13})$, wherein $C_{1-3}$alkyl and $C_{3-6}$cycloalkyl are optionally substituted with one or more $R^{20}$j; each $R^{11c}$ is independently selected from —$OR^{12}$, $C_{1-3}$alkyl, $C_{3-4}$cycloalkyl, —$CH_2$-$C_{3-4}$cycloalkyl, and 5-6 membered heterocycloalkyl, wherein $C_{1-3}$alkyl, $C_{3-4}$cycloalkyl, —$CH_2$-$C_{3-4}$cycloalkyl, and 5-6 membered heterocycloalkyl are optionally substituted with one, two, or three $R^{20k}$; each $R^{20k}$ is independently selected from halogen, —$N(R^{22})(R^{23})$, and —$OR^{21}$; each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20l}$; each $R^{13}$ is independently selected from hydrogen and $C_{1-6}$alkyl; each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20}$m; each $R^{20}$j is independently selected from halogen and —$OR^{21}$; each $R^{20l}$ is independently selected from halogen, —CN, $C_{3-10}$cycloalkyl, —$OR^{21}$, and —$N(R^{22})(R^{23})$; each $R^{20}$m is independently selected from halogen, —CN, $C_{3-10}$cycloalkyl, —$OR^{21}$, and —$N(R^{22})(R^{23})$; each $R^{21}$ is independently selected from H, $C_{1-3}$alkyl, $C_{1-3}$haloalkyl, $C_{3-6}$cycloalkyl, and 3-4 membered heterocycloalkyl; each $R^{21}$b is independently selected from H and halogen; each $R^{22}$ is independently selected from H; each $R^{23}$ is independently selected from H; and ----- indicates a single or double bond such that all valences are satisfied.

In embodiments of any formulae described herein, $R^6$ is selected from hydrogen and halogen; $L^7$ is a bond; $R^{17}$ is

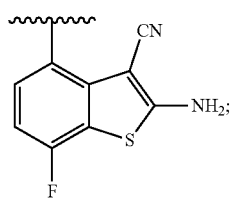 [SMILES: *c1ccc(F)c2sc(N)c(C#N)c12]

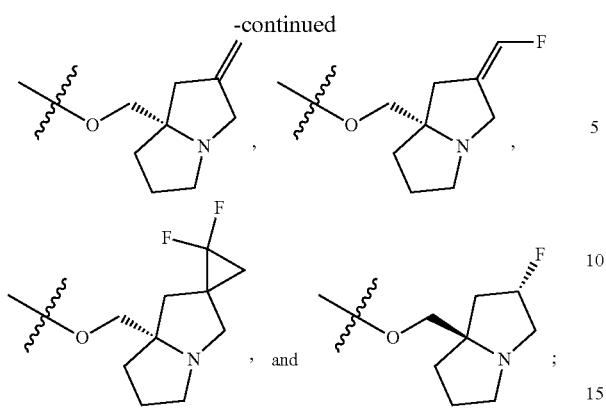

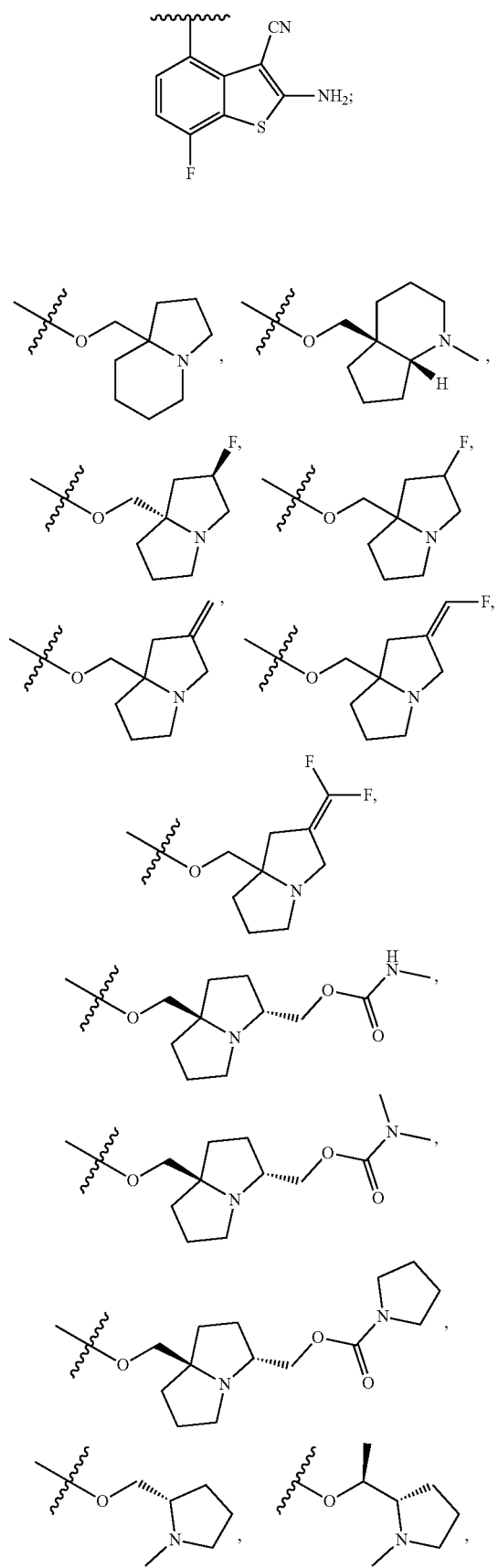

$R^2$ is selected from $R^8$ is selected from hydrogen and halogen; $R^4$ is $-L^4-R^{4a}$; each $L^4$ is independently selected from a bond and $CR^{4c}R^{4c}$; each $R^{4c}$ is independently selected from hydrogen and $C_{1-3}$alkyl; each $R^{4a}$ is independently selected from $C_{3-4}$cycloalkyl and 5-6 membered heterocycloalkyl, wherein $C_{3-4}$cycloalkyl and 5-6 membered heterocycloalkyl are optionally substituted with one, two, three, or four $R^{46}$; each $R^{4b}$ is independently selected from halogen, oxo, —CN, $C_{1-3}$alkyl, $C_{3-6}$cycloalkyl, $-OR^{12}$, $-N(R^{12})(R^{13})$, $-C(R^{21}b)_2$, $-C(O)R^{12}$, $-N(R^{14})C(O)R^{12}$, $-S(O)_2R^{15}$, and $-C(O)N(R^{12})(R^{13})$, wherein $C_{1-3}$alkyl and $C_{3-6}$cycloalkyl are optionally substituted with one or more $R^{20}j$; each $R^{11c}$ is independently selected from $-OR^{12}$, $C_{1-3}$alkyl, $C_{3-4}$cycloalkyl, $-CH_2-C_{3}$-4cycloalkyl, and 5-6 membered heterocycloalkyl, wherein $C_{1-3}$alkyl, $C_{3-4}$cycloalkyl, $-CH_2-C_{3-4}$cycloalkyl, and 5-6 membered heterocycloalkyl are optionally substituted with one, two, or three $R^{20k}$; each $R^{20k}$ is independently selected from halogen, $-N(R^{22})(R^{23})$, and $-OR^{21}$; each $R^{12}$ is independently selected from hydrogen, $C_{1-6}$alkyl, and $C_{2-9}$heterocycloalkyl, wherein $C_{1-6}$alkyl, and $C_{2-9}$heterocycloalkyl are optionally substituted with one, two, or three $R^{20l}$; each $R^{13}$ is independently selected from hydrogen and $C_{1-6}$alkyl; each $R^{15}$ is independently selected from $C_{1-6}$alkyl and $C_{2-9}$heterocycloalkyl, wherein $C_{1-6}$alkyl and $C_{2-9}$heterocycloalkyl are optionally substituted with one, two, or three $R^{20}m$; each $R^{20}j$ is independently selected from halogen and $-OR^{21}$; each $R^{20t}$ is independently selected from halogen, —CN, $C_{3-10}$cycloalkyl, $-OR^{21}$, and $-N(R^{22})(R^{23})$; each $R^{20}m$ is independently selected from halogen, —CN, $C_{3-10}$cycloalkyl, $-OR^{21}$, and $-N(R^{22})(R^{23})$; each $R^{21}$ is independently selected from H, $C_{1-3}$alkyl, $C_{1-3}$haloalkyl, $C_{3-6}$cycloalkyl, and 3-4 membered heterocycloalkyl; each $R^{21}b$ is independently selected from H and halogen; each $R^{22}$ is independently selected from H;

each $R^{23}$ is independently selected from H; and ----- indicates a single or double bond such that all valences are satisfied.

In embodiments of any formulae described herein, $R^6$ is selected from hydrogen and halogen; $L^7$ is a bond; $R^{17}$ is -continued

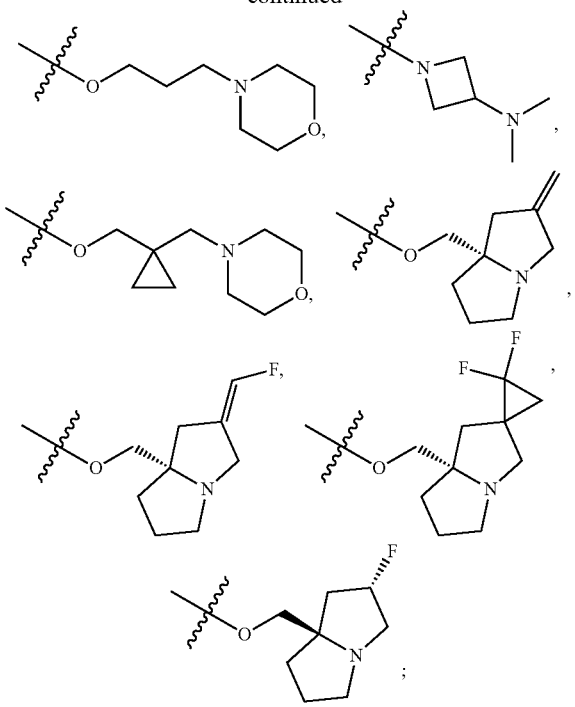

R² is selected from

R⁸ is selected from hydrogen and halogen; R⁴ is -L⁴-R⁴ᵃ; each L⁴ is independently selected from a bond and CH₂; each R⁴ᶜ is independently selected from hydrogen and C₁₋₃alkyl; each R⁴ᵃ is independently selected from C₃₋₄cycloalkyl and 5 membered heterocycloalkyl, wherein C₃₋₄cycloalkyl and 5 membered heterocycloalkyl are optionally substituted with one or two R⁴ᵇ; each R⁴ᵇ is independently selected from halogen, —OR¹², and —N(R¹²)(R¹³); each R¹¹ᶜ is independently selected from —OR¹², C₁₋₃alkyl, C₃cycloalkyl, —CH₂-C₃₋₄cycloalkyl, and 5 membered heterocycloalkyl, wherein C₁₋₃alkyl, C₃cycloalkyl, —CH₂-C₃₋₄cycloalkyl, and 5 membered heterocycloalkyl are optionally substituted with one, two, or three R²⁰ᵏ; each R²⁰ᵏ is independently selected from halogen, —N(R²²)(R²³), and —OR²¹; each R¹² is independently selected from hydrogen; each R¹³ is independently selected from hydrogen; each R²¹ is independently selected from hydrogen and C₁₋₃alkyl; each R²² is hydrogen; each R²³ is hydrogen; and ----- indicates a single or double bond such that all valences are satisfied. such that all valences are satisfied.

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

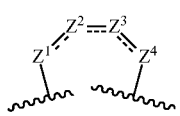

is

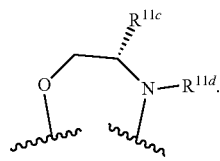

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

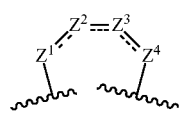

is

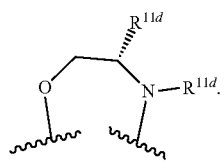

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

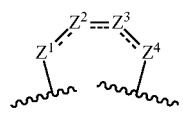

is

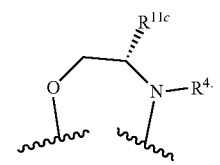

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof, is

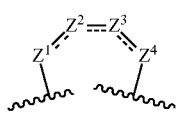

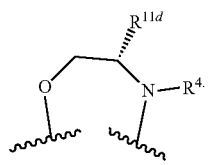

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

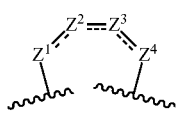

is

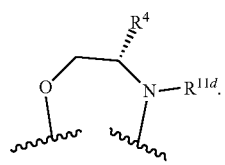

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (X VIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

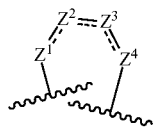

is

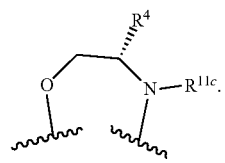

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

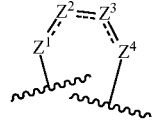

is

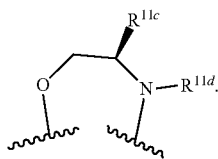

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

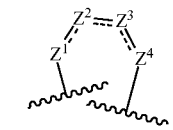

is

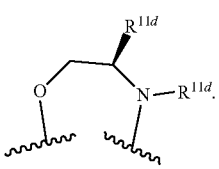

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

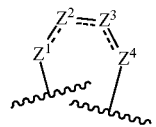

is

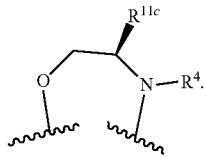

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

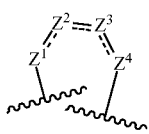

is

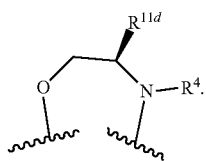

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

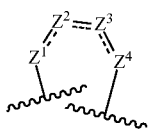

is

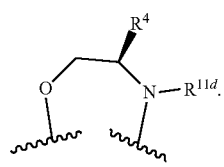

In some embodiments of a compound of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), or any embodiment thereof,

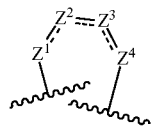

is

The individual embodiments herein below, or combinations thereof, (e.g., embodiments of $R^2$, $R^{11d}$, $Z^2$, $Z^3$, $R^4$, or $R^{11c}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12a}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{206}$. In embodiments of the formulae above, $R^2$ is hydrogen.

In embodiments of the formulae above, $R^2$ is not hydrogen and $R^{11d}$ is not independently selected from H and —$CH_2CN$. In embodiments of the formulae above, $R^2$ is not hydrogen and $R^{11c}$ is not independently selected from H and —$CH_2CN$.

In embodiments of the formulae above, $R^2$ is not hydrogen, $Z^2$ is not-C(H)$_2$—, and $Z^3$ is not-C(H)(CH$_2$CN)—.

In embodiments of the formulae above, $R^2$ is not hydrogen, $Z^3$ is not-C(H)$_2$—, and $Z^2$ is not-C(H)(CH$_2$CN)—.

In embodiments of the formulae above, $R^4$ is not

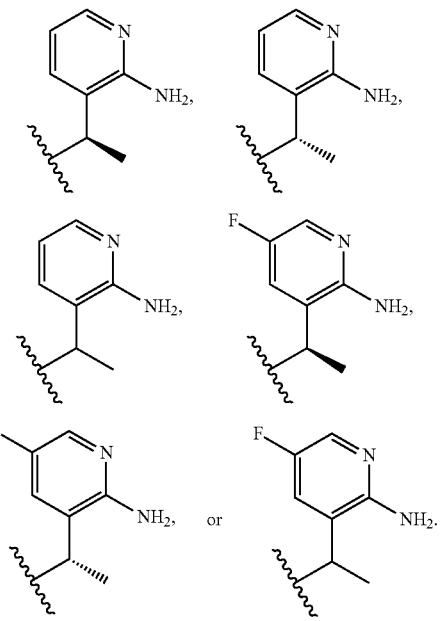

In embodiments of the formulae above, $R^{11c}$ is not

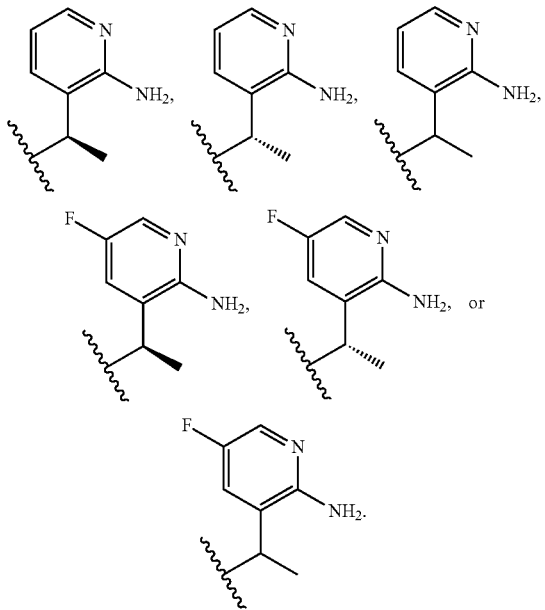

In embodiments of the formulae above, $R^{11d}$ is not

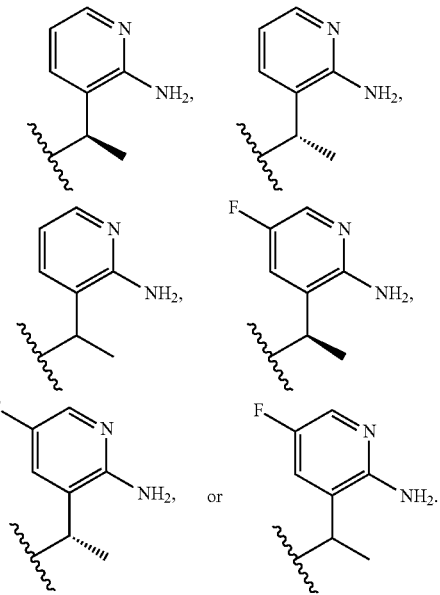

In embodiments of the formulae above, $R^{4a}$ is not a pyridyl substituted with —$NH_2$. In embodiments of the formulae above, $R^{4a}$ is not a 6 membered nitrogen containing heteroaryl substituted with —$NH_2$.

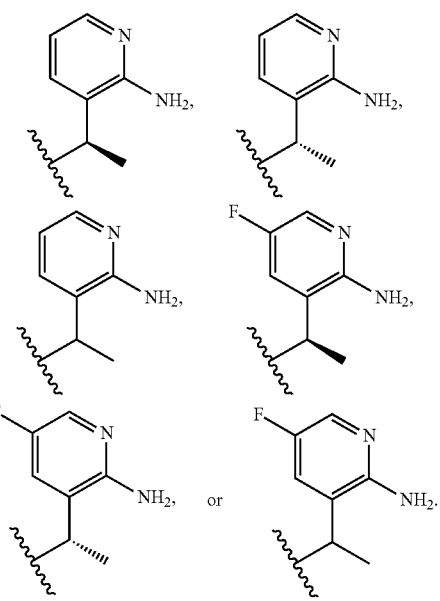

In embodiments of the formulae above, $R^4$ is

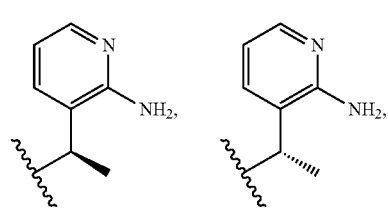

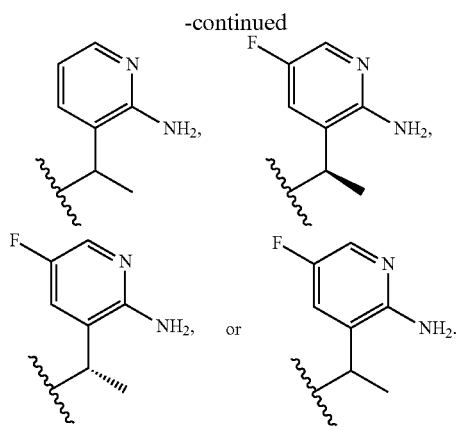

In embodiments of the formulae above, $R^{11c}$ is

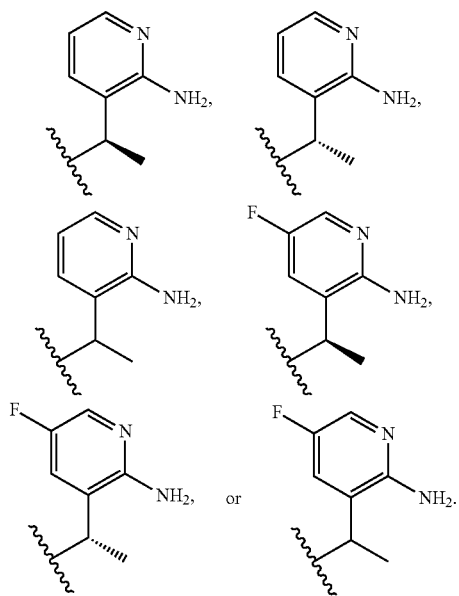

In embodiments of the formulae above, $R^{4a}$ is pyridyl substituted with —$NH_2$. In embodiments of the formulae above, $R^{4a}$ is 6 membered nitrogen containing heteroaryl substituted with —$NH_2$.

The individual embodiments herein below, or combinations thereof, (e.g., embodiments of $L^4$, $R^{4a}$, $R^{4b}$, $R^{20j}$, or $R^4$ are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'- 1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"- 1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $L^4$ is independently a bond. In embodiments of the formulae above, $L^4$ is independently —O—. In embodiments of the formulae above, $L^4$ is independently —$N(R^{4d})$—. In embodiments of the formulae above, $L^4$ is independently —C(O)—. In embodiments of the formulae above, $L^4$ is independently —S—. In embodiments of the formulae above, $L^4$ is independently —$S(O)_2$—. In embodiments of the formulae above, $L^4$ is independently —S(O)—. In embodiments of the formulae above, $L^4$ is independently —$P(O)R^{4d}$—. In embodiments of the formulae above, $L^4$ is independently $CR^{4c}R^{4c}$. In embodiments of the formulae above, $L^4$ is independently —$OCR^{4c}R^{4c}$—. In embodiments of the formulae above, $L^4$ is independently —$N(R^{4d})CR^{4c}R^{4c}$—. In embodiments of the formulae above, $L^4$ is independently —$C(O)CR^4R^4$—. In embodiments of the formulae above, $L^4$ is independently —$SCR^4CR^{4c}$—. In embodiments of the formulae above, $L^4$ is independently —$S(O)_2CR^{4o}$ C. $R^{4c}$—. In embodiments of the formulae above, $L^4$ is independently —$S(O)CR^4R^{4c}$—. In embodiments of the formulae above, $L^4$ is independently —$P(O)R^4dCR^4CR^{4c}$—. In embodiments of the formulae above, $L^4$ is independently —$CR^4R^4CR^4R^{4c}$. In embodiments of the formulae above, $L^4$ is independently —$CR^{4c}R^{4c}O$—. In embodiments of the formulae above, $L^4$ is independently —$CR^{4c}R^4CN(R^{4d})$—. In embodiments of the formulae above, $L^4$ is independently —$CR^4R^4C(O)$—. In embodiments of the formulae above, $L^4$ is independently —$CR^4R^{4c}S$—. In embodiments of the formulae above, $L^4$ is independently —$CR^{4c}R^{4c}S(O)_2$—. In embodiments of the formulae above, $L^4$ is independently —$CR^{4c}R^{4c}S(O)$—. In embodiments of the formulae above, $L^4$ is independently —$CR^{4c}R^4 cP(O)R^{4d}$—. In embodiments of the formulae above, $L^4$ is independently —$N(R^{4d})C(O)$—. In embodiments of the formulae above, $L^4$ is independently —$N(R^{4d})S(O)_2$—. In embodiments of the formulae above, $L^4$ is independently —$N(R^{4d})S(O)$—. In embodiments of the formulae above, $L^4$ is independently —$N(R^{4d})P(O)R^{4d}$—. In embodiments of the formulae above, $L^4$ is independently —$C(O)N(R^{4d})$—. In embodiments of the formulae above, $L^4$ is independently —$S(O)_2N(R^{4d})$—. In embodiments of the formulae above, $L^4$ is independently —$S(O)N(R^{4d})$—. In embodiments of the formulae above, $L^4$ is independently —$P(O)R^{4d}N(R^{4d})$—. In embodiments of the formulae above, $L^4$ is independently —OC(O)—. In embodiments of the formulae above, $L^4$ is independently —$OS(O)_2$—. In embodiments of the formulae above, $L^4$ is independently —OS(O)—. In embodiments of the formulae above, $L^4$ is independently —$OP(O)R^{4d}$—. In embodiments of the formulae above, $L^4$ is independently —C(O)O—. In embodiments of the formulae above, $L^4$ is independently —S(O)$_2$O—. In embodiments of the formulae above, $L^4$ is independently —S(O)O—. In embodiments of the formulae above, $L^4$ is independently —P(O)R$^{4d}$O—. In embodiments of the formulae above, $L^4$ is independently CH$_2$. In embodiments of the formulae above, $L^4$ is independently —OCH$_2$—. In embodiments of the formulae above, $L^4$ is independently —N(H)CH$_2$—. In embodiments of the formulae above, $L^4$ is independently —C(O)CH$_2$—. In embodiments of the formulae above, $L^4$ is independently —SCH$_2$—. In embodiments of the formulae above, $L^4$ is independently —S(O)$_2$CH$_2$—. In embodiments of the formulae above, $L^4$ is independently —S(O)CH$_2$—. In embodiments of the formulae above, $L^4$ is independently —P(O)R$^{4d}$CH$_2$—. In embodiments of the formulae above, $L^4$ is independently —CH$_2$CH$_2$—. In embodiments of the formulae above, $L^4$ is independently —CH$_2$O—. In embodiments of the formulae above, $L^4$ is independently —CH$_2$N(H)—. In embodiments of the formulae above, $L^4$ is independently —CH$_2$C(O)—. In embodiments of the formulae above, $L^4$ is independently —CH$_2$S—. In embodiments of the formulae above, $L^4$ is independently —CH$_2$S(O)$_2$—. In embodiments of the formulae above, $L^4$ is independently —CH$_2$S(O)—. In embodiments of the formulae above, $L^4$ is independently —CH$_2$P(O)R$^{4d}$—. In embodiments of the formulae above, $L^4$ is independently —N(H)C(O)—. In embodiments of the formulae above, $L^4$ is independently —N(H)S(O)$_2$—. In embodiments of the formulae above, $L^4$ is independently —N(H)S(O)—. In embodiments of the formulae above, $L^4$ is independently —N(H)P(O)R$^{4d}$—. In embodiments of the formulae above, $L^4$ is independently —C(O)N(H)—. In embodiments of the formulae above, $L^4$ is independently —S(O)$_2$N(H)—. In embodiments of the formulae above, $L^4$ is independently —S(O)N(H)—.

In embodiments of the formulae above, each $R^{4a}$ is independently $C_{3-10}$cycloalkyl. In embodiments of the formulae above, each $R^{4a}$ is independently $C_{2-9}$heterocycloalkyl. In embodiments of the formulae above, each $R^{4a}$ is independently $C_{6-10}$aryl. In embodiments of the formulae above, each $R^{4a}$ is independently $C_{1-9}$heteroaryl. In embodiments of the formulae above, each $R^{4a}$ is independently $C_{3-10}$cycloalkyl substituted with one, two, three, or four $R^{4b}$. In embodiments of the formulae above, each $R^{4a}$ is independently $C_{2-9}$heterocycloalkyl substituted with one, two, three, or four $R^{4b}$. In embodiments of the formulae above, each $R^{4a}$ is independently $C_{6-10}$aryl substituted with one, two, three, or four $R^{4b}$. In embodiments of the formulae above, each $R^{4a}$ is independently $C_{1-9}$heteroaryl substituted with one, two, three, or four $R^{4b}$. In embodiments of the formulae above, each $R^{4a}$ is independently $C_{3-8}$cycloalkyl. In embodiments of the formulae above, each $R^{4a}$ is independently $C_{2-7}$heterocycloalkyl. In embodiments of the formulae above, each $R^{4a}$ is independently phenyl. In embodiments of the formulae above, each $R^{4a}$ is independently $C_{1-5}$heteroaryl. In embodiments of the formulae above, each $R^{4a}$ is independently $C_3$-cycloalkyl substituted with one, two, three, or four $R^{4b}$. In embodiments of the formulae above, each $R^{4a}$ is independently $C_{2-7}$heterocycloalkyl substituted with one, two, three, or four $R^{4b}$. In embodiments of the formulae above, each $R^{4a}$ is independently phenyl substituted with one, two, three, or four $R^{4b}$. In embodiments of the formulae above, each $R^{4a}$ is independently $C_{1-5}$heteroaryl substituted with one, two, three, or four $R^{4b}$. In embodiments of the formulae above, each $R^{4a}$ is independently $C_{3-6}$cycloalkyl. In embodiments of the formulae above, each $R^{4a}$ is independently $C_2$-sheterocycloalkyl. In embodiments of the formulae above, each $R^{4a}$ is independently $C_{1-4}$heteroaryl. In embodiments of the formulae above, each $R^{4a}$ is independently $C_{3-6}$cycloalkyl substituted with one, two, three, or four $R^{4b}$. In embodiments of the formulae above;

each $R^{4a}$ is independently $C_2$-sheterocycloalkyl substituted with one, two, three, or four $R^{4b}$. In embodiments of the formulae above;

each $R^{4a}$ is independently $C_{1-4}$heteroaryl substituted with one, two, three, or four $R^{4b}$. In embodiments of the formulae above, each $R^4$a is independently 3-6 membered cycloalkyl. In embodiments of the formulae above, each $R^{4a}$ is independently 3-6 membered heterocycloalkyl. In embodiments of the formulae above, each $R^{4a}$ is independently 5-6 membered heteroaryl. In embodiments of the formulae above, each $R^{4a}$ is independently 3-6 membered cycloalkyl substituted with one, two, three, or four $R^{4b}$. In embodiments of the formulae above, each $R^{4a}$ is independently 3-6 membered heterocycloalkyl substituted with one, two, three, or four $R^{4b}$. In embodiments of the formulae above, each $R^{4a}$ is independently 5-6 membered heteroaryl substituted with one, two, three, or four $R^{4b}$. In embodiments of the formulae above, each $R^{4a}$ is independently 3-6 membered heterocycloalkyl including at least one ring nitrogen. In embodiments of the formulae above, each $R^{4a}$ is independently 5-6 membered heteroaryl including at least one ring nitrogen. In embodiments of the formulae above, each $R^4$a is independently 3-6 membered heterocycloalkyl including at least one ring nitrogen and substituted with one, two, three, or four $R^{4b}$. In embodiments of the formulae above, each $R^{4a}$ is independently 5-6 membered heteroaryl including at least one ring nitrogen and substituted with one, two, three, or four $R^{4b}$. In embodiments of the formulae above;

each $R^{4a}$ is independently 3-6 membered heterocycloalkyl including at least one ring oxygen. In embodiments of the formulae above;

each $R^{4a}$ is independently 5-6 membered heteroaryl including at least one ring oxygen. In embodiments of the formulae above, each $R^{4a}$ is independently 3-6 membered heterocycloalkyl including at least one ring oxygen and substituted with one, two, three, or four $R^{4b}$. In embodiments of the formulae above, each $R^{4a}$ is independently 5-6 membered heteroaryl including at least one ring oxygen and substituted with one, two, three, or four $R^{4b}$.

In embodiments of the formulae above, $R^{4a}$ is 3-12 membered cycloalkyl. In embodiments of the formulae above, $R^{4a}$ is 5-12 membered cycloalkyl. In embodiments of the formulae above, $R^{4a}$ is 3-12 membered heterocycloalkyl. In embodiments of the formulae above, $R^{4a}$ is 6-12 membered aryl. In embodiments of the formulae above, $R^{4a}$ is 7-12 membered aryl. In embodiments of the formulae above, $R^{4a}$ is 5-12 membered heteroaryl.

In embodiments of the formulae above, $R^{4a}$ is 4-12 membered cycloalkyl comprising one or more ring nitrogen atoms. In embodiments of the formulae above, $R^{4a}$ is 5-12 membered cycloalkyl comprising one or more ring nitrogen atoms. In embodiments of the formulae above, $R^{4a}$ is 3-12 membered heterocycloalkyl comprising one or more ring nitrogen atoms. In embodiments of the formulae above, $R^{4a}$ is 6-12 membered aryl comprising one or more ring nitrogen atoms. In embodiments of the formulae above, $R^{4a}$ is 7-12 membered aryl comprising one or more ring nitrogen atoms. In embodiments of the formulae above, $R^{4a}$ is 5-12 membered heteroaryl comprising one or more ring nitrogen atoms.

In embodiments of the formulae above, $R^{4a}$ is 4-12 membered cycloalkyl comprising one or more ring oxygen atoms. In embodiments of the formulae above, $R^{4a}$ is 5-12 membered cycloalkyl comprising one or more ring oxygen atoms. In embodiments of the formulae above, $R^{4a}$ is 3-12 membered heterocycloalkyl comprising one or more ring oxygen atoms. In embodiments of the formulae above, $R^{4a}$ is 6-12 membered aryl comprising one or more ring oxygen atoms. In embodiments of the formulae above, $R^{4a}$ is 7-12 membered aryl comprising one or more ring oxygen atoms. In embodiments of the formulae above, $R^{4a}$ is 5-12 membered heteroaryl comprising one or more ring oxygen atoms.

In embodiments of the formulae above, $R^{4a}$ is 3-12 membered cycloalkyl optionally substituted with one, two, three, or four $R^{4b}$. In embodiments of the formulae above, $R^{4a}$ is 5-12 membered cycloalkyl optionally substituted with one, two, three, or four $R^{4b}$. In embodiments of the formulae above, $R^{4a}$ is 3-12 membered heterocycloalkyl optionally substituted with one, two, three, or four $R^{4b}$. In embodiments of the formulae above, $R^{4a}$ is 6-12 membered aryl optionally substituted with one, two, three, or four $R^{4b}$. In embodiments of the formulae above, $R^{4a}$ is 7-12 membered aryl optionally substituted with one, two, three, or four $R^{4b}$. In embodiments of the formulae above, $R^{4a}$ is 5-12 membered heteroaryl optionally substituted with one, two, three, or four $R^{4b}$.

In embodiments of the formulae above, $R^{4a}$ is 3-12 membered cycloalkyl comprising one or more ring nitrogen atoms and optionally substituted with one, two, three, or four $R^{4b}$. In embodiments of the formulae above, $R^{4a}$ is 5-12 membered cycloalkyl comprising one or more ring nitrogen atoms and optionally substituted with one, two, three, or four $R^{4b}$. In embodiments of the formulae above, $R^{4a}$ is 3-12 membered heterocycloalkyl comprising one or more ring nitrogen atoms and optionally substituted with one, two, three, or four $R^{4b}$. In embodiments of the formulae above, $R^{4a}$ is 6-12 membered aryl comprising one or more ring nitrogen atoms and optionally substituted with one, two, three, or four $R^{4b}$. In embodiments of the formulae above, $R^{4a}$ is 7-12 membered aryl comprising one or more ring nitrogen atoms and optionally substituted with one, two, three, or four $R^{4b}$. In embodiments of the formulae above, $R^{4a}$ is 5-12 membered heteroaryl comprising one or more ring nitrogen atoms and optionally substituted with one, two, three, or four $R^{4b}$.

In embodiments of the formulae above, $R^{4a}$ is a 3-12 membered cycloalkyl comprising one or more ring oxygen atoms and optionally substituted with one, two, three, or four $R^{4b}$. In embodiments of the formulae above, $R^{4a}$ is a 5-12 membered cycloalkyl comprising one or more ring oxygen atoms and optionally substituted with one, two, three, or four $R^{4b}$. In embodiments of the formulae above, $R^{4a}$ is 3-12 membered heterocycloalkyl comprising one or more ring oxygen atoms and optionally substituted with one, two, three, or four $R^{4b}$. In embodiments of the formulae above, $R^{4a}$ is 6-12 membered aryl comprising one or more ring oxygen atoms and optionally substituted with one, two, three, or four $R^{4b}$. In embodiments of the formulae above, $R^{4a}$ is 7-12 membered aryl comprising one or more ring oxygen atoms and optionally substituted with one, two, three, or four $R^{4b}$. In embodiments of the formulae above, $R^{4a}$ is 5-12 membered heteroaryl comprising one or more ring oxygen atoms and optionally substituted with one, two, three, or four $R^{4b}$.

In embodiments of the formulae above, $R^{4a}$ is a $C_3$cycloalkyl optionally substituted with one, two, three, or four $R^{4b}$. In embodiments of the formulae above, $R^{4a}$ is a $C_4$cycloalkyl optionally substituted with one, two, three, or four $R^{4b}$. In embodiments of the formulae above, $R^{4a}$ is a $C_5$cycloalkyl optionally substituted with one, two, three, or four $R^{4b}$. In embodiments of the formulae above, $R^{4a}$ is a $C_6$cycloalkyl optionally substituted with one, two, three, or four $R^{4b}$. In embodiments of the formulae above, $R^{4a}$ is a $C_7$cycloalkyl optionally substituted with one, two, three, or four $R^{4b}$. In embodiments of the formulae above, $R^{4a}$ is a $C_8$cycloalkyl optionally substituted with one, two, three, or four $R^{4b}$. In embodiments of the formulae above, $R^{4a}$ is a $C_9$cycloalkyl optionally substituted with one, two, three, or four $R^{4b}$. In embodiments of the formulae above, $R^{4a}$ is a $C_{10}$cycloalkyl optionally substituted with one, two, three, or four $R^{4b}$. In embodiments of the formulae above, $R^{4a}$ is a monocyclic $C_3$cycloalkyl optionally substituted with one, two, three, or four $R^{4b}$. In embodiments of the formulae above, $R^{4a}$ is a monocyclic $C_8$cycloalkyl optionally substituted with one, two, three, or four $R^{4b}$. In embodiments of the formulae above, $R^{4a}$ is a monocyclic $C_5$cycloalkyl optionally substituted with one, two, three, or four $R^{4b}$. In embodiments of the formulae above, $R^{4a}$ is a monocyclic $C_9$cycloalkyl optionally substituted with one, two, three, or four $R^{4b}$. In embodiments of the formulae above, $R^{4a}$ is a monocyclic $C_7$cycloalkyl optionally substituted with one, two, three, or four $R^4b$. In embodiments of the formulae above, $R^{4a}$ is a monocyclic $C_8$cycloalkyl optionally substituted with one, two, three, or four $R^{4b}$. In embodiments of the formulae above, $R^{4a}$ is a monocyclic $C_9$cycloalkyl optionally substituted with one, two, three, or four $R^{4b}$. In embodiments of the formulae above, $R^{4a}$ is a monocyclic $C_{10}$cycloalkyl optionally substituted with one, two, three, or four $R^{4b}$. In embodiments of the formulae above, $R^{4a}$ is a fused bicyclic $C_5$cycloalkyl optionally substituted with one, two, three, or four $R^{4b}$. In embodiments of the formulae above, $R^{4a}$ is a fused bicyclic $C_9$cycloalkyl optionally substituted with one, two, three, or four $R^{4b}$. In embodiments of the formulae above, $R^{4a}$ is a fused bicyclic $C_7$cycloalkyl optionally substituted with one, two, three, or four $R^{4b}$. In embodiments of the formulae above, $R^{4a}$ is a fused bicyclic $C_8$cycloalkyl optionally substituted with one, two, three, or four $R^{4b}$. In embodiments of the formulae above, $R^{4a}$ is a fused bicyclic $C_9$cycloalkyl optionally substituted with one, two, three, or four $R^{4b}$. In embodiments of the formulae above, $R^{4a}$ is a fused bicyclic $C_{10}$cycloalkyl optionally substituted with one, two, three, or four $R^{4b}$. In embodiments of the formulae above, $R^{4a}$ is a bridged bicyclic $C_5$cycloalkyl optionally substituted with one, two, three, or four $R^{4b}$. In embodiments of the formulae above, $R^{4a}$ is a bridged bicyclic $C_9$cycloalkyl optionally substituted with one, two, three, or four $R^{4b}$. In embodiments of the formulae above, $R^{4a}$ is a bridged bicyclic $C_7$cycloalkyl optionally substituted with one, two, three, or four $R^{4b}$. In embodiments of the formulae above, $R^{4a}$ is a bridged bicyclic $C_8$cycloalkyl optionally substituted with one, two, three, or four $R^{4b}$. In embodiments of the formulae above, $R^{4a}$ is a bridged bicyclic $C_9$cycloalkyl optionally substituted with one, two, three, or four $R^{4b}$. In embodiments of the formulae above, $R^{4a}$ is a bridged bicyclic $C_{10}$cycloalkyl optionally substituted with one, two, three, or four $R^{4b}$. In embodiments of the formulae above, $R^{4a}$ is a spirocyclic bicyclic $C_5$cycloalkyl optionally substituted with one, two, three, or four $R^{4b}$. In embodiments of the formulae above, $R^{4a}$ is a spirocyclic bicyclic $C_6$cycloalkyl optionally substituted with one, two, three, or four $R^{4b}$. In embodiments of the formulae above, $R^{4a}$ is a spirocyclic bicyclic C-cycloalkyl optionally substituted with one, two, three, or four $R^{4b}$. In embodiments of the formulae above, $R^{4a}$ is a spirocyclic bicyclic $C_8$cycloalkyl optionally substituted with one, two, three, or four $R^{4b}$. In embodiments of the formulae above, $R^{4a}$ is a spirocyclic bicyclic $C_9$cycloalkyl optionally substituted with one, two, three, or four $R^{4b}$. In embodiments of the formulae above, $R^{4a}$ is a spirocyclic bicyclic $C_{10}$cycloalkyl optionally substituted with one, two, three, or four $R^{4b}$.

In embodiments of the formulae above, $R^{4a}$ is a $C_6$aryl optionally substituted with one, two, three, or four $R^{4b}$. In embodiments of the formulae above, $R^{4a}$ is a $C_7$aryl optionally substituted with one, two, three, or four $R^{4b}$. In embodiments of the formulae above, $R^{4a}$ is a $C_8$aryl optionally substituted with one, two, three, or four $R^{4b}$. In embodiments of the formulae above, $R^{4a}$ is a $C_6$aryl optionally substituted with one, two, three, or four $R^{4b}$. In embodiments of the formulae above, $R^{4a}$ is a $C_{10}$aryl optionally substituted with one, two, three, or four $R^{4b}$. In embodiments of the formulae above, $R^{4a}$ is a monocyclic $C_7$aryl optionally substituted with one, two, three, or four $R^{4b}$. In embodiments of the formulae above, $R^{4a}$ is a monocyclic $C_7$aryl optionally substituted with one, two, three, or four $R^{4b}$. In embodiments of the formulae above, $R^{4a}$ is a monocyclic $C_8$aryl optionally substituted with one, two, three, or four $R^{4b}$. In embodiments of the formulae above, $R^{4a}$ is a monocyclic $C_6$aryl optionally substituted with one, two, three, or four $R^{4b}$. In embodiments of the formulae above, $R^{4a}$ is a monocyclic $C_{10}$aryl optionally substituted with one, two, three, or four $R^{4b}$. In embodiments of the formulae above, $R^{4a}$ is a fused bicyclic $C_8$aryl optionally substituted with one, two, three, or four $R^{4b}$. In embodiments of the formulae above, $R^{4a}$ is a fused bicyclic $C_6$aryl optionally substituted with one, two, three, or four $R^{4b}$. In embodiments of the formulae above, $R^{4a}$ is a fused bicyclic $C_7$aryl optionally substituted with one, two, three, or four $R^{4b}$. In embodiments of the formulae above, $R^{4a}$ is a fused bicyclic $C_8$aryl optionally substituted with one, two, three, or four $R^{4b}$. In embodiments of the formulae above, $R^{4a}$ is a fused bicyclic $C_7$aryl optionally substituted with one, two, three, or four $R^{4b}$. In embodiments of the formulae above, $R^{4a}$ is a fused bicyclic $C_{10}$aryl optionally substituted with one, two, three, or four $R^{4b}$. In embodiments of the formulae above, $R^{4a}$ is a bridged bicyclic $C_8$aryl optionally substituted with one, two, three, or four $R^{4b}$. In embodiments of the formulae above, $R^{4a}$ is a bridged bicyclic $C_6$aryl optionally substituted with one, two, three, or four $R^{4b}$. In embodiments of the formulae above, $R^{4a}$ is a bridged bicyclic $C_7$aryl optionally substituted with one, two, three, or four $R^{4b}$. In embodiments of the formulae above, $R^{4a}$ is a bridged bicyclic $C_7$aryl optionally substituted with one, two, three, or four $R^{4b}$. In embodiments of the formulae above, $R^{4a}$ is a bridged bicyclic $C_6$aryl optionally substituted with one, two, three, or four $R^{4b}$. In embodiments of the formulae above, $R^{4a}$ is a bridged bicyclic $C_{10}$aryl optionally substituted with one, two, three, or four $R^{4b}$.

In embodiments of the formulae above, $R^{4a}$ is a 3 membered heterocycloalkyl optionally substituted with one, two, three, or four $R^{4b}$. In embodiments of the formulae above, $R^{4a}$ is a 4 membered heterocycloalkyl optionally substituted with one, two, three, or four $R^{4b}$. In embodiments of the formulae above, $R^{4a}$ is a 5 membered heterocycloalkyl optionally substituted with one, two, three, or four $R^{4b}$. In embodiments of the formulae above, $R^{4a}$ is a 6 membered heterocycloalkyl optionally substituted with one, two, three, or four $R^{4b}$. In embodiments of the formulae above, $R^{4a}$ is a 7 membered heterocycloalkyl optionally substituted with one, two, three, or four $R^{4b}$. In embodiments of the formulae above, $R^{4a}$ is a 8 membered heterocycloalkyl optionally substituted with one, two, three, or four $R^{4b}$. In embodiments of the formulae above, $R^{4a}$ is a 9 membered heterocycloalkyl optionally substituted with one, two, three, or four $R^{4b}$. In embodiments of the formulae above, $R^{4a}$ is a 10 membered heterocycloalkyl optionally substituted with one, two, three, or four $R^{4b}$. In embodiments of the formulae above, $R^{4a}$ is a 11 membered heterocycloalkyl optionally substituted with one, two, three, or four $R^{4b}$. In embodiments of the formulae above, $R^{4a}$ is a 12 membered heterocycloalkyl optionally substituted with one, two, three, or four $R^{4b}$.

In embodiments of the formulae above, $R^{4a}$ is a monocyclic 3 membered heterocycloalkyl optionally substituted with one, two, three, or four $R^{4b}$. In embodiments of the formulae above, $R^4$a is a monocyclic 4 membered heterocycloalkyl optionally substituted with one, two, three, or four $R^{4b}$. In embodiments of the formulae above, $R^{4a}$ is a monocyclic 5 membered heterocycloalkyl optionally substituted with one, two, three, or four $R^{4b}$. In embodiments of the formulae above, $R^{4a}$ is a monocyclic 6 membered heterocycloalkyl optionally substituted with one, two, three, or four $R^{4b}$. In embodiments of the formulae above, $R^{4a}$ is a monocyclic 7 membered heterocycloalkyl optionally substituted with one, two, three, or four $R^{4b}$. In embodiments of the formulae above, $R^{4a}$ is a monocyclic 8 membered heterocycloalkyl optionally substituted with one, two, three, or four $R^{4b}$. In embodiments of the formulae above, $R^{4a}$ is a monocyclic 9 membered heterocycloalkyl optionally substituted with one, two, three, or four $R^{4b}$. In embodiments of the formulae above, $R^{4a}$ is a monocyclic 10 membered heterocycloalkyl optionally substituted with one, two, three, or four $R^{4b}$.

In embodiments of the formulae above, $R^{4a}$ is a fused bicyclic 5 membered heterocycloalkyl optionally substituted with one, two, three, or four $R^{4b}$. In embodiments of the formulae above, $R^{4a}$ is a fused bicyclic 6 membered heterocycloalkyl optionally substituted with one, two, three, or four $R^{4b}$. In embodiments of the formulae above, $R^{4a}$ is a fused bicyclic 7 membered heterocycloalkyl optionally substituted with one, two, three, or four $R^{4b}$. In embodiments of the formulae above, $R^{4a}$ is a fused bicyclic 8 membered heterocycloalkyl optionally substituted with one, two, three, or four $R^{4b}$. In embodiments of the formulae above, $R^{4a}$ is a fused bicyclic 9 membered heterocycloalkyl optionally substituted with one, two, three, or four $R^{4b}$. In embodiments of the formulae above, $R^{4a}$ is a fused bicyclic 10 membered heterocycloalkyl optionally substituted with one, two, three, or four $R^{4b}$. In embodiments of the formulae above, $R^{4a}$ is a fused bicyclic 11 membered heterocycloalkyl optionally substituted with one, two, three, or four $R^{4b}$. In embodiments of the formulae above, $R^{4a}$ is a fused bicyclic 12 membered heterocycloalkyl optionally substituted with one, two, three, or four $R^{4b}$.

In embodiments of the formulae above, $R^{4a}$ is a bridged bicyclic 5 membered heterocycloalkyl optionally substituted with one, two, three, or four $R^{4b}$. In embodiments of the formulae above, $R^{4a}$ is a bridged bicyclic 6 membered heterocycloalkyl optionally substituted with one, two, three, or four $R^{4b}$. In embodiments of the formulae above, $R^{4a}$ is a bridged bicyclic 7 membered heterocycloalkyl optionally substituted with one, two, three, or four $R^{4b}$. In embodiments of the formulae above, $R^{4a}$ is a bridged bicyclic 8 membered heterocycloalkyl optionally substituted with one, two, three, or four $R^{4b}$. In embodiments of the formulae above, $R^{4a}$ is a bridged bicyclic 9 membered heterocycloalkyl optionally substituted with one, two, three, or four $R^{4b}$. In embodiments of the formulae above, $R^{4a}$ is a bridged bicyclic 10 membered heterocycloalkyl optionally substituted with one, two, three, or four $R^{4b}$. In embodiments of the formulae above, $R^{4a}$ is a bridged bicyclic 11 membered heterocycloalkyl optionally substituted with one, two, three, or four $R^{4b}$. In embodiments of the formulae above, $R^{4a}$ is a bridged bicyclic 12 membered heterocycloalkyl optionally substituted with one, two, three, or four $R^{4b}$.

In embodiments of the formulae above, $R^{4a}$ is a spirocyclic bicyclic 5 membered heterocycloalkyl optionally substituted with one, two, three, or four $R^{4b}$. In embodiments of the formulae above, $R^{4a}$ is a spirocyclic bicyclic 6 membered heterocycloalkyl optionally substituted with one, two, three, or four $R^{4b}$. In embodiments of the formulae above, $R^{4a}$ is a spirocyclic bicyclic 7 membered heterocycloalkyl optionally substituted with one, two, three, or four $R^{4b}$. In embodiments of the formulae above, $R^{4a}$ is a spirocyclic bicyclic 8 membered heterocycloalkyl optionally substituted with one, two, three, or four $R^{4b}$. In embodiments of the formulae above, $R^{4a}$ is a spirocyclic bicyclic 9 membered heterocycloalkyl optionally substituted with one, two, three, or four $R^{4b}$. In embodiments of the formulae above, $R^{4a}$ is a spirocyclic bicyclic 10 membered heterocycloalkyl optionally substituted with one, two, three, or four $R^{4b}$. In embodiments of the formulae above, $R^{4a}$ is a spirocyclic bicyclic 11 membered heterocycloalkyl optionally substituted with one, two, three, or four $R^{4b}$. In embodiments of the formulae above, $R^{4a}$ is a spirocyclic bicyclic 12 membered heterocycloalkyl optionally substituted with one, two, three, or four $R^{4b}$.

In embodiments of the formulae above, $R^{4a}$ is a 3 membered heterocycloalkyl including at least one nitrogen atom and optionally substituted with one, two, three, or four $R^{4b}$. In embodiments of the formulae above, $R^4$a is a 4 membered heterocycloalkyl including at least one nitrogen atom and optionally substituted with one, two, three, or four $R^{4b}$. In embodiments of the formulae above, $R^{4a}$ is a 5 membered heterocycloalkyl including at least one nitrogen atom and optionally substituted with one, two, three, or four $R^{4b}$. In embodiments of the formulae above, $R^{4a}$ is a 6 membered heterocycloalkyl including at least one nitrogen atom and optionally substituted with one, two, three, or four $R^{4b}$. In embodiments of the formulae above, $R^{4a}$ is a 7 membered heterocycloalkyl including at least one nitrogen atom and optionally substituted with one, two, three, or four $R^{4b}$. In embodiments of the formulae above, $R^{4a}$ is a 8 membered heterocycloalkyl including at least one nitrogen atom and optionally substituted with one, two, three, or four $R^{4b}$. In embodiments of the formulae above, $R^{4a}$ is a 9 membered heterocycloalkyl including at least one nitrogen atom and optionally substituted with one, two, three, or four $R^{4b}$. In embodiments of the formulae above, $R^{4a}$ is a 10 membered heterocycloalkyl including at least one nitrogen atom and optionally substituted with one, two, three, or four $R^{4b}$. In embodiments of the formulae above, $R^{4a}$ is a 11 membered heterocycloalkyl including at least one nitrogen atom and optionally substituted with one, two, three, or four $R^{4b}$. In embodiments of the formulae above, $R^{4a}$ is a 12 membered heterocycloalkyl including at least one nitrogen atom and optionally substituted with one, two, three, or four $R^{4b}$.

In embodiments of the formulae above, $R^{4a}$ is a monocyclic 3 membered heterocycloalkyl including at least one nitrogen atom and optionally substituted with one, two, three, or four $R^{4b}$. In embodiments of the formulae above, $R^{4a}$ is a monocyclic 4 membered heterocycloalkyl including at least one nitrogen atom and optionally substituted with one, two, three, or four $R^{4b}$. In embodiments of the formulae above, $R^{4a}$ is a monocyclic 5 membered heterocycloalkyl including at least one nitrogen atom and optionally substituted with one, two, three, or four $R^{4b}$. In embodiments of the formulae above, $R^{4a}$ is a monocyclic 6 membered heterocycloalkyl including at least one nitrogen atom and optionally substituted with one, two, three, or four $R^{4b}$. In embodiments of the formulae above, $R^{4a}$ is a monocyclic 7 membered heterocycloalkyl including at least one nitrogen atom and optionally substituted with one, two, three, or four $R^{4b}$. In embodiments of the formulae above, $R^{4a}$ is a monocyclic 8 membered heterocycloalkyl including at least one nitrogen atom and optionally substituted with one, two, three, or four $R^{4b}$. In embodiments of the formulae above, $R^{4a}$ is a monocyclic 9 membered heterocycloalkyl including at least one nitrogen atom and optionally substituted with one, two, three, or four $R^{4b}$. In embodiments of the formulae above, $R^{4a}$ is a monocyclic 10 membered heterocycloalkyl including at least one nitrogen atom and optionally substituted with one, two, three, or four $R^{4b}$.

In embodiments of the formulae above, $R^{4a}$ is a fused bicyclic 5 membered heterocycloalkyl including at least one nitrogen atom and optionally substituted with one, two, three, or four $R^{4b}$. In embodiments of the formulae above, $R^{4a}$ is a fused bicyclic 6 membered heterocycloalkyl including at least one nitrogen atom and optionally substituted with one, two, three, or four $R^{4b}$. In embodiments of the formulae above, $R^{4a}$ is a fused bicyclic 7 membered heterocycloalkyl including at least one nitrogen atom and optionally substituted with one, two, three, or four $R^{4b}$. In embodiments of the formulae above, $R^{4a}$ is a fused bicyclic 8 membered heterocycloalkyl including at least one nitrogen atom and optionally substituted with one, two, three, or four $R^{4b}$. In embodiments of the formulae above, $R^{4a}$ is a fused bicyclic 9 membered heterocycloalkyl including at least one nitrogen atom and optionally substituted with one, two, three, or four $R^{4b}$. In embodiments of the formulae above, $R^{4a}$ is a fused bicyclic 10 membered heterocycloalkyl including at least one nitrogen atom and optionally substituted with one, two, three, or four $R^{4b}$. In embodiments of the formulae above, $R^{4a}$ is a fused bicyclic 11 membered heterocycloalkyl including at least one nitrogen atom and optionally substituted with one, two, three, or four $R^{4b}$. In embodiments of the formulae above, $R^{4a}$ is a fused bicyclic 12 membered heterocycloalkyl including at least one nitrogen atom and optionally substituted with one, two, three, or four $R^{4b}$.

In embodiments of the formulae above, $R^{4a}$ is a bridged bicyclic 5 membered heterocycloalkyl including at least one nitrogen atom and optionally substituted with one, two, three, or four $R^{4b}$. In embodiments of the formulae above, $R^{4a}$ is a bridged bicyclic 6 membered heterocycloalkyl including at least one nitrogen atom and optionally substituted with one, two, three, or four $R^{4b}$. In embodiments of the formulae above, $R^{4a}$ is a bridged bicyclic 7 membered heterocycloalkyl including at least one nitrogen atom and optionally substituted with one, two, three, or four $R^{4b}$. In embodiments of the formulae above, $R^{4a}$ is a bridged bicyclic 8 membered heterocycloalkyl including at least one nitrogen atom and optionally substituted with one, two, three, or four $R^{4b}$. In embodiments of the formulae above, $R^{4a}$ is a bridged bicyclic 9 membered heterocycloalkyl including at least one nitrogen atom and optionally substituted with one, two, three, or four $R^{4b}$. In embodiments of the formulae above, $R^{4a}$ is a bridged bicyclic 10 membered heterocycloalkyl including at least one nitrogen atom and optionally substituted with one, two, three, or four $R^{4b}$. In embodiments of the formulae above, $R^{4a}$ is a bridged bicyclic 11 membered heterocycloalkyl including at least one nitrogen atom and optionally substituted with one, two, three, or four $R^{4b}$. In embodiments of the formulae above, $R^{4a}$ is a bridged bicyclic 12 membered heterocycloalkyl including at least one nitrogen atom and optionally substituted with one, two, three, or four $R^{4b}$.

In embodiments of the formulae above, $R^{4a}$ is a spirocyclic bicyclic 5 membered heterocycloalkyl including at least one nitrogen atom and optionally substituted with one, two, three, or four $R^{4b}$. In embodiments of the formulae above, $R^{4a}$ is a spirocyclic bicyclic 6 membered heterocycloalkyl including at least one nitrogen atom and optionally substituted with one, two, three, or four $R^{4b}$. In embodiments of the formulae above, $R^{4a}$ is a spirocyclic bicyclic 7 membered heterocycloalkyl including at least one nitrogen atom and optionally substituted with one, two, three, or four $R^{4b}$. In embodiments of the formulae above, $R^{4a}$ is a spirocyclic bicyclic 8 membered heterocycloalkyl including at least one nitrogen atom and optionally substituted with one, two, three, or four $R^{4b}$. In embodiments of the formulae above, $R^{4a}$ is a spirocyclic bicyclic 9 membered heterocycloalkyl including at least one nitrogen atom and optionally substituted with one, two, three, or four $R^{4b}$. In embodiments of the formulae above, $R^{4a}$ is a spirocyclic bicyclic 10 membered heterocycloalkyl including at least one nitrogen atom and optionally substituted with one, two, three, or four $R^{4b}$. In embodiments of the formulae above, $R^{4a}$ is a spirocyclic bicyclic 11 membered heterocycloalkyl including at least one nitrogen atom and optionally substituted with one, two, three, or four $R^{4b}$. In embodiments of the formulae above, $R^{4a}$ is a spirocyclic bicyclic 12 membered heterocycloalkyl including at least one nitrogen atom and optionally substituted with one, two, three, or four $R^{4b}$.

In embodiments of the formulae above, $R^{4a}$ is a 5 membered heteroaryl optionally substituted with one, two, three, or four $R^{4b}$. In embodiments of the formulae above, $R^{4a}$ is a 6 membered heteroaryl optionally substituted with one, two, three, or four $R^{4b}$. In embodiments of the formulae above, $R^{4a}$ is a 7 membered heteroaryl optionally substituted with one, two, three, or four $R^{4b}$. In embodiments of the formulae above, $R^{4a}$ is a 8 membered heteroaryl optionally substituted with one, two, three, or four $R^{4b}$. In embodiments of the formulae above, $R^{4a}$ is a 9 membered heteroaryl optionally substituted with one, two, three, or four $R^{4b}$. In embodiments of the formulae above, $R^{4a}$ is a 10 membered heteroaryl optionally substituted with one, two, three, or four $R^{4b}$. In embodiments of the formulae above, $R^{4a}$ is a monocyclic 5 membered heteroaryl optionally substituted with one, two, three, or four $R^{4b}$. In embodiments of the formulae above, $R^{4a}$ is a monocyclic 6 membered heteroaryl optionally substituted with one, two, three, or four $R^{4b}$. In embodiments of the formulae above, $R^{4a}$ is a monocyclic 7 membered heteroaryl optionally substituted with one, two, three, or four $R^{4b}$. In embodiments of the formulae above, $R^{4a}$ is a monocyclic 8 membered heteroaryl optionally substituted with one, two, three, or four $R^{4b}$. In embodiments of the formulae above, $R^{4a}$ is a monocyclic 9 membered heteroaryl optionally substituted with one, two, three, or four $R^{4b}$. In embodiments of the formulae above, $R^{4a}$ is a monocyclic 10 membered heteroaryl optionally substituted with one, two, three, or four $R^{4b}$.

In embodiments of the formulae above, $R^{4a}$ is a fused bicyclic 6 membered heteroaryl optionally substituted with one, two, three, or four $R^{4b}$. In embodiments of the formulae above, $R^{4a}$ is a fused bicyclic 7 membered heteroaryl optionally substituted with one, two, three, or four $R^{4b}$. In embodiments of the formulae above, $R^{4a}$ is a fused bicyclic 8 membered heteroaryl optionally substituted with one, two, three, or four $R^{4b}$. In embodiments of the formulae above, $R^{4a}$ is a fused bicyclic 9 membered heteroaryl optionally substituted with one, two, three, or four $R^{4b}$. In embodiments of the formulae above, $R^{4a}$ is a fused bicyclic 10 membered heteroaryl optionally substituted with one, two, three, or four $R^{4b}$.

In embodiments of the formulae above, $R^{4a}$ is a bridged bicyclic 6 membered heteroaryl optionally substituted with one, two, three, or four $R^{4b}$. In embodiments of the formulae above, $R^{4a}$ is a bridged bicyclic 7 membered heteroaryl optionally substituted with one, two, three, or four $R^{4b}$. In embodiments of the formulae above, $R^{4a}$ is a bridged bicyclic 8 membered heteroaryl optionally substituted with one, two, three, or four $R^{4b}$. In embodiments of the formulae above, $R^{4a}$ is a bridged bicyclic 9 membered heteroaryl optionally substituted with one, two, three, or four $R^{4b}$. In embodiments of the formulae above, $R^{4a}$ is a bridged bicyclic 10 membered heteroaryl optionally substituted with one, two, three, or four $R^{4b}$.

In embodiments of the formulae above, $R^{4a}$ is a spirocyclic bicyclic 6 membered heteroaryl optionally substituted with one, two, three, or four $R^{4b}$. In embodiments of the formulae above, $R^{4a}$ is a spirocyclic bicyclic 7 membered heteroaryl optionally substituted with one, two, three, or four $R^{4b}$. In embodiments of the formulae above, $R^{4a}$ is a spirocyclic bicyclic 8 membered heteroaryl optionally substituted with one, two, three, or four $R^{4b}$. In embodiments of the formulae above, $R^{4a}$ is a spirocyclic bicyclic 9 membered heteroaryl optionally substituted with one, two, three, or four $R^{4b}$. In embodiments of the formulae above, $R^{4a}$ is a spirocyclic bicyclic 10 membered heteroaryl optionally substituted with one, two, three, or four $R^{4b}$.

In embodiments of the formulae above, $R^{4a}$ is a 5 membered heteroaryl including at least one nitrogen atom and optionally substituted with one, two, three, or four $R^{4b}$. In embodiments of the formulae above, $R^{4a}$ is a 6 membered heteroaryl including at least one nitrogen atom and optionally substituted with one, two, three, or four $R^{4b}$. In embodiments of the formulae above, $R^{4a}$ is a 7 membered heteroaryl including at least one nitrogen atom and optionally substituted with one, two, three, or four $R^{4b}$. In embodiments of the formulae above, $R^{4a}$ is a 8 membered heteroaryl including at least one nitrogen atom and optionally substituted with one, two, three, or four $R^{4b}$. In embodiments of the formulae above, $R^{4a}$ is a 9 membered heteroaryl including at least one nitrogen atom and optionally substituted with one, two, three, or four $R^{4b}$. In embodiments of the formulae above, $R^{4a}$ is a 10 membered heteroaryl including at least one nitrogen atom and optionally substituted with one, two, three, or four $R^{4b}$.

In embodiments of the formulae above, $R^{4a}$ is a monocyclic 5 membered heteroaryl including at least one nitrogen atom and optionally substituted with one, two, three, or four $R^{4b}$. In embodiments of the formulae above, $R^{4a}$ is a monocyclic 6 membered heteroaryl including at least one nitrogen atom and optionally substituted with one, two, three, or four $R^{4b}$. In embodiments of the formulae above, $R^{4a}$ is a monocyclic 7 membered heteroaryl including at least one nitrogen atom and optionally substituted with one, two, three, or four $R^{4b}$. In embodiments of the formulae above, $R^{4a}$ is a monocyclic 8 membered heteroaryl including at least one nitrogen atom and optionally substituted with one, two, three, or four $R^{4b}$. In embodiments of the formulae above, $R^{4a}$ is a monocyclic 9 membered heteroaryl including at least one nitrogen atom and optionally substituted with one, two, three, or four $R^{4b}$. In embodiments of the formulae above, $R^{4a}$ is a monocyclic 10 membered heteroaryl including at least one nitrogen atom and optionally substituted with one, two, three, or four $R^{4b}$.

In embodiments of the formulae above, $R^{4a}$ is a fused bicyclic 6 membered heteroaryl including at least one nitrogen atom and optionally substituted with one, two, three, or four $R^{4b}$. In embodiments of the formulae above, $R^{4a}$ is a fused bicyclic 7 membered heteroaryl including at least one nitrogen atom and optionally substituted with one, two, three, or four $R^{4b}$. In embodiments of the formulae above, $R^{4a}$ is a fused bicyclic 8 membered heteroaryl including at least one nitrogen atom and optionally substituted with one, two, three, or four $R^{4b}$. In embodiments of the formulae above, $R^{4a}$ is a fused bicyclic 9 membered heteroaryl including at least one nitrogen atom and optionally substituted with one, two, three, or four $R^{4b}$. In embodiments of the formulae above, $R^{4a}$ is a fused bicyclic 10 membered heteroaryl including at least one nitrogen atom and optionally substituted with one, two, three, or four $R^{4b}$.

In embodiments of the formulae above, $R^{4a}$ is a bridged bicyclic 6 membered heteroaryl including at least one nitrogen atom and optionally substituted with one, two, three, or four $R^{4b}$. In embodiments of the formulae above, $R^{4a}$ is a bridged bicyclic 7 membered heteroaryl including at least one nitrogen atom and optionally substituted with one, two, three, or four $R^{4b}$. In embodiments of the formulae above, $R^{4a}$ is a bridged bicyclic 8 membered heteroaryl including at least one nitrogen atom and optionally substituted with one, two, three, or four $R^{4b}$. In embodiments of the formulae above, $R^{4a}$ is a bridged bicyclic 9 membered heteroaryl including at least one nitrogen atom and optionally substituted with one, two, three, or four $R^{4b}$. In embodiments of the formulae above, $R^{4a}$ is a bridged bicyclic 10 membered heteroaryl including at least one nitrogen atom and optionally substituted with one, two, three, or four $R^{4b}$.

In embodiments of the formulae above, $R^{4a}$ is a spirocyclic bicyclic 6 membered heteroaryl including at least one nitrogen atom and optionally substituted with one, two, three, or four $R^{4b}$. In embodiments of the formulae above, $R^{4a}$ is a spirocyclic bicyclic 7 membered heteroaryl including at least one nitrogen atom and optionally substituted with one, two, three, or four $R^{4b}$. In embodiments of the formulae above, $R^{4a}$ is a spirocyclic bicyclic 8 membered heteroaryl including at least one nitrogen atom and optionally substituted with one, two, three, or four $R^{4b}$. In embodiments of the formulae above, $R^{4a}$ is a spirocyclic bicyclic 9 membered heteroaryl including at least one nitrogen atom and optionally substituted with one, two, three, or four $R^{4b}$. In embodiments of the formulae above, $R^{4a}$ is a spirocyclic bicyclic 10 membered heteroaryl including at least one nitrogen atom and optionally substituted with one, two, three, or four $R^{4b}$.

In embodiments of the formulae above, $R^{4a}$ is a 3 membered heterocycloalkyl including at least one oxygen atom and optionally substituted with one, two, three, or four $R^{4b}$. In embodiments of the formulae above, $R^{4a}$ is a 4 membered heterocycloalkyl including at least one oxygen atom and optionally substituted with one, two, three, or four $R^{4b}$. In embodiments of the formulae above, $R^{4a}$ is a 5 membered heterocycloalkyl including at least one oxygen atom and optionally substituted with one, two, three, or four $R^{4b}$. In embodiments of the formulae above, $R^{4a}$ is a 6 membered heterocycloalkyl including at least one oxygen atom and optionally substituted with one, two, three, or four $R^{4b}$. In embodiments of the formulae above, $R^{4a}$ is a 7 membered heterocycloalkyl including at least one oxygen atom and optionally substituted with one, two, three, or four $R^{4b}$. In embodiments of the formulae above, $R^{4a}$ is a 8 membered heterocycloalkyl including at least one oxygen atom and optionally substituted with one, two, three, or four $R^{4b}$. In embodiments of the formulae above, $R^{4a}$ is a 9 membered heterocycloalkyl including at least one oxygen atom and optionally substituted with one, two, three, or four $R^{4b}$. In embodiments of the formulae above, $R^{4a}$ is a 10 membered heterocycloalkyl including at least one oxygen atom and optionally substituted with one, two, three, or four $R^{4b}$. In embodiments of the formulae above, $R^{4a}$ is a 11 membered heterocycloalkyl including at least one oxygen atom and optionally substituted with one, two, three, or four $R^{4b}$. In embodiments of the formulae above, $R^{4a}$ is a 12 membered heterocycloalkyl including at least one oxygen atom and optionally substituted with one, two, three, or four $R^{4b}$. In embodiments of the formulae above, $R^{4a}$ is a monocyclic 4 membered heterocycloalkyl including at least one oxygen atom and optionally substituted with one, two, three, or four $R^{4b}$.

In embodiments of the formulae above, $R^{4a}$ is a 11 membered heterocycloalkyl including at least one oxygen atom and optionally substituted with one, two, three, or four $R^{4b}$. In embodiments of the formulae above, $R^{4a}$ is a 12 membered heterocycloalkyl including at least one oxygen atom and optionally substituted with one, two, three, or four $R^{4b}$. In embodiments of the formulae above, $R^{4a}$ is a monocyclic 4 membered heterocycloalkyl including at least one oxygen atom and optionally substituted with one, two, three, or four $R^{4b}$. In embodiments of the formulae above, $R^{4a}$ is a monocyclic 5 membered heterocycloalkyl including at least one oxygen atom and optionally substituted with one, two, three, or four $R^{4b}$. In embodiments of the formulae above, $R^{4a}$ is a monocyclic 6 membered heterocycloalkyl including at least one oxygen atom and optionally substituted with one, two, three, or four $R^{4b}$. In embodiments of the formulae above, $R^{4a}$ is a monocyclic 7 membered heterocycloalkyl including at least one oxygen atom and optionally substituted with one, two, three, or four $R^{4b}$. In embodiments of the formulae above, $R^{4a}$ is a monocyclic 8 membered heterocycloalkyl including at least one oxygen atom and optionally substituted with one, two, three, or four $R^{4b}$. In embodiments of the formulae above, $R^{4a}$ is a monocyclic 9 membered heterocycloalkyl including at least one oxygen atom and optionally substituted with one, two, three, or four $R^{4b}$. In embodiments of the formulae above, $R^{4a}$ is a monocyclic 10 membered heterocycloalkyl including at least one oxygen atom and optionally substituted with one, two, three, or four $R^{4b}$.

In embodiments of the formulae above, $R^{4a}$ is a fused bicyclic 5 membered heterocycloalkyl including at least one oxygen atom and optionally substituted with one, two, three, or four $R^{4b}$. In embodiments of the formulae above, $R^{4a}$ is a fused bicyclic 6 membered heterocycloalkyl including at least one oxygen atom and optionally substituted with one, two, three, or four $R^{4b}$. In embodiments of the formulae above, $R^{4a}$ is a fused bicyclic 7 membered heterocycloalkyl including at least one oxygen atom and optionally substituted with one, two, three, or four $R^{4b}$. In embodiments of the formulae above, $R^{4a}$ is a fused bicyclic 8 membered heterocycloalkyl including at least one oxygen atom and optionally substituted with one, two, three, or four $R^{4b}$. In embodiments of the formulae above, $R^{4a}$ is a fused bicyclic 9 membered heterocycloalkyl including at least one oxygen atom and optionally substituted with one, two, three, or four $R^{4b}$. In embodiments of the formulae above, $R^{4a}$ is a fused bicyclic 10 membered heterocycloalkyl including at least one oxygen atom and optionally substituted with one, two, three, or four $R^{4b}$. In embodiments of the formulae above, $R^{4a}$ is a fused bicyclic 11 membered heterocycloalkyl including at least one oxygen atom and optionally substituted with one, two, three, or four $R^{4b}$. In embodiments of the formulae above, $R^{4a}$ is a fused bicyclic 12 membered heterocycloalkyl including at least one oxygen atom and optionally substituted with one, two, three, or four $R^{4b}$.

In embodiments of the formulae above, $R^{4a}$ is a bridged bicyclic 5 membered heterocycloalkyl including at least one oxygen atom and optionally substituted with one, two, three, or four $R^{4b}$. In embodiments of the formulae above, $R^{4a}$ is a bridged bicyclic 6 membered heterocycloalkyl including at least one oxygen atom and optionally substituted with one, two, three, or four $R^{4b}$. In embodiments of the formulae above, $R^{4a}$ is a bridged bicyclic 7 membered heterocycloalkyl including at least one oxygen atom and optionally substituted with one, two, three, or four $R^{4b}$. In embodiments of the formulae above, $R^{4a}$ is a bridged bicyclic 8 membered heterocycloalkyl including at least one oxygen atom and optionally substituted with one, two, three, or four $R^{4b}$. In embodiments of the formulae above, $R^{4a}$ is a bridged bicyclic 9 membered heterocycloalkyl including at least one oxygen atom and optionally substituted with one, two, three, or four $R^{4b}$. In embodiments of the formulae above, $R^{4a}$ is a bridged bicyclic 10 membered heterocycloalkyl including at least one oxygen atom and optionally substituted with one, two, three, or four $R^{4b}$. In embodiments of the formulae above, $R^{4a}$ is a bridged bicyclic 11 membered heterocycloalkyl including at least one oxygen atom and optionally substituted with one, two, three, or four $R^{4b}$. In embodiments of the formulae above, $R^{4a}$ is a bridged bicyclic 12 membered heterocycloalkyl including at least one oxygen atom and optionally substituted with one, two, three, or four $R^{4b}$.

In embodiments of the formulae above, $R^{4a}$ is a spirocyclic bicyclic 5 membered heterocycloalkyl including at least one oxygen atom and optionally substituted with one, two, three, or four $R^{4b}$. In embodiments of the formulae above, $R^{4a}$ is a spirocyclic bicyclic 6 membered heterocycloalkyl including at least one oxygen atom and optionally substituted with one, two, three, or four $R^{4b}$. In embodiments of the formulae above, $R^{4a}$ is a spirocyclic bicyclic 7 membered heterocycloalkyl including at least one oxygen atom and optionally substituted with one, two, three, or four $R^{4b}$. In embodiments of the formulae above, $R^{4a}$ is a spirocyclic bicyclic 8 membered heterocycloalkyl including at least one oxygen atom and optionally substituted with one, two, three, or four $R^{4b}$. In embodiments of the formulae above, $R^{4a}$ is a spirocyclic bicyclic 9 membered heterocycloalkyl including at least one oxygen atom and optionally substituted with one, two, three, or four $R^{4b}$. In embodiments of the formulae above, $R^{4a}$ is a spirocyclic bicyclic 10 membered heterocycloalkyl including at least one oxygen atom and optionally substituted with one, two, three, or four $R^{4b}$. In embodiments of the formulae above, $R^{4a}$ is a spirocyclic bicyclic 11 membered heterocycloalkyl including at least one oxygen atom and optionally substituted with one, two, three, or four $R^{4b}$. In embodiments of the formulae above, $R^{4a}$ is a spirocyclic bicyclic 12 membered heterocycloalkyl including at least one oxygen atom and optionally substituted with one, two, three, or four $R^{4b}$.

In embodiments of the formulae above, $R^{4a}$ is a 5 membered heteroaryl including at least one oxygen atom and optionally substituted with one, two, three, or four $R^{4b}$. In embodiments of the formulae above, $R^{4a}$ is a 6 membered heteroaryl including at least one oxygen atom and optionally substituted with one, two, three, or four $R^{4b}$. In embodiments of the formulae above, $R^{4a}$ is a 7 membered heteroaryl including at least one oxygen atom and optionally substituted with one, two, three, or four $R^{4b}$. In embodiments of the formulae above, $R^{4a}$ is a 8 membered heteroaryl including at least one oxygen atom and optionally substituted with one, two, three, or four $R^{4b}$. In embodiments of the formulae above, $R^{4a}$ is a 9 membered heteroaryl including at least one oxygen atom and optionally substituted with one, two, three, or four $R^{4b}$. In embodiments of the formulae above, $R^{4a}$ is a 10 membered heteroaryl including at least one oxygen atom and optionally substituted with one, two, three, or four $R^{4b}$.

In embodiments of the formulae above, $R^{4a}$ is a monocyclic 5 membered heteroaryl including at least one oxygen atom and optionally substituted with one, two, three, or four $R^{4b}$. In embodiments of the formulae above, $R^{4a}$ is a monocyclic 6 membered heteroaryl including at least one oxygen atom and optionally substituted with one, two, three, or four $R^{4b}$. In embodiments of the formulae above, $R^{4a}$ is a monocyclic 7 membered heteroaryl including at least one oxygen atom and optionally substituted with one, two, three, or four $R^{4b}$. In embodiments of the formulae above, $R^{4a}$ is a monocyclic 8 membered heteroaryl including at least one oxygen atom and optionally substituted with one, two, three, or four $R^{4b}$. In embodiments of the formulae above, $R^{4a}$ is a monocyclic 9 membered heteroaryl including at least one oxygen atom and optionally substituted with one, two, three, or four $R^{4b}$. In embodiments of the formulae above, $R^{4a}$ is a monocyclic 10 membered heteroaryl including at least one oxygen atom and optionally substituted with one, two, three, or four $R^{4b}$.

In embodiments of the formulae above, $R^{4a}$ is a fused bicyclic 6 membered heteroaryl including at least one oxygen atom and optionally substituted with one, two, three, or four $R^{4b}$. In embodiments of the formulae above, $R^{4a}$ is a fused bicyclic 7 membered heteroaryl including at least one oxygen atom and optionally substituted with one, two, three, or four $R^{4b}$. In embodiments of the formulae above, $R^{4a}$ is a fused bicyclic 8 membered heteroaryl including at least one oxygen atom and optionally substituted with one, two, three, or four $R^{4b}$. In embodiments of the formulae above, $R^{4a}$ is a fused bicyclic 9 membered heteroaryl including at least one oxygen atom and optionally substituted with one, two, three, or four $R^{4b}$. In embodiments of the formulae above, $R^{4a}$ is a fused bicyclic 10 membered heteroaryl including at least one oxygen atom and optionally substituted with one, two, three, or four $R^{4b}$.

In embodiments of the formulae above, $R^{4a}$ is a bridged bicyclic 6 membered heteroaryl including at least one oxygen atom and optionally substituted with one, two, three, or four $R^{4b}$. In embodiments of the formulae above, $R^{4a}$ is a bridged bicyclic 7 membered heteroaryl including at least one oxygen atom and optionally substituted with one, two, three, or four $R^{4b}$. In embodiments of the formulae above, $R^{4a}$ is a bridged bicyclic 8 membered heteroaryl including at least one oxygen atom and optionally substituted with one, two, three, or four $R^{4b}$. In embodiments of the formulae above, $R^{4a}$ is a bridged bicyclic 9 membered heteroaryl including at least one oxygen atom and optionally substituted with one, two, three, or four $R^{4b}$. In embodiments of the formulae above, $R^{4a}$ is a bridged bicyclic 10 membered heteroaryl including at least one oxygen atom and optionally substituted with one, two, three, or four $R^{4b}$.

In embodiments of the formulae above, $R^{4a}$ is a spirocyclic bicyclic 6 membered heteroaryl including at least one oxygen atom and optionally substituted with one, two, three, or four $R^{4b}$. In embodiments of the formulae above, $R^{4a}$ is a spirocyclic bicyclic 7 membered heteroaryl including at least one oxygen atom and optionally substituted with one, two, three, or four $R^{4b}$. In embodiments of the formulae above, $R^{4a}$ is a spirocyclic bicyclic 8 membered heteroaryl including at least one oxygen atom and optionally substituted with one, two, three, or four $R^{4b}$. In embodiments of the formulae above, $R^{4a}$ is a spirocyclic bicyclic 9 membered heteroaryl including at least one oxygen atom and optionally substituted with one, two, three, or four $R^{4b}$. In embodiments of the formulae above, $R^{4a}$ is a spirocyclic bicyclic 10 membered heteroaryl including at least one oxygen atom and optionally substituted with one, two, three, or four $R^{4b}$.

In embodiments of the formulae above, $R^{4a}$ is a 4-12 membered cycloalkyl comprising one or more ring nitrogen atoms. In embodiments of the formulae above, $R^{4a}$ is a 5-12 membered cycloalkyl comprising one or more ring nitrogen atoms. In embodiments of the formulae above, $R^{4a}$ is 3-12 membered heterocycloalkyl comprising one or more ring nitrogen atoms. In embodiments of the formulae above, $R^{4a}$ is 7-12 membered aryl comprising one or more ring nitrogen atoms. In embodiments of the formulae above, $R^{4a}$ is 5-12 membered heteroaryl comprising one or more ring nitrogen atoms.

In some embodiments of the formulae above, each $R^{4b}$ is independently halogen. In some embodiments of the formulae above, each $R^{4b}$ is independently oxo. In some embodiments of the formulae above, each $R^{4b}$ is independently —CN. In some embodiments of the formulae above, each $R^{4b}$ is independently $C_{1-6}$alkyl. In some embodiments of the formulae above, each $R^{4b}$ is independently $C_{2-6}$alkenyl. In some embodiments of the formulae above, each $R^{4b}$ is independently $C_{2-6}$alkynyl. In some embodiments of the formulae above, each $R^{4b}$ is independently $C_{3-12}$cycloalkyl. In some embodiments of the formulae above, each $R^{4b}$ is independently $C_{2-11}$heterocycloalkyl. In some embodiments of the formulae above, each $R^{4b}$ is independently $C_{6-10}$aryl. In some embodiments of the formulae above, each $R^{4b}$ is independently $C_{1-9}$heteroaryl. In some embodiments of the formulae above, each $R^{4b}$ is independently —$OR^{12}$. In some embodiments of the formulae above, each $R^{4b}$ is independently —$SR^{12}$. In some embodiments of the formulae above, each $R^{4b}$ is independently —$N(R^{12})(R^{13})$. In some embodiments of the formulae above, each $R^{4b}$ is independently —$C(O)OR^{12}$. In some embodiments of the formulae above,
each $R^{4b}$ is independently —$OC(O)N(R^{12})(R^{13})$. In some embodiments of the formulae above, each $R^{4b}$ is independently —$N(R^{14})C(O)N(R^{12})(R^{13})$. In some embodiments of the formulae above, each $R^{4b}$ is independently —$N(R^{14})C(O)OR^{15}$. In some embodiments of the formulae above, each $R^{4b}$ is independently —$N(R^{14})S(O)_2R^{15}$. In some embodiments of the formulae above, each $R^{4b}$ is independently —$C(O)R^{15}$. In some embodiments of the formulae above, each $R^{4b}$ is independently —$C(O)R^{12}$. In some embodiments of the formulae above, each $R^{4b}$ is independently —$S(O)R^{15}$. In some embodiments of the formulae above, each $R^{4b}$ is independently —$OC(O)R^{15}$. In some embodiments of the formulae above, each $R^{4b}$ is independently —$C(O)N(R^{12})(R^{13})$. In some embodiments of the formulae above, each $R^{4b}$ is independently —$C(O)C(O)N(R^{12})(R^{13})$. In some embodiments of the formulae above, each $R^{4b}$ is independently —$N(R^{14})C(O)R^{15}$. In some embodiments of the formulae above, each $R^{4b}$ is independently —$C(O)C(O)N(R^{12})(R^{13})$. In some embodiments of the formulae above, each $R^{4b}$ is independently —$N(R^{14})C(O)R^{12}$.

In some embodiments of the formulae above, each $R^{4b}$ is independently —$S(O)_2R^{15}$. In some embodiments of the formulae above, each $R^{4b}$ is independently —$S(O)_2N(R^{12})(R^{13})$—. In some embodiments of the formulae above, each $R^{4b}$ is independently —$S(=O)(=NH)N(R^{12})(R^{13})$. In some embodiments of the formulae above, each $R^{4b}$ is independently —$CH_2C(O)N(R^{12})(R^{13})$. In some embodiments of the formulae above, each $R^{4b}$ is independently —$CH_2N(R^{14})C(O)R^{15}$. In some embodiments of the formulae above;

each $R^{4b}$ is independently —$CH_2S(O)_2R^{15}$. In some embodiments of the formulae above, each $R^{4b}$ is independently —$CH_2S(O)_2N(R^{12})(R^{13})$. In some embodiments of the formulae above, each $R^{4b}$ is independently —$C(O)R^{12}$. In some embodiments of the formulae above, each $R^{4b}$ is independently —$C(O)H$. In some embodiments of the formulae above, each $R^{4b}$ is independently —$P(=O)(R^{12})_2$. In embodiments of the formulae above, each $R^{4b}$ is independently —$CH_2N(R^{14})C(O)R^{12}$. In embodiments of the formulae above, each $R^{4b}$ is independently —$N(R^{14})C(O)R^{12}$.

In some embodiments of the formulae above, each $R^{4b}$ is independently $C_{1-6}$alkyl substituted with one or more $R^{20}j$. In some embodiments of the formulae above, each $R^{4b}$ is independently $C_{2-6}$alkenyl substituted with one or more $R^{20}j$. In some embodiments of the formulae above, each $R^{4b}$ is independently $C_{2-6}$alkynyl substituted with one or more $R^{20}j$. In some embodiments of the formulae above, each $R^{4b}$ is independently $C_{3-12}$cycloalkyl substituted with one or more $R^{20}j$. In some embodiments of the formulae above, each $R^{4b}$ is independently $C_{2-11}$heterocycloalkyl substituted with one or more $R^{20}j$. In some embodiments of the formulae above;

each $R^{4b}$ is independently $C_{6-10}$aryl substituted with one or more $R^{20}j$. In some embodiments of the formulae above, each $R^{4b}$ is independently $C_{1-9}$heteroaryl substituted with one or more $R^{20}j$.

In embodiments of the formulae above, $R^{4b}$ is independently halogen. In embodiments of the formulae above, $R^{4b}$ is independently F. In embodiments of the formulae above, $R^{4b}$ is independently $C_1$. In embodiments of the formulae above, $R^{4b}$ is independently Br. In embodiments of the formulae above, $R^{4b}$ is independently I. In embodiments of the formulae above, $R^{4b}$ is independently $R^{4b}$ is independently oxo. In embodiments of the formulae above, $R^{4b}$ is independently —CN. In embodiments of the formulae above, $R^{4b}$ is independently $C_{1-6}$alkyl. In embodiments of the formulae above, $R^{4b}$ is independently methyl. In embodiments of the formulae above, $R^{4b}$ is independently ethyl. In embodiments of the formulae above, $R^{4b}$ is independently isopropyl. In embodiments of the formulae above, $R^{4b}$ is independently $C_{2-6}$alkenyl. In embodiments of the formulae above, $R^{4b}$ is independently $C_{2-6}$alkynyl. In embodiments of the formulae above, $R^{4b}$ is independently $C_{1-6}$haloalkyl. In embodiments of the formulae above, $R^{4b}$ is independently —CF3. In embodiments of the formulae above, $R^{4b}$ is independently $C_{3-12}$cycloalkyl. In embodiments of the formulae above, $R^{4b}$ is independently —$CH_2$-$C_{3-12}$cycloalkyl. In embodiments of the formulae above, $R^{4b}$ is independently $C_{2-11}$heterocycloalkyl. In embodiments of the formulae above, $R^{4b}$ is independently —$CH_2$-$C_{2-11}$heterocycloalkyl. In embodiments of the formulae above, $R^{4b}$ is independently $C_{6-12}$aryl. In embodiments of the formulae above, $R^{4b}$ is independently —$CH_2$-$C_6$-12aryl. In embodiments of the formulae above, $R^{4b}$ is independently —$CH_2$-$C_{1-11}$heteroaryl. In embodiments of the formulae above, $R^{4b}$ is independently $C_{1-11}$heteroaryl. In embodiments of the formulae above, $R^{4b}$ is independently —OH. In embodiments of the formulae above, $R^{4b}$ is independently —$OCH_3$. In embodiments of the formulae above, $R^{4b}$ is independently —SH. In embodiments of the formulae above, $R^{4b}$ is independently —$SCH_3$. In embodiments of the formulae above, $R^{4b}$ is independently —$N(CH_3)_2$. In embodiments of the formulae above, $R^{4b}$ is independently —$N(H)_2$. In embodiments of the formulae above, $R^{4b}$ is independently —C(O)OH. In embodiments of the formulae above, $R^{4b}$ is independently —$C(O)OCH_3$. In embodiments of the formulae above, $R^{4b}$ is independently —$OC(O)N(H)_2$. In embodiments of the formulae above, $R^{4b}$ is independently —$OC(O)N(CH_3)_2$. In embodiments of the formulae above, $R^{4b}$ is independently —$N(H)C(O)N(CH_3)_2$. In embodiments of the formulae above, $R^{4b}$ is independently —$N(H)C(O)N(H)_2$. In embodiments of the formulae above, $R^{4b}$ is independently —N(H)C(O)OH. In embodiments of the formulae above, $R^{4b}$ is independently —$N(H)C(O)OCH_3$. In embodiments of the formulae above, $R^{4b}$ is independently —$N(H)S(O)_2CH_3$. In embodiments of the formulae above, $R^{4b}$ is independently —$C(O)CH_3$. In embodiments of the formulae above, $R^{4b}$ is independently —C(O)H. In embodiments of the formulae above, $R^{4b}$ is independently —$S(O)CH_3$. In embodiments of the formulae above, $R^{4b}$ is independently —$OC(O)CH_3$. In embodiments of the formulae above, $R^{4b}$ is independently —OC(O)H. In embodiments of the formulae above, $R^{4b}$ is independently —$C(O)N(CH_3)_2$. In embodiments of the formulae above, $R^{4b}$ is independently —$C(O)C(O)N(CH_3)_2$. In embodiments of the formulae above, $R^{4b}$ is independently —N(H)C(O)H. In embodiments of the formulae above, $R^{4b}$ is independently —$N(H)C(O)CH_3$. In embodiments of the formulae above, $R^{4b}$ is independently —$S(O)_2CH_3$. In embodiments of the formulae above, $R^{4b}$ is independently —$S(O)_2N(H)_2$. In embodiments of the formulae above, $R^{4b}$ is independently —$S(O)_2N(CH_3)_2$. In embodiments of the formulae above, $R^{4b}$ is independently $S(=O)(=NH)N(H)_2$. In embodiments of the formulae above, $R^{4b}$ is independently $S(=O)(=NH)N(CH_3)_2$. In embodiments of the formulae above, $R^{4b}$ is independently —$CH_2C(O)N(H)_2$. In embodiments of the formulae above, $R^{4b}$ is independently —$CH_2C(O)N(CH_3)_2$. In embodiments of the formulae above, $R^{4b}$ is independently —$CH_2N(H)C(O)H$. In embodiments of the formulae above, $R^{4b}$ is independently —$CH_2N(H)C(O)CH_3$. In embodiments of the formulae above, $R^{4b}$ is independently —$CH_2S(O)_2H$. In embodiments of the formulae above, $R^{4b}$ is independently —$CH_2S(O)_2CH_3$. In embodiments of the formulae above, $R^{4b}$ is independently and —$CH_2S(O)_2N(CH_3)_2$. In embodiments of the formulae above, $R^{4b}$ is independently and —$CH_2S(O)_2N(H)_2$. In embodiments of the formulae above, $R^{4b}$ is independently and $=C(R^{21}b)_2$.

In embodiments of the formulae above, $R^{4b}$ is independently $C_{1-6}$alkyl optionally substituted with one, two, or three $R^{20}j$. In embodiments of the formulae above, $R^{4b}$ is independently $C_{2-6}$alkenyl optionally substituted with one, two, or three $R^{20}j$. In embodiments of the formulae above, $R^{4b}$ is independently $C_{2-6}$alkynyl optionally substituted with one, two, or three $R^{20}j$. In embodiments of the formulae above, $R^{4b}$ is independently $C_{1-6}$haloalkyl optionally substituted with one, two, or three $R^{20}j$. In embodiments of the formulae above, $R^{4b}$ is independently $C_{3-12}$cycloalkyl optionally substituted with one, two, or three $R^{20}j$. In embodiments of the formulae above, $R^{4b}$ is independently —$CH_2$-$C_{3-12}$cycloalkyl optionally substituted with one, two, or three $R^{20}j$. In embodiments of the formulae above, $R^{4b}$ is independently $C_{2-11}$heterocycloalkyl optionally substituted with one, two, or three $R^{20}j$. In embodiments of the formulae above, $R^{4b}$ is independently —$CH_2$-$C_{2-11}$heterocycloalkyl optionally substituted with one, two, or three $R^{20}j$. In embodiments of the formulae above, $R^{4b}$ is independently $C_{6-12}$aryl optionally substituted with one, two, or three $R^{20}j$. In embodiments of the formulae above, $R^{4b}$ is independently —$CH_2$-$C_6$-12aryl optionally substituted with one, two, or three $R^{20}j$. In embodiments of the formulae above, $R^{4b}$ is independently —$CH_2$-$C_{1-11}$heteroaryl optionally substituted with one, two, or three $R^{20}j$. In embodiments of the formulae above, $R^{4b}$ is independently $C_{1-11}$heteroaryl optionally substituted with one, two, or three $R^{20}j$.

In embodiments of the formulae above, each $R^{20}j$ is independently halogen. In embodiments of the formulae above;

each $R^{20}j$ is independently oxo. In embodiments of the formulae above, each $R^{20}j$ is independently —CN. In embodiments of the formulae above, each $R^{20}j$ is independently $C_{1-6}$alkyl. In embodiments of the formulae above, each $R^{20}j$ is independently $C_{2-6}$alkenyl. In embodiments of the formulae above, each $R^{20}j$ is independently $C_{2-6}$alkynyl. In embodiments of the formulae above, each $R^{20}j$ is independently $C_{3-10}$cycloalkyl. In embodiments of the formulae above, each $R^{20}j$ is independently —$CH_2$-$C_{3-10}$cycloalkyl. In embodiments of the formulae above, each $R^{20}j$ is independently $C_{2-9}$heterocycloalkyl. In embodiments of the formulae above, each $R^{20}j$ is independently —$CH_2$-$C_{2-9}$heterocycloalkyl. In embodiments of the formulae above, each $R^{20}j$ is independently $C_{6-10}$aryl. In embodiments of the formulae above, each $R^{20}j$ is independently —$CH_2$-$C_6$-10aryl. In embodiments of the formulae above, each $R^{20}j$ is independently —$CH_2$-$C_{1-9}$heteroaryl. In embodiments of the formulae above, each $R^{20}j$ is independently $C_{1-9}$heteroaryl. In embodiments of the formulae above, each $R^{20}j$ is independently —$OR^{21}$. In embodiments of the formulae above, each $R^{20j}$ is independently —$SR^{21}$. In embodiments of the formulae above, each $R^{20j}$ is independently —$N(R^{22})(R^{23})$. In embodiments of the formulae above, each $R^{20j}$ is independently —$C(O)OR^{22}$. In embodiments of the formulae above, each $R^{20j}$ is independently —$C(O)N(R^{22})(R^{23})$. In embodiments of the formulae above, each $R^{20j}$ is independently —$C(O)C(O)N(R^{22})(R^{23})$. In embodiments of the formulae above, each $R^{20j}$ is independently —$OC(O)N(R^{22})(R^{23})$. In embodiments of the formulae above, each $R^{20j}$ is independently —$N(R^{24})C(O)N(R^{22})(R^{23})$. In embodiments of the formulae above, each $R^{20j}$ is independently —$N(R^{24})C(O)OR^{25}$. In embodiments of the formulae above, each $R^{20j}$ is independently —$N(R^{24})C(O)R^{25}$. In embodiments of the formulae above, each $R^{20j}$ is independently —$N(R^{24})C(O)R^{21}$. In embodiments of the formulae above, each $R^{20j}$ is independently —$C(O)R^{21}$. In embodiments of the formulae above, each $R^{20j}$ is independently —$N(R^{24})S(O)_2R^{25}$. In embodiments of the formulae above, each $R^{20j}$ is independently —$C(O)R^{25}$. In embodiments of the formulae above;

each $R^{20j}$ is independently —$S(O)_2R^{25}$. In embodiments of the formulae above, each $R^{20j}$ is independently —$S(O)_2N(R^{22})(R^{23})$. In embodiments of the formulae above, each $R^{20j}$ is independently —$OCH_2C(O)OR^{22}$. In embodiments of the formulae above, each $R^{20j}$ is independently —$OC(O)R^{25}$. In embodiments of the formulae above, each $R^{20j}$ is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above;

each $R^{20j}$ is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently $C_{2-6}$alkynyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently $C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently —$CH_2$-$C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently $C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above;

each $R^{20j}$ is independently —$CH_2$-$C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently $C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently —$CH_2$-$C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently —$CH_2$-$C_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20j}$ is independently $C_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.
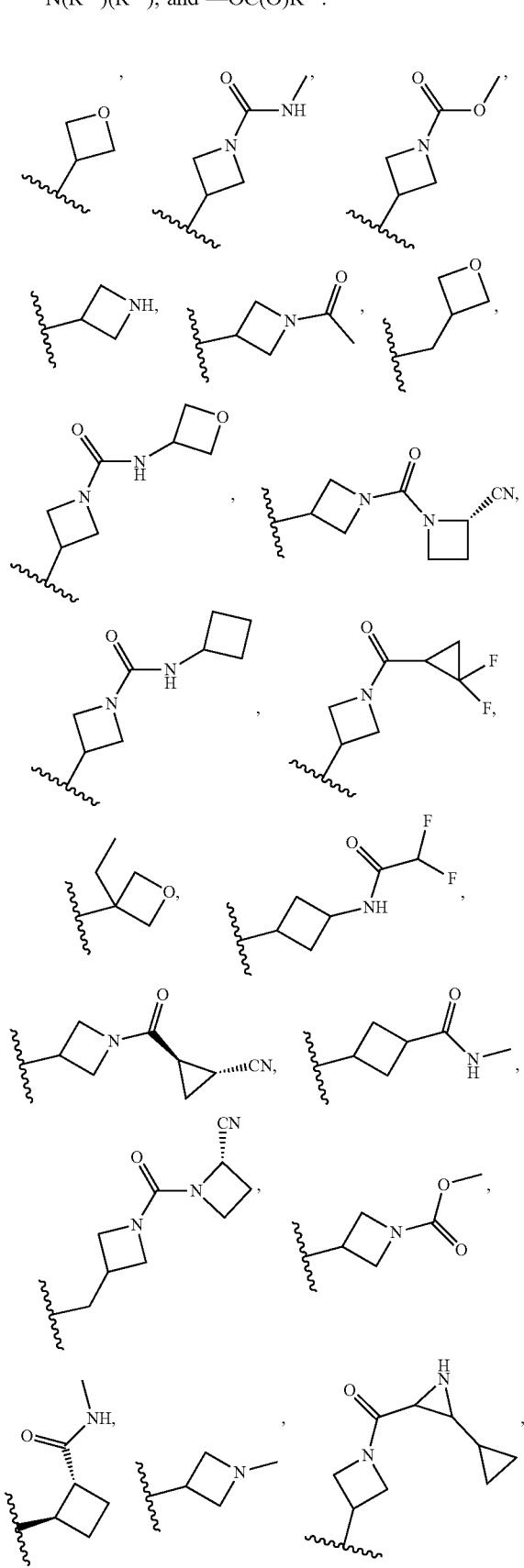
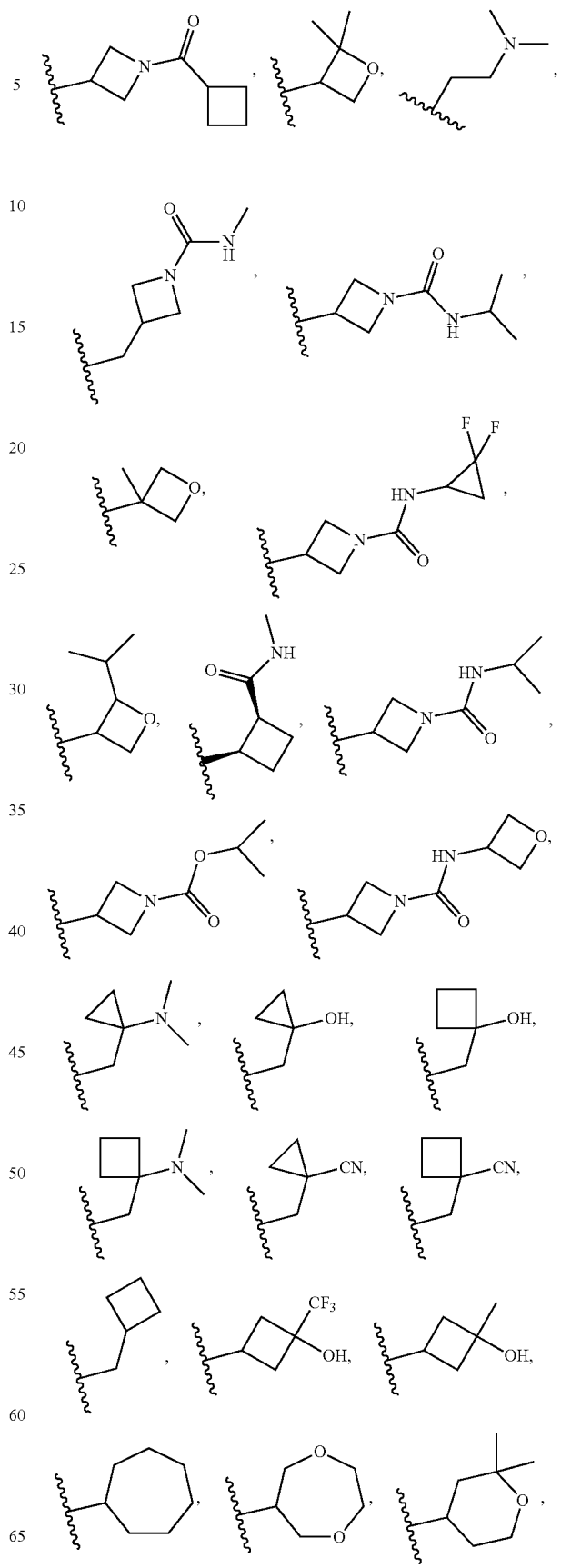

563
-continued
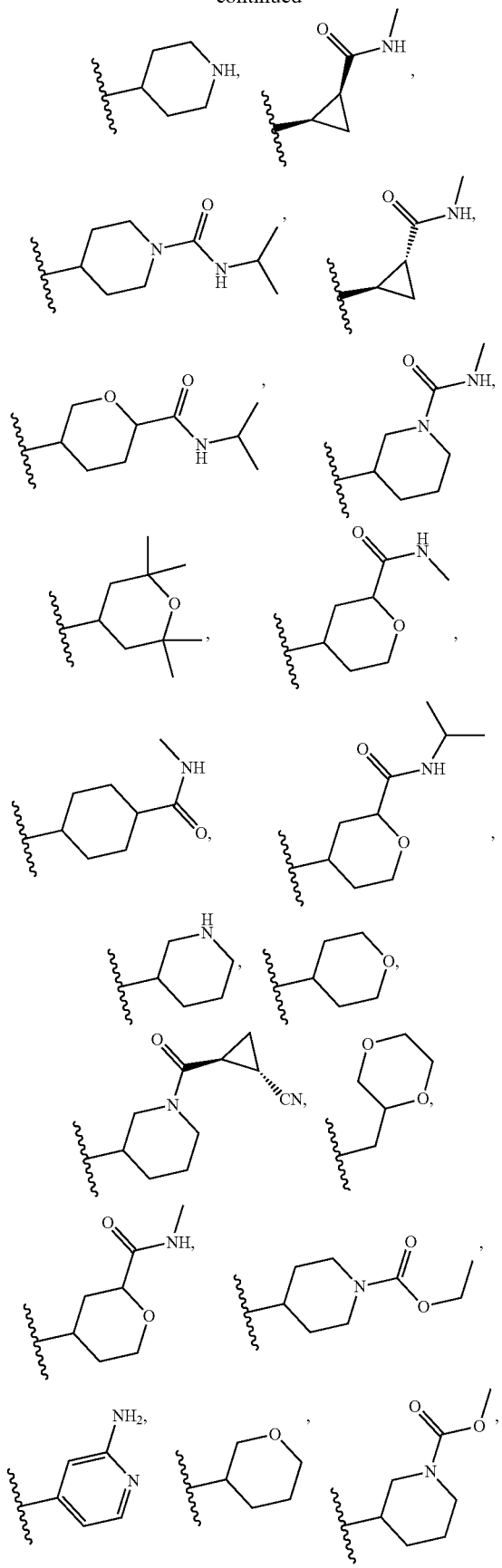
564
-continued
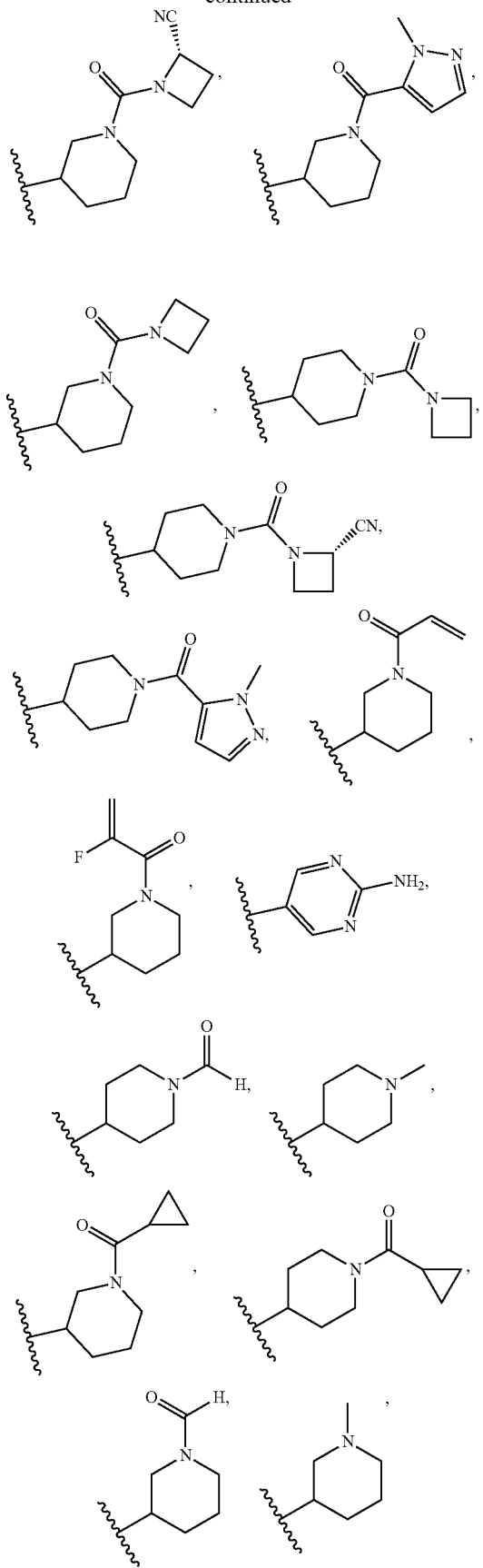

565
-continued
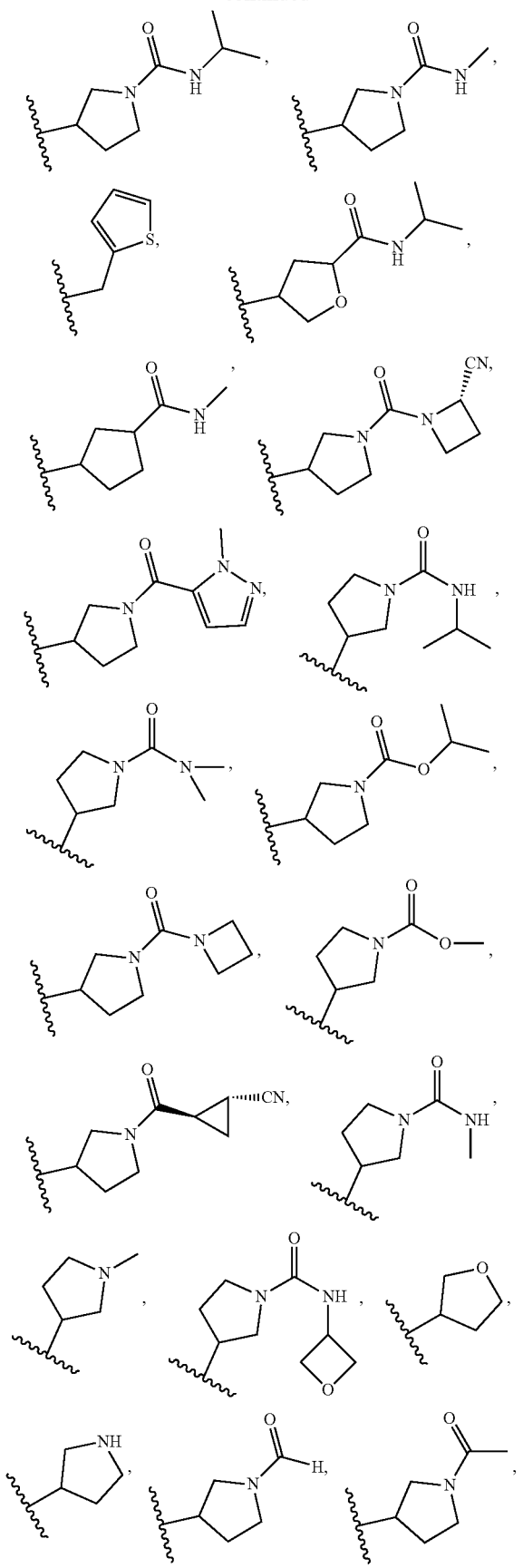
566
-continued
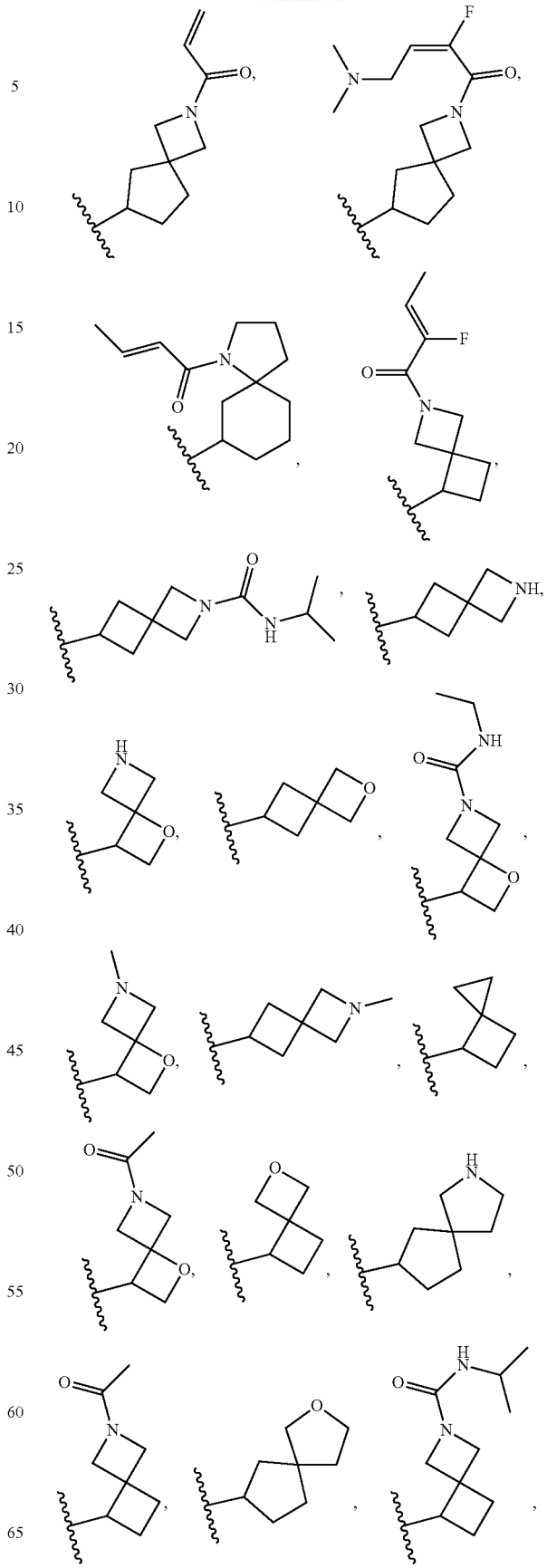

567
-continued
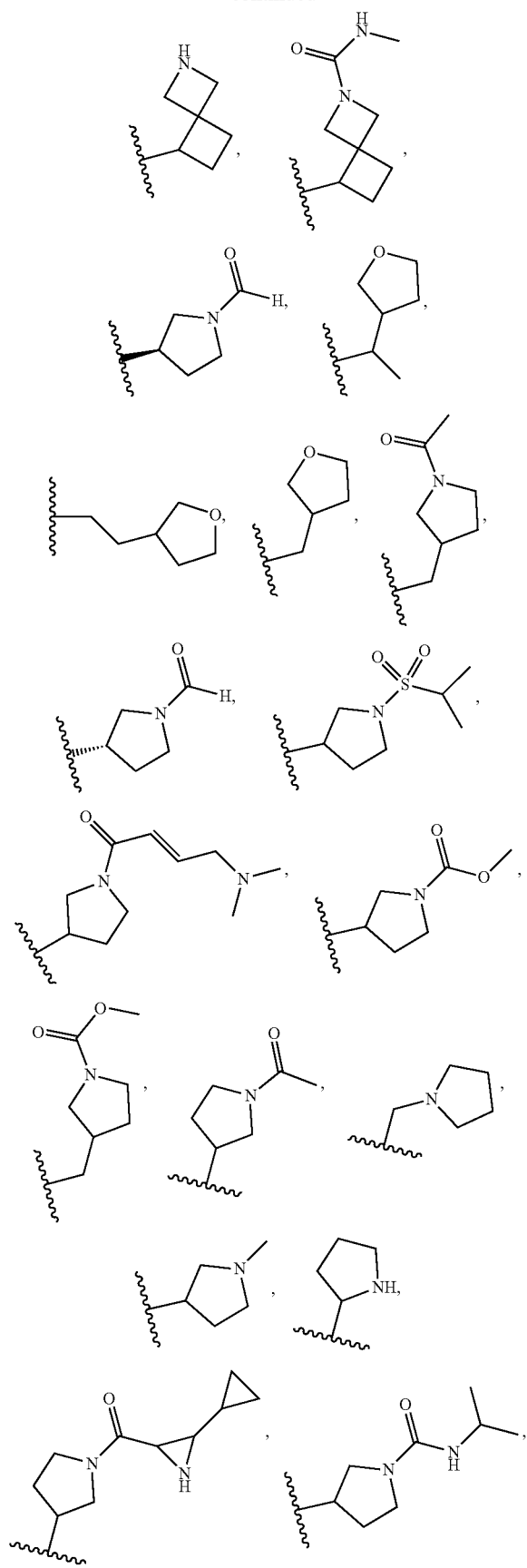
568
-continued
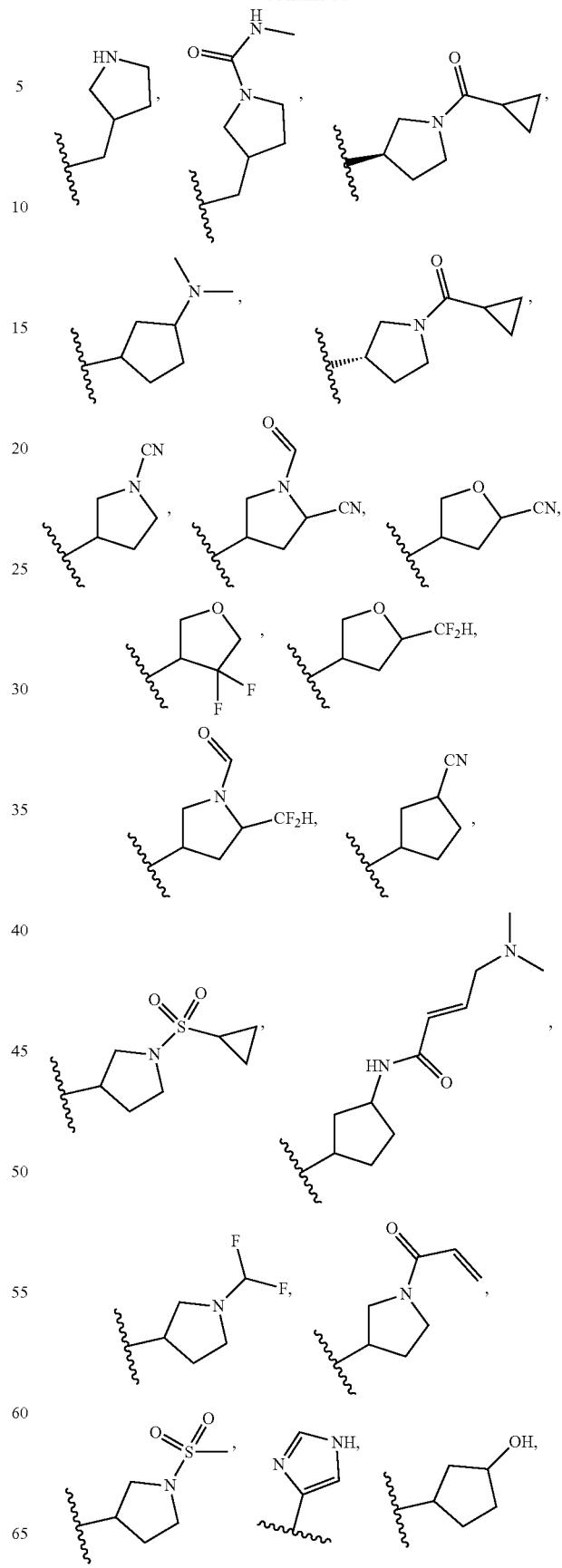

-continued
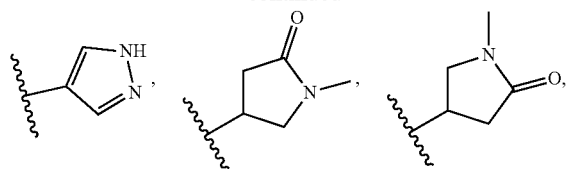
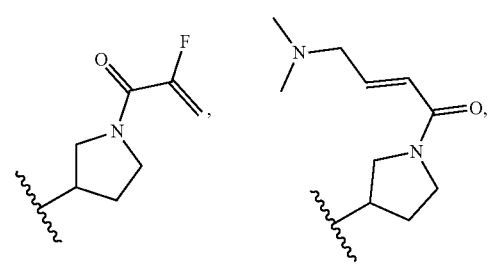
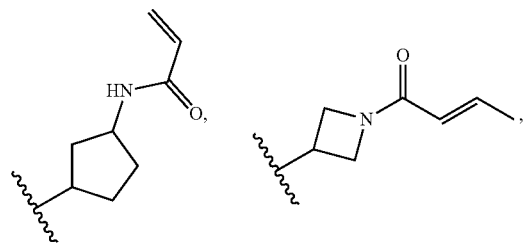
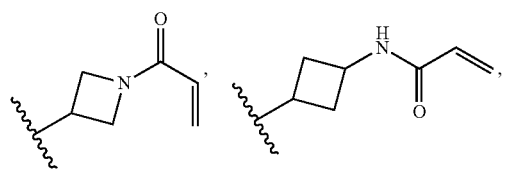
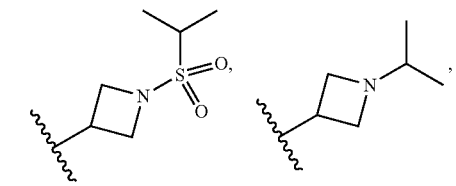
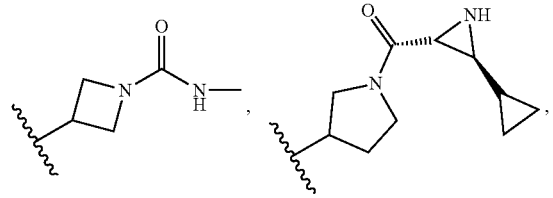
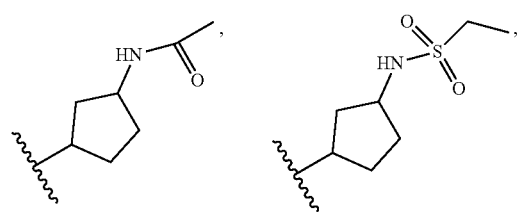
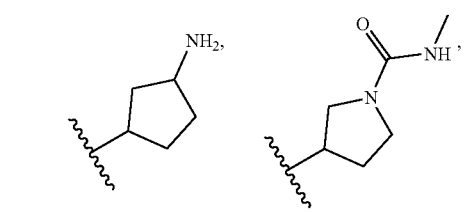
-continued
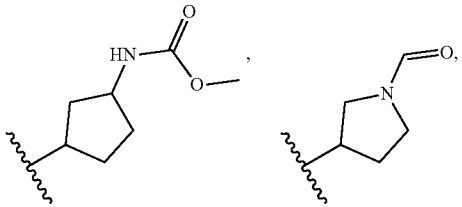
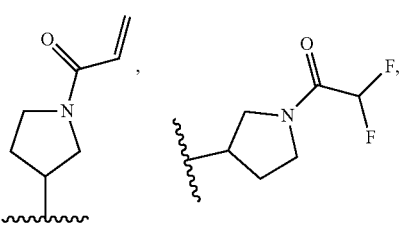
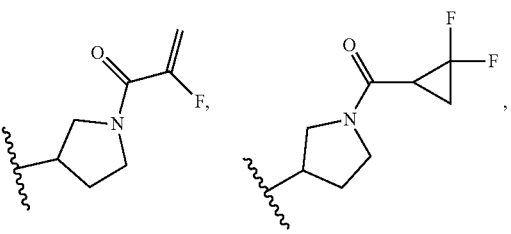
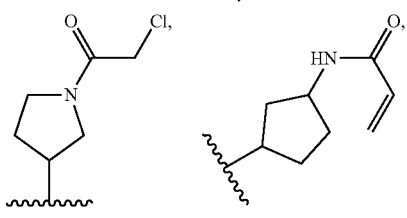
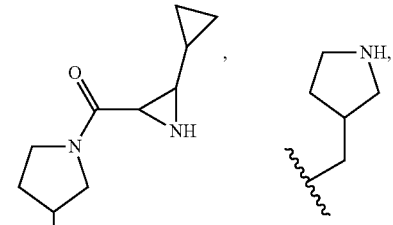
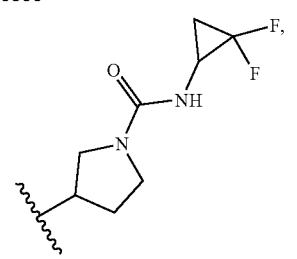
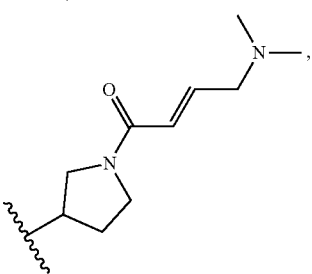

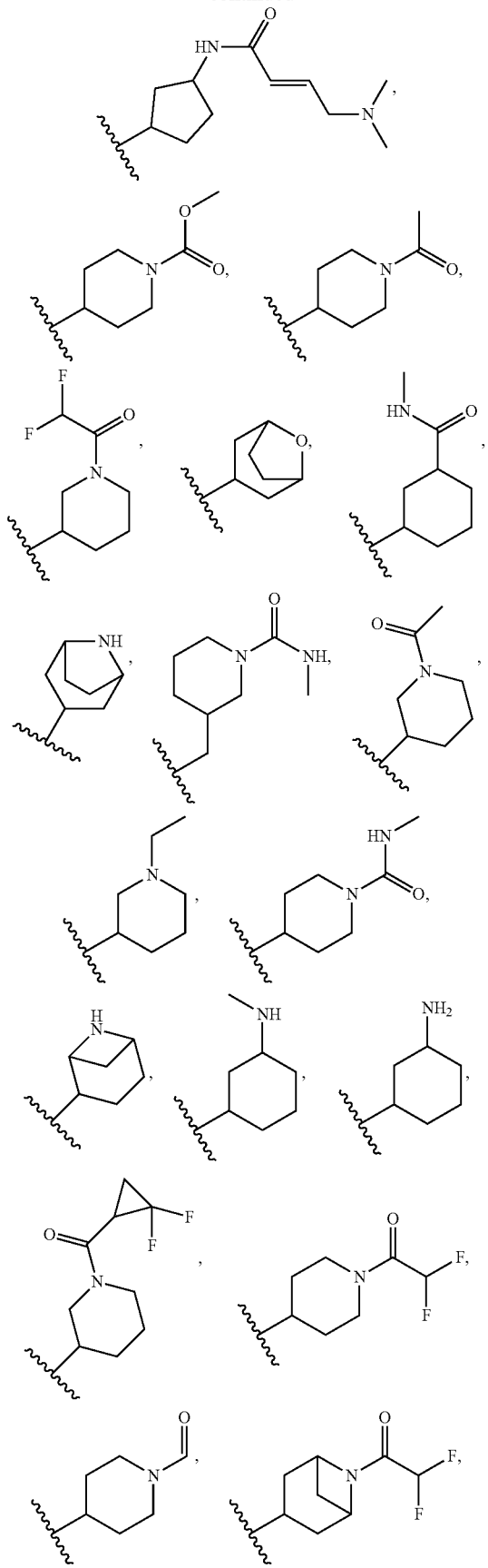
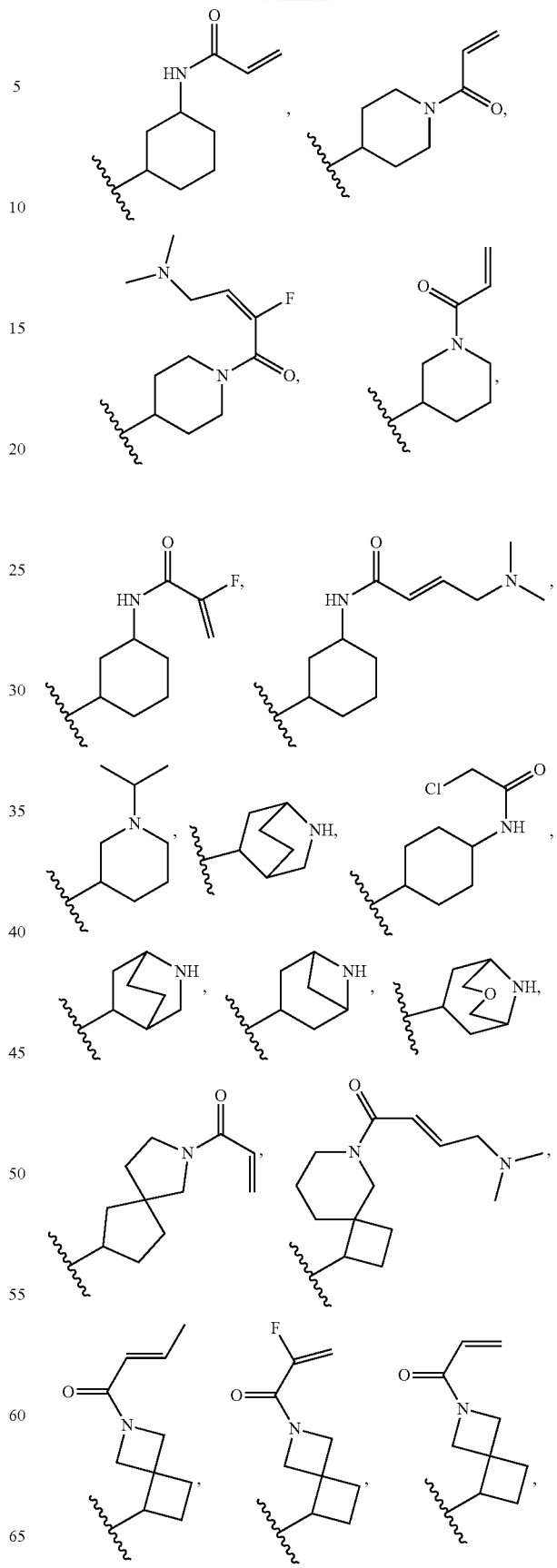

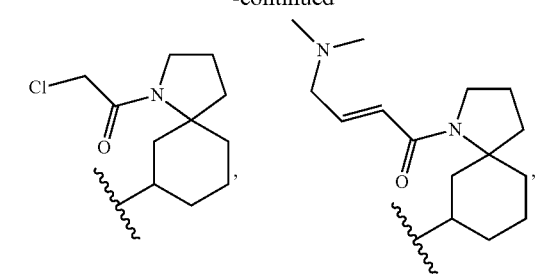
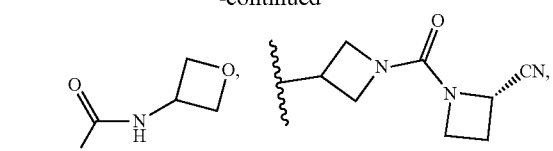
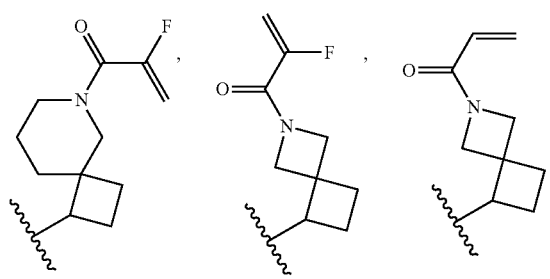
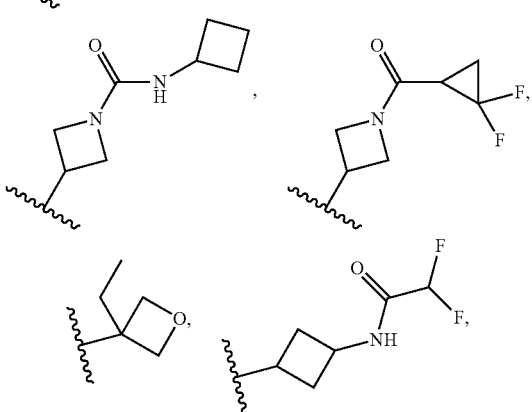
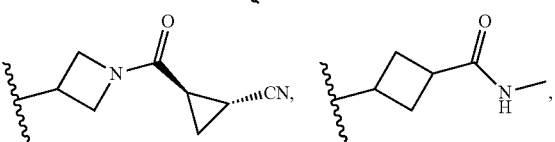
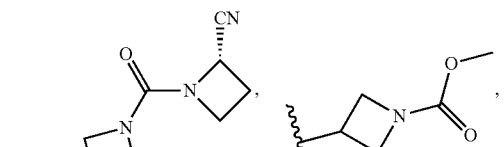
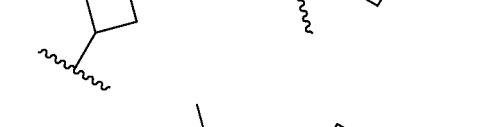
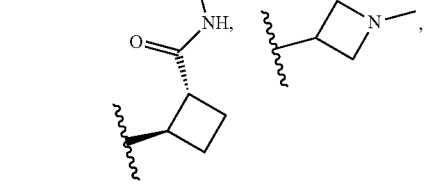
In embodiments of the formulae above, R⁴ is independently selected from
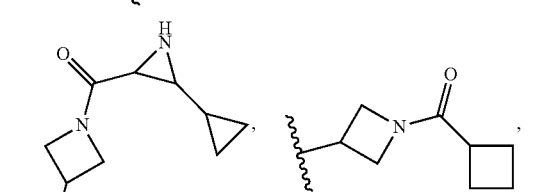
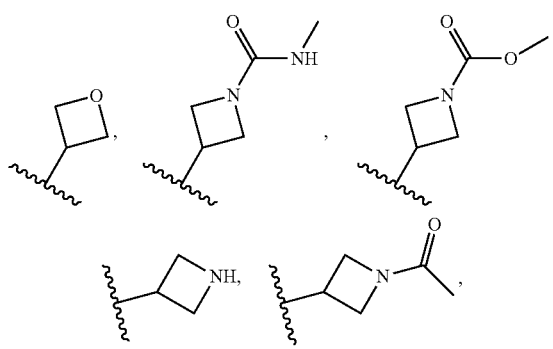
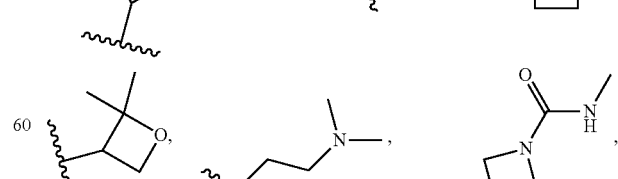
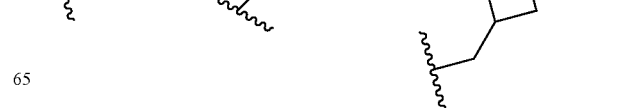

575
-continued
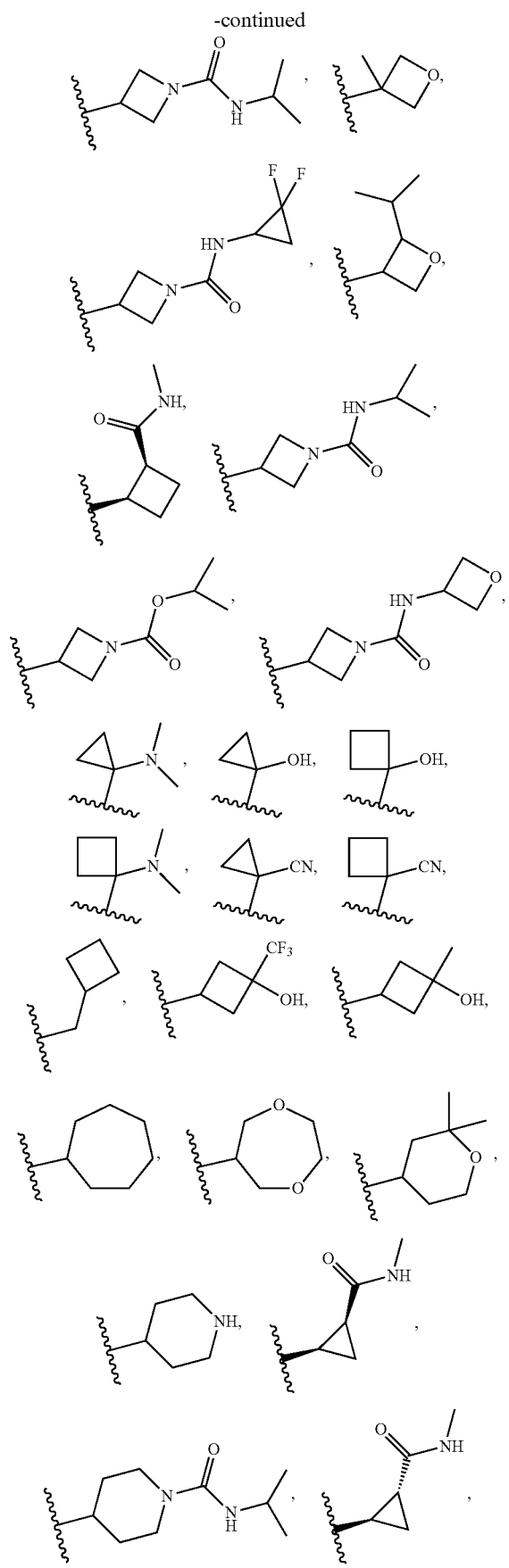
576
-continued
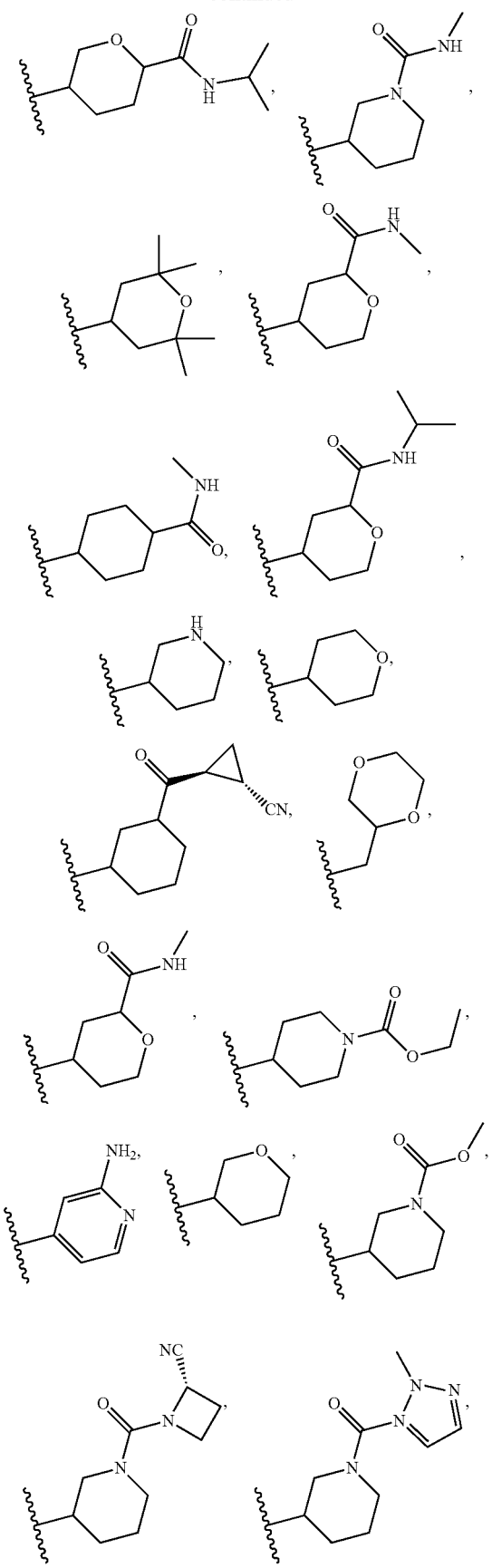

577
-continued
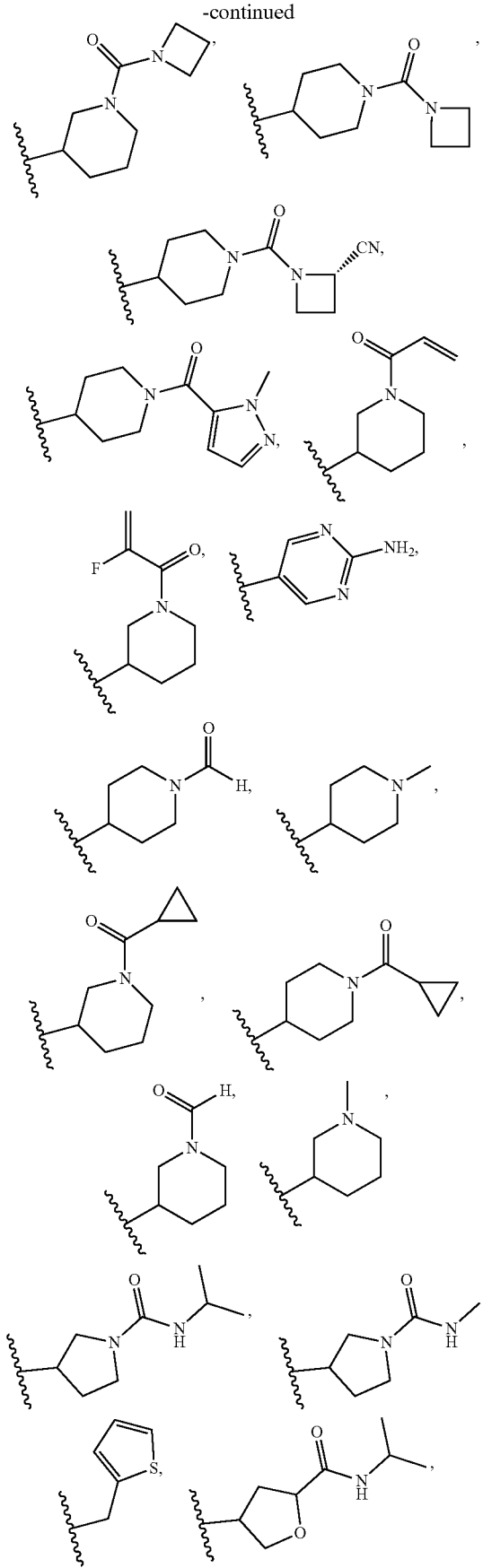
578
-continued
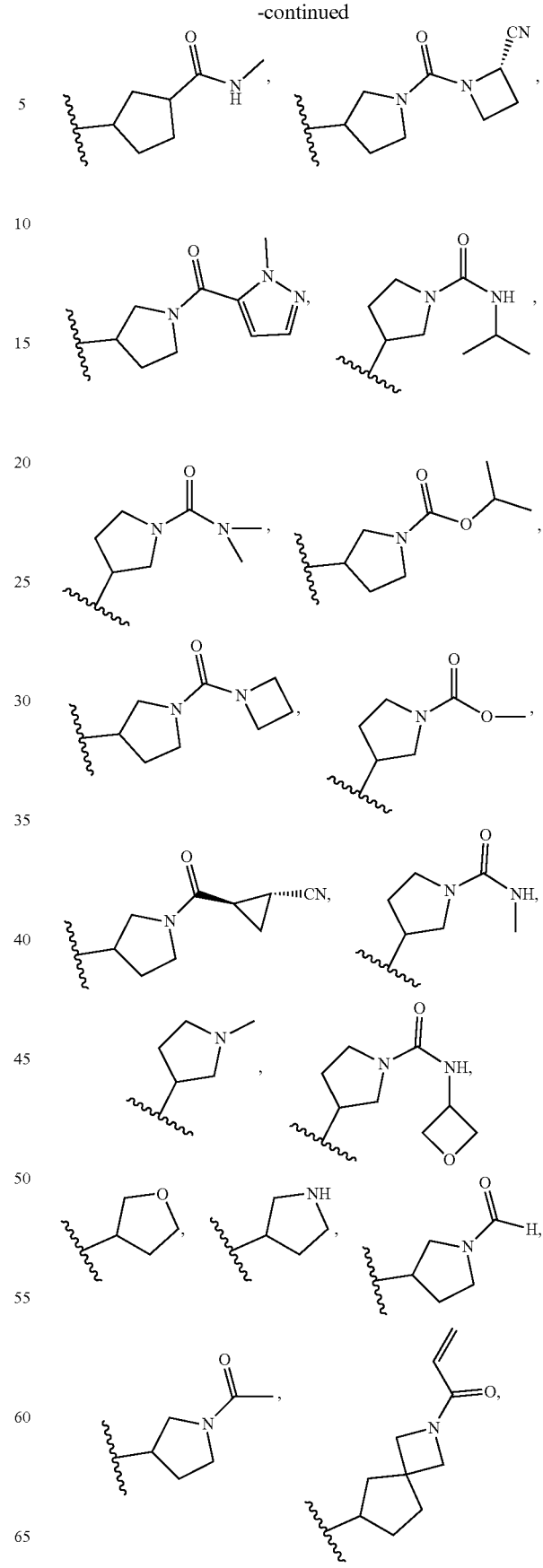

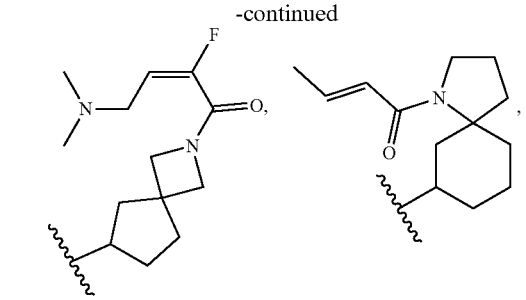
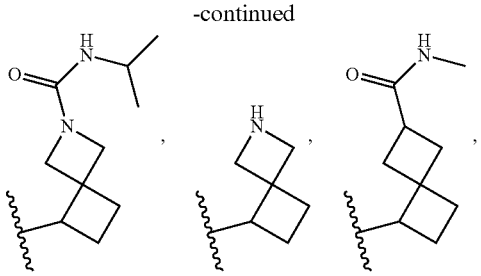
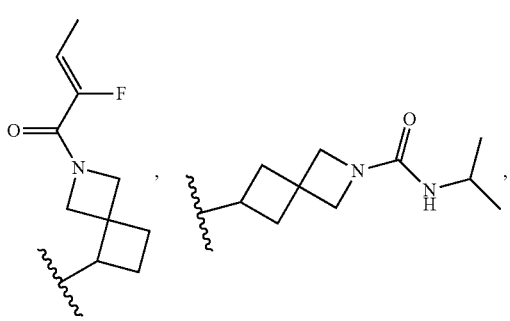
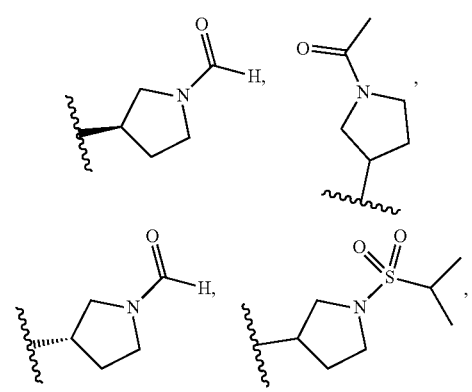
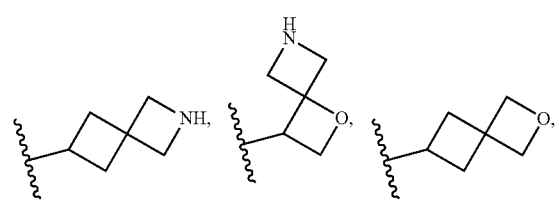
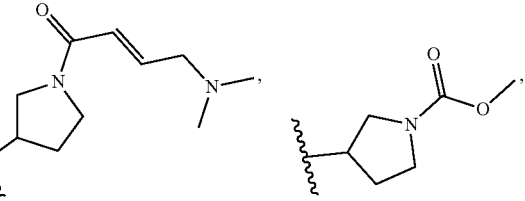
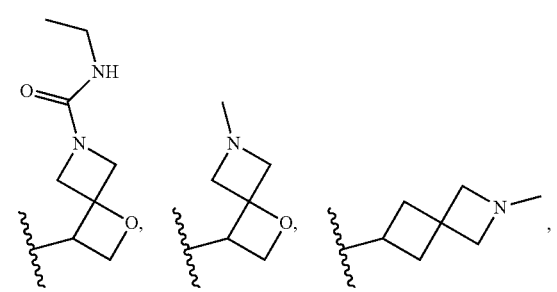
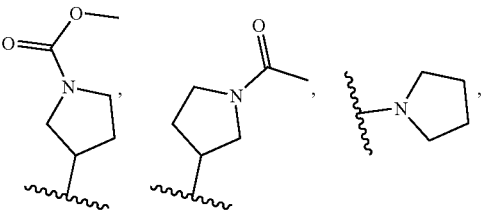
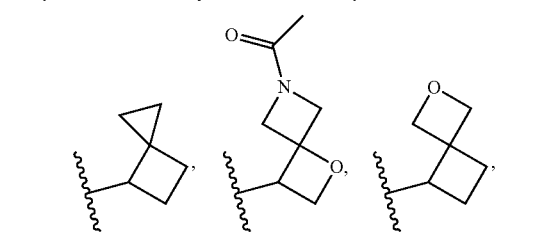
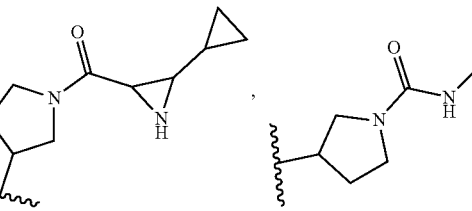
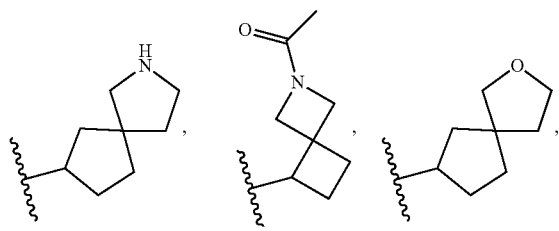
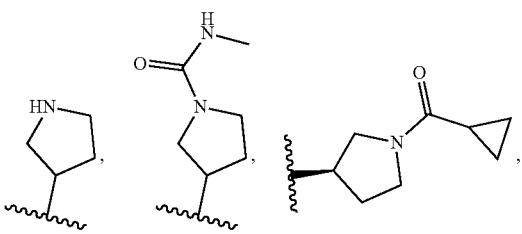

581
-continued
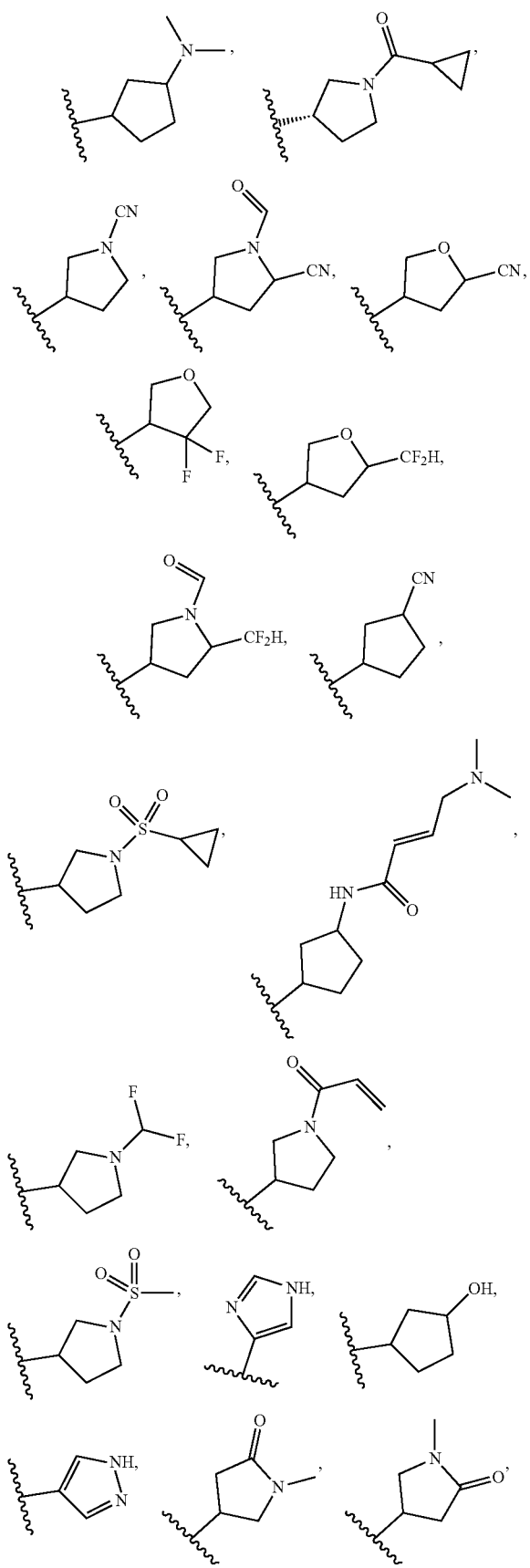
582
-continued
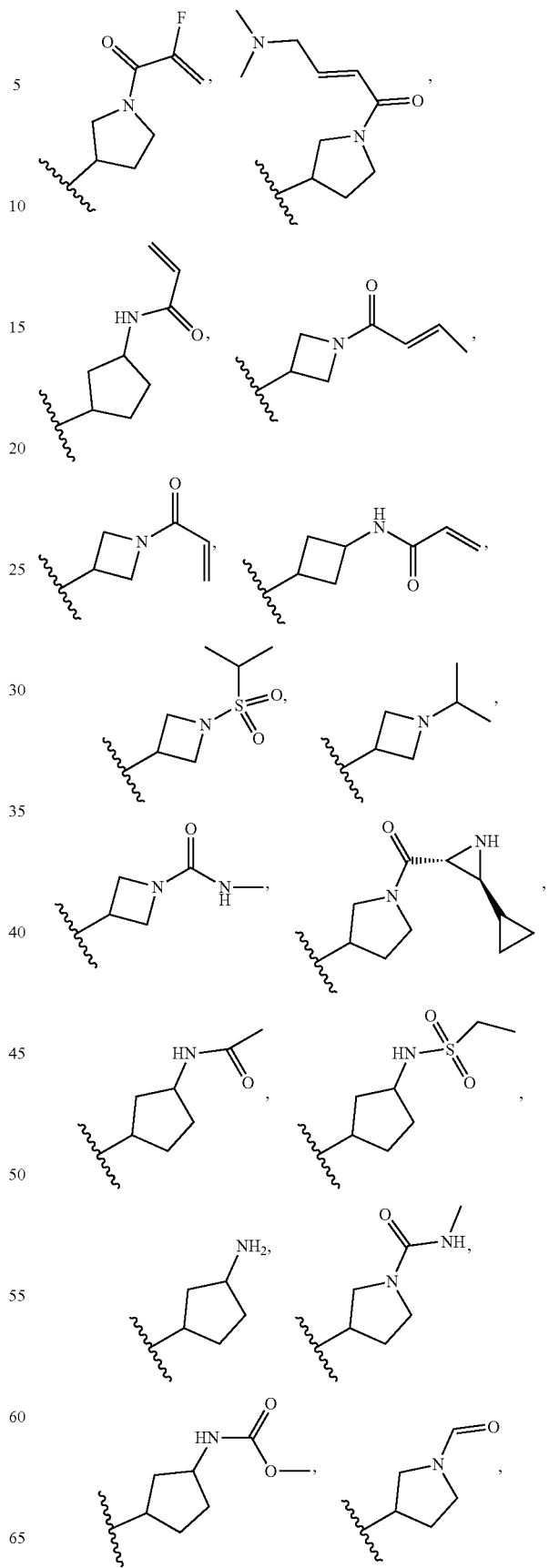

583
-continued
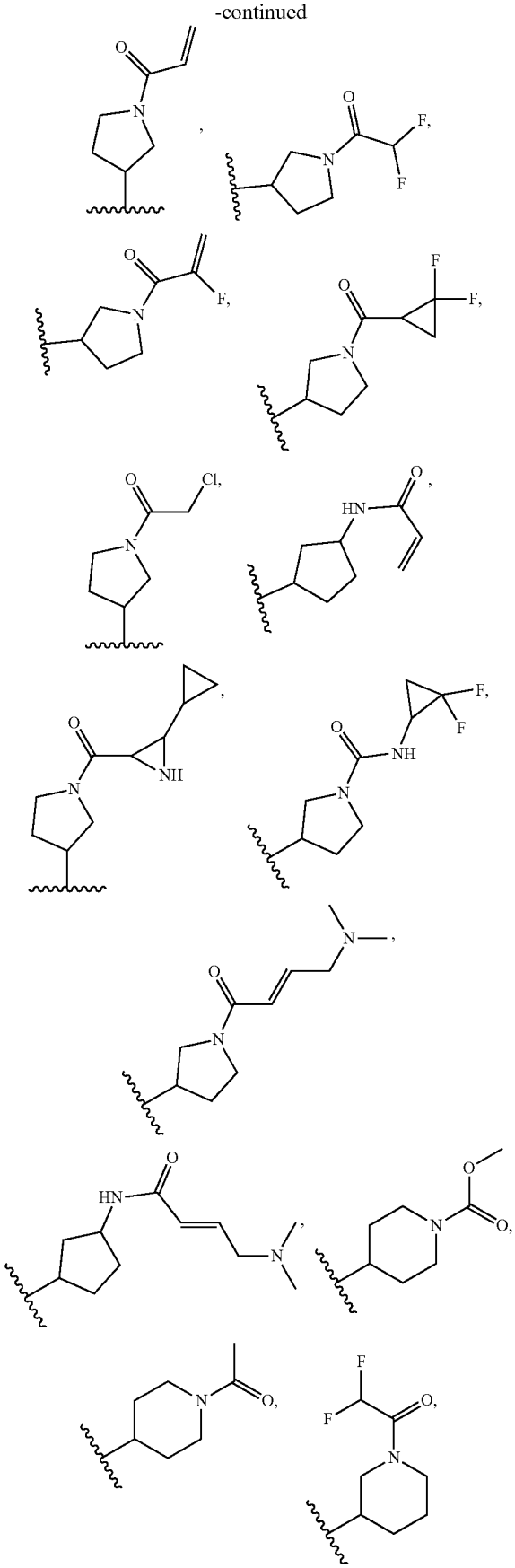
584
-continued
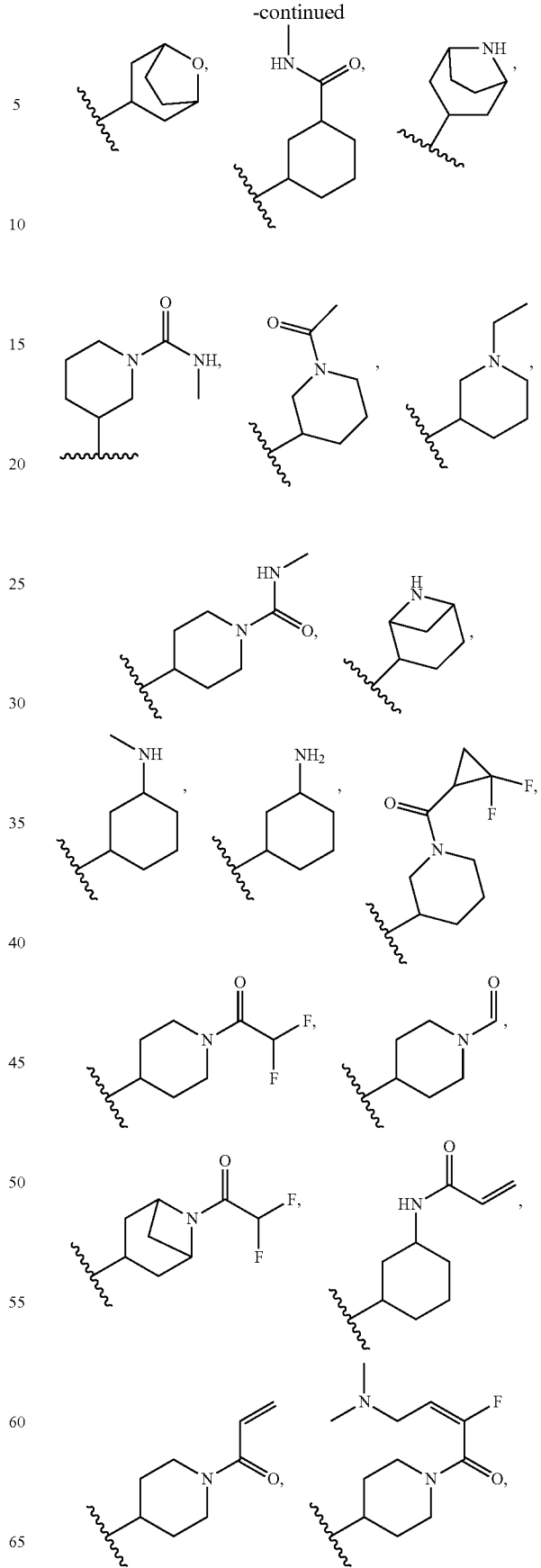

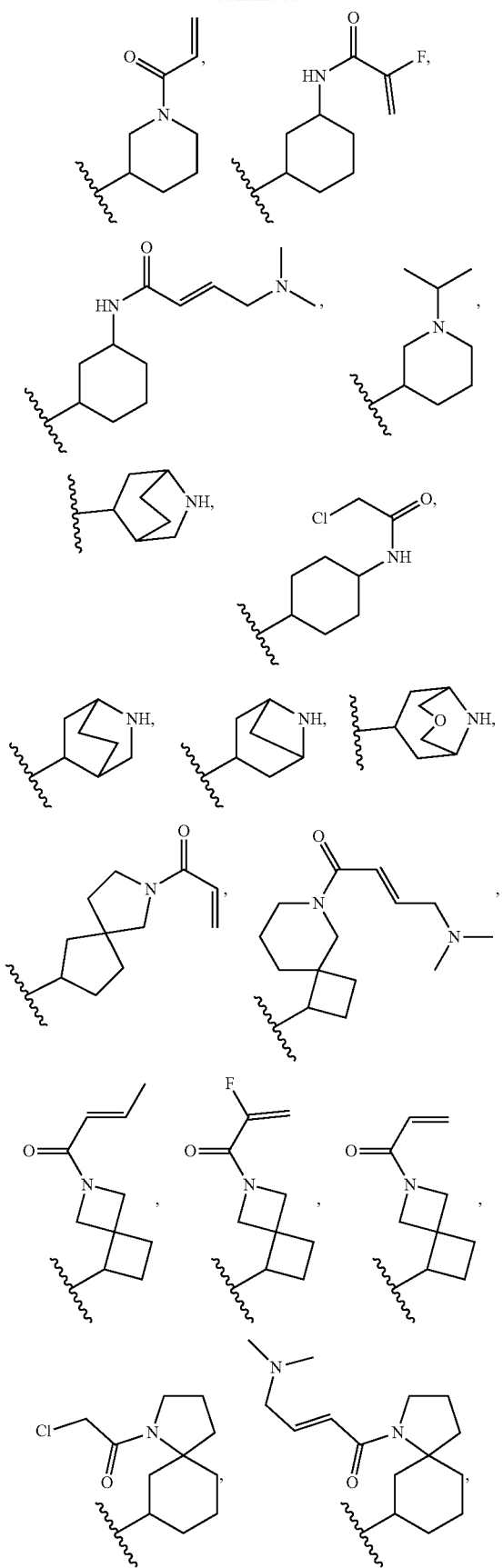
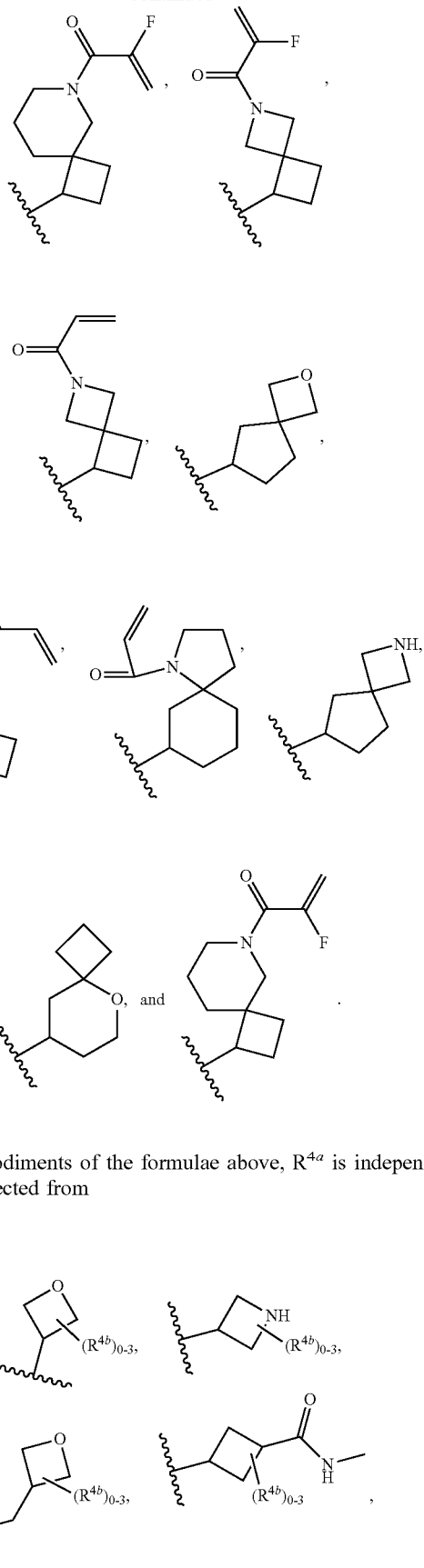
In embodiments of the formulae above, $R^{4a}$ is independently selected from
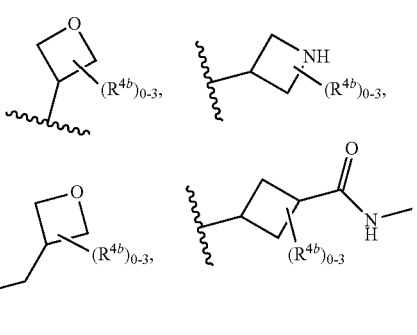

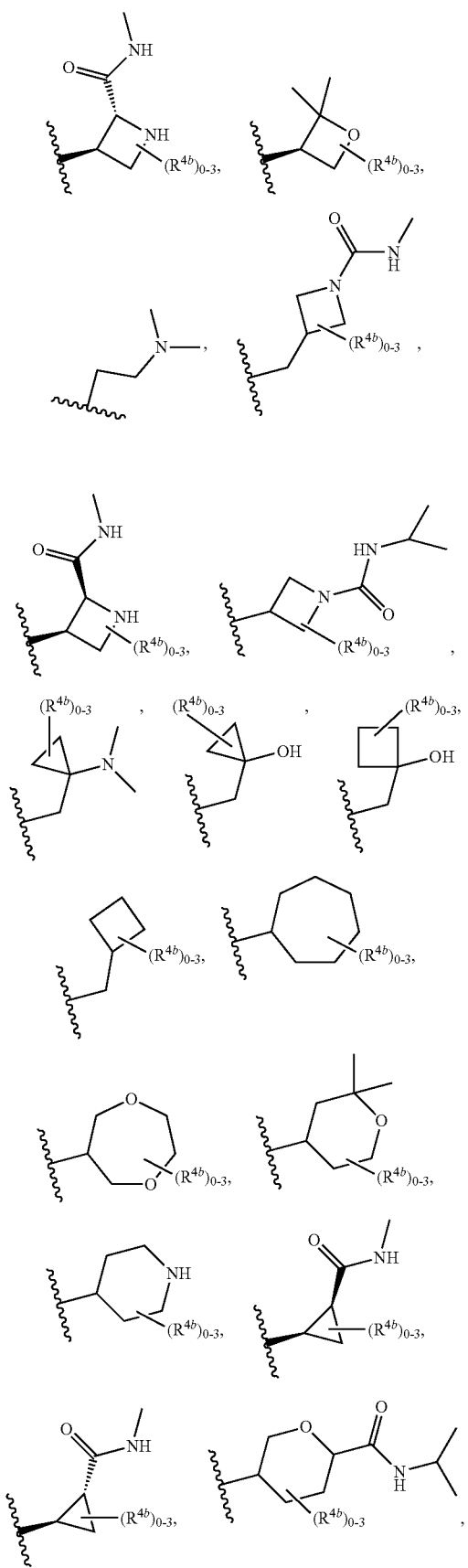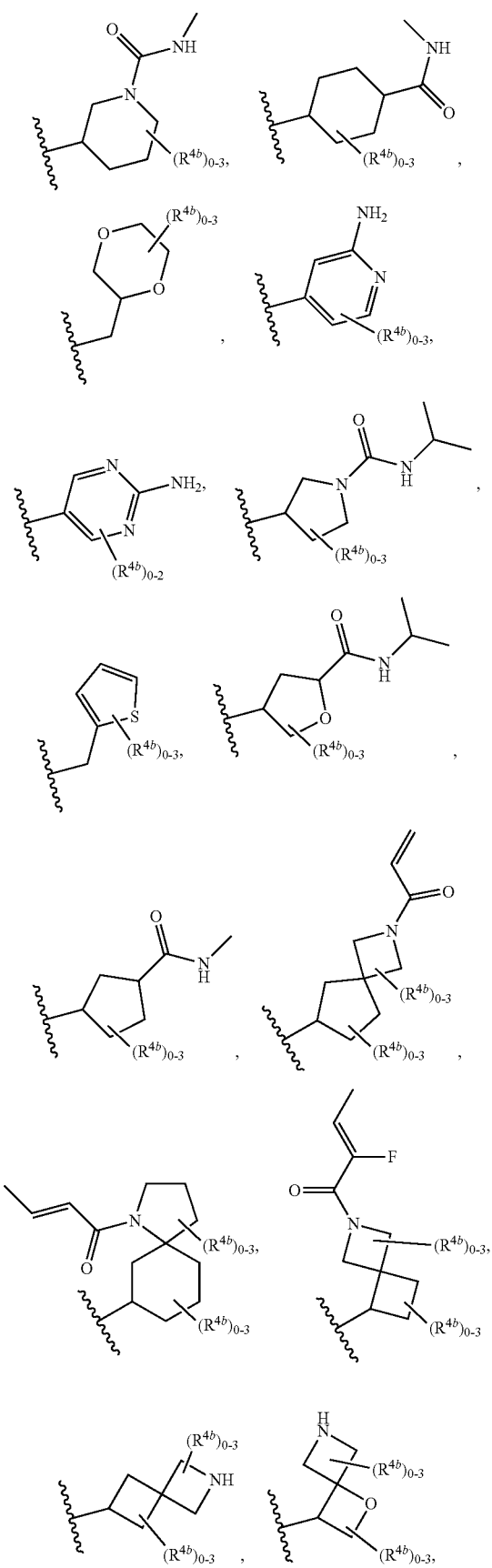

589
-continued
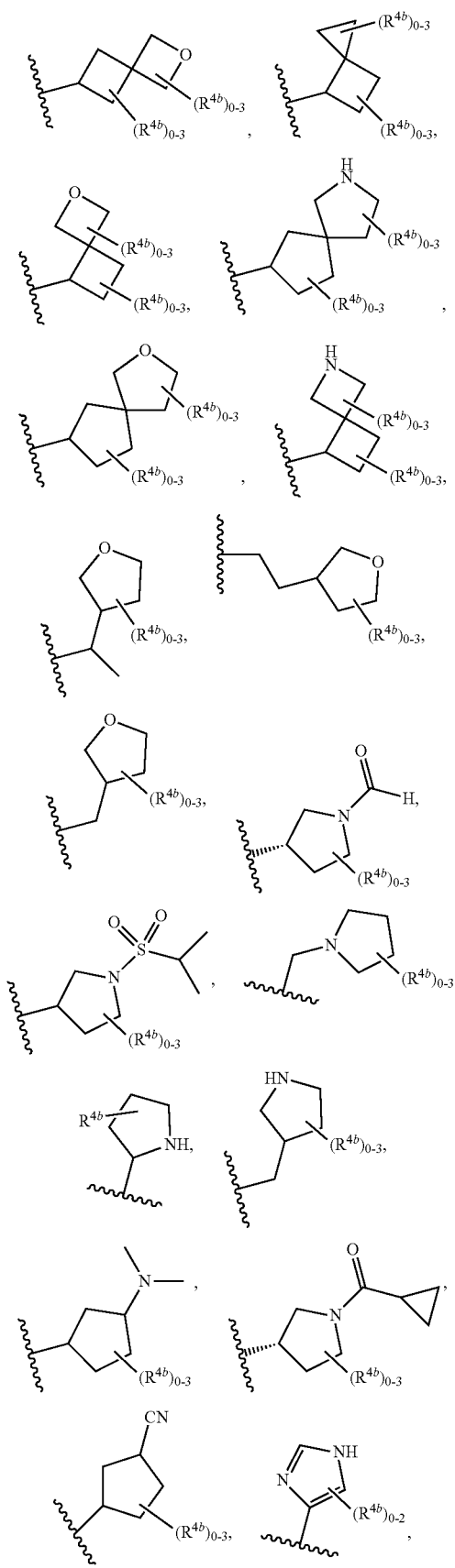
590
-continued
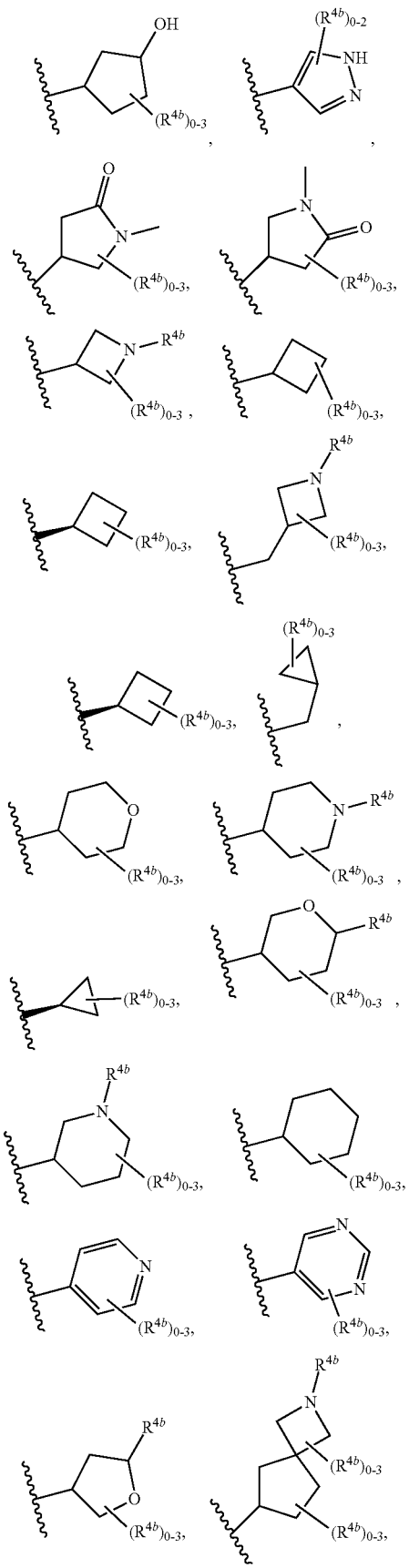

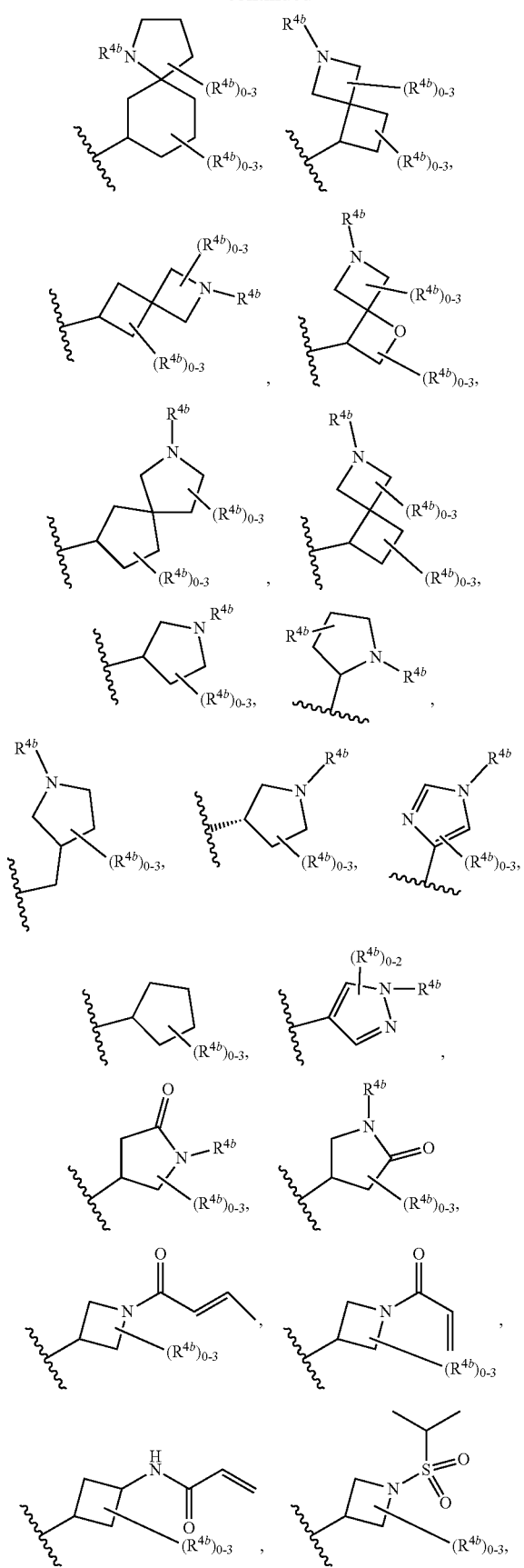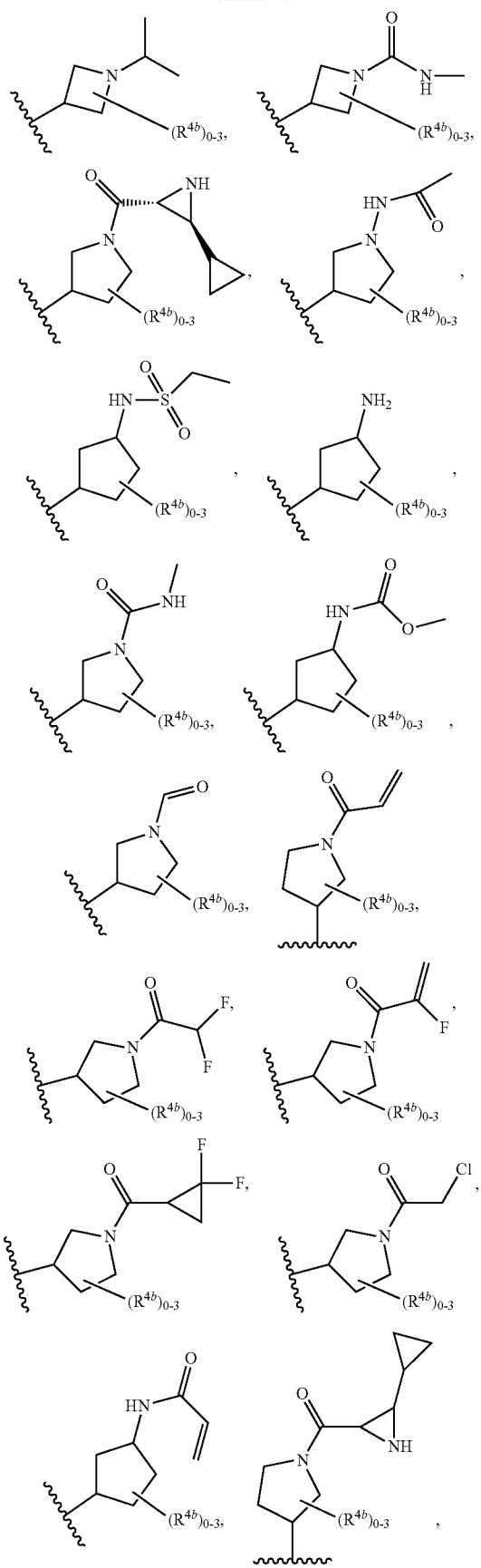

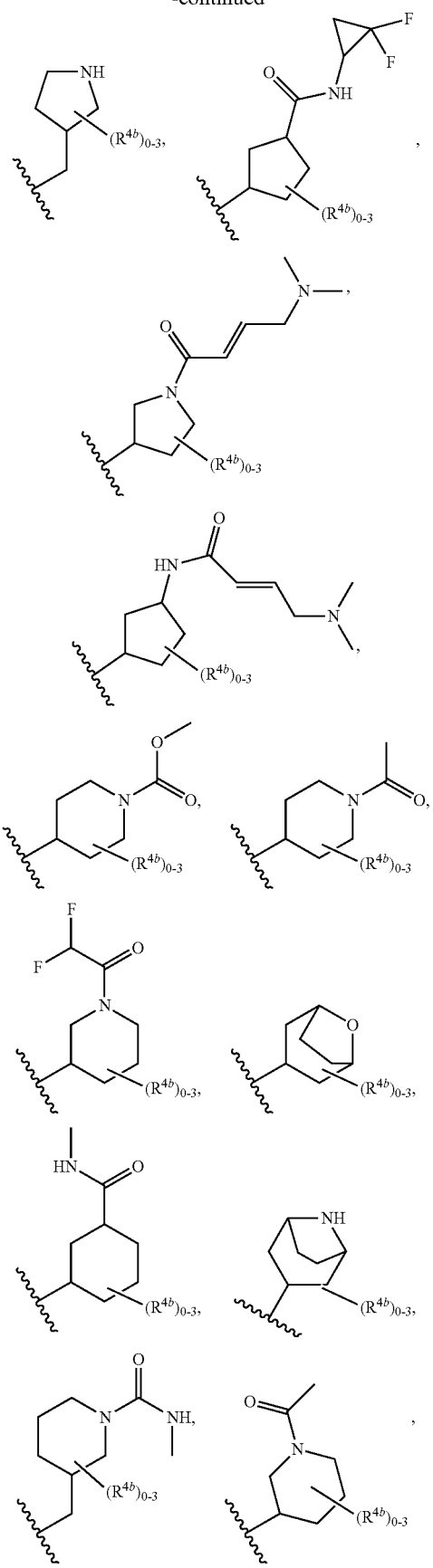
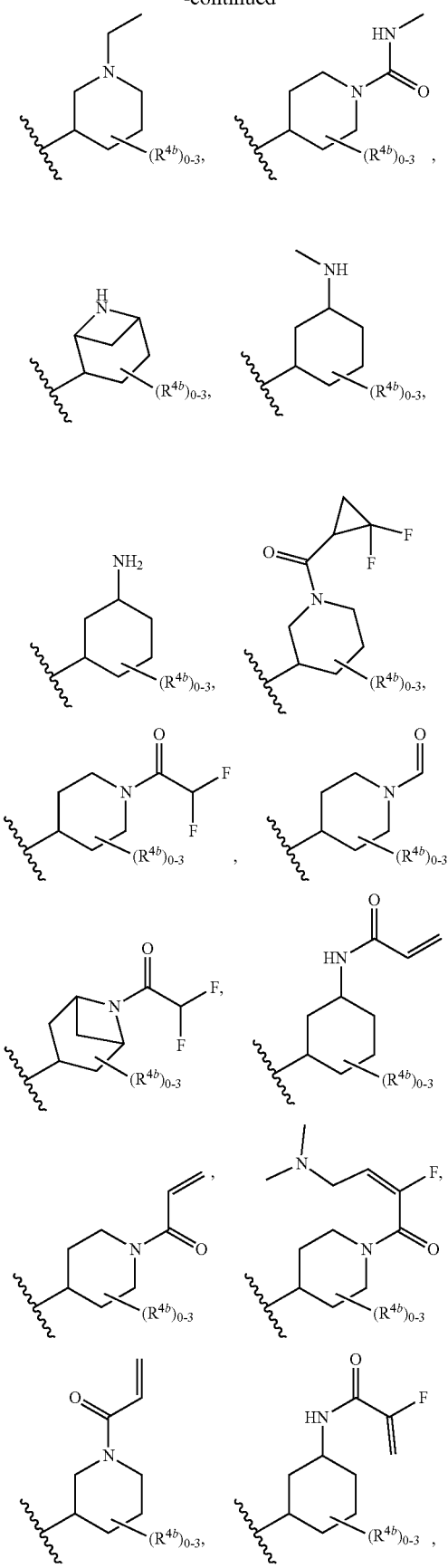

-continued
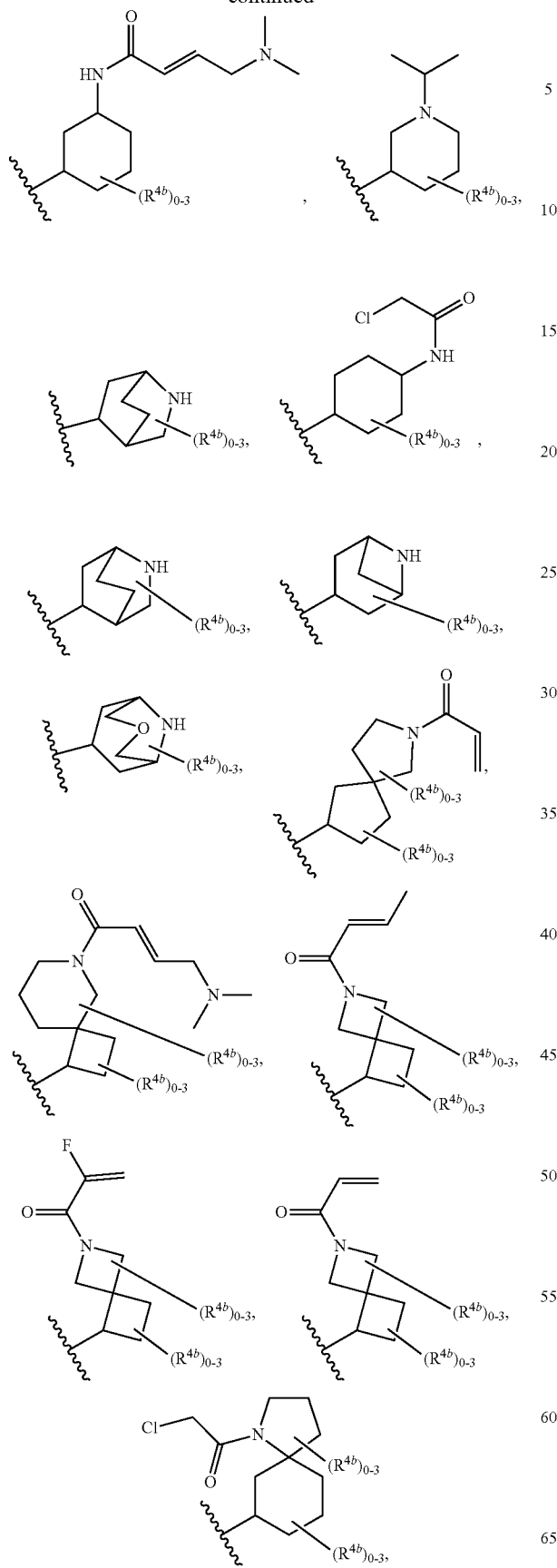 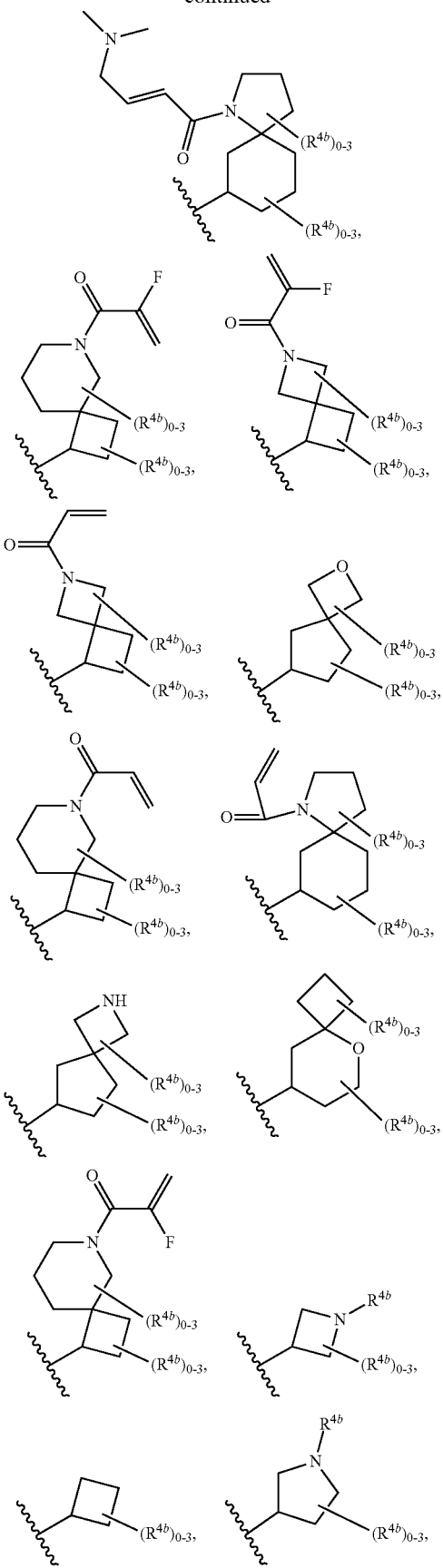

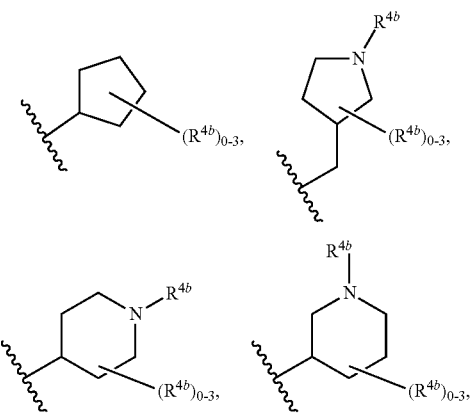
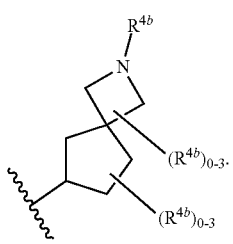
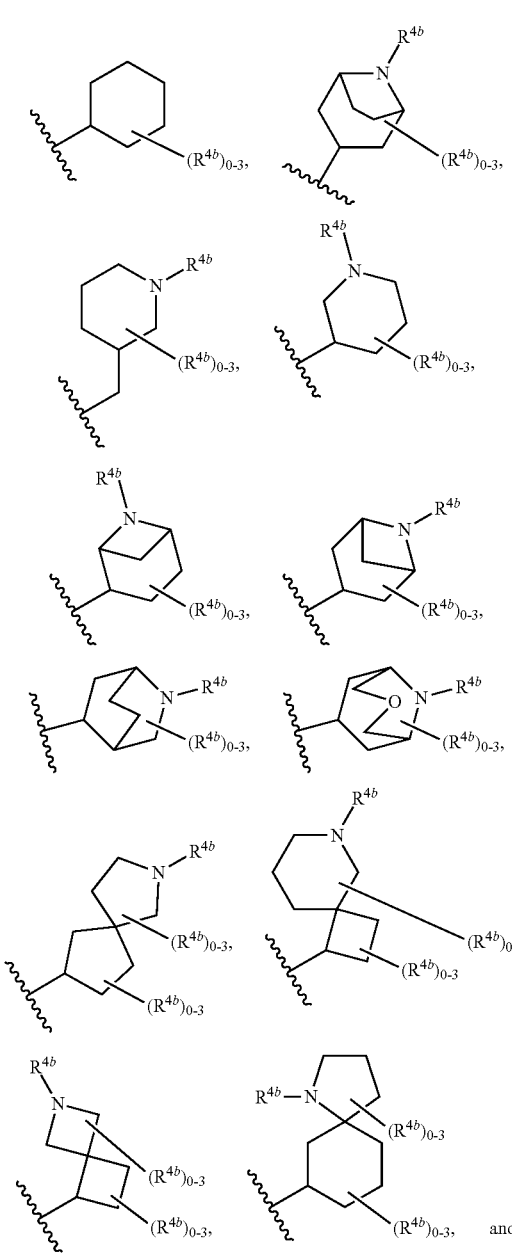
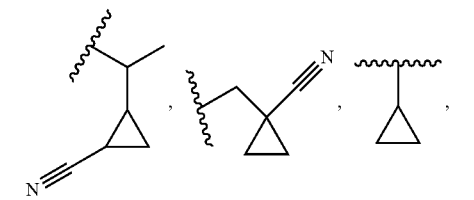
In embodiments of the formulae above, R⁴ is independently selected from
In embodiments of the formulae above, each R⁴ is independently selected from 599
-continued
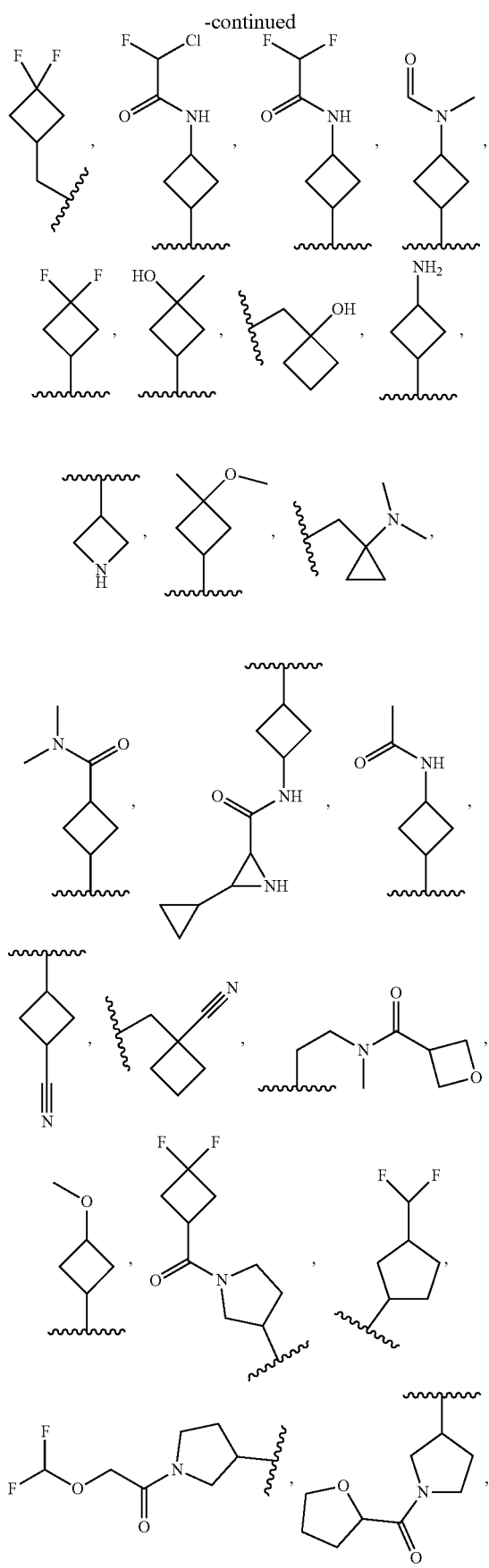
600
-continued
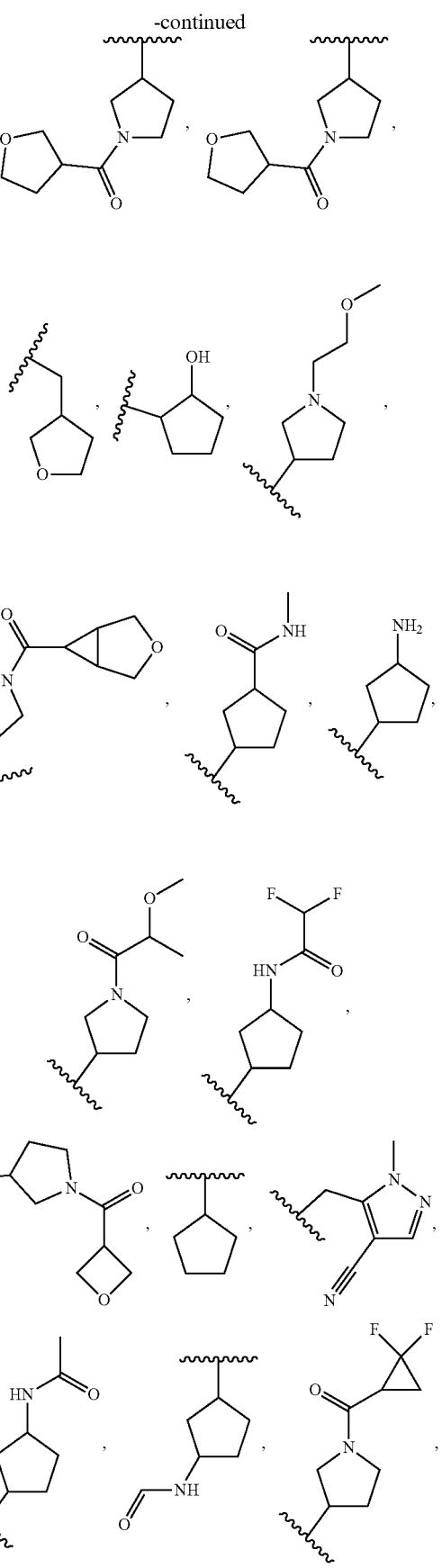

601
-continued
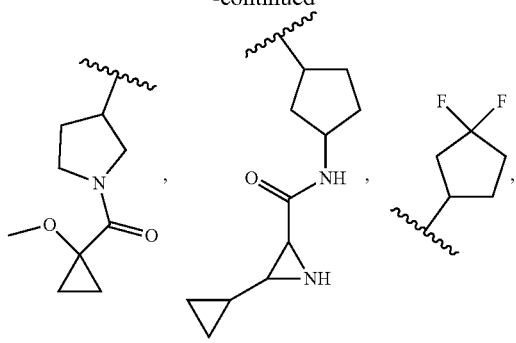
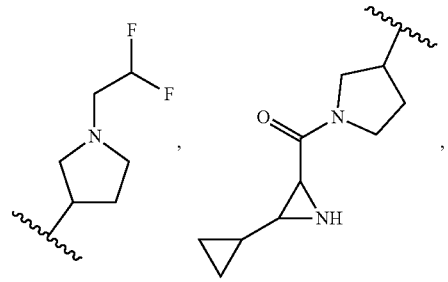
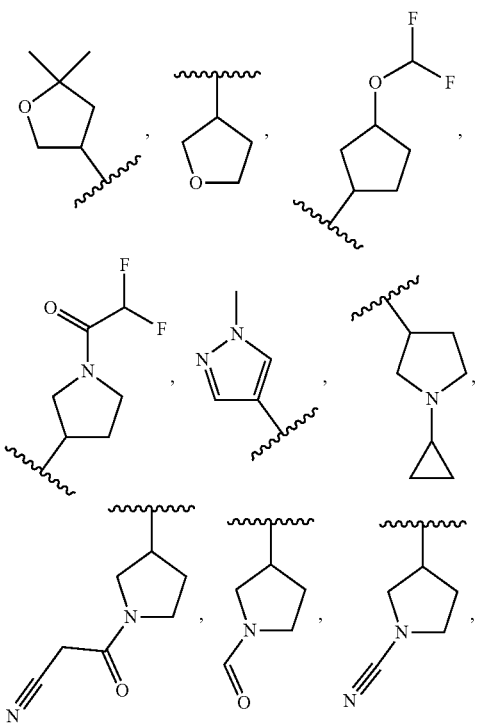
602
-continued
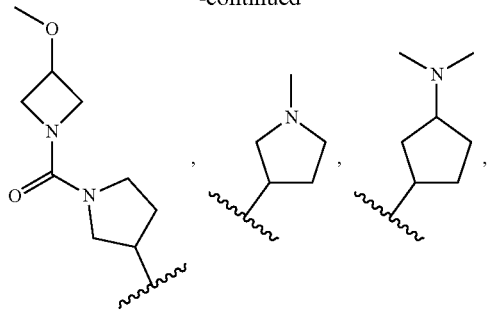
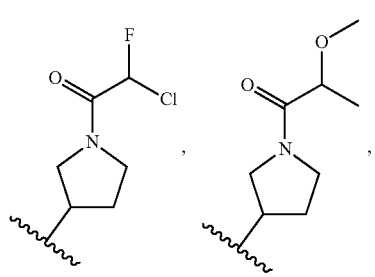
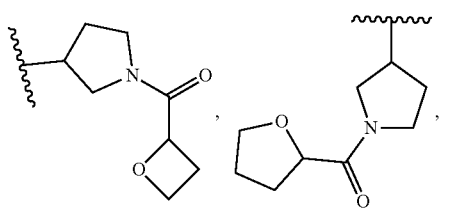
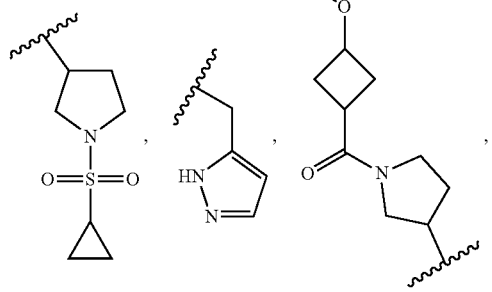
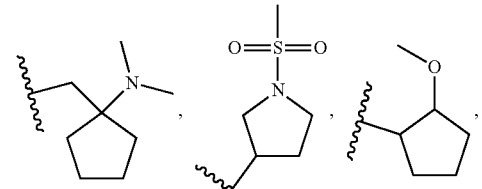
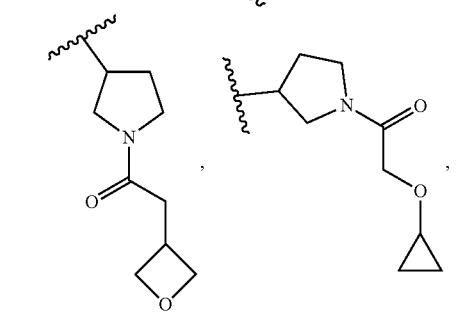

603
-continued
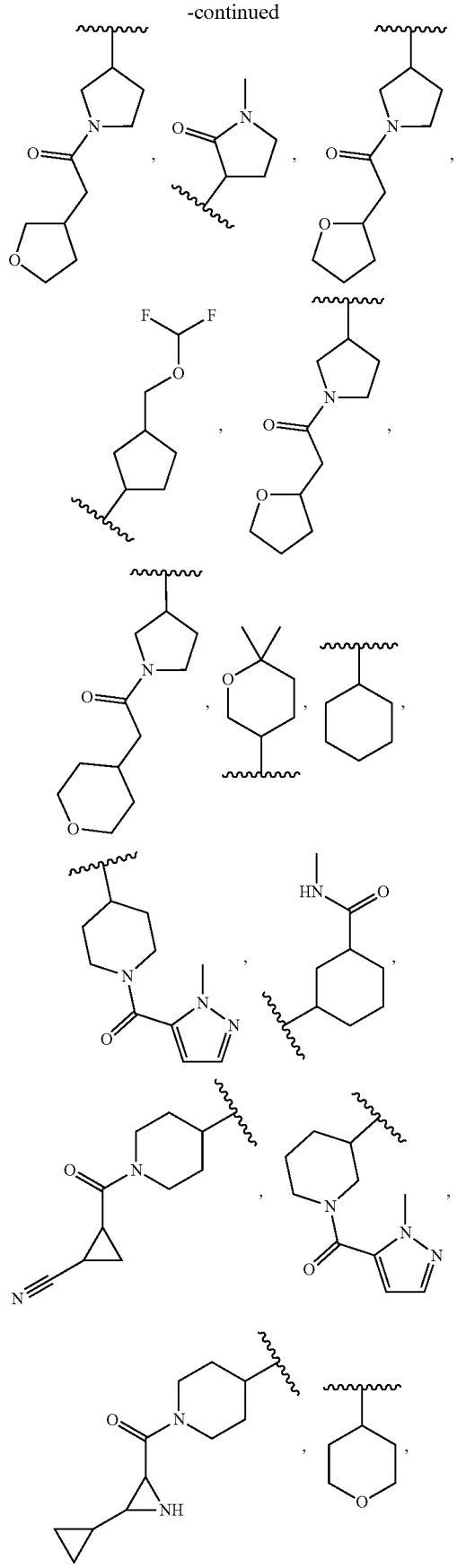
604
-continued
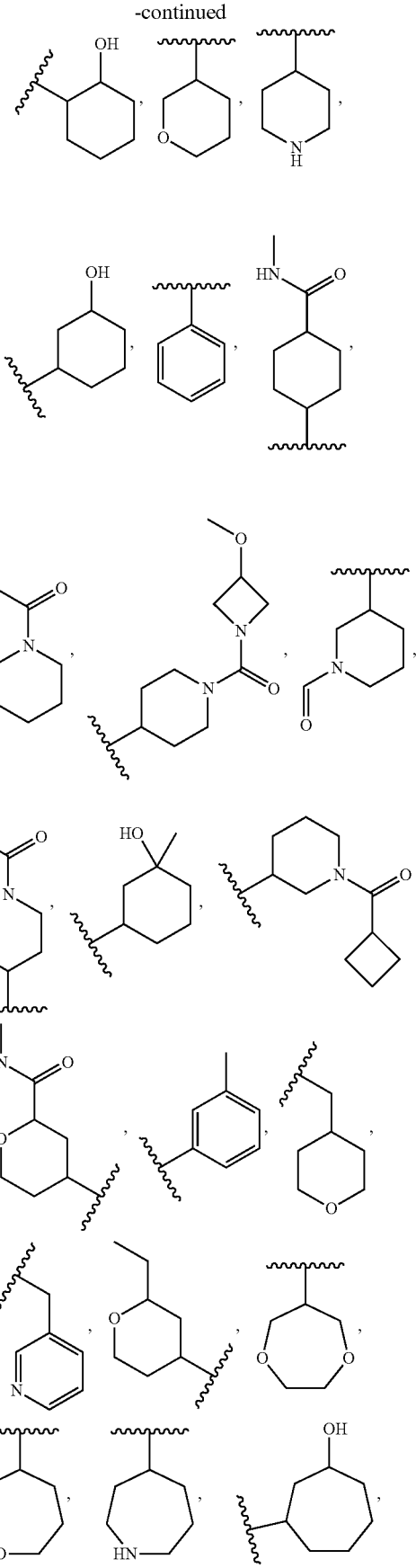

605
-continued
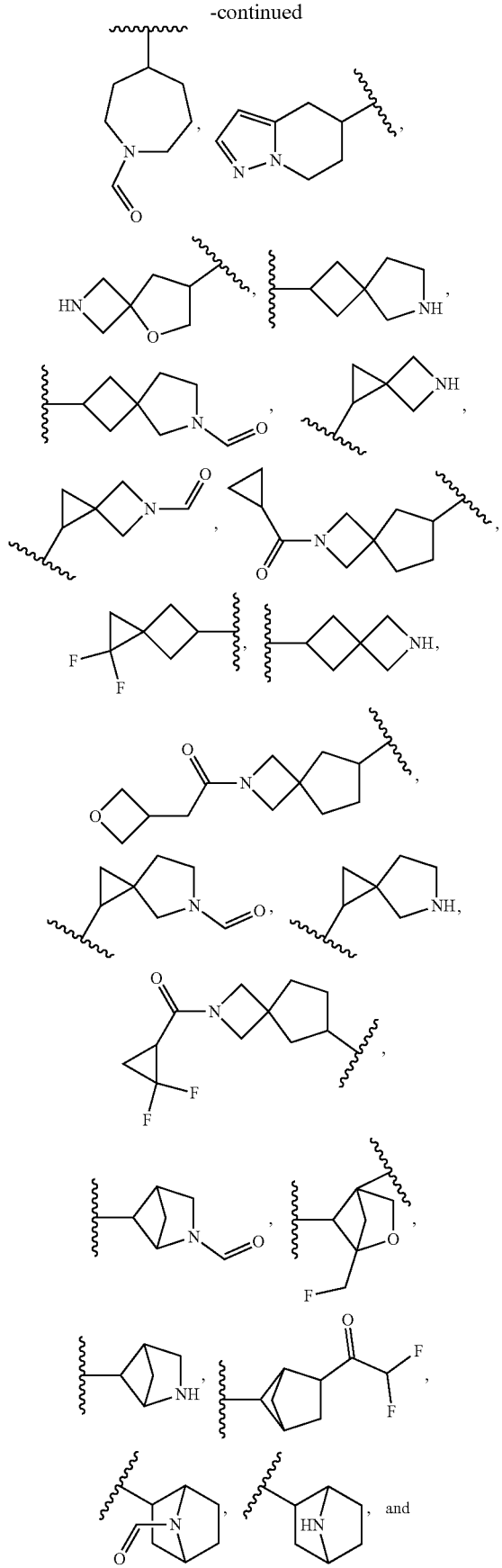
606
-continued
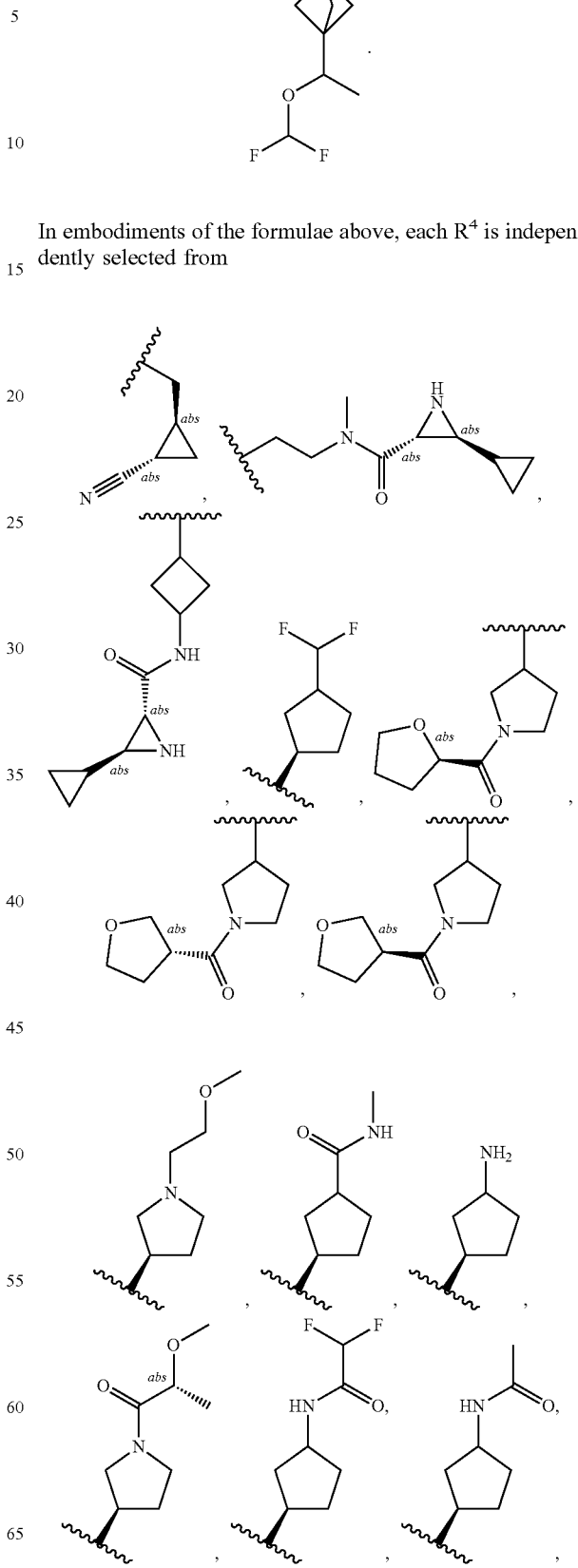
In embodiments of the formulae above, each $R^4$ is independently selected from 607
-continued
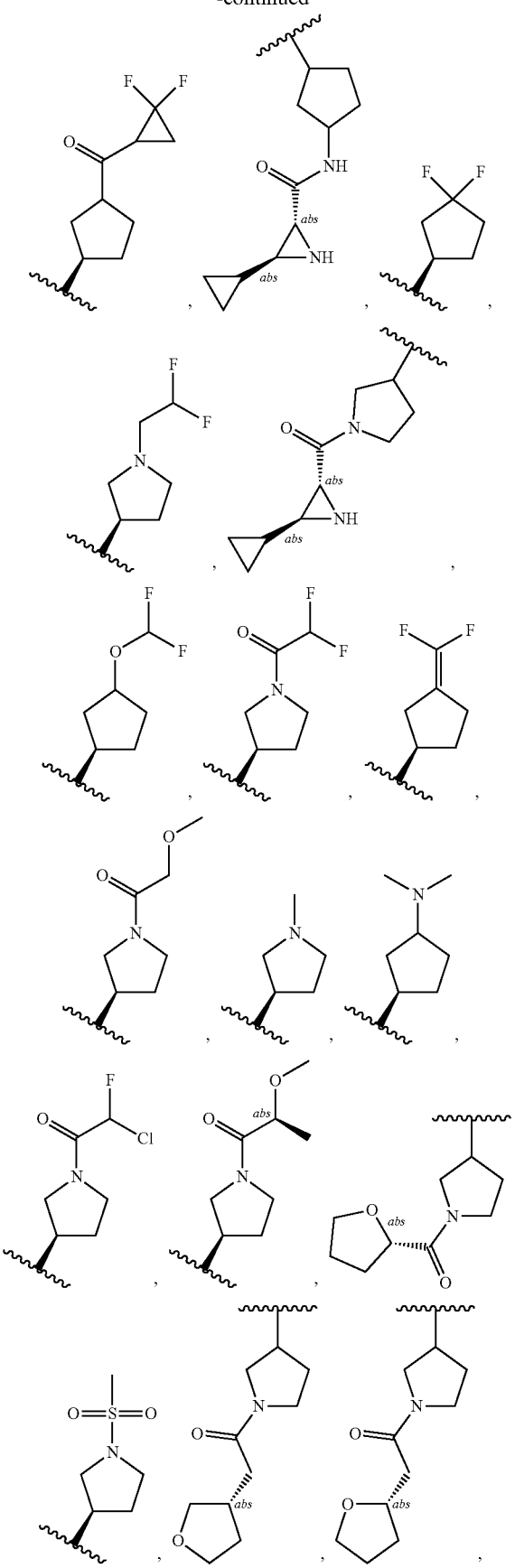
608
-continued
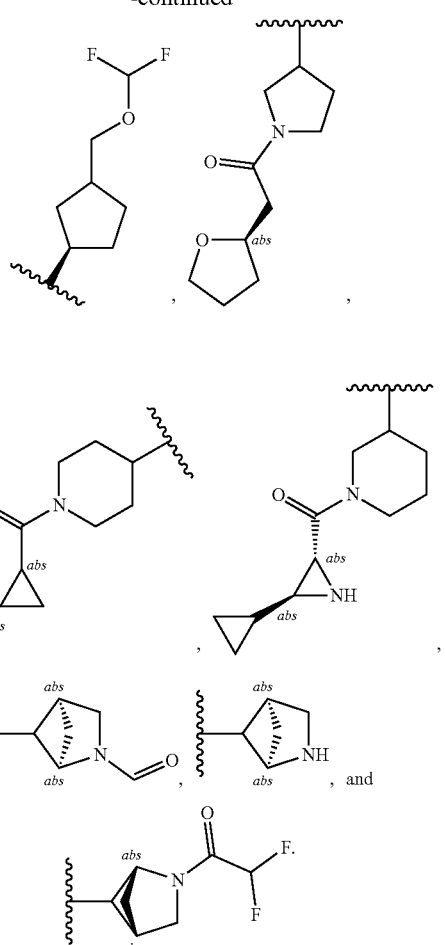
In embodiments of the formulae above, each R⁴ is independently selected from
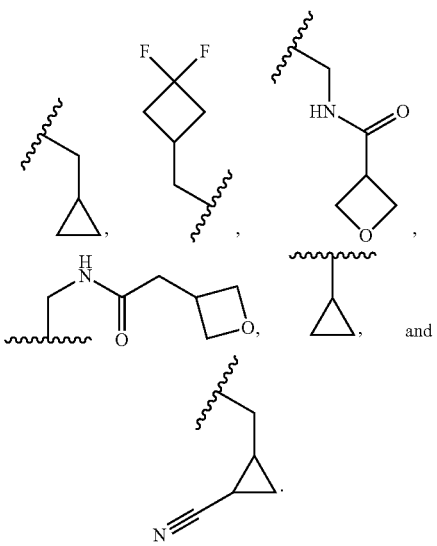
In embodiments of the formulae above, each R⁴ is independently

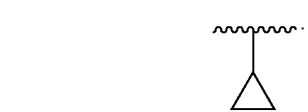
In embodiments of the formulae above, each R⁴ is independently selected from
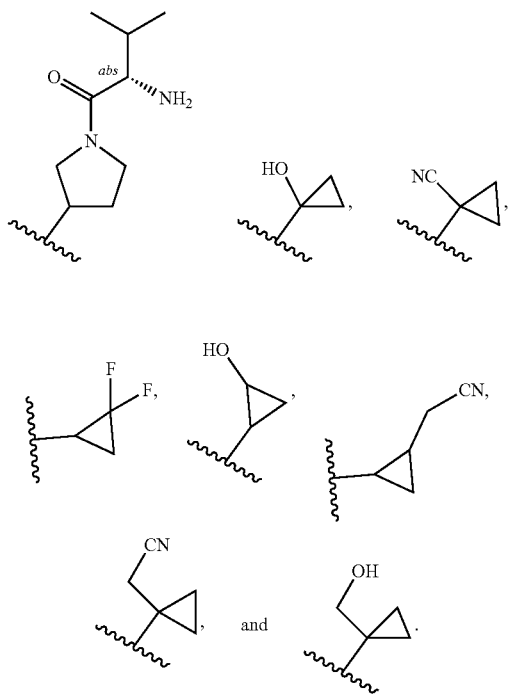
and
In embodiments of the formulae above, each R⁴ is independently
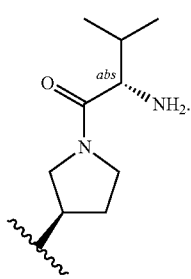 [SMILES: *[C@@H]1CCN(C(=O)[C@@H](N)C(C)C)C1]
In embodiments of the formulae above, each R⁴ is independently selected from
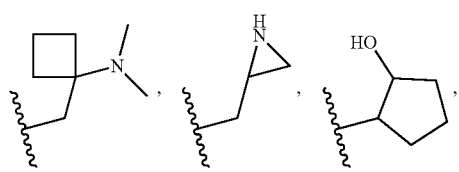
-continued
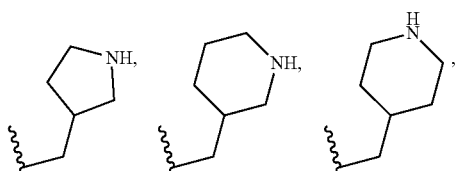
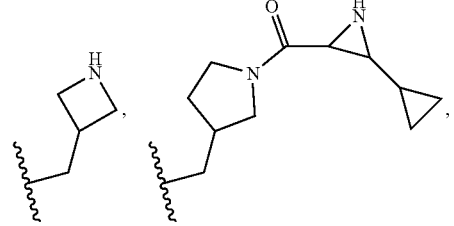
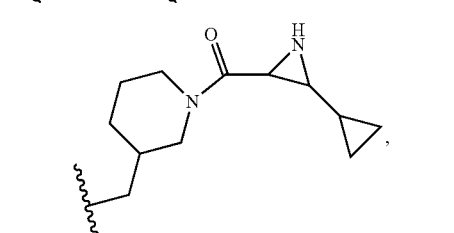
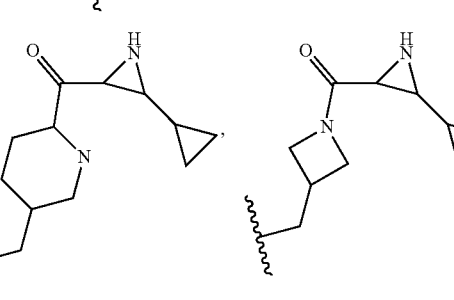
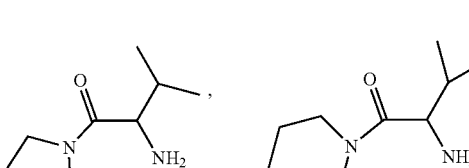

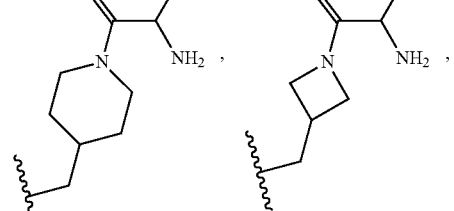
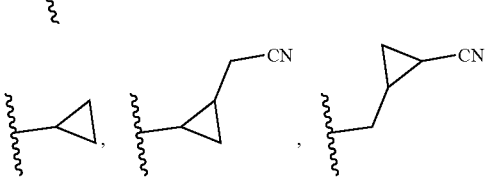

-continued
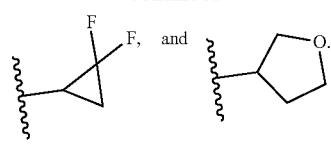
In embodiments of the formulae above, each $R^4$ is independently selected from
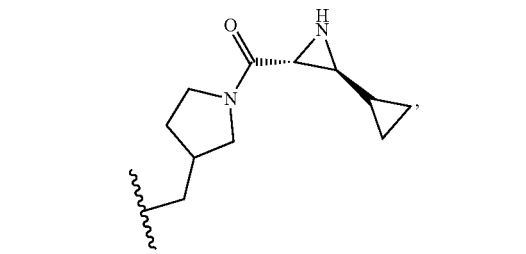
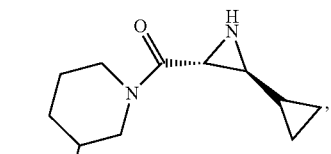
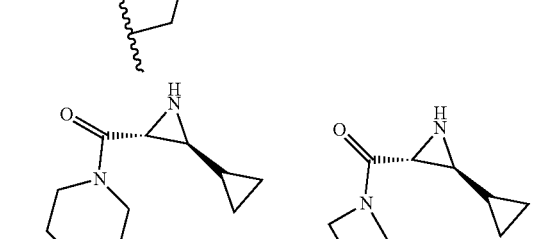
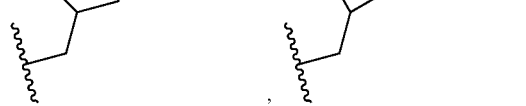
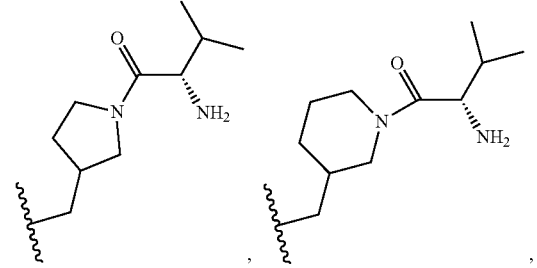
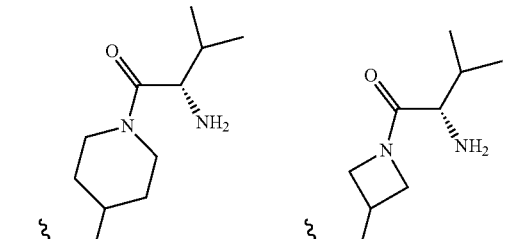
, and
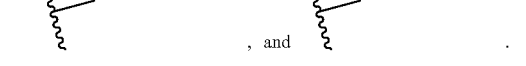
In embodiments of the formulae above, $R^{4a}$ is independently selected from
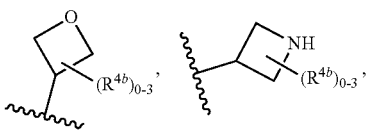
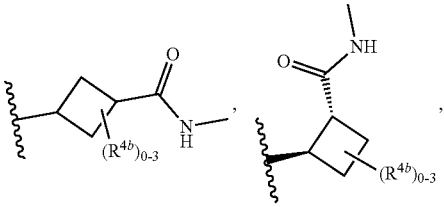
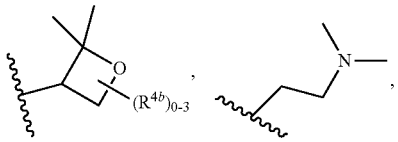
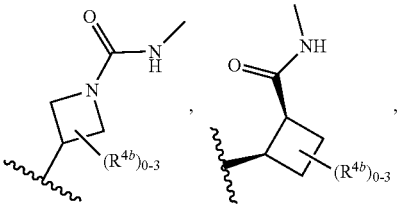
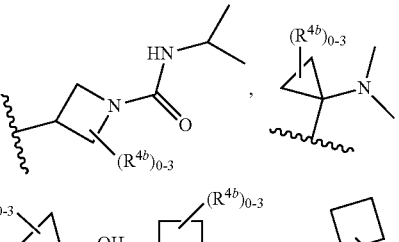
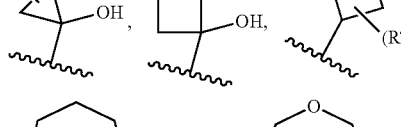
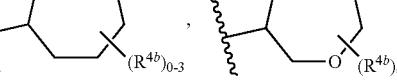
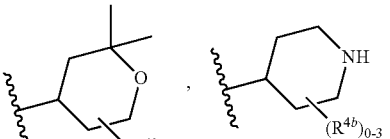
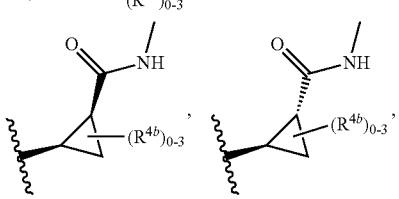
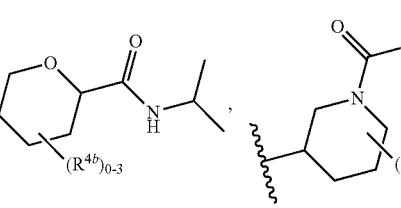

613
-continued
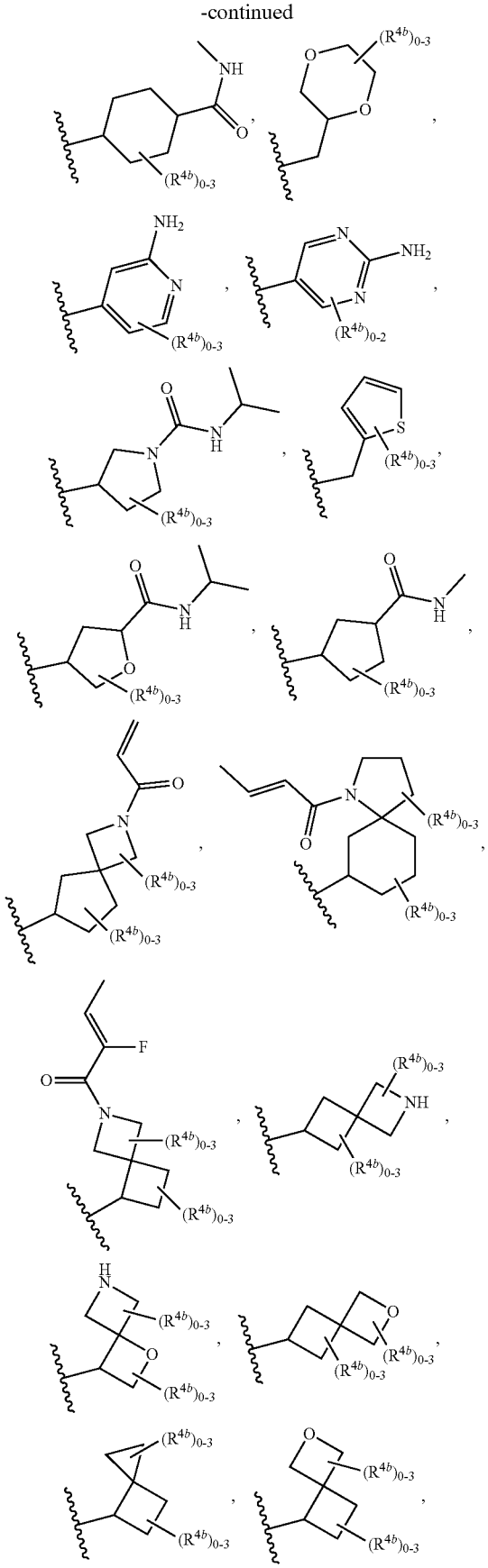
614
-continued
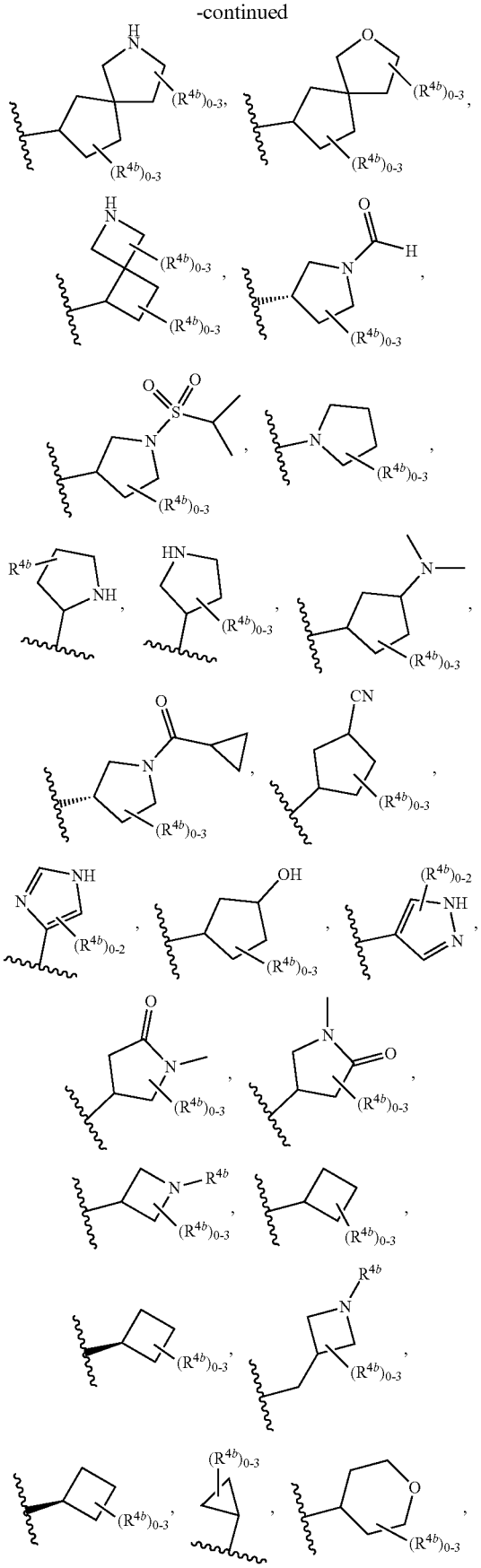


617
-continued
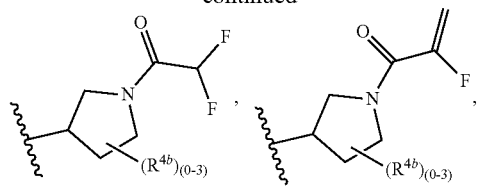
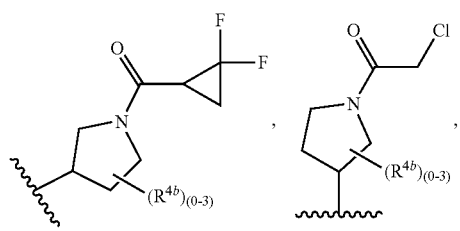
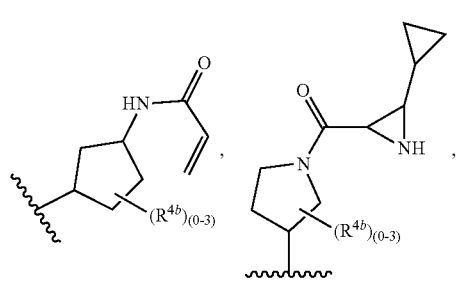
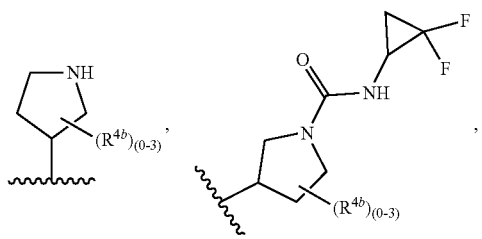
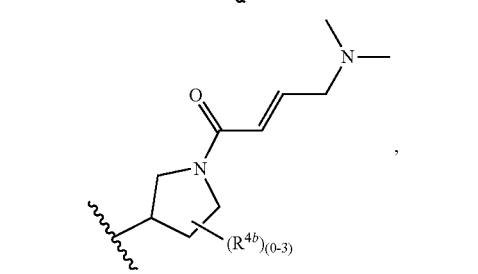
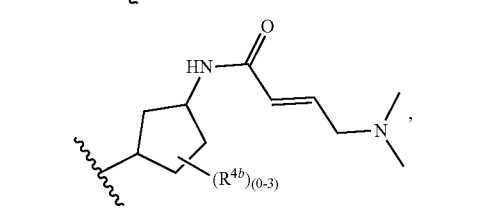
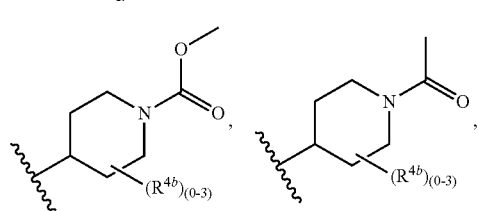
618
-continued
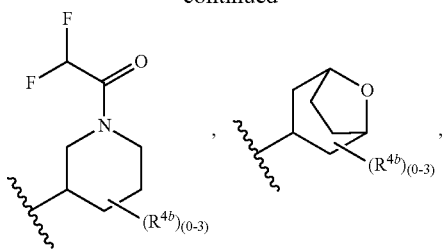
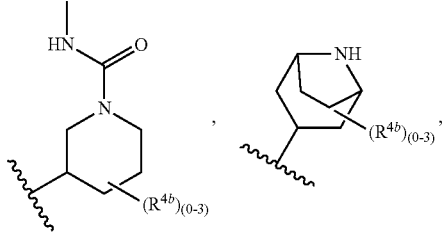
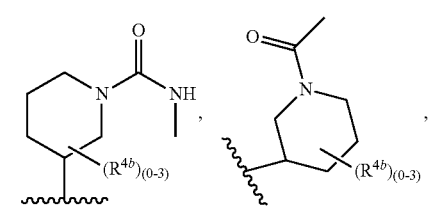
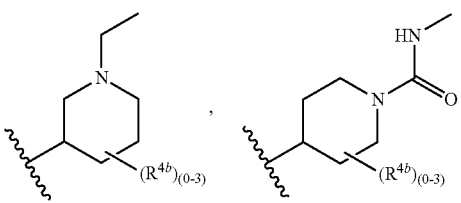
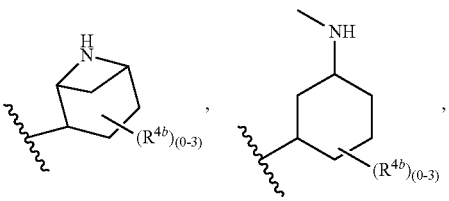
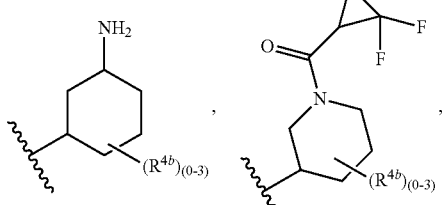
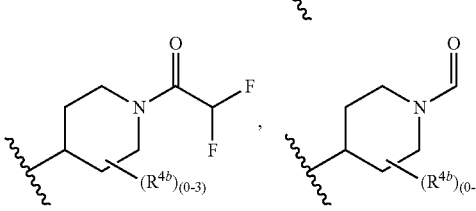

-continued
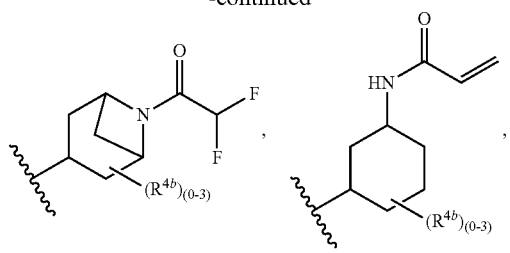
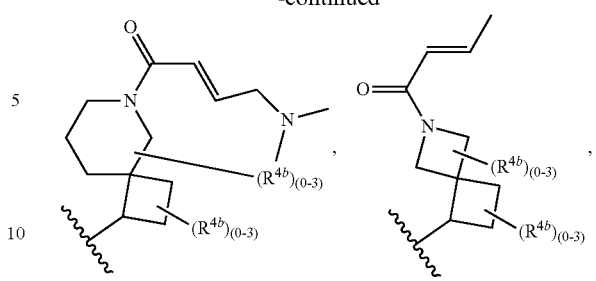
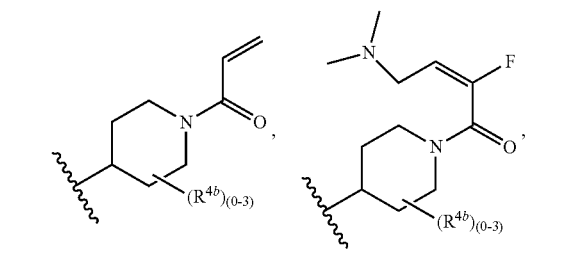
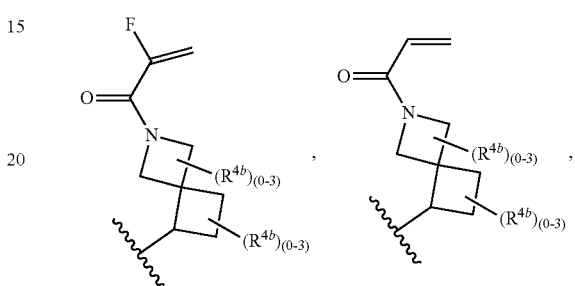
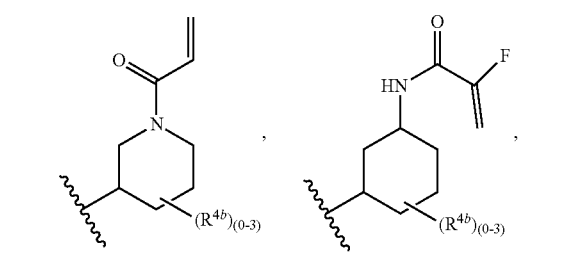
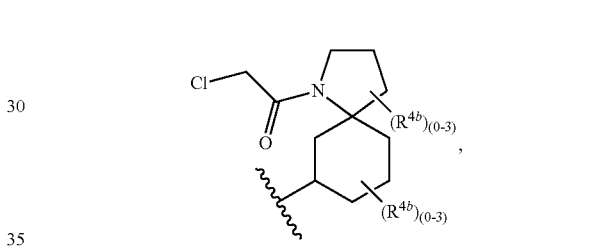
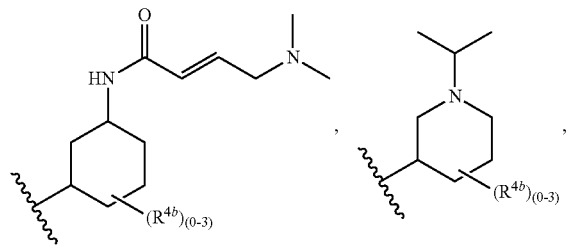
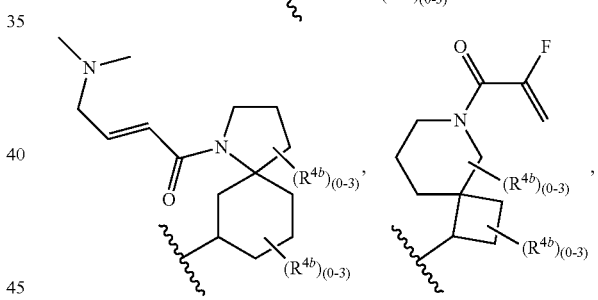
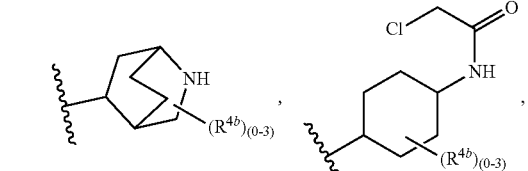
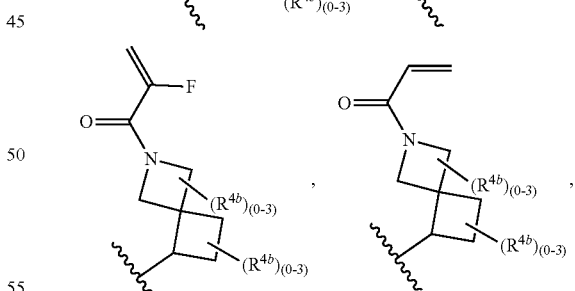
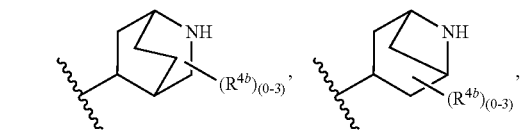
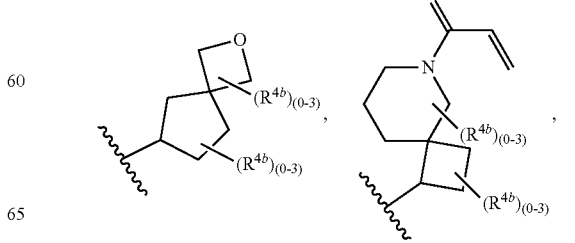

621
-continued

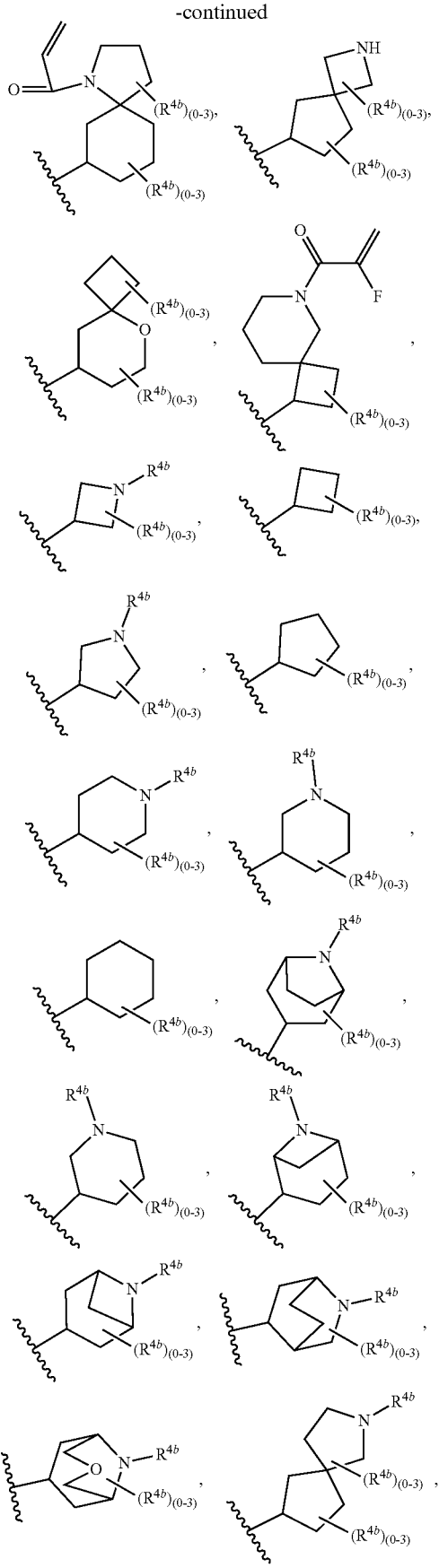

622
-continued

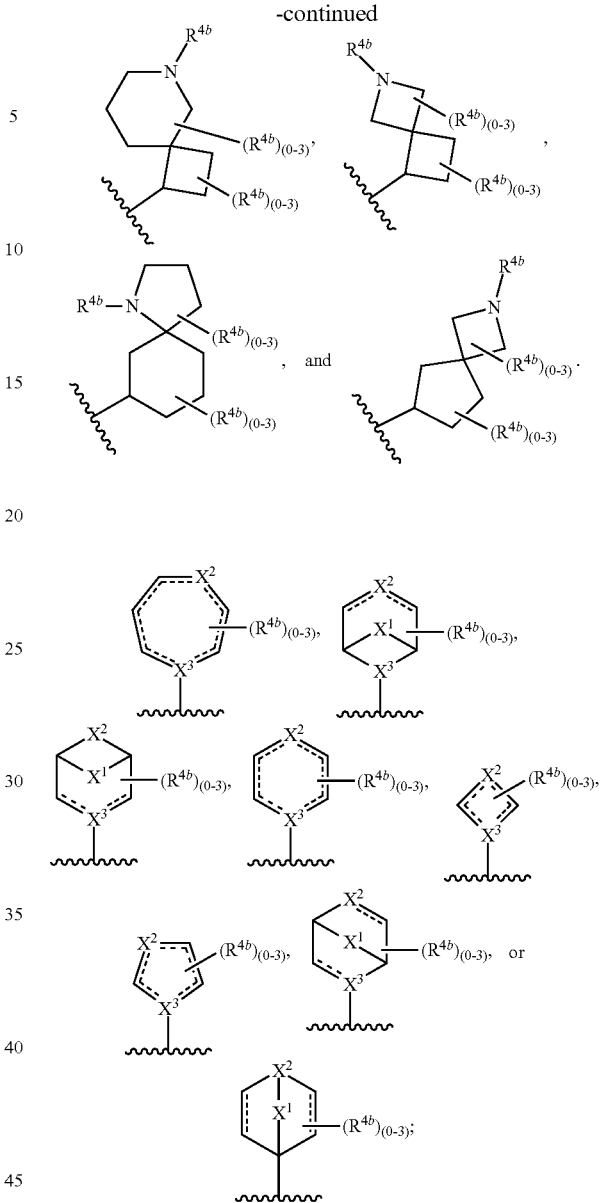

In embodiments of the formulae above, $R^{4a}$ is
$X^1$ is selected from $CH_2$, $C(R^4b)(H)$, $C=N-OH$, $C=NNH2$, $N(R^{46})$, $N(H)$, $O$, $S$, $S(O)$, $S(=O)(=NH)$, $S(O)_2$, $C=N-OH$, $C-NN(H)(H)$, $C(R^4b)(R^4b)$,$C(O)N(R^4b)$, $S(O)_2N(R^4b)$, $S(O)N(R^{46})$, $CH_2C(R^4b)(H)$, $C(R^4b)(H)C=N-OH$, $CH_2C=NNH2$, $C(R^4b)(H)N(R^4b)$, $C(R^4b)(H)N(H)$, $C(R^4b)(H)O$, $C(R^4b)(H)S(O)$, $C(R^4b)(H)S(=O)(=NH)$, $C(R^{4b})(H)S(O)_2$, $C=NNH_2$, $C(R^4b)(H)$, $CH_2C(R^{46})(R^4b)$, $C(R^4b)(R^4b)C=N-OH, CH_2C=NNH_2, C(R^{4b})(R^4b)N(R^4b), C(R^4b)(R^4b)N(H)$, $C(R^4b)(R^4b)O$, $C(R^4b)(R^4b)S$, $C(R^4b)(R^4b)S(O)$, $C(R^4b)(R^4b)S(=O)(=NH)$, $C(R^4b)(R^4b)S(O)_2, C=NN(R^4b)(R^4b)C(R^4b)(R^4b)$, $C(O)N(H)$, $S(O)_2N(H)$, $S(O)N(H)$, $CH_2CH_2$, $CH_2C=N-OH$, $CH_2C=NNH_2$, $CH_2N(H)$, $CH_2O$, $CH_2S(O)$, $CH_2S(-O)(=NH)$, $CH_2S(O)_2$, $C-NN(H)(H)CH_2$, $CH_2C=N-OH$, $CH_2S$, $N(R^4b)S(O)N(R^4b)$, $N(R^4b)S(O)_2N(R^4b),OC(O)N(R^4b)$, $N(R^4b)C(O)N(R^4b)$, $CH_2C(R^4b)(H)CH_2$, $C(R^4b)(H)C(R^4b)(H)C(R^4b)(H)$, $C(R^4b)(H)C(O)N(R^4b)$, $C(R^4b)(H)OC(R^4b)$ (H), C(R⁴b)(H)S, C(R⁴b)(H)SC(R⁴b)(H), C(R⁴b)(H)S(O)C(R⁴b)(H), C(R⁴b)(H)S(O)₂C(R⁴b)(H), C(R⁴b)(H)S(O)₂N(R⁴b),C(R⁴b)(H)N(R⁴b)S(O)N(R⁴b), C(R⁴b)(H)N(R⁴b)S(O)₂N(R⁴b), C(R⁴b)(H)S(O)N(R⁴b), C(O)N(R⁴b)C(R⁴b)(H), S(O)₂N(R⁴b)C(R⁴b)(H), S(O)N(R⁴b)C(R⁴b)(H), CH₂C(R⁴b)(R⁴b)CH₂, C(R⁴b)(R⁴b)C(R⁴b)(H)C(R⁴b)(R⁴b), C(R⁴b)(R⁴b)C(R⁴b)(R⁴b)C(R⁴b)(R⁴b),C(R⁴b)(R⁴b)C(O)N(R⁴b), C(R⁴b)(R⁴b)OC(R⁴b)(R⁴b), C(R⁴b)(R⁴b)SC(R⁴b)(R⁴b), C(R⁴b)(R⁴b)S(O)C(R⁴b)(R⁴b),C(R⁴b)(R⁴b)S(O)₂C(R⁴b)(R⁴b),C(R⁴b)(R⁴b)S(O)₂N(R⁴b), C(R⁴b)(R⁴b)S(O)N(R⁴b), C(O)N(R⁴b)C(R⁴b)(R⁴b), S(O)₂N(R⁴b)C(R⁴b)(R⁴b), S(O)N(R⁴b)C(R⁴b)(R⁴b), N(H)S(O)N(H), N(H)S(O)₂N(H), OC(O)N(H), N(H)C(O)N(H), CH₂CH₂CH₂, CH₂C(O)N(H), CH₂OCH₂, CH₂S, CH₂SCH₂, CH₂S(O)CH₂, CH₂S(O)₂CH₂, CH₂S(O)₂N(H), CH₂N(H)S(O)N(H), CH₂N(H)S(O)₂N(H), CH₂S(O)N(H), C(O)N(H)CH₂, S(O)₂N(H)CH₂, S(O)N(H)CH₂, CH₂C(O)N(H), CH₂S(O)₂N(H), CH₂S(O)N(H), C(O)N(H)CH₂, S(O)₂N(H)CH₂, S(O)N(H)CH₂, CH₂OC(O)N(H), CH₂N(H)C(O)N(H), OC(O)N(H)CH₂, CH₂N(H)S(O)N(H), CH₂N(H)S(O)₂N(H), CH₂OC(O)N(H), CH₂N(R⁴b)C(O)N(H), and OC(O)N(H)CH₂;

$X^2$ is selected from N, N(H), N(R⁴b), O, S, S(O), C, C(R⁴b), CH, C(H)(R⁴b), C(R⁴b)₂, CH₂, S(=O)(=NH), S(O)₂; and $X^3$ is selected from N, C, C(H), and C(R⁴b).

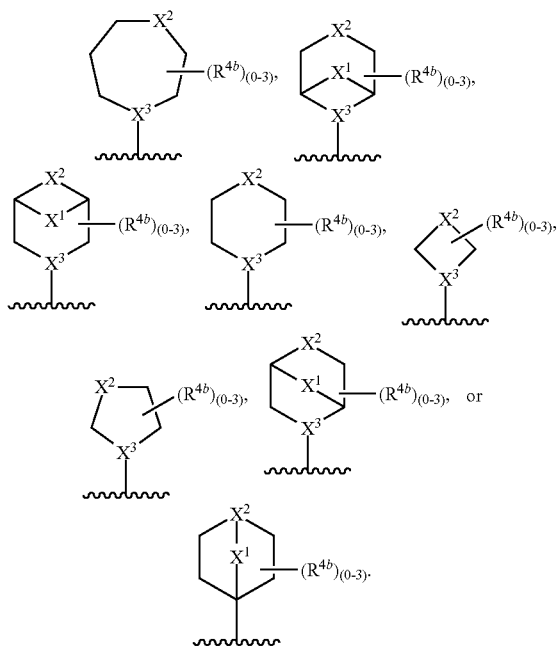

In embodiments of the formulae above, $R^{4a}$ is

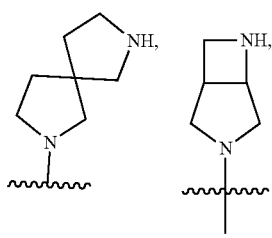

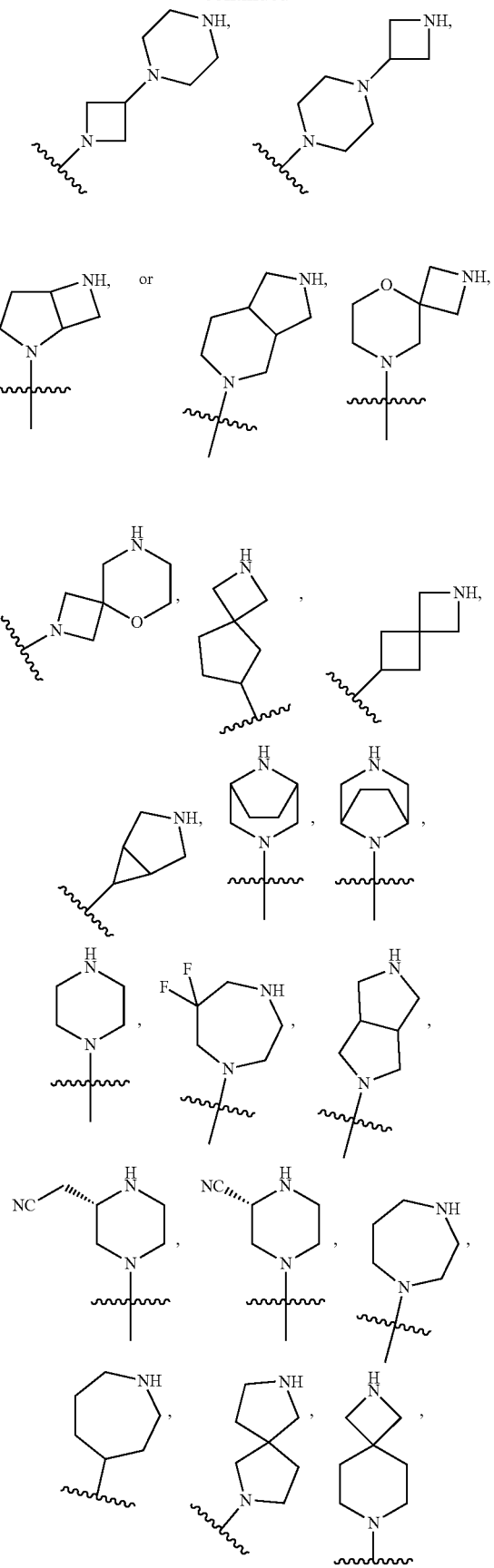

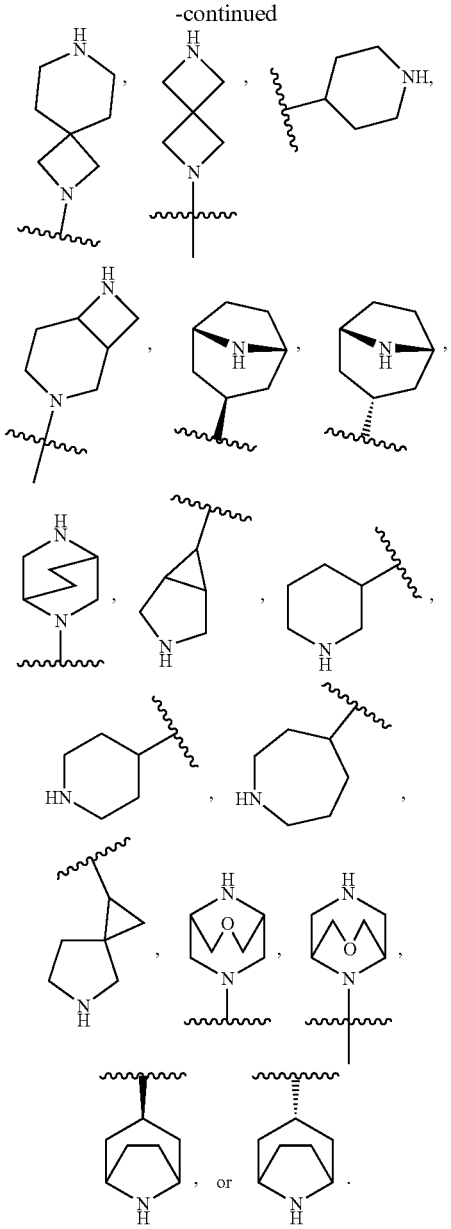
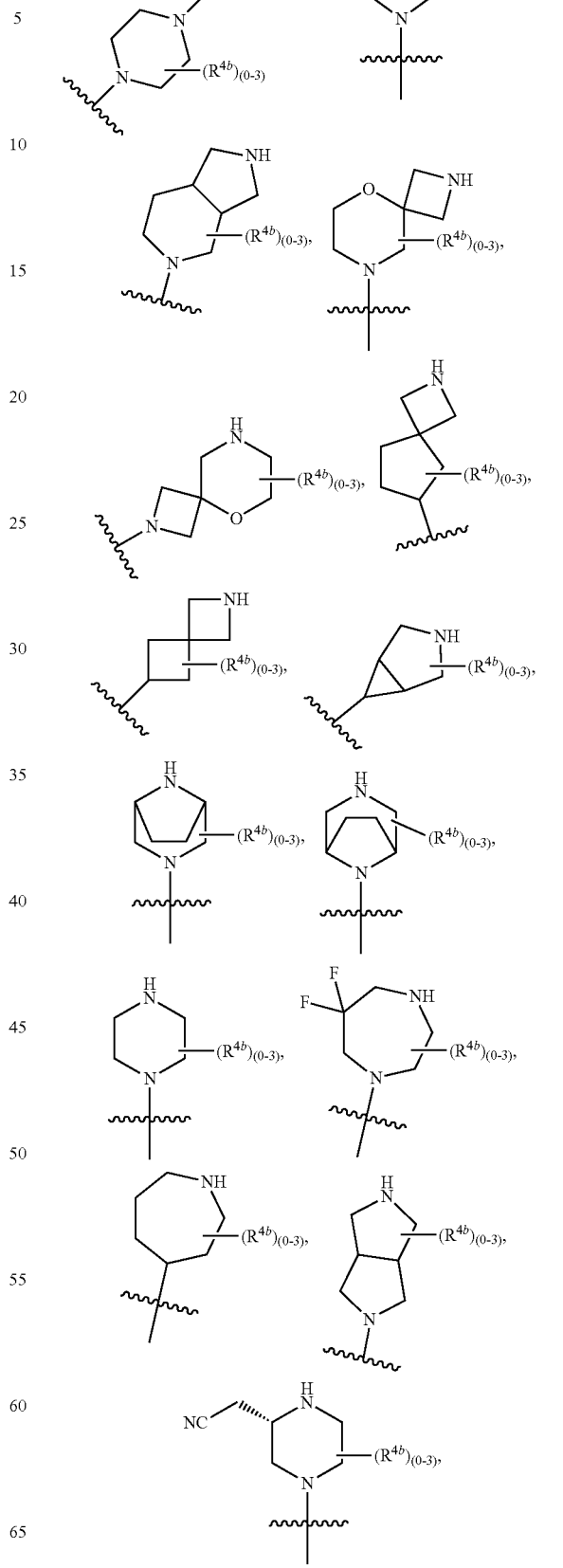
In embodiments of the formulae above, $R^{4a}$ is
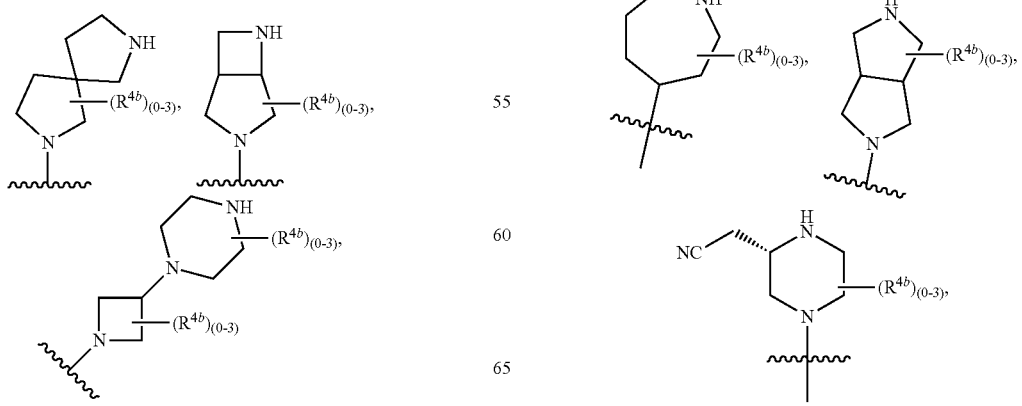

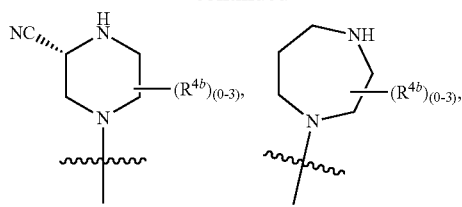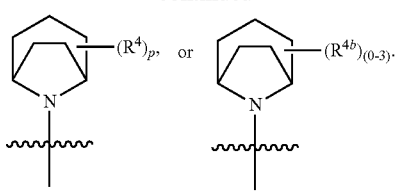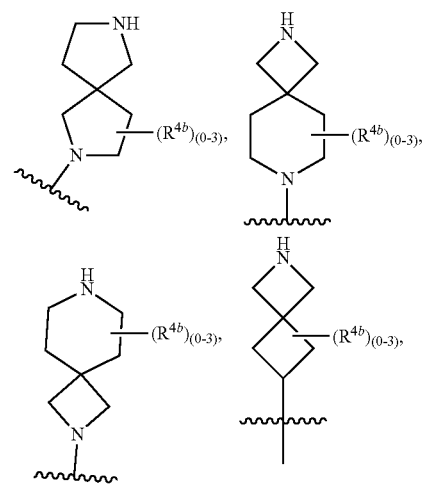
In embodiments of the formulae above, $R^{4a}$ is
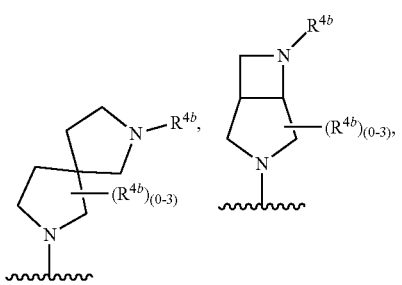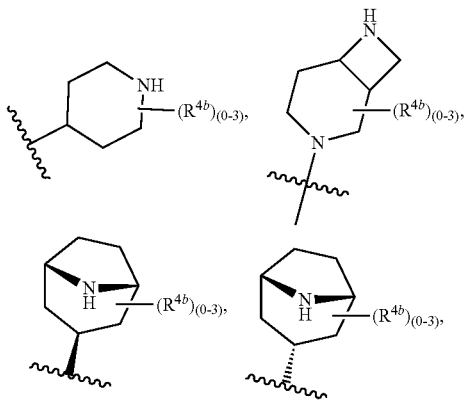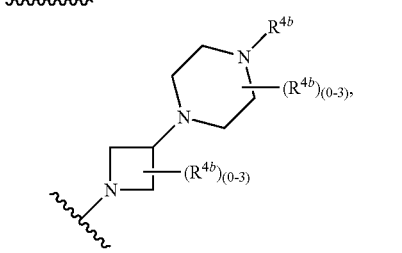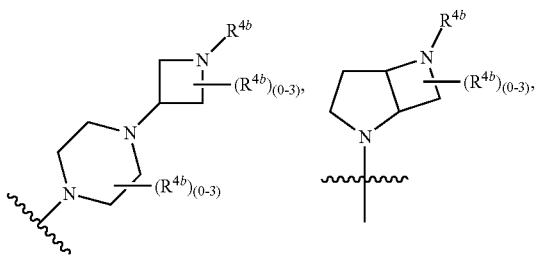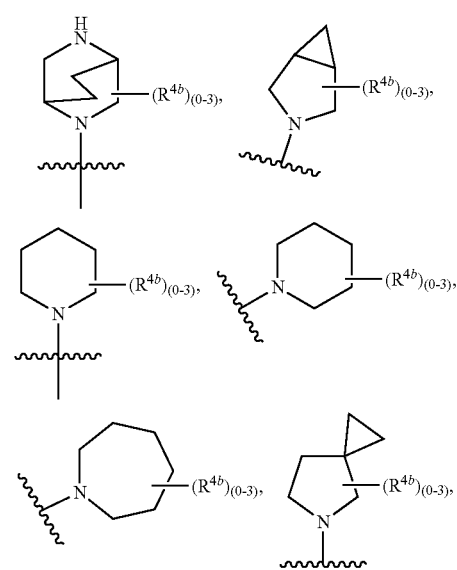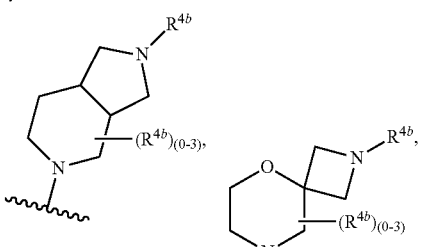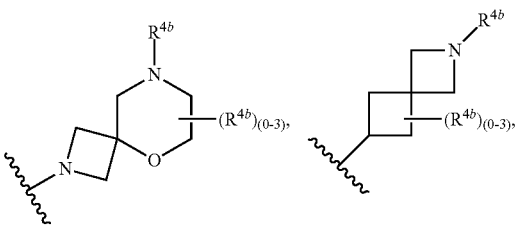

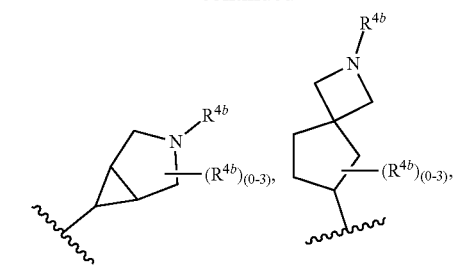
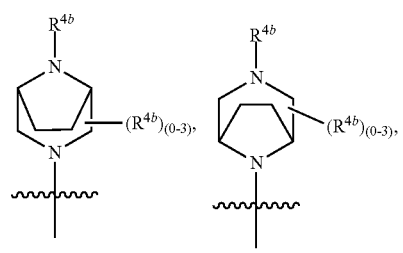
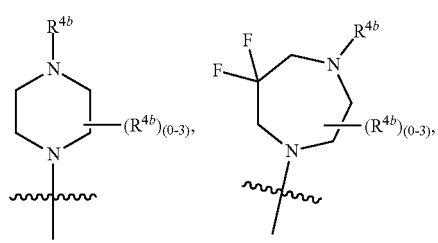
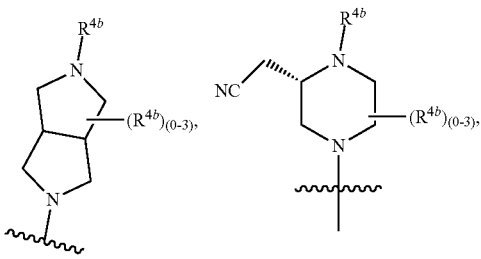
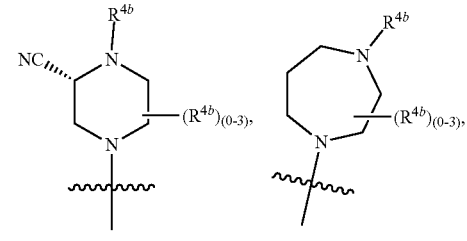
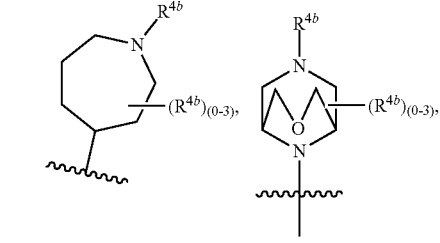
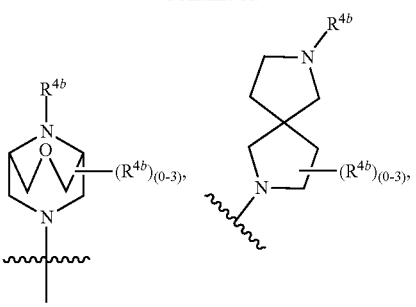
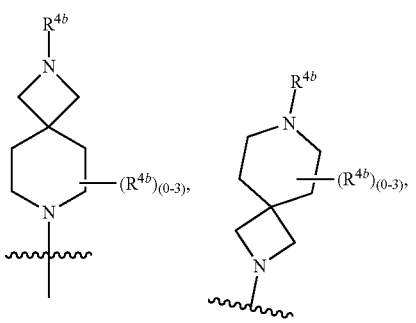
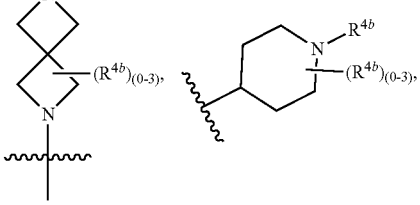
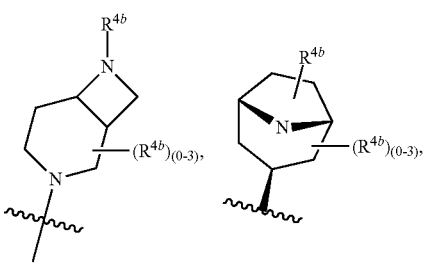
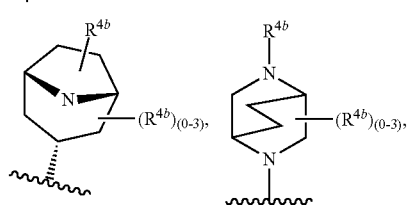
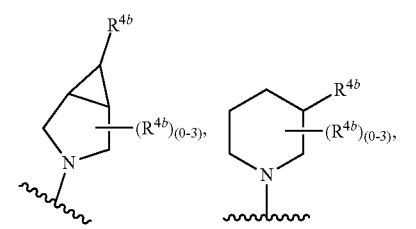

631
-continued
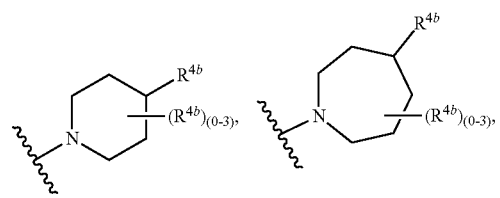
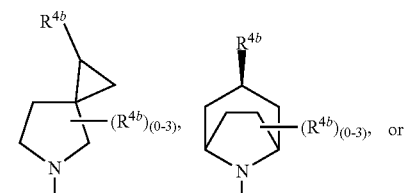
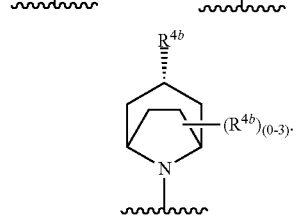
In embodiments of the formulae above, $R^{4a}$ is
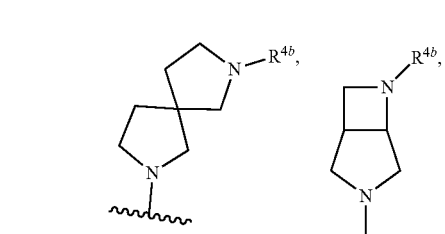
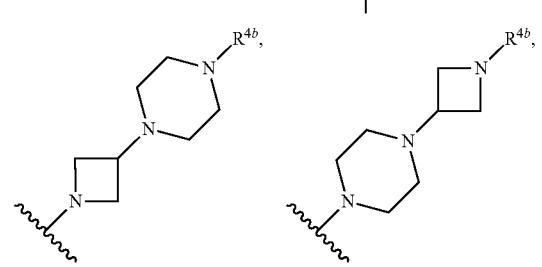
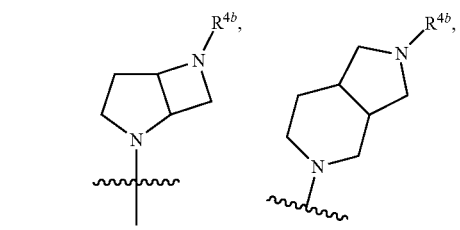
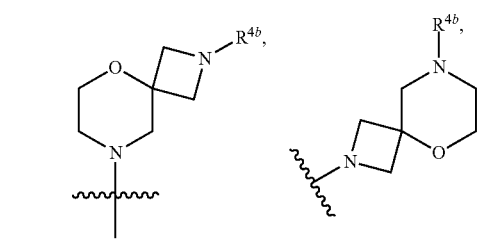
632
-continued
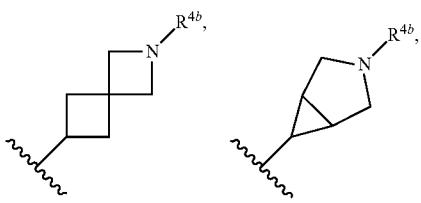
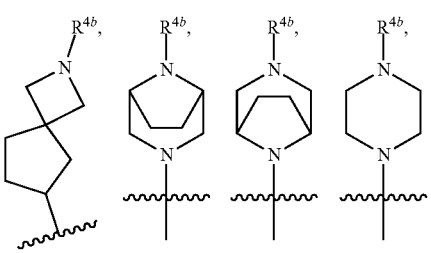
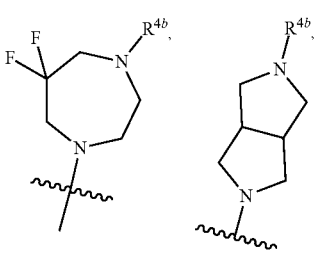
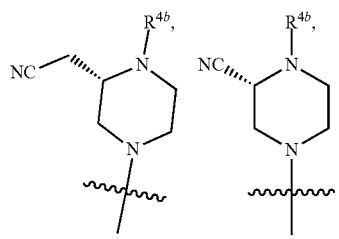
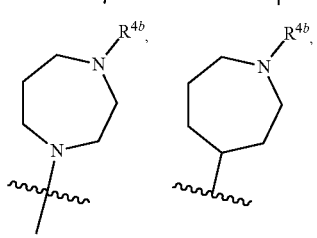
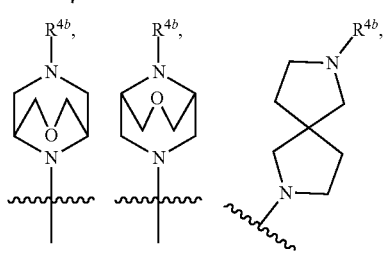
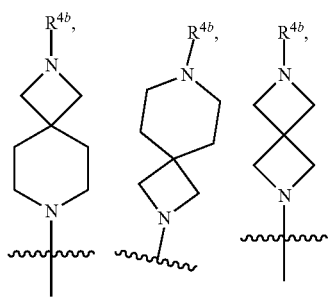

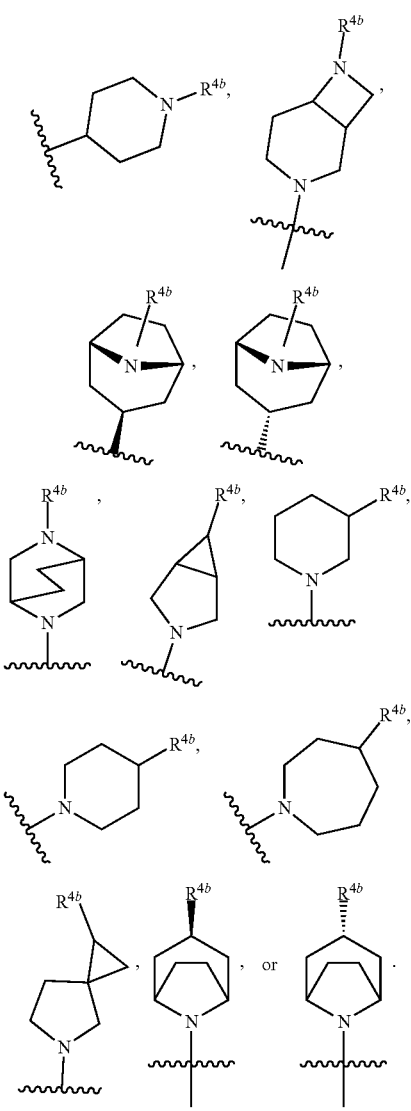
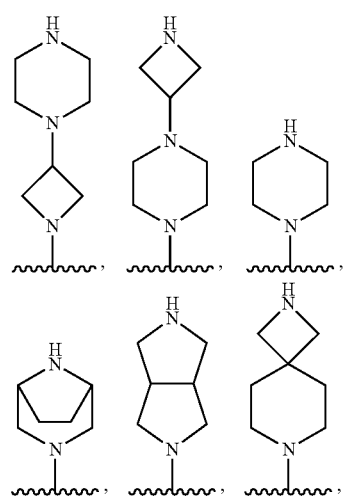
In embodiments of the formulae above, $R^{4a}$ is
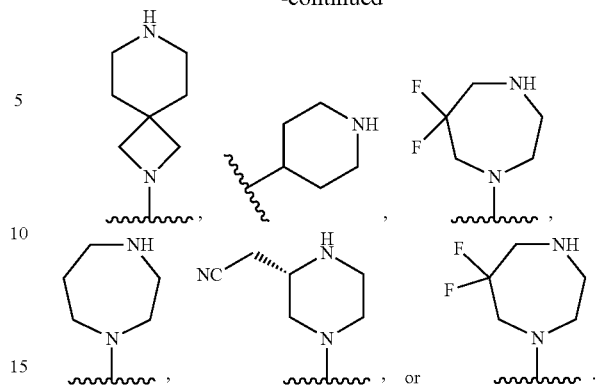
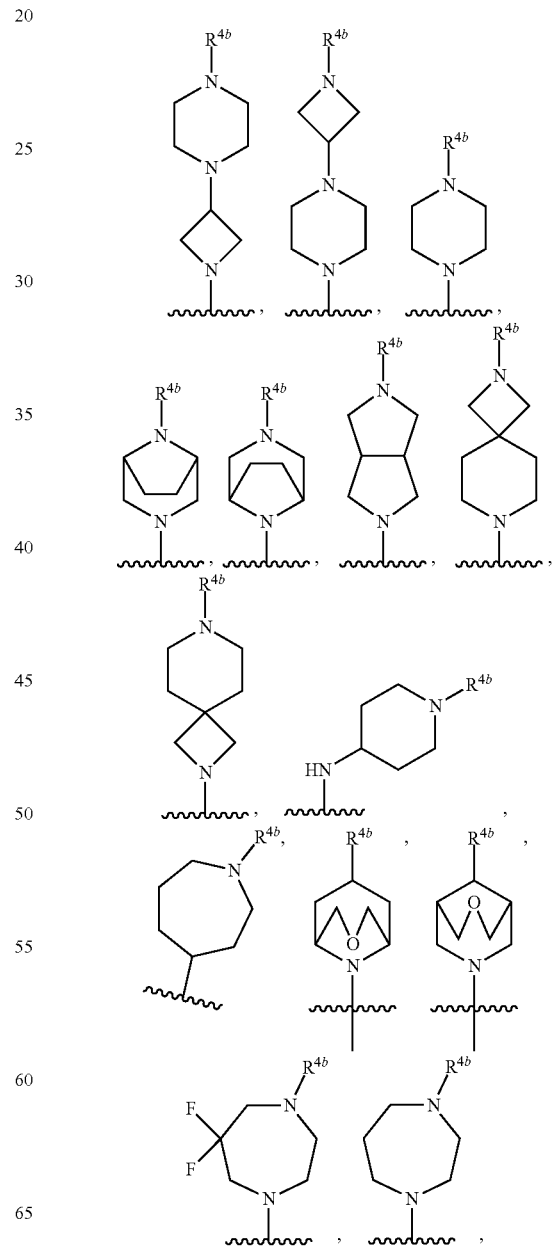
In embodiments of the formulae above, $R^{4a}$ is -continued
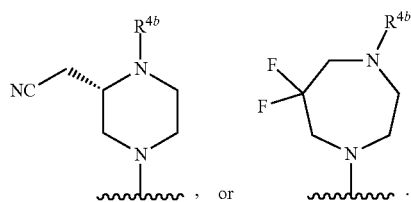
In embodiments of the formulae above, R$^{4a}$ is
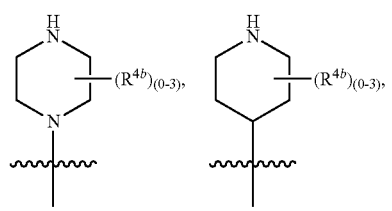
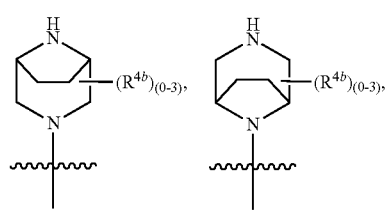
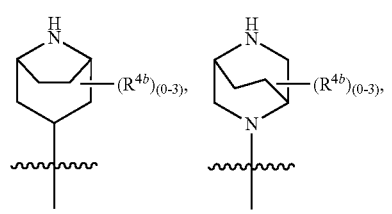
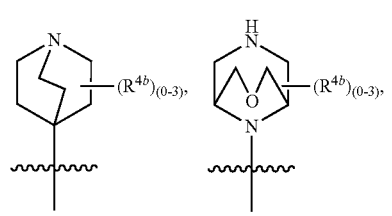
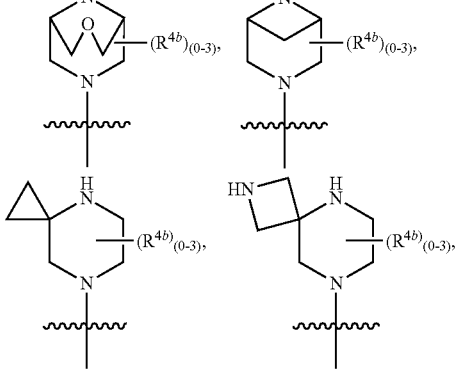
-continued
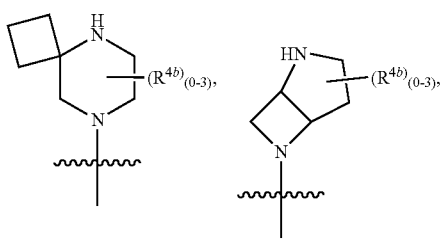
In embodiments of the formulae above, R$^{4a}$ is

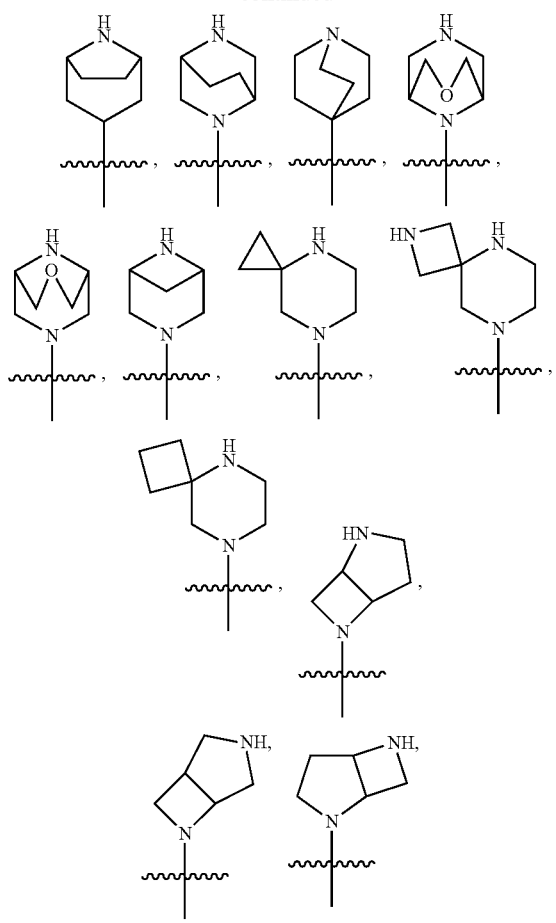

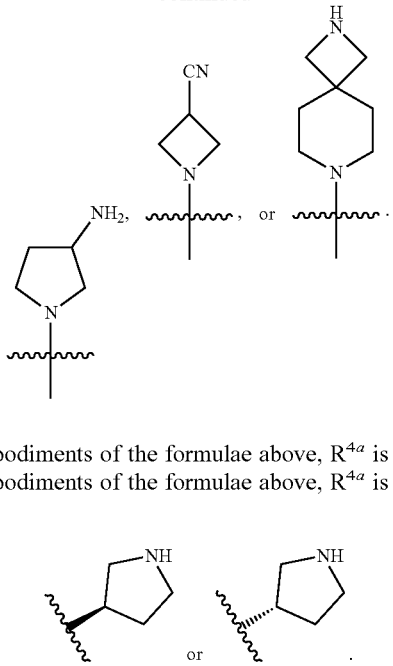

In embodiments of the formulae above, $R^{4a}$ is
In embodiments of the formulae above, $R^{4a}$ is

[structures: two pyrrolidine-NH stereoisomers] or .

In embodiments of the formulae above, $R^{4a}$ is

[structures: two tetrahydrofuran stereoisomers] or .

The individual embodiments herein below, or combinations thereof, (e.g., embodiments of $R^{11c}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In embodiments of the formulae above, each $R^{11c}$ is independently hydrogen.

The individual embodiments herein below, or combinations thereof, (e.g., embodiments of $R^{11c}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{11c}$ is independently halogen. In embodiments of the formulae above, each $R^{11c}$ is independently F. In embodiments of the formulae above, each $R^{11c}$ is independently $C_1$. In embodiments of the formulae above, each $R^{11c}$ is independently Br. In embodiments of the formulae above, each $R^{11c}$ is independently I. In embodiments of the formulae above, each $R^{11c}$ is independently oxo. In embodiments of the formulae above, each $R^{11c}$ is independently —CN. In embodiments of the formulae above, each $R^{11c}$ is independently $C_{1-6}$alkyl. In embodiments of the formulae above, each $R^{11c}$ is independently $C_{2-6}$alkenyl. In embodiments of the formulae above, each $R^{11c}$ is independently $C_{2-6}$alkynyl. In embodiments of the formulae above, each $R^{11c}$ is independently $C_{1-6}$haloalkyl. In embodiments of the formulae above, each $R^{11c}$ is independently $C_{3-12}$cycloalkyl. In embodiments of the formulae above, each $R^{11c}$ is independently —$CH_2$-$C_{3-12}$cycloalkyl. In embodiments of the formulae above, each $R^{11c}$ is independently $C_{1-11}$heterocycloalkyl. In embodiments of the formulae above, each $R^{11c}$ is independently —$CH_2$-$C_{1-11}$heterocycloalkyl. In embodiments of the formulae above, each $R^{11c}$ is independently $C_{6-10}$aryl. In embodiments of the formulae above, each $R^{11c}$ is independently —$CH_2$-$C_{6-10}$aryl. In embodiments of the formulae above, each $R^{11c}$ is independently —$CH_2$-$C_{1-11}$heteroaryl. In embodiments of the formulae above, each $R^{11c}$ is independently $C_{1-11}$heteroaryl. In embodiments of the formulae above, each $R^{11c}$ is independently —$OR^{12}$. In embodiments of the formulae above, each $R^{11c}$ is independently —$SR^{12}$. In embodiments of the formulae above, each $R^{11c}$ is independently —$N(R^{12})(R^{13})$. In embodiments of the formulae above, each $R^{11c}$ is independently —$C(O)OR^{12}$. In embodiments of the formulae above, each $R^{11c}$ is independently —$OC(O)N(R^{12})(R^{13})$. In embodiments of the formulae above, each $R^{11c}$ is independently —$N(R^{14})C(O)N(R^{12})(R^{13})$. In embodiments of the formulae above, each $R^{11c}$ is independently —$N(R^{14})C(O)OR^{15}$. In embodiments of the formulae above, each $R^{11c}$ is independently —$N(R^{14})S(O)_2R^{15}$. In embodiments of the formulae above, each $R^{11c}$ is independently —$C(O)R^{15}$. In embodiments of the formulae above, each $R^{11c}$ is independently —$S(O)R^{15}$. In embodiments of the formulae above, each $R^{11c}$ is independently —$OC(O)R^{15}$. In embodiments of the formulae above, each $R^{11c}$ is independently —$C(O)N(R^{12})(R^{13})$. In embodiments of the formulae above, each $R^{11c}$ is independently —$C(O)C(O)N(R^{12})(R^{13})$. In embodiments of the formulae above, each $R^{11c}$ is independently —$N(R^{14})C(O)R^{15}$. In embodiments of the formulae above, each $R^{11c}$ is independently —$S(O)_2R^{15}$. In embodiments of the formulae above, each $R^{11c}$ is independently —$S(O)_2N(R^{12})(R^{13})$—. In embodiments of the formulae above, each $R^{11c}$ is independently $S(=O)(=NH)N(R^{12})(R^{13})$. In embodiments of the formulae above, each $R^{11c}$ is independently —$CH_2C(O)N(R^{12})(R^{13})$. In embodiments of the formulae above, each $R^{11c}$ is independently —$CH_2N(R^{14})C(O)R^{15}$. In embodiments of the formulae above, each $R^{11c}$ is independently —$CH_2S(O)_2R^{15}$. In embodiments of the formulae above, each $R^{11c}$ is independently —$CH_2S(O)_2N(R^{12})(R^{13})$. In embodiments of the formulae above, each $R^{11c}$ is independently $C_{1-6}$alkyl substituted with one, two, or three $R^{20k}$; In embodiments of the formulae above, each $R^{11c}$ is independently $C_{2-6}$alkenyl substituted with one, two, or three $R^{20k}$; In embodiments of the formulae above, each $R^{11c}$ is independently $C_{2-6}$alkynyl substituted with one, two, or three $R^{20k}$; In embodiments of the formulae above, each $R^{11c}$ is independently $C_{1-6}$haloalkyl substituted with one, two, or three $R^{20k}$; In embodiments of the formulae above, each $R^{11c}$ is independently $C_{3-12}$cycloalkyl substituted with one, two, or three $R^{20k}$; In embodiments of the formulae above, each $R^{11c}$ is independently —$CH_2$-$C_{3-12}$cycloalkyl substituted with one, two, or three $R^{20k}$; In embodiments of the formulae above, each $R^{11c}$ is independently $C_{1-11}$heterocycloalkyl substituted with one, two, or three $R^{20k}$; In embodiments of the formulae above, each $R^{11c}$ is independently —$CH_2$-$C_{1-11}$heterocycloalkyl substituted with one, two, or three $R^{20k}$; In embodiments of the formulae above, each $R^{11c}$ is independently $C_{6-10}$aryl substituted with one, two, or three $R^{20k}$; In embodiments of the formulae above;

each $R^{11c}$ is independently —$CH_2$-$C_{6-10}$aryl substituted with one, two, or three $R^{20k}$; In embodiments of the formulae above, each $R^{11c}$ is independently —$CH_2$-$C_{1-11}$heteroaryl substituted with one, two, or three $R^{20k}$; In embodiments of the formulae above, each $R^{11c}$ is independently $C_{1-11}$heteroaryl substituted with one, two, or three $R^{20k}$; In embodiments of the formulae above, each $R^{11c}$ is independently —$C(O)R^{12}$. In embodiments of the formulae above, each $R^{11c}$ is independently —$N(R^{14})C(O)R^{12}$. In embodiments of the formulae above, each $R^{11c}$ is independently —$(C_{1-6}$alkyl$)$-$C(O)N(R^{12})(R^{13})$ wherein $C_{1-6}$alkyl is optionally substituted with one, two, or three $R^{20k}$; In embodiments of the formulae above, each $R^{11c}$ is independently —$(C_{1-6}$alkyl$)$-$N(R^{14})C(O)R^{12}$ wherein $C_{1-6}$alkyl is optionally substituted with one, two, or three $R^{20k}$; In embodiments of the formulae above, each $R^{11c}$ is independently —$(C_{1-6}$alkyl$)$-$S(O)_2R^{15}$ wherein $C_{1-6}$alkyl is optionally substituted with one, two, or three $R^{20k}$; In embodiments of the formulae above, each $R^{11c}$ is independently —$(C_{1-6}$alkyl$)$-$S(O)_2N(R^{12})(R^{13})$. In embodiments of the formulae above, each $R^{11c}$ is independently —$C(O)H$. In embodiments of the formulae above, each $R^{11c}$ is independently —$N(R^{14})C(O)H$. In embodiments of the formulae above, each $R^{11c}$ is independently —$(C_{1-6}$alkyl$)$-N ($R^{14}$)C(O)H wherein $C_{1-6}$alkyl is optionally substituted with one, two, or three $R^{20k}$. In embodiments of the formulae above, each $R^{11c}$ is independently —($C_{1-6}$alkyl)-N($R^{12}$)($R^{13}$) wherein $C_{1-6}$alkyl is optionally substituted with one, two, or three $R^{20k}$.
In embodiments of the formulae above, each $R^{110}$ is independently selected from
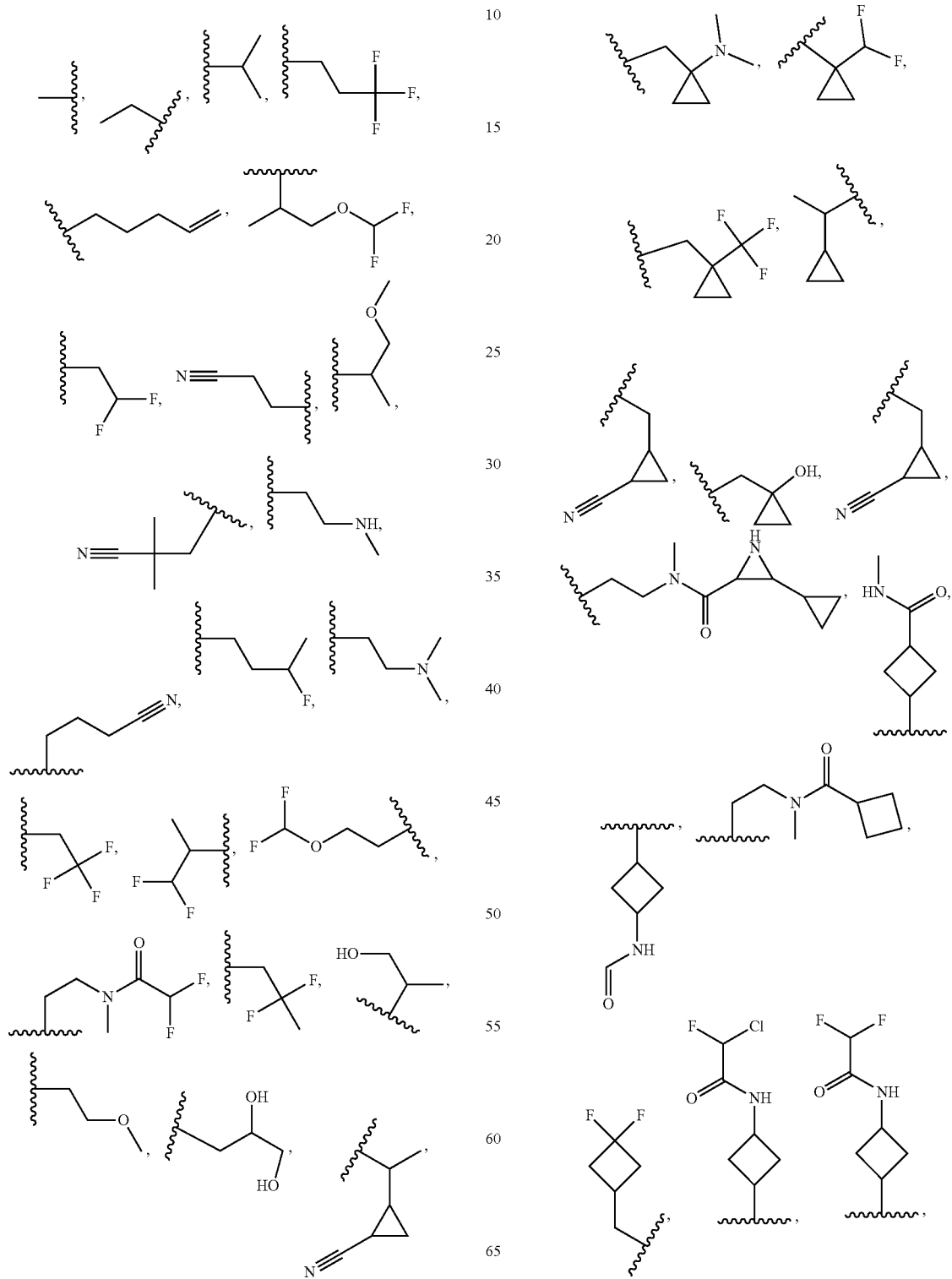

643
-continued
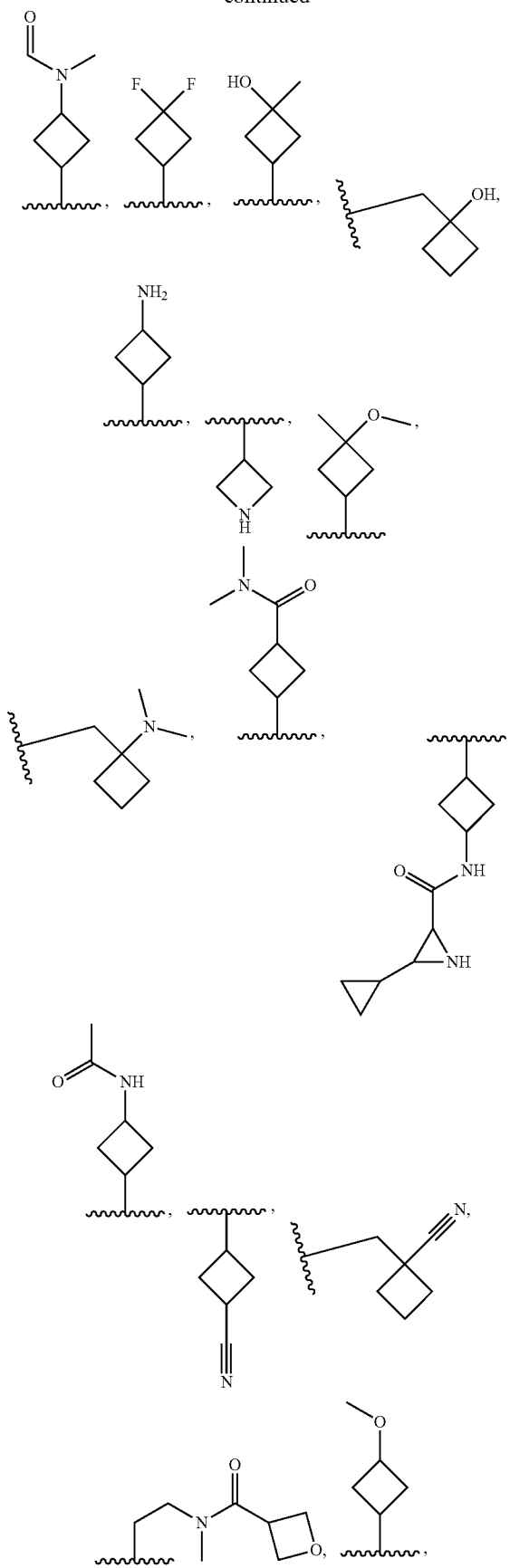
644
-continued
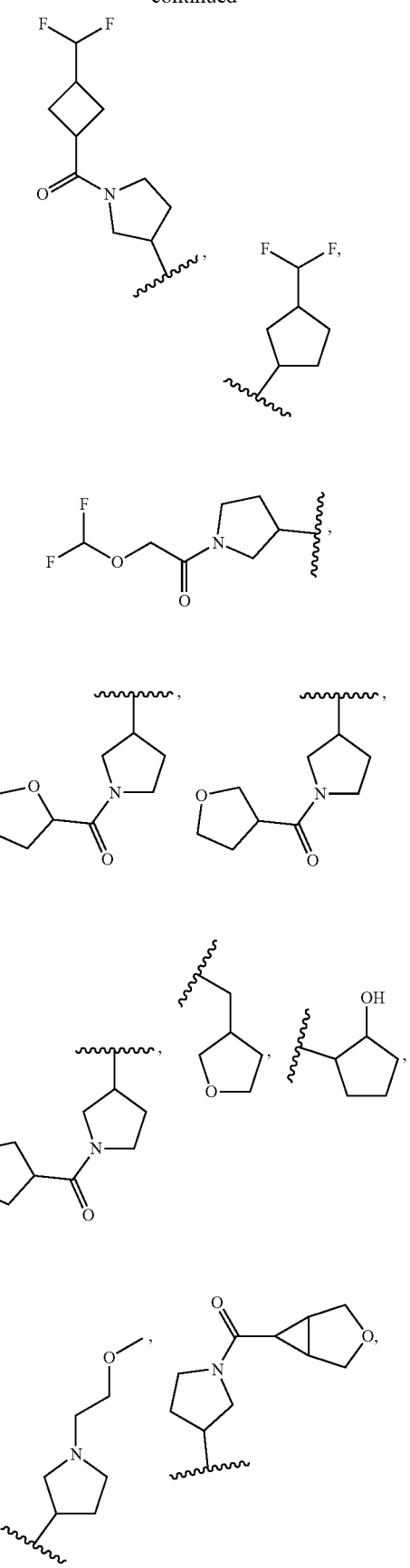

-continued
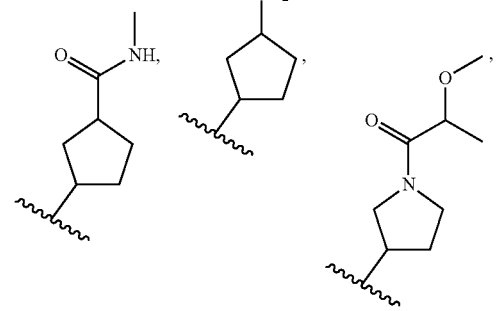
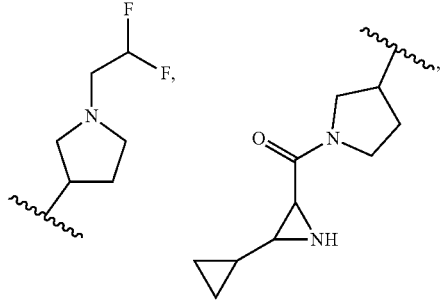
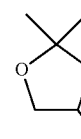
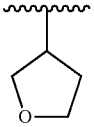
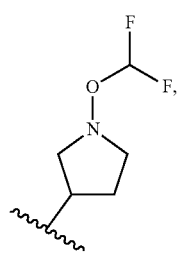
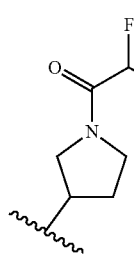
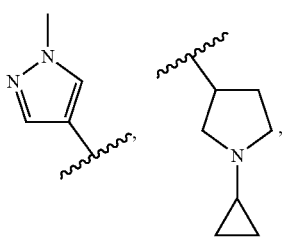
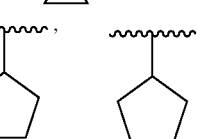
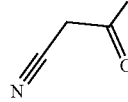
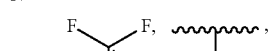
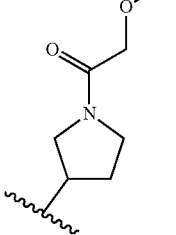

647
-continued
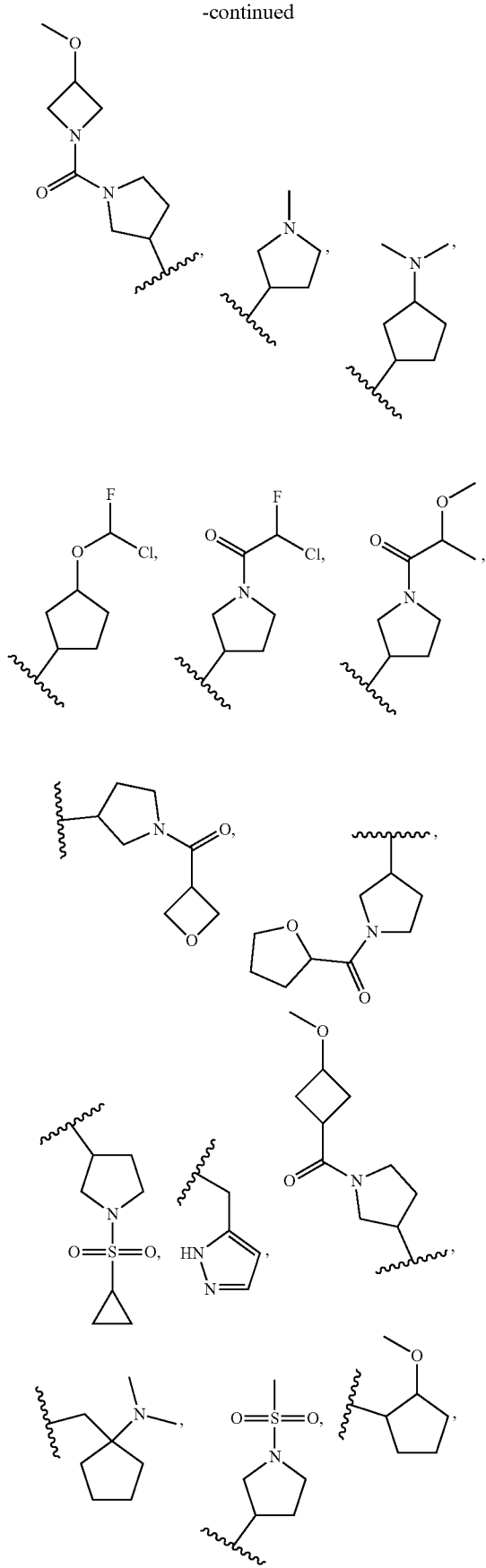
648
-continued
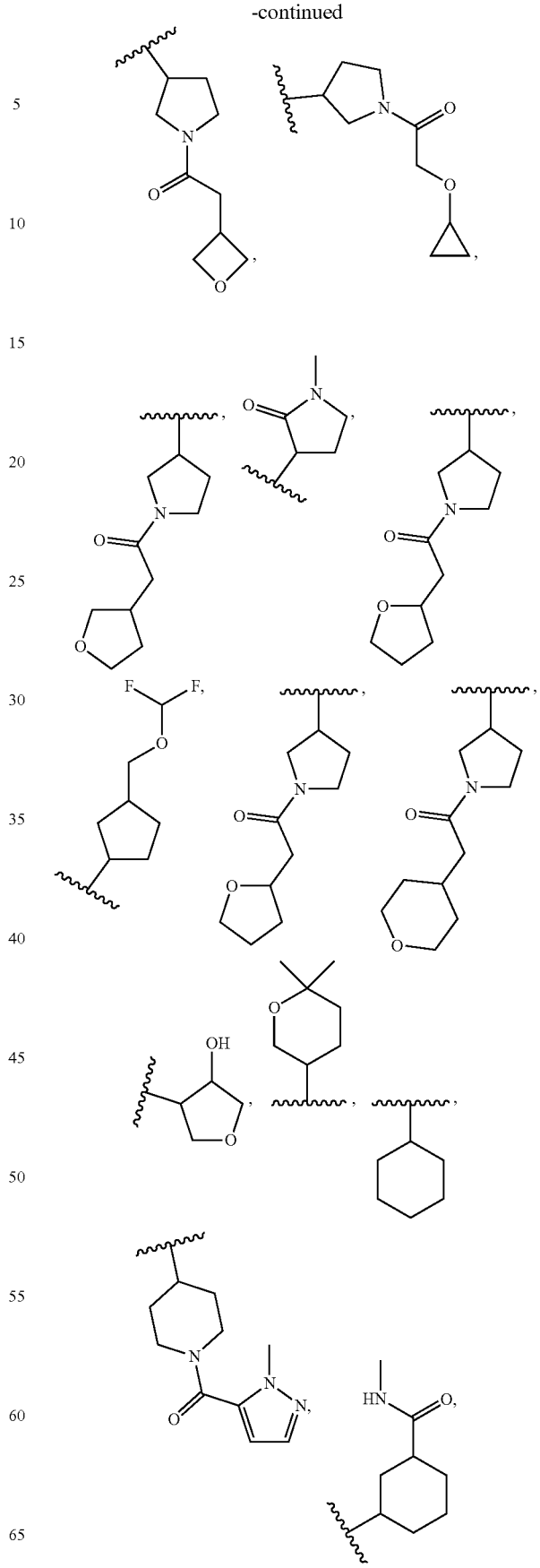

649
-continued
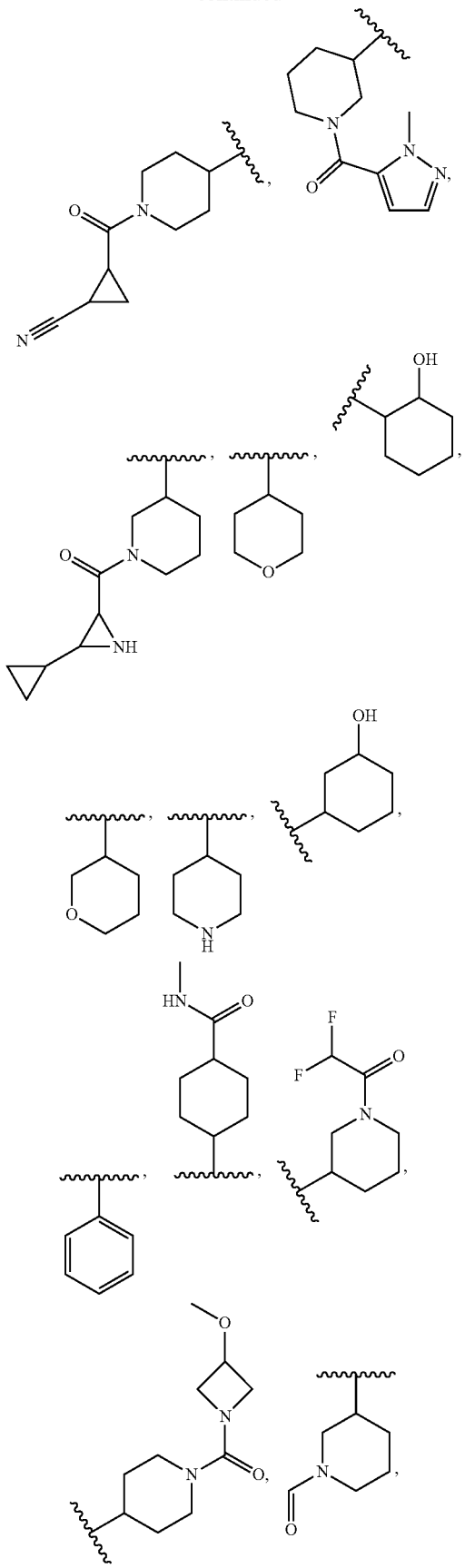
650
-continued
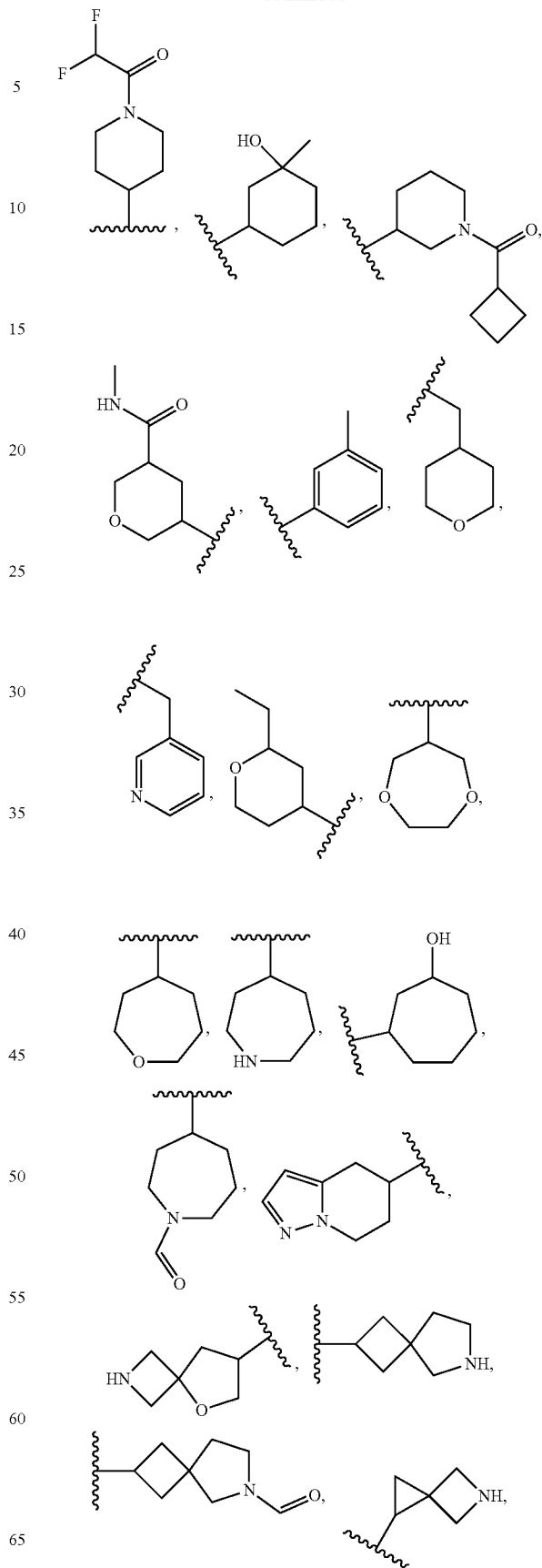

651
-continued
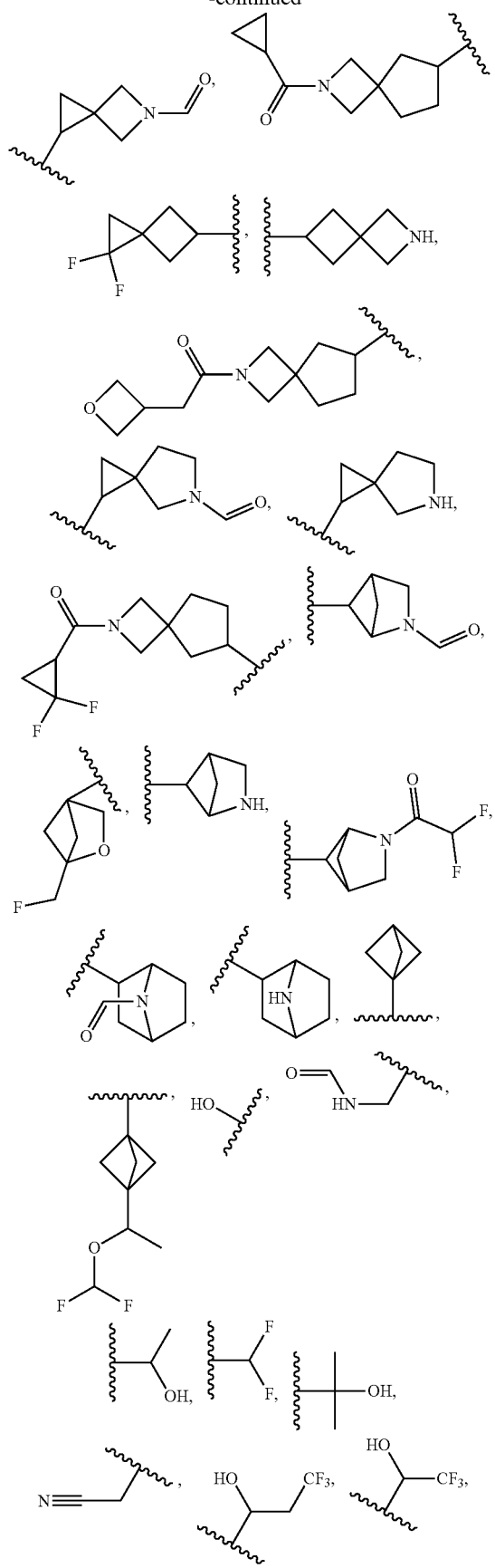
652
-continued
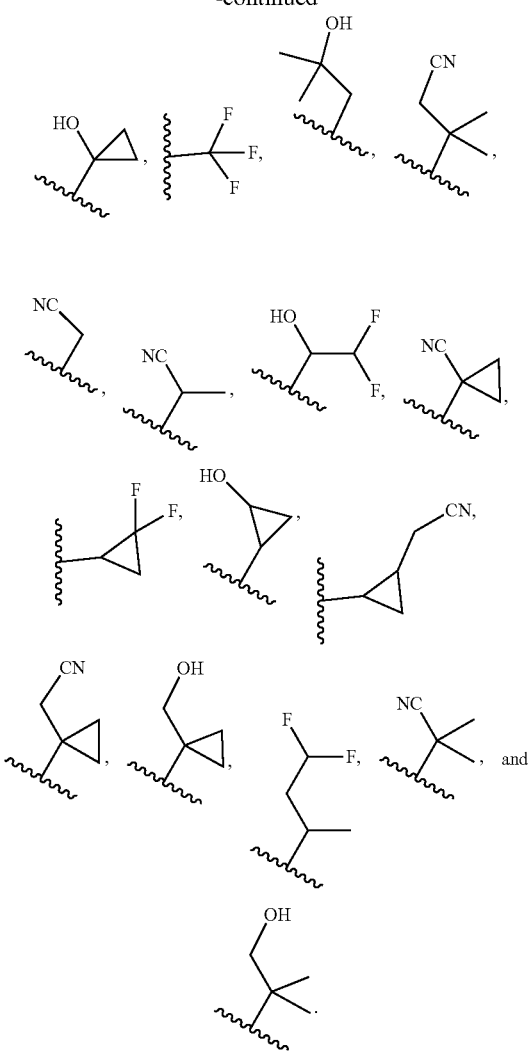
In embodiments of the formulae above, each $R^{11c}$ is independently selected from
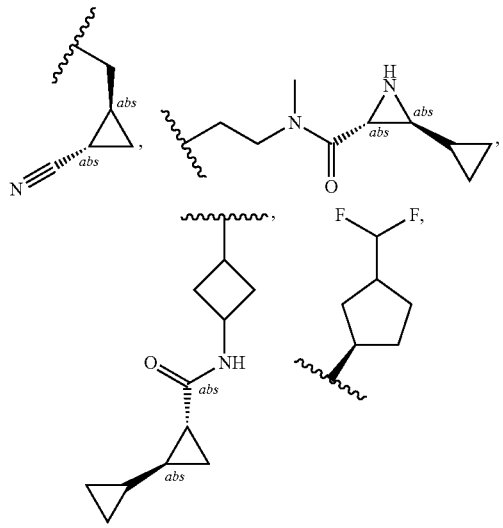

653
-continued
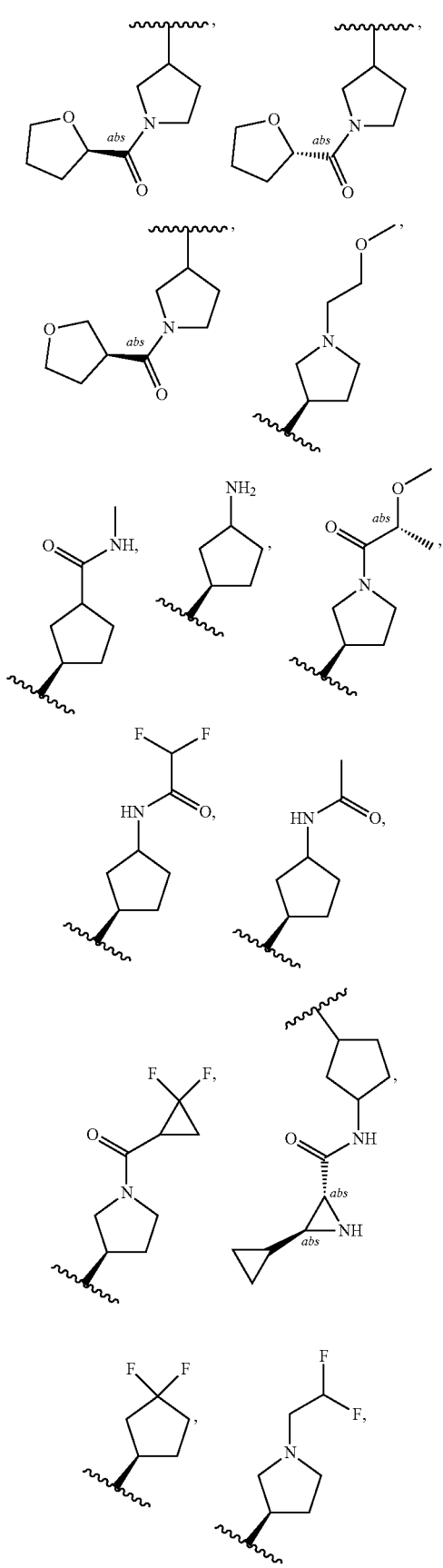
654
-continued
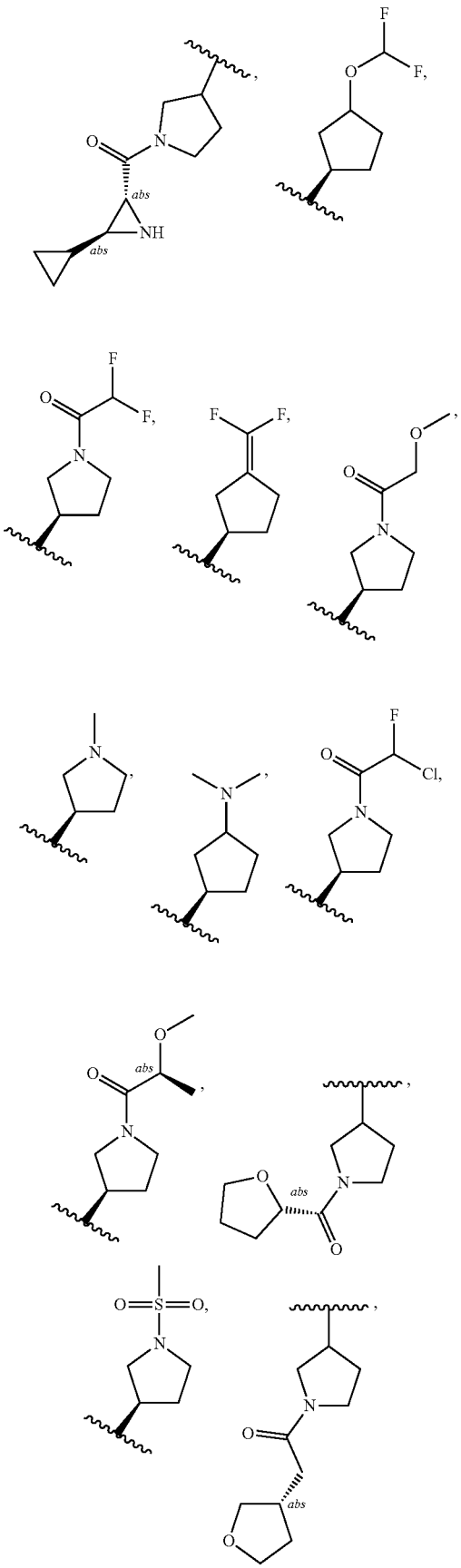

-continued
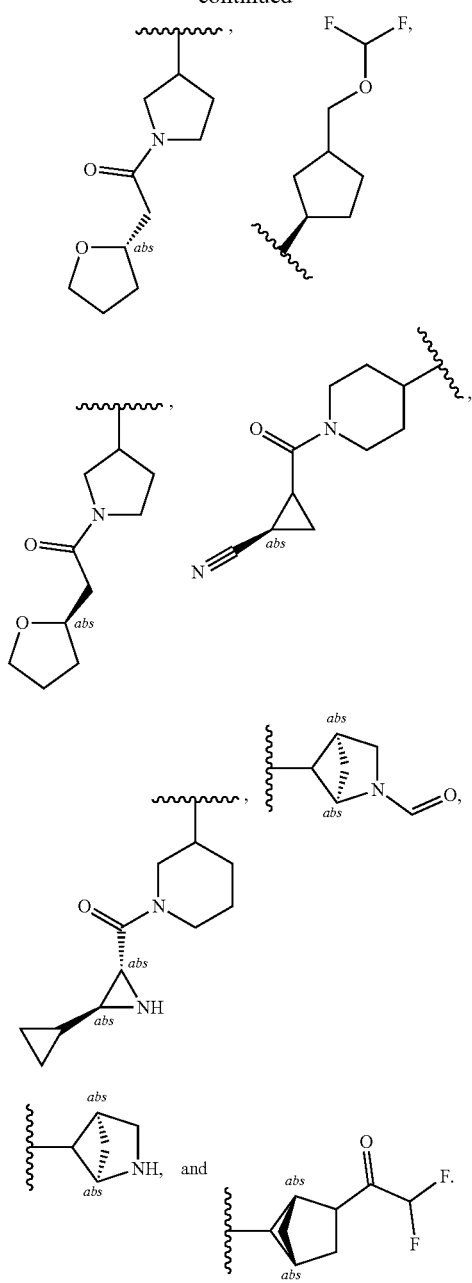
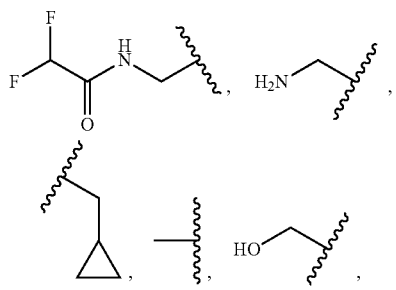
In embodiments of the formulae above, each $R^{11c}$ is independently selected from
-continued
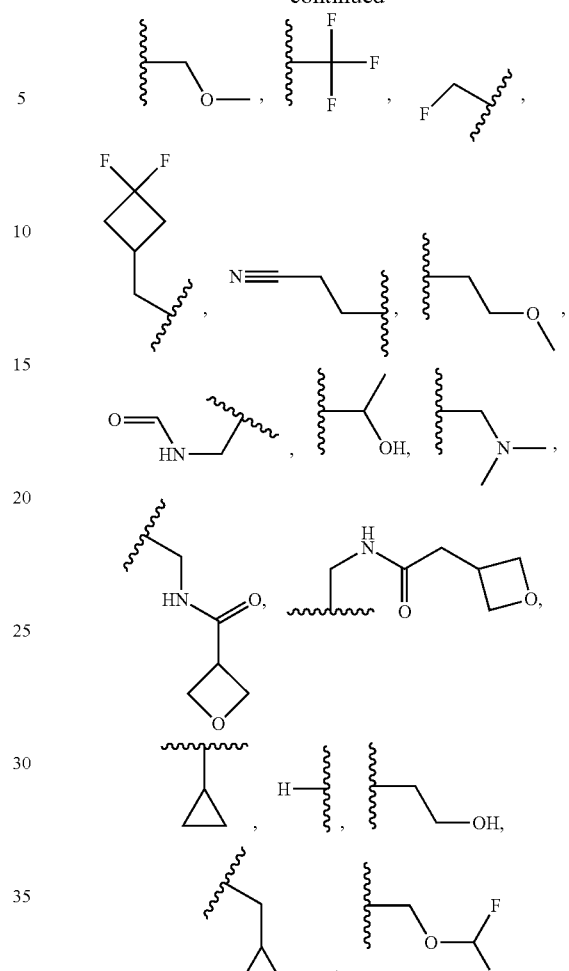
In embodiments of the formulae above, each $R^{11c}$ is independently selected from
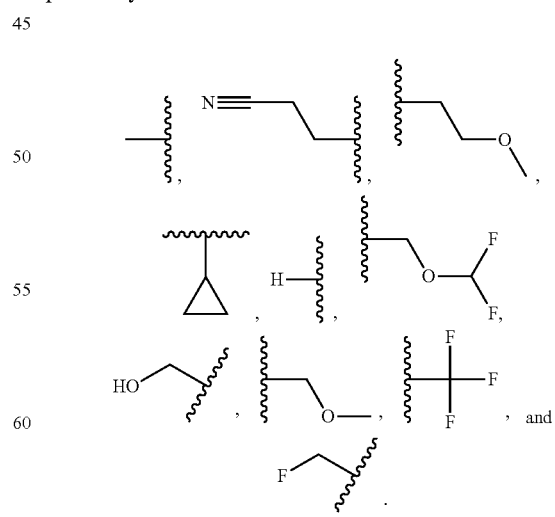
In embodiments of the formulae above, each $R^{11c}$ is independently selected from

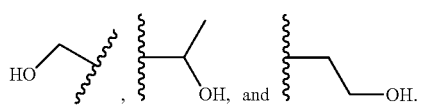
In embodiments of the formulae above, each $R^{11o}$ is independently selected from
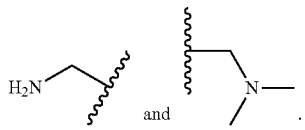
In embodiments of the formulae above, each $R^{11c}$ is independently selected from
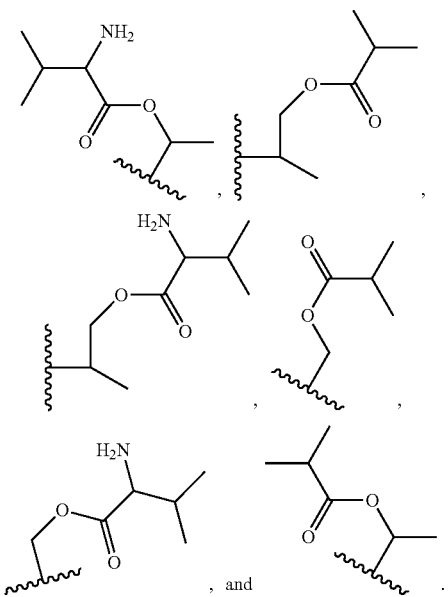
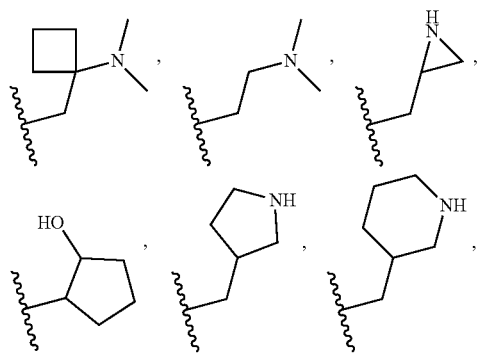
In embodiments of the formulae above, each $R^{11c}$ is independently selected from
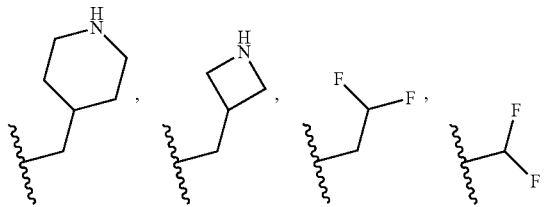
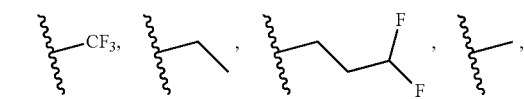
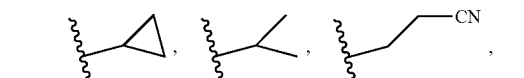
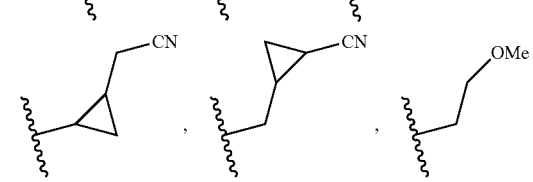
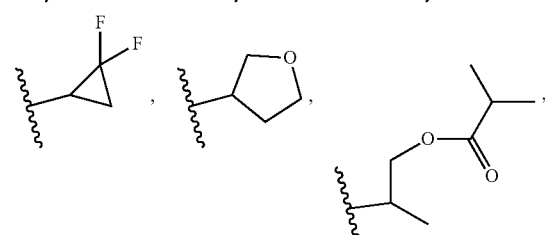
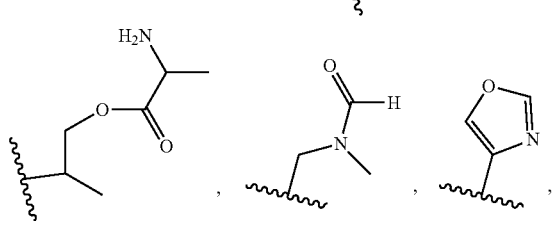
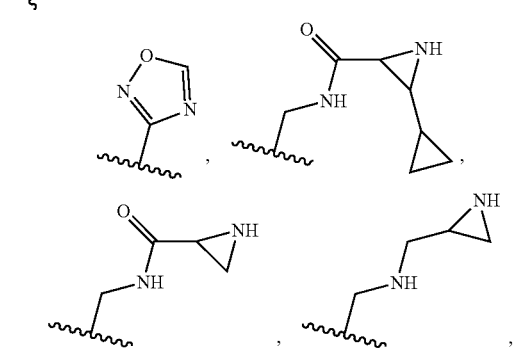
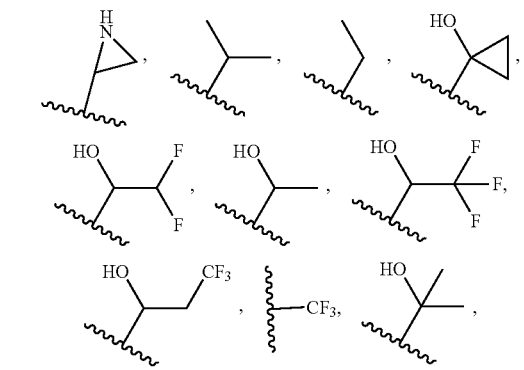

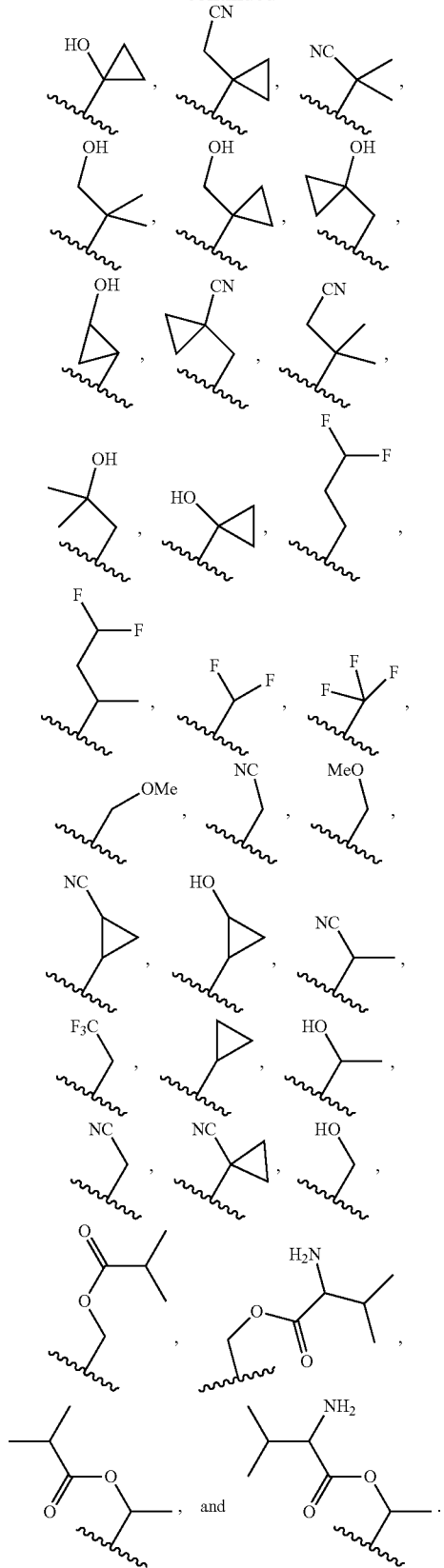
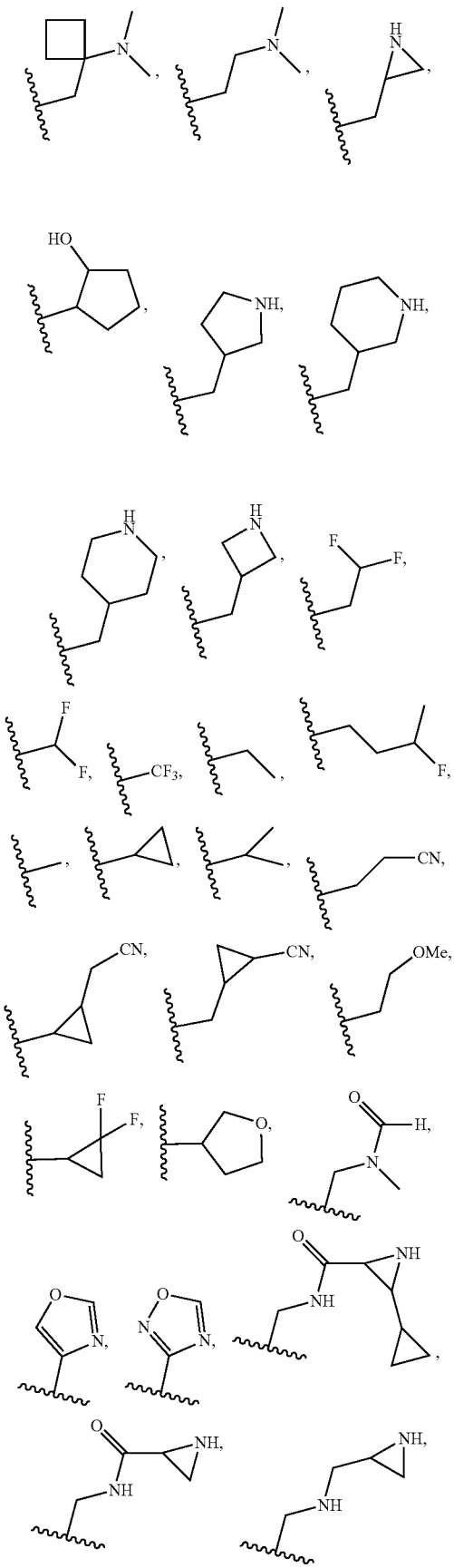
In embodiments of the formulae above, each $R^{11c}$ is independently selected from -continued

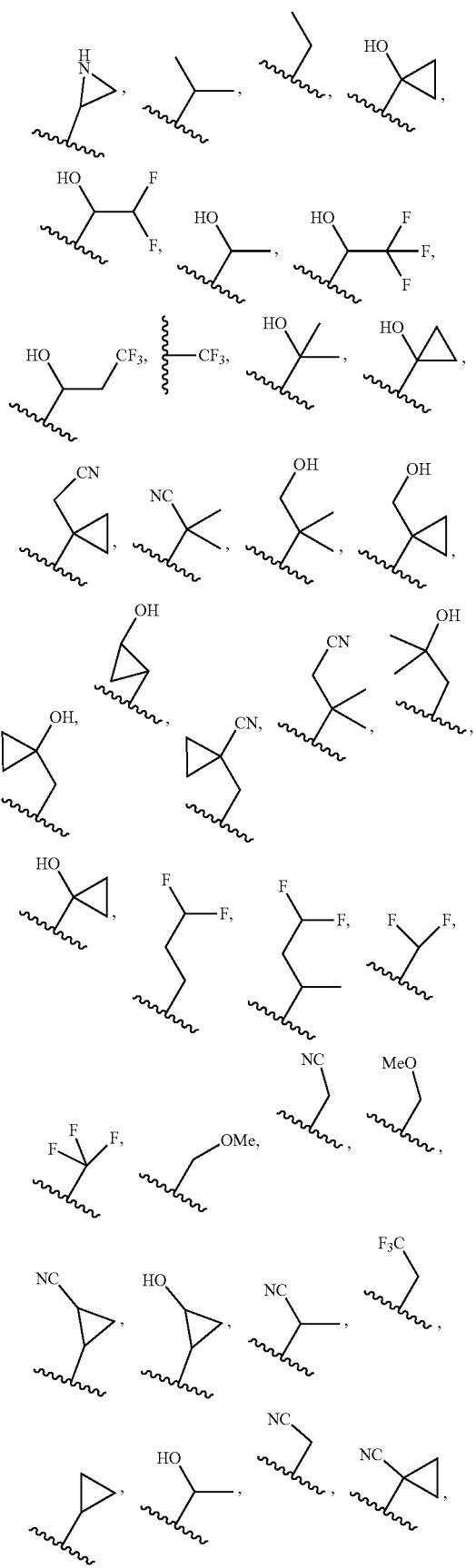

-continued

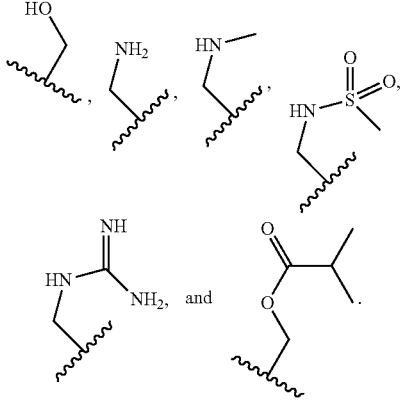

In embodiments of the formulae above, each $R^{11c}$ is independently selected from

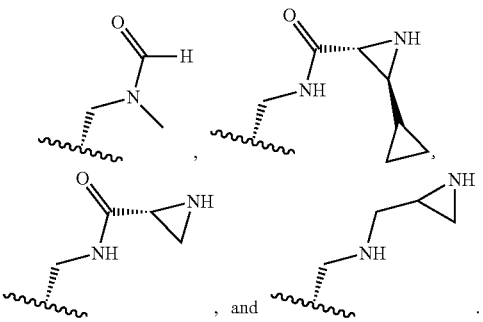

In embodiments of the formulae above, each $R^{11c}$ is independently halogen. In embodiments of the formulae above, each $R^{11c}$ is independently F. In embodiments of the formulae above, each $R^{11c}$ is independently Cl. In embodiments of the formulae above, each $R^{11c}$ is independently Br. In embodiments of the formulae above, each $R^{11c}$ is independently I. In embodiments of the formulae above; each $R^{11c}$ is independently oxo. In embodiments of the formulae above, each $R^{11c}$ is independently —CN. In embodiments of the formulae above, each $R^{11c}$ is independently $C_{1-6}$alkyl. In embodiments of the formulae above, each $R^{11c}$ is independently $C_{2-6}$alkenyl. In embodiments of the formulae above, each $R^{11c}$ is independently $C_{2-6}$alkynyl. In embodiments of the formulae above, each $R^{11c}$ is independently $C_{1-6}$haloalkyl. In embodiments of the formulae above, each $R^{11c}$ is independently $C_{3-12}$cycloalkyl. In embodiments of the formulae above, each $R^{11c}$ is independently —$CH_2$-$C_{3-12}$cycloalkyl. In embodiments of the formulae above, each $R^{11c}$ is independently $C_{1-11}$heterocycloalkyl. In embodiments of the formulae above, each $R^{11c}$ is independently —$CH_2$-$C_{1-11}$heterocycloalkyl. In embodiments of the formulae above, each $R^{11c}$ is independently $C_{6-10}$aryl. In embodiments of the formulae above, each $R^{11c}$ is independently —$CH_2$-$C_{6-10}$aryl. In embodiments of the formulae above, each $R^{11c}$ is independently —$CH_2$-$C_{1-11}$heteroaryl. In embodiments of the formulae above, each $R^{11c}$ is independently $C_{1-11}$heteroaryl. In embodiments of the formulae above, each $R^{11c}$ is independently —$OR^{12}$. In embodiments of the formulae above, each $R^{11c}$ is independently —$SR^{12}$. In embodiments of the formulae above, each $R^{11c}$ is independently —$N(R^{12})(R^{13})$. In embodiments of the formulae above, each $R^{11c}$ is independently —$C(O)OR^{12}$. In embodiments of the formulae above, each $R^{11c}$ is independently —OC(O)N($R^{12}$)($R^{13}$). In embodiments of the formulae above, each $R^{11c}$ is independently —N($R^{14}$)C(O)N($R^{12}$)($R^{13}$). In embodiments of the formulae above, each $R^{11c}$ is independently —N($R^{14}$)C(O)O$R^{15}$. In embodiments of the formulae above, each $R^{11c}$ is independently —N($R^{14}$)S(O)$_2$$R^{15}$. In embodiments of the formulae above, each $R^{11c}$ is independently —C(O)$R^{15}$. In embodiments of the formulae above, each $R^{11c}$ is independently —C(O)$R^{12}$. In embodiments of the formulae above, each $R^{11c}$ is independently —S(O)$R^{15}$. In embodiments of the formulae above, each $R^{11c}$ is independently —OC(O)$R^{15}$. In embodiments of the formulae above, each $R^{11c}$ is independently —C(O)N($R^{12}$)($R^{13}$). In embodiments of the formulae above, each $R^{11c}$ is independently —C(O)C(O)N($R^{12}$)($R^{13}$). In embodiments of the formulae above, each $R^{11c}$ is independently —N($R^{14}$)C(O)$R^{15}$. In embodiments of the formulae above, each $R^{11c}$ is independently —N($R^{14}$)C(O)$R^{12}$. In embodiments of the formulae above, each $R^{11c}$ is independently —S(O)$_2$$R^{15}$. In embodiments of the formulae above, each $R^{11c}$ is independently —S(O)$_2$N($R^{12}$)($R^{13}$)—. In embodiments of the formulae above, each $R^{11c}$ is independently S(=O)(=NH)N($R^{12}$)($R^{13}$). In embodiments of the formulae above, each $R^{11c}$ is independently —CH$_2$C(O)N($R^{12}$)($R^{13}$). In embodiments of the formulae above, each $R^{11c}$ is independently —CH$_2$N($R^{14}$)C(O)$R^{15}$. In embodiments of the formulae above, each $R^{11c}$ is independently —CH$_2$S(O)$_2$$R^{15}$. In embodiments of the formulae above, each $R^{11c}$ is independently —CH$_2$S(O)$_2$N($R^{12}$)($R^{13}$). In embodiments of the formulae above, each $R^{11c}$ is independently $C_{1-6}$alkyl substituted with one, two, or three $R^{20k}$; In embodiments of the formulae above, each $R^{11c}$ is independently $C_{2-6}$alkenyl substituted with one, two, or three $R^{20k}$; In embodiments of the formulae above, each $R^{11c}$ is independently $C_{2-6}$alkynyl substituted with one, two, or three $R^{20k}$; In embodiments of the formulae above, each $R^{11c}$ is independently $C_{1-6}$haloalkyl substituted with one, two, or three $R^{20k}$; In embodiments of the formulae above, each $R^{11c}$ is independently $C_{3-12}$cycloalkyl substituted with one, two, or three $R^{20k}$; In embodiments of the formulae above, each $R^{11c}$ is independently —CH$_2$-$C_{3-12}$cycloalkyl substituted with one, two, or three $R^{20k}$; In embodiments of the formulae above, each $R^{11c}$ is independently $C_{1-11}$heterocycloalkyl substituted with one, two, or three $R^{20k}$; In embodiments of the formulae above, each $R^{11c}$ is independently —CH$_2$-$C_{1-11}$heterocycloalkyl substituted with one, two, or three $R^{20k}$; In embodiments of the formulae above, each $R^{11c}$ is independently $C_{6-10}$aryl substituted with one, two, or three $R^{20k}$; In embodiments of the formulae above;

each $R^{11c}$ is independently —CH$_2$-$C_6$-10aryl substituted with one, two, or three $R^{20k}$; In embodiments of the formulae above, each $R^{11c}$ is independently —CH$_2$-$C_{1-11}$heteroaryl substituted with one, two, or three $R^{20k}$; In embodiments of the formulae above, each $R^{11c}$ is independently $C_{1-11}$heteroaryl substituted with one, two, or three $R^{20k}$;

In embodiments of the formulae above, each $R^{11c}$ is independently —C(O)$R^{12}$. In embodiments of the formulae above, each $R^{11c}$ is independently —N($R^{14}$)C(O)$R^{12}$. In embodiments of the formulae above, each $R^{11c}$ is independently —(C$_{1-6}$alkyl)-C(O)N($R^{12}$)($R^{13}$) wherein C$_{1-6}$alkyl is optionally substituted with one, two, or three $R^{20k}$; In embodiments of the formulae above, each $R^{11c}$ is independently —(C$_{1-6}$alkyl)-N($R^{14}$)C(O)$R^{12}$ wherein C$_{1-6}$alkyl is optionally substituted with one, two, or three $R^{20k}$; In embodiments of the formulae above, each $R^{11c}$ is independently —(C$_{1-6}$alkyl)-S(O)$_2$$R^{15}$ wherein C$_{1-6}$alkyl is optionally substituted with one, two, or three $R^{20k}$; In embodiments of the formulae above, each $R^{11c}$ is independently —(C$_{1-6}$alkyl)-S(O)$_2$N($R^{12}$)($R^{13}$). In embodiments of the formulae above, each $R^{11c}$ is independently —C(O)H. In embodiments of the formulae above, each $R^{11c}$ is independently —N($R^{14}$)C(O)H. In embodiments of the formulae above, each $R^{11c}$ is independently —(C$_{1-6}$alkyl)-N($R^{14}$)C(O)H wherein C$_{1-6}$alkyl is optionally substituted with one, two, or three $R^{20k}$; In embodiments of the formulae above, each $R^{11c}$ is independently —(C$_{1-6}$alkyl)-N($R^{12}$)($R^{13}$) wherein C$_{1-6}$alkyl is optionally substituted with one, two, or three $R^{20k}$.

The individual embodiments herein below, or combinations thereof, (e.g., embodiments of $R^{11}$d) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In embodiments of the formulae above, each $R^{11d}$ is independently halogen. In embodiments of the formulae above, each $R^{11d}$ is independently F. In embodiments of the formulae above, each $R^{11d}$ is independently $C_1$. In embodiments of the formulae above, each $R^{11d}$ is independently Br. In embodiments of the formulae above, each $R^{11d}$ is independently I. In embodiments of the formulae above, each $R^{11d}$ is independently oxo. In embodiments of the formulae above, each $R^{11d}$ is independently —CN. In embodiments of the formulae above;

each $R^{11d}$ is independently $C_{1-6}$alkyl. In embodiments of the formulae above, each $R^{11d}$ is independently $C_{2-6}$alkenyl. In embodiments of the formulae above, each $R^{11d}$ is independently $C_{2-6}$alkynyl. In embodiments of the formulae above, each $R^{11d}$ is independently $C_{1-6}$haloalkyl. In embodiments of the formulae above, each $R^{11d}$ is independently $C_{3-12}$cycloalkyl. In embodiments of the formulae above;

each $R^{11d}$ is independently —CH$_2$-$C_{3-12}$cycloalkyl. In embodiments of the formulae above, each $R^{11d}$ is independently $C_{1-1}$heterocycloalkyl. In embodiments of the formulae above, each $R^{11d}$ is independently —CH$_2$-$C_{1-11}$heterocycloalkyl. In embodiments of the formulae above, each $R^{11d}$ is independently $C_{6-10}$aryl. In embodiments of the formulae above, each $R^{11d}$ is independently —$CH_2$-$C_{6-10}$aryl. In embodiments of the formulae above, each $R^{11d}$ is independently —$CH_2$-$C_{1-11}$heteroaryl. In embodiments of the formulae above, each $R^{11d}$ is independently $C_{1-11}$heteroaryl. In embodiments of the formulae above, each $R^{11d}$ is independently —$OR^{12}$. In embodiments of the formulae above, each $R^{11d}$ is independently —$SR^{12}$. In embodiments of the formulae above, each $R^{11d}$ is independently —$N(R^{12})(R^{13})$. In embodiments of the formulae above, each $R^{11d}$ is independently —$C(O)OR^{12}$. In embodiments of the formulae above, each $R^{11d}$ is independently —$OC(O)N(R^{12})(R^{13})$. In embodiments of the formulae above, each $R^{11d}$ is independently —$N(R^{14})C(O)N(R^{12})(R^{13})$. In embodiments of the formulae above, each $R^{11d}$ is independently —$N(R^{14})C(O)OR^{15}$. In embodiments of the formulae above, each $R^{11d}$ is independently —$N(R^{14})S(O)_2R^{15}$. In embodiments of the formulae above, each $R^{11d}$ is independently —$C(O)R^{15}$. In embodiments of the formulae above, each $R^{11d}$ is independently —$S(O)R^{15}$. In embodiments of the formulae above, each $R^{11d}$ is independently —$OC(O)R^{15}$. In embodiments of the formulae above, each $R^{11d}$ is independently —$C(O)N(R^{12})(R^{13})$. In embodiments of the formulae above, each $R^{11d}$ is independently —$C(O)C(O)N(R^{12})(R^{13})$. In embodiments of the formulae above, each $R^{11d}$ is independently —$N(R^{14})C(O)R^{15}$. In embodiments of the formulae above, each $R^{11d}$ is independently —$S(O)_2R^{15}$. In embodiments of the formulae above, each $R^{11d}$ is independently —$S(O)_2N(R^{12})(R^{13})$—. In embodiments of the formulae above, each $R^{11d}$ is independently $S(=O)(=NH)N(R^{12})(R^{13})$. In embodiments of the formulae above, each $R^{11d}$ is independently —$CH_2C(O)N(R^{12})(R^{13})$. In embodiments of the formulae above, each $R^{11d}$ is independently —$CH_2N(R^{14})C(O)R^{15}$. In embodiments of the formulae above, each $R^{11d}$ is independently —$CH_2S(O)_2R^{15}$. In embodiments of the formulae above, each $R^{11d}$ is independently —$CH_2S(O)_2N(R^{12})(R^{13})$. In embodiments of the formulae above, each $R^{11d}$ is independently $C_{1-6}$alkyl substituted with one, two, or three $R^{20k}$; In embodiments of the formulae above, each $R^{11d}$ is independently $C_{2-6}$alkenyl substituted with one, two, or three $R^{20k}$; In embodiments of the formulae above, each $R^{11d}$ is independently $C_{2-6}$alkynyl substituted with one, two, or three $R^{20k}$; In embodiments of the formulae above, each $R^{11d}$ is independently $C_{1-6}$haloalkyl substituted with one, two, or three $R^{20k}$; In embodiments of the formulae above, each $R^{11d}$ is independently $C_{3-12}$cycloalkyl substituted with one, two, or three $R^{20k}$; In embodiments of the formulae above, each $R^{11d}$ is independently —$CH_2$-$C_{3-12}$cycloalkyl substituted with one, two, or three $R^{20k}$; In embodiments of the formulae above, each $R^{11d}$ is independently $C_{1-11}$heterocycloalkyl substituted with one, two, or three $R^{20k}$; In embodiments of the formulae above, each $R^{11d}$ is independently —$CH_2$-$C_{1-11}$heterocycloalkyl substituted with one, two, or three $R^{20k}$; In embodiments of the formulae above, each $R^{11d}$ is independently $C_{6-10}$aryl substituted with one, two, or three $R^{20k}$; In embodiments of the formulae above, each $R^{11d}$ is independently —$CH_2$-$C_{6}$-10aryl substituted with one, two, or three $R^{20k}$; In embodiments of the formulae above, each $R^{11d}$ is independently —$CH_2$-$C_1$-nheteroaryl substituted with one, two, or three $R^{20k}$; In embodiments of the formulae above, each $R^{11d}$ is independently $C_{1-11}$heteroaryl substituted with one, two, or three $R^{20k}$; In embodiments of the formulae above, each $R^{11d}$ is independently —$C(O)R^{12}$. In embodiments of the formulae above, each $R^{11d}$ is independently —$N(R^{14})C(O)R^{12}$. In embodiments of the formulae above, each $R^{11d}$ is independently —$(C_{1-6}alkyl)$-$C(O)N(R^{12})(R^{13})$ wherein $C_{1-6}$alkyl is optionally substituted with one, two, or three $R^{20k}$; In embodiments of the formulae above, each $R^{11d}$ is independently —$(C_{1-6}alkyl)$-$N(R^{14})C(O)R^{12}$ wherein $C_{1-6}$alkyl is optionally substituted with one, two, or three $R^{20k}$; In embodiments of the formulae above, each $R^{11d}$ is independently —$(C_{1-6}alkyl)$-$S(O)_2R^{15}$ wherein $C_{1-6}$alkyl is optionally substituted with one, two, or three $R^{20k}$; In embodiments of the formulae above, each $R^{11d}$ is independently —$(C_{1-6}alkyl)$-$S(O)_2N(R^{12})(R^{13})$. In embodiments of the formulae above, each $R^{11d}$ is independently —$C(O)H$. In embodiments of the formulae above, each $R^{11d}$ is independently —$N(R^{14})C(O)H$. In embodiments of the formulae above, each $R^{11d}$ is independently —$(C_{1-6}alkyl)$-$N(R^{14})C(O)H$ wherein $C_{1-6}$alkyl is optionally substituted with one, two, or three $R^{20k}$; In embodiments of the formulae above, each $R^{11d}$ is independently —$(C_{1-6}alkyl)$-$N(R^{12})(R^{13})$ wherein $C_{1-6}$alkyl is optionally substituted with one, two, or three $R^{20k}$; In embodiments of the formulae above, each $R^{11d}$ is independently selected from

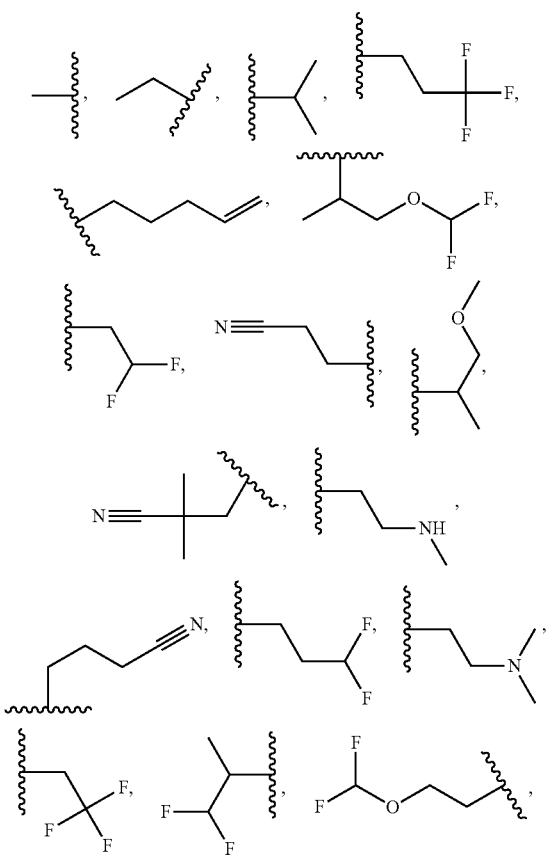

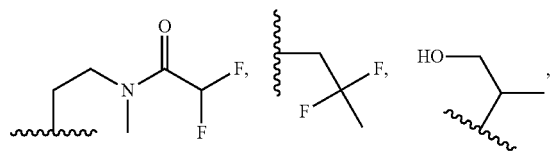
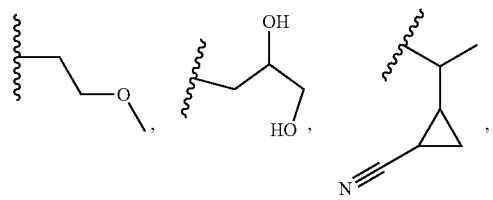
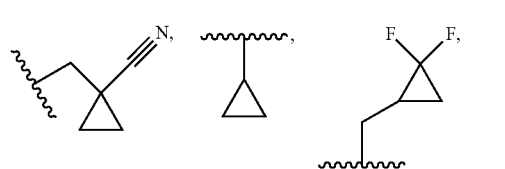
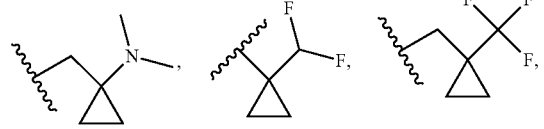
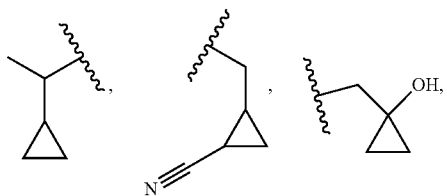
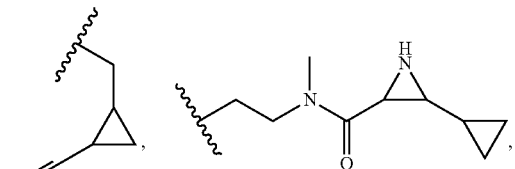
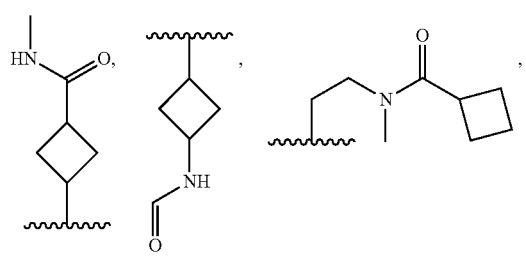
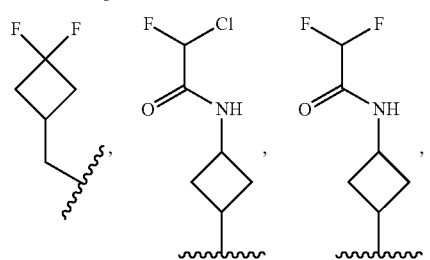
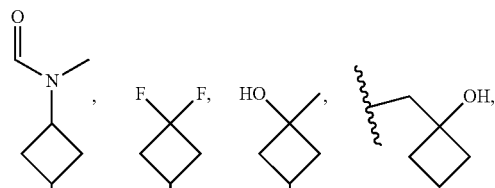
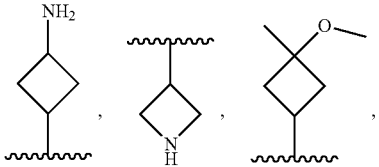
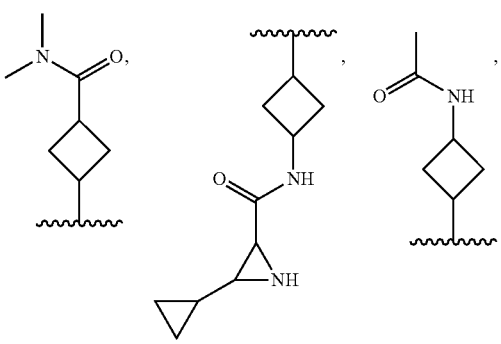
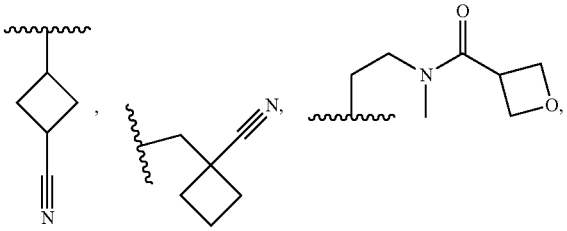
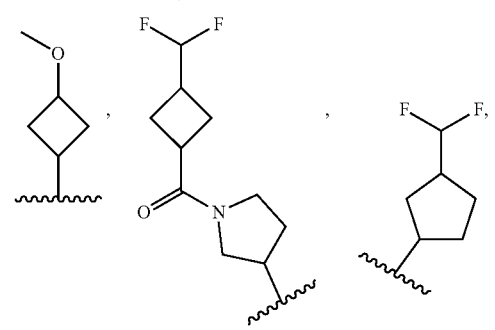
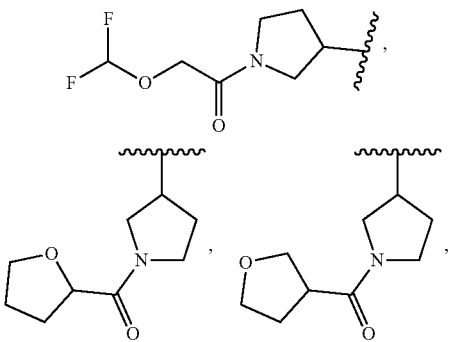

669
-continued
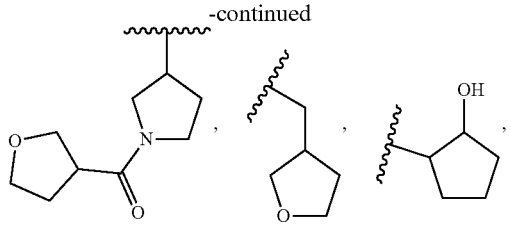
670
-continued
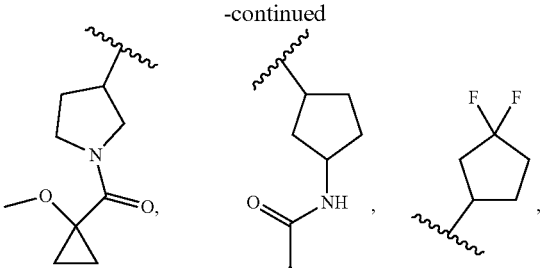
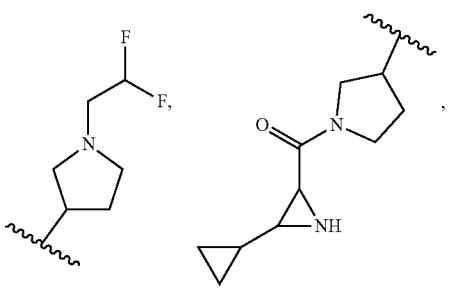
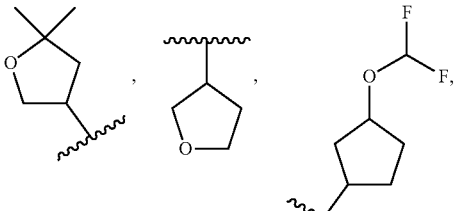
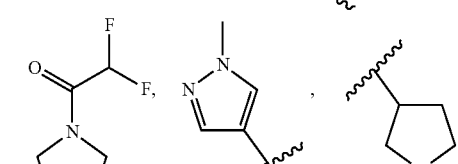
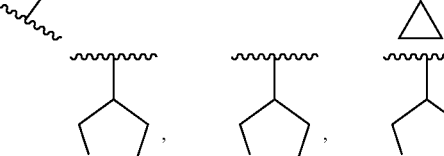
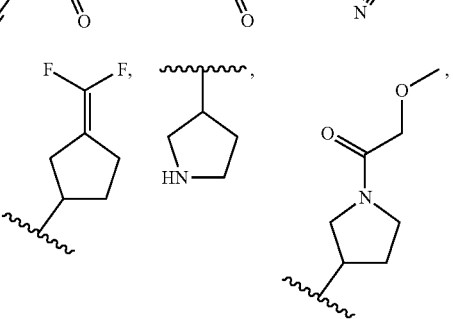

671
-continued
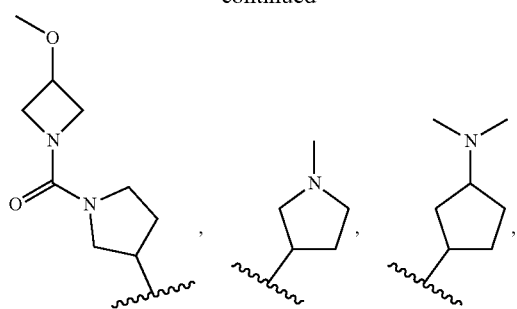
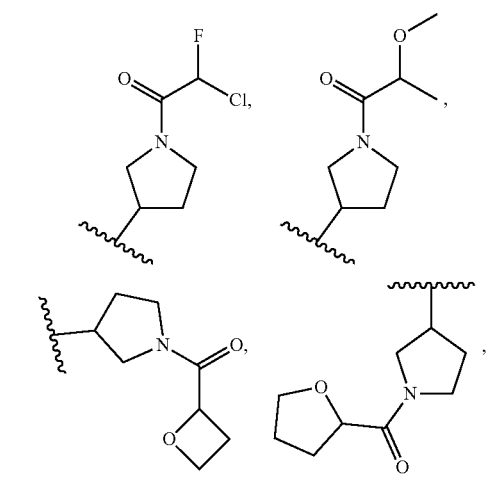
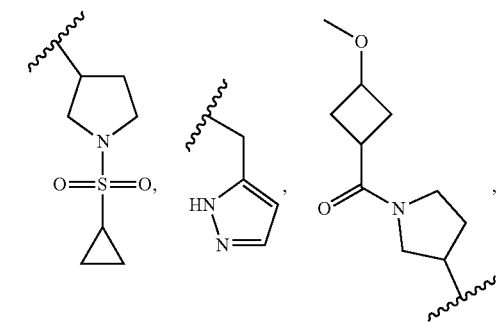
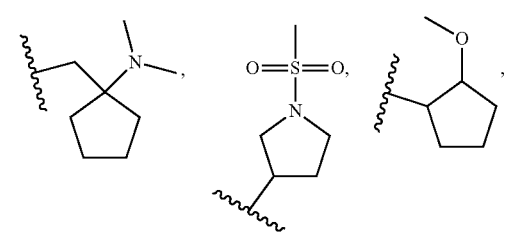
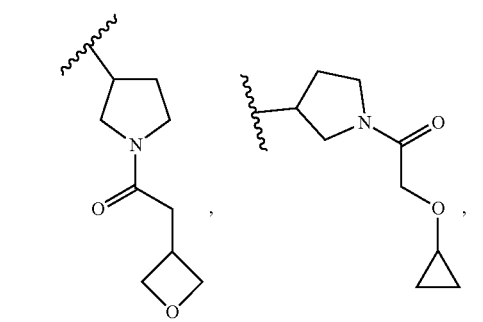
672
-continued
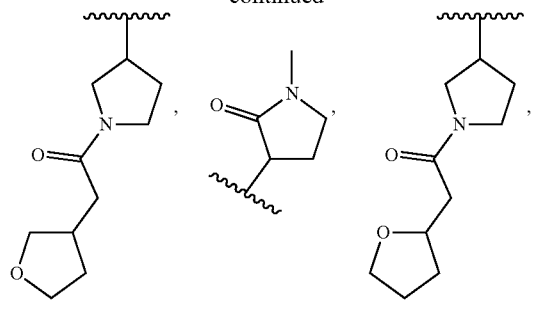
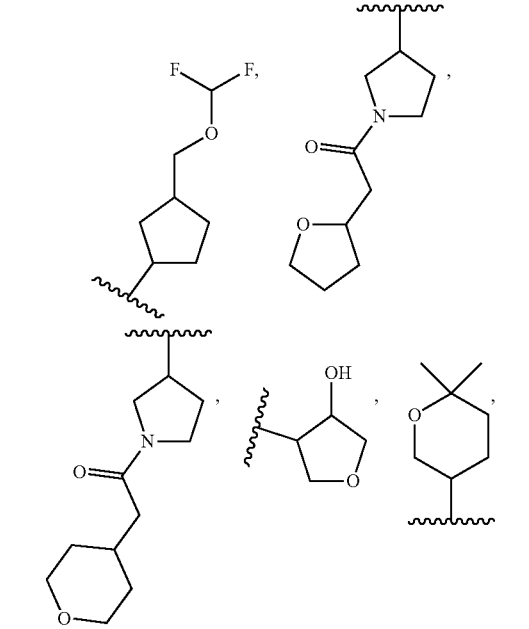
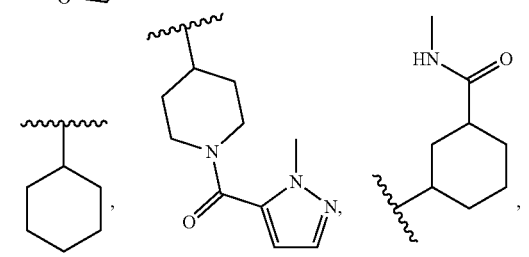
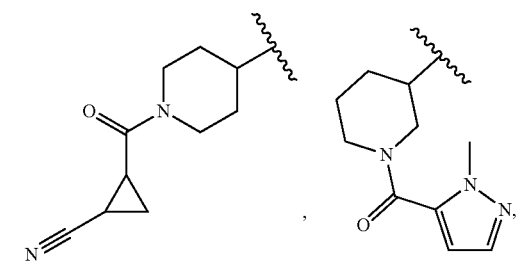
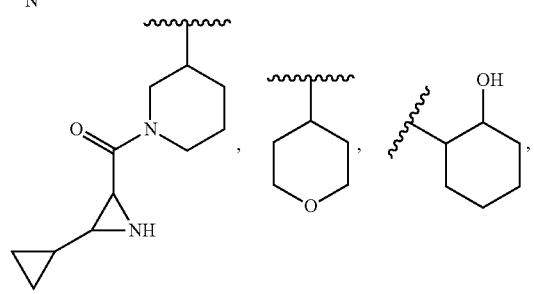

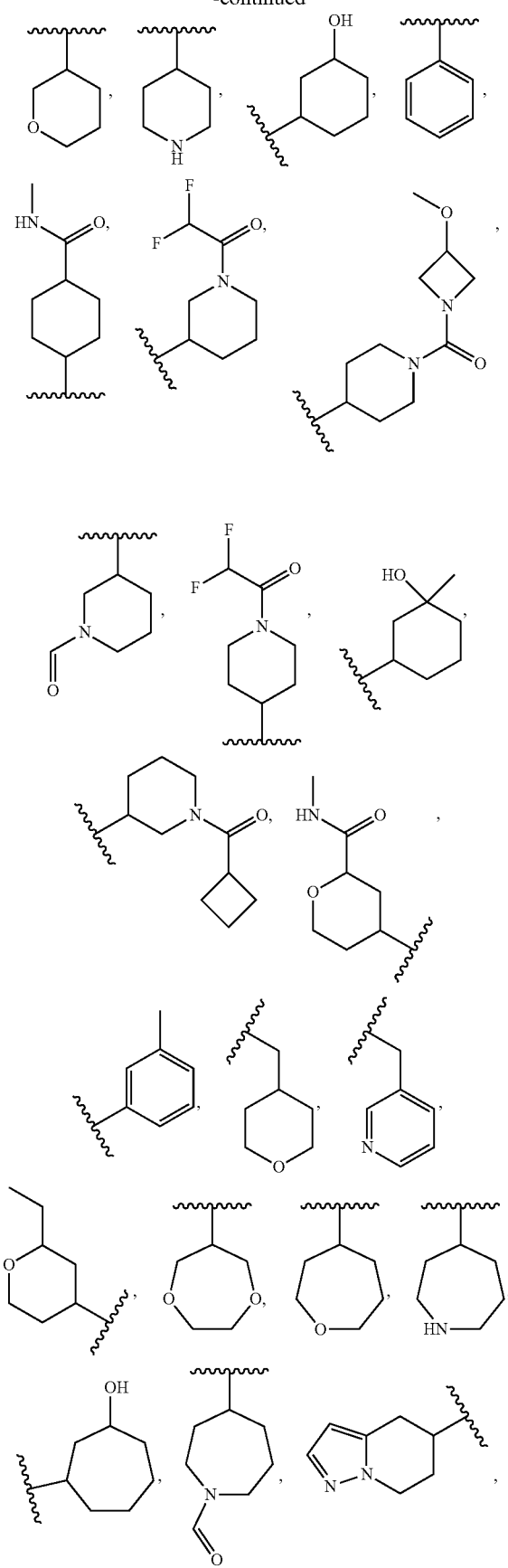
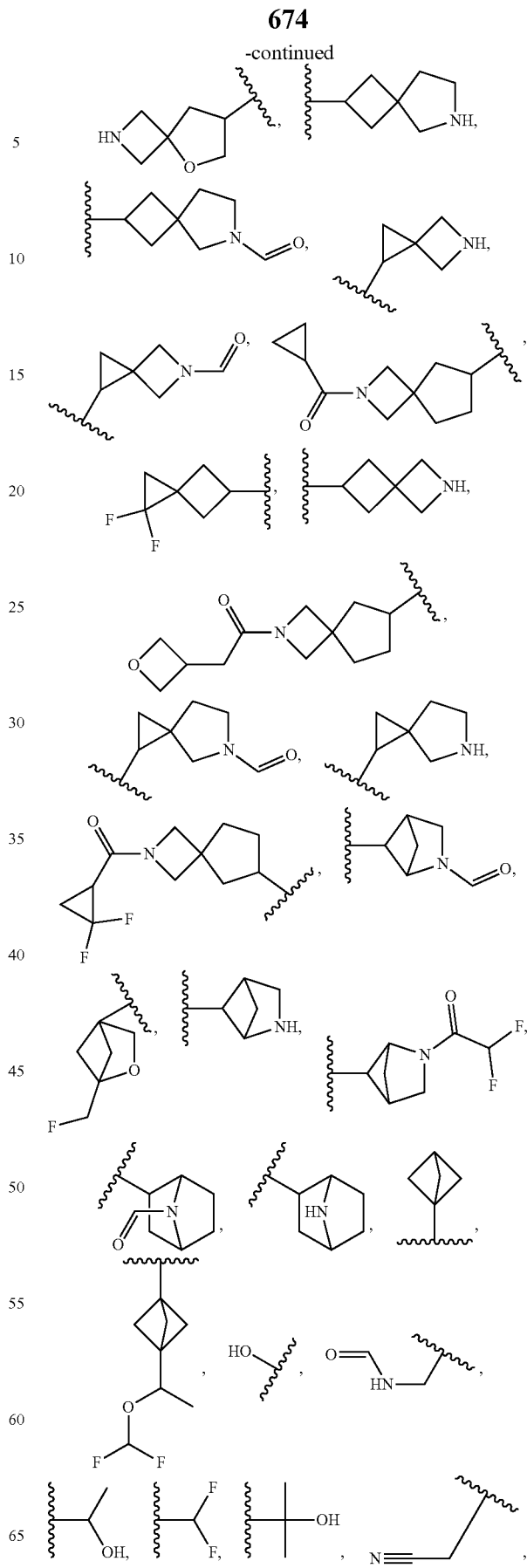

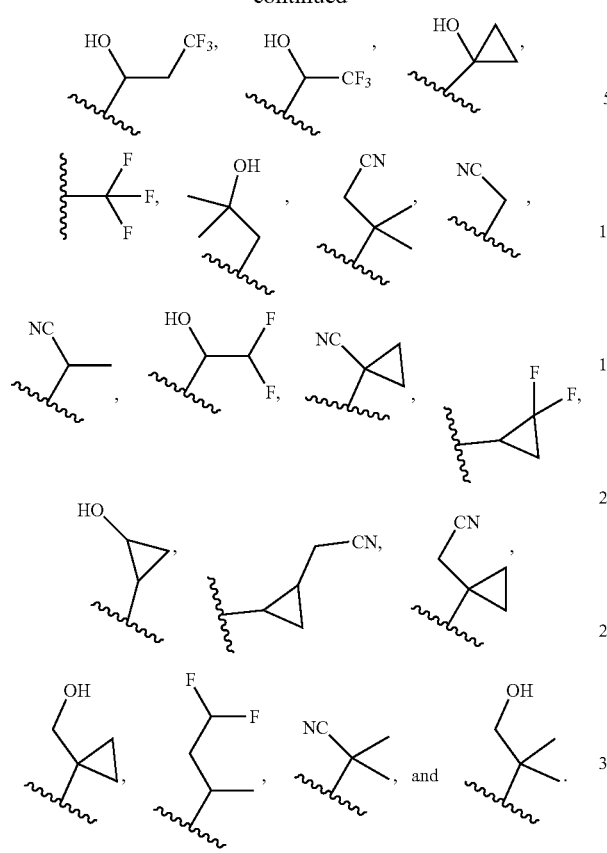
In embodiments of the formulae above, each $R^{11d}$ is independently selected from
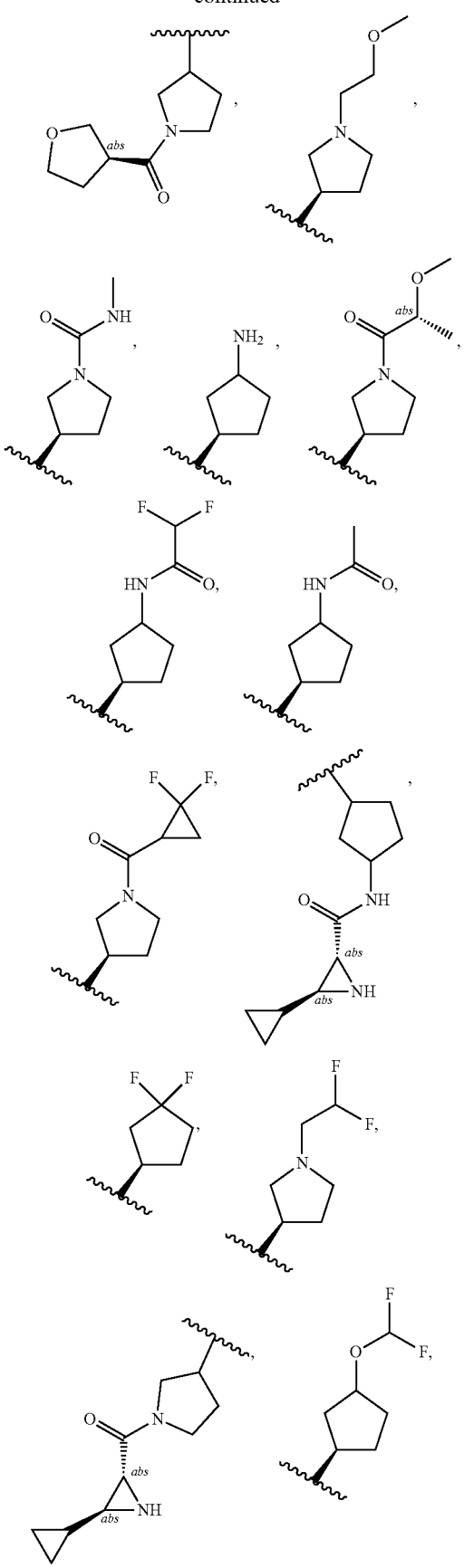

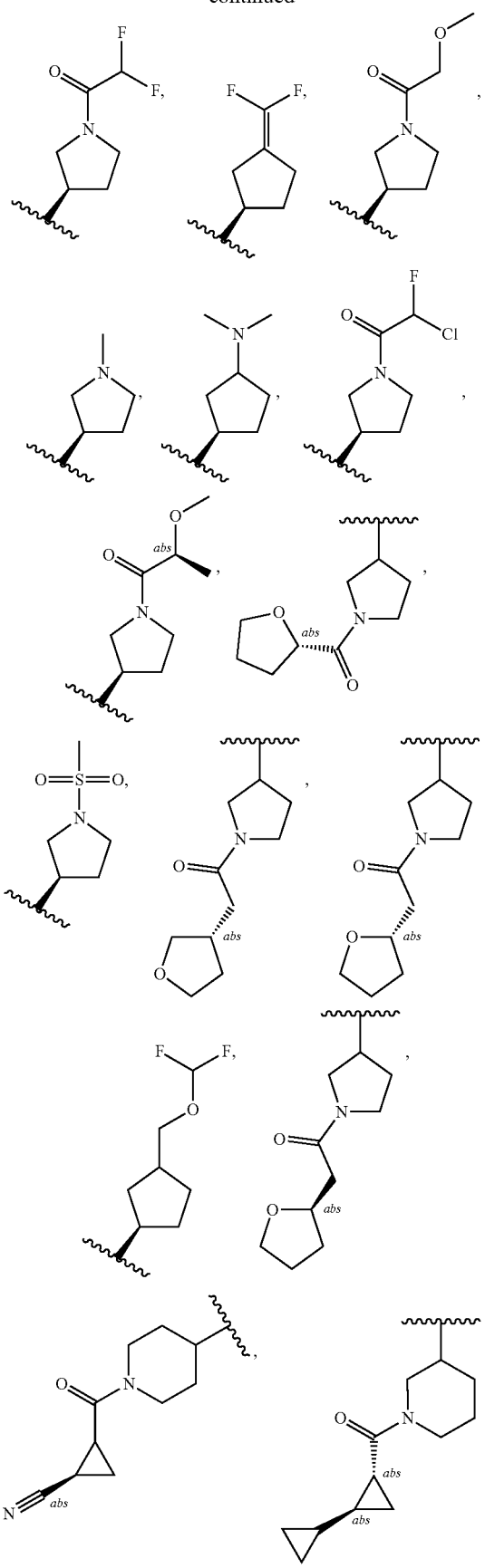
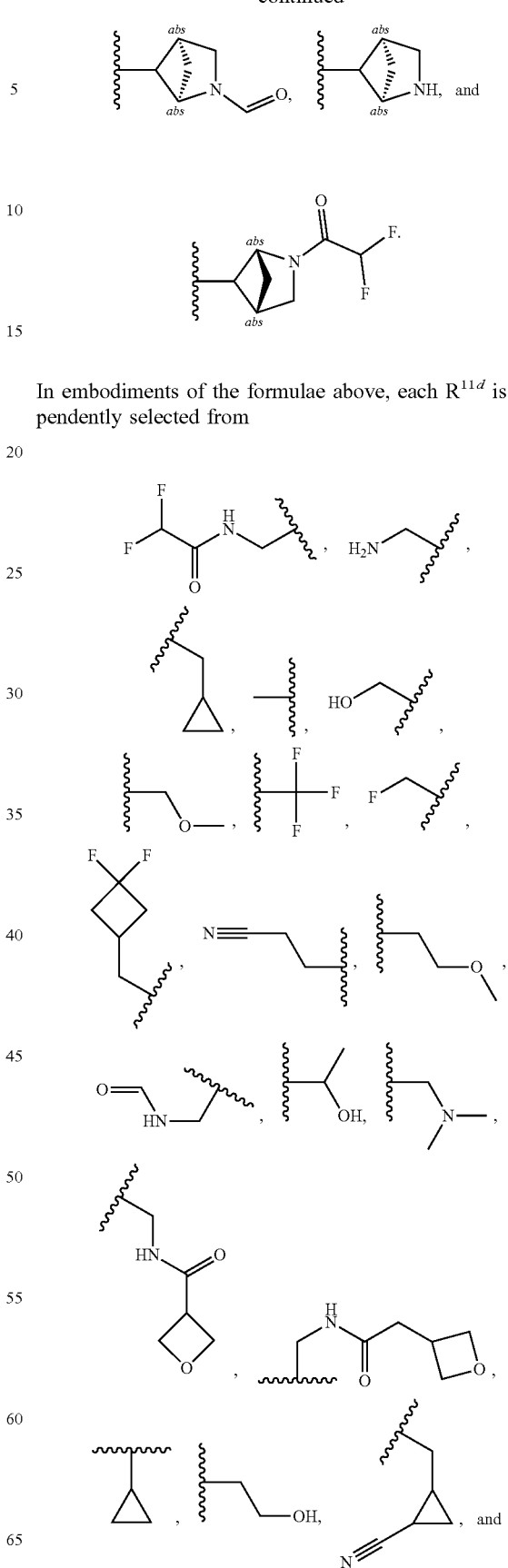
In embodiments of the formulae above, each $R^{11d}$ is independently selected from

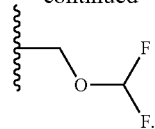

In embodiments of the formulae above, each $R^{11d}$ is independently selected from

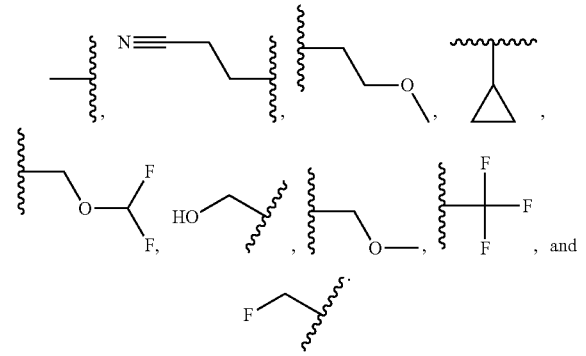

In embodiments of the formulae above, each $R^{11d}$ is independently selected from

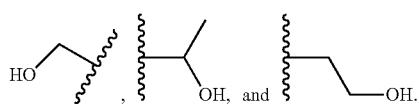

In embodiments of the formulae above, each $R^{11d}$ is independently selected from

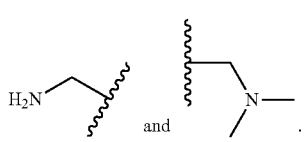

In embodiments of the formulae above, each $R^{11d}$ is independently selected from

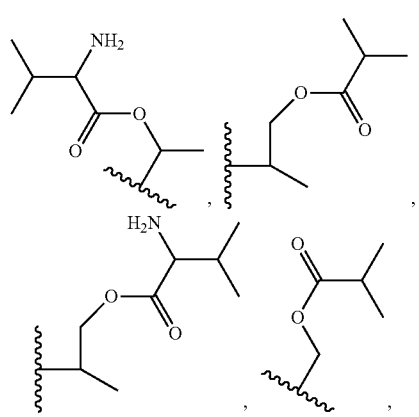

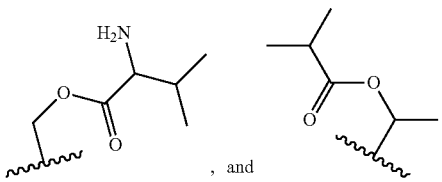, and

In embodiments of the formulae above, each $R^{11d}$ is independently selected from

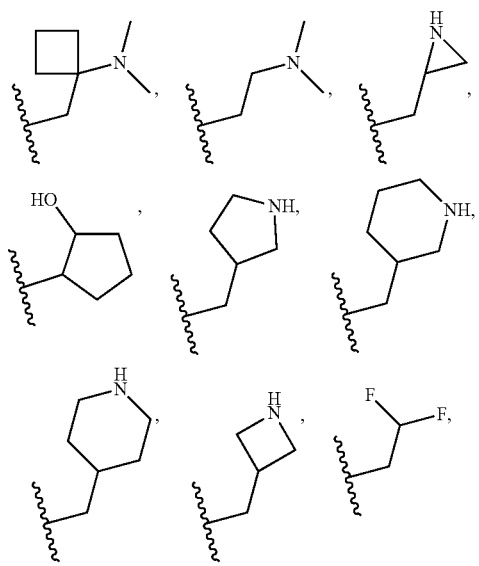

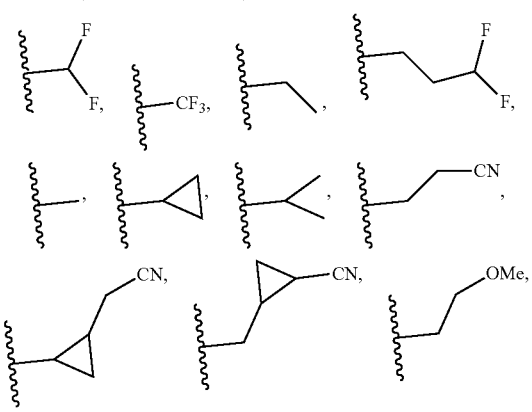

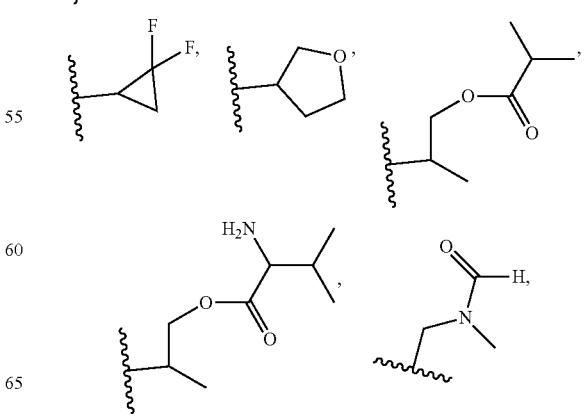

681
-continued
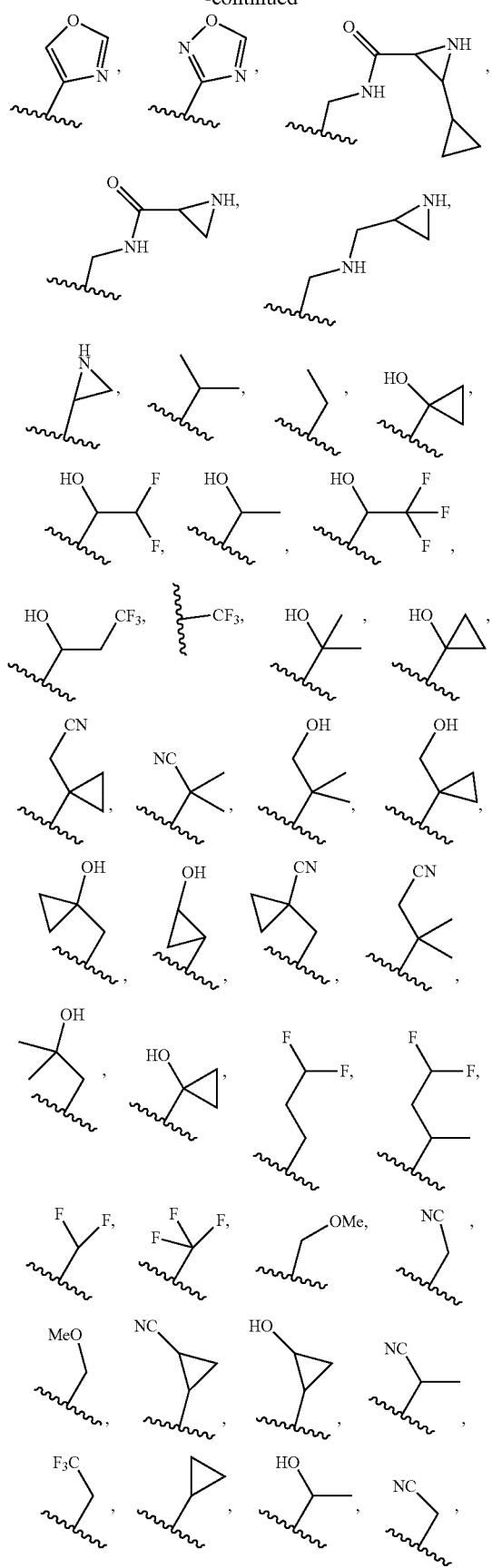
682
-continued
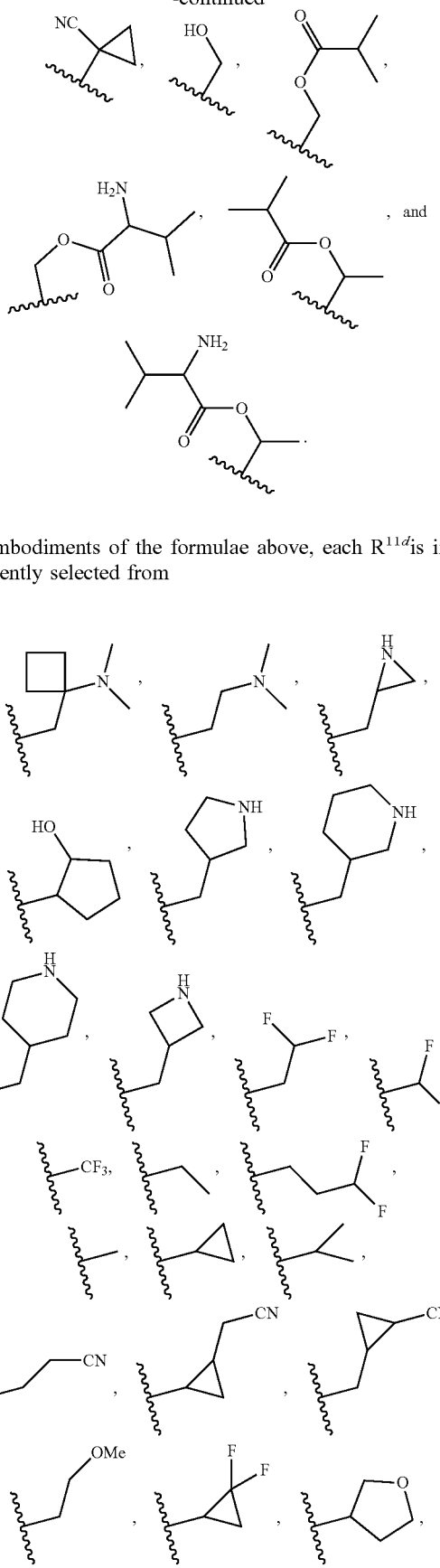
In embodiments of the formulae above, each $R^{11d}$ is independently selected from

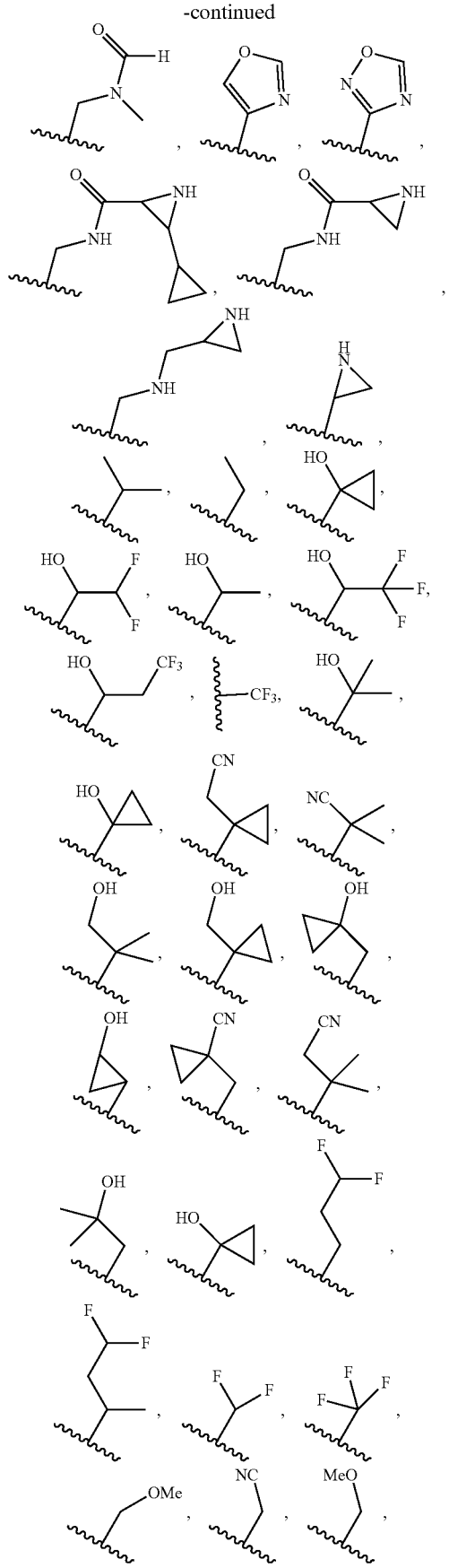

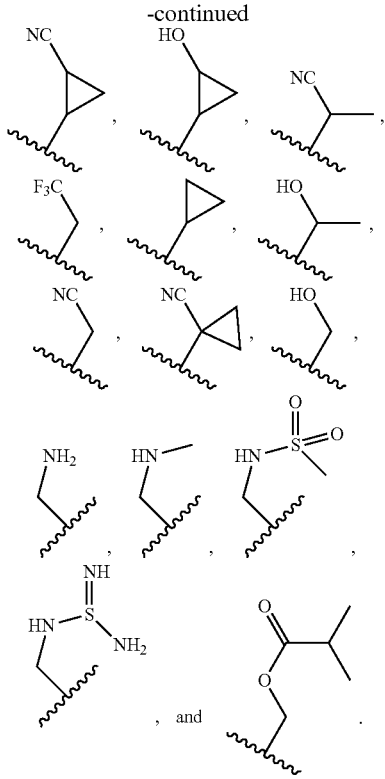

In embodiments of the formulae above, each $R^{11d}$ is independently selected from

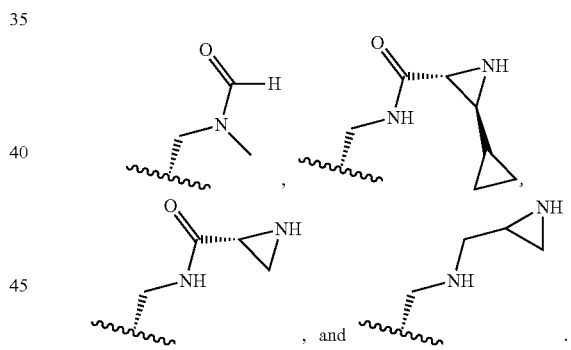

The individual embodiments herein below, or combinations thereof, (e.g., embodiments of $R^{20k}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{20k}$ is independently halogen. In embodiments of the formulae above, each $R^{20k}$ is independently oxo. In embodiments of the formulae above, each $R^{20k}$ is independently —CN. In embodiments of the formulae above, each $R^{20k}$ is independently $C_{1-6}$alkyl. In embodiments of the formulae above, each $R^{20k}$ is independently $C_{2-6}$alkenyl. In embodiments of the formulae above, each $R^{20k}$ is independently $C_{2-6}$alkynyl. In embodiments of the formulae above, each $R^{20k}$ is independently $C_{3-10}$cycloalkyl. In embodiments of the formulae above, each $R^{20k}$ is independently —$CH_2$-$C_{3-10}$cycloalkyl. In embodiments of the formulae above, each $R^{20k}$ is independently $C_{2-9}$heterocycloalkyl. In embodiments of the formulae above, each $R^{20k}$ is independently —$CH_2$-$C_{2-9}$heterocycloalkyl. In embodiments of the formulae above, each $R^{20k}$ is independently $C_{6-10}$aryl. In embodiments of the formulae above, each $R^{20k}$ is independently —$CH_2$-$C_6$-10aryl. In embodiments of the formulae above, each $R^{20k}$ is independently —$CH_2$-$C_{1-9}$heteroaryl. In embodiments of the formulae above, each $R^{20k}$ is independently $C_{1-9}$heteroaryl. In embodiments of the formulae above, each $R^{20k}$ is independently —$OR^{21}$. In embodiments of the formulae above, each $R^{20k}$ is independently —$SR^{21}$. In embodiments of the formulae above, each $R^{20k}$ is independently —$N(R^{22})(R^{23})$. In embodiments of the formulae above, each $R^{20k}$ is independently —$C(O)OR^{22}$. In embodiments of the formulae above, each $R^{20k}$ is independently —$C(O)N(R^{22})(R^{23})$. In embodiments of the formulae above, each $R^{20k}$ is independently —$C(O)C(O)N(R^{22})(R^{23})$. In embodiments of the formulae above, each $R^{20k}$ is independently —$OC(O)N(R^{22})(R^{23})$. In embodiments of the formulae above, each $R^{20k}$ is independently —$N(R^{24})C(O)N(R^{22})(R^{23})$. In embodiments of the formulae above, each $R^{20k}$ is independently —$N(R^{24})C(O)OR^{25}$. In embodiments of the formulae above, each $R^{20k}$ is independently —$N(R^{24})C(O)R^{25}$. In embodiments of the formulae above, each $R^{20k}$ is independently —$N(R^{24})C(O)R^{21}$. In embodiments of the formulae above, each $R^{20k}$ is independently —$C(O)R^{21}$. In embodiments of the formulae above; each $R^{20k}$ is independently —$N(R^{24})S(O)_2R^{25}$. In embodiments of the formulae above, each $R^{20k}$ is independently —$C(O)R^{25}$. In embodiments of the formulae above, each $R^{20k}$ is independently —$S(O)_2R^{25}$. In embodiments of the formulae above, each $R^{20k}$ is independently —$S(O)_2N(R^{22})(R^{23})$. In embodiments of the formulae above, each $R^{20k}$ is independently —$OCH_2C(O)OR^{22}$. In embodiments of the formulae above, each $R^{20k}$ is independently —$OC(O)R^{25}$. In embodiments of the formulae above, each $R^{20k}$ is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20k}$ is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20k}$ is independently $C_{2-6}$alkynyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20k}$ is independently $C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20k}$ is independently —$CH_2$-$C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above; each $R^{20k}$ is independently $C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{20k}$ is independently —$CH_2$-$C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$.

In embodiments of the formulae above, each $R^{20k}$ is independently $C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above;

each $R^{20k}$ is independently —CH$_2$-C$_{6}$-10aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20k}$ is independently —CH$_2$-C$_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20k}$ is independently $C_{1-9}$heteroaryl substituted with one, two, or three groups independently selected from halogen, oxo, —CN, $C_{1-6}$alkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. The individual embodiments herein below, or combinations thereof, (e.g., embodiments of $R^{4b}$, $R^{20k}$, or $R^{12}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In embodiments of the formulae above, $R^{4b}$ is selected from

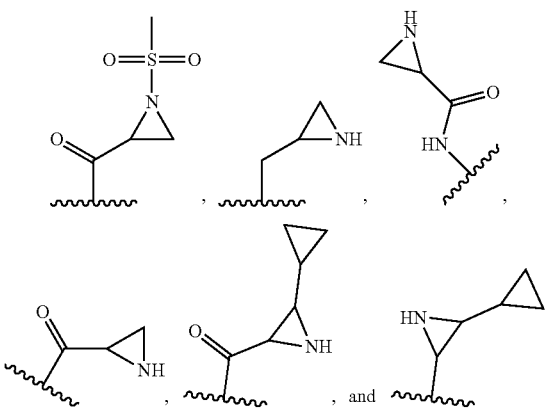

In embodiments of the formulae above, $R^{12}$ is selected from

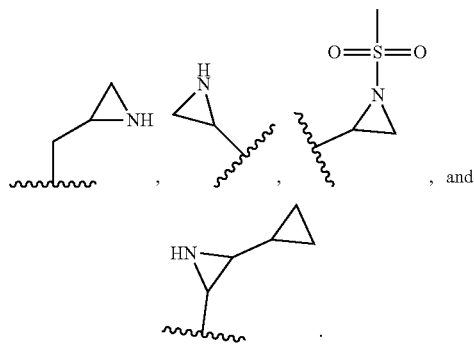

In embodiments of the formulae above, $R^{20k}$ is selected from

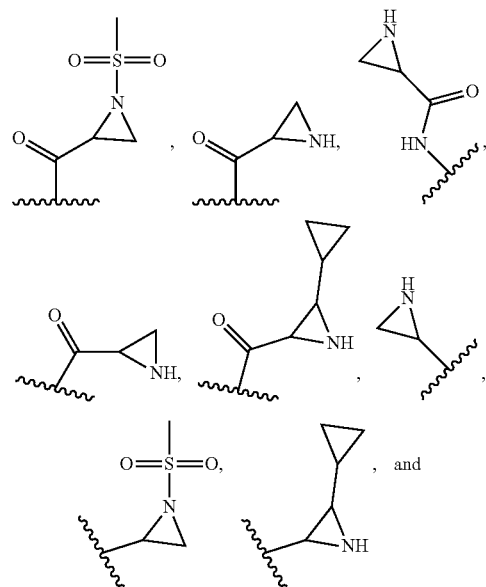

-continued

In embodiments of the formulae above, $R^{4b}$ is selected from

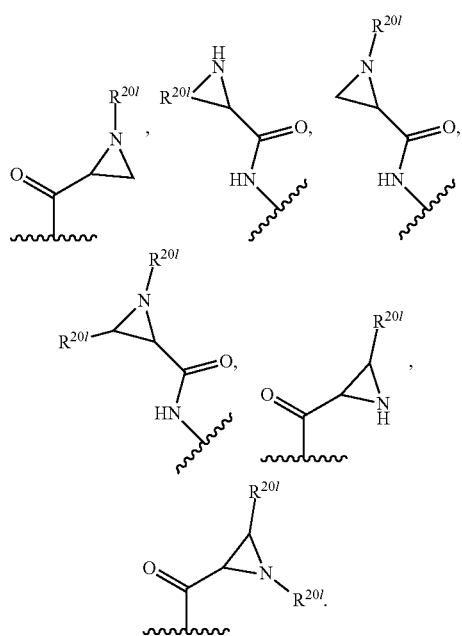

The individual embodiments herein below, or combinations thereof, (e.g., embodiments of $R^{12}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In embodiments of the formulae above, each $R^{12}$ is independently hydrogen. In embodiments of the formulae above, each $R^{12}$ is independently $C_{1-6}$alkyl. In embodiments of the formulae above, each $R^{12}$ is independently $C_{2-6}$alkenyl. In embodiments of the formulae above, each $R^{12}$ is independently $C_{2-6}$alkynyl. In embodiments of the formulae above, each $R^{12}$ is independently $C_{3-10}$cycloalkyl. In embodiments of the formulae above, each $R^{12}$ is independently —$C(R^{12}b)_2$-$C_{3-10}$cycloalkyl. In embodiments of the formulae above, each $R^{12}$ is independently $C_{2-9}$heterocycloalkyl. In embodiments of the formulae above, each $R^{12}$ is independently —$C(R^{12}b)_2$-$C_{2-9}$heterocycloalkyl. In embodiments of the formulae above, each $R^{12}$ is independently $C_{6-10}$aryl. In embodiments of the formulae above, each $R^{12}$ is independently —$C(R^{12}b)_2$-$C_{6}$-10aryl. In embodiments of the formulae above, each $R^{12}$ is independently —$C(R^{12}b)_2$-$C_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above, each $R^{12}$ is independently $C_2$-falkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —$C(R^{12}b)_2$-$C_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —$C(R^{12}b)_2$-$C_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —$C(R^{12}b)_2$-$C_6$-10aryl substituted with one, two, or three $R^{201}$. In embodiments of the formulae above, each $R^{12}$ is independently —$C(R^{12}b)_2$-$C_{1-9}$heteroaryl substituted with one, two, or three $R^{201}$. In embodiments of the formulae above, each $R^{12}$ is independently $C_{1-9}$heteroaryl substituted with one, two, or three $R^{201}$. In embodiments of the formulae above, each $R^{12}$ is independently hydrogen. In embodiments of the formulae above, each $R^{12}$ is independently $C_{1-6}$alkyl. In embodiments of the formulae above, each $R^{12}$ is independently $C_{2-6}$alkenyl. In embodiments of the formulae above, each $R^{12}$ is independently $C_{2-6}$alkynyl. In embodiments of the formulae above, each $R^{12}$ is independently $C_{3-10}$cycloalkyl. In embodiments of the formulae above, each $R^{12}$ is independently —$C(H)_2$-$C_{3-10}$cycloalkyl. In embodiments of the formulae above, each $R^{12}$ is independently $C_{2-9}$heterocycloalkyl. In embodiments of the formulae above, each $R^{12}$ is independently —$C(H)_2$-$C_{2-9}$heterocycloalkyl. In embodiments of the formulae above, each $R^{12}$ is independently $C_{6-10}$aryl. In embodiments of the formulae above, each $R^{12}$ is independently —$C(H)_2$-$C_6$-10aryl. In embodiments of the formulae above, each $R^{12}$ is independently —$C(H)_2$-$C_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above, each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —$C(H)_2$-$C_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C(H)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C(H)$_2$-C$_{6-10}$aryl substituted with one, two, or three $R^{201}$. In embodiments of the formulae above, each $R^{12}$ is independently —C(H)$_2$-C$_{1-9}$heteroaryl substituted with one, two, or three $R^{201}$. In embodiments of the formulae above, each $R^{12}$ is independently $C_{1-9}$heteroaryl substituted with one, two, or three $R^{201}$. In embodiments of the formulae above, each $R^{12}$ is independently methyl. In embodiments of the formulae above, each $R^{12}$ is independently ethyl. In embodiments of the formulae above, each $R^{12}$ is independently —C($R^{12}$b)$_2$-C$_{3-10}$cycloalkyl. In embodiments of the formulae above, each $R^{12}$ is independently $C_{2-9}$heterocycloalkyl. In embodiments of the formulae above, each $R^{12}$ is independently —C($R^{12}$b)$_2$-C$_{2-9}$heterocycloalkyl. In embodiments of the formulae above, each $R^{12}$ is independently $C_{6-10}$aryl. In embodiments of the formulae above, each $R^{12}$ is independently —C($R^{12}$b)$_2$-C$_6$-10aryl. In embodiments of the formulae above, each $R^{12}$ is independently —C($R^{12}$b)$_2$-C$_{1-9}$heteroaryl. In embodiments of the formulae above, each $R^{12}$ is independently $C_{1-9}$heteroaryl.

In embodiments of the formulae above, each $R^{12}$ is independently —C($R^{12}$b)$_2$-C$_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C($R^{12}$b)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C($R^{12}$b)$_2$-C$_6$-10aryl substituted with one, two, or three $R^{201}$. In embodiments of the formulae above, each $R^{12}$ is independently —C($R^{12}$b)$_2$-C$_{1-9}$heteroaryl substituted with one, two, or three $R^{20t}$ In embodiments of the formulae above, each $R^{12}$ is independently selected from hydrogen and methyl. In embodiments of the formulae above, each $R^{12}$ is independently selected from hydrogen and ethyl.

In embodiments of the formulae above, each $R^{12}$ is independently —C($R^{12}$b)$_2$-C$_{3-10}$cycloalkyl. In embodiments of the formulae above, each $R^{12}$ is independently $C_{2-9}$heterocycloalkyl. In embodiments of the formulae above, each $R^{12}$ is independently —C($R^{12}$b)$_2$-C$_{2-9}$heterocycloalkyl. In embodiments of the formulae above, each $R^{12}$ is independently $C_{6-10}$aryl. In embodiments of the formulae above, each $R^{12}$ is independently —C($R^{12}$b)$_2$-C$_6$-10aryl. In embodiments of the formulae above, each $R^{12}$ is independently —C($R^{12}$b)$_2$-C$_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above;

each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —C($R^{12}$b)$_2$-C$_{3-10}$ cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C($R^{12}$b)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C($R^{12}$b)$_2$-C$_{6-10}$aryl substituted with one, two, or three $R^{201}$. In embodiments of the formulae above, each $R^{12}$ is independently —C($R^{12}$b)$_2$-C$_{1-9}$heteroaryl substituted with one, two, or three $R^{201}$. In embodiments of the formulae above, each $R^{12}$ is independently $C_{1-9}$heteroaryl substituted with one, two, or three $R^{201}$. In embodiments of the formulae above, each $R^{12}$ is independently hydrogen. In embodiments of the formulae above, each $R^{12}$ is independently $C_{1-6}$alkyl. In embodiments of the formulae above, each $R^{12}$ is independently $C_{2-6}$alkenyl. In embodiments of the formulae above, each $R^{12}$ is independently $C_{2-6}$alkynyl. In embodiments of the formulae above, each $R^{12}$ is independently $C_{3-10}$cycloalkyl. In embodiments of the formulae above, each $R^{12}$ is independently —C(H)$_2$-C$_{3-10}$cycloalkyl. In embodiments of the formulae above, each $R^{12}$ is independently $C_{2-9}$heterocycloalkyl. In embodiments of the formulae above, each $R^{12}$ is independently —C(H)$_2$-C$_{2-9}$heterocycloalkyl. In embodiments of the formulae above, each $R^{12}$ is independently $C_{6-10}$aryl. In embodiments of the formulae above, each $R^{12}$ is independently —C(H)$_2$-C$_6$-10aryl. In embodiments of the formulae above, each $R^{12}$ is independently —C(H)$_2$-C$_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above, each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —C(H)$_2$-C$_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C(H)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C(H)$_2$-C$_6$-10aryl substituted with one, two, or three $R^{201}$. In embodiments of the formulae above, each $R^{12}$ is independently —C(H)$_2$-C$_{1-9}$heteroaryl substituted with one, two, or three $R^{201}$. In embodiments of the formulae above, each $R^{12}$ is independently $C_{1-9}$heteroaryl substituted with one, two, or three $R^{20l}$.

In embodiments of the formulae above, $R^{12}$ is $C_{1-6}$alkyl optionally substituted with one, two, or three $R^{201}$. In embodiments of the formulae above of the subject compound, $R^{12}$ is methylene optionally substituted with one or two $R^{201}$. In further embodiments of the subject compound, $R^{12}$ is methylene. In embodiments of the formulae above of the subject compound, $R^{12}$ is ethylene optionally substituted with one, two, or three $R^{201}$. In embodiments of the formulae above of the subject compound, $R^{12}$ is ethylene. In embodiments of the formulae above of the subject compound, $R^{12}$ is propylene optionally substituted with one, two, or three $R^{201}$. In embodiments of the formulae above of the subject compound, $R^{12}$ is propylene. In embodiments of the formulae above, $R^{12}$ is -$CH_2$-$C_{2-9}$heterocycloalkyl optionally substituted with one, two, or three $R^{201}$. In embodiments of the formulae above, $R^{12}$ is —$CH_2$-(monocyclic $C_2$-sheterocycloalkyl) optionally substituted with one, two, or three $R^{201}$. In embodiments of the formulae above, $R^{12}$ is-$CH_2$-(monocyclic $C_3$-sheterocycloalkyl) optionally substituted with one, two, or three $R^{201}$. In embodiments of the formulae above, $R^{12}$ is -$CH_2$-(spirocyclic $C_{2-11}$heterocycloalkyl) optionally substituted with one, two, or three $R^{201}$. In embodiments of the formulae above, $R^{12}$ is -$CH_2$-(spirocyclic $C_{3-11}$heterocycloalkyl) optionally substituted with one, two, or three $R^{201}$. In embodiments of the formulae above, $R^{12}$ is -$CH_2$-(fused $C_{2-11}$heterocycloalkyl) optionally substituted with one, two, or three $R^{201}$. In embodiments of the formulae above, $R^{12}$ is -$CH_2$-(spirocyclic $C_{6-8}$heterocycloalkyl) optionally substituted with one, two, or three $R^{20t}$;

In embodiments of the formulae above, $R^{12}$ is $C_{1-6}$alkyl optionally substituted with one, two, or three $R^{201}$. In embodiments of the formulae above of the compound, $R^{12}$ is methylene optionally substituted with one or two $R^{201}$. In further embodiments of the compound, $R^{12}$ is methylene. In embodiments of the formulae above of the compound, $R^{12}$ is ethylene optionally substituted with one, two, or three $R^{201}$. In embodiments of the formulae above of the compound, $R^{12}$ is ethylene. In embodiments of the formulae above of the compound, $R^{12}$ is propylene optionally substituted with one, two, or three $R^{201}$. In embodiments of the formulae above of the compound, $R^{12}$ is propylene. In embodiments of the formulae above, $R^{12}$ is -$CH_2$-$C_{2-9}$heterocycloalkyl optionally substituted with one, two, or three $R^{201}$. In embodiments of the formulae above, $R^{12}$ is -$CH_2$-(monocyclic $C_{2-8}$heterocycloalkyl) optionally substituted with one, two, or three $R^{201}$. In embodiments of the formulae above, $R^{12}$ is -$CH_2$-(monocyclic $C_3$-sheterocycloalkyl) optionally substituted with one, two, or three $R^{201}$. In embodiments of the formulae above, $R^{12}$ is -$CH_2$-(spirocyclic $C_{2-11}$heterocycloalkyl) optionally substituted with one, two, or three $R^{201}$. In embodiments of the formulae above, $R^{12}$ is -$CH_2$-(spirocyclic $C_{3-11}$heterocycloalkyl) optionally substituted with one, two, or three $R^{201}$. In embodiments of the formulae above, $R^{12}$ is -$CH_2$-(fused $C_{2-11}$heterocycloalkyl) optionally substituted with one, two, or three $R^{201}$. In embodiments of the formulae above, $R^{12}$ is -$CH_2$-(spirocyclic $C_6$—¿heterocycloalkyl) optionally substituted with one, two, or three $R^{20t}$;

The individual embodiments herein below, or combinations thereof, (e.g., embodiments of $R^{12}$) are applicable to compounds of Formula (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"- 1d), (B"- 1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{12}$ is independently hydrogen. In embodiments of the formulae above, each $R^{12}$ is independently $C_{1-6}$alkyl. In embodiments of the formulae above, each $R^{12}$ is independently $C_{2-6}$alkenyl. In embodiments of the formulae above, each $R^{12}$ is independently $C_{2-6}$alkynyl. In embodiments of the formulae above, each $R^{12}$ is independently $C_{3-10}$cycloalkyl. In embodiments of the formulae above, each $R^{12}$ is independently —$C(R^{12}c)_2$-$C_{3-10}$cycloalkyl. In embodiments of the formulae above, each $R^{12}$ is independently $C_{2-9}$heterocycloalkyl. In embodiments of the formulae above, each $R^{12}$ is independently —$C(R^{12}c)_2$-$C_{2-9}$heterocycloalkyl. In embodiments of the formulae above, each $R^{12}$ is independently $C_{6-10}$aryl. In embodiments of the formulae above, each $R^{12}$ is independently —$C(R^{12}c)_2$-$C_6$-10aryl. In embodiments of the formulae above, each $R^{12}$ is independently —$C(R^{12}c)_2$-$C_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above;

each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —$C(R^{12}c)_2$-$C_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —$C(R^{12}c)_2$-$C_{2-9}$heterocycloalkyl substituted with one, two, or three $R^{201}$. In embodiments of the formulae above, each $R^{12}$ is independently $C_6$-10aryl substituted with one, two, or three $R^{201}$. In embodiments of the formulae above, each $R^{12}$ is independently —$C(R^{12}c)_2$-$C_{6-10}$aryl substituted with one, two, or three $R^{201}$. In embodiments of the formulae above, each $R^{12}$ is independently —$C(R^{12}c)_2$-$C_{1-9}$heteroaryl substituted with one, two, or three $R^{201}$. In embodiments of the formulae above, each $R^{12}$ is independently $C_{1-9}$heteroaryl substituted with one, two, or three $R^{201}$. In embodiments of the formulae above, each $R^{12}$ is independently hydrogen. In embodiments of the formulae above, each $R^{12}$ is independently $C_{1-6}$alkyl. In embodiments of the formulae above, each $R^{12}$ is independently $C_{2-6}$alkenyl. In embodiments of the formulae above, each $R^{12}$ is independently $C_{2-6}$alkynyl. In embodiments of the formulae above, each $R^{12}$ is independently $C_{3-10}$cycloalkyl. In embodiments of the formulae above, each $R^{12}$ is independently —$C(H)_2$-$C_{3-10}$cycloalkyl. In embodiments of the formulae above, each $R^{12}$ is independently $C_{2-9}$heterocycloalkyl. In embodiments of the formulae above, each $R^{12}$ is independently —$C(H)_2$-$C_{2-9}$heterocycloalkyl. In embodiments of the formulae above, each $R^{12}$ is independently $C_{6-10}$aryl. In embodiments of the formulae above, each $R^{12}$ is independently —$C(H)_2$-$C_6$-10aryl. In embodiments of the formulae above, each $R^{12}$ is independently —$C(H)_2$-$C_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above, each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —C(H)$_2$-C$_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C(H)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C(H)$_2$-C$_6$-10aryl substituted with one, two, or three $R^{201}$. In embodiments of the formulae above, each $R^{12}$ is independently —C(H)$_2$-C$_{1-9}$heteroaryl substituted with one, two, or three $R^{201}$. In embodiments of the formulae above, each $R^{12}$ is independently $C_{1-9}$heteroaryl substituted with one, two, or three $R^{201}$. In embodiments of the formulae above, each $R^{12}$ is independently methyl. In embodiments of the formulae above, each $R^{12}$ is independently ethyl. In embodiments of the formulae above, each $R^{12}$ is independently —C(R$^{12}$c)$_2$-C$_{3-10}$ cycloalkyl. In embodiments of the formulae above, each $R^{12}$ is independently $C_{2-9}$heterocycloalkyl. In embodiments of the formulae above, each $R^{12}$ is independently —C(R$^{12}$c)$_2$-C$_{2-9}$heterocycloalkyl. In embodiments of the formulae above, each $R^{12}$ is independently $C_{6-10}$aryl. In embodiments of the formulae above, each $R^{12}$ is independently —C(R$^{12}$c)$_2$-C$_{6-10}$aryl. In embodiments of the formulae above;

each $R^{12}$ is independently —C(R$^{12}$c)$_2$-C$_{1-9}$heteroaryl. In embodiments of the formulae above, each $R^{12}$ is independently $C_{1-9}$heteroaryl.

In embodiments of the formulae above, each $R^{12}$ is independently —C(R$^{12}$c)$_2$-C$_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C(R$^{12}$c)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C(R$^{12}$c)$_2$-C$_6$-10aryl substituted with one, two, or three $R^{201}$. In embodiments of the formulae above, each $R^{12}$ is independently —C(R$^{12}$c)$_2$-C$_{1-9}$heteroaryl substituted with one, two, or three $R^{20l}$.

In embodiments of the formulae above, each $R^{12}$ is independently selected from hydrogen and methyl. In embodiments of the formulae above, each $R^{12}$ is independently selected from hydrogen and ethyl.

In embodiments of the formulae above, each $R^{12}$ is independently —C(R$^{12}$c)$_2$-C$_{3-10}$cycloalkyl. In embodiments of the formulae above, each $R^{12}$ is independently $C_{2-9}$heterocycloalkyl. In embodiments of the formulae above, each $R^{12}$ is independently —C(R$^{12}$c)$_2$-C$_{2-9}$heterocycloalkyl. In embodiments of the formulae above, each $R^{12}$ is independently $C_{6-10}$aryl. In embodiments of the formulae above, each $R^{12}$ is independently —C(R$^{12}$c)$_2$-C$_6$-10aryl. In embodiments of the formulae above, each $R^{12}$ is independently —C(R$^{12}$c)$_2$-C$_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above, each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —C(R$^{12}$c)$_2$-C$_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C(R$^{12}$c)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C(R$^{12}$c)$_2$-C$_{6-10}$aryl substituted with one, two, or three $R^{201}$. In embodiments of the formulae above, each $R^{12}$ is independently —C(R$^{12}$c)$_2$-C$_{1-9}$heteroaryl substituted with one, two, or three $R^{201}$. In embodiments of the formulae above, each $R^{12}$ is independently $C_{1-9}$heteroaryl substituted with one, two, or three $R^{201}$. In embodiments of the formulae above, each $R^{12}$ is independently hydrogen. In embodiments of the formulae above, each $R^{12}$ is independently $C_{1-6}$alkyl. In embodiments of the formulae above, each $R^{12}$ is independently $C_{2-6}$alkenyl. In embodiments of the formulae above, each $R^{12}$ is independently $C_{2-6}$alkynyl. In embodiments of the formulae above, each $R^{12}$ is independently $C_{3-10}$cycloalkyl. In embodiments of the formulae above, each $R^{12}$ is independently —C(H)$_2$-C$_{3-10}$cycloalkyl. In embodiments of the formulae above, each $R^{12}$ is independently $C_{2-9}$heterocycloalkyl. In embodiments of the formulae above, each $R^{12}$ is independently —C(H)$_2$-C$_{2-9}$heterocycloalkyl. In embodiments of the formulae above, each $R^{12}$ is independently $C_{6-10}$aryl. In embodiments of the formulae above, each $R^{12}$ is independently —C(H)$_2$-C$_6$-10aryl. In embodiments of the formulae above, each $R^{12}$ is independently —C(H)$_2$-C$_{1-9}$heteroaryl. In embodiments of the formulae above, each $R^{12}$ is independently $C_{1-9}$heteroaryl. In embodiments of the formulae above, each $R^{12}$ is independently $C_{1-6}$alkyl substituted with one, two, or three $R^{201}$. In embodiments of the formulae above, each $R^{12}$ is independently $C_{2-6}$alkenyl substituted with one, two, or three $R^{201}$. In embodiments of the formulae above, each $R^{12}$ is independently $C_{2-6}$alkynyl substituted with one, two, or three $R^{201}$. In embodiments of the formulae above, each $R^{12}$ is independently $C_{3-10}$cycloalkyl substituted with one, two, or three $R^{201}$. In embodiments of the formulae above, each $R^{12}$ is independently —C(H)$_2$-C$_{3-10}$cycloalkyl substituted with one, two, or three $R^{201}$. In embodiments of the formulae above, each $R^{12}$ is independently $C_{2-9}$heterocycloalkyl substituted with one, two, or three $R^{201}$. In embodiments of the formulae above, each $R^{12}$ is independently —C(H)$_2$-C$_{2-9}$heterocycloalkyl substituted with one, two, or three $R^{201}$. In embodiments of the formulae above, each $R^{12}$ is independently $C_{6-10}$aryl substituted with one, two, or three $R^{201}$. In embodiments of the formulae above, each $R^{12}$ is independently —C(H)$_2$-

$C_{6\text{-}10}$aryl substituted with one, two, or three $R^{201}$. In embodiments of the formulae above, each $R^{12}$ is independently —$C(H)_2$-$C_{1\text{-}9}$heteroaryl substituted with one, two, or three $R^{201}$. In embodiments of the formulae above, each $R^{12}$ is independently $C_{1\text{-}9}$heteroaryl substituted with one, two, or three $R^{201}$.

In embodiments of the formulae above, $R^{12}$ is $C_{1\text{-}6}$alkyl optionally substituted with one, two, or three $R^{201}$. In embodiments of the formulae above of the subject compound, $R^{12}$ is methylene optionally substituted with one or two $R^{201}$. In further embodiments of the subject compound, $R^{12}$ is methylene. In embodiments of the formulae above of the subject compound, $R^{12}$ is ethylene optionally substituted with one, two, or three $R^{201}$. In embodiments of the formulae above of the subject compound, $R^{12}$ is ethylene. In embodiments of the formulae above of the subject compound, $R^{12}$ is propylene optionally substituted with one, two, or three $R^{201}$. In embodiments of the formulae above of the subject compound, $R^{12}$ is propylene. In embodiments of the formulae above, $R^{12}$ is -$CH_2$-$C_{2\text{-}9}$heterocycloalkyl optionally substituted with one, two, or three $R^{201}$. In embodiments of the formulae above, $R^{12}$ is —$CH_2$-(monocyclic $C_{2\text{-}8}$heterocycloalkyl) optionally substituted with one, two, or three $R^{201}$. In embodiments of the formulae above, $R^{12}$ is-$CH_2$-(monocyclic $C_3$-sheterocycloalkyl) optionally substituted with one, two, or three $R^{201}$. In embodiments of the formulae above, $R^{12}$ is -$CH_2$-(spirocyclic $C_{2\text{-}11}$heterocycloalkyl) optionally substituted with one, two, or three $R^{201}$. In embodiments of the formulae above, $R^{12}$ is -$CH_2$-(spirocyclic $C_{3\text{-}11}$heterocycloalkyl) optionally substituted with one, two, or three $R^{201}$. In embodiments of the formulae above, $R^{12}$ is -$CH_2$-(fused $C_{2\text{-}11}$heterocycloalkyl) optionally substituted with one, two, or three $R^{201}$. In embodiments of the formulae above, $R^{12}$ is -$CH_2$-(spirocyclic $C_6$-sheterocycloalkyl) optionally substituted with one, two, or three $R^{201}$.

In embodiments of the formulae above, $R^{12}$ is $C_{1\text{-}6}$alkyl optionally substituted with one, two, or three $R^{201}$. In embodiments of the formulae above of the compound, $R^{12}$ is methylene optionally substituted with one or two $R^{201}$. In further embodiments of the compound, $R^{12}$ is methylene. In embodiments of the formulae above of the compound, $R^{12}$ is ethylene optionally substituted with one, two, or three $R^{201}$. In embodiments of the formulae above of the compound, $R^{12}$ is ethylene. In embodiments of the formulae above of the compound, $R^{12}$ is propylene optionally substituted with one, two, or three $R^{201}$. In embodiments of the formulae above of the compound, $R^{12}$ is propylene. In embodiments of the formulae above, $R^{12}$ is -$CH_2$-$C_{2\text{-}9}$heterocycloalkyl optionally substituted with one, two, or three $R^{201}$. In embodiments of the formulae above, $R^{12}$ is -$CH_2$-(monocyclic $C_{2\text{-}8}$heterocycloalkyl) optionally substituted with one, two, or three $R^{201}$. In embodiments of the formulae above, $R^{12}$ is -$CH_2$-(monocyclic $C_3$-sheterocycloalkyl) optionally substituted with one, two, or three $R^{201}$. In embodiments of the formulae above, $R^{12}$ is -$CH_2$-(spirocyclic $C_{2\text{-}11}$heterocycloalkyl) optionally substituted with one, two, or three $R^{201}$. In embodiments of the formulae above, $R^{12}$ is —$CH_2$-(spirocyclic $C_{3\text{-}11}$heterocycloalkyl) optionally substituted with one, two, or three $R^{201}$. In embodiments of the formulae above, $R^{12}$ is-$CH_2$-(fused $C_{2\text{-}11}$heterocycloalkyl) optionally substituted with one, two, or three $R^{201}$. In embodiments of the formulae above, $R^{12}$ is —$CH_2$-(spirocyclic $C_{6\text{-}8}$heterocycloalkyl) optionally substituted with one, two, or three $R^{201}$;

The individual embodiments herein below, or combinations thereof, (e.g., embodiments of $R^{12a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (X VIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), or (XXVIf), or a pharmaceutically acceptable salt or solvate thereof. In embodiments of the formulae above, each $R^{12a}$ is independently hydrogen. In embodiments of the formulae above, each $R^{12a}$ is independently $C_{1\text{-}6}$alkyl. In embodiments of the formulae above, each $R^{12a}$ is independently $C_{2\text{-}6}$alkenyl. In embodiments of the formulae above, each $R^{12a}$ is independently $C_{2\text{-}6}$alkynyl. In embodiments of the formulae above, each $R^{12a}$ is independently $C_{3\text{-}10}$cycloalkyl. In embodiments of the formulae above, each $R^{12a}$ is independently —$C(R^{12}b)_2$-$C_{3\text{-}10}$cycloalkyl. In embodiments of the formulae above, each $R^{12a}$ is independently $C_{2\text{-}9}$heterocycloalkyl. In embodiments of the formulae above, each $R^{12}a$ is independently —$C(R^{12}b)_2$-$C_{2\text{-}9}$heterocycloalkyl. In embodiments of the formulae above, each $R^{12}a$ is independently $C_{6\text{-}10}$aryl. In embodiments of the formulae above, each $R^{12}a$ is independently —$C(R^{12}b)_2$-$C_6$-10aryl. In embodiments of the formulae above, each $R^{12}a$ is independently —$C(R^{12}b)_2$-$C_{1\text{-}9}$heteroaryl. In embodiments of the formulae above, each $R^{12a}$ is independently $C_{1\text{-}9}$heteroaryl. In embodiments of the formulae above, each $R^{12a}$ is independently $C_{1\text{-}6}$alkyl substituted with one, two, or three $R^{201}$. In embodiments of the formulae above, each $R^{12}a$ is independently $C_{2\text{-}6}$alkenyl substituted with one, two, or three $R^{201}$. In embodiments of the formulae above, each $R^{12}a$ is independently $C_{2\text{-}6}$alkynyl substituted with one, two, or three $R^{201}$. In embodiments of the formulae above, each $R^{12a}$ is independently $C_{3\text{-}10}$cycloalkyl substituted with one, two, or three $R^{201}$. In embodiments of the formulae above, each $R^{12}a$ is independently —$C(R^{12}b)_2$-$C_{3\text{-}10}$cycloalkyl substituted with one, two, or three $R^{201}$. In embodiments of the formulae above, each $R^{12a}$ is independently $C_{2\text{-}9}$heterocycloalkyl substituted with one, two, or three $R^{201}$. In embodiments of the formulae above, each $R^{12}a$ is independently —$C(R^{12}b)_2$-$C_{2\text{-}9}$heterocycloalkyl substituted with one, two, or three $R^{201}$. In embodiments of the formulae above, each $R^{12}a$ is independently $C_{6\text{-}10}$aryl substituted with one, two, or three $R^{201}$. In embodiments of the formulae above, each $R^{12}a$ is independently —$C(R^{12}b)_2$-$C_6$-10aryl substituted with one, two, or three $R^{201}$. In embodiments of the formulae above, each $R^{12}a$ is independently —$C(R^{12}b)_2$-$C_{1\text{-}9}$heteroaryl substituted with one, two, or three $R^{201}$. In embodiments of the formulae above, each $R^{12}a$ is independently $C_{1\text{-}9}$heteroaryl substituted with one, two, or three $R^{201}$. In embodiments of the formulae above, each $R^{12}a$ is independently hydrogen. In embodiments of the formulae above, each $R^{12}a$ is independently $C_{1-6}$alkyl. In embodiments of the formulae above, each $R^{12}a$ is independently $C_{2-6}$alkenyl. In embodiments of the formulae above, each $R^{12a}$ is independently $C_{2-6}$alkynyl. In embodiments of the formulae above, each $R^{12}a$ is independently $C_{3-10}$cycloalkyl. In embodiments of the formulae above, each $R^{12}a$ is independently —C(H)$_2$-C$_{3-10}$cycloalkyl. In embodiments of the formulae above, each $R^{12a}$ is independently $C_{2-9}$heterocycloalkyl. In embodiments of the formulae above, each $R^{12}a$ is independently —C(H)$_2$-C$_{2-9}$heterocycloalkyl. In embodiments of the formulae above, each $R^{12}a$ is independently $C_{6-10}$aryl. In embodiments of the formulae above, each $R^{12a}$ is independently —C(H)$_2$-C$_{6-10}$aryl. In embodiments of the formulae above, each $R^{12}a$ is independently —C(H)$_2$-C$_{1-9}$heteroaryl. In embodiments of the formulae above, each $R^{12}a$ is independently $C_{1-9}$heteroaryl. In embodiments of the formulae above, each $R^{12}a$ is independently $C_{1-6}$alkyl substituted with one, two, or three $R^{201}$. In embodiments of the formulae above;
each $R^{12}a$ is independently $C_{2-6}$alkenyl substituted with one, two, or three $R^{201}$. In embodiments of the formulae above, each $R^{12a}$ is independently $C_{2-6}$alkynyl substituted with one, two, or three $R^{201}$. In embodiments of the formulae above, each $R^{12a}$ is independently $C_{3-10}$cycloalkyl substituted with one, two, or three $R^{201}$. In embodiments of the formulae above, each $R^{12}a$ is independently —C(H)$_2$-C$_{3-10}$cycloalkyl substituted with one, two, or three $R^{201}$. In embodiments of the formulae above, each $R^{12}a$ is independently $C_{2-9}$heterocycloalkyl substituted with one, two, or three $R^{201}$. In embodiments of the formulae above, each $R^{12}a$ is independently —C(H)$_2$-C$_{2-9}$heterocycloalkyl substituted with one, two, or three $R^{201}$. In embodiments of the formulae above, each $R^{12a}$ is independently $C_{6-10}$aryl substituted with one, two, or three $R^{201}$. In embodiments of the formulae above, each $R^{12}a$ is independently —C(H)$_2$-C$_{6-10}$aryl substituted with one, two, or three $R^{201}$. In embodiments of the formulae above, each $R^{12}a$ is independently —C(H)$_2$-C$_{1-9}$heteroaryl substituted with one, two, or three $R^{201}$. In embodiments of the formulae above, each $R^{12a}$ is independently $C_{1-9}$heteroaryl substituted with one, two, or three $R^{201}$. In embodiments of the formulae above, each $R^{12a}$ is independently methyl. In embodiments of the formulae above, each $R^{12a}$ is independently ethyl. In embodiments of the formulae above, each $R^{12}a$ is independently —C(R$^{12}$b)$_2$-C$_{3-10}$cycloalkyl. In embodiments of the formulae above, each $R^{12}a$ is independently $C_{2-9}$heterocycloalkyl. In embodiments of the formulae above, each $R^{12}a$ is independently —C(R$^{12}$b)$_2$-C$_{2-9}$heterocycloalkyl. In embodiments of the formulae above, each $R^{12}a$ is independently $C_{6-10}$aryl. In embodiments of the formulae above, each $R^{12}a$ is independently —C(R$^{12}$b)$_2$-C$_6$-10aryl. In embodiments of the formulae above, each $R^{12a}$ is independently —C(R$^{12}$b)$_2$-C$_{1-9}$heteroaryl. In embodiments of the formulae above, each $R^{12}a$ is independently $C_{1-9}$heteroaryl.

In embodiments of the formulae above, each $R^{12}a$ is independently —C(R$^{12}$b)$_2$-C$_{3-10}$cycloalkyl substituted with one, two, or three $R^{201}$. In embodiments of the formulae above, each $R^{12a}$ is independently $C_{2-9}$heterocycloalkyl substituted with one, two, or three $R^{201}$. In embodiments of the formulae above, each $R^{12a}$ is independently —C(R$^{12}$b)$_2$-C$_{2-9}$heterocycloalkyl substituted with one, two, or three $R^{201}$. In embodiments of the formulae above, each $R^{12}a$ is independently $C_{6-10}$aryl substituted with one, two, or three $R^{201}$. In embodiments of the formulae above, each $R^{12}a$ is independently —C(R$^{12}$b)$_2$-C$_6$-10aryl substituted with one, two, or three $R^{201}$. In embodiments of the formulae above, each $R^{12a}$ is independently —C(R$^{12}$b)$_2$-C$_{1-9}$heteroaryl substituted with one, two, or three $R^{20l}$.

In embodiments of the formulae above, each $R^{12}a$ is independently selected from hydrogen and methyl. In embodiments of the formulae above, each $R^{12a}$ is independently selected from hydrogen and ethyl.

In embodiments of the formulae above, each $R^{12}a$ is independently —C(R$^{12}$b)$_2$-C$_{3-10}$cycloalkyl. In embodiments of the formulae above, each $R^{12a}$ is independently $C_{2-9}$heterocycloalkyl. In embodiments of the formulae above, each $R^{12a}$ is independently —C(R$^{12}$b)$_2$-C$_{2-9}$heterocycloalkyl. In embodiments of the formulae above, each $R^{12a}$ is independently $C_{6-10}$aryl. In embodiments of the formulae above, each $R^{12}a$ is independently —C(R$^{12}$b)$_2$-C$_6$-10aryl. In embodiments of the formulae above, each $R^{12a}$ is independently —C(R$^{12}$b)$_2$-C$_{1-9}$heteroaryl. In embodiments of the formulae above, each $R^{12}a$ is independently $C_{1-9}$heteroaryl. In embodiments of the formulae above, each $R^{12}a$ is independently $C_{1-6}$alkyl substituted with one, two, or three $R^{201}$. In embodiments of the formulae above;
each $R^{12}a$ is independently $C_{2-6}$alkenyl substituted with one, two, or three $R^{201}$. In embodiments of the formulae above, each $R^{12}a$ is independently $C_{2-6}$alkynyl substituted with one, two, or three $R^{201}$. In embodiments of the formulae above, each $R^{12a}$ is independently $C_{3-10}$cycloalkyl substituted with one, two, or three $R^{201}$. In embodiments of the formulae above, each $R^{12}a$ is independently —C(R$^{12}$b)$_2$-C$_{3-10}$cycloalkyl substituted with one, two, or three $R^{201}$. In embodiments of the formulae above, each $R^{12}a$ is independently $C_{2-9}$heterocycloalkyl substituted with one, two, or three $R^{201}$. In embodiments of the formulae above, each $R^{12}a$ is independently —C(R$^{12}$b)$_2$-C$_{2-9}$heterocycloalkyl substituted with one, two, or three $R^{201}$. In embodiments of the formulae above, each $R^{12a}$ is independently $C_{6-10}$aryl substituted with one, two, or three $R^{201}$. In embodiments of the formulae above, each $R^{12}a$ is independently —C(R$^{12}$b)$_2$-C$_{6-10}$aryl substituted with one, two, or three $R^{201}$. In embodiments of the formulae above, each $R^{12}a$ is independently —C(R$^{12}$b)$_2$-C$_{1-9}$heteroaryl substituted with one, two, or three $R^{201}$. In embodiments of the formulae above, each $R^{12}a$ is independently $C_{1-9}$heteroaryl substituted with one, two, or three $R^{201}$. In embodiments of the formulae above, each $R^{12}a$ is independently hydrogen. In embodiments of the formulae above, each $R^{12a}$ is independently $C_{1-6}$alkyl. In embodiments of the formulae above, each $R^{12}a$ is independently $C_{2-6}$alkenyl. In embodiments of the formulae above, each $R^{12a}$ is independently $C_{2-6}$alkynyl. In embodiments of the formulae above, each $R^{12}a$ is independently $C_{3-10}$cycloalkyl. In embodiments of the formulae above, each $R^{12a}$ is independently —C(H)$_2$-C$_{3-10}$cycloalkyl. In embodiments of the formulae above, each $R^{12a}$ is independently $C_{2-9}$heterocycloalkyl. In embodiments of the formulae above, each
$R^{12}a$ is independently —C(H)$_2$-C$_{2-9}$heterocycloalkyl. In embodiments of the formulae above, each $R^{12}a$ is independently $C_{6-10}$aryl. In embodiments of the formulae above, each $R^{12}a$ is independently —C(H)$_2$-C$_6$-

10aryl. In embodiments of the formulae above, each $R^{12}a$ is independently —C(H)$_2$-C$_{1-9}$heteroaryl. In embodiments of the formulae above, each $R^{12}a$ is independently C$_{1-9}$heteroaryl. In embodiments of the formulae above, each $R^{12}a$ is independently C$_{1-6}$alkyl substituted with one, two, or three $R^{201}$. In embodiments of the formulae above, each $R^{12a}$ is independently C$_{2-6}$alkenyl substituted with one, two, or three $R^{201}$. In embodiments of the formulae above, each $R^{12a}$ is independently C$_{2-6}$alkynyl substituted with one, two, or three $R^{201}$. In embodiments of the formulae above, each $R^{12a}$ is independently C$_{3-10}$cycloalkyl substituted with one, two, or three $R^{201}$. In embodiments of the formulae above, each $R^{12a}$ is independently —C(H)$_2$-C$_{3-10}$cycloalkyl substituted with one, two, or three $R^{201}$. In embodiments of the formulae above, each $R^{12}a$ is independently C$_{2-9}$heterocycloalkyl substituted with one, two, or three $R^{201}$. In embodiments of the formulae above, each $R^{12}a$ is independently —C(H)$_2$-C$_{2-9}$heterocycloalkyl substituted with one, two, or three $R^{201}$. In embodiments of the formulae above, each $R^{12}a$ is independently C$_{6-10}$aryl substituted with one, two, or three $R^{201}$. In embodiments of the formulae above, each $R^{12}a$ is independently —C(H)$_2$-C$_6$-10aryl substituted with one, two, or three $R^{201}$. In embodiments of the formulae above, each $R^{12}a$ is independently —C(H)$_2$-C$_{1-9}$heteroaryl substituted with one, two, or three $R^{201}$. In embodiments of the formulae above, each $R^{12a}$ is independently C$_{1-9}$heteroaryl substituted with one, two, or three $R^{20r}$;

In embodiments of the formulae above, $R^{12}a$ is C$_{1-6}$alkyl optionally substituted with one, two, or three $R^{201}$. In embodiments of the formulae above of the subject compound, $R^{12}a$ is methylene optionally substituted with one or two $R^{201}$. In further embodiments of the subject compound, $R^{12}a$ is methylene. In embodiments of the formulae above of the subject compound, $R^{12a}$ is ethylene optionally substituted with one, two, or three $R^{201}$. In embodiments of the formulae above of the subject compound, $R^{12}a$ is ethylene. In embodiments of the formulae above of the subject compound, $R^{12a}$ is propylene optionally substituted with one, two, or three $R^{201}$. In embodiments of the formulae above of the subject compound, $R^{12}a$ is propylene. In embodiments of the formulae above, $R^{12a}$ is -CH$_2$-C$_{2-9}$heterocycloalkyl optionally substituted with one, two, or three $R^{201}$. In embodiments of the formulae above, $R^{12}a$ is —CH$_2$-(monocyclic C$_2$-sheterocycloalkyl) optionally substituted with one, two, or three $R^{201}$. In embodiments of the formulae above, $R^{12}a$ is-CH$_2$-(monocyclic C$_3$-sheterocycloalkyl) optionally substituted with one, two, or three $R^{201}$. In embodiments of the formulae above, $R^{12}a$ is -CH$_2$-(spirocyclic C$_{2-11}$heterocycloalkyl) optionally substituted with one, two, or three $R^{201}$. In embodiments of the formulae above, $R^{12}a$ is -CH$_2$-(spirocyclic C$_{3-11}$heterocycloalkyl) optionally substituted with one, two, or three $R^{201}$. In embodiments of the formulae above, $R^{12a}$ is -CH$_2$-(fused C$_{2-11}$heterocycloalkyl) optionally substituted with one, two, or three $R^{201}$. In embodiments of the formulae above, $R^{12}a$ is -CH$_2$-(spirocyclic C$_{6-8}$heterocycloalkyl) optionally substituted with one, two, or three $R^{20r}$ In embodiments of the formulae above, $R^{12}a$ is C$_{1-6}$alkyl optionally substituted with one, two, or three $R^{201}$. In embodiments of the formulae above of the compound, $R^{12}a$ is methylene optionally substituted with one or two $R^{201}$. In further embodiments of the compound, $R^{12a}$ is methylene. In embodiments of the formulae above of the compound, $R^{12}a$ is ethylene optionally substituted with one, two, or three $R^{201}$. In embodiments of the formulae above of the compound, $R^{12}a$ is ethylene. In embodiments of the formulae above of the compound, $R^{12a}$ is propylene optionally substituted with one, two, or three $R^{201}$. In embodiments of the formulae above of the compound, $R^{12a}$ is propylene. In embodiments of the formulae above, $R^{12a}$ is -CH$_2$-C$_{2-9}$heterocycloalkyl optionally substituted with one, two, or three $R^{201}$. In embodiments of the formulae above, $R^{12a}$ is -CH$_2$-(monocyclic C$_{2-8}$heterocycloalkyl) optionally substituted with one, two, or three $R^{201}$. In embodiments of the formulae above, $R^{12}a$ is -CH$_2$-(monocyclic C$_3$-sheterocycloalkyl) optionally substituted with one, two, or three $R^{201}$. In embodiments of the formulae above, $R^{12}a$ is -CH$_2$-(spirocyclic C$_{2-11}$heterocycloalkyl) optionally substituted with one, two, or three $R^{201}$. In embodiments of the formulae above, $R^{12}a$ is -CH$_2$-(spirocyclic C$_{3-11}$heterocycloalkyl) optionally substituted with one, two, or three $R^{201}$. In embodiments of the formulae above, $R^{12}a$ is -CH$_2$-(fused C$_{2-11}$heterocycloalkyl) optionally substituted with one, two, or three $R^{201}$. In embodiments of the formulae above, $R^{12a}$ is -CH$_2$-(spirocyclic C$_{6-8}$heterocycloalkyl) optionally substituted with one, two, or three $R^{20r}$;

The individual embodiments herein below, or combinations thereof, (e.g., embodiments of $R^{201}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''- 1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each $R^{20r}$ is independently halogen. In embodiments of the formulae above, each $R^{20r}$ is independently oxo. In embodiments of the formulae above, each $R^{20r}$ is independently —CN. In embodiments of the formulae above, each $R^{20r}$ is independently C$_{1-6}$alkyl. In embodiments of the formulae above, each $R^{20t}$ is independently $C_{2-6}$alkenyl. In embodiments of the formulae above, each $R^{20t}$ is independently $C_{2-6}$alkynyl. In embodiments of the formulae above, each $R^{20t}$ is independently $C_{3-10}$cycloalkyl. In embodiments of the formulae above, each $R^{20t}$ is independently —CH$_2$-C$_{3-10}$cycloalkyl. In embodiments of the formulae above, each $R^{20t}$ is independently $C_{2-9}$heterocycloalkyl. In embodiments of the formulae above, each $R^{20t}$ is independently —CH$_2$-C$_{2-9}$heterocycloalkyl. In embodiments of the formulae above, each $R^{20t}$ is independently $C_{6-10}$aryl. In embodiments of the formulae above, each $R^{20t}$ is independently —CH$_2$-C$_6$-10aryl. In embodiments of the formulae above, each $R^{20t}$ is independently —CH$_2$-C$_{1-9}$heteroaryl. In embodiments of the formulae above, each $R^{20t}$ is independently $C_{1-9}$heteroaryl. In embodiments of the formulae above, each $R^{20t}$ is independently —OR$^{21}$. In embodiments of the formulae above, each $R^{20t}$ is independently —SR$^{21}$. In embodiments of the formulae above, each $R^{20t}$ is independently —N(R$^{22}$)(R$^{23}$). In embodiments of the formulae above, each $R^{20t}$ is independently —C(O)OR$^{22}$. In embodiments of the formulae above, each $R^{20t}$ is independently —C(O)N(R$^{22}$)(R$^{23}$). In embodiments of the formulae above, each $R^{20t}$ is independently —C(O)C(O)N(R$^{22}$)(R$^{23}$). In embodiments of the formulae above, each $R^{20t}$ is independently —OC(O)N(R$^{22}$)(R$^{23}$). In embodiments of the formulae above, each $R^{20t}$ is independently —N(R$^{24}$)C(O)N(R$^{22}$)(R$^{23}$). In embodiments of the formulae above, each $R^{20t}$ is independently —N(R$^{24}$)C(O)OR$^{25}$. In embodiments of the formulae above, each $R^{20t}$ is independently —N(R$^{24}$)C(O)R$^{25}$. In embodiments of the formulae above, each $R^{20t}$ is independently —N(R$^{24}$)S(O)$_2$R$^{25}$. In embodiments of the formulae above, each $R^{20t}$ is independently —C(O)R$^{25}$. In embodiments of the formulae above, each $R^{20t}$ is independently —S(O)$_2$R$^{25}$. In embodiments of the formulae above, each $R^{20t}$ is independently —S(O)$_2$N(R$^{22}$)(R$^{23}$). In embodiments of the formulae above, each $R^{20t}$ is independently —OCH$_2$C(O)OR$^{22}$. In embodiments of the formulae above, each $R^{20t}$ is independently —OC(O)R$^{25}$. In embodiments of the formulae above, each $R^{20t}$ is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently $C_{2-6}$alkynyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently $C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently —CH$_2$-C$_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently $C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above;

each $R^{20t}$ is independently —CH$_2$-C$_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently $C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently —CH$_2$-C$_6$-10aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently —CH$_2$-C$_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20t}$ is independently $C_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above;

each R$^{20t}$ is independently=NR$^{21}$.

The individual embodiments herein below, or combinations thereof, (e.g., embodiments of R$^{12}$a, R$^{12b}$, R$^{12}$, R$^{12c}$, or R$^2$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each R$^{12}$a is independently C$_{1-6}$alkyl. In embodiments of the formulae above, each R$^{12a}$ is independently C$_{2-6}$alkenyl. In embodiments of the formulae above, each R$^{12}$a is independently C$_{2-6}$alkynyl. In embodiments of the formulae above, each R$^{12}$a is independently C$_{3-10}$cycloalkyl. In embodiments of the formulae above, each R$^{12}$a is independently —C(R$^{12}$b)$_2$-C$_{3-10}$cycloalkyl. In embodiments of the formulae above, each R$^{12a}$ is independently C$_{2-9}$heterocycloalkyl. In embodiments of the formulae above, each R$^{12}$a is independently —C(R$^{12}$b)$_2$-C$_{2-9}$heterocycloalkyl. In embodiments of the formulae above, each R$^{12}$a is independently C$_{6-10}$aryl. In embodiments of the formulae above, each R$^{12}$a is independently —C(R$^{12}$b)$_2$-C$_6$-10aryl. In embodiments of the formulae above, each R$^{12a}$ is independently —C(R$^{12}$b)$_2$-C$_{1-9}$heteroaryl. In embodiments of the formulae above, each R$^{12a}$ is independently C$_{1-9}$heteroaryl. In embodiments of the formulae above, each R$^{12a}$ is independently C$_{1-6}$alkyl substituted with one, two, or three R$^{201}$. In embodiments of the formulae above, each R$^{12}$a is independently C$_2$-falkenyl substituted with one, two, or three R$^{201}$. In embodiments of the formulae above, each R$^{12}$a is independently C$_{2-6}$alkynyl substituted with one, two, or three R$^{201}$. In embodiments of the formulae above, each R$^{12a}$ is independently C$_{3-10}$cycloalkyl substituted with one, two, or three R$^{201}$. In embodiments of the formulae above, each R$^{12}$a is independently —C(R$^{126}$)$_2$-C$_{3-10}$cycloalkyl substituted with one, two, or three R$^{201}$. In embodiments of the formulae above, each R$^{12}$a is independently C$_{2-9}$heterocycloalkyl substituted with one, two, or three R$^{201}$. In embodiments of the formulae above, each R$^{12a}$ is independently —C(R$^{12}$b)$_2$-C$_{2-9}$heterocycloalkyl substituted with one, two, or three R$^{201}$. In embodiments of the formulae above, each R$^{12a}$ is independently C$_{6-10}$aryl substituted with one, two, or three R$^{201}$. In embodiments of the formulae above, each R$^{12a}$ is independently —C(R$^{12}$b)$_2$-C$_6$-10aryl substituted with one, two, or three R$^{201}$. In embodiments of the formulae above, each R$^{12}$a is independently —C(R$^{12}$b)$_2$-C$_{1-9}$heteroaryl substituted with one, two, or three R$^{201}$. In embodiments of the formulae above, each R$^{12}$a is independently C$_{1-9}$heteroaryl substituted with one, two, or three R$^{201}$. In embodiments of the formulae above, each R$^{12}$a is independently hydrogen. In embodiments of the formulae above, each R$^{12}$a is independently C$_{1-6}$alkyl. In embodiments of the formulae above, each R$^{12}$a is independently C$_{2-6}$alkenyl. In embodiments of the formulae above, each R$^{12}$a is independently C$_{2-6}$alkynyl. In embodiments of the formulae above, each R$^{12}$a is independently C$_{3-10}$ cycloalkyl. In embodiments of the formulae above, each R$^{12}$a is independently —C(H)$_2$-C$_{3-10}$cycloalkyl. In embodiments of the formulae above, each R$^{12a}$ is independently C$_{2-9}$heterocycloalkyl. In embodiments of the formulae above, each R$^{12}$a is independently —C(H)$_2$-C$_{2-9}$heterocycloalkyl. In embodiments of the formulae above, each R$^{12}$a is independently C$_{6-10}$aryl. In embodiments of the formulae above, each R$^{12a}$ is independently —C(H)$_2$-C$_6$-10aryl. In embodiments of the formulae above, each R$^{12a}$ is independently —C(H)$_2$-C$_{1-9}$heteroaryl. In embodiments of the formulae above, each R$^{12a}$ is independently C$_{1-9}$heteroaryl. In embodiments of the formulae above, each R$^{12a}$ is independently C$_{1-6}$alkyl substituted with one, two, or three R$^{201}$. In embodiments of the formulae above;

each R$^{12}$a is independently C$_{2-6}$alkenyl substituted with one, two, or three R$^{201}$. In embodiments of the formulae above, each R$^{12}$a is independently C$_{2-6}$alkynyl substituted with one, two, or three R$^{201}$. In embodiments of the formulae above, each R$^{12}$a is independently C$_{3-10}$cycloalkyl substituted with one, two, or three R$^{201}$. In embodiments of the formulae above, each R$^{12}$a is independently —C(H)$_2$-C$_{3-10}$cycloalkyl substituted with one, two, or three R$^{201}$. In embodiments of the formulae above, each R$^{12}$a is independently C$_{2-9}$heterocycloalkyl substituted with one, two, or three R$^{201}$. In embodiments of the formulae above, each R$^{12}$a is independently —C(H)$_2$-C$_{2-9}$heterocycloalkyl substituted with one, two, or three R$^{201}$. In embodiments of the formulae above, each R$^{12a}$ is independently C$_{6-10}$aryl substituted with one, two, or three R$^{201}$. In embodiments of the formulae above, each R$^{12a}$ is independently —C(H)$_2$-C$_{6-10}$aryl substituted with one, two, or three R$^{201}$. In embodiments of the formulae above, each $R^{12}a$ is independently —C(H)$_2$-C$_{1-9}$heteroaryl substituted with one, two, or three $R^{201}$. In embodiments of the formulae above, each $R^{12a}$ is independently C$_{1-9}$heteroaryl substituted with one, two, or three $R^{20l}$.

In embodiments of the formulae above, $R^2$ is —O—$R^{12}$a. In embodiments of the formulae above of the subject compound, $R^2$ is —O—$R^{12}$.

In select embodiments of the formulae above, $R^{12}a$ is C$_{1-6}$alkyl optionally substituted with one, two, or three $R^{201}$. In embodiments of the formulae above, $R^{12}a$ is methylene optionally substituted with one or two $R^{201}$. In further embodiments of the formulae above, $R^{12a}$ is methylene. In embodiments of the formulae above of the subject compound, $R^{12a}$ is ethylene optionally substituted with one, two, or three $R^{201}$. In embodiments of the formulae above, $R^{12}a$ is ethylene. In embodiments of the formulae above of the subject compound, $R^{12}a$ is propylene optionally substituted with one, two, or three $R^{201}$. In embodiments of the formulae above of the subject compound, $R^{12}a$ is propylene. In embodiments of the formulae above, $R^{12}a$ is -CH$_2$-C$_{2-9}$heterocycloalkyl optionally substituted with one, two, or three $R^{201}$. In embodiments of the formulae above, $R^{12}a$ is -CH$_2$-(monocyclic C$_{2-8}$heterocycloalkyl) optionally substituted with one, two, or three $R^{201}$. In embodiments of the formulae above, $R^{12}a$ is -CH$_2$-(monocyclic C$_3$-sheterocycloalkyl) optionally substituted with one, two, or three $R^{201}$. In embodiments of the formulae above, $R^{12a}$ is -CH$_2$-(spirocyclic C$_{2-11}$heterocycloalkyl) optionally substituted with one, two, or three $R^{201}$. In embodiments of the formulae above, $R^{12a}$ is -CH$_2$-(spirocyclic C$_{3-11}$heterocycloalkyl) optionally substituted with one, two, or three $R^{201}$. In embodiments of the formulae above, $R^{12a}$ is —CH$_2$-(fused C$_{2-11}$heterocycloalkyl) optionally substituted with one, two, or three $R^{201}$. In embodiments of the formulae above, $R^{12a}$ is —CH$_2$-(spirocyclic C$_{6-8}$heterocycloalkyl) optionally substituted with one, two, or three $R^{20l}$;

In embodiments of the formulae above, $R^{12}a$ is C$_{1-6}$alkyl optionally substituted with one, two, or three $R^{201}$. In embodiments of the formulae above of the compound, $R^{12}a$ is methylene optionally substituted with one or two $R^{201}$. In embodiments of the formulae above, $R^{12}a$ is methylene. In embodiments of the formulae above of the compound, $R^{12}a$ is ethylene optionally substituted with one, two, or three $R^{201}$. In embodiments of the formulae above, $R^{12}a$ is ethylene. In embodiments of the formulae above of the compound, $R^{12}a$ is propylene optionally substituted with one, two, or three $R^{201}$. In embodiments of the formulae above, $R^{12}a$ is propylene. In embodiments of the formulae above, $R^{12}a$ is -CH$_2$-C$_{2-9}$heterocycloalkyl optionally substituted with one, two, or three $R^{201}$. In embodiments of the formulae above, $R^{12}a$ is -CH$_2$-(monocyclic C$_{2-8}$heterocycloalkyl) optionally substituted with one, two, or three $R^{201}$. In embodiments of the formulae above, $R^{12}a$ is -CH$_2$-(monocyclic C$_3$-sheterocycloalkyl) optionally substituted with one, two, or three $R^{201}$. In embodiments of the formulae above, $R^{12a}$ is -CH$_2$-(spirocyclic C$_{2-11}$heterocycloalkyl) optionally substituted with one, two, or three $R^{201}$. In embodiments of the formulae above, $R^{12}a$ is -CH$_2$-(fused C$_{2-11}$heterocycloalkyl) optionally substituted with one, two, or three $R^{201}$. In embodiments of the formulae above, $R^{12}a$ is -CH$_2$-(spirocyclic C$_{6-8}$heterocycloalkyl) optionally substituted with one, two, or three $R^{20l}$;

In embodiments of the formulae above, $R^{12}a$ is C$_{1-6}$alkyl. In embodiments of the formulae above, $R^{12a}$ is C$_{2-6}$alkenyl. In embodiments of the formulae above, $R^{12}a$ is C$_{2-6}$alkynyl. In embodiments of the formulae above, $R^{12}a$ is C$_{3-10}$cycloalkyl. In embodiments of the formulae above, $R^{12a}$ is -CH$_2$-C$_{3-10}$cycloalkyl. In embodiments of the formulae above, $R^{12a}$ is C$_{2-9}$heterocycloalkyl. In embodiments of the formulae above, $R^{12}a$ is -CH$_2$-C$_{2-9}$heterocycloalkyl. In embodiments of the formulae above, $R^{12}a$ is C$_{6-10}$aryl. In embodiments of the formulae above, $R^{12}a$ is -CH$_2$-C$_{6-10}$aryl. In embodiments of the formulae above, $R^{12}a$ is -CH$_2$-C$_{1-9}$heteroaryl. In embodiments of the formulae above, $R^{12}a$ is C$_{1-9}$heteroaryl.

In embodiments of the formulae above, $R^{12}a$ is C$_{1-6}$alkyl optionally substituted with one, two, or three $R^{201}$. In embodiments of the formulae above, $R^{12}a$ is C$_{2-6}$alkenyl optionally substituted with one, two, or three $R^{201}$. In embodiments of the formulae above, $R^{12a}$ is C$_{2-6}$alkynyl optionally substituted with one, two, or three $R^{201}$. In embodiments of the formulae above, $R^{12a}$ is C$_{3-10}$cycloalkyl optionally substituted with one, two, or three $R^{201}$. In embodiments of the formulae above, $R^{12a}$ is -CH$_2$-C$_{3-10}$cycloalkyl optionally substituted with one, two, or three $R^{201}$. In embodiments of the formulae above, $R^{12}a$ is C$_{2-9}$heterocycloalkyl optionally substituted with one, two, or three $R^{201}$. In embodiments of the formulae above, $R^{12}a$ is -CH$_2$-C$_{2-9}$heterocycloalkyl optionally substituted with one, two, or three $R^{201}$. In embodiments of the formulae above, $R^{12}a$ is C$_{6-10}$aryl optionally substituted with one, two, or three $R^{201}$. In embodiments of the formulae above, $R^{12}a$ is -CH$_2$-C$_6$-10aryl optionally substituted with one, two, or three $R^{201}$. In embodiments of the formulae above, $R^{12}a$ is -CH$_2$-C$_{1-9}$heteroaryl optionally substituted with one, two, or three $R^{201}$. In embodiments of the formulae above, $R^{12a}$ is C$_{1-9}$heteroaryl optionally substituted with one, two, or three $R^{20l}$.

In embodiments of the formulae above, $R^{12}$ is C$_{1-6}$alkyl optionally substituted with one, two, or three $R^{201}$. In embodiments of the formulae above of the subject compound, $R^{12}$ is methylene optionally substituted with one or two $R^{201}$. In further embodiments of the formulae above of the subject compound, $R^{12}$ is methylene. In embodiments of the formulae above of the subject compound, $R^{12}$ is ethylene optionally substituted with one, two, or three $R^{201}$. In embodiments of the formulae above of the subject compound, $R^{12}$ is ethylene. In embodiments of the formulae above of the subject compound, $R^{12}$ is propylene optionally substituted with one, two, or three $R^{201}$. In embodiments of the formulae above, $R^{12}$ is propylene. In embodiments of the formulae above, $R^{12}$ is —CH$_2$-C$_{2-9}$heterocycloalkyl optionally substituted with one, two, or three $R^{201}$. In embodiments of the formulae above, $R^{12}$ is -CH$_2$-(monocyclic C$_2$-sheterocycloalkyl) optionally substituted with one, two, or three $R^{201}$. In embodiments of the formulae above, $R^{12}$ is —CH$_2$-(monocyclic C$_3$-sheterocycloalkyl) optionally substituted with one, two, or three $R^{201}$. In embodiments of the formulae above, $R^{12}$ is-CH$_2$-(spirocyclic C$_{2-11}$heterocycloalkyl) optionally substituted with one, two, or three $R^{201}$. In embodiments of the formulae above, $R^{12}$ is -CH$_2$-(spirocyclic C$_{3-11}$heterocycloalkyl) optionally substituted with one, two, or three $R^{201}$. In embodiments of the formulae above, $R^{12}$ is -CH$_2$-(fused C$_{2-11}$heterocycloalkyl) optionally substituted with one, two, or three $R^{201}$. In embodiments of the formulae above, $R^{12}$ is -CH$_2$-(spirocyclic C$_{6-8}$heterocycloalkyl) optionally substituted with one, two, or three $R^{20l}$.

In embodiments of the formulae above, $R^{12}$ is $C_{1-6}$alkyl optionally substituted with one, two, or three $R^{201}$. In embodiments of the compound, $R^{12}$ is methylene optionally substituted with one or two $R^{201}$. In further embodiments of the compound, $R^{12}$ is methylene. In embodiments of the formulae above of the compound, $R^{12}$ is ethylene optionally substituted with one, two, or three $R^{201}$. In embodiments of the compound, $R^{12}$ is ethylene. In embodiments of the formulae above of the compound, $R^{12}$ is propylene optionally substituted with one, two, or three $R^{201}$. In embodiments of the compound, $R^{12}$ is propylene. In embodiments of the formulae above, $R^{12}$ is -$CH_2$-$C_{2-9}$heterocycloalkyl optionally substituted with one, two, or three $R^{201}$. In embodiments of the formulae above, $R^{12}$ is -$CH_2$-(monocyclic $C_2$-sheterocycloalkyl) optionally substituted with one, two, or three $R^{201}$. In embodiments of the formulae above, $R^{12}$ is -$CH_2$-(monocyclic $C_3$-sheterocycloalkyl) optionally substituted with one, two, or three $R^{201}$. In embodiments of the formulae above, $R^{12}$ is -$CH_2$-(spirocyclic $C_{2-11}$heterocycloalkyl) optionally substituted with one, two, or three $R^{201}$. In embodiments of the formulae above, $R^{12}$ is -$CH_2$-(spirocyclic $C_{3-11}$heterocycloalkyl) optionally substituted with one, two, or three $R^{201}$. In embodiments of the formulae above, $R^{12}$ is -$CH_2$-(fused $C_{2-11}$heterocycloalkyl) optionally substituted with one, two, or three $R^{201}$. In embodiments of the formulae above, $R^{12}$ is -$CH_2$-(spirocyclic $C_{6-8}$heterocycloalkyl) optionally substituted with one, two, or three $R^{20r}$;

In embodiments of the formulae above, each $R^{12}b$ is independently hydrogen. In embodiments of the formulae above, each $R^{12}b$ is independently halogen. In embodiments of the formulae above, each $R^{12}b$ is independently oxo. In embodiments of the formulae above, each $R^{12}b$ is independently —CN. In embodiments of the formulae above, each $R^{12}b$ is independently $C_{1-6}$alkyl. In embodiments of the formulae above, each $R^{12}b$ is independently $C_{2-6}$alkenyl. In embodiments of the formulae above, each $R^{12}b$ is independently $C_{2-6}$alkynyl. In embodiments of the formulae above, each $R^{12}b$ is independently $C_{3-10}$cycloalkyl. In embodiments of the formulae above, each $R^{12}b$ is independently —$CH_2$-$C_{3-10}$cycloalkyl. In embodiments of the formulae above, each $R^{12}b$ is independently $C_{2-9}$heterocycloalkyl. In embodiments of the formulae above, each $R^{12}b$ is independently —$CH_2$-$C_{2-9}$heterocycloalkyl. In embodiments of the formulae above, each $R^{12}b$ is independently $C_{6-10}$aryl. In embodiments of the formulae above, each $R^{12}b$ is independently —$CH_2$-$C_{6-10}$aryl. In embodiments of the formulae above, each $R^{12}b$ is independently —$CH_2$-$C_{1-9}$heteroaryl. In embodiments of the formulae above, each $R^{12}b$ is independently $C_{1-9}$heteroaryl. In embodiments of the formulae above, each $R^{12}b$ is independently —$OR^{21}$. In embodiments of the formulae above, each $R^{12}b$ is independently —$SR^{21}$. In embodiments of the formulae above, each $R^{12}b$ is independently —$N(R^{22})(R^{23})$. In embodiments of the formulae above, each $R^{12}b$ is independently —$C(O)OR^{22}$. In embodiments of the formulae above, each $R^{12}b$ is independently —$C(O)N(R^{22})(R^{23})$. In embodiments of the formulae above, each $R^{12}b$ is independently —$C(O)C(O)N(R^{22})(R^{23})$. In embodiments of the formulae above, each $R^{12}b$ is independently —$OC(O)N(R^{22})(R^{23})$. In embodiments of the formulae above, each $R^{12}b$ is independently —$N(R^{24})C(O)N(R^{22})(R^{23})$. In embodiments of the formulae above, each $R^{12}b$ is independently —$N(R^{24})C(O)OR^{25}$. In embodiments of the formulae above, each $R^{12}b$ is independently —$N(R^{24})C(O)R^{25}$. In embodiments of the formulae above, each $R^{12}b$ is independently —$N(R^{24})S(O)_2R^{25}$. In embodiments of the formulae above, each $R^{12}b$ is independently —$C(O)R^{25}$. In embodiments of the formulae above, each $R^{12}b$ is independently —$S(O)_2R^{25}$. In embodiments of the formulae above, each $R^{12}b$ is independently —$S(O)_2N(R^{22})(R^{23})$. In embodiments of the formulae above, each $R^{12}b$ is independently —$OCH_2C(O)OR^{22}$. In embodiments of the formulae above, each $R^{12}b$ is independently —$OC(O)R^{25}$. In embodiments of the formulae above, each $R^{12}b$ is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}b$ is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}b$ is independently $C_{2-6}$alkynyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}b$ is independently $C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}b$ is independently —$CH_2$-$C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}b$ is independently $C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$.

In embodiments of the formulae above, each $R^{12}b$ is independently —$CH_2$-$C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$b is independently $C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above;

each $R^{12}$b is independently —CH$_2$-C$_6$-10aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$b is independently —CH$_2$-C$_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$b is independently $C_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above;

each $R^{12}$b is independently methyl. In embodiments of the formulae above, each $R^{12}$b is independently ethyl. In embodiments of the formulae above, each $R^{12}$b is independently propyl. In embodiments of the formulae above, each $R^{12}$b is independently selected from hydrogen and methyl.

In embodiments of the formulae above, each $R^{12}$c is independently hydrogen. In embodiments of the formulae above, each $R^{12}$c is independently halogen. In embodiments of the formulae above, each $R^{12}$c is independently oxo. In embodiments of the formulae above, each $R^{12}$c is independently —CN. In embodiments of the formulae above, each $R^{12}$c is independently $C_{1-6}$alkyl. In embodiments of the formulae above, each $R^{12}$c is independently $C_{2-6}$alkenyl. In embodiments of the formulae above, each $R^{12}$c is independently $C_{2-6}$alkynyl. In embodiments of the formulae above, each $R^{12}$c is independently $C_{3-10}$cycloalkyl. In embodiments of the formulae above, each $R^{12}$c is independently —CH$_2$-C$_{3-10}$cycloalkyl. In embodiments of the formulae above, each $R^{12}$c is independently $C_{2-9}$heterocycloalkyl. In embodiments of the formulae above, each $R^{12}$c is independently —CH$_2$-C$_{2-9}$heterocycloalkyl. In embodiments of the formulae above, each $R^{12}$c is independently $C_{6-10}$aryl. In embodiments of the formulae above, each $R^{12}$c is independently —CH$_2$-C$_{6-10}$aryl. In embodiments of the formulae above, each $R^{12}$c is independently —CH$_2$-C$_{1-9}$heteroaryl. In embodiments of the formulae above, each $R^{12}$c is independently $C_{1-9}$heteroaryl. In embodiments of the formulae above, each $R^{12}$c is independently —O$R^{21}$. In embodiments of the formulae above, each $R^{12}$c is independently —S$R^{21}$. In embodiments of the formulae above, each $R^{12}$c is independently —N($R^{22}$)($R^{23}$). In embodiments of the formulae above, each $R^{12}$c is independently —C(O)O$R^{22}$. In embodiments of the formulae above, each $R^{12}$c is independently —C(O)N($R^{22}$)($R^{23}$). In embodiments of the formulae above, each $R^{12}$ is independently —C(O)C(O)N($R^{22}$)($R^{23}$). In embodiments of the formulae above, each $R^{12}$c is independently —OC(O)N($R^{22}$)($R^{23}$). In embodiments of the formulae above, each $R^{12}$c is independently —N($R^{24}$)C(O)N($R^{22}$)($R^{23}$). In embodiments of the formulae above, each $R^{12}$c is independently —N($R^{24}$)C(O)O$R^{25}$. In embodiments of the formulae above, each $R^{12}$c is independently —N($R^{24}$)C(O)$R^{25}$. In embodiments of the formulae above, each $R^{12}$c is independently —N($R^{24}$)S(O)$_2R^{25}$. In embodiments of the formulae above, each $R^{12}$c is independently —C(O)$R^{25}$. In embodiments of the formulae above, each $R^{12}$c is independently —S(O)$_2R^{25}$. In embodiments of the formulae above, each $R^{12}$c is independently —S(O)$_2$N($R^{22}$)($R^{23}$). In embodiments of the formulae above, each $R^{12}$c is independently —OCH$_2$C(O)O$R^{22}$. In embodiments of the formulae above, each $R^{12}$c is independently —OC(O)$R^{25}$. In embodiments of the formulae above, each $R^{12}$c is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$c is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$c is independently $C_{2-6}$alkynyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$c is independently $C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, each $R^{12}$c is independently —CH$_2$-C$_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above;

each $R^{12}c$ is independently $C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}c$ is independently —$CH_2$-$C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}c$ is independently $C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above;

each $R^{12}c$ is independently —$CH_2$-$C_6$-10aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}c$ is independently —$CH_2$-$C_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_1$-haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, each $R^{12}c$ is independently $C_{1-9}$heteroaryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above;

each $R^{12}c$ is independently methyl. In embodiments of the formulae above, each $R^{12}c$ is independently ethyl. In embodiments of the formulae above, each $R^{12}c$ is independently propyl.

The individual embodiments herein below, or combinations thereof, (e.g., embodiments of $R^{13}$, $R^{14}$, $R^{14a}$, or $R^{15}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{13}$ is independently hydrogen. In embodiments of the formulae above, each $R^{13}$ is independently $C_{1-6}$alkyl. In embodiments of the formulae above, each $R^{13}$ is independently $C_{1-6}$haloalkyl. In embodiments of the formulae above, each $R^{12}$ and $R^{13}$, together with the nitrogen to which they are attached, form a $C_{2-9}$heterocycloalkyl ring optionally substituted with one, two, or three $R^{20t}$;

In embodiments of the formulae above, each $R^{14}$ is independently hydrogen. In embodiments of the formulae above;

each $R^{14}$ is independently $C_{1-6}$alkyl. In embodiments of the formulae above, each $R^{14}$ is independently $C_{1-6}$haloalkyl.

In embodiments of the formulae above, each $R^{14}a$ is independently $C_{1-6}$alkyl. In embodiments of the formulae above;

each $R^{14a}$ is independently $C_{1-6}$haloalkyl.

In embodiments of the formulae above, each $R^{15}$ is independently $C_{1-6}$alkyl. In embodiments of the formulae above;

each $R^{15}$ is independently $C_{2-6}$alkenyl. In embodiments of the formulae above, each $R^{15}$ is independently $C_{2-6}$alkynyl. In embodiments of the formulae above, each $R^{15}$ is independently $C_{3-10}$cycloalkyl. In embodiments of the formulae above, each $R^{15}$ is independently $C_{2-9}$heterocycloalkyl. In embodiments of the formulae above, each $R^{15}$ is independently $C_{6-10}$aryl. In embodiments of the formulae above, each $R^{15}$ is independently $C_{1-9}$heteroaryl.

In embodiments of the formulae above, each $R^{15}$ is independently $C_{1-6}$alkyl substituted with one, two, or three $R^{20}m$. In embodiments of the formulae above, each $R^{15}$ is independently $C_{2-6}$alkenyl substituted with one, two, or three $R^{20}m$. In embodiments of the formulae above, each $R^{15}$ is independently $C_{2-6}$alkynyl substituted with one, two, or three $R^{20}m$. In embodiments of the formulae above, each $R^{15}$ is independently $C_{3-10}$cycloalkyl substituted with one, two, or three $R^{20}m$. In embodiments of the formulae above, each $R^{15}$ is independently $C_{2-9}$heterocycloalkyl substituted with one, two, or three $R^{20}m$. In embodiments of the formulae above, each $R^{15}$ is independently $C_{6-10}$aryl substituted with one, two, or three $R^{20}m$. In embodiments of the formulae above, each $R^{15}$ is independently $C_{1-9}$heteroaryl substituted with one, two, or three $R^{20}m$. In embodiments of the formulae above, each $R^{15}$ is independently ethenyl substituted with one, two, or three $R^{20}m$. In embodiments of the formulae above, each $R^{15}$ is independently propenyl substituted with one, two, or three $R^{20}m$. In embodiments of the formulae above, each $R^{15}$ is independently butenyl substituted with one, two, or three $R^{20}m$. In embodiments of the formulae above, each $R^{15}$ is independently ethenyl. In embodiments of the formulae above, each $R^{15}$ is independently propenyl. In embodiments of the formulae above, each $R^{15}$ is independently butenyl.

The individual embodiments herein below, or combinations thereof, (e.g., embodiments of $R^{20}m$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{20}m$ is independently halogen. In embodiments of the formulae above, each $R^{20}m$ is independently oxo. In embodiments of the formulae above, each $R^{20}m$ is independently —CN. In embodiments of the formulae above, each $R^{20}m$ is independently $C_{1-6}$alkyl. In embodiments of the formulae above, each $R^{20}m$ is independently $C_{2-6}$alkenyl. In embodiments of the formulae above, each $R^{20}m$ is independently $C_{2-6}$alkynyl. In embodiments of the formulae above, each $R^{20}m$ is independently $C_{3-10}$cycloalkyl. In embodiments of the formulae above, each $R^{20}m$ is independently —CH$_2$-C$_{3-10}$cycloalkyl. In embodiments of the formulae above, each $R^{20}m$ is independently $C_{2-9}$heterocycloalkyl. In embodiments of the formulae above, each $R^{20}m$ is independently —CH$_2$-C$_{2-9}$heterocycloalkyl. In embodiments of the formulae above, each $R^{20}m$ is independently $C_{6-10}$aryl. In embodiments of the formulae above, each $R^{20}m$ is independently —CH$_2$-C$_{6-10}$aryl. In embodiments of the formulae above, each $R^{20}m$ is independently —CH$_2$-C$_{1-9}$heteroaryl. In embodiments of the formulae above, each $R^{20}m$ is independently $C_{1-9}$heteroaryl. In embodiments of the formulae above, each $R^{20}m$ is independently —OR$^{21}$. In embodiments of the formulae above, each $R^{20}m$ is independently —SR$^{21}$. In embodiments of the formulae above, each $R^{20}m$ is independently —N(R$^{22}$)(R$^{23}$). In embodiments of the formulae above, each $R^{20}m$ is independently —C(O)OR$^{22}$. In embodiments of the formulae above, each $R^{20}m$ is independently —C(O)N(R$^{22}$)(R$^{23}$). In embodiments of the formulae above, each $R^{20}m$ is independently —C(O)C(O)N(R$^{22}$)(R$^{23}$). In embodiments of the formulae above, each $R^{20}m$ is independently —OC(O)N(R$^{22}$)(R$^{23}$). In embodiments of the formulae above, each $R^{20}m$ is independently —N(R$^{24}$)C(O)N(R$^{22}$)(R$^{23}$). In embodiments of the formulae above, each $R^{20}m$ is independently —N(R$^{24}$)C(O)OR$^{25}$. In embodiments of the formulae above, each $R^{20}m$ is independently —N(R$^{24}$)C(O)R$^{25}$. In embodiments of the formulae above, each $R^{20}m$ is independently —N(R$^{24}$)C(O)R$^{21}$. In embodiments of the formulae above, each $R^{20}m$ is independently —C(O)R$^{21}$. In embodiments of the formulae above, each $R^{20}m$ is independently —N(R$^{24}$)S(O)$_2$R$^{25}$. In embodiments of the formulae above, each $R^{20}m$ is independently —C(O)R$^{25}$. In embodiments of the formulae above, each $R^{20}m$ is independently —S(O)$_2$R$^{25}$. In embodiments of the formulae above, each $R^{20}m$ is independently —S(O)$_2$N(R$^{22}$)(R$^{23}$). In embodiments of the formulae above, each $R^{20}m$ is independently —OCH$_2$C(O)OR$^{22}$. In embodiments of the formulae above, each $R^{20}m$ is independently —OC(O)R$^{25}$. In embodiments of the formulae above, each $R^{20}m$ is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each $R^{20}m$ is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above;

each R$^{20}$m is independently C$_{2-6}$alkynyl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently C$_{3-10}$cycloalkyl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently —CH$_2$-C$_{3-10}$cycloalkyl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently C$_{2-9}$heterocycloalkyl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently —CH$_2$-C$_{2-9}$heterocycloalkyl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently C$_{6-10}$aryl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above;

each R$^{20}$m is independently —CH$_2$-C$_{6-10}$aryl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently —CH$_2$-C$_{1-9}$heteroaryl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, each R$^{20}$m is independently C$_{1-9}$heteroaryl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.

The individual embodiments herein below, or combinations thereof, (e.g., embodiments of R$^{21}$, R$^{22}$, R$^{23}$, R$^{24}$, or R$^{25}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''-1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each R$^{21}$ is independently H. In embodiments of the formulae above, each R$^{21}$ is independently C$_{1-6}$alkyl. In embodiments of the formulae above, each R$^{21}$ is independently C$_{1-6}$haloalkyl. In embodiments of the formulae above, each R$^{21}$ is independently C$_{2-6}$alkenyl. In embodiments of the formulae above, each R$^{21}$ is independently C$_{2-6}$alkynyl. In embodiments of the formulae above, each R$^{21}$ is independently C$_{3-10}$cycloalkyl. In embodiments of the formulae above, each $R^{21}$ is independently $C_{2-9}$heterocycloalkyl. In embodiments of the formulae above, each $R^{21}$ is independently $C_{6-10}$aryl. In embodiments of the formulae above, each $R^{21}$ is independently $C_{1-9}$heteroaryl.

In embodiments of the formulae above, each $R^{22}$ is independently H. In embodiments of the formulae above, each $R^{22}$ is independently $C_{1-6}$alkyl. In embodiments of the formulae above, each $R^{22}$ is independently $C_{1-6}$haloalkyl. In embodiments of the formulae above, each $R^{22}$ is independently $C_{2-6}$alkenyl. In embodiments of the formulae above, each $R^{22}$ is independently $C_{2-6}$alkynyl. In embodiments of the formulae above, each $R^{22}$ is independently $C_{3-10}$cycloalkyl. In embodiments of the formulae above, each $R^{22}$ is independently $C_{2-9}$heterocycloalkyl. In embodiments of the formulae above, each $R^{22}$ is independently $C_{6-10}$aryl. In embodiments of the formulae above, each $R^{22}$ is independently $C_{1-9}$heteroaryl.

In embodiments of the formulae above, each $R^{23}$ is independently H. In embodiments of the formulae above, each $R^{23}$ is independently $C_{1-6}$alkyl.

In embodiments of the formulae above, each $R^{24}$ is independently H. In embodiments of the formulae above, each $R^{24}$ is independently $C_{1-6}$alkyl.

In embodiments of the formulae above, each $R^{25}$ is independently $C_{1-6}$alkyl. In embodiments of the formulae above;

each $R^{25}$ is independently $C_{2-6}$alkenyl. In embodiments of the formulae above, each $R^{25}$ is independently $C_{2-6}$alkynyl. In embodiments of the formulae above, each $R^{25}$ is independently $C_{3-6}$cycloalkyl. In embodiments of the formulae above, each $R^{25}$ is independently $C_{2-9}$heterocycloalkyl. In embodiments of the formulae above, each $R^{25}$ is independently $C_{6-10}$aryl. In embodiments of the formulae above;

each $R^{25}$ is independently $C_{1-9}$heteroaryl.

The individual embodiments herein below, or combinations thereof, (e.g., embodiments of $R^1$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"- 1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^1$ is independently hydrogen. In embodiments of the formulae above, each $R^1$ is independently halogen. In embodiments of the formulae above, each $R^1$ is independently oxo. In embodiments of the formulae above, each $R^1$ is independently —CN. In embodiments of the formulae above, each $R^1$ is independently $C_{1-6}$alkyl. In embodiments of the formulae above, each $R^1$ is independently $C_{2-6}$alkenyl. In embodiments of the formulae above, each $R^1$ is independently $C_{2-6}$alkynyl. In embodiments of the formulae above, each $R^1$ is independently —$OR^{12}$. In embodiments of the formulae above, each $R^1$ is independently —$SR^{12}$. In embodiments of the formulae above, each $R^1$ is independently —$N(R^{12})(R^{13})$. In embodiments of the formulae above, each $R^1$ is independently —$C(O)OR^{12}$. In embodiments of the formulae above, each $R^1$ is independently —$OC(O)N(R^{12})(R^{13})$. In embodiments of the formulae above, each $R^1$ is independently —$N(R^{14})C(O)N(R^{12})(R^{13})$. In embodiments of the formulae above, each $R^1$ is independently —$N(R^{14})C(O)OR^{15}$. In embodiments of the formulae above, each $R^1$ is independently —$N(R^{14})S(O)_2R^{15}$. In embodiments of the formulae above, each $R^1$ is independently —$C(O)R^{15}$. In embodiments of the formulae above;

each $R^1$ is independently —$S(O)R^{15}$. In embodiments of the formulae above, each $R^1$ is independently —$OC(O)R^{15}$. In embodiments of the formulae above, each $R^1$ is independently —$C(O)N(R^{12})(R^{13})$. In embodiments of the formulae above, each $R^1$ is independently —$C(O)C(O)N(R^{12})(R^{13})$. In embodiments of the formulae above, each $R^1$ is independently —$N(R^{14})C(O)R^{15}$. In embodiments of the formulae above, each $R^1$ is independently —$C(O)C(O)N(R^{12})(R^{13})$. In embodiments of the formulae above, each $R^1$ is independently —$S(O)_2R^{15}$. In embodiments of the formulae above, each $R^1$ is independently —$S(O)_2N(R^{12})(R^{13})$—. In embodiments of the formulae above, each $R^1$ is independently —$S(=O)(=NH)N(R^{12})(R^{13})$. In embodiments of the formulae above, each $R^1$ is independently —$CH_2C(O)N(R^{12})(R^{13})$. In embodiments of the formulae above, each $R^1$ is independently —$CH_2N(R^{14})C(O)R^{15}$. In embodiments of the formulae above, each $R^1$ is independently —$CH_2S(O)_2R^{15}$. In embodiments of the formulae above, each $R^1$ is independently —$CH_2S(O)_2N(R^{12})(R^{13})$. In embodiments of the formulae above, each $R^1$ is independently $C_{1-6}$alkyl substituted with one, two, or three $R^{20}$a. In embodiments of the formulae above, each $R^1$ is independently $C_{2-6}$alkenyl substituted with one, two, or three $R^{20}$a. In embodiments of the formulae above, each $R^1$ is independently $C_{2-6}$alkynyl substituted with one, two, or three $R^{20}$a. In embodiments of the formulae above, $R^1$ is independently halogen. In embodiments of the formulae above, $R^1$ is independently F. In embodiments of the formulae above, $R^1$ is independently $C_1$. In embodiments of the formulae above, $R^1$ is independently Br. In embodiments of the formulae above, $R^1$ is independently I. In embodiments of the formulae above, $R^1$ is independently oxo. In embodiments of the formulae above, $R^1$ is independently —CN. In embodiments of the formulae above, $R^1$ is independently $C_{1-6}$alkyl. In embodiments of the formulae above, $R^1$ is independently methyl. In embodiments of the formulae above, $R^1$ is independently ethyl. In embodiments of the formulae above, $R^1$ is independently isopropyl. In embodiments of the formulae above, $R^1$ is independently $C_2$-falkenyl. In embodiments of the formulae above, $R^1$ is independently $C_{2-6}$alkynyl. In embodiments of the formulae above, $R^1$ is independently $C_{1-6}$haloalkyl. In embodiments of the formulae above, $R^1$ is independently —$CF_3$. In embodiments of the formulae above, $R^1$ is independently —OH. In embodiments of the formulae above, $R^1$ is independently —$OCH_3$. In embodiments of the formulae above, $R^1$ is independently —SH. In embodiments of the formulae above, $R^1$ is independently —$SCH_3$. In embodiments of the formulae above, $R^1$ is independently —$N(CH_3)_2$. In embodiments of the formulae above, $R^1$ is independently —$N(H)_2$. In embodiments of the formulae above, $R^1$ is independently —C(O)OH. In embodiments of the formulae above, $R^1$ is independently —$C(O)OCH_3$. In embodiments of the formulae above, $R^1$ is independently —$OC(O)N(H)_2$. In embodiments of the formulae above, $R^1$ is independently —$OC(O)N(CH_3)_2$. In embodiments of the formulae above, $R^1$ is independently —$N(H)C(O)N(CH_3)_2$. In embodiments of the formulae above, $R^1$ is independently —$N(H)C(O)N(H)_2$. In embodiments of the formulae above, $R^1$ is independently —N(H)C(O)OH. In embodiments of the formulae above, $R^1$ is independently —$N(H)C(O)OCH_3$. In embodiments of the formulae above, $R^1$ is independently —$N(H)S(O)_2CH_3$. In embodiments of the formulae above, $R^1$ is independently —$C(O)CH_3$. In embodiments of the formulae above, $R^1$ is independently —C(O)H. In embodiments of the formulae above, $R^1$ is independently —$S(O)CH_3$. In embodiments of the formulae above, $R^1$ is independently —$OC(O)CH_3$. In embodiments of the formulae above, $R^1$ is independently —OC(O)H. In embodiments of the formulae above, $R^1$ is independently —$C(O)N(CH_3)_2$. In embodiments of the formulae above, $R^1$ is independently —$C(O)C(O)N(CH_3)_2$. In embodiments of the formulae above, $R^1$ is independently —N(H)C(O)H. In embodiments of the formulae above, $R^1$ is independently —$N(H)C(O)CH_3$. In embodiments of the formulae above, $R^1$ is independently —$S(O)_2CH_3$. In embodiments of the formulae above, $R^1$ is independently —$S(O)_2N(H)_2$. In embodiments of the formulae above, $R^1$ is independently —$S(O)_2N(CH_3)_2$. In embodiments of the formulae above, $R^1$ is independently S(=O)(=NH)N(H)_2$. In embodiments of the formulae above, $R^1$ is independently S(=O)(=NH)N(CH_3)_2$. In embodiments of the formulae above, $R^1$ is independently —$CH_2C(O)N(H)_2$. In embodiments of the formulae above, $R^1$ is independently —$CH_2C(O)N(CH_3)_2$. In embodiments of the formulae above, $R^1$ is independently —$CH_2N(H)C(O)H$. In embodiments of the formulae above, $R^1$ is independently —$CH_2N(H)C(O)CH_3$. In embodiments of the formulae above, $R^1$ is independently —$CH_2S(O)_2H$. In embodiments of the formulae above, $R^1$ is independently —$CH_2S(O)_2CH_3$. In embodiments of the formulae above, $R^1$ is independently and —$CH_2S(O)_2N(CH_3)_2$. In embodiments of the formulae above, $R^1$ is independently and —$CH_2S(O)_2N(H)_2$.

The individual embodiments herein below, or combinations thereof, (e.g., embodiments of $R^2$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R_2$ is independently hydrogen. In embodiments of the formulae above, each $R_2$ is independently halogen. In embodiments of the formulae above, each $R_2$ is independently oxo. In embodiments of the formulae above, each $R_2$ is independently —CN. In embodiments of the formulae above, each $R_2$ is independently $C_{1-6}$alkyl. In embodiments of the formulae above, each $R_2$ is independently $C_{2-6}$alkenyl. In embodiments of the formulae above, each $R_2$ is independently $C_{2-6}$alkynyl. In embodiments of the formulae above, each $R_2$ is independently $C_{3-12}$cycloalkyl. In embodiments of the formulae above, each $R_2$ is independently $C_{2-11}$heterocycloalkyl. In embodiments of the formulae above, each $R_2$ is independently $C_{6-10}$aryl. In embodiments of the formulae above, each $R_2$ is independently $C_{1-9}$heteroaryl. In embodiments of the formulae above, each $R^2$ is independently —$OR^{12}$. In embodiments of the formulae above, each $R_2$ is independently —$OR^{12}a$. In embodiments of the formulae above, each $R_2$ is independently —$SR^{12}$. In embodiments of the formulae above, each $R_2$ is independently —$N(R^{12})(R^{13})$. In embodiments of the formulae above, each $R_2$ is independently —$C(O)OR^{12}$. In embodiments of the formulae above, each $R_2$ is independently —$OC(O)N(R^{12})(R^{13})$. In embodiments of the formulae above, each $R_2$ is independently —$N(R^{14})C(O)N(R^{12})(R^{13})$. In embodiments of the formulae above, each $R_2$ is independently —$N(R^{14})C(O)OR^{15}$. In embodiments of the formulae above, each $R_2$ is independently —$N(R^{14})S(O)_2R^{15}$. In embodiments of the formulae above, each $R_2$ is independently —$C(O)R^{15}$. In embodiments of the formulae above;

each $R^2$ is independently —S(O)$R^{15}$. In embodiments of the formulae above, each $R_2$ is independently —OC(O)$R^{15}$. In embodiments of the formulae above, each $R_2$ is independently —C(O)N($R^{12}$)($R^{13}$). In embodiments of the formulae above, each $R_2$ is independently —C(O)C(O)N($R^{12}$)($R^{13}$). In embodiments of the formulae above, each $R_2$ is independently —N($R^{14}$)C(O)$R^{15}$. In embodiments of the formulae above, each $R_2$ is independently —C(O)C(O)N($R^{12}$)($R^{13}$). In embodiments of the formulae above, each $R_2$ is independently —S(O)$_2R^{15}$. In embodiments of the formulae above, each $R_2$ is independently —S(O)$_2$N($R^{12}$)($R^{13}$)—. In embodiments of the formulae above, each $R_2$ is independently —S(=O)(=NH)N($R^{12}$)($R^{13}$). In embodiments of the formulae above, each $R_2$ is independently —CH$_2$C(O)N($R^{12}$)($R^{13}$). In embodiments of the formulae above, each $R_2$ is independently —CH$_2$N($R^{14}$)C(O)$R^{15}$. In embodiments of the formulae above, each $R_2$ is independently —CH$_2$S(O)$_2R^{15}$. In embodiments of the formulae above, each $R_2$ is independently —CH$_2$S(O)$_2$N($R^{12}$)($R^{13}$). In embodiments of the formulae above, each $R_2$ is independently $C_{1-6}$alkyl substituted with one, two, or three $R^{20}$b. In embodiments of the formulae above, each $R_2$ is independently $C_{2-6}$alkenyl substituted with one, two, or three $R^{20}$b. In embodiments of the formulae above, each $R_2$ is independently $C_{2-6}$alkynyl substituted with one, two, or three $R^{20}$b. In embodiments of the formulae above, each $R_2$ is independently $C_{3-12}$cycloalkyl substituted with one, two, or three $R^{20b}$. In embodiments of the formulae above, each $R_2$ is independently $C_{2-11}$heterocycloalkyl substituted with one, two, or three $R^{20b}$. In embodiments of the formulae above;

each $R^2$ is independently $C_{6-10}$aryl substituted with one, two, or three $R^{20o}$. In embodiments of the formulae above, each $R_2$ is independently $C_{1-9}$heteroaryl substituted with one, two, or three $R^{20o}$. In embodiments of the formulae above, $R^2$ is independently halogen. In embodiments of the formulae above, $R^2$ is independently F. In embodiments of the formulae above, $R^2$ is independently $C_1$. In embodiments of the formulae above, $R^2$ is independently Br. In embodiments of the formulae above, $R^2$ is independently I. In embodiments of the formulae above, $R^2$ is independently $R^2$ is independently oxo. In embodiments of the formulae above, $R^2$ is independently —CN. In embodiments of the formulae above, $R^2$ is independently $C_{1-6}$alkyl. In embodiments of the formulae above, $R^2$ is independently methyl. In embodiments of the formulae above, $R^2$ is independently ethyl. In embodiments of the formulae above, $R^2$ is independently isopropyl. In embodiments of the formulae above, $R^2$ is independently $C_{2-6}$alkenyl. In embodiments of the formulae above, $R^2$ is independently $C_{2-6}$alkynyl. In embodiments of the formulae above, $R^2$ is independently $C_{1-6}$haloalkyl. In embodiments of the formulae above, $R^2$ is independently —CF$_3$. In embodiments of the formulae above, $R^2$ is independently $C_{3-12}$cycloalkyl. In embodiments of the formulae above, $R^2$ is independently $C_{2-11}$heterocycloalkyl. In embodiments of the formulae above, $R^2$ is independently $C_{6-12}$aryl. In embodiments of the formulae above, $R^2$ is independently $C_{1-11}$heteroaryl. In embodiments of the formulae above, $R^2$ is independently —OH. In embodiments of the formulae above, $R^2$ is independently —OCH$_3$. In embodiments of the formulae above, $R^2$ is independently —SH. In embodiments of the formulae above, $R^2$ is independently —SCH$_3$. In embodiments of the formulae above, $R^2$ is independently —N(CH$_3$)$_2$. In embodiments of the formulae above, $R^2$ is independently —N(H)$_2$. In embodiments of the formulae above, $R^2$ is independently —C(O)OH. In embodiments of the formulae above, $R^2$ is independently —C(O)OCH$_3$. In embodiments of the formulae above, $R^2$ is independently —OC(O)N(H)$_2$. In embodiments of the formulae above, $R^2$ is independently —OC(O)N(CH$_3$)$_2$. In embodiments of the formulae above, $R^2$ is independently —N(H)C(O)N(CH$_3$)$_2$. In embodiments of the formulae above, $R^2$ is independently —N(H)C(O)N(H)$_2$. In embodiments of the formulae above, $R^2$ is independently —N(H)C(O)OH. In embodiments of the formulae above, $R^2$ is independently —N(H)C(O)OCH$_3$. In embodiments of the formulae above, $R^2$ is independently —N(H)S(O)$_2$CH$_3$. In embodiments of the formulae above, $R^2$ is independently —C(O)CH$_3$. In embodiments of the formulae above, $R^2$ is independently —C(O)H. In embodiments of the formulae above, $R^2$ is independently —S(O)CH$_3$. In embodiments of the formulae above, $R^2$ is independently —OC(O)CH$_3$. In embodiments of the formulae above, $R^2$ is independently —OC(O)H. In embodiments of the formulae above, $R^2$ is independently —C(O)N(CH$_3$)$_2$. In embodiments of the formulae above, $R^2$ is independently —C(O)C(O)N(CH$_3$)$_2$. In embodiments of the formulae above, $R^2$ is independently —N(H)C(O)H. In embodiments of the formulae above, $R^2$ is independently —N(H)C(O)CH$_3$. In embodiments of the formulae above, $R^2$ is independently —S(O)$_2$CH$_3$. In embodiments of the formulae above, $R^2$ is independently —S(O)$_2$N(H)$_2$. In embodiments of the formulae above, $R^2$ is independently —S(O)$_2$N(CH$_3$)$_2$. In embodiments of the formulae above, $R^2$ is independently S(=O)(=NH)N(H)$_2$. In embodiments of the formulae above, $R^2$ is independently S(=O)(=NH)N(CH$_3$)$_2$. In embodiments of the formulae above, $R^2$ is independently —CH$_2$C(O)N(H)$_2$. In embodiments of the formulae above, $R^2$ is independently —CH$_2$C(O)N(CH$_3$)$_2$. In embodiments of the formulae above, $R^2$ is independently —CH$_2$N(H)C(O)H. In embodiments of the formulae above, $R^2$ is independently —CH$_2$N(H)C(O)CH$_3$. In embodiments of the formulae above, $R^2$ is independently —CH$_2$S(O)$_2$H. In embodiments of the formulae above, $R^2$ is independently —CH$_2$S(O)$_2$CH$_3$. In embodiments of the formulae above, $R^2$ is independently and —CH$_2$S(O)$_2$N(CH$_3$)$_2$. In embodiments of the formulae above, $R^2$ is independently and —CH$_2$S(O)$_2$N(H)$_2$.

In embodiments of the formulae above, $R^2$ is

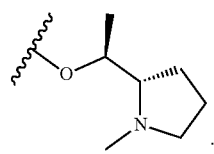 [SMILES: *O[C@@H](C)[C@@H]1CCCN1C]

In embodiments of the formulae above, R² is

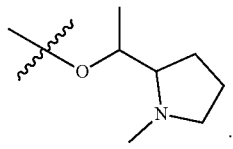 [SMILES: *OC(C)C1CCCN1C]

In embodiments of the formulae above, R² is

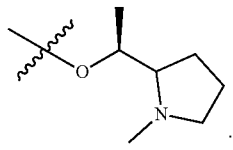 [SMILES: *O[C@@H](C)C1CCCN1C]

In embodiments of the formulae above, R² is

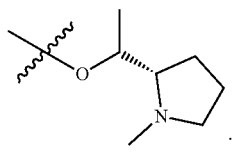 [SMILES: *OC(C)[C@@H]1CCCN1C]

In embodiments of the formulae above, R² is

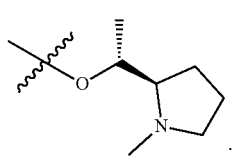 [SMILES: *O[C@H](C)[C@H]1CCCN1C]

In embodiments of the formulae above, R² is

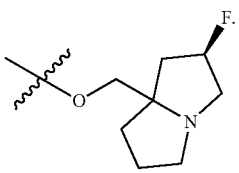 [SMILES: *OCC12CCCN1C[C@H](F)C2]

In embodiments of the formulae above, R² is

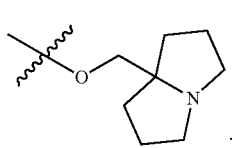 [SMILES: *OCC12CCCN1CCC2]

In embodiments of the formulae above, R² is

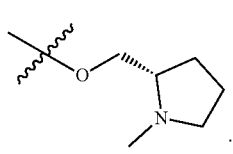 [SMILES: *OC[C@@H]1CCCN1C]

In embodiments of the formulae above, R² is

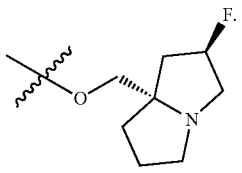 [SMILES: *OC[C@@]12CCCN1C[C@H](F)C2]

In embodiments of the formulae above, R² is selected from

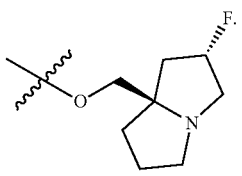 [SMILES: *OC[C@]12CCCN1C[C@@H](F)C2]

In embodiments of the formulae above, R² is selected from

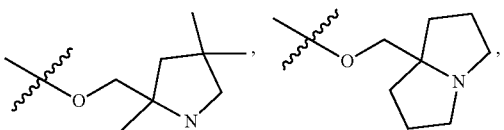
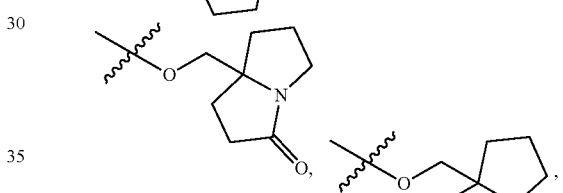
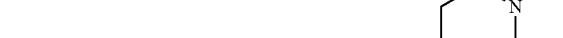
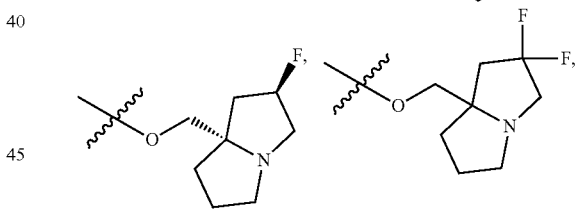
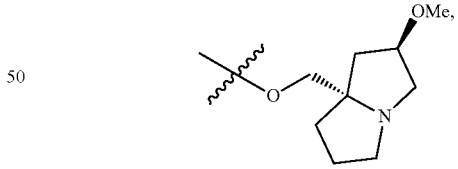
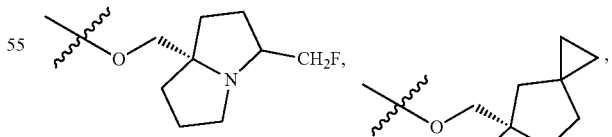
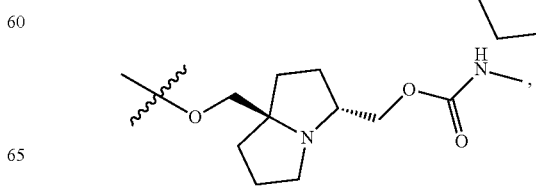

727
-continued
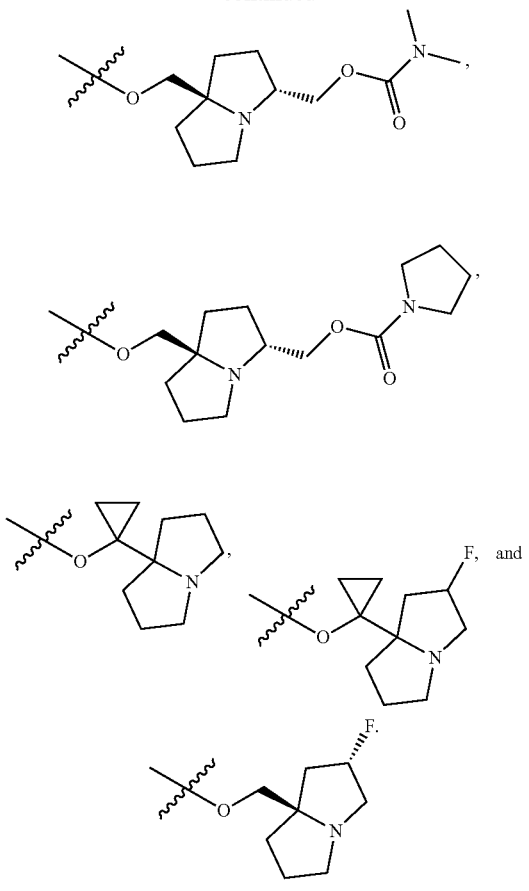
In embodiments of the formulae above, R² is selected from
728
-continued
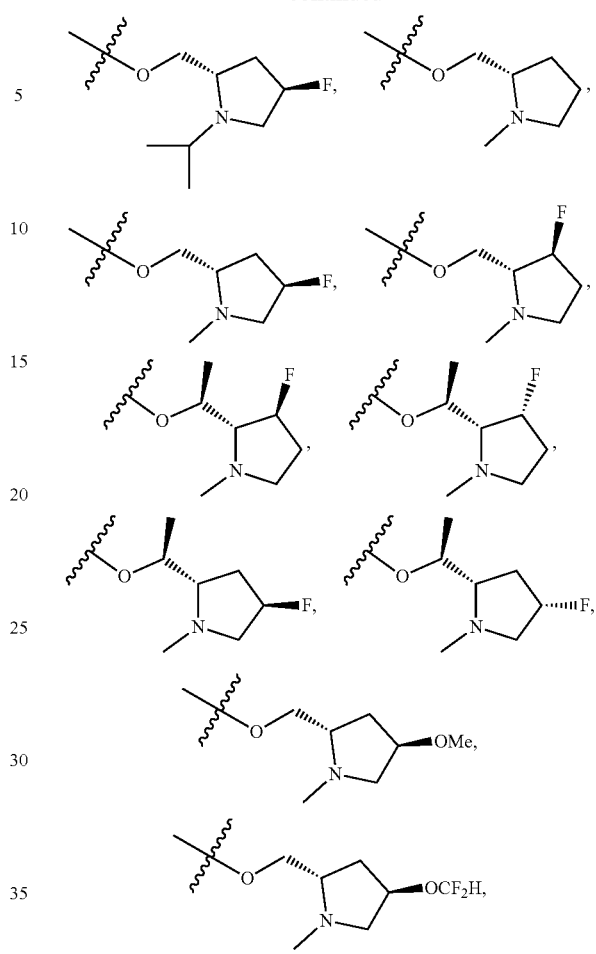
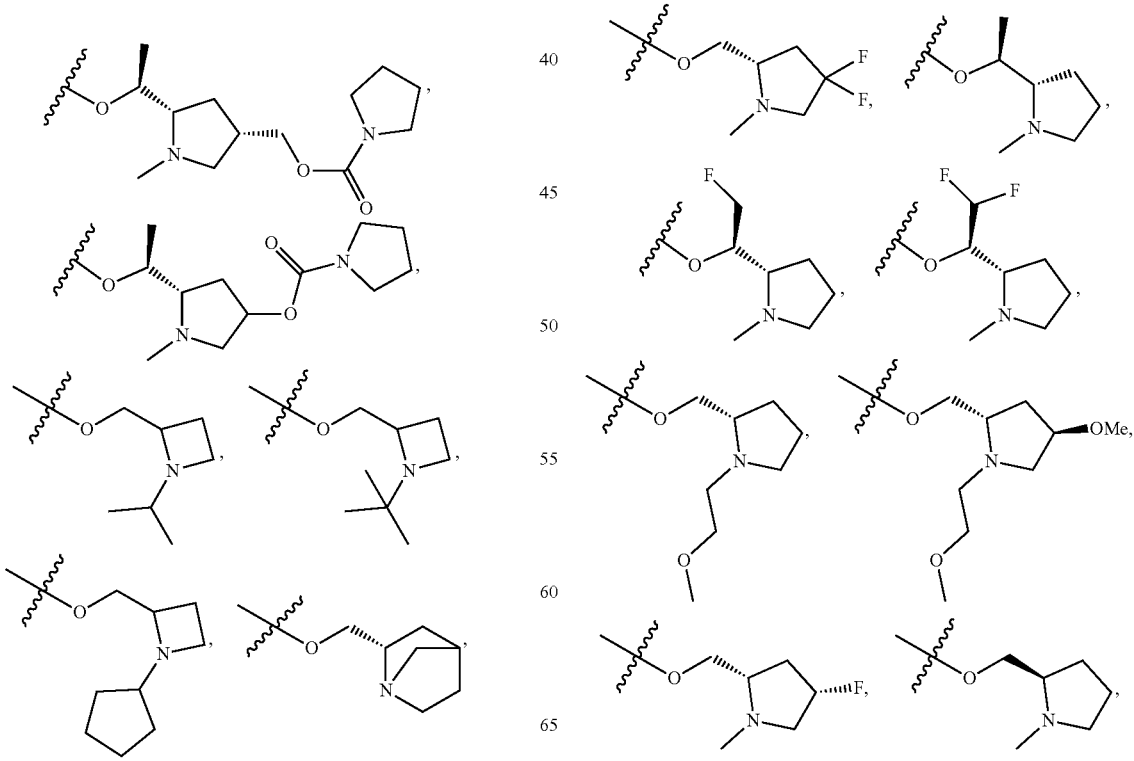

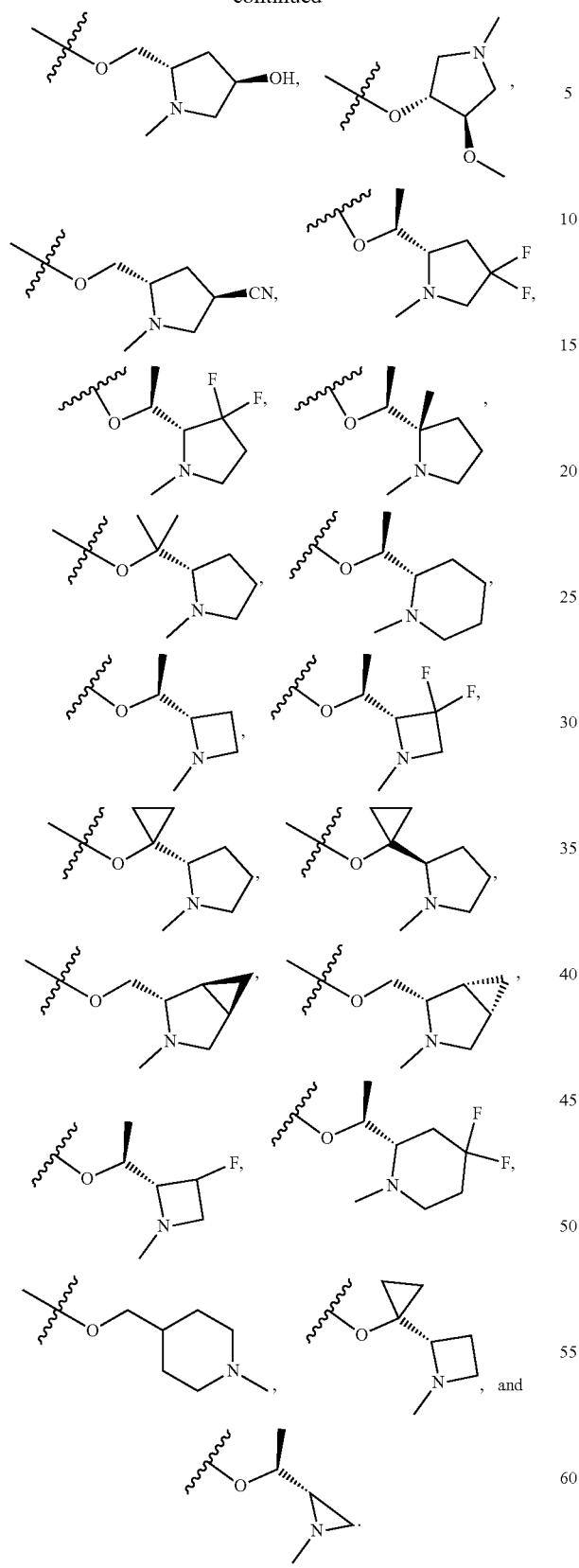
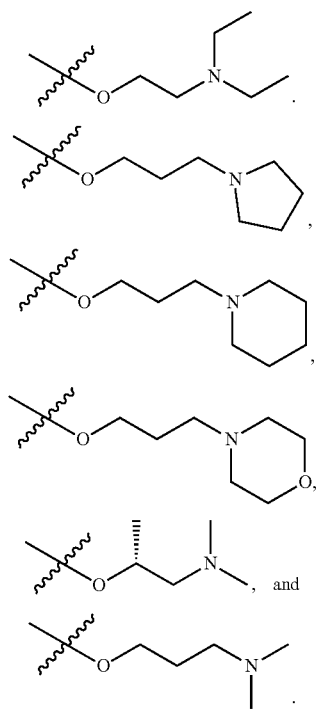
In embodiments of the formulae above, R² is selected from
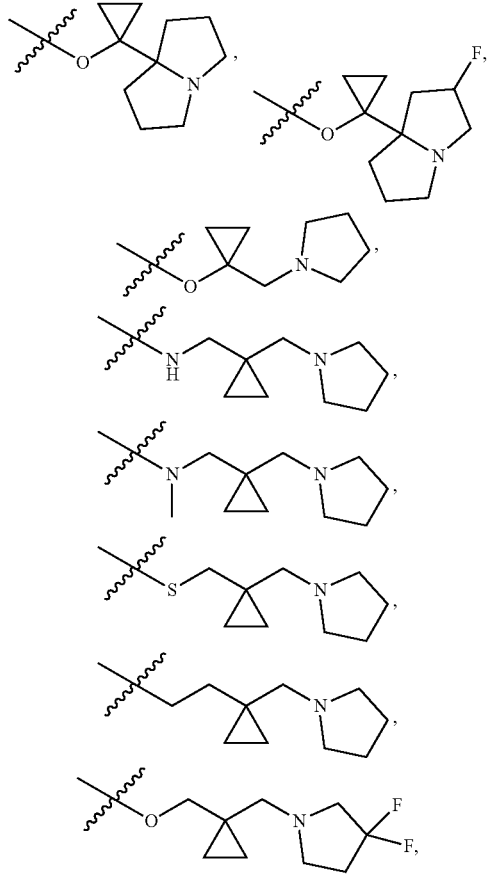
In embodiments of the formulae above, R² is selected from

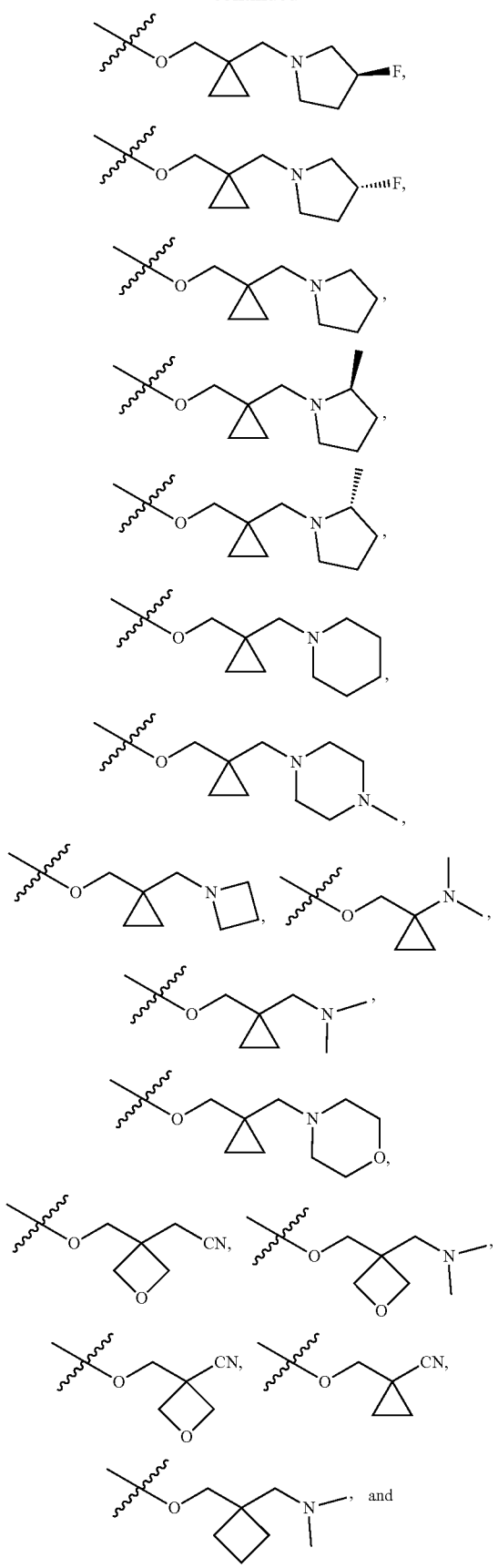
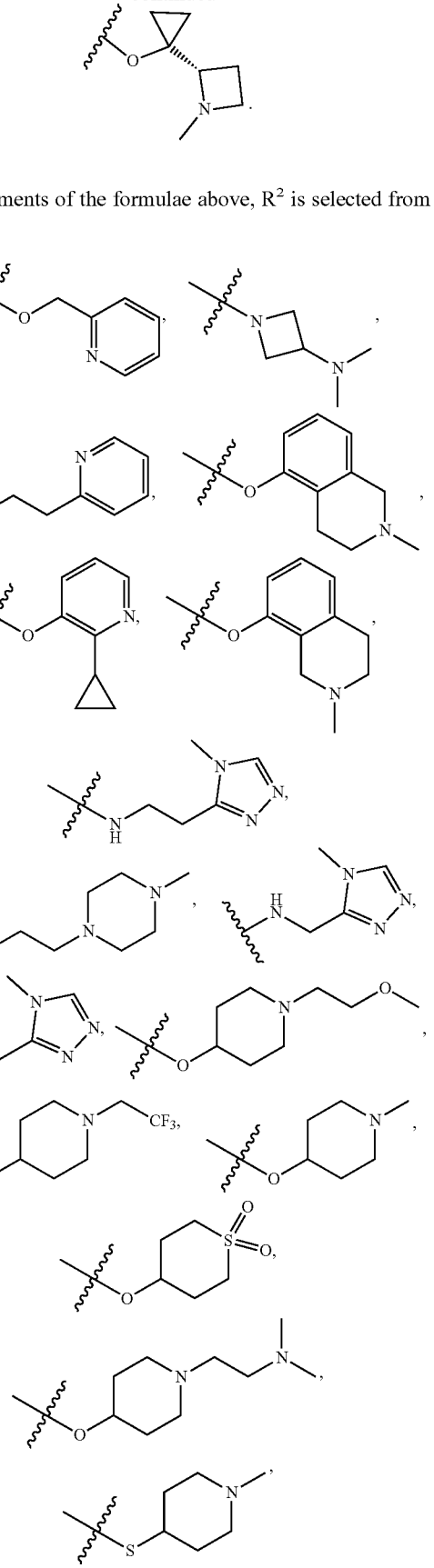
In embodiments of the formulae above, R² is selected from

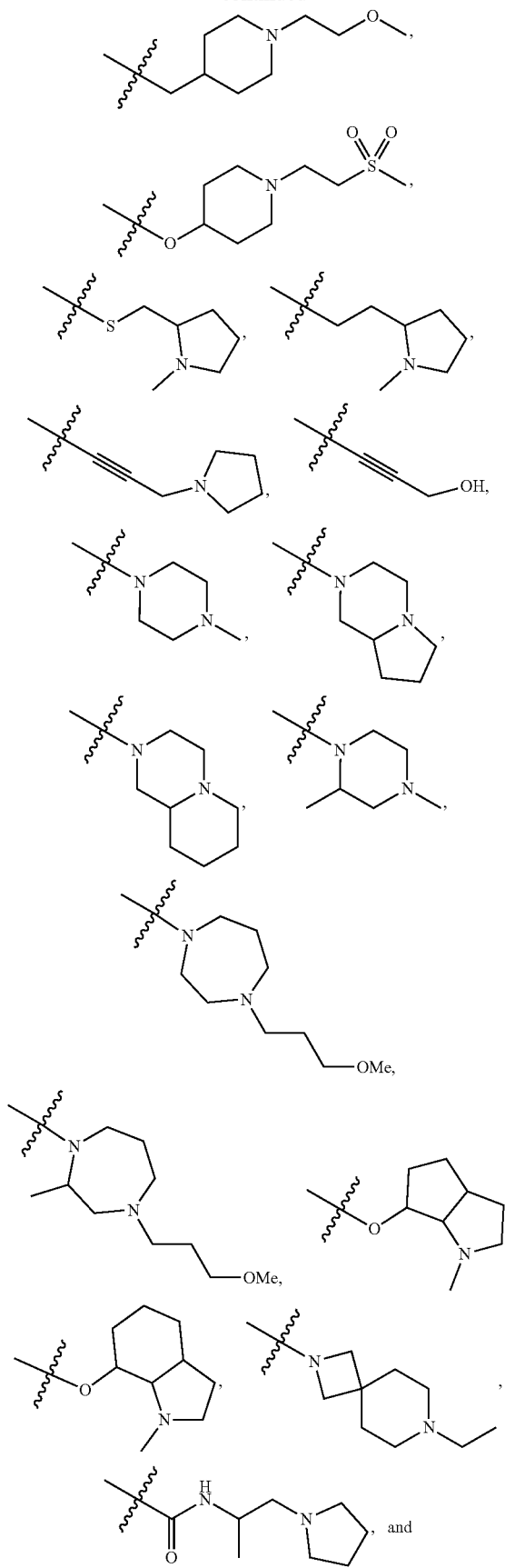
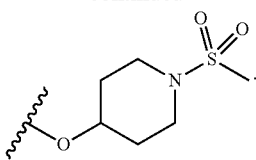 [SMILES: *OC1CCN(S(C)(=O)=O)CC1]
In embodiments of the compounds of the formulae above, $R^2$ is selected from
In embodiments of the compounds of the formulae above, $R^2$ is selected from 735
-continued
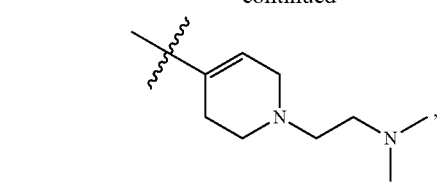
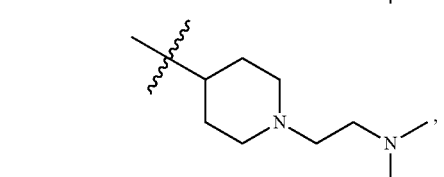
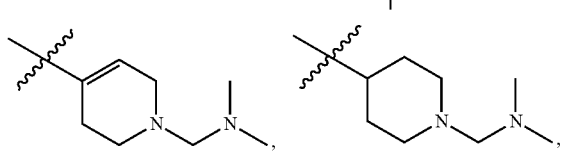
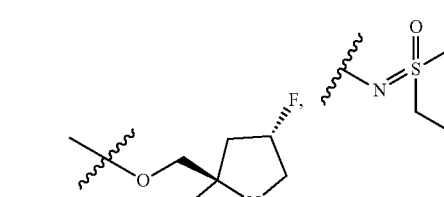
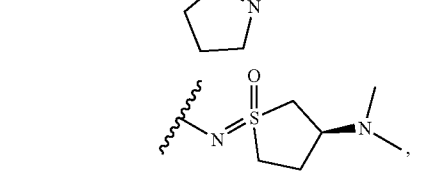
In embodiments of the compounds of the formulae above, R² is selected from
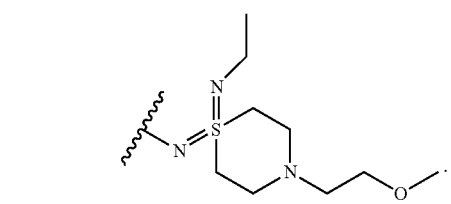
736
-continued
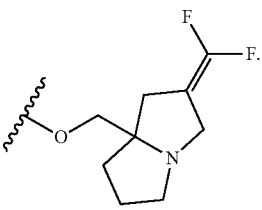
In embodiments of the formulae above, R² is
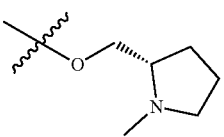
In embodiments of the formulae above, R² is
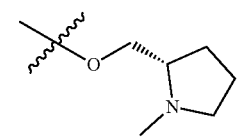
In embodiments of the formulae above, R² is
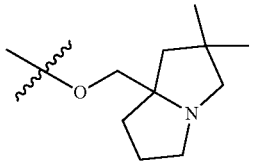
In embodiments of the formulae above, R² is
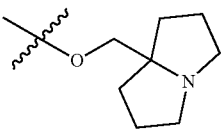
In embodiments of the formulae above, R² is
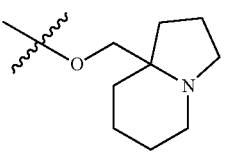

In embodiments of the formulae above, R² is

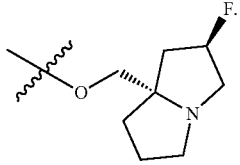 [SMILES: *OC[C@@]12CCCN1C[C@H](F)C2]

In embodiments of the formulae above, R² is

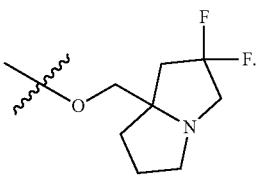 [SMILES: *OCC12CCCN1CC(F)(F)C2]

In embodiments of the formulae above, R² is

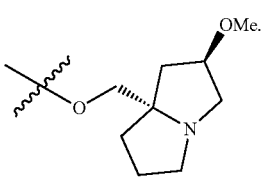 [SMILES: *OC[C@@]12CCCN1C[C@H](OC)C2]

In embodiments of the formulae above, R² is

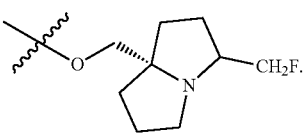

In embodiments of the formulae above, R² is

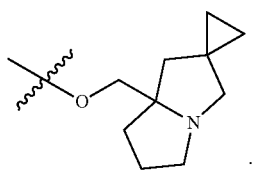 [SMILES: *OCC12CCCN1CC1(CC1)C2]

In embodiments of the formulae above, R² is

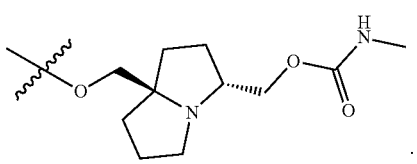 [SMILES: *OC[C@]12CCCN1[C@@H](COC(=O)NC)CC2]

In embodiments of the formulae above, R² is

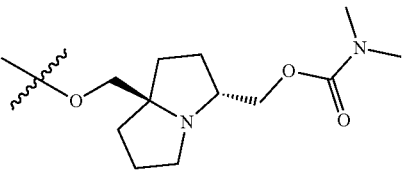

In embodiments of the formulae above, R² is

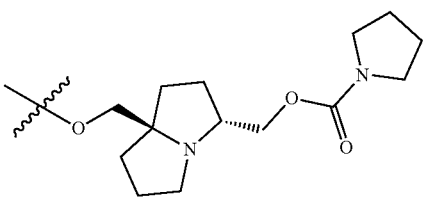

In embodiments of the formulae above, R² is

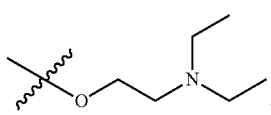

In embodiments of the formulae above, R² is

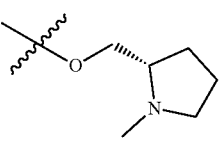

In embodiments of the formulae above, R² is

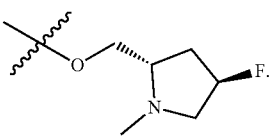 [SMILES: *OC[C@@H]1C[C@@H](F)CN1C]

In embodiments of the formulae above, R² is

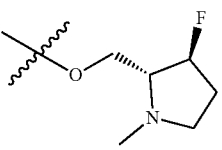

In embodiments of the formulae above, R² is

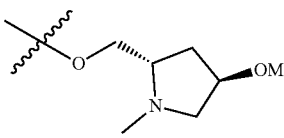

In embodiments of the formulae above, R² is

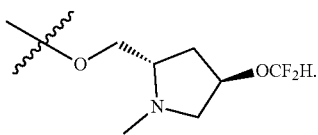

In embodiments of the formulae above, R² is

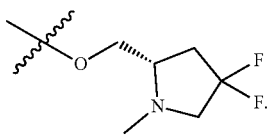 [SMILES: *OC[C@@H]1CC(F)(F)CN1C]

In embodiments of the formulae above, R² is

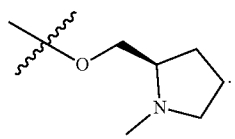 [SMILES: *OC[C@H]1CCCN1C]

In embodiments of the formulae above, R² is

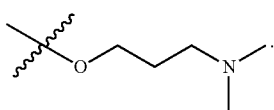 [SMILES: *OCCCN(C)C]

In embodiments of the formulae above, R² is

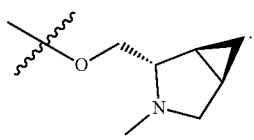 [SMILES: *OC[C@@H]1[C@H]2C[C@H]2CN1C]

In embodiments of the formulae above, R² is

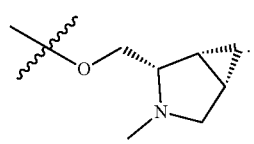 [SMILES: *OC[C@@H]1[C@@H]2C[C@@H]2CN1C]

In embodiments of the formulae above, R² is

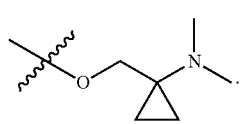 [SMILES: *OCC1(N(C)C)CC1]

In embodiments of the formulae above, R² is

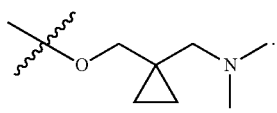 [SMILES: *OCC1(CN(C)C)CC1]

In embodiments of the formulae above, R² is

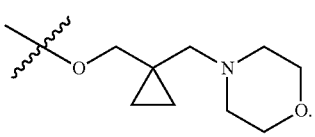 [SMILES: *OCC1(CN2CCOCC2)CC1]

In embodiments of the formulae above, R² is

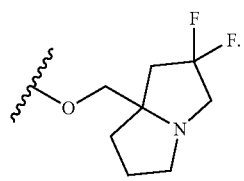 [SMILES: *OCC12CCCN1CC(F)(F)C2]

In embodiments of the formulae above, R² is

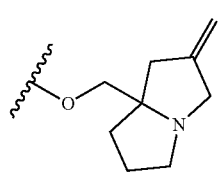

In embodiments of formulae above, R² is

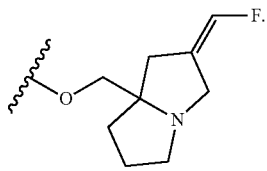 [SMILES: *OCC12CCCN1C/C(=C\F)C2]

In embodiments of formulae above, R² is

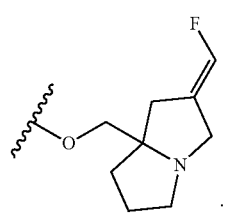 [SMILES: *OCC12CCCN1C/C(=C/F)C2]

In embodiments of formulae above, R² is

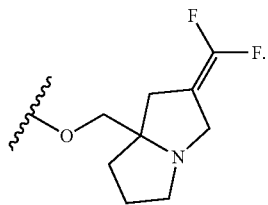 [SMILES: *OCC12CCCN1CC(=C(F)F)C2]

In embodiments of formulae above, R² is

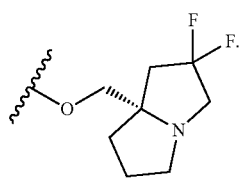 [SMILES: *OC[C@@]12CCCN1CC(F)(F)C2]

In embodiments of formulae above, R² is

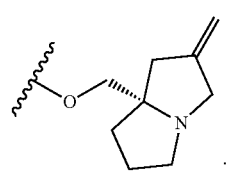

In embodiments of formulae above, R² is

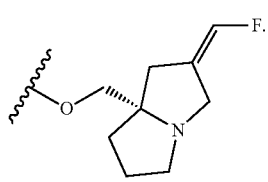 [SMILES: *OC[C@@]12CCCN1C/C(=C\F)C2]

In embodiments of formulae above, R² is

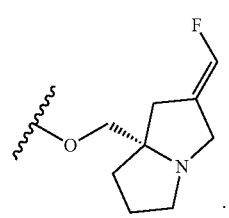 [SMILES: *OC[C@@]12CCCN1C/C(=C/F)C2]

In embodiments of formulae above, R² is

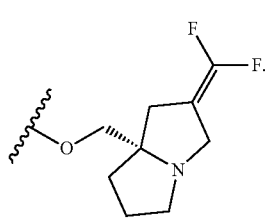 [SMILES: *OC[C@@]12CCCN1CC(=C(F)F)C2]

In embodiments of formulae above, R² is

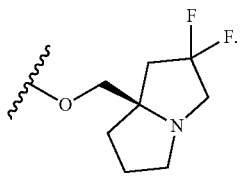 [SMILES: *OC[C@]12CCCN1CC(F)(F)C2]

In embodiments of formulae above, R² is

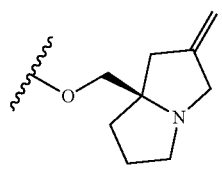

In embodiments of formulae above, R² is

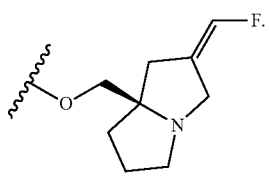 [SMILES: *OC[C@]12CCCN1C/C(=C\F)C2]

In embodiments of formulae above, R² is

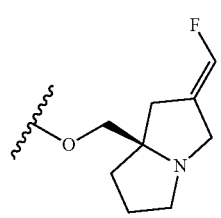

In embodiments of formulae above, R² is

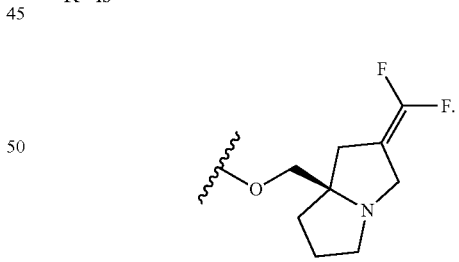

The individual embodiments herein below, or combinations thereof, (e.g., embodiments of $R^{2a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"- 1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{2a}$ is independently hydrogen. In embodiments of the formulae above, each $R^2a$ is independently halogen. In embodiments of the formulae above, each $R^{2a}$ is independently oxo. In embodiments of the formulae above, each $R^2a$ is independently —CN. In embodiments of the formulae above, each $R^{2a}$ is independently $C_{1-6}$alkyl. In embodiments of the formulae above, each $R^{2a}$ is independently $C_{2-6}$alkenyl. In embodiments of the formulae above, each $R^{2a}$ is independently $C_{2-6}$alkynyl. In embodiments of the formulae above, each $R^{2a}$ is independently $C_{3-12}$cycloalkyl. In embodiments of the formulae above, each $R^{2a}$ is independently $C_{2-11}$heterocycloalkyl. In embodiments of the formulae above, each $R^{2a}$ is independently $C_{6-10}$aryl. In embodiments of the formulae above, each $R^{2a}$ is independently $C_{1-9}$heteroaryl. In embodiments of the formulae above;

each $R^{2a}$ is independently —$OR^{12}$. In embodiments of the formulae above, each $R^{2a}$ is independently —$SR^{12}$. In embodiments of the formulae above, each $R^{2a}$ is independently —$N(R^{12})(R^{13})$. In embodiments of the formulae above, each $R^{2a}$ is independently —$C(O)OR^{12}$. In embodiments of the formulae above, each $R^{2a}$ is independently —$OC(O)N(R^{12})(R^{13})$. In embodiments of the formulae above, each $R^{2a}$ is independently —$N(R^{14})C(O)N(R^{12})(R^{13})$. In embodiments of the formulae above, each $R^{2a}$ is independently —$N(R^{14})C(O)OR^{15}$. In embodiments of the formulae above, each $R^2a$ is independently —$N(R^{14})S(O)_2R^{15}$. In embodiments of the formulae above, each $R^{2a}$ is independently —$C(O)R^{15}$. In embodiments of the formulae above, each $R^2a$ is independently —$S(O)R^{15}$. In embodiments of the formulae above, each $R^{2a}$ is independently —$OC(O)R^{15}$. In embodiments of the formulae above, each $R^{2a}$ is independently —$C(O)N(R^{12})(R^{13})$. In embodiments of the formulae above, each $R^{2a}$ is independently —$C(O)C(O)N(R^{12})(R^{13})$. In embodiments of the formulae above, each $R^{2a}$ is independently —$N(R^{14})C(O)R^{15}$. In embodiments of the formulae above, each $R^2a$ is independently —$C(O)C(O)N(R^{12})(R^{13})$. In embodiments of the formulae above, each $R^{2a}$ is independently —$S(O)_2R^{15}$. In embodiments of the formulae above, each $R^{2a}$ is independently —$S(O)_2N(R^{12})(R^{13})$—. In embodiments of the formulae above, each $R^2a$ is independently —$S(=O)(=NH)N(R^{12})(R^{13})$. In embodiments of the formulae above, each $R^{2a}$ is independently —$CH_2C(O)N(R^{12})(R^{13})$. In embodiments of the formulae above, each $R^{2a}$ is independently —$CH_2N(R^{14})C(O)R^{15}$. In embodiments of the formulae above, each $R^{2a}$ is independently —$CH_2S(O)_2R^{15}$. In embodiments of the formulae above, each $R^2a$ is independently —$CH_2S(O)_2N(R^{12})(R^{13})$. In embodiments of the formulae above, each $R^{2a}$ is independently $C_{1-6}$alkyl substituted with one, two, or three $R^{20}b$. In embodiments of the formulae above, each $R^2a$ is independently $C_{2-6}$alkenyl substituted with one, two, or three $R^{20b}$. In embodiments of the formulae above, each $R^2a$ is independently $C_{2-6}$alkynyl substituted with one, two, or three $R^{20b}$. In embodiments of the formulae above, each $R^{2a}$ is independently $C_{3-12}$cycloalkyl substituted with one, two, or three $R^{20}b$. In embodiments of the formulae above, each $R^2a$ is independently $C_{2-11}$heterocycloalkyl substituted with one, two, or three $R^{20}b$. In embodiments of the formulae above, each $R^{2a}$ is independently $C_{6-10}$aryl substituted with one, two, or three $R^{20b}$. In embodiments of the formulae above, each $R^{2a}$ is independently $C_{1-9}$heteroaryl substituted with one, two, or three $R^{20}b$. In embodiments of the formulae above, $R^{2a}$ is independently halogen. In embodiments of the formulae above, $R^{2a}$ is independently F. In embodiments of the formulae above, $R^2a$ is independently $C_1$. In embodiments of the formulae above, $R^{2a}$ is independently Br. In embodiments of the formulae above, $R^{2a}$ is independently I. In embodiments of the formulae above, $R^{2a}$ is independently oxo. In embodiments of the formulae above, $R^2a$ is independently —CN. In embodiments of the formulae above, $R^{2a}$ is independently $C_{1-6}$alkyl. In embodiments of the formulae above, $R^2a$ is independently methyl. In embodiments of the formulae above, $R^{2a}$ is independently ethyl. In embodiments of the formulae above, $R^{2a}$ is independently isopropyl. In embodiments of the formulae above, $R^{2a}$ is independently $C_{2-6}$alkenyl. In embodiments of the formulae above, $R^{2a}$ is independently $C_{2-6}$alkynyl. In embodiments of the formulae above, $R^{2a}$ is independently $C_{1-6}$haloalkyl. In embodiments of the formulae above, $R^{2a}$ is independently —$CF_3$. In embodiments of the formulae above, $R^{2a}$ is independently $C_{3-12}$cycloalkyl. In embodiments of the formulae above, $R^{2a}$ is independently $C_{2-11}$heterocycloalkyl. In embodiments of the formulae above, $R^{2a}$ is independently $C_{6-12}$aryl. In embodiments of the formulae above, $R^{2a}$ is independently $C_{1-11}$heteroaryl. In embodiments of the formulae above, $R^{2a}$ is independently —OH. In embodiments of the formulae above, $R^2a$ is independently —$OCH_3$. In embodiments of the formulae above, $R^{2a}$ is independently —SH. In embodiments of the formulae above, $R^{2a}$ is independently —$SCH_3$. In embodiments of the formulae above, $R^2a$ is independently —$N(CH_3)_2$. In embodiments of the formulae above, $R^{2a}$ is independently —$N(H)_2$. In embodiments of the formulae above, $R^{2a}$ is independently —$C(O)OH$. In embodiments of the formulae above, $R^{2a}$ is independently —$C(O)OCH_3$. In embodiments of the formulae above, $R^{2a}$ is independently —$OC(O)N(H)_2$. In embodiments of the formulae above, $R^{2a}$ is independently —$OC(O)N(CH_3)_2$. In embodiments of the formulae above, $R^{2a}$ is independently —$N(H)C(O)N(CH_3)_2$. In embodiments of the formulae above, R$^{2a}$ is independently —N(H)C(O)N(H)$_2$. In embodiments of the formulae above, R$^{2a}$ is independently —N(H)C(O)OH. In embodiments of the formulae above, R$^{2a}$ is independently —N(H)C(O)OCH$_3$. In embodiments of the formulae above, R$^{2a}$ is independently —N(H)S(O)$_2$CH$_3$. In embodiments of the formulae above, R$^{2a}$ is independently —C(O)CH$_3$. In embodiments of the formulae above, R$^{2a}$ is independently —C(O)H. In embodiments of the formulae above, R$^{2a}$ is independently —S(O)CH$_3$. In embodiments of the formulae above, R$^{2a}$ is independently —OC(O)CH$_3$. In embodiments of the formulae above, R$^{2a}$ is independently —OC(O)H. In embodiments of the formulae above, R$^{2a}$ is independently —C(O)N(CH$_3$)$_2$. In embodiments of the formulae above, R$^{2a}$ is independently —C(O)C(O)N(CH$_3$)$_2$. In embodiments of the formulae above, R$^{2a}$ is independently —N(H)C(O)H. In embodiments of the formulae above, R$^{2a}$ is independently —N(H)C(O)CH$_3$. In embodiments of the formulae above, R$^{2a}$ is independently —S(O)$_2$CH$_3$. In embodiments of the formulae above, R$^{2a}$ is independently —S(O)$_2$N(H)$_2$. In embodiments of the formulae above, R$^{2a}$ is independently —S(O)$_2$N(CH$_3$)$_2$. In embodiments of the formulae above, R$^{2a}$ is independently S(=O)(=NH)N(H)$_2$. In embodiments of the formulae above, R$^{2a}$ is independently S(=O)(=NH)N(CH$_3$)$_2$. In embodiments of the formulae above, R$^{2a}$ is independently —CH$_2$C(O)N(H)$_2$. In embodiments of the formulae above, R$^{2a}$ is independently —CH$_2$C(O)N(CH$_3$)$_2$. In embodiments of the formulae above, R$^{2a}$ is independently —CH$_2$N(H)C(O)H. In embodiments of the formulae above, R$^{2a}$ is independently —CH$_2$N(H)C(O)CH$_3$. In embodiments of the formulae above, R$^{2a}$ is independently —CH$_2$S(O)$_2$H. In embodiments of the formulae above, R$^{2a}$ is independently —CH$_2$S(O)$_2$CH$_3$. In embodiments of the formulae above, R$^{2a}$ is independently and —CH$_2$S(O)$_2$N(CH$_3$)$_2$. In embodiments of the formulae above, R$^{2a}$ is independently and —CH$_2$S(O)$_2$N(H)$_2$.

The individual embodiments herein below, or combinations thereof, (e.g., embodiments of R$^3$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"- 1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each R$^3$ is independently hydrogen. In embodiments of the formulae above, each R$^3$ is independently halogen. In embodiments of the formulae above, each R$^3$ is independently oxo. In embodiments of the formulae above, each R$^3$ is independently —CN. In embodiments of the formulae above, each R$^3$ is independently C$_{1-6}$alkyl. In embodiments of the formulae above, each R$^3$ is independently C$_{2-6}$alkenyl. In embodiments of the formulae above, each R$^3$ is independently C$_{2-6}$alkynyl. In embodiments of the formulae above, each R$^3$ is independently C$_{3-12}$cycloalkyl. In embodiments of the formulae above, each R$^3$ is independently C$_{2-11}$heterocycloalkyl. In embodiments of the formulae above, each R$^3$ is independently C$_{6-10}$aryl. In embodiments of the formulae above, each R$^3$ is independently C$_{1-9}$heteroaryl. In embodiments of the formulae above, each R$^3$ is independently selected from —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, each R$^3$ is independently C$_{1-6}$alkyl substituted with one, two, or three R$^{20}$c. In embodiments of the formulae above, each R$^3$ is independently C$_{2-6}$alkenyl substituted with one, two, or three R$^{20}$c. In embodiments of the formulae above, each R$^3$ is independently C$_{2-6}$alkynyl substituted with one, two, or three R$^{20}$c. In embodiments of the formulae above, each R$^3$ is independently C$_{3-12}$cycloalkyl substituted with one, two, or three R$^{20}$c. In embodiments of the formulae above, each R$^3$ is independently C$_{2-11}$heterocycloalkyl substituted with one, two, or three R$^{20}$c. In embodiments of the formulae above, each R$^3$ is independently C$_{6-10}$aryl substituted with one, two, or three R$^{20}$c. In embodiments of the formulae above;

each R$^3$ is independently C$_{1-9}$heteroaryl substituted with one, two, or three R$^{20}$c. In embodiments of the formulae above, R$^3$ is independently F. In embodiments of the formulae above, R$^3$ is independently C$_1$. In embodiments of the formulae above, R$^3$ is independently Br. In embodiments of the formulae above, R$^3$ is independently I. In embodiments of the formulae above, R$^3$ is independently R$^3$ is independently oxo. In embodiments of the formulae above, R$^3$ is independently methyl. In embodiments of the formulae above, R$^3$ is independently ethyl. In embodiments of the formulae above, R$^3$ is independently isopropyl. In embodiments of the formulae above, R$^3$ is independently C$_{2-6}$alkenyl. In embodiments of the formulae above, R$^3$ is independently C$_{2-6}$alkynyl. In embodiments of the formulae above, R$^3$ is independently C$_{1-6}$haloalkyl. In embodiments of the formulae above, R$^3$ is independently —CF$_3$. In embodiments of the formulae above, R$^3$ is independently C$_{6-12}$aryl. In embodiments of the formulae above, R$^3$ is independently C$_{1-11}$heteroaryl. In embodiments of the formulae above, R$^3$ is independently selected from —OH, —OCH$_3$, —SH, —SCH$_3$, —N(CH$_3$)$_2$, —N(H)$_2$, —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the compounds of the formulae above, or a pharmaceutically acceptable salt or solvate thereof, R$^3$ is hydrogen or CN. In embodiments of the compounds of the formulae above, or a pharmaceutically acceptable salt or solvate thereof, R$^3$ is hydrogen. In embodiments of the compounds of the formulae above, or a pharmaceutically acceptable salt or solvate thereof, R$^3$ is CN.

In embodiments of the formulae above, each R$^3$ is independently —OR$^{12}$. In embodiments of the formulae above, each R$^3$ is independently —SR$^{12}$. In embodiments of the formulae above, each R$^3$ is independently —N(R$^{12}$)(R$^{13}$). In embodiments of the formulae above, each R$^3$ is independently —C(O)OR$^{12}$. In embodiments of the formulae above, each R$^3$ is independently selected from —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, R$^3$ is independently halogen. In embodiments of the formulae above, R$^3$ is independently halogen.

In embodiments of the formulae above, R$^3$ is independently C$_{3-12}$cycloalkyl. In embodiments of the formulae above, R$^3$ is independently C$_{2-11}$heterocycloalkyl. In embodiments of the formulae above, R$^3$ is independently C$_{6-12}$aryl. In embodiments of the formulae above, R$^3$ is independently C$_{1-11}$heteroaryl. In embodiments of the formulae above, R$^3$ is independently —OH. In embodiments of the formulae above, R$^3$ is independently —OCH$_3$. In embodiments of the formulae above, R$^3$ is independently —SH. In embodiments of the formulae above, R$^3$ is independently —SCH$_3$. In embodiments of the formulae above, R$^3$ is independently —N(CH$_3$)$_2$. In embodiments of the formulae above, R$^3$ is independently —N(H)$_2$. In embodiments of the formulae above, R$^3$ is independently —C(O)OH. In embodiments of the formulae above, R$^3$ is independently selected from —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

The individual embodiments herein below, or combinations thereof, (e.g., embodiments of R$^{3a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each R$^{3a}$ is independently hydrogen. In embodiments of the formulae above, each R$^{3a}$ is independently halogen. In embodiments of the formulae above, each R$^{3a}$ is independently oxo. In embodiments of the formulae above, each R$^{3a}$ is independently —CN. In embodiments of the formulae above, each R$^{3a}$ is independently C$_{1-6}$alkyl. In embodiments of the formulae above, each R$^{3a}$ is independently C$_{2-6}$alkenyl. In embodiments of the formulae above, each R$^{3a}$ is independently C$_{2-6}$alkynyl. In embodiments of the formulae above, each R$^{3a}$ is independently C$_{3-12}$cycloalkyl. In embodiments of the formulae above, each R$^{3a}$ is independently C$_{2-11}$heterocycloalkyl. In embodiments of the formulae above, each R$^{3a}$ is independently C$_{6-10}$aryl. In embodiments of the formulae above, each R$^{3a}$ is independently C$_{1-9}$heteroaryl. In embodiments of the formulae above, each R$^{3a}$ is independently selected from —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, each R$^{3a}$ is independently C$_{1-6}$alkyl substituted with one, two, or three R$^{20}$c. In embodiments of the formulae above, each R$^{3a}$ is independently C$_{2-6}$alkenyl substituted with one, two, or three R$^{20}$c. In embodiments of the formulae above, each R$^{3a}$ is independently C$_{2-6}$alkynyl substituted with one, two, or three R$^{20}$c. In embodiments of the formulae above, each R$^{3a}$ is independently C$_{3-12}$cycloalkyl substituted with one, two, or three R$^{20}$c. In embodiments of the formulae above, each R$^{3a}$ is independently $C_{2-11}$heterocycloalkyl substituted with one, two, or three $R^{20}$c. In embodiments of the formulae above, each $R^{3a}$ is independently $C_{6-10}$aryl substituted with one, two, or three $R^{20}$c. In embodiments of the formulae above, each $R^{3a}$ is independently $C_{1-9}$heteroaryl substituted with one, two, or three $R^{20}$c. In embodiments of the formulae above, $R^{3a}$ is independently halogen. In embodiments of the formulae above, $R^{3a}$ is independently F. In embodiments of the formulae above, $R^{3a}$ is independently $C_1$. In embodiments of the formulae above, $R^{3a}$ is independently Br. In embodiments of the formulae above, $R^{3a}$ is independently I. In embodiments of the formulae above, $R^{3a}$ is independently $R^{3a}$ is independently oxo. In embodiments of the formulae above, $R^{3a}$ is independently —CN. In embodiments of the formulae above, $R^{3a}$ is independently methyl. In embodiments of the formulae above, $R^{3a}$ is independently ethyl. In embodiments of the formulae above, $R^{3a}$ is independently isopropyl. In embodiments of the formulae above, $R^{3a}$ is independently $C_{2-6}$alkenyl. In embodiments of the formulae above, $R^{3a}$ is independently $C_{2-6}$alkynyl. In embodiments of the formulae above, $R^{3a}$ is independently $C_{1-6}$haloalkyl. In embodiments of the formulae above, $R^{3a}$ is independently —CF$_3$. In embodiments of the formulae above, $R^{3a}$ is independently $C_{6-12}$aryl. In embodiments of the formulae above, $R^{3a}$ is independently $C_{1-11}$heteroaryl. In embodiments of the formulae above, $R^{3a}$ is independently selected from —OH, —OCH$_3$, —SH, —SCH$_3$, —N(CH$_3$)$_2$, —N(H)$_2$, —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the formulae above, each $R^{3a}$ is independently —OR$^{12}$. In embodiments of the formulae above, each $R^{3a}$ is independently —SR$^{12}$. In embodiments of the formulae above, each $R^{3a}$ is independently —N(R$^{12}$)(R$^{13}$). In embodiments of the formulae above, each $R^{3a}$ is independently —C(O)OR$^{12}$. In embodiments of the formulae above, each $R^{3a}$ is independently selected from —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, $R^{3a}$ is independently $C_{1-6}$alkyl. In embodiments of the formulae above, $R^{3a}$ is independently $C_{3-12}$cycloalkyl. In embodiments of the formulae above, $R^{3a}$ is independently $C_{2-11}$heterocycloalkyl. In embodiments of the formulae above, $R^{3a}$ is independently —OH. In embodiments of the formulae above, $R^{3a}$ is independently —OCH$_3$. In embodiments of the formulae above, $R^{3a}$ is independently —SH. In embodiments of the formulae above, $R^{3a}$ is independently —SCH$_3$. In embodiments of the formulae above, $R^{3a}$ is independently —N(CH$_3$)$_2$. In embodiments of the formulae above, $R^{3a}$ is independently —N(H)$_2$. In embodiments of the formulae above, $R^{3a}$ is independently —C(O)OH. In embodiments of the formulae above, $R^{3a}$ is independently selected from —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

The individual embodiments herein below, or combinations thereof, (e.g., embodiments of R$^3$b) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''- 1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each R$^3$b is independently hydrogen. In embodiments of the formulae above, each R$^3$b is independently —CN. In embodiments of the formulae above, each R$^3$b is independently $C_{1-6}$alkyl. In embodiments of the formulae above, each R$^3$b is independently $C_{2-6}$alkenyl. In embodiments of the formulae above, each R$^3$b is independently $C_{2-6}$alkynyl. In embodiments of the formulae above, each R$^3$b is independently $C_{3-12}$cycloalkyl. In embodiments of the formulae above;

each R$^3$b is independently $C_{2-11}$heterocycloalkyl. In embodiments of the formulae above, each R$^3$b is independently $C_{6-10}$aryl. In embodiments of the formulae above, each R$^3$b is independently $C_{1-9}$heteroaryl. In embodiments of the formulae above, each R$^3$b is independently selected from —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^3b$ is independently $C_{1-6}$ alkyl substituted with one, two, or three $R^{20}c$. In embodiments of the formulae above, each $R^3b$ is independently $C_{2-6}$alkenyl substituted with one, two, or three $R^{20}c$. In embodiments of the formulae above, each $R^3b$ is independently $C_{2-6}$alkynyl substituted with one, two, or three $R^{20}c$. In embodiments of the formulae above, each $R^3b$ is independently $C_{3-12}$cycloalkyl substituted with one, two, or three $R^{20}c$. In embodiments of the formulae above, each $R^3b$ is independently $C_{2-6}$heterocycloalkyl substituted with one, two, or three $R^{20}c$. In embodiments of the formulae above, each $R^3b$ is independently $C_{6-10}$aryl substituted with one, two, or three $R^{20}c$. In embodiments of the formulae above, each $R^3b$ is independently $C_{1-9}$heteroaryl substituted with one, two, or three $R^{20}c$. In embodiments of the formulae above, $R^3b$ is independently methyl. In embodiments of the formulae above, $R^3b$ is independently ethyl. In embodiments of the formulae above, $R^3b$ is independently isopropyl. In embodiments of the formulae above, $R^3b$ is independently $C_2$-falkenyl. In embodiments of the formulae above, $R^3b$ is independently $C_{2-6}$alkynyl. In embodiments of the formulae above, $R^3b$ is independently $C_{1-6}$haloalkyl. In embodiments of the formulae above, $R^3b$ is independently —$CF_3$. In embodiments of the formulae above, $R^3b$ is independently $C_{6-12}$aryl. In embodiments of the formulae above, $R^3b$ is independently $C_{1-11}$heteroaryl. In embodiments of the formulae above, $R^3b$ is independently selected from —OH, —$OCH_3$, —SH, —$SCH_3$, —C(O)OH, —$C(O)OCH_3$, —$OC(O)N(H)_2$, —$OC(O)N(CH_3)_2$, —$C(O)CH_3$, —C(O)H, —$S(O)CH_3$, —$OC(O)CH_3$, —OC(O)H, —$C(O)N(CH_3)_2$, —$C(O)C(O)N(CH_3)_2$, —$S(O)_2CH_3$, —$S(O)_2N(H)_2$, —$S(O)_2N(CH_3)_2$, $S(=O)(=NH)N(H)_2$, $S(=O)(=NH)N(CH_3)_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2CH_3$, —$CH_2S(O)_2N(CH_3)_2$, and —$CH_2S(O)_2N(H)_2$. In embodiments of the formulae above;

each $R^3b$ is independently —$OR^{12}$. In embodiments of the formulae above, each $R^3b$ is independently —$SR^{12}$. In embodiments of the formulae above, each $R^3b$ is independently —$C(O)OR^{12}$. In embodiments of the formulae above, each $R^3b$ is independently selected from —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, $R^3b$ is independently $C_{1-6}$alkyl. In embodiments of the formulae above, $R^3b$ is independently $C_{3-12}$cycloalkyl. In embodiments of the formulae above, $R^3b$ is independently $C_{2-11}$heterocycloalkyl. In embodiments of the formulae above, $R^3b$ is independently —OH. In embodiments of the formulae above, $R^3b$ is independently —$OCH_3$. In embodiments of the formulae above, $R^3b$ is independently —SH. In embodiments of the formulae above, $R^3b$ is independently —$SCH_3$. In embodiments of the formulae above, $R^3b$ is independently —C(O)OH. In embodiments of the formulae above, $R^3b$ is independently selected from —$C(O)OCH_3$, —$OC(O)N(H)_2$, —$OC(O)N(CH_3)_2$, —$C(O)CH_3$, —C(O)H, —$S(O)CH_3$, —$OC(O)CH_3$, —OC(O)H, —$C(O)N(CH_3)_2$, —$C(O)C(O)N(CH_3)_2$, —$S(O)_2CH_3$, —$S(O)_2N(H)_2$, —$S(O)_2N(CH_3)_2$, $S(=O)(=NH)N(H)_2$, $S(=O)(=NH)N(CH_3)_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2CH_3$, —$CH_2S(O)_2N(CH_3)_2$, and —$CH_2S(O)_2N(H)_2$.

The individual embodiments herein below, or combinations thereof, (e.g., embodiments of $R^3c$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"- 1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^3c$ is independently hydrogen. In embodiments of the formulae above, each $R^3c$ is independently —CN. In embodiments of the formulae above, each $R^3c$ is independently $C_{1-6}$alkyl. In embodiments of the formulae above, each $R^3c$ is independently $C_{2-6}$alkenyl. In embodiments of the formulae above, each $R^3c$ is independently $C_{2-6}$alkynyl. In embodiments of the formulae above, each $R^3c$ is independently $C_{3-12}$cycloalkyl. In embodiments of the formulae above, each $R^3c$ is independently $C_{2-11}$heterocycloalkyl. In embodiments of the formulae above, each $R^3c$ is independently $C_{6-10}$aryl. In embodiments of the formulae above, each $R^3c$ is independently $C_{1-9}$heteroaryl. In embodiments of the formulae above, each $R^3c$ is independently selected from —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^3c$ is independently $C_{1-6}$alkyl substituted with one, two, or three $R^{20}c$. In embodiments of the formulae above, each $R^3c$ is independently $C_{2-6}$alkenyl substituted with one, two, or three $R^{20}c$. In embodiments of the formulae above, each $R^3c$ is independently $C_{2-6}$alkynyl substituted with one, two, or three $R^{20}c$. In embodiments of the formulae above, each $R^3c$ is independently $C_{3-12}$cycloalkyl substituted with one, two, or three $R^{20}c$. In embodiments of the formulae above, each $R^3c$ is independently $C_{2-11}$heterocycloalkyl substituted with one, two, or three
$R^{20}c$. In embodiments of the formulae above, each $R^3c$ is independently $C_{6-10}$aryl substituted with one, two, or three $R^{20}c$. In embodiments of the formulae above, each $R^3c$ is independently $C_{1-9}$heteroaryl substituted with one, two, or three $R^{20}c$. In embodiments of the formulae above, $R^3c$ is independently methyl. In embodiments of the formulae above, $R^3c$ is independently ethyl. In embodiments of the formulae above, $R^3c$ is independently isopropyl. In embodiments of the formulae above, $R^3c$ is independently $C_2$-falkenyl. In embodiments of the formulae above, $R^3c$ is independently $C_{2-6}$alkynyl. In embodiments of the formulae above, $R^3c$ is independently $C_{1-6}$haloalkyl. In embodiments of the formulae above, $R^3c$ is independently —$CF_3$. In embodiments of the formulae above, $R^3c$ is independently $C_{6-12}$aryl. In embodiments of the formulae above, $R^3c$ is independently $C_{1-11}$heteroaryl. In embodiments of the formulae above, $R^3c$ is independently selected from —OH, —$OCH_3$, —SH, —$SCH_3$, —C(O)OH, —C(O)$OCH_3$, —OC(O)N(H)$_2$, —OC(O)N($CH_3$)$_2$, —C(O)$CH_3$, —C(O)H, —S(O)$CH_3$, —OC(O)$CH_3$, —OC(O)H, —C(O)N($CH_3$)$_2$, —C(O)C(O)N($CH_3$)$_2$, —S(O)$_2CH_3$, —S(O)$_2$N(H)$_2$, —S(O)$_2$N($CH_3$)$_2$, S(=OX=NH)N(H)$_2$, S(=O)(=NH)N($CH_3$)$_2$, —$CH_2$C(O)N(H)$_2$, —$CH_2$C(O)N($CH_3$)$_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2$N($CH_3$)$_2$, and —$CH_2$S(O)$_2$N(H)$_2$.

The individual embodiments herein below, or combinations thereof, (e.g., embodiments of $R^5$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"- 1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^5$ is independently hydrogen. In embodiments of the formulae above, each $R^5$ is independently halogen. In embodiments of the formulae above, each $R^5$ is independently oxo. In embodiments of the formulae above, each $R^5$ is independently —CN. In embodiments of the formulae above, each $R^5$ is independently $C_{1-6}$alkyl. In embodiments of the formulae above, each $R^5$ is independently $C_{2-6}$alkenyl. In embodiments of the formulae above, each $R^5$ is independently $C_{2-6}$alkynyl. In embodiments of the formulae above, each $R^5$ is independently selected from —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —C(O)C(O)N($R^{12}$)($R^{13}$), —S(O)$_2R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$). In embodiments of the formulae above, each $R^5$ is independently $C_{1-6}$alkyl substituted with one, two, or three $R^{20}d$. In embodiments of the formulae above;
each $R^5$ is independently $C_{2-6}$alkenyl substituted with one, two, or three $R^{20}d$. In embodiments of the formulae above, each $R^5$ is independently $C_{2-6}$alkynyl substituted with one, two, or three $R^{20}d$. In embodiments of the formulae above, $R^5$ is independently F. In embodiments of the formulae above, $R^5$ is independently $C_1$. In embodiments of the formulae above, $R^5$ is independently Br. In embodiments of the formulae above, $R^5$ is independently I. In embodiments of the formulae above, $R^5$ is independently $C_{1-6}$alkyl. In embodiments of the formulae above, $R^5$ is independently methyl. In embodiments of the formulae above, $R^5$ is independently ethyl. In embodiments of the formulae above, $R^5$ is independently isopropyl. In embodiments of the formulae above, $R^5$ is independently $C_2$-falkenyl. In embodiments of the formulae above, $R^5$ is independently $C_{2-6}$alkynyl. In embodiments of the formulae above, $R^5$ is independently $C_{1-6}$haloalkyl. In embodiments of the formulae above, $R^5$ is independently selected from —$CF_3$, —OH, —$OCH_3$, —SH, —$SCH_3$, —N($CH_3$)$_2$, —N(H)$_2$, —C(O)OH, —C(O)$OCH_3$, —OC(O)N(H)$_2$, —OC(O)N($CH_3$)$_2$, —N(H)C(O)N($CH_3$)$_2$, —N(H)C(O)N(H)$_2$, —N(H)C(O)OH, —N(H)C(O)$OCH_3$, —N(H)S(O)$_2CH_3$, —C(O)$CH_3$, —C(O)H, —S(O)$CH_3$, —OC(O)$CH_3$, —OC(O)H, —C(O)N($CH_3$)$_2$, —C(O)C(O)N($CH_3$)$_2$, —N(H)C(O)H, —N(H)C(O)$CH_3$, —S(O)$_2CH_3$, —S(O)$_2$N(H)$_2$, —S(O)$_2$N($CH_3$)$_2$, S(=O)(=NH)N(H)$_2$, S(=O)(=NH)N($CH_3$)$_2$, —$CH_2$C(O)N(H)$_2$, —$CH_2$C(O)N($CH_3$)$_2$, —$CH_2$N(H)C(O)H, —$CH_2$N(H)C(O)$CH_3$, —$CH_2$S(O)$_2$H, —$CH_2$S(O)$_2$ $CH_3$, —$CH_2$S(O)$_2$N($CH_3$)$_2$, and —$CH_2$S(O)$_2$N(H)$_2$. In embodiments of the formulae above, each $R^5$ is independently —$OR^{12}$. In embodiments of the formulae above, each $R^5$ is independently —$SR^{12}$. In embodiments of the formulae above, each $R^5$ is independently —N($R^{12}$)($R^{13}$). In embodiments of the formulae above, each $R^5$ is independently —C(O)$OR^{12}$. In embodiments of the formulae above, each $R^5$ is independently selected from —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)

($R^{13}$), —C(O)C(O)N($R^{12}$)($R^{13}$), —N($R^{14}$)C(O)$R^{15}$, —C(O)C(O)N($R^{12}$)($R^{13}$), —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$). In embodiments of the formulae above, $R^5$ is independently halogen. In embodiments of the formulae above, $R^5$ is independently $R^5$ is independently oxo. In embodiments of the formulae above, $R^5$ is independently —CN. In embodiments of the formulae above, $R^5$ is independently —CF$_3$. In embodiments of the formulae above, $R^5$ is independently —OH. In embodiments of the formulae above, $R^5$ is independently —OCH$_3$. In embodiments of the formulae above, $R^5$ is independently —SH. In embodiments of the formulae above, $R^5$ is independently —SCH$_3$. In embodiments of the formulae above, $R^5$ is independently —N(CH$_3$)$_2$. In embodiments of the formulae above, $R^5$ is independently —N(H)$_2$. In embodiments of the formulae above, $R^5$ is independently —C(O)OH. In embodiments of the formulae above, $R^5$ is independently selected from —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

The individual embodiments herein below, or combinations thereof, (e.g., embodiments of $R^6$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^6$ is independently hydrogen. In embodiments of the formulae above, each $R^6$ is independently halogen. In embodiments of the formulae above, each $R^6$ is independently oxo. In embodiments of the formulae above, each $R^6$ is independently —CN. In embodiments of the formulae above, each $R^6$ is independently $C_{1-6}$alkyl. In embodiments of the formulae above, each $R^6$ is independently $C_{2-6}$alkenyl. In embodiments of the formulae above, each $R^6$ is independently $C_{2-6}$alkynyl. In embodiments of the formulae above, each $R^6$ is independently $C_{3-12}$cycloalkyl. In embodiments of the formulae above, each $R^6$ is independently $C_{2-11}$heterocycloalkyl. In embodiments of the formulae above, each $R^6$ is independently $C_{6-10}$aryl. In embodiments of the formulae above, each $R^6$ is independently $C_{1-9}$heteroaryl. In embodiments of the formulae above;

each $R^6$ is independently selected-O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —C(O)C(O)N($R^{12}$)($R^{13}$), —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$). In embodiments of the formulae above, each $R^6$ is independently $C_{1-6}$alkyl substituted with one, two, or three $R^{20}$c. In embodiments of the formulae above, each $R^6$ is independently $C_{2-6}$alkenyl substituted with one, two, or three $R^{20}$e. In embodiments of the formulae above, each $R^6$ is independently $C_{2-6}$alkynyl substituted with one, two, or three $R^{20}$e. In embodiments of the formulae above, each $R^6$ is independently $C_{3-12}$cycloalkyl substituted with one, two, or three $R^{20}$c. In embodiments of the formulae above, each $R^6$ is independently $C_{2-11}$heterocycloalkyl substituted with one, two, or three $R^{20}$c. In embodiments of the formulae above, each $R^6$ is independently $C_{6-10}$aryl substituted with one, two, or three $R^{20}$c. In embodiments of the formulae above;

each $R^6$ is independently $C_{1-9}$heteroaryl substituted with one, two, or three $R^{20}$e. In embodiments of the formulae above, $R^6$ is independently F. In embodiments of the formulae above, $R^6$ is independently Cl. In embodiments of the formulae above, $R^6$ is independently Br. In embodiments of the formulae above, $R^6$ is independently I. In embodiments of the formulae above, $R^6$ is independently $C_{1-6}$alkyl. In embodiments of the formulae above, $R^6$ is independently methyl. In embodiments of the formulae above, $R^6$ is independently ethyl. In embodiments of the formulae above, $R^6$ is independently isopropyl. In embodiments of the formulae above, $R^6$ is independently $C_{2-6}$alkenyl. In embodiments of the formulae above, $R^6$ is independently $C_{2-6}$alkynyl. In embodiments of the formulae above, $R^6$ is independently $C_{1-6}$haloalkyl. In embodiments of the formulae above, $R^6$ is independently —CF$_3$ In embodiments of the formulae above, $R^6$ is independently $C_{6-12}$aryl. In embodiments of the formulae above, $R^6$ is independently $C_{1-11}$heteroaryl. In embodiments of the formulae above, $R^6$ is independently selected from —OH, —OCH$_3$, —SH, —SCH$_3$, —N(CH$_3$)$_2$, —N(H)$_2$, —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)

C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the compounds of the formulae above, or a pharmaceutically acceptable salt or solvate thereof, R$^6$ is selected from hydrogen, C$_{1-6}$alkyl, C$_{2-6}$alkenyl, C$_{2-6}$alkynyl, C$_{3-10}$cycloalkyl, and C$_{2-9}$heterocycloalkyl, wherein C$_{1-6}$alkyl, C$_{2-6}$alkenyl, C$_{2-6}$alkynyl, C$_{3-10}$cycloalkyl, and C$_{2-9}$heterocycloalkyl are optionally substituted with one, two, or three R$^{20}$e. In embodiments of the compounds of the formulae above, or a pharmaceutically acceptable salt or solvate thereof, R$^6$ is selected from hydrogen, C$_{1-6}$alkyl, C$_{3-10}$cycloalkyl, and C$_{2-9}$heterocycloalkyl, wherein C$_{1-6}$alkyl, C$_{3-10}$cycloalkyl, and C$_{2-9}$heterocycloalkyl are optionally substituted with one, two, or three R$^{20}$c independently selected from halogen, C$_{1-6}$alkyl, C$_{2-6}$alkenyl, C$_{2-6}$alkynyl, C$_{3-10}$cycloalkyl, and C$_{2-9}$heterocycloalkyl. In embodiments of the compounds of the formulae above, or a pharmaceutically acceptable salt or solvate thereof, R$^6$ is selected from hydrogen, methyl, cyclopropyl, cyclobutyl, and oxetanyl, wherein said methyl, cyclopropyl, cyclobutyl, and oxetanyl are optionally substituted with one, two, or three R$^{20}$e independently selected from fluoro, methyl, cyclopropyl, cyclobutyl, and oxetanyl. In embodiments of the compounds of the formulae above, or a pharmaceutically acceptable salt or solvate thereof, R$^6$ is selected from hydrogen, methyl, cyclopropyl, cyclobutyl, and oxetanyl. In embodiments of the compounds of the formulae above, or a pharmaceutically acceptable salt or solvate thereof, R$^6$ is selected from C$_{1-6}$alkyl, C$_{3-10}$cycloalkyl, and C$_{2-9}$heterocycloalkyl, wherein C$_{1-6}$alkyl, C$_{3-10}$cycloalkyl, and C$_{2-9}$heterocycloalkyl are optionally substituted with one, two, or three R$^{20}$e independently selected from halogen, C$_{1-6}$alkyl, C$_{2-6}$alkenyl, C$_{2-6}$alkynyl, C$_{3-10}$cycloalkyl, and C$_{2-9}$heterocycloalkyl. In embodiments of the compounds of the formulae above, or a pharmaceutically acceptable salt or solvate thereof, R$^6$ is selected from methyl, cyclopropyl, cyclobutyl, and oxetanyl, wherein said methyl, cyclopropyl, cyclobutyl, and oxetanyl are optionally substituted with one, two, or three R$^{20}$c independently selected from fluoro, methyl, cyclopropyl, cyclobutyl, and oxetanyl. In embodiments of the compounds of the formulae above, or a pharmaceutically acceptable salt or solvate thereof, R$^6$ is selected from methyl, cyclopropyl, cyclobutyl, and oxetanyl. In embodiments of the formulae above R$^6$ is F. In embodiments of the formulae above R$^6$ is C$_1$. In embodiments of the formulae above R$^6$ is Br. In embodiments of the formulae above R$^6$ is I. In embodiments of the formulae above, each R$^6$ is independently —OR$^{12}$. In embodiments of the formulae above, each R$^6$ is independently —SR$^{12}$. In embodiments of the formulae above, each R$^6$ is independently —N(R$^{12}$)(R$^{13}$). In embodiments of the formulae above, each R$^6$ is independently —C(O)OR$^{12}$. In embodiments of the formulae above;
each R$^6$ is independently selected from —OC(O)N(R$^{12}$)(R$^{13}$), —N(R$^{14}$)C(O)N(R$^{12}$)(R$^{13}$), —N(R$^{14}$)C(O) OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, R$^6$ is independently —CF$_3$. In embodiments of the formulae above, R$^6$ is independently C$_{3-12}$cycloalkyl. In embodiments of the formulae above, R$^6$ is independently C$_{2-11}$heterocycloalkyl. In embodiments of the formulae above, R$^6$ is independently C$_{6-12}$aryl. In embodiments of the formulae above, R$^6$ is independently C$_{1-11}$heteroaryl. In embodiments of the formulae above, R$^6$ is independently —OH. In embodiments of the formulae above, R$^6$ is independently —OCH$_3$. In embodiments of the formulae above, R$^6$ is independently —SH. In embodiments of the formulae above, R$^6$ is independently —SCH$_3$. In embodiments of the formulae above, R$^6$ is independently —N(CH$_3$)$_2$. In embodiments of the formulae above, R$^6$ is independently —N(H)$_2$. In embodiments of the formulae above, R$^6$ is independently —C(O)OH. In embodiments of the formulae above, R$^6$ is independently selected from —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$ CH$_3$, —CH$_2$S(O)$_2$N(CH$_3$)$_2$, and —CH$_2$S(O)$_2$N(H)$_2$. In embodiments of the formulae above, R$^6$ is selected from halogen, —CN, C$_{1-6}$alkyl, C$_{2-6}$alkenyl, C$_{2-6}$alkynyl, C$_{3-6}$cycloalkyl, C$_{2-9}$ heterocycloalkyl, C$_{6-10}$aryl, C$_{1-9}$heteroaryl, —OR$^{12}$, —SR$^{12}$, —N(H)(R$^{12}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20}$c.

The individual embodiments herein below, or combinations thereof, (e.g., embodiments of R$^{6a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^6a$ is independently hydrogen. In embodiments of the formulae above, each $R^6a$ is independently halogen. In embodiments of the formulae above, each $R^{6a}$ is independently oxo. In embodiments of the formulae above, each $R^6a$ is independently —CN. In embodiments of the formulae above, each $R^{6a}$ is independently $C_{1-6}$alkyl. In embodiments of the formulae above, each $R^6a$ is independently $C_{2-6}$alkenyl. In embodiments of the formulae above, each $R^{6a}$ is independently $C_{2-6}$alkynyl. In embodiments of the formulae above, each $R^{6a}$ is independently $C_{3-12}$cycloalkyl. In embodiments of the formulae above, each $R^{6a}$ is independently $C_{2-11}$heterocycloalkyl. In embodiments of the formulae above, each $R^{6a}$ is independently $C_{6-10}$aryl. In embodiments of the formulae above, each $R^{6a}$ is independently $C_{1-9}$heteroaryl. In embodiments of the formulae above, each $R^{6a}$ is independently selected from —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^{6a}$ is independently $C_{1-6}$alkyl substituted with one, two, or three $R^{20}c$. In embodiments of the formulae above, each $R^{6a}$ is independently $C_{2-6}$alkenyl substituted with one, two, or three $R^{20}e$. In embodiments of the formulae above, each $R^{6a}$ is independently $C_{2-6}$alkynyl substituted with one, two, or three $R^{20}c$. In embodiments of the formulae above, each $R^{6a}$ is independently $C_{3-12}$cycloalkyl substituted with one, two, or three $R^{20}c$. In embodiments of the formulae above, each $R^{6a}$ is independently $C_{2-11}$heterocycloalkyl substituted with one, two, or three $R^{20}c$. In embodiments of the formulae above, each $R^{6a}$ is independently $C_{6-10}$aryl substituted with one, two, or three $R^{20}c$. In embodiments of the formulae above, each $R^6a$ is independently $C_{1-9}$heteroaryl substituted with one, two, or three $R^{20}c$. In embodiments of the formulae above, $R^{6a}$ is independently F. In embodiments of the formulae above, $R^{6a}$ is independently $C_1$. In embodiments of the formulae above, $R^{6a}$ is independently Br. In embodiments of the formulae above, $R^{6a}$ is independently I. In embodiments of the formulae above, $R^{6a}$ is independently $C_{1-6}$alkyl. In embodiments of the formulae above, $R^6a$ is independently methyl. In embodiments of the formulae above, $R^{6a}$ is independently ethyl. In embodiments of the formulae above, $R^{6a}$ is independently isopropyl. In embodiments of the formulae above, $R^{6a}$ is independently $C_{2-6}$alkenyl. In embodiments of the formulae above, $R^{6a}$ is independently $C_{2-6}$alkynyl. In embodiments of the formulae above, $R^{6a}$ is independently $C_{1-6}$haloalkyl. In embodiments of the formulae above, $R^{6a}$ is independently —$CF_3$. In embodiments of the formulae above, $R^{6a}$ is independently $C_{6-12}$aryl. In embodiments of the formulae above, $R^6a$ is independently $C_{1-11}$heteroaryl. In embodiments of the formulae above, $R^{6a}$ is independently selected from —OH, —$OCH_3$, —SH, —$SCH_3$, —$N(CH_3)_2$, —$N(H)_2$, —C(O)OH, —$C(O)OCH_3$, —$OC(O)N(H)_2$, —$OC(O)N(CH_3)_2$, —$N(H)C(O)N(CH_3)_2$, —$N(H)C(O)N(H)_2$, —$N(H)C(O)OH$, —$N(H)C(O)OCH_3$, —$N(H)S(O)_2CH_3$, —$C(O)CH_3$, —C(O)H, —$S(O)CH_3$, —$OC(O)CH_3$, —OC(O)H, —$C(O)N(CH_3)_2$, —$C(O)C(O)N(CH_3)_2$, —$N(H)C(O)H$, —$N(H)C(O)CH_3$, —$S(O)_2CH_3$, —$S(O)_2N(H)_2$, —$S(O)_2N(CH_3)_2$, $S(=O)(=NH)N(H)_2$, $S(=O)(=NH)N(CH_3)_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2 CH_3$, —$CH_2S(O)_2N(CH_3)_2$, and —$CH_2S(O)_2N(H)_2$. In embodiments of the formulae above, each $R^{6a}$ is independently —$OR^{12}$. In embodiments of the formulae above, each $R^{6a}$ is independently —$SR^{12}$. In embodiments of the formulae above, $R^{6a}$ is independently —$N(R^{12})(R^{13})$. In embodiments of the formulae above, each $R^{6a}$ is independently —$C(O)OR^{12}$. In embodiments of the formulae above, each $R^{6a}$ is independently selected from —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2 R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, $R^{6a}$ is independently —OH. In embodiments of the formulae above, $R^{6a}$ is independently —$OCH_3$. In embodiments of the formulae above, $R^6a$ is independently —SH. In embodiments of the formulae above, $R^{6a}$ is independently —$SCH_3$. In embodiments of the formulae above, $R^6a$ is independently —$N(CH_3)_2$. In embodiments of the formulae above, $R^{6a}$ is independently —$N(H)_2$. In embodiments of the formulae above, $R^{6a}$ is independently —C(O)OH. In embodiments of the formulae above, $R^{6a}$ is independently selected from —$C(O)OCH_3$, —$OC(O)N(H)_2$, —$OC(O)N(CH_3)_2$, —$N(H)C(O)N(CH_3)_2$, —$N(H)C(O)N(H)_2$, —$N(H)C(O)OH$, —$N(H)C(O)OCH_3$, —$N(H)S(O)_2CH_3$, —$C(O)CH_3$, —C(O)H, —$S(O)CH_3$, —$OC(O)CH_3$, —OC(O)H, —$C(O)N(CH_3)_2$, —$C(O)C(O)N(CH_3)_2$, —$N(H)C(O)H$, —$N(H)C(O)CH_3$, —$S(O)_2CH_3$, —$CH_2N(H)C(O)CH_3$, —$CH_2S(O)_2H$, —$CH_2S(O)_2 CH_3$, —$CH_2S(O)_2N(CH_3)_2$, and —$CH_2S(O)_2N(H)_2$.

The individual embodiments herein below, or combinations thereof, (e.g., embodiments of $R^6b$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"- 1c), (B"-1c), (C"-1c), (A"-1d), (B"-1d), (C"-1d), (A"-1e), (B"-1e), (C"-1e), (A"-1f), (B"-1f), or (C"-1f) or a pharmaceutically acceptable salt or solvate thereof. In embodiments of the formulae above, each $R^{6b}$ is independently hydrogen. In embodiments of the formulae above, each $R^{6b}$ is independently —CN. In embodiments of the formulae above, each $R^6b$ is independently $C_{1-6}$alkyl. In embodiments of the formulae above, each $R^{6b}$ is independently $C_{2-6}$alkenyl. In embodiments of the formulae above, each $R^{6b}$ is independently $C_{2-6}$alkynyl. In embodiments of the formulae above, each $R^{6}\%$ is independently $C_{3-12}$cycloalkyl. In embodiments of the formulae above;

each $R^{6b}$ is independently $C_{2-11}$heterocycloalkyl. In embodiments of the formulae above, each $R^{6b}$ is independently $C_{6-10}$aryl. In embodiments of the formulae above, each $R^6b$ is independently $C_{1-9}$heteroaryl. In embodiments of the formulae above, each $R^{6b}$ is independently selected from —$OR^{12}$, —$SR^{12}$, —C(O)$OR^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2R^{15}$), —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$). In embodiments of the formulae above, each $R^{6}\%$ is independently $C_{1-6}$alkyl substituted with one, two, or three $R^{20}$c. In embodiments of the formulae above, each $R^{6b}$ is independently $C_{2-6}$alkenyl substituted with one, two, or three $R^{20}$e. In embodiments of the formulae above, each $R^{6b}$ is independently $C_{2-6}$alkynyl substituted with one, two, or three $R^{20}$e. In embodiments of the formulae above, each $R^{6b}$ is independently $C_{3-12}$cycloalkyl substituted with one, two, or three $R^{20}$e. In embodiments of the formulae above, each $R^{6b}$ is independently $C_{2-11}$heterocycloalkyl substituted with one, two, or three $R^{20}$c. In embodiments of the formulae above, each $R^{6b}$ is independently $C_{6-10}$aryl substituted with one, two, or three $R^{20}$e. In embodiments of the formulae above, each $R^6b$ is independently $C_{1-9}$heteroaryl substituted with one, two, or three $R^{20}$c. In embodiments of the formulae above, $R^6$ is independently $C_{1-6}$alkyl. In embodiments of the formulae above, $R^{6b}$ is independently methyl. In embodiments of the formulae above, $R^{6b}$ is independently ethyl. In embodiments of the formulae above, $R^6b$ is independently isopropyl. In embodiments of the formulae above, $R^{6b}$ is independently $C_{2-6}$alkenyl. In embodiments of the formulae above, $R^6$ is independently $C_{2-6}$alkynyl. In embodiments of the formulae above, $R^{6b}$ is independently $C_{1-6}$haloalkyl. In embodiments of the formulae above, $R^{6b}$ is independently —CF$_3$. In embodiments of the formulae above, $R^6b$ is independently $C_{6-12}$aryl. In embodiments of the formulae above, $R^6\%$ is independently $C_{1-11}$heteroaryl. In embodiments of the formulae above, $R^6b$ is independently selected from —OH, —OCH$_3$, —SH, —SCH$_3$, —C(O)OH, —C(O)OCH$_3$, —OC(O)N(H)$_2$, —OC(O)N(CH$_3$)$_2$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the compounds of the formulae above, or a pharmaceutically acceptable salt or solvate thereof, $R^6$ is selected from hydrogen, $C_{1-6}$alkyl, $C_{2-6}$alkenyl, $C_{2-6}$alkynyl, $C_{3-10}$cycloalkyl, and $C_{2-9}$heterocycloalkyl, wherein $C_{1-6}$alkyl, $C_2$-6alkenyl, $C_{2-6}$alkynyl, $C_{3-10}$cycloalkyl, and $C_{2-9}$heterocycloalkyl are optionally substituted with one, two, or three $R^{20}$e. In embodiments of the compounds of the formulae above, or a pharmaceutically acceptable salt or solvate thereof, $R^6b$ is selected from hydrogen, $C_{1-6}$alkyl, $C_{3-10}$cycloalkyl, and $C_{2-9}$heterocycloalkyl, wherein $C_{1-6}$alkyl, $C_{3-10}$cycloalkyl, and $C_{2-9}$heterocycloalkyl are optionally substituted with one, two, or three $R^{20}$c independently selected from halogen, $C_{1-6}$alkyl, $C_{2-6}$alkenyl, $C_{2-6}$alkynyl, $C_{3-10}$cycloalkyl, and $C_{2-9}$heterocycloalkyl. In embodiments of the compounds of the formulae above, or a pharmaceutically acceptable salt or solvate thereof, $R^6$b is selected from hydrogen, methyl, cyclopropyl, cyclobutyl, and oxetanyl, wherein said methyl, cyclopropyl, cyclobutyl, and oxetanyl are optionally substituted with one, two, or three $R^{20}$c independently selected from fluoro, methyl, cyclopropyl, cyclobutyl, and oxetanyl. In embodiments of the compounds of the formulae above, or a pharmaceutically acceptable salt or solvate thereof, $R^6b$ is selected from hydrogen, methyl, cyclopropyl, cyclobutyl, and oxetanyl. RIn embodiments of the compounds of the formulae above, or a pharmaceutically acceptable salt or solvate thereof, $R^{6b}$ is selected from $C_{1-6}$alkyl, $C_{3-10}$cycloalkyl, and $C_2$-heterocycloalkyl, wherein $C_{1-6}$alkyl, $C_{3-10}$cycloalkyl, and $C_{2-9}$heterocycloalkyl are optionally substituted with one, two, or three $R^{20}$c independently selected from halogen, $C_{1-6}$alkyl, $C_{2-6}$alkenyl, $C_{2-6}$alkynyl, $C_{3-10}$cycloalkyl, and $C_{2-9}$heterocycloalkyl. In embodiments of the compounds of the formulae above, or a pharmaceutically acceptable salt or solvate thereof, $R^{6b}$ is selected from methyl, cyclopropyl, cyclobutyl, and oxetanyl, wherein said methyl, cyclopropyl, cyclobutyl, and oxetanyl are optionally substituted with one, two, or three $R^{20}$c independently selected from fluoro, methyl, cyclopropyl, cyclobutyl, and oxetanyl. In embodiments of the compounds of the formulae above, or a pharmaceutically acceptable salt or solvate thereof, Rób is selected from methyl, cyclopropyl, cyclobutyl, and oxetanyl. In embodiments of the formulae above, each $R^6$b is independently —$OR^{12}$. In embodiments of the formulae above, each $R^{6b}$ is independently —$SR^{12}$. In embodiments of the formulae above, each $R^{6}b$ is independently —$C(O)OR^{12}$. In embodiments of the formulae above, each $R^{6}b$ is independently selected from —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, $R^{6b}$ is independently $C_{3-12}$cycloalkyl. In embodiments of the formulae above, $R^{6}b$ is independently $C_{2-11}$heterocycloalkyl. In embodiments of the formulae above, $R^{6b}$ is independently $C_{6-12}$aryl. In embodiments of the formulae above, $R^{6\%}$ is independently $C_{1-11}$heteroaryl. In embodiments of the formulae above, $R^{6}b$ is independently —OH. In embodiments of the formulae above, $R^{6b}$ is independently —$OCH_3$. In embodiments of the formulae above, $R^{6}b$ is independently —SH. In embodiments of the formulae above, $R^{6}b$ is independently —$SCH_3$. In embodiments of the formulae above, $R^{6b}$ is independently —C(O)OH. In embodiments of the formulae above, $R^{6}b$ is independently selected from —$C(O)OCH_3$ In embodiments of the formulae above, —$OC(O)N(H)_2$, —$OC(O)N(CH_3)_2$, —$C(O)CH_3$, —C(O)H, —$S(O)CH_3$, —$OC(O)CH_3$, —OC(O)H, —$C(O)N(CH_3)_2$, —$C(O)C(O)N(CH_3)_2$, —$S(O)_2CH_3$, —$S(O)_2N(H)_2$, —$S(O)_2N(CH_3)_2$, $S(=O)(=NH)N(H)_2$, $S(=O)(=NH)N(CH_3)_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2CH_3$, —$CH_2S(O)_2N(CH_3)_2$, and —$CH_2S(O)_2N(H)_2$. In embodiments, $R^{6}b$ is selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(H)(R^{12})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20}e$.

The individual embodiments herein below, or combinations thereof, (e.g., embodiments of $R^{7a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^{7a}$ is independently hydrogen. In embodiments of the formulae above, each $R^{7a}$ is independently halogen. In embodiments of the formulae above, each $R^{7a}$ is independently oxo. In embodiments of the formulae above, each $R^{7a}$ is independently —CN. In embodiments of the formulae above, each $R^{7a}$ is independently $C_{1-6}$alkyl. In embodiments of the formulae above, each $R^{7a}$ is independently $C_{2-6}$alkenyl. In embodiments of the formulae above, each $R^{7a}$ is independently $C_{2-6}$alkynyl. In embodiments of the formulae above, each $R^{7a}$ is independently $C_{3-12}$cycloalkyl. In embodiments of the formulae above, each $R^{7a}$ is independently $C_{2-11}$heterocycloalkyl. In embodiments of the formulae above, each $R^{7a}$ is independently $C_{6-10}$aryl. In embodiments of the formulae above, each $R^{7a}$ is independently $C_{1-9}$heteroaryl. In embodiments of the formulae above, each $R^{7a}$ is independently selected from —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^{7a}$ is independently $C_{1-6}$alkyl substituted with one, two, or three $R^{20}f$. In embodiments of the formulae above, each $R^{a}$ is independently $C_{2-6}$alkenyl substituted with one, two, or three $R^{20}f$. In embodiments of the formulae above, each $R^{7a}$ is independently $C_{2-6}$alkynyl substituted with one, two, or three $R^{20}f$. In embodiments of the formulae above, each $R^{7a}$ is independently $C_{3-12}$cycloalkyl substituted with one, two, or three $R^{20}f$. In embodiments of the formulae above, each $R^{7a}$ is independently $C_{2-11}$heterocycloalkyl substituted with one, two, or three $R^{20}f$. In embodiments of the formulae above, each $R^{7a}$ is independently $C_{6-10}$aryl substituted with one, two, or three $R^{20}f$. In embodiments of the formulae above, each $R^{7a}$ is independently $C_{1-9}$heteroaryl substituted with one, two, or three $R^{20}f$. In embodiments of the formulae above, $R^{7a}$ is independently F. In embodiments of the formulae above, $R^{7a}$ is independently $C_1$. In embodiments of the formulae above, $R^{7a}$ is independently Br. In embodiments of the formulae above, $R^{7a}$ is independently I. In embodiments of the formulae above, $R^{7a}$ is independently $C_{1-6}$alkyl. In embodiments of the formulae above, $R^{7a}$ is independently methyl. In embodiments of the formulae above, $R^{7a}$ is independently ethyl. In embodiments of the formulae above, $R^{7a}$ is independently isopropyl. In embodiments of the formulae above, $R^{7a}$ is independently $C_{2-6}$alkenyl. In embodiments of the formulae above, $R^{7a}$ is independently $C_{2-6}$alkynyl. In embodiments of the formulae above, $R^{7a}$ is independently $C_{1-6}$haloalkyl. In embodiments of the formulae above, $R^{7a}$ is independently —$CF_3$. In embodiments of the formulae above, $R^{7a}$ is independently $C_{6-12}$aryl. In embodiments of the formulae above, $R^{7a}$ is independently $C_{1-11}$heteroaryl. In embodiments of the formulae above, $R^{7a}$ is independently selected from —OH, —$OCH_3$, —SH, —$SCH_3$, —$N(CH_3)_2$, —$N(H)_2$, —C(O)OH, —$C(O)OCH_3$, —$OC(O)N(H)_2$, —$OC(O)N(CH_3)_2$, —$N(H)C(O)N(CH_3)_2$, —$N(H)C(O)N(H)_2$, —N(H)C(O)OH, —$N(H)C(O)OCH_3$, —$N(H)S(O)_2CH_3$, —$C(O)CH_3$, —C(O)H, —$S(O)CH_3$, —OC(O)$CH_3$, —OC(O)H, —$C(O)N(CH_3)_2$, —C(O)C(O)N$(CH_3)_2$, —N(H)C(O)H, —$N(H)C(O)CH_3$, —$S(O)_2CH_3$, —$S(O)_2N(H)_2$, —$S(O)_2N(CH_3)_2$, S(=O)(=NH)N(H)$_2$, S(=O)(=NH)N(CH$_3$)$_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2$ $CH_3$, —$CH_2S(O)_2N(CH_3)_2$, and —$CH_2S(O)_2N(H)_2$. In embodiments of the formulae above, each $R^{7a}$ is independently —$OR^{12}$. In embodiments of the formulae above, each $R^{7a}$ is independently —$SR^{12}$. In embodiments of the formulae above, each $R^{7a}$ is independently —$N(R^{12})(R^{13})$. In embodiments of the formulae above, each $R^{7a}$ is independently —$C(O)OR^{12}$. In embodiments of the formulae above, each $R^{7a}$ is independently selected from —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$—, —S(=O)(=NH)$N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, $R^{7a}$ is independently —OH. In embodiments of the formulae above, $R^{7a}$ is independently —$OCH_3$. In embodiments of the formulae above, $R^7a$ is independently —SH. In embodiments of the formulae above, $R^{7a}$ is independently —$SCH_3$. In embodiments of the formulae above, $R^7a$ is independently —$N(CH_3)_2$. In embodiments of the formulae above, $R^{7a}$ is independently —$N(H)_2$. In embodiments of the formulae above, $R^{7a}$ is independently —C(O)OH. In embodiments of the formulae above, $R^{7a}$ is independently selected from —$C(O)OCH_3$, —$OC(O)N(H)_2$, —$OC(O)N(CH_3)_2$, —$N(H)C(O)N(CH_3)_2$, —$N(H)C(O)N(H)_2$, —N(H)C(O)OH, —$N(H)C(O)OCH_3$, —N(H)C(O)$OCH_3$, —$N(H)S(O)_2CH_3$, —$C(O)CH_3$, —C(O)H, —$S(O)CH_3$, —$OC(O)CH_3$, —OC(O)H, —C(O)N$(CH_3)_2$, —C(O)C(O)N(CH$_3$)$_2$, —N(H)C(O)H, —N(H)C(O)CH$_3$, —$S(O)_2CH_3$, —$S(O)_2N(H)_2$, —$S(O)_2N(CH_3)_2$, S(=O)(=NH)N(H)$_2$, S(=O)(=NH)N(CH$_3$)$_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2CH_3$, —$CH_2S(O)_2N(CH_3)_2$, and —$CH_2S(O)_2N(H)_2$.

The individual embodiments herein below, or combinations thereof, (e.g., embodiments of $R^7c$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"- 1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^7c$ is independently hydrogen. In embodiments of the formulae above, each $R^7c$ is independently halogen. In embodiments of the formulae above, each $R^7c$ is independently oxo. In embodiments of the formulae above, each $R^7c$ is independently —CN. In embodiments of the formulae above, each $R^7c$ is independently $C_{1-6}$alkyl. In embodiments of the formulae above, each $R^7c$ is independently $C_{2-6}$alkenyl. In embodiments of the formulae above, each $R^7c$ is independently $C_{2-6}$alkynyl. In embodiments of the formulae above, each $R^7c$ is independently $C_{3-12}$cycloalkyl. In embodiments of the formulae above, each $R^7c$ is independently $C_{2-11}$heterocycloalkyl. In embodiments of the formulae above, each $R^7c$ is independently $C_{6-10}$aryl. In embodiments of the formulae above, each $R^7c$ is independently $C_{1-9}$heteroaryl. In embodiments of the formulae above, each $R^7c$ is independently selected from —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$—, —S(=O)(=NH)$N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^7c$ is independently $C_{1-6}$alkyl substituted with one, two, or three $R^{20}f$. In embodiments of the formulae above, each $R^7c$ is independently $C_{2-6}$alkenyl substituted with one, two, or three $R^{20}f$. In embodiments of the formulae above, each $R^7c$ is independently $C_{2-6}$alkynyl substituted with one, two, or three $R^{20}f$. In embodiments of the formulae above, each $R^7c$ is independently $C_{3-12}$cycloalkyl substituted with one, two, or three $R^{20}f$. In embodiments of the formulae above, each $R^7c$ is independently $C_{2-11}$heterocycloalkyl substituted with one, two, or three $R^{20}f$. In embodiments of the formulae above, each $R^7c$ is independently $C_{6-10}$aryl substituted with one, two, or three $R^{20}f$. In embodiments of the formulae above, each $R^7c$ is independently $C_{1-9}$heteroaryl substituted with one, two, or three $R^{20}$f. In embodiments of the formulae above, $R^7$c is independently F. In embodiments of the formulae above, $R^7$c is independently $C_1$. In embodiments of the formulae above, $R^7$c is independently Br. In embodiments of the formulae above, $R^7$c is independently I. In embodiments of the formulae above, $R^7$c is independently $C_{1-6}$alkyl. In embodiments of the formulae above, $R^7$c is independently methyl. In embodiments of the formulae above, $R^7$c is independently ethyl. In embodiments of the formulae above, $R^7$c is independently isopropyl. In embodiments of the formulae above, $R^7$c is independently $C_{2-6}$alkenyl. In embodiments of the formulae above, $R^7$c is independently $C_{2-6}$alkynyl. In embodiments of the formulae above, $R^7$c is independently $C_{1-6}$haloalkyl. In embodiments of the formulae above, $R^7$c is independently —$CF_3$. In embodiments of the formulae above, $R^7$c is independently $C_{6-12}$aryl. In embodiments of the formulae above, $R^7$c is independently $C_{1-11}$heteroaryl. In embodiments of the formulae above, $R^7$c is independently selected from —OH, —$OCH_3$, —SH, —$SCH_3$, —$N(CH_3)_2$, —$N(H)_2$, —C(O)OH, —C(O)$OCH_3$, —OC(O)$N(H)_2$, —OC(O)$N(CH_3)_2$, —N(H)C(O)$N(CH_3)_2$, —N(H)C(O)$N(H)_2$, —N(H)C(O)OH, —N(H)C(O)$OCH_3$, —N(H)S(O)$_2$$CH_3$, —C(O)$CH_3$, —C(O)H, —S(O)$CH_3$, —OC(O)$CH_3$, —OC(O)H, —C(O)$N(CH_3)_2$, —C(O)C(O)N$(CH_3)_2$, —N(H)C(O)H, —N(H)C(O)$CH_3$, —S(O)$_2$$CH_3$, —S(O)$_2$$N(H)_2$, —S(O)$_2$$N(CH_3)_2$, S(=O)(=NH)$N(H)_2$, S(=O)(=NH)$N(CH_3)_2$, —$CH_2$C(O)$N(H)_2$, —$CH_2$C(O)$N(CH_3)_2$, —$CH_2$N(H)C(O)H, —$CH_2$N(H)C(O)$CH_3$, —$CH_2$S(O)$_2$H, —$CH_2$S(O)$_2$ $CH_3$, —$CH_2$S(O)$_2$$N(CH_3)_2$, and —$CH_2$S(O)$_2$$N(H)_2$. In embodiments of the formulae above, each $R^7$c is independently —$OR^{12}$. In embodiments of the formulae above, each $R^7$ is independently —$SR^{12}$. In embodiments of the formulae above, each $R^7$c is independently —N($R^{12}$)($R^{13}$). In embodiments of the formulae above, each $R^7$c is independently —C(O)$OR^{12}$. In embodiments of the formulae above, each $R^7$c is independently selected from —OC(O)N($R^{12}$)($R^{13}$) In embodiments of the formulae above, —N($R^{14}$)C(O)N($R^{12}$)($R^{13}$) In embodiments of the formulae above, —N($R^{14}$)C(O)$OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2$$R^{15}$, and —$CH_2$S(O)$_2$N($R^{12}$)($R^{13}$). In embodiments of the formulae above, $R^7$c is independently —OH. In embodiments of the formulae above, $R^7$c is independently —$OCH_3$. In embodiments of the formulae above, $R^7$c is independently —SH. In embodiments of the formulae above, $R^7$c is independently —$SCH_3$. In embodiments of the formulae above, $R^7$c is independently —$N(CH_3)_2$. In embodiments of the formulae above, $R^7$c is independently —$N(H)_2$. In embodiments of the formulae above, $R^7$c is independently —C(O)OH. In embodiments of the formulae above, $R^7$c is independently selected from —C(O)$OCH_3$, —OC(O)$N(H)_2$, —OC(O)$N(CH_3)_2$, —N(H)C(O)$N(CH_3)_2$, —N(H)C(O)$N(H)_2$, —N(H)C(O)OH, —N(H)C(O)$OCH_3$, —N(H)S(O)$_2$$CH_3$, —OC(O)H, —C(O)H, —S(O)$CH_3$, —OC(O)$CH_3$, —OC(O)H, —C(O)N($CH_3)_2$, —C(O)C(O)N$(CH_3)_2$, —N(H)C(O)H, —N(H)C(O)$CH_3$, —S(O)$_2$$CH_3$, —S(O)$_2$$N(H)_2$, —S(O)$_2$$N(CH_3)_2$, S(=O)(=NH)$N(H)_2$, S(=O)(=NH)$N(CH_3)_2$, —$CH_2$C(O)$N(H)_2$, —$CH_2$C(O)$N(CH_3)_2$, —$CH_2$N(H)C(O)H, —$CH_2$N(H)C(O)$CH_3$, —$CH_2$S(O)$_2$H, —$CH_2$S(O)$_2$$CH_3$, —$CH_2$S(O)$_2$$N(CH_3)_2$, and —$CH_2$S(O)$_2$$N(H)_2$.

The individual embodiments herein below, or combinations thereof, (e.g., embodiments of $R^7$d) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''- 1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each $R^7$d is independently hydrogen. In embodiments of the formulae above, each $R^7$d is independently —CN. In embodiments of the formulae above, each $R^7$d is independently $C_{1-6}$alkyl. In embodiments of the formulae above, each $R^7$d is independently $C_{2-6}$alkenyl. In embodiments of the formulae above, each $R^7$d is independently $C_{2-6}$alkynyl. In embodiments of the formulae above, each $R^7$d is independently $C_{3-12}$cycloalkyl. In embodiments of the formulae above;

each $R^7$d is independently $C_{2-11}$heterocycloalkyl. In embodiments of the formulae above, each $R^7$d is independently $C_{6-10}$aryl. In embodiments of the formulae above, each $R^7$d is independently $C_{1-9}$heteroaryl. In embodiments of the formulae above, each $R^7$d is independently selected from —$OR^{12}$, —$SR^{12}$, —C(O)$OR^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —C(O)C(O)N($R^{12}$)($R^{13}$), —S(O)$_2$$R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2$$R^{15}$, and —$CH_2$S(O)$_2$N($R^{12}$)($R^{13}$). In embodiments of the formulae above, each $R^7$d is independently $C_{1-6}$ alkyl substituted with one, two, or three $R^{20}$f. In embodiments of the formulae above, each $R^7$d is independently $C_{2-6}$alkenyl substituted with one, two, or three $R^{20}$f. In embodiments of the formulae above, each $R^7$d is independently $C_{2-6}$alkynyl substituted with one, two, or three $R^{20}$f. In embodiments of the formulae above, each $R^7d$ is independently $C_{3-12}$cycloalkyl substituted with one, two, or three $R^{20}f$. In embodiments of the formulae above, each $R^7d$ is independently $C_{2-11}$heterocycloalkyl substituted with one, two, or three $R^{20}f$. In embodiments of the formulae above, each $R^7d$ is independently $C_{6-10}$aryl substituted with one, two, or three $R^{20}f$. In embodiments of the formulae above, each $R^7d$ is independently $C_{1-9}$heteroaryl substituted with one, two, or three $R^{20}f$. In embodiments of the formulae above, $R^7d$ is independently $C_{1-6}$alkyl. In embodiments of the formulae above, $R^7d$ is independently methyl. In embodiments of the formulae above, $R^7d$ is independently ethyl. In embodiments of the formulae above, $R^{7d}$ is independently isopropyl. In embodiments of the formulae above, $R^7d$ is independently $C_{2-6}$alkenyl. In embodiments of the formulae above, $R^7d$ is independently $C_{2-6}$alkynyl. In embodiments of the formulae above, $R^7d$ is independently $C_{1-6}$haloalkyl. In embodiments of the formulae above, $R^7d$ is independently —$CF_3$, In embodiments of the formulae above, $R^7d$ is independently $C_{6-12}$aryl. In embodiments of the formulae above, $R^7d$ is independently $C_{1-11}$heteroaryl. In embodiments of the formulae above, $R^7d$ is independently selected from —OH, —$OCH_3$, —SH, —$SCH_3$, —C(O)OH, —C(O)$OCH_3$, —OC(O)N(H)$_2$, —OC(O)N($CH_3$)$_2$, —C(O)$CH_3$, —C(O)H, —S(O)$CH_3$, —OC(O)$CH_3$, —OC(O)H, —C(O)N($CH_3$)$_2$, —C(O)C(O)N($CH_3$)$_2$, —S(O)$_2CH_3$, —S(O)$_2$N(H)$_2$, —S(O)$_2$N($CH_3$)$_2$, S(=O)(=NH)N(H)$_2$, S(=O)(=NH)N($CH_3$)$_2$, —$CH_2$C(O)N(H)$_2$, —$CH_2$C(O)N($CH_3$)$_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2$N($CH_3$)$_2$, and —$CH_2$S(O)$_2$N(H)$_2$. In embodiments of the formulae above, each $R^7d$ is independently —$OR^{12}$. In embodiments of the formulae above;

each $R^7d$ is independently —$SR^{12}$. In embodiments of the formulae above, each $R^7d$ is independently —C(O)$OR^{12}$. In embodiments of the formulae above, each $R^7d$ is independently selected from —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —C(O)C(O)N($R^{12}$)($R^{13}$), —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$). In embodiments of the formulae above, $R^7d$ is independently —OH. In embodiments of the formulae above, $R^7d$ is independently —$OCH_3$. In embodiments of the formulae above, $R^7d$ is independently —SH. In embodiments of the formulae above, $R^7d$ is independently —$SCH_3$. In embodiments of the formulae above, $R^7d$ is independently —C(O)OH. In embodiments of the formulae above, Rød is independently selected from —C(O)$OCH_3$, —OC(O)N(H)$_2$, —OC(O)N($CH_3$)$_2$, —C(O)$CH_3$, —C(O)H, —S(O)$CH_3$, —OC(O)$CH_3$, —OC(O)H, —C(O)N($CH_3$)$_2$, —C(O)C(O)N($CH_3$)$_2$, —S(O)$_2CH_3$, —S(O)$_2$N(H)$_2$, —S(O)$_2$N($CH_3$)$_2$, S(=O)(=NH)N(H)$_2$, S(=O)(=NH)N($CH_3$)$_2$, —$CH_2$C(O)N(H)$_2$, —$CH_2$C(O)N($CH_3$)$_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2$N($CH_3$)$_2$, and —$CH_2$S(O)$_2$N(H)$_2$.

The individual embodiments herein below, or combinations thereof, (e.g., embodiments of $R^{17}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"- 1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, or a pharmaceutically acceptable salt or solvate thereof, $R^{17}$ is a monocyclic ring. In embodiments of the compounds of the formulae above, or a pharmaceutically acceptable salt or solvate thereof, $R^{17}$ is a bicyclic ring system. In embodiments of the compounds of the formulae above, or a pharmaceutically acceptable salt or solvate thereof, $R^{17}$ is a polycyclic ring system.

In select embodiments of the compound, $R^{17}$ is a $C_{3-12}$cycloalkyl optionally substituted with one, two, or three $R^{20g}$. In embodiments of the compounds of the formulae above, $R^{17}$ is a $C_{2-11}$heterocycloalkyl optionally substituted with one, two, or three $R^{20g}$. In embodiments of the compounds of the formulae above, $R^{17}$ is a $C_{6-12}$aryl optionally substituted with one, two, or three $R^{20g}$. In embodiments of the compounds of the formulae above, $R^{17}$ is a $C_{2-12}$heteroaryl optionally substituted with one, two, or three $R^{20g}$. In embodiments of the compounds of the formulae above, $R^{17}$ is a $C_{3-12}$cycloalkyl. In select embodiments of the compound, $R^{17}$ is a $C_{2-11}$heterocycloalkyl. In embodiments of the compounds of the formulae above, $R^{17}$ is a $C_{6-12}$aryl. In embodiments of the compounds of the formulae above, $R^{17}$ is a $C_{2-12}$heteroaryl. In embodiments of the compounds of the formulae above, or a pharmaceutically acceptable salt or solvate thereof, $R^{17}$ is a monocyclic $C_{3-9}$cycloalkyl optionally substituted with one, two, or three $R^{20g}$. In embodiments of the compounds of the formulae above, or a pharmaceutically acceptable salt or solvate thereof, $R^{17}$ is a monocyclic $C_{1-8}$heterocycloalkyl optionally substituted with one, two, or three $R^{20g}$. In embodiments of the compounds of the formulae above, or a pharmaceutically acceptable salt or solvate thereof, $R^{17}$ is a monocyclic phenyl optionally substituted with one, two, or three $R^{20g}$. In embodiments of the compounds of the formulae above, or a pharmaceutically acceptable salt or solvate thereof, $R^{17}$ is a monocyclic $C_{1-5}$heteroaryl optionally substituted with one, two, or three $R^{20g}$. In embodiments of the compounds of the formulae above, or a pharmaceutically acceptable salt or solvate thereof, $R^{17}$ is a spirocyclic $C_{5-12}$cycloalkyl optionally substituted with one, two, or three $R^{20g}$. In embodiments of the compounds of the formulae above, or a pharmaceutically acceptable salt or solvate thereof, $R^{17}$ is a spirocyclic $C_{2-11}$heterocycloalkyl optionally substituted with one, two, or three $R^{20g}$. In embodiments of the compounds of the formulae above, or a pharmaceutically acceptable salt or solvate thereof, $R^{17}$ is a fused $C_{5-12}$cycloalkyl optionally substituted with one, two, or three $R^{20g}$. In embodiments of the compounds of the formulae above, or a pharmaceutically acceptable salt or solvate thereof, $R^{17}$ is a fused $C_{2-11}$heterocycloalkyl optionally substituted with one, two, or three $R^{20g}$. In embodiments of the compounds of the formulae above, or a pharmaceutically acceptable salt or solvate thereof, $R^{17}$ is a fused $C_{6-12}$aryl, optionally substituted with one, two, or three $R^{20g}$. In embodiments of the compounds of the formulae above, or a pharmaceutically acceptable salt or solvate thereof, $R^{17}$ is a fused 5 to 12 membered heteroaryl optionally substituted with one, two, or three $R^{20g}$.

In embodiments of the compounds of the formulae above, or a pharmaceutically acceptable salt or solvate thereof,

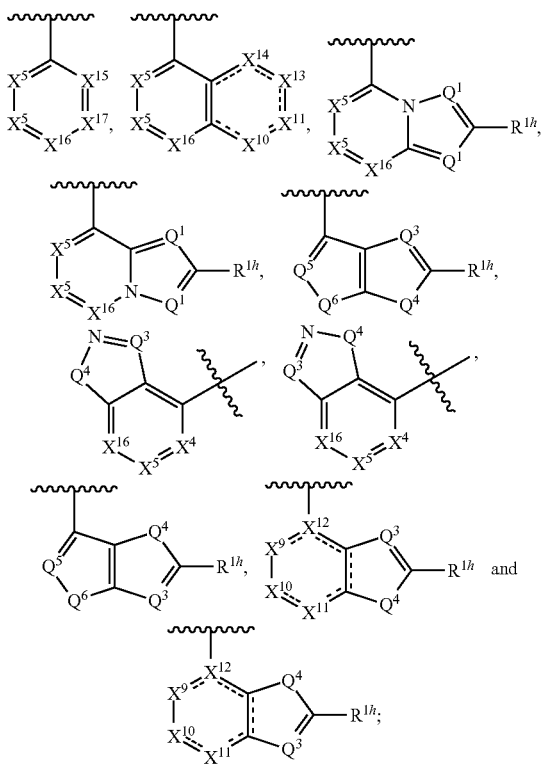

$R^{17}$ is selected from:
$Q^1$, $Q^3$, and $Q^5$ are independently N or $C(R^1d)$; $Q^4$ and $Q^6$ are independently O, S, $C(R^{1a})(R^1b)$, or $N(R^1c)$;
$X^4$, $X^5$, $X^{16}$, $X^{17}$, and $X^{15}$ are independently selected from $C(R^{1a})$ or N;
$X^9$ is bond, $C(R^{1a})$, N, $C(O)$, $C(R^{1a})(R^1b)$, $C(O)C(R^{1a})(R^1b)$, $C(R^{1a})(R^1b)C(R^{1a})(R^1b)$, $C(R^{1a})(R^1b)N(R^1c)$, or $N(R^1c)$ $X^{10}$, $X^{11}$, $X^{13}$, and $X^{14}$ are independently $C(O)$, $C(R^{1a})$, N, $C(R1a)(R^1b)$, or $N(R^1c)$;
$X^{12}$ is C, N, or $C(R^{1a})$;
each $R^{1a}$, $R^{1b}$, $R^{1d}$, and $R^1h$ is independently selected from from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-6}$heteroaryl, —$OR^{12}$, —$SR^{12}$, —$N(R^{12})(R^{13})$, —$C(O)OR^{12}$, —OC (O)$N(R^{12})(R^{13})$, —$N(R^{14})C(O)N(R^{12})(R^{13})$, —$N(R^{14})$ $C(O)OR^{15}$, —$N(R^{14})S(O)_2R^{15}$, —$C(O)R^{15}$, —$S(O)$ $R^{15}$, —$OC(O)R^{15}$, —$C(O)N(R^{12})(R^{13})$, —$C(O)C(O)N$ $(R^{12})(R^{13})$, —$N(R^{14})C(O)R^{15}$, —$S(O)_2R^{15}$, —$S(O)_2N$ $(R^{12})(R^{13})$—, $S(=O)(=NH)N(R^{12})(R^{13})$, —$CH_2C(O)$ $N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{207}$;

$R^1c$ is independently selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20}z$.

each $R^{207}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_6$-10aryl, —$CH_2$-$C_{1-9}$heteroaryl, $C_{1-9}$heteroaryl, —$OR^{21a}$, —$SR^{21a}$, —$N(R^{22a})(R^{23a})$, —$C(O)OR^{22a}$, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, —$OCH_2C(O)OR^{22a}$, and —$OC(O)R^{25a}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_6$-10aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21a}$, —$SR^{21a}$, —$N(R^{22a})(R^{23a})$, —$C(O)$ $OR^{22a}$, —$C(O)N(R^{22a})(R^{23a})$, —$C(O)C(O)N(R^{22a})(R^{23a})$, —$OC(O)N(R^{22a})(R^{23a})$, —$N(R^{24})C(O)N(R^{22a})(R^{23a})$, —$N(R^{24a})C(O)OR^{25a}$, —$N(R^{24a})C(O)R^{25a}$, —$N(R^{24a})S$ $(O)_2R^{25a}$, —$C(O)R^{25a}$, —$S(O)_2R^{25a}$, —$S(O)_2N(R^{22a})$ $(R^{23a})$, and —$OC(O)R^{25}a$;

each $R^{21a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23a}$ is independently selected from H and $C_{1-6}$alkyl;
each $R^{24}a$ is independently selected from H and $C_{1-6}$alkyl; and each $R^{25}a$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl.

The individual embodiments herein below, or combinations thereof, (e.g., embodiments of $Q^1$, $Q^3$, $Q^5$, $Q^4$, $Q^6$, $X^4$, $X^5$, $X^{16}$, $X^{17}$, $X^{15}$, $X^9$, $X^{10}$, $X^{11}$, $X^{13}$, $X^{14}$, and $X^{12}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $Q^1$ is N. In embodiments of the formulae above, $Q^1$ is $C(R^1d)$. In embodiments of the formulae above, $Q^3$ is N. In embodiments of the formulae above, $Q^3$ is $C(R^1d)$. In embodiments of the formulae above, $Q^5$ is N. In embodiments of the formulae above, $Q^5$ is $C(R^1d)$. In embodiments of the formulae above, $Q^4$ is O. In embodiments of the formulae above, $Q^4$ is S. In embodiments of the formulae above, $Q^4$ is $C(R^{1a})(R^1b)$. In embodiments of the formulae above, $Q^4$ is $N(R^1c)$. In embodiments of the formulae above, $Q^6$ is O. In embodiments of the formulae above, $Q^6$ is S. In embodiments of the formulae above, $Q^6$ is $C(R^{1a})(R^1b)$. In embodiments of the formulae above, $Q^6$ is $N(R^1c)$. In embodiments of the formulae above, $X^4$ is $C(R^{1a})$. In embodiments of the formulae above, $X^4$ is N. In embodiments of the formulae above, $X^5$ is $C(R^{1a})$. In embodiments of the formulae above, $X^5$ is N. In embodiments of the formulae above, $X^{16}$ is $C(R^{1a})$. In embodiments of the formulae above, $X^{16}$ is N. In embodiments of the formulae above, $X^{17}$ is $C(R^{1a})$. In embodiments of the formulae above, $X^{17}$ is N. In embodiments of the formulae above, $X^{15}$ is $C(R^{1a})$. In embodiments of the formulae above, $X^{15}$ is N. In embodiments of the formulae above, $X^9$ is a bond. In embodiments of the formulae above, $X^9$ is $C(R^{1a})$. In embodiments of the formulae above, $X^9$ is N. In embodiments of the formulae above, $X^9$ is C(O). In embodiments of the formulae above, $X^9$ is $C(R^{1a})(R^1b)$. In embodiments of the formulae above, $X^9$ is $C(O)C(R^{1a})(R^1b)$. In embodiments of the formulae above, $X^9$ is $C(R^{1a})(R^1b)C(R^{1a})(R^1b)$. In embodiments of the formulae above, $X^9$ is $C(R^{1a})(R^1b)N(R^1c)$. In embodiments of the formulae above, $X^9$ is $N(R^1c)$. In embodiments of the formulae above, $X^{10}$ is C(O). In embodiments of the formulae above, $X^{10}$ is $C(R^{1a})$. In embodiments of the formulae above, $X^{10}$ is N. In embodiments of the formulae above, $X^{10}$ is $C(R^{1a})(R^1b)$. In embodiments of the formulae above, $X^{10}$ is $N(R^1c)$. In embodiments of the formulae above, $X^{11}$ is C(O). In embodiments of the formulae above, $X^{11}$ is $C(R^{1a})$. In embodiments of the formulae above, $X^{11}$ is $C(R^{1a})(R^1b)$. In embodiments of the formulae above, $X^{11}$ is N. In embodiments of the formulae above, $X^{11}$ is $N(R^1c)$. In embodiments of the formulae above, $X^{13}$ is C(O). In embodiments of the formulae above, $X^{13}$ is $C(R^{1a})$. In embodiments of the formulae above, $X^{13}$ is $C(R^{1a})(R^1b)$. In embodiments of the formulae above, $X^{13}$ is N. In embodiments of the formulae above, $X^{13}$ is $N(R^1c)$. In embodiments of the formulae above, $X^{14}$ is C(O). In embodiments of the formulae above, $X^{14}$ is $C(R^{1a})$. In embodiments of the formulae above, $X^{14}$ is $C(R^{1a})(R^1b)$. In embodiments of the formulae above, $X^{14}$ is N. In embodiments of the formulae above, $X^{14}$ is $N(R^1c)$. In embodiments of the formulae above, $X^{12}$ is C. In embodiments of the formulae above, $X^{12}$ is N. In embodiments of the formulae above, $X^{12}$ is $C(R^{1a})$. In embodiments of the formulae above, $X^9$, $X^{10}$, and $X^{11}$ are independently C(O), $C(R^{1a})$, or $C(R^{1a})(R^1b)$. In embodiments of the formulae above, $X^{12}$ is C, N, or $C(R^{1a})$. In embodiments of the formulae above, $X^7$ is $C(R^{1a})$. In embodiments of the formulae above, $X^7$ is N. In embodiments of the formulae above, $X^6$ is C. In embodiments of the formulae above, $X^6$ is $C(R^{1a})$. In embodiments of the formulae above, $X^7$ is C. In embodiments of the formulae above, $X^7$ is $C(R^{1a})$. In embodiments of the formulae above, $X^8$ is C. In embodiments of the formulae above, $X^8$ is $C(R^{1a})$.

In embodiments of the compounds of the formulae above, or a pharmaceutically acceptable salt or solvate thereof, $R^{17}$ is selected from:

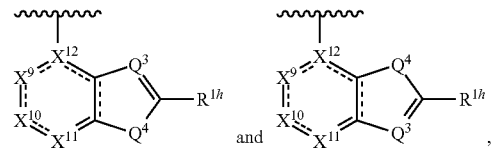

$Q^3$ is N or $C(R^1d)$; $Q^4$ is O or S;

each $R^{1a}$, $R^{1b}$, $R^{1d}$, and $R^1h$ is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, and $C_{1-9}$heteroaryl are optionally substituted with one, two, or three $R^{20}z$;

each $R^{20}z$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_6$-10aryl, —$CH_2$-$C_{1-9}$heteroaryl, $C_{1-9}$heteroaryl, —$OR^{21a}$, —$SR^{21a}$, —$N(R^{22a})(R^{23a})$, —$C(O)OR^{22a}$, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, —$OCH_2C(O)OR^{22a}$, and —$OC(O)R^{25a}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_6$-10aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21a}$, —SR$^{21a}$, —N(R$^{22a}$)(R$^{23a}$), —C(O)OR$^{22a}$, —C(O)N(R$^{22a}$)(R$^{23a}$), —C(O)C(O)N(R$^{22a}$)(R$^{23a}$), —OC(O)N(R$^{22a}$)(R$^{23a}$), —N(R$^{24}$)C(O)N(R$^{22a}$)(R$^{23a}$), —N(R$^{24a}$)C(O)OR$^{25a}$, —N(R$^{24a}$)C(O)R$^{25a}$, —N(R$^{24a}$)S(O)$_2$R$^{25a}$, —C(O)R$^{25a}$, —S(O)$_2$R$^{25a}$, —S(O)$_2$N(R$^{22a}$)(R$^{23a}$), and —OC(O)R$^{25}$a;

each R$^{21a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{22a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{23a}$ is independently selected from H and $C_{1-6}$alkyl;
each R$^{24a}$ is independently selected from H and $C_{1-6}$alkyl; and
each R$^{25a}$ is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl.

In embodiments of the formulae above, R$^{17}$ is selected from:

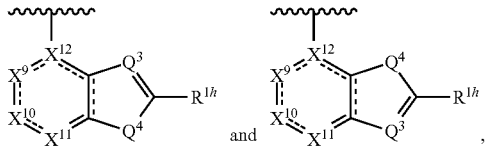

$Q^3$ is N or C(R$^1$d); $Q^4$ is O or S;
$X^9$, $X^{10}$, and $X^{11}$ are independently C(O), C(R$^{1a}$), or C(R$^{1a}$)(R$^1$b);
$X^{12}$ is C, N, or C(R$^{1a}$);
each R$^{1a}$, R$^{1b}$, R$^{1d}$, and R$^1$h is independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —C(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—,S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{207;}$ each R$^{20}$z is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6}$-10aryl, —CH$_2$-C$_{1-9}$heteroaryl, $C_{1-9}$heteroaryl, —OR$^{21a}$, —SR$^{21a}$, —N(R$^{22a}$)(R$^{23a}$), —C(O)OR$^{22a}$, —C(O)N(R$^{22a}$)(R$^{23a}$), —C(O)C(O)N(R$^{22a}$)(R$^{23a}$), —OC(O)N(R$^{22a}$)(R$^{23a}$), —N(R$^{24a}$)C(O)N(R$^{22a}$)(R$^{23a}$), —N(R$^{24a}$)C(O)OR$^{25a}$, —N(R$^{24a}$)C(O)R$^{25a}$, —N(R$^{24a}$)S(O)$_2$R$^{25a}$, —C(O)R$^{25a}$, —S(O)$_2$R$^{25a}$, —S(O)$_2$N(R$^{22a}$)(R$^{23a}$), —OCH$_2$C(O)OR$^{22a}$, and —OC(O)R$^{25a}$, wherein $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6}$-10aryl, —CH$_2$-C$_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21a}$, —SR$^{21a}$, —N(R$^{22a}$)(R$^{23a}$), —C(O)OR$^{22a}$, —C(O)N(R$^{22a}$)(R$^{23a}$), —C(O)C(O)N(R$^{22a}$)(R$^{23a}$), —OC(O)N(R$^{22a}$)(R$^{23a}$), —N(R$^{24}$)C(O)N(R$^{22a}$)(R$^{23a}$), —N(R$^{24a}$)C(O)OR$^{25a}$, —N(R$^{24a}$)C(O)R$^{25a}$, —N(R$^{24a}$)S(O)$_2$R$^{25a}$, —C(O)R$^{25a}$, —S(O)$_2$R$^{25a}$, —S(O)$_2$N(R$^{22a}$)(R$^{23a}$), and —OC(O)R$^{25}$a;

each R$^{21}$a is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{22a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{23a}$ is independently selected from H and $C_{1-6}$alkyl;
each R$^{24}$a is independently selected from H and $C_{1-6}$alkyl; and
each R$^{25}$a is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl.

The individual embodiments herein below, or combinations thereof, (e.g., embodiments of $Q^3$, $Q^4$, $X^9$, $X^{10}$, $X^{11}$, and $X^{12}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'- 1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''- 1a), (A''-1b), (B''-1b), (C''-1b), (A''-1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, $Q^3$ is N. In embodiments of the formulae above, $Q^3$ is C(R$^1$d). In embodiments of the formulae above, $Q^4$ is O. In embodiments of the formulae above, $Q^4$ is S. In embodiments of the formulae above, $X^9$ is C(R$^{1a}$). In embodiments of the formulae above, $X^9$ is C(O). In embodiments of the formulae above, $X^9$ is C(R$^{1a}$)(R$^1$b). In embodiments of the formulae above, $X^{10}$ is C(O). In embodiments of the formulae above, $X^{10}$ is C(R$^{1a}$). In embodiments of the formulae above, $X^{10}$ is $C(R^1)(R^{15})$. In embodiments of the formulae above, $X^{11}$ is $C(O)$. In embodiments of the formulas above, $X^{11}$ is $C(R^{14})$. In embodiments of the formulae above, $X^{11}$ is $C(R^1)(R^{15})$. In embodiments of the formulae above, $X^{12}$ is C. In embodiments of the formulae above, $X^{12}$ is N. In embodiments of the formulae above, $X^{12}$ is $C(R^1)$.

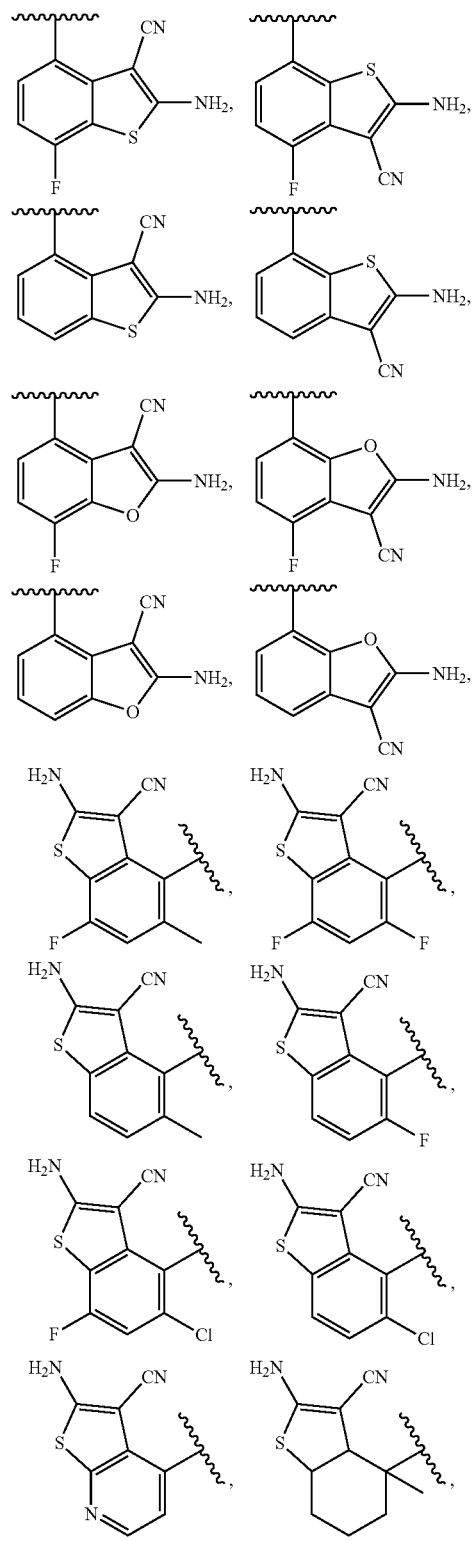

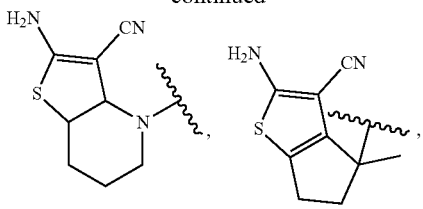

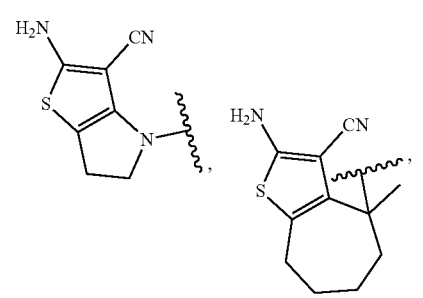

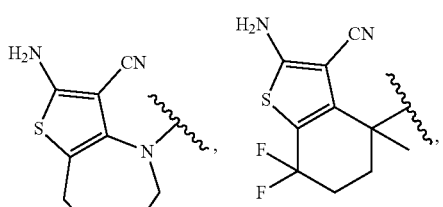

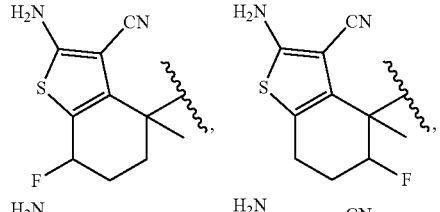

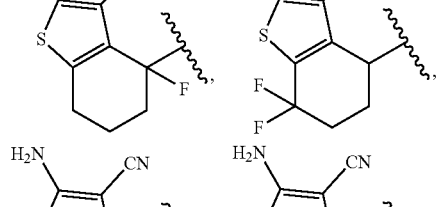


In embodiments of the compounds of the formulae above, $R^{17}$ is selected from

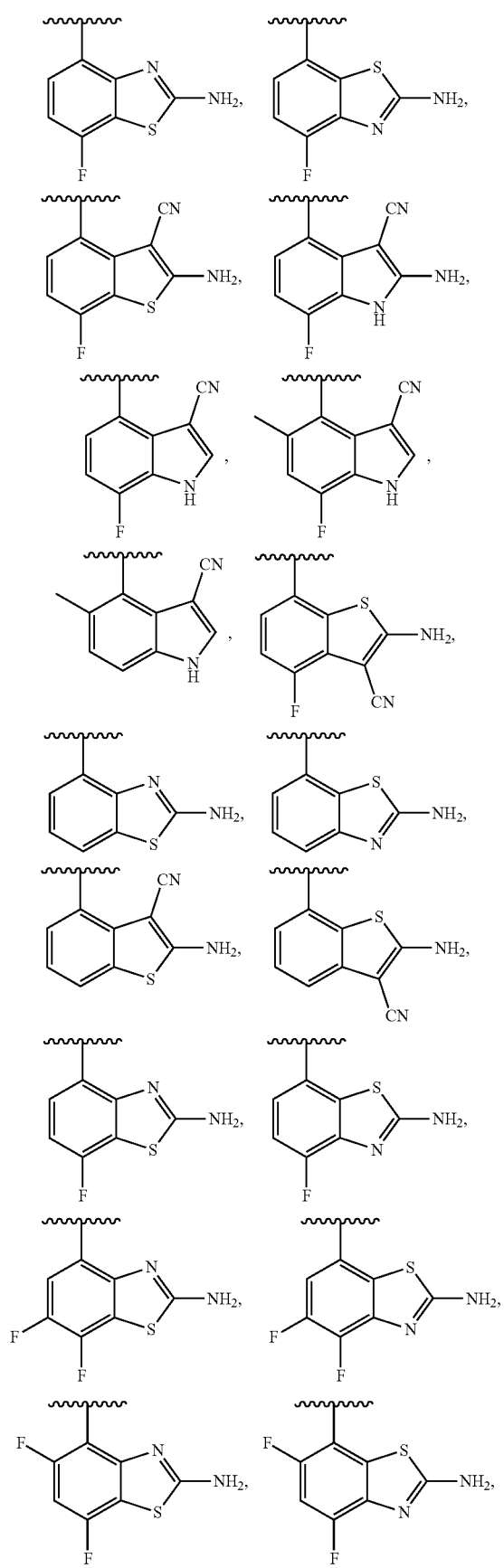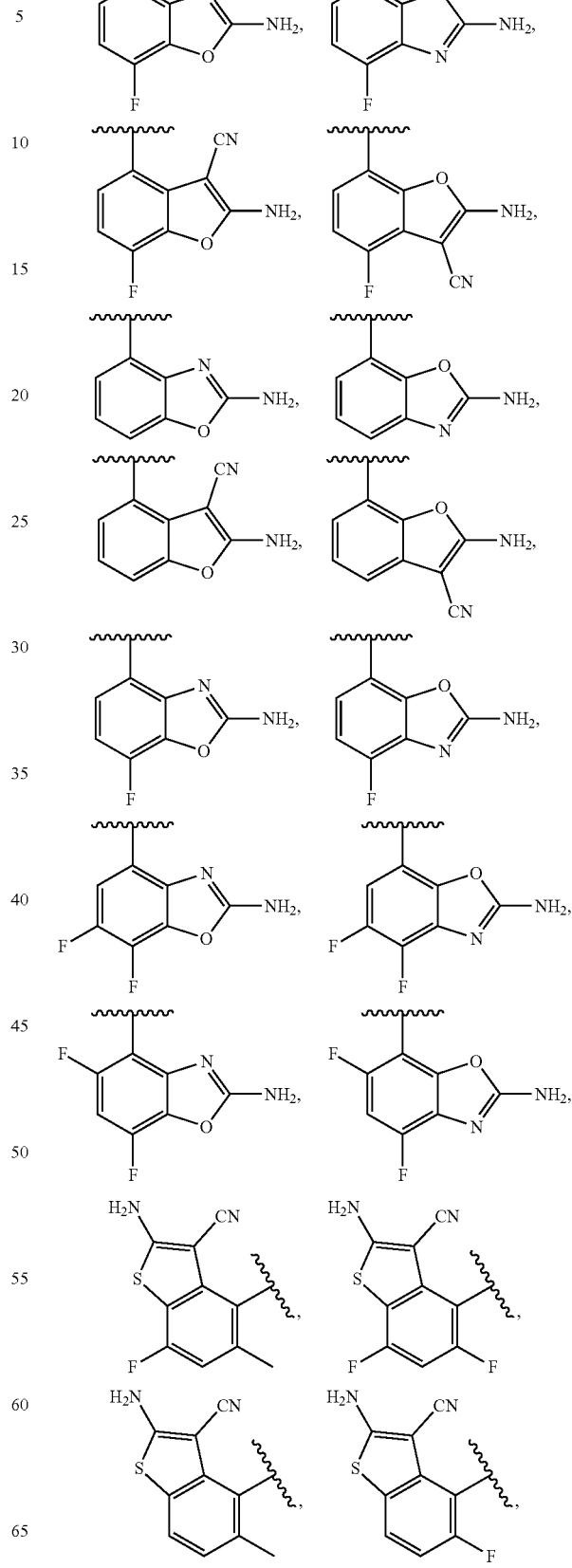

-continued
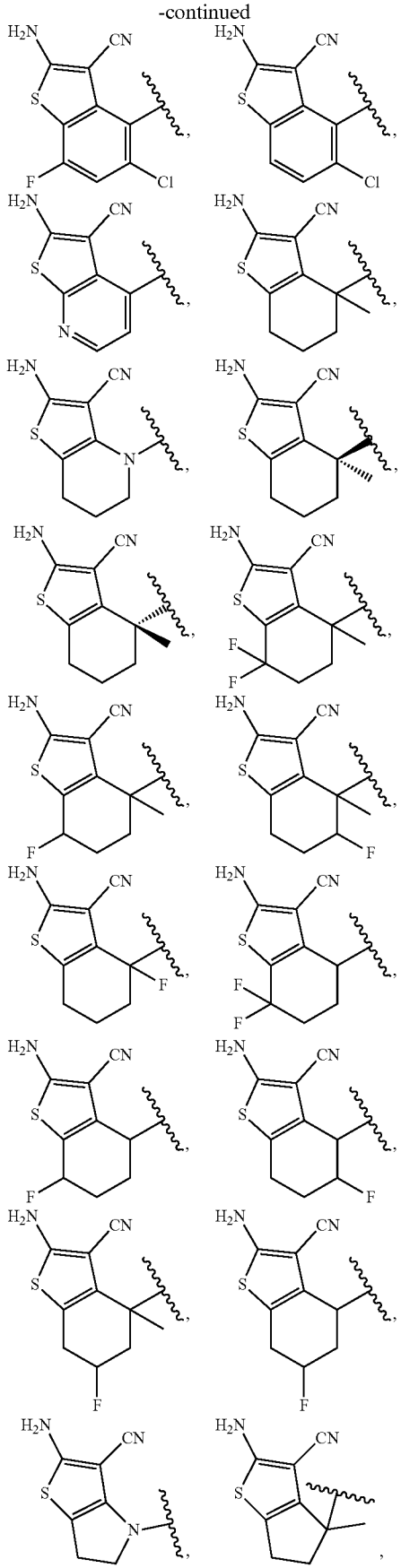
-continued
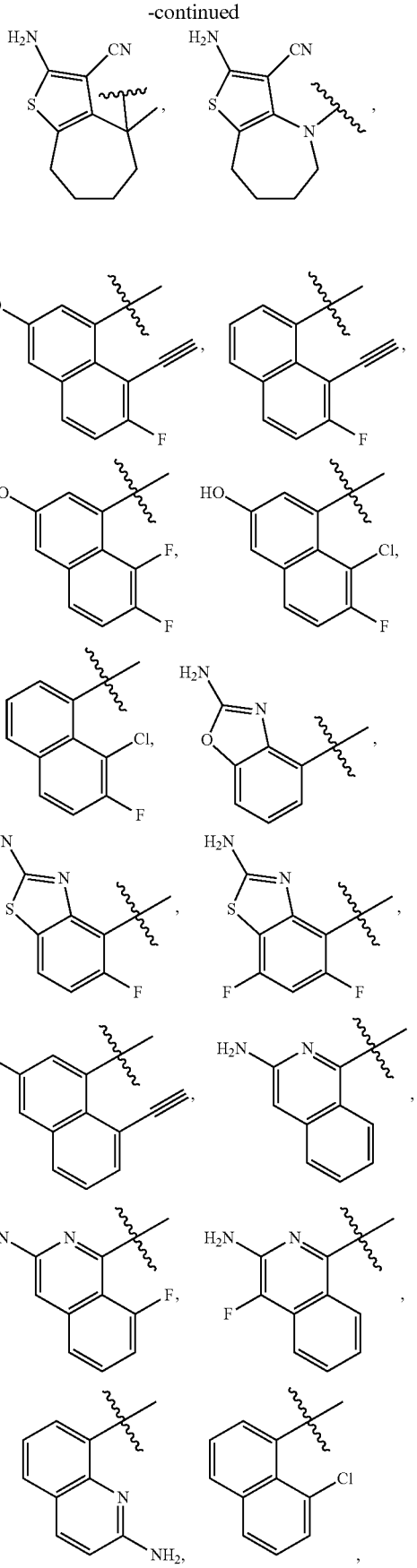

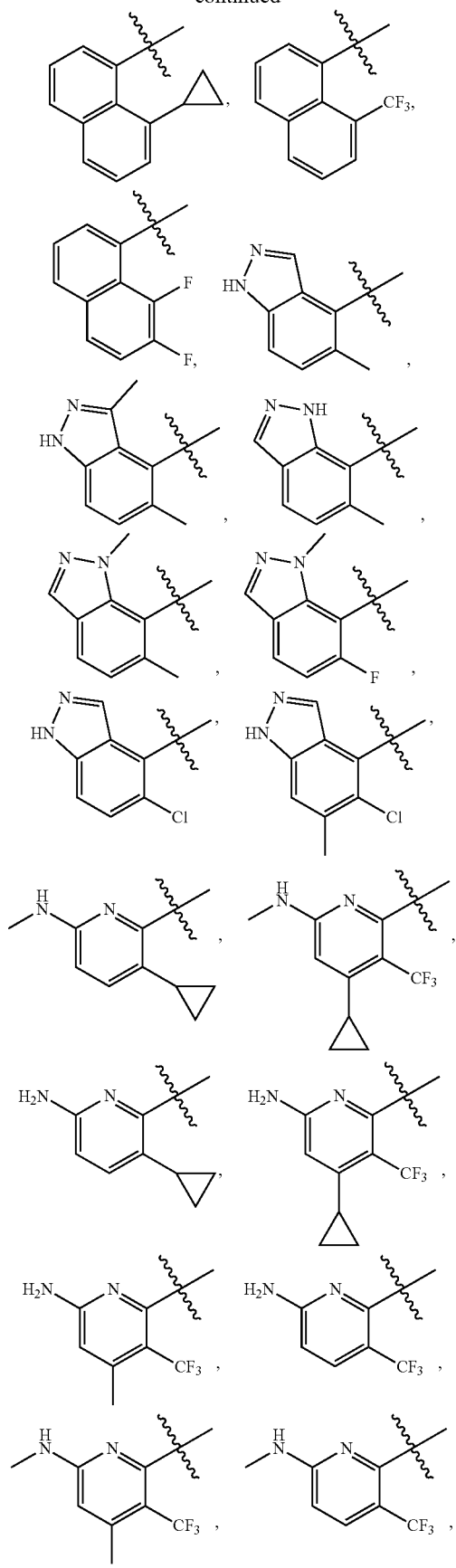
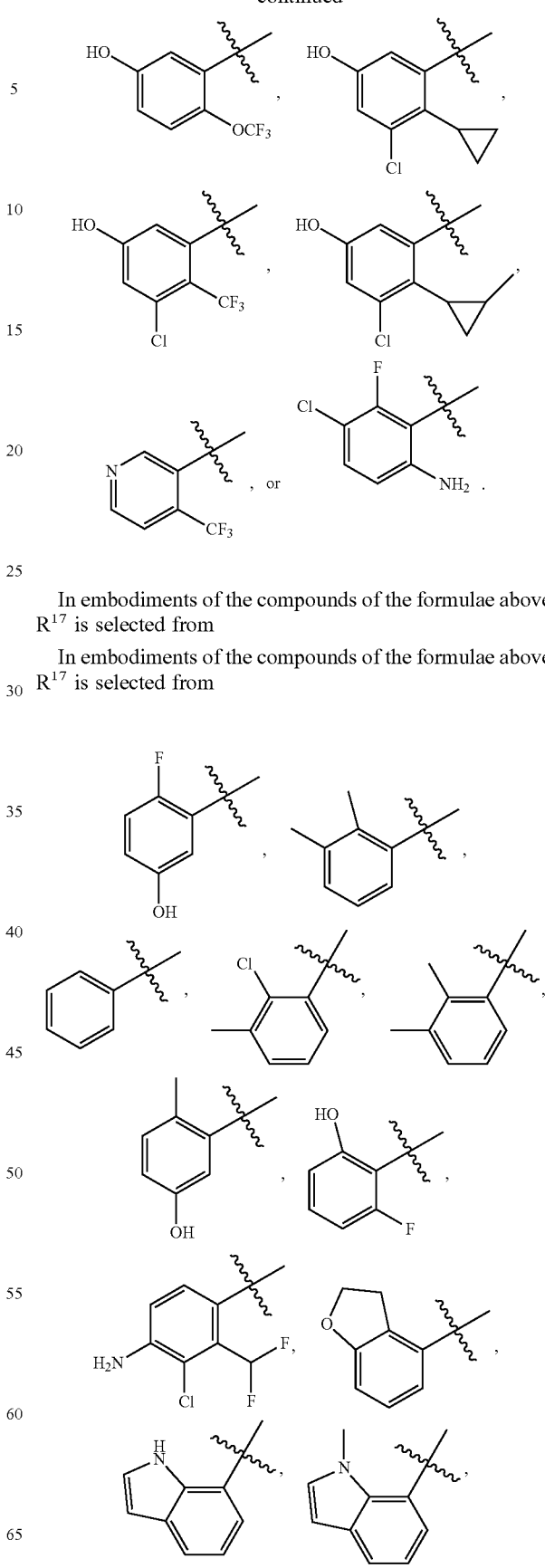
In embodiments of the compounds of the formulae above, $R^{17}$ is selected from
In embodiments of the compounds of the formulae above, $R^{17}$ is selected from

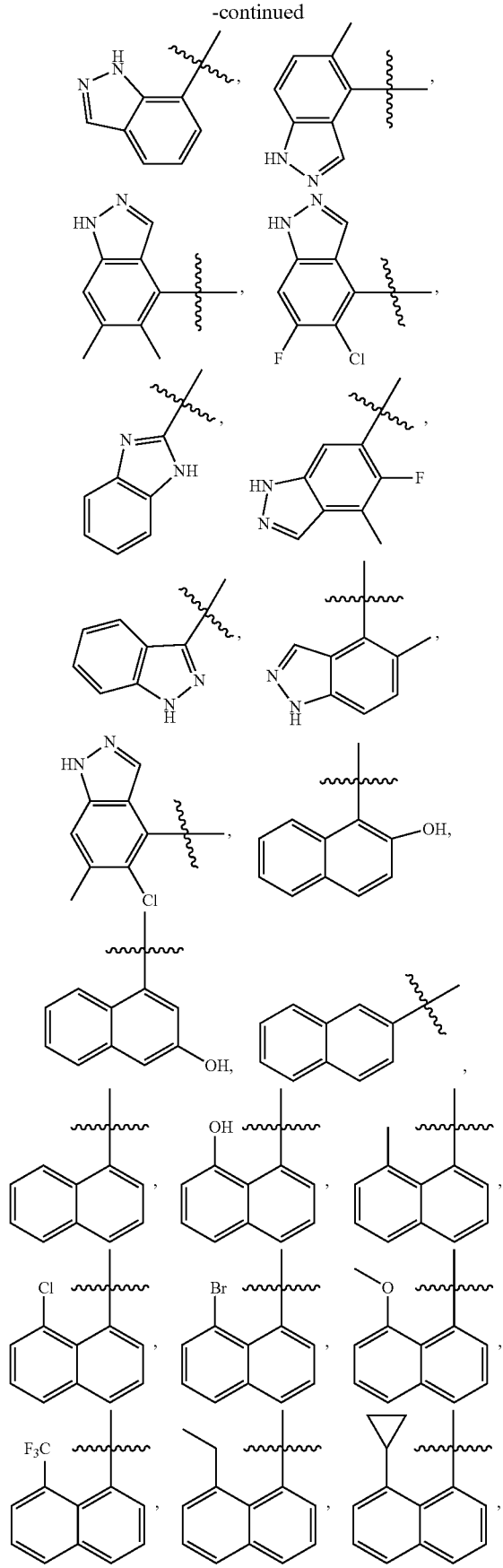
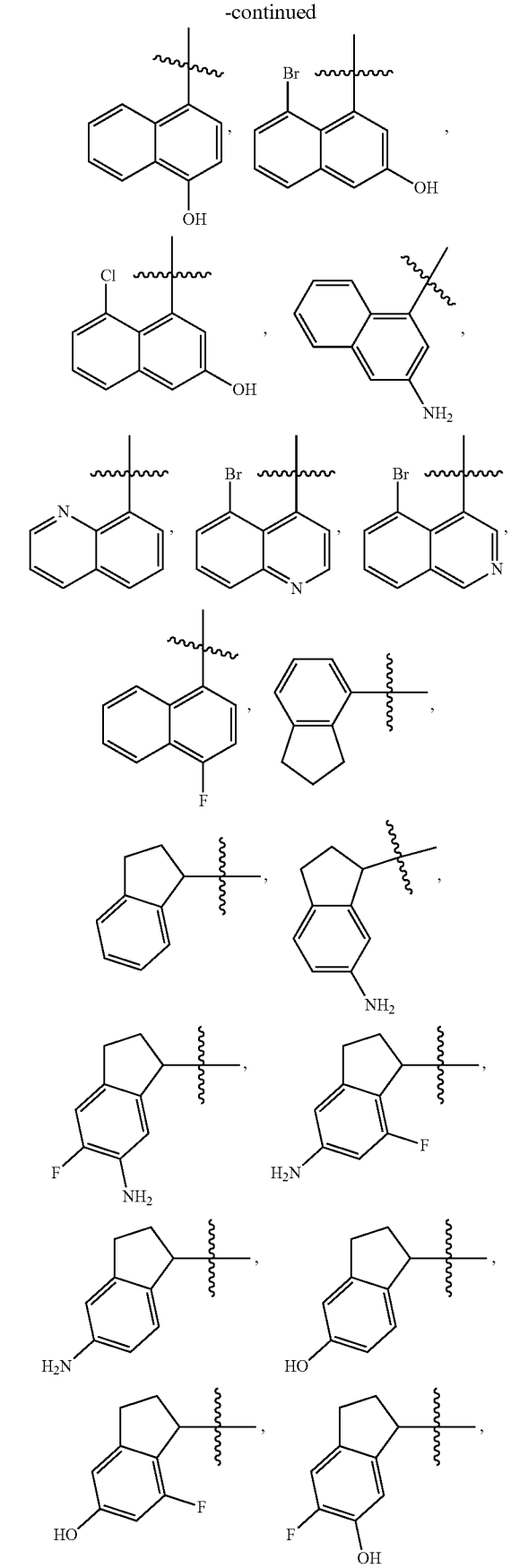

787
-continued
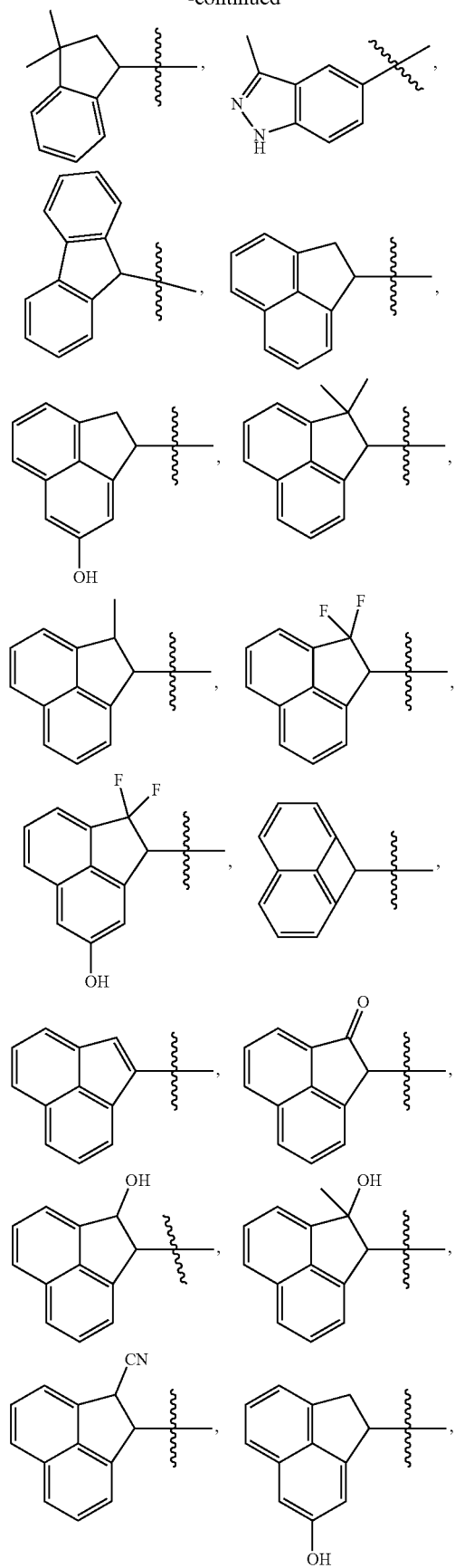
788
-continued
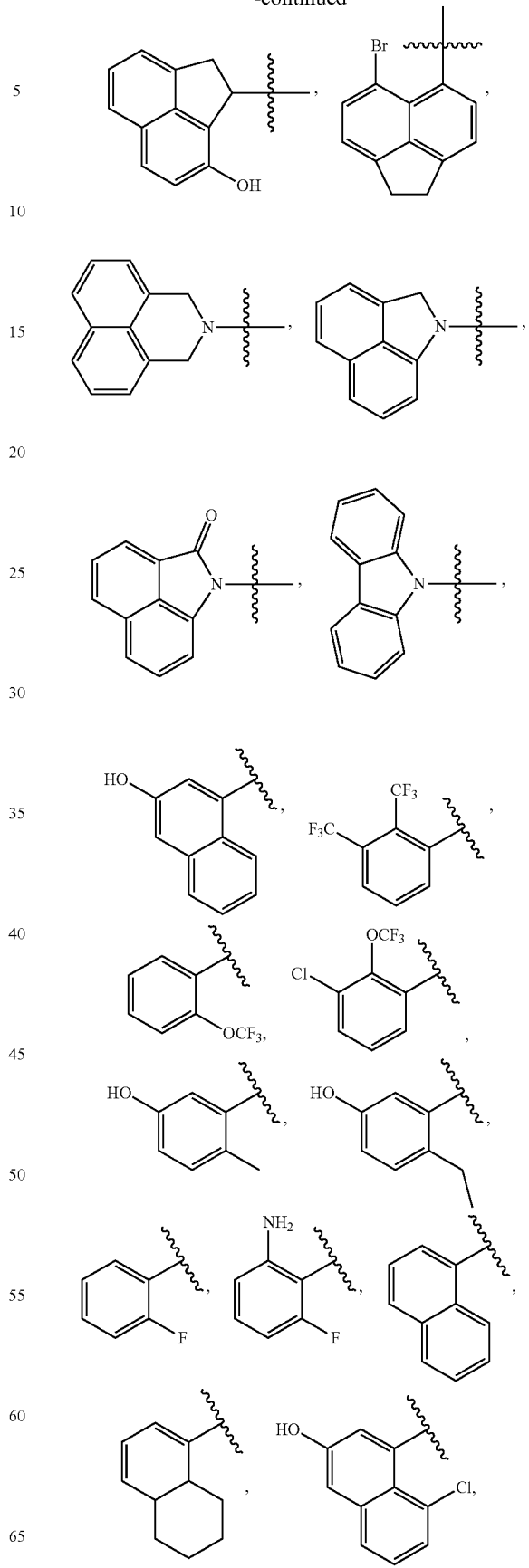

-continued
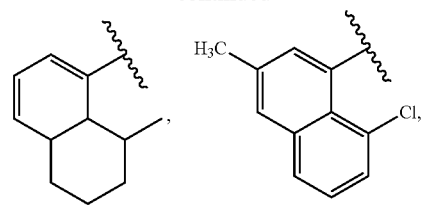
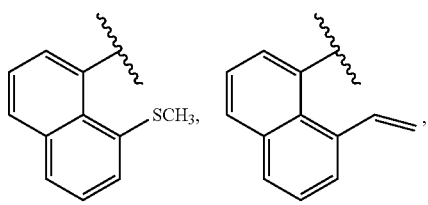
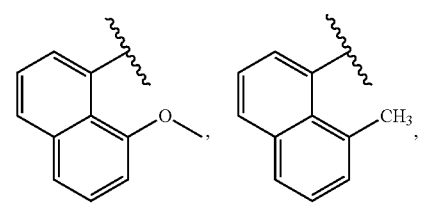
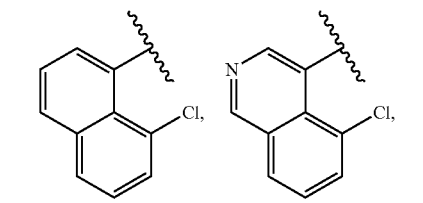
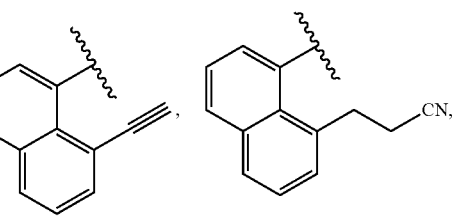
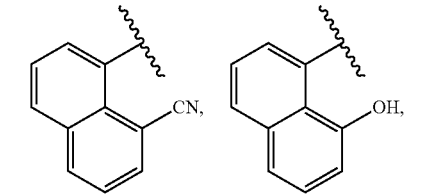
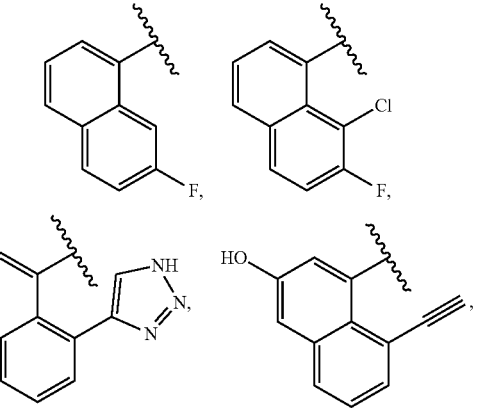
-continued
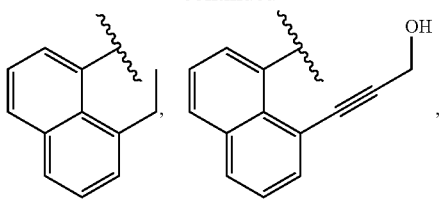
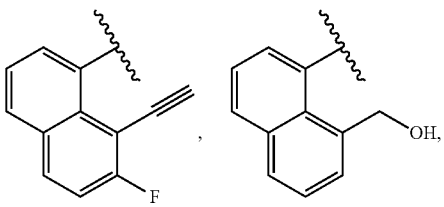
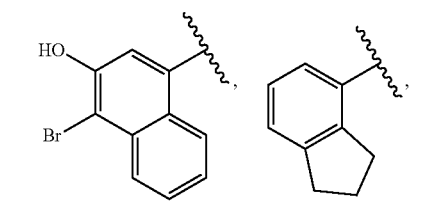
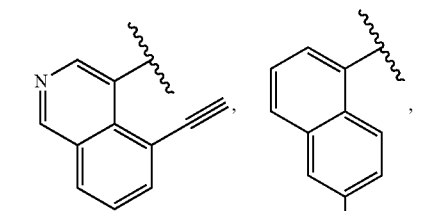
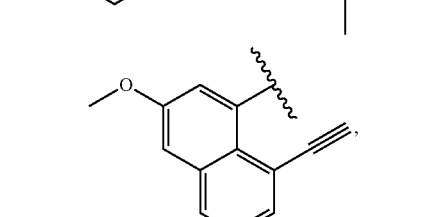
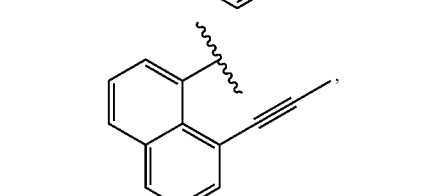
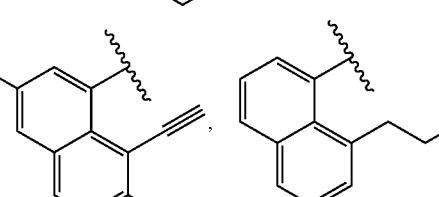
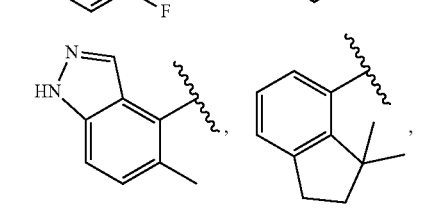

791
-continued
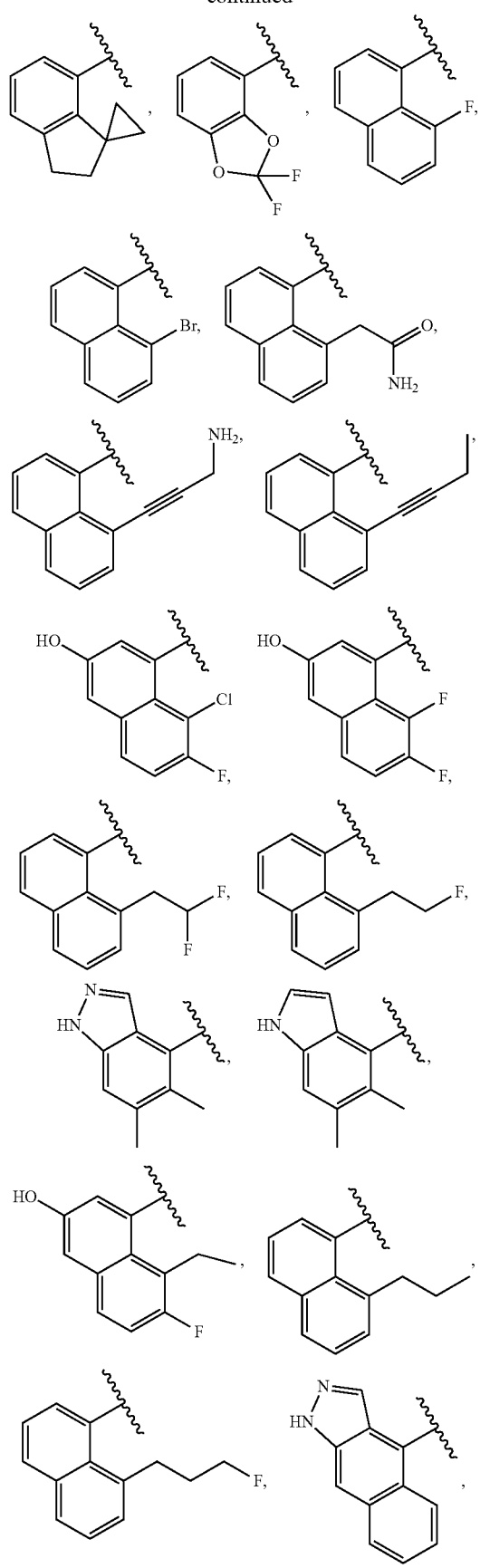
792
-continued
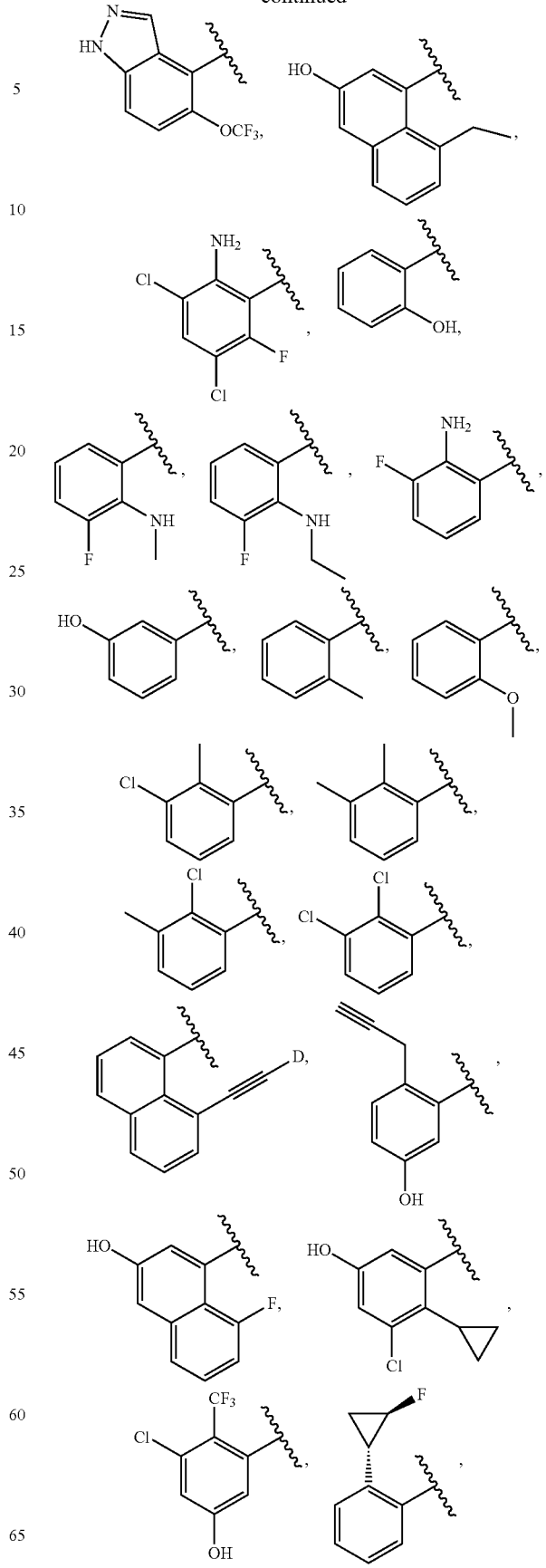

-continued
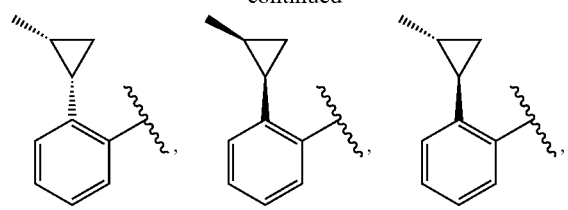
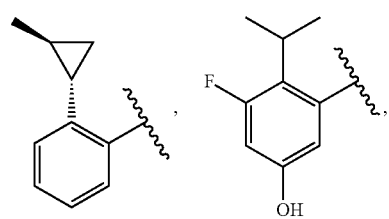
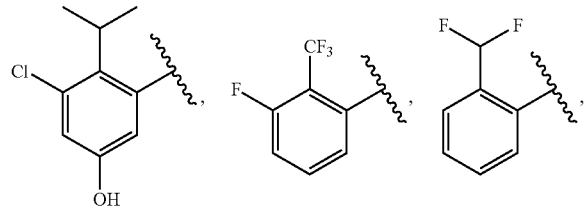
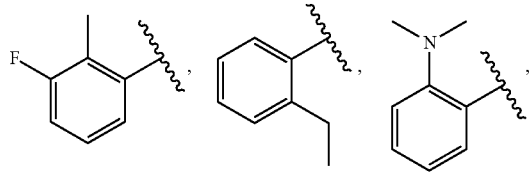
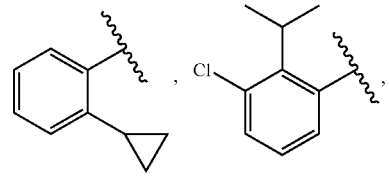
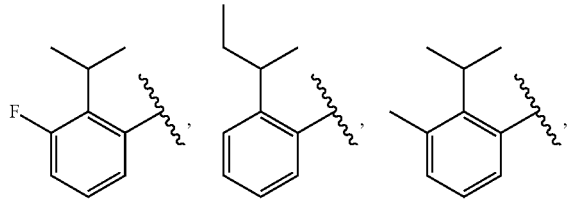
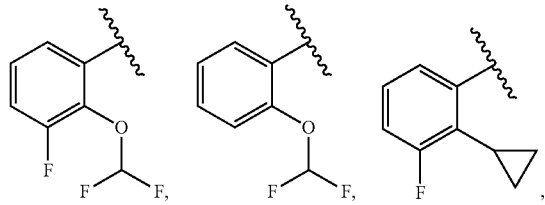
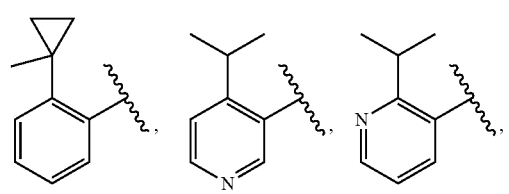
-continued
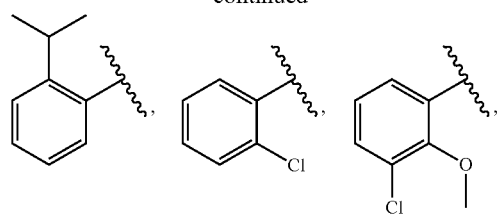
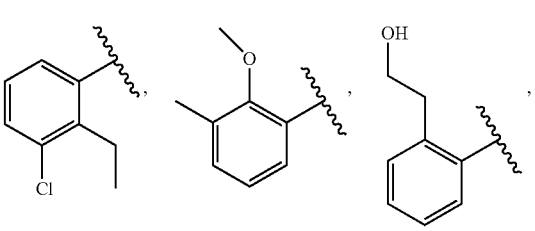
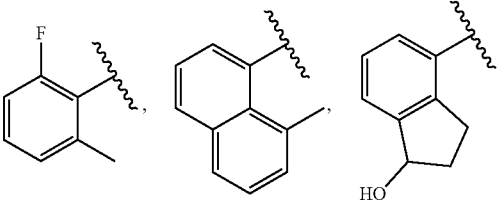
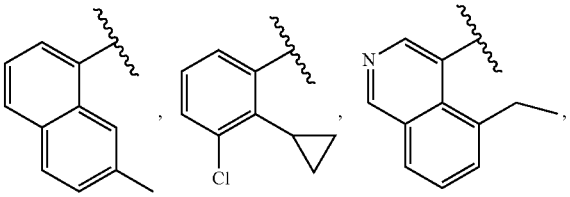
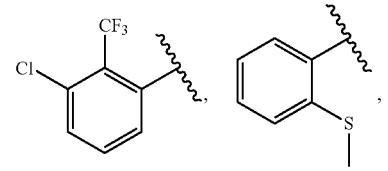
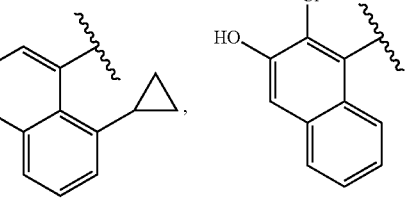
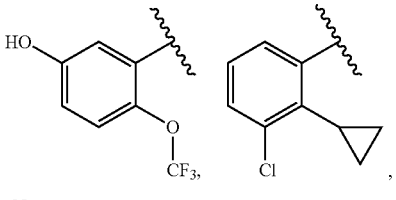
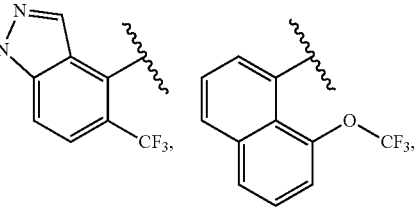

-continued
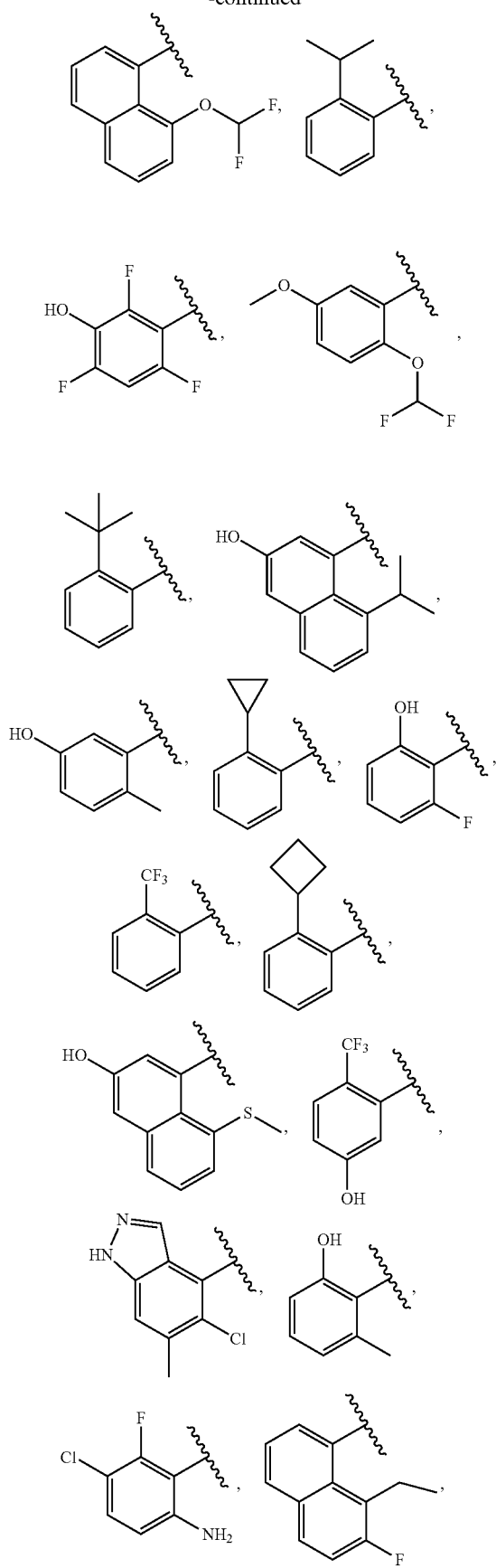
-continued
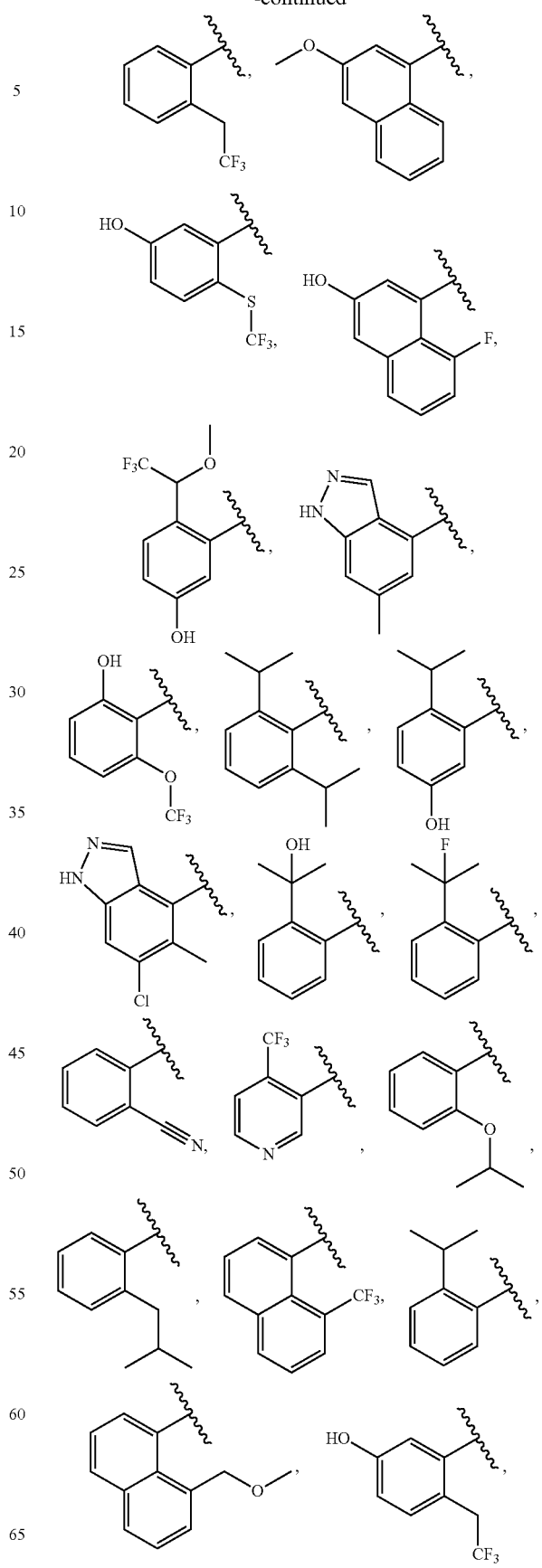

-continued
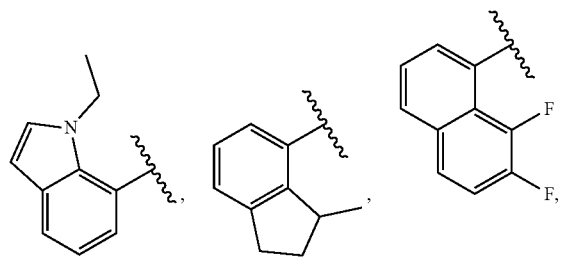
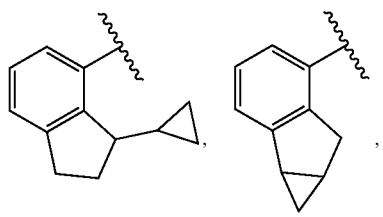
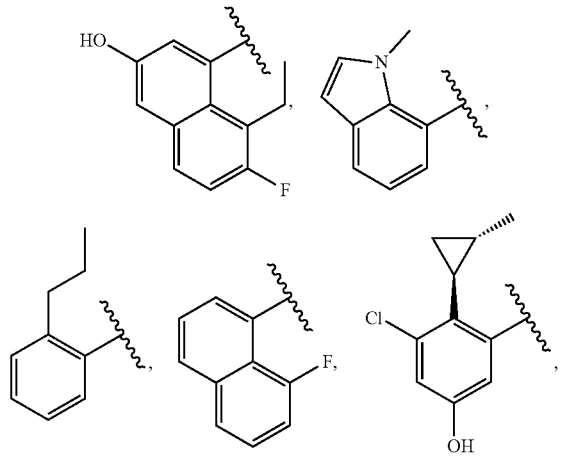
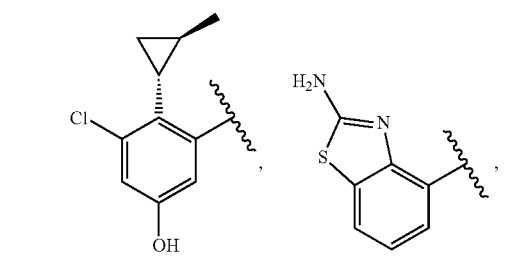
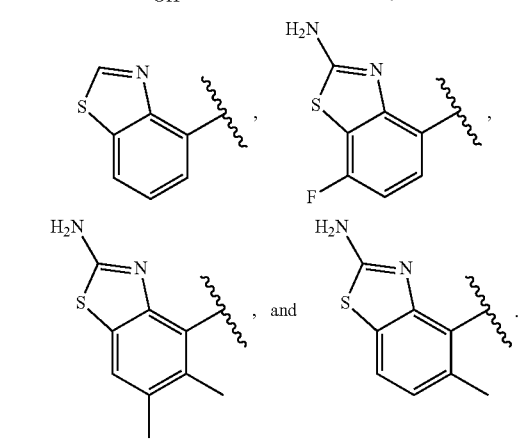
In embodiments of the formulae above, $R^{17}$ is selected from
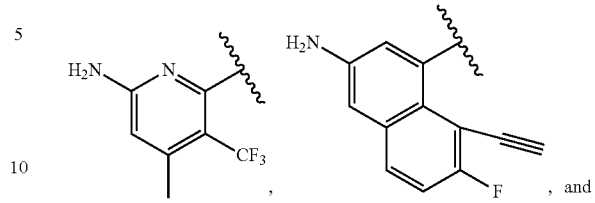
, and
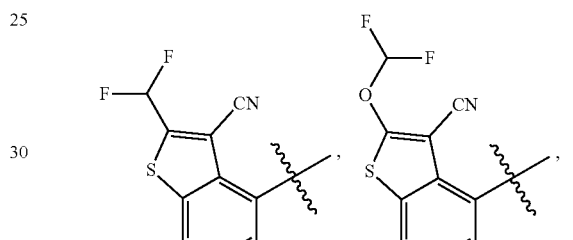
In embodiments of the compounds of the formulae above, $R^{17}$ is selected from
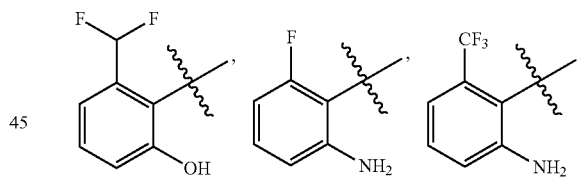
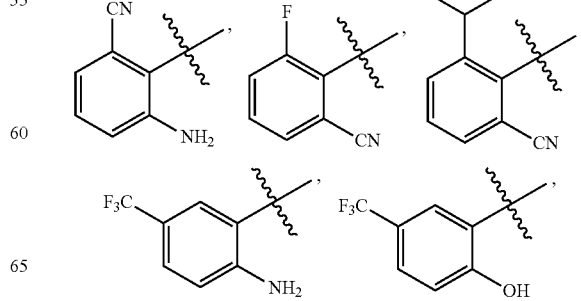

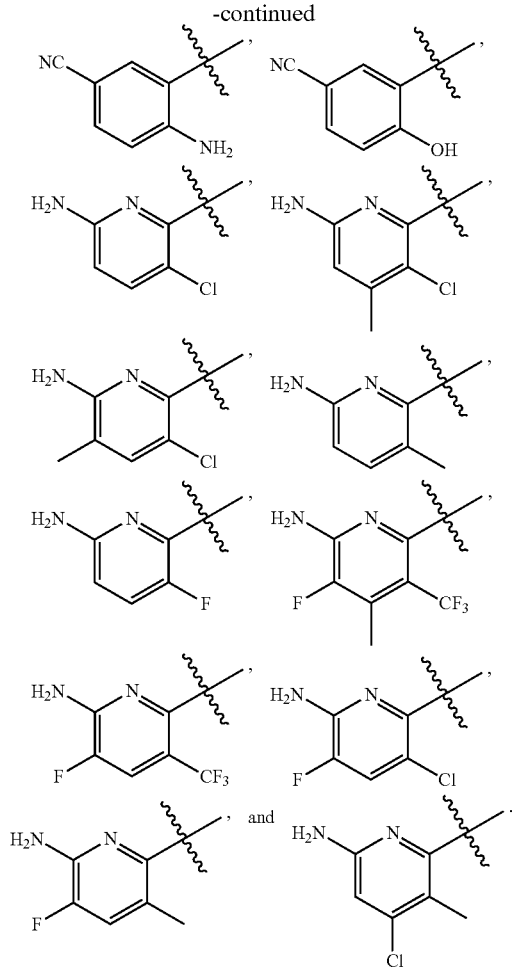
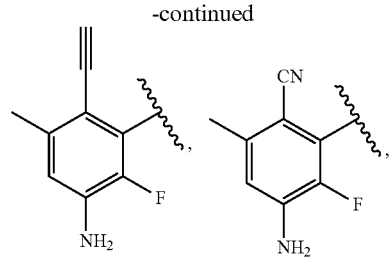
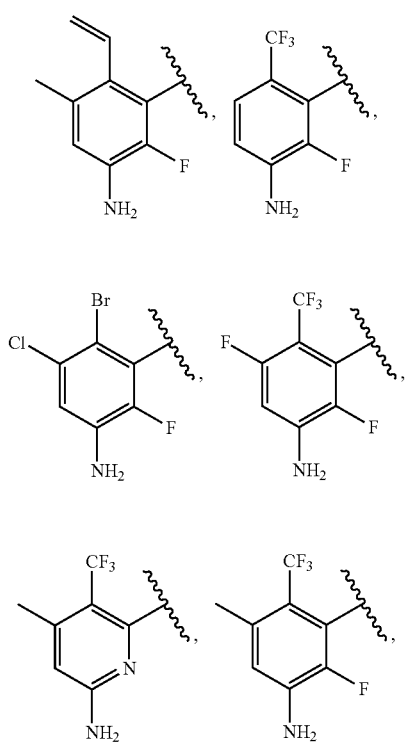
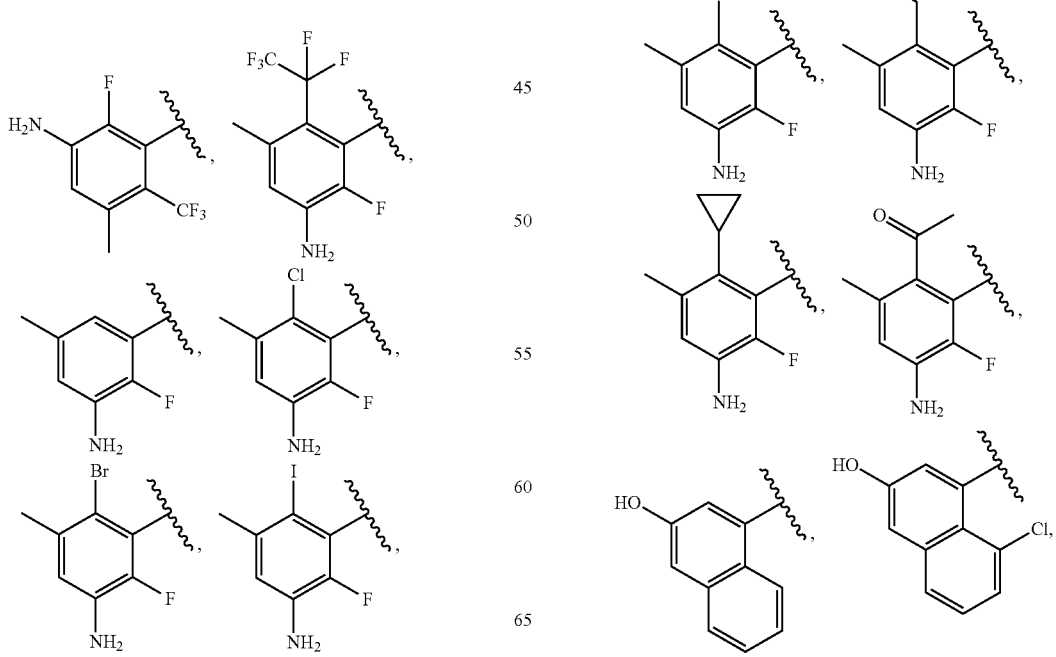
In embodiments of the compounds of the formulae above, $R^{17}$ is selected from 801
-continued

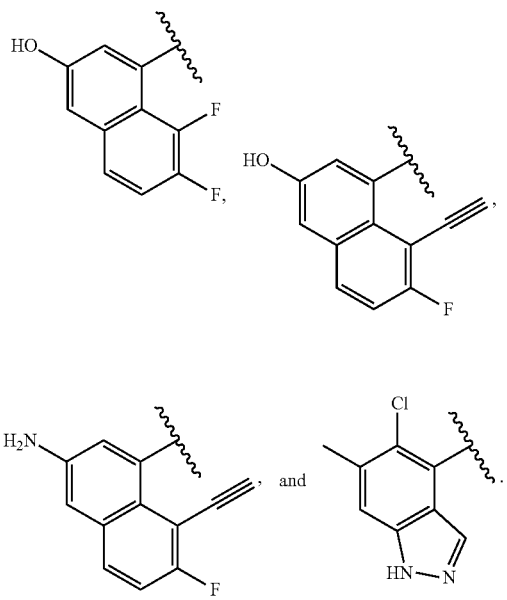

In embodiments of the compounds of the formulae above, R$^{17}$ is selected from

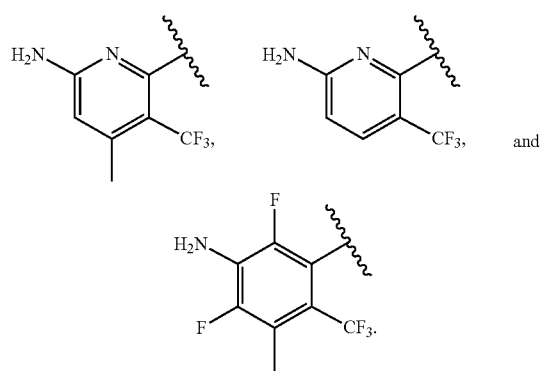

In embodiments of the compounds of the formulae above, R$^{17}$ is selected from

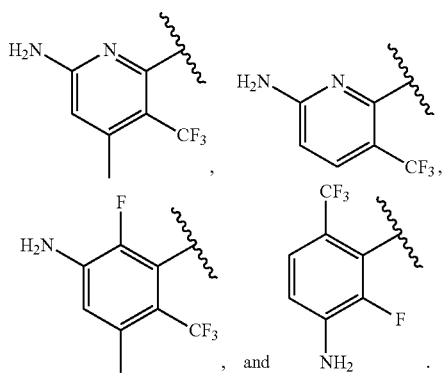

In embodiments of the compounds of the formulae above, R$^{17}$ is selected from:

802

Q$^3$ is C(R$^1$d);
Q$^4$ is S;
X$^9$, X$^{10}$, and X$^{11}$ are independently C(O), C(R$^{1a}$), or C(R$^{1a}$)(R$^1$b);
X$^{12}$ is C, N, or C(R$^{1a}$);
each R$^{1a}$, R$^{1b}$, R$^{1d}$, and R$^1$h are each independently selected from hydrogen, halogen, —CN, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20}$z;
each R$^{20}$z is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_6$-10aryl, —CH$_2$-C$_{1-9}$heteroaryl, C$_{1-9}$heteroaryl, —OR$^{21a}$, —SR$^{21a}$, —N(R$^{22a}$)(R$^{23a}$), —C(O)OR$^{22a}$, —C(O)N(R$^{22a}$)(R$^{23a}$), —C(O)C(O)N(R$^{22a}$)(R$^{23a}$), —OC(O)N(R$^{22a}$)(R$^{23a}$), —N(R$^{24a}$)C(O)N(R$^{22a}$)(R$^{23a}$), —N(R$^{24a}$)C(O)OR$^{25a}$, —N(R$^{24a}$)C(O)R$^{25a}$, —N(R$^{24a}$)S(O)$_2$R$^{25a}$, —C(O)R$^{25a}$, —S(O)$_2$R$^{25a}$, —S(O)$_2$N(R$^{22a}$)(R$^{23a}$), —OCH$_2$C(O)OR$^{22a}$, and —OC(O)R$^{25a}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_6$-10aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21a}$, —SR$^{21a}$, —N(R$^{22a}$)(R$^{23a}$), —C(O)OR$^{22a}$, —C(O)N(R$^{22a}$)(R$^{23a}$), —C(O)C(O)N(R$^{22a}$)(R$^{23a}$), —OC(O)N(R$^{22a}$)(R$^{23a}$), —N(R$^{24}$)C(O)N(R$^{22a}$)(R$^{23a}$), —N(R$^{24a}$)C(O)OR$^{25a}$, —N(R$^{24a}$)C(O)R$^{25a}$, —N(R$^{24a}$)S(O)$_2$R$^{25a}$, —C(O)R$^{25a}$, —S(O)$_2$R$^{25a}$, —S(O)$_2$N(R$^{22a}$)(R$^{23a}$), and —OC(O)R$^{25}$a;
each R$^{21a}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;
each R$^{22a}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;
each R$^{23a}$ is independently selected from H and C$_{1-6}$alkyl;
each R$^{24}$a is independently selected from H and C$_{1-6}$alkyl; and
each R$^{25}$a is independently selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl.

In embodiments of the compounds of the formulae above, $R^{17}$ is selected from:

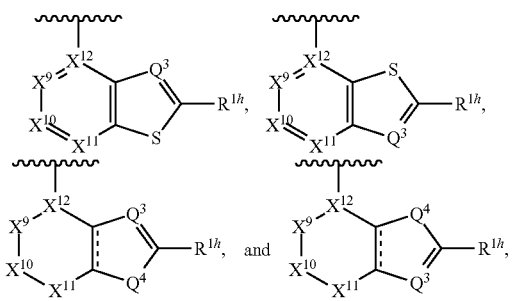

$Q^3$ is $C(R^1d)$;
$Q^4$ is O or S;
$X^9$, $X^{10}$, and $X^{11}$ are independently C(O), $C(R^{1a})$, or $C(R^{1a})(R^1b)$;
$X^{12}$ is C, N, or $C(R^{1a})$;
each $R^{1a}$, $R^{1b}$, $R^{1d}$, and $R^1h$ are each independently selected from hydrogen, halogen, —CN, $C_{1-6}$alkyl, $C_{1-6}$haloalkyl, $C_{2-6}$alkenyl, $C_2$-salkynyl, $C_{3-10}$cycloalkyl, $C_2$-heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20}z$;
each $R^{20}z$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_6$-10aryl, —CH$_2$-$C_{1-9}$heteroaryl, $C_{1-9}$heteroaryl, —$OR^{21a}$, —$SR^{21a}$, —N($R^{22a}$)($R^{23a}$), —C(O)O$R^{22a}$, —C(O)N($R^{22a}$)($R^{23a}$), —C(O)C(O)N($R^{22a}$)($R^{23a}$), —OC(O)N($R^{22a}$)($R^{23a}$), —N($R^{24a}$)C(O)N($R^{22a}$)($R^{23a}$), —N($R^{24a}$)C(O)O$R^{25a}$, —N($R^{24a}$)C(O)$R^{25a}$, —N($R^{24a}$)S(O)$_2R^{25a}$, —C(O)$R^{25a}$, —S(O)$_2R^{25a}$, —S(O)$_2$N($R^{22a}$)($R^{23a}$), —OCH$_2$C(O)O$R^{22a}$, and —OC(O)$R^{25a}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_6$-10aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21a}$, —$SR^{21a}$, —N($R^{22a}$)($R^{23a}$), —C(O)O$R^{22a}$, —C(O)N($R^{22a}$)($R^{23a}$), —C(O)C(O)N($R^{22a}$)($R^{23a}$), —OC(O)N($R^{22a}$)($R^{23a}$), —N($R^{24}$)C(O)N($R^{22a}$)($R^{23a}$), —N($R^{24a}$)C(O)O$R^{25a}$, —N($R^{24a}$)C(O)$R^{25a}$, —N($R^{24a}$)S(O)$_2R^{25a}$, —C(O)$R^{25a}$, —S(O)$_2R^{25a}$, —S(O)$_2$N($R^{22a}$)($R^{23a}$), and —OC(O)$R^{25}$a;
each $R^{21a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;
each $R^{22a}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;
each $R^{23a}$ is independently selected from H and $C_{1-6}$alkyl;
each $R^{24}$a is independently selected from H and $C_{1-6}$alkyl; and
each $R^{25}$a is independently selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl.

In embodiments of the compounds of the formulae above, $R^{17}$ is selected from:

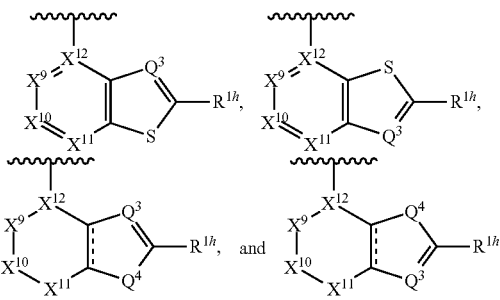

$Q^3$ is $C(R^{14})$;
$Q^4$ is O or S;
$X^9$, $X^{10}$, and $X^{11}$ are independently $C(R^{1a})$ or $C(R^{1a})(R^1b)$;
$X^{12}$ is C, N, or $C(R^{1a})$;
each $R^{1a}$, $R^{1b}$, and $R^1h$ is independently selected from hydrogen, halogen, —CN, $C_{1-4}$alkyl, $C_{1-4}$haloalkyl, —OH, and —NH$_2$; and
$R^{1D}$ is selected from hydrogen, —CN, $C_{1-4}$alkyl, and $C_{1-4}$haloalkyl;

In embodiments of the compounds of the formulae above, $R^{17}$ is

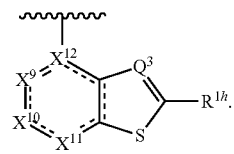

In embodiments of the compounds of the formulae above, $R^{17}$ is

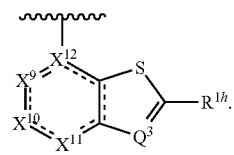

In embodiments of the compounds of the formulae above, $R^{17}$ is

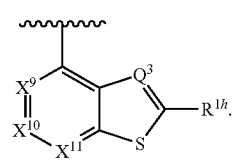

In embodiments of the compounds of the formulae above, $R^{17}$ is

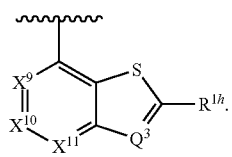
In embodiments of the compounds of the formulae above, $R^{17}$ is
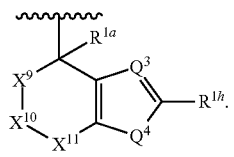
In embodiments of the compounds of the formulae above, $R^{17}$ is
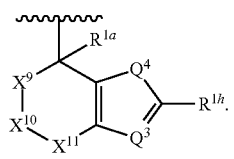
In embodiments of the compounds of the formulae above, $R^{17}$ is
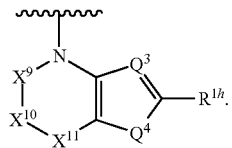
In embodiments of the compounds of the formulae above, $R^{17}$ is
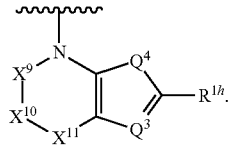
In embodiments of the compounds of the formulae above, $R^{17}$ is selected from
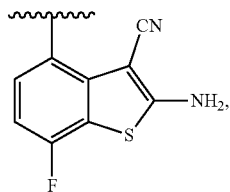 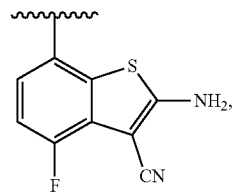
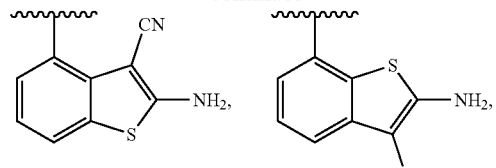
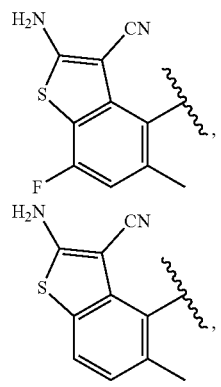 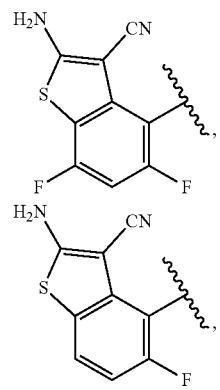
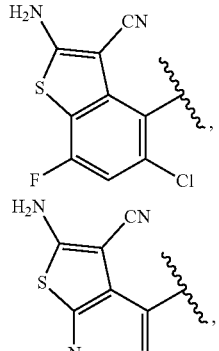 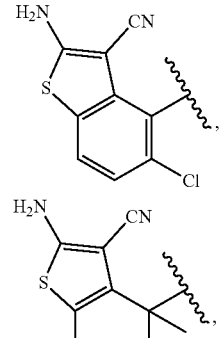
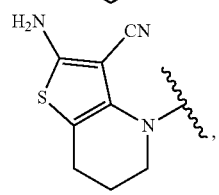 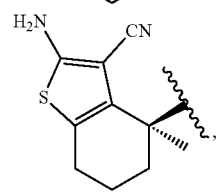
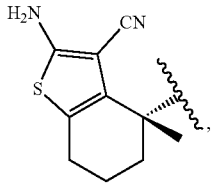 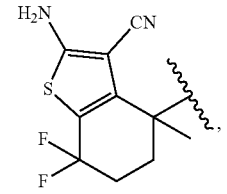
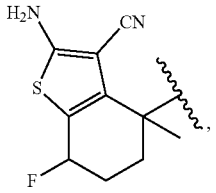 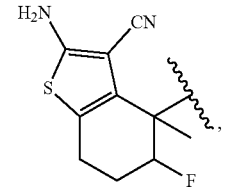
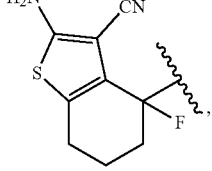 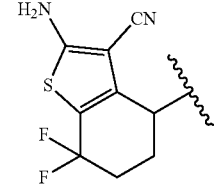

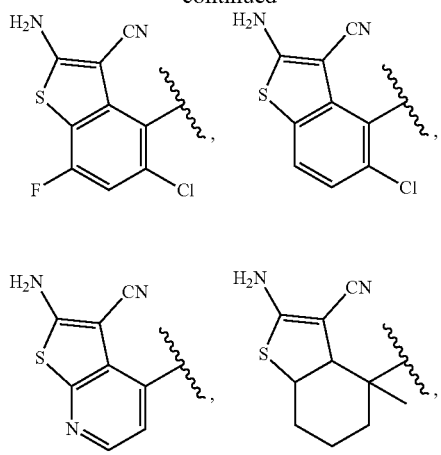
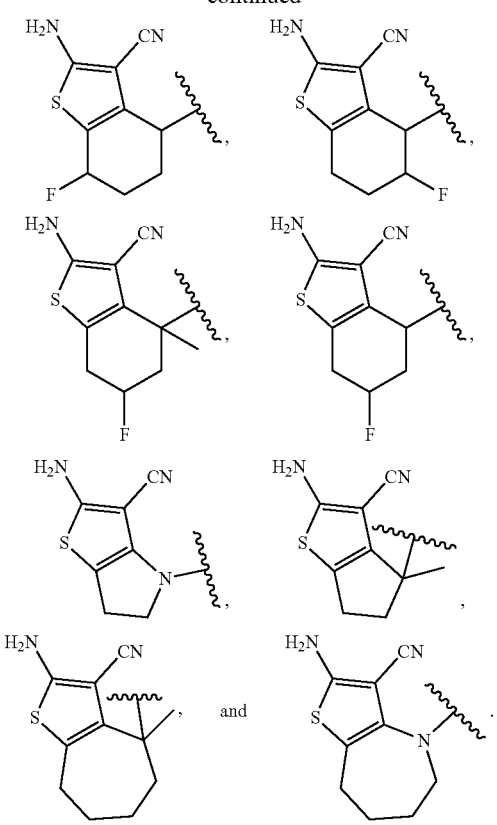
In embodiments of the compounds of the formulae above, $R^{17}$ is selected from
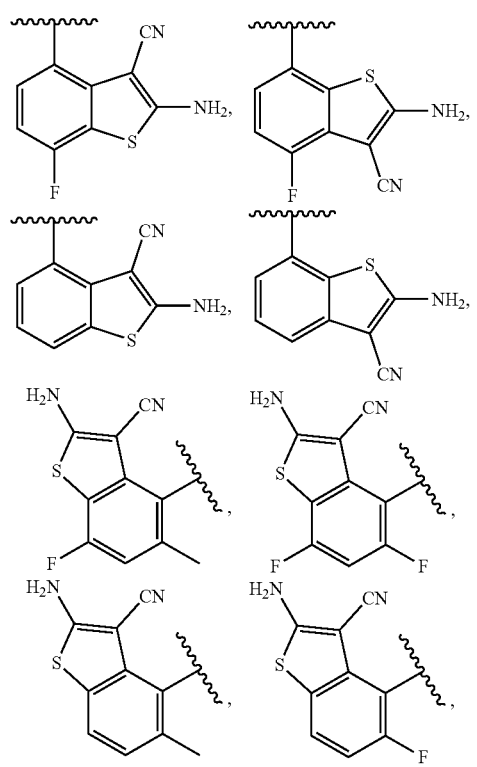
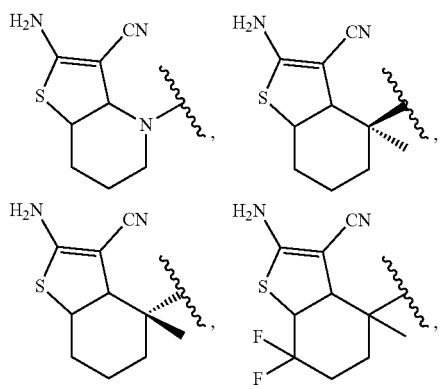
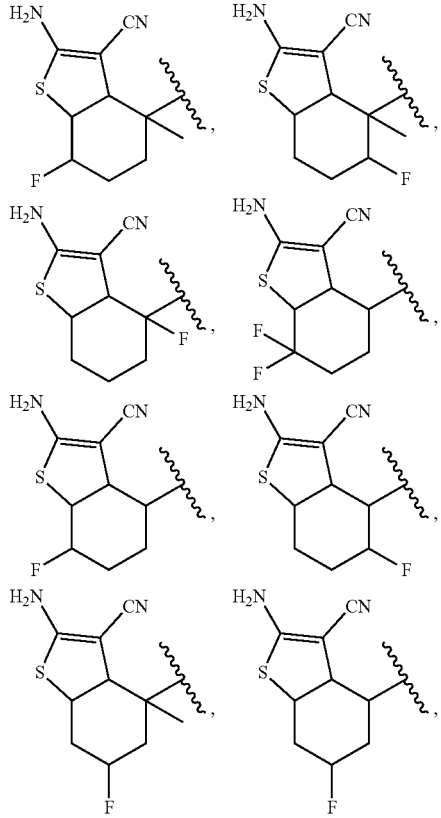

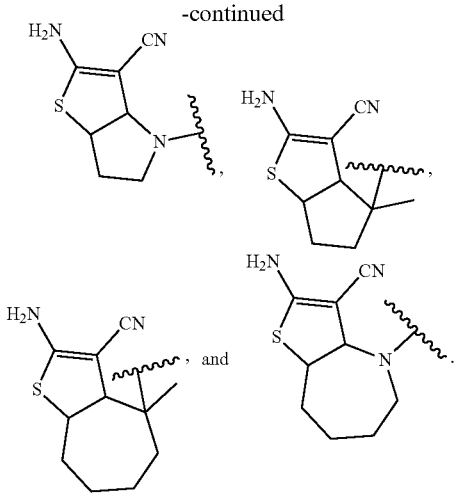

The individual embodiments herein below, or combinations thereof, (e.g., embodiments of $R^8$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''-1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each $R^8$ is independently hydrogen. In embodiments of the formulae above, each $R^8$ is independently halogen. In embodiments of the formulae above $R^8$ is F. In embodiments of the formulae above $R^8$ is $C_1$. In embodiments of the formulae above $R^8$ is Br. In embodiments of the formulae above $R^8$ is I. In embodiments of the formulae above, each $R^8$ is independently oxo. In embodiments of the formulae above, each $R^8$ is independently —CN. In embodiments of the formulae above, each $R^8$ is independently $C_{1-6}$alkyl. In embodiments of the formulae above, each $R^8$ is independently $C_{2-6}$alkenyl. In embodiments of the formulae above, each $R^8$ is independently $C_{2-6}$alkynyl. In embodiments of the formulae above, each $R^8$ is independently $C_{3-12}$cycloalkyl. In embodiments of the formulae above, each $R^8$ is independently $C_{2-11}$heterocycloalkyl. In embodiments of the formulae above, each $R^8$ is independently $C_{6-10}$aryl. In embodiments of the formulae above, each $R^8$ is independently $C_{1-9}$heteroaryl. In embodiments of the formulae above, each $R^8$ is independently selected from —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^8$ is independently $C_{1-6}$alkyl substituted with one, two, or three $R^{20}$h. In embodiments of the formulae above; each $R^8$ is independently $C_{2-6}$alkenyl substituted with one, two, or three $R^{20}$h. In embodiments of the formulae above, each $R^8$ is independently $C_{2-6}$alkynyl substituted with one, two, or three $R^{20}$h. In embodiments of the formulae above, each $R^8$ is independently $C_{3-12}$cycloalkyl substituted with one, two, or three $R^{20}$h. In embodiments of the formulae above, each $R^8$ is independently $C_2$-nheterocycloalkyl substituted with one, two, or three $R^{20}$h. In embodiments of the formulae above, each $R^8$ is independently $C_{6-10}$aryl substituted with one, two, or three $R^{20}$h. In embodiments of the formulae above, each $R^8$ is independently $C_{1-9}$heteroaryl substituted with one, two, or three $R^{20}$h. In embodiments of the formulae above, $R^8$ is independently F. In embodiments of the formulae above, $R^8$ is independently $C_1$. In embodiments of the formulae above, $R^8$ is independently Br. In embodiments of the formulae above, $R^8$ is independently I. In embodiments of the formulae above, $R^8$ is independently $C_{1-6}$alkyl. In embodiments of the formulae above, $R^8$ is independently methyl. In embodiments of the formulae above, $R^8$ is independently ethyl. In embodiments of the formulae above, $R^8$ is independently isopropyl. In embodiments of the formulae above, $R^8$ is independently $C_{2-6}$alkenyl. In embodiments of the formulae above, $R^8$ is independently $C_{2-6}$alkynyl. In embodiments of the formulae above, $R^8$ is independently $C_{1-6}$haloalkyl. In embodiments of the formulae above, $R^8$ is independently —$CF_3$. In embodiments of the formulae above, $R^8$ is independently $C_{6-12}$aryl. In embodiments of the formulae above, $R^8$ is independently $C_{1-11}$heteroaryl. In embodiments of the formulae above, $R^8$ is independently selected from —OH, —$OCH_3$, —SH, —$SCH_3$, —$N(CH_3)_2$, —$N(H)_2$, —$C(O)OH$, —$C(O)OCH_3$, —$OC(O)N(H)_2$, —$OC(O)N(CH_3)_2$, —$N(H)C(O)N(CH_3)_2$, —$N(H)C(O)N(H)_2$, —$N(H)C(O)OH$, —$N(H)C(O)OCH_3$, —$N(H)S(O)_2CH_3$, —$C(O)CH_3$, —$C(O)H$, —$S(O)CH_3$, —$OC(O)CH_3$, —$OC(O)H$, —$C(O)N(CH_3)_2$, —$C(O)C(O)N(CH_3)_2$, —$N(H)C(O)H$, —$N(H)C(O)CH_3$, —$S(O)_2CH_3$, —$S(O)_2N(H)_2$, —$S(O)_2N(CH_3)_2$, $S(=O)(=NH)N(H)_2$, $S(=O)(=NH)N(CH_3)_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2CH_3$, —$CH_2S(O)_2N(CH_3)_2$, and —$CH_2S(O)_2N(H)_2$. In additional embodiments of the subject compound, or a pharmaceutically acceptable salt or solvate thereof, $R^8$ is independently selected from hydrogen, halogen, —CN, $C_{1-6}$alkyl, $C_{2-6}$alkenyl, $C_{2-6}$alkynyl, and $C_{3-6}$cycloalkyl, wherein $C_{1-6}$alkyl, $C_{2-6}$alkenyl, $C_{2-6}$alkynyl, and $C_{3-6}$cycloalkyl are optionally substituted with one, two, or three $R^{20h}$. In embodiments of the formulae above, or a pharmaceutically acceptable salt or solvate thereof, $R^8$ is independently selected from hydrogen and halogen. In embodiments of the formulae above, or a pharmaceutically acceptable salt or solvate thereof, $R^8$ is independently selected from hydrogen and fluoro. In embodiments of the formulae above, or a pharmaceutically acceptable salt or solvate thereof, $R^8$ is hydrogen. In embodiments of the formulae above, or a pharmaceutically acceptable salt or solvate thereof, $R^8$ is fluoro. In embodiments of the formulae above, each $R^8$ is independently —$OR^{12}$. In embodiments of the formulae above, each $R^8$ is independently —$SR^{12}$. In embodiments of the formulae above, each $R^8$ is independently —$N(R^{12})(R^{13})$. In embodiments of the formulae above, each $R^8$ is independently —$C(O)OR^{12}$. In embodiments of the formulae above, each $R^8$ is independently selected from —$OC(O)N(R^{12})(R^{13})$ In embodiments of the formulae above, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, $R^8$ is independently —OH. In embodiments of the formulae above, $R^8$ is independently —$OCH_3$. In embodiments of the formulae above, $R^8$ is independently —SH. In embodiments of the formulae above, $R^8$ is independently —$SCH_3$. In embodiments of the formulae above, $R^8$ is independently —$N(CH_3)_2$. In embodiments of the formulae above, $R^8$ is independently —$N(H)_2$. In embodiments of the formulae above, $R^8$ is independently —$C(O)OH$. In embodiments of the formulae above, $R^8$ is independently selected from —$C(O)OCH_3$, —$OC(O)N(H)_2$, —$OC(O)N(CH_3)_2$, —$N(H)C(O)N(CH_3)_2$, —$N(H)C(O)N(H)_2$, —$N(H)C(O)OH$, —$N(H)C(O)OCH_3$, —$N(H)S(O)_2CH_3$, —$C(O)CH_3$, —$C(O)H$, —$S(O)CH_3$, —$OC(O)CH_3$, —$OC(O)H$, —$C(O)N(H)_2$, —$C(O)N(CH_3)_2$, —$C(O)C(O)N(CH_3)_2$, —$N(H)C(O)H$, —$N(H)C(O)CH_3$, —$S(O)_2CH_3$, —$S(O)_2N(H)_2$, —$S(O)_2N(CH_3)_2$, $S(=O)(=NH)N(H)_2$, $S(=O)(=NH)N(CH_3)_2$, —$CH_2C(O)N(H)_2$, —$CH_2C(O)N(CH_3)_2$, —$CH_2N(H)C(O)H$, —$CH_2N(H)C(O)CH_3$, —$CH_2S(O)_2H$, —$CH_2S(O)_2CH_3$, —$CH_2S(O)_2N(CH_3)_2$, and —$CH_2S(O)_2N(H)_2$.

The individual embodiments herein below, or combinations thereof, (e.g., embodiments of $R^{8a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''-1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each $R^{8a}$ is independently hydrogen. In embodiments of the formulae above, each $R^{8a}$ is independently halogen. In embodiments of the formulae above, each $R^{8a}$ is independently oxo. In embodiments of the formulae above, each $R^{8a}$ is independently —CN. In embodiments of the formulae above, each $R^{8a}$ is independently $C_{1-6}$alkyl. In embodiments of the formulae above, each $R^{8a}$ is independently $C_{2-6}$alkenyl. In embodiments of the formulae above, each $R^{8a}$ is independently $C_{2-6}$alkynyl. In embodiments of the formulae above, each $R^{8a}$ is independently $C_{3-12}$cycloalkyl. In embodiments of the formulae above, each $R^{8a}$ is independently $C_{2-11}$heterocycloalkyl. In embodiments of the formulae above, each $R^{8a}$ is independently $C_{6-10}$aryl. In embodiments of the formulae above, each $R^{8a}$ is independently $C_{1-9}$heteroaryl. In embodiments of the formulae above, each $R^{8a}$ is independently selected from —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$. In embodiments of the formulae above, each $R^{8a}$ is independently $C_{1-6}$alkyl substituted with one, two, or three $R^{20h}$. In embodiments of the formulae above, each $R^{8a}$ is independently $C_{2-6}$alkenyl substituted with one, two, or three $R^{20h}$. In embodiments of the formulae above, each $R^8$a is independently $C_{2-6}$alkynyl substituted with one, two, or three $R^{20h}$. In embodiments of the formulae above, each $R^{8a}$ is independently $C_{3-12}$cycloalkyl substituted with one, two, or three $R^{20h}$. In embodiments of the formulae above, each $R^{8a}$ is independently $C_{2-11}$heterocycloalkyl substituted with one, two, or three $R^{20h}$. In embodiments of the formulae above, each $R^{8a}$ is independently $C_{6-10}$aryl substituted with one, two, or three $R^{20h}$. In embodiments of the formulae above, each $R^{8a}$ is independently $C_{1-9}$heteroaryl substituted with one, two, or three $R^{20h}$. In embodiments of the formulae above, $R^{8a}$ is independently F. In embodiments of the formulae above, $R^{8a}$ is independently $C_1$. In embodiments of the formulae above, $R^{8a}$ is independently Br. In embodiments of the formulae above, $R^{8a}$ is independently I. In embodiments of the formulae above, $R^{8a}$ is independently $C_{1-6}$alkyl. In embodiments of the formulae above, $R^{8a}$ is independently methyl. In embodiments of the formulae above, $R^{8a}$ is independently ethyl. In embodiments of the formulae above, $R^{8a}$ is independently isopropyl. In embodiments of the formulae above, $R^{8a}$ is independently $C_{2-6}$alkenyl. In embodiments of the formulae above, $R^{8a}$ is independently $C_{2-6}$alkynyl. In embodiments of the formulae above, $R^{8a}$ is independently $C_{1-6}$haloalkyl. In embodiments of the formulae above, $R^{8a}$ is independently —$CF_3$. In embodiments of the formulae above, $R^{8a}$ is independently $C_{3-12}$cycloalkyl. In embodiments of the formulae above, $R^{8a}$ is independently $C_{2-11}$heterocycloalkyl. In embodiments of the formulae above, $R^{8a}$ is independently $C_{6-12}$aryl. In embodiments of the formulae above, $R^{8a}$ is independently $C_{1-11}$heteroaryl. In embodiments of the formulae above, $R^{8a}$ is independently selected from —OH, —$OCH_3$, —SH, —$SCH_3$, —$N(CH_3)_2$, —$N(H)_2$, —C(O)OH, —C(O)$OCH_3$, —OC(O)$N(H)_2$, —OC(O)$N(CH_3)_2$, —N(H)C(O)$N(CH_3)_2$, —N(H)C(O)$N(H)_2$, —N(H)C(O)OH, —N(H)C(O)$OCH_3$, —N(H)S(O)$_2CH_3$, —C(O)$CH_3$, —C(O)H, —S(O)$CH_3$, —OC(O)$CH_3$, —OC(O)H, —C(O)$N(CH_3)_2$, —C(O)C(O)$N(CH_3)_2$, —N(H)C(O)H, —N(H)C(O)$CH_3$, —S(O)$_2CH_3$, —S(O)$_2N(H)_2$, —S(O)$_2N(CH_3)_2$, S(=O)(=NH)$N(H)_2$, S(=O)(=NH)$N(CH_3)_2$, —$CH_2$C(O)$N(H)_2$, —$CH_2$C(O)$N(CH_3)_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2N(CH_3)_2$, and —$CH_2$S(O)$_2N(H)_2$. In embodiments of the formulae above, each $R^{8a}$ is independently —$OR^{12}$. In embodiments of the formulae above, each $R^{8a}$ is independently —$SR^{12}$. In embodiments of the formulae above, each $R^{8a}$ is independently —N($R^{12}$)($R^{13}$). In embodiments of the formulae above, each $R^{8a}$ is independently —C(O)$OR^{12}$. In embodiments of the formulae above, each $R^{8a}$ is independently selected from —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —C(O)C(O)N($R^{12}$)($R^{13}$), —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$). In embodiments of the formulae above, $R^{8a}$ is independently —OH. In embodiments of the formulae above, $R^{8a}$ is independently —$OCH_3$. In embodiments of the formulae above, $R^{8a}$ is independently —SH. In embodiments of the formulae above, $R^{8a}$ is independently —$SCH_3$. In embodiments of the formulae above, $R^{8a}$ is independently —$N(CH_3)_2$. In embodiments of the formulae above, $R^{8a}$ is independently —$N(H)_2$. In embodiments of the formulae above, $R^{8a}$ is independently —C(O)OH. In embodiments of the formulae above, $R^{8a}$ is independently selected from —C(O)$OCH_3$, —OC(O)$N(H)_2$, —OC(O)$N(CH_3)_2$, —N(H)C(O)$N(CH_3)_2$, —N(H)C(O)$N(H)_2$, —N(H)C(O)OH, —N(H)C(O)$OCH_3$, —N(H)S(O)$_2CH_3$, —C(O)$CH_3$, —C(O)H, —S(O)$CH_3$, —OC(O)$CH_3$, —OC(O)H, —C(O)$N(CH_3)_2$, —C(O)C(O)$N(CH_3)_2$, —N(H)C(O)H, —N(H)C(O)$CH_3$, —S(O)$_2CH_3$, —S(O)$_2N(H)_2$, —S(O)$_2N(CH_3)_2$, S(=O)(=NH)$N(H)_2$, S(=O)(=NH)$N(CH_3)_2$, —$CH_2$C(O)$N(H)_2$, —$CH_2$C(O)$N(CH_3)_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2N(CH_3)_2$, and —$CH_2$S(O)$_2N(H)_2$. In embodiments of the formulae above, $R^8b$ is independently —OH. In embodiments of the formulae above, $R^8b$ is independently —$OCH_3$. In embodiments of the formulae above, $R^8b$ is independently —SH. In embodiments of the formulae above, $R^8b$ is independently —$SCH_3$. In embodiments of the formulae above, $R^8b$ is independently —C(O)OH. In embodiments of the formulae above, $R^8b$ is independently selected from —C(O)$OCH_3$, —OC(O)$N(H)_2$, —OC(O)$N(CH_3)_2$, —C(O)$CH_3$, —C(O)H, —S(O)$CH_3$, —OC(O)$CH_3$, —OC(O)H, —C(O)$N(CH_3)_2$, —C(O)C(O)$N(CH_3)_2$, —S(O)$_2CH_3$, —S(O)$_2N(H)_2$, —S(O)$_2N(CH_3)_2$, S(=O)(=NH)$N(H)_2$, S(=O)(=NH)$N(CH_3)_2$, —$CH_2$C(O)$N(H)_2$, —$CH_2$C(O)$N(CH_3)_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2N(CH_3)_2$, and —$CH_2$S(O)$_2N(H)_2$.

The individual embodiments herein below, or combinations thereof, (e.g., embodiments of $R^8b$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^8b$ is independently hydrogen. In embodiments of the formulae above, each $R^8b$ is independently —CN. In embodiments of the formulae above, each $R^8b$ is independently $C_{1-6}$alkyl. In embodiments of the formulae above, each $R^8b$ is independently $C_{2-6}$alkenyl. In embodiments of the formulae above, each $R^8b$ is independently $C_{2-6}$alkynyl. In embodiments of the formulae above, each $R^8b$ is independently $C_{3-12}$cycloalkyl. In embodiments of the formulae above;

each $R^8b$ is independently $C_{2-11}$heterocycloalkyl. In embodiments of the formulae above, each $R^8b$ is independently $C_{6-10}$aryl. In embodiments of the formulae above, each $R^8b$ is independently $C_{1-9}$heteroaryl. In embodiments of the formulae above, each $R^8b$ is independently selected from —$OR^{12}$, —$SR^{12}$, —C(O)$OR^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —C(O)C(O)N($R^{12}$)($R^{13}$), —S(O)$_2R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$). In embodiments of the formulae above, each $R^8b$ is independently $C_{1-6}$alkyl substituted with one, two, or three $R^{20}$h. In embodiments of the formulae above, each $R^8$b is independently $C_{2-6}$alkenyl substituted with one, two, or three $R^{20}$h. In embodiments of the formulae above, each $R^8$b is independently $C_{2-6}$alkynyl substituted with one, two, or three $R^{20}$h. In embodiments of the formulae above, each $R^8$b is independently $C_{3-12}$cycloalkyl substituted with one, two, or three $R^{20}$h. In embodiments of the formulae above, each $R^8$b is independently $C_{2-11}$heterocycloalkyl substituted with one, two, or three
$R^{20}$h. In embodiments of the formulae above, each $R^8$b is independently $C_{6-10}$aryl substituted with one, two, or three $R^{20}$h. In embodiments of the formulae above, each $R^8$b is independently $C_{1-9}$heteroaryl substituted with one, two, or three $R^{20}$h. In embodiments of the formulae above, $R^{8b}$ is independently $C_{1-6}$alkyl. In embodiments of the formulae above, $R^8$b is independently methyl. In embodiments of the formulae above, $R^8$b is independently ethyl. In embodiments of the formulae above, $R^8$b is independently isopropyl. In embodiments of the formulae above, $R^8$b is independently $C_{2-6}$alkenyl. In embodiments of the formulae above, $R^8$b is independently $C_{2-6}$alkynyl. In embodiments of the formulae above, $R^8$b is independently $C_{1-6}$haloalkyl. In embodiments of the formulae above, $R^8$b is independently —$CF_3$. In embodiments of the formulae above, $R^8$b is independently $C_{6-12}$aryl. In embodiments of the formulae above, $R^{8b}$ is independently $C_{1-11}$heteroaryl. In embodiments of the formulae above, $R^8$b is independently selected from —OH, —$OCH_3$, —SH, —$SCH_3$, —C(O)OH, —C(O)$OCH_3$, —OC(O)N(H)$_2$, —OC(O)N($CH_3$)$_2$, —C(O)$CH_3$, —C(O)H, —S(O)$CH_3$, —OC(O)$CH_3$, —OC(O)H, —C(O)N($CH_3$)$_2$, —C(O)C(O)N($CH_3$)$_2$, —S(O)$_2CH_3$, —S(O)$_2$N(H)$_2$, —S(O)$_2$N($CH_3$)$_2$, S(=O)(=NH)N(H)$_2$, S(=O)(=NH)N($CH_3$)$_2$, —$CH_2$C(O)N(H)$_2$, —$CH_2$C(O)N($CH_3$)$_2$, —$CH_2$N(H)C(O)H, —$CH_2$N(H)C(O)$CH_3$, —$CH_2$S(O)$_2$H, —$CH_2$S(O)$_2CH_3$, —$CH_2$S(O)$_2$N($CH_3$)$_2$, and —$CH_2$S(O)$_2$N(H)$_2$. In embodiments of the formulae above, each $R^8$b is independently —$OR^{12}$. In embodiments of the formulae above;
each $R^8$b is independently —$SR^{12}$. In embodiments of the formulae above, each $R^8$b is independently —C(O)$OR^{12}$. In embodiments of the formulae above, each $R^8$b is independently selected from —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —C(O)C(O)N($R^{12}$)($R^{13}$), —S(O)$_2R^{15}$, —S(O)$_2$N($R^{12}$)($R^{13}$), —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$).

The individual embodiments herein below, or combinations thereof, (e.g., embodiments of $R^9$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"- 1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each $R^9$ is independently hydrogen. In embodiments of the formulae above, each R' is independently $C_{1-6}$alkyl substituted with one, two, or three $R^{20i}$. In embodiments of the formulae above, each $R^9$ is independently $C_{2-6}$alkenyl substituted with one, two, or three $R^{20i}$. In embodiments of the formulae above, each $R^9$ is independently $C_{2-6}$alkynyl substituted with one, two, or three $R^{20i}$. In embodiments of the formulae above, each $R^9$ is independently $C_{3-12}$cycloalkyl substituted with one, two, or three $R^{20i}$. In embodiments of the formulae above, each R' is independently $C_{2-11}$heterocycloalkyl substituted with one, two, or three $R^{20i}$. In embodiments of the formulae above, each $R^9$ is independently $C_{6-10}$aryl substituted with one, two, or three $R^{20i}$. In embodiments of the formulae above, each $R^9$ is independently $C_{1-9}$heteroaryl substituted with one, two, or three $R^{20i}$. In embodiments of the formulae above, $R^9$ is independently $C_{1-6}$alkyl. In embodiments of the formulae above, R' is independently methyl. In embodiments of the formulae above, $R^9$ is independently ethyl. In embodiments of the formulae above, $R^9$ is independently isopropyl. In embodiments of the formulae above, R' is independently $C_{2-6}$alkenyl. In embodiments of the formulae above, R' is independently $C_{2-6}$alkynyl. In embodiments of the formulae above, R' is independently $C_{1-6}$haloalkyl. In embodiments of the formulae above, R' is independently —$CF_3$. In embodiments of the formulae above, $R^9$ is independently $C_{3-12}$cycloalkyl. In embodiments of the formulae above, R' is independently $C_{2-11}$heterocycloalkyl. In embodiments of the formulae above, $R^9$ is independently $C_{6-12}$aryl. In embodiments of the formulae above, $R^9$ is independently $C_{1-11}$heteroaryl.

The individual embodiments herein below, or combinations thereof, (e.g., embodiments of $R^{20a}$, $R^{20b}$, $R^{20c}$, $R^{20}$d, $R^{20}€$, $R^{20f}$, $R^{20g}$, $R^{20h}$, $R^{20i}$, $R^{20j}$, $R^{20k}$, or $R^{20t}$ are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XX Va), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B- 1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, $R^{20}a$ is independently halogen. In embodiments of the formulae above, $R^{20}a$ is independently oxo. In embodiments of the formulae above, $R^{20}a$ is independently —CN. In embodiments of the formulae above, $R^{20}a$ is independently $C_{1-6}$alkyl. In embodiments of the formulae above, $R^{20}a$ is independently $C_{2-6}$alkenyl. In embodiments of the formulae above, $R^{20}a$ is independently $C_{2-6}$alkynyl. In embodiments of the formulae above, $R^{20}a$ is independently $C_{3-6}$cycloalkyl. In embodiments of the formulae above, $R^{20}a$ is independently —CH$_2$-C$_{3-6}$cycloalkyl. In embodiments of the formulae above, $R^{20}a$ is independently $C_{2-9}$heterocycloalkyl. In embodiments of the formulae above, $R^{20}a$ is independently —CH$_2$-C$_{2-9}$heterocycloalkyl. In embodiments of the formulae above, $R^{20}a$ is independently $C_{6-10}$aryl. In embodiments of the formulae above, $R^{20}a$ is independently —CH$_2$-C$_{6-10}$aryl. In embodiments of the formulae above, $R^{20}a$ is independently —CH$_2$-C$_{1-9}$heteroaryl. In embodiments of the formulae above, $R^{20}a$ is independently $C_{1-9}$heteroaryl. In embodiments of the formulae above, $R^{20}a$ is independently —OR$^{21}$. In embodiments of the formulae above, $R^{20}a$ is independently —SR$^{21}$. In embodiments of the formulae above, $R^{20}a$ is independently —N(R$^{22}$)(R$^{23}$). In embodiments of the formulae above, $R^{20}a$ is independently —C(O)OR$^{22}$. In embodiments of the formulae above, $R^{20}a$ is independently —C(O)N(R$^{22}$)(R$^{23}$). In embodiments of the formulae above, $R^{20}a$ is independently —C(O)C(O)N(R$^{22}$)(R$^{23}$). In embodiments of the formulae above, $R^{20}a$ is independently —OC(O)N(R$^{22}$)(R$^{23}$). In embodiments of the formulae above, $R^{20}a$ is independently —N(R$^{24}$)C(O)N(R$^{22}$)(R$^{23}$). In embodiments of the formulae above, $R^{20}a$ is independently —N(R$^{24}$)C(O)OR$^{25}$. In embodiments of the formulae above, $R^{20}a$ is independently —N(R$^{24}$)C(O)R$^{25}$. In embodiments of the formulae above, $R^{20}a$ is independently —N(R$^{24}$)C(O)R$^{21}$. In embodiments of the formulae above, $R^{20}a$ is independently —C(O)R$^{21}$. In embodiments of the formulae above, $R^{20}a$ is independently —N(R$^{24}$)S(O)$_2$R$^{25}$. In embodiments of the formulae above, $R^{20}a$ is independently —C(O)R$^{25}$. In embodiments of the formulae above, $R^{20}a$ is independently —S(O)$_2$R$^{25}$. In embodiments of the formulae above, $R^{20}a$ is independently —S(O)$_2$N(R$^{22}$)(R$^{23}$). In embodiments of the formulae above, $R^{20}a$ is independently —OCH$_2$C(O)OR$^{22}$. In embodiments of the formulae above, $R^{20}a$ is independently —OC(O)R$^{25}$. In embodiments of the formulae above, $R^{20}a$ is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20}a$ is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20}a$ is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20}a$ is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20}a$ is independently —CH$_2$-C$_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20}a$ is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20}a$ is independently —CH$_2$-C$_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$a is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$a is independently —CH$_2$-C$_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$a is independently —CH$_2$-C$_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$a is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.

In embodiments of the formulae above, R$^{20}$b is independently halogen. In embodiments of the formulae above, R$^{20}$b is independently oxo. In embodiments of the formulae above, R$^{20o}$ is independently —CN. In embodiments of the formulae above, R$^{20}$b is independently $C_{1-6}$alkyl. In embodiments of the formulae above, R$^{20}$b is independently $C_{2-6}$alkenyl. In embodiments of the formulae above, R$^{20}$b is independently $C_{2-6}$alkynyl. In embodiments of the formulae above, R$^{20o}$ is independently $C_{3-6}$cycloalkyl. In embodiments of the formulae above, R$^{20}$b is independently —CH$_2$-C$_{3-6}$cycloalkyl. In embodiments of the formulae above, R$^{20o}$ is independently $C_{2-9}$heterocycloalkyl. In embodiments of the formulae above, R$^{20}$b is independently —CH$_2$-C$_{2-9}$heterocycloalkyl. In embodiments of the formulae above, R$^{20}$b is independently $C_{6-10}$aryl. In embodiments of the formulae above, R$^{20}$b is independently —CH$_2$-C$_6$-10aryl. In embodiments of the formulae above, R$^{20o}$ is independently —CH$_2$-C$_{1-9}$heteroaryl. In embodiments of the formulae above, R$^{20}$b is independently $C_{1-9}$heteroaryl. In embodiments of the formulae above, R$^{20}$b is independently —OR$^{21}$. In embodiments of the formulae above, R$^{20}$b is independently —SR$^{21}$.

In embodiments of the formulae above, R$^{20o}$ is independently —N(R$^{22}$)(R$^{23}$). In embodiments of the formulae above, R$^{20}$b is independently —C(O)OR$^{22}$. In embodiments of the formulae above, R$^{20}$b is independently —C(O)N(R$^{22}$)(R$^{23}$). In embodiments of the formulae above, R$^{20}$b is independently —C(O)C(O)N(R$^{22}$)(R$^{23}$). In embodiments of the formulae above, R$^{20o}$ is independently —OC(O)N(R$^{22}$)(R$^{23}$). In embodiments of the formulae above, R$^{20}$b is independently —N(R$^{24}$)C(O)N(R$^{22}$)(R$^{23}$). In embodiments of the formulae above, R$^{20}$b is independently —N(R$^{24}$)C(O)OR$^{25}$. In embodiments of the formulae above, R$^{20k}$ is independently —N(R$^{24}$)C(O)R$^{25}$. In embodiments of the formulae above, R$^{20}$b is independently —N(R$^{24}$)C(O)R$^{21}$. In embodiments of the formulae above, R$^{20}$b is independently —C(O)R$^{21}$. In embodiments of the formulae above, R$^{20}$b is independently —N(R$^{24}$)S(O)$_2$R$^{25}$. In embodiments of the formulae above, R$^{20}$b is independently —C(O)R$^{25}$. In embodiments of the formulae above, R$^{20}$b is independently —S(O)$_2$R$^{25}$. In embodiments of the formulae above, R$^{20k}$ is independently —S(O)$_2$N(R$^{22}$)(R$^{23}$). In embodiments of the formulae above, R$^{20}$b is independently —OCH$_2$C(O)OR$^{22}$. In embodiments of the formulae above, R$^{20}$b is independently —OC(O)R$^{25}$. In embodiments of the formulae above, R$^{20}$b is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$b is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$b is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20o}$ is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$b is independently —CH$_2$-C$_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)

($R^{23}$), —N($R^{24}$)C(O)N($R^{22}$)($R^{23}$), —N($R^{24}$)C(O) O$R^{25}$, —N($R^{24}$)C(O)$R^{25}$, —N($R^{24}$)S(O)$_2R^{25}$, —C(O) $R^{25}$, —S(O)$_2R^{25}$, —S(O)$_2$N($R^{22}$)($R^{23}$), and —OC(O) $R^{25}$. In embodiments of the formulae above, $R^{20}$b is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{200}$ is independently —CH$_2$-$C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$b is independently $C_{6-10}$aryl optionally substituted with one, two, or three independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N ($R^{22}$)($R^{23}$), —OC(O)N($R^{22}$)($R^{23}$), —N($R^{24}$)C(O)N ($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$ N($R^{22}$)($R^{23}$), and —OC(O)$R^{25}$. In embodiments of the formulae above, $R^{20}$b is independently —CH$_2$-$C_6$-10aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O) O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S (O)$_2R^{25}$, —C(O)$R^{25}$, —S(O)$_2R^{25}$, —S(O)$_2$N($R^{22}$) ($R^{23}$), and —OC(O)$R^{25}$. In embodiments of the formulae above, $R^{200}$ is independently —CH$_2$-$C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N ($R^{22}$)($R^{23}$), —OC(O)N($R^{22}$)($R^{23}$), —N($R^{24}$)C(O)N ($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$b is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$.

In embodiments of the formulae above, $R^{20}$c is independently halogen. In embodiments of the formulae above, $R^{20}$c is independently oxo. In embodiments of the formulae above, $R^{20}$c is independently —CN. In embodiments of the formulae above, $R^{20}$c is independently $C_{1-6}$alkyl. In embodiments of the formulae above, $R^{20}$c is independently $C_{2-6}$alkenyl. In embodiments of the formulae above, $R^{20}$c is independently $C_{2-6}$alkynyl. In embodiments of the formulae above, $R^{20}$c is independently $C_{3-6}$cycloalkyl. In embodiments of the formulae above, $R^{20}$c is independently —CH$_2$-$C_{3-6}$cycloalkyl. In embodiments of the formulae above, $R^{20}$c is independently $C_{2-9}$heterocycloalkyl. In embodiments of the formulae above, $R^{20}$c is independently —CH$_2$-$C_{2-9}$heterocycloalkyl. In embodiments of the formulae above, $R^{20}$c is independently $C_{6-10}$aryl. In embodiments of the formulae above, $R^{20}$c is independently —CH$_2$-$C_6$-10aryl. In embodiments of the formulae above, $R^{20}$c is independently —CH$_2$-$C_{1-9}$heteroaryl. In embodiments of the formulae above, $R^{20}$c is independently $C_{1-9}$heteroaryl. In embodiments of the formulae above, $R^{20}$c is independently selected from —O$R^{21}$, —S$R^{21}$, —N($R^{22}$)($R^{23}$), —C(O)O$R^{22}$, —C(O)N ($R^{22}$)($R^{23}$), —C(O)C(O)N($R^{22}$)($R^{23}$), —OC(O)N($R^{22}$) ($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2$ $R^{25}$, —S(O)$_2$N($R^{22}$)($R^{23}$), —OCH$_2$C(O)O$R^{22}$, and —OC(O)$R^{25}$. In embodiments of the formulae above, $R^{20}$c is independently selected from $C_{1-6}$alkyl, $C_{2-6}$alkenyl, $C_{2-6}$alkynyl, $C_{3-6}$cycloalkyl, —CH$_2$-$C_{3-6}$cycloalkyl, $C_{2-9}$heterocycloalkyl, —CH$_2$-$C_{2-9}$heterocycloalkyl, $C_{6-10}$aryl, —CH$_2$-$C_6$-10aryl, —CH$_2$-$C_{1-9}$heteroaryl, and $C_{1-9}$heteroaryl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N ($R^{22}$)($R^{23}$), —N($R^{24}$)C(O)N($R^{22}$)($R^{23}$), —N($R^{24}$)C(O) O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$c is independently —O$R^{21}$. In embodiments of the formulae above, $R^{20}$c is independently —S$R^{21}$. In embodiments of the formulae above, $R^{20}$c is independently —N($R^{22}$)($R^{23}$). In embodiments of the formulae above, $R^{20}$c is independently —C(O) O$R^{22}$. In embodiments of the formulae above, $R^{20}$c is independently —C(O)N($R^{22}$)($R^{23}$). In embodiments of the formulae above, $R^{20}$c is independently —C(O)C(O)N($R^{22}$) ($R^{23}$). In embodiments of the formulae above, $R^{20}$c is independently —OC(O)N($R^{22}$)($R^{23}$). In embodiments of the formulae above, $R^{20}$c is independently —N($R^{24}$)C(O)N ($R^{22}$)($R^{23}$). In embodiments of the formulae above, $R^{20}$c is independently —N($R^{24}$)C(O)O$R^{25}$. In embodiments of the formulae above, $R^{20}$c is independently —N($R^{24}$)C(O)$R^{25}$. In embodiments of the formulae above, $R^{20}$c is independently —N($R^{24}$)S(O)$_2R^{25}$. In embodiments of the formulae above, $R^{20}$c is independently —C(O)$R^{25}$. In embodiments of the formulae above, $R^{20}$c is independently —C(O)$R^{21}$. In embodiments of the formulae above, $R^{20}$c is independently —N($R^{24}$)C(O)$R^{21}$. In embodiments of the formulae above, $R^{20}$c is independently —S(O)$_2R^{25}$. In embodiments of the formulae above, $R^{20}$c is independently —S(O)$_2$N($R^{22}$)($R^{23}$). In embodiments of the formulae above, $R^{20}$c is independently —OCH$_2$C(O)O$R^{22}$. In embodiments of the formulae above, $R^{20}$c is independently —OC(O)$R^{25}$. In embodiments of the formulae above, $R^{20}$c is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$) C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{2-6}$alkenyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{2-6}$alkynyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{3-6}$cycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently —CH$_2$-C$_{3-6}$cycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{2-9}$heterocycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently —CH$_2$-C$_{2-9}$heterocycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently —CH$_2$-C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently —CH$_2$-C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$.

In embodiments of the formulae above, $R^{20}$d is independently halogen. In embodiments of the formulae above, $R^{20}$d is independently oxo. In embodiments of the formulae above, $R^{20}$d is independently —CN. In embodiments of the formulae above, $R^{20}$d is independently C$_{1-6}$alkyl. In embodiments of the formulae above, $R^{20}$d is independently C$_{2-6}$alkenyl. In embodiments of the formulae above, $R^{20}$d is independently C$_{2-6}$alkynyl. In embodiments of the formulae above, $R^{20}$d is independently C$_{3-6}$cycloalkyl. In embodiments of the formulae above, $R^{20}$d is independently —CH$_2$-C$_{3-6}$cycloalkyl. In embodiments of the formulae above, $R^{20}$d is independently C$_{2-9}$heterocycloalkyl. In embodiments of the formulae above, $R^{20}$d is independently —CH$_2$-C$_{2-9}$heterocycloalkyl. In embodiments of the formulae above, $R^{20}$d is independently C$_{6-10}$aryl. In embodiments of the formulae above, $R^{20}$d is independently —CH$_2$-C$_{6}$-10aryl. In embodiments of the formulae above, $R^{20}$d is independently —CH$_2$-C$_{1-9}$heteroaryl. In embodiments of the formulae above, $R^{20}$d is independently C$_{1-9}$heteroaryl. In embodiments of the formulae above, $R^{20}$d is independently —O$R^{21}$. In embodiments of the formulae above, $R^{20}$d is independently —S$R^{21}$. In embodiments of the formulae above, $R^{20}$d is independently —N($R^{22}$)($R^{23}$). In embodiments of the formulae above, $R^{20}$d is independently —C(O)O$R^{22}$. In embodiments of the formulae above, $R^{20}$d is independently —C(O)N($R^{22}$)($R^{23}$). In embodiments of the formulae above, $R^{20}$d is independently —C(O)C(O)N($R^{22}$)($R^{23}$). In embodiments of the formulae above, $R^{20}$d is independently —OC(O)N($R^{22}$)($R^{23}$). In embodiments of the formulae above, $R^{20}$d is independently —N($R^{24}$)C(O)N($R^{22}$)($R^{23}$). In embodiments of the formulae above, $R^{20}$d is independently —N($R^{24}$)C(O)O$R^{25}$. In embodiments of the formulae above, $R^{20}$d is independently —N($R^{24}$)C(O)$R^{25}$. In embodiments of the formulae above, $R^{20}$d is independently —N($R^{24}$)C(O)$R^{21}$. In embodiments of the formulae above, $R^{20}$d is independently —C(O)$R^{21}$. In embodiments of the formulae above, $R^{20}$d is independently —N($R^{24}$)S(O)$_2R^{25}$. In embodiments of the formulae above, $R^{20}$d is independently —C(O)$R^{25}$. In embodiments of the formulae above, $R^{20}$d is independently —S(O)$_2R^{25}$. In embodiments of the formulae above, $R^{20}$d is independently —S(O)$_2$N($R^{22}$)($R^{23}$). In embodiments of the formulae above, $R^{20}$d is independently —OCH$_2$C(O)O$R^{22}$. In embodiments of the formulae above, $R^{20}$d is independently —OC(O)$R^{25}$. In embodiments of the formulae above, $R^{20}$d is independently selected from $C_{1-6}$alkyl, $C_{2-6}$alkenyl, $C_{2-6}$alkynyl, $C_{3-6}$cycloalkyl, —CH$_2$-$C_{3-6}$cycloalkyl, $C_{2-9}$heterocycloalkyl, —CH$_2$-$C_{2-9}$heterocycloalkyl, $C_{6-10}$aryl, —CH$_2$-$C_6$-10aryl, —CH$_2$-$C_{1-9}$heteroaryl, and $C_{1-9}$heteroaryl; each optionally substituted with one, two, or three groups independently selected from halogen, oxo, —CN, $C_{1-6}$alkyl, $C_{1-6}$haloalkyl, $C_{1-6}$ alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2$ $R^{25}$, —S(O)$_2$N($R^{22}$)($R^{23}$), and —OC(O)$R^{25}$. In embodiments of the formulae above, $R^{20}$d is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$.

In embodiments of the formulae above, $R^{20}$d is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently —CH$_2$-$C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently —CH$_2$-$C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently —CH$_2$-$C_6$-10aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently —CH$_2$-$C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20}$d is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$.

In embodiments of the formulae above, $R^{20}$c is independently halogen. In embodiments of the formulae above, $R^{20}$c is independently oxo. In embodiments of the formulae above, $R^{20}c$ is independently —CN. In embodiments of the formulae above, $R^{20}c$ is independently $C_{1-6}$alkyl. In embodiments of the formulae above, $R^{20}e$ is independently $C_{2-6}$alkenyl. In embodiments of the formulae above, $R^{20}c$ is independently $C_{2-6}$alkynyl. In embodiments of the formulae above, $R^{20}e$ is independently $C_{3-6}$cycloalkyl. In embodiments of the formulae above, $R^{20}e$ is independently —$CH_2$-$C_{3-6}$cycloalkyl. In embodiments of the formulae above, $R^{20}e$ is independently $C_2$-heterocycloalkyl. In embodiments of the formulae above, $R^{20}c$ is independently —$CH_2$-$C_{2-9}$heterocycloalkyl. In embodiments of the formulae above, $R^{20}c$ is independently $C_{6-10}$aryl. In embodiments of the formulae above, $R^{20}c$ is independently —$CH_2$-$C_{6-10}$aryl. In embodiments of the formulae above, $R^{20}c$ is independently —$CH_2$-$C_{1-9}$heteroaryl. In embodiments of the formulae above, $R^{20}e$ is independently $C_{1-9}$heteroaryl. In embodiments of the formulae above, $R^{20}c$ is independently —$OR^{21}$. In embodiments of the formulae above, $R^{20}c$ is independently —$SR^{21}$. In embodiments of the formulae above, $R^{20}c$ is independently —$N(R^{22})(R^{23})$. In embodiments of the formulae above, $R^{20}e$ is independently —$C(O)OR^{22}$. In embodiments of the formulae above, $R^{20}c$ is independently —$C(O)N(R^{22})(R^{23})$. In embodiments of the formulae above, $R^{20}c$ is independently —$C(O)C(O)N(R^{22})(R^{23})$. In embodiments of the formulae above, $R^{20}e$ is independently —$OC(O)N(R^{22})(R^{23})$. In embodiments of the formulae above, $R^{20}c$ is independently —$N(R^{24})C(O)N(R^{22})(R^{23})$. In embodiments of the formulae above, $R^{20}c$ is independently —$N(R^{24})C(O)OR^{25}$. In embodiments of the formulae above, $R^{20}c$ is independently —$N(R^{24})C(O)R^{25}$. In embodiments of the formulae above, $R^{20}e$ is independently —$N(R^{24})C(O)R^{21}$. In embodiments of the formulae above, $R^{20}c$ is independently —$C(O)R^{21}$. In embodiments of the formulae above, $R^{20}c$ is independently —$N(R^{24})S(O)_2R^{25}$. In embodiments of the formulae above, $R^{20}c$ is independently —$C(O)R^{25}$. In embodiments of the formulae above, $R^{20}c$ is independently —$S(O)_2R^{25}$. In embodiments of the formulae above, $R^{20}c$ is independently —$S(O)_2N(R^{22})(R^{23})$. In embodiments of the formulae above, $R^{20}c$ is independently —$OCH_2C(O)OR^{22}$. In embodiments of the formulae above, $R^{20}e$ is independently —$OC(O)R^{25}$. In embodiments of the formulae above, $R^{20}c$ is independently selected from $C_{1-6}$alkyl, $C_{2-6}$alkenyl, $C_{2-6}$alkynyl, $C_{3-6}$cycloalkyl, —$CH_2$-$C_{3-6}$cycloalkyl, $C_2$-heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently —$N(R^{24})S(O)_2R^{25}$. In embodiments of the formulae above, $R^{20}c$ is independently —$C(O)R^{25}$. In embodiments of the formulae above, $R^{20}c$ is independently —$C(O)R^{21}$. In embodiments of the formulae above, $R^{20}c$ is independently —$N(R^{24})C(O)R^{21}$. In embodiments of the formulae above, $R^{20}c$ is independently —$S(O)_2R^{25}$. In embodiments of the formulae above, $R^{20}c$ is independently —$S(O)_2N(R^{22})(R^{23})$. In embodiments of the formulae above, $R^{20}e$ is independently —$OCH_2C(O)OR^{22}$. In embodiments of the formulae above, $R^{20}e$ is independently —$OC(O)R^{25}$. In embodiments of the formulae above, $R^{20}c$ is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently —$CH_2$-$C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20}c$ is independently —$CH_2$-$C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC$ (O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$e is independently —CH$_2$-C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$c is independently —CH$_2$-C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$e is independently C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$.

In embodiments of the formulae above, $R^{20}$f is independently halogen. In embodiments of the formulae above, $R^{20}$f is independently oxo. In embodiments of the formulae above, $R^{20}$f is independently —CN. In embodiments of the formulae above, $R^{20}$f is independently C$_{1-6}$alkyl. In embodiments of the formulae above, $R^{20}$f is independently C$_{2-6}$alkenyl. In embodiments of the formulae above, $R^{20}$f is independently C$_{2-6}$alkynyl. In embodiments of the formulae above, $R^{20}$f is independently C$_{3-6}$cycloalkyl. In embodiments of the formulae above, $R^{20}$f is independently —CH$_2$-C$_{3-6}$cycloalkyl. In embodiments of the formulae above, $R^{20}$f is independently C$_2$-heterocycloalkyl. In embodiments of the formulae above, $R^{20}$f is independently —CH$_2$-C$_{2-9}$heterocycloalkyl. In embodiments of the formulae above, $R^{20}$f is independently C$_{6-10}$aryl. In embodiments of the formulae above, $R^{20}$f is independently —CH$_2$-C$_6$-10aryl. In embodiments of the formulae above, $R^{20}$f is independently —CH$_2$-C$_{1-9}$heteroaryl. In embodiments of the formulae above, $R^{20}$f is independently C$_{1-9}$heteroaryl. In embodiments of the formulae above, $R^{20}$f is independently —O$R^{21}$. In embodiments of the formulae above, $R^{20}$f is independently —S$R^{21}$. In embodiments of the formulae above, $R^{20}$f is independently —N($R^{22}$)($R^{23}$). In embodiments of the formulae above, $R^{20}$f is independently —C(O)O$R^{22}$. In embodiments of the formulae above, $R^{20}$f is independently —C(O)N($R^{22}$)($R^{23}$). In embodiments of the formulae above, $R^{20}$f is independently —C(O)C(O)N($R^{22}$)($R^{23}$). In embodiments of the formulae above, $R^{20}$f is independently —OC(O)N($R^{22}$)($R^{23}$). In embodiments of the formulae above, $R^{20}$f is independently —N($R^{24}$)C(O)N($R^{22}$)($R^{23}$). In embodiments of the formulae above, $R^{20}$f is independently —N($R^{24}$)C(O)O$R^{25}$. In embodiments of the formulae above, $R^{20}$f is independently —N($R^{24}$)C(O)$R^{25}$. In embodiments of the formulae above, $R^{20}$f is independently —N($R^{24}$)C(O)$R^{21}$. In embodiments of the formulae above, $R^{20}$f is independently —C(O)$R^{21}$. In embodiments of the formulae above, $R^{20}$f is independently —N($R^{24}$)S(O)$_2$$R^{25}$. In embodiments of the formulae above, $R^{20}$f is independently —C(O)$R^{25}$. In embodiments of the formulae above, $R^{20}$f is independently —S(O)$_2$$R^{25}$. In embodiments of the formulae above, $R^{20}$f is independently —S(O)$_2$N($R^{22}$)($R^{23}$). In embodiments of the formulae above, $R^{20}$f is independently —OCH$_2$C(O)O$R^{22}$. In embodiments of the formulae above, $R^{20}$f is independently —OC(O)$R^{25}$. In embodiments of the formulae above, $R^{20}$f is independently selected from C$_{1-6}$alkyl, C$_{2-6}$alkenyl, C$_{2-6}$alkynyl, C$_{3-6}$cycloalkyl, —CH$_2$-C$_{3-6}$cycloalkyl, C$_{2-9}$heterocycloalkyl, —CH$_2$-C$_{2-9}$heterocycloalkyl, C$_{6-10}$aryl, —CH$_2$-C$_6$-10aryl, —CH$_2$-C$_{1-9}$heteroaryl, and C$_{1-9}$heteroaryl; each optionally substituted with one, two, or three groups independently selected from halogen, oxo, —CN, C$_{1-6}$alkyl, C$_{1-6}$haloalkyl, C$_{1-6}$alkoxy, C$_1$-haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$f is independently C$_{1-6}$alkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$.

In embodiments of the formulae above, $R^{20}$f is independently C$_{2-6}$alkenyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$f is independently C$_{2-6}$alkynyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$. In embodiments of the formulae above, $R^{20}$f is independently C$_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently —CH$_2$-C$_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently —CH$_2$-C$_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently —CH$_2$-C$_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently —CH$_2$-C$_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20}$f is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.

In embodiments of the formulae above, R$^{20g}$ is independently halogen. In embodiments of the formulae above, R$^{20g}$ is independently oxo. In embodiments of the formulae above, R$^{20g}$ is independently —CN. In embodiments of the formulae above, R$^{20g}$ is independently $C_{1-6}$alkyl. In embodiments of the formulae above, R$^{20g}$ is independently $C_{2-6}$alkenyl. In embodiments of the formulae above, R$^{20g}$ is independently $C_{2-6}$alkynyl. In embodiments of the formulae above, R$^{20g}$ is independently $C_{3-6}$cycloalkyl. In embodiments of the formulae above, R$^{20g}$ is independently —CH$_2$-C$_{3-6}$cycloalkyl. In embodiments of the formulae above, R$^{20g}$ is independently $C_{2-9}$heterocycloalkyl. In embodiments of the formulae above, R$^{20g}$ is independently —CH$_2$-C$_{2-9}$heterocycloalkyl. In embodiments of the formulae above, R$^{20g}$ is independently $C_{6-10}$aryl. In embodiments of the formulae above, R$^{20g}$ is independently —CH$_2$-C$_{6-10}$aryl. In embodiments of the formulae above, R$^{20g}$ is independently —CH$_2$-C$_{1-9}$heteroaryl. In embodiments of the formulae above, R$^{20g}$ is independently $C_{1-9}$heteroaryl. In embodiments of the formulae above, R$^{20g}$ is independently —OR$^{21}$. In embodiments of the formulae above, R$^{20g}$ is independently —SR$^{21}$. In embodiments of the formulae above, R$^{20g}$ is independently —N(R$^{22}$)(R$^{23}$). In embodiments of the formulae above, R$^{20g}$ is independently —C(O)OR$^{22}$. In embodiments of the formulae above, R$^{20g}$ is independently —C(O)N(R$^{22}$)(R$^{23}$). In embodiments of the formulae above, R$^{20g}$ is independently —C(O)C(O)N(R$^{22}$)(R$^{23}$). In embodiments of the formulae above, R$^{20g}$ is independently —OC(O)N(R$^{22}$)(R$^{23}$). In embodiments of the formulae above, R$^{20g}$ is independently —N(R$^{24}$)C(O)N(R$^{22}$)(R$^{23}$). In embodiments of the formulae above, R$^{20g}$ is independently —N(R$^{24}$)C(O)OR$^{25}$. In embodiments of the formulae above, R$^{20g}$ is independently —N(R$^{24}$)C(O)R$^{25}$. In embodiments of the formulae above, R$^{20g}$ is independently —N(R$^{24}$)C(O)R$^{21}$. In embodiments of the formulae above, R$^{20g}$ is independently —C(O)R$^{21}$. In embodiments of the formulae above, R$^{20g}$ is independently —N(R$^{24}$)S(O)$_2$R$^{25}$. In embodiments of the formulae above, R$^{20g}$ is independently —C(O)R$^{25}$. In embodiments of the formulae above, R$^{20g}$ is independently —S(O)$_2$R$^{25}$. In embodiments of the formulae above, R$^{20g}$ is independently —S(O)$_2$N(R$^{22}$)(R$^{23}$). In embodiments of the formulae above, R$^{20g}$ is independently —OCH$_2$C(O)OR$^{22}$. In embodiments of the formulae above, R$^{20g}$ is independently —OC(O)R$^{25}$. In embodiments of the formulae above, R$^{20g}$ is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20g}$ is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently —CH$_2$-$C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently —CH$_2$-$C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently —CH$_2$-$C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently —CH$_2$-$C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20g}$ is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$. In embodiments of the formulae above, $R^{20h}$ is independently halogen. In embodiments of the formulae above, $R^{20h}$ is independently oxo. In embodiments of the formulae above, $R^{20h}$ is independently —CN. In embodiments of the formulae above, $R^{20h}$ is independently $C_{1-6}$alkyl. In embodiments of the formulae above, $R^{20h}$ is independently $C_{2-6}$alkenyl. In embodiments of the formulae above, $R^{20h}$ is independently $C_{2-6}$alkynyl. In embodiments of the formulae above, $R^{20h}$ is independently $C_{3-6}$cycloalkyl. In embodiments of the formulae above, $R^{20h}$ is independently —CH$_2$-$C_{3-6}$cycloalkyl. In embodiments of the formulae above, $R^{20h}$ is independently $C_{2-9}$heterocycloalkyl. In embodiments of the formulae above, $R^{20h}$ is independently —CH$_2$-$C_{2-9}$heterocycloalkyl. In embodiments of the formulae above, $R^{20h}$ is independently $C_{6-10}$aryl. In embodiments of the formulae above, $R^{20h}$ is independently —CH$_2$-$C_{6-10}$aryl. In embodiments of the formulae above, $R^{20h}$ is independently —CH$_2$-$C_{1-9}$heteroaryl. In embodiments of the formulae above, $R^{20h}$ is independently $C_{1-9}$heteroaryl. In embodiments of the formulae above, $R^{20h}$ is independently —O$R^{21}$. In embodiments of the formulae above, $R^{20h}$ is independently —S$R^{21}$. In embodiments of the formulae above, $R^{20h}$ is independently —N($R^{22}$)($R^{23}$). In embodiments of the formulae above, $R^{20h}$ is independently —C(O)O$R^{22}$. In embodiments of the formulae above, $R^{20h}$ is independently —C(O)N($R^{22}$)($R^{23}$). In embodiments of the formulae above, $R^{20h}$ is independently —C(O)C(O)N($R^{22}$)($R^{23}$). In embodiments of the formulae above, $R^{20h}$ is independently —OC(O)N($R^{22}$)($R^{23}$). In embodiments of the formulae above, $R^{20h}$ is independently —N($R^{24}$)C(O)N($R^{22}$)($R^{23}$). In embodiments of the formulae above, $R^{20h}$ is independently —N($R^{24}$)C(O)O$R^{25}$. In embodiments of the formulae above, $R^{20h}$ is independently —N($R^{24}$)C(O)$R^{25}$. In embodiments of the formulae above, $R^{20h}$ is independently —N($R^{24}$)C(O)$R^{21}$. In embodiments of the formulae above, $R^{20h}$ is independently —C(O)$R^{21}$. In embodiments of the formulae above, $R^{20h}$ is independently —N($R^{24}$)S(O)$_2R^{25}$. In embodiments of the formulae above, $R^{20h}$ is independently —C(O)$R^{25}$. In embodiments of the formulae above, $R^{20h}$ is independently $-S(O)_2R^{25}$. In embodiments of the formulae above, $R^{20h}$ is independently $-S(O)_2N(R^{22})(R^{23})$. In embodiments of the formulae above, $R^{20h}$ is independently $-OCH_2C(O)OR^{22}$. In embodiments of the formulae above, $R^{20h}$ is independently $-OC(O)R^{25}$. In embodiments of the formulae above, $R^{20h}$ is independently selected from $C_{1-6}$alkyl, $C_{2-6}$alkenyl, $C_{2-6}$alkynyl, $C_{3-6}$cycloalkyl, $-CH_2-C_{3-6}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl; each optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{1-6}$alkyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{2-6}$alkenyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{2-6}$alkynyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{3-6}$cycloalkyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $-CH_2-C_{3-6}$cycloalkyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{2-9}$heterocycloalkyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $-CH_2-C_{2-9}$heterocycloalkyl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{6-10}$aryl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $-CH_2-C_{6-10}$aryl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $-CH_2-C_{1-9}$heteroaryl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$. In embodiments of the formulae above, $R^{20h}$ is independently $C_{1-9}$heteroaryl optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$.

In embodiments of the formulae above, $R^{20i}$ is independently halogen. In embodiments of the formulae above, $R^{20i}$ is independently oxo. In embodiments of the formulae above, $R^{20i}$ is independently $-CN$. In embodiments of the formulae above, $R^{20i}$ is independently $C_{1-6}$alkyl. In embodiments of the formulae above, $R^{20i}$ is independently $C_{2-6}$alkenyl. In embodiments of the formulae above, $R^{20i}$ is independently $C_{2-6}$alkynyl. In embodiments of the formulae above, $R^{20i}$ is independently $C_{3-6}$cycloalkyl. In embodiments of the formulae above, $R^{20i}$ is independently —CH$_2$-C$_{3-6}$cycloalkyl. In embodiments of the formulae above, $R^{20i}$ is independently $C_{2-9}$heterocycloalkyl. In embodiments of the formulae above, $R^{20i}$ is independently —CH$_2$-C$_{2-9}$heterocycloalkyl. In embodiments of the formulae above, $R^{20i}$ is independently $C_{6-10}$aryl. In embodiments of the formulae above, $R^{20i}$ is independently —CH$_2$-C$_{6-10}$aryl. In embodiments of the formulae above, $R^{20i}$ is independently —CH$_2$-C$_{1-9}$heteroaryl. In embodiments of the formulae above, $R^{20i}$ is independently $C_{1-9}$heteroaryl. In embodiments of the formulae above, $R^{20i}$ is independently —OR$^{21}$. In embodiments of the formulae above, $R^{20i}$ is independently —SR$^{21}$. In embodiments of the formulae above, $R^{20i}$ is independently —N(R$^{22}$)(R$^{23}$). In embodiments of the formulae above, $R^{20i}$ is independently —C(O)OR$^{22}$. In embodiments of the formulae above, $R^{20i}$ is independently —C(O)N(R$^{22}$)(R$^{23}$). In embodiments of the formulae above, $R^{20i}$ is independently —C(O)C(O)N(R$^{22}$)(R$^{23}$). In embodiments of the formulae above, $R^{20i}$ is independently —OC(O)N(R$^{22}$)(R$^{23}$). In embodiments of the formulae above, $R^{20i}$ is independently —N(R$^{24}$)C(O)N(R$^{22}$)(R$^{23}$). In embodiments of the formulae above, $R^{20i}$ is independently —N(R$^{24}$)C(O)OR$^{25}$. In embodiments of the formulae above, $R^{20i}$ is independently —N(R$^{24}$)C(O)R$^{25}$. In embodiments of the formulae above, $R^{20i}$ is independently —N(R$^{24}$)C(O)R$^{21}$. In embodiments of the formulae above, $R^{20i}$ is independently —C(O)R$^{21}$. In embodiments of the formulae above, $R^{20i}$ is independently —N(R$^{24}$)S(O)$_2$R$^{25}$. In embodiments of the formulae above, $R^{20i}$ is independently —C(O)R$^{25}$. In embodiments of the formulae above, $R^{20i}$ is independently —S(O)$_2$R$^{25}$. In embodiments of the formulae above, $R^{20i}$ is independently —S(O)$_2$N(R$^{22}$)(R$^{23}$). In embodiments of the formulae above, $R^{20i}$ is independently —OCH$_2$C(O)OR$^{22}$. In embodiments of the formulae above, $R^{20i}$ is independently —OC(O)R$^{25}$. In embodiments of the formulae above, $R^{20i}$ is independently selected from $C_{1-6}$alkyl, $C_{2-6}$alkenyl, $C_{2-6}$alkynyl, $C_{3-6}$cycloalkyl, —CH$_2$-C$_{3-6}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, and $C_{1-9}$heteroaryl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently —CH$_2$-C$_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently —CH$_2$-C$_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently —CH$_2$-C$_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, $R^{20i}$ is independently —CH$_2$-C$_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20i}$ is independently $C_{1-9}$heteroaryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$.

In embodiments of the formulae above, $R^{20j}$ is independently halogen. In embodiments of the formulae above, $R^{20j}$ is independently oxo. In embodiments of the formulae above, $R^{20j}$ is independently —CN. In embodiments of the formulae above, $R^{20j}$ is independently $C_{1-6}$alkyl. In embodiments of the formulae above, $R^{20j}$ is independently $C_{2-6}$alkenyl. In embodiments of the formulae above, $R^{20j}$ is independently $C_{2-6}$alkynyl. In embodiments of the formulae above, $R^{20j}$ is independently $C_{3-6}$cycloalkyl. In embodiments of the formulae above, $R^{20j}$ is independently —$CH_2$-$C_{3-6}$cycloalkyl. In embodiments of the formulae above, $R^{20j}$ is independently $C_{2-9}$heterocycloalkyl. In embodiments of the formulae above, $R^{20j}$ is independently —$CH_2$-$C_{2-9}$heterocycloalkyl. In embodiments of the formulae above, $R^{20j}$ is independently $C_{6-10}$aryl. In embodiments of the formulae above, $R^{20j}$ is independently —$CH_2$-$C_{6-10}$aryl. In embodiments of the formulae above, $R^{20j}$ is independently —$CH_2$-$C_{1-9}$heteroaryl. In embodiments of the formulae above, $R^{20j}$ is independently $C_{1-9}$heteroaryl. In embodiments of the formulae above, $R^{20j}$ is independently —$OR^{21}$. In embodiments of the formulae above, $R^{20j}$ is independently —$SR^{21}$. In embodiments of the formulae above, $R^{20j}$ is independently —$N(R^{22})(R^{23})$. In embodiments of the formulae above, $R^{20j}$ is independently —$C(O)OR^{22}$. In embodiments of the formulae above, $R^{20j}$ is independently —$C(O)N(R^{22})(R^{23})$. In embodiments of the formulae above, $R^{20j}$ is independently —$C(O)C(O)N(R^{22})(R^{23})$. In embodiments of the formulae above, $R^{20j}$ is independently —$OC(O)N(R^{22})(R^{23})$. In embodiments of the formulae above, $R^{20j}$ is independently —$N(R^{24})C(O)N(R^{22})(R^{23})$. In embodiments of the formulae above, $R^{20j}$ is independently —$N(R^{24})C(O)OR^{25}$. In embodiments of the formulae above, $R^{20j}$ is independently —$N(R^{24})C(O)R^{25}$. In embodiments of the formulae above, $R^{20j}$ is independently —$N(R^{24})C(O)R^{21}$. In embodiments of the formulae above, $R^{20j}$ is independently —$C(O)R^{21}$. In embodiments of the formulae above, $R^{20j}$ is independently —$N(R^{24})S(O)_2R^{25}$. In embodiments of the formulae above, $R^{20j}$ is independently —$C(O)R^{25}$. In embodiments of the formulae above, $R^{20j}$ is independently —$S(O)_2R^{25}$. In embodiments of the formulae above, $R^{20j}$ is independently —$S(O)_2N(R^{22})(R^{23})$. In embodiments of the formulae above, $R^{20j}$ is independently —$OCH_2C(O)OR^{22}$. In embodiments of the formulae above, $R^{20j}$ is independently —$OC(O)R^{25}$. In embodiments of the formulae above, $R^{20j}$ is independently $C_{1-6}$alkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently $C_{2-6}$alkenyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently $C_{2-6}$alkynyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently —$CH_2$-$C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently $C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently —$CH_2$-$C_{2-9}$heterocycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently $C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$. In embodiments of the formulae above, $R^{20j}$ is independently —$CH_2$-$C_{6-10}$aryl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$. In embodiments of the formulae above, $R^{20j}$ is independently —CH$_2$-C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$. In embodiments of the formulae above, $R^{20j}$ is independently C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$ haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$ R$^{25}$, —S(O)$_2$N($R^{22}$)($R^{23}$), and —OC(O)R$^{25}$.

In embodiments of the formulae above, $R^{20k}$ is independently halogen. In embodiments of the formulae above, $R^{20k}$ is independently oxo. In embodiments of the formulae above, $R^{20k}$ is independently —CN. In embodiments of the formulae above, $R^{20k}$ is independently C$_{1-6}$alkyl. In embodiments of the formulae above, $R^{20k}$ is independently C$_{2-6}$alkenyl. In embodiments of the formulae above, $R^{20k}$ is independently C$_{2-6}$alkynyl. In embodiments of the formulae above, $R^{20k}$ is independently C$_{3-6}$cycloalkyl. In embodiments of the formulae above, $R^{20k}$ is independently —CH$_2$-C$_{3-6}$cycloalkyl. In embodiments of the formulae above, $R^{20k}$ is independently C$_{2-9}$heterocycloalkyl. In embodiments of the formulae above, $R^{20k}$ is independently —CH$_2$-C$_{2-9}$heterocycloalkyl. In embodiments of the formulae above, $R^{20k}$ is independently C$_{6-10}$aryl. In embodiments of the formulae above, $R^{20k}$ is independently —CH$_2$-C$_{6-10}$aryl. In embodiments of the formulae above, $R^{20k}$ is independently —CH$_2$-C$_{1-9}$heteroaryl. In embodiments of the formulae above, $R^{20k}$ is independently C$_{1-9}$heteroaryl. In embodiments of the formulae above, $R^{20k}$ is independently —OR$^{21}$. In embodiments of the formulae above, $R^{20k}$ is independently —SR$^{21}$. In embodiments of the formulae above, $R^{20k}$ is independently —N($R^{22}$)($R^{23}$). In embodiments of the formulae above, $R^{20k}$ is independently —C(O)OR$^{22}$. In embodiments of the formulae above, $R^{20k}$ is independently —C(O)N($R^{22}$)($R^{23}$). In embodiments of the formulae above, $R^{20k}$ is independently —C(O)C(O)N($R^{22}$)($R^{23}$). In embodiments of the formulae above, $R^{20k}$ is independently —OC(O)N($R^{22}$)($R^{23}$). In embodiments of the formulae above, $R^{20k}$ is independently —N($R^{24}$)C(O)N($R^{22}$)($R^{23}$). In embodiments of the formulae above, $R^{20k}$ is independently —N($R^{24}$)C(O)OR$^{25}$. In embodiments of the formulae above, $R^{20k}$ is independently —N($R^{24}$)C(O)R$^{25}$. In embodiments of the formulae above, $R^{20k}$ is independently —N($R^{24}$)C(O)R$^{21}$. In embodiments of the formulae above, $R^{20k}$ is independently —C(O)R$^{21}$. In embodiments of the formulae above, $R^{20k}$ is independently —N($R^{24}$)S(O)$_2$R$^{25}$. In embodiments of the formulae above, $R^{20k}$ is independently —C(O)R$^{25}$. In embodiments of the formulae above, $R^{20k}$ is independently —S(O)$_2$R$^{25}$. In embodiments of the formulae above, $R^{20k}$ is independently —S(O)$_2$N($R^{22}$)($R^{23}$). In embodiments of the formulae above, $R^{20k}$ is independently —OCH$_2$C(O)OR$^{22}$. In embodiments of the formulae above, $R^{20k}$ is independently —OC(O)R$^{25}$. In embodiments of the formulae above, $R^{20k}$ is independently C$_{1-6}$alkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$. In embodiments of the formulae above, $R^{20k}$ is independently C$_{2-6}$alkenyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$ R$^{25}$, —S(O)$_2$N($R^{22}$)($R^{23}$), and —OC(O)R$^{25}$. In embodiments of the formulae above, $R^{20k}$ is independently C$_{2-6}$alkynyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$ R$^{25}$, —S(O)$_2$N($R^{22}$)($R^{23}$), and —OC(O)R$^{25}$. In embodiments of the formulae above, $R^{20k}$ is independently C$_{3-6}$cycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$ R$^{25}$, —S(O)$_2$N($R^{22}$)($R^{23}$), and —OC(O)R$^{25}$. In embodiments of the formulae above, $R^{20k}$ is independently —CH$_2$-C$_{3-6}$cycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$. In embodiments of the formulae above, $R^{20k}$ is independently C$_{2-9}$heterocycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$ R$^{25}$, —S(O)$_2$N($R^{22}$)($R^{23}$), and —OC(O)R$^{25}$. In embodiments of the formulae above, $R^{20k}$ is independently —CH$_2$-C$_{2-9}$heterocycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$. In embodiments of the formulae above, $R^{20k}$ is independently C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)

(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵. In embodiments of the formulae above, R²⁰ᵏ is independently —CH₂-C₆₋₁₀aryl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵. In embodiments of the formulae above, R²⁰ᵏ is independently —CH₂-C₁₋₉heteroaryl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵. In embodiments of the formulae above, R²⁰ᵏ is independently C₁₋₉heteroaryl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵.

In embodiments of the formulae above, R²⁰ˡ is independently halogen. In embodiments of the formulae above, R²⁰ˡ is independently oxo. In embodiments of the formulae above, R²⁰ˡ is independently —CN. In embodiments of the formulae above, R²⁰ˡ is independently C₁₋₆alkyl. In embodiments of the formulae above, R²⁰ˡ is independently C₂₋₆alkenyl. In embodiments of the formulae above, R²⁰ˡ is independently C₂₋₆alkynyl. In embodiments of the formulae above, R²⁰ˡ is independently C₃₋₆cycloalkyl. In embodiments of the formulae above, R²⁰ˡ is independently —CH₂-C₃₋₆cycloalkyl. In embodiments of the formulae above, R²⁰ˡ is independently C₂₋₉heterocycloalkyl. In embodiments of the formulae above, R²⁰ˡ is independently —CH₂-C₂₋₉heterocycloalkyl. In embodiments of the formulae above, R²⁰ˡ is independently C₆₋₁₀aryl. In embodiments of the formulae above, R²⁰ˡ is independently —CH₂-C₆₋₁₀aryl. In embodiments of the formulae above, R²⁰ˡ is independently —CH₂-C₁₋₉heteroaryl. In embodiments of the formulae above, R²⁰ˡ is independently C₁₋₉heteroaryl. In embodiments of the formulae above, R²⁰ˡ is independently —OR²¹. In embodiments of the formulae above, R²⁰ˡ is independently —SR²¹. In embodiments of the formulae above, R²⁰ˡ is independently —N(R²²)(R²³). In embodiments of the formulae above, R²⁰ˡ is independently —C(O)OR²². In embodiments of the formulae above, R²⁰ˡ is independently —C(O)N(R²²)(R²³). In embodiments of the formulae above, R²⁰ˡ is independently —C(O)C(O)N(R²²)(R²³). In embodiments of the formulae above, R²⁰ˡ is independently —OC(O)N(R²²)(R²³). In embodiments of the formulae above, R²⁰ˡ is independently —N(R²⁴)C(O)N(R²²)(R²³). In embodiments of the formulae above, R²⁰ˡ is independently —N(R²⁴)C(O)OR²⁵. In embodiments of the formulae above, R²⁰ˡ is independently —N(R²⁴)C(O)R²⁵. In embodiments of the formulae above, R²⁰ˡ is independently —N(R²⁴)C(O)R²¹. In embodiments of the formulae above, R²⁰ˡ is independently —C(O)R²¹. In embodiments of the formulae above, R²⁰ˡ is independently —N(R²⁴)S(O)₂R²⁵. In embodiments of the formulae above, R²⁰ˡ is independently —C(O)R²⁵. In embodiments of the formulae above, R²⁰ˡ is independently —S(O)₂R²⁵. In embodiments of the formulae above, R²⁰ˡ is independently —S(O)₂N(R²²)(R²³). In embodiments of the formulae above, R²⁰ˡ is independently —OCH₂C(O)OR²². In embodiments of the formulae above, R²⁰ˡ is independently —OC(O)R²⁵. In embodiments of the formulae above, R²⁰ˡ is independently C₁₋₆alkyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵. In embodiments of the formulae above, R²⁰ˡ is independently C₂₋₆alkenyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵. In embodiments of the formulae above, R²⁰ˡ is independently C₂₋₆alkynyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵. In embodiments of the formulae above, R²⁰ˡ is independently C₃₋₆cycloalkyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂ R²⁵, —S(O)₂N(R²²)(R²³), and —OC(O)R²⁵. In embodiments of the formulae above, R²⁰ˡ is independently —CH₂-C₃₋₆cycloalkyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵. In embodiments of the formulae above, R²⁰ˡ is independently C₂₋₉heterocycloalkyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵. In embodiments of the formulae above, R²⁰ˡ is independently —CH₂-C₂₋₉heterocycloalkyl optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)

OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20l}$ is independently C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20l}$ is independently —CH$_2$-C$_{6-10}$aryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20l}$ is independently —CH$_2$-C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$. In embodiments of the formulae above, R$^{20l}$ is independently C$_{1-9}$heteroaryl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.

The individual embodiments herein below, or combinations thereof, (e.g., embodiments of R$^{1a}$, R$^{1b}$, R$^{1c}$, R$^{1d}$, R$^{1h}$, or R$^{20z}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A"), (B"), (C"), (A"-1), (B"-1), (C"-1), (A"-1a), (B"-1a), (C"-1a), (A"-1b), (B"-1b), (C"-1b), (A"-1c), (B"-1c), (C"-1c), (A"-1d), (B"-1d), (C"-1d), (A"-1e), (B"-1e), (C"-1e), (A"-1f), (B"-1f), or (C"-1f), or a pharmaceutically acceptable salt or solvate thereof. In embodiments of the formulae above, each R$^{1a}$ is independently hydrogen. In embodiments of the formulae above, each R$^{1a}$ is independently halogen. In embodiments of the formulae above, each R$^{1a}$ is independently oxo. In embodiments of the formulae above, each R$^{1a}$ is independently —CN. In embodiments of the formulae above, each R$^{1a}$ is independently C$_{1-6}$alkyl. In embodiments of the formulae above, each R$^{1a}$ is independently C$_{2-6}$alkenyl. In embodiments of the formulae above, each R$^{1a}$ is independently C$_{2-6}$alkynyl. In embodiments of the formulae above, each R$^{1a}$ is independently C$_{3-12}$cycloalkyl. In embodiments of the formulae above, each R$^{1a}$ is independently C$_{2-11}$heterocycloalkyl. In embodiments of the formulae above, each R$^{1a}$ is independently C$_{6-10}$aryl. In embodiments of the formulae above, each R$^{1a}$ is independently C$_{1-9}$heteroaryl. In embodiments of the formulae above, each R$^{1a}$ is independently —OR$^{12}$. In embodiments of the formulae above, each R$^{1a}$ is independently —SR$^{12}$. In embodiments of the formulae above, each R$^{1a}$ is independently —N(R$^{12}$)(R$^{13}$). In embodiments of the formulae above, each R$^{1a}$ is independently selected from —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and -CH$_2$S(O)$_2$N(R$^{12}$)(R$^{13}$). In embodiments of the formulae above, each R$^{1a}$ is independently C$_{1-6}$alkyl substituted with one, two, or three R$^{20z}$. In embodiments of the formulae above, each R$^{1a}$ is independently C$_{2-6}$alkenyl substituted with one, two, or three R$^{20z}$. In embodiments of the formulae above, each R$^{1a}$ is independently C$_{2-6}$alkynyl substituted with one, two, or three R$^{20z}$. In embodiments of the formulae above, each R$^{1a}$ is independently C$_{3-12}$cycloalkyl substituted with one, two, or three R$^{20z}$. In embodiments of the formulae above, each R$^{1a}$ is independently C$_{2-11}$heterocycloalkyl substituted with one, two, or three R$^{20z}$. In embodiments of the formulae above, each R$^{1a}$ is independently C$_{6-10}$aryl substituted with one, two, or three R$^{20z}$. In embodiments of the formulae above, each R$^{1a}$ is independently C$_{1-9}$heteroaryl substituted with one, two, or three R$^{20z}$. In embodiments of the formulae above, R$^{1a}$ is independently F. In embodiments of the formulae above, R$^{1a}$ is independently C$_{1-6}$ In embodiments of the formulae above, R$^{1a}$ is independently Br. In embodiments of the formulae above, R$^{1a}$ is independently I. In embodiments of the formulae above, Rla is independently C$_{1-6}$alkyl. In embodiments of the formulae above, R$^{1a}$ is independently methyl. In embodiments of the formulae above, R$^{1a}$ is independently ethyl. In embodiments of the formulae above, R$^{1a}$ is independently isopropyl. In embodiments of the formulae above, R$^{1a}$ is independently C$_{2-6}$alkenyl. In embodiments of the formulae above, R$^{1a}$ is independently C$_{2-6}$alkynyl. In embodiments of the formulae above, R$^{1a}$ is independently C$_{1-6}$haloalkyl. In embodiments of the formulae above, R$^{1a}$ is independently —CF$_3$. In embodiments of the formulae above, R$^{1a}$ is independently C$_{6-12}$aryl. In embodiments of the formulae above, R$^{1a}$ is independently C$_{1-11}$heteroaryl. In embodiments of the formulae above, R$^{1a}$ is independently —OH. In embodiments of the formulae above, R$^{1a}$ is independently —OCH$_3$. In embodiments of the formulae above, $R^{1a}$ is independently —SH. In embodiments of the formulae above, $R^{1a}$ is independently —SCH$_3$. In embodiments of the formulae above, $R^{1a}$ is independently —N(CH$_3$)$_2$. In embodiments of the formulae above, $R^{1a}$ is independently —N(H)$_2$. In embodiments of the formulae above, $R^{1a}$ is independently selected from —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the formulae above, each $R^{1a}$ is independently —C(O)OR$^{12}$. In embodiments of the formulae above, each $R^{1a}$ is independently selected from —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, $R^{1a}$ is independently —OH. In embodiments of the formulae above, $R^{1a}$ is independently —OCH$_3$. In embodiments of the formulae above, Rla is independently —SH. In embodiments of the formulae above, $R^{1a}$ is independently —SCH$_3$. In embodiments of the formulae above, Rla is independently —N(CH$_3$)$_2$. In embodiments of the formulae above, $R^{1a}$ is independently —N(H)$_2$. In embodiments of the formulae above, $R^{1a}$ is independently —C(O)OH. In embodiments of the formulae above, $R^{1a}$ is independently selected from —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

In embodiments of the formulae above, each $R^{1b}$ is independently hydrogen. In embodiments of the formulae above, each $R^{1b}$ is independently halogen. In embodiments of the formulae above, each $R^{1b}$ is independently oxo. In embodiments of the formulae above, each $R^{1b}$ is independently —CN. In embodiments of the formulae above, each $R^{1b}$ is independently C$_{1-6}$alkyl. In embodiments of the formulae above, each $R^{1b}$ is independently C$_{2-6}$alkenyl. In embodiments of the formulae above, each $R^{1b}$ is independently C$_{2-6}$alkynyl. In embodiments of the formulae above, each $R^{1b}$ is independently C$_{3-12}$cycloalkyl. In embodiments of the formulae above, each $R^{1b}$ is independently C$_{2-11}$heterocycloalkyl. In embodiments of the formulae above, each $R^{1b}$ is independently C$_{6-10}$aryl. In embodiments of the formulae above, each $R^{1b}$ is independently C$_{1-9}$heteroaryl. In embodiments of the formulae above, each $R^{1b}$ is independently —OR$^{12}$. In embodiments of the formulae above, each $R^{1b}$ is independently —SR$^{12}$. In embodiments of the formulae above, each $R^{1b}$ is independently —N(R$^{12}$)(R$^{13}$). In embodiments of the formulae above, each $R^{1b}$ is independently selected from —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, each $R^{1b}$ is independently C$_{1-6}$alkyl substituted with one, two, or three R$^{20z}$. In embodiments of the formulae above, each $R^{1b}$ is independently C$_{2-6}$alkenyl substituted with one, two, or three R$^{20z}$. In embodiments of the formulae above, each $R^{1b}$ is independently C$_{2-6}$alkynyl substituted with one, two, or three R$^{20z}$. In embodiments of the formulae above, each $R^{1b}$ is independently C$_{3-12}$cycloalkyl substituted with one, two, or three R$^{20z}$. In embodiments of the formulae above, each $R^{1b}$ is independently C$_{2-11}$heterocycloalkyl substituted with one, two, or three R$^{20z}$. In embodiments of the formulae above, each $R^{1b}$ is independently C$_{6-10}$aryl substituted with one, two, or three R$^{20z}$. In embodiments of the formulae above, each $R^{1b}$ is independently C$_{1-9}$heteroaryl substituted with one, two, or three R$^{20z}$. In embodiments of the formulae above, $R^{1b}$ is independently F. In embodiments of the formulae above, $R^{1b}$ is independently C$_{1-6}$ In embodiments of the formulae above, $R^{1b}$ is independently Br. In embodiments of the formulae above, $R^{1b}$ is independently I. In embodiments of the formulae above, $R^{1b}$ is independently C$_{1-6}$alkyl. In embodiments of the formulae above, $R^{1b}$ is independently methyl. In embodiments of the formulae above, $R^{1b}$ is independently ethyl. In embodiments of the formulae above, $R^{1b}$ is independently isopropyl. In embodiments of the formulae above, $R^{1b}$ is independently C$_{2-6}$alkenyl. In embodiments of the formulae above, $R^{1b}$ is independently C$_{2-6}$alkynyl. In embodiments of the formulae above, $R^{1b}$ is independently C$_{1-6}$haloalkyl. In embodiments of the formulae above, $R^{1b}$ is independently —CF$_3$. In embodiments of the formulae above, $R^{1b}$ is independently C$_{6-12}$aryl. In embodiments of the formulae above, $R^{1b}$ is independently C$_{1-11}$heteroaryl. In embodiments of the formulae above, $R^{1b}$ is independently —OH. In embodiments of the formulae above, $R^{1b}$ is independently —OCH$_3$. In embodiments of the formulae above, $R^{1b}$ is independently —SH. In embodiments of the formulae above, $R^{1b}$ is independently —SCH$_3$. In embodiments of the formulae above, $R^{1b}$ is independently —N(CH$_3$)$_2$. In embodiments of the formulae above, $R^{1b}$ is independently —N(H)$_2$. In embodiments of the formulae above, $R^{1b}$ is independently selected from —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the formulae above, each $R^{1b}$ is independently —C(O)OR$^{12}$. In embodiments of the formulae above, each $R^{1b}$ is independently selected from —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, $R^{1b}$ is independently —OH. In embodiments of the formulae above, $R^{1b}$ is independently —OCH$_3$. In embodiments of the formulae above, R$^{16}$ is independently —SH. In embodiments of the formulae above, R$^{1b}$ is independently —SCH$_3$. In embodiments of the formulae above, R$^{1b}$ is independently —N(CH$_3$)$_2$. In embodiments of the formulae above, R$^{16}$ is independently —N(H)$_2$. In embodiments of the formulae above, R$^{1b}$ is independently —C(O)OH. In embodiments of the formulae above, R$^{1b}$ is independently —C(O)OCH$_3$. In embodiments of the formulae above, R$^{1b}$ is independently selected from —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

In embodiments of the formulae above, each R$^{1d}$ is independently hydrogen. In embodiments of the formulae above, each R$^{1d}$ is independently halogen. In embodiments of the formulae above, each R$^{1d}$ is independently oxo. In embodiments of the formulae above, each R$^{1d}$ is independently —CN. In embodiments of the formulae above, each R$^{1d}$ is independently C$_{1-6}$alkyl. In embodiments of the formulae above, each R$^{1d}$ is independently C$_{2-6}$alkenyl. In embodiments of the formulae above, each Rid is independently C$_{2-6}$alkynyl. In embodiments of the formulae above, each R$^{1d}$ is independently C$_{3-12}$cycloalkyl. In embodiments of the formulae above, each R$^{1d}$ is independently C$_{2-11}$heterocycloalkyl. In embodiments of the formulae above, each Rid is independently C$_{6-10}$aryl. In embodiments of the formulae above, each R$^{1d}$ is independently C$_{1-9}$heteroaryl. In embodiments of the formulae above, each R$^{1d}$ is independently —OR$^{12}$. In embodiments of the formulae above, each R$^{1d}$ is independently —SR$^{12}$. In embodiments of the formulae above, each R$^{1d}$ is independently —N(R$^{12}$)(R$^{13}$). In embodiments of the formulae above, each R$^{1d}$ is independently selected from —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, each R$^{1d}$ is independently C$_{1-6}$alkyl substituted with one, two, or three R$^{20z}$. In embodiments of the formulae above, each R$^{1d}$ is independently C$_{2-6}$alkenyl substituted with one, two, or three R$^{20z}$. In embodiments of the formulae above, each R$^{1d}$ is independently C$_{2-6}$alkynyl substituted with one, two, or three R$^{20z}$. In embodiments of the formulae above, each Rid is independently C$_{3-12}$cycloalkyl substituted with one, two, or three R$^{20z}$. In embodiments of the formulae above, each R$^{1d}$ is independently C$_{2-11}$heterocycloalkyl substituted with one, two, or three R$^{20z}$. In embodiments of the formulae above, each R$^{1d}$ is independently C$_{6-10}$aryl substituted with one, two, or three R$^{20z}$. In embodiments of the formulae above, each R$^{1d}$ is independently C$_{1-9}$heteroaryl substituted with one, two, or three R$^{20z}$. In embodiments of the formulae above, R$^{1d}$ is independently F. In embodiments of the formulae above, R$^{1d}$ is independently C$_{1-6}$ In embodiments of the formulae above, R$^{1d}$ is independently Br. In embodiments of the formulae above, R$^{1d}$ is independently I. In embodiments of the formulae above, Rid is independently C$_{1-6}$alkyl. In embodiments of the formulae above, Rd is independently methyl. In embodiments of the formulae above, R$^{1d}$ is independently ethyl. In embodiments of the formulae above, R$^{1d}$ is independently isopropyl. In embodiments of the formulae above, R$^{1d}$ is independently C$_{2-6}$alkenyl. In embodiments of the formulae above, R$^{1d}$ is independently C$_{2-6}$alkynyl. In embodiments of the formulae above, R$^{1d}$ is independently C$_{1-6}$haloalkyl. In embodiments of the formulae above, R$^{1d}$ is independently —CF$_3$. In embodiments of the formulae above, R$^{1d}$ is independently C$_{6-12}$aryl. In embodiments of the formulae above, R$^{1d}$ is independently C$_{1-11}$heteroaryl. In embodiments of the formulae above, R$^{1d}$ is independently —OH. In embodiments of the formulae above, R$^{1d}$ is independently —OCH$_3$. In embodiments of the formulae above, R$^{1d}$ is independently —SH. In embodiments of the formulae above, R$^{1d}$ is independently —SCH$_3$. In embodiments of the formulae above, R$^{1d}$ is independently —N(CH$_3$)$_2$. In embodiments of the formulae above, R$^{1d}$ is independently —N(H)$_2$. In embodiments of the formulae above, R$^{1d}$ is independently selected from —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the formulae above, each R$^{1d}$ is independently —C(O)OR$^{12}$. In embodiments of the formulae above, each R$^{1d}$ is independently selected from —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, R$^{1d}$ is independently —OH. In embodiments of the formulae above, R$^{1d}$ is independently —OCH$_3$. In embodiments of the formulae above, R$^{1d}$ is independently —SH. In embodiments of the formulae above, R$^{1d}$ is independently —SCH$_3$. In embodiments of the formulae above, R$^{1d}$ is independently —N(CH$_3$)$_2$. In embodiments of the formulae above, R$^{1d}$ is independently —N(H)$_2$. In embodiments of the formulae above, R$^{1d}$ is independently —C(O)OH. In embodiments of the formulae above, R$^{1d}$ is independently —C(O)OCH$_3$. In embodiments of the formulae above, R$^{1d}$ is independently selected from —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

In embodiments of the formulae above, each R$^{1h}$ is independently hydrogen. In embodiments of the formulae above, each R$^{1h}$ is independently halogen. In embodiments of the formulae above, each R$^{1h}$ is independently oxo. In embodiments of the formulae above, each R$^{1h}$ is independently —CN. In embodiments of the formulae above, each R$^{1h}$ is independently C$_{1-6}$alkyl. In embodiments of the formulae above, each R$^{1h}$ is independently C$_{2-6}$alkenyl. In embodiments of the formulae above, each R$^{1h}$ is independently C$_{2-6}$alkynyl. In embodiments of the formulae above, each R$^{1h}$ is independently C$_{3-12}$cycloalkyl. In embodiments of the formulae above, each R$^{1h}$ is independently C$_{2-11}$heterocycloalkyl. In embodiments of the formulae above, each R$^{1h}$ is independently C$_{6-10}$aryl. In embodiments of the formulae above, each R$^{1h}$ is independently C$_{1-9}$heteroaryl. In embodiments of the formulae above, each R$^{1h}$ is independently —OR$^{12}$. In embodiments of the formulae above, each R$^{1h}$ is independently —SR$^{12}$. In embodiments of the formulae above, each R$^{1h}$ is independently —N(R$^{12}$)(R$^{13}$). In embodiments of the formulae above, each R$^{1h}$ is independently selected from —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, each R$^{1h}$ is independently C$_{1-6}$alkyl substituted with one, two, or three R$^{20z}$. In embodiments of the formulae above, each R$^{1h}$ is independently C$_{2-6}$alkenyl substituted with one, two, or three R$^{20z}$. In embodiments of the formulae above, each R$^{1h}$ is independently C$_{2-6}$alkynyl substituted with one, two, or three R$^{20z}$. In embodiments of the formulae above, each R$^{1h}$ is independently C$_{3-12}$cycloalkyl substituted with one, two, or three R$^{20z}$. In embodiments of the formulae above, each R$^{1h}$ is independently C$_{2-11}$heterocycloalkyl substituted with one, two, or three R$^{20z}$. In embodiments of the formulae above, each R$^{1h}$ is independently C$_{6-10}$aryl substituted with one, two, or three R$^{20z}$. In embodiments of the formulae above, each R$^{1h}$ is independently C$_{1-9}$heteroaryl substituted with one, two, or three R$^{20z}$. In embodiments of the formulae above, R$^{1h}$ is independently F. In embodiments of the formulae above, R$^{1h}$ is independently C$_{1-6}$ In embodiments of the formulae above, R$^{1h}$ is independently Br. In embodiments of the formulae above, R$^{1h}$ is independently I. In embodiments of the formulae above, R$^{1h}$ is independently C$_{1-6}$alkyl. In embodiments of the formulae above, R$^{1h}$ is independently methyl. In embodiments of the formulae above, R$^{1h}$ is independently ethyl. In embodiments of the formulae above, R$^{1h}$ is independently isopropyl. In embodiments of the formulae above, R$^{1h}$ is independently C$_{2-6}$alkenyl. In embodiments of the formulae above, R$^{1h}$ is independently C$_{2-6}$alkynyl. In embodiments of the formulae above, R$^{1h}$ is independently C$_{1-6}$haloalkyl. In embodiments of the formulae above, R$^{1h}$ is independently —CF$_3$. In embodiments of the formulae above, R$^{1h}$ is independently C$_{6-12}$aryl. In embodiments of the formulae above, R$^{1h}$ is independently C$_{1-11}$heteroaryl. In embodiments of the formulae above, R$^{1h}$ is independently —OH. In embodiments of the formulae above, R$^{1h}$ is independently —OCH$_3$. In embodiments of the formulae above, R$^{1h}$ is independently —SH. In embodiments of the formulae above, R$^{1h}$ is independently —SCH$_3$. In embodiments of the formulae above, R$^{1h}$ is independently —N(CH$_3$)$_2$. In embodiments of the formulae above, R$^{1h}$ is independently —N(H)$_2$. In embodiments of the formulae above, R$^{1h}$ is independently selected from —C(O)OH, —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$. In embodiments of the formulae above, each R$^{1h}$ is independently —C(O)OR$^{12}$. In embodiments of the formulae above, each R$^{1h}$ is independently selected from —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$). In embodiments of the formulae above, R$^{1h}$ is independently —OH. In embodiments of the formulae above, R$^{1h}$ is independently —OCH$_3$. In embodiments of the formulae above, R$^{1h}$ is independently —SH. In embodiments of the formulae above, R$^{1h}$ is independently —SCH$_3$. In embodiments of the formulae above, R$^{1h}$ is independently —N(CH$_3$)$_2$. In embodiments of the formulae above, R$^{1h}$ is independently —N(H)$_2$. In embodiments of the formulae above, R$^{1h}$ is independently —C(O)OH. In embodiments of the formulae above, R$^{1h}$ is independently selected from —C(O)OCH$_3$, —OC(O)N(H)$_2$, —OC(O)N(CH$_3$)$_2$, —N(H)C(O)N(CH$_3$)$_2$, —N(H)C(O)N(H)$_2$, —N(H)C(O)OH, —N(H)C(O)OCH$_3$, —N(H)S(O)$_2$CH$_3$, —C(O)CH$_3$, —C(O)H, —S(O)CH$_3$, —OC(O)CH$_3$, —OC(O)H, —C(O)N(CH$_3$)$_2$, —C(O)C(O)N(CH$_3$)$_2$, —N(H)C(O)H, —N(H)C(O)CH$_3$, —S(O)$_2$CH$_3$, —S(O)$_2$N(H)$_2$, —S(O)$_2$N(CH$_3$)$_2$, S(=O)(=NH)N(H)$_2$, S(=O)(=NH)N(CH$_3$)$_2$, —CH$_2$C(O)N(H)$_2$, —CH$_2$C(O)N(CH$_3$)$_2$, —CH$_2$N(H)C(O)H, —CH$_2$N(H)C(O)CH$_3$, —CH$_2$S(O)$_2$H, —CH$_2$S(O)$_2$CH$_3$, —CH$_2$S(O)$_2$N(CH$_3$)$_2$, and —CH$_2$S(O)$_2$N(H)$_2$.

In embodiments of the formulae above, each R$^{1c}$ is independently hydrogen. In embodiments of the formulae above, each R$^{1c}$ is independently C$_{1-6}$alkyl. In embodiments of the formulae above, each R$^{1c}$ is independently C$_{2-6}$alkenyl. In embodiments of the formulae above, each R$^{1c}$ is independently C$_{2-6}$alkynyl. In embodiments of the formulae above, each R$^{1c}$ is independently C$_{3-12}$cycloalkyl. In embodiments of the formulae above, each R$^{1c}$ is independently C$_{2-11}$heterocycloalkyl. In embodiments of the formulae above, each R$^{1c}$ is independently C$_{6-10}$aryl. In embodiments of the formulae above, each R$^{1c}$ is independently C$_{1-9}$heteroaryl. In embodiments of the formulae above, each R$^{1c}$ is independently C$_{1-6}$alkyl substituted with one, two, or three R$^{20z}$. In embodiments of the formulae above, each R$^{1c}$ is independently C$_{2-6}$alkenyl substituted with one, two, or three R$^{20z}$. In embodiments of the formulae above, each R$^{1c}$ is independently C$_{2-6}$alkynyl substituted with one, two, or three R$^{20z}$. In embodiments of the formulae above, each R$^{1c}$ is independently C$_{3-12}$cycloalkyl substituted with one, two, or three R$^{20z}$. In embodiments of the formulae above, each R$^{1c}$ is independently C$_{2-11}$heterocycloalkyl substituted with one, two, or three R$^{20z}$. In embodiments of the formulae above, each R$^{1c}$ is independently C$_{6-10}$aryl substituted with one, two, or three R$^{20z}$. In embodiments of the formulae above, each R$^{1c}$ is independently C$_{1-9}$heteroaryl substituted with one, two, or three R$^{20z}$. In embodiments of the formulae above, R$^{1c}$ is independently halogen. In embodiments of the formulae above, R$^{1c}$ is independently F. In embodiments of the formulae above, R$^{1c}$ is independently C$_{1-6}$ In embodiments of the formulae above, R$^{1c}$ is independently Br. In embodiments of the formulae above, R$^{1c}$ is independently I. In embodiments of the formulae above, R$^{1c}$ is independently R$^{1c}$ is independently oxo. In embodiments of the formulae above, R$^{1c}$ is independently —CN. In embodiments of the formulae above, R$^{1c}$ is independently C$_{1-6}$alkyl. In embodiments of the formulae above, Rlc is independently methyl. In embodiments of the formulae above, R$^{1c}$ is independently ethyl. In embodiments of the formulae above, $R^{1c}$ is independently isopropyl. In embodiments of the formulae above, $R^{1c}$ is independently $C_{2-6}$alkenyl. In embodiments of the formulae above, $R^{1c}$ is independently $C_{2-6}$alkynyl. In embodiments of the formulae above, $R^{1c}$ is independently $C_{1-6}$haloalkyl. In embodiments of the formulae above, $R^{1c}$ is independently —$CF_3$. In embodiments of the formulae above, $R^{1c}$ is independently $C_{3-12}$cycloalkyl. In embodiments of the formulae above, $R^{1c}$ is independently $C_{2-11}$heterocycloalkyl. In embodiments of the formulae above, $R^{1c}$ is independently $C_{6-12}$aryl. In embodiments of the formulae above, $R^{1c}$ is independently $C_{1-11}$heteroaryl.

In embodiments of the formulae above, each $R^{20z}$ is independently halogen. In embodiments of the formulae above, each $R^{20z}$ is independently oxo. In embodiments of the formulae above, each $R^{20z}$ is independently —CN. In embodiments of the formulae above, each $R^{20z}$ is independently $C_{1-6}$alkyl. In embodiments of the formulae above, each $R^{20z}$ is independently $C_{2-6}$alkenyl. In embodiments of the formulae above, each $R^{20z}$ is independently $C_{2-6}$alkynyl. In embodiments of the formulae above, each $R^{20z}$ is independently $C_{3-10}$cycloalkyl. In embodiments of the formulae above, each $R^{20z}$ is independently —$CH_2$-$C_{3-10}$cycloalkyl. In embodiments of the formulae above, each $R^{20z}$ is independently $C_{2-9}$heterocycloalkyl. In embodiments of the formulae above, each $R^{20z}$ is independently —$CH_2$-$C_{2-9}$heterocycloalkyl. In embodiments of the formulae above, each $R^{20z}$ is independently $C_{6-10}$aryl. In embodiments of the formulae above, each $R^{20z}$ is independently —$CH_2$-$C_{6-10}$aryl. In embodiments of the formulae above, each $R^{20z}$ is independently —$CH_2$-$C_{1-9}$heteroaryl. In embodiments of the formulae above, each $R^{20z}$ is independently $C_{1-9}$heteroaryl. In embodiments of the formulae above, each $R^{20z}$ is independently —$OR^{21}$a. In embodiments of the formulae above, each $R^{20z}$ is independently —$SR^{21}$a. In embodiments of the formulae above, each $R^{20z}$ is independently —$N(R^{22a})(R^{23a})$. In embodiments of the formulae above, each $R^{20z}$ is independently —$C(O)OR^{22}$a. In embodiments of the formulae above, each $R^{20z}$ is independently —$C(O)N(R^{22a})(R^{23a})$. In embodiments of the formulae above, each $R^{20z}$ is independently —$C(O)C(O)N(R^{22a})(R^{23a})$. In embodiments of the formulae above, each $R^{20z}$ is independently —$OC(O)N(R^{22a})(R^{23a})$. In embodiments of the formulae above, each $R^{20z}$ is independently —$N(R^{24a})C(O)N(R^{224})(R^{23a})$. In embodiments of the formulae above, each $R^{20z}$ is independently —$N(R^{24a})C(O)OR^{25}$a. In embodiments of the formulae above, each $R^{20z}$ is independently —$N(R^{24a})C(O)R^{25a}$. In embodiments of the formulae above, each $R^{20z}$ is independently —$N(R^{24a})S(O)_2R^{25a}$. In embodiments of the formulae above, each $R^{20z}$ is independently —$C(O)R^{25a}$. In embodiments of the formulae above, each $R^{20z}$ is independently —$S(O)_2R^{25a}$. In embodiments of the formulae above, each $R^{20z}$ is independently —$S(O)_2N(R^{22a})(R^{23a})$. In embodiments of the formulae above, each $R^{20z}$ is independently —$OCH_2C(O)OR^{22}$a. In embodiments of the formulae above, each $R^{20z}$ is independently —$OC(O)R^{25a}$. In embodiments of the formulae above, each $R^{20}$ is independently $C_{1-6}$alkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{224})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently $C_{2-6}$alkenyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{224})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently $C_{2-6}$alkynyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{224})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently $C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25}$a. In embodiments of the formulae above, each $R^{20z}$ is independently —$CH_2$-$C_{3-10}$cycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently $C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently —$CH_2$-$C_{2-9}$heterocycloalkyl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21a}$, —$SR^{21}$a, —$N(R^{2a})(R^{23})$, —$C(O)OR^{223}$, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently $C_{6-10}$aryl substituted with one, two, or three groups independently selected from halogen, oxo, —CN, $C_{1-6}$alkyl, $C_1$-haloalkyl, $C_{1-6}$alkoxy, $C_{1-6}$haloalkoxy, —$OR^{21}$a, —$SR^{21}$a, —$N(R^{22a})(R^{23a})$, —$C(O)OR^{22}$a, —$C(O)N(R^{22a})(R^{23a})$, —$C(O)C(O)N(R^{22a})(R^{23a})$, —$OC(O)N(R^{22a})(R^{23a})$, —$N(R^{24a})C(O)N(R^{22a})(R^{23a})$, —$N(R^{24a})C(O)OR^{25a}$, —$N(R^{24a})C(O)R^{25a}$, —$N(R^{24a})S(O)_2R^{25a}$, —$C(O)R^{25a}$, —$S(O)_2R^{25a}$, —$S(O)_2N(R^{22a})(R^{23a})$, and —$OC(O)R^{25a}$. In embodiments of the formulae above, each $R^{20z}$ is independently —$CH_2$-$C_{6-10}$aryl substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$a, —$SR^{21}$a, —N($R^{22a}$)($R^{23a}$), —C(O)O$R^{22a}$, —C(O)N($R^{22a}$)($R^{23a}$), —C(O)C(O)N($R^{22a}$)($R^{23a}$), —OC(O)N($R^{224}$)($R^{23a}$), —N($R^{24a}$)C(O)N($R^{22a}$)($R^{23a}$), —N($R^{24a}$)C(O)O$R^{25a}$, —N($R^{24a}$)C(O)O$R^{25a}$, —N($R^{24a}$)S(O)$_2R^{25a}$, —C(O)$R^{25a}$, —S(O)$_2R^{25a}$, —S(O)$_2$N($R^{22a}$)($R^{23a}$), and —OC(O)$R^{25}$a. In embodiments of the formulae above, each $R^{20z}$ is independently —CH$_2$-C$_{1-9}$heteroaryl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$a, —S$R^{21}$a, —N($R^{22a}$)($R^{23a}$), —C(O)O$R^{22}$a, —C(O)N($R^{22a}$)($R^{23a}$), —C(O)C(O)N($R^{22a}$)($R^{23a}$), —OC(O)N($R^{22a}$)($R^{23a}$), —N($R^{24a}$)C(O)N($R^{22a}$)($R^{23a}$), —N($R^{24a}$)C(O)O$R^{25a}$, —N($R^{24a}$)C(O)$R^{25a}$, —N($R^{24a}$)S(O)$_2R^{25a}$, —C(O)$R^{25a}$, —S(O)$_2R^{25a}$, —S(O)$_2$N($R^{22a}$)($R^{23a}$), and —OC(O)$R^{25a}$. In embodiments of the formulae above, each $R^{20z}$ is independently C$_{1-9}$heteroaryl substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$a, —S$R^{21}$a, —N($R^{22a}$)($R^{23a}$), —C(O)O$R^{22}$a, —C(O)N($R^{22a}$)($R^{23a}$), —C(O)C(O)N($R^{224}$)($R^{23a}$), —OC(O)N($R^{22a}$)($R^{23a}$), —N($R^{24a}$)C(O)N($R^{22a}$)($R^{23a}$), —N($R^{24a}$)C(O)O$R^{25a}$, —N($R^{24a}$)C(O)$R^{25a}$, —N($R^{24a}$)S(O)$_2R^{25a}$, —C(O)$R^{25a}$, —S(O)$_2R^{25a}$, —S(O)$_2$N($R^{22a}$)($R^{23a}$), and —OC(O)$R^{25a}$.

The individual embodiments herein below, or combinations thereof, (e.g., embodiments of $R^{21a}$, $R^{22a}$, $R^{23a}$, $R^{24a}$, or $R^{25a}$) are applicable to compounds of Formula (I), (II), (III), (IV), (XVI), (XVII), (Ia), (IIa), (IIIa), (IVa), (XVIa), (XVIIa), (Ib), (IIb), (IIIb), (IVb), (XVIb), (XVIIb), (Ic), (IIc), (IIIc), (IVc), (XVIc), (XVIIc), (Id), (IId), (IIId), (IVd), (XVId), (XVIId), (Ie), (IIe), (IIIe), (IVe), (XVIe), (XVIIe), (If), (IIf), (IIIf), (IVf), (XVIf), (XVIh), (XVIIf), (Va), (VIIa), (VIIIa), (IXa), (Xa), (XIa), (XIIa), (XIIIa), (XIVa), (XVa), (XVIIIa), (XIXa), (XXa), (XXIa), (XXIIa), (XXIIIa), (XXIVa), (XXVa), (XXVIa), (VIIb), (VIIIb), (IXb), (Xb), (XIb), (XIIb), (XIIIb), (XIVb), (XVb), (XVIIIb), (XIXb), (XXb), (XXIb), (XXIIb), (XXIIIb), (XXIVb), (XXVb), (XXVIb), (Vc), (VIIc), (VIIIc), (IXc), (Xc), (XIc), (XIIc), (XIIIc), (XIVc), (XVc), (XVIIIc), (XIXc), (XXc), (XXIc), (XXIIc), (XXIIIc), (XXIVc), (XXVc), (XXVIc), (VIId), (VIIId), (IXd), (Xd), (XId), (XIId), (XIIId), (XIVd), (XVd), (XVIIId), (XIXd), (XXd), (XXId), (XXIId), (XXIIId), (XXIVd), (XXVd), (XXVId), (Ve), (VIIe), (VIIIe), (IXe), (Xe), (XIe), (XIIe), (XIIIe), (XIVe), (XVe), (XVIIIe), (XIXe), (XXe), (XXIe), (XXIIe), (XXIIIe), (XXIVe), (XXVe), (XXVIe), (VIIf), (VIIIf), (IXf), (Xf), (XIf), (XIIf), (XIIIf), (XIVf), (XVf), (XVIIIf), (XIXf), (XXf), (XXIf), (XXIIf), (XXIIIf), (XXIVf), (XXVf), (XXVIf), (A), (B), (C), (A-1), (B-1), (C-1), (A-1a), (B-1a), (C-1a), (A-1b), (B-1b), (C-1b), (A-1c), (B-1c), (C-1c), (A-1d), (B-1d), (C-1d), (A-1e), (B-1e), (C-1e), (A-1f), (B-1f), (C-1f), (A'), (B'), (C'), (A'-1), (B'-1), (C'-1), (A'-1a), (B'-1a), (C'-1a), (A'-1b), (B'-1b), (C'-1b), (A'-1c), (B'-1c), (C'-1c), (A'-1d), (B'-1d), (C'-1d), (A'-1e), (B'-1e), (C'-1e), (A'-1f), (B'-1f), (C'-1f), (A''), (B''), (C''), (A''-1), (B''-1), (C''-1), (A''-1a), (B''-1a), (C''-1a), (A''-1b), (B''-1b), (C''-1b), (A''-1c), (B''-1c), (C''-1c), (A''-1d), (B''-1d), (C''-1d), (A''-1e), (B''-1e), (C''-1e), (A''-1f), (B''-1f), or (C''-1f), or a pharmaceutically acceptable salt or solvate thereof. In embodiments of the formulae above, each $R^{21a}$ is independently H. In embodiments of the formulae above, each $R^{21a}$ is independently C$_{1-6}$alkyl. In embodiments of the formulae above, each $R^{21a}$ is independently C$_{1-6}$haloalkyl. In embodiments of the formulae above, each $R^{21a}$ is independently C$_{2-6}$alkenyl. In embodiments of the formulae above, each $R^{21a}$ is independently C$_{2-6}$alkynyl. In embodiments of the formulae above, each $R^{21a}$ is independently C$_{3-10}$cycloalkyl. In embodiments of the formulae above, each $R^{21a}$ is independently C$_{2-9}$heterocycloalkyl. In embodiments of the formulae above, each $R^{21a}$ is independently C$_{6-10}$aryl. In embodiments of the formulae above, each $R^{21a}$ is independently C$_{1-9}$heteroaryl.

In embodiments of the formulae above, each $R^{22a}$ is independently H. In embodiments of the formulae above, each $R^{22a}$ is independently C$_{1-6}$alkyl. In embodiments of the formulae above, each $R^{22a}$ is independently C$_{1-6}$haloalkyl. In embodiments of the formulae above, each $R^{22a}$ is independently C$_{2-6}$alkenyl. In embodiments of the formulae above, each $R^{22a}$ is independently C$_{2-6}$alkynyl. In embodiments of the formulae above, each $R^{22a}$ is independently C$_{3-10}$cycloalkyl. In embodiments of the formulae above, each $R^{22a}$ is independently C$_{2-9}$heterocycloalkyl. In embodiments of the formulae above, each $R^{22a}$ is independently C$_{6-10}$aryl. In embodiments of the formulae above, each $R^{22a}$ is independently C$_{1-9}$heteroaryl.

In embodiments of the formulae above, each $R^{23a}$ is independently H. In embodiments of the formulae above, each $R^{23a}$ is independently C$_{1-6}$alkyl.

In embodiments of the formulae above, each $R^{24a}$ is independently H. In embodiments of the formulae above, each $R^{24a}$ is independently C$_{1-6}$alkyl.

In embodiments of the formulae above, each $R^{25a}$ is independently C$_{1-6}$alkyl. In embodiments of the formulae above, each $R^{25a}$ is independently C$_{2-6}$alkenyl. In embodiments of the formulae above, each $R^{25a}$ is independently C$_{2-6}$alkynyl. In embodiments of the formulae above, each $R^{25a}$ is independently C$_{3-6}$cycloalkyl. In embodiments of the formulae above, each $R^{25a}$ is independently C$_{2-9}$heterocycloalkyl. In embodiments of the formulae above, each $R^{25a}$ is independently C$_{6-10}$aryl. In embodiments of the formulae above, each $R^{25a}$ is independently C$_{1-9}$heteroaryl.

In some embodiments of a compound of Formula (I), (II), (III), (IV), (XVI), or (XVII), or a pharmaceutically acceptable salt or solvate thereof, the compound has a formula selected from:

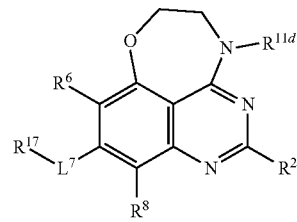

Formula (VIIa)

and

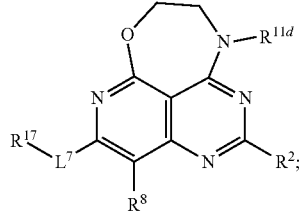

Formula (VIId)

wherein $R^6$ and $R^8$ are independently selected from hydrogen and halogen;

$L^7$ is a bond;

$R^{17}$ is selected from:

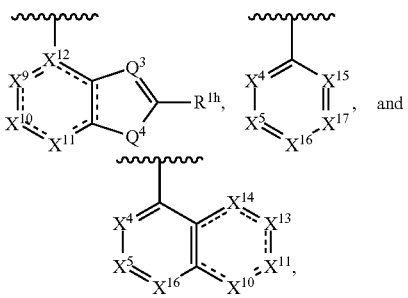

$Q^3$ is N or $C(R^{1d})$; $Q^4$ is S;
$X^4$, $X^5$, $X^{15}$, $X^{16}$, and $X^{17}$ are independently selected from $C(R^{1a})$ or N;
$X^9$ is $C(R^{1a})$; $X^{10}$, $X^{11}$, $X^{13}$, and $X^{14}$ are independently $C(R^{18})$ or N; $X^{12}$ is C; each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_3$. 4 cycloalkyl, $C_{2-4}$heterocycloalkyl, —OH, —NH2, —C(O)OH, —OC(O)NH2, and —C(O)CH$_3$;
$R^{1d}$ is selected from hydrogen, —CN, $C_{1-4}$alkyl, and $C_{1-4}$haloalkyl;
$R^2$ is selected from

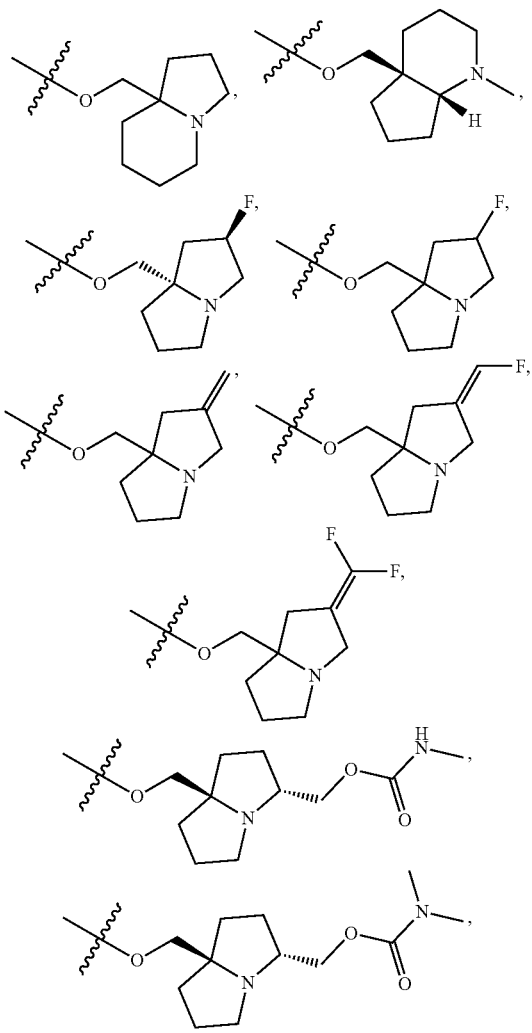

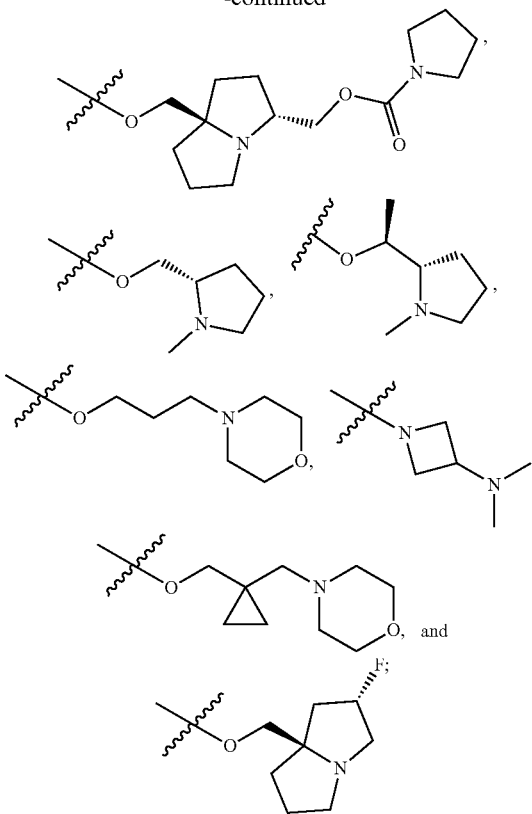

each $R^{11d}$ is independently selected from $C_{1-6}$alkyl, $C_{2-6}$alkenyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{1-11}$heteroaryl, $C_{1-11}$heteroaryl, —(C$_{1-6}$alkyl)-N(R$^{14}$)C(O)R$^{12}$, wherein $C_{1-6}$alkyl, $C_{2-6}$alkenyl, $C_3$. 12 cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{1-11}$heteroaryl, and $C_{1-11}$heteroaryl are optionally substituted with one, two, or three $R^{20k}$, each $R^{12}$ is independently selected from hydrogen, $C_{1-6}$alkyl, $C_{3-10}$cycloalkyl, $C_{2-9}$heterocycloalkyl, —CH$_2$-$C_{2-9}$heterocycloalkyl, wherein $C_{1-6}$alkyl, $C_{3-10}$cycloalkyl, $C_{2-9}$heterocycloalkyl, and —CH$_2$-$C_{2-9}$heterocycloalkyl are optionally substituted with one, two, or three $R^{20l}$; each $R^{1d}$ is independently selected from hydrogen, $C_{1-6}$alkyl, and $C_{1-6}$haloalkyl; each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-6}$heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —OR$^{21}$, and —N(R$^{22}$)(R$^{23}$); each $R^{20l}$ is independently selected from halogen, —OR$^{21}$, and $C_{3-10}$cycloalkyl; each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl; each $R^{22}$ is independently selected from H and $C_{1-6}$alkyl; each $R^{23}$ is independently selected from H and $C_{1-6}$alkyl; each $R^{24}$ is independently selected from H and $C_{1-6}$alkyl; and each $R^{25}$ is independently selected from $C_{1-6}$alkyl and $C_{3-6}$cycloalkyl.

In some embodiments of a compound of Formula (I), (II), (III), (IV), (XVI), or (XVII), or a pharmaceutically acceptable salt or solvate thereof, the compound has a formula selected from:

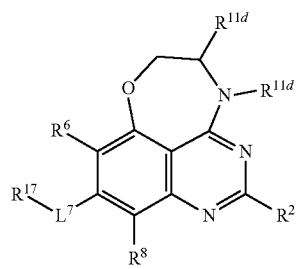

Formula (XVIIIa)

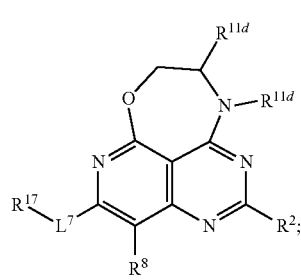

Formula (XVIIId)

wherein
$R^6$ and $R^8$ are independently selected from hydrogen and halogen;
$L^7$ is a bond;
$R^{17}$ is selected from:

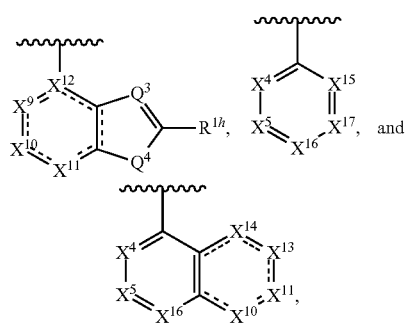

$Q^3$ is N or $C(R^{14})$; $Q^4$ is S;
$X^4, X^3, X^{15}, X^{16},$ and $X^{17}$ are independently selected from $C(R^{1a})$ or N;
$X^9$ is $C(R^{1a})$; $X^{10}, X^{11}, X^{13},$ and $X^{14}$ are independently $C(R^{1a})$ or N; $X^{12}$ is C; each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH2, —C(O)OH, —OC(O)NH2, and —C(O)CH$_3$;
$R^{1d}$ is selected from hydrogen, —CN, $C_{1-4}$alkyl, and $C_{1-4}$haloalkyl;

$R^2$ is selected from

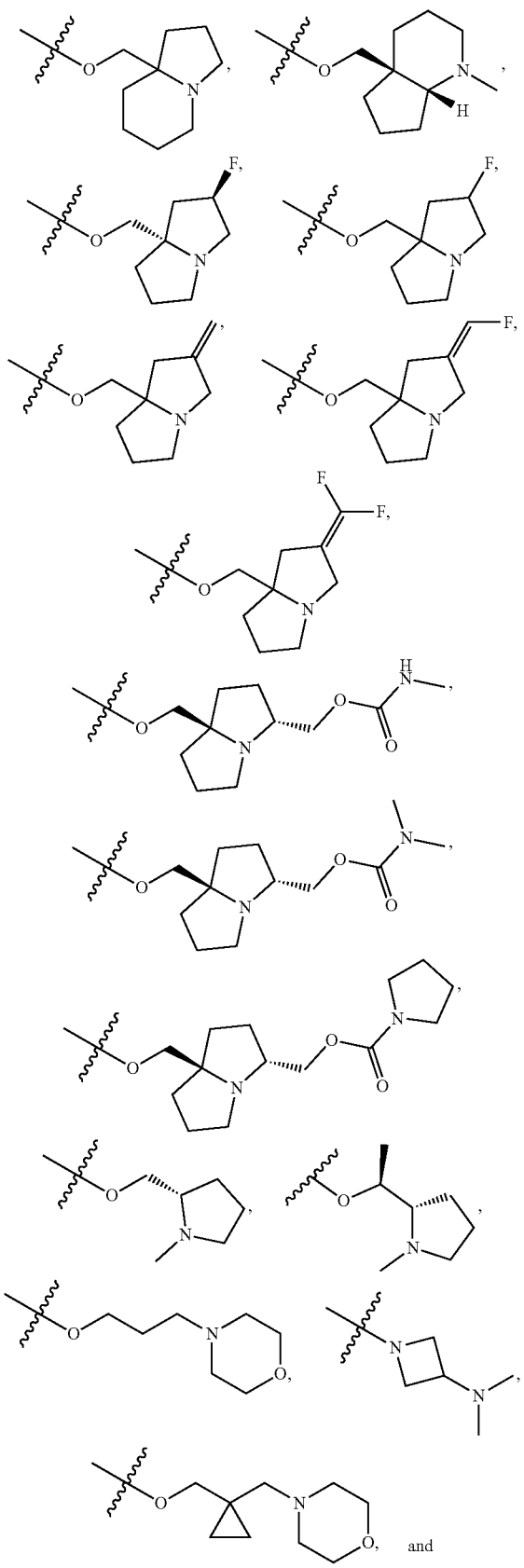

-continued

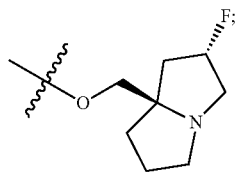

each R$^{11d}$ is independently selected from C$_{1-6}$alkyl, C$_{2-6}$alkenyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{1-11}$heteroaryl, C$_{1-11}$heteroaryl, —(C$_{1-6}$alkyl)-N(R$^{14}$)C(O)R$^{12}$, wherein C$_{1-6}$alkyl, C$_{2-6}$alkenyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{1-11}$heteroaryl, and C$_{1-11}$heteroaryl are optionally substituted with one, two, or three R$^{20k}$; each R$^{12}$ is independently selected from hydrogen, C$_{1-6}$alkyl, C$_{3-10}$cycloalkyl, C$_{2-9}$heterocycloalkyl, —CH$_2$-C$_{2-9}$heterocycloalkyl, wherein C$_{1-6}$alkyl, C$_{3-10}$cycloalkyl, C$_{2-9}$heterocycloalkyl, and —CH$_2$-C$_{2-9}$heterocycloalkyl are optionally substituted with one, two, or three R$^{20l}$; each R$^{1d}$ is independently selected from hydrogen, C$_{1-6}$alkyl, and C$_{1-6}$haloalkyl; each R$^{20k}$ is independently selected from halogen, oxo, —CN, C$_{1-6}$alkyl, C$_{2-6}$alkenyl, C$_{3-10}$cycloalkyl, C$_{2-9}$heterocycloalkyl, C$_{1-9}$heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein C$_{1-6}$alkyl, C$_{2-6}$alkenyl, C$_{3-10}$cycloalkyl, C$_{2-9}$heterocycloalkyl, and C$_{1-9}$heteroaryl are optionally substituted with one, two, or three groups independently selected from halogen, —CN, C$_{1-6}$alkyl, C$_{1-6}$haloalkyl, —OR$^{21}$, and —N(R$^{22}$)(R$^{23}$); each R$^{20l}$ is independently selected from halogen, —OR$^{21}$, and C$_{3-10}$cycloalkyl; each R$^{21}$ is independently selected from H, C$_{1-6}$alkyl, C$_{1-6}$haloalkyl, C$_{3-10}$cycloalkyl, C$_{2-9}$heterocycloalkyl, and C$_{1-9}$heteroaryl; each R$^{22}$ is independently selected from H and C$_{1-6}$alkyl; each R$^{23}$ is independently selected from H and C$_{1-6}$alkyl; each R$^{24}$ is independently selected from H and C$_{1-6}$alkyl; and each R$^{25}$ is independently selected from C$_{1-6}$alkyl and C$_{3-6}$cycloalkyl.

In some embodiments of a compound of Formula (I), (II), (III), (IV), (XVI), or (XVII), or a pharmaceutically acceptable salt or solvate thereof, the compound has a formula selected from:

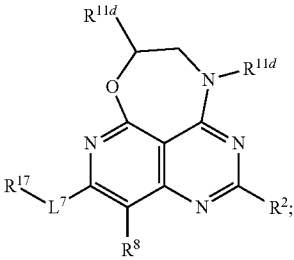

Formula (XIXa)

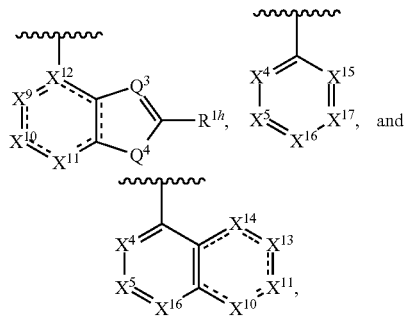

Formula (XIXd)

wherein
R$^6$ and R$^8$ are independently selected from hydrogen and halogen;
L$^7$ is a bond;
R$^{17}$ is selected from:

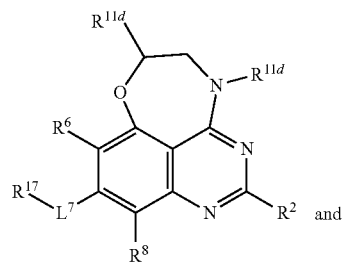

Q$^3$ is N or C(R$^{1a}$); Q$^4$ is S;
X$^4$, X$^5$, X$^{15}$, X$^{16}$, and X$^{17}$ are independently selected from C(R$^{1a}$) or N;
X$^9$ is C(R$^{1a}$); X$^{10}$, X$^{11}$, X$^{13}$, and X$^{14}$ are independently C(R$^{1a}$) or N; X$^{12}$ is C; each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH2, —C(O)OH, —OC(O)NH2, and —C(O)CH$_3$;
R$^{1d}$ is selected from hydrogen, —CN, C$_{1-4}$alkyl, and C$_{1-4}$haloalkyl;
R$^2$ is selected from

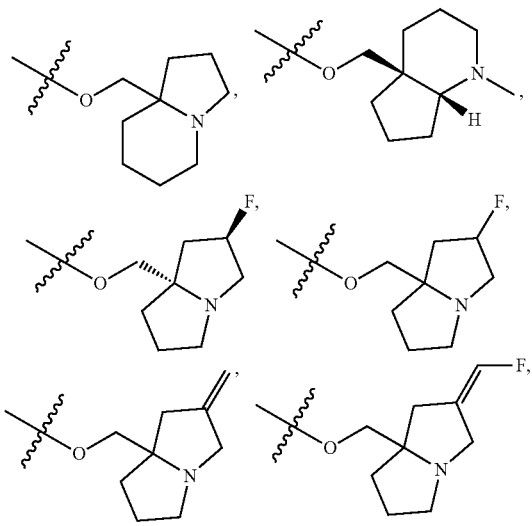

863
-continued

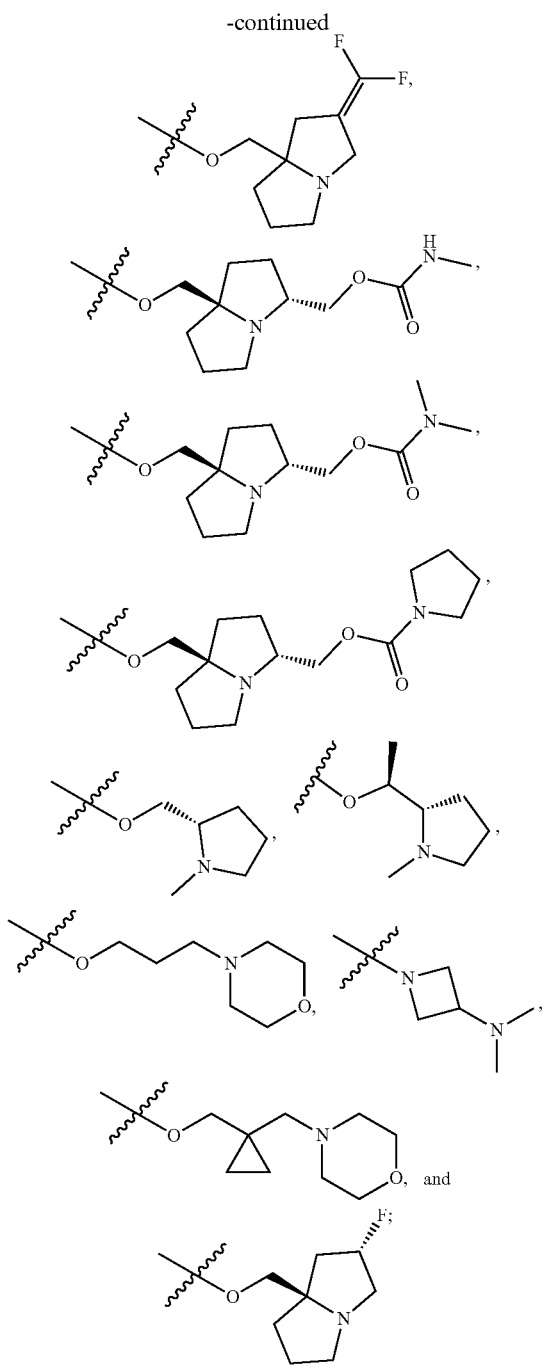

each $R^{11d}$ is independently selected from $C_{1-6}$alkyl, $C_{2-6}$alkenyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, $C_{1-11}$heteroaryl, —($C_{1-6}$alkyl)-N($R^{14}$)C(O)$R^{12}$, wherein $C_{1-6}$alkyl, $C_{2-6}$alkenyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{3-10}$cycloalkyl, $C_{2-9}$heterocycloalkyl, —$CH_2$-$C_{2-9}$heterocycloalkyl, wherein $C_{1-6}$alkyl, $C_{3-10}$cycloalkyl, $C_{2-9}$heterocycloalkyl, and —$CH_2$-$C_{2-9}$heterocycloalkyl are

864 optionally substituted with one, two, or three $R^{20l}$ each $R^{1d}$ is independently selected from hydrogen, $C_{1-6}$alkyl, and $C_{1-6}$haloalkyl;

each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{21}$, —N($R^{22}$)($R^{23}$), —C(O)N($R^{22}$)($R^{23}$), —N($R^{24}$)C(O)$R^{21}$, —C(O)$R^{21}$, and —S(O)$_2R^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —$OR^{21}$, and —N($R^{22}$)($R^{23}$); each $R^{20l}$ is independently selected from halogen, —$OR^{21}$, and $C_{3-10}$cycloalkyl; each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl; each $R^{22}$ is independently selected from H and $C_{1-6}$alkyl; each $R^{23}$ is independently selected from H and $C_{1-6}$alkyl; each $R^{24}$ is independently selected from H and $C_{1-6}$alkyl; and each $R^{25}$ is independently selected from $C_{1-6}$alkyl and $C_{3-6}$cycloalkyl.

In some embodiments of a compound of Formula (I), (II), (III), (IV), (XVI), or (XVII), or a pharmaceutically acceptable salt or solvate thereof, the compound has a formula selected from:

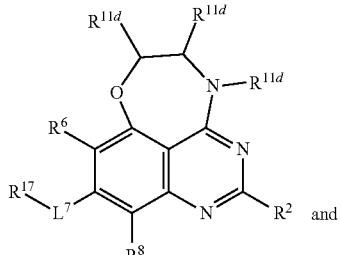

Formula (XXa)

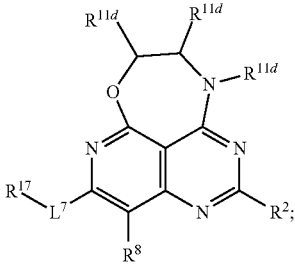

Formula (XXd)

wherein $R^6$ and $R^8$ are independently selected from hydrogen and halogen;

$L^7$ is a bond;

$R^{17}$ is selected from:

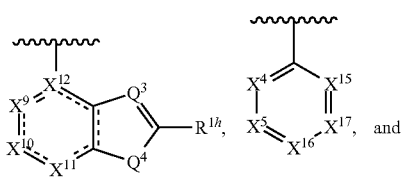

-continued

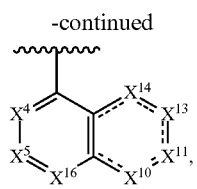

$Q^3$ is N or $C(R^{14})$; $Q^4$ is S;

$X^4, X^5, X^{15}, X^{16}$, and $X^{17}$ are independently selected from $C(R^{1a})$ or N;

$X^9$ is $C(R^{1a})$; $X^{10}, X^{11}, X^{13}$, and $X^{14}$ are independently $C(R^{1a})$ or N; $X^{12}$ is C; each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH2, —C(O)OH, —OC(O)NH2, and —C(O)CH_3$;

$R^{1d}$ is selected from hydrogen, —CN, $C_{1-4}$alkyl, and $C_{1-4}$haloalkyl;

$R^2$ is selected from

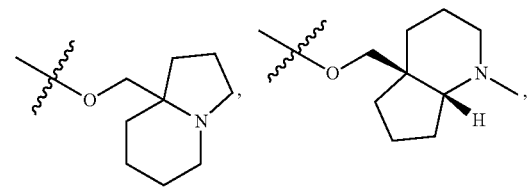

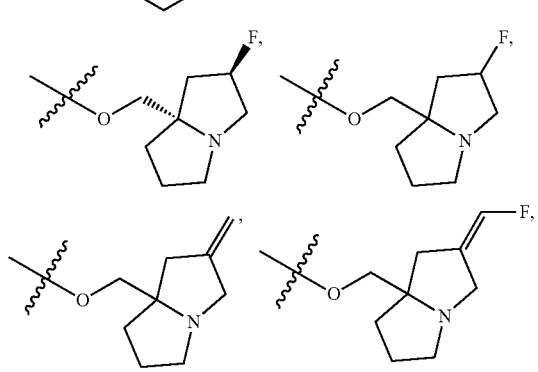

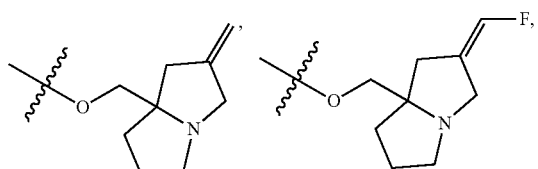

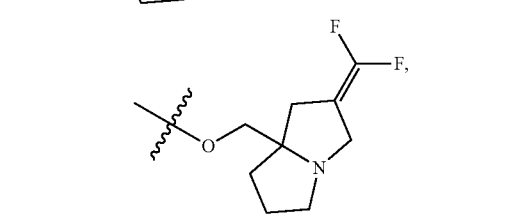

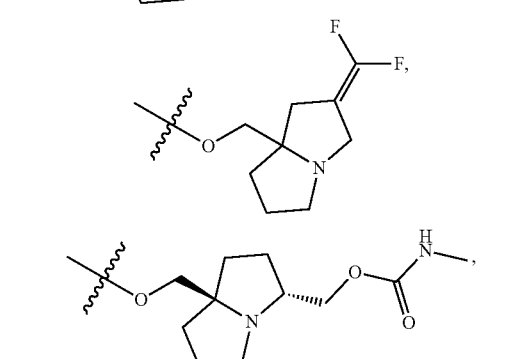

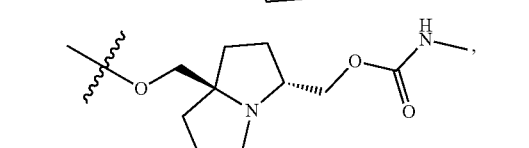

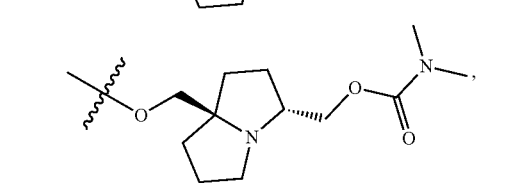

-continued

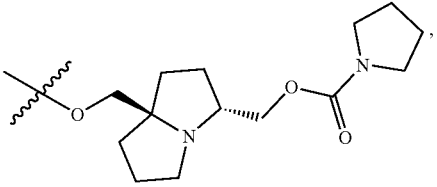

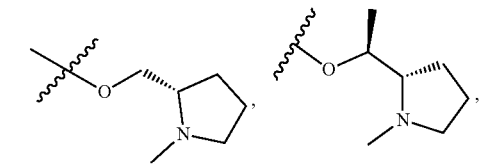

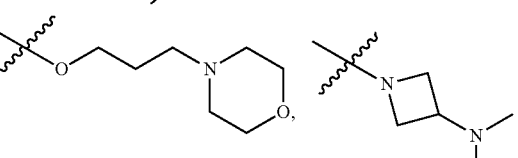

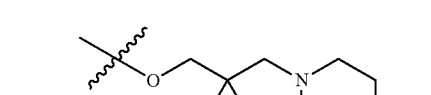, and

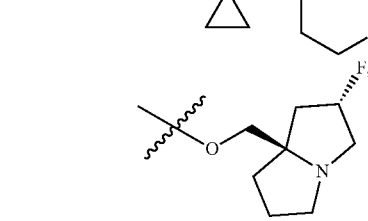;

each $R^{11d}$ is independently selected from $C_{1-6}$alkyl, $C_{2-6}$alkenyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, $C_{1-11}$heteroaryl, —($C_{1-6}$alkyl)-$N(R^{14})C(O)R^{12}$, wherein $C_{1-6}$alkyl, $C_{2-6}$alkenyl, $C_{3-12}$ cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{3-10}$cycloalkyl, $C_{2-9}$heterocycloalkyl, —$CH_2$-$C_{2-9}$heterocycloalkyl, wherein $C_{1-6}$alkyl, $C_{3-10}$cycloalkyl, $C_{2-9}$heterocycloalkyl, and —$CH_2$-$C_{2-9}$heterocycloalkyl are optionally substituted with one, two, or three $R^{20l}$; each $R^{1d}$ is independently selected from hydrogen, $C_{1-6}$alkyl, and $C_{1-6}$haloalkyl; each $R^{20k}$ is independently selected from halogen, oxo, —CN, $C_{1-6}$alkyl, $C_{2-6}$alkenyl, $C_{3-10}$cycloalkyl, $C_{2-9}$heterocycloalkyl, $C_{1-9}$heteroaryl, —$OR^{21}$, —$N(R^{22})(R^{23})$, —$C(O)N(R^{22})(R^{23})$, —$N(R^{24})C(O)R^{21}$, —$C(O)R^{21}$, and —$S(O)_2R^{25}$, wherein $C_{1-6}$alkyl, $C_{2-6}$alkenyl, $C_{3-10}$ cycloalkyl, $C_{2-9}$heterocycloalkyl, and $C_{1-9}$heteroaryl are optionally substituted with one, two, or three groups independently selected from halogen, —CN, $C_{1-6}$alkyl, $C_{1-6}$haloalkyl, —$OR^{21}$, and —$N(R^{22})(R^{23})$; each $R^{20l}$ is independently selected from halogen, —$OR^{21}$, and $C_{3-10}$cycloalkyl; each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl; each $R^{22}$ is independently selected from H and $C_{1-6}$alkyl; each $R^{23}$ is independently selected from H and $C_{1-6}$alkyl; each $R^{24}$ is independently selected from H and $C_{1-6}$alkyl; and each $R^{25}$ is independently selected from $C_{1-6}$alkyl and $C_{3-6}$cycloalkyl.

In some embodiments of a compound of Formula (I), (II), (III), (IV), (XVI), or (XVII), or a pharmaceutically acceptable salt or solvate thereof, the compound has a formula selected from:

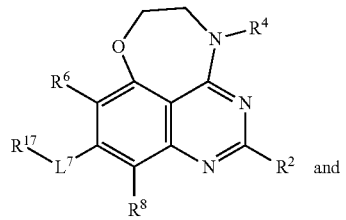

Formula (XVa)

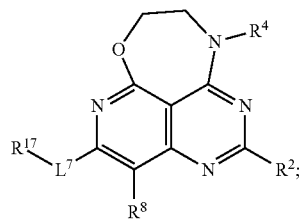

Formula (XVd)

wherein
R$^6$ and R$^8$ are independently selected from hydrogen and halogen;
L$^7$ is a bond;
R$^{17}$ is selected from:

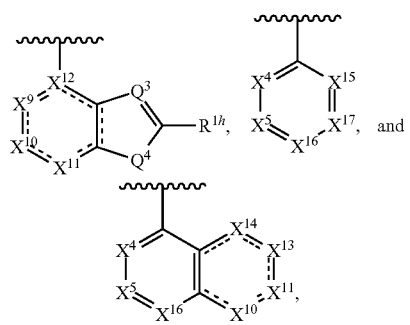

Q$^3$ is N or C(R$^{1d}$); Q$^4$ is S;
X$^4$, X$^5$, X$^{15}$, X$^{16}$, and X$^{17}$ are independently selected from C(R$^{1a}$) or N;
X$^9$ is C(R$^{1a}$); X$^{10}$, X$^{11}$, X$^{13}$, and X$^{14}$ are independently C(R$^{1a}$) or N; X$^{12}$ is C; each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;
R$^{1d}$ is selected from hydrogen, —CN, C$_{1-4}$alkyl, and C$_{1-4}$haloalkyl;

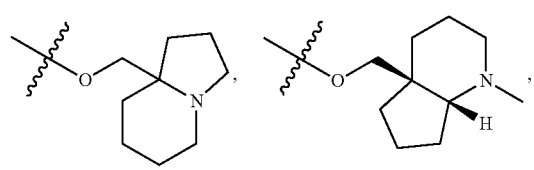

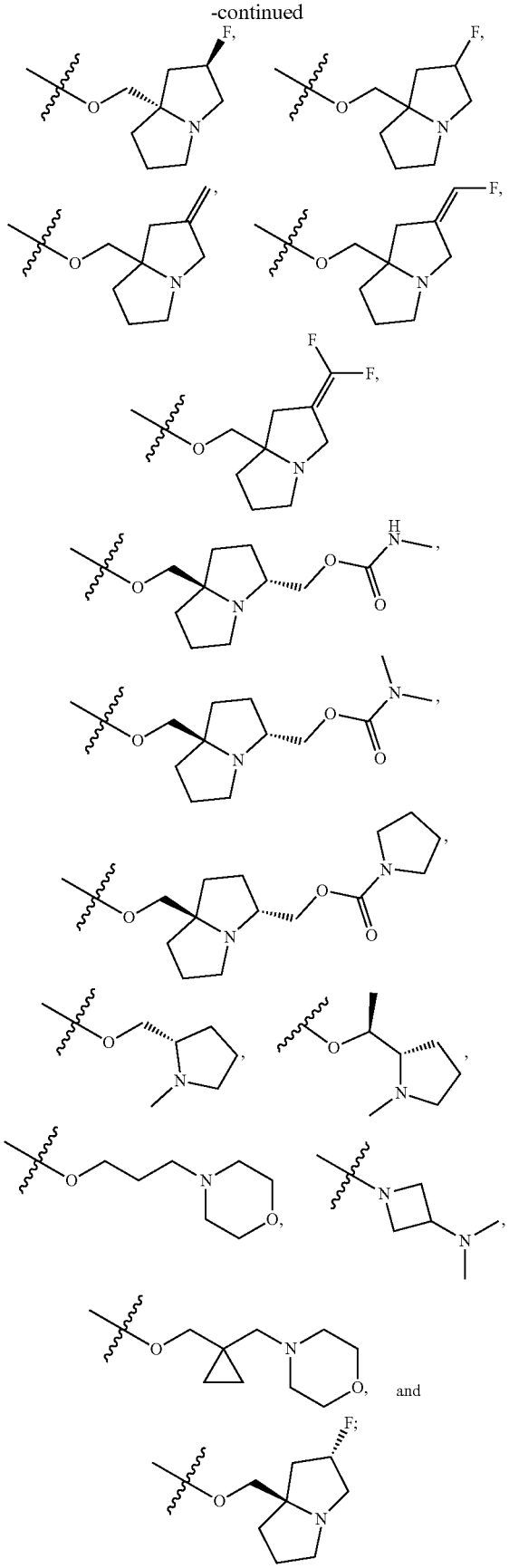

R⁴ is -L4-R⁴ᵃ;

L⁴ is a bond, —O—, —C(O)—, —S(O)₂—, CR⁴R⁴, —CR⁴R⁴CR⁴R⁴, —N(R⁴ᵈ)C(O)—, or —C(O)N(R⁴ᵈ)—;

each R⁴ᶜ is independently selected from hydrogen and C₁₋₆alkyl;

each R⁴ᵈ is independently selected from hydrogen and C₁₋₆alkyl;

each R⁴ᵃ is independently selected from C₃₋₇cycloalkyl, C₂₋₉heterocycloalkyl, phenyl, and C₁₋₆heteroaryl, wherein C₃₋₇cycloalkyl, C₂₋₉heterocycloalkyl, phenyl, and C₁₋₆heteroaryl are optionally substituted with one, two, three, or four R⁴ᵇ;

each R⁴ᵇ is independently selected from halogen, oxo, —CN, C₁₋₆alkyl, C₂₋₆alkenyl, C₃₋₁₂cycloalkyl, C₂₋₁₁heterocycloalkyl, —OR¹², —N(R¹²)(R¹³), —C(R²¹ᵇ)₂, —C(O)R¹², —N(R¹⁴)C(O)R¹², —S(O)₂R¹⁵, and —C(O)N(R¹²)(R¹³), wherein C₁₋₆alkyl, C₃₋₁₂cycloalkyl, and C₂₋₁₁heterocycloalkyl, are optionally substituted with one or more R²⁰ʲ;

each R¹² is independently selected from hydrogen, C₁₋₆alkyl, C₂₋₆alkenyl, C₃₋₁₀cycloalkyl, C₂₋₉heterocycloalkyl, and C₁₋₉heteroaryl, wherein C₁₋₆alkyl, C₃₋₁₀cycloalkyl, C₂₋₉heterocycloalkyl, and C₁₋₉heteroaryl are optionally substituted with one, two, or three R²⁰ˡ;

each R¹³ is independently selected from hydrogen and C₁₋₆alkyl;

each R¹ᵈ is independently selected from hydrogen, C₁₋₆alkyl, and C₁₋₆haloalkyl;

each R¹⁵ is independently selected C₃₋₁₀cycloalkyl;

each R²⁰⁰ is independently selected from halogen, —CN, C₁₋₆alkyl, C₃₋₁₀cycloalkyl, C₂₋₉heterocycloalkyl, C₆₋₁₀aryl, C₁₋₉heteroaryl, —OR²¹, —N(R²²)(R²³), and —N(R²⁴)C(O)R²⁵, wherein C₁₋₆alkyl, C₃₋₁₀cycloalkyl C₂₋₉heterocycloalkyl, C₆₋₁₀aryl, — and C₁₋₉heteroaryl are optionally substituted with one, two, or three groups independently selected from halogen;

each R²⁰ˡ is independently selected from halogen, —CN, C₁₋₆alkyl, C₃₋₁₀cycloalkyl, C₂₋₉heterocycloalkyl, C₆₋₁₀aryl, C₁₋₉heteroaryl, —OR²¹, —N(R²²)(R²³), and —N(R²⁴)C(O)R²⁵, wherein C₁₋₆alkyl, C₃₋₁₀cycloalkyl, C₂₋₉heterocycloalkyl, C₆₋₁₀aryl, and C₁₋₉heteroaryl are optionally substituted with one, two, or three groups independently selected from halogen; each R²¹ is independently selected from H, C₁₋₆alkyl, C₁₋₆haloalkyl, and C₃₋₁₀cycloalkyl;

each R²² is independently C₁₋₆alkyl;

each R²³ is independently C₁₋₆alkyl; and each R²⁵ is independently C₂₋₉heterocycloalkyl.

In some embodiments of a compound of Formula (I), (II), (III), (IV), (XVI), or (XVII), or a pharmaceutically acceptable salt or solvate thereof, the compound has a formula selected from:

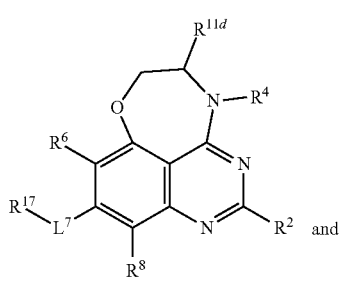

Formula (XXIa)

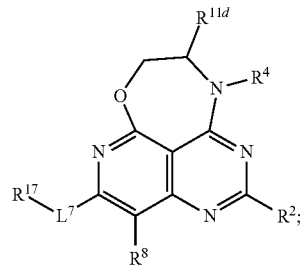

Formula (XXId)

wherein

R⁶ and R⁸ are independently selected from hydrogen and halogen;

L⁷ is a bond;

R¹⁷ is selected from:

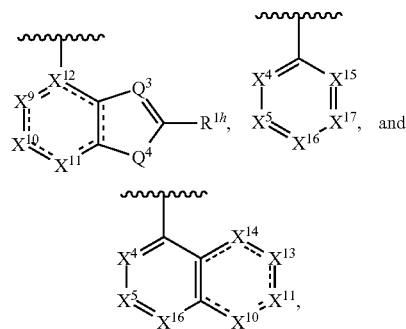

Q³ is N or C(R¹ᵈ); Q⁴ is S;

X⁴, X⁵, X¹⁵, X¹⁶, and X¹⁷ are independently selected from C(R¹ᵃ) or N;

X⁹ is C(R¹ᵃ); X¹⁰, X¹¹, X¹³, and X¹⁴ are independently C(R¹ᵃ) or N; X¹² is C; each R¹ᵃ and R¹ʰ is independently selected from hydrogen, halogen, —CN, C₁₋₄alkyl, C₁₋₄haloalkyl, C₂₋₄alkenyl, C₂₋₄alkynyl, C₃₋₄cycloalkyl, C₂₋₄heterocycloalkyl, —OH, —NH₂, —C(O)OH, —OC(O)NH₂, and —C(O)CH₃;

R¹ᵈ is selected from hydrogen, —CN, C₁₋₄alkyl, and C₁₋₄haloalkyl;

R² is selected from

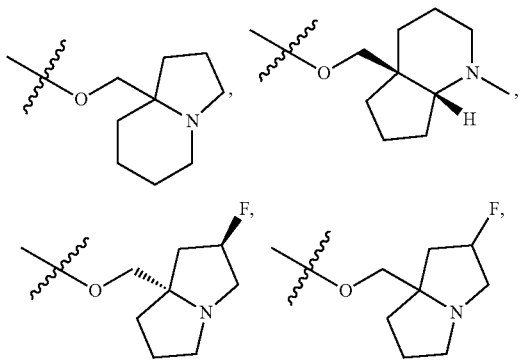

-continued

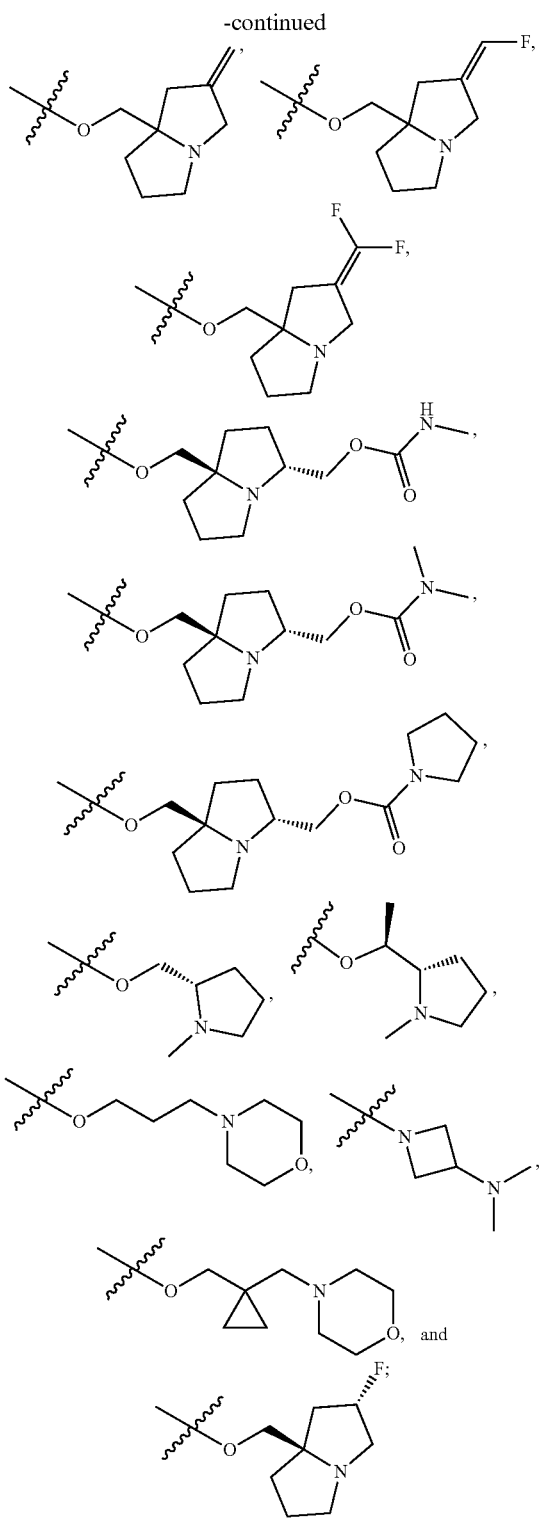

R⁴ is -L⁴-R⁴ᵃ;

L⁴ is a bond, —O—, —C(O)—, —S(O)₂—, CR⁴R⁴, —CR⁴R⁴ᶜCR⁴R⁴ᶜ, —N(R⁴ᵈ)C(O)—, or —C(O)N(R⁴ᵈ)—;

each R⁴ᶜ is independently selected from hydrogen and C₁₋₆alkyl;

each R⁴ᵈ is independently selected from hydrogen and C₁₋₆alkyl;

each R⁴ᵃ is independently selected from C₃₋₇cycloalkyl, C₂₋₉heterocycloalkyl, phenyl, and C₁-6heteroaryl, wherein C₃₋₇cycloalkyl, C₂-heterocycloalkyl, phenyl, and C₁-6heteroaryl are optionally substituted with one, two, three, or four R⁴ᵇ;

each R⁴ᵇ is independently selected from halogen, oxo, —CN, C₁₋₆alkyl, C₂₋₆alkenyl, C₃₋₁₂cycloalkyl, C₂₋₁₁heterocycloalkyl, —OR¹², —N(R¹²)(R¹³), =C(R²¹ᵇ)₂, —C(O)R¹², —N(R¹⁴)C(O)R¹², —S(O)₂R¹⁵, and —C(O)N(R¹²)(R¹³), wherein C₁₋₆alkyl, C₃₋₁₂cycloalkyl, and C₂₋₁₁heterocycloalkyl, are optionally substituted with one or more R²⁰ʲ; each R¹¹ᵈ is independently selected from C₁₋₆alkyl, —CH₂-C₃₋₁₂cycloalkyl, —(C₁₋₆alkyl)-N(R¹⁴)C(O)R¹², wherein C₁₋₆alkyl and —CH₂-C₃₋₁₂cycloalkyl, are optionally substituted with one, two, or three R²⁰ᵏ; each R¹² is independently selected from hydrogen, C₁₋₆alkyl, C₂₋₆alkenyl, C₃₋₁₀cycloalkyl, C₂₋₉heterocycloalkyl, —CH₂-C₂₋₉heterocycloalkyl, and C₁₋₉heteroaryl, wherein C₁₋₆alkyl, C₃₋₁₀cycloalkyl, C₂₋₉heterocycloalkyl, —CH₂-C₂₋₉heterocycloalkyl, and C₁₋₉heteroaryl are optionally substituted with one, two, or three R²⁰ˡ, each R¹³ is independently selected from hydrogen and C₁₋₆alkyl; each R¹ᵈ is independently selected from hydrogen, C₁₋₆alkyl, and C₁₋₆haloalkyl; each R¹⁵ is independently selected C₃₋₁₀cycloalkyl; each R²⁰ʲ is independently selected from halogen, —CN, C₁₋₆alkyl, C₃₋₁₀cycloalkyl, C₂₋₉heterocycloalkyl, C₆₋₁₀aryl, C₁₋₉heteroaryl, —OR²¹, —N(R²²)(R²³), and —N(R²⁴)C(O)R²⁵, wherein C₁₋₆alkyl, C₃₋₁₀cycloalkylC₂₋₉heterocycloalkyl, C₆₋₁₀aryl, — and C₁₋₉heteroaryl are optionally substituted with one, two, or three groups independently selected from halogen; each R²⁰ᵏ is independently selected from halogen, —CN, —OR²¹, —N(R²²)(R²³), and —N(R²⁴)C(O)R²¹; each R²⁰ˡ is independently selected from halogen, —CN, C₁₋₆alkyl, C₃₋₁₀cycloalkyl, C₂₋₉heterocycloalkyl, C₆₋₁₀aryl, C₁₋₉heteroaryl, —OR²¹, —N(R²²)(R²³), and —N(R²⁴)C(O)R²⁵, wherein C₁₋₆alkyl, C₃₋₁₀cycloalkyl, C₂₋₉heterocycloalkyl, C₆₋₁₀aryl, and C₁₋₉heteroaryl are optionally substituted with one, two, or three groups independently selected from halogen; each R²¹ is independently selected from H, C₁₋₆alkyl, C₁₋₆haloalkyl, C₃₋₁₀cycloalkyl, C₂₋₉heterocycloalkyl, and C₁₋₉heteroaryl; each R²² is independently selected from H and C₁₋₆alkyl; each R²³ is independently selected from H and C₁₋₆alkyl; each R²⁴ is independently selected from H and C₁₋₆alkyl; and each R²⁵ is independently selected from C₁₋₆alkyl, C₃₋₆cycloalkyl, and C₂₋₉heterocycloalkyl.

In some embodiments of a compound of Formula (I), (II), (III), (IV), (XVI), or (XVII), or a pharmaceutically acceptable salt or solvate thereof, the compound has a formula selected from:

Formula (XXIIa)

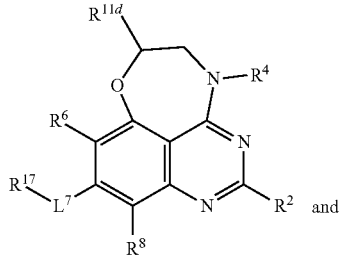

and

-continued

Formula (XXIId)

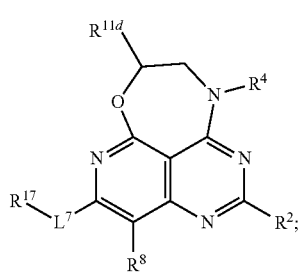

wherein
R⁶ and R⁸ are independently selected from hydrogen and halogen;
L⁷ is a bond;
R¹⁷ is selected from:

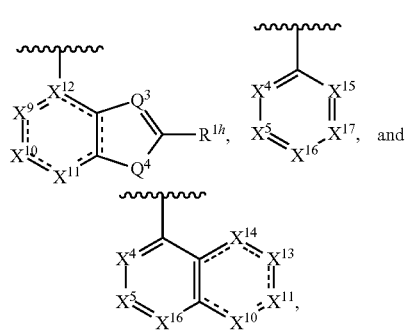

Q³ is N or C(R¹⁴); Q⁴ is S;
X⁴, X³, X¹⁵, X¹⁶, and X¹⁷ are independently selected from C(R¹ᵃ) or N;
X⁹ is C(R¹ᵃ); X¹⁰, X¹¹, X¹³, and X¹⁴ are independently C(R¹ᵃ) or N; X¹² is C; each R¹ᵃ and R¹ʰ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH₂, —C(O)OH, —OC(O)NH₂, and —C(O)CH₃;
R¹ᵈ is selected from hydrogen, —CN, $C_{1-4}$alkyl, and $C_{1-4}$haloalkyl;
R² is selected from

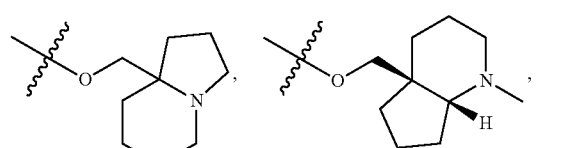

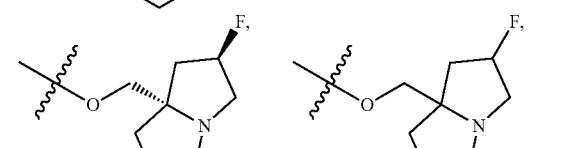

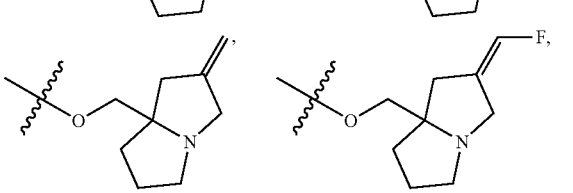

-continued

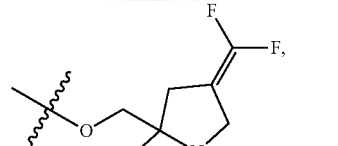

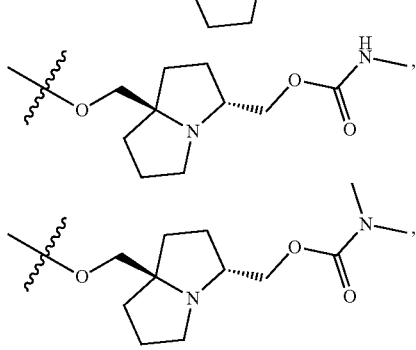

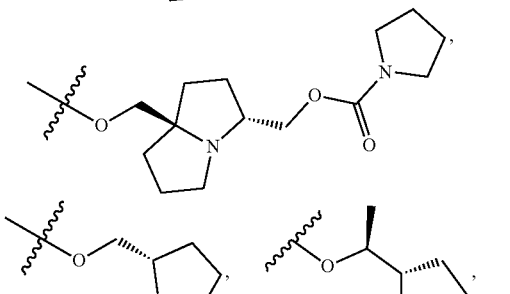

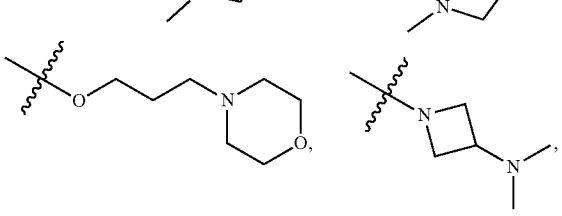

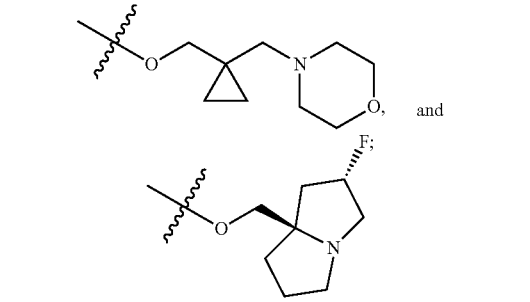

R⁴ is -L⁴-R⁴ᵃ;
L⁴ is a bond, —O—, —C(O)—, —S(O)₂—, CR⁴R⁴, —CR⁴R⁴ᶜCR4R⁴ᶜ, —N(R⁴ᵈ)C(O)—, or —C(O)N(R⁴ᵈ)—; each R⁴ is independently selected from hydrogen and $C_{1-6}$alkyl; each R⁴ᵈ is independently selected from hydrogen and $C_{1-6}$alkyl; each R⁴ᵃ is independently selected from $C_{3-7}$cycloalkyl, $C_{2-9}$heterocycloalkyl, phenyl, and $C_{1-6}$heteroaryl, wherein $C_{3-7}$cycloalkyl, $C_{2-9}$heterocycloalkyl, phenyl, and $C_{1-6}$heteroaryl are optionally substituted with one, two, three, or four R⁴ᵇ; each R⁴ᵇ is independently selected from halogen, oxo, —CN, $C_{1-6}$alkyl, $C_{2-6}$alkenyl, $C_{3-12}$cycloalkyl, $C_{2-11}$heterocycloalkyl, —OR¹², —N(R¹²)(R¹³), =C(R$^{21b}$)$_2$, —C(O)R$^{12}$, —N(R$^{14}$)C(O)R$^{12}$, —S(O)$_2$R$^{15}$, and —C(O)N(R$^{12}$)(R$^{13}$), wherein C$_{1-6}$alkyl, C$_{3-12}$cycloalkyl, and C$_{2-11}$heterocycloalkyl, are optionally substituted with one or more R$^{20j}$; each R$^{11d}$ is independently selected from C$_{1-6}$alkyl, —CH$_2$-C$_{3-12}$cycloalkyl, —(C$_{1-6}$alkyl)-N(R$^{14}$)C(O)R$^{12}$, wherein C$_{1-6}$alkyl and —CH$_2$-C$_{3-12}$cycloalkyl, are optionally substituted with one, two, or three R$^{20k}$; each R$^{12}$ is independently selected from hydrogen, C$_{1-6}$alkyl, C$_{2-6}$alkenyl, C$_{3-10}$cycloalkyl, C$_{2-9}$heterocycloalkyl, —CH$_2$-C$_{2-9}$heterocycloalkyl, and C$_{1-9}$heteroaryl, wherein C$_{1-6}$alkyl, C$_{3-10}$cycloalkyl, C$_{2-9}$heterocycloalkyl, —CH$_2$-C$_{2-9}$heterocycloalkyl, and C$_{1-9}$heteroaryl are optionally substituted with one, two, or three R$^{20l}$; each R$^{13}$ is independently selected from hydrogen and C$_{1-6}$alkyl; each R$^{1d}$ is independently selected from hydrogen, C$_{1-6}$alkyl, and C$_{1-6}$haloalkyl; each R$^{15}$ is independently selected C$_{3-10}$cycloalkyl; each R$^{20j}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkylC$_{2-9}$heterocycloalkyl, C$_{6-10}$aryl, — and C$_{1-9}$heteroaryl are optionally substituted with one, two, or three groups independently selected from halogen; each R$^{20k}$ is independently selected from halogen, —CN, —OR$^{21}$, —N(R$^{22}$)(R$^{23}$), and —N(R$^{24}$)C(O)R$^{21}$; each R$^{20l}$ is independently selected from halogen, —CN, C$_{1-6}$alkyl, C$_{3-10}$cycloalkyl, C$_{2-9}$heterocycloalkyl, C$_{6-10}$aryl, C$_{1-9}$heteroaryl, —OR$^{21}$, —N(R$^{22}$)(R$^{23}$), and —N(R$^{24}$)C(O)R$^{25}$, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three groups independently selected from halogen; each R$^{21}$ is independently selected from H, C$_{1-6}$alkyl, C$_{1-6}$haloalkyl, C$_{3-10}$cycloalkyl, C$_{2-9}$heterocycloalkyl, and C$_{1-9}$heteroaryl;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH; each R$^{22}$ is independently selected from H and C$_{1-6}$alkyl; each R$^{23}$ is independently selected from H and C$_{1-6}$alkyl; each R$^{24}$ is independently selected from H and C$_{1-6}$alkyl; and each R$^{25}$ is independently selected from C$_{1-6}$alkyl, C$_{3-6}$cycloalkyl, and C$_{2-9}$heterocycloalkyl.

In some embodiments of a compound of Formula (I), (II), (III), (IV), (XVI), or (XVII), or a pharmaceutically acceptable salt or solvate thereof, the compound has a formula selected from:

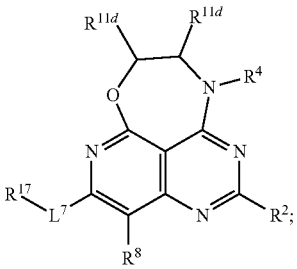

Formula (XXIIIa)

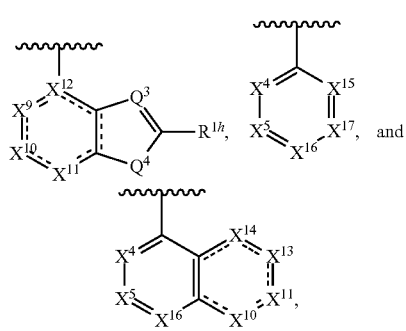

Formula (XXIIId)

wherein
R$^6$ and R$^8$ are independently selected from hydrogen and halogen;
L$^7$ is a bond;
R$^{17}$ is selected from:

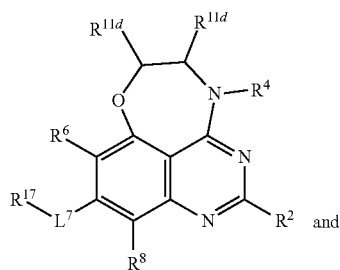

Q$^3$ is N or C(R$^{1d}$); Q$^4$ is S;
X$^4$, X$^5$, X$^{15}$, X$^{16}$, and X$^{17}$ are independently selected from C(R$^{1a}$) or N;
X$^9$ is C(R$^{18}$); X$^{10}$, X$^{11}$, X$^{13}$, and X$^{14}$ are independently C(R$^{1a}$) or N; X$^{12}$ is C; each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;
R$^{1d}$ is selected from hydrogen, —CN, C$_{1-4}$alkyl, and C$_{1-4}$haloalkyl;
R$^2$ is selected from

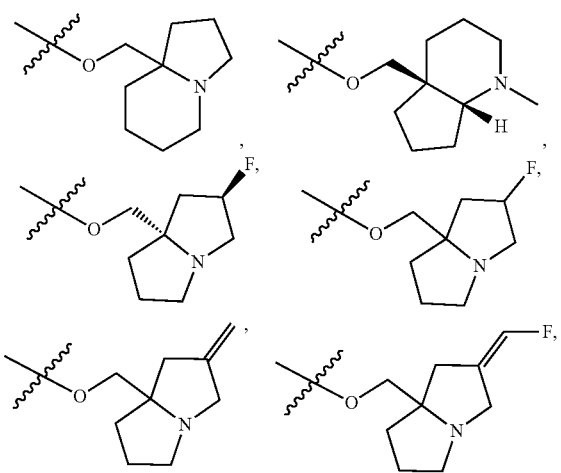

R⁴ is -L⁴-R⁴⁸;
L⁴ is a bond, —O—, —C(O)—, —S(O)₂—, CR⁴R⁴, —CR⁴R⁴CR⁴R⁴, —N(R⁴ᵈ)C(O)—, or —C(O)N(R⁴ᵈ)—; each R* is independently selected from hydrogen and C₁₋₆alkyl; each R⁴ᵈ is independently selected from hydrogen and C₁₋₆alkyl; each R⁴ᵃ is independently selected from C₃₋₇cycloalkyl, C₂₋₉heterocycloalkyl, phenyl, and C₁-6heteroaryl, wherein C₃₋₇cycloalkyl, C₂₋₉heterocycloalkyl, phenyl, and C₁-6heteroaryl are optionally substituted with one, two, three, or four R⁴⁰; each R⁴ᵇ is independently selected from halogen, oxo, —CN, C₁₋₆alkyl, C₂₋₆alkenyl, C₃₋₁₂cycloalkyl, C₂₋₁₁heterocycloalkyl, —OR¹², —N(R¹²)(R¹³), =C(R²¹ᵇ)₂, —C(O)R¹², —N(R¹⁴)C(O)R¹², —S(O)₂R¹⁵, and —C(O)N(R¹²)(R¹³), wherein C₁₋₆alkyl, C₃₋₁₂cycloalkyl, and C₂₋₁₁heterocycloalkyl, are optionally substituted with one or more R²⁰ʲ; each R¹¹ᵈ is independently selected from C₁₋₆alkyl, —CH₂-C₃₋₁₂cycloalkyl, —(C₁₋₆alkyl)-N(R¹⁴)C(O)R¹², wherein C₁₋₆alkyl and —CH₂-C₃. 12 cycloalkyl, are optionally substituted with one, two, or three R²⁰ᵏ; each R¹² is independently selected from hydrogen, C₁₋₆alkyl, C₂₋₆alkenyl, C₃₋₁₀cycloalkyl, C₂₋₉heterocycloalkyl, —CH₂-C₂₋₉heterocycloalkyl, and C₁₋₉heteroaryl, wherein C₁₋₆alkyl, C₃₋₁₀cycloalkyl, C₂₋₉heterocycloalkyl, —CH₂-C₂₋₉heterocycloalkyl, and C₁-9heteroaryl are optionally substituted with one, two, or three R²⁰ˡ; each R¹³ is independently selected from hydrogen and C₁₋₆alkyl; each R¹ᵈ is independently selected from hydrogen, C₁₋₆alkyl, and C₁₋₆haloalkyl; each R¹⁵ is independently selected C₃₋₁₀cycloalkyl; each R²⁰ʲ is independently selected from halogen, —CN, C₁₋₆alkyl, C₃₋₁₀cycloalkyl, C₂₋₉heterocycloalkyl, C₆₋₁₀aryl, C₁₋₉heteroaryl, —OR²¹, —N(R²²)(R²³), and —N(R²⁴)C(O)R²⁵, wherein C₁₋₆alkyl, C₃₋₁₀cycloalkylC₂₋₉heterocycloalkyl, C₆₋₁₀aryl, — and C₁₋₉heteroaryl are optionally substituted with one, two, or three groups independently selected from halogen; each R²⁰ᵏ is independently selected from halogen, —CN, —OR²¹, —N(R²²)(R²³), and —N(R²⁴)C(O)R²¹; each R²⁰ˡ is independently selected from halogen, —CN, C₁₋₆alkyl, C₃₋₁₀cycloalkyl, C₂₋₉heterocycloalkyl, C₆₋₁₀aryl, C₁₋₉heteroaryl, —OR²¹, —N(R²²)(R²³), and —N(R²⁴)C(O)R²⁵, wherein C₁₋₆alkyl, C₃₋₁₀cycloalkyl, C₂₋₉heterocycloalkyl, C₆₋₁₀aryl, and C₁₋₉heteroaryl are optionally substituted with one, two, or three groups independently selected from halogen; each R²¹ is independently selected from H, C₁₋₆alkyl, C₁₋₆haloalkyl, C₃₋₁₀cycloalkyl, C₂₋₉heterocycloalkyl, and C₁₋₉heteroaryl;

R²¹ᵇ is independently selected at each occurrence from hydrogen, halogen, C₁₋₆alkyl, C₁₋₆haloalkyl, C₂₋₆alkenyl, C₂₋₆alkynyl, C₃₋₁₀cycloalkyl, C₂₋₉heterocycloalkyl, C₆₋₁₀aryl, and C₁₋₉heteroaryl, or two R²¹ᵇ are taken together with the carbon atom to which they are attached to form C₃₋₁₀cycloalkyl or C₂₋₉heterocycloalkyl; each of which is optionally substituted with one, two, or three substituents independently selected from halogen, C₁₋₃ alkyl, C₁₋₃ haloalkyl, and —OH; each R²² is independently selected from H and C₁₋₆alkyl; each R²³ is independently selected from H and C₁₋₆alkyl; each R²⁴ is independently selected from H and C₁₋₆alkyl; and each R²⁵ is independently selected from C₁₋₆alkyl, C₃₋₆cycloalkyl, and C₂₋₉heterocycloalkyl.

In some embodiments of a compound of Formula (I), (II), (III), (IV), (XVI), or (XVII), or a pharmaceutically acceptable salt or solvate thereof, the compound has a formula selected from:

Formula (XXVIa)

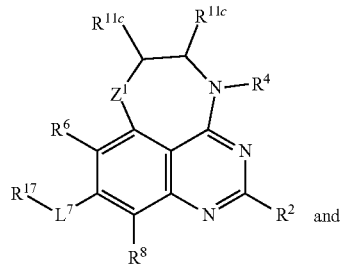

and

-continued

Formula (XXVId)

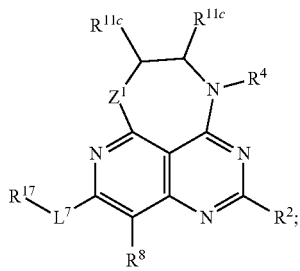

wherein $Z^1$ is selected from $N(R^{11c})$ and O;
$R^6$ and $R^8$ are independently selected from hydrogen and halogen;
$L^7$ is a bond;
$R^{17}$ is selected from:

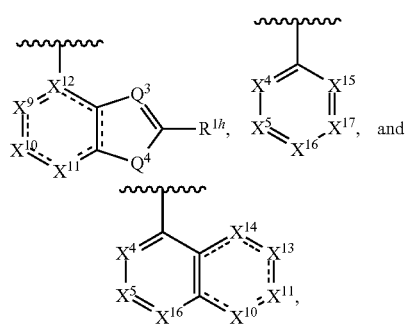

$Q^3$ is N or $C(R^{1a})$; $Q^4$ is S;
$X^4, X^5, X^{15}, X^{16}$, and $X^{17}$ are independently selected from $C(R^{1a})$ or N;
$X^9$ is $C(R^{1a})$; $X^{10}, X^{11}, X^{13}$, and $X^{14}$ are independently $C(R^{1a})$ or N; $X^{12}$ is C; each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH$_2$, —C(O)OH, —OC(O)NH$_2$, and —C(O)CH$_3$;
$R^{1d}$ is selected from hydrogen, —CN, $C_{1-4}$alkyl, and $C_{1-4}$haloalkyl;
$R^2$ is selected from

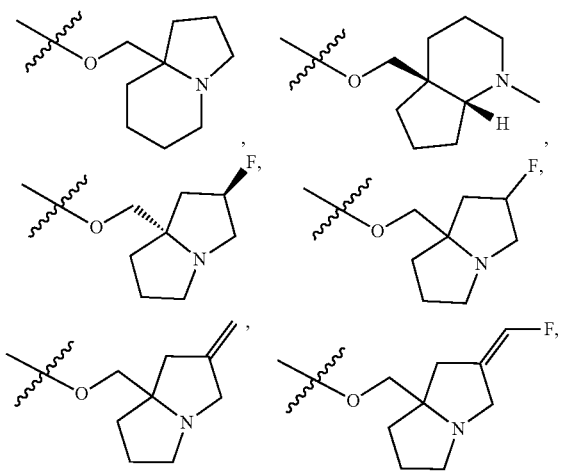

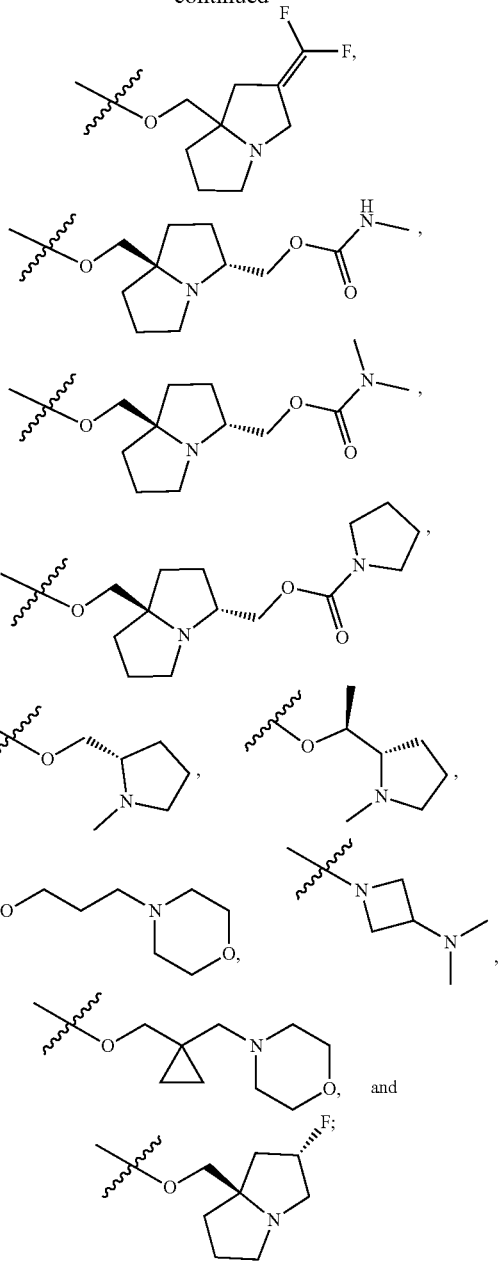

$R^4$ is -$L^4$-$R^{4a}$;
$L^4$ is a bond, $CR^4R^4$; each $R^4$ is independently selected from hydrogen and $C_{1-6}$alkyl; each $R^{4a}$ is independently selected from $C_{3-7}$cycloalkyl and $C_{2-9}$heterocycloalkyl, wherein $C_{3-7}$cycloalkyl and $C_{2-9}$heterocycloalkyl are optionally substituted with one, two, three, or four $R^4$; each $R^{4b}$ is independently selected from halogen, —CN, $C_{1-6}$alkyl, —OR$^{12}$, —N(R$^{12}$)(R$^{13}$), =C(R$^{21b}$)$_2$, and —C(O)R$^{12}$, wherein $C_{1-6}$alkyl is optionally substituted with one or more $R^{20j}$; each $R^{11c}$ is independently selected from hydrogen, $C_{1-6}$alkyl, $C_{3-12}$cycloalkyl, —CH$_2$-$C_{3-12}$cycloalkyl, $C_{1-11}$heterocycloalkyl, CH$_2$-$C_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-$C_{3-12}$cycloalkyl, $C_{1-11}$heterocycloalkyl, CH$_2$-$C_{1-11}$heterocycloalkyl, and $C_{1-11}$heteroaryl are optionally substituted with one, two, or three R$^{20k}$; each R$^{12}$ is independently selected from hydrogen, C$_{1-6}$alkyl, C$_{2-9}$heterocycloalkyl, and —CH$_2$-C$_{2-9}$heterocycloalkyl, wherein C$_{1-6}$alkyl, C$_{2-9}$heterocycloalkyl, and —CH$_2$-C$_{2-9}$heterocycloalkyl are optionally substituted with one, two, or three R$^{20l}$; each R$^{13}$ is independently selected from hydrogen, C$_{1-6}$alkyl; each R$^{1d}$ is independently selected from hydrogen and C$_{1-6}$alkyl; each R$^{20j}$ is independently selected from halogen; each R$^{20k}$ is independently selected from halogen, —CN, C$_{1-6}$alkyl, —OR$^{21}$, —N(R$^{22}$)(R$^{23}$), and —C(O)R$^{21}$, wherein C$_{1-6}$alkyl, is optionally substituted with one, two, or three groups independently selected from halogen, —CN, C$_{1-6}$alkyl, C$_{1-6}$haloalkyl, —OR$^{21}$, —N(R$^{22}$)(R$^{23}$);

each R$^{20l}$ is independently selected from halogen, C$_{3-10}$cycloalkyl, and —N(R$^{22}$)(R$^{23}$);

each R$^{21}$ is independently selected from H and C$_{1-6}$haloalkyl;

R$^{21b}$ is independently selected at each occurrence from hydrogen, halogen, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, or two R$^{21b}$ are taken together with the carbon atom to which they are attached to form C$_{3-10}$cycloalkyl or C$_{2-9}$heterocycloalkyl; each of which is optionally substituted with one, two, or three substituents independently selected from halogen, C$_{1-3}$ alkyl, C$_{1-3}$ haloalkyl, and —OH;

each R$^{22}$ is independently selected from H and C$_{1-6}$alkyl; and each R$^{23}$ is independently selected from H and C$_{1-6}$alkyl.

In some embodiments of a compound of Formula (I), (II), (III), (IV), (XVI), or (XVII), or a pharmaceutically acceptable salt or solvate thereof, the compound has a formula selected from:

Formula (XXVa)

Formula (XXVd)

wherein Z$^1$ is selected from N(R$^{11c}$) and O;

R$^6$ and R$^8$ are independently selected from hydrogen and halogen;

L$^7$ is a bond;

R$^{17}$ is selected from:

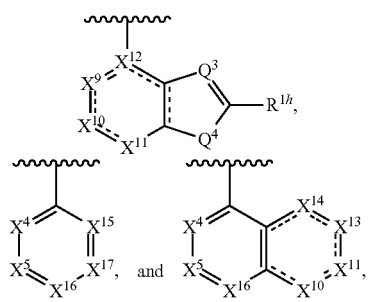

Q$^3$ is N or C(R$^{14}$); Q$^4$ is S;
X$^4$, X$^3$, X$^{15}$, X$^{16}$, and X$^{17}$ are independently selected from C(R$^{1a}$) or N;
X$^9$ is C(R$^{1a}$); X$^{10}$, X$^{11}$, X$^{13}$, and X$^{14}$ are independently C(R$^{1a}$) or N; X$^{12}$ is C;
each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, and —C(O)CH$_3$;
R$^{1d}$ is selected from hydrogen, —CN, C$_{1-4}$alkyl, and C$_{1-4}$haloalkyl;

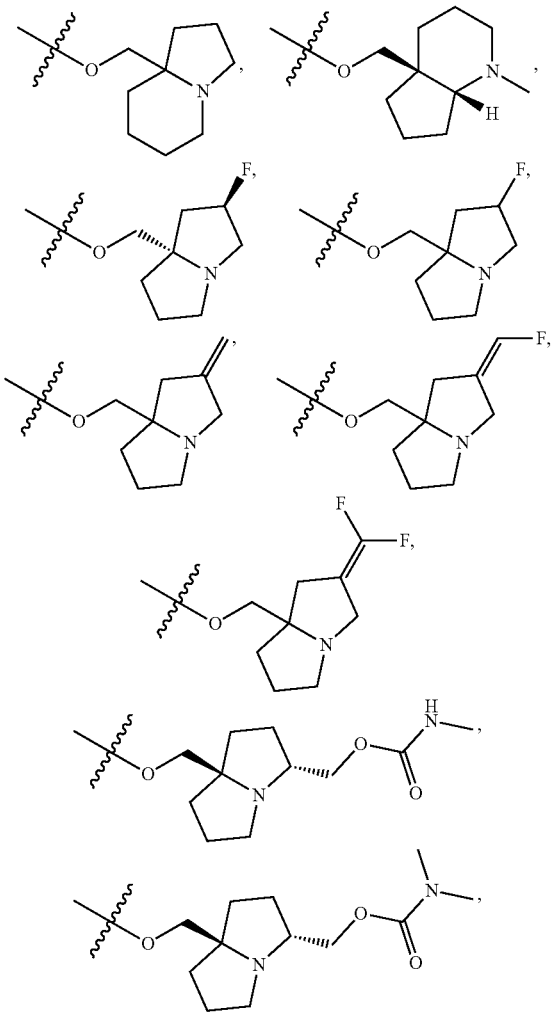

-continued

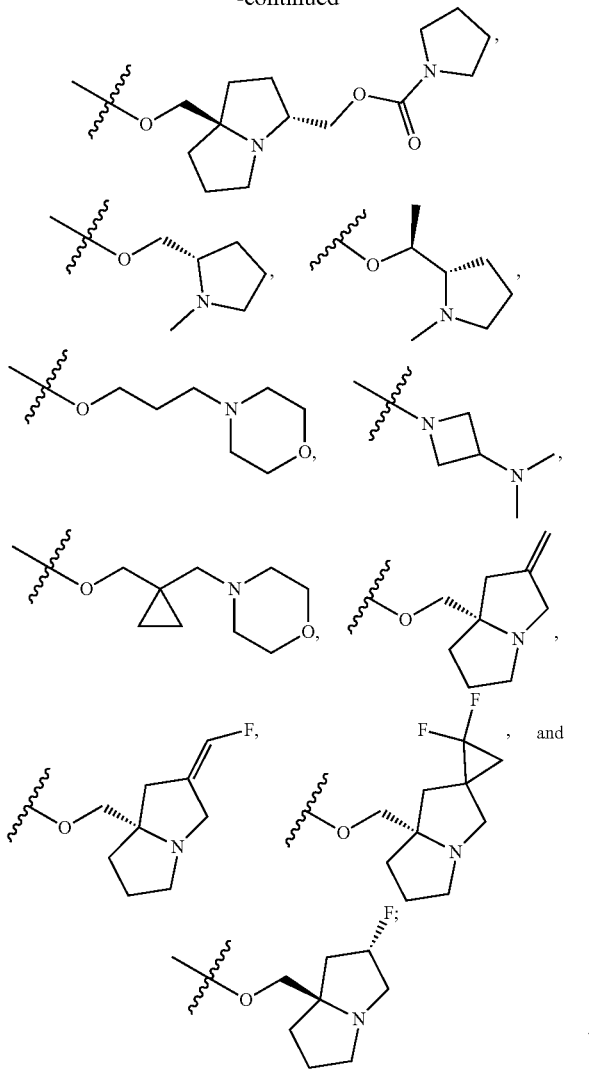

each $R^{11c}$ is independently selected from hydrogen, $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, $C_{1-11}$heteroaryl, —($C_{1-6}$alkyl)-N($R^{14}$)C(O)$R^{12}$, and —($C_{1-6}$alkyl)-N($R^{12}$)($R^{13}$), wherein $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, and $C_{1-11}$heteroaryl are optionally substituted with one, two, or three $R^{20k}$.

each $R^{11d}$ is independently selected from $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, $C_{1-11}$heteroaryl, —($C_{1-6}$alkyl)-N($R^{14}$)C(O)$R^{12}$, and —($C_{1-6}$alkyl)-N($R^{12}$)($R^{13}$), wherein $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, and $C_{1-11}$heteroaryl are optionally substituted with one, two, or three $R^{20k}$.

each $R^{12}$ is independently selected from hydrogen, $C_{1-6}$alkyl, $C_{2-9}$heterocycloalkyl, and —$CH_2$-$C_{2-9}$heterocycloalkyl, wherein $C_{1-6}$alkyl, $C_{2-9}$heterocycloalkyl, and —$CH_2$-$C_{2-9}$heterocycloalkyl are optionally substituted with one, two, or three $R^{20l}$;

each $R^{13}$ is independently selected from hydrogen, $C_{1-6}$alkyl;

each $R^{1d}$ is independently selected from hydrogen and $C_{1-6}$alkyl;

each $R^{20j}$ is independently selected from halogen;

each $R^{20k}$ is independently selected from halogen, —CN, $C_{1-6}$alkyl, —$OR^{21}$, —N($R^{22}$)($R^{23}$), and —C(O)$R^{21}$, wherein $C_{1-6}$alkyl, is optionally substituted with one, two, or three groups independently selected from halogen, —CN, $C_{1-6}$alkyl, $C_{1-6}$haloalkyl, —$OR^{21}$, —N($R^{22}$)($R^{23}$);

each $R^{20l}$ is independently selected from halogen, $C_{3-10}$cycloalkyl, and —N($R^{22}$)($R^{23}$);

each $R^{21}$ is independently selected from H and $C_{1-6}$haloalkyl;

each $R^{22}$ is independently selected from H and $C_{1-6}$alkyl; and each $R^{23}$ is independently selected from H and $C_{1-6}$alkyl.

In some embodiments of a compound of Formula (I), (II), (III), (IV), (XVI), or (XVII), or a pharmaceutically acceptable salt or solvate thereof, the compound has a formula selected from:

Formula (XXVa)

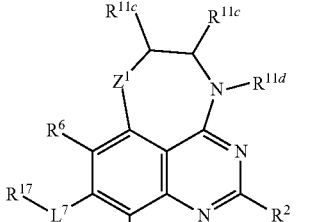

and

Formula (XXVd)

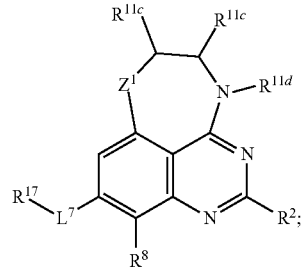

wherein $Z^1$ is selected from N($R^{11c}$) and O;

$R^6$ and $R^8$ are independently selected from hydrogen and halogen;

$L^7$ is a bond;

$R^{17}$ is selected from $C_{2-9}$heterocycloalkyl, $C_{6-10}$aryl, and $C_{1-9}$heteroaryl, wherein bicyclic $C_{2-9}$heterocycloalkyl, $C_{6-10}$aryl, and $C_1$-heteroaryl are optionally substituted with one, two, three, four, or five $R^{20g}$;

$R^2$ is —O—C($R^{12b}$)$_2$-$C_{2-9}$heterocycloalkyl optionally substituted with one, two, or three $R^{20l}$, each $R^{11c}$ is independently selected from hydrogen, $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, $C_{1-11}$heteroaryl, —($C_{1-6}$alkyl)-N($R^{14}$)C(O)$R^{12}$, and —($C_{1-6}$alkyl)-N($R^{12}$)($R^{13}$), wherein $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, and $C_{1-11}$heteroaryl are optionally substituted with one, two, or three $R^{20k}$;

each $R^{11d}$ is independently selected from $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, and C$_{1-11}$heteroaryl are optionally substituted with one, two, or three R$^{20k}$.

each R$^{12}$ is independently selected from hydrogen, C$_{1-6}$alkyl, C$_{2-9}$heterocycloalkyl, and —CH$_2$-C$_{2-9}$heterocycloalkyl, wherein C$_{1-6}$alkyl, C$_{2-9}$heterocycloalkyl, and —CH$_2$-C$_{2-9}$heterocycloalkyl are optionally substituted with one, two, or three R$^{20l}$, each R$^{12b}$ is independently selected from hydrogen and C$_{1-6}$alkyl;

each R$^{13}$ is independently selected from hydrogen, C$_{1-6}$alkyl;

each R$^{1d}$ is independently selected from hydrogen and C$_{1-6}$alkyl;

each R$^{20j}$ is independently selected from halogen;

each R$^{20g}$ is independently selected from halogen, —CN, C$_{1-6}$alkyl, C$_{2-6}$alkenyl, C$_{2-6}$alkynyl, C$_{3-10}$cycloalkyl, —OR$^{21}$, and —N(R$^{22}$)(R$^{23}$), wherein C$_{1-6}$alkyl, C$_{2-6}$alkenyl, C$_{2-6}$alkynyl, and C$_{3-10}$cycloalkyl are optionally substituted with one, two, or three groups independently selected from halogen, —OR$^{21}$, and —N(R$^{22}$)(R$^{23}$);

each R$^{20l}$ is independently selected from halogen, C$_{1-6}$alkyl, C$_{3-10}$cycloalkyl, C$_{2-9}$heterocycloalkyl, —CH$_2$-C$_{2-9}$heterocycloalkyl, and =C(R$^{21b}$)$_2$, wherein C$_{1-6}$alkyl, C$_{3-10}$cycloalkyl, C$_{2-9}$heterocycloalkyl, and —CH$_2$-C$_{2-9}$heterocycloalkyl, are optionally substituted with one, two, or three groups independently selected from —OC(O)N(R$^{22}$)(R$^{23}$) and —OC(O)R$^{25}$;

each R$^{20k}$ is independently selected from halogen, —CN, C$_{1-6}$alkyl, —OR$^{21}$, —N(R$^{22}$)(R$^{23}$), and —C(O)R$^{21}$, wherein C$_{1-6}$alkyl, is optionally substituted with one, two, or three groups independently selected from halogen, —CN, C$_{1-6}$alkyl, C$_{1-6}$haloalkyl, —OR$^{21}$, —N(R$^{22}$)(R$^{23}$);

each R$^{21}$ is independently selected from H and C$_{1-6}$haloalkyl;

each R$^{21b}$ is independently selected from hydrogen and halogen;

each R$^{22}$ is independently selected from H and C$_{1-6}$alkyl;

each R$^{23}$ is independently selected from H and C$_{1-6}$alkyl.

each R$^{25}$ is independently selected from C$_{2-9}$heterocycloalkyl; and

------ indicates a single or double bond such that all valences are satisfied.

In some embodiments of a compound of Formula (I), (II), (III), (IV), (XVI), or (XVII), or a pharmaceutically acceptable salt or solvate thereof, the compound has a formula selected from:

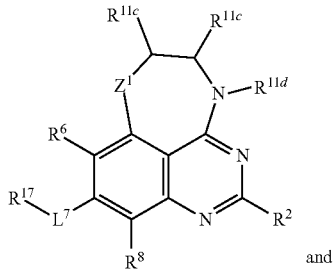

Formula (XXVa)

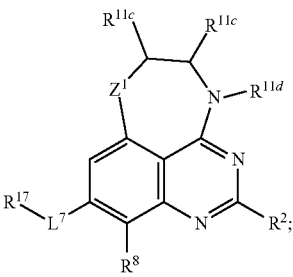

Formula (XXVd)

wherein Z$^1$ is selected from N(R$^{11c}$) and O;

R$^6$ and R$^8$ are independently selected from hydrogen and halogen;

L$^7$ is a bond;

R$^{17}$ is selected from bicyclic 9-10 membered heterocycloalkyl, phenyl, naphthyl, pyridyl, and bicyclic 9-10 membered heteroaryl, wherein bicyclic 9-10 membered heterocycloalkyl, phenyl, naphthyl, pyridyl, and bicyclic 9-10 membered heteroaryl are optionally substituted with one, two, three, four, or five R$^{20g}$;

R$^2$ is —O—C(R$^{12b}$)$_2$-C$_{2-9}$heterocycloalkyl optionally substituted with one, two, or three R$^{20l}$;

each R$^{11c}$ is independently selected from hydrogen, C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, C$_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, and C$_{1-11}$heteroaryl are optionally substituted with one, two, or three R$^{20k}$;

each R$^{11d}$ is independently selected from C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, C$_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein C$_{1-6}$alkyl, C$_{3-12}$cycloalkyl, —CH$_2$-C$_{3-12}$cycloalkyl, C$_{1-11}$heterocycloalkyl, CH$_2$-C$_{1-11}$heterocycloalkyl, and C$_{1-11}$heteroaryl are optionally substituted with one, two, or three R$^{20k}$.

each R$^{12}$ is independently selected from hydrogen, C$_{1-6}$alkyl, C$_{2-9}$heterocycloalkyl, and —CH$_2$-C$_{2-9}$heterocycloalkyl, wherein C$_{1-6}$alkyl, C$_{2-9}$heterocycloalkyl, and —CH$_2$-C$_{2-9}$heterocycloalkyl are optionally substituted with one, two, or three R$^{20l}$;

each R$^{12b}$ is independently selected from hydrogen and C$_{1-6}$alkyl;

each R$^{13}$ is independently selected from hydrogen, C$_{1-6}$alkyl;

each R$^{1d}$ is independently selected from hydrogen and C$_{1-6}$alkyl;

each R$^{20j}$ is independently selected from halogen;

each R$^{20g}$ is independently selected from halogen, —CN, C$_{1-6}$alkyl, C$_{2-6}$alkenyl, C$_{2-6}$alkynyl, C$_{3-10}$cycloalkyl, —OR$^{21}$, and —N(R$^{22}$)(R$^{23}$), wherein C$_{1-6}$alkyl, C$_{2-6}$alkenyl, C$_{2-6}$alkynyl, and C$_{3-10}$cycloalkyl are optionally substituted with one, two, or three groups independently selected from halogen, —OR$^{21}$, and —N(R$^{22}$)(R$^{23}$);

each R$^{20l}$ is independently selected from halogen, C$_{1-6}$alkyl, C$_{3-10}$cycloalkyl, C$_{2-9}$heterocycloalkyl, —CH$_2$-C$_{2-9}$heterocycloalkyl, =NR21, —N(R$^{22}$)(R$^{23}$), and =C(R$^{21b}$)$_2$, wherein C$_{1-6}$alkyl, C$_{3-10}$cycloalkyl, C$_{2-9}$heterocycloalkyl, and —CH$_2$-C$_{2-9}$heterocycloalkyl, are optionally substituted with one, two, or three groups independently selected from —OC(O)N(R$^{22}$)(R$^{23}$) and —OC(O)R$^{25}$;

each R$^{20k}$ is independently selected from halogen, —CN, C$_{1-6}$alkyl, —OR$^{21}$, —N(R$^{22}$)(R$^{23}$), —N(R$^{24}$)S(O)$_2$R$^{25}$, and —C(O)R$^{21}$, wherein C$_{1-6}$alkyl, is optionally substituted with one, two, or three groups independently selected from halogen, —CN, C$_{1-6}$alkyl, C$_{1-6}$haloalkyl, —OR$^{21}$, —N(R$^{22}$)(R$^{23}$);

each R$^{21}$ is independently selected from H and C$_{1-6}$haloalkyl;

each R$^{21b}$ is independently selected from hydrogen and halogen;

each R$^{22}$ is independently selected from H and C$_{1-6}$alkyl;

each R$^{23}$ is independently selected from H and C$_{1-6}$alkyl;

each R$^{24}$ is H;

each R$^{25}$ is independently selected from C$_{2-9}$heterocycloalkyl; and

----- indicates a single or double bond such that all valences are satisfied.

In some embodiments of a compound of Formula (I), (II), (III), (IV), (XVI), or (XVII), or a pharmaceutically acceptable salt or solvate thereof, the compound has a formula selected from:

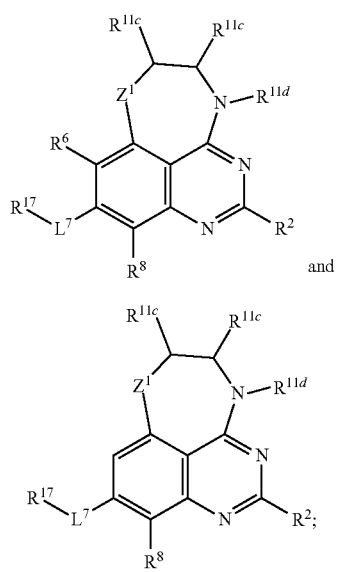

Formula (XXVa)

and

Formula (XXVd)

wherein Z$^1$ is selected from N(R$^{11c}$) and O;

R$^6$ and R$^8$ are independently selected from hydrogen and halogen;

L$^7$ is a bond;

R$^{17}$ is selected from:

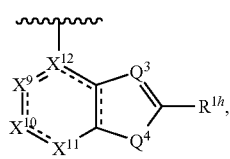

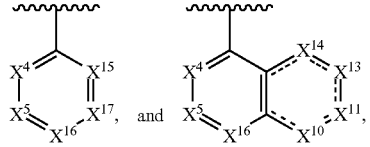

Q$^3$ is N or C(R$^{1d}$); Q$^4$ is S;

X$^4$, X$^3$, X$^{15}$, X$^{16}$, and X$^{17}$ are independently selected from C(R$^{1a}$) or N;

X$^9$ is C(R$^{1a}$); X$^{10}$, X$^{11}$, X$^{13}$, and X$^{14}$ are independently C(R$^{1a}$) or N; X$^{12}$ is C;

each R$^{1a}$ and R$^{1h}$ is independently selected from hydrogen, halogen, —CN, C$_{1-4}$alkyl, C$_{1-4}$haloalkyl, C$_{2-4}$alkenyl, C$_{2-4}$alkynyl, C$_3$-cycloalkyl, C$_{2-4}$heterocycloalkyl, —OH, —NH$_2$, —C(O)OH, —OC(O)NH$_2$, and —C(O)CH$_3$;

R$^{1d}$ is selected from hydrogen, —CN, C$_{1-4}$alkyl, and C$_1$-haloalkyl;

R$^2$ is selected from

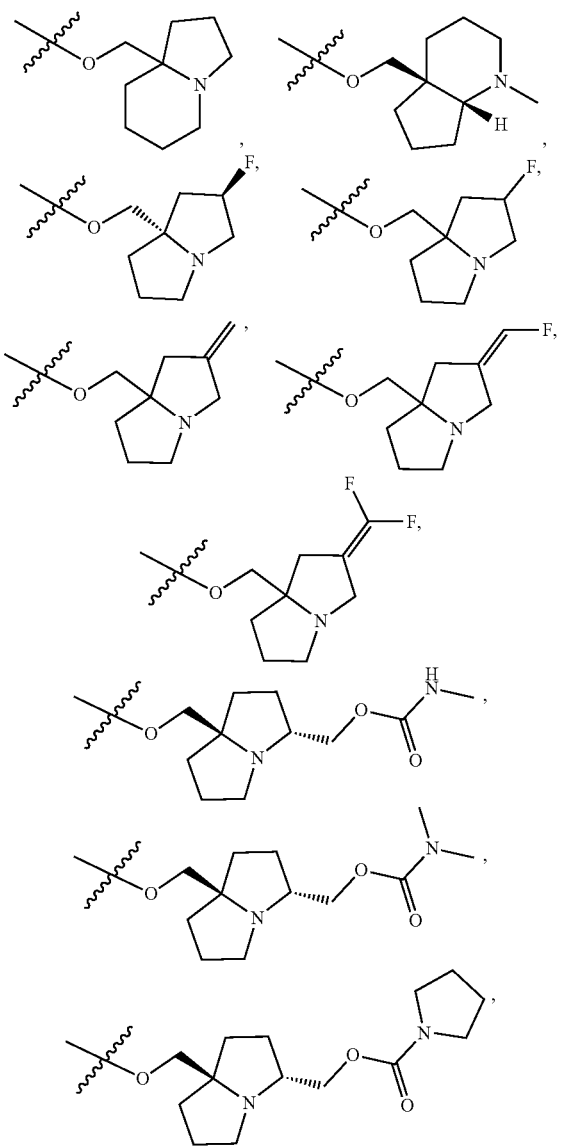

-continued

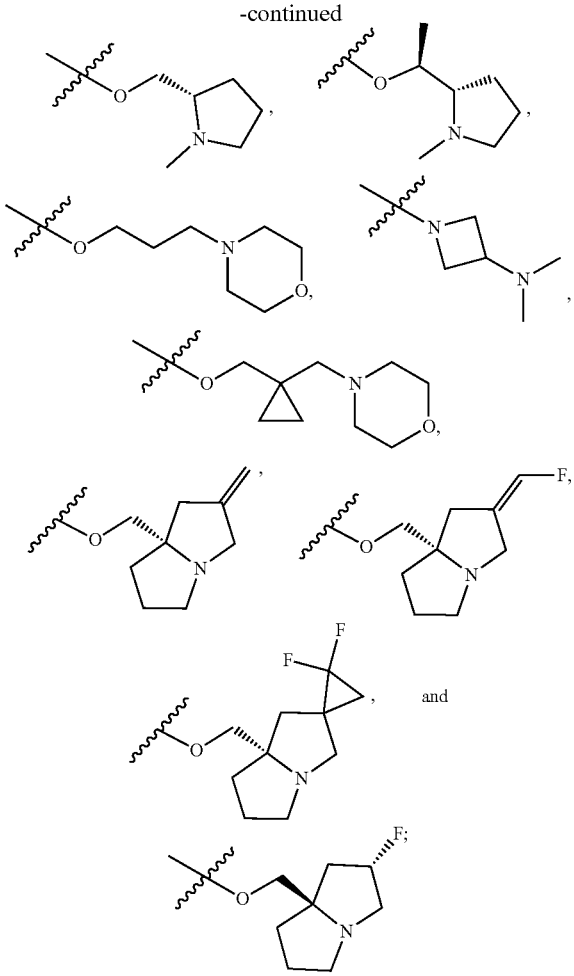

each $R^{11c}$ is independently selected from hydrogen, $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, $C_{1-11}$heteroaryl, —($C_{1-6}$alkyl)-$N(R^{14})C(O)R^{12}$, and —($C_{1-6}$alkyl)-$N(R^{12})(R^{13})$, wherein $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, and $C_{1-11}$heteroaryl are optionally substituted with one, two, or three $R^{20j}$;

each $R^{11d}$ is independently selected from $C_{1-6}$alkyl, $C_{3-12}$cycloalkyl, —$CH_2$-$C_{3-12}$cycloalkyl, $C_{1-11}$heterocycloalkyl, $CH_2$-$C_{1-6}$ 11heterocycloalkyl, $C_{1-11}$heteroaryl, —($C_{1-6}$alkyl)-$N(R^{14})C(O)R^{12}$, and —($C_{1-6}$alkyl)-$N(R^{12})(R^{13})$, wherein $C_{1-6}$alkyl, $C_{3-12}$cycloalkyl, —$CH_2$-$C_{3-12}$cycloalkyl, $C_{1-11}$heterocycloalkyl, $CH_2$-$C_{1-11}$heterocycloalkyl, and $C_{1-11}$heteroaryl are optionally substituted with one, two, or three $R^{20k}$.

each $R^{12}$ is independently selected from hydrogen, $C_{1-6}$alkyl, $C_{2-9}$heterocycloalkyl, and —$CH_2$-$C_{2-9}$heterocycloalkyl, wherein $C_{1-6}$alkyl, $C_{2-9}$heterocycloalkyl, and —$CH_2$-$C_{2-9}$heterocycloalkyl are optionally substituted with one, two, or three $R^{20l}$;

each $R^{13}$ is independently selected from hydrogen, $C_{1-6}$alkyl;

each $R^{1d}$ is independently selected from hydrogen and $C_{1-6}$alkyl;

each $R^{20j}$ is independently selected from halogen;

each $R^{20k}$ is independently selected from halogen, —CN, $C_{1-6}$alkyl, —$OR^{21}$, —$N(R^{22})(R^{23})$, —$N(R^{24})$ $S(O)_2R^{25}$, and —$C(O)R^{21}$, wherein $C_{1-6}$alkyl, is optionally substituted with one, two, or three groups independently selected from halogen, —CN, $C_{1-6}$alkyl, $C_{1-6}$haloalkyl, —$OR^{21}$, —$N(R^{22})(R^{23})$;

each $R^{20l}$ is independently selected from halogen, $C_{3-10}$cycloalkyl, =NR21, and —$N(R^{22})(R^{23})$;

each $R^{21}$ is independently selected from H and $C_{1-6}$haloalkyl;

each $R^{22}$ is independently selected from H and $C_{1-6}$alkyl;

each $R^{23}$ is independently selected from H and $C_{1-6}$alkyl;

each $R^{24}$ is H; and each $R^{25}$ is independently $C_{1-6}$alkyl.

In some embodiments of a compound of Formula (I), (II), (III), (IV), (XVI), or (XVII), or a pharmaceutically acceptable salt or solvate thereof, the compound has a formula selected from:

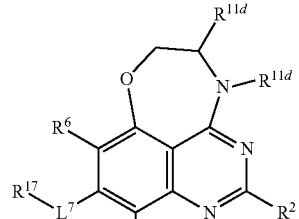

Formula (XXVIIIa)

and

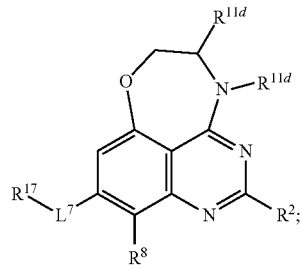

Formula (XXVIIId)

wherein
$R^6$ and $R^8$ are independently selected from hydrogen and halogen;
$L^7$ is a bond;
$R^{17}$ is selected from:

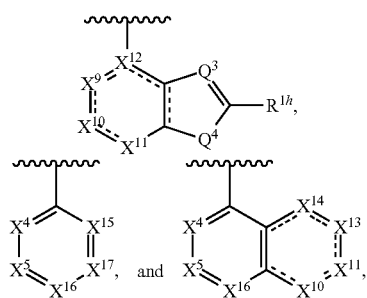

$Q^3$ is N or $C(R^{1d})$; $Q^4$ is S;
$X^4$, $X^5$, $X^{15}$, $X^{16}$, and $X^{17}$ are independently selected from $C(R^{1a})$ or N;
$X^9$ is $C(R^{1a})$; $X^{10}$, $X^{11}$, $X^{13}$, and $X^{14}$ are independently $C(R^{1a})$ or N; $X^{12}$ is C;
each $R^{1a}$ and $R^{1h}$ is independently selected from hydrogen, halogen, —CN, $C_{1-4}$alkyl, $C_{1-4}$haloalkyl, $C_{2-4}$alkenyl, C$_{2-4}$alkynyl, C$_{3-4}$cycloalkyl, C$_{2-4}$heterocycloalkyl, —OH, —NH$_2$, —C(O)OH, —OC(O)NH$_2$, —C(O)CH$_3$, —NHC(O)H;

R$^{1d}$ is selected from hydrogen, —CN, C$_{1-4}$alkyl, and C$_{1-4}$haloalkyl;

R$^2$ is selected from

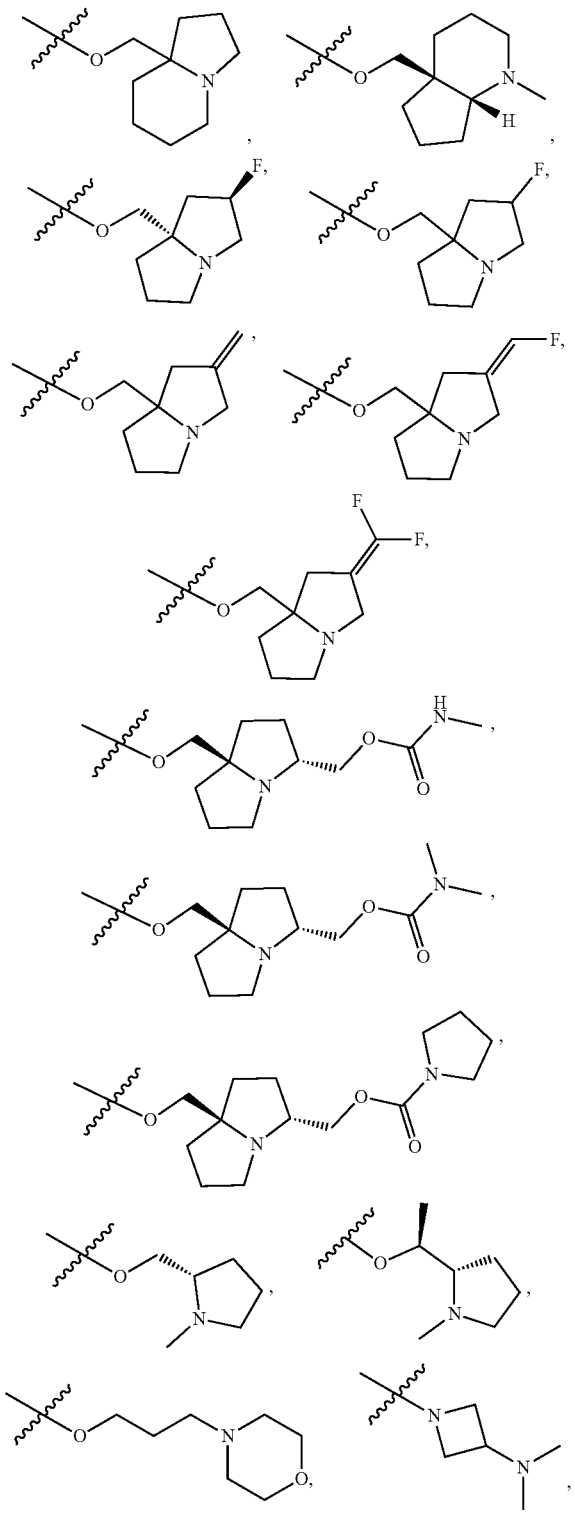

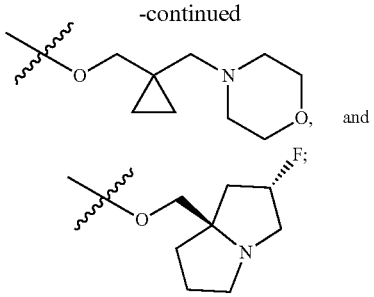

each R$^{11d}$ is independently selected from C$_{1-6}$alkyl, C$_{2-6}$alkenyl, C$_{3-12}$cycloalkyl, —CH$_2$-C$_{5-12}$cycloalkyl, C$_{1-11}$heterocycloalkyl, —CH$_2$-C$_{1-11}$heterocycloalkyl, C$_{6-10}$aryl, —CH$_2$-C$_{1-11}$heteroaryl, C$_{1-11}$heteroaryl, —(C$_{1-6}$alkyl)-N(R$^{14}$)C(O)R$^{12}$, wherein C$_{1-6}$alkyl, C$_{2-6}$alkenyl, C$_{3-12}$cycloalkyl, —CH$_2$-C$_{5-12}$cycloalkyl, C$_{1-11}$heterocycloalkyl, —CH$_2$-C$_{1-11}$heterocycloalkyl, C$_{6-10}$aryl, —CH$_2$-C$_{1-11}$heteroaryl, and C$_{1-11}$heteroaryl are optionally substituted with one, two, or three R$^{20k}$;

each R$^{12}$ is independently selected from hydrogen, C$_{1-6}$alkyl, C$_{3-10}$cycloalkyl, C$_{2-9}$heterocycloalkyl, —CH$_2$-C$_{2-9}$heterocycloalkyl, wherein C$_{1-6}$alkyl, C$_{3-10}$cycloalkyl, C$_{2-9}$heterocycloalkyl, and —CH$_2$-C$_{2-9}$heterocycloalkyl are optionally substituted with one, two, or three R$^{20l}$ each R$^{1d}$ is independently selected from hydrogen, C$_{1-6}$alkyl, and C$_{1-6}$haloalkyl;

each R$^{20k}$ is independently selected from halogen, oxo, —CN, C$_{1-6}$alkyl, C$_{2-6}$alkenyl, C$_{5-10}$cycloalkyl, C$_{2-9}$heterocycloalkyl, C$_1$-9heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein C$_{1-6}$alkyl, C$_{2-6}$alkenyl, C$_5$-10cycloalkyl, C$_{2-9}$heterocycloalkyl, and C$_{1-9}$heteroaryl are optionally substituted with one, two, or three groups independently selected from halogen, —CN, C$_{1-6}$alkyl, C$_{1-6}$haloalkyl, —OR$^{21}$, and —N(R$^{22}$)(R$^{23}$);

each R$^{20l}$ is independently selected from halogen, —OR$^{21}$, and C$_{3-10}$cycloalkyl;

each R$^{21}$ is independently selected from H, C$_{1-6}$alkyl, C$_{1-6}$haloalkyl, C$_{3-10}$cycloalkyl, C$_{2-9}$heterocycloalkyl, and C$_{1-9}$heteroaryl;

each R$^{22}$ is independently selected from H and C$_{1-6}$alkyl;

each R$^{23}$ is independently selected from H and C$_{1-6}$alkyl;

each R$^{24}$ is independently selected from H and C$_{1-6}$alkyl; and each R$^{25}$ is independently selected from C$_{1-6}$alkyl and C$_{3-6}$cycloalkyl.

In some embodiments of a compound of Formula (I), (II), (III), (IV), (XVI), or (XVII), (XVI), or (XVII), or a pharmaceutically acceptable salt or solvate thereof, the compound has a formula selected from:

Formula (XVIIIa)

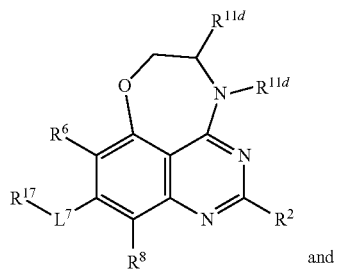

and

893
-continued

Formula (XVIIId)

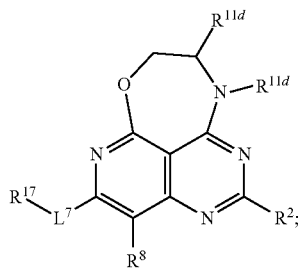

wherein
R⁶ and R⁸ are independently selected from hydrogen and halogen;
L⁷ is a bond;
R¹⁷ is selected from:

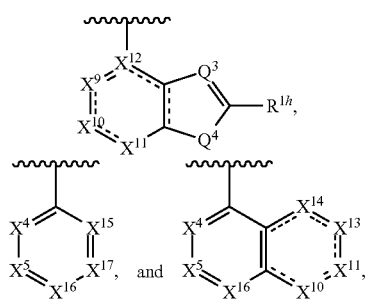

$Q^3$ is N or $C(R^{14})$; $Q^4$ is S;
$X^4$, $X^5$, $X^{15}$, $X^{16}$, and $X^{17}$ are independently selected from $C(R^{1a})$ or N;
$X^9$ is $C(R^{1a})$; $X^{10}$, $X^{11}$, $X^{13}$, and $X^{14}$ are independently $C(R^{1a})$ or N; $X^{12}$ is C;
each $R^{1a}$ and $R^{1h}$ is independently selected from hydrogen, halogen, —CN, $C_{1-4}$alkyl, $C_{1-4}$haloalkyl, $C_{2-4}$alkenyl, $C_{2-4}$alkynyl, $C_{3-4}$cycloalkyl, $C_{2-4}$heterocycloalkyl, —OH, —NH₂, —C(O)OH, —OC(O)NH₂, and —C(O)CH₃;
$R^{1d}$ is selected from hydrogen, —CN, $C_{1-4}$alkyl, and $C_{1-4}$haloalkyl;
$R^2$ is selected from

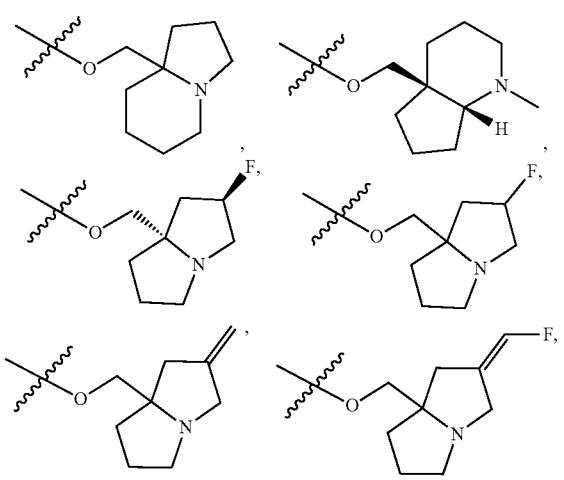

894
-continued

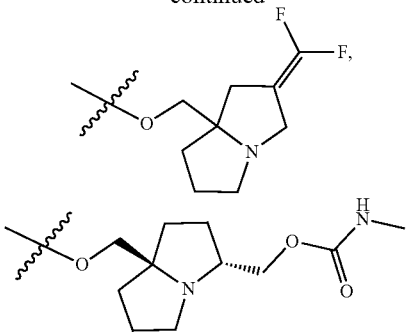

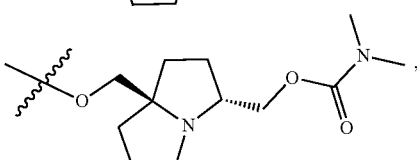

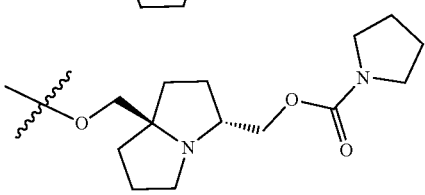

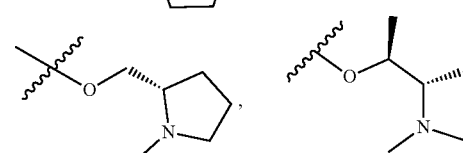

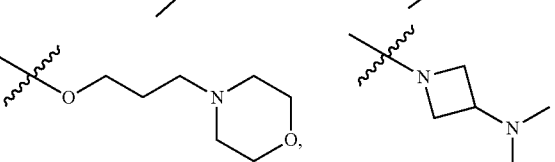

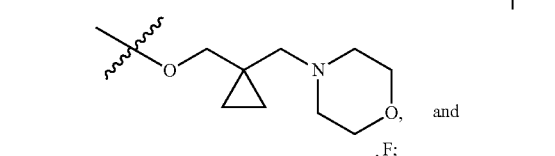

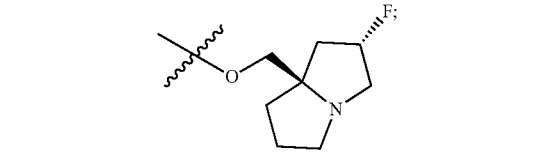

each $R^{11d}$ is independently selected from $C_{1-6}$alkyl, $C_{2-6}$alkenyl, $C_{3-12}$cycloalkyl, —CH₂-$C_{3-12}$cycloalkyl, $C_{1-11}$heterocycloalkyl, —CH₂-$C_{1-11}$heterocycloalkyl, $C_{6-10}$aryl, —CH₂-$C_{1-11}$heteroaryl, $C_{1-11}$heteroaryl, —($C_{1-6}$alkyl)-N(R¹⁴)C(O)R¹², wherein $C_{1-6}$alkyl, $C_{2-6}$alkenyl, $C_{3-12}$cycloalkyl, —CH₂-$C_{3-12}$cycloalkyl, $C_{1-11}$heterocycloalkyl, —CH₂-$C_{1-11}$heterocycloalkyl, $C_{6-10}$aryl, —CH₂-$C_{1-11}$heteroaryl, and $C_{1-11}$heteroaryl are optionally substituted with one, two, or three $R^{20k}$;
each $R^{12}$ is independently selected from hydrogen, $C_{1-6}$alkyl, $C_{3-10}$cycloalkyl, $C_{2-9}$heterocycloalkyl, —CH₂-$C_{2-9}$heterocycloalkyl, wherein $C_{1-6}$alkyl, $C_{3-10}$cycloalkyl, $C_{2-9}$heterocycloalkyl, and —CH₂-$C_{2-9}$heterocycloalkyl are optionally substituted with one, two, or three $R^{20l}$;
each $R^{1d}$ is independently selected from hydrogen, $C_{1-6}$alkyl, and $C_{1-6}$haloalkyl;

each $R^{20k}$ is independently selected from oxo, —CN, $C_{1-6}$alkyl, $C_{2-6}$alkenyl, $C_{5-10}$cycloalkyl, $C_{2-9}$heterocycloalkyl, $C_{1-9}$heteroaryl, —OR$^{21}$, —N(R$^{22}$)(R$^{23}$), —C(O)N(R$^{22}$)(R$^{23}$), —N(R$^{24}$)C(O)R$^{21}$, —C(O)R$^{21}$, and —S(O)$_2$R$^{25}$, wherein $C_{1-6}$alkyl, $C_{2-6}$alkenyl, $C_{3-10}$cycloalkyl, $C_{2-9}$heterocycloalkyl, and $C_{1-9}$heteroaryl are optionally substituted with one, two, or three groups independently selected from —CN, $C_{1-6}$alkyl, $C_{1-6}$haloalkyl, —OR$^{21}$, and —N(R$^{22}$)(R$^{23}$);

each $R^{20l}$ is independently selected from halogen, —OR$^{21}$, and $C_{3-10}$cycloalkyl;

each $R^{21}$ is independently selected from H, $C_{1-6}$alkyl, $C_{1-6}$haloalkyl, $C_{3-10}$cycloalkyl, $C_{2-9}$heterocycloalkyl, and $C_{1-9}$heteroaryl;

each $R^{22}$ is independently selected from H and $C_{1-6}$alkyl;
each $R^{23}$ is independently selected from H and $C_{1-6}$alkyl;
each $R^{24}$ is independently selected from H and $C_{1-6}$alkyl; and each $R^{25}$ is independently selected from $C_{1-6}$alkyl and $C_{3-6}$cycloalkyl.

In some embodiments of a compound of Formula (I), (II), (III), (IV), (XVI), or (XVII), or a pharmaceutically acceptable salt or solvate thereof, the compound has a formula selected from:

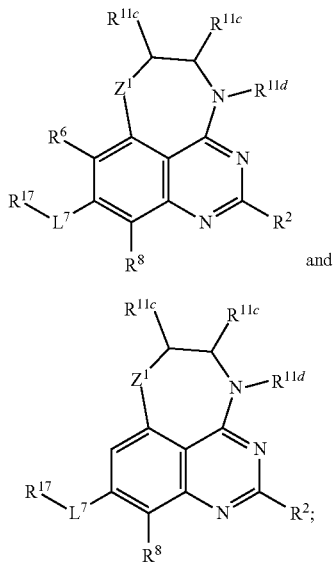

Formula (XXVa)

and

Formula (XXVd)

wherein $Z^1$ is selected from N(R$^{11c}$) and O;
$R^6$ and $R^8$ are independently selected from hydrogen and halogen;
$L^7$ is a bond;
$R^{17}$ is selected from $C_{2-9}$heterocycloalkyl, $C_{6-10}$aryl, and $C_{1-9}$heteroaryl, wherein bicyclic $C_{2-9}$heterocycloalkyl, $C_{6-10}$aryl, and $C_{1-6\ 9}$heteroaryl are optionally substituted with one, two, three, four, or five $R^{20g}$;
$R^2$ is —O—C(R$^{12b}$)$_2$-C$_{2-9}$heterocycloalkyl optionally substituted with one, two, or three $R^{20l}$;
each $R^{11c}$ is independently selected from hydrogen, $C_{1-6}$alkyl, $C_{3-12}$cycloalkyl, —CH$_2$-C$_{5-12}$cycloalkyl, $C_{1-11}$heterocycloalkyl, CH$_2$-C$_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-C$_{5-12}$cycloalkyl, $C_{1-11}$hetero-cycloalkyl, CH$_2$-C$_{1-11}$heterocycloalkyl, and $C_{1-11}$heteroaryl are optionally substituted with one, two, or three R$^{20k}$;

each $R^{11d}$ is independently selected from $C_{1-6}$alkyl, $C_{3-12}$cycloalkyl, —CH$_2$-C$_{3-12}$cycloalkyl, $C_{1-11}$hetero-cycloalkyl, CH$_2$-C$_{1-11}$heterocycloalkyl, $C_{1-11}$heteroaryl, —(C$_{1-6}$alkyl)-N(R$^{14}$)C(O)R$^{12}$, and —(C$_{1-6}$alkyl)-N(R$^{12}$)(R$^{13}$), wherein $C_{1-6}$alkyl, $C_{3-12}$cycloalkyl, —CH$_2$-C$_{3-12}$cycloalkyl, $C_{1-11}$heterocycloalkyl, CH$_2$-C$_{1-11}$heterocycloalkyl, and $C_{1-11}$heteroaryl are optionally substituted with one, two, or three $R^{20k}$;

each $R^{12}$ is independently selected from hydrogen, $C_{1-6}$alkyl, $C_{2-9}$heterocycloalkyl, and —CH$_2$-C$_{2-9}$heterocycloalkyl, wherein $C_{1-6}$alkyl, $C_{2-9}$heterocycloalkyl, and —CH$_2$-C$_{2-9}$heterocycloalkyl are optionally substituted with one, two, or three $R^{20l}$;

each $R^{12b}$ is independently selected from hydrogen and $C_{1-6}$alkyl;

each $R^{13}$ is independently selected from hydrogen, $C_{1-6}$alkyl;

each $R^{1d}$ is independently selected from hydrogen and $C_{1-6}$alkyl;

each $R^{20j}$ is independently selected from halogen;
each $R^{20g}$ is independently selected from halogen, —CN, $C_{1-6}$alkyl, $C_{2-6}$alkenyl, $C_{2-6}$alkynyl, $C_{3-10}$cycloalkyl, —OR$^{21}$, and —N(R$^{22}$)(R$^{23}$), wherein $C_{1-6}$alkyl, $C_{2-6}$alkenyl, $C_{2-6}$alkynyl, and $C_{3-10}$cycloalkyl are optionally substituted with one, two, or three groups independently selected from halogen, —OR$^{21}$, and —N(R$^{22}$)(R$^{23}$);

each $R^{20l}$ is independently selected from halogen, $C_{1-6}$alkyl, $C_{3-10}$cycloalkyl, $C_{2-9}$heterocycloalkyl, —CH$_2$-C$_{2-9}$heterocycloalkyl, and =C(R$^{21b}$)$_2$, wherein $C_{1-6}$alkyl, $C_{3-10}$cycloalkyl, $C_{2-9}$heterocycloalkyl, and —CH$_2$-C$_{2-9}$heterocycloalkyl, are optionally substituted with one, two, or three groups independently selected from —OC(O)N(R$^{22}$)(R$^{23}$) and —OC(O)R$^{25}$;

each $R^{20k}$ is independently selected from halogen, —CN, $C_{1-6}$alkyl, —OR$^{21}$, —N(R$^{22}$)(R$^{23}$), and —C(O)R$^{21}$, wherein $C_{1-6}$alkyl, is optionally substituted with one, two, or three groups independently selected from halogen, —CN, $C_{1-6}$alkyl, $C_{1-6}$haloalkyl, —OR$^{21}$, —N(R$^{22}$)(R$^{23}$);

each $R^{21}$ is independently selected from H and $C_{1-6}$haloalkyl;

each $R^{21b}$ is independently selected from hydrogen and halogen;

each $R^{22}$ is independently selected from H and $C_{1-6}$alkyl;
each $R^{23}$ is independently selected from H and $C_{1-6}$alkyl.
each $R^{25}$ is independently selected from $C_{2-9}$heterocycloalkyl; and ----- indicates a single or double bond such that all valences are satisfied.

In embodiments is a compound, or a pharmaceutically acceptable salt or solvate thereof, selected from:

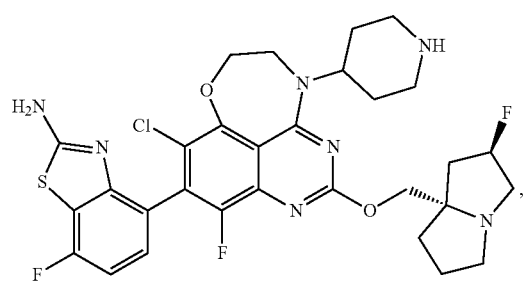

897
-continued
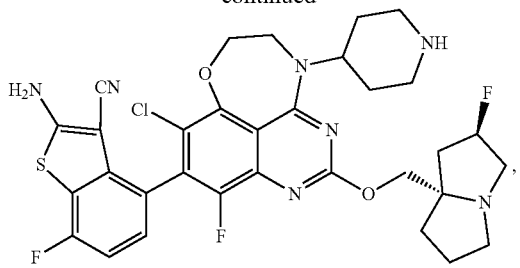
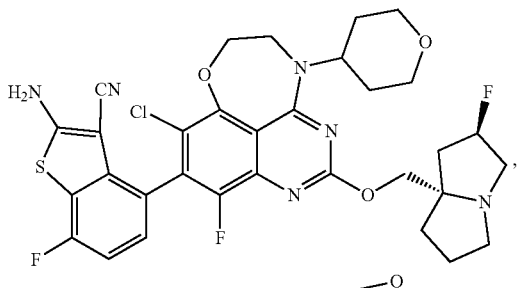
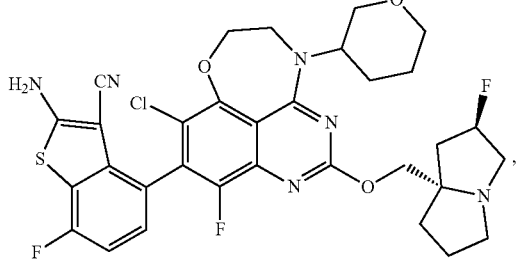
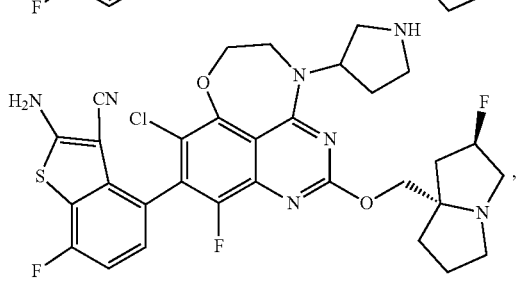
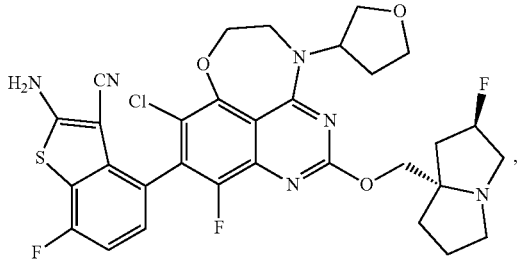
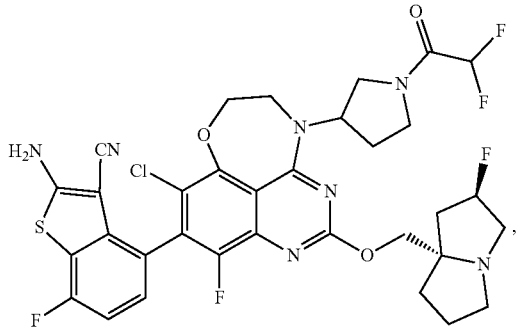
898
-continued
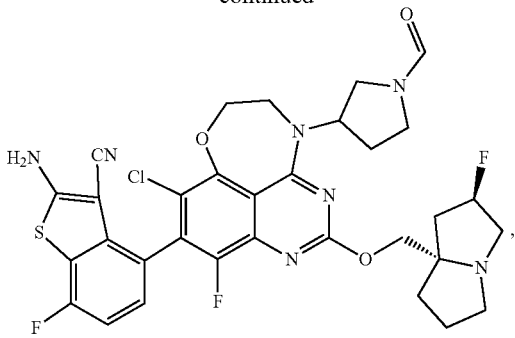
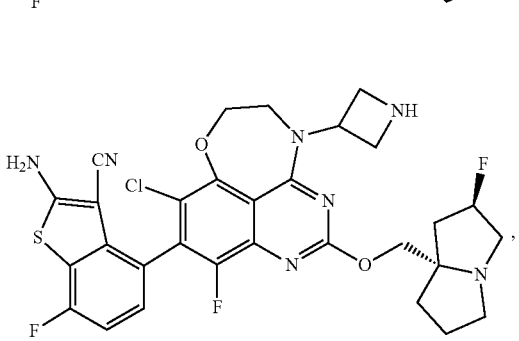
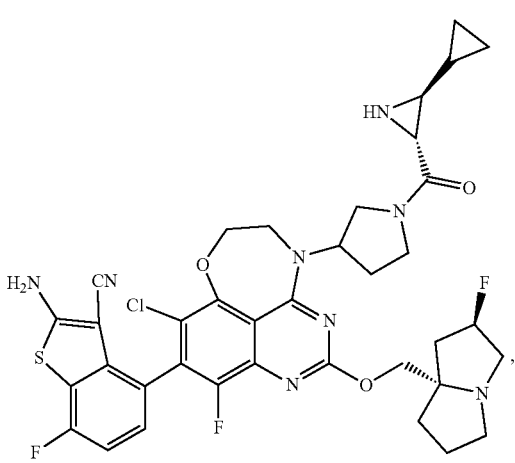
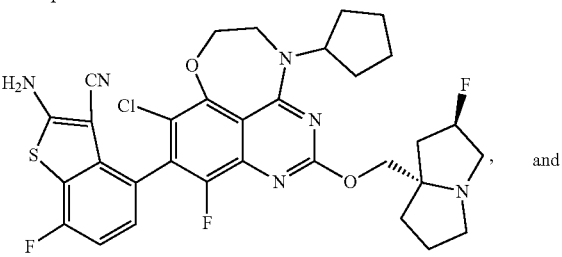, and
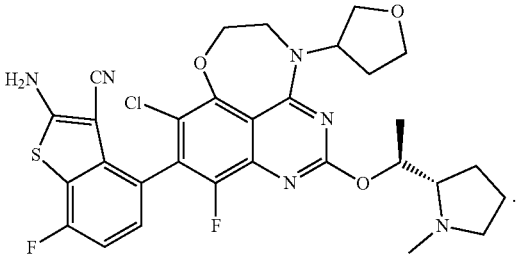
In embodiments is a compound, or a pharmaceutically acceptable salt or solvate thereof, selected from:

899
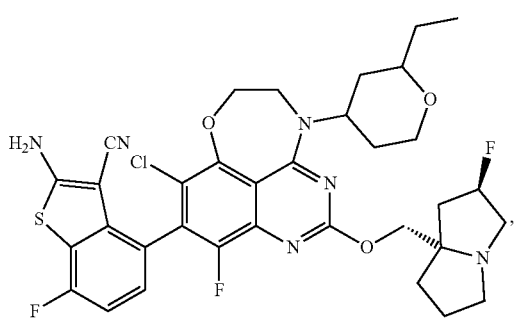
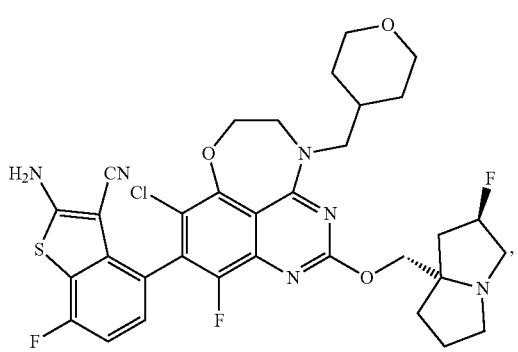
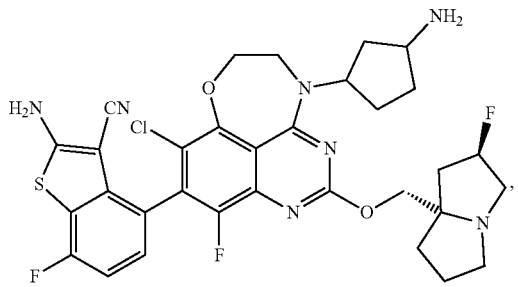
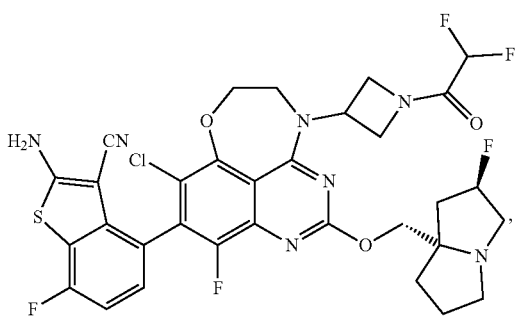
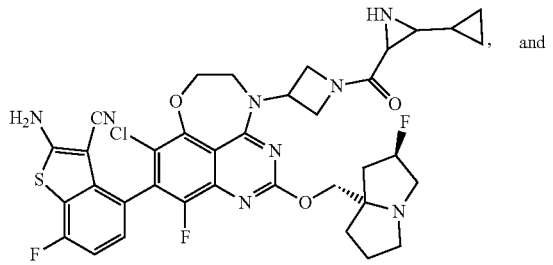, and
900
-continued
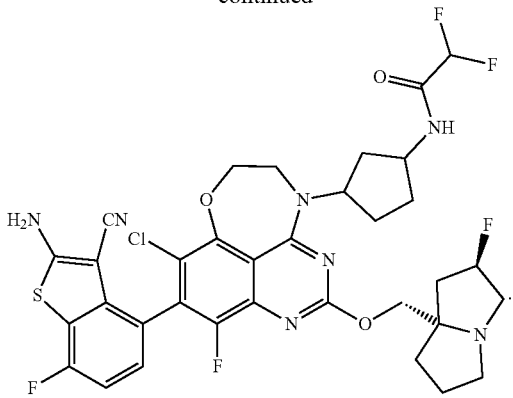
In embodiments is a compound, or a pharmaceutically acceptable salt or solvate thereof, selected from:
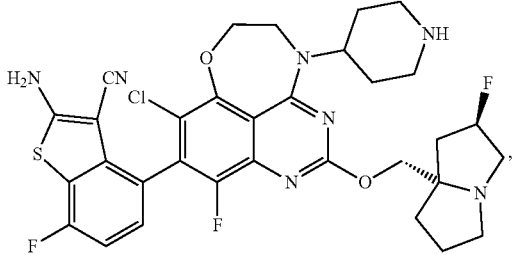
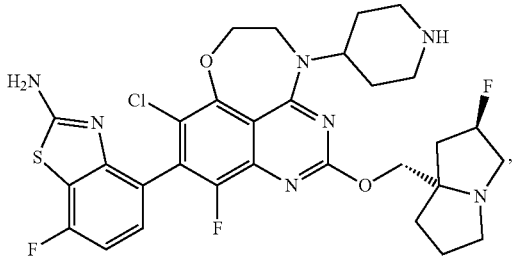
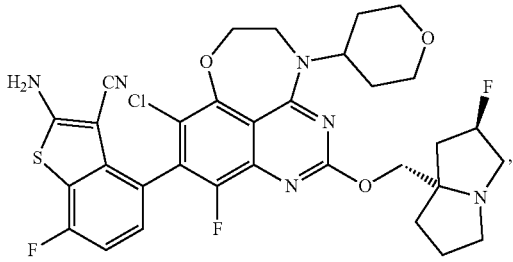
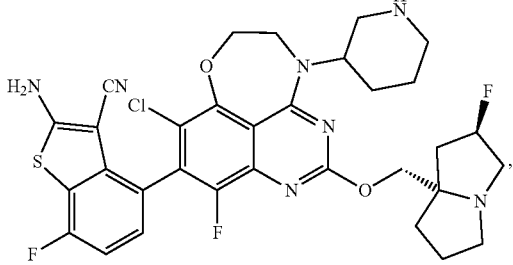, 901
-continued
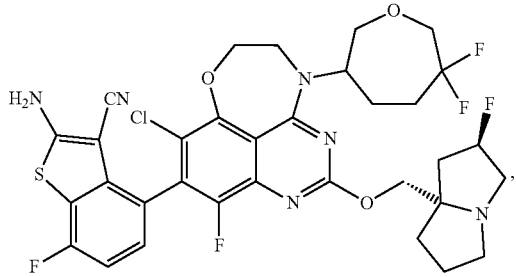
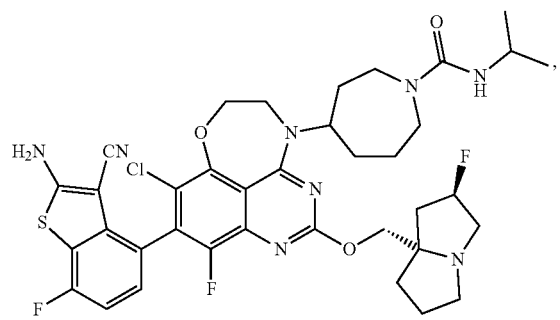
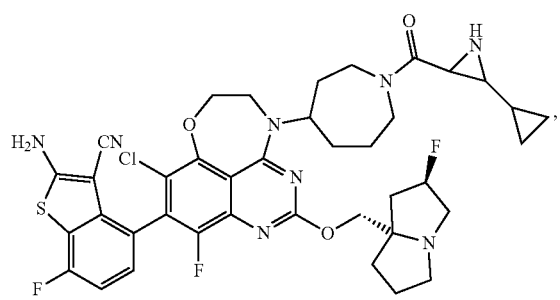
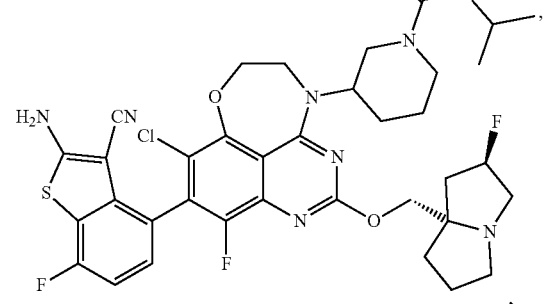
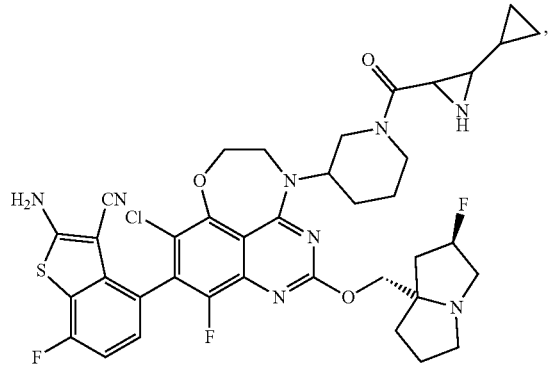
902
-continued
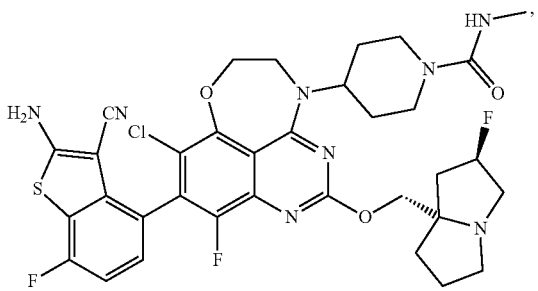
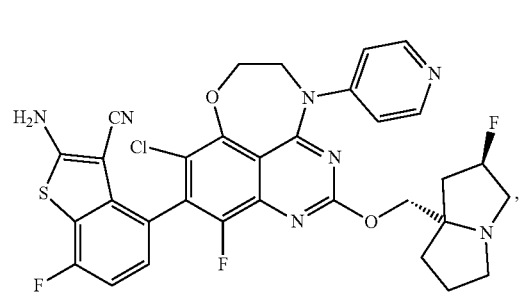
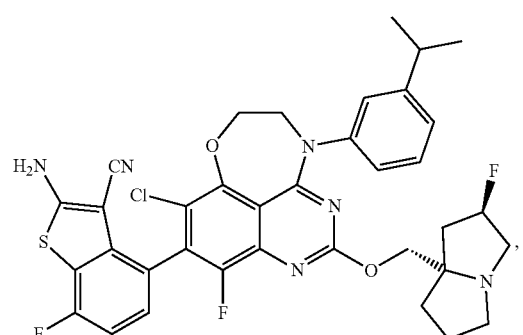
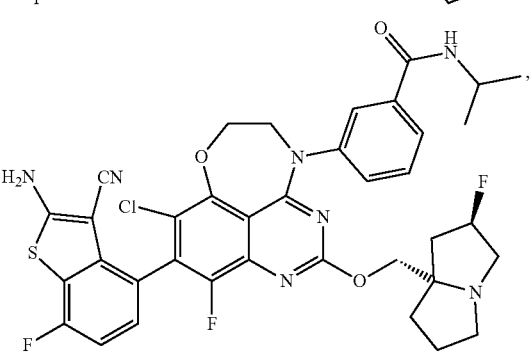
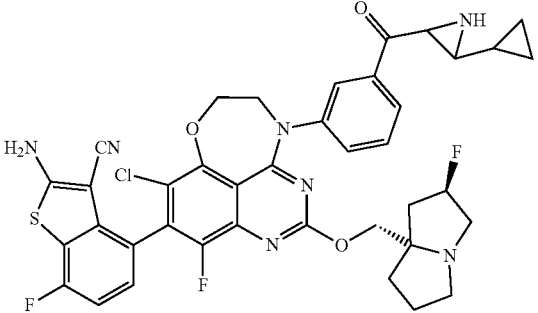

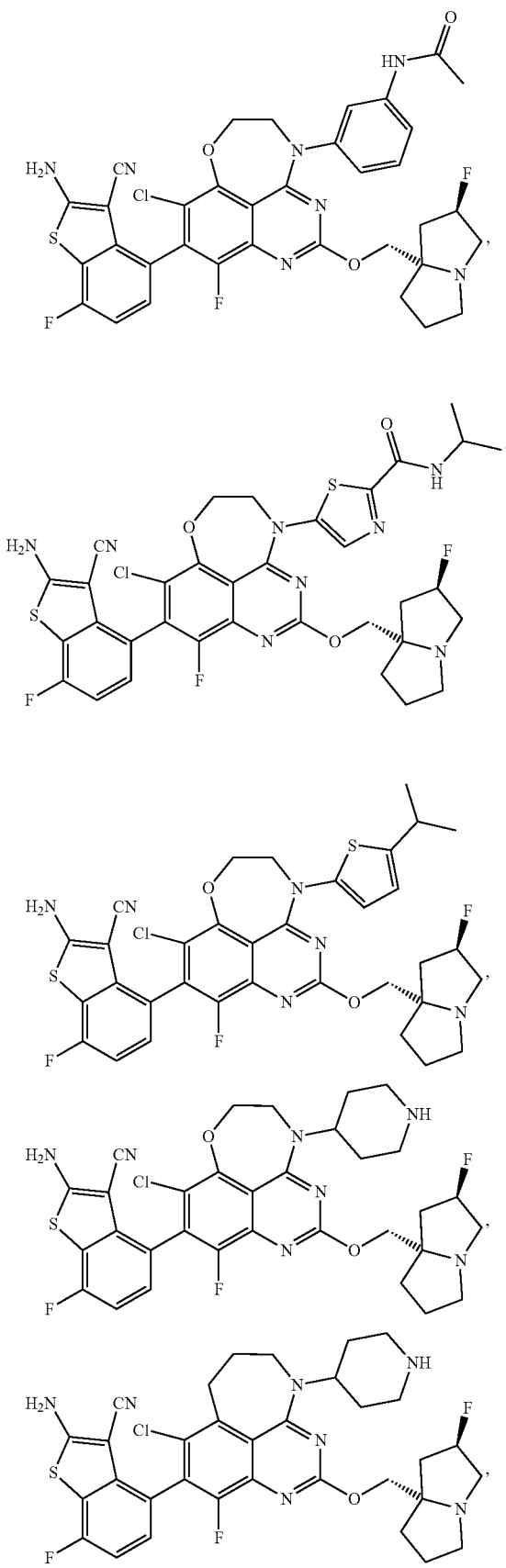
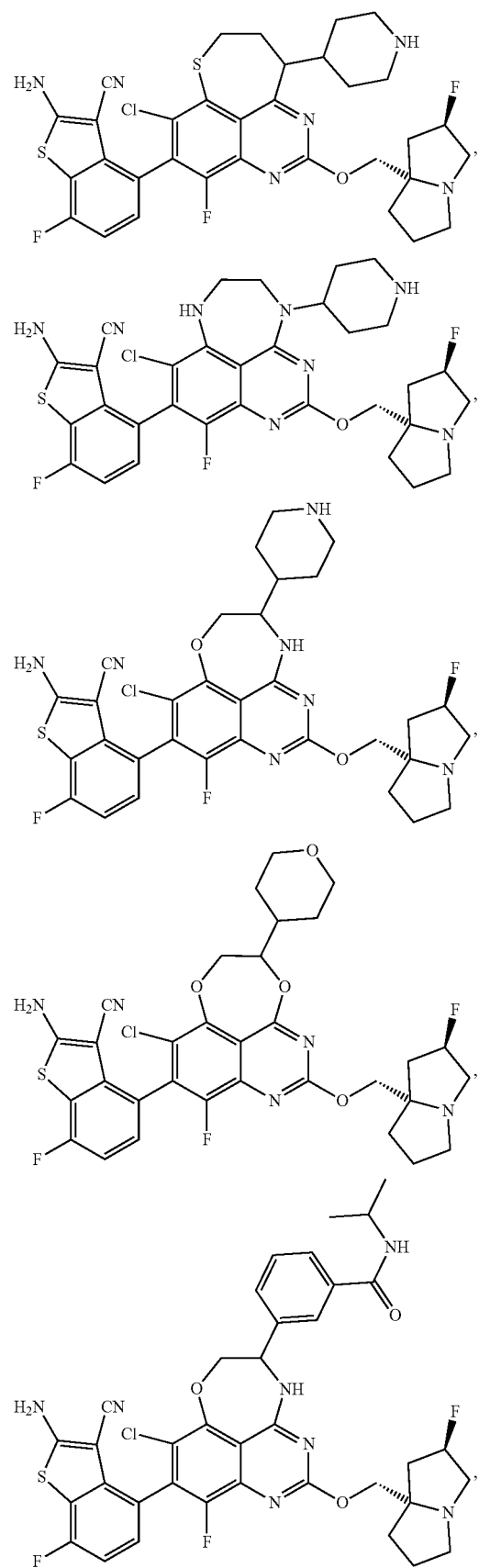

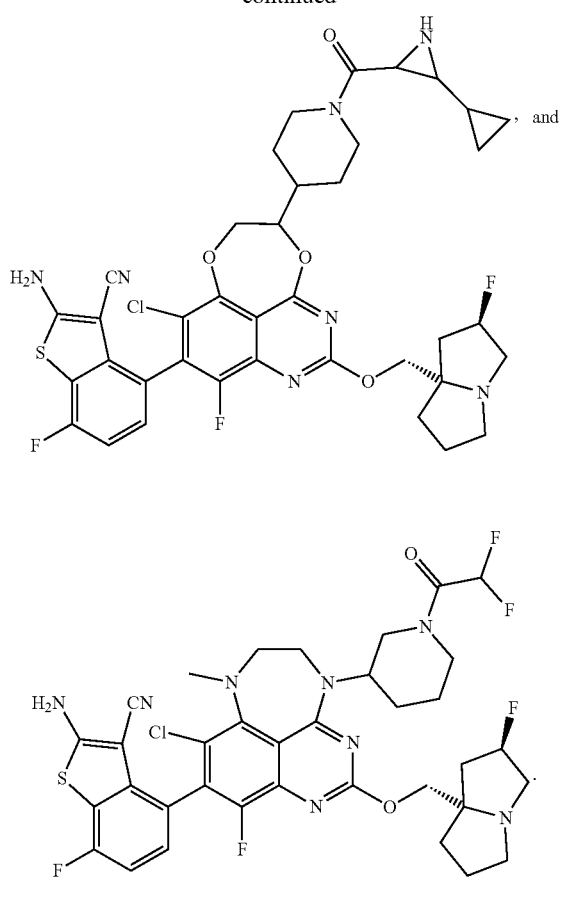
In embodiments is a compound, or a pharmaceutically acceptable salt or solvate thereof, selected from:
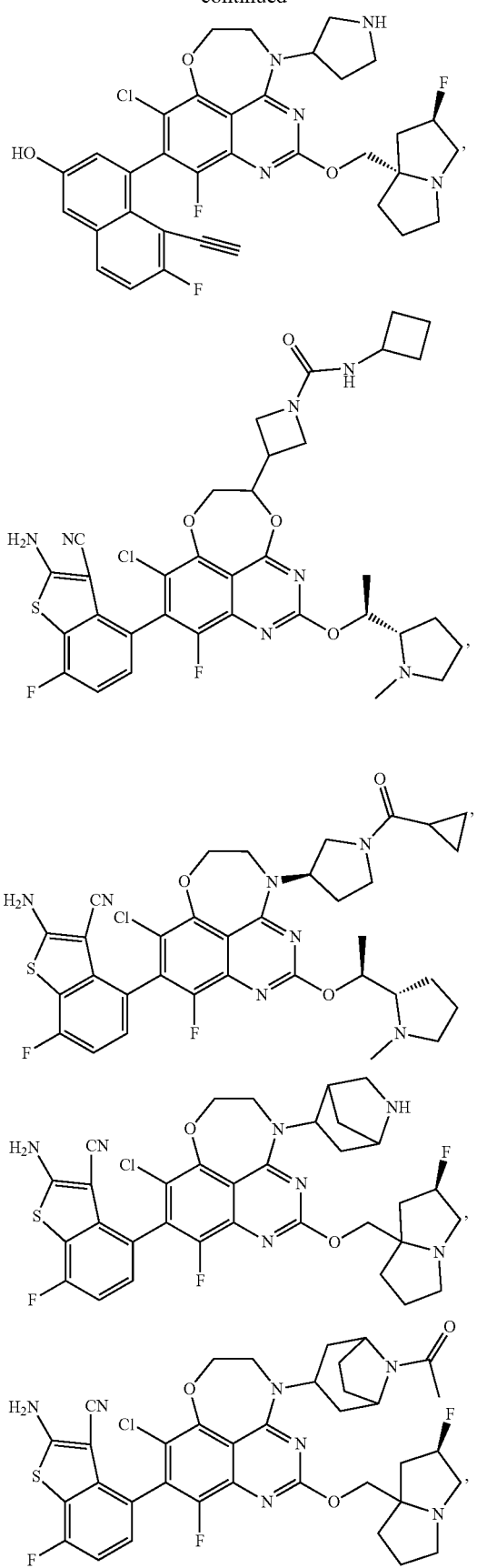

907
-continued
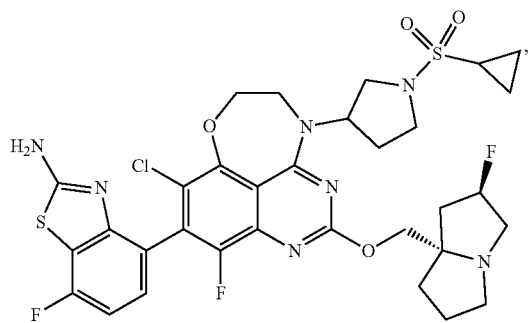
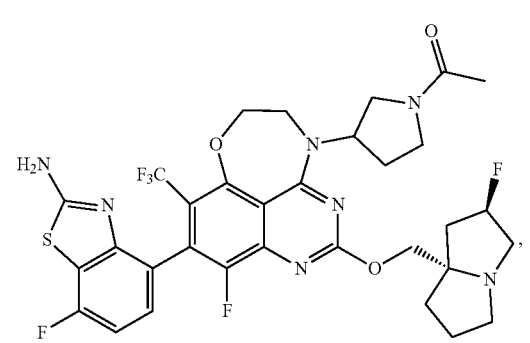
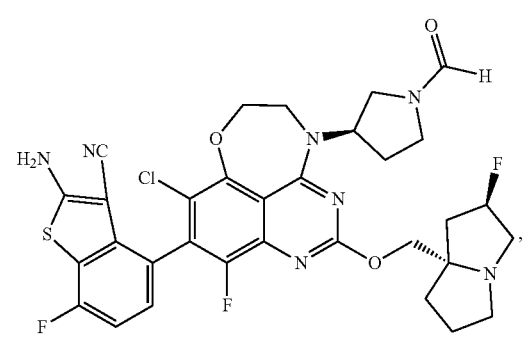
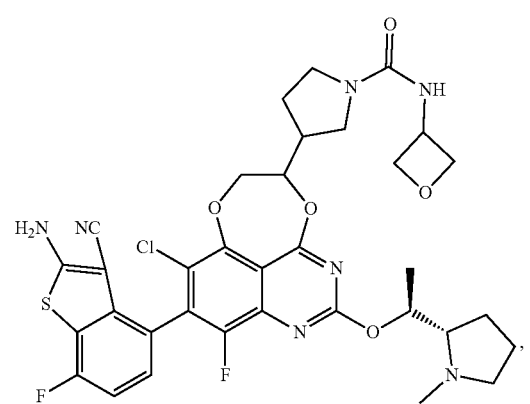
908
-continued
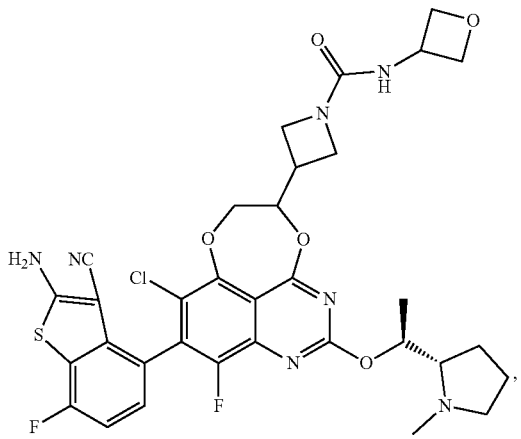
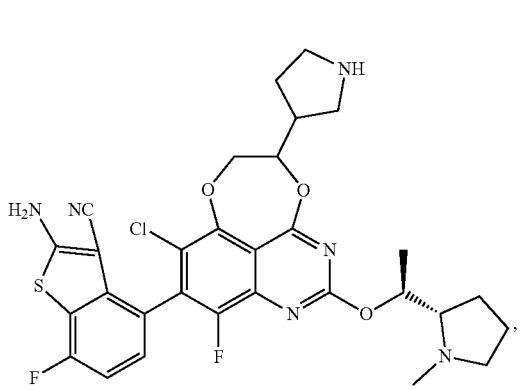
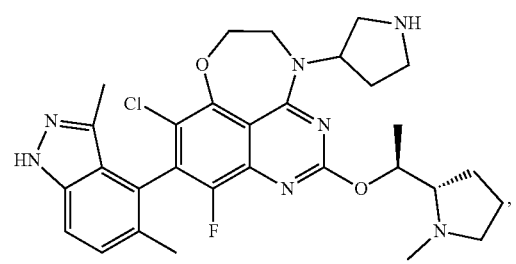
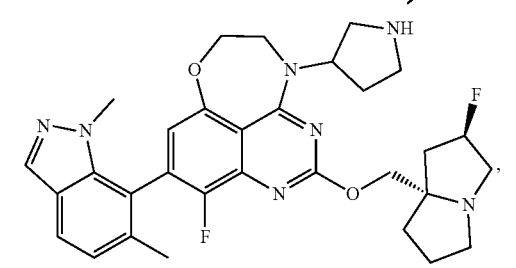
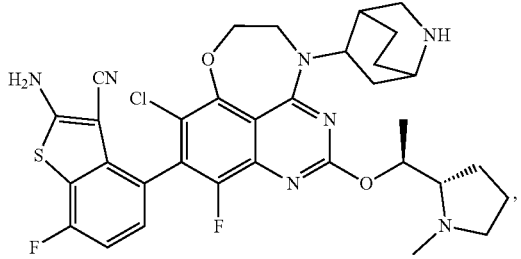

909
-continued
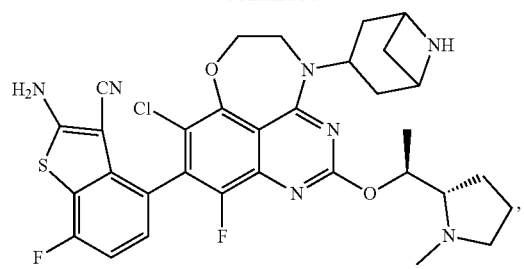
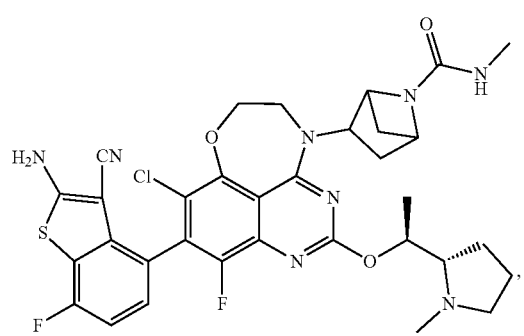
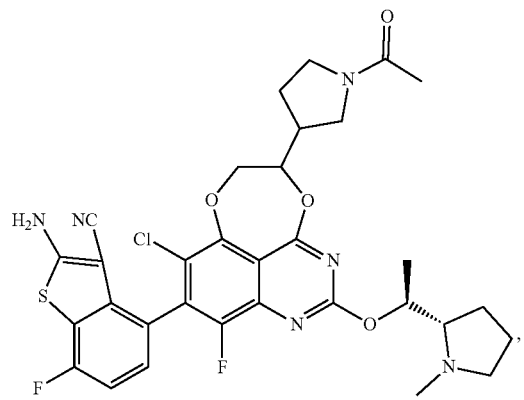
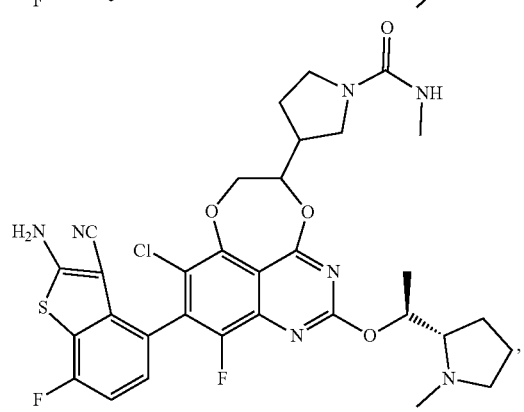
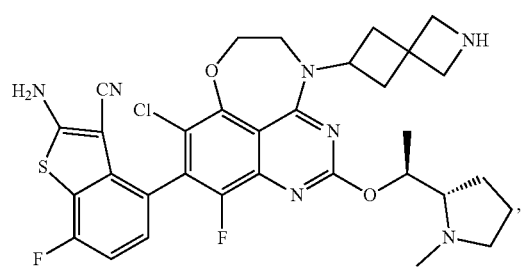
910
-continued
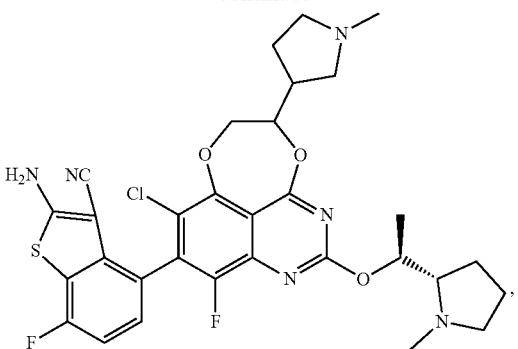
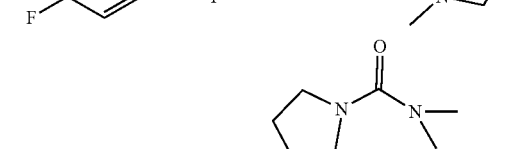
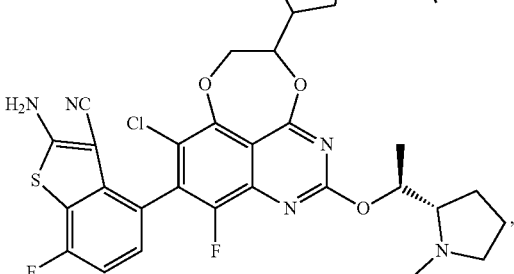
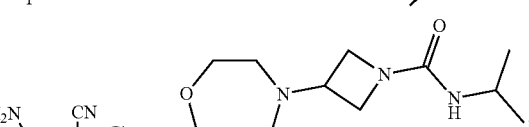
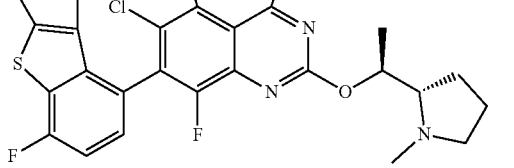
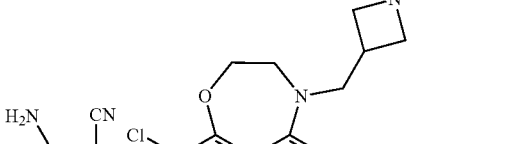
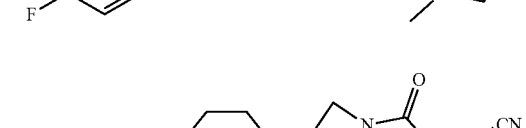
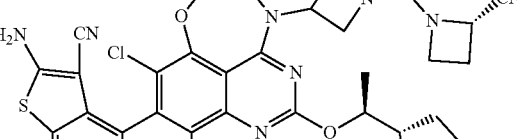

911
-continued
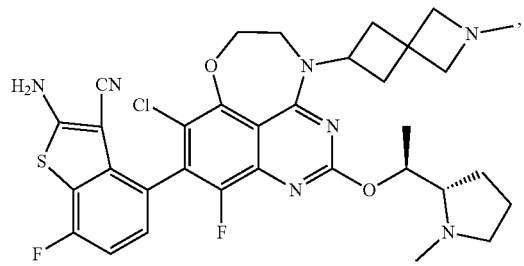
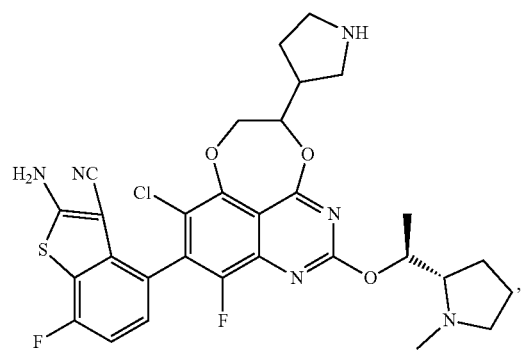
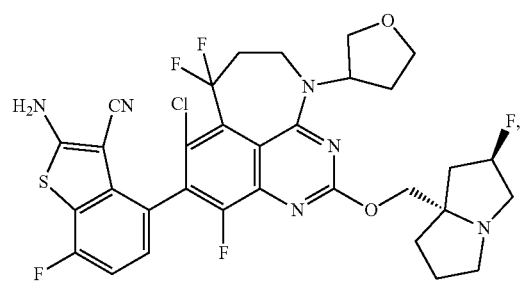
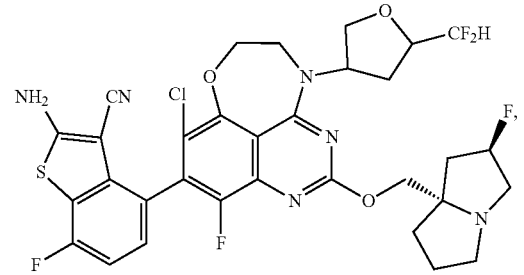
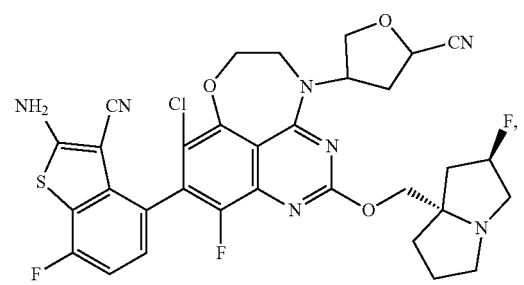
912
-continued
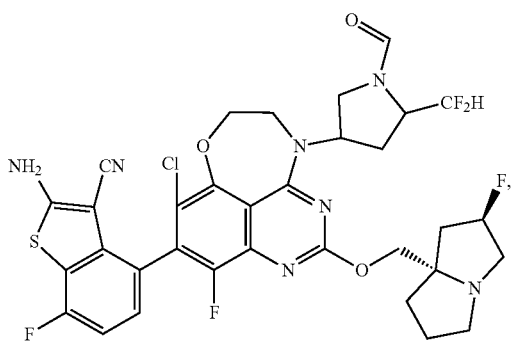
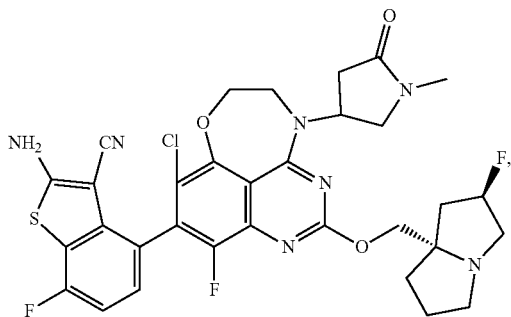
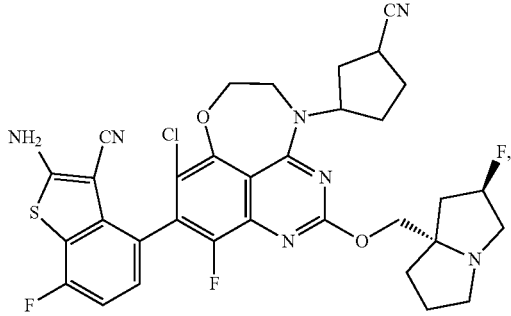
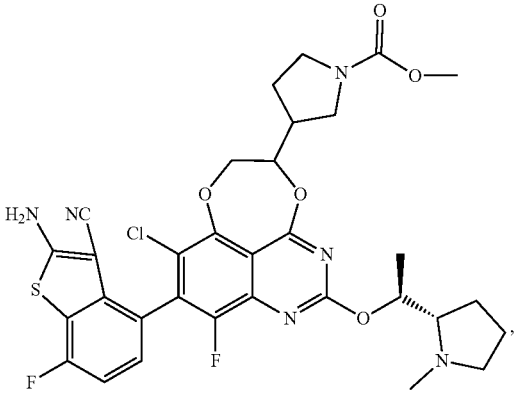
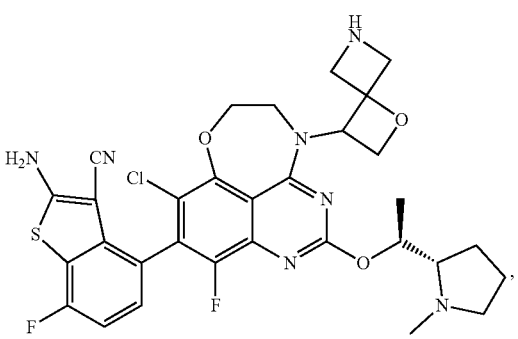

913
-continued
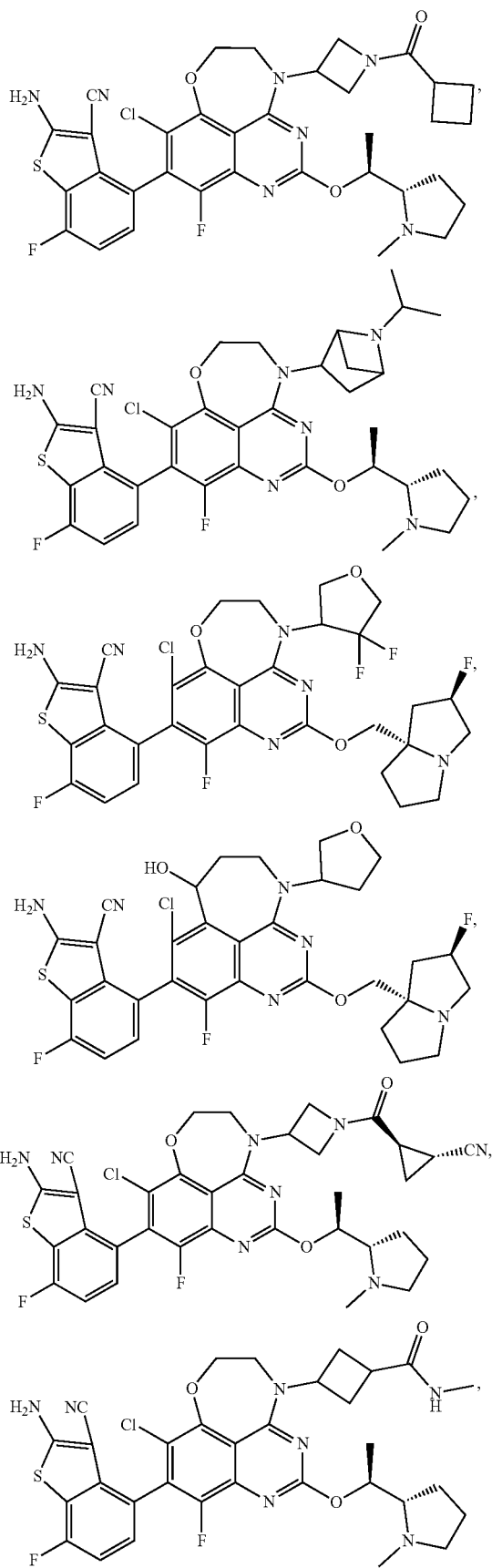
914
-continued
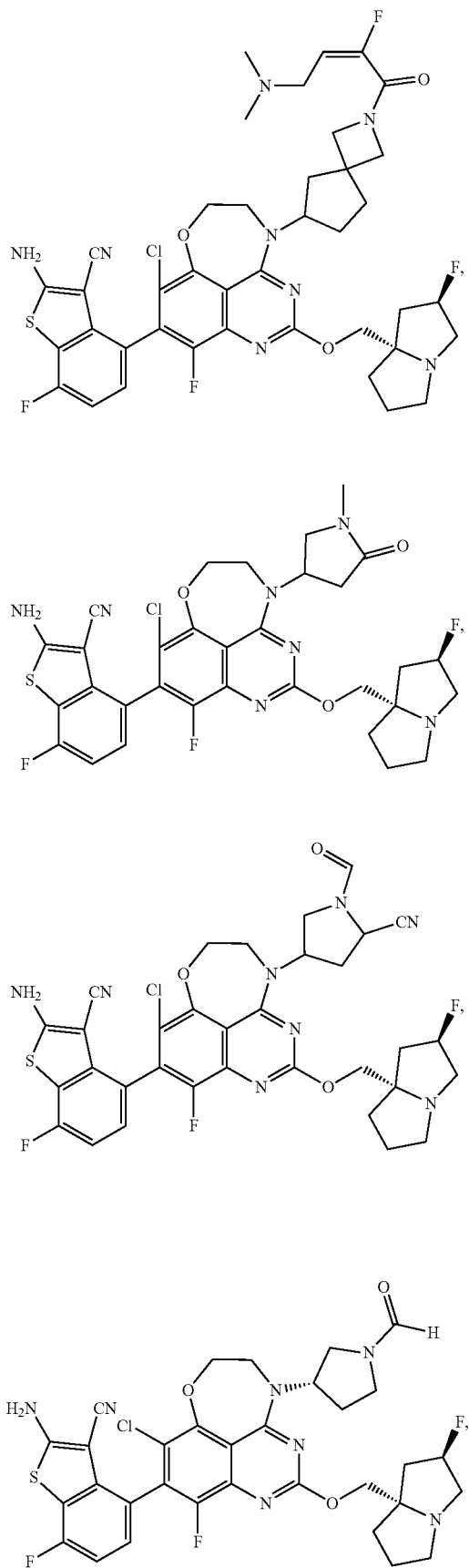

915
-continued

916
-continued

917
-continued
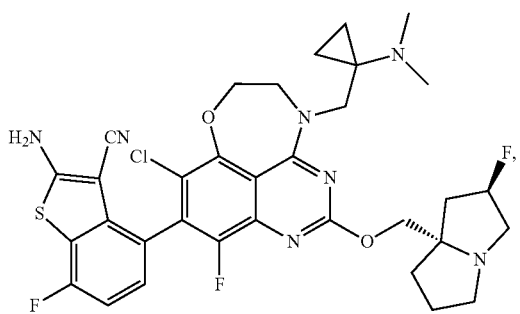
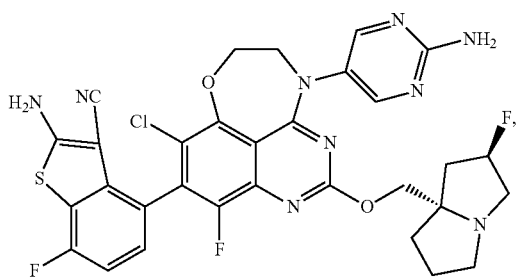
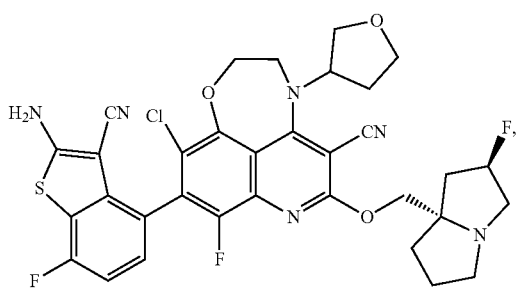
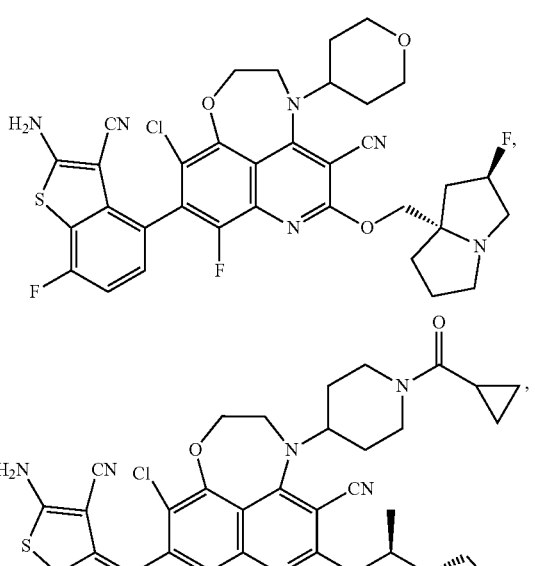
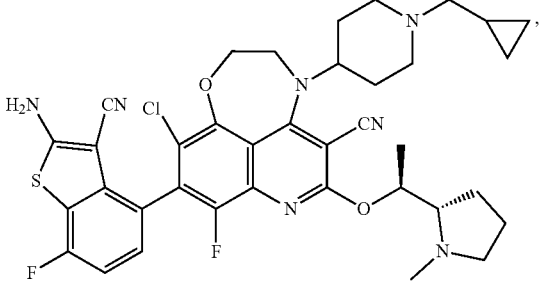
918
-continued
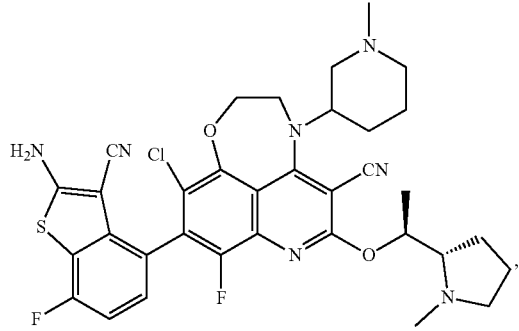
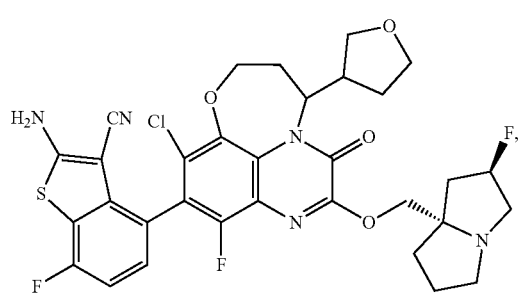
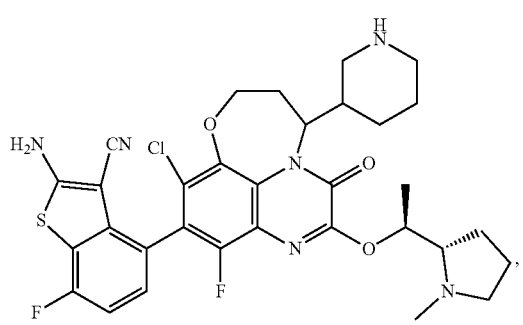
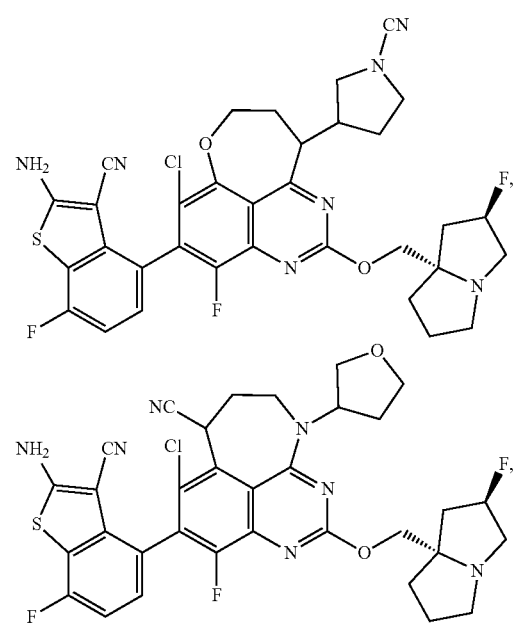

919
-continued
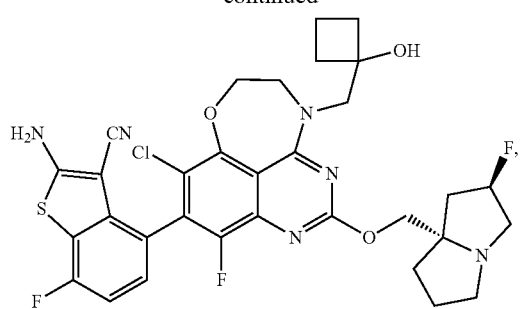
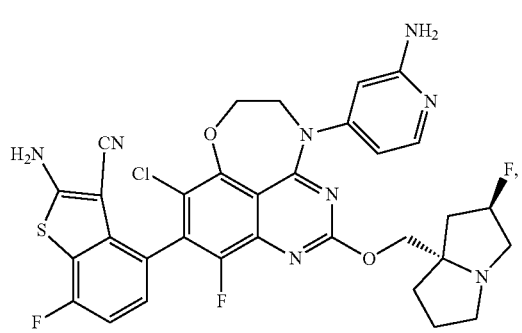
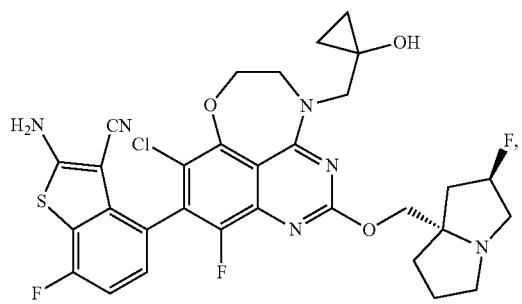
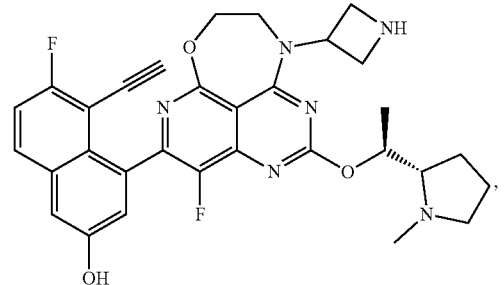
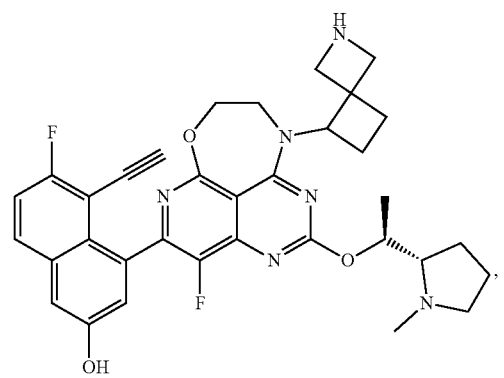
920
-continued
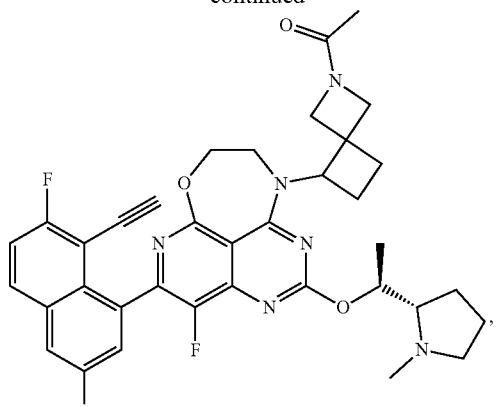
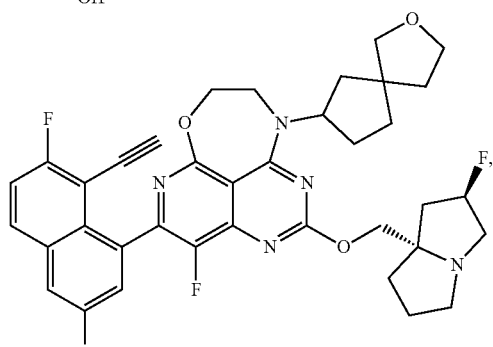
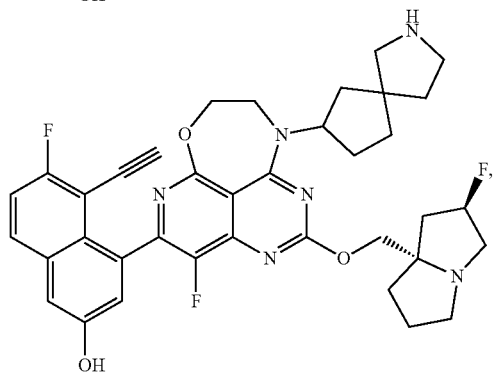
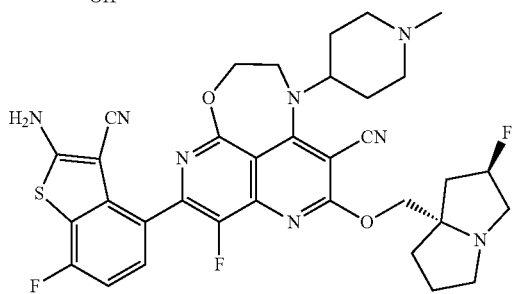
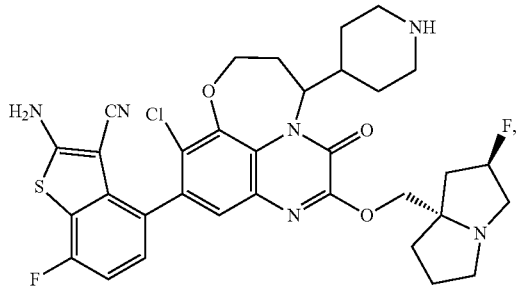

921
-continued
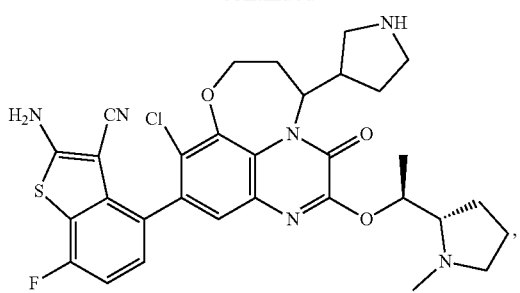
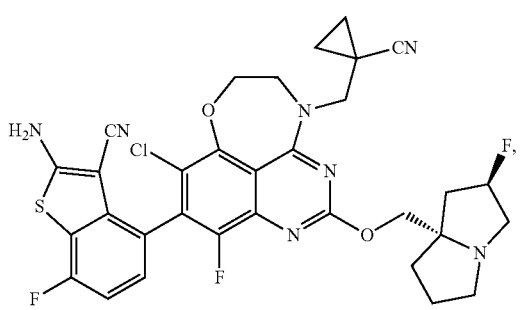
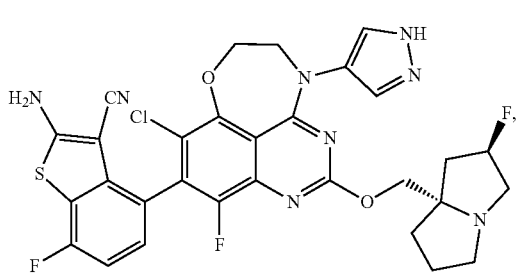
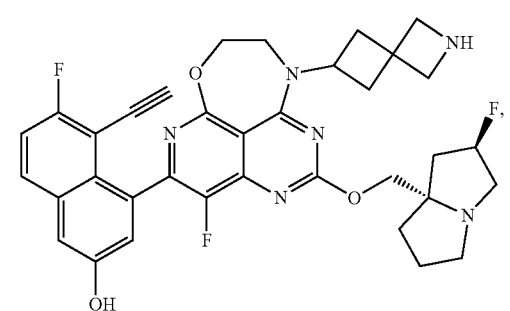
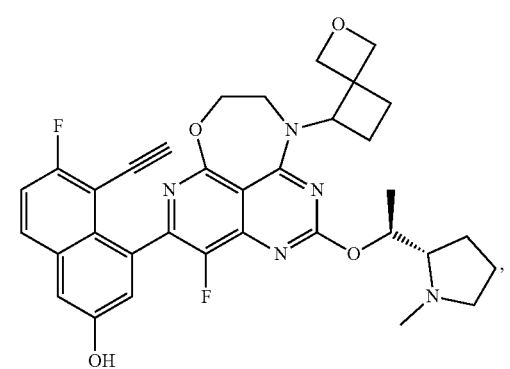
922
-continued
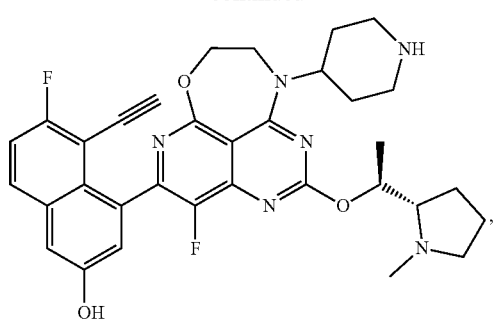
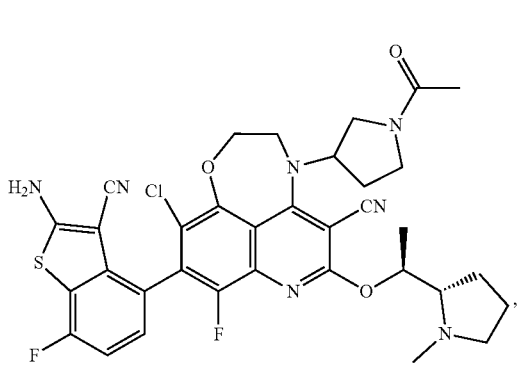
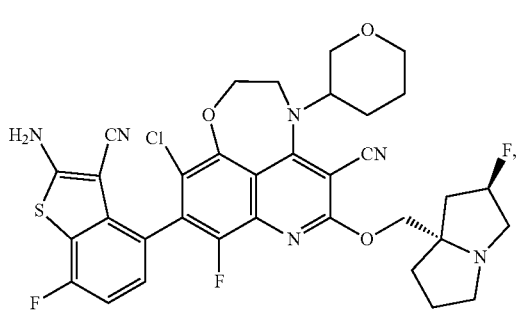
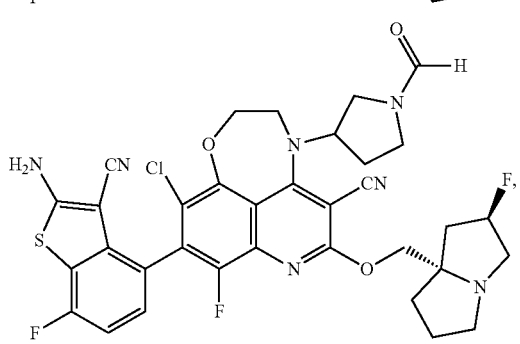
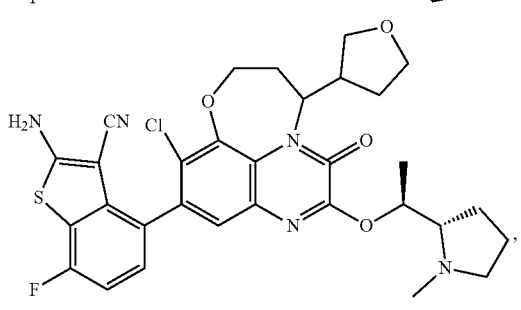

923
-continued
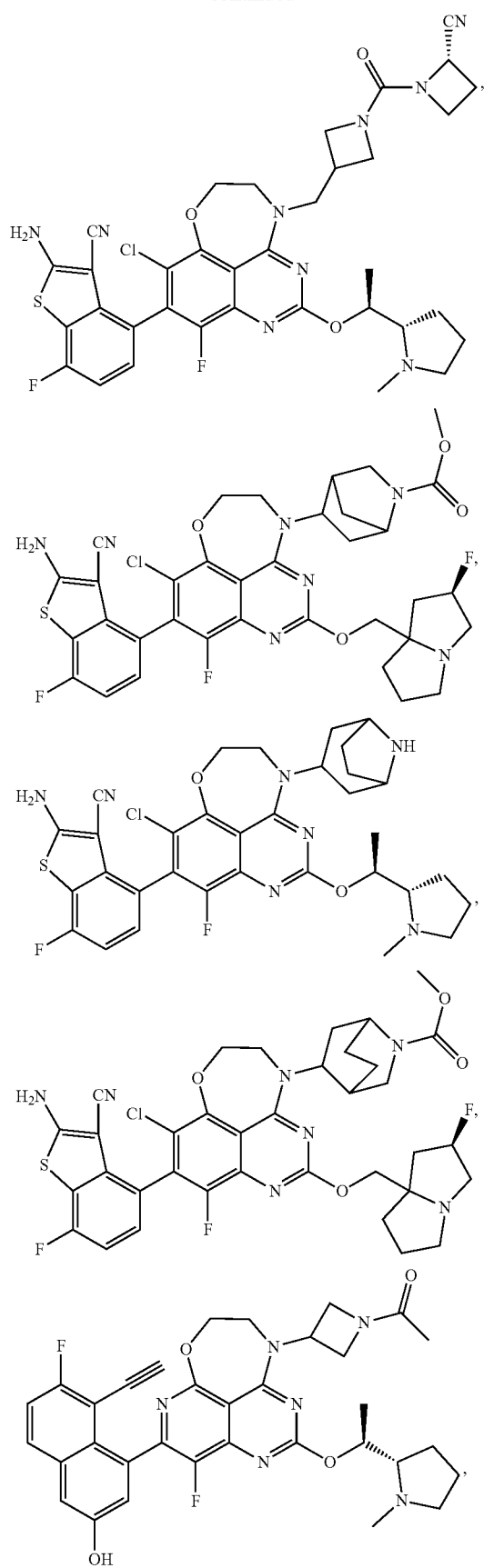
924
-continued
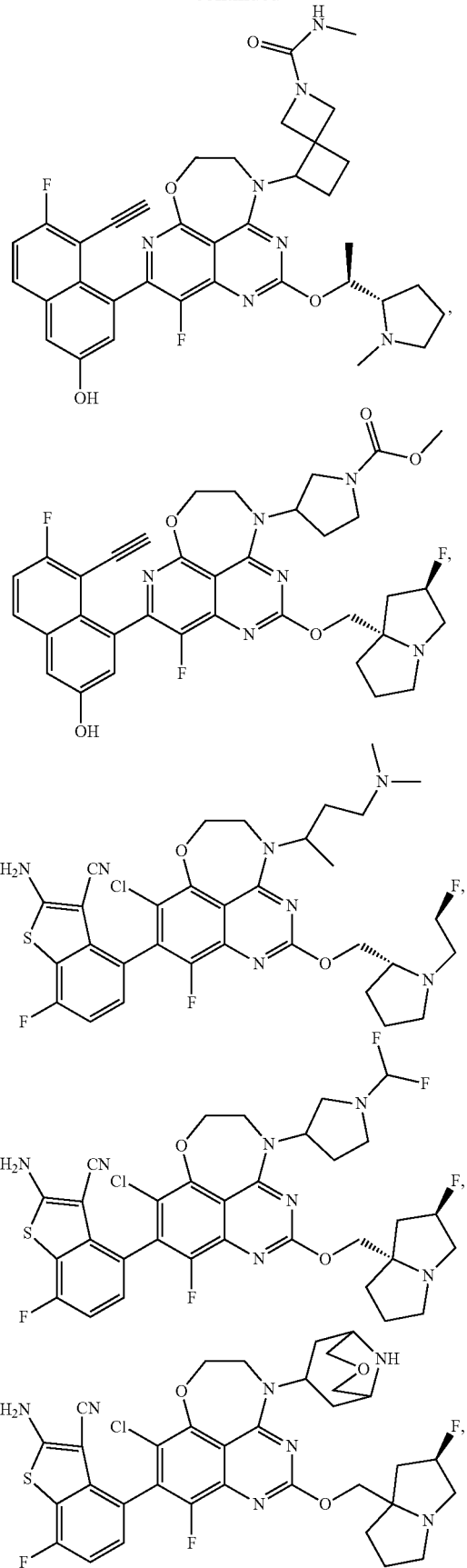

925
-continued
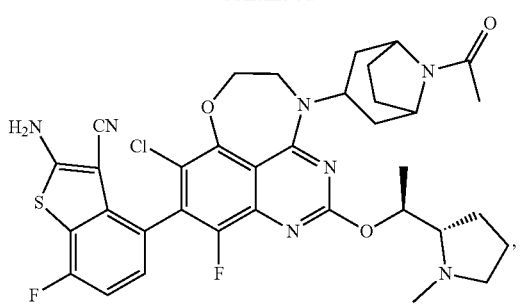
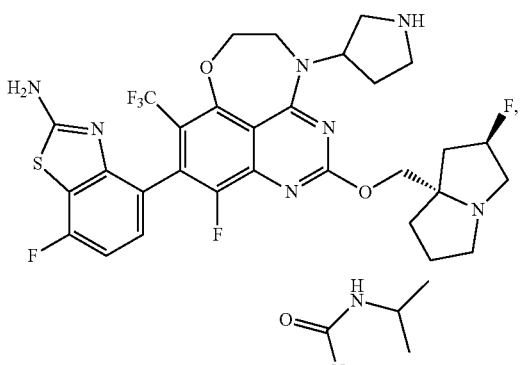
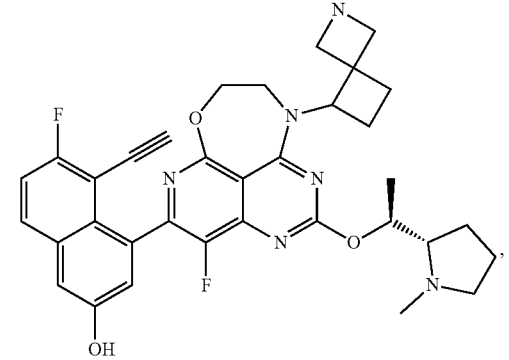
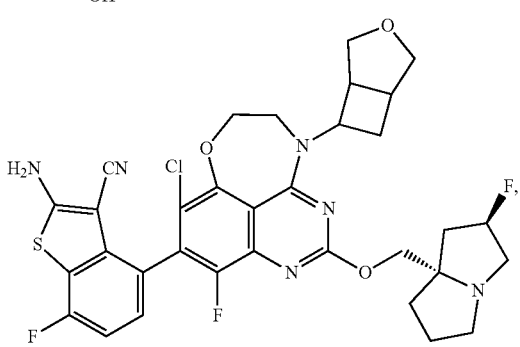
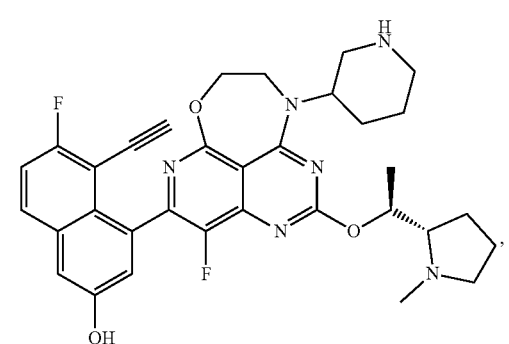
926
-continued
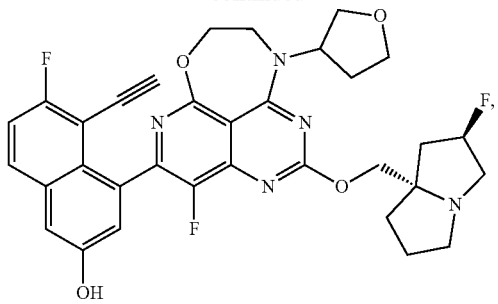
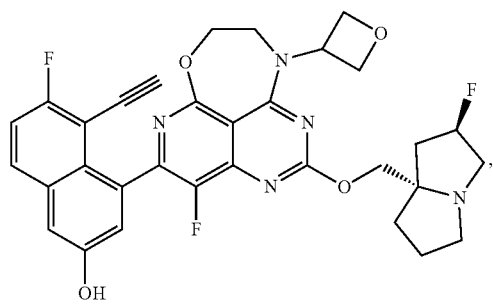
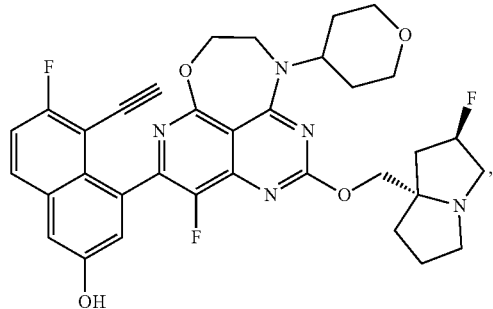
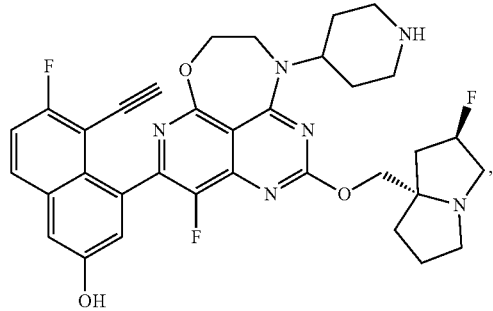
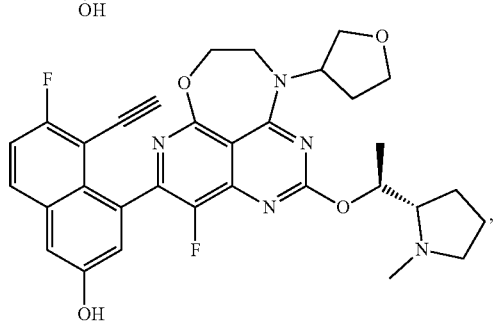

927
-continued
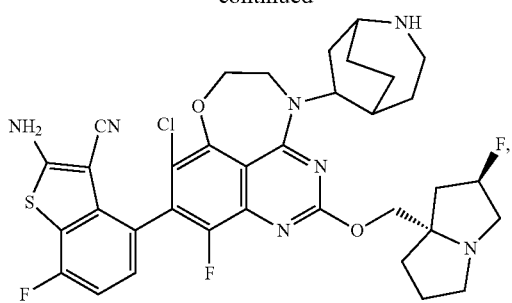
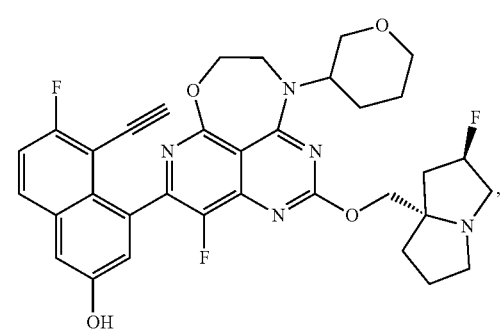
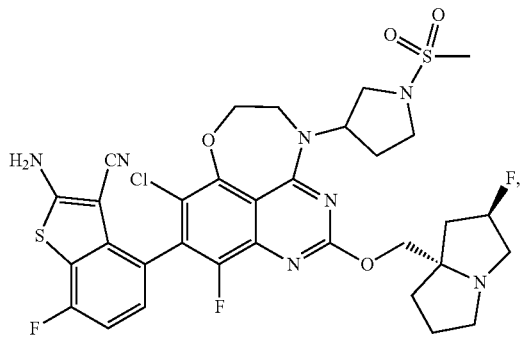
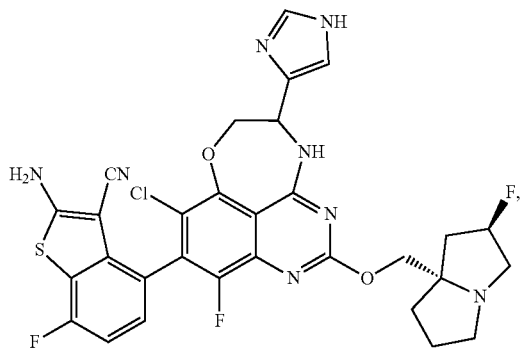
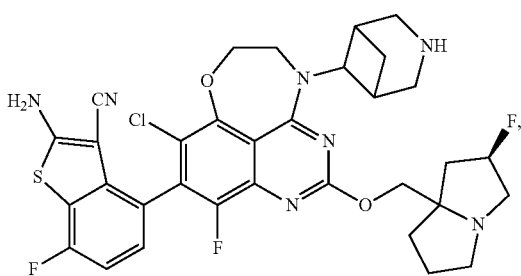
928
-continued
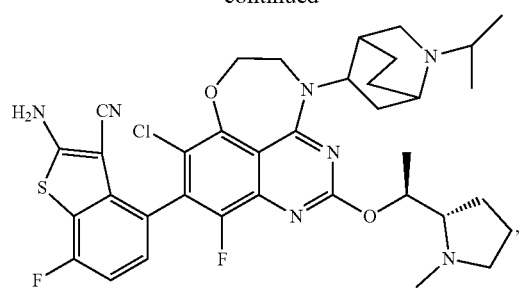
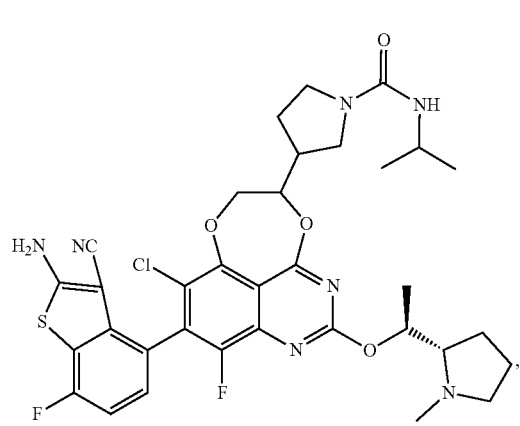
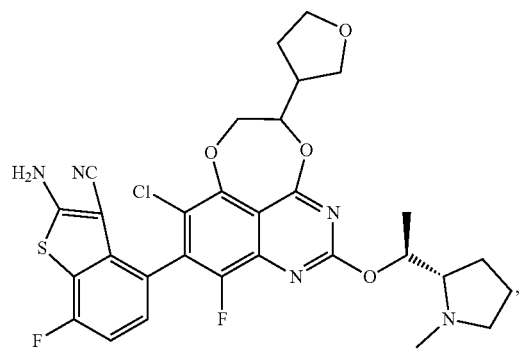
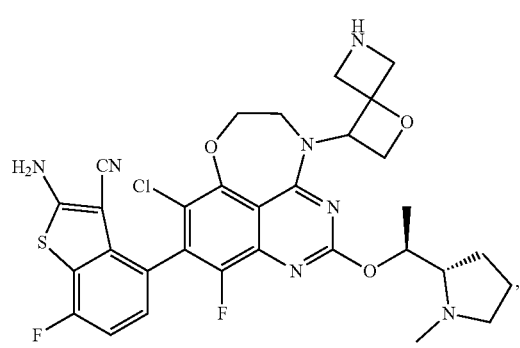

929
-continued
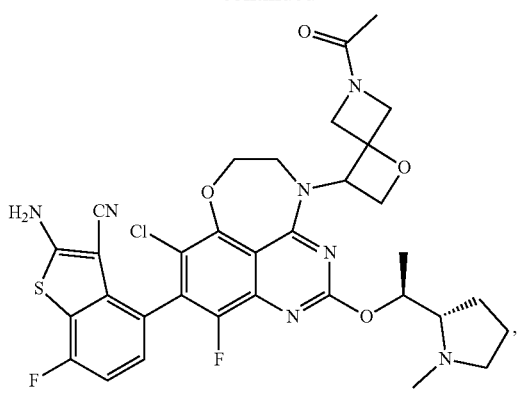
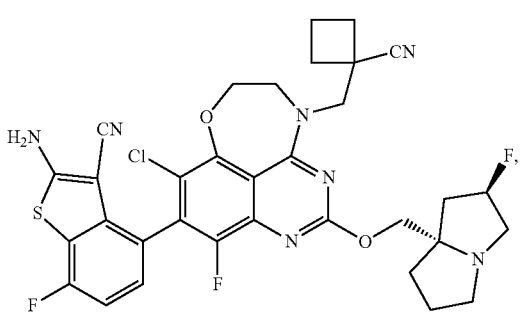
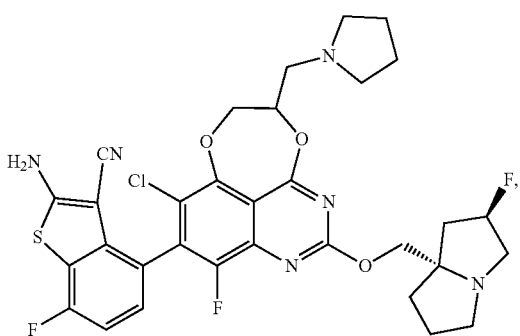
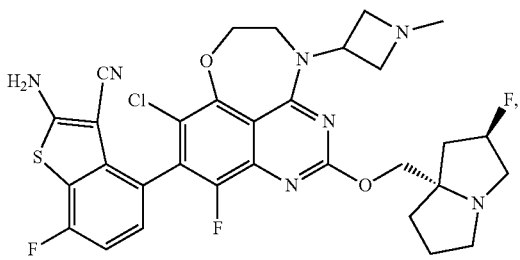
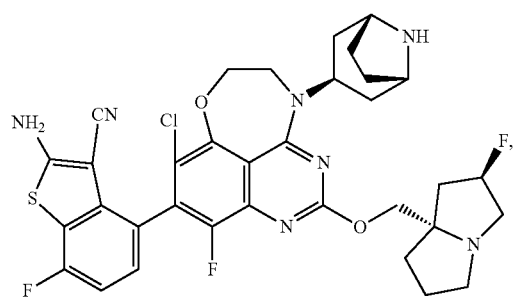
930
-continued
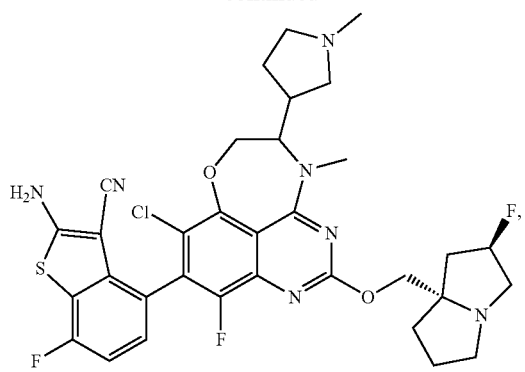
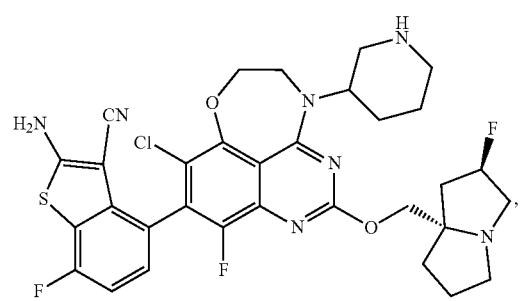
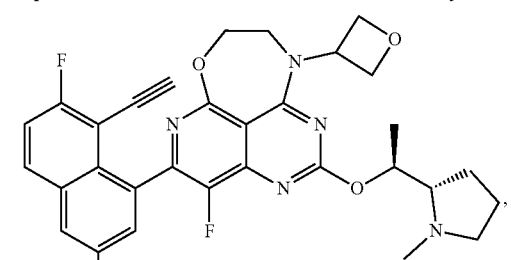
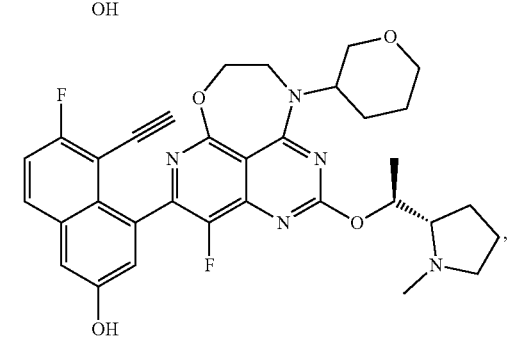
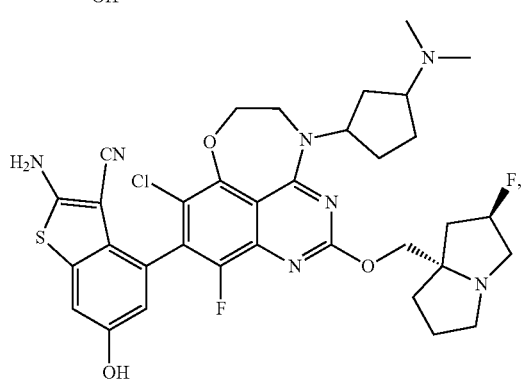

931
-continued
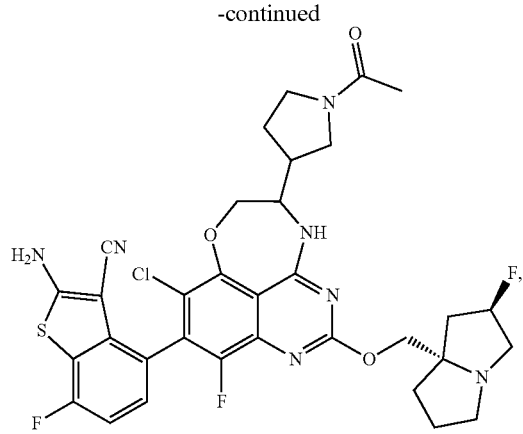
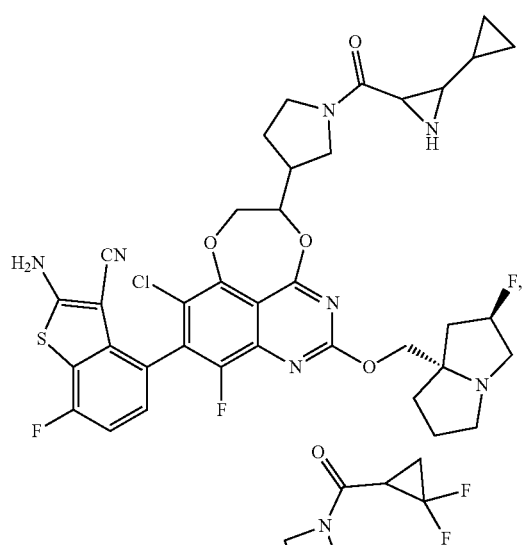
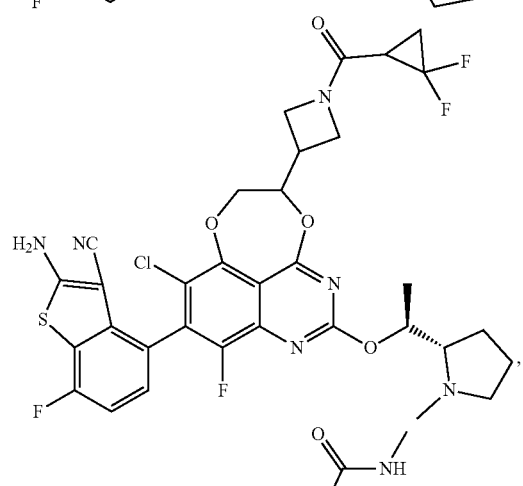
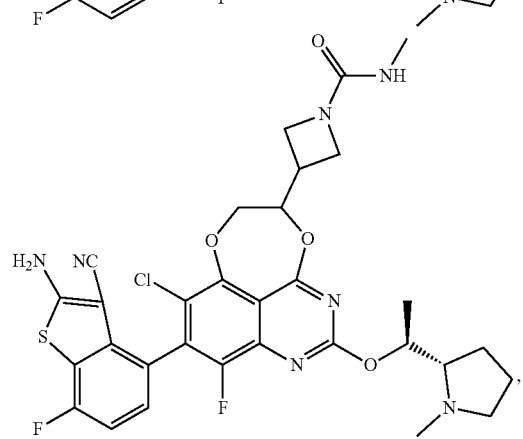
932
-continued
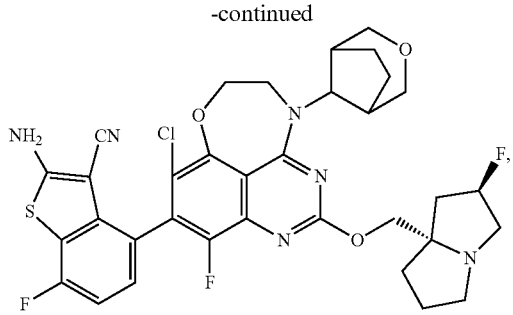
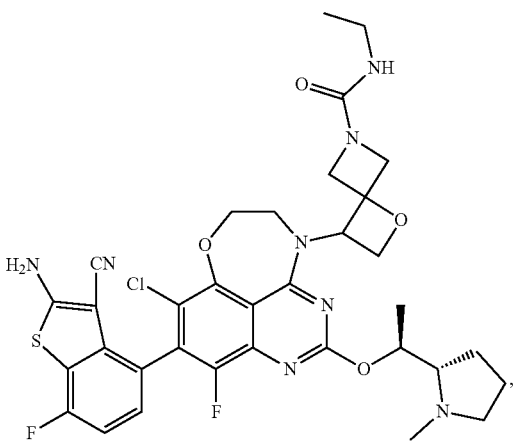
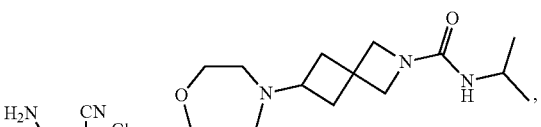
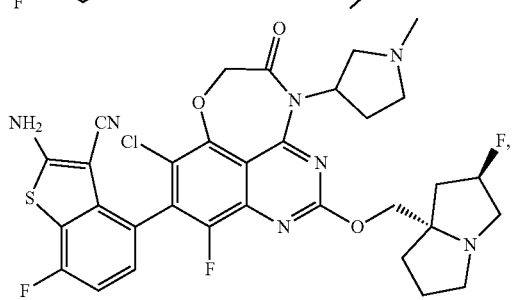
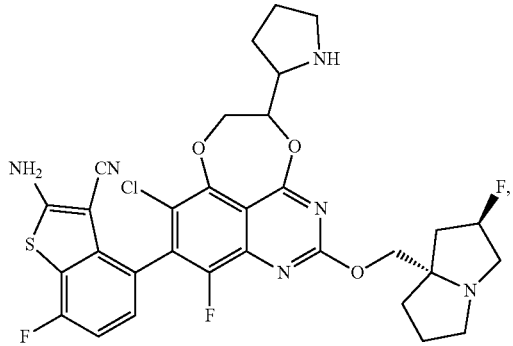

933
-continued
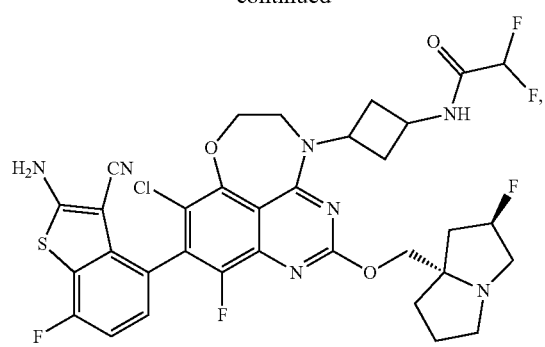
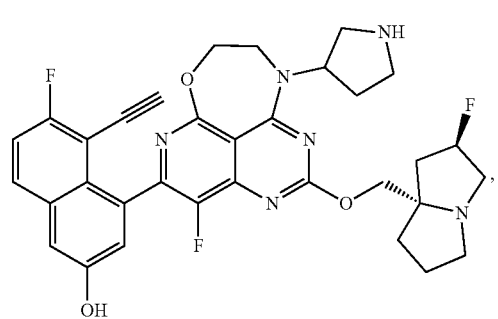
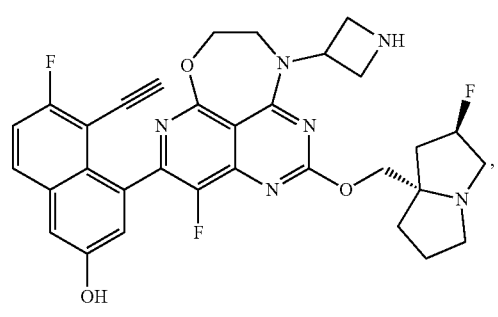
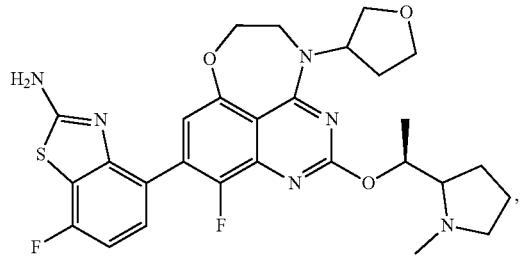
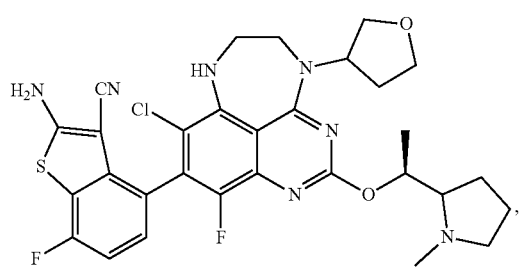
934
-continued
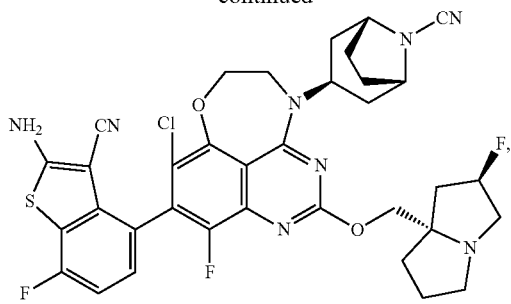
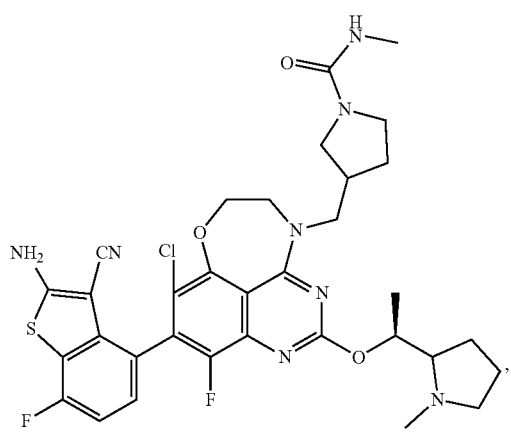
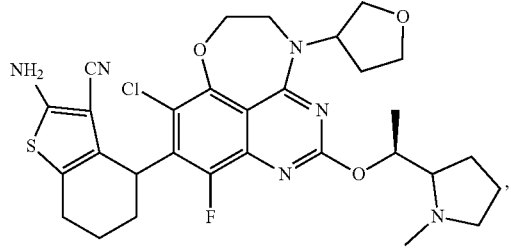
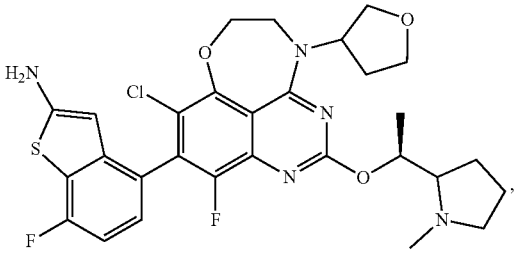
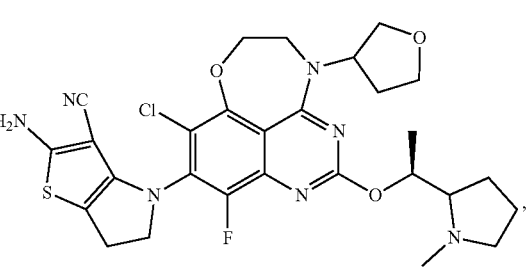

935
-continued
936
-continued
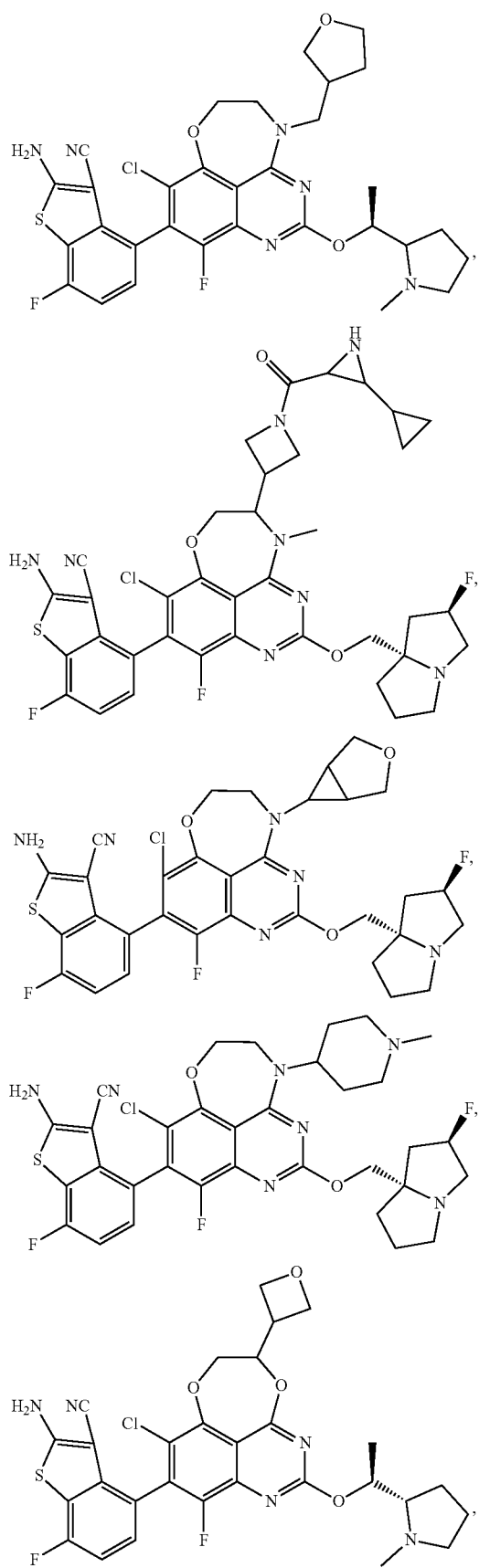
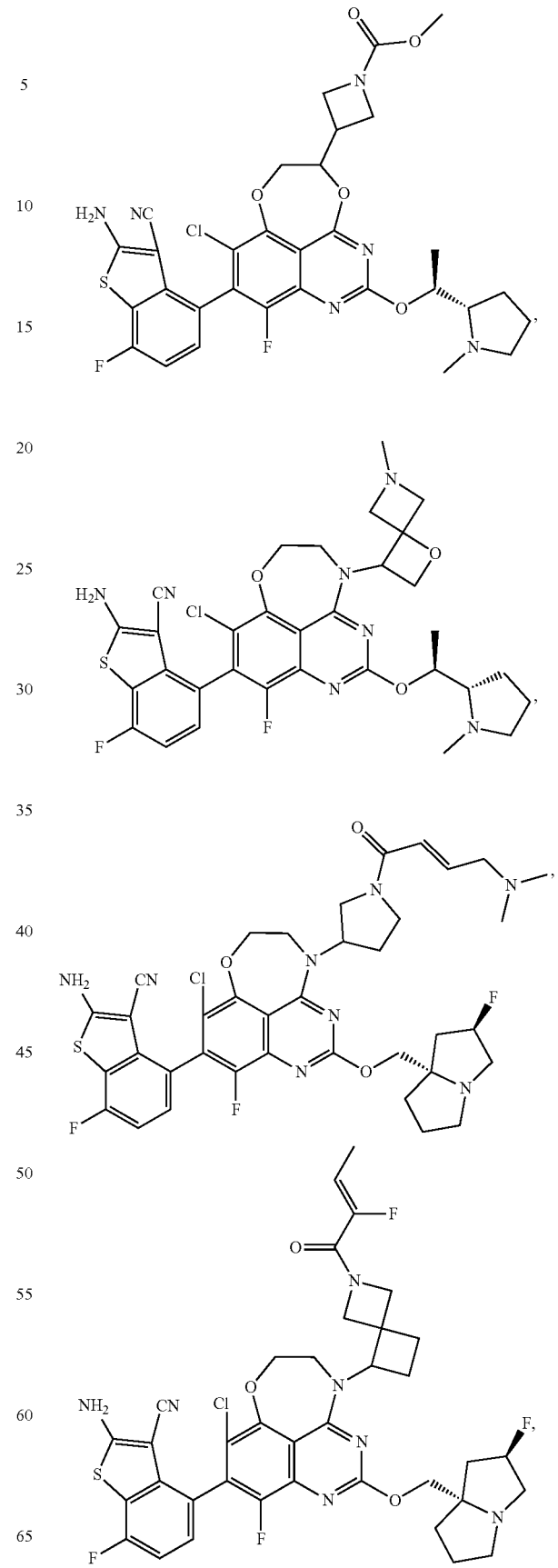

937
-continued
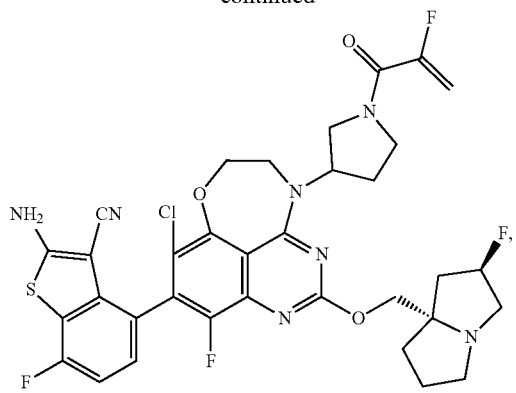
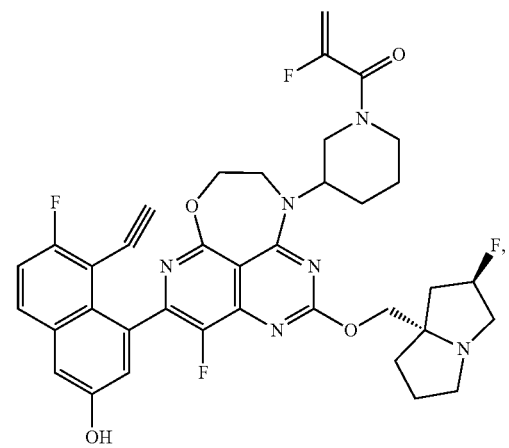
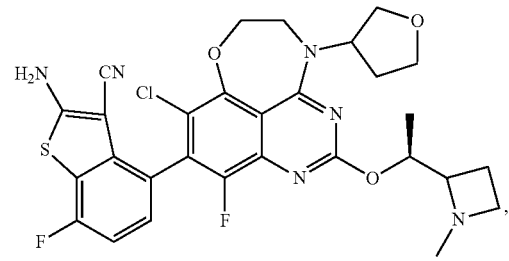
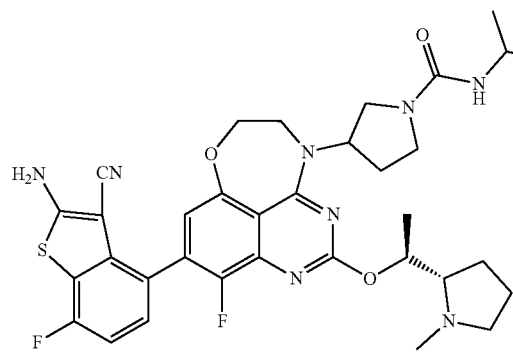
938
-continued
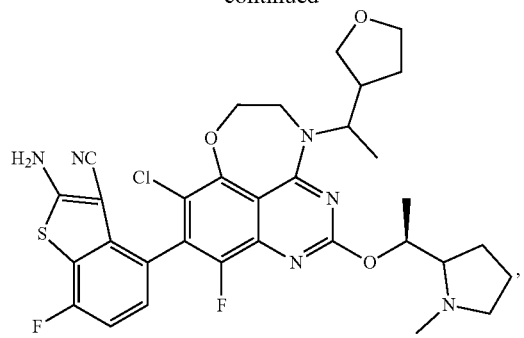
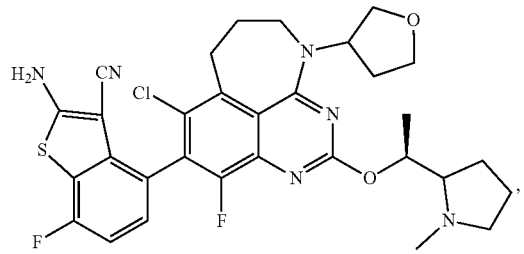
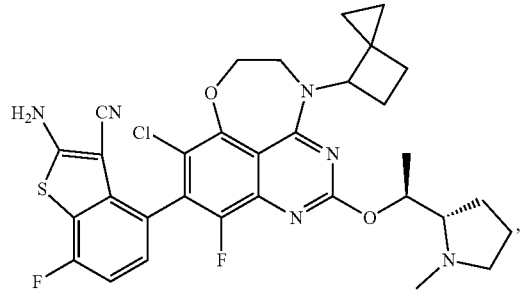
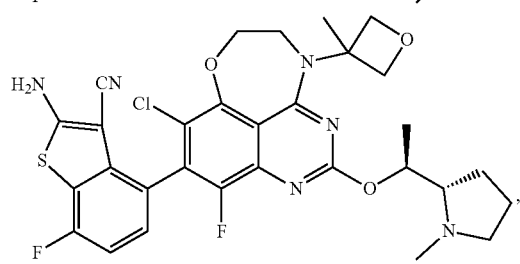
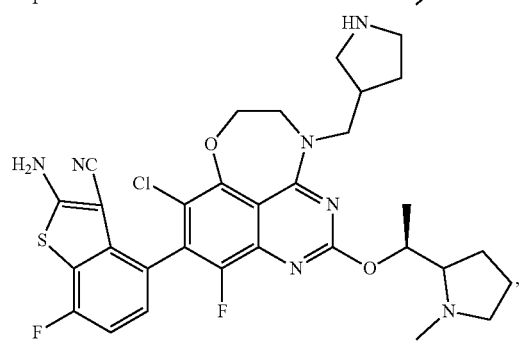
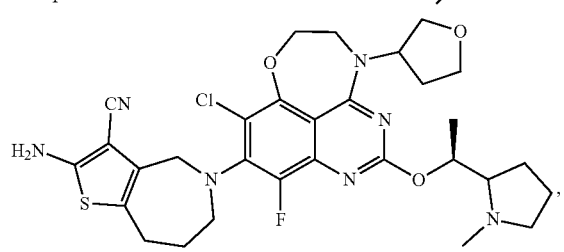

-continued
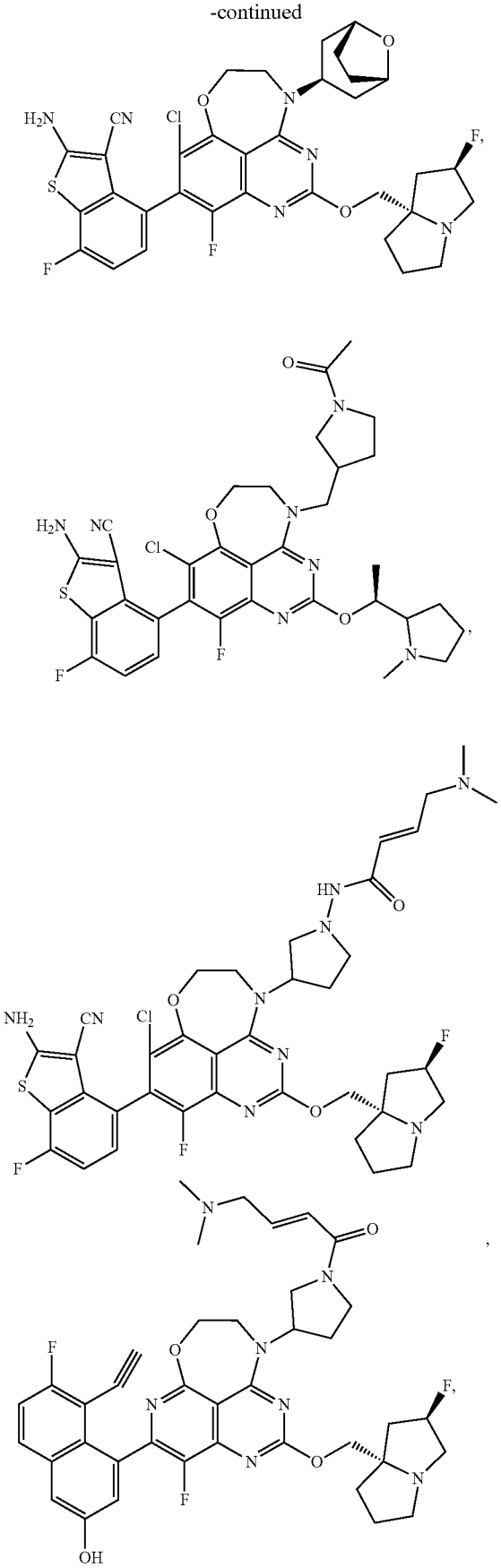
-continued
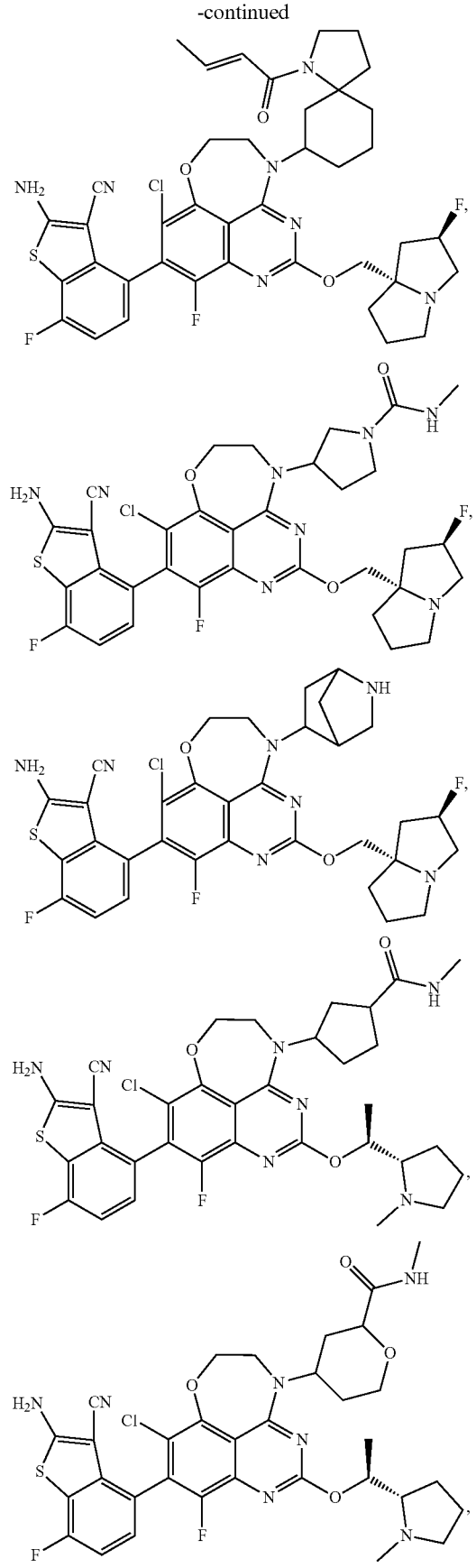

-continued
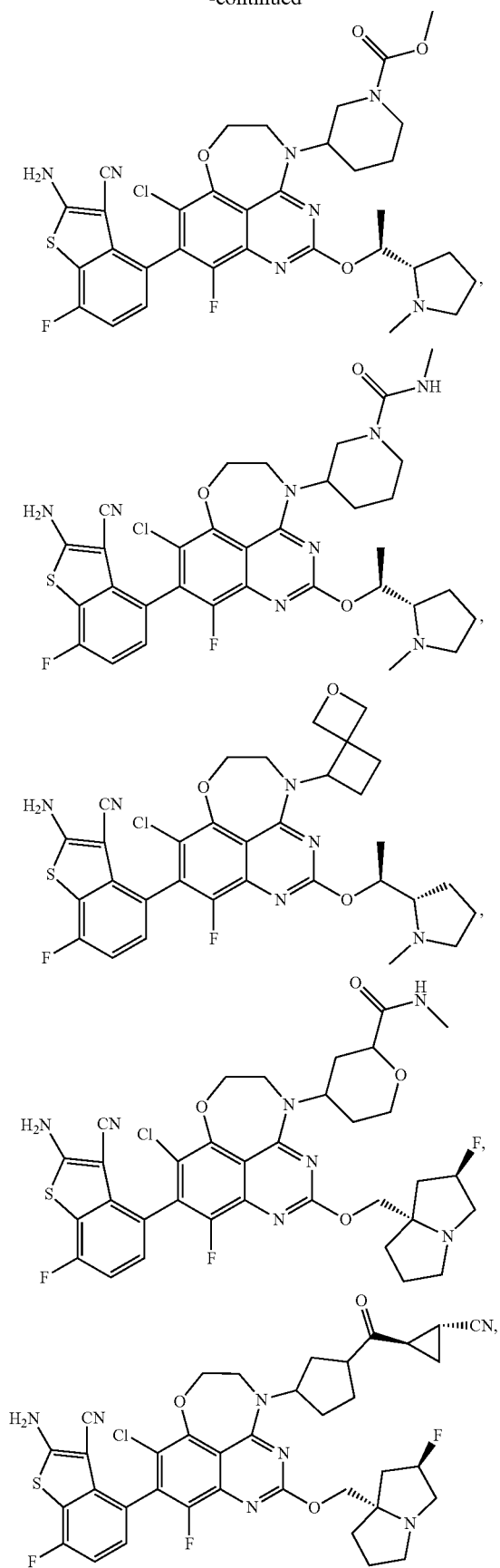
-continued
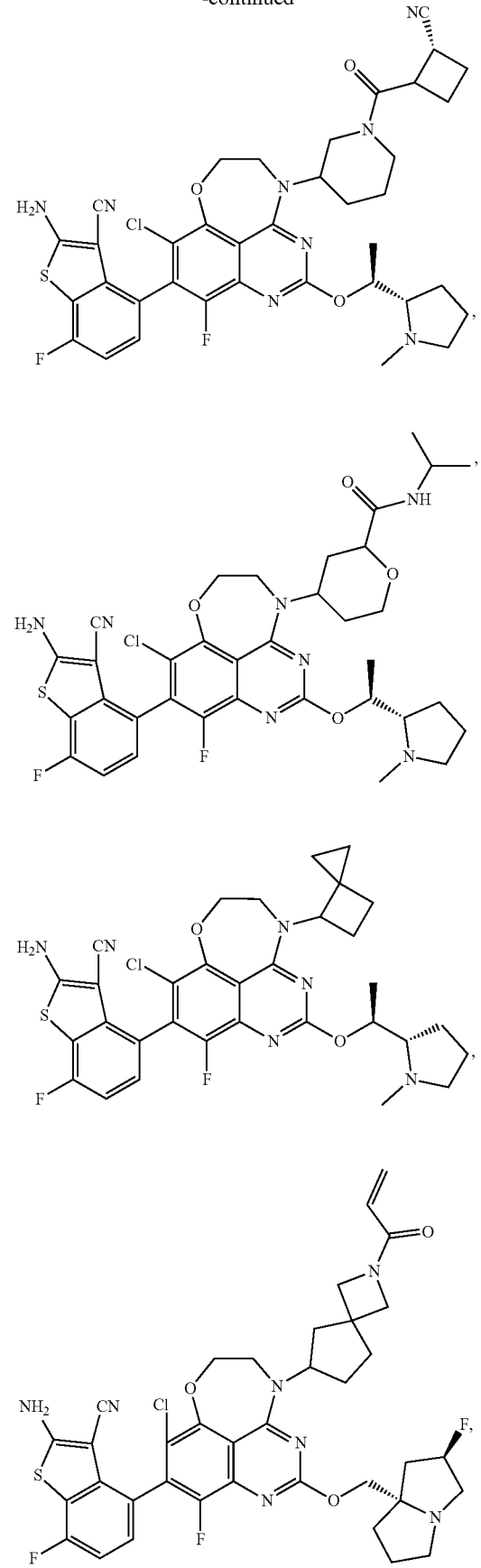

943
-continued
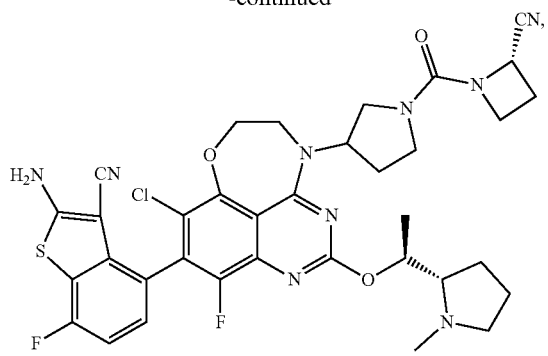
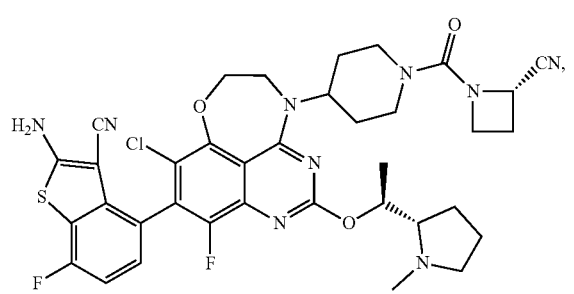
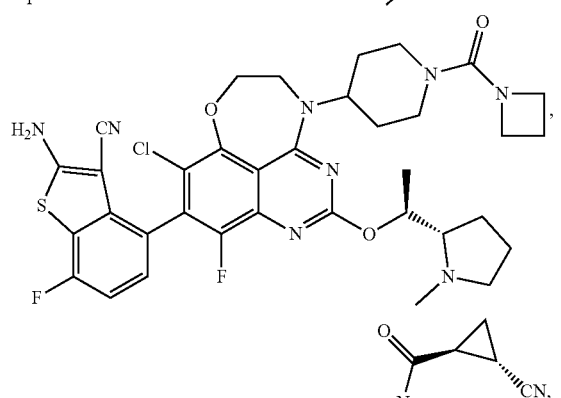
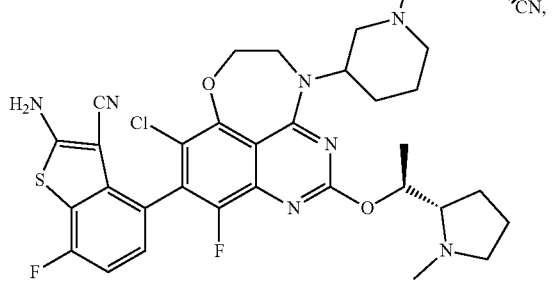
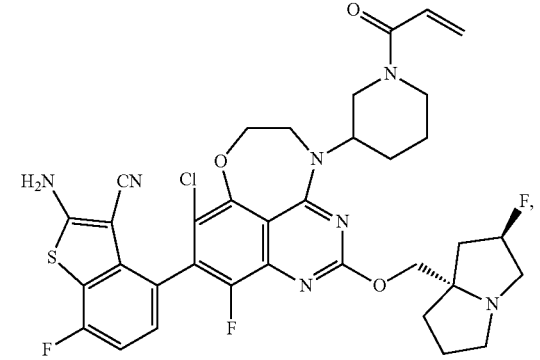
944
-continued
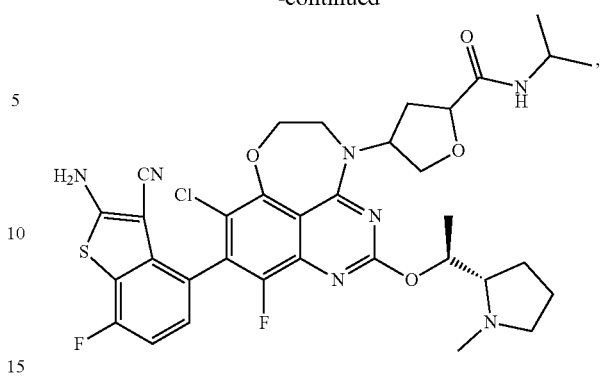
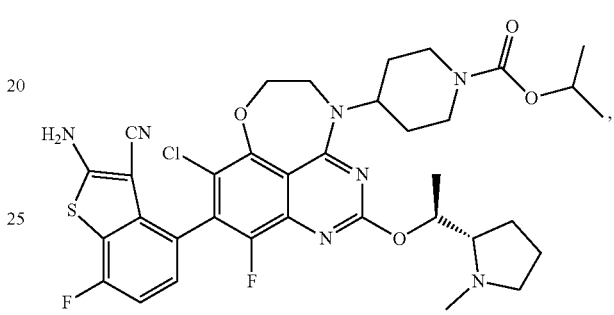
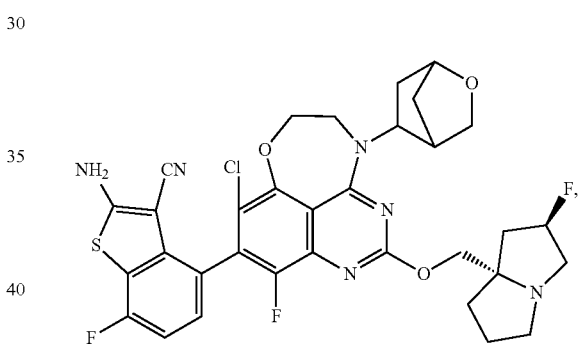
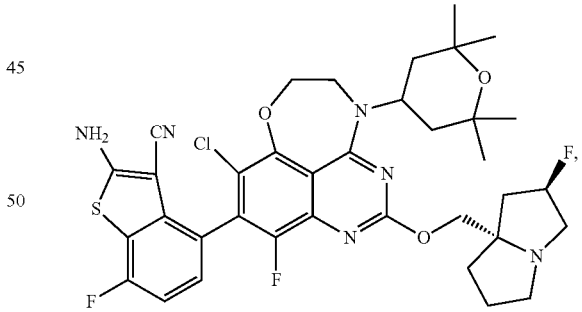
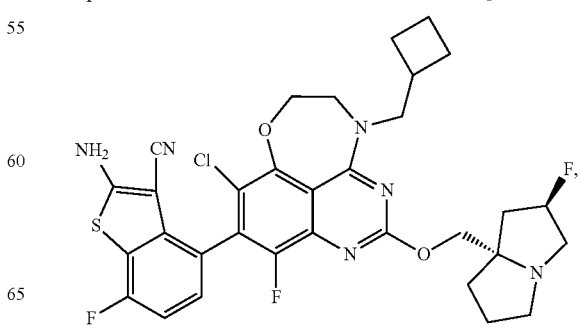

945
-continued
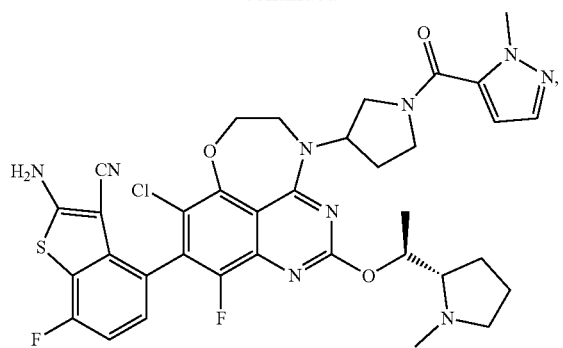
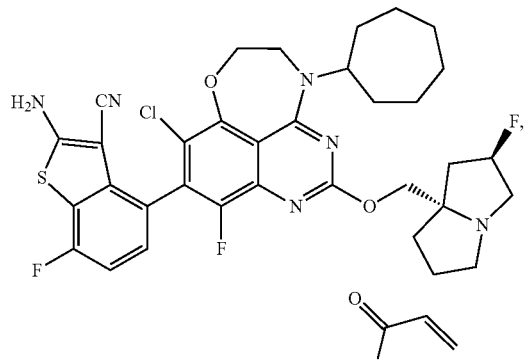
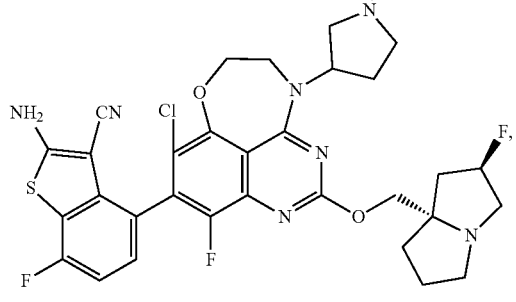
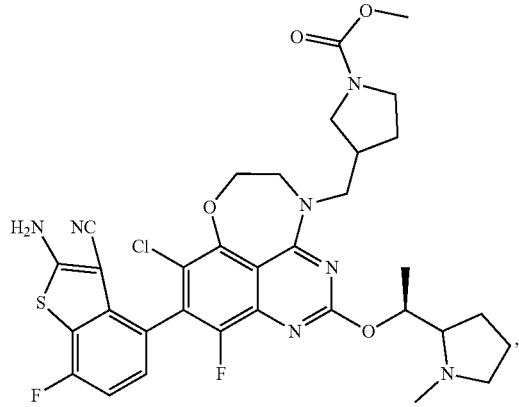
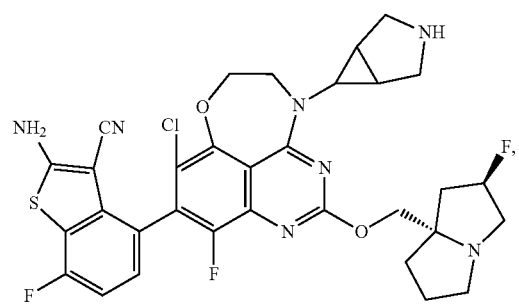
946
-continued
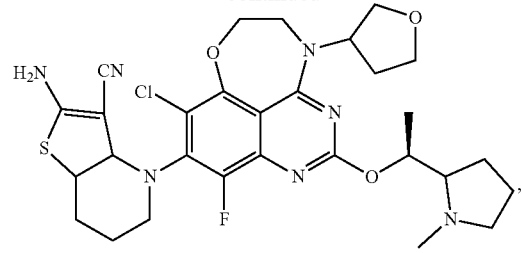
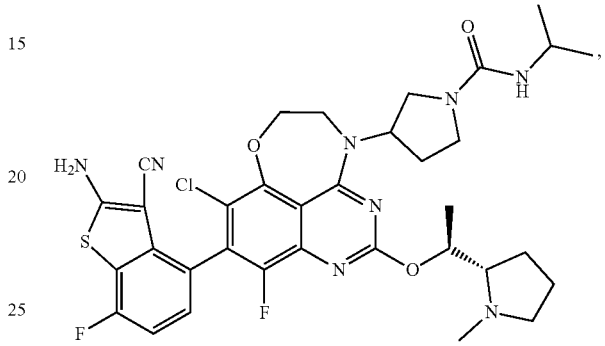
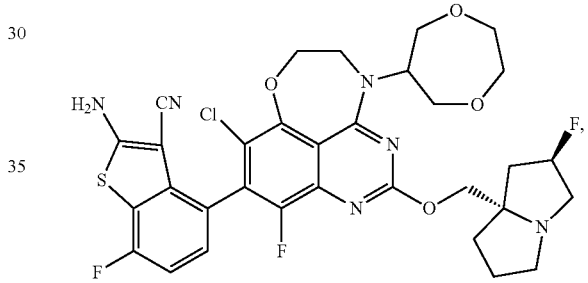
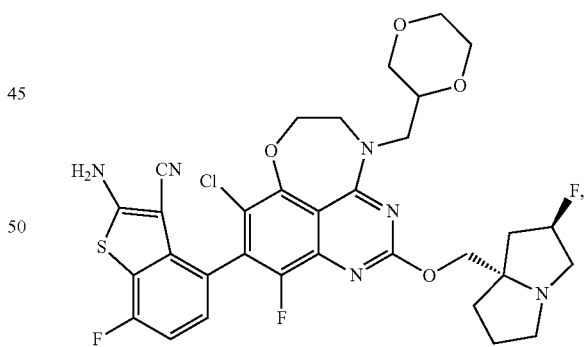
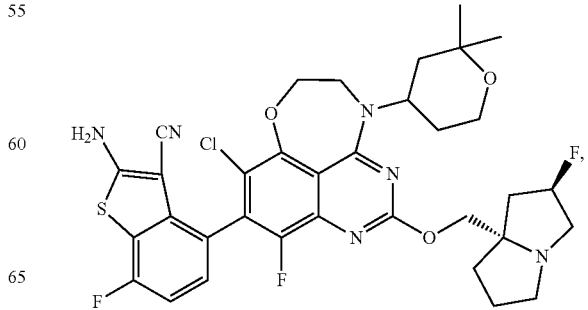

947
-continued
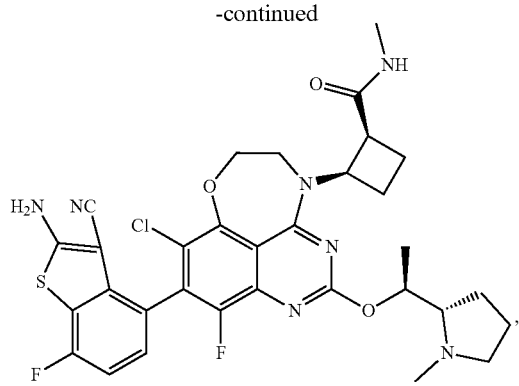
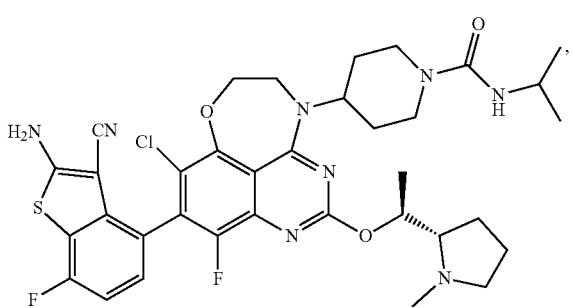
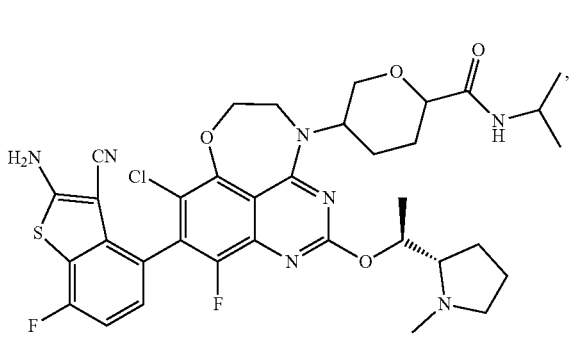
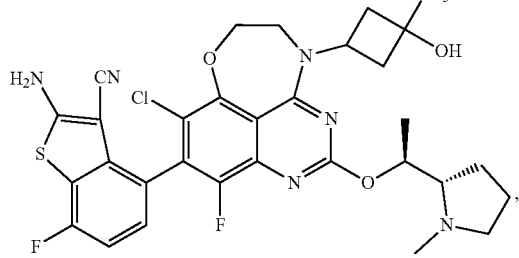
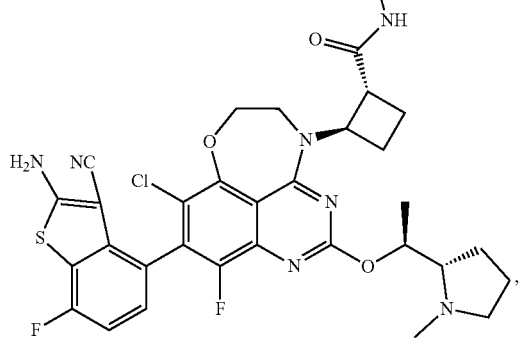
948
-continued
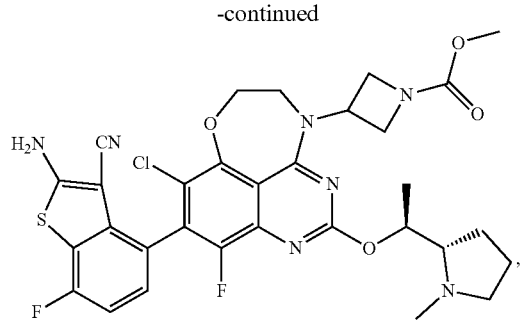
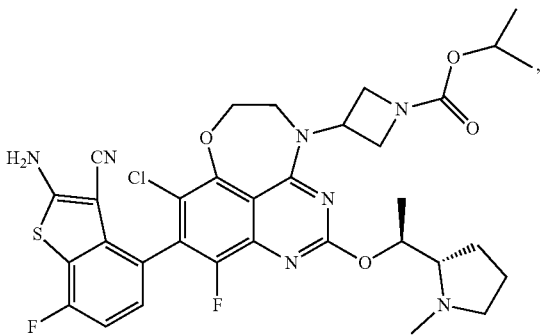
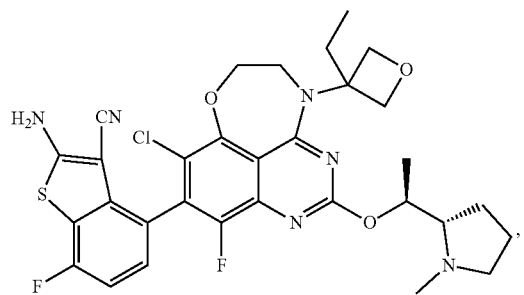
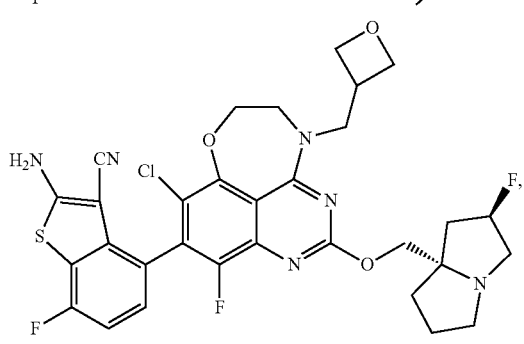
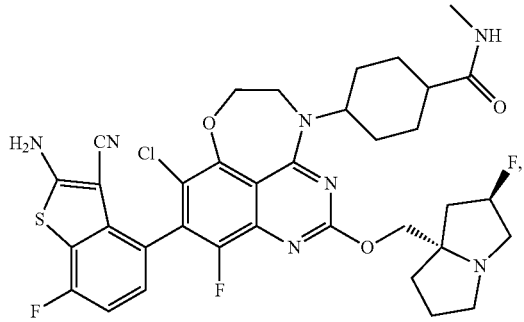

949
-continued
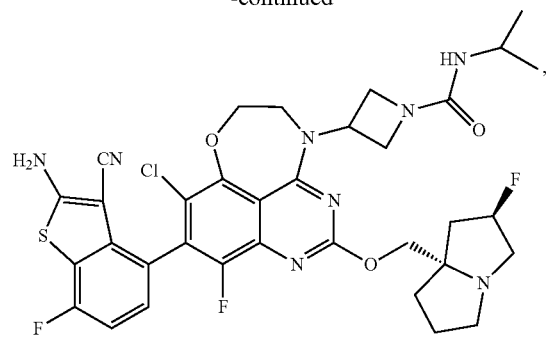
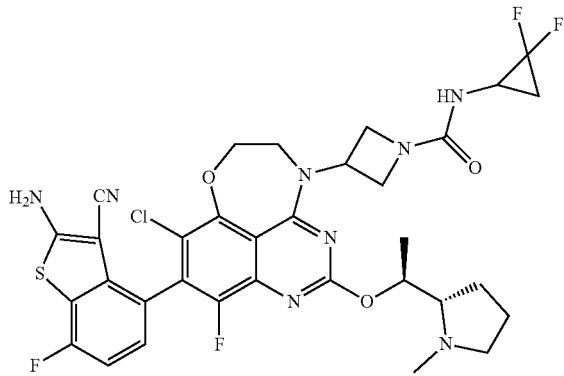
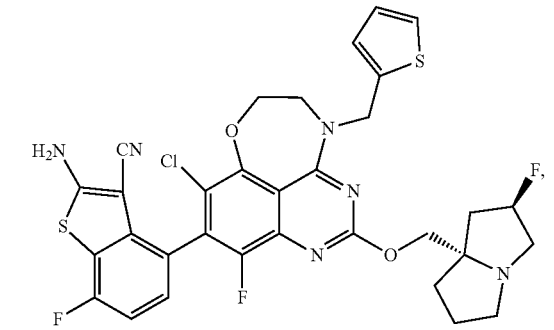
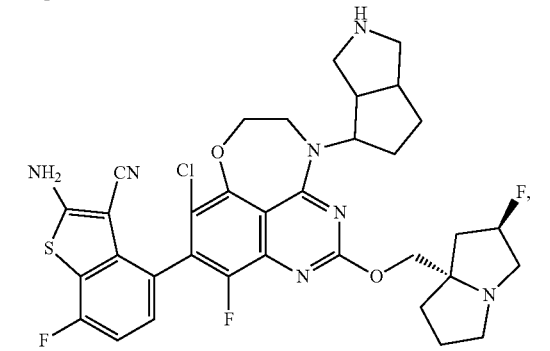
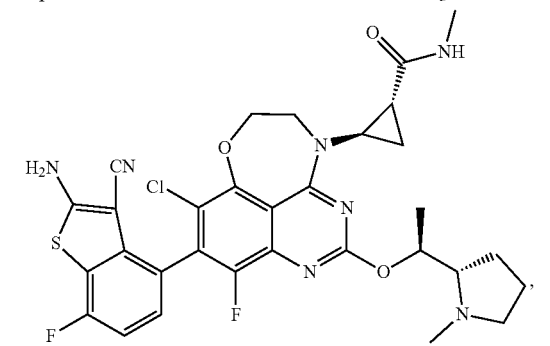
950
-continued
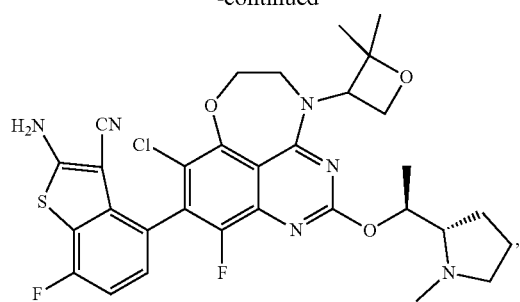
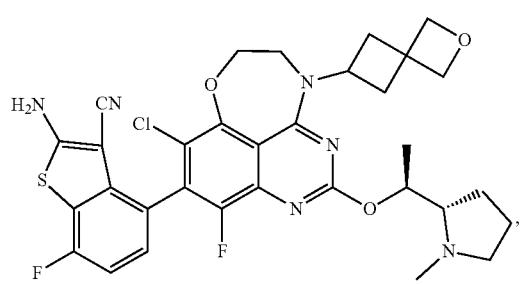
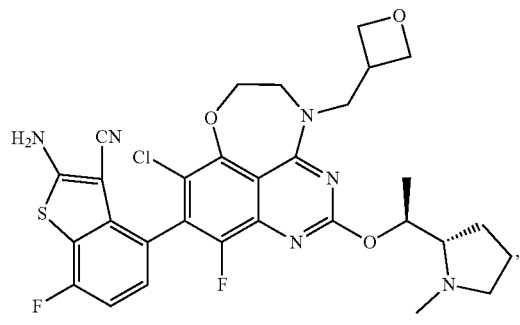
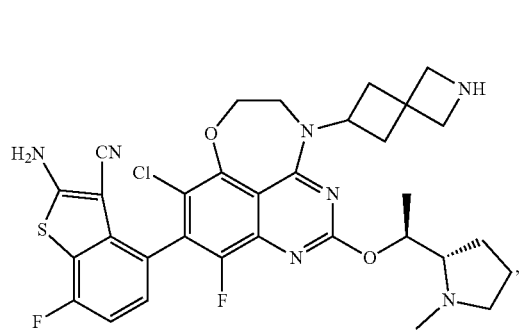
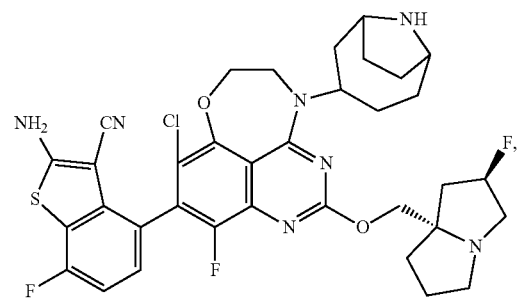

951
-continued
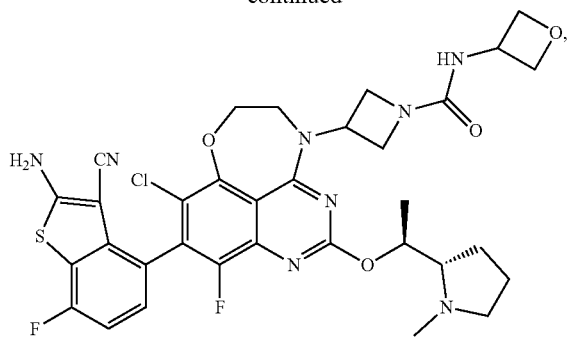
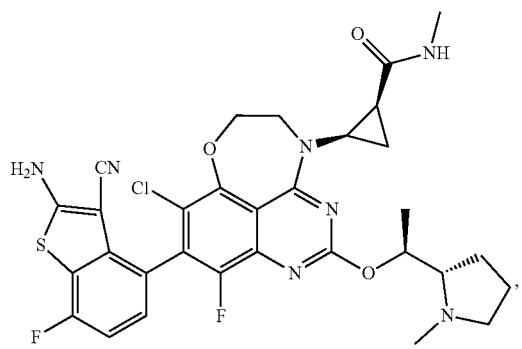
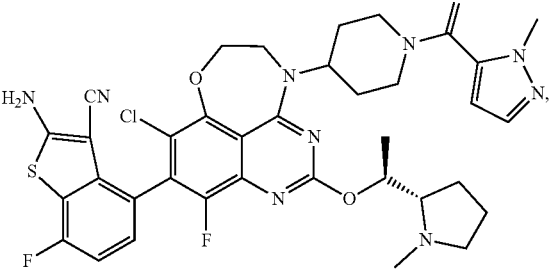
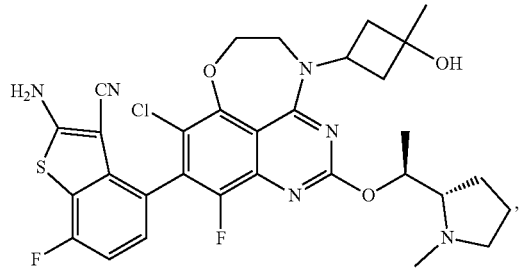
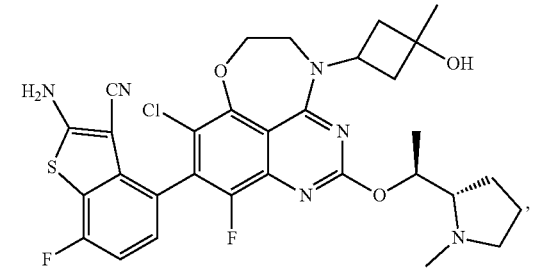
952
-continued
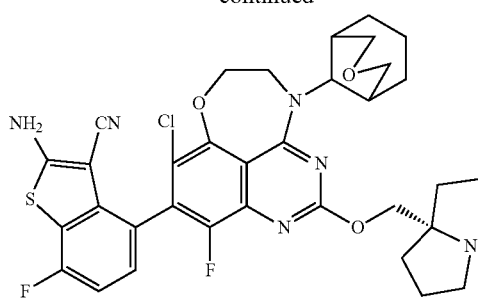
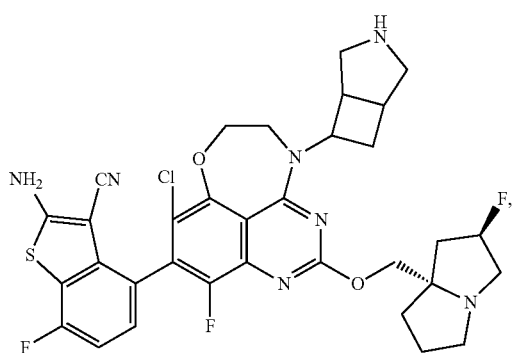
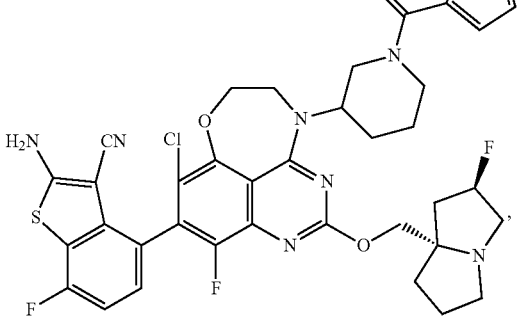

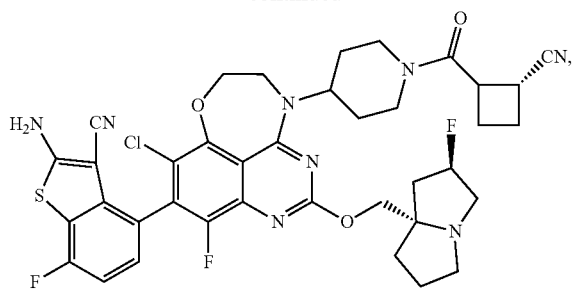
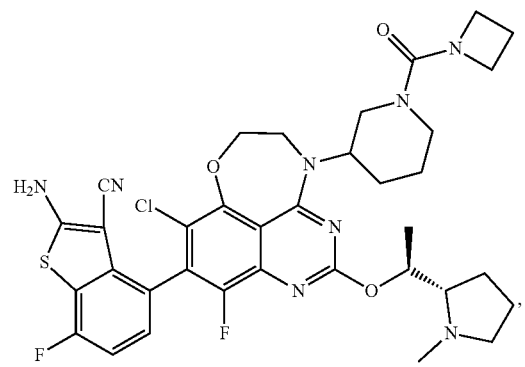
and
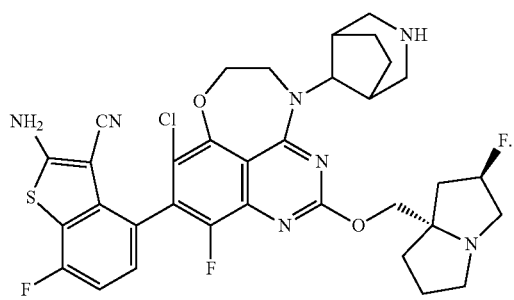
In embodiments is a compound, or a pharmaceutically acceptable salt or solvate thereof, selected from:
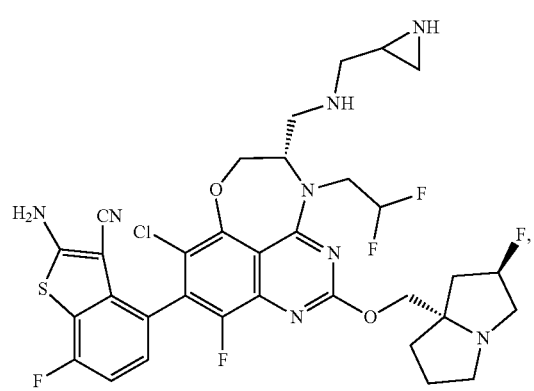
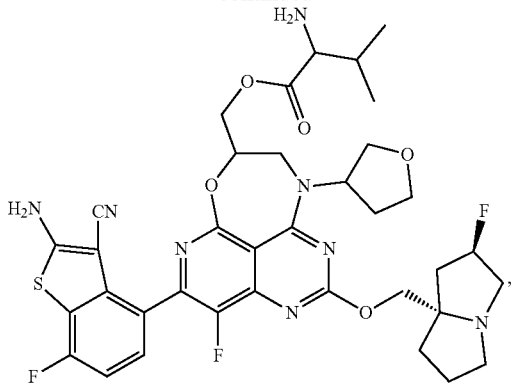
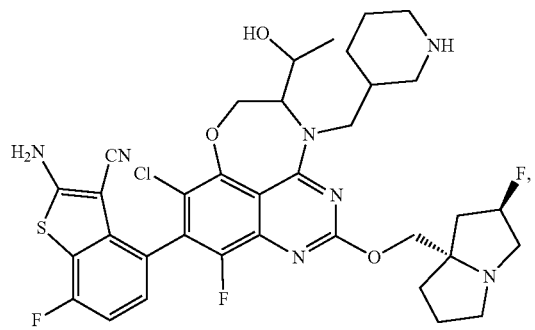
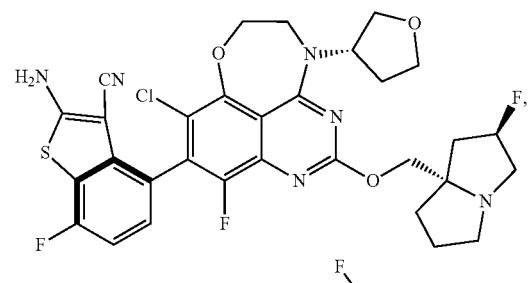
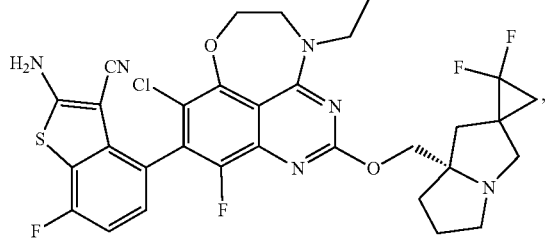
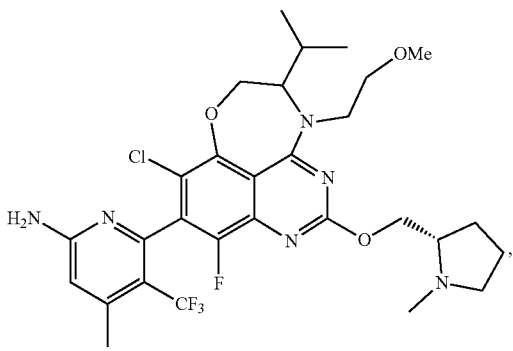

955
-continued
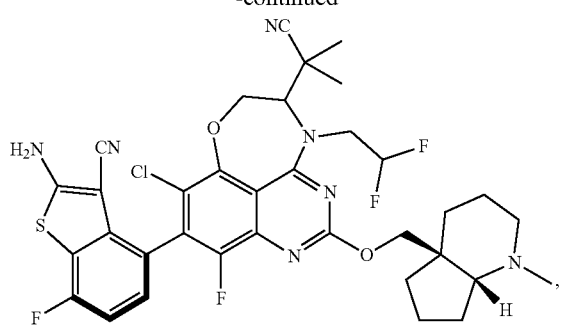
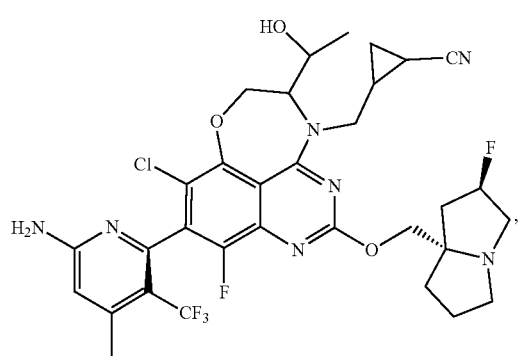
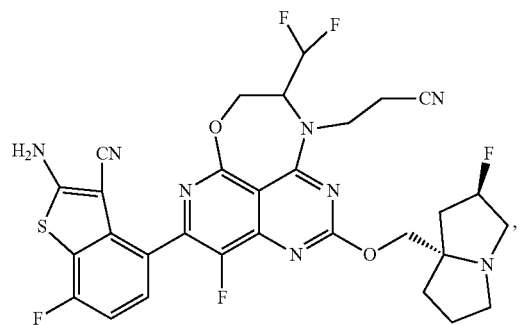
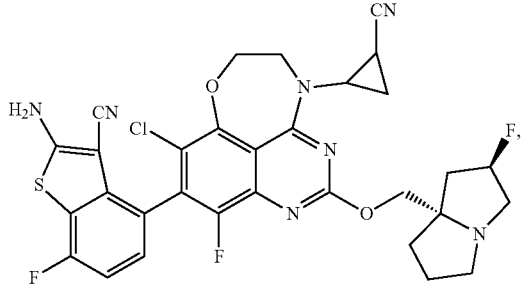
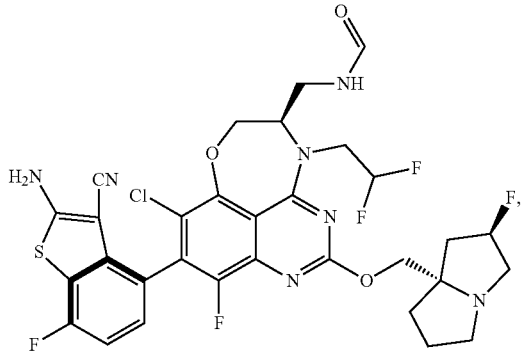
956
-continued
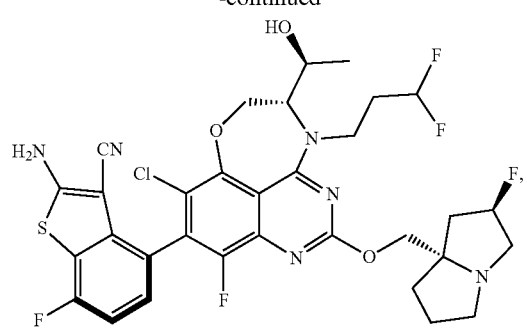
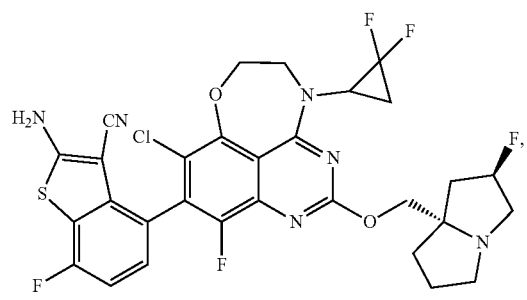
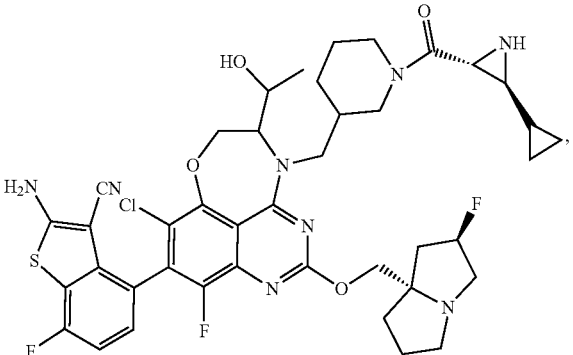
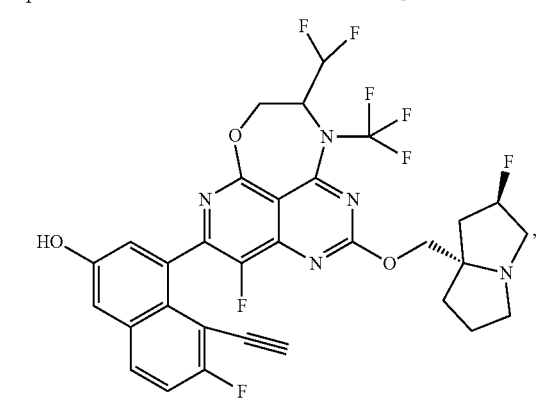
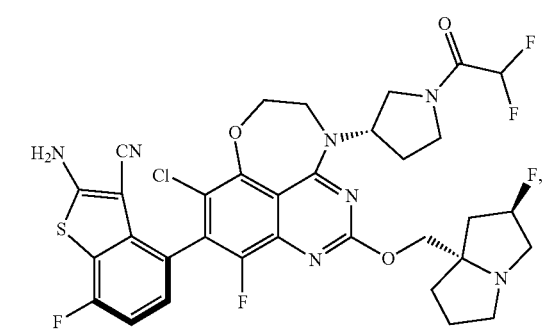

957
-continued
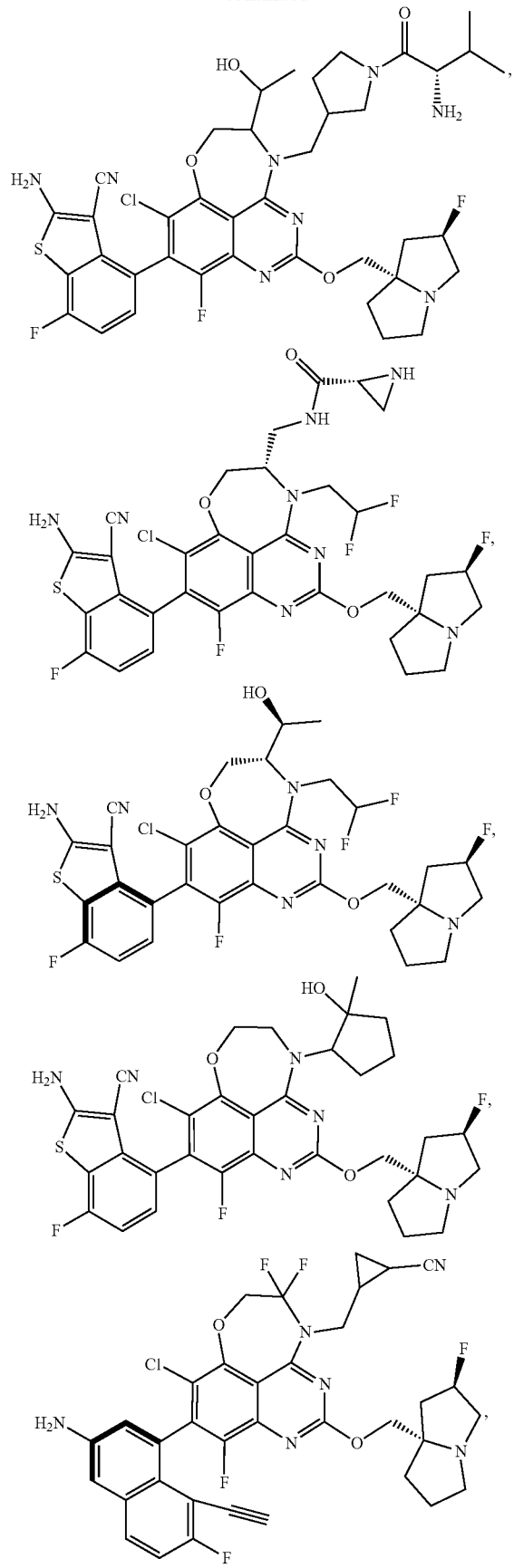
958
-continued
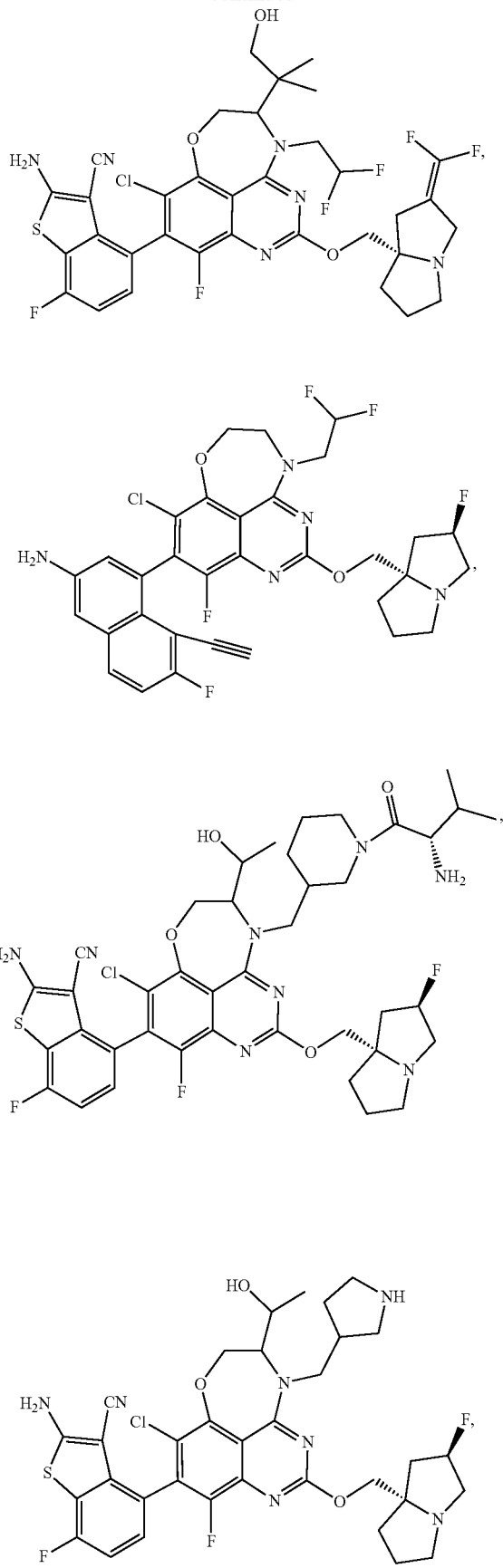

-continued
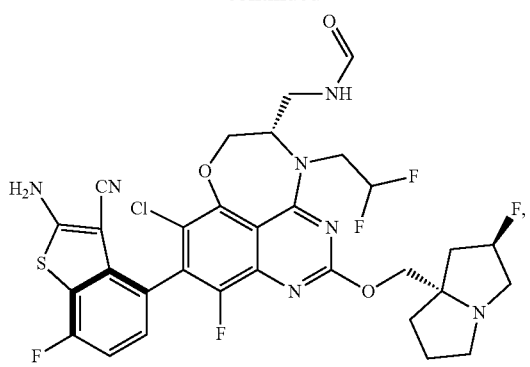
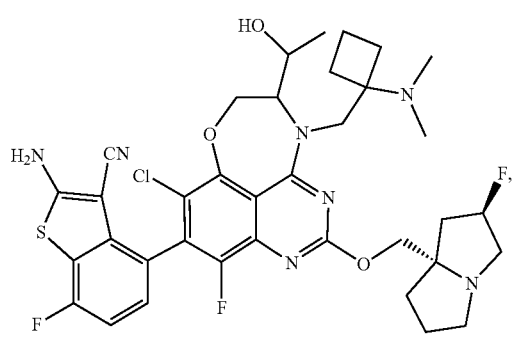
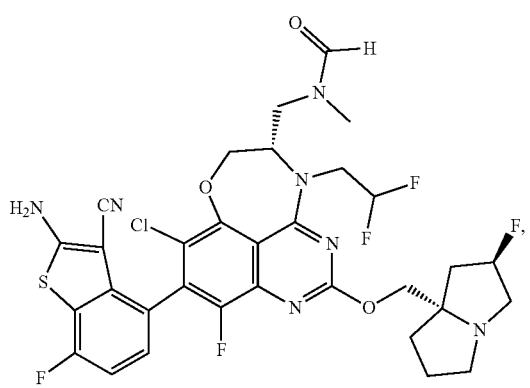
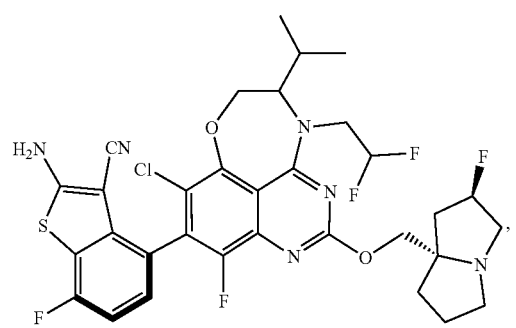
-continued
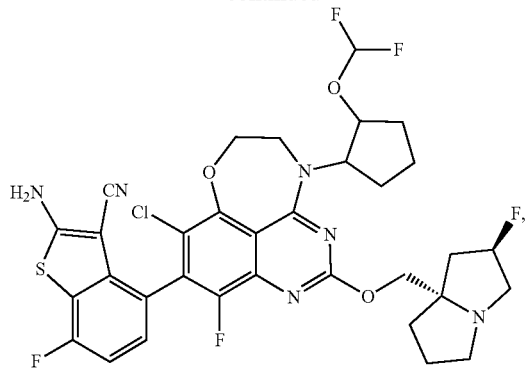
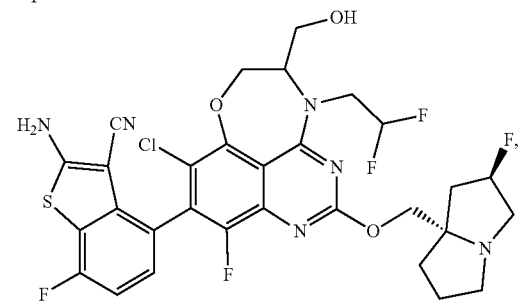
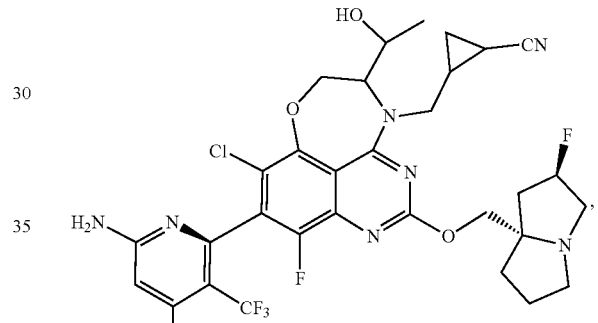
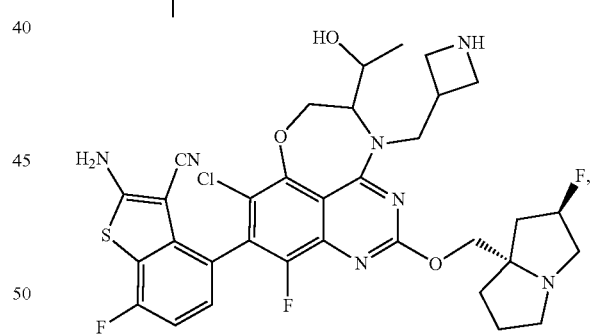
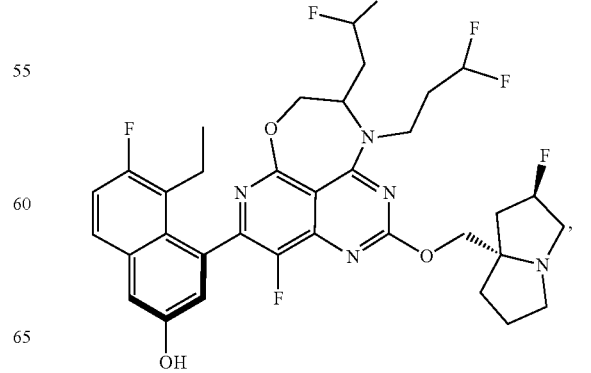

961
-continued
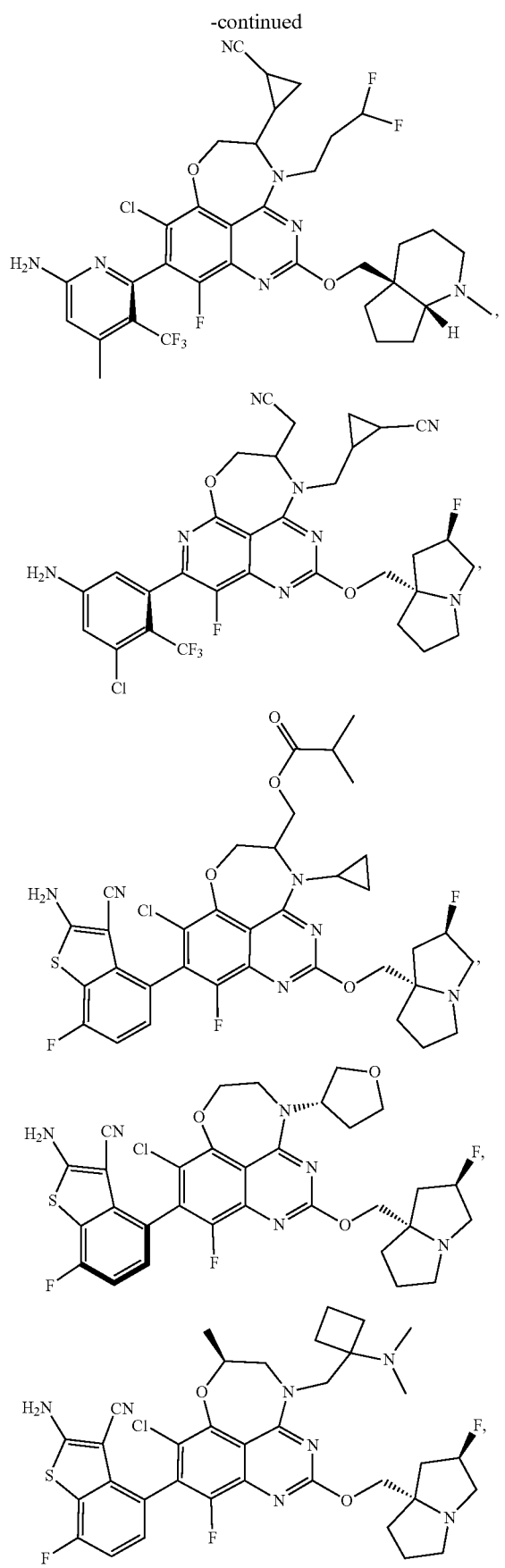
962
-continued
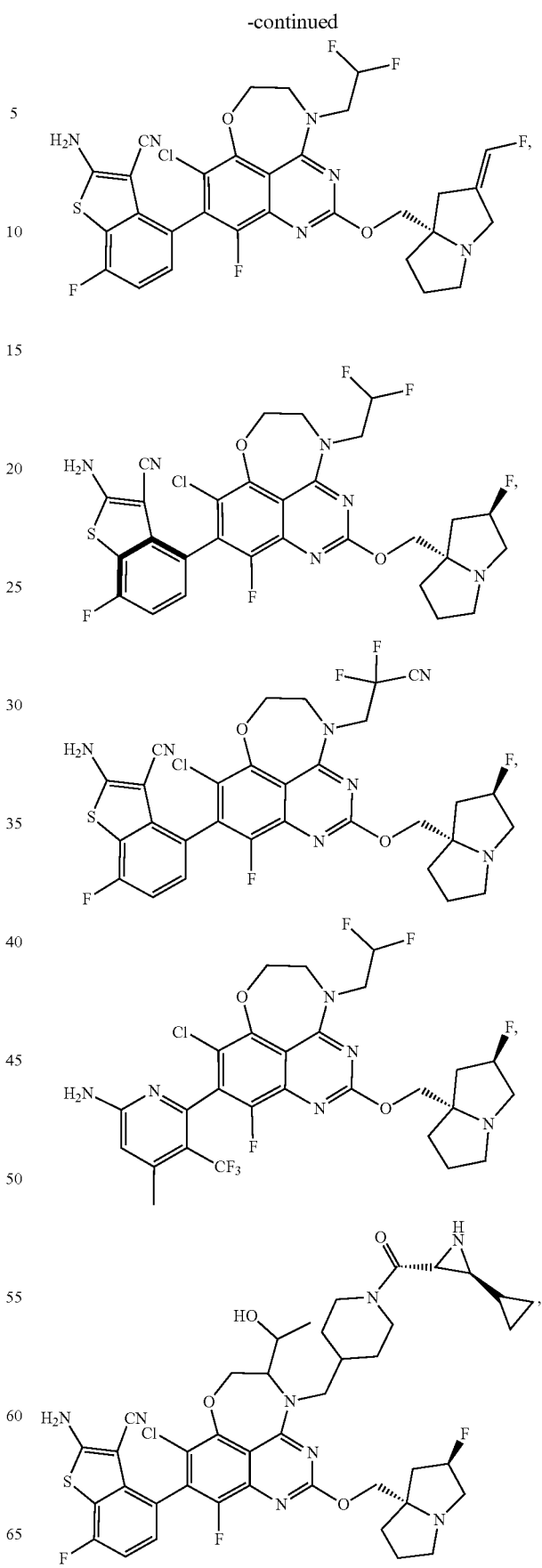

963
-continued
964
-continued
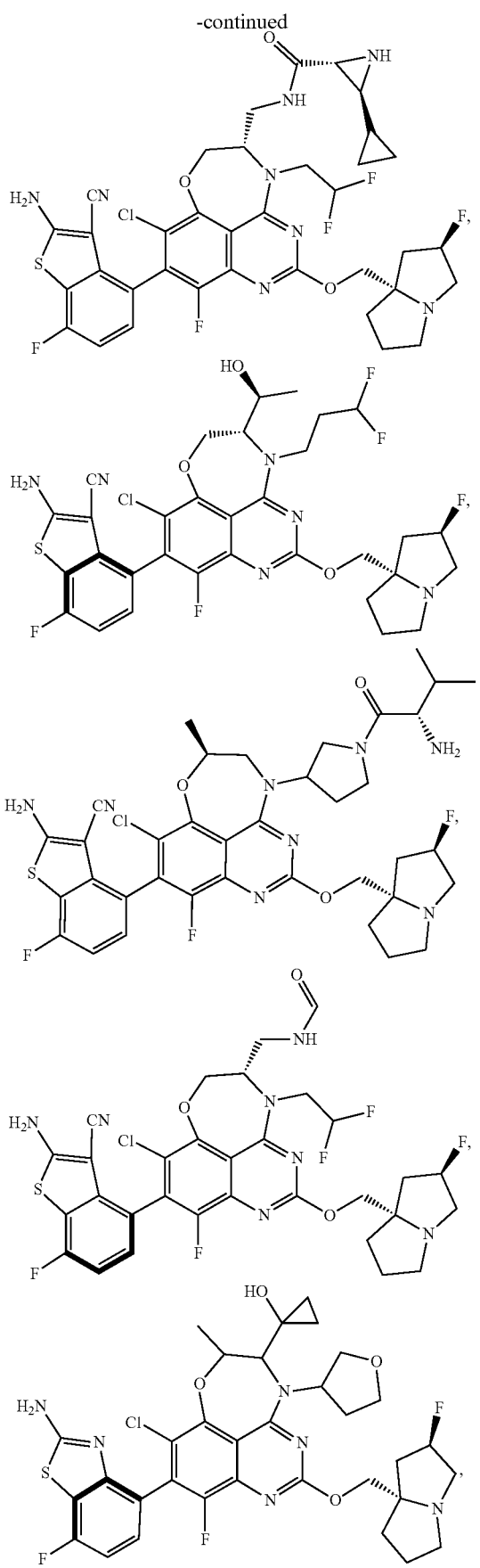
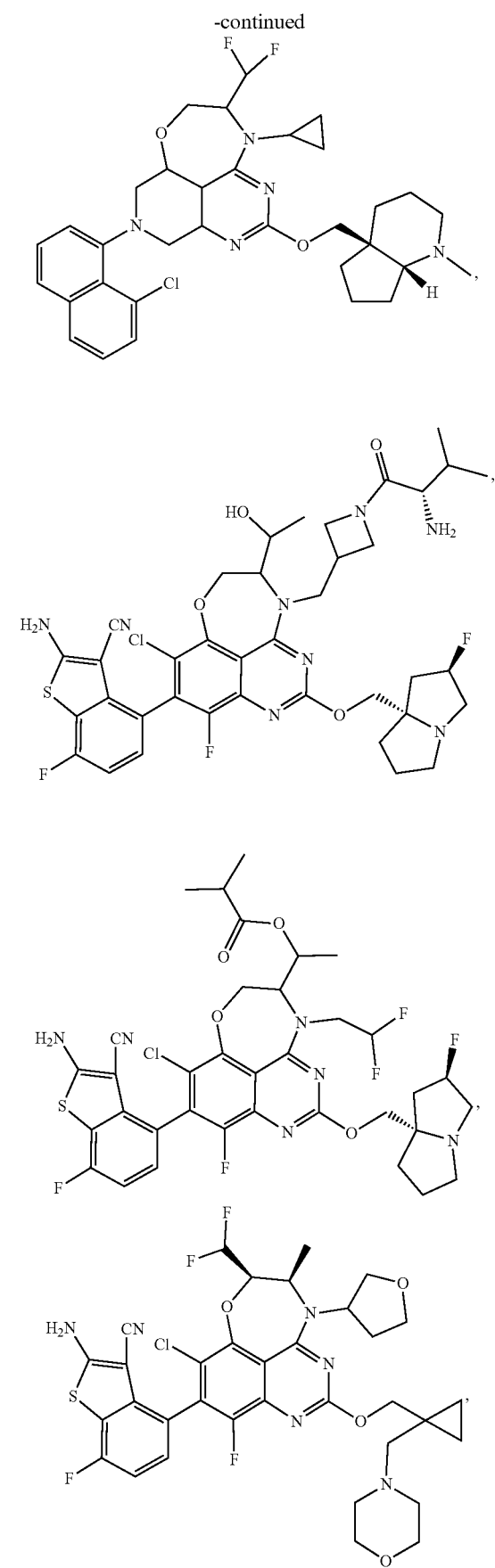

965
-continued
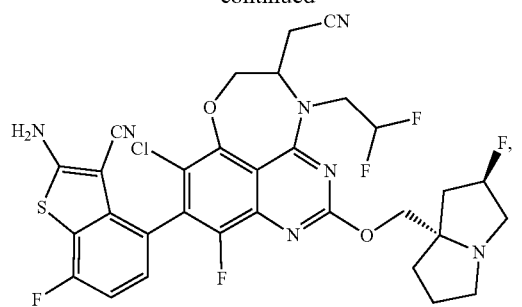
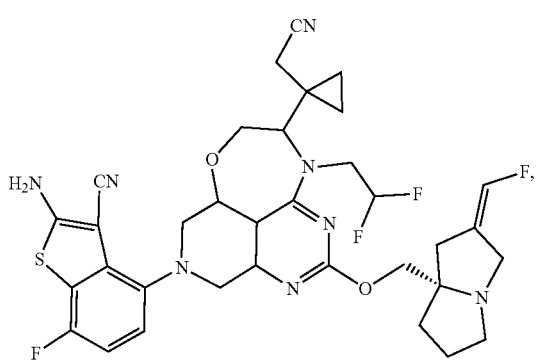
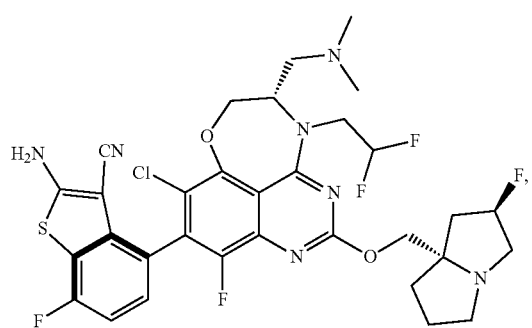
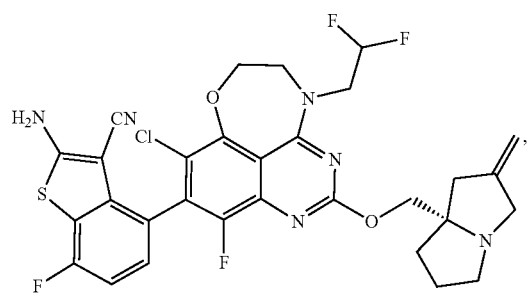
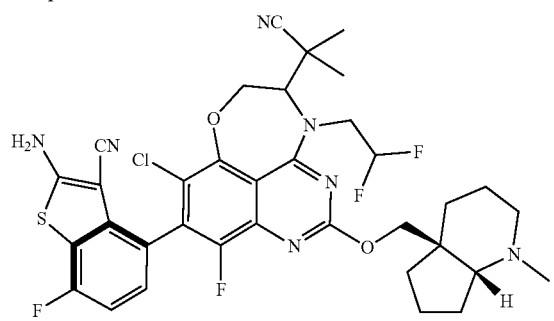
966
-continued
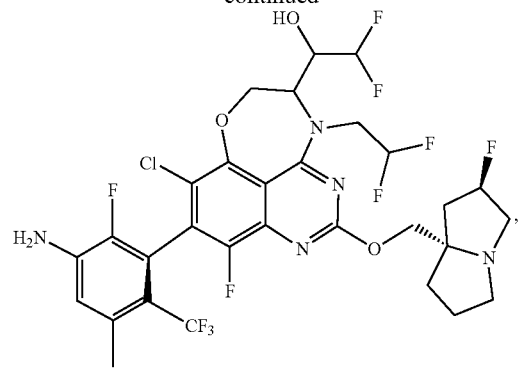
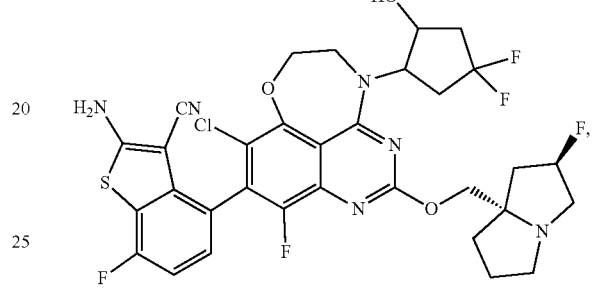
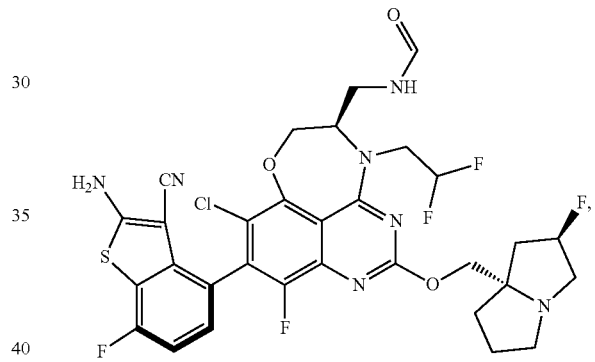
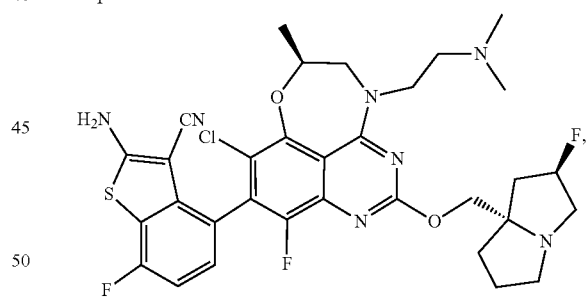
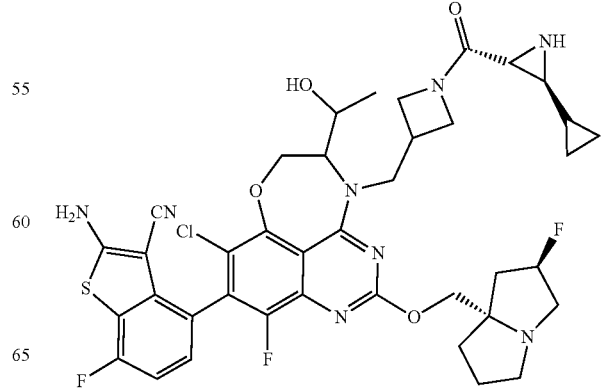

967
-continued
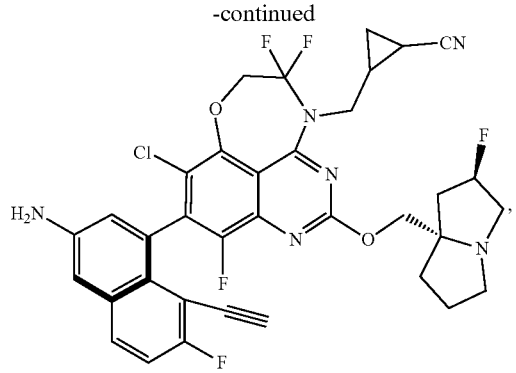
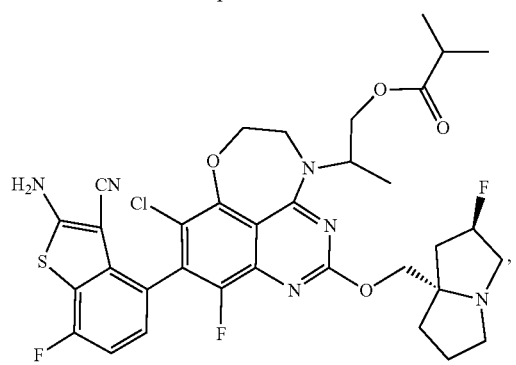
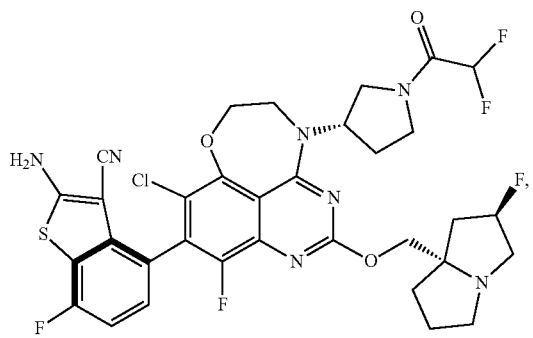
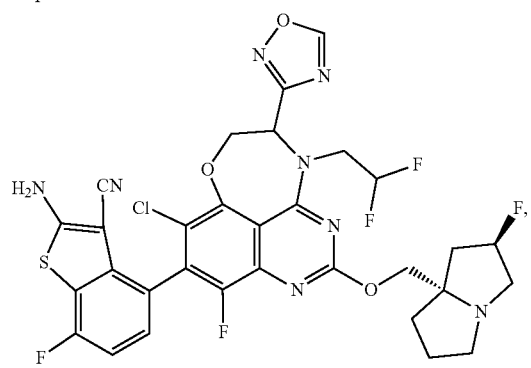
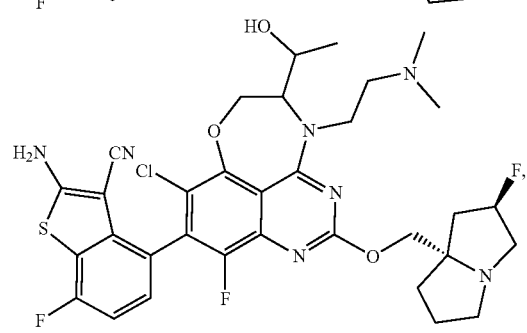
968
-continued
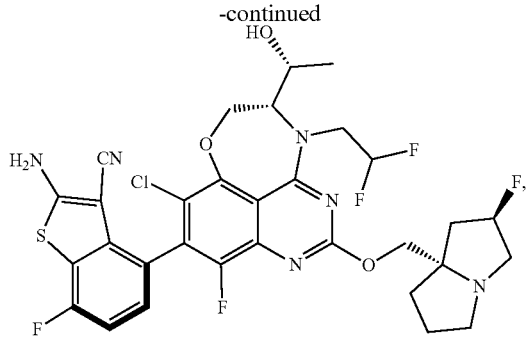
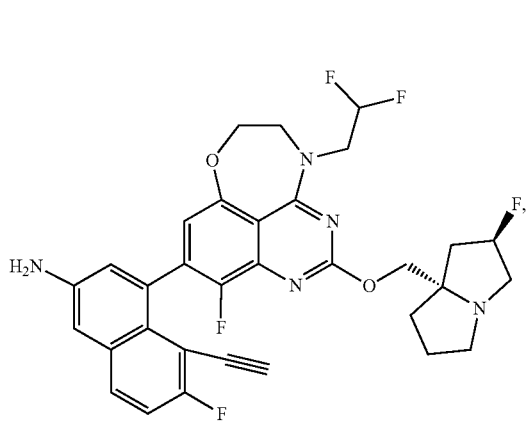
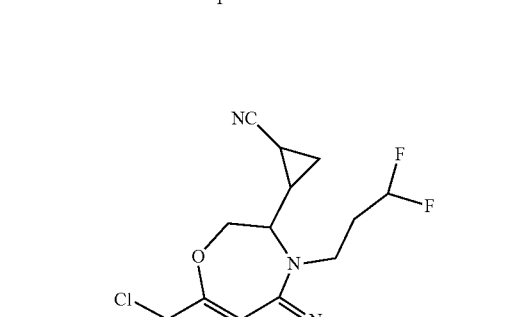
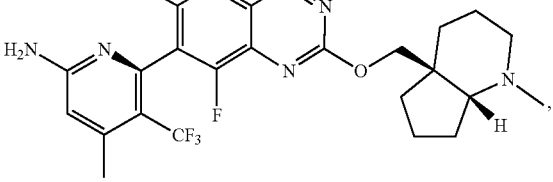
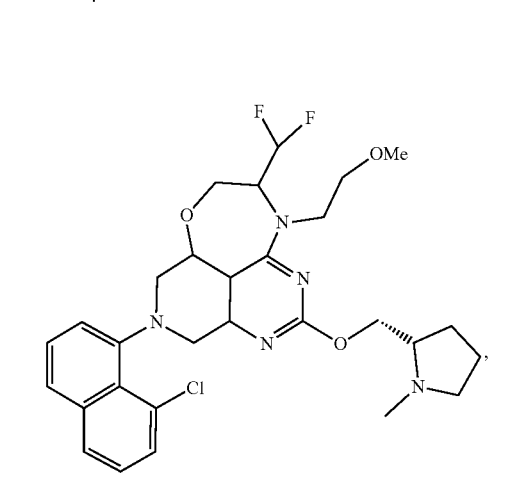

969
-continued
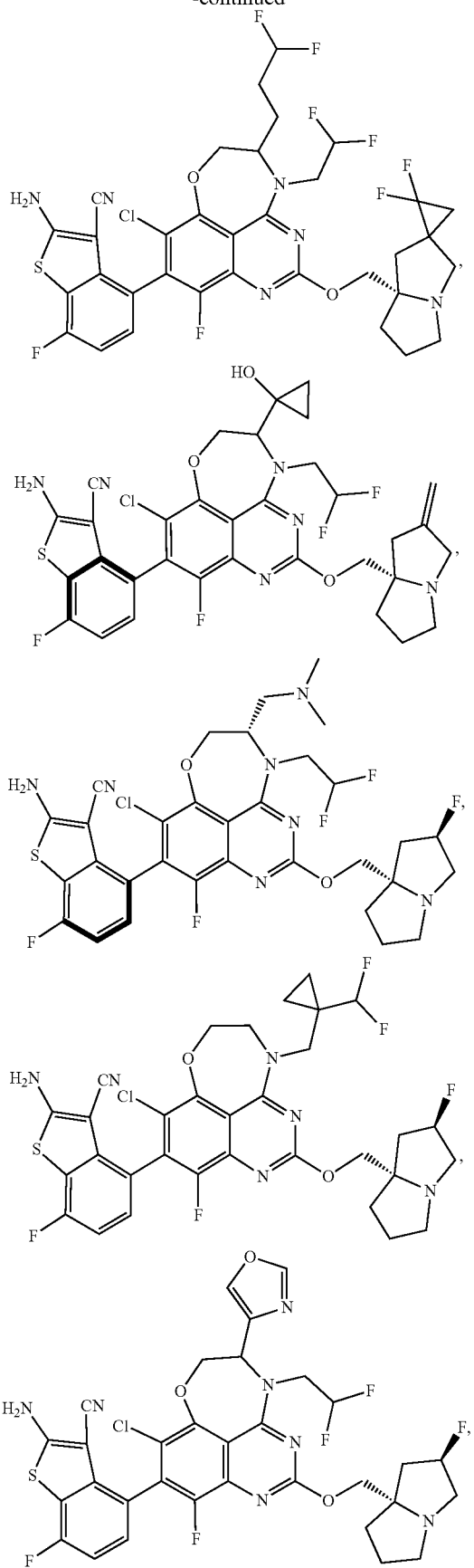
970
-continued
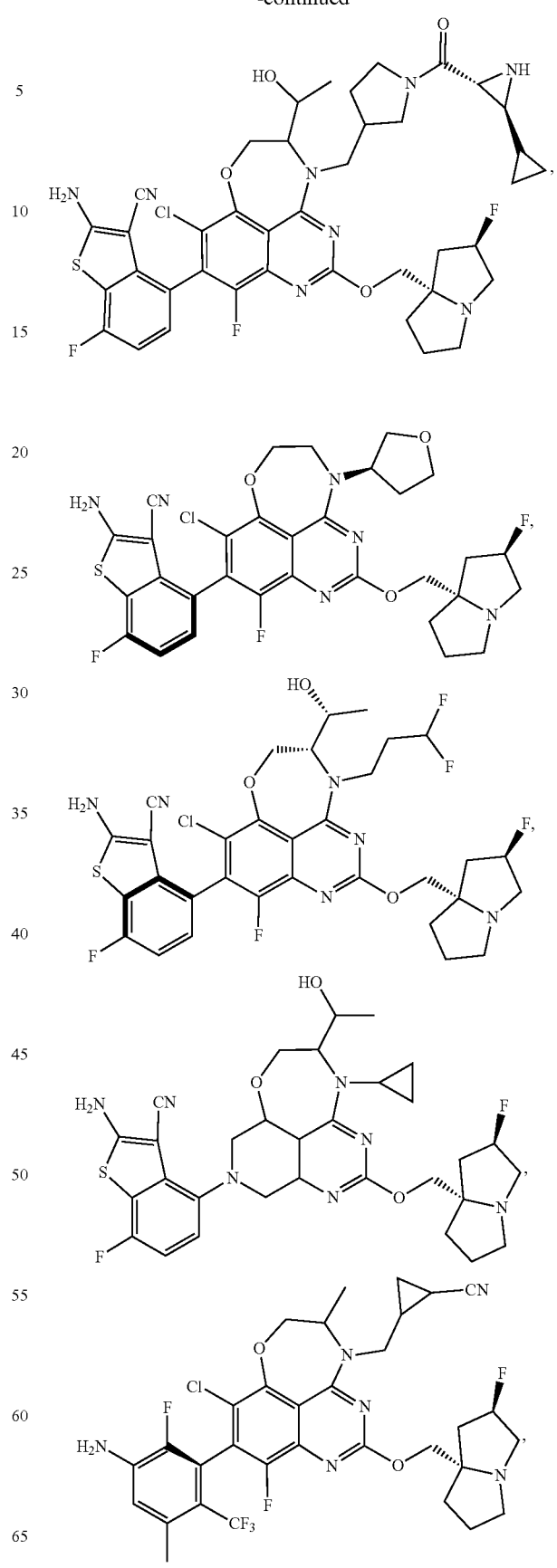

971
-continued
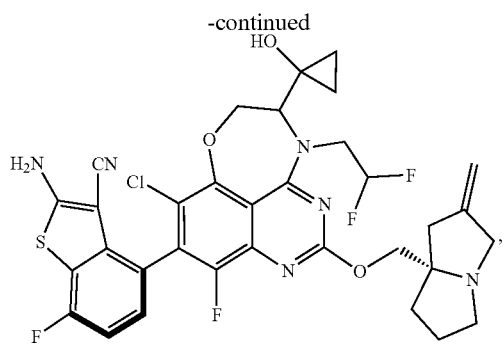
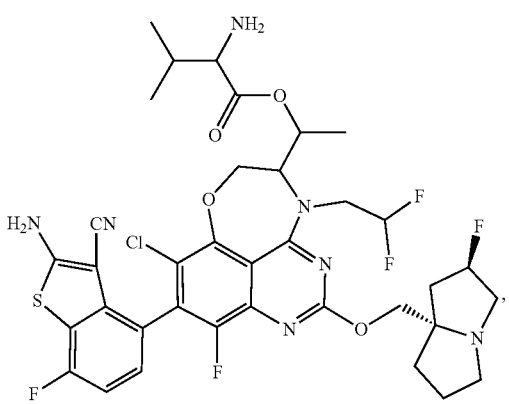
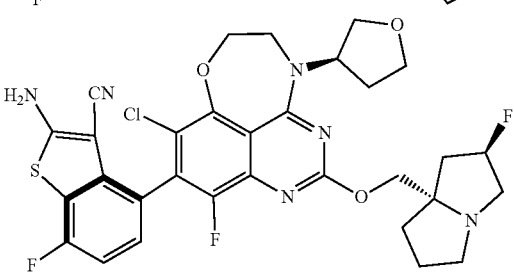
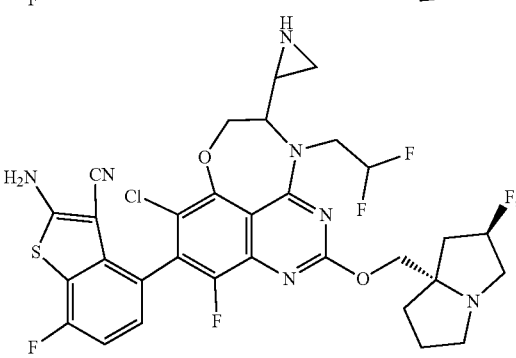
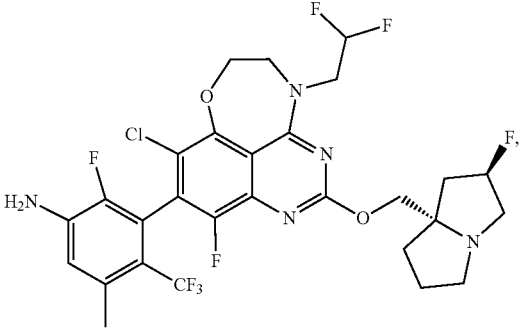
972
-continued
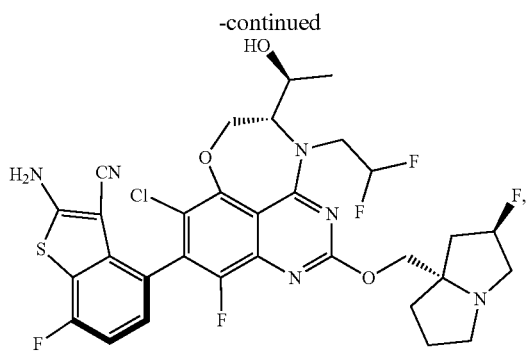
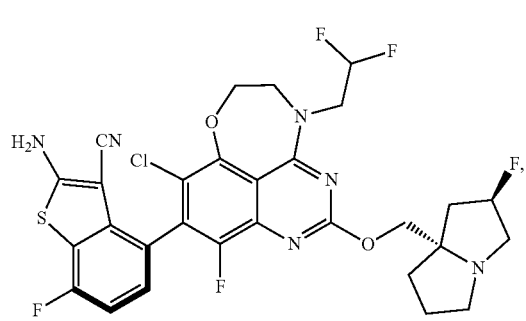
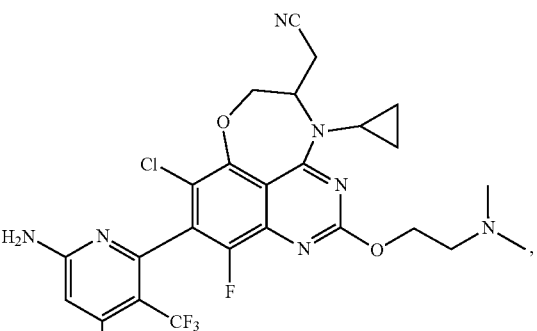
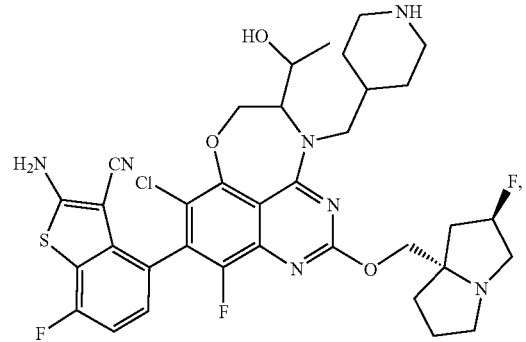

973
-continued
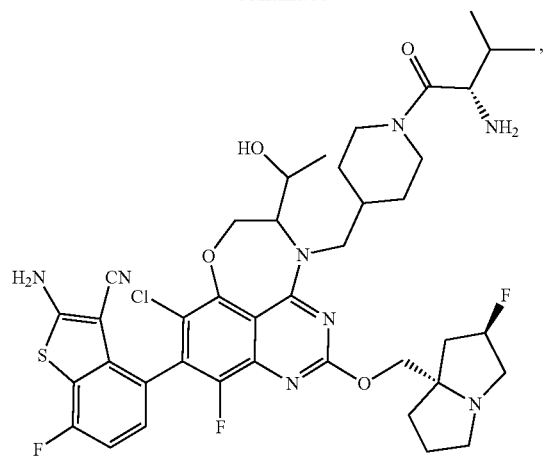
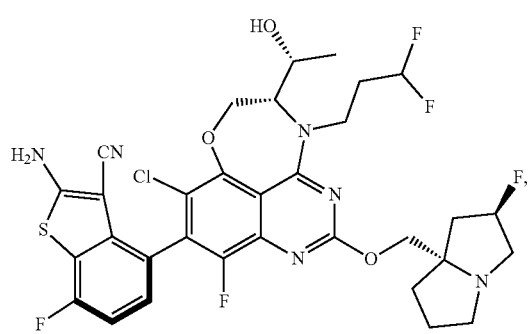
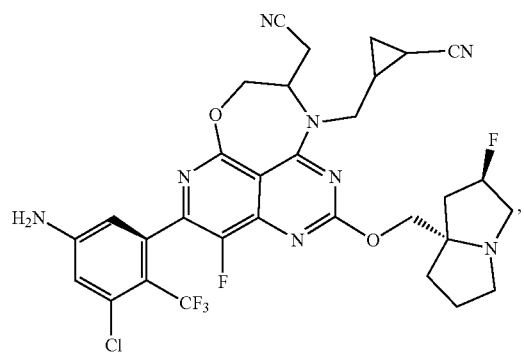
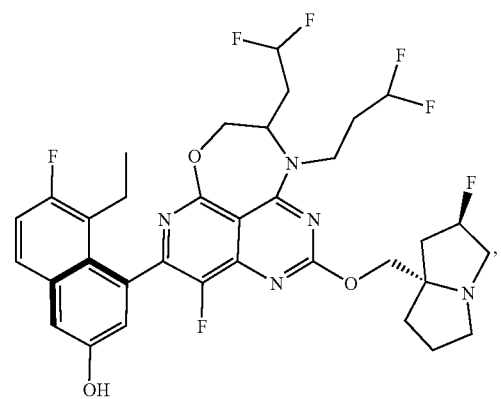
974
-continued
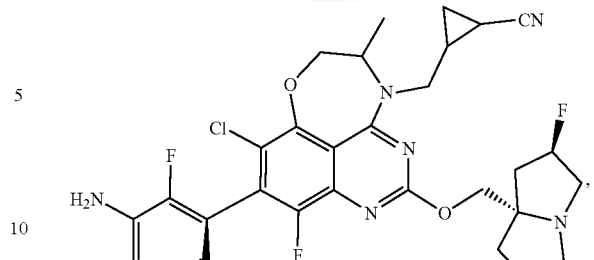
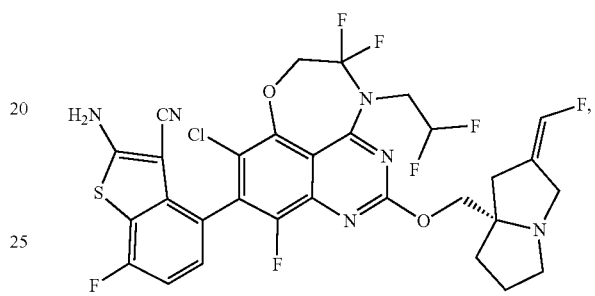
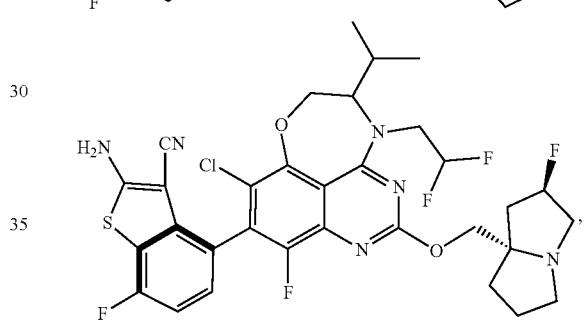
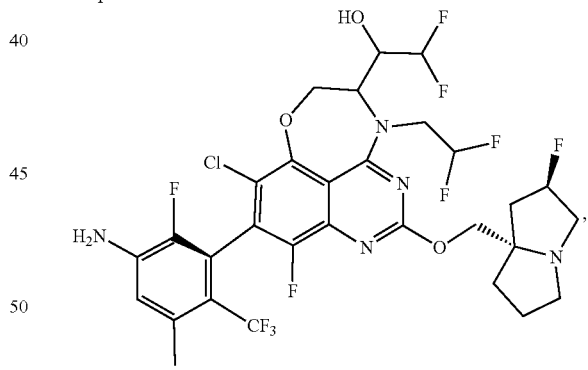
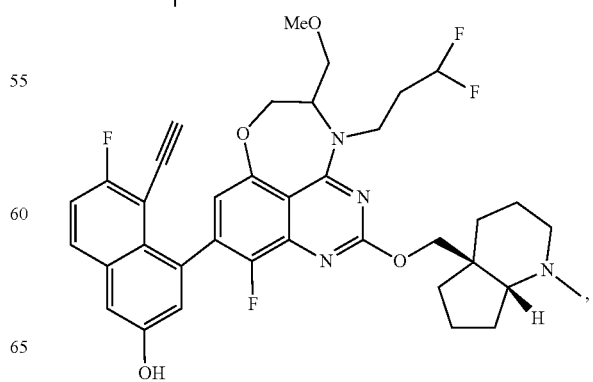

-continued
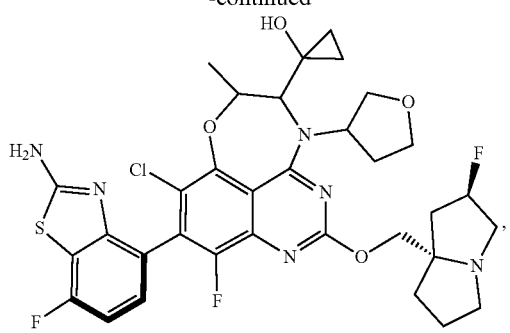
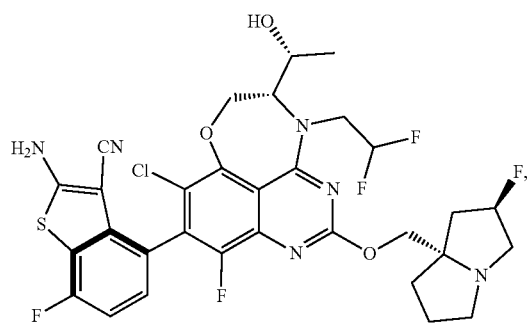
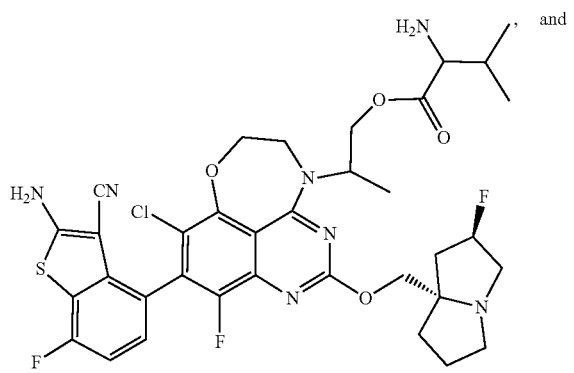, and
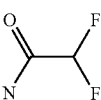
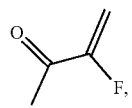
In embodiments, the compound is a compound described herein.
In an aspect is provided a compound selected from:
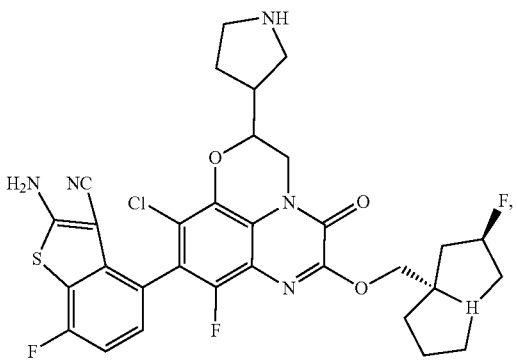
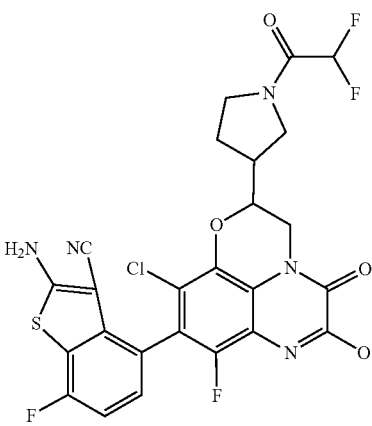
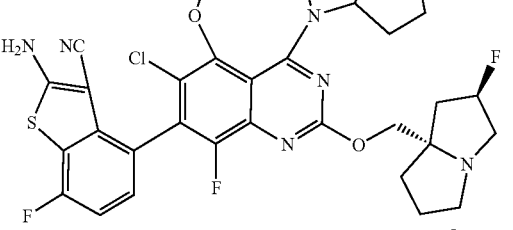
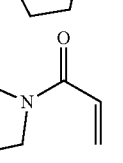
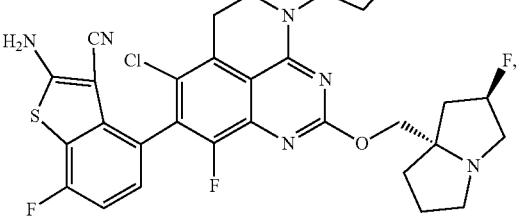

977
-continued
978
-continued
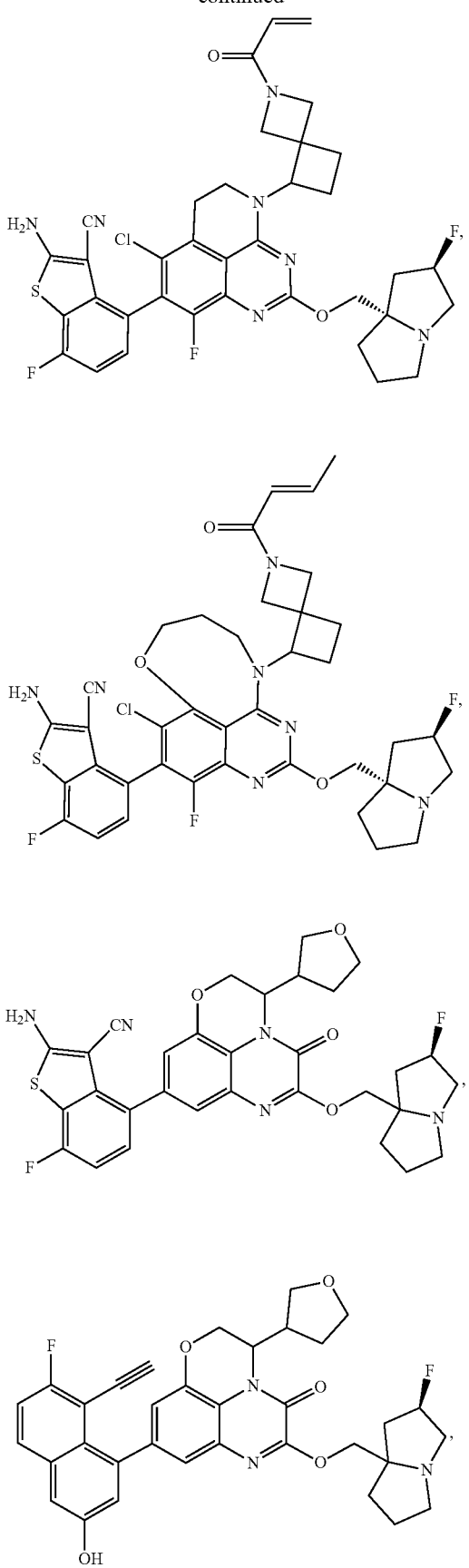
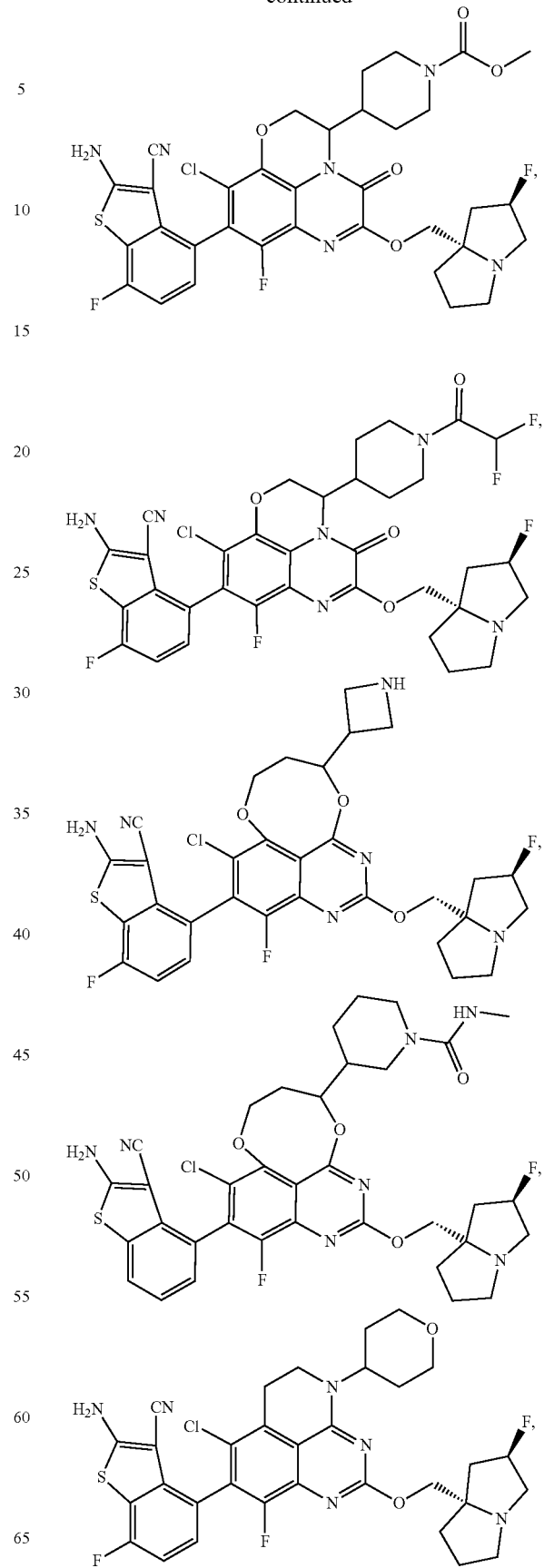

979
-continued
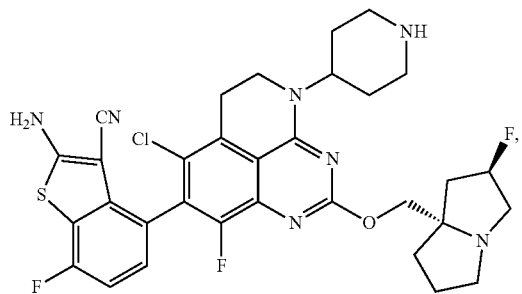
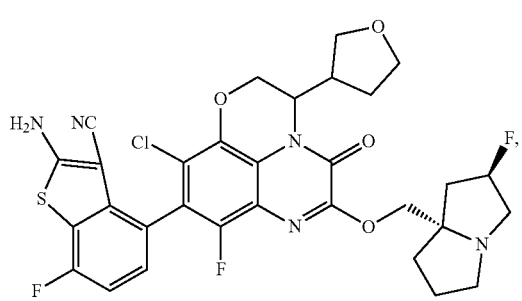
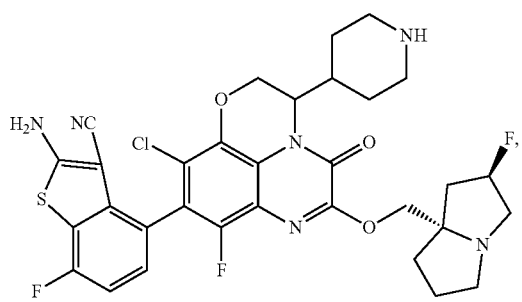
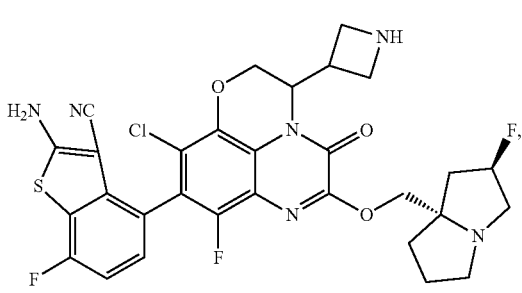
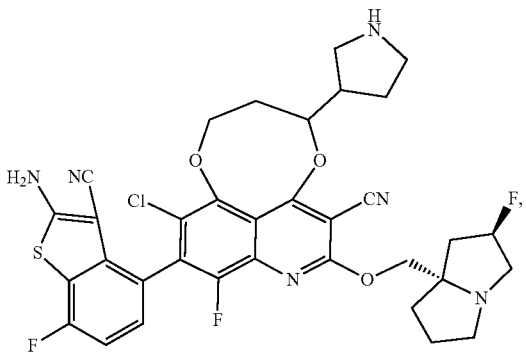
980
-continued
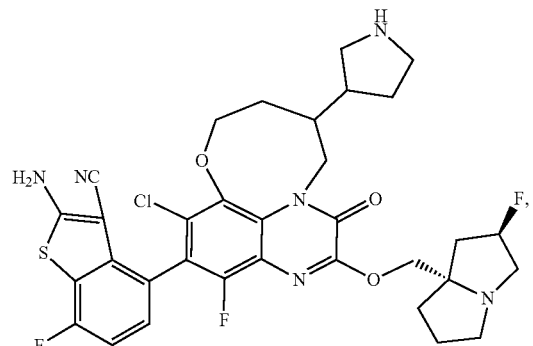
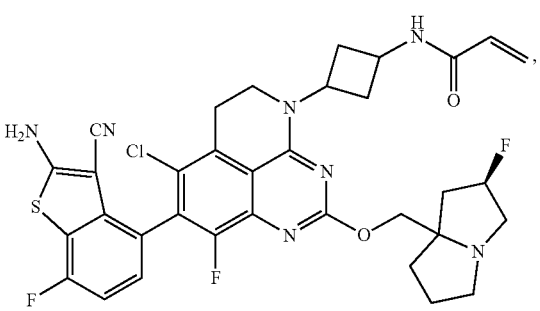
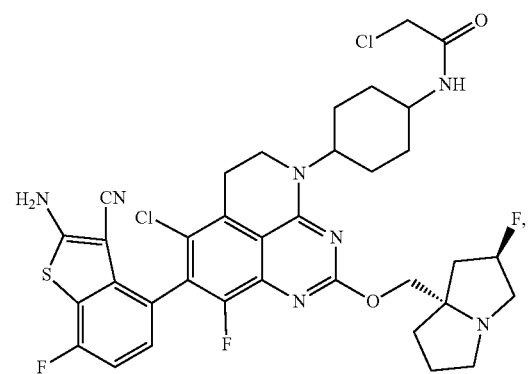
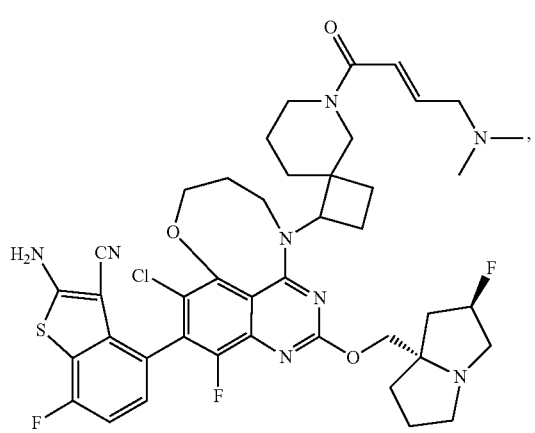

981
-continued
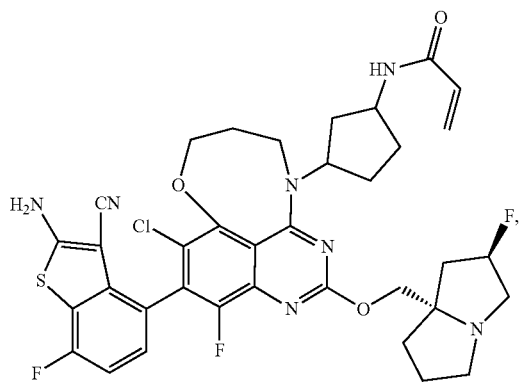
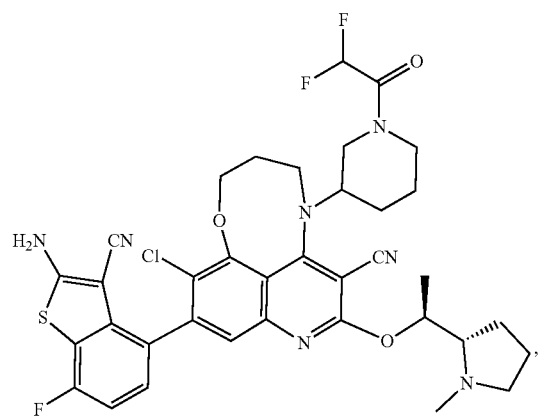
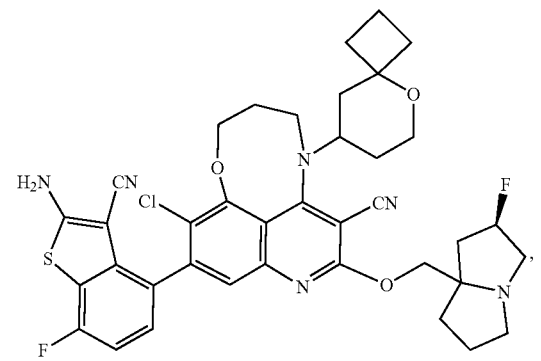
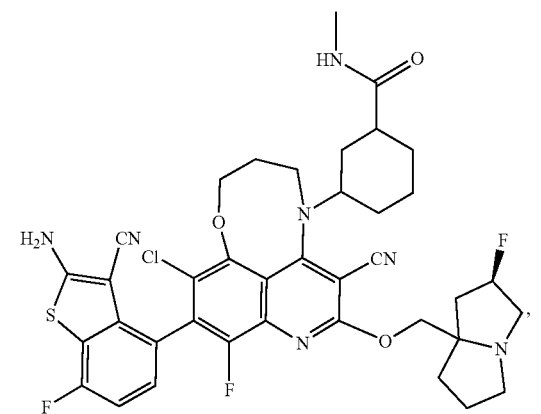
982
-continued
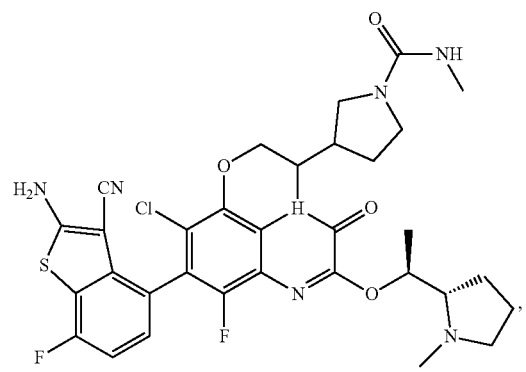
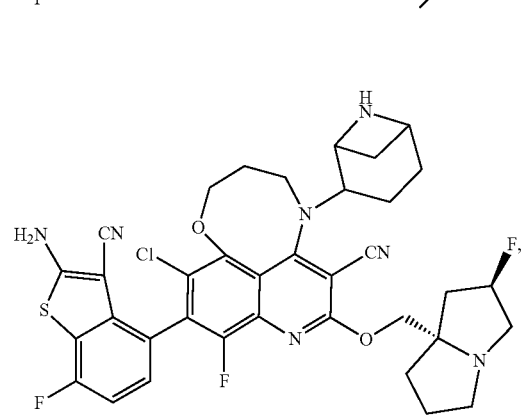
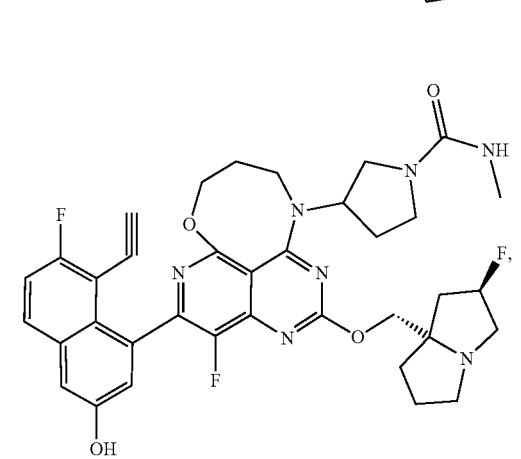
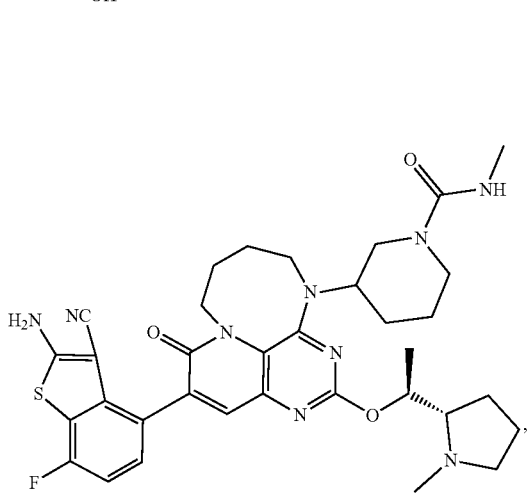

983
-continued
984
-continued
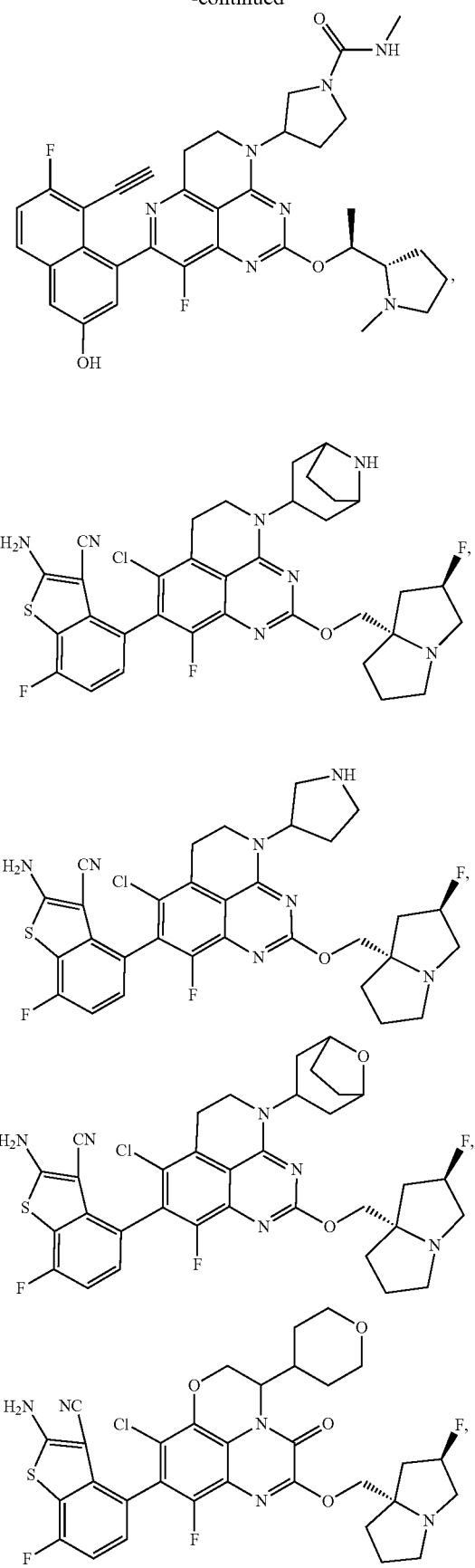
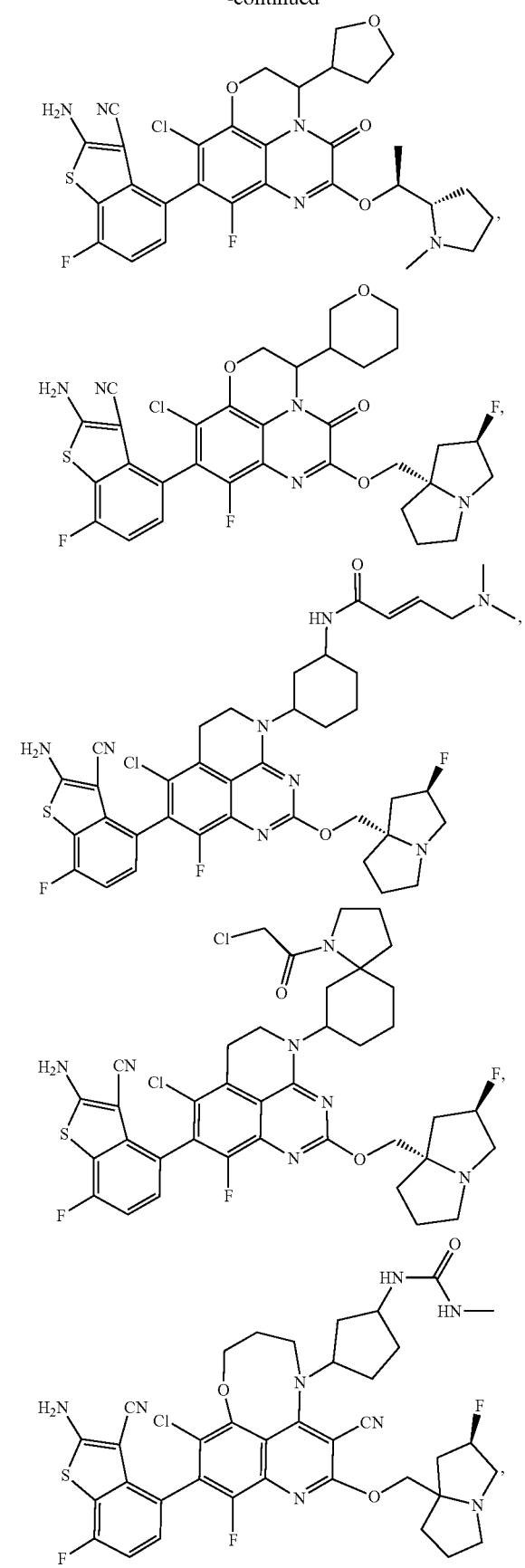

985
-continued
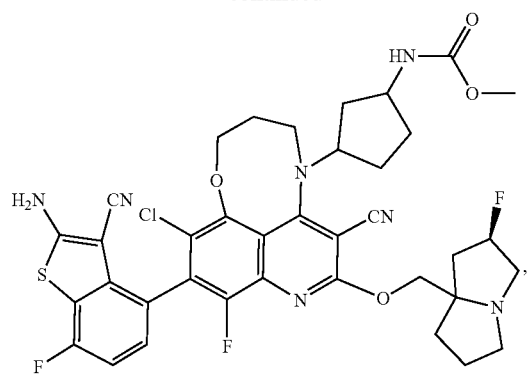
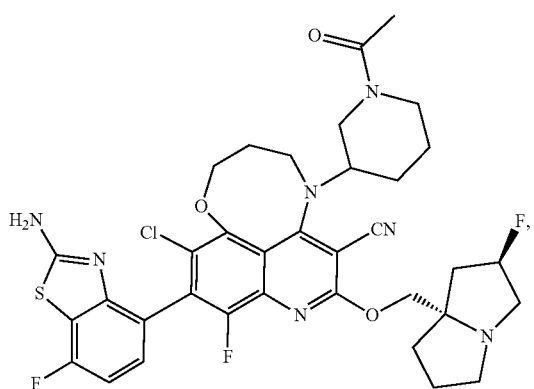
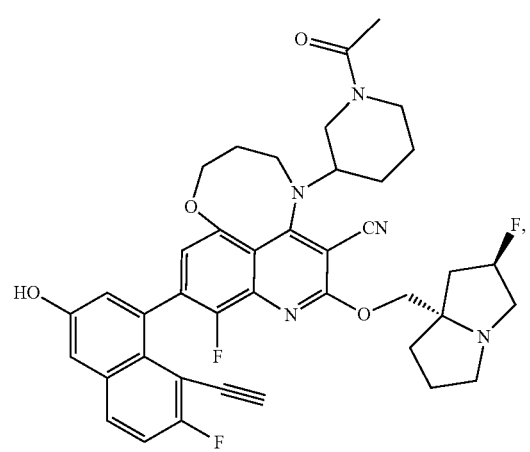
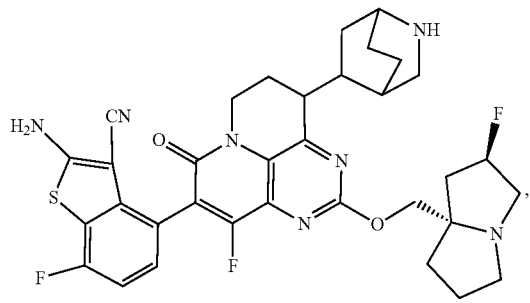
986
-continued
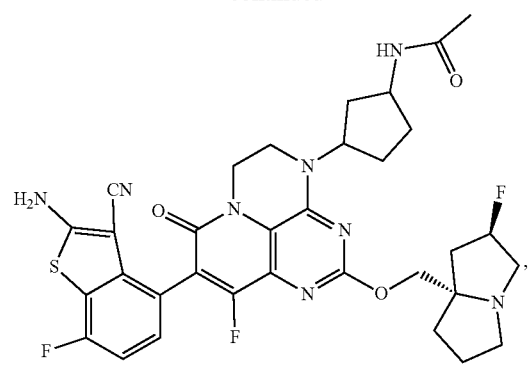
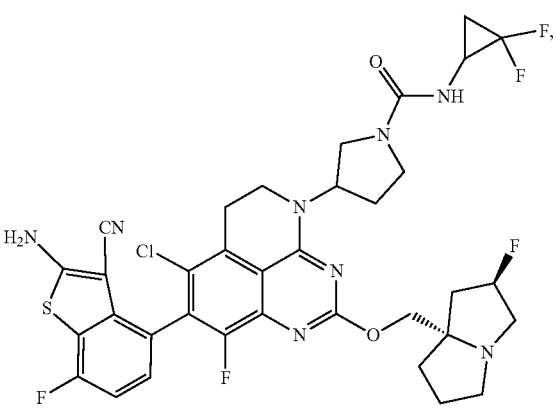
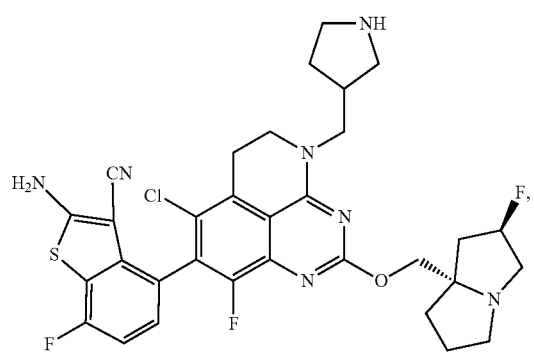
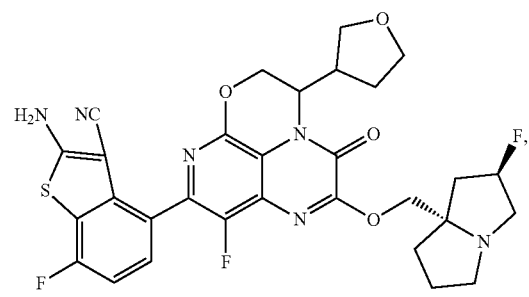

987
-continued
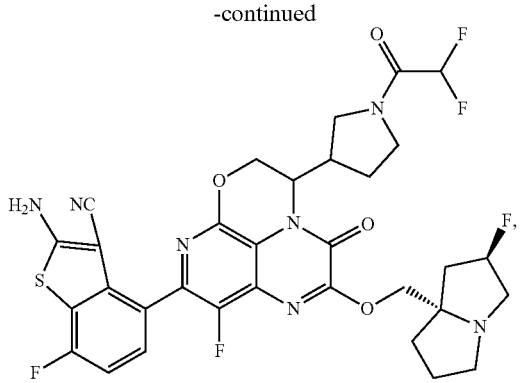
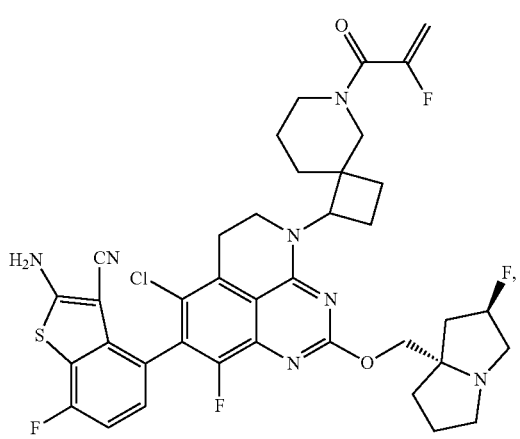
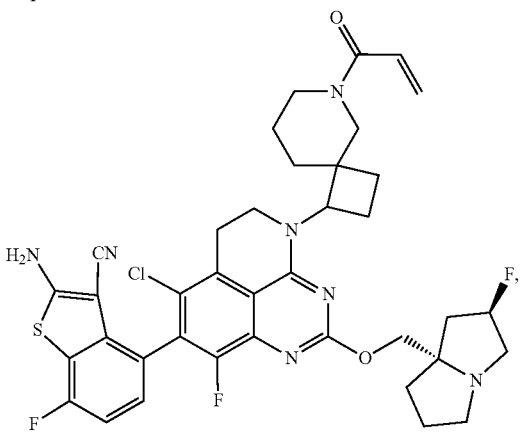
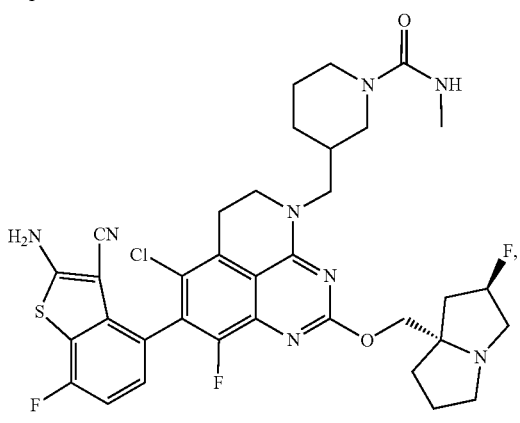
988
-continued
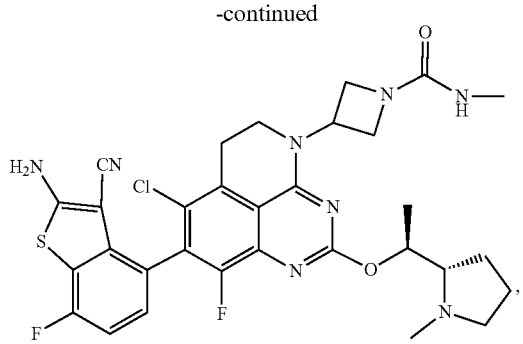
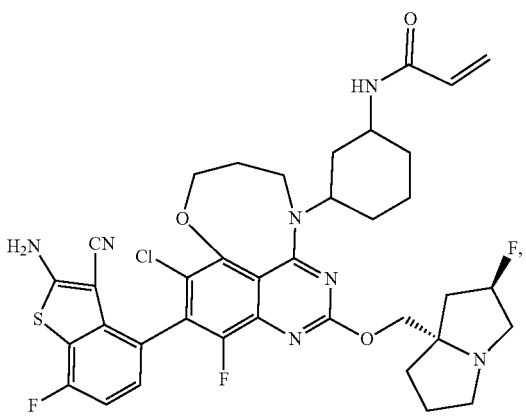
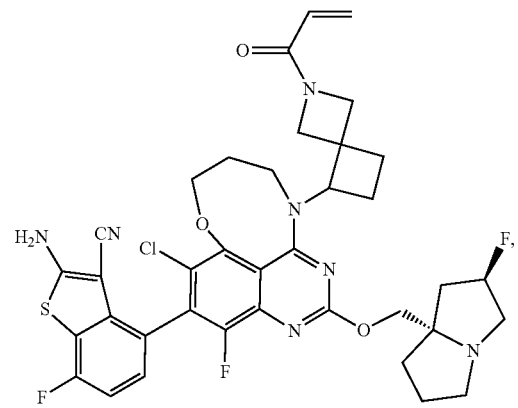
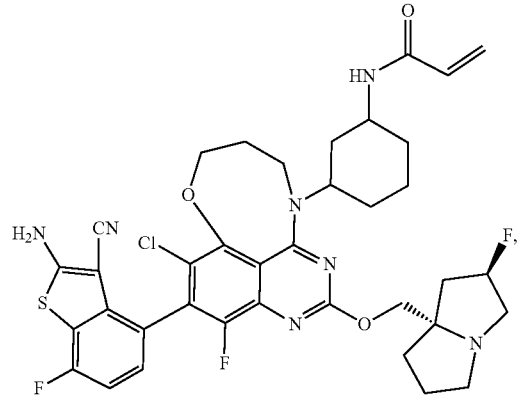

989
-continued
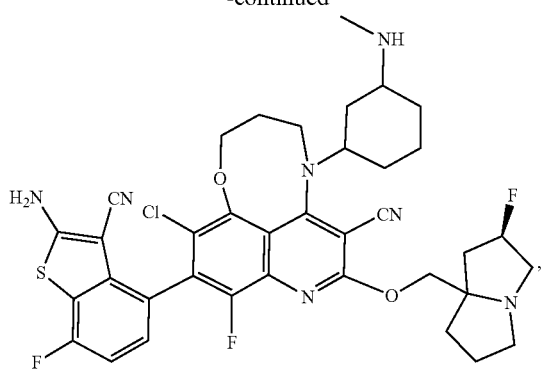
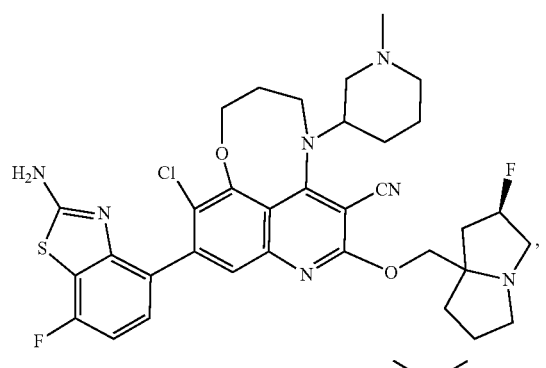
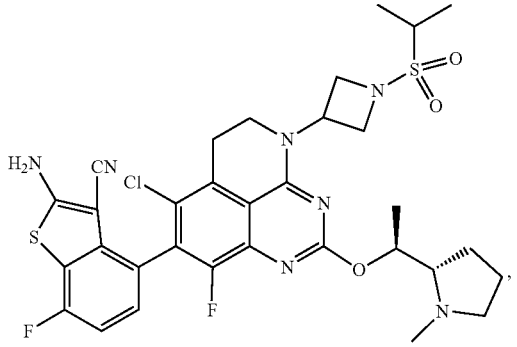
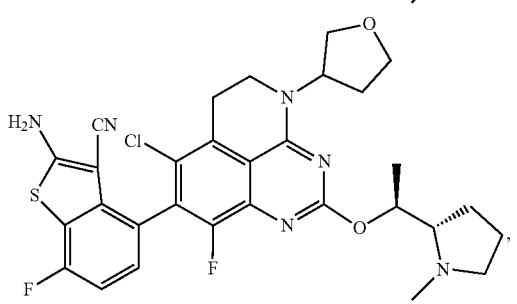
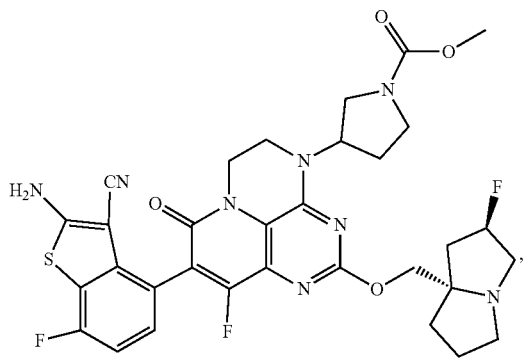
990
-continued
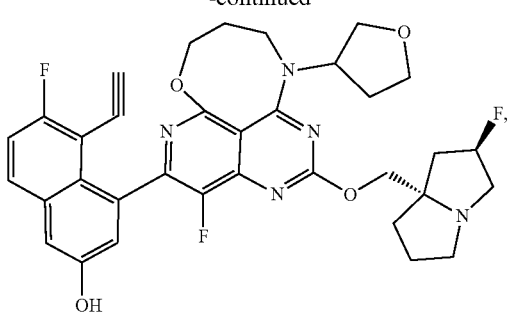
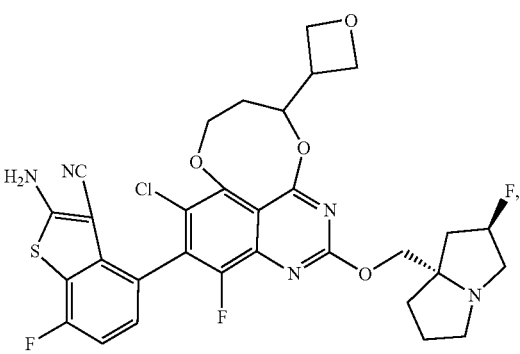
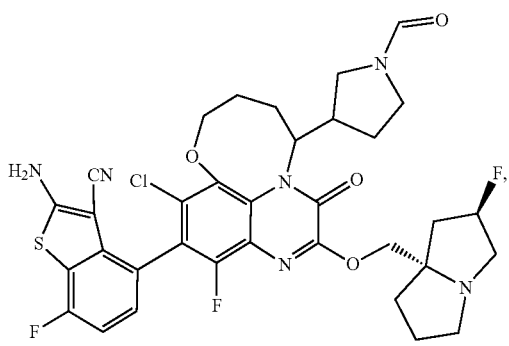
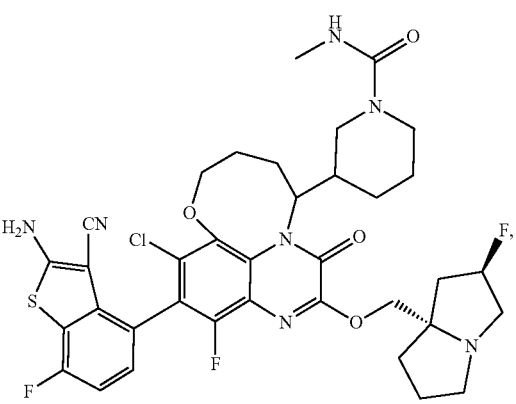

991
-continued
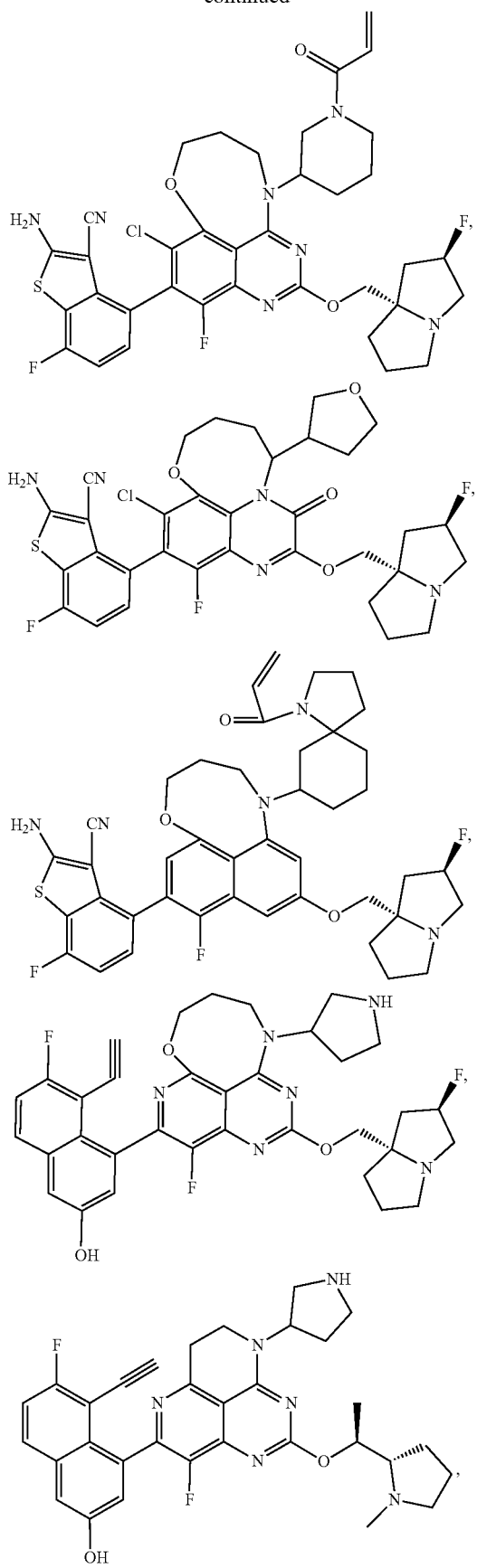
992
-continued
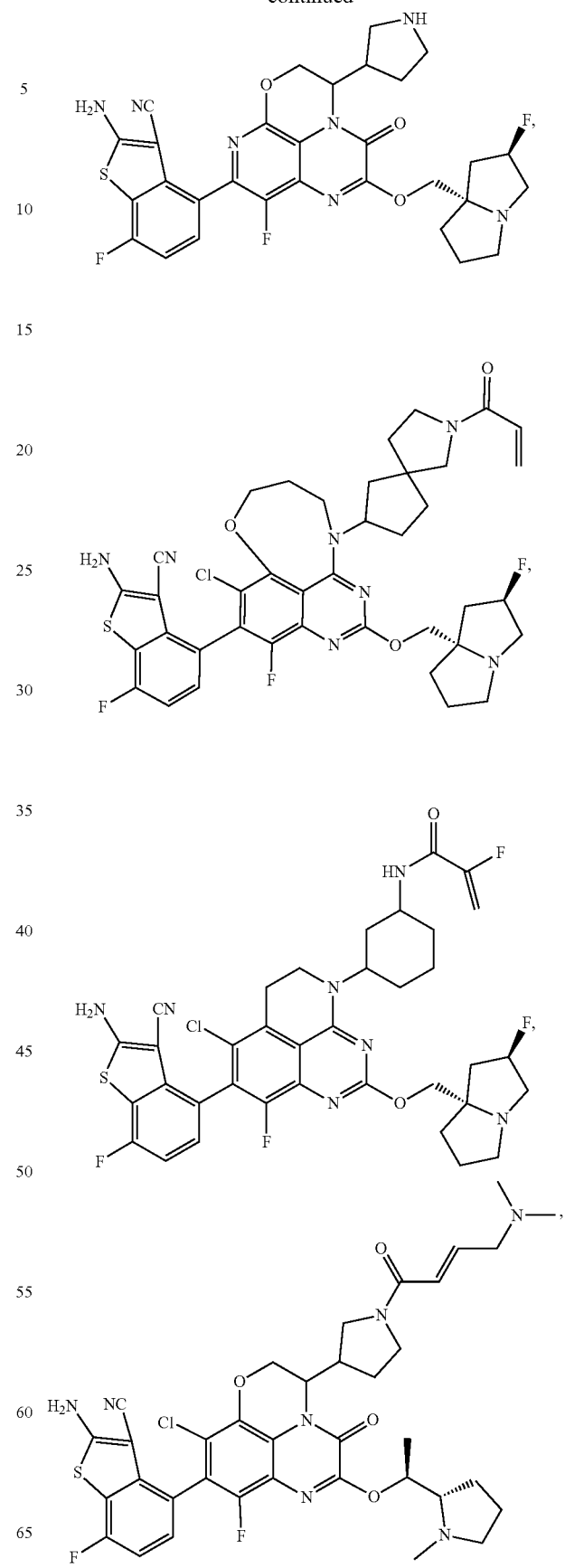

993
-continued
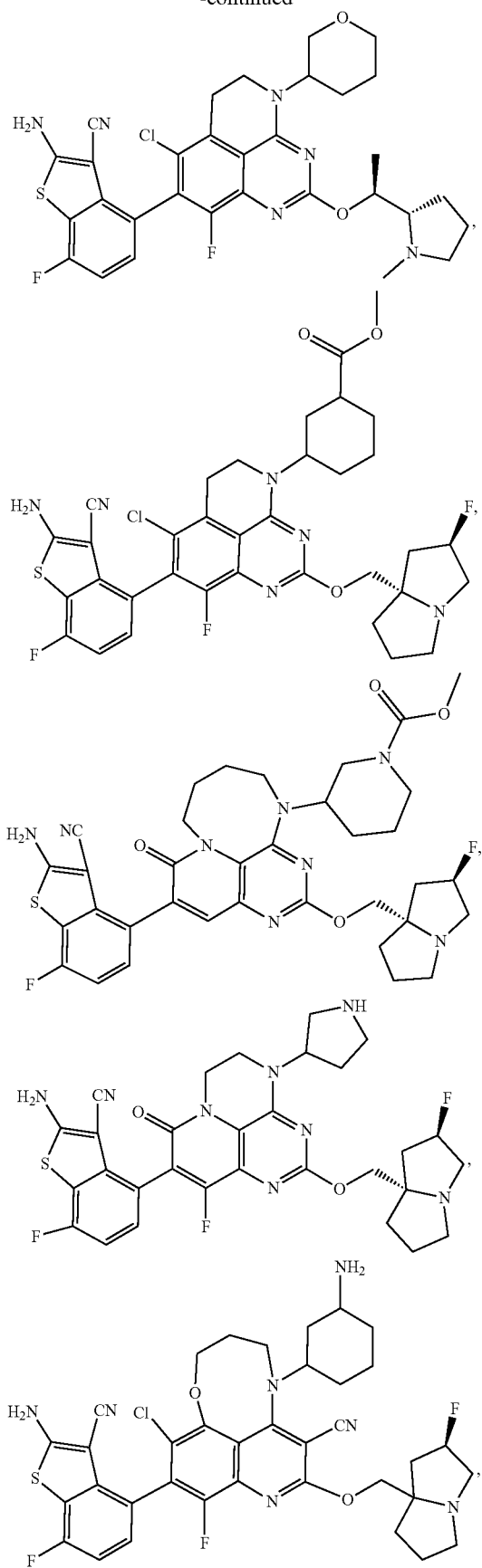
994
-continued
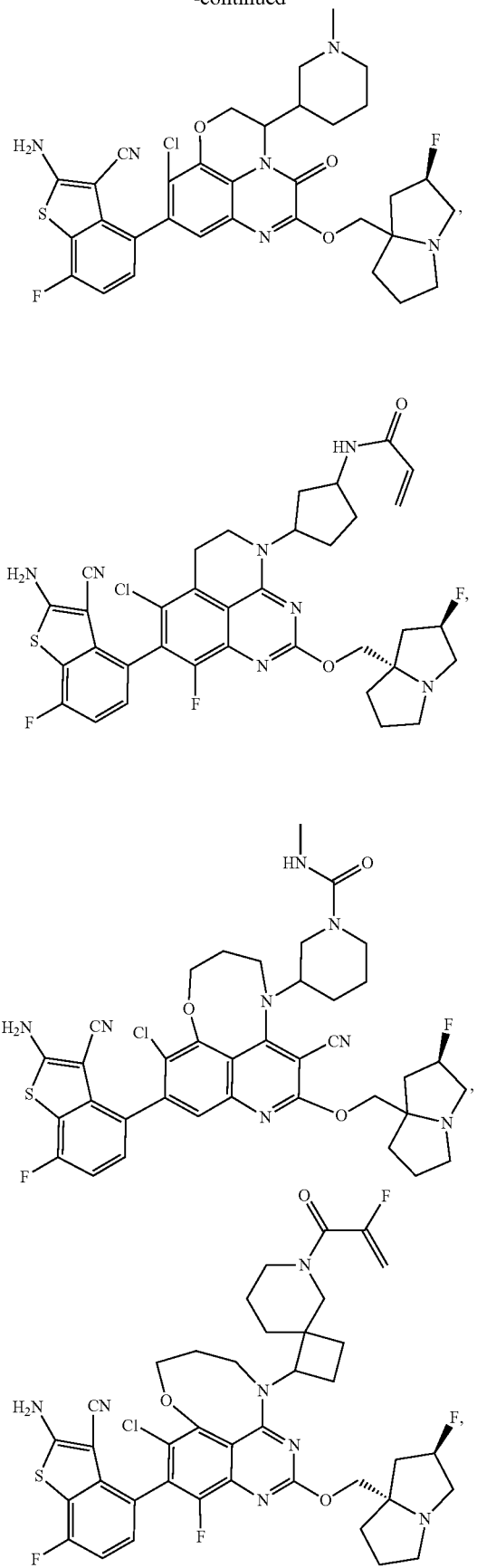

995
-continued
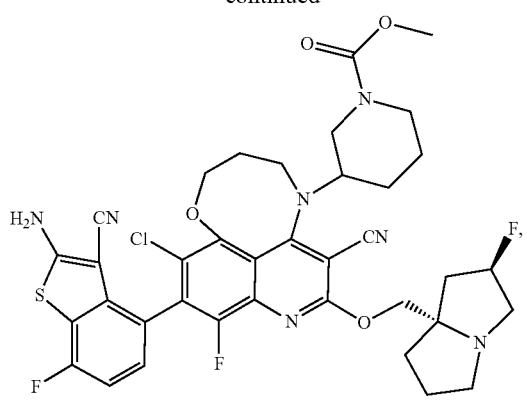
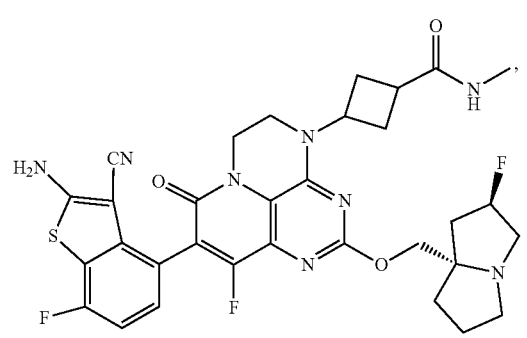
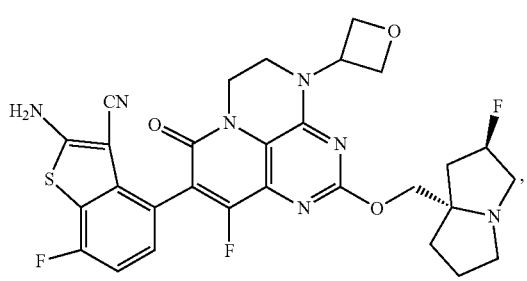
996
-continued
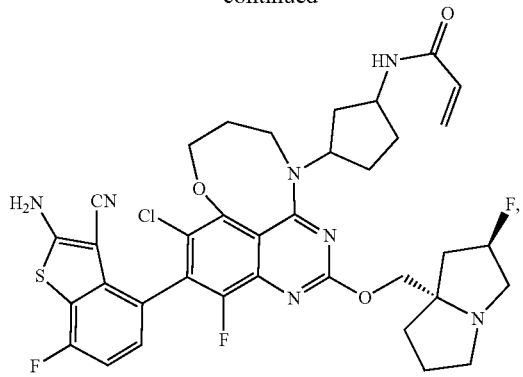
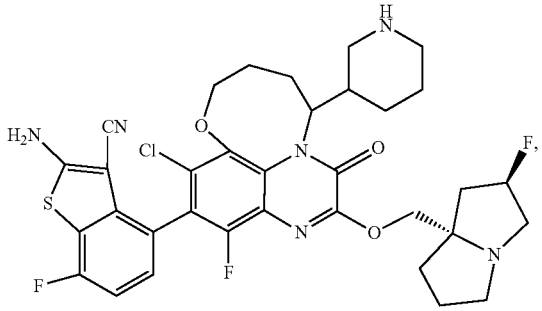
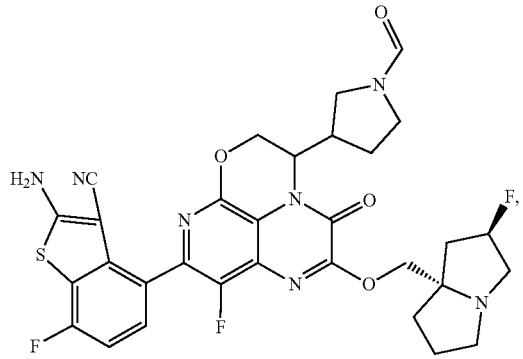
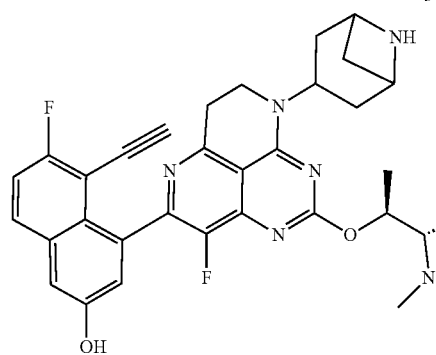
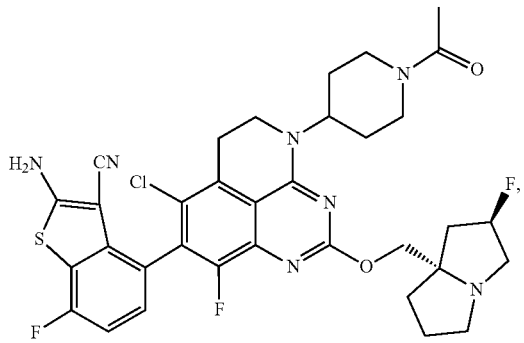

997
-continued
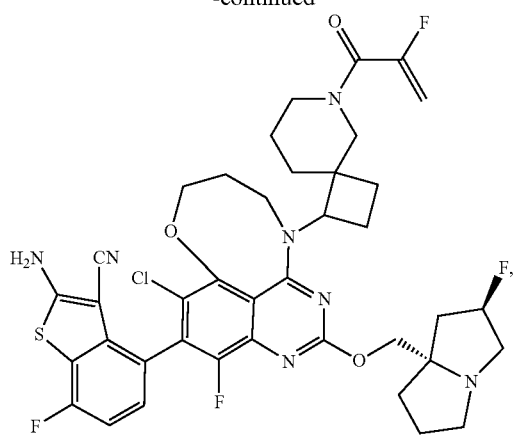
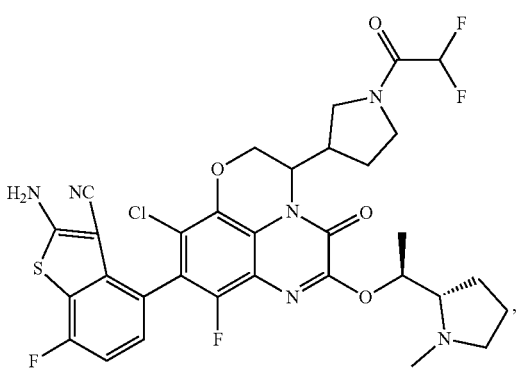
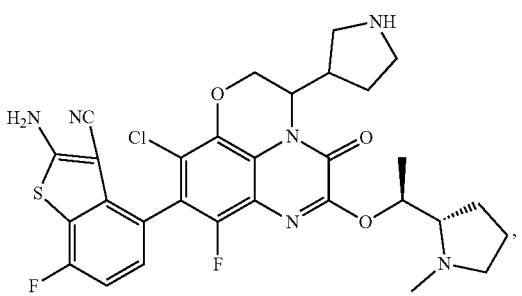
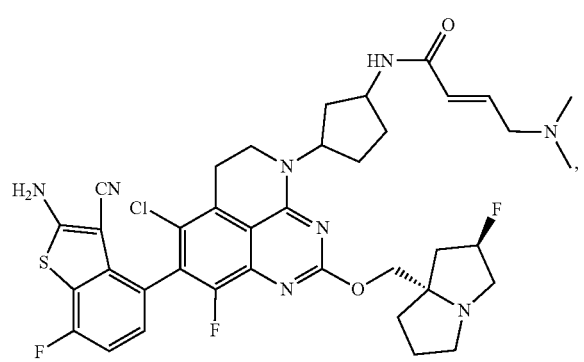
998
-continued
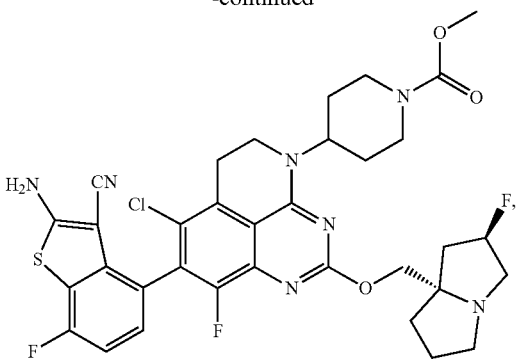
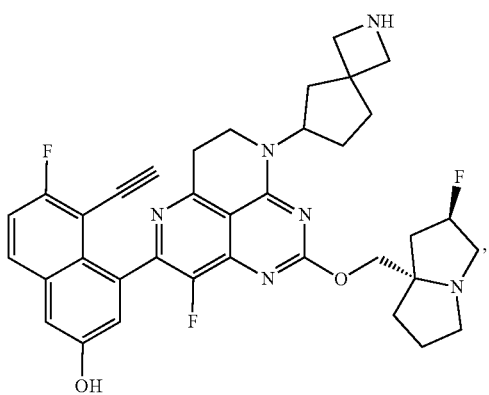
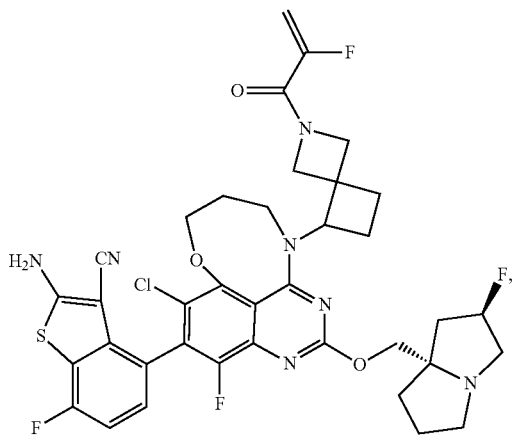
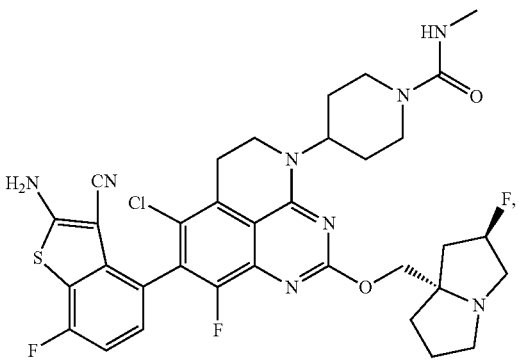

999
-continued
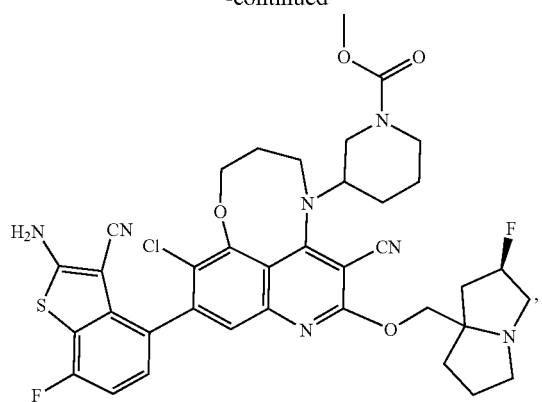
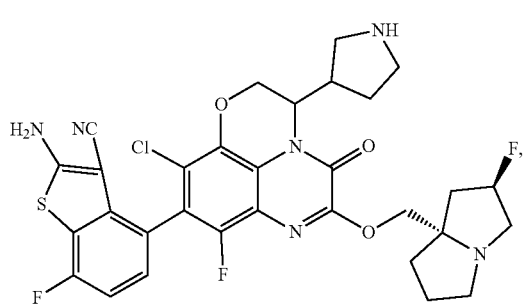
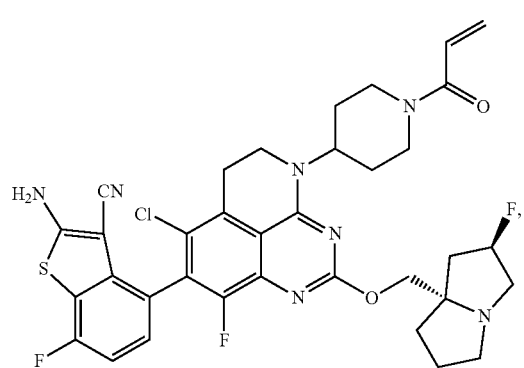
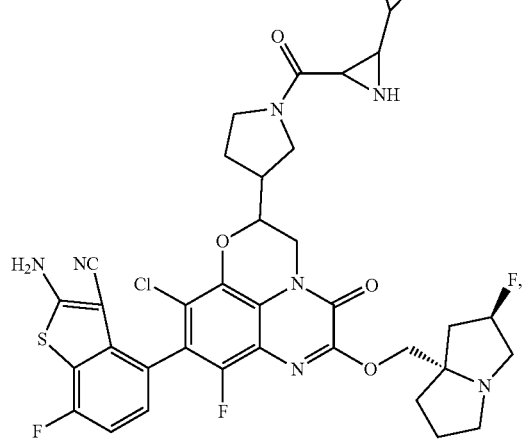
1000
-continued
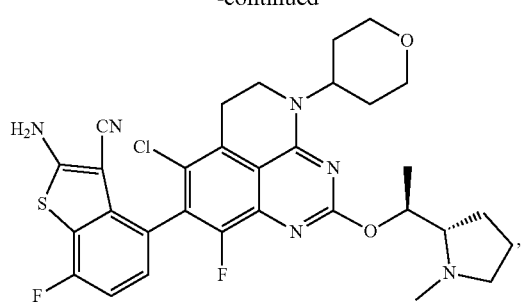
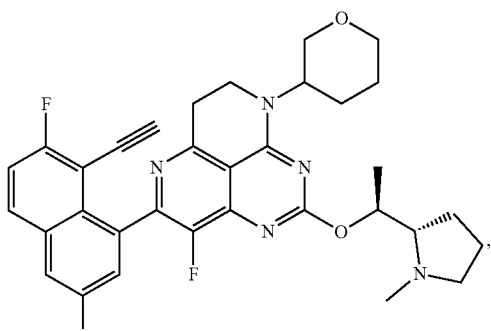
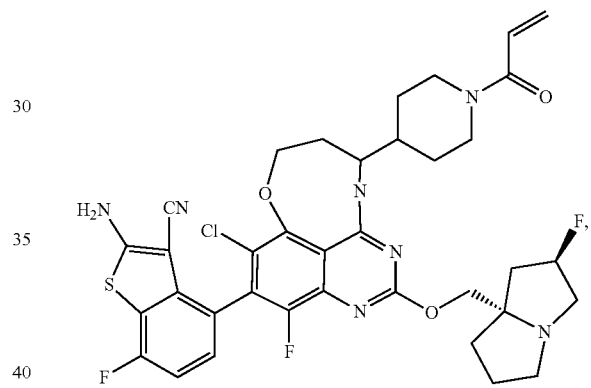
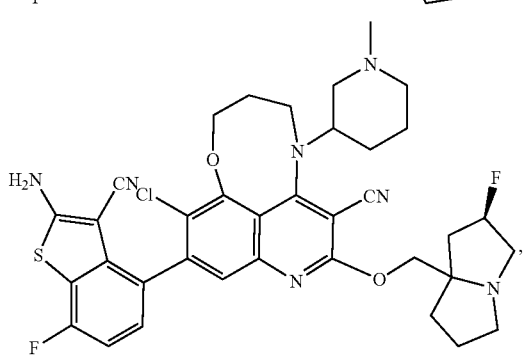
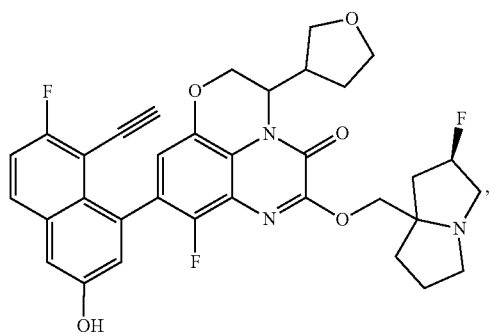

1001
-continued
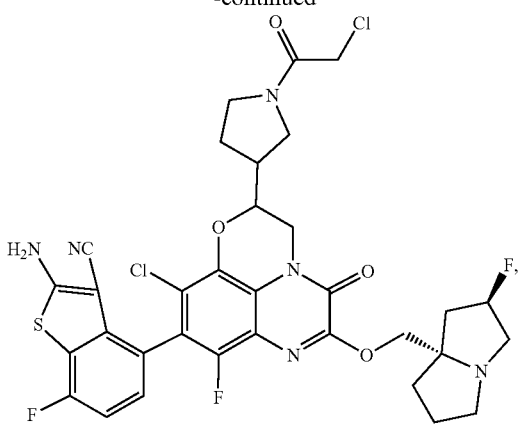
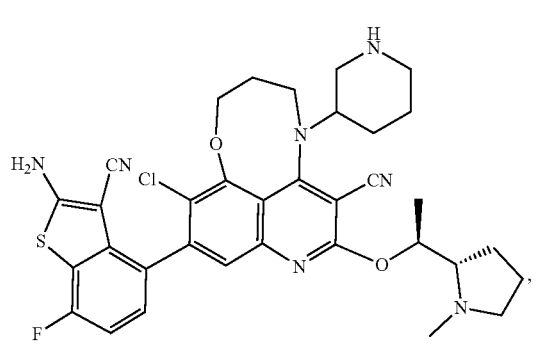
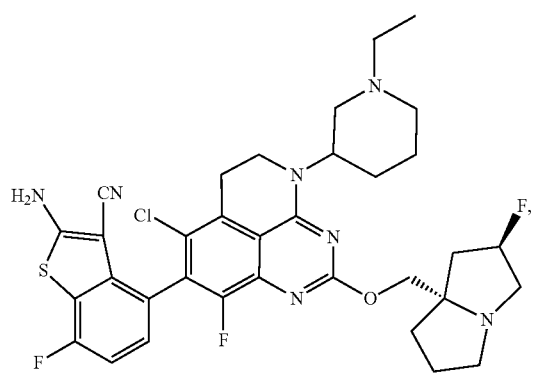
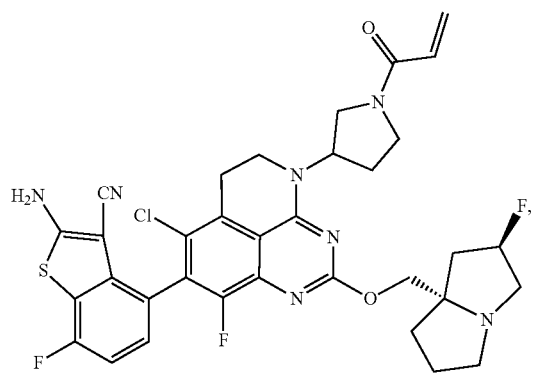
1002
-continued
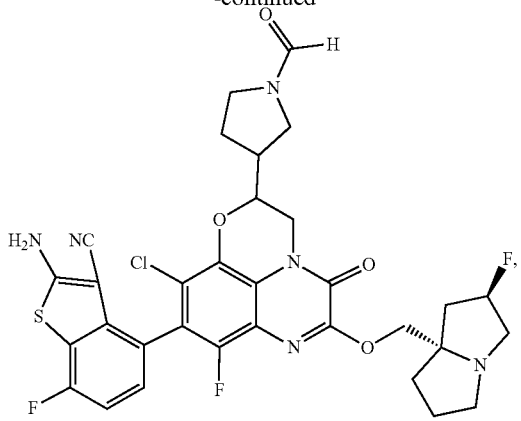
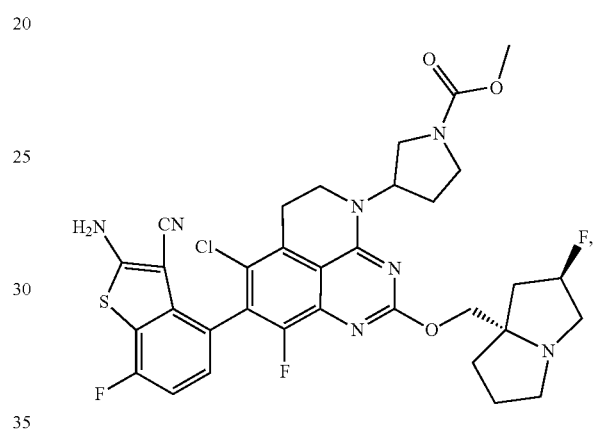
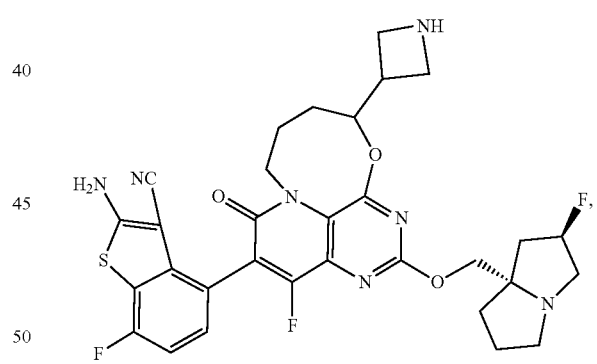
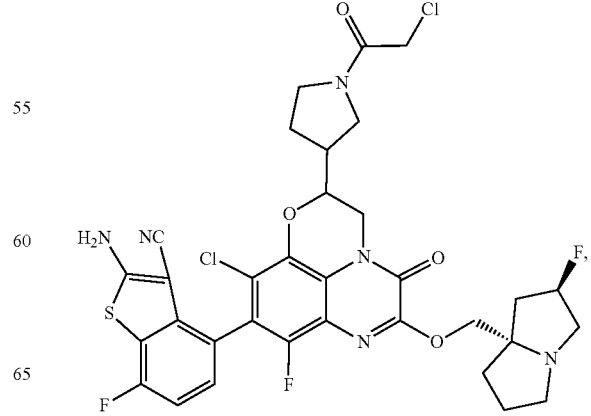

1003
-continued
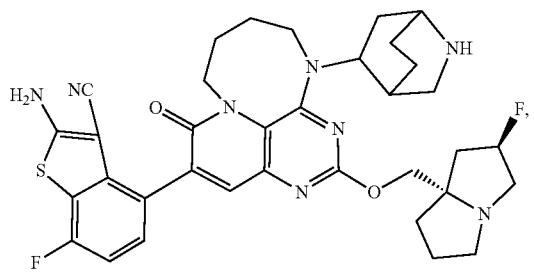
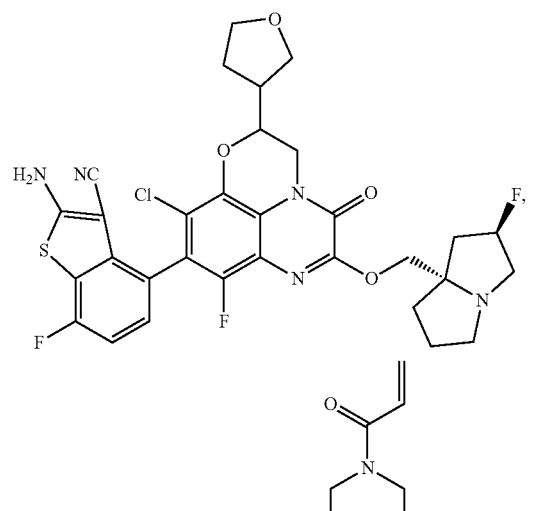
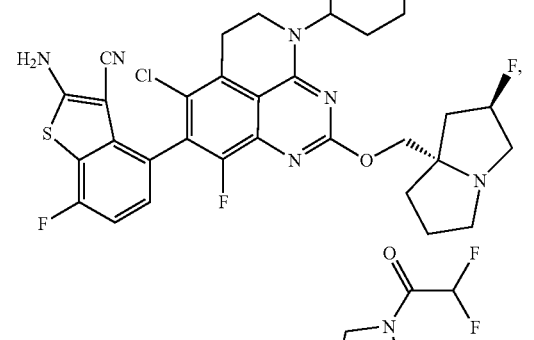
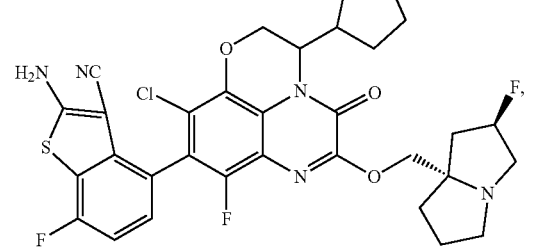
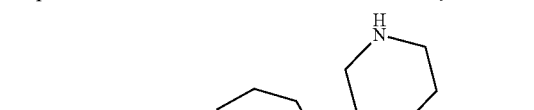
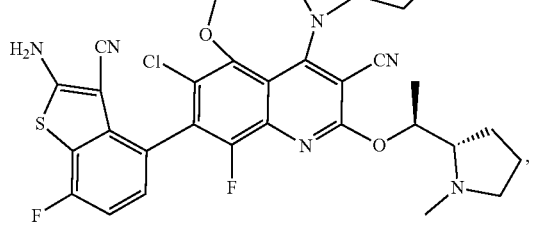
1004
-continued
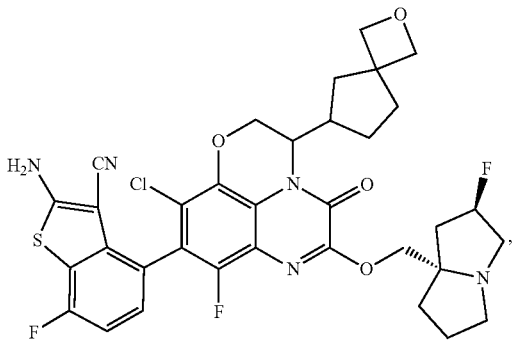
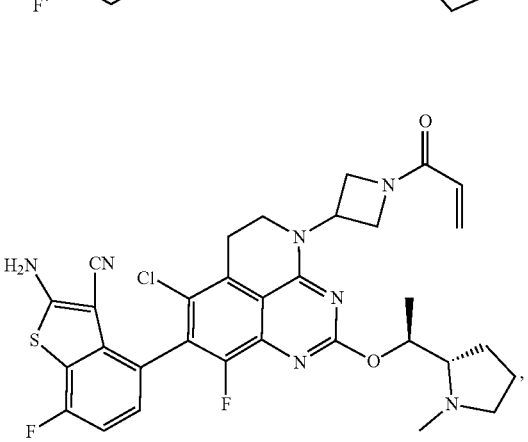
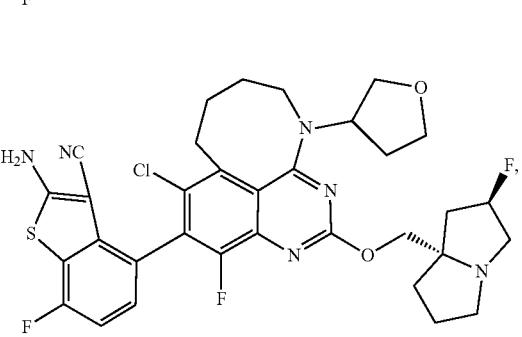
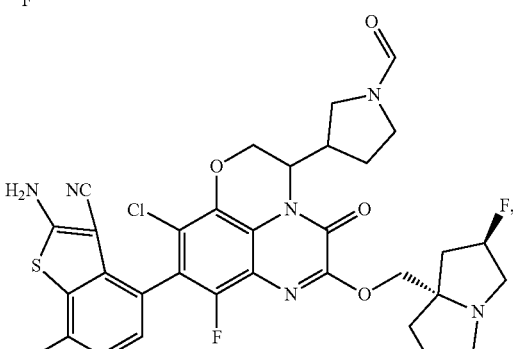
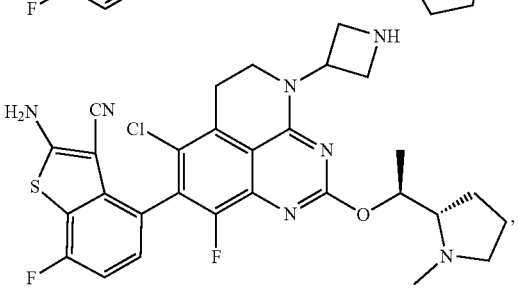

1005
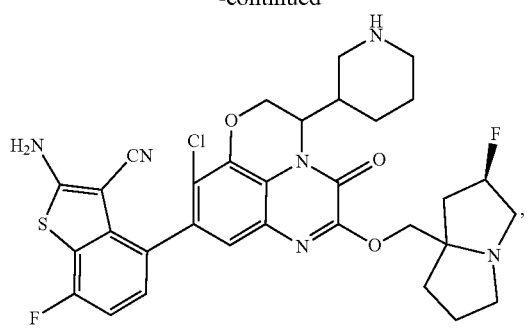
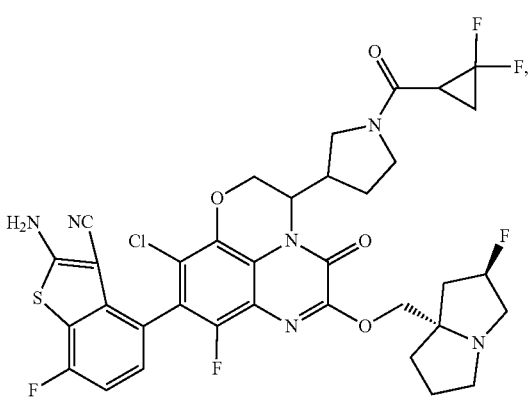
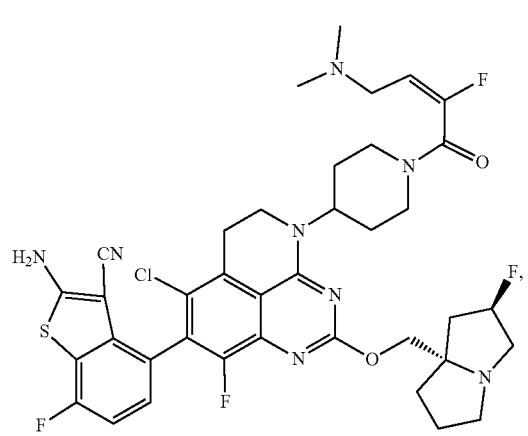
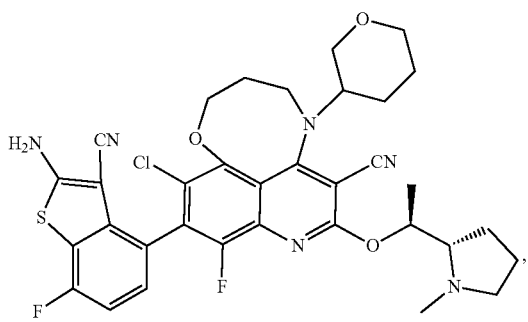
1006
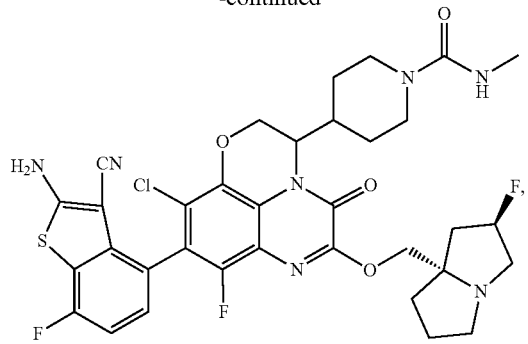
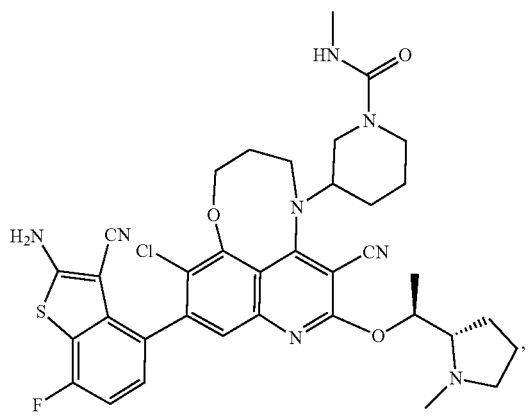
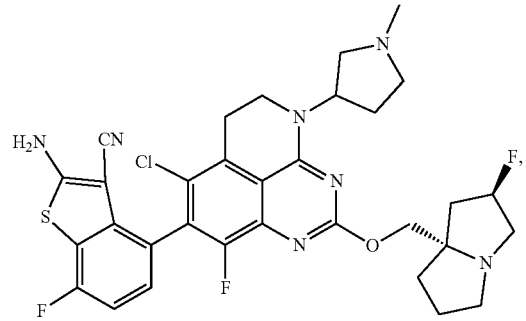
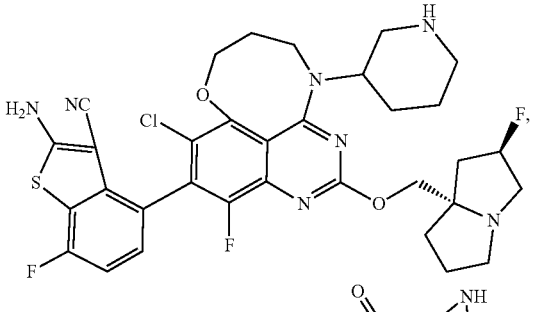
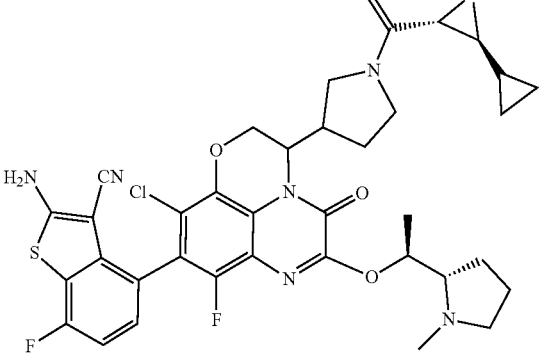

1007
-continued
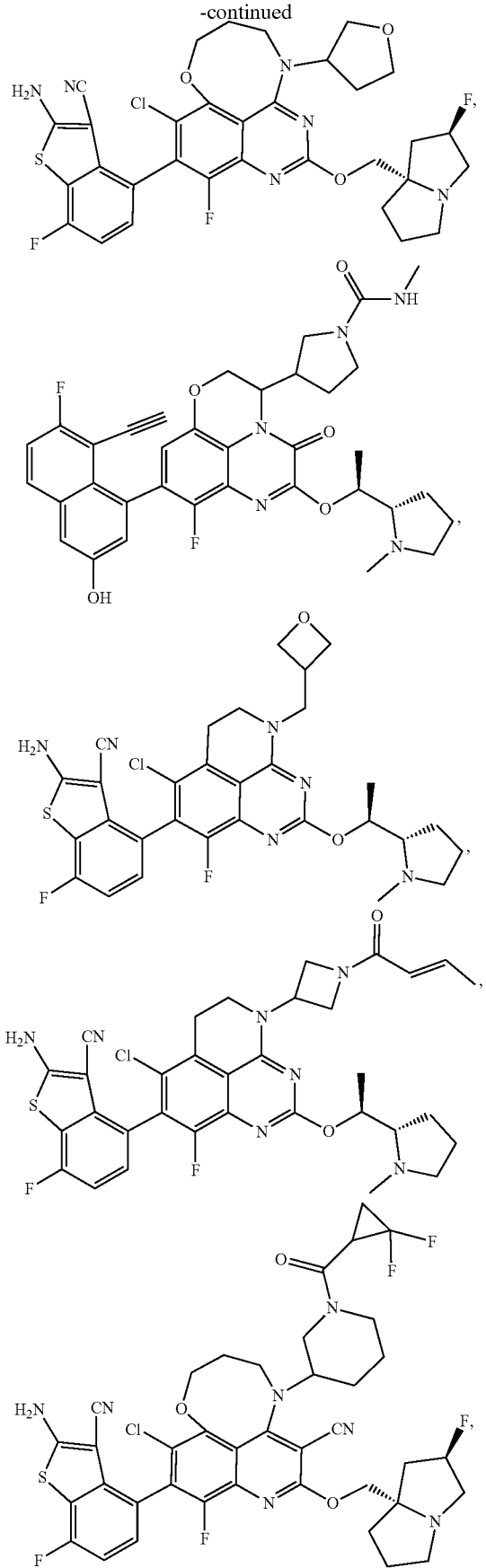
1008
-continued
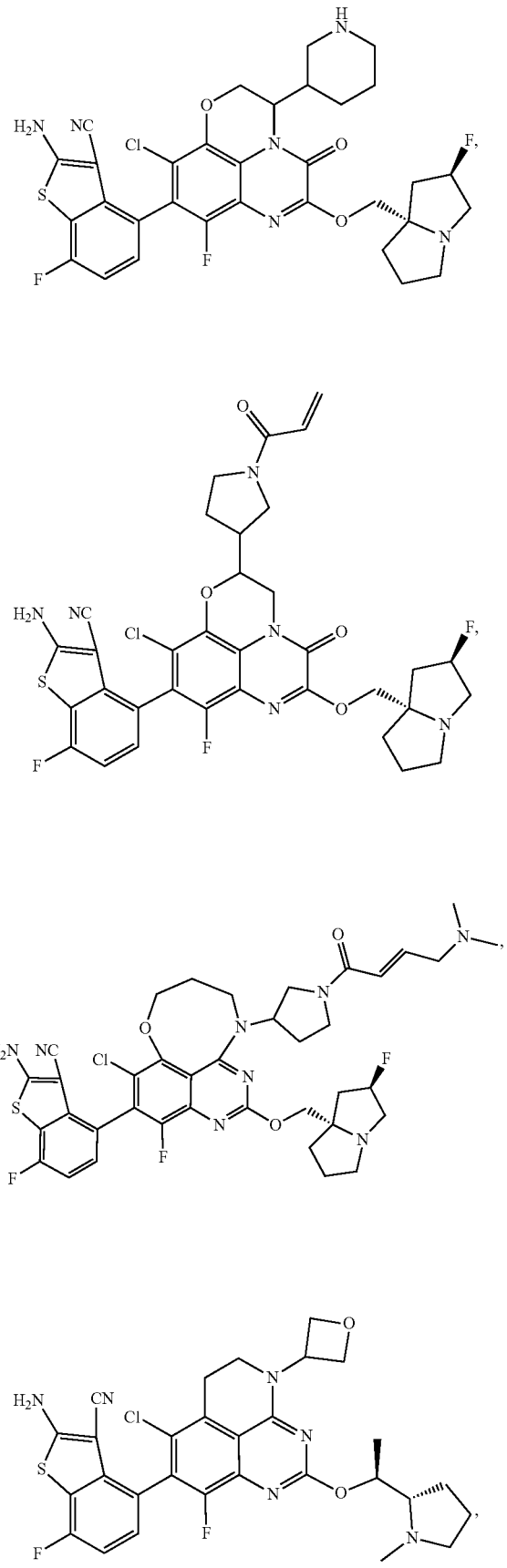

1009
-continued
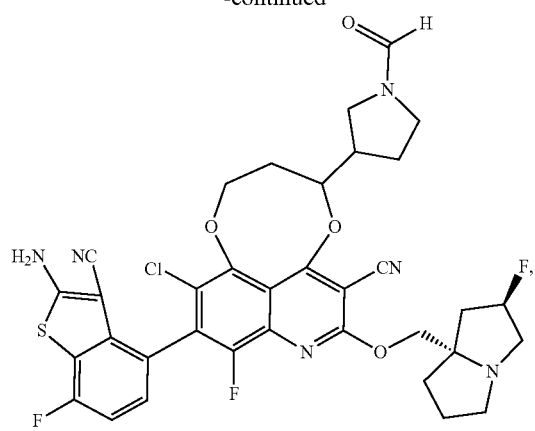
1010
-continued
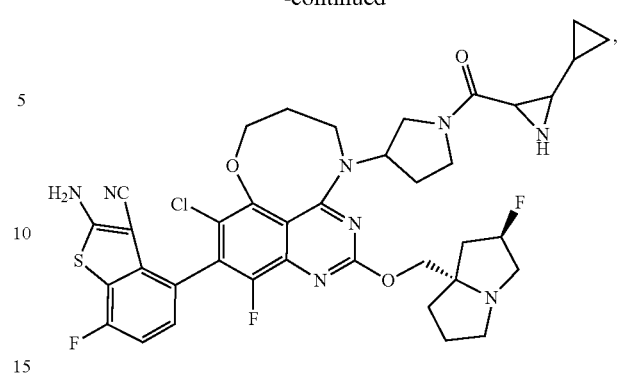
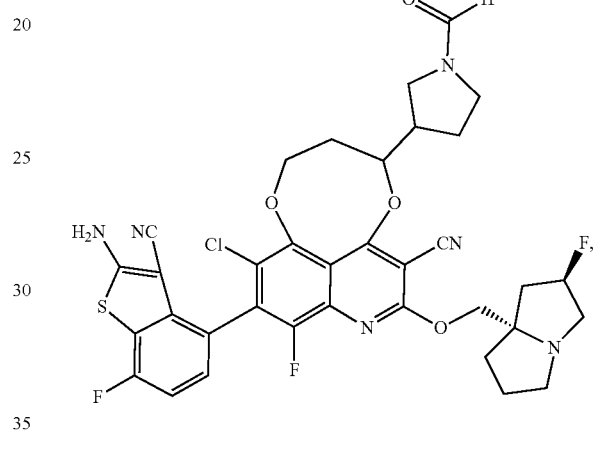
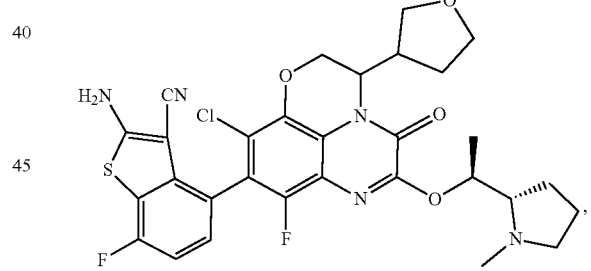
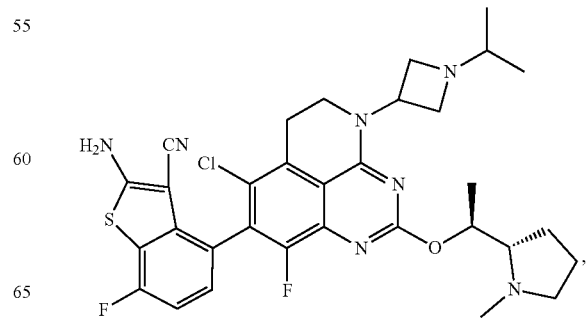

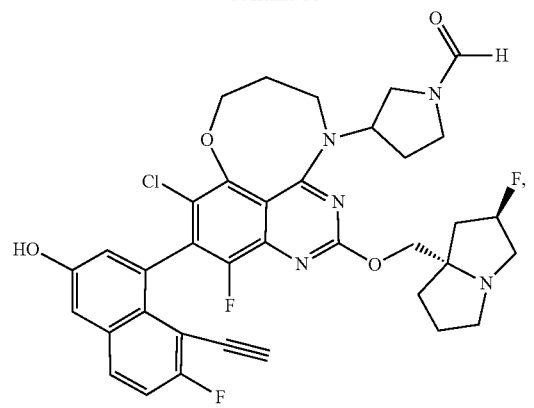
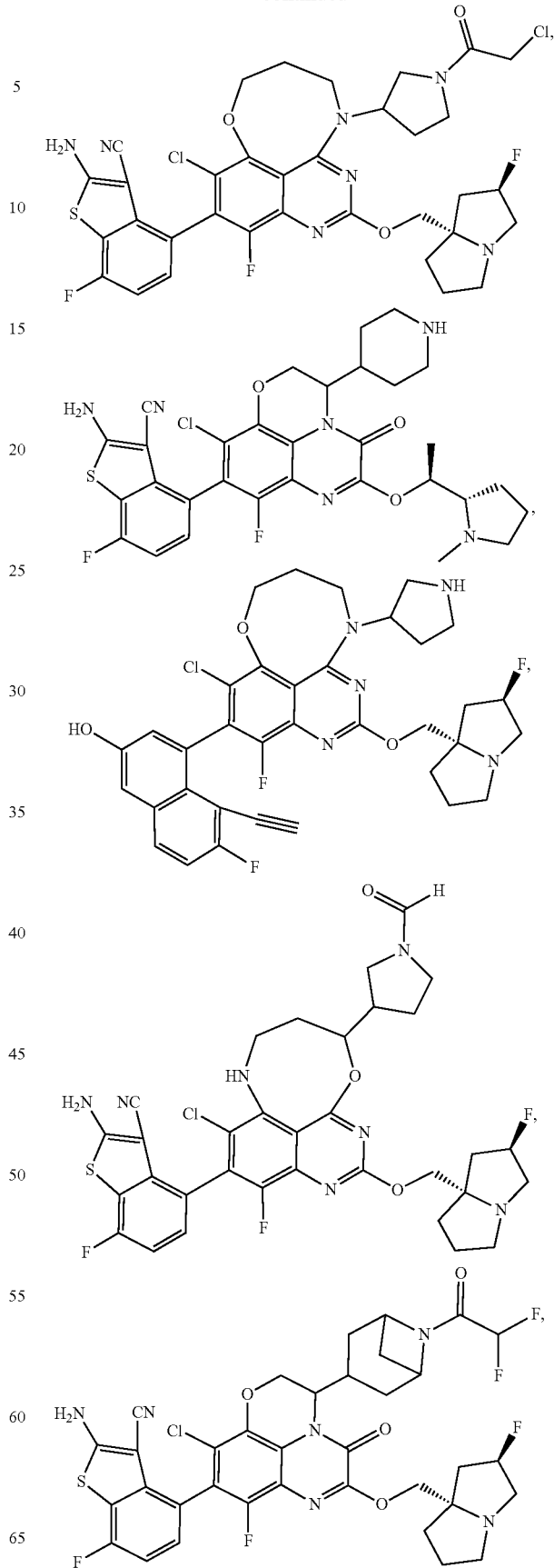

1013
-continued
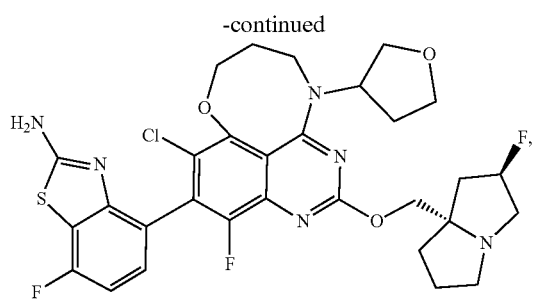
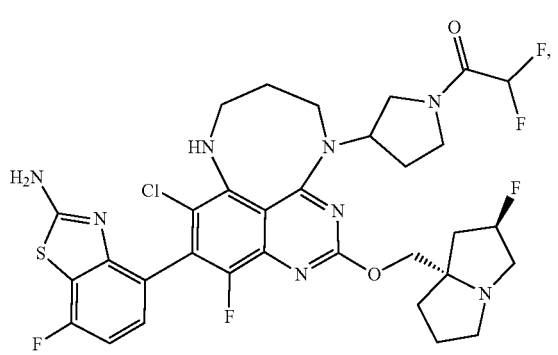
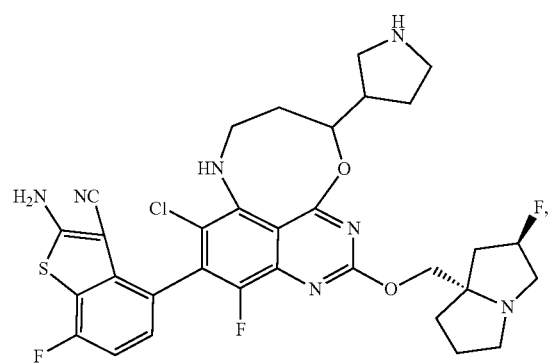
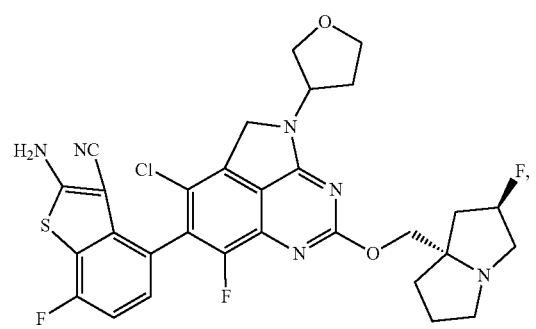
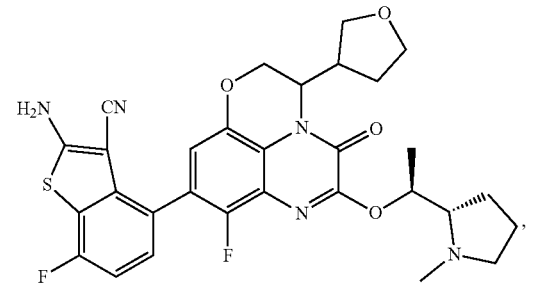
1014
-continued
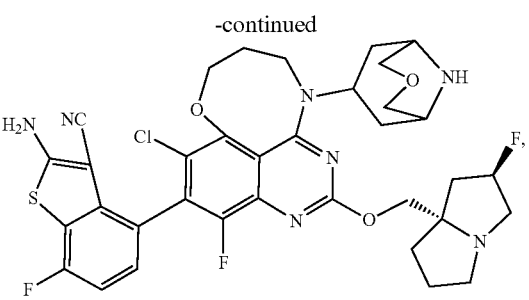
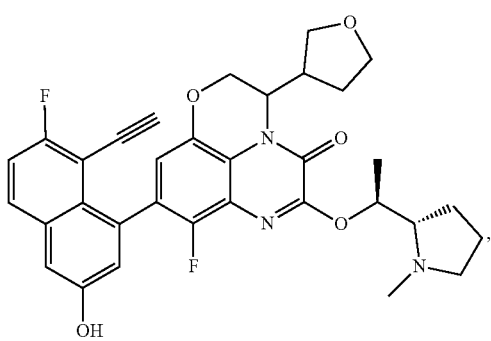
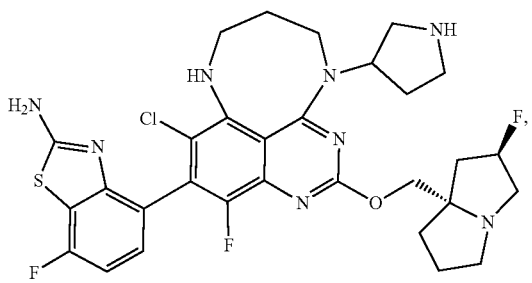
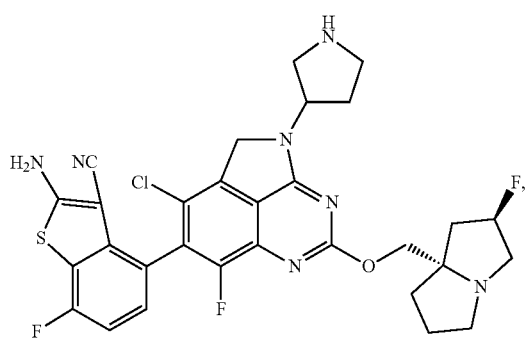
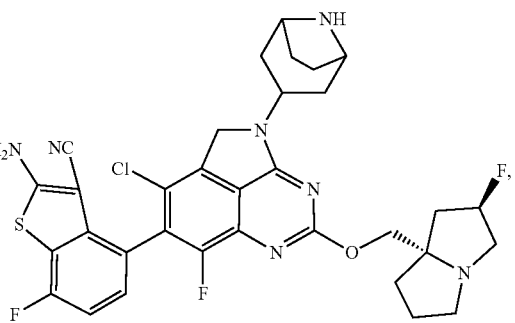

1015
-continued
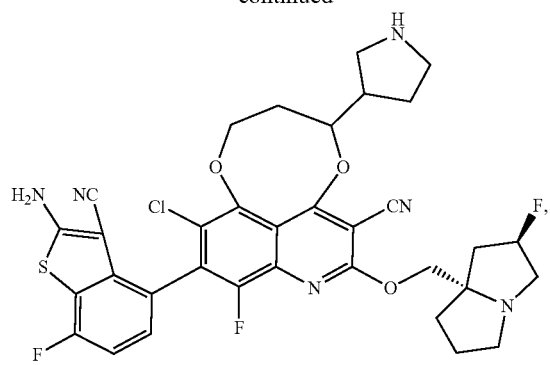
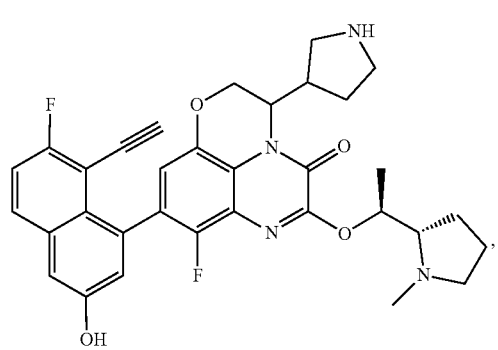
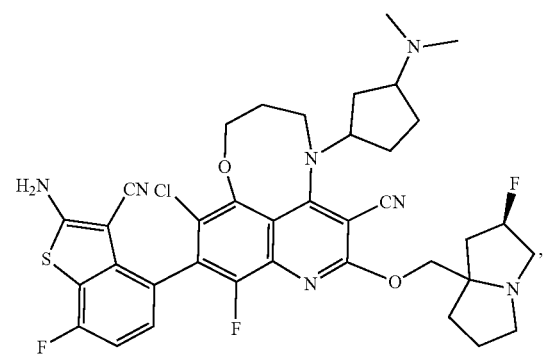
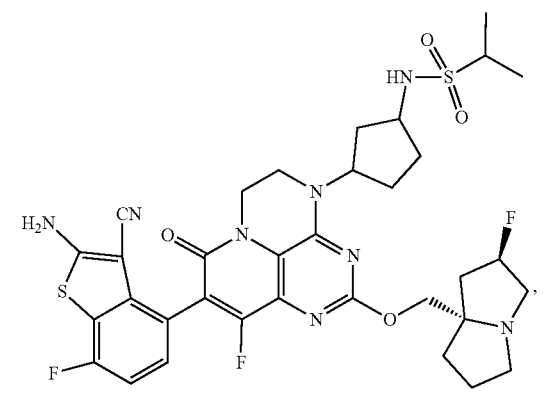
1016
-continued
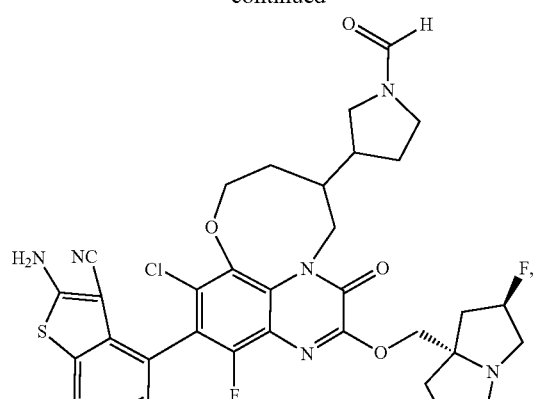
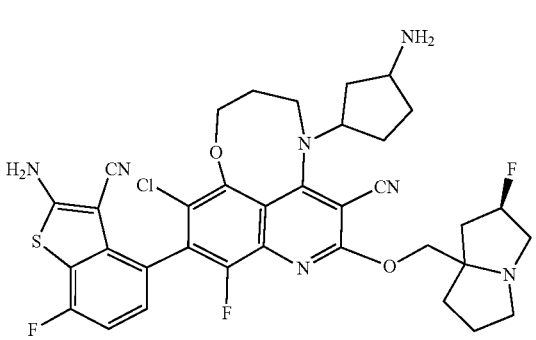
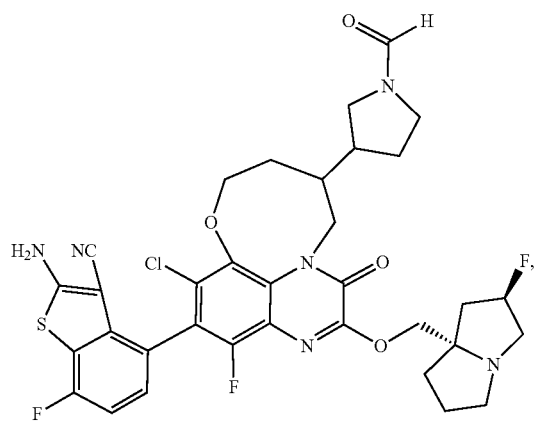
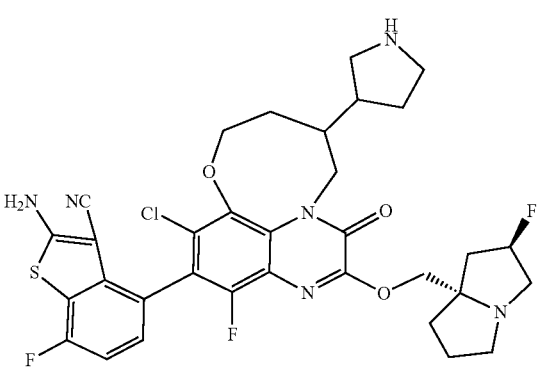

1017
-continued
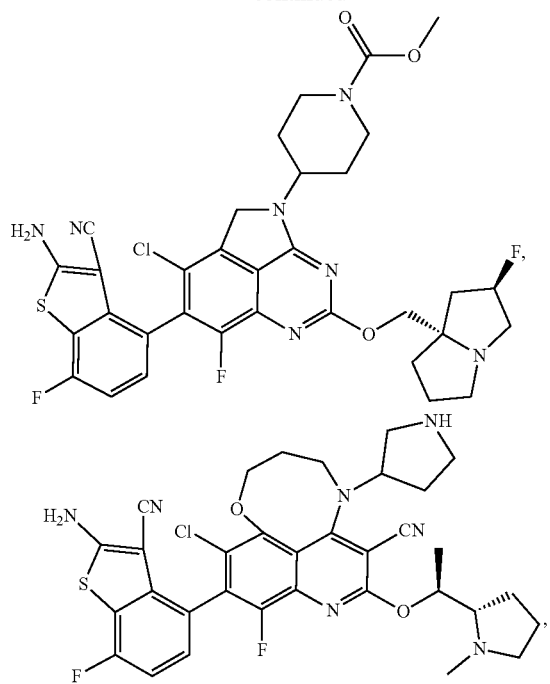
or a pharmaceutically acceptable salt or solvate thereof.
In an aspect is provided a compound selected from:
1018
-continued
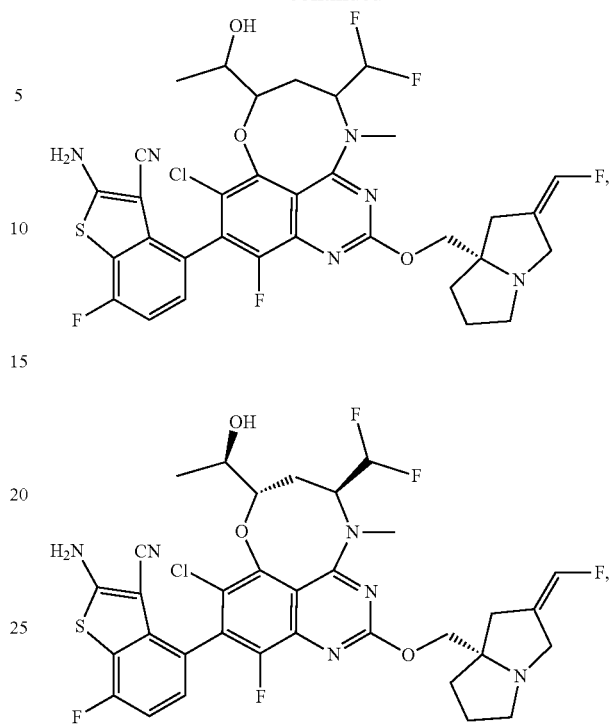
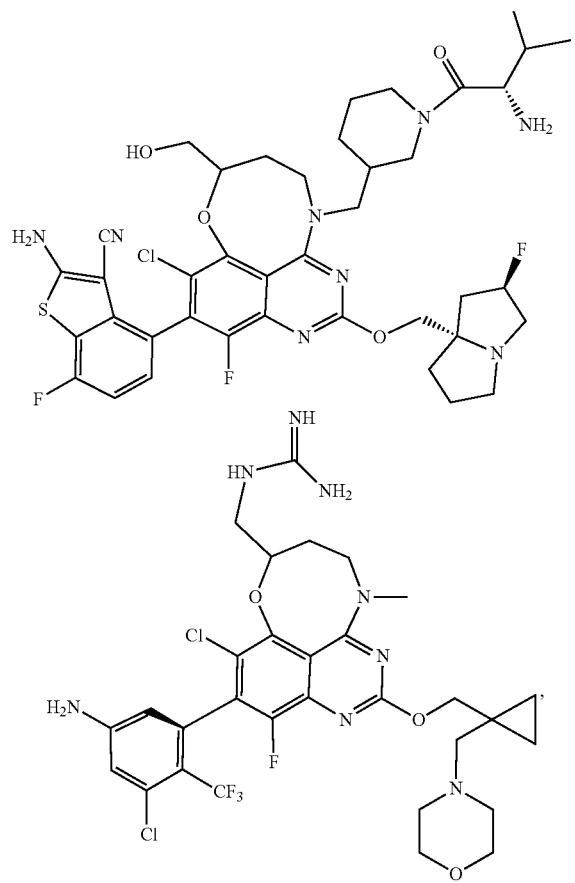
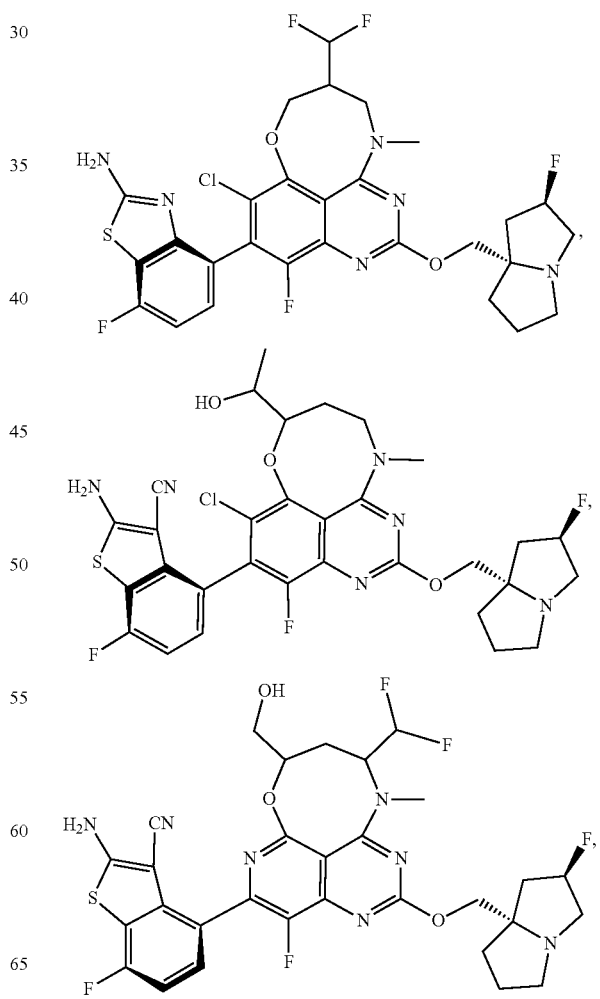

1019
-continued
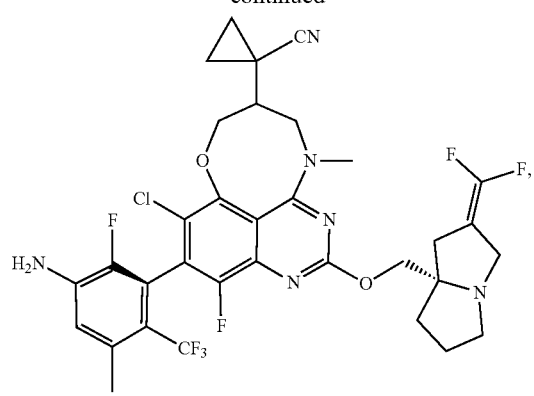
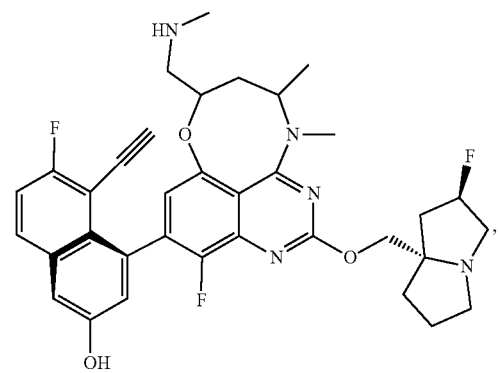
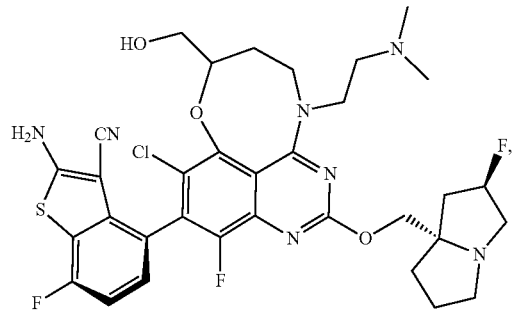
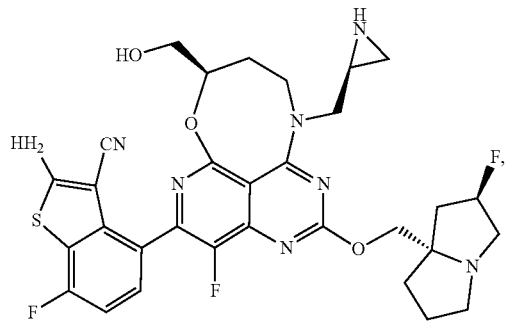
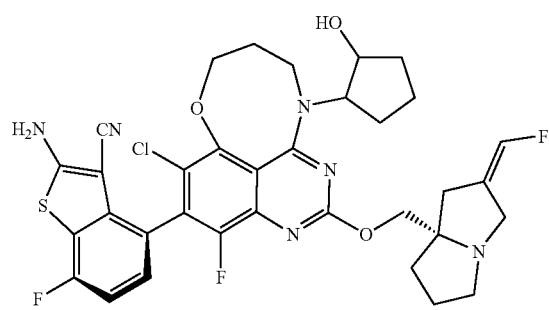
1020
-continued
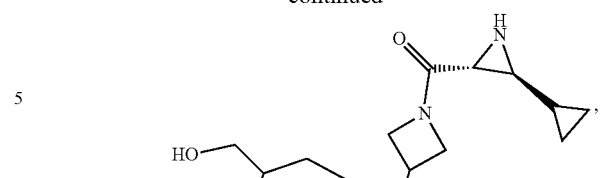
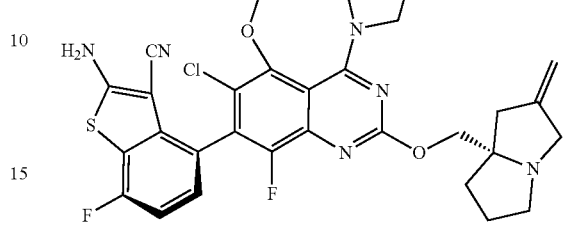
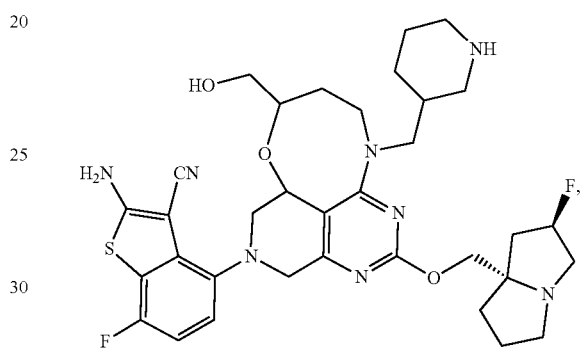
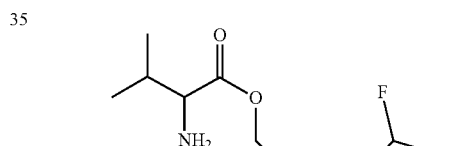
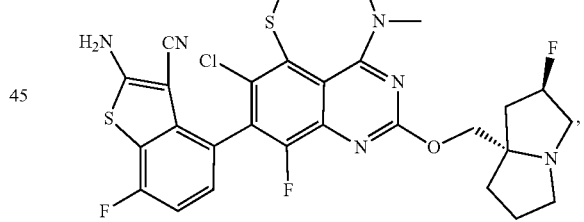
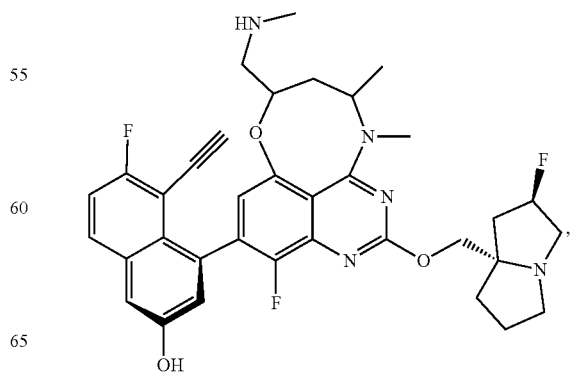

1021
-continued
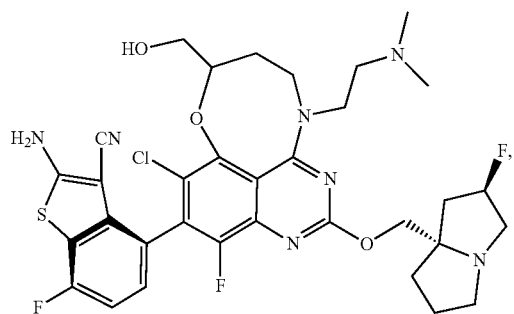
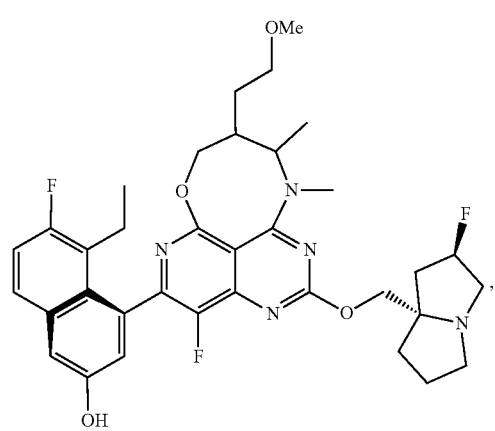
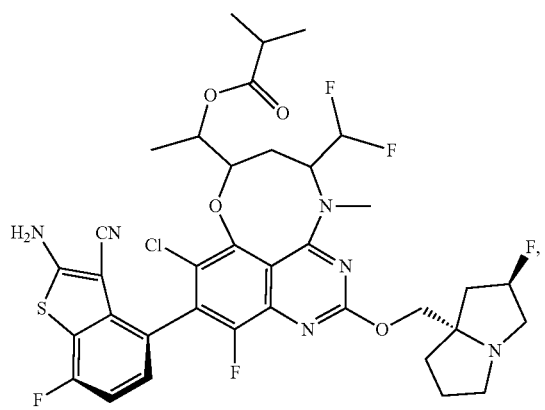
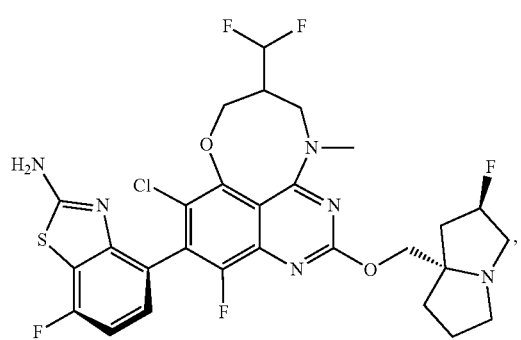
1022
-continued
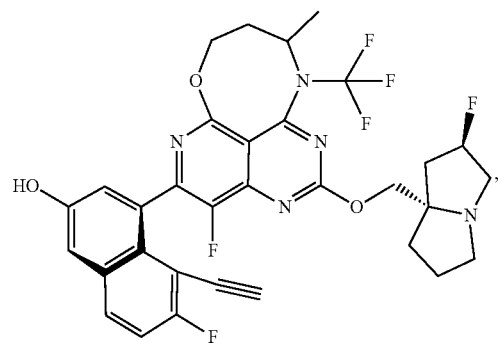
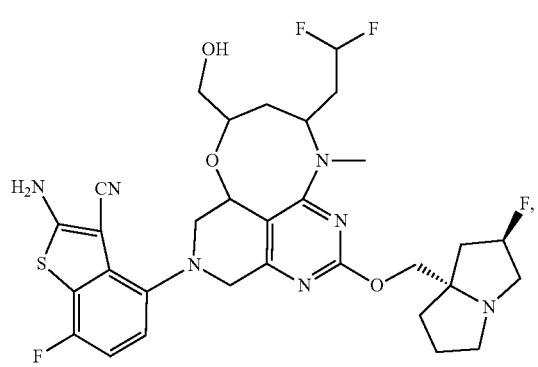
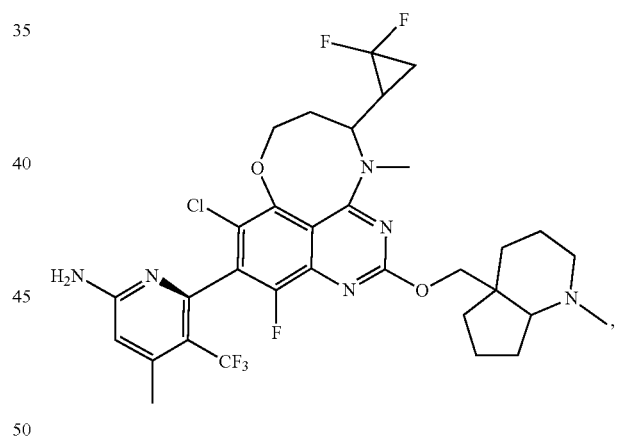
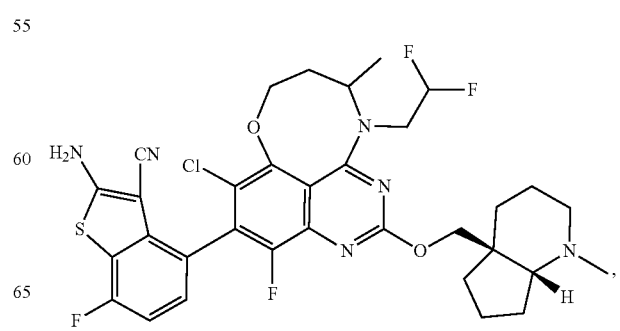

1023
-continued
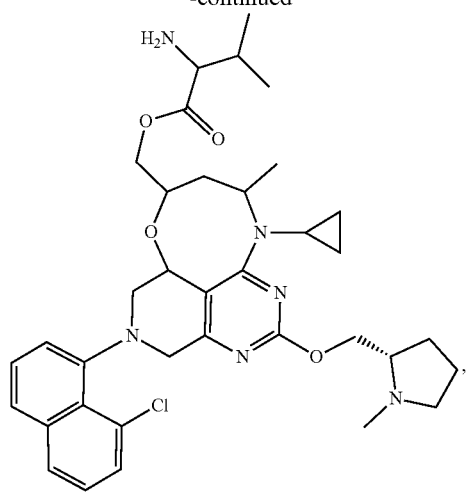
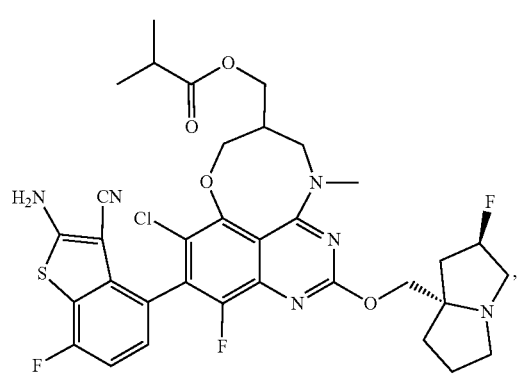
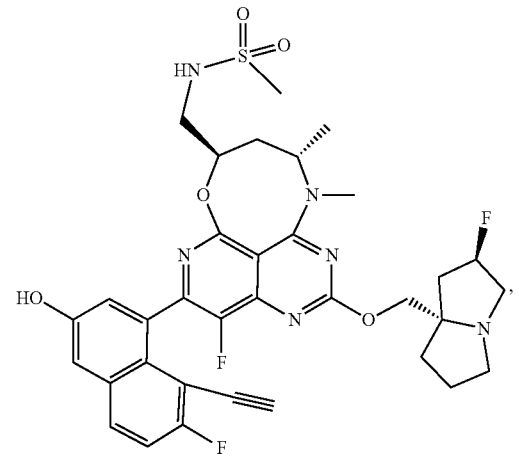
1024
-continued
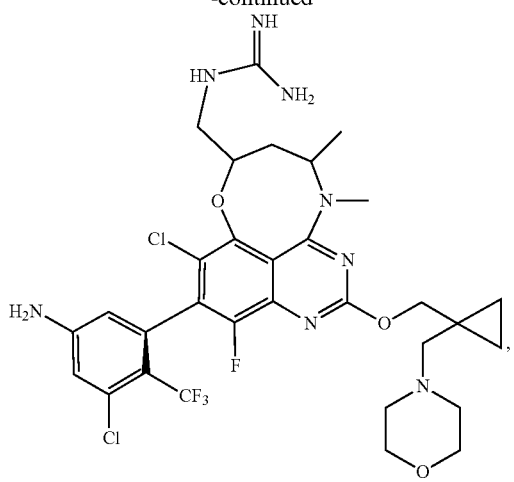
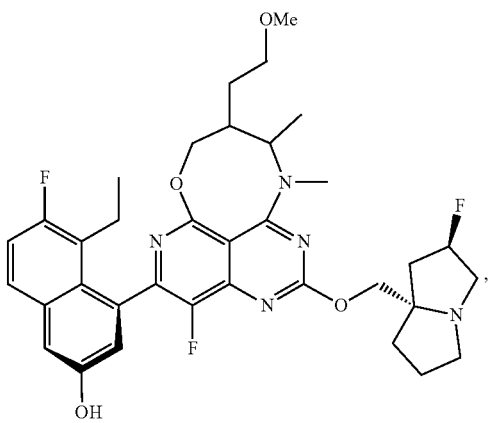
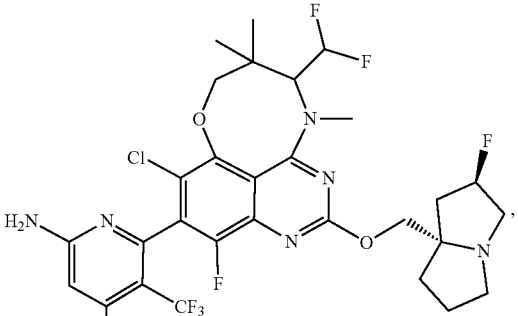
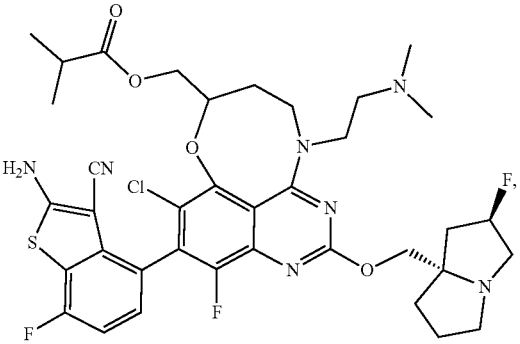

1025
-continued
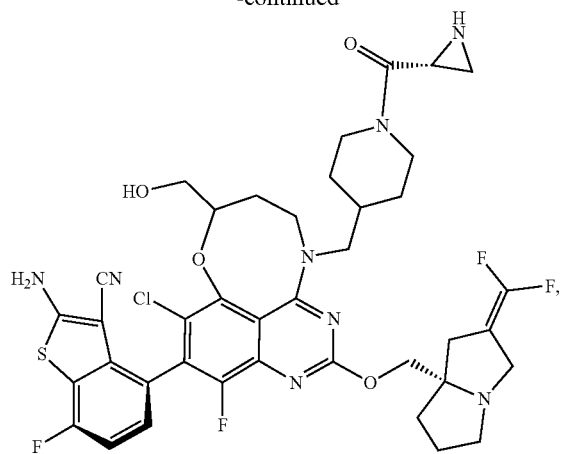
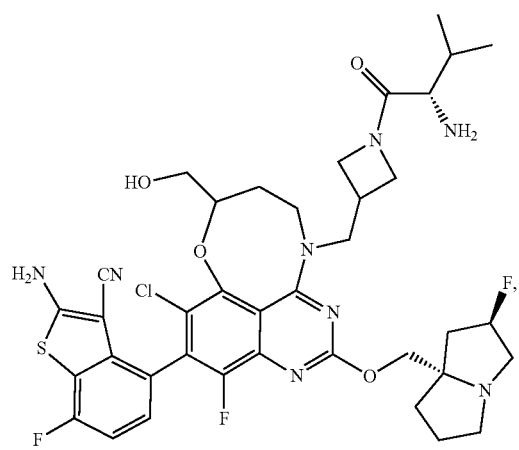
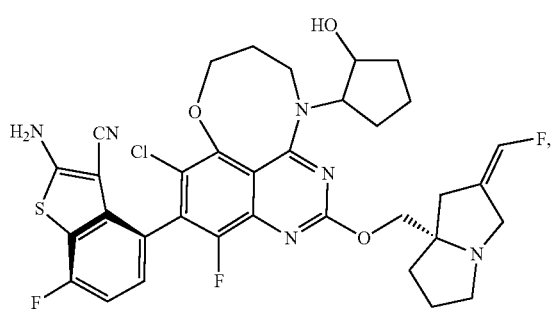
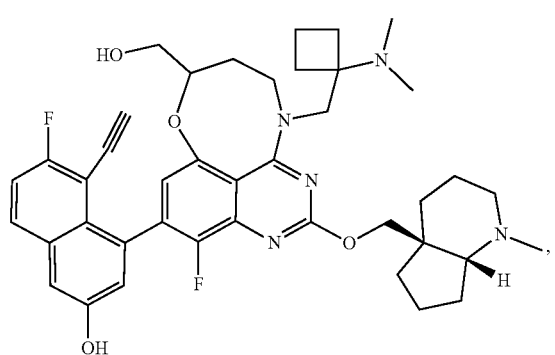
1026
-continued
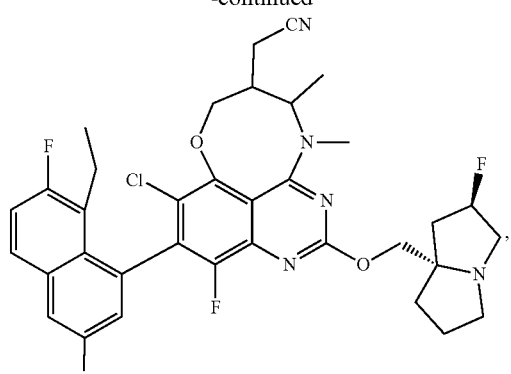
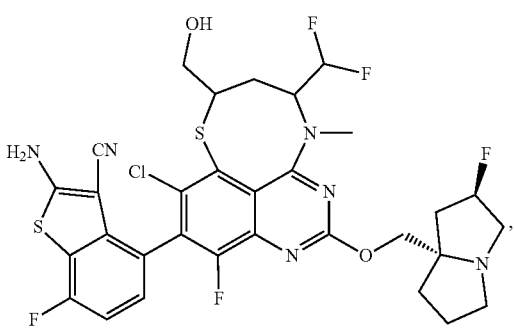
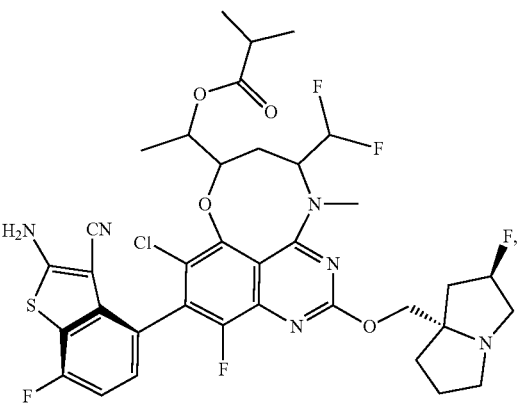
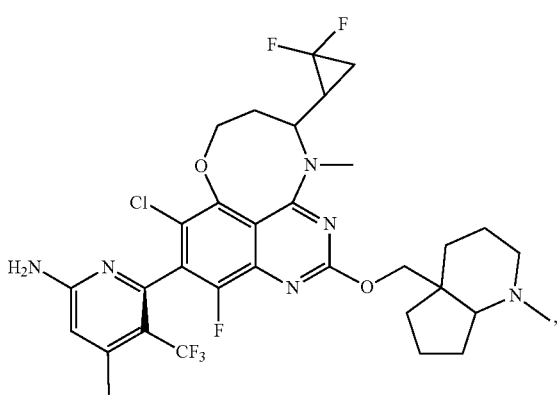

1027
-continued
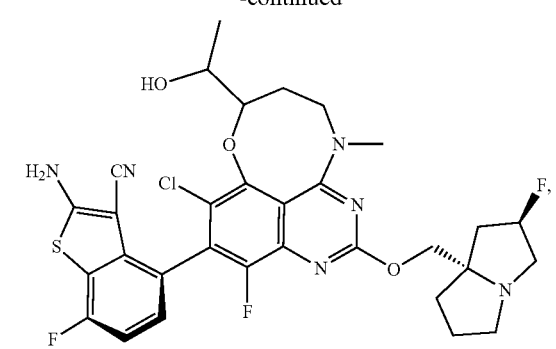
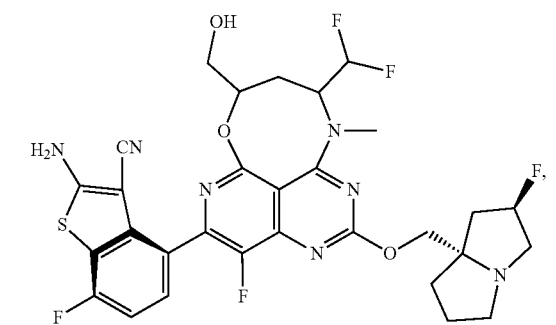
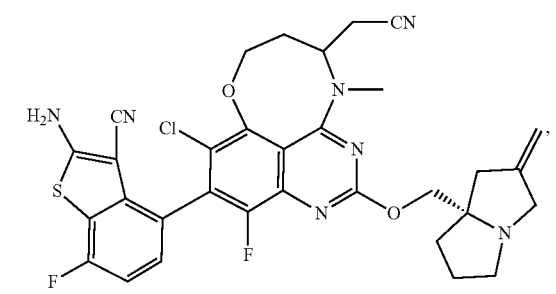
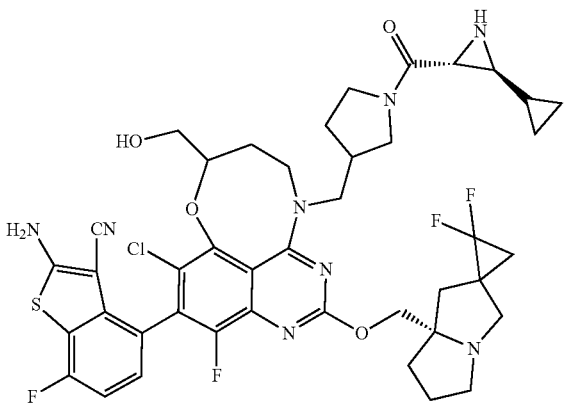
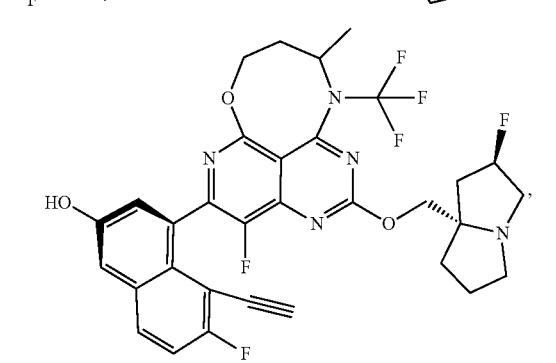
1028
-continued
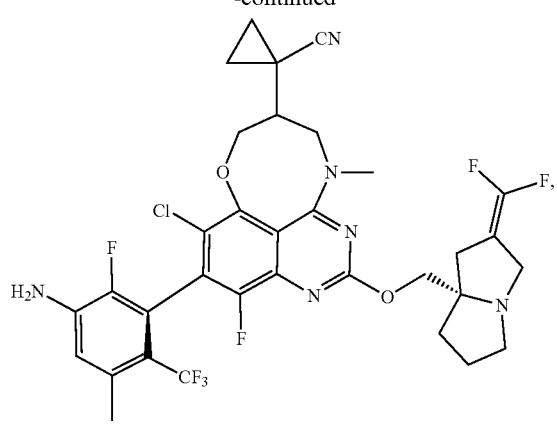
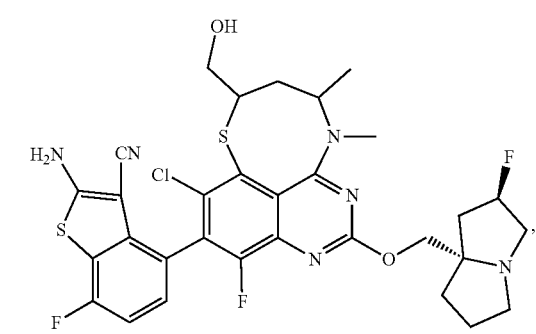
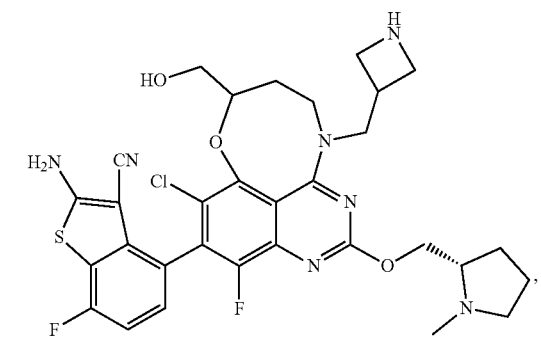
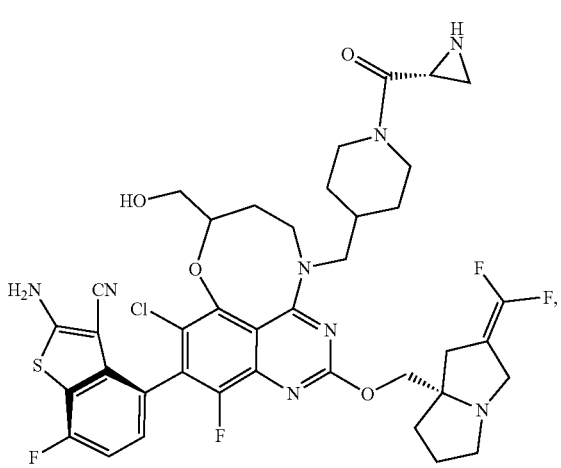

1029
-continued
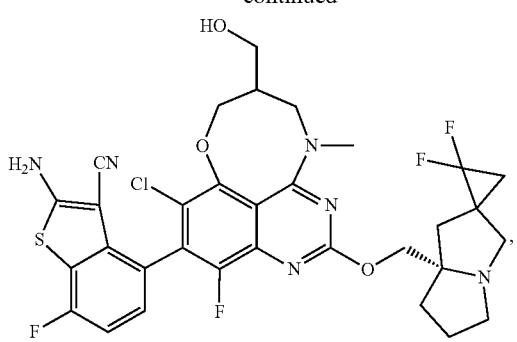
and
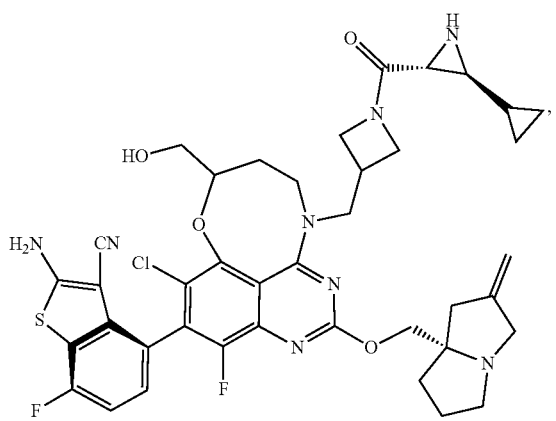
or a pharmaceutically acceptable salt or solvate thereof. In an aspect is provided a compound selected from:
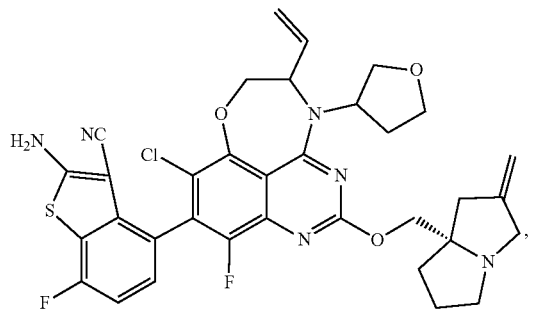
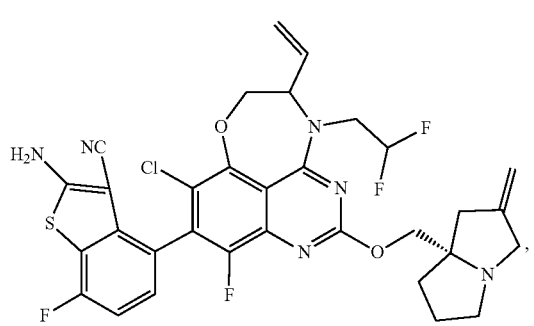
1030
-continued
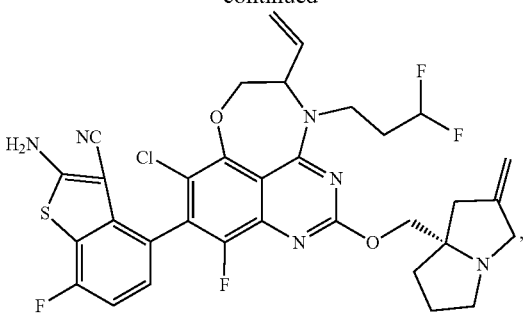
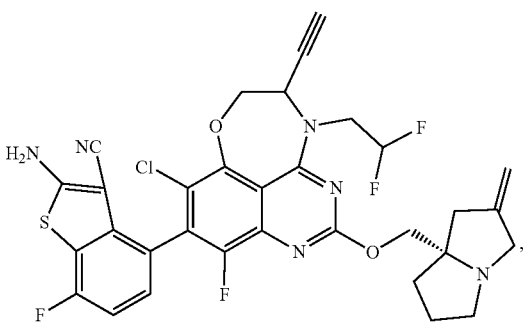
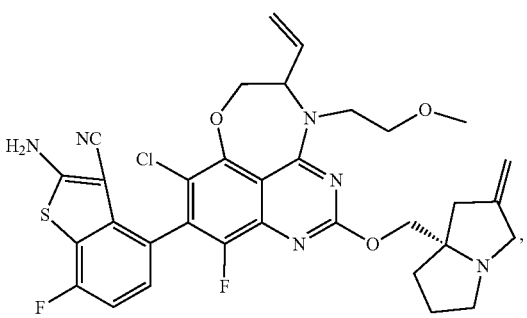
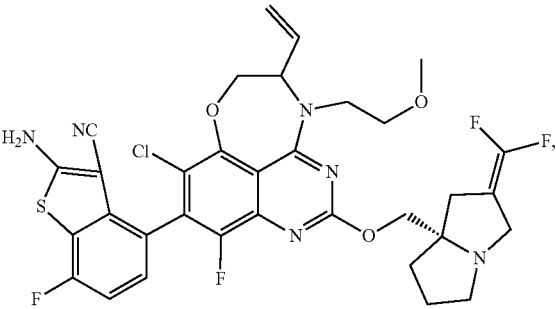

1031
-continued
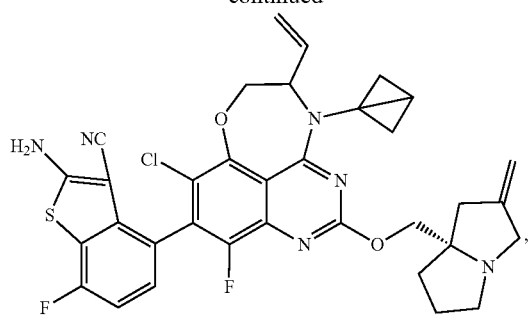
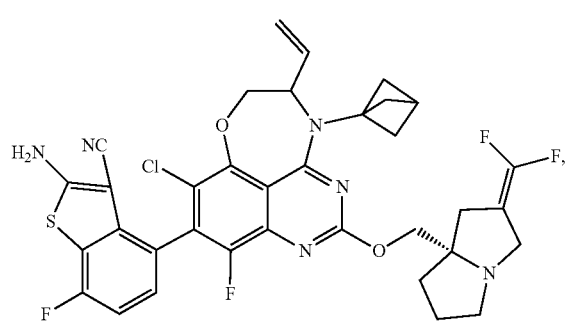
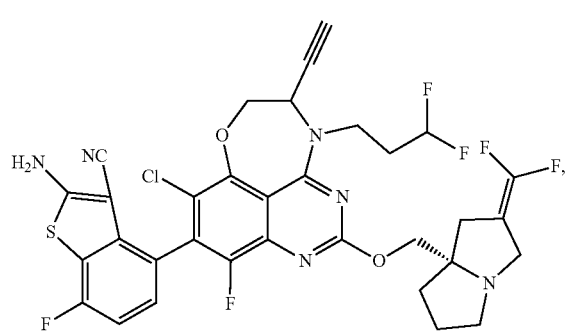
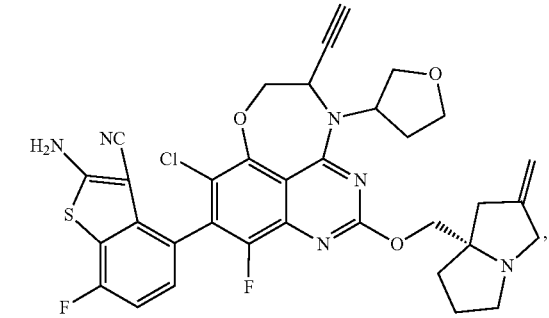
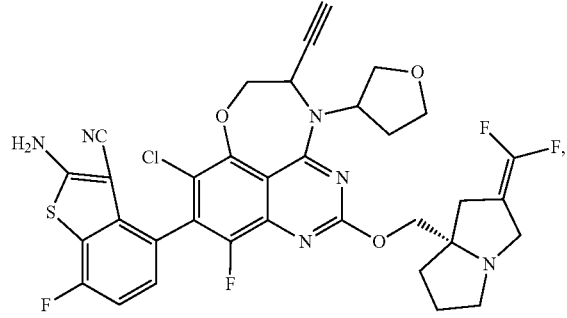
1032
-continued
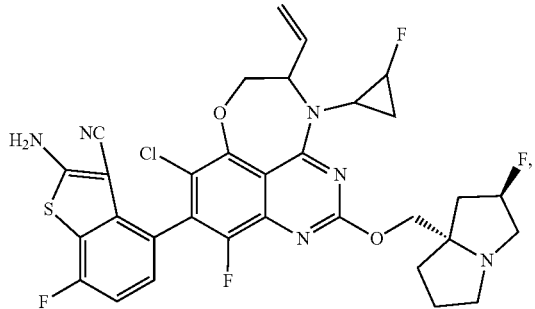
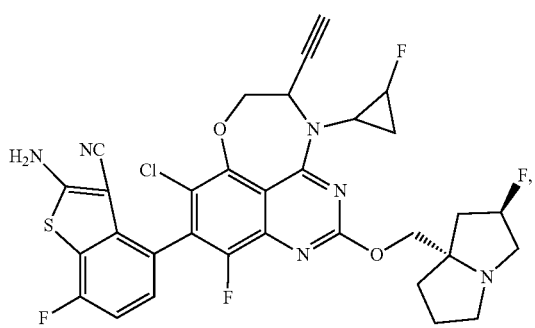
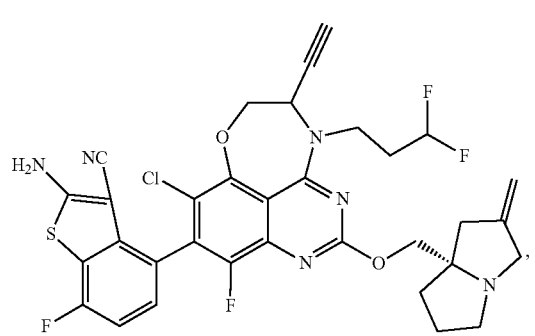
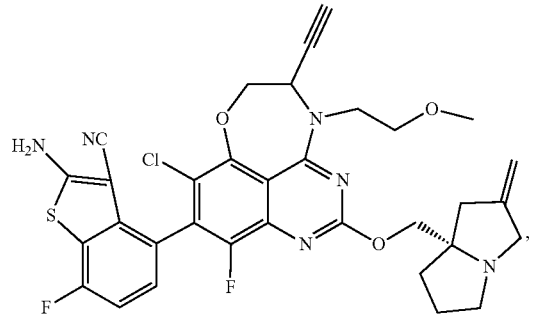
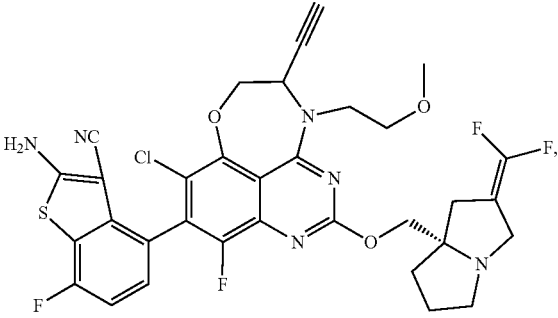

1033
-continued
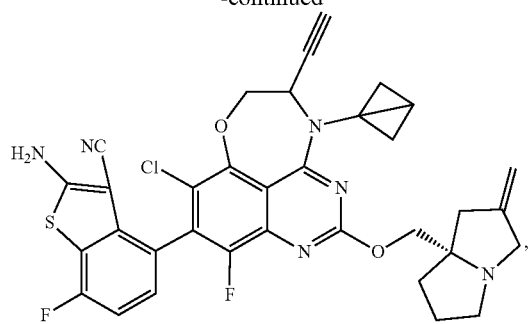
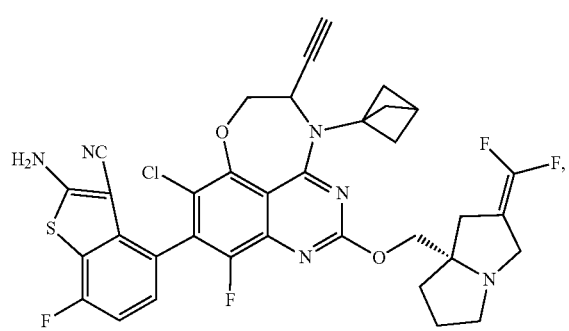
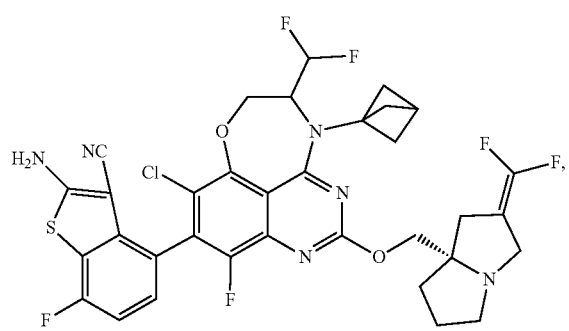
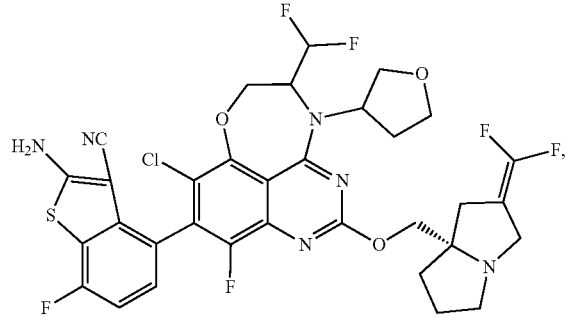
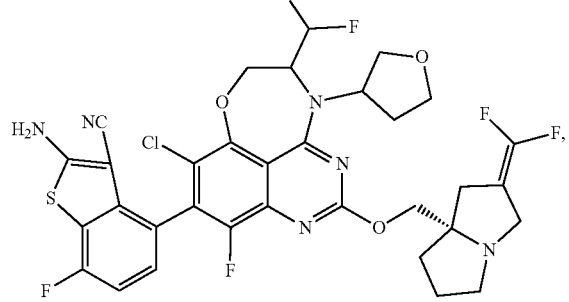
1034
-continued
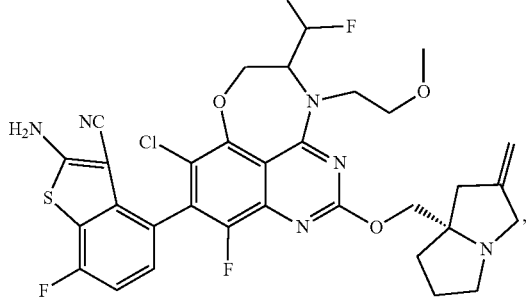
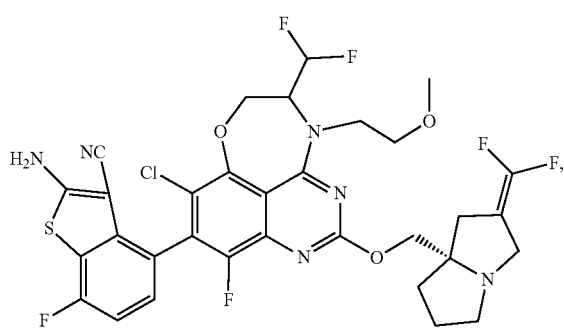
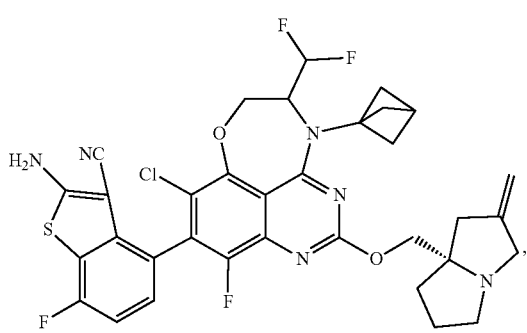
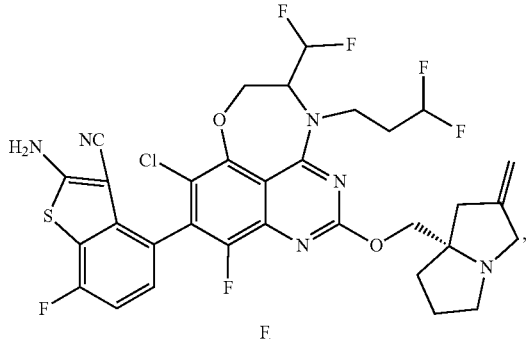
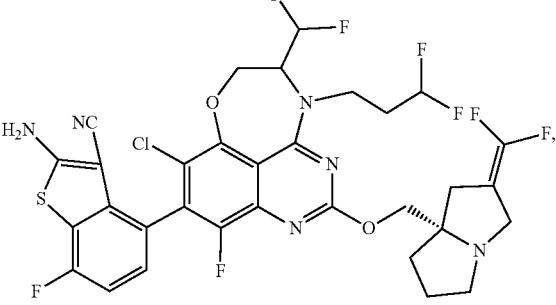

1035
-continued
1036
-continued
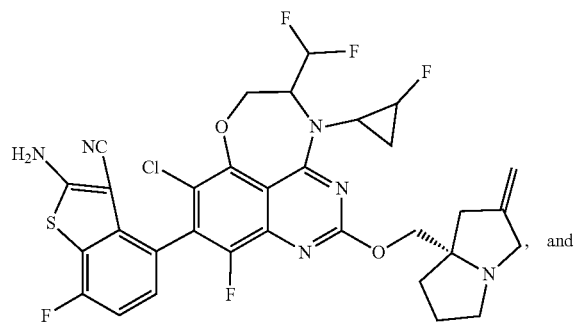
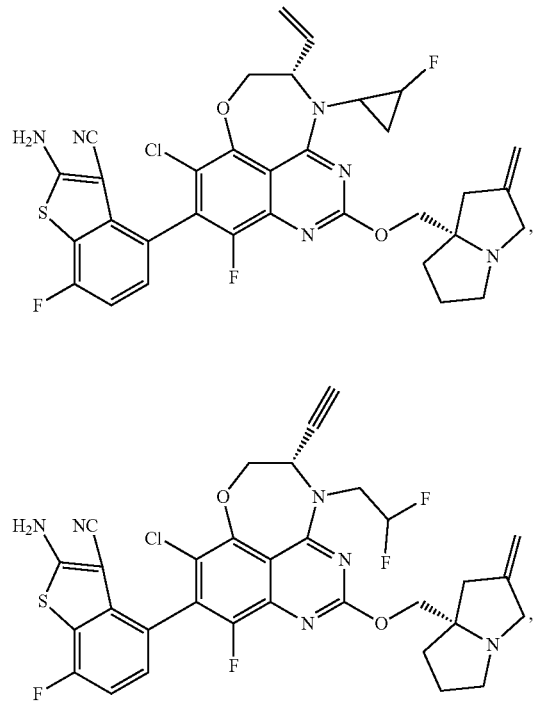
In an aspect is provided a compound selected from:
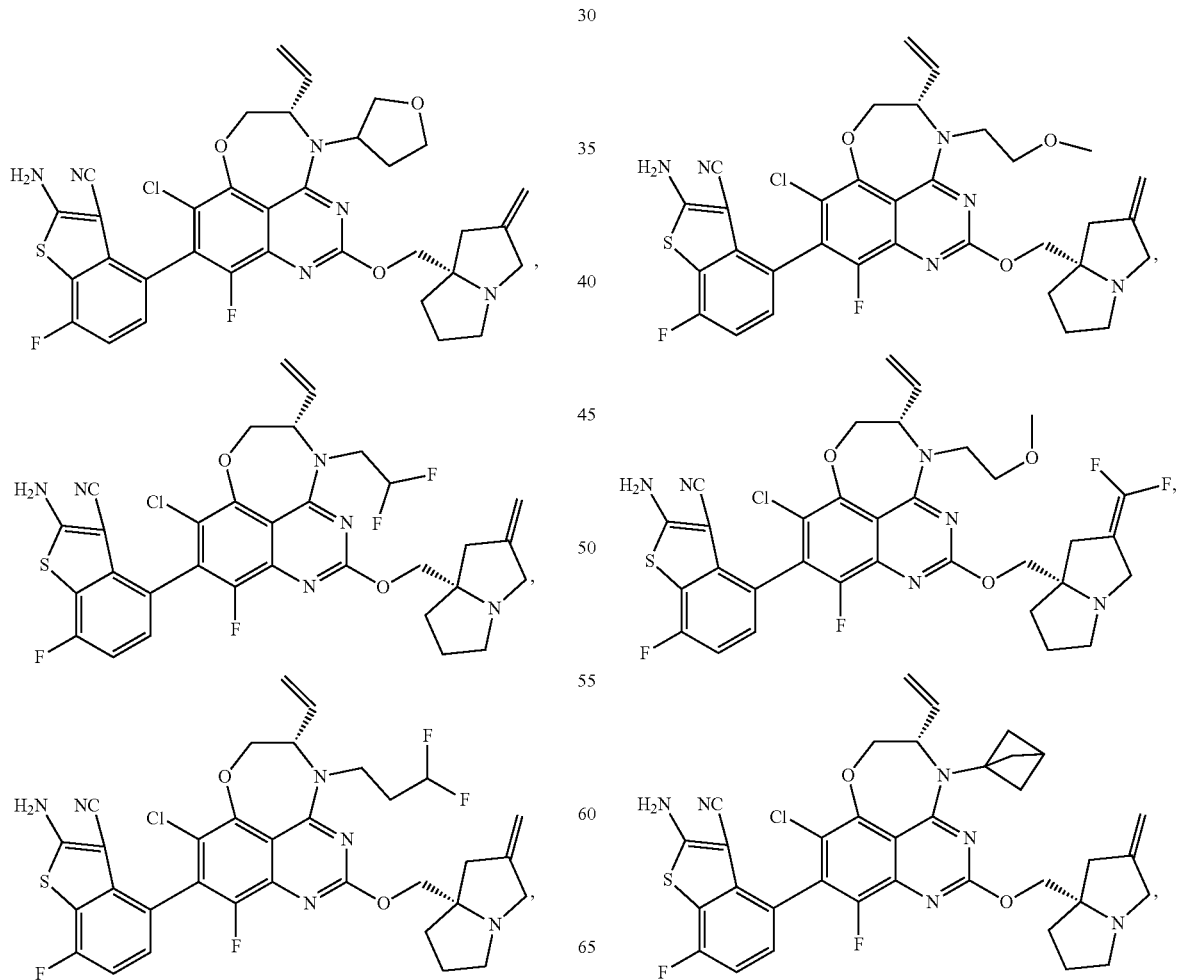

1037
-continued
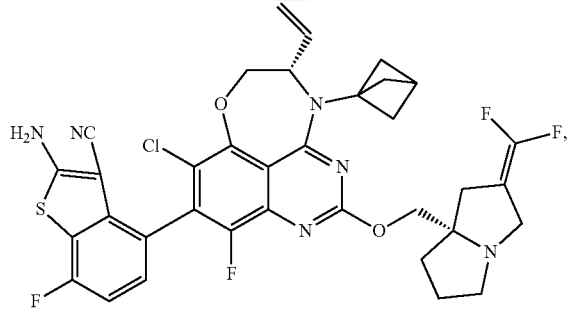
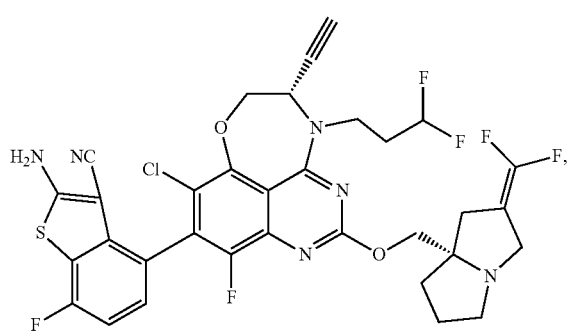
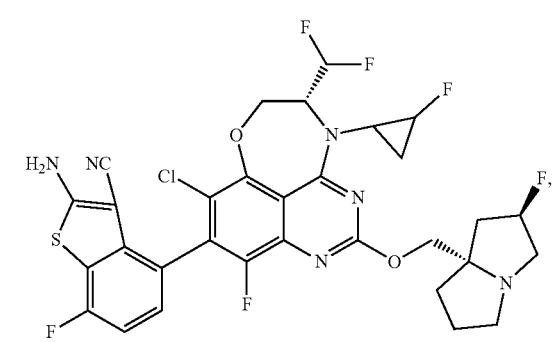
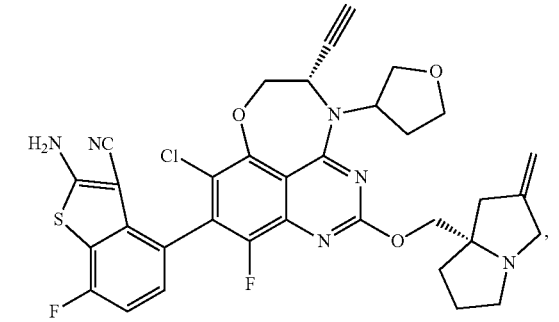
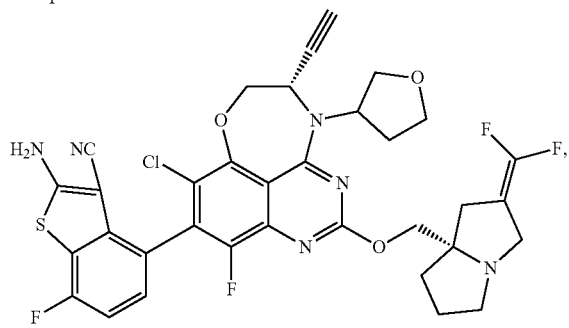
1038
-continued
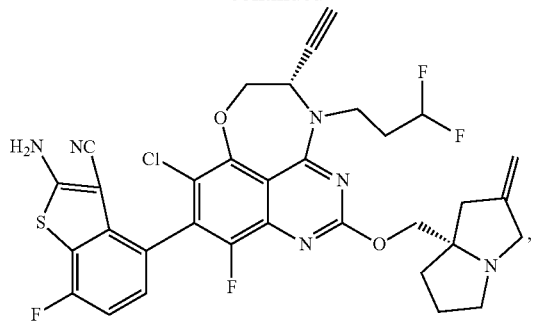
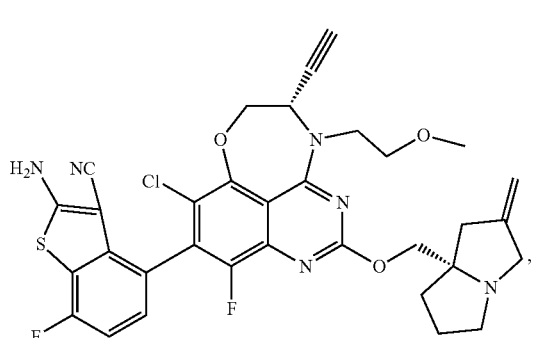
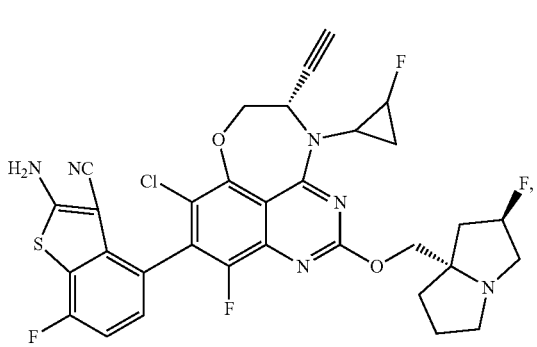
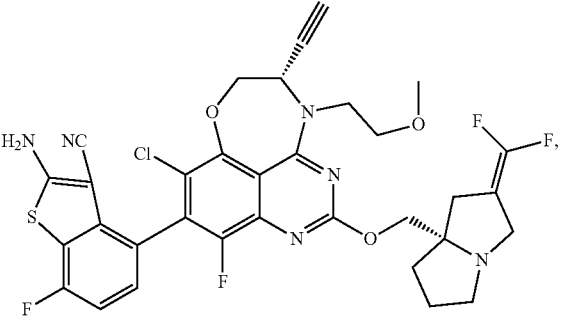
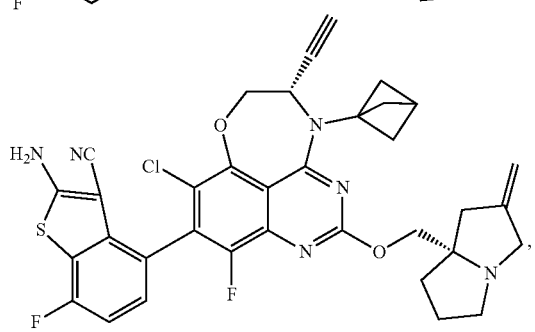

1039
-continued
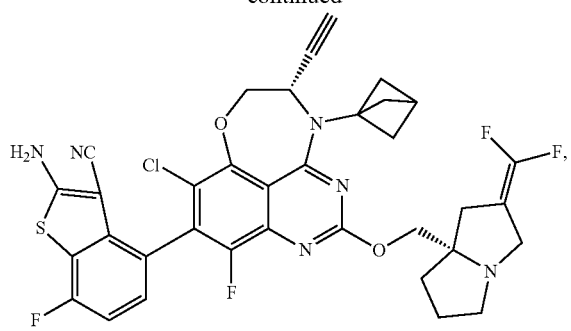
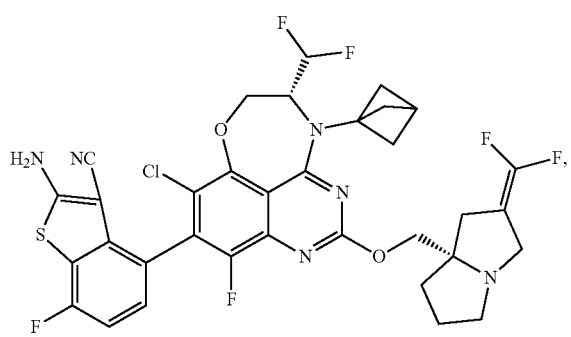

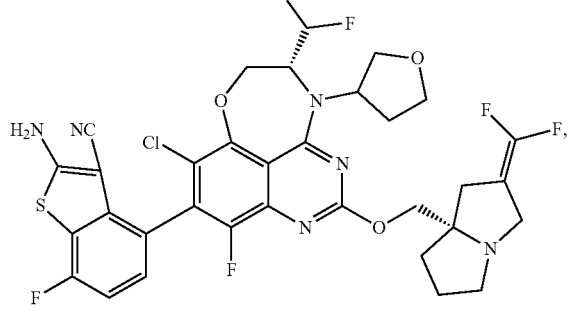
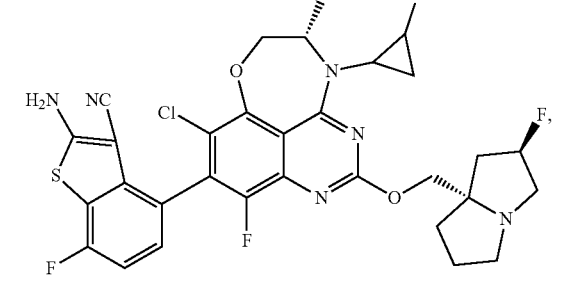
1040
-continued
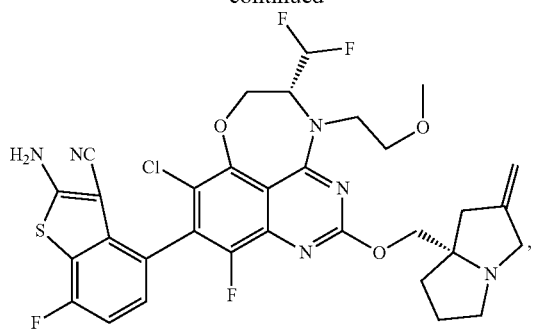
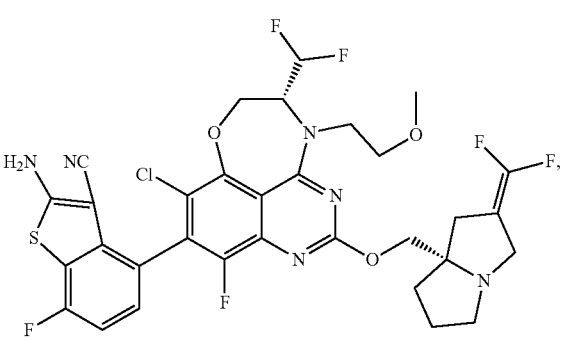
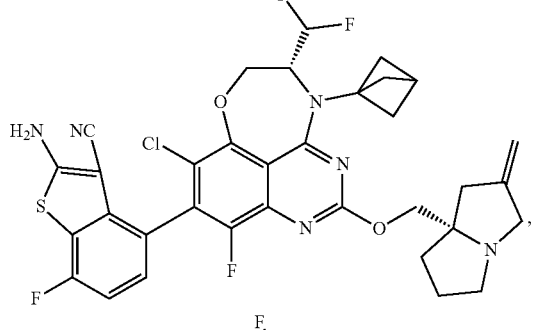
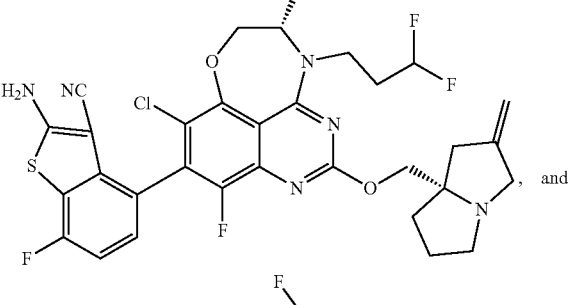
, and
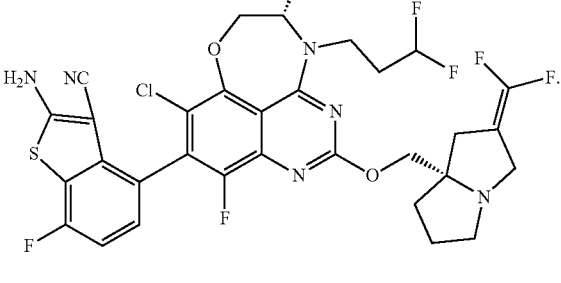

In an aspect is provided a compound selected from:
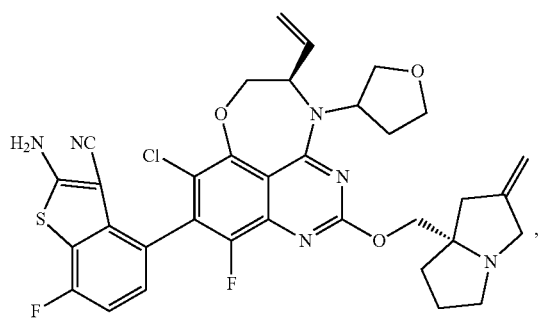
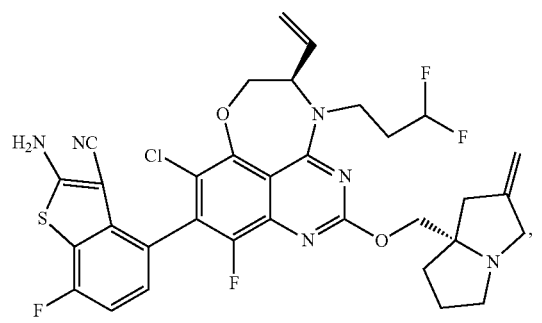
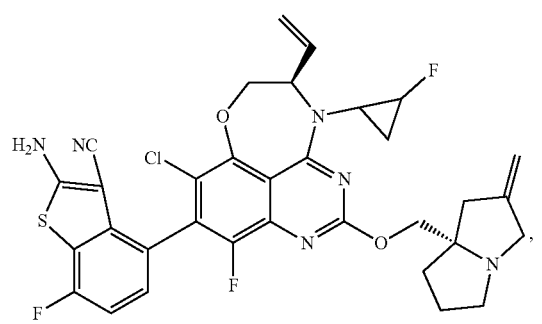
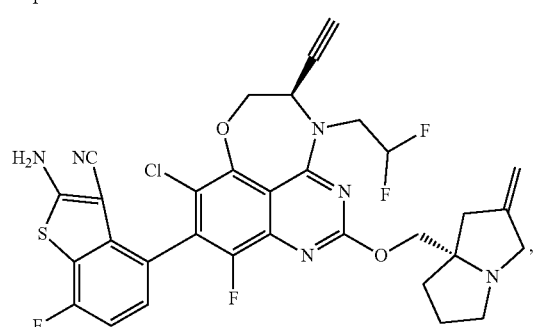
-continued
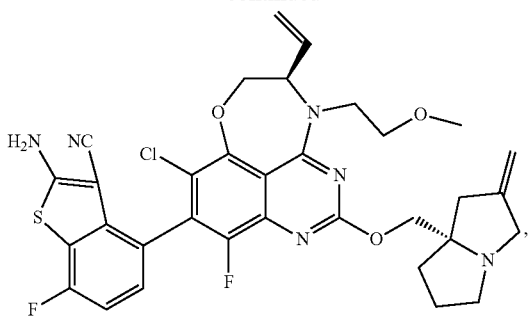
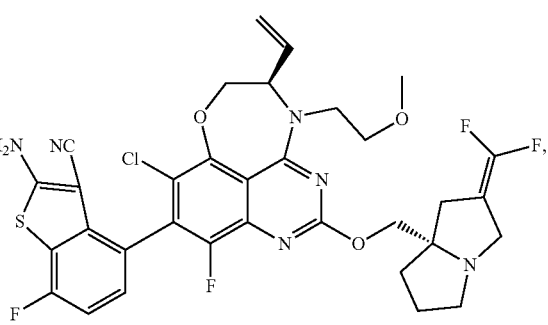
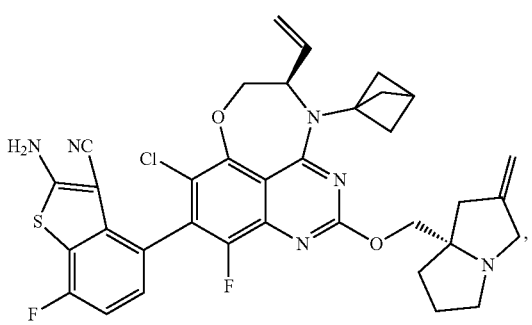
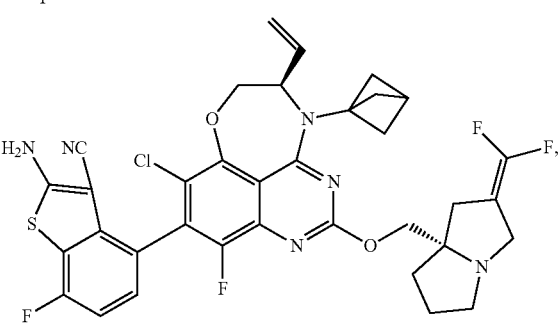
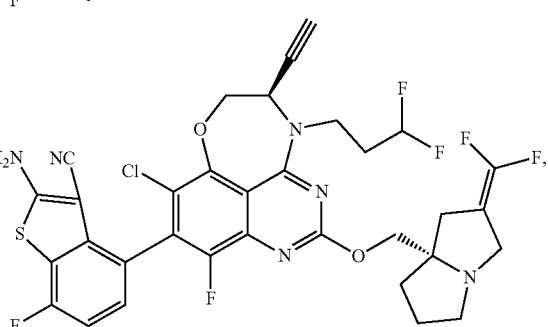

1043
-continued
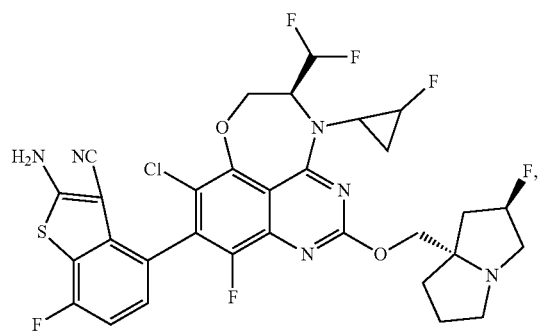
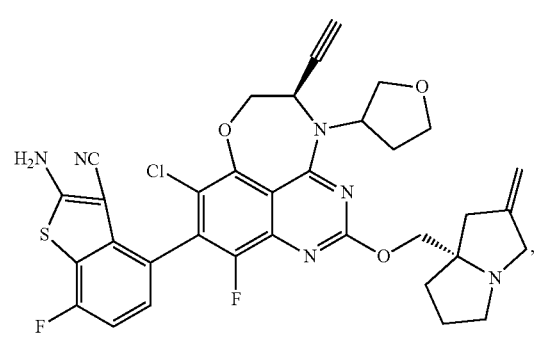
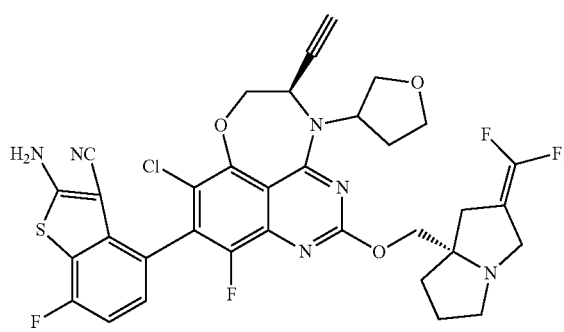
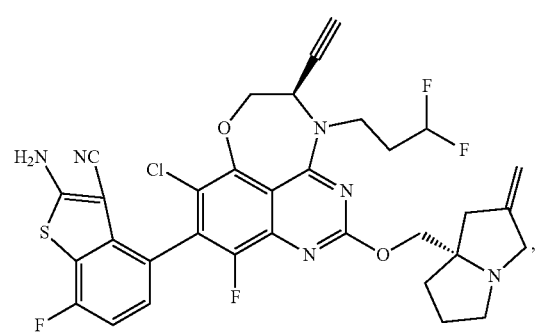
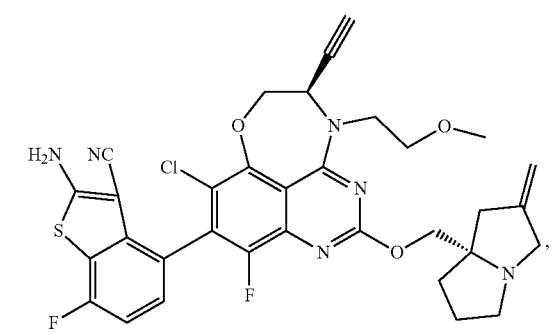
1044
-continued
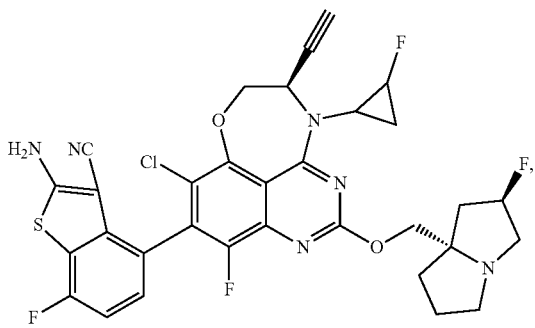
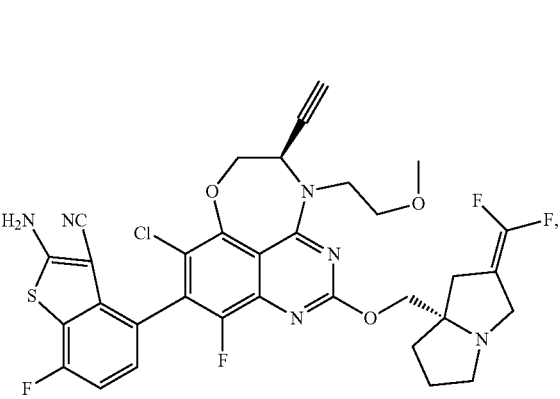
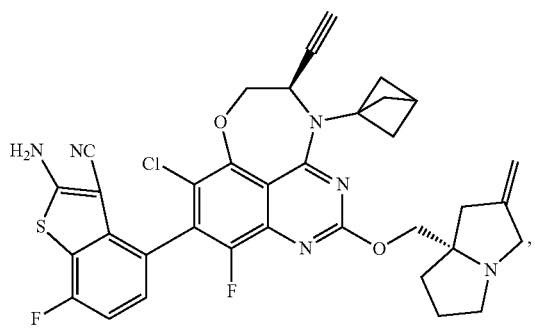
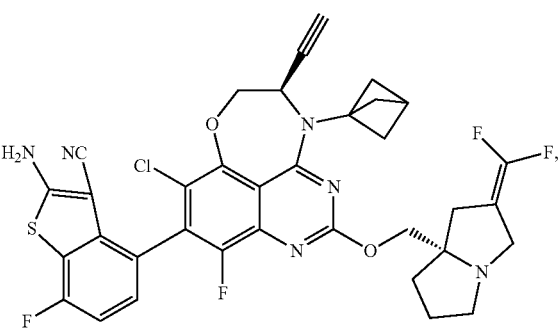
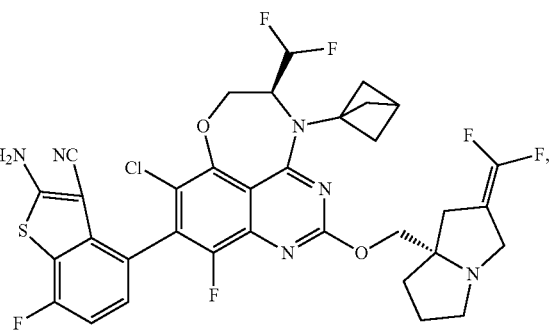

-continued

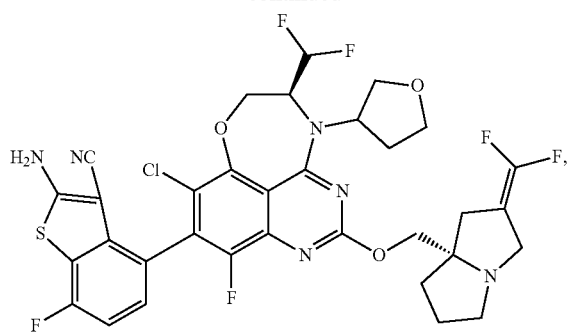

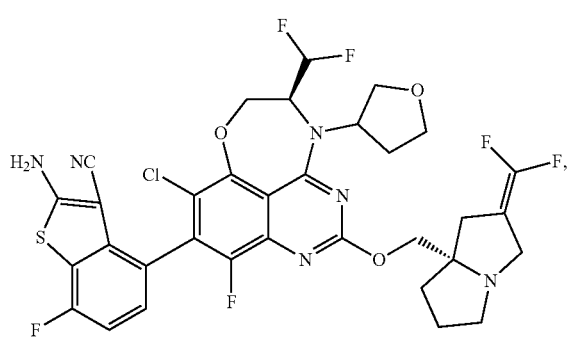

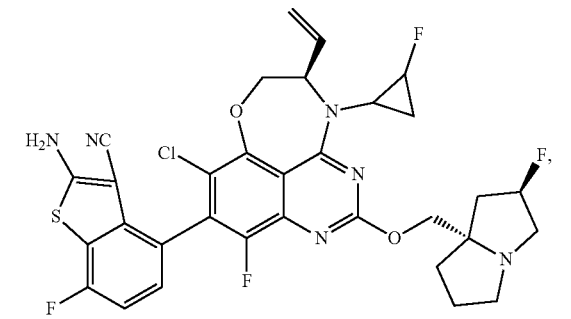

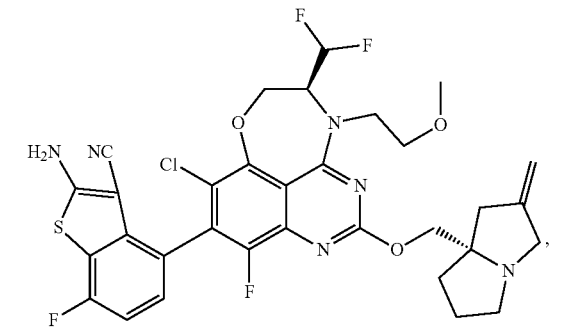

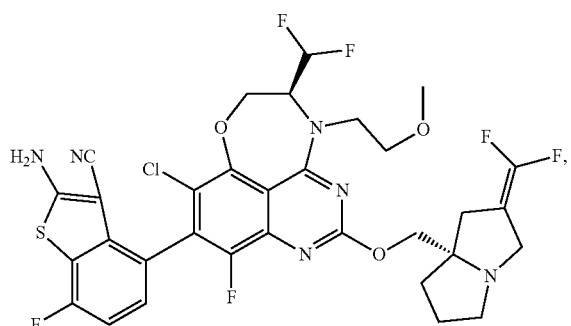

-continued

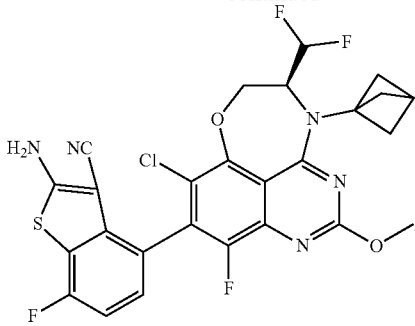

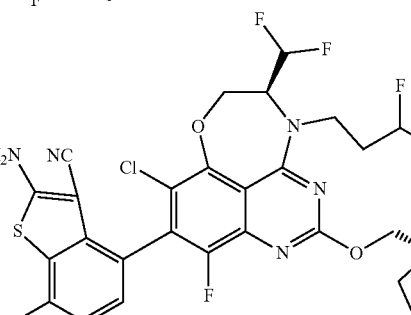

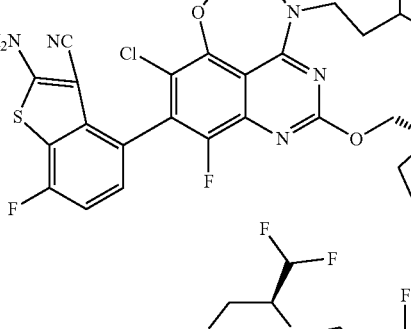

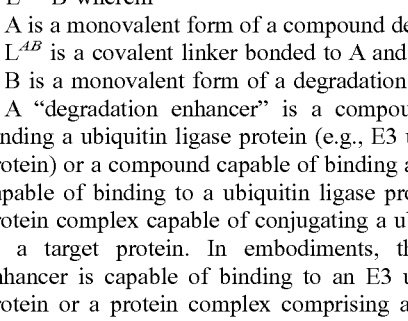

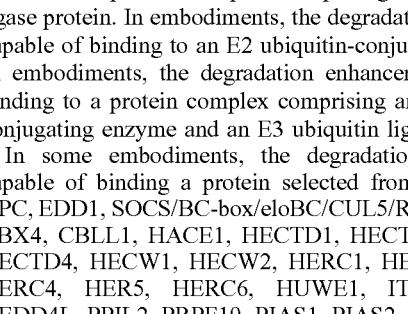, and

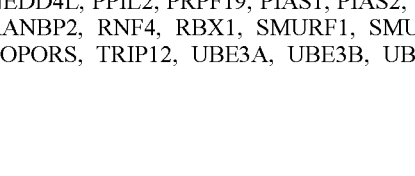

In some embodiments is a compound having the formula A-L$^{AB}$-B wherein

A is a monovalent form of a compound described herein;
L$^{AB}$ is a covalent linker bonded to A and B; and
B is a monovalent form of a degradation enhancer.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In embodiments, the degradation enhancer is capable of binding to an E3 ubiquitin ligase protein or a protein complex comprising an E3 ubiquitin ligase protein. In embodiments, the degradation enhancer is capable of binding to an E2 ubiquitin-conjugating enzyme. In embodiments, the degradation enhancer is capable of binding to a protein complex comprising an E2 ubiquitin-conjugating enzyme and an E3 ubiquitin ligase protein.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4$^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L$^3$, UBE2L$^6$, UBE2L$^1$, UBE2L$^2$, UBE2L$^4$, UBE2M, UBE2N, UBE2O, UBE2Q$^1$, UBE2Q$^2$, UBE2R$^1$, UBE2R$^2$, UBE2S, UBE2T, UBE2U, UBE2V1, UBE2V2, UBE2W, UBE2Z, ATG3, BIRC6, and UFC1.

In embodiments, the degradation enhancer is a compound described in Ishida and Ciulli, SLAS Discovery 2021, Vol. 25(4) 484-502, which is incorporated by reference in its entirety for any purpose, for example VH032, VH101, VH298, thalidomide, bestatin, methyl bestatin, nutlin, idasanutlin, bardoxolone, bardoxolone methyl, indisulam (E7070), E7820, chloroquinoxaline sulfonamide (CQS), nimbolide, KB02, ASTX660, lenalidomide, or pomalidomide.

In embodiments, the degradation enhancer is a compound described in US20180050021, WO2016146985, WO2018189554, WO2018119441, WO2018140809, WO2018119448, WO2018119357, WO2018118598, WO2018102067, WO201898280, WO201889736, WO201881530, WO201871606, WO201864589, WO201852949, WO2017223452, WO2017204445, WO2017197055, WO2017197046, WO2017180417, WO2017176958, WO201711371, WO2018226542, WO2018223909, WO2018189554, WO2016169989, WO2016146985, CN105085620B, CN106543185B, U.S. Pat. Nos. 10,040,804, 9,938,302, 10,144,745, 10,145,848, 9,938,264, 9,632,089, 9,821,068, 9,758,522, 9,500,653, 9,765,019, 8,507,488, 8,299,057, 20180298027, US 20180215731, US 20170065719, US 20170037004, US 20160272639, US 20150291562, or US 20140356322, which are incorporated by reference in their entirety for any purpose.

In some embodiments, $L^{AB}$ is -$L^{AB1}$-$L^{AB2}$-$L^{AB3}$-$L^{AB4}$-$L^{AB5}$-;

$L^{AB1}$, $L^{AB2}$, $L^{AB3}$, $L^{AB4}$, and $L^{AB5}$ are independently a bond, —O—, —N($R^{14}$)—, —C(O)—, —N($R^{14}$)C(O)—, —C(O)N($R^{14}$)—, —S—, —S(O)$_2$—, —S(O)—, —S(O)$_2$N($R^{14}$)—, —S(O)N($R^{14}$)—, —N($R^{14}$)S(O)—, —N($R^{14}$)S(O)$_2$—, $C_{1-6}$alkylene, (—O—$C_{1-6}$alkyl)$_2$—, (—$C_{1-6}$alkyl-O)$_2$—, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, wherein $C_{1-6}$alkylene, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, are optionally substituted with one, two, or three $R^{20l}$, wherein each $C_{1-6}$alkyl of (—O—$C_{1-6}$alkyl)$_z$- and (—$C_{1-6}$alkyl-O), — is optionally substituted with one, two, or three $R^{20m}$;

z is independently an integer from 0 to 10;

each $R^{12}$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{1d}$ is independently selected from hydrogen, $C_{1-6}$alkyl, and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20l}$, $R^{20m}$, and $R^{20n}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-}$heteroaryl.

In some embodiments, $L^{AB}$ is —(O-$C_2$alkyl), — and z is an integer from 1 to 10.

In some embodiments, $L^{AB}$ is —($C_2$alkyl-O—)$_z$— and z is an integer from 1 to 10.

In some embodiments, $L^{AB}$ is —(CH$_2$)$_{zz1}$ $L^{AB2}$ (CH$_2$O)$_{zz2}$—, wherein $L^{AB2}$ is a bond, a 5 or 6 membered heterocycloalkylene or heteroarylene, phenylene, —(C$_2$-C$_4$) alkynylene, —$_5$O$_2$— or —NH—; and zz1 and zz2 are independently an integer from 0 to 10.
In some embodiments, L$^{AB}$ is —(CH$_2$)zz1(CH$_2$O)$_{zz2}$—, wherein zz1 and zz2 are each independently an integer from 0 to 10.
In some embodiments, L$^{AB}$ is a PEG linker.
In some embodiments, B is a monovalent form of a compound selected from
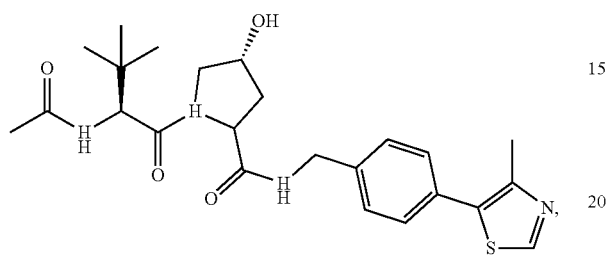
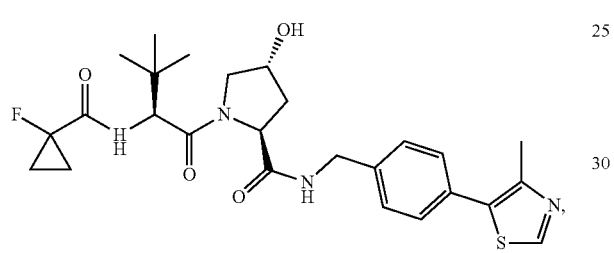
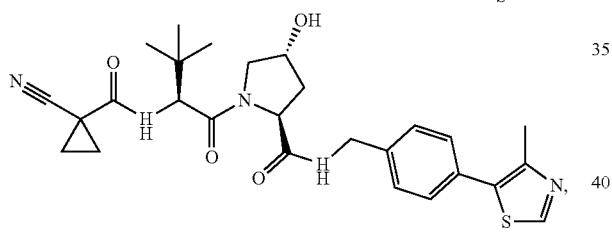
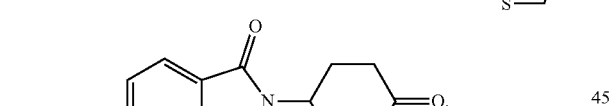
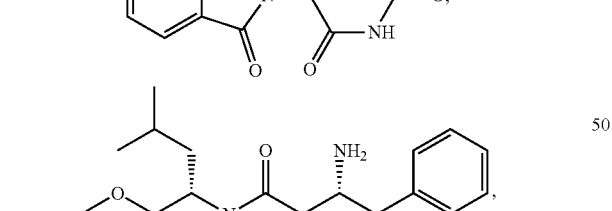
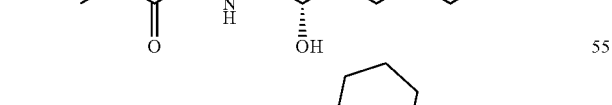
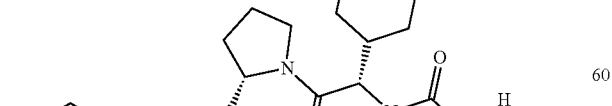
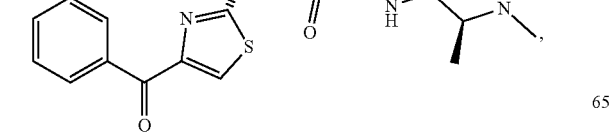
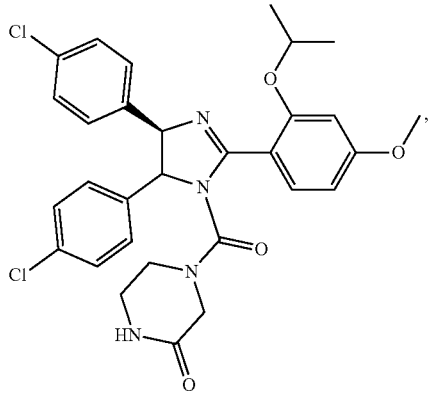
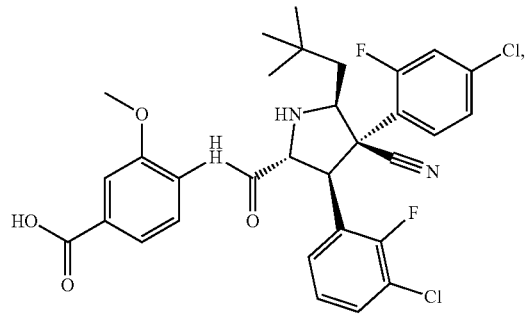
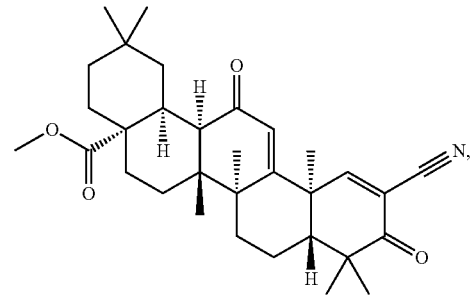
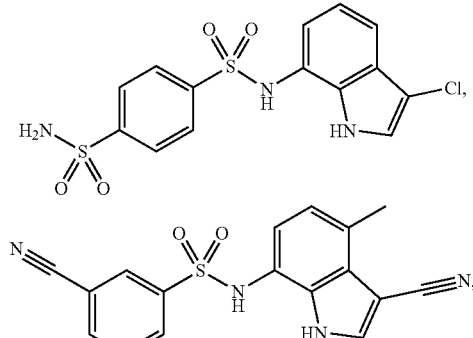
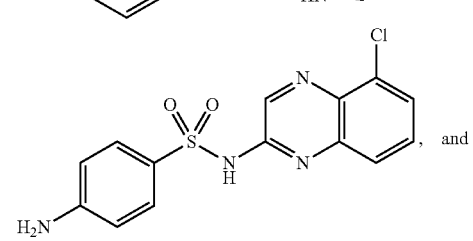
, and

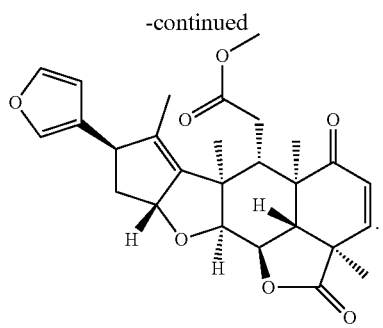

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

The skilled person will appreciate that certain compounds disclosed herein can exist in one or more isomeric forms (e.g., stereoisomers, geometric isomers, atropisomers, tautomers). Unless otherwise indicated or clear from context, a depicted structure can be understood to represent any such isomeric form, individually or in combination. In some embodiments, a compound of the present disclosure is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99%, or at least 99.9% enantiomeric excess. In some embodiments, a compound of the present disclosure is provided as a substantially pure atropisomer. In some embodiments, the atropisomer is provided in enantiomeric excess. In some embodiments, the atropisomer is provided in at least 80% enantiomeric excess, such as at least 85%, at least 90%, at least 95%, at least 96%, at least 97%, at least 98%, at least 99%, or at least 99.9% enantiomeric excess. In some embodiments, a compound of the present disclosure is preferably used as a non-racemic mixture, wherein one atropisomer is present in excess of its corresponding enantiomer or epimer. Typically, such mixture will contain a mixture of the two isomers in a ratio of at least 9:1, preferably at least 19:1. In some embodiments, the atropisomer is provided in at least 96% enantiomeric excess, meaning the compound has less than 2% of the corresponding enantiomer. In some embodiments, the atropisomer is provided in at least 96% diastereomeric excess, meaning the compound has less than 2% of the corresponding diastereomer.

The term "atropisomers" refers to conformational stereoisomers which occur when rotation about a single bond in the molecule is prevented, restricted, or greatly slowed as a result of steric interactions with other parts of the molecule and wherein the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom. For example, the skilled person would understand that a compound of Formula (Ia) substituted with 2-amino-7-fluorobenzo[b]thiophene-3-carbonitrile as depicted below can exist in two atropisomeric forms:

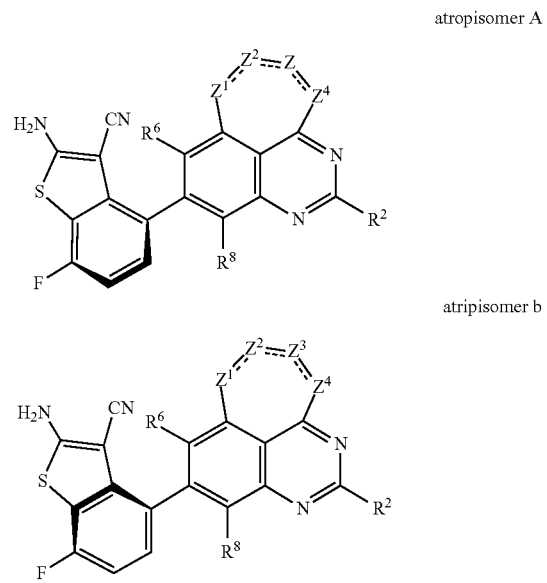

Atropisomers are typically considered stable if the barrier to interconversion is high enough to permit the atropisomers to undergo little or no interconversion at room temperature for a least a week, preferably at least a year. In some embodiments, an atropisomeric compound of the disclosure does not undergo more than about 5% interconversion to its opposite atropisomer at room temperature during one week when the atropisomeric compound is in substantially pure form, which is generally a solid state. In some embodiments, an atropisomeric compound of the disclosure does not undergo more than about 5% interconversion to its opposite atropisomer at room temperature (approximately 25° C.) during one year. The present chemical entities, pharmaceutical compositions, and methods are meant to include all such possible atropisomers, including racemic mixtures, diastereomeric mixtures, epimeric mixtures, optically pure forms of single atropisomers, and intermediate mixtures.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2H$, $^3H$, $^{13}C$, $^{14}C$, $^{15}N$, $^{17}O$, 180, 31 P, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as 3H and 14C are incorporated, are useful in drug and/or substrate tissue distribution assays. Tritiated, i.e., 3H and carbon-14, i.e., 14C, isotopes are particularly preferred for their ease of preparation and detectability. Further, substitution with heavy isotopes such as deuterium, i.e., 2H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. In some embodiments, the following synthetic method may be utilized.

In some embodiments, the compounds described herein are prepared as outlined in one of the following synthetic schemes:

General synthetic scheme 1

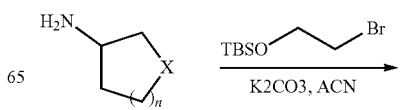

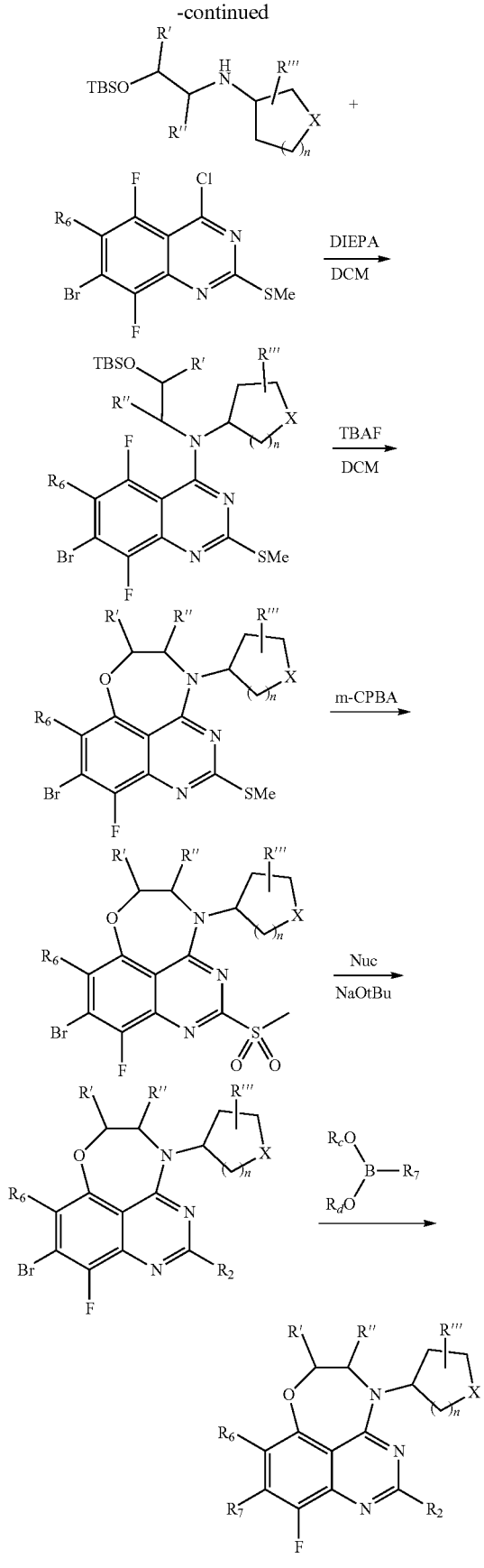

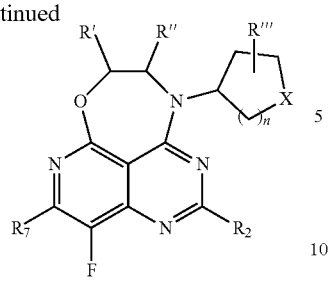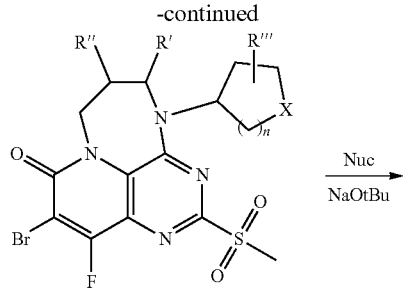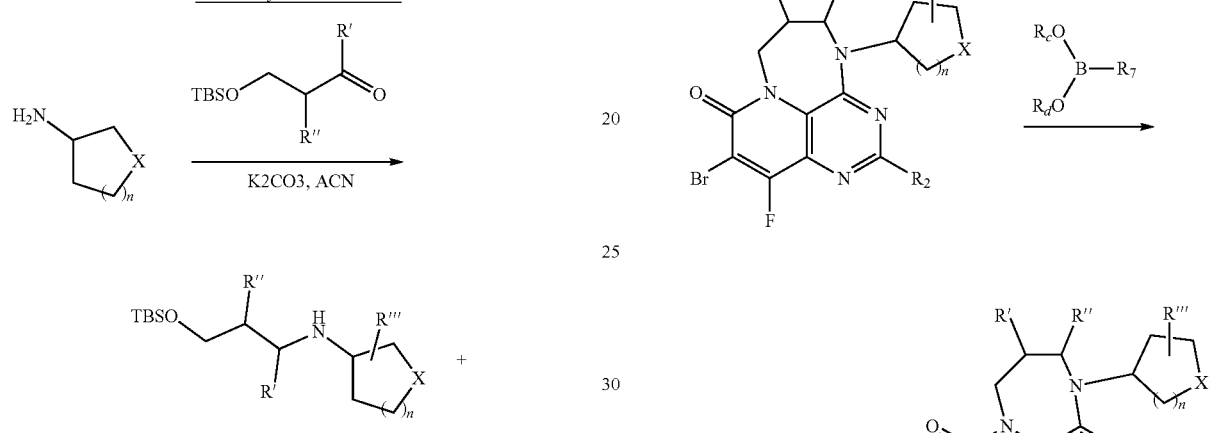
General synthetic scheme 3
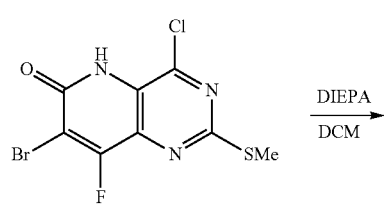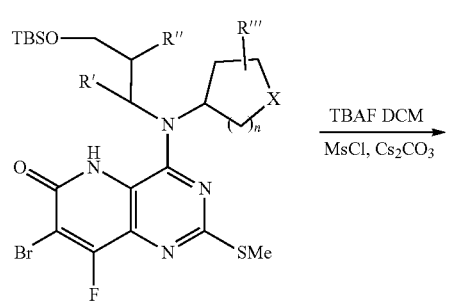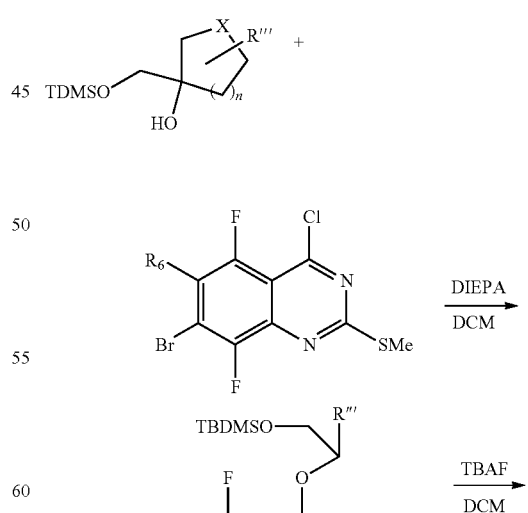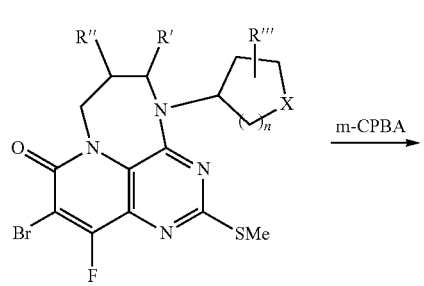
General synthetic scheme 4
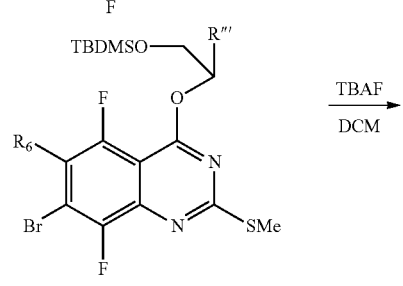

1059
-continued
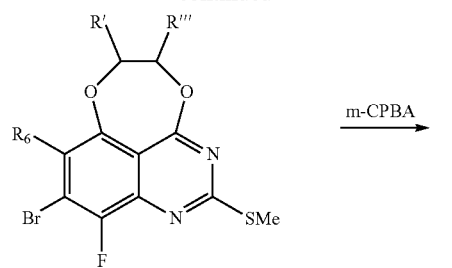
1060
-continued
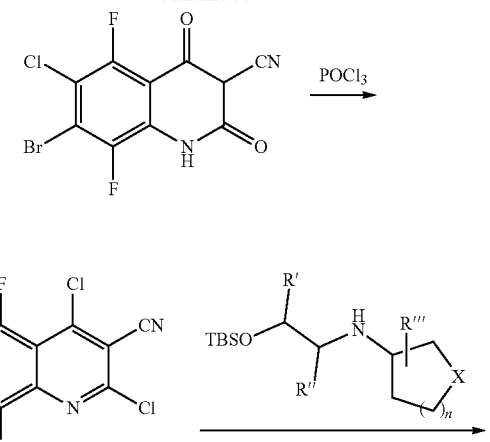
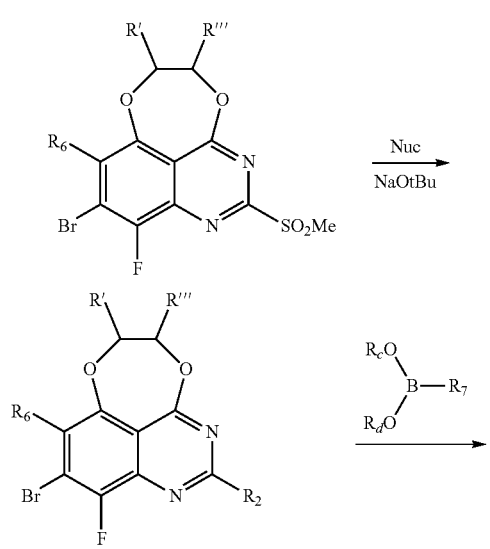
General synthetic scheme 5
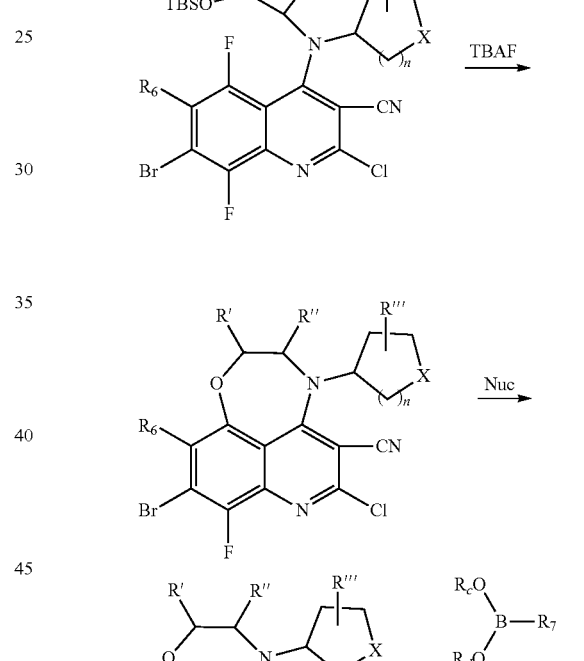
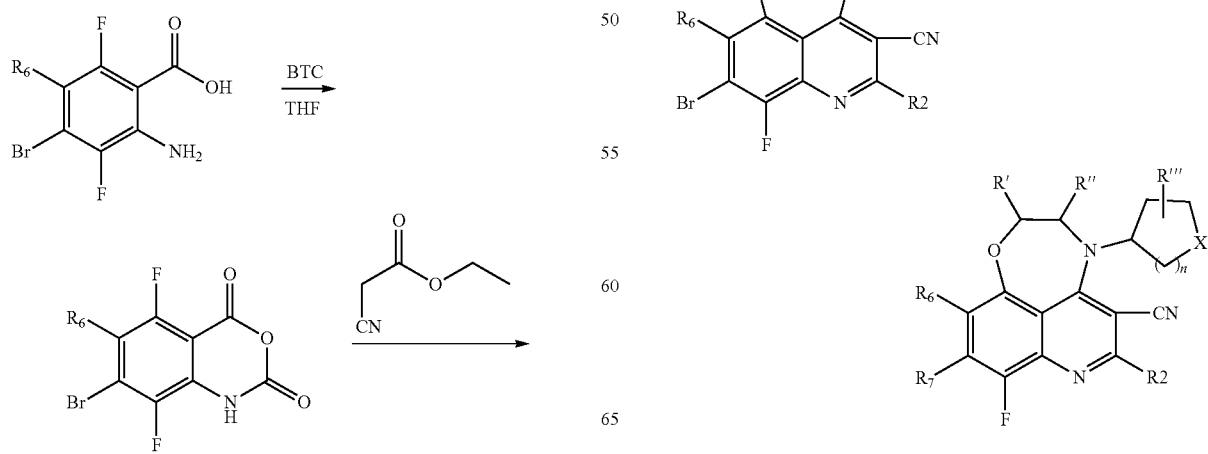

General sythetic scheme 6
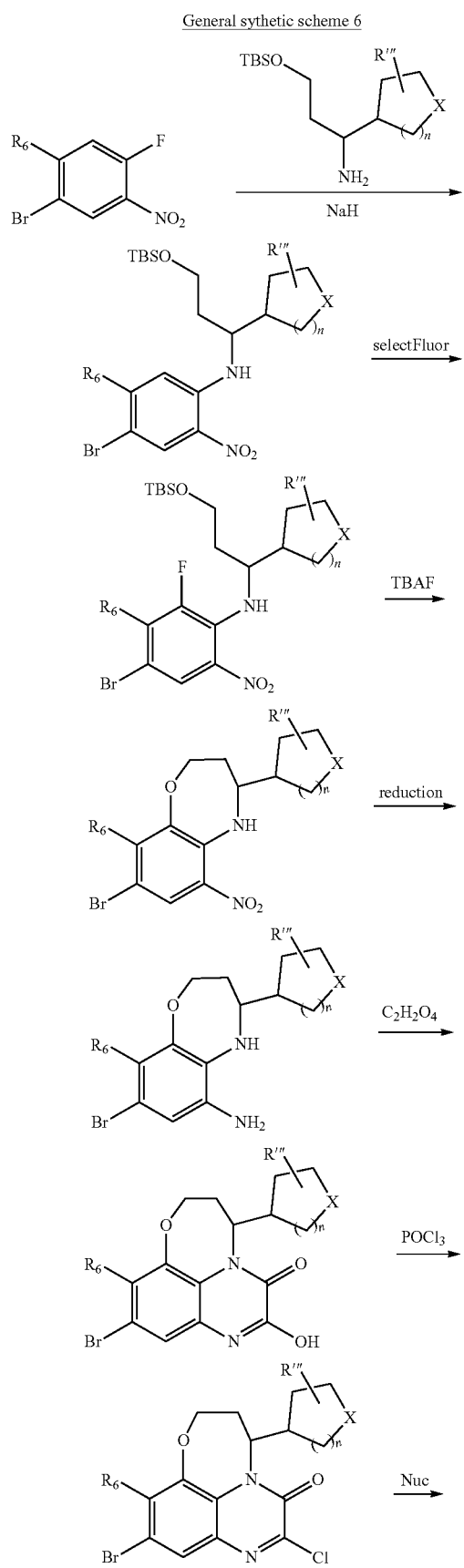
General synthetic scheme 7
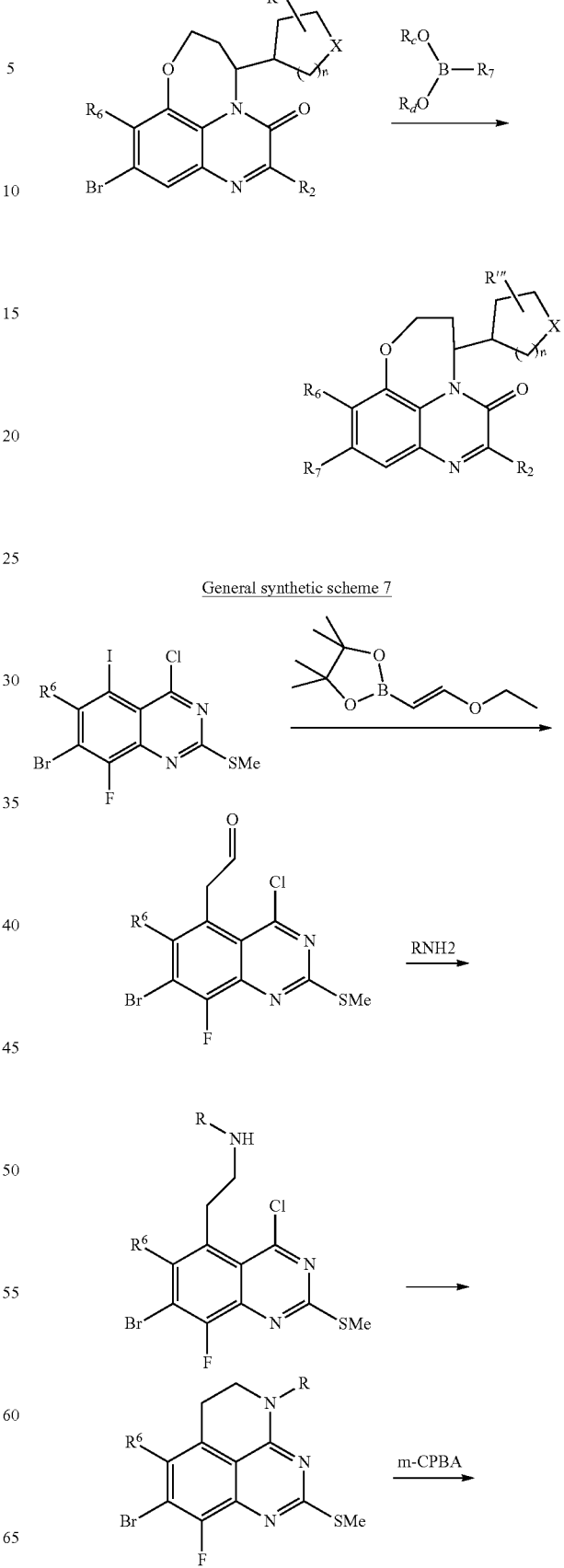

1063
-continued
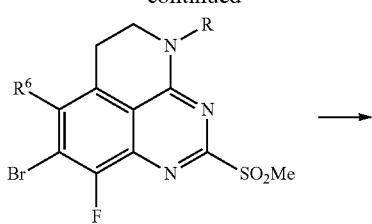
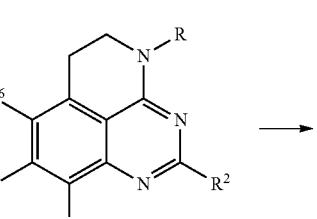
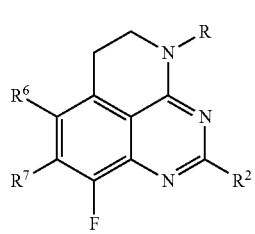
General synthetic scheme 8
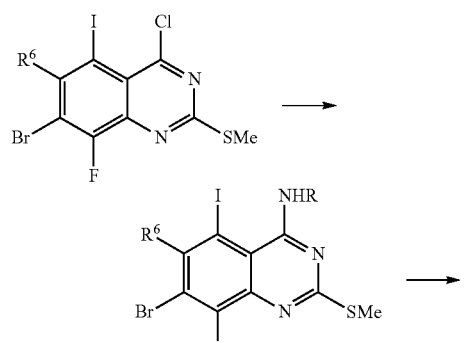
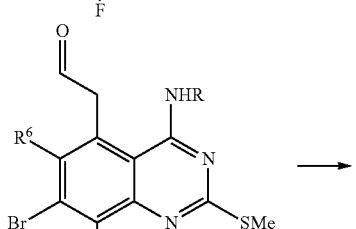
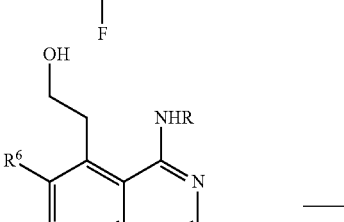
1064
-continued
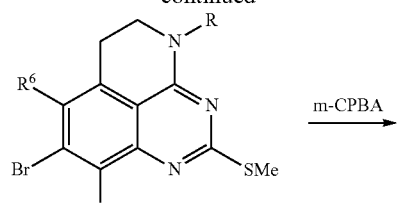
m-CPBA
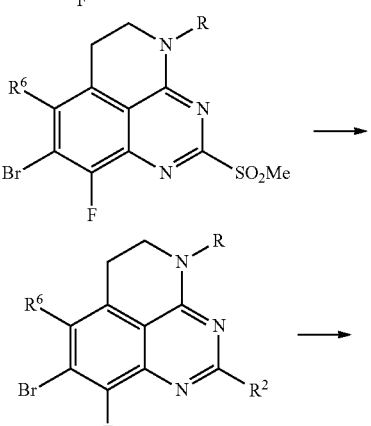
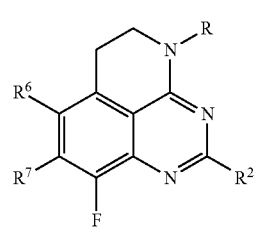
General synthetic scheme 9
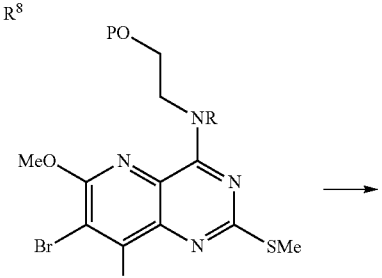
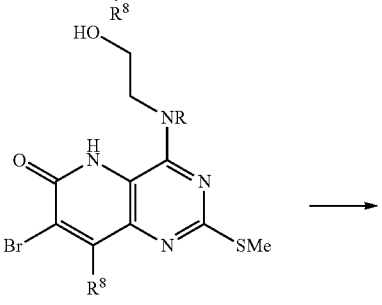

1065
-continued
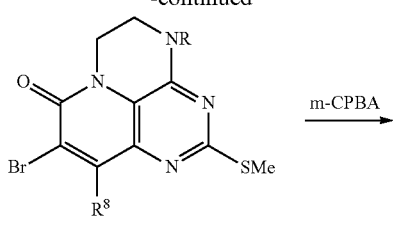
m-CPBA →
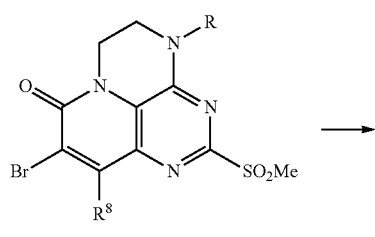
→
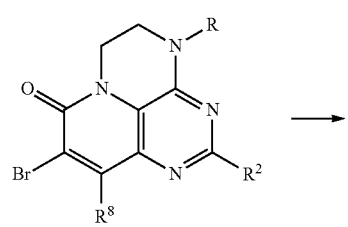
→
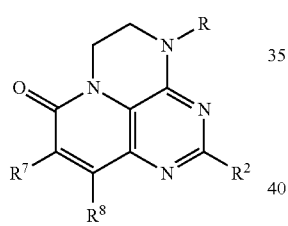
General synthetic scheme 10
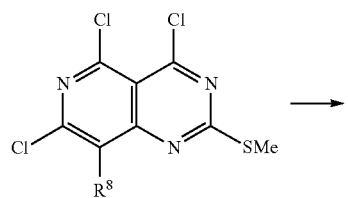
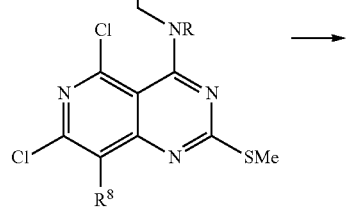
1066
-continued
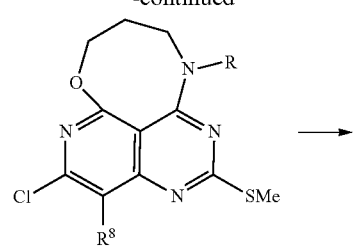
→
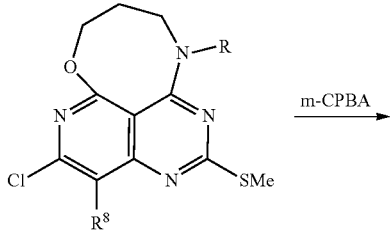
m-CPBA →
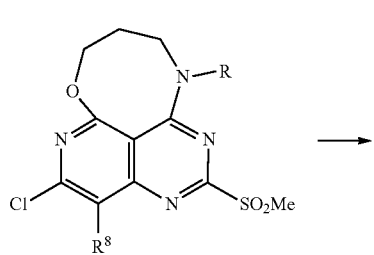
→
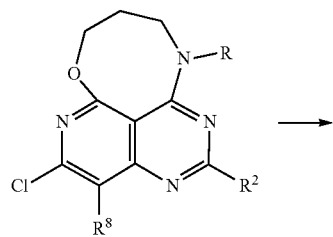
General synthetic scheme 11
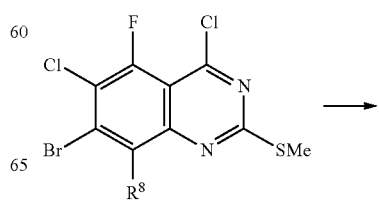
→

1067
-continued
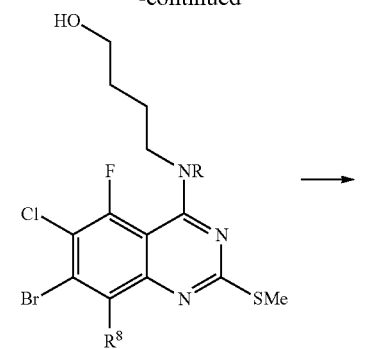
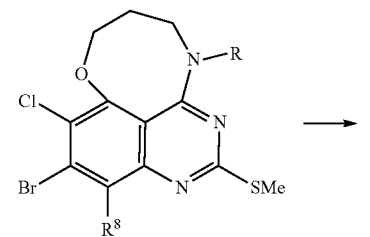
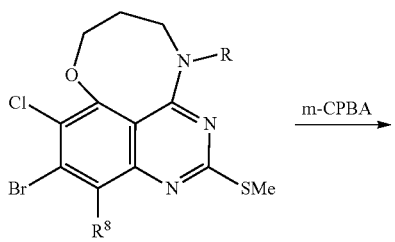 m-CPBA →
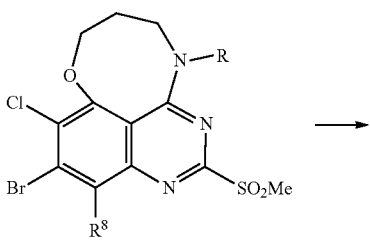
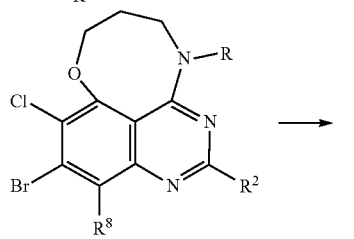
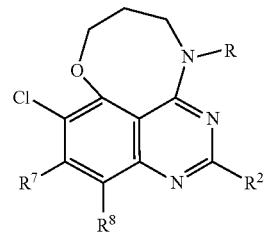
General synthetic scheme 12
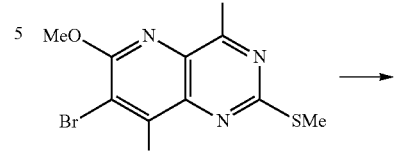
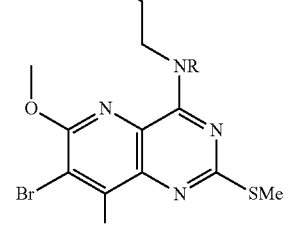
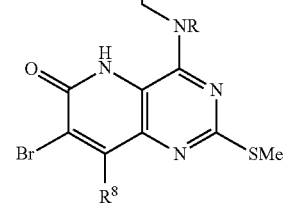
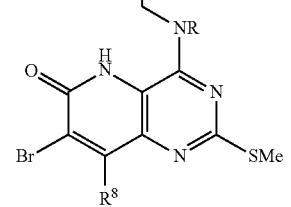
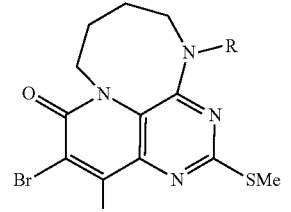
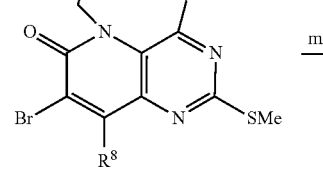 m-CPBA →

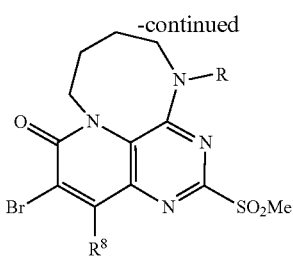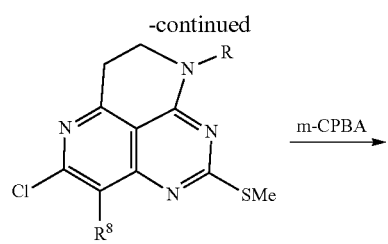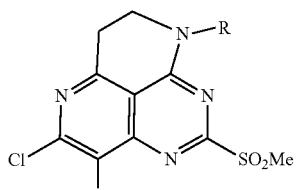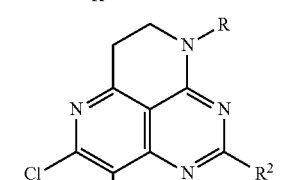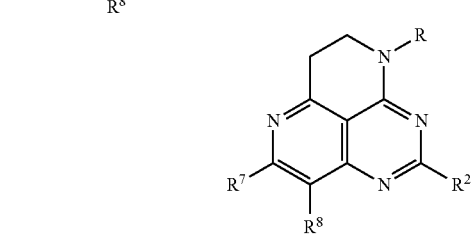
General synthetic scheme 13
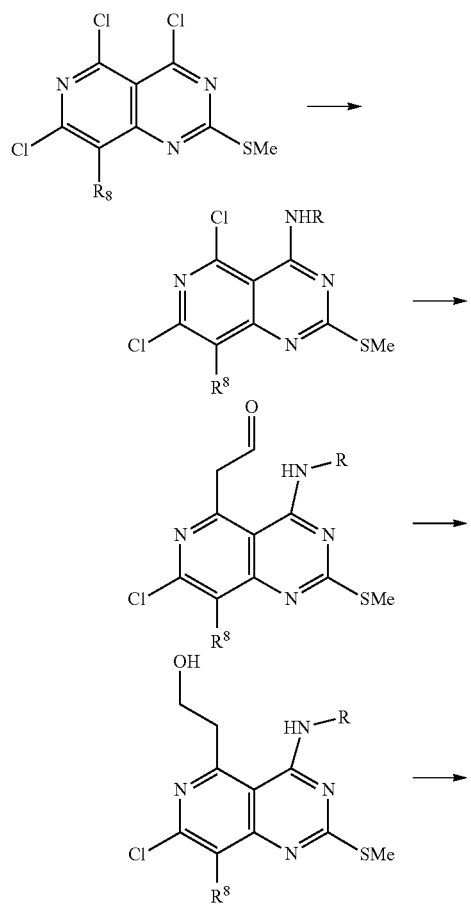
General synthetic scheme 14
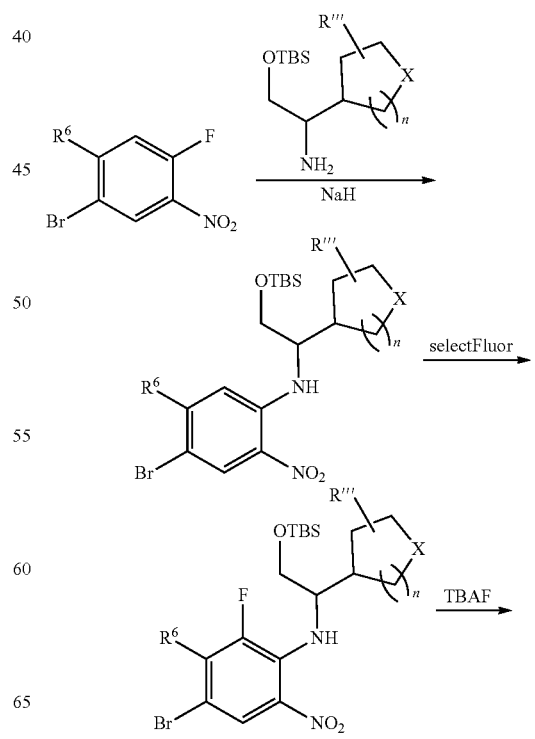

-continued
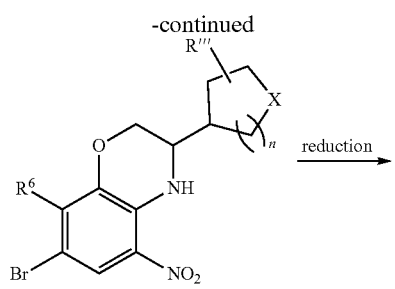
reduction →
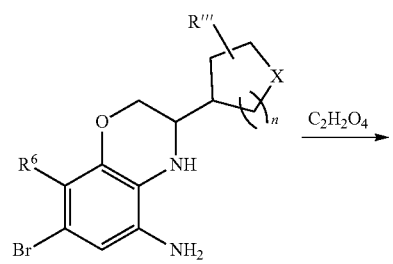
C₂H₂O₄ →
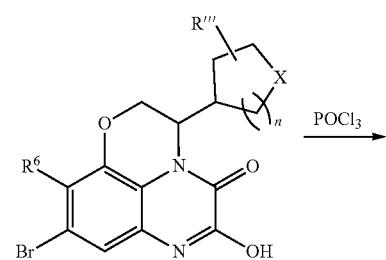
POCl₃ →
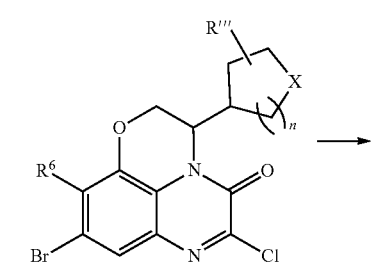
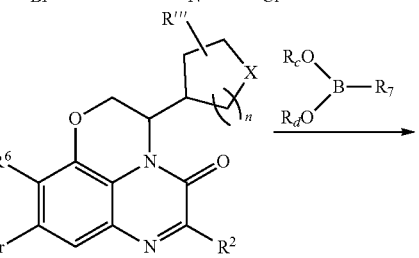
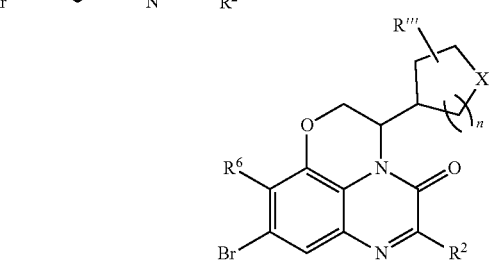
General synthetic scheme 15
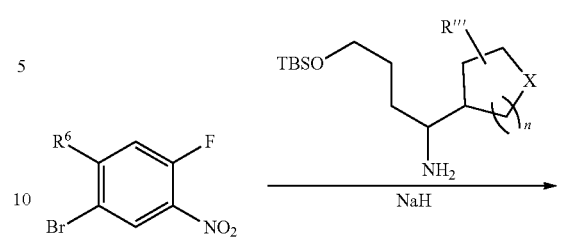
NaH →
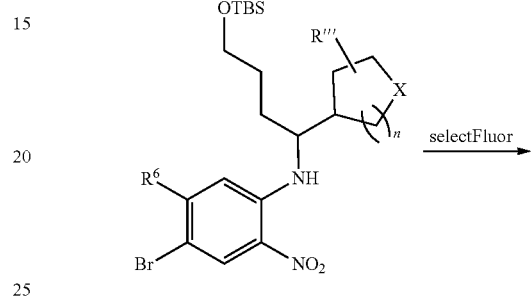
selectFluor →
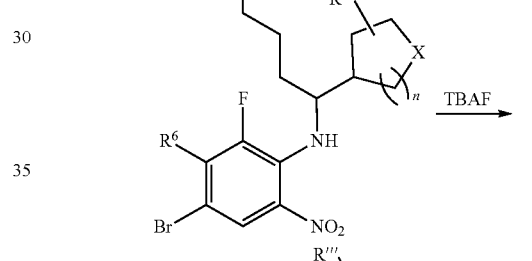
TBAF →
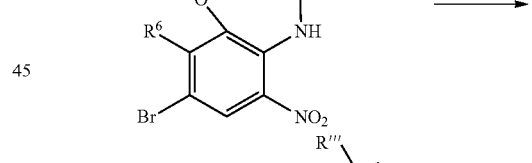
reduction →
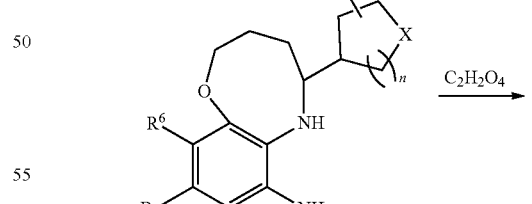
C₂H₂O₄ →
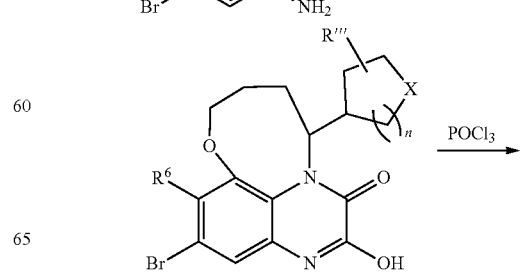
POCl₃ →

1073
-continued

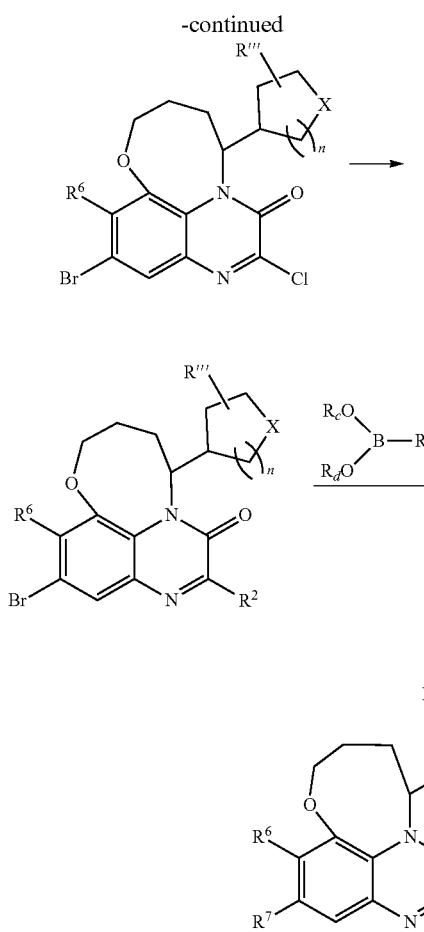

General synthetic scheme 16

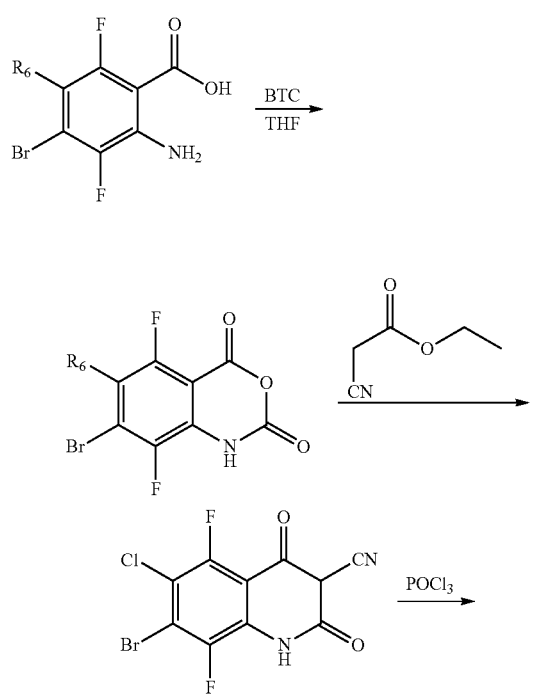

1074
-continued

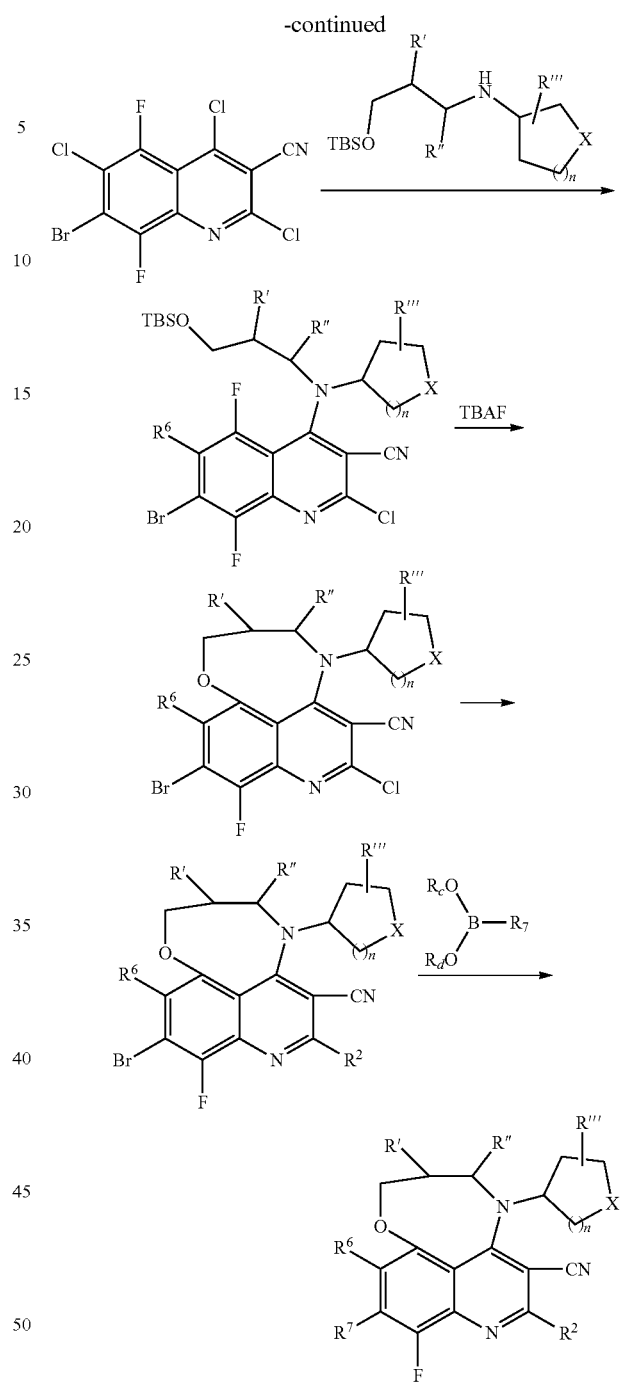

In some embodiments, the compounds of the present invention exhibit one or more functional characteristics disclosed herein. For example, a subject compound binds to a Ras protein, Kras protein or a mutant form thereof. In some embodiments, a subject compound binds specifically and also inhibits a Ras protein, Kras protein or a mutant form thereof. In some embodiments, a subject compound selectively inhibits a Kras mutant relative to a wildtype Kras or a different Kras mutant. In some embodiments, a subject compound selectively inhibits KrasG12D relative to wildtype Kras and/or a different Kras mutant. In some embodiments, a subject compound selectively inhibits KrasG12S relative to wildtype Kras and/or a different Kras mutant. In some embodiments, a subject compound selectively inhibits KrasG12V relative to wildtype Kras and/or a different Kras mutant. In some embodiments, a subject compound inhibits both Kras mutants (including for example, KrasG12D, Kras12S, Kras12V) and wildtype Kras. Such compounds characterized as Kras pan-inhibitors may exhibit comparable inhibition potency as ascertained by IC50 value in an in vitro biochemical or cellular assay disclosed herein. In some embodiments, the IC50 of a subject compound for a Kras mutant (e.g., including G12D, G12S, G12V) is less than about 5 µM, less than about 1 uM, less than about 50 nM, less than about 10 nM, less than about 1 nM, less than about 0.5 nM, less than about 100 µM, or less than about 50 µM, as measured in an in vitro assay known in the art or exemplified herein. In some embodiments, a subject Kras pan-inhibitor exhibits an IC50 as measured in an in vitro assay known in the art or exemplified herein of less than about 5 µM, less than about 1 µM, less than about 50 nM, less than about 10 nM, less than about 1 nM, or even less than about 0.5 nM. In some embodiments, a subject compound covalently binds to a Kras mutants (e.g., KrasG12D, KrasG12C, and/or G13D).

In some embodiments, a subject compound of the present disclosure is capable of reducing Ras signaling output. Such reduction can be evidenced by one or more members of the following: (i) an increase in steady state level of GDP-bound Ras protein; (ii) a reduction of phosphorylated AKTs473, (iii) a reduction of phosphorylated ERKT202/y204, (iv) a reduction of phosphorylated S6S235/236, and (v) reduction (e.g., inhibition) of cell growth of Ras-driven tumor cells (e.g., those derived from a tumor cell line disclosed herein). In some cases, the reduction in Ras signaling output can be evidenced by two, three, four or all of (i)-(v) above.

It shall be understood that different aspects of the invention can be appreciated individually, collectively, or in combination with each other. Various aspects of the invention described herein may be applied to any of the particular applications disclosed herein. The compositions of matter including compounds of any formulae disclosed herein in the composition section of the present disclosure may be utilized in the method section including methods of use and production disclosed herein, or vice versa.

Methods

The compounds described herein, or a pharmaceutically acceptable salt or solvate thereof, are Ras inhibitors capable of inhibiting a Ras protein. Ras proteins being inhibited can be Ras mutants (e.g., G12C, G12D, G12S, G1V, G13C, or G13D) from K-Ras, H-Ras or N-Ras. The compounds, a pharmaceutically acceptable salt or solvate thereof disclosed herein, have a wide range of applications in therapeutics, diagnostics, and other biomedical research.

In an aspect is provided a method of treating cancer in a subject in need thereof, comprising administering to the subject a therapeutically effective amount of a compound described herein, or a pharmaceutically acceptable salt or solvate thereof.

In an aspect is provided a method of treating cancer in a subject comprising a Ras mutant (e.g., G12C, G12D, G12S, G1V, G13C, or G13D) protein, comprising inhibiting amplified wildtype Ras or the Ras mutant (e.g., G12C, G12D, G12S, G1V, G13C, or G13D) protein of said subject by administering to said subject a compound, wherein compound is characterized in that upon contacting the Ras mutant (e.g., G12C, G12D, G12S, G1V, G13C, or G13D) protein, said the Ras mutant (e.g., G12C, G12D, G12S, G1V, G13C, or G13D) protein activity or function is inhibited (e.g., partially inhibited or completely inhibited), such that said inhibited Ras mutant (e.g., G12C, G12D, G12S, G1V, G13C, or G13D) protein exhibits reduced Ras signaling output (e.g., compared to a corresponding Ras protein not contacted by the compound).

In an aspect is provided a method of modulating activity of a Ras protein (e.g., K-Ras, mutant K-Ras, G12C, G12D, G12S, G1V, G13C, or G13D), comprising contacting a Ras protein with an effective amount of a compound described herein, or a pharmaceutically acceptable salt or solvate thereof, thereby modulating the activity of the Ras protein.

In an aspect is provided a method of inhibiting cell growth, comprising administering an effective amount of a compound described herein, or a pharmaceutically acceptable salt or solvate thereof, to a cell expressing a Ras (e.g., K-Ras) protein, thereby inhibiting growth of said cells. In embodiments, the subject method comprises administering an additional agent to said cell.

In embodiments, the cancer is a solid tumor. In embodiments, the cancer is a hematological cancer.

In practicing any of the methods disclosed herein, the Ras target to which a subject compound binds (e.g., covalently) can be a Ras mutant (e.g., G12C, G12D, G1V, G13C, or G13D), including a mutant of K-Ras, H-Ras, and N-Ras. In some embodiments, the methods of treating cancer can be applied to treat a solid tumor or a hematological cancer. In some embodiments, the cancer being treated can be, without limitation, prostate cancer, brain cancer, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound described herein, or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, and (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiments, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof.

In one embodiment, a subject treatment method is combined with a chemotherapeutic agent.

Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; *vinca* alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In an aspect, compositions provided herein can be administered in combination with radiotherapy such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-L$^1$, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-L1 antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab), anti-LAG3 antibodies (e.g., $C_{9B}7W$, $410C_9$), anti-B7-H3 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldesleukin. Aldesleukin can be administered in low dose or high dose. A high dose aldesleukin regimen can involve administering aldesleukin intravenously every 8 hours, as tolerated, for up to about 14 d oses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 d ays after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some embodiments, any of the compounds herein that is capable of binding a Ras protein (e.g., KRAS) to modulate activity of such Ras protein may be administered in combination or in conjunction with one or more pharmacologically active agents comprising (1) an inhibitor of MEK (e.g., MEK1, MEK2) or of mutants thereof (e.g., trametinib, cobimetinib, binimetinib, selumetinib, refametinib); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., $R^{428}$, amuvatinib, XL-880); (16) an inhibitor of NTRK1 and/or of mutants thereof (e.g., Merestinib); (17) an inhibitor of RET and/or of mutants thereof (e.g., BLU-667, Lenvatinib); (18) an inhibitor of A-Raf and/or B-Raf and/or C-Raf and/or of mutants thereof (RAF-709, LY-3009120); (19) an inhibitor of ERK and/or of mutants thereof (e.g., ulixertinib); (20) an MDM2 inhibitor (e.g., HDM-201, NVP-CGM097, RG-71-12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor, as well as SHIP1 inhibitors; (27) an inhibitor of SRC (e.g., dasatinib); (28) an inhibitor of JAK (e.g., tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of SHP pathway including SHP2 inhibitor (e.g., 6-(4-amino-4-methylpiperidin-1-yl)-3-(2,3-dichlorophenyl)pyrazin-2-amine, as well as SHP1 inhibitors, or (33) an inhibitor of Src, FLT3, HDAC, VEGFR, PDGFR, LCK, Bcr-Abl or AKT or (34) an inhibitor of KrasG12C mutant (e.g., including but not limited to AMG510, MRTX849, and any covalent inhibitors binding to the cysteine residue 12 of Kras, the structures of these compounds are publically known)(e.g., an inhibitor of Ras G12C as described in US20180334454, US20190144444, US20150239900, U.S. Pat. No. 10,246,424, US20180086753, WO2018143315, WO2018206539, WO20191107519, WO2019141250, WO2019150305, U.S. Pat. No. 9,862,701, US20170197945, US20180086753, U.S. Pat. No. 10,144,724, US20190055211, US20190092767, US20180127396, US20180273523, U.S. Pat. No. 10,280,172, US20180319775, US 20180273515, US 20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety)), (35) a SHC inhibitor (e.g., PP2, AID371185), (36) a GAB inhibitor (e.g., GAB-0001), (37) a GRB inhibitor, (38) a PI-3 kinase inhibitor (e.g., Idelalisib, Copanlisib, Duvelisib, Alpelisib, Taselisib, Perifosine, Buparlisib, Umbralisib, NVP-BEZ235-AN), (39) a MARPK inhibitor, (40) CDK4/6 (e.g., palbociclib, ribociclib, abemaciclib), or (41) MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), or (42) an inhibitor of SHP pathway including SHP2 inhibitor (e.g., 6-(4-amino-4-methylpiperidin-1-yl)-3-(2,3-dichlorophenyl)pyrazin-2-amine, RMC-4630, ERAS-601,

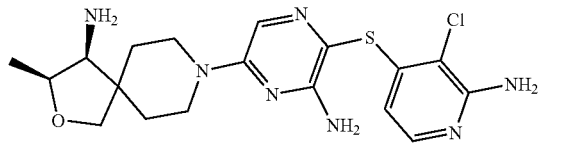

TNO155

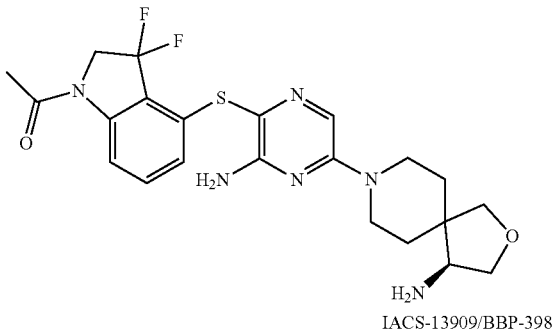

JAB-3068

IACS-13909/BBP-398

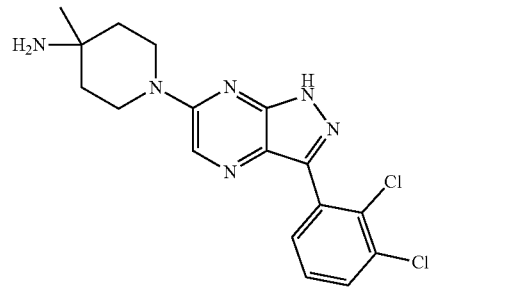

SHP099

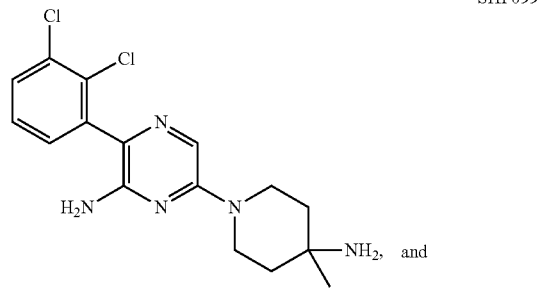

RMC-4550

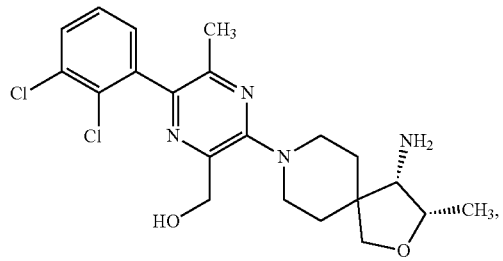

as well as SHP1 inhibitors. In some embodiments, any of the compounds herein that is capable of binding a Ras protein (e.g., Kras) to modulate activity of such Ras protein may be administered in combination or in conjunction with one or more checkpoint immune blockade agents (e.g., anti-PD-1 and/or anti-PD-L1 antibody, anti-CLTA-4 antibody). In some embodiments, any of the compounds herein that is capable of binding a Ras protein (e.g., KRAS) to modulate activity of such Ras protein may be administered in combination or in conjunction with one or more pharmacologically active agents comprising an inhibitor against one or more targets selected from the group of: MEK, epidermal growth factor receptor (EGFR), FGFR1, FGFR2, FGFR3, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHIP1, SHIP2, SHP2, SRC, JAK, PARP, BTK, FLT3, HDAC, VEGFR, PDGFR, LCK, Bcr-Abl, AKT, KrasG12C mutant, and ROS1. Where desired, the additional agent can be an inhibitor against one or more targets selected from the group of: MEK, epidermal growth factor receptor (EGFR), FGFR1, FGFR2, FGFR3, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHP2, SRC, JAK, PARP, BTK, FLT3, HDAC, VEGFR, PDGFR, LCK, Bcr-Abl, AKT, KrasG12C mutant, and ROS1. In some embodiments, any of the compounds herein that is capable of binding a Ras protein (e.g., KRAS, mutant Ras protein) to modulate activity of such Ras mutant (e.g., G12C, G12D, G12S, G1V, G13C, or G13D) may be administered in combination or in conjunction with one or more additional pharmacologically active agents comprising an inhibitor of SOS (e.g., SOS1, SOS2) or of mutants thereof. In embodiments, the additional pharmacologically active agent administered in combination or in conjunction with a compound described herein (e.g., compound capable of binding a Ras protein) is an inhibitor of SOS (e.g., SOS1, SOS2). In embodiments, the additional pharmacologically active agent administered in combination or in conjunction with a compound (e.g., compound capable of binding a Ras protein) described herein is an inhibitor of SOS (e.g., SOS1, SOS2). In embodiments, the additional pharmacologically active agent administered in combination or in conjunction with a compound (e.g., compound capable of binding a Ras protein) described herein is an inhibitor of SOS (e.g., SOS1, SOS2) selected from

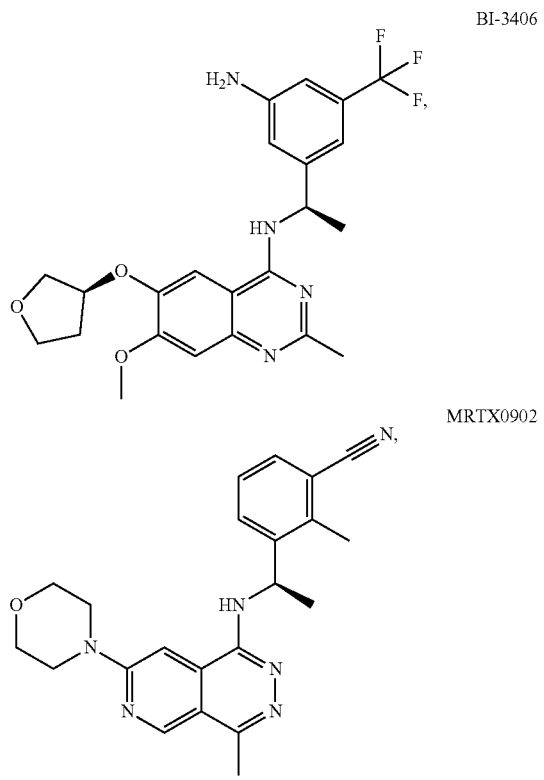

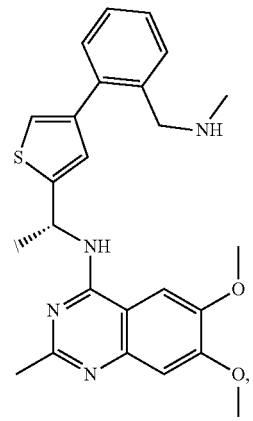

RMC-5845, and BI-1701963. In embodiments, the additional pharmacologically active agent administered in combination or in conjunction with a compound described herein (e.g., compound capable of binding a Ras protein) is an inhibitor of SOS (e.g., SOS1, SOS2) described in WO2021092115, WO2018172250, WO2019201848, WO2019122129, WO2018115380, WO2021127429, WO2020180768, or WO2020180770, all of which are herein incorporated by reference in their entirety for all purposes.

In some embodiments, any of the compounds herein that is capable of binding a Ras protein (e.g., Kras) to modulate activity of such Ras protein may be administered in combination or in conjunction with one or more checkpoint immune blockade agents (e.g., anti-PD-1 and/or anti-PD-L1 antibody, anti-CLTA-4 antibody).

In some embodiments, any of the compounds described herein that is capable of binding a Ras protein (e.g., KRAS) may be administered in combination or in conjunction with one or more pharmacologically active agents comprising an inhibitor of: (1) SOS1 or a mutant thereof (e.g., RMC-5845, BI-3406, BAY-293, BI-1701963); (2) SHP2 or a mutant thereof (e.g., 6-(4-amino-4-methylpiperidin-1-yl)-3-(2,3-dichlorophenyl)pyrazin-2-amine, TNO155, RMC-4630, ERAS-601, JAB-3068, IACS-13909/BBP-398, SHP099, RMC-4550); (3) SHC or a mutant thereof (e.g., PP2, AID371185); (4) GAB or a mutant thereof (e.g., GAB-0001); (5) GRB or a mutant thereof; (6) JAK or a mutant thereof (e.g., tofacitinib); (7) A-RAF, B-RAF, C-RAF, or a mutant thereof (e.g., RAF-709, LY-3009120); (8) BRAF or a mutant thereof (e.g., sorafenib, vemurafenib, dabrafenib, encorafenib, regorafenib, GDC-879); (9) MEK or a mutant thereof (e.g., trametinib, cobimetinib, binimetinib, selumetinib, refametinib, AZD6244); (10) ERK or a mutant thereof (e.g., ulixertinib, MK-8353, LTT462, AZD0364, $SCH_{772984}$, BIX02189, LY3214996, ravoxertinib); (11) PI3K or a mutant thereof (e.g., idelalisib, copanlisib, duvelisib, alpelisib, taselisib, perifosine, buparlisib, umbralisib, NVP-BEZ235-AN); (12) MAPK or a mutant thereof (e.g., VX-745, VX-702, RO-4402257, SCIO-469, BIRB-796, SD-0006, PH-797804, AMG-548, LY2228820, SB-681323, GW-856553, RWJ67657, BCT-197); (13) EGFR or a mutant thereof (e.g., afatinib, erlotinib, gefitinib, lapatinib, cetuximab panitumumab, osimertinib, olmutinib, EGF-816); (14) c-MET or a mutant thereof (e.g., K252a, SU11274, PHA665752, PF2341066); (15) ALK or a mutant thereof (e.g. crizotinib, alectinib, entrectinib, brigatinib); (16) FGFR1, FGFR-2, FGFR-3, FGFR-4 or a mutant thereof (e.g., nintedanib); (17) BCR-ABL or a mutant thereof (e.g., imatinib, dasatinib, nilotinib); (18) ErbB2 (Her2) or a mutant thereof (e.g., afatinib, lapatinib, trastuzumab, pertuzumab); (19) AXL or a mutant thereof (e.g., R$^{428}$, amuvatinib, XL-880); (20) NTRK1 or a mutant thereof (e.g., merestinib); (21) ROS1 or a mutant thereof (e.g., entrectinib); (22) RET or a mutant thereof (e.g., BLU-667, Lenvatinib); (23) MDM2 or a mutant thereof (e.g., HDM-201, NVP-CGM097, RG-71-12, MK-8242, RG-7388, SAR405838, AMG-232, DS-3032, RG-7775, APG-115); (24) mTOR or a mutant thereof (e.g., rapamycin, temsirolimus, everolimus, ridaforolimus); (25) BET or a mutant thereof (e.g., I-BET 151, I-BET 762, OTX-015, TEN-010, CPI-203, CPI-0610, olionon, RVX-208, ABBC-744, LY294002, AZD5153, MT-1, MS645); (26) IGF1, IGF2, IGF1R, or a mutant thereof (e.g., xentuzumab, MEDI-573); (27) CDK9 or a mutant thereof (e.g., DRB, flavopiridol, CR8, AZD 5438, purvalanol B, AT7519, dinaciclib, SNS-032); or (28) CDK4/6 (e.g., palbociclib, ribociclib, abemaciclib).

In combination therapy, a compound provided herein and other anti-cancer agent(s) may be administered either simultaneously, concurrently or sequentially with no specific time limits, wherein such administration provides therapeutically effective levels of the two compounds in the body of the patient.

In some embodiments, the compound of the present disclosure and the other anti-cancer agent(s) are generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a 3$^{rd}$ or 4th generation, can be cephalosporin or a quinolone. An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides. An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin. In some cases, an antibiotic can be 1st generation, 2nd generation, 3$^{rd}$ generation, 4th generation, or 5th generation. A first-generation antibiotic can have a narrow spectrum. Examples of 1st generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be 2nd generation. 2nd generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be 3$^{rd}$ generation. A 3$^{rd}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a 4th generation antibiotic. A 4th generation antibiotic can be Cephipime. An antibiotic can also be 5th generation. 5th generation antibiotics can be Cephtaroline or Cephtobiprole.

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount.

In some cases, a treatment regime may be dosed according to a body weight of a subject. In subjects who are determined obese (BMI>35) a practical weight may need to be utilized. BMI is calculated by: BMI=weight (kg)/[height (m)]$^2$.

Body weight may be calculated for men as 50 kg+2.3* (number of inches over 60 inches) or for women 45.5 kg+2.3 (number of inches over 60 inches). An adjusted body weight may be calculated for subjects who are more than 20% of their ideal body weight. An adjusted body weight may be the sum of an ideal body weight+(0.4× (Actual body weight-ideal body weight)). In some cases, a body surface area may be utilized to calculate a dosage. A body surface area (BSA) may be calculated by: BSA (m2)=√Height (cm)*Weight (kg)/3600.

In an aspect is provided a method of modulating activity of a Ras (e.g., K-Ras) protein, comprising contacting a Ras protein with an effective amount of a compound described herein, or a pharmaceutically acceptable salt or solvate thereof, thereby modulating the activity of the Ras (e.g., K-Ras) protein.

In some embodiments, the subject method comprises administering an additional agent or therapy.

In some embodiments is a method of modulating activity of a Ras protein, comprising contacting a Ras protein with an effective amount of a compound described, or a pharmaceutically acceptable salt or solvate thereof, wherein said modulating comprises inhibiting the Ras (e.g., K-Ras) protein activity. In some embodiments is a method of modulating activity of a Ras protein including Ras mutant (e.g., G12C, G12D, G12S, G1V, G13C, or G13D) proteins such as K-Ras, H-Ras, and N-Ras, comprising contacting the Ras protein with an effective amount of a compound described herein, or a pharmaceutically acceptable salt or solvate thereof.

In some embodiments, provided is a method of reducing Ras signaling output in a cell by contacting the cell with a compound described herein. A reduction in Ras signalling can be evidenced by one or more members of the following: (i) an increase in steady state level of GDP-bound modified protein or a decrease in steady state level of GTP-bound modified protein; (ii) a reduction of phosphorylated AKTs473, (iii) a reduction of phosphorylated ERKT202/y204, (iv) a reduction of phosphorylated S6S235/236, and (v) reduction of cell growth of a tumor cell expressing a Ras mutant (e.g., G12C, G12D, G12S, G1V, G13C, or G13D) protein, and (vi) reduction in Ras interaction with a Ras-pathway signaling protein. Non-limiting examples of Ras-pathway signaling protein include SOS (including SOS1 and SOS2), RAF, SHC, SHP (including SHP1 and SHP2), MEK, MAPK, ERK, GRB, RASA1, and GNAQ. In some cases, the reduction in Ras signaling output can be evidenced by two, three, four or all of (i)-(v) above. In some embodiments, the reduction any one or more of (i)-(v) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to control untreated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine (i.e. colon)), endometrium, stomach, hematopoietic tissue (e.g., lymphoid tissue), etc. Examples of the tumor cell line with a K-Ras mutation may include, but are not limited to, A549 (e.g., K-Ras G12S), AGS (e.g., K-Ras G12D), ASPC1 (e.g., K-Ras G12D), Calu-6 (e.g., K-Ras $Q^{61}K$), CFPAC-1 (e.g., K-Ras G12V), CL40 (e.g., K-Ras G12D), COLO678 (e.g., K-Ras G12D), COR-L$^{23}$ (e.g., K-Ras G12V), DAN-G (e.g., K-Ras G12V), GP2D (e.g., K-Ras G12D), GSU (e.g., K-Ras G12F), HCT116 (e.g., K-Ras G13D), HECIA (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANCI (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK—CO-1 (e.g., K-Ras G12V), SKLU1 (e.g., K-Ras G12D), SKM-1 (e.g., K-Ras K117N), SNUI (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-$C_2$A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras $Q^{61}L$), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In an aspect is provided a modified Ras mutant protein comprising a compound described herein (or a remnant of a compound described herein wherein the remnant of said compound is modified from a stand-alone compound described herein upon covalently bonding to the amino acid) covalently bonded to the amino acid corresponding to position 12 or 13 of SEQ ID No: 1. In some embodiments, such covalently bonded modified Ras mutant protein exhibits a reduced Ras signaling output (e.g., compared to a corresponding unmodified Ras mutant absent of the covalently bonded compound). In some embodiments, a modified Ras mutant protein is a K-Ras G12D mutant, an H-Ras G12D mutant, or a N-Ras G12D mutant. In some embodiments, a modified Ras mutant protein comprises an amino acid sequence selected from the group consisting of SEQ ID No. 2, SEQ ID No. 6, SEQ ID No. 8, and a respective fragment thereof comprising the aspartate residue corresponding to position 12 of SEQ ID No: 2. In embodiments, the modified Ras mutant protein comprises a compound described herein covalently bonded to the amino acid residue corresponding to position 12 or 13 of SEQ ID No: 1, wherein the Ras mutant protein is a human protein selected from KRas G12D, KRas G12C, KRas G13D, and KRas G13C. In embodiments, the modified Ras mutant protein comprises a compound described herein covalently bonded to the amino acid residue corresponding to position 12 or 13 of SEQ ID No: 1, wherein the Ras mutant protein is a—mammalian Ras protein (including human protein) selected from NRas G12D, NRas G12C, NRas G13D, and NRas G13C. In embodiments, the modified Ras mutant protein comprises a compound described herein covalently bonded to the amino acid residue corresponding to position 12 or 13 of SEQ ID No: 1, wherein the Ras mutant protein is a mammalian protein (including human protein) selected from HRas G12D, HRas G12C, HRas G13D, and HRas G13C. It will be understood that a compound described herein may be modified upon covalently binding an amino acid (e.g., mutant amino acid other than G) corresponding to position 12 or 13 of human KRas (e.g., SEQ ID. No: 1). A subject compound of the present disclosure encompasses a compound described herein immediately prior to covalently bonding the Ras mutant protein as well as the resulting compound covalently bonded to the modified Ras mutant protein. For example, a subject compound of the present disclosure can be covalently bonded to a mutant Ras protein to form a modified Ras mutant protein when a ring of the compound opened upon covalently bonding to the amino acid corresponding to position 12 or 13 of SEQ ID No: 1. The compound prior to and subsequent to such covalent binding are all considered a subject compound of the present invention.

In embodiments of a modified Ras mutant protein described herein, the reduced Ras signaling output is evidenced by one or more a reduced output selected from the group consisting of (i) an increase in steady state level of GDP-bound modified protein or a decrease in steady state level of GTP-bound modified protein; (ii) a reduction of phosphorylated AKTs473, (iii) a reduction of phosphorylated ERK T202/Y204, (iv) a reduction of phosphorylated S6 S235/236, (v) reduction of cell growth of a tumor cell expressing a Ras mutant protein (e.g., G12D, G12C, G12S, G13D, G13C, or G13S), and (vi) reduction in Ras interaction with a Ras-pathway signaling protein In embodiments, the modified Ras mutant protein described herein is formed by contacting a compound described herein with the aspartate residue of an unmodified Ras G12D mutant protein, wherein the compound comprises a moiety susceptible to reacting with a nucleophilic aspartate residue corresponding to position 12 of SEQ ID No: 2. In some embodiments, the compound selectively labels the aspartate residue corresponding to position 12 of SEQ ID No. 2 (a G12D mutant) relative to a valine (G12V) residue at the same position. In some embodiments, the compound selectively labels the aspartate residue as compared to (i) a serine residue of a K-Ras G12S mutant protein, said serine corresponding to residue 12 of SEQ ID NO: 4, and/or (ii) a valine residue of a K-Ras G12V mutant protein, said valine corresponding to residue 12 of SEQ ID NO: 3. In some embodiments, the compound selectively labels the aspartate residue as compared to (i) an serine residue of a K-Ras G12S mutant protein, said aspartate corresponding to residue 12 of SEQ ID NO: 4, and/or (ii) a valine residue of a K-Ras G12V mutant protein, said valine corresponding to residue 12 of SEQ ID NO: 3, by at least 1, 2, 3, 4, 5, 10 folds or more, when assayed under comparable conditions. In some embodiments, the compound selectively labels the aspartate residue corresponding to position 12 of SEQ ID No. 2 (a G12D KRas mutant) relative to a glycine residue at the same position in wildtype KRas.

In embodiments of the modified Ras mutant protein described herein, the compound contacts the aspartate residue of an unmodified Ras G12D protein corresponding to position 12 of SEQ ID No: 2 in vitro.

In embodiments of the modified Ras mutant protein described herein, the compound contacts the aspartate residue of an unmodified K-Ras G12D protein corresponding to position 12 of SEQ ID No: 2 in vivo.

In an aspect is provided a method of treating cancer in a subject comprising a Ras mutant protein (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S), the method comprising modifying the Ras mutant protein of said subject by administering to said subject a compound described herein, wherein the compound is characterized in that upon contacting a Ras mutant protein, said Ras mutant protein is modified covalently at a residue corresponding to reside 12 or 13 of SEQ ID No: 1, such that said modified Ras mutant protein exhibits reduced Ras signaling output (e.g., compared to a control such as an unmodified Ras mutant protein not covalently bonded with any compound such as a compound disclosed herein).

In some aspects, a subject compound exhibits one or more of the following characteristics: it is capable of reacting with a mutant residue (e.g., KRas G12D, KRas G12C, KRas G13D, KRas G13C, NRas G12D, NRas G12C, NRas G13D, NRas G13C, HRas G12D, HRas G12C, HRas G13D, or HRas G13C) of a Ras mutant protein and covalently modify such Ras mutant and/or it comprises a moiety susceptible to reacting with a nucleophilic amino acid residue corresponding to position 12 or 13 of SEQ ID No: 1 (e.g., KRas G12D, KRas G12C, KRas G13D, KRas G13C, NRas G12D, NRas G12C, NRas G13D, NRas G13C, HRas G12D, HRas G12C, HRas G13D, or HRas G13C). In some embodiments, a subject compound when used to modify a Ras mutant protein, reduces the Ras protein's signaling output. In some embodiments, a subject compound exhibits an IC50 (against a mutant Ras (e.g., KRas G12D, KRas G12C, KRas G13D, KRas G13C, NRas G12D, NRas G12C, NRas G13D, NRas G13C, HRas G12D, HRas G12C, HRas G13D, or HRas G13C), as ascertained by reduction of Ras:: SOS1 interaction) of less than 10 uM, 5 uM, 1 uM, 500 nM, less than 100 nM, less than 50 nM, 10 nM, 5 nM, 1 nM, 500 pM, 50 pM, 10 pM or less. In some embodiments, a subject compound exhibits an IC50 (against a mutant Ras (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S), as ascertained by an assay described herein) of less than 10 uM, 5 uM, 1 uM, 500 nM, less than 100 nM, less than 50 nM, 10 nM, 5 nM, 1 nM, 500 pM, 50 pM, 10 pM or less.

In some embodiments, a modified Ras mutant protein disclosed herein exhibits a reduced Ras signaling output. A reduction of signaling output can be ascertained by a wide variety of methods known in the art. For example, phosphorylation of a substrate or a specific amino acid residue thereof can be detected and/or quantified one or more techniques, such as kinase activity assays, phospho-specific antibodies, Western blot, enzyme-linked immunosorbent assays (ELISA), cell-based ELISA, intracellular flow cytometry, mass spectrometry, and multi-analyte profiling. A host of readout can evidence a reduction of Ras signaling output including without limitation: (i) an increase in steady state level of GDP-bound modified protein or a decrease in steady state level of GTP-bound modified protein; (ii) a reduction of phosphorylated AKTs473, (iii) a reduction of phosphorylated ERK T202/Y204, (iv) a reduction of phosphorylated S6 S235/236, and (v) reduction of cell growth of a tumor cell expressing a Ras mutant protein (e.g., KRas G12D, KRas G12C, KRas G12S, KRas G13D, KRas G13C, KRas G13S, NRas G12D, NRas G12C, NRas G12S, NRas G13D, NRas G13C, NRas G13S, HRas G12D, HRas G12C, HRas G12S, HRas G13D, HRas G13C, or HRas G13S), and (vi) reduction in Ras interaction with a Ras-pathway signaling protein. In some embodiments, a reduction is evidenced by 2, 3, 4 or more of items (i)-(vi). In some embodiments, the reduction in Ras signaling output can be evidenced by any one of (i)-(vi) as compared to control unmodified corresponding Ras proteins that is not covalently bonded to any compound disclosed herein. For example, a control Ras protein, as described herein, can be a Ras protein (e.g., wildtype or mutated) that is not complexed with any subject compound of the present disclosure. The increase in item (i) or reduction in items (ii) through (vi) can be at least about 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to the control Ras proteins. In some embodiments, a reduction in Ras interaction with a Ras-pathway signaling protein is established by a reduced interaction with SOS (including SOS1 and SOS2), RAF, SHC, SHP (including SHP1 and SHP2), MEK, MAPK, ERK, GRB, RASA1, or GNAQ.

In embodiments the modified Ras mutant protein described herein is formed by contacting a compound with the aspartate residue of an unmodified Ras G12D mutant protein, wherein the compound comprises a moiety susceptible to reacting with a nucleophilic aspartate residue corresponding to position 12 of SEQ ID No: 2. Non-limiting examples of a moiety susceptible to reaction with a nucleophilic serine residue of a K-Ras G12D protein comprise an optionally substituted aziridinyl.

Signaling output measured in terms of IC50 values can be obtained, a ratio of IC50 against one mutant relative to another mutant can be calculated. For instance, a selective reduction of K-Ras G12D signaling output can be evidenced by a ratio greater than one. In particular, a selective reduction of K-Ras G12D signaling relative to K-Ras G12S signaling is evidenced as the ratio of IC50 (against K-Ras G12S) to IC50 (against K-Ras G12D) is greater than 1.

It will be understood that when a compound described herein selectively labels the aspartate residue of a K-Ras G12D protein compared to another K-Ras protein(s) (e.g., WT, G12S, or G12V), the compound labels the K-Ras G12D protein with greater speed or to a greater degree or by any other quantifiable measurement compared to the other K-Ras protein (e.g., WT, G12S, G12V), under similar or identical reaction conditions for the proteins being compared. In some embodiments, the greater labeling of K-Ras G12D can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5- fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to another K-Ras protein (e.g., WT, G12S, or G12V).

In embodiments, the compounds described herein, or a pharmaceutically acceptable salt or solvate thereof, are Ras modulators (including Ras inhibitors) capable of covalently modifying a Ras protein. Ras proteins being modified can be Ras G12D mutants from K-Ras, H-Ras or N-Ras. The compounds, a pharmaceutically acceptable salt or solvate thereof disclosed herein, have a wide range of applications in therapeutics, diagnostics, and other biomedical research.

In an aspect is provided a method of treating cancer in a subject comprising a Ras G12D mutant protein, comprising modifying the Ras G12D mutant protein of said subject by administering to said subject a compound described herein, wherein said compound is characterized in that upon contacting the Ras G12D mutant protein, said the Ras G12D mutant protein is modified covalently at an aspartate residue corresponding to reside 12 of SEQ ID No: 2, such that said modified K-Ras G12D protein exhibits reduced Ras signaling output (e.g., compared to a corresponding unmodified Ras protein unbound to the covalent compound).

In an aspect is provided a method of modulating activity of a Ras protein (e.g., K-Ras, mutant K-Ras, K-Ras G12D), comprising contacting a Ras protein with an effective amount of a compound described herein, or a pharmaceutically acceptable salt or solvate thereof, thereby modulating the activity of the Ras protein.

In practicing any of the methods disclosed herein, the Ras target to which a subject compound binds covalently can be a Ras mutant (e.g., KRas G12D, KRas G12C, KRas G13D, KRas G13C, NRas G12D, NRas G12C, NRas G13D, NRas G13C, HRas G12D, HRas G12C, HRas G13D, or HRas G13C).

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

The compounds described herein, or a pharmaceutically acceptable salt or solvate thereof, are administered to subjects in a biologically compatible form suitable for administration to treat or prevent diseases, disorders or conditions. Administration of the compounds described herein can be in any pharmacological form including a therapeutically effective amount of a compound described herein, or a pharmaceutically acceptable salt or solvate thereof, alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s) (or carrier(s)) is acceptable or suitable if the excipient is compatible with the other ingredients of the composition and not deleterious to the recipient (i.e., the subject) of the composition.

In some embodiments of the methods described herein, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments of the methods described herein, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

ADDITIONAL EMBODIMENTS

Embodiment 1. A Compound of Formula (I), or a Pharmaceutically Acceptable Salt or Solvate Thereof:

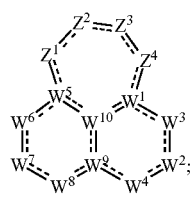

Formula (I)

wherein:
$Z^1$, $Z^2$, z3, and $Z^4$ are each independently selected from $N(R^4)$, $N(R^{11c})$, $N(R^{11d})$, N, $C(R^4)$, $C(R^{11c})$, $C(R^{11d})$, $C(R^4)(R^{11c})$, $C(R^{11c})(R^{11c})$, $C(R^4)(R^4)$, $C(R^{11c})(R^{11d})$, S, O, and C(O); wherein at least one of $Z^1$, $Z^2$, z3, and $Z^4$ is $N(R^4)$, $N(R^{11d})$, $C(R^4)$, $C(R^{11d})$, $C(R^4)(R^{11c})$, $C(R^4)(R^4)$, $C(R^{11c})(R^{11d})$, or C(O);

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $N(R^{2a})$, N, $C(R^2)$, $C(R^2)(R^{2a})$, $S(O)_2$, or S(O);

$R^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12a}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$R^{2a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-9heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is $N(R^{3b})$, N, $C(R^3)$, $C(R^3)(R^{3a})$, C(O), $S(O)_2$, or S(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$;

$W^4$ is N or N(R$^{3c}$);

$R^{3c}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three $R^{20c}$;

$W^5$ is C(R$^5$), C, or N;

$R^5$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three $R^{20d}$;

$W^6$ is N(R$^{6b}$), N, C(R$^6$), C(R$^6$)(R$^{6a}$), C(O), S(O), or S(O)$_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$ heteroaryl are optionally substituted with one, two, or three $R^{20e}$;

$R^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$;

$W^7$ is N(R$^7$), C(R$^7$), or C(R$^7$)(R$^{7a}$);

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20f}$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three $R^{20f}$;

$R^7$ is -L$^7$-R$^{17}$;

$L^7$ is a bond, —O—, —N(R$^{7d}$)—, —C(O)—, —S—, —S(O)$_2$—, —S(O)—, —P(O)R$^{7d}$, CR$^7$°R$^{7c}$, —OCR7R$^{7c}$—, —N(R$^{7d}$)CR$^7$GR$^{7c}$—, —C(O)CR$^7$R$^{7c}$—, —$^5$CR7R$^{7c}$—, —S(O)$_2$CR$^7$GR$^{7c}$—, —S(O)CR$^7$R$^{7c}$—, —P(O)R$^{7d}$ CR$^7$CR$^{7c}$—, —CR$^7$CR$^7$cCR7GR7c, —CR$^7$CR$^7$CO—, —CR$^7$GR$^7$°N(R$^{7d}$)—, —CR$^7$GR7° C.(O)—, —CR$^7$CR$^{7c}$S—, —CR$^7$°R$^7$CS(O)$_2$—, —CR$^7$GR$^{7c}$S(O)—, —CR$^7$R$^7$ cP(O)R$^{7d}$ —, —N(R$^{7d}$)C(O)—, —N(R$^{7d}$)S(O)$_2$—, —N(R$^{7d}$)S(O)—, —N(R$^{7d}$)P(O)R$^{7d}$ —, —C(O)N(R$^{7d}$)—, —S(O)$_2$N(R$^{7d}$)—, —S(O)N(R$^{7d}$)—, —P(O)R$^{7a}$N(R$^{7d}$)—, —OC(O)—, —OS(O)$_2$—, —OS(O)—, —OP(O)R$^{7d}$—, —C(O)O—, —S(O)$_{20}$—, —S(O)O—, or —P(O)R$^{7d}$ O—;

$R^{17}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$W^8$ is C(R$^8$), C(R$^8$)(R$^{8a}$), N, N(R$^{8b}$), C(O), S(O), or S(O)$_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20h}$;

R8b is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$ R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three R$^{20h}$;

W$^9$ is C(R$^9$), C, or N;

W$^{10}$ is C(R$^9$), C, or N;

each R$^9$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three R$^{20i}$;

R$^4$ is -L$^4$-R$^{4a}$;

L$^4$ is a bond, —O—, —N(R$^{4d}$)—, —C(O)—, —S—, —S(O)$_2$—, —S(O)—, —P(O)R$^{4d}$—, CR$^{4c}$R$^4$, —OCR$_4$R$^{4c}$—, —N(R$^{4d}$)CR$^{4c}$R$^{4c}$—, —C(O)CR$^4$R$^{4d}$—, —SCR$^4$R$^{4c}$—, —S(O)$_2$CR$^4$R$^{4c}$—, —S(O)CR$^4$R$^{4c}$—, —P(O)R$^{4d}$CR4R$^{4c}$—, —CR$^4$R$^4$CR$^4$R$^4$, —CR$^4$R$^{4O}$—, —CR$^4$R$^4$CN(R$^{4d}$)—, —CR$^4$R$^{4c}$C(O)—, —CR$^{4c}$R$^{4c}$S—, —CR$^4$R$^{4c}$S(O)$_2$—, —CR$^4$GR4CS(O)—, —CR$^4$R$^4$ cP(O)R$^{4d}$—, —N(R$^{4d}$)C(O)—, —N(R$^{4d}$)S(O)$_2$—, —N(R$^{4d}$)S(O)—, —N(R$^{4d}$)P(O)R$^{4d}$—, —C(O)N(R$^{4d}$)—, —S(O)$_2$N(R$^{4d}$)—, —S(O)N(R$^{4d}$)—, —P(O)R$^{4d}$N(R$^{4d}$)—, —OC(O)—, —OS(O)$_2$—, —OS(O)—, —OP(O)R$^{4d}$—, —C(O)O—, —S(O)$_{20}$—, —S(O)O—, or —P(O)R$^{44}$O—;

each R$^{4c}$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, —OC(O)R$^{14}$a, —N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14a}$, and —N(R$^{14}$)S(O)$_2$R$^{14}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each R$^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, and —OC(O)R$^{14}$a, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_2$-heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14}$a, —S(O)$_2$R$^{14}$, —S(O)$_2$N(R$^{14}$)(R$^{14}$), and —OC(O)R$^{14a}$;

each R$^{4a}$ is independently selected from $C_{3-10}$cycloalkyl, $C_{2-9}$heterocycloalkyl, $C_{6-10}$aryl, and $C_1$-heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four R$^{4b}$;

each R$^4$b is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more R$^{20}$j;

each R$^{11}$c is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three R$^{20}$k;

each R$^{11d}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three $R^{20}k$.

each $R^{12}$ is independently selected from hydrogen, $C_{1-6}$alkyl, $C_{2-6}$alkenyl, $C_{2-6}$alkynyl, $C_{3-10}$cycloalkyl, —C(R$^{12}$b)$_2$-C$_{3-10}$cycloalkyl, $C_{2-9}$heterocycloalkyl, —C(R$^{12}$b)$_2$-C$_{2-9}$heterocycloalkyl, $C_{6-10}$aryl, —C(R$^{12}$b)$_2$-C$_{6-10}$aryl, —C(R$^{12}$b)$_2$-C$_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C(R$^{12}$b)$_2$-C$_{3-10}$cycloalkyl, $C_{2-9}$heterocycloalkyl, —C(R$^{12}$b)$_2$-C$_{2-9}$heterocycloalkyl, $C_{6-10}$aryl, —C(R$^{12}$b)$_2$-C$_{6-10}$aryl, —C(R$^{12}$b)$_2$-C$_{1-9}$heteroaryl, and $C_{1-9}$heteroaryl are optionally substituted with one, two, or three $R^{20l}$;

$R^{12}$a is selected from $C_{1-6}$alkyl, $C_{2-6}$alkenyl, $C_{2-6}$alkynyl, $C_{3-10}$cycloalkyl, —C(R$^{12}$b)$_2$-C$_{3-10}$cycloalkyl, $C_{2-9}$heterocycloalkyl, —C(R$^{12}$b)$_2$-C$_{2-9}$heterocycloalkyl, $C_{6-10}$aryl, —C(R$^{12}$b)$_2$-C$_{6-10}$aryl, —C(R$^{12}$b)$_2$-C$_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C(R$^{12}$b)$_2$-C$_{3-10}$cycloalkyl, $C_{2-9}$heterocycloalkyl, —C(R$^{12}$b)$_2$-C$_{2-9}$heterocycloalkyl, $C_{6-10}$aryl, —C(R$^{12}$b)$_2$-C$_{6}$-10aryl, —C(R$^{12}$b)$_2$-C$_{1-9}$heteroaryl, and $C_{1-9}$heteroaryl are optionally substituted with one, two, or three $R^{20l}$, each $R^{12}$b is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$, each $R^{1d}$ is independently selected from hydrogen, $C_{1-6}$alkyl, and $C_{1-6}$haloalkyl;

each $R^{14}$a is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$-C$_{3-10}$cycloalkyl, $C_{2-9}$heterocycloalkyl, —CH$_2$-C$_{2-9}$heterocycloalkyl, $C_{6-10}$aryl, —CH$_2$-C$_{6-10}$aryl, —CH$_2$-C$_1$-9heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

Embodiment 2. A Compound of Formula (II), or a Pharmaceutically Acceptable Salt or Solvate Thereof:

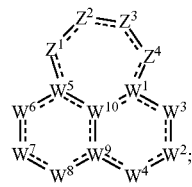

Formula (II)

wherein:

$Z^1$, $Z^2$, and $Z^3$ are each independently selected from N(R$^4$), N(R$^{11c}$), N(R$^{11d}$), N, C(R$^4$), C(R$^{11c}$), C(R$^{11d}$), C(R$^4$)(R$^{11c}$), C(R$^{11c}$)(R$^{11c}$), C(R$^4$)(R$^4$),C(R$^{11c}$)(R$^{11d}$), S, O, and C(O); $Z^4$ is selected from N(R$^4$), N(R$^{11c}$), N(R$^{11d}$), N, C(R$^4$), C(R$^{11c}$), C(R$^{11d}$), C(R$^4$)(R$^{11c}$), C(R$^{11c}$)(R$^{11c}$), C(R$^4$)(R$^4$), C(R$^{11c}$)(R$^{11d}$), S, and O;

wherein at least one of $Z^1$, $Z^2$, z3 and $Z^4$ is N(R$^4$), N(R$^{1d}$), C(R$^4$), C(R$^{11d}$), C(R$^4$)(R$^{11c}$), C(R$^4$)(R$^4$), or C(R$^{11c}$)(R$^{11d}$);

$W^1$ is C(R$^1$), C, or N;

$R^1$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three $R^{20a}$, $W^2$ is N(R$^{2a}$), N, C(R$^2$), C(R$^2$)(R$^{2a}$), C(O), S(O)$_2$, or S(O);

$R^2$ is selected from halogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20o}$;

$R^{2a}$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20b}$;

$W^3$ is N(R$^{3b}$), N, C(R$^3$), C(R$^3$)(R$^{3a}$), C(O), S(O)$_2$, or S(O);

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20c}$.

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20c}$;

$W^4$ is N or N(R$^{3c}$);

$R^{3c}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-heteroaryl are optionally substituted with one, two, or three R$^{20c}$;

$W^5$ is C(R$^5$), C, or N;

$R^5$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three R$^{20d}$;

$W^6$ is N(R$^{6b}$), N, C(R$^6$), C(R$^6$)(R$^{6a}$), C(O), S(O), or S(O)$_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20e}$;

$R^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-}$,heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$ R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20e}$, $W^7$ is N(R$^7$), C(R$^7$), or C(R$^7$)(R$^{7a}$);

$R^{7a}$ and each R$^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20f}$, $R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three R$^{20f}$, $R^7$ is -L$^7$-R$^{17}$;

$L^7$ is a bond, —O—, —N(R$^{7d}$)—, —C(O)—, —S—, —S(O)$_2$—, —S(O)—, —P(O)R$^{7d}$, CR$^7$R$^{7c}$, —OCR$_7$R$^{7c}$—, —N(R$^{7d}$)CR$^7$R$^{7c}$—, —C(O)CR$^{7o}$R$^{7c}$—, —SCR$^7$GR$^{7c}$—, —S(O)$_2$CR$^7$GR7c—, —S(O)CR$^7$GR$^{7c}$—, —P(O)R$^{7d}$ CR7CR$^{7c}$—, —CR$^7$CR$^7$&CR$^7$CR$^7$c, —CR$^7$CR$^7$CO—, —CR$^7$R$^{7o}$N $(R^{7d})$—, —$CR^7CR^{7o}$ C.(O)—, —$CR^7cR7CS$—, —$CR^7CR^{7c}S(O)_2$—, —$CR^7cR^{7c}S(O)$—, —$CR^7GR7cP(O)R^{7d}$—, —$N(R^{7d})C(O)$—, —$N(R^{7d})S(O)_2$—, —$N(R^{7d})S(O)$—, —$N(R^{7d})P(O)R^{7d}$—, —C(O)N$(R^{7d})$—, —$S(O)_2N(R^{7d})$—, —$S(O)N(R^{7d})$—, —$P(O)R^{7a}N(R^{7d})$—, —OC(O)—, —$OS(O)_2$—, —OS(O)—, —$OP(O)R^{74}$—, —C(O)O—, —$S(O)_{20}$—, —S(O)O—, or —$P(O)R^{7a}O$—;

$R^{17}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$W^8$ is $C(R^8)$, $C(R^8)(R^{8a})$, N, $N(R^{8b})$, C(O), S(O), or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$—,heteroaryl are optionally substituted with one, two, or three $R^{20h}$;

$W^9$ is $C(R^9)$, C, or N; $W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$, $R^4$ is -$L^4$-$R^{4a}$;

$L^4$ is a bond, —O—, —$N(R^{4d})$—, —C(O)—, —S—, —$S(O)_2$—, —S(O)—, —$P(O)R^{4d}$—, $CR^4CR^4$, —$OCR_4R^{4c}$—, —$N(R^{4d})CR^4GR^{4c}$—, —$C(O)CR^{4o}$ C.$R^{4c}$—, —$SCR^4R^{4c}$—, —$S(O)_2CR^4R^{4c}$—, —$S(O)CR^4R^{4c}$—, —$P(O)R^{4d}CR4R^{4c}$, —$CR^4R^4CR^4R^4$, —$CR^4R^4CO$—, —$CR^4R^4CN(R^{4d})$—, —$CR^4GR4CC(O)$—, —$CR^4R^{4S}$—, —$CR^4CR^{4c}S(O)_2$—, —$CR^4CR^{4c}S(O)$—, —$CR^{4o}$ C. $R^4CP(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^4ON(R^{4d})$—, —OC(O)—, —$OS(O)_2$—, —OS(O)—, —$OP(O)R^{4d}$—, —C(O)O—, —$S(O)_{20}$—, —S(O)O—, or —$P(O)R^{4d}O$—;

each $R^4$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{143}$, —$S(O)_2R^{14}$, —$S(O)_2N(R^{14})(R^{14})$, —$OCH_2C(O)OR^{14}$, —$OC(O)R^{14}$a, —$N(R^{14})(R^{14})$, —$N(R^{14})C(O)N(R^{14})(R^{14})$, —$N(R^{14})C(O)OR^{14}$, —$N(R^{14})C(O)R^{14a}$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{143}$, —$S(O)_2R^{14}$, —$S(O)_2N(R^{14})(R^{14})$, —$OCH_2C(O)OR^{14}$, and —$OC(O)R^{14}$a, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from hydrogen, halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12}$ ($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, S(=O) (=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, or three $R^{20k}$, each $R^{11d}$ is independently selected from halogen, oxo, —CN, C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, C$_{1-11}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, C$_{2-6}$alkynyl, C$_{1-6}$haloalkyl, C$_{3-12}$cycloalkyl, —CH$_2$-C$_{3-12}$cycloalkyl, C$_{1-11}$heterocycloalkyl, —CH$_2$-C$_{1-11}$heterocycloalkyl, C$_{6-10}$aryl, —CH$_2$-C$_{6-10}$aryl, —CH$_2$-C$_{1-11}$heteroaryl, and C$_{1-11}$heteroaryl are optionally substituted with one, two, or three $R^{20k}$;

each $R^{12}$ is independently selected from hydrogen, C$_{1-6}$alkyl, C$_{2-6}$alkenyl, C$_{2-6}$alkynyl, C$_{3-10}$cycloalkyl, —C($R^{12b}$)$_2$-C$_{3-10}$cycloalkyl, C$_{2-9}$heterocycloalkyl, —C($R^{12b}$)$_2$-C$_{2-9}$heterocycloalkyl, C$_{6-10}$aryl, —C($R^{12b}$)$_2$-C$_{6-10}$aryl, —C($R^{12b}$)$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —C($R^{12b}$)$_2$-C$_{3-10}$cycloalkyl, C$_{2-9}$heterocycloalkyl, —C($R^{12}$b)$_2$-C$_{2-9}$heterocycloalkyl, C$_{6-10}$aryl, —C($R^{12}$b)$_2$-C$_{6-10}$aryl, —C($R^{12}$b)$_2$-C$_{1-9}$heteroaryl, and C$_{1-9}$heteroaryl are optionally substituted with one, two, or three $R^{20l}$;

each $R^{12}$b is independently selected from hydrogen and $R^{20l}$;

each $R^{13}$ is independently selected from hydrogen, C$_{1-6}$alkyl, and C$_{1-6}$haloalkyl; or $R^{12}$ and $R^{13}$, together with the nitrogen to which they are attached, form a C$_{2-9}$heterocycloalkyl ring optionally substituted with one, two, or three $R^{20l}$;

each $R^{1d}$ is independently selected from hydrogen, C$_{1-6}$alkyl, and C$_{1-6}$haloalkyl;

each $R^{14}$a is independently selected from C$_{1-6}$alkyl and C$_{1-6}$haloalkyl;

each $R^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three $R^{20m}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), —OCH$_2$C(O)O$R^{22}$, and —OC(O)$R^{25}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1}$-9heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$;

each $R^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each $R^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each $R^{23}$ is independently selected from H and C$_{1-6}$alkyl;
each $R^{24}$ is independently selected from H and C$_{1-6}$alkyl;
each $R^{25}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl; and ----- indicates a single or double bond such that all valences are satisfied.

Embodiment 3 a Compound of Formula (I), or a Pharmaceutically Acceptable Salt or Solvate Thereof:

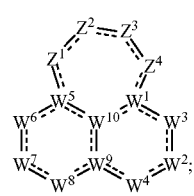

Formula (I)

wherein:
$Z^1$, $Z^2$, $Z^3$, and $Z^4$ are each independently selected from N($R^4$), N($R^{11c}$), N($R^{11d}$), N, C($R^4$), C($R^{11c}$), C($R^{11d}$), C($R^4$)($R^{11c}$), C($R^{11c}$)($R^{11d}$), C($R^4$)($R^4$), C($R^{11c}$)($R^{11d}$), S, O, and C(O); wherein at least one of $Z^1$, $Z^2$, z3, and $Z^4$ is N($R^4$), N($R^{11d}$), C($R^4$), C($R^{11d}$), C($R^4$)($R^{11c}$), C($R^4$)($R^4$), C($R^{11c}$)($R^{11d}$), or C(O);

$W^1$ is C, C($R^1$), or N;

$R^1$ is selected from hydrogen, halogen, —CN, C$_{1-6}$alkyl, C$_{2-6}$alkenyl, C$_{2-6}$alkynyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein C$_{1-6}$alkyl, C$_{2-6}$alkenyl, and C$_{2-6}$alkynyl are optionally substituted with one, two, or three $R^{20}$;

$W^2$ is C($R^2$), N($R^{2a}$), N, C($R^2$)($R^{2a}$), S(O)$_2$, or S(O);

$R^2$ is selected from $-OR^{12}a$, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-9heteroaryl, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2a}$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$;

$W^3$ is N, $N(R^3b)$, $C(R^3)$, $C(R^3)(R^{3a})$, $C(O)$, $S(O)_2$, or $S(O)$;

$R^3$ and $R^{3a}$ are independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=OX=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$;

$R^3b$ is selected from hydrogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-C(O)OR^{12}$, $-OC(O)N(R^{12})(R^{13})$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-S(O)_2R^{15}$, $-S(O)_2N(R^{12})(R^{13})-$, $-S(=OX=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$;

$W^4$ is N or $N(R^3c)$;

$R^3c$ is selected from hydrogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-C(O)OR^{12}$, $-OC(O)N(R^{12})(R^{13})$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-S(O)_2R^{15}$, $-S(O)_2N(R^{12})(R^{13})-$, $-S(=OX=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$, $W^5$ is C, $C(R^5)$, or N;

$R^5$ is selected from hydrogen, halogen, $-CN$, $C_{1-6}$alkyl, $C_{2-6}$alkenyl, $C_{2-6}$alkynyl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$, $W^6$ is $C(R^6)$, $N(R^{6\%})$, N, $C(R^6)(R^{6a})$, $C(O)$, $S(O)$, or $S(O)_2$;

$R^6$ and $R^{6a}$ are independently selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=OX=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6\ 9}$heteroaryl are optionally substituted with one, two, or three $R^{20}e$;

$R^6$ is selected from hydrogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-C(O)OR^{12}$, $-OC(O)N(R^{12})(R^{13})$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-S(O)_2R^{15}$, $-S(O)_2N(R^{12})(R^{13})-$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20}e$;

$W^7$ is $C(R^7)$, $N(R^7)$, or $C(R^7)(R^{7a})$;

$R^{7a}$ and each $R^7c$ are independently selected from hydrogen, halogen, $-CN$, $C_{1-6}$alkyl, $C_{2-6}$alkenyl, $C_{2-6}$alkynyl, $C_{3-10}$cycloalkyl, $C_2$-heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})-$, $-S(=OX=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20}f$;

$R^{7d}$ is independently selected from hydrogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-C(O)OR^{12}$, $-OC(O)N(R^{12})(R^{13})$, $-C(O)R^{15}$, $-S(O)R^{15}$, $-OC(O)R^{15}$, $-C(O)N(R^{12})$ (R¹³), —C(O)C(O)N(R¹²)(R¹³), —S(O)₂R¹⁵, —S(O)₂N(R¹²)(R¹³)—, —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20}f$, $R^7$ is -$L^7$-$R^{17}$;

$L^7$ is a bond, —O—, —N($R^{7d}$)—, —C(O)—, —S—, —S(O)₂—, —S(O)—, —P(O)$R^{74}$—, $CR^{7o}R^{7c}$, —OC$R^7$C$R^7$c, —N($R^{74}$)C$R^7R^{7c}$—, —C(O) $CR^{7o}R^{7c}$—, —SC$R^7R^{76}$—, —S(O)₂$CR^{7o}R^7$c—, —S(O)C$R^7R^{7c}$—, —P(O)$R^{7d}$ $CR^7CR^{7c}$—, —$CR^7CR^{7c}$C$CR^{7o}R^7$c, —$CR^7CR^7$CO—, —$CR^7GR^{7a}$N($R^{74}$)—, —$CR^7GR^{7o}$ C.(O)—, —$CR^7CR^{7c}$S—, —$CR^7CR^{7c}$S(O)₂—, —$CR^{7o}R^{7c}$S(O)—, —$CR^7CR^7$cP(O)$R^{74}$—, —N($R^{74}$)C(O)—, —N($R^{7d}$)S(O)₂—, —N($R^{7d}$)S(O)—, —N($R^{7d}$)P(O)$R^{74}$—, —C(O)N($R^{74}$)—, —S(O)₂N($R^{74}$)—, —S(O)N($R^{7d}$)—, —P(O)$R^{7a}$N($R^{7d}$)—, —OC(O)—, —OS(O)₂—, —OS(O)—, —OP(O)$R^{7d}$—, —C(O)O—, —S(O)₂O—, —S(O)O—, or —P(O)$R^{7d}$O—;

$R^{17}$ is selected from

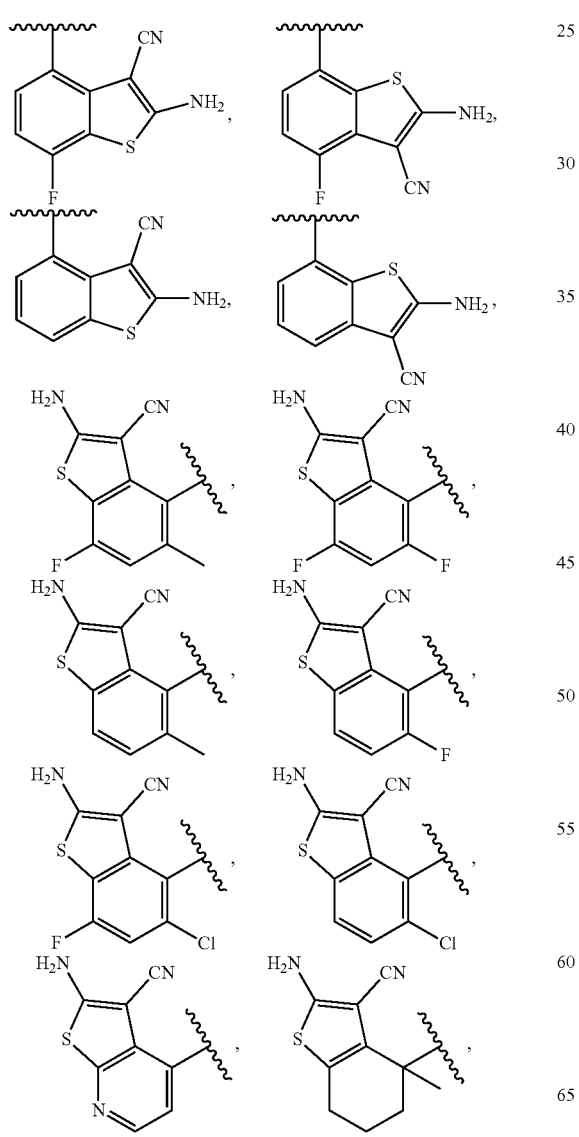

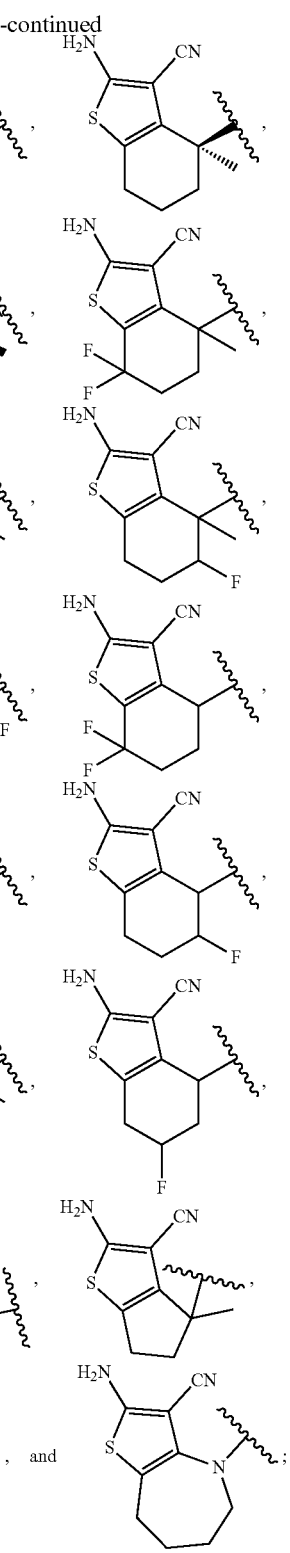

, and

;

$W^8$ is C($R^8$), C($R^8$)($R^{8a}$), N, N($R^8$b), C(O), S(O), or S(O)₂;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N $(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$W^9$ is C, C(R'), or N; $W^{10}$ is C, C($R^9$), or N;

each R9 is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$, $R^4$ is -$L^4$-$R^{4a}$;

$L^4$ is a bond, —O—, —$N(R^{4d})$—, —$C(O)$—, —S—, —$S(O)_2$—, —$S(O)$—, —$P(O)R^{4d}$—, $CR^4R^4$, —$OCR_4R^{4c}$—, —$N(R^{4d})CR^4R^{4c}$—, —$C(O)CR^4R^{4c}$—, —$SCR^4R^{4c}$—, $CR^4R^{4c}S(O)_2$—, —$CR^4CR^{4c}S(O)$—, —$CR^4R^4CP(O)R^{4d}$—, —$N(R^{4d})C(O)$—, —$N(R^{4d})S(O)_2$—, —$N(R^{4d})S(O)$—, —$N(R^{4d})P(O)R^{4d}$—, —$C(O)N(R^{4d})$—, —$S(O)_2N(R^{4d})$—, —$S(O)N(R^{4d})$—, —$P(O)R^{4d}N(R^{4d})$—, —$OC(O)$—, —$OS(O)_2$—, —$OS(O)$—, —$OP(O)R^{4d}$—, —$C(O)O$—, —$S(O)_{20}$—, —$S(O)O$—, or —$P(O)R^{4d}O$—;

each $R^4$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH_2C(O)OR^{14}$, —$OC(O)R^{14}a$, —$N(R^{14})(R^{14})$, —$N(R^{14})C(O)N(R^{14})(R^{14})$, —$N(R^{14})C(O)OR^{14}$, —$N(R^{14})C(O)R^{14a}$, and —$N(R^{14})S(O)_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14a}$, —$S(O)_2R^{14}$, —$S(O)_2N(R^{14})(R^{14})$, —$OCH_2C(O)OR^{14}$, and —$OC(O)R^{14}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14a}$, —$S(O)_2R^{14}$, —$S(O)_2N(R^{14})(R^{14})$, and —$OC(O)R^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from $C_{2-6}$alkenyl, $C_{2-6}$alkynyl, hydrogen, halogen, oxo, —CN, $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—,S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$, each $R^{11d}$ is independently selected from $C_{2-6}$alkenyl, $C_{2-6}$alkynyl, halogen, oxo, —CN, $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})

($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —C($R^{12b}$)$_2$-$C_{3-10}$cycloalkyl, $C_{2-9}$heterocycloalkyl, —C($R^{12b}$)$_2$-$C_{2-9}$heterocycloalkyl, $C_{6-10}$aryl, —C($R^{12b}$)$_2$-$C_{6-10}$aryl, —C($R^{12b}$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12b}$)$_2$-$C_{3-10}$cycloalkyl, $C_{2-9}$heterocycloalkyl, —C($R^{12b}$)$_2$-$C_{2-9}$heterocycloalkyl, $C_{6-10}$aryl, —C($R^{12b}$)$_2$-$C_{6-10}$aryl, —C($R^{12b}$)$_2$-$C_{1-9}$heteroaryl, and $C_{1-9}$heteroaryl are optionally substituted with one, two, or three $R^{20l}$;

$R^{12a}$ is selected from —C($R^{12b}$)$_2$-$C_{2-9}$heterocycloalkyl, $C_{1-6}$alkyl, $C_{2-6}$alkenyl, $C_{2-6}$alkynyl, $C_{3-10}$cycloalkyl, —C($R^{12b}$)$_2$-$C_{3-10}$cycloalkyl, $C_{2-9}$heterocycloalkyl, $C_{6-10}$aryl, —C($R^{12b}$)$_2$-$C_{6-10}$aryl, —C($R^{12b}$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12b}$)$_2$-$C_{3-10}$cycloalkyl, $C_{2-9}$heterocycloalkyl, —C($R^{12b}$)$_2$-$C_{2-9}$heterocycloalkyl, $C_{6-10}$aryl, —C($R^{12b}$)$_2$-$C_6$-10aryl, —C($R^{12b}$)$_2$-$C_{1-9}$heteroaryl, and $C_{1-9}$heteroaryl are optionally substituted with one, two, or three $R^{20l}$;

each $R^{12b}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{1d}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), —OCH$_2$C(O)O$R^{22}$, and —OC(O)$R^{25}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_1$-9heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

Embodiment 4 a Compound of Formula (II), or a Pharmaceutically Acceptable Salt or Solvate Thereof:

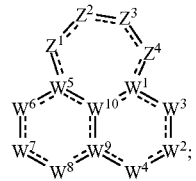

Formula (II)

wherein:

$Z^1$, $Z^2$, and $Z^3$ are each independently selected from N($R^4$), N($R^{11c}$), N($R^{11d}$), N, C($R^4$), C($R^{11c}$), C($R^{11d}$), C($R^4$)($R^{11c}$), C($R^{11c}$)($R^{11c}$), C($R^4$)($R^4$), C($R^{11c}$)($R^{11d}$), S, O, and C(O); $Z^4$ is selected from N($R^4$), N($R^{11c}$), N($R^{11d}$), N, C($R^4$), C($R^{11c}$), C($R^{11d}$), C($R^4$)($R^{11c}$), C($R^{11c}$)($R^{11c}$), C($R^4$)($R^4$), C($R^{11c}$)($R^{11d}$), S, and O;

wherein at least one of $Z^1$, $Z^2$, z3 and $Z^4$ is N($R^4$), N($R^{11d}$), C($R^4$), C($R^{11d}$), C($R^4$)($R^{11c}$), C($R^4$)($R^4$), or C($R^{11c}$)($R^{11d}$); $W^1$ is C, C($R^1$), or N;

$R^1$ is selected from hydrogen, halogen, —CN, $C_{1-6}$alkyl, $C_{2-6}$alkenyl, $C_{2-6}$alkynyl, —OR$^{12}$, —SR$^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, and $C_{2-6}$alkynyl are optionally substituted with one, two, or three $R^{20a}$;

$W^2$ is N($R^{2a}$), N, C($R^2$), C($R^2$)($R^{2a}$), C(O), S(O)$_2$, or S(O);

$R^2$ is selected from halogen, —OR$^{12}$, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-9heteroaryl, —SR$^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —CH$_2$C(O)N $(R^{12})(R^{13})$, —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

R$^{2a}$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$;

W$^3$ is N, N(R$^{3b}$), C(R$^3$), C(R$^3$)(R$^{3a}$), C(O), S(O)$_2$, or S(O);

R$^3$ and R$^{3a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-heteroaryl are optionally substituted with one, two, or three R$^{20c}$;

R$^{3b}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

W$^4$ is N or N(R$^{3c}$);

R$^{3c}$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

W$^5$ is C, C(R$^5$), or N;

R$^5$ is selected from hydrogen, halogen, —CN, C$_{1-6}$alkyl, C$_{2-6}$alkenyl, C$_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, and C$_{2-6}$alkynyl are optionally substituted with one, two, or three R$^{20d}$;

W$^6$ is C(R$^6$), N(R$^{6a}$%), N, C(R$^6$)(R$^{6a}$), C(O), S(O), or S(O)$_2$;

R$^6$ and R$^{6a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20e}$;

R$^6$ is selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20c}$;

W$^7$ is C(R$^7$), N(R$^7$), or C(R$^7$)(R$^{7a}$);

R$^{7a}$ and each R$^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-9heteroaryl are optionally substituted with one, two, or three R$^{20f}$;

R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl are optionally substituted with one, two, or three R$^{20f}$;

R$^7$ is -L$^7$-R$^{17}$;

1117

$L^7$ is a bond, —O—, —N($R^{74}$)—, —C(O)—, —S—, —S(O)$_2$—, —S(O)—, —P(O)$R^{7d}$, $CR^7CR^7c$, —OCR$^7$R$^{7c}$—, —N($R^{74}$)CR$^7$CR$^{7c}$—, —C(O)CR$^{7o}$R$^{7c}$—, —SCR$^7$R$^{7c}$—, —S(O)$_2$CR$^7$GR$^{7c}$—, —S(O)CR$^7$GR$^{7c}$—, —P(O)$R^{7d}$ CR7GR$^{7c}$—, —CR$^7$CR$^7$CCR$^7$R$^{7c}$, —CR$^7$GR$^7$CO—, —CR$^7$R$^{7a}$N($R^{7d}$)—, —CR$^7$GR$^{7o}$ C.(O)—, —CR$^7$R$^{7c}$S—, —CR$^7$GR$^7$CS(O)$_2$—, —CR$^7$CR$^{7c}$S(O)—, —CR$^7$R$^7$cP(O)$R^{7d}$ —, —N($R^{74}$)C(O)—, —N($R^{7d}$)S(O)$_2$—, —N($R^{7d}$)S(O)—, —N($R^{7d}$)P(O)$R^{7d}$ —, —C(O)N($R^{7d}$)—, —S(O)$_2$N($R^{74}$)—, —S(O)N($R^{74}$)—, —P(O)$R^{74N}$(R$^{74}$)—, —OC(O)—, —OS(O)$_2$—, —OS(O)—, —OP(O)$R^{74}$—, —C(O)O—, —S(O)$_2$O—, —S(O)O—, or —P(O)$R^{7a}$O—;

$R^{17}$ is selected from

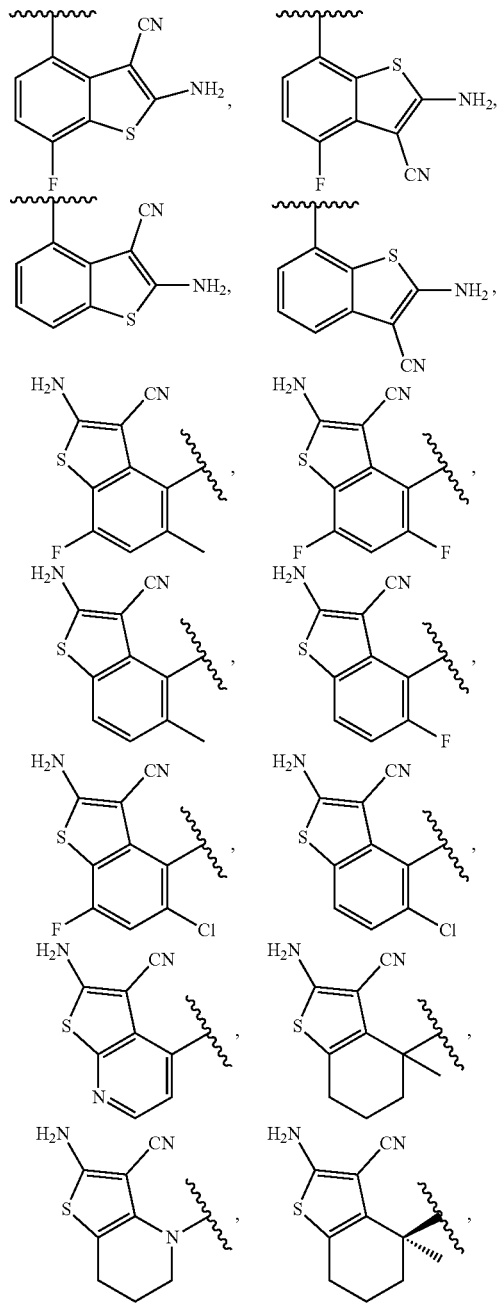

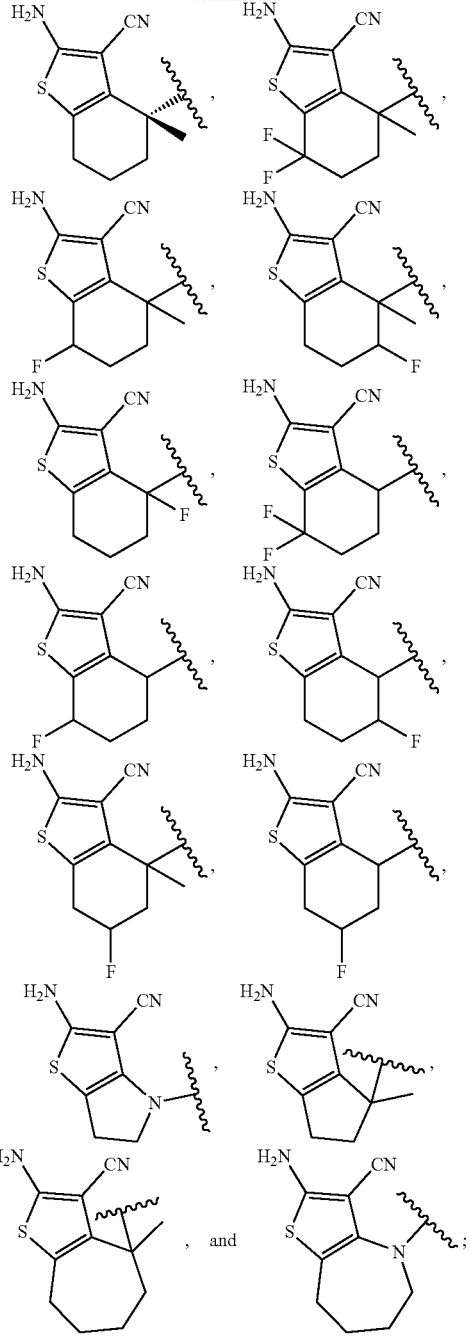

$W^8$ is $C(R^8)$, $C(R^8)(R^{8a})$, N, $N(R^{8b})$, C(O), S(O), or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20h}$;

$R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20h}$;

$W^9$ is C, C(R$^9$), or N;
$W^{10}$ is C, C(R$^9$), or N;

each $R^9$ is independently selected from hydrogen, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, and $C_{1-9}$heteroaryl are optionally substituted with one, two, or three $R^{20i}$, $R^4$ is -L$^4$-R$^{4a}$, L$^4$ is a bond, —O—, —N(R$^{4d}$)—, —C(O)—, —S—, —S(O)$_2$—, —S(O)—, —P(O)R$^{4d}$—, CR$^{4c}$R$^4$, —OCR$^4$R$^{4c}$—, —N(R$^{4d}$)CR$^{4c}$R$^{4c}$, —C(O)CR$^4$R$^{4c}$—, —SCR$^4$R$^{4c}$—, —S(O)$_2$CR$^{4c}$R$^{4c}$—, —S(O)CR$^4$R$^{4c}$—, —P(O)R$^{4d}$CR4cR$^{4c}$—, —CR$^4$R$^4$CR$^4$R$^4$, —CR$^4$R$^4$CO—, —CR$^4$R$^{4c}$CN(R$^{4d}$)—, —CR$^4$R$^{4c}$C(O)—, —CR$^4$R$^{4c}$S—, —CR$^4$GR$^{4c}$S(O)$_2$—, —CR$^4$CR$^{4c}$S(O)—, —CR$^4$R$^{4c}$P(O)R$^{4d}$—, —N(R$^{4d}$)C(O)—, —N(R$^{4d}$)S(O)$_2$—, —N(R$^{4d}$)S(O)—, —N(R$^{4d}$)P(O)R$^{4d}$—, —C(O)N(R$^{4d}$)—, —S(O)$_2$N(R$^{4d}$)—, —S(O)N(R$^{4d}$)—, —P(O)R$^{4a}$N(R$^{4d}$)—, —OC(O)—, —OS(O)$_2$—, —OS(O)—, —OP(O)R$^{4d}$—, —C(O)O—, —S(O)$_{20}$—, —S(O)O—, or —P(O)R$^{4d}$O—;

each $R^4$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, —OC(O)R$^{14}$a, —N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14a}$, and —N(R$^{14}$)S(O)$_2$R$^{14}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$, each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —CH$_2$-$C_{3-10}$cycloalkyl, $C_{2-9}$heterocycloalkyl, —CH$_2$-$C_{2-9}$heterocycloalkyl, —OR$^{14}$, —SR$^{14}$, —C(O)OR$^{14}$, —C(O)

N(R$^{14}$)(R$^{14}$), —C(O)C(O)N(R$^{14}$)(R$^{14}$), —OC(O)N(R$^{14}$)(R$^{14}$), —C(O)R$^{14a}$, —S(O)$_2$R$^{14}$, —S(O)$_2$N(R$^{14}$)(R$^{14}$), —OCH$_2$C(O)OR$^{14}$, and —OC(O)R$^{14}$a, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, and —CH$_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{14}$, —SR$^{14}$, —N(R$^{14}$)(R$^{14}$), —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$, —N(R$^{14}$)S(O)$_2$R$^{14}$, —C(O)R$^{14a}$, —S(O)$_2$R$^{14}$, —S(O)$_2$N(R$^{14}$)(R$^{14}$), and —OC(O)R$^{14a}$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), and —P(=O)(R$^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from $C_{2-6}$alkenyl, $C_{2-6}$alkynyl, hydrogen, halogen, oxo, —CN, $C_{1-6}$alkyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—,S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, and $C_{1-11}$heteroaryl are optionally substituted with one, two, or three $R^{20k}$, each $R^{11d}$ is independently selected from $C_{2-6}$alkenyl, $C_{2-6}$alkynyl, halogen, oxo, —CN, $C_{1-6}$alkyl, $C_{1-6}$haloalkyl, $C_{3-12}$cycloalkyl, —CH$_2$-$C_{3-12}$cycloalkyl, $C_{1-11}$heterocycloalkyl, —CH$_2$-$C_{1-11}$heterocycloalkyl, $C_{6-10}$aryl, —CH$_2$-$C_{6-10}$aryl, —CH$_2$-$C_{1-11}$heteroaryl, $C_{1-11}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl are optionally substituted with one, two, or three $R^{20k}$, each $R^{12}$ is independently selected from —$C(R^{12b})_2$-$C_{2-9}$heterocycloalkyl, hydrogen, $C_{1-6}$alkyl, $C_{2-6}$alkenyl, $C_{2-6}$alkynyl, $C_{3-10}$cycloalkyl, —$C(R^{12}b)_2$-$C_{3-10}$cycloalkyl, $C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12b})_2$-$C_{3-10}$cycloalkyl, $C_{2-9}$heterocycloalkyl, —$C(R^{12b})_2$-$C_{2-9}$heterocycloalkyl, $C_{6-10}$aryl, —$C(R^{12b})_2$-$C_{6-10}$aryl, —$C(R^{12b})_2$-$C_{1-9}$heteroaryl, and $C_{1-9}$heteroaryl are optionally substituted with one, two, or three $R^{20l}$, each $R^{12b}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{1d}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$, $R^{20o}$, $R^{20c}$, $R^{20d}$, $R^{20e}$, $R^{20}f$, $R^{20}g$, $R^{20h}$, $R^{20i}$, $R^{20j}$, $R^{20k}$, $R^{20l}$, and $R^{20m}$ is independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_2$,heterocycloalkyl, $C_{6-10}$aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

Embodiment 5. The compound of any one of embodiments 1-4, or a pharmaceutically acceptable salt or solvate thereof, wherein $W^4$ is N.

Embodiment 6. The compound of any one of embodiments 1-4, or a pharmaceutically acceptable salt or solvate thereof, wherein $W^4$ is $N(R^{3c})$.

Embodiment 7. The compound of any one of embodiments 1-6, or a pharmaceutically acceptable salt or solvate thereof, wherein $W^1$ is C.

Embodiment 8. The compound of any one of embodiments 1-6, or a pharmaceutically acceptable salt or solvate thereof, wherein $W^1$ is $C(R^1)$.

Embodiment 9. The compound of any one of embodiments 1-6, or a pharmaceutically acceptable salt or solvate thereof, wherein $W^1$ is N.

Embodiment 10. The compound of any one of embodiments 1-9, or a pharmaceutically acceptable salt or solvate thereof, wherein $W^5$ is C.

Embodiment 11. The compound of any one of embodiments 1-9, or a pharmaceutically acceptable salt or solvate thereof, wherein $W^5$ is $C(R^5)$.

Embodiment 12. The compound of any one of embodiments 1-9, or a pharmaceutically acceptable salt or solvate thereof, wherein $W^5$ is N.

Embodiment 13. The compound of any one of embodiments 1-12, or a pharmaceutically acceptable salt or solvate thereof, wherein $W^2$ is $C(R^2)$.

Embodiment 14. The compound of any one of embodiments 1-12, or a pharmaceutically acceptable salt or solvate thereof, wherein $W^2$ is $C(R^2)(R^{2a})$.

Embodiment 15. The compound of any one of embodiments 1-12, or a pharmaceutically acceptable salt or solvate thereof, wherein $W^2$ is N.

Embodiment 16. The compound of any one of embodiments 1-12, or a pharmaceutically acceptable salt or solvate thereof, wherein $W^2$ is $N(R^{2a})$.

Embodiment 17. The compound of any one of embodiments 1-16, or a pharmaceutically acceptable salt or solvate thereof, wherein $W^3$ is N.

Embodiment 18. The compound of any one of embodiments 1-16, or a pharmaceutically acceptable salt or solvate thereof, wherein $W^3$ is $N(R^{3b})$.

Embodiment 19. The compound of any one of embodiments 1-16, or a pharmaceutically acceptable salt or solvate thereof, wherein $W^3$ is $C(R^3)$.

Embodiment 20. The compound of any one of embodiments 1-16, or a pharmaceutically acceptable salt or solvate thereof, wherein $W^3$ is $C(R^3)(R^{3a})$.

Embodiment 21. The compound of any one of embodiments 1-16, or a pharmaceutically acceptable salt or solvate thereof, wherein $W^3$ is C(O).

Embodiment 22. The compound of any one of embodiments 1-21, or a pharmaceutically acceptable salt or solvate thereof, wherein $W^6$ is $C(R^6)$.

Embodiment 23. The compound of any one of embodiments 1-21, or a pharmaceutically acceptable salt or solvate thereof, wherein $W^6$ is $C(R^6)(R^{6a})$.

Embodiment 24 The compound of any one of embodiments 1-21, or a pharmaceutically acceptable salt or solvate thereof, wherein $W^6$ is N.

Embodiment 25 The compound of any one of embodiments 1-21, or a pharmaceutically acceptable salt or solvate thereof, wherein $W^6$ is $N(R^{6\%})$.

Embodiment 26 The compound of any one of embodiments 1-21, or a pharmaceutically acceptable salt or solvate thereof, wherein $W^6$ is C(O).

Embodiment 27 The compound of any one of embodiments 1-26, or a pharmaceutically acceptable salt or solvate thereof, wherein $W^7$ is $C(R^7)$.

Embodiment 28 The compound of any one of embodiments 1-26, or a pharmaceutically acceptable salt or solvate thereof, wherein $W^7$ is $C(R^7)(R^{7a})$.

Embodiment 29 The compound of any one of embodiments 1-26, or a pharmaceutically acceptable salt or solvate thereof, wherein $W^7$ is $N(R^7)$.

Embodiment 30 The compound of any one of embodiments 1-29, or a pharmaceutically acceptable salt or solvate thereof, wherein $W^8$ is $C(R^8)$.

Embodiment 31 The compound of any one of embodiments 1-29, or a pharmaceutically acceptable salt or solvate thereof, wherein $W^8$ is $C(R^8)(R^{8a})$.

Embodiment 32 The compound of any one of embodiments 1-29, or a pharmaceutically acceptable salt or solvate thereof, wherein $W^8$ is N.

Embodiment 33 The compound of any one of embodiments 1-29, or a pharmaceutically acceptable salt or solvate thereof, wherein $W^8$ is $N(R^{8b})$.

Embodiment 34 The compound of any one of embodiments 1-29, or a pharmaceutically acceptable salt or solvate thereof, wherein w8 is C(O).

Embodiment 35 The compound of any one of embodiments 1-34, or a pharmaceutically acceptable salt or solvate thereof, wherein $W^9$ is C.

Embodiment 36 The compound of any one of embodiments 1-34, or a pharmaceutically acceptable salt or solvate thereof, wherein $W^9$ is N.

Embodiment 37 The compound of any one of embodiments 1-36, or a pharmaceutically acceptable salt or solvate thereof, wherein $W^{10}$ is C.

Embodiment 38 The compound of any one of embodiments 1-36, or a pharmaceutically acceptable salt or solvate thereof, wherein $W^{10}$ is N.

Embodiment 39 The compound of any one of embodiments 1-4, or a pharmaceutically acceptable salt or solvate thereof, having the structure of Formula (Ia):

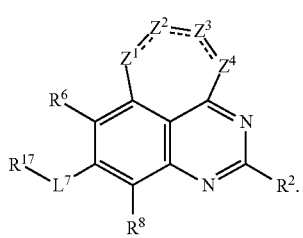

Formula (Ia)

Embodiment 40 The compound of any one of embodiments 1-4, or a pharmaceutically acceptable salt or solvate thereof, having the structure of Formula (Ib):

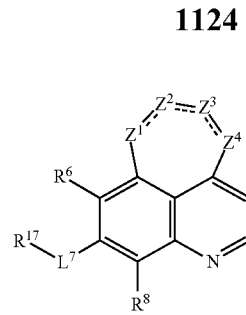

Formula (Ib)

Embodiment 41 The compound of any one of embodiments 1-4, or a pharmaceutically acceptable salt or solvate thereof, having the structure of Formula (Ic):

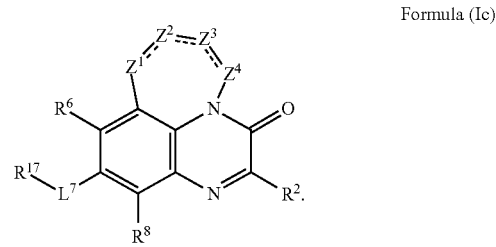

Formula (Ic)

Embodiment 42 The compound of any one of embodiments 1-4, or a pharmaceutically acceptable salt or solvate thereof, having the structure of Formula (Id):

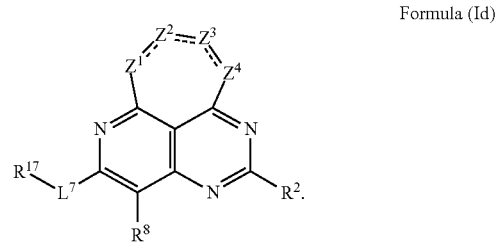

Formula (Id)

Embodiment 43 The compound of any one of embodiments 1-4, or a pharmaceutically acceptable salt or solvate thereof, having the structure of Formula (Ie):

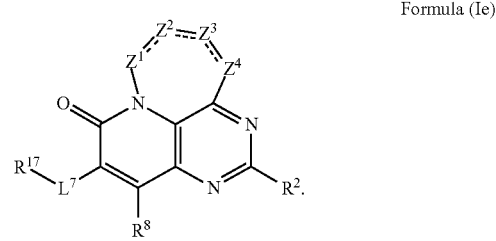

Formula (Ie)

Embodiment 44 The compound of any one of embodiments 1-4, or a pharmaceutically acceptable salt or solvate thereof, having the structure of Formula (If):

Formula (If)

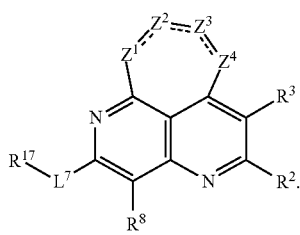

Embodiment 45 The compound of any one of embodiments 1-44, or a pharmaceutically acceptable salt or solvate thereof, wherein $R^2$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{124}$, $-SR^{12}$, and $-N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{206}$.

Embodiment 46 The compound of any one of embodiments 1-45, or a pharmaceutically acceptable salt or solvate thereof, wherein $R^2$ is selected from $-OR^{124}$, $-SR^{12}$, $-N(R^{12})(R^{13})$, and $C_{1-6}$alkyl optionally substituted with one, two, or three $R^{20b}$.

Embodiment 47 The compound of any one of embodiments 1-46, or a pharmaceutically acceptable salt or solvate thereof, wherein $R^2$ is selected from

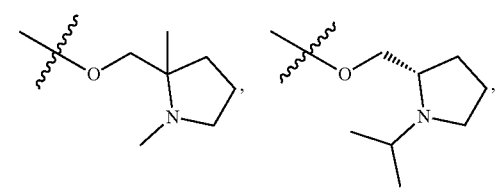

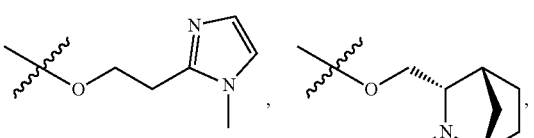

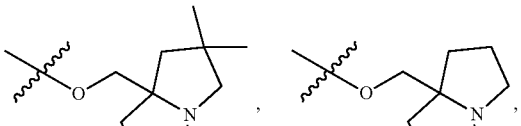

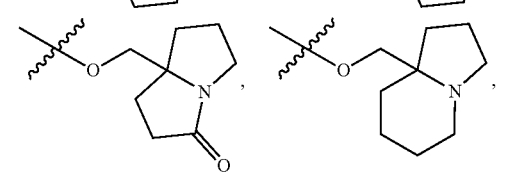

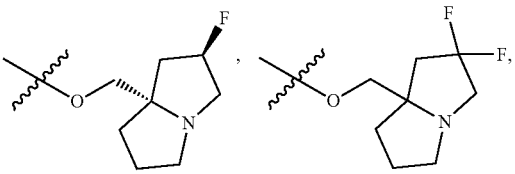

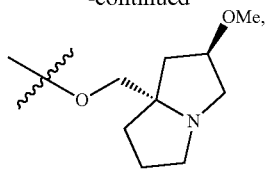

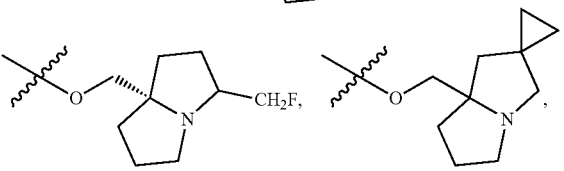

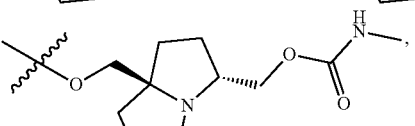

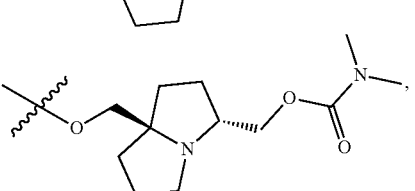

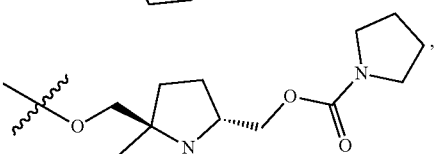

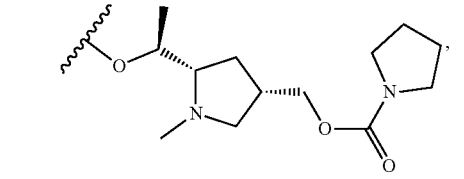

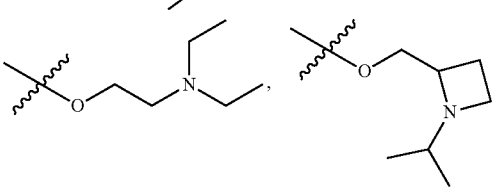

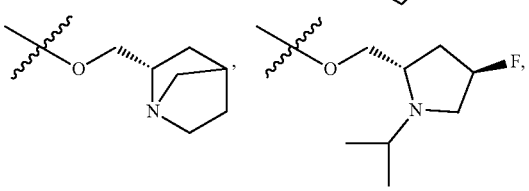

1127
-continued
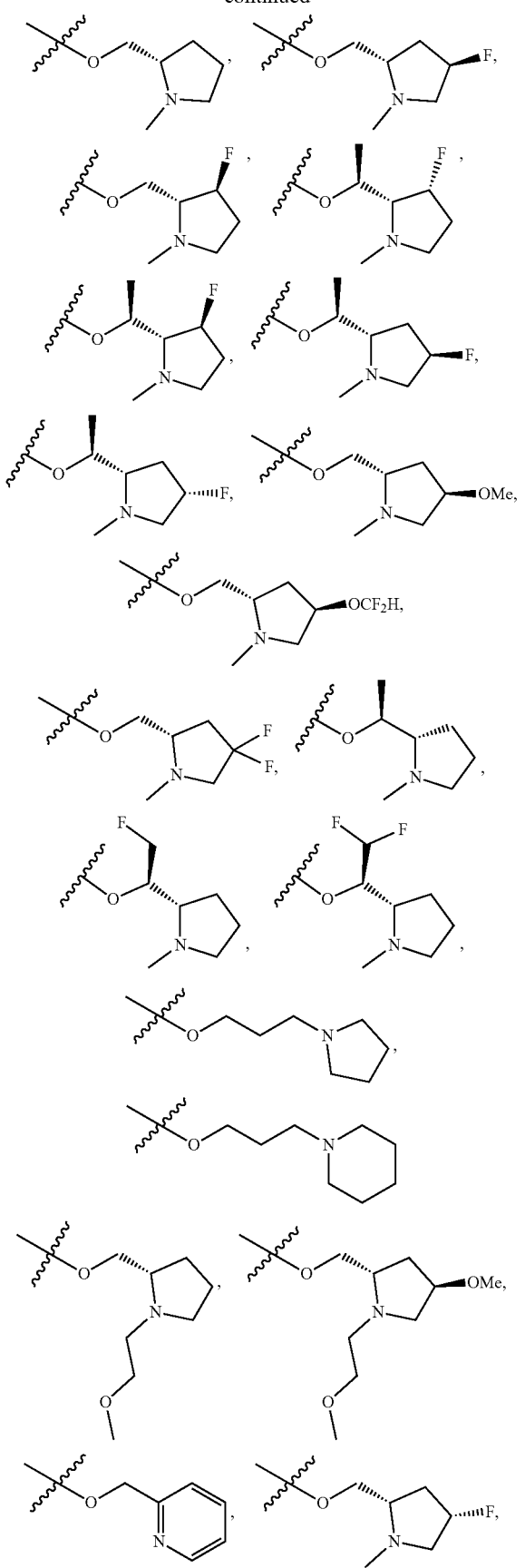
1128
-continued
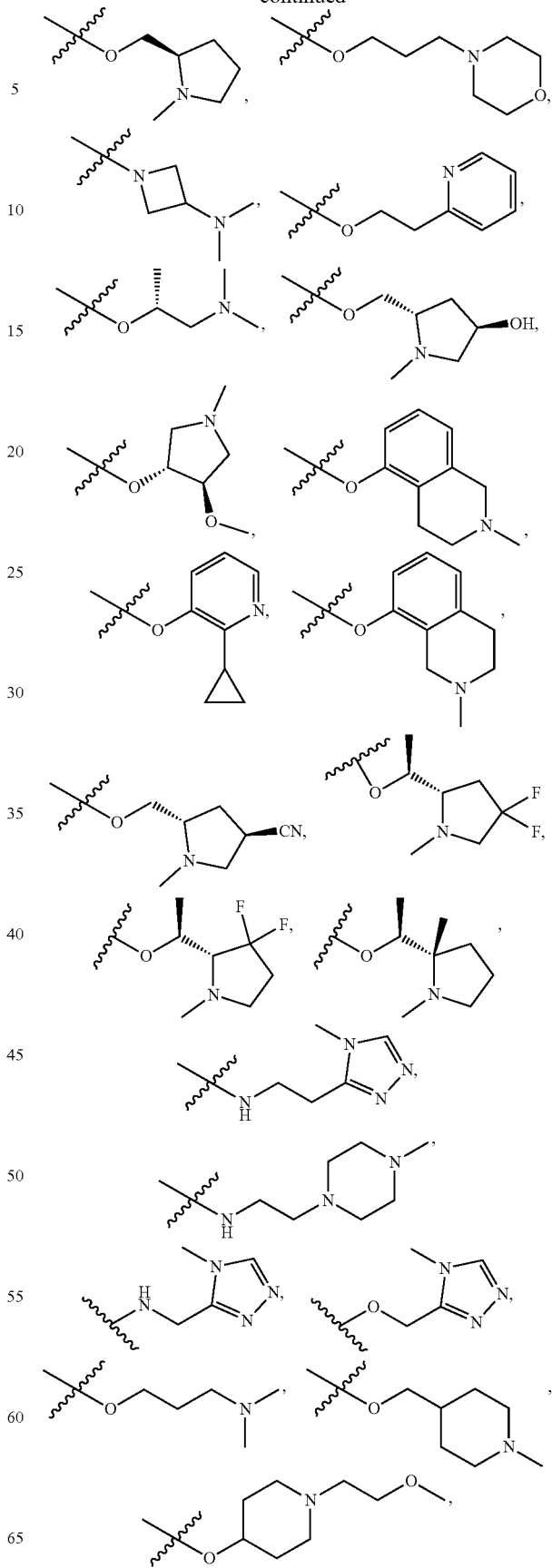

1129
-continued
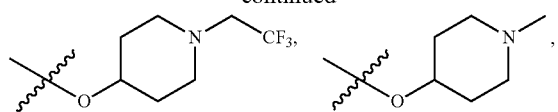
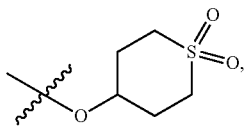
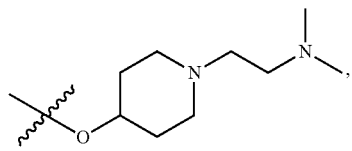
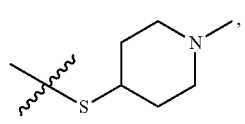
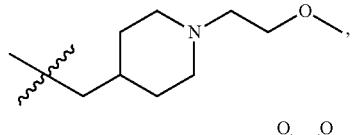
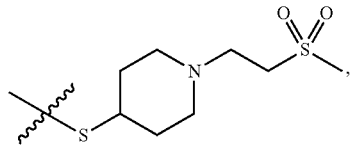
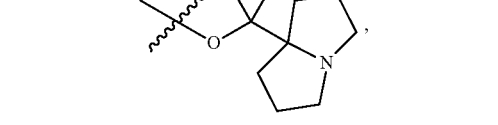
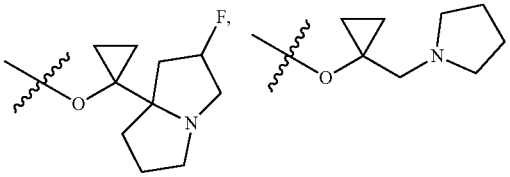
1130
-continued
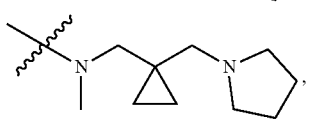
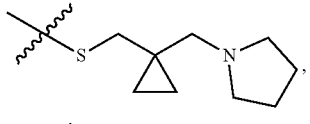
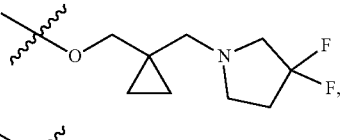
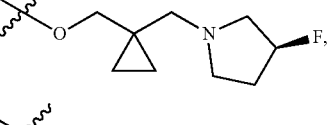
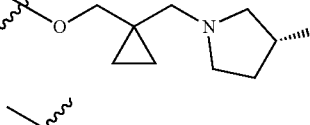
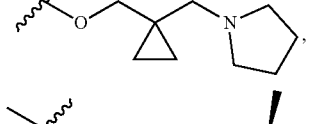
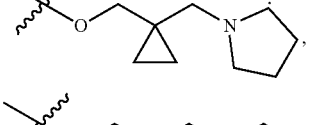
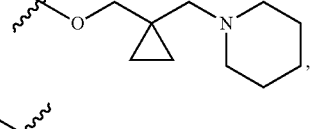
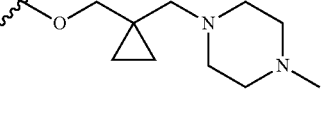
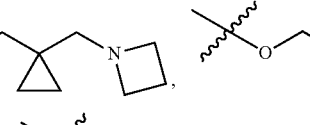
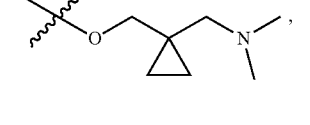

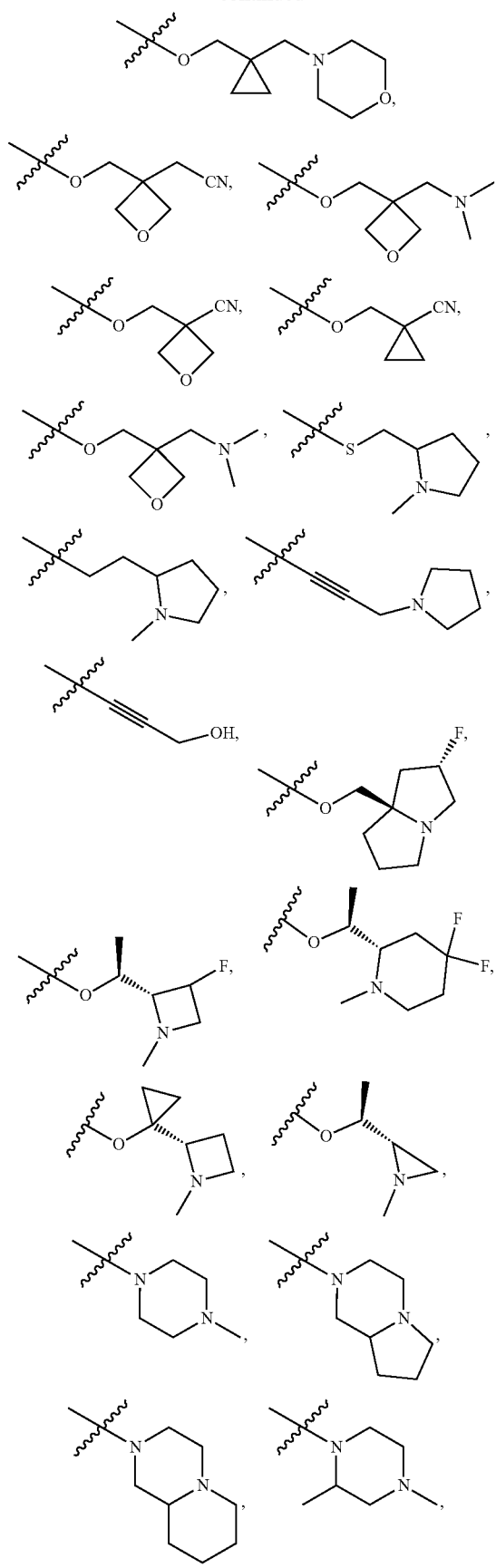

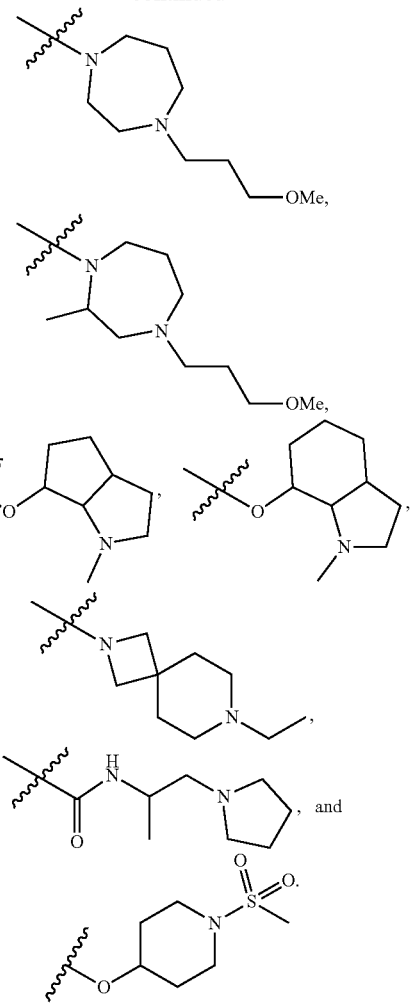

Embodiment 48 The compound of any one of embodiments 1-47, or a pharmaceutically acceptable salt or solvate thereof, wherein $R^3$ is selected from hydrogen, halogen, —CN, $C_{1-6}$alkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$)—, wherein $C_{1-6}$alkyl is optionally substituted with one, two, or three $R^{20c}$.

Embodiment 49 The compound of any one of embodiments 1-48, or a pharmaceutically acceptable salt or solvate thereof, wherein $R^3$ is selected from hydrogen, halogen, —CN, $C_{1-6}$alkyl, and —OR$^{12}$, wherein $C_{1-6}$alkyl is optionally substituted with one, two, or three $R^{20c}$.

Embodiment 50 The compound of any one of embodiments 1-49, or a pharmaceutically acceptable salt or solvate thereof, wherein $R^6$ is selected from hydrogen, halogen, —CN, $C_{1-6}$alkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$)—, wherein $C_{1-6}$alkyl is optionally substituted with one, two, or three $R^{20e}$.

Embodiment 51 The compound of any one of embodiments 1-50, or a pharmaceutically acceptable salt or solvate thereof, wherein $R^6$ is selected from hydrogen, halogen, —CN, $C_{1-6}$alkyl, and —OR$^{12}$, wherein $C_{1-6}$alkyl is optionally substituted with one, two, or three $R^{20c}$.

Embodiment 52 The compound of any one of embodiments 1-51, or a pharmaceutically acceptable salt or solvate thereof, wherein $R^{17}$ is $C_{3-10}$cycloalkyl optionally substituted with one, two, or three $R^{20g}$.

Embodiment 53 The compound of any one of embodiments 1-51, or a pharmaceutically acceptable salt or solvate thereof, wherein $R^{17}$ is $C_{2-9}$heterocycloalkyl optionally substituted with one, two, or three $R^{20g}$.

Embodiment 54 The compound of any one of embodiments 1-51, or a pharmaceutically acceptable salt or solvate thereof, wherein $R^{17}$ is $C_{6-10}$aryl optionally substituted with one, two, or three $R^{20g}$ Embodiment 55 The compound of any one of embodiments 1-51, or a pharmaceutically acceptable salt or solvate thereof, wherein $R^{17}$ is $C_{1-9}$heteroaryl optionally substituted with one, two, or three $R^{20g}$ Embodiment 56 The compound of any one of embodiments 1-55, or a pharmaceutically acceptable salt or solvate thereof, wherein $L^7$ is a bond, —O—, —N($R^{74}$)—, —C(O)—, or $CR^{7o}R^{7c}$.

Embodiment 57 The compound of any one of embodiments 1-56, or a pharmaceutically acceptable salt or solvate thereof, wherein $L^7$ is a bond.

Embodiment 58 The compound of any one of embodiments 1-57, or a pharmaceutically acceptable salt or solvate thereof, wherein $R^{17}$ is selected from:

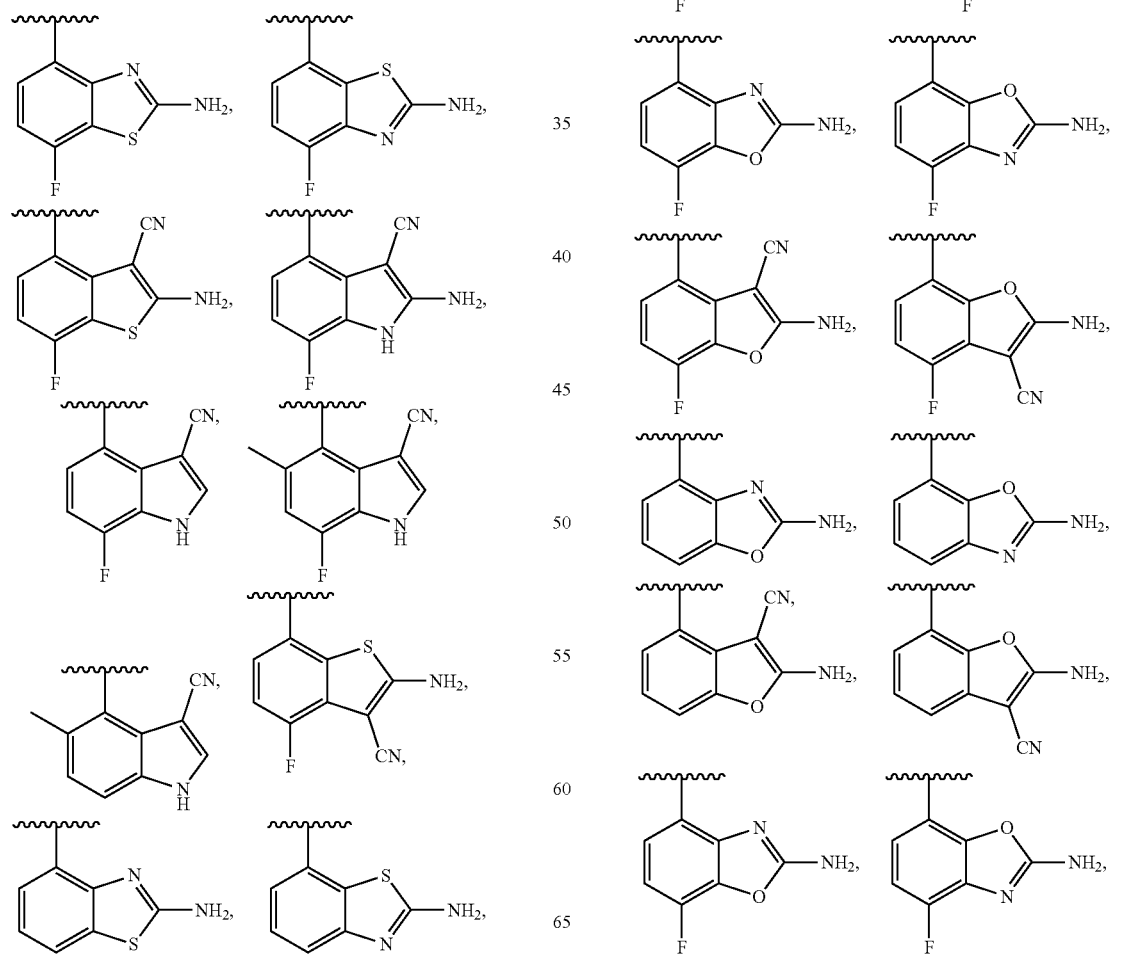

-continued

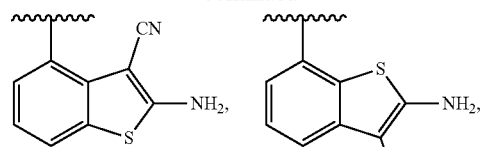
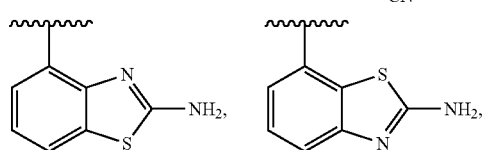
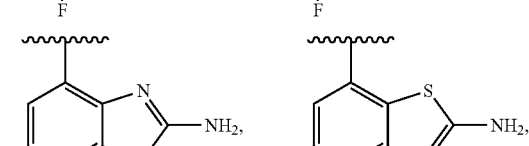
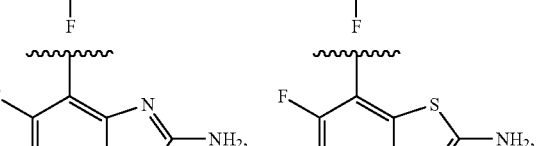
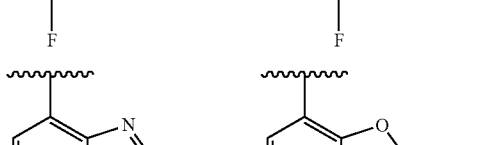
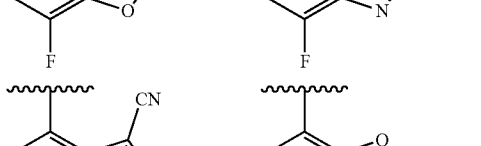
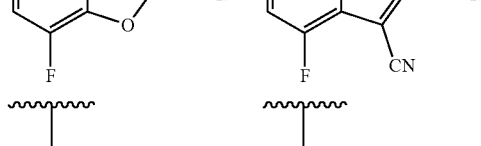
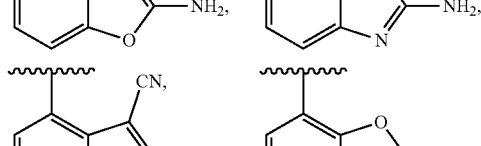
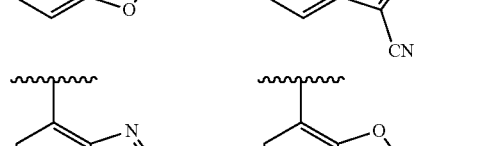
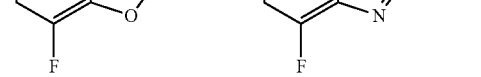

1135
-continued
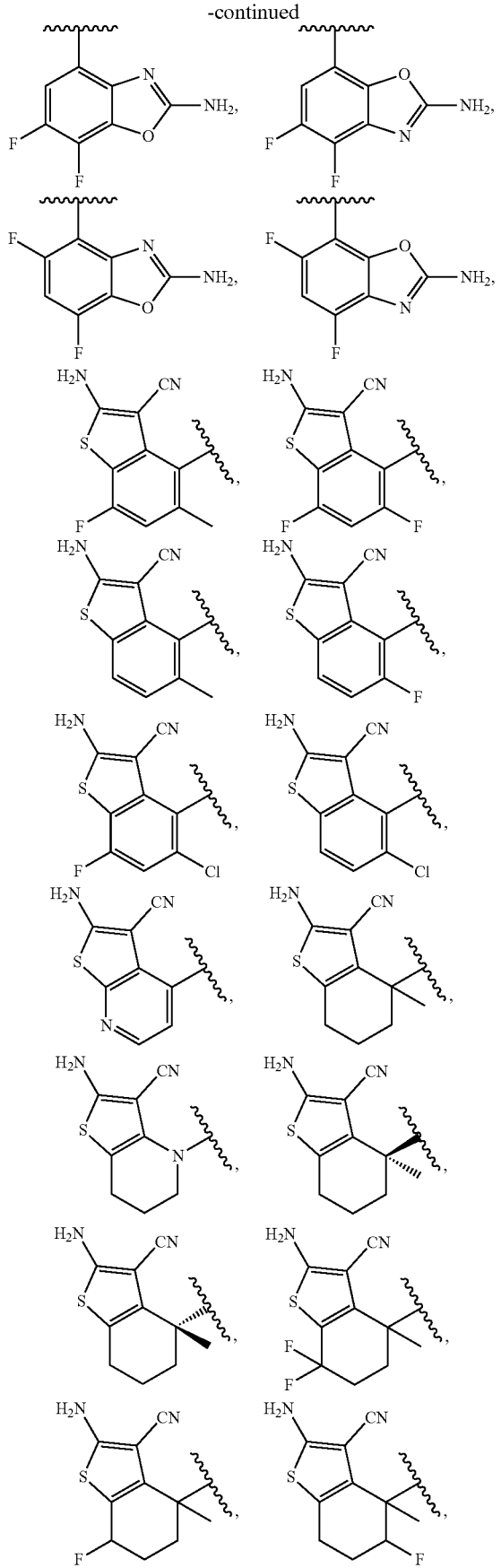
1136
-continued
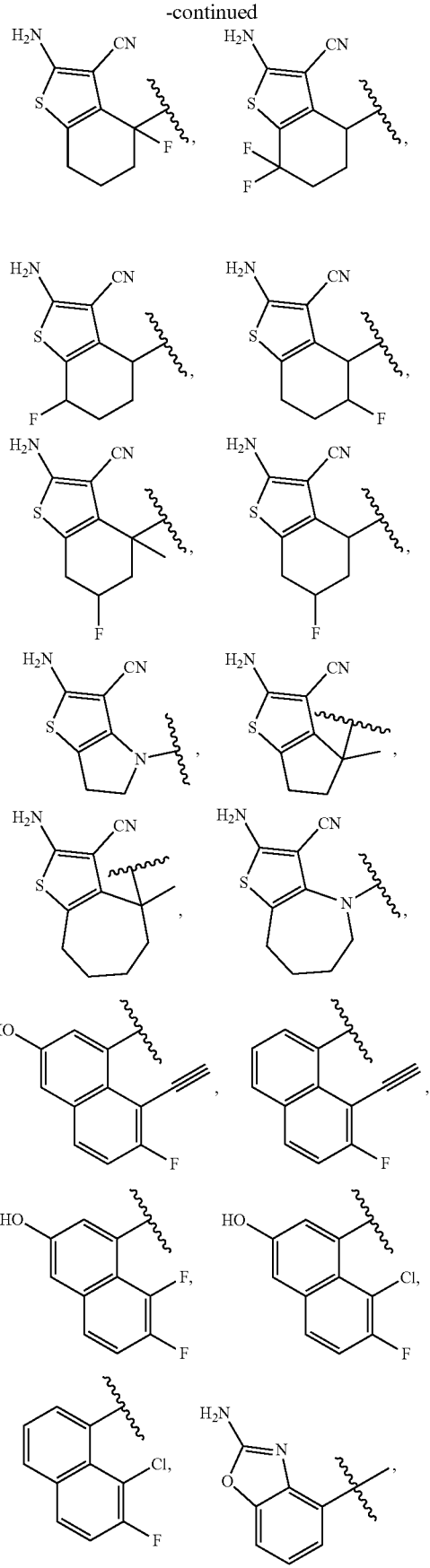

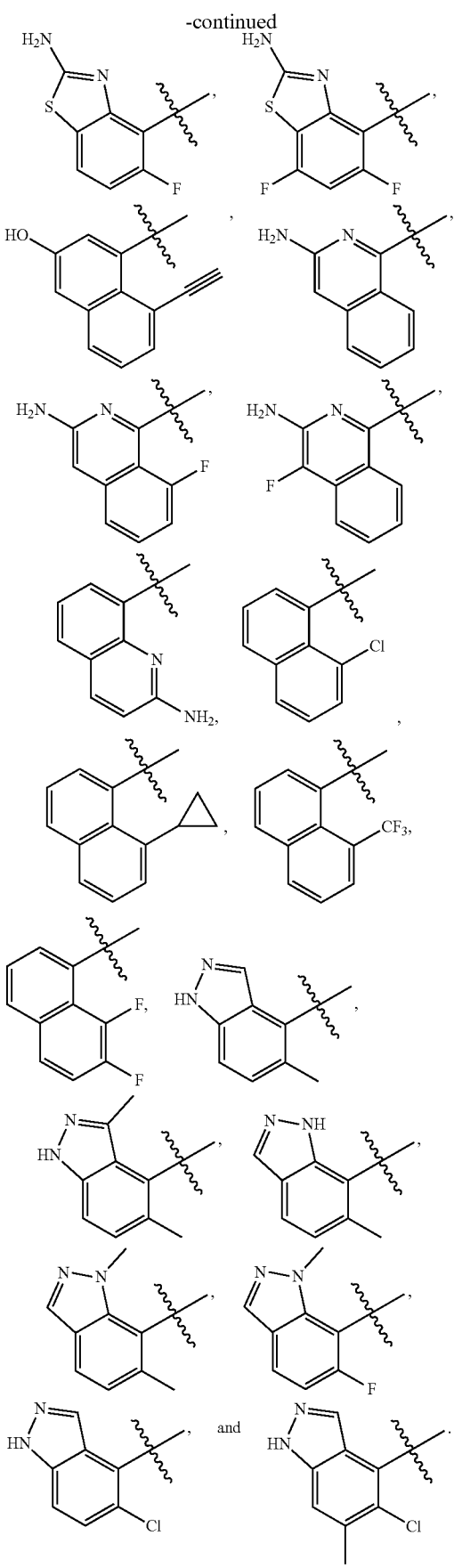

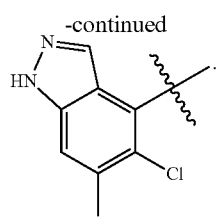

Embodiment 59 The compound of any one of embodiments 1-58, or a pharmaceutically acceptable salt or solvate thereof, wherein $R^8$ is selected from hydrogen, halogen, —CN, $C_{1-6}$alkyl, —$OR^{12}$, —$SR^{12}$, —$N(R^{12})(R^{13})$, —$C(O)OR^{12}$, —$C(O)R^{15}$, —$C(O)N(R^{12})(R^{13})$, —$S(O)_2R^{15}$, and —$S(O)_2N(R^{12})(R^{13})$—, wherein $C_{1-6}$alkyl is optionally substituted with one, two, or three $R^{20h}$ Embodiment 60 The compound of any one of embodiments 1-58, or a pharmaceutically acceptable salt or solvate thereof, wherein $R^8$ is selected from hydrogen, halogen, —CN, $C_{1-6}$alkyl, and —$OR^{12}$, wherein $C_{1-6}$alkyl is optionally substituted with one, two, or three $R^{20h}$.

Embodiment 61 The compound of any one of embodiments 1-60, or a pharmaceutically acceptable salt or solvate thereof, wherein $Z^1$ is O, $Z^2$ is $C(R^{11c})(R^{11c})$, $Z^3$ is $C(R^{11c})(R^{11c})$, and $Z^4$ is $N(R^4)$.

Embodiment 62 The compound of any one of embodiments 1-60, or a pharmaceutically acceptable salt or solvate thereof, wherein $Z^1$ is S, $Z^2$ is $C(R^{11c})(R^{11c})$, $Z^3$ is $C(R^{11c})(R^{11c})$, and $Z^4$ is $N(R^4)$.

Embodiment 63 The compound of any one of embodiments 1-60, or a pharmaceutically acceptable salt or solvate thereof, wherein $Z^1$ is $N(R^{11c})$, $Z^2$ is $C(R^{11c})(R^{11c})$, $Z^3$ is $C(R^{11c})(R^{11c})$, and $Z^4$ is $N(R^4)$.

Embodiment 64 The compound of any one of embodiments 1-60, or a pharmaceutically acceptable salt or solvate thereof, wherein $Z^1$ is $C(R^{11c})(R^{11c})$, $Z^2$ is $C(R^{11c})(R^{11c})$, $Z^3$ is $C(R^{11c})(R^{11c})$, and $Z^4$ is $N(R^4)$.

Embodiment 65 The compound of any one of embodiments 1-60, or a pharmaceutically acceptable salt or solvate thereof, wherein $Z^1$ is O, $Z^2$ is $C(R^{11c})(R^{11c})$, $Z^3$ is C(O), and $Z^4$ is $N(R^4)$.

Embodiment 66 The compound of any one of embodiments 1-60, or a pharmaceutically acceptable salt or solvate thereof, wherein $Z^1$ is O, $Z^2$ is $C(R^{11c})(R^{11c})$, $Z^3$ is $C(R^4)(R^{11c})$, and $Z^4$ is $N(R^{11c})$.

Embodiment 67 The compound of any one of embodiments 1-60, or a pharmaceutically acceptable salt or solvate thereof, wherein $Z^1$ is O, $Z^2$ is $C(R^{11c})(R^{11c})$, $Z^3$ is $C(R^{11c})(R^{11c})$, and $Z^4$ is $C(R^4)(R^{11c})$.

Embodiment 68 The compound of any one of embodiments 1-60, or a pharmaceutically acceptable salt or solvate thereof, wherein $Z^1$ is O, $Z^2$ is $C(R^{11c})(R^{11c})$, $Z^3$ is $C(R^4)(R^{11c})$, and $Z^4$ is $C(R^{11c})(R^{11c})$.

Embodiment 69 The compound of any one of embodiments 1-60, or a pharmaceutically acceptable salt or solvate thereof, wherein $Z^1$ is O, $Z^2$ is $C(R^{11c})(R^{11c})$, $Z^3$ is $C(R^4)(R^{11c})$, and $Z^4$ is O.

Embodiment 70 The compound of any one of embodiments 1-69, or a pharmaceutically acceptable salt or solvate thereof, wherein
each $R^{11c}$ is independently selected from hydrogen, halogen, $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_{6-10}$aryl, —$CH_2$-$C_{1-11}$heteroaryl, and $C_{1-11}$heteroaryl, wherein $C_{1-6}$alkyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-10}$aryl, —$CH_2$-$C_6$-10aryl, —$CH_2$-$C_{1-11}$heteroaryl, and $C_{1-11}$heteroaryl are optionally substituted with one, two, or three $R^{20}k$.

Embodiment 71 The compound of any one of embodiments 1-70, or a pharmaceutically acceptable salt or solvate thereof, wherein
each $R^{11}c$ is independently selected from hydrogen and $C_{1-6}$alkyl optionally substituted with one, two, or three $R^{20}k$ Embodiment 72 The compound of any one of embodiments 1-71, or a pharmaceutically acceptable salt or solvate thereof, wherein
each $R^{11}c$ is hydrogen.

Embodiment 73 The compound of any one of embodiments 1-72, or a pharmaceutically acceptable salt or solvate thereof, wherein
each $R^{4a}$ is $C_{3-10}$cycloalkyl optionally substituted with one, two, three, or four $R^4b$.

Embodiment 74 The compound of any one of embodiments 1-72, or a pharmaceutically acceptable salt or solvate thereof, wherein
each $R^{4a}$ is $C_{2-9}$heterocycloalkyl optionally substituted with one, two, three, or four $R^4b$.

Embodiment 75 The compound of any one of embodiments 1-72, or a pharmaceutically acceptable salt or solvate thereof, wherein
each $R^{4a}$ is $C_{6-10}$aryl optionally substituted with one, two, three, or four $R^4b$.

Embodiment 76 The compound of any one of embodiments 1-72, or a pharmaceutically acceptable salt or solvate thereof, wherein
each $R^{4a}$ is $C_{1-9}$heteroaryl optionally substituted with one, two, three, or four $R^4b$.

Embodiment 77 The compound of any one of embodiments 1-72, or a pharmaceutically acceptable salt or solvate thereof, wherein
each $R^{4a}$ is $C_{3-10}$cycloalkyl, $C_{2-9}$heterocycloalkyl, $C_{6-10}$aryl, and $C_{1-9}$heteroaryl optionally substituted with one, two, three, or four $R^4b$.

Embodiment 78 The compound of any one of embodiments 1-77, or a pharmaceutically acceptable salt or solvate thereof, wherein $L^4$ is a bond, —O—, —N($R^{4d}$)—, —C(O)—, or $CR^4R^{4c}$.

Embodiment 79 The compound of any one of embodiments 1-78, or a pharmaceutically acceptable salt or solvate thereof, wherein $L^4$ is a bond.

Embodiment 80 The compound of any one of embodiments 1-44, or a pharmaceutically acceptable salt or solvate thereof, wherein $Z^1$ is O.

Embodiment 81 The compound of embodiment 80, or a pharmaceutically acceptable salt or solvate thereof, wherein $Z^2$ is C($R^{11}c$)(H).

Embodiment 82 The compound of embodiment 80, or a pharmaceutically acceptable salt or solvate thereof, wherein $Z^2$ is C($R^{11d}$)(H).

Embodiment 83 The compound of embodiment 80, or a pharmaceutically acceptable salt or solvate thereof, wherein $Z^2$ is C($R^4$)(H).

Embodiment 84 The compound of embodiment 80, or a pharmaceutically acceptable salt or solvate thereof, wherein $Z^2$ is C(H)(H).

Embodiment 85 The compound of any one of embodiments 80-84, or a pharmaceutically acceptable salt or solvate thereof, wherein $Z^3$ is C($R^{11}c$)(H).

Embodiment 86 The compound of any one of embodiments 80-84, or a pharmaceutically acceptable salt or solvate thereof, wherein $Z^3$ is C($R^{11d}$)(H).

Embodiment 87 The compound of any one of embodiments 80-84, or a pharmaceutically acceptable salt or solvate thereof, wherein $Z^3$ is C($R^4$)(H).

Embodiment 88 The compound of any one of embodiments 80-84, or a pharmaceutically acceptable salt or solvate thereof, wherein $Z^3$ is C(H)(H).

Embodiment 89 The compound of any one of embodiments 80-88, or a pharmaceutically acceptable salt or solvate thereof, wherein $Z^4$ is N($R^4$).

Embodiment 90 The compound of any one of embodiments 80-88, or a pharmaceutically acceptable salt or solvate thereof, wherein $Z^4$ is N($R^{11d}$).

Embodiment 91 The compound of any one of embodiments 80-90, or a pharmaceutically acceptable salt or solvate thereof, wherein $R^6$ is halogen.

Embodiment 92 The compound of any one of embodiments 80-91, or a pharmaceutically acceptable salt or solvate thereof, wherein $R^8$ is halogen.

Embodiment 93 The compound of any one of embodiments 80-92, or a pharmaceutically acceptable salt or solvate thereof, wherein
$L^7$ is a bond and $R^{17}$ is

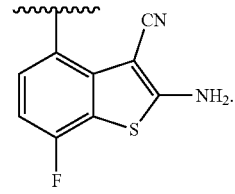 [SMILES: *c1ccc(F)c2sc(N)c(C#N)c12]

Embodiment 94 The compound of any one of embodiments 80-93, or a pharmaceutically acceptable salt or solvate thereof, wherein $R^{11}c$ is independently $C_{2-3}$alkenyl optionally substituted with one, two, or three $R^{20}k$ Embodiment 95 The compound of any one of embodiments 80-93, or a pharmaceutically acceptable salt or solvate thereof, wherein $R^{11}c$ is independently $C_{2-3}$alkynyl optionally substituted with one, two, or three $R^{20}k$ Embodiment 96 The compound of any one of embodiments 80-93, or a pharmaceutically acceptable salt or solvate thereof, wherein $R^{11}c$ is independently $C_{1-3}$haloalkyl optionally substituted with one, two, or three $R^{20}k$ Embodiment 97 The compound of any one of embodiments 80-93, or a pharmaceutically acceptable salt or solvate thereof, wherein $R^{11}c$ is independently $C_{3-6}$cycloalkyl optionally substituted with one, two, or three $R^{20}k$ Embodiment 98 The compound of any one of embodiments 80-93, or a pharmaceutically acceptable salt or solvate thereof, wherein $R^{11}c$ is independently —$CH_2$-$C_{3-6}$cycloalkyl optionally substituted with one, two, or three $R^{20}k$.

Embodiment 99 The compound of any one of embodiments 80-93, or a pharmaceutically acceptable salt or solvate thereof, wherein $R^{11}c$ is independently 3-6 membered heterocycloalkyl optionally substituted with one, two, or three $R^{20}k$ Embodiment 100 The compound of any one of embodiments 80-93, or a pharmaceutically acceptable salt or solvate thereof, wherein $R^{11}c$ is independently —$CH_2$-(3-6 membered heterocycloalkyl) optionally substituted with one, two, or three $R^{20}k$.

Embodiment 101 The compound of any one of embodiments 80-93, or a pharmaceutically acceptable salt or solvate thereof, wherein $R^{11c}$ is independently phenyl optionally substituted with one, two, or three $R^{20k}$ Embodiment 102 The compound of any one of embodiments 80-93, or a pharmaceutically acceptable salt or solvate thereof, wherein $R^{11c}$ is independently —CH$_2$-phenyl optionally substituted with one, two, or three $R^{20k}$ Embodiment 103 The compound of any one of embodiments 80-93, or a pharmaceutically acceptable salt or solvate thereof, wherein $R^{11c}$ is independently —CH$_2$-(5-6 membered heteroaryl) optionally substituted with one, two, or three $R^{20k}$ Embodiment 104 The compound of any one of embodiments 80-93, or a pharmaceutically acceptable salt or solvate thereof, wherein $R^{11c}$ is independently 5-6 membered heteroaryl optionally substituted with one, two, or three $R^{20k}$ Embodiment 105 The compound of any one of embodiments 80-104, or a pharmaceutically acceptable salt or solvate thereof, wherein $R^{11d}$ is independently $C_{2-3}$alkenyl optionally substituted with one, two, or three $R^{20k}$ Embodiment 106 The compound of any one of embodiments 80-104, or a pharmaceutically acceptable salt or solvate thereof, wherein $R^{11d}$ is independently $C_{2-3}$alkynyl optionally substituted with one, two, or three $R^{20k}$ Embodiment 107 The compound of any one of embodiments 80-104, or a pharmaceutically acceptable salt or solvate thereof, wherein $R^{11d}$ is independently $C_{1-3}$haloalkyl optionally substituted with one, two, or three $R^{20k}$ Embodiment 108 The compound of any one of embodiments 80-104, or a pharmaceutically acceptable salt or solvate thereof, wherein $R^{11d}$ is independently $C_{3-6}$cycloalkyl optionally substituted with one, two, or three $R^{20k}$ Embodiment 109 The compound of any one of embodiments 80-104, or a pharmaceutically acceptable salt or solvate thereof, wherein $R^{11d}$ is independently —CH$_2$-$C_{3-6}$cycloalkyl optionally substituted with one, two, or three $R^{20k}$.

Embodiment 110 The compound of any one of embodiments 80-104, or a pharmaceutically acceptable salt or solvate thereof, wherein $R^{11d}$ is independently 3-6 membered heterocycloalkyl optionally substituted with one, two, or three $R^{20k}$.

Embodiment 111 The compound of any one of embodiments 80-104, or a pharmaceutically acceptable salt or solvate thereof, wherein $R^{11d}$ is independently —CH$_2$-(3-6 membered heterocycloalkyl) optionally substituted with one, two, or three $R^{20k}$ Embodiment 112 The compound of any one of embodiments 80-104, or a pharmaceutically acceptable salt or solvate thereof, wherein $R^{11d}$ is independently phenyl optionally substituted with one, two, or three $R^{20k}$ Embodiment 113 The compound of any one of embodiments 80-104, or a pharmaceutically acceptable salt or solvate thereof, wherein $R^{11d}$ is independently —CH$_2$-phenyl optionally substituted with one, two, or three $R^{20k}$ Embodiment 114 The compound of any one of embodiments 80-104, or a pharmaceutically acceptable salt or solvate thereof, wherein $R^{11d}$ is independently —CH$_2$-(5-6 membered heteroaryl) optionally substituted with one, two, or three $R^{20k}$ Embodiment 115 The compound of any one of embodiments 80-104, or a pharmaceutically acceptable salt or solvate thereof, wherein $R^{11d}$ is independently 5-6 membered heteroaryl optionally substituted with one, two, or three $R^{20k}$.

Embodiment 116 The compound of any one of embodiments 80-104, or a pharmaceutically acceptable salt or solvate thereof, wherein $R^{11d}$ is independently $C_{1-3}$alkyl optionally substituted with one, two, or three $R^{20k}$ Embodiment 117 The compound of any one of embodiments 80-116, or a pharmaceutically acceptable salt or solvate thereof, wherein $R^{20k}$ is independently halogen.

Embodiment 118 The compound of any one of embodiments 80-116, or a pharmaceutically acceptable salt or solvate thereof, wherein $R^{20k}$ is independently F.

Embodiment 119 The compound of any one of embodiments 80-116, or a pharmaceutically acceptable salt or solvate thereof, wherein $R^{20k}$ is independently halogen, —CN, or —OCH$_3$.

Embodiment 120 A compound having the formula A-L$^{AB}$-B wherein
A is a monovalent form of a compound of one of embodiments 1 to 119;
L$^{AB}$ is a covalent linker bonded to A and B; and
B is a monovalent form of a degradation enhancer.

Embodiment 121 The compound of embodiment 120, wherein the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4CRBN) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

Embodiment 122 The compound of embodiment 120, wherein the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L$^3$, UBE2L$^6$, UBE2L$^1$, UBE2L$^2$, UBE2L$^4$, UBE2M, UBE2N, UBE2O, UBE2Q$^1$, UBE2Q$^2$, UBE2R$^1$, UBE2R$^2$, UBE2S, UBE2T, UBE2U, UBE2V1, UBE2V2, UBE2W, UBE2Z, ATG3, BIRC6, and UFC1.

Embodiment 123 The compound of any one of embodiments 120-122, wherein L$^{AB}$ is -L$^{AB1}$-L$^{AB2}$-L$^{AB3}$-L$^{AB4}$-L$^{AB5}$-. L$^{AB1}$, L$^{AB2}$, L$^{AB3}$, L$^{AB4}$, and L$^{AB5}$ are independently a bond, —O—, —N(R$^{14}$)—, —C(O)—, —N(R$^{14}$)C(O)—, —C(O)N(R$^{14}$)—, —S—, —S(O)$_2$—, —S(O)—, —S(O)$_2$N(R$^{14}$)—, —S(O)N(R$^{14}$)—, —N(R$^{14}$)S(O)—, —N(R$^{14}$)S(O)$_2$—, $C_{1-6}$alkylene, (—O—$C_{1-6}$alkyl)$_2$—, (—$C_{1-6}$alkyl-O)$_2$—, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, wherein $C_{1-6}$alkylene, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, are optionally substituted with one, two, or three R$^{20n}$; wherein each C$_{1-6}$alkyl of (—O—C$_{1-6}$alkyl)$_7$ and (—C$_{1-6}$alkyl-O)$_z$ — is optionally substituted with one, two, or three R$^{20l}$;

z is independently an integer from 0 to 10;

each R$^{12}$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_6$-10aryl, —CH$_2$-C$_{1-9}$heteroaryl, and C$_{1-9}$heteroaryl are optionally substituted with one, two, or three R$^{20l}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{1d}$ is independently selected from hydrogen, C$_{1-6}$alkyl, and C$_{1-6}$haloalkyl;

each R$^{15}$ is independently selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20m}$;

each R$^{20l}$, R$^{20m}$, and R$^{20n}$ is independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{23}$ is independently selected from H and C$_{1-6}$alkyl;
each R$^{24}$ is independently selected from H and C$_{1-6}$alkyl; and
each R$^{25}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl.

Embodiment 124 The compound of any one of embodiments 120-122, wherein L$^{AB}$ is —(O-C$_2$alkyl)$_z$— and z is an integer from 1 to 10.

Embodiment 125 The compound of any one of embodiments 120-122, wherein L$^{AB}$ is —(C$_2$alkyl-O—)$_z$— and z is an integer from 1 to 10.

Embodiment 126 The compound of any one of embodiments 120-122, wherein L$^{AB}$ is —(CH$_2$)zz1 L$^{AB2}$ (CH$_2$O)$_{zz2}$—, wherein L$^{AB2}$ is a bond, a 5 or 6 membered heterocycloalkylene or heteroarylene, phenylene, —(C$_2$-C$_4$) alkynylene, —$_sO2$— or —NH—; and zz1 and zz2 are independently an integer from 0 to 10.

Embodiment 127 The compound of any one of embodiments 120-122, wherein L$^{AB}$ is —(CH$_2$)zz1(CH$_2$O)$_{zz2}$—, wherein zz1 and zz2 are each independently an integer from 0 to 10.

Embodiment 128 The compound of any one of embodiments 120-122, wherein L$^{AB}$ is a PEG linker.

Embodiment 129 The compound of any one of embodiments 120-128, wherein B is a monovalent form of a compound selected from

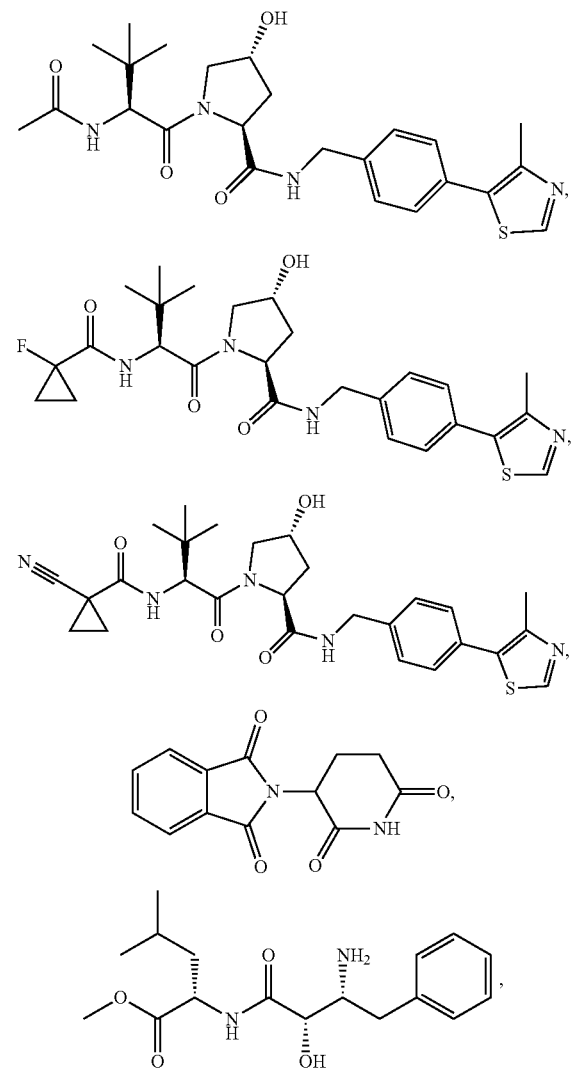

-continued

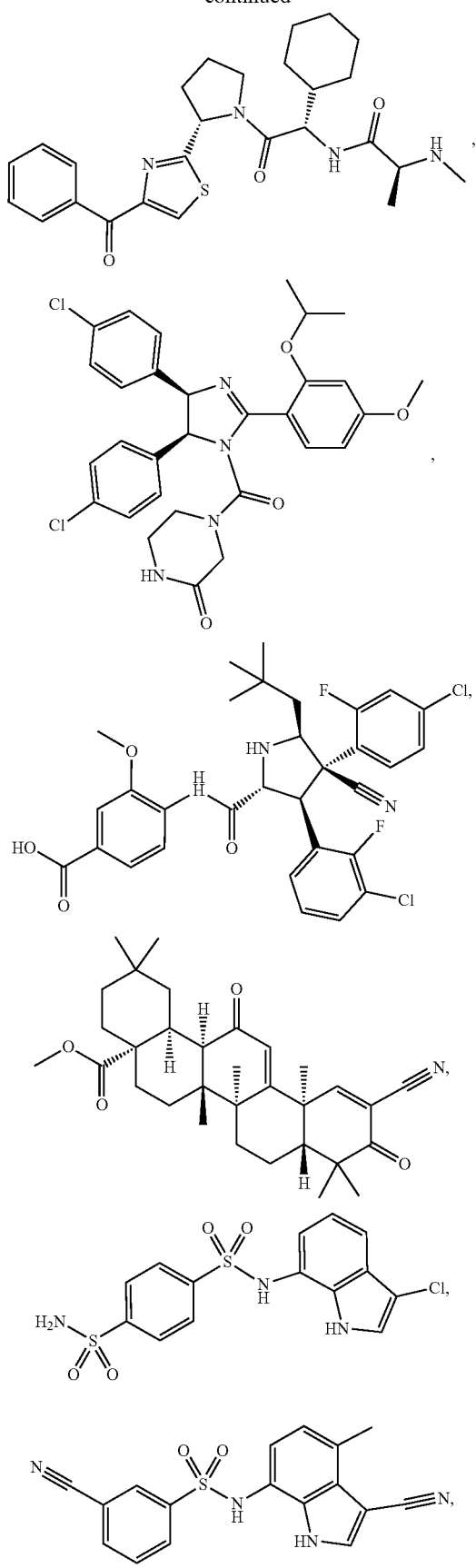

-continued

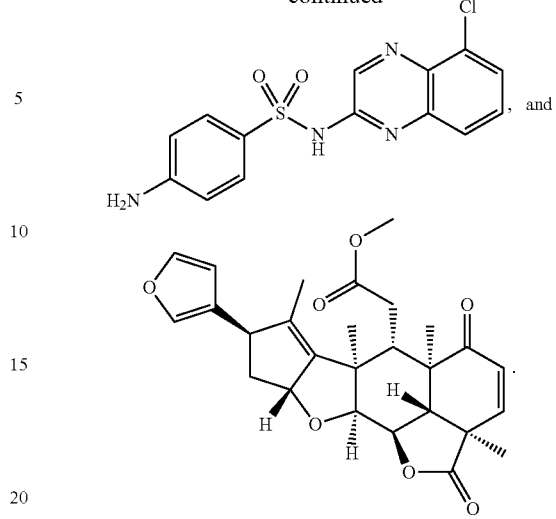

Embodiment 130 A pharmaceutical composition comprising a compound of any one of embodiments 1-129, or a pharmaceutically acceptable salt or solvate thereof, and a pharmaceutically acceptable excipient.

Embodiment 131 A method of treating cancer in a subject in need thereof, comprising administering to the subject a therapeutically effective amount of a compound or compound of any one of embodiments 1-129, or a pharmaceutically acceptable salt or solvate thereof.

Embodiment 132 A method of treating cancer in a subject comprising a Ras mutant protein, the method comprising: inhibiting the Ras mutant protein of said subject by administering to said subject a compound, wherein compound is characterized in that upon contacting the Ras mutant protein, said Ras mutant protein exhibits reduced Ras signaling output.

Embodiment 133 The method of embodiment 131 or embodiment 132, wherein the cancer is a solid tumor.

Embodiment 134 The method of embodiment 131 or embodiment 132, wherein the cancer is a hematological cancer.

Embodiment 135 The method of embodiment 131 or embodiment 132, wherein the compound is a compound of any one of embodiments 1-129.

Embodiment 136 A method of modulating signaling output of a Ras protein, comprising contacting a Ras protein with an effective amount of a compound or compound of any one of embodiments 1-129, or a pharmaceutically acceptable salt or solvate thereof, thereby modulating the signaling output of the Ras protein.

Embodiment 137 A method of inhibiting cell growth, comprising administering an effective amount of a compound or compound of one of embodiments 1-129, or a pharmaceutically acceptable salt or solvate thereof, to a cell expressing a Ras protein, thereby inhibiting growth of said cells.

Embodiment 138 The method of any one of embodiments 131-137 comprising administering an additional agent.

Embodiment 139 The method of embodiment 138, wherein the additional agent comprises (1) an inhibitor of MEK; (2) an inhibitor of epidermal growth factor receptor (EGFR) and/or of mutants thereof; (3) an immunotherapeutic agent; (4) a taxane; (5) an anti-metabolite; (6) an inhibitor of FGFR1 and/or FGFR2 and/or FGFR3 and/or of mutants thereof; (7) a mitotic kinase inhibitor; (8) an anti-angiogenic drug; (9) a topoisomerase inhibitor; (10) a platinum-containing compound; (12) an inhibitor of c-MET and/or of mutants thereof; (13) an inhibitor of BCR-ABL and/or of mutants thereof; (14) an inhibitor of ErbB2 (Her2) and/or of mutants thereof; (15) an inhibitor of AXL and/or of mutants thereof; (16) an inhibitor of NTRK1 and/or of mutants thereof; (17) an inhibitor of RET and/or of mutants thereof; (18) an inhibitor of A-Raf and/or B-Raf and/or C-Raf and/or of mutants thereof; (19) an inhibitor of ERK and/or of mutants thereof; (20) an MDM2 inhibitor; (21) an inhibitor of mTOR; (23) an inhibitor of IGF1/2 and/or of IGF1-R; (24) an inhibitor of CDK9; (25) an inhibitor of farnesyl transferase; (26) an inhibitor of SHIP pathway; (27) an inhibitor of SRC; (28) an inhibitor of JAK; (29) a PARP inhibitor, (31) a ROS1 inhibitor; (32) an inhibitor of SHP pathway, or (33) an inhibitor of Src, FLT3, HDAC, VEGFR, PDGFR, LCK, Bcr-Abl or AKT; (34) an inhibitor of KrasG12C mutant; (35) a SHC inhibitor (e.g., PP2, AID371185); (36) a GAB inhibitor; (38) a PI-3 kinase inhibitor; (39) a MARPK inhibitor; (40) CDK4/6 inhibitor; (41) MAPK inhibitor; (42) SHP2 inhibitor; (43) checkpoint immune blockade agents; (44) or SOS1 inhibitor; or (45) a SOS 2 inhibitor.

Embodiment 140 The method of embodiment 138, wherein the additional agent comprises an inhibitor of SHP2 selected from RMC-4630, ERAS-601,

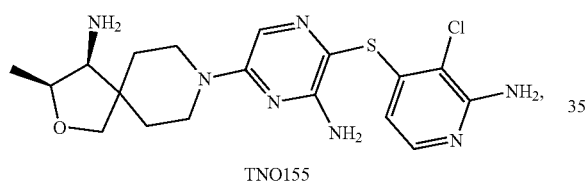

TNO155

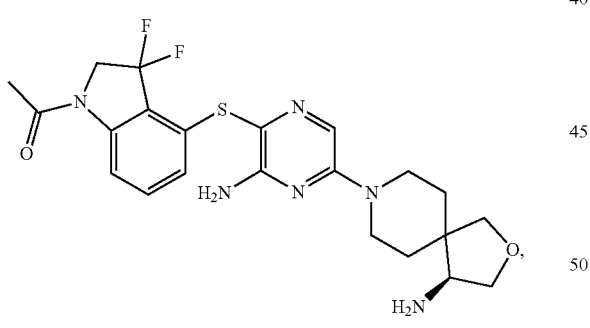

JAB-3068

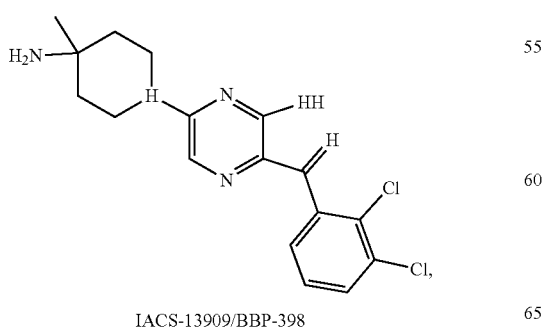

IACS-13909/BBP-398

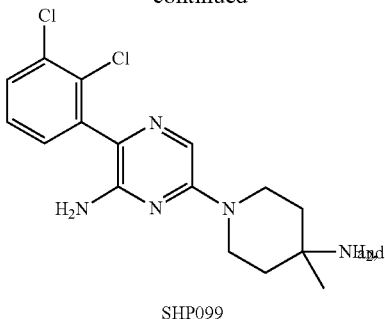

SHP099

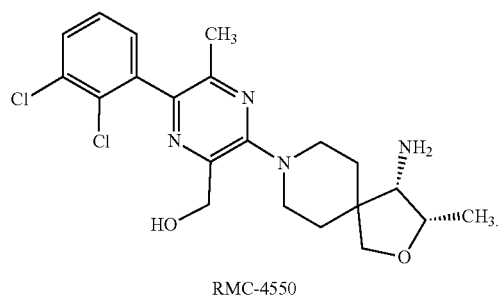

RMC-4550

Embodiment 141 The method of embodiment 138, wherein the additional agent comprises an inhibitor of SOS selected from

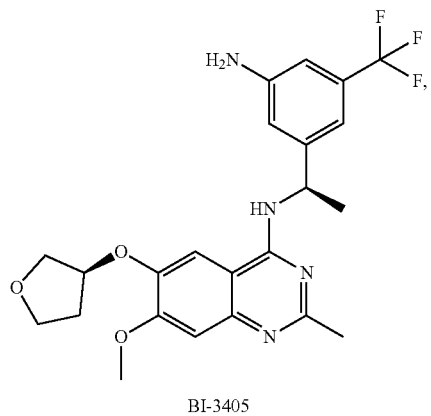

BI-3405

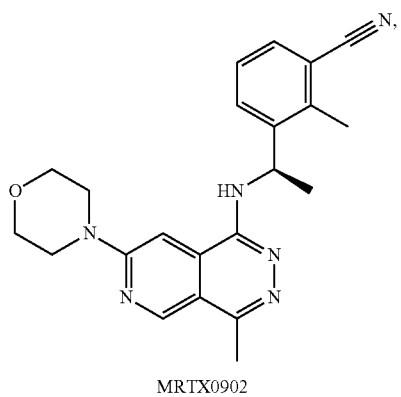

MRTX0902

-continued

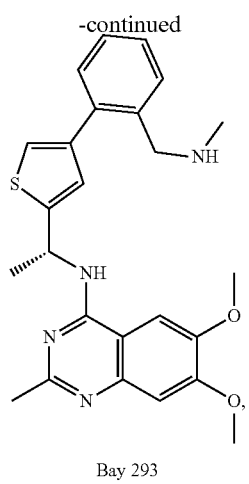

Bay 293

RMC-5845, and BI-1701963.

Embodiment 142 The method of embodiment 138, wherein the additional agent comprises an inhibitor of EGFR selected from afatinib, erlotinib, gefitinib, lapatinib, cetuximab panitumumab, osimertinib, olmutinib, and EGF-816.

Embodiment 143 The method of embodiment 138, wherein the additional agent comprises an inhibitor of MEK selected from trametinib, cobimetinib, binimetinib, selumetinib, refametinib, and AZD6244.

Embodiment 144 The method of embodiment 138, wherein the additional agent comprises an inhibitor of ERK selected from ulixertinib, MK-8353, LTT462, AZD0364, SCH772984, BIX02189, LY3214996, and ravoxertinib.

Embodiment 145 The method of embodiment 138, wherein the additional agent comprises an inhibitor of CDK4/6 selected from palbociclib, ribociclib, and abemaciclib.

Embodiment 146 The method of embodiment 138, wherein the additional agent comprises an inhibitor of BRAF selected from sorafenib, vemurafenib, dabrafenib, encorafenib, regorafenib, and GDC-879.

Embodiment 201 A compound of Formula (A), or a pharmaceutically acceptable salt or solvate thereof:

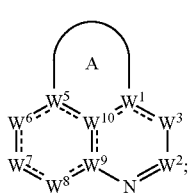

Formula (A)

wherein:
Ring A is a 5-10 membered cycloalkyl or 5-10 membered heterocycloalkyl ring, wherein the 5-10 membered cycloalkyl and 5-10 membered heterocycloalkyl ring are substituted with one or more $R^4$ and optionally substituted with one or more $R^{11c}$;

$W^1$ is $C(R^1)$, C, or N;

$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $C(R^2)$;

$R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_1$-9heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20b}$;

$W^3$ is $N(R^{3b})$, N, $C(R^3)$, $C(R^3)(R^{3a})$, or $C(O)$;

$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_2$—,heterocycloalkyl, $C_{6-10}$aryl, $C_1$-9heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$;

$W^5$ is $C(R^5)$, C, or N;

$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, C(O), S(O), or $S(O)_2$;

$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$, $R^{6b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20e}$;

$W^7$ is $N(R^7)$, $C(R^7)$, or $C(R^7)(R^{7a})$;

$R^{7a}$ and each $R^{7c}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20f}$;

$R^{7d}$ is independently selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl are optionally substituted with one, two, or three $R^{20f}$;

$R^7$ is -$L^7$-$R^{17}$;

$L^7$ is a bond, —O—, —$N(R^{7d})$—, —C(O)—, —S—, —$S(O)_2$—, —S(O)—, —$P(O)R^{7d}$—, $CR^{7o}R^{7c}$, —$OCR^7GR^{7c}$—, —$N(R^{7d})CR^7cR^{7c}$—, —C(O)$CR^7CR^{7c}$—, —$SCR^7R^{7c}$—, —$S(O)_2CR^7GR^{7c}$—, —$S(O)CR^7GR^{7c}$—, —$P(O)R^{7d}$ $CR7GR^{7c}$—, —$CR^7GR^7CR^7CR^7c$, —$CR^7R^7CO$—, —$CR^7CR^{7o}N(R^{7d})$—, —$CR^7GR^{7o}$ C.(O)—, —$CR^7CR^{7c}S$—, —$CR^7CR^7CS(O)_2$—, —$CR^7CR^{7c}S(O)$—, —$CR^7CR^7CP(O)R^{7d}$—, —$N(R^{7d})C(O)$—, —$N(R^{7d})S(O)_2$—, —$N(R^{7d})S(O)$—, —$N(R^{7d})P(O)R^{7d}$—, —$C(O)N(R^{7d})$—, —$S(O)_2N(R^{7d})$—, —$S(O)N(R^{7d})$—, —$P(O)R^{7a}N(R^{7d})$—, —OC(O)—, —$OS(O)_2$—, —OS (O)—, —$OP(O)R^{7d}$ —, —C(O)O—, —$S(O)_{20}$—, —S(O)O—, or —$P(O)R^{7d}$ O—;

$R^{17}$ is selected from

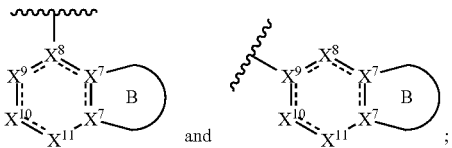

and

Ring B is a 5- or 6-membered cycloalkyl ring, 5- or 6-membered heterocycloalkyl ring, or 5- or 6-membered heteroaryl ring; wherein the 5- or 6-membered cycloalkyl ring, 5- or 6-membered heterocycloalkyl ring, and 5- or 6-membered heteroaryl ring are optionally substituted with one or more $R^{1c}$;

$X^6$, $X^7$, and $X^8$ are independently C or $C(R^{1a})$;

$X^9$, $X^{10}$, and $X^{11}$ are independently C(O), $C(R^{1a})$, or $C(R^{1a})(R^{1b})$;

each $R^{1a}$, $R^{1b}$, and $R^{1c}$ are each independently selected from hydrogen, halogen, —CN, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20g}$;

$W^8$ is $C(R^8)$, $C(R^8)(R^{8a})$, N, $N(R^{8b})$, C(O), S(O), or $S(O)_2$;

$R^8$ and $R^{8a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$ heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20h}$, $R^{8b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=OX(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20h}$, $W^9$ is C(R'), C, or N;

$W^{10}$ is $C(R^9)$, C, or N;

each $R^9$ is independently selected from hydrogen, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20i}$;

$R^4$ is -$L^4$-$R^{4a}$;

each $L^4$ is independently selected from a bond, —O—, —N($R^{4d}$)—, —C(O)—, —S—, —S(O)$_2$—, —S(O)—, —P(O)$R^{4d}$—, $CR^{4c}R^{4c}$, —$OCR^4R^{4c}$—, —N($R^{4d}$)$CR^4GR^{4c}$—, —C(O)$CR^4R^{4c}$—, —$SCR^4R^{4c}$—, —S(O)$_2$ $CR^4R^{4c}$—, —S(O)$CR^4R^{4c}$—, —P(O)$R^{4d}CR^4R^{4c}$—, —$CR^4R^4CR^4R^{4c}$—, —$CR^4CR^4CO$—, —$CR^4GRAN(R^{4d})$—, —$CR^4GR^{4c}CC(O)$—, —$CR^4R^{4c}S$—, —$CR^4R^{4c}S(O)_2$—, —$CR^4R^{4S}(O)$—, —$CR^4R^4CP(O)R^{4d}$—, —N($R^{4d}$)C(O)—, —N($R^{4d}$)S(O)$_2$—, —N($R^{4d}$)S(O)—, —N($R^{4d}$)P(O)$R^{4d}$—, —C(O)N($R^{4d}$)—, —S(O)$_2$N($R^{4d}$)—, —S(O)N($R^{4d}$)—, —P(O)$R^{4d}$ON($R^{4d}$)—, —OC(O)—, —OS(O)$_2$—, —OS(O)—, —OP(O)$R^{4d}$—, —C(O)O—, —S(O)$_{20}$—, —S(O)O—, and —P(O)$R^{4d}$O—;

each $R^4$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —C(O)$OR^{14}$, —C(O)N($R^{14}$)($R^{14}$), —C(O)C(O)N($R^{14}$)($R^{14}$), —OC(O)N($R^{14}$)($R^{14}$), —C(O)$R^{14a}$, —S(O)$_2R^{14}$, —S(O)$_2$N($R^{14}$)($R^{14}$), —OCH$_2$C(O)$OR^{14}$, —OC(O)$R^{14}$a, —N($R^{14}$)($R^{14}$), —N($R^{14}$)C(O)N($R^{14}$)($R^{14}$), —N($R^{14}$)C(O)$OR^{14}$, —N($R^{14}$)C(O)$R^{14a}$, and —N($R^{14}$)S(O)$_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —N($R^{14}$)($R^{14}$), —C(O)$OR^{14}$, —C(O)N($R^{14}$)($R^{14}$), —C(O)C(O)N($R^{14}$)($R^{14}$), —OC(O)N($R^{14}$)($R^{14}$), —N($R^{14}$)C(O)N($R^{14}$)($R^{14}$), —N($R^{14}$)C(O)$OR^{14}$, —N($R^{14}$)C(O)$R^{14}$, —N($R^{14}$)S(O)$_2R^{14}$, —C(O)$R^{14a}$, —S(O)$_2R^{14}$, —S(O)$_2$N($R^{14}$)($R^{14}$), and —OC(O)$R^{14a}$;

each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —C(O)$OR^{14}$, —C(O)N($R^{14}$)($R^{14}$), —C(O)C(O)N($R^{14}$)($R^{14}$), —OC(O)N($R^{14}$)($R^{14}$), —C(O)$R^{14a}$, —S(O)$_2R^{14}$, —S(O)$_2$N($R^{14}$)($R^{14}$), —OCH$_2$C(O)$OR^{14}$, and —OC(O)$R^{14}$a, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —N($R^{14}$)($R^{14}$), —C(O)$OR^{14}$, —C(O)N($R^{14}$)($R^{14}$), —C(O)C(O)N($R^{14}$)($R^{14}$), —OC(O)N($R^{14}$)($R^{14}$), —N($R^{14}$)C(O)N($R^{14}$)($R^{14}$), —N($R^{14}$)C(O)$OR^{14}$, —N($R^{14}$)C(O)$R^{14}$, —N($R^{14}$)S(O)$_2R^{14}$, —C(O)$R^{14a}$, —S(O)$_2R^{14}$, —S(O)$_2$N($R^{14}$)($R^{14}$), and —OC(O)$R^{143}$;

each $R^{4a}$ is independently selected from $C_{2-9}$heterocycloalkyl, wherein $C_{2-9}$heterocycloalkyl, are optionally substituted with one, two, three, or four $R^{4b}$;

each $R^{4b}$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O) (=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, —$CH_2$S(O)$_2$N($R^{12}$)($R^{13}$), and —P(=O)($R^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20j}$;

each $R^{11c}$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N ($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, or three $R^{20k}$;

each $R^{12}$ is independently selected from hydrogen, $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_2$—,heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_{2-9}$heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl are optionally substituted with one, two, or three $R^{20l}$;

each $R^{12c}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{1d}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$, each $R^{20a}$, $R^{20\%}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ are each independently selected from halogen, oxo, —CN, $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, —CH$_2$-$C_{2-9}$heterocycloalkyl, $C_{6-10}$aryl, —CH$_2$-$C_{6-10}$aryl, —CH$_2$-$C_{1-9}$heteroaryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$-$C_{3-10}$cycloalkyl, $C_{2-9}$heterocycloalkyl, $C_{2-9}$heterocycloalkyl, $C_{6-10}$aryl, —CH$_2$-$C_{6-10}$aryl, —CH$_2$-$C_1$-9heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl;

each R$^{23}$ is independently selected from H and $C_{1-6}$alkyl;
each R$^{24}$ is independently selected from H and $C_{1-6}$alkyl;
each R$^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and
------ indicates a single or double bond such that all valences are satisfied.

Embodiment 202 A compound of Formula (B), or a pharmaceutically acceptable salt or solvate thereof:

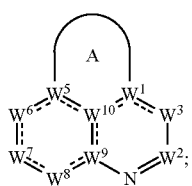

Formula (B)

wherein:
Ring A is a 5-10 membered cycloalkyl or 5-10 membered heterocycloalkyl ring, wherein the 5-10 membered cycloalkyl and 5-10 membered heterocycloalkyl ring are optionally substituted substituted with one or more R$^4$ and optionally substituted with one or more R$^{11c}$;

W$^1$ is C(R$^1$), C, or N;
R$^1$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three R$^{20a}$, W$^2$ is C(R$^2$);
R$^2$ is selected from halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three R$^{20b}$;

W$^3$ is N(R$^{3b}$), N, C(R$^3$), C(R$^3$)(R$^{3a}$), or C(O);
R$^3$ and R$^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$heteroaryl are optionally substituted with one, two, or three R$^{20c}$, R$^{3b}$ is selected from hydrogen, —CN, $C_{1-6}$alkyl, $C_2$-calkenyl, $C_{2-6}$alkynyl, $C_{3-10}$cycloalkyl, $C_{2-9}$heterocycloalkyl, $C_{6-10}$aryl, $C_1$-heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three R$^{20c}$;

W$^5$ is C(R$^5$), C, or N;
R$^5$ is selected from hydrogen, halogen, —CN, $C_{1-6}$alkyl, $C_{2-6}$alkenyl, $C_{2-6}$alkynyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, and $C_{2-6}$alkynyl are optionally substituted with one, two, or three R$^{20d}$, W$^6$ is N(R$^{6b}$), N, C(R$^6$), C(R$^6$)(R$^{6a}$), C(O), S(O), or S(O)$_2$;
R$^6$ and R$^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_2$-9heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20e}$;

R$^{6b}$ is selected from hydrogen, —CN, C$_{1-6}$alkyl, C$_2$-calkenyl, C$_{2-6}$alkynyl, C$_{3-10}$cycloalkyl, C$_2$-heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and -CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20e}$;

W$^7$ is N(R$^7$), C(R$^7$), or C(R$^7$)(R$^{7a}$);

R$^{7a}$ and each R$^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20f}$;

R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_6$-10aryl, and C$_{1-9}$heteroaryl are optionally substituted with one, two, or three R$^{20f}$;

R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$—, CR$^7$cR7c, —OCR$^7$GR$^{7c}$—, —N(R$^{74}$)CR$^7$R$^{7c}$—, —C(O)CR$^{7o}$R$^{7c}$—, —SCR$^7$R$^{7c}$—, —S(O)$_2$CR$^7$GR$^{7c}$—, —S(O)CR$^7$GR$^{7c}$—, —P(O)R$^{7d}$CR7GR$^{7c}$—, —CR$^7$R$^7$CR$^7$CR$^7$c, —CR$^7$GR$^7$CO—, —CR$^7$R$^{7a}$N(R$^{7d}$)—, —CR$^7$GR$^{7o}$C.(O)—, —CR$^7$cR$^7$cS—, —CR$^7$GR$^7$CS(O)$_2$—, —CR$^7$GR$^{7c}$S(O)—, —CR$^7$GR$^7$cP(O)R$^{7d}$—, —N(R$^{7d}$)C(O)—, —N(R$^{7d}$)S(O)$_2$—, —N(R$^{7d}$)S(O)—, —N(R$^{7d}$)P(O)R$^{7d}$—, —C(O)N(R$^{7d}$)—, —S(O)$_2$N(R$^{7d}$)—, —S(O)N(R$^{74}$)—, —P(O)R$^7$ON(R$^{74}$)—, —OC(O)—, —OS(O)$_2$—, —OS(O)—, —OP(O)R$^{7d}$—, —C(O)O—, —S(O)$_{20}$—, —S(O)O—, or —P(O)R$^{7d}$O—;

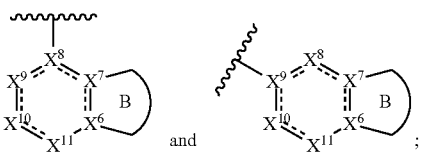

R$^{17}$ is selected from Ring B is a 5- or 6-membered cycloalkyl ring, 5- or 6-membered heterocycloalkyl ring, 5- or 6-membered heteroaryl ring, or 6-membered aryl ring, wherein the 5- or 6-membered cycloalkyl ring, 5- or 6-membered heterocycloalkyl ring, 5- or 6-membered heteroaryl ring, and 6-membered aryl ring are optionally substituted with one or more R$^{1c}$;

X$^6$, X$^7$, and X$^8$ are independently C or C(R$^{1a}$);

X$^9$, X$^{10}$, and X$^{11}$ are independently C(O), C(R$^{1a}$), or C(R$^{1a}$)(R$^1$b);

each R$^{1a}$, R$^1$b, and R$^{1c}$ are each independently selected from hydrogen, halogen, —CN, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20}$g;

W$^8$ is C(R$^8$), C(R$^8$)(R$^{8a}$), N, N(R$^8$b), C(O), S(O), or S(O)$_2$;

R$^8$ and R$^{8a}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and -CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20}$h, each R$^8$ is independently selected from hydrogen, C$_{1-6}$alkyl, C$_{2-6}$alkenyl, C$_{3-10}$cycloalkyl, C$_{2-9}$heterocycloalkyl, CH$_{6-10}$ aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20}$h, W$^9$ is C(R$^9$), C, or N;

W$^{10}$ is C(R$^9$), C, or N;

each R$^9$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_{1-9}$heteroaryl, and $C_{1-9}$heteroaryl are optionally substituted with one, two, or three $R^{20}i$;

$R^4$ is -$L^4$-$R^4a$, each $L^4$ is independently selected from a bond, —O—, —N($R^{4d}$)—, —C(O)—, —S—, —S(O)$_2$—, —S(O)—, —P(O)$R^{4d}$—, $CR^{4c}R^{4c}$, —$OCR^4CR^{4c}$—, —N($R^{4d}$)$CR^4GR^{4c}$—, —C(O)$CR^4R^{4c}$—, —$SCR^4GR^{4c}$—, —S(O)$_2CR^4R^{4c}$—, —S(O)$CR^4R^{4c}$—, —P(O)$R^{4d}CR^4R^{4c}$—, —$CR^{4c}R^4CR^{4c}R^{4c}$—, —$CR^{4c}R^4O$—, —$CR^{4c}R^4N(R^{4d})$—, —$CR^4R^4C(O)$—, —$CR^4R^4CS$—, —$CR^4R^{4c}S(O)_2$—, —$CR^4R^{4c}S(O)$—, —$CR^4R^4 cP(O)R^{4d}$—, —N($R^{4d}$)C(O)—, —N($R^{4d}$)S(O)$_2$—, —N($R^{4d}$)S(O)—, —N($R^{4d}$)P(O)$R^{4d}$—, —C(O)N($R^{4d}$)—, —S(O)$_2$N($R^{4d}$)—, —S(O)N($R^{4d}$)—, —P(O)$R^{4d}$N($R^{4d}$)—, —OC(O)—, —OS(O)$_2$—, —OS(O)—, —OP(O)$R^{4d}$—, —C(O)O—, —S(O)$_{20}$—, —S(O)O—, and —P(O)$R^{4d}$O—;

each $R^4$ is independently selected from hydrogen, halogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —C(O)$OR^{14}$, —C(O)N($R^{14}$)($R^{14}$), —C(O)C(O)N($R^{14}$)($R^{14}$), —OC(O)N($R^{14}$)($R^{14}$), —C(O)$R^{14}a$, —S(O)$_2R^{14}$, —S(O)$_2$N($R^{14}$)($R^{14}$), —$OCH_2C(O)OR^{14}$, —OC(O)$R^{143}$, —N($R^{14}$)($R^{14}$), —N($R^{14}$)C(O)N($R^{14}$)($R^{14}$), —N($R^{14}$)C(O)$OR^{14}$, —N($R^{14}$)C(O)$R^{14}a$, and —N($R^{14}$)S(O)$_2R^{14}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —N($R^{14}$)($R^{14}$), —C(O)$OR^{14}$, —C(O)N($R^{14}$)($R^{14}$), —C(O)C(O)N($R^{14}$)($R^{14}$), —OC(O)N($R^{14}$)($R^{14}$), —N($R^{14}$)C(O)N($R^{14}$)($R^{14}$), —N($R^{14}$)C(O)$OR^{14}$, —N($R^{14}$)C(O)$R^{14}$, —N($R^{14}$)S(O)$_2R^{14}$, —C(O)$R^{14}a$, —S(O)$_2R^{14}$, —S(O)$_2$N($R^{14}$)($R^{14}$), and —OC(O)$R^{14}a$;

each $R^{4a}$ is independently selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are optionally substituted with one, two, three, or four $R^4b$;

each $R^4b$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, —$CH_2$S(O)$_2$N($R^{12}$)($R^{13}$), and —P(=O)($R^{12}$)$_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20}j$;

each $R^{11}c$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$OR^{12}$, —$SR^{12}$, —N($R^{12}$)($R^{13}$), —C(O)$OR^{12}$, —OC(O)N($R^{12}$)($R^{13}$), —N($R^{14}$)C(O)N($R^{12}$)($R^{13}$), —N($R^{14}$)C(O)$OR^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, —S(=O)(=NH)N($R^{12}$)($R^{13}$), —$CH_2$C(O)N($R^{12}$)($R^{13}$), —$CH_2$N($R^{14}$)C(O)$R^{15}$, —$CH_2$S(O)$_2R^{15}$, and —$CH_2$S(O)$_2$N($R^{12}$)($R^{13}$), wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, or three $R^{20}k$;

each $R^{12}$ is independently selected from hydrogen, $C_{1-6}$alkyl, $C_{2-6}$alkenyl, $C_{2-6}$alkynyl, $C_{3-10}$cycloalkyl, —C($R^{12}c$)$_2$-$C_{3-10}$cycloalkyl, $C_{2-9}$heterocycloalkyl, —C($R^{12}c$)$_2$-$C_{2-9}$heterocycloalkyl, $C_{6-10}$aryl, —C($R^{12}c$)$_2$-$C_{6-10}$aryl, —C($R^{12}c$)$_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —C($R^{12c}$)$_2$-$C_{3-10}$cycloalkyl, $C_{2-9}$heterocycloalkyl, —C($R^{12c}$)$_2$-$C_{2-9}$heterocycloalkyl, $C_{6-10}$aryl, —C($R^{12c}$)$_2$-$C_{6-10}$aryl, —C($R^{12c}$)$_2$-$C_{1-9}$heteroaryl, and $C_{1-9}$heteroaryl are optionally substituted with one, two, or three $R^{20l}$;

each $R^{12c}$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$;

each $R^{1d}$ is independently selected from hydrogen, $C_{1-6}$alkyl, and $C_{1-6}$haloalkyl;

each $R^{14a}$ is independently selected from $C_{1-6}$alkyl and $C_{1-6}$haloalkyl;

each $R^{15}$ is independently selected $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20m}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, $R^{20k}$, $R^{20l}$, and $R^{20m}$ are each independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_6$-10aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_1$-9heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;
each $R^{24}$ is independently selected from H and $C_{1-6}$alkyl;
each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ------ indicates a single or double bond such that all valences are satisfied.

Embodiment 203 A compound of Formula (C), or a pharmaceutically acceptable salt or solvate thereof:

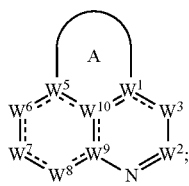

Formula (C)

wherein:
Ring A is a 5-10 membered cycloalkyl or 5-10 membered heterocycloalkyl ring, wherein the 5-10 membered cycloalkyl and 5-10 membered heterocycloalkyl ring are substituted with at least one $R^4$, and wherein the 5-10 membered cycloalkyl and 5-10 membered heterocycloalkyl ring are optionally substituted with one or more $R^{11c}$;
$W^1$ is $C(R^1)$, C, or N;
$R^1$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20a}$;

$W^2$ is $C(R^2)$;
$R^2$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20b}$;

$W^3$ is $N(R^{3b})$, N, $C(R^3)$, $C(R^3)(R^{3a})$, or $C(O)$;
$R^3$ and $R^{3a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl are optionally substituted with one, two, or three $R^{20c}$;

$R^{3b}$ is selected from hydrogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-6}$heteroaryl are optionally substituted with one, two, or three $R^{20c}$;

$W^5$ is $C(R^5)$, C, or N;
$R^5$ is selected from hydrogen, halogen, —CN, $C_{1-6}$alkyl, $C_{2-6}$alkenyl, $C_{2-6}$alkynyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, and $C_{2-6}$alkynyl are optionally substituted with one, two, or three $R^{20d}$;

$W^6$ is $N(R^{6b})$, N, $C(R^6)$, $C(R^6)(R^{6a})$, $C(O)$, $S(O)$, or $S(O)_2$;
$R^6$ and $R^{6a}$ are independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-6}$heteroaryl are optionally substituted with one, two, or three R$^{20e}$;

R$^{8b}$ is selected from hydrogen, —CN, C$_{1-6}$alkyl, C$_{2-6}$alkenyl, C$_{2-6}$alkynyl, C$_{3-10}$cycloalkyl, C$_2$-heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-9heteroaryl are optionally substituted with one, two, or three R$^{20e}$;

W$^7$ is N(R$^7$), C(R$^7$), or C(R$^7$)(R$^{7a}$);

R$^{7a}$ and each R$^{7c}$ are independently selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-9heteroaryl are optionally substituted with one, two, or three R$^{20f}$;

R$^{7d}$ is independently selected from hydrogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_6$-oaryl, and C$_{1-9}$heteroaryl are optionally substituted with one, two, or three R$^{20f}$;

R$^7$ is -L$^7$-R$^{17}$;

L$^7$ is a bond, —O—, —N(R$^{7d}$)—, —C(O)—, —S—, —S(O)$_2$—, —S(O)—, —P(O)R$^{7d}$, CR$^{7o}$R$^{7c}$, —OCR$^7$R$^{7c}$—, —N(R$^{7d}$)CR$^7$CR$^{7c}$—, —C(O)CR$^7$GR$^{7c}$—, —SCR$^7$GR$^{7c}$—, —S(O)$_2$CR$^7$GR$^{7c}$—, —S(O)CR$^7$GR$^{7c}$—, —P(O)R$^{7d}$ CR$^7$CR$^{7c}$—, —CR$^7$GR$^{7c}$CR$^7$CR$^7$c, —CR$^7$cRICO—, —CR$^7$GR$^{7c}$N(R$^{7d}$)—, —CR$^7$GR$^{7o}$ C.(O)—, —CR$^7$R$^{7S}$—, —CR$^7$CR$^{7c}$S(O)$_2$—, —CR$^7$CR$^{7c}$S(O)—, —CR$^7$GR$^{7o}$P(O)R$^{7d}$ —, —N(R$^{74}$)C(O)—, —N(R$^{7d}$)S(O)$_2$—, —N(R$^{7d}$)S(O)—, —N(R$^{7d}$)P(O)R$^{7d}$ —, —C(O)N(R$^{7d}$)—, —S(O)$_2$N(R$^{7d}$)—, —S(O)N(R$^{7d}$)—, —P(O)R$^{7a}$N(R$^{7d}$)—, —P(O)R$^{7a}$N(R$^{7d}$)—, —OC(O)—, —OS(O)$_2$—, —OS(O)—, —OP(O)R$^{7d}$ —, —C(O)O—, —S(O)$_{20}$—, —S(O)O—, or —P(O)R$^{7d}$ O—;

R$^{17}$ is selected from C$_{2-9}$heterocycloalkyl and C$_{1-9}$heteroaryl, wherein C$_{2-9}$heterocycloalkyl and C$_{1-9}$heteroaryl are optionally substituted with one, two, or three R$^{20g}$;

W$^8$ is C(R$^8$), C(R$^8$)(R$^{8a}$), N, N(R$^{8b}$), C(O), S(O), or S(O)$_2$;

R$^8$ and R$^{8a}$ are independently selected from hydrogen, halogen, —CN, C$_{1-6}$alkyl, C$_{2-6}$alkenyl, C$_{2-6}$alkynyl, C$_{3-10}$cycloalkyl, C$_2$-9 heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, —S(=OX—NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and -CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20h}$, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$)—, —S(=OX=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-9heteroaryl are optionally substituted with one, two, or three R$^{20h}$, W$^9$ is C(R$^9$), C, or N;

W$^{10}$ is C(R$^9$), C, or N;

each R$^9$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_2$-heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three R$^{20i}$, R$^4$ is -L$^4$-R$^4$a, L$^4$ is a bond, —O—, —N(R$^{4d}$)—, —C(O)—, —S—, —S(O)$_2$—, —S(O)—, —P(O)R$^{4d}$—, CR$^{4c}$R$^{4c}$, —OCR$^4$R$^{4c}$—, —N(R$^{4d}$)CR$^4$R$^4$—, —C(O)CR$^4$R$^4$—, —SCR$^4$R$^{4c}$—, —S(O)$_2$CR$^4$R$^{4c}$—, —S(O)CR$^4$R$^4$—, —P(O)R$^{4d}$CR$^4$R$^4$—, —CR$^4$R$^4$CR$^4$R$^4$, —CR$^4$RO—, —CR$^4$R$^4$N(R$^{4d}$)—, —CR$^4$R$^{4c}$C(O)—, —CR$^{4c}$R$^{4c}$S—, —CR$^4$R$^4$S(O)$_2$—, —CR$^{4c}$R$^{4c}$S(O)—, —CR$^4$R$^4$ cP(O)R$^{4d}$—, —N(R$^{4d}$)C(O)—, —N(R$^{4d}$)S(O)$_2$—, —N(R$^{4d}$)S(O)—, —N(R$^{4d}$)P(O)R$^{4d}$—, —C(O)N(R$^{4d}$)—, —S(O)$_2$N(R$^{4d}$)—, —S(O)N(R$^{4d}$)—, —P(O)R$^{4d}$N(R$^{4d}$)—, —OC(O)—, —OS(O)$_2$—, —OS(O)—, —OP(O)R$^{4d}$—, —C(O)O—, —S(O)$_{20}$—, —S(O)O—, or —P(O)R$^{4d}$O—;

each R$^{4c}$ is independently selected from hydrogen, halogen, —CN, C$_{1-6}$alkyl, C$_{2-6}$alkenyl, C$_{2-6}$alkynyl, C$_{1-6}$haloalkyl, C$_{1-6}$alkoxy, C$_{1-6}$haloalkoxy, C$_{3-10}$cycloalkyl, —CH$_2$-C$_{3-10}$cycloalkyl, C$_{2-9}$heterocycloalkyl, —CH$_2$-C$_{2-9}$heterocycloalkyl, —OR$^{14}$, —SR$^{14}$, —C(O)OR$^{14}$, —C(O)N(R$^{14}$)(R$^{14}$), —C(O)C(O)N(R$^{14}$)(R$^{14}$), —OC(O)N(R$^{14}$)(R$^{14}$), —C(O)R$^{14}$a, —S(O)$_2$R$^{14}$, —S(O)$_2$N(R$^{14}$)(R$^{14}$), —OCH$_2$C(O)OR$^{14}$, —OC(O)R$^{14}$a, —N(R$^{14}$)(R$^{14}$), —N(R$^{14}$)C(O)N(R$^{14}$)(R$^{14}$), —N(R$^{14}$)C(O)OR$^{14}$, —N(R$^{14}$)C(O)R$^{14}$a, and —N(R$^{14}$)S(O)$_2$R$^{14}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, $C_{2-9}$heterocycloalkyl, and —$CH_2$-$C_{2-9}$heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14}a$, —$S(O)_2R^{14}$, —$S(O)_2N(R^{14})(R^{14})$, and —$OC(O)R^{14}a$, each $R^{4d}$ is independently selected from hydrogen, —CN, $C_{1-6}$alkyl, $C_{2-6}$alkenyl, $C_{2-6}$alkynyl, $C_{1-6}$haloalkyl, $C_{1-6}$alkoxy, $C_{1-6}$haloalkoxy, $C_{3-10}$cycloalkyl, —$CH_2$-$C_{3-10}$cycloalkyl, $C_{2-9}$heterocycloalkyl, —$CH_2$-$C_{2-9}$heterocycloalkyl, —$OR^{14}$, —$SR^{14}$, —$C(O)OR^{14}$, —$C(O)N(R^{14})(R^{14})$, —$C(O)C(O)N(R^{14})(R^{14})$, —$OC(O)N(R^{14})(R^{14})$, —$C(O)R^{14}a$, —$S(O)_2R^{14}$, —$S(O)_2N(R^{14})(R^{14})$, —$OCH_2C(O)OR^{14}$, and —$OC(O)R^{14}a$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, and —$CH_2$-$C_2$-heterocycloalkyl, are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{14}$, —$SR^{14}$, —$N(R^{14})(R^{14})$, —$C(O)OR^{14}$, —$C(O)N(R^{14})(R^{14})$, —$C(O)C(O)N(R^{14})(R^{14})$, —$OC(O)N(R^{14})(R^{14})$, —$N(R^{14})C(O)N(R^{14})(R^{14})$, —$N(R^{14})C(O)OR^{14}$, —$N(R^{14})C(O)R^{14}$, —$N(R^{14})S(O)_2R^{14}$, —$C(O)R^{14}a$, —$S(O)_2R^{14}$, —$S(O)_2N(R^{14})(R^{14})$, and —$OC(O)R^{14}a$;

$R^{4a}$ is selected from $C_{3-10}$cycloalkyl, $C_{2-9}$heterocycloalkyl, and $C_{6-10}$aryl, wherein $C_{3-10}$cycloalkyl, $C_{2-9}$heterocycloalkyl, and $C_{6-10}$aryl are optionally substituted with one, two, three, or four $R^4b$;

each $R^4b$ is independently selected from halogen, oxo, —CN, $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, and —$P(=O)(R^{12})_2$, wherein $C_{1-6}$alkyl, $C_{2-6}$alkenyl, $C_{2-6}$alkynyl, $C_{3-12}$cycloalkyl, $C_{2-11}$heterocycloalkyl, $C_{6-10}$aryl, and $C_{1-9}$heteroaryl are optionally substituted with one or more $R^{20}j$;

each $R^{11}c$ is independently selected from halogen, oxo, —CN, $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, $C_{1-11}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{1-6}$haloalkyl, $C_{3-12}$cycloalkyl, —$CH_2$-$C_{3-12}$cycloalkyl, $C_{1-11}$heterocycloalkyl, —$CH_2$-$C_{1-11}$heterocycloalkyl, $C_{6-12}$aryl, —$CH_2$-$C_{6-12}$aryl, —$CH_2$-$C_{1-11}$heteroaryl, and $C_{1-11}$heteroaryl are optionally substituted with one, two, or three $R^{20}k$;

each $R^{12}$ is independently selected from hydrogen, $C_{1-6}$alkyl, $C_{2-6}$alkenyl, $C_{2-6}$alkynyl, $C_{3-10}$cycloalkyl, —$C(R^{12}c)_2$-$C_{3-10}$cycloalkyl, $C_{2-9}$heterocycloalkyl, —$C(R^{12}c)_2$-$C_{2-9}$heterocycloalkyl, $C_{6-10}$aryl, —$C(R^{12}c)_2$-$C_{6-10}$aryl, —$C(R^{12}c)_2$-$C_{1-9}$heteroaryl, and $C_{1-9}$heteroaryl, wherein $C_{1-6}$alkyl, $C_{2-6}$alkenyl, $C_{2-6}$alkynyl, $C_{3-10}$cycloalkyl, —$C(R^{12}c)_2$-$C_{3-10}$cycloalkyl, $C_{2-9}$heterocycloalkyl, —$C(R^{12}c)_2$-$C_{2-9}$heterocycloalkyl, $C_{6-10}$aryl, —$C(R^{12}c)_2$-$C_{6-10}$aryl, —$C(R^{12}c)_2$-$C_{1-9}$heteroaryl, and $C_{1-9}$heteroaryl are optionally substituted with one, two, or three $R^{20l}$, each $R^{12}c$ is independently selected from hydrogen and $R^{20l}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20l}$, each $R^{1d}$ is independently selected from hydrogen, $C_{1-6}$alkyl, and $C_{1-6}$haloalkyl;

each $R^{14}a$ is independently selected from $C_{1-6}$alkyl and $C_{1-6}$haloalkyl;

each $R^{15}$ is independently selected $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_1$-9heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20}m$;

each $R^{20}a$, $R^{20b}$, $R^{20}c$, $R^{20d}$, $R^{20}e$, $R^{20}f$, $R^{20}g$, $R^{20}h$, $R^{20}i$, $R^{20}j$, $R^{20}k$, $R^{20l}$, and $R^{20}m$ are each independently selected from halogen, oxo, —CN, $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_6$-10aryl, —$CH_2$-$C_{6-10}$aryl, —$CH_2$-$C_{1-9}$heteroaryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$-$C_{3-10}$cycloalkyl, $C_{2-9}$heterocycloalkyl, —$CH_2$-$C_{2-9}$heterocycloalkyl, $C_{6-10}$aryl, —$CH_2$-$C_{6-10}$aryl, —$CH_2$-$C_1$-9heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, $C_6$-10aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl; and ----- indicates a single or double bond such that all valences are satisfied.

Embodiment 204 The compound of embodiment 201, or a pharmaceutically acceptable salt or solvate thereof, having the structure of Formula (A-1):

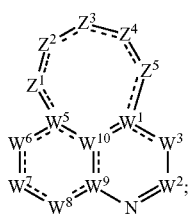

Formula (A-1)

wherein $Z^1$, $Z^3$, and $Z^5$ are each independently selected from $N(R^4)$, $N(R^{11}c)$, $N(H)$, $N$, $C(R^4)$, $C(R^{11}c)$, $C(H)$, $C(R^4)(H)$, $C(R^4)(R^{11}c)$, $C(R^{11}c)(R^{11}c)$, $C(R^4)(R^4)$, $C(R^{11}c)(H)$, $CH_2$, $S$, $O$, and $C(O)$; and $Z^2$ and $Z^4$ are each independently selected from a bond, $N(R^4)$, $N(R^{11}c)$, $N(H)$, $N$, $C(R^4)$, $C(R^{11}c)$, $C(H)$, $C(R^4)(H)$, $C(R^4)(R^{11}c)$, $C(R^{11}c)(R^{11}c)$, $C(R^4)(R^4)$, $C(R^{11}c)(H)$, $CH_2$, $S$, $O$, and $C(O)$;

wherein at least one of $Z^1$, $Z^2$, z3, $Z^4$, and $Z^5$ is $N(R^4)$, $C(R^4)$, $C(R^4)(H)$, $C(R^4)(R^{11}c)$, or $C(R^4)(R^4)$.

Embodiment 205 The compound of embodiment 202, or a pharmaceutically acceptable salt or solvate thereof, having the structure of Formula (B-1):

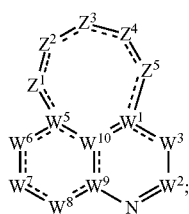

Formula (B-1)

wherein $Z^1$, $Z^3$, and $Z^5$ are each independently selected from $N(R^4)$, $N(R^{11}c)$, $N(H)$, $N$, $C(R^4)$, $C(R^{11}c)$, $C(H)$, $C(R^4)(H)$, $C(R^4)(R^{11}c)$, $C(R^{11}c)(R^{11}c)$, $C(R^4)(R^4)$, $C(R^{11}c)(H)$, $CH_2$, $S$, $O$, and $C(O)$; and $Z^2$ and $Z^4$ are each independently selected from a bond, $N(R^4)$, $N(R^{11}c)$, $N(H)$, $N$, $C(R^4)$, $C(R^{11}c)$, $C(H)$, $C(R^4)(H)$, $C(R^4)(R^{11}c)$, $C(R^{11}c)(R^{11}c)$, $C(R^4)(R^4)$, $C(R^{11}c)(H)$, $CH_2$, $S$, $O$, and $C(O)$.

Embodiment 206 The compound of embodiment 203, or a pharmaceutically acceptable salt or solvate thereof, having the structure of Formula (C-1):

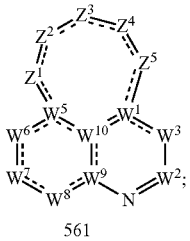

Formula (C-1)

wherein $Z^1$, $Z^3$, and $Z^3$ are each independently selected from $N(R^4)$, $N(R^{11}c)$, $N(H)$, $N$, $C(R^4)$, $C(R^{11}c)$, $C(H)$, $C(R^4)(H)$, $C(R^4)(R^{11}c)$, $C(R^{11}c)(R^{11}c)$, $C(R^4)(R^4)$, $C(R^{11}c)(H)$, $CH_2$, $S$, $O$, and $C(O)$; and $Z^2$ and $Z^4$ are each independently selected from a bond, $N(R^4)$, $N(R^{11}c)$, $N(H)$, $N$, $C(R^4)$, $C(R^{11}c)$, $C(H)$, $C(R^4)(H)$, $C(R^4)(R^{11}c)$, $C(R^{11}c)(R^{11}c)$, $C(R^4)(R^4)$, $C(R^{11}c)(H)$, $CH_2$, $S$, $O$, and $C(O)$;

wherein at least one of $Z^1$, $Z^2$, z3, $Z^4$, and $Z^5$ is $N(R^4)$, $C(R^4)$, $C(R^4)(H)$, $C(R^4)(R^{11}c)$, or $C(R^4)(R^4)$.

Embodiment 207 The compound of any one of embodiments 201-206, or a pharmaceutically acceptable salt or solvate thereof, wherein $W^1$ is C.

Embodiment 208 The compound of any one of embodiments 201-206, or a pharmaceutically acceptable salt or solvate thereof, wherein $W^1$ is $C(R^1)$.

Embodiment 209 The compound of any one of embodiments 201-206, or a pharmaceutically acceptable salt or solvate thereof, wherein $W^1$ is N.

Embodiment 210 The compound of any one of embodiments 201-209, or a pharmaceutically acceptable salt or solvate thereof, wherein $W^5$ is C.

Embodiment 211 The compound of any one of embodiments 201-209, or a pharmaceutically acceptable salt or solvate thereof, wherein $W^5$ is $C(R^5)$.

Embodiment 212 The compound of any one of embodiments 201-209, or a pharmaceutically acceptable salt or solvate thereof, wherein $W^5$ is N.

Embodiment 213 The compound of any one of embodiments 201-212, or a pharmaceutically acceptable salt or solvate thereof, wherein $W^2$ is $C(R^2)$.

Embodiment 214 The compound of any one of embodiments 201-212, or a pharmaceutically acceptable salt or solvate thereof, wherein $W^2$ is $C(R^2)(R^{2a})$.

Embodiment 215 The compound of any one of embodiments 201-212, or a pharmaceutically acceptable salt or solvate thereof, wherein $W^2$ is N.

Embodiment 216 The compound of any one of embodiments 201-212, or a pharmaceutically acceptable salt or solvate thereof, wherein $W^2$ is $N(R^{2a})$.

Embodiment 217 The compound of any one of embodiments 201-216, or a pharmaceutically acceptable salt or solvate thereof, wherein $W^3$ is N.

Embodiment 218 The compound of any one of embodiments 201-216, or a pharmaceutically acceptable salt or solvate thereof, wherein $W^3$ is $N(R^{3b})$.

Embodiment 219 The compound of any one of embodiments 201-216, or a pharmaceutically acceptable salt or solvate thereof, wherein $W^3$ is $C(R^3)$.

Embodiment 220 The compound of any one of embodiments 201-216, or a pharmaceutically acceptable salt or solvate thereof, wherein $W^3$ is $C(R^3)(R^{3a})$.

Embodiment 221 The compound of any one of embodiments 201-216, or a pharmaceutically acceptable salt or solvate thereof, wherein $W^3$ is C(O).

Embodiment 222 The compound of any one of embodiments 201-221, or a pharmaceutically acceptable salt or solvate thereof, wherein $W^6$ is $C(R^6)$.

Embodiment 223 The compound of any one of embodiments 201-221, or a pharmaceutically acceptable salt or solvate thereof, wherein $W^6$ is $C(R^6)(R^{6a})$.

Embodiment 224 The compound of any one of embodiments 201-221, or a pharmaceutically acceptable salt or solvate thereof, wherein $W^6$ is N.

Embodiment 225 The compound of any one of embodiments 201-221, or a pharmaceutically acceptable salt or solvate thereof, wherein $W^6$ is $N(R^{6b})$.

Embodiment 226 The compound of any one of embodiments 201-221, or a pharmaceutically acceptable salt or solvate thereof, wherein $W^6$ is C(O).

Embodiment 227 The compound of any one of embodiments 201-226, or a pharmaceutically acceptable salt or solvate thereof, wherein $W^7$ is $C(R^7)$.

Embodiment 228 The compound of any one of embodiments 201-226, or a pharmaceutically acceptable salt or solvate thereof, wherein $W^7$ is $C(R^7)(R^{7a})$.

Embodiment 229 The compound of any one of embodiments 201-226, or a pharmaceutically acceptable salt or solvate thereof, wherein $W^7$ is $N(R^7)$.

Embodiment 230 The compound of any one of embodiments 201-229, or a pharmaceutically acceptable salt or solvate thereof, wherein $W^8$ is $C(R^8)$.

Embodiment 231 The compound of any one of embodiments 201-229, or a pharmaceutically acceptable salt or solvate thereof, wherein $W^8$ is $C(R^8)(R^{8a})$.

Embodiment 232 The compound of any one of embodiments 201-229, or a pharmaceutically acceptable salt or solvate thereof, wherein $W^8$ is N.

Embodiment 233 The compound of any one of embodiments 201-229, or a pharmaceutically acceptable salt or solvate thereof, wherein $W^8$ is $N(R^{8b})$.

Embodiment 234 The compound of any one of embodiments 201-229, or a pharmaceutically acceptable salt or solvate thereof, wherein $W^8$ is C(O).

Embodiment 235 The compound of any one of embodiments 201-234, or a pharmaceutically acceptable salt or solvate thereof, wherein $W^9$ is C.

Embodiment 236 The compound of any one of embodiments 201-234, or a pharmaceutically acceptable salt or solvate thereof, wherein $W^9$ is N.

Embodiment 237 The compound of any one of embodiments 201-236, or a pharmaceutically acceptable salt or solvate thereof, wherein $W^{10}$ is C.

Embodiment 238 The compound of any one of embodiments 201-236, or a pharmaceutically acceptable salt or solvate thereof, wherein $W^{10}$ is N.

Embodiment 239 The compound of embodiment 204, or a pharmaceutically acceptable salt or solvate thereof, having the structure of Formula (A-1a):

Formula (A-1a)

Embodiment 240 The compound of embodiment 204, or a pharmaceutically acceptable salt or solvate thereof, having the structure of Formula (A-1b):

Formula (A-1b)

Embodiment 241 The compound of embodiment 204, or a pharmaceutically acceptable salt or solvate thereof, having the structure of Formula (A-1c):

Formula (A-1c)

Embodiment 242 The compound of embodiment 204, or a pharmaceutically acceptable salt or solvate thereof, having the structure of Formula (A-1d):

Formula (A-1d)

Embodiment 243 The compound of embodiment 204, or a pharmaceutically acceptable salt or solvate thereof, having the structure of Formula (A-1e):

Formula (A-1e)

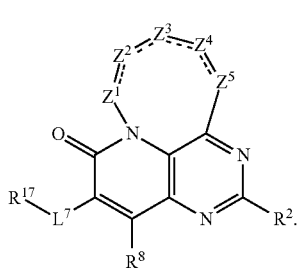

Embodiment 244 The compound of embodiment 204, or a pharmaceutically acceptable salt or solvate thereof, having the structure of Formula (A-1f):

Formula (A-1f)

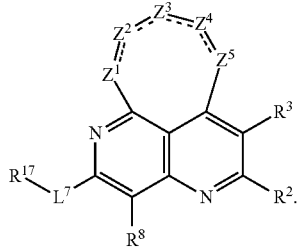

Embodiment 245 The compound of any one of embodiments 239-244, or a pharmaceutically acceptable salt or solvate thereof,

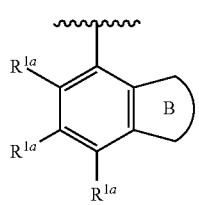

wherein $R^{17}$ is

Embodiment 246 The compound of any one of embodiments 239-244, or a pharmaceutically acceptable salt or solvate thereof,

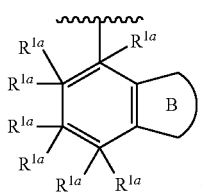

wherein $R^{17}$ is

Embodiment 247 The compound of any one of embodiments 239-244, or a pharmaceutically acceptable salt or solvate thereof,

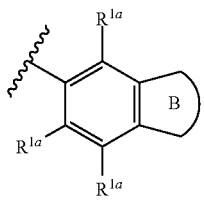

wherein $R^{17}$ is

Embodiment 248 The compound of any one of embodiments 239-244, or a pharmaceutically acceptable salt or solvate thereof,

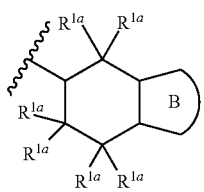

wherein $R^{17}$ is

Embodiment 249 The compound of any one of embodiments 245-248, or a pharmaceutically acceptable salt or solvate thereof, wherein each $R^{1a}$ is independently selected from hydrogen, halogen, $C_{1-6}$alkyl, and $-OR^{12}$, wherein $C_{1-6}$alkyl is optionally substituted with one, two, or three $R^{20g}$.

Embodiment 250 The compound of any one of embodiments 245-249, or a pharmaceutically acceptable salt or solvate thereof, wherein Ring B is a 5- or 6-membered heteroaryl ring optionally substituted with one or more $R^{1c}$.

Embodiment 251 The compound of any one of embodiments 239-248, or a pharmaceutically acceptable salt or solvate thereof,

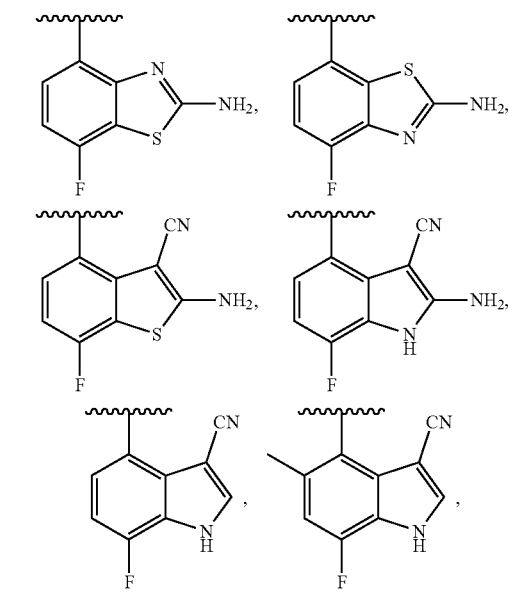

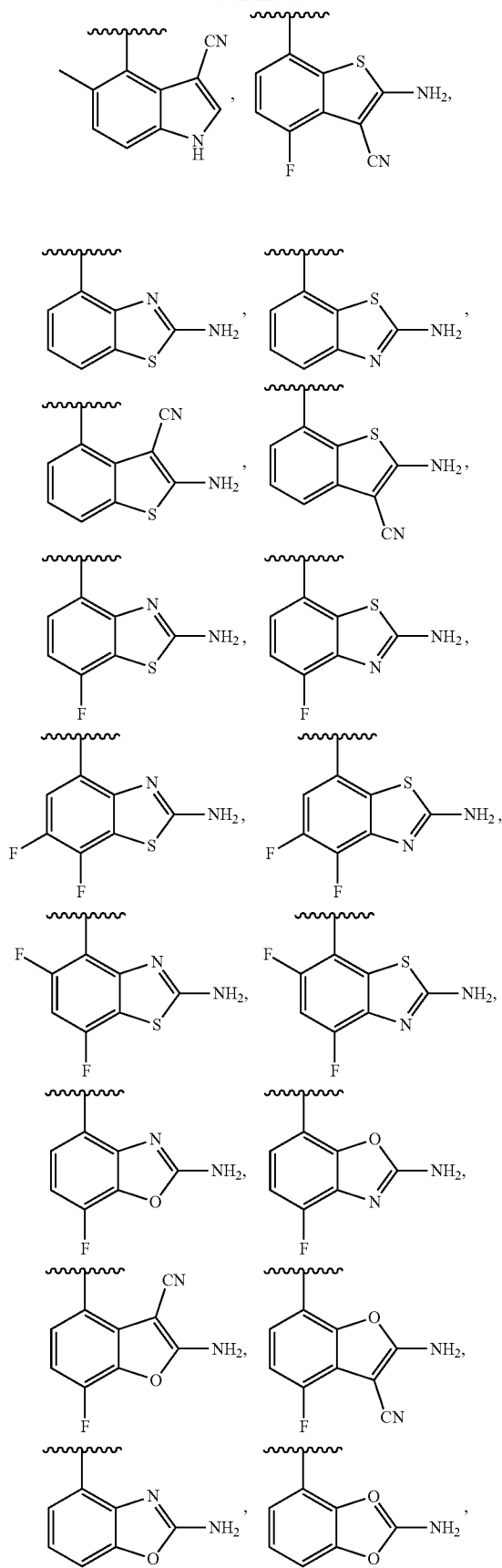
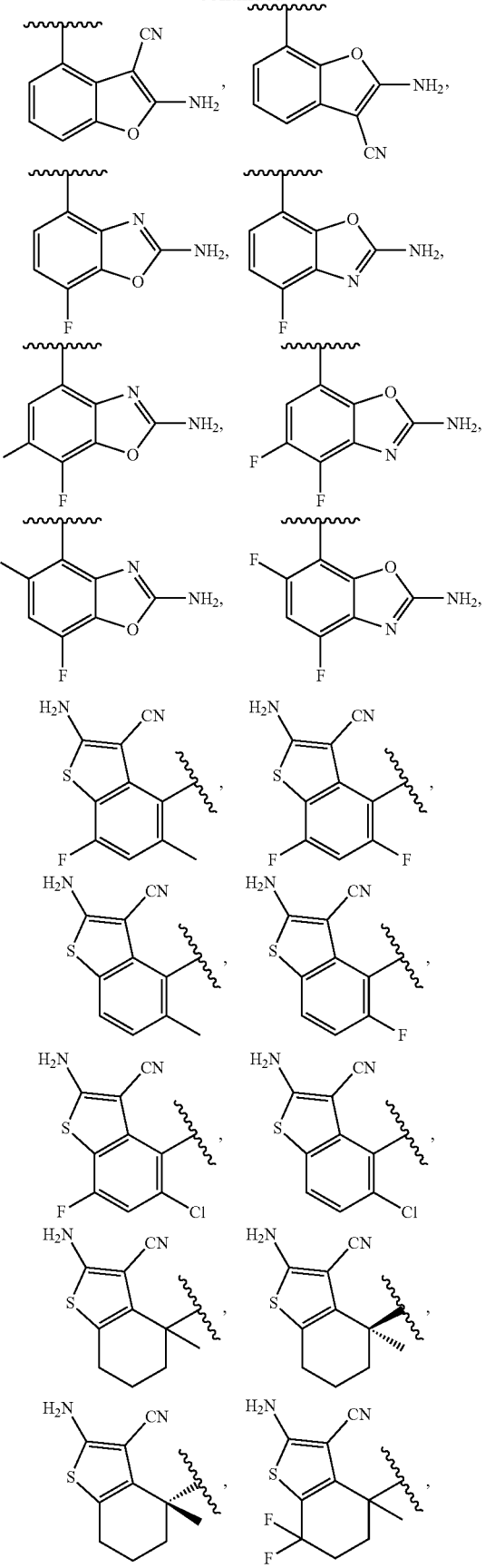

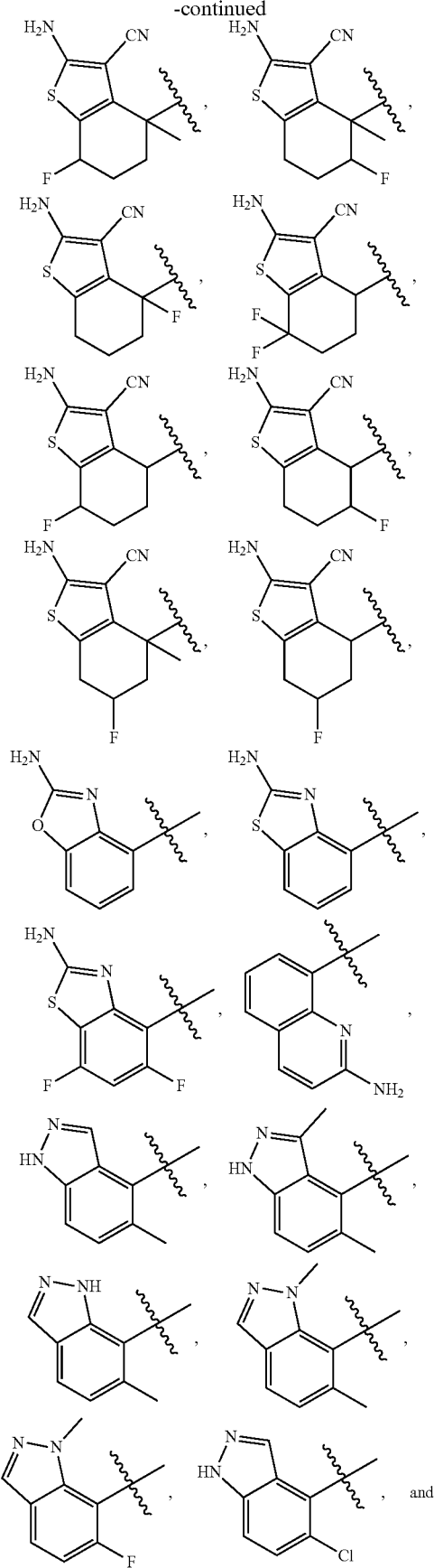

-continued

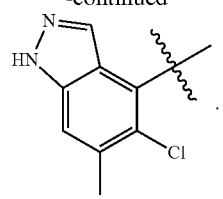

wherein $R^{17}$ is selected from:

Embodiment 252 The compound of embodiment 205, or a pharmaceutically acceptable salt or solvate thereof, having the structure of Formula (B-1a):

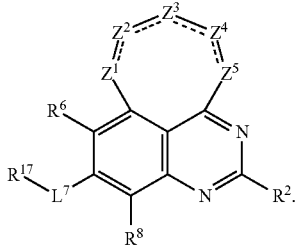

Formula (B-1a)

Embodiment 253 The compound of embodiment 205, or a pharmaceutically acceptable salt or solvate thereof, having the structure of Formula (B-1b):

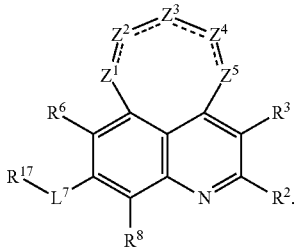

Formula (B-1b)

Embodiment 254 The compound of embodiment 205, or a pharmaceutically acceptable salt or solvate thereof, having the structure of Formula (B-1c):

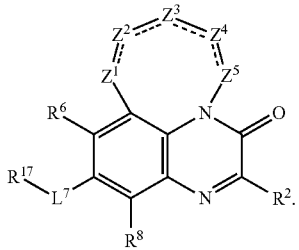

Formula (B-1c)

Embodiment 255 The compound of embodiment 205, or a pharmaceutically acceptable salt or solvate thereof, having the structure of Formula B-1d):

Embodiment 256 The compound of embodiment 205, or a pharmaceutically acceptable salt or solvate thereof, having the structure of Formula (B-1e):

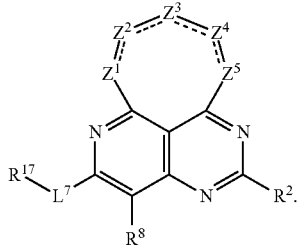

Formula (B-1e)

Embodiment 257 The compound of embodiment 205, or a pharmaceutically acceptable salt or solvate thereof, having the structure of Formula (B-1f):

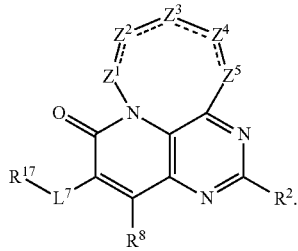

Formula (B-1f)

Embodiment 258 The compound of any one of embodiments 252-257, or a pharmaceutically acceptable salt or solvate thereof,

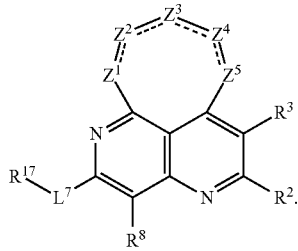

wherein $R^{17}$ is

Embodiment 259 The compound of any one of embodiments 252-257, or a pharmaceutically acceptable salt or solvate thereof,

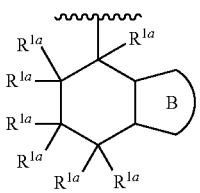

wherein $R^{17}$ is

Embodiment 260 The compound of any one of embodiments 252-257, or a pharmaceutically acceptable salt or solvate thereof,

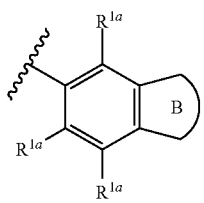

wherein $R^{17}$ is

Embodiment 261 The compound of any one of embodiments 252-257, or a pharmaceutically acceptable salt or solvate thereof,

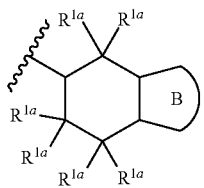

wherein $R^{17}$ is

Embodiment 262 The compound of any one of embodiments 258-261, or a pharmaceutically acceptable salt or solvate thereof, wherein each $R^{1a}$ is independently selected from hydrogen, halogen, $C_{1-6}$alkyl, and —$OR^{12}$, wherein $C_{1-6}$alkyl is optionally substituted with one, two, or three $R^{20g}$ Embodiment 263 The compound of any one of embodiments 258-262, or a pharmaceutically acceptable salt or solvate thereof, wherein Ring B is a 5- or 6-membered heteroaryl ring optionally substituted with one or more $R^{1c}$.

Embodiment 264 The compound of any one of embodiments 258-262, or a pharmaceutically acceptable salt or solvate thereof, wherein Ring B is a 6-membered aryl ring optionally substituted with one or more RIc.

Embodiment 265 The compound of any one of embodiments 252-261, or a pharmaceutically acceptable salt or solvate thereof,

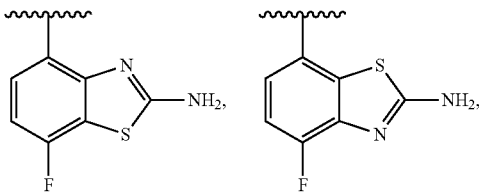

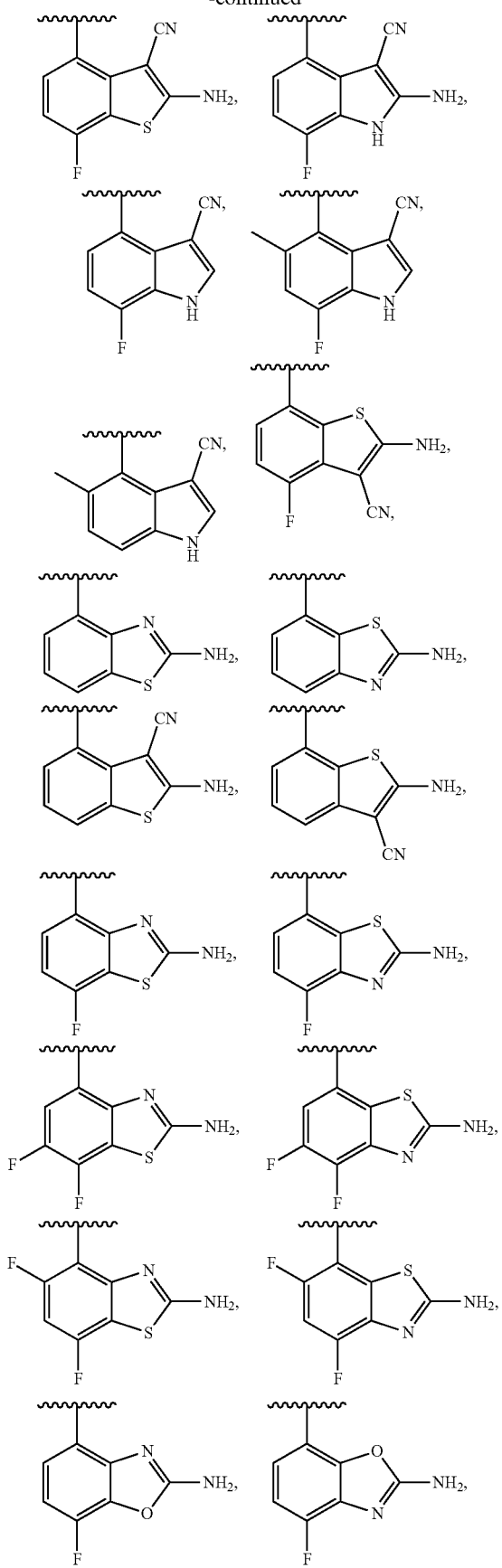
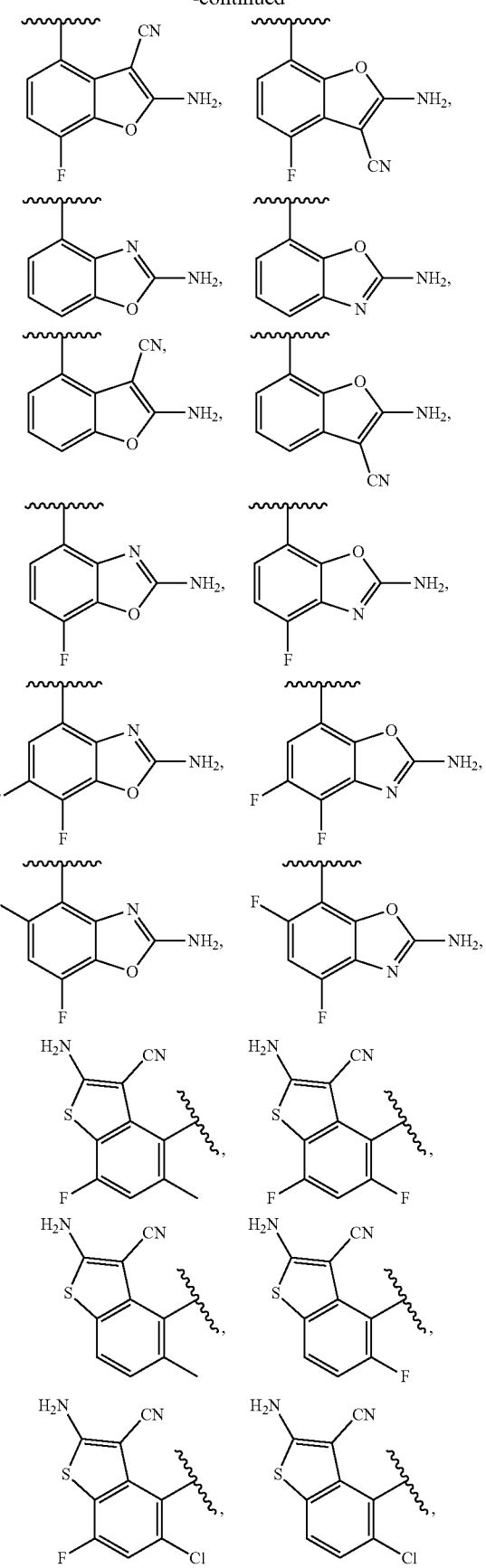

-continued

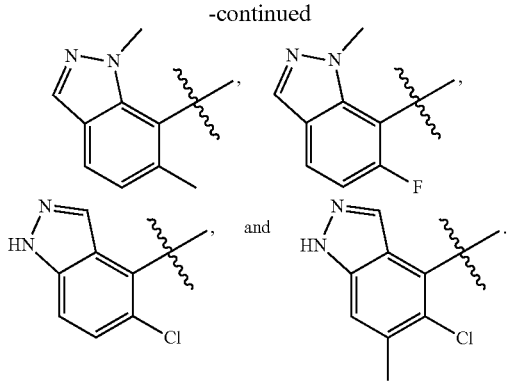

wherein R[17] is selected from:

Embodiment 266 The compound of embodiment 206, or a pharmaceutically acceptable salt or solvate thereof, having the structure of Formula (C-1a):

Formula (C-1a)

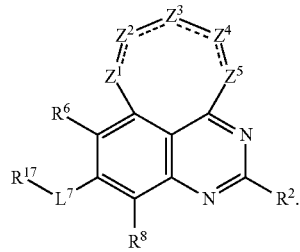

Embodiment 267 The compound of embodiment 206, or a pharmaceutically acceptable salt or solvate thereof, having the structure of Formula (C-1b):

Formula C-1b)

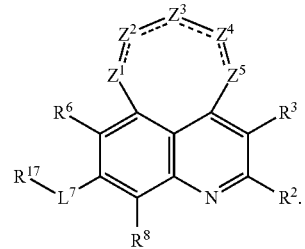

Embodiment 268 The compound of embodiment 206, or a pharmaceutically acceptable salt or solvate thereof, having the structure of Formula (C-1c):

Formula (C-1c)

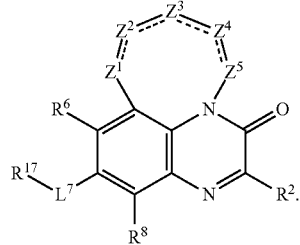

Embodiment 269 The compound of embodiment 206, or a pharmaceutically acceptable salt or solvate thereof, having the structure of Formula C-1d):

Formula (C-1d)

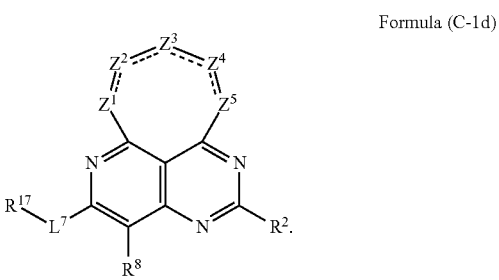

Embodiment 270 The compound of embodiment 206, or a pharmaceutically acceptable salt or solvate thereof, having the structure of Formula (C-1e):

Formula (C-1e)

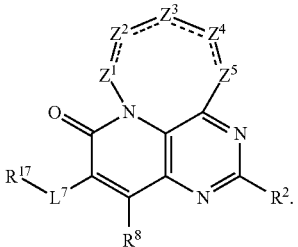

Embodiment 271 The compound of embodiment 206, or a pharmaceutically acceptable salt or solvate thereof, having the structure of Formula (C-1f):

Formula (C-1f)

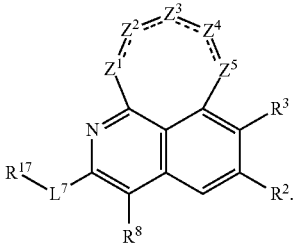

Embodiment 272 The compound of any one of embodiments 266-271, or a pharmaceutically acceptable salt or solvate thereof, wherein R[17] is $C_{2-9}$heterocycloalkyl optionally substituted with one, two, or three $R^{20g}$.

Embodiment 273 The compound of any one of embodiments 266-271, or a pharmaceutically acceptable salt or solvate thereof, wherein R[17] is $C_{1-9}$heteroaryl optionally substituted with one, two, or three $R^{20g}$.

Embodiment 274 The compound of any one of embodiments 266-271, or a pharmaceutically acceptable salt or solvate thereof,

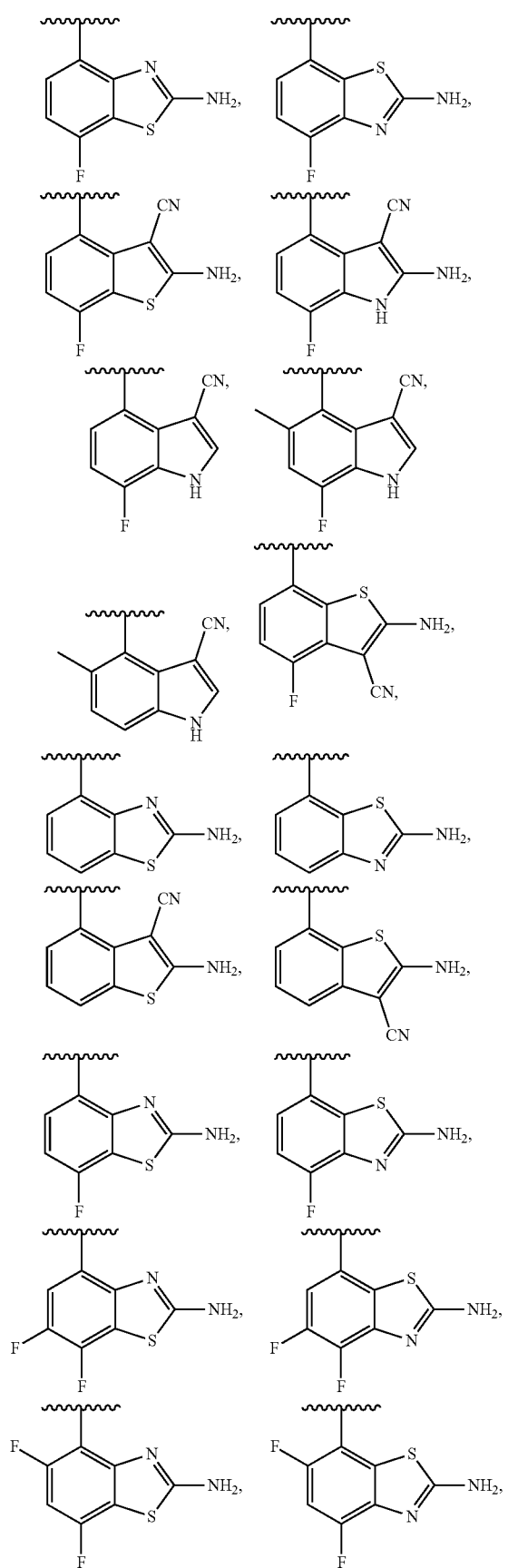
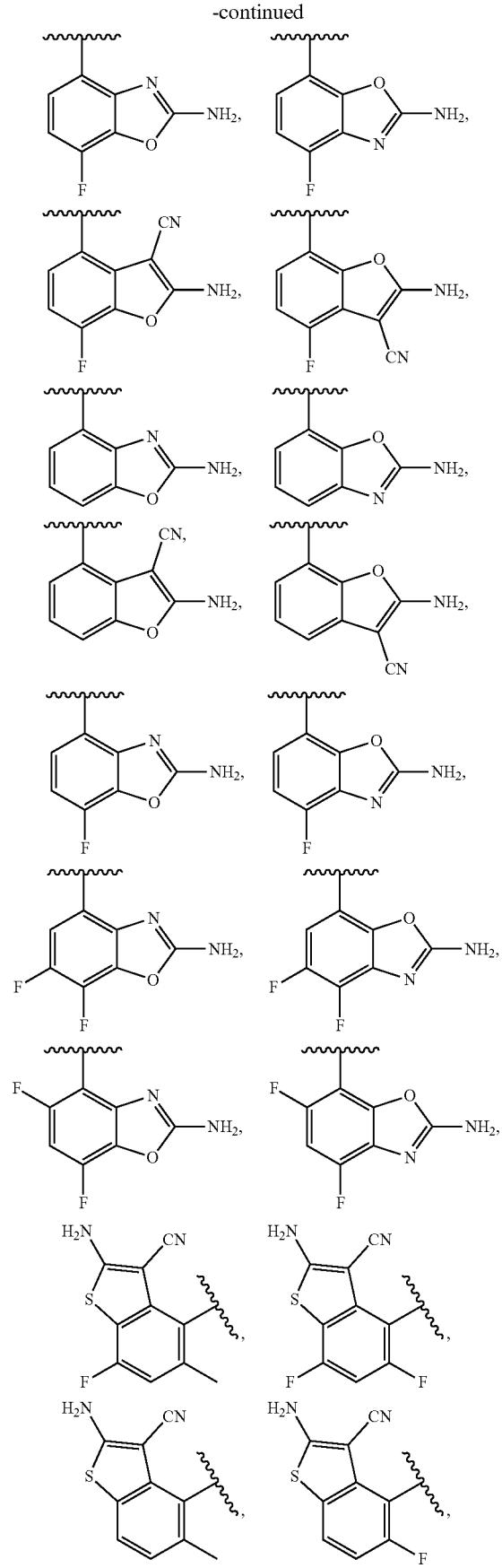

-continued
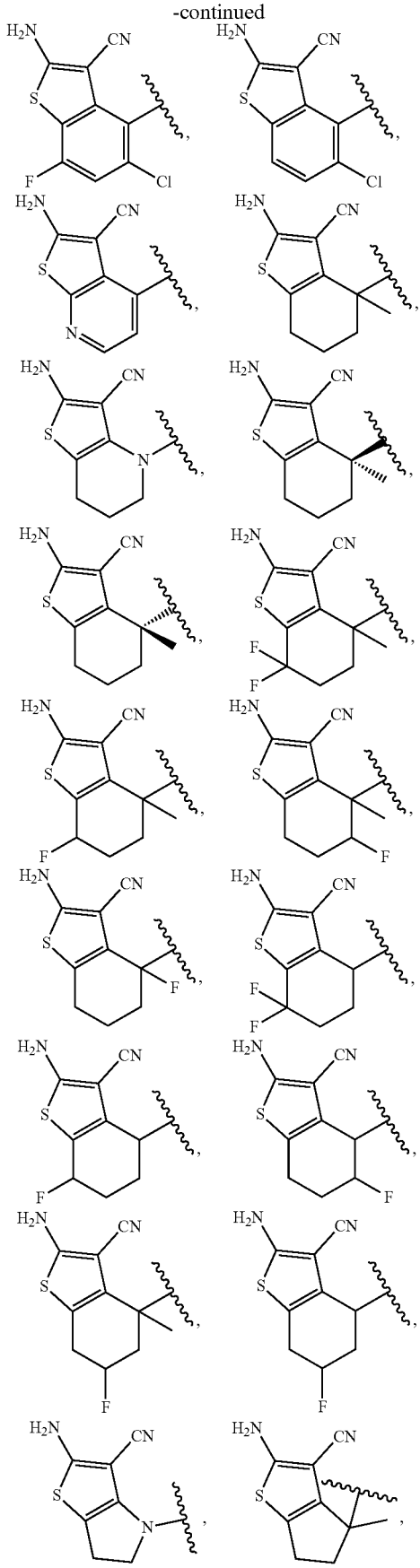
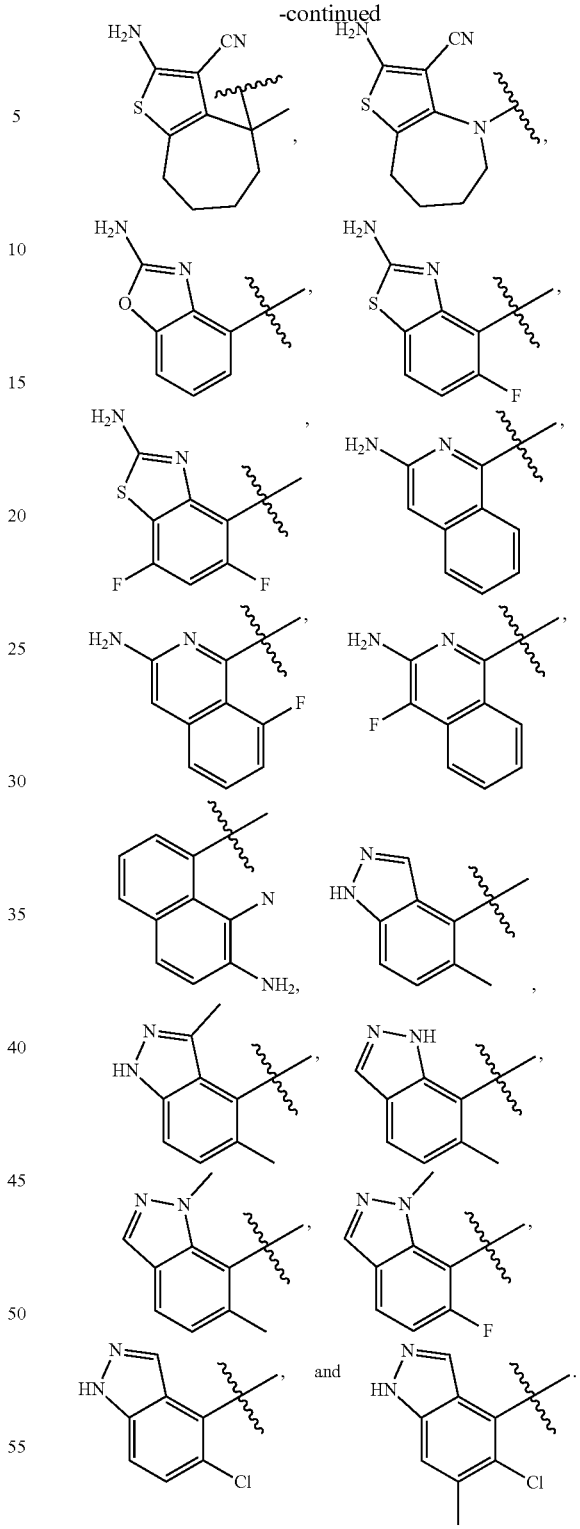
wherein $R^{17}$ is selected from
Embodiment 275 The compound of any one of embodiments 201-274, or a pharmaceutically acceptable salt or solvate thereof, wherein $L^7$ is a bond, —O—, —N(R$^7$)—, —C(O)—, or CR 7OR$^{76}$.
Embodiment 276 The compound of any one of embodiments 201-275, or a pharmaceutically acceptable salt or solvate thereof, wherein $L^7$ is a bond.

Embodiment 277 The compound of any one of embodiments 201-276, or a pharmaceutically acceptable salt or solvate thereof, wherein $R^2$ is selected from $C_{1-6}$ alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$ heteroaryl, —$OR^{12}$, $SR^{12}$, and —$N(H)(R^{12})$, wherein $C_{1-6}$ alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl are optionally substituted with one, two, or three $R^{20}$%.

Embodiment 278 The compound of any one of embodiments 201-277, or a pharmaceutically acceptable salt or solvate thereof, wherein $R^2$ is selected from —$OR^{12}$, —$SR^{12}$, —$N(H)(R^{12})$, and $C_{1-6}$alkyl optionally substituted with one, two, or three $R^{20}$.

Embodiment 279 The compound of any one of embodiments 201-278, or a pharmaceutically acceptable salt or solvate thereof, wherein $R^2$ is selected from

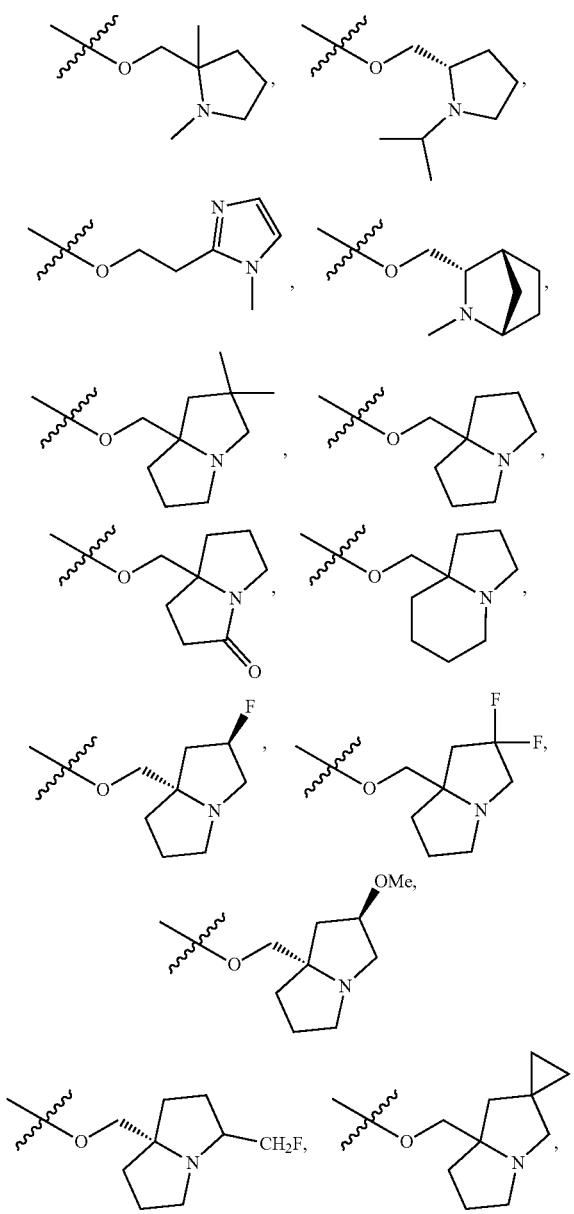
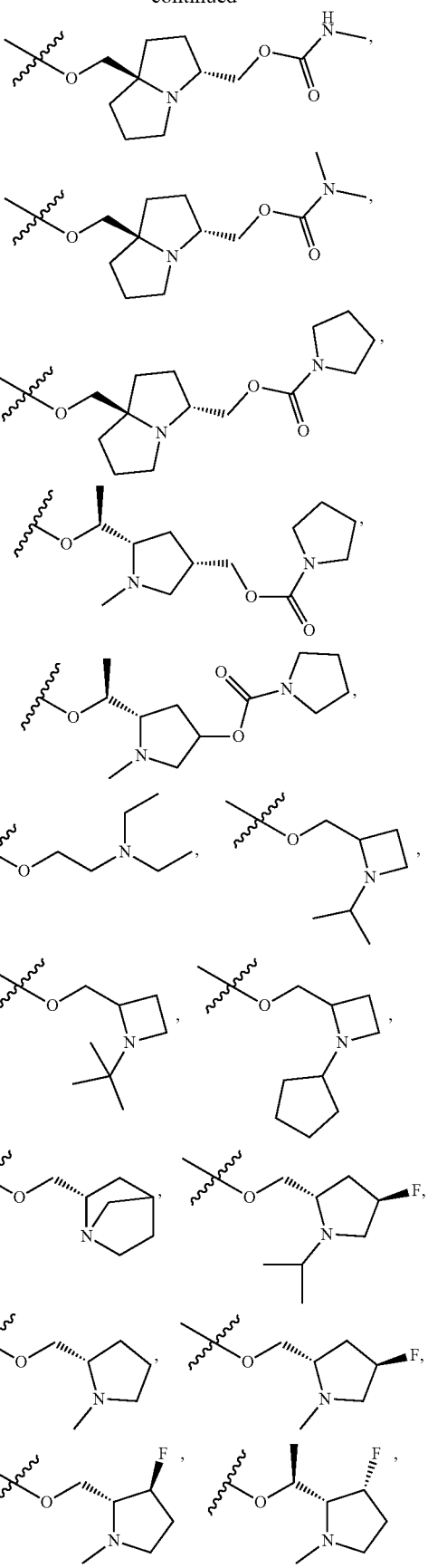

1191
-continued
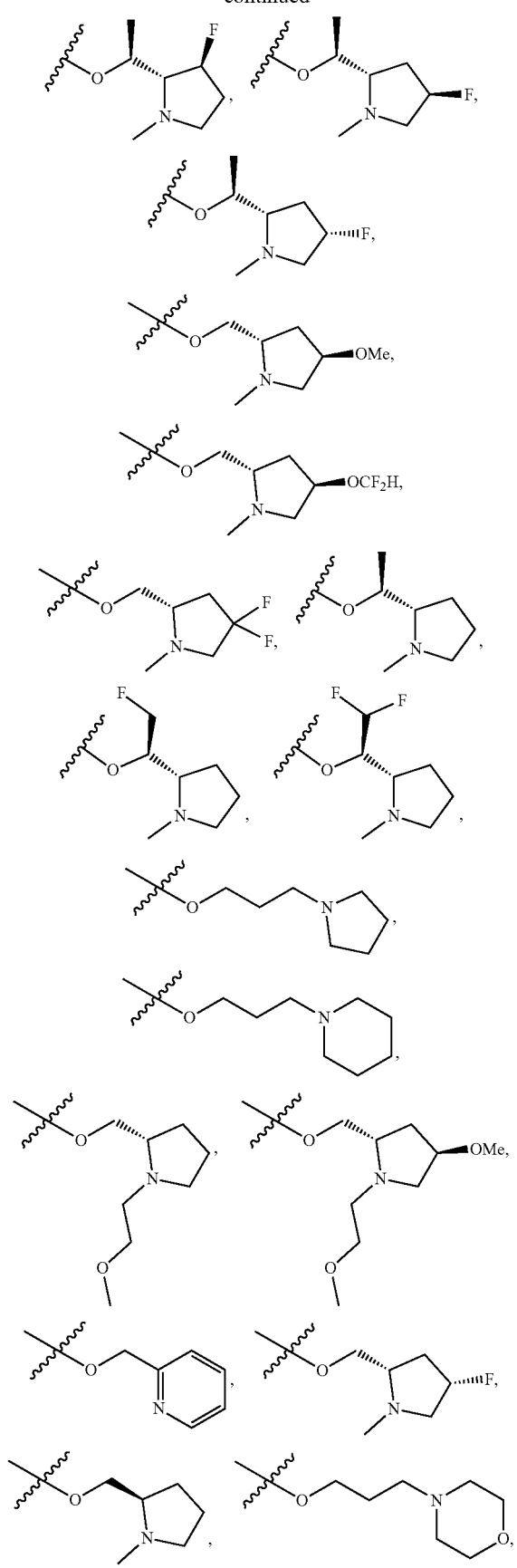
1192
-continued
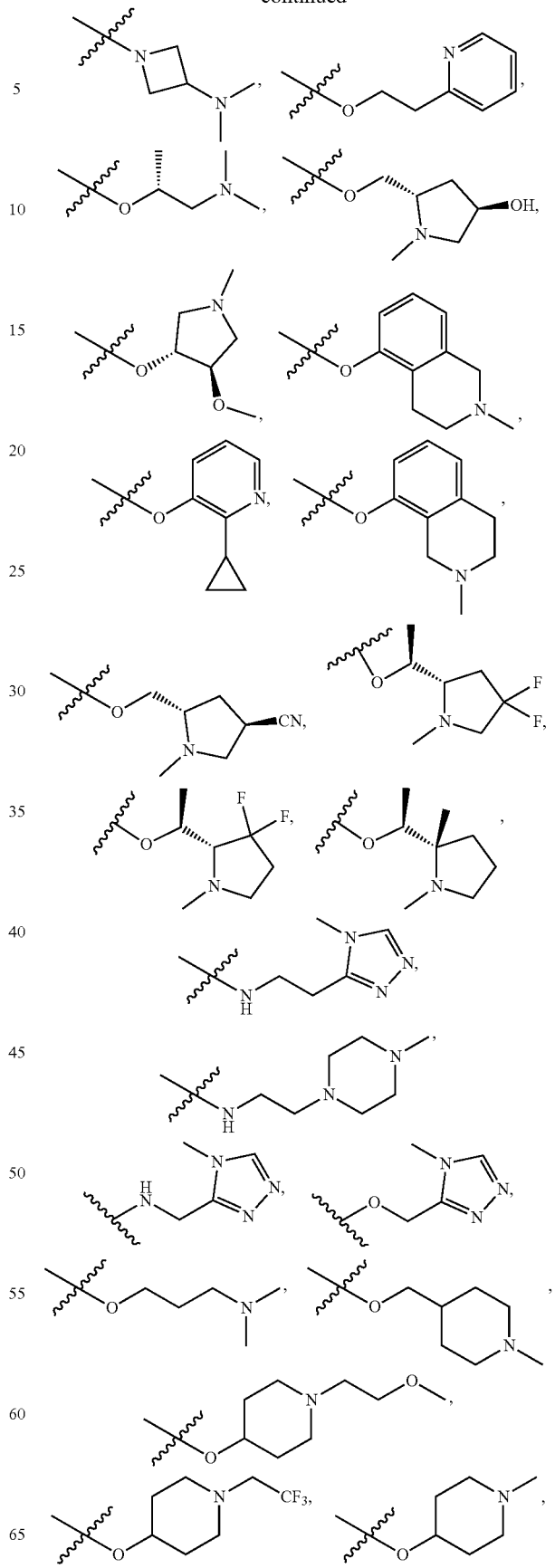

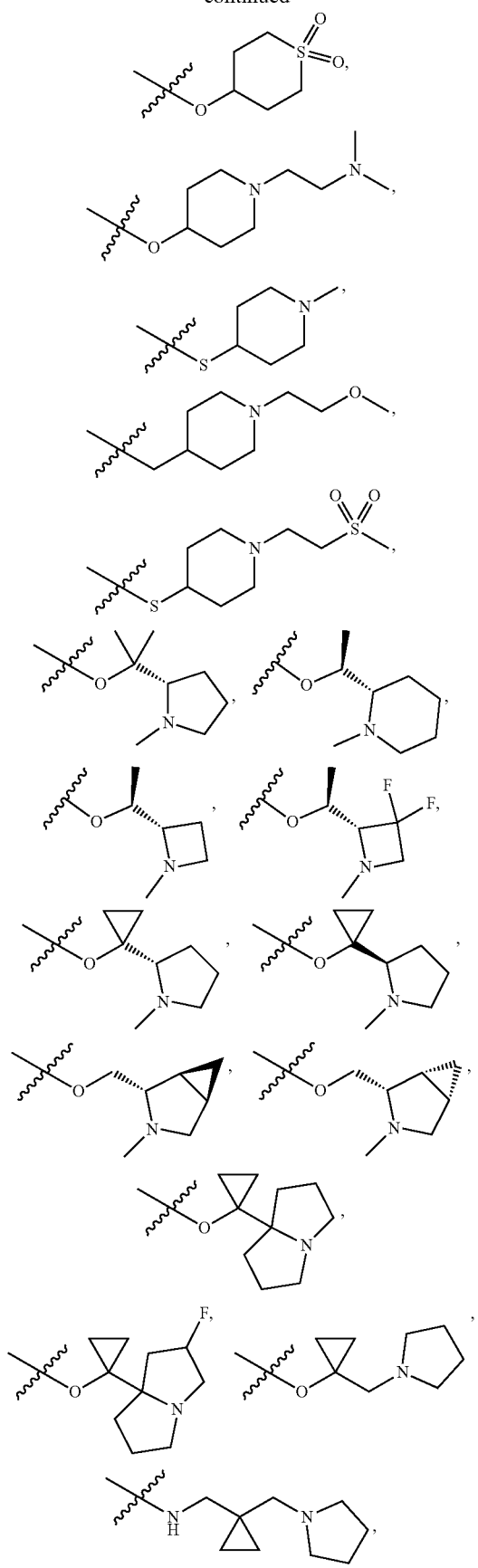
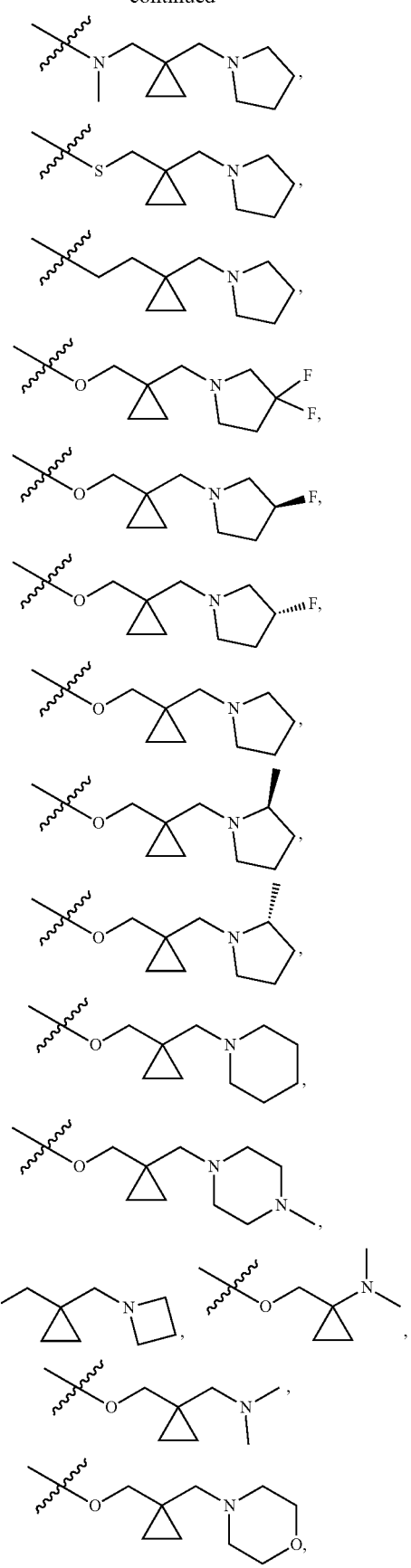

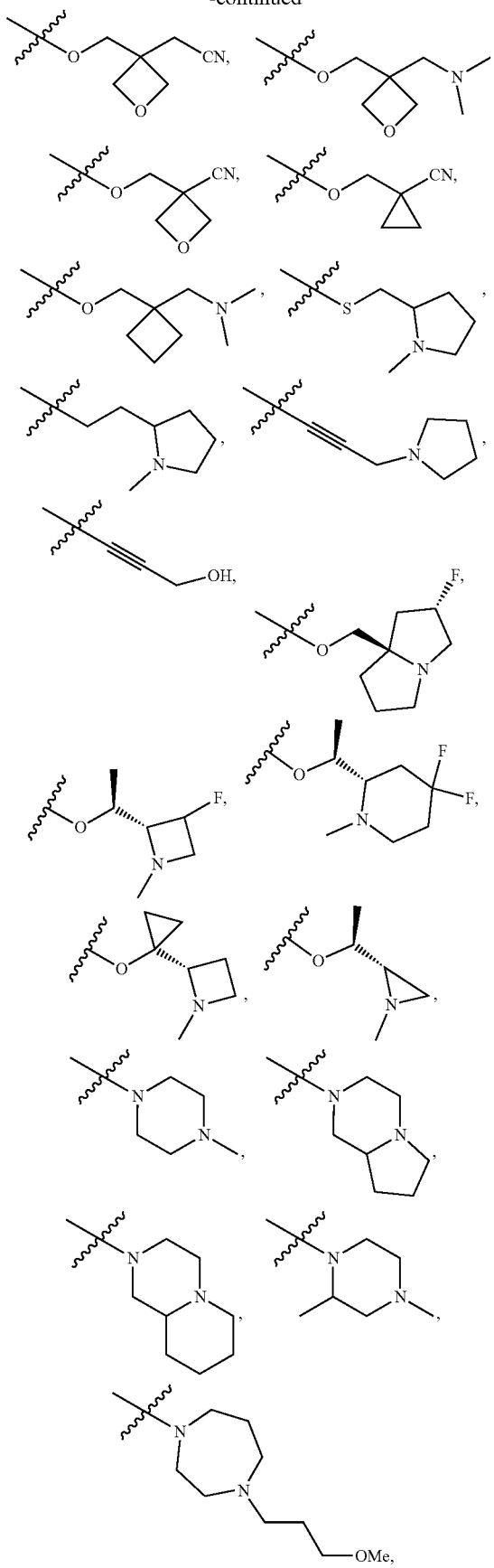

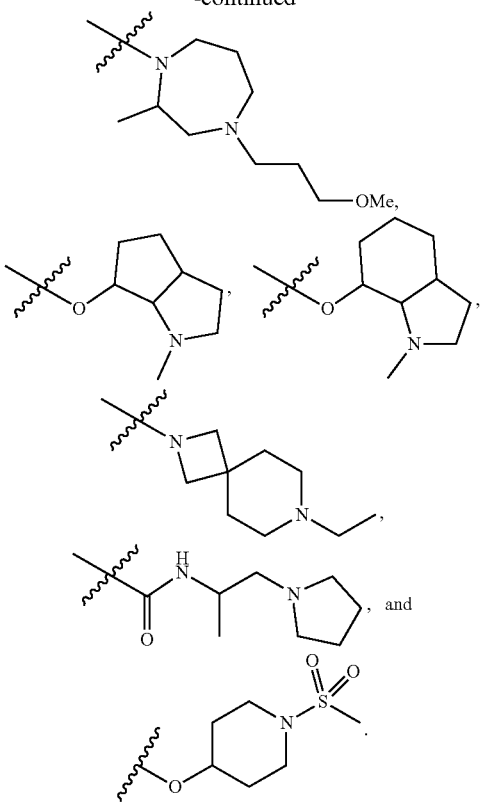

Embodiment 280 The compound of any one of embodiments 201-279, or a pharmaceutically acceptable salt or solvate thereof, wherein $R^3$ is selected from hydrogen, halogen, —CN, $C_{1-6}$alkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$)—, wherein $C_{1-6}$alkyl is optionally substituted with one, two, or three R$^{20c}$.

Embodiment 281 The compound of any one of embodiments 201-280, or a pharmaceutically acceptable salt or solvate thereof, wherein $R^3$ is selected from hydrogen, halogen, —CN, $C_{1-6}$alkyl, and —OR$^{12}$, wherein $C_{1-6}$alkyl is optionally substituted with one, two, or three R$^{20c}$.

Embodiment 282 The compound of any one of embodiments 201-281, or a pharmaceutically acceptable salt or solvate thereof, wherein $R^6$ is selected from hydrogen, halogen, —CN, $C_{1-6}$alkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$)—, wherein $C_{1-6}$alkyl is optionally substituted with one, two, or three R$^{20e}$.

Embodiment 283 The compound of any one of embodiments 201-282, or a pharmaceutically acceptable salt or solvate thereof, wherein $R^6$ is selected from hydrogen, halogen, —CN, $C_{1-6}$alkyl, and —OR$^{12}$, wherein $C_{1-6}$alkyl is optionally substituted with one, two, or three R$^{20c}$.

Embodiment 284 The compound of any one of embodiments 201-283, or a pharmaceutically acceptable salt or solvate thereof, wherein $R^8$ is selected from hydrogen, halogen, —CN, $C_{1-6}$alkyl, —OR$^{12}$, —SR$^{12}$, —N(R$^{12}$)(R$^{13}$), —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$)—, wherein $C_{1-6}$alkyl is optionally substituted with one, two, or three R$^{20h}$.

Embodiment 285 The compound of any one of embodiments 201-284, or a pharmaceutically acceptable salt or solvate thereof, wherein $R^8$ is selected from hydrogen, Embodiment 286 The compound of any one of embodiments 204-285, or a pharmaceutically acceptable salt or solvate thereof, wherein $Z^1$ is O, $Z^2$ is $CH_2$, $Z^3$ is $CH_2$, $Z^4$ is $CH_2$, and $Z^5$ is $N(R^4)$.

Embodiment 287 The compound of any one of embodiments 204-285, or a pharmaceutically acceptable salt or solvate thereof, wherein $Z^1$ is S, $Z^2$ is $CH_2$, $Z^3$ is $CH_2$, $Z^4$ is $CH_2$, and $Z^5$ is $N(R^4)$.

Embodiment 288 The compound of any one of embodiments 204-285, or a pharmaceutically acceptable salt or solvate thereof, wherein $Z^1$ is N(H), $Z^2$ is $CH_2$, $Z^3$ is $CH_2$, $Z^4$ is $CH_2$, and $Z^5$ is $N(R^4)$.

Embodiment 289 The compound of any one of embodiments 204-285, or a pharmaceutically acceptable salt or solvate thereof, wherein $Z^1$ is $CH_2$, $Z^2$ is $CH_2$, $Z^3$ is $CH_2$, $Z^4$ is $CH_2$, and $Z^5$ is $N(R^4)$.

Embodiment 290 The compound of any one of embodiments 204-285, or a pharmaceutically acceptable salt or solvate thereof, wherein $Z^1$ is O, $Z^2$ is $CH_2$, $Z^3$ is $CH_2$, $Z^4$ is $C(R^4)(H)$, and $Z^5$ is O.

Embodiment 291 The compound of any one of embodiments 204-285, or a pharmaceutically acceptable salt or solvate thereof, wherein $Z^1$ is O, $Z^2$ is $CH_2$, $Z^3$ is $C(R^4)(H)$, $Z^4$ is $CH_2$, and $Z^5$ is O.

Embodiment 292 The compound of any one of embodiments 204-285, or a pharmaceutically acceptable salt or solvate thereof, wherein $Z^1$ is O, $Z^2$ is $C(R^4)(H)$, $Z^3$ is $CH_2$, $Z^4$ is $CH_2$, and $Z^5$ is O.

Embodiment 293 The compound of any one of embodiments 204-285, or a pharmaceutically acceptable salt or solvate thereof, wherein $Z^1$ is O, $Z^2$ is $CH_2$, $Z^3$ is $CH_2$, $Z^4$ is $CH_2$, and $Z^5$ is $C(R^4)(H)$.

Embodiment 294 The compound of any one of embodiments 204-285, or a pharmaceutically acceptable salt or solvate thereof, wherein $Z^1$ is O, $Z^2$ is $CH_2$, $Z^3$ is $CH_2$, $Z^4$ is $C(R^4)(H)$, and $Z^5$ is $CH_2$.

Embodiment 295 The compound of any one of embodiments 204-285, or a pharmaceutically acceptable salt or solvate thereof, wherein $Z^1$ is O, $Z^2$ is $CH_2$, $Z^3$ is $C(R^4)(H)$, $Z^4$ is $CH_2$, and $Z^5$ is $CH_2$.

Embodiment 296 The compound of any one of embodiments 204-285, or a pharmaceutically acceptable salt or solvate thereof, wherein $Z^1$ is O, $Z^2$ is $C(R^4)(H)$, $Z^3$ is $CH_2$, $Z^4$ is $CH_2$, and $Z^5$ is $CH_2$.

Embodiment 297 The compound of any one of embodiments 204-285, or a pharmaceutically acceptable salt or solvate thereof, wherein $Z^1$ is O, $Z^2$ is a bond, $Z^3$ is $CH_2$, $Z^4$ is a bond, and $Z^5$ is $C(R^4)(H)$.

Embodiment 298 The compound of any one of embodiments 204-285, or a pharmaceutically acceptable salt or solvate thereof, wherein $Z^1$ is O, $Z^2$ is a bond, $Z^3$ is $C(R^4)(H)$, $Z^4$ is a bond, and $Z^5$ is $CH_2$.

Embodiment 299 The compound of any one of embodiments 204-285, or a pharmaceutically acceptable salt or solvate thereof, wherein $Z^1$ is N(H), $Z^2$ is a bond, $Z^3$ is $CH_2$, $Z^4$ is a bond, and $Z^5$ is $C(R^4)(H)$.

Embodiment 300 The compound of any one of embodiments 204-285, or a pharmaceutically acceptable salt or solvate thereof, wherein $Z^1$ is N(H), $Z^2$ is a bond, $Z^3$ is $C(R^4)(H)$, $Z^4$ is a bond, and $Z^5$ is $CH_2$.

Embodiment 301 The compound of any one of embodiments 204-285, or a pharmaceutically acceptable salt or solvate thereof, wherein $Z^1$ is $N(R^{11c})$, $Z^2$ is a bond, $Z^3$ is $CH_2$, $Z^4$ is a bond, and $Z^5$ is $C(R^4)(H)$.

Embodiment 302 The compound of any one of embodiments 204-285, or a pharmaceutically acceptable salt or solvate thereof, wherein $Z^1$ is $N(R^{11c})$, $Z^2$ is a bond, $Z^3$ is $C(R^4)(H)$, $Z^4$ is a bond, and $Z^5$ is $CH_2$.

Embodiment 303 The compound of any one of embodiments 204-285, or a pharmaceutically acceptable salt or solvate thereof, wherein $Z^1$ is O, $Z^2$ is a bond, $Z^3$ is $CH_2$, $Z^4$ is a bond, and $Z^5$ is $N(R^4)$.

Embodiment 304 The compound of any one of embodiments 201-303, or a pharmaceutically acceptable salt or solvate thereof, wherein each $R^{4a}$ is $C_{3-10}$cycloalkyl optionally substituted with one, two, three, or four $R^{4b}$.

Embodiment 305 The compound of any one of embodiments 201-303, or a pharmaceutically acceptable salt or solvate thereof, wherein each $R^{4a}$ is $C_{2-9}$heterocycloalkyl optionally substituted with one, two, three, or four $R^{4b}$.

Embodiment 306 The compound of any one of embodiments 201-303, or a pharmaceutically acceptable salt or solvate thereof, wherein each $R^{4a}$ is $C_{6-10}$aryl optionally substituted with one, two, three, or four $R^{4b}$.

Embodiment 307 The compound of any one of embodiments 201-303, or a pharmaceutically acceptable salt or solvate thereof, wherein each $R^{4a}$ is $C_{1-9}$heteroaryl optionally substituted with one, two, three, or four $R^{4b}$.

Embodiment 308 The compound of any one of embodiments 201-303, or a pharmaceutically acceptable salt or solvate thereof, wherein each $R^{4a}$ is $C_{3-10}$cycloalkyl, $C_{2-9}$heterocycloalkyl, $C_{6-10}$aryl, and $C_{1-9}$heteroaryl optionally substituted with one, two, three, or four $R^{4b}$.

Embodiment 309 The compound of any one of embodiments 201-308, or a pharmaceutically acceptable salt or solvate thereof, wherein $L^4$ is a bond, —O—, —N($R^{4d}$)—, —C(O)—, or $CR^{4o}$ C. $R^{4c}$.

Embodiment 310 The compound of any one of embodiments 201-309, or a pharmaceutically acceptable salt or solvate thereof, wherein $L^4$ is a bond.

Embodiment 311 A compound having the formula A-$L^{AB}$-B wherein
  A is a monovalent form of a compound of one of embodiments 201-310;
  $L^{AB}$ is a covalent linker bonded to A and B; and
  B is a monovalent form of a degradation enhancer.

Embodiment 312 The compound of embodiment 311, wherein the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4CRBN) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

Embodiment 313 The compound of embodiment 312, wherein the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L$^3$, UBE2L$^6$, UBE2L$^1$, UBE2L$^2$, UBE2L$^4$, UBE2M, UBE2N, UBE2O, UBE2Q$^1$, UBE2Q$^2$, UBE2R$^1$, UBE2R$^2$, UBE2S, UBE2T, UBE2U, UBE2V1, UBE2V2, UBE2W, UBE2Z, ATG3, BIRC6, and UFC1.

Embodiment 314 The compound of any one of embodiments 311-313, wherein $L^{AB}$ is -$L^{AB1}$-$L^{AB2}$-$L^{AB3}$-$L^{AB4}$-$L^{AB5}$-; $L^{AB1}$, $L^{AB2}$, $L^{AB3}$, $L^{AB4}$, and $L^{AB5}$ are independently a bond, —O—, —N(R$^{14}$)—, —C(O)—, —N(R$^{14}$)C(O)—, —C(O)N(R$^{14}$)—, —S—, —S(O)$_2$—, —S(O)—, —S(O)$_2$N(R$^{14}$)—, —S(O)N(R$^{14}$)—, —N(R$^{14}$)S(O)—, —N(R$^{14}$)S(O)$_2$—, C$_{1-6}$alkylene, (—O—C$_{1-6}$alkyl)$_2$—, (—C$_{1-6}$alkyl-O)$_2$—, C$_{2-6}$alkenylene, C$_{2-6}$alkynylene, C$_{1-6}$haloalkylene, C$_{3-12}$cycloalkylene, C$_{1-11}$heterocycloalkylene, C$_{6-12}$arylene, or C$_{1-11}$heteroarylene, wherein C$_{1-6}$alkylene, C$_{2-6}$alkenylene, C$_{2-6}$alkynylene, C$_{1-6}$haloalkylene, C$_{3-12}$cycloalkylene, C$_{1-11}$heterocycloalkylene, C$_{6-12}$arylene, or C$_{1-6}$nheteroarylene, are optionally substituted with one, two, or three R$^{20l}$; wherein each C$_{1-6}$alkyl of (—O—C$_{1-6}$alkyl)$_7$— and (—C$_{1-6}$alkyl-O), — is optionally substituted with one, two, or three R$^{20l}$;

z is independently an integer from 0 to 10;

each R$^{12}$ is independently selected from hydrogen, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_6$-10aryl, —CH$_2$-C$_{1-9}$heteroaryl, and C$_{1-9}$heteroaryl are optionally substituted with one, two, or three R$^{20l}$, each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20l}$;

each R$^{1d}$ is independently selected from hydrogen, C$_{1-6}$alkyl, and C$_{1-6}$haloalkyl;

each R$^{15}$ is independently selected C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_1$-9heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20m}$, each R$^{20l}$, R$^{20m}$, and R$^{20n}$ are each independently selected from halogen, oxo, —CN, C$_{1-6}$alkyl, C$_{2-6}$alkenyl, C$_{2-6}$alkynyl, C$_{3-10}$cycloalkyl, —CH$_2$-C$_{3-10}$cycloalkyl, C$_{2-9}$heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-10}$cycloalkyl, —CH$_2$-C$_{3-10}$cycloalkyl, C$_2$-heterocycloalkyl, —CH$_2$-C$_{2-9}$heterocycloalkyl, C$_{6-10}$aryl, —CH$_2$-C$_{6-10}$aryl, —CH$_2$-C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl;

each R$^{23}$ is independently selected from H and C$_{1-6}$alkyl;
each R$^{24}$ is independently selected from H and C$_{1-6}$alkyl; and each R$^{25}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl.

Embodiment 315 The compound of any one of embodiments 311-314, wherein $L^{AB}$ is —(O-C$_2$alkyl)- and z is an integer from 1 to 10.

Embodiment 316 The compound of any one of embodiments 311-314, wherein $L^{AB}$ is —(C$_2$alkyl-O—)$_z$— and z is an integer from 1 to 10.

Embodiment 317 The compound of any one of embodiments 311-314, wherein $L^{AB}$ is —(CH$_2$)zz1 $L^{AB2}$ (CH$_2$O)$_{722}$—, wherein $L^{AB2}$ is a bond, a 5 or 6 membered heterocycloalkylene or heteroarylene, phenylene, —(C$_2$-C$_4$) alkynylene, —$_5$O2— or —NH—; and zz1 and zz2 are independently an integer from 0 to 10.

Embodiment 318 The compound of any one of embodiments 311-314, wherein $L^{AB}$ is —(CH$_2$)zz1(CH$_2$O)$_{zz2}$—, wherein zz1 and zz2 are each independently an integer from 0 to 10.

Embodiment 319 The compound of any one of embodiments 311-314, wherein $L^{AB}$ is a PEG linker.

Embodiment 320 The compound of any one of embodiments 311-319, wherein B is a monovalent form of a compound selected from

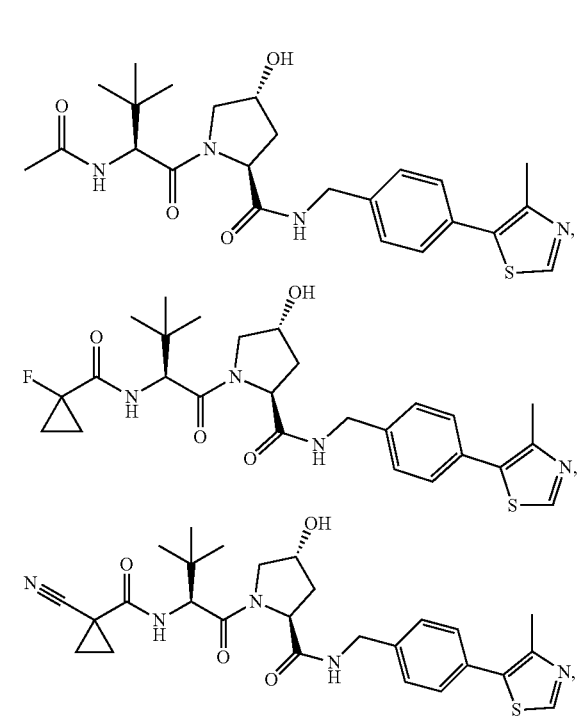

1201

-continued

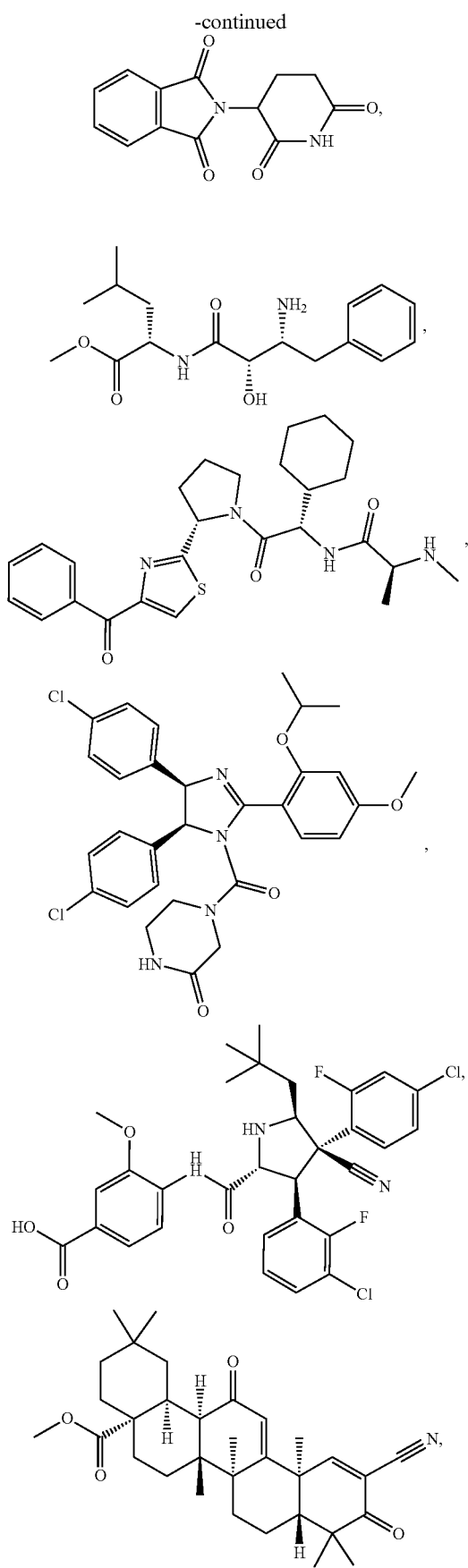

1202

-continued

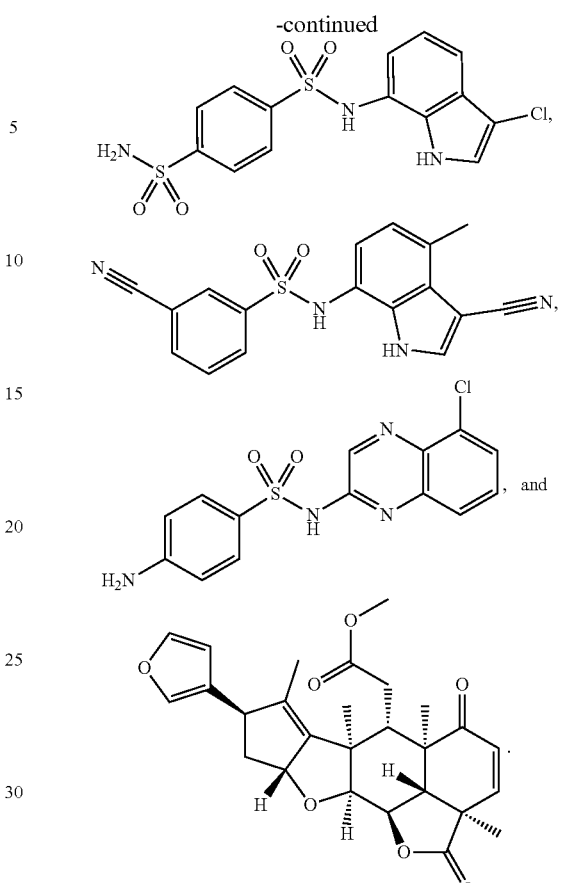

Embodiment 321 A pharmaceutical composition comprising a compound of any one of embodiments 201-320, or a pharmaceutically acceptable salt or solvate thereof, and a pharmaceutically acceptable excipient.

Embodiment 322 A method of treating cancer in a subject in need thereof, comprising administering to the subject a therapeutically effective amount of a compound or compound of any one of embodiments 201-320, or a pharmaceutically acceptable salt or solvate thereof.

Embodiment 323 A method of treating cancer in a subject comprising a Ras mutant protein, the method comprising: inhibiting the Ras mutant protein of said subject by administering to said subject a compound, wherein compound is characterized in that upon contacting the Ras mutant protein, said Ras mutant protein exhibits reduced Ras signaling output.

Embodiment 324 The method of embodiment 322 or embodiment 323, wherein the cancer is a solid tumor.

Embodiment 325 The method of embodiment 322 or embodiment 323, wherein the cancer is a hematological cancer.

Embodiment 326 The method of embodiment 322 or embodiment 323, wherein the compound is a compound of any one of embodiments 201-320.

Embodiment 327 A method of modulating signaling output of a Ras protein, comprising contacting a Ras protein with an effective amount of a compound or compound of any one of embodiments 201-320, or a pharmaceutically acceptable salt or solvate thereof, thereby modulating the signaling output of the Ras protein.

Embodiment 328 A method of inhibiting cell growth, comprising administering an effective amount of a compound or compound of one of embodiments 201-320, or a pharmaceutically acceptable salt or solvate thereof, to a cell expressing a Ras protein, thereby inhibiting growth of said cells.

Embodiment 329 The method of any one of embodiments 322-328 comprising administering an additional agent.

Embodiment 330 The method of embodiment 329, wherein the additional agent comprises (1) an inhibitor of MEK; (2) an inhibitor of epidermal growth factor receptor (EGFR) and/or of mutants thereof; (3) an immunotherapeutic agent; (4) a taxane; (5) an anti-metabolite; (6) an inhibitor of FGFR1 and/or FGFR2 and/or FGFR3 and/or of mutants thereof; (7) a mitotic kinase inhibitor; (8) an anti-angiogenic drug; (9) a topoisomerase inhibitor; (10) a platinum-containing compound; (12) an inhibitor of c-MET and/or of mutants thereof; (13) an inhibitor of BCR-ABL and/or of mutants thereof; (14) an inhibitor of ErbB2 (Her2) and/or of mutants thereof; (15) an inhibitor of AXL and/or of mutants thereof; (16) an inhibitor of NTRK1 and/or of mutants thereof; (17) an inhibitor of RET and/or of mutants thereof; (18) an inhibitor of A-Raf and/or B-Raf and/or C-Raf and/or of mutants thereof; (19) an inhibitor of ERK and/or of mutants thereof; (20) an MDM2 inhibitor; (21) an inhibitor of mTOR; (23) an inhibitor of IGF1/2 and/or of IGF1-R; (24) an inhibitor of CDK9; (25) an inhibitor of farnesyl transferase; (26) an inhibitor of SHIP pathway; (27) an inhibitor of SRC; (28) an inhibitor of JAK; (29) a PARP inhibitor, (31) a ROS1 inhibitor; (32) an inhibitor of SHP pathway, or (33) an inhibitor of Src, FLT3, HDAC, VEGFR, PDGFR, LCK, Bcr-Abl or AKT; (34) an inhibitor of KrasG12C mutant; (35) a SHC inhibitor (e.g., PP2, AID371185); (36) a GAB inhibitor; (38) a PI-3 kinase inhibitor; (39) a MARPK inhibitor; (40) CDK4/6 inhibitor; (41) MAPK inhibitor; (42) SHP2 inhibitor; (43) checkpoint immune blockade agents; (44) or SOS1 inhibitor; or (45) a SOS 2 inhibitor.

Embodiment 331 The method of embodiment 329, wherein the additional agent comprises an inhibitor of SHP2 selected from

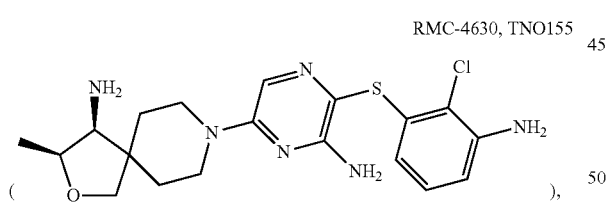
(RMC-4630, TNO155),

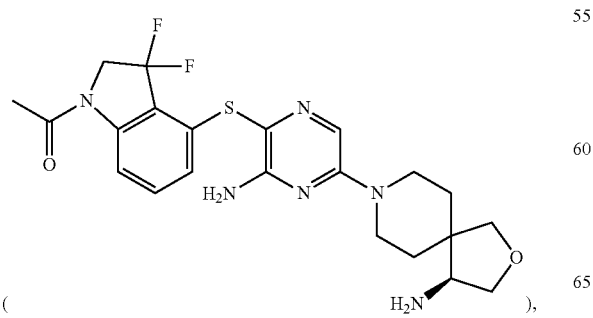
(JAB-3068),

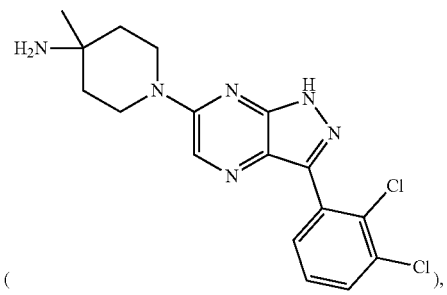
(IACS-13909/BBP-398),

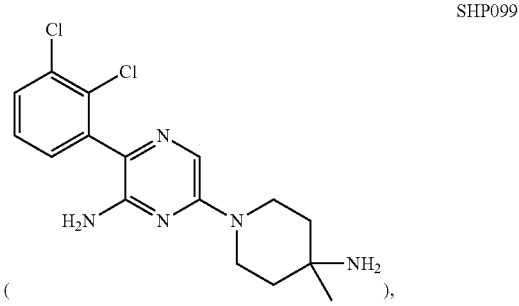
(SHP099),

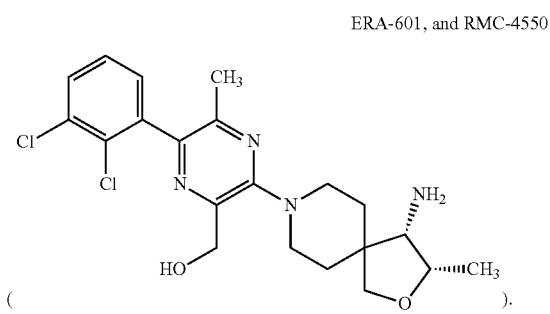
(ERA-601, and RMC-4550).

Embodiment 332 The method of embodiment 329, wherein the additional agent comprises an inhibitor of SOS selected from RMC—

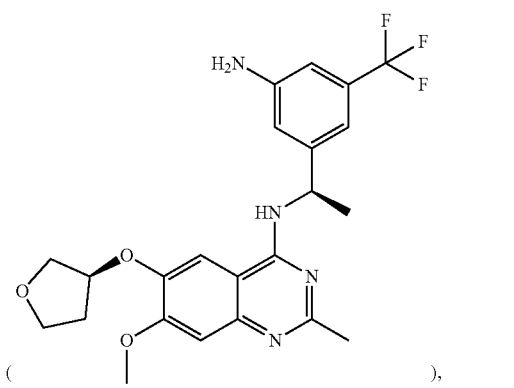
(5845, BI-3406),

BI-1701963, and BAY 293

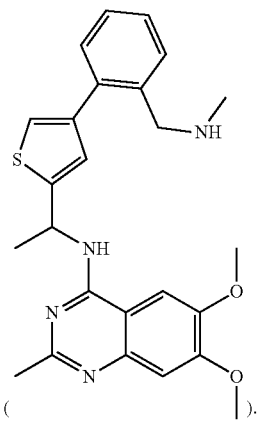

Embodiment 333 The method of embodiment 329, wherein the additional agent comprises an inhibitor of EGFR selected from afatinib, erlotinib, gefitinib, lapatinib, cetuximab panitumumab, osimertinib, olmutinib, and EGF-816.

Embodiment 334 The method of embodiment 329, wherein the additional agent comprises an inhibitor of MEK selected from trametinib, cobimetinib, binimetinib, selumetinib, refametinib, and AZD6244.

Embodiment 335 The method of embodiment 329, wherein the additional agent comprises an inhibitor of ERK selected from ulixertinib, MK-8353, LTT462, AZD0364, SCH772984, BIX02189, LY3214996, and ravoxertinib.

Embodiment 336 The method of embodiment 329, wherein the additional agent comprises an inhibitor of CDK4/6 selected from palbociclib, ribociclib, and abemaciclib.

Embodiment 337 The method of embodiment 329, wherein the additional agent comprises an inhibitor of BRAF selected from sorafenib, vemurafenib, dabrafenib, encorafenib, regorafenib, and GDC-879.

EXAMPLES

Example 1a: Synthesis of 2-amino-4-(8-chloro-4-((3,3-difluorocyclobutyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (951)

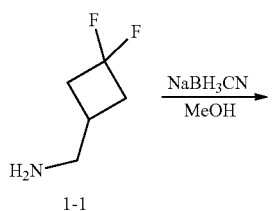

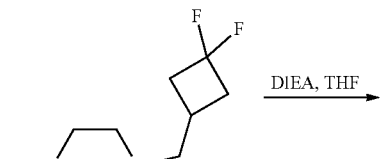

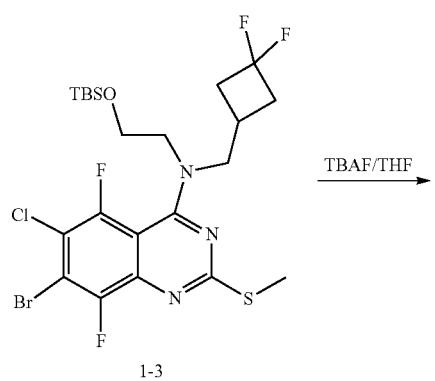

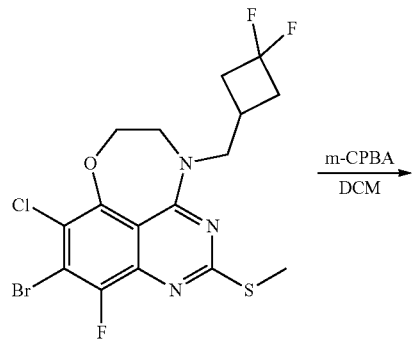

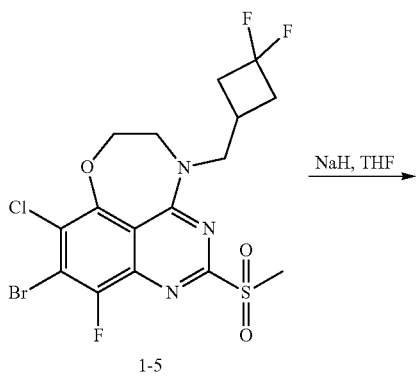

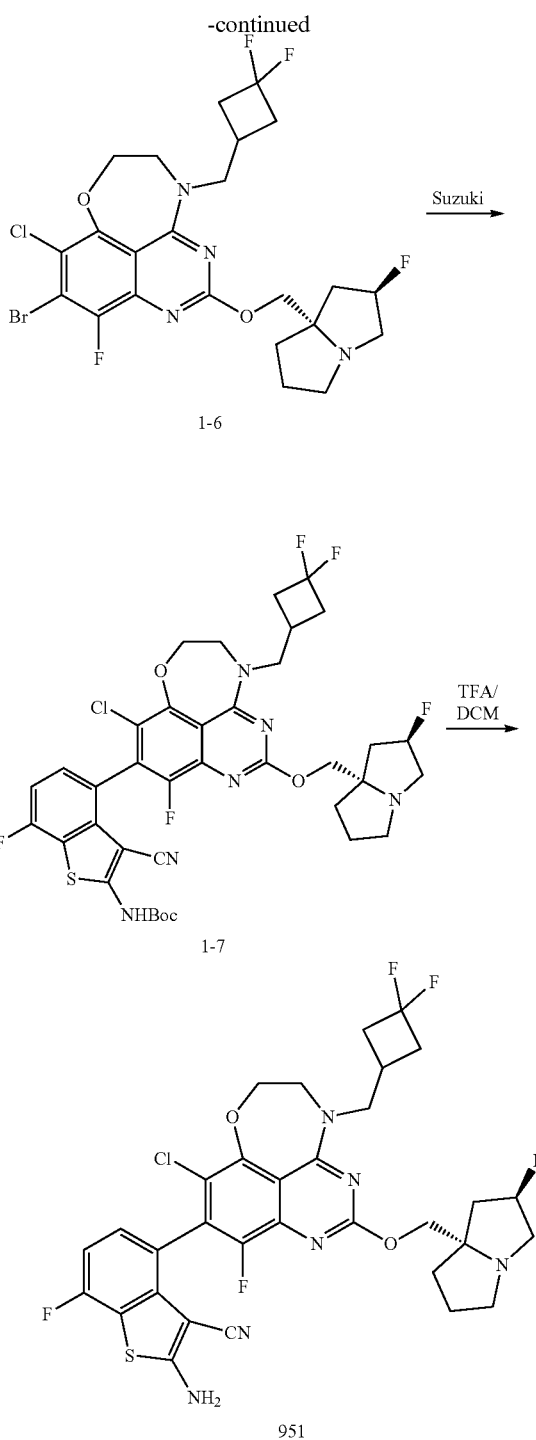

Step 1: To a solution of (3,3-difluorocyclobutyl)methanamine (1-1) (500 mg, 1.2 eq) and 2-((tert-butyldimethylsilyl)oxy) acetaldehyde (600 mg, 1.0 eq) in 15 mL of MeOH were added NaBH3CN (778 mg, 3.0 eq) and AcOH (25 mg, 0.1 eq). The resulting mixture was stirred at RT overnight. The mixture was partitioned between water and ethyl acetate. The organic layer was washed with brine, dried over Na$_{25}$O4, filtered, and concentrated in vacuo. The residue was purified by flash column chromatography on silica gel to afford compound 1-2 (260 mg). ESI-MS m/z: 280.4 [M+H]$^+$.

Step 2: To a solution of compound 1-2 (260 mg, 0.93 mmol, 1.0 eq) in THF (15 mL) at RT were added DIEA (360 mg, 2.79 mmol, 3 eq) and 7-bromo-4,6-dichloro-5,8-difluoro-2-(methylthio)quinazoline (335 mg, 0.93 mmol, 1 eq). The resulting solution was stirred at RT for 2 h. The mixture was partitioned between EtOAc and water. The organic layer was concentrated, and the residue was purified on a silica gel column eluting with ethyl acetate/petroleum ether (1:4) to afford compound 1-3 (450 mg). ESI-MS m/z: 602.1 [M+H]$^+$.

Step 3: To a stirred solution of compound 1-3 (450 mg, 0.75 mmol) in THF (5 mL) was added TBAF (1 mL) and the resulting mixture was stirred at RT for 2 h. The mixture was partitioned between water and ethyl acetate. The organic layer was washed with brine, dried over Na$_{25}$O4, filtered, and concentrated in vacuo. The residue was purified by flash column chromatography on silica gel to afford compound 1-4 (360 mg). ESI-MS m/z: 468.0 [M+H]$^+$.

Step 4: To a stirred solution of compound 1-4 (180 mg, 0.38 mmol, 1 eq) in DCM (15 mL) was added m-CPBA (200 mg, 1.15 mmol, 3 eq) and the resulting mixture was stirred at RT for 2 h. The mixture was partitioned between NaHCO$_3$ (aq) and dichloromethane. The organic layer was washed with brine, dried over Na$_{25}$O4, filtered, and concentrated in vacuo. The residue was purified by flash column chromatography on silica gel to afford compound 1-5 (140 mg). ESI-MS m/z: 500.0 [M+H]$^+$.

Step 5: To a stirred solution of ((2R,7aS)-2-fluorohexahydro-1H-pyrrolizin-7a-yl)methanol (220 mg, 1.4 mmol, 5 eq) in THF (5 mL) was added NaH (60%, 56 mg, 1.4 mmol, 5 eq) at 0° C. and the mixture was stirred for 30 min. Compound 1-5 (140 mg, 0.28 mmol) was added and the resulting mixture was stirred at RT for 2 h. The mixture was poured into ice-water and partitioned between ice-water and ethyl acetate. The organic layer was washed with brine, dried over Na$_{25}$O4, filtered, and concentrated in vacuo. The residue was purified by flash column chromatography on silica gel to afford compound 1-6 (90 mg). ESI-MS m/z: 579.1 [M+H]$^+$.

Step 6: To a stirred solution of compound 1-6 (90 mg, 0.73 mmol, 1 eq) in anhydrous toluene (6 mL) were added tert-butyl (3-cyano-4-(5,5-dimethyl-1,3,2-dioxaborinan-2-yl)-7-fluorobenzo[b]thiophen-2-yl)carbamate (188 mg, 0.47 mmol, 3 eq), PdCl$_2$(dpephos) (11 mg, 0.016 mmol, 0.1 eq) and Cs$_2$CO$_3$ (150 mg, 0.47 mmol, 3 eq) and the resulting mixture was stirred at 105° C. under nitrogen for 3 h. The mixture was partitioned between water and ethyl acetate. The organic layer was washed with brine, dried over Na$_2$SO$_4$, filtered, and concentrated in vacuo. The residue was purified by flash column chromatography on silica gel to afford compound 1-7 (50 mg). ESI-MS m/z: 791.3 [M+H]$^+$.

Step 7: To a solution of compound 1-7 (50 mg) in DCM (5 mL) was added TFA (1.5 mL) and the resulting mixture was stirred at RT for 2 h. The mixture was concentrated in vacuo to remove the solvent, then diluted with NaHCO$_3$(aq), extracted with EtOAc (10 mL×3), dried over Na$_2$SO$_4$ and concentrated in vacuo. The residue was purified by flash column chromatography on silica gel to afford compound 951 (18 mg). ESI-MS m/z: 691.16 [M+H]$^+$; $^1$HNMR (400 MHZ, DMSO-d6): δ 8.15 (s, 2H), 7.13-7.23 (m, 2H), 5.48-5.62 (m, 1H), 4.49-4.65 (m, 4H), 3.82-4.12 (m, 3H), 3.48-3.68 (m, 3H), 3.22-3.39 (m, 2H), 2.58-2.78 (m, 5H), 2.10-2.64 (m, 5H).

Example 1b: Synthesis of 2-amino-4-((5S)-5-(aminomethyl)-8-chloro-10-fluoro-2-(((2R,7aS)-2-fluorotetrahydro-1H-pyrrolizin-7a(5H)-yl)methoxy)-4-methyl-5,6-dihydro-4H-[1,4]oxazepino[5,6,7-de]quinazolin-9-yl)-7-fluorobenzo[b]thiophene-3-carbonitrile (1113)
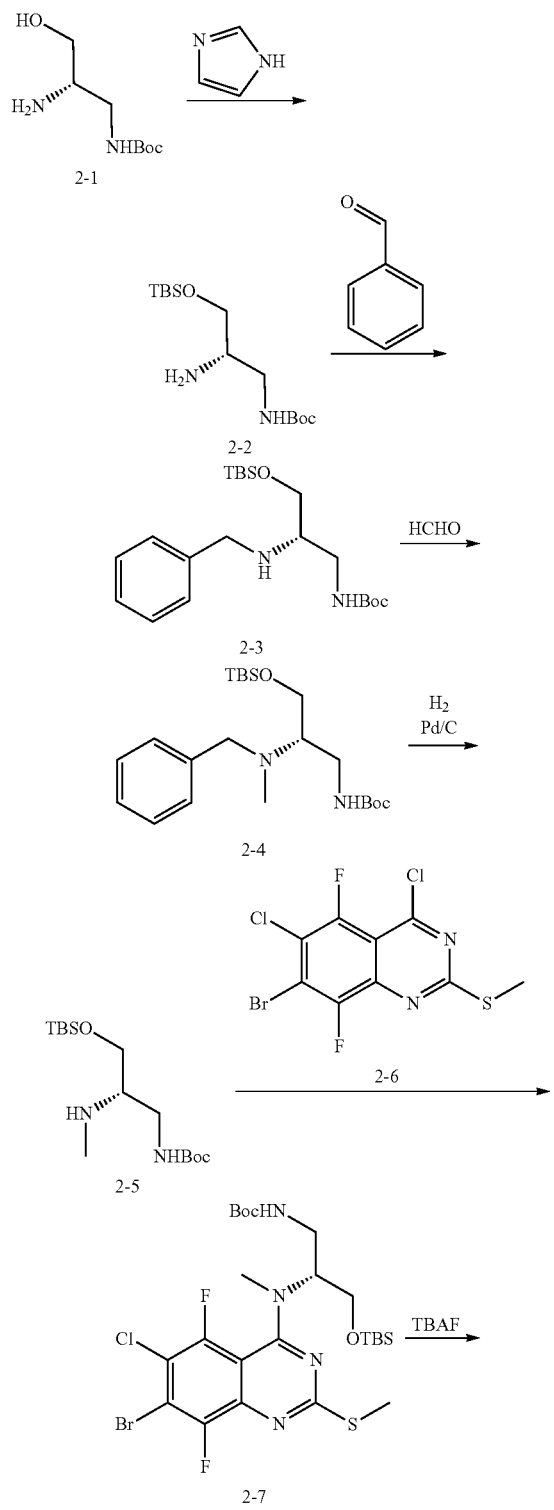
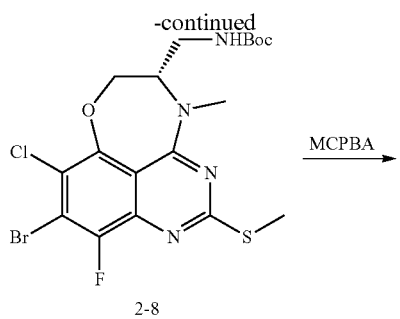
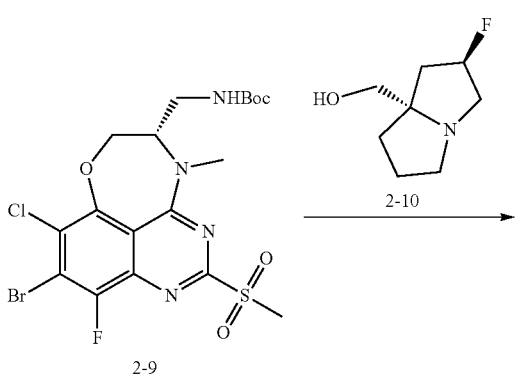
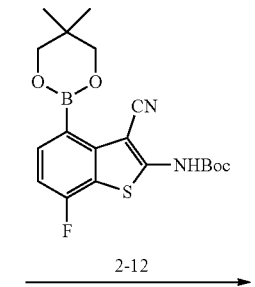
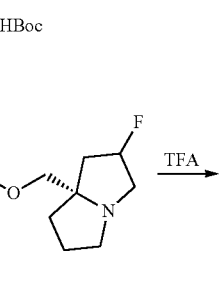
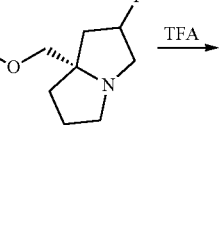

-continued

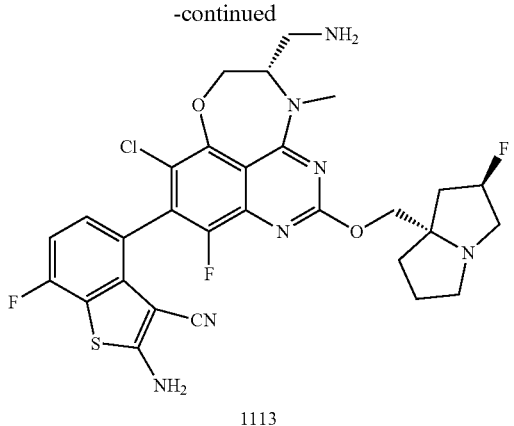

1113

Step 1: To a solution of tert-butyl (S)-(2-amino-3-hydroxypropyl)carbamate (2-1) (600 mg, 3.15 mmol) in DCM (20 mL) were added TBSCI (571 mg, 3.79 mmol) and 1H-imidazole (644 mg, 9.47 mmol). The mixture was stirred at RT for 2 h. The crude was purified by flash chromatography on silica gel (dichloromethane:methyl alcohol=50:1) to afford compound 2-2 (910 mg). ESI-MS m/z: 304 [M+H]$^+$.

Step 2: To a solution of compound 2-2 (910 mg, 3.0 mmol) in MeOH (15 mL) were added benzaldehyde (380 mg, 3.6 mmol) and HOAc (36 mg, 0.6 mmol). The mixture was stirred at RT for 0.5 h, then NaBH$_3$CN (565 mg, 9.0 mmol) was added. The mixture was stirred at RT for 16 h, then the pH was adjusted to 7~8 with NaHCO$_3$. The mixture was extracted with ethyl acetate (50 mL×3). The organic extracts were combined, washed with brine, and dried over Na$_2$SO$_4$. The solvent was removed under reduced pressure to give a crude residue. The crude residue was purified by flash chromatography on silica gel (dichloromethane:methyl alcohol=80:1) to afford compound 2-3 (1.1 g). ESI-MS m/z: 394 [M+H]$^+$.

Step 3: To a solution of tert-butyl compound 2-3 (1.1 g, 2.8 mmol) in MeOH (15 mL) were added formaldehyde (aq, 314 mg, 37%~42%, 4.2 mmol) and HOAc (33 mg, 0.56 mmol). The mixture was stirred at RT for 0.5 h, then NaBH$_3$CN (527 mg, 8.3 mmol) was added and the mixture was stirred at RT for 16 h. The pH was adjusted to 7~8 with NaHCO$_3$. The mixture was extracted with ethyl acetate (50 mL×3) and the organic extracts were combined, washed with brine, and dried over Na$_2$SO$_4$. The solvent was removed under reduced pressure to give a crude residue. The crude residue was purified by flash chromatography on silica gel (petroleum ether:ethyl acetate=10:1) to afford compound 2-4 (1.05 g). ESI-MS m/z: 408 [M+H]$^+$.

Step 4: To a solution of compound 2-4 (1.05 g, 2.57 mmol) in MeOH (20 mL) was added Pd/C (200 mg, 10%). The mixture was stirred under H$_2$ at RT for 16 h. The mixture was filtered and the filtrate was concentrated in vacuo to afford compound 2-5 (710 mg). ESI-MS m/z: 318 [M+H]$^+$.

Step 5: To a solution of compound 2-5 (710 mg, 2.23 mmol) in THF (15 mL) were added 7-bromo-4,6-dichloro-5,8-difluoro-2-(methylthio)quinazoline (2-6) (802 mg, 2.23 mmol) and N-ethyl-N-isopropylpropan-2-amine (864 mg, 6.7 mmol). The mixture was stirred at 80° C. for 2 h, then extracted with ethyl acetate (50 mL×3). The organic extracts were combined, washed with brine, and dried over Na$_2$SO$_4$. Solvent was removed under reduced pressure to give a crude residue, which was purified by flash chromatography on silica gel (petroleum ether:ethyl acetate=10:1) to afford compound 2-7 (1.1g).

Step 6: To a solution of compound 2-7 (1.1 g, 1.71 mmol) in THF (10 mL) was added tetrabutylammonium fluoride (5 mL, 1 M in THF). The mixture was stirred at RT for 2 h, then extracted with ethyl acetate (50 mL×3). The organic extracts were combined, washed with brine, and dried over Na$_2$SO$_4$. The solvent was removed under reduced pressure to give a crude residue, which was purified by flash chromatography on silica gel (petroleum ether:ethyl acetate=5:1) to afford compound 2-8 (810 mg). ESI-MS m/z: 508 [M+H]$^+$.

Step 7: To a solution of compound 2-8 (810 mg, 1.6 mmol) in DCM (20 mL) was added 3-chlorobenzoperoxoic acid (825 mg, 4.8 mmol). The mixture was stirred at RT for 2 h, then solvent was removed under reduced pressure to give a crude residue. The crude residue was purified by flash chromatography on silica gel (dichloromethane:methyl alcohol=100:1) to afford compound 2-9 (560 mg). ESI-MS m/z: 540 [M+H]$^+$.

Step 8: To a solution of ((2R,7aS)-2-fluorotetrahydro-1H-pyrrolizin-7a(5H)-yl)methanol (2-10) (990 mg, 6.2 mmol) in THF (10 mL) was added sodium hydride (248 mg, 60%, 6.2 mmol). The mixture was stirred at 0° C. for 0.5 h, then compound 2-9 (560 mg, 1.0 mmol) was added. The mixture was stirred at 0° C. for 0.5 h, then extracted with ethyl acetate (50 mL×3). The organic extracts were combined, washed with brine, and dried over Na$_2$SO$_4$. The solvent was removed under reduced pressure to give a crude residue, which was purified by flash chromatography on silica gel (dichloromethane:methyl alcohol=30:1) to afford compound 2-11 (340 mg). ESI-MS m/z: 619 [M+H]$^+$.

Step 9: To a solution of compound 2-11 (340 mg, 0.55 mmol) in toluene (20 mL) were added tert-butyl (3-cyano-4-(5,5-dimethyl-1,3,2-dioxaborinan-2-yl)-7-fluorobenzo[b]thiophen-2-yl)carbamate (2-12) (443 mg, 1.1 mmol), dichloropalladium,[2-(2-diphenylphosphanylphenoxy)phenyl]-diphenylphosphane (78 mg, 0.11 mmol) and Cs$_2$CO$_3$ (537 mg, 1.64 mmol). The mixture was stirred at 105° C. for 16 h, then extracted with ethyl acetate (50 mL×3). The organic extracts were combined, washed with brine, and dried over Na$_2$SO$_4$. The solvent was removed under reduced pressure to give a crude residue, which was purified by flash chromatography on silica gel (dichloromethane:methyl alcohol=30:1) to afford compound 2-13 (240 mg). ESI-MS m/z: 830 [M+H]$^+$.

Step 10: To a solution of 2-13 (30 mg, 0.036 mmol) in DCM (10 mL) was added 2,2,2-trifluoroacetic acid (5 mL). The mixture was stirred at RT for 2 h, then the pH was adjusted to 7~8 with NaHCO$_3$. The mixture was extracted with dichloromethane (20 mL×3). The organic extracts were combined, washed with brine, and dried over Na$_2$SO$_4$. The solvent was removed under reduced pressure to give a crude residue. The crude residue was purified by prep-HPLC to afford compound 1113 (1.5 mg). ESI-MS m/z: 630 [M+H]$^+$; $^1$HNMR (400 MHZ, CD3OD): δ 7.21-7.18 (m, 1H), 7.08-7.04 (m, 1H), 5.54-5.41 (m, 1H), 4.83-4.81 (m, 1H), 4.63-4.47 (m, 6H), 4.10 (m, 1H), 3.68-3.64 (m, 2H), 3.52 (s, 3H), 2.51-2.46 (m, 1H), 2.34 (m, 1H), 2.26-2.19 (m, 3H), 2.07-2.02 (m, 2H).

Example 1c: Synthesis of 2-amino-4-((5S)-5-(aminomethyl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (914)

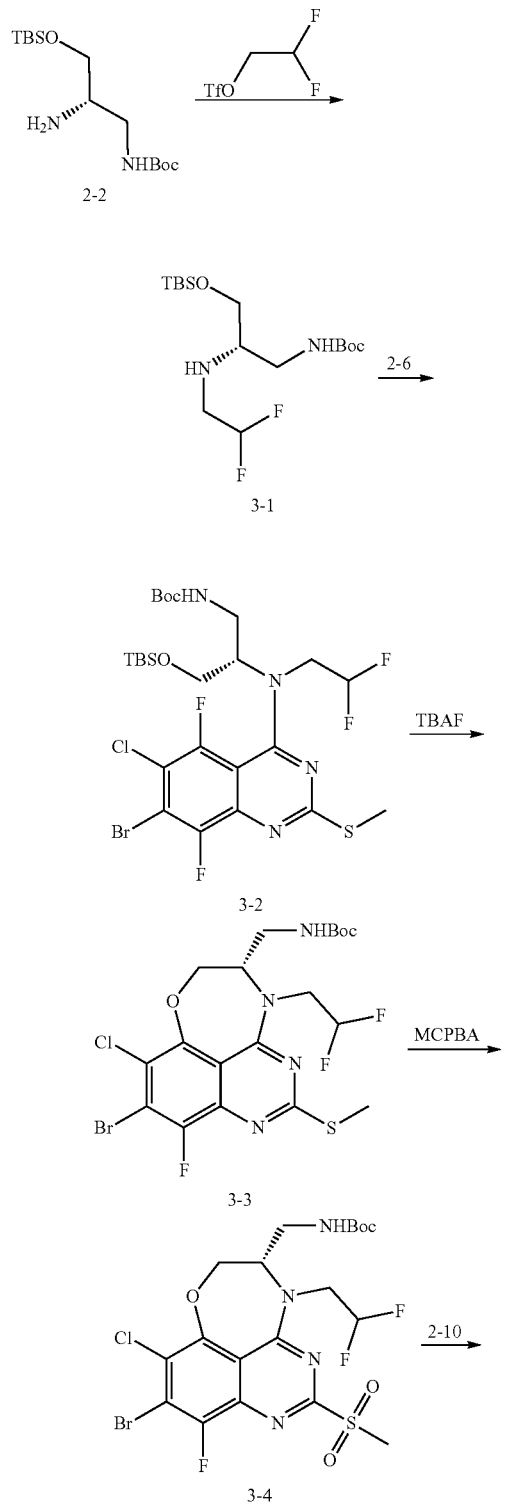

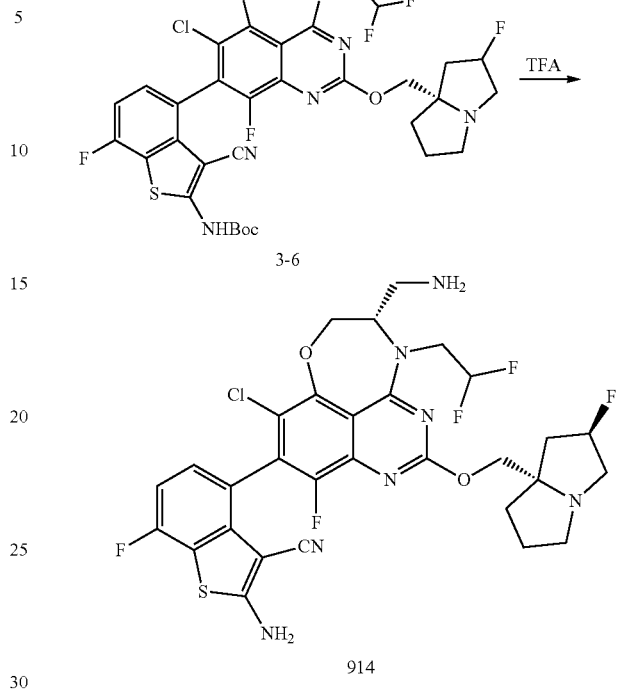

Step 1: To a solution of compound 2-2 (760 mg, 2.5 mmol) in MeCN (15 mL) were added 2,2-difluoroethyl trifluoromethanesulfonate (1.07 g, 5 mmol) and DIEA (967 mg, 7.5 mmol). The mixture was stirred at RT for 16 h, then the crude residue was purified by flash chromatography on silica gel (petroleum ether:ethyl acetate=5:1) to afford compound 3-1 (890 mg). ESI-MS m/z: 368 [M+H]$^+$.

Step 2: To a solution of compound 3-1 (890 mg, 2.4 mmol) in TAA (20 mL) were added 2-6 (870 mg, 2.4 mmol) and 2,6-dimethylpyridine (776 mg, 7.25 mmol). The mixture was stirred at 105° C. for 16 h, then the crude residue was purified by flash chromatography on silica gel (petroleum ether:ethyl acetate=20:1) to afford compound 3-2 (1.5 g).

Step 3: To a solution of compound 3-2 (1.5 g, 2.16 mmol) in DMF (20 mL) was added CsF (1.2 g, 8.6 mmol). The mixture was stirred at 80° C. for 2 h, then extracted with ethyl acetate (50 mL×3). The organic extracts were combined, washed with brine, and dried over $Na_2SO_4$. The solvent was removed under reduced pressure to give a crude residue. The crude residue was purified by flash chromatography on silica gel (petroleum ether:ethyl acetate=5:1) to afford compound 3-3 (720 mg). ESI-MS m/z: 558 [M+H]$^+$.

Step 4: To a solution of compound 3-3 (720 mg, 1.29 mmol) in DCM (20 mL) was added 3-chlorobenzoperoxoic acid (667 mg, 3.8 mmol). The mixture was stirred at RT for 2 h. The solvent was removed under reduced pressure and the crude residue was purified by flash chromatography on silica gel (dichloromethane:methyl alcohol=100:1) to afford compound 3-4 (730 mg). ESI-MS m/z: 590 [M+H]$^+$.

Step 5: To a solution of 2-10 (1.1 mg, 7.4 mmol) in THF (10 mL) was added sodium hydride (296 mg, 60%, 7.4 mmol). The mixture was stirred at 0° C. for 0.5 h, then compound 3-4 (730 mg, 1.23 mmol) was added. The mixture was stirred at 0° C. for 0.5 h, then extracted with ethyl acetate (50 mL×3). Organic extracts were combined, washed with brine, and dried over Na₂SO₄. The solvent was removed under reduced pressure to give a crude residue, which was purified by flash chromatography on silica gel (dichloromethane:methyl alcohol=30:1) to afford compound 3-5 (790 mg). ESI-MS m/z: 669 [M+H]⁺.

Step 6: To a solution of compound 3-5 (790 mg, 1.18 mmol) in toluene (20 mL) were added 2-12 (954 mg, 2.36 mmol), dichloropalladium,[2-(2-diphenylphosphanylphenoxy)phenyl]-diphenylphosphane (168 mg, 0.24 mmol) and Cs₂CO₃ (1.15 g, 3.54 mmol). The mixture was stirred at 105° C. for 16 h, then extracted with ethyl acetate (50 mL×3). The organic extracts were combined, washed with brine, and dried over Na₂SO₄. The solvent was removed under reduced pressure to give a crude residue, which was purified by flash chromatography on silica gel (dichloromethane:methyl alcohol=30:1) to afford compound 3-6 (610 mg). ESI-MS m/z: 880 [M+H]⁺.

Step 7: To a solution of compound 3-6 (35 mg, 0.039 mmol) in DCM (10 mL) was added 2,2,2-trifluoroacetic acid (5 mL). The mixture was stirred at RT for 2 h, then the pH was adjusted to 7~8 with NaHCO₃. The mixture was extracted with dichloromethane (20 mL×3) and the organic extracts combined, washed with brine, and dried over Na₂SO₄. The solvent was removed under reduced pressure and the resulting residue was purified by prep-HPLC to afford compound 914 (1.3 mg). ESI-MS m/z: 680 [M+H]⁺; ¹HNMR (400 MHZ, CD3OD): δ 7.09-7.06 (m, 1H), 6.96-6.91 (m, 1H), 6.48-6.19 (m, 1H), 5.38-5.25 (m, 1H), 4.94-4.90 (m, 1H), 4.45-4.41 (m, 2H), 4.35-4.29 (m, 1H), 4.07-3.87 (m, 2H), 3.48-3.37 (m, 3H), 3.06-3.02 (m, 2H), 2.39-2.29 (m, 2H), 2.19-2.05 (m, 4H), 1.93-1.88 (m, 2H).

Example 1d: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (827)

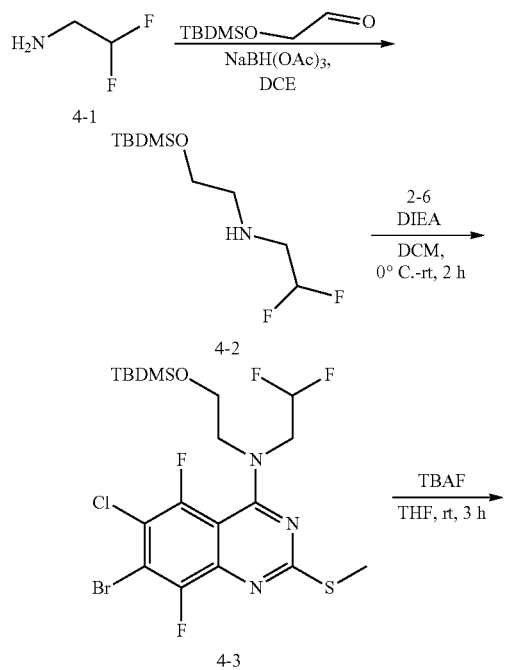

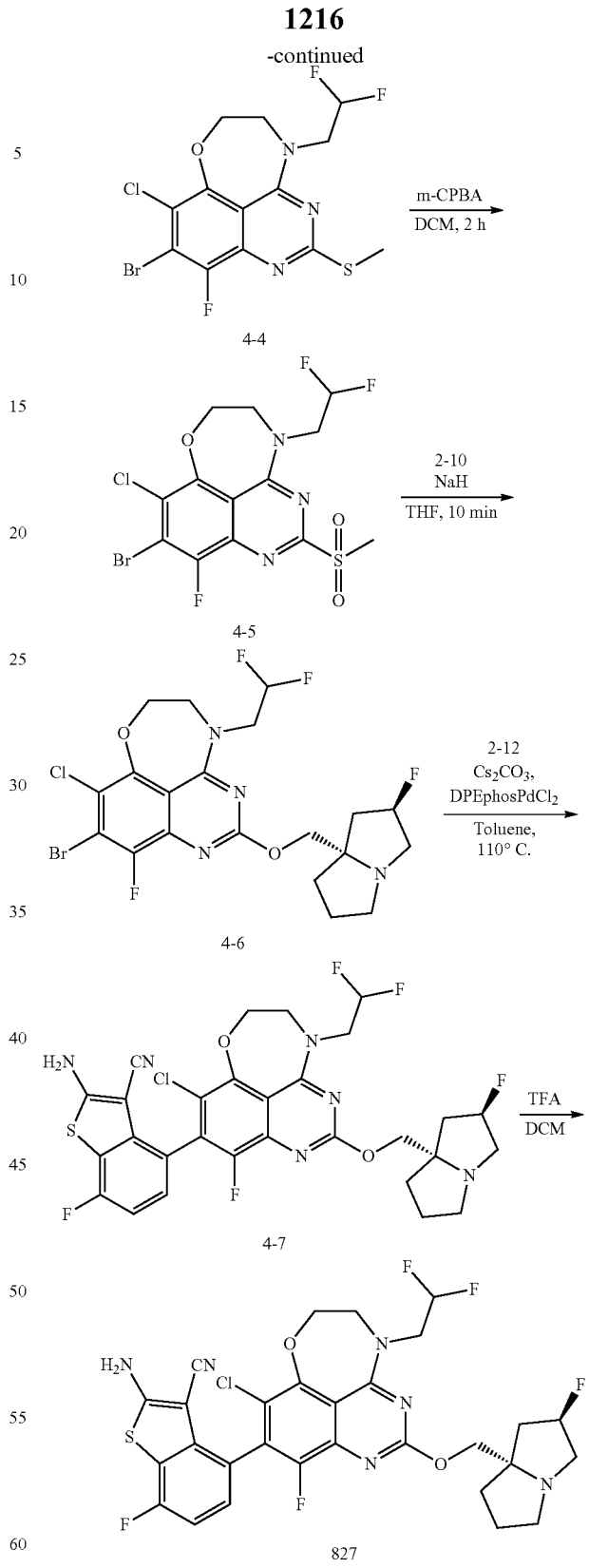

Step 1: To a solution of 4-1 (500 mg, 6.17 mmol) and NaBH(OAc)₃ (3.92 g, 18.5 mmol) in DCE (5.0 mL) was added a solution of 2-((tert-butyldimethylsilyl)oxy)acetaldehyde (1.07 g, 6.17 mmol) in DCE (15 mL) dropwise at 0° C. for 1 h under N₂ atmosphere. The mixture was stirred at room temperature for 0.1 h. After completion, the mixture was quenched with aq. NaHCO₃ (15 mL) and adjusted to pH=7~8. The residue was extracted with DCM (40 mL×3). The organic phase was washed with brine, dried over anhydrous Na₂SO₄, and concentrated under reduced pressure to get a crude residue. The crude residue was purified by silica gel column chromatography (eluting with 0~5% of MeOH in DCM) to afford compound 4-2 (400 mg). ESI-MS m/z: 240.1 [M+H]⁺.

Step 2: To a solution of 4-2 (200 mg, 0.560 mmol) in DCM (20 mL) was added DIEA (216 mg, 1.67 mmol). The mixture was cooled to 0° C. with an ice bath and then 2-6 (266 mg, 1.11 mmol) was added. The mixture was stirred for 2 h at RT, then the solvent was removed and the residue was purified by silica gel column chromatography (eluting with 0~5% of EA in PE) to afford compound 4-3 (300 mg). ESI-MS m/z: 561.6 [M+H]⁺.

Step 3: To a solution of 4-3 (300 mg, 0.53 mmol) in THF (10 mL) was added a solution of TBAF (2.0 M, 0.67 mL, 1.36 mmol) and the resulting mixture stirred for 2 h at RT. The mixture was diluted with ethyl acetate (100 mL) and washed with water and brine, the organic layer was concentrated in vacuo and purified by silica gel column chromatography (eluting with 0~5% of MeOH in DCM) to afford compound 4-4 (180 mg). ESI-MS m/z: 427.6 [M+H]⁺.

Step 4: To a solution of 4-4 (180 mg, 0.42 mmol) in DCM (10 mL) cooled to 0° C. was added m-CPBA (145 mg, 0.84 mmol) and the resulting mixture stirred for 2 h at RT. The reaction mixture was quenched with aq. NaHSO3 and stirred for 15 min, then aq. NaHCO₃ was added. The organic layer was washed with water and brine, dried and concentrated in vacuo to afford compound 4-5 (200 mg). ESI-MS m/z: 459.5 [M+H]⁺.

Step 5: To a solution of 2-10 (138 mg, 0.86 mmol) in THF (2 mL) was added NaH (60%, 52.0 mg, 1.30 mmol) at 0° C. under N₂. The mixture was stirred for 30 min, then a solution of 4-5 (200 mg, 0.43 mmol) in THF (5 mL) was added and stirred for 5 min. The reaction mixture was quenched with aq. NH₄Cl and extracted with ethyl acetate (100 mL×2). The combined extracts were washed with brine and dried, concentrated in vacuo, and the residue was purified by silica gel column chromatography (eluting with 0~10% of MeOH in DCM) to afford compound 4-6 (180 mg). ESI-MS m/z: 539.2 [M+H]⁺.

Step 6: To a solution of 4-6 (180 mg, 0.33 mmol) in toluene (5 mL) were added 2-12 (270 mg, 0.66 mmol), Cs₂CO₃ (272 mg, 0.83 mmol) and DPEphosPdCl₂ (60 mg, 0.083 mmol) under N₂. The mixture was stirred at 110° C. for 3 h. The mixture was diluted with DCM (50 mL), then filtered through a celite pad and the filtrate purified by flash silica column chromatography (eluting with 0~10% of MeOH in DCM) to afford compound 4-7 (270 mg). ESI-MS m/z: 750.6 [M+H]⁺.

Step 7: To a solution of 4-7 (270 mg, 0.360 mmol) in DCM (5 mL) was added TFA (2 mL) and the resulting solution was stirred for 2 h at RT. The solvent was removed and the resulting residue was dissolved in DCM (100 mL) and adjusted to pH=7~8 with aq. NaHCO₃. The organic layer was concentrated in vacuo and purified by silica gel column chromatography (eluting with 0~10% of MeOH in DCM) to afford compound 827. ESI-MS m/z: 651.1 [M+H]⁺.

Example 1e: Synthesis of 2-amino-4-(8-chloro-10-fluoro-2-(((2R,7aS)-2-fluorotetrahydro-1H-pyrrolizin-7a(5H)-yl)methoxy)-4-(3-hydroxycycloheptyl)-5,6-dihydro-4H-[1,4]oxazepino[5,6,7-de]quinazolin-9-yl)-7-fluorobenzo[b]thiophene-3-carbonitrile (682)

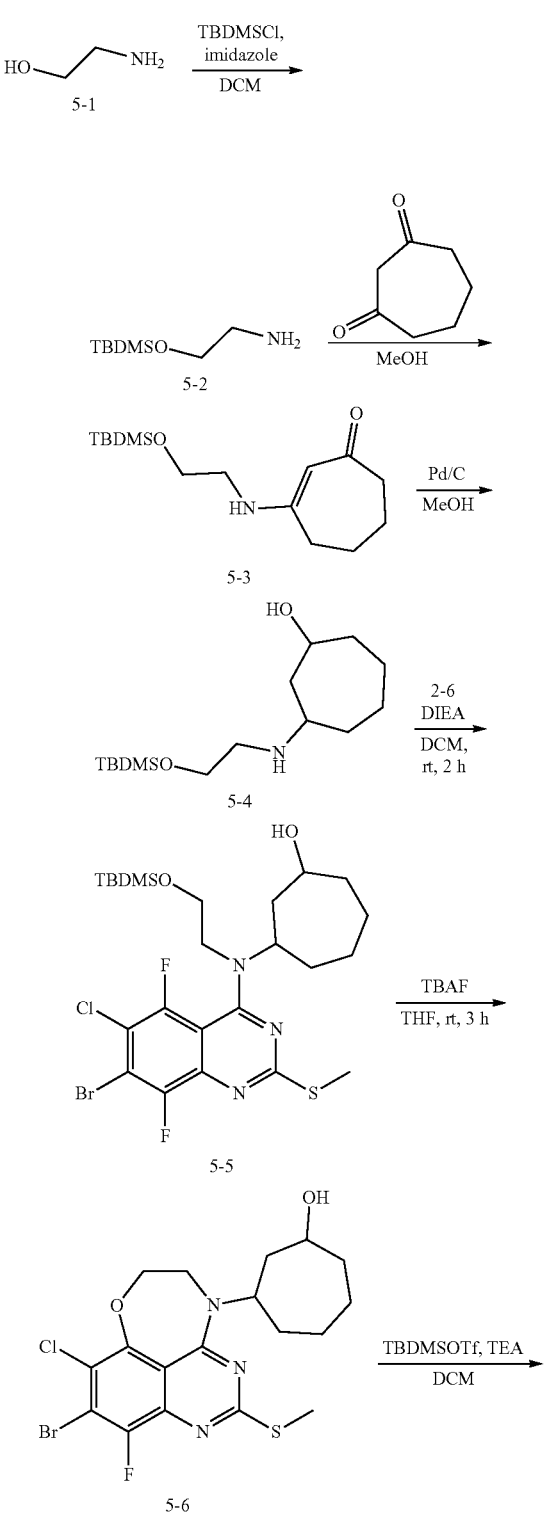

-continued

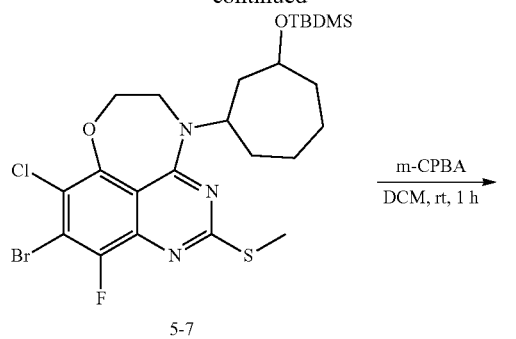

5-7

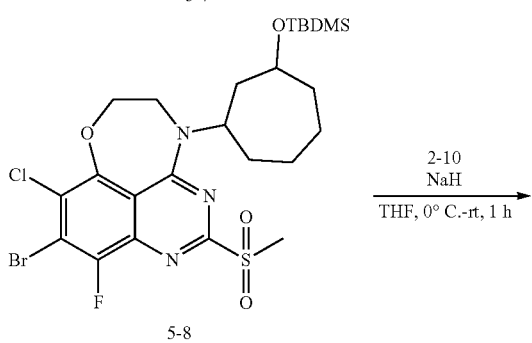

5-8

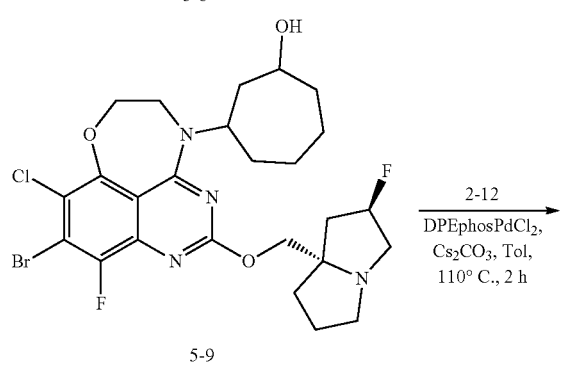

5-9

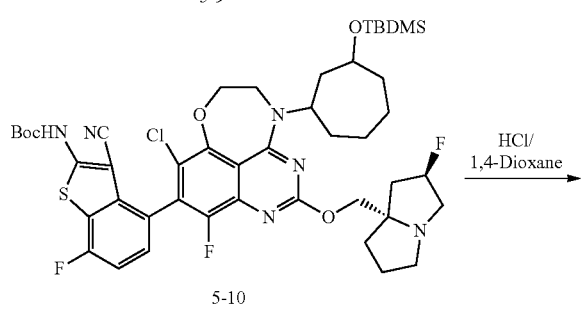

5-10

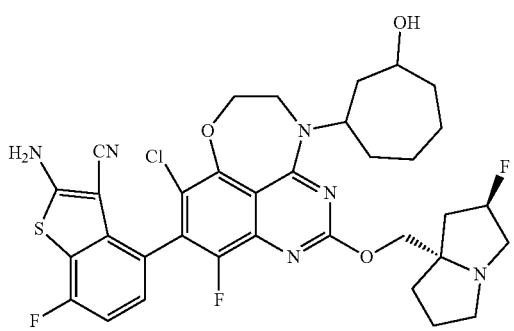

682

Step 1: To a solution of 5-1 (10.0 g, 164 mmol) in DCM (100 mL) were added imidazole (33.4 g, 492 mmol) and TBDMSCl (24.8 g, 164 mmol) and the resulting mixture stirred at 25° C. for 2 h. The mixture was quenched with H$_2$O and extracted with DCM (300 mL×3). The organic layer was dried and concentrated in vacuo, and the residue purified by flash silica column chromatography (eluting with 0~10% of EA in PE) to afford compound 5-2 (20.0 g). ESI-MS m/z: 176.2 [M+H]$^+$.

Step 2: To a solution of cycloheptane-1,3-dione (650 mg, 5.16 mmol) in MeOH (20 mL) was added compound 5-2 (903 mg, 5.16 mmol) at 0° C. and the mixture was stirred at 25° C. for 2 h. The solution was used directly in the next reaction without purification. ESI-MS m/z: 284.1 [M+H]$^+$.

Step 3: Pd/C (325 mg) was added to the above obtained mixture of 5-3 under H2. The mixture was filtered through a celite pad and the filtrate concentrated to give the crude product, which was purified by flash silica column chromatography (eluting with 0~50% of EA in PE) to give 5-4 (760 mg). ESI-MS m/z: 288.3 [M+H]$^+$.

Step 4: To a solution of 2-6 (200 mg, 0.560 mmol) in DCM (10 mL) were added 5-4 (321 mg, 1.12 mmol) and TEA (169 mg, 1.68 mmol) at 0° C. and the resulting mixture stirred at 25° C. for 1 h. The mixture was quenched with H$_2$O and extracted with DCM (100 mL×3). The organic layer was dried and concentrated in vacuo, then the residue was purified by flash silica column chromatography (eluting with 0~20% of EA in PE) to afford 5-5 (300 mg). ESI-MS m/z: 609.7 [M+H]$^+$.

Step 5: To a solution of 5-5 (280 mg, 0.46 mmol) in THF (10 mL) was added TBAF (1.38 mL) and the resulting mixture stirred at 25° C. for 2 h. The mixture was quenched with H$_2$O and extracted with DCM (70 mL×3). The organic layer was dried and concentrated in vacuo and the residue purified by flash silica column chromatography (eluting with 0~20% of EA in PE to afford compound 5-6 (160 mg). ESI-MS m/z: 478.0 [M+H]$^+$.

Step 6: To a solution of 5-6 (160 mg, 0.34 mmol) in DCM (10 mL) were added TEA (102 mg, 1.01 mmol) and TBDMSOTf (133 mg, 0.51 mmol) at 0° C. The resulting mixture was stirred at 25° C. for 2 h, then quenched with H$_2$O and extracted with DCM (50 mL×3). The organic layer was dried and concentrated in vacuo and the residue was purified by flash silica column chromatography (eluting with 0~20% of EA in PE) to afford 5-7 (178 mg). ESI-MS m/z: 589.7 [M+H]$^+$.

Step 7: To a solution of 5-7 (178 mg, 0.30 mmol) in DCM (5 mL) was added m-CPBA (105 mg, 0.60 mmol) and the mixture was stirred at 25° C. for 1 h. The mixture was quenched with aq. Na$_2$SO$_3$, then aq. NaHCO$_3$ was added and the product extracted with DCM (100 mL×3). The organic layer was dried and concentrated in vacuo and the residue was purified by flash silica column chromatography (eluting with 0~100% of EA in PE) to afford 5-8 (140 mg). ESI-MS m/z: 624.1 [M+H]$^+$.

Step 8: To a solution of 2-10 (61.0 mg, 0.39 mmol) in THF (1 mL) was added NaH (60%, 23.0 mg, 0.58 mmol) at 0° C. under N$_2$. The mixture was stirred for 0.5 h, then compound 5-8 (120 mg, 0.19 mmol) in THF (1 mL) was added and the mixture was stirred at 0° C. for 0.5 h. The mixture was quenched with aq. NH$_4$Cl and extracted with DCM (100 mL×3). The organic layer was dried and concentrated in vacuo and the residue was purified by flash silica column chromatography (eluting with 0~10% of MeOH in DCM) to afford 5-9 (120 mg). ESI-MS m/z: 589.1 [M+H]$^+$.

Step 9: To a solution of 5-9 (60.0 mg, 0.09 mmol) in toluene (2 mL) were added 2-12 (69.0 mg, 0.17 mmol), Cs₂CO₃ (84.0 mg, 0.26 mmol) and DPEphosPdCl₂ (15.0 mg, 0.02 mmol) under N₂. The mixture was stirred at 110° C. for 4 h, then DCM (5 mL) was added and the mixture was filtered through a celite pad. The filtrate was purified by flash silica column chromatography (eluting with 0~10% of MeOH in DCM) to afford 5-10 (50.0 mg). ESI-MS m/z: 913.4 [M+H]⁺.

Step 10: A solution of 5-10 (40.0 mg, 0.04 mmol) in HCl/1,4-dioxane (5 mL) was stirred at 25° C. for 1 h. The solvent was removed under reduced pressure and the residue was purified by prep-HPLC to afford four diastereomers. Compound 682 was one of the diastereomers isolated (4.12 mg). ESI-MS m/z: 699.2 [M+H]⁺; ¹H NMR (400 MHZ, DMSO-d6) δ 8.10 (d, J=27.1 Hz, 2H), 7.20 (dd, J=8.2, 5.3 Hz, 1H), 7.13 (t, J=8.9 Hz, 1H), 5.32 (d, J=54.5 Hz, 2H), 4.61-4.49 (m, 3H), 4.21 (s, 1H), 3.99 (s, 1H), 3.75 (s, 2H), 3.29-3.03 (m, 4H), 2.90 (s, 1H), 2.28-2.00 (m, 4H), 1.98-1.80 (m, 5H), 1.78-1.66 (m, 4H), 1.65-1.50 (m, 2H), 1.36 (d, J=9.0 Hz, 1H).

Example 1f: Synthesis of 5-((9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)methyl)-1-methyl-1H-pyrazole-4-carbonitrile (641)

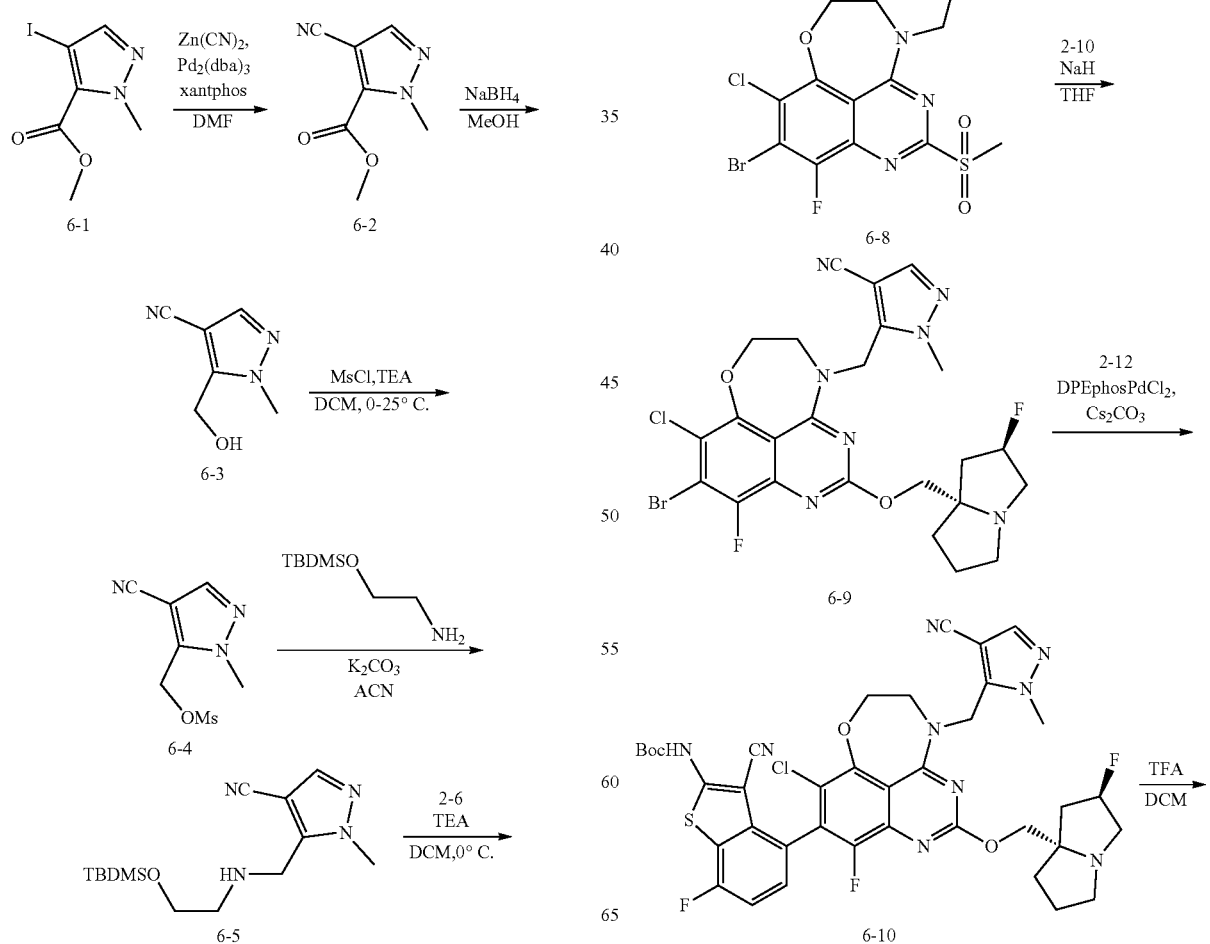

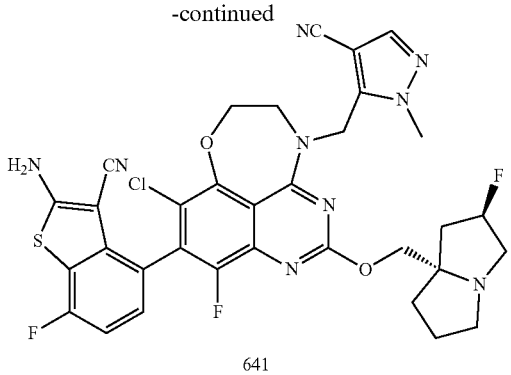

641

Step 1: To a solution of 6-1 (2.66 g, 10.0 mmol) in DMF (10 mL) were added Zn(CN)$_2$ (1.17 g, 10.0 mmol), xantphos (1.16 g, 2.00 mmol) and Pd(dba)$_3$ (0.91 g, 1.00 mmol). The mixture was stirred at 80° C. for 2 h under N$_2$. The mixture was purified by flash silica column chromatography (eluting with 0~20% of EA in PE) to afford 6-2 (1.50 g). ESI-MS m/z: 165.9 [M+H]$^+$.

Step 2: To a solution of 6-2 (1.50 g, 9.09 mmol) in MeOH (10 mL) was added NaBH$_4$ (0.35 g, 9.09 mmol) at 0° C. The mixture was stirred at 25° C. for 2 h, then concentrated in vacuo. Water (30 mL) was added and the residue was extracted with EA (20 mL×3). The organic layers were concentrated and the residue was purified by flash silica column chromatography (eluting with 0~100% of EA in PE) to afford 6-3 (690 mg). ESI-MS m/z: 138.2 [M+H]$^+$.

Step 3: To a solution of 6-3 (520 mg, 3.80 mmol) in DCM (10 mL) were added MsCl (649 mg, 5.69 mmol) and TEA (1.15 g, 11.4 mmol) at 0° C. The mixture was stirred at 25° C. for 2 h. Water (30 mL) was added and the product was extracted with DCM (20 mL×3). The organic layers were concentrated and the residue was purified by flash silica column chromatography (eluting with 0~20% of EA in PE) to afford 6-4 (750 mg). ESI-MS m/z: 215.8 [M+H]$^+$.

Step 4: To a solution of compound 6-4 (750 mg, 3.49 mmol) in ACN (20 mL) was added 2-((tert-butyldimethylsilyl)oxy) ethan-1-amine (610 mg, 3.49 mmol) and K$_2$CO$_3$ (1444 mg, 10.47 mmol). The mixture was stirred at 25° C. for 16 h. The mixture was purified by flash silica column chromatography (eluting with 0~50% of EA in PE to compound 6-5 (670 mg). ESI-MS m/z: 295.0 [M+H]$^+$.

Step 5: To a solution of 2-6 (200 mg, 0.56 mmol) in ACN (10 mL) was added 6-5 (328 mg, 1.12 mmol) at 25° C. and the resulting mixture stirred at 70° C. for 1 h. The mixture was purified by flash silica column chromatography (eluting with 0~20% of EA in PE) to afford 6-6 (260 mg). ESI-MS m/z: 618.6 [M+H]$^+$.

Step 6: To a solution of 6-6 (240 mg, 0.39 mmol) in THF (10 mL) was added TBAF (1.17 mL) and the resulting mixture stirred at 25° C. for 2 h. Water (30 mL) was added and the product was extracted with DCM (20 mL×3). The organic layers were concentrated, and the residue was purified by flash column chromatography on silica gel (eluting with 0~20% of EA in PE) to afford 6-7 (154 mg). ESI-MS m/z: 484.6 [M+H]$^+$.

Step 7: To a solution of 6-7 (154 mg, 0.32 mmol) in DCM (10 mL) was added m-CPBA (166 mg, 0.96 mmol) and the resulting mixture stirred at 25° C. for 1 h. The mixture was quenched with aq. Na$_2$SO$_3$, then aq. NaHCO$_3$ was added and the product extracted with DCM (30×3). The organic layer was dried and concentrated on vacuo. The residue was purified by flash silica column chromatography (eluting with 0~30% of EA in PE) to afford 6-8 (120 mg). ESI-MS m/z: 517.0 [M+H]$^+$.

Step 8: To a solution of 2-10 (62.0 mg, 0.390 mmol) in THF (1 mL) was added NaH (60%, 23 mg, 0.58 mmol) at 0° C. under N$_2$. The mixture was stirred for 0.5 h, then compound 6-8 (100 mg, 0.19 mmol) in THF (1 mL) was added and the mixture was stirred at 0° C. for 0.5 h. The mixture was quenched with aq. NH$_4$Cl and extracted with DCM (20×3). The organic layer was dried and concentrated in vacuo. The residue was purified by flash silica column chromatography (eluting with 0~10% of MeOH in DCM) to afford 6-9 (90 mg). ESI-MS m/z: 596.0 [M+H]$^+$.

Step 9: To a solution of 6-9 (40.0 mg, 0.07 mmol) in toluene (2 mL) were added 2-12 (55.0 mg, 0.13 mmol), Cs$_2$CO$_3$ (66.0 mg, 0.20 mmol) and DPEphosPdCl$_2$ (12.0 mg, 0.02 mmol) under argon atmosphere. The mixture was stirred at 110° C. for 4 h, then DCM (5 mL) was added and the mixture was filtered through a celite pad. The filtrate was purified by flash silica column chromatography (eluting with 0~10% of MeOH in DCM) to afford 6-10 (40 mg). ESI-MS m/z: 806.1 [M+H]$^+$.

Step 10: To a solution of 6-10 (30 mg, 0.04 mmol) in DCM (2 mL) was added TFA (1 mL). The mixture was stirred at RT for 1 h, then concentrated under reduced pressure. The residue was purified by prep-HPLC to afford compound 641 (5.65 mg). ESI-MS m/z: 706.1 [M+H]$^+$; $^1$H NMR (400 MHZ, DMSO-d6): δ 8.08 (s, 2H), 7.98 (s, 1H), 7.29-7.18 (m, 1H), 7.14 (t, J=9.0 Hz, 1H), 5.68-5.30 (m, 1H), 5.29-5.20 (m, 1H), 5.02 (d, J=15.8 Hz, 1H), 4.68 (d, J=12.7 Hz, 2H), 4.18 (s, 4H), 4.00 (s, 3H), 3.51 (s, 4H), 2.07 (s, 6H).

Example 1g: Synthesis of 2-amino-4-(8-chloro-10-fluoro-2-(((2R,7aS)-2-fluorotetrahydro-1H-pyrrolizin-7a(5H)-yl)methoxy)-5-(hydroxymethyl)-4-methyl-5,6-dihydro-4H-[1,4]oxazepino[5,6,7-de]quinazolin-9-yl)-7-fluorobenzo[b]thiophene-3-carbonitrile (900)

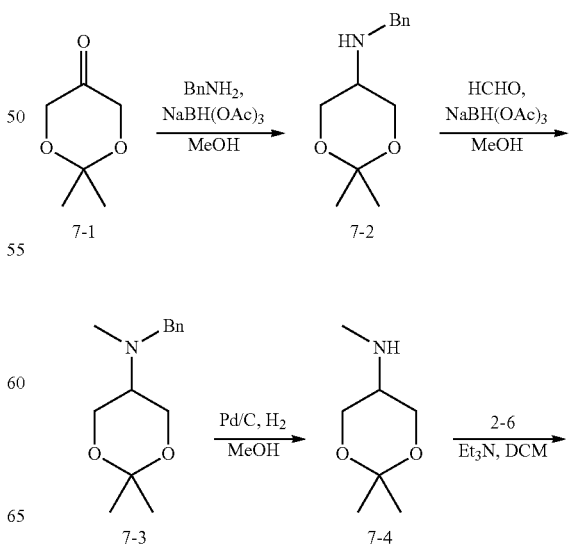

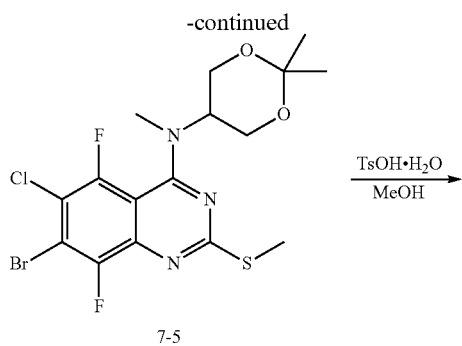

7-5

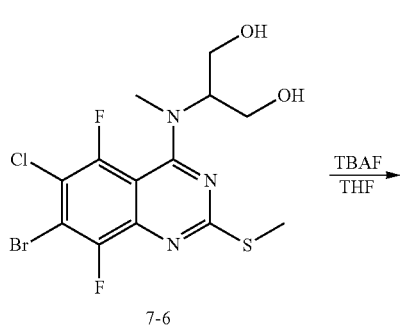

7-6

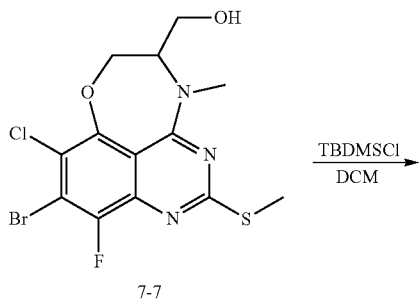

7-7

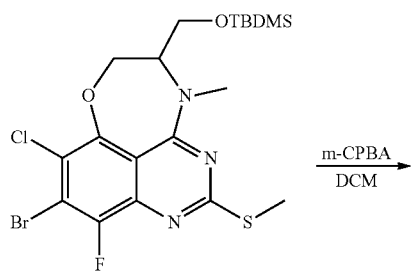

7-8

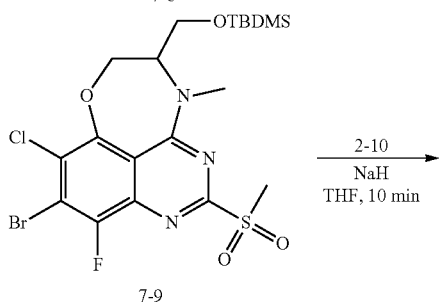

7-9

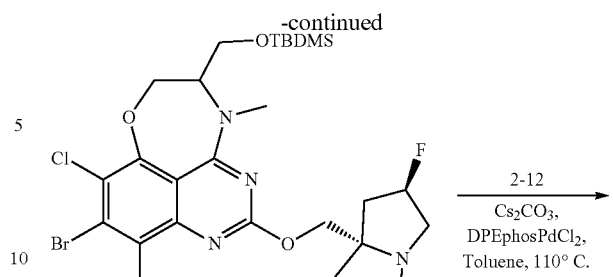

7-10

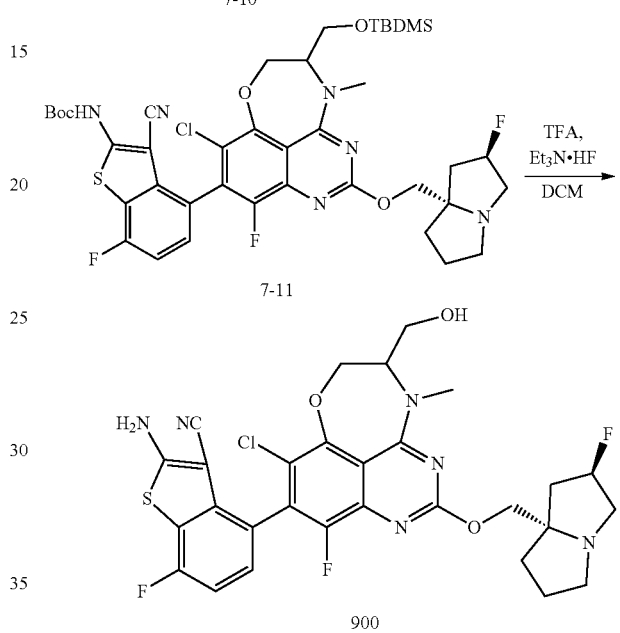

7-11

900

Step 1: To a solution of 7-1 (1.30 g, 10.0 mmol) in THF (50 mL) was added BnNH$_2$ (1.10 g, 10.0 mmol) and the resulting mixture stirred for 2 h at RT. NaBH$_4$ (0.760 g, 20.0 mmol) was then added and stirred continued for 1 h. Removed the solvent, the residue was purified by flash silica column chromatography (eluting with 0~5% of MeOH in DCM) to afford compound 7-2 (1.38 g). ESI-MS m/z: 222.2 [M+H]$^+$.

Step 2: To a solution of 7-2 (1.00 g, 4.50 mmol) in MeOH (15 mL) were added HCHO (37%, 5 mL) and NaBH(OAc)$_3$ (1.90 g, 9.00 mmol) and the resulting mixture was stirred for 2 h at RT. The solvent was removed and the residue was purified by flash silica column chromatography (eluting with 0~5% of MeOH in DCM) to afford 7-3 (1.1 g). ESI-MS m/z: 235.9 [M+H]$^+$.

Step 3: To a solution of 7-3 (1.00 g, 4.26 mmol) in MeOH (50 mL) was added Pd/C (200 mg) under H$_2$ atmosphere and the mixture was stirred for 1 h at RT. The catalyst was removed by filtration and the filtrate was concentrated in vacuo to afford compound 7-4 (500 mg). ESI-MS m/z: 146.0 [M+H]$^+$.

Step 4: To a solution of 2-6 (150 mg, 0.42 mmol) in DCM (20 mL) was added DIEA (108 mg, 0.840 mmol), and the resulting mixture was cooled to 0° C. with an ice bath before adding 7-4 (200 mg, 1.38 mmol). The mixture was stirred for 2 h at RT, then solvent was removed and the residue was purified by flash silica column chromatography (eluting with 0~10% of EA in PE) to afford 7-5 (200 m). ESI-MS m/z: 467.6 [M+H]$^+$.

Step 5: To a solution of 7-5 (200 mg, 0.43 mmol) in THF (10 mL) was added TsOH·H₂O (16.0 mg, 0.08 mmol) and the mixture was stirred for 3 h at RT. Solvent was removed and the residue was purified by flash silica column chromatography (eluting with 0~5% of MeOH in DCM) to afford 7-6 (180 mg). ESI-MS m/z: 427.6 [M+H]⁺.

Step 6: To a solution of 7-6 (150 mg, 0.35 mmol) in THF (10 mL) was added a solution of TBAF (2.0 M, 0.5 mL, 0.870 mmol) and the resulting mixture was stirred for 2 h at RT. The mixture was diluted with ethyl acetate (100 mL) and washed with water and brine. The organic layer was concentrated in vacuo and purified by flash silica column chromatography (eluting with 0~7% of MeOH in DCM) to afford compound 7-7 (125 mg). ESI-MS m/z: 407.6 [M+H]⁺.

Step 7: To a solution of 7-7 (120 mg, 0.290 mmol) in DCM (10 mL) was added imidazole (40.0 mg, 0.58 mmol) the resulting mixture was cooled to 0° C. TBDMSCl (67.0 mg, 0.45 mmol) was added and the resulting mixture was stirred for 1 h at RT. The solvent was removed and the residue purified by flash silica column chromatography (eluting with 0~5% of MeOH in DCM) to afford 7-8 (80 mg). ESI-MS m/z: 508.7 [M+H]⁺.

Step 8: To a solution of 7-8 (80 mg, 0.15 mmol) in DCM (10 mL) at 0° C. was added m-CPBA (80 mg, 0.46 mmol) and the resulting mixture stirred for 1 h at RT. The reaction was quenched with aq. NaHSO₃ and stirred for 15 min, then aq. NaHCO₃ was added. The organic layer was washed with water and brine, dried and concentrated in vacuo to afford compound 7-9 (80 mg). ESI-MS m/z: 553.7 [M+H]⁺.

Step 9: To a solution of 2-10 (46.0 mg, 0.289 mmol) in THF (1 mL) was added NaH (60%, 20.0 mg, 0.430 mmol) at 0° C. under N₂. The resulting mixture was stirred for 30 min, then a solution of compound 7-9 (80 mg, 0.144 mmol) in THF (5 mL) was added and stirred for 5 min. The reaction was quenched with aq. NH₄Cl and extracted with ethyl acetate (50 mL×3), then the combined extracts were washed with brine, dried, and concentrated in vacuo to afford 7-10 (100 mg). ESI-MS m/z: 633.0 [M+H]⁺.

Step 10: To a solution of 7-10 (63.0 mg, 0.100 mmol) in toluene (2 mL) were added 2-12 (80 mg, 0.20 mmol), Cs₂CO₃ (100 mg, 0.30 mmol) and DPEphosPdCl₂ (18.0 mg, 0.025 mmol) under N₂. The mixture was stirred at 110° C. for 3 h. The mixture was diluted with DCM (50 ml), then was filtered through a celite pad and the filtrate purified by flash silica column chromatography (eluting with 0~10% of MeOH in DCM) to afford compound 7-11 (80 mg). ESI-MS m/z: 845.8 [M+H]⁺.

Step 11: To a solution of 7-11 (80.0 mg, 0.095 mmol) in DCM (2 mL) was added TFA (1 mL) and the resulting mixture stirred for 1 h. The mixture was then concentrated in vacuo, the residue dissolved in THF (1 mL), and Et₃N·HF (2 mL) added. The resulting mixture was stirred for 30 min, then solvent was removed and the residue was purified by prep-HPLC to afford compound 900 (3.72 mg). ESI-MS m/z: 631.2 [M+H]⁺; ¹H NMR (400 MHZ, CD3OD): δ 8.52 (s, 1H), 7.20 (dd, J=8.2, 5.2 Hz, 1H), 7.03 (t, J=8.9 Hz, 1H), 5.40 (d, J=50 Hz, 1H), 4.92 (m, 2H), 4.55-4.35 (m, 3H), 4.02 (m, 1H), 3.90 (m, 1H), 3.83 (m, 1H), 3.50 (m, 5H), 3.21 (m, 1H), 2.38 (m, 2H), 2.23 (m, 1H), 2.14 (m, 2H), 1.97 (m, 1H).

Example 1h: Synthesis of N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)formamide (988)

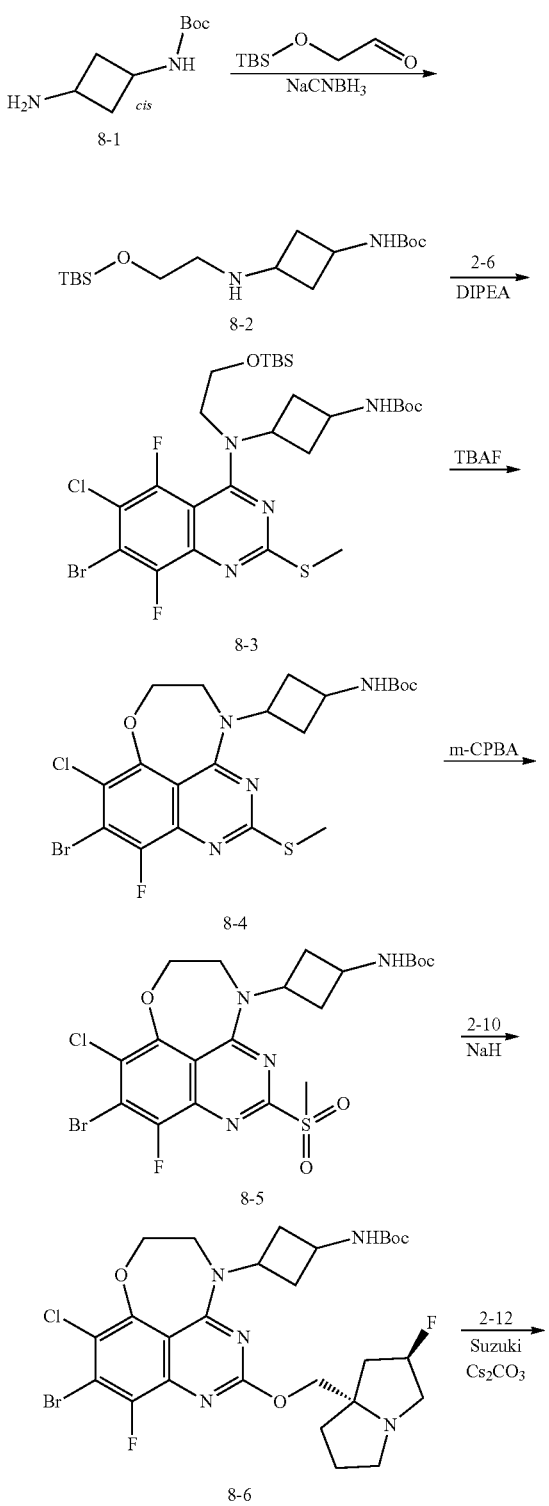

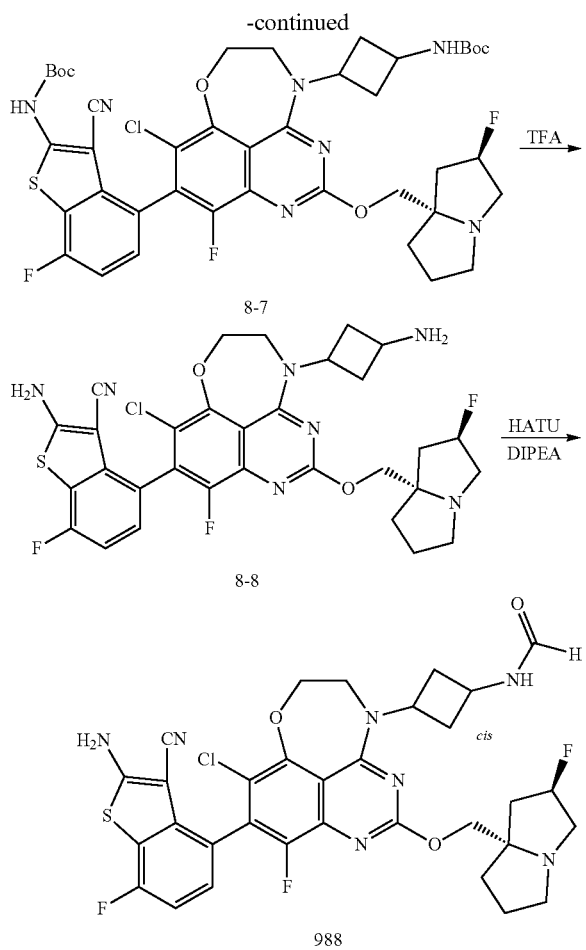

Step 1: To a solution of 8-1 (1 g, 5.37 mmol, 1.2 eq) in MeOH (15 mL) were added 2-((tert-butyldimethylsilyl)oxy) acetaldehyde (780 mg, 4.47 mmol, 1 eq), NaBH$_3$CN (421 mg, 6.7 mmol, 1.5 eq), and AcOH (0.1 ml) and the resulting mixture was stirred at RT overnight. The mixture was partitioned between water and ethyl acetate. The organic layer was washed with brine, dried over Na$_2$SO$_4$, filtered, and concentrated in vacuo. The residue was purified by flash column chromatography on silica gel to afford 8-2 (1.2 g). ESI-MS m/z: 345 [M+H]$^+$.

Step 2: To a solution of 8-2 (1.2 g, 3.48 mmol, 1.5 eq) in THF (15 mL) at RT were added TEA (704 mg, 6.97 mmol, 3 eq) and 2-6 (837 mg, 2.32 mmol, 1 eq). The resulting solution was stirred at RT overnight, then the mixture was partitioned between dichloromethane and water. The organic layer was concentrated and the residue purified on a silica gel column eluting with ethyl acetate/petroleum ether (1:4) to afford 8-3 (1.4 g). ESI-MS m/z: 669 [M+H]$^+$.

Step 3: To a stirred solution of 8-3 (1.4 g, 2.09 mmol) in THF (3 mL) was added TBAF (9 mL). The resulting mixture was stirred at RT for 2 h, then partitioned between water and ethyl acetate. The organic layer was washed with brine, dried over Na$_2$SO$_4$, filtered, and concentrated in vacuo. The residue was purified by flash column chromatography on silica gel to afford 8-4 (700 mg). ESI-MS m/z: 535 [M+H]$^+$.

Step 4: To a stirred solution of 8-4 (700 mg, 1.31 mmol, 1 eq) in DCM (15 mL) was added m-CPBA (680 mg, 3.93 mmol, 3 eq) and the resulting mixture stirred at RT for 2 h. The mixture was partitioned between water and dichloromethane. The organic layer was washed with brine, dried over Na$_2$SO$_4$, filtered, and concentrated in vacuo. The residue was purified by flash column chromatography on silica gel to afford 8-5 (650 mg). ESI-MS m/z: 567 [M+H]$^+$.

Step 5: To a stirred solution of 2-10 (547 mg, 3.44 mmol, 3 eq) in THF (5 mL) was added 60% NaH (138 mg, 3.44 mmol, 3 eq) at 0° C. The mixture was stirred for 30 min, then compound 8-5 (650 mg, 1.15 mmol, 1 eq) was added and the resulting mixture stirred at RT for 2 h. The mixture was added to ice water and partitioned between water and ethyl acetate. The organic layer was washed with brine, dried over Na$_2$SO$_4$, filtered, and concentrated in vacuo. The residue was purified by flash column chromatography on silica gel to afford 8-6 (440 mg). ESI-MS m/z: 646 [M+H]$^+$.

Step 6: To a stirred solution of 8-6 (440 mg, 0.68 mmol, 1 eq) in anhydrous DMF (8 mL) were added 2-12 (330 mg, 0.82 mmol, 1.2 eq), PdCl$_2$(dpephos) (97 mg, 0.14 mmol, 0.2 eq) and Cs$_2$CO$_3$ (665 mg, 2.04 mmol, 3 eq) and the resulting mixture stirred at 105° C. under nitrogen for 3 h. The mixture was partitioned between water and ethyl acetate. The organic layer was washed with brine, dried over Na$_2$SO$_4$, filtered, and concentrated in vacuo. The residue was purified by flash column chromatography on silica gel to afford 8-7 (210 mg). ESI-MS m/z: 856 [M+H]$^+$.

Step 7: To a solution of 8-7 (100 mg) in DCM (6 mL) at RT was added TFA (2 mL) and the resulting mixture stirred at RT for 2 h. The mixture was concentrated in vacuo to remove the solvent. The residue was purified by flash column chromatography on silica gel to afford 8-8 (60 mg). ESI-MS m/z:656 [M+H]$^+$.

Step 8: To a solution of 8-8 (60 mg, 0.09) in THF (4 mL) at RT were added HATU (52 mg, 0.137 mmol, 1.5 eq) and DIPEA (35 mg, 0.27 mmol, 3 eq) at 0° C., then formic acid (6.3 mg, 0.137 mmol, 1.5 eq) was added slowly. The resulting mixture was stirred at RT for 2 h, then concentrated in vacuo to remove the solvent. The residue was purified by flash column chromatography on silica gel to afford 988 (23 mg). ESI-MS m/z: 684 [M+H]$^+$; $^1$HNMR (400 MHZ, CD3OD): δ 8.03 (s, 1H), 7.24-7.22 (m, 1H), 7.08-7.04 (m, 1H), 5.62-5.48 (m, 1H), 4.76-4.58 (m, 5H), 4.26-4.22 (m, 1H), 3.99-3.86 (m, 5H), 3.47-3.45 (m, 1H), 2.97-2.91 (m, 2H), 2.63-1.96 (m, 7H).

Example 1i: Synthesis of 4-(4-(2-azabicyclo[2.1.1] hexan-5-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile (991)

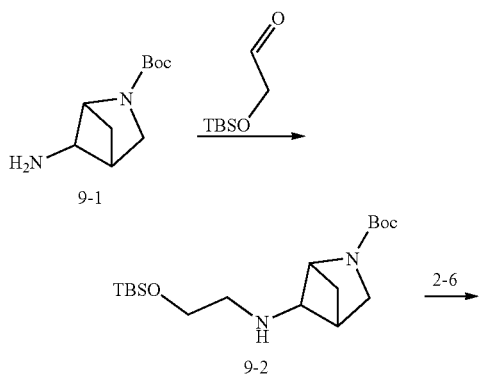

-continued

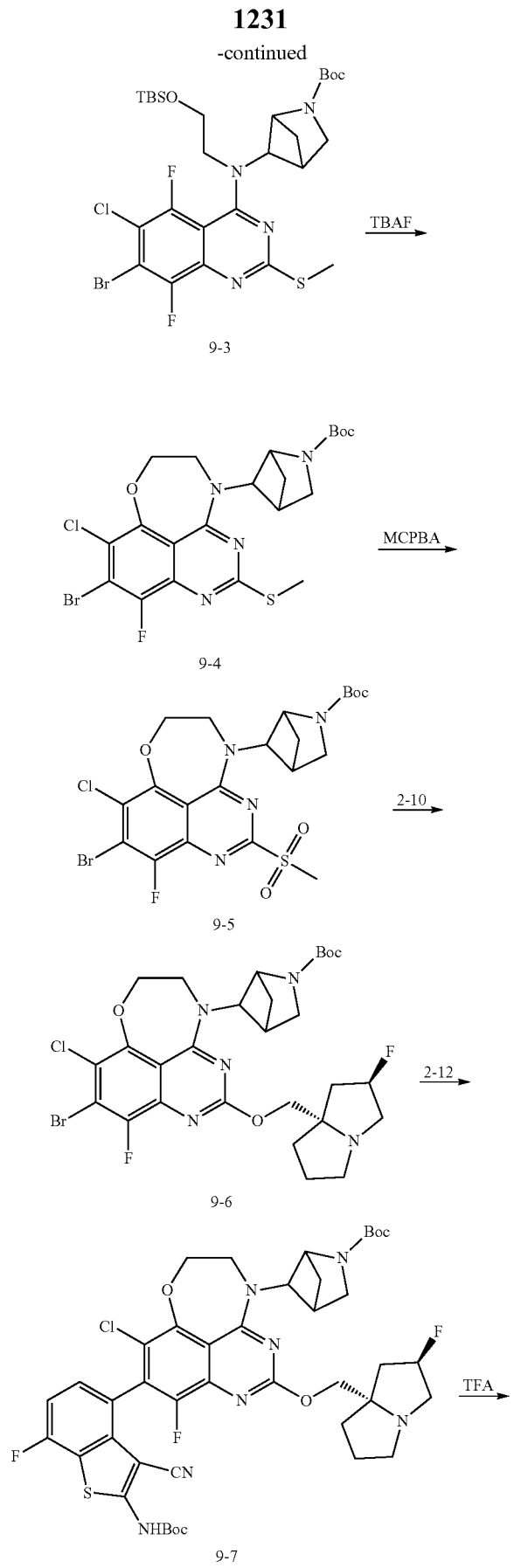

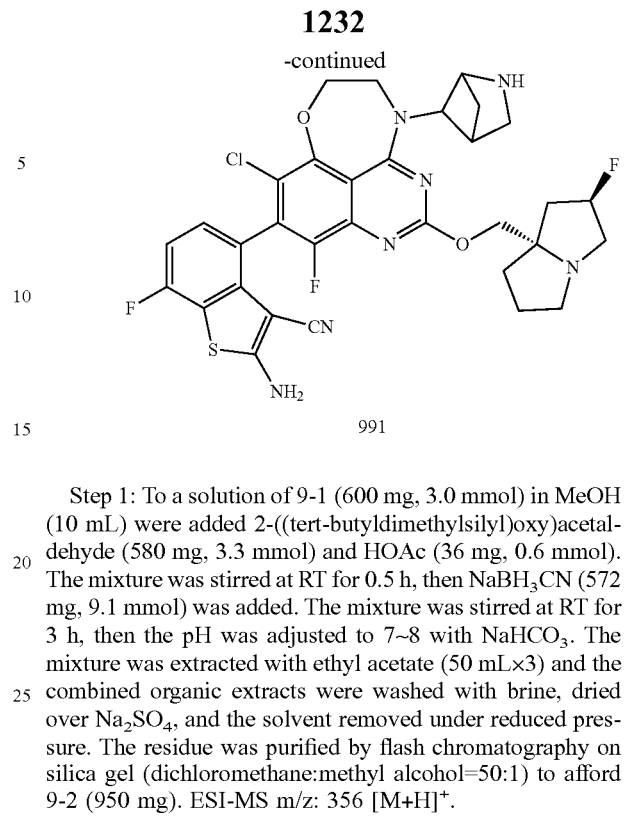

Step 1: To a solution of 9-1 (600 mg, 3.0 mmol) in MeOH (10 mL) were added 2-((tert-butyldimethylsilyl)oxy)acetaldehyde (580 mg, 3.3 mmol) and HOAc (36 mg, 0.6 mmol). The mixture was stirred at RT for 0.5 h, then NaBH$_3$CN (572 mg, 9.1 mmol) was added. The mixture was stirred at RT for 3 h, then the pH was adjusted to 7~8 with NaHCO$_3$. The mixture was extracted with ethyl acetate (50 mL×3) and the combined organic extracts were washed with brine, dried over Na$_2$SO$_4$, and the solvent removed under reduced pressure. The residue was purified by flash chromatography on silica gel (dichloromethane:methyl alcohol=50:1) to afford 9-2 (950 mg). ESI-MS m/z: 356 [M+H]$^+$.

Step 2: To a solution of 9-2 (950 mg, 2.66 mmol) in THF (15 mL) were added 2-6 (960 mg, 2.66 mmol) and N-ethyl-N-isopropylpropan-2-amine (1.0 g, 8 mmol). The mixture was stirred at 80° C. for 2 h, then extracted with ethyl acetate (50 mL×3). The organic extracts were combined, washed with brine, dried over Na$_2$SO$_4$, and the solvent removed under reduced pressure. The residue was purified by flash chromatography on silica gel (petroleum ether:ethyl acetate=10:1) to afford 9-3 (930 mg).

Step 3: To a solution of 9-3 (930 mg, 1.36 mmol) in THF (10 mL) was added tetrabutylammonium fluoride (5 mL, 1 M in THF). The mixture was stirred at RT for 2 h, then extracted with ethyl acetate (50 mL×3). The organic extracts were combined, washed with brine, and dried over Na$_2$SO$_4$. The solvent was removed under reduced pressure and the residue was purified by flash chromatography on silica gel (petroleum ether:ethyl acetate=5:1) to afford 9-4 (520 mg). ESI-MS m/z: 546 [M+H]$^+$.

Step 4: To a solution of 9-4 (520 mg, 0.95 mmol) in DCM (20 mL) was added 3-chlorobenzoperoxoic acid (492 mg, 2.85 mmol). The mixture was stirred at RT for 2 h, then the solvent was removed under reduced pressure. The residue was purified by flash chromatography on silica gel (dichloromethane:methyl alcohol=100:1) to afford 9-5 (540 mg). ESI-MS m/z: 578 [M+H]$^+$.

Step 5: To a solution of 2-10 (891 mg, 5.6 mmol) in THF (10 mL) was added sodium hydride (224 mg, 60%, 5.6 mmol) and the resulting mixture stirred at 0° C. for 0.5 h. Compound 9-5 (540 mg, 0.934 mmol) was added and the mixture stirred at 0° C. for 0.5 h. The mixture was extracted with ethyl acetate (50 mL×3) and the combined organic extracts were washed with brine, dried over Na$_2$SO$_4$, and solvent removed under reduced pressure. The residue was purified by flash chromatography on silica gel (dichloromethane:methyl alcohol=30:1) to afford 9-6 (480 mg). ESI-MS m/z: 657 [M+H]$^+$.

Step 6: To a solution of 9-6 (480 mg, 0.73 mmol) in toluene (20 mL) were added 2-12 (590 mg, 1.46 mmol), dichloropalladium [2-(2-diphenylphosphanylphenoxy)phenyl]-diphenylphosphane (104 mg, 0.15 mmol), and Cs$_2$CO$_3$ (714 mg, 2.19 mmol). The mixture was stirred at 105° C. for 16 h, then extracted with ethyl acetate (50 mL×3). The organic extracts were combined, washed with brine, and dried over Na$_2$SO$_4$. The solvent was removed under reduced pressure and the residue purified by flash chromatography on silica gel (dichloromethane:methyl alcohol=30:1) to afford 9-7 (310 mg). ESI-MS m/z: 868 [M+H]$^+$.

Step 7: To a solution of 9-7 (50 mg, 0.05 mmol) in DCM (10 mL) was added 2,2,2-trifluoroacetic acid (5 mL). The mixture was stirred at RT for 2 h, then the pH adjusted to 7~8 with NaHCO$_3$. The mixture was extracted with dichloromethane (20 mL×3). The organic extracts were combined, washed with brine, and dried over Na$_2$SO$_4$, then solvent was removed under reduced pressure and the residue purified by prep-HPLC to afford 991 (8.9 mg). ESI-MS m/z: 668 [M+H]$^+$; $^1$HNMR (400 MHZ, CD$_3$OD): δ 7.21-7.17 (m, 1H), 7.07-7.03 (m, 1H), 5.42-5.29 (m, 1H), 4.82-4.81 (m, 1H), 4.67-4.66 (m, 1H), 4.59 (m, 1H), 4.39-4.28 (m, 2H), 3.97 (s, 1H), 3.78-3.71 (m, 2H), 3.43-3.37 (m, 4H), 3.15-3.11 (m, 1H), 2.88-2.18 (m, 4H), 2.10-1.95 (m, 5H), 1.56-1.52 (m, 1H).

Example 1j: Synthesis of 2-amino-4-(8-chloro-4-(1-((2R,3S)-3-cyclopropylaziridine-2-carbonyl)piperidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (643)

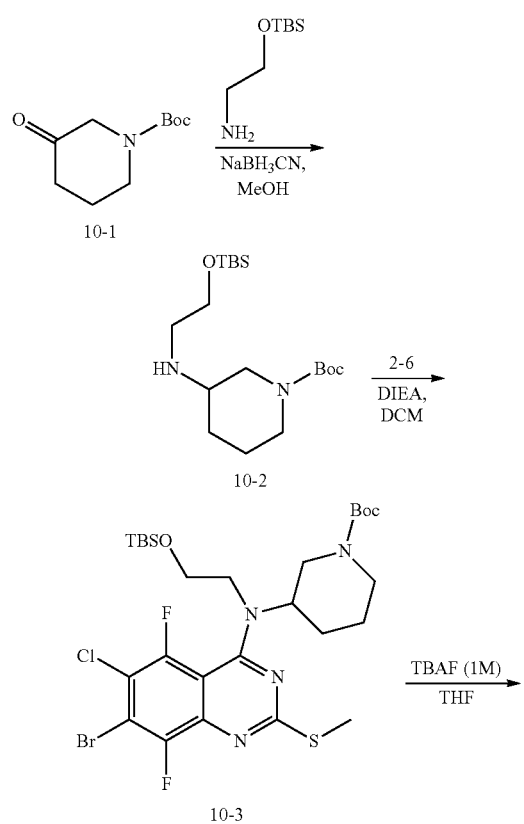

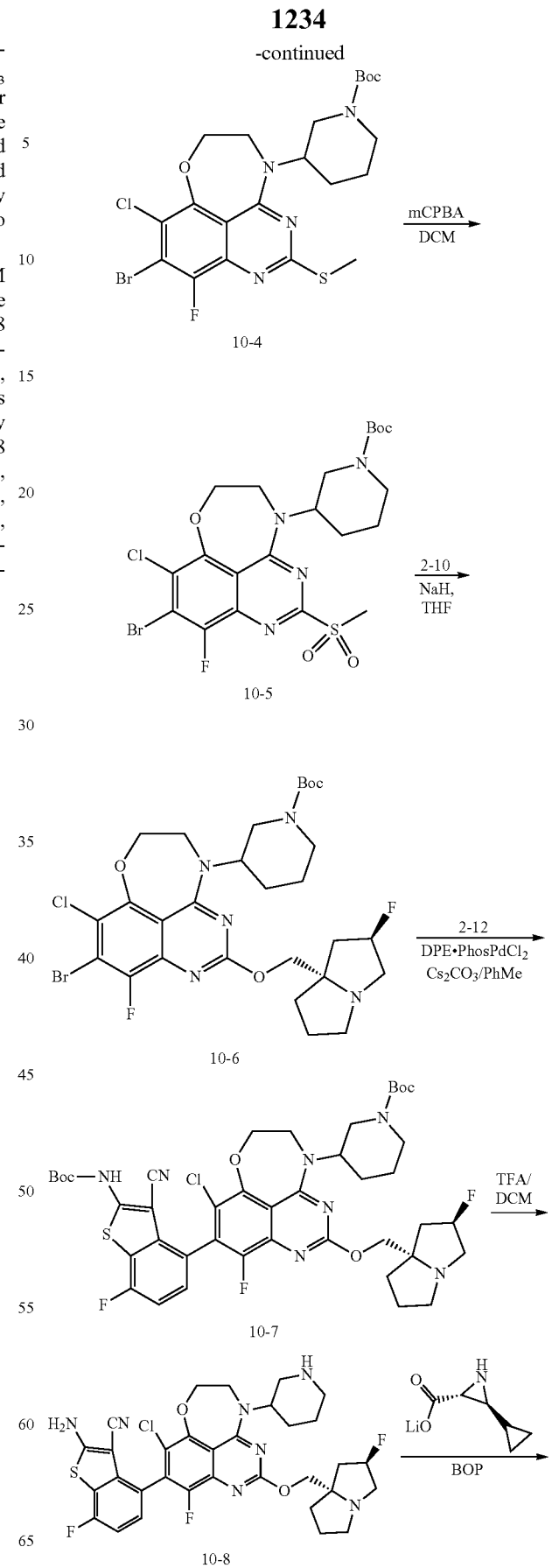

-continued

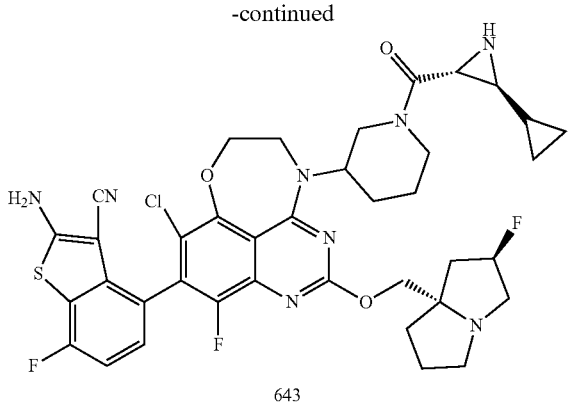

643

Step 1: To a solution of tert-butyl 3-oxopiperidine-1-carboxylate (10-1) (0.5 g, 0.25 mmol) in MeOH (20 mL) were added 2-((tert-butyldimethylsilyl)oxy)ethan-1-amine (0.503 g, 3.02 mmol), AcOH (0.1 mL) and NaBH$_3$CN (237 mg, 0.37 mmol) and the resulting mixture stirred at RT overnight. The mixture was concentrated in vacuo, then partitioned between DCM and water. The combined organic layer was concentrated in vacuo. The residue was purified on a silica gel column to afford 10-2 (0.3 g). ESI-MS m/z: 358.27 [M+H]$^+$.

Step 2: To a stirred solution of 10-2 (0.3 g, 0.77 mmol) in DCM (20 mL) were added DIEA (0.26 g, 2.09 mmol) and 2-6 (0.3 g, 0.69 mmol) and the resulting mixture stirred at RT for 16 h. The mixture was partitioned between water and DCM. The organic layer was washed with brine, dried over Na$_2$SO$_4$, filtered, and concentrated in vacuo. The residue was purified by flash column chromatography on silica gel to afford 10-3 (0.28 g).

Step 3: To a stirred solution of 10-3 (240 mg, 0.34 mmol) in THF (8 mL) was added TBAF (0.41 mL, 1M) and the resulting mixture stirred at RT for 1 h. The temperature was raised to 65° C. and the reaction stirred an additional 1 h before cooling to RT and partitioning between water and ethyl acetate. The organic layer was washed with brine, dried over Na$_2$SO$_4$, filtered, and concentrated in vacuo. The residue was purified by flash column chromatography on silica gel to afford 10-4 (140 mg). ESI-MS m/z: 546.05 [M+H]$^+$.

Step 4: To a stirred solution of 10-4 (140 mg, 0.25 mmol, 1 eq) in DCM (15 mL) was added m-CPBA (133 mg, 0.77 mmol, 3 eq). The resulting mixture was stirred at RT for 1 h, then partitioned between water and dichloromethane. The organic layer was washed with brine, dried over Na$_2$SO$_4$, filtered, and concentrated in vacuo. The residue was purified by flash column chromatography on silica gel to afford 10-5 (140 mg). ESI-MS m/z: 578.04 [M+H]$^+$.

Step 5: To a stirred solution of 2-10 (231 mg, 1.9 mmol, 6 eq) in THF (5 mL) was added 60% NaH (58 mg, 1.95 mmol, 6 eq) at −20° C. and the resulting mixture stirred for 60 min under argon. Compound 10-5 (140 mg) was added, and the resulting mixture was stirred at RT for 1 h under argon. The mixture was added to ice water and partitioned between water and ethyl acetate, then the organic layer was washed with brine, dried over Na$_2$SO$_4$, filtered, and concentrated in vacuo. The residue was purified by flash column chromatography on silica gel to afford 10-6 (80 mg). ESI-MS m/z: 657.15 [M+H]$^+$.

Step 6: To a stirred solution of 10-6 (80 mg, 0.12 mmol, 1eq) in anhydrous toluene (5 mL) were added 2-12 (150 mg, 0.36 mmol, 3 eq), PdCl$_2$(dpephos) (20 mg, 0.025 mmol, 0.2 eq) and Cs$_2$CO$_3$ (40 mg, 0.122 mmol, 3 eq) and the resulting mixture stirred at 105° C. under nitrogen for 18 h. The mixture was partitioned between water and ethyl acetate. The organic layer was washed with brine, dried over Na$_2$SO$_4$, filtered, and concentrated in vacuo. The residue was purified by flash column chromatography on silica gel to afford 10-7 (70 mg). ESI-MS m/z: 869.29 [M+H]$^+$.

Step 7: To a solution of 10-7 (70 mg) in DCM (6 mL) at RT was added TFA (2 mL) and the resulting mixture stirred at RT for 2 h. The mixture was concentrated in vacuo to remove the solvent. The residue was purified by flash column chromatography on silica gel to afford 10-8 (50 mg). ESI-MS m/z: 669.19 [M+H]$^+$.

Step 8: To a solution of 10-8 (50 mg, 0.048 mmol) in THF (4 mL) at RT were added Bop (32 mg, 0.08 mmol, 1.5 eq) and DIPEA (21 mg, 0.016 mmol, 3 eq) at 0° C., then lithium (2R,3S)-3-cyclopropylaziridine-2-carboxylate (11 mg, 0.08 mmol, 1.5 eq) in DMF (1 mL) was added slowly. The resulting mixture was stirred at RT for 2 h, then concentrated in vacuo to remove the solvent. The residue was purified by flash column chromatography on silica gel to afford 643 (4.9 mg). ESI-MS m/z: 778.24 [M+H]$^+$; $^1$HNMR (400 MHz, CD$_3$OD): δ 7.18 (m, 1H), 7.02 (m, 1H), 5.44 (m, 2H), 4.53 (m, 3H), 3.80 (m, 5H), 3.17 (m, 1H), 2.78 (m, 1H), 2.48 (m, 3H), 2.10 (m, 9H), 1.62 (m,2 H), 0.87 (m, 4H), 0.53 (m, 4H).

Example 1k: Synthesis of N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclopentyl)formamide (829)

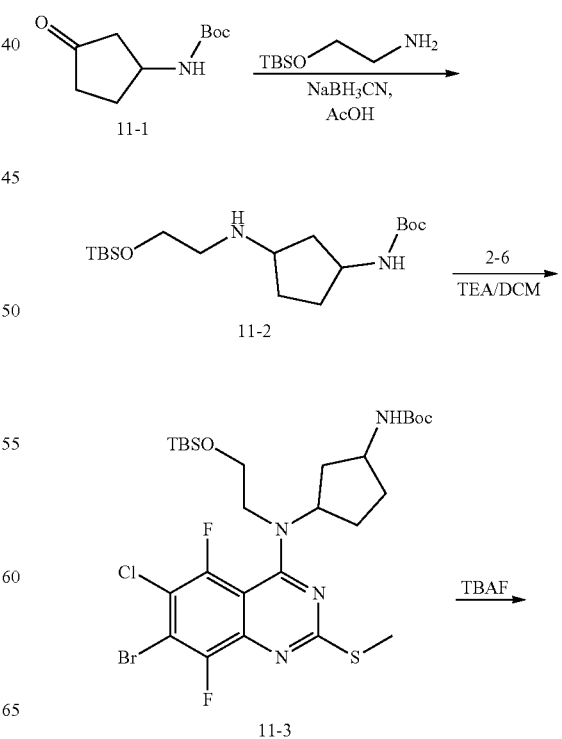

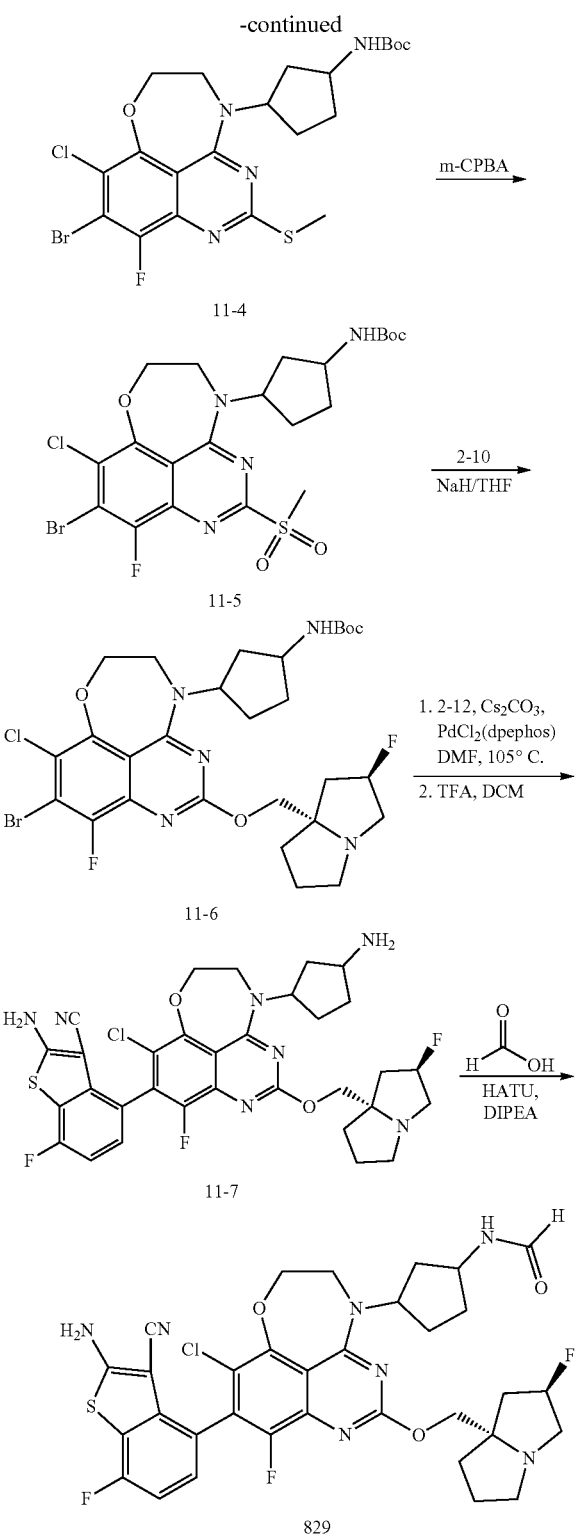

centrated in vacuo. The residue was purified by flash column chromatography on silica gel to afford 11-2 (896 mg). ESI-MS m/z: 358.60 [M+H]+.

Step 2: To a solution of 11-2 (744 mg, 2.08 mmol, 1.5 eq) in DCM (15 mL) at RT, were added TEA (420 mg, 4.16 mmol, 3 eq) and 2-6 (500 mg, 1.39 mmol, 1 eq). The resulting solution was stirred at RT overnight, then partitioned between dichloromethane and water. The organic layer was concentrated and the residue was purified on a silica gel column eluting with ethyl acetate/petroleum ether (1:4) to afford 11-3 (880 mg). ESI-MS m/z: 682.14 [M+H]+.

Step 3: To a stirred solution of 11-3 (880 mg, 1.29 mmol) in THF (2 mL), TBAF (6 mL) was added, and the resulting mixture was stirred at RT for 2 h. The mixture was partitioned between water and ethyl acetate. The organic layer was washed with brine, dried over $Na_2SO_4$, filtered, and concentrated in vacuo. The residue was purified by flash column chromatography on silica gel to afford 11-4 (680 mg). ESI-MS m/z: 547.87 [M+H]+.

Step 4: To a stirred solution of compound 11-4 (680 mg, 1.24 mmol, 1 eq) in DCM (15 mL), was added m-CPBA (644 mg, 3.72 mmol, 3 eq) and the resulting mixture stirred at RT for 2 h. The mixture was partitioned between water and dichloromethane. The organic layer was washed with brine, dried over $Na_2SO_4$, filtered, and concentrated in vacuo. The residue was purified by flash column chromatography on silica gel to afford 11-5 (660 mg). ESI-MS m/z: 579.87 [M+H]+.

Step 5: To a stirred solution of 2-10 (906 mg, 5.69 mmol, 5 eq) in THF (5 mL), 60% NaH (228 mg, 5.69 mmol, 5 eq) was added at 0° C. and the resulting solution stirred for 30 min. Compound 11-5 (660 mg) was added and the resulting mixture was stirred at RT for 2 h. The mixture was added to ice water and partitioned between water and ethyl acetate. The organic layer was washed with brine, dried over $Na_2SO_4$, filtered, and concentrated in vacuo. The residue was purified by flash column chromatography on silica gel to afford 11-6 (480 mg). ESI-MS m/z: 658.97 [M+H]+.

Step 6: To a stirred solution of 11-6 (480 mg, 0.73 mmol, 1 eq) in anhydrous DMF (8 mL) were added 2-12 (354 mg, 0.88 mmol, 1.2 eq), $PdCl_2$(dpephos) (105 mg, 0.146 mmol, 0.2 eq) and $Cs_2CO_3$ (714 mg, 2.19 mmol, 3 eq) and the resulting mixture stirred at 105° C. under nitrogen for 3 h. The mixture was partitioned between water and ethyl acetate. The organic layer was washed with brine, dried over $Na_2SO_4$, filtered, and concentrated in vacuo. The residue was purified by flash column chromatography on silica gel to afford the Boc-protected intermediate (450 mg). ESI-MS m/z: 870.39 [M+H]+.

Step 7: To a solution of the product of Step 6 (450 mg) in DCM (6 mL) at RT was added TFA (2 mL) and the resulting mixture stirred at RT for 2 h. The mixture was concentrated in vacuo to remove the solvent. The residue was purified by flash column chromatography on silica gel to afford 11-7 (160 mg). ESI-MS m/z: 670.15 [M+H]+.

Step 8: To a solution of 11-7 (10 mg, 0.015) in DCM (4 mL) at RT were added HATU (9 mg, 0.022 mmol, 1.5 eq), formic acid (3 mg, 0.022 mmol, 1.5 eq) and DIPEA (6 mg, 0.045 mmol, 3 eq) and the resulting mixture stirred at RT for 2 h. The mixture was concentrated in vacuo to remove the solvent. The residue was purified by flash column chromatography on silica gel to afford 829 (2.6 mg). ESI-MS m/z: 697.16 [M+H]+; $^1$HNMR (400 MHZ, $CD_3OD$): δ 7.12-7.08 (m, 1H), 6.96-6.92 (m, 1H), 5.49-5.45 (m, 1H), 4.61- 4.46

Step 1: To a solution of tert-butyl (3-oxocyclopentyl) carbamate (11-1) (682 mg, 3.42 mmol, 1.2 eq) in MeOH (15 mL), 2-((tert-butyldimethylsilyl)oxy)ethan-1-amine (500 mg, 2.85 mmol, 1 eq), $NaBH_3CN$ (269 mg, 4.3 mmol, 1.5 eq), AcOH (0.1 ml) were added and the resulting mixture was stirred at RT overnight. The mixture was partitioned between water and ethyl acetate. The organic layer was washed with brine, dried over $Na_2SO_4$, filtered, and con- (m, 4H), 3.81-3.71 (m, 5H), 3.38-3.29 (m, 1H), 2.55-2.42 (m, 2H), 2.32-1.85 (m, 10H), 1.64-1.46 (m, 2H).

Example 11: Synthesis of (2R,3S)—N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclopentyl)-3-cyclopropylaziridine-2-carboxamide (920)

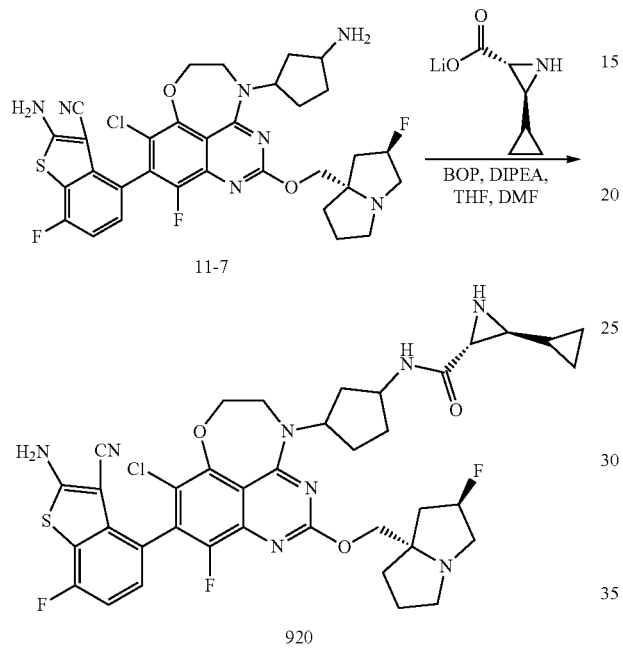

To a solution of 11-7 (10 mg, 0.015 mmol) in THF (4 mL) at RT were added Bop (10 mg, 0.022 mmol, 1.5 eq) and DIPEA (6 mg, 0.045 mmol, 3 eq) at 0° C., then lithium (2R,3S)-3-cyclopropylaziridine-2-carboxylate (3 mg, 0.022 mmol, 1.5 eq) in DMF (1 mL) was added slowly. The resulting mixture was stirred at RT for 2 h. The mixture was concentrated in vacuo to remove the solvent. The residue was purified by flash column chromatography on silica gel to afford 920 (4.9 mg). ESI-MS m/z: 779.28 [M+H]⁺; ¹HNMR (400 MHZ, CD₃OD): δ 7.24-7.20 (m, 1H), 7.08-7.04 (m, 1H), 5.58-5.45 (m, 1H), 4.71-4.54 (m, 5H), 3.89-3.73 (m, 6H), 3.01 (m, 1H), 2.88 (m, 1H), 2.61-1.98 (m, 12H), 0.97-0.88 (m, 2H), 0.55 (m, 2H), 0.37 (m, 2H).

Example 1m: Synthesis of 2-amino-4-(8-chloro-4-(1-(cyclopropylsulfonyl)pyrrolidin-3-yl)-10-fluoro-2-(((2R,7aS)-2—fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (922)

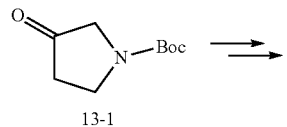

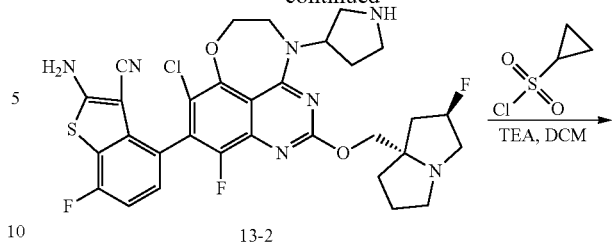

Compound 13-2 was prepared starting from tert-butyl 3-oxopyrrolidine-1-carboxylate (13-1) following the general procedure described for compound 10-8 in Example 10. ESI-MS m/z: 855.26 [M+H]⁺.

To a solution of 13-2 (25 mg, 0.028 mmol) in DCM (4 mL) at 0° C. was added TEA (12 mg, 0.12 mmol, 3 eq) followed by cyclopropanesulfonyl chloride (7 mg, 0.045 mmol, 1.2 eq). The resulting mixture was stirred at RT for 0.5 h, then partitioned between water and DCM. The organic layer was washed with brine, dried over Na₂SO₄, concentrated, purified by prep-HPLC to afford 922 (3 mg). ESI-MS m/z: 759.17 [M+H]⁺; ¹HNMR (400 MHZ, CD₃OD): δ 7.19 (m, 1H), 7.03 (t, 1H), 5.52 (m, 2H), 4.63 (m, 4H), 3.85 (m, 5H), 3.66 (m, 1H), 3.46 (m, 3H), 2.62 (m, 3H), 2.43 (m, 2H), 2.28 (m, 2H), 2.01 (m, 2H), 1.58 (m, 1H), 1.06 (m, 4H).

Example 1n: Synthesis of 2-amino-4-(8-chloro-4-(1-(2-chloro-2-fluoroacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (949)

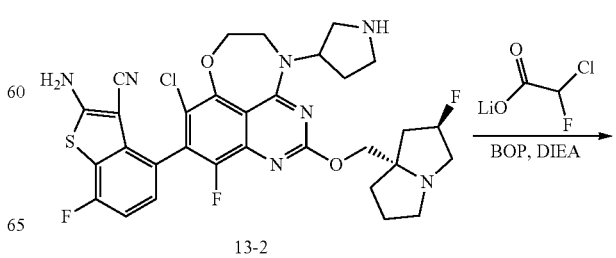

-continued

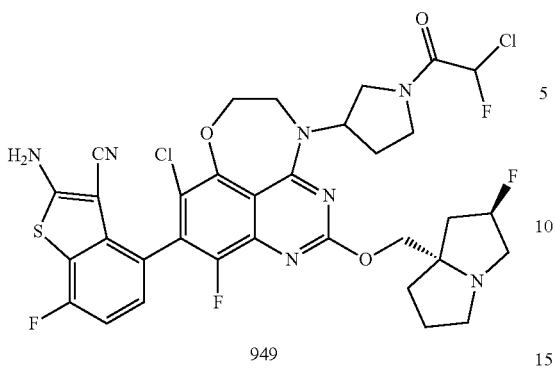

949

To a solution of 13-2 (25 mg, 0.032 mmol) in THF (5 mL) at RT were added Bop (24 mg, 0.05 mmol, 1.5 eq) and DIPEA (14 mg, 0.14 mmol, 3 eq), then lithium 2-chloro-2-fluoroacetate (6 mg, 0.05 mmol, 1.5 eq) in DMF (1 mL) was added at 0° C. The resulting mixture was stirred at RT for 2 h, then partitioned between water and ethyl acetate. The organic layer was washed with brine, dried over Na$_2$SO$_4$, and concentrated in vacuo. The residue was purified by prep-HPLC to afford 949 (6.3 mg). ESI-MS m/z: 750.59 [M+H]$^+$; $^1$HNMR (400 MHZ, CD$_3$OD): δ 7.20 (m, 1H), 7.05 (m, 1H), 5.60 (m, 2H), 4.62 (m, 4H), 3.88 (m, 6H), 3.58 (m,1 H), 3.45 (m, 1H), 2.54 (m, 2H), 2.32 (m, 5H), 2.13 (m, 1H), 1.31 (m, 3H).

Example 10: Synthesis of 2-amino-4-(8-chloro-10-fluoro-2-(((2R,7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazolin-9-yl)-7-fluorobenzo[b]thiophene-3-carbonitrile (819)

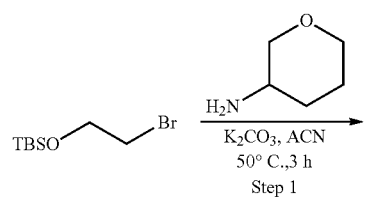

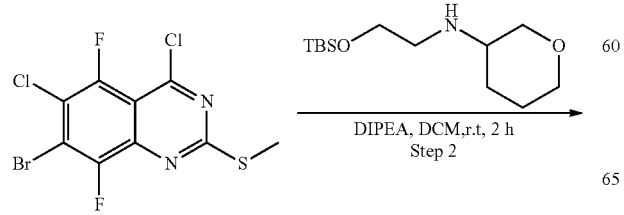

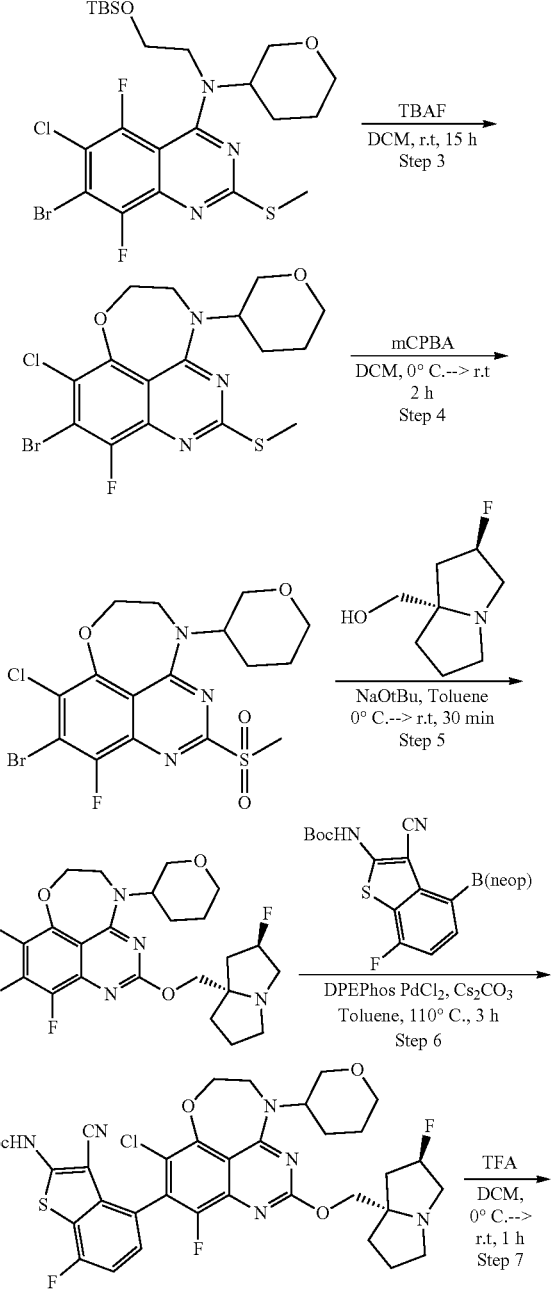

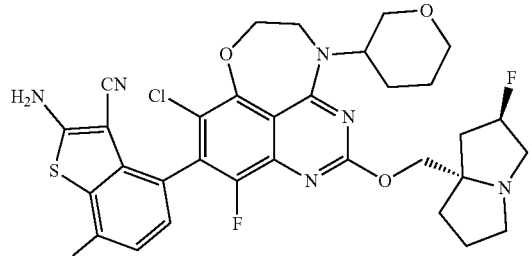

819

Step 1: K2CO$_3$ (240 mg, 1.70 mmol, 1.3 eq) was added to a mixture of (2-bromoethoxy)(tert-butyl)dimethylsilane (323 mg, 1.34 mmol, 1.0 eq) and N-(2-((tert-butyldimethylsilyl)oxy)ethyl)tetrahydro-2H-pyran-3-amine (150 mg, 1.48 mmol, 1.1 eq) in 2 mL acetonitrile solution. The mixture was heated at 50° C. for 3 hours. The solvent was removed under reduced pressure and the residue was partitioned between DCM (3 mL) and water (3 mL). After the layers were separated, the aqueous layer was washed with DCM (3 mL×2). The combined organic layers were dried over $Na_2SO_4$, filtered and concentrated. The residue was purified by silica gel chromatography eluting with 0-60% EtOAc/hexanes to yield N-(2-((tert-butyldimethylsilyl)oxy)ethyl)tetrahydro-2H-pyran-3-amine as a clear liquid (130 mg, 37% yield). LCMS calc. for $C_{13}H_{30}NO2Si$ [M+H]$^+$: m/z=260.2; Found: 260.3.

Step 2: Diisopropylethylamine (43.0 μL, 0.245 mmol, 1.6 eq) was added to a mixture of 7-bromo-4,6-dichloro-5,8-difluoro-2-(methylthio)quinazoline (55 mg, 0.154 mmol, 1.0 eq) and N-(2-((tert-butyldimethylsilyl)oxy)ethyl)tetrahydro-2H-pyran-3-amine (47.7 mg, 0.185 mmol, 1.2 eq) in DCM (2 mL). The mixture stirred at 25° C. for 2 hours and then concentrated. The residue was purified on silica gel chromatography eluting with 0-60% EtOAc/hexanes to yield 7-bromo-N-(2-((tert-butyldimethylsilyl)oxy)ethyl)-6-chloro-5,8-difluoro-2-(methylthio)-N-(tetrahydro-2H-pyran-3-yl)quinazolin-4-amine as a light green solid (58.4 mg, 65% yield). LCMS calc. for $C_{22}H_{32}BrClF_2N_3O_2SSi$ [M+H]$^+$: m/z=582.1; Found: 582.3.

Step 3: Tetra-n-butylammonium fluoride (400 μL, 0.400 mmol, 4.0 eq) (1.0 M in THF) was added dropwise to a suspension of 7-bromo-N-(2-((tert-butyldimethylsilyl)oxy)ethyl)-6-chloro-5,8-difluoro-2-(methylthio)-N-(tetrahydro-2H-pyran-3-yl)quinazolin-4-amine (58.4 mg, 0.100 mmol, 1.0 eq) in anhydrous THF (2 mL) at 0° C. The reaction mixture was warmed to room temperature and stirred for 2 hours. Water (3 mL) and EtOAc (2 mL) were added to the reaction. After layers were separated, the water phase was washed with EtOAc (3 mL×2). The combined organic layers were dried over $Na_2SO_4$, filtered and concentrated. The residue was purified by silica gel chromatography eluting with 0-20% MeOH/DCM to yield 9-bromo-8-chloro-10-fluoro-2-(methylthio)-4-(tetrahydro-2H-pyran-3-yl)-5,6-dihydro-4H-[1,4]oxazepino[5,6,7-de]quinazoline as a white solid (39.5 mg, 88% yield). LCMS calc. for $C_{16}H_{17}BrClFN_3O_2S$ [M+H]$^+$: m/z=448.0; Found: 448.1.

Step 4: m-Chloroperoxybenzoic acid (47.7 mg, 0.194 mmol, 2.2 eq) (≤77%) was added in portions to a suspension of 9-bromo-8-chloro-10-fluoro-2-(methylthio)-4-(tetrahydro-2H-pyran-3-yl)-5,6-dihydro-4H-[1,4]oxazepino[5,6,7-de]quinazoline (39.5 mg, 0.0883 mmol, 1.0 eq) in DCM (3 mL) at 0° C. The reaction was warmed to room temperature upon the completion of the addition. After 2 hours, the reaction was quenched by the addition of sat. $Na_2SO_3$ solution (3 mL). The layers were separated, and the aqueous layer was washed with DCM (2 mL×2). The combined organic layers were dried over dried over $Na_2SO_4$, filtered and concentrated. The residue was purified by silica gel chromatography eluting with 0-20% MeOH/DCM to yield 9-bromo-8-chloro-10-fluoro-2-(methylsulfonyl)-4-(tetrahydro-2H-pyran-3-yl)-5,6-dihydro-4H-[1,4]oxazepino[5,6,7-de]quinazoline as a white solid (38.9 mg, 92% yield). LCMS calc. for $C_{16}H_{17}BrClFN_3O_4S$ [M+H]$^+$: m/z=480.0; Found: 480.1.

Step 5: To a mixture of 9-bromo-8-chloro-10-fluoro-2-(methylsulfonyl)-4-(tetrahydro-2H-pyran-3-yl)-5,6-dihydro-4H-[1,4]oxazepino[5,6,7-de]quinazoline (38.9 mg, 0.0809 mmol, 1.0 eq) and ((2R,7aS)-2-fluorotetrahydro-1H-pyrrolizin-7a(5H)-yl)methanol (51.5 mg, 0.324 mmol, 4.0 eq) in anhydrous toluene (3 mL) was added NaOtBu (23.0 mg, 0.240 mmol, 3.0 eq) at 0° C. The reaction was warmed to room temperature. After 30 minutes, the solvent was removed under reduced pressure. The residue was purified by silica gel chromatography eluting with 0-20% MeOH/DCM to yield 9-bromo-8-chloro-10-fluoro-2-(((2R, 7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazoline as a colorless oil (31.5 mg, 70% yield). LCMS calc. for $C_{23}H_{27}BrClF_2N_4O_3$ [M+H]$^+$: m/z=559.1; Found: 559.3.

Step 6: A suspension of 9-bromo-8-chloro-10-fluoro-2-(((2R,7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazoline (31.5 mg, 0.0564 mmol, 1.0 eq), tert-butyl (3-cyano-4-(5,5-dimethyl-1,3,2-dioxaborinan-2-yl)-7-fluorobenzo[b]thiophen-2-yl)carbamate (34.2 mg, 0.0846 mmol, 1.5 eq), dichloro[bis(2-(diphenylphosphino)phenyl)ether]palladium(II) (8.72 mg, 8.46×10-3 mmol, 0.15 eq), and $Cs_2CO_3$ (59.4 mg, 0.169 mmol, 3.0 eq) in anhydrous toluene (2 mL) was heated to 110° C. under $N_2$ atmosphere for 3 hours. The reaction was cooled to room temperature and partitioned between EtOAc (2 mL) and water (4 mL). The organic layer was separated, and the aqueous layer was extracted with EtOAc (3 mL×2). The combined organic layers were washed with brine (4 mL), dried over $Na_2SO_4$, filtered and concentrated. The residue was purified by silica gel chromatography eluting with 0-20% MeOH/DCM to yield tert-butyl (4-(8-chloro-10-fluoro-2-(((2R,7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazolin-9-yl)-3-cyano-7-fluorobenzo[b]thiophen-2-yl)carbamate as a dark solid (9.35 mg, 22% yield). LCMS calc. for $C_{3-7}H_{39}ClF_3N_6O_5S$ [M+H]$^+$: m/z=771.2; Found: 771.4.

Step 7: To a solution of tert-butyl (4-(8-chloro-10-fluoro-2-(((2R,7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazolin-9-yl)-3-cyano-7-fluorobenzo[b]thiophen-2-yl)carbamate (9.35 mg, 0.0121 mmol) in DCM (2 mL) was added trifluoroacetic acid (0.5 mL) dropwise at 0° C. Upon finishing the addition, the reaction was warmed to room temperature and stirred for 1 hour. The mixture was concentrated under reduced pressure and the residue was purified via prep-HPLC on a C18 column (0-60% MeCN/$H_2O$ containing 0.1% HCOOH) to afford 2-amino-4-(8-chloro-10-fluoro-2-(((2R,7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazolin-9-yl)-7-fluorobenzo[b]thiophene-3-carbonitrile (819) as its formic acid salt (6.70 mg, 78% yield). LCMS calc. for $C_{32}H_{31}ClF_3N_6O_3S$ [M+H]$^+$: m/z=671.2; Found: 671.3.

Example 1p: Synthesis of 2-amino-4-(8-chloro-10-fluoro-2-(((2R,7aS)-2-fluorotetrahydro-1H-pyrrolizin-7a(5H)-yl)methoxy)-4-((R)-tetrahydrofuran-3-yl)-5,6-dihydro-4H-[1,4]oxazepino[5,6,7-de]quinazolin-9-yl)-7-fluorobenzo[b]thiophene-3-carbonitrile (617)

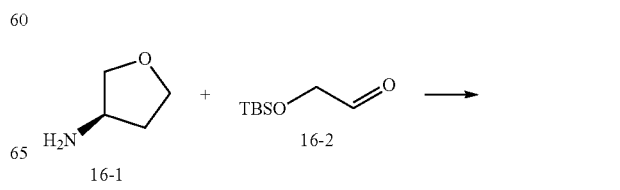

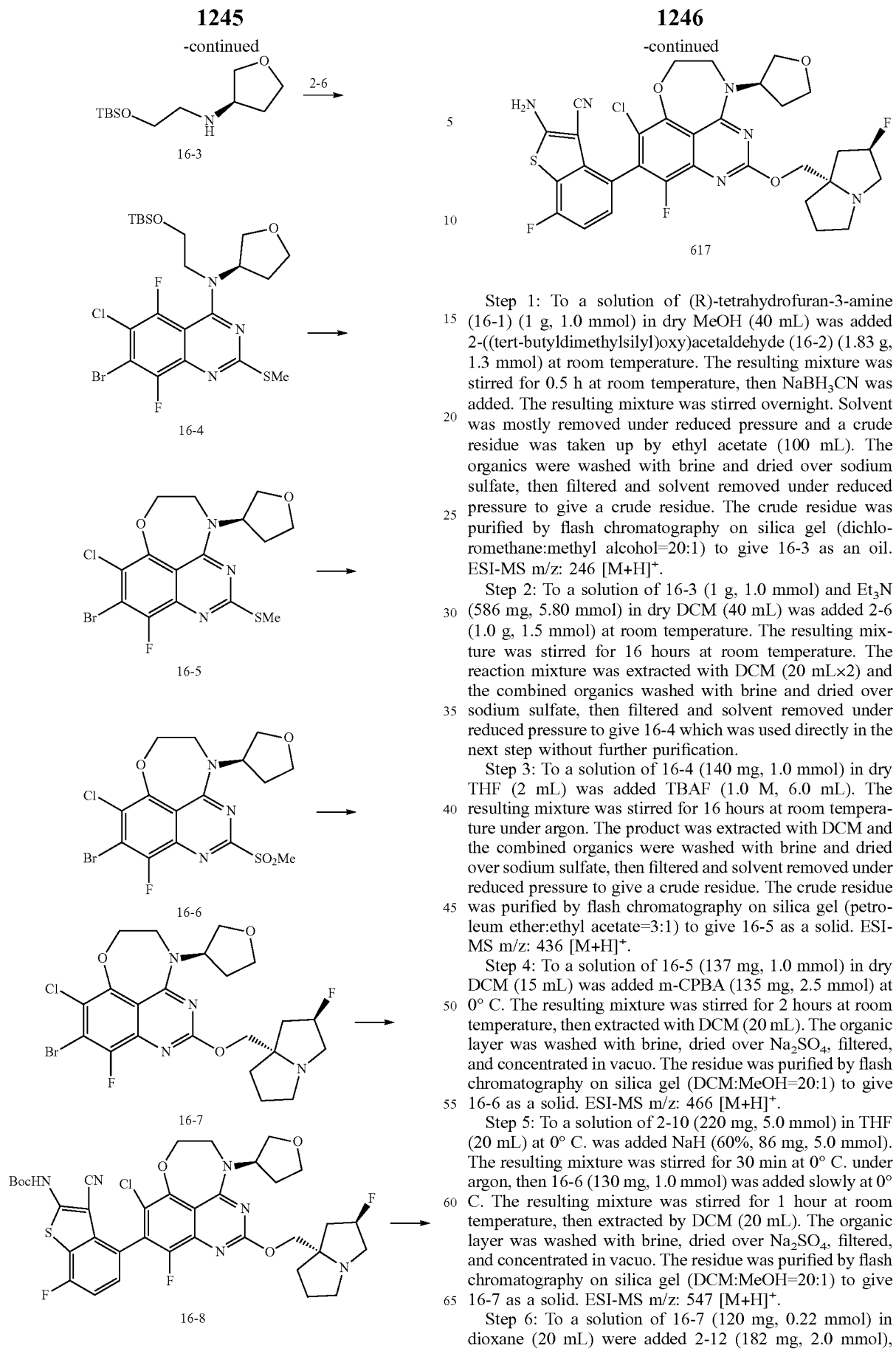

Step 1: To a solution of (R)-tetrahydrofuran-3-amine (16-1) (1 g, 1.0 mmol) in dry MeOH (40 mL) was added 2-((tert-butyldimethylsilyl)oxy)acetaldehyde (16-2) (1.83 g, 1.3 mmol) at room temperature. The resulting mixture was stirred for 0.5 h at room temperature, then NaBH$_3$CN was added. The resulting mixture was stirred overnight. Solvent was mostly removed under reduced pressure and a crude residue was taken up by ethyl acetate (100 mL). The organics were washed with brine and dried over sodium sulfate, then filtered and solvent removed under reduced pressure to give a crude residue. The crude residue was purified by flash chromatography on silica gel (dichloromethane:methyl alcohol=20:1) to give 16-3 as an oil. ESI-MS m/z: 246 [M+H]$^+$.

Step 2: To a solution of 16-3 (1 g, 1.0 mmol) and Et$_3$N (586 mg, 5.80 mmol) in dry DCM (40 mL) was added 2-6 (1.0 g, 1.5 mmol) at room temperature. The resulting mixture was stirred for 16 hours at room temperature. The reaction mixture was extracted with DCM (20 mL×2) and the combined organics washed with brine and dried over sodium sulfate, then filtered and solvent removed under reduced pressure to give 16-4 which was used directly in the next step without further purification.

Step 3: To a solution of 16-4 (140 mg, 1.0 mmol) in dry THF (2 mL) was added TBAF (1.0 M, 6.0 mL). The resulting mixture was stirred for 16 hours at room temperature under argon. The product was extracted with DCM and the combined organics were washed with brine and dried over sodium sulfate, then filtered and solvent removed under reduced pressure to give a crude residue. The crude residue was purified by flash chromatography on silica gel (petroleum ether:ethyl acetate=3:1) to give 16-5 as a solid. ESI-MS m/z: 436 [M+H]$^+$.

Step 4: To a solution of 16-5 (137 mg, 1.0 mmol) in dry DCM (15 mL) was added m-CPBA (135 mg, 2.5 mmol) at 0° C. The resulting mixture was stirred for 2 hours at room temperature, then extracted with DCM (20 mL). The organic layer was washed with brine, dried over Na$_2$SO$_4$, filtered, and concentrated in vacuo. The residue was purified by flash chromatography on silica gel (DCM:MeOH=20:1) to give 16-6 as a solid. ESI-MS m/z: 466 [M+H]$^+$.

Step 5: To a solution of 2-10 (220 mg, 5.0 mmol) in THF (20 mL) at 0° C. was added NaH (60%, 86 mg, 5.0 mmol). The resulting mixture was stirred for 30 min at 0° C. under argon, then 16-6 (130 mg, 1.0 mmol) was added slowly at 0° C. The resulting mixture was stirred for 1 hour at room temperature, then extracted by DCM (20 mL). The organic layer was washed with brine, dried over Na$_2$SO$_4$, filtered, and concentrated in vacuo. The residue was purified by flash chromatography on silica gel (DCM:MeOH=20:1) to give 16-7 as a solid. ESI-MS m/z: 547 [M+H]$^+$.

Step 6: To a solution of 16-7 (120 mg, 0.22 mmol) in dioxane (20 mL) were added 2-12 (182 mg, 2.0 mmol), K₂CO₃ (182 mg, 6.0 mmol) and Pd(dppf)Cl₂·DCM (36 mg, 0.2 mmol) under argon. The resulting mixture was degassed for 20 min with argon, then heated to 110° C. under argon and stirred for 16 hours. The reaction was cooled to room temperature and ethyl acetate (15 mL) was added. The organic layer was washed with brine, dried over Na₂SO₄, filtered, and concentrated in vacuo. The residue was purified by flash chromatography on silica gel (dichloromethane: methyl alcohol=15:1) to afford 16-8 as a solid. ESI-MS m/z: 757 [M+H]⁺.

Step 7: To a solution of 16-8 (100 mg, 1.0 mmol) in DCM (10 mL) was added TFA (4 mL) slowly at room temperature. The resulting mixture was stirred for an additional 1 hour, then concentrated to remove TFA, affording a residue. The residue was partitioned between saturated NaHCO₃ (5 mL) and dichloromethane (5 mL). The aqueous layer was extracted with dichloromethane (15 mL×2). The combined organics were washed with brine, dried over Na₂SO₄, filtered, and concentrated in vacuo. The residue was purified by prep-TLC (DCM:MeOH=15:1) to afford 617 as a solid. ESI-MS m/z: 657 [M+H]⁺. ¹H NMR (400 MHZ, MeOD): 7.19 (m, 1H), 7.04 (m, 1H), 5.49 (m, 1H), 4.63 (m, 4H), 3.92 (m, 5H), 2.54 (m, 4H), 2.27 (m, 4H), 1.29 (m, 5H).

Example 1q: Synthesis of 2-amino-4-(8-chloro-4-(1-(trans-2-cyanocyclopropane-1-carbonyl)piperidin-4-yl)-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile (839)

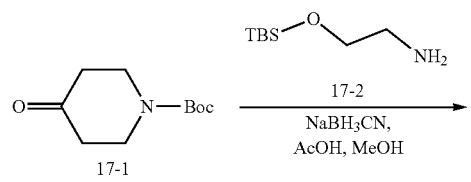

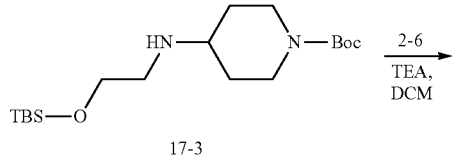

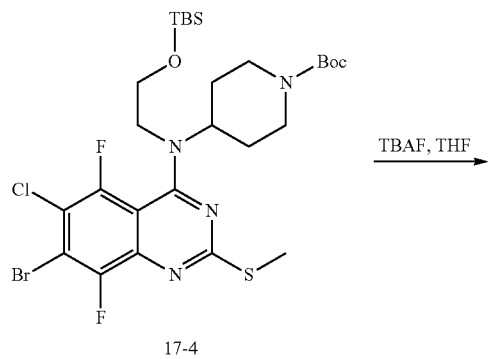

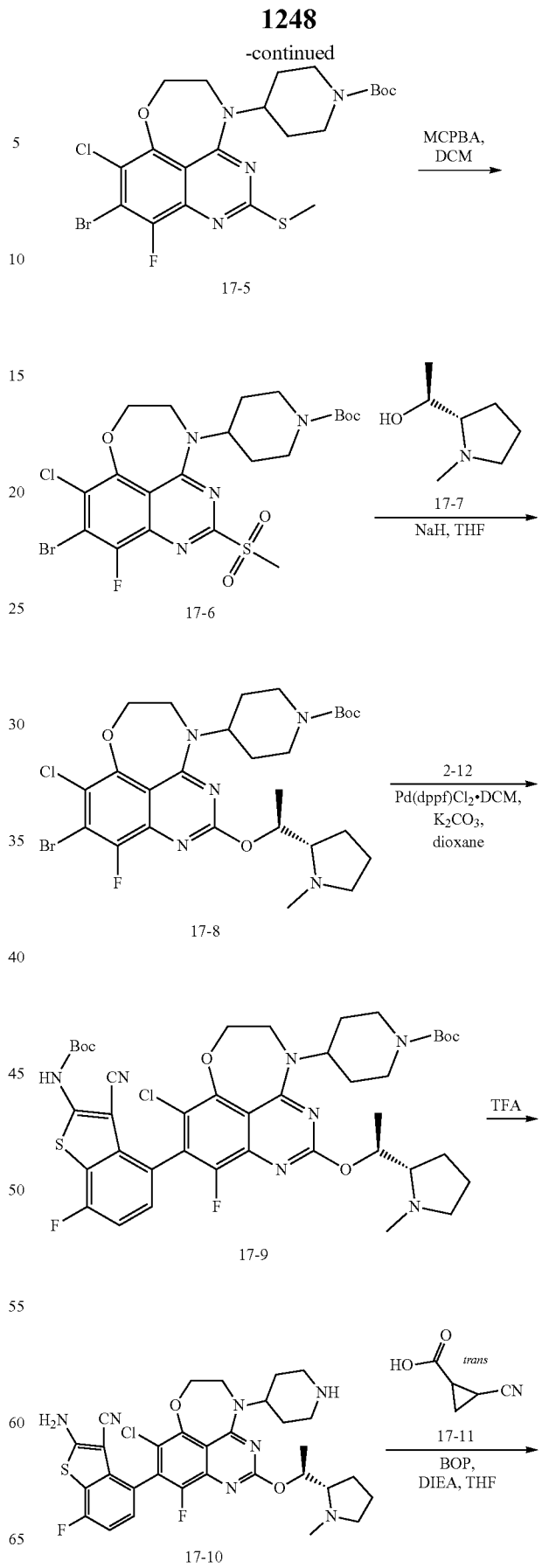

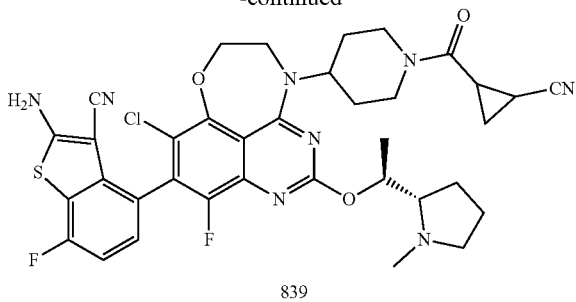

839

Step 1: To a solution of tert-butyl 4-oxopiperidine-1-carboxylate (17-1) (2.26 g, 11.36 mmol) and 2-((tert-butyldimethylsilyl)oxy)ethan-1-amine (17-2) (1 g, 5.68 mmol) in MeOH (20 mL) was added AcOH (1 drop) and the resulting mixture stirred for 1 hour. NaBH$_3$CN (1.79 g, 28.4 mmol) was added and the mixture was stirred for overnight. Solvent was mostly removed under reduced pressure and the residue was taken up in ethyl acetate. The organics were washed with brine, dried over Na$_2$SO$_4$, filtered, and concentrated in vacuo. The residue was purified by flash chromatography on silica gel (petroleum ether:ethyl acetate=3:1) to afford 17-3 as a white solid. ESI-MS m/z: 358 [M+H]$^+$.

Step 2: To a solution of 2-6 (800 mg, 2.22 mmol) in DCM (20 mL) was added TEA (1 mL) at 0° C. 17-3 was added dropwise and the resulting mixture was stirred for 2 hours. The organics were washed with brine, dried over Na$_2$SO$_4$, filtered, and concentrated in vacuo. The residue was purified by flash chromatography on silica gel (petroleum ether:ethyl acetate=10:1) to afford 17-4 as a yellow solid. ESI-MS m/z: 680 [M+H]$^+$.

Step 3: To a solution of 17-4 (400 mg, 0.588 mL) in THF (2.5 mL) was added TBAF (5 mL) slowly. The resulting mixture was stirred for overnight, then diluted with DCM (10 mL). The organic layer was washed with brine, dried over Na$_2$SO$_4$, filtered, and concentrated in vacuo. The residue was purified by flash chromatography on silica gel (petroleum ether:ethyl acetate=3:1) to afford 17-5 as a yellow solid. ESI-MS m/z: 546 [M+H]$^+$.

Step 4: To a solution of 17-5 (260 mg, 0.476 mmol) in DCM (20 mL) cooled to 0° C. was added mCPBA (164 mg, 0.95 mmol) slowly. The resulting mixture was stirred for 1 hour. The organic layer was washed with brine, dried over Na$_2$SO$_4$, filtered, and concentrated in vacuo. The residue was purified by flash chromatography on silica gel (DCM:MeOH=20:1) to afford 17-6 as a white solid. ESI-MS m/z: 578 [M+H]$^+$.

Step 5: To a solution of (S)-1-((S)-1-methylpyrrolidin-2-yl)ethan-1-ol (17-7) (200 mg, 0.346 mmol) in THF (20 mL) cooled to 0° C. was added NaH (69 mg, 1.73 mmol) dropwise. The resulting mixture was stirred for 30 min at 0° C., then 17-6 was added and the resulting mixture was stirred for 10 min at 0° C. The organic layer was washed with brine, dried over Na$_2$SO$_4$, filtered, and concentrated in vacuo. The residue was purified by flash chromatography on silica gel (DCM:MeOH=10:1) to afford 17-8 as a white solid. ESI-MS m/z: 627 [M+H]$^+$.

Step 6: To a solution of 17-8 (200 mg, 0.319 mmol) in dioxane (10 mL) were added 2-12 (257 mg, 0.638 mmol), Pd(dppf)Cl$_2$:DCM (26 mg, 0.0319 mmol), and K2CO$_3$ (101 mg, 0.95 mmol). The resulting mixture was degassed for 20 min with argon, then stirred for overnight at 100° C. under argon. The reaction was cooled to room temperature, then ethyl acetate (20 mL) was added. The organic layer was washed with brine, dried over Na$_2$SO$_4$, filtered, and concentrated in vacuo. The residue was purified by flash chromatography on silica gel (DCM:MeOH=10:1) to afford 17-9 as a white solid. ESI-MS m/z: 839 [M+H]$^+$.

Step 7: To a solution of 17-9 (185 mg, 0.22 mmol) in DCM (20 mL) was added TFA (5 mL) slowly and the resulting mixture stirred for 1 hour. The reaction was partitioned between saturated NaHCO$_3$ (5 mL) and dichloromethane (20 mL). The organics were separated and the aqueous layer was extracted with dichloromethane (20 mL×2). The combined organics were washed with brine, dried over Na$_2$SO$_4$, filtered, and concentrated in vacuo. The residue was purified by flash chromatography on silica gel (DCM:methanol=15:1) to afford 17-10 as a white solid. ESI-MS m/z: 639 [M+H]$^+$.

Step 8: To a solution of 17-10 (20 mg, 0.031 mmol) in THF (10 mL) were added (1S,2R)-2-cyanocyclopropane-1-carboxylic acid (17-11) (6.9 mg, 0.062 mmol) and BOP (27.6 mg, 0.062 mmol). The resulting mixture was stirred for 1 hour, then DIEA (1 mL) was added and the resulting mixture stirred overnight. Ethyl acetate (20 mL) was added, then the organic layer was washed with brine, dried over Na$_2$SO$_4$, filtered, and concentrated in vacuo. The residue was purified by flash chromatography on silica gel (DCM:MeOH=10:1) to afford 839 as a white solid. ESI-MS m/z: 732 [M+H]$^+$. $^1$HNMR (400 MHZ, DMSO-d6) δ:7.24~7.20 (m, 1H), 7.08~7.04 (m, 1H), 5.39~5.33 (m, 1H), 5.24~5.20 (m, 1H), 4.75~4.60 (m, 4H), 3.86~3.65 (m, 4H), 3.40 (m, 1H), 3.33 (s, 3H), 3.32~3.08 (m, 4H), 2.85 (m, 2H), 2.80 (m, 1H), 2.21~1.96 (m, 7H), 1.56 (s, 3H), 1.35~1.31 (m, 2H).

Example 1r: Synthesis of 5-ethynyl-6-fluoro-4-(4-fluoro-2-(((2R,7aS)-2-fluorotetrahydro-1H-pyrrolizin-7a(5H)-yl)methoxy)-10-(tetrahydrofuran-3-yl)-7,8,9,10-tetrahydro-1,3,6,7,10-pentaazacyclohepta[de] naphthalen-5-yl)naphthalen-2-ol (615)

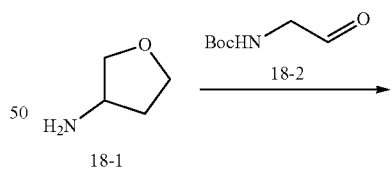

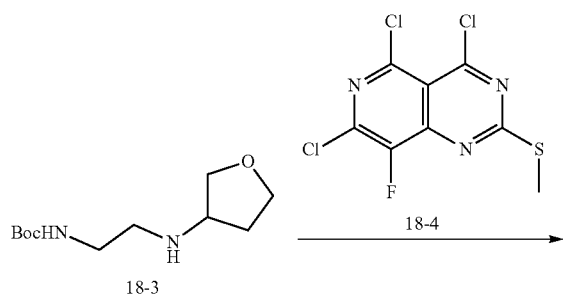

-continued

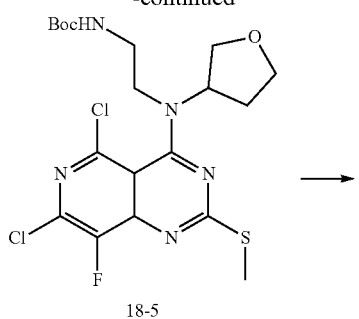

18-5

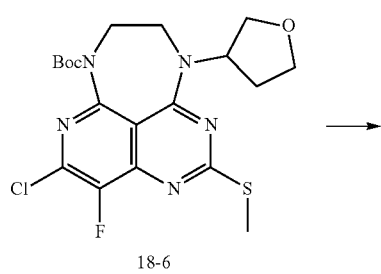

18-6

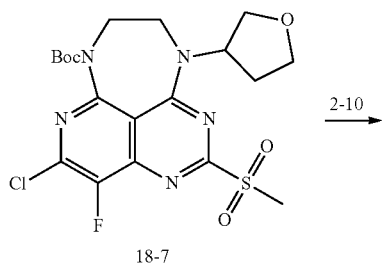

2-10

18-7

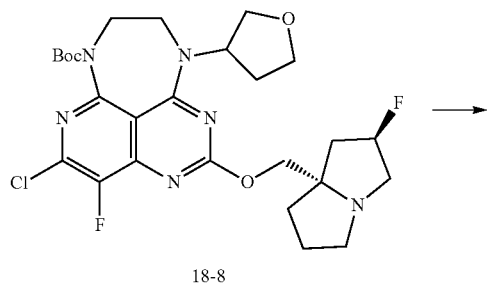

18-8

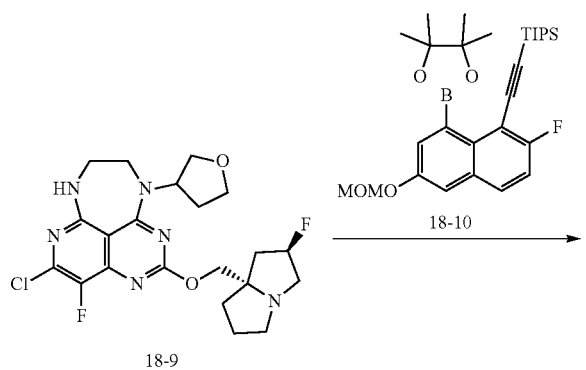

18-9

-continued

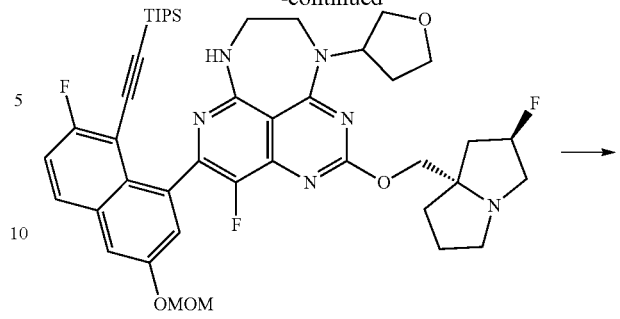

18-11

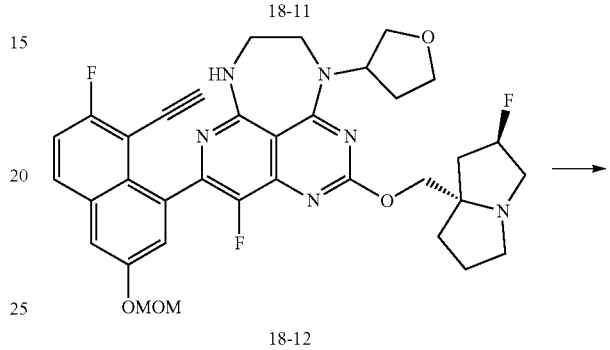

18-12

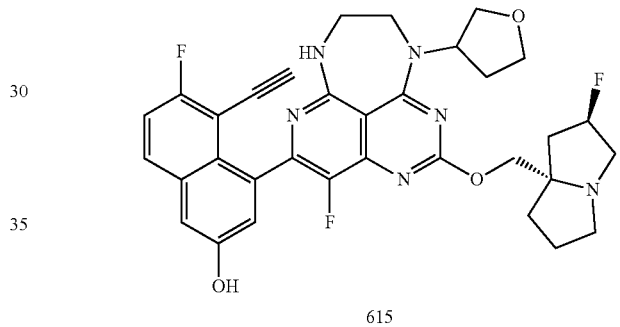

615

Step 1: To a stirred mixture of oxolan-3-amine (18-1) (500 mg, 5.7 mmol) and tert-butyl N-(2-oxoethyl)carbamate (18-2) (1004 mg, 6.3 mmol) in DCM (10 mL) was added $Na_2SO_4$ (1630 mg, 11.4 mmol) at room temperature. After stirring for 3 hours at room temperature, MeOH (2 mL) and $NaBH_4$ (325 mg, 8.6 mmol) were added and the resulting mixture stirred an additional hour. After completion of reaction, it was concentrated under reduced pressure to give crude product which was purified by column chromatography on silica gel (Combiflash) (MeOH/DCM=1:10) to afford 18-3 as a yellow oil. ESI-MS m/z: 231 [M+H]$^+$.

Step 2: To a stirred mixture of 18-3 (270 mg, 1.2 mmol) and 4,5,7-trichloro-8-fluoro-2-(methylsulfanyl)pyrido[4,3-d]pyrimidine (18-4) (385 mg, 1.3 mmol) in DCM (10 mL) was added triethyl amine (237 mg, 2.4 mmol) at room temperature and the resulting mixture was stirred for 3 hour. The reaction mixture was concentrated under reduced pressure to give a crude residue which was purified by column chromatography (ethyl acetate:petroleum ether=1:99 to 1:4) to afford 18-5 as a yellow solid. ESI-MS m/z: 492 [M+H]$^+$.

Step 3: To a stirred solution of 18-5 (460 mg, 0.9 mmol) in anhydrous THF (15 mL) was added NaH (74 mg, 1.8 mmol, 60%) and the resulting mixture stirred 6 hours at 40° C. After completion of the reaction, the reaction mixture was quenched with saturated $NH_4Cl$ (10 mL). The organic layer was separated and the aqueous layer extracted with ethyl acetate (2×50 mL). The combined organics were washed with brine, dried over Na$_2$SO$_4$, filtered, and concentrated in vacuo. The residue was purified by column chromatography on silica gel (Combiflash) (ethyl acetate/petroleum ether=1:6) to afford 18-6 as a yellow solid. ESI-MS m/z: 456 [M+H]$^+$.

Step 4: To a stirred solution of 18-6 (350 mg, 0.76 mmol) in anhydrous DCM (20 mL) was added m-CPBA (397.4 mg, 2.3 mmol) at −10° C. and the mixture was stirred for 4 hours at 0° C. The reaction mixture was quenched by saturated NaHSO$_3$ (10 mL) and the product extracted with ethyl acetate (3×40 mL). The combined organic phase was washed with brine (10 mL), dried over anhydrous sodium sulfate and concentrated under reduced pressure to afford 18-7 (310 mg, crude) as a yellow solid which was used directly in the next step without further purification. ESI-MS m/z: 488 [M+H]$^+$.

Step 5: To a stirred solution of 18-7 (270 mg, 0.553 mmol) and 2-10 (132 mg, 0.83 mmol) in anhydrous THF (15 mL) was added LDA (540 µL, 1.1 mmol) at −40° C. The reaction mixture was stirred at −10° C. for 3 hours, then quenched by addition of NH$_4$Cl (10 mL). The product was extracted with ethyl acetate (3×30 mL). The combined organic layer was washed with brine, dried over Na$_2$SO$_4$, filtered, and concentrated in vacuo. The residue was purified by reverse flash chromatography (column, C$_{18}$; mobile phase, MeCN in water (0.05% NH$_4$HCO$_3$), 5% to 85% gradient in 18 min) to afford 18-8 as a yellow solid. ESI-MS m/z: 567 [M+H]$^+$.

Step 6: A solution of 18-8 (175 mg, 0.309 mmol) in HCl solution (4 M in 1,4-dioxane, 5 mL) was stirred for 1 hour at room temperature. The reaction mixture was concentrated under reduced pressure to afford 18-9 as a yellow solid which was used directly in the next step without further purification. ESI-MS m/z: 467 [M+H]$^+$.

Step 7: To a stirred solution of 18-9 (150 mg, 0.321 mmol) and {2-[2-fluoro-6-(methoxymethoxy)-8-(4,4,5,5-tetramethyl-1,3,2-dioxaborolan-2-yl) naphthalen-1-yl]ethynyl} triisopropylsilane (18-10) (246 mg, 0.482 mmol, 1.5 equiv) in dioxane (6 mL) and H$_2$O (2 mL) was added K$_3$PO$_4$ (204 mg, 0.963 mmol) followed by catalytic amount of bis(adamantan-1-yl)(butyl)phosphane; {2'-amino-[1,1'-biphenyl]-2-yl}palladio methanesulfonate (46 mg, 0.064 mmol) at room temperature. The reaction mixture was stirred at 80° C. for 4 hours, then cooled to room temperature and quenched by addition of water (10 mL). The organics were separated and the aqueous layer was extracted with ethyl acetate (3×30 mL). The combined organic phase was washed with brine (10 mL), dried over anhydrous sodium sulfate, and concentrated under reduced pressure to give a crude residue, which was purified by reverse flash chromatography (column, C$_{18}$; mobile phase, MeCN in water (0.05% TFA, 5% to 45% gradient in 16 min) to afford 18-11 as a yellow solid. ESI-MS m/z: 817 [M+H]$^+$.

Step 8: To a solution of 18-11 (60 mg, 0.073 mmol) in DMF (2 mL) was added CsF (111 mg, 0.730 mmol). The mixture was stirred for 1 hour at room temperature, then quenched by addition of water (30 mL). The product was extracted with ethyl acetate (3×30 mL). The combined organic phase was washed with brine (20 mL), dried over anhydrous sodium sulfate and concentrated under reduced pressure to afford 18-12 as a yellow solid which was used directly in the next step without further purification. ESI-MS m/z: 661 [M+H]$^+$.

Step 9: A mixture of 18-12 (55 mg, 0.083 mmol, 1 equiv) and HCl (gas) in 1,4-dioxane (2 mL, 65.8 mmol) in ACN (2 mL) was stirred for 1 hour at room temperature under air atmosphere. The resulting mixture was concentrated under reduced pressure. The residue was dissolved in ethyl acetate (5 mL), then treated with NH$_3$·H$_2$O to adjust to pH 8. The resulting mixture was extracted with ethyl acetate (3×20 mL). The combined organic layers were washed with water (10 mL) and dried over anhydrous Na$_2$SO$_4$, then concentrated under reduced pressure to give the crude product. The crude product was purified by prep-HPLC with the following conditions (Column:Kinetex EVO prep C$_{18, 30*150, 5}$ um; Mobile Phase A: water (10 mmol/L NH$_4$HCO$_3$), Mobile Phase B: ACN; Flow rate: 60 mL/min) to afford 615 as a yellow solid. ESI-MS m/z: 616 [M+H]$^+$. $^1$H NMR (400 MHZ, DMSO-d6) δ 10.02 (s, 1H), 7.91 (dd, J=9.2, 5.9 Hz, 1H), 7.63-7.57 (m, 1H), 7.42 (t, J=9.0 Hz, 1H), 7.31 (d, J=2.6 Hz, 1H), 7.10 (t, J=2.3 Hz, 1H), 5.84-5.73 (m, 1H), 5.29 (d, J=54.4 Hz, 1H), 4.16-4.06 (m, 2H), 4.06-3.94 (m, 2H), 3.86-3.69 (m, 3H), 3.69-3.61 (m, 1H), 3.60-3.36 (m, 3H), 3.18-2.98 (m, 3H), 2.87-2.81 (m, 1H), 2.40-2.25 (m, 1H), 2.20-2.11 (m, 1H), 2.08-1.98 (m, 2H), 1.98-1.68 (m, 4H).

Example 1s: Synthesis of 5-ethynyl-6-fluoro-4-(4-fluoro-2-(((2R,7aS)-2-fluorotetrahydro-1H-pyrrolizin-7a(5H)-yl)methoxy)-10-phenyl-9,10-dihydro-8H-7-oxa-1,3,6,10-tetraazacyclohepta[de]naphthalen-5-yl)naphthalen-2-ol (948)

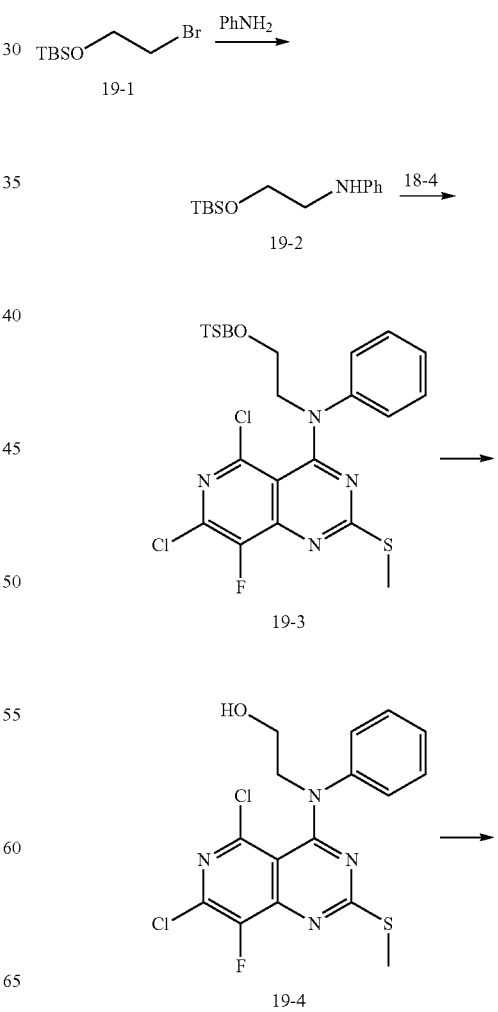

-continued

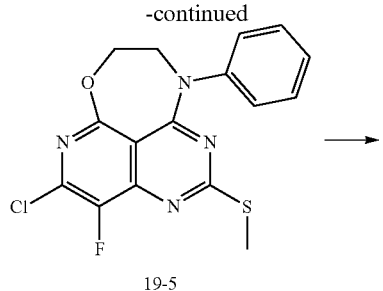

19-5

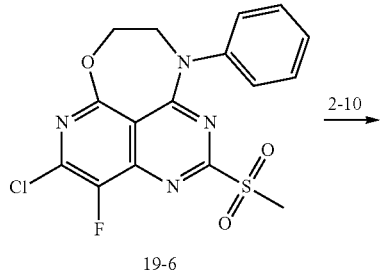

19-6

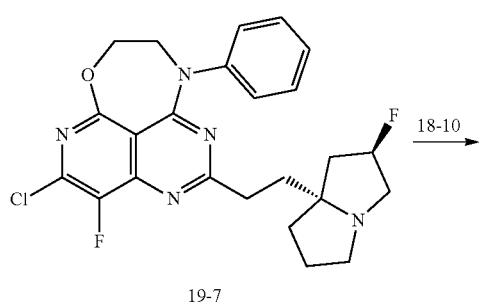

19-7

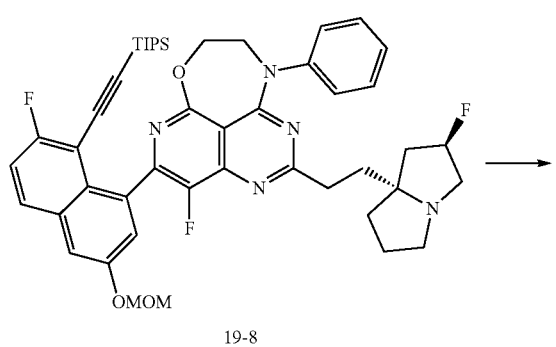

19-8

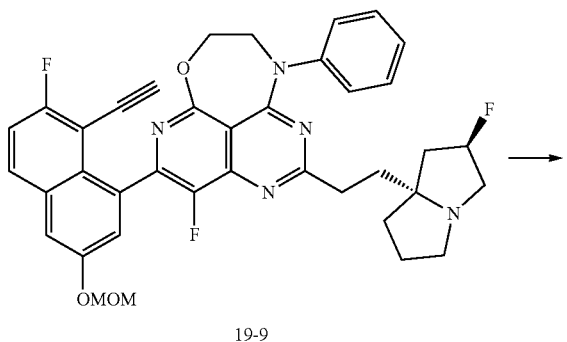

19-9

-continued

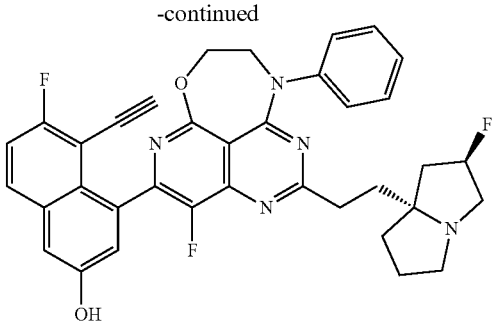

948

Step 1: A solution of (2-bromoethoxy) (tert-butyl) dimethylsilane (19-1) (500 mg, 2.09 mmol), $K_2CO_3$ (1444 mg, 10.45 mmol) and aniline (194 mg, 2.09 mmol) in ACN (5 mL) was stirred for 3 hours at 80° C. under nitrogen atmosphere. The resulting mixture was cooled to room temperature and filtered. The filter cake was washed with ACN (2×20 mL) and the filtrate was concentrated under reduced pressure to give a residue. The residue was purified by silica gel column chromatography, eluting with petroleum ether/ethyl acetate (10:1) to afford 19-2 as a light yellow oil. ESI-MS m/z: 252 [M+H]⁺.

Step 2: A solution of 19-2 (160 mg, 0.64 mmol), DIEA (328 mg, 2.54 mmol) and 18-4 (189 mg, 0.64 mmol) in DCM (4 mL) was stirred for 3 hours at room temperature under nitrogen atmosphere. The reaction was quenched by the addition of water (50 mL) at room temperature. The resulting mixture was extracted with ethyl acetate (3×50 mL). The combined organic layers were washed with brine, dried over $Na_2SO_4$, filtered, and concentrated in vacuo. The residue was purified by silica gel column chromatography (petroleum ether:ethyl acetate=10:1) to afford 19-3 as a yellow solid. ESI-MS m/z: 513 [M+H]⁺.

Step 3: A solution of 19-3 (410 mg, 0.8 mmol) and TBAF (521 mg, 1.99 mmol) in THF (16 mL) was stirred for 1 hour at 40° C. under nitrogen atmosphere. The reaction mixture was cooled to room temperature and quenched by the addition of water (100 mL). The resulting mixture was extracted with ethyl acetate (3×100 mL). The combined organic layers were washed with brine, dried over $Na_2SO_4$, filtered, and concentrated in vacuo. The residue was purified by silica gel column chromatography (petroleum ether:ethyl acetate=1:1) to afford 19-4 as a yellow solid. ESI-MS m/z: 399 [M+H]⁺.

Step 4: A solution of 19-4 (230 mg, 0.58 mmol) and CsF (350 mg, 2.3 mmol) in DMF (10 mL) was stirred for 2 hours at 80° C. under nitrogen atmosphere. The reaction mixture was cooled to room temperature and quenched by the addition of water (50 mL). The resulting mixture was extracted with ethyl acetate (3×50 mL). The combined organic layers were washed with brine, dried over $Na_2SO_4$, filtered, and concentrated in vacuo. The residue was purified by silica gel column chromatography (petroleum ether:ethyl acetate=1:1) to afford 19-5 as a white solid. ESI-MS m/z: 363 [M+H]⁺.

Step 5: To a stirred solution of 19-5 (140 mg, 0.39 mmol) in DCM (4 mL) was added m-CPBA (199 mg, 1.16 mmol) in portions at −10° C. under nitrogen atmosphere. The resulting mixture was stirred for 2 hours at 0° C., then quenched by the addition of $NaHSO_3$ (5 mL) at room temperature. The mixture was treated with saturated $NaHCO_3$(aq.) to adjust to pH 9. The resulting mixture was extracted with ethyl acetate (3×50 mL). The combined organic layers were washed with brine (1×50 mL), dried over anhydrous Na$_2$SO$_4$, filtered, and the filtrate concentrated under reduced pressure to afford 19-6 as a yellow solid. ESI-MS m/z: 395 [M+H]$^+$.

Step 6: To a stirred solution of 19-6 (160 mg, 0.41 mmol) and 2-10 (77.4 mg, 0.49 mmol) in toluene (4 mL) was added t-BuONa (116.8 mg, 1.22 mmol) in portions at 0° C. under nitrogen atmosphere and the resulting mixture stirred at the same temperature for an additional hour. The reaction was then quenched by the addition of sat. NH$_4$Cl (aq.) (5 mL) at room temperature. The resulting mixture was extracted with ethyl acetate (3×50 mL). The combined organic layers were washed with brine, dried over Na$_2$SO$_4$, filtered, and concentrated in vacuo. The residue was purified by silica gel column chromatography (petroleum ether:ethyl acetate=1:1) to afford 19-7 as a white solid. ESI-MS m/z: 474 [M+H]$^+$.

Step 7: A solution of 19-7 (140 mg, 0.29 mmol), 18-10 (227 mg, 0.44 mmol), K$_3$PO$_4$ (188 mg, 0.88 mmol) and bis(adamantan-1-yl)(butyl)phosphane; {2'-amino-[1,1'-biphenyl]-2-yl} palladio methanesulfonate (43 mg, 0.06 mmol) in dioxane (2 mL) and water (0.5 mL) was stirred for 4 hours at 80° C. under nitrogen atmosphere. The reaction mixture was cooled to room temperature and quenched by the addition of water (50 mL) at room temperature. The resulting mixture was extracted with ethyl acetate (3×50 mL). The combined organic layers were washed with brine, dried over Na$_2$SO$_4$, filtered, and concentrated in vacuo. The residue was purified by reversed-phase flash chromatography (column, C$_{18}$; mobile phase, MeCN in water (0.1% NH$_3$·H$_2$O), 10% to 50% gradient in 30 min) to afford 19-8 as a yellow solid. ESI-MS m/z: 824 [M+H]$^+$.

Step 8: A solution of 19-8 (130 mg, 0.16 mmol) and CsF (239 mg, 1.58 mmol) in DMF (3 mL) was stirred for 20 min at room temperature under nitrogen atmosphere. The reaction was quenched by addition of water (50 mL) at room temperature. The resulting mixture was extracted with ethyl acetate (3×50 mL). The combined organic layers were washed with brine (1×50 mL), dried over anhydrous Na$_2$SO$_4$, filtered, and the filtrate concentrated under reduced pressure to afford 19-9 as a yellow oil which was used directly in the next step without further purification. ESI-MS m/z: 668 [M+H]$^+$.

Step 9: A solution of 19-9 (170 mg, 0.26 mmol) and HCl (gas) in 1,4-dioxane (1 mL) in ACN (1 mL) was stirred for 30 min at room temperature under nitrogen atmosphere. The mixture was neutralized to pH~7 by addition of NH$_3$·H$_2$O solution. The resulting mixture was extracted with ethyl acetate (3×50 mL). The combined organic layers were washed with brine, dried over Na$_2$SO$_4$, filtered, and concentrated in vacuo. The residue was purified by prep-HPLC with the following conditions (Column:Kinetex EVO prep C$_{18, 30}$×150, 5 um; Mobile Phase A: water (10 mmol/L NH$_4$HCO$_3$), Mobile Phase B: ACN) to afford 948 as a white solid. ESI-MS m/z: 624 [M+H]$^+$. $^1$H NMR (400 MHZ, DMSO-d6) δ 10.16 (s, 1H), 7.97 (dd, J=9.2, 5.9 Hz, 1H), 7.57-7.49 (m, 2H), 7.47 (t, J=9.0 Hz, 1H), 7.45-7.34 (m, 4H), 7.17 (d, J=2.5 Hz, 1H), 5.08 (s, 1H), 4.73 (s, 2H), 4.28-4.16 (m, 2H), 4.14 (d, J=1.0 Hz, 1H), 3.76 (s, 2H), 3.01-2.88 (m, 3H), 2.82 (ddd, J=13.6, 7.3, 3.0 Hz, 1H), 1.97-1.89 (m, 1H), 1.89-1.70 (m, 3H), 1.59 (dd, J=19.7, 8.0 Hz, 2H).

Example 1t: Synthesis of 2-amino-4-(8-chloro-10-fluoro-2-(((2R,7aS)-2-fluorotetrahydro-1H-pyrrolizin-7a(5H)-yl)methoxy)-6-(hydroxymethyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (681)

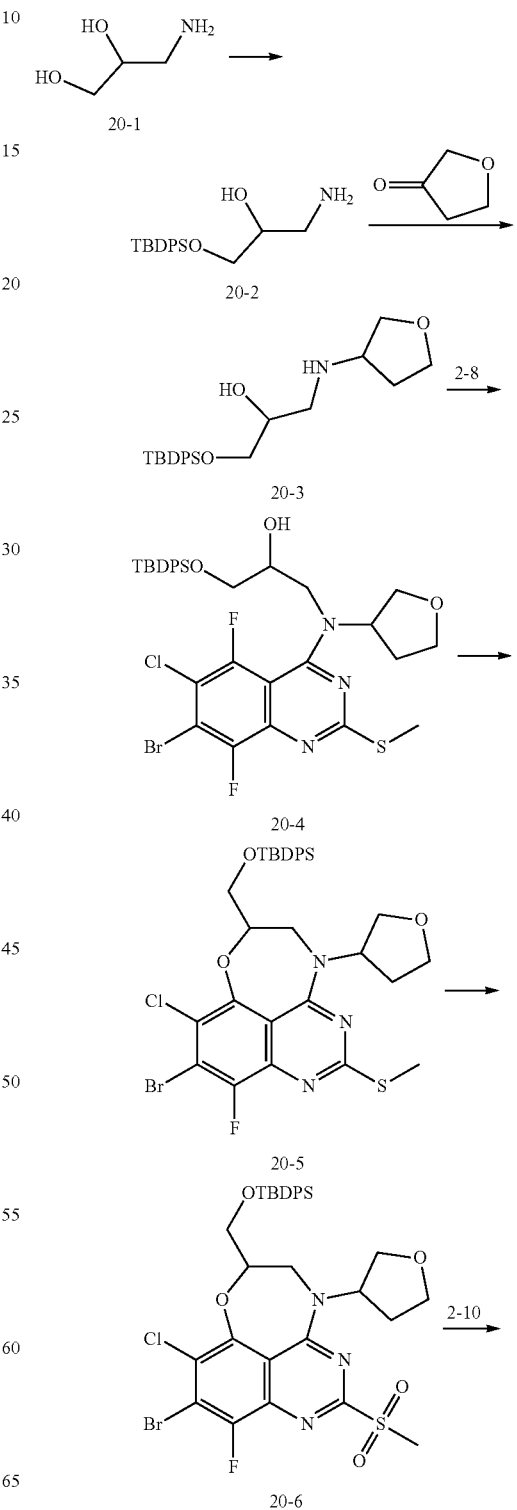

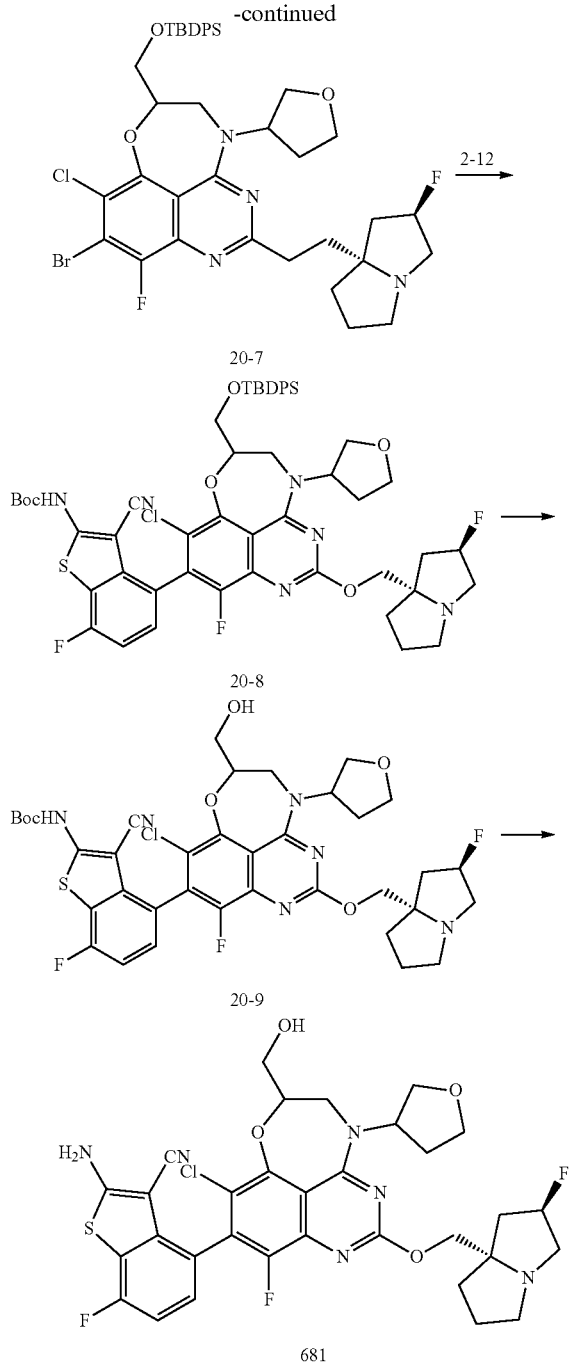

Step 1: A solution of 3-aminopropane-1,2-diol (20-1) (5.0 g, 54.8 mmol), TBDPSCl (16.6 g, 60.3 mmol) and imidazole (7.47 g, 109.7 mmol) in DCM (100 mL) was stirred for 2 hours at room temperature under nitrogen atmosphere. The reaction was quenched by addition of water (200 mL). The resulting mixture was extracted with DCM (3×200 mL). The combined organic layers were washed with brine, dried over $Na_2SO_4$, filtered, and concentrated in vacuo. The residue was purified by silica gel column chromatography, eluting with $CH_2Cl_2$ (0.1% TEA)/MeOH (13:1) to afford 20-2 as a white oil. ESI-MS m/z: 330 [M+H]$^+$.

Step 2: A solution of 20-2 (3.2 g, 9.71 mmol) in DCM (65 mL) was stirred with dihydrofuran-3-one (0.84 g, 9.71 mmol) for 10 min at room temperature under nitrogen atmosphere followed by the addition of STAB (4.12 g, 19.42 mmol) in portions at 0° C. The reaction mixture was stirred for an additional hour from 0° C. to room temperature. The reaction was then quenched with water (150 mL). The mixture was treated with $NaHCO_3$(eq.) to adjust the pH~9, then extracted with DCM (3×200 mL). The combined organic layers were washed with brine, dried over $Na_2SO_4$, filtered, and concentrated in vacuo. The residue was purified by silica gel column chromatography, eluting with $CH_2Cl_2$ (0.1% TEA)/MeOH (15:1) to afford 20-3 as a white viscous oil. ESI-MS m/z: 400 [M+H]$^+$.

Step 3: A solution of 20-3 (400 mg, 1.00 mmol), 2-6 (360 mg, 1.00 mmol) and DIEA (517 mg, 4.00 mmol) in 2-methylpropan-2-ol (10 mL) was stirred for 3 hours at 90° C. under nitrogen atmosphere, then cooled to room temperature and the resulting mixture diluted with water (80 mL). It was extracted with ethyl acetate (3×80 mL). The combined organic layers were washed with brine, dried over $Na_2SO_4$, filtered, and concentrated in vacuo. The residue was purified by silica gel column chromatography, eluting with $CH_2Cl_2$/MeOH (10:1) to afford 20-4 as a yellow oil. ESI-MS m/z: 722 [M+H]$^+$.

Step 4: A solution of 20-4 (130 mg, 0.18 mmol) and NaH (14 mg, 0.36 mmol, 60%) in THF (5.0 mL) was stirred for 1 hour at room temperature under nitrogen atmosphere. The reaction mixture was quenched by water and extracted with DCM (3×50 mL). The combined organic layers were washed with brine, dried over $Na_2SO_4$, filtered, and concentrated in vacuo. The residue was purified by reversed-phase flash chromatography (column, $C_{18}$; mobile phase, MeCN in water (10 mmol/L $NH_4HCO_3$), 30% to 80% gradient in 15 min) to afford 20-5 as a white solid. ESI-MS m/z: 702 [M+H]$^+$.

Step 5: To a solution of 20-5 (60 mg, 0.08 mmol) in DCM (6 mL) was added m-CPBA (44 mg, 0.25 mmol) under nitrogen, in portions at −10° C. The resulting mixture was stirred for 1 hour at −5° C. under nitrogen atmosphere. The reaction was quenched by the addition of $NaHSO_3$ (5 mL) at 0° C. The residue was basified to pH 8 with saturated $NaHCO_3$(aq.), then extracted with ethyl acetate (3×25 mL). The combined organic layers were washed with brine (1×30 mL), dried over anhydrous $Na_2SO_4$, filtered, and the filtrate concentrated under reduced pressure to afford 20-6 as a yellow solid which was used directly in the next step without further purification. ESI-MS m/z: 734 [M+H]$^+$.

Step 6: A solution of 20-6 (60 mg, 0.08 mmol) and 2-10 (19.4 mg, 0.12 mmol) in t-BuOH (3 mL) was stirred at room temperature under nitrogen atmosphere followed by the addition of t-BuONa (23.5 mg, 0.24 mmol) in portions at −5° C. The resulting mixture was stirred for 1 hour at 0° C. under nitrogen atmosphere. The reaction was quenched by the addition of sat. $NH_4Cl$ (aq.) (5 mL) at 0° C., then extracted with ethyl acetate (3×20 mL). The combined organic layers were washed with brine, dried over $Na_2SO_4$, filtered, and concentrated in vacuo. The residue was purified by reversed-phase flash chromatography (column, $C_{18}$; mobile phase, MeCN in water (10 mmol/L $NH_4HCO_3$)) to afford 20-7 as a yellow solid. ESI-MS m/z: 813 [M+H]$^+$.

Step 7: To a reaction tube charged with a magnetic bar was added 20-7 (20 mg, 0.02 mmol), 2-12 (14.9 mg, 0.04 mmol, 1.50 equiv), dichloropalladium; {2-[2-(diphenylphosphanyl)phenoxy]phenyl} diphenylphosphane (17.6 mg, 0.02 mmol), and $Cs_2CO_3$ (24.0 mg, 0.07 mmol). The reaction system was evacuated and refilled with $N_2$ three times. Then, anhydrous toluene (1 mL) was added via syringe. The mixture was evacuated and backfilled with $N_2$ three times before stirring at 100° C. for 2.5 hours. The reaction mixture was cooled to room temperature and concentrated under vacuum to give a residue. The residue was purified by prep-TLC (CH$_2$Cl$_2$/MeOH 10:1) to afford 20-8 as a yellow solid. ESI-MS m/z: 1025 [M+H]$^+$.

Step 8: A solution of 20-8 (17 mg, 0.01 mmol) and caesium fluoride (29.6 mg, 0.17 mmol) in DMF (1 mL) was stirred for 1 hour at room temperature. The resulting mixture was diluted with water (10 mL), then extracted with ethyl acetate (2×20 mL). The combined organic layers were washed with brine, dried over Na$_2$SO$_4$, filtered, and concentrated in vacuo. The residue was purified by prep-TLC (CH$_2$Cl$_2$/MeOH 10:1) to afford 20-9 as a yellow solid. ESI-MS m/z: 787 [M+H]$^+$.

Step 9: A solution of 20-9 (13 mg, 0.02 mmol) and HCl (gas) in 1,4-dioxane (0.3 mL, 4 N) in ACN (0.6 mL) was stirred for 2 hours at room temperature. The solvent was removed under reduced pressure to give a residue which was taken up in DCM and washed with sodium bicarbonate. The organics was dried over sodium sulfate, then filtered and solvent removed under reduced pressure to give a residue. The residue was purified by prep-HPLC (Column:Atlantis Prep T3 OBD Column, 19*150 mm 5 um; Mobile Phase A: Water (0.05% FA), Mobile Phase B: ACN) to afford 681 as a white solid. ESI-MS m/z: 686.75 [M+H]$^+$. $^1$H NMR (400 MHZ, DMSO-d$_6$) δ 8.18-8.03 (m, 2H), 7.27-7.07 (m, 2H), 5.44 (s, 1H), 5.28 (d, J=54.2 Hz, 1H), 5.14 (s, 1H), 4.68 (s, 1H), 4.16-4.07 (m, 1H), 4.02 (m, 2H), 3.95-3.79 (m, 4H), 3.79 (s, 1H), 3.60 (td, J=17.0, 8.1 Hz, 2H), 3.09 (d, J=10.5 Hz, 2H), 3.02 (s, 1H), 2.82 (s, 1H), 2.37 (d, J=29.5 Hz, 2H), 2.12 (t, J=7.3 Hz, 1H), 2.05 (m, 2H), 2.01 (s, 1H), 1.81-1.71 (m, 2H).

Example 1u: Synthesis of 2-amino-4-(8-chloro-10-fluoro-2-(((2R,7aS)-2-fluorotetrahydro-1H-pyrrolizin-7a(5H)-yl)methoxy)-4-isopropyl-5,6-dihydro-4H-[1,4]oxazepino[5,6,7-de]quinazolin-9-yl)-7-fluorobenzo[b]thiophene-3-carbonitrile (1025)

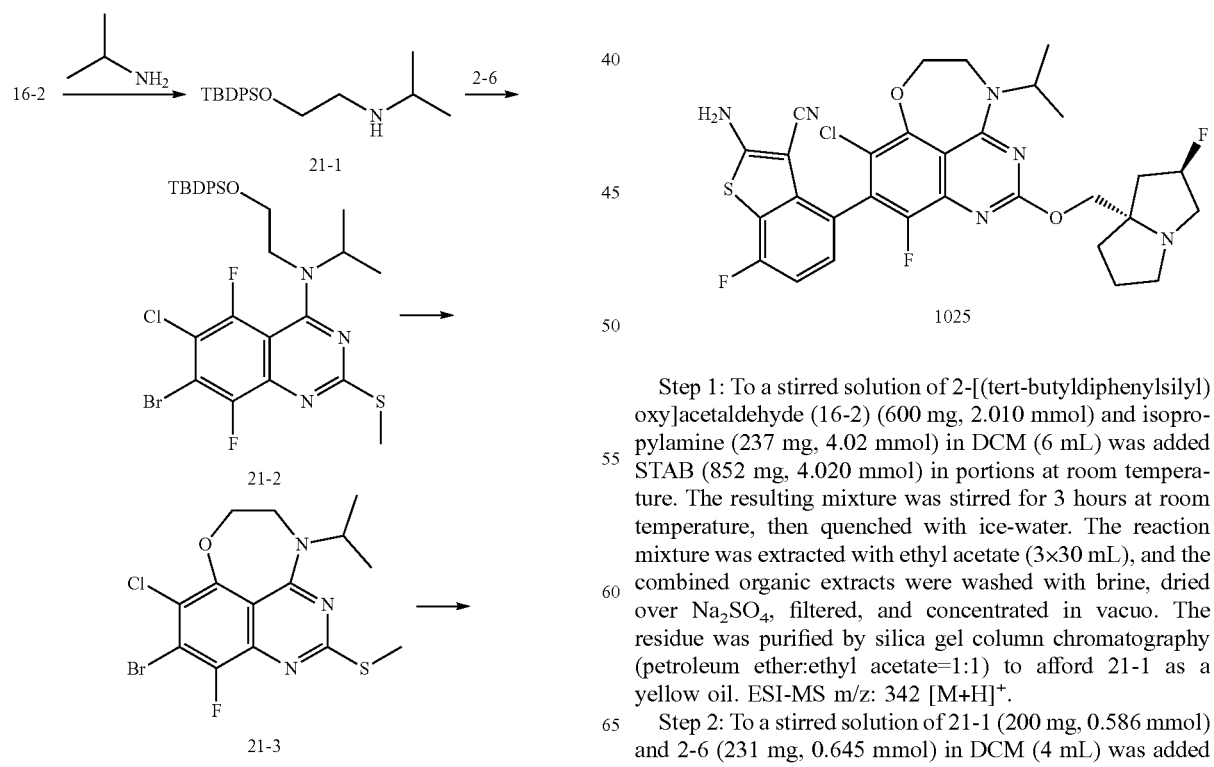

Step 1: To a stirred solution of 2-[(tert-butyldiphenylsilyl)oxy]acetaldehyde (16-2) (600 mg, 2.010 mmol) and isopropylamine (237 mg, 4.02 mmol) in DCM (6 mL) was added STAB (852 mg, 4.020 mmol) in portions at room temperature. The resulting mixture was stirred for 3 hours at room temperature, then quenched with ice-water. The reaction mixture was extracted with ethyl acetate (3×30 mL), and the combined organic extracts were washed with brine, dried over Na$_2$SO$_4$, filtered, and concentrated in vacuo. The residue was purified by silica gel column chromatography (petroleum ether:ethyl acetate=1:1) to afford 21-1 as a yellow oil. ESI-MS m/z: 342 [M+H]$^+$.

Step 2: To a stirred solution of 21-1 (200 mg, 0.586 mmol) and 2-6 (231 mg, 0.645 mmol) in DCM (4 mL) was added DIEA (151 mg, 1.172 mmol) at room temperature. The resulting mixture was stirred overnight, then concentrated under reduced pressure to give a residue. The residue was purified by reversed-phase flash chromatography (column, $C_{18}$; mobile phase, MeCN in water (10 mmol/L $NH_4HCO_3$)) to afford 21-2 as a light yellow solid. ESI-MS m/z: 664 $[M+H]^+$.

Step 3: To a stirred solution of 21-2 (300 mg, 0.451 mmol, 1 eq.) in THF (12 mL) was added TBAF (294 mg, 1.127 mmol) at room temperature. The resulting mixture was stirred for 2 hours at 40° C., then diluted with ethyl acetate (50 mL). The organic layer was washed with brine, dried over $Na_2SO_4$, filtered, and concentrated in vacuo. The residue was purified by reverse-phase flash chromatography (column, $C_{18}$; mobile phase, MeCN in water (10 mmol/L $NH_4HCO_3$)) to afford 21-3 as a yellow solid. ESI-MS m/z: 406 $[M+H]^+$.

Step 4: To a stirred solution of 21-3 (140 mg, 0.344 mmol) in DCM (3 mL) was added mCPBA (178 mg, 1.032 mmol, 3 eq) at −10° C. The resulting mixture was stirred for 2 hours at 0° C., then diluted with $CH_2Cl_2$ (30 mL). The resulting mixture was washed with 2×20 mL of $Na_2CO_3$ (aq.), dried over anhydrous sodium sulfate and concentrated under vacuum to give 21-4 as a yellow solid, which was used directly in the next step without further purification. ESI-MS m/z: 438 $[M+H]^+$.

Step 5: To a stirred solution of 21-4 (60 mg, 0.137 mmol) and 2-10 (26.13 mg, 0.164 mmol) in toluene (1.2 mL, 11.278 mmol) was added t-BuONa (39 mg, 0.411 mmol) at 0° C. The resulting mixture was stirred for 1 hour at 0° C., quenched with ice-water, then extracted with ethyl acetate (3×30 mL). The organics were combined, washed with brine, dried over $Na_2SO_4$, filtered, and concentrated in vacuo. The residue was purified by reverse-phase flash chromatography (column, $C_{18}$; mobile phase, MeCN in water (10 mmol/L $NH_4HCO_3$)) to afford 21-5 as a yellow solid. ESI-MS m/z: 517 $[M+H]^+$.

Step 6: To a stirred solution of 21-5 (50 mg, 0.097 mmol) and 2-12 (97 mg, 0.242 mmol) in toluene (5 mL) were added $DPEphosPdCl_2$ (11 mg, 0.015 mmol) and $Cs_2CO_3$ (94 mg, 0.291 mmol) at room temperature. The resulting mixture was purged and degassed with nitrogen three times, then heated to 100° C. and stirred for 2.5 hours under nitrogen atmosphere. The reaction mixture was cooled to room temperature and diluted with ethyl acetate (30 mL). The organics were washed with brine, dried over $Na_2SO_4$, filtered, and concentrated in vacuo. The residue was purified by reverse-phase flash chromatography (column, $C_{18}$; mobile phase, MeCN in water (10 mmol/L $NH_4HCO_3$)) to afford 21-6 as a brown solid. ESI-MS m/z: 729 $[M+H]^+$.

Step 7: To a stirred mixture of 21-6 (30 mg, 0.041 mmol) in DCM (1 mL) was added TFA (0.2 mL) at room temperature. The resulting mixture was stirred for 1 hour at room temperature, then concentrated under vacuum to give a residue. The crude residue was purified by Chiral-Prep-HPLC (19×150 mm 5 um; mobile phase, water (0.05% FA) and ACN (20% ACN up to 50% in 10 min) to afford 1025 as a white solid. ESI-MS m/z: 629 $[M+H]^+$. $^1$H NMR (400 MHZ, DMSO-$d_6$) δ 8.06 (br, 2H), 7.23-7.20 (m, 1H), 7.15-7.11 (m, 1H), 5.34-5.16 (m, 2H), 4.54-4.43 (m, 2H), 4.38-4.35 (m, 2H), 4.11-4.06 (m, 1H), 4.04-3.99 (m, 1H), 3.77-3.64 (m, 2H), 3.43-3.42 (m, 1H), 3.10-3.08 (m, 1H), 3.02 (s, 1H), 2.83-2.82 (m, 1H), 2.18-2.12 (m, 1H), 2.05-1.99 (m, 4H), 1.85-1.81 (m, 1H), 1.80-1.76 (m, 1H), 1.25 (d, J=6.8 Hz, 6H).

Example 1v: Synthesis of 2-amino-4-(8-chloro-6-cyclopropyl-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (1128)

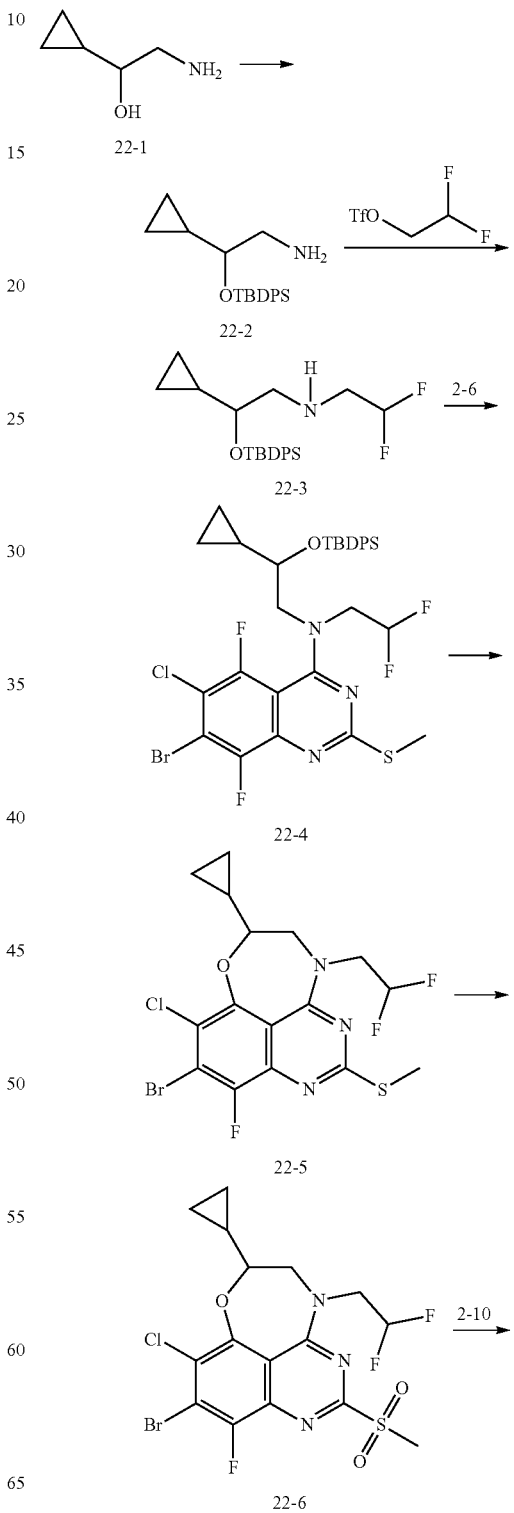

-continued

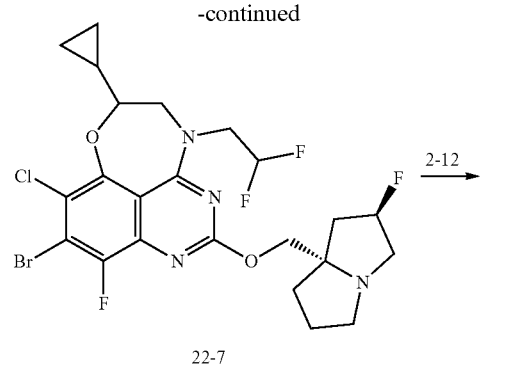

Step 1: To a stirred mixture of 2-amino-1-cyclopropyl-ethanol (22-1) (900 mg, 8.898 mmol) and imidazole (1.82 g, 26.694 mmo) in DCM (18 mL) was added TBDPSCl (2.69 g, 9.788 mmol, 1.10 eq) in portions at 0° C. under nitrogen atmosphere. The resulting mixture was stirred overnight at room temperature. The mixture was diluted with water (10 mL) and extracted with $CH_2Cl_2$ (3×10 mL). The combined organic layers were washed with brine, dried over $Na_2SO_4$, filtered, and concentrated in vacuo. The residue was purified by silica gel column chromatography (ethyl acetate=2:3) to afford 22-2 as a colorless oil. ESI-MS m/z: 340 [M+H]$^+$.

Step 2: A mixture of 22-2 (1.29 g, 3.799 mmol) and 2,2-difluoroethyl trifluoromethanesulfonate (894 mg, 4.179 mmol) in dioxane (12.9 mL, 152.264 mmol) was stirred for 1 hour at room temperature under nitrogen atmosphere. The resulting mixture was diluted with water (20 mL) and extracted with $CH_2Cl_2$ (3×20 mL). The combined organic layers were washed with brine, dried over $Na_2SO_4$, filtered, and concentrated in vacuo. The residue was purified by silica gel column chromatography (petroleum ether:ethyl acetate=19:1) to afford 22-3 as a colorless oil. ESI-MS m/z: 404 [M+H]$^+$.

Step 3: A mixture of 2-6 (405 mg, 1.126 mmol) and DIEA (582 mg, 4.505 mmol) in t-BuOH (9.09 mL, 95.673 mmol) was stirred overnight at 90° C. under nitrogen atmosphere, then cooled to room temperature and the mixture diluted with water (20 mL) and extracted with ethyl acetate (3×20 mL). The combined organic layers were washed with brine, dried over $Na_2SO_4$, filtered, and concentrated in vacuo. The residue was purified by silica gel column chromatography, eluting with petroleum ether:ethyl acetate=9:1 to afford 22-4 as a yellow solid. ESI-MS m/z: 726 [M+H]$^+$.

Step 4: A mixture of 22-4 (550 mg, 0.756 mmol) and CsF (459 mg, 3.024 mmol) in DMF (11.0 mL) was stirred for 2 hours at 80° C. under nitrogen atmosphere, then diluted with water (20 mL) and extracted with ethyl acetate (3×20 mL). The combined organic layers were washed with brine, dried over $Na_2SO_4$, filtered, and concentrated in vacuo. The residue was purified by silica gel column chromatography, eluting with petroleum ether/ethyl acetate (1:19) to afford 22-5 as a white solid. ESI-MS m/z: 468 [M+H]$^+$.

Step 5: A mixture of 22-5 (390 mg, 0.832 mmol) and m-CPBA (506 mg, 2.496 mmol, 85%) in DCM (7.8 mL, 122.687 mmol) was stirred for 2 hour at 0° C. under nitrogen atmosphere. The mixture was treated with $NaHCO_3$(aq.) and extracted with ethyl acetate (3×20 mL). The combined organic layers were washed with NaCl (3×20 mL), dried over anhydrous $Na_2SO_4$, filtered, and the filtrate concentrated under reduced pressure to give 22-6 as a white solid which was used directly in the next step without further purification. ESI-MS m/z: 500 [M+H]$^+$.

Step 6: To a stirred mixture of 22-6 (310 mg, 0.619 mmol) and 2-10 (177 mg, 1.114 mmol) in toluene (6 mL) was added t-BuONa (178 mg, 1.857 mmol) in portions at 0° C. under argon atmosphere. After completion of the reaction, the mixture was diluted with water (20 mL) and extracted with ethyl acetate (3×20 mL). The combined organic layers were washed with brine, dried over $Na_2SO_4$, filtered, and concentrated in vacuo. The residue was purified by silica gel column chromatography, eluting with petroleum ether/ethyl acetate (1/1) to afford 22-7 as a white solid. ESI-MS m/z: 579 [M+H]$^+$.

Step 7: A mixture of 22-7 (130 mg, 0.225 mmol), 2-12 (272 mg, 0.675 mmol), dichloropalladium;{2-[2-(diphenylphosphanyl) phenoxy]phenyl}diphenylphosphane (32 mg, 0.045 mmol) and $Cs_2CO_3$ (659 mg, 2.025 mmol) in toluene (13 mL, 122.229 mmol) was stirred for 2 hours at 110° C. under nitrogen atmosphere, then cooled to room temperature, diluted with water (50 mL) and extracted with ethyl acetate (3×50 mL). The combined organic layers were washed with brine, dried over $Na_2SO_4$, filtered, and concentrated in vacuo. The residue was purified by Prep-TLC (petroleum ether:ethyl acetate=1:1) to afford 22-8 as a yellow solid. ESI-MS m/z: 791 [M+H]$^+$.

Step 8: A mixture of 22-8 (200 mg, 0.253 mmol) in DCM (10 mL) and TFA (2 mL) was stirred for 1 hour at room temperature under nitrogen atmosphere, then treated with $NH_3 \cdot H_2O$ and extracted with ethyl acetate (3×50 mL). The combined organic layers were washed with brine, dried over $Na_2SO_4$, filtered, and concentrated in vacuo. The residue was purified by prep-HPLC (Column: XBridge Shield RP18 OBD Column, 30*150 mm, 5 um; Mobile Phase A: Water (10 mmol/L $NH_4HCO_3$), Mobile Phase B: ACN; Flow rate: 60 mL/min; Gradient: 40% B to 75% B in 10 min, 75% B) to afford 1128 as a white solid. ESI-MS m/z: 691 [M+H]$^+$.
$^1$H NMR (400 MHZ, DMSO-d$_6$) δ 8.08 (s, 2H), 7.23 (ddd, J=11.3, 8.3, 5.2 Hz, 1H), 7.13 (t, J=8.9 Hz, 1H), 6.60- 6.27 (m, 1H), 5.27 (d, J=54.3 Hz, 1H), 4.14-4.06 (m, 2H), 4.05-3.96 (m, 3H), 3.01 (s, 1H), 2.19-2.10 (m, 1H), 2.07-1.96 (m, 2H), 1.87-1.72 (m, 3H), 1.22 (d, J=8.1 Hz, 1H), 0.66-0.44 (m, 4H).

1267

Example 1w: Synthesis of 2-amino-4-(8-chloro-4-(2,2-difluoroethyl)-10-fluoro-2-(((2R,7aS)-2-fluoro-tetrahydro-1H-pyrrolizin-7a(5H)-yl)methoxy)-6-(trifluoromethyl)-5,6-dihydro-4H-[1,4]oxazepino[5,6,7-de]quinazolin-9-yl)-7-fluorobenzo[b]thiophene-3-carbonitrile (1008)

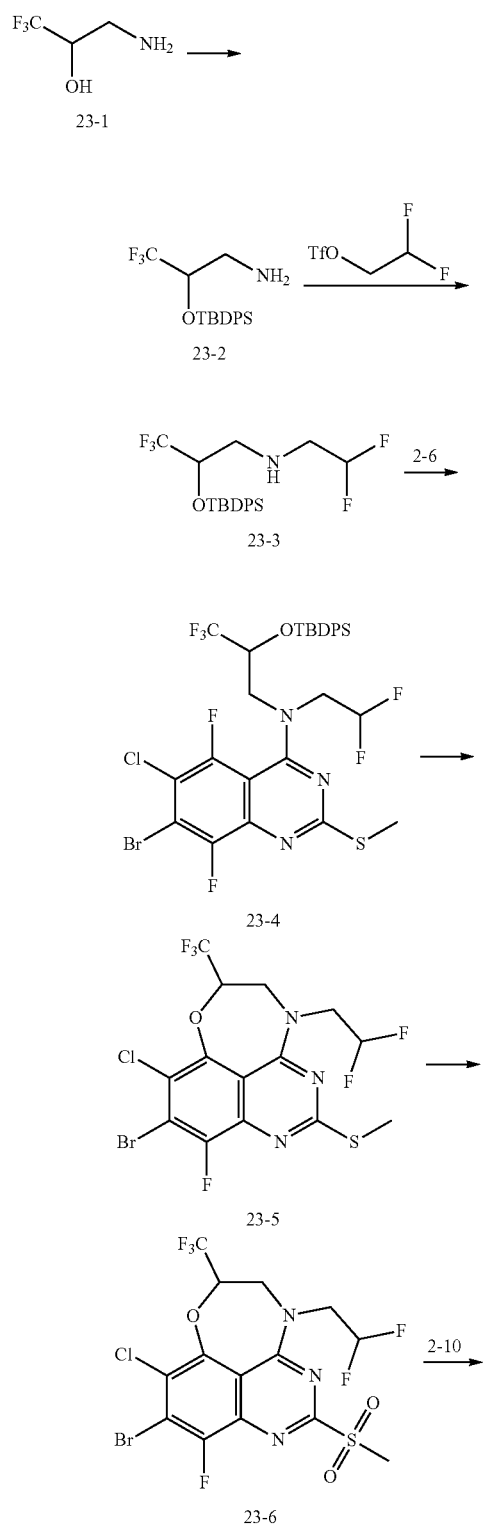

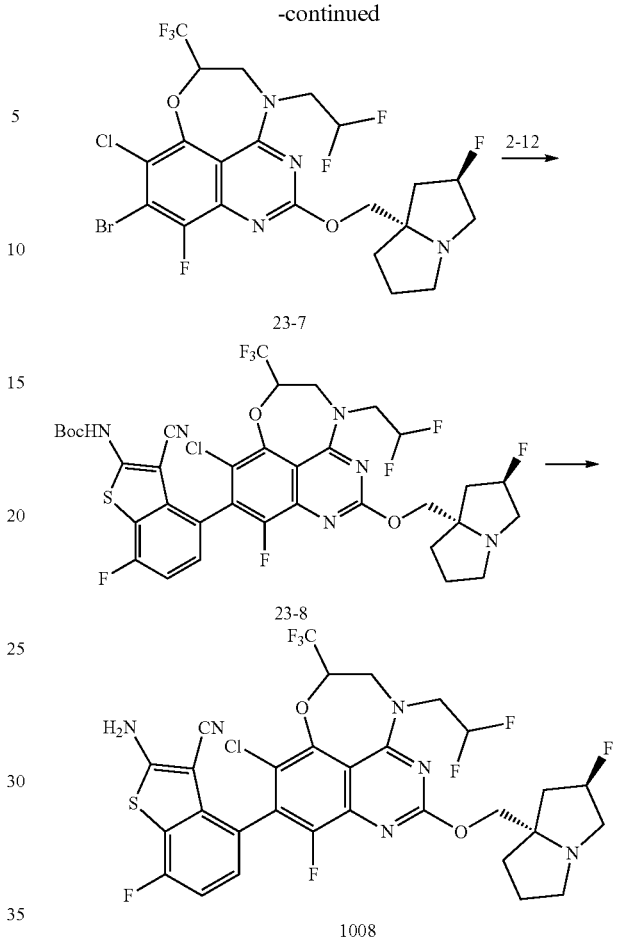

Step 1: A solution of 3-amino-1,1,1-trifluoropropan-2-ol (23-1) (1.00 g, 7.74 mmol) in DCM (20.0 mL) was treated with imidazole (1.05 g, 15.49 mmol) for 5 min at 0° C. under nitrogen atmosphere, then TBDPSCl (2.56 g, 9.29 mmol, 1.20 eq) was added dropwise at 0° C. The resulting mixture was stirred overnight at room temperature under nitrogen atmosphere, then extracted with $CH_2Cl_2$ (3×100 mL). The combined organic layers were washed with brine, dried over $Na_2SO_4$, filtered, and concentrated in vacuo. The residue was purified by silica gel column chromatography (petroleum ether:ethyl acetate=5:1) to afford 23-2 as an off-white oil. ESI-MS m/z: 368 [M+H]$^+$.

Step 2: To an 8 mL reaction vial were added 23-2 (1.90 g, 5.17 mmol), 2,2-difluoroethyl trifluoromethanesulfonate (2.21 g, 10.35 mmol), DIEA (2.00 g, 15.51 mmol) and dioxane (27 mL) at room temperature. The resulting mixture was stirred for 3 hours at room temperature under nitrogen atmosphere, then extracted with ethyl acetate (3×50 mL). The combined organic layers were washed with brine, dried over $Na_2SO_4$, filtered, and concentrated in vacuo. The residue was purified by silica gel column chromatograph (petroleum ether:ethyl acetate=5:1) to afford 23-3 as a colorless oil. ESI-MS m/z: 432 [M+H]$^+$.

Step 3: To a 50 mL reaction vial were added 23-3 (1.10 g, 2.54 mmol), 2,6-lutidine (682 mg, 6.37 mmol), 2-6, and 2-methyl-2-butanol (16 mL) at room temperature. The resulting mixture was stirred overnight at 110° C. under nitrogen atmosphere, then cooled to room temperature and extracted with ethyl acetate (3×100 mL). The combined organic layers were washed with brine, dried over Na₂SO₄, filtered, and concentrated in vacuo. The residue was purified by reverse-phase flash chromatography (column, $C_{18}$; mobile phase, MeCN in water (10 mmol/L NH₄HCO₃)) to afford 23-4 as a white solid. ESI-MS m/z: 754 [M+H]⁺.

Step 4: To a 20 mL reaction vial were added 23-4 (550 mg, 0.72 mmol) and DMF (10 mL, 129.21 mmol) at room temperature. The resulting mixture was stirred for 30 min at 80° C. under nitrogen atmosphere, then cooled to room temperature and extracted with ethyl acetate (3×100 mL). The combined organic layers were washed with brine, dried over Na₂SO₄, filtered, and concentrated in vacuo. The residue was purified by reverse-phase flash chromatography (column, $C_{18}$; mobile phase, MeCN in water (10 mmol/L NH₄HCO₃)) to afford 23-5 as a white solid. ESI-MS m/z: 496 [M+H]⁺.

Step 5: A solution of 23-5 (300 mg, 0.6 mmol) in DCM (6.0 mL) was treated with m-CPBA (312 mg, 1.81 mmol) at −10° C. under nitrogen atmosphere. The resulting mixture was stirred for 1 hour at 0° C. under nitrogen atmosphere, then quenched with sat. sodium hyposulfite (aq.) at 0° C. The mixture was treated with saturated NaHCO₃(aq.) and extracted with EtOAc (3×50 mL). The combined organic layers were washed with brine (2×20 mL), dried over anhydrous Na₂SO₄, filtered, and the filtrate concentrated under reduced pressure to afford 23-6 as a yellow solid, used in the next step without further purification. ESI-MS m/z: 528 [M+H]⁺.

Step 6: A solution of 23-6 (400 mg, 0.53 mmol, 1.00 eq) in toluene (28 mL) was treated with 2-10 (252 mg, 1.59 mmol) for 5 min at 0° C. under nitrogen atmosphere, then t-BuONa (458 mg, 4.77 mmol) was added dropwise at 0° C. The resulting mixture was stirred for 1 hour at 0° C. under nitrogen atmosphere and extracted with ethyl acetate (3×50 mL). The combined organic layers were washed with brine, dried over Na₂SO₄, filtered, and concentrated in vacuo. The residue was purified by reverse-phase flash chromatography (column, $C_{18}$; mobile phase, MeCN in water (10 mmol/L NH₄HCO₃)) to afford 23-7 as a white solid. ESI-MS m/z: 607 [M+H]⁺.

Step 7: To a 40 mL vial were added 23-7 (130 mg, 0.21 mmol), 2-12 (257 mg, 0.638 mmol), (II)/Dichloro[bis(2-(diphenylphosphino)phenyl) ether]palladium(II) (23 mg, 0.03 mmol) and toluene (15 mL) at room temperature and the resulting mixture was degassed for 20 min with argon. The reaction was stirred for 2 hours at 110° C. under argon atmosphere, then cooled to room temperature and extracted with ethyl acetate (3×30 mL). The combined organic layers were washed with brine, dried over Na₂SO₄, filtered, and concentrated in vacuo. The residue was purified by reverse-phase flash chromatography (column, $C_{18}$; mobile phase, MeCN in water (10 mmol/L NH₄HCO₃)) to afford 23-8 as a white solid. ESI-MS m/z: 819 [M+H]⁺.

Step 8: To an 8 mL reaction vial were added 23-8 (100 mg, 0.12 mmol) and TFA (1.0 mL, 13.46 mmol) at room temperature. The resulting mixture was stirred for 2 hours at room temperature under nitrogen atmosphere, then diluted with DCM (10 mL). The mixture was treated with saturated NaHCO₃(aq.) and extracted with ethyl acetate (3×50 mL). The crude product was purified by Prep-HPLC (Column: XBridge Prep OBD C18 Column, 30*150 mm, 5 um; Mobile Phase A: Water (10 mmol/L NH₄HCO₃), Mobile Phase B: ACN; Flow rate: 60 mL/min; Gradient: 50% B to 70% B in 10 min, 70% B) to afford 1008 as a white solid. ESI-MS m/z: 718.80 [M+H]⁺. ¹H NMR (400 MHZ, Chloroform-d) δ 7.26-7.15 (m, 1H), 7.07-6.97 (m, 1H), 6.50-6.08 (m, 1H), 5.73 (s, 1H), 5.59 (d, J=10.9 Hz, 1H), 5.33 (d, J=53.4 Hz, 1H), 4.94 (dtt, J=40.4, 6.2, 3.0 Hz, 1H), 4.77-4.39 (m, 1H), 4.35-4.25 (m, 2H), 4.16-3.64 (m, 3H), 3.46 (s, 1H), 3.34-3.19 (m, 1H), 3.05 (d, J=5.0 Hz, 1H), 2.34 (d, J=11.7 Hz, 1H), 2.26 (s, 1H), 2.16 (d, J=9.9 Hz, 1H), 2.00 (s, 2H).

Example 1x: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxyethyl)-5,6-dihydro-4H-[1,4]oxazepino[5,6,7-de]quinazolin-9-yl)-7-fluorobenzo[b]thiophene-3-carbonitrile (1049 and 882)

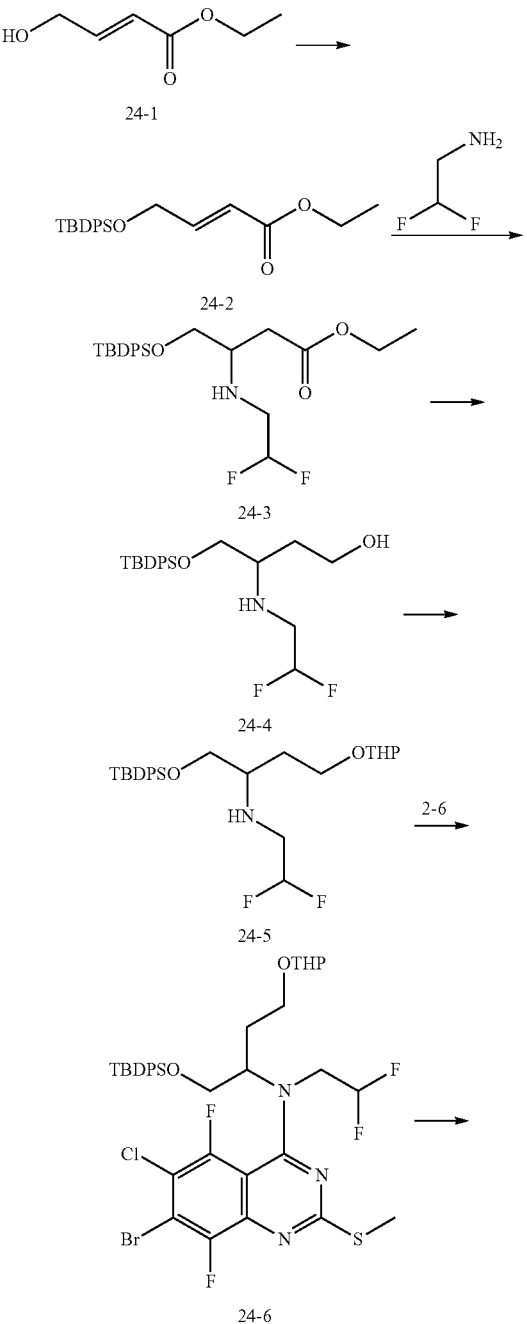

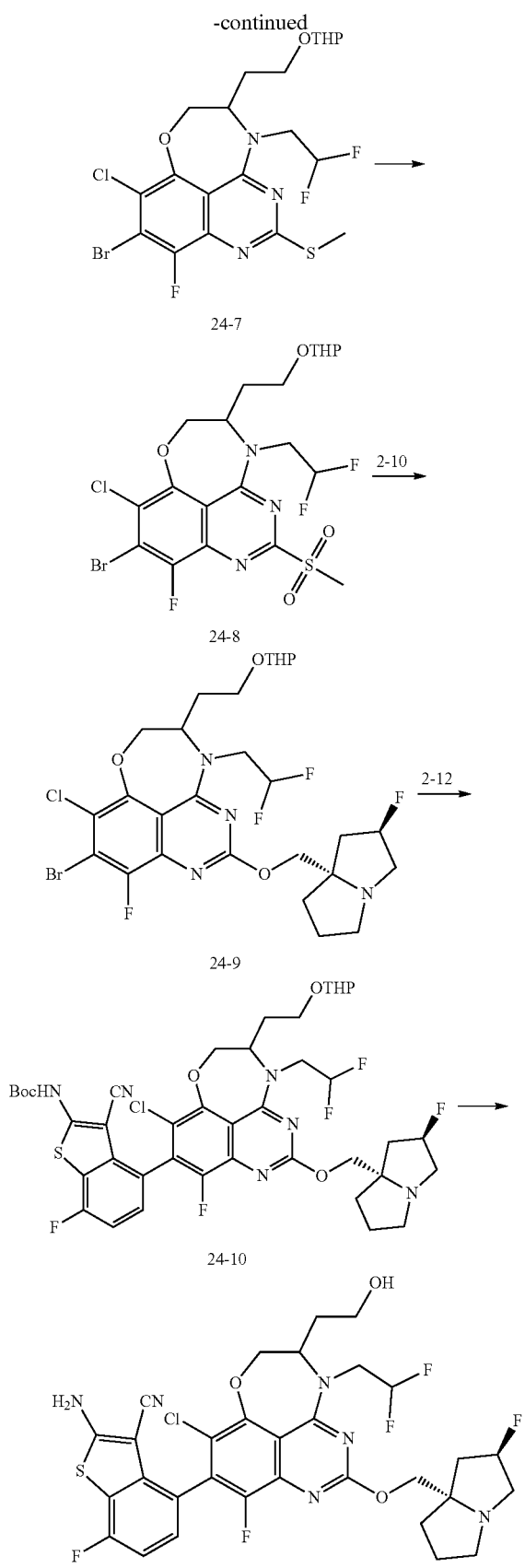

Step 1: To a stirred mixture of ethyl (2E)-4-hydroxybut-2-enoate (24-1) (9.30 g, 71.46 mmol) and imidazole (9.73 g, 142.92 mmol) in DCM (10 mL) was added TBDPSCl (23.57 g, 85.75 mmol) in portions at 0° C. under nitrogen atmosphere. The resulting mixture was stirred overnight at room temperature, then diluted with water (10 mL) and extracted with $CH_2Cl_2$ (3×10 mL). The combined organic layers were washed with brine, dried over $Na_2SO_4$, filtered, and concentrated in vacuo. The residue was purified by prep-TLC (petroleum ether:ethyl acetate=10:1) to afford 24-2 as a colorless oil. ESI-MS m/z: 369 $[M+H]^+$.

Step 2: A solution of 24-2 (100.0 mg, 0.27 mmol), 2,2-difluoroethan-1-amine (16.50 g, 203.5 mmol) and DBU (608 μL, 4.07 mmol) in EtOH (195 mL) was stirred for 24 h at 50° C. The reaction was quenched by the addition of water (200 mL) at room temperature, then extracted with ethyl acetate (3×150 mL). The combined organic layers were washed with brine, dried over $Na_2SO_4$, filtered, and concentrated in vacuo. The residue was purified by silica gel column chromatography, eluting with petroleum ether/ethyl acetate (10:1) to afford 24-3 as a yellow oil. ESI-MS m/z: 450 $[M+H]^+$.

Step 3: A solution of 24-3 (2.30 g, 5.11 mmol) and $LiBH_4$ (10 mL) in THF (10 mL) was stirred overnight at room temperature. The reaction was quenched by the addition of water (30 mL) at room temperature and extracted with ethyl acetate (3×30 mL). The combined organic layers were washed with brine (1×70 mL), dried over anhydrous $Na_2SO_4$, filtered, and the filtrate concentrated under reduced pressure to give 24-4 which was used in the next step directly without further purification. ESI-MS m/z: 408 $[M+H]^+$.

Step 4: A solution of 24-4 (1.85 g, 4.53 mmol), DHP (2.29 g, 27.23 mmol) and TsOH (0.94 g, 5.44 mmol) in DCM (23 mL) was stirred overnight at room temperature. The reaction was quenched by the addition of water (20 mL) at room temperature and extracted with $CH_2Cl_2$ (3×15 mL). The combined organic layers were washed with brine, dried over $Na_2SO_4$, filtered, and concentrated in vacuo. The residue was purified by silica gel column chromatography, eluting with petroleum ether/ethyl acetate (9:1) to afford 24-5 as a yellow oil. ESI-MS m/z: 492 $[M+H]^+$.

Step 5: A solution of 24-5 (1.10 g, 2.23 mmol), 2-6 (724.8 mg, 2.01 mmol) and 2,6-lutidine (664 μL, 5.7 mmol) in 2-methyl-2-butanol (22 mL) was stirred overnight at 80° C. The reaction mixture was cooled to room temperature and quenched by the addition of water (40 mL). The mixture was extracted with ethyl acetate (3×25 mL). The combined organic layers were washed with brine, dried over $Na_2SO_4$, filtered, and concentrated in vacuo. The residue was purified by reverse-phase flash chromatography (column, $C_{18}$; mobile phase, MeCN in water (10 mmol/L $NH_4HCO_3$) to afford 24-6. ESI-MS m/z: 814 $[M+H]^+$.

Step 6: A solution of 24-6 (0.90 g, 1.1 mmol) and CsF (0.67 g, 4.41 mmol) in DMF (27 mL) was stirred for 3 hours at 80° C., then cooled to room temperature and quenched with water (40 mL). The mixture was extracted with ethyl acetate (3×25 mL). The combined organic layers were washed with brine, dried over $Na_2SO_4$, filtered, and concentrated in vacuo. The residue was purified by silica gel column chromatography, eluting with petroleum ether/ethyl acetate (10:1) to afford 24-7 as a white solid.

Step 7: A solution of 24-7 (270.0 mg, 0.48 mmol) in DCM (8 mL) was treated with m-CPBA (251.0 mg, 1.45 mmol) and $NaHCO_3$ (122.2 mg, 1.45 mmol) in water (8 mL) for 2.5 hours at −10° C. under nitrogen atmosphere. The reaction was quenched by the addition of ice-water at 0° C. and extracted with EA (3×20 mL). The combined organic layers were washed with brine (1×40 mL), dried over anhydrous Na$_2$SO$_4$, filtered, and the filtrate concentrated under reduced pressure to afford 24-8 as a yellow solid which was used in the next step directly without further purification. ESI-MS m/z: 588 [M+H]$^+$.

Step 8: To a solution of 24-8 (320.0 mg, 0.54 mmol) and 2-10 (173.0 mg, 1.08 mmol) in toluene (8 mL) at at −10° C. under nitrogen atmosphere was added t-BuONa (156.6 mg, 1.62 mmol) portionwise. The resulting mixture was stirred for 1 hour at −10° C. under nitrogen atmosphere, then quenched by the addition of sat. NH$_4$Cl (aq.) (15 mL) at 0° C. and the mixture extracted with ethyl acetate (3×20 mL). The combined organic layers were washed with brine, dried over Na$_2$SO$_4$, filtered, and concentrated in vacuo. The residue was purified by reverse-phase flash chromatography (column, C$_{18}$; mobile phase, MeCN in water (10 mmol/L NH$_4$HCO$_3$)) to afford 24-9 as a white solid. ESI-MS m/z: 667 [M+H]$^+$.

Step 9: To a reaction vial charged with a magnetic bar was added 24-9 (200.0 mg, 0.29 mmol), washed with brine, dried over Na$_2$SO$_4$, filtered, and concentrated in vacuo. The residue was purified by 2-12 (363.1 mg, 0.89 mmol), Cs$_2$CO$_3$ (878.0 mg, 2.69 mmol) and dichloropalladium; {2-[2-(diphenylphosphanyl)phenoxy] phenyl}diphenylphosphane (32.1 mg, 0.04 mmol). The reaction system was degassed and backfilled with N$_2$ three times, then anhydrous toluene (20.0 mL) was added via syringe. The mixture was degassed and refilled with N$_2$ three times before stirring at 110° C. for 2 hours. The resulting mixture was cooled to room temperature and concentrated under vacuum. The residue was purified by reverse-phase flash chromatography (column, C$_{18}$; mobile phase, MeCN in water (10 mmol/L NH$_4$HCO$_3$)) to afford 24-10 as a white solid. ESI-MS m/z: 879 [M+H]$^+$.

Step 10: A solution of 24-10 (120.0 mg, 0.13 mmol) and TFA (1.2 mL) in DCM (6 mL) was stirred for 2 hours at room temperature under nitrogen atmosphere. The mixture was treated with NH$_3$·H$_2$O, then extracted with CH$_2$Cl$_2$ (3×15 mL). The combined organic layers were washed with brine, dried over Na$_2$SO$_4$, filtered, and concentrated in vacuo. The residue was purified by prep-HPLC with the following conditions (Column: XBridge Prep OBD C18 Column, 30*150 mm, 5 um; Mobile Phase A: water (10 mmol/L NH$_4$HCO$_3$), Mobile Phase B: ACN) to afford two products of peak 1 and peak 2.1049 (Peak 1): ESI-MS m/z: 695 [M+H]$^+$; $^1$H NMR (400 MHZ, DMSO-d$_6$) δ 8.08 (s, 2H), 7.22 (dd, J=8.4, 5.3 Hz, 1H), 7.12 (dd, J=9.4, 8.4 Hz, 1H), 6.73-6.29 (m, 1H), 5.28 (d, J=54.2 Hz, 1H), 4.84 (dd, J=13.0, 4.6 Hz, 1H), 4.79 (t, J=4.8 Hz, 1H), 4.64 (dq, J=24.0, 13.6, 11.0 Hz, 1H), 4.36 (dd, J=12.9, 1.9 Hz, 1H), 4.18 (q, J=7.2 Hz, 1H), 4.09 (d, J=10.3 Hz, 1H), 4.02 (d, J=10.2 Hz, 1H), 3.92-3.84 (m, 1H), 3.54 (dp, J=16.0, 5.3 Hz, 2H), 3.09 (dd, J=7.5, 4.6 Hz, 2H), 3.01 (s, 1H), 2.82 (q, J=8.1 Hz, 1H), 2.40-2.28 (m, OH), 2.21-1.91 (m, 3H), 1.81 (d, J=6.9 Hz, 5H). 882 (Peak 2): ESI-MS m/z: 695 [M+H]$^+$; $^1$H NMR (400 MHZ, DMSO-d$_6$) δ 8.06 (s, 2H), 7.26 (dd, J=8.4, 5.2 Hz, 1H), 7.15 (dd, J=9.5, 8.4 Hz, 1H), 6.64-6.27 (m, 1H), 5.29 (d, J=54.3 Hz, 1H), 4.86-4.77 (m, 2H), 4.65 (s, 1H), 4.50 (d, J=12.8 Hz, 1H), 4.19 (q, J=6.9 Hz, 1H), 4.09 (s, 1H), 4.04 (s, 1H), 3.87 (d, J=13.9 Hz, 1H), 3.51 (dp, J=23.2, 5.4 Hz, 2H), 3.06 (d, J=31.9 Hz, 3H), 2.84 (s, 1H), 2.21-1.94 (m, 3H), 1.81 (m, 5H).

Example 1y: Synthesis of 2-amino-4-(8-chloro-4-(2, 2-difluoroethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de] quinazolin-9-yl)-7-fluorobenzo[b]thiophene-3-carbonitrile (616 and 1073)

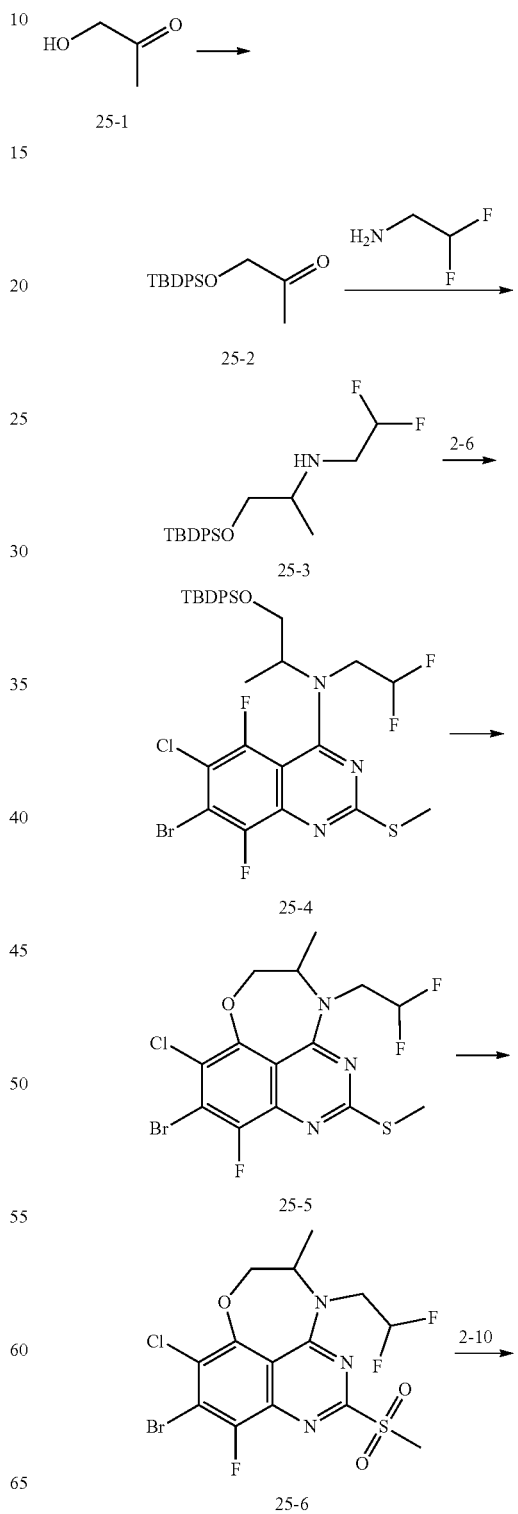

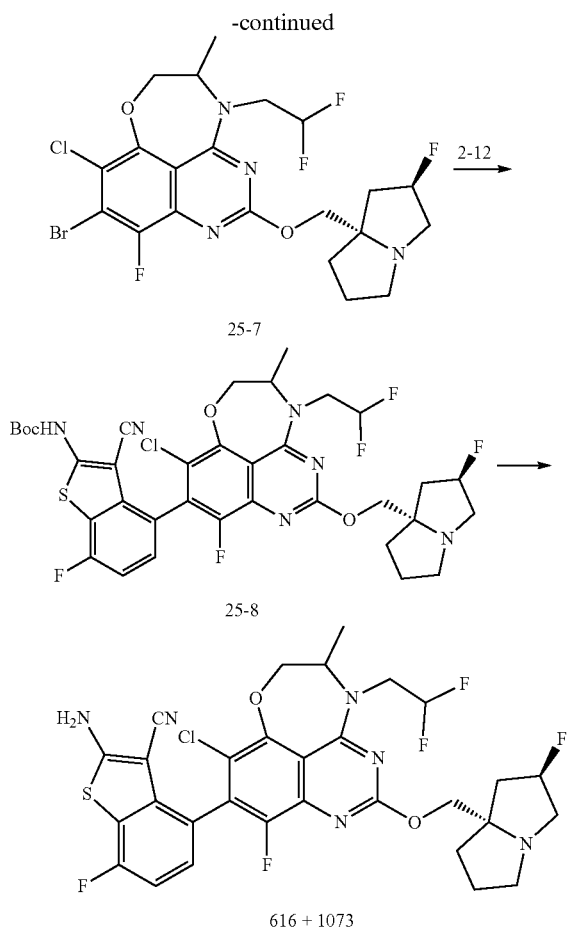

The combined organic layers were washed with brine, dried over Na$_2$SO$_4$, filtered, and concentrated in vacuo. The residue was purified by silica gel column chromatography, eluting with petroleum ether/ethyl acetate (5:1) to afford 25-4 as an off-white solid. ESI-MS m/z: 701.75 [M+H]$^+$.

Step 4: To a stirred solution of 25-4 (590 mg, 0.84 mmol)) in DMF (10 mL) was added CsF (384 mg, 2.53 mmol, and the resulting reaction mixture stirred for 4 hours at 80° C. under nitrogen atmosphere. The reaction mixture was cooled to room temperature, then quenched with water and extracted with ethyl acetate (3×150 mL). The combined organic layers were washed with brine, dried over Na$_2$SO$_4$, filtered, and concentrated in vacuo. The residue was purified by silica gel column chromatography, eluting with petroleum ether/ethyl acetate (5:1) to afford 25-5 as an off-white solid. ESI-MS m/z: 443.80 [M+H]$^+$.

Step 5: To a stirred solution of 25-5 (150 mg, 0.34 mmol) in DCM (4 mL) was added mCPBA (206.37 mg, 1.017 mmol, 85%) at −5° C. under nitrogen atmosphere. The reaction mixture was stirred for an additional hour at −5° C., then quenched with sat. sodium hyposulfite (aq.) at 0° C. and extracted with ethyl acetate (3×50 mL). The combined organic layers were washed with NaHCO$_3$(aq) (3×100 mL), dried over anhydrous Na$_2$SO$_4$, filtered, and the filtrate concentrated under reduced pressure to afford 25-6 as a yellow solid which was used directly in the next step without further purification. ESI-MS m/z: 475.75 [M+H]$^+$.

Step 6: To a stirred solution of 25-6 and 2-10 (120 mg, 0.76 mmol) in toluene (5 mL) was added t-BuONa (109 mg, 1.14 mmol) in portions at −5° C. under nitrogen atmosphere. The reaction mixture was stirred for 1 hour at 0° C., then quenched with sat. NH$_4$Cl (aq.) and extracted with ethyl acetate (3×50 mL). The combined organic layers were washed with brine, dried over Na$_2$SO$_4$, filtered, and concentrated in vacuo. The residue was purified by silica gel column chromatography, eluting with petroleum ether/ethyl acetate (1:2), to afford 25-7 as an off-white solid. ESI-MS m/z: 554.90 [M+H]$^+$.

Step 7: A solution of 25-7 (100 mg, 0.181 mmol) and 2-12 (182 mg, 0.45 mmol) in toluene (4 mL) was stirred for 2 hours at 100° C. under argon atmosphere, then cooled to room temperature and the resulting mixture extracted with ethyl acetate (3×50 mL). The combined organic layers were washed with brine, dried over Na$_2$SO$_4$, filtered, and concentrated in vacuo. The residue was purified by prep-TLC (CH$_2$Cl$_2$/MeOH 20:1) to afford 25-8 as a white solid.

Step 8: To a stirred solution of 25-8 (60 mg, 0.08 mmol) in DCM (2 mL) was added TFA (0.4 mL), and the reaction mixture was stirred for 2 hours at room temperature. The resulting mixture was concentrated under vacuum. The crude product was purified by prep-HPLC (Column, XBridge Prep OBD C18 Column, 30×150 mm, 5 um; mobile phase, water (10 mmol/L NH$_4$HCO$_3$) and CAN) to afford two peaks. 616 (Peak 1): ESI-MS m/z: 664.90 [M+H]$^+$. $^1$H NMR (400 MHZ, DMSO-d$_6$) δ 8.05 (s, 2H), 7.26 (dd, J=8.4, 5.2 Hz, 1H), 7.15 (t, J=8.9 Hz, 1H), 6.46 (t, J=56.4 Hz, 1H), 5.28 (d, J=52.6 Hz, 1H), 4.70 (dd, J=12.7, 4.6 Hz, 1H), 4.46 (d, J=12.8 Hz, 1H), 4.38 (s, 1H), 4.23-3.91 (m, 4H), 3.09 (s, 2H), 3.02 (s, 1H), 2.83 (s, 1H), 2.13 (s, 1H), 2.03 (d, J=20.3 Hz, 2H), 1.79 (s, 3H), 1.26 (d, J=6.7 Hz, 3H). 1073 (Peak 2): ESI-MS m/z: 664.90 [M+H]$^+$. $^1$H NMR (400 MHZ, DMSO-d$_6$) δ 8.07 (s, 2H), 7.23 (dd, J=8.4, 5.3 Hz, 1H), 7.13 (dd, J=9.5, 8.3 Hz, 1H), 6.47 (t, J=56.4 Hz, 1H), 5.34 (d, J=53.8 Hz, 1H), δ 4.73 (dd, J=13.0, 4.3 Hz, 1H), 4.45-4.35 (m, 1H), 4.32 (d, J=12.6 Hz, 1H), 4.15 (t, J=5.9 Hz, 2H), 4.09 (dd, J=10.2, 2.0 Hz, 1H), 4.02 (d, J=10.3 Hz, 1H).3.08 (d, J=8.3 Hz, 2H), 3.01 (s, 1H), 2.88-2.79 (m, 1H), δ 2.16-2.10 (m, 1H), 2.05 (d, J=4.1 Hz, 1H), 2.00 (s, 1H), 1.85 (s, 1H), 1.80-1.70 (m, 2H), 1.31 (d, J=6.7 Hz, 3H).
Example 1z: Synthesis of 2-amino-4-(8-chloro-5-((2-cyanocyclopropyl)methyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (674 and 1003)
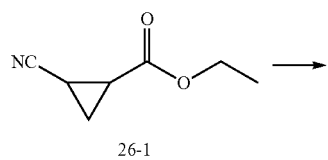
26-1
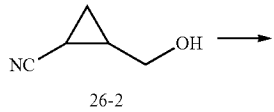
26-2
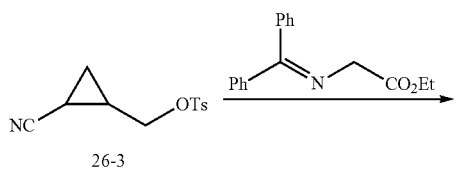
26-3
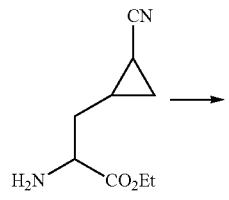
26-4
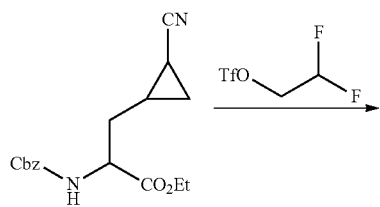
6-5
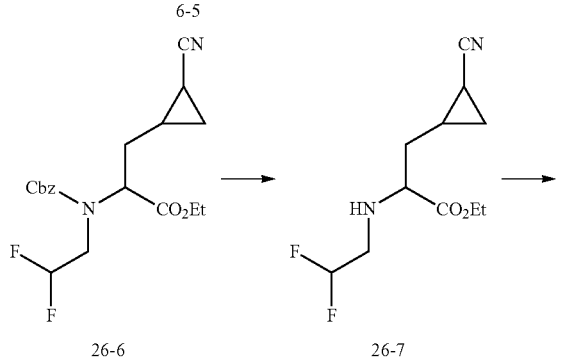
26-6     26-7
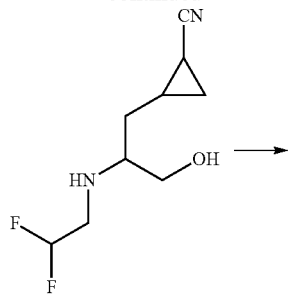
26-8
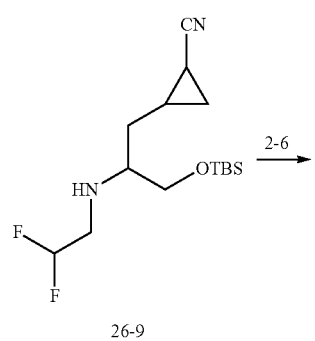
26-9
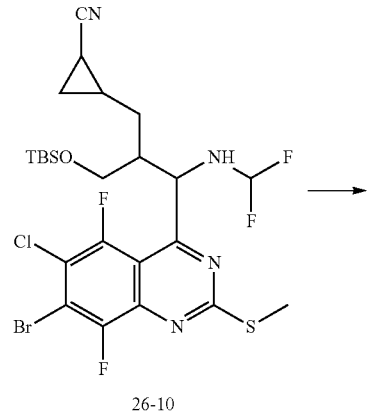
26-10
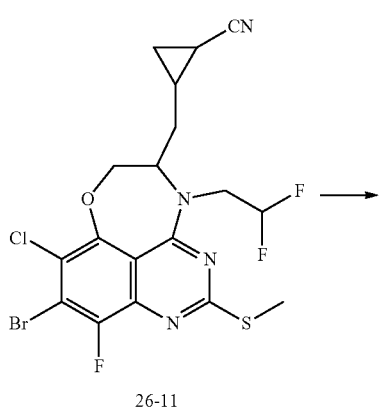
26-11

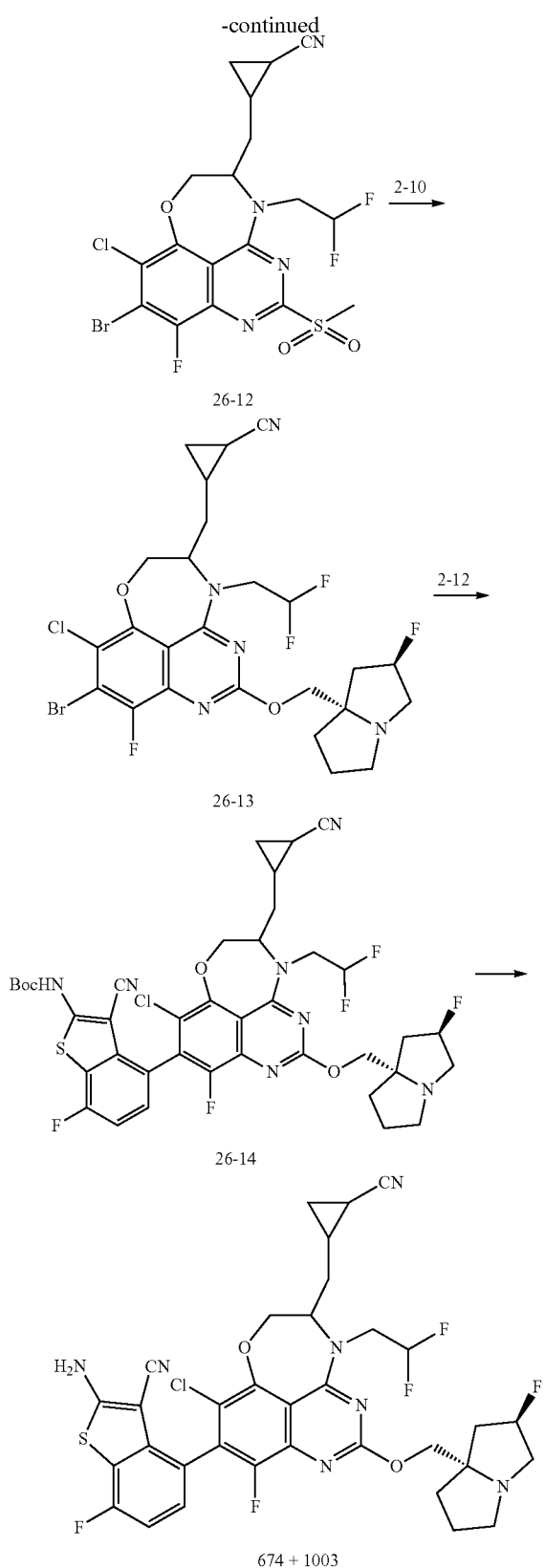

reaction mixture was allowed to warm to room temperature and stirred for 12 hours. The reaction mixture was then cooled to 0° C., quenched with water (20 mL), extracted with Et$_{20}$ (3×10 mL), and dried over MgSO$_4$. It was filtered and solvent was removed to give 26-2, used in the next step directly without further purification.

Step 2: 26-2 (3 g, 30.891 mmol), DMAP (0.27 g, 3.089 mmol) and TEA (6.25 g, 61.782 mmol) were dissolved in DCM (30 mL). TsCl (7.07 g, 37.069 mmol) was carefully added in portions slowly, and the reaction mixture was stirred at room temperature for 4 hours. The reaction mixture was washed with water (3×10 mL), extracted with DCM (3×10 mL), and dried over MgSO$_4$, then filtered and solvent removed to give 26-3, used in the next step directly without further purification. ESI-MS m/z: 293 [M+ACN]$^+$.

Step 3: A stirred solution of ethyl 2-[(diphenylmethylidene)amino]acetate (4.34 g, 16.236 mmol) in dry THF (25 mL) under nitrogen atmosphere was cooled to −78° C. and treated with a solution of tBuOK (15.6 mL, 1.15 equiv). The reaction mixture was stirred at 0° C. and treated with 26-3 (3.4 g, 13.53 mmol), then stirred at room temperature for an additional 6 hours. The reaction mixture was treated with aqueous HCl (2 M, 8 mL), stirred at room temperature for 10 min and concentrated in vacuo to give 26-4, which was used in the next step directly without further purification. ESI-MS m/z: 183 [M+H]$^+$.

Step 4: To a stirred suspension of 26-4 (8 g, 43.902 mmol) was added TEA (13.33 g, 131.706 mmol) in CH$_2$Cl$_2$ (40 mL) at room temperature and the reaction mixture was cooled to 0° C. CbzCl (11.23 g, 65.853 mmol) was added dropwise to the reaction mixture and the reaction mixture was allowed to warm to room temperature. Water (15 mL) was added, and the organic layer was separated after 3 hours of stirring. The aqueous layer was extracted with CH$_2$Cl$_2$ (3×10 mL) and the combined organic layers were washed with water (30 mL), dried over Na$_2$SO$_4$, filtered, and concentrated in vacuo to give a residue. The residue was purified by silica gel column chromatography, eluting with PE/EA (12:1) to afford 26-5 as a colorless oil. ESI-MS m/z: 317 [M+H]$^+$.

Step 5: To a solution of 26-5 (600 mg, 1.897 mmol) in 10 mL of THF was added potassium bis(trimethylsilyl)amide (1 M in THF, 3.8 mL, 3.8 mmol), then the resulting mixture was stirred for 10 min at 0° C. 2,2-difluoroethyl trifluoromethanesulfonate (487.3 mg, 2.276 mmol) was added dropwise and the reaction mixture was allowed to warm to room temperature and stirred for 7 hours. The reaction mixture was diluted with DCM, washed with brine, dried over Na$_2$SO$_4$, filtered, and concentrated in vacuo. The residue was purified by silica gel column chromatography, eluting with petroleum ether/ethyl acetate (9:1) to afford 26-6 as a colorless oil. ESI-MS m/z: 381 [M+H]$^+$.

Step 6: A solution of 26-6 (600 mg, 1.577 mmol) in MeOH (5 mL) was treated with Pd/C (167.86 mg, 1.577 mmol) under H$_2$ atmosphere at room temperature for 1.5 hours. The mixture was filtered through celite and the filtrate was concentrated under vacuum to afford 26-7 as a yellow oil. ESI-MS m/z: 247 [M+H]$^+$.

Step 7: 26-7 (350 mg, 1.421 mmol) was dissolved in anhydrous THF (10 mL) and the solution was cooled to 0° C. LiBH4 P (118.08 mg, 5.684 mmol) was carefully added in small portions, and the reaction mixture was allowed to warm to room temperature and stirred for 4 hours. The reaction was quenched with water at 0° C., then the aqueous layer was extracted with CH$_2$Cl$_2$ (3×5 mL). The organics were combined and washed with brine, dried over sodium Step 1: Ethyl 2-cyanocyclopropane-1-carboxylate (26-1) (4.8 g, 34.494 mmol) was dissolved in anhydrous THF (40 mL) and the solution cooled to 0° C. LiBH4 (2.69 mL, 2 M in THF) was carefully added in small portions, and the sulfate, filtered, and solvent removed to give 26-8 which was used in the next step without further purification. ESI-MS m/z: 205 [M+H]$^+$.

Step 8: To a solution of 26-8 (150 mg, 0.734 mmol) in DCM (5 mL) was added imidazole (60.0 mg, 0.881 mmol) at room temperature followed by TBSCl (166.06 mg, 1.101 mmol) dropwise at 0° C. The resulting mixture was stirred for 7 hours at room temperature, then diluted with DCM and washed with brine, dried over Na$_2$SO$_4$, filtered, and concentrated in vacuo. The residue was purified by silica gel column chromatography, eluting with petroleum ether/ethyl acetate (5:1) to afford 26-9 as a colorless oil. ESI-MS m/z: 319 [M+H]$^+$.

Step 9: To a solution of 26-9 (80 mg, 0.251 mmol) in tBuOH (2 mL) was added 2-6 (90.43 mg, 0.251 mmol) at room temperature under nitrogen atmosphere followed by the addition of DIEA (97.4 mg, 0.753 mmol) in portions. The resulting mixture was stirred overnight at 90° C. under nitrogen atmosphere, then cooled to room temperature and solvent removed. The residue was dissolved in DCM, washed with brine, dried over Na$_2$SO$_4$, filtered, and concentrated in vacuo. The residue was purified by silica gel column chromatography, eluting with petroleum ether/ethyl acetate (10:1) to afford 26-10 as a brown oil. ESI-MS m/z: 641 [M+H]$^+$.

Step 10: A solution of 26-10 (110 mg, 0.171 mmol) in DMF (0.2 mL) was treated with CsF (78.08 mg, 0.513 mmol) overnight at 80° C. under nitrogen atmosphere, then cooled to room temperature and diluted with DCM, washed with brine, dried over Na$_2$SO$_4$, filtered, and concentrated in vacuo. The residue was purified by silica gel column chromatography, eluting with petroleum ether/ethyl acetate (5:1) to afford 26-11 as a colorless oil. ESI-MS m/z: 507 [M+H]$^+$.

Step 11: To a stirred solution of 26-11 (100 mg, 0.197 mmol) in DCM (1 mL) was added m-CPBA (101.96 mg, 0.591 mmol) at −10° C. The resulting mixture was stirred for 1.5 hours at room temperature, then quenched by addition of sat. Na$_2$SO$_3$ (aq.) (5 mL). The aqueous layer was extracted with CH$_2$Cl$_2$ (3×5 mL). The combined organics were washed with brine, dried over Na$_2$SO$_4$, filtered, and concentrated in vacuo. The residue was purified by silica gel column chromatography, eluting with petroleum ether/ethyl acetate (7:3) to afford 26-12 as a colorless oil. ESI-MS m/z: 539 [M+H]$^+$.

Step 12: To a stirred solution of 26-12 (80 mg, 0.148 mmol) and 2-10 (47.19 mg, 0.296 mmol) in THF (1 mL) was added potassium 2-methylpropan-2-olate (24.95 mg, 0.222 mmol) dropwise at 0° C. The resulting mixture was stirred for 2 hours at room temperature. The reaction was diluted with DCM, washed with brine, dried over Na$_2$SO$_4$, filtered, and concentrated in vacuo. The residue was purified by silica gel column chromatography, eluting with CH$_2$Cl$_2$/MeOH (10:1) to afford 26-13 as a colorless oil. ESI-MS m/z: 618 [M+H]$^+$.

Step 13: A solution of 26-13 (54 mg, 0.087 mmol), 2-12 (105.28 mg, 0.261 mmol), (II)/Dichloro[bis(2-(diphenylphosphino)phenyl)ether]palladium(II) (9.37 mg, 0.013 mmol) and t-BuONa (16.77 mg, 0.174 mmol) in anhydrous toluene (2 mL) was treated with 4 Å MS for 15 min at room temperature under nitrogen atmosphere. The resulting mixture was stirred for 2.5 hours at 120° C. under nitrogen atmosphere, then allowed to cool to room temperature. The reaction mixture was concentrated under reduced pressure to give a residue, which was purified by prep-TLC (CH$_2$Cl$_2$/MeOH 15:1) to afford 26-14 as a colorless oil. ESI-MS m/z: 830 [M+H]$^+$.

Step 14: A solution of 26-14 (35 mg, 0.042 mmol) was treated with DCM/TFA (2 mL, 3:1) for 2 hours at room temperature. The resulting mixture was concentrated under reduced pressure to give a residue, which was purified by prep-HPLC (Column:Kinetex EVO prep C$_{18, 30*150, 5}$ um; Mobile Phase A: Water (10 mmol/L NH$_4$HCO$_3$), Mobile Phase B: ACN) to afford two peaks. 674 (Peak 1): ESI-MS m/z: 730 [M+H]$^+$. $^1$H NMR (400 MHZ, Chloroform-d) δ=7.20-7.13 (m, 1H), 7.07-6.95 (m, 1H), 6.38 (t, J=57.0 Hz, 1H), 5.67-5.36 (m, 2H), 5.26 (s, 1H), 4.95-4.80 (m, 1H), 4.68-4.53 (m, 1H), 4.47 (dd, J=13.2, 7.7 Hz, 1H), 4.39-4.18 (m, 2H), 4.04-3.90 (m, 1H), 3.66 (s, 1H), 3.54-3.10 (m, 3H), 3.05 (s, 1H), 2.40-2.28 (m, 1H), 2.28-2.19 (m, 1H), 2.15 (s, 1H), 1.93-1.81 (m, 2H), 1.45 (dd, J=9.2, 4.6 Hz, 1H), 1.40-1.30 (m, 2H), 1.26 (d, J=5.0 Hz, 2H), 1.21-1.13 (m, 1H), 0.95-0.87 (m, 1H). 1003 (Peak 2): ESI-MS m/z: 730 [M+H]$^+$. $^1$H NMR (400 MHZ, Chloroform-d) δ=7.26-7.18 (m, 1H), 7.04 (td, J=8.8, 4.2 Hz, 1H), 6.41 (t, J=56.7 Hz, 1H), 5.53-5.34 (m, 2H), 5.29 (s, 1H), 4.98-4.82 (m, 1H), 4.75-4.20 (m, 4H), 4.00 (dd, J=9.8, 5.2 Hz, 1H), 3.62 (s, 2H), 3.33 (s, 2H), 3.09 (s, 1H), 2.49-2.29 (m, 1H), 2.26-2.13 (m, 1H), 2.04 (s, 3H), 1.91-1.78 (m, 1H), 1.49-1.39 (m, 2H), 1.26 (d, J=5.6 Hz, 1H), 1.22-1.07 (m, 2H), 0.90-0.77 (m, 1H).

Example 1aa: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile (899 and 1102)

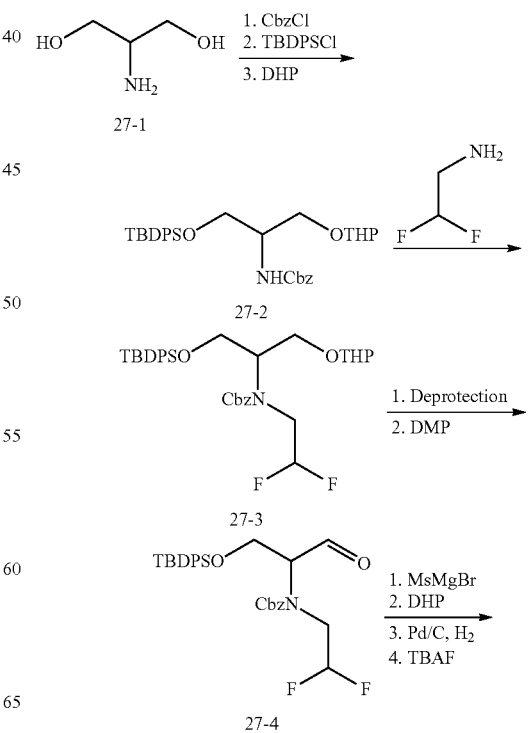

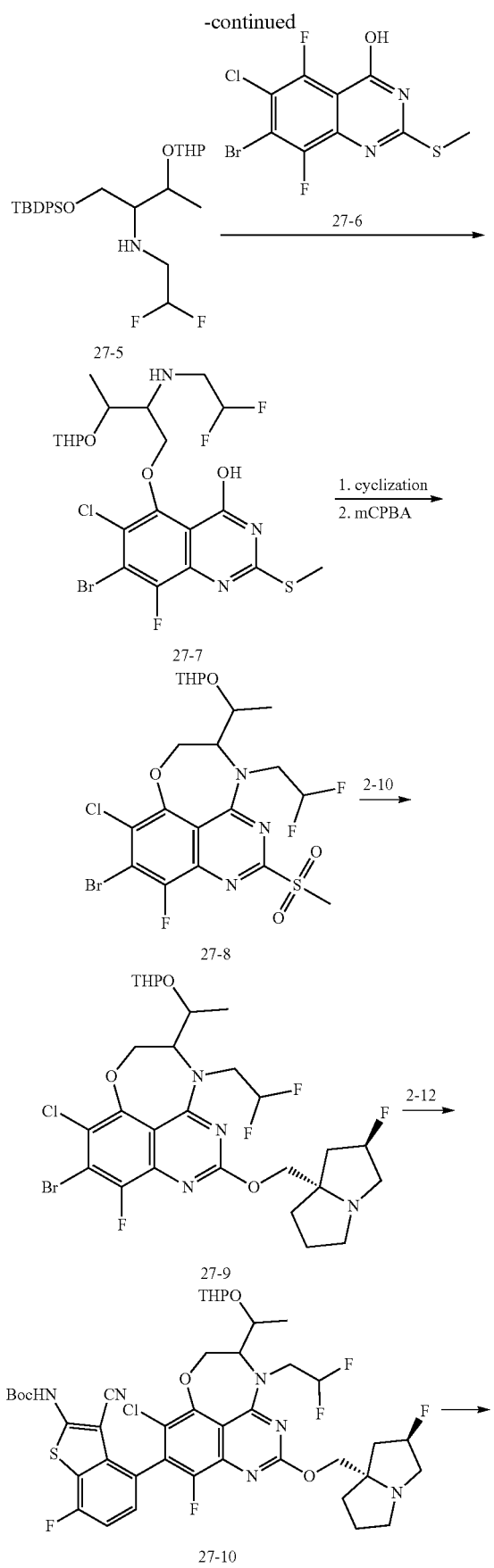

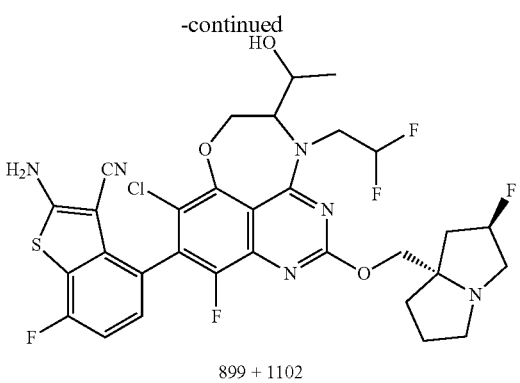

Step 1: To a solution of 2-aminopropane-1,3-diol (27-1) (10.00 g, 109.77 mmol) in EtOH (30 mL) was added TEA (16.78 mL, 120.73 mmol) and CbzCl (18.72 g, 109.76 mmol) at 0° C. The reaction mixture was allowed to warm to room temperature and stirred for 2 hours. The resulting mixture was concentrated under reduced pressure to give a mixture, then filtered and the filter cake washed with ethyl acetate (3×20 mL). The filtrate was concentrated under reduced pressure to give a residue, which was purified by silica gel column chromatography, eluting with $CH_2Cl_2$/MeOH (20:1-10:1) to afford benzyl N-(1,3-dihydroxypropan-2-yl)carbamate as a white solid. ESI-MS m/z: 226 $[M+H]^+$.

Step 2: To a solution of benzyl N-(1,3-dihydroxypropan-2-yl)carbamate (10.20 g, 45.28 mmol) in DMF (90 mL) was added TBDPSCl (16.18 g, 58.87 mmol) and imidazole (4.01 g, 58.87 mmol) at 0° C. The reaction was allowed to warm to room temperature and stirred for 2 hours. The resulting mixture was concentrated under reduced pressure, filtered, and the filter cake washed with ethyl acetate (3×20 mL). The filtrate was combined and concentrated under reduced pressure to give a residue. The residue was purified by silica gel column chromatography, eluting with petroleum ether/ethyl acetate (3:1 to 1:1) to afford benzyl N-{1-[(tert-butyldiphenylsilyl)oxy]-3-hydroxypropan-2-yl} carbamate as a colorless oil. ESI-MS m/z: 464 $[M+H]^+$.

Step 3: To a solution of benzyl N-{1-[(tert-butyldiphenylsilyl)oxy]-3-hydroxypropan-2-yl} carbamate (35 g, 75.49 mmol) in DCM (400) was added DHP (34.5 mL, 377.45 mmol) and 4-methylbenzene-1-sulfonic acid (3.71 mg, 0.022 mmol) at 0° C. The reaction was allowed to warm to room temperature and stirred for 2.5 hours, then quenched by the addition of water. The reaction mixture was extracted with $CH_2Cl_2$ (3×20 mL) and the combined organic layers were washed with brine, dried over $Na_2SO_4$, filtered, and concentrated in vacuo. The residue was purified by silica gel column chromatography, eluting with PE/EA (20:1) to afford 27-2 as a yellow oil. ESI-MS m/z: 548 $[M+H]^+$.

Step 4: To a solution of 27-2 (37.0 g, 67.55 mmol) in THF (230 mL) was added KHMDS (26.95 g, 135.09 mmol) at 0° C. The mixture was stirred for 5 min and 2,2-difluoroethyl trifluoromethanesulfonate (17.91 mL, 135.09 mmol, 2.00 eq) was added. The mixture was allowed to warm to room temperature and stirred for 2 hours, then quenched by water and extracted with ethyl acetate (3×10 mL). The organics were combined and washed with brine, dried over $Na_2SO_4$, filtered, and concentrated in vacuo. The residue was purified by silica gel column chromatography, eluting with petroleum ether/ethyl acetate (5:1) to afford 27-3 as a colorless oil. ESI-MS m/z: 634 $[M+Na]^+$.

Step 5: To a solution of 27-3 (10.0 g, 18.26 mmol) in EtOH (112 mL) was added PPTS (421.0 mg, 1.68 mmol) at room temperature. The mixture was stirred overnight at 60° C., then cooled to room temperature and the reaction quenched by the addition of sat. NH$_4$Cl (aq.) (10 mL) at 0° C. The resulting mixture was concentrated under vacuum to remove EtOH, then extracted with ethyl acetate (3×10 mL). The residue was purified by silica gel column chromatography, eluting with petroleum ether/ethyl acetate (5:1) to afford benzyl N-{1-[(tert-butyldiphenylsilyl)oxy]-3-(oxan-2-yloxy)propan-2-yl}-N-(2,2-difluoroethyl)carbamate as a yellow oil. ESI-MS m/z: 528 [M+H]$^+$.

Step 6: To a solution of benzyl N-{1-[(tert-butyldiphenylsilyl)oxy]-3-hydroxypropan-2-yl}-N-(2,2-difluoroethyl) carbamate (8.1 g, 15.35 mmol) in DCM (50 mL) was added DMP (7.16 g, 16.89 mmol) at 0° C. The mixture was allowed to warm to room temperature and stirred overnight, then quenched by addition of water. The resulting mixture was extracted with CH$_2$Cl$_2$ (3×10 mL). The combined organic layers were washed with brine, dried over Na$_2$SO$_4$, filtered, and concentrated in vacuo. The residue was purified by silica gel column chromatography, eluting with petroleum ether/ethylacetate (20:1) to afford 27-4 as a colorless oil. ESI-MS m/z: 526 [M+H]$^+$.

Step 7: To a solution of 27-4 (3.0 g, 5.71 mmol) in THF (30.0 mL) was added bromo(methyl)magnesium (1.53 g, 12.84 mmol) at −78° C. The mixture was stirred for 30 min at room temperature, then quenched by the addition of sat. NH$_4$Cl (aq.) (10 mL) at 0° C. The reaction mixture was concentrated under vacuum to remove THF, then the aqueous phase was extracted with ethyl acetate (3×10 mL). The combined organic layers were dried over anhydrous Na$_2$SO$_4$, filtered, and the filtrate concentrated under reduced pressure to give a residue. The residue was purified by silica gel column chromatography, eluting with petroleum ether/ethyl acetate (10:1) to afford benzyl N-{1-[(tert-butyldiphenylsilyl)oxy]-3-hydroxybutan-2-yl}-N-(2,2-difluoroethyl) carbamate as a colorless oil. ESI-MS m/z: 542 [M+H]$^+$.

Step 8: To a solution of benzyl N-{1-[(tert-butyldiphenylsilyl)oxy]-3-hydroxypropan-2-yl} carbamate (2.5 g, 5.39 mmol) in DCM (25 mL) were added DHP (2.47 mL, 26.96 mmol), 4-methylbenzene-1-sulfonic acid, and pyridine (135.5 mg, 0.54 mmol) at 0° C. The reaction was allowed to warm to room temperrure and stirred overnight, then quenched with water at 0° C. The aqueous layer was extracted with CH$_2$Cl$_2$ (3×10 mL). The combined organic layers were dried over anhydrous Na$_2$SO$_4$, filtered, and the filtrate concentrated under reduced pressure to afford benzyl N-{1-[(tert-butyldiphenylsilyl)oxy]-3-(oxan-2-yloxy)propan-2-yl} carbamate as a colorless oil which was used directly in the next step without further purification. ESI-MS m/z: 626 [M+H]$^+$.

Step 9: To a solution of benzyl N-{1-[(tert-butyldiphenylsilyl)oxy]-3-(oxan-2-yloxy)butan-2-yl}-N-(2,2-difluoroethyl) carbamate (2.4 g, 3.84 mmol) in 25 mL MeOH was added Pd/C (408.1 mg, 0.384 mmol, 10%) under hydrogen atmosphere in a 50 mL reaction vial. The mixture was hydrogenated at room temperature overnight under a hydrogen balloon. The reaction mixture was filtered through a Celite pad and the celite pad washed with MeOH (3×10 mL). The filtrate was concentrated under reduced pressure to afford {1-[(tert-butyldiphenylsilyl)oxy]-3-(oxan-2-yloxy)butan-2-yl}(2,2-difluoroethyl)amine as a colorless oil, which was used directly in the next step without further purification. ESI-MS m/z: 492 [M+H]$^+$.

Step 10: To a solution of {1-[(tert-butyldiphenylsilyl)oxy]-3-(oxan-2-yloxy)butan-2-yl}(2,2-difluoroethyl)amine (1 g, 2.03 mmol) in THF (10 mL) was added TBAF (0.80 g, 3.05 mmol) dropwise. After stirring for 2 h at rt under a nitrogen atmosphere, the mixture was concentrated under vacuum to give a residue. The residue was purified by silica gel column chromatography, eluting with petroleum ether/ethyl acetate (100-0%) to afford 27-5 as a colorless oil. ESI-MS m/z: 254 [M+H]$^+$.

Step 11: To a solution of 27-5 (267.0 mg, 1.05 mmol) and 7-bromo-6-chloro-5,8-difluoro-2-(methylsulfanyl)quinazolin-4-ol (27-6) (300 mg, 0.88 mmol) in THF (3 mL) was added NaH (105.4 mg, 2.63 mmol, 60%) at 0° C. The mixture was allowed to warm to room temperature and stirred overnight, then quenched with sat. NH$_4$Cl (aq.) at 0° C. The reaction mixture was extracted with CH$_2$Cl$_2$ (3×5 mL) and the organics were combined, washed with brine, dried over Na$_2$SO$_4$, filtered, and concentrated in vacuo. The residue was purified by silica gel column chromatography, eluting with CH$_2$Cl$_2$/MeOH (1% MeOH) to afford 27-7 as a yellow solid. ESI-MS m/z: 574 [M+H]$^+$.

Step 12: To a solution of 27-7 (300 mg, 0.52 mmol) and POCl3 (224.04 mg, 1.46 mmol) in dioxane (3 mL) was added TEA (591.5 mg, 5.85 mmol) at room temperature and the resulting mixture stirred for 3 hours. The reaction mixture was concentrated under reduced pressure to give a residue, which was purified by silica gel column chromatography, eluting with petroleum ether/ethyl acetate (7:3), to afford 7-bromo-8-chloro-13-(2,2-difluoroethyl)-6-fluoro-3-(methylsulfanyl)-12-[1-(oxan-2-yloxy)ethyl]-10-oxa-2,4,13-triazatricyclo[7.4.1.0^{5,14}]tetradeca-1,3,5(14),6,8-pentaene as an off-white solid. ESI-MS m/z: 556 [M+H]$^+$.

Step 13: To a solution of 7-bromo-8-chloro-13-(2,2-difluoroethyl)-6-fluoro-3-(methylsulfanyl)-12-[1-(oxan-2-yloxy)ethyl]-10-oxa-2,4,13-triazatricyclo[7.4.1.0^{5,14}]tetradeca-1,3,5(14),6,8-pentaene (230 mg, 0.41 mmol) in DCM (2 mL) was added m-CPBA (143.8 mg, 1.24 mmol) at −10° C. The mixture was stirred for 1.5 hours, then quenched by the addition of sat. Na$_2$SO$_3$(aq.) (5 mL) at room temperature. The reaction mixture was extracted with CH$_2$Cl$_2$ (3×5 mL). The extracts were combined, washed with brine, dried over Na$_2$SO$_4$, filtered, and concentrated in vacuo. The residue was purified by silica gel column chromatography, eluting with petroleum ether/ethyl acetate (7:3) to afford 27-8 as an off-white solid. ESI-MS m/z: 588 [M+H]$^+$.

Step 14: To a solution of 27-8 (140 mg, 0.238 mmol) and 2-10 (45.4 mg, 0.29 mmol) in THF (2 mL) were added t-BuOK (40.0 mg, 0.36 mmol) dropwise at 0° C. After stirring for 1 hour at rt under a nitrogen atmosphere, the resulting mixture was concentrated under reduced pressure to give a residue. The residue was purified by reverse-phase flash chromatography (column, C$_{18}$; mobile phase, MeCN in water (10 mmol/L NH$_4$HCO$_3$)) to afford 27-9 as an off-white solid. ESI-MS m/z: 667 [M+H]$^+$.

Step 15: To a solution of 27-9 (90 mg, 0.16 mmol) and 2-12 (163 mg, 0.41 mmol) in toluene (5.4 mL) were added Cs$_2$CO$_3$ (395 mg, 1.22 mmol) and dichloropalladium; {2-[2-(diphenylphosphanyl) phenoxy]phenyl} diphenylphosphane (14.5 mg, 0.02 mmol). After stirring for 2 hours at 110° C. under a nitrogen atmosphere, the reaction mixture was cooled to room temperature and concentrated under reduced pressure to give a residue. The residue was purified by reverse-phase flash chromatography (column, C$_{18}$; mobile phase, MeCN in water (10 mmol/L NH$_4$HCO$_3$)) to afford 27-10 as a yellow solid. ESI-MS m/z: 879 [M+H]$^+$.

Step 16: To a solution of 27-10 (62 mg, 0.071 mmol) in DCM/EtOH (3 mL/1 mL) was added CF$_3$COOH (1 mL) at room temperature. The mixture was stirred for 2 hours, then solvent was removed under reduced pressure to give a residue. The residue was dissolved in DCM (3 mL) and CF₃COOH (0.1 mL) was added. The resulting mixture was stirred for 1 hour and solvent was removed under reduced pressure to give a crude product, which was purified by prep-HPLC (Column: XBridge Prep OBD C18 Column, 30*150 mm, 5 um; Mobile Phase A: water (10 mmol/L NH₄HCO₃), Mobile Phase B: ACN) to afford two peaks as off-white solids. 899 (Peak 1): ESI-MS m/z: 695.25 [M+H]⁺. ¹HNMR (400 MHZ, DMSO-d₆): δ 8.08 (s, 2H), 7.29-7.00 (m, 2H), 6.72-6.32 (m, 1H), 5.29 (d, J=54.3 Hz, 1H), 5.11 (d, J=4.8 Hz, 1H), 5.02 (dd, J=12.8, 4.5 Hz, 1H), 4.87-4.63 (m, 1H), 4.25 (d, J=12.9 Hz, 1H), 4.16-4.06 (m, 1H), 4.05-3.94 (m, 2H), 3.93-3.75 (m, 2H), 3.11 (s, 2H), 3.03 (s, 1H), 2.84 (s, 1H), 2.23-2.11 (m, 1H), 2.10-1.94 (m, 2H), 1.92-1.63 (m, 3H), 1.16 (d, J=6.2 Hz, 3H). 1102 (Peak 2): ESI-MS m/z: 694.80 [M+H]⁺. ¹HNMR (400 MHZ, DMSO-d6):(400 MHZ, DMSO-d₆): δ 8.07 (s, 2H), 7.37-7.18 (m, 1H), 7.14 (t, J=8.9 Hz, 1H), 6.66-6.26 (m, 1H), 5.28 (d, J=54.4 Hz, 1H), 5.15 (d, J=4.7 Hz, 1H), 4.96 (dd, J=12.7, 4.7 Hz, 1H), 4.90-4.68 (m, 1H), 4.39 (d, J=12.4 Hz, 1H), 4.20-3.95 (m, 3H), 3.94- 3.69 (m, 2H), 3.09 (d, J=7.7 Hz, 2H), 3.02 (s, 1H), 2.84 (t, J=7.7 Hz, 1H), 2.23-2.10 (m, 1H), 2.04 (d, J=19.8 Hz, 2H), 1.88-1.71 (m, 3H), 1.07 (d, J=6.2 Hz, 3H).

Example 1ab: Synthesis of 3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-4-yl)-N,N-dimethylcyclobutane-1-carboxamide (754 and 640)

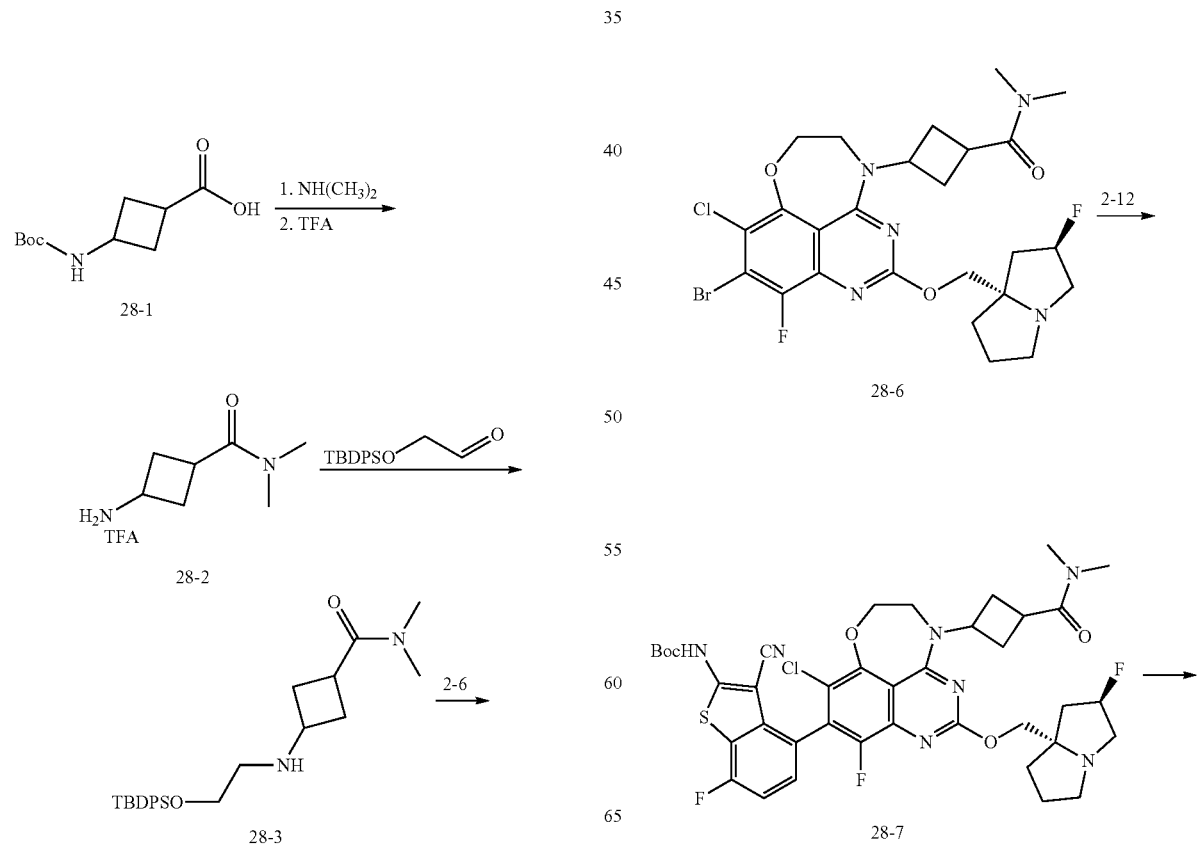

-continued

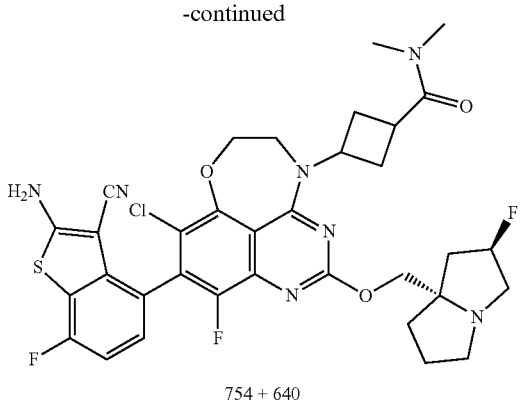

754 + 640

Step 1: To a stirred solution of dimethylamine hydrochloride (909 mg, 11.150 mmol) in DMF (30.0 mL) were added DIEA (1200 mg, 9.292 mmol), 3-[(tert-butoxycarbonyl) amino]cyclobutane-1-carboxylic acid (28-1) (2 g, 9.292 mmol) and [(dimethylamino)({3H-[1,2,3]triazolo[4,5-b]pyridin-3-yloxy}) methylidene]dimethylazanium; hexafluoro-lambda5-phosphanuide (5299 mg, 13.938 mmol) at 0° C. under nitrogen atmosphere. The resulting mixture was stirred for 2 hours at room temperature and concentrated under reduced pressure to give a residue. The residue was purified by silica gel column chromatography, eluting with petroleum ether/ethyl acetate (2:1) to afford tert-butyl N-[3-(dimethylcarbamoyl)cyclobutyl]carbamate as a yellow liquid. ESI-MS m/z: 243 [M+H]$^+$.

Step 2: A solution of tert-butyl N-[3-(dimethylcarbamoyl) cyclobutyl]carbamate (2 g, 8.25 mmol) in DCM (30 mL) was treated with TFA (10 mL) for 2 hours at room temperature under nitrogen atmosphere. The resulting mixture was concentrated under reduced pressure to afford 28-2 as a brown oil. The crude product was used in the next step directly without further purification. ESI-MS m/z: 241 [M+H]$^+$.

Step 3: To a stirred solution of 28-2 (1.1 g, 7.735 mmol) and 2-[(tert-butyldiphenylsilyl)oxy]acetaldehyde (2.31 g, 7.735 mmol) in DCM was added sodium bis(acetyloxy) boranuidyl acetate (3.28 g, 15.470 mmol) dropwise at 0° C. under nitrogen atmosphere. The resulting mixture was stirred for 2 hours at room temperature, then concentrated under reduced pressure to afford 28-3. The crude product was used in the next step directly without further purification. ESI-MS m/z: 425 [M+H]$^+$.

Step 4: To a 40 mL vial were added 28-3 (1 g, 2.35 mmol), 2-6 (0.42 g, 1.17 mmol), 2-methylpropan-2-ol (10 mL) and DIEA (0.76 g, 5.88 mmol) at room temperature. The resulting mixture was stirred overnight at 90° C. under nitrogen atmosphere, then cooled to room temperature and concentrated under reduced pressure. The product was extracted with CH$_2$Cl$_2$ (3×50 mL). The combined organic layers were dried over anhydrous Na$_2$SO$_4$, filtered, and the filtrate concentrated under reduced pressure to give a residue. The residue was purified by silica gel column chromatography, eluting with petroleum ether/ethyl acetate (10:1) to afford 28-4 as a light brown solid. ESI-MS m/z: 747 [M+H]$^+$.

Step 5: To an 8 mL vial were added 28-4 (246 mg, 0.329 mmol) in DMF (2 mL) and CsF (100 mg, 0.658 mmol) at room temperature. The resulting mixture was stirred for 3 hours at 80° C. under nitrogen atmosphere, then cooled to room temperature, diluted with water and extracted with DCM. The combined organic layers were washed with brine, dried over Na$_2$SO$_4$, filtered, and concentrated in vacuo. The residue was purified by silica gel column chromatography, eluting with petroleum/ethyl acetate (1:1) to afford 3-[7-bromo-8-chloro-6-fluoro-3-(methylsulfanyl)-10-oxa-2,4, 13-triazatricyclo[7.4.1.0^{5,14}] tetradeca-1,3,5(14),6,8-pentaen- 13-yl]-N,N-dimethylcyclobutane-1-carboxamide as a white solid. ESI-MS m/z: 489 [M+H]$^+$.

Step 6: To an 8 mL vial were added 3-[7-bromo-8-chloro-6-fluoro-3-(methylsulfanyl)-10-oxa-2,4,13-triazatricyclo [7.4.1.0^{5,14}] tetradeca-1,3,5(14),6,8-pentaen-13-yl]-N, N-dimethylcyclobutane-1-carboxamide (100 mg, 0.204 mmol), DCM (5 mL) and m-CPBA (105.69 mg, 0.612 mmol) at −10° C. The resulting mixture was stirred for 1 hour at −10° C. to room temperature under nitrogen atmosphere, then quenched by the addition of sat. NaHCO$_3$(aq.). The resulting mixture was diluted with CH$_2$Cl$_2$ (25 mL) and washed with sat. NaHCO$_3$(aq.). The organic layer was dried over anhydrous Na$_2$SO$_4$ and concentrated under reduced pressure to afford 28-5, which was used in the next step without further purification. ESI-MS m/z: 521 [M+H]$^+$.

Step 7: To an 8 mL vial were added 28-5 (120 mg, 0.23 mmol), 2-10 (40 mg, 0.253 mmol) and THF (2 mL) at 0° C. Then, t-BuOK (0.34 mL, 0.345 mmol) was added dropwise at 0° C. under nitrogen atmosphere. The reaction was quenched by the addition of water at room temperature. The resulting mixture was concentrated under reduced pressure and purified by silica gel column chromatography, eluting with CH$_2$Cl$_2$/MeOH (20:1) to afford 28-6 as a white solid. ESI-MS m/z: 600 [M+H]$^+$.

Step 8: To an 8 mL vial were added 28-6 (22 mg, 0.037 mmol), 2-12 (22.2 mg, 0.055 mmol), dicyclohexyl[2', 4', 6'-tris(propan-2-yl)-[1,1'-biphenyl]-2-yl]phosphane; {2'-amino-[1,1'-biphenyl]-2-yl}(chloro)palladium (2.88 mg, 0.004 mmol) and K$_3$PO$_4$ (23.31 mg, 0.111 mmol) at room temperature. THF (1 mL) was injected under nitrogen atmosphere and the resulting mixture was stirred overnight at 65° C. The reaction mixture was cooled to room temperature, then concentrated under reduced pressure to give a residue. The residue was purified by prep-TLC (CH$_2$Cl$_2$/MeOH 12:1) to afford 28-7 as a light brown oil. ESI-MS m/z: 812 [M+H]$^+$.

Step 9: To a 20 mL reaction vial were added 28-7 (22 mg, 0.011 mmol), DCM (1.5 mL) and TFA (0.5 mL) at room temperature. The resulting mixture was stirred for 2 hours, then concentrated under reduced pressure. The crude product was purified by prep-HPLC (Column: XBridge Shield RP18 OBD Column, 30×150 mm, 5 um; Mobile Phase A: water (10 mmol/L NH$_4$HCO$_3$), Mobile Phase B: ACN) to afford desired product of peak 1 and peak 2.754 (Peak 1): ESI-MS m/z: 712 [M+H]$^+$. $^1$H NMR:(400 MHZ, Chloroform-d) δ 7.24-7.18 (m, 1H), 7.01 (td, J=8.8, 4.4 Hz, 1H), 5.59 (d, J=45.8 Hz, 2H), 5.50-5.31 (m, 1H), 5.23 (q, J=8.6 Hz, 1H), 4.72-4.44 (m, 4H), 3.99-3.87 (m, 1H), 3.87-3.59 (m, 2H), 3.53-3.36 (d, 1H), 3.28-3.11 (m, 2H), 3.04 (s, 3H), 2.97 (s, 3H), 2.79-2.59 (m, 2H), 2.58-2.38 (m, 5H), 2.21-2.00 (m, 3H), 1.26 (s, 1H). 640 (Peak 2): ESI-MS m/z: 712 [M+H]$^+$. $^1$H NMR (400 MHz, Chloroform-d) δ 7.25-7.13 (m, 1H), 7.04-6.86 (m, 1H), 6.67-6.43 (m, 2H), 5.67-5.22 (m, 1H), 4.95 (d, J=8.5 Hz, 1H), 4.70-4.31 (m, 4H), 4.01-3.58 (m, 4H), 3.43 (s, 1H), 3.30-3.11 (m, 2H), 3.02 (d, J=5.3 Hz, 3H), 2.98 (d, J=5.0 Hz, 3H), 2.90-2.76 (m, 2H) 2.65-2.55 (m, 5H), 2.21-1.93 (m, 3H), 1.40-1.17 (m, 2H).

Example 1ac: Synthesis of 2-amino-4-(8-chloro-4-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (1060)

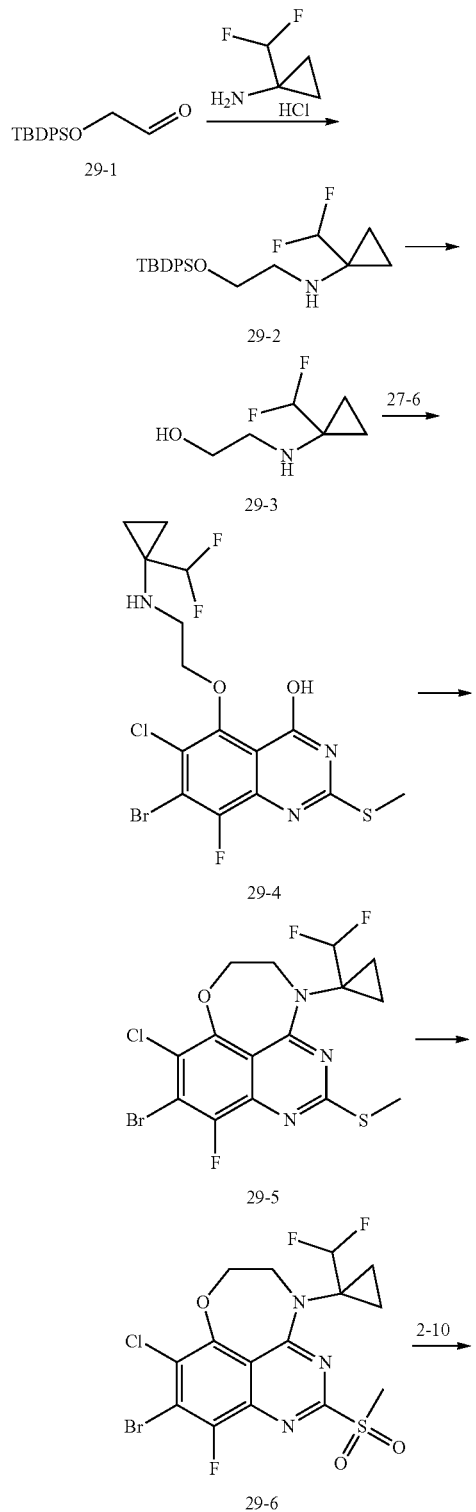

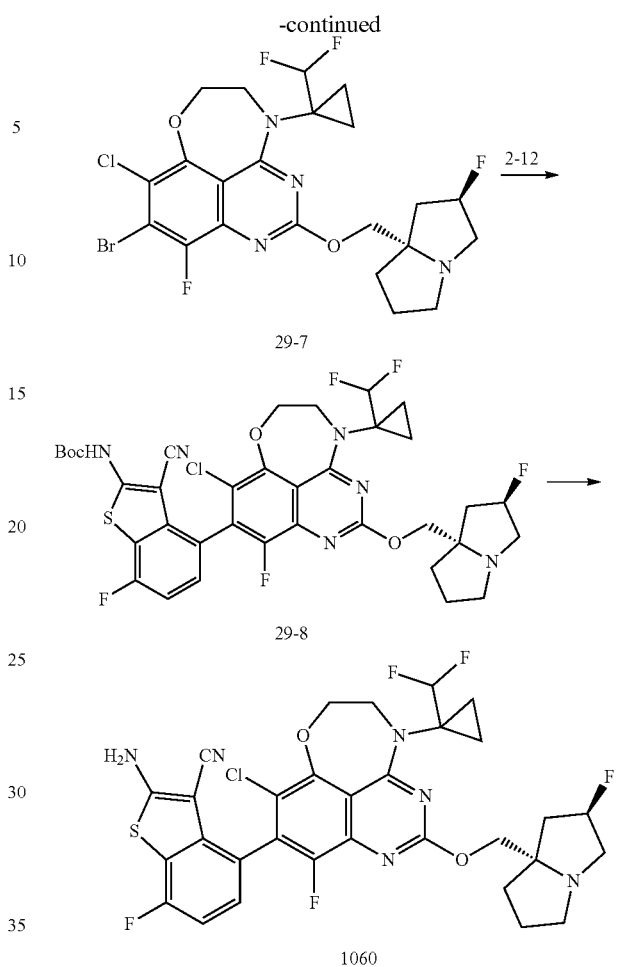

Step 1: To a stirred solution of 1-(difluoromethyl) cyclopropan-1-amine hydrochloride (1125 mg, 7.83 mmol) and TEA (793 mg, 7.83 mmol) in DCM (15.6 mL) were added 2-[(tert-butyldiphenylsilyl) oxy]acetaldehyde (29-1) (780 mg, 2.613 mmol) and STAB (1661 mg, 7.83 mmol) at room temperature. The resulting mixture was stirred for 2 hours at room temperature, then quenched with ice water. The resulting mixture was extracted with $CH_2Cl_2$ (3×30 mL), and organics were combined, washed with brine, dried over $Na_2SO_4$, filtered, and concentrated in vacuo. The residue was purified by silica gel column chromatography, eluting with petroleum ether/ethyl acetate (1:1) to afford 29-2 as a colorless oil. ESI-MS m/z: 390 [M+H]$^+$.

Step 2: To a stirred solution of 29-2 (360 mg, 0.924 mmol) in DMF (3.6 mL) was added CsF (280 mg, 1.848 mmol) in portions at room temperature. The resulting mixture was stirred for 2 hours at room temperature, then quenched with water at room temperature and extracted with $CH_2Cl_2$ (3×30 mL). The organics were combined, washed with brine, dried over anhydrous $Na_2SO_4$, filtered, and the filtrate concentrated under reduced pressure to give 29-3 as a colorless oil which was used directly in the next step without further purification. ESI-MS m/z: 152 [M+H]$^+$.

Step 3: To a stirred solution of 29-3 (220 mg, 1.455 mmol) in THF (2.5 mL) was added NaH (419 mg, 17.46 mmol) in portions at 0° C. The resulting mixture was stirred for 1 hour at room temperature, then 27-6 (248 mg, 0.728 mmol) was added and the mixture was stirred overnight at room temperature. The reaction was quenched with ice water at room temperature, then extracted with ethyl acetate (3×20 mL). The extracts were combined and washed with brine, dried over Na$_2$SO$_4$, filtered, and concentrated in vacuo. The residue was purified by reverse-phase flash chromatography (column, C$_{18}$; mobile phase, MeCN in water (10 mmol/L NH$_4$HCO$_3$)) to afford 29-4 as a yellow solid. ESI-MS m/z: 472 [M+H]$^+$.

Step 4: To a stirred solution of 29-4 (293 mg, 0.620 mmol) in SOCl2 (4.5 mL) was added DMF (2.27 mg, 0.031 mmol) dropwise at room temperature. The resulting mixture was stirred for 3 hours at 80° C. under nitrogen atmosphere, then cooled to room temperature and concentrated under vacuum. The residue was treated with water (5 mL) and extracted with ethyl acetate (3×10 mL). The extracts were combined, washed with brine, dried over Na$_2$SO$_4$, filtered, and concentrated in vacuo. The residue was purified by reverse-phase flash chromatography (column, C$_{18}$; mobile phase, MeCN in water (10 mmol/L NH$_4$HCO$_3$)) to afford 29-5 as a yellow solid. ESI-MS m/z: 454 [M+H]$^+$.

Step 5: To a stirred solution of 29-5 (130 mg, 0.286 mmol) in DCM (3 mL) was added m-CPBA (123 mg, 0.715 mmol) in portions at 0° C. The resulting mixture was stirred for 2 hours at 0° C. and diluted with ethyl acetate (30 mL), then washed with 2×10 mL of NaHCO$_3$(aq.). The organics were washed with brine, dried over sodium sulfate, filtered and solvent removed under reduced pressure to give 29-6 (150 mg, crude) as a yellow solid which was used directly in the next step without further purification. ESI-MS m/z: 486 [M+H]$^+$.

Step 6: To a stirred solution of 29-6 (150 mg, 0.308 mmol) and 2-10 (88 mg, 0.554 mmol) in toluene (3 mL) was added t-BuONa (88 mg, 0.924 mmol) at 0° C. The resulting mixture was stirred for 1 hour at 0° C. and quenched with ice water. The mixture was extracted with ethyl acetate (3×30 mL). The organics were combined and washed with brine, dried over Na$_2$SO$_4$, filtered, and concentrated in vacuo. The residue was purified by reverse-phase flash chromatography (column, C$_{18}$; mobile phase, MeCN in water (10 mmol/L NH$_4$HCO$_3$)) to afford 29-7 as a yellow solid. ESI-MS m/z: 565 [M+H]$^+$.

Step 7: To a stirred solution of 29-7 (95 mg, 0.168 mmol) and 2-12 (135 mg, 0.336 mmol) in toluene (2 mL) were added DPEPhosPdCl2 (18 mg, 0.025 mmol) and Cs$_2$CO$_3$ (164 mg, 0.504 mmol) at room temperature. The resulting mixture was purged and degassed with nitrogen three times, then heated to 100° C. and stirred for 3 hours under nitrogen atmosphere. The reaction was cooled to room temperature and the resulting mixture was diluted with ethyl acetate (30 mL). The combined organics were washed with brine, dried over Na$_2$SO$_4$, filtered, and concentrated in vacuo. The residue was purified by reverse-phase flash chromatography (column, C$_{18}$; mobile phase, MeCN in water (10 mmol/L NH$_4$HCO$_3$)) to afford 29-8 as a yellow solid. ESI-MS m/z: 777 [M+H]$^+$.

Step 8: To a stirred mixture of 29-8 (35 mg, 0.045 mmol) in DCM (5.0 mL) was added TFA (1.0 mL) at room temperature. The resulting mixture was stirred for 1 hour at room temperature and concentrated under vacuum to give a crude residue, which was purified by Chiral-prep-HPLC (Column 30×150 mm, 5 um; mobile phase, water (10 mmol/L NH$_4$HCO$_3$) and ACN (40% ACN up to 75% in 10 min)) to afford 1060 as a white solid. ESI-MS m/z: 677 [M+H]$^+$. $^1$H NMR (400 MHZ, DMSO-d$_6$) δ 8.08 (br, 2H), 7.18-7.13 (m, 2H), 6.72-6.43 (m, 1H), 5.35-5.22 (m, 1H), 4.60-4.54 (m, 2H), 4.11-3.99 (m, 4H), 3.10 (s, 2H), 3.02 (s, 1H), 2.84 (s, 1H), 2.16-2.00 (m, 3H), 1.86-1.79 (m, 3H), 1.30-1.24 (m, 4H).

Example 1ad: Synthesis of 2-amino-4-(8-chloro-4-(3,3-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (807)

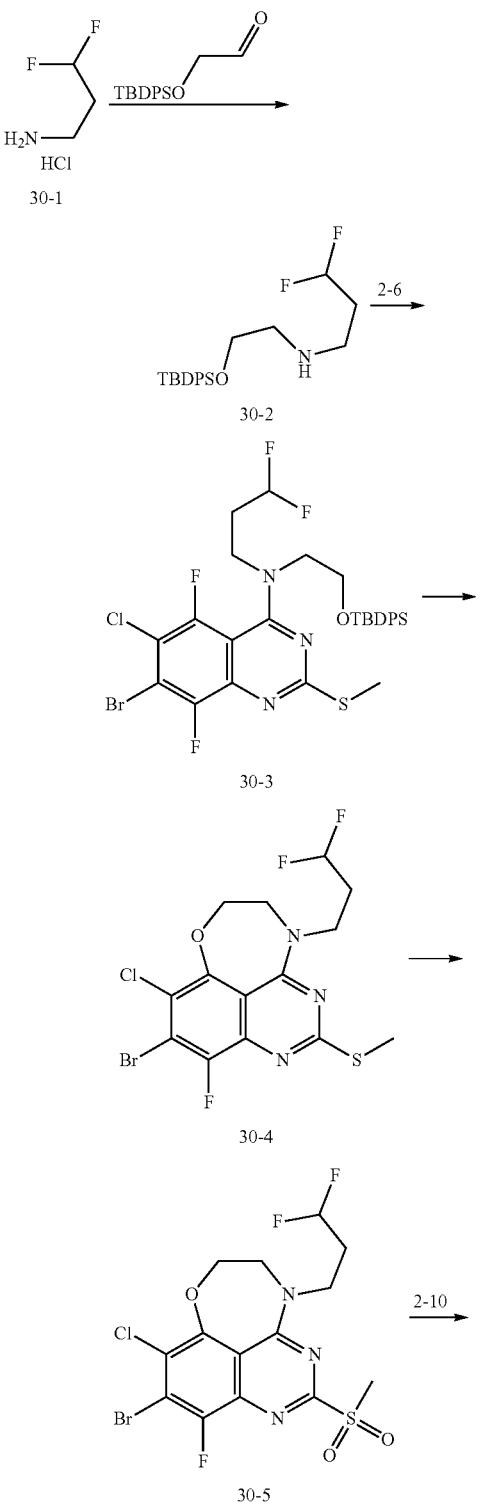

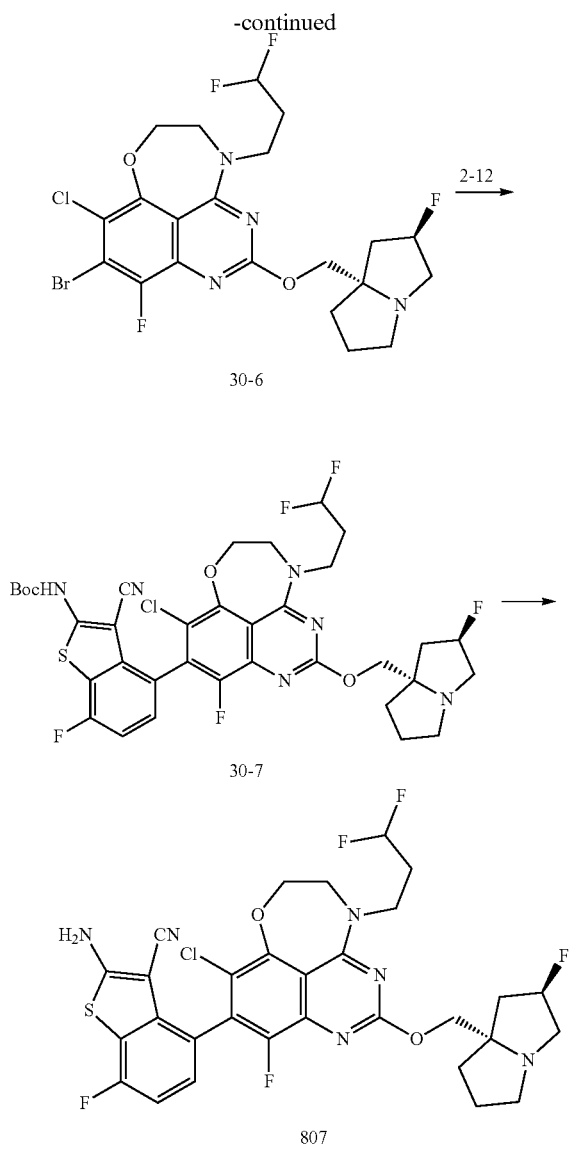

Step 1: To a stirred mixture of 3,3-difluoropropan-1-amine hydrochloride (30-1) (260 mg, 1.976 mmol) and 2-[(tert-butyldiphenylsilyl)oxy]acetaldehyde (589 mg, 1.976 mmol) in DCM (5.2 mL, 81.787 mmol) was added NaBH$_3$CN (372 mg, 5.928 mmol) at room temperature. The final reaction mixture was stirred for 2 hours at room temperature. The reaction was quenched with ice water and extracted with CH$_2$Cl$_2$ (3×50 mL). The combined organic layers were dried over anhydrous Na$_2$SO$_4$, filtered, and the filtrate concentrated under reduced pressure to give a residue. The residue was purified by reverse-phase flash chromatography (column, C$_{18}$; mobile phase, MeCN in water (0.1% TFA)) to afford 30-2 as a light yellow oil. ESI-MS m/z: 378 [M+H]$^+$.

Step 2: To a stirred mixture of 30-2 (260 mg, 0.689 mmol) and 2-6 (198 mg, 0.551 mmol) in t-BuOH (5.2 mL) were added DIEA (178 mg, 1.378 mmol) at room temperature. The final reaction mixture was stirred for 30 min at 80° C., then cooled and the resulting mixture diluted with water (20 mL). The mixture was extracted with ethyl acetate (3×20 mL) and the combined organic layers were washed with brine, dried over Na$_2$SO$_4$, filtered, and concentrated in vacuo. The residue was purified by reverse-phase flash chromatography (column, C$_{18}$; mobile phase, MeCN in water (0.1% TFA)) to afford 30-3 as a light yellow solid. ESI-MS m/z: 700 [M+H]$^+$.

Step 3: To a stirred solution of 30-3 (360 mg, 0.513 mmol) in DMF (16 mL, 206.745 mmol) was added CsF (234 mg, 1.539 mmol) at room temperature. The reaction mixture was stirred for 30 min at 80° C., then cooled to room temperature and the resulting mixture diluted with ethyl acetate (200 mL). The combined organic layers were washed with water (5×50 mL), dried over anhydrous Na$_2$SO$_4$, filtered, and the filtrate concentrated under reduced pressure to give a residue. The residue was purified by reverse-phase flash chromatography (column, C$_{18}$; mobile phase, MeCN in water (10 mmol/L NH$_4$HCO$_3$)) to afford 30-4 as a yellow solid. ESI-MS m/z: 442 [M+H]$^+$.

Step 4: To a stirred solution of 30-4 (200 mg, 0.452 mmol) in DCM (4 mL) was added m-CPBA (233.88 mg, 1.356 mmol) in portions at −10° C. The final reaction mixture was stirred for 3 hours at 0° C., then quenched with sat. NaHCO$_3$ (aq.) and the mixture extracted with CH$_2$Cl$_2$ (3×50 mL). The combined organic layers were dried over anhydrous Na$_2$SO$_4$, filtered, and the filtrate concentrated under reduced pressure to give 30-5 which was used directly in the next step without further purification. ESI-MS m/z: 474 [M+H]$^+$.

Step 5: To a stirred solution of 30-5 (250 mg, 0.527 mmol) and 2-10 (167.7 mg, 1.054 mmol) in toluene (5 mL) was added t-BuONa (151 mg, 1.581 mmol) at 0° C. The final reaction mixture was stirred for 1 h at 0° C., then quenched with sat. NH$_4$Cl (aq.) at room temperature and extracted with ethyl acetate (3×40 mL). The combined organic layers were dried over anhydrous Na$_2$SO$_4$, filtered, and the filtrate concentrated under reduced pressure to give a reside. The residue was purified by reverse-phase flash chromatography (column, C$_{18}$; mobile phase, MeCN in water (10 mmol/L NH$_4$HCO$_3$)) to afford 30-6 as a light yellow solid. 553 [M+H]$^+$.

Step 6: To a solution of 30-6 (80 mg, 0.144 mmol) and 2-12 (175 mg, 0.432 mmol) in toluene (8 mL) were added Cs$_2$CO$_3$ (423 mg, 1.296 mmol) and DPEPhosPdCl$_2$ (20 mg, 0.029 mmol). The mixture was purged and degassed with argon three times, then heated to 110° C. and stirred for 1.5 hours under argon atmosphere. The reaction was cooled to room temperature, quenched with water, and extracted with ethyl acetate (3×30 mL). The combined organic layers were dried over anhydrous Na$_2$SO$_4$, filtered, and the filtrate concentrated under reduced pressure to give a residue. The residue was purified by prep-TLC (CH$_2$Cl$_2$/MeOH 5:1) to afford 30-7 as a light yellow solid. ESI-MS m/z: 765 [M+H]$^+$.

Step 7: To a stirred solution of 30-7 (80 mg, 0.084 mmol, 80%) in DCM (1 mL) was added TFA (0.2 mL) at room temperature. The final reaction mixture was stirred for 1.5 hour at room temperature and concentrated under reduced pressure to give a residue. The residue was purified by prep-HPLC (Column, Kinetex EVO prep C$_{18, 30*150, 5}$ um; mobile phase, water (10 mmol/L NH$_4$HCO$_3$) and ACN (30% ACN up to 70% in 8 min)) to afford 807 as a light yellow solid. ESI-MS m/z: 665 [M+H]$^+$.

$^1$H NMR (400 MHZ, DMSO-d$_6$) δ 8.07 (br, 2H), 7.22-7.18 (m, 1H), 7.15-7.11 (m, 1H), 6.41-6.11 (m, 1H), 5.34-5.20 (m, 1H), 4.59-4.52 (m, 2H), 4.13-4.03 (m, 2H), 4.00-3.89 (m, 4H), 3.09 (d, J=10.4 Hz, 2H), 3.01 (s, 1H), 2.86-2.80 (m, 1H), 2.40-2.27 (m, 2H), 2.18-1.97 (m, 3H), 1.86-1.74 (m, 3H).

Example 1ae: Synthesis of 2-amino-4-(9-chloro-11-fluoro-2-(((2R,7aS)-2-fluorotetrahydro-1H-pyrrolizin-7a(5H)-yl)methoxy)-6-hydroxy-4-(tetrahydrofuran-3-yl)-4,5,6,7-tetrahydro-[1,5]oxazocino[4,3,2-de]quinazolin-10-yl)-7-fluorobenzo[b]thiophene-3-carbonitrile (1225)

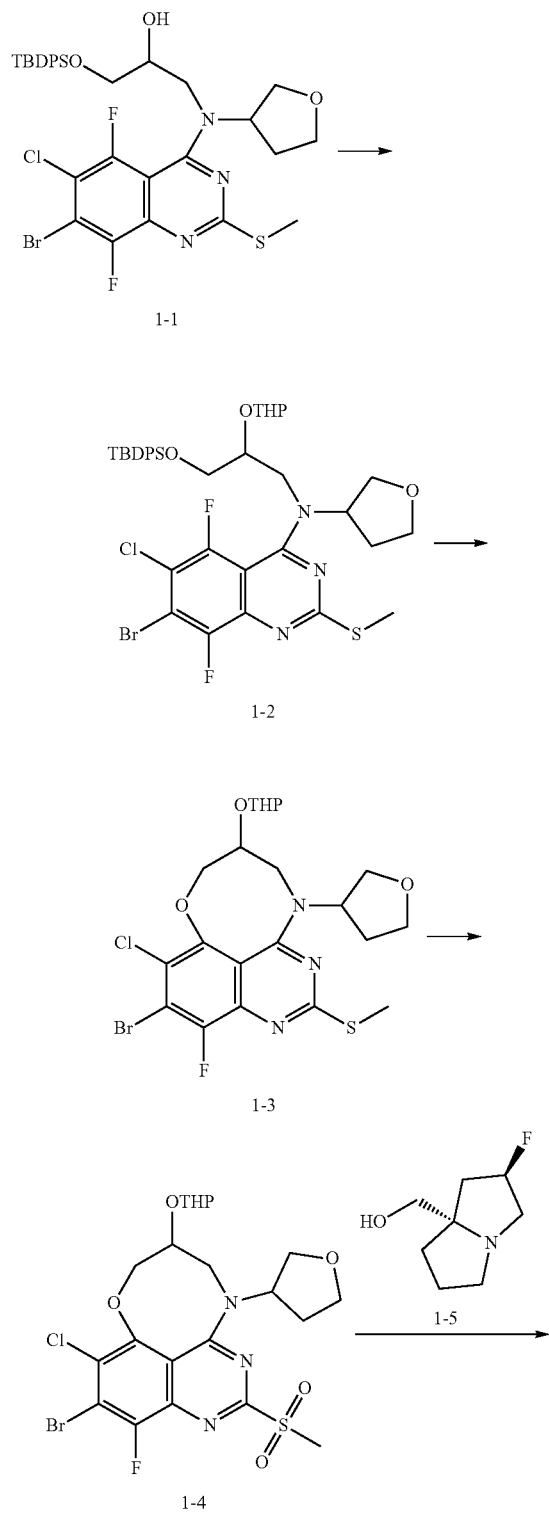

-continued

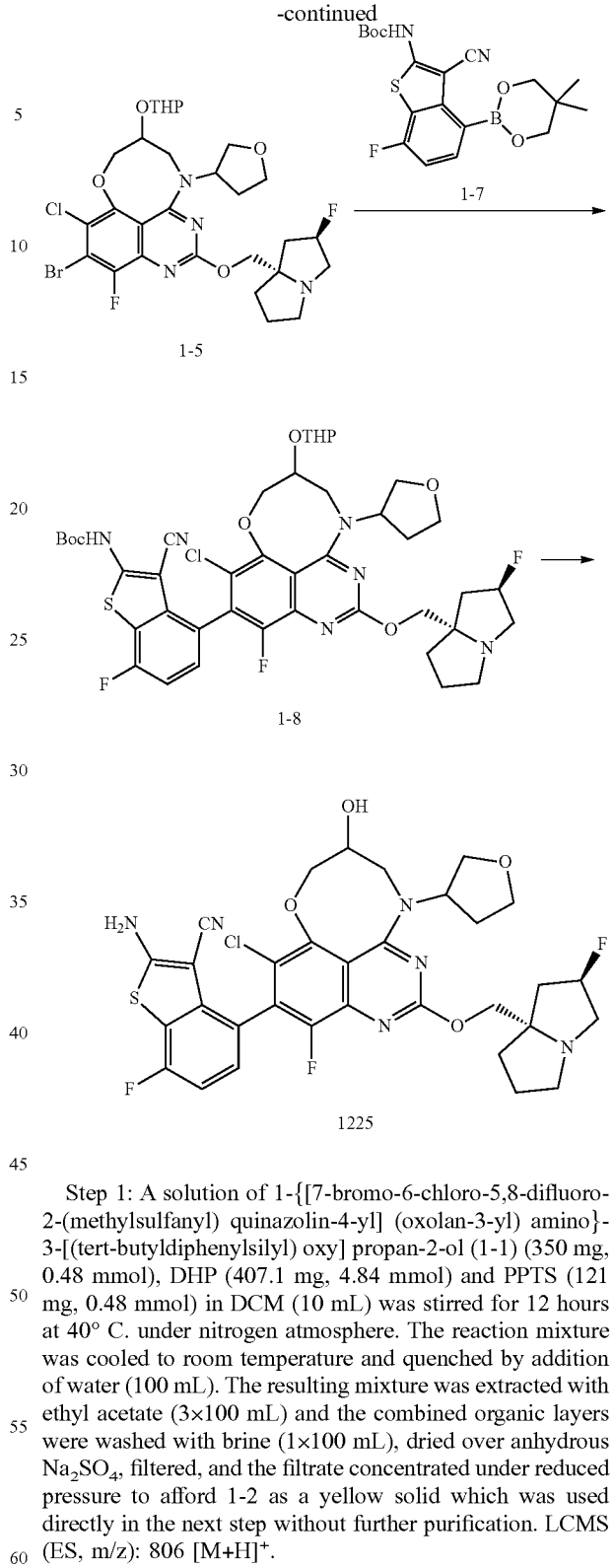

Step 1: A solution of 1-{[7-bromo-6-chloro-5,8-difluoro-2-(methylsulfanyl) quinazolin-4-yl] (oxolan-3-yl) amino}-3-[(tert-butyldiphenylsilyl) oxy] propan-2-ol (1-1) (350 mg, 0.48 mmol), DHP (407.1 mg, 4.84 mmol) and PPTS (121 mg, 0.48 mmol) in DCM (10 mL) was stirred for 12 hours at 40° C. under nitrogen atmosphere. The reaction mixture was cooled to room temperature and quenched by addition of water (100 mL). The resulting mixture was extracted with ethyl acetate (3×100 mL) and the combined organic layers were washed with brine (1×100 mL), dried over anhydrous Na$_2$SO$_4$, filtered, and the filtrate concentrated under reduced pressure to afford 1-2 as a yellow solid which was used directly in the next step without further purification. LCMS (ES, m/z): 806 [M+H]$^+$.

Step 2: A solution of 1-2 (300 mg, 0.37 mmol) and CsF (225 mg, 1.49 mmol) in DMF (6 mL) was stirred for 2 hours at 80° C. under nitrogen atmosphere. The reaction mixture was cooled to room temperature, then quenched by addition of water (100 mL) and extracted with ethyl acetate (3×100 mL). The combined organic layers were washed with brine (1×100 mL), dried over anhydrous Na$_2$SO$_4$, filtered, and the filtrate concentrated under reduced pressure to give a residue. The residue was purified by prep-TLC (petroleum/ethyl acetate=3:1) to afford 1-3 as a white solid. LCMS (ES, m/z): 548 [M+H]⁺.

Step 3: To a solution of 1-3 (110 mg, 0.2 mmol) in DCM (2 mL) at −10° C. under nitrogen atmosphere was added mCPBA (103 mg, 0.6 mmol) in portions. The resulting mixture was stirred for 3 hours at −10 to 0° C., then quenched by the addition of NaHSO₃ (2 mL) at 0° C. The residue was basified to pH 8 with saturated NaHCO₃(aq.) and extracted with ethyl acetate (3×50 mL). The combined organic layers were washed with brine (1×50 mL), dried over anhydrous Na₂SO₄, filtered, and the filtrate concentrated under reduced pressure to afford 1-4 as a yellow solid which was used directly in the next step without further purification. LCMS (ES, m/z): 580 [M+H]⁺.

Step 4: To a stirred solution of 1-4 (120 mg, 0.21 mmol) and [(2R,7aS)-2-fluoro-hexahydropyrrolizin-7a-yl] methanol (1-5) (39 mg, 0.25 mmol) in toluene (2 mL) was added t-BuONa (59 mg, 0.62 mmol) in portions at 0° C. under nitrogen atmosphere. The reaction was quenched by the addition of sat. NH₄Cl (aq.) (2 mL) at 0° C., then extracted with ethyl acetate (3×50 mL). The combined organic layers were washed with brine (1×50 mL), dried over anhydrous Na₂SO₄, filtered, and the filtrate concentrated under reduced pressure to give a residue. The residue was purified by reverse-phase flash chromatography (column, C₁₈; mobile phase, MeCN in water (0.1% NH₃·H₂O)) to afford 1-6 as a colorless oil. LCMS (ES, m/z): 659 [M+H]⁺.

Step 5: To an 8 mL reaction vial were added 1-6 (50 mg, 0.07 mmol), dichloropalladium {2-[2-(diphenylphosphanyl)phenoxy]phenyl}diphenylphosphane (8 mg, 0.011 mmol), tert-butyl N-[3-cyano-4-(5,5-dimethyl-1,3,2-dioxaborinan-2-yl)-7-fluoro-1-benzothiophen-2-yl]carbamate (1-7) (36.7 mg, 0.09 mmol) and Cs₂CO₃ (74 mg, 0.23 mmol) at room temperature. The reaction mixture was degassed and back filled with argon, then toluene (1 mL) was added dropwise. The reaction mixture was irradiated in a microwave reactor for 2.5 h at 100° C., then cooled to room temperature and the reaction quenched by the addition of water (50 mL). The resulting mixture was extracted with ethyl acetate (3×50 mL) and the combined organic layers were washed with brine (1×50 mL), dried over anhydrous Na₂SO₄, filtered, and the filtrate concentrated under reduced pressure to give a residue. The residue was purified by prep-TLC (CH₂Cl₂/MeOH 10:1) to afford 1-8 as a yellow solid. LCMS (ES, m/z): 871 [M+H]⁺.

Step 6: A solution of 1-8 (30 mg, 0.03 mmol) and HCl (gas) in 1,4-dioxane (1 mL) in ACN (1 mL) was stirred for 30 min at room temperature under nitrogen atmosphere. The residue was basified to pH 9 with NH₃·H₂O, then extracted with ethyl acetate (3×50 mL). The combined organic layers were washed with brine (1×50 mL), dried over anhydrous Na₂SO₄, filtered, and the filtrate concentrated under reduced pressure to give a residue. The residue was purified by prep-HPLC (Column: Kinetex EVO C18 Column, 30×150, 5 um; Mobile Phase A: water (10 mmol/L NH₄HCO₃), Mobile Phase B: ACN) to afford 1225 as a white solid. LCMS (ES, m/z):687 [M+H]⁺. ¹H NMR (400 MHZ, DMSO-d₆) δ 8.51 (s, 1H), 7.26(s,1H), 7.09 (s, 1H), 6.07 (s, 2H), 5.46 (s, 2H), 5.21 (s, 1H), 5.16 (s, 1H), 4.68 (s, 1H), 4.16-3.97 (m, 1H), 3.90-3.82 (m, 1H), 3.80 (d, J=4.7 Hz, 2H), 3.65 (d, J=8.4 Hz, 2H), 3.09 (d, J=10.6 Hz, 2H), 3.02 (s, 1H), 2.84 (s, 1H), 2.03 (d, J=16.3 Hz, 5H), 1.79 (dd, J=12.2, 7.5 Hz, 3H).

Example 1af: Synthesis of 2-amino-4-((R)-9-chloro-4-(2,2-difluoroethyl)-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino [4,3,2-de]quinazolin-10-yl)-7-fluorobenzo[b]thiophene-3-carbonitrile (1203)

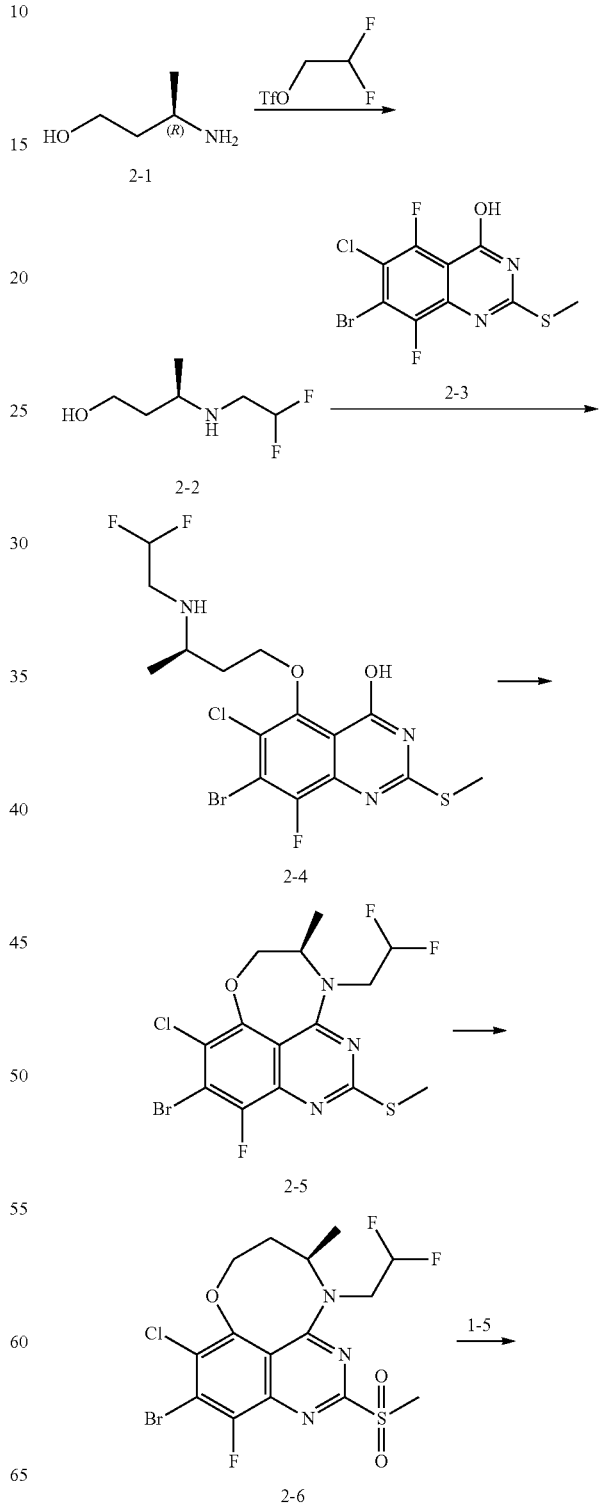

-continued

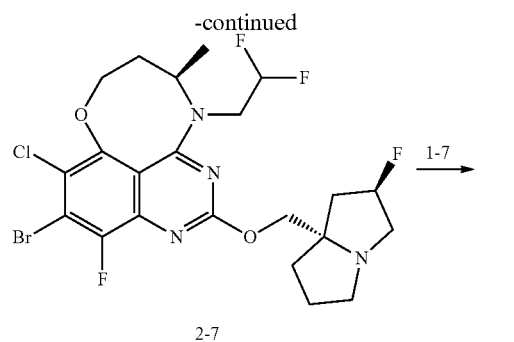

2-7

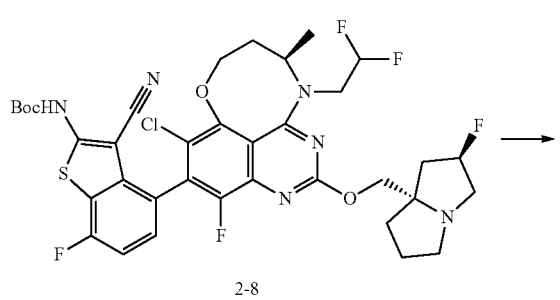

2-8

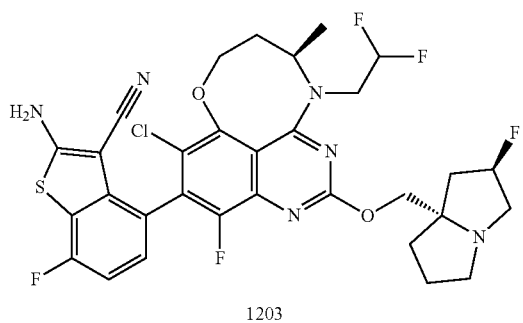

1203

Step 1: A solution of (3R)-3-aminobutan-1-ol (2-1) (1 g, 11.219 mmol), TEA (1.36 g, 13.463 mmol) and 2,2-difluoroethyl trifluoromethanesulfonate (2.88 g, 13.463 mmol) in THF (10 mL) was stirred for 2 hours at room temperature under nitrogen atmosphere. The resulting mixture was concentrated under reduced pressure to give a residue. The residue was purified by silica gel column chromatography, eluting with $CH_2Cl_2$/MeOH (10:1) to afford 2-2 as a light yellow oil. (ESI, m/z): 154 $[M+H]^+$.

Step 2: To a stirred solution of 2-2 (3 g, 19.586 mmol) and 7-bromo-6-chloro-5,8-difluoro-2-(methylsulfanyl)quinazolin-4-ol (2-3) (0.80 g, 2.350 mmol) in THF (50 mL) was added NaH (2.35 g, 97.930 mmol) in portions at 0° C. under nitrogen atmosphere. The resulting mixture was stirred for 1 hour at 0° C., then quenched with ice water and the resulting mixture extracted with ethyl acetate (3×100 mL). The combined organic layers were washed with brine (100 mL), dried over anhydrous $Na_2SO_4$, filtered, and the filtrate concentrated under reduced pressure to give a residue. The residue was purified by reverse-phase flash chromatography (column, $C_{18}$; mobile phase, MeCN in water (10 mmol/L $NH_4HCO_3$)) to afford 2-4 as an off-white solid. (ESI, m/z): 474$[M+H]^+$.

Step 3: A solution of 2-4 (600 mg, 1.264 mmol), POCl3 (678 mg, 4.424 mmol) and TEA (1407 mg, 13.904 mmol) in dry 1,4-dioxane (10 mL) was stirred for 1 hour at 60° C. under nitrogen atmosphere, then cooled to room temperature and quenched with water. The resulting mixture was extracted with ethyl acetate (3×50 mL). The combined organic layers were washed with brine (50 mL), dried over anhydrous $Na_2SO_4$, filtered, and the filtrate concentrated under reduced pressure to give a residue. The residue was purified by silica gel column chromatography, eluting with PE/EA (10:1) to afford 2-5 as a light-yellow solid. (ESI, m/z): 456 $[M+H]^+$.

Step 4: To a stirred solution of 2-5 (150 mg, 0.328 mmol) and 3 Å molecular sieves in DCM (5 mL) was added m-CPBA (200 mg, 0.984 mmol, 85%) in portions at −10° C. under nitrogen atmosphere. The resulting mixture was stirred for 1 hour at 0° C., then quenched with sat. $NaHSO_3$ (aq.) and the resulting mixture was extracted with $CH_2Cl_2$ (3×20 mL). The combined organic layers were washed with sat. $NaHCO_3$(aq.) (3×20 mL) and brine (20 mL), dried over anhydrous $Na_2SO_4$, filtered, and the filtrate concentrated under reduced pressure to afford 2-6 as a yellow solid which was used in the next step directly without further purification. (ESI, m/z): 488 $[M+H]^+$.

Step 5: To a stirred solution of 2-6 (150 mg, 0.307 mmol), 3 Å molecular sieves and 1-5 (98 mg, 0.614 mmol) in toluene (5 mL) was added t-BuONa (88 mg, 0.921 mmol) in portions at 0° C. under nitrogen atmosphere. The resulting mixture was stirred for 1 hour at 0° C. and quenched with sat. $NH_4Cl$ (aq.) at room temperature. The reaction mixture was extracted with ethyl acetate (3×20 mL), then the combined organic layers were washed with brine (20 mL), dried over anhydrous $Na_2SO_4$, filtered, and the filtrate concentrated under reduced pressure to give a residue. The residue was purified by silica gel column chromatography, eluting with $CH_2Cl_2$/MeOH (10:1) to afford 2-7 as a light-yellow solid. (ESI, m/z): 567 $[M+H]^+$.

Step 6: A mixture of 2-7 (120 mg, 0.211 mmol), 1-7 (214 mg, 0.527 mmol), dichloropalladium; {2-[2-(diphenylphosphanyl) phenoxy]phenyl}diphenylphosphane (30 mg, 0.042 mmol), 3 Å molecular sieves and $Cs_2CO_3$ (275 mg, 0.844 mmol, 4.00 eq) in toluene (5 mL) was stirred for 1 hour at 110° C. under argon atmosphere. The reaction mixture was cooled to room temperature and quenched with water, then extracted with ethyl acetate (3×20 mL). The combined organic layers were washed with brine (20 mL), dried over anhydrous $Na_2SO_4$, filtered, and the filtrate concentrated under reduced pressure to give a residue. The residue was purified by prep-TLC ($CH_2Cl_2$/MeOH=20:1) to afford 2-8 as a light-yellow solid. (ESI, m/z): 779 $[M+H]^+$.

Step 7: A solution of 2-8 (73 mg, 0.094 mmol) and TFA (1.0 mL) in DCM (5.0 mL) was stirred for 2 hours at room temperature under nitrogen atmosphere. The resulting mixture was concentrated under reduced pressure to give a residue. The residue was purified by prep-HPLC (Column, XBridge Shield RP18 OBD Column, 30×150 mm, 5 um; mobile phase, water (10 mmol/L $NH_4HCO_3$) and ACN (35% ACN up to 80% in 8 min)) to afford 1203 as a white solid. (ESI, m/z): 679 $[M+H]^+$. 1H-NMR (400 MHZ, DMSO-$d_6$) δ 8.08 (s, 2H), 7.33-7.19 (m, 1H), 7.18-7.09 (m, 1H), 6.70-6.35 (m, 1H), 5.35-5.21 (m, 1H), 4.51-4.41 (m, 1H), 4.40-4.27 (m, 1H), 4.25-4.15 (m, 1H), 4.13-4.02 (m, 2H), 4.02-3.95 (m, 2H), 3.14-3.03 (m, 2H), 3.00 (s, 1H), 2.86-2.80 (m, 1H), 2.19-2.11 (m, 1H), 2.05 (m, 1H), 2.02-1.90 (m, 3H), 1.86-1.73 (m, 3H), 1.29-1.22 (m, 3H).

Example 1ag: Synthesis of 2-amino-4-(9-chloro-4-(2,2-difluoroethyl)-11-fluoro-2-(((2R,7aS)-2-fluoro-tetrahydro-1H-pyrrolizin-7a(5H)-yl)methoxy)-7-(hydroxymethyl)-4,5,6,7-tetrahydro-[1,5]oxazocino[4,3,2-de]quinazolin-10-yl)-7-fluorobenzo[b]thiophene-3-carbonitrile (1207 and 1216)

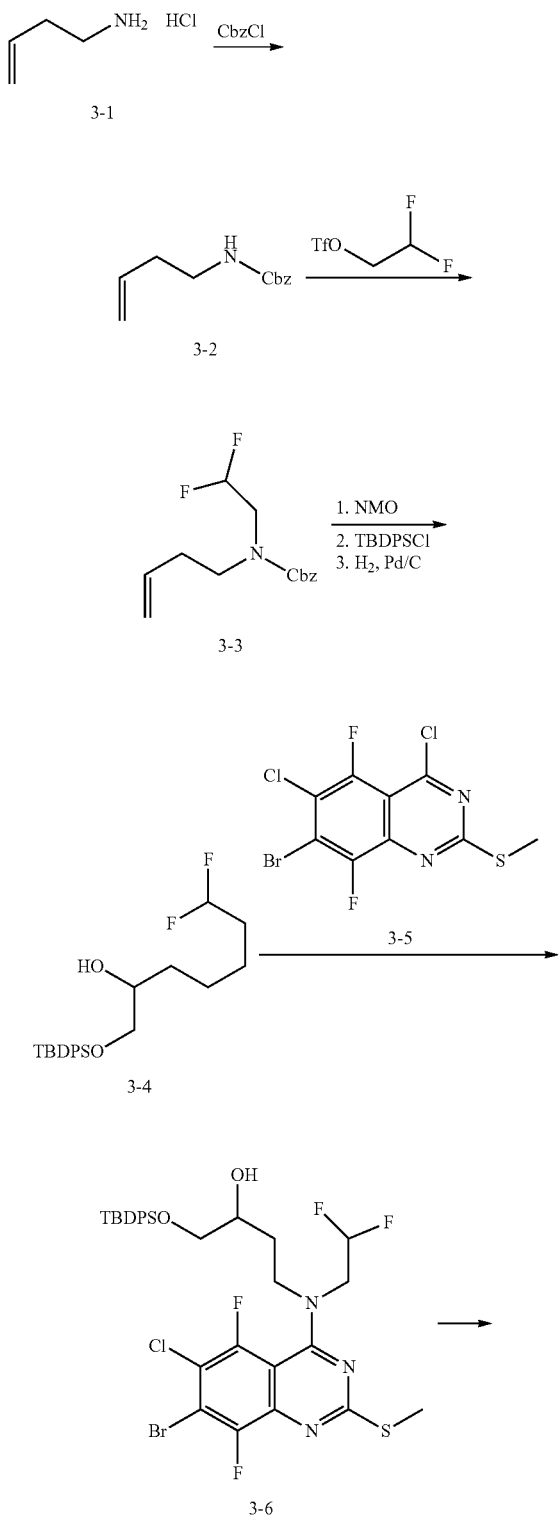

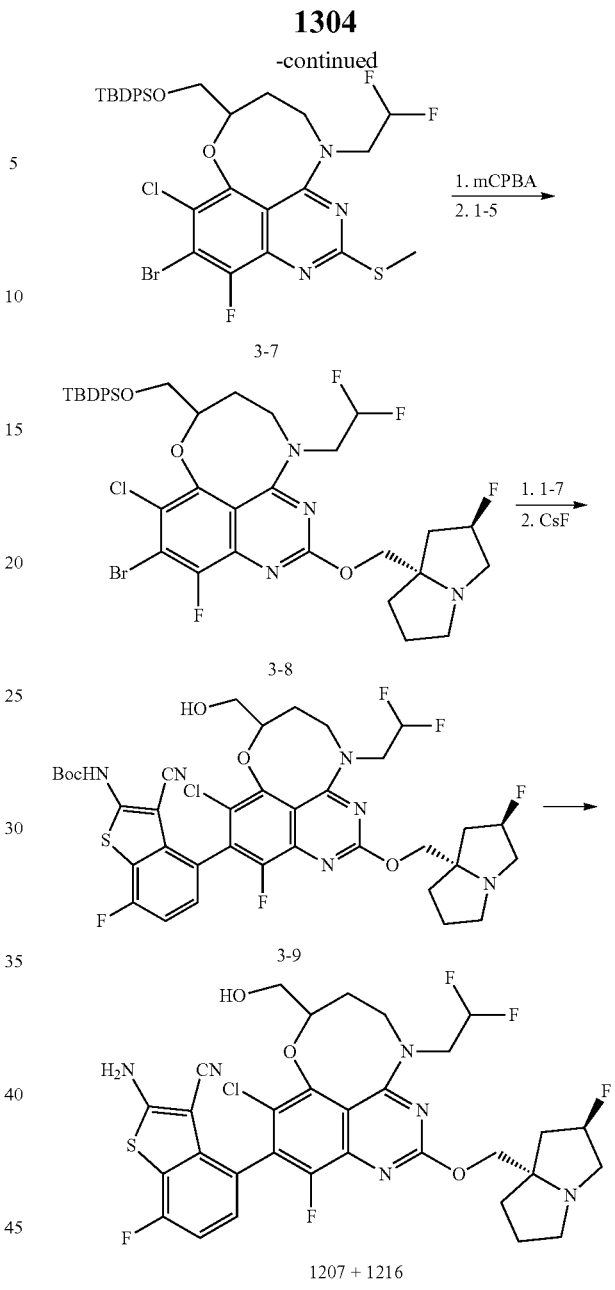

Step 1: A solution of 3-buten-1-amine hydrochloride (3-1) (1.00 g, 9.29 mmol) in THF (10.0 mL) and $H_2O$ (10.0 mL) was treated with $NaHCO_3$ (3.90 g, 46.47 mmol) at room temperature under nitrogen atmosphere followed by the addition of benzyl chloroformate (2.38 g, 13.94 mmol) dropwise at 0° C. The resulting mixture was stirred for 1 hour at room temperature under nitrogen atmosphere, then extracted with ethyl acetate (3×50 mL). The combined organic layers were washed with brine (3×20 mL), dried over anhydrous $Na_2SO_4$, filtered, and the filtrate concentrated under reduced pressure to give a residue. The residue was purified by silica gel column chromatography, eluting with petroleum/ethyl acetate (5:1) to afford 3-2 as a yellow oil. (ESI, m/z): 206 [M+H]$^+$.

Step 2: To a solution of 3-2 (1.30 g, 13.13 mmol, 86% purity) in THF (10.0 mL) was added NaH (1.05 g, 26.26 mmol, 60%) in portions and the mixture was stirred for 30 min at 0° C. under nitrogen atmosphere followed by the addition of 2,2-difluoroethyl trifluoromethanesulfonate (5.62 g, 26.26 mmol) dropwise at 0° C. The resulting mixture was stirred for 1 hour at room temperature, then quenched with water at 0° C. and the resulting mixture was extracted with ethyl acetate (3×50 mL). The combined organic layers were washed with brine (3×20 mL), dried over anhydrous Na$_2$SO$_4$, filtered, and the filtrate concentrated under reduced pressure to give a residue. The residue was purified by silica gel column chromatography, eluting with petroleum/ethyl acetate (5:1) to afford 3-3 as a yellow oil. (ESI, m/z): 270 [M+H]$^+$.

Step 3: A solution of 3-3 (1.40 g, 4.99 mmol) in water (10.0 mL) and t-BuOH (10.0 mL) was treated with NMO (0.88 g, 7.48 mmol) at 0° C. under nitrogen atmosphere followed by the addition of K$_2$OsO4.2H$_2$O (0.18 g, 0.5 mmol) dropwise at 0° C. The resulting mixture was stirred overnight at room temperature under nitrogen atmosphere, then extracted with ethyl acetate (3×50 mL). The combined organic layers were washed with brine (3×20 mL), dried over anhydrous Na$_2$SO$_4$, filtered, and the filtrate concentrated under reduced pressure to afford benzyl N-(2,2-difluoroethyl)-N-(3,4-dihydroxybutyl)carbamate as a brown oil which was used directly in the next step without purification. (ESI, m/z): 304 [M+H]$^+$.

Step 4: A solution of benzyl N-(2,2-difluoroethyl)-N-(3,4-dihydroxybutyl)carbamate (1.00 g, 2.64 mmol, 80%) in DMF (10.0 mL) was treated with imidazole (0.45 g, 6.59 mmol) at room temperature under nitrogen atmosphere followed by the addition of tert-butyl(chloro)diphenylsilane (1.09 g, 3.95 mmol) dropwise at 0° C. The resulting mixture was stirred overnight at room temperature under nitrogen atmosphere, then extracted with ethyl acetate (3×50 mL). The combined organic layers were washed with brine (3×20 mL), dried over anhydrous Na$_2$SO$_4$, filtered, and the filtrate concentrated under reduced pressure to give a residue. The residue was purified by silica gel column chromatography, eluting with petroleum/ethyl acetate (5:1), to afford benzyl N-{4-[(tert-butyldiphenylsilyl)oxy]-3-hydroxybutyl}-N-(2,2-difluoroethyl)carbamate as a colorless oil. (ESI, m/z): 542 [M+H]$^+$.

Step 5: A solution of benzyl N-{4-[(tert-butyldiphenylsilyl)oxy]-3-hydroxybutyl}-N-(2,2-difluoroethyl)carbamate (1.65 g, 2.01 mmol) and Pd/C (0.32 g, 0.3 mmol, 10%) in EtOH (21.8 mL) was stirred for 2 hours at room temperature under hydrogen atmosphere. The resulting mixture was filtered and the filter cake washed with ethyl acetate (3×100 mL). The filtrate was concentrated under reduced pressure to give a residue. The residue was purified by silica gel column chromatography, eluting with petroleum/ethyl aceate (1:1), to afford 3-4 as a colorless oil. (ESI, m/z): 408 [M+H]$^+$.

Step 6: A solution of 3-4 (970.0 mg, 2.26 mmol) and 7-bromo-4,6-dichloro-5,8-difluoro-2-(methylsulfanyl)quinazoline (3-5) (813.9 mg, 2.26 mmol) in t-BuOH (9.2 mL) was treated with DIEA (730.5 mg, 5.65 mmol) at room temperature under nitrogen atmosphere. The resulting mixture was stirred for 4 hours at 90° C. under nitrogen atmosphere, then cooled to room temperature and the resulting mixture quenched with water (30 mL) and extracted with ethyl acetate (3×30 mL). The combined organic layers were washed with brine (3×10 mL), dried over anhydrous Na$_2$SO$_4$, filtered, and the filtrate concentrated under reduced pressure to give a residue. The residue was purified by silica gel column chromatography, eluting with petroleum/ethyl acetate (2:1), to afford 3-6 as a yellow solid. (ESI, m/z): 730 [M+H]$^+$.

Step 7: A solution of 3-6 (1.15 g, 1.5 mmol) in THF (4.3 mL) was treated with NaH (0.12 g, 3.00 mmol, 60%) at 0° C. under nitrogen atmosphere and the mixture was stirred for 30 min at 0° C. The reaction mixture was irradiated with microwave radiation for 1 hour at 60° C., then cooled to room temperature and quenched with sat. NH$_4$Cl (aq.) at 0° C. The resulting mixture was extracted with ethyl acetate (3×30 mL) and the combined organic layers were washed with brine (3×10 mL), dried over anhydrous Na$_2$SO$_4$, filtered, and the filtrate concentrated under reduced pressure to give a residue. The residue was purified by silica gel column chromatography, eluting with petroleum/acetate (5:1), to afford 3-7 as an off-white solid. (ESI, m/z): 710 [M+H]$^+$.

Step 8: A solution of 3-7 (350.0 mg, 0.49 mmol) in DCM (7.0 mL) was treated with m-CPBA (351.6 mg, 1.73 mmol, 85% wt) for 2 hours at −10-0° C. under nitrogen atmosphere. The reaction was quenched with NaHSO$_3$ at 0° C., then neutralized to PH~8 with NaHCO$_3$. The mixture was extracted with CH$_2$Cl$_2$ (3×30 mL) and the combined organic layers were washed with brine (3×10 mL), dried over anhydrous Na$_2$SO$_4$, filtered, and the filtrate concentrated under reduced pressure to afford 7-bromo-11-{[(tert-butyldiphenylsilyl)oxy]methyl}-8-chloro-14-(2,2-difluoroethyl)-6-fluoro-3-methanesulfonyl-10-oxa-2,4,14-triazatricyclo[7.5.1.0^{5,15}] ] pentadeca-1,3,5(15),6,8-pentaene (400.0 mg, crude) as a yellow solid. (ESI, m/z): 742 [M+H]$^+$.

Step 9: A solution of 7-bromo-11-{[(tert-butyldiphenylsilyl)oxy]methyl}-8-chloro-14-(2,2-difluoroethyl)-6-fluoro-3-methanesulfonyl-10-oxa-2,4,14-triazatricyclo[7.5.1.0^{5,15}] ]pentadeca-1,3,5(15),6,8-pentaene (400.0 mg, 0.53 mmol) in toluene (8.0 mL) was treated with 1-5 (154.2 mg, 0.96 mmol) at 0° C. under nitrogen atmosphere followed by the addition of t-BuONa (155.1 mg, 1.61 mmol) dropwise at 0° C. The resulting solution was stirred for 1 hour at 0° C., then quenched with sat. NH$_4$Cl (aq.) at 0° C. The mixture was extracted with ethyl acetate (3×30 mL) and the combined organic layers were washed with brine (3×10 mL), dried over anhydrous Na$_2$SO$_4$, filtered, and the filtrate concentrated under reduced pressure to give a residue. The residue was purified by silica gel column chromatography, eluting with petroleum/ethyl acetate (1:1), to afford 3-8 as a white solid. (ESI, m/z): 821 [M+H]$^+$.

Step 10: To a stirred solution of 3-8 (150.0 mg, 0.17 mmol) and 1-7 (203.5 mg, 0.5 mmol) in Cs$_2$CO$_3$ (492.1 mg, 1.51 mmol) was added (II)/dichloro[bis(2-(diphenylphosphino)phenyl)ether]palladium(II) (18.0 mg, 0.02 mmol) in portions at room temperature under nitrogen atmosphere, then toluene (15.0 mL) was added dropwise. The resulting mixture was stirred an additional 1 hour at 110° C., then cooled to room temperature and quenched with water (30 mL) and extracted with ethyl acetate (3×30 mL). The combined organic layers were washed with brine (3×10 mL), dried over anhydrous Na$_2$SO$_4$, filtered, and the filtrate concentrated under reduced pressure to give a residue. The residue was purified by silica gel column chromatography, eluting with CH$_2$Cl$_2$/MeOH (20:1), to afford 3-{[(2R,7aS)-2-fluoro-hexahydropyrrolizin-7a-yl]methoxy}-7-bromo-11-{[(tert-butyldiphenylsilyl)oxy]methyl}-8-chloro-14-(2,2-difluoroethyl)-6-fluoro-10-oxa-2,4,14-triazatricyclo[7.5.1.0^{5,15}] ]pentadeca-1,3,5(15),6,8-pentaene as a white solid. (ESI, m/z): 1033 [M+H]$^+$.

Step 11: To an 8 mL vial were added tert-butyl N-[4-(3-{[(2R,7aS)-2-fluoro-hexahydropyrrolizin-7a-yl]methoxy}-11-{[(tert-butyldiphenylsilyl)oxy]methyl}-8-chloro-14-(2,2-difluoroethyl)-6-fluoro-10-oxa-2,4,14-triazatricyclo[7.5.1.0^{5,15}] ]pentadeca-1,3,5(15),6,8-pentaen-7-yl)-3-cyano-7-fluoro-1-benzothiophen-2-yl]carbamate (110.0 mg, 0.11 mmol), CsF (64.6 mg, 0.42 mmol) and DMF (2.0 mL) at room temperature. The resulting mixture was stirred overnight at room temperature under air atmosphere, then extracted with ethyl acetate (3×50 mL). The combined organic layers were washed with brine (2×20 mL), dried over anhydrous Na$_2$SO$_4$, filtered, and the filtrate concentrated under reduced pressure to give a residue. The residue was purified by reverse-phase flash chromatography (column, C$_{18}$; mobile phase, MeCN in water (10 mmol/L NH$_4$HCO$_3$)) to afford 3-9 as an off-white solid. (ESI, m/z): 795 [M+H]$^+$.

Step 12: To a stirred solution of 3-9 (45.0 mg, 0.06 mmol) in DCM (1.0 mL) was added TFA (0.2 mL) at 0° C. The resulting mixture was stirred for 1 hour at room temperature under air atmosphere, then concentrated under reduced pressure to give a residue which neutralized to pH 8 with NH$_3$·H$_2$O. The mixture was extracted with ethyl acetate, washed with brine, dried over sodium sulfate, filtered and solvent was removed under reduced pressure to give a residue. The residue was purified by prep-HPLC (Column: Kinetex EVO C18 Column, 30*150, 5 um; Mobile Phase A: water (10 mmol/L NH$_4$HCO$_3$), Mobile Phase B: ACN) to afford peak 1 (1207) and peak 2 (1216) as white solids. 1207: (ESI, m/z): 695 [M+H]$^+$. $^1$H NMR: (400 MHz, DMSO-d$_6$) δ 8.05 (s, 2H), 7.27 (dd, J=8.4, 5.3 Hz, 1H), 7.15 (dd, J=9.5, 8.4 Hz, 1H), 6.68-6.29 (m, 1H), 5.27 (d, J=54.0 Hz, 1H), 4.87-4.80 (m, 1H), 4.42 (s, 1H), 4.30 (s, 1H), 4.10 (dd, J=10.1, 6.9 Hz, 1H), 4.06-3.95 (m, 2H), 3.82-3.48 (m, 4H), 3.08 (d, J=7.4 Hz, 2H), 3.00 (s, 1H), 2.82 (d, J=6.9 Hz, 1H), 2.23-2.01 (m, 2H), 2.02-1.90 (m, 1H), 1.88 (d, J=13.9 Hz, 1H), 1.79 (dd, J=20.7, 6.5 Hz, 4H), 1.23 (s, 1H). 1216: (ESI, m/z): 695 [M+H]$^+$. $^1$H NMR (400 MHZ, DMSO-d$_6$) δ 8.09 (s, 2H), 7.27 (dd, J=8.4, 5.3 Hz, 1H), 7.15 (dd, J=9.5, 8.4 Hz, 1H), 6.69-6.33 (m, 1H), 5.27 (d, J=53.4 Hz, 1H), 4.85 (td, J=5.6, 2.3 Hz, 1H), 4.43 (s, 1H), 4.38 (d, J=14.5 Hz, 1H), 4.28 (s, 1H), 4.14-3.97 (m, 2H), 3.79 (ddd, J=23.9, 12.4, 6.9 Hz, 2H), 3.66 (dt, J=11.5, 5.9 Hz, 1H), 3.52 (s, 1H), 3.11-3.05 (m, 2H), 3.00 (s, 1H), 2.82 (q, J=8.1 Hz, 1H), 2.15-1.97 (m, 5H), 1.87-1.74 (m, 3H), 1.24 (s, 1H).

Example 1ah: Synthesis of 2-amino-4-((5S)-8-chloro-5-((E)-2-cyanovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (786)

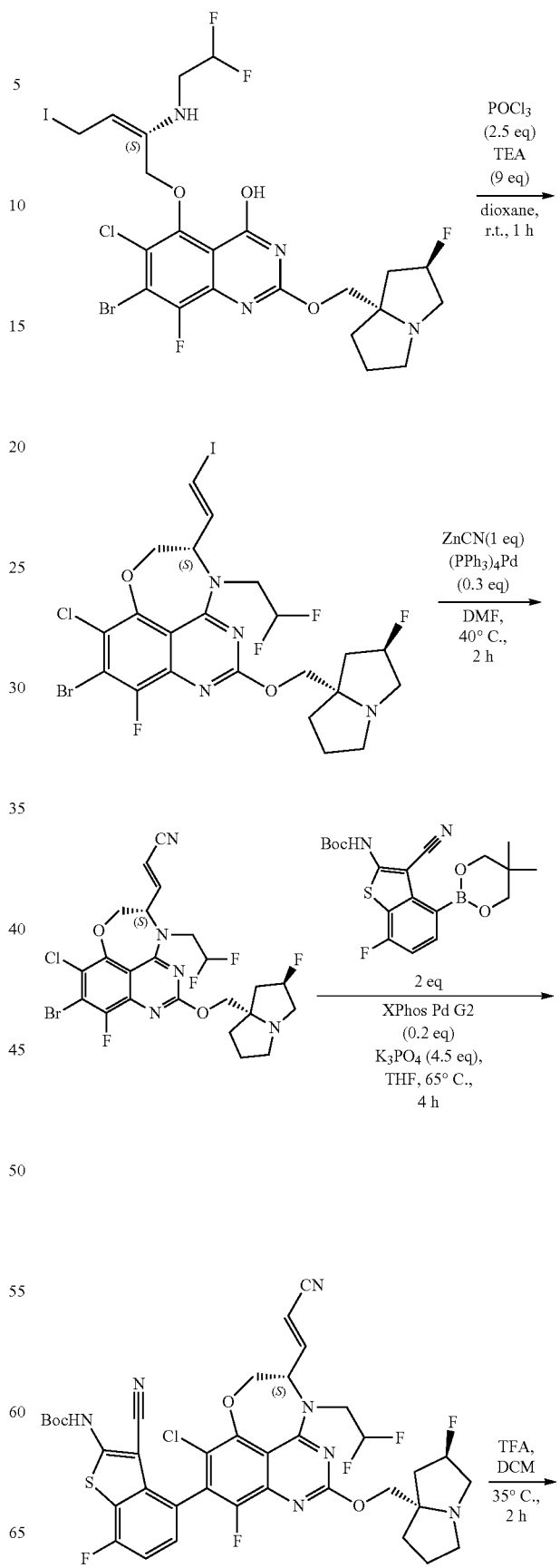

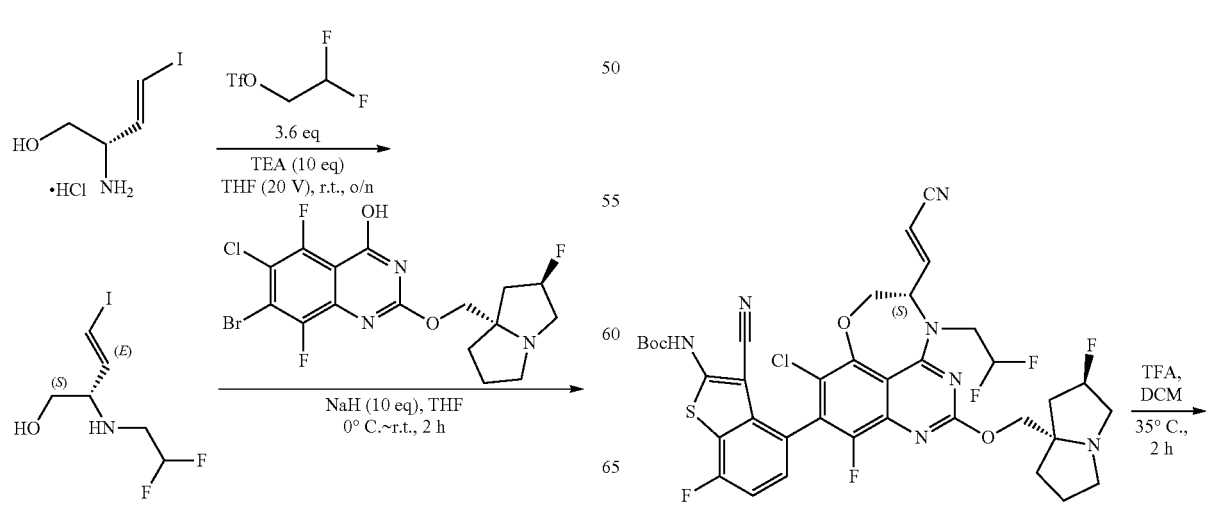

-continued

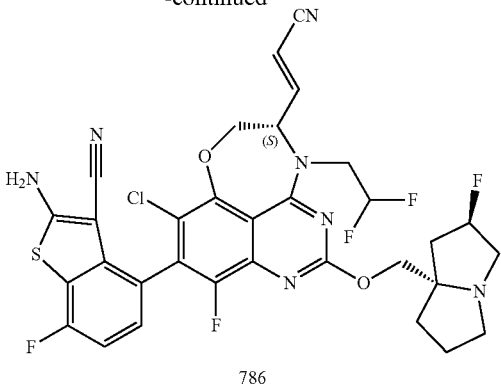

786

(2S,3E)-2-[(2,2-difluoroethyl)amino]-4-iodobut-3-en-1-ol To a solution of (2S,3E)-2-[(2,2-difluoroethyl)amino]-4-iodobut-3-en-1-ol (0.4 g, 1.444 mmol, 1 equiv) in THF (10 mL) was added 2,2-difluoroethyl trifluoromethanesulfonate (1.11 g, 5.198 mmol, 3.6 equiv) and triethylamine (1.46 g, 14.440 mmol, 10 equiv). The mixture was stirred overnight at room temperature. And concentrated in vacuo to give crude. The crude was purification by column gel (ethyl acetate in petroleum from 10% to 100%) to give the desired product as a colorless oil.

$^1$H NMR: (400 MHZ, Methanol-$d_4$, ppm) δ 6.49 (d, J=14.6 Hz, 1H), 6.39 (dd, J=14.5, 8.1 Hz, 1H), 5.87 (tt, J=56.4, 4.3 Hz, 1H), 3.54 (dd, J=10.9, 5.0 Hz, 1H), 3.45 (dd, J=10.9, 6.7 Hz, 1H), 3.29-3.19 (m, 1H), 2.99-2.78 (m, 2H).

7-Bromo-6-chloro-5-(((S,E)-2-((2,2-difluoroethyl)amino)-4-iodobut-3-en-1-yl)oxy)-8-fluoro-2-(((2R,7aS)-2-fluorotetrahydro-1H-pyrrolizin-7a(5H)-yl)methoxy)quinazolin-4-ol To a solution of (2S)-2-[(2,2-difluoroethyl)amino]-4-iodobut-3-en-1-ol (198 mg, 0.715 mmol, 1 equiv) in THF (5 mL) was 7-bromo-6-chloro-5,8-difluoro-2-(((2R,7aS)-2-fluorotetrahydro-1H-pyrrolizin-7a(5H)-yl)methoxy)quinazolin-4-ol (323 mg, 0.715 mmol, 1 equiv). Then NaH (286 mg, 7.150 mmol, 10 equiv, 60%) was added slowly at 0° C. The resulting mixture was stirred at room temperature for 2 hours and quenched with 1% AcOH solution slowly at 0° C., extracted with ethyl acetate (20 mL×2). The combined organic phase was dried with over $Na_2SO_4$. It was concentrated in vacuo to give crude the desired product as a brown oil. (ESI, m/z): 710.6 [M+H]$^+$.

(S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((E)-2-iodovinyl)-5,6-dihydro-4H-[1,4]oxazepino[5,6,7-de]quinazoline To a solution of 7-bromo-6-chloro-5-(((S,E)-2-((2,2-difluoroethyl)amino)-4-iodobut-3-en-1-yl)oxy)-8-fluoro-2-(((2R,7aS)-2-fluorotetrahydro-1H-pyrrolizin-7a(5H)-yl)methoxy)quinazolin-4-ol (620 mg, 0.874 mmol, 1 equiv) in dioxane (5 mL) was added triethylamine (795 mg, 7.866 mmol, 9 equiv) and POCl3 (335 mg, 2.185 mmol, 2.5 equiv), and the mixture was stirred at room temperature for 1 hour. Water (20 mL) was added, and the mixture was extracted with ethyl acetate (20 mL×2). The extracts were combined, washed with brine (20 mL), and dried with over $Na_2SO_4$. It was filtered and concentrated in vacuo to give the crude. The crude was purified by flash chromatography with the following conditions: MeOH in DCM (from 0% to 10%) to afford the desired product as a white solid. (ESI, m/z): 693.1 [M+H]$^+$.

(E)-3-((S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)acrylonitrile To a solution of (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((E)-2-iodovinyl)-5,6-dihydro-4H-[1,4]oxazepino[5,6,7-de]quinazoline (210 mg, 0.304 mmol, 1 equiv) in DMF (5 mL) was added zinc cyanide (35 mg, 0.304 mmol, 1 equiv) and Pd(PPh3)$_4$ (105 mg, 0.091 mmol, 0.3 equiv). The mixture was stirred at 40° C. for 2 hours. It was cooled ot room temperature and filtered. The filtrate was concentrated in vacuo to give the crude. The crude was purified by reversed-phase flash chromatography with the following conditions: MeOH in DCM, 0% to 10% to afford the desired product as a yellow solid. (ESI, m/z): 590.3 [M+H]$^+$.

Tert-butyl (4-((5S)-8-chloro-5-((E)-2-cyanovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate To a solution of (E)-3-((S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)acrylonitrile (120 mg, 0.203 mmol, 1 equiv) in THF (4.0 mL) was added tert-butyl N-[3-cyano-4-(5,5-dimethyl-1,3,2-dioxaborinan-2-yl)-7-fluoro-1-benzothiophen-2-yl]carbamate (246 mg, 0.609 mmol, 3 equiv), $K_3PO_4$ (388 mg, 1.827 mmol, 9 equiv) and 2nd Generation XPhos precatalyst (48 mg, 0.061 mmol, 0.3 equiv). The mixture was stirred at 65° C. for 2 hours. It was cooled and water was added. The mixture was extracted with ethyl acetate (10 mL×2). The extracts were combined, washed with brine (20 mL), dried with over $Na_2SO_4$. It was filtered and concentrated in vacuo to give the crude. The crude was purified by flash chromatography with the following conditions: MeOH in DCM (from 0% to 10%) to afford the desired product as a brown solid. (ESI, m/z): 801.9 [M+H]$^+$.

2-Amino-4-((5S)-8-chloro-5-((E)-2-cyanovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile To a solution of tert-butyl (4-((5S)-8-chloro-5-((E)-2-cyanovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate (0.1 g, 0.125 mmol, 1 equiv) in DCM (6 mL) was added TFA (2 mL) and the mixture was stirred at 35° C. for 2 hours. It was cooled to room temperature, concentrated in vacuo to give crude. The crude was purification by Prep-HPLC (Column: Sunfire C18 5 m, 30 mm*150 mm; Mobile Phase A: Water (0.1% FA), Mobile Phase B: ACN; Flow rate: 60 mL/min; Gradient: 15% B to 40% B in 10 min; Wave Length: UV 254 nm/220 nm; RT1(min): 10.12/10.06) to give desired product as an off-white solid. (ESI, m/z): 701.8 [M+H]$^+$ $^1$H NMR: (400 MHZ, DMSO-$d_6$, ppm) δ 8.16 (d, J=17.8 Hz, 2H), 7.27-7.21 (m, 1H), 7.16 (t, J=8.9 Hz, 1H), 6.98 (dd, J=16.4, 1.1 Hz, 1H), 5.78 (d, J=16.2 Hz, 1H), 5.30 (d, J=54.0 Hz, 1H), 4.67-4.50 (m, 1H), 4.20-4.18 (m, 2H), 3.14 (s, 2H), 3.06 (s, 1H), 2.86 (s, 1H), 2.22-1.95 (m, 6H), 1.89-1.78 (m, 3H), 1.24 (d, J=7.4 Hz, 1H), 1.17 (t, J=7.3 Hz, 1H).

Example 1ai: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-((E)-1-(methoxyimino)ethyl)-5,6-dihydro-4H-[1,4]oxazepino[5,6,7-de]quinazolin-9-yl)-7-fluorobenzo[b]thiophene-3-carbonitrile (941 and 780)

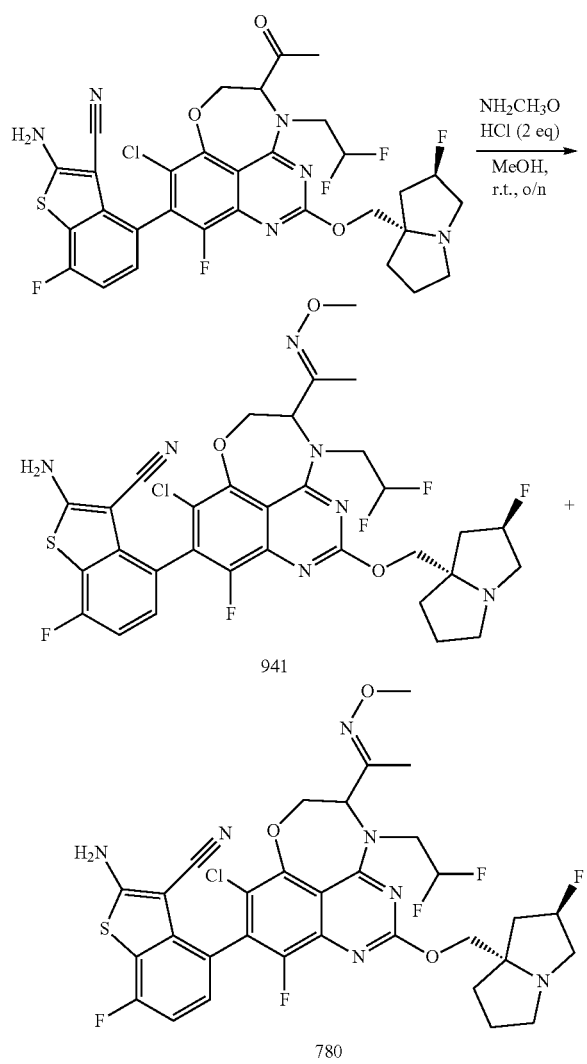

2-Amino-4-(8-chloro-4-(2,2-difluoroethyl)-10-fluoro-2-(((2R,7aS)-2-fluorotetrahydro-1H-pyrrolizin-7a(5H)-yl)methoxy)-5-((E)-1-(methoxyimino)ethyl)-5,6-dihydro-4H-[1,4]oxazepino[5,6,7-de]quinazolin-9-yl)-7-fluorobenzo[b]thiophene-3-carbonitrile To a stirred solution of 4-(5-acetyl-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile (55 mg, 0.08 mmol, 1.00 equiv) in MeOH (2 mL) was added O-methylhydroxylamine (8 mg, 0.16 mmol, 2.00 equiv) in portions at room temperature. The resulting mixture was stirred for overnight at room temperature. It was concentrated to give a crude. The crude product was purified by Prep-HPLC with the following conditions (Column: YMC Triart C18 ExRs 5 m, 30 mm×150 mm; Mobile Phase A: Water (10 mmol/L NH₄HCO₃), Mobile Phase B: ACN; Flow rate: 60 mL/min; Gradient: 55% B to 70% B in 10 min; Wave Length: UV 254 nm/220 nm; RT1(min): 8.85/9.40) to afford descried products: the first eluting (941; peak 1; polar) as a white solid and the second eluting (780; peak 2; less polar) as a white solid. 941: (ESI, m/z): 721.90[M+H]⁺.

¹H NMR: (400 MHZ, DMSO-d₆, ppm) δ 8.07 (s, 2H), 7.21 (dd, J=8.4, 5.3 Hz, 1H), 7.14 (t, J=8.9 Hz, 1H), 6.45 (s, 1H), 5.35-5.22 (m, 1H), 5.04-4.97 (m, 1H), 4.81 (d, J=4.4 Hz, 1H), 4.54 (d, J=13.2 Hz, 1H), 4.37 (s, 1H), 4.16-4.01 (m, 2H), 3.92 (s, 1H), 3.61 (s, 3H), 3.10 (s, 2H), 3.01 (s, 1H), 2.83 (s, 1H), 2.14 (d, J=15.0 Hz, 1H), 2.07 (s, 1H), 2.01 (s, 1H), 1.83 (s, 6H). 780: (ESI, m/z): 721.90[M+H]⁺.

¹H NMR: (400 MHZ, DMSO-d₆, ppm) δ 8.10 (s, 2H), 7.23 (dd, J=8.3, 5.3 Hz, 1H), 7.17-7.08 (m, 1H), 6.61-6.32 (m, 1H), 5.33 (d, J=17.4 Hz, 1H), 5.16-5.08 (m, 1H), 4.87 (d, J=4.2 Hz, 1H), 4.43-4.37 (m, 2H), 4.07 (m, 2H), 3.60 (s, 4H), 3.09 (d, J=8.5 Hz, 2H), 3.01 (s, 1H), 2.83 (s, 1H), 2.18-2.10 (m, 1H), 2.06 (s, 1H), 2.01 (s, 1H), 1.87 (s, 3H), 1.81 (s, 3H).

Example 1aj: Synthesis of 2-amino-4-((5S)-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (629 and 912)

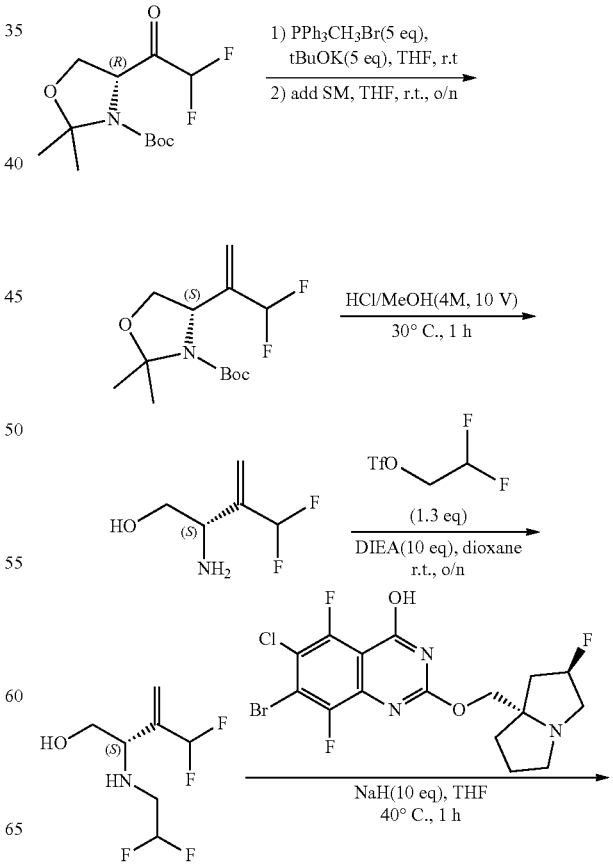

-continued

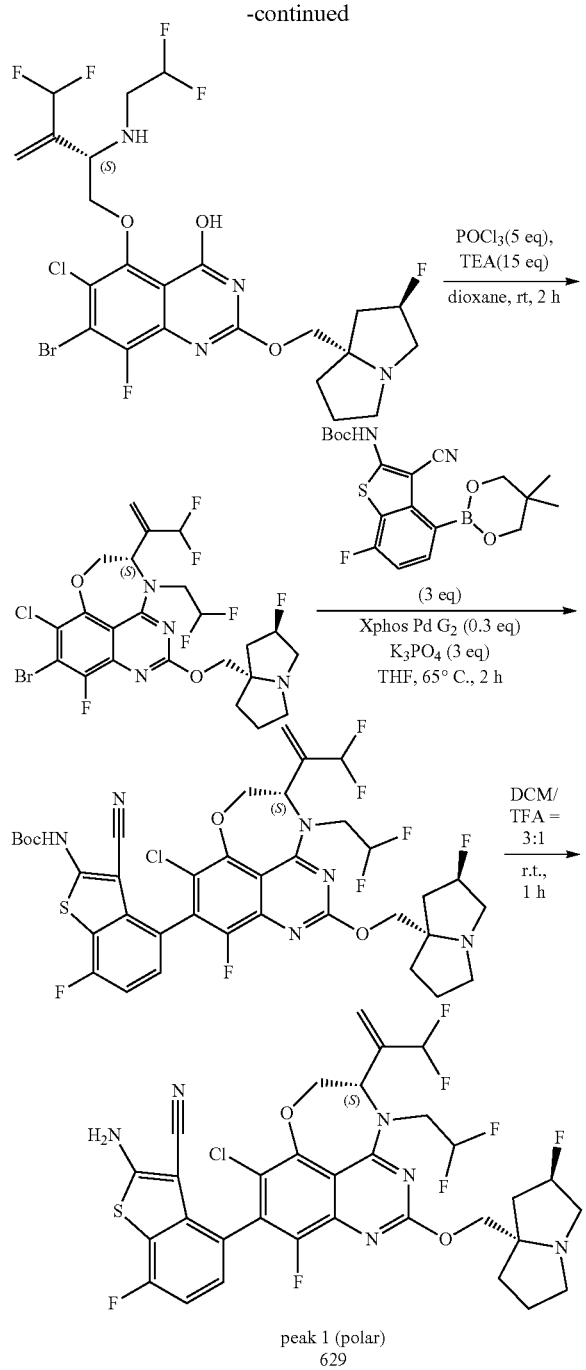

peak 1 (polar)
629

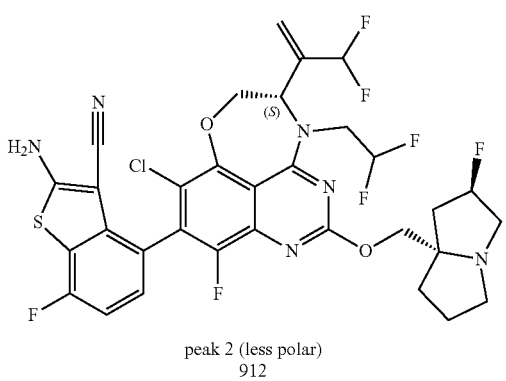

peak 2 (less polar)
912

Tert-butyl (4S)-4-(3,3-difluoroprop-1-en-2-yl)-2,2-dimethyl-1,3-oxazolidine-3-carboxylate To a stirred solution of PPh$_3$CH$_3$Br (5098 mg, 14.320 mmol, 5 equiv) in THF (8 mL) was added t-t-BuOK (1607 mg, 14.320 mmol, 5 equiv) at 0° C. under nitrogen atmosphere. The resulting mixture was stirred for 1 hour at room temperature under nitrogen atmosphere. To above mixture was added tert-butyl (4R)-4-(2,2-difluoroacetyl)-2,2-dimethyl-1,3-oxazolidine-3-carboxylate (800 mg, 2.864 mmol, 1 equiv) in THF (4 mL) dropwise at room temperature under nitrogen atmosphere. The resulting mixture was stirred overnight at room temperature, quenched with water/ice at room temperature and extracted with CH$_2$Cl$_2$ (3×60 mL). The extracts were combined, washed with brine, and dried over anhydrous Na$_2$SO$_4$. After filtration, the filtrate was concentrated under reduced pressure to give a residue. The residue was purified by silica gel column chromatography, eluted with petroleum/ethyl acetate (3:1) to afford the desired product as a colorless oil. (ESI, m/z): 278 [M+H]$^+$.

(S)-2-amino-3-(difluoromethyl)but-3-en-1-ol A solution of tert-butyl (4S)-4-(3,3-difluoroprop-1-en-2-yl)-2,2-dimethyl-1,3-oxazolidine-3-carboxylate (420 mg, 1.515 mmol, 1 equiv) in HCl/MeOH (4 M, 4.2 mL) was stirred for 1 hour at 30° C. under nitrogen atmosphere. The resulting mixture was concentrated under vacuum to give the desired product which was used in the next step directly without further purification. (ESI, m/z): 138 [M+H]$^+$.

(2S)-2-[(2,2-difluoroethyl)amino]-3-(difluoromethyl)but-3-en-1-ol To a stirred solution of (2S)-2-amino-3-(difluoromethyl)but-3-en-1-ol (500 mg, 3.646 mmol, 1 equiv) and DIEA (4712 mg, 36.460 mmol, 10 equiv) in dioxane (6 mL) was added 2,2-difluoroethyl trifluoromethanesulfonate (1015 mg, 4.740 mmol, 1.3 equiv) dropwise at room temperature under nitrogen atmosphere. The resulting mixture was stirred overnight, quenched with water/ice, and extracted with CH$_2$Cl$_2$ (3×50 mL). The extracts were combined, washed with brine, and dried over anhydrous Na$_2$SO$_4$. After filtration, the filtrate was concentrated under reduced pressure to give a residue. The residue was purified by silica gel column chromatography, eluted with petroleum/ethyl acetate (1:1) to afford the desired product as a colorless oil. (ESI, m/z): 202 [M+H]$^+$.

7-Bromo-6-chloro-5-(((S)-2-((2,2-difluoroethyl)amino)-3-(difluoromethyl)but-3-en-1-yl)oxy)-8-fluoro-2-(((2R,7aS)-2-fluorotetrahydro-1H-pyrrolizin-7a(5H)-yl)methoxy)quinazolin-4-ol To a stirred solution of (2S)-2-[(2,2-difluoroethyl)amino]-3-(difluoromethyl)but-3-en-1-ol (90 mg, 0.447 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (202 mg, 0.447 mmol, 1 equiv) in THF (3 mL) was added NaH (107 mg, 4.470 mmol, 10 equiv) at 0° C. under nitrogen atmosphere. The resulting mixture was stirred for 1 h at 40° C. under nitrogen atmosphere. It was cooled down to room temperature, quenched with water/ice, and extracted with CH$_2$Cl$_2$ (3×30 mL). The extracts were combined, washed with brine, and dried over anhydrous Na$_2$SO$_4$. After filtration, the filtrate was concentrated under reduced pressure the desired product which was used in the next step directly without further purification. (ESI, m/z): 633 [M+H]$^+$.

(S)-9-bromo-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline To a stirred solution of 7-bromo-6-chloro-5-(((S)-2-((2,2-difluoroethyl)amino)-3-(difluoromethyl)but-3-en-1-yl)oxy)-8-fluoro-2-(((2R,7aS)-2-fluorotetrahydro-1H-pyrrolizin-7a(5H)-yl)methoxy)quinazolin-4-ol (350 mg, 0.552 mmol, 1 equiv) and triethylamine (838 mg, 8.280 mmol, 15 equiv) in dioxane (5 mL) was added POCl3 (423 mg, 2.760 mmol, 5 equiv) dropwise at 0° C. under nitrogen atmosphere. The resulting mixture was stirred for 2 hours at room temperature under nitrogen atmosphere. The reaction was quenched with water/ice at room temperature, extracted with $CH_2Cl_2$ (3×30 mL). The extracts were combined, washed with brine, and dried over anhydrous $Na_2SO_4$. After filtration, the filtrate was concentrated under reduced pressure to give a crude. The residue was purified by reversed-phase flash chromatography with the following conditions: column, $C_{18}$; mobile phase, MeCN in Water (10 mmol/L $NH_4HCO_3$), 30% to 70% gradient in 15 min; detector, UV 254 nm to afford the desired product as a yellow solid. (ESI, m/z): 615 $[M+H]^+$.

Tert-butyl (4-((5S)-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate To a stirred solution of (S)-9-bromo-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline (140 mg, 0.227 mmol, 1 equiv) and tert-butyl N-[3-cyano-4-(5,5-dimethyl-1,3,2-dioxaborinan-2-yl)-7-fluoro-1-benzothiophen-2-yl]carbamate (275 mg, 0.681 mmol, 3 equiv) in THF (3 mL) was added XPhos Pd G2 (53 mg, 0.068 mmol, 0.3 equiv) and $K_3PO_4$ (144 mg, 0.681 mmol, 3 equiv) at room temperature. The resulting mixture was stirred for 2 hours at 65° C. under argon atmosphere. It was cooled to room temperature, concentrated under vacuum to give a residue. The residue was purified by reversed-phase flash chromatography with the following conditions: column, $C_{18}$; mobile phase, MeCN in Water (10 mmol/L $NH_4HCO_3$), 30% to 100% gradient in 20 min; detector, UV 254 nm to give the desired product as a yellow solid. (ESI, m/z): 827 $[M+H]^+$.

2-Amino-4-((5S)-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile To a stirred mixture of tert-butyl (4-((5S)-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate (100 mg, 0.121 mmol, 1 equiv) in DCM (5 mL) was added TFA (1.5 mL) at room temperature. The resulting mixture was stirred for 1 hour and concentrated under vacuum to give a residue. The residue was purified Prep-HPLC: Column: XBridge BEH C18 OBD Prep Column 130, 5 m, 30 mm*150 mm; Mobile Phase A: Water (10 mmol/L $NH_4HCO_3$), Mobile Phase B: ACN; Flow rate: 60 mL/min; Gradient: 48% B to 65% B in 10 min; Wave Length: UV 254 nm/220 nm; RT1(min): 8.68/9.07 to afford desired products: the first eluting (629; peak 1; polar) as a white solid and the second eluting (912; peak 2; less polar) as white solids. 629:(ESI, m/z): 727 $[M+H]^+$.

$^1$H NMR (400 MHZ, DMSO-$d_6$, ppm) δ 8.09 (s, 2H), 7.22 (dd, J=8.4, 5.3 Hz, 1H), 7.14 (dd, J=9.4, 8.4 Hz, 1H), 6.83-6.39 (m, 2H), 5.73 (s, 1H), 5.36-5.22 (m, 1H), 5.17 (s, 1H), 4.84 (s, 1H), 4.79-4.75 (m, 1H), 4.68-4.64 (m, 1H), 4.47-4.36 (m, 1H), 4.11-4.03 (m, 2H), 3.75-3.73 (m, 1H), 3.09 (s, 2H), 3.01 (s, 1H), 2.84 (s, 1H), 2.13-2.00 (m, 3H), 1.80-1.76 (m, 3H). 912:(ESI, m/z): 727 $[M+H]^+$.

$^1$H NMR (400 MHZ, DMSO-$d_6$, ppm) δ 8.06 (s, 2H), 7.25 (dd, J=8.4, 5.3 Hz, 1H), 7.12 (dd, J=9.4, 8.4 Hz, 1H), 6.85-6.55 (m, 2H), 5.83 (s, 1H), 5.34-5.21 (m, 2H), 4.85-4.81 (m, 2H), 4.48-4.45 (m, 2H), 4.13-4.10 (m, 1H), 4.06-4.02 (m, 1H), 3.71-3.60 (m, 1H), 3.09 (s, 2H), 3.01 (s, 1H), 2.86-2.80 (m, 1H), 2.19-2.12 (m, 1H), 2.09-1.97 (m, 2H), 1.86-1.74 (m, 3H).

Example 1ak: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiazol-5-yl)-5,6-dihydro-4H-[1,4]oxazepino[5,6,7-de]quinazolin-9-yl)-7-fluorobenzo[b]thiophene-3-carbonitrile (789)

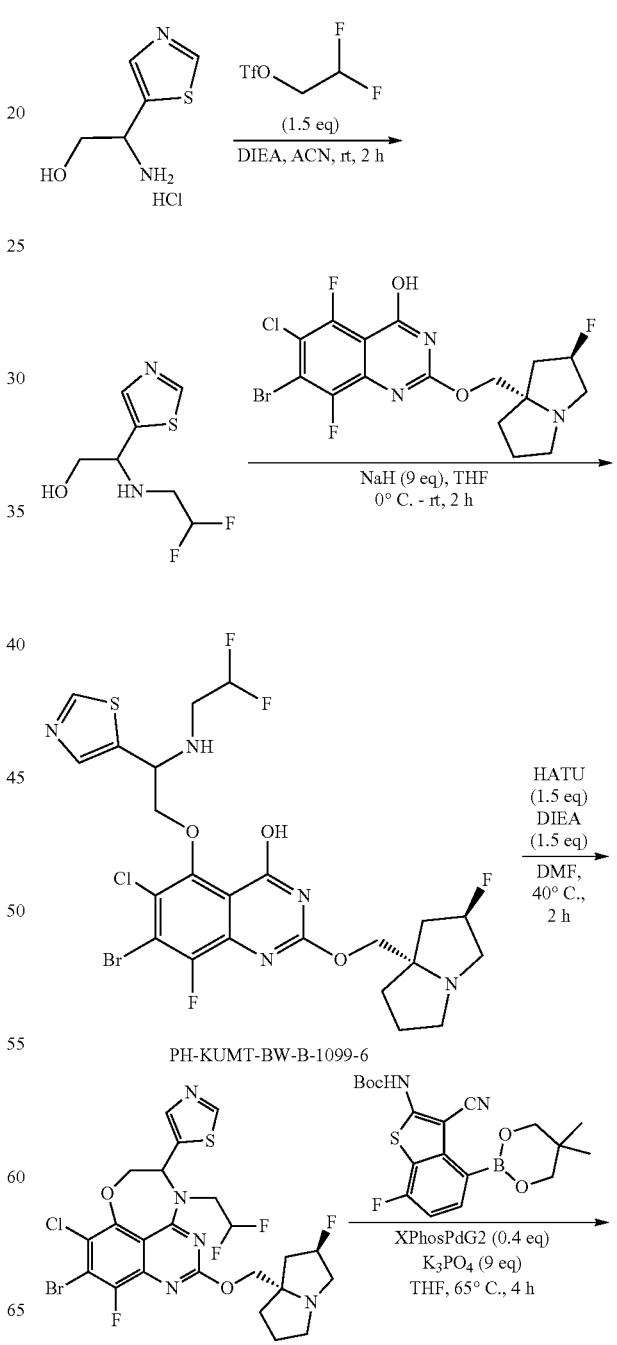

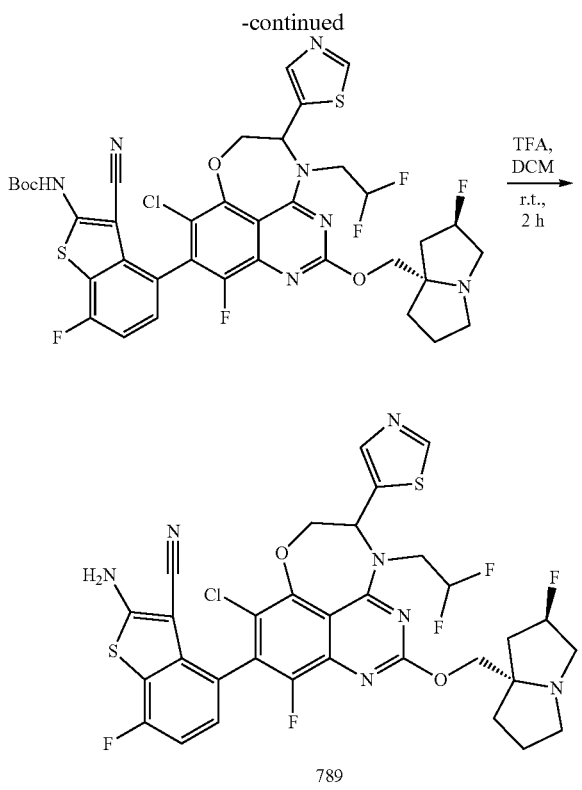

oxazepino[5,6,7-de]quinazoline To a stirred mixture of 7-bromo-6-chloro-5-(2-((2,2-difluoroethyl)amino)-2-(thiazol-5-yl)ethoxy)-8-fluoro-2-(((2R,7aS)-2-fluorotetrahydro-1H-pyrrolizin-7a(5H)-yl)methoxy)quinazolin-4-ol (513 mg, 0.520 mmol, 1 equiv, 65%) and HATU (296 mg, 0.780 mmol, 1.5 equiv) in DMF (7.43 mL) was added DIEA (100 mg, 0.780 mmol, 1.5 equiv) dropwise at room temperature. The resulting mixture was stirred for 2 hours at 40° C. It was cooled and concentrated under reduced pressure to give a residue. The residue was purified by reversed-phase flash chromatography with the following conditions: column, $C_{18}$; mobile phase, MeCN in Water (10 mmol/L $NH_4HCO_3$), 5% to 75% gradient in 15 min; detector, UV 254 nm to afford the desired product as a yellow solid. (ESI, m/z):622 [M+H]$^+$.

Tert-butyl (4-(8-chloro-4-(2,2-difluoroethyl)-10-fluoro-2-(((2R,7aS)-2-fluorotetrahydro-1H-pyrrolizin-7a(5H)-yl) methoxy)-5-(thiazol-5-yl)-5,6-dihydro-4H-[1,4]oxazepino [5,6,7-de]quinazolin-9-yl)-3-cyano-7-fluorobenzo[b] thiophen-2-yl)carbamate To a stirred solution of 9-bromo-8-chloro-4-(2,2-difluoroethyl)-10-fluoro-2-(((2R,7aS)-2-fluorotetrahydro-1H-pyrrolizin-7a(5H)-yl)methoxy)-5-(thiazol-5-yl)-5,6-dihydro-4H-[1,4]oxazepino[5,6,7-de] quinazoline (205 mg, 0.329 mmol, 1 equiv) and tert-butyl N-[3-cyano-4-(5,5-dimethyl-1,3,2-dioxaborinan-2-yl)-7-fluoro-1-benzothiophen-2-yl]carbamate (399 mg, 0.987 mmol, 3.0 equiv) in THF (4.88 mL) were added $K_3PO_4$ (628 mg, 2.961 mmol, 9.00 equiv) and dicyclohexyl[2', 4', 6'-tris (propan-2-yl)-[1,1'-biphenyl]-2-yl]phosphane; (2'-amino-[1, 1'-biphenyl]-2-yl(chloro)palladium (103.58 mg, 0.132 mmol, 0.40 equiv) in portions at room temperature under nitrogen atmosphere. The resulting mixture was stirred for 4 hours at 65° C. under nitrogen atmosphere. It was cooled and concentrated under reduced pressure to give a residue. The residue was purified by reversed-phase flash chromatography with the following conditions: column, C18 silica gel; mobile phase, MeCN in Water (10 mmol/L $NH_4HCO_3$), 5% to 70% gradient in 20 min; detector, UV 254 nm to afford the desired product as a white solid. (ESI, m/z):834 [M+H]$^+$.

2-Amino-4-(8-chloro-4-(2,2-difluoroethyl)-10-fluoro-2-(((2R,7aS)-2-fluorotetrahydro-1H-pyrrolizin-7a(5H)-yl) methoxy)-5-(thiazol-5-yl)-5,6-dihydro-4H-[1,4]oxazepino [5,6,7-de]quinazolin-9-yl)-7-fluorobenzo[b]thiophene-3-carbonitrile (789) To a stirred solution of tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(thiazol-5-yl)-5,6-dihydro-4H-[1,4]oxazepino[5,6,7-de] quinazolin-9-yl)-3-cyano-7-fluorobenzo[b]thiophen-2-yl) carbamate (86 mg, 0.103 mmol, 1 equiv) in DCM (2 mL) was added TFA (1 mL) dropwise at 0° C. The resulting mixture was stirred for 2 hours at room temperature and concentrated under reduced pressure to give residue. It was basified to pH~7 with triethylamine. The resulting mixture was extracted with DCM (3×10 mL). The extracts were combined, washed with brine, and dried over sodium sulfate. It was filtered and concentrated to give a crude. The crude product was purified by Prep-HPLC with the following conditions (Column: XBridge BEH Shield RP18 5 m, 30 mm*150 mm; Mobile Phase A: Water (10 mmol/L $NH_4HCO_3$), Mobile Phase B: ACN; Flow rate: 60 mL/min; Gradient: 40% B to 65% B in 8 min; Wave Length: UV 254 nm/220 nm; RT1(min): 7.57) to afford 0A/OB (35 mg). The 0A/OB (35 mg) was sent to chiral separation with the following conditions (Column: CHIRALPAK-ID 2*25 cm, 5m; Mobile Phase A: HEX(0.1% DEA), Mobile Phase B: HEX(0.1% DEA); Flow rate: 20 mL/min; Gradient: isocratic 30; Wave Length: UV 254/220 nm; RT1(min): 6.18;

2-((2,2-difluoroethyl)amino)-2-(thiazol-5-yl)ethan-1-ol To a stirred solution of 2-amino-2-(thiazol-5-yl)ethan-1-ol hydrochloride hydrochloride (1.4 g, 7.750 mmol, 1 equiv) and DIEA (4.05 mL, 23.251 mmol, 3.00 equiv) in ACN (28.0 mL) were added 2,2-difluoroethyl trifluoromethanesulfonate (1.54 mL, 11.616 mmol, 1.50 equiv) dropwise at room temperature. The resulting mixture was stirred for 4 hours at room temperature under nitrogen atmosphere. It was concentrated under reduced pressure, treated with water and extracted with ethyl acetate (5×50 mL). The extracts were combined, washed with water (3×30 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford desired product as a yellow oil. (ESI, m/z): 209 [M+H] +

7-Bromo-6-chloro-5-(2-((2,2-difluoroethyl)amino)-2-(thiazol-5-yl)ethoxy)-8-fluoro-2-(((2R,7aS)-2-fluorotetrahydro-1H-pyrrolizin-7a(5H)-yl)methoxy)quinazolin-4-ol To a stirred solution of 2-((2,2-difluoroethyl)amino)-2-(thiazol-5-yl)ethan-1-ol (207.01 mg, 0.995 mmol, 1.50 equiv) and 7-bromo-6-chloro-5,8-difluoro-2-(((2R,7aS)-2-fluorotetrahydro-1H-pyrrolizin-7a(5H)-yl)methoxy)quinazolin-4-ol (300 mg, 0.663 mmol, 1.00 equiv) in THF (60.0 mL) was added NaH (238 mg, 5.965 mmol, 9.00 equiv, 60%) in portions at 0° C. The resulting mixture was stirred for 2 hours at room temperature under nitrogen atmosphere, quenched with water at 0° C., and extracted with ethyl acetate (3×50 mL). The extracts were combined, washed with water (3×10 mL), and dried over anhydrous $Na_2SO_4$. After filtration, the filtrate was concentrated under reduced pressure to give the desired product which was used in the next step directly without further purification. (ESI, m/z) 640 [M+H]$^+$ 9-Bromo-8-chloro-4-(2,2-difluoroethyl)-10-fluoro-2-(((2R,7aS)-2- fluorotetrahydro-1H-pyrrolizin-7a (5H)-yl)methoxy)-5-(thiazol-5-yl)-5,6-dihydro-4H-[1,4]

1319

RT2(min): 8.96; Sample Solvent: MeOH; Injection Volume: 2.0 mL; Number Of Runs: 2) to give desired product as a white solid. (ESI, m/z):733 [M+H]$^+$.

$^1$H NMR: (400 MHZ, DMSO-d$_6$, ppm) δ 8.83 (s, 1H), 7.91 (s, 1H), 7.24-7.18 (m, 1H), 7.04 (dd, J=9.2, 8.3 Hz, 1H), 6.60 (t, J=56.7 Hz, 1H), 5.82-5.16 (m, 4H), 4.78 (dd, J=13.0, 4.1 Hz, 1H), 4.67 (d, J=13.0 Hz, 1H), 4.54 (m, 2H), 3.65 (s, 2H), 3.43 (m, 2H), 2.98 (m, 2H), 2.05 (m, 6H).

1320

Example 1al: Synthesis of 4-[(12R)-3-([(2R,7aS)-2-fluoro-hexahydropyrrolizin-7a-yl]methoxy-8-chloro-13-[(trans-2-cyanocyclopropyl)methyl]-6-fluoro-12-(1-hydroxycyclopropyl)-10-oxa-2,4,13-triazatricyclo [7.4.1.0^(5,14]tetradeca-1,3,5,7,9(14)-pentaen-7-yl]-2-amino-7-fluoro-1-benzothiophene-3-carbonitrile (821, 1123, 942, 729)

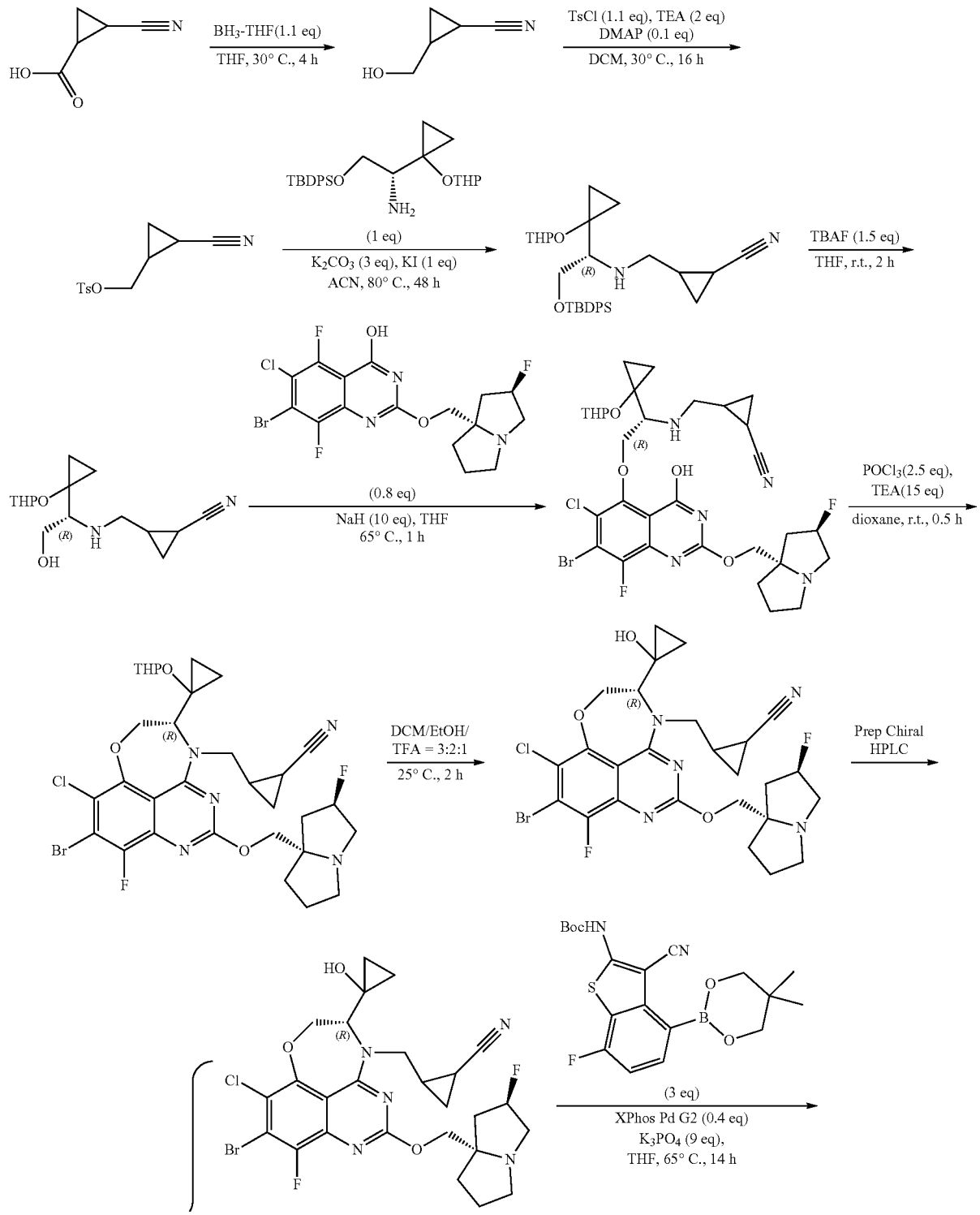

1321
peak 1 (polar)
peak 2 (less polar)
1322
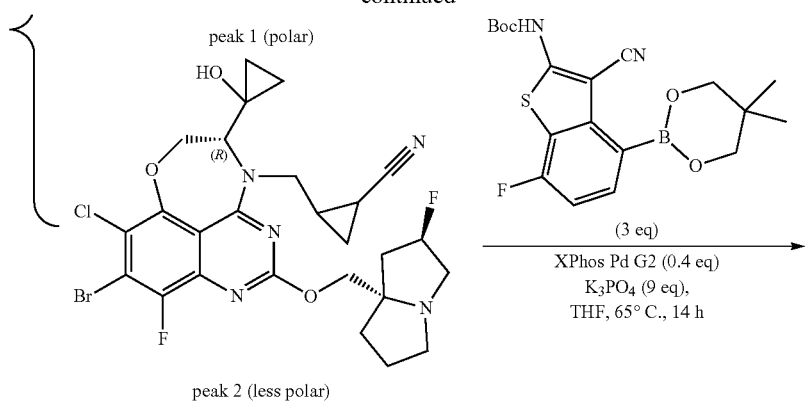
(3 eq)
XPhos Pd G2 (0.4 eq)
K₃PO₄ (9 eq),
THF, 65° C., 14 h
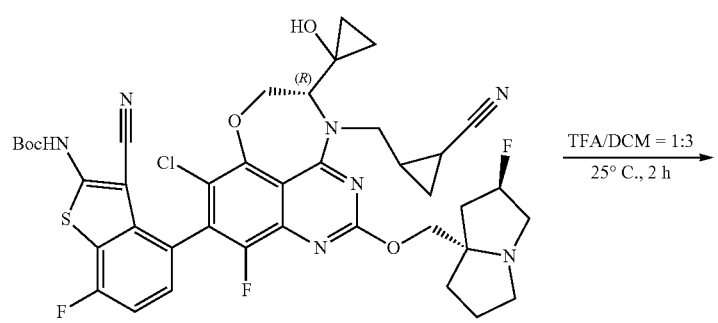
TFA/DCM = 1:3
25° C., 2 h
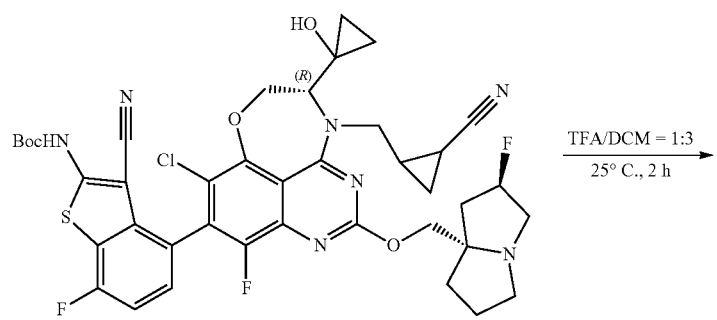
TFA/DCM = 1:3
25° C., 2 h
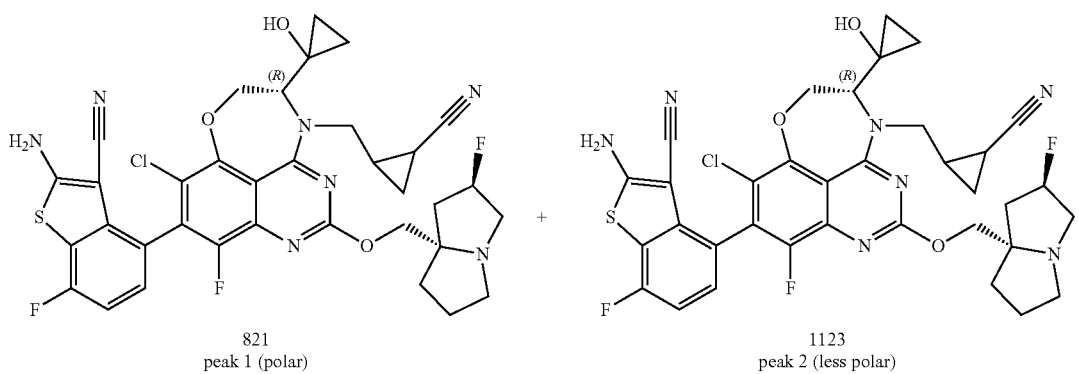
821
peak 1 (polar)
1123
peak 2 (less polar)

-continued

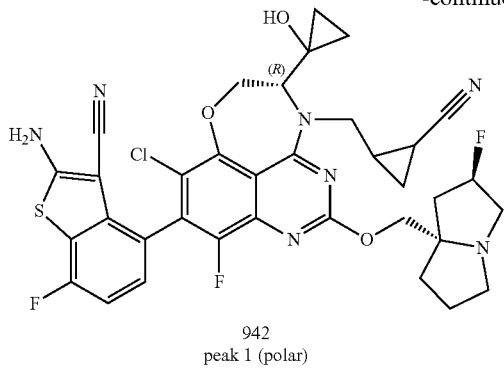

942
peak 1 (polar)

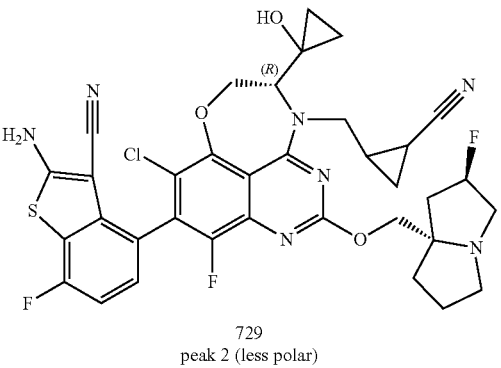

729
peak 2 (less polar)

2-Trans-(hydroxymethyl)cyclopropane-1-carbonitrile A solution of trans-2-cyanocyclopropane-1-carboxylic acid (3.95 g, 35.55 mmol, 1 equiv) and BH$_3$-THF (3.74 mL, 39.11 mmol, 1.1 equiv) in THF (40 mL, 493.711 mmol) was stirred for 4 hours at 30° C. under nitrogen atmosphere. The reaction was quenched by the addition of MeOH (40 mL) at 0° C. It was quenched with water and extracted with ethyl acetate. The extracts were combined, washed with brine and dried over Na$_2$SO$_4$. It was filtered and solvent was removed under reduced pressure to give the desired product as a yellow oil which was used directly in the next step without further purification.
$^1$H NMR: (400 MHZ, Chloroform-d) § 3.71 (dd, J=11.5, 5.1 Hz, 1H), 3.57 (dd, J=11.5, 5.8 Hz, 1H), 1.77 (ddt, J=10.9, 9.0, 5.4 Hz, 1H), 1.36 (dt, J=9.3, 4.9 Hz, 1H), 1.25 (dt, J=8.9, 5.1 Hz, 1H), 1.05 (ddd, J=8.9, 6.5, 5.2 Hz, 1H).

(Trans-2-cyanocyclopropyl)methyl 4-methylbenzenesulfonate A mixture of trans-2-(hydroxymethyl)cyclopropane-1-carbonitrile (3.4 g, 35.01 mmol, 1 equiv), TsCI (7.34 g, 38.51 mmol, 1.1 equiv), DMAP (0.9 mL, 14.16 mmol, 0.1 equiv) and triethylamine (9.73 mL, 70.02 mmol, 2 equiv) in DCM (30 mL, 471.92 mmol) was stirred for 16 hours at 30° C. under nitrogen atmosphere. The mixture was extracted with ethyl acetate (2×30 mL). The extracts were combined, washed with brine (1×30 mL), dried over anhydrous Na$_2$SO$_4$. After filtration, the filtrate was concentrated under reduced pressure to give a residue. The residue was purified by silica gel column chromatography, eluted with petroleum/ethyl acetate (5: 1) to afford the desired product as a colorless oil. $^1$H NMR: (400 MHZ, DMSO-d$_6$, ppm) δ 7.83-7.76 (m, 2H), 7.52-7.47 (m, 2H), 4.02 (dd, J=11.1, 6.6 Hz, 1H), 3.92 (dd, J=11.1, 7.6 Hz, 1H), 2.43 (s, 3H), 1.86-1.77 (m, 1H), 1.72 (ddd, J=9.0, 5.4, 4.5 Hz, 1H), 1.27 (dt, J=8.9, 5.2 Hz, 1H), 1.00 (ddd, J=9.0, 6.3, 5.0 Hz, 1H).

Trans-2-(([(1R)-2-[(tert-butyldiphenylsilyl)oxy]-1-[1-(oxan-2-yloxy)cyclopropyl]ethyl]-aminomethyl)cyclopropane-1-carbonitrile A mixture of (trans-2-cyanocyclopropyl) methyl 4-methylbenzenesulfonate (1 g, 3.979 mmol, 1 equiv), [(2R)-2-amino-2-[1-(oxan-2-yloxy)cyclopropyl]ethoxy](tert-butyl)diphenylsilane (1.75 g, 3.98 mmol, 1 equiv), K$_2$CO$_3$ (1.65 g, 11.94 mmol, 3 equiv) and KI (0.66 g, 3.98 mmol, 1 equiv) in ACN (10 mL, 190.242 mmol) was stirred for 48 hours at 80° C. It was cooled down to room temperature and extracted with ethyl acetate (3×10 mL). The extracts were combined, washed with brine (1×20 mL), and dried over anhydrous Na$_2$SO$_4$. After filtration, the filtrate was concentrated under reduced pressure to give a residue. The residue was purified by silica gel column chromatography, eluted with DCM/MeOH (10: 1) to afford the desired product (as a colorless oil. (ESI, m/z): 519 [M+H]$^+$ Trans-2-((([(1R)-2-hydroxy-1-[1-(oxan-2-yloxy)cyclopropyl]ethyl]aminomethyl)cyclopropane-1-carbonitrile A solution of trans-2-(([(1R)-2-[(tert-butyldiphenylsilyl)oxy]-1-[1-(oxan-2-yloxy)cyclopropyl]ethyl]aminomethyl) cyclopropane-1-carbonitrile (2 g, 3.85 mmol, 1 equiv) and TBAF (1.51 g, 5.78 mmol, 1.5 equiv) in THF (20 mL, 246.85 mmol) was stirred for 2 hours at room temperature under nitrogen atmosphere and extracted with ethyl acetate (2×5 mL). The extracts were combined, washed with brine (1×10 mL), dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10: 1) to afford the desired product as a light-yellow oil. (ESI, m/z): 281 [M+H]$^+$ Trans-2-((([(1R)-2-[(2-([(2R,7aS)-2-fluoro-hexahydropyrrolizin-7α-yl]methoxy-7-bromo-6-chloro-8-fluoro-4-hydroxyquinazolin-5-yl)oxy]-1-[1-(oxan-2-yloxy)cyclopropyl]ethyl]-aminomethyl)cyclopropane-1-carbonitrile A mixture of trans-2-((([(1R)-2-hydroxy-1-[1-(oxan-2-yloxy) cyclopropyl]ethyl]aminomethyl) cyclopropane-1-carbonitrile (750 mg, 2.67 mmol, 1 equiv), 2-{[(2R,7aS)-2-fluoro-hexahydropyrrolizin-7a-yl]methoxy}-7-bromo-6-chloro-5,8-difluoroquinazolin-4-ol (968 mg, 2.14 mmol, 0.8 equiv), and NaH (1069 mg, 26.75 mmol, 10 equiv, 60%) in THF (5 mL, 61.714 mmol) was stirred for 1 hour at 65° C. under nitrogen atmosphere. The reaction was quenched with ice at 0° C. and extracted with ethyl acetate (3×5 mL). The extracts were combined, washed with brine (1×10 mL), and dried over anhydrous Na$_2$SO$_4$. After filtration, the filtrate was concentrated under reduced pressure to afford the desired product as a grey solid which was used in the next step directly without further purification. (ESI, m/z): 712 [M+H]$^+$ Trans-2-([(12R)-3-([(2R,7aS)-2-fluoro-hexahydropyrrolizin-7a-yl]methoxy-7-bromo-8-chloro-6-fluoro-12-[1-(oxan-2-yloxy)cyclopropyl]-10-oxa-2,4,13-triazatricyclo-[7.4.1.0 (5,14]tetradeca-1,3,5,7,9(14)-pentaen-13-yl] methylcyclopropane-1-carbonitrile A solution of trans-2-((([(1R)-2-[(2-([(2R,7aS)-2-fluoro-hexahydropyrrolizin-7a-yl]methoxy-7-bromo-6-chloro-8-fluoro-4-hydroxyquinazolin-5-yl)oxy]-1-[1-(oxan-2-yloxy) cyclopropyl]ethyl]aminomethyl)cyclopropane-1-carbonitrile (2.2 g, 3.08 mmol, 1 equiv), triethylamine (6.43 mL, 46.27 mmol, 15 equiv) and POCl$_3$ (0.72 mL, 7.713 mmol, 2.5 equiv) in dioxane (50 mL, 590.19 mmol) was stirred for 0.5 hours at room temperature under nitrogen atmosphere. It was then extracted with ethyl acetate (2×10 mL). The extracts were combined, washed with brine (1×10 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (20:1) to afford the desired product as a yellow solid. (ESI, m/z): 694 $[M+H]^+$ Trans-2-([(12R)-3-([(2R,7aS)-2-fluoro-hexahydropyrrolizin-7a-yl]methoxy-7-bromo-8-chloro-6-fluoro-12-(1-hydroxycyclopropyl)-10-oxa-2,4,13-triazatricyclo [7.4.1.0 (5,14] tetradeca-1,3,5,7,9(14)-pentaen-13-yl]methylcyclopropane-1-carbonitrile A solution of trans-2-([(12R)-3-([(2R,7aS)-2-fluoro-hexahydropyrrolizin-7a-yl]methoxy-7-bromo-8-chloro-6-fluoro-12-[1-(oxan-2-yloxy) cyclopropyl]-10-oxa-2,4,13-triazatricyclo[7.4.1.0 (5,14] tetradeca-1,3,5,7,9(14)-pentaen-13-yl]methylcyclopropane-1-carbonitrile (1 g, 1.44 mmol, 1 equiv), TFA (2 mL, 26.92 mmol), EtOH (4 mL, 68.85 mmol) in DCM (6 mL, 94.38 mmol) was stirred for 2 hours at 25° C. The resulting mixture was concentrated under reduced pressure to give a crude. The crude product (1.1 g) was purified by Prep-HPLC with the following conditions (Column: CHIRAL ART Cellulose-SB 3*25 cm, 5m; Mobile Phase A: HEX(0.1% DEA), Mobile Phase B: EtOH: DCM=1: 1; Flow rate: 40 mL/min; Gradient: isocratic 10; Wave Length: UV 254/220 nm; RT1(min): 28.787; RT2(min): 32.76; Sample Solvent: MeOH; Sample concentration: mg/mL; Injection Volume: 0.33 mL; Number Of Runs: 24) to afford desired product, desired intermediate A (polar) and desired intermediate B (less polar) as a light yellow solids.

Desired intermediate A (Peak A): (ESI, m/z): 610 $[M+H]^+$
Desired intermediate B (Peak B): (ESI, m/z): 610 $[M+H]^+$ Tert-butyl N-(4-[(12R)-3-([(2R,7aS)-2-fluoro-hexahydropyrrolizin-7a-yl]methoxy-8-chloro-13-[(trans-2-cyanocyclopropyl)methyl]-6-fluoro-12-(1-hydroxycyclopropyl)-10-oxa-2,4,13-triazatricyclo[7.4.1.0 (5,14]tetradeca-1,3,5,7,9 (14)-pentaen-7-yl]-3-cyano-7-fluoro-1-benzothiophen-2-ylcarbamate A mixture of trans-2-([(12R)-3-([(2R,7aS)-2-fluoro-hexahydropyrrolizin-7a-yl]methoxy-7-bromo-8-chloro-6-fluoro-12-(1-hydroxycyclopropyl)-10-oxa-2,4,13-triazatricyclo[7.4.1.0 (5,14]tetradeca-1,3,5,7,9(14)-pentaen-13-yl]methylcyclopropane-1-carbonitrile (from desirer product A: peak A from previous step) (250 mg, 0.41 mmol, 1 equiv), tert-butyl N-[3-cyano-4-(5,5-dimethyl-1,3,2-dioxaborinan-2-yl)-7-fluoro-1-benzothiophen-2-yl]carbamate (496.32 mg, 1.227 mmol, 3 equiv), 2nd Generation XPhos precatalyst (117 mg, 0.164 mmol, 0.4 equiv) and $K_3PO_4$ (781 mg, 3.681 mmol, 9 equiv) in THF (4 mL, 49.371 mmol, 120 equiv) was stirred for 14 hours at 65° C. under nitrogen atmosphere. It was cooled and extracted with ethyl acetate (3×5 mL). The extracts were combined, washed with brine (1×10 mL), dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a yellow solid. (ESI, m/z): 822 $[M+H]^+$ 4-[(12R)-3-([(2R,7aS)-2-fluoro-hexahydropyrrolizin-7a-yl]methoxy-8-chloro-13-[(trans-2-cyanocyclopropyl) methyl]-6-fluoro-12-(1-hydroxycyclopropyl)-10-oxa-2,4, 13-triazatricyclo[7.4.1.0 (5,14]tetradeca-1,3,5,7,9(14)-pentaen-7-yl]-2-amino-7-fluoro-1-benzothiophene-3-carbonitrile A solution of tert-butyl N-(4-[(12R)-3-([(2R, 7aS)-2-fluoro-hexahydropyrrolizin-7a-yl]methoxy-8-chloro-13-[(trans-2-cyanocyclopropyl)methyl]-6-fluoro-12-(1-hydroxycyclopropyl)-10-oxa-2,4,13-triazatricyclo [7.4.1.0 (5,14]tetradeca-1,3,5,7,9(14)-pentaen-7-yl]-3-cyano-7-fluoro-1-benzothiophen-2-ylcarbamate (105 mg, 0.128 mmol, 1 equiv) and TFA (1 mL, 13.463 mmol) in DCM (3 mL, 47.192 mmol) was stirred for 2 hours at 25° C. The resulting mixture was concentrated under reduced pressure and basified to pH~8 with $NH_3 \cdot H_2O$. It was concentrated to give a crude. The crude product (110 mg) was purified by Prep-HPLC with the following conditions (Column: XBridge BEH Shield RP18 5 m, 30 mm*150 mm; Mobile Phase A: Water (10 mmol/L $NH_4HCO_3$), Mobile Phase B: ACN; Flow rate: 60 mL/min; Gradient: 38% B to 58% B in 10 min; Wave Length: UV 254 nm/220 nm; RT1(min): 8.52/9.45) to afford desired final product 821 (peak 1, polar) as a white solid and desired final product 1123 (peak 2, less polar) as a white solid.

821 (peak 1, polar): (ESI, m/z): 722 $[M+H]^+$; $^1H$ NMR: (400 MHZ, DMSO-$d_6$, ppm) δ 8.09 (s, 2H), 7.19 (dd, J=8.4, 5.4 Hz, 1H), 7.13 (dd, J=9.4, 8.4 Hz, 1H), 5.42 (s, 1H), 5.28 (d, J=54.5 Hz, 1H), 4.90 (dd, J=12.9, 4.9 Hz, 1H), 4.41-4.35 (m, 1H), 4.35-4.26 (m, 1H), 4.13 (d, J=10.3 Hz, 1H), 4.05 (d, J=10.3 Hz, 1H), 3.61 (d, J=4.6 Hz, 1H), 3.25 (s, 1H), 3.16-3.06 (m, 2H), 3.04 (d, J=7.8 Hz, 1H), 2.90-2.78 (m, 1H), 2.21-1.99 (m, 4H), 1.95-1.72 (m, 4H), 1.26 (ddt, J=14.1, 9.4, 5.1 Hz, 2H), 0.82-0.55 (m, 4H).

1123 (peak 2, less polar): (ESI, m/z): 722 $[M+H]^+$; $^1H$ NMR: (400 MHZ, DMSO-$d_6$, ppm) δ 8.07 (s, 2H), 7.22 (dd, J=8.4, 5.3 Hz, 1H), 7.14 (dd, J=9.4, 8.4 Hz, 1H), 5.48 (s, 1H), 5.28 (d, J=54.6 Hz, 1H), 4.90 (dd, J=12.9, 5.3 Hz, 1H), 4.48 (d, J=12.6 Hz, 1H), 4.41 (dd, J=14.0, 5.3 Hz, 1H), 4.15 (d, J=10.3 Hz, 1H), 4.02 (d, J=10.3 Hz, 1H), 3.95 (d, J=5.2 Hz, 1H), 3.24-3.15 (m, 1H), 3.14-3.07 (m, 2H), 3.04 (d, J=9.4 Hz, 1H), 2.83 (d, J=7.1 Hz, 1H), 2.20-2.11 (m, 1H), 2.04 (d, J=12.9 Hz, 3H), 1.91-1.70 (m, 4H), 1.27-1.20 (m, 2H), 0.68-0.42 (m, 4H).

Starting from desired intermediate B, following the same procedure for the synthesis of desired final product 821 and desired final product 1123, desired final product 942 and desired final product 729 were synthesized.

942 (peak 1, polar): (ESI, m/z): 722 $[M+H]^+$; $^1H$ NMR: (400 MHZ, DMSO-$d_6$, ppm) δ 8.08 (s, 2H), 7.19 (dd, J=8.4, 5.4 Hz, 1H), 7.13 (t, J=8.9 Hz, 1H), 5.39 (s, 1H), 5.28 (d, J=54.2 Hz, 1H), 4.91 (dd, J=12.9, 5.0 Hz, 1H), 4.28 (dd, J=13.3, 4.4 Hz, 2H), 4.07 (q, J=10.3 Hz, 2H), 3.67 (d, J=4.7 Hz, 1H), 3.40 (d, J=7.3 Hz, 1H), 3.10 (d, J=10.7 Hz, 2H), 3.02 (s, 1H), 2.83 (q, J=8.8, 8.1 Hz, 1H), 2.23-2.11 (m, 1H), 2.05 (d, J=10.1 Hz, 3H), 1.97 (dt, J=9.4, 4.9 Hz, 1H), 1.80 (dt, J=17.4, 11.6 Hz, 3H), 1.34- 1.19 (m, 2H), 0.85-0.77 (m, 1H), 0.77-0.61 (m, 3H).

729 (peak 2, polar): (ESI, m/z): 722 $[M+H]^+$; $^1H$ NMR: (400 MHZ, DMSO-$d_6$, ppm) δ 8.07 (s, 2H), 7.22 (dd, J=8.3, 5.3 Hz, 1H), 7.14 (dd, J=9.5, 8.4 Hz, 1H), 5.44 (s, 1H), 5.28 (d, J=54.7 Hz, 1H), 4.90 (dd, J=12.9, 5.4 Hz, 1H), 4.48 (d, J=12.6 Hz, 1H), 4.39 (dd, J=14.0, 5.2 Hz, 1H), 4.11 (d, J=10.3 Hz, 1H), 4.08-3.95 (m, 2H), 3.21 (dd, J=14.1, 7.4 Hz, 1H), 3.09 (d, J=9.5 Hz, 2H), 3.01 (s, 1H), 2.83 (q, J=8.8, 8.3 Hz, 1H), 2.23-2.12 (m, 1H), 2.11-2.01 (m, 3H), 1.96 (dt, J=9.5, 4.9 Hz, 1H), 1.91-1.72 (m, 3H), 1.31-1.23 (m, 1H), 1.24-1.14 (m, 1H), 0.70-0.54 (m, 3H), 0.48 (td, J=9.1, 8.4, 4.3 Hz, 1H). Example 1 am: Synthesis of 2-amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (1031, 831, 702, 712)

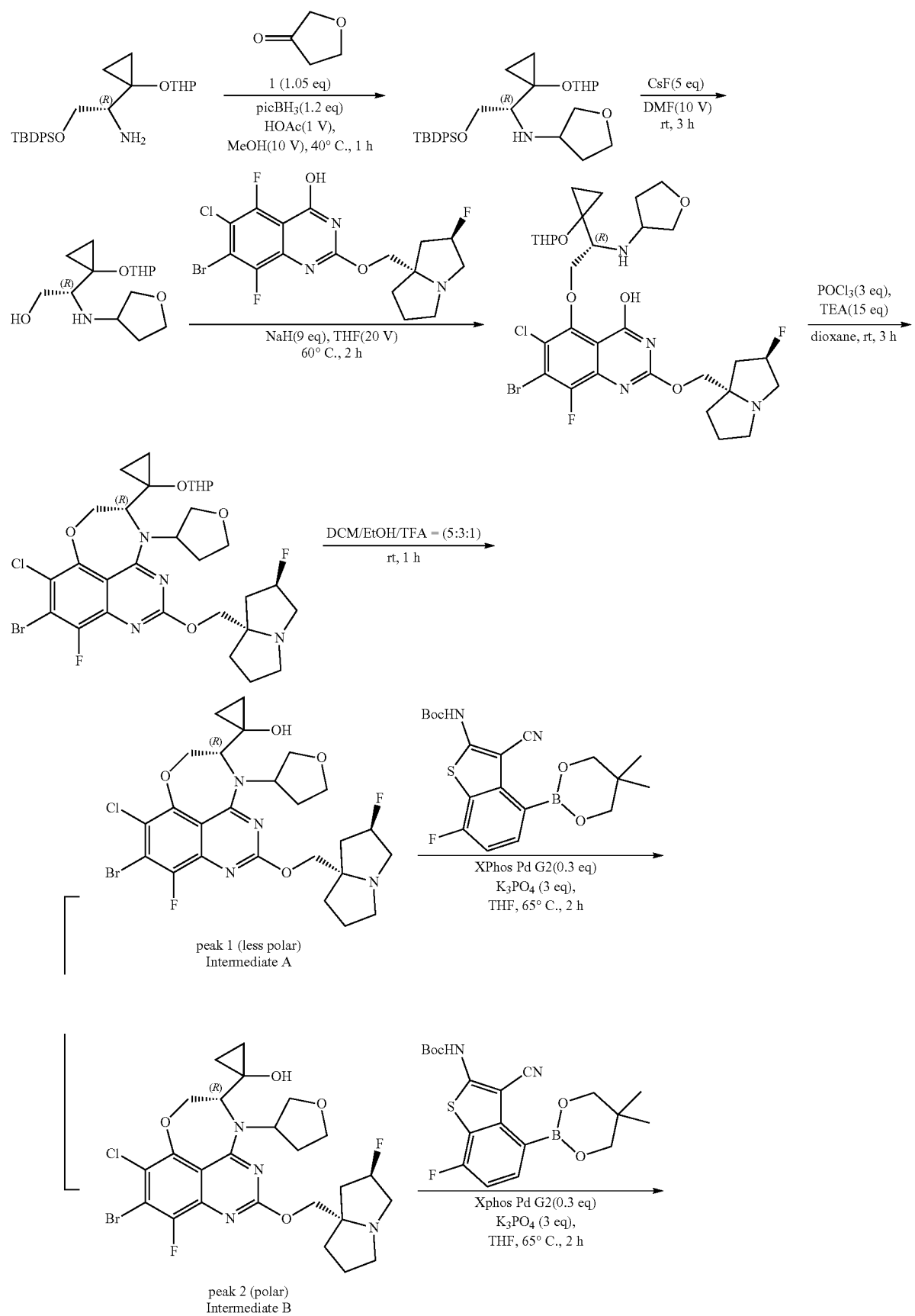

-continued

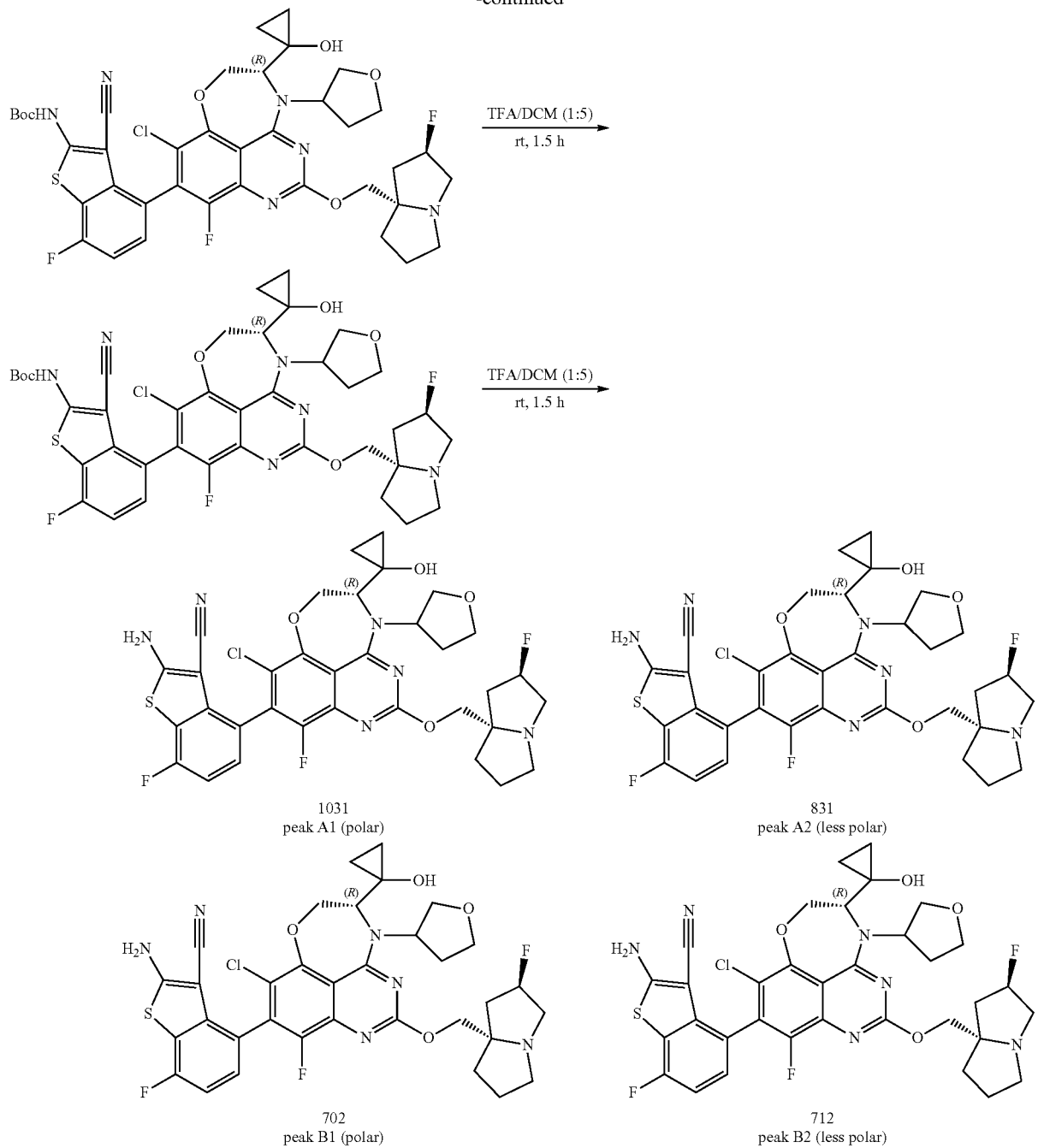

1031
peak A1 (polar)

831
peak A2 (less polar)

702
peak B1 (polar)

712
peak B2 (less polar)

N-[(1R)-2-[(tert-butyldiphenylsilyl)oxy]-1-[1-(oxan-2-yloxy)cyclopropyl]ethyl]oxolan-3-amine To a stirred solution of [(2R)-2-amino-2-[1-(oxan-2-yloxy) cyclopropyl] ethoxy](tert-butyl)diphenylsilane (1000 mg, 2.274 mmol, 1 equiv) and dihydrofuran-3-one (205 mg, 2.388 mmol, 1.05 equiv) in HOAc (1.0 mL) and MeOH (10.0 mL) was added PicBH3 (291 mg, 2.729 mmol, 1.2 equiv) at room temperature. The resulting mixture was stirred for 1 hour at 40° C. It was cooled to room temperature and the reaction was quenched with sat. NH$_4$Cl (aq.), extracted with ethyl acetate (3×50 mL). The extracts were combined, washed with brine (1×20 mL), dried over anhydrous Na$_2$SO$_4$. After filtration, the filtrate was concentrated under reduced pressure to give a residue. The residue was purified by silica gel column chromatography, eluted with petroleum/ethyl acetate (3:1) to afford the desired product as a colorless oil: (ESI, m/z): 510[M+H]$^+$ (2R)-2-[1-(oxan-2-yloxy)cyclopropyl]-2-(oxolan-3-ylamino)ethanol To a stirred solution of N-[(1R)-2-[(tert-butyldiphenylsilyl)oxy]-1-[1-(oxan-2-yloxy) cyclopropyl] ethyl] oxolan-3-amine (415 mg, 0.814 mmol, 1 equiv) in DMF (5 mL) was added CsF (618 mg, 4.070 mmol, 5 equiv) at room temperature. The resulting mixture was stirred for 3 hours at room temperature. It was filtered and the filter cake was washed with CH$_2$Cl$_2$ (2×10 mL). The filtrate was concentrated under reduced pressure to give a residue. The residue was purified by silica gel column chromatography, eluted with CH$_2$Cl$_2$/MeOH (10:1) to afford the desired product as a colorless oil: (ESI, m/z): 272 [M+H]$^+$ Bis(2-{[(2R,7aS)-2-fluoro-hexahydropyrrolizin-7a-yl]methoxy}-7-bromo-6-chloro-8-fluoro-5-[(2R)-2-[1-(oxan-2-yloxy)cyclopropyl]-2-(oxolan-3-ylamino) ethoxy]quinazolin-4-ol) To a stirred solution of bis((2R)-2-[1-(oxan-2-yloxy)cyclopropyl]-2-(oxolan-3-ylamino)ethanol) (371 mg, 0.684 mmol, 1 equiv) and 2-{[(2R,7aS)-2-fluoro-hexahydropyrrolizin-7a-yl]methoxy}-7-bromo-6-chloro-5,8-difluoroquinazolin-4-ol (185 mg, 0.410 mmol, 0.6 equiv) in THF (7.5 mL) was added NaH (147 mg, 6.156 mmol, 9 equiv) at room temperature under nitrogen atmosphere. The resulting mixture was stirred for 2 hours at 60° C. under nitrogen atmosphere. It was cooled to room temperature, and the reaction was quenched with water/Ice at room temperature, extracted with ethyl acetate (3×100 mL). The extracts were combined, washed with brine (1×50 mL), dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 30% to 60% gradient in 20 min; detector, UV 254 nm to afford the desired product as a white solid:(ESI, m/z): 703 [M+H]$^+$ (5R)-9-bromo-8-chloro-10-fluoro-2-(((2R,7aS)-2-fluorotetrahydro-1H-pyrrolizin-7a(5H)-yl)methoxy)-5-(1-((tetrahydro-2H-pyran-2-yl)oxy)cyclopropyl)-4-(tetrahydrofuran-3-yl)-5,6-dihydro-4H-[1,4]oxazepino[5,6,7-de]quinazoline To a stirred solution of 2-{[(2R,7aS)-2-fluoro-hexahydropyrrolizin-7a-yl]methoxy}-7-bromo-6-chloro-8-fluoro-5-[(2R)-2-[1-(oxan-2-yloxy)cyclopropyl]-2-(oxolan-3-ylamino)ethoxy]quinazolin-4-ol (360 mg, 0.511 mmol, 1 equiv) and TEA (776 mg, 7.665 mmol, 15 equiv) in dioxane (18.0 mL) was added POCl$_3$ (235 mg, 1.533 mmol, 3 equiv) dropwise at 0° C. The resulting mixture was stirred for 3 hours at room temperature, quenched with water/ice and extracted with CH$_2$Cl$_2$ (3×50 mL). The extracts were combined, washed with brine (1×20 mL), dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 35% to 65% gradient in 20 min; detector, UV 254 nm to afford the desired product as a yellow green solid: (ESI, m/z): 685 [M+H]$^+$ 1-((5R)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-5-yl)cyclopropan-1-ol To a stirred solution of (5R)-9-bromo-8-chloro-10-fluoro-2-(((2R,7aS)-2-fluorotetrahydro-1H-pyrrolizin-7a(5H)-yl)methoxy)-5-(1-((tetrahydro-2H-pyran-2-yl)oxy)cyclopropyl)-4-(tetrahydrofuran-3-yl)-5,6-dihydro-4H-[1,4]oxazepino[5,6,7-de]quinazoline (330 mg, 0.481 mmol, 1 equiv) in DCM (8.25 mL) and EtOH (4.95 mL) was added TFA (1.65 mL) at room temperature. The resulting mixture was stirred for 1 hour at room temperature and concentrated under vacuum to give a residue. The residue was purified by Hexane (0.1% DEA):(EtOH/DCM)=1/1=80/20 to afford two desired intermediate: Intermediate A (peak 1, less polar):(ESI, m/z): 601 [M+H]$^+$ and Intermediate B (peak 2, polar):(ESI, m/z): 601 [M+H]$^+$ as yellow solids.

Intermediate A and Intermediate B were used in the following step separately for the final desired product.

Tert-butyl (4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate To a stirred solution of 1-((5R)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-5-yl)cyclopropan-1-ol (Intermediate A) (95 mg, 0.158 mmol, 1 equiv) and tert-butyl N-[3-cyano-4-(5,5-dimethyl-1,3,2-dioxaborinan-2-yl)-7-fluoro-1-benzothiophen-2-yl]carbamate (255 mg, 0.632 mmol, 4 equiv) in THF (9.5 mL) were added XPhos Pd G2 (31 mg, 0.040 mmol, 0.25 equiv) and K$_3$PO$_4$ (100 mg, 0.474 mmol, 3.0 equiv) at room temperature. The resulting mixture was stirred for 2 hours at 65° C. under argon atmosphere. It was cooled and concentrated under vacuum to give a residue. The residue was purified by reversed-phase flash chromatography with the following conditions: column, C18; mobile phase, MeCN in Water (10 mmol/L NH$_4$HCO$_3$), 30% to 70% gradient in 20 min; detector, UV 254 nm to afford the desired product as a yellow solid: (ESI, m/z): 813 [M+H]$^+$ 2-Amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile To a stirred solution of tert-butyl (4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate (60 mg, 0.074 mmol, 1 equiv) in DCM (3 mL) was added TFA (0.6 mL) at room temperature. The resulting mixture was stirred for 1.5 hours and concentrated under vacuum. The residue was purified prep-HPLC with the following conditions (Column: Xselect CSHTM Prep C18 5 µm 19*150 mm OBD; Mobile Phase A: Water (0.1% FA), Mobile Phase B: 20 mm NaOH+ 10% ACN; Flow rate: 60 mL/min; Gradient: 20% B to 40% B in 10 min; Wave Length: UV 254 nm/220 nm; RT1(min): 7.2) to afford two desired final product. Final desired product 1031 (polar) and final desired product 831 (less polar) as while solids 1031:(ESI, m/z):713 [M+H]$^+$; $^1$H NMR (400 MHZ, DMSO-d$_6$, ppm) δ 10.75 (s, 1H), 8.09 (br, 2H), 7.20-7.12 (m, 2H), 5.65-5.51 (m, 1H), 5.38-5.32 (m, 1H), 5.12-5.07 (m, 1H), 4.90-4.85 (m, 1H), 4.64-4.61 (m, 3H), 4.56-4.53 (m, 3H), 4.38-4.35 (m, 3H), 4.18-4.13 (m, 3H), 4.08-4.04 (m, 3H), 3.96-3.89 (m, 2H), 3.78-3.70 (m, 4H), 3.34-3.30 (m, 2H), 2.61-2.54 (m, 1H), 2.46-2.41 (m, 1H), 2.33-2.27 (m, 2H), 2.23-2.16 (m, 2H), 2.09-1.99 (m, 1H), 0.72-0.71 (m, 4H).

831: (ESI, m/z):713 [M+H]$^+$; $^1$H NMR (400 MHZ, DMSO-d$_6$, ppm) δ 8.10 (br, 2H), 7.23-7.13 (m, 2H), 5.66-5.64 (m, 1H), 5.52-5.46 (m, 1H), 5.06-5.04 (m, 1H), 4.94-4.89 (m, 1H), 4.61-4.51 (m, 3H), 4.11-4.02 (m, 3H), 3.98-3.94 (m, 1H), 3.92-3.84 (m, 1H), 3.80-3.69 (m, 3H), 3.30-3.26 (m, 2H), 2.61-2.57 (m, 1H), 2.44-2.43 (m, 1H), 2.33-2.28 (m, 1H), 2.23-2.15 (m, 3H), 2.07-2.04 (m, 1H), 0.67-0.57 (m, 3H), 0.53-0.48 (m, 1H).

2-Amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile Starting with intermediate B, final desired product 702 (polar) and final desired product 712 (less polar) were synthesized.

702:(ESI, m/z):713[M+H]⁺; ¹H NMR (400 MHZ, DMSO-d₆, ppm) δ 8.08 (br, 2H), 7.22-7.18 (m, 1H), 7.16-7.12 (m, 1H), 5.64-5.50 (m, 1H), 5.22-5.13 (m, 1H), 4.95-4.91 (m, 1H), 4.59 (s, 2H), 4.33-4.30 (m, 1H), 4.24-4.20 (m, 1H), 4.16-4.11 (m, 1H), 3.88-3.83 (m, 3H), 3.76-3.72 (m, 2H), 3.34-3.29 (m, 2H), 2.45-2.41 (m, 2H), 2.34-2.29 (m, 3H), 2.21-2.14 (m, 2H), 2.09-2.04 (m, 1H), 0.74-0.71 (m, 2H), 0.66-0.64 (m, 2H).

712:(ESI, m/z):713[M+H]⁺; ¹H NMR (400 MHZ, DMSO-d₆, ppm) δ 8.09 (br, 2H), 7.23-7.19 (m, 1H), 7.17-7.13 (m, 1H), 5.64-5.51 (m, 2H), 5.04-4.97 (m, 2H), 4.56 (s, 2H), 4.49-4.46 (m, 1H), 4.23-4.21 (m, 1H), 4.17-4.15 (m, 1H), 4.08-4.05 (m, 1H), 3.92-3.84 (m, 3H), 3.81-3.70 (m, 4H), 2.44-2.42 (m, 2H), 2.31-2.30 (m, 1H), 2.22-2.12 (m, 4H), 2.04-2.02 (m, 1H), 0.62-0.57 (m, 2H), 0.55-0.50 (m, 1H), 0.44-0.40 (m, 1H).

Example 1an: Synthesis of 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (697 and 890)

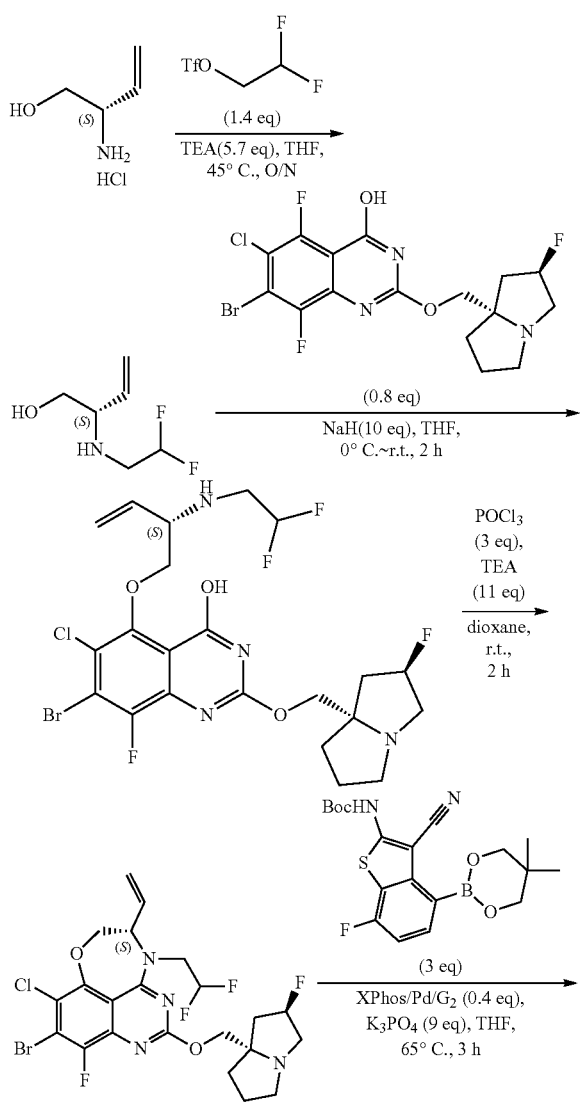

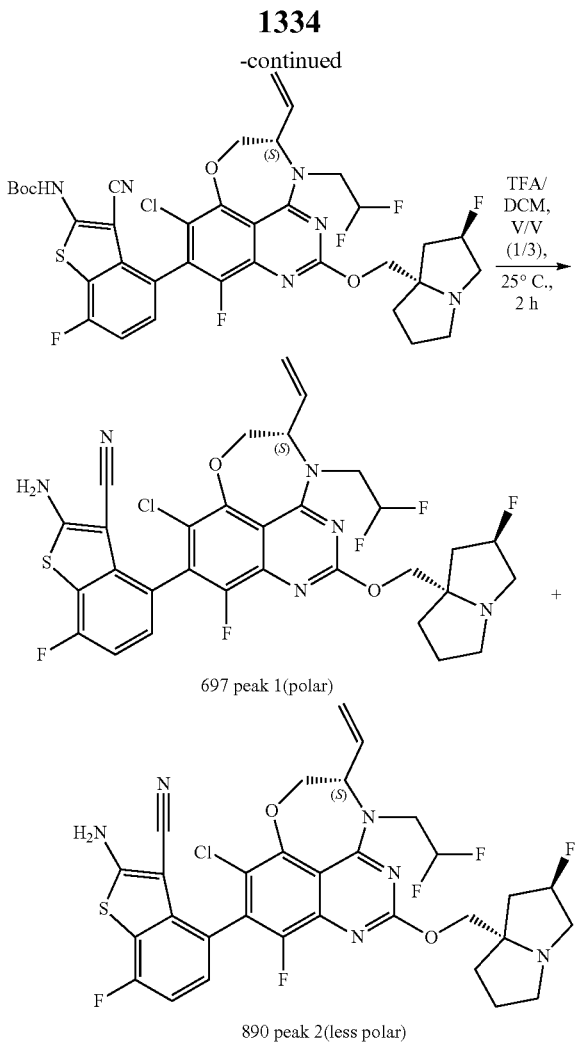

(2S)-2-[(2,2-difluoroethyl)amino]but-3-en-1-ol A mixture of (2S)-2-aminobut-3-en-1-ol hydrochloride (1.5 g, 12.138 mmol, 1 equiv), triethylamine (7.00 g, 69.187 mmol, 5.7 equiv) and 2,2-difluoroethyl trifluoromethanesulfonate (3.64 g, 16.993 mmol, 1.4 equiv) in THF (15 mL, 185.142 mmol) was stirred for overnight at 45° C. It was cooled to room temperature and diluted with water (50 mL), extracted with ethyl acetate (3×50 mL). The extracts were combined, washed with brine (1×70 mL), dried over anhydrous Na₂SO₄. After filtration, the filtrate was concentrated under reduced pressure to give a residue. The residue was purified by silica gel column chromatography, eluted with petroleum/ethyl acetate (1: 4) to afford the desired product as a colorless oil. ¹H NMR (400 MHZ, DMSO-d₆, ppm) δ 5.99 (tt, J=56.5, 4.3 Hz, 1H), 5.58 (ddd, J=17.6, 10.3, 7.5 Hz, 1H), 5.26-5.07 (m, 2H), 4.73 (t, J=5.5 Hz, 1H), 3.42-3.31 (m, 1H), 3.27 (ddd, J=10.6, 7.3, 5.6 Hz, 1H), 3.09 (td, J=7.3, 4.7 Hz, 1H), 2.89-2.76 (m, 2H), 2.09 (s, 1H).

7-Bromo-6-chloro-5-(((S)-2-((2,2-difluoroethyl)amino)but-3-en-1-yl)oxy)-8-fluoro-2-(((2R,7aS)-2-fluorotetrahydro-1H-pyrrolizin-7a(5H)-yl)methoxy)quinazolin-4-ol A solution of (2S)-2-[(2,2-difluoroethyl)amino]but-3-en-1-ol (180 mg, 1.191 mmol, 1 equiv) and 2-([(2R,7aS)-2-fluorohexahydropyrrolizin-7a-yl]methoxy-7-bromo-6-chloro-5,8-difluoroquinazolin-4-ol (431 mg, 0.953 mmol, 0.8 equiv) in THF (5 mL) was treated with NaH (476 mg, 11.910 mmol, 10 equiv, 60%) for 5 minutes at 0° C. under nitrogen atmosphere. The resulting mixture was stirred for 2 hours at room temperature. It was quenched with water (10 mL) and extracted with DCM (3×40 mL). The extracts were combined, washed with brine (1×60 mL), dried over anhydrous $Na_2SO_4$. After filtration, the filtrate was concentrated under reduced pressure to the desired product as a brown yellow oil which was used in the next step directly without further purification. (ESI, m/z): 583 $[M+H]^+$ (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazoline A mixture of 7-bromo-6-chloro-5-(((S)-2-((2,2-difluoroethyl)amino)but-3-en-1-yl)oxy)-8-fluoro-2-(((2R,7aS)-2-fluorotetrahydro-1H-pyrrolizin-7a(5H)-yl)methoxy)quinazolin-4-ol (680 mg, 1.165 mmol, 1 equiv), triethylamine (1296 mg, 12.815 mmol, 11 equiv) and $POCl_3$ (535 mg, 3.495 mmol, 3 equiv) in dioxane (10 mL) was stirred for 2 hours at room temperature under nitrogen atmosphere. It was quenched with water (10 mL) and extracted with ethyl acetate (3×50 mL). The extracts were combined, washed with brine (1×70 mL), dried over anhydrous $Na_2SO_4$. After filtration, the filtrate was concentrated under reduced pressure to give a residue. The residue was purified by silica gel column chromatography, eluted with DCM/MeOH (10: 1) to the desired product as a light brown solid. (ESI, m/z): 567 $[M+H]^+$ Tert-butyl (4-((S)-8-chloro-4-(2,2-difluoroethyl)-10-fluoro-2-(((2R,7aS)-2-fluorotetrahydro-1H-pyrrolizin-7a (5H)-yl)methoxy)-5-vinyl-5,6-dihydro-4H-[1,4]oxazepino[5,6,7-de]quinazolin-9-yl)-3-cyano-7-fluorobenzo[b]thiophen-2-yl)carbamate A mixture of (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazoline (500 mg, 0.884 mmol, 1 equiv), tert-butyl N-[3-cyano-4-(5,5-dimethyl-1,3,2-dioxaborinan-2-yl)-7-fluoro-1-benzothiophen-2-yl]carbamate (1071 mg, 2.652 mmol, 3 equiv), 2nd Generation XPhos Precatalyst/X-Phos aminobiphenyl palladium chloride precatalyst (253 mg, 0.354 mmol, 0.4 equiv) and $K_3PO_4$ (1688.2 mg, 7.956 mmol, 9 equiv) in THF (5 mL, 61.714 mmol) was stirred for 3 hours at 65° C. under argon atmosphere. It was cooled to room temperature and extracted with ethyl acetate (2×10 mL). The extracts were combined, washed with brine (1×10 mL), dried over anhydrous $Na_2SO_4$. After filtration, the filtrate was concentrated under reduced pressure to give a residue. The residue was purified by silica gel column chromatography, eluted with DCM/MeOH (10: 1) to afford the desired product as a yellow solid. (ESI, m/z): 777 $[M+H]^+$ 2-Amino-4-((5S)-8-chloro-4-(2,2-difluoroethyl)-10-fluoro-2-(((2R,7aS)-2-fluorotetrahydro-1H-pyrrolizin-7a (5H)-yl)methoxy)-5-vinyl-5,6-dihydro-4H-[1,4]oxazepino[5,6,7-de]quinazolin-9-yl)-7-fluorobenzo[b]thiophene-3-carbonitrile A solution of tert-butyl (4-((S)-8-chloro-4-(2,2-difluoroethyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-3-cyano-7-fluorobenzo[b]thiophen-2-yl)carbamate (500 mg, 0.643 mmol, 1 equiv) and TFA (3 mL, 40.389 mmol) in DCM (1 mL, 15.731 mmol) was stirred for 2 hours at 25° C. The resulting mixture was concentrated under reduced pressure to give a residue. The residue was basified to PH~8 with $NH_3 \cdot H_2O$. It was extracted with DCM and washed with brine and dried over $Na_2SO_4$. It was filtered and solvent was removed under reduced pressure to give a crude. The crude product (500 mg) was purified by Prep-HPLC with the following conditions (Column: XBridge BEH C18 OBD Prep Column 130, 5 m, 30 mm*150 mm; Mobile Phase A: Water (10 mmol/L $NH_4HCO_3$), Mobile Phase B: ACN; Flow rate: 60 mL/min; Gradient: 50% B to 63% B in 8 min; Wave Length: UV 254 nm/220 nm; RT1(min): 6.7/7.75) to afford two desired product: 697 (peak 1, polar) and 890 (peak 2 (less polar) as light yellow solids.

697: (ESI, m/z): 677/679 $[M+H]^+$; $^1H$ NMR:(400 MHZ, DMSO-$d_6$, ppm) δ 8.07 (s, 2H), 7.24 (m, 5.2 Hz, 1H), 7.18-7.08 (m, 1H), 6.76-6.31 (m, 1H), 5.90 (ddd, J=16.5, 10.4, 5.5 Hz, 1H), 5.39-5.07 (m, 3H), 4.87-4.63 (m, 2H), 4.53 (d, J=12.6 Hz, 2H), 4.17-3.94 (m, 2H), 3.78 (m, 1H), 3.09 (m, 2H), 3.01 (m, 1H), 2.86 (m, 1H), 2.22-1.97 (m, 3H), 1.80 (m, 3H).

890: (ESI, m/z): 677/679 $[M+H]^+$; $^1H$ NMR:(400 MHZ, DMSO-$d_6$, ppm) δ 8.10 (s, 2H), 7.22 (dd, J=8.4, 5.2 Hz, 1H), 7.12 (t, J=8.9 Hz, 1H), 6.54 (t, J=56.2 Hz, 1H), 6.02-5.91 (m, 1H), 5.36-5.20 (m, 2H), 5.12 (d, J=17.1 Hz, 1H), 4.90 (dd, J=12.9, 4.4 Hz, 1H), 4.71 (m, 1H), 4.65-4.46 (m, 1H), 4.38 (s, 1H), 4.12 (d, J=9.9 Hz, 1H), 4.03 (d, J=10.2 Hz, 1H), 3.76 (m, 1H), 3.09 (m, 2H), 3.01 (m, 1H), 2.83 (m, 1H), 2.13 (m, 1H), 2.04 (m, 2H), 1.94-1.77 (m, 3H).

Example 1ao: Synthesis of 2-amino-4-((5S)-8-chloro-4-(2,2-difluoroethyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (730)

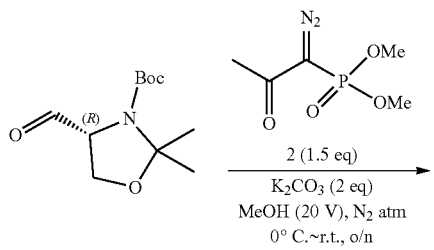

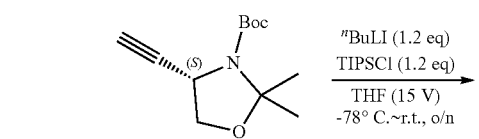

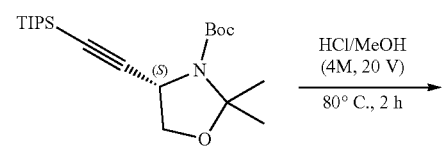

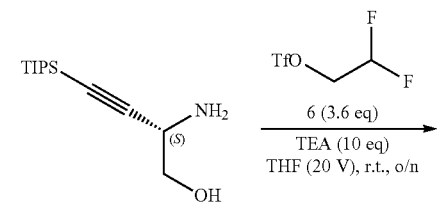

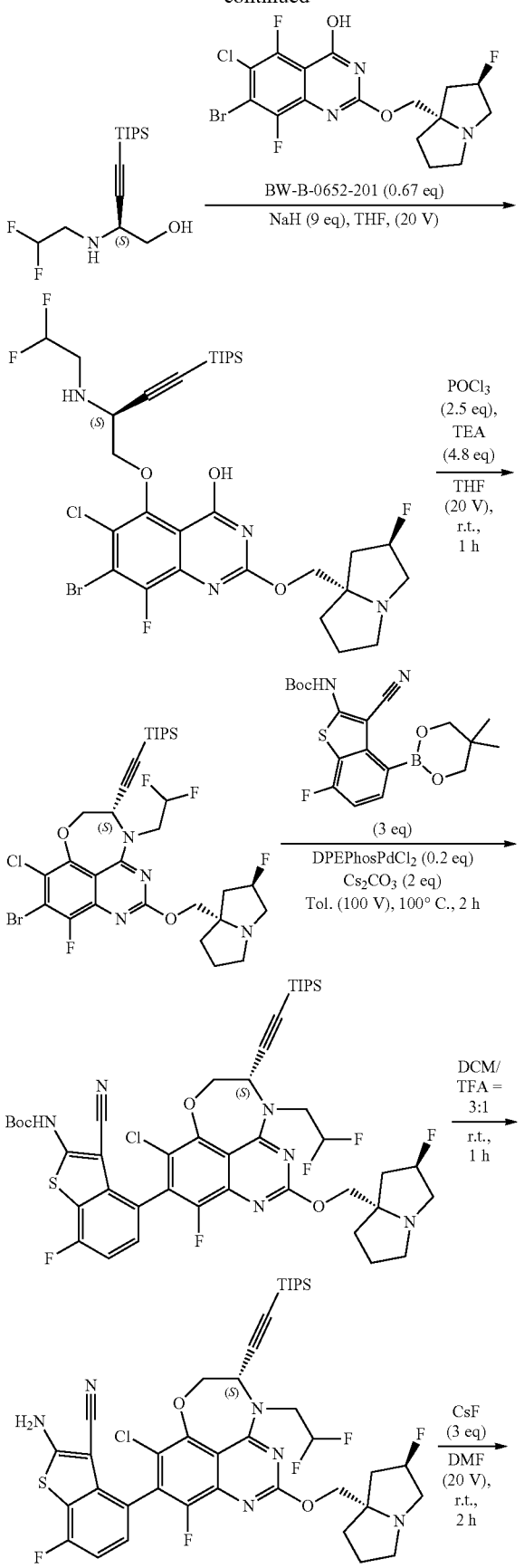

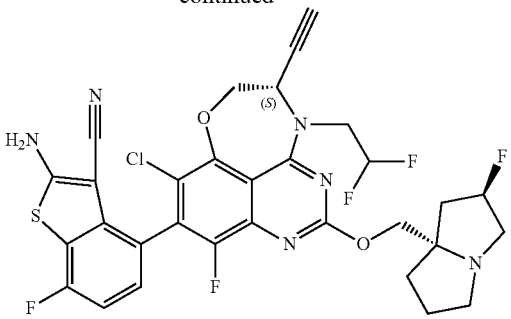

Tert-Butyl (4S)-4-ethynyl-2,2-dimethyl-1,3-oxazolidine-3-carboxylate To a stirred solution of tert-butyl (4R)-4-formyl-2,2-dimethyl-1,3-oxazolidine-3-carboxylate (14 g, 61.062 mmol, 1.0 equiv) and dimethyl (1-diazo-2-oxopropyl)phosphonate (17.60 g, 91.593 mmol, 1.5 equiv) in MeOH (280 mL) was added $K_2CO_3$ (16.88 g, 122.124 mmol, 2.0 equiv) in portions at 0° C. under nitrogen atmosphere. The reaction was stirred overnight at room temperature and concentrated under reduced pressure to give a residue. The residue was dissolved in water (100 mL), extracted with $CH_2Cl_2$ (8×100 mL). The extracts were combined, washed with brine, dried over anhydrous $Na_2SO_4$. After filtration, the filtrate was concentrated under reduced pressure to give a residue. The residue was purified by silica gel column chromatography, eluted with petroleum/ethyl acetate (9:1) to afford the desired product as a colorless oil. (ESI, m/z):226 [M+H]$^+$ Tert-butyl (4S)-2,2-dimethyl-4-[2-(triisopropylsilyl)ethynyl]-1,3-oxazolidine-3-carboxy To a stirred solution of tert-butyl (4S)-4-ethynyl-2,2-dimethyl-1,3-oxazolidine-3-carboxylate (4.00 g, 17.755 mmol, 1.0 equiv) in THF (60 mL) was added n-BuLi (1.57 g, 24.50 mmol, 1.2 equiv) dropwise at −78° C. under nitrogen atmosphere. The resulting mixture was stirred for additional 5 minutes at 0° C. Then chlorotris (propan-2-yl)silane (4.72 g, 24.50 mmol, 1.2 equiv) was added dropwise over 15 minutes at −78° C. The reaction was stirred overnight at room temperature under nitrogen atmosphere. It was quenched with water/Ice, extracted with $CH_2Cl_2$ (5×50 mL). The extracts were combined, washed with brine, dried over anhydrous $Na_2SO_4$. After filtration, the filtrate was concentrated under reduced pressure to give a residue. The residue was purified by silica gel column chromatography, eluted with petroleum/ethyl acetate (12:1) to afford the desired product as a colorless oil. (ESI, m/z): 326 [M−56] $^+$ (S)-2-amino-4-(triisopropylsilyl)but-3-yn-1-ol A solution of tert-butyl (4S)-2,2-dimethyl-4-[2-(triisopropylsilyl)ethynyl]-1,3-oxazolidine-3-carboxylate (7.80 g, 20.439 mmol, 1.0 equiv) and HCl in MeOH (4M, 140 mL) was stirred for 2 hours at 80° C. It was cooled to room temperature, concentrated under vacuum to give the desired product which was used in the next step directly without further purification. (ESI, m/z):242[M+H]$^+$ (2S)-2-[(2,2-difluoroethyl)amino]-4-(triisopropylsilyl) but-3-yn-1-ol To a stirred solution of (2S)-2-amino-4-(triisopropylsilyl)but-3-yn-1-ol (6.0 g, 24.8 mmol, 1.0 equiv.) and triethylamine (34.5 mL, 248.5 mmol, 10.0 equiv.) in THF (120 mL) was added 2,2-difluoroethyl trifluoromethanesulfonate (19.20 g, 89.5 mmol, 3.6 equiv) at room temperature. The reaction was stirred overnight at room temperature. The resulting mixture was concentrated under vacuum and extracted with $CH_2Cl_2$ (5×100 mL). The extracts were combined, washed with brine, dried over anhydrous Na$_2$SO$_4$. After filtration, the filtrate was concentrated under reduced pressure to give a residue. The residue was purified by silica gel column chromatography, eluted with CH$_2$Cl$_2$/MeOH (9:1) to afford the desired product as a colorless oil. (ESI, m/z): 306[M+H]$^+$ 2-{[(2R,7aS)-2-fluoro-hexahydropyrrolizin-7a-yl]methoxy}-7-bromo-6-chloro-5-{[(2S)-2-[(2,2-difluoroethyl)amino]-4-(triisopropylsilyl)but-3-yn-1-yl]oxy}-8-fluoroquinazolin-4-ol A solution of (2S)-2-[(2,2-difluoroethyl)amino]-4-(triisopropylsilyl)but-3-yn-1-ol (50 mg, 0.164 mmol, 1.00 equiv) in THF (2 mL, 24.686 mmol) was treated with 2-{[(2R,7aS)-2-fluoro-hexahydropyrrolizin-7a-yl]methoxy}-7-bromo-6-chloro-5,8-difluoroquinazolin-4-ol (50 mg, 0.110 mmol, 0.67 equiv) for 10 minutes at room temperature under nitrogen atmosphere followed by the addition of NaH (58 mg, 1.476 mmol, 9.00 equiv, 60%) in portions at room temperature . . . . It was quenched by the addition of water/ice (50 mL) at room temperature, extracted with ethyl acetate (3×50 mL). The extracts were combined, washed with sat. NaCl(aq.) (2×50 mL), dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 10% to 95% gradient in 30 min; detector, UV 254 nm to afford the desired product as a brown solid. (ESI, m/z):737 [M+H]$^+$ (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazoline A solution of 2-{[(2R,7aS)-2-fluoro-hexahydropyrrolizin-7a-yl]methoxy}-7-bromo-6-chloro-5-{[(2S)-2-[(2,2-difluoroethyl)amino]-4-(triisopropylsilyl)but-3-yn-1-yl]oxy}-8-fluoroquinazolin-4-ol (407 mg, 0.551 mmol, 1.0 equiv) and triethylamine (268 mg, 2.645 mmol, 4.8 equiv) in THF (8.1 mL) was stirred for 10 minutes at room temperature under nitrogen atmosphere. POCl$_3$ (211 mg, 1.378 mmol, 2.5 equiv) was added at room temperature, the reaction mixture was stirred for 1 hour at room temperature. It was quenched by the addition of water (30 mL) at room temperature, extracted with ethyl acetate (3×50 mL). The combined organic layers were washed with sat. NaCl(aq.) (2×50 mL), dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 10% to 50% gradient in 10 min; detector, UV 254 nm to afford the desired product as a brown solid. (ESI, m/z): 719 [M+H]$^+$ Tert-butyl N-{4-[(12S)-3-{[(2R,7aS)-2-fluoro-hexahydropyrrolizin-7a-yl]methoxy}-8-chloro-13-(2,2-difluoroethyl)-6-fluoro-12-[2-(triisopropylsilyl)ethynyl]-10-oxa-2,4,13-triazatricyclo[7.4.1.0ˆ{5,14}]tetradeca-1,3,5,7,9(14)-pentaen-7-yl]-3-cyano-7-fluoro-1-benzothiophen-2-yl}carbamate A mixture of (12S)-3-{[(2R,7aS)-2-fluoro-hexahydropyrrolizin-7a-yl]methoxy}-7-bromo-8-chloro-13-(2,2-difluoroethyl)-6-fluoro-12-[2-(triisopropylsilyl)ethynyl]-10-oxa-2,4,13-triazatricyclo[7.4.1.0ˆ{5,14}]tetradeca-1,3,5,7,9(14)-pentaene (302 mg, 0.419 mmol, 1.0 equiv) and tert-butyl N-[3-cyano-4-(5,5-dimethyl-1,3,2-dioxaborinan-2-yl)-7-fluoro-1-benzothiophen-2-yl]carbamate (508 mg, 1.257 mmol, 3.0 equiv) and 2nd Generation XPhos Precatalyst/X-Phos aminobiphenyl palladium chloride precatalyst (66 mg, 0.084 mmol, 0.2 equiv) and K$_3$PO$_4$ (801 mg, 3.771 mmol, 9.0 equiv) in THF (20 mL, 246.85 mmol) was degassed and back filled with nitrogen for 3 times. The reaction mixture was stirred for 4 hours at 65° C. under argon atmosphere. It was cooled to room temperature, quenched with water (50 mL), and extracted with ethyl acetate (3×50 mL). The extracts were combined, washed with sat. NaCl(aq.) (2×50 mL), dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 100% to 100% gradient in 20 min; detector, UV 254 nm to afford the desired product as a brown solid. (ESI, m/z): 931[M+H]$^+$ 2-Amino-4-((S)-8-chloro-4-(2,2-difluoroethyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazolin-9-yl)-7-fluorobenzo[b]thiophene-3-carbonitrile A solution of tert-butyl N-{4-[(12S)-3-{[(2R,7aS)-2-fluoro-hexahydropyrrolizin-7a-yl]methoxy}-8-chloro-13-(2,2-difluoroethyl)-6-fluoro-12-[2-(triisopropylsilyl)ethynyl]-10-oxa-2,4,13-triazatricyclo[7.4.1.0ˆ{5,14}]tetradeca-1,3,5,7,9(14)-pentaen-7-yl]-3-cyano-7-fluoro-1-benzothiophen-2-yl} carbamate (76 mg, 0.082 mmol, 1.0 equiv) and TFA (1 mL, 13.463 mmol) in DCM (3 mL, 47.192 mmol) was stirred for 1 hour at room temperature under nitrogen atmosphere. The resulting mixture was concentrated under vacuum to give the desired product which was used in the next step directly without further purification. (ESI, m/z): 831 [M+H]$^+$ 2-Amino-4-((5S)-8-chloro-4-(2,2-difluoroethyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile A solution of 4-[(12S)-3-{[(2R,7aS)-2-fluoro-hexahydropyrrolizin-7a-yl]methoxy}-8-chloro-13-(2,2-difluoroethyl)-6-fluoro-12-[2-(triisopropylsilyl)ethynyl]-10-oxa-2,4,13-triazatricyclo[7.4.1.0ˆ{5,14} ]tetradeca-1,3,5,7,9(14)-pentaen-7-yl]-2-amino-7-fluoro-1-benzothiophene-3-carbonitrile (76 mg, 0.091 mmol, 1.0 equiv) and CsF (6 mg, 0.036 mmol, 3 equiv) in DMF (1 mL, 12.92 mmol) was stirred for 2 hours at room temperature under nitrogen atmosphere. It was concentrated to give a crude. The crude product was purified by Prep-HPLC with the following conditions (Column: YMC Triart C18 ExRs 5 m, 30 mm*150 mm; Mobile Phase A: Water (10 mmol/L NH$_4$HCO$_3$), Mobile Phase B: ACN; Flow rate: 60 mL/min; Gradient: 55% B to 85% B in 10 min; Wavelength: UV 254 nm/220 nm; RT1(min): 8.12) to afford the desired product as a grey solid.

(ESI, m/z):675[M+H]$^+$ $^1$H NMR (400 MHZ, DMSO-d$_6$): δ 8.11-8.09 (m, 1H), 7.27-7.20 (m, 1H), 7.17-7.12 (m, 1H), 6.61-6.32 (m, 1H), 5.35-5.21 (m, 1H), 5.16-5.15 (m, 1H), 4.86-4.75 (m, 1H), 4.57-4.35 (m, 2H), 4.27-4.19 (m, 1H), 4.16-4.03 (m, 2H), 3.56-3.44 (m, 1H), 3.09-3.08 (m, 2H), 3.01-3.00 (m, 1H), 2.84-2.82 (m, 1H), 2.14-2.12 (m, 1H), 2.08-2.01 (m, 2H), 1.86-1.77 (m, 3H). 2-amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-7-fluorobenzo[b]thiophene-3-carbonitrile

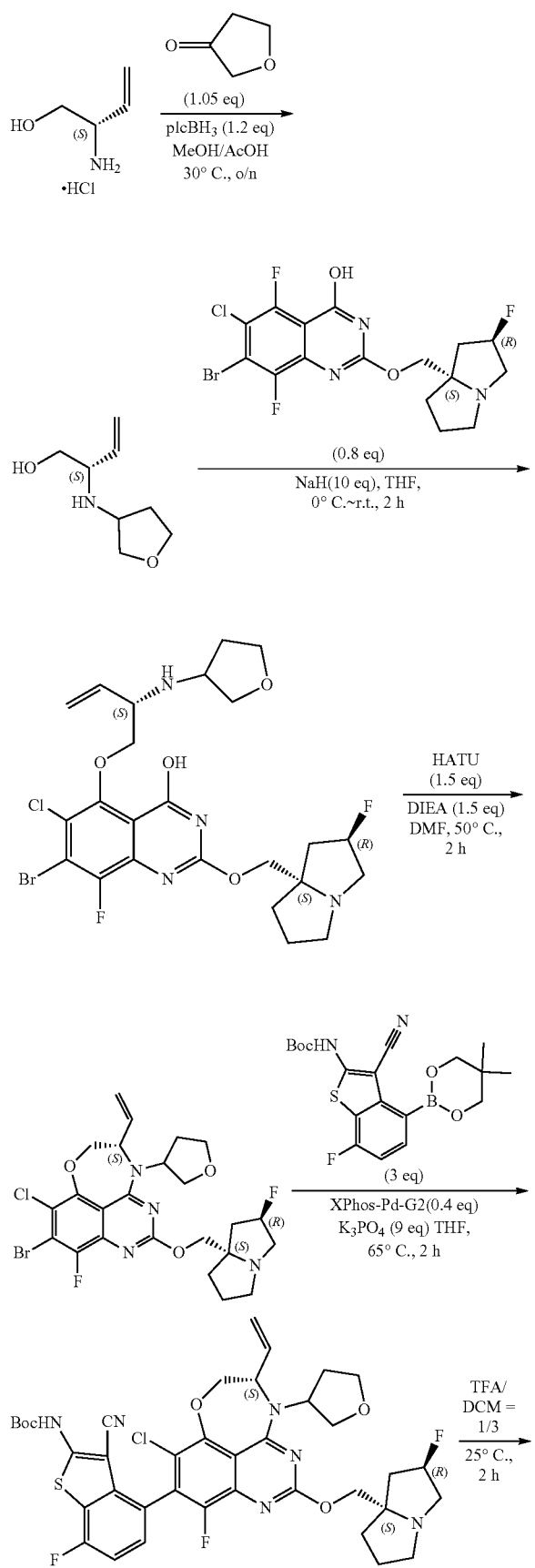

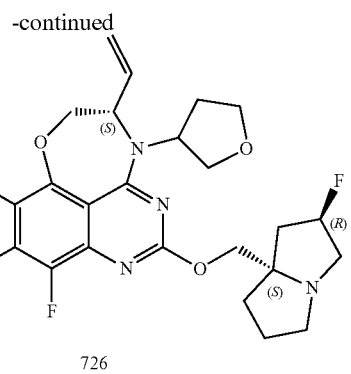

726

(2S)-2-(oxolan-3-ylamino)but-3-en-1-ol To a stirred solution of (2S)-2-aminobut-3-en-1-ol hydrochloride (3 g, 24.276 mmol, 1 equiv) and dihydrofuran-3-one (2.19 g, 25.49 mmol, 1.05 equiv) in MeOH (81 mL) in AcOH (8.1 mL) was added 2-methylpyridine borane (3.12 g, 29.13 mmol, 1.2 equiv) in portions at room temperature. The resulting mixture was stirred for overnight at 30° C. It was cooled to room temperature, concentrated under reduced pressure, extracted with DCM (3×30 mL). The extracts were combined, washed with brine (1×30 mL), dried over anhydrous $Na_2SO_4$. After filtration, the filtrate was concentrated under reduced pressure to give a residue. The residue was purified by silica gel column chromatography, eluted with DCM/MeOH (9:1) to afford the desired product as a yellow liquid.

$^1$H NMR: (400 MHZ, DMSO-$d_6$, ppm) δ 5.59 (m, 1H), 5.18 (m, 1H), 5.09 (m, 1H), 3.78-3.55 (m, 3H), 3.41-3.19 (m, 4H), 3.05 (m, 1H), 2.02-1.87 (m, 3H), 1.65-1.53 (m, 1H).

7-Bromo-6-chloro-8-fluoro-2-(((2R,7aS)-2-fluorotetrahydro-1H-pyrrolizin-7a(5H)-yl)methoxy)-5-(((2S)-2-((tetrahydrofuran-3-yl)amino)but-3-en-1-yl)oxy)quinazolin-4-ol To a stirred solution of (2S)-2-(oxolan-3-ylamino)but-3-en-1-ol (350 mg, 2.226 mmol, 1 equiv), 2-{[(2R,7aS)-2-fluorohexahydropyrrolizin-7a-yl]methoxy}-7-bromo-6-chloro-5,8-difluoroquinazolin-4-ol (806 mg, 1.781 mmol, 0.8 equiv) in THF (14 mL) were added NaH (890.4 mg, 22.260 mmol, 10 equiv, 60%) in portions at 0° C. under nitrogen atmosphere. The resulting mixture was stirred for additional 2 hours at room temperature, quenched with water at 0° C. and extracted with ethyl acetate (3×20 mL). The extracts were combined, washed with brine (3×20 mL), dried over anhydrous $Na_2SO_4$. After filtration, the filtrate was concentrated under reduced pressure to give the desired product which was used in the next step directly without further purification. (ESI, m/z): 589/591 [M+H]$^+$ (5S)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazoline A solution of 2-([[(2R,7aS)-2-fluorohexahydropyrrolizin-7a-yl]methoxy-7-bromo-6-chloro-8-fluoro-5-([[(2S)-2-(oxolan-3-ylamino)but-3-en-1-yl] oxyquinazolin-4-ol (1.93 g, 3.272 mmol, 1 equiv), HATU (1.87 g, 4.908 mmol, 1.5 equiv) and DIEA (0.63 g, 4.908 mmol, 1.5 equiv) in DMF (100 mL) was stirred for 2 hours at 50° C. under nitrogen atmosphere. It was cooled to room temperature and extracted with ethyl acetate (3×100 mL). The extracts were combined, washed with brine (5×50 mL), dried over anhydrous $Na_2SO_4$. After filtration, the filtrate was concentrated under reduced pressure to give a residue. The residue was purified by silica gel column chromatography, eluted with DCM/MeOH (10: 1) to give a crude. The crude product (400 mg) was purified by Prep-HPLC with the following conditions (Column: CHIRAL ART Cellulose-SB 2*25 cm, 5m; Mobile Phase A: HEX(0.1% DEA), Mobile Phase B: EtOH: DCM=1: 1; Flow rate: 20 mL/min; Gradient: isocratic 15; Wave Length: UV 254/220 nm; RT1(min): 9.253; RT2(min): 10.937; Sample Solvent: MeOH: EtOH; Injection Volume: 0.3 mL; Number Of Runs: 14) to afford two desired intermediate: Desired intermediate 1 (polar) and desired intermediate 2 (less polar) as white solids.

Desired intermediate 2 (less polar): (ESI, m/z): 571/573 [M+H]$^+$

Tert-butyl (4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-3-cyano-7-fluorobenzo[b]thiophen-2-yl)carbamate A mixture of ((5S)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazoline (desired intermediate 2, less polar from previous step) (160 mg, 0.280 mmol, 1 equiv), tert-butyl N-[3-cyano-4-(5,5-dimethyl-1,3,2-dioxaborinan-2-yl)-7-fluoro-1-benzothiophen-2-yl]carbamate (339 mg, 0.840 mmol, 3 equiv), 2nd Generation XPhos Precatalyst/X-Phos aminobiphenyl palladium chloride precatalyst (88 mg, 0.112 mmol, 0.4 equiv) and K$_3$PO$_4$ (534 mg, 2.520 mmol, 9 equiv) in THF (5 mL) was stirred for 2 hours at 65° C. under argon atmosphere. It was cooled to room temperature, extracted with ethyl acetate (3×5 mL). The extracts were combined, washed with brine (1×10 mL), dried over anhydrous Na$_2$SO$_4$. After filtration, the filtrate was concentrated under reduced pressure to give a residue. The residue was purified by silica gel column chromatography, eluted with DCM/MeOH (10: 1) to afford the desired product as a brown solid. (ESI, m/z): 783 [M+H]$^+$ 2-Amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-7-fluorobenzo[b]thiophene-3-carbonitrile A solution of tert-butyl (4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-3-cyano-7-fluorobenzo[b]thiophen-2-yl)carbamate (100 mg, 0.128 mmol, 1 equiv) and TFA (1 mL, 13.463 mmol) in DCM (3 mL, 47.192 mmol) was stirred for 2 hours at 25° C. It was concentrated under reduced pressure and basified to pH 8 with NH$_3$.H$_2$O. Solvent was removed to give a crude. The crude product (100 mg) was purified by Prep-HPLC with the following conditions (Column: Kinetex 5 m EVO C18, 30 mm*150 mm; Mobile Phase A: Water (10 mmol/L NH$_4$HCO$_3$), Mobile Phase B: ACN; Flow rate: 60 mL/min; Gradient: 35% B to 65% B in 10 min; Wave Length: UV 254 nm/220 nm; RT1(min): 8.17) to afford the desired product as a light yellow solid. (ESI, m/z): 683 [M+H]$^+$; $^1$H NMR (400 MHZ, DMSO-d$_6$, ppm) δ 8.07 (s, 2H), 7.20 (dd, J=8.4, 5.3 Hz, 1H), 7.11 (t, J=8.9 Hz, 1H), 6.02 (m, 1H), 5.65 (m, 1H), 5.40-5.13 (m, 2H), 5.00-4.84 (m, 2H), 4.74 (s, 1H), 4.42 (m, 1H), 4.12 (m, 1H), 3.97 (m, 3H), 3.83 (m, 1H), 3.71 (m, 1H), 3.09 (m, 2H), 3.02 (m, 1H), 2.83 (m, 1H), 2.26-2.10 (m, 2H), 2.06 (t, J=15.9 Hz, 3H), 1.91-1.67 (m, 3H).

Example 1ap: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazolin-9-yl)-7-fluorobenzo[b]thiophene-3-carbonitrile (651)

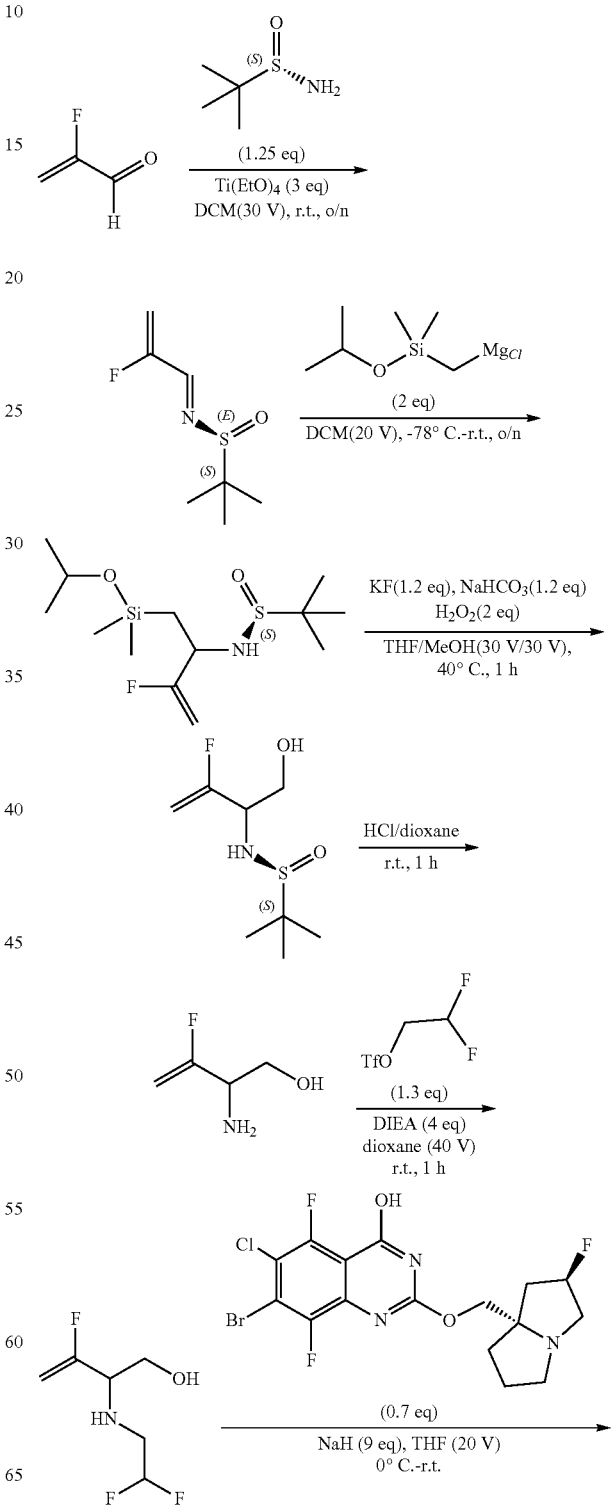

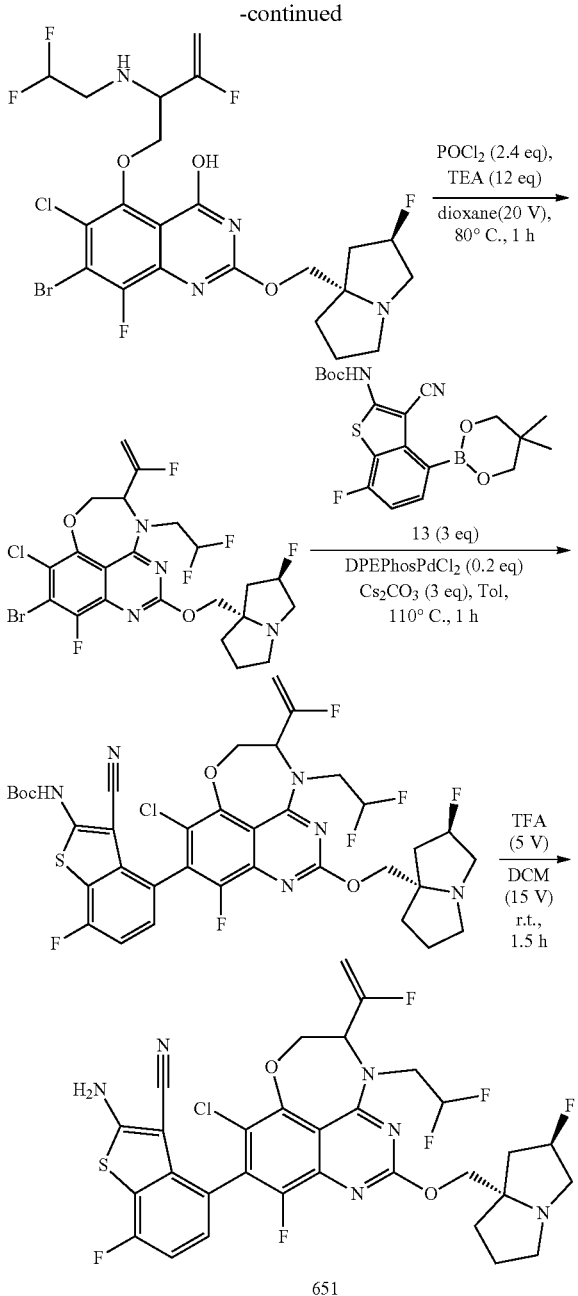

(S)—N-(2-fluoroprop-2-en-1-ylidene)-2-methylpropane-2-sulfinamide A solution of 2-fluoroprop-2-enal (4 g, 54.015 mmol, 1 equiv), Ti(OEt)$_4$ (36.96 g, 162.045 mmol, 3 equiv) and (S)-2-methylpropane-2-sulfinamide (8.18 g, 67.519 mmol, 1.25 equiv) in DCM (50 mL) was stirred for overnight at room temperature. The reaction was quenched by the addition of water (50 mL) at room temperature and filtered. The filter cake was washed with DCM (3×20 mL) and the filtrate was extracted with CH$_2$Cl$_2$ (3×50 mL). The extracts were combined, washed with brine, dried over anhydrous Na$_2$SO$_4$. After filtration, the filtrate was concentrated under reduced pressure to give a residue. The residue was purified by silica gel column chromatography, eluted with petroleum/ethyl acetate (5:1) to the desired product as a colorless oil. (ESI, m/z): 178 [M+H]$^+$ (S)—N-(3-fluoro-1-(isopropoxydimethylsilyl)but-3-en-2-yl)-2-methylpropane-2-sulfinamide A solution of (S)—N-(2-fluoroprop-2-en-1-ylidene)-2-methylpropane-2-sulfinamide (3 g, 16.926 mmol, 1 equiv) and [(chloromagnesio)methyl](isopropoxy)dimethylsilane (6.47 g, 33.852 mmol, 2 equiv) in DCM (30 mL) was stirred for overnight at −78° C. under nitrogen atmosphere. The reaction was quenched by the addition of water (20 mL) at 0° C. and extracted with CH$_2$Cl$_2$ (3×30 mL). The extracts were combined, washed with brine, and dried over anhydrous Na$_2$SO$_4$. After filtration, the filtrate was concentrated under reduced pressure the desired product which was used in the next step directly without further purification. (ESI, m/z):310 [M+H]$^+$.

(S)—N-(3-fluoro-1-hydroxybut-3-en-2-yl)-2-methylpropane-2-sulfinamide A solution of (S)—N-(3-fluoro-1-(isopropoxydimethylsilyl)but-3-en-2-yl)-2-methylpropane-2-sulfinamide (5 g, 15.831 mmol, 1 equiv, 98%), KF (1.10 g, 18.997 mmol, 1.2 equiv), NaHCO$_3$ (1.60 g, 18.997 mmol, 1.2 equiv) and H$_2$O2 (1.08 g, 31.662 mmol, 2 equiv) in THF/MeOH(150 mL/150 mL) was stirred for 1 hour at 40° C. It was cooled to room temperature, concentrated under reduced pressure, extracted with CH$_2$Cl$_2$ (5×30 mL). The extracts were combined, washed with brine, and dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10:1) to afford the desired product as a white solid. (ESI, m/z):210[M+H]$^+$ 2-Amino-3-fluorobut-3-en-1-ol A mixture of ((S)—N-(3-fluoro-1-hydroxybut-3-en-2-yl)-2-methylpropane-2-sulfinamide (800 mg, 3.823 mmol, 1 equiv) in 4M HCl in dioxane (2 mL) was stirred for 1 hour at room temperature. The resulting mixture was concentrated under reduced pressure to give the desired product which was used in the next step directly without further purification. (ESI, m/z): 106 [M+H]$^+$ 2-((2,2-Difluoroethyl)amino)-3-fluorobut-3-en-1-ol A solution of 2-amino-3-fluorobut-3-en-1-ol (430 mg, 4.091 mmol, 1 equiv), 2,2-difluoroethyl trifluoromethanesulfonate (1138 mg, 5.318 mmol, 1.3 equiv) and DIEA (2115 mg, 16.364 mmol, 4 equiv) in dioxane (16 mL) was stirred for 1 hour at room temperature. The reaction was quenched with water (30 mL) and extracted with CH$_2$Cl$_2$ (3×30 mL). The extracts were combined, washed with brine, dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10:1) to afford the desired product as a yellow oil. (ESI, m/z): 170[M+H]$^+$ 7-Bromo-6-chloro-5-((2-((2,2-difluoroethyl)amino)-3-fluorobut-3-en-1-yl)oxy)-8-fluoro-2-(((2R,7aS)-2-fluorotetrahydro-1H-pyrrolizin-7a(5H)-yl)methoxy)quinazolin-4-ol A solution of (2R)-2-[(2,2-difluoroethyl)amino]-3-fluorobut-3-en-1-ol (380 mg, 2.247 mmol, 1 equiv) and NaH (485 mg, 20.223 mmol, 9 equiv) in THF (8 mL) was stirred for 10 minutes at 0° C. and 1 hour at room temperature. It was quenched with water/ice at 0° C. and extracted with CH$_2$Cl$_2$ (3×20 mL). The extracts were combined, washed with brine, dried over anhydrous Na$_2$SO$_4$. After filtration, the filtrate was concentrated under reduced pressure to give the desired product which was used in the next step directly without further purification. (ESI, m/z):601 [M+H]$^+$ 9-Bromo-8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazoline A solution of 7-bromo-6-chloro-5-((2-((2,2-difluoroethyl)amino)-3-fluorobut-3-en-1-yl)oxy)-8-fluoro-2-(((2R,7aS)-2-fluorotetrahydro-1H-pyrrolizin-7a (5H)-yl)methoxy)quinazolin-4-ol (900 mg, 1.496 mmol, 1 equiv), POCl₃ (1146.46 mg, 7.480 mmol, 2.4 equiv) and triethylamine (1816 mg, 17.952 mmol, 12 equiv) in dioxane (20 mL) was stirred for 1 hour at 80° C. It was cooled down to room temperature, quenched with water/ice at 0° C. and extracted with CH₂Cl₂ (3×30 mL). The extracts were combined, washed with brine, dried over anhydrous Na₂SO₄. After filtration, the filtrate was concentrated under reduced pressure to give a residue. The residue was purified by reversed-phase flash chromatography with the following conditions: column, C18; mobile phase, MeCN in Water (0.1% TFA), 50% to 100% gradient in 15 min; detector, UV 254 nm to afford the desired product as a yellow solid. (ESI, m/z):583[M+H]⁺

Tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazolin-9-yl)-3-cyano-7-fluorobenzo[b]thiophen-2-yl)carbamate A solution of 9-bromo-8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazoline (300 mg, 0.514 mmol, 1 equiv), tert-butyl N-[3-cyano-4-(5,5-dimethyl-1,3,2-dioxaborinan-2-yl)-7-fluoro-1-benzothiophen-2-yl]carbamate (623 mg, 1.542 mmol, 3 equiv), Cs₂CO₃ (502 mg, 1.542 mmol, 3 equiv) and DPEPhosPdCl₂ (72 mg, 0.103 mmol, 0.2 equiv) in toluene (30 mL) was stirred for 1 hour at 110° C. under argon atmosphere. It was cooled to room temperature, quenched with water, and extracted with CH₂Cl₂ (3×10 mL). The extracts were combined, washed with brine, and dried over anhydrous Na₂SO₄. After filtration, the filtrate was concentrated under reduced pressure to give a residue. The residue was purified by reversed-phase flash chromatography with the following conditions: column, C18; mobile phase, MeCN in Water (0.1% TFA), 70% to 100% gradient in 10 min; detector, UV 254 nm to afford the desired product as a yellow solid. (ESI, m/z):795 [M+H]⁺

2-Amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazolin-9-yl)-7-fluorobenzo[b]thiophene-3-carbonitrile A solution of tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazolin-9-yl)-3-cyano-7-fluorobenzo[b]thiophen-2-yl)carbamate (160 mg, 0.179 mmol, 1 equiv) and TFA (1.5 mL) in DCM (4.5 mL) was stirred for 1.5 hours at room temperature. The resulting mixture was concentrated under reduced pressure to give a residue. The residue was purified by reversed-phase flash chromatography with the following conditions: Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 47% B to 63% B in 10 min; Wave Length: UV 254 nm/220 nm; RT1(min): 8.17/8.97 to afford the desired product as an off-white solid. (ESI, m/z):695 [M+H]⁺

¹H NMR (400 MHZ, DMSO-d₆, ppm) δ 8.06 (s, 2H), 7.24-7.21 (m, 1H), 7.14 (t, J=8.4 Hz, 1H), 6.66-6.36 (m, 1H), 5.35-5.21 (m, 1H), 4.96-4.82 (m, 3H), 4.60-4.43 (m, 3H), 4.11-4.00 (m, 3H), 3.09-3.08 (m, 2H), 3.01 (s, 1H), 2.84-2.82 (m, 1H), 2.19-2.13 (m, 1H), 2.07-1.97 (m, 2H), 1.86-1.76 (m, 3H).

Example 1aq: Synthesis of 2-amino-4-(8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (913)

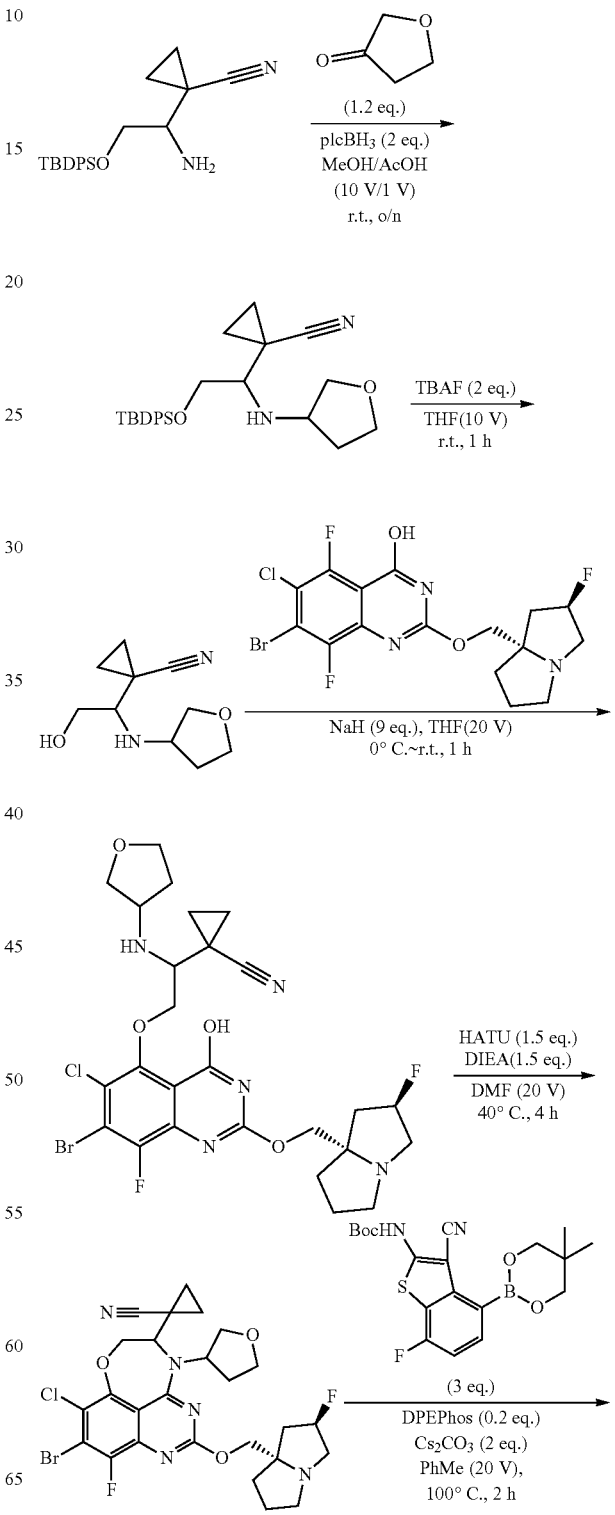

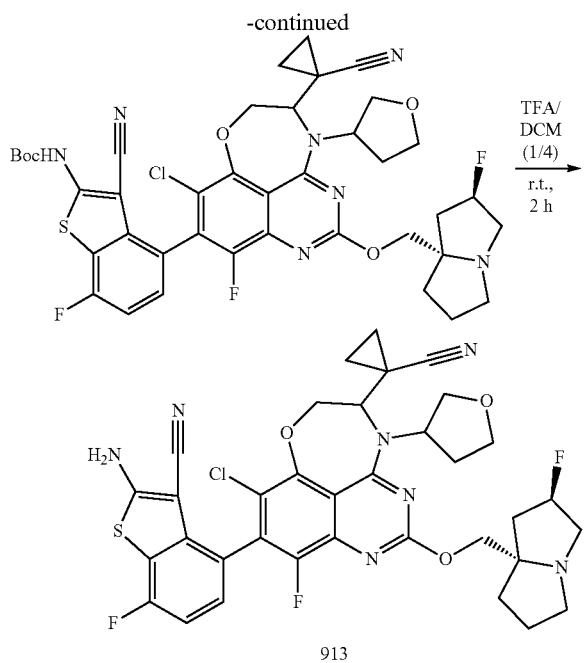

913

1-(2-((Tert-butyldiphenylsilyl)oxy)-1-((tetrahydrofuran-3-yl)amino)ethyl)cyclopropane-1-carbonitrile A solution of 1-(1-amino-2-((tert-butyldiphenylsilyl)oxy)ethyl)cyclopropane-1-carbonitrile (2 g, 5.486 mmol, 1 equiv), dihydrofuran-3-one (566 mg, 6.583 mmol, 1.2 equiv) and borane-2-picoline complex (1173 mg, 10.972 mmol, 2 equiv) in MeOH (100.0 mL) and AcOH (10.0 mL) was stirred overnight at room temperature. It was quenched with NaHCO$_3$ (aq.) at room temperature and extracted with CH$_2$Cl$_2$ (3×30 mL). The extracts were combined, washed with brine, and dried over anhydrous Na$_2$SO$_4$. After filtration, the filtrate was concentrated under reduced pressure to give a residue. The residue was purified by silica gel column chromatography, eluted with CH$_2$Cl$_2$/MeOH (20:1) to afford the desired product as a light brown oil. (ESI, m/z): 435 [M+H]$^+$ 1-(2-Hydroxy-1-((tetrahydrofuran-3-yl)amino)ethyl)cyclopropane-1-carbonitrile A solution of 1-(2-((tert-butyldiphenylsilyl)oxy)-1-((tetrahydrofuran-3-yl)amino)ethyl)cyclopropane-1-carbonitrile (800 mg, 1.841 mmol, 1 equiv) and TBAF (962 mg, 3.682 mmol, 2 equiv) in THF (16.0 mL) was stirred for 1 hour at room temperature. It was concentrated under reduced pressure to give a residue. The residue was purified by silica gel column chromatography, eluted with CH$_2$Cl$_2$/MeOH (20:1) to afford the desired product as a brown oil. (ESI, m/z): 197 [M+H]$^+$ 1-(2-((7-Bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)-1-((tetrahydrofuran-3-yl)amino)ethyl) cyclopropane-1-carbonitrile A solution of 1-(2-hydroxy-1-((tetrahydrofuran-3-yl)amino)ethyl)cyclopropane-1-carbonitrile (320 mg, 1.631 mmol, 1 equiv) in THF (64.0 mL) was treated with NaH (352.17 mg, 14.679 mmol, 9 equiv) for 15 minutes at 0° C. under nitrogen atmosphere followed by the addition of 7-bromo-6-chloro-5,8-difluoro-2-(((2R,7aS)-2-fluorotetrahydro-1H-pyrrolizin-7a(5H)-yl)methoxy)quinazolin-4-ol (738 mg, 1.631 mmol, 1 equiv) at 0° C. The resulting mixture was stirred for 7 hours at room temperature, quenched with water/ice at 0° C., and extracted with CH$_2$Cl$_2$ (3×40 mL). The extracts were combined, washed with brine, and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 30% to 70% gradient in 10 min; detector, UV 254 nm to give the desired product as a light-yellow solid. (ESI, m/z): 628 [M+H]$^+$ 1-(9-Bromo-8-chloro-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-5-yl)cyclopropane-1-carbonitrile A mixture of 1-(2-((7-bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)-1-((tetrahydrofuran-3-yl) amino)ethyl)cyclopropane-1-carbonitrile (600 mg, 0.954 mmol, 1 equiv), DIEA (184 mg, 1.431 mmol, 1.5 equiv) and HATU (544 mg, 1.431 mmol, 1.5 equiv) in DMF (40 mL) was stirred for 4 hours at 40° C. It was cooled to room temperature, quenched with water, and extracted with ethyl acetate (4×20 mL). The extracts were combined, washed with brine, and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 30% to 70% gradient in 10 min; detector, UV 254 nm to afford the desired product as a light-yellow solid. (ESI, m/z): 610 [M+H]$^+$ Tert-butyl (4-(8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate A mixture of 1-(9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-5-yl)cyclopropane-1-carbonitrile (460 mg, 0.753 mmol, 1 equiv), tert-butyl N-[3-cyano-4-(5,5-dimethyl-1,3,2-dioxaborinan-2-yl)-7-fluoro-1-benzothiophen-2-yl]carbamate (913 mg, 2.259 mmol, 3 equiv), Bis(diphenylphosphinophenyl)ether palladium (II) dichloride (108 mg, 0.151 mmol, 0.2 equiv) and Cs$_2$CO$_3$ (490 mg, 1.506 mmol, 2 equiv) in toluene (60 mL) was stirred for 2 hours at 100° C. under nitrogen atmosphere. It was cooled to room temperature, quenched with water at room temperature, and extracted with CH$_2$Cl$_2$ (3×30 mL). The extracts were combined, washed with brine, and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 30% to 70% gradient in 10 min; detector, UV 254 nm to give the desired product as a light-yellow solid. (ESI, m/z): 822 [M+H]$^+$ 2-Amino-4-(8-chloro-5-(1-cyanocyclopropyl)-10-fluoro-2-(((2R,7aS)-2-fluorotetrahydro-1H-pyrrolizin-7a(5H)-yl) methoxy)-4-(tetrahydrofuran-3-yl)-5,6-dihydro-4H-[1,4] oxazepino[5,6,7-de]quinazolin-9-yl)-7-fluorobenzo[b] thiophene-3-carbonitrile A solution of tert-butyl (4-(8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate (480 mg, 0.584 mmol, 1 equiv) and trifluoroacetaldehyde (1 mL) in DCM (4 mL) was stirred for 2 hours at room temperature. It was concentrated under reduced pressure to give a residue. The residue was purified by reversed-phase flash chromatography with the following conditions: Column: XBridge BEH Shield RP18 5 m, 30 mm*150 mm; Mobile Phase A: Water (10 mmol/L NH$_4$HCO$_5$), Mobile Phase B: ACN; Flow rate: 60 mL/min; Gradient: 38% B to 60% B in 10 min; Wave Length: UV 254 nm/220 nm; RT1(min): 8.3 to give desired product as a white solid. (ESI, m/z): 722 [M+H]$^+$ $^1$H NMR (400 MHZ, DMSO-d$_6$, ppm) δ 8.10-8.08 (m, 2H), 7.23-7.18 (m, 1H), 7.17-7.11 (m, 1H), 5.35-5.22 (m, 1H), 4.95-4.74 (m, 2H), 4.62-4.35 (m, 1H), 4.31-4.15 (m, 2H), 4.12-3.96 (m, 3H), 3.93-3.87 (m, 1H), 3.84-3.80 (m, 1H), 3.14-3.09 (m, 2H), 3.03-3.02 (m, 1H), 2.89-2.83 (m, 1H), 2.40-2.18 (m, 2H), 2.15-2.01 (m, 3H), 1.85-1.78 (m, 3H), 1.63-1.45 (m, 2H), 1.35-1.30 (m, 1H), 1.26-1.11 (m, 1H).

2-amino-4-(8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile 846)

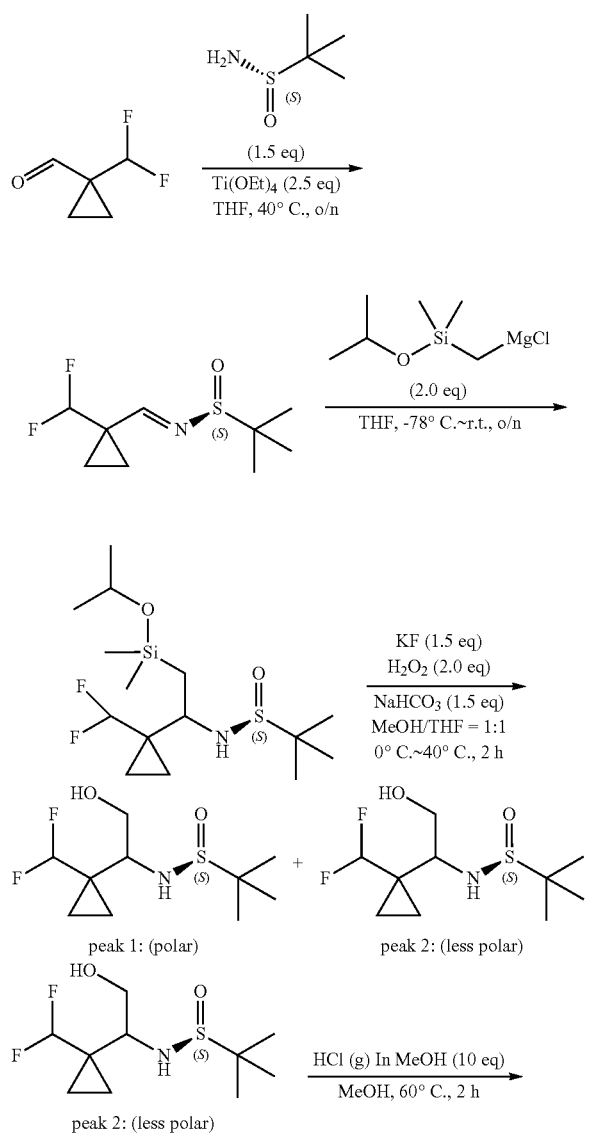

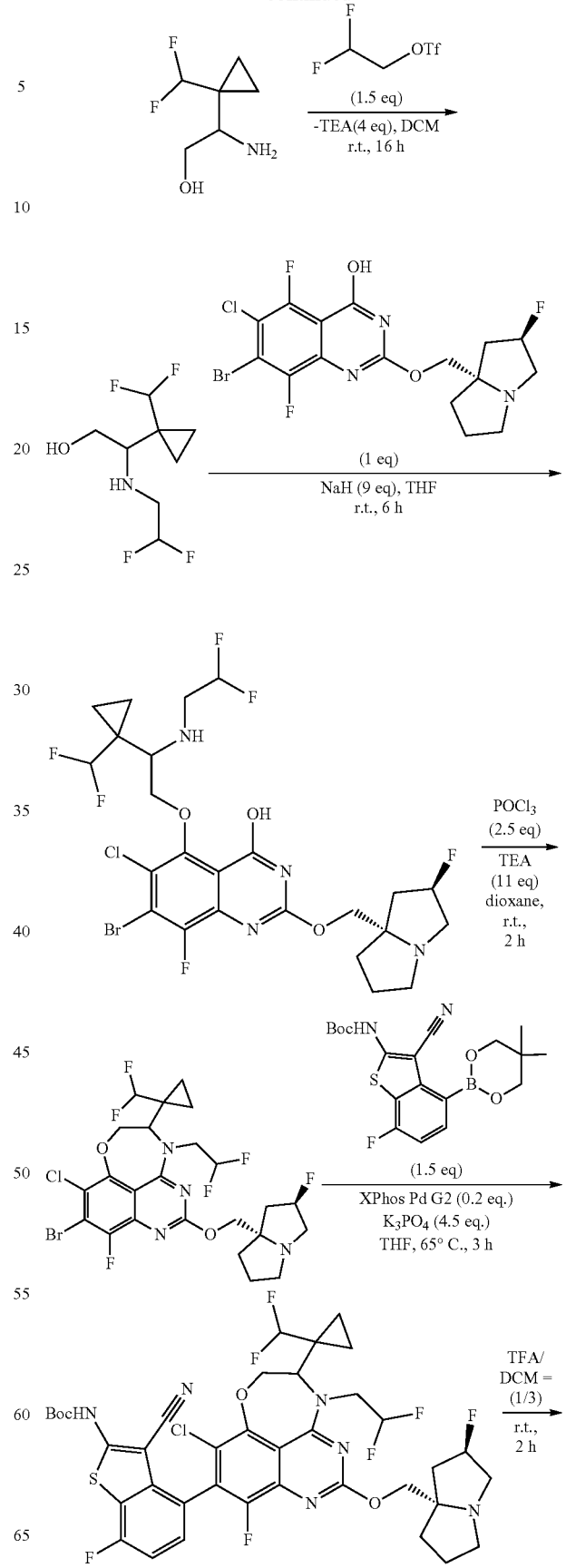

-continued

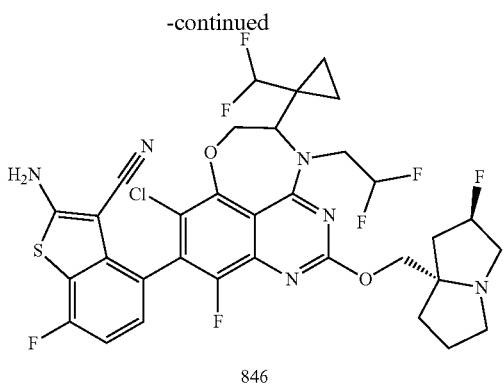

846

(S)—N-([1-(difluoromethyl) cyclopropyl]methylidene-2-methylpropane-2-sulfinamide A solution of 1-(difluoromethyl)cyclopropane-1-carbaldehyde (5.5 g, 45.796 mmol, 1 equiv) in DCM (300 mL) was treated with (S)-2-methylpropane-2-sulfinamide (8.33 g, 68.694 mmol, 1.5 equiv) under nitrogen atmosphere followed by the addition of Ti(OEt)$_4$ (26.12 g, 114.490 mmol, 2.5 equiv) dropwise at room temperature. The resulting mixture was stirred for overnight at 40° C. under nitrogen atmosphere. It was cooled to room temperature, washed with water (3×100 mL), and dried over anhydrous Na$_2$SO$_4$. After filtration, the filtrate was concentrated under reduced pressure to give a residue. The residue was purified by silica gel column chromatography, eluted with petroleum/ethyl acetate (2:1) to afford the desired product as an off-white oil. (ESI, m/z): 224 [M+H]$^+$ (S)—N-[1-[1-(difluoromethyl)cyclopropyl]-2-(isopropoxydimethylsilyl)ethyl]-2-methylpropane-2-sulfinamide A solution of (S)—N-([1-(difluoromethyl)cyclopropyl]methylidene-2-methylpropane-2-sulfinamide (800 mg, 3.583 mmol, 1 equiv) in THF (12 mL, 148.113 mmol) was treated with [(chloromagnesio)methyl] (isopropoxy)dimethylsilane (7.2 mL, 0.224 mmol, 2 equiv) dropwise for 0.5 h at −78° C. under nitrogen atmosphere. The resulting mixture was stirred for overnight at room temperature, quenched by the addition of sat. NH$_4$Cl (aq.) (5 mL) at 0° C. and extracted with DCM (3×100 mL). The extracts were combined washed with water (3×50 mL) and dried over anhydrous Na$_2$SO$_4$. After filtration, the filtrate was concentrated under reduced pressure to afford the desired product as a yellow oil which was used in the next step directly without further purification. (ESI, m/z): 356 [M+H]$^+$ (S)—N-(1-(1-(difluoromethyl)cyclopropyl)-2-hydroxyethyl)-2-methylpropane-2-sulfinamide A solution of (S)—N-[1-[1-(difluoromethyl)cyclopropyl]-2-(isopropoxydimethylsilyl)ethyl]-2-methylpropane-2-sulfinamide (1.5 g, 4.219 mmol, 1 equiv) in MeOH (10 mL, 246.988 mmol) and THF (10 mL, 123.428 mmol) was treated with KF (0.37 g, 6.329 mmol, 1.5 equiv) at room temperature under nitrogen atmosphere followed by the addition of H$_2$O$_2$ (0.96 g, 8.438 mmol, 2 equiv, 30%) dropwise at 0° C. The resulting mixture was stirred for 2 hours at room temperature under nitrogen atmosphere. It was quenched by the addition of Na$_2$S$_2$O$_3$ solution at room temperature, extracted with ethyl acetate. The extracts were combined, washed with bring and dried over Na$_2$SO$_4$. It was filtered and concentrated under reduced pressure to give a residue. The residue was purified by reversed-phase flash chromatography with the following conditions: column, C18; mobile phase, MeCN in Water (10 mmol/L NH$_4$HCO$_3$), 10% to 50% gradient in 10 min; detector, UV 254 nm to afford two desired products: intermediate 1 (polar) and intermediate 2 (less polar) as yellow solid.

Intermediate 1 (polar): $^1$H NMR: (400 MHZ, Chloroform-d) § 5.78 (t, J=57.3 Hz, 1H), 3.86 (d, J=6.6 Hz, 1H), 3.81 (m, 2H), 3.02 (m, 1H), 2.46-2.36 (m, 1H), 1.26 (s, 9H), 1.01-0.83 (m, 4H).

Intermediate 2 (less polar): $^1$H NMR: (400 MHZ, DMSO-d$_6$, ppm) δ 6.07 (t, J=57.3 Hz, 1H), 4.80-4.73 (m, 2H), 3.54 (td, J=6.2, 2.5 Hz, 2H), 3.03 (q, J=6.3 Hz, 1H), 1.15 (s, 9H), 0.79-0.65 (m, 4H).

2-Amino-2-(1-(difluoromethyl)cyclopropyl)ethan-1-ol A mixture of (S)—N-(1-(1-(difluoromethyl)cyclopropyl)-2-hydroxyethyl)-2-methylpropane-2-sulfinamide (intermediate 2, less polar) (220 mg, 0.862 mmol, 1 equiv) and HCl (g) in MeOH (1M, 8.6 mL, 8.620 mmol, 10 equiv) in MeOH (2 mL,) was stirred for 2 hours at 60° C. It was cooled to room temperature, concentrated under reduced pressure to afford the desired product as HCl salt (220 mg, crude) as colorless oil. (ESI, m/z): 152 [M+H]$^+$ 2-((2,2-Difluoroethyl)amino)-2-(1-(difluoromethyl)cyclopropyl)ethan-1-ol A mixture of 2-amino-2-(1-(difluoromethyl)cyclopropyl)ethan-1-ol HCl salt (220 mg, 1.455 mmol, 1 equiv), 2,2-difluoroethyl trifluoromethanesulfonate (376 mg, 1.760 mmol, 1.5 equiv) and triethylamine (474 mg, 4.692 mmol, 4 equiv) in DCM (5 mL, 78.653 mmol) was stirred for 16 hours at room temperature. It was quenched with water, extracted with ethyl acetate (3×10 mL). The extracts were combined, washed with brine (1×5 mL), dried over anhydrous Na$_2$SO$_4$. After filtration, the filtrate was concentrated under reduced pressure to give a residue. The residue was purified by silica gel column chromatography, eluted with petroleum/ethyl acetate (1: 1) to afford the desired product as a colorless oil. (ESI, m/z): 216 [M+H]$^+$ 7-Bromo-6-chloro-5-(2-((2,2-difluoroethyl)amino)-2-(1-(difluoromethyl)cyclopropyl) ethoxy)-8-fluoro-2-(((2R,7aS)-2-fluorotetrahydro-1H-pyrrolizin-7a(5H)-yl)methoxy) quinazolin-4-ol A mixture of 2-((2,2-difluoroethyl)amino)-2-(1-(difluoromethyl)cyclopropyl)ethan-1-ol (120 mg, 0.558 mmol, 1 equiv), 2-{[(2R,7aS)-2-fluoro-hexahydropyrrolizin-7a-yl]methoxy}-7-bromo-6-chloro-5,8-difluoroquinazolin-4-ol (252.42 mg, 0.558 mmol, 1 equiv) and NaH (200.73 mg, 5.022 mmol, 9 equiv, 60%) in THF (3 mL, 37.028 mmol) was stirred for 6 hours at room temperature under nitrogen atmosphere. It was quenched with water (5 mL) at 0° C. and extracted with ethyl acetate (3×10 mL). The extracts were combined, washed with brine (1×10 mL), dried over anhydrous Na$_2$SO$_4$. After filtration, the filtrate was concentrated under reduced pressure to afford desired product (393 mg, crude) as white solid. (ESI, m/z): 647 [M+H]$^+$ 9-Bromo-8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline A solution of 7-bromo-6-chloro-5-(2-((2,2-difluoroethyl)amino)-2-(1-(difluoromethyl)cyclopropyl) ethoxy)-8-fluoro-2-(((2R,7aS)-2-fluorotetrahydro-1H-pyrrolizin-7a(5H)-yl)methoxy) quinazolin-4-ol (390 mg, 0.602 mmol, 1 equiv) triethylamine (670 mg, 6.622 mmol, 11 equiv) and POCl$_3$ (231 mg, 1.505 mmol, 2.5 equiv) in dioxane (20 mL, 236.079 mmol) was stirred for 2 hours at room temperature under nitrogen atmosphere. It was quenched with water and extracted with ethyl acetate (3×10 mL). The extracts were combined, washed with brine (1×20 mL), dried over anhydrous Na₂SO₄. After filtration, the filtrate was concentrated under reduced pressure to give a residue. The residue was purified by silica gel column chromatography, eluted with DCM/MeOH (20: 1) to the desired product as a white solid. (ESI, m/z): 629 [M+H]⁺

Tert-butyl (4-(8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate A mixture of 9-bromo-8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline (220 mg, 0.349 mmol, 1 equiv), tert-butyl N-[3-cyano-4-(5,5-dimethyl-1,3,2-dioxaborinan-2-yl)-7-fluoro-1-benzothiophen-2-yl]carbamate (211 mg, 0.523 mmol, 1.5 equiv), 2nd Generation XPhos Precatalyst/X-Phos aminobiphenyl palladium chloride precatalyst (55 mg, 0.070 mmol, 0.2 equiv) and K₃PO₄ (333 mg, 1.571 mmol, 4.5 equiv) in THF (4 mL) was stirred for 3 hours at 65° C. under argon atmosphere. It was cooled to room temperature, concentrated under reduced pressure, and extracted with ethyl acetate (3×5 mL). The extracts were combined, washed with brine (1×10 mL), dried over anhydrous Na₂SO₄. After filtration, the filtrate was concentrated under reduced pressure to give a residue. The residue was purified by silica gel column chromatography, eluted with DCM/MeOH (10: 1) to afford the desired product as a yellow solid. (ESI, m/z): 841 [M+H]⁺

2-Amino-4-(8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile A solution of tert-butyl (4-(8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate (200 mg, 0.238 mmol, 1 equiv) and TFA (1 mL) in DCM (3 mL) was stirred for 2 hours at room temperature. The resulting mixture was concentrated under reduced pressure to give a residue. The residue was basified to pH 8 with NH₃·H₂O. The crude product (200 mg) was purified by Prep-HPLC with the following conditions (Column: Sunfire C18 5 m, 30 mm*150 mm; Mobile Phase A: Water (0.1% TFA), Mobile Phase B: ACN; Flow rate: 60 mL/min; Gradient: 25% B to 38% B in 10 min; Wave Length: UV 254 nm/220 nm; RT1(min): 10.25/10.5) to afford the desired product as a white solid. (ESI, m/z): 741 [M+H]⁺

¹H NMR:(400 MHZ, DMSO-d₆, ppm) δ 8.14 (s, 2H), 7.26 (m, 1H), 7.14 (m, 1H), 6.75-6.33 (m, 1H), 6.03 (m, 1H), 5.28 (m, 1H), 4.98 (m, 1H), 4.63 (m, 1H), 4.43 (m, 1H), 4.21-3.95 (m, 3H), 3.78 (m, 1H), 3.09 (m, 2H), 3.01 (m, 1H), 2.83 (m, 1H), 2.07 (m, 4H), 1.80 (m, 2H), 1.04 (m, 1H), 0.86 (m, 3H).

Example 1ar: Synthesis of 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (855)

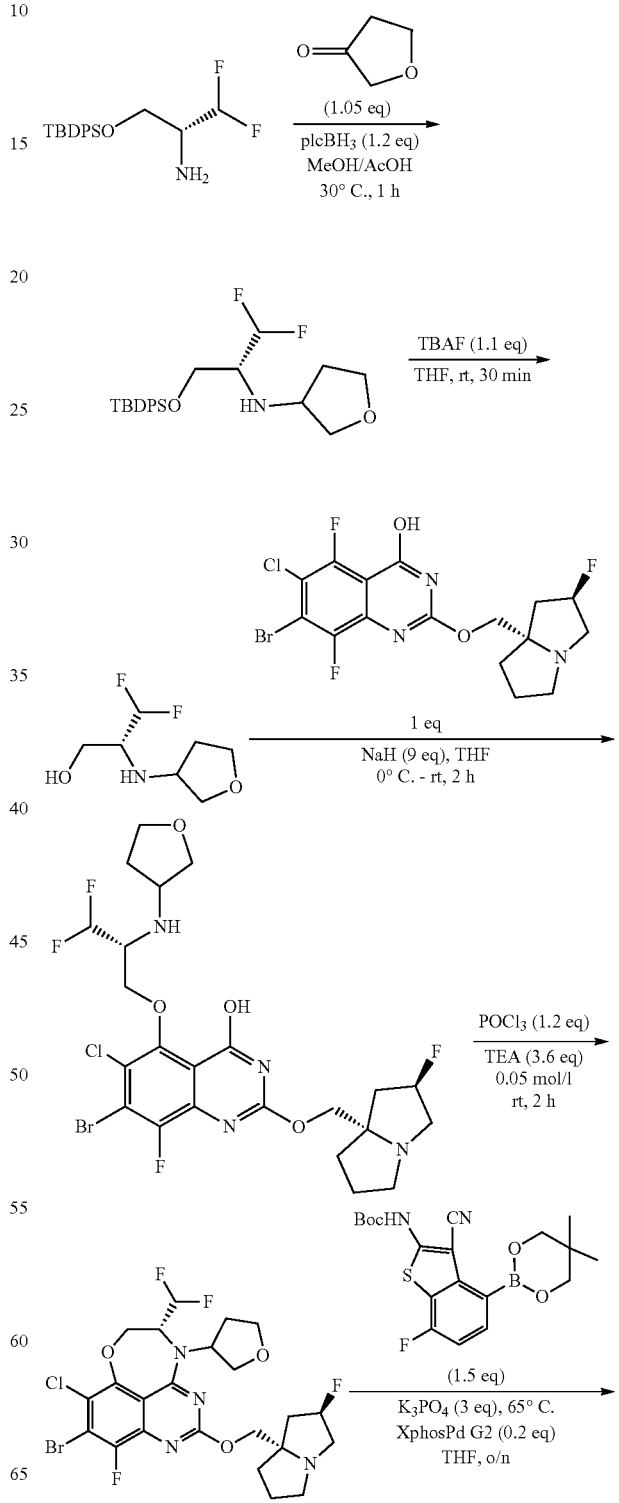

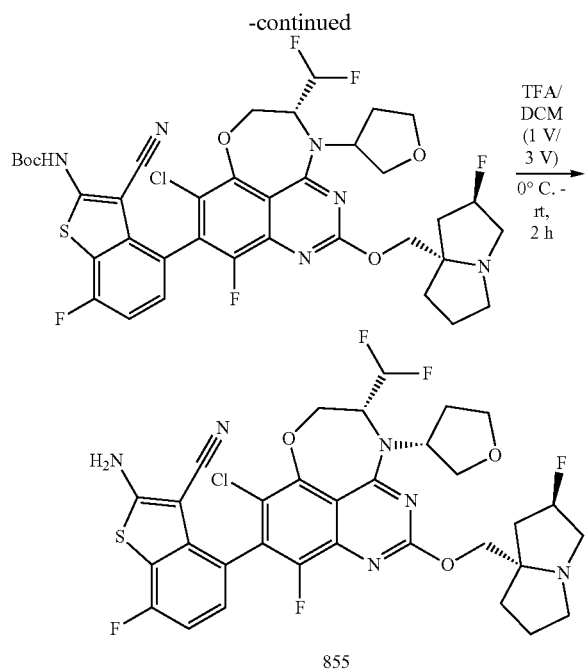

855

N-[(2R)-3-[(tert-butyldiphenylsilyl)oxy]-1,1-difluoropropan-2-yl]oxolan-3-amine To a degassed solution of [(2R)-2-amino-3,3-difluoropropoxy](tert-butyl)diphenylsilane (1.3 g, 2.604 mmol, 1 equiv, 70%) in MeOH (12 mL)/AcOH (1 mL) was added dihydrofuran-3-one (235.36 mg, 2.734 mmol, 1.05 equiv) and 2-methylpyridine borane (334.2 mg, 3.125 mmol, 1.2 equiv) at room temperature. The reaction mixture was stirred at 30° C. for 1 hour. It was cooled to room temperature, concentrated under reduced pressure to give a residue. The residue was purified by column chromatography on silica gel (Combiflash) (ethyl acetate/petroleum=¼) to afford the desired product as yellow oil. (ESI, m/z):420[M+H]$^+$ (2R)-3,3-difluoro-2-(oxolan-3-ylamino)propan-1-ol To a stirred solution of N-[(2R)-3-[(tert-butyldiphenylsilyl)oxy]-1,1-difluoropropan-2-yl]oxolan-3-amine (1.138 g, 2.712 mmol, 1 equiv) in anhydrous THF (10 mL) was added TBAF (3 mL, 2.98 mmol, 1.1 equiv) at room temperature and stirred for 30 minutes. It was concentrated under reduced pressure to give crude product which was purified by column chromatography using 1% to 5% MeOH in DCM gradient to afford desired compound as a pale yellow oil. (ESI, m/z): 182[M+H]$^+$ 7-Bromo-6-chloro-5-((2R)-3,3-difluoro-2-((tetrahydrofuran-3-yl)amino)propoxy)-8-fluoro-2-(((2R,7aS)-2-fluorotetrahydro-1H-pyrrolizin-7a(5H)-yl)methoxy)quinazolin-4-ol To a solution of 7-bromo-6-chloro-5,8-difluoro-2-(((2R,7aS)-2-fluorotetrahydro-1H-pyrrolizin-7a(5H)-yl)methoxy)quinazolin-4-ol (1.2 g, 2.651 mmol, 1.00 equiv) and (2R)-3,3-difluoro-2-(oxolan-3-ylamino)propan-1-ol (0.50 g, 2.784 mmol, 1.05 equiv) in THF (12 mL) was added NaH (950 mg, 23.859 mmol, 9 equiv, 60%) at 0° C. The mixture was allowed to warm to room temperature and stirred for 2 hours, quenched with sat. NH$_4$Cl (200 mL) and extracted with DCM (2×200 mL). The extracts were combined, washed with brine (10 mL), dried over anhydrous Na$_2$SO$_4$. It was filtered, concentrated under reduced pressure to give crude product which was purified by column chromatography using 1% to 5% MeOH in DCM gradient to afford desired compound as an off-white solid. (ESI, m/z):613[M+H]$^+$ (5R)-9-bromo-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino-[5,6,7-de]quinazoline To a stirred solution of 7-bromo-6-chloro-5-((2R)-3,3-difluoro-2-((tetrahydrofuran-3-yl)amino)propoxy)-8-fluoro-2-(((2R,7aS)-2-fluorotetrahydro-1H-pyrrolizin-7a(5H)- yl)methoxy)quinazolin-4-ol (770 mg, 1.254 mmol, 1 equiv) in anhydrous 1,4-dioxane (25 mL) was added POCl$_3$ (230 mg, 1.505 mmol, 1.2 equiv) and triethylamine (457 mg, 4.514 mmol, 3.6 equiv) dropwise at room temperature. The reaction mixture was stirred at room temperature for a additional 2 hours. The reaction mixture was concentrated under reduced pressure to give crude product which was purified by column chromatography using 1% to 5% MeOH in DCM gradient and further purified by chiral-prep HPLC with the following conditions: (Column: CHIRALPAK-IA 2*25 cm, 5m; Mobile Phase A: HEX(0.1% DEA), Mobile Phase B: ETOH: DCM=1: 1; Flow rate: 20 mL/min; Gradient: isocratic 25; Wave Length: 254/220 nm; RT1(min): 6.743; RT2(min): 7.003; Sample Solvent: MEOH; Injection Volume: 1.7 mL; Number Of Runs: 3) to afford two desired intermediates: Intermediate A:(ESI, m/z):595[M+H]$^+$ and intermediate B:(ESI, m/z): 595[M+H]$^+$ as pale yellow solids.

Tert-butyl (4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate To a degassed solution of (5R)-9-bromo-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino-[5,6,7-de]quinazoline (intermediate A from previous step) (140 mg, 0.235 mmol, 1 equiv) in THF (2.4 mL) was added tert-butyl N-[3-cyano-4-(5,5-dimethyl-1,3,2-dioxaborinan-2-yl)-7-fluoro-1-benzothiophen-2-yl]carbamate (142 mg, 0.352 mmol, 1.5 equiv) followed by dicyclohexyl[2',4',6'-tris(propan-2-yl)-[1,1'-biphenyl]-2-yl]phosphane; (2'-amino-[1,1'-biphenyl]-2-yl(chloro)palladium (37 mg, 0.047 mmol, 0.2 equiv) and K$_3$PO$_4$ (150 mg, 0.705 mmol, 3 equiv) at room temperature under nitrogen atmosphere. The reaction mixture was stirred at 65° C. for overnight. It was cooled to room temperature and quenched with water, extracts with ethyl acetate. The extracts were combined, washed with brine, dried over Na$_2$SO$_4$. It was filtered and concentrated to give a residue. The residue was purified by reversed-phase flash chromatography with the following conditions: (column, C18; mobile phase, ACN in H$_2$O, 10% to 100% gradient in 20 min; detector, UV 254 nm) to afford the desired product as a yellow solid. (ESI, m/z): 707 [M+H]$^+$ 2-Amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile To a solution of tert-butyl (4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate (150 mg, 0.212 mmol, 1 equiv) in DCM (6 mL) was added TFA (2 mL) at 0° C. The mixture was stirred for 1 hour at room temperature. It was concentrated to give a crude. The crude product was purified by Prep-HPLC with the following conditions: (Column: CHIRAL ART Cellulose-SB 2*25 cm, 5m; Mobile Phase A: HEX(0.1% DEA), Mobile Phase B: IPA: DCM=1: 1; Flow rate: 20 mL/min;

Gradient: isocratic 30; Wave Length: UV 254/220 nm; RT1(min): 8.073; RT2(min): 9.157; Injection Volume: 0.25 mL; Number Of Runs: 10). The Column: CHIRAL ART Cellulose-SB 2*25 cm, 5m; Mobile Phase A: HEX(0.1% DEA), Mobile Phase B: IPA: DCM=1: 1; Flow rate: 20 mL/min; Gradient: isocratic 30; Wave Length: UV 254/220 nm; RT1(min): 8.073; RT2(min): 9.157; Injection Volume: 0.25 mL; Number Of Runs: 10 to afford the desired product as a white solid. (ESI, m/z):707 [M+H]+; 1H NMR: (400 MHZ, Chloroform-d) δ 7.25-7.21 (m, 1H), 7.04 (t, J=8.8 Hz, 1H), 5.93 (td, J=54.9, 6.9 Hz, 1H), 5.63-5.54 (m, 1H), 5.49-5.28 (m, 3H), 4.97 (dd, J=12.5, 4.2 Hz, 1H), 4.62-4.42 (m, 3H), 4.41-4.29 (m, 1H), 4.20 (td, J=8.7, 4.9 Hz, 1H), 4.03-3.89 (m, 2H), 3.81 (q, J=8.3 Hz, 1H), 3.76-3.53 (m, 2H), 3.44-3.28 (m, 1H), 3.19-3.06 (m, 1H), 2.60-2.50 (m, 1H), 2.51-2.44 (m, 1H), 2.43-2.37 (m, 1H), 2.37-2.24 (m, 3H), 2.14-2.08 (m, 3H).

Example 1as: Synthesis of 2-amino-4-((5R)-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (1057)

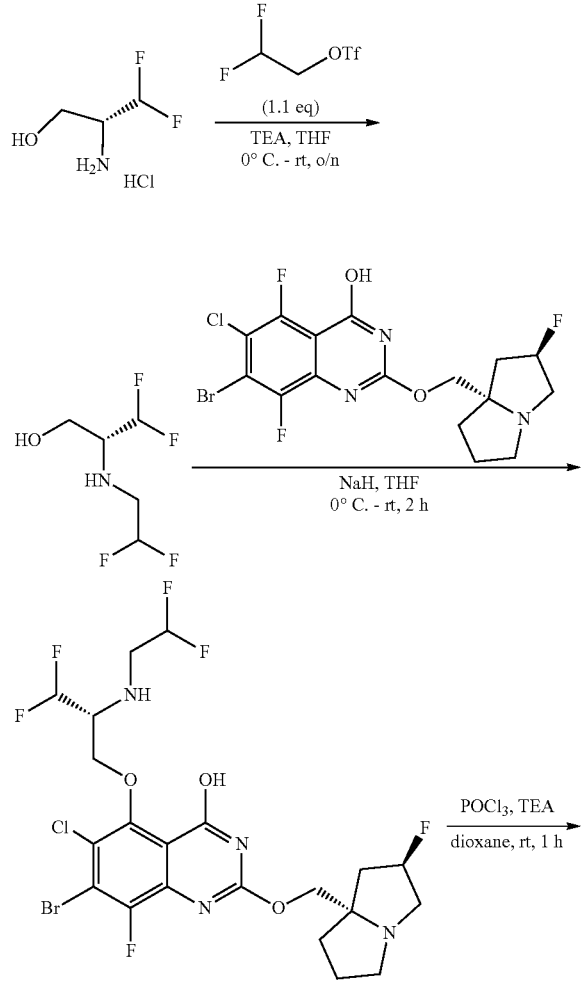

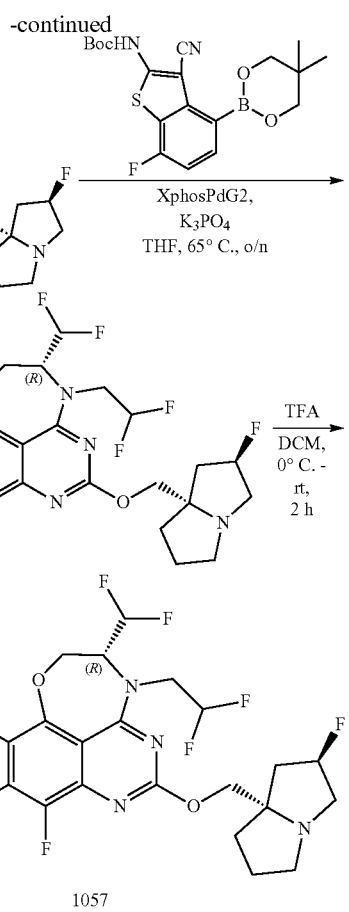

(2R)-2-[(2,2-difluoroethyl)amino]-3,3-difluoropropan-1-ol A solution of (2R)-2-amino-3,3-difluoropropan-1-ol hydrochloride (600 mg, 4.1 mmol, 1 equiv) in THF (14 mL) was treated with triethylamine (3.4 mL, 24.5 mmol, 6 equiv) at room temperature under nitrogen atmosphere followed by the addition of 2,2-difluoroethyl trifluoromethanesulfonate (958 mg, 4.5 mmol, 1.1 equiv) at room temperature. The resulting mixture was stirred for overnight at room temperature under nitrogen atmosphere. It was concentrated under reduced pressure to give a residue. The residue was purified by silica gel column chromatography, eluted with petroleum/ethyl acetate (1:1) to afford the desired product as a yellow oil. (ESI, m/z): 176.20 [M+1]+

7-Bromo-6-chloro-5-((R)-2-((2,2-difluoroethyl)amino)-3,3-difluoropropoxy)-8-fluoro-2-(((2R,7aS)-2-fluorotetrahydro-1H-pyrrolizin-7a(5H)-yl)methoxy)quinazolin-4-ol A solution of (2R)-2-[(2,2-difluoroethyl)amino]-3,3-difluoropropan-1-ol (200 mg, 1.142 mmol, 1 equiv) in THF (3 mL) was treated with 7-bromo-6-chloro-5,8-difluoro-2-(((2R, 7aS)-2-fluorotetrahydro-1H-pyrrolizin-7a(5H)-yl)methoxy) quinazolin-4-ol (646 mg, 1.4 mmol, 1 equiv) followed by the addition of NaH (308 mg, 12.9 mmol, 9 equiv) at 0° C. The resulting mixture was stirred for 2 hours at room temperature under nitrogen atmosphere. It was concentrated to give a residue. The residue was purified by silica gel column chromatography, eluted with CH2Cl2/MeOH (5%) to afford the desired product as a yellow solid. (ESI, m/z): 607.25 [M+1]+

(R)-9-bromo-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline A solution of 7-bromo-6-chloro-5-((R)-2-((2,2-difluoroethyl)amino)-3,3-difluoropropoxy)-8-fluoro-2-(((2R,7aS)-2-fluorotetrahydro-1H-pyrrolizin-7a(5H)-yl)methoxy)quinazolin-4-ol (290 mg, 0.5 mmol, 1 equiv) in dioxane (3 mL) was treated with triethylamine (0.28 mL) followed by the addition of POCl₃ (0.12 mL, 1.3 mmol, 2.8 equiv) dropwise. The resulting mixture was stirred for 1 hour at room temperature under nitrogen atmosphere. It was concentrated under reduced pressure to give a residue. The residue was purified by silica gel column chromatography, eluted with CH₂Cl₂/MeOH (1%) to afford the desired product (203 mg, 72.26%) as a yellow solid. (ESI, m/z): 588.90 [M+1]+

Tert-butyl (4-((5R)-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate To a stirred solution of (R)-9-bromo-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline (180 mg, 0.3 mmol, 1 equiv) in THF (5 mL) was treated with tert-butyl N-[3-cyano-4-(5,5-dimethyl-1,3,2-dioxaborinan-2-yl)-7-fluoro-1-benzothiophen-2-yl]carbamate (185 mg, 0.5 mmol, 1.5 equiv) and K₃PO₄ (194 mg, 0.9 mmol, 3 equiv) under nitrogen atmosphere followed by the addition of 2nd Generation XPhos Precatalyst (48 mg, 0.06 mmol, 0.2 equiv) at 65° C. for overnight under nitrogen atmosphere. It was cooled to room temperature, concentrated under reduced pressure to give a residue. The residue was purified by reversed-phase flash chromatography with the following conditions: column, C18; mobile phase, MeCN in Water (10 mmol/L NH₄HCO₃), 0% to 100% gradient in 10 min; detector, UV 254 nm to afford the desired product as a yellow solid. (ESI, m/z): 801.10 [M+1]+

2-Amino-4-((5R)-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile A solution of tert-butyl (4-((5R)-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate (200 mg, 0.3 mmol, 1 equiv) in DCM (6 mL) was treated with TFA (1 mL) at 0° C. The resulting mixture was stirred for 2 hours at room temperature under nitrogen atmosphere. It was concentrated under reduced pressure to give a crude. The crude product (220 mg) was purified by Prep-HPLC with the following conditions (Column: XBridge Prep OBD C18 Column, 30*150 mm, 5 µm; Mobile Phase A: Water (10 mmol/L NH₄HCO₃), Mobile Phase B: ACN; Flow rate: 60 mL/min; Gradient: 25% B to 40% B in 10 min, 70% B; Wave Length: UV 220 nm; RT1(min): 8.88; Number Of Runs: 0) to afford the desired product as a solid.(ESI, m/z): 701.30 [M+1]+

¹H NMR: δ 7.15 (dd, J=8.4, 5.0 Hz, 1H), 6.99 (t, J=8.7 Hz, 1H), 6.55 (t, J=56.1 Hz, 1H), 6.22-5.92 (m, 1H), 5.91-5.71 (m, 1H), 5.42 (d, J=53.5 Hz, 1H), 5.00 (dd, J=13.4, 4.4 Hz, 1H), 4.97-4.84 (m, 1H), 4.55-4.35 (m, 2H), 4.33-4.17 (m, 1H), 3.89-3.58 (m, 2H), 3.50-3.32 (m, 1H), 3.24-3.03 (m, 1H), 2.71-2.41 (m, 1H), 2.46-2.24 (m, 2H), 2.16 (s, 3H).

Example 1at: Synthesis of 2-amino-4-((R)-9-chloro-4-(2,2-difluoroethyl)-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-7-fluorobenzo[b]thiophene-3-carbonitrile (1203)

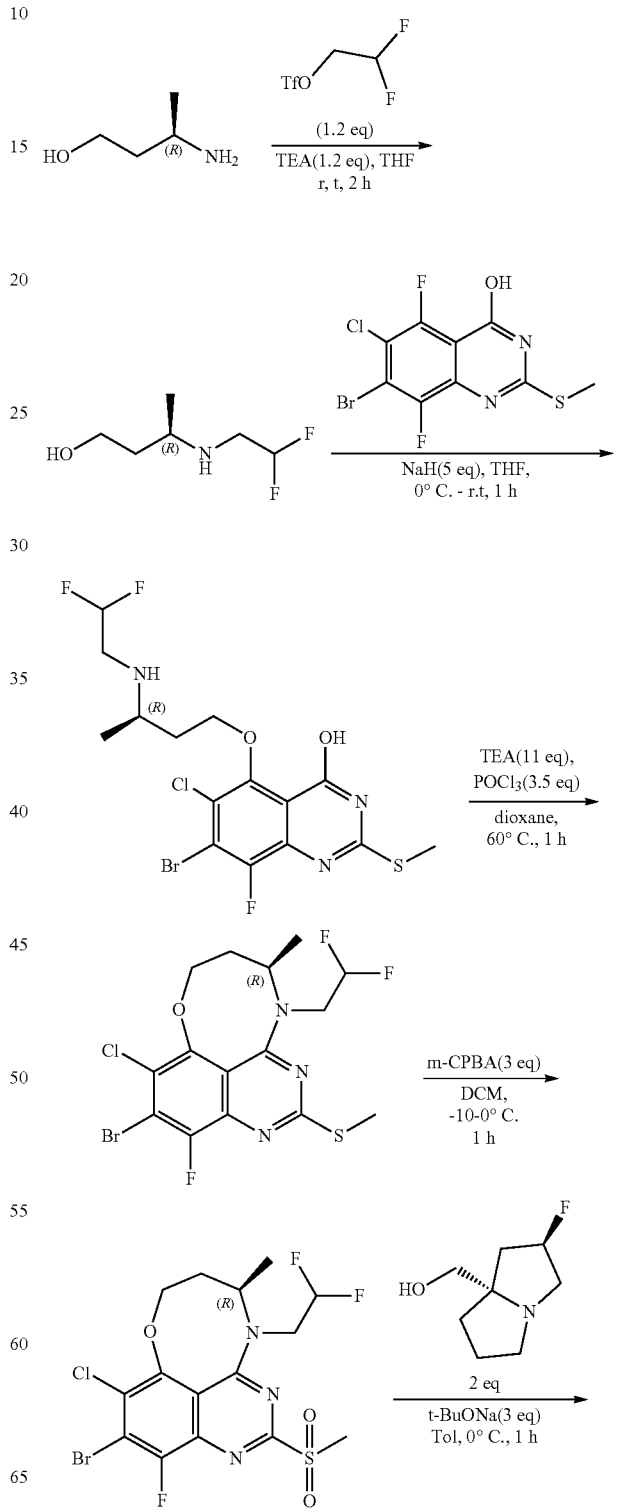

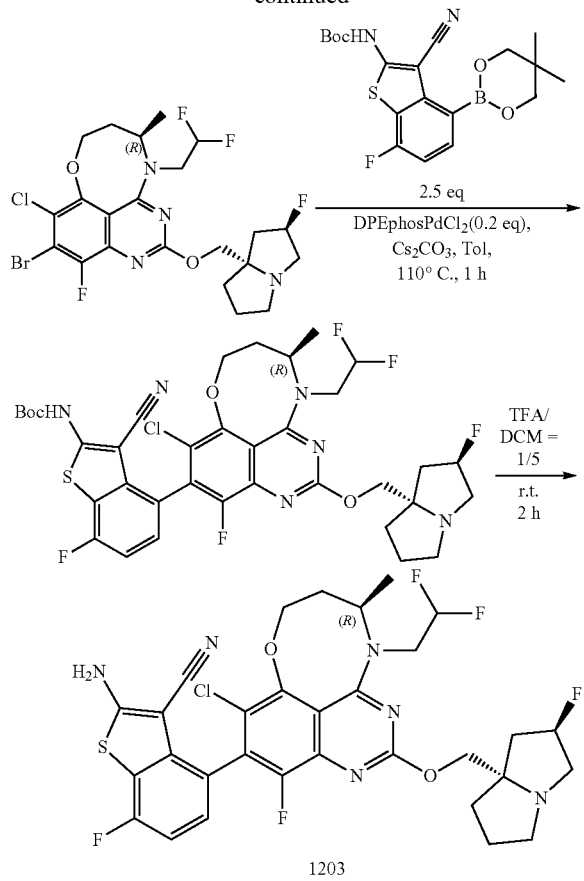

(3R)-3-[(2,2-difluoroethyl) amino] butan-1-ol A solution of (3R)-3-aminobutan-1-ol (1 g, 11.219 mmol, 1.00 equiv), triethylamine (1.36 g, 13.463 mmol, 1.20 equiv) and 2,2-difluoroethyl trifluoromethanesulfonate (2.88 g, 13.463 mmol, 1.20 equiv) in THF (10 mL) was stirred for 2 hours at room temperature under nitrogen atmosphere. The resulting mixture was concentrated under vacuum to give a residue. The residue was purified by silica gel column chromatography, eluted with $CH_2Cl_2$/MeOH (10:1) to afford the desired product as a light yellow oil. (ESI, m/z): 154 $[M+H]^+$ (R)-7-bromo-6-chloro-5-(3-((2,2-difluoroethyl)amino) butoxy)-8-fluoro-2-(methylthio)-quinazolin-4-ol To a stirred solution of (3R)-3-[(2,2-difluoroethyl)amino]butan-1-ol (3 g, 19.586 mmol, 1.0 equiv) and 7-bromo-6-chloro-5,8-difluoro-2-(methylsulfanyl)quinazolin-4-ol (0.80 g, 2.350 mmol, 0.12 equiv) in THF (50 mL) was added NaH (2.35 g, 97.930 mmol, 5.0 equiv) in portions at 0° C. under nitrogen atmosphere. The resulting mixture was stirred for 1 hour at 0° C. under nitrogen atmosphere, quenched with water/ice, extracted with ethyl acetate (3×100 mL). The extracts were combined, washed with brine (100 mL), dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 20% to 70% gradient in 30 min; detector, UV 254 nm to afford the desired product as an off-white solid. (ESI, m/z): 474 $[M+H]^+$ (R)-10-bromo-9-chloro-4-(2,2-difluoroethyl)-11-fluoro-5-methyl-2-(methylthio)-4,5,6,7-tetrahydro-[1,5]oxazocino[4,3,2-de]quinazoline A solution of (R)-7-bromo-6-chloro-5-(3-((2,2-difluoroethyl)amino)butoxy)-8-fluoro-2-(methylthio)-quinazolin-4-ol (600 mg, 1.264 mmol, 1.0 equiv), $POCl_3$ (678 mg, 4.424 mmol, 3.50 equiv) and triethylamine (1407 mg, 13.904 mmol, 11.0 equiv) in 1,4-dioxane (10 mL) was stirred for 1 hour at 60° C. under nitrogen atmosphere. It was cooled to room temperature, quenched with water, and extracted with ethyl acetate (3×50 mL). The extracts were combined, washed with brine (50 mL), and dried over anhydrous $Na_2SO_4$. After filtration, the filtrate was concentrated under reduced pressure to give a residue. The residue was purified by silica gel column chromatography, eluted with petroleum/ethyl acetate (10:1) to afford the desired product as a light-yellow solid. (ESI, m/z): 456 $[M+H]^+$ (R)-10-bromo-9-chloro-4-(2,2-difluoroethyl)-11-fluoro-5-methyl-2-(methylsulfonyl)-4,5,6,7-tetrahydro-[1,5]oxazocino[4,3,2-de]quinazoline To a stirred solution of (R)-10-bromo-9-chloro-4-(2,2-difluoroethyl)-11-fluoro-5-methyl-2-(methylthio)-4,5,6,7-tetrahydro-[1,5]oxazocino[4,3,2-de]quinazoline (150 mg, 0.328 mmol, 1.0 equiv) and molecular sieves 3A in DCM (5 mL) was added m-CPBA (200 mg, 0.984 mmol, 3.0 equiv, 85%) in portions at −10° C. under nitrogen atmosphere. The resulting mixture was stirred for 1 hour at 0° C., quenched with sat. $NaHSO_3$ (aq.) at room temperature and extracted with $CH_2Cl_2$ (3×20 mL). The extracts were combined, washed with sat. $NaHCO_3$(aq.) (3×20 mL) and brine (20 mL), dried over anhydrous $Na_2SO_4$. After filtration, the filtrate was concentrated under reduced pressure to give the desired product as a yellow solid which was used in the next step directly without further purification. (ESI, m/z): 488$[M+H]^+$ (R)-10-bromo-9-chloro-4-(2,2-difluoroethyl)-11-fluoro-2-(((2R,7aS)-2-fluorotetrahydro-1H-pyrrolizin-7a(5H)-yl) methoxy)-5-methyl-4,5,6,7-tetrahydro-[1,5]oxazocino[4,3,2-de]quinazoline To a stirred solution of (R)-10-bromo-9-chloro-4-(2,2-difluoroethyl)-11-fluoro-5-methyl-2-(methylsulfonyl)-4,5,6,7-tetrahydro-[1,5]oxazocino[4,3,2-de]quinazoline (150 mg, 0.307 mmol, 1.0 equiv), molecular sieves 3A and [(2R,7aS)-2-fluoro-hexahydropyrrolizin-7a-yl]methanol (98 mg, 0.614 mmol, 2.00 equiv) in toluene (5 mL) was added t-BuONa (88 mg, 0.921 mmol, 3.00 equiv) in portions at 0° C. under nitrogen atmosphere. The resulting mixture was stirred for 1 hour at 0° C. under nitrogen atmosphere, quenched with sat. $NH_4Cl$ (aq.) at room temperature and extracted with ethyl acetate (3×20 mL). The extracts were combined, washed with brine (20 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a light-yellow solid. (ESI, m/z): 567$[M+H]^+$ Tert-butyl (4-((R)-9-chloro-4-(2,2-difluoroethyl)-11-fluoro-2-(((2R,7aS)-2-fluorotetrahydro-1H-pyrrolizin-7a (5H)-yl)methoxy)-5-methyl-4,5,6,7-tetrahydro-[1,5]oxazocino[4,3,2-de]quinazolin-10-yl)-3-cyano-7-fluorobenzo[b] thiophen-2-yl)carbamate A solution of (R)-10-bromo-9-chloro-4-(2,2-difluoroethyl)-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazoline (120 mg, 0.211 mmol, 1.00 equiv), tert-butyl N-[3-cyano-4-(5,5-dimethyl-1,3,2-dioxaborinan-2-yl)-7-fluoro-1-benzothiophen-2-yl]carbamate (214 mg, 0.527 mmol, 2.50 equiv), dichloropalladium; {2-[2-(diphenylphosphanyl)phenoxy]phenyl}diphenylphosphane (30 mg, 0.042 mmol, 0.20 equiv), molecular sieves 3A and Cs₂CO₃ (275 mg, 0.844 mmol, 4.00 equiv) in toluene (5 mL) was stirred for 1 hour at 110° C. under argon atmosphere. It was cooled to room temperature, quenched with water, and extracted with ethyl acetate (3×20 mL). The extracts were combined, washed with brine (20 mL), and dried over anhydrous Na₂SO₄. After filtration, the filtrate was concentrated under reduced pressure to give a residue. The residue was purified by prep-TLC (CH₂Cl₂/MeOH=20:1) to afford the desired product as a light-yellow solid. (ESI, m/z): 779[M+H]⁺

2-Amino-4-((R)-9-chloro-4-(2,2-difluoroethyl)-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-7-fluorobenzo[b]thiophene-3-carbonitrile A solution of tert-butyl (4-((R)-9-chloro-4-(2,2-difluoroethyl)-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-3-cyano-7-fluorobenzo[b]thiophen-2-yl)carbamate (73 mg, 0.094 mmol, 1.00 equiv) and TFA (1.0 mL) in DCM (5.0 mL) was stirred for 2 hours at room temperature under nitrogen atmosphere. The resulting mixture was concentrated under vacuum to give a crude. The crude product was purified by prep-HPLC with the following conditions: Column, XBridge Shield RP18 OBD Column, 30×150 mm, 5 μm; mobile phase, Water (10 mmol/L NH₄HCO₃) and ACN (35% ACN up to 80% in 8 min); Detector, UV 220 nm to afford the desired product as a white solid. (ESI, m/z): 679 [M+H]⁺

H-NMR (400 MHZ, DMSO-d₆) δ 8.08 (br, 2H), 7.33-7.19 (m, 1H), 7.18-7.09 (m, 1H), 6.70-6.35 (m, 1H), 5.35-5.21 (m, 1H), 4.51-4.41 (m, 1H), 4.40-4.27 (m, 1H), 4.25-4.15 (m, 1H), 4.13-4.02 (m, 2H), 4.02-3.95 (m, 2H), 3.14-3.03 (m, 2H), 3.00 (s, 1H), 2.86-2.80 (m, 1H), 2.19-2.11 (m, 1H), 2.05 (m, 1H), 2.02-1.90 (m, 3H), 1.86-1.73 (m, 3H), 1.29-1.22 (m, 3H).

Example 1au: Synthesis of 2-amino-4-((R)-9-chloro-11-fluoro-2-(((2R,7aS)-2-fluorotetrahydro-1H-pyrrolizin-7a(5H)-yl)methoxy)-4,5-dimethyl-4,5,6,7-tetrahydro-[1,5]oxazocino[4,3,2-de]quinazolin-10-yl)-7-fluorobenzo[b]thiophene-3-carbonitrile (1222)

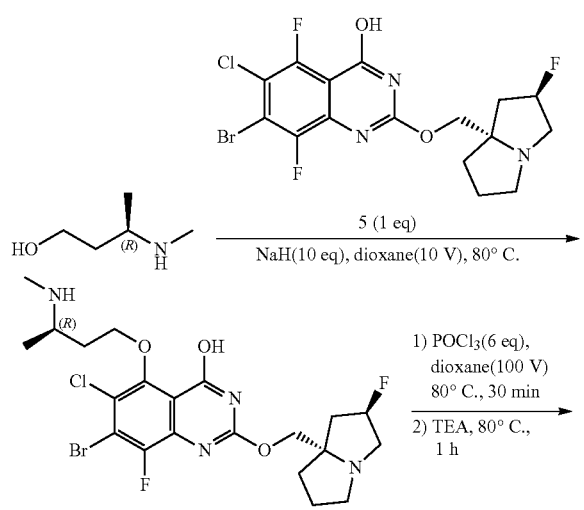

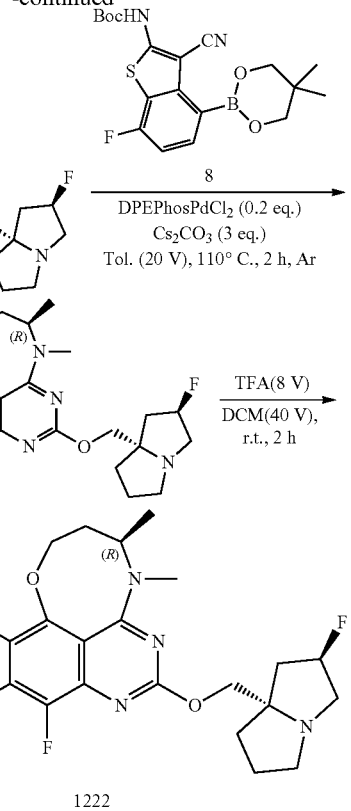

1222

7-Bromo-6-chloro-8-fluoro-2-(((2R,7aS)-2-fluorotetrahydro-1H-pyrrolizin-7a(5H)-yl)methoxy)-5-((R)-3-(methylamino)butoxy)quinazolin-4-ol To a solution of (3R)-3-(methylamino)butan-1-ol (256 mg, 2.486 mmol, 1.5 equiv) and 7-bromo-6-chloro-5,8-difluoro-2-(((2R,7aS)-2-fluorotetrahydro-1H-pyrrolizin-7a(5H)-yl)methoxy)quinazolin-4-ol (750 mg, 1.657 mmol, 1.0 equiv) in dioxane (7.5 mL) was added NaH (397 mg, 16.570 mmol, 10 equiv) in portions at 0° C. The resulting mixture was heated to 80° C. and stirred for 1 hour. It was cooled to 0° C. and quenched with ice/water, then extracted with ethyl acetate (30 mL×3). The extracts were combined, dried over anhydrous sodium sulfate, filtered and concentrated under vacuum to give a residue. The residue was purified by reversed-phase flash chromatography with the following conditions: column, C18; mobile phase, water in ACN, 10% to 50% gradient in 10 min; detector, UV 254 nm. to afford the desired product as a white solid. (ESI, m/z): 535 [M+H]⁺

(R)-10-bromo-9-chloro-11-fluoro-2-(((2R,7aS)-2-fluorotetrahydro-1H-pyrrolizin-7a(5H)-yl)methoxy)-4,5-dimethyl-4,5,6,7-tetrahydro-[1,5]oxazocino[4,3,2-de]quinazoline A solution of 7-bromo-6-chloro-8-fluoro-2-(((2R,7aS)-2-fluorotetrahydro-1H-pyrrolizin-7a(5H)-yl)methoxy)-5-((R)-3-(methylamino)butoxy)quinazolin-4-ol (160 mg, 0.346 mmol, 1 equiv) and POCl₃ (318 mg, 2.076 mmol, 6 equiv) in dioxane (16 mL) was stirred at 80° C. for 0.5 hours. Then the mixture was cooled to room temperature, treated with triethylamine (419 mg, 4.152 mmol, 12 equiv) and stirred at 80° C. for additional 1 hour. It was cooled to room temperature, quenched with water (20 mL), and extracted with DCM (15 mL×2). The extracts were combined, washed with brine, and dried over anhydrous Na₂SO₄. It was filtered and concentrated under vacuum to give a residue. The residue was purified by reverse phase column to afford the desired product as a white solid. (ESI, m/z): 517 [M+H]+

Tert-butyl (4-((R)-9-chloro-11-fluoro-2-(((2R,7aS)-2-fluorotetrahydro-1H-pyrrolizin-7a(5H)-yl)methoxy)-4,5-dimethyl-4,5,6,7-tetrahydro-[1,5]oxazocino[4,3,2-de]quinazolin-10-yl)-3-cyano-7-fluorobenzo[b]thiophen-2-yl) carbamate A solution of (R)-10-bromo-9-chloro-11-fluoro-2-(((2R,7aS)-2-fluorotetrahydro-1H-pyrrolizin-7a(5H)-yl) methoxy)-4,5-dimethyl-4,5,6,7-tetrahydro-[1,5]oxazocino [4,3,2-de]quinazoline (90 mg, 0.174 mmol, 1 equiv), tert-butyl (3-cyano-4-(5,5-dimethyl-1,3,2-dioxaborinan-2-yl)-7-fluorobenzo[b]thiophen-2-yl)carbamate (210 mg, 0.522 mmol, 3 equiv), bis(diphenylphosphinophenyl)ether palladium (II) dichloride (25 mg, 0.035 mmol, 0.2 equiv) and $Cs_2CO_3$ (169 mg, 0.522 mmol, 3 equiv) in toluene (4 mL) was stirred for 2 hours at 110° C. under argon atmosphere. The resulting mixture was cooled to room temperature, concentrated under vacuum to give a residue. The residue product was purified by reverse phase column to afford the desired product as a white solid. (ESI, m/z): [M+H]+

2-Amino-4-((R)-9-chloro-11-fluoro-2-(((2R,7aS)-2-fluorotetrahydro-1H-pyrrolizin-7a(5H)-yl)methoxy)-4,5-dimethyl-4,5,6,7-tetrahydro-[1,5]oxazocino[4,3,2-de]quinazolin-10-yl)-7-fluorobenzo[b]thiophene-3-carbonitrile Into a 25 mL flask were added tert-butyl (4-((R)-9-chloro-11-fluoro-2-(((2R,7aS)-2-fluorotetrahydro-1H-pyrrolizin-7a (5H)-yl)methoxy)-4,5-dimethyl-4,5,6,7-tetrahydro-[1,5] oxazocino[4,3,2-de]quinazolin-10-yl)-3-cyano-7-fluorobenzo[b]thiophen-2-yl)carbamate (50 mg, 0.060 mmol, 1 equiv), trifluoroacetic acid (0.4 mL) and methylene chloride (2.0 mL) at room temperature. It was stirred for 2 hours at room temperature. The resulting mixture was concentrated under reduced pressure to give a crude. The crude product (50 mg) was purified by prep-HPLC with the following conditions (XBridge BEH C18 OBD Prep Column 130 Å, 5 μm, 30 mm*150 mm; Mobile Phase A: Water (10 mmol/L $NH_4HCO_3$), Mobile Phase B: ACN; Flow rate: 60 mL/min; Gradient: 35% B to 70% B in 8 min; Wave Length: UV 254 nm/220 nm; RT1(min): 7.42) to afford the desired product as a white solid. (ESI, m/z): 629 [M+H]+

$^1$H NMR (400 MHZ, DMSO-$d_6$, ppm) δ 8.00 (br, 2H), 7.25-7.03 (m, 2H), 5.27-5.14 (m, 1H), 4.39-4.33 (m, 1H), 4.24-4.17 (m, 1H), 4.02-4.00 (m, 1H), 3.93-3.89 (m, 1H), 3.83-3.79 (m, 1H), 3.08-3.07 (m, 3H), 3.03-3.00 (m, 2H), 2.97-2.94 (m, 1H), 2.78-2.72 (m, 1H), 2.08-2.05 (m, 1H), 2.01-1.93 (m, 3H), 1.84-1.69 (m, 4H), 1.22-1.19 (m, 3H).

Example 1av: Synthesis of 2-amino-4-((5S)-9-chloro-11-fluoro-5-(1-fluorocyclopropyl)-2-(((2R,7aS)-2-fluorotetrahydro-1H-pyrrolizin-7a(5H)-yl) methoxy)-4-methyl-4,5,6,7-tetrahydro-[1,5] oxazocino[4,3,2-de]quinazolin-10-yl)-7-fluorobenzo [b]thiophene-3-carbonitrile (1221)

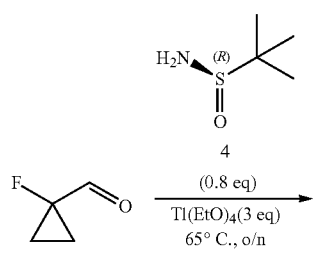

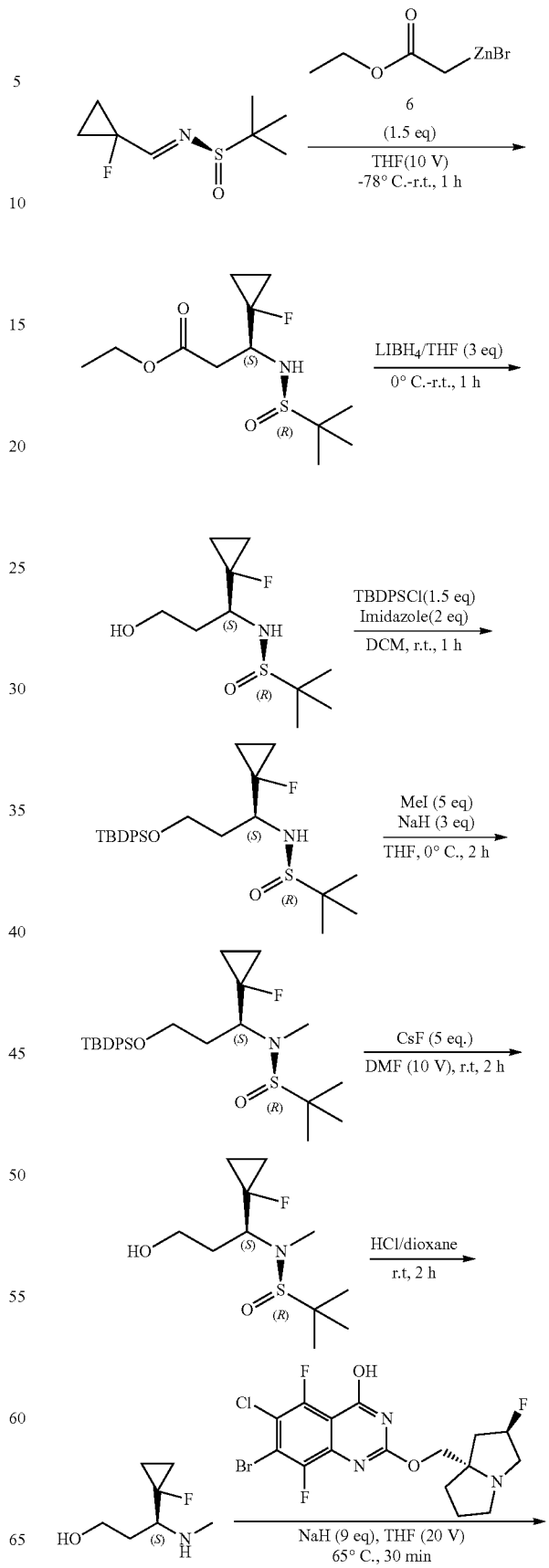

-continued

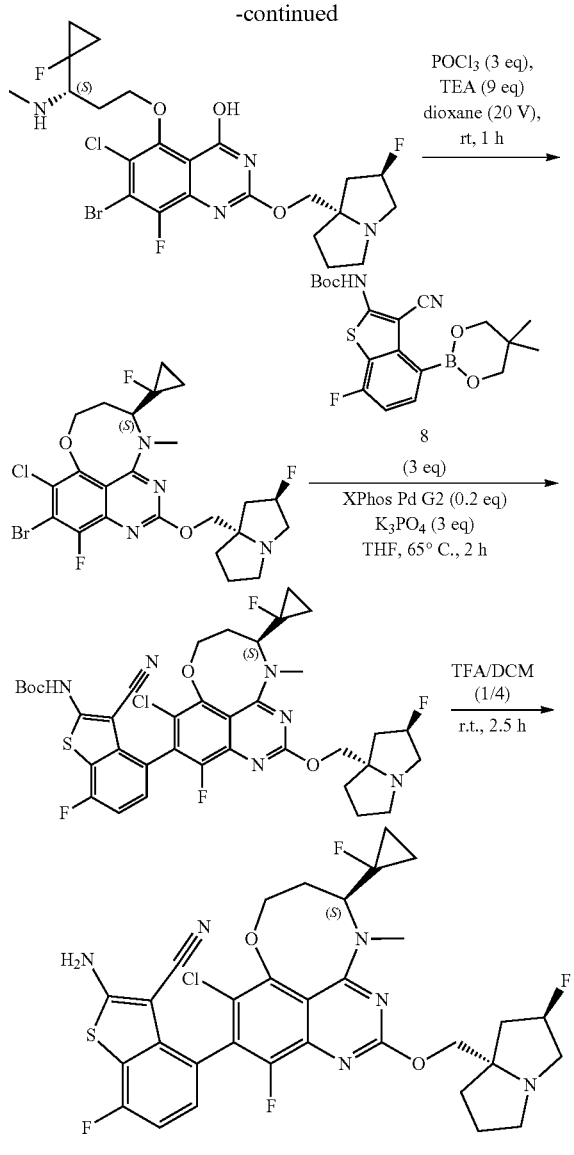

1221

(R)—N-[(1-fluorocyclopropyl)methylidene]-2-methylpropane-2-sulfinamide To a 100 mL 3-necked round-bottom flask were added 1-fluorocyclopropane-1-carbaldehyde, CuSO$_4$ (6.66 g, 41.722 mmol, 2.5 equiv) and DCE (15 mL) at room temperature. The resulting mixture was stirred overnight at room temperature. Ti(OEt)$_4$ (9.52 g, 41.722 mmol, 2.5 equiv) was added and the mixture was stirred overnight at 65° C. It was cooled to room temperature, extracted with ethyl acetate (3×20 mL). The extracts were combined, dried over anhydrous Na$_2$SO$_4$. After filtration, the filtrate was concentrated under reduced pressure to give a residue. The residue was purified by silica gel column chromatography, eluted with petroleum/ethyl acetate (4:1) to afford the desired product as a yellow oil. 192 [M+H]$^+$ Ethyl (3S)-3-(1-fluorocyclopropyl)-3-{[(R)-2-methylpropane-2-sulfinyl]amino}propanoate To a 100 mL 3-necked round-bottom flask were added (R)—N-[(1-fluorocyclopropyl)methylidene]-2-methylpropane-2-sulfinamide (500 mg, 2.614 mmol, 1 equiv) and THF (5 mL, 61.714 mmol) was added ethybromozincacetate (0.5 M in THF, 7.84 mL, 3.921 mmol, 1.5 equiv) dropwise at −78° C. The resulting mixture was warmed to room temperature slowly and stirred for overnight. It was quenched with water, extracted with ethyl acetate (3×20 mL). The extracts were combined, dried over anhydrous Na$_2$SO$_4$. After filtration, the filtrate was concentrated under reduced pressure to give a residue. The residue was purified by silica gel column chromatography, eluted with petroleum/ethyl acetate (1:1) to afford the desired product as a colorless oil. (ESI, m/z): 280 [M+H]$^+$ (R)—N-[(1S)-1-(1-fluorocyclopropyl)-3-hydroxypropyl]-2-methylpropane-2-sulfinamide To a stirred solution of ethyl (3S)-3-(1-fluorocyclopropyl)-3-{[(R)-2-methylpropane-2-sulfinyl]amino}propanoate (600 mg, 2.148 mmol, 1 equiv) in THF (6 mL) was added LiBH4 (187 mg, 8.592 mmol, 3 equiv) in portions at 0° C. under nitrogen atmosphere. The resulting mixture was stirred for 1 hour at room temperature, quenched with sat. NH$_4$Cl (aq.) at room temperature at 0° C., and extracted with CH$_2$Cl$_2$ (3×30 mL). It extracts were combined, washed with brine, and dried over anhydrous Na$_2$SO$_4$. After filtration, the filtrate was concentrated under reduced pressure to give the desired product as a colorless oil which was used directly in the next step without purification. (ESI, m/z): 238 [M+H]$^+$ (R)—N-[(1S)-3-[(tert-butyldiphenylsilyl)oxy]-1-(1-fluorocyclopropyl)propyl]-2-methylpropane-2-sulfinamide To stirred mixture of (R)—N-[(1S)-1-(1-fluorocyclopropyl)-3-hydroxypropyl]-2-methylpropane-2-sulfinamide (517 mg, 2.178 mmol, 1 equiv) and imidazole (296 mg, 4.356 mmol, 2 equiv) in THF (5 mL) was added TBDPSCl (898.13 mg, 3.267 mmol, 1.5 equiv) at 0° C. The resulting mixture was stirred for 1 hour at room temperature, extracted with EtOAc (3×20 mL). The extracts were combined, dried over anhydrous Na$_2$SO$_4$. After filtration, the filtrate was concentrated under reduced pressure to give a residue. The residue was purified by silica gel column chromatography, eluted with petroleum/ethyl acetate (3:1) to the desired product as a yellow oil. (ESI, m/z): 476[M+H]$^+$ (R)—N-[(1S)-3-[(tert-butyldiphenylsilyl)oxy]-1-(1-fluorocyclopropyl)propyl]-N,2-dimethylpropane-2-sulfinamide To a stirred solution of (R)—N-[(1S)-3-[(tert-butyldiphenylsilyl)oxy]-1-(1-fluorocyclopropyl)propyl]-2-methylpropane-2-sulfinamide (700 mg, 1.471 mmol, 1 equiv) in THF (8.75 mL) was added NaH (176.55 mg, 4.413 mmol, 3 equiv, 60%) at 0° C. under nitrogen atmosphere. The resulting mixture was stirred for 1 hour at room temperature followed by the addition of MeI (1044 mg, 7.335 mmol, 5 equiv) into the mixture. The resulting mixture was stirred for additional 1 hour at room temperature, extracted with ethyl acetate (3×10 mL). The extracts were combined, dried over anhydrous Na$_2$SO$_4$. After filtration, the filtrate was concentrated under reduced pressure to give a residue. The residue was purified by silica gel column chromatography, eluted with petroleum/ethyl acetate (3:1) to afford the desired product as a colorless oil. (ESI, m/z): 490 [M+H]$^+$ (R)—N-[(1S)-1-(1-fluorocyclopropyl)-3-hydroxypropyl]-N,2-dimethylpropane-2-sulfinamide To a stirred solution of (R)—N-[(1S)-3-[(tert-butyldiphenylsilyl)oxy]-1-(1-fluorocyclopropyl)propyl]-N,2-dimethylpropane-2-sulfinamide (500 mg, 1.021 mmol, 1 equiv) in DMF (5.0 mL) was added CsF (775 mg, 5.105 mmol, 5 equiv) at room temperature. The resulting mixture was stirred for 2 hours at room temperature. It was diluted with ethyl acetate (50 mL), washed with 7 mL of saturated brine, dried over anhydrous Na$_2$SO$_4$. After filtration, the filtrate was concentrated under reduced pressure to give a residue. The residue was purified by silica gel column chromatography, eluted with petroleum/ethyl acetate (1:1) to afford the desired product as a colorless solid. (ESI, m/z): 252[M+H]⁺

(3S)-3-(1-fluorocyclopropyl)-3-(methylamino)propan-1-ol A mixture of (R)—N-[(1S)-1-(1-fluorocyclopropyl)-3-hydroxypropyl]-N,2-dimethylpropane-2-sulfinamide (330 mg, 1.313 mmol, 1 equiv) in HCl in 1,4-dioxane (4M, 3 mL) was stirred for 2 hours at room temperature. The resulting mixture was concentrated under vacuum to give the desired product as a colorless oil. (ESI, m/z): 148 [M+H]⁺7-Bromo-6-chloro-8-fluoro-5-((S)-3-(1-fluorocyclopropyl)-3-(methylamino)propoxy)-2-(((2R,7aS)-2-fluorotetrahydro-1H-pyrrolizin-7a(5H)- yl)methoxy)quinazolin-4-ol To a stirred solution of (3S)-3-(1-fluorocyclopropyl)-3-(methylamino)propan-1-ol (450 mg, 3.057 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (968.71 mg, 2.140 mmol, 0.7 equiv) in THF (10 mL) was added NaH (660 mg, 27.513 mmol, 9 equiv) at 0° C. under nitrogen atmosphere. The resulting mixture was stirred for 30 minutes at 65° C. under nitrogen atmosphere. It was cooled to room temperature, quenched with water/ice, and extracted with $CH_2Cl_2$ (3×20 mL). The extracts were combined, washed with brine, and dried over anhydrous $Na_2SO_4$. After filtration, the filtrate was concentrated under reduced pressure to give the desired product as a white solid which was used directly in the next step without purification. (ESI, m/z): 579 [M+H]⁺

(S)-10-bromo-9-chloro-11-fluoro-5-(1-fluorocyclopropyl)-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazoline To a stirred solution of 7-bromo-6-chloro-8-fluoro-5-((S)-3-(1-fluorocyclopropyl)-3-(methylamino)propoxy)-2-(((2R,7aS)-2-fluorotetrahydro-1H-pyrrolizin-7a(5H)-yl)methoxy)quinazolin-4-ol (500 mg, 0.862 mmol, 1 equiv) and triethylamine (785 mg, 7.758 mmol, 9 equiv) in dioxane (10 mL, 118.040 mmol, 136.89 equiv) was added $POCl_3$ (396 mg, 2.586 mmol, 3 equiv) dropwise at 0° C. The resulting mixture was stirred for 1 hour at room temperature, quenched with water/Ice and extracted with $CH_2Cl_2$ (3×20 mL). The extracts were combined, washed with brine, and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 30% to 70% gradient in 20 min; detector, UV 254 nm to afford the desired product as an off-white solid. (ESI, m/z): 561[M+H]⁺

Tert-butyl (4-((5S)-9-chloro-11-fluoro-5-(1-fluorocyclopropyl)-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazolin-10-yl)-3-cyano-7-fluorobenzo[b]thiophen-2-yl)carbamate To a stirred solution of (S)-10-bromo-9-chloro-11-fluoro-5-(1-fluorocyclopropyl)-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazoline (80 mg, 0.142 mmol, 1 equiv) and tert-butyl N-[3-cyano-4-(5,5-dimethyl-1,3,2-dioxaborinan-2-yl)-7-fluoro-1-benzothiophen-2-yl]carbamate (172 mg, 0.426 mmol, 3 equiv) in THF (5 mL) were added XPhos Pd G2 (22 mg, 0.028 mmol, 0.2 equiv) and $K_3PO_4$ (90 mg, 0.426 mmol, 3 equiv) at room temperature. The resulting mixture was stirred for 2 hours at 65° C. under nitrogen atmosphere. It was cooled, concentrated under reduced pressure to give a residue. The residue was purified by reversed-phase flash chromatography with the following conditions: column, C18; mobile phase, MeCN in Water (10 mmol/L $NH_4HCO_3$), 35% to 100% gradient in 20 min; detector, UV 254 nm to give the desired product as a yellow solid. (ESI, m/z): 773[M+H]⁺

2-Amino-4-((5S)-9-chloro-11-fluoro-5-(1-fluorocyclopropyl)-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazolin-10-yl)-7-fluorobenzo[b]thiophene-3-carbonitrile To a stirred solution tert-butyl (4-((5S)-9-chloro-11-fluoro-5-(1-fluorocyclopropyl)-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazolin-10-yl)-3-cyano-7-fluorobenzo[b]thiophen-2-yl)carbamate (35 mg, 0.045 mmol, 1 equiv) in DCM (1 mL) was added TFA (0.25 mL) at room temperature. The resulting mixture was stirred for 2.5 hours at room temperature and concentrated under vacuum to give a residue. The residue was purified by Prep-HPLC with the following conditions Column: 30 mm*150 mm; Mobile Phase A: Water (10 mmol/L $NH_4HCO_3$), Mobile Phase B: ACN; Flow rate: 60 ml/min mL/min; Gradient: 58% B to 75% B in 10 min; Wave Length: 254 nm/220 nm nm; RT1(min): 8.98. to give desired product. as a white solid. (ESI, m/z): 673[M+H]⁺

¹H NMR (400 MHZ, DMSO-d₆, ppm) δ 8.08 (s, 2H), 7.21-7.18 (m, 1H), 7.15-7.11 (m, 1H), 5.36-5.23 (m, 1H), 4.48-4.45 (m, 1H), 4.37-4.33 (m, 1H), 4.11-4.03 (m, 3H), 3.88-3.80 (m, 1H), 3.10 (s, 3H), 2.95 (s, 1H), 2.85 (s, 1H), 2.43 (s, 1H), 2.29-2.23 (m, 1H), 2.17-1.95 (m, 4H), 1.95-1.75 (m, 3H), 1.13-1.05 (m, 2H), 0.98-0.94 (m, 1H), 0.85-0.78 (m, 1H).

Example 1aw: Synthesis of 2-amino-4-(9-chloro-11-fluoro-2-(((2R,7aS)-2-fluorotetrahydro-1H-pyrrolizin-7a(5H)-yl)methoxy)-6-hydroxy-4-(tetrahydrofuran-3-yl)-4,5,6,7-tetrahydro-[1,5]oxazocino[4,3,2-de]quinazolin-10-yl)-7-fluorobenzo[b]thiophene-3-carbonitrile (1225)

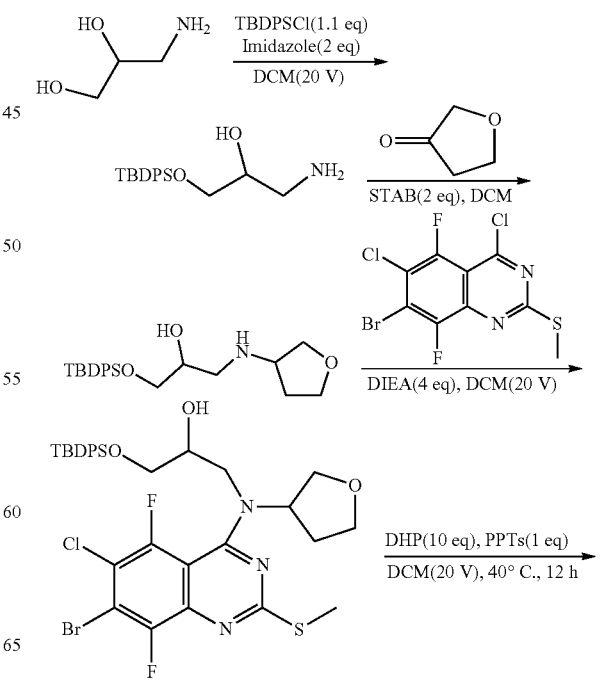

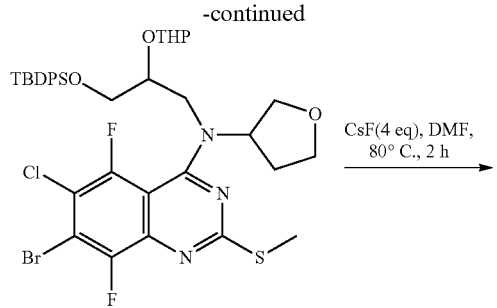
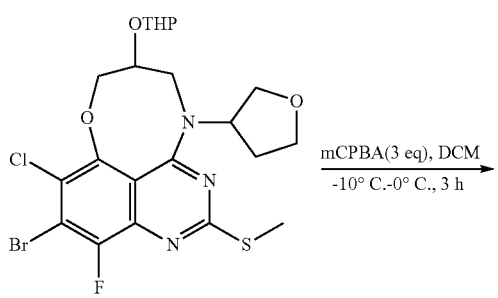
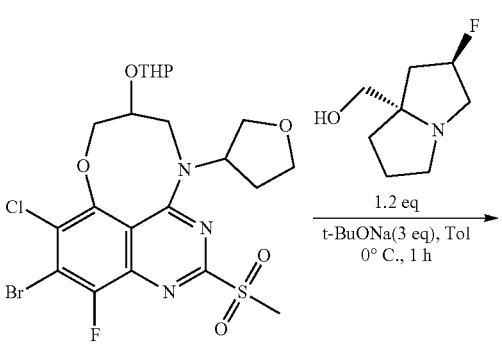
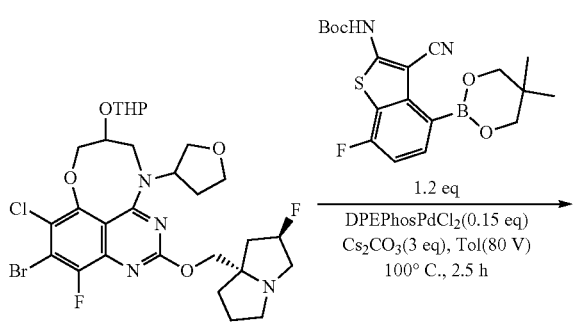
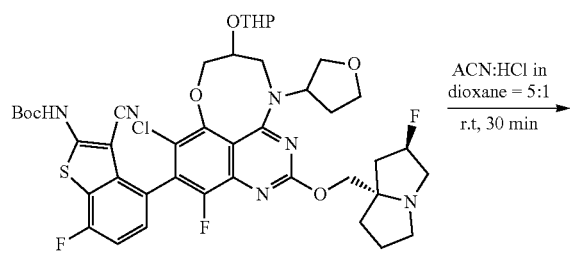

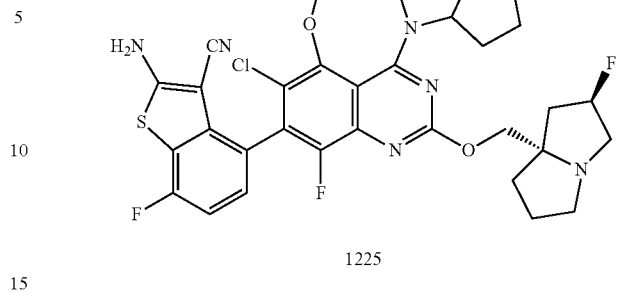

1-Amino-3-[(tert-butyldiphenylsilyl)oxy]propan-2-ol A solution of 3-aminopropane-1,2-diol (5.0 g, 54.8 mmol, 1.00 equiv), TBDPSCl (16.6 g, 60.3 mmol, 1.10 equiv) and imidazole (7.47 g, 109.7 mmol, 2.00 equiv) in DCM (100 mL) was stirred for 2 hours at room temperature under nitrogen atmosphere. The reaction was quenched with water (200 mL) and extracted with DCM (3×200 mL). The extracts were combined, washed with brine (1×260 mL), dried over anhydrous $Na_2SO_4$. After filtration, the filtrate was concentrated under reduced pressure to give a residue. The residue was purified by silica gel column chromatography, eluted with $CH_2Cl2(0.1\%$ TEA)/MeOH (13:1) to afford the desired product as a white oil. (ES, m/z): 330 $[M+H]^+$1-[(Tert-butyldiphenylsilyl)oxy]-3-(oxolan-3-ylamino)propan-2-ol A solution of 1-amino-3-[(tert-butyldiphenylsilyl)oxy]propan-2-ol (3.2 g, 9.71 mmol, 1.0 equiv) in DCM(65 mL) was treated with dihydrofuran-3-one (0.84 g, 9.71 mmol, 1.0 equiv) for 10 minutes at room temperature under nitrogen atmosphere followed by the addition of STAB (4.12 g, 19.42 mmol, 2.0 equiv) in portions at 0° C. It was stirred for 1 hour from 0° C. to room temperature, quenched with water (150 mL). The mixture was treated with $NaHCO_3$(eq.) to make pH~9, extracted with DCM (3×200 mL). The extracts were combined, washed with brine (1×80 mL), dried over anhydrous $Na_2SO_4$. After filtration, the filtrate was concentrated under reduced pressure to give a residue. The residue was purified by silica gel column chromatography, eluted with $CH_2Cl_2(0.1\%$ TEA)/MeOH (15:1) to afford the desired product as a white viscous oil. (ES, m/z): 400 $[M+H]^+$ 1-((7-Bromo-6-chloro-5,8-difluoro-2-(methylthio)quinazolin-4-yl)(tetrahydrofuran-3-yl)amino)-3-((tert-butyldiphenylsilyl)oxy)propan-2-ol A solution of 1-[(tert-butyldiphenylsilyl)oxy]-3-(oxolan-3-ylamino)propan-2-ol (400 mg, 1.00 mmol, 1.0 equiv), 7-bromo-4,6-dichloro-5,8-difluoro-2-(methylthio)quinazoline (360 mg, 1.00 mmol, 1.0 equiv) and DIEA (517 mg, 4.00 mmol, 4.0 equiv) in 2-methylpropan-2-ol (10 mL) was stirred for 3 hours at 90° C. under nitrogen atmosphere. It was cooled, diluted with water (80 mL), and extracted with ethyl acetate (3×80 mL). The extracts were combined, washed with brine (3×80 mL), dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a yellow oil. (ES, m/z): 722 $[M+H]^+$ 7-Bromo-N-(3-((tert-butyldiphenylsilyl)oxy)-2-((tetrahydro-2H-pyran-2-yl)oxy)propyl)-6-chloro-5,8-difluoro-2-(methylthio)-N-(tetrahydrofuran-3-yl)quinazolin-4-amine A solution of 1-((7-bromo-6-chloro-5,8-difluoro-2-(methylthio)quinazolin-4-yl)(tetrahydrofuran-3-yl)amino)-3-((tert-butyldiphenylsilyl)oxy)propan-2-ol (350 mg, 0.48 mmol, 1.0 equiv), DHP (407 mg, 4.84 mmol, 10.0 equiv) and PPTS (121 mg, 0.48 mmol, 1.0 equiv) in DCM (10 mL) was stirred for 12 hours at 40° C. under nitrogen atmosphere. It was cooled to room temperature, quenched by the addition of water (100 mL) at room temperature, and extracted with ethyl acetate (3×100 mL). The extracts were combined, washed with brine (1×100 mL), dried over anhydrous $Na_2SO_4$. After filtration, the filtrate was concentrated under reduced pressure to afford the desired product as a yellow solid. (ES, m/z):806 $[M+H]^+$ 10-Bromo-9-chloro-11-fluoro-2-(methylthio)-6-((tetra-hydro-2H-pyran-2-yl)oxy)-4-(tetrahydrofuran-3-yl)-4,5,6,7-tetrahydro-[1,5]oxazocino[4,3,2-de]quinazoline A solution of 7-bromo-N-(3-((tert-butyldiphenylsilyl)oxy)-2-((tetrahydro-2H-pyran-2-yl)oxy)propyl)-6-chloro-5,8-difluoro-2-(methylthio)-N-(tetrahydrofuran-3-yl)quinazolin-4-amine (300 mg, 0.37 mmol, 1.0 equiv) and CsF (225 mg, 1.49 mmol, 4.0 equiv) in DMF (6 mL) was stirred for 2 hours at 80° C. under nitrogen atmosphere. It was cooled to room temperature, quenched by the addition of water (100 mL) at room temperature, and extracted with ethyl acetate (3×100 mL). The extracs were combined, washed with brine (1×100 mL), and dried over anhydrous $Na_2SO_4$. After filtration, the filtrate was concentrated under reduced pressure to give a residue. The residue was purified by Prep-TLC (petroleum/ethyl acetate 3:1) to afford the desired product as a white solid. (ES, m/z):548 $[M+H]^+$ 10-Bromo-9-chloro-11-fluoro-2-(methylsulfonyl)-6-((tetrahydro-2H-pyran-2-yl)oxy)-4-(tetrahydrofuran-3-yl)-4,5,6,7-tetrahydro-[1,5]oxazocino[4,3,2-de]quinazoline To a solution of 10-bromo-9-chloro-11-fluoro-2-(methylthio)-6-((tetrahydro-2H-pyran-2-yl)oxy)-4-(tetrahydrofuran-3-yl)-4,5,6,7-tetrahydro-[1,5]oxazocino[4,3,2-de]quinazoline (110 mg, 0.2 mmol, 1.0 equiv) in DCM (2 mL) was added m-CPBA (103 mg, 0.6 mmol, 3.0 equiv) in portions at −10° C. The resulting mixture was stirred for 3 hours at −10° C. to 0° C. under nitrogen atmosphere. It was quenched by the addition of $NaHSO_3$ (2 mL) at 0° C. The residue was treated with saturated $NaHCO_3$(aq.) to pH~8 and extracted with ethyl acetate (3×50 mL). The extracts combined, washed with brine (1×50 mL), and dried over anhydrous $Na_2SO_4$. After filtration, the filtrate was concentrated under reduced pressure to afford the desired product as a yellow solid which was used in the next step without purification. (ES, m/z): 580 $[M+H]^+$ 10-Bromo-9-chloro-11-fluoro-2-(((2R,7aS)-2-fluorotetrahydro-1H-pyrrolizin-7a(5H)-yl)methoxy)-6-((tetrahydro-2H-pyran-2-yl)oxy)-4-(tetrahydrofuran-3-yl)-4,5,6,7-tetrahydro-[1,5]oxazocino[4,3,2-de]quinazoline To a stirred solution of 10-bromo-9-chloro-11-fluoro-2-(methylsulfonyl)-6-((tetrahydro-2H-pyran-2-yl)oxy)-4-(tetrahydrofuran-3-yl)-4,5,6,7-tetrahydro-[1,5]oxazocino[4,3,2-de]quinazoline (120 mg, 0.21 mmol, 1.0 equiv) and [(2R,7aS)-2-fluorohexahydropyrrolizin-7a-yl] methanol (39 mg, 0.25 mmol, 1.2 equiv) in toluene (2 mL) was added t-BuONa (59 mg, 0.62 mmol, 3.0 equiv) in portions at 0° C. under nitrogen atmosphere. After reaction completion, it was quenched by the addition of sat. $NH_4Cl$ (aq.) (2 mL) at 0° C. and the mixture was extracted with ethyl acetate (3×50 mL). The extracts were combined, washed with brine (1×50 mL), and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (0.1% $NH_3 \cdot H_2O$), 10% to 50% gradient in 30 min; detector, UV 254 nm to afford the desired product as a colorless oil. (ES, m/z):659 $[M+H]^+$ Tert-butyl (4-(9-chloro-11-fluoro-2-(((2R,7aS)-2-fluorotetrahydro-1H-pyrrolizin-7a(5H)-yl)methoxy)-6-((tetrahydro-2H-pyran-2-yl)oxy)-4-(tetrahydrofuran-3-yl)-4,5,6,7-tetrahydro-[1,5]oxazocino[4,3,2-de]quinazolin-10-yl)-3-cyano-7-fluorobenzo[b]thiophen-2-yl)carbamate To a 8 mL vial were added 10-bromo-9-chloro-11-fluoro-2-(((2R,7aS)-2-fluorotetrahydro-1H-pyrrolizin-7a(5H)-yl)methoxy)-6-((tetrahydro-2H-pyran-2-yl)oxy)-4-(tetrahydrofuran-3-yl)-4,5,6,7-tetrahydro-[1,5]oxazocino[4,3,2-de]quinazoline (50 mg, 0.07 mmol, 1.0 equiv), dichloropalladium; {2-[2-(diphenylphosphanyl)phenoxy]phenyl} diphenylphosphane (8 mg, 0.011 mmol, 0.15 equiv), tert-butyl N-[3-cyano-4-(5,5-dimethyl-1,3,2-dioxaborinan-2-yl)-7-fluoro-1-benzothiophen-2-yl]carbamate (36 mg, 0.09 mmol, 1.2 equiv), $Cs_2CO_3$ (74 mg, 0.23 mmol, 3.0 equiv) and toluene (1 mL) at room temperature under nitrogen. The reaction mixture was irradiated with microwave reactor for 2.5 hours at 100° C. It was cooled to room temperature, quenched by the addition of water (50 mL) at room temperature. The resulting mixture was extracted with ethyl acetate (3×50 mL). The extracts were combined, washed with brine (1×50 mL), and dried over anhydrous $Na_2SO_4$. After filtration, the filtrate was concentrated under reduced pressure to give a residue. The residue was purified by Prep-TLC ($CH_2Cl_2$/MeOH 10:1) to afford the desired product as a yellow solid. (ES, m/z): 871 $[M+H]^+$ 2-Amino-4-(9-chloro-11-fluoro-2-(((2R,7aS)-2-fluorotetrahydro-1H-pyrrolizin-7a(5H)-yl)methoxy)-6-hydroxy-4-(tetrahydrofuran-3-yl)-4,5,6,7-tetrahydro-[1,5]oxazocino[4,3,2-de]quinazolin-10-yl)-7-fluorobenzo[b]thiophene-3-carbonitrile A solution of tert-butyl (4-(9-chloro-11-fluoro-2-(((2R,7aS)-2-fluorotetrahydro-1H-pyrrolizin-7a(5H)-yl)methoxy)-6-((tetrahydro-2H-pyran-2-yl)oxy)-4-(tetrahydrofuran-3-yl)-4,5,6,7-tetrahydro-[1,5]oxazocino[4,3,2-de]quinazolin-10-yl)-3-cyano-7-fluorobenzo[b]thiophen-2-yl)carbamate (30 mg, 0.03 mmol, 1.0 equiv) and HCl in 1,4-dioxane (1 mL) and ACN (1 mL) was stirred for 30 minutes at room temperature under nitrogen atmosphere. The residue was basified to pH 9 with $NH_3 \cdot H_2O$, extracted with ethyl acetate (3×50 mL). The extracts were combined, washed with brine (1×50 mL), and dried over anhydrous $Na_2SO_4$. After filtration, the filtrate was concentrated under reduced pressure to give a crude. The crude product (20 mg) was purified by Prep-HPLC with the following conditions (Column: Kinetex EVO C18 Column, 30×150, 5 μm; Mobile Phase A: Water (10 mmol/L $NH_4HCO_3$), Mobile Phase B: ACN; Flow rate: 60 mL/min; Gradient: 20% B to 55% B in 10 min, 55% B; Wave Length: UV 220 nm; RT1(min): 8.73; Number Of Runs: 0) to afford the desired product as a white solid. (ES, m/z): 687 $[M+H]^+$ $^1$H NMR (400 MHZ, DMSO-$d_6$) δ 8.51 (s, 1H), 7.26(s, 1H), 7.09 (s, 1H), 6.07 (s, 2H), 5.46 (s, 2H), 5.21 (s, 1H), 5.16 (s, 1H), 4.68 (s, 1H), 4.16-3.97 (m, 1H), 3.90-3.82 (m, 1H), 3.80 (d, J=4.7 Hz, 2H), 3.65 (d, J=8.4 Hz, 2H), 3.09 (d, J=10.6 Hz, 2H), 3.02 (s, 1H), 2.84 (s, 1H), 2.03 (d, J=16.3 Hz, 5H), 1.79 (dd, J=12.2, 7.5 Hz, 3H).

Example 1ax: Synthesis of 2-amino-4-((5R)-9-chloro-11-fluoro-2-(((2R,7aS)-2-fluorotetrahydro-1H-pyrrolizin-7a(5H)-yl)methoxy)-4,5,6-trimethyl-4,5,6,7-tetrahydro-[1,5]oxazocino[4,3,2-de]quinazolin-10-yl)-7-fluorobenzo[b]thiophene-3-carbonitrile (1206)

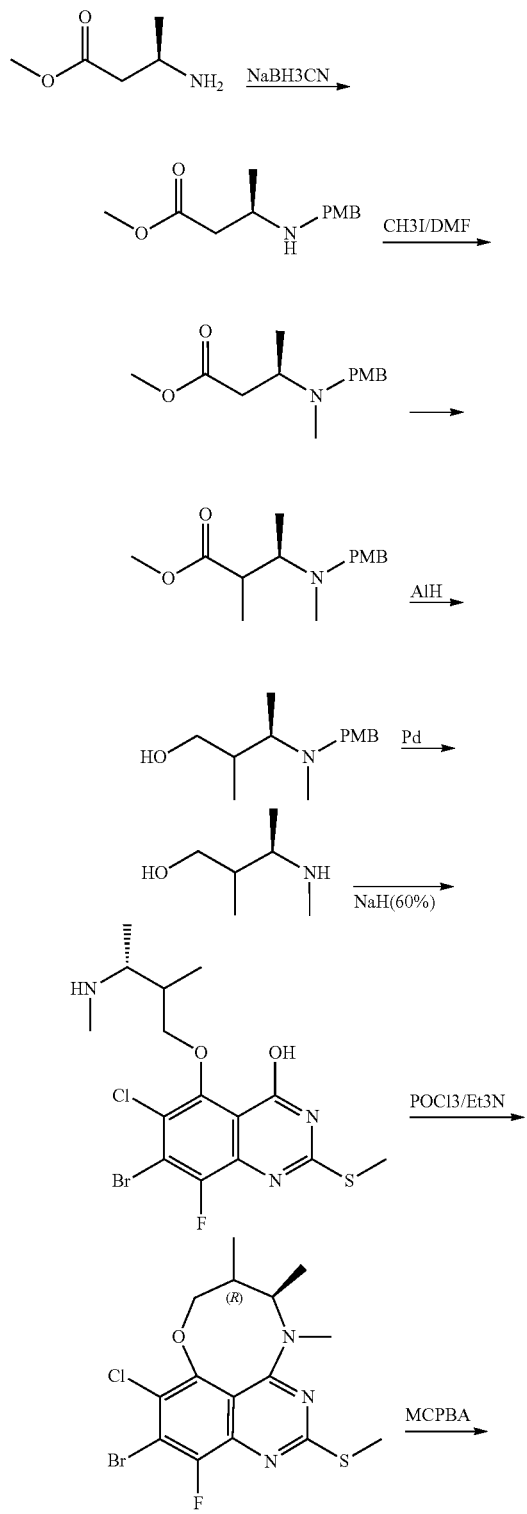

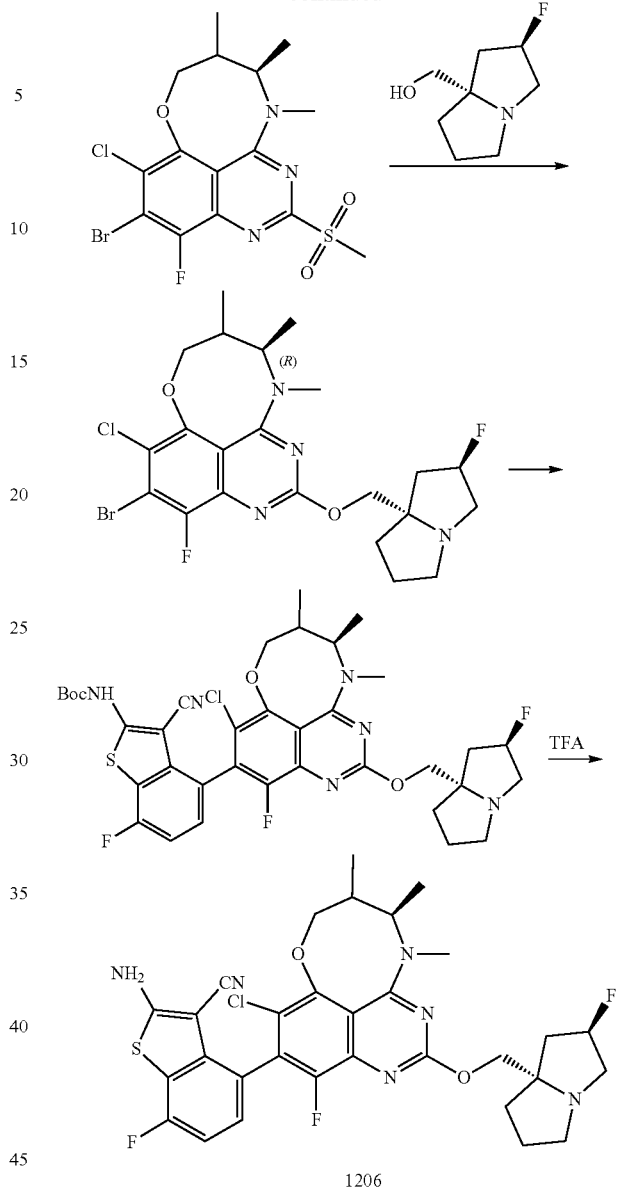

1206

Methyl (R)-3-((4-methoxybenzyl)amino)butanoate A solution of methyl (R)-3-aminobutanoate (3.0 g, 25.64 mmol), 4-methoxybenzaldehyde (3.84 g, 28.21 mmol) and AcOH (311 mg, 5.18 mmol) in MeOH (45 mL) stirred for 0.5 hours at room temperature, NaBH₃CN (4.85g, 76.92 mmol) was added at 0° C. The resulting mixture was stirred for 16 hours at room temperature. It was filtered and solvent was removed under reduced pressure to give a crude. The crude was purified by flash chromatography on silica gel (petroleum: ethyl acetate=1:1) to give the desired product as an oil. ESI-MS m/z: 238[M+H]⁺.

Methyl (R)-3-((4-methoxybenzyl)(methyl)amino)butanoate A solution of methyl (R)-3-((4-methoxybenzyl)amino) butanoate (2.6 g, 10.97 mmol), Cs₂CO₃ (5.4 g, 16.46 mmol) and CH₃I (1.9 g, 13.11 mmol) in DMF (35 mL) was stirred for 5 hours at room temperature. The reaction mixture was extracted with ethyl acetate (20 mL×2), washed with NH₄Cl (aq) and brine, dried over Na₂SO₄. It was filtered and solvent was removed under reduced pressure to give a crude. The crude was purified by flash chromatography on silica gel (petroleum: ethyl acetate=3:1) to give the desired product as an oil. ESI-MS m/z: 252[M+H]$^+$.

Methyl (3R)-3-((4-methoxybenzyl)(methyl)amino)-2-methylbutanoate A solution of methyl (R)-3-((4-methoxybenzyl)(methyl)amino)butanoate (2.45 g, 9.8 mmol)in dry THF (45 mL) was cooled to −78° C. under argon. LDA (10.0 ml, 1.2 M in THF) was added dropwise and the resulting mixture was stirred for 0.5 hours at −78° C. under argon. Then CH$_3$I (1.7 g, 11.71 mmol) was added. The resulting mixture was stirred for 16 hours at −78° C. to room temperature. It was quenched with saturated NH$_4$Cl (30 ml) and extracted with ethyl acetate (30 mL×2). Organic extracts were combined, washed with brine, and dried over Na$_2$SO$_4$. It was filtered and solvent was removed under reduced pressure to give a crude. The crude was purified by flash chromatography on silica gel (petroleum: ethylacetate=3:1) to give the desired product as an oil. ESI-MS m/z: 266[M+H]$^+$.

(3R)-3-((4-methoxybenzyl)(methyl)amino)-2-methylbutan-1-ol A solution of methyl (3R)-3-((4-methoxybenzyl)(methyl)amino)-2-methylbutanoate (450 mg, 1.70 mmol) in dry THF (45 mL) was cooled to −78° C. LiAlH4 (97 mg, 2.55 mmol) was added at −78° C. The resulting mixture was stirred for 3 hours at −78° C. to 0° C. Ethyl acetate (10 ml) was added dropwise at 0° C. followed by the addition of water (0.3 ml) was added dropwise at 0° C. The organics were separated, washed with brine, and dried over Na$_2$SO$_4$. It was filtered and solvent was removed under reduced pressure to give the desired product as an oil. ESI-MS m/z: 238 [M+H]$^+$.

(3R)-2-methyl-3-(methylamino)butan-1-ol A solution of (3R)-3-((4-methoxybenzyl)(methyl)amino)-2-methylbutan-1-ol (362 mg, 1.53 mmol) in MeOH (15 mL) was added Pd/C(10%, 73 mg, 0.31 mmol) and Pd(OH)$_2$ (10%, 73 mg, 0.31 mmol). The resulting mixture was stirred for 5 hours at reflux under hydrogen. It was cooled to room temperature and DCM (7 mL) was added. It was filtered and solvent was removed under reduced pressure to give the desired product as an oil. ESI-MS m/z: 118[M+H]$^+$.

7-Bromo-6-chloro-8-fluoro-5-((3R)-2-methyl-3-(methylamino)butoxy)-2-(methylthio)quinazolin-4-ol A solution of 7-bromo-6-chloro-5,8-difluoro-2-(methylthio)quinazolin-4-ol (165 mg, 0.49 mmol) and (3R)-2-methyl-3-(methylamino)butan-1-ol (170 mg, 1.46 mmol) in dry THF (15 mL) was added NaH (60%, 98 mg, 2.45 mmol) at 0° C. The resulting mixture was stirred for 3 hours at 55° C. It was cooled to room temperature, quenched with water and extracted with ethyl acetate (20 mL×2). The extracts were combined, washed with NH$_4$Cl (aq) and brine, and dried over Na$_2$SO$_4$. It was filtered and solvent was removed under reduced pressure to give a crude. The crude was purified by flash chromatography on silica gel (DCM: MeOH=15: 1) to give the desired product as a solid. ESI-MS m/z: 438[M+H]$^+$.

(5R)-10-bromo-9-chloro-11-fluoro-4,5,6-trimethyl-2-(methylthio)-4,5,6,7-tetrahydro-[1,5]oxazocino[4,3,2-de]quinazoline A solution of 7-bromo-6-chloro-8-fluoro-5-((3R)-2-methyl-3-(methylamino)butoxy)-2-(methylthio)quinazolin-4-ol (155 mg, 0.36 mmol) in dry dioxane (15 ml) was added POCl$_3$ (164 mg, 1.07 mmol) dropwise followed by the addition of triethylamine (361 mg, 3.6 mmol) was. The resulting mixture was stirred for 5 hours at room temperature and extracted with ethyl acetate (20 mL×2). The extracts were combined, washed with NaHCO$_3$(aq) and brine, dried over Na$_2$SO$_4$. It was filtered and solvent was removed under reduced pressure to give a crude. The crude was purified by flash chromatography on silica gel (petroleum: ethyl acetate=3:1) to give the desired product as a solid. ESI-MS m/z: 420[M+H]$^+$;

(5R)-10-bromo-9-chloro-11-fluoro-4,5,6-trimethyl-2-(methylsulfonyl)-4,5,6,7-tetrahydro-[1,5]oxazocino[4,3,2-de]quinazoline To a solution of (5R)-10-bromo- 9-chloro-11-fluoro-4,5,6-trimethyl-2-(methylthio)-4,5,6,7-tetrahydro-[1,5]oxazocino[4,3,2-de]quinazoline (125 mg, 0.3 mmol) in dry DCM (15 mL), was added m-CPBA (129 mg, 0.75 mmol) at 0° C. The resulting mixture was stirred for 1.5 hours at room temperature. The reaction mixture was quenched with Na$_2$SO$_3$ (aq), extracted with DCM (15 mL×2). The extracts were combined, washed with water and brine, dried over Na$_2$SO$_4$, It was filtered and solvent was removed under reduced pressure to give a crude. The crude was purified by flash chromatography on silica gel (DCM: MeOH=30: 1) to give the desired product as a solid. ESI-MS m/z: 452[M+H]$^+$;

(5R)-10-bromo-9-chloro-11-fluoro-2-(((2R,7aS)-2-fluorotetrahydro-1H-pyrrolizin-7a(5H)-yl)methoxy)-4,5,6-trimethyl-4,5,6,7-tetrahydro-[1,5]oxazocino[4,3,2-de]quinazoline To a solution of ((2R,7aS)-2-fluorotetrahydro-1H-pyrrolizin-7a(5H)-yl)methanol (177 mg, 1.11 mmol)in THF (15 ml) at 0° C. was added NaH (60%, 45 mg, 1.11 mmol) and the resulting mixture was stirred for 30 minutes at 0° C. under argon. Then (5R)-10-bromo-9-chloro-11-fluoro-4,5,6-trimethyl-2-(methylsulfonyl)-4,5,6,7-tetrahydro-[1,5]oxazocino[4,3,2-de]quinazoline (100 mg,0.22 mmol) was added slowly at 0° C., and the resulting mixture was stirred for 1 hour at room temperature. It was filtered and solvent was removed under reduced pressure to give a crude. The crude was purified by flash chromatography on silica gel (DCM: MeOH=20:1) to give the desired product as a solid. ESI-MS m/z: 531 [M+H]$^+$;

Tert-butyl (4-((5R)-9-chloro-11-fluoro-2-(((2R,7aS)-2-fluorotetrahydro-1H-pyrrolizin-7a(5H)-yl)methoxy)-4,5,6-trimethyl-4,5,6,7-tetrahydro-[1,5]oxazocino[4,3,2-de]quinazolin-10-yl)-3-cyano-7-fluorobenzo[b]thiophen-2-yl) carbamate To a solution of (5R)-10-bromo-9-chloro-11-fluoro-2-(((2R,7aS)-2-fluorotetrahydro-1H-pyrrolizin-7a (5H)-yl)methoxy)-4,5,6-trimethyl-4,5,6,7-tetrahydro-[1,5] oxazocino[4,3,2-de]quinazoline (45 mg, 0.09 mmol) in dioxane (15 ml) was added tert-butyl (3-cyano-4-(5,5-dimethyl-1,3,2-dioxaborinan-2-yl)-7-fluorobenzo[b]thiophen-2-yl)carbamate (103 mg, 0.26 mmol), K$_2$CO$_3$(71 mg, 0.51 mmol) and Pd(dppf)C12.DCM(8 mg, 0.01 mmol) under argon. The resulting mixture was heated at 110° C. under argon and stirred for 16 hours. It was cooled to room temperature and ethyl acetate (15 mL) was added. The organics were separated, washed with brine, and dried over Na$_2$SO$_4$. It was filtered and solvent was removed under reduced pressure to give a crude. The crude was purified by flash chromatography on silica gel (dichloromethane: methyl alcohol=20:1) to afford the desired product as a solid. ESI-MS m/z: 743 [M+H]$^+$;

2-Amino-4-((5R)-9-chloro-11-fluoro-2-(((2R,7aS)-2-fluorotetrahydro-1H-pyrrolizin-7a(5H)-yl)methoxy)-4,5,6-trimethyl-4,5,6,7-tetrahydro-[1,5]oxazocino[4,3,2-de]quinazolin-10-yl)-7-fluorobenzo[b]thiophene-3-carbonitrile A solution of tert-butyl (4-((5R)-9-chloro-11-fluoro-2-(((2R, 7aS)-2-fluorotetrahydro-1H-pyrrolizin-7a(5H)-yl) methoxy)-4,5,6-trimethyl-4,5,6,7-tetrahydro-[1,5]oxazocino[4,3,2-de]quinazolin-10-yl)-3-cyano-7-fluorobenzo[b] thiophen-2-yl)carbamate (20 mg, 0.03 mmol) in DCM (10 mL) was added TFA (4 ml) slowly at 0° C. The resulting mixture was stirred for 1 hour at room temperature. The reaction mixture was concentrated to remove TFA. the resulted residue was partitioned with 5 mL saturated NaHCO$_3$ and dichloromethane (5 mL) and the aqueous layer was extracted with dichloromethane (15 mL×2). The organics were separated, washed with brine, dried over Na$_2$SO$_4$. It was filtered and solvent was removed under reduced pressure to give a crude. The crude was purified by prep-TLC (DCM: MeOH=15: 1) to afford the desired product as a solid. ESI-MS m/z: 643 [M+H]$^+$;

Example 1ay: Synthesis of 2-amino-4-(4-((1-aminocyclobutyl)methyl)-9-chloro-11-fluoro-2-(((2R,7aS)-2-fluorotetrahydro-1H-pyrrolizin-7a(5H)-yl)methoxy)-4,5,6,7-tetrahydro-[1,5]oxazocino [4,3,2-de]quinazolin-10-yl)-7-fluorobenzo[b]thiophene-3-carbonitrile (1213)

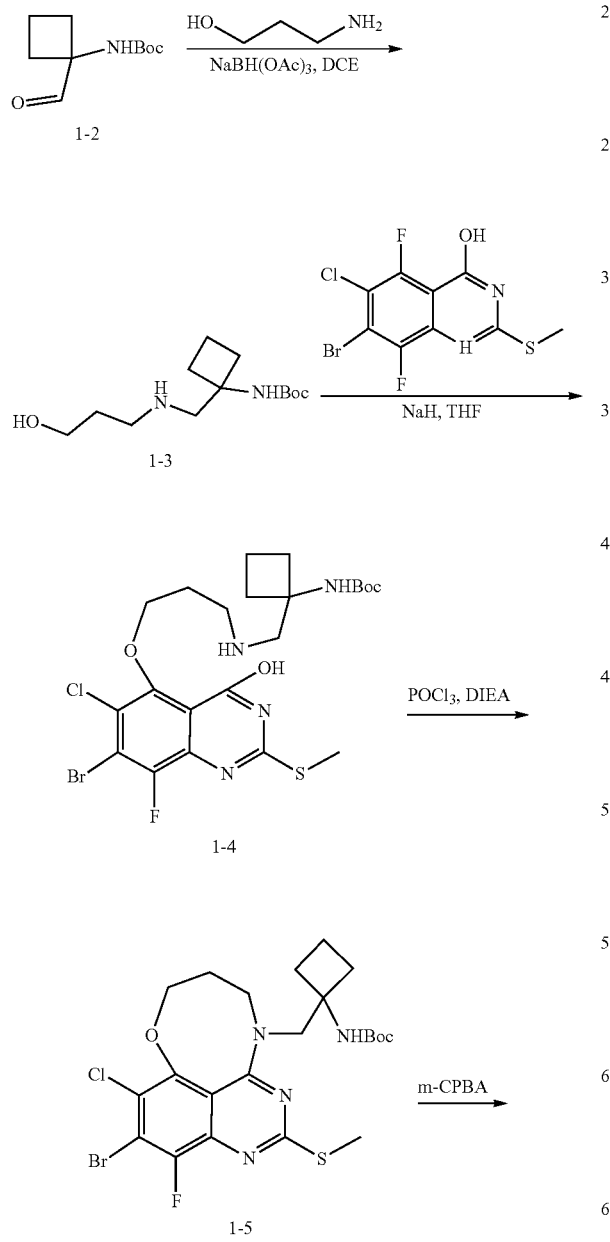

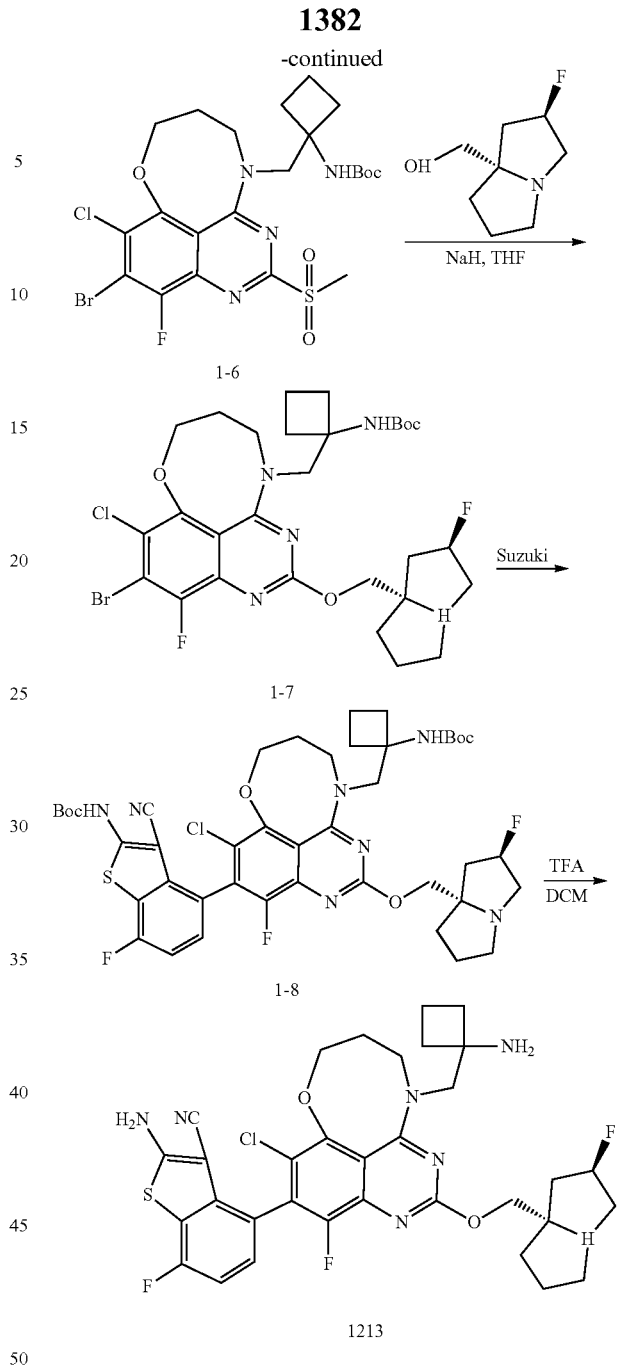

Tert-butyl (1-(((3-hydroxypropyl)amino)methyl)cyclobutyl)carbamate To a solution of 3-aminopropan-1-ol (283 mg, 3.77 mmol) in DCE (5 mL) at 0° C. was added NaBH(OAc)$_3$ (1.6 g, 7.54 mmol), then tert-butyl (1-formylcyclobutyl)carbamate (500 mg, 2.51 mmol) in DCE (15 mL) was added dropwise. The resulting mixture was stirred at 25° C. for 2 hours. It was concentrated, and the residue was purified by silica gel column chromatography to afford the desired product which was used directly in the next step without further purification. ESI-MS m/z: 259.0 [M+H]$^+$.

Tert-butyl (1-(((3-((7-bromo-6-chloro-8-fluoro-4-hydroxy-2-(methylthio)quinazolin-5-yl)oxy)propyl)amino)methyl)cyclobutyl)carbamate To a solution of compound tert-butyl (1-(((3-hydroxypropyl)amino)methyl)cyclobutyl) carbamate (400 mg, 1.55 mmol) and 7-bromo-6-chloro-5,8-difluoro-2-(methylthio)quinazolin-4-ol (633 mg, 1.86 mmol) in THF (10 mL) at 0° C. was added NaH (310 mg, 7.75 mmol), and the resulting mixture was stirred at 25° C. for 12 hours. Then NH$_4$Cl (aq., 20 mL) was added to quench the reaction. The organic layer was separated, and the aqueous layer was extracted with ethyl acetate (3×20 mL). The combined organic layers were washed with brine, dried over Na$_2$SO$_4$, filtered, and concentrated in vacuo to give a residue. The residue was purified by silica gel column chromatography to obtain the desired product. ESI-MS m/z: 580.9 [M+H]$^+$.

Tert-butyl (1-((10-bromo-9-chloro-11-fluoro-2-(methylthio)-6,7-dihydro-[1,5]oxazocino[4,3,2-de]quinazolin-4 (5H)-yl)methyl)cyclobutyl)carbamate To a solution of tert-butyl (1-(((3-((7-bromo-6-chloro-8-fluoro-4-hydroxy-2-(methylthio)quinazolin-5-yl)oxy)propyl)amino)methyl) cyclobutyl)carbamate (210 mg, 0.36 mmol) in dioxane (2 mL) was added DIEA (2 mL) and POCl$_3$ (0.5 mL), and the resulting mixture was stirred at 25° C. for 2 hours. The mixture was quenched by the addition of 5 mL saturated aqueous NaHCO$_3$ dropwise, extracted with DCM (3×30 mL). The combined organic layer was washed with brine and dried over Na$_2$SO$_4$. It was filtered and solvent was removed to give a residue. The residue was purified by silica gel column chromatography to obtain the desired product. ESI-MS m/z: 563.0 [M+H]$^+$.

Tert-butyl (1-((10-bromo-9-chloro-11-fluoro-2-(methylsulfonyl)-6,7-dihydro-[1,5]oxazocino[4,3,2-de]quinazolin-4 (5H)-yl)methyl)cyclobutyl)carbamate To a solution of tert-butyl (1-((10-bromo-9-chloro-11-fluoro-2-(methylthio)-6,7-dihydro-[1,5]oxazocino[4,3,2-de]quinazolin-4(5H)-yl) methyl)cyclobutyl)carbamate (270 mg, 0.48 mmol) in DCM (3 mL) at 0° C. was added m-CPBA (196 mg, 0.96 mmol), then the mixture was stirred at 25° C. for 2 hours. The mixture was quenched by the addition of 5 ml saturated NaHSO$_3$ and extracted with DCM (3×50 mL). The organics was combined, washed with brine, and dried over Na$_2$SO$_4$. It was filtered and solvent was removed under reduced pressure to give a residue. The residue was purified by silica gel column chromatography to obtain the desired product. ESI-MS m/z: 594.9 [M+H]$^+$.

Tert-butyl (1-((10-bromo-9-chloro-11-fluoro-2-(((2R, 7aS)-2-fluorotetrahydro-1H-pyrrolizin-7a(5H)-yl) methoxy)-6,7-dihydro-[1,5]oxazocino[4,3,2-de]quinazolin-4(5H)-yl)methyl)cyclobutyl)carbamate To a solution of ((2R,7aS)-2-fluorotetrahydro-1H-pyrrolizin-7a(5H)-yl) methanol (67 mg, 0.422 mmol) in THF (1 mL) at 0° C. under nitrogen was added NaH (20 mg, 0.51 mmol), the mixture was stirred at 25° C. for 30 minutes. tert-butyl (1-((10-bromo-9-chloro-11-fluoro-2-(methylsulfonyl)-6,7-dihydro-[1,5]oxazocino[4,3,2-de]quinazolin-4(5H)-yl)methyl)cyclobutyl)carbamate (100 mg, 0.17 mmol) in THF (1 mL) was added and the resulting mixture was stirred for 5 minutes at room temperature. Then NH$_4$Cl (aq., 20 mL) was added to quench the reaction. The organic layer was collected, and the aqueous layer was extracted with ethyl acetate (3×20 mL). The combined organic layers were washed with brine, dried over Na$_2$SO$_4$, filtered, and concentrated in vacuo to obtain the desired product which was used directly in the next step without further purification. ESI-MS m/z: 673.7 [M+H]$^+$.

Tert-butyl (4-(4-((1-((tert-butoxycarbonyl)amino)cyclobutyl)methyl)-9-chloro-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-3-cyano-7-fluorobenzo[b]thiophen-2-yl)carbamate To a solution of tert-butyl (1-((10-bromo-9-chloro-11-fluoro-2-(((2R,7aS)-2-fluorotetrahydro-1H-pyrrolizin-7a(5H)-yl)methoxy)-6,7-dihydro-[1,5]oxazocino[4,3,2-de]quinazolin-4(5H)-yl) methyl)cyclobutyl)carbamate (60 mg, 0.089 mmol) in dry toluene (2 mL) was added tert-butyl (3-cyano-4-(5,5-dimethyl-1,3,2-dioxaborinan-2-yl)-7-fluorobenzo[b]thiophen-2-yl)carbamate (72 mg, 0.18 mmol) and CsCO3 (87 mg, 0.29 mmol) and DPEPhosPdC12 (16.0 mg, 0.022 mmol) under nitrogen. The mixture was stirred at 110° C. for 3 hours under nitrogen and cooled to room temperature. The resulting mixture was diluted with DCM (10 mL) and filtered. The filtrate was collected and concentrated in vacuo. The residue was purified by silica gel column chromatography to obtain the desired product. ESI-MS m/z: 884.2 [M+H]$^+$.

2-Amino-4-(4-((1-aminocyclobutyl)methyl)-9-chloro-11-fluoro-2-(((2R,7aS)-2-fluorotetrahydro-1H-pyrrolizin-7a (5H)-yl)methoxy)-4,5,6,7-tetrahydro-[1,5]oxazocino [4,3,2-de]quinazolin-10-yl)-7-fluorobenzo[b]thiophene-3-carbonitrile To a solution of tert-butyl (4-(4-((1-((tert-butoxycarbonyl)amino)cyclobutyl)methyl)-9-chloro-11-fluoro-2-(((2R,7aS)-2-fluorotetrahydro-1H-pyrrolizin-7a (5H)-yl)methoxy)-4,5,6,7-tetrahydro-[1,5]oxazocino[4,3,2-de]quinazolin-10-yl)-3-cyano-7-fluorobenzo[b]thiophen-2-yl)carbamate (100 mg, 0.11 mmol) in DCM (3 mL) was added TFA (1 mL), the mixture was stirred at 25° C. for 1 hour. It was concentrated in vacuo and purified by prep-HPLC to obtain the desired product. ESI-MS m/z: 684.2 [M+H]$^+$.

Example 1az: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazolin-9-yl)-7-fluorobenzo[b]thiophene-3-carbonitrile (763, 860)

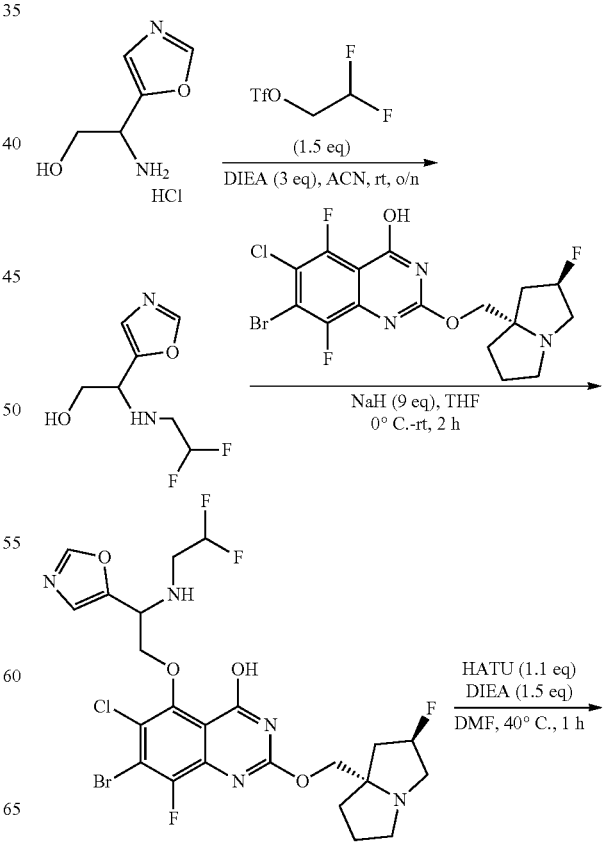

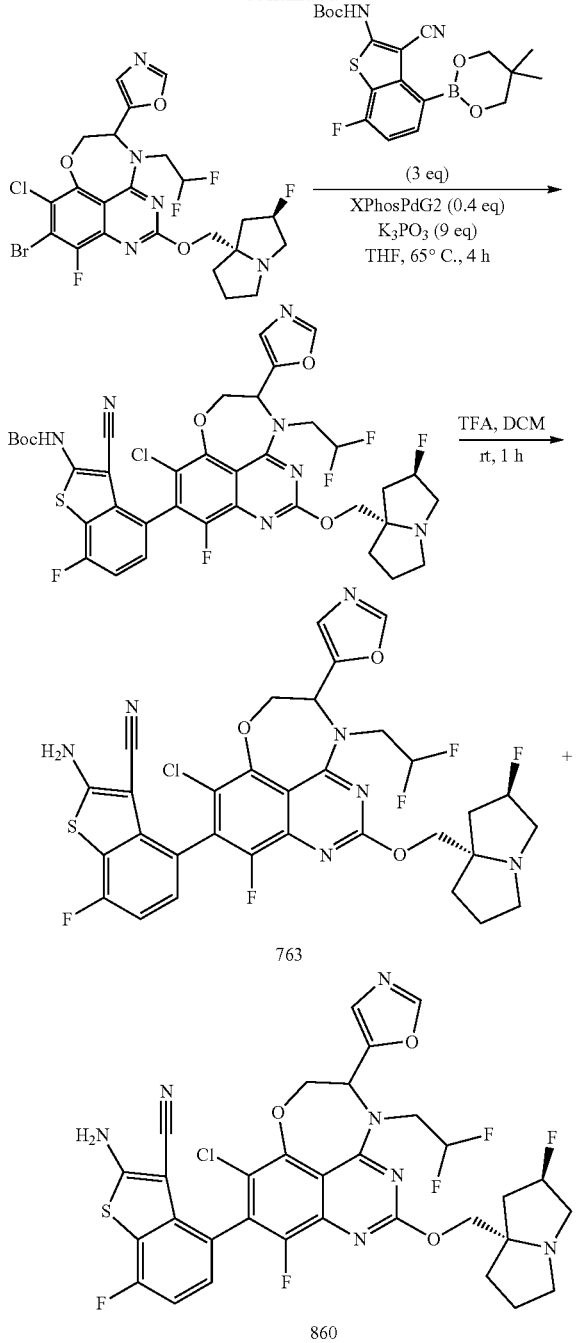

763

860

2-[(2,2-Difluoroethyl)amino]-2-(1,3-oxazol-5-yl)ethanol To a 250 mL round-bottom flask was added 2-amino-2-(1,3-oxazol-5-yl)ethanol hydrochloride (1 g, 6.076 mmol, 1 equiv) in ACN (60 mL) at room temperature followed by addition of DIEA (3.17 mL, 18.228 mmol, 3 equiv) and 2,2-difluoroethyl trifluoromethanesulfonate (1.95 g, 9.114 mmol, 1.5 equiv) at room temperature. The reaction mixture was stirred overnight, s was concentrated under reduced pressure to give a residue. The residue was purified by flash chromatography with the following conditions (column: silica gel; mobile phase: MeOH in DCM, 0% to 15% gradient in 20 min; detector, UV 254 nm) to afford the desired product as a yellow oil. (ESI, m/z): 193.00 [M+H]$^+$ 7-Bromo-6-chloro-5-(2-((2,2-difluoroethyl)amino)-2-(oxazol-5-yl)ethoxy)-8-fluoro-2-(((2R,7aS)-2-fluorotetrahydro-1H-pyrrolizin-7a(5H)-yl)methoxy)quinazolin-4-ol To a 40 mL vial were added 2-[(2,2-difluoroethyl)amino]-2-(1,3-oxazol-5-yl)ethanol (254.72 mg, 1.326 mmol, 2 equiv) and 7-bromo-6-chloro-5,8-difluoro-2-(((2R,7aS)-2-fluorotetrahydro-1H-pyrrolizin-7a(5H)-yl)methoxy)quinazolin-4-ol (300 mg, 0.663 mmol, 1 equiv) in THF (4 mL) at room temperature followed by the addition of NaH (238 mg, 5.967 mmol, 9 equiv, 60%) in portions at 0° C. The resulting mixture was stirred for 2 hours at room temperature and quenched with sat. NH$_4$Cl (aq.) at 0° C. The resulting mixture was extracted with ethyl acetate (3×50 mL) and water (20 mL). The combined organic layers were washed with brine (1×10 mL), dried over anhydrous Na$_2$SO$_4$. After filtration, the filtrate was concentrated under reduced pressure to afford the desired product as a yellow solid which was used in the next step directly without further purification. (ESI, m/z): 624.30 [M+H]$^+$ 9-Bromo-8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazoline To a 50 mL round-bottom flask were added 2-([[(2R,7aS)-2-fluoro-hexahydropyrrolizin-7a-yl]methoxy)-7-bromo-6-chloro-5-[(2R)-2-[(2,2-difluoroethyl)amino]-2-(1,3-oxazol-5-yl)ethoxy]-8-fluoroquinazolin-4-ol (510 mg, 0.816 mmol, 1 equiv) in DMF (8 mL) at room temperature followed by the addition of DIEA (213 µL, 1.224 mmol, 1.5 equiv) and HATU (341 mg, 0.898 mmol, 1.1 equiv) in portions at room temperature. The reaction mixture was stirred for 1 hour at 40° C. The resulting mixture was filtered, and the filter cake was washed with ethyl acetate (3×10 mL). The filtrate was concentrated under vacuum to give a residue. The residue was purified by reversed-phase flash chromatography with the following conditions (column: C18; mobile phase: MeCN in Water (10 mmol/L NH$_4$HCO$_3$), 0% to 100% gradient in 20 min, 80% MeCN; detector: UV 254 nm) to afford the desired product as a yellow solid. (ESI, m/z): 607.95 [M+H]$^+$ Tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazolin-9-yl)-3-cyano-7-fluorobenzo[b]thiophen-2-yl)carbamate To a 40 mL vial were added 9-bromo-8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazoline (290 mg, 0.478 mmol, 1 equiv), tert-butyl N-[3-cyano-4-(5,5-dimethyl-1,3,2-dioxaborinan-2-yl)-7-fluoro-1-benzothiophen-2-yl]carbamate (579 mg, 1.434 mmol, 3 equiv), K$_3$PO$_4$ (913 mg, 4.302 mmol, 9 equiv) and dicyclohexyl[2',4',6'-tris(propan-2-yl)-[1,1'-biphenyl]-2-yl]phosphane; (2'-amino-[1,1'-biphenyl]-2-yl(chloro)palladium (150 mg, 0.191 mmol, 0.4 equiv) in THF (16 mL) at room temperature under nitrogen atmosphere. The reaction mixture was stirred for 4 hours at 65° C. under nitrogen atmosphere. The resulting mixture was filtered, and the filter cake was washed with ethyl acetate (3×10 mL). The filtrate was concentrated under reduced pressure to give a residue. The residue was purified by reversed-phase flash chromatography with the following conditions (column: C18; mobile phase: MeCN in Water (10 mmol/L NH$_4$HCO$_3$), 0% to 100% gradient in 20 min; detector, UV 254 nm) to afford the desired product as a yellow solid. (ESI, m/z): 818.10 [M+H]$^+$ 2-Amino-4-(8-chloro-4-(2,2-difluoroethyl)-10-fluoro-2-(((2R,7aS)-2-fluorotetrahydro-1H-pyrrolizin-7a(5H)-yl)

methoxy)-5-(oxazol-5-yl)-5,6-dihydro-4H-[1,4]oxazepino[5,6,7-de]quinazolin-9-yl)-7-fluorobenzo[b]thiophene-3-carbonitrile To a 50 mL round-bottom flask were added tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazolin-9-yl)-3-cyano-7-fluorobenzo[b]thiophen-2-yl)carbamate mate (120 mg, 0.147 mmol, 1 equiv) in DCM (3 mL) at room temperature followed by the addition of CF₃COOH (1 mL) dropwise. The reaction solution was stirred for 1 hour at room temperature and concentrated under reduced pressure to give a crude. The crude product was purified by Prep-HPLC with the following conditions (Column: YMC Triart C18 ExRs 5 m, 30 mm*150 mm; Mobile Phase A: Water (10 mmol/L NH₄HCO₃), Mobile Phase B: ACN; Flow rate: 60 mL/min; Gradient: 47% B to 62% B in 10 min; Wave Length: UV 254 nm/220 nm; RT1(min): 7.95/9.07) to afford 763 (peak 1: polar) as an off-white solid and 860 (peak 2: less polar) as an off-white solid. 763 (Peak 1): (ESI, m/z): 717.80 [M+H]⁺

¹H NMR (400 MHZ, CDCl₃, ppm): δ 7.91 (s, 1H), 7.18 (dd, 1H), 7.08 (s, 1H), 7.00 (t, J=8.8 Hz, 1H), 6.74-6.34 (m, 1H), 5.69 (s, 2H), 5.47-5.15 (m, 2H), 4.97 (dd, J=13.2, 4.2 Hz, 1H), 4.80-4.58 (m, 2H), 4.36 (s, 2H), 3.97-3.46 (m, 2H), 3.35 (s, 2H), 3.10 (s, 1H), 2.62-2.14 (m, 3H), 2.03 (d, J=17.7 Hz, 3H).

860 (Peak 2): (ESI, m/z): 717.80 [M+H]⁺

¹H NMR (400 MHZ, CDCl₃, ppm): δ 7.90 (s, 1H), 7.20 (t, J=8.4, 5.0 Hz, 1H), 7.12 (s, 1H), 7.01 (t, J=8.7 Hz, 1H), 6.69-6.23 (m, 1H), 5.66 (s, 2H), 5.44-5.20 (m, 2H), 4.95 (dd, J=13.0, 4.8 Hz, 1H), 4.75-4.57 (m, 2H), 4.35 (s, 2H), 3.62-3.48 (m, 1H), 3.47-3.15 (m, 3H), 3.04 (s, 1H), 2.49-2.13 (m, 3H), 2.09-1.90 (m, 3H).

Example 1ba: Synthesis of 2-amino-4-((5S)-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (779, 751)

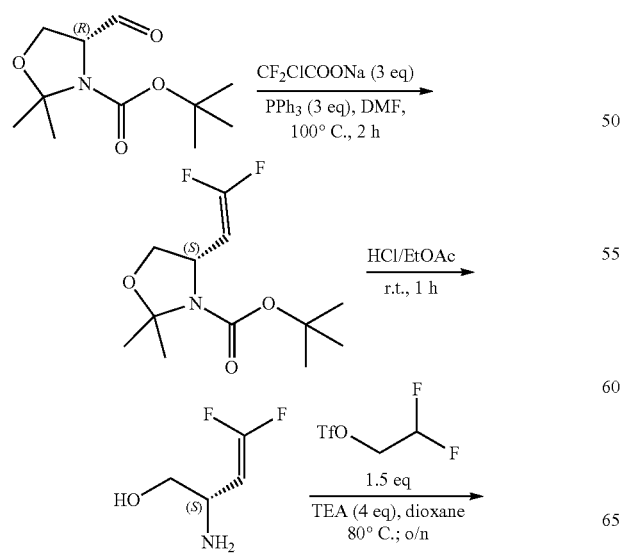

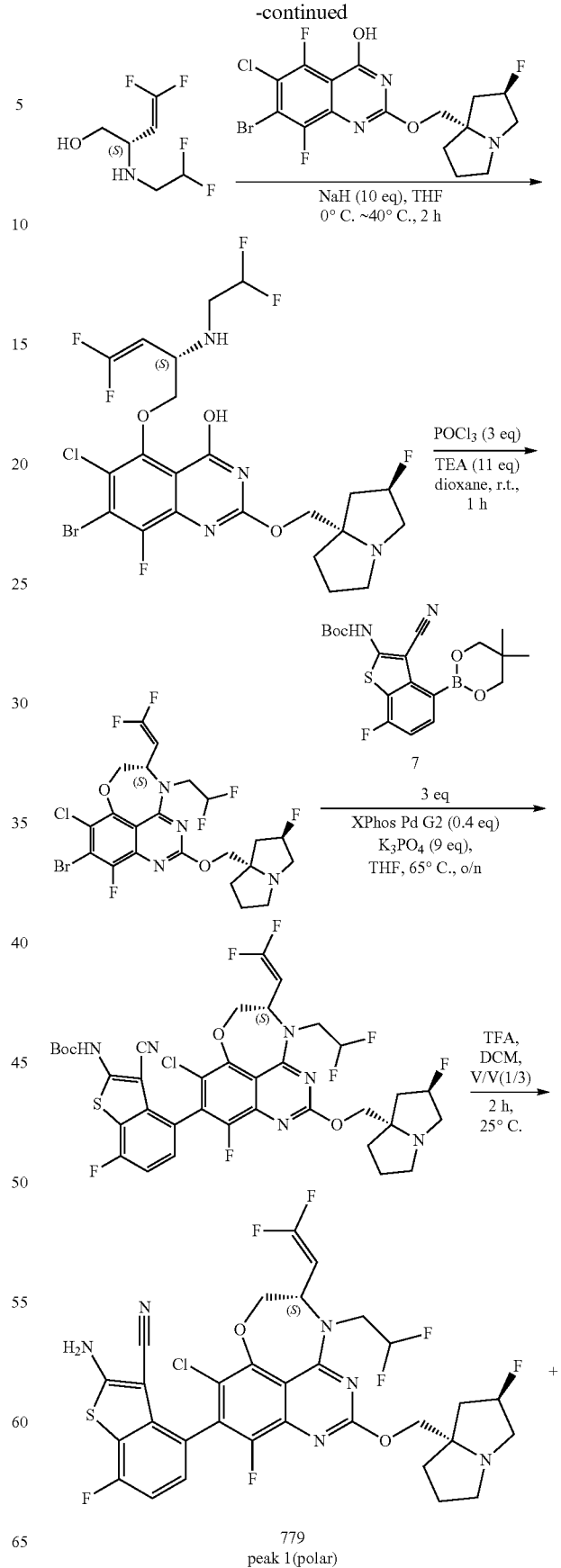

779
peak 1(polar)

-continued

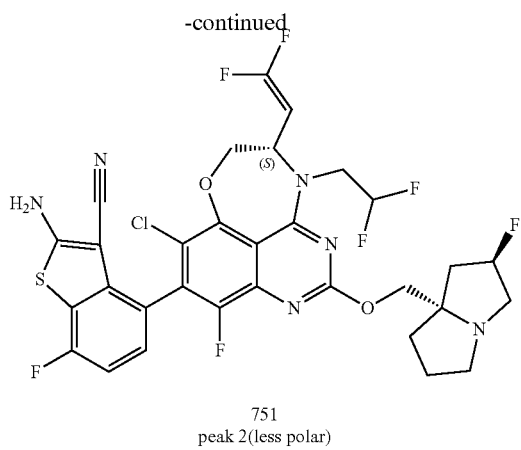

751
peak 2(less polar)

Tert-butyl (4S)-4-(2,2-difluoroethenyl)-2,2-dimethyl-1,3-oxazolidine-3-carboxylate To a stirred mixture of tert-butyl (4R)-4-formyl-2,2-dimethyl-1,3-oxazolidine-3-carboxylate (2 g, 8.72 mmol, 1 equiv) and sodium 2-chloro-2,2-difluoroacetate (3.99 g, 26.169 mmol, 3 equiv) in DMF (20 mL) was added PPh3 (6.86 g, 26.169 mmol, 3 equiv) in portions at room temperature. The resulting mixture was stirred for additional 2 hours at 100° C. It was cooled to room temperature, extracted with ethyl acetate (3×20 mL). The extracts were combined, washed with brine (3×20 mL), dried over anhydrous $Na_2SO_4$. After filtration, the filtrate was concentrated under reduced pressure to give a residue. The residue was purified by silica gel column chromatography, eluted with petroleum/ethyl acetate (12:1) to afford the desired product as a light-yellow liquid. (ESI, m/z): 264 [M+H]$^+$ (2S)-2-amino-4,4-difluorobut-3-en-1-ol A solution of tert-butyl (4S)-4-(2,2-difluoroethenyl)-2,2-dimethyl-1,3-oxazolidine-3-carboxylate (120 mg, 0.456 mmol, 1 equiv) and HCl (6M) solution in ethyl acetate (1 mL) was stirred for 1 hour at room temperature under nitrogen atmosphere. The resulting mixture was concentrated under reduced pressure to give desired product as a light-yellow liquid. (ESI, m/z): 124 [M+H]

(2S)-2-[(2,2-difluoroethyl)amino]-4,4-difluorobut-3-en-1-ol To a stirred solution of (2S)-2-amino-4,4-difluorobut-3-en-1-ol (1.1 g, 8.936 mmol, 1 equiv) and 2,2-difluoroethyl trifluoromethanesulfonate (2869 mg, 13.404 mmol, 1.5 equiv) in dioxane (11 mL, 129.844 mmol, 14.5 equiv) was added triethyl amine (3616 mg, 35.744 mmol, 4 equiv) dropwise at 80° C. under nitrogen atmosphere. The resulting mixture was stirred for additional overnight at 80° C. It was cooled to room temperature, extracted with ethyl acetate (3×10 mL). The extracts were combined, washed with brine (3×10 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (12:1) to afford the desired product as a yellow liquid. (ESI, m/z): 188 [M+H]$^+$ 7-Bromo-6-chloro-5-(((S)-2-((2,2-difluoroethyl)amino)-4,4-difluorobut-3-en-1-yl)oxy)-8-fluoro-2-(((2R,7aS)-2-fluorotetrahydro-1H-pyrrolizin-7a(5H)-yl)methoxy)quinazolin-4-ol To a stirred solution of (2S)-2-[(2,2-difluoroethyl)amino]-4,4-difluorobut-3-en-1-ol (200 mg, 1.069 mmol, 1 equiv) and 27-bromo-6-chloro-5,8-difluoro-2-(((2R,7aS)-2-fluorotetrahydro-1H-pyrrolizin-7a(5H)-yl) methoxy)quinazolin-4-ol (483 mg, 1.069 mmol, 1 equiv) in THF (4 mL) were added NaH (427 mg, 10.690 mmol, 10 equiv, 60%) in portions at 0° C. under nitrogen atmosphere. The resulting mixture was stirred for additional 2 hours at 40° C. It was cooled to room temperature, quenched with water at 0° C., and extracted with ethyl acetate (3×5 mL). The extracts were combined, washed with brine (3×5 mL), dried over anhydrous $Na_2SO_4$. After filtration, the filtrate was concentrated under reduced pressure the desired product which was used in the next step directly without further purification. (ESI, m/z):619 [M+H]$^+$ (S)-9-bromo-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline To a stirred solution of 7-bromo-6-chloro-5-(((S)-2-((2,2-difluoroethyl)amino)-4,4-difluorobut-3-en-1-yl)oxy)-8-fluoro-2-(((2R,7aS)-2-fluorotetrahydro-1H-pyrrolizin-7a(5H)-yl)methoxy) quinazolin- 4-ol (1.2 g, 1.936 mmol, 1 equiv) in dioxane (20 mL) was added triethylamine (2155 mg, 21.296 mmol, 11 equiv) and $POCl_3$ (890 mg, 5.808 mmol, 3 equiv) dropwise at room temperature. The resulting mixture was stirred for additional 1 hour at room temperature, extracted with ethyl acetate (3×10 mL). The extracts were combined, washed with brine (3×10 mL), dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a yellow liquid. (ESI, m/z):601 [M+H]$^+$.

Tert-butyl (4-((S)-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4] oxazepino[5,6,7-de]quinazolin-9-yl)-3-cyano-7-fluorobenzo[b]thiophen-2-yl)carbamate To a stirred solution of (S)-9-bromo-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline (229 mg, 0.381 mmol, 1 equiv) and tert-butyl N-[3-cyano-4-(5,5-dimethyl-1,3,2-dioxaborinan-2-yl)-7-fluoro-1-benzothiophen-2-yl]carbamate (461 mg, 1.143 mmol, 3 equiv) in THF (5 mL) were added X-Phos Pd G2 (72 mg, 0.152 mmol, 0.4 equiv) and $K_3PO_4$ (726 mg, 3.429 mmol, 9 equiv) in portions at room temperature under argon atmosphere. The resulting mixture was stirred for additional overnight at 65° C. It was cooled, extracted with ethyl acetate (3×2 mL). The extracts were combined, washed with brine (3×2 mL), dried over anhydrous $Na_2SO_4$. It was filtered, solvent was removed under reduced pressure to give a residue. The residue was purified by silica gel column chromatography, eluted with $CH_2Cl_2$/MeOH (10:1) to afford the desired product as an off-white liquid. (ESI, m/z): 813 [M+H]$^+$ 2-Amino-4-((5S)-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4] oxazepino[5,6,7-de]quinazolin-9-yl)-7-fluorobenzo[b] thiophene-3-carbonitrile A solution of tert-butyl (4-((S)-8-chloro-4-(2,2-difluoroethyl)-5-(2,2-difluorovinyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate (85 mg, 0.105 mmol, 1 equiv) in DCM (1.8 mL) was treated with TFA (0.6 mL) for 2 hours at 25° C. The resulting mixture was concentrated under reduced pressure to give a residue. The residue was basified to pH 8 with saturated $NaHCO_3$(aq.). The resulting mixture was extracted with $CH_2Cl_2$ (3×2 mL). The extracts were combined, washed with brine (3×2 mL), dried over anhydrous Na₂SO₄. After filtration, the filtrate was concentrated under reduced pressure to give a crude. The crude product (80 mg) was purified by Prep-HPLC with the following conditions (Column: Xselect CSHTM Prep C18 5 μm 19*150 mm OBD; Mobile Phase A: Water (0.1% FA), Mobile Phase B: ACN; Flow rate: 60 mL/min; Gradient: 25% B to 45% B in 10 min; Wave Length: UV 254 nm/220 nm; RT1(min): 7.17) to afford 779 (peak 1; polar) as an off-white solid and 751 (peak 2; less polar) (8.9 mg, 11.80%) as an off-white solid as desired products. 779 (Peak 1):(ESI, m/z): 713 [M+H]⁺

¹H NMR: (400 MHZ, DMSO-d₆, ppm) 88.10 (s, 2H), 7.28 (dd, J=8.4, 5.2 Hz, 1H), 7.15 (t, J=8.9 Hz, 1H), 6.45 (s, 1H), 5.34 (s, 1H), 5.21 (s, 1H), 4.91-4.84 (m, 1H), 4.76-4.66 (m, 2H), 4.66-4.59 (m, 1H), 4.33 (d, J=15.0 Hz, 2H), 4.02 (d, J=10.2 Hz, 1H), 3.08 (d, J=7.4 Hz, 2H), 3.01 (s, 1H), 2.82 (s, 1H), 2.17-2.06 (m, 1H), 2.05 (s, 1H), 2.00 (s, 1H), 1.87-1.74 (m, 3H). 751 (Peak 2): (ESI, m/z):713 [M+H]⁺

¹H NMR: (400 MHZ, DMSO-d₆, ppm) § 8.13 (d, J=17.6 Hz, 2H), 7.18 (d, J=12.4 Hz, 1H), 7.13 (d, J=8.7 Hz, 1H), 6.48 (d, J=4.1 Hz, 1H), 5.35 (s, 1H), 5.21 (s, 1H), 4.97 (dd, J=8.9, 2.6 Hz, 1H), 4.80 (d, J=8.0 Hz, 1H), 4.43 (dd, J=12.2, 2.1 Hz, 1H), 4.36-4.27 (m, 1H), 4.08-3.97 (m, 3H), 3.10 (s, 2H), 3.02 (s, 1H), 2.84 (s, 1H), 2.21-2.10 (m, 3H), 1.92-1.71 (m, 3H).

Example 1bb: Synthesis of 2-amino-4-(8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (604 and 609)

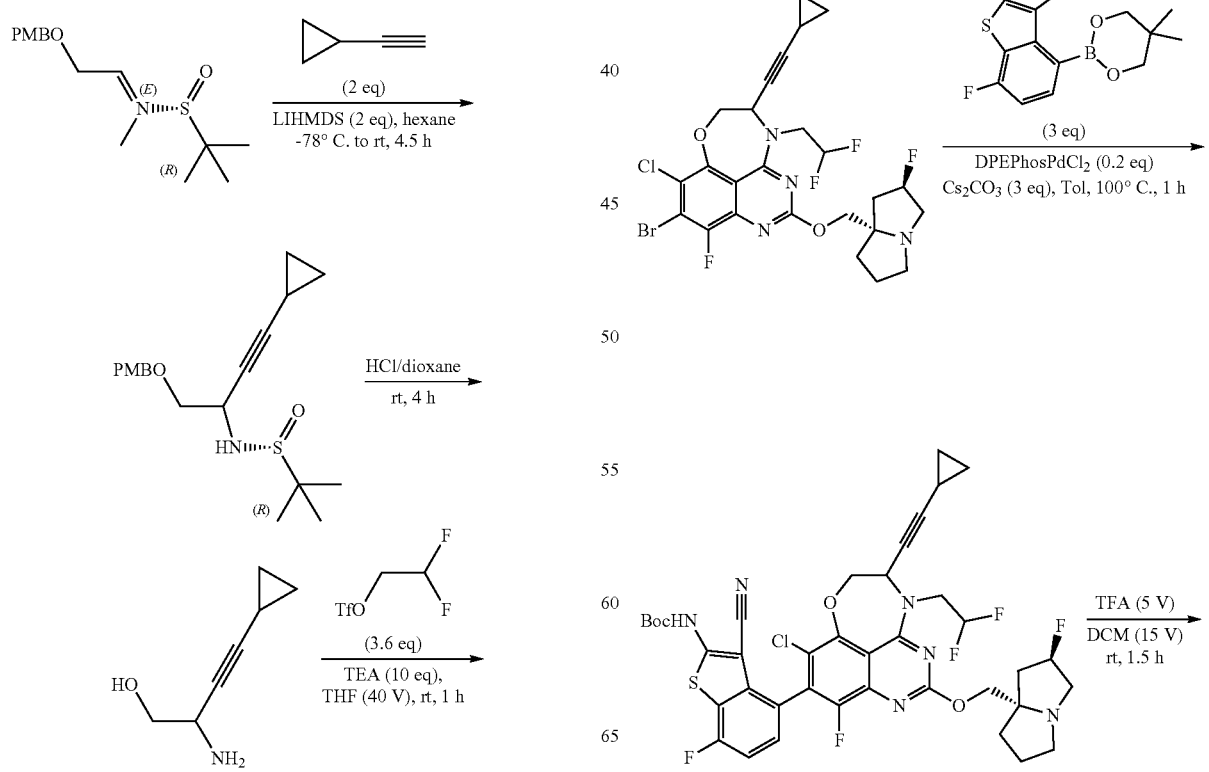

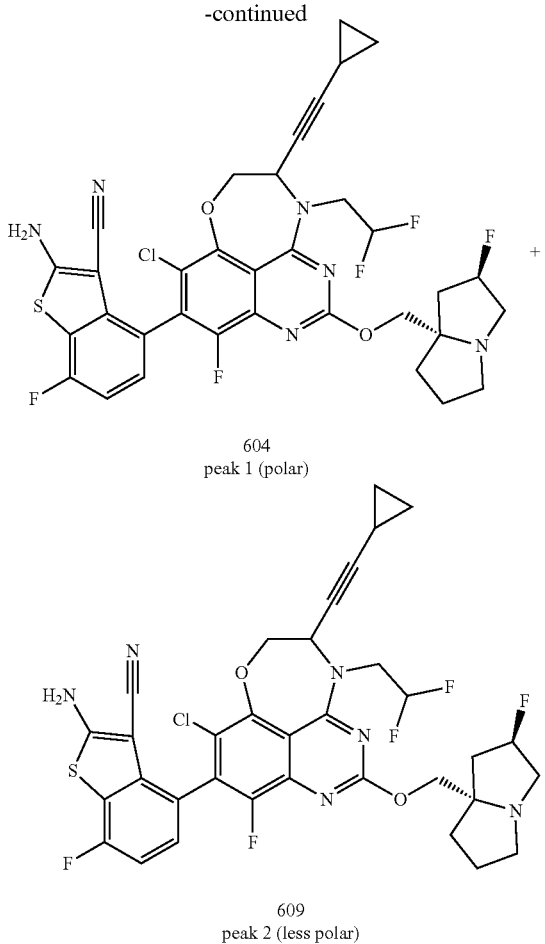

604
peak 1 (polar)

609
peak 2 (less polar)

(R)—N-(4-cyclopropyl-1-((4-methoxybenzyl)oxy)but-3-yn-2-yl)-2-methylpropane-2-sulfinamide A solution of ethynylcyclopropane (2332 mg, 35.288 mmol, 2 equiv) in hexane (50 mL) was treated with LiHMDS (5904 mg, 35.288 mmol, 2 equiv) for 30 minutes at −78° C. under nitrogen atmosphere followed by the addition of (R)—N-(2-[(4-methoxyphenyl)methoxy]ethylidene-2-methylpropane-2-sulfinamide (5 g, 17.644 mmol, 1 equiv) dropwise at −78° C. under nitrogen atmosphere. The resulting mixture was stirred for 4.5 hours at room temperature under nitrogen atmosphere. It was quenched with sat. NH$_4$Cl (30 mL) at 0° C., extracted with ethyl acetate (3×50 mL). The extracts were combined, dried over anhydrous Na$_2$SO$_4$. After filtration, the filtrate was concentrated under reduced pressure to give a residue. The residue was purified by silica gel column chromatography, eluted with petroleum/ethyl acetate (2:1) to afford the desired product as a brown oil. (ESI, m/z): 350 [M+H]$^+$ 2-Amino-4-cyclopropylbut-3-yn-1-ol A solution of (R)—N-(4-cyclopropyl-1-((4-methoxybenzyl)oxy)but-3-yn-2-yl)-2-methylpropane-2-sulfinamide (800 mg, 2.289 mmol, 1 equiv) in HCl/1,4-dioxane (4 M, 8 mL) was stirred for 4 hours at room temperature. The resulting mixture was concentrated under reduced pressure to give the desired product which was used in the next step directly without further purification. (ESI, m/z): 126 [M+H]$^+$ 4-Cyclopropyl-2-((2,2-difluoroethyl)amino)but-3-yn-1-ol A solution of 2-amino-4-cyclopropylbut-3-yn-1-ol (530 mg, 2.117 mmol, 1 equiv), 2,2-difluoroethyl trifluoromethanesulfonate (1631 mg, 7.621 mmol, 3.6 equiv) and triethylamine (2142 mg, 21.170 mmol, 10 equiv) in THF (20 mL) was stirred for 1 hour at room temperature. The resulting mixture was concentrated under reduced pressure to give a residue. The residue was purified by silica gel column chromatography, eluted with CH$_2$Cl$_2$/MeOH (10:1) to afford the desired product as a brown oil. (ESI, m/z): 190 [M+H]$^+$ 7-Bromo-6-chloro-5-((4-cyclopropyl-2-((2,2-difluoroethyl)amino)but-3-yn-1-yl)oxy)-8-fluoro-2-(((2R,7aS)-2-fluorotetrahydro-1H-pyrrolizin-7a(5H)-yl)methoxy)quinazolin-4-ol A solution of 4-cyclopropyl-2-((2,2-difluoroethyl)amino)but-3-yn-1-ol (220 mg, 1.163 mmol, 1 equiv) in THF (5.0 mL) was treated with NaH (251 mg, 10.467 mmol, 9 equiv) for 20 minutes at 0° C. under nitrogen atmosphere followed by the addition of 2-([(2R,7aS)-2-fluoro-hexahydropyrrolizin-7a-yl]methoxy)-7-bromo-6-chloro-5,8-difluoroquinazolin-4-ol (315 mg, 0.698 mmol, 0.6 equiv) at 0° C. The resulting mixture was stirred for 2 hours at 40° C. It was cooled to room temperature, concentrated under reduced pressure to give the desired product which was used in the next step directly without further purification. (ESI, m/z): 621 [M+H]$^+$ 9-Bromo-8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline A solution of 7-bromo-6-chloro-5-((4-cyclopropyl-2-((2,2-difluoroethyl)amino)but-3-yn-1-yl)oxy)-8-fluoro-2-(((2R,7aS)-2-fluorotetrahydro-1H-pyrrolizin-7a(5H)-yl)methoxy)quinazolin-4-ol (650 mg, 0.669 mmol, 1 equiv, 64%), POCl$_3$ (39 mg, 0.255 mmol, 5 equiv) and triethylamine (676 mg, 6.690 mmol, 10 equiv) in dioxane (13 mL) was stirred for 1 hour at 50° C. It was cooled to room temperature, concentrated under vacuum, extracted with CH$_2$Cl$_2$ (3×20 mL). The extracts were combined, dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (0.1% TFA), 30% to 50% gradient in 10 min; detector, UV 254 nm to give the desired product as a yellow solid. (ESI, m/z): 603[M+H]$^+$ Tert-butyl (4-(8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate A mixture of 9-bromo-8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline (110 mg, 0.182 mmol, 1 equiv), tert-butyl N-[3-cyano-4-(5,5-dimethyl-1,3,2-dioxaborinan-2-yl)-7-fluoro-1-benzothiophen-2-yl]carbamate (220 mg, 0.546 mmol, 3 equiv), Cs$_2$CO$_3$ (178 mg, 0.546 mmol, 3 equiv) and DPEPhosPdCl$_2$ (26 mg, 0.352 mmol, 0.2 equiv) in toluene (11.0 mL) was stirred for 1 hour at 100° C. under argon atmosphere. It was cooled to room temperature, concentrated under reduced pressure to give a residue. The residue was purified by reversed-phase flash chromatography with the following conditions: column, C18; mobile phase, MeCN in Water (0.1% TFA), 80% to 90% gradient in 10 min; detector, UV 254 nm to give the desired product as a yellow solid. (ESI, m/z):815[M+H]$^+$ 2-Amino-4-(8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (604-first peak and 609) A solution of tert-butyl (4-(8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate (80 mg, 0.098 mmol, 1 equiv) and TFA (2 mL) in DCM (6 mL) was stirred for 1.5 hours at room temperature. The resulting mixture was concentrated under vacuum to give a crude. The crude product (90 mg) was purified by Prep-HPLC with the following conditions (Column: Kinetex 5 m EVO C18, 30 mm*150 mm; Mobile Phase A: Water (10 mmol/L NH$_4$HCO$_3$), Mobile Phase B: ACN; Flow rate: 60 mL/min; Gradient: 50% B to 65% B in 10 min; Wave Length: UV 254 nm/220 nm; RT1(min): 8.63) to afford desired products: 604 (peak 1; polar) and 609 (peak 2; less polar) (as white solid respectively. 604 Peak 1 (polar):(ESI, m/z):715[M+H]$^+$ $^1$H NMR (400 MHZ, DMSO-d$_6$, ppm) § 8.08 (brs, 2H), 7.21 (dd, J=8.4, 5.4 Hz, 1H), 7.14 (t, J=8.8 Hz, 1H), 6.57-6.22 (m, 1H), 5.34-5.21 (m, 1H), 5.04 (d, J=4.0 Hz, 1H), 4.70 (dd, J=12.8, 5.0 Hz, 1H), 4.49 (d, J=12.8 Hz, 1H), 4.43-4.36 (m, 1H), 4.24-3.97 (m, 3H), 3.09-3.08 (m, 2H), 3.01 (s, 1H), 2.83-2.82 (m, 1H), 2.18-2.14 (m, 1H), 2.12-2.11 (m, 1H), 2.07-2.01 (m, 1H), 1.85-1.77 (m, 3H), 1.30-1.23 (m, 1H), 0.72-0.69 (m, 2H), 0.57-0.55 (m, 2H).

609 Peak 2 (less polar): (ESI, m/z): 715[M+H]$^+$ $^1$H NMR (400 MHZ, DMSO-d$_6$, ppm) δ 8.09 (brs, 2H), 7.20-7.13 (m, 2H), 6.62-6.26 (m, 1H), 5.34-5.21 (m, 1H), 5.05-5.04 (m, 1H), 4.74 (dd, J=12.6, 4.6 Hz, 1H), 4.6 (d, J=12.4 Hz, 1H), 4.38-4.31 (m, 1H), 4.22-4.20 (m, 1H), 4.10-3.99 (m, 2H), 3.09-3.08 (m, 2H), 3.01 (s, 1H), 2.83-2.82 (m, 1H), 2.23-2.11 (m, 1H), 2.05-1.95 (m, 2H), 1.85-1.77 (m, 3H), 1.31-1.23 (m, 1H), 0.76-0.71 (m, 2H), 0.50-0.46 (m, 1H), 0.36-0.29 (m, 1H).

Example 1bc: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-(hydroxyimino)ethyl)-5,6-dihydro-4H-[1,4]oxazepino[5,6,7-de]quinazolin-9-yl)-7-fluorobenzo[b]thiophene-3-carbonitrile (644 and 802)

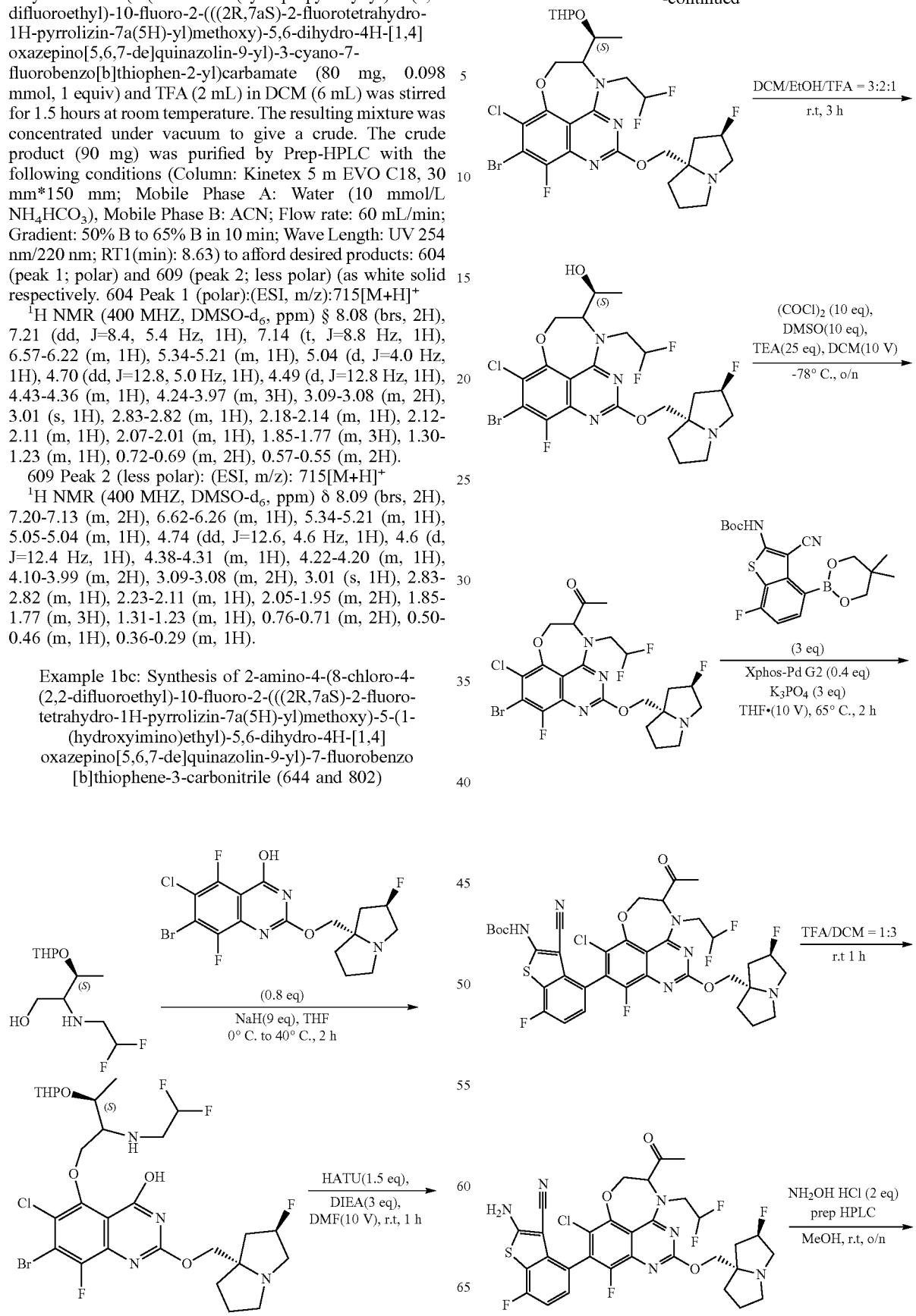

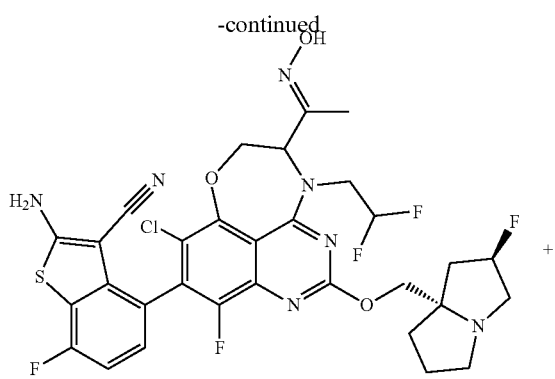

peak 1 (first polar)
644

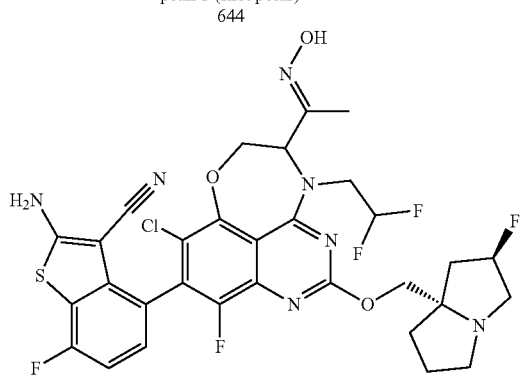

peak 2 (second polar)
802

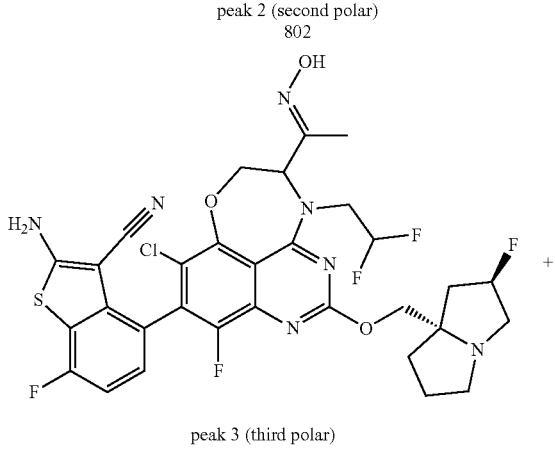

peak 3 (third polar)
1086

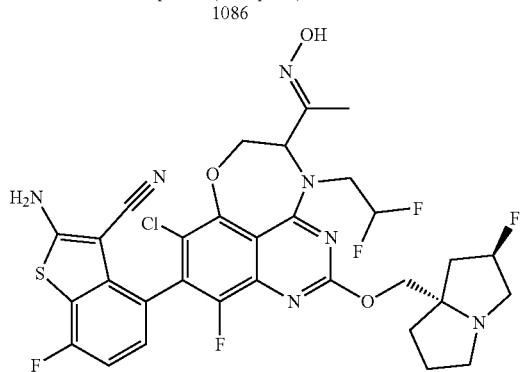

peak 4 (fourth polar)
759

7-Bromo-6-chloro-5-((3S)-2-((2,2-difluoroethyl)amino)-3-((tetrahydro-2H-pyran-2-yl)oxy)butoxy)-8-fluoro-2-(((2R,7aS)-2-fluorotetrahydro-1H-pyrrolizin-7a(5H)-yl)methoxy)quinazolin-4-ol To a stirred solution of (3S)-2-((2,2-difluoroethyl)amino)-3-((tetrahydro-2H-pyran-2-yl)oxy)butan-1-ol (500 mg, 1.97 mmol, 1.0 equiv) and 2-([(2R,7aS)-2-fluoro-hexahydropyrrolizin-7a-yl]methoxy)-7-bromo-6-chloro-5,8-difluoroquinazolin-4-ol (714 mg, 1.58 mmol, 0.8 equiv) in THF (5 mL) was added NaH (426 mg, 17.77 mmol, 9.0 equiv) in portions at 0° C. under nitrogen atmosphere. The resulting mixture was stirred for additional 2 hours at 40° C. It was cooled to room temperature, quenched with water, and extracted with $CH_2Cl_2$ (3×100 mL). The extracts were combined, washed with brine (1×50 mL), and dried over anhydrous $Na_2SO_4$. After filtration, the filtrate was concentrated under reduced pressure to give the desired product. (ESI, m/z): 685[M+H]$^+$ 9-Bromo-8-chloro-4-(2,2-difluoroethyl)-10-fluoro-2-(((2R,7aS)-2-fluorotetrahydro-1H-pyrrolizin-7a(5H)-yl)methoxy)-5-((1S)-1-((tetrahydro-2H-pyran-2-yl)oxy)ethyl)-5,6-dihydro-4H-[1,4]oxazepino[5,6,7-de]quinazoline To a stirred solution of 7-bromo-6-chloro-5-((3S)-2-((2,2-difluoroethyl)amino)-3-((tetrahydro-2H-pyran-2-yl)oxy)butoxy)-8-fluoro-2-(((2R,7aS)-2-fluorotetrahydro-1H-pyrrolizin-7a(5H)-yl)methoxy)quinazolin-4-ol (1.57 g, 2.29 mmol, 1.0 equiv) and HATU (1.31 g, 3.43 mmol, 1.5 equiv) in DMF (16 mL) was added DIEA (0.89 g, 6.87 mmol, 3.0 equiv) in portions at room temperature. The resulting mixture was stirred for additional 1 hour at room temperature, quenched with water, and extracted with $CH_2Cl_2$ (3×50 mL). The extracts were combined, washed with brine (1×50 mL), and dried over anhydrous $Na_2SO_4$. After filtration, the filtrate was concentrated under reduced pressure to give the desired product which was used in the next step directly without further purification. (ESI, m/z): 667 [M+H]$^+$ (1S)-1-(9-bromo-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)ethan-1-ol To a stirred solution of 9-bromo-8-chloro-4-(2,2-difluoroethyl)-10-fluoro-2-(((2R,7aS)-2-fluorotetrahydro-1H-pyrrolizin-7a(5H)-yl)methoxy)-5-((1S)-1-((tetrahydro-2H-pyran-2-yl)oxy)ethyl)-5,6-dihydro-4H-[1,4]oxazepino[5,6,7-de]quinazoline (2.0 g, 2.99 mmol, 1.0 equiv) and EtOH (6 mL) in DCM (9 mL) was added TFA (3 mL) in portions at room temperature. The resulting mixture was stirred for additional 3 hour at room temperature and concentrated under reduced pressure to give a residue. The residue was dissolved in DCM (20 mL), basified to pH~9 with saturated $NaHCO_3$(aq.), and extracted with $CH_2Cl_2$ (3×50 mL). The extracts were combined, washed with brine (1×50 mL), and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 10% to 50% gradient in 10 min; detector, UV 254 nm to give the desired product as a light-yellow solid. (ESI, m/z): 583 [M+H]$^+$ 1-(9-Bromo-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)ethan-1-one To a stirred solution of $(COCl)_2$ (1391 mg, 10.96 mmol, 10.0 equiv) in DCM (7 mL) were added DMSO (856 mg, 10.96 mmol, 10.0 equiv) in portions at −78° C. under argon atmosphere. The resulting mixture was stirred for additional 30 minutes at −78° C. To the above mixture was added (1S)-1-(9-bromo-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino

[5,6,7-de]quinazolin-5-yl)ethan-1-ol (640 mg, 1.09 mmol, 1.0 equiv) in portions at −78° C. The resulting mixture was stirred for additional 1 hour at −78° C. followed by the addition of triethylamine (2773 mg, 27.4 mmol, 25.0 equiv) in portions at −78° C. It was gradually warmed up and stirred for additional 30 minutes at room temperature, quenched with water, and extracted with CH$_2$Cl$_2$ (3×50 mL). The extracts were combined, washed with brine (1×50 mL), dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 10% to 50% gradient in 10 min; detector, UV 254 nm to give the desired product as a light brown solid. (ESI, m/z): 581 [M+H]$^+$ Tert-butyl (4-(5-acetyl-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate To a stirred solution of 1-(9-bromo-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)ethan-1-one (370 mg, 0.64 mmol, 1.0 equiv) and tert-butyl N-[3-cyano-4-(5,5-dimethyl-1,3,2-dioxaborinan-2-yl)-7-fluoro-1-benzothiophen-2-yl]carbamate (771 mg, 1.91 mmol, 3.0 equiv) in THF (1 mL) was added XPhos-Pd G2 (200 mg, 0.25 mmol, 0.4 equiv) and K$_3$PO$_4$ (71 mg, 0.34 mmol, 3.0 equiv) in portions at room temperature under nitrogen atmosphere. The resulting mixture was stirred for additional 2 hour at 65° C. It was cooled to room temperature, quenched with water, extracted with CH$_2$Cl$_2$ (3×30 mL). The extracts were combined, washed with brine (1×30 mL), and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 10% to 50% gradient in 10 min; detector, UV 254 nm to give the desired product as a light brown solid. (ESI, m/z): 793 [M+H]$^+$ 4-(5-Acetyl-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile To a stirred solution of tert-butyl (4-(5-acetyl-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate (80 mg, 0.1 mmol, 1.0 equiv) in DCM (0.6 mL) was added TFA (0.2 mL) in portions at room temperature. The resulting mixture was stirred for additional 1 hour. It was concentrated under reduced pressure to give the desired product as a light brown solid which was used in the next step directly without further purification. (ESI, m/z): 693 [M+H]$^+$ Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-(hydroxyimino)ethyl)-5,6-dihydro-4H-[1,4]oxazepino[5,6,7-de]quinazolin-9-yl)-7-fluorobenzo[b]thiophene-3-carbonitrile (644, 802) To a stirred solution of 4-(5-acetyl-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile (55 mg, 0.08 mmol, 1.0 equiv) in MeOH (2 mL) was added hydroxylamine hydrochloride (11 mg, 0.16 mmol, 2.0 equiv) in portions at room temperature. The resulting mixture was stirred for overnight at room temperature. It was concentrated to give a crude. The crude product was purified by Prep-HPLC with the following conditions (Column: XBridge BEH Shield RP18 5 m, 30 mm×150 mm; Mobile Phase A: Water (10 mmol/L NH$_4$HCO$_3$), Mobile Phase B: ACN; Flow rate: 60 mL/min; Gradient: 47% B to 70% B in 10 min; Wave Length: UV 254 nm/220 nm; RT1(min): 8.68) to afford desired products: 644 (peak 1), 802 (peak 2), 1086 (peak 3) and 759 (peak 4) white solids.

644 (Peak 1): (ESI, m/z): 707.80[M+H]$^+$
$^1$H NMR:$^1$H NMR (400 MHZ, DMSO-d$_6$, ppm) § 11.12 (s, 1H), 8.19-8.11 (m, 2H), 7.32-7.08 (m, 2H), 6.46-6.19 (m, 1H), 5.36-5.13 (m, 1H), 5.03-4.48 (m, 2H), 4.10 (s, 1H), 3.86 (d, J=14.7 Hz, 1H), 3.08 (s, 2H), 3.01 (s, 1H), 2.83 (s, 1H), 2.27-2.01 (s, 6H), 1.88-1.62 (s, 6H).

802 (Peak 2): (ESI, m/z): 707.80[M+H]$^+$
$^1$H NMR: (400 MHZ, DMSO-d$_6$, ppm) § 11.40 (d, J=4.7 Hz, 1H), 8.13 (s, 2H), 7.36-7.28 (m, 1H), 7.13 (dd, J=9.5, 8.4 Hz, 1H), 6.41 (t, J=4.1 Hz, 1H), 5.36 (s, 1H), 4.47 (q, J=14.7 Hz, 1H), 4.11 (t, J=10.3 Hz, 1H), 4.03 (dd, J=10.4, 3.7 Hz, 2H), 3.13-3.03 (m, 2H), 3.02 (s, 1H), 2.83 (d, J=6.9 Hz, 1H), 2.32-2.02 (m, 6H), 1.85-1.75 (m, 6H).

1086 (Peak 3): (ESI, m/z): 707.80[M+H]$^+$
$^1$H NMR: (400 MHZ, DMSO-d$_6$, ppm) § 11.15 (s, 1H), 8.15 (d, J=13.2 Hz, 2H), 7.21-7.18 (m, 1H), 7.16-7.11 (m, 1H), 6.47-6.19 (m, 1H), 5.35-5.22 (m, 1H), 4.58-4.52 (m, 1H), 4.22 (t, J=6.5 Hz, 1H), 4.13 (d, J=10.5 Hz, 1H), 4.01 (d, J=10.5 Hz, 1H), 3.09 (d, J=9.0 Hz, 2H), 3.02 (s, 1H), 2.84 (s, 1H), 2.13-2.02 (s, 6H), 1.90-1.74 (s, 6H).

759 (Peak 4): (ESI, m/z): 707.80[M+H]$^+$
$^1$H NMR: (400 MHZ, DMSO-d$_6$, ppm) § 11.16 (s, 1H), 8.13 (s, 2H), 7.21 (dd, J=8.3, 5.3 Hz, 1H), 7.18-7.10 (m, 1H), 6.33 (m, 1H), 5.35 (m, 1H), 4.54 (q, J=14.9 Hz, 1H), 4.12-4.01 (m, 2H), 4.04-3.93 (m, 1H), 3.09 (d, J=7.6 Hz, 2H), 3.01 (s, 1H), 2.83 (d, J=7.3 Hz, 1H), 2.23-2.14 (d, J=11.4 Hz, 1H), 2.06-2.00 (s, 5H), 1.86-1.78 (s, 6H).

Example 1bd: Synthesis of 2-amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-7-fluorobenzo[b]thiophene-3-carbonitrile (980)

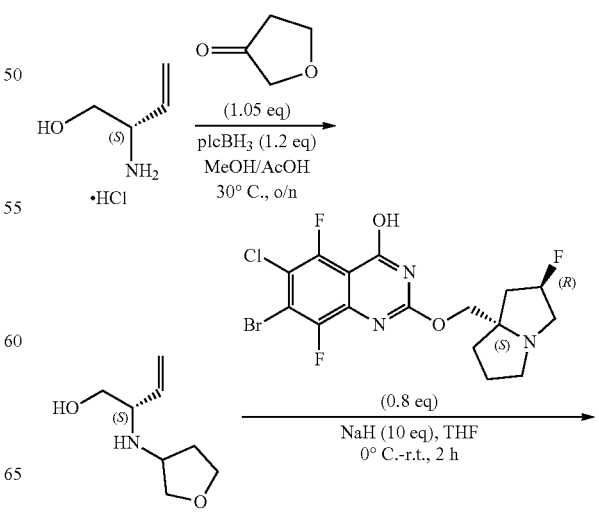

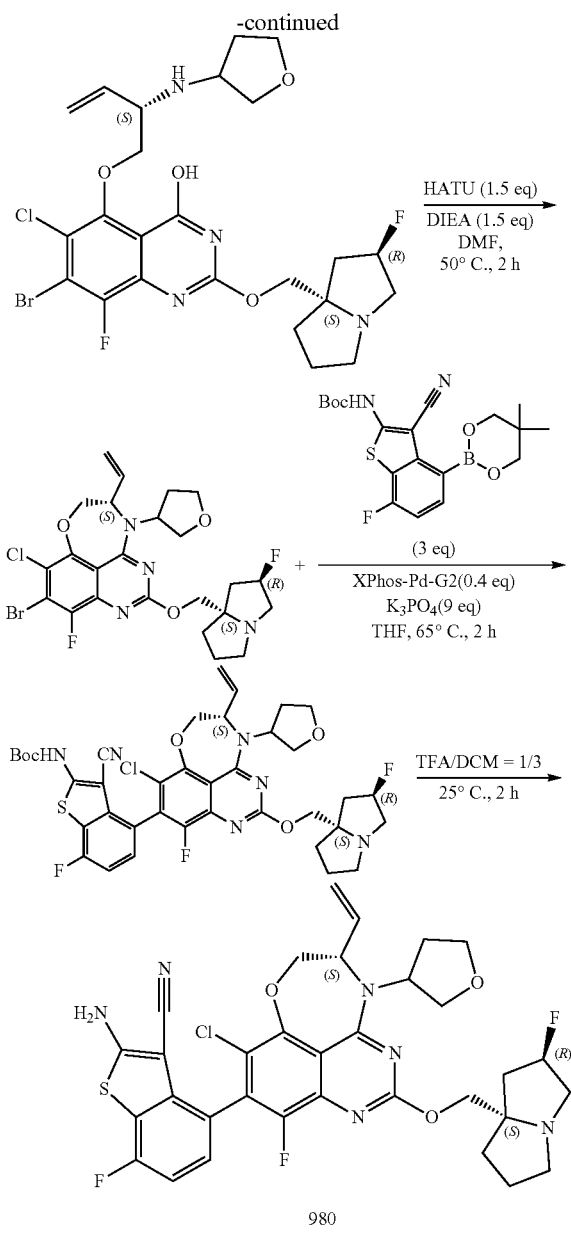

980

(2S)-2-(oxolan-3-ylamino)but-3-en-1-ol To a stirred solution of (2S)-2-aminobut-3-en-1-ol hydrochloride (3 g, 24.276 mmol, 1 equiv) and dihydrofuran-3-one (2.19 g, 25.490 mmol, 1.05 equiv) in MeOH (81 mL) were added AcOH (8.1 mL) and 2-methylpyridine borane (3.12 g, 29.131 mmol, 1.2 equiv) in portions at room temperature. The resulting mixture was stirred for overnight at 30° C. It was concentrated under reduced pressure and extracted with DCM (3×30 mL). The extracts were combined, washed with brine (1×30 mL), and dried over anhydrous Na$_2$SO$_4$. After filtration, the filtrate was concentrated under reduced pressure to give a residue. The residue was purified by silica gel column chromatography, eluted with DCM/MeOH (9: 1) to afford the desired product as a yellow liquid.

$^1$H NMR: (400 MHZ, DMSO-d$_6$, ppm) δ 5.59 (m, 1H), 5.18 (m, 1H), 5.09 (m, 1H), 3.78-3.55 (m, 3H), 3.41-3.19 (m, 4H), 3.05 (m, 1H), 2.02-1.87 (m, 3H), 1.65-1.53 (m, 1H).

7-Bromo-6-chloro-8-fluoro-2-(((2R,7aS)-2-fluorotetrahydro-1H-pyrrolizin-7a(5H)-yl)methoxy)-5-(((2S)-2-((tetrahydrofuran-3-yl)amino)but-3-en-1-yl)oxy)quinazolin-4-ol To a stirred solution of (2S)-2-(oxolan-3-ylamino)but-3-en-1-ol (350 mg, 2.226 mmol, 1 equiv), 7-bromo-6-chloro-5,8-difluoro-2-(((2R,7aS)-2-fluorotetrahydro-1H-pyrrolizin-7a(5H)-yl)methoxy)quinazolin-4-ol (806 mg, 1.781 mmol, 0.8 equiv) in THF (14 mL) were added NaH (890 mg, 22.260 mmol, 10 equiv, 60%) in portions at 0° C. under nitrogen atmosphere. The resulting mixture was stirred for additional 2 hours at room temperature. It was quenched with water at 0° C. and extracted with ethyl acetate (3×20 mL). The extracts were combined, washed with brine (3×20 mL), and dried over anhydrous Na$_2$SO$_4$. After filtration, the filtrate was concentrated under reduced pressure to give the desired product which was used in the next step directly without further purification. (ESI, m/z): 589 [M+H]$^+$ (5S)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazoline A solution of 7-bromo-6-chloro-8-fluoro-2-(((2R,7aS)-2-fluorotetrahydro-1H-pyrrolizin-7a(5H)-yl)methoxy)-5-(((2S)-2-((tetrahydrofuran-3-yl)amino)but-3-en-1-yl)oxy)quinazolin-4-ol (1.93 g, 3.272 mmol, 1 equiv), HATU (1.87 g, 4.908 mmol, 1.5 equiv) and DIEA (0.63 g, 4.908 mmol, 1.5 equiv) in DMF (100 mL) was stirred for 2 hours at 50° C. under nitrogen atmosphere. It was cooled to room temperature, extracted with ethyl acetate (3×100 mL). The extracts were combined, washed with brine (5×50 mL), and dried over anhydrous Na$_2$SO$_4$. After filtration, the filtrate was concentrated under reduced pressure to give a residue. The residue was purified by silica gel column chromatography, eluted with DCM/MeOH (10: 1) to give a light-yellow solid which was further purified by Prep-HPLC with the following conditions (Column: CHIRAL ART Cellulose-SB 2*25 cm, 5m; Mobile Phase A: HEX(0.1% DEA), Mobile Phase B: EtOH: DCM=1: 1; Flow rate: 20 mL/min; Gradient: isocratic 15; Wave Length: UV 254/220 nm; RT1(min): 9.253; RT2(min): 10.937; Sample Solvent: MeOH: EtOH; Injection Volume: 0.3 mL; Number Of Runs: 14) to afford desired product of the first peak (160 mg, 8.55%) as a white solid. (ESI, m/z): 571 [M+H]$^+$ Tert-butyl (4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-3-cyano-7-fluorobenzo[b]thiophen-2-yl)carbamate A mixture of (5S)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazoline (200 mg, 0.350 mmol, 1 equiv), K$_3$PO$_4$ (668 mg, 3.150 mmol, 9 equiv), 2nd Generation XPhos Precatalyst/X-Phos aminobiphenyl palladium chloride precatalyst (110 mg, 0.140 mmol, 0.4 equiv) and tert-butyl N-[3-cyano-4-(5,5-dimethyl-1,3,2-dioxaborinan-2-yl)-7-fluoro-1-benzothiophen-2-yl]carbamate (424 mg, 1.050 mmol, 3 equiv) in THF (5 mL) was stirred for 2 hours at 65° C. under argon atmosphere. It was cooled to room temperature, diluted with water (30 mL) and was extracted with ethyl acetate (3×50 mL). The extracts were combined, washed with brine (80 mL), and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (0.1% NH$_3$·H$_2$O), 10% to 50% gradient in 10 min; detector, UV 254 nm to give the desired product as a light brown oil. (ESI, m/z): 783 [M+H]$^+$ 2-Amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-7-fluorobenzo[b]thiophene-3-carbonitrile A mixture of tert-butyl (4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-3-cyano-7-fluorobenzo[b]thiophen-2-yl)carbamate (50 mg, 0.064 mmol, 1 equiv) in DCM (3 mL) and TFA (1 mL) was stirred for 2 hours at 25° C. The resulting mixture was concentrated under reduced pressure to give a crude. The crude product was purified by Prep-HPLC with the following conditions (Column: XBridge BEH C18 OBD Prep Column 130, 5 m, 30 mm*150 mm; Mobile Phase A: Water (10 mmol/L $NH_4HCO_3$), Mobile Phase B: ACN; Flow rate: 60 mL/min; Gradient: 20% B to 72% B in 10 min; Wave Length: UV 254 nm/220 nm; RT1(min): 9.35) to afford desired product as a white solid. (ESI, m/z): 683 $[M+H]^+$ $^1$H NMR: (400 MHZ, DMSO-$d_6$, ppm) δ 8.08 (s, 2H), 7.20 (dd, J=8.4, 5.3 Hz, 1H), 7.11 (t, J=8.9 Hz, 1H), 6.06 (ddd, J=17.2, 10.6, 3.8 Hz, 1H), 5.56 (s, 1H), 5.35 (s, 1H), 5.24-5.14 (m, 1H), 4.97-4.89 (m, 2H), 4.77 (s, 1H), 4.37 (d, J=12.6 Hz, 1H), 4.11 (d, J=10.2 Hz, 1H), 4.01 (dd, J=14.6, 9.3 Hz, 1H), 3.92 (dd, J=10.0, 3.6 Hz, 1H), 3.76-3.64 (m, 2H), 3.02 (s, 1H), 2.83 (d, J=6.9 Hz, 1H), 2.22-2.11 (m, 1H), 2.05 (d, J=15.0 Hz, 3H), 1.88-1.75 (m, 3H).

Example 1be: Synthesis of 2-amino-4-((5S)-8-chloro-4-(3,3-difluoropropyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (727 and 906)

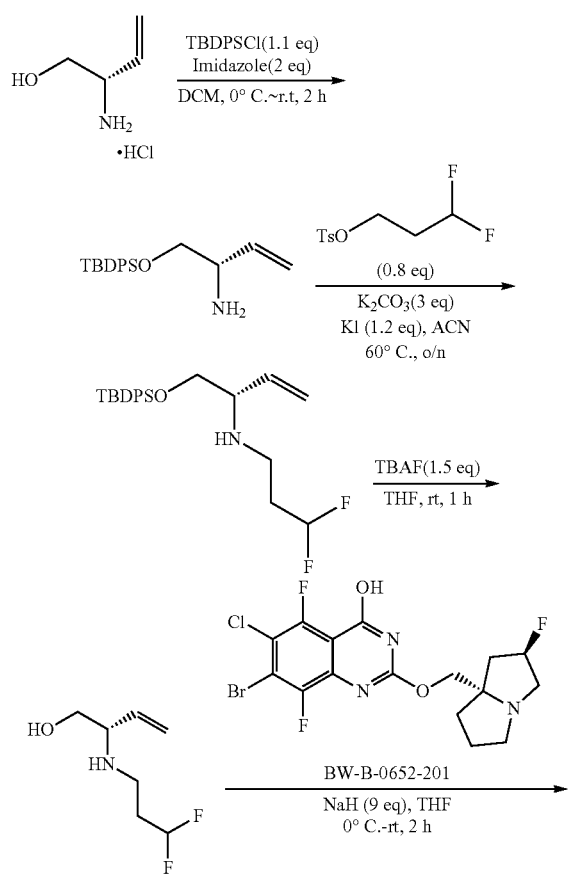

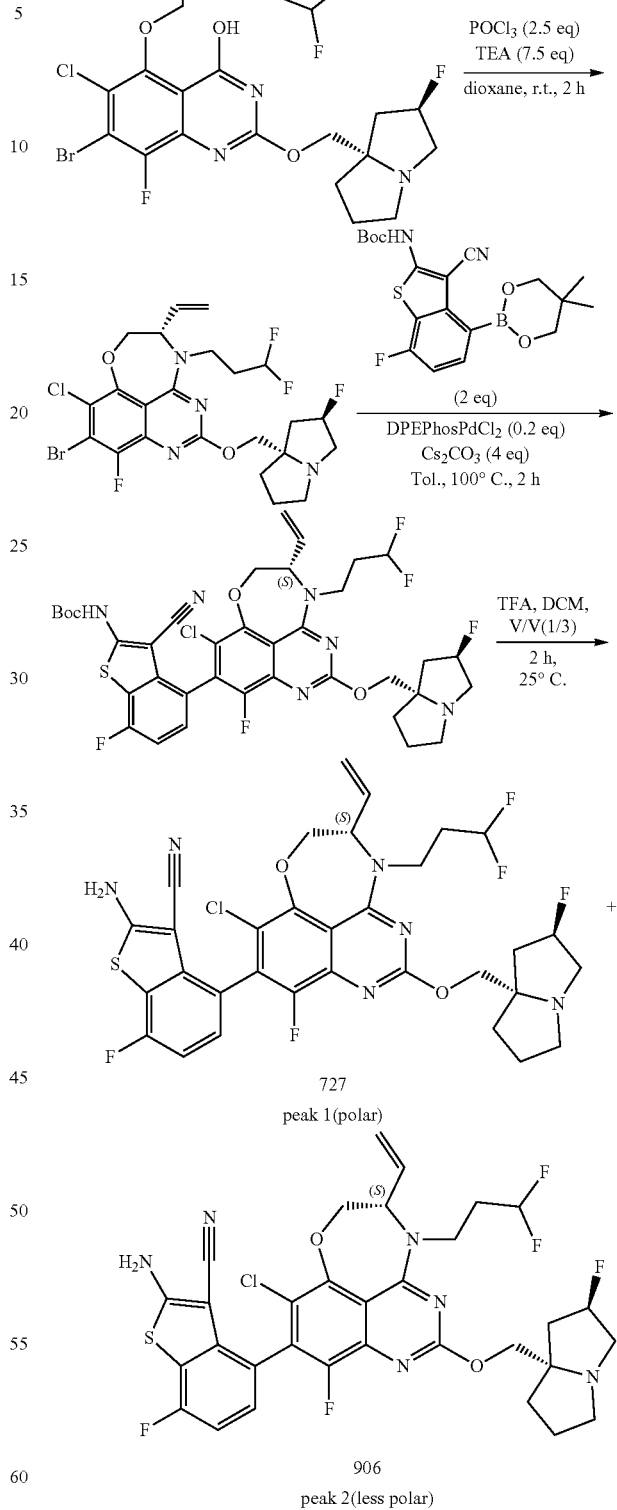

([(2S)-2-aminobut-3-en-1-yl]oxy(tert-butyl)diphenylsilane To a stirred solution of (2S)-2-aminobut-3-en-1-ol hydrochloride (1.4 g, 11.329 mmol, 1 equiv) and TBDPSCl (3425 mg, 12.462 mmol, 1.1 equiv) in DCM (28 mL) were added imidazole (1542 mg, 22.658 mmol, 2 equiv) in portions at 0° C. The resulting mixture was stirred for additional 2 hours at room temperature, extracted with CH$_2$Cl$_2$ (3×30 mL). The extracts were combined, washed with brine (3×30 mL), and dried over anhydrous Na$_2$SO$_4$. After filtration, the filtrate was concentrated under reduced pressure to afford the desired product as a colorless liquid. (ESI, m/z): 326[M+H]$^+$ (2S)-1-[(tert-butyldiphenylsilyl)oxy]but-3-en-2-yl](3,3-difluoropropyl)amine To a stirred mixture of ([(2S)-2-aminobut-3-en-1-yl]oxy(tert-butyl)diphenylsilane (1.2 g, 3.686 mmol, 1 equiv) and 3,3-difluoropropyl 4-methylbenzenesulfonate (738 mg, 2.949 mmol, 0.8 equiv) in ACN (20 mL) were added K$_2$CO$_3$ (1528 mg, 11.058 mmol, 3 equiv) and KI (734 mg, 4.423 mmol, 1.2 equiv) in portions at room temperature. The resulting mixture was stirred for overnight at 60° C. It was cooled down to room temperature, extracted with ethyl acetate (3×20 mL). The extracts were combined, washed with brine (3×20 mL), and dried over anhydrous Na$_2$SO$_4$. After filtration, the filtrate was concentrated under reduced pressure to give a residue. The residue was purified by silica gel column chromatography, eluted with petroleum/ethyl acetate (1:1) to afford the desired product as a colorless liquid. (ESI, m/z):404 [M+H]$^+$ (2S)-2-[(3,3-difluoropropyl)amino]but-3-en-1-ol To a stirred solution of [(2S)-1-[(tert-butyldiphenylsilyl)oxy]but-3-en-2-yl](3,3-difluoropropyl)amine (1.3 g, 3.221 mmol, 1 equiv) in THF (26 mL) was added TBAF (1263 mg, 4.832 mmol, 1.5 equiv) in portions at room temperature. The resulting mixture was stirred for additional 1 hour at room temperature and concentrated under reduced pressure to give a residue. The residue was purified by silica gel column chromatography, eluted with CH$_2$Cl$_2$/MeOH (10:1) to afford the deaired product as an off-white liquid. (ESI, m/z): 166 [M+H]$^+$ 7-Bromo-6-chloro-5-(((S)-2-((3,3-difluoropropyl)amino) but-3-en-1-yl)oxy)-8-fluoro-2-(((2R,7aS)-2-fluorotetrahydro-1H-pyrrolizin-7a(5H)-yl)methoxy)quinazolin-4-ol To a stirred solution of (2S)-2-[(3,3-difluoropropyl)amino]but-3-en-1-ol (150 mg, 0.908 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (548 mg, 0.726 mmol, 0.8 equiv) in THF (5 mL) were added NaH (196 mg, 8.172 mmol, 9 equiv) in portions at 0° C. under nitrogen atmosphere. The resulting mixture was stirred for 2 hours at room temperature, quenched with water at 0° C., and extracted with ethyl acetate (3×10 mL). The extracts were combined, washed with brine (3×10 mL), and dried over anhydrous Na$_2$SO$_4$. After filtration, the filtrate was concentrated under reduced pressure to give the desired product which was used in the next step directly without further purification. (ESI, m/z): 597[M+H]$^+$ (S)-9-bromo-8-chloro-4-(3,3-difluoropropyl)-10-fluoro-2-(((2R,7aS)-2-fluorotetrahydro-1H-pyrrolizin-7a(5H)-yl) methoxy)-5-vinyl-5,6-dihydro-4H-[1,4]oxazepino[5,6,7-de] quinazoline To a stirred solution of 7-bromo-6-chloro-5-(((S)-2-((3,3-difluoropropyl)amino)but-3-en-1-yl)oxy)-8-fluoro-2-(((2R,7aS)-2-fluorotetrahydro-1H-pyrrolizin-7a (5H)-yl)methoxy)quinazolin-4-ol (440 mg, 0.736 mmol, 1 equiv) in dioxane (0.5 mLl) were added triethylamine (35 μL, 0.247 mmol, 7.5 equiv) and POCl$_3$ (8 μL, 0.083 mmol, 2.5 equiv) dropwise at room temperature. The resulting mixture was stirred for 2 hours at room temperature and extracted with ethyl acetate (3×15 mL). The extracts were combined, washed with brine (3×20 mL), and dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10:1) to afford the desired product as a light-yellow oil. (ESI, m/z): 579[M+H]$^+$ Tert-butyl (4-((5S)-8-chloro-4-(3,3-difluoropropyl)-10-fluoro-2-(((2R,7aS)-2-fluorotetrahydro-1H-pyrrolizin-7a (5H)-yl)methoxy)-5-vinyl-5,6-dihydro-4H-[1,4]oxazepino [5,6,7-de]quinazolin-9-yl)-3-cyano-7-fluorobenzo[b] thiophen-2-yl)carbamate To a stirred solution of (S)-9-bromo-8-chloro-4-(3,3-difluoropropyl)-10-fluoro-2-(((2R, 7aS)-2-fluorotetrahydro-1H-pyrrolizin-7a(5H)-yl) methoxy)-5-vinyl-5,6-dihydro-4H-[1,4]oxazepino[5,6,7-de] quinazoline (320 mg, 0.552 mmol, 1 equiv) and tert-butyl N-[3-cyano-4-(5,5-dimethyl-1,3,2-dioxaborinan-2-yl)-7-fluoro-1-benzothiophen-2-yl]carbamate (446.22 mg, 1.104 mmol, 2 equiv) in toluene (8 mL) were added Dichloro[bis (2-(diphenylphosphino)phenyl)ether]palladium(II)) (79 mg, 0.110 mmol, 0.2 equiv) and Cs$_2$CO$_3$ (719 mg, 2.208 mmol, 4 equiv) in portions at room temperature under argon atmosphere. The resulting mixture was stirred for 2 h at 100° C. It was cooled to room temperature, extracted with ethyl acetate (3×10 mL). The extracts were combined, washed with brine (3×10 mL), and dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10:1) to afford the desired product as a light-yellow oil. (ESI, m/z): 791/793[M+H]$^+$ 2-Amino-4-((5S)-8-chloro-4-(3,3-difluoropropyl)-10-fluoro-2-(((2R,7aS)-2-fluorotetrahydro-1H-pyrrolizin-7a (5H)-yl)methoxy)-5-vinyl-5,6-dihydro-4H-[1,4]oxazepino [5,6,7-de]quinazolin-9-yl)-7-fluorobenzo[b]thiophene-3-carbonitrile To a stirred solution of tert-butyl (4-((5S)-8-chloro-4-(3,3-difluoropropyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-3-cyano-7-fluorobenzo[b]thiophen-2-yl)carbamate (140 mg, 0.177 mmol, 1 equiv) in DCM (3 mL) were added TFA (1 mL) dropwise at room temperature. The resulting mixture was stirred for 2 hours at 25° C., concentrated under reduced pressure to give a residue. It was basified to pH~8 with saturated NaHCO$_3$(aq.) and extracted with CH$_2$Cl$_2$ (3×5 mL). The extracts were combined, washed with brine (3×5 mL), dried over anhydrous Na$_2$SO$_4$. After filtration, the filtrate was concentrated under reduced pressure to give a crude. The crude product (110 mg) was purified by Prep-HPLC with the following conditions (Column: Sunfire C18 5 m, 30 mm*150 mm; Mobile Phase A: Water (0.1% FA), Mobile Phase B: ACN; Flow rate: 60 mL/min; Gradient: 25% B to 45% B in 10 min; Wave Length: UV 254 nm/220 nm; RT1(min): 7.33/8.02) to afford desired products: 727 (peak 1; polar) and 906 (peak 2; less polar) as off-white solids. 727 (Peak 1): (ESI, m/z):691 [M+H]$^+$ $^1$H NMR: (400 MHZ, DMSO-d$_6$, ppm) 810.71-10.90 (m, 1H), 8.12 (d, J=15.7 Hz, 2H), 7.22 (dd, J=8.4, 5.3 Hz, 1H), 7.12 (t, J=8.9 Hz, 1H), 6.02 (ddd, J=16.2, 10.3, 4.8 Hz, 1H), 5.29 (d, J=10.4 Hz, 1H), 5.11 (d, J=17.1 Hz, 1H), 4.85 (d, J=12.8 Hz, 1H), 4.70 (s, 1H), 4.33 (d, J=12.9 Hz, 1H), 4.26 (dd, J=13.4, 6.9 Hz, 1H), 4.13 (s, 2H), 3.75 (s, 1H), 3.41-3.59 (m, 2H), 2.39-2.45 (m, 2H), 2.51-2.63 (m, 2H), 2.05 (s, 5H). 906 (Peak 2): (ESI, m/z):691 [M+H]$^+$ $^1$H NMR: (400 MHZ, DMSO-d$_6$, ppm) § 8.12 (s, 2H), 7.23 (ddd, J=11.4, 8.6, 5.7 Hz, 1H), 7.14 (td, J=8.9, 3.1 Hz, 1H), 6.26 (t, J=4.3 Hz, 1H), 6.15-5.97 (m, 1H), 5.48-5.36 (m, 2H), 5.27 (d, J=10.7 Hz, 1H), 4.18-4.01 (m, 2H), 3.84-3.70 (m, 2H), 3.08 (d, J=8.0 Hz, 2H), 3.01 (s, 1H), 2.86-2.77 (m, 1H),, 2.22-2.31 (m, 2H)2.14 (d, J=13.1 Hz, 1H), 2.06 (s, 1H), 2.01 (s, 1H), 1.93 (d, J=16.9 Hz, 3H), 1.87-1.75 (m, 3H).
Example 1bf: Synthesis of 2-amino-4-((5R)-8-chloro-10-fluoro-5-(1-fluorocyclopropyl)-2-(((2R, 7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (844 and 772)
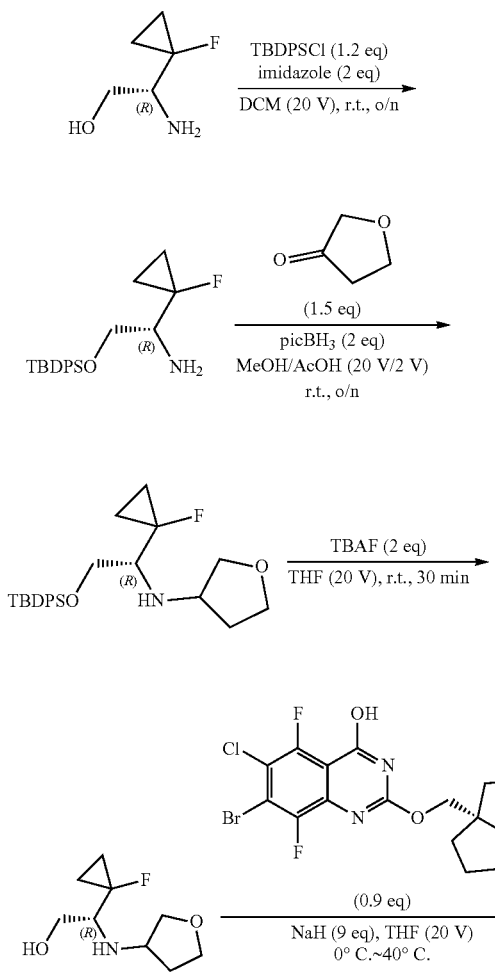
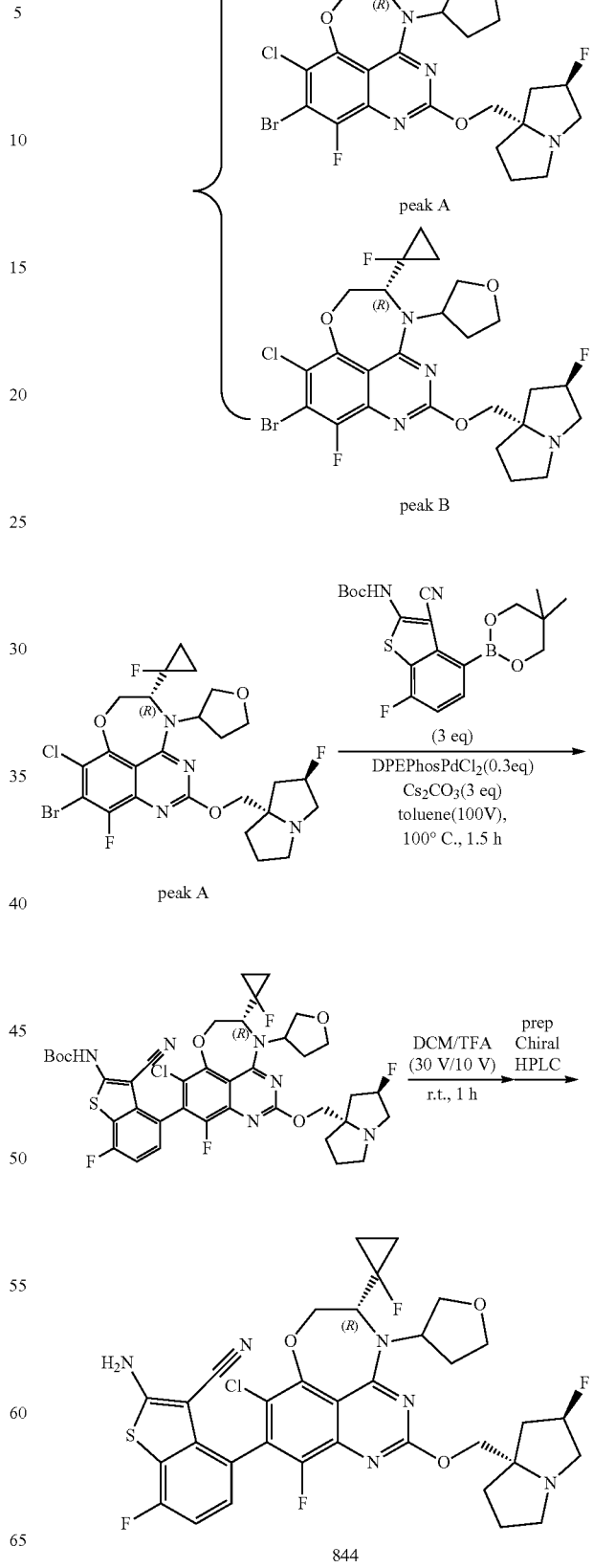

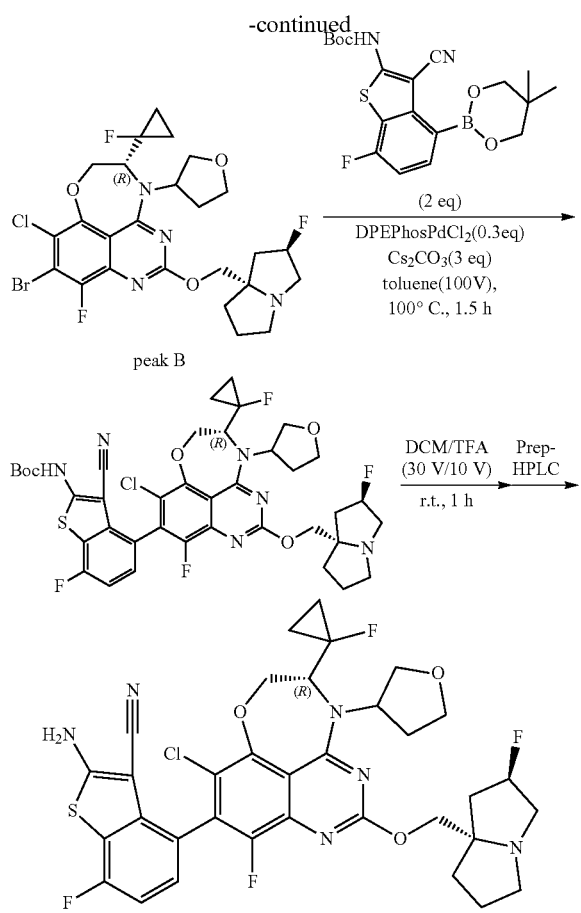

peak B

772

[(2R)-2-amino-2-(1-fluorocyclopropyl)ethoxy](tert-butyl)diphenylsilane To a stirred solution (2R)-2-amino-2-(1-fluorocyclopropyl)ethanol (2.5 g, 20.984 mmol, 1 equiv) in DCM (50 mL) were added TBDPSCl (6.92 g, 25.181 mmol, 1.2 equiv) and imidazole (2.86 g, 41.968 mmol, 2 equiv) in portions at room temperature. The reaction mixture was treated with water, extracted with $CH_2Cl_2$ (3×150 mL). The extracts were combined, washed with brined, and dried over $Na_2SO_4$. It was filtered and concentrated under reduced pressure to give a residue. The residue was purified by silica gel column chromatography, eluted with $CH_2Cl_2$/MeOH (20:1) to afford the desired product as a yellow oil. (ESI, m/z):358 [M+H]$^+$ N-[(1R)-2-[(tert-butyldiphenylsilyl)oxy]-1-(1-fluorocyclopropyl)ethyl]oxolan-3-amine A solution of [(2R)-2-amino-2-(1-fluorocyclopropyl)ethoxy](tert-butyl)diphenylsilane (2.3 g, 6.433 mmol, 1 equiv) in MeOH (46 mL) and AcOH (4.6 mL) was treated with dihydrofuran-3-one (0.83 g, 9.649 mmol, 1.5 equiv) for 5 minutes at room temperature under nitrogen atmosphere followed by the addition of 2-methylpyridine borane (1.38 g, 12.866 mmol, 2 equiv) in portions at room temperature. The resulting mixture was stirred for overnight and basified to pH~8 with saturated $NaHCO_3$(aq.). It was treated with water, extracted with $CH_2Cl_2$ (3×50 mL). The extracts were combined, washed with brine and dried over $Na_2SO_4$. It was filtered, concentrated under reduced pressure to give a ersidue. The residue was purified by reversed-phase flash chromatography with the following conditions: column, C18; mobile phase, MeCN in Water (10 mmol/L $NH_4HCO_3$), 80% to 100% gradient in 10 min; detector, UV 254 nm to afford the desired product as a yellow oil. (ESI, m/z): 428[M+H]$^+$ 2R)-2-(1-fluorocyclopropyl)-2-(oxolan-3-ylamino)ethanol To a stirred solution N-[(1R)-2-[(tert-butyldiphenylsilyl)oxy]-1-(1-fluorocyclopropyl)ethyl]oxolan-3-amine (2.35 g, 5.495 mmol, 1 equiv) in THF (47 mL) was added TBAF (2.87 g, 10.990 mmol, 2 equiv) dropwise at room temperature. The resulting mixture was stirred for 2 hour and concentrated under reduced pressure to give a residue. The residue was purified by silica gel column chromatography, eluted with $CH_2Cl_2$/MeOH (10:1) to afford the desired product as a yellow oil. (ESI, m/z): 190[M+H]$^+$ 7-Bromo-6-chloro-8-fluoro-5-((2R)-2-(1-fluorocyclopropyl)-2-((tetrahydrofuran-3-yl)amino)ethoxy)-2-(((2R,7aS)-2-fluorotetrahydro-1H-pyrrolizin-7a(5H)-yl)methoxy)quinazolin-4-ol A solution of (2R)-2-(1-fluorocyclopropyl)-2-(oxolan-3-ylamino)ethanol (320 mg, 1.691 mmol, 1 equiv) in THF (6.4 mL) was treated with 7-bromo-6-chloro-5,8-difluoro-2-(((2R,7aS)-2-fluorotetrahydro-1H-pyrrolizin-7a(5H)-yl)methoxy) quinazolin-4-ol (688 mg, 1.522 mmol, 0.9 equiv) for 5 minutes at 0° C. under nitrogen atmosphere followed by the addition of NaH (365 mg, 15.219 mmol, 9 equiv) in portions at 0° C. The resulting mixture was stirred for 30 minutes at 40° C. It was cooled to room temperature, quenched by the addition of water (15 mL) at 0° C., and extracted with $CH_2Cl_2$ (3×150 mL). The extracts were combined, washed with brine, and dried over anhydrous $Na_2SO_4$. After filtration, the filtrate was concentrated under reduced pressure to the desired product which was used in the next step directly without further purification. (ESI, m/z): 621[M+H]$^+$ (5R)-9-bromo-8-chloro-10-fluoro-5-(1-fluorocyclopropyl)-2-(((2R,7aS)-2-fluorotetrahydro-1H-pyrrolizin-7a (5H)-yl)methoxy)-4-(tetrahydrofuran-3-yl)-5,6-dihydro-4H-[1,4]oxazepino[5,6,7-de]quinazoline To a stirred solution of 7-bromo-6-chloro-8-fluoro-5-((2R)-2-(1-fluorocyclopropyl)-2-((tetrahydrofuran-3-yl)amino)ethoxy)-2-(((2R,7aS)-2-fluorotetrahydro-1H-pyrrolizin-7a(5H)-yl) methoxy)quinazolin-4-ol (1 g, 1.608 mmol, 1 equiv) in DMF (30 mL) was added HATU (1.22 g, 3.216 mmol, 2 equiv) and DIEA (0.42 g, 3.216 mmol, 2 equiv) at room temperature. The resulting mixture was stirred for 1 hour at 40° C. It was cooled to room temperature, quenched with water at room temperature, and extracted with $CH_2Cl_2$ (3×400 mL). The extracts were combined, washed with brine, and dried over anhydrous $Na_2SO_4$. After filtration, the filtrate was concentrated under reduced pressure to give a residue. The residue was purified by Prep-Chiral-HPLC with the following conditions:Column: Lux 5u Celluloes-42.12*25 cm, 5m; Mobile Phase A: HEX(0.1% DEA), Mobile Phase B: EtOH; Flow rate: 20 mL/min; Gradient: isocratic 40; Wave Length: UV 254/220 nm; RT1(min): 6.033; RT2(min): 10.29; Sample Solvent: MeOH; Injection Volume: 1.0 mL; Number Of Runs: 6, to afford the desired intermediates: Intermediate A: the first eluting (peak A) and Intermediate B: the second eluting (peak B) (205 mg, 20.06%) as light yellow solids.

Peak A:(ESI, m/z): 603[M+H]$^+$

Peak B:(ESI, m/z): 603[M+H]$^+$

Tert-butyl (4-((5R)-8-chloro-10-fluoro-5-(1-fluorocyclopropyl)-2-(((2R,7aS)-2-fluorotetrahydro-1H-pyrrolizin-7a (5H)-yl)methoxy)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate To a stirred mixture of (5R)-9-bromo-8-chloro-10-fluoro-5-(1-fluorocyclopropyl)-2-(((2R,7aS)-2-fluorotetrahydro-1H-pyrrolizin-7a (5H)-yl)methoxy)-4-(tetrahydrofuran-3-yl)-5,6-dihydro-4H-[1,4]oxazepino[5,6,7-de]quinazoline (Intermediate A: 180 mg, 0.149 mmol, 1 equiv) and tert-butyl N-[3-cyano-4-(5,5-dimethyl-1,3,2-dioxaborinan-2-yl)-7-fluoro-1-benzothiophen-2-yl]carbamate (180 mg, 0.447 mmol, 3 equiv) in toluene (18 mL) was added dichloro[bis(2-(diphenylphosphino)phenyl)ether]palladium(II) (32 mg, 0.045 mmol, 0.3 equiv) and Cs$_2$CO$_3$ (145 mg, 0.447 mmol, 3 equiv) at room temperature under argon atmosphere. The resulting mixture was stirred for 90 minutes at 100° C. under argon atmosphere. It was cooled to room temperature, filtered and the filter cake was washed with DCM (5×60 mL). The filtrate was concentrated under reduced pressure to give a residue. The residue was purified by reversed-phase flash chromatography with the following conditions: column, C18; mobile phase, MeCN in Water (10 mmol/L NH$_4$HCO$_3$), 60% to 80% gradient in 10 min; detector, UV 254 nm to afford the desired product as a light-yellow solid. (ESI, m/z): 815[M+H]$^+$ 2-Amino-4-((5R)-8-chloro-10-fluoro-5-(1-fluorocyclopropyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (844) To a stirred solution of tert-butyl (4-((5R)-8-chloro-10-fluoro-5-(1-fluorocyclopropyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate (220 mg, 0.270 mmol, 1 equiv) in DCM (6.6 mL) was added TFA (2.2 mL) at room temperature. The mixture was stirred for 1 hour at room temperature and concentrated under vacuum to give a crude. The crude product was purified by prep Chiral HPLC with the following conditions: CHIRALPAK-IE 2*25 cm, 5m; Mobile Phase A: HEX(0.1% DEA), Mobile Phase B: EtOH: DCM=1: 1; Flow rate: 20 mL/min; Gradient: isocratic 60; Wave Length: UV 254/220 nm; RT1(min): 4.023; RT2(min): 5.483; Sample Solvent: MeOH; Injection Volume: 0.9 mL; Number Of Runs: 3 to afford the desired product as light yellow solid. 844 (ESI, m/z): 715 [M+H]$^+$ $^1$H NMR: (400 MHZ, DMSO-d$_6$, ppm) § 8.08 (s, 2H), 7.24-7.20 (m 1H), 7.14-7.10 (m, 1H), 5.36-5.23 (m, 1H), 5.22-5.18 (m, 1H), 4.96-4.91 (m, 1H), 4.41 (d, J=12.8 Hz, 1H), 4.27-4.21 (m, 1H), 4.16-4.01 (m, 3H), 3.99-3.95 (m, 1H), 3.89- 3.83 (m, 1H), 3.77-3.71 (m, 1H), 3.13-3.07 (m, 2H), 3.02 (s, 1H), 2.86-2.80 (m, 1H), 2.40-2.32 (m, 2H), 2.18-2.10 (m, 1H), 2.08-2.04 (m, 1H), 2.02-1.97 (m, 1H), 1.88-1.75 (m, 3H), 1.24-1.11 (m, 2H), 1.09-0.98 (m, 2H).

2-Amino-4-((5R)-8-chloro-10-fluoro-5-(1-fluorocyclopropyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile (772)

Starting from Intermediate B, desired product 772 was obtained by following the same procedure. (ESI, m/z): 715[M+H]$^+$ $^1$H NMR: (400 MHZ, DMSO-d$_6$, ppm) § 8.07 (s, 2H), 7.23-7.19 (m, 1H), 7.14-7.09 (m, 1H), 5.36-5.21 (m, 2H), 4.96-4.90 (m, 1H), 4.21-4.06 (m, 5H), 3.91 (t, J=8.4 Hz, 1H), 3.76 (q, J=7.6 Hz, 1H), 3.14-3.05 (m, 2H), 3.02 (s, 1H), 2.87-2.79 (m, 1H), 2.31-2.18 (m, 2H), 2.13-1.98 (m, 3H), 1.89-1.73 (m, 3H), 1.26-1.06 (m, 2H), 1.03-1.96 (m, 2H).

Example 1bg: Synthesis of 2-amino-4-((5S)-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino[5,6,7-de]quinazolin-9-yl)-7-fluorobenzo[b]thiophene-3-carbonitrile (824 and 917)

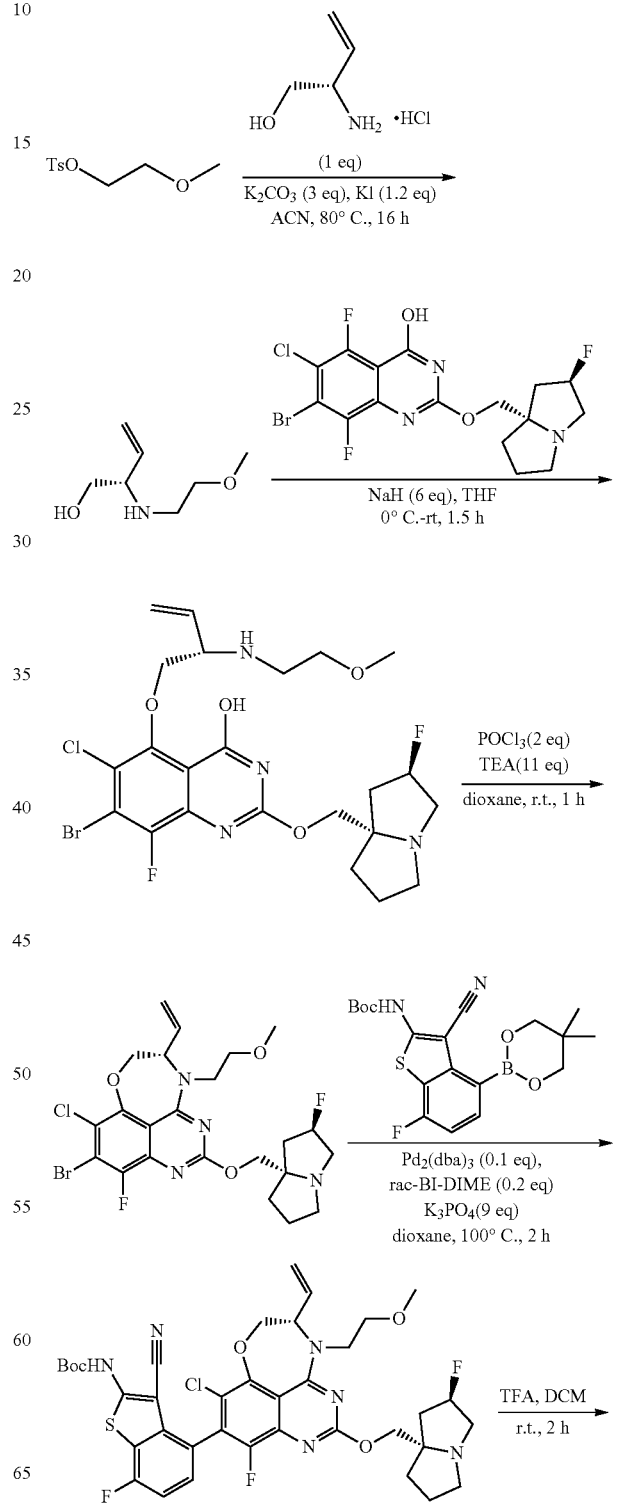

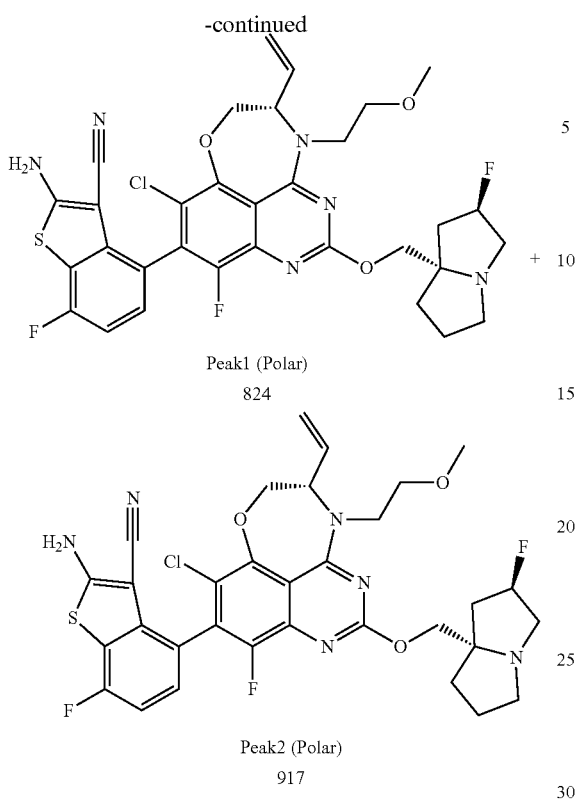

Peak1 (Polar)
824

Peak2 (Polar)
917

(2S)-2-[(2-methoxyethyl)amino]but-3-en-1-ol To a stirred solution of 2-methoxyethyl 4-methylbenzenesulfonate (748 mg, 3.248 mmol, 1 equiv) in anhydrous ACN (15 mL) was added (2S)-2-aminobut-3-en-1-ol (282 mg, 3.248 mmol, 1 equiv) and K$_2$CO$_3$ (1346.76 mg, 9.744 mmol, 3 equiv) followed by addition of KI (647 mg, 3.898 mmol, 1.2 equiv). The reaction mixture was stirred at 80° C. for a period of 16 hours. It was cooled down to room temperature, quenched by addition of water (30 mL), and extracted with DCM (3×20 mL). The extracts were combined, washed with brine (1×50 mL), and dried over anhydrous sodium sulfate. It was filtered, concentrated under reduced pressure to give crude product which was purified by column chromatography using 0% to 6% MeOH in DCM gradient to afford desired product as a yellow oil. (ESI, m/z): 146 [M+H]$^+$ 7-Bromo-6-chloro-8-fluoro-2-(((2R,7aS)-2-fluorotetrahydro-1H-pyrrolizin-7a(5H)-yl)methoxy)-5-(((S)-2-((2-methoxyethyl)amino)but-3-en-1-yl)oxy)quinazolin-4-ol To a stirred solution of (2S)-2-[(2-methoxyethyl)amino]but-3-en-1-ol (200 mg, 1.377 mmol, 1 equiv) in anhydrous THF (10 mL) was added NaH (330 mg, 8.262 mmol, 6 equiv, 60%) and 7-bromo-6-chloro-5,8-difluoro-2-(((2R,7aS)-2-fluorotetrahydro-1H-pyrrolizin-7a(5H)-yl)methoxy)quinazolin-4-ol (623 mg, 1.377 mmol, 1 equiv). The reaction mixture was stirred at room temperature for 1.5 hours. It was quenched by addition of water (20 mL), extracted with ethyl acetate (3×20 mL). The extracts were combined, washed with brine (1×40 mL), and dried over anhydrous sodium sulfate. It was filtered and concentrated under reduced pressure to give the desired product as a yellow solid which was used directly in the next step without further purification. (ESI, m/z):577 [M+H]$^+$ (S)-9-bromo-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino[5,6,7-de]quinazoline To a stirred solution of 7-bromo-6-chloro-8-fluoro-2-(((2R,7aS)-2-fluorotetrahydro-1H-pyrrolizin-7a(5H)-yl)methoxy)-5-(((S)-2-((2-methoxyethyl)amino)but-3-en-1-yl)oxy)quinazolin-4-ol (600 mg, 1.038 mmol, 1 equiv) in anhydrous dioxane (10 mL) was added triethylamine (1155 mg, 11.418 mmol, 11 equiv) and POCl$_3$ (318 mg, 2.076 mmol, 2 equiv). The reaction mixture was stirred at room temperature for 1 hour. It was quenched by addition of water (25 mL) and extracted with DCM (3×20 mL). The extracts were combined, washed with brine (1×40 mL), and dried over anhydrous sodium sulfate. It was filtered and concentrated under reduced pressure to give crude product which was purified by column chromatography using 0% to 6% MeOH in DCM gradient to afford desired the desired product as a yellow solid. (ESI, m/z):559 [M+H]$^+$ Tert-butyl (4-((5S)-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino[5,6,7-de]quinazolin-9-yl)-3-cyano-7-fluorobenzo[b]thiophen-2-yl)carbamate To a stirred solution of (S)-9-bromo-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino[5,6,7-de]quinazoline (200 mg, 0.357 mmol, 1 equiv) in anhydrous dioxane (8 mL) was added tert-butyl N-[3-cyano-4-(5,5-dimethyl-1,3,2-dioxaborinan-2-yl)-7-fluoro-1-benzothiophen-2-yl]carbamate (288 mg, 0.714 mmol, 2 equiv) and K$_3$PO$_4$ (682 mg, 3.213 mmol, 9 equiv) followed by catalytic amount of Pd2(dba)$_3$ (32 mg, 0.036 mmol, 0.1 equiv) and 3-tert-butyl-4-(2,6-dimethoxyphenyl)-2,3-dihydro[d]-[1,3]-oxaphosphole (23 mg, 0.071 mmol, 0.2 equiv). The reaction mixture was stirred at 100° C. for 2 hours under nitrogen atmosphere. It was cooled to room temperature, was quenched by addition of water (20 mL) and extracted with DCM (3×20 mL). The extracts were combined, washed with brine (1×40 mL), and dried anhydrous sodium sulfate. It was filtered and concentrated under reduced pressure to give crude product which was purified by column chromatography using 0% to 6% MeOH in DCM gradient to afford the desired product as a yellow solid. (ESI, m/z): 771 [M+H]$^+$ 2-Amino-4-(5S)-8-chloro-10-fluoro-2-(2R,7aS)-2-fluorotetrahydro-1H-pyrolizin-7a(5H)-yl)methoxy)-4-(2-methoxyethyl)-5-vinyl-5,6-dihydro-4H-[1,4]oxazepino[5,6,7-de]quinazolin-9-yl)-7-fluorobenzo[b]thiophene-3-carbonitrile (824 and 917) To a stirred solution of tert-butyl (4-((5S)-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino-[5,6,7-de]quinazolin-9-yl)-3-cyano-7-fluorobenzo[b]thiophen-2-yl)carbamate (180 mg, 0.233 mmol, 1 equiv) in anhydrous DCM (5 mL) was added TFA (1 mL). The reaction mixture was stirred at room temperature for 2 hours and concentrated under vacuum to give a crude. The crude product was purified by Prep-HPLC with the following conditions (Column: YMC Triart C18 ExRs 5 m, 30 mm*150 mm; Mobile Phase A: Water (10 mmol/L NH$_4$HCO$_3$), Mobile Phase B: ACN; Flow rate: 60 mL/min; Gradient: 50% B to 65% B in 10 min; Wave Length: UV 254 nm/220 nm; RT1(min): 8.38/9.17) to afford desired products (824) the first eluting (peak 1; polar) and (917) the second eluting (peak 2; less polar) as white solids.

824:(ESI, m/z): 671 [M+H]$^+$; $^1$H NMR (400 MHZ, DMSO-d$_6$, ppm) § 7.21 (dd, J=8.3, 5.0 Hz, 1H), 7.00 (t, J=8.8 Hz, 1H), 5.93 (m, 1H), 5.64 (s, 2H), 5.41-5.11 (m, 3H), 4.71 (dd, J=12.7, 4.7 Hz, 1H), 4.61 (m, 1H), 4.50-4.37 (m, 2H), 4.25 (m, 2H), 3.96 (m, 1H), 3.70 (m, 1H), 3.47 (m, 1H), 3.36 (s, 4H), 3.26 (m, 2H), 3.01 (s, 1H), 2.44-2.09 (m, 3H), 1.95 (d, J=12.1 Hz, 3H).

917:(ESI, m/z):671 [M+H]⁺; ¹H NMR: (400 MHz, DMSO-d₆, ppm) δ 7.17 (m, 1H), 6.97 (m, 1H), 6.15 (d, J=4.1 Hz, 2H), 5.97 (m, 1H), 5.40-5.10 (m, 3H), 4.78-4.63 (m, 2H), 4.59-4.49 (m, 1H), 4.43 (dd, J=12.8, 4.1 Hz, 1H), 4.26 (dd, J=10.3, 4.1 Hz, 1H), 4.19-4.07 (m, 1H), 3.94 (m, 1H), 3.75-3.62 (m, 1H), 3.45 (m, 1H), 3.36 (d, J=4.3 Hz, 4H), 3.27-3.12 (m, 2H), 3.00 (m, 1H), 2.38-2.08 (m, 3H), 2.03-1.83 (m, 3H).

Example 1bh: Synthesis of 2-amino-4-((5R)-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (959)

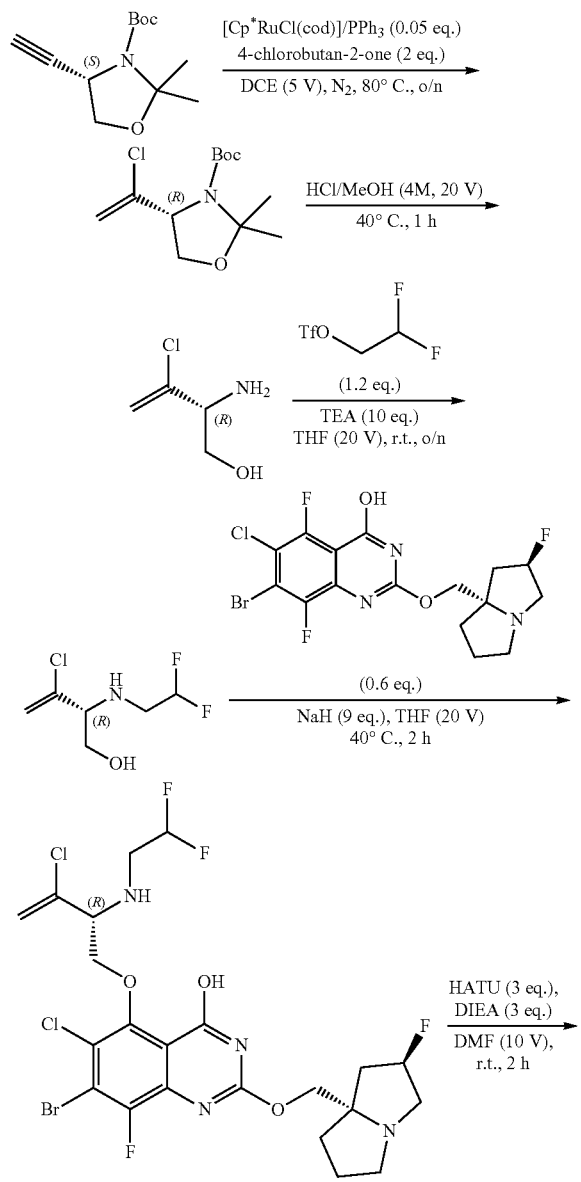

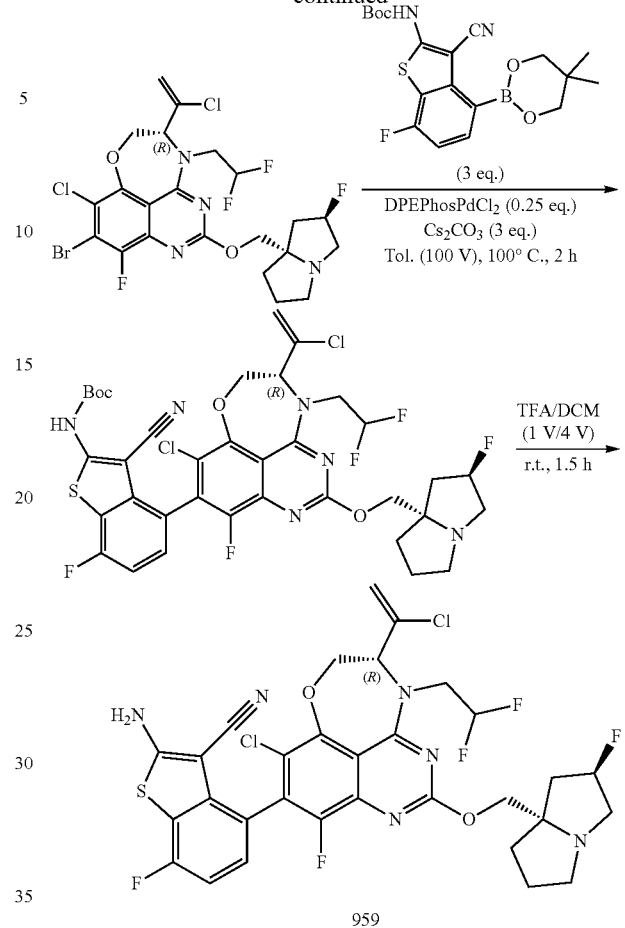

Tert-butyl (R)-4-(1-chlorovinyl)-2,2-dimethyloxazolidine-3-carboxylate To a stirred solution of chloro(1,5-cyclooctadiene)(pentamethylcyclopentadienyl)ruthenium(II) (0.25 g, 0.666 mmol, 0.05 equiv) and triphenylphosphine (0.17 g, 0.666 mmol, 0.05 equiv) in DCE (30 mL) were added tert-butyl (4S)-4-ethynyl-2,2-dimethyl-1,3-oxazolidine-3-carboxylate (3 g, 13.316 mmol, 1 equiv) and 4-chlorobutan-2-one (2.84 g, 26.632 mmol, 2 equiv) in portions at 80° C. under nitrogen atmosphere and stirred for overnight at the same temperature. It was cooled to room temperature, treated with water (50 mL) and extracted with CH₂Cl₂ (5×30 mL). The extracts were combined, washed with water (3×30 mL), and dried over anhydrous MgSO4. After filtration, the filtrate was concentrated under reduced pressure to give a residue. The residue was purified by silica gel column chromatography, eluted with petroleum/ethyl acetate (20:1) to afford the desired product as a yellow oil. (ESI, m/z):262 [M+H]⁺

(R)-2-amino-3-chlorobut-3-en-1-ol A solution of tert-butyl (R)-4-(1-chlorovinyl)-2,2-dimethyloxazolidine-3-carboxylate (650 mg, 2.483 mmol, 1 equiv) and HCl in MeOH (4 M, 15 mL) was stirred for 1 hour at 40° C. It was cooled and concentrated under reduced pressure the desired productas brown solid which was used in the next step directly without further purification. (ESI, m/z): 122[M+H]⁺

(2R)-3-chloro-2-[(2,2-difluoroethyl)amino]but-3-en-1-ol To a stirred solution of (2R)-2-amino-3-chlorobut-3-en-1-ol (480 mg, 2.448 mmol, 1 equiv, 62%) and triethylamine (3.4 mL, 24.480 mmol, 10 equiv) in THF (10 mL) was added 2,2-difluoroethyl trifluoromethanesulfonate (629 mg, 2.938 mmol, 1.2 equiv) at room temperature. The reaction was stirred for overnight at room temperature and concentrated under reduced pressure to give a residue. The residue was dissolved in DCM (20 mL), treated with water, and extracted with $CH_2Cl_2$ (3×20 mL). The extracts were combined, dried over anhydrous MgSO4. After filtration, the filtrate was concentrated under reduced pressure to give a residue. The residue was purified by silica gel column chromatography, eluted with $CH_2Cl_2$/MeOH (20:1) to the desired product as a yellow oil. (ESI, m/z): 186[M+H]$^+$ 7-Bromo-6-chloro-5-(((R)-3-chloro-2-((2,2-difluoroethyl)amino)but-3-en-1-yl)oxy)-8-fluoro-2-(((2R,7aS)-2-fluorotetrahydro-1H-pyrrolizin-7a(5H)-yl)methoxy)quinazolin-4-ol To a stirred solution of (2R)-3-chloro-2-[(2,2-difluoroethyl)amino]but-3-en-1-ol (205.01 mg, 1.105 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (300 mg, 0.663 mmol, 0.6 equiv) in THF (6 mL) was added NaH (238 mg, 9.945 mmol, 9 equiv) in portions at 0° C. The reaction was stirred for 2 hours at 40° C., cooled to room temperature, quenched with water at 0° C., and extracted with $CH_2Cl_2$ (5×30 mL). The extracts were combined, dried over anhydrous MgSO$_4$. After filtration, the filtrate was concentrated under reduced pressure to give the desired product as brown solid which was used in the next step directly without further purification. (ESI, m/z):617 [M+H]$^+$ (R)-9-bromo-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline To a stirred solution of 7-bromo-6-chloro-5-(((R)-3-chloro-2-((2,2-difluoroethyl)amino)but-3-en-1-yl)oxy)-8-fluoro-2-(((2R,7aS)-2-fluorotetrahydro-1H-pyrrolizin-7a(5H)-yl)methoxy)quinazolin-4-ol (325 mg, 0.473 mmol, 1 equiv, 90%) and DIEA (183 mg, 1.419 mmol, 3 equiv) in DMF (3 mL) was added HATU (539 mg, 1.419 mmol, 3 equiv), and the resulting mixture was stirred for 2 hours at room temperature. It was washed with 2×20 ml of water, extracted with ethyl acetate (5×30 mL). The extracts were combined, washed with water (5×30 mL), and dried over anhydrous MgSO$_4$. After filtration, the filtrate was concentrated under reduced pressure to give a residue. The residue was purified by reversed-phase flash chromatography with the following conditions (column, C18; mobile phase, MeCN in Water (10 mmol/L NH$_4$HCO$_3$), 40% to 70% gradient in 25 min; detector, UV 254/220 nm) to afford the desired product as a solid. (ESI, m/z): 599 [M+H]$^+$ Tert-butyl (4-((5R)-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-3-cyano-7-fluorobenzo[b]thiophen-2-yl)carbamate To a stirred solution of (R)-9-bromo-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazoline (108 mg, 0.180 mmol, 1 equiv) and tert-butyl N-[3-cyano-4-(5,5-dimethyl-1,3,2-dioxaborinan-2-yl)-7-fluoro-1-benzothiophen-2-yl]carbamate (218 mg, 0.540 mmol, 3 equiv) in toluene (5 mL) were added Cs$_2$CO$_3$ (175 mg, 0.540 mmol, 3 equiv) and dichloropalladium (2-[2-(diphenylphosphanyl)phenoxy]phenyl)diphenylphosphane (32 mg, 0.045 mmol, 0.25 equiv) at room temperature under argon atmosphere. The reaction was stirred for 2 hours at 100° C. under argon atmosphere. It was cooled to room temperature and concentrated under reduced pressure to give a residue. The residue was dissolved in DCM (20 mL), washed with 3×20 ml of water, and dried over anhydrous MgSO$_4$. After filtration, the filtrate was concentrated under reduced pressure to give a residue. The residue was purified by reversed-phase flash chromatography with the following conditions (column, C18; mobile phase, MeCN in Water (10 mmol/L NH$_4$HCO$_3$), 60% to 90% gradient in 15 min; detector, UV 254/220 nm) to afford the desired product as a solid. (ESI, m/z):811[M+H]$^+$ 2-Amino-4-((5R)-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile A solution of tert-butyl (4-((5R)-8-chloro-5-(1-chlorovinyl)-4-(2,2-difluoroethyl)-10-fluoro-2-(((2R,7aS)-2-fluorotetrahydro-1H-pyrrolizin-7a(5H)-yl) methoxy)-5,6-dihydro-4H-[1,4]oxazepino[5,6,7-de]quinazolin-9-yl)-3-cyano-7-fluorobenzo[b]thiophen-2-yl)carbamate (86 mg, 0.106 mmol, 1 equiv) and TFA (1 mL) in DCM (4 mL) was stirred for 1.5 hours at room temperature. The resulting mixture was concentrated under reduced pressure to give a residue. The residue was basified to PH~8 with saturated NaHCO$_3$(aq.) and extracted with DCM. The extracts were combined, washed with brine and dried overs Na$_2$SO$_4$. It was filtered and concentrated under vacuum to give a crude. The crude product was purified by Prep-HPLC with the following conditions (Column: YMC Triart C18 ExRs 5 m, 30 mm*150 mm; Mobile Phase A: Water (10 mmol/L NH$_4$HCO$_3$), Mobile Phase B: ACN; Flow rate: 60 mL/min; Gradient: 55% B to 75% B in 10 min; Wave Length: UV 254 nm/220 nm; RT1(min): 8.5/9.17) to afford the desired product as a white solid. (ESI, m/z):711 [M+H]$^+$ $^1$H NMR: (400 MHZ, DMSO-d$_6$, ppm) § 8.10 (brs, 2H), 7.25-7.22 (m, 1H), 7.14-7.10 (m, 1H), 6.68-6.41 (m, 1H), 5.57-5.56 (m, 1H), 5.43-5.42 (m, 1H), 5.35-5.21 (m, 1H), 5.05 (dd, J1=13.36 Hz, J2=4.52 Hz, 1H), 4.90-4.89 (m, 1H), 4.62-4.51 (m, 1H), 4.40 (d, J=13.08 Hz, 1H), 4.13 (d, J=10.28 Hz, 1H), 4.03 (d, J=10.2 Hz, 1H), 3.86-3.80 (m, 1H), 3.09-3.08 (m, 2H), 3.04-3.01 (m, 1H), 2.83-2.82 (m, 1H), 2.18-2.12 (m, 1H), 2.06-2.01 (m, 2H), 1.86-1.77 (m, 3H).

Example 1bi: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4] oxazepino[5,6,7-de]quinazolin-9-yl)-7-fluorobenzo[b]thiophene-3-carbonitrile (849)

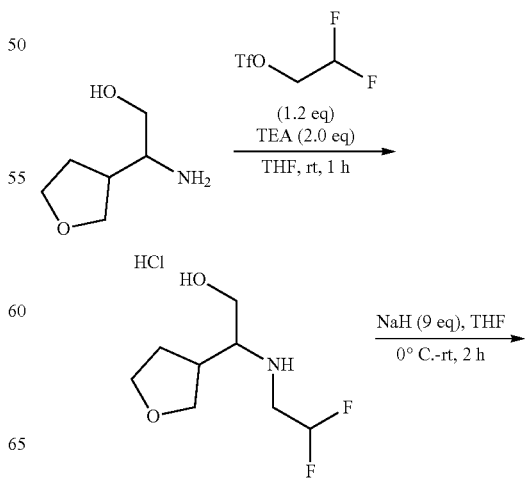

1419

-continued

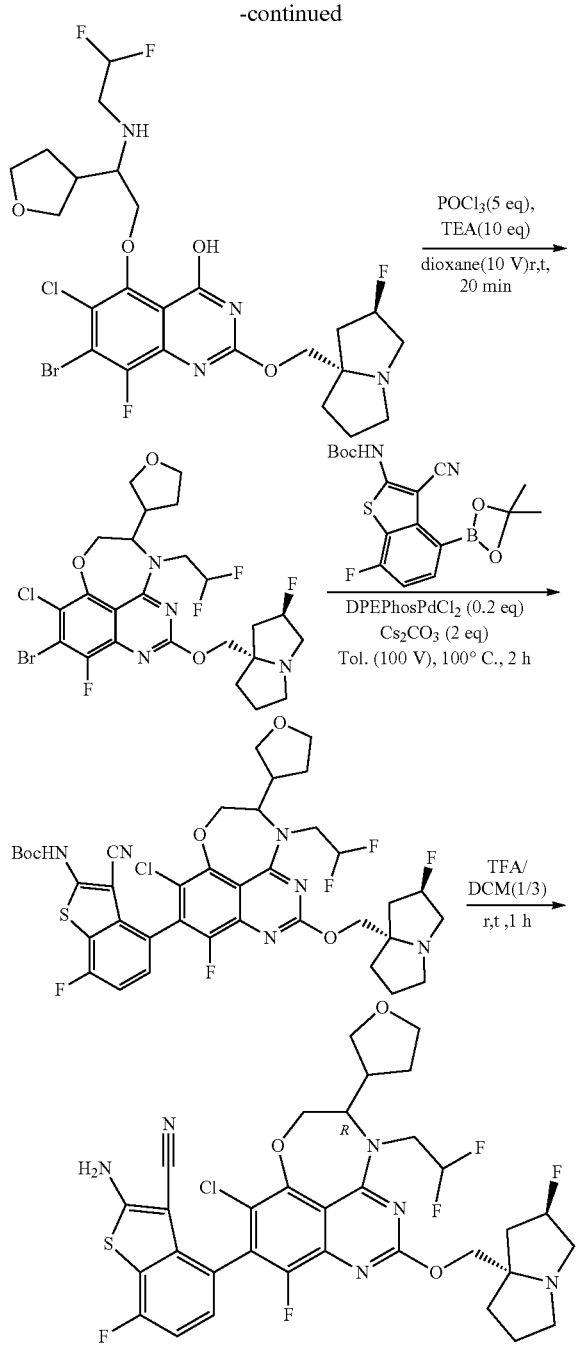

849

2-((2,2-Difluoroethyl)amino)-2-(tetrahydrofuran-3-yl)ethan-1-ol To a stirred solution of 2-amino-2-(tetrahydrofuran-3-yl)ethan-1-ol (840 mg, 3.202 mmol, 1 equiv, 50%) in THF (10 mL) was added triethylamine (972 mg, 9.606 mmol, 3 equiv) in portions at room temperature under nitrogen atmosphere. The resulting mixture was stirred for 1 hour and extracted with $CH_2Cl_2$ (2×50 mL). The extracts were combined, washed with water (2×50 mL), and dried over anhydrous $Na_2SO_4$. After filtration, the filtrate was concentrated under reduced pressure to give a residue. The residue was purified by silica gel column chromatography, eluted with $CH_2Cl_2/MeOH$ (10:1) to afford the desired product as a yellow oil. (ESI, m/z): 195 [M+H]$^+$

1420

7-Bromo-6-chloro-5-(2-((2,2-difluoroethyl)amino)-2-(tetrahydrofuran-3-yl)ethoxy)-8-fluoro-2-(((2R,7aS)-2-fluorotetrahydro-1H-pyrrolizin-7a(5H)-yl)methoxy)quinazolin-4-ol To a stirred solution of 2-((2,2-difluoroethyl)amino)-2-(tetrahydrofuran-3-yl)ethan-1-ol (200 mg, 1.025 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (463 mg, 1.025 mmol, 1 equiv) in THF (4 mL) were added NaH (221 mg, 9.225 mmol, 9 equiv) at 0° C. under nitrogen atmosphere. The resulting mixture was stirred for 2 hours at 0° C. under nitrogen atmosphere and diluted with $CH_2Cl_2$ (2×50 mL). It was quenched with water at 0° C. and organic layers were separated, washed with brine (1×40 mL), and dried over anhydrous $Na_2SO_4$. After filtration, the filtrate was concentrated under reduced pressure to give the desired product as a yellow solid which was used directly in the next step without further purification. (ESI, m/z): 627[M+H]$^+$ 9-Bromo-8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazoline To a stirred solution of 7-bromo-6-chloro-5-(2-((2,2-difluoroethyl)amino)-2-(tetrahydrofuran-3-yl)ethoxy)-8-fluoro-2-(((2R,7aS)-2-fluorotetrahydro-1H-pyrrolizin-7a(5H)-yl)methoxy)quinazolin-4-ol (700 mg, 0.892 mmol, 1 equiv, 80%) in dioxane (7 mL) were added triethyl amine (902 mg, 8.920 mmol, 10 equiv) and $POCl_3$ (683 mg, 4.460 mmol, 5 equiv) in portions at room temperature for 20 minutes under nitrogen atmosphere. The reaction was quenched by the addition of Water (20 mL) at 0° C. and the resulting mixture was extracted with $CH_2Cl_2$. The extracts were combined, washed with brine (1×20 mL), and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 10% to 90% gradient in 20 min; detector, UV 254 nm to afford the desired product as a yellow solid. (ESI, m/z):609 [M+H]$^+$ Tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate To a stirred solution of 9-bromo-8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazoline (240 mg, 0.394 mmol, 1 equiv) and tert-butyl N-[3-cyano-4-(4,4-dimethyl-1,3,2-dioxaboretan-2-yl)-7-fluoro-1-benzothiophen-2-yl]carbamate (222 mg, 0.591 mmol, 1.5 equiv) in toluene (3 mL) were added $Cs_2CO_3$ (256 mg, 0.788 mmol, 2 equiv) and dichloropalladium (2-[2-(diphenylphosphanyl)phenoxy]phenyl)diphenylphosphane (56 mg, 0.079 mmol, 0.2 equiv) in portions at room temperature under nitrogen atmosphere. The resulting mixture was stirred for 2 hours at 100° C. under nitrogen atmosphere. It was cooled to room temperature, quenched with water (20 mL), and extracted with $CH_2Cl_2$. The extracts were combined, washed with brine (1×20 mL), and dried over anhydrous $Na_2SO_4$. After filtration, the filtrate was concentrated under reduced pressure to give a resdiue. The residue was purified by reversed-phase flash chromatography with the following conditions: column, C18; mobile phase, MeCN in Water (10 mmol/L NH₄HCO₃), 20% to 90% gradient in 20 min; detector, UV 254 nm to give the desired product as a yellow solid. (ESI, m/z): 820[M+H]⁺

2-Amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazolin-9-yl)-7-fluorobenzo[b]thiophene-3-carbonitrile To a stirred solution of tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazolin-9-yl)-3-cyano-7-fluorobenzo[b]thiophen-2-yl)carbamate (185 mg, 0.225 mmol, 1 equiv) in DCM (3 mL) were added TFA (1 mL) dropwise at room temperature under nitrogen atmosphere. The resulting mixture was stirred for 1 hour at room temperature and neutralized to pH~10 with NH₃. H₂O. It was concentrated under reduced pressure to give a crude. The crude product was purified by Prep-HPLC with the following conditions (Column: YMC Triart C18 ExRs 5 m, 30 mm*150 mm; Mobile Phase A: Water (10 mmol/L NH₄HCO₃), Mobile Phase B: ACN; Flow rate: 60 mL/min; Gradient: 48% B to 68% B in 10 min; Wave Length: UV 254 nm/220 nm; RT1(min): 8.67/9.33) to afford mixture product. This product was purified by Prep-CHIRAL-HPLC with the following conditions(Column: CHIRAL ART Cellulose-SB 3*25 cm, 5m; Mobile Phase A: HEX(0.1% DEA), Mobile Phase B: IPA: DCM=1: 1; Flow rate: 40 mL/min; Gradient: isocratic 25; Wave Length: UV 254/220 nm; RT1(min): 11.5; RT2(min): 19; Sample Solvent: MeOH) to afford the desired product as a white solid. (ESI, m/z):720.9 [M+H]⁺

¹H NMR: (400 MHZ, DMSO-d₆, ppm) 88.10 (s, 2H), 7.27 (dd, J=8.4, 5.2 Hz, 1H), 7.15 (dd, J=9.6, 8.4 Hz, 1H), 6.62-6.32 (m, 1H), 5.38-5.20 (m, 1H), 4.92 (dd, J=13.0, 5.0 Hz, 1H), 4.88-4.75 (m, 1H), 4.53 (d, J=12.8 Hz, 1H), 4.17-3.94 (m, 3H), 3.85-3.75 (m, 1H), 3.70-3.49 (m, 4H), 3.09 (s, 2H), 3.02 (s, 1H), 2.83 (s, 1H), 2.54 (s, 1H), 2.25-1.94 (m, 4H), 1.94-1.58 (m, 4H).

Example 1bj: Synthesis of 2-amino-4-(8-chloro-4-(2,2-difluoroethyl)-10-fluoro-2-(((2R,7aS)-2-fluoro-tetrahydro-1H-pyrrolizin-7a(5H)-yl)methoxy)-5-(oxetan-3-yl)-5,6-dihydro-4H-[1,4]oxazepino[5,6,7-de]quinazolin-9-yl)-7-fluorobenzo[b]thiophene-3-carbonitrile (866 and 1100)

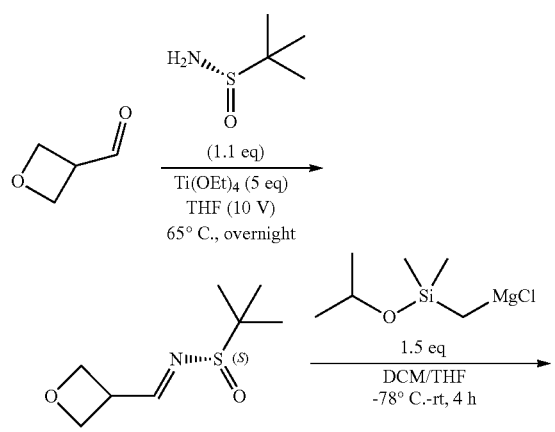

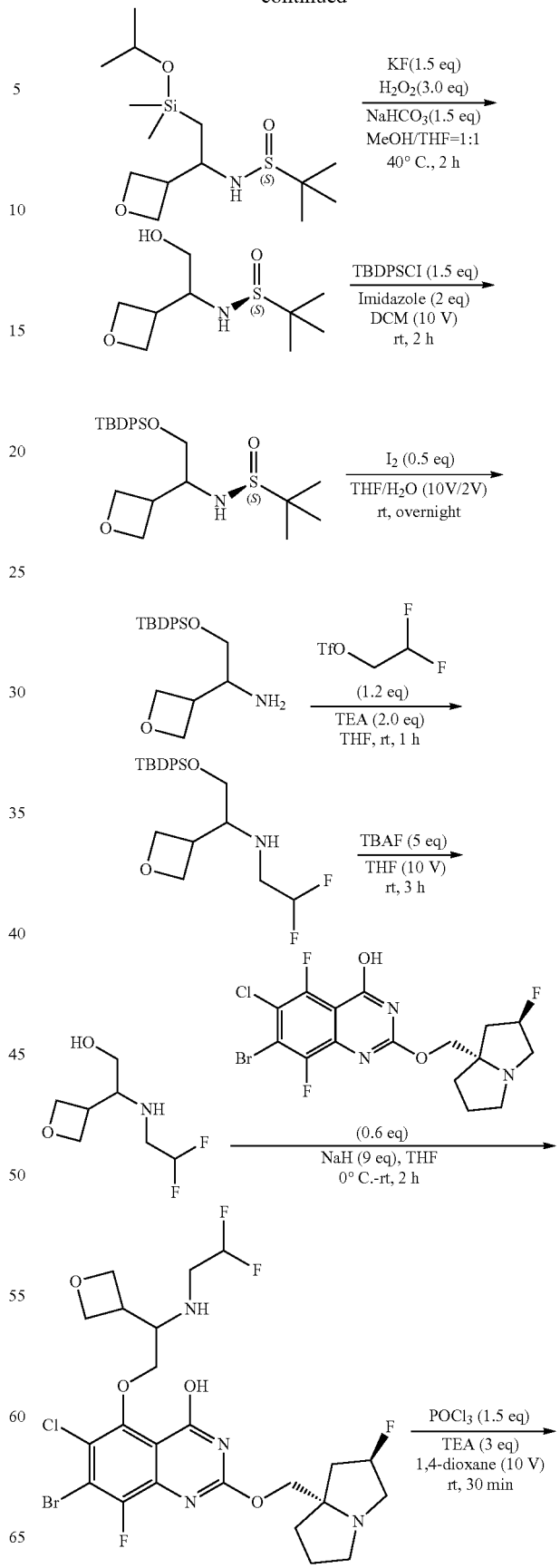

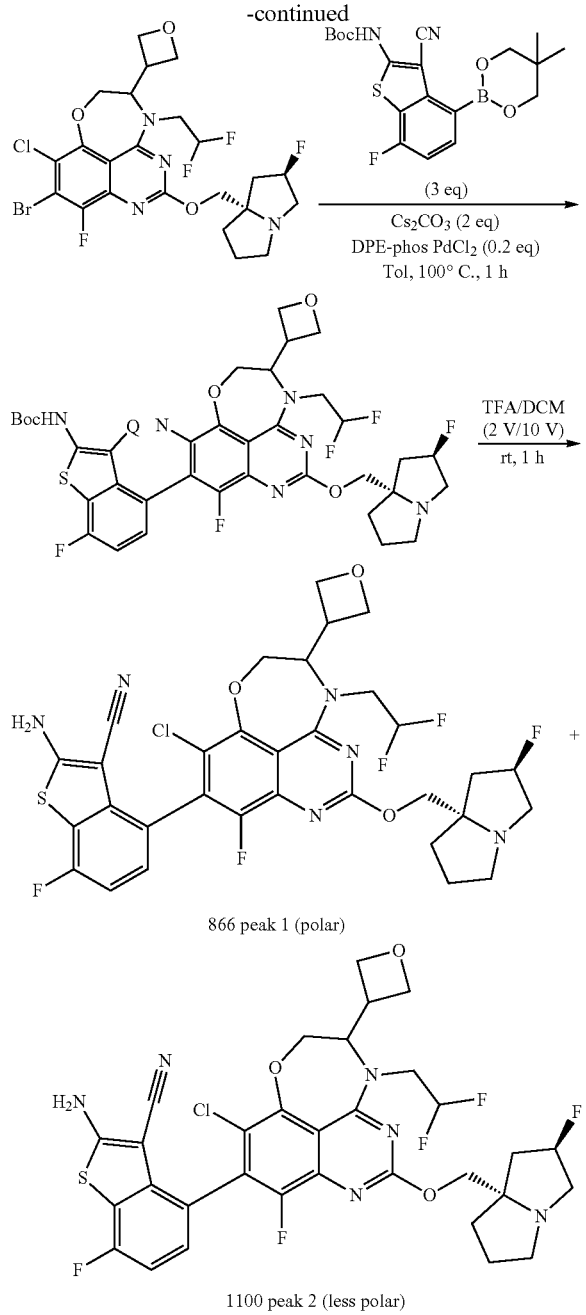

(S)-2-methyl-N-(oxetan-3-ylmethylidene)propane-2-sulfinamide To a stirred mixture of oxetane-3-carbaldehyde (5 g, 58.079 mmol, 1 equiv) and (S)-2-methylpropane-2-sulfinamide (7.74 g, 63.887 mmol, 1.1 equiv) in THF (50 mL) was added Ti(OEt)$_4$ (66.24 g, 290.395 mmol, 5 equiv) in portions at room temperature under nitrogen atmosphere. The resulting mixture was stirred for overnight at 65° C. under nitrogen atmosphere. It was cooled down to room temperature, quenched with water. The resulting mixture was filtered and the filter cake was washed with ethyl acetate (2×30 mL). The filtrates were combined, concentrated under reduced pressure to give a residue. The residue was purified by silica gel column chromatography, eluted with petroleum/ethyl acetate (3:1) to the desired product as a white solid. (ESI, m/z): 190 [M+H]$^+$ (S)—N-(2-(isopropoxydimethylsilyl)-1-(oxetan-3-yl)ethyl)-2-methylpropane-2-sulfinamide To a stirred solution of (S)-2-methyl-N-(oxetan-3-ylmethylidene)propane-2-sulfinamide (4.6 g, 24.304 mmol, 1 equiv) in DCM (50 mL) was added [(chloromagnesio)methyl](isopropoxy)dimethylsilane (6.96 g, 36.456 mmol, 1.5 equiv) in THF (50 mL) dropwise at −78° C. under nitrogen atmosphere. The resulting mixture was stirred for 3 hours at −78° C. and warmed to room temperature and stirred for additional 1 hour under nitrogen atmosphere. It was quenched with water at room temperature and extracted with CH$_2$Cl$_2$ (3×20 mL). The extracts were combined, washed with brine (2×20 mL), and dried over anhydrous Na$_2$SO$_4$. After filtration, the filtrate was concentrated under reduced pressure to give the desired product which was used in the next step directly without further purification. (ESI, m/z): 322 [M+H]$^+$ (S)—N-(2-hydroxy-1-(oxetan-3-yl)ethyl)-2-methylpropane-2-sulfinamide To a stirred solution of (S)—N-(2-(isopropoxydimethylsilyl)-1-(oxetan-3-yl)ethyl)-2-methylpropane-2-sulfinamide (5.8 g, 18.038 mmol, 1 equiv) in MeOH (25 mL) and THF (25 mL) were added KF (1.57 g, 27.057 mmol, 1.5 equiv), H$_2$O$_2$ (1.23 g, 36.076 mmol, 2 equiv) and NaHCO$_3$ (2.27 g, 27.057 mmol, 1.5 equiv) in portions at room temperature under nitrogen atmosphere. The resulting mixture was stirred for 2 hours at 40° C. and cooled to room temperature. It was concentrated under reduced pressure to give a residue. The residue was dissolved in DCM (40 mL), dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10:1) to afford the desired product as a colorless oil. (ESI, m/z): 222 [M+H]$^+$ (S)—N-(2-((tert-butyldiphenylsilyl)oxy)-1-(oxetan-3-yl)ethyl)-2-methylpropane-2-sulfinamide To a stirred mixture of (S)—N-(2-hydroxy-1-(oxetan-3-yl)ethyl)-2-methylpropane-2-sulfinamide (2.2 g, 9.940 mmol, 1 equiv) and TBDPSCl (4.10 g, 14.910 mmol, 1.5 equiv) in DCM (20 mL) was added imidazole (1.35 g, 19.880 mmol, 2 equiv) in portions at room temperature under nitrogen atmosphere. The resulting mixture was stirred for 2 hours at room temperature and quenched with water, extracted with CH$_2$Cl$_2$ (3×20 mL). The extracts were combined, washed with brine (2×20 mL), and dried over anhydrous Na$_2$SO$_4$. After filtration, the filtrate was concentrated under reduced pressure to give a residue. The residue was purified by silica gel column chromatography, eluted with CH$_2$Cl$_2$/MeOH (10:1) to afford the desired product as a colorless oil. (ESI, m/z): 460 [M+H]$^+$ 2-((Tert-butyldiphenylsilyl)oxy)-1-(oxetan-3-yl)ethan-1-amine To a stirred solution of (S)—N-(2-((tert-butyldiphenylsilyl)oxy)-1-(oxetan-3-yl)ethyl)-2-methylpropane-2-sulfinamide (2.3 g, 5.003 mmol, 1 equiv) in THF (20 mL) and H$_2$O (4 mL) was added I2 (0.63 g, 2.502 mmol, 0.5 equiv) in portions at room temperature under nitrogen atmosphere. The resulting mixture was stirred for overnight, quenched with sat. Na$_2$S$_2$O$_3$ (aq.) at room temperature, and extracted with CH$_2$Cl$_2$ (3×20 mL). The extracts were combined, washed with brine (2×10 mL), and dried over anhydrous Na$_2$SO$_4$. After filtration, the filtrate was concentrated under reduced pressure to give the desired product which was used in the next step directly without further purification. (ESI, m/z): 356 [M+H]$^+$ 2-((Tert-butyldiphenylsilyl)oxy)-N-(2,2-difluoroethyl)-1-(oxetan-3-yl)ethan-1-amine To a stirred solution of 2-((tert-butyldiphenylsilyl)oxy)-1-(oxetan-3-yl)ethan-1-amine (2.8 g, 7.875 mmol, 1 equiv) in THF (30 mL) were added triethylamine (1.59 g, 15.750 mmol, 2 equiv) and 2,2- difluoroethyl trifluoromethanesulfonate (2.02 g, 9.450 mmol, 1.2 equiv) dropwise at room temperature under nitrogen atmosphere. The resulting mixture was stirred for 1 hour, quenched with water at room temperature, and extracted with $CH_2Cl_2$ (3×20 mL). The extracts were combined, washed with brine (2×10 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a colorless oil. (ESI, m/z): 420 $[M+H]^+$ 2-((2,2-Difluoroethyl)amino)-2-(oxetan-3-yl)ethan-1-ol
To a stirred solution of 2-((tert-butyldiphenylsilyl)oxy)-N-(2,2-difluoroethyl)-1-(oxetan-3-yl)ethan-1-amine (1.5 g, 3.575 mmol, 1 equiv) in THF (15 mL) was added TBAF (4.67 g, 17.875 mmol, 5 equiv) dropwise at room temperature under nitrogen atmosphere. The resulting mixture was stirred for 3 hours and concentrated under reduced pressure to give a residue. The residue was purified by silica gel column chromatography, eluted with $CH_2Cl_2$/MeOH (10:1) to afford the desired product as a colorless oil. (ESI, m/z): 182 $[M+H]^+$ 7-Bromo-6-chloro-5-(2-((2,2-difluoroethyl)amino)-2-(oxetan-3-yl)ethoxy)-8-fluoro-2-(((2R,7aS)-2-fluorotetrahydro-1H-pyrrolizin-7a(5H)-yl)methoxy)quinazolin-4-ol To a stirred mixture of 2-((2,2-difluoroethyl)amino)-2-(oxetan-3-yl)ethan-1-ol (200 mg, 1.104 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (300 mg, 0.663 mmol, 0.60 equiv) in THF (4 mL) was added NaH (238 mg, 9.936 mmol, 9 equiv) in portions at 0° C. under nitrogen atmosphere. The resulting mixture was stirred for 2 hours at room temperature under nitrogen atmosphere, quenched with water/ice at 0° C., and extracted with $CH_2Cl_2$ (3×5 mL). The extracts were combined, washed with brine (2×5 mL), and dried over anhydrous $Na_2SO_4$. After filtration, the filtrate was concentrated under reduced pressure to give the desired product which was used in the next step directly without further purification. (ESI, m/z): 613 $[M+H]^+$ 9-Bromo-8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazoline To a stirred mixture of 7-bromo-6-chloro-5-(2-((2,2-difluoroethyl)amino)-2-(oxetan-3-yl)ethoxy)-8-fluoro-2-(((2R,7aS)-2-fluorotetrahydro-1H-pyrrolizin-7a(5H)-yl)methoxy)quinazolin-4-ol (310 mg, 0.505 mmol, 1 equiv) and triethylamine (153 mg, 1.515 mmol, 3 equiv) in 1,4-dioxane (3 mL) was added $POCl_3$ (116 mg, 0.758 mmol, 1.5 equiv) in portions at room temperature under nitrogen atmosphere. The resulting mixture was stirred for 30 minutes at room temperature, quenched with water/ice, and extracted with $CH_2Cl_2$ (3×5 mL). The extracts were combined, washed with brine (2×5 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a yellow solid. (ESI, m/z): 595 $[M+H]^+$ Tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazolin-9-yl)-3-cyano-7-fluorobenzo[b]thiophen-2-yl)carbamate To a stirred mixture of 9-bromo-8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazoline (120 mg, 0.201 mmol, 1 equiv) and tert-butyl N-[3-cyano-4-(5,5-dimethyl-1,3,2-dioxaborinan-2-yl)-7-fluoro-1-benzothiophen-2-yl]carbamate (244 mg, 0.603 mmol, 3 equiv) in Toluene (2 mL) was added $Cs_2CO_3$ (131 mg, 0.402 mmol, 2 equiv) and dichloropalladium; (2-[2-(diphenylphosphanyl)phenoxy]phenyl)diphenylphosphane (29 mg, 0.040 mmol, 0.2 equiv) in portions at room temperature under nitrogen atmosphere. The resulting mixture was stirred for 1 hour at 100° C. under nitrogen atmosphere. It was cooled to room temperature, quenched with water, and extracted with $CH_2Cl_2$ (3×5 mL). The extracts were combined, washed with brine (2×5 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desire product as a yellow solid. (ESI, m/z): 807 $[M+H]^+$ 2-Amino-4-(8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazolin-9-yl)-7-fluorobenzo[b]thiophene-3-carbonitrile (866 and 1100) To a stirred mixture of tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazolin-9-yl)-3-cyano-7-fluorobenzo[b]thiophen-2-yl)carbamate (60 mg, 0.074 mmol, 1 equiv) in DCM (0.6 mL) was added TFA (0.12 mL) dropwise at room temperature under nitrogen atmosphere. The resulting mixture was stirred for 1 hour at room temperature, basified to pH~8 with $NH_3 \cdot H_2O$ at 0° C., and extracted with $CH_2Cl_2$ (3×5 mL). The extracts were combined, washed with brine (2×5 mL), and dried over anhydrous $Na_2SO_4$. After filtration, the filtrate was concentrated under reduced pressure to give a crude. The crude product was purified by Prep-HPLC with the following conditions: Column: XBridge BEH Shield RP18 5 m, 30 mm×150 mm; Mobile Phase A: Water (10 mmol/L $NH_4HCO_3$), Mobile Phase B: ACN; Flow rate: 60 mL/min; Gradient: 35% B to 60% B in 10 min; Wave Length: UV 254 nm/220 nm; RT1(min): 9.07/9.82 to afford desired products: the first eluting (866; peak 1; polar) and afford the second eluting (1100; peak 2; less polar) (2.94 mg, 5.43%) as white solids.

866: (ESI, m/z): 707 $[M+H]^+$ $^1$H NMR:(400 MHZ, DMSO-$d_6$, ppm) 88.09 (s, 2H), 7.23 (dd, J=8.4, 5.2 Hz, 1H), 7.14 (dd, J=9.4, 8.4 Hz, 1H), 6.49 (t, J=56.2 Hz, 1H), 5.28 (d, J=54.4 Hz, 1H), 4.90 (dd, J=13.0, 4.9 Hz, 1H), 4.70 (dt, J=19.5, 6.8 Hz, 2H), 4.64-4.49 (m, 4H), 4.31 (d, J=12.9 Hz, 1H), 4.15-3.94 (m, 3H), 3.43-3.35 (m, 1H), 3.08 (d, J=7.7 Hz, 2H), 3.01 (s, 1H), 2.82 (s, 1H), 2.13 (d, J=9.1 Hz, 1H), 2.09-1.95 (m, 2H), 1.90-1.71 (m, 3H).

1100: (ESI, m/z): 707 $[M+H]^+$ $^1$H NMR:(400 MHZ, DMSO-$d_6$, ppm) § 8.13 (s, 2H), 7.27 (dd, J=8.4, 5.2 Hz, 1H), 7.15 (dd, J=9.6, 8.4 Hz, 1H), 6.47 (t, J=56.4 Hz, 1H), 5.28 (d, J=54.4 Hz, 1H), 4.89 (dd, J=13.0, 5.2 Hz, 1H), 4.65 (dt, J=9.2, 6.8 Hz, 2H), 4.59-4.53 (m, 3H), 4.50- 4.37 (m, 2H), 4.13-3.97 (m, 3H), 3.44-3.39 (m, 1H), 3.09 (s, 3H), 3.01 (s, 1H), 2.86-2.79 (m, 1H), 2.18-2.11 (m, 1H), 2.07-1.99 (m, 2H), 1.89-1.74 (m, 3H).

1427

Example 1bk: Synthesis of 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazolin-9-yl)-7-fluorobenzo[b]thiophene-3-carbonitrile (695)

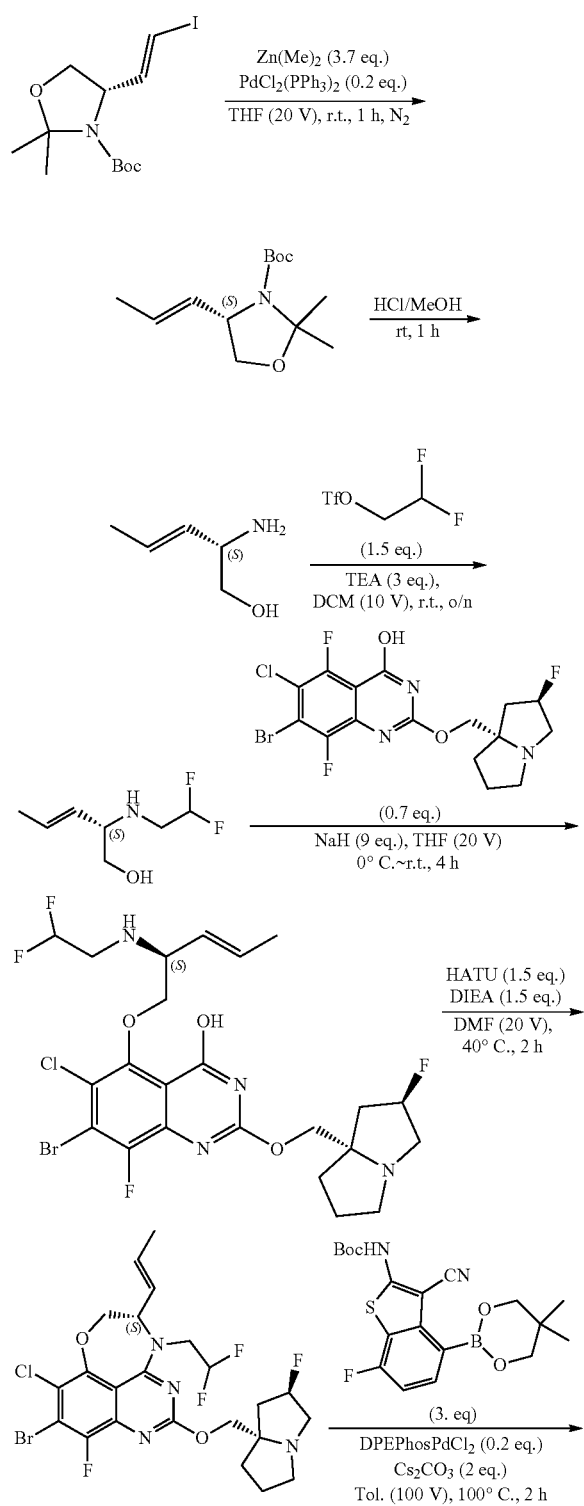

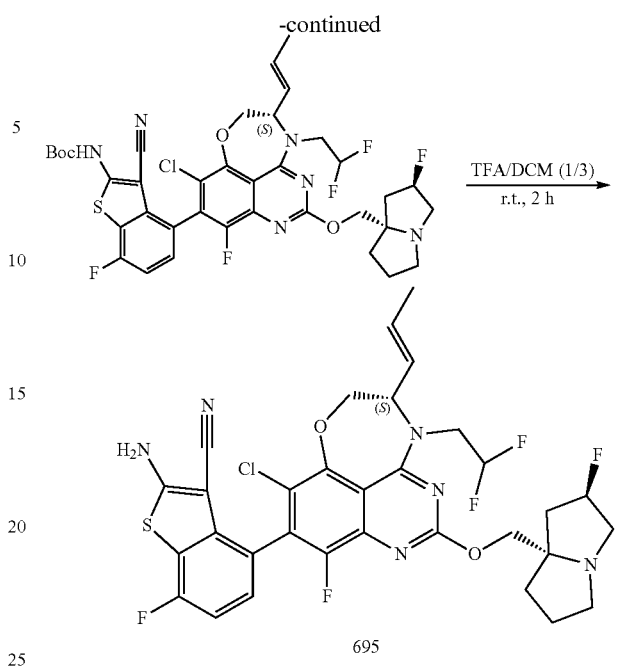

695

Tert-butyl (4S)-2,2-dimethyl-4-(prop-1-en-1-yl)-1,3-oxazolidine-3-carboxylate A solution of tert-butyl (4S)-4-(2-iodoethenyl)-2,2-dimethyl-1,3-oxazolidine-3-carboxylate (3 g, 8.494 mmol, 1 equiv) and dichloropalladium; bis(triphenylphosphane) (1.19 g, 1.699 mmol, 0.2 equiv) in THF (400 mL) was treated with dimethylzinc (31.6 mL, 1M in hexane, 3.7 equiv) at 0° C., and the mixture was stirred for 1 hour at room temperature. It was quenched with water and extracted with ethyl acetate (3×100 mL). The extracts were combined, dried over anhydrous $Na_2SO_4$. After filtration, the filtrate was concentrated under reduced pressure to give a residue. The residue was purified by silica gel column chromatography, eluted with petroleum/ethyl acetate (20:1) to afford the desired product as a colorless oil.

(S,E)-2-aminopent-3-en-1-ol A solution of tert-butyl (4S)-2,2-dimethyl-4-(prop-1-en-1-yl)-1,3-oxazolidine-3-carboxylate (500 mg, 2.072 mmol, 1 equiv) and HCl/MeOH (4M, 10 mL) was stirred for 1 hour at room temperature. The resulting mixture was concentrated under reduced pressure to give desired product which was used in the next step directly without further purification. (ESI, m/z): 102 $[M+H]^+$ 2-[(2,2-Difluoroethyl)amino]pent-3-en-1-ol A mixture of (2S,3E)-2-aminopent-3-en-1-ol (700 mg, 6.920 mmol, 1 equiv), Et3N (2100.91 mg, 20.760 mmol, 3 equiv) and 2,2-difluoroethyl trifluoromethanesulfonate (2222.62 mg, 10.380 mmol, 1.5 equiv) in DCM (62.2 mL) was stirred overnight at room temperature. The resulting mixture was concentrated under reduced pressure to give a residue. The residue was purified by reversed-phase flash chromatography with the following conditions: column, C18; mobile phase, $CH_3CN$ in Water (10 mmol/L $NH_4HCO_3$), 0% to 30% gradient in 10 min; detector, UV 254 nm to give the desired product as a light-yellow oil. (ESI, m/z): 166 $[M+H]^+$ 7-Bromo-6-chloro-5-(((S,E)-2-((2,2-difluoroethyl)amino)pent-3-en-1-yl)oxy)-8-fluoro-2-(((2R,7aS)-2-fluorotetrahydro-1H-pyrrolizin-7a(5H)-yl)methoxy)quinazolin-4-ol A solution of (2S,3E)-2-[(2,2-difluoroethyl)amino]pent-3-en-1-ol (200 mg, 1.211 mmol, 1 equiv) in THF (20.0 mL) was treated with NaH (261 mg, 10.899 mmol, 9 equiv) for 10 minutes at 0° C. followed by the addition of 7-bromo-6-chloro-5,8-difluoro-2-(((2R,7aS)-2-fluorotetrahydro-1H-pyrrolizin-7a(5H)-yl)methoxy)quinazolin-4-ol (383 mg, 0.848 mmol, 0.7 equiv) in portions at 0° C. The mixture was stirred for 4 hours at room temperature, quenched with water/ice at 0° C., and extracted with CH$_2$Cl$_2$ (3×20 mL). The extracts were combined, dried over anhydrous Na$_2$SO$_4$. After filtration, the filtrate was concentrated under reduced pressure the desired product which was used in the next step directly without further purification. (ESI, m/z): 597 [M+H]$^+$ (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazoline A solution of 7-bromo-6-chloro-5-(((S,E)-2-((2,2-difluoroethyl)amino)pent-3-en-1-yl)oxy)-8-fluoro-2-(((2R,7aS)-2-fluorotetrahydro-1H-pyrrolizin-7a(5H)-yl)methoxy)quinazolin-4-ol (800 mg, 1.338 mmol, 1 equiv), HATU (763.23 mg, 2.007 mmol, 1.5 equiv) and DIEA (259 mg, 2.007 mmol, 1.5 equiv) in DMF (45.71 mL) was stirred for 2 hours at 40° C. It was cooled to room temperature, quenched with water, and extracted with ethyl acetate (3×50 mL). The extracts were combined, dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 30% to 70% gradient in 10 min; detector, UV 254 nm to afford the desired product as a light-yellow solid. (ESI, m/z): 579 [M+H]$^+$ Tert-butyl (4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazolin-9-yl)-3-cyano-7-fluorobenzo[b]thiophen-2-yl)carbamate A mixture of (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazoline (160 mg, 0.276 mmol, 1 equiv), tert-butyl N-[3-cyano-4-(5,5-dimethyl-1,3,2-dioxaborinan-2-yl)-7-fluoro-1-benzothiophen-2-yl]carbamate (334 mg, 0.828 mmol, 3 equiv), dichloropalladium; (2-[2-(diphenylphosphanyl)phenoxy]phenyl)diphenylphosphane (40 mg, 0.055 mmol, 0.2 equiv) and Cs$_2$CO$_3$ (180 mg, 0.552 mmol, 2 equiv) in toluene (32 mL) was stirred for 2 hours at 100° C. under nitrogen atmosphere. It was cooled to room temperature, quenched with water, and extracted with CH$_2$Cl$_2$ (3×20 mL). The extracts were combined, dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 30% to 80% gradient in 10 min; detector, UV 254 nm to afford the desire product as a light-yellow solid. (ESI, m/z): 791 [M+H]$^+$ 2-Amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazolin-9-yl)-7-fluorobenzo[b]thiophene-3-carbonitrile A solution of tert-butyl (4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazolin-9-yl)-3-cyano-7-fluorobenzo[b]thiophen-2-yl)carbamate (78 mg, 0.099 mmol, 1 equiv) and trifluoroacetaldehyde (1 mL) in DCM (3 mL) was stirred for 2 hours at room temperature. It was concentrated under reduced pressure to give a residue. The residue was treated with DCM (10 mL) and water (20 mL) and extracted with CH$_2$Cl$_2$ (3×10 mL). The extracts were combined, dried over anhydrous Na$_2$SO$_4$. After filtration, the filtrate was concentrated under reduced pressure to give a crude. The crude product (100 mg) was purified by Prep-HPLC with the following conditions (Column: XBridge BEH Shield RP18 5 m, 30 mm*150 mm; Mobile Phase A: Water (10 mmol/L NH$_4$HCO$_3$), Mobile Phase B: ACN; Flow rate: 60 mL/min; Gradient: 50% B to 70% B in 10 min; Wave Length: UV 254 nm/220 nm; RT1(min): 8.4/9) to afford the desired product as a white solid. (ESI, m/z): 691 [M+H]$^+$ $^1$H NMR: (400 MHZ, DMSO-d$_6$, ppm) § 8.03 (brs, 2H), 7.17-7.14 (m, 1H), 7.06 (t, J=9.32 Hz, 1H), 6.59-6.28 (m, 1H), 5.68-5.59 (m, 1H), 5.52-5.47 (m, 1H), 5.28-5.14 (m, 1H), 4.73-4.69 (m, 1H), 4.49-4.48 (m, 1H), 4.45-4.37 (m, 1H), 4.26 (d, J=12.64 Hz, 1H), 4.03 (d, J=10.20 Hz, 1H), 3.95 (d, J=10.24 Hz, 1H), 3.73-3.62 (m, 1H), 3.02-3.01 (m, 2H), 2.98-2.94 (m, 1H), 2.78-2.73 (m, 1H), 2.11-2.05 (m, 1H), 2.01-1.94 (m, 2H), 1.84-1.66 (m, 3H), 1.61 (d, J=6.28 Hz, 3H).

Example 1b1: Synthesis of 2-amino-4-((5S)-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazolin-9-yl)-7-fluorobenzo[b]thiophene-3-carbonitrile (715)

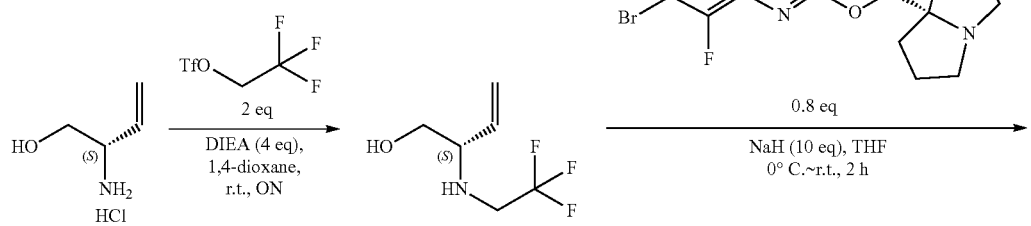

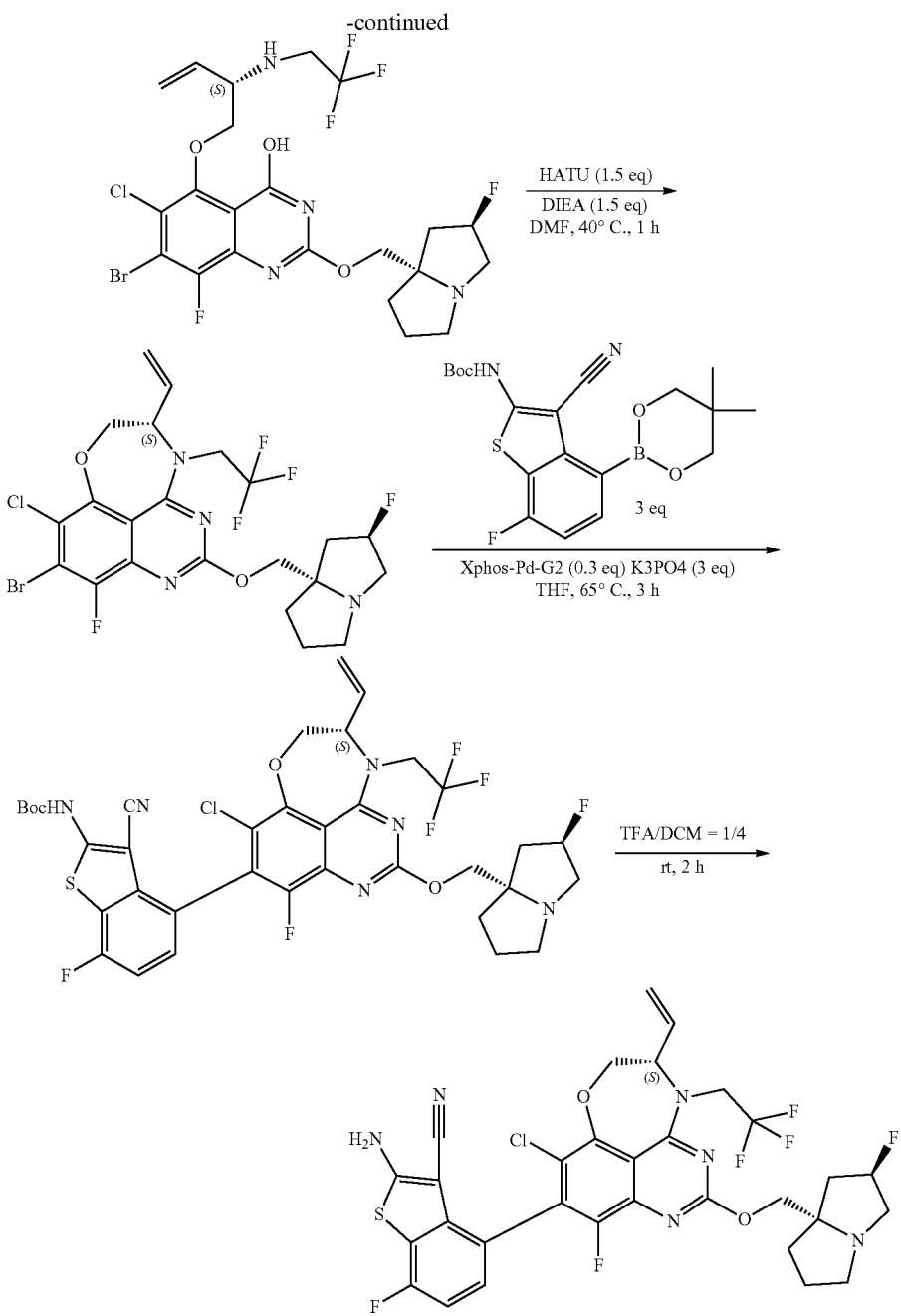

(2S)-2-[(2,2,2-trifluoroethyl)amino]but-3-en-1-ol A solution of (2S)-2-aminobut-3-en-1-ol hydrochloride (1 g, 8.092 mmol, 1 equiv) in 1,4-dioxane (20 mL) was treated with 2,2,2-trifluoroethyl trifluoromethanesulfonate (3.76 g, 16.184 mmol, 2 equiv) under nitrogen atmosphere followed by the addition of DIEA (4.18 g, 32.368 mmol, 4 equiv) dropwise portions at room temperature. The resulting mixture was stirred for overnight at room temperature and extracted with ethyl acetate (3×100 mL). The extracts were combined, washed with brine (3×30 mL), and dried over anhydrous $Na_2SO_4$. After filtration, the filtrate was concentrated under reduced pressure to give a residue. The residue was purified by silica gel column chromatography, eluted with petroleum/ethyl acetate (1:1) to afford the desired product as a colorless oil. (ESI, m/z): 170 [M+H]$^+$ 7-Bromo-6-chloro-8-fluoro-2-(((2R,7aS)-2-fluorotetrahydro-1H-pyrrolizin-7a(5H)-yl)methoxy)-5-(((S)-2-((2,2,2-trifluoroethyl)amino)but-3-en-1-yl)oxy)quinazolin-4-ol A solution of (2S)-2-[(2,2,2-trifluoroethyl)amino]but-3-en-1-ol (280 mg, 1.655 mmol, 1 equiv) in THF (3 mL) was treated with 7-bromo-6-chloro-5,8-difluoro-2-(((2R,7aS)-2-fluorotetrahydro-1H-pyrrolizin-7a(5H)-yl)methoxy)quinazolin-4-ol (599 mg, 1.324 mmol, 0.8 equiv) at room temperature under nitrogen atmosphere followed by the addition of NaH (662 mg, 16.550 mmol, 10 equiv, 60%) in portions at 0° C. The resulting mixture was stirred for 10 min at 0° C. and warmed up gradually to room temperature and stirred for additional 2 hour under nitrogen atmosphere. The resulting mixture was extracted with ethyl acetate (3×60 mL). The extracts were combined, washed with brine (3×30 mL), and dried over anhydrous Na$_2$SO$_4$. After filtration, the filtrate was concentrated under reduced pressure to give the desired product which was used in the next step directly without further purification. (ESI, m/z): 601 [M+H]$^+$ (S)-9-bromo-8-chloro-10-fluoro-2-(((2R,7aS)-2-fluoro-tetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazoline A solution of 7-bromo-6-chloro-8-fluoro-2-(((2R,7aS)-2-fluorotetrahydro-1H-pyrrolizin-7a(5H)-yl)methoxy)-5-(((S)-2-((2,2,2-trifluoroethyl)amino)but-3-en-1-yl)oxy)quinazolin-4-ol (900 mg, 1.496 mmol, 1 equiv) in DMF (26 mL) was treated with HATU (853 mg, 2.244 mmol, 1.5 equiv) at room temperature under nitrogen atmosphere followed by the addition of DIEA (290 mg, 2.244 mmol, 1.5 equiv) dropwise. The resulting mixture was stirred for 1 hour at 40° C. under nitrogen atmosphere and cooled down to room temperature. The resulting mixture was concentrated under reduced pressure to give a residue. The residue was purified by silica gel column chromatography, eluted with CH$_3$CN/H$_2$O (5:1) to afford the desired product as a yellow solid. (ESI, m/z): 583 [M+H]$^+$ Tert-butyl (4-((S)-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazolin-9-yl)-3-cyano-7-fluorobenzo[b]thiophen-2-yl)carbamate A solution of ((S)-9-bromo-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazoline (400 mg, 0.685 mmol, 1 equiv) in THF (40 mL) was treated with tert-butyl N-[3-cyano-4-(5,5-dimethyl-1,3,2-dioxaborinan-2-yl)-7-fluoro-1-benzothiophen-2-yl]carbamate (831 mg, 2.055 mmol, 3 equiv) and 2nd Generation XPhos Precatalyst/X-Phos aminobiphenyl palladium chloride precatalyst (162 mg, 0.206 mmol, 0.3 equiv) at room temperature under nitrogen atmosphere followed by the addition of K$_3$PO$_4$ (436 mg, 2.055 mmol, 3 equiv) at room temperature. The resulting mixture was stirred for 3 hours at 65° C. under nitrogen atmosphere and cooled down to room temperature. The resulting mixture was extracted with ethyl acetate (3×100 mL). The extracts were combined, washed with brine (3×30 mL), and dried over anhydrous Na$_2$SO$_4$. After filtration, the filtrate was concentrated under reduced pressure to give a residue. The residue was purified by silica gel column chromatography, eluted with CH$_3$CN/H$_2$O (5:1) to afford the desired product as a yellow solid. (ESI, m/z): 795 [M+H]$^+$ 2-Amino-4-((5S)-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazolin-9-yl)-7-fluorobenzo[b]thiophene-3-carbonitrile A solution of tert-butyl (4-((S)-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazolin-9-yl)-3-cyano-7-fluorobenzo[b]thiophen-2-yl)carbamate (300 mg, 0.377 mmol, 1 equiv) in DCM (4 mL) was treated with TFA (1 mL) at room temperature under nitrogen atmosphere. The resulting mixture was stirred for 2 hours and concentrated under reduced pressure to give a crude. The crude product (300 mg) was purified by Prep-HPLC with the following conditions (Column: XBridge BEH C18 OBD Prep Column 130, 5 m, 30 mm*150 mm; Mobile Phase A: Water (10 mmol/L NH$_4$HCO$_3$), Mobile Phase B: ACN; Flow rate: 60 mL/min; Gradient: 47% B to 67% B in 10 min; Wave Length: UV 254 nm/220 nm; RT1(min): 8.98) to afford a mixture (150 mg) as a white solid. Then the mixture (150 mg) was purified by Prep-CHIRAL-HPLC with the following conditions (Column: CHIRALPAK-IA 2*25 cm, 5m; Mobile Phase A: HEX(0.1% DEA), Mobile Phase B: EtOH:DCM=1: 1; Flow rate: 20 mL/min; Gradient: isocratic 30; Wave Length: UV 254/220 nm; RT1(min): 4.107; RT2(min): 7.783; Sample Solvent: EtOH; Injection Volume: 1.8 mL; Number Of Runs: 10) to afford the desired product as a white solid. (ESI, m/z): 695 [M+H]$^+$ $^1$H NMR: (400 MHZ, DMSO-d$_6$, ppm) δ 8.10 (s, 2H), 7.23 (dd, J=8.4, 5.2 Hz, 1H), 7.13 (dd, J=9.5, 8.4 Hz, 1H), 5.97 (ddd, J=17.2, 10.5, 4.8 Hz, 1H), 5.40-5.21 (m, 2H), 5.21-5.04 (m, 2H), 4.94 (dd, J=12.9, 4.9 Hz, 1H), 4.78 (t, J=5.0 Hz, 1H), 4.41 (m, 2H), 4.15 (s, 1H), 4.05 (s, 1H), 3.11-3.03 (m, 3H), 2.85 (s, 1H), 2.14 (s, 1H), 2.07-2.02 (m, 2H), 1.83 (m, 3H).

Example 1bm: Synthesis of 2-amino-4-((5S)-8-chloro-4-cyclobutyl-10-fluoro-2-(((2R,7aS)-2-fluoro-tetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (683)

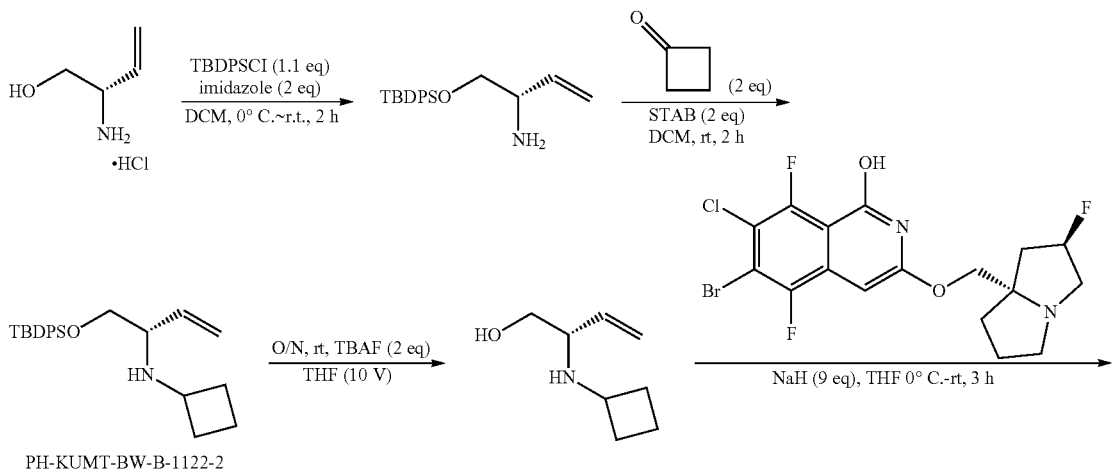

PH-KUMT-BW-B-1122-2

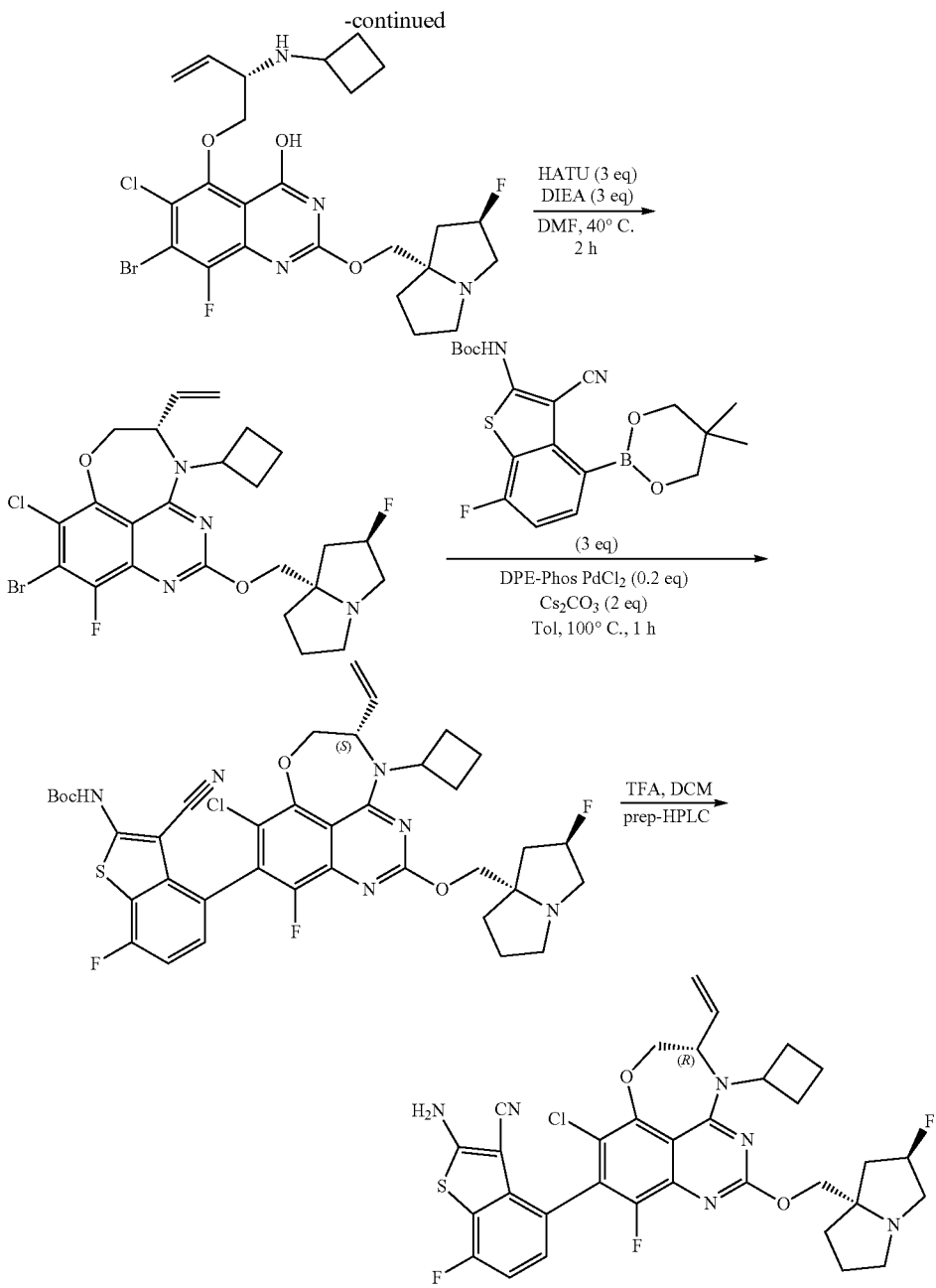

683

([(2S)-2-aminobut-3-en-1-yl]oxy(tert-butyl)diphenylsilane A solution of (2S)-2-aminobut-3-en-1-ol hydrochloride (600 mg, 4.855 mmol, 1 equiv) and imidazole (661 mg, 9.710 mmol, 2 equiv) in DCM (12 mL) was added TBDPSCl (1468 mg, 5.341 mmol, 1.1 equiv) and then stirred for 2 hours at room temperature under nitrogen atmosphere. The resulting mixture was diluted with DCM (50 mL). The mixture was washed with water (3×10 mL). It was dried over sodium sulfate, filtered and concentrated under vacuum to give a residue. The residue was purified by silica gel column chromatography, eluted with petroleum/ethyl acetate (5:1) to the desired product as a colorless oil. (ESI, m/z):326.15 [M+H]$^+$ N-[(2S)-1-[(tert-butyldiphenylsilyl)oxy]but-3-en-2-yl]cyclobutanamine A solution of ([(2S)-2-aminobut-3-en-1-yl]oxy(tert-butyl)diphenylsilane (400 mg, 1.229 mmol, 1 equiv) and cyclobutanone (172 mg, 2.458 mmol, 2 equiv) in DCM (4 mL) was added sodium triacetoxyboronate (521 mg, 2.458 mmol, 2 equiv) and the mixture was stirred for 2 hours at room temperature under nitrogen atmosphere. The mixture was diluted with DCM (20 mL). washed with water (3×10 mL). The organics were dried over sodium sulfate, filtered and concentrated under vacuum to give a residue. The residue was purified by silica gel column chromatography, eluted with petroleum/ethyl acetate (5:1) to afford the desired product as a colorless oil. (ESI, m/z):380.15 [M+H]$^+$ (2S)-2-(cyclobutylamino)but-3-en-1-ol A solution of N-[(2S)-1-[(tert-butyldiphenylsilyl)oxy]but-3-en-2-yl]cyclobutanamine (200 mg, 0.527 mmol, 1 equiv) in THF (2 mL) was added TBAF (1 mL) and the mixture was stirred for overnight at room temperature under nitrogen atmosphere. The reaction was quenched with water (20 mL) and the aqueous layer was extracted with ethyl acetate (3×10 mL). The combined extracts were washed with water (3×10 mL) and dried over sodium sulfate. It was filtered and solvent was removed under reduced pressure to give a residue. The residue was purified by silica gel column chromatography, eluted with $CH_2Cl_2$/MeOH (10:1) to afford the desired product as a yellow oil. (ESI, m/z): 142.10 $[M+H]^+$ 7-Bromo-6-chloro-5-(((S)-2-(cyclobutylamino)but-3-en-1-yl)oxy)-8-fluoro-2-(((2R,7aS)-2-fluorotetrahydro-1H-pyrrolizin-7a(5H)-yl)methoxy)quinazolin-4-ol A solution of (2S)-2-(cyclobutylamino)but-3-en-1-ol (450 mg, 1.593 mmol, 1 equiv, 50%) in THF (12.5 mL) was treated with NaH (344.13 mg, 14.337 mmol, 9 equiv) for 30 min at 0° C. under nitrogen atmosphere followed by the addition of 6-bromo-7-chloro-5,8-difluoro-3-(((2R,7aS)-2-fluorotetrahydro-1H-pyrrolizin-7a(5H)-yl)methoxy)isoquinolin-1-ol (216 mg, 0.478 mmol, 0.30 equiv) dropwise at 0° C. The resulting mixture was stirred for 3 hours at room temperature under nitrogen atmosphere and quenched with water at 0° C. The aqueous layer was extracted with ethyl acetate (3×10 mL). The extracts were combined, washed with brine, and dried over sodium sulfate. It was filtered and solvent was removed under reduced pressure to afford the desired product as a yellow solid which was used directly in the next step without further purification. (ESI, m/z):573.10 $[M+H]^+$ (S)-9-bromo-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazoline A solution of 7-bromo-6-chloro-5-(((S)-2-(cyclobutylamino)but-3-en-1-yl)oxy)-8-fluoro-2-(((2R,7aS)-2-fluorotetrahydro-1H-pyrrolizin-7a(5H)-yl)methoxy)quinazolin-4-ol (356 mg, 0.310 mmol, 1 equiv, 50%), DIEA (120.27 mg, 0.930 mmol, 3 equiv) and HATU (353 mg, 0.930 mmol, 3 equiv) in DMF (2.0 mL) was stirred for 2 hours at 40° C. under nitrogen atmosphere. It was cooled down to room temperature, filtered and the filter cake was washed with DMF (2×2 mL). The mixture was purified by reverse phase column with the following conditions (0.5% $NH_4HCO_3$ in water, 65%) to afford the desired product as a yellow solid. (ESI, m/z):557.05 $[M+H]^+$ Tert-butyl (4-((5S)-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-3-cyano-7-fluorobenzo[b]thiophen-2-yl)carbamate A solution of (S)-9-bromo-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazoline (140 mg, 0.252 mmol, 1 equiv) and tert-butyl (3-cyano-4-(5,5-dimethyl-1,3,2-dioxaborinan-2-yl)-7-fluorobenzo[b]thiophen-2-yl)carbamate (204 mg, 0.504 mmol, 2 equiv) dichloropalladium; {2-[2-(diphenylphosphanyl)phenoxy]phenyl}diphenylphosphane (36 mg, 0.050 mmol, 0.2 equiv), $Cs_2CO_3$ (164 mg, 0.504 mmol, 2 equiv) in toluene (15 mL) was stirred for 1 hour at 100° C. under nitrogen atmosphere. I was cooled to room temperature, filtered, the filter cake was washed with DCM (3×10 mL). The filtrate was concentrated under reduced pressure to give a residue. The residue was purified by reverse phase flash with the following conditions (0.5% $NH_4HCO_3$ in water, 82%) to afford the desired product as a yellow solid. (ESI, m/z):767.10 $[M+H]^+$2-Amino-4-((5S)-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile A solution of tert-butyl (4-((5S)-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-3-cyano-7-fluorobenzo[b]thiophen-2-yl)carbamate (80 mg, 0.104 mmol, 1 equiv) in DCM (3 mL) was added TFA (1 mL) and the mixture was stirred for 1 hour at room temperature under nitrogen atmosphere. The resulting mixture was concentrated under vacuum to give a residue. The residue was basified to pH=7 with $NH_3 \cdot H_2O$ and concentrate to give a crude. The crude product (80 mg) was purified by Prep-HPLC with the following conditions (Column: XBridge BEH Shield RP18 5 m, 30 mm*150 mm; Mobile Phase A: Water (10 mmol/L $NH_4HCO_3$), Mobile Phase B: ACN; Flow rate: 60 mL/min; Gradient: 49% B to 65% B in 10 min; Wave Length: UV 254 nm/220 nm; RT1(min): 8.93/9.58) to afford crude. The crude was purified by Prep-Chiral HPLC with the following conditions: Column: CHIRALPAK-IA 2*25 cm, 5m; Mobile Phase A: HEX(0.1% DEA), Mobile Phase B: EtOH: DCM=1: 1; Flow rate: 20 mL/min; Gradient: isocratic 45; Wave Length: UV 254/220 nm; RT1(min): 4.29; RT2(min): 6.607; Injection Volume: 2.0 mL; Number Of Runs: 2 to afford the desired product as a white solid. (ESI, m/z):666.85 $[M+H]^+$ $^1$H NMR: (400 MHZ, DMSO-$d_6$, ppm) § 8.07 (s, 2H), 7.21 (dd, J=8.4, 5.2 Hz, 1H), 7.11 (dd, J=9.4, 8.4 Hz, 1H), 6.02 (m, 1H), 5.38-5.17 (m, 2H), 5.04-4.94 (m, 2H), 4.90-4.77 (m, 2H), 4.42-4.24 (m, 1H), 4.12 (m, 1H), 4.02 (m, 1H), 3.10 (d, J=9.2 Hz, 2H), 3.03 (s, 1H), 2.84 (d, J=7.2 Hz, 1H), 2.42-2.22 (m, 2H), 2.22-1.92 (m, 5H), 1.91-1.74 (m, 3H), 1.74-1.59 (m, 2H).

Example 1bn: Synthesis of 2-amino-4-((5S)-8-chloro-4-(dihydro-2H-313-pyran-3(4H)-yl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (996)

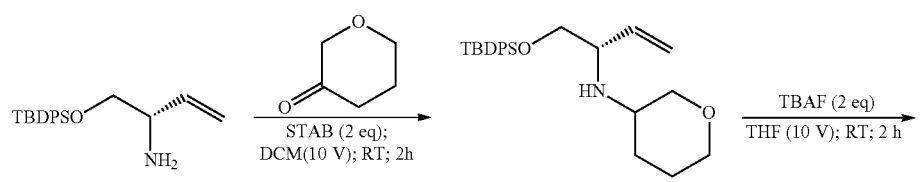

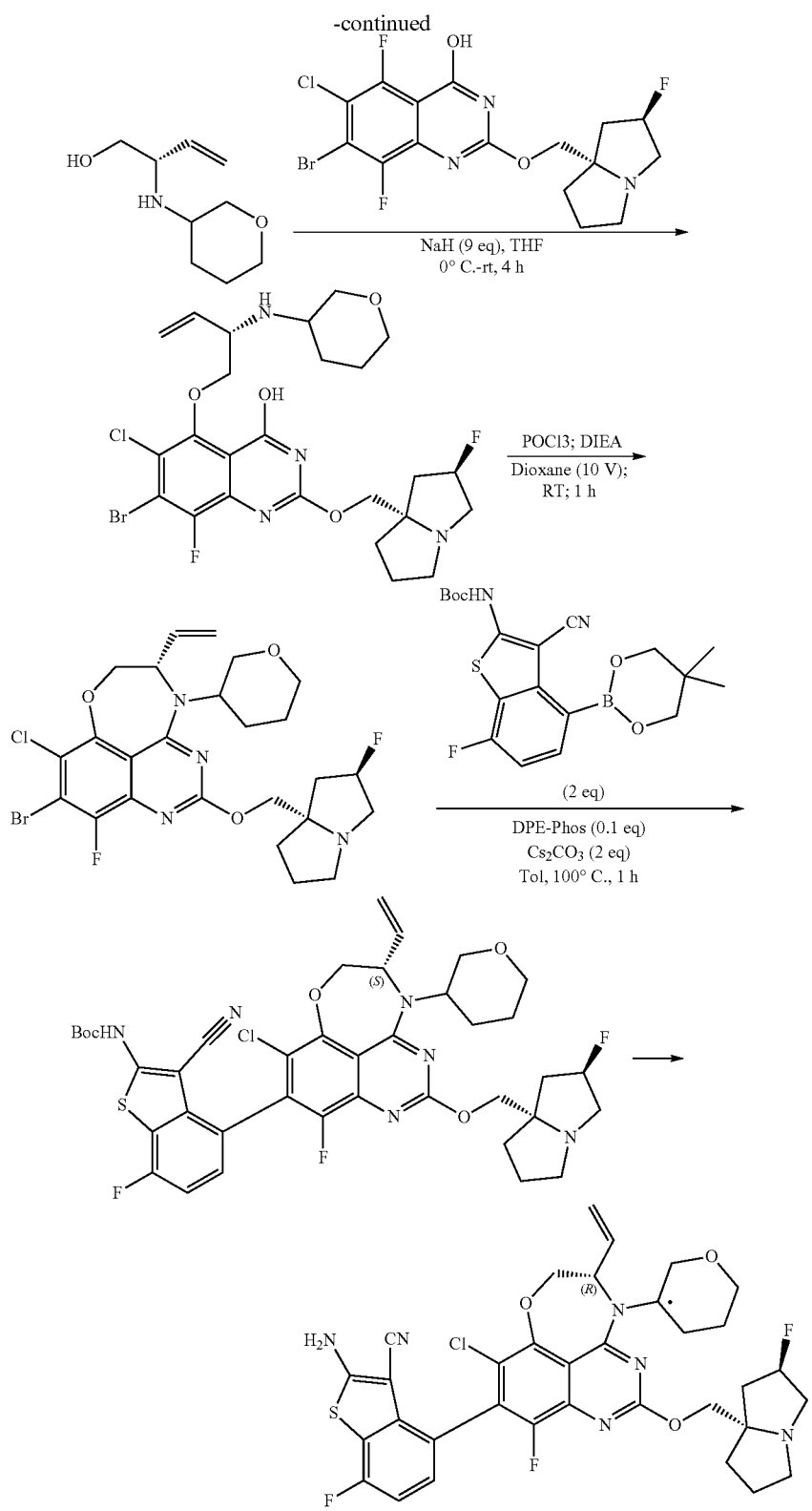
996
N-[(2S)-1-[(tert-butyldiphenylsilyl)oxy]but-3-en-2-yl]oxan-3-amine A solution of ([(2S)-2-aminobut-3-en-1-yl]oxy(tert-butyl)diphenylsilane (350 mg, 1.075 mmol, 1 equiv) and oxan-3-one (215 mg, 2.150 mmol, 2 equiv) in DCM (4 mL) was stirred for 30 minutes at room temperature. Sodium triacetoxyboronate (455 mg, 2.150 mmol, 2 equiv) was added in portions at room temperature. The resulting mixture was stirred for additional 2 hours at room temperature, washed with brine and dried over sodium sulfate. It was filtered and filtrate concentrated under reduced pressure to give a residue. The residue was purified by reversed-phase flash chromatography with the following conditions: column, C18; mobile phase, MeCN in Water (10 mmol/L NH$_4$HCO$_3$), 20% to 100% gradient in 15 min; detector, UV 254 nm to afford the desired product as a light-yellow oil. (ESI, m/z):410 [M+H]$^+$ (2S)-2-(oxan-3-ylamino)but-3-en-1-ol A solution of N-[(2S)-1-[(tert-butyldiphenylsilyl)oxy]but-3-en-2-yl]oxan-3-amine (380 mg, 0.928 mmol, 1 equiv) and TBAF (363 mg, 1.392 mmol, 1.5 equiv) in THF (4 mL) was stirred for 1 hour at room temperature. It was concentrated and purified by silica gel column chromatography, eluted with CH$_2$Cl$_2$/MeOH (12:1) to afford the desired product as a light-yellow oil. (ESI, m/z): 172 [M+H]$^+$ 7-Bromo-6-chloro-8-fluoro-2-(((2R,7aS)-2-fluorotetrahydro-1H-pyrrolizin-7a(5H)-yl)methoxy)-5-(((2S)-2-((tetrahydro-2H-pyran-3-yl)amino)but-3-en-1-yl)oxy)quinazolin-4-ol To a stirred solution of (2S)-2-(oxan-3-ylamino)but-3-en-1-ol (130 mg, 0.759 mmol, 1 equiv) in THF (2 mL) was added NaH (163 mg, 6.831 mmol, 9 equiv) in portions at 0° C. under nitrogen atmosphere. The resulting mixture was stirred for 30 minutes at 0° C. under nitrogen atmosphere. To the above mixture was added 7-bromo-6-chloro-5,8-difluoro-2-(((2R,7aS)-2-fluorotetrahydro-1H-pyrrolizin-7a (5H)-yl)methoxy)quinazolin-4-ol (206 mg, 0.455 mmol, 0.6 equiv) in portions at 0° C. The resulting mixture was stirred for additional 4 hour and quenched with water and extracted with ethyl acetate (3×30 mL). The extracts were combined, washed with brine (1×100 mL), and dried over anhydrous Na$_2$SO$_4$. After filtration, the filtrate was concentrated under reduced pressure to give the desired product as a yellow solid which was used in the next step directly without further purification. (ESI, m/z): 604 [M+H]$^+$ (5S)-9-bromo-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazoline To a stirred solution of 7-bromo-6-chloro-8-fluoro-2-(((2R,7aS)-2-fluorotetrahydro-1H-pyrrolizin-7a(5H)-yl)methoxy)-5-(((2S)-2-((tetrahydro-2H-pyran-3-yl)amino)but-3-en-1-yl)oxy)quinazolin-4-ol (350 mg, 0.580 mmol, 1 equiv) and triethylamine (439 mg, 4.350 mmol, 7.5 equiv) in 1,4-dioxane(4 mL) was added POCl$_3$ (222 mg, 1.450 mmol, 2.5 equiv) dropwise at room temperature. The resulting mixture was stirred for 1 hour at room temperature, quenched with water, and extracted with CH$_2$Cl$_2$ (3×30 mL). The extracts were combined, washed with brine (1×100 mL), and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 20% to 100% gradient in 15 min; detector, UV 254 nm to give the desired product as a yellow solid. (ESI, m/z):586 [M+H]$^+$ Tert-butyl (4-((5S)-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazolin-9-yl)-3-cyano-7-fluorobenzo[b]thiophen-2-yl)carbamate A solution of (5S)-9-bromo-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazoline (150 mg, 0.256 mmol, 1 equiv) and tert-butyl N-[3-cyano-4-(5,5-dimethyl-1,3,2-dioxaborinan-2-yl)-7-fluoro-1-benzothiophen-2-yl]carbamate (207.0 mg, 0.512 mmol, 2 equiv) and dichloropalladium; (2-[2-(diphenylphosphanyl)phenoxy]phenyl)diphenylphosphane (37 mg, 0.051 mmol, 0.2 equiv) and Cs$_2$CO$_3$ (167 mg, 0.512 mmol, 2 equiv) in toluene (15 mL) was stirred for 1 hour at 100° C. under nitrogen atmosphere. It was cooled to room temperature, filtered and the filter cake was washed with CH$_2$Cl$_2$ (3×10 mL). The filtrate was concentrated under reduced pressure to give a residue. The residue was purified by reversed-phase flash chromatography with the following conditions: column, C18; mobile phase, MeCN in Water (10 mmol/L NH$_4$HCO$_3$), 20% to 100% gradient in 10 min; detector, UV 254 nm to afford the desired product as a yellow solid. (ESI, m/z): 798 [M+H]$^+$ 2-Amino-4-((5S)-8-chloro-4-(dihydro-2H-3l3-pyran-3 (4H)-yl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (996) A solution of tert-butyl (4-((5S)-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazolin-9-yl)-3-cyano-7-fluorobenzo[b]thiophen-2-yl)carbamate (95 mg, 0.119 mmol, 1 equiv) and TFA (20 mg, 0.178 mmol, 1.5 equiv) in DCM(1 mL) was stirred for 1 hour at room temperature. The resulting mixture was concentrated under vacuum to give a crude. The crude product was purified by Prep-HPLC with the following conditions (Column: XBridge BEH C18 OBD Prep Column 130, 5 m, 30 mm*150 mm; Mobile Phase A: Water (10 mmol/L NH$_4$HCO$_3$), Mobile Phase B: ACN; Flow rate: 60 mL/min; Gradient: 45% B to 65% B in 10 min; Wave Length: UV 254 nm/220 nm; RT1(min): 6.52/7.4/8.22) to afford the desired product as a white solid. (ESI, m/z):697 [M+H]$^+$ $^1$H NMR: (400 MHZ, DMSO-d$_6$, ppm) δ 8.05 (s, 2H), 7.22 (dd, J=8.4, 5.3 Hz, 1H), 7.13 (dd, J=9.5, 8.4 Hz, 1H), 5.89-5.79 (m, 1H), 5.38-5.20 (m, 1H), 5.19-5.01 (m, 3H), 4.96-4.90 (m, 1H), 4.80 (dd, J=12.4, 5.1 Hz, 1H), 4.45 (d, J=12.4 Hz, 1H), 4.10 (d, J=10.3 Hz, 1H), 4.03 (d, J=10.3 Hz, 1H), 3.87-3.75 (m, 2H), 3.51 (t, J=10.4 Hz, 1H), 3.40-3.35 (m, 1H), 3.13-3.05 (m, 2H), 3.01 (d, J=2.2 Hz, 1H), 2.83 (d, J=7.3 Hz, 1H), 2.19-1.93 (m, 5H), 1.88-1.73 (m, 5H). 2-amino-4-((5S)-8-chloro-5-ethynyl-10-fluoro-2-(((2R, 7aS)-2-fluorotetrahydro-1H-pyrrolizin-7a(5H)-yl) methoxy)-4-(tetrahydrofuran-3-yl)-5,6-dihydro-4H-[1,4] oxazepino[5,6,7-de]quinazolin-9-yl)-7-fluorobenzo[b] thiophene-3-carbonitrile (843)

1443 1444
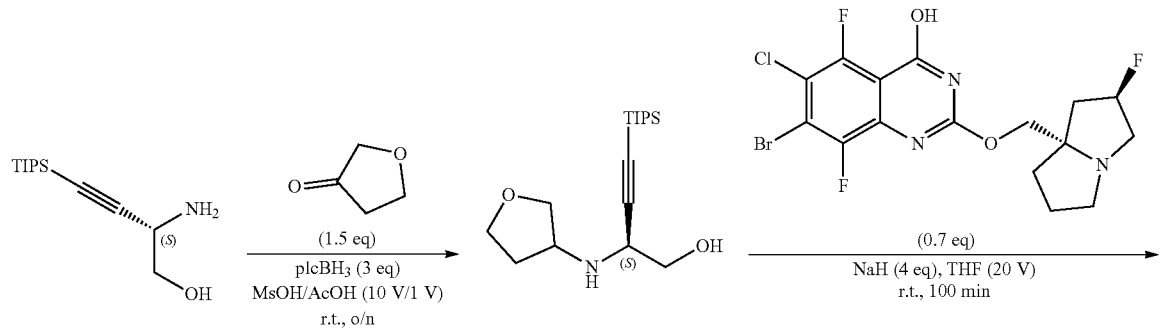
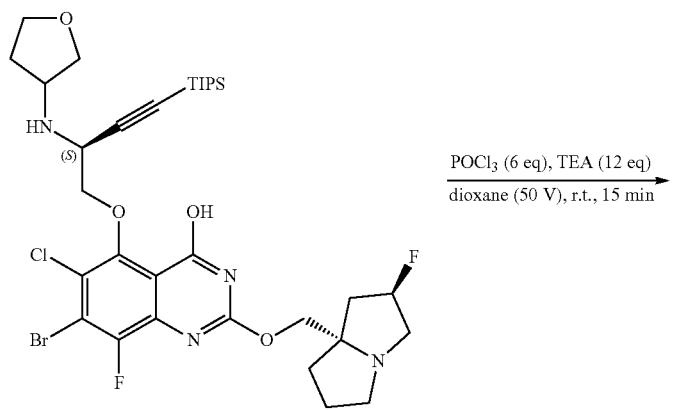
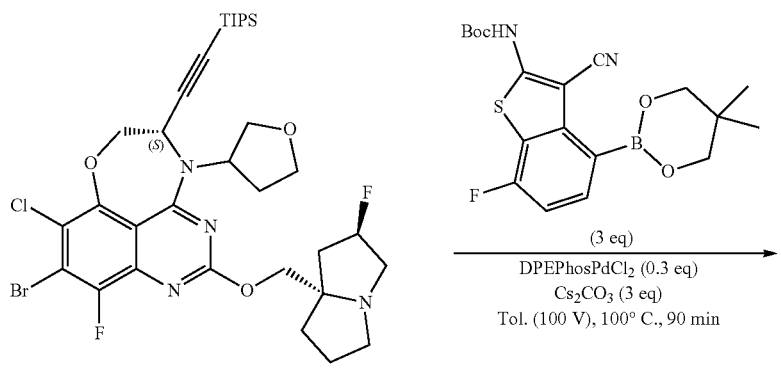
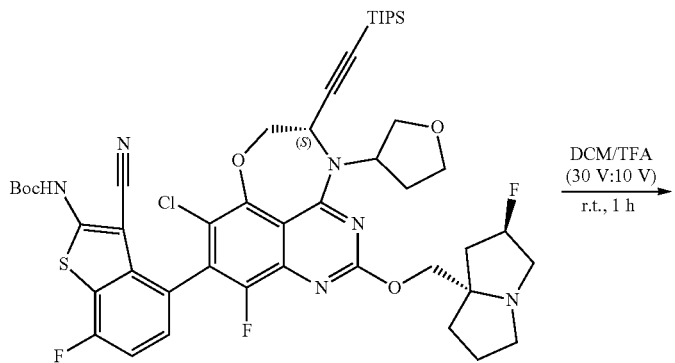

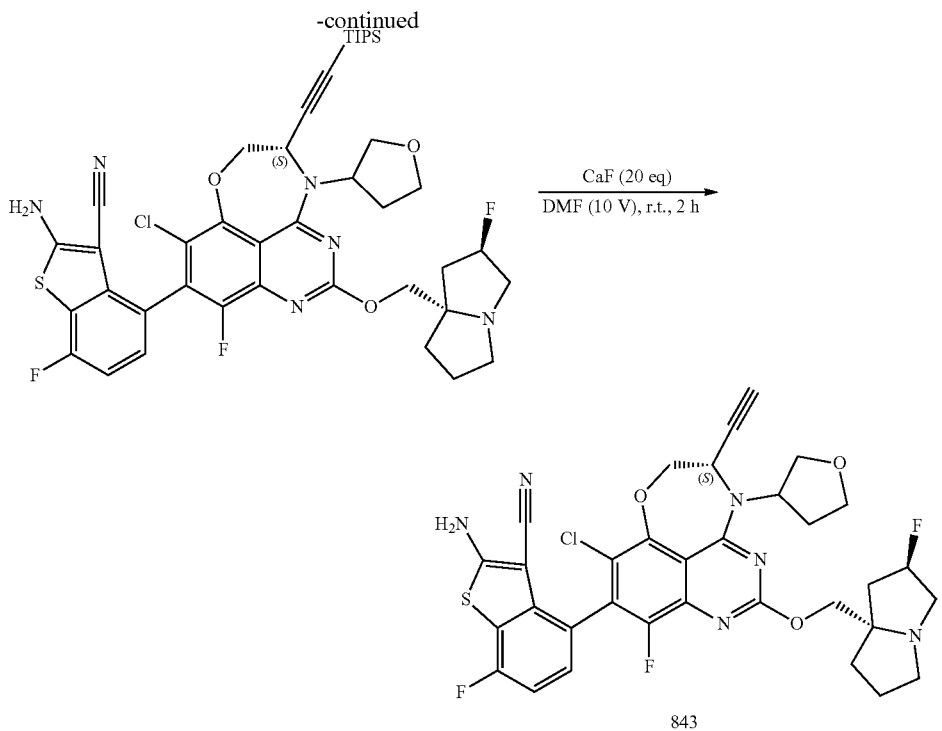

843

(2S)-2-(oxolan-3-ylamino)-4-(triisopropylsilyl)but-3-yn-1-ol To a stirred mixture of (2S)-2-amino-4-(triisopropylsilyl)but-3-yn-1-ol (1.1 g, 4.556 mmol, 1 equiv) and dihydrofuran-3-one (0.78 g, 9.112 mmol, 2 equiv) in MeOH (11 mL) and AcOH (1.1 mL) was added pyridine borane (1.27 g, 13.668 mmol, 3 equiv) in portions at room temperature. It was stirred overnight, quenched with water at room temperature, and extracted with $CH_2Cl_2$ (3×100 mL). The extracts were combined, dried over anhydrous $Na_2SO_4$. After filtration, the filtrate was concentrated under reduced pressure to give a residue. The residue was purified by silica gel column chromatography, eluted with $CH_2Cl_2$/MeOH (12:1) to afford the desired product as an off-white oil. (ESI, m/z): 312 $[M+H]^+$ 7-Bromo-6-chloro-8-fluoro-2-(((2R,7aS)-2-fluorotetrahydro-1H-pyrrolizin-7a(5H)-yl)methoxy)-5-(((2S)-2-((tetrahydrofuran-3-yl)amino)-4-(triisopropylsilyl)but-3-yn-1-yl)oxy)quinazolin-4-ol To a stirred mixture of (2S)-2-(oxolan-3-ylamino)-4-(triisopropylsilyl)but-3-yn-1-ol (100 mg, 0.321 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (102 mg, 0.225 mmol, 0.7 equiv) in THF (4.0 mL) was added NaH (31 mg, 1.284 mmol, 4 equiv) in portions at 0° C. The resulting mixture was stirred for 100 minutes at room temperature, quenched with water/Ice, and extracted with $CH_2Cl_2$ (3×100 mL). After filtration, the filtrate was concentrated under reduced pressure to give a residue. The residue was purified by silica gel column chromatography, eluted with $CH_2Cl_2$/MeOH (10:1) to afford the desired product as a yellow solid. (ESI, m/z): 743 $[M+H]^+$ (5S)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5-((triisopropylsilyl)ethynyl)-5,6-dihydro-4H-[1,4]oxazepino[5,6,7-de]quinazoline To a stirred mixture of 7-bromo-6-chloro-8-fluoro-2-(((2R,7aS)-2-fluorotetrahydro-1H-pyrrolizin-7a(5H)-yl)methoxy)-5-(((2S)-2-((tetrahydrofuran-3-yl)amino)-4-(triisopropylsilyl)but-3-yn-1-yl)oxy)quinazolin-4-ol (590 mg, 0.793 mmol, 1 equiv) and $POCl_3$ (729 mg, 4.758 mmol, 6 equiv) in dioxane (12 mL) was added triethylamine (963 mg, 9.516 mmol, 12 equiv) dropwise at room temperature. The resulting mixture was stirred for 20 minutes, quenched with water/ice, and extracted with $CH_2Cl_2$ (3×200 mL). The extracts were combined, washed with brine, and dried over anhydrous $Na_2SO_4$. After filtration, the filtrate was concentrated under reduced pressure to give a residue. The residue was purified by silica gel column chromatography, eluted with $CH_2Cl_2$/MeOH (12:1) to afford the desired product as a yellow solid. (ESI, m/z): 725 $[M+H]^+$ Tert-butyl (4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-((triisopropylsilyl)ethynyl)-5,6-dihydro-4H-[1,4]oxazepino[5,6,7-de]quinazolin-9-yl)-3-cyano-7-fluorobenzo[b]thiophen-2-yl)carbamate To a stirred mixture of (5S)-9-bromo-8-chloro-10-fluoro-2-(((2R,7aS)-2-fluorotetrahydro-1H-pyrrolizin-7a(5H)-yl)methoxy)-4-(tetrahydrofuran-3-yl)-5-((triisopropylsilyl)ethynyl)-5,6-dihydro-4H-[1,4]oxazepino[5,6,7-de]quinazoline (500 mg, 0.689 mmol, 1 equiv) and tert-butyl N-[3-cyano-4-(5,5-dimethyl-1,3,2-dioxaborinan-2-yl)-7-fluoro-1-benzothiophen-2-yl]carbamate (835 mg, 2.067 mmol, 3 equiv) in toluene (50 mL,) was added Dichloro[bis(2-(diphenylphosphino)phenyl)ether]palladium(II) (148 mg, 0.207 mmol, 0.3 equiv) and $Cs_2CO_3$ (673 mg, 2.067 mmol, 3 equiv) at room temperature under argon atmosphere. The resulting mixture was stirred for 90 minutes at 100° C. under argon atmosphere. It was cooled to room temperature, filtered and the filter cake was washed with $CH_2Cl_2$ (4×50 mL). The filtrate was concentrated under reduced pressure to give a residue. The residue was purified by silica gel column chromatography, eluted with $CH_2Cl_2$/MeOH (12:1) to afford the desired product as a light-yellow solid. (ESI, m/z): 937 $[M+H]^+$ 2-Amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-((triisopropylsilyl)ethynyl)-5,6-dihydro-4H-[1,4]oxazepino[5,6,7-de]quinazolin-9-yl)-7-fluorobenzo[b]thiophene-3-carbonitrile To a stirred solution of tert-butyl (4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-((triisopropylsilyl)ethynyl)-5,6-dihydro-4H-[1,4]oxazepino[5,6,7-de]quinazolin-9-yl)-3-cyano-7-fluorobenzo[b]thiophen-2-yl)carbamate (670 mg, 0.715 mmol, 1 equiv) in DCM (20.1 mL,) was added TFA (6.7 mL) at room temperature. The resulting mixture was stirred for 1 hour at room temperature and concentrated under reduced pressure to give the desired product which was used in the next step directly without further purification. (ESI, m/z): 837 [M+H]$^+$ 2-Amino-4-((5S)-8-chloro-5-ethynyl-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile To a stirred solution of 2-amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-((triisopropylsilyl)ethynyl)-5,6-dihydro-4H-[1,4]oxazepino[5,6,7-de]quinazolin-9-yl)-7-fluorobenzo[b]thiophene-3-carbonitrile (500 mg, 0.597 mmol, 1 equiv) in DMF (5 mL) was added CsF (1814 mg, 11.940 mmol, 20 equiv) at room temperature. The resulting mixture was stirred for 2 hours at room temperature. The mixture was directly purified by reversed-phase flash chromatography with the following conditions: Column: Sunfire C18 5 m, 30 mm*150 mm; Mobile Phase A: Water (0.1% FA), Mobile Phase B: ACN; Flow rate: 60 mL/min; Gradient: 20% B to 45% B in 10 min; Wave Length: UV 254 nm/220 nm; RT1(min): 6.48/7.22/7.6. the desired product as a white solid. (ESI, m/z): 681[M+H]$^+$ $^1$H NMR: (400 MHZ, DMSO-d$_6$, ppm) § 8.07 (d, J=11.4 Hz, 2H), 7.26-7.19 (m, 1H), 7.16-7.11 (m, 1H), 5.67-5.56 (s, 1H), 5.38-5.24 (m, 1H), 5.11 (s, 1H), 4.79-4.71 (m, 1H), 4.61-4.47 (m, 1H), 4.22-4.14 (m, 1H), 4.14-4.03 (m, 2H), 3.96-3.78 (m, 2H), 3.75-3.63 (m, 1H), 3.47-3.42 (m, 1H), 3.23-3.12 (m, 2H), 2.92-2.82 (s, 1H), 2.46-2.36 (m, 2H), 2.27-1.96 (m, 4H), 1.93-1.74 (m, 3H).

Example 1bo: Synthesis of 2-amino-4-((5S)-8-chloro-4-(3,3-difluoropropyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (788)

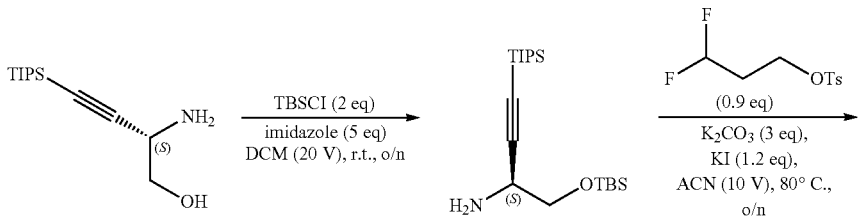

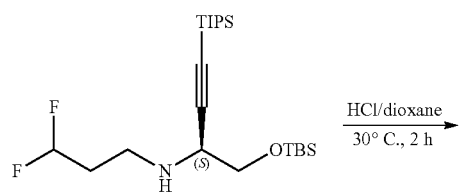

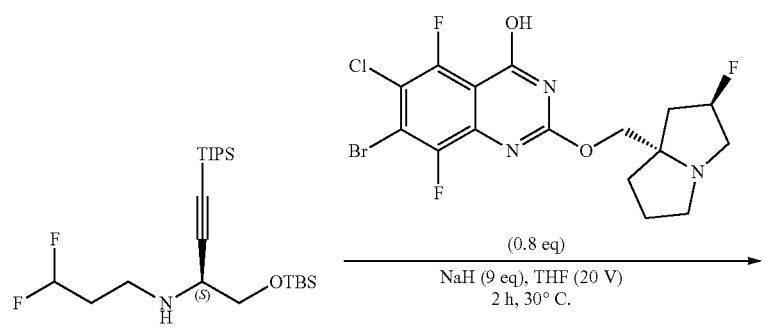

-continued
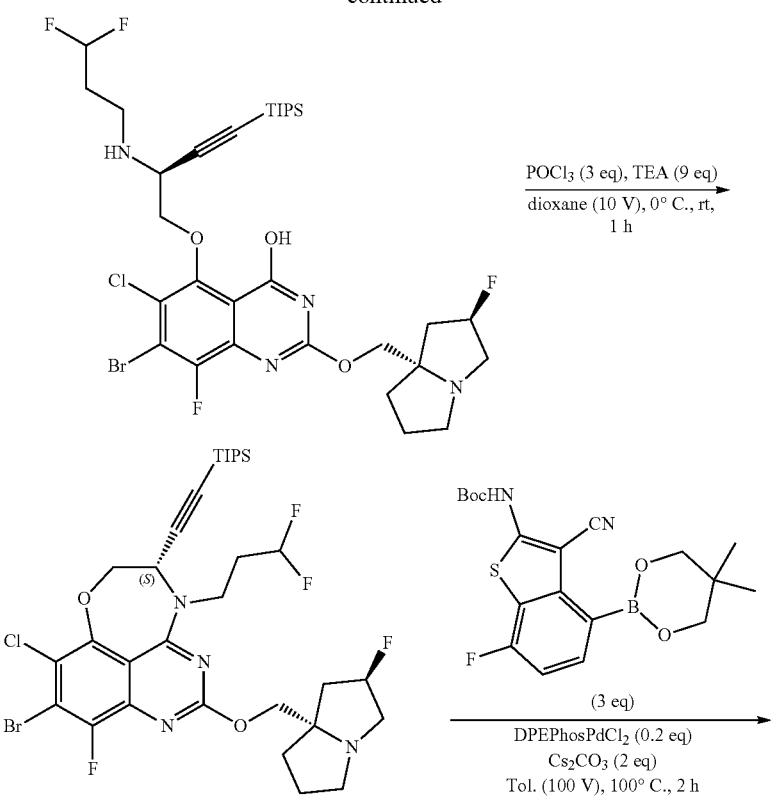
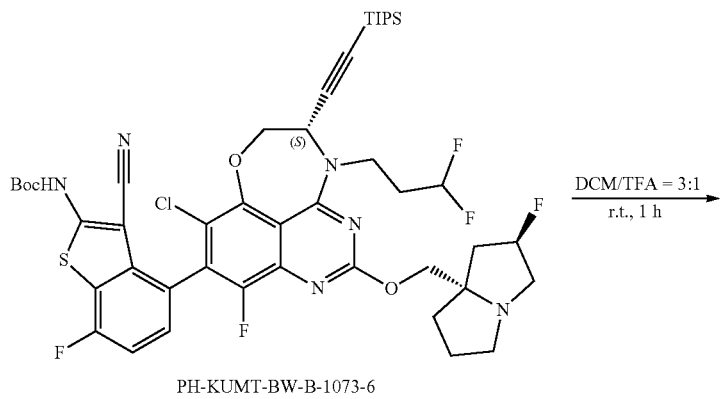
PH-KUMT-BW-B-1073-6
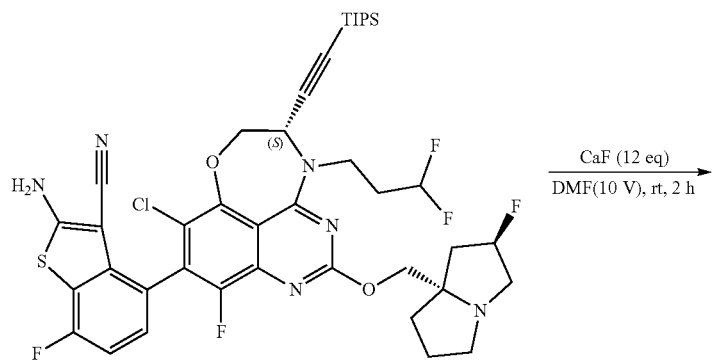

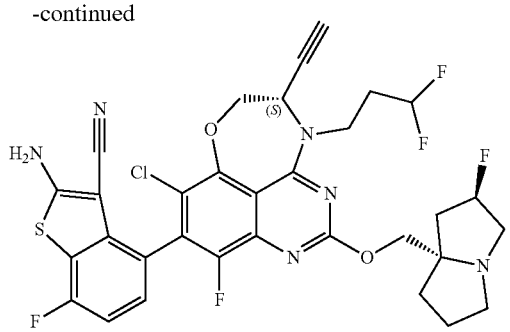

718

[(3S)-3-amino-4-[(tert-butyldimethylsilyl)oxy]but-1-yn-1-yl]triisopropylsilane A solution of (2S)-2-amino-4-(triisopropylsilyl)but-3-yn-1-ol (5.4 g, 22.365 mmol, 1 equiv). TBSCl (6.74 g, 44.730 mmol, 2 equiv) and imidazole (7.61 g, 111.825 mmol, 5 equiv) in DCM (100 mL) was stirred overnight at room temperature under nitrogen atmosphere. The resulting mixture was concentrated under reduced pressure to give a residue. The residue was purified by silica gel column chromatography, eluted with petroleum/ethyl acetate (1:1) to afford the desired product as a colorless liquid. (ESI, m/z):356[M+H]$^+$

[(2S)-1-[(tert-butyldimethylsilyl)oxy]-4-(triisopropylsilyl)but-3-yn-2-yl](3,3-difluoropropyl)-amine To a stirred solution of [(3S)-3-amino-4-[(tert-butyldimethylsilyl)oxy]but-1-yn-1-yl]triisopropylsilane (1 g, 2.811 mmol, 1 equiv) and 3,3-difluoropropyl 4-methylbenzenesulfonate (0.63 g, 2.530 mmol, 0.9 equiv) in ACN (10 mL) was added $K_2CO_3$ (1.17 g, 8.433 mmol, 3 equiv) and KI (0.56 g, 3.373 mmol, 1.2 equiv) in portions at room temperature. The resulting mixture was stirred overnight at 80° C. It was cooled to room temperature, quenched with water, and extracted with $CH_2Cl_2$ (3×50 mL). The extracts were combined, washed with brine (1×150 mL), and dried over anhydrous $Na_2SO_4$. After filtration, the filtrate was concentrated under reduced pressure to give a residue. The residue was purified by silica gel column chromatography, eluted with petroleum/ethyl acetate (1:1) to afford the desired product as a brown solid. (ESI, m/z): 434 [M+H]$^+$ (S)-2-((3,3-difluoropropyl)amino)-4-(triisopropylsilyl)but-3-yn-1-ol A solution of [(2S)-1-[(tert-butyldimethylsilyl)oxy]-4-(triisopropylsilyl)but-3-yn-2-yl](3,3-difluoropropyl) amine (480 mg, 1.107 mmol, 1 equiv) in HCl/1,4-dioxane (4 M, 5 mL) was stirred for 2 hours at 30° C. The resulting mixture was concentrated under reduced pressure to give the desired product which was used directly in the next step without purification. (ESI, m/z): 320[M+H]$^+$ 7-Bromo-6-chloro-5-(((S)-2-((3,3-difluoropropyl)amino)-4-(triisopropylsilyl)but-3-yn-1-yl)oxy)-8-fluoro-2-(((2R,7aS)-2-fluorotetrahydro-1H-pyrrolizin-7a(5H)-yl)methoxy)quinazolin-4-ol To a stirred solution of (S)-2-((3,3-difluoropropyl)amino)-4-(triisopropylsilyl)but-3-yn-1-ol (499.8 mg, 1.075 mmol, 1 equiv, 68.7%) and 7-bromo-6-chloro-5,8-difluoro-2-(((2R,7aS)-2-fluorotetrahydro-1H-pyrrolizin-7a(5H)-yl)methoxy)quinazolin-4-ol (389 mg, 0.860 mmol, 0.8 equiv) in THF (20 mL) was added NaH (232 mg, 9.675 mmol, 9 equiv) in portions at 0° C. The resulting mixture was stirred for 2 hours at 30° C. It was quenched with water/ice at 0° C. and extracted with ethyl acetate (3×10 mL). The extracts were combined, washed with water (3×30 mL), and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 85% to 100% gradient in 15 min; detector, UV 254 nm to afford the desired product as a yellow solid. (ESI, m/z): 751 [M+H]$^+$ (S)-9-bromo-8-chloro-4-(3,3-difluoropropyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazoline A solution of 7-bromo-6-chloro-5-(((S)-2-((3,3-difluoropropyl)amino)-4-(triisopropylsilyl)but-3-yn-1-yl)oxy)-8-fluoro-2-(((2R,7aS)-2-fluorotetrahydro-1H-pyrrolizin-7a(5H)-yl)methoxy)quinazolin-4-ol (513 mg, 0.682 mmol, 1 equiv) in dioxane (5 mL) was treated with triethylamine (621 mg, 6.138 mmol, 9 equiv) for 2 min at room temperature followed by the addition of $POCl_3$ (313 mg, 2.046 mmol, 3 equiv) dropwise at 0° C. The resulting mixture was stirred for 1 hour at room temperature and extracted with ethyl acetate (3×10 mL). The extracts were combined, washed with water (3×30 mL), and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 50% to 70% gradient in 10 min; detector, UV 254 nm to give desired product as a yellow solid. (ESI, m/z): 733 [M+H]$^+$ Tert-butyl (4-((S)-8-chloro-4-(3,3-difluoropropyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazolin-9-yl)-3-cyano-7-fluorobenzo[b]thiophen-2-yl)carbamate To a stirred solution of ((S)-9-bromo-8-chloro-4-(3,3-difluoropropyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazoline (227 mg, 0.309 mmol, 1 equiv), tert-butyl N-[3-cyano-4-(5,5-dimethyl-1,3,2-dioxaborinan-2-yl)-7-fluoro-1-benzothiophen-2-yl]carbamate (375 mg, 0.927 mmol, 3 equiv) and $Cs_2CO_3$ (201 mg, 0.618 mmol, 2 equiv) in toluene (23 mL) was added dichloropalladium; (2-[2-(diphenylphosphanyl)phenoxy]phenyl)-diphenylphosphane (44 mg, 0.062 mmol, 0.2 equiv) at room temperature under nitrogen atmosphere. The resulting mixture was stirred for 2 hours at 100° C. It was cooled down to room temperature, extracted with DCM, washed with brine and dried over sodium sulfate. It was filtered and concentrated under reduced pressure to give a residue. The residue was purified by reversed-phase flash chromatography with the following conditions: column, C18; mobile phase, MeOH in Water (10 mmol/L NH₄HCO₃), 85% to 100% gradient in 15 min; detector, UV 254 nm to afford the desired product as a solid. (ESI, m/z):945 [M+H]⁺

2-Amino-4-((S)-8-chloro-4-(3,3-difluoropropyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazolin-9-yl)-7-fluorobenzo[b]thiophene-3-carbonitrile A solution of tert-butyl (4-((S)-8-chloro-4-(3,3-difluoropropyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazolin-9-yl)-3-cyano-7-fluorobenzo[b]thiophen-2-yl)carbamate (98 mg, 0.104 mmol, 1 equiv) and TFA (0.5 mL) in DCM (1.5 mL) was stirred for 1 hour at room temperature. The resulting mixture was concentrated under reduced pressure to afford the desired product as a yellow oil which was used in the next step directly without further purification. (ESI, m/z):845 [M+H]⁺

2-Amino-4-((5S)-8-chloro-4-(3,3-difluoropropyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile To a stirred solution of 2-amino-4-((S)-8-chloro-4-(3,3-difluoropropyl)-10-fluoro-2-(((2R,7aS)-2-fluorotetrahydro-1H-pyrrolizin-7a(5H)-yl)methoxy)-5-((triisopropylsilyl)ethynyl)-5,6-dihydro-4H-[1,4]oxazepino[5,6,7-de]quinazolin-9-yl)-7-fluorobenzo[b]thiophene-3-carbonitrile (163 mg, 0.193 mmol, 1 equiv) in DMF (1 mL) was added CsF (351 mg, 2.316 mmol, 12 equiv) in portions at room temperature under nitrogen atmosphere. The resulting mixture was stirred for 2 hours at room temperature under nitrogen atmosphere. It was concentrated to give a crude. The crude product was purified by Prep-HPLC with the following conditions (Column: Kinetex 5 m EVO C18, 30 mm*150 mm; Mobile Phase A: Water (10 mmol/L NH₄HCO₃), Mobile Phase B: ACN; Flow rate: 60 mL/min; Gradient: 45% B to 69% B in 10 min; Wave Length: UV 254 nm/220 nm; RT1(min): 6.62/8.62/8.92) to afford the desired product as a white solid. (ESI, m/z): 689 [M+H]⁺

¹H NMR:(400 MHZ, DMSO-d₆, ppm) § 8.08-8.07 (m, 2H), 7.26-7.19 (m, 1H), 7.16-7.11 (m, 1H), 6.42-6.13 (m, 1H), 5.34-5.21 (m, 1H), 5.13-5.12 (m, 1H), 4.81-4.70 (m, 1H), 4.50-4.39 (m, 1H), 4.22-4.07 (m, 3H), 3.88-3.78 (m, 1H), 3.56-3.47 (m, 1H), 3.18-3.10 (m, 2H), 3.01-3.00 (m, 1H), 2.83-2.82 (m, 1H), 2.34-2.32 (m, 2H), 2.15-1.98 (m, 3H), 1.90-1.80 (m, 3H).

Example 1 bp: Synthesis of 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazolin-9-yl)-7-fluorobenzo[b]thiophene-3-carbonitrile (1032)

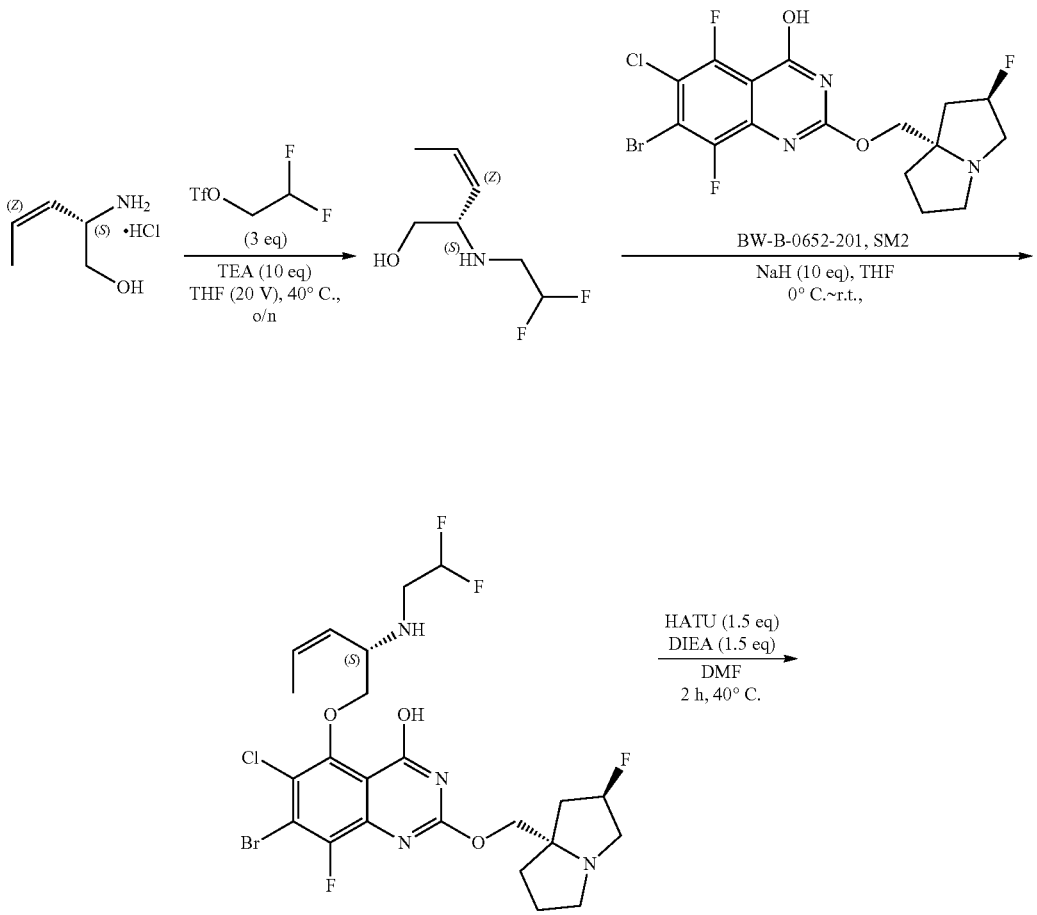

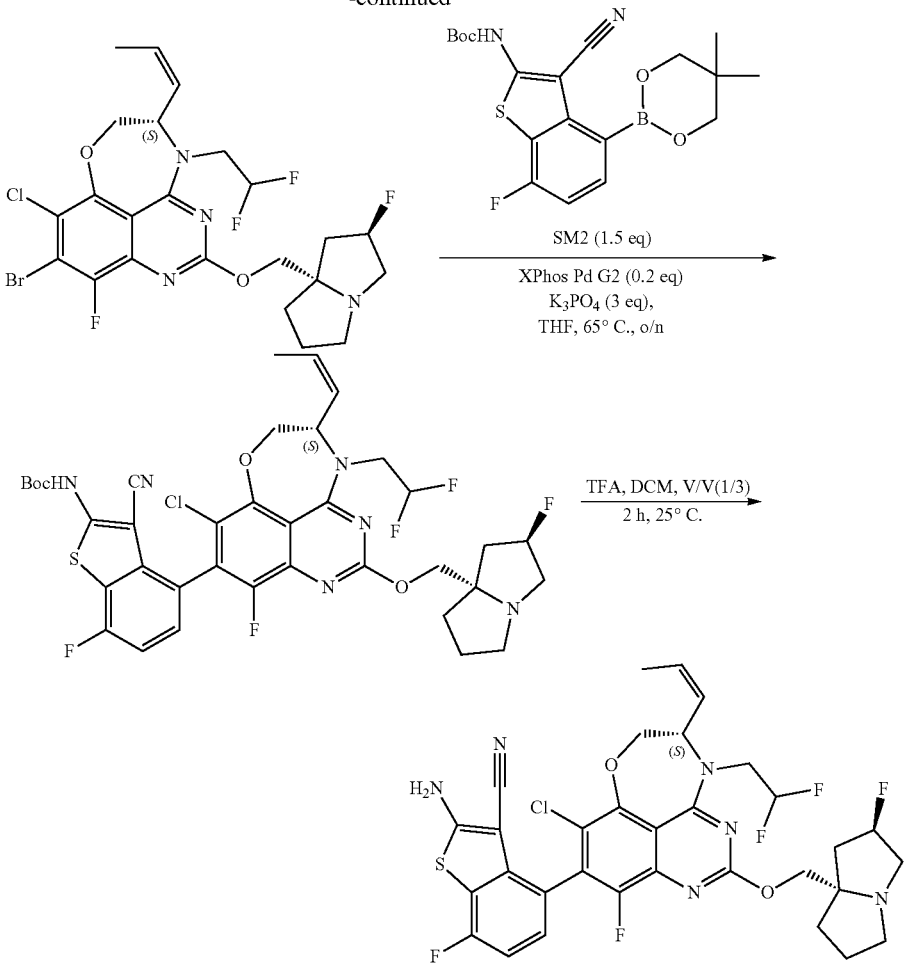

(2S)-2-[(2,2-difluoroethyl)amino]pent-3-en-1-ol To a stirred solution of (2S)-2-aminopent-3-en-1-ol hydrochloride (900 mg, 6.540 mmol, 1 equiv) and 2,2-difluoroethyl trifluoromethanesulfonate (4201 mg, 19.620 mmol, 3 equiv) in THF (18.0 mL) was added triethylamine (6618 mg, 65.400 mmol, 10 equiv) dropwise at room temperature. The resulting mixture was stirred for overnight at 40° C. and concentrated under vacuum to give a residue. The residue was purified by silica gel column chromatography, eluted with petroleum/ethyl acetate (1:8) to afford the desired product as a colorless liquid. (ESI, m/z): 166[M+H]+

7-Bromo-6-chloro-5-(((S,Z)-2-((2,2-difluoroethyl)amino)pent-3-en-1-yl)oxy)-8-fluoro-2-(((2R,7aS)-2-fluorotetrahydro-1H-pyrrolizin-7a(5H)-yl)methoxy)quinazolin-4-ol To a stirred solution of (2S)-2-[(2,2-difluoroethyl)amino]pent-3-en-1-ol (230 mg, 1.392 mmol, 1 equiv) and 7-bromo-6-chloro-5,8-difluoro-2-(((2R,7aS)-2-fluorotetrahydro-1H-pyrrolizin-7a(5H)-yl)methoxy)quinazolin-4-ol (630 mg, 1.392 mmol, 1 equiv) in THF (5 mL) were added NaH (334 mg, 13.920 mmol, 10 equiv) in portions at 0° C. under nitrogen atmosphere. The resulting mixture was stirred for additional 2 hour at room temperature, quenched with water/Ice at 0° C., and extracted with ethyl acetate (3×3 mL). The extracts were combined, washed with brine (3×3 mL), and dried over anhydrous Na2SO4. After filtration, the filtrate was concentrated under reduced pressure to give the desired product which was used in the next step directly without further purification. (ESI, m/z):597 [M+H]+

(S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazoline To a stirred solution of 7-bromo-6-chloro-5-(((S,Z)-2-((2,2-difluoroethyl)amino)pent-3-en-1-yl)oxy)-8-fluoro-2-(((2R,7aS)-2-fluorotetrahydro-1H-pyrrolizin-7a(5H)-yl)methoxy)quinazolin-4-ol (1 g, 1.673 mmol, 1 equiv) in DMF (20 mL, 258.431 mmol) was added HATU (954 mg, 2.510 mmol, 1.5 equiv) and DIEA (324.29 mg, 2.510 mmol, 1.5 equiv) in portions at room temperature. The resulting mixture was stirred for additional 2 h at 40° C. It was cooled to room temperature, extracted with ethyl acetate (3×10 mL). The extracts were combined, washed with brine (3×10 mL), and dried over anhydrous Na2SO4. After filtration, the filtrate was concentrated under reduced pressure to give a residue. The residue was purified by silica gel column chromatography, eluted with petroleum/ethyl acetate (8:1) to afford the desired product as a yellow liquid. (ESI, m/z): 579[M+H]+

Tert-butyl (4-((S)-8-chloro-4-(2,2-difluoroethyl)-10-fluoro-2-(((2R,7aS)-2-fluorotetrahydro-1H-pyrrolizin-7a (5H)-yl)methoxy)-5-((Z)-prop-1-en-1-yl)-5,6-dihydro-4H-[1,4]oxazepino[5,6,7-de]quinazolin-9-yl)-3-cyano-7-fluorobenzo[b]thiophen-2-yl)carbamate To a stirred solution of (S)-9-bromo-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazoline (200 mg, 0.345 mmol, 1 equiv) and tert-butyl N-[3-cyano-4-(5,5-dimethyl-1,3,2-dioxaborinan-2-yl)-7-fluoro-1-benzothiophen-2-yl]carbamate (209 mg, 0.517 mmol, 1.5 equiv) in THF (5.0 mL, 61.724 mmol) were added X-Phos Pd G2 (33 mg, 0.069 mmol, 0.2 equiv) and K$_3$PO$_4$ (219 mg, 1.035 mmol, 3 equiv) in portions at room temperature under argon atmosphere. The resulting mixture was stirred for overnight at 65° C. It was cooled to room temperature and extracted with CH$_2$Cl$_2$ (3×5 mL). The extracts were combined, washed with brine (3×5 mL), and dried over anhydrous Na$_2$SO$_4$. After filtration, the filtrate was concentrated under reduced pressure to give a residue. The residue was purified by reversed-phase flash chromatography with the following conditions: column, C18; mobile phase, MeCN in Water (10 mmol/L NH$_4$HCO$_3$), 55% to 75% gradient in 10 min; detector, UV 254 nm. to afford the desired product as a light-yellow solid. (ESI, m/z):791 [M+H]$^+$ 2-Amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazolin-9-yl)-7-fluorobenzo[b]thiophene-3-carbonitrile To a stirred solution of tert-butyl (4-((S)-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazolin-9-yl)-3-cyano-7-fluorobenzo[b]thiophen-2-yl)carbamate (70 mg, 0.088 mmol, 1 equiv) in DCM (0.9 mL, 14.158 mmol) was added TFA (0.3 mL, 4.039 mmol) dropwise at room temperature.

The resulting mixture was stirred for 1 hour at room temperature and concentrated under vacuum to give a residue. The residue was basified to pH~8 with saturated NaHCO$_3$ (aq.) and extracted with CH$_2$Cl$_2$ (3×2 mL). The extracts were combined, washed with brine (3×2 mL), and dried over anhydrous Na$_2$SO$_4$. After filtration, the filtrate was concentrated under reduced pressure to give a crude. The crude product (70 mg) was purified by Prep-HPLC with the following conditions (Column: YMC Triart C18 ExRs 5 m, 30 mm*150 mm; Mobile Phase A: Water(10 mmol/L NH$_4$HCO$_3$), Mobile Phase B: ACN; Flow rate: 60 mL/min mL/min; Gradient: 58% B to 78% B in 10 min; Wave Length: 254 nm/220 nm nm; RT1(min): 7.73/8.85/9.35) to afford the desired product as an off-white solid. (ESI, m/z): 691 [M+H]$^+$ $^1$H NMR: (400 MHZ, DMSO-d$_6$, ppm) § 8.10 (s, 2H), 7.22 (dd, J=8.4, 5.3 Hz, 1H), 7.18-7.09 (m, 1H), 6.49 (s, 1H), 5.84 (dd, J=10.9, 7.0 Hz, 1H), 5.46 (t, J=10.0 Hz, 1H), 5.35-5.21 (m, 1H), 4.88 (s, 1H), 4.71 (d, J=8.9 Hz, 1H), 4.42 (d, J=12.8 Hz, 1H), 4.36 (s, 1H), 4.10 (d, J=10.3 Hz, 1H), 4.03 (d, J=10.5 Hz, 1H), 3.82 (s, 1H), 3.09 (s, 2H), 3.01 (s, 1H), 2.83 (s, 1H), 2.12 (s, 1H), 2.05 (s, 1H), 2.00 (s, 1H), 1.93-1.65 (m, 6H).

Example 1bq: Synthesis of 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile (758)

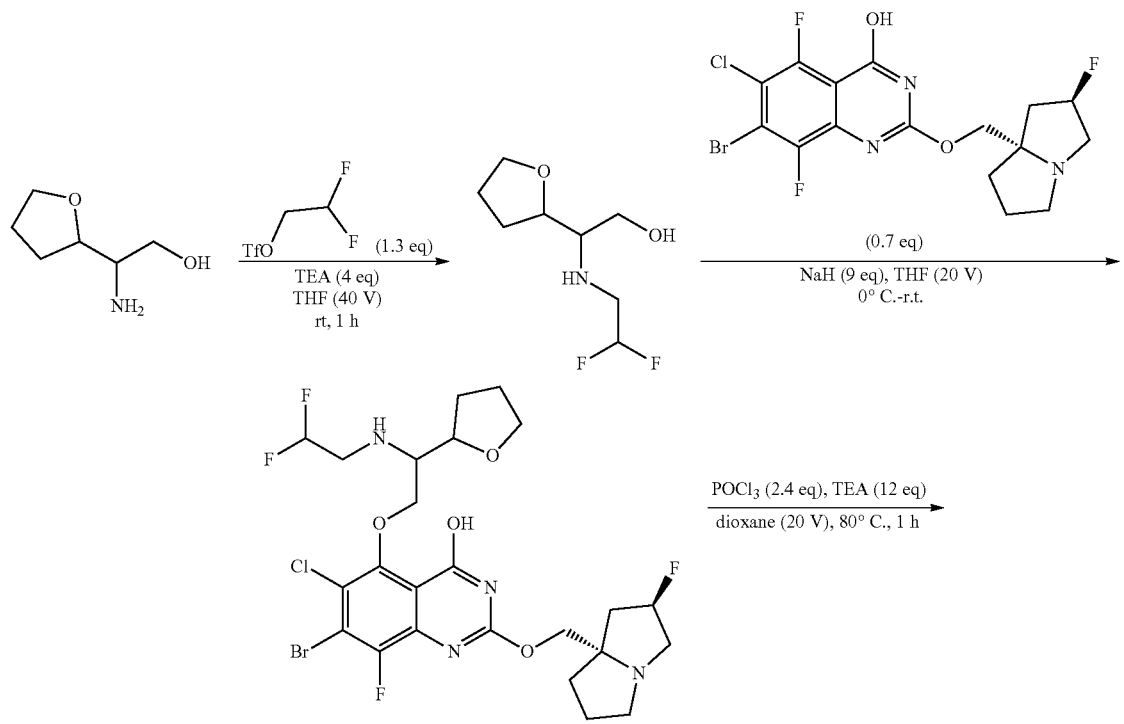

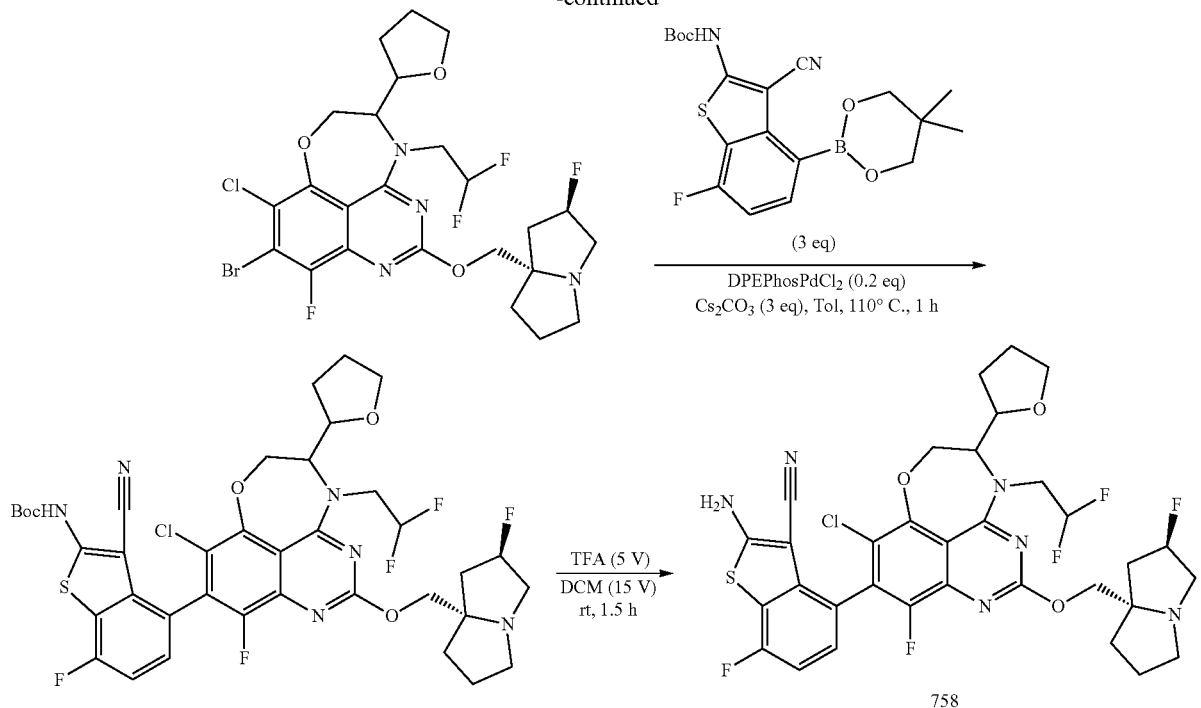

2-((2,2-Difluoroethyl)amino)-2-(tetrahydrofuran-2-yl) ethan-1-ol To a stirred solution of (2R)-2-amino-2-(oxolan-2-yl)ethanol (990 mg, 7.547 mmol, 1 equiv) in anhydrous THF (20 mL, 246.855 mmol, 32.71 equiv) was added triethylamine (5.25 mL, 37.735 mmol, 5 equiv) followed by 2,2-difluoroethyl trifluoromethanesulfonate (1.78 g, 8.302 mmol, 1.1 equiv) at room temperature. The reaction mixture was stirred at room temperature for 1 hour and concentrated under reduced pressure to give crude product which was further purified by silica gel column chromatography, eluted with $CH_2Cl_2$/MeOH (17:1) to afford desired product as a light yellow oil. (ESI, m/z): 196 [M+H]$^+$ 7-Bromo-6-chloro-5-(2-((2,2-difluoroethyl)amino)-2-(tetrahydrofuran-2-yl)ethoxy)-8-fluoro-2-(((2R,7aS)-2-fluorotetrahydro-1H-pyrrolizin-7a(5H)-yl)methoxy)quinazolin-4-ol To a stirred solution of 2-((2,2-difluoroethyl)amino)-2-(tetrahydrofuran-2-yl)ethan-1-ol (235 mg, 1.204 mmol, 1.00 equiv) in anhydrous THF (4.59 mL, 56.600 mmol, 47.01 equiv) was added 7-bromo-6-chloro-5,8-difluoro-2-(((2R,7aS)-2-fluorotetrahydro-1H-pyrrolizin-7a(5H)-yl)methoxy)quinazolin-4-ol (299 mg, 0.662 mmol, 0.55 equiv) followed by NaH (260 mg, 10.836 mmol, 9.00 equiv) at 0° C. under nitrogen atmosphere. The reaction mixture was stirred at 0° C. to room temperature for 1 hour and quenched by addition of water 20 mL at 0° C. The aqueous layer was extracted with DCM (3×50 mL). The extracts were combined, washed with brine (50 mL), and dried over anhydrous $Na_2SO_4$. It was filtered and concentrated under reduced pressure to afford the desired product as a yellow solid which was used directly in the next step without further purification. (ESI, m/z): 627 [M+H]$^+$ 9-Bromo-8-chloro-4-(2,2-difluoroethyl)-10-fluoro-2-(((2R,7aS)-2-fluorotetrahydro-1H-pyrrolizin-7a(5H)-yl) methoxy)-5-(tetrahydrofuran-2-yl)-5,6-dihydro-4H-[1,4] oxazepino[5,6,7-de]quinazoline To a stirred solution of 7-bromo-6-chloro-5-(2-((2,2-difluoroethyl)amino)-2-(tetrahydrofuran-2-yl)ethoxy)-8-fluoro-2-(((2R,7aS)-2-fluorotetrahydro-1H-pyrrolizin-7a(5H)-yl)methoxy)quinazolin-4-ol (630 mg, 1.003 mmol, 1 equiv) in anhydrous dioxane (12.6 mL, 148.730 mmol, 148.22 equiv) was added triethylamine (1.67 mL, 12.036 mmol, 12 equiv) and $POCl_3$ (923 mg, 6.018 mmol, 6 equiv) at room temperature. The reaction mixture was stirred at 80° C. for a period of 1 hour. After completion of reaction, the reaction mixture was quenched by addition of water (30 mL) and extracted with DCM (3×50 mL). The extracts were combined, dried over anhydrous sodium sulfate. It was filtered, concentrated under reduced pressure to give crude product, which was purified by reversed-phase flash chromatography with the following conditions: column, C18; mobile phase, MeCN in Water (0.5% $NH_4HCO_3$), 50% to 60% gradient in 10 min; detector, UV 254 nm to afford the desired product as a yellow solid. (ESI, m/z): 609 [M+H]$^+$ Tert-butyl (4-(8-chloro-4-(2,2-difluoroethyl)-10-fluoro-2-(((2R,7aS)-2-fluorotetrahydro-1H-pyrrolizin-7a(5H)-yl) methoxy)-5-(tetrahydrofuran-2-yl)-5,6-dihydro-4H-[1,4] oxazepino[5,6,7-de]quinazolin-9-yl)-3-cyano-7-fluorobenzo[b]thiophen-2-yl)carbamate To a stirred solution of 9-bromo-8-chloro-4-(2,2-difluoroethyl)-10-fluoro-2-(((2R,7aS)-2-fluorotetrahydro-1H-pyrrolizin-7a(5H)-yl) methoxy)-5-(tetrahydrofuran-2-yl)-5,6-dihydro-4H-[1,4] oxazepino[5,6,7-de]quinazoline (110 mg, 0.180 mmol, 1 equiv) in anhydrous toluene (10 mL, 93.986 mmol, 521.06 equiv) was added tert-butyl N-[3-cyano-4-(5,5-dimethyl-1,3,2-dioxaborinan-2-yl)-7-fluoro-1-benzothiophen-2-yl]carbamate (219 mg, 0.540 mmol, 3 equiv) and $Cs_2CO_3$ (176 mg, 0.540 mmol, 3 equiv) followed by dichloropalladium; (2-[2-(diphenylphosphanyl)phenoxy]phenyl)diphenylphosphane (32 mg, 0.045 mmol, 0.25 equiv) at room temperature. The reaction mixture was stirred at 110° C. for 1 hour under nitrogen atmosphere. After completion of reaction, the reaction mixture was cooled to room temperature, quenched with water (20 mL), and extracted with DCM (4×50 mL). The extracts were combined washed with brine and dried over anhydrous sodium sulfate. It was filtered and concentrated under reduced pressure to give crude product which was purified by reversed-phase flash chromatography with the following conditions: column, C18; mobile phase, MeCN in Water (0.5% NH$_4$HCO$_3$), 10% to 50% gradient in 10 min; detector, UV 254 nm to afford the desired product as a light-yellow solid. (ESI, m/z): 821 [M+H]$^+$ 2-Amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile A solution of tert-butyl (4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-3-cyano-7-fluorobenzo[b]thiophen-2-yl)carbamate (100 mg, 0.122 mmol, 1 equiv) in TFA (0.5 mL, 6.732 mmol, 55.28 equiv) and DCM (1.5 mL, 23.596 mmol, 193.78 equiv) was stirred at room temperature for 1 hour and concentrated under reduced pressure to give a crude. The crude product was purified by Prep-HPLC with the following conditions (Column: XBridge BEH Shield RP18 5 m, 30 mm*150 mm; Mobile Phase A: Water (10 mmol/L NH$_4$HCO$_3$), Mobile Phase B: ACN; Flow rate: 60 mL/min; Gradient: 46% B to 71% B in 10 min; Wave Length: UV 254 nm/220 nm; RT1(min): 8.13/9.32) to afford the desired product as a white solid. (ESI, m/z): 721 [M+H]$^+$ $^1$H NMR: (400 MHZ, DMSO-d$_6$, ppm) § 8.09 (s, 2H), 7.26 (dd, J=8.4, 5.3 Hz, 1H), 7.17-6.99 (m, 1H), 6.64-6.32 (m, 1H), 5.46-5.17 (m, 1H), 4.97 (dd, J=13.4, 4.7 Hz, 1H), 4.90-4.73 (m, 1H), 4.45-4.31 m, 1H), 4.2-3.99 (m, 3H), 3.96-3.78 (m, 3H), 3.64 (q, J=7.4 Hz, 1H), 3.23-3.08 (m, 2H), 3.02 (s, 1H), 2.89-2.79 (m, 1H), 2.21-1.92 (m, 5H), 1.89-1.69 (m, 5H).

Example 1br: Synthesis of ((2R)—N-(3-(9-(2-amino-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)-N-methylaziridine-2-carboxamide (709)

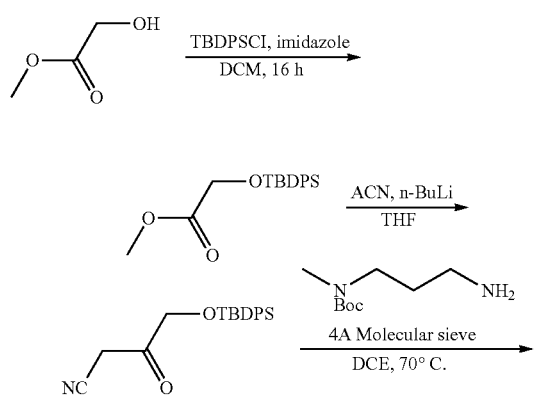

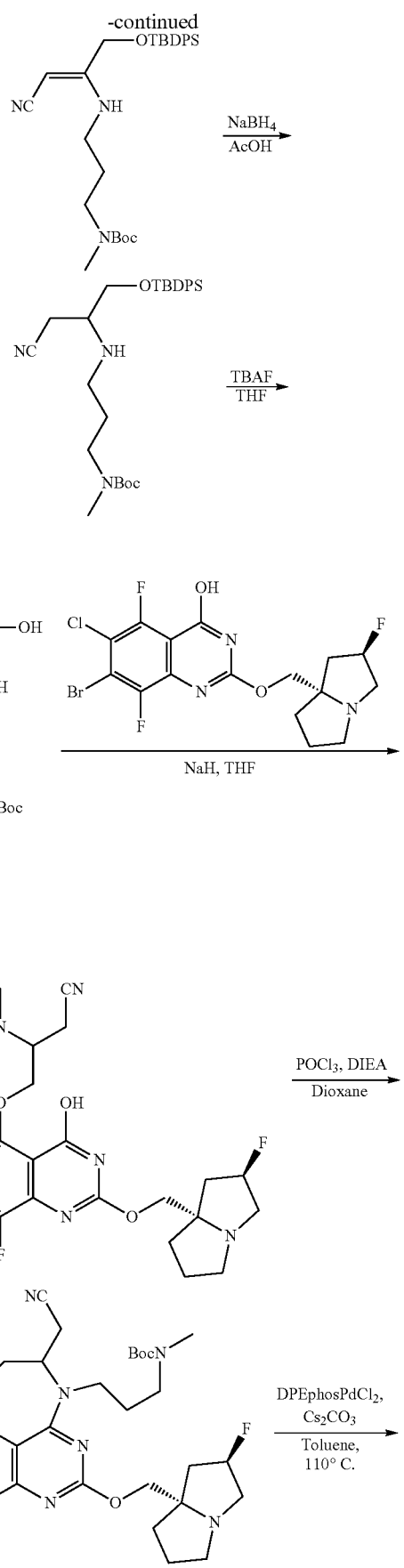

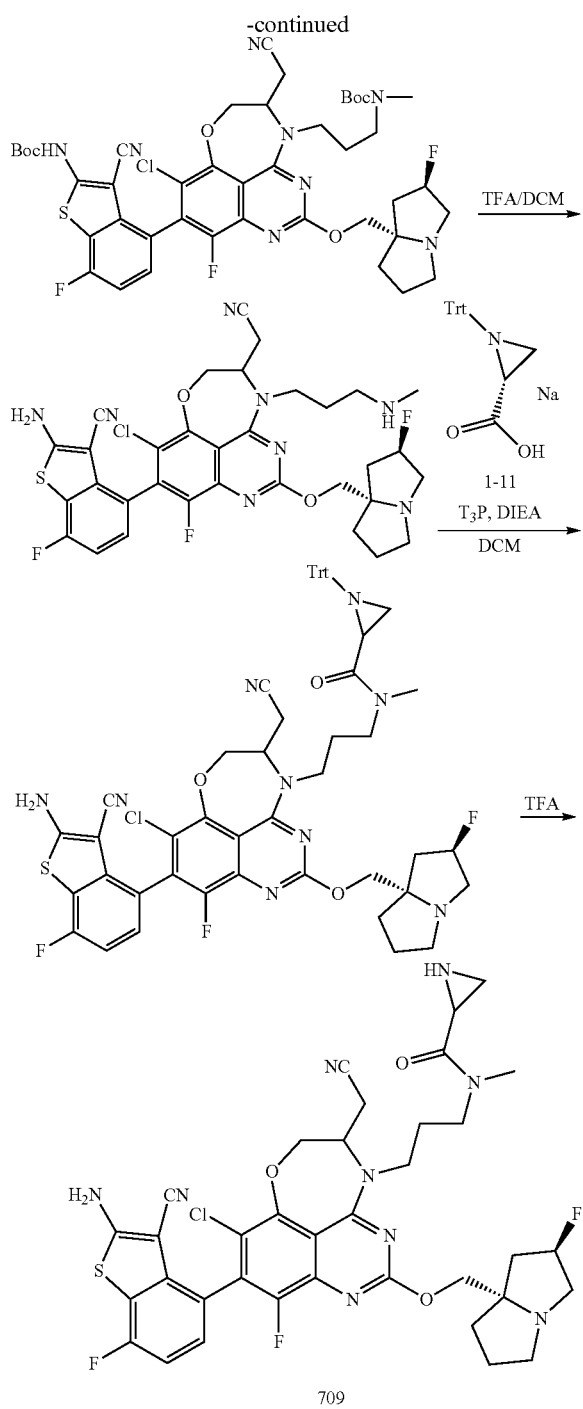

709

Methyl 2-((tert-butyldiphenylsilyl)oxy)acetate To a solution of tert-butyl (1-(hydroxymethyl)cyclobutyl)carbamate (1-1) (5.0 g, 1 eq., 55.56 mmol) in DCM (40 ml) was added imidazole (11.32 g, 166.67 mmol) and TBDPSCl (22.93 g, 83.25 mmol) at 0° C., the mixture was stirred for 16 hours at room temperature. The reaction was quenched with H$_2$O (50 mL), extracted with DCM (3×50 mL). The extracts were combined, dried over anhydrous sodium sulfate. It was filtered and concentrated under vacuum to give a residue. The residue was purified by silica gel column chromatography (petroleum: ethyl acetate=20:1) to obtain the desired product. ESI-MS m/z: 351.1 [M+Na]$^+$.

4-((Tert-butyldiphenylsilyl)oxy)-3-oxobutanenitrile To a solution of ACN (1.37 g, 33.38 mmol) in THF (30 mL) was added n-BuLi (15.3 mL, 24.48 mmol) slowly at −78° C. under nitrogen, and the resulting mixture was stirred-78° C. for 0.5 hours. Methyl 2-((tert-butyldiphenylsilyl)oxy)acetate (7.3 g, 22.3 mmol) in THF (20 mL) was added at −78° C. and stirred for 2 hours. The mixture was quenched with aqueous NH$_4$Cl (50 mL) and extracted with ethyl acetate (3×80 mL). The extracts were combined, washed with bine, and dried over anhydrous sodium sulfate. It was filtered and concentrated under pressure to give a residue. The residue was purified by silica gel column chromatography (petroleum: ethyl acetate=20:1) to obtain the desired product as a yellow solid. ESI-MS m/z: 359.9 [M+Na]$^+$.

Tert-butyl (Z)-(3-((3-((tert-butyldiphenylsilyl)oxy)-1-cyanoprop-1-en-2-yl)amino)propyl)-(methyl)carbamate To a solution of 4-((tert-butyldiphenylsilyl)oxy)-3-oxobutanenitrile (2.03 g, 6.035 mmol), tert-butyl (3-aminopropyl)(methyl)carbamate (1.14 g, 6.035 mmol) and 4A molecular sieve in DCE (20 mL) was stirred at 60° C. for 12 hours. It was cooled, quenched by water (20 mL) and extracted with DCM (2×50 ml). The extracts were combined, washed with brine, and dried over anhydrous sodium sulfate. It was filtered and concentrated under vacuum to give a residue. The residue was purified by silica gel column chromatography (petroleum: ethyl acetate=5:1) to obtain the desired product ESI-MS m/z: 507.9 [M+H]$^+$.

Tert-butyl (3-((1-((tert-butyldiphenylsilyl)oxy)-3-cyanopropan-2-yl)amino)propyl)(methyl)-carbamate The mixture of tert-butyl (Z)-(3-((3-((tert-butyldiphenylsilyl)oxy)-1-cyanoprop-1-en-2-yl)amino)propyl)-(methyl)carbamate (2.64 g, 5.2 mmol) and NaBH$_3$CN (327 mg, 2.5 mmol) in AcOH (10 mL) was stirred at room temperature for 1 hour. The mixture was basified with aqueous NaHCO$_3$ to PH~8 and extracted with ethyl acetate (3×10 mL). The extracts were combined, dried over anhydrous sodium sulfate. It was filtered and concentrated under vacuum to give a residue. The residue was purified by silica gel column chromatography (petroleum: ethyl acetate=3:1) to obtain the desired product. ESI-MS m/z: 510.3 [M+H]$^+$.

Tert-butyl (3-((1-cyano-3-hydroxypropan-2-yl)amino)propyl)(methyl)carbamate To a solution of tert-butyl (3-((1-((tert-butyldiphenylsilyl)oxy)-3-cyanopropan-2-yl)amino)propyl)(methyl)-carbamate (960 mg, 1.19 mmol) in 10 mL of THF was added TBAF (3.77 mL, 3.77 mmol, 1M in THF) and the mixture was stirred at room temperature for 1 hour. The mixture was diluted with water (10 mL) and extracted with IPA/DCM=⅓ (3×10 mL). The combined organic layer was dried over anhydrous sodium sulfate. It was filtered and concentrated under pressure to give a residue. The residue was purified by silica gel column chromatography (DCM: MeOH=10:1) to obtain the desired product. ESI-MS m/z: 272.0 [M+H]$^+$.

Tert-butyl (3-((1-((7-bromo-6-chloro-8-fluoro-2-(((2R, 7aS)-2-fluorotetrahydro-1H-pyrrolizin-7a(5H)-yl) methoxy)-4-hydroxyquinazolin-5-yl)oxy)-3-cyanopropan-2-yl)amino)-propyl)(methyl)carbamate The mixture of tert-butyl (3-((1-cyano-3-hydroxypropan-2-yl)amino)propyl) (methyl)carbamate (120 mg, 0.44 mmol), 7-bromo-6-chloro-5,8-difluoro-2-(((2R,7aS)-2-fluorotetrahydro-1H-pyrrolizin-7a(5H)-yl)methoxy)-quinazolin-4-ol (100 mg, 0.0.221 mmol) and NaH (44.3 mg, 1.10 mmol, 60%) in THF (2 mL) was stirred at room temperature for 12 hours. The reaction was quenched with water (10 mL), extracted with ethyl acetate (2×15 mL). The extracts were combined, washed with brine and dried over anhydrous sodium sulfate. It was filtered and concentrated under vacuum to give a residue. The residue was purified by silica gel column chromatography (DCM:MeOH=10:1) to obtain the desired product. ESI-MS m/z: 705.1 [M+H]$^+$.

Tert-butyl (3-(9-bromo-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)(methyl)carbamate The mixture of tert-butyl (3-((1-((7-bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)-3-cyanopropan-2-yl)amino)-propyl)(methyl)carbamate (116 mg, 0.17 mmol), DIEA (2 mL) and POCl$_3$ (0.5 mL) in 1,4-dioxane (2 mL) was stirred at room temperature for 1 hour. The reaction was quenched with water (20 mL), extracted with ethyl acetate (2×10 mL). The extracts were combined, washed with brine, and dried over anhydrous sodium sulfate. It was filtered and concentrated under vacuum obtain the desired product. ESI-MS m/z: 686.9 [M+H]$^+$.

Tert-butyl (3-(9-(2-((tert-butoxycarbonyl)amino)-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)(methyl)carbamate The mixture of tert-butyl (3-(9-bromo-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)(methyl)carbamate (140 mg, 0.21 mmol), tert-butyl (3-cyano-4-(5,-dimethyl-1,3-dioxan-2-yl)-7-fluoro-1H-inden-2-yl)carbamate (165 mg, 0.41 mmol), DPEphosPdCl2 (36 mg, 0.051 mmol) and Cs$_2$CO$_3$ (200 mg, 0.61 mmol) in toluene (2 mL) was stirred at 110° C. for 5 hours under nitrogen. It was cooled to room temperature, filtered through a short pad of silica gel with DCM (3×15 mL) as eluting solvent. The filtrate was concentrated under vacuum to give a residue. The residue was purified by silica gel column chromatography (DCM:MeOH=10:1) to obtain the desired product. ESI-MS m/z: 897.2 [M+H]$^+$.

2-Amino-4-(8-chloro-5-(cyanomethyl)-10-fluoro-2-(((2R,7aS)-2-fluorotetrahydro-1H-pyrrolizin-7a(5H)-yl)methoxy)-4-(3-(methylamino)propyl)-5,6-dihydro-4H-[1,4]oxazepino[5,6,7-de]quinazolin-9-yl)-7-fluorobenzo[b]thiophene-3-carbonitrile The mixture of tert-butyl (3-(9-(2-((tert-butoxycarbonyl)amino)-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)(methyl)carbamate (110 mg, 0.12 mmol) and TFA (1 mL) in 2 mL of DCM was stirred at 30° C. for 1 hour. The mixture was basified with NH$_3$-MeOH (7 N) to PH~8 and concentrated under vacuum to give a residue. The residue was purified by silica gel column chromatography (DCM:MeOH=5:1) to obtain the desired product. ESI-MS m/z: 697.2 [M+H]$^+$.

(2R)—N-(3-(9-(2-amino-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)-N-methyl-1-tritylaziridine-2-carboxamide To a solution of 2-amino-4-(8-chloro-5-(cyanomethyl)-10-fluoro-2-(((2R,7aS)-2-fluorotetrahydro-1H-pyrrolizin-7a(5H)-yl)methoxy)-4-(3-(methylamino)propyl)-5,6-dihydro-4H-[1,4]oxazepino[5,6,7-de]quinazolin-9-yl)-7-fluorobenzo[b]thiophene-3-carbonitrile (50 mg, leq, 0.071 mmol), (R)-1-tritylaziridine-2-carboxylic acid, sodium salt (50 mg, 2 eq, 0.14 mmol) and DIEA (28 mg, 3 eq, 0.215 mmol) in dry DCM (3 mL) was added T3P (34 mg, 1.5 eq, 0.11 mmol) in dry DCM (1 mL) at 0° C. under nitrogen. The mixture was stirred at room temperature for 30 minutes. The mixture was poured into ice water (10 mL), extracted with ethyl acetate (30 mL×3). The extracts were combined, washed with brine (20 mL×2), and dried over anhydrous sodium sulfate. It was filtered and the filtrate was concentrated to dryness under reduced pressure to give a residue. The residue was purified by prep-TLC (NH$_3$ in MeOH(7N): DCM=1:10)) to give the desired product. MS m/z (ESI): 1007.9 [M+H]$^+$.

(2R)—N-(3-(9-(2-amino-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)-N-methylaziridine-2-carboxamide To a solution of (2R)—N-(3-(9-(2-amino-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)-N-methyl-1-tritylaziridine-2-carboxamide (12 mg, 0.012 mmol) in dry DCM (2 mL) was added TFA (1 mL) at 0° C. The mixture was stirred at 20° C. for 30 minutes and basified with NH$_3$-MeOH (7N) to PH~8. It was concentrated under vacuum to give a residue. The residue was purified by prep-HPLC (NH$_4$HCO$_3$) to obtain the desired product. ESI-MS m/z: 766.1 [M+H]$^+$.

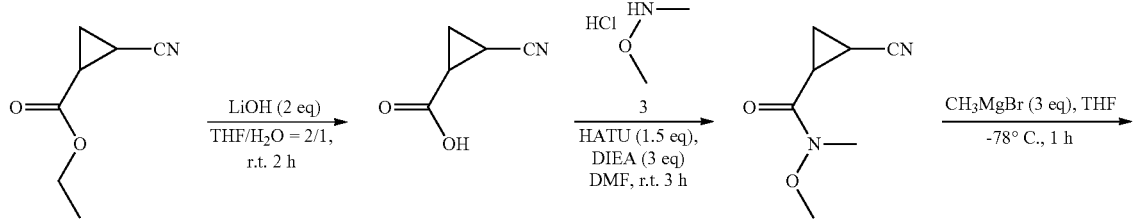

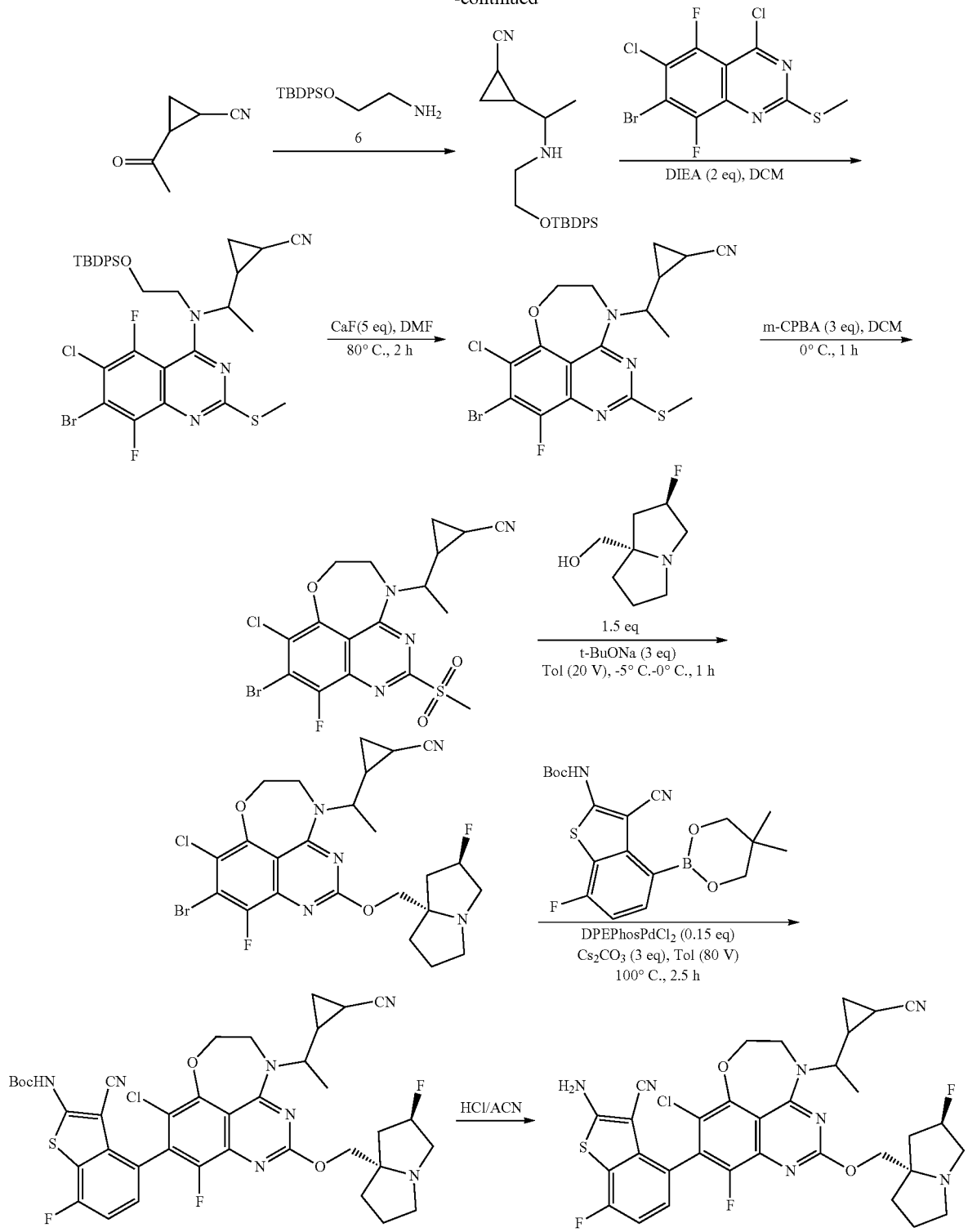

2-Cyanocyclopropane-1-carboxylic acid A solution of ethyl 2-cyanocyclopropane-1-carboxylate (1.0 g, 7.18 mmol, 1.00 equiv) and lithium hydroxide (430 mg, 17.96 mmol, 2.5 equiv) in THF (15 mL) and water (15 mL) was stirred for 3 hours at room temperature. The resulting mixture was diluted with water (35 mL). The mixture was acidified to pH~3 with HCl (aq.). The resulting mixture was extracted with ethyl acetate (3×50 mL). the extracts were combined, washed with brine and dried over anhydrous $Na_2SO_4$. After filtration, the filtrate was concentrated under reduced pressure to afford the desired product as a white solid which was used directly in the next step without further purification. (ES, m/z): 110 [M−H]-2-Cyano-N-methoxy-N-methylcyclopropane-1-carboxamide To a solution of 2-cyanocyclopropane-1-carboxylic acid (900 mg, 8.1 mmol, 1.0 equiv) and N,O-dimethylhydroxylamine (989 mg, 16.2 mmol, 2.0 equiv) in DCM (12 mL) was add HATU (4620 mg, 12.15 mmol, 1.50 equiv) and triethylamine (2459 mg, 24.3 mmol, 3.0 equiv). The resulting mixture was stirred for 2 hours at room temperature. It was diluted with water (15 mL) and extracted with ethyl acetate (2×40 mL). The extracts were combined, washed with brine (2×60 mL), dried over anhydrous $Na_2SO_4$. After filtration, the filtrate was concentrated under reduced pressure to give a residue. The residue was purified by silica gel column chromatography, eluted with petroleum/ethyl acetate (7:1) to afford the desired product as a colorless oil. (ES, m/z): 155 $[M+H]^+$ 2-Acetylcyclopropane-1-carbonitrile To a solution of 2-cyano-N-methoxy-N-methylcyclopropane-1-carboxamide (800 mg, 5.83 mmol, 1.0 equiv) in THF (4 mL) was added $CH_3MgBr$ (2784 mg, 23.35 mmol, 4.0 equiv) at −78° C. under nitrogen atmosphere, and the mixture was stirred for 3 hours at −78° C. The reaction was quenched by adding water at room temperature. The resulting mixture was extracted with ethyl acetate (3×25 mL). The extracts were combined, washed with brine (2×30 mL), and dried over anhydrous $Na_2SO_4$. After filtration, the filtrate was concentrated under reduced pressure to afford the desired product which was used directly in the next step without further purification as a colorless oil. (ES, m/z): 110 $[M+H]^+$ 2-[1-({2-[(Tert-butyldiphenylsilyl)oxy]ethyl}amino) ethyl]cyclopropane-1-carbonitrile To a solution of 2-acetyl-cyclopropane-1-carbonitrile (500 mg, 4.58 mmol, 1.0 equiv) and (2-aminoethoxy)(tert-butyl)diphenylsilane (1783 mg, 5.95 mmol, 1.3 equiv) in DCM (10 mL) was added $NaBH_3CN$ (575 mg, 9.16 mmol, 2.00 equiv) and AcOH (1375 mg, 22.91 mmol, 5.0 equiv). The mixture was stirred for 2 hours at 0° C. It was diluted with water (40 mL) and extracted with ethyl acetate (2×40 mL). The extracts were combined, washed with brine (2×60 mL), and dried over anhydrous $Na_2SO_4$. After filtration, the filtrate was concentrated under reduced pressure to give a residue. The residue was purified by silica gel column chromatography, eluted with $CH_2Cl_2$/MeOH (10:1) to afford the desired product as a colorless oil. (ES, m/z): 393 $[M+H]^+$ 2-(1-{[7-Bromo-6-chloro-5,8-difluoro-2-(methylsulfanyl)quinazolin-4-yl]({2-[(tert-butyldiphenylsilyl)oxy]ethyl})amino}ethyl)cyclopropane-1-carbonitrile A solution of 2-[1-({2-[(tert-butyldiphenylsilyl)oxy]ethyl}amino)ethyl]cyclopropane-1-carbonitrile (400 mg, 1.01 mmol, 1.0 equiv) TEA (206 mg, 2.03 mmol, 2.0 equiv) and 7-bromo-4,6-dichloro-5,8-difluoro-2-(methylsulfanyl)quinazoline (366 mg, 1.01 mmol, 1.0 equiv) in DCM (6 mL) was stirred for overnight at room temperature. The resulting mixture was diluted with water (30 mL) and extracted with ethyl acetate (2×40 mL). The extracts were combined, washed with brine (2×60 mL), and dried over anhydrous $Na_2SO_4$. After filtration, the filtrate was concentrated under reduced pressure to give a residue. The residue was purified by silica gel column chromatography, eluted with petroleum/ethyl acetate (8:1) to afford the desired product as a yellow solid. (ES, m/z): 715 $[M+H]^+$ 2-{1-[7-Bromo-8-chloro-6-fluoro-3-(methylsulfanyl)-10-oxa-2,4,13-triazatricyclo [7.4.1.0^{5,14}]tetradeca-1,3,5 (14),6,8-pentaen-13-yl]ethyl}cyclopropane-1-carbonitrile To a solution of 2-(1-{[7-bromo-6-chloro-5,8-difluoro-2-(methylsulfanyl)quinazolin-4-yl]({2-[(tert-butyldiphenylsilyl)oxy]-ethyl}) amino}ethyl)cyclopropane-1-carbonitrile (340 mg, 0.47 mmol, 1.0 equiv) in DMF (4 mL) was CsF (360 mg, 2.37 mmol, 5.0 equiv) and the resulting mixture was stirred for 1.5 hours at 80° C. The reaction mixture was cooled to room temperature, diluted with water (15 mL) and extracted with ethyl acetate (2×35 mL). The extracts combined, washed with brine (2×45 mL), and dried over anhydrous $Na_2SO_4$. After filtration, the filtrate was concentrated under reduced pressure to give a residue. The residue was purified by silica gel column chromatography, eluted with petroleum/ethyl acetate (8:1) to afford the desired product as a white solid. (ES, m/z): 457 $[M+H]^+$ 2-(1-{7-Bromo-8-chloro-6-fluoro-3-methanesulfonyl-10-oxa-2,4,13-triazatricyclo[7.4.1.0 -{5,14}]tetradeca-1,3,5 (14),6,8-pentaen-13-yl}ethyl)cyclopropane-1-carbonitrile To a solution of 2-{1-[7-bromo-8-chloro-6-fluoro-3-(methylsulfanyl)-10-oxa-2,4,13-triazatricyclo[7.4.1.0 -{5,14}] tetradeca-1,3,5(14),6,8-pentaen-13-yl]ethyl} cyclopropane-1-carbonitrile (120 mg, 0.26 mmol, 1.0 equiv) in DCM (5 mL) was added MCPBA (135 mg, 0.78 mmol, 3.0 equiv) in portions at −10° C. under nitrogen atmosphere. The resulting mixture was stirred for 3 hours at the same temperature. The reaction was quenched by the addition of $NaHSO_3$ (5 mL) at 0° C. it was treated with saturated $NaHCO_3$(aq.) to adjust pH~8. The resulting mixture was extracted with ethyl acetate (3×50 mL). The extracts were combined, washed with brine (1×50 mL), and dried over anhydrous $Na_2SO_4$. After filtration, the filtrate was concentrated under reduced pressure to afford the desired product as a yellow solid which was used in the next step without further purification. (ES, m/z): 489 $[M+H]^+$ 2-[1-(3-{[(2R,7aS)-2-fluoro-hexahydropyrrolizin-7a-yl]methoxy}-7-bromo-8-chloro-6-fluoro-10-oxa-2,4,13-triazatricyclo[7.4.1.0^{5,14}]tetradeca-1,3,5(14),6,8-pentaen-13-yl)ethyl]cyclopropane-1-carbonitrile To a solution of 2-(1-{7-bromo-8-chloro-6-fluoro-3-methanesulfonyl-10-oxa-2,4,13-triazatricyclo[7.4.1.0^{5,14} ]tetradeca-1,3,5(14),6,8-pentaen-13-yl}ethyl)cyclopropane-1-carbonitrile (280 mg, 0.57 mmol, 1.0 equiv) and [(2R,7aS)-2-fluoro-hexahydro-pyrrolizin-7a-yl]methanol (136 mg, 0.85 mmol, 1.5 equiv) in DCM (5 mL) was added t-BuONa (164 mg, 1.71 mmol, 3.0 equiv) in portions at −10° C. The resulting mixture was stirred for 1 hour at −10° C. under nitrogen atmosphere. It was quenched by the addition of sat. $NH_4Cl$ (aq.) (5 mL) at 0° C. and extracted with ethyl acetate (3×50 mL). The extracts were combined, washed with brine (1×50 mL), and dried over anhydrous $Na_2SO_4$. After filtration, the filtrate was concentrated under reduced pressure to give a residue The residue was purified by reversed-phase flash chromatography with the following conditions: column, C18; mobile phase, MeCN in Water (10 mmol/L $NH_4HCO_3$), 20% to 50% gradient in 10 min; detector, UV 254 nm to afford the desired product as a white solid. (ES, m/z): 568 $[M+H]^+$ Tert-butyl N-[4-(3-{[(2R,7aS)-2-fluoro-hexahydropyr-rolizin-7a-yl]methoxy}-8-chloro-13-[1-(2-cyanocyclopro-pyl)ethyl]-6-fluoro-10-oxa-2,4,13-triazatricyclo[7.4.1.0^{5, 14}]tetradeca-1,3,5(14),6,8-pentaen-7-yl)-3-cyano-7-fluoro-1-benzothiophen-2-yl]carbamate To a reaction tube charged with magnetic bar was added 32-[1-(3-{[(2R,7aS)-2-fluoro-hexahydropyrrolizin-7a-yl]methoxy}-7-bromo-8-chloro-6-fluoro-10-oxa-2,4,13-triazatricyclo [7.4.1.0^{5,14} ]tetradeca-1,3,5(14),6,8-pentaen-13-yl)ethyl]cyclopropane-1-carbonitrile (60 mg, 0.1 mmol, 1.0 equiv), dichloropalladium; {2-[2-(diphenylphosphanyl)phenoxy]phenyl} diphenylphospha (75 mg, 0.1 mmol, 1.0 equiv), $Cs_2CO_3$ (103.1 mg, 0.31 mmol, 3.00 equiv), tert-butyl N-[3-cyano-4-(5,5-dimethyl-1,3,2-dioxaborinan-2-yl)-7-fluoro-1-benzothiophen-2-yl]carbamate (85 mg, 0.21 mmol, 2.0 equiv) and toluene (2 mL). It was evacuated and refilled with nitrogen, and this was repeated for three times before the reaction mixture was stirred at 100° C. for 2.5 hours. It was cooled to room temperature and the resulting mixture was concentrated under vacuum to give a residue. The residue was purified by prep-TLC (CH$_2$Cl$_2$/MeOH 10:1) to afford the desired product as a yellow solid. (ES, m/z): 780 [M+H]$^+$ 4-(3-{[(2R,7aS)-2-fluoro-hexahydropyrrolizin-7a-yl]methoxy}-8-chloro-13-[1-(2-cyanocyclopropyl)ethyl]-6-fluoro-10-oxa-2,4,13-triazatricyclo[7.4.1.0^{5,14}]tetradeca-1,3,5(14),6,8-pentaen-7-yl)-2-amino-7-fluoro-1-benzothiophene-3-carbonitrile A solution of tert-butyl N-[4-(3-{[(2R,7aS)-2-fluoro-hexahydropyrrolizin-7a-yl]methoxy}-8-chloro-13-[1-(2-cyanocyclopropyl)ethyl]-6-fluoro-10-oxa-2,4,13-triazatricyclo[7.4.1.0^{5,14}]tetradeca-1,3,5(14),6,8-pentaen-7-yl)-3-cyano-7-fluoro-1-benzothiophen-2-yl]carbamate (30 mg, 0.04 mmol, 1.0 equiv) and HCl (gas) in 1,4-dioxane (0.1 mL) in ACN (0.4 mL) was stirred for 1 hour at room temperature. The mixture was basified to pH~8 with saturated NH$_4$Cl (aq.) and extracted with ethyl acetate (2×30 mL). The extracts were combined, washed with brine, and dried over anhydrous Na$_2$SO$_4$. After filtration, the filtrate was concentrated under reduced pressure to give a crude. The crude product was purified by prep-HPLC with the following conditions (Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 30% B to 70% B in 10 min, 70% B; Wave Length: UV 220 nm; RT1(min): 9.57; Number Of Runs: 0) to afford the desired product as a white solid. (ES, m/z): 679.85 [M+H]$^+$ $^1$H NMR (400 MHZ, DMSO-d$_6$) δ 8.12 (s, 2H), 7.21 (dt, J=8.4, 4.3 Hz, 1H), 7.14 (t, J=8.9 Hz, 1H), 5.41 (d, J=53.3 Hz, 1H), 4.76-4.56 (m, 2H), 4.48-4.11 (m, 3H), 3.92 (dd, J=27.5, 10.1 Hz, 2H), 3.41 (d, J=5.8 Hz, 2H), 3.15 (s, 2H), 2.33 (s, 3H), 2.12 (dd, J=9.3, 4.9 Hz, 2H), 2.05-1.84 (m, 3H), 1.44-1.34 (m, 2H), 1.33-1.04 (m, 3H).

Example 1bs: Synthesis of 2-amino-4-(9-chloro-4-(2,2-difluoroethyl)-11-fluoro-2-(((2R,7aS)-2-fluoro-tetrahydro-1H-pyrrolizin-7a(5H)-yl)methoxy)-7-(hydroxymethyl)-4,5,6,7-tetrahydro-[1,5]oxazocino[4,3,2-de]quinazolin-10-yl)-7-fluorobenzo[b]thiophene-3-carbonitrile (1207 and 1216)

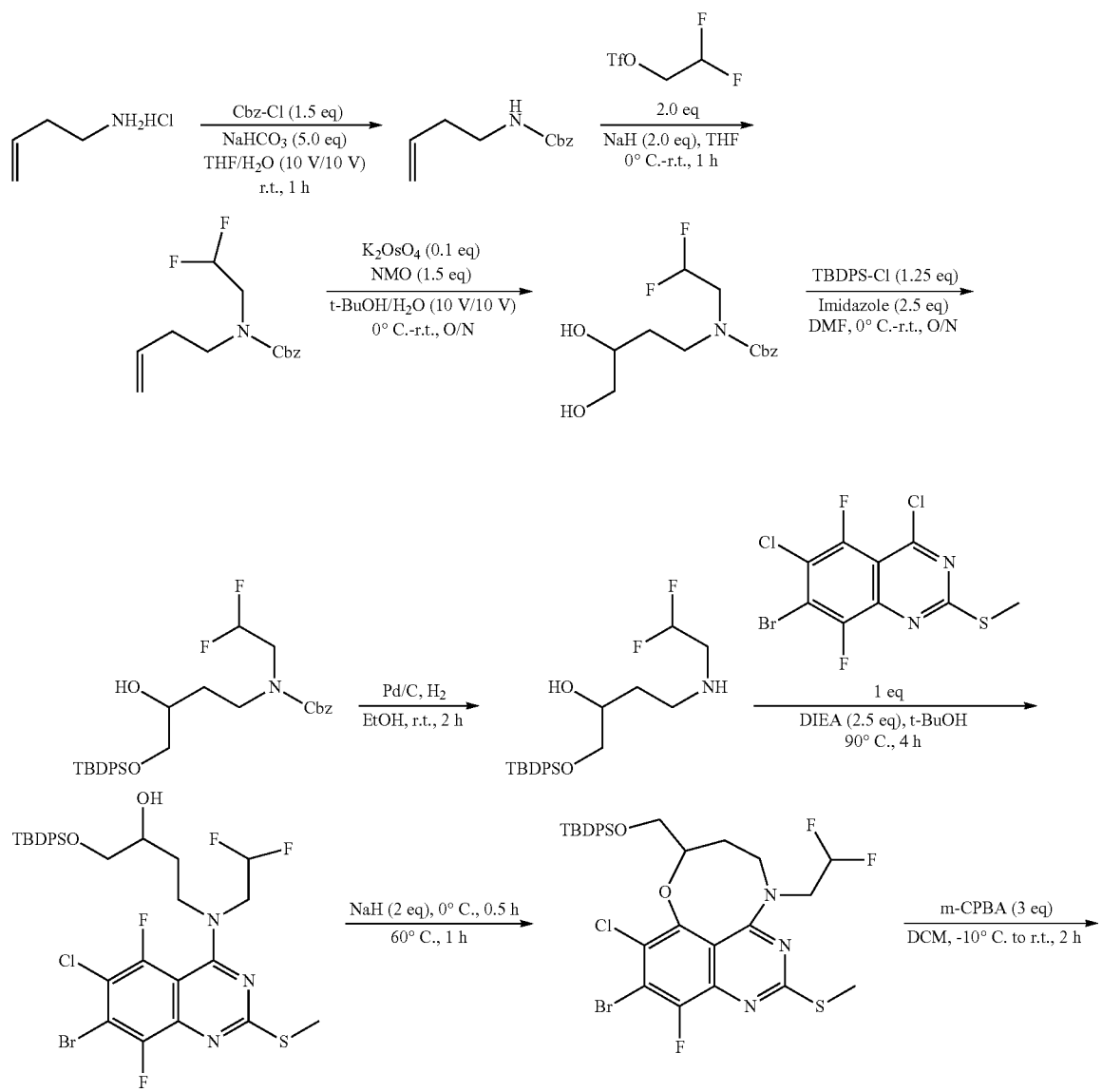

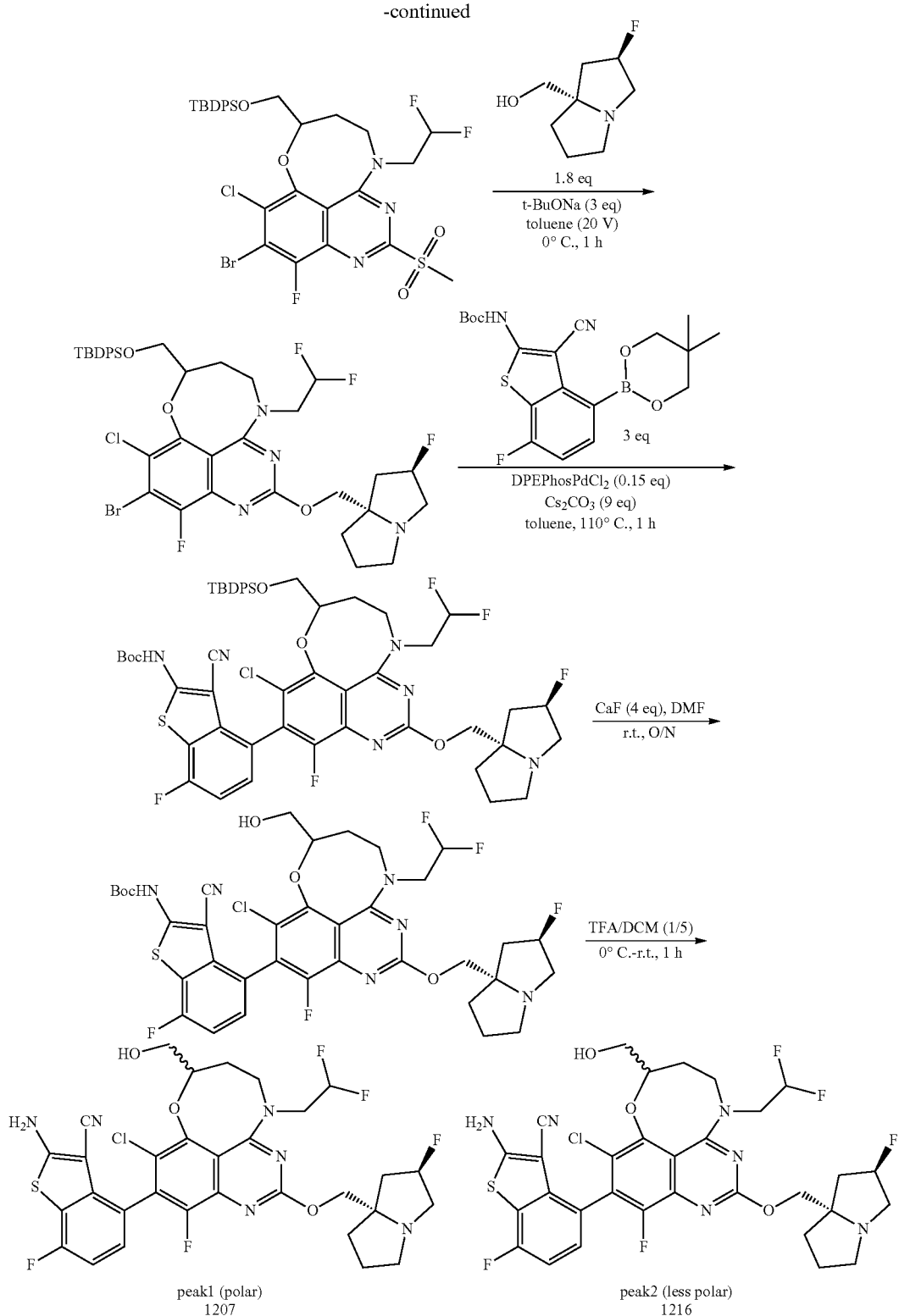

peak1 (polar)
1207 peak2 (less polar)
1216

Benzyl N-(but-3-en-1-yl)carbamate A solution of 3-buten-1-amine hydrochloride (1.00 g, 9.29 mmol, 1.0 equiv) in THF (10.0 mL) and H$_2$O (10.0 mL) was treated with NaHCO$_3$ (3.90 g, 46.47 mmol, 5.0 equiv) for at room temperature under nitrogen atmosphere followed by addition of benzyl chloroformate (2.38 g, 13.94 mmol, 1.5 equiv) dropwise at 0° C. The resulting mixture was stirred for 1 hour at room temperature under nitrogen atmosphere. The resulting mixture was extracted with ethyl acetate (3×50 mL). The extracts were combined, washed with brine (3×20 mL), dried over anhydrous Na$_2$SO$_4$. After filtration, the filtrate was concentrated under reduced pressure to give a residue. The residue was purified by silica gel column chromatography, eluted with petroleum/ethyl acetate (5:1) to afford the desired product as a yellow oil. (ESI, m/z): 206 [M+H]$^+$ Benzyl N-(but-3-en-1-yl)-N-(2,2-difluoroethyl)carbamate A suspension of NaH (1.05 g, 26.26 mmol, 2.0 equiv, 60%) in THF (10 mL) was treated with but-3-en-1-yl(methyl)amine (1.30 g, 13.13 mmol, 1.0 equiv, 86% purity) for 30 minutes at 0° C. under nitrogen atmosphere. 2,2-difluoroethyl trifluoromethanesulfonate (5.62 g, 26.26 mmol, 2.0 equiv) was added dropwise at 0° C. and the resulting mixture was stirred for 1 hour at room temperature. The reaction was quenched by water at 0° C. and the mixture was extracted with ethyl acetate (3×50 mL). The extracts were combined, washed with brine (3×20 mL), dried over anhydrous Na$_2$SO$_4$. After filtration, the filtrate was concentrated under reduced pressure to give a residue. The residue was purified by silica gel column chromatography, eluted with petroleum/ethyl acetate (5:1) to afford the desired product as a yellow oil. (ESI, m/z): 270 [M+H]$^+$ Benzyl N-(2,2-difluoroethyl)-N-(3,4-dihydroxybutyl)carbamate A solution of benzyl N-(but-3-en-1-yl)-N-(2,2-difluoroethyl)carbamate (1.40 g, 4.99 mmol, 1.0 equiv, 96% purity) in H$_2$O (10 mL) and t-BuOH (10 mL) was treated with NMO (0.88 g, 7.48 mmol, 1.5 equiv) at 0° C. under nitrogen atmosphere followed by the addition of K$_2$Os$_4$·2H$_2$O (0.18 g, 0.5 mmol, 0.1 equiv) dropwise at 0° C. The resulting mixture was stirred for overnight at room temperature under nitrogen atmosphere. It was extracted with ethyl acetate (3×50 mL). The extracts were combined, washed with brine (3×20 mL), dried over anhydrous Na$_2$SO$_4$. After filtration, the filtrate was concentrated under reduced pressure to give desire product as a brown oil which was used directly in the next step without further purification. (ESI, m/z): 304 [M+H]$^+$ Benzyl N-{4-[(tert-butyldiphenylsilyl)oxy]-3-hydroxybutyl}-N-(2,2-difluoroethyl)carbamate A solution of benzyl N-(2,2-difluoroethyl)-N-(3,4-dihydroxybutyl)carbamate (1.00 g, 2.64 mmol, 1.0 equiv, 80%) in DMF (10 mL) was treated with imidazole (0.45 g, 6.59 mmol, 2.5 equiv) at room temperature under nitrogen atmosphere followed by the addition of tert-butyl(chloro)diphenylsilane (1.09 g, 3.95 mmol, 1.5 equiv) dropwise at 0° C. The resulting mixture was stirred for overnight at room temperature under nitrogen atmosphere. It was extracted with ethyl acetate (3×50 mL). The extracts were combined, washed with brine (3×20 mL), dried over anhydrous Na$_2$SO$_4$. After filtration, the filtrate was concentrated under reduced pressure to give a residue. The residue was purified by silica gel column chromatography, eluted with petroleum/ethyl acetate (5:1) to afford the desired product as a colorless oil. (ESI, m/z): 542 [M+H]$^+$ Benzyl N-{4-[(tert-butyldiphenylsilyl)oxy]-3-hydroxybutyl}-N-(2,2-difluoroethyl)carbamate To a solution of benzyl N-{4-[(tert-butyldiphenylsilyl)oxy]-3-hydroxybutyl}-N-(2,2-difluoroethyl)carbamate (1.65 g, 2.01 mmol, 1.0 equiv, 95%) in EtOH (21.8 mL) was added Pd/C (0.32 g, 0.3 mmol, 0.15 equiv, 10%) and the resulting mixture was stirred for 2 hours at room temperature under hydrogen atmosphere. It was filtered and the filter cake was washed with EtOAc (3×100 mL). The filtrate was concentrated under reduced pressure to give a residue. The residue was purified by silica gel column chromatography, eluted with petroleum/ethyl acetate (1:1) to afford the desired product as a colorless oil. (ESI, m/z): 408 [M+H]$^+$ 7-Bromo-N-{4-[(tert-butyldiphenylsilyl)oxy]-3-hydroxybutyl}-6-chloro-N-(2,2-difluoroethyl)-5,8-difluoro-2-(methylsulfanyl)quinazolin-4-amine A solution of {4-[(tert-butyldiphenylsilyl)oxy]-3-hydroxybutyl}(2,2-difluoroethyl)amine (970 mg, 2.26 mmol, 1.0 equiv, 95%) and 7-bromo-4,6-dichloro-5,8-difluoro-2-(methylsulfanyl)quinazoline (813.9 mg, 2.26 mmol, 1.0 equiv) in t-BuOH (9.2 mL) was treated with DIEA (730.5 mg, 5.65 mmol, 2.5 equiv) at room temperature under nitrogen atmosphere. The resulting mixture was stirred for 4 hours at 90° C. It was cooled to room temperature, quenched with water (30 mL), and extracted with ethyl acetate (3×30 mL). The extracts were combined, washed with brine (3×10 mL), and dried over anhydrous Na$_2$SO$_4$. After filtration, the filtrate was concentrated under reduced pressure to give a residue. The residue was purified by silica gel column chromatography, eluted with petroleum/ethyl acetate (2:1) to afford the desired product as a yellow solid. (ESI, m/z): 730 [M+H]$^+$ 7-Bromo-11-{[(tert-butyldiphenylsilyl)oxy]methyl}-8-chloro-14-(2,2-difluoroethyl)-6-fluoro-3-(methylsulfanyl)-10-oxa-2,4,14-triazatricyclo[7.5.1.0ˆ{5,15}]pentadeca-1,3,5(15),6,8-pentaene A suspension of NaH (0.12 g, 3.0 mmol, 2.0 equiv, 60%) in THF (4.3 mL) was treated with 7-bromo-N-{4-[(tert-butyldiphenylsilyl)oxy]-3-hydroxybutyl}-6-chloro-N-(2,2-difluoroethyl)-5-fluoro-2-(methylsulfanyl)quinazolin-4-amine (1.15 g, 1.5 mmol, 1.0 equiv, 93% purity) for 30 minutes at 0° C. under nitrogen atmosphere. The mixture was irradiated with microwave radiation for 1 hour at 60° C. and cooled to room temperature. It was quenched with sat. NH$_4$Cl (aq.) at 0° C., and extracted with ethyl acetate (3×30 mL). The extracts were combined, washed with brine (3×10 mL), and dried over anhydrous Na$_2$SO$_4$. After filtration, the filtrate was concentrated under reduced pressure to give a residue. The residue was purified by silica gel column chromatography, eluted with petroleum/ethyl acetate (5:1) to afford the desired product as an off-white solid. (ESI, m/z): 710 [M+H]$^+$ 7-Bromo-11-{[(tert-butyldiphenylsilyl)oxy]methyl}-8-chloro-14-(2,2-difluoroethyl)-6-fluoro-3-methanesulfonyl-10-oxa-2,4,14-triazatricyclo[7.5.1.0ˆ{5,15}]pentadeca-1,3,5(15),6,8-pentaene A solution of 7-bromo-11-{[(tert-butyldiphenylsilyl)oxy]methyl}-8-chloro-14-(2,2-difluoroethyl)-6-fluoro-3-(methylsulfanyl)-10-oxa-2,4,14-triazatricyclo[7.5.1.0ˆ{5,15}]-pentadeca-1,3,5(15),6,8-pentaene (350 mg, 0.49 mmol, 1.0 equiv) in DCM (7.0 mL) was treated with m-CPBA (351 mg, 1.73 mmol, 3.5 equiv, 85% wt) for 2 hours at −10-0° C. under nitrogen atmosphere. The reaction was then quenched with NaHSO$_3$ at 0° C. The mixture was neutralized to pH~8 with NaHCO$_3$ and extracted with CH$_2$Cl$_2$ (3×30 mL). The extracts were combined, washed with brine (3×10 mL), and dried over anhydrous Na$_2$SO$_4$. After filtration, the filtrate was concentrated under reduced pressure to give the desired product as a yellow solid which was used directly in the next step without further purification. (ESI, m/z): 742 [M+H]$^+$ 3-{[(2R,7aS)-2-fluoro-hexahydropyrrolizin-7a-yl]methoxy}-7-bromo-8-chloro-14-(2,2-difluoroethyl)-6-fluoro-11-(methoxymethyl)-10-oxa-2,4,14-triazatricyclo[7.5.1.0ˆ{5,15}]-pentadeca-1,3,5(15),6,8-pentaene A solution of 7-bromo-11-{[(tert-butyldiphenylsilyl)oxy]methyl}-8-chloro-14-(2,2-difluoroethyl)-6-fluoro-3-methanesulfonyl-10-oxa-2,4,14-triazatricyclo[7.5.1.0ˆ{5,15}]pentadeca-1,3,5(15),6,8-pentaene (400 mg, 0.53 mmol, 1.0 equiv) in toluene (8.0 mL) was treated with [(2R,7aS)-2-fluoro-hexahydropyrrolizin-7a-yl]methanol (154 mg, 0.96 mmol, 1.8 equiv) at 0° C. under nitrogen atmosphere followed by the addition of t-BuONa (155 mg, 1.61 mmol, 3.0 equiv) at 0° C. The resulting solution was stirred for 1 hour at 0° C. and the reaction was quenched with sat. NH₄Cl (aq.). It was extracted with ethyl acetate (3×30 mL). The extracts were combined, washed with brine (3×10 mL), dried over anhydrous Na₂SO₄. After filtration, the filtrate was concentrated under reduced pressure to give a residue. The residue was purified by silica gel column chromatography, eluted with petroleum/ethyl acetate (1:1) to afford the desired product as a white solid. (ESI, m/z): 821 [M+H]⁺

3-{[(2R,7aS)-2-fluoro-hexahydropyrrolizin-7a-yl] methoxy}-7-bromo-11-{[(tert-butyldiphenylsilyl)oxy]methyl}-8-chloro-14-(2,2-difluoroethyl)-6-fluoro-10-oxa-2,4,14-triazatricyclo[7.5.1.0^{5,15}]pentadeca-1,3,5(15),6,8-pentaene To a round bottom flask was added 3-{[(2R,7aS)-2-fluoro-hexahydropyrrolizin-7a-yl]methoxy}-7-bromo-11-{[(tert-butyldiphenylsilyl)oxy]methyl}-8-chloro-14-(2,2-difluoroethyl)-6-fluoro-10-oxa-2,4,14-triazatricyclo[7.5.1.0^{5,15}]pentadeca-1,3,5(15),6,8-pentaene (150.0 mg, 0.17 mmol, 1.00 equiv, 92% purity), tert-butyl N-[3-cyano-4-(5,5-dimethyl-1,3,2-dioxaborinan-2-yl)-7-fluoro-1-benzothiophen-2-yl]carbamate (203.5 mg, 0.5 mmol, 3.00 equiv) in Cs₂CO₃ (492 mg, 1.51 mmol, 9.0 equiv) was added (II)/Dichloro[bis(2-(diphenylphosphino)phenyl)ether]palladium(II) (18 mg, 0.02 mmol, 0.15 equiv) and toluene (15 mL) at room temperature under nitrogen atmosphere. The resulting mixture was stirred for additional 1 hour at 110° C. and cooled to room temperature. It was quenched with water (30 mL), extracted with ethyl acetate (3×30 mL). The extracts were combined, washed with brine (3×10 mL), dried over anhydrous Na₂SO₄. After filtration, the filtrate was concentrated under reduced pressure to give a residue. The residue was purified by silica gel column chromatography, eluted with CH₂Cl₂/MeOH (20:1) to afford the desired product as a white solid. (ESI, m/z): 1033 [M+H]⁺

Tert-butyl N-[4-(3-{[(2R,7aS)-2-fluoro-hexahydropyrrolizin-7a-yl]methoxy}-8-chloro-14-(2,2-difluoroethyl)-6-fluoro-11-(hydroxymethyl)-10-oxa-2,4,14-triazatricyclo[7.5.1.0^{5,15}]pentadeca-1,3,5(15),6,8-pentaen-7-yl)-3-cyano-7-fluoro-1-benzothiophen-2-yl]carbamate Into a reaction vial were added tert-butyl N-[4-(3-{[(2R,7aS)-2-fluoro-hexahydropyrrolizin-7a-yl]methoxy}-11-{[(tert-butyldiphenylsilyl)oxy]methyl}-8-chloro-14-(2,2-difluoroethyl)-6-fluoro-10-oxa-2,4,14-triazatricyclo[7.5.1.0^{5,15}]pentadeca-1,3,5(15),6,8-pentaen-7-yl)-3-cyano-7-fluoro-1-benzothiophen-2-yl]carbamate (110 mg, 0.11 mmol, 1.0 equiv), CsF (64.6 mg, 0.42 mmol, 4.00 equiv) and DMF (2 mL) at room temperature. The resulting mixture was stirred for overnight at room temperature under air atmosphere. It was extracted with ethyl acetate (3×50 mL). The extracts were combined, washed with brine (2×20 mL), dried over anhydrous Na₂SO₄. After filtration, the filtrate was concentrated under reduced pressure to give a residue. The residue was purified by reversed-phase flash chromatography with the following conditions: column, C18; mobile phase, MeCN in Water (10 mmol/L NH₄HCO₃), 10% to 90% gradient in 30 min; detector, UV 254 nm to afford the desired product as an off-white solid. (ESI, m/z): 795 [M+H]⁺

2-Amino-4-(9-chloro-4-(2,2-difluoroethyl)-11-fluoro-2-(((2R,7aS)-2-fluorotetrahydro-1H-pyrrolizin-7a(5H)-yl)methoxy)-7-(hydroxymethyl)-4,5,6,7-tetrahydro-[1,5]oxazocino[4,3,2-de]quinazolin-10-yl)-7-fluorobenzo[b]thiophene-3-carbonitrile (peak 1 and peak 2) To a stirred solution of tert-butyl N-[4-(3-{[(2R,7aS)-2-fluoro-hexahydropyrrolizin-7a-yl]methoxy}-8-chloro-14-(2,2-difluoroethyl)-6-fluoro-11-(hydroxymethyl)-10-oxa-2,4,14-triazatricyclo[7.5.1.0^{5,15}]-pentadeca-1,3,5(15),6,8-pentaen-7-yl)-3-cyano-7-fluoro-1-benzothiophen-2-yl]carbamate (45 mg, 0.06 mmol, 1.0 equiv) in DCM (1 mL) were added TFA (0.2 mL) at 0° C. The resulting mixture was stirred for 1 hour at room temperature. The resulting mixture was concentrated under reduced pressure and neutralized to pH~8 with NH₃. H₂O as a crude. The crude product was purified by prep-HPLC with the following conditions (Column: Kinetex EVO C18 Column, 30*150, 5 μm; Mobile Phase A: Water (10 mmol/L NH₄HCO₃), Mobile Phase B: ACN; Flow rate: 60 mL/min; Gradient: 25% B to 60% B in 10 min, 60% B; Wave Length: UV 220 nm; RT1(min): 9.45; Number Of Runs: 0) to afford desired products: 1207: peak 1 (polar) as a white solid. ESI, m/z): 695 [M+H]⁺; 1H NMR: (400 MHZ, DMSO-d₆) δ 8.05 (s, 2H), 7.27 (dd, J=8.4, 5.3 Hz, 1H), 7.15 (dd, J=9.5, 8.4 Hz, 1H), 6.68-6.29 (m, 1H), 5.27 (d, J=54.0 Hz, 1H), 4.87-4.80 (m, 1H), 4.42 (s, 1H), 4.30 (s, 1H), 4.10 (dd, J=10.1, 6.9 Hz, 1H), 4.06-3.95 (m, 2H), 3.82-3.48 (m, 4H), 3.08 (d, J=7.4 Hz, 2H), 3.00 (s, 1H), 2.82 (d, J=6.9 Hz, 1H), 2.23-2.01 (m, 2H), 2.02-1.90 (m, 1H), 1.88 (d, J=13.9 Hz, 1H), 1.79 (dd, J=20.7, 6.5 Hz, 4H), 1.23 (s, 1H); and 1216: peak 2 (less polar) as a white solid. (ESI, m/z): 695 [M+H]⁺; 1H NMR—PH-KUMT-BW-B-0631-0B: (400 MHZ, DMSO-d₆) δ 8.09 (s, 2H), 7.27 (dd, J=8.4, 5.3 Hz, 1H), 7.15 (dd, J=9.5, 8.4 Hz, 1H), 6.69-6.33 (m, 1H), 5.27 (d, J=53.4 Hz, 1H), 4.85 (td, J=5.6, 2.3 Hz, 1H), 4.43 (s, 1H), 4.38 (d, J=14.5 Hz, 1H), 4.28 (s, 1H), 4.14-3.97 (m, 2H), 3.79 (ddd, J=23.9, 12.4, 6.9 Hz, 2H), 3.66 (dt, J=11.5, 5.9 Hz, 1H), 3.52 (s, 1H), 3.11-3.05 (m, 2H), 3.00 (s, 1H), 2.82 (q, J=8.1 Hz, 1H), 2.15-1.97 (m, 5H), 1.87-1.74 (m, 3H), 1.24 (s, 1H).

Example 1bt: Synthesis of 2-amino-4-(8-chloro-5-(cyanomethyl)-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile (1015)

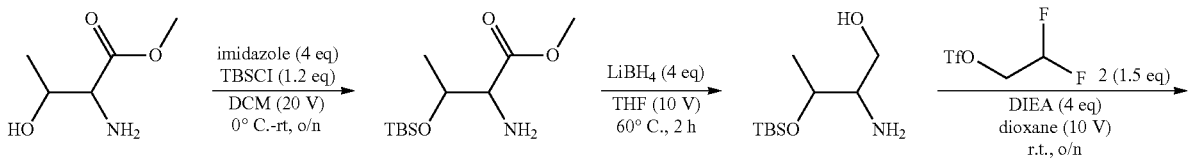

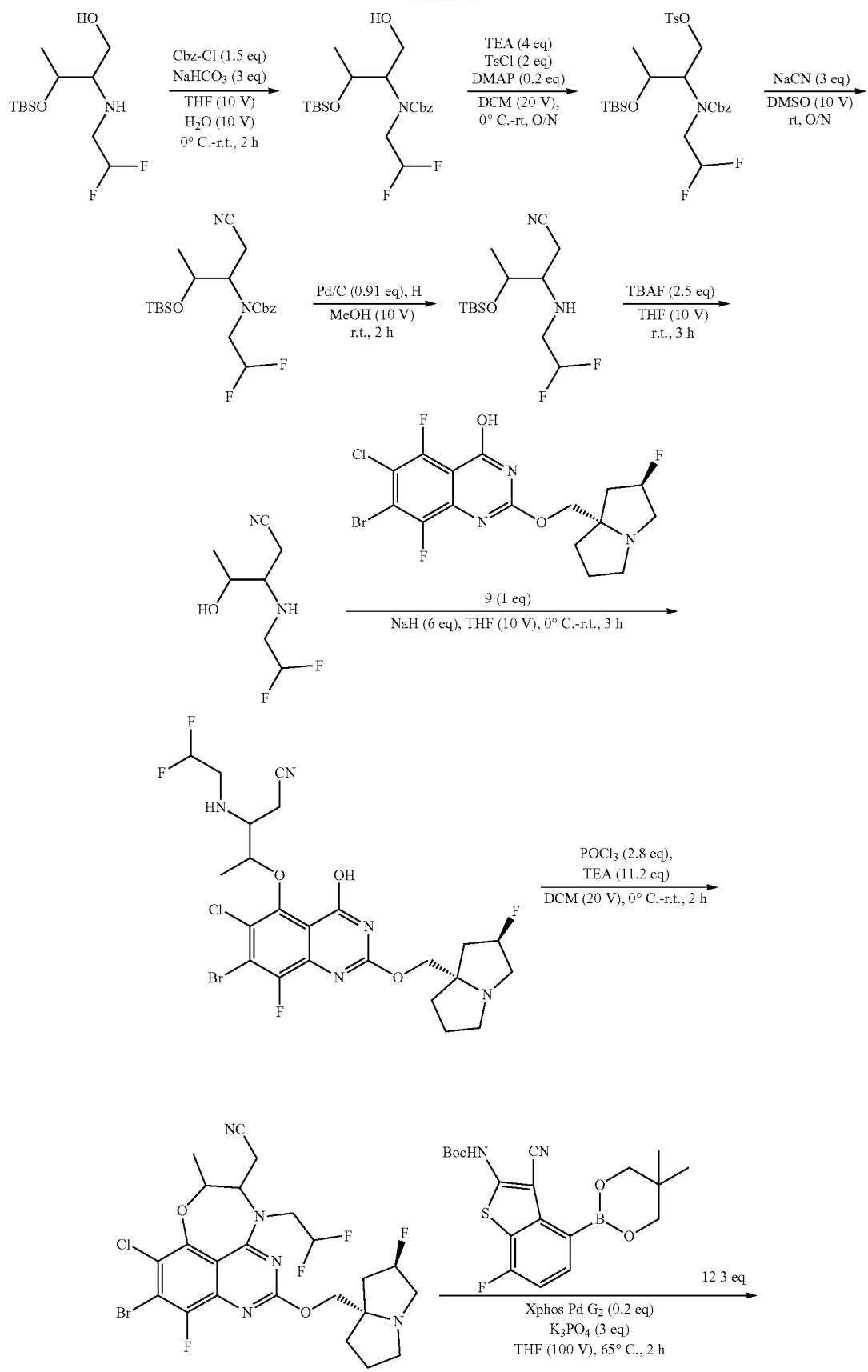

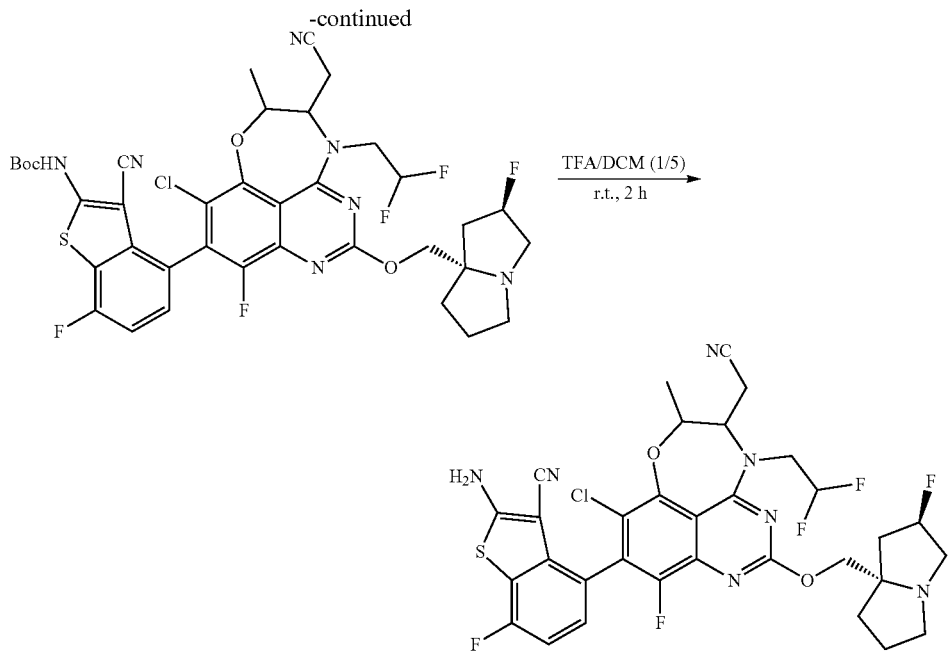

Methyl 2-amino-3-((tert-butyldimethylsilyl)oxy)butanoate To a stirred solution of methyl-2-amino-3-hydroxybutanoate hydrochloride (20 g, 117.92 mmol, 1 equiv) and Imidazole (32.11 g, 471.67 mmol, 4 equiv) in DCM (400 mL) was added TBSCl (21.33 g, 141.502 mmol, 1.2 equiv) at 0° C. The resulting mixture was stirred overnight at room temperature. It was washed with brine. The aqueous phase was extracted with ethyl acetate (3×200 mL). The organics were combined, washed with brine, dried over anhydrous $Na_2SO_4$. After filtration, the filtrate was concentrated under reduced pressure to give a residue. The residue was purified by silica gel column chromatography, eluted with petroleum/ethyl acetate (3:1) to afford the desired product as a colorless oil. (ESI, m/z): 248 $[M+H]^+$ 2-Amino-3-[(tert-butyldimethylsilyl) oxy] butan-1-ol To a stirred solution of methyl-2-amino-3-[(tert-butyldimethylsilyl) oxy] butanoate (18 g, 72.75 mmol, 1 equiv) in THF (180 mL) was added $LiBH_4$ (6.34 g, 291.01 mmol, 4 equiv) at room temperature. The resulting mixture was stirred for 2 hours at 60° C. It was cooled to room temperature and quenched with water/Ice. The resulting mixture was extracted with ethyl acetate (3×200 mL). The extracts were combined, washed with brine, and dried over anhydrous $Na_2SO_4$. After filtration, the filtrate was concentrated under reduced pressure to give desired product as a colorless oil which was used directly in the next step without purification. (ESI, m/z): 220 $[M+H]^+$ 3-[(Tert-butyldimethylsilyl)oxy]-2-[(2,2-difluoroethyl)amino]butan-1-ol To a stirred solution of 2-amino-3-[(tert-butyldimethylsilyl)oxy]butan-1-ol (13.5 g, 61.53 mmol, 1 equiv) and DIEA (31.81 g, 246.12 mmol, 4 equiv) in dioxane (135 mL) was added 2,2-difluoroethyl trifluoromethanesulfonate (19.76 g, 92.29 mmol, 1.5 equiv) dropwise at room temperature. The resulting mixture was stirred overnight and diluted with ethyl acetate (200 mL). The extracts were combined, washed with brine and dried over $Na_2SO_4$. It was filtered and solvent was removed under reduced pressure to give a residue. The residue was purified by silica gel column chromatography, eluted with petroleum/ethyl acetate (3:1) to afford the desired product as a colorless oil. (ESI, m/z): 266 $[M+H]^+$ Benzyl (3-((tert-butyldimethylsilyl)oxy)-1-hydroxybutan-2-yl)(2,2-difluoroethyl)carbamate To a stirred solution of 3-[(tert-butyldimethylsilyl)oxy]-2-[(2,2-difluoroethyl)amino]butan-1-ol (4 g, 14.113 mmol, 1 equiv) in THF (40 mL,) was added $NaHCO_3$ (3.56 g, 42.33 mmol, 3 equiv) in water (40 mL) at room temperature. Then Cbz-Cl (3.61 g, 21.16 mmol, 1.5 equiv) was added dropwise at 0° C. The resulting mixture was stirred for 2 hours at room temperature and extracted with ethyl acetate (3×100 mL). The extracts were combined, washed with brine (2×40 mL), dried over anhydrous $Na_2SO_4$. After filtration, the filtrate was concentrated under reduced pressure to give a residue. The residue was purified by silica gel column chromatography, eluted with petroleum/ethyl acetate (3:1) to afford the desired product as a colorless oil. (ESI, m/z): 418 $[M+H]^+$ 2-(((Benzyloxy)carbonyl)(2,2-difluoroethyl)amino)-3-((tert-butyldimethylsilyl)oxy)butyl 4-methylbenzenesulfonate To a stirred solution of benzyl (3-((tert-butyldimethylsilyl)oxy)-1-hydroxybutan-2-yl)(2,2-difluoroethyl)carbamate (1 g, 2.39 mmol, 1 equiv), triethylamine (0.97 g, 9.58 mmol, 4 equiv) and DMAP (0.06 g, 0.48 mmol, 0.2 equiv) in DCM (20 mL) was added TsCl (0.91 g, 4.79 mmol, 2 equiv) in portions at 0° C. The resulting mixture was stirred overnight at room temperature. The reaction was quenched with water/Ice and extracted with ethyl acetate (3×30 mL). The extracts were combined, washed with brine, and dried over anhydrous $Na_2SO_4$. After filtration, the filtrate was concentrated under reduced pressure to give a residue. The residue was purified by silica gel column chromatography, eluted with petroleum/ethyl acetate (5:1) to afford the desired product as a colorless oil. (ESI, m/z): 572$[M+H]^+$ Benzyl (3-((tert-butyldimethylsilyl)oxy)-1-cyanobutan-2-yl)(2,2-difluoroethyl)carbamate To a stirred solution of 2-(((benzyloxy)carbonyl)(2,2-difluoroethyl)amino)-3-((tert-butyldimethylsilyl)oxy)butyl 4-methylbenzenesulfonate (1 g, 1.75 mmol, 1 equiv) in DMSO (10 mL) was added NaCN (0.26 g, 5.25 mmol, 3 equiv) at room temperature. The resulting mixture was stirred overnight, quenched with sat. NaCl (aq.), and extracted with ethyl acetate (3×50 mL). The extracts were combined, washed with brine, and dried over anhydrous $Na_2SO_4$. After filtration, the filtrate was concentrated under reduced pressure to give a residue. The residue was purified by silica gel column chromatography, eluted with $CH_2Cl_2$/petroleum (3:1) to afford the desired product as a colorless oil (ESI, m/z): 427 [M+H]$^+$ 4-((Tert-butyldimethylsilyl)oxy)-3-((2,2-difluoroethyl) amino)pentanenitrile To a stirred solution of benzyl (3-((tert-butyldimethylsilyl)oxy)-1-cyanobutan-2-yl)(2,2-difluoroethyl)carbamate (440 mg, 1.03 mmol, 1 equiv) in MeOH (4 mL) was added 10% Pd/C (100 mg, 0.94 mmol, 0.91 equiv) at room temperature. The resulting mixture was stirred for 2 hours under hydrogen atmosphere. It was filtered, and the filtrate was concentrated under reduced pressure to give the desired product as a colorless oil which was used directly in the next step without further purification. (ESI, m/z): 293 [M+H]$^+$ 3-((2,2-Difluoroethyl)amino)-4-hydroxypentanenitrile To a stirred solution of 4-((tert-butyldimethylsilyl)oxy)-3-((2, 2-difluoroethyl)amino)pentanenitrile (400 mg, 1.37 mmol, 1 equiv) in THF (4 mL) was added TBAF (3.42 mL, 3.42 mmol, 1 M in THF, 2.5 equiv) at room temperature. The resulting mixture was stirred for 3 hours and concentrated under reduced pressure to give a residue. The residue was purified by silica gel column chromatography, eluted with petroleum/ethyl acetate (1:1) to afford the desired product as a colorless oil. (ESI, m/z): 179 [M+H]$^+$ 4-((7-Bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)-3-((2,2-difluoroethyl)amino)pentanenitrile To a stirred mixture of 3-((2,2-difluoroethyl)amino)-4-hydroxypentanenitrile (100 mg, 0.56 mmol, 1 equiv) and (7-bromo-6-chloro-5,8-difluoro-2-(((2R,7aS)-2-fluorotetrahydro-1H-pyrrolizin-7a(5H)-yl)methoxy)quinazolin-4-ol (248 mg, 0.56 mmol, 1 equiv) in THF (2 mL) was added NaH (81 mg, 3.36 mmol, 6 equiv) in portions at 0° C. The resulting mixture was stirred for 3 hours at room temperature. The reaction was quenched with water/Ice at room temperature. And extracted with ethyl acetate (3×10 mL). The extracts were combined, washed with brine, and dried over anhydrous $Na_2SO_4$. After filtration, the filtrate was concentrated under reduced pressure to give a crude. The residue was purified by reversed-phase flash chromatography with the following conditions: column, C18; mobile phase, MeCN in Water (10 mmol/L $NH_4HCO_3$), 30% to 50% gradient in 20 min; detector, UV 254 nm to give desired product as a yellow solid. (ESI, m/z): 610 [M+H]$^+$ 2-(9-Bromo-8-chloro-4-(2,2-difluoroethyl)-10-fluoro-2-(((2R,7aS)-2-fluorotetrahydro-1H-pyrrolizin-7a(5H)-yl) methoxy)-6-methyl-5,6-dihydro-4H-[1,4]oxazepino[5,6,7-de]quinazolin-5-yl)acetonitrile To a stirred solution of 4-((7-bromo-6-chloro-8-fluoro-2-(((2R,7aS)-2-fluorotetrahydro-1H-pyrrolizin-7a(5H)-yl)methoxy)-4-hydroxyquinazolin-5-yl)oxy)-3-((2,2-difluoroethyl)amino)pentanenitrile (160 mg, 0.26 mmol, 1 equiv) and triethylamine (297 mg, 2.93 mmol, 11.2 equiv) in DCM (3.2 mL) was added POCl$_3$ (112 mg, 0.734 mmol, 2.8 equiv) dropwise at 0° C. under nitrogen atmosphere. The resulting mixture was stirred for 2 hours at room temperature, quenched with water/ice, and extracted with ethyl acetate (3×10 mL). The extracts were combined, washed with brine, and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 30% to 60% gradient in 20 min; detector, UV 254 nm to afford the desired product as a yellow solid. (ESI, m/z): 592 [M+H]$^+$ Tert-butyl (4-(8-chloro-5-(cyanomethyl)-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4] oxazepino[5,6,7-de]quinazolin-9-yl)-3-cyano-7-fluorobenzo[b]thiophen-2-yl)carbamate To a stirred solution 2-(9-bromo-8-chloro-4-(2,2-difluoroethyl)-10-fluoro-2-(((2R,7aS)-2-fluorotetrahydro-1H-pyrrolizin-7a(5H)-yl) methoxy)-6-methyl-5,6-dihydro-4H-[1,4]oxazepino[5,6,7-de]quinazolin-5-yl)acetonitrile (100 mg, 0.169 mmol, 1 equiv) and tert-butyl N-[3-cyano-4-(5,5-dimethyl-1,3,2-dioxaborinan-2-yl)-7-fluoro-1-benzothiophen-2-yl]carbamate (204 mg, 0.507 mmol, 3 equiv) in THF (10 mL) were added XPhos Pd G2 (27 mg, 0.034 mmol, 0.2 equiv) and K$_3$PO$_4$ (107 mg, 0.506 mmol, 3.0 equiv) at room temperature. The resulting mixture was stirred for 2 hours at 65° C. under nitrogen atmosphere. It was cooled down to room temperature, quenched with water, and extracted with ethyl acetate (3×30 mL). The extracts were combined, washed with brine, and dried over anhydrous $Na_2SO_4$. After filtration, the filtrate was concentrated under reduced pressure to give a residue. The residue was purified by reversed-phase flash chromatography with the following conditions: column, C18; mobile phase, MeCN in Water (10 mmol/L $NH_4HCO_3$), 30% to 80% gradient in 20 min; detector, UV 254 nm to give the desired product as a yellow solid. (ESI, m/z):704 [M+H]$^+$ 2-Amino-4-(8-chloro-5-(cyanomethyl)-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4] oxazepino[5,6,7-de]quinazolin-9-yl)-7-fluorobenzo[b] thiophene-3-carbonitrile To a stirred solution of tert-butyl (4-(8-chloro-5-(cyanomethyl)-4-(2,2-difluoroethyl)-10-fluoro-2-(((2R,7aS)-2-fluorotetrahydro-1H-pyrrolizin-7a (5H)-yl)methoxy)-6-methyl-5,6-dihydro-4H-[1,4]oxazepino[5,6,7-de]quinazolin-9-yl)-3-cyano-7-fluorobenzo[b] thiophen-2-yl)carbamate (40 mg, 0.057 mmol, 1 equiv) in DCM (5 mL) was added TFA (1 mL) dropwise at room temperature. The resulting mixture was stirred for 2 hours and concentrated under vacuum to give a residue. The residue was purified by prep-HPLC with the following conditions: column, C18; mobile phase, MeCN in Water (10 mmol/L $NH_4HCO_3$), 50% to 80% gradient in 10 min; detector, UV 254 nm to give the desired product as a white solid. (ESI, m/z): 604 [M+H]$^+$; $^1$H NMR (400 MHZ, DMSO-d$_6$, ppm) δ 8.11 (s, 2H), 7.33 (dd, J=8.4, 5.2 Hz, 1H), 7.17-7.13 (m, 1H), 6.63-6.35 (m, 1H), 5.35-5.20 (m, 1H), 5.05-5.02 (m, 1H), 4.75-4.64 (m, 1H), 4.57-4.52 (m, 1H), 4.12-4.09 (m, 1H), 4.04-4.00 (m, 1H), 3.96-3.92(m.1H), 3.08-3.06 (m, 5H), 2.86-2.82 (m, 1H), 2.19-2.12 (m, 1H), 2.08-2.06 (m, 1H), 2.03-1.97 (m, 1H), 1.86-1.75 (m, 3H), 1.25-1.23 (m, 3H).

Example 1bu: Synthesis of 2-amino-4-((5R)-8-chloro-4-(3,3-difluoropropyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile (peak 1: 820; peak 2: 826)
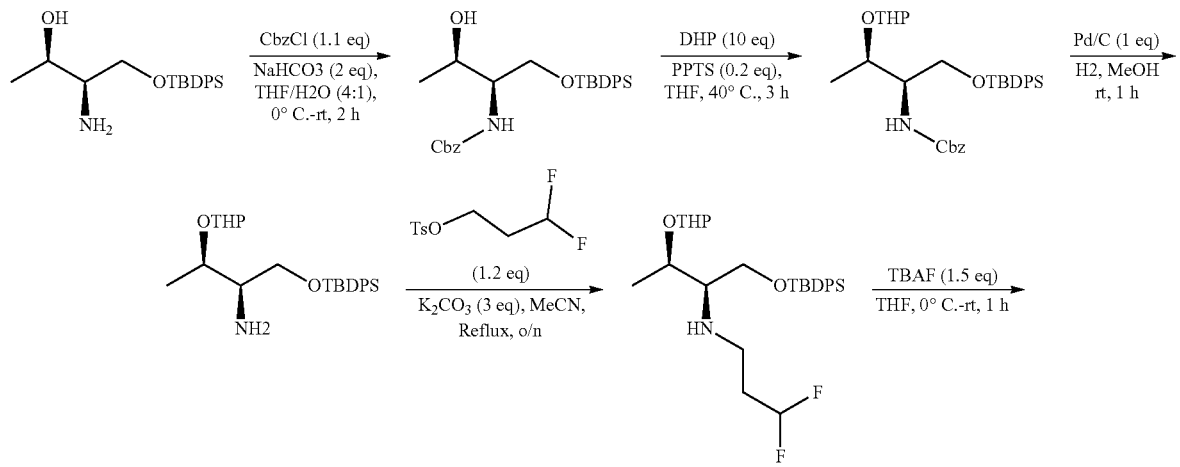
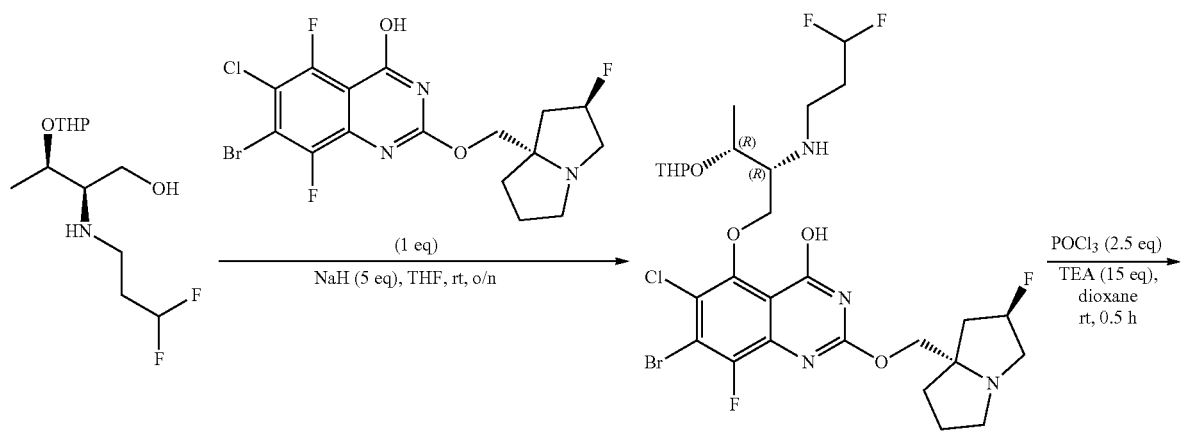
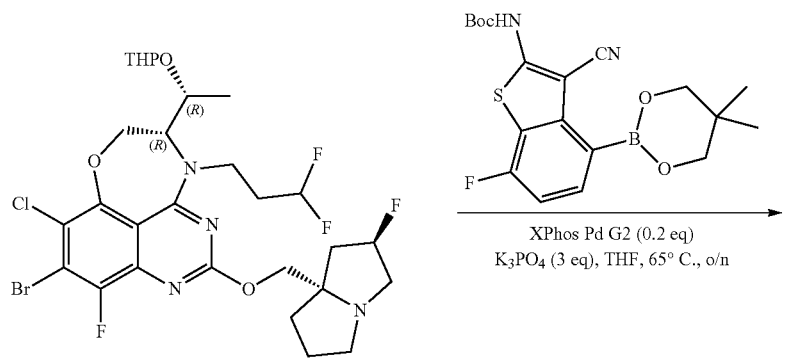

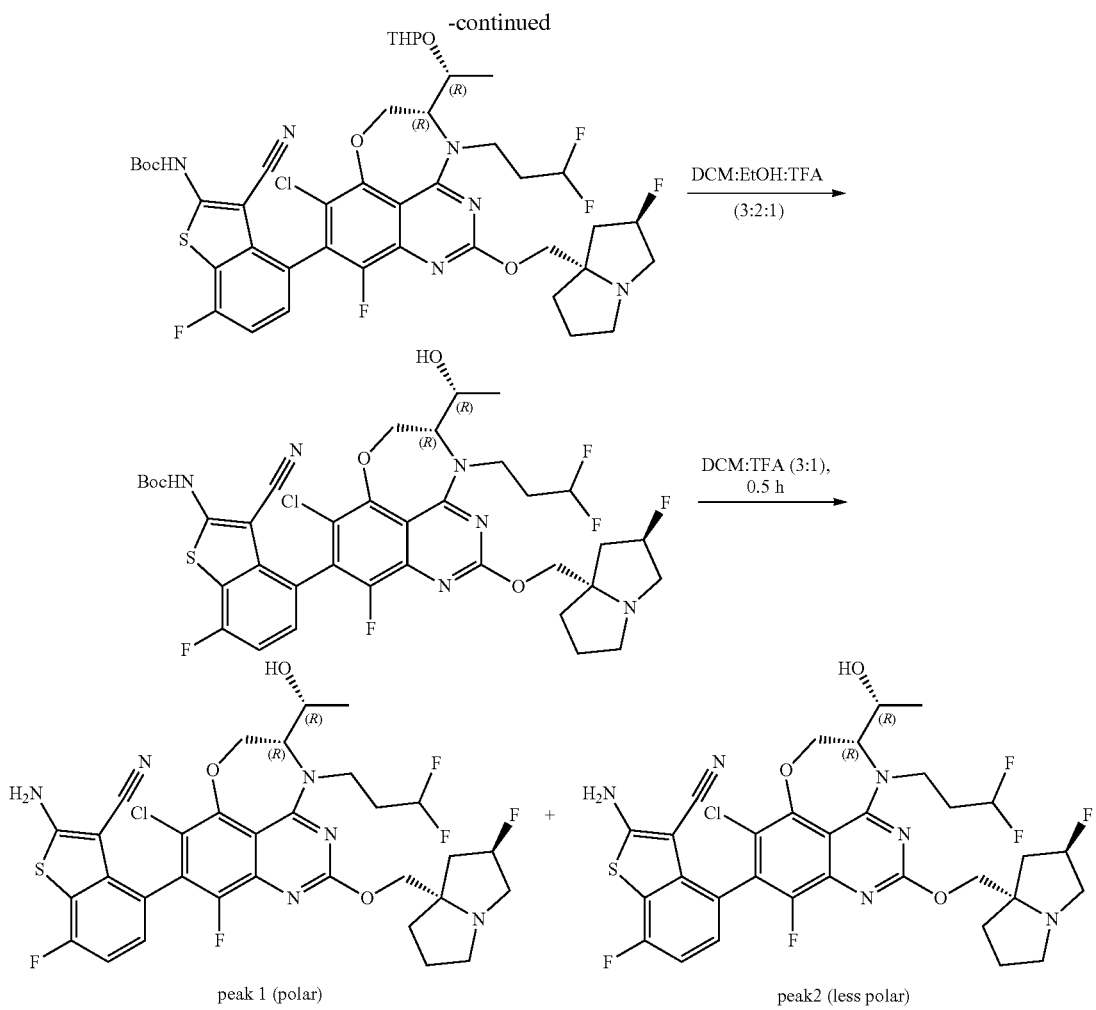

peak 1 (polar)     peak2 (less polar)

Benzyl N-[(2R,3R)-1-[(tert-butyldiphenylsilyl)oxy]-3-hydroxybutan-2-yl]carbamate A solution of (2R,3R)-3-amino-4-[(tert-butyldiphenylsilyl)oxy]butan-2-ol (11 g, 32.019 mmol, 1 equiv) in THF/H$_2$O (100 mL, 4/1) was treated with NaHCO$_3$(5.38 g, 64.03 mmol, 2 equiv) followed by the addition of CbzCl (6.01 g, 35.22 mmol, 1.1 equiv) dropwise at 0° C. The resulting mixture was stirred for 2 hours at room temperature, water (40 mL) was added, and the mixture was extracted with ethyl acetate (3×10 mL). The extracts were combined, washed with brine and dried over Na$_2$SO$_4$. It was filtered and solvent was removed under reduced pressure to give a reside. The residue was purified by silica gel column chromatography, eluted with CH$_2$Cl$_2$/MeOH (10:1) to afford the desired product as a colorless oil. (ESI, m/z): 478 [M+H]$^+$ Benzyl N-[(2R,3R)-1-[(tert-butyldiphenylsilyl)oxy]-3-(oxan-2-yloxy)butan-2-yl]carbamate A solution of benzyl N-[(2R,3R)-1-[(tert-butyldiphenylsilyl)oxy]-3-hydroxybutan-2-yl]carbamate (13 g, 27.21 mmol, 1 equiv) in THF (50 mL) was treated with PPTS (1.37 g, 5.44 mmol, 0.2 equiv) followed by the addition of DHP (22.89 g, 272.15 mmol, 10 equiv) dropwise at room temperature. The resulting mixture was stirred for 3 hours at 40° C. It was cooled down to room temperature and concentrated under reduced pressure to give a residue. The residue was purified by silica gel column chromatography, eluted with PE/EA (6:1) to afford the desired product as a colorless oil. (ESI, m/z): 562 [M+H]$^+$ (2R,3R)-1-((tert-butyldiphenylsilyl)oxy)-3-((tetrahydro-2H-pyran-2-yl)oxy)butan-2-amine A solution of benzyl N-[(2R,3R)-1-[(tert-butyldiphenylsilyl)oxy]-3-(oxan-2-yloxy)butan-2-yl]carbamate (12.5 g, 22.25 mmol, 1 equiv) in MeOH (25 mL) was treated with Pd/C (2.37 g, 22.25 mmol, 1 equiv) for 1 hour at room temperature under hydrogen atmosphere. It was filtered and the filtrate was concentrated under reduced pressure to obtain the desired product (11.5 g) which was used in the next step directly without further purification. (ESI, m/z): 428 [M+H]$^+$

[(2R,3R)-1-[(tert-butyldiphenylsilyl)oxy]-3-(oxan-2-yloxy)butan-2-yl](3,3-difluoropropyl)amine A solution of [(2R,3R)-2-amino-3-(oxan-2-yloxy)butoxy](tert-butyl)diphenylsilane (3 g, 7.01 mmol, 1 equiv) in MeCN (15 mL) was treated with 3,3-difluoropropyl 4-methylbenzenesulfonate (2.11 g, 8.41 mmol, 1.2 equiv) followed by the addition of K$_2$CO$_3$ (2.91 g, 21.04 mmol, 3 equiv) in portions at room temperature. The resulting mixture was stirred for overnight at 78° C. under nitrogen atmosphere. The mixture was allowed to cool down to room temperature, added water and extracted with ethyl acetate. The extracts were combined, washed with brine, and dried over Na$_2$SO$_4$. It was filtered and concentrated under reduced pressure to give a residue. The residue was purified by silica gel column chromatography, eluted with petroleum/ethyl acetate (5:1) to afford the desired product as a colorless oil. (ESI, m/z): 506 [M+H]$^+$ (2R,3R)-2-[(3,3-difluoropropyl)amino]-3-(oxan-2-yloxy) butan-1-ol A solution of [(2R,3R)-1-[(tert-butyldiphenylsilyl)oxy]-3-(oxan-2-yloxy)butan-2-yl](3,3-difluoropropyl) amine (2.7 g, 5.33 mmol, 1 equiv) in THF (5 mL) was added TBAF (2.09 g, 8.01 mmol, 1.5 equiv) dropwise at 0° C. The resulting mixture was stirred for 1 hour at room temperature and concentrated to give a residue. The residue was purified by silica gel column chromatography, eluted with $CH_2Cl_2$/MeOH (10:1) to afford the desired product as a colorless oil. (ESI, m/z): 268 [M+H]$^+$ 7-Bromo-6-chloro-5-((2R,3R)-2-((3,3-difluoropropyl) amino)-3-((tetrahydro-2H-pyran-2-yl)oxy)butoxy)-8-fluoro-2-(((2R,7aS)-2-fluorotetrahydro-1H-pyrrolizin-7a (5H)-yl)methoxy)quinazolin-4-ol A solution of (2R,3R)-2-[(3,3-difluoropropyl)amino]-3-(oxan-2-yloxy)butan-1-ol (250 mg, 0.93 mmol, 1 equiv) in THF (5 mL) was treated with 7-bromo-6-chloro-5,8-difluoro-2-(((2R,7aS)-2-fluorotetrahydro-1H-pyrrolizin-7a(5H)-yl)methoxy)quinazolin-4-ol (423 mg, 0.93 mmol, 1 equiv) followed by the addition of NaH (202 mg, 8.415 mmol, 9 equiv) in portions at 0° C. The resulting mixture was stirred for overnight at room temperature and treated with water. The mixture was extracted with $CH_2Cl_2$ (3×10 mL), washed with brine, and dried over $Na_2SO_4$. It was filtered and solvent was removed under reduced pressure to obtain the desired product which was used in the next step directly without further purification. (ESI, m/z): 699 [M+H]$^+$ (5R)-9-bromo-8-chloro-4-(3,3-difluoropropyl)-10-fluoro-2-(((2R,7aS)-2-fluorotetrahydro-1H-pyrrolizin-7a (5H)-yl)methoxy)-5-((1R)-1-((tetrahydro-2H-pyran-2-yl) oxy)ethyl)-5,6-dihydro-4H-[1,4]oxazepino[5,6,7-de] quinazoline A solution of 2-{[(2R,7aS)-2-fluoro-hexahydropyrrolizin-7a-yl]methoxy}-7-bromo-6-chloro-5-[(2R,3R)-2-[(3,3-difluoropropyl)amino]-3-(oxan-2-yloxy) butoxy]-8-fluoroquinazolin-4-ol (500 mg, 0.714 mmol, 1 equiv) in 1,4-dioxane (5 mL) was treated with POCl$_3$ (273 mg, 1.78 mmol, 2.5 equiv) at room temperature followed by the addition of triethylamine (1084.26 mg, 10.710 mmol, 15 equiv) dropwise at room temperature. The resulting mixture was stirred for 0.5 hours at room temperature. It was concentrated under reduced pressure to give a residue. The residue was purified by reversed-phase flash chromatography with the following conditions: column, C18; mobile phase, MeCN in Water (10 mmol/L NH$_4$HCO$_3$), 0 to 100% gradient in 20 min; detector, UV 254 nm to obtain the desired product as white solid. (ESI, m/z): 681 [M+H]$^+$ Tert-butyl (4-((5R)-8-chloro-4-(3,3-difluoropropyl)-10-fluoro-2-(((2R,7aS)-2-fluorotetrahydro-1H-pyrrolizin-7a (5H)-yl)methoxy)-5-((1R)-1-((tetrahydro-2H-pyran-2-yl) oxy)ethyl)-5,6-dihydro-4H-[1,4]oxazepino[5,6,7-de] quinazolin-9-yl)-3-cyano-7-fluorobenzo[b]thiophen-2-yl) carbamate (12R)-3-{[(2R,7aS)-2-fluoro-hexahydropyrrolizin-7a-yl]methoxy}-7-bromo-8-chloro-13-(3,3-difluoropropyl)-6-fluoro-12-[(1R)-1-(oxan-2-yloxy)ethyl]-10-oxa-2,4,13-triazatricyclo[7.4.1.0ˆ{5,14}]] tetradeca-1,3,5,7,9(14)-pentaene (250 mg, 0.367 mmol, 1 equiv), tert-butyl N-[3-cyano-4-(5,5-dimethyl-1,3,2-dioxaborinan-2-yl)-7-fluoro-1-benzothiophen-2-yl]carbamate (222 mg, 0.55 mmol, 1.5 equiv), 2nd Generation XPhos precatalyst (57 mg, 0.073 mmol, 0.2 equiv) and K$_3$PO$_4$ (233 mg, 1.101 mmol, 3 equiv) were dissolved in THF (3 mL) under nitrogen atmosphere. The resulting mixture was stirred for overnight at 65° C. under nitrogen atmosphere. The mixture was allowed to cool down to room temperature and concentrated under reduced pressure to give a residue. The residue was purified by reversed-phase flash chromatography with the following conditions: column, C18; mobile phase, MeCN in Water (10 mmol/L NH$_4$HCO$_3$), 0% to 100% gradient in 10 min; detector, UV 254 nm to obtain 120 mg desired product as white solid. (ESI, m/z): 893 [M+H]$^+$ Tert-butyl (4-((5R)-8-chloro-4-(3,3-difluoropropyl)-10-fluoro-2-(((2R,7aS)-2-fluorotetrahydro-1H-pyrrolizin-7a (5H)-yl)methoxy)-5-((R)-1-hydroxyethyl)-5,6-dihydro-4H-[1,4]oxazepino[5,6,7-de]quinazolin-9-yl)-3-cyano-7-fluorobenzo[b]thiophen-2-yl)carbamate A solution of tert-butyl N-{4-[(12R)-3-{[(2R,7aS)-2-fluoro-hexahydropyrrolizin-7a-yl]methoxy}-8-chloro-13-(3,3-difluoropropyl)-6-fluoro-12-[(1R)-1-(oxan-2-yloxy)ethyl]-10-oxa-2,4,13-triazatricyclo[7.4.1.0ˆ{5,14} ]tetradeca-1,3,5,7,9(14)-pentaen-7-yl]-3-cyano-7-fluoro-1-benzothiophen-2-yl} carbamate (120 mg, 0.134 mmol, 1 equiv) in DCM/EtOH (5 mL, 3/2) was added TFA (1 mL, 13.46 mmol) dropwise at 0° C. The resulting mixture was stirred for 3 hours at room temperature. It was concentrated under reduced pressure to give the desired product which was (120 mg) used in the next step directly without further purification. (ESI, m/z): 809 [M+H]$^+$ 2-Amino-4-((5R)-8-chloro-4-(3,3-difluoropropyl)-10-fluoro-2-(((2R,7aS)-2-fluorotetrahydro-1H-pyrrolizin-7a (5H)-yl)methoxy)-5-((R)-1-hydroxyethyl)-5,6-dihydro-4H-[1,4]oxazepino[5,6,7-de]quinazolin-9-yl)-7-fluorobenzo[b] thiophene-3-carbonitrile A solution of tert-butyl N-{4-[(12R)-3-{[(2R,7aS)-2-fluoro-hexahydropyrrolizin-7a-yl] methoxy}-8-chloro-13-(3,3-difluoropropyl)-6-fluoro-12-[(1R)-1-hydroxyethyl]-10-oxa-2,4,13-triazatricyclo [7.4.1.0ˆ{5,14} ]tetradeca-1,3,5,7,9(14)-pentaen-7-yl]-3-cyano-7-fluoro-1-benzothiophen-2-yl} carbamate (120 mg, 0.148 mmol, 1 equiv) in DCM (3 mL) followed was added TFA (1 mL, 13.463 mmol) dropwise at 0° C. The resulting mixture was stirred for 0.5 hours at room temperature. It was concentrated under reduced pressure to give a residue. The residue was purified by Prep-TLC (XBridge BEN Shield PR 18.5 μm, 30 mm*150 mm; mobile phase, MeCN in Water (10 mmol/L NH$_4$HCO$_3$), 40% to 65% gradient in 10 min; detector, UV 254 nm.) to afford desired product peak 1 (polar) and peak 2 (less polar) as white solids.

820: Peak 1 (polar):(ESI, m/z): 709 [M+H]$^+$, $^1$H NMR (400 MHZ, DMSO-d$_6$) δ=8.07 (s, 2H), 7.22 (dd, J=8.4, 5.2 Hz, 1H), 7.12 (t, J=8.9 Hz, 1H), 6.62-6.01 (m, 1H), 5.58-5.35 (m, 1H), 5.14 (d, J=5.3 Hz, 1H), 4.92-4.84 (m, 1H), 4.42 (s, 2H), 4.34 (s, 1H), 3.84 (s, 1H), 3.79-3.74 (m, 2H), 3.52 (s, 2H), 3.19-3.09 (m, 2H), 2.44-2.30 (m, 3H), 2.22-1.85 (m, 5H), 1.32-1.18 (m, 4H).

826: Peak 2 (less polar) (ES,m/z): 709 [M+H]$^{+1}$H NMR (400 MHZ, DMSO-d$_6$) δ=8.05 (s, 2H), 7.37-6.97 (m, 2H), 6.51-6.01 (m, 1H), 5.45-5.20 (m, 1H), 5.15-5.02 (m, 1H), 4.92-4.73 (m, 1H), 4.60-4.22 (m, 2H), 4.25-3.91 (m, 2H), 3.79 (s, 2H), 3.73-3.57 (m, 1H), 3.12 (s, 2H), 3.04 (s, 1H), 2.85 (s, 1H), 2.38 (s, 2H), 2.15-1.95 (m, 3H), 1.90-1.73 (m, 3H), 1.26 (s, 3H).

The compounds in Table 1 were prepared according to one of the general routes outlined in Schemes 1-16, Examples 1a-1bu, or by methods generally known in the art. In some embodiments, exemplary compounds may include, but are not limited to, a compound selected from Table 1, or a salt, solvate, atropisomer, stereoisomer, or other isomeric form thereof.

TABLE 1

| No. | Structure | Chemical Name | [M + H]+ |
|---|---|---|---|
| 601 | 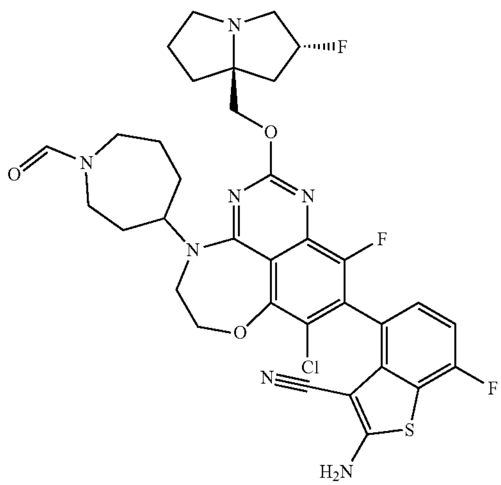 [SMILES: N#Cc1c(N)sc2c(F)ccc(-c3c(Cl)c4c5c(nc(OC[C@@]67CCCN6C[C@H](F)C7)nc5c3F)N(C3CCCN(C=O)CC3)CCO4)c12] | 2-amino-4-(8-chloro-10-fluoro-2-(((2R,7aS)-2-fluorotetrahydro-1H-pyrrolizin-7a(5H)-yl)methoxy)-4-(1-formylazepan-4-yl)-5,6-dihydro-4H-[1,4]oxazepino[5,6,7-de]quinazolin-9-yl)-7-fluorobenzo[b]thiophene-3-carbonitrile | 356.8 [m / 2 + H]+ |
| 602 | 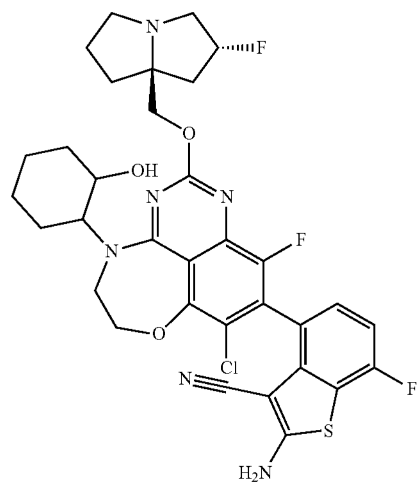 [SMILES: N#Cc1c(N)sc2c(F)ccc(-c3c(Cl)c4c5c(nc(OC[C@@]67CCCN6C[C@H](F)C7)nc5c3F)N(C3CCCCC3O)CCO4)c12] | 2-amino-4-(8-chloro-10-fluoro-2-(((2R,7aS)-2-fluorotetrahydro-1H-pyrrolizin-7a(5H)-yl)methoxy)-4-(2-hydroxycyclohexyl)-5,6-dihydro-4H-[1,4]oxazepino[5,6,7-de]quinazolin-9-yl)-7-fluorobenzo[b]thiophene-3-carbonitrile | 685.2 |
| 603 | 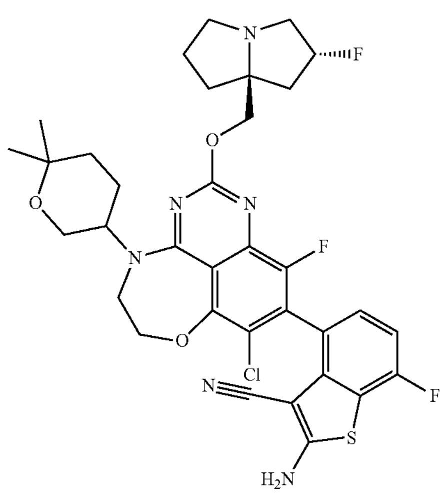 [SMILES: CC1(C)CCC(N2CCOc3c(Cl)c(-c4ccc(F)c5sc(N)c(C#N)c45)c(F)c4nc(OC[C@@]56CCCN5C[C@H](F)C6)nc2c34)CO1] | 2-amino-4-(8-chloro-4-(6,6-dimethyltetrahydro-2H-pyran-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 700.4 |

TABLE 1-continued

| No. | Structure | Chemical Name | [M + H]⁺ |
|---|---|---|---|
| 604 | 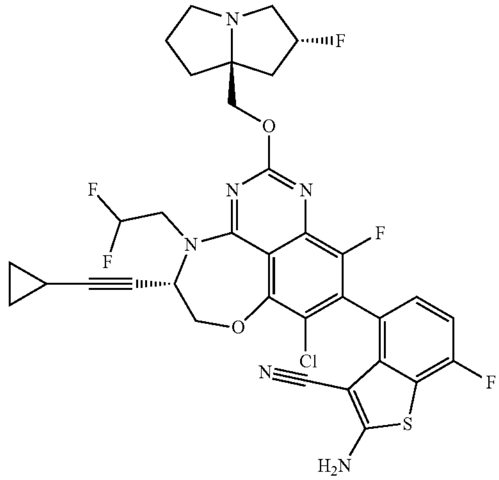 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C#CC3CC3)CO4)c12] | 2-amino-4-((S)-8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 714.9 |
| 605 | 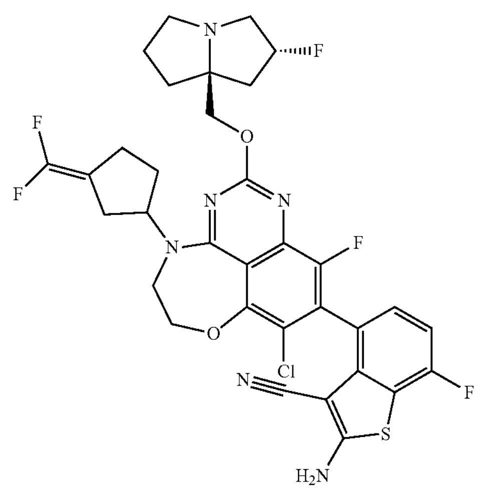 [SMILES: N#Cc1c(N)sc2c(F)ccc(-c3c(Cl)c4c5c(nc(OC[C@@]67CCCN6C[C@H](F)C7)nc5c3F)N(C3CCC(=C(F)F)C3)CCO4)c12] | 2-amino-4-(8-chloro-4-(3-(difluoromethylene)cyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 703.3 |
| 606 | 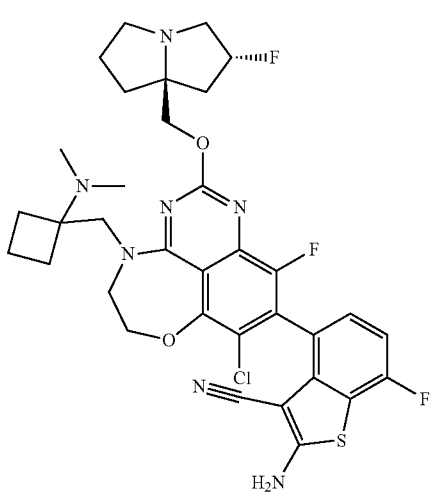 [SMILES: CN(C)C1(CN2CCOc3c(Cl)c(-c4ccc(F)c5sc(N)c(C#N)c45)c(F)c4nc(OC[C@@]56CCCN5C[C@H](F)C6)nc2c34)CCC1] | 2-amino-4-(8-chloro-4-((1-(dimethylamino)cyclobutyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 697.7 |

TABLE 1-continued

| No. | Structure | Chemical Name | [M + H]+ |
|---|---|---|---|
| 607 | 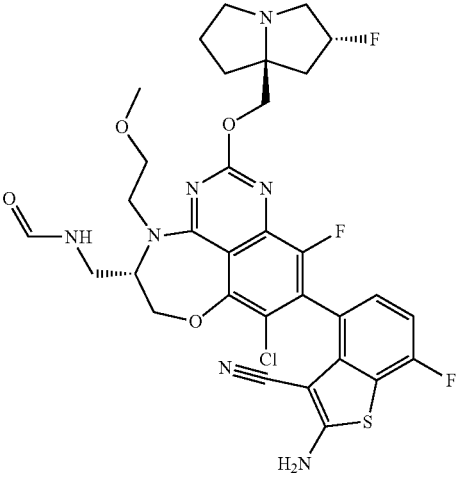 [SMILES: COCCN1c2nc(OC[C@@]34CCCN3C[C@H](F)C4)nc3c(F)c(-c4ccc(F)c5sc(N)c(C#N)c45)c(Cl)c(c23)OC[C@@H]1CNC=O] | N-(((5S)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-4-(2-methoxyethyl)-5,6-dihydro-4H-[1,4]oxazepino[5,6,7-de]quinazolin-5-yl)methyl)formamide | 702.3 |
| 608 | 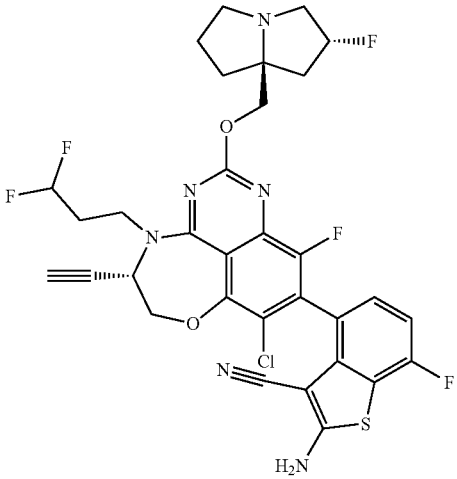 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 688.9 |
| 609 | 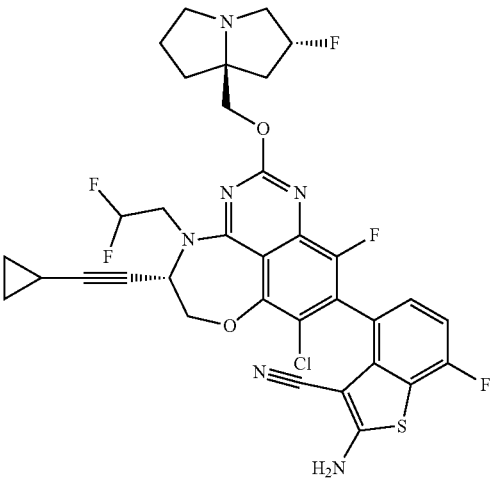 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C#CC3CC3)CO4)c12] | 2-amino-4-((S)-8-chloro-5-(cyclopropylethynyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 714.9 |

TABLE 1-continued

| No. | Structure | Chemical Name | [M + H]+ |
|---|---|---|---|
| 610 | 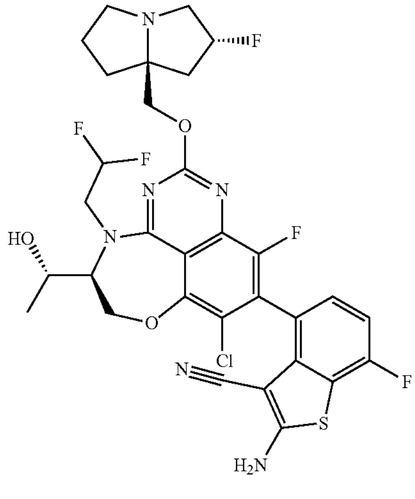 [SMILES: C[C@H](O)[C@@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 694.9 |
| 611 | 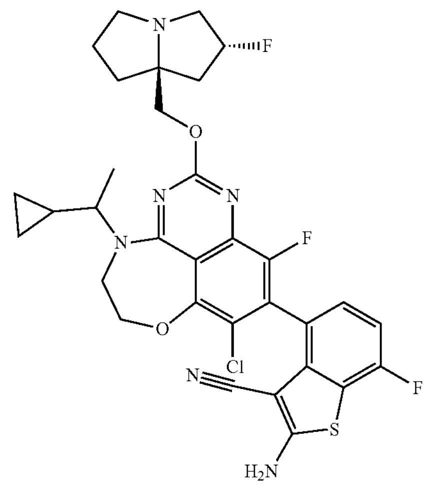 [SMILES: CC(C1CC1)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(1-cyclopropylethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 654.7 |
| 612 | 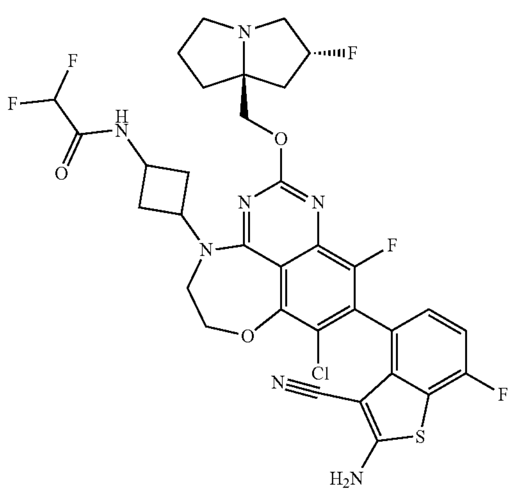 [SMILES: N#Cc1c(N)sc2c(F)ccc(-c3c(Cl)c4c5c(nc(OC[C@@]67CCCN6C[C@H](F)C7)nc5c3F)N(C3CC(NC(=O)C(F)F)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)-2,2-difluoroacetamide | 734.3 |

TABLE 1-continued

| No. | Chemical Name | [M + H]⁺ |
|---|---|---|
| 613 | (2R,3S)-N-(2-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)-3-cyclopropyl-N-methylaziridine-2-carboxamide | 751.5 [M − H]⁻ |
| 614 | N-(((5S)-9-(2-amino-3-cyano-7-fluorobenzo[b]thiophen-4-yl)-8-chloro-4-(3,3-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)formamide | 722.3 |
| 615 | 5-ethynyl-6-fluoro-4-(4-fluoro-2-(((2R,7aS)-2-fluorotetrahydro-1H-pyrrolizin-7a(5H)-yl)methoxy)-10-(tetrahydrofuran-3-yl)-9,10-dihydro-8H-7-oxa-1,3,6,10-tetraazacyclohepta[de]naphthalen-5-yl)naphthalen-2-ol | 617.9 |

TABLE 1-continued

| No. | Structure | Chemical Name | [M + H]+ |
|---|---|---|---|
| 616 | 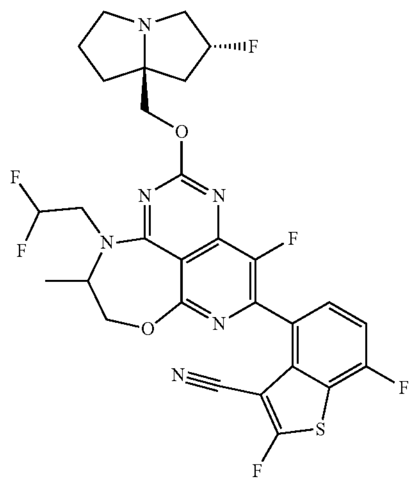 [SMILES: CC1COc2nc(-c3ccc(F)c4sc(F)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 664.9 |
| 617 | 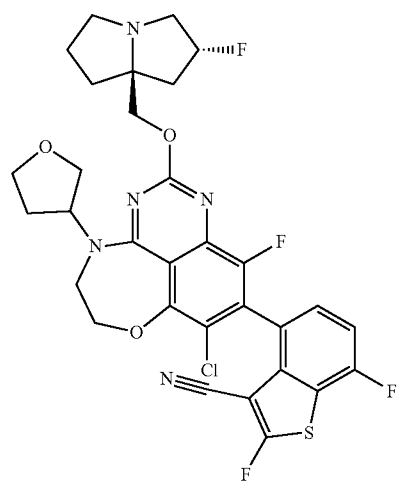 [SMILES: N#Cc1c(F)sc2c(F)ccc(-c3c(Cl)c4c5c(nc(OC[C@@]67CCCN6C[C@H](F)C7)nc5c3F)N(C3CCOC3)CCO4)c12] | 2-amino-4-(8-chloro-10-fluoro-2-(((2R,7aS)-2-fluorotetrahydro-1H-pyrrolizin-7a(5H)-yl)methoxy)-4-((R)-tetrahydrofuran-3-yl)-5,6-dihydro-4H-[1,4]oxazepino[5,6,7-de]quinazolin-9-yl)-7-fluorobenzo[b]thiophene-3-carbonitrile | 657.2 |
| 618 | 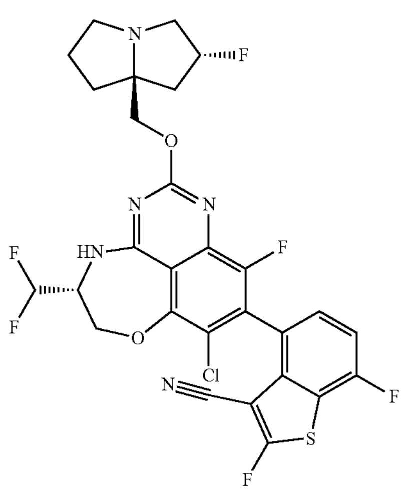 [SMILES: N#Cc1c(F)sc2c(F)ccc(-c3c(Cl)c4c5c(nc(OC[C@@]67CCCN6C[C@H](F)C7)nc5c3F)N[C@@H](C(F)F)CO4)c12] | 2-amino-4-((R)-8-chloro-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 636.9 |

TABLE 1-continued

| No. | Structure | Chemical Name | [M + H]+ |
|---|---|---|---|
| 619 | 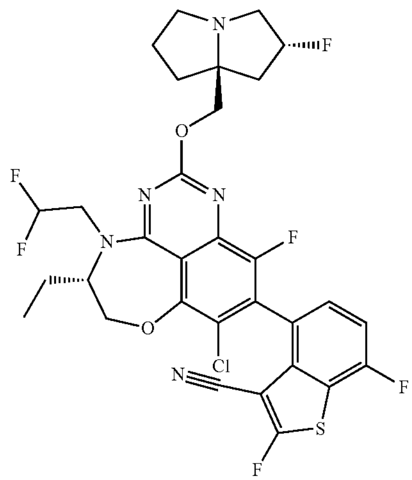 [SMILES: CC[C@H]1COc2c(Cl)c(-c3ccc(F)c4sc(F)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-ethyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 678.9 |
| 620 | 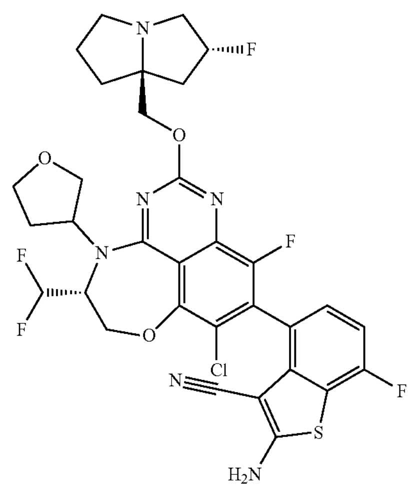 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C(F)F)CO4)c12] | 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 707 |
| 621 | 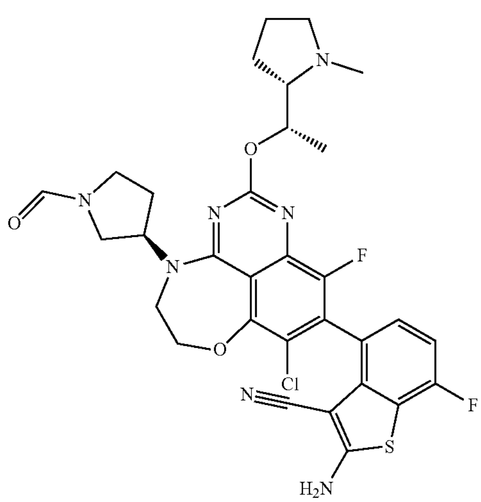 [SMILES: C[C@H](Oc1nc2c3c(c(Cl)c(-c4ccc(F)c5sc(N)c(C#N)c45)c(F)c3n1)OCCN2[C@@H]1CCN(C=O)C1)[C@@H]1CCCN1C] | 2-amino-4-(8-chloro-10-fluoro-4-((R)-1-formylpyrrolidin-3-yl)-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile | 654.3 |

TABLE 1-continued

| No. | Structure | Chemical Name | [M + H]+ |
|---|---|---|---|
| 622 | 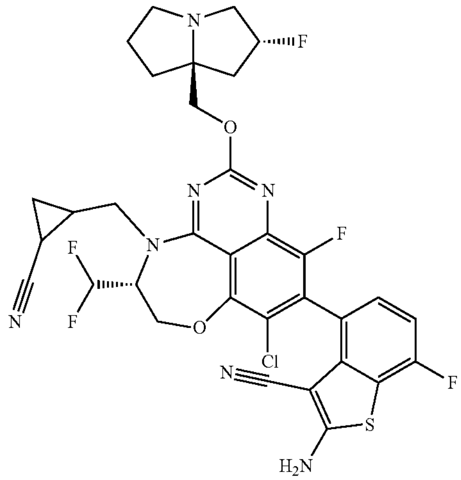 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716.4 |
| 623 | 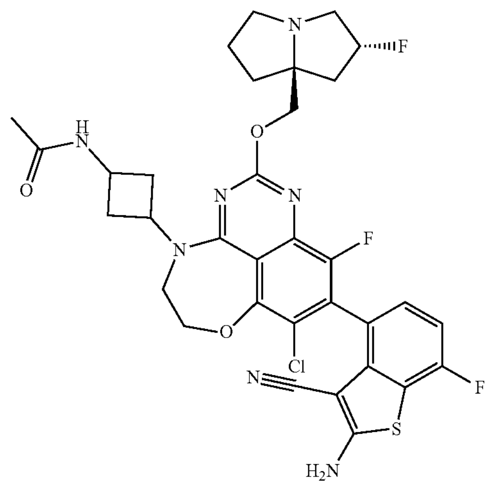 [SMILES: CC(=O)NC1CC(N2CCOc3c(Cl)c(-c4ccc(F)c5sc(N)c(C#N)c45)c(F)c4nc(OC[C@@]56CCCN5C[C@H](F)C6)nc2c34)C1] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)acetamide | 698.3 |
| 624 | 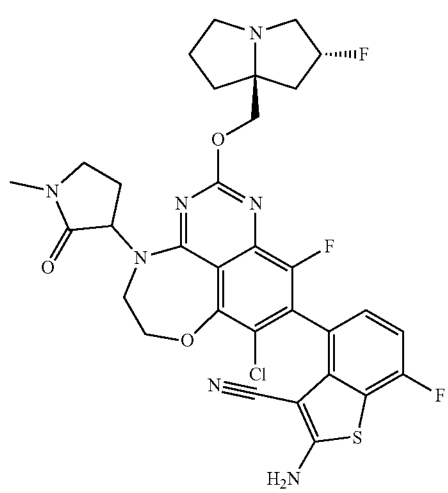 [SMILES: CN1CCC(N2CCOc3c(Cl)c(-c4ccc(F)c5sc(N)c(C#N)c45)c(F)c4nc(OC[C@@]56CCCN5C[C@H](F)C6)nc2c34)C1=O] | 2-amino-4-(8-chloro-10-fluoro-2-(((2R,7aS)-2-fluorotetrahydro-1H-pyrrolizin-7a(5H)-yl)methoxy)-4-(1-methyl-2-oxopyrrolidin-3-yl)-5,6-dihydro-4H-[1,4]oxazepino[5,6,7-de]quinazolin-9-yl)-7-fluorobenzo[b]thiophene-3-carbonitrile | 684.3 |

TABLE 1-continued

| No. | Structure | Chemical Name | [M + H]+ |
|---|---|---|---|
| 625 | 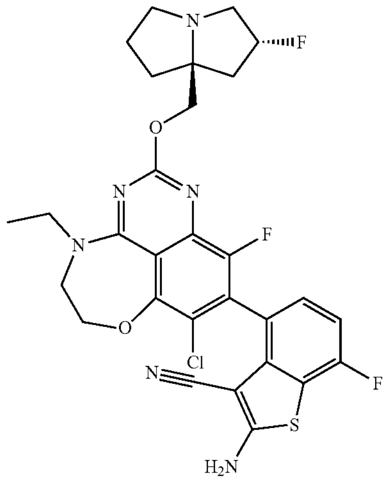 [SMILES: CCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-ethyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 615.3 |
| 626 | 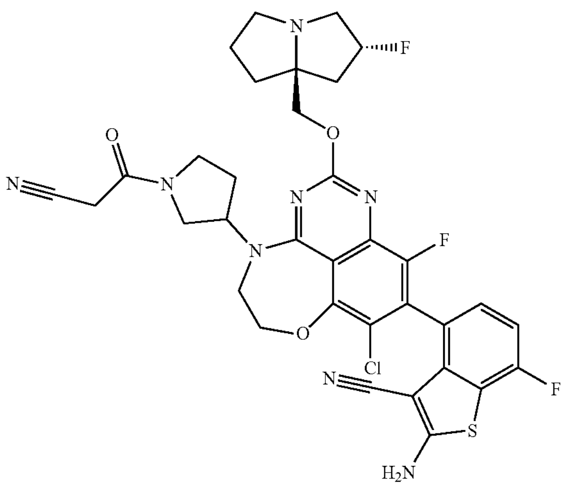 [SMILES: N#CCC(=O)N1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-(1-(2-cyanoacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 723.3 |
| 627 | 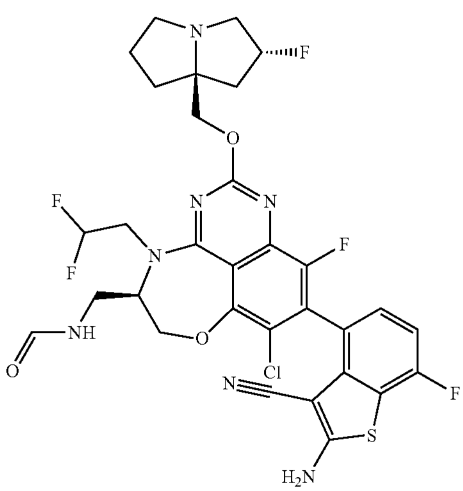 [SMILES: N#Cc1c(N)sc2c(F)ccc(-c3c(Cl)c4c5c(nc(OC[C@@]67CCCN6C[C@H](F)C7)nc5c3F)N(CC(F)F)[C@H](CNC=O)CO4)c12] | N-(((5R)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)formamide | 708.4 |

TABLE 1-continued

| No. | Structure | Chemical Name | [M + H]+ |
|---|---|---|---|
| 628 | 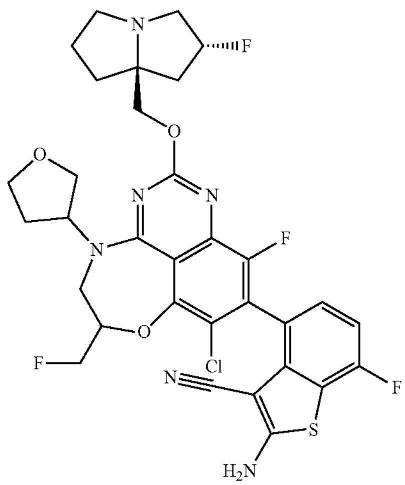 [SMILES: N#Cc1c(N)sc2c(F)ccc(-c3c(Cl)c4c5c(nc(OC[C@@]67CCCN6C[C@H](F)C7)nc5c3F)N(C3CCOC3)CC(CF)O4)c12] | 2-amino-4-(8-chloro-10-fluoro-6-(fluoromethyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 689 |
| 629 | 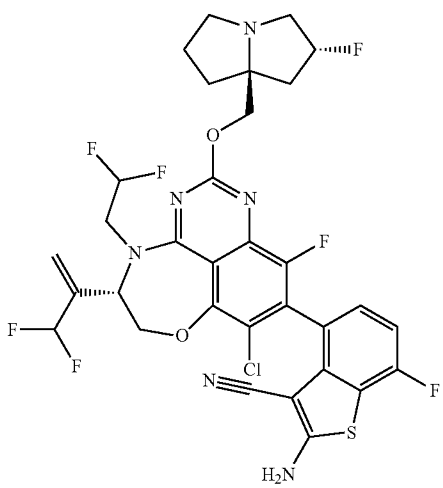 [SMILES: C=C(C(F)F)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 726.9 |
| 630 | 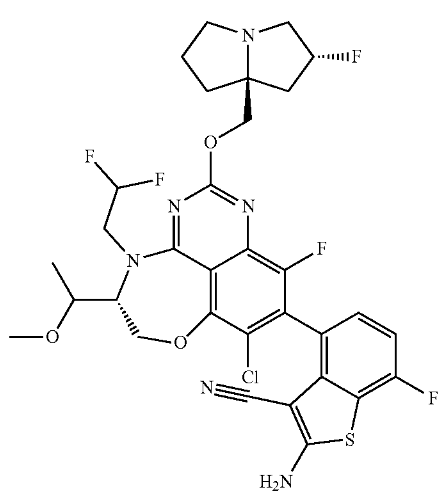 [SMILES: COC(C)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-(1-methoxyethyl)-5,6-dihydro-4H-[1,4]oxazepino[5,6,7-de]quinazolin-9-yl)-7-fluorobenzo[b]thiophene-3-carbonitrile | 708.9 |

TABLE 1-continued

| No. | Structure | Chemical Name | [M + H]⁺ |
|---|---|---|---|
| 631 | 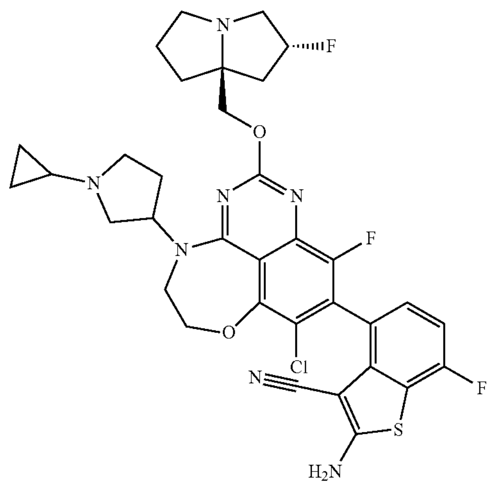 [SMILES: N#Cc1c(N)sc2c(F)ccc(-c3c(Cl)c4c5c(nc(OC[C@@]67CCCN6C[C@H](F)C7)nc5c3F)N(C3CCN(C5CC5)C3)CCO4)c12] | 2-amino-4-(8-chloro-4-(1-cyclopropylpyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 696.4 |
| 632 | 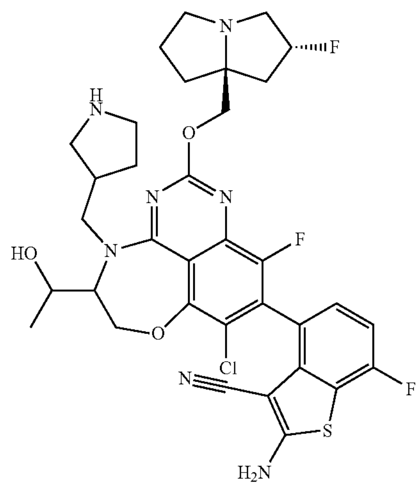 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC1CCNC1] | 2-amino-4-(8-chloro-10-fluoro-2-(((2R,7aS)-2-fluorotetrahydro-1H-pyrrolizin-7a(5H)-yl)methoxy)-5-(1-hydroxyethyl)-4-(pyrrolidin-3-ylmethyl)-5,6-dihydro-4H-[1,4]oxazepino[5,6,7-de]quinazolin-9-yl)-7-fluorobenzo[b]thiophene-3-carbonitrile | 714.3 |
| 633 | 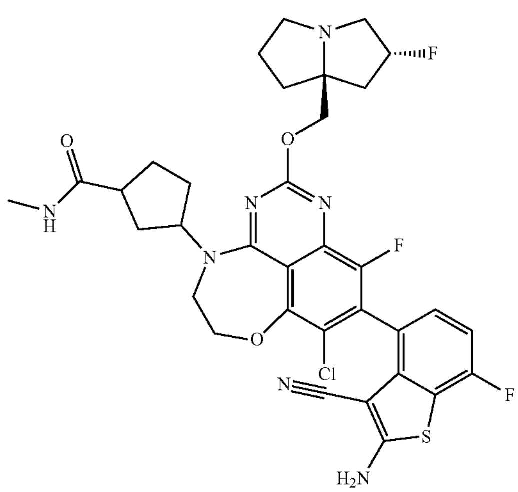 [SMILES: CNC(=O)C1CCC(N2CCOc3c(Cl)c(-c4ccc(F)c5sc(N)c(C#N)c45)c(F)c4nc(OC[C@@]56CCCN5C[C@H](F)C6)nc2c34)C1] | 3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N-methylcyclopentane-1-carboxamide | 712.3 |

TABLE 1-continued

| No. | Structure | Chemical Name | [M + H]+ |
|---|---|---|---|
| 634 | 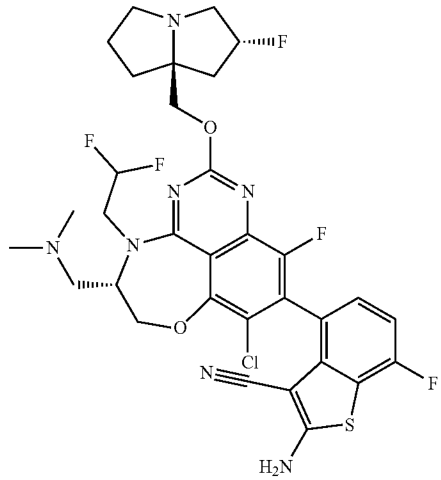 [SMILES: CN(C)C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-((dimethylamino)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 708.3 |
| 635 | 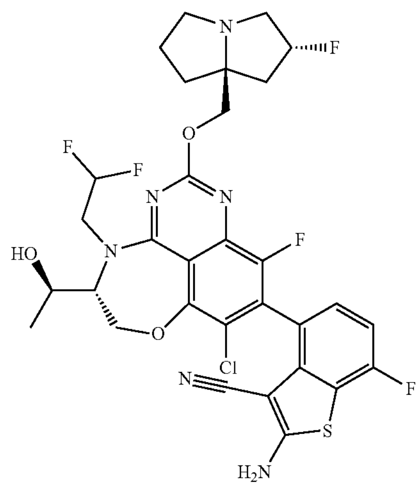 [SMILES: C[C@@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile | 694.9 |
| 636 | 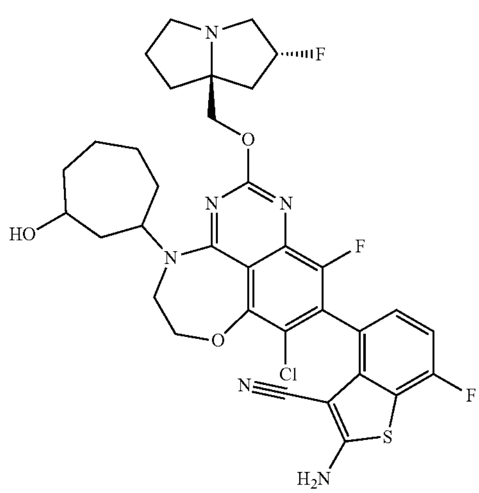 [SMILES: N#Cc1c(N)sc2c(F)ccc(-c3c(Cl)c4c5c(nc(OC[C@@]67CCCN6C[C@H](F)C7)nc5c3F)N(C3CCCCC(O)C3)CCO4)c12] | 2-amino-4-(8-chloro-10-fluoro-2-(((2R,7aS)-2-fluorotetrahydro-1H-pyrrolizin-7a(5H)-yl)methoxy)-4-(3-hydroxycycloheptyl)-5,6-dihydro-4H-[1,4]oxazepino[5,6,7-de]quinazolin-9-yl)-7-fluorobenzo[b]thiophene-3-carbonitrile | 745 |

TABLE 1-continued

| No. | Structure | Chemical Name | [M + H]+ |
|---|---|---|---|
| 637 | 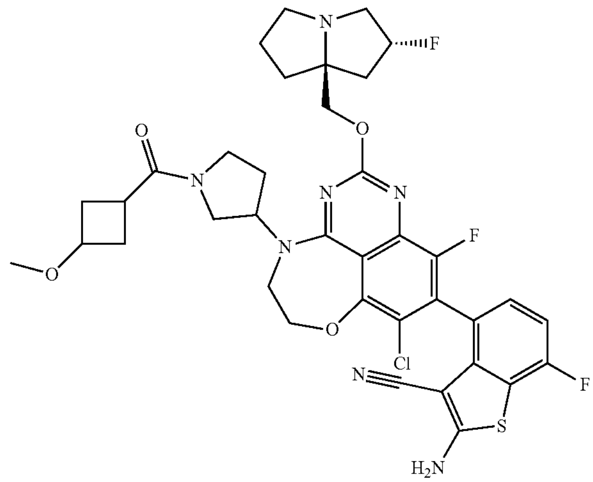 | 2-amino-4-(8-chloro-10-fluoro-2-(((2R,7aS)-2-fluorotetrahydro-1H-pyrrolizin-7a(5H)-yl)methoxy)-4-(1-(3-methoxycyclobutane-1-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 768.4 |
| 638 | 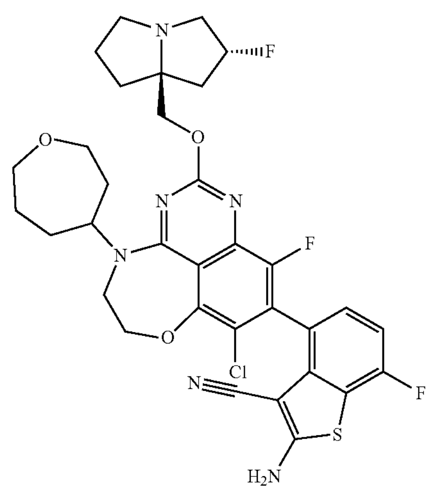 | 2-amino-4-(8-chloro-10-fluoro-2-(((2R,7aS)-2-fluorotetrahydro-1H-pyrrolizin-7a(5H)-yl)methoxy)-4-(oxepan-4-yl)-5,6-dihydro-4H-[1,4]oxazepino[5,6,7-de]quinazolin-9-yl)-7-fluorobenzo[b]thiophene-3-carbonitrile | 686.4 |
| 639 | 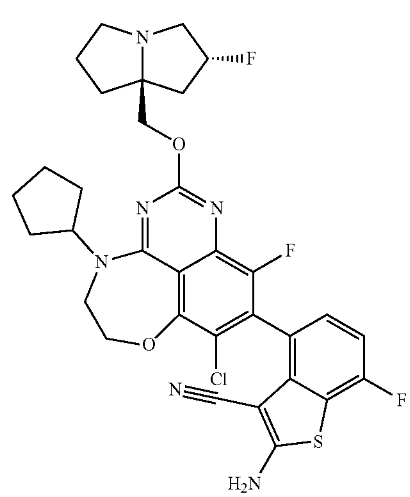 [SMILES: N#Cc1c(N)sc2c(F)ccc(-c3c(Cl)c4c5c(nc(OC[C@@]67CCCN6C[C@H](F)C7)nc5c3F)N(C3CCCC3)CCO4)c12] | 2-amino-4-(8-chloro-4-cyclopentyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 655.5 |

TABLE 1-continued

| No. | Structure | Chemical Name | [M + H]⁺ |
|---|---|---|---|
| 640 | 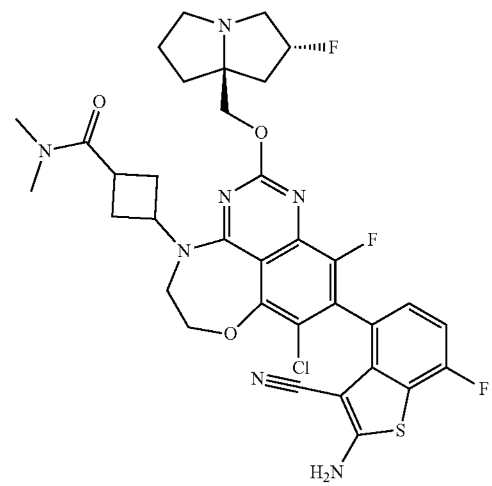 [SMILES: CN(C)C(=O)C1CC(N2CCOc3c(Cl)c(-c4ccc(F)c5sc(N)c(C#N)c45)c(F)c4nc(OC[C@@]56CCCN5C[C@H](F)C6)nc2c34)C1] | 3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N,N-dimethylcyclobutane-1-carboxamide | 711.8 |
| 641 | 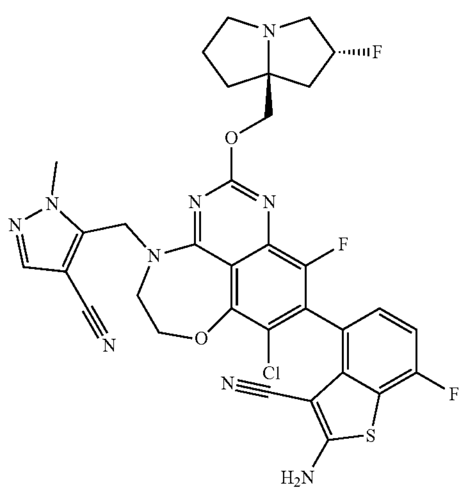 [SMILES: Cn1ncc(C#N)c1CN1CCOc2c(Cl)c(-c3ccc(F)c4sc(N)c(C#N)c34)c(F)c3nc(OC[C@@]45CCCN4C[C@H](F)C5)nc1c23] | 5-((9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)methyl)-1-methyl-1H-pyrazole-4-carbonitrile | 706.1 |
| 642 | 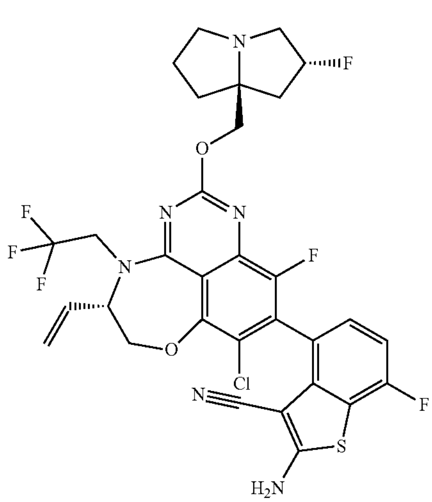 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CC(F)(F)F] | 2-amino-4-((5S)-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazolin-9-yl)-7-fluorobenzo[b]thiophene-3-carbonitrile | 694.9 |

TABLE 1-continued

| No. | Structure | Chemical Name | [M + H]+ |
|---|---|---|---|
| 643 | 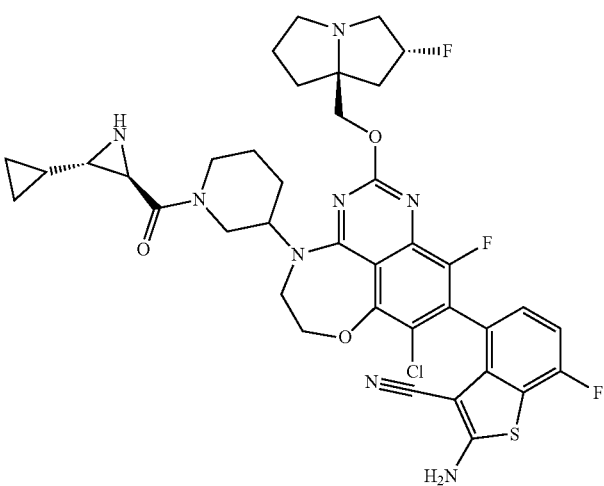 [SMILES: N#Cc1c(N)sc2c(F)ccc(-c3c(Cl)c4c5c(nc(OC[C@@]67CCCN6C[C@H](F)C7)nc5c3F)N(C3CCCN(C(=O)[C@@H]5N[C@H]5C5CC5)C3)CCO4)c12] | 2-amino-4-(8-chloro-4-(1-((2R,3S)-3-cyclopropylaziridine-2-carbonyl)piperidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 779.4 |
| 644 | 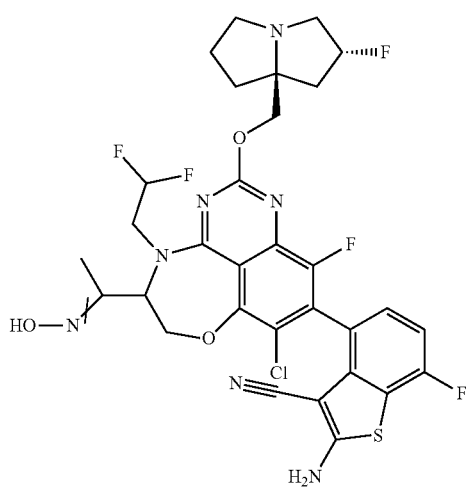 [SMILES: CC(NO)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-(hydroxyimino)ethyl)-5,6-dihydro-4H-[1,4]oxazepino[5,6,7-de]quinazolin-9-yl)-7-fluorobenzo[b]thiophene-3-carbonitrile | 707.9 |
| 645 | 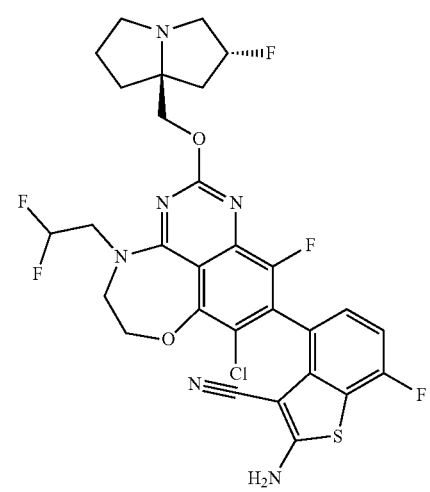 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 651.1 |

TABLE 1-continued

| No. | Structure | Chemical Name | [M + H]+ |
|---|---|---|---|
| 646 | 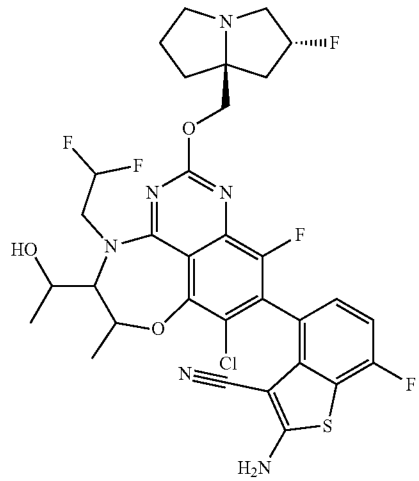 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 647 | 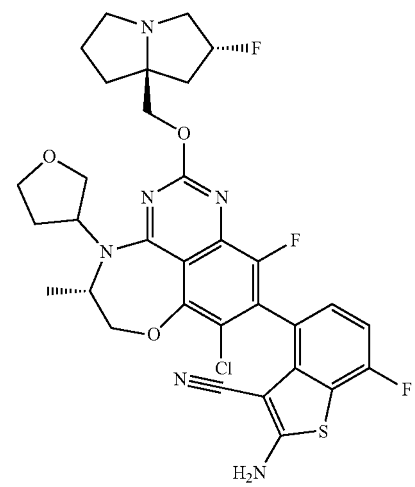 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-5-methyl-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 671.3 |
| 648 | 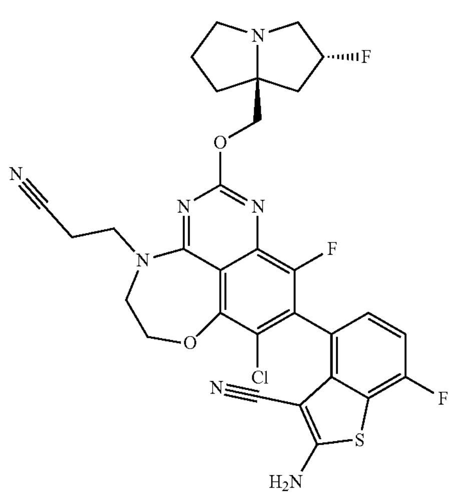 [SMILES: N#CCCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(2-cyanoethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 640.3 |

TABLE 1-continued

| No. | Structure | Chemical Name | [M + H]+ |
|---|---|---|---|
| 649 | 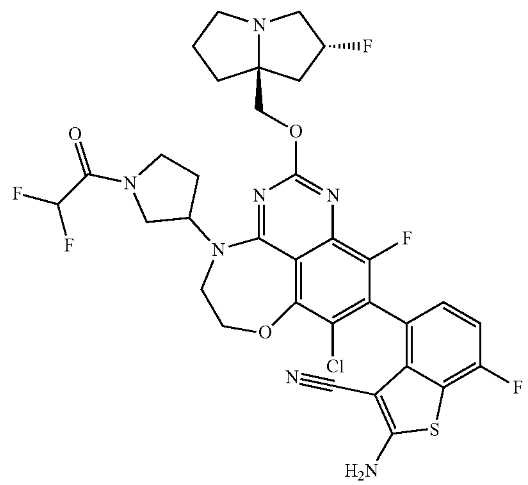 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C(F)F)C3)CCO4)c12] | 2-amino-4-(8-chloro-4-(1-(2,2-difluoroacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 734.2 |
| 650 | 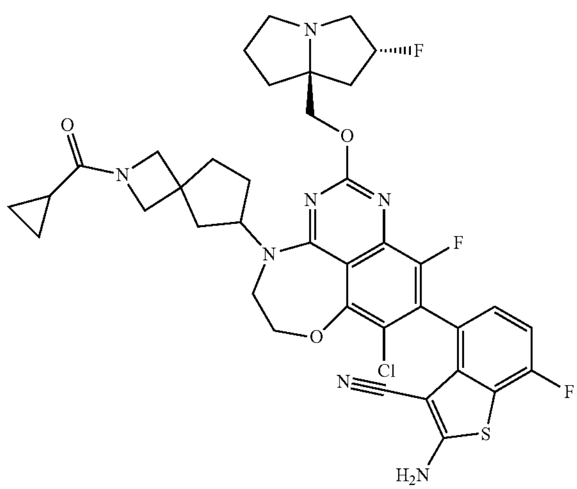 [SMILES: N#Cc1c(N)sc2c(F)ccc(-c3c(Cl)c4c5c(nc(OC[C@@]67CCCN6C[C@H](F)C7)nc5c3F)N(C3CCC5(C3)CN(C(=O)C3CC3)C5)CCO4)c12] | 2-amino-4-(8-chloro-4-(2-(cyclopropanecarbonyl)-2-azaspiro[3.4]octan-6-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 764 |
| 651 | 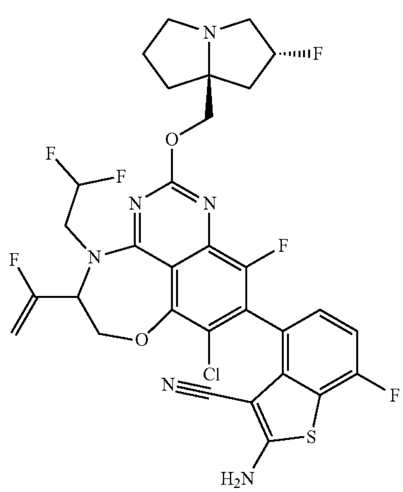 [SMILES: C=C(F)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazolin-9-yl)-7-fluorobenzo[b]thiophene-3-carbonitrile | 695 |

TABLE 1-continued

| No. | Structure | Chemical Name | [M + H]⁺ |
|---|---|---|---|
| 652 | 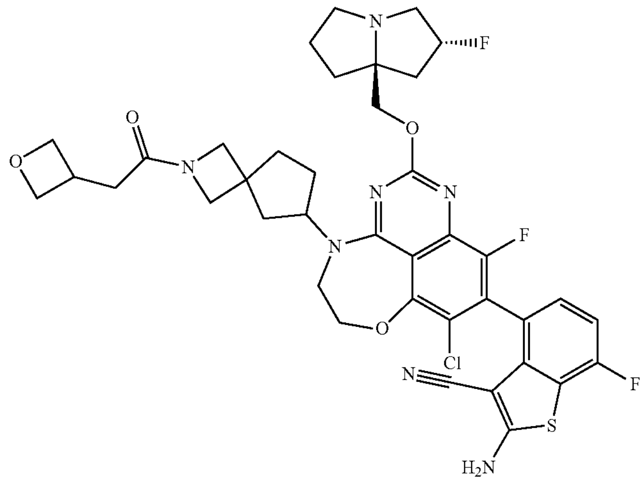 [SMILES: N#Cc1c(N)sc2c(F)ccc(-c3c(Cl)c4c5c(nc(OC[C@@]67CCCN6C[C@H](F)C7)nc5c3F)N(C3CCC5(C3)CN(C(=O)CC3COC3)C5)CCO4)c12] | 2-amino-4-(8-chloro-10-fluoro-2-(((2R,7aS)-2-fluorotetrahydro-1H-pyrrolizin-7a(5H)-yl)methoxy)-4-(2-(2-(oxetan-3-yl)acetyl)-2-azaspiro[3.4]octan-6-yl)-5,6-dihydro-4H-[1,4]oxazepino[5,6,7-de]quinazolin-9-yl)-7-fluorobenzo[b]thiophene-3-carbonitrile | 794 |
| 653 | 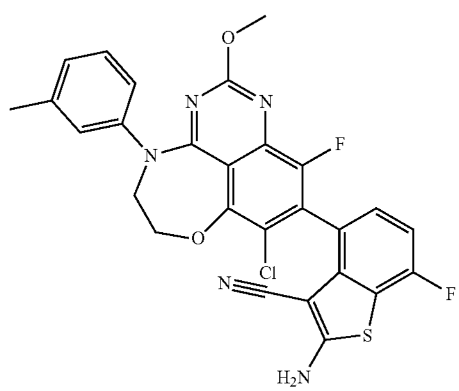 [SMILES: COc1nc2c3c(c(Cl)c(-c4ccc(F)c5sc(N)c(C#N)c45)c(F)c3n1)OCCN2c1cccc(C)c1] | 2-amino-4-(8-chloro-10-fluoro-2-methoxy-4-(m-tolyl)-5,6-dihydro-4H-[1,4]oxazepino[5,6,7-de]quinazolin-9-yl)-7-fluorobenzo[b]thiophene-3-carbonitrile | 549.7 |
| 654 | 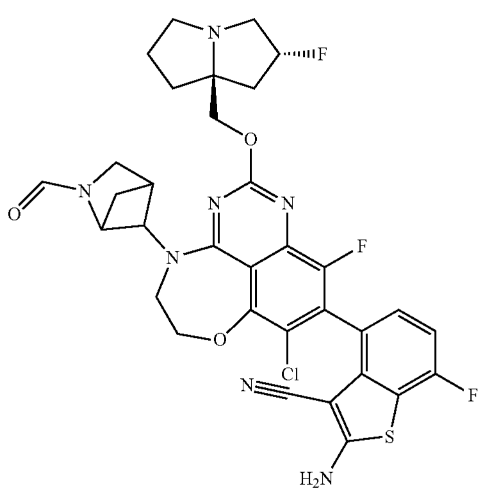 [SMILES: N#Cc1c(N)sc2c(F)ccc(-c3c(Cl)c4c5c(nc(OC[C@@]67CCCN6C[C@H](F)C7)nc5c3F)N(C3C5CC3N(C=O)C5)CCO4)c12] | 2-amino-4-(8-chloro-10-fluoro-2-(((2R,7aS)-2-fluorotetrahydro-1H-pyrrolizin-7a(5H)-yl)methoxy)-4-(2-formyl-2-azabicyclo[2.1.1]hexan-5-yl)-5,6-dihydro-4H-[1,4]oxazepino[5,6,7-de]quinazolin-9-yl)-7-fluorobenzo[b]thiophene-3-carbonitrile | 696.3 |

TABLE 1-continued

| No. | Structure | Chemical Name | [M + H]+ |
|---|---|---|---|
| 655 | 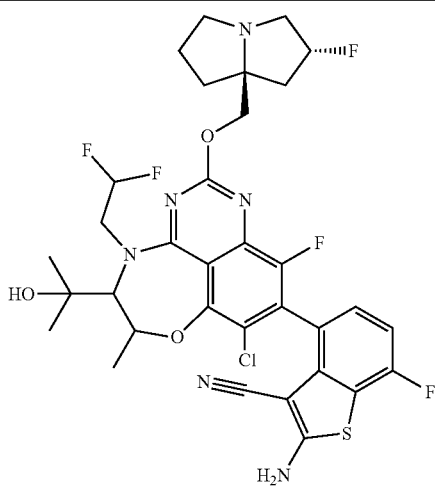 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropan-2-yl)-6-methyl-5,6-dihydro-4H-[1,4]oxazepino[5,6,7-de]quinazolin-9-yl)-7-fluorobenzo[b]thiophene-3-carbonitrile | 722.9 |
| 656 | 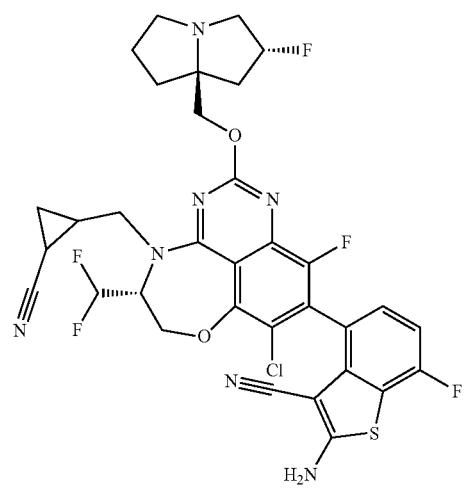 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |
| 657 | 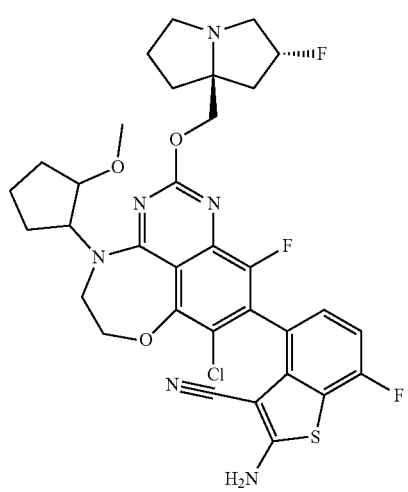 [SMILES: COC1CCCC1N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(2-methoxycyclopentyl)-5,6-dihydro-4H-[1,4]oxazepino[5,6,7-de]quinazolin-9-yl)-7-fluorobenzo[b]thiophene-3-carbonitrile | 685.1 |

TABLE 1-continued

| No. | Structure | Chemical Name | [M + H]+ |
|---|---|---|---|
| 658 | 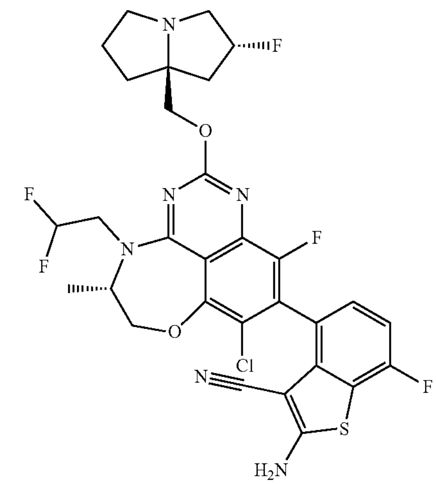 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 665 |
| 659 | 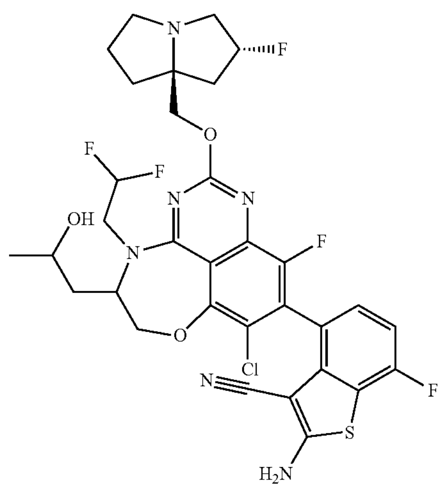 [SMILES: CC(O)CC1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropyl)-5,6-dihydro-4H-[1,4]oxazepino[5,6,7-de]quinazolin-9-yl)-7-fluorobenzo[b]thiophene-3-carbonitrile | 709.4 |
| 660 | 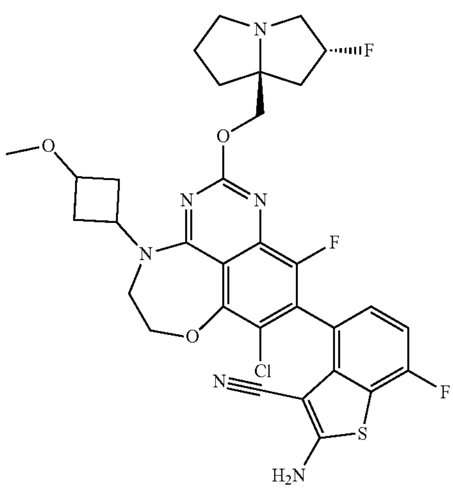 [SMILES: COC1CC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(3-methoxycyclobutyl)-5,6-dihydro-4H-[1,4]oxazepino[5,6,7-de]quinazolin-9-yl)-7-fluorobenzo[b]thiophene-3-carbonitrile | 671.2 |

TABLE 1-continued

| No. | Structure | Chemical Name | [M + H]⁺ |
|---|---|---|---|
| 661 | 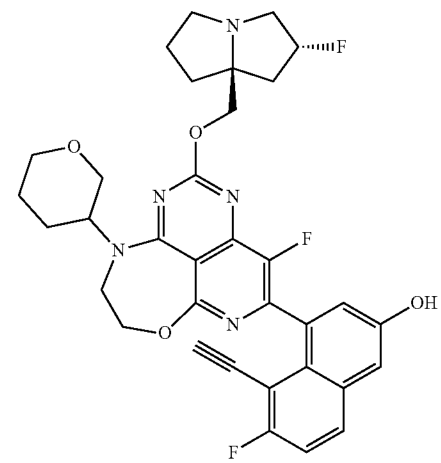 [SMILES: C#Cc1c(F)ccc2cc(O)cc(-c3nc4c5c(nc(OC[C@@]67CCCN6C[C@H](F)C7)nc5c3F)N(C3CCCOC3)CCO4)c12] | 5-ethynyl-6-fluoro-4-(4-fluoro-2-(((2R,7aS)-2-fluorotetrahydro-1H-pyrrolizin-7a(5H)-yl)methoxy)-10-(tetrahydro-2H-pyran-3-yl)-9,10-dihydro-8H-7-oxa-1,3,6,10-tetraazacyclohepta[de]naphthalen-5-yl)naphthalen-2-ol | 631.9 |
| 662 | 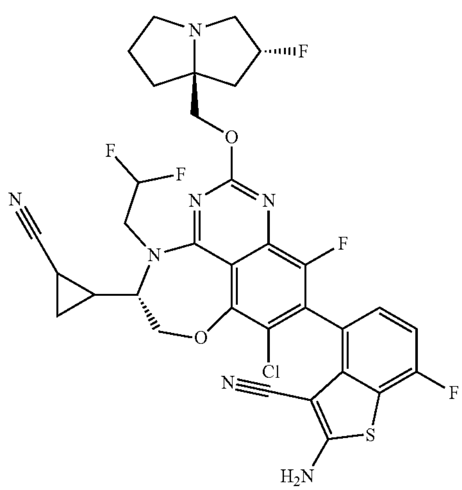 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3C#N)CO4)c12] | 2-amino-4-((5S)-8-chloro-5-(2-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716.4 |
| 663 | 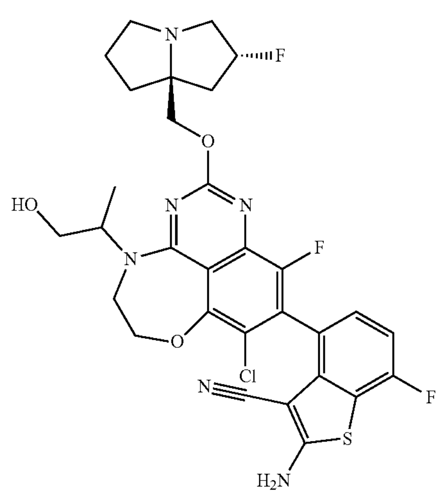 [SMILES: CC(CO)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(1-hydroxypropan-2-yl)-5,6-dihydro-4H-[1,4]oxazepino[5,6,7-de]quinazolin-9-yl)-7-fluorobenzo[b]thiophene-3-carbonitrile | 644.7 |

TABLE 1-continued

| No. | Structure | Chemical Name | [M + H]+ |
|---|---|---|---|
| 664 | 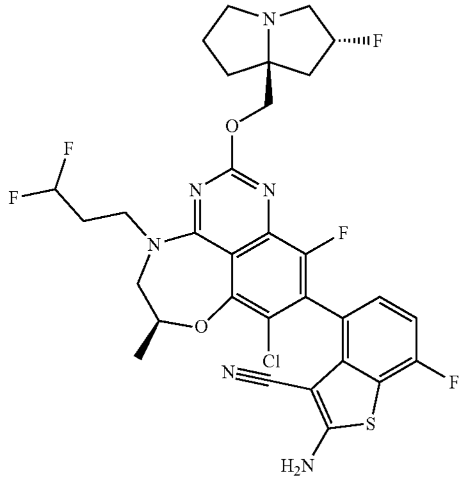 [SMILES: C[C@H]1CN(CCC(F)F)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-(3,3-difluoropropyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 678.9 |
| 665 | 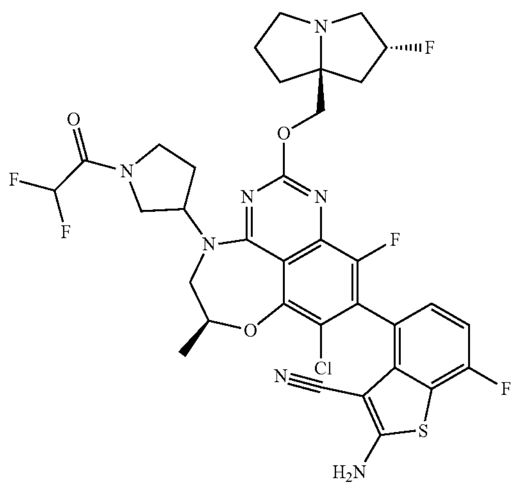 [SMILES: C[C@H]1CN(C2CCN(C(=O)C(F)F)C2)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-(1-(2,2-difluoroacetyl)pyrrolidin-3-yl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 748.3 |
| 666 | 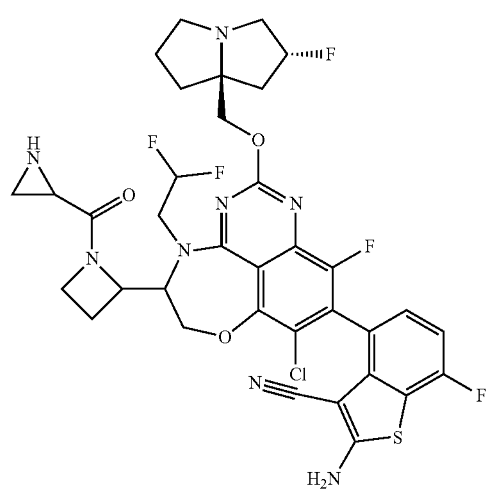 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCN3C(=O)C3CN3)CO4)c12] | 2-amino-4-(5-(1-(aziridine-2-carbonyl)azetidin-2-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 774.9 |

TABLE 1-continued

| No. | Structure | Chemical Name | [M + H]+ |
|---|---|---|---|
| 667 | 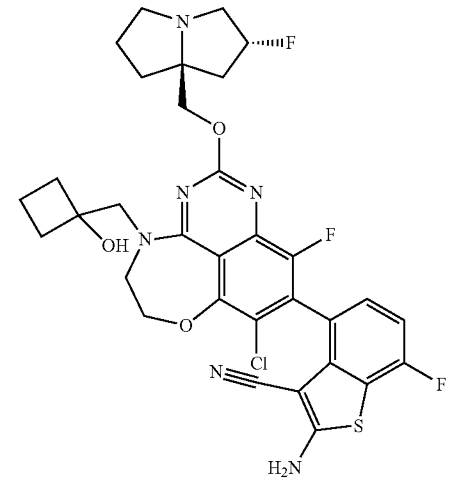 [SMILES: N#Cc1c(N)sc2c(F)ccc(-c3c(Cl)c4c5c(nc(OC[C@@]67CCCN6C[C@H](F)C7)nc5c3F)N(CC3(O)CCC3)CCO4)c12] | 2-amino-4-(8-chloro-10-fluoro-2-(((2R,7aS)-2-fluorotetrahydro-1H-pyrrolizin-7a(5H)-yl)methoxy)-4-((1-hydroxycyclobutyl)methyl)-5,6-dihydro-4H-[1,4]oxazepino[5,6,7-de]quinazolin-9-yl)-7-fluorobenzo[b]thiophene-3-carbonitrile | 671.2 |
| 668 | 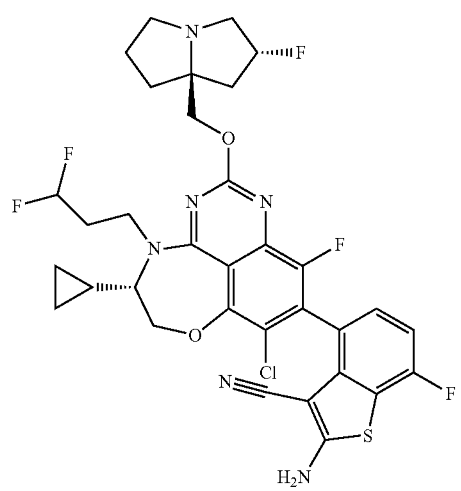 [SMILES: N#Cc1c(N)sc2c(F)ccc(-c3c(Cl)c4c5c(nc(OC[C@@]67CCCN6C[C@H](F)C7)nc5c3F)N(CCC(F)F)[C@@H](C3CC3)CO4)c12] | 2-amino-4-((S)-8-chloro-5-cyclopropyl-4-(3,3-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 705 |
| 669 | 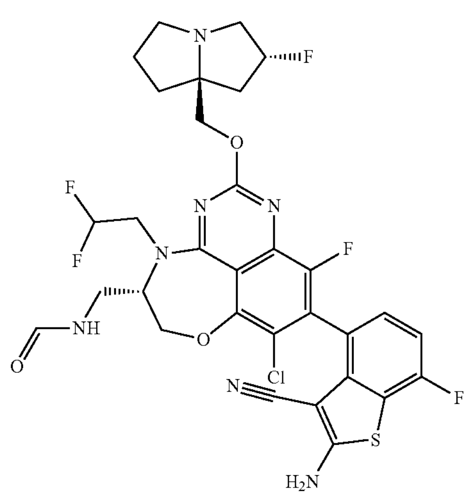 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](CNC=O)CO4)c12] | N-(((5S)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)formamide | 708.2 |

TABLE 1-continued

| No. | Structure | Chemical Name | [M + H]+ |
|---|---|---|---|
| 670 | 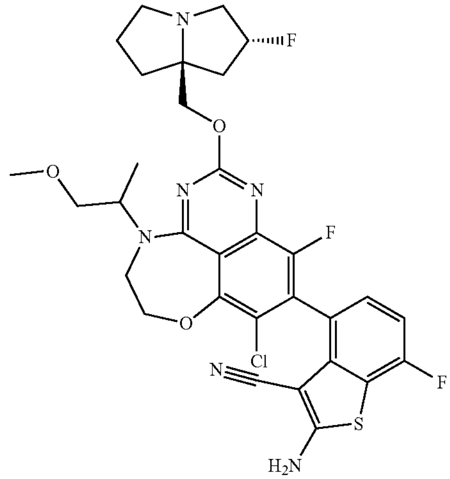 [SMILES: COCC(C)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(1-methoxypropan-2-yl)-5,6-dihydro-4H-[1,4]oxazepino[5,6,7-de]quinazolin-9-yl)-7-fluorobenzo[b]thiophene-3-carbonitrile | 658.8 |
| 671 | 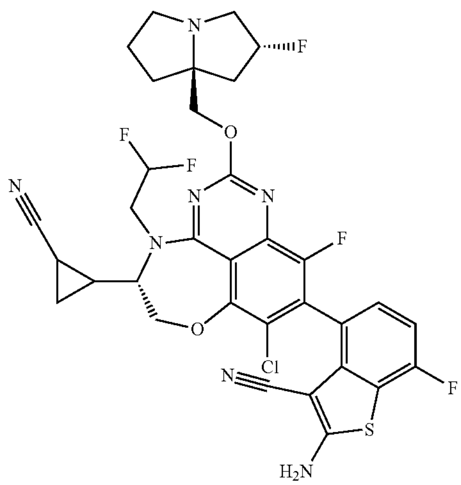 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3C#N)CO4)c12] | 2-amino-4-((5S)-8-chloro-5-(2-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 715.9 |
| 672 | 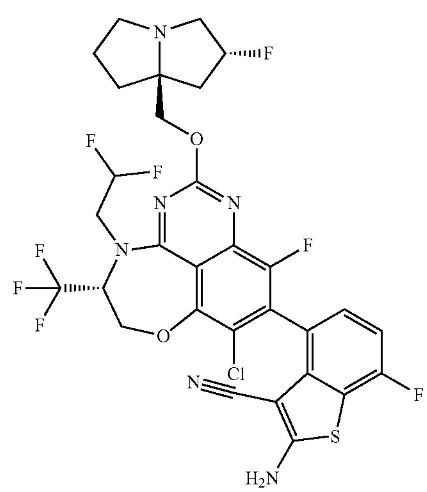 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C(F)(F)F)CO4)c12] | 2-amino-4-((R)-8-chloro-4-(2,2-difluoroethyl)-10-fluoro-2-(((2R,7aS)-2-fluorotetrahydro-1H-pyrrolizin-7a(5H)-yl)methoxy)-5-(trifluoromethyl)-5,6-dihydro-4H-[1,4]oxazepino[5,6,7-de]quinazolin-9-yl)-7-fluorobenzo[b]thiophene-3-carbonitrile | 718.9 |

TABLE 1-continued

| No. | Structure | Chemical Name | [M + H]⁺ |
|---|---|---|---|
| 673 | 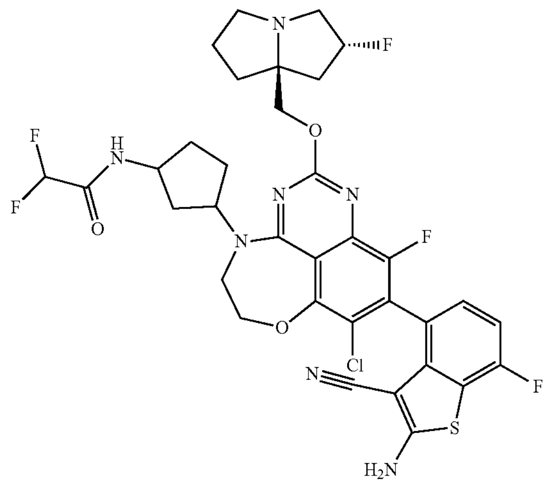 [SMILES: N#Cc1c(N)sc2c(F)ccc(-c3c(Cl)c4c5c(nc(OC[C@@]67CCCN6C[C@H](F)C7)nc5c3F)N(C3CCC(NC(=O)C(F)F)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclopentyl)-2,2-difluoroacetamide | 746.5 [M − H]⁻ |
| 674 | 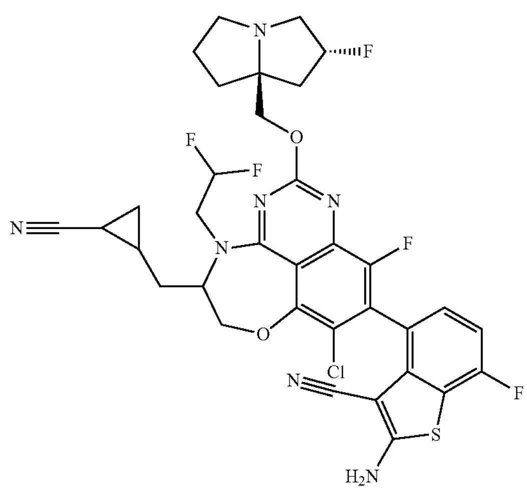 [SMILES: N#Cc1c(N)sc2c(F)ccc(-c3c(Cl)c4c5c(nc(OC[C@@]67CCCN6C[C@H](F)C7)nc5c3F)N(CC(F)F)C(CC3CC3C#N)CO4)c12] | 2-amino-4-(8-chloro-5-((2-cyanocyclopropyl)methyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 729.7 |
| 675 | 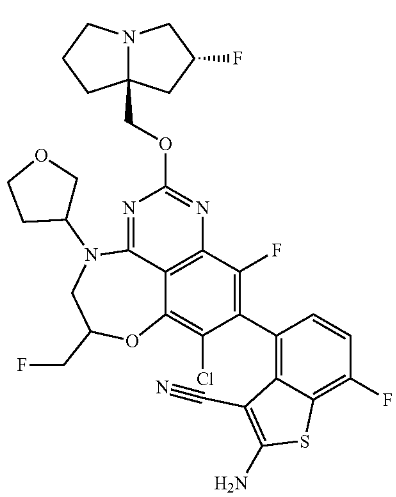 [SMILES: N#Cc1c(N)sc2c(F)ccc(-c3c(Cl)c4c5c(nc(OC[C@@]67CCCN6C[C@H](F)C7)nc5c3F)N(C3CCOC3)CC(CF)O4)c12] | 2-amino-4-(8-chloro-10-fluoro-6-(fluoromethyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 689 |

| No. | Structure | Chemical Name | [M + H]⁺ |
|---|---|---|---|
| 676 | 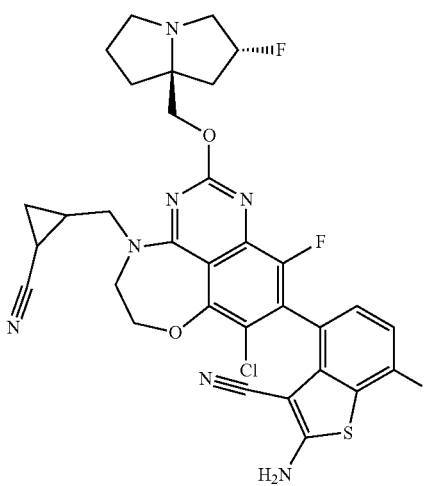 | 2-amino-4-(8-chloro-4-((2-cyanocyclopropyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 665.9 |
| 677 | 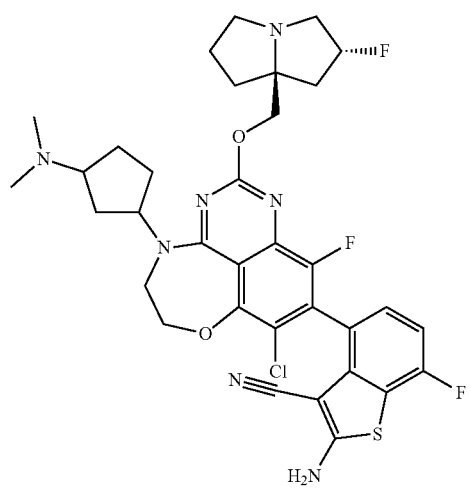 [SMILES: CN(C)C1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-4-(3-(dimethylamino)cyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 698.3 |
| 678 | 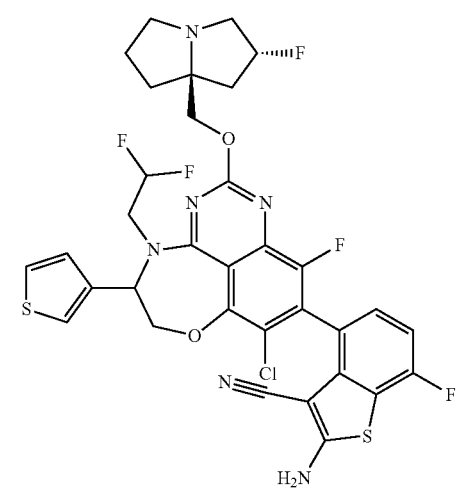 [SMILES: N#Cc1c(N)sc2c(F)ccc(-c3c(Cl)c4c5c(nc(OC[C@@]67CCCN6C[C@H](F)C7)nc5c3F)N(CC(F)F)C(c3ccsc3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiophen-3-yl)-5,6-dihydro-4H-[1,4]oxazepino[5,6,7-de]quinazolin-9-yl)-7-fluorobenzo[b]thiophene-3-carbonitrile | 732.8 |

TABLE 1-continued

| No. | Structure | Chemical Name | [M + H]+ |
|---|---|---|---|
| 679 | 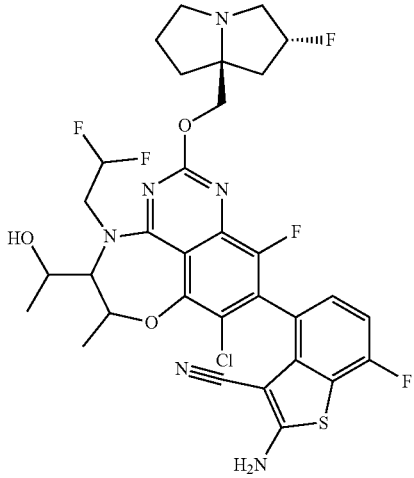 [SMILES: CC(O)C1C(C)Oc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 680 | 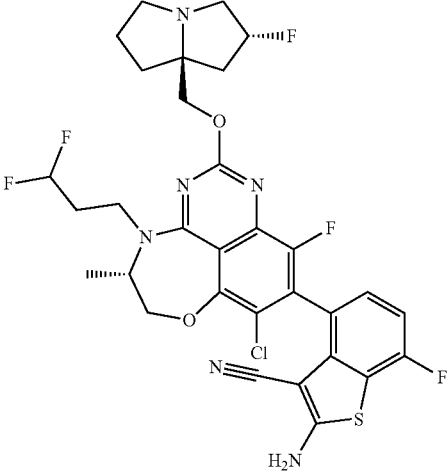 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 679.3 |
| 681 | 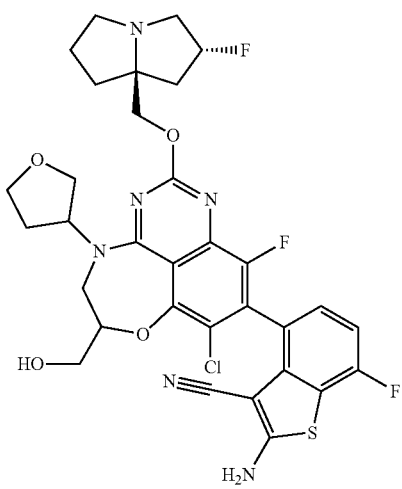 [SMILES: N#Cc1c(N)sc2c(F)ccc(-c3c(Cl)c4c5c(nc(OC[C@@]67CCCN6C[C@H](F)C7)nc5c3F)N(C3CCOC3)CC(CO)O4)c12] | 2-amino-4-(8-chloro-10-fluoro-2-(((2R,7aS)-2-fluorotetrahydro-1H-pyrrolizin-7a(5H)-yl)methoxy)-6-(hydroxymethyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 688.7 |

TABLE 1-continued

| No. | Structure | Chemical Name | [M + H]+ |
|---|---|---|---|
| 682 | 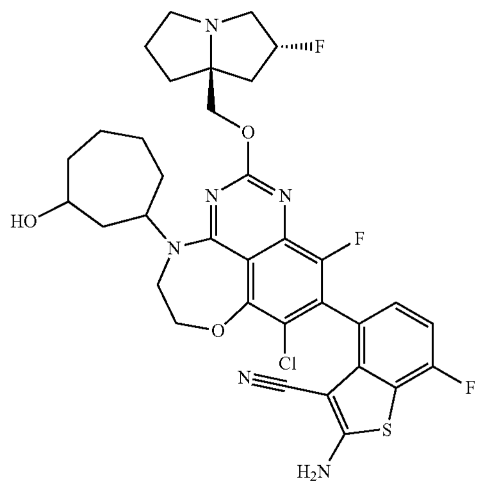 [SMILES: N#Cc1c(N)sc2c(F)ccc(-c3c(Cl)c4c5c(nc(OC[C@@]67CCCN6C[C@H](F)C7)nc5c3F)N(C3CCCCC(O)C3)CCO4)c12] | 2-amino-4-(8-chloro-10-fluoro-2-(((2R,7aS)-2-fluorotetrahydro-1H-pyrrolizin-7a(5H)-yl)methoxy)-4-(3-hydroxycycloheptyl)-5,6-dihydro-4H-[1,4]oxazepino[5,6,7-de]quinazolin-9-yl)-7-fluorobenzo[b]thiophene-3-carbonitrile | 699.3 |
| 683 | 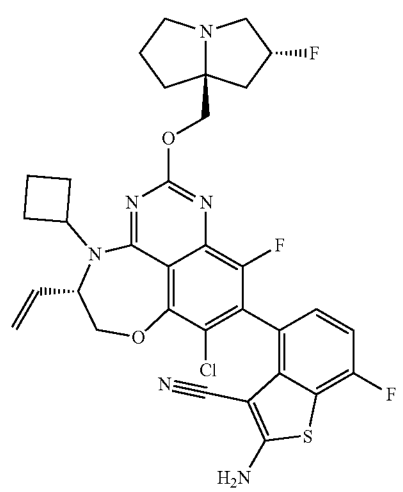 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCC1] | 2-amino-4-((5S)-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 666.9 |
| 684 | 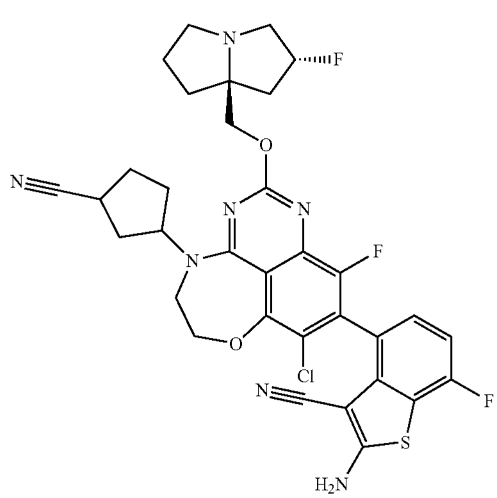 [SMILES: N#Cc1c(N)sc2c(F)ccc(-c3c(Cl)c4c5c(nc(OC[C@@]67CCCN6C[C@H](F)C7)nc5c3F)N(C3CCC(C#N)C3)CCO4)c12] | 2-amino-4-(8-chloro-4-(3-cyanocyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 680.2 |

TABLE 1-continued

| No. | Structure | Chemical Name | [M + H]+ |
|---|---|---|---|
| 685 | 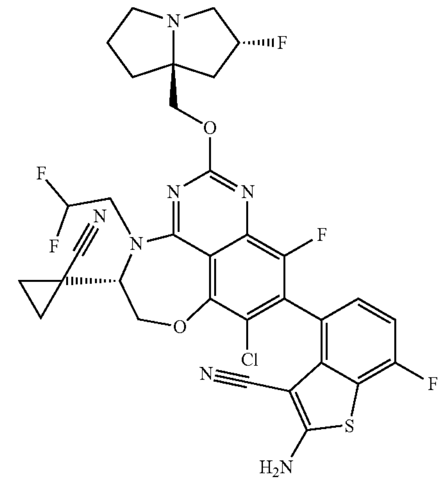 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(C#N)CC3)CO4)c12] | 2-amino-4-((S)-8-chloro-5-(1-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |
| 686 | 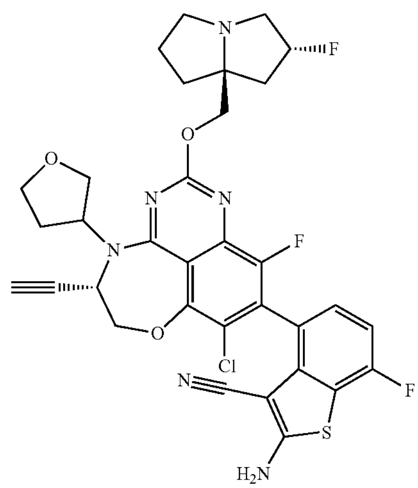 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-5-ethynyl-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 681.3 |
| 687 | 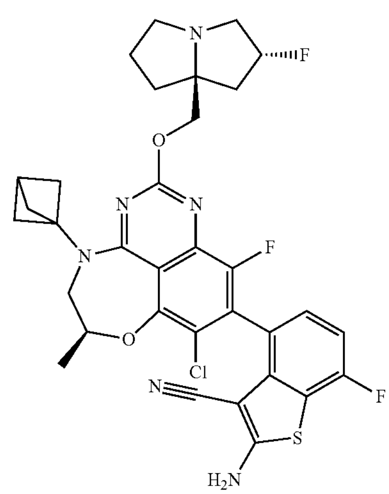 [SMILES: C[C@H]1CN(C23CC(C2)C3)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-4-(bicyclo[1.1.1]pentan-1-yl)-8-chloro-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 667 |

| No. | Structure | Chemical Name | [M + H]+ |
|---|---|---|---|
| 688 | 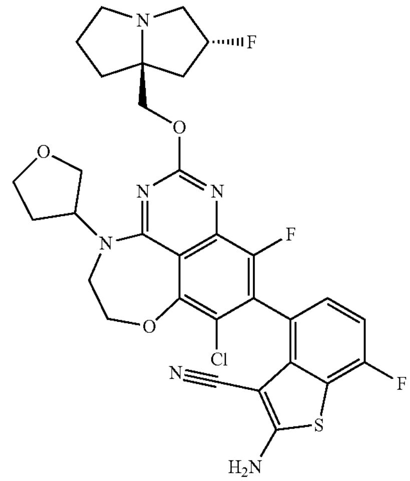 [SMILES: N#Cc1c(N)sc2c(F)ccc(-c3c(Cl)c4c5c(nc(OC[C@@]67CCCN6C[C@H](F)C7)nc5c3F)N(C3CCOC3)CCO4)c12] | 2-amino-4-(8-chloro-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 657.2 |
| 689 | 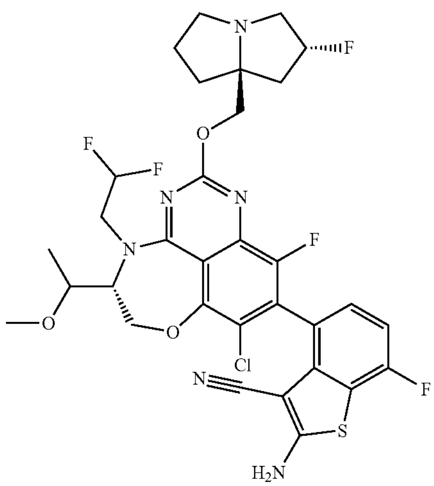 [SMILES: COC(C)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-(1-methoxyethyl)-5,6-dihydro-4H-[1,4]oxazepino[5,6,7-de]quinazolin-9-yl)-7-fluorobenzo[b]thiophene-3-carbonitrile | 708.9 |
| 690 | 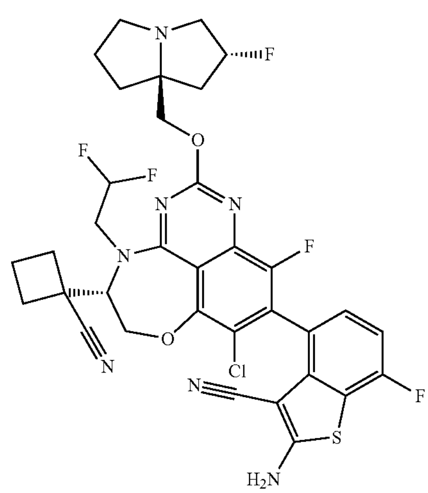 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(C#N)CCC3)CO4)c12] | 2-amino-4-((S)-8-chloro-5-(1-cyanocyclobutyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 730.1 |

TABLE 1-continued

| No. | Structure | Chemical Name | [M + H]+ |
|---|---|---|---|
| 691 | 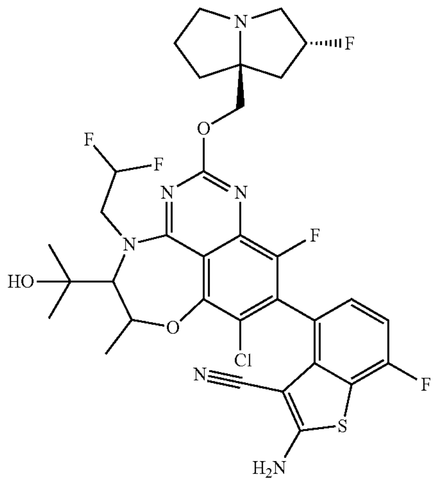 [SMILES: CC1Oc2c(Cl)c(-c3ccc(F)c4sc(N)c(C#N)c34)c(F)c3nc(OC[C@@]45CCCN4C[C@H](F)C5)nc(c23)N(CC(F)F)C1C(C)(C)O] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropan-2-yl)-6-methyl-5,6-dihydro-4H-[1,4]oxazepino[5,6,7-de]quinazolin-9-yl)-7-fluorobenzo[b]thiophene-3-carbonitrile | 722.9 |
| 692 | 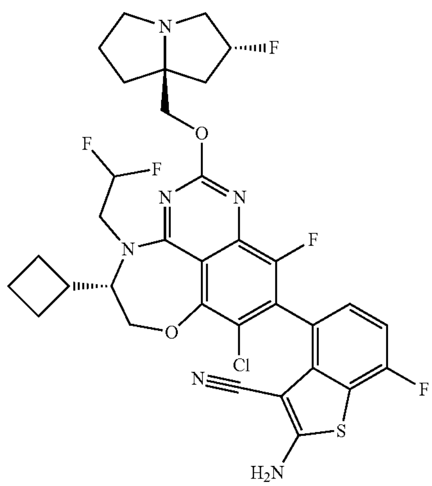 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CCC3)CO4)c12] | 2-amino-4-((S)-8-chloro-5-cyclobutyl-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 705.3 |
| 693 | 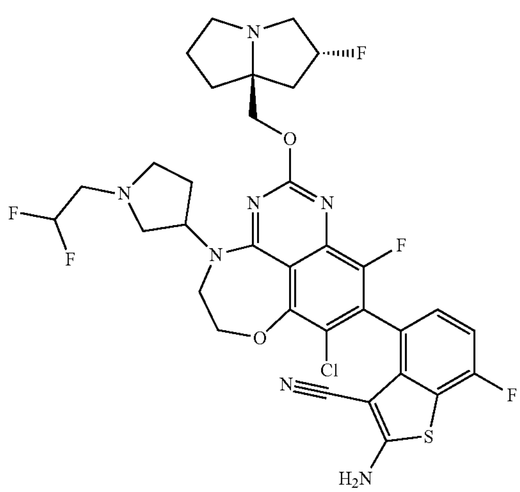 [SMILES: N#Cc1c(N)sc2c(F)ccc(-c3c(Cl)c4c5c(nc(OC[C@@]67CCCN6C[C@H](F)C7)nc5c3F)N(C3CCN(CC(F)F)C3)CCO4)c12] | 2-amino-4-(8-chloro-4-(1-(2,2-difluoroethyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 720.4 |

TABLE 1-continued

| No. | Chemical Name | [M + H]⁺ |
|---|---|---|
| 694 | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-(prop-1-yn-1-yl)-5,6-dihydro-4H-[1,4]oxazepino[5,6,7-de]quinazolin-9-yl)-7-fluorobenzo[b]thiophene-3-carbonitrile | 688.9 |
| 695 | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazolin-9-yl)-7-fluorobenzo[b]thiophene-3-carbonitrile | 690.9 |
| 696 | 2-amino-4-((S)-8-chloro-5-(3-cyanocyclobutyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 729.9 |

TABLE 1-continued

| No. | Structure | Chemical Name | [M + H]+ |
|---|---|---|---|
| 697 | 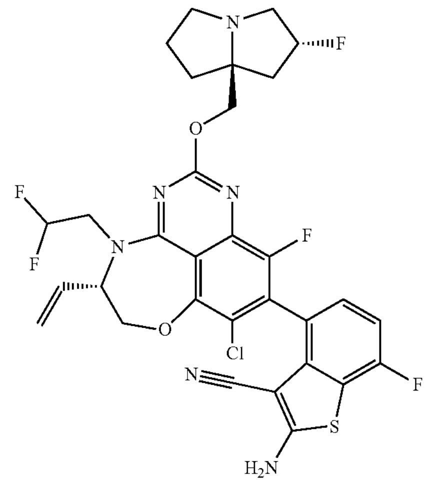 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 677 |
| 698 | 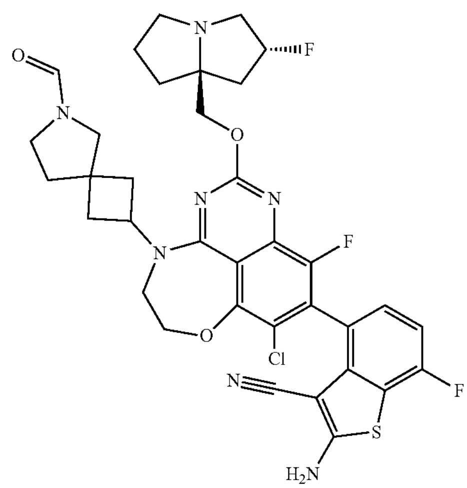 [SMILES: N#Cc1c(N)sc2c(F)ccc(-c3c(Cl)c4c5c(nc(OC[C@@]67CCCN6C[C@H](F)C7)nc5c3F)N(C3CC5(CCN(C=O)C5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(6-formyl-6-azaspiro[3.4]octan-2-yl)-5,6-dihydro-4H-[1,4]oxazepino[5,6,7-de]quinazolin-9-yl)-7-fluorobenzo[b]thiophene-3-carbonitrile | 742.2 |
| 699 | 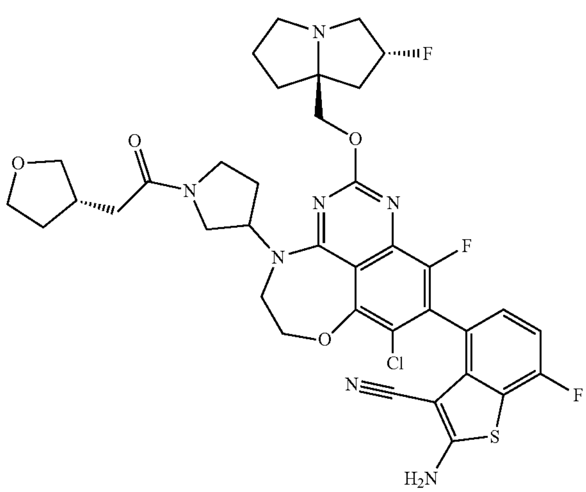 | 2-amino-4-(8-chloro-10-fluoro-2-(((2R,7aS)-2-fluorotetrahydro-1H-pyrrolizin-7a(5H)-yl)methoxy)-4-(1-(2-((S)-tetrahydrofuran-3-yl)acetyl)pyrrolidin-3-yl)-5,6-dihydro-4H-[1,4]oxazepino[5,6,7-de]quinazolin-9-yl)-7-fluorobenzo[b]thiophene-3-carbonitrile | 768.4 |

TABLE 1-continued

| No. | Structure | Chemical Name | [M + H]+ |
|---|---|---|---|
| 700 | 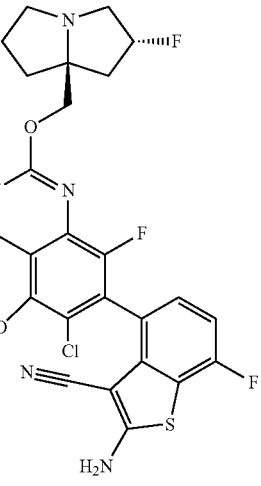 | 2-amino-4-(8-chloro-5-(cyanomethyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 690.1 |
| 701 | 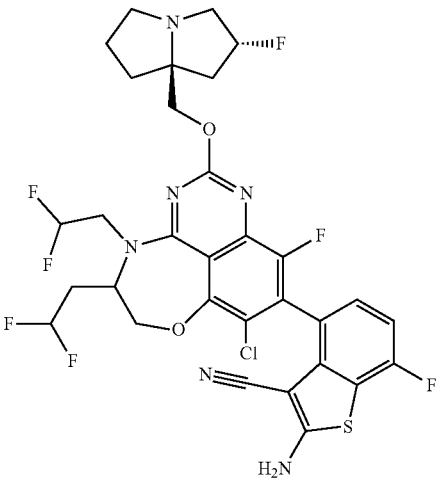 [SMILES: N#Cc1c(N)sc2c(F)ccc(-c3c(Cl)c4c5c(nc(OC[C@@]67CCCN6C[C@H](F)C7)nc5c3F)N(CC(F)F)C(CC(F)F)CO4)c12] | 2-amino-4-(8-chloro-4,5-bis(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 714.9 |
| 702 | 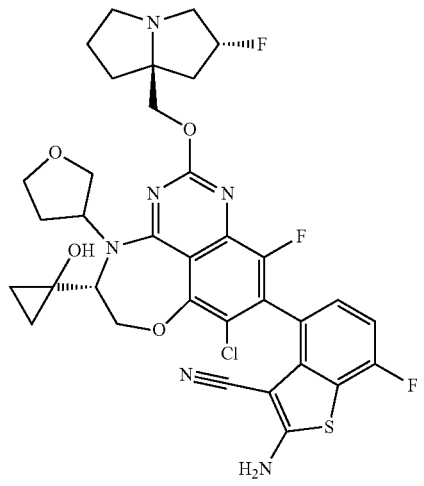 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(O)CC3)CO4)c12] | 2-amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 713 |

TABLE 1-continued

| No. | Structure | Chemical Name | [M + H]+ |
|---|---|---|---|
| 703 | 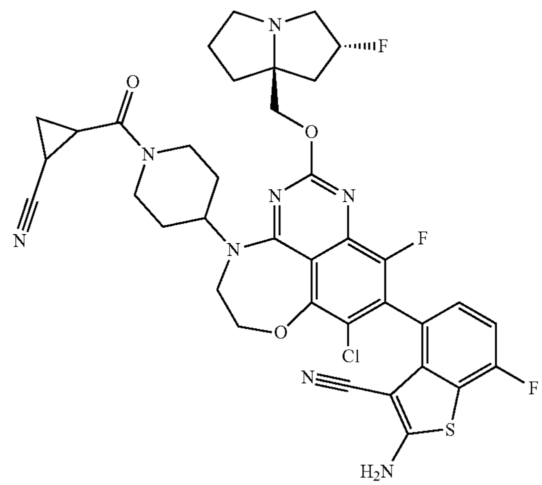 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C5CC5C#N)CC3)CCO4)c12] | 2-amino-4-(8-chloro-4-(1-(2-cyanocyclopropane-1-carbonyl)piperidin-4-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 763.4 |
| 704 | 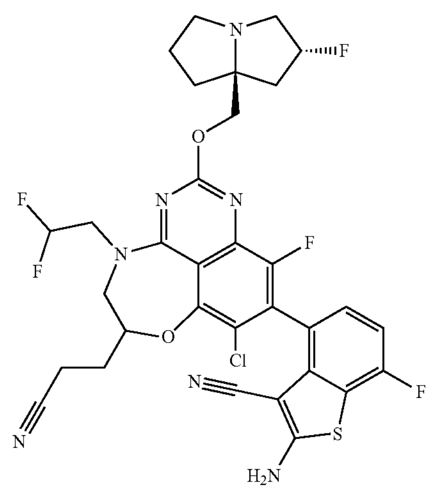 [SMILES: N#CCCC1CN(CC(F)F)c2nc(OC[C@@]34CCCN3C[C@H](F)C4)nc3c(F)c(-c4ccc(F)c5sc(N)c(C#N)c45)c(Cl)c(c23)O1] | 2-amino-4-(8-chloro-6-(2-cyanoethyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 704 |
| 705 | 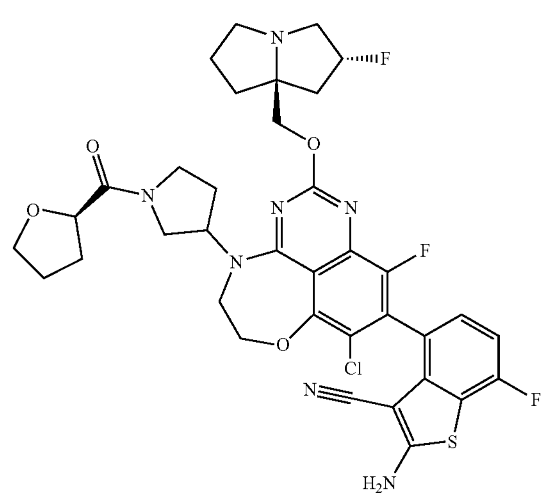 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)[C@H]5CCCO5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-((R)-tetrahydrofuran-2-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 754.4 |

TABLE 1-continued

| No. | Structure | Chemical Name | [M + H]⁺ |
|---|---|---|---|
| 706 | 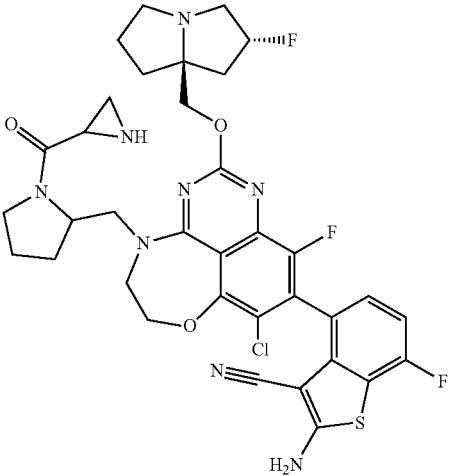 [SMILES: N#Cc1c(N)sc2c(F)ccc(-c3c(Cl)c4c5c(nc(OC[C@@]67CCCN6C[C@H](F)C7)nc5c3F)N(CC3CCCN3C(=O)C3CN3)CCO4)c12] | 2-amino-4-(4-((1-(aziridine-2-carbonyl)pyrrolidin-2-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 739.4 |
| 707 | 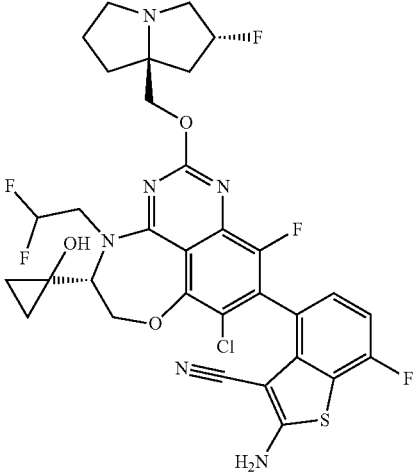 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(O)CC3)CO4)c12] | 2-amino-4-((R)-8-chloro-4-(2,2-difluoroethyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 707.3 |
| 708 | 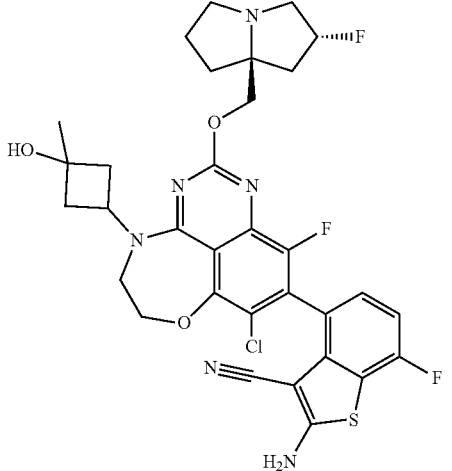 [SMILES: CC1(O)CC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(3-hydroxy-3-methylcyclobutyl)-5,6-dihydro-4H-[1,4]oxazepino[5,6,7-de]quinazolin-9-yl)-7-fluorobenzo[b]thiophene-3-carbonitrile | 671.2 |

TABLE 1-continued

| No. | Structure | Chemical Name | [M + H]+ |
|---|---|---|---|
| 709 | 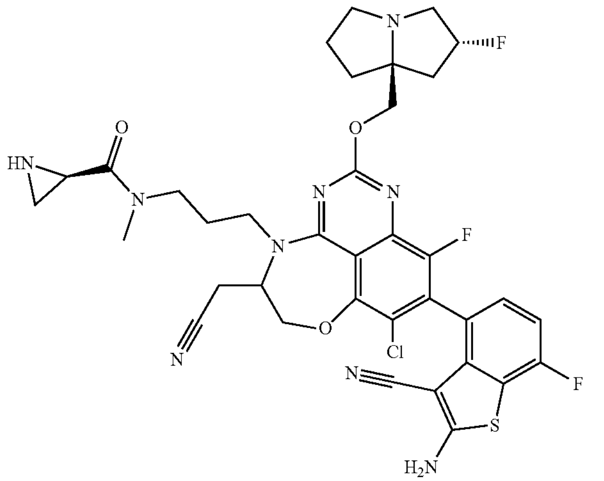 [SMILES: CN(CCCN1c2nc(OC[C@@]34CCCN3C[C@H](F)C4)nc3c(F)c(-c4ccc(F)c5sc(N)c(C#N)c45)c(Cl)c(c23)OCC1CC#N)C(=O)[C@H]1CN1] | (2R)-N-(3-(9-(2-amino-3-cyano-7-fluorobenzo[b]thiophen-4-yl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)-N-methylaziridine-2-carboxamide | 766.1 |
| 710 | 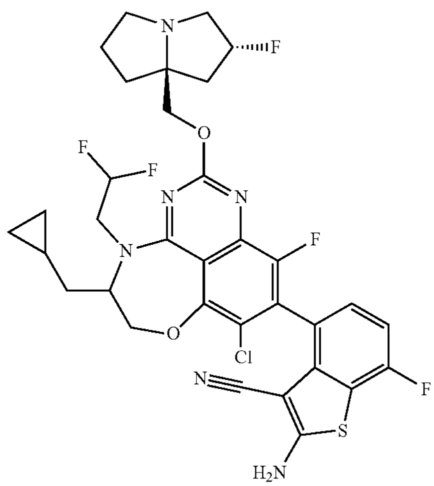 [SMILES: N#Cc1c(N)sc2c(F)ccc(-c3c(Cl)c4c5c(nc(OC[C@@]67CCCN6C[C@H](F)C7)nc5c3F)N(CC(F)F)C(CC3CC3)CO4)c12] | 2-amino-4-(8-chloro-5-(cyclopropylmethyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 705 |
| 711 | 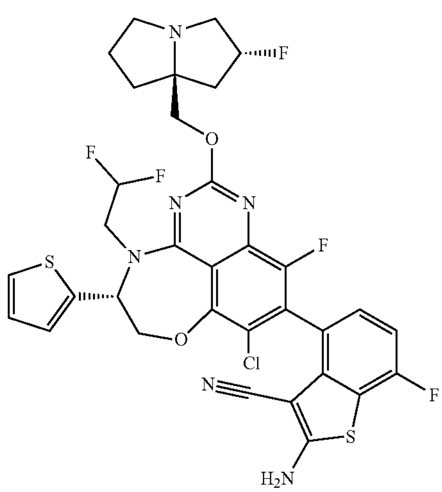 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](c3cccs3)CO4)c12] | 2-amino-4-((R)-8-chloro-4-(2,2-difluoroethyl)-10-fluoro-2-(((2R,7aS)-2-fluorotetrahydro-1H-pyrrolizin-7a(5H)-yl)methoxy)-5-(thiophen-2-yl)-5,6-dihydro-4H-[1,4]oxazepino[5,6,7-de]quinazolin-9-yl)-7-fluorobenzo[b]thiophene-3-carbonitrile | 732.8 |

TABLE 1-continued

| No. | Structure | Chemical Name | [M + H]+ |
|---|---|---|---|
| 712 | 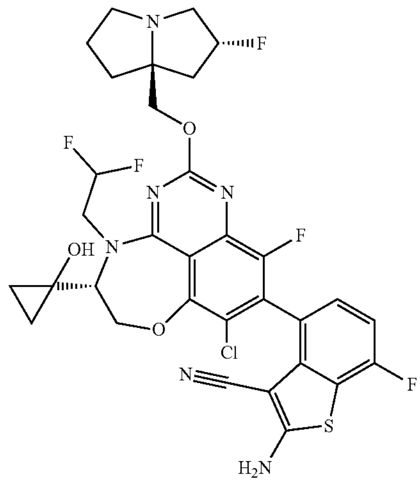 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(O)CC3)CO4)c12] | 2-amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 713 |
| 713 | 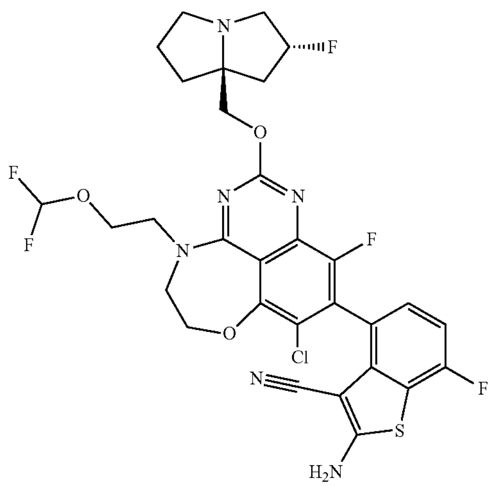 [SMILES: N#Cc1c(N)sc2c(F)ccc(-c3c(Cl)c4c5c(nc(OC[C@@]67CCCN6C[C@H](F)C7)nc5c3F)N(CCOC(F)F)CCO4)c12] | 2-amino-4-(8-chloro-4-(2-(difluoromethoxy)ethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 680.9 |
| 714 | 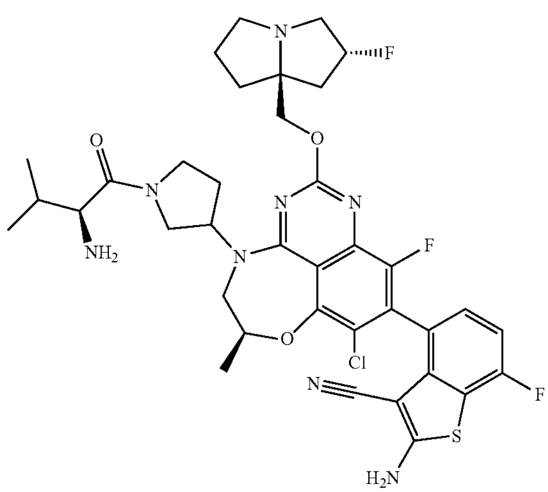 [SMILES: CC(C)[C@H](N)C(=O)N1CCC(N2C[C@H](C)Oc3c(Cl)c(-c4ccc(F)c5sc(N)c(C#N)c45)c(F)c4nc(OC[C@@]56CCCN5C[C@H](F)C6)nc2c34)C1] | 4-((6S)-4-(1-(L-valyl)pyrrolidin-3-yl)-8-chloro-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-2-amino-7-fluorobenzo[b]thiophene-3-carbonitrile | 768.5 |

TABLE 1-continued

| No. | Structure | Chemical Name | [M + H]+ |
|---|---|---|---|
| 715 | 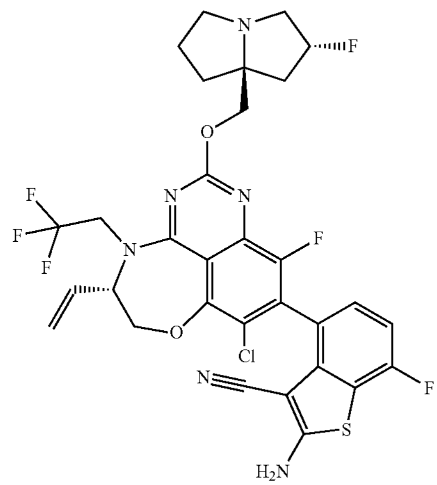 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CC(F)(F)F] | 2-amino-4-((5S)-8-chloro-10-fluoro-2-(((2R,7aS)-2-fluorotetrahydro-1H-pyrrolizin-7a(5H)-yl)methoxy)-4-(2,2,2-trifluoroethyl)-5-vinyl-5,6-dihydro-4H-[1,4]oxazepino[5,6,7-de]quinazolin-9-yl)-7-fluorobenzo[b]thiophene-3-carbonitrile | 694.9 |
| 716 | 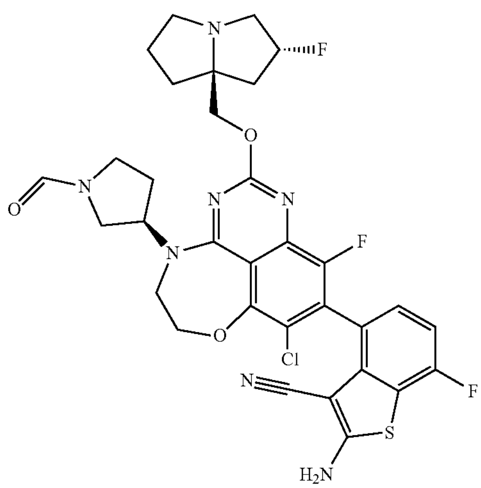 [SMILES: N#Cc1c(N)sc2c(F)ccc(-c3c(Cl)c4c5c(nc(OC[C@@]67CCCN6C[C@H](F)C7)nc5c3F)N([C@@H]3CCN(C=O)C3)CCO4)c12] | 2-amino-4-(8-chloro-10-fluoro-2-(((2R,7aS)-2-fluorotetrahydro-1H-pyrrolizin-7a(5H)-yl)methoxy)-4-((R)-1-formylpyrrolidin-3-yl)-5,6-dihydro-4H-[1,4]oxazepino[5,6,7-de]quinazolin-9-yl)-7-fluorobenzo[b]thiophene-3-carbonitrile | 684.3 |
| 717 | 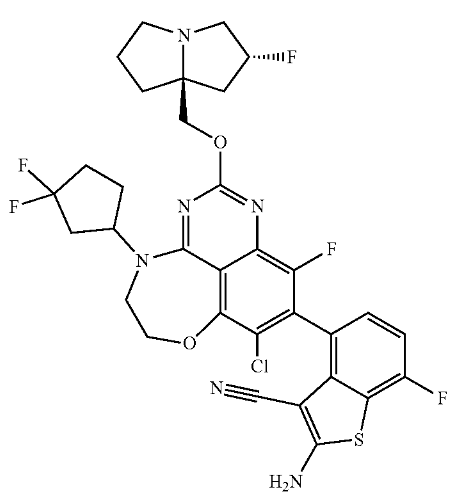 [SMILES: N#Cc1c(N)sc2c(F)ccc(-c3c(Cl)c4c5c(nc(OC[C@@]67CCCN6C[C@H](F)C7)nc5c3F)N(C3CCC(F)(F)C3)CCO4)c12] | 2-amino-4-(8-chloro-4-(3,3-difluorocyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 691 |

TABLE 1-continued

| No. | Structure | Chemical Name | [M + H]+ |
|---|---|---|---|
| 718 | 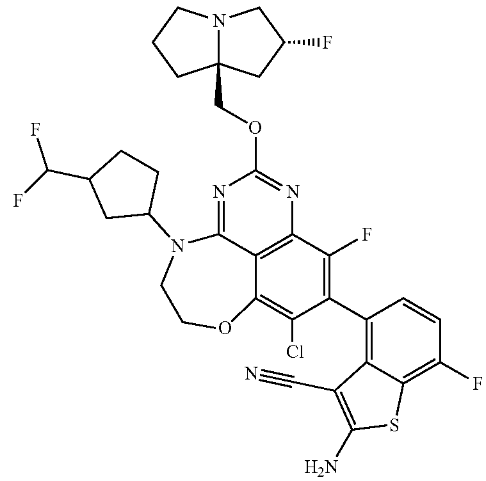 [SMILES: N#Cc1c(N)sc2c(F)ccc(-c3c(Cl)c4c5c(nc(OC[C@@]67CCCN6C[C@H](F)C7)nc5c3F)N(C3CCC(C(F)F)C3)CCO4)c12] | 2-amino-4-(8-chloro-4-(3-(difluoromethyl)cyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 704.8 |
| 719 | 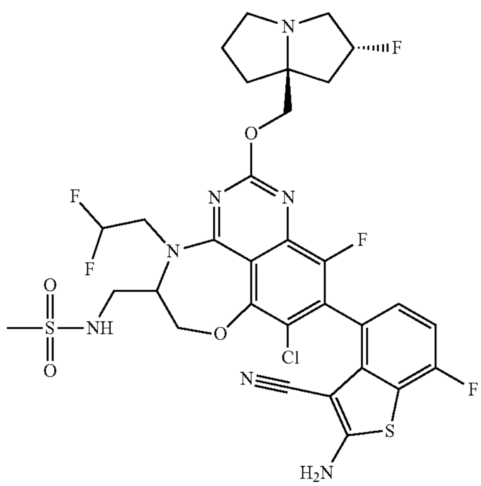 [SMILES: CS(=O)(=O)NCC1COc2c(Cl)c(-c3ccc(F)c4sc(N)c(C#N)c34)c(F)c3nc(OC[C@@]45CCCN4C[C@H](F)C5)nc(c23)N1CC(F)F] | N-((9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)methanesulfonamide | 758.3 |
| 720 | 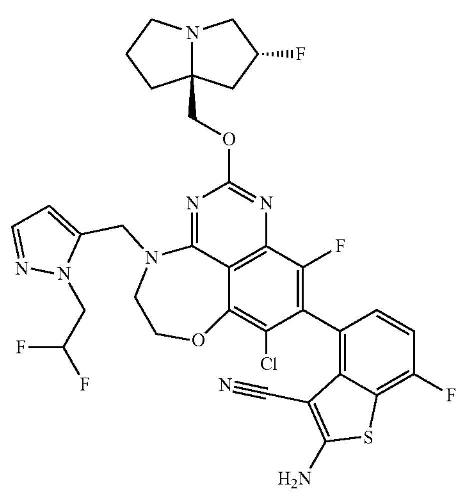 [SMILES: N#Cc1c(N)sc2c(F)ccc(-c3c(Cl)c4c5c(nc(OC[C@@]67CCCN6C[C@H](F)C7)nc5c3F)N(Cc3ccnn3CC(F)F)CCO4)c12] | 2-amino-4-(8-chloro-4-((1-(2,2-difluoroethyl)-1H-pyrazol-5-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 731.3 |

TABLE 1-continued

| No. | Structure | Chemical Name | [M + H]⁺ |
|-----|-----------|---------------|----------|
| 721 | 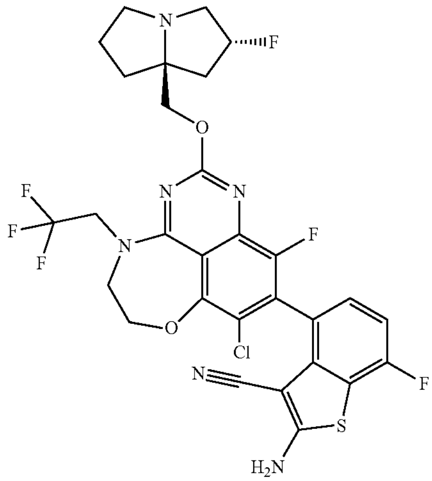 [SMILES: N#Cc1c(N)sc2c(F)ccc(-c3c(Cl)c4c5c(nc(OC[C@@]67CCCN6C[C@H](F)C7)nc5c3F)N(CC(F)(F)F)CCO4)c12] | 2-amino-4-(8-chloro-10-fluoro-2-(((2R,7aS)-2-fluorotetrahydro-1H-pyrrolizin-7a(5H)-yl)methoxy)-4-(2,2,2-trifluoroethyl)-5,6-dihydro-4H-[1,4]oxazepino[5,6,7-de]quinazolin-9-yl)-7-fluorobenzo[b]thiophene-3-carbonitrile | 669.1 |
| 722 | 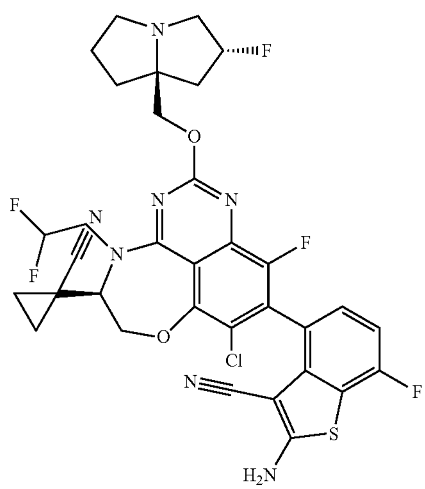 [SMILES: N#Cc1c(N)sc2c(F)ccc(-c3c(Cl)c4c5c(nc(OC[C@@]67CCCN6C[C@H](F)C7)nc5c3F)N(CC(F)F)[C@H](C3(C#N)CC3)CO4)c12] | 2-amino-4-((R)-8-chloro-5-(1-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |
| 723 | 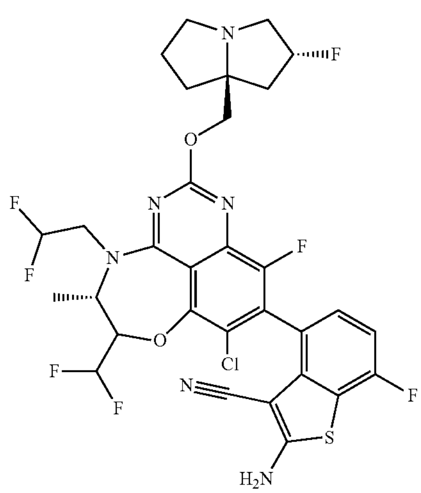 [SMILES: C[C@H]1C(C(F)F)Oc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-6-(difluoromethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 714.9 |

TABLE 1-continued

| No. | Structure | Chemical Name | [M + H]⁺ |
|---|---|---|---|
| 724 | 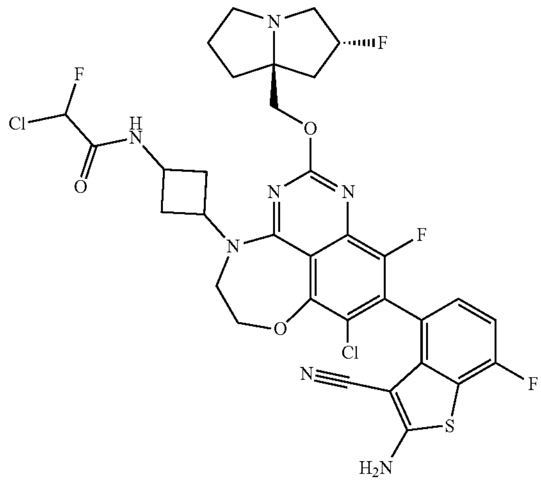 [SMILES: N#Cc1c(N)sc2c(F)ccc(-c3c(Cl)c4c5c(nc(OC[C@@]67CCCN6C[C@H](F)C7)nc5c3F)N(C3CC(NC(=O)C(F)Cl)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)-2-chloro-2-fluoroacetamide | 750.3 |
| 725 | 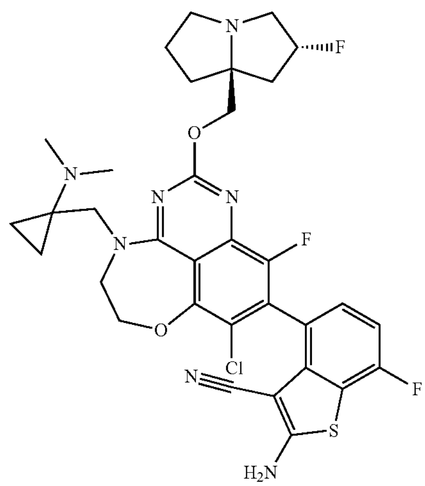 [SMILES: CN(C)C1(CN2CCOc3c(Cl)c(-c4ccc(F)c5sc(N)c(C#N)c45)c(F)c4nc(OC[C@@]56CCCN5C[C@H](F)C6)nc2c34)CC1] | 2-amino-4-(8-chloro-4-((1-(dimethylamino)cyclopropyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 684.3 |
| 726 | 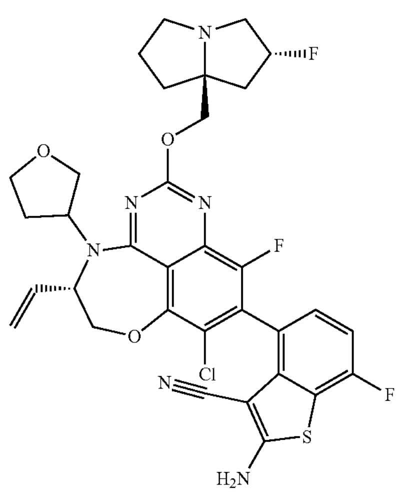 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-7-fluorobenzo[b]thiophene-3-carbonitrile | 683 |

TABLE 1-continued

| No. | Structure | Chemical Name | [M + H]+ |
|---|---|---|---|
| 727 | 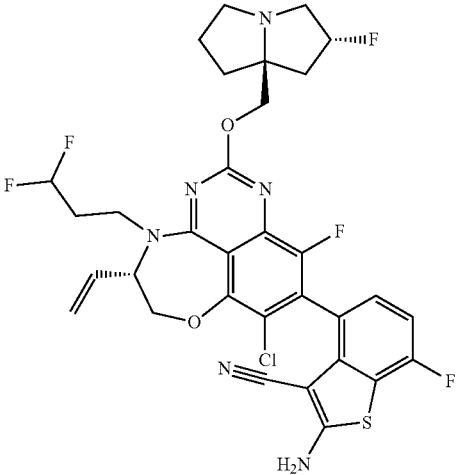 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 691.1 |
| 728 | 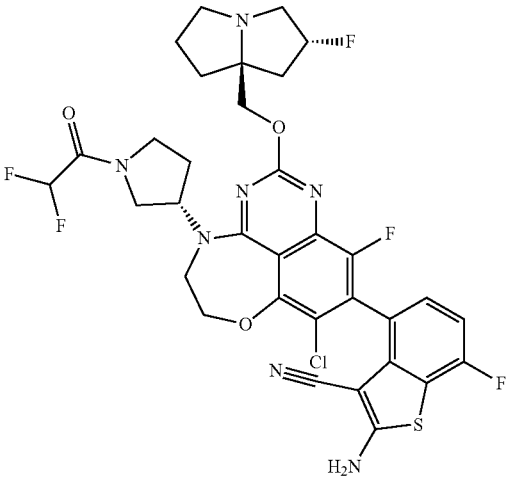 [SMILES: N#Cc1c(N)sc2c(F)ccc(-c3c(Cl)c4c5c(nc(OC[C@@]67CCCN6C[C@H](F)C7)nc5c3F)N([C@H]3CCN(C(=O)C(F)F)C3)CCO4)c12] | 2-amino-4-(8-chloro-4-((S)-1-(2,2-difluoroacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 734.2 |
| 729 | 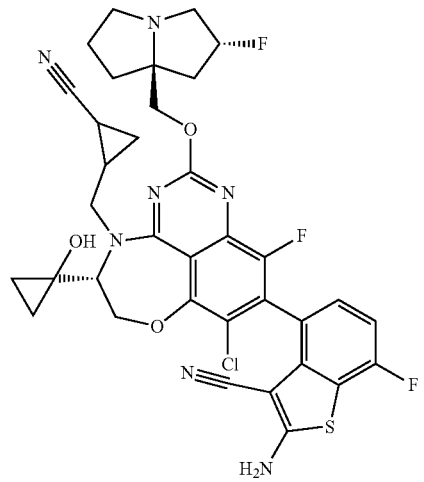 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |

TABLE 1-continued

| No. | Structure | Chemical Name | [M + H]⁺ |
|---|---|---|---|
| 730 | 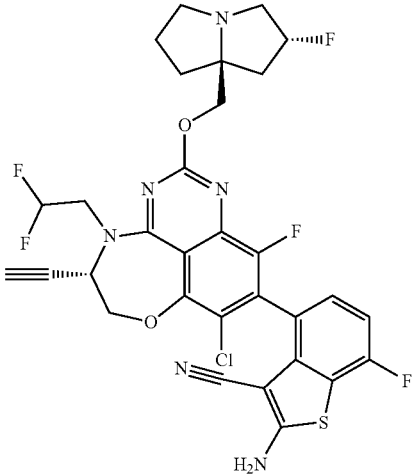 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 675 |
| 731 | 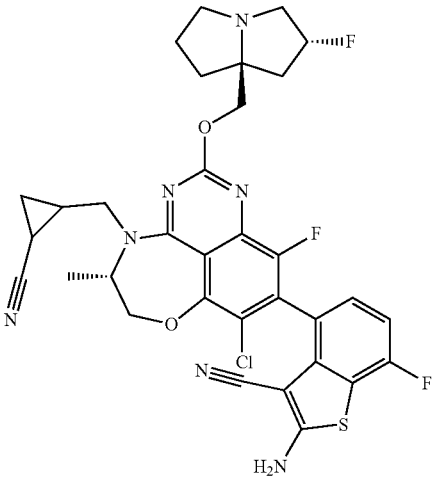 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CC1CC1C#N] | 2-amino-4-((5S)-8-chloro-4-((2-cyanocyclopropyl)methyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 680 |
| 732 | 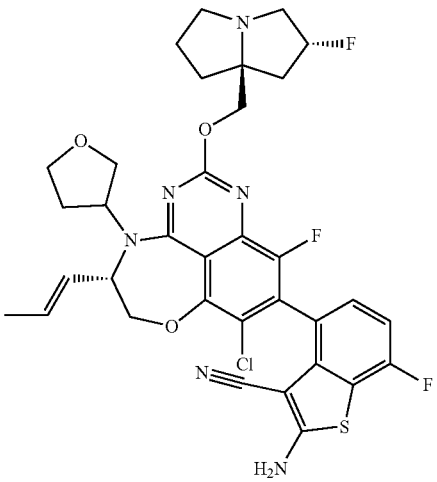 [SMILES: C/C=C/[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-5-((E)-prop-1-en-1-yl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 697.3 |

TABLE 1-continued

| No. | Structure | Chemical Name | [M + H]+ |
|---|---|---|---|
| 733 | 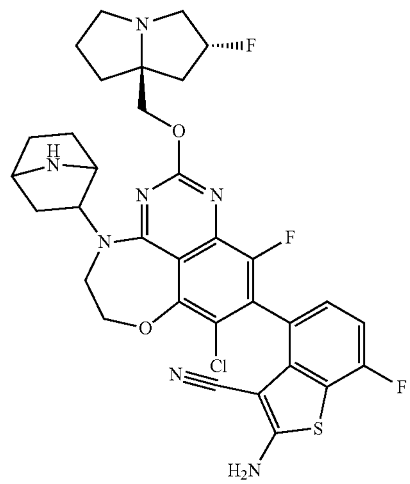 [SMILES: N#Cc1c(N)sc2c(F)ccc(-c3c(Cl)c4c5c(nc(OC[C@@]67CCCN6C[C@H](F)C7)nc5c3F)N(C3CC5CCC3N5)CCO4)c12] | 4-(4-(7-azabicyclo[2.2.1]heptan-2-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 683.3 |
| 734 | 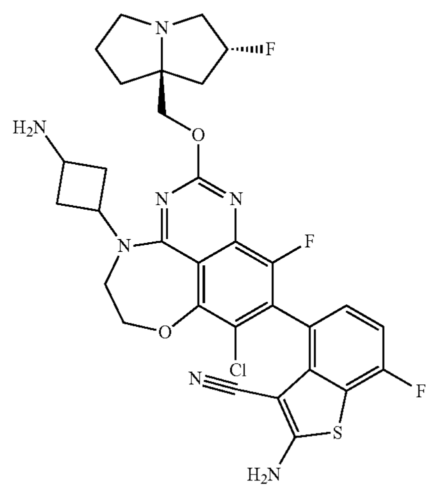 [SMILES: N#Cc1c(N)sc2c(F)ccc(-c3c(Cl)c4c5c(nc(OC[C@@]67CCCN6C[C@H](F)C7)nc5c3F)N(C3CC(N)C3)CCO4)c12] | 2-amino-4-(4-(3-aminocyclobutyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 656.5 |
| 735 | 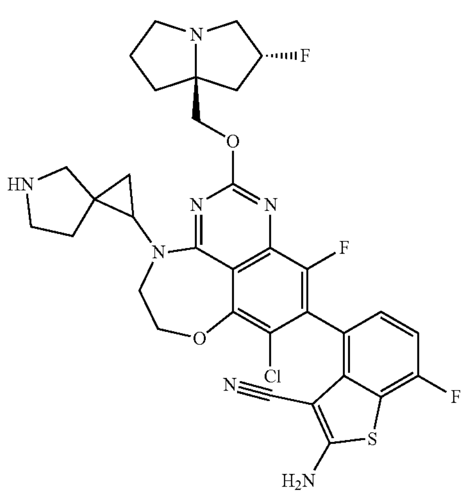 [SMILES: N#Cc1c(N)sc2c(F)ccc(-c3c(Cl)c4c5c(nc(OC[C@@]67CCCN6C[C@H](F)C7)nc5c3F)N(C3CC35CCNC5)CCO4)c12] | 2-amino-4-(8-chloro-10-fluoro-2-(((2R,7aS)-2-fluorotetrahydro-1H-pyrrolizin-7a(5H)-yl)methoxy)-4-(5-azaspiro[2.4]heptan-1-yl)-5,6-dihydro-4H-[1,4]oxazepino[5,6,7-de]quinazolin-9-yl)-7-fluorobenzo[b]thiophene-3-carbonitrile | 682.2 |

TABLE 1-continued

| No. | Structure | Chemical Name | [M + H]⁺ |
|---|---|---|---|
| 736 | 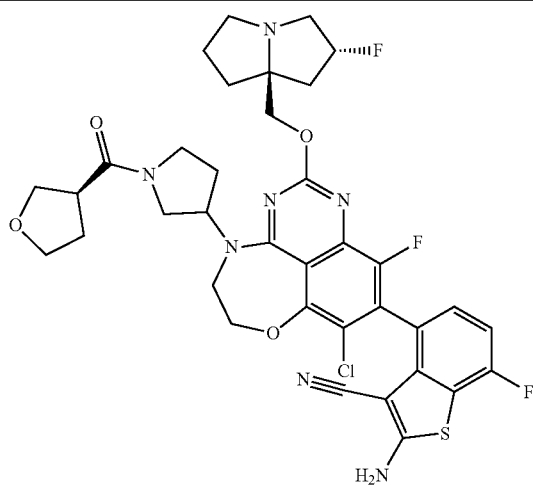 | 2-amino-4-(8-chloro-10-fluoro-2-(((2R,7aS)-2-fluorotetrahydro-1H-pyrrolizin-7a(5H)-yl)methoxy)-4-(1-((S)-tetrahydrofuran-3-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 754.3 |
| 737 | 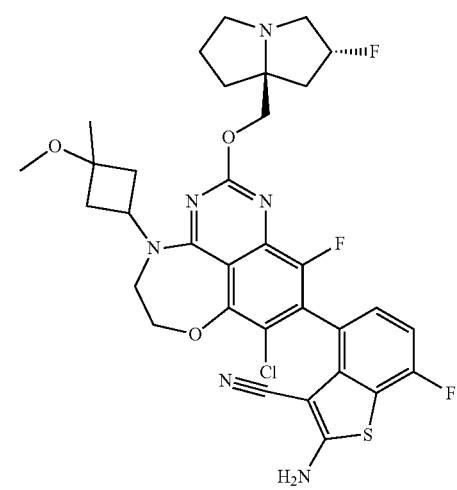 [SMILES: COC1(C)CC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(3-methoxy-3-methylcyclobutyl)-5,6-dihydro-4H-[1,4]oxazepino[5,6,7-de]quinazolin-9-yl)-7-fluorobenzo[b]thiophene-3-carbonitrile | 685.3 |
| 738 | 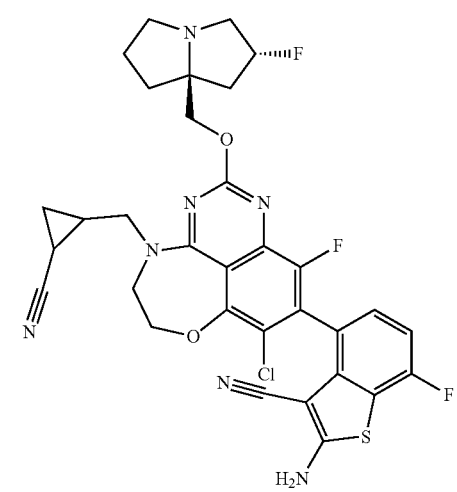 [SMILES: N#Cc1c(N)sc2c(F)ccc(-c3c(Cl)c4c5c(nc(OC[C@@]67CCCN6C[C@H](F)C7)nc5c3F)N(CC3CC3C#N)CCO4)c12] | 2-amino-4-(8-chloro-4-((2-cyanocyclopropyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 666.3 |

TABLE 1-continued

| No. | Structure | Chemical Name | [M + H]+ |
|---|---|---|---|
| 739 | 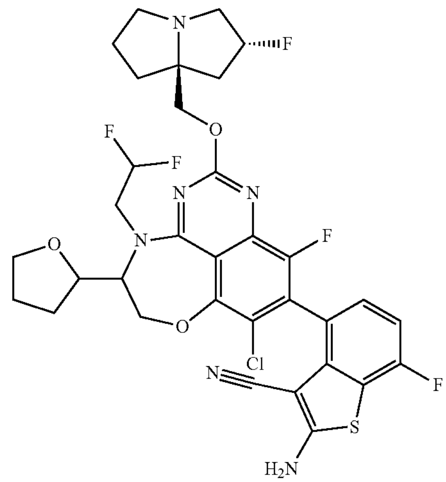 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCO3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile | 720.9 |
| 740 | 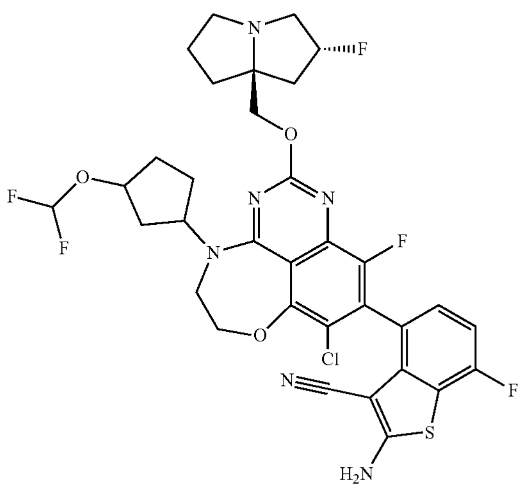 [SMILES: N#Cc1c(N)sc2c(F)ccc(-c3c(Cl)c4c5c(nc(OC[C@@]67CCCN6C[C@H](F)C7)nc5c3F)N(C3CCC(OC(F)F)C3)CCO4)c12] | 2-amino-4-(8-chloro-4-(3-(difluoromethoxy)cyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 721.3 |
| 741 | 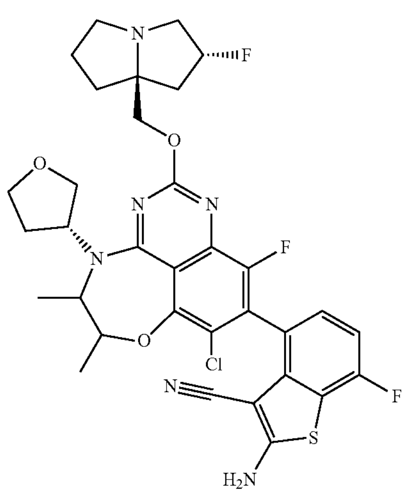 [SMILES: CC1Oc2c(Cl)c(-c3ccc(F)c4sc(N)c(C#N)c34)c(F)c3nc(OC[C@@]45CCCN4C[C@H](F)C5)nc(c23)N([C@@H]2CCOC2)C1C] | 2-amino-4-(8-chloro-10-fluoro-2-(((2R,7aS)-2-fluorotetrahydro-1H-pyrrolizin-7a(5H)-yl)methoxy)-5,6-dimethyl-4-((R)-tetrahydrofuran-3-yl)-5,6-dihydro-4H-[1,4]oxazepino[5,6,7-de]quinazolin-9-yl)-7-fluorobenzo[b]thiophene-3-carbonitrile | 684.9 |

TABLE 1-continued

| No. | Structure | Chemical Name | [M + H]+ |
|---|---|---|---|
| 742 | 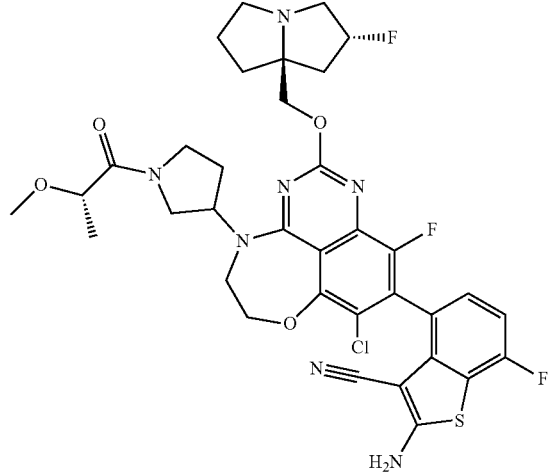 [SMILES: CO[C@@H](C)C(=O)N1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(1-((S)-2-methoxypropanoyl)pyrrolidin-3-yl)-5,6-dihydro-4H-[1,4]oxazepino[5,6,7-de]quinazolin-9-yl)-7-fluorobenzo[b]thiophene-3-carbonitrile | 742.5 |
| 743 | 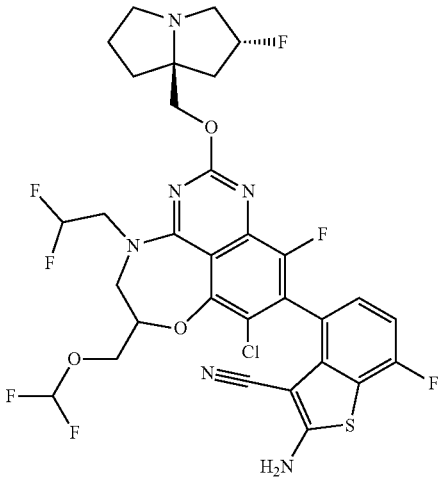 [SMILES: N#Cc1c(N)sc2c(F)ccc(-c3c(Cl)c4c5c(nc(OC[C@@]67CCCN6C[C@H](F)C7)nc5c3F)N(CC(F)F)CC(COC(F)F)O4)c12] | 2-amino-4-(8-chloro-4-(2,2-difluoroethyl)-6-((difluoromethoxy)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 730.9 |
| 744 | 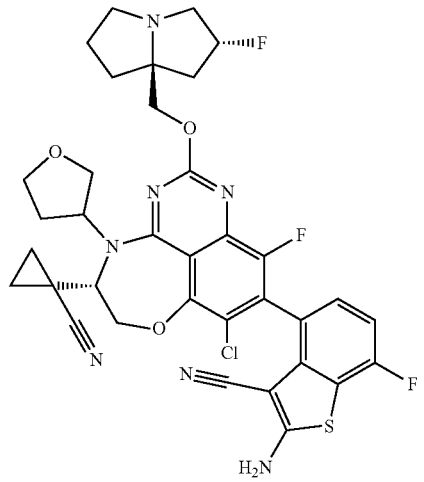 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(C#N)CC3)CO4)c12] | 2-amino-4-((5S)-8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 721.9 |

TABLE 1-continued

| No. | Structure | Chemical Name | [M + H]⁺ |
|---|---|---|---|
| 745 | 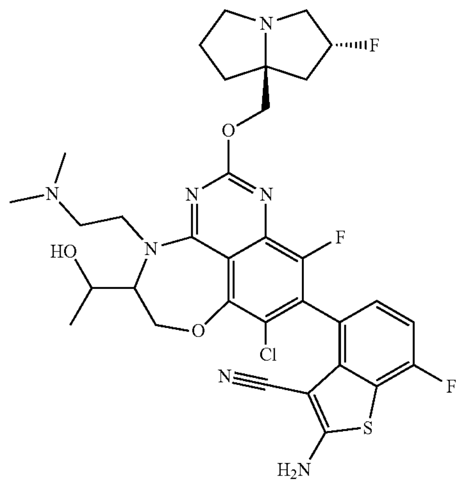 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CCN(C)C] | 2-amino-4-(8-chloro-4-(2-(dimethylamino)ethyl)-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile | 702.2 |
| 746 | 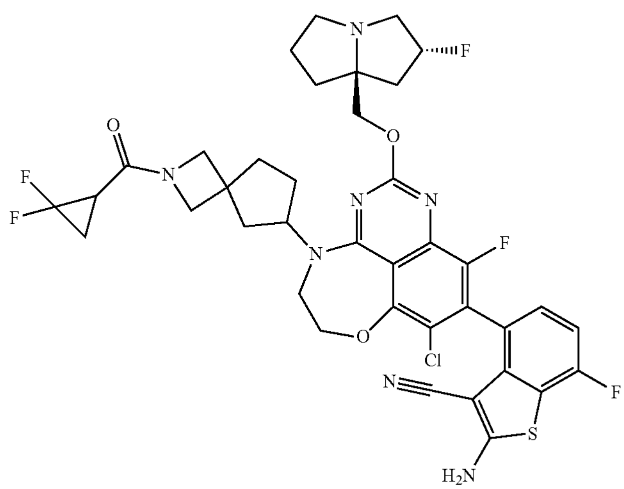 [SMILES: N#Cc1c(N)sc2c(F)ccc(-c3c(Cl)c4c5c(nc(OC[C@@]67CCCN6C[C@H](F)C7)nc5c3F)N(C3CCC5(C3)CN(C(=O)C3CC3(F)F)C5)CCO4)c12] | 2-amino-4-(8-chloro-4-(2-(2,2-difluorocyclopropane-1-carbonyl)-2-azaspiro[3.4]octan-6-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 800.4 |
| 747 | 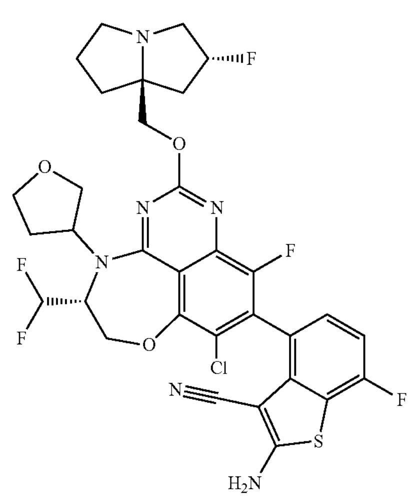 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C(F)F)CO4)c12] | 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 706.9 |

TABLE 1-continued

| No. | Structure | Chemical Name | [M + H]+ |
|---|---|---|---|
| 748 | 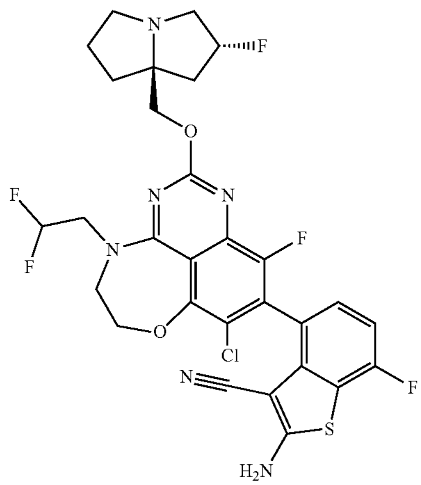 [SMILES: N#Cc1c(N)sc2c(F)ccc(-c3c(Cl)c4c5c(nc(OC[C@@]67CCCN6C[C@H](F)C7)nc5c3F)N(CC(F)F)CCO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 651.1 |
| 749 | 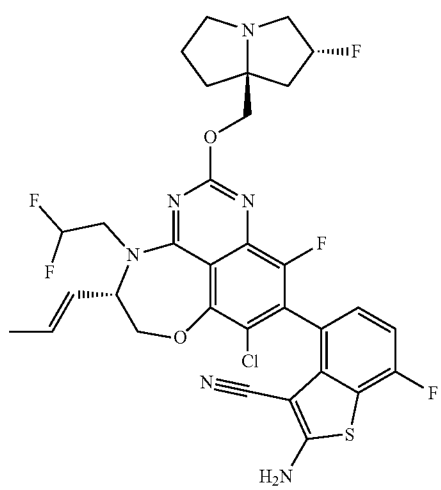 [SMILES: C/C=C/[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((E)-prop-1-en-1-yl)-5,6-dihydro-4H-[1,4]oxazepino[5,6,7-de]quinazolin-9-yl)-7-fluorobenzo[b]thiophene-3-carbonitrile | 690.9 |
| 750 | 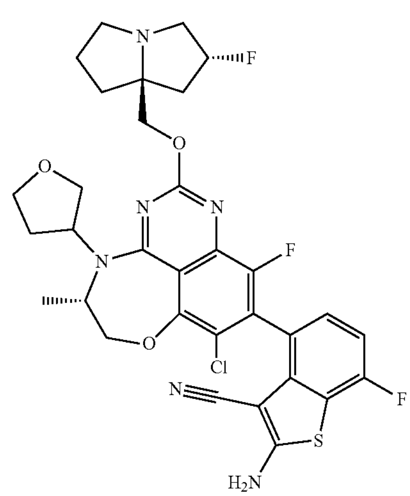 | 2-amino-4-((5S)-8-chloro-10-fluoro-2-(((2R,7aS)-2-fluorotetrahydro-1H-pyrrolizin-7a(5H)-yl)methoxy)-5-methyl-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 671.3 |

TABLE 1-continued

| No. | Structure | Chemical Name | [M + H]+ |
|---|---|---|---|
| 751 | 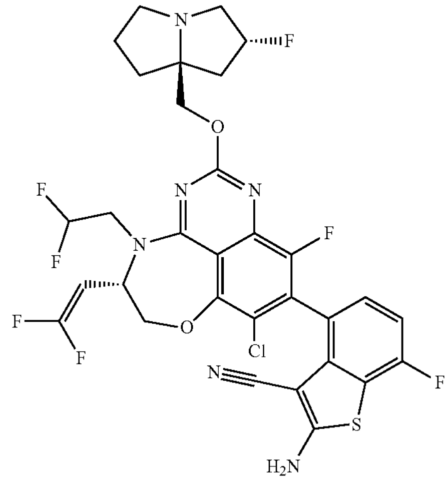 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C=C(F)F)CO4)c12] | 2-amino-4-((S)-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 712.9 |
| 752 | 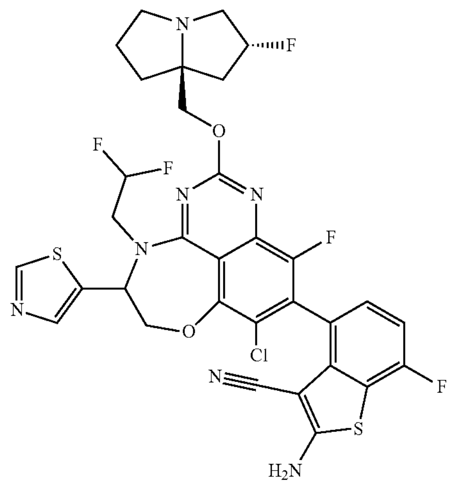 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiazol-5-yl)-5,6-dihydro-4H-[1,4]oxazepino[5,6,7-de]quinazolin-9-yl)-7-fluorobenzo[b]thiophene-3-carbonitrile | 734.2 |
| 753 | 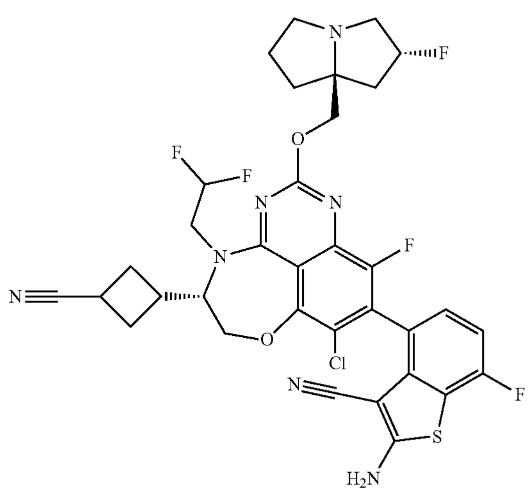 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC(C#N)C3)CO4)c12] | 2-amino-4-((S)-8-chloro-5-(3-cyanocyclobutyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 729.9 |

TABLE 1-continued

| No. | Structure | Chemical Name | [M + H]+ |
|---|---|---|---|
| 754 | 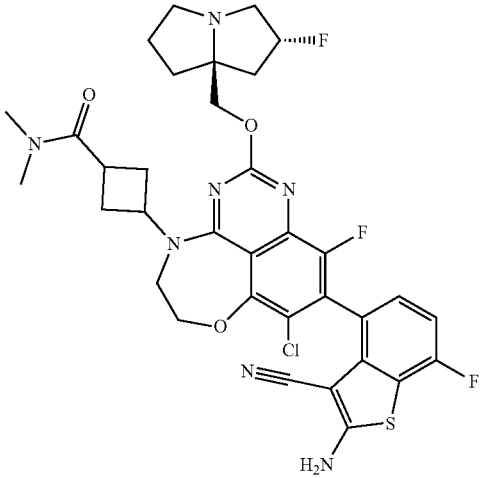 [SMILES: CN(C)C(=O)C1CC(N2CCOc3c(Cl)c(-c4ccc(F)c5sc(N)c(C#N)c45)c(F)c4nc(OC[C@@]56CCCN5C[C@H](F)C6)nc2c34)C1] | 3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N,N-dimethylcyclobutane-1-carboxamide | 711.8 |
| 755 | 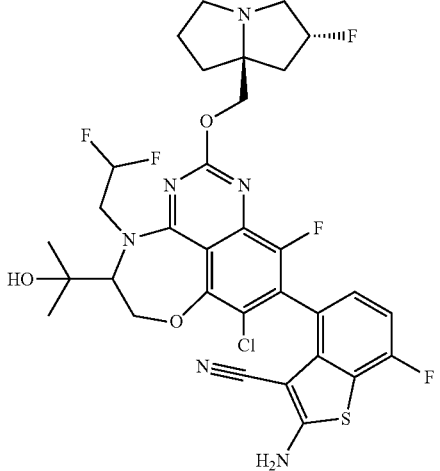 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropan-2-yl)-5,6-dihydro-4H-[1,4]oxazepino[5,6,7-de]quinazolin-9-yl)-7-fluorobenzo[b]thiophene-3-carbonitrile | 709.3 |
| 756 | 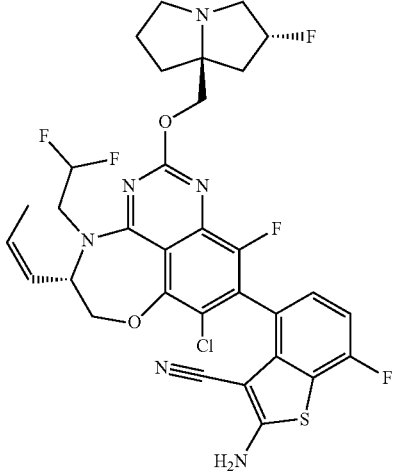 [SMILES: C/C=C\[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazolin-9-yl)-7-fluorobenzo[b]thiophene-3-carbonitrile | 690.9 |

TABLE 1-continued

| No. | Structure | Chemical Name | [M + H]+ |
|---|---|---|---|
| 757 | 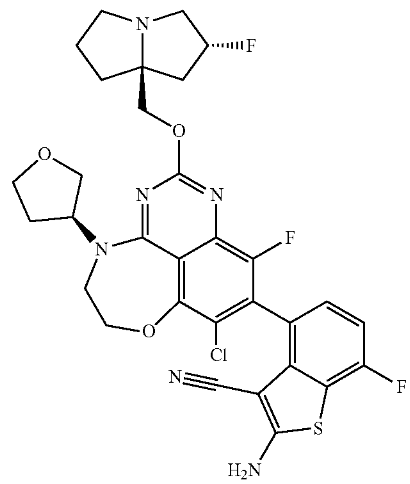 [SMILES: N#Cc1c(N)sc2c(F)ccc(-c3c(Cl)c4c5c(nc(OC[C@@]67CCCN6C[C@H](F)C7)nc5c3F)N([C@H]3CCOC3)CCO4)c12] | 2-amino-4-(8-chloro-10-fluoro-2-(((2R,7aS)-2-fluorotetrahydro-1H-pyrrolizin-7a(5H)-yl)methoxy)-4-(1-(oxetane-3-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 740.3 |
| 758 | 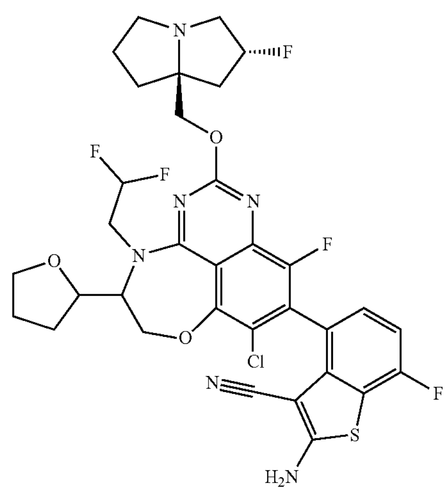 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCO3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile | 720.9 |
| 759 | 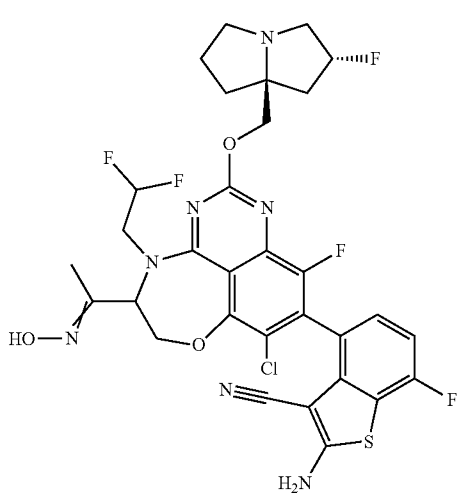 [SMILES: CC(=NO)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-(hydroxyimino)ethyl)-5,6-dihydro-4H-[1,4]oxazepino[5,6,7-de]quinazolin-9-yl)-7-fluorobenzo[b]thiophene-3-carbonitrile | 707.9 |

TABLE 1-continued

| No. | Structure | Chemical Name | [M + H]+ |
|---|---|---|---|
| 760 | 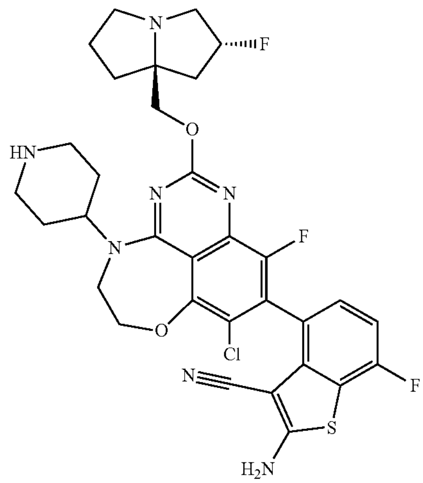 [SMILES: N#Cc1c(N)sc2c(F)ccc(-c3c(Cl)c4c5c(nc(OC[C@@]67CCCN6C[C@H](F)C7)nc5c3F)N(C3CCNCC3)CCO4)c12] | 2-amino-4-(8-chloro-10-fluoro-2-(((2R,7aS)-2-fluorotetrahydro-1H-pyrrolizin-7a(5H)-yl)methoxy)-4-(piperidin-4-yl)-5,6-dihydro-4H-[1,4]oxazepino[5,6,7-de]quinazolin-9-yl)-7-fluorobenzo[b]thiophene-3-carbonitrile | 670.2 |
| 761 | 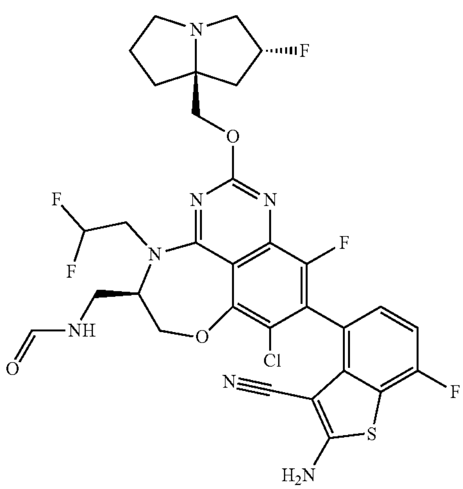 [SMILES: N#Cc1c(N)sc2c(F)ccc(-c3c(Cl)c4c5c(nc(OC[C@@]67CCCN6C[C@H](F)C7)nc5c3F)N(CC(F)F)[C@H](CNC=O)CO4)c12] | N-(((5R)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)formamide | 708.2 |
| 762 | 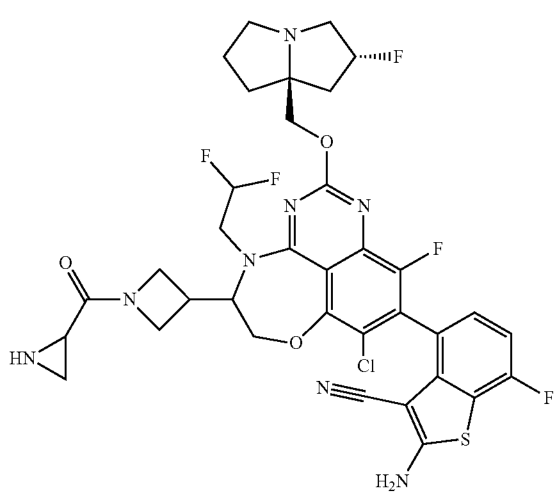 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CN(C(=O)C5CN5)C3)CO4)c12] | 2-amino-4-(5-(1-(aziridine-2-carbonyl)azetidin-3-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 774.9 |

| No. | Structure | Chemical Name | [M + H]+ |
|---|---|---|---|
| 763 | 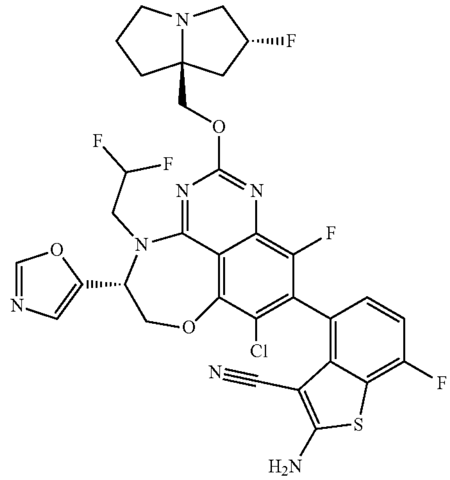 | 2-amino-4-((R)-8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazolin-9-yl)-7-fluorobenzo[b]thiophene-3-carbonitrile | 717.8 |
| 764 | 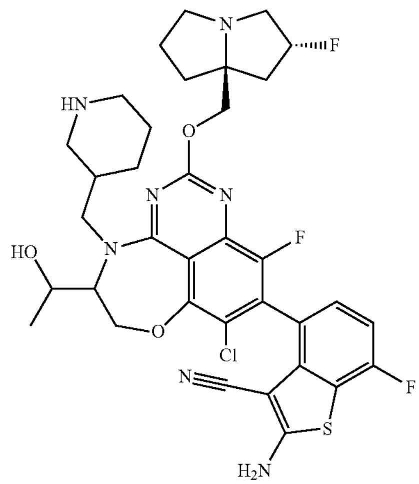 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC1CCCNC1] | 2-amino-4-(8-chloro-10-fluoro-2-(((2R,7aS)-2-fluorotetrahydro-1H-pyrrolizin-7a(5H)-yl)methoxy)-5-(1-hydroxyethyl)-4-(piperidin-3-ylmethyl)-5,6-dihydro-4H-[1,4]oxazepino[5,6,7-de]quinazolin-9-yl)-7-fluorobenzo[b]thiophene-3-carbonitrile | 728.2 |
| 765 | 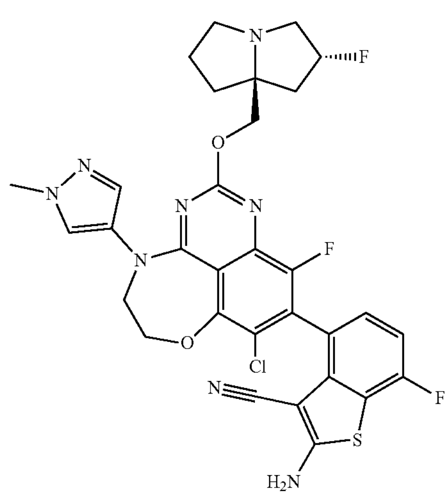 [SMILES: Cn1cc(N2CCOc3c(Cl)c(-c4ccc(F)c5sc(N)c(C#N)c45)c(F)c4nc(OC[C@@]56CCCN5C[C@H](F)C6)nc2c34)cn1] | 2-amino-4-(8-chloro-10-fluoro-2-(((2R,7aS)-2-fluorotetrahydro-1H-pyrrolizin-7a(5H)-yl)methoxy)-4-(1-methyl-1H-pyrazol-4-yl)-5,6-dihydro-4H-[1,4]oxazepino[5,6,7-de]quinazolin-9-yl)-7-fluorobenzo[b]thiophene-3-carbonitrile | 667.3 |

TABLE 1-continued

| No. | Structure | Chemical Name | [M + H]+ |
|---|---|---|---|
| 766 | 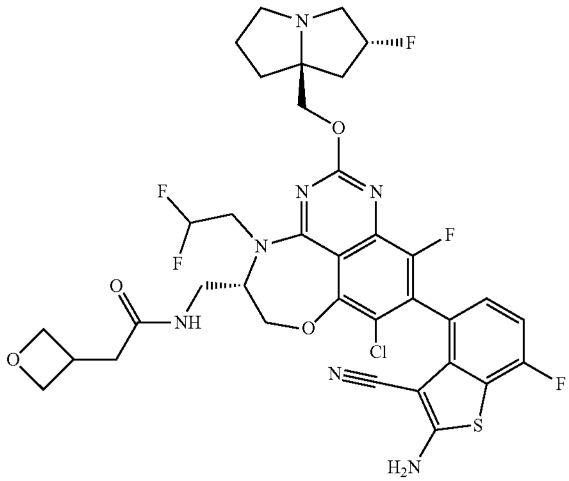 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](CNC(=O)CC3COC3)CO4)c12] | N-(((5S)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)-2-(oxetan-3-yl)acetamide | 778.3 |
| 767 | 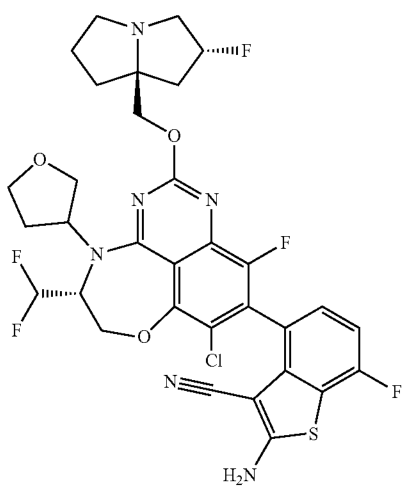 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C(F)F)CO4)c12] | 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 706.9 |
| 768 | 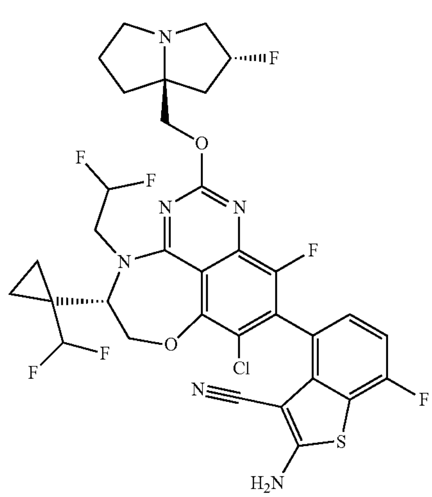 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(C(F)F)CC3)CO4)c12] | 2-amino-4-((S)-8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 741.1 |

TABLE 1-continued

| No. | Structure | Chemical Name | [M + H]+ |
|---|---|---|---|
| 769 | 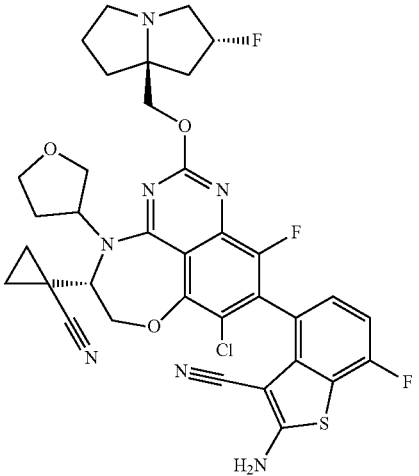 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(C#N)CC3)CO4)c12] | 2-amino-4-((5S)-8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 721.9 |
| 770 | 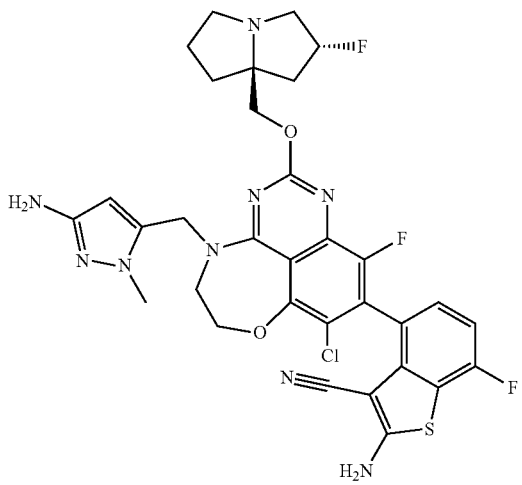 [SMILES: Cn1nc(N)cc1CN1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((3-amino-1-methyl-1H-pyrazol-5-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 696.3 |
| 771 | 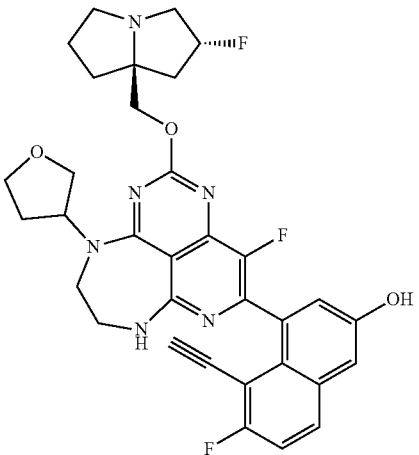 [SMILES: C#Cc1c(F)ccc2cc(O)cc(-c3nc4c5c(nc(OC[C@@]67CCCN6C[C@H](F)C7)nc5c3F)N(C3CCOC3)CCN4)c12] | 5-ethynyl-6-fluoro-4-(4-fluoro-2-(((2R,7aS)-2-fluorotetrahydro-1H-pyrrolizin-7a(5H)-yl)methoxy)-10-(tetrahydrofuran-3-yl)-7,8,9,10-tetrahydro-1,3,6,7,10-pentaazacyclohepta[de]naphthalen-5-yl)naphthalen-2-ol | 616.8 |

TABLE 1-continued

| No. | Structure | Chemical Name | [M + H]⁺ |
|---|---|---|---|
| 772 | 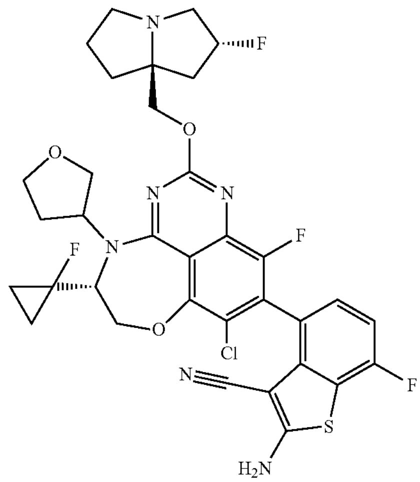 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(F)CC3)CO4)c12] | 2-amino-4-((5R)-8-chloro-10-fluoro-5-(1-fluorocyclopropyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 715.4 |
| 773 | 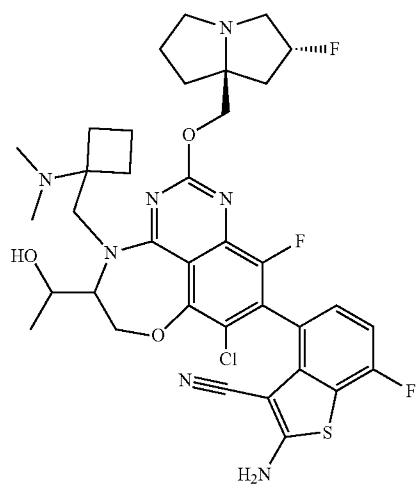 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC1(N(C)C)CCC1] | 2-amino-4-(8-chloro-4-((1-(dimethylamino)cyclobutyl)methyl)-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile | 742.1 |
| 774 | 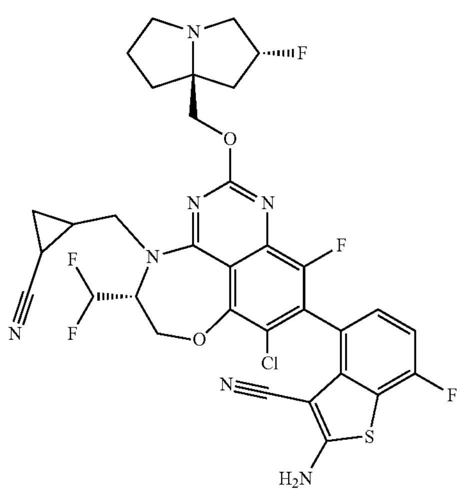 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716.4 |

TABLE 1-continued

| No. | Structure | Chemical Name | [M + H]⁺ |
|---|---|---|---|
| 775 | 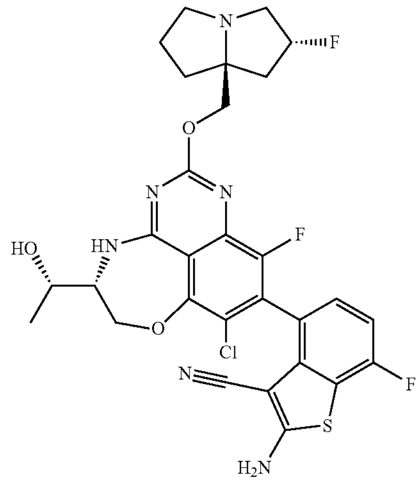 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1] | 2-amino-4-((5R)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 630.9 |
| 776 | 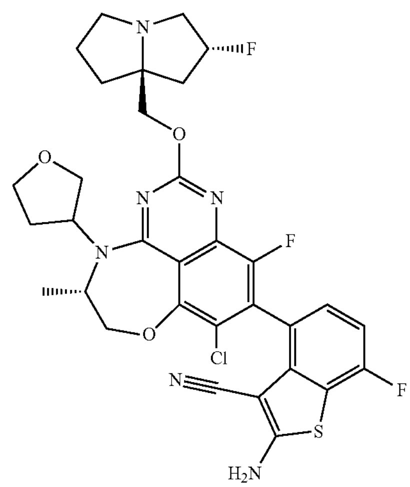 | 2-amino-4-((5S)-8-chloro-10-fluoro-2-(((2R,7aS)-2-fluorotetrahydro-1H-pyrrolizin-7a(5H)-yl)methoxy)-5-methyl-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 671.3 |
| 777 | 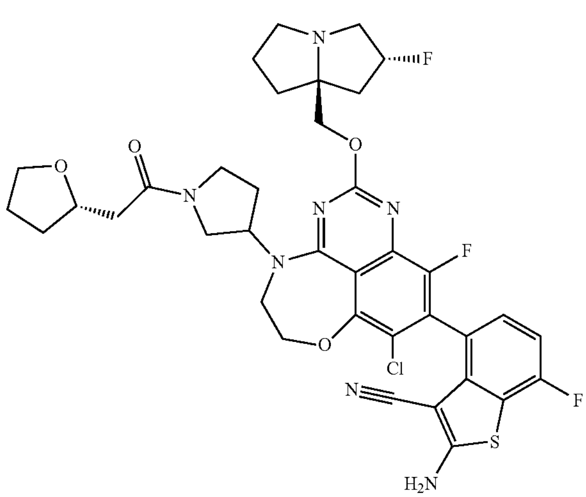 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C[C@@H]5CCCO5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-(2-((S)-tetrahydrofuran-2-yl)acetyl)pyrrolidin-3-yl)-5,6-dihydro-4H-[1,4]oxazepino[5,6,7-de]quinazolin-9-yl)-7-fluorobenzo[b]thiophene-3-carbonitrile | 768.4 |

TABLE 1-continued

| No. | Structure | Chemical Name | [M + H]⁺ |
|---|---|---|---|
| 778 | 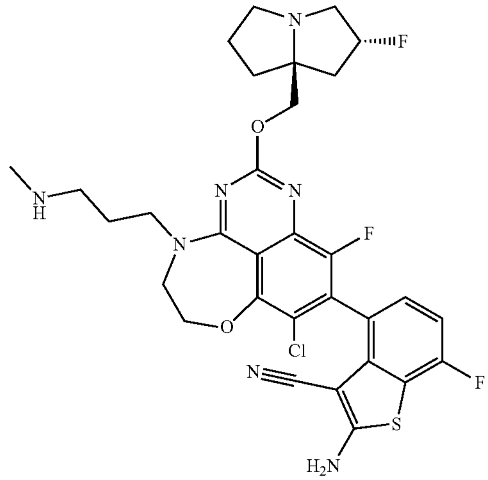 [SMILES: CNCCCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(3-(methylamino)propyl)-5,6-dihydro-4H-[1,4]oxazepino[5,6,7-de]quinazolin-9-yl)-7-fluorobenzo[b]thiophene-3-carbonitrile | 658.2 |
| 779 | 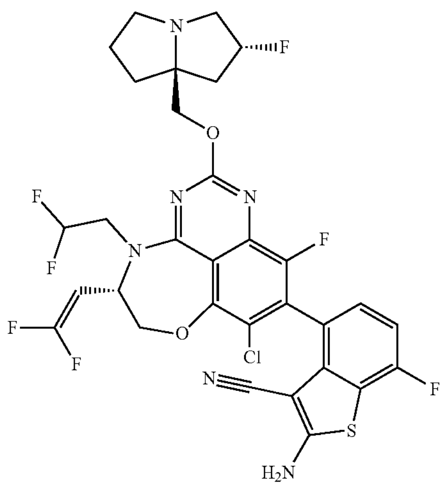 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C=C(F)F)CO4)c12] | 2-amino-4-((S)-8-chloro-4-(2,2-difluoroethyl)-5-(2,2-difluorovinyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 712.9 |
| 780 | 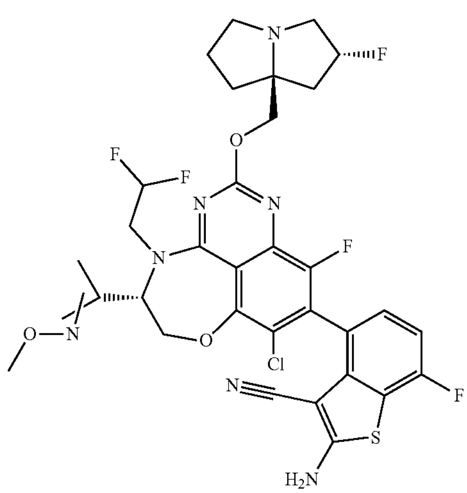 | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-(1-(methoxyimino)ethyl)-5,6-dihydro-4H-[1,4]oxazepino[5,6,7-de]quinazolin-9-yl)-7-fluorobenzo[b]thiophene-3-carbonitrile | 721.9 |

TABLE 1-continued

| No. | Structure | Chemical Name | [M + H]+ |
|---|---|---|---|
| 781 | 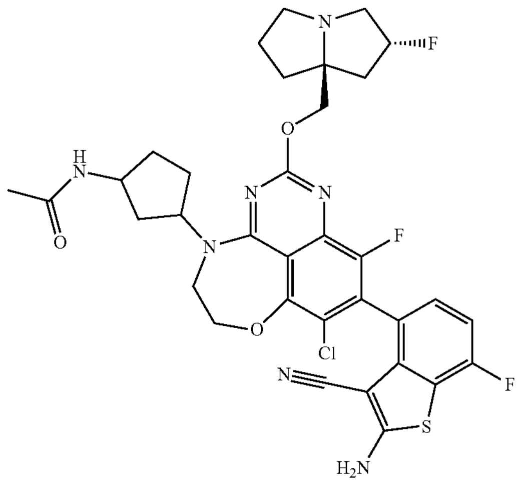 [SMILES: CC(=O)NC1CCC(N2CCOc3c(Cl)c(-c4ccc(F)c5sc(N)c(C#N)c45)c(F)c4nc(OC[C@@]56CCCN5C[C@H](F)C6)nc2c34)C1] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclopentyl)acetamide | 712.3 |
| 782 | 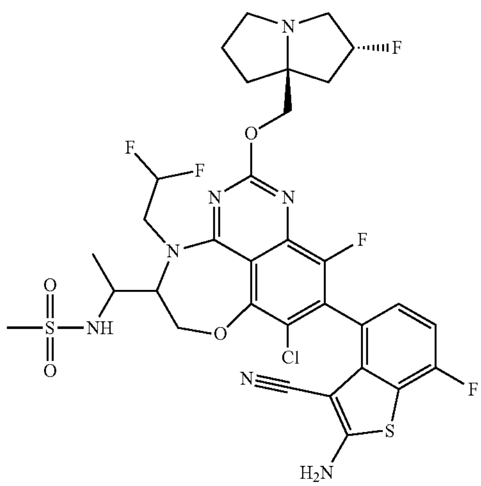 [SMILES: CC(NS(C)(=O)=O)C1COc2c(Cl)c(-c3ccc(F)c4sc(N)c(C#N)c34)c(F)c3nc(OC[C@@]45CCCN4C[C@H](F)C5)nc(c23)N1CC(F)F] | N-(1-(9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)ethyl)methanesulfonamide | 772.3 |
| 783 | 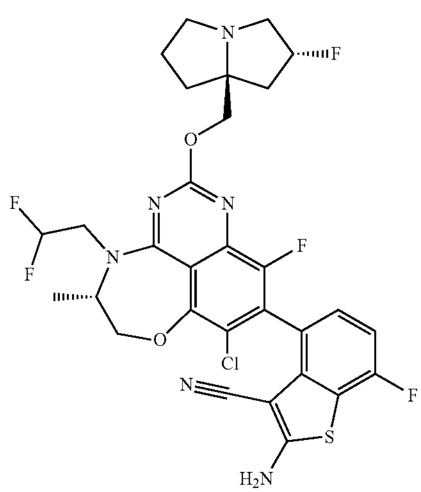 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 665 |

TABLE 1-continued

| No. | Structure | Chemical Name | [M + H]⁺ |
|---|---|---|---|
| 784 | 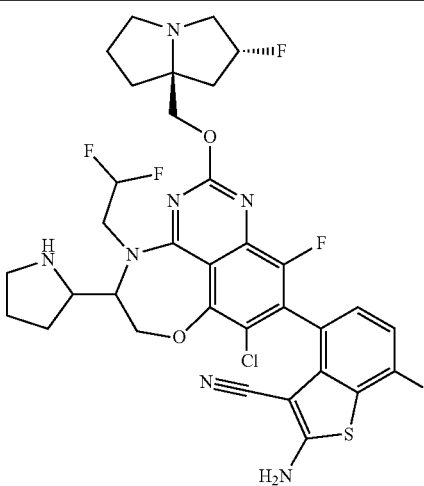 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(pyrrolidin-2-yl)-5,6-dihydro-4H-[1,4]oxazepino[5,6,7-de]quinazolin-9-yl)-7-fluorobenzo[b]thiophene-3-carbonitrile | 720.1 |
| 785 | 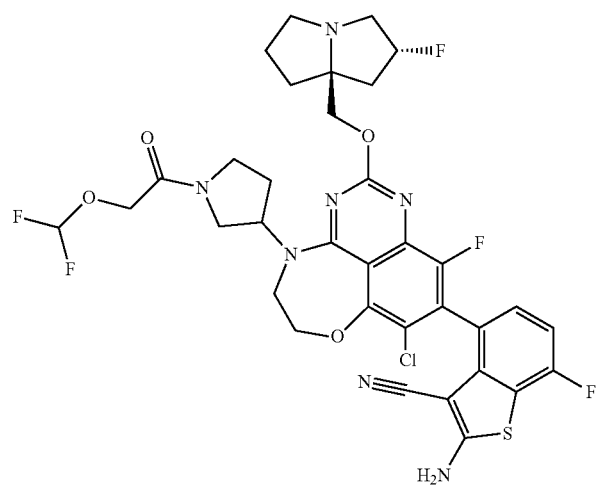 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)COC(F)F)C3)CCO4)c12] | 2-amino-4-(8-chloro-4-(1-(2-(difluoromethoxy)acetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 764.4 |
| 786 | 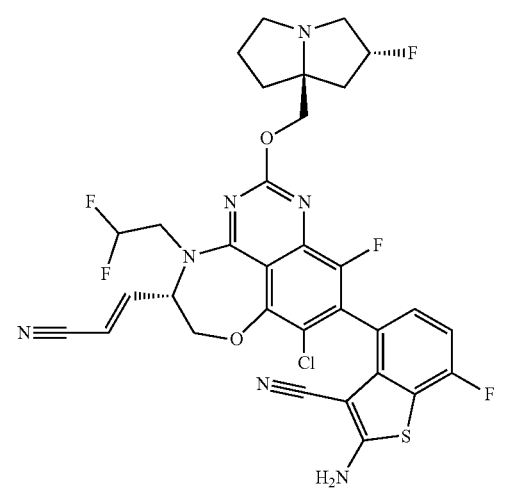 [SMILES: N#C/C=C/[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-5-((E)-2-cyanovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 701.8 |

TABLE 1-continued

| No. | Structure | Chemical Name | [M + H]+ |
|---|---|---|---|
| 787 | 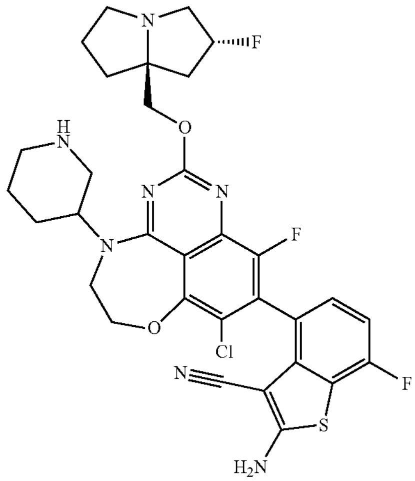 [SMILES: N#Cc1c(N)sc2c(F)ccc(-c3c(Cl)c4c5c(nc(OC[C@@]67CCCN6C[C@H](F)C7)nc5c3F)N(C3CCCNC3)CCO4)c12] | 2-amino-4-(8-chloro-10-fluoro-2-(((2R,7aS)-2-fluorotetrahydro-1H-pyrrolizin-7a(5H)-yl)methoxy)-4-(piperidin-3-yl)-5,6-dihydro-4H-[1,4]oxazepino[5,6,7-de]quinazolin-9-yl)-7-fluorobenzo[b]thiophene-3-carbonitrile | 668.4 (m/z [M − H]+ |
| 788 | 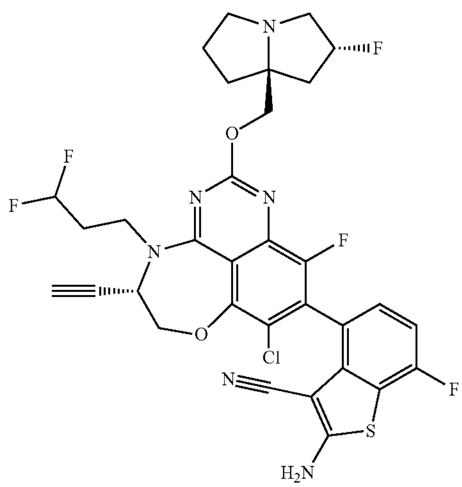 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 688.9 |
| 789 | 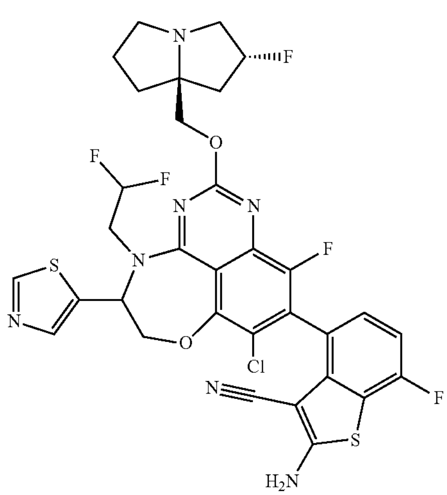 [SMILES: N#Cc1c(N)sc2c(F)ccc(-c3c(Cl)c4c5c(nc(OC[C@@]67CCCN6C[C@H](F)C7)nc5c3F)N(CC(F)F)C(c3cncs3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiazol-5-yl)-5,6-dihydro-4H-[1,4]oxazepino[5,6,7-de]quinazolin-9-yl)-7-fluorobenzo[b]thiophene-3-carbonitrile | 734.2 |

| No. | Structure | Chemical Name | [M + H]+ |
|---|---|---|---|
| 790 | 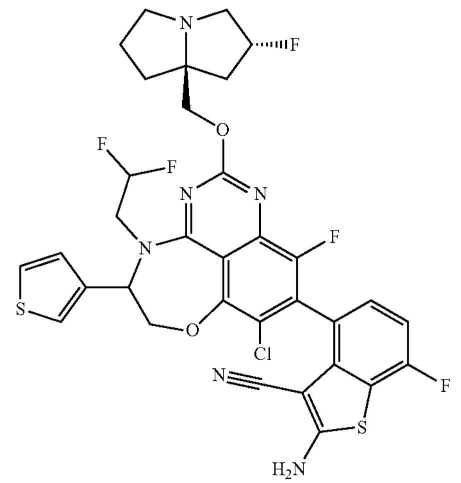 [SMILES: N#Cc1c(N)sc2c(F)ccc(-c3c(Cl)c4c5c(nc(OC[C@@]67CCCN6C[C@H](F)C7)nc5c3F)N(CC(F)F)C(c3ccsc3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiophen-3-yl)-5,6-dihydro-4H-[1,4]oxazepino[5,6,7-de]quinazolin-9-yl)-7-fluorobenzo[b]thiophene-3-carbonitrile | 732.8 |
| 791 | 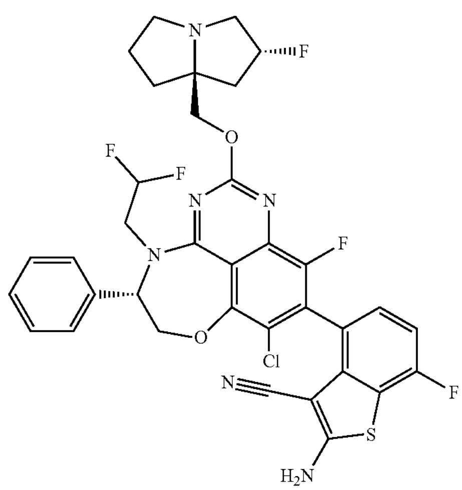 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](c3ccccc3)CO4)c12] | 2-amino-4-((S)-8-chloro-4-(2,2-difluoroethyl)-10-fluoro-2-(((2R,7aS)-2-fluorotetrahydro-1H-pyrrolizin-7a(5H)-yl)methoxy)-5-phenyl-5,6-dihydro-4H-[1,4]oxazepino[5,6,7-de]quinazolin-9-yl)-7-fluorobenzo[b]thiophene-3-carbonitrile | 726.9 |
| 792 | 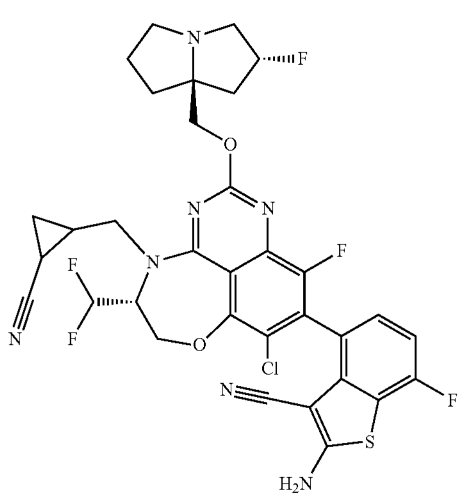 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |

TABLE 1-continued

| No. | Structure | Chemical Name | [M + H]+ |
|---|---|---|---|
| 793 | 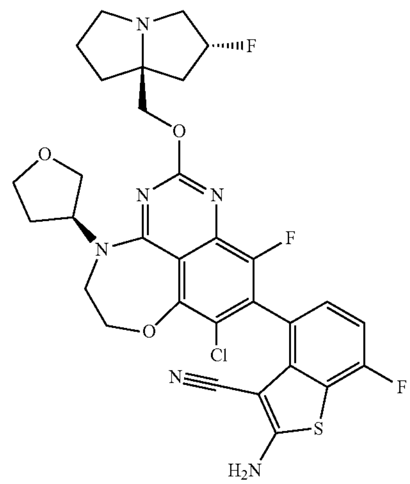 [SMILES: N#Cc1c(N)sc2c(F)ccc(-c3c(Cl)c4c5c(nc(OC[C@@]67CCCN6C[C@H](F)C7)nc5c3F)N([C@H]3CCOC3)CCO4)c12] | 2-amino-4-(8-chloro-10-fluoro-2-(((2R,7aS)-2-fluorotetrahydro-1H-pyrrolizin-7a(5H)-yl)methoxy)-4-((S)-tetrahydrofuran-3-yl)-5,6-dihydro-4H-[1,4]oxazepino[5,6,7-de]quinazolin-9-yl)-7-fluorobenzo[b]thiophene-3-carbonitrile | 657.2 |
| 794 | 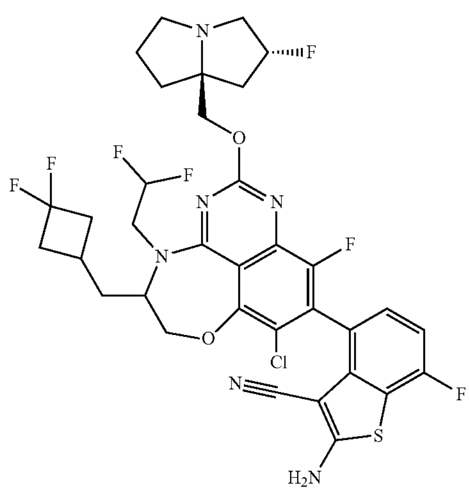 [SMILES: N#Cc1c(N)sc2c(F)ccc(-c3c(Cl)c4c5c(nc(OC[C@@]67CCCN6C[C@H](F)C7)nc5c3F)N(CC(F)F)C(CC3CC(F)(F)C3)CO4)c12] | 2-amino-4-(8-chloro-5-((3,3-difluorocyclobutyl)methyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 755.4 |
| 795 | 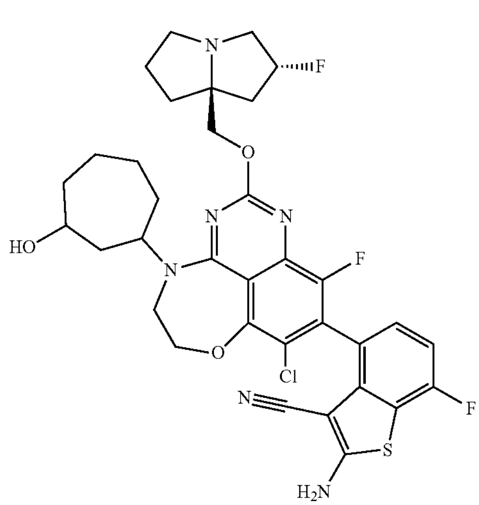 [SMILES: N#Cc1c(N)sc2c(F)ccc(-c3c(Cl)c4c5c(nc(OC[C@@]67CCCN6C[C@H](F)C7)nc5c3F)N(C3CCCCC(O)C3)CCO4)c12] | 2-amino-4-(8-chloro-10-fluoro-2-(((2R,7aS)-2-fluorotetrahydro-1H-pyrrolizin-7a(5H)-yl)methoxy)-4-(3-hydroxycycloheptyl)-5,6-dihydro-4H-[1,4]oxazepino[5,6,7-de]quinazolin-9-yl)-7-fluorobenzo[b]thiophene-3-carbonitrile | 745 |

TABLE 1-continued

| No. | Structure | Chemical Name | [M + H]+ |
|---|---|---|---|
| 796 | 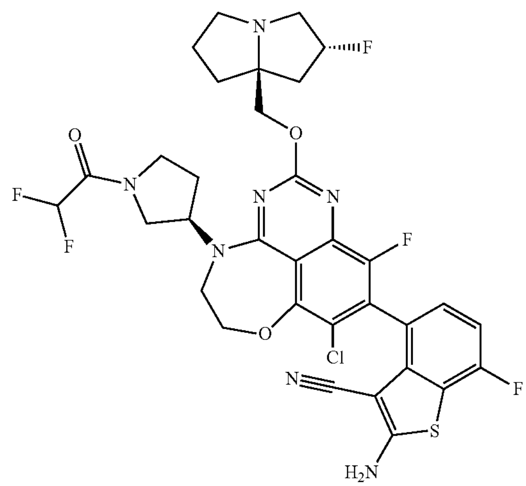 [SMILES: N#Cc1c(N)sc2c(F)ccc(-c3c(Cl)c4c5c(nc(OC[C@@]67CCCN6C[C@H](F)C7)nc5c3F)N([C@@H]3CCN(C(=O)C(F)F)C3)CCO4)c12] | 2-amino-4-(8-chloro-4-((R)-1-(2,2-difluoroacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 734.3 |
| 797 | 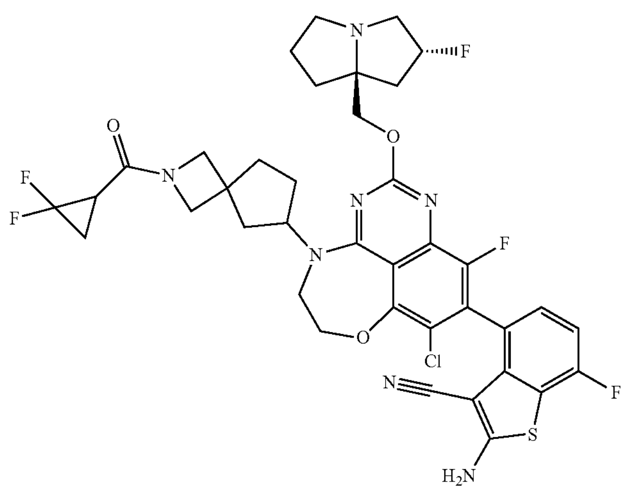 [SMILES: N#Cc1c(N)sc2c(F)ccc(-c3c(Cl)c4c5c(nc(OC[C@@]67CCCN6C[C@H](F)C7)nc5c3F)N(C3CCC5(C3)CN(C(=O)C3CC3(F)F)C5)CCO4)c12] | 2-amino-4-(8-chloro-4-(2-(2,2-difluorocyclopropane-1-carbonyl)-2-azaspiro[3.4]octan-6-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 800.4 |
| 798 | 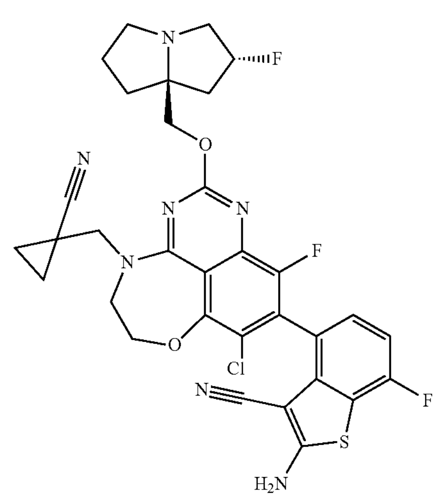 [SMILES: N#Cc1c(N)sc2c(F)ccc(-c3c(Cl)c4c5c(nc(OC[C@@]67CCCN6C[C@H](F)C7)nc5c3F)N(CC3(C#N)CC3)CCO4)c12] | 2-amino-4-(8-chloro-4-((1-cyanocyclopropyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 666.2 |

TABLE 1-continued

| No. | Structure | Chemical Name | [M + H]+ |
|---|---|---|---|
| 799 | 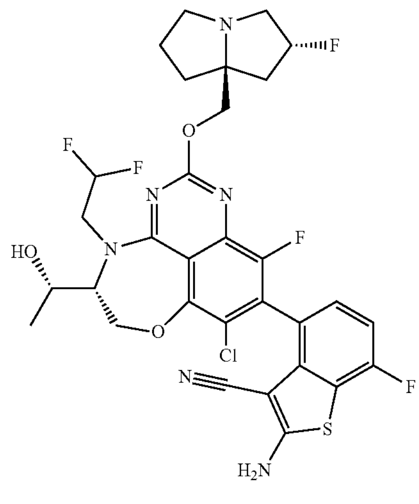 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 694.5 |
| 800 | 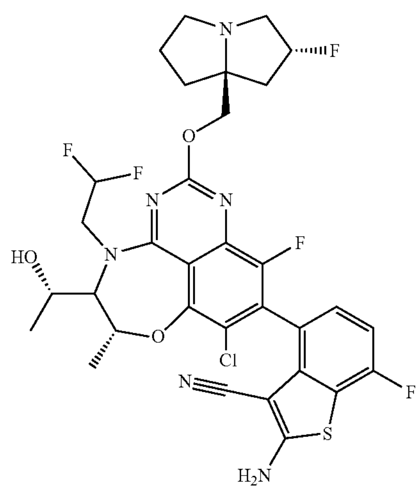 | 2-amino-4-((5S,6R)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 801 | 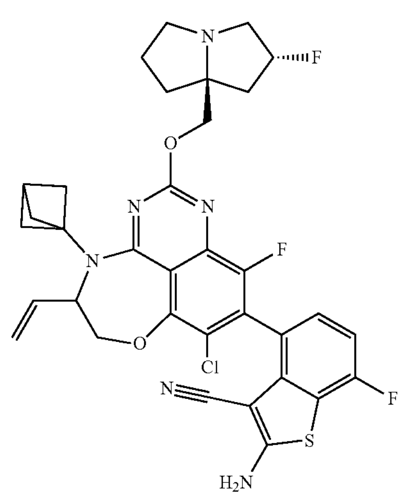 [SMILES: C=CC1COc2c(Cl)c(-c3ccc(F)c4sc(N)c(C#N)c34)c(F)c3nc(OC[C@@]45CCCN4C[C@H](F)C5)nc(c23)N1C12CC(C1)C2] | 2-amino-4-(4-(bicyclo[1.1.1]pentan-1-yl)-8-chloro-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 679.1 |

TABLE 1-continued

| No. | Structure | Chemical Name | [M + H]⁺ |
|---|---|---|---|
| 802 | 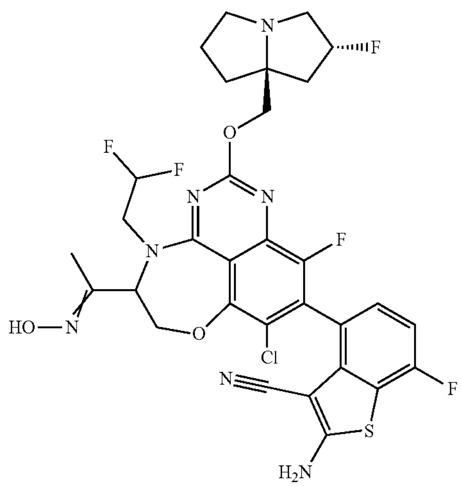 [SMILES: CC(=NO)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-(hydroxyimino)ethyl)-5,6-dihydro-4H-[1,4]oxazepino[5,6,7-de]quinazolin-9-yl)-7-fluorobenzo[b]thiophene-3-carbonitrile | 707.9 |
| 803 | 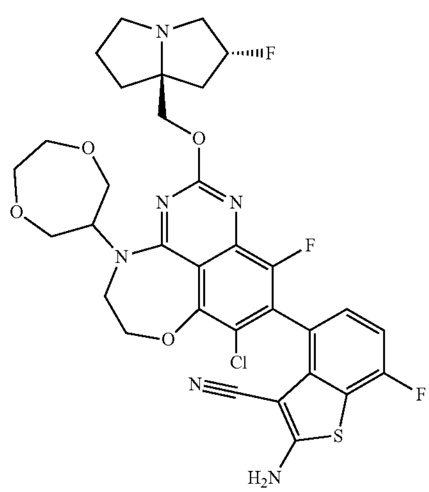 [SMILES: N#Cc1c(N)sc2c(F)ccc(-c3c(Cl)c4c5c(nc(OC[C@@]67CCCN6C[C@H](F)C7)nc5c3F)N(C3COCCOC3)CCO4)c12] | 2-amino-4-(8-chloro-4-(1,4-dioxepan-6-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 678.2 |
| 804 | 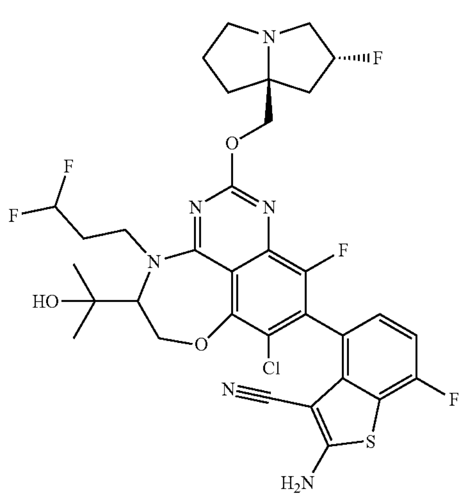 [SMILES: CC(C)(O)C1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-(8-chloro-4-(3,3-difluoropropyl)-10-fluoro-2-(((2R,7aS)-2-fluorotetrahydro-1H-pyrrolizin-7a(5H)-yl)methoxy)-5-(2-hydroxypropan-2-yl)-5,6-dihydro-4H-[1,4]oxazepino[5,6,7-de]quinazolin-9-yl)-7-fluorobenzo[b]thiophene-3-carbonitrile | 722.9 |

TABLE 1-continued

| No. | Structure | Chemical Name | [M + H]+ |
|---|---|---|---|
| 805 | 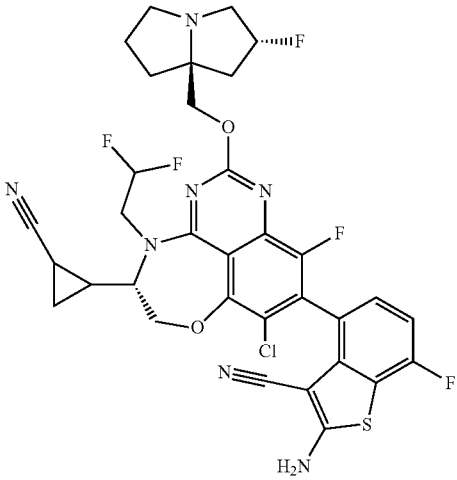 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3C#N)CO4)c12] | 2-amino-4-((5S)-8-chloro-5-(2-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 715.9 |
| 806 | 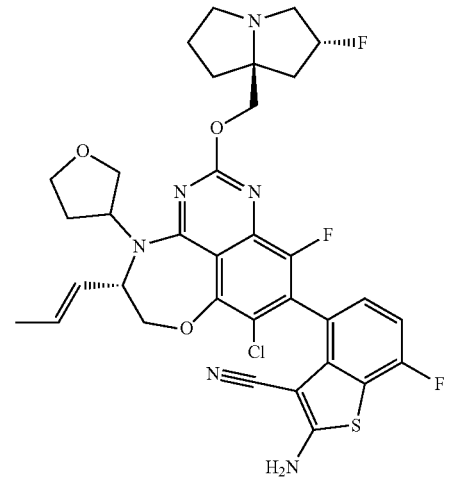 [SMILES: C/C=C/[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-5-((E)-prop-1-en-1-yl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 697.3 |
| 807 | 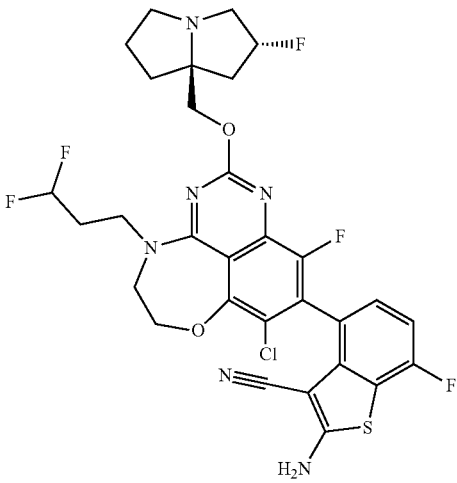 [SMILES: N#Cc1c(N)sc2c(F)ccc(-c3c(Cl)c4c5c(nc(OC[C@@]67CCCN6C[C@H](F)C7)nc5c3F)N(CCC(F)F)CCO4)c12] | 2-amino-4-(8-chloro-4-(3,3-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 664.8 |

TABLE 1-continued

| No. | Structure | Chemical Name | [M + H]+ |
|---|---|---|---|
| 808 | 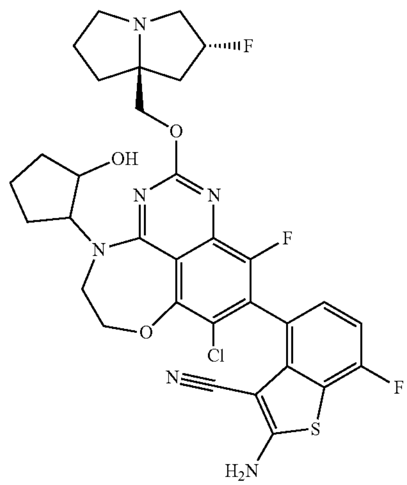 [SMILES: N#Cc1c(N)sc2c(F)ccc(-c3c(Cl)c4c5c(nc(OC[C@@]67CCCN6C[C@H](F)C7)nc5c3F)N(C3CCCC3O)CCO4)c12] | 2-amino-4-(8-chloro-10-fluoro-2-(((2R,7aS)-2-fluorotetrahydro-1H-pyrrolizin-7a(5H)-yl)methoxy)-4-(2-hydroxycyclopentyl)-5,6-dihydro-4H-[1,4]oxazepino[5,6,7-de]quinazolin-9-yl)-7-fluorobenzo[b]thiophene-3-carbonitrile | 671.1 |
| 809 | 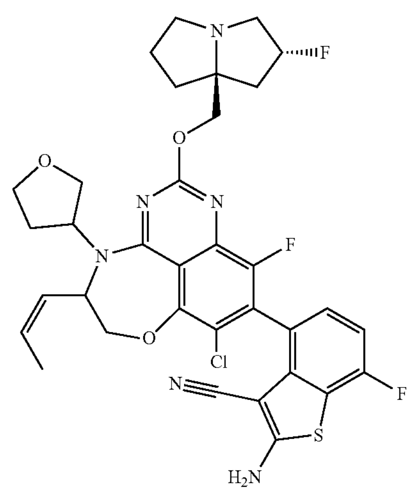 [SMILES: C/C=C\C1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-(8-chloro-10-fluoro-2-(((2R,7aS)-2-fluorotetrahydro-1H-pyrrolizin-7a(5H)-yl)methoxy)-5-((Z)-prop-1-en-1-yl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 697.1 |
| 810 | 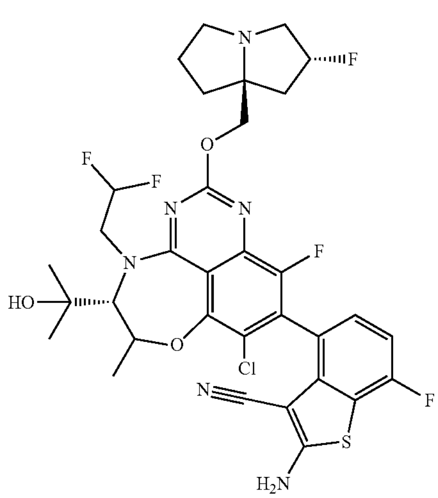 | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropan-2-yl)-6-methyl-5,6-dihydro-4H-[1,4]oxazepino[5,6,7-de]quinazolin-9-yl)-7-fluorobenzo[b]thiophene-3-carbonitrile | 723 |

TABLE 1-continued

| No. | Structure | Chemical Name | [M + H]⁺ |
|---|---|---|---|
| 811 | 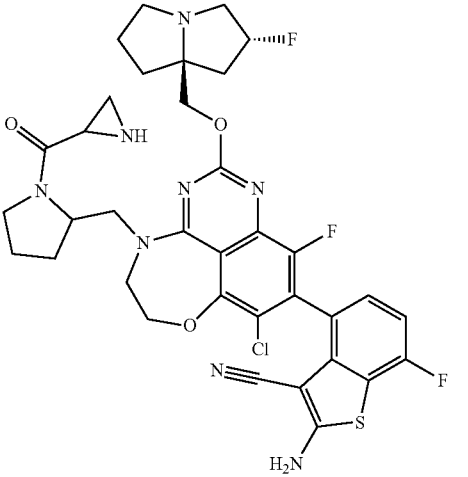 [SMILES: N#Cc1c(N)sc2c(F)ccc(-c3c(Cl)c4c5c(nc(OC[C@@]67CCCN6C[C@H](F)C7)nc5c3F)N(CC3CCCN3C(=O)C3CN3)CCO4)c12] | 2-amino-4-(4-((1-(aziridine-2-carbonyl)pyrrolidin-2-yl)methyl)-8-chloro-10-fluoro-2-((((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 739.4 |
| 812 | 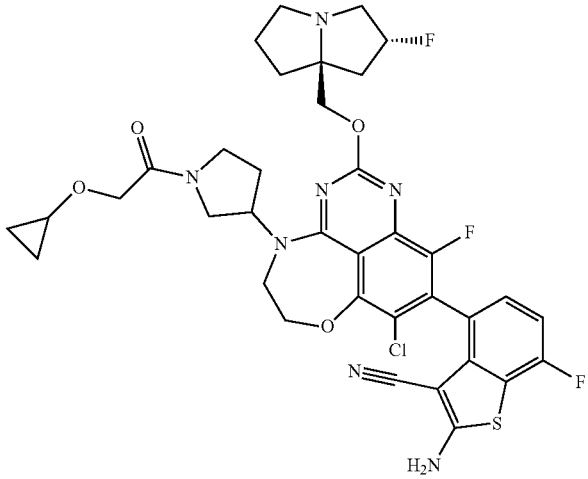 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)COC5CC5)C3)CCO4)c12] | 2-amino-4-(8-chloro-4-(1-(2-cyclopropoxyacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 754.4 |
| 813 | 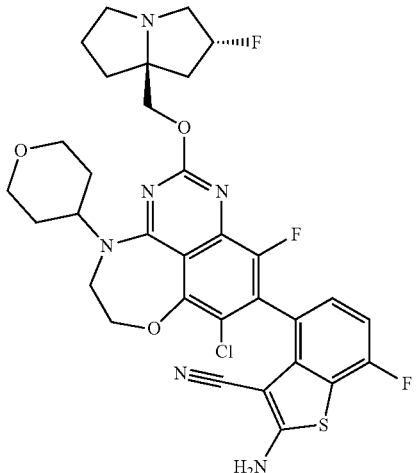 | 2-amino-4-(8-chloro-10-fluoro-2-(((2R,7aS)-2-fluorotetrahydro-1H-pyrrolizin-7a(5H)-yl)methoxy)-4-(tetrahydro-2H-pyran-4-yl)-5,6-dihydro-4H-[1,4]oxazepino[5,6,7-de]quinazolin-9-yl)-7-fluorobenzo[b]thiophene-3-carbonitrile | 671.2 |

TABLE 1-continued

| No. | Structure | Chemical Name | [M + H]⁺ |
|---|---|---|---|
| 814 | 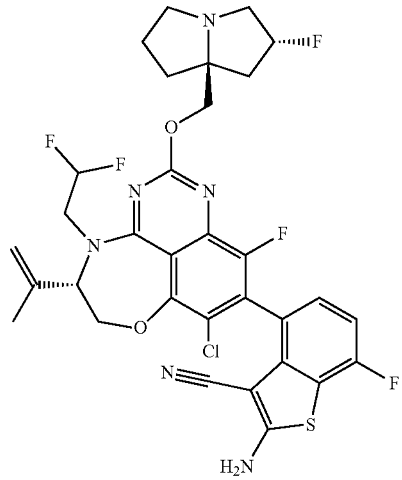 [SMILES: C=C(C)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-(prop-1-en-2-yl)-5,6-dihydro-4H-[1,4]oxazepino[5,6,7-de]quinazolin-9-yl)-7-fluorobenzo[b]thiophene-3-carbonitrile | 690.9 |
| 815 | 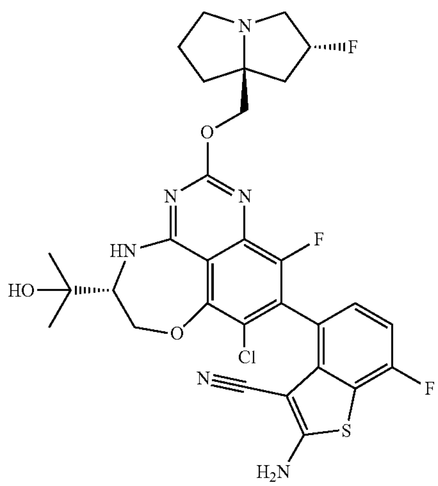 [SMILES: CC(C)(O)[C@H]1COc2c(Cl)c(-c3ccc(F)c4sc(N)c(C#N)c34)c(F)c3nc(OC[C@@]45CCCN4C[C@H](F)C5)nc(c23)N1] | 2-amino-4-((5R)-8-chloro-10-fluoro-2-(((2R,7aS)-2-fluorotetrahydro-1H-pyrrolizin-7a(5H)-yl)methoxy)-5-(2-hydroxypropan-2-yl)-5,6-dihydro-4H-[1,4]oxazepino[5,6,7-de]quinazolin-9-yl)-7-fluorobenzo[b]thiophene-3-carbonitrile | 644.9 |
| 816 | 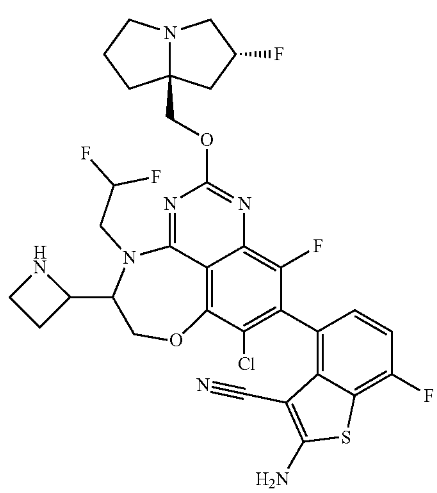 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCN3)CO4)c12] | 2-amino-4-(5-(azetidin-2-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 706.1 |

TABLE 1-continued

| No. | Structure | Chemical Name | [M + H]+ |
|---|---|---|---|
| 817 | 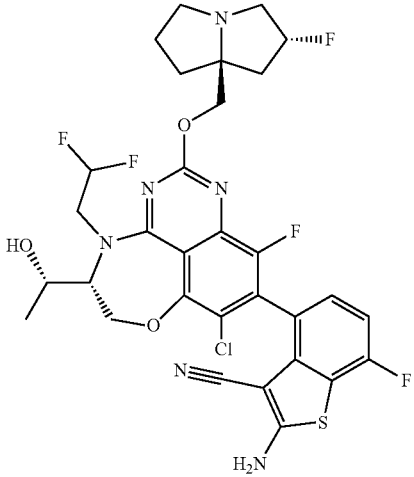 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 695.3 |
| 818 | 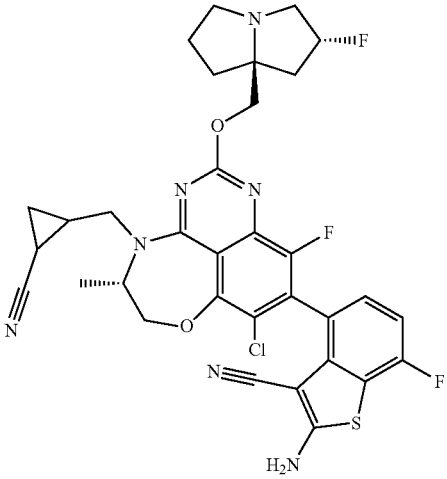 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CC1CC1C#N] | 2-amino-4-((5S)-8-chloro-4-((2-cyanocyclopropyl)methyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 680 |
| 819 | 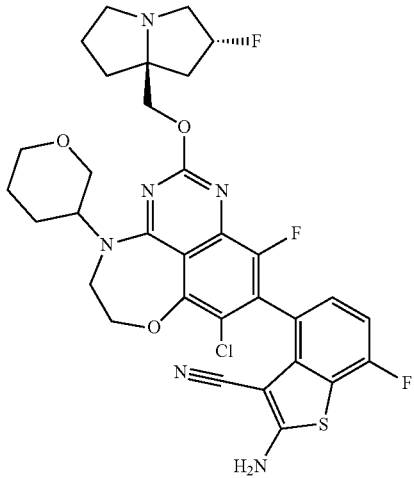 [SMILES: N#Cc1c(N)sc2c(F)ccc(-c3c(Cl)c4c5c(nc(OC[C@@]67CCCN6C[C@H](F)C7)nc5c3F)N(C3CCCOC3)CCO4)c12] | 2-amino-4-(8-chloro-10-fluoro-2-(((2R,7aS)-2-fluorotetrahydro-1H-pyrrolizin-7a(5H)-yl)methoxy)-4-(tetrahydro-2H-pyran-3-yl)-5,6-dihydro-4H-[1,4]oxazepino[5,6,7-de]quinazolin-9-yl)-7-fluorobenzo[b]thiophene-3-carbonitrile | 671.3 |

TABLE 1-continued

| No. | Structure | Chemical Name | [M + H]+ |
|---|---|---|---|
| 820 | 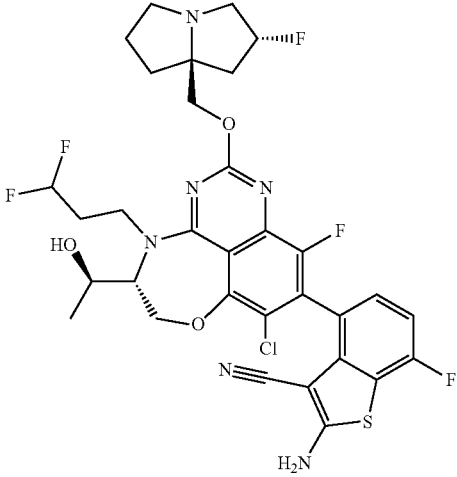 [SMILES: C[C@@H](O)[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5R)-8-chloro-4-(3,3-difluoropropyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile | 708.9 |
| 821 | 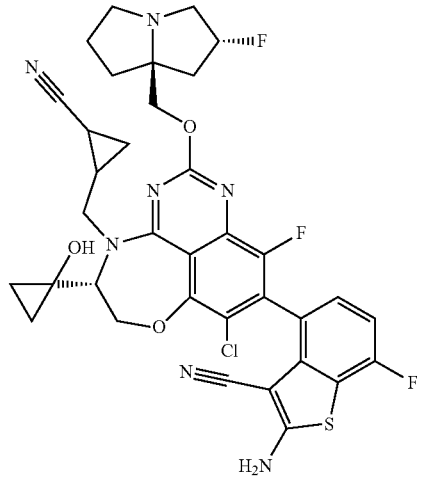 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |
| 822 | 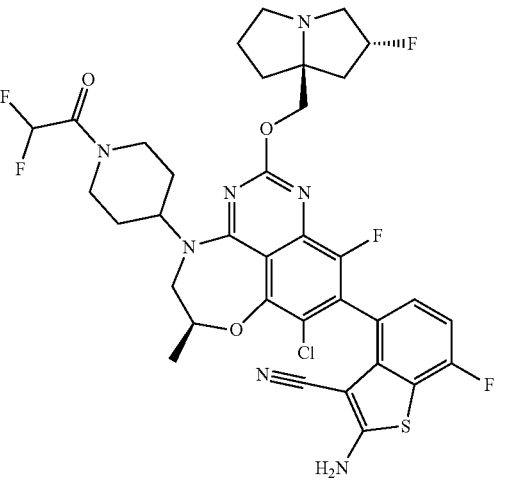 [SMILES: C[C@H]1CN(C2CCN(C(=O)C(F)F)CC2)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-(1-(2,2-difluoroacetyl)piperidin-4-yl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 762.4 |

TABLE 1-continued

| No. | Structure | Chemical Name | [M + H]+ |
|---|---|---|---|
| 823 | 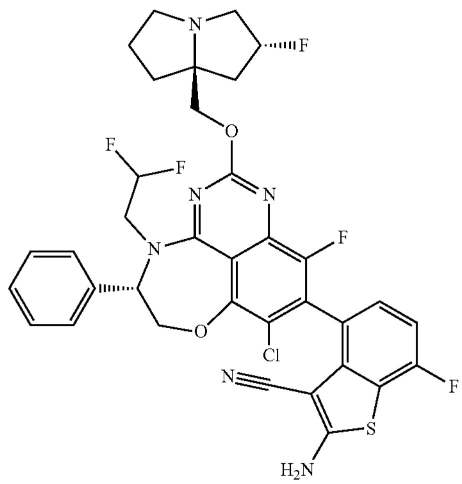 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](c3ccccc3)CO4)c12] | 2-amino-4-((S)-8-chloro-4-(2,2-difluoroethyl)-10-fluoro-2-(((2R,7aS)-2-fluorotetrahydro-1H-pyrrolizin-7a(5H)-yl)methoxy)-5-phenyl-5,6-dihydro-4H-[1,4]oxazepino[5,6,7-de]quinazolin-9-yl)-7-fluorobenzo[b]thiophene-3-carbonitrile | 726.9 |
| 824 | 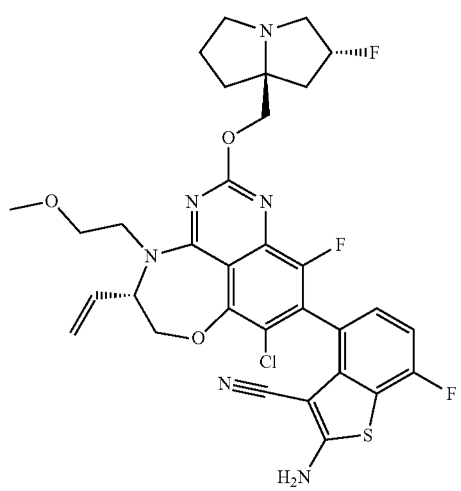 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CCOC] | 2-amino-4-((5S)-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino[5,6,7-de]quinazolin-9-yl)-7-fluorobenzo[b]thiophene-3-carbonitrile | 671.3 |
| 825 | 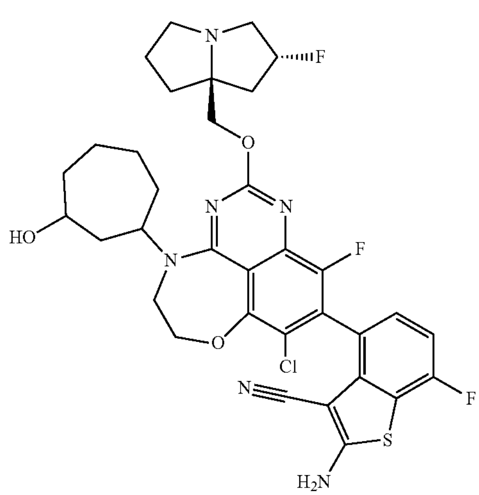 [SMILES: N#Cc1c(N)sc2c(F)ccc(-c3c(Cl)c4c5c(nc(OC[C@@]67CCCN6C[C@H](F)C7)nc5c3F)N(C3CCCCC(O)C3)CCO4)c12] | 2-amino-4-(8-chloro-10-fluoro-2-(((2R,7aS)-2-fluorotetrahydro-1H-pyrrolizin-7a(5H)-yl)methoxy)-4-(3-hydroxycycloheptyl)-5,6-dihydro-4H-[1,4]oxazepino[5,6,7-de]quinazolin-9-yl)-7-fluorobenzo[b]thiophene-3-carbonitrile | 699.3 |

TABLE 1-continued

| No. | Structure | Chemical Name | [M + H]+ |
|---|---|---|---|
| 826 | 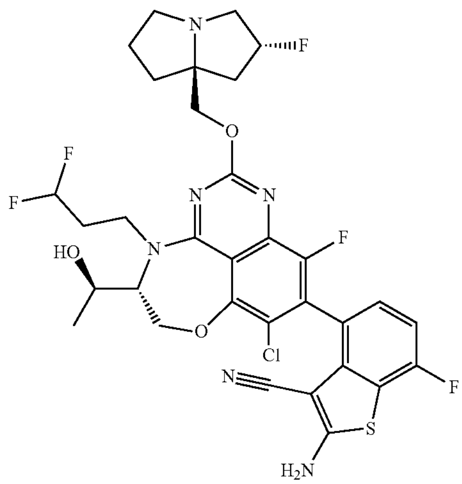 [SMILES: C[C@@H](O)[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5R)-8-chloro-4-(3,3-difluoropropyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile | 708.9 |
| 827 | 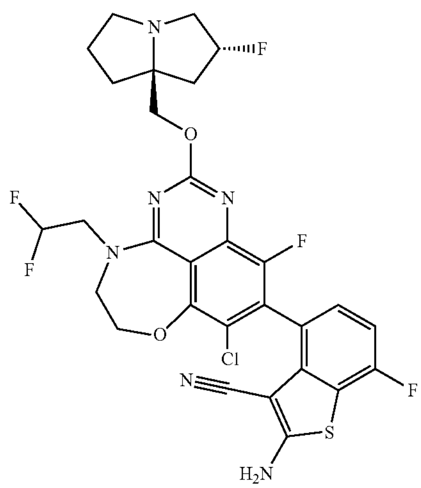 [SMILES: N#Cc1c(N)sc2c(F)ccc(-c3c(Cl)c4c5c(nc(OC[C@@]67CCCN6C[C@H](F)C7)nc5c3F)N(CC(F)F)CCO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 651.1 |
| 828 | 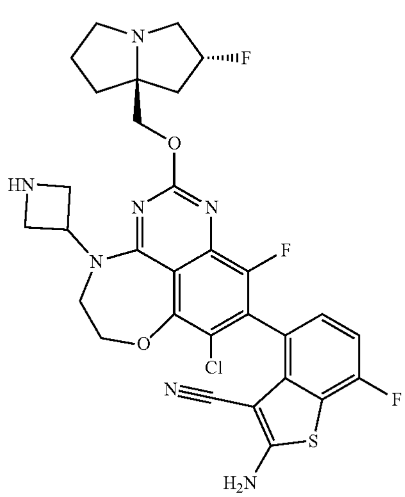 [SMILES: N#Cc1c(N)sc2c(F)ccc(-c3c(Cl)c4c5c(nc(OC[C@@]67CCCN6C[C@H](F)C7)nc5c3F)N(C3CNC3)CCO4)c12] | 2-amino-4-(4-(azetidin-3-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 642.3 |

TABLE 1-continued

| No. | Structure | Chemical Name | [M + H]+ |
|---|---|---|---|
| 829 | 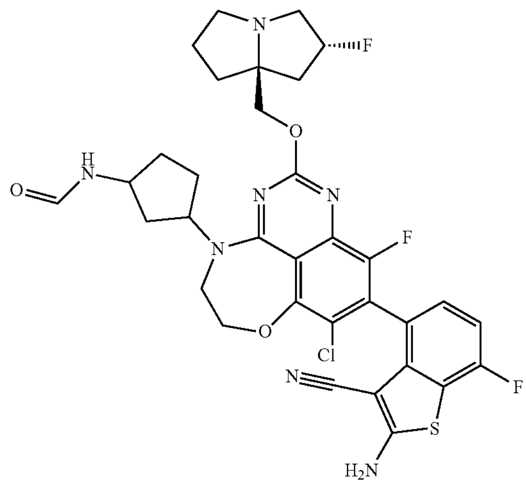 [SMILES: N#Cc1c(N)sc2c(F)ccc(-c3c(Cl)c4c5c(nc(OC[C@@]67CCCN6C[C@H](F)C7)nc5c3F)N(C3CCC(NC=O)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclopentyl)formamide | 698.2 |
| 830 | 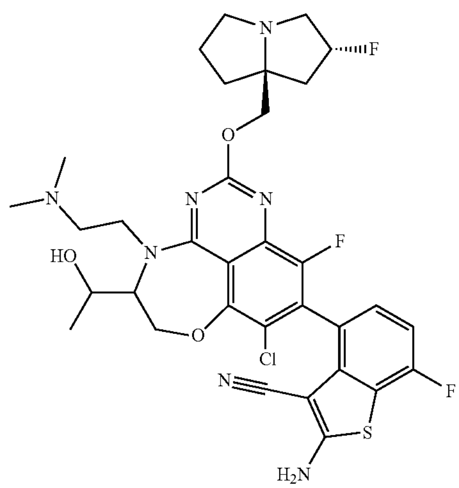 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CCN(C)C] | 2-amino-4-(8-chloro-4-(2-(dimethylamino)ethyl)-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile | 702.2 |
| 831 | 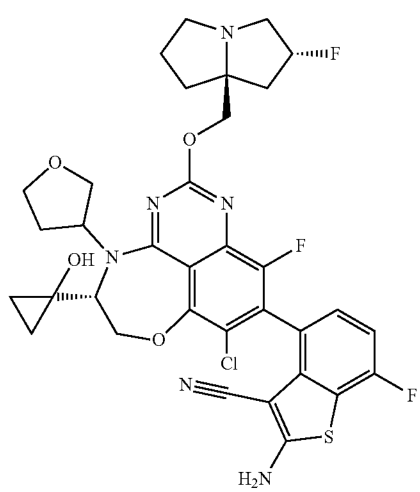 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(O)CC3)CO4)c12] | 2-amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 713 |

TABLE 1-continued

| No. | Structure | Chemical Name | [M + H]⁺ |
|---|---|---|---|
| 832 | 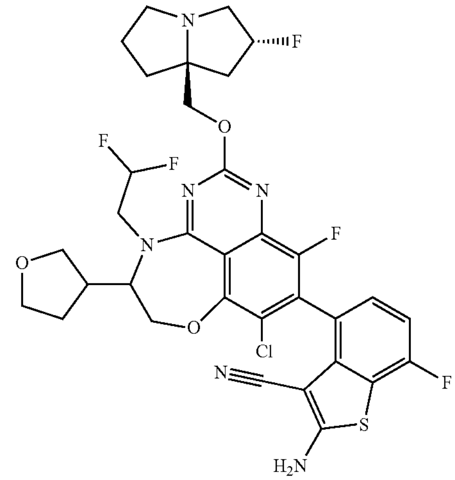 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCOC3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazolin-9-yl)-7-fluorobenzo[b]thiophene-3-carbonitrile | 720.9 |
| 833 | 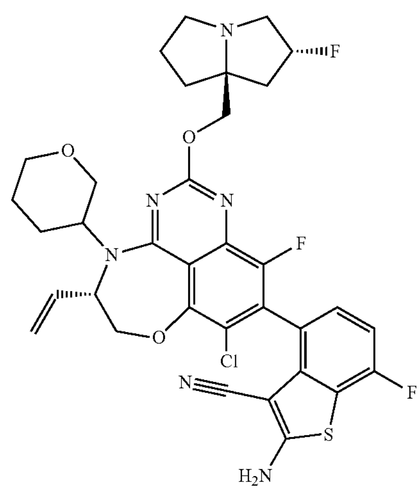 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCCOC1] | 2-amino-4-((5S)-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazolin-9-yl)-7-fluorobenzo[b]thiophene-3-carbonitrile | 696.9 |
| 834 | 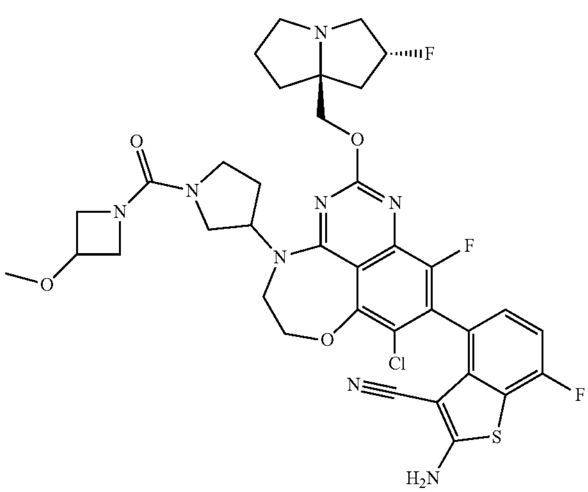 | 2-amino-4-(8-chloro-10-fluoro-2-(((2R,7aS)-2-fluorotetrahydro-1H-pyrrolizin-7a(5H)-yl)methoxy)-4-(1-(3-methoxyazetidine-1-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 769.4 |

TABLE 1-continued

| No. | Structure | Chemical Name | [M + H]+ |
|---|---|---|---|
| 835 | 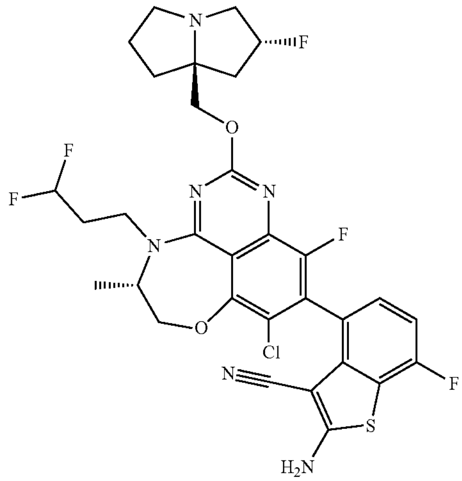 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 679.3 |
| 836 | 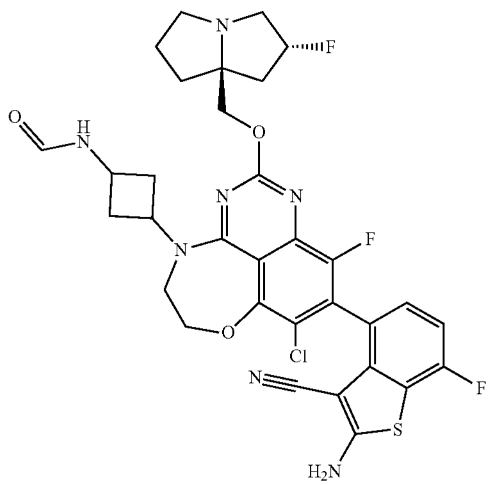 [SMILES: N#Cc1c(N)sc2c(F)ccc(-c3c(Cl)c4c5c(nc(OC[C@@]67CCCN6C[C@H](F)C7)nc5c3F)N(C3CC(NC=O)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)formamide | 684.3 |
| 837 | 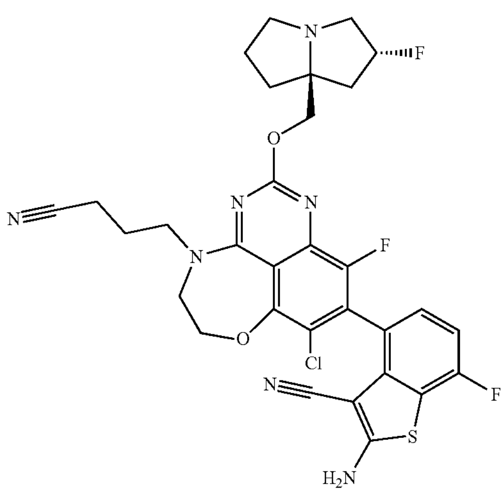 [SMILES: N#CCCCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(3-cyanopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 654.1 |

TABLE 1-continued

| No. | Structure | Chemical Name | [M + H]+ |
|---|---|---|---|
| 838 | 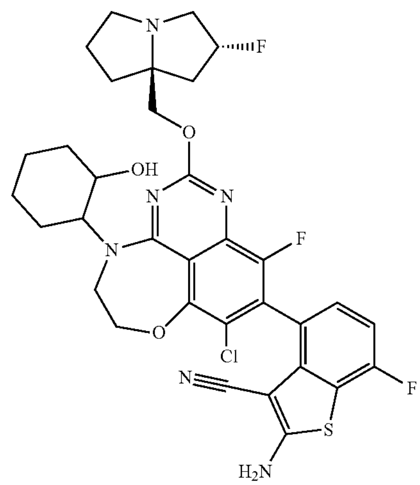 [SMILES: N#Cc1c(N)sc2c(F)ccc(-c3c(Cl)c4c5c(nc(OC[C@@]67CCCN6C[C@H](F)C7)nc5c3F)N(C3CCCCC3O)CCO4)c12] | 2-amino-4-(8-chloro-10-fluoro-2-(((2R,7aS)-2-fluorotetrahydro-1H-pyrrolizin-7a(5H)-yl)methoxy)-4-(2-hydroxycyclohexyl)-5,6-dihydro-4H-[1,4]oxazepino[5,6,7-de]quinazolin-9-yl)-7-fluorobenzo[b]thiophene-3-carbonitrile | 685.2 |
| 839 | 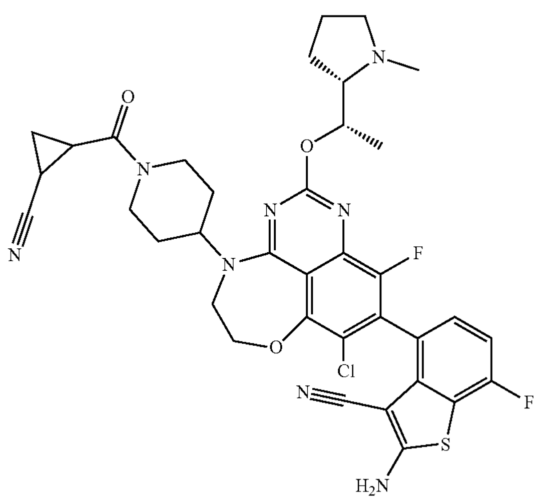 [SMILES: C[C@H](Oc1nc2c3c(c(Cl)c(-c4ccc(F)c5sc(N)c(C#N)c45)c(F)c3n1)OCCN2C1CCN(C(=O)C2CC2C#N)CC1)[C@@H]1CCCN1C] | 2-amino-4-(8-chloro-4-(1-(2-cyanocyclopropane-1-carbonyl)piperidin-4-yl)-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile | 733.4 |
| 840 | 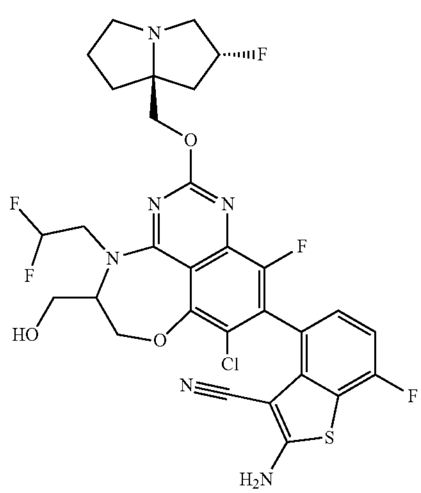 [SMILES: N#Cc1c(N)sc2c(F)ccc(-c3c(Cl)c4c5c(nc(OC[C@@]67CCCN6C[C@H](F)C7)nc5c3F)N(CC(F)F)C(CO)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(hydroxymethyl)-5,6-dihydro-4H-[1,4]oxazepino[5,6,7-de]quinazolin-9-yl)-7-fluorobenzo[b]thiophene-3-carbonitrile | 681.1 |

| No. | Structure | Chemical Name | [M + H]+ |
|---|---|---|---|
| 841 | 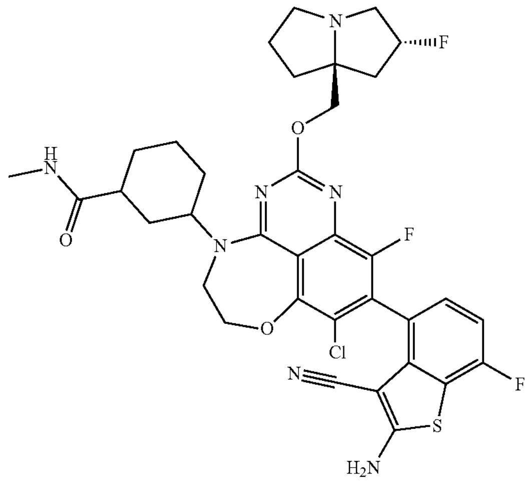 | 3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N-methylcyclohexane-1-carboxamide | 726.3 |
| 842 | 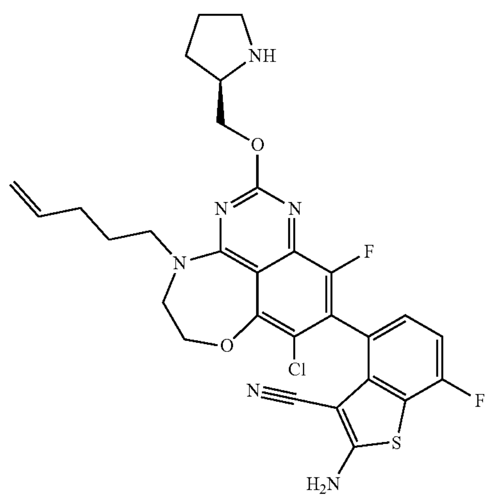 [SMILES: C=CCCCN1CCOc2c(Cl)c(-c3ccc(F)c4sc(N)c(C#N)c34)c(F)c3nc(OC[C@H]4CCCN4)nc1c23] | 2-amino-4-(8-chloro-10-fluoro-4-(pent-4-en-1-yl)-2-(((R)-pyrrolidin-2-yl)methoxy)-5,6-dihydro-4H-[1,4]oxazepino[5,6,7-de]quinazolin-9-yl)-7-fluorobenzo[b]thiophene-3-carbonitrile | 597.3 |
| 843 | 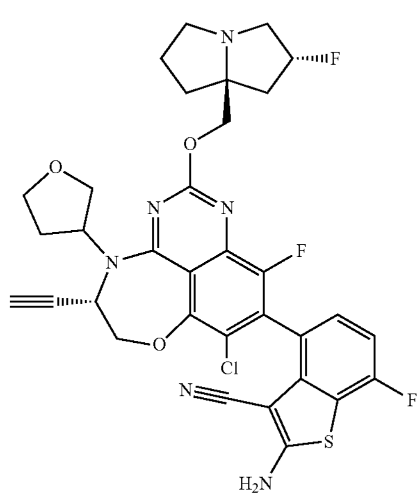 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-5-ethynyl-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 681.3 |

TABLE 1-continued

| No. | Structure | Chemical Name | [M + H]+ |
|---|---|---|---|
| 844 | 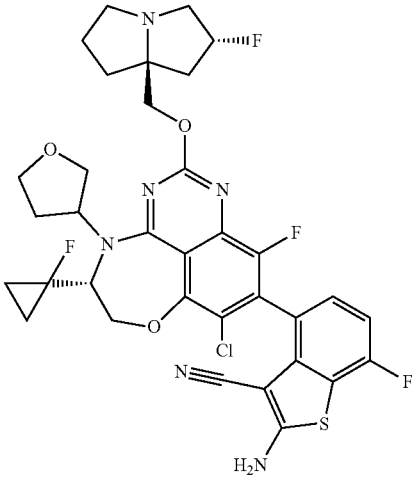 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(F)CC3)CO4)c12] | 2-amino-4-((5R)-8-chloro-10-fluoro-5-(1-fluorocyclopropyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 715.4 |
| 845 | 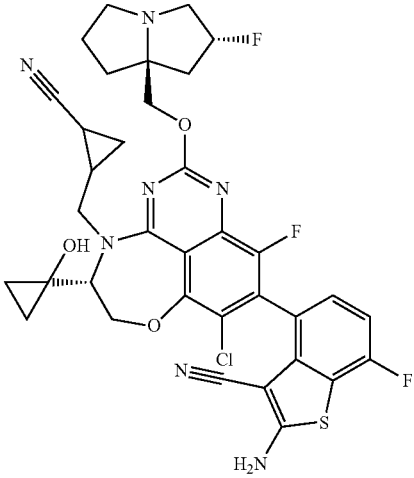 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |
| 846 | 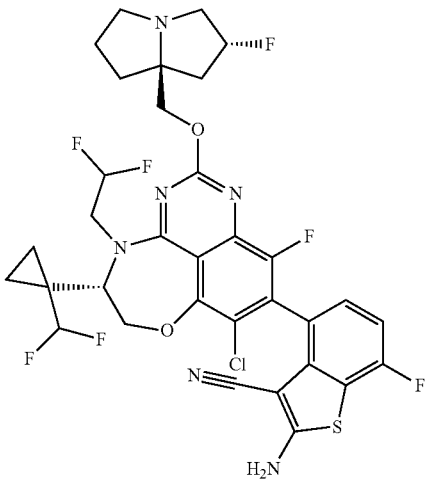 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(C(F)F)CC3)CO4)c12] | 2-amino-4-((S)-8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 741.1 |

TABLE 1-continued

| No. | Structure | Chemical Name | [M + H]+ |
|---|---|---|---|
| 847 | 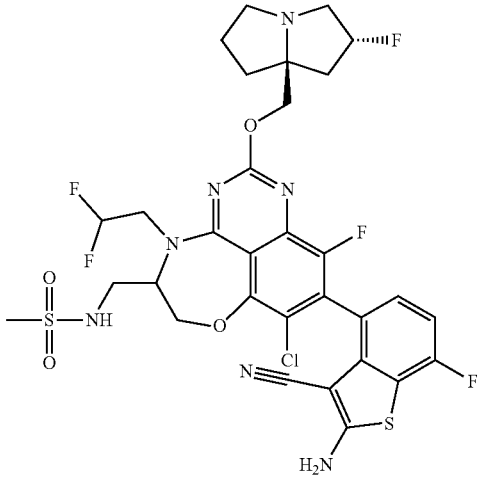 [SMILES: CS(=O)(=O)NCC1COc2c(Cl)c(-c3ccc(F)c4sc(N)c(C#N)c34)c(F)c3nc(OC[C@@]45CCCN4C[C@H](F)C5)nc(c23)N1CC(F)F] | N-((9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)methanesulfonamide | 758.3 |
| 848 | 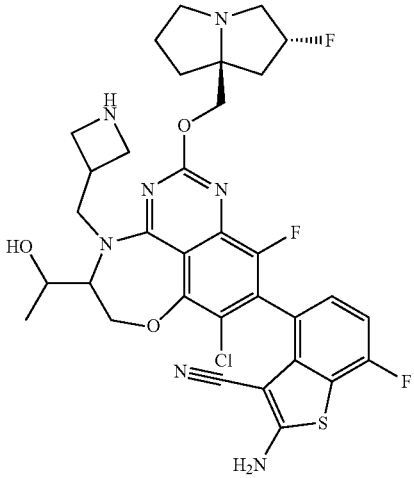 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC1CNC1] | 2-amino-4-(4-(azetidin-3-ylmethyl)-8-chloro-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile | 700.2 |
| 849 | 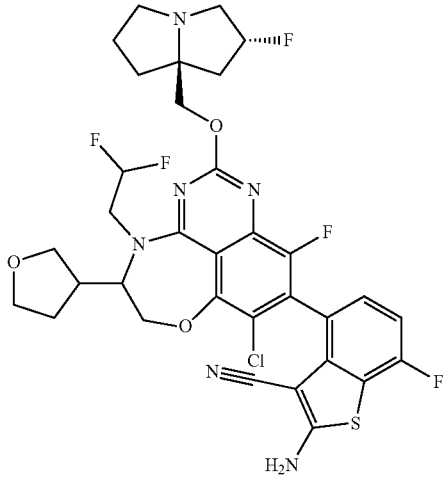 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-3-yl)-5,6-dihydro-4H-[1,4]oxazepino[5,6,7-de]quinazolin-9-yl)-7-fluorobenzo[b]thiophene-3-carbonitrile | 720.9 |

TABLE 1-continued

| No. | Structure | Chemical Name | [M + H]+ |
|---|---|---|---|
| 850 | 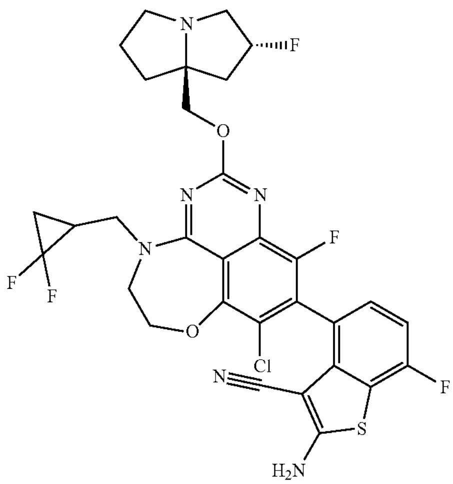 [SMILES: N#Cc1c(N)sc2c(F)ccc(-c3c(Cl)c4c5c(nc(OC[C@@]67CCCN6C[C@H](F)C7)nc5c3F)N(CC3CC3(F)F)CCO4)c12] | 2-amino-4-(8-chloro-4-((2,2-difluorocyclopropyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 677.3 |
| 851 | 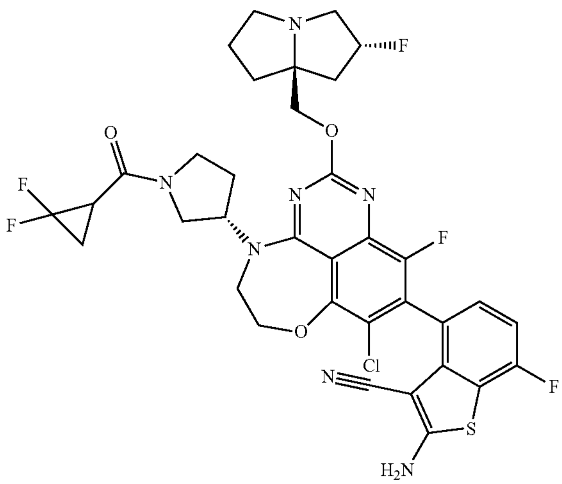 [SMILES: N#Cc1c(N)sc2c(F)ccc(-c3c(Cl)c4c5c(nc(OC[C@@]67CCCN6C[C@H](F)C7)nc5c3F)N([C@H]3CCN(C(=O)C5CC5(F)F)C3)CCO4)c12] | 2-amino-4-(8-chloro-4-((3S)-1-(2,2-difluorocyclopropane-1-carbonyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 760.4 |
| 852 | 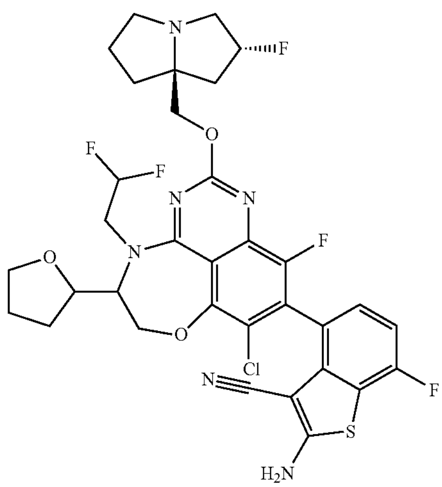 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCO3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile | 720.9 |

TABLE 1-continued

| No. | Structure | Chemical Name | [M + H]+ |
|---|---|---|---|
| 853 | 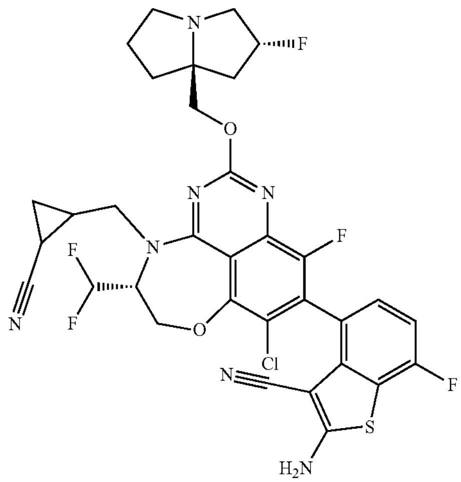 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716.4 |
| 854 | 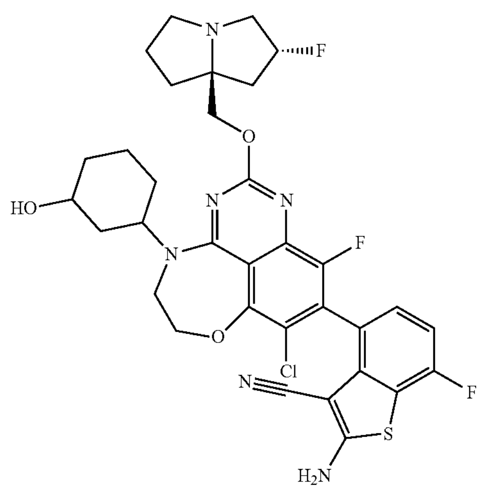 [SMILES: N#Cc1c(N)sc2c(F)ccc(-c3c(Cl)c4c5c(nc(OC[C@@]67CCCN6C[C@H](F)C7)nc5c3F)N(C3CCCC(O)C3)CCO4)c12] | 2-amino-4-(8-chloro-10-fluoro-2-(((2R,7aS)-2-fluorotetrahydro-1H-pyrrolizin-7a(5H)-yl)methoxy)-4-(3-hydroxycyclohexyl)-5,6-dihydro-4H-[1,4]oxazepino[5,6,7-de]quinazolin-9-yl)-7-fluorobenzo[b]thiophene-3-carbonitrile | 685.4 |
| 855 | 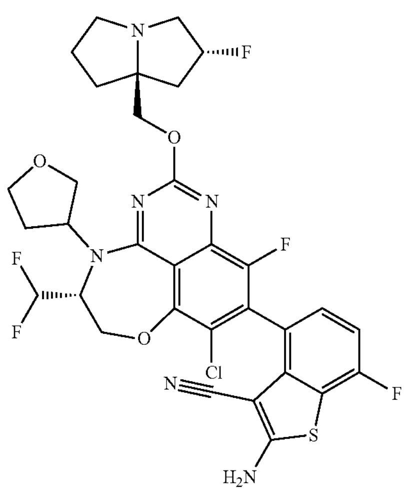 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C(F)F)CO4)c12] | 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 706.9 |

TABLE 1-continued

| No. | Structure | Chemical Name | [M + H]⁺ |
|---|---|---|---|
| 856 | 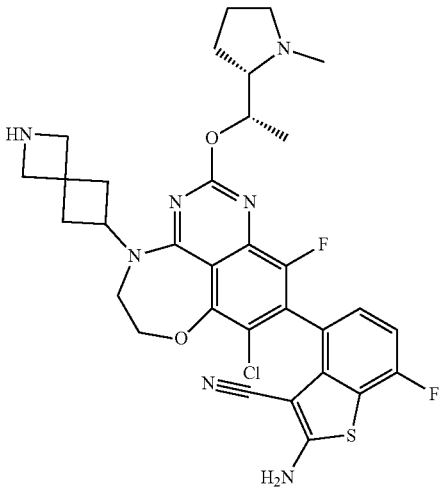 [SMILES: C[C@H](Oc1nc2c3c(c(Cl)c(-c4ccc(F)c5sc(N)c(C#N)c45)c(F)c3n1)OCCN2C1CC2(CNC2)C1)[C@@H]1CCCN1C] | 2-amino-4-(8-chloro-10-fluoro-2-((S)-1-((S)-1-methylpyrrolidin-2-yl)ethoxy)-4-(2-azaspiro[3.3]heptan-6-yl)-5,6-dihydro-4H-[1,4]oxazepino[5,6,7-de]quinazolin-9-yl)-7-fluorobenzo[b]thiophene-3-carbonitrile | 652.5 |
| 857 | 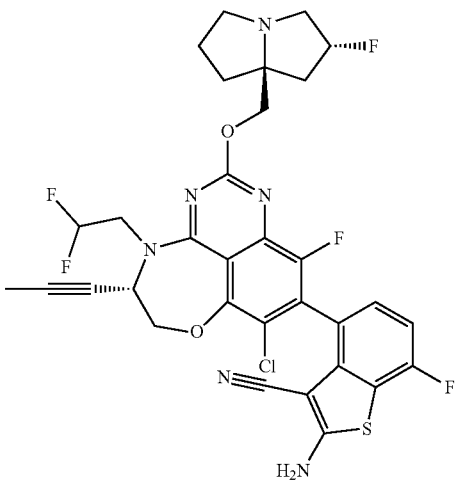 [SMILES: CC#C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-(prop-1-yn-1-yl)-5,6-dihydro-4H-[1,4]oxazepino[5,6,7-de]quinazolin-9-yl)-7-fluorobenzo[b]thiophene-3-carbonitrile | 688.9 |
| 858 | 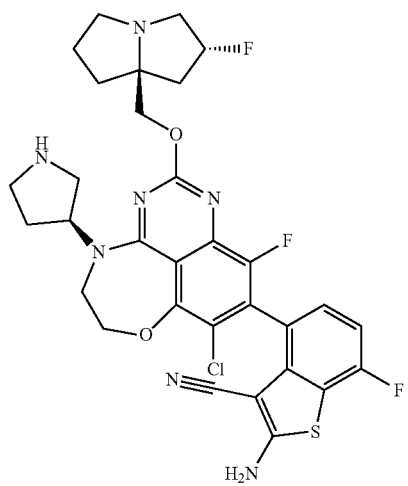 | 2-amino-4-(8-chloro-10-fluoro-2-(((2R,7aS)-2-fluorotetrahydro-1H-pyrrolizin-7a(5H)-yl)methoxy)-4-((S)-pyrrolidin-3-yl)-5,6-dihydro-4H-[1,4]oxazepino[5,6,7-de]quinazolin-9-yl)-7-fluorobenzo[b]thiophene-3-carbonitrile | 654.3 [M − H]⁻ |

TABLE 1-continued

| No. | Structure | Chemical Name | [M + H]+ |
|---|---|---|---|
| 859 | 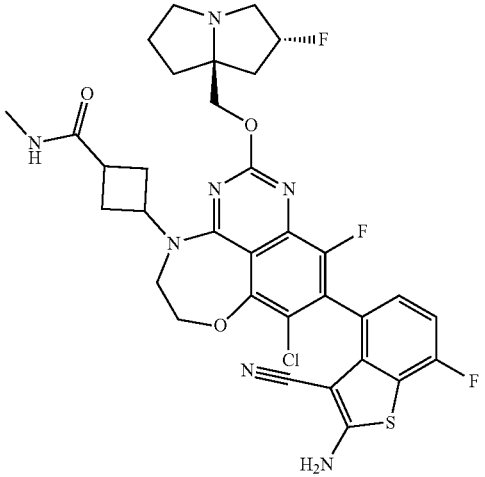 [SMILES: CNC(=O)C1CC(N2CCOc3c(Cl)c(-c4ccc(F)c5sc(N)c(C#N)c45)c(F)c4nc(OC[C@@]56CCCN5C[C@H](F)C6)nc2c34)C1] | 3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N-methylcyclobutane-1-carboxamide | 698.3 |
| 860 | 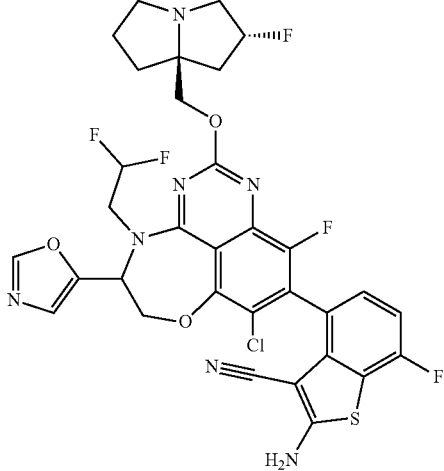 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(oxazol-5-yl)-5,6-dihydro-4H-[1,4]oxazepino[5,6,7-de]quinazolin-9-yl)-7-fluorobenzo[b]thiophene-3-carbonitrile | 717.8 |
| 861 | 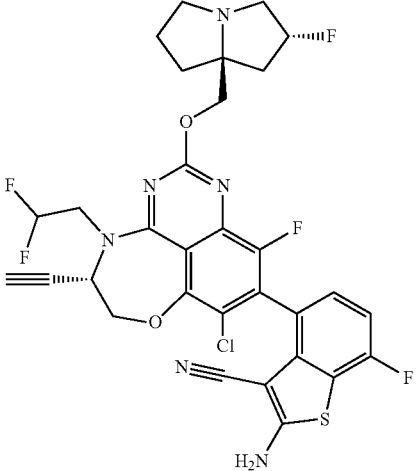 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 675 |

TABLE 1-continued

| No. | Structure | Chemical Name | [M + H]+ |
|---|---|---|---|
| 862 | 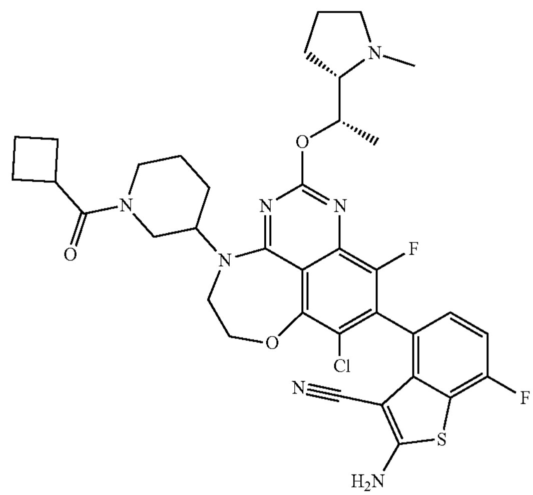 [SMILES: C[C@H](Oc1nc2c3c(c(Cl)c(-c4ccc(F)c5sc(N)c(C#N)c45)c(F)c3n1)OCCN2C1CCCN(C(=O)C2CCC2)C1)[C@@H]1CCCN1C] | 2-amino-4-(8-chloro-4-(1-(cyclobutanecarbonyl)piperidin-3-yl)-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile | 746.7 [M + Na]+ |
| 863 | 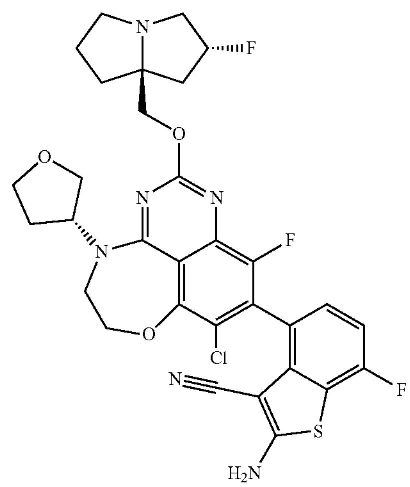 | 2-amino-4-(8-chloro-10-fluoro-2-(((2R,7aS)-2-fluorotetrahydro-1H-pyrrolizin-7a(5H)-yl)methoxy)-4-((R)-tetrahydrofuran-3-yl)-5,6-dihydro-4H-[1,4]oxazepino[5,6,7-de]quinazolin-9-yl)-7-fluorobenzo[b]thiophene-3-carbonitrile | 657.3 |
| 864 | 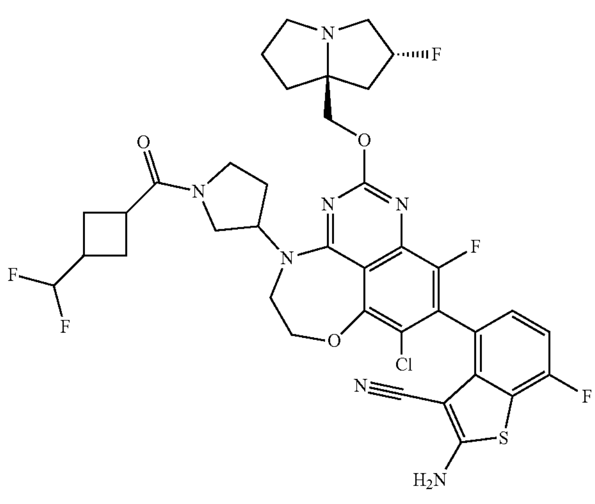 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C5CC(C(F)F)C5)C3)CCO4)c12] | 2-amino-4-(8-chloro-4-(1-(3-(difluoromethyl)cyclobutane-1-carbonyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 788.4 |

TABLE 1-continued

| No. | Structure | Chemical Name | [M + H]+ |
|---|---|---|---|
| 865 | 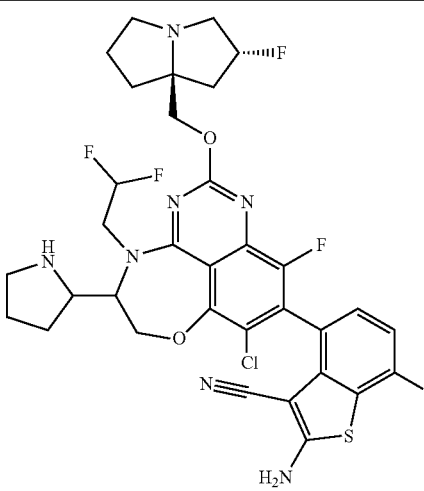 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(pyrrolidin-2-yl)-5,6-dihydro-4H-[1,4]oxazepino[5,6,7-de]quinazolin-9-yl)-7-fluorobenzo[b]thiophene-3-carbonitrile | 720.1 |
| 866 | 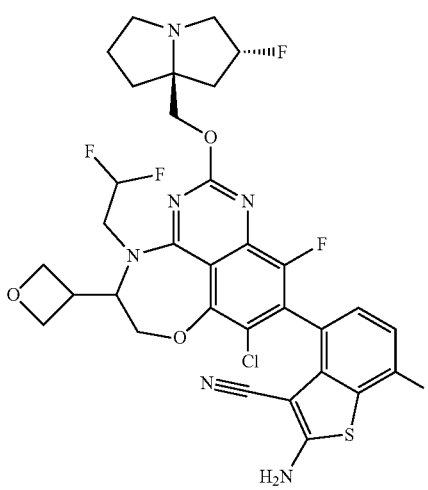 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazolin-9-yl)-7-fluorobenzo[b]thiophene-3-carbonitrile | 706.9 |
| 867 | 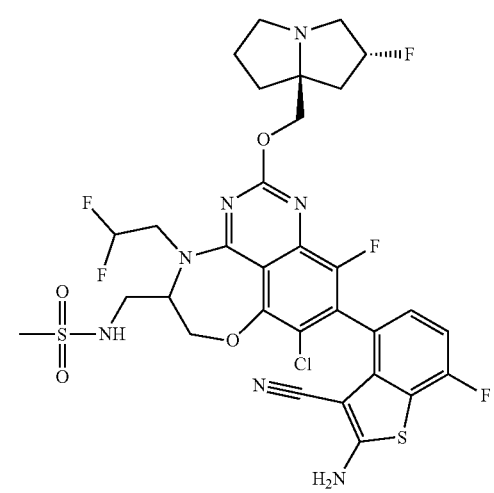 [SMILES: CS(=O)(=O)NCC1COc2c(Cl)c(-c3ccc(F)c4sc(N)c(C#N)c34)c(F)c3nc(OC[C@@]45CCCN4C[C@H](F)C5)nc(c23)N1CC(F)F] | N-((9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)methanesulfonamide | 758.3 |

TABLE 1-continued

| No. | Structure | Chemical Name | [M + H]⁺ |
|---|---|---|---|
| 868 | 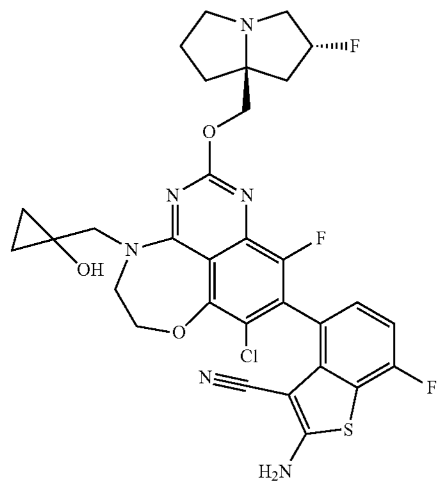 [SMILES: N#Cc1c(N)sc2c(F)ccc(-c3c(Cl)c4c5c(nc(OC[C@@]67CCCN6C[C@H](F)C7)nc5c3F)N(CC3(O)CC3)CCO4)c12] | 2-amino-4-(8-chloro-10-fluoro-2-(((2R,7aS)-2-fluorotetrahydro-1H-pyrrolizin-7a(5H)-yl)methoxy)-4-((1-hydroxycyclopropyl)methyl)-5,6-dihydro-4H-[1,4]oxazepino[5,6,7-de]quinazolin-9-yl)-7-fluorobenzo[b]thiophene-3-carbonitrile | 658.6 |
| 869 | 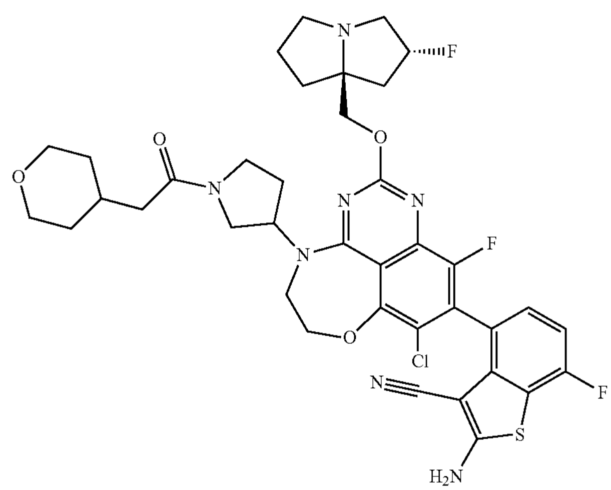 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)CC5CCOCC5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-(2-(tetrahydro-2H-pyran-4-yl)acetyl)pyrrolidin-3-yl)-5,6-dihydro-4H-[1,4]oxazepino[5,6,7-de]quinazolin-9-yl)-7-fluorobenzo[b]thiophene-3-carbonitrile | 782.4 |
| 870 | 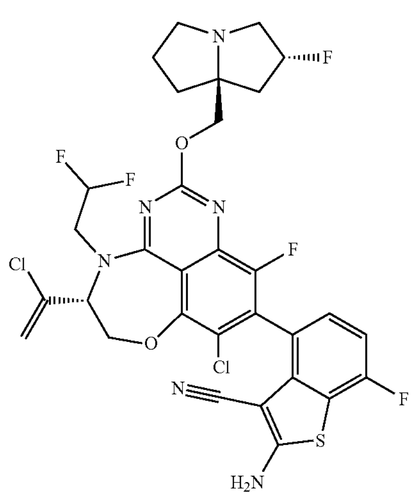 [SMILES: C=C(Cl)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 710.8 |

TABLE 1-continued

| No. | Structure | Chemical Name | [M + H]⁺ |
|---|---|---|---|
| 871 | 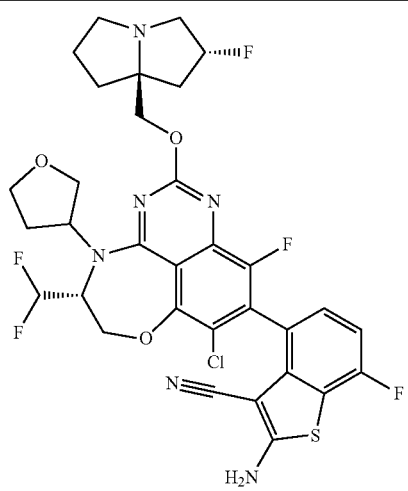 | 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 706.9 |
| 872 | 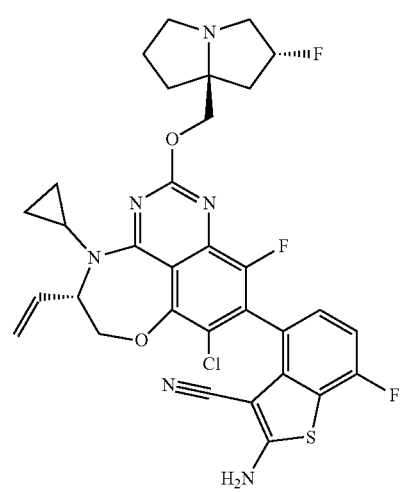 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CC1] | 2-amino-4-((5S)-8-chloro-4-cyclopropyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 652.9 |
| 873 | 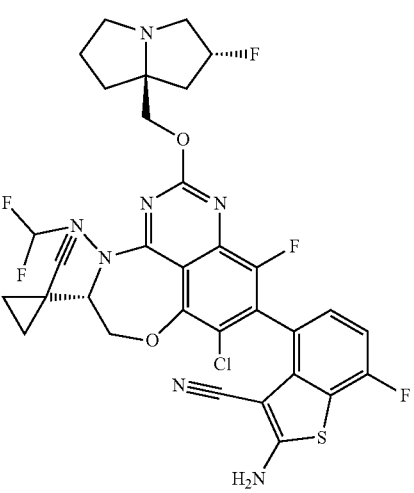 | 2-amino-4-((S)-8-chloro-5-(1-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |

TABLE 1-continued

| No. | Structure | Chemical Name | [M + H]⁺ |
|---|---|---|---|
| 874 | 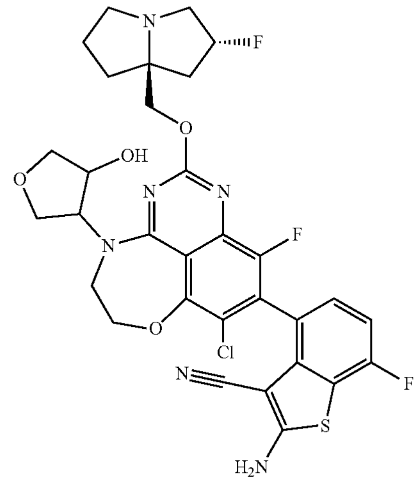 [SMILES: N#Cc1c(N)sc2c(F)ccc(-c3c(Cl)c4c5c(nc(OC[C@@]67CCCN6C[C@H](F)C7)nc5c3F)N(C3COCC3O)CCO4)c12] | 2-amino-4-(8-chloro-10-fluoro-2-(((2R,7aS)-2-fluorotetrahydro-1H-pyrrolizin-7a(5H)-yl)methoxy)-4-(4-hydroxytetrahydrofuran-3-yl)-5,6-dihydro-4H-[1,4]oxazepino[5,6,7-de]quinazolin-9-yl)-7-fluorobenzo[b]thiophene-3-carbonitrile | 674.3 |
| 875 | 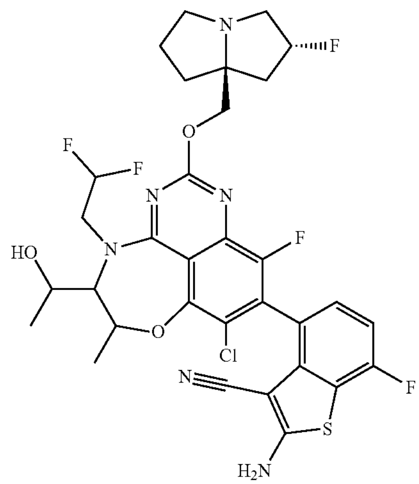 [SMILES: CC(O)C1C(C)Oc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 876 | 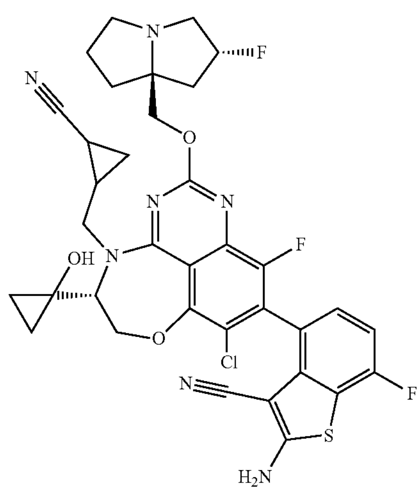 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |

TABLE 1-continued

| No. | Structure | Chemical Name | [M + H]+ |
|---|---|---|---|
| 877 | 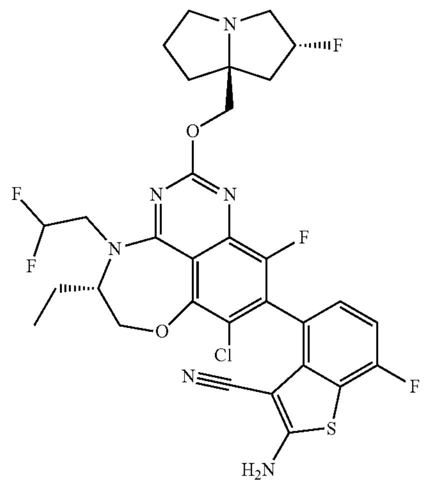 [SMILES: CC[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-ethyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 678.9 |
| 878 | 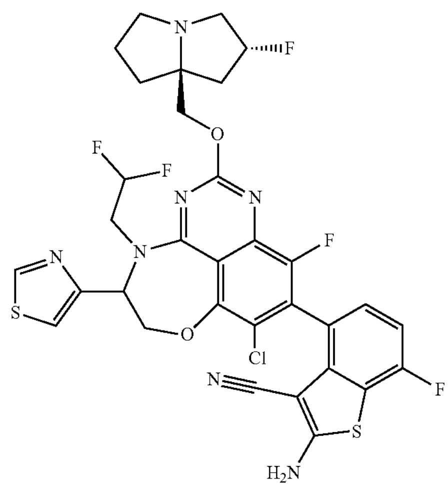 [SMILES: N#Cc1c(N)sc2c(F)ccc(-c3c(Cl)c4c5c(nc(OC[C@@]67CCCN6C[C@H](F)C7)nc5c3F)N(CC(F)F)C(c3cscn3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiazol-4-yl)-5,6-dihydro-4H-[1,4]oxazepino[5,6,7-de]quinazolin-9-yl)-7-fluorobenzo[b]thiophene-3-carbonitrile | 734.2 |
| 879 | 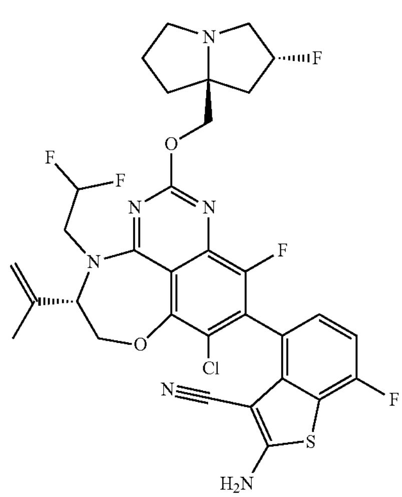 [SMILES: C=C(C)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-(prop-1-en-2-yl)-5,6-dihydro-4H-[1,4]oxazepino[5,6,7-de]quinazolin-9-yl)-7-fluorobenzo[b]thiophene-3-carbonitrile | 690.9 |

TABLE 1-continued

| No. | Structure | Chemical Name | [M + H]+ |
|---|---|---|---|
| 880 | 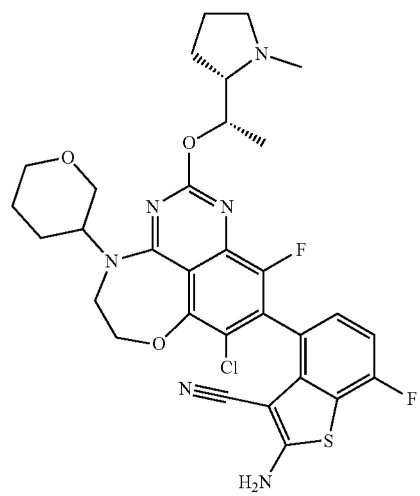 [SMILES: C[C@H](Oc1nc2c3c(c(Cl)c(-c4ccc(F)c5sc(N)c(C#N)c45)c(F)c3n1)OCCN2C1CCCOC1)[C@@H]1CCCN1C] | 2-amino-4-(8-chloro-10-fluoro-2-((S)-1-((S)-1-methylpyrrolidin-2-yl)ethoxy)-4-(tetrahydro-2H-pyran-3-yl)-5,6-dihydro-4H-[1,4]oxazepino[5,6,7-de]quinazolin-9-yl)-7-fluorobenzo[b]thiophene-3-carbonitrile | 642.3 |
| 881 | 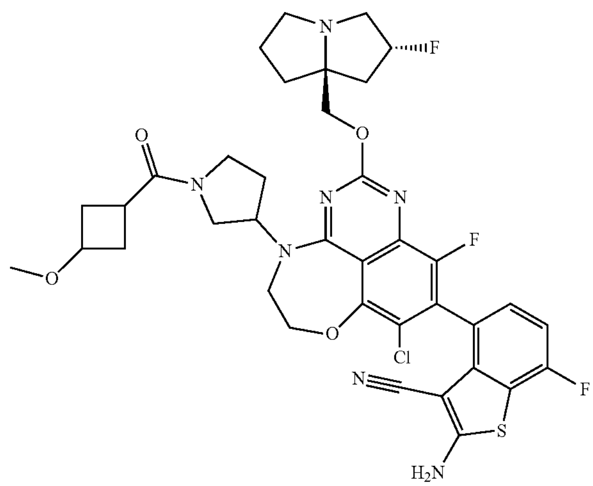 [SMILES: COC1CC(C(=O)N2CCC(N3CCOc4c(Cl)c(-c5ccc(F)c6sc(N)c(C#N)c56)c(F)c5nc(OC[C@@]67CCCN6C[C@H](F)C7)nc3c45)C2)C1] | 2-amino-4-(8-chloro-10-fluoro-2-(((2R,7aS)-2-fluorotetrahydro-1H-pyrrolizin-7a(5H)-yl)methoxy)-4-(1-(3-methoxycyclobutane-1-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 768.4 |
| 882 | 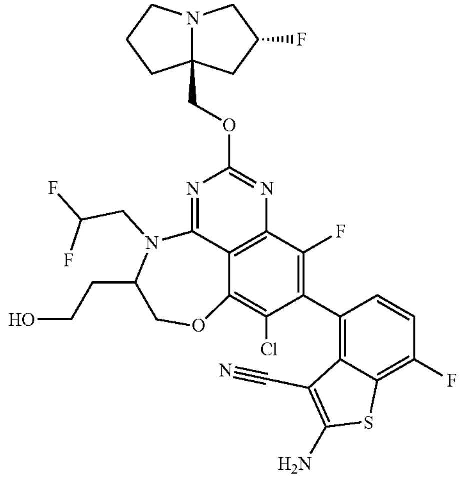 [SMILES: N#Cc1c(N)sc2c(F)ccc(-c3c(Cl)c4c5c(nc(OC[C@@]67CCCN6C[C@H](F)C7)nc5c3F)N(CC(F)F)C(CCO)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxyethyl)-5,6-dihydro-4H-[1,4]oxazepino[5,6,7-de]quinazolin-9-yl)-7-fluorobenzo[b]thiophene-3-carbonitrile | 694.8 |

TABLE 1-continued

| No. | Structure | Chemical Name | [M + H]+ |
|---|---|---|---|
| 883 | 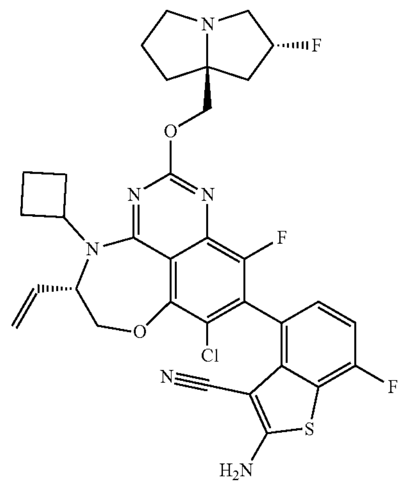 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCC1] | 2-amino-4-((5S)-8-chloro-4-cyclobutyl-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 666.9 |
| 884 | 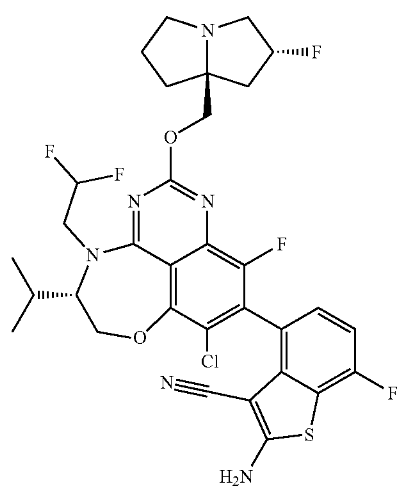 [SMILES: CC(C)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-isopropyl-5,6-dihydro-4H-[1,4]oxazepino[5,6,7-de]quinazolin-9-yl)-7-fluorobenzo[b]thiophene-3-carbonitrile | 692.9 |
| 885 | 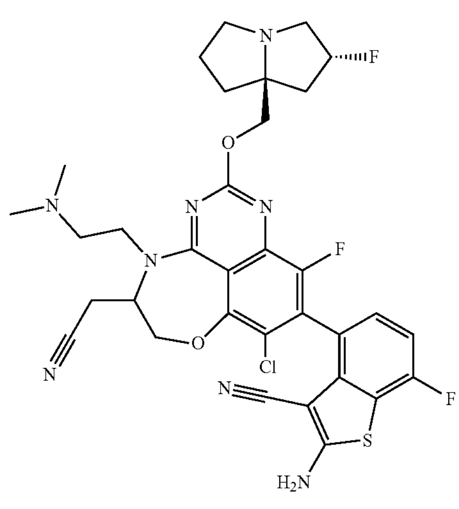 [SMILES: CN(C)CCN1c2nc(OC[C@@]34CCCN3C[C@H](F)C4)nc3c(F)c(-c4ccc(F)c5sc(N)c(C#N)c45)c(Cl)c(c23)OCC1CC#N] | 2-amino-4-(8-chloro-5-(cyanomethyl)-4-(2-(dimethylamino)ethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 697.1 |

TABLE 1-continued

| No. | Structure | Chemical Name | [M + H]+ |
|---|---|---|---|
| 886 | 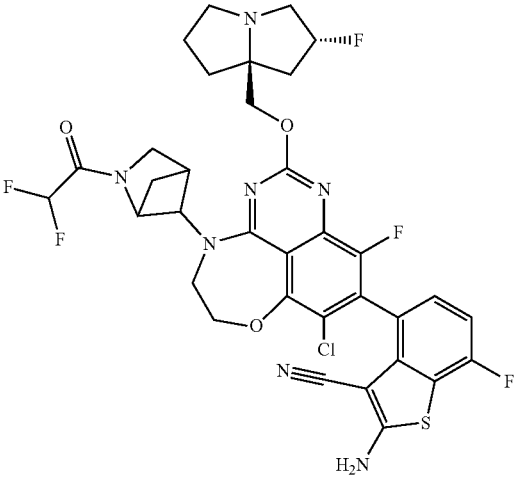 [SMILES: N#Cc1c(N)sc2c(F)ccc(-c3c(Cl)c4c5c(nc(OC[C@@]67CCCN6C[C@H](F)C7)nc5c3F)N(C3C5CC3N(C(=O)C(F)F)C5)CCO4)c12] | 2-amino-4-(8-chloro-4-(2-(2,2-difluoroacetyl)-2-azabicyclo[2.1.1]hexan-5-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 746.3 |
| 887 | 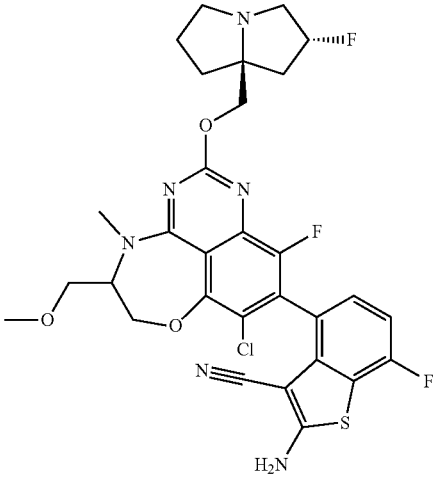 [SMILES: COCC1COc2c(Cl)c(-c3ccc(F)c4sc(N)c(C#N)c34)c(F)c3nc(OC[C@@]45CCCN4C[C@H](F)C5)nc(c23)N1C] | 2-amino-4-(8-chloro-10-fluoro-2-(((2R,7aS)-2-fluorotetrahydro-1H-pyrrolizin-7a(5H)-yl)methoxy)-5-(methoxymethyl)-4-methyl-5,6-dihydro-4H-[1,4]oxazepino[5,6,7-de]quinazolin-9-yl)-7-fluorobenzo[b]thiophene-3-carbonitrile | 645.3 |
| 888 | 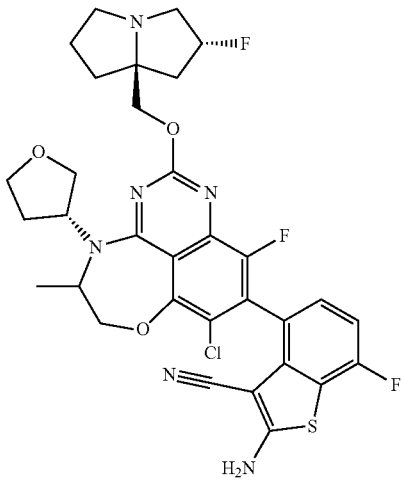 [SMILES: CC1COc2c(Cl)c(-c3ccc(F)c4sc(N)c(C#N)c34)c(F)c3nc(OC[C@@]45CCCN4C[C@H](F)C5)nc(c23)N1[C@@H]1CCOC1] | 2-amino-4-(8-chloro-10-fluoro-2-(((2R,7aS)-2-fluorotetrahydro-1H-pyrrolizin-7a(5H)-yl)methoxy)-5-methyl-4-((R)-tetrahydrofuran-3-yl)-5,6-dihydro-4H-[1,4]oxazepino[5,6,7-de]quinazolin-9-yl)-7-fluorobenzo[b]thiophene-3-carbonitrile | 670.9 |

TABLE 1-continued

| No. | Structure | Chemical Name | [M + H]+ |
|---|---|---|---|
| 889 | 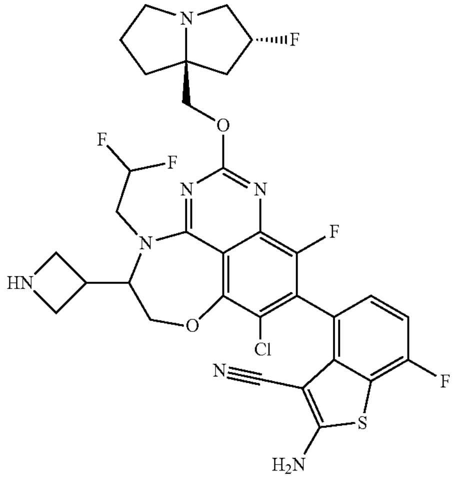 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CNC3)CO4)c12] | 2-amino-4-(5-(azetidin-3-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 706.2 |
| 890 | 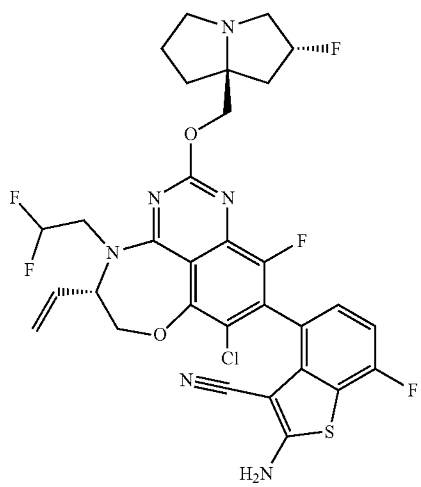 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 677 |
| 891 | 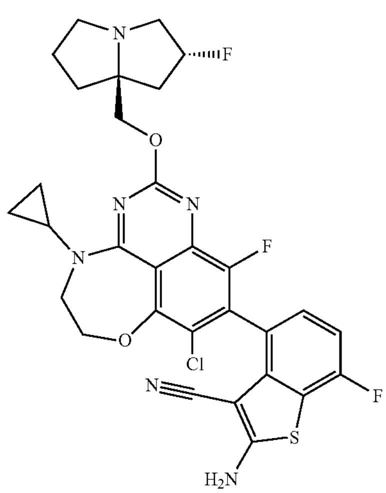 [SMILES: N#Cc1c(N)sc2c(F)ccc(-c3c(Cl)c4c5c(nc(OC[C@@]67CCCN6C[C@H](F)C7)nc5c3F)N(C3CC3)CCO4)c12] | 2-amino-4-(8-chloro-4-cyclopropyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 627.2 |

TABLE 1-continued

| No. | Structure | Chemical Name | [M + H]⁺ |
|---|---|---|---|
| 892 | 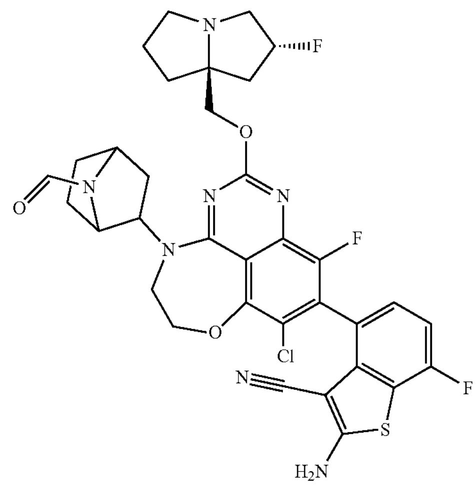 [SMILES: N#Cc1c(N)sc2c(F)ccc(-c3c(Cl)c4c5c(nc(OC[C@@]67CCCN6C[C@H](F)C7)nc5c3F)N(C3CC5CCC3N5C=O)CCO4)c12] | 2-amino-4-(8-chloro-10-fluoro-2-(((2R,7aS)-2-fluorotetrahydro-1H-pyrrolizin-7a(5H)-yl)methoxy)-4-(7-formyl-7-azabicyclo[2.2.1]heptan-2-yl)-5,6-dihydro-4H-[1,4]oxazepino[5,6,7-de]quinazolin-9-yl)-7-fluorobenzo[b]thiophene-3-carbonitrile | 711.4 |
| 893 | 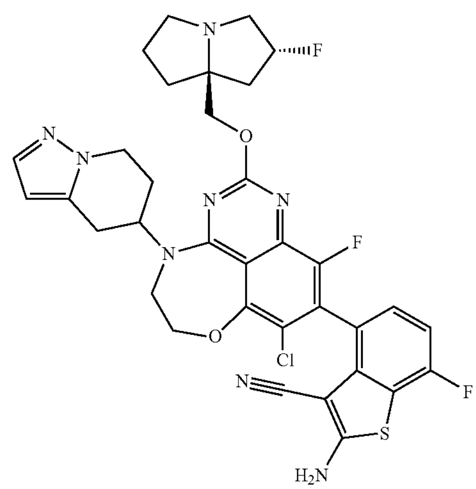 [SMILES: N#Cc1c(N)sc2c(F)ccc(-c3c(Cl)c4c5c(nc(OC[C@@]67CCCN6C[C@H](F)C7)nc5c3F)N(C3CCn5nccc5C3)CCO4)c12] | 2-amino-4-(8-chloro-10-fluoro-2-(((2R,7aS)-2-fluorotetrahydro-1H-pyrrolizin-7a(5H)-yl)methoxy)-4-(4,5,6,7-tetrahydropyrazolo[1,5-a]pyridin-5-yl)-5,6-dihydro-4H-[1,4]oxazepino[5,6,7-de]quinazolin-9-yl)-7-fluorobenzo[b]thiophene-3-carbonitrile | 707.3 |
| 894 | 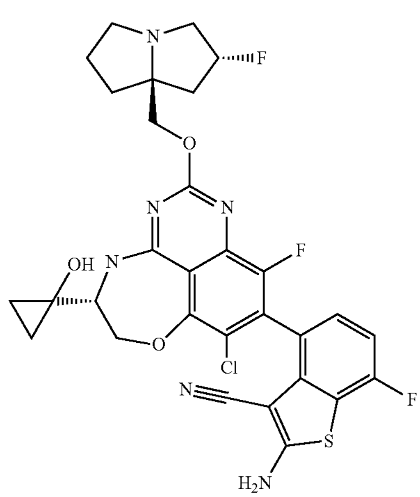 [SMILES: N#Cc1c(N)sc2c(F)ccc(-c3c(Cl)c4c5c(nc(OC[C@@]67CCCN6C[C@H](F)C7)nc5c3F)N[C@@H](C3(O)CC3)CO4)c12] | 2-amino-4-((R)-8-chloro-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 643 |

TABLE 1-continued

| No. | Structure | Chemical Name | [M + H]⁺ |
|---|---|---|---|
| 895 | 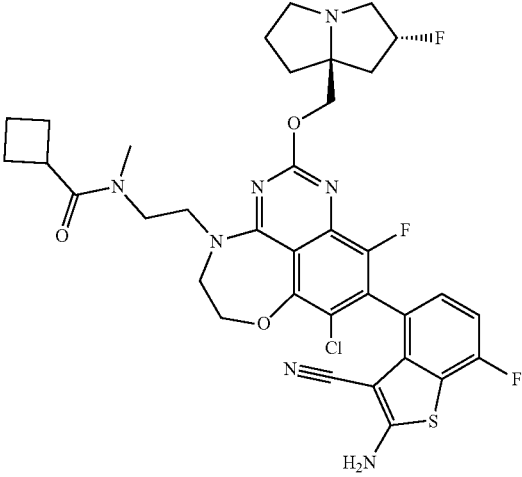 [SMILES: CN(CCN1CCOc2c(Cl)c(-c3ccc(F)c4sc(N)c(C#N)c34)c(F)c3nc(OC[C@@]45CCCN4C[C@H](F)C5)nc1c23)C(=O)C1CCC1] | N-(2-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)-N-methylcyclobutanecarboxamide | 726.3 |
| 896 | 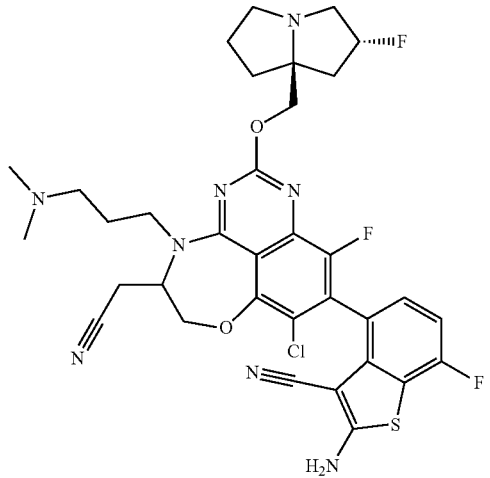 [SMILES: CN(C)CCCN1c2nc(OC[C@@]34CCCN3C[C@H](F)C4)nc3c(F)c(-c4ccc(F)c5sc(N)c(C#N)c45)c(Cl)c(c23)OCC1CC#N] | 2-amino-4-(8-chloro-5-(cyanomethyl)-4-(3-(dimethylamino)propyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 711.2 |
| 897 | 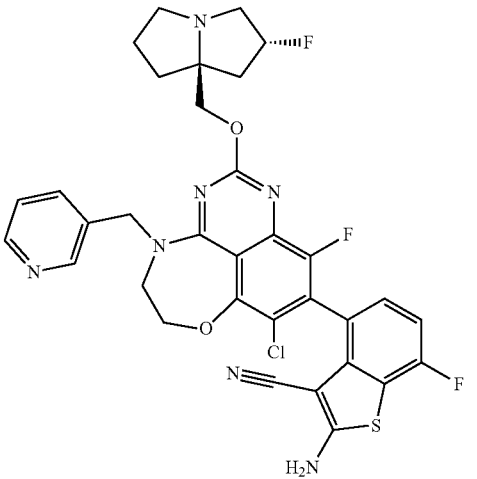 [SMILES: N#Cc1c(N)sc2c(F)ccc(-c3c(Cl)c4c5c(nc(OC[C@@]67CCCN6C[C@H](F)C7)nc5c3F)N(Cc3cccnc3)CCO4)c12] | 2-amino-4-(8-chloro-10-fluoro-2-(((2R,7aS)-2-fluorotetrahydro-1H-pyrrolizin-7a(5H)-yl)methoxy)-4-(pyridin-3-ylmethyl)-5,6-dihydro-4H-[1,4]oxazepino[5,6,7-de]quinazolin-9-yl)-7-fluorobenzo[b]thiophene-3-carbonitrile | 678.1 |

TABLE 1-continued

| No. | Structure | Chemical Name | [M + H]+ |
|---|---|---|---|
| 898 | 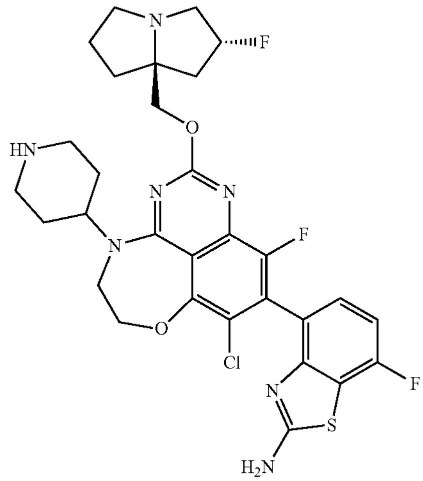 [SMILES: Nc1nc2c(-c3c(Cl)c4c5c(nc(OC[C@@]67CCCN6C[C@H](F)C7)nc5c3F)N(C3CCNCC3)CCO4)ccc(F)c2s1] | 4-(8-chloro-10-fluoro-2-(((2R,7aS)-2-fluorotetrahydro-1H-pyrrolizin-7a(5H)-yl)methoxy)-4-(piperidin-4-yl)-5,6-dihydro-4H-[1,4]oxazepino[5,6,7-de]quinazolin-9-yl)-7-fluorobenzo[d]thiazol-2-amine | 646.2 |
| 899 | 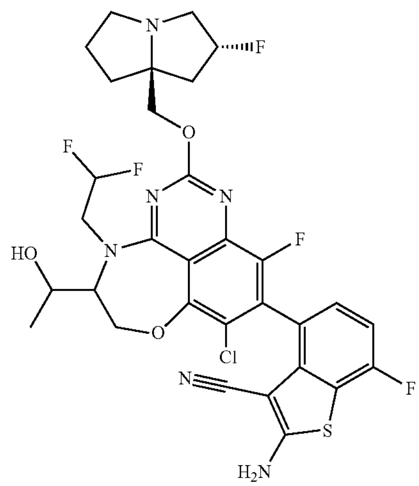 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile | 695.2 |
| 900 | 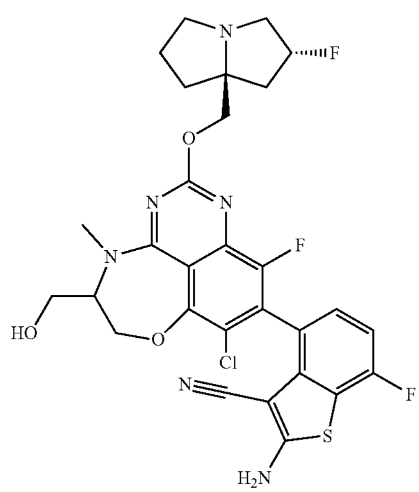 [SMILES: CN1c2nc(OC[C@@]34CCCN3C[C@H](F)C4)nc3c(F)c(-c4ccc(F)c5sc(N)c(C#N)c45)c(Cl)c(c23)OCC1CO] | 2-amino-4-(8-chloro-10-fluoro-2-(((2R,7aS)-2-fluorotetrahydro-1H-pyrrolizin-7a(5H)-yl)methoxy)-5-(hydroxymethyl)-4-methyl-5,6-dihydro-4H-[1,4]oxazepino[5,6,7-de]quinazolin-9-yl)-7-fluorobenzo[b]thiophene-3-carbonitrile | 631.2 |

TABLE 1-continued

| No. | Structure | Chemical Name | [M + H]⁺ |
|---|---|---|---|
| 901 | 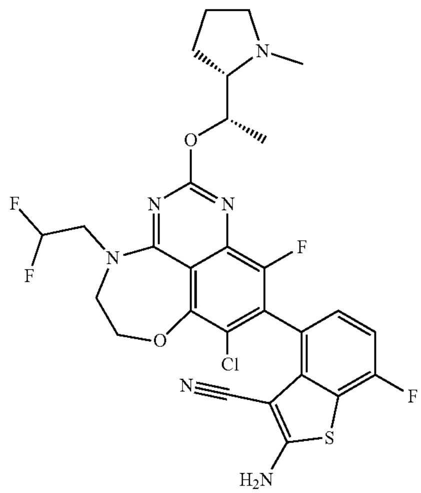 [SMILES: C[C@H](Oc1nc2c3c(c(Cl)c(-c4ccc(F)c5sc(N)c(C#N)c45)c(F)c3n1)OCCN2CC(F)F)[C@@H]1CCCN1C] | 2-amino-4-(8-chloro-4-(2,2-difluoroethyl)-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile | 621.1 |
| 902 | 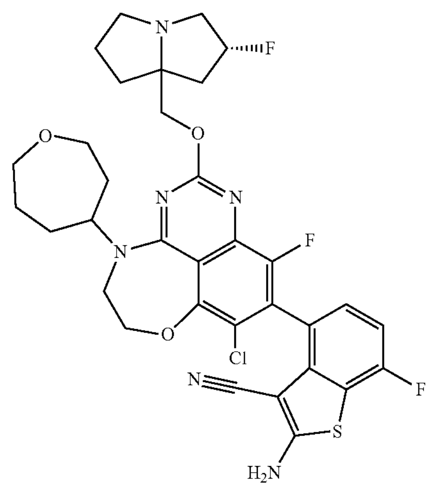 [SMILES: N#Cc1c(N)sc2c(F)ccc(-c3c(Cl)c4c5c(nc(OCC67CCCN6C[C@H](F)C7)nc5c3F)N(C3CCCOCC3)CCO4)c12] | 2-amino-4-(8-chloro-10-fluoro-2-(((2R)-2-fluorotetrahydro-1H-pyrrolizin-7a(5H)-yl)methoxy)-4-(oxepan-4-yl)-5,6-dihydro-4H-[1,4]oxazepino[5,6,7-de]quinazolin-9-yl)-7-fluorobenzo[b]thiophene-3-carbonitrile | 686.4 |
| 903 | 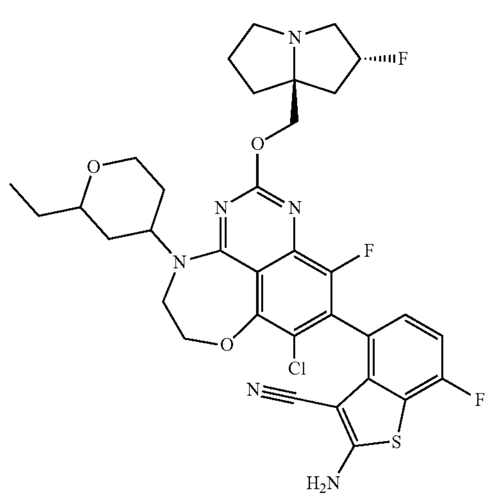 [SMILES: CCC1CC(N2CCOc3c(Cl)c(-c4ccc(F)c5sc(N)c(C#N)c45)c(F)c4nc(OC[C@@]56CCCN5C[C@H](F)C6)nc2c34)CCO1] | 2-amino-4-(8-chloro-4-(2-ethyltetrahydro-2H-pyran-4-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 699.4 |

TABLE 1-continued

| No. | Structure | Chemical Name | [M + H]+ |
|---|---|---|---|
| 904 | 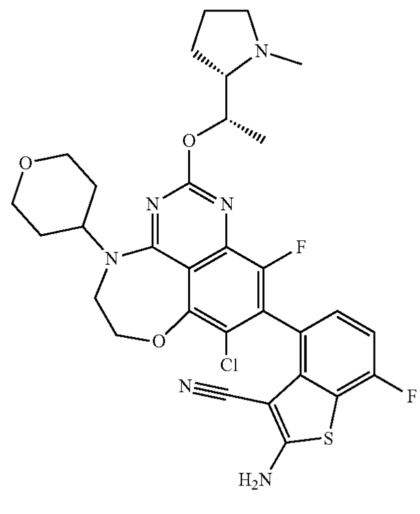 [SMILES: C[C@H](Oc1nc2c3c(c(Cl)c(-c4ccc(F)c5sc(N)c(C#N)c45)c(F)c3n1)OCCN2C1CCOCC1)[C@@H]1CCCN1C] | 2-amino-4-(8-chloro-10-fluoro-2-((S)-1-((S)-1-methylpyrrolidin-2-yl)ethoxy)-4-(tetrahydro-2H-pyran-4-yl)-5,6-dihydro-4H-[1,4]oxazepino[5,6,7-de]quinazolin-9-yl)-7-fluorobenzo[b]thiophene-3-carbonitrile | 641.2 |
| 905 | 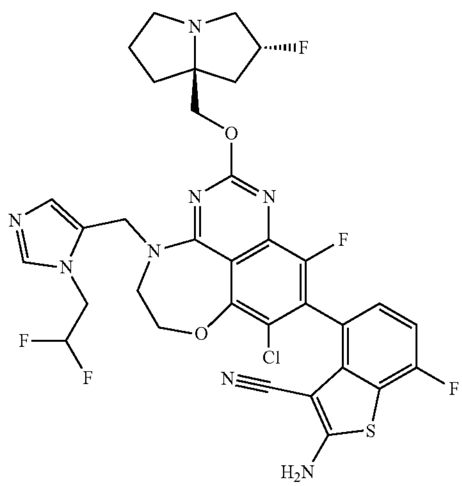 [SMILES: N#Cc1c(N)sc2c(F)ccc(-c3c(Cl)c4c5c(nc(OC[C@@]67CCCN6C[C@H](F)C7)nc5c3F)N(Cc3cncn3CC(F)F)CCO4)c12] | 2-amino-4-(8-chloro-4-((1-(2,2-difluoroethyl)-1H-imidazol-5-yl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 731.2 |
| 906 | 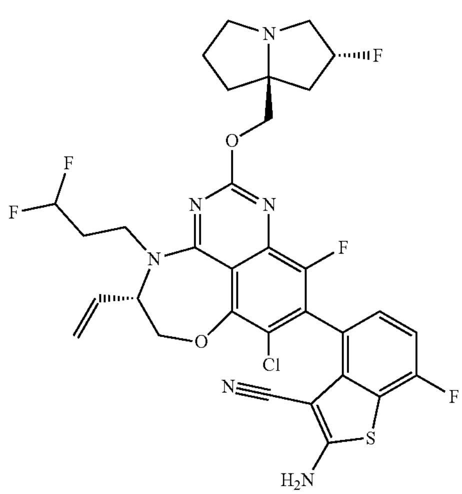 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile | 691.1 |

TABLE 1-continued

| No. | Structure | Chemical Name | [M + H]⁺ |
|---|---|---|---|
| 907 | 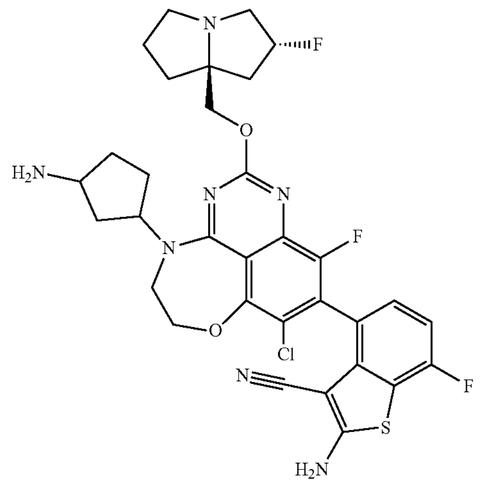 [SMILES: N#Cc1c(N)sc2c(F)ccc(-c3c(Cl)c4c5c(nc(OC[C@@]67CCCN6C[C@H](F)C7)nc5c3F)N(C3CCC(N)C3)CCO4)c12] | 2-amino-4-(4-(3-aminocyclopentyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 668.5 [M − H]⁻ |
| 908 | 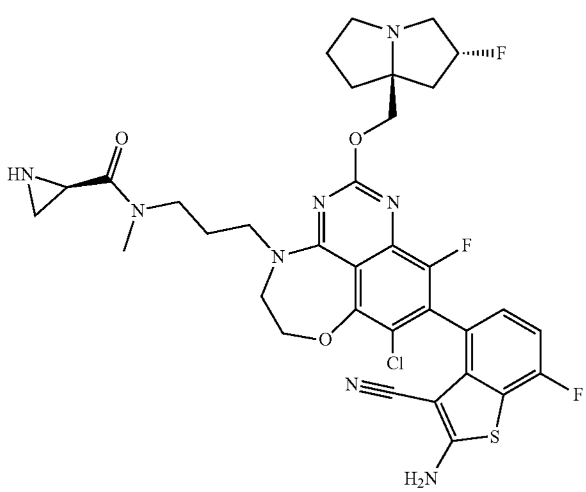 [SMILES: CN(CCCN1CCOc2c(Cl)c(-c3ccc(F)c4sc(N)c(C#N)c34)c(F)c3nc(OC[C@@]45CCCN4C[C@H](F)C5)nc1c23)C(=O)[C@H]1CN1] | (2R)-N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)propyl)-N-methylaziridine-2-carboxamide | 727.5 |
| 909 | 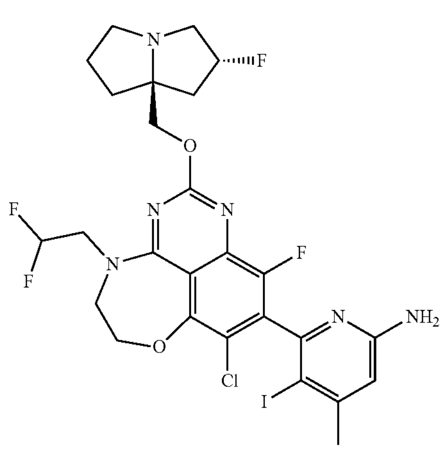 [SMILES: Cc1cc(N)nc(-c2c(Cl)c3c4c(nc(OC[C@@]56CCCN5C[C@H](F)C6)nc4c2F)N(CC(F)F)CCO3)c1I] | 6-(8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-5-iodo-4-methylpyridin-2-amine | 693.1 |

TABLE 1-continued

| No. | Structure | Chemical Name | [M + H]+ |
|---|---|---|---|
| 910 | 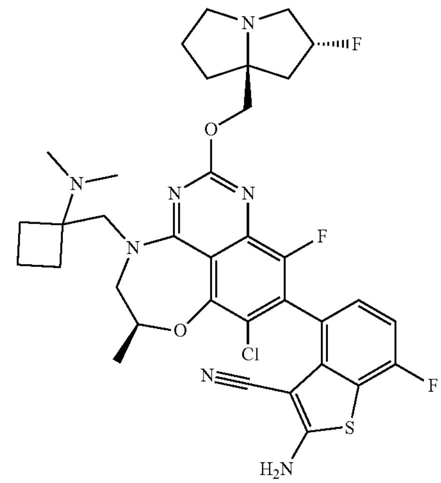 [SMILES: C[C@H]1CN(CC2(N(C)C)CCC2)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-((1-(dimethylamino)cyclobutyl)methyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 712.3 |
| 911 | 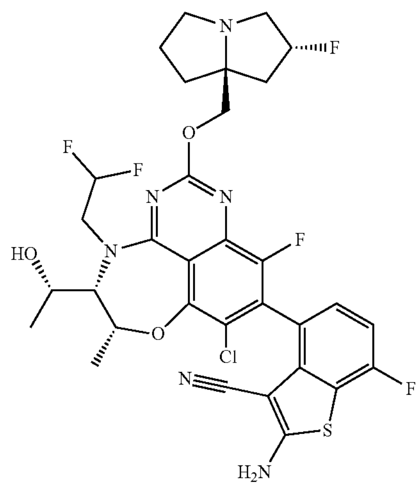 [SMILES: C[C@H](O)[C@H]1[C@@H](C)Oc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S,6R)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 912 | 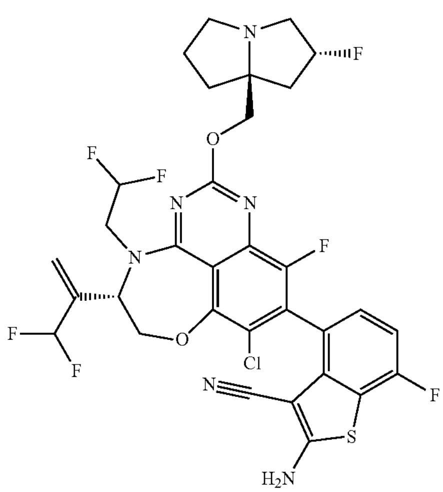 [SMILES: C=C(C(F)F)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-(3,3-difluoroprop-1-en-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 726.9 |

TABLE 1-continued

| No. | Structure | Chemical Name | [M + H]+ |
|---|---|---|---|
| 913 | 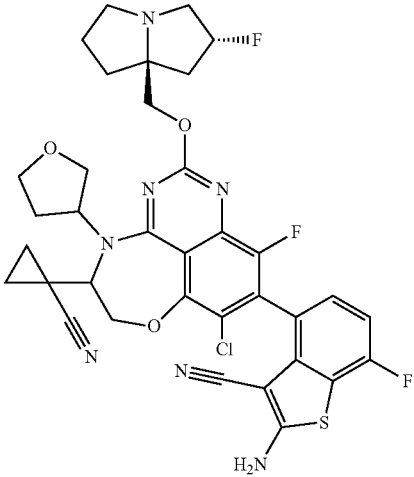 | 2-amino-4-(8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 722 |
| 914 | 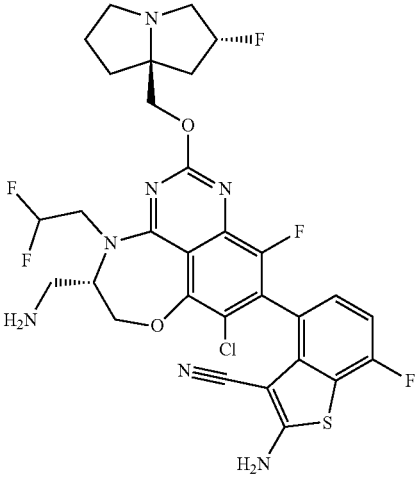 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](CN)CO4)c12] | 2-amino-4-((S)-5-(aminomethyl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 680.4 |
| 915 | 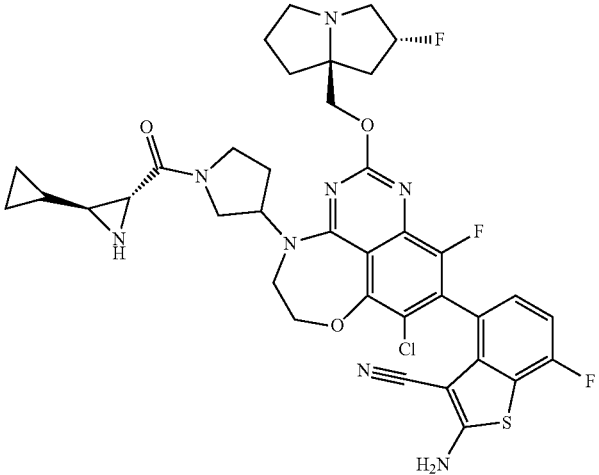 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)[C@@H]5N[C@H]5C5CC5)C3)CCO4)c12] | 2-amino-4-(8-chloro-4-(1-((2R,3S)-3-cyclopropylaziridine-2-carbonyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 765.5 |

TABLE 1-continued

| No. | Structure | Chemical Name | [M + H]⁺ |
|---|---|---|---|
| 916 | 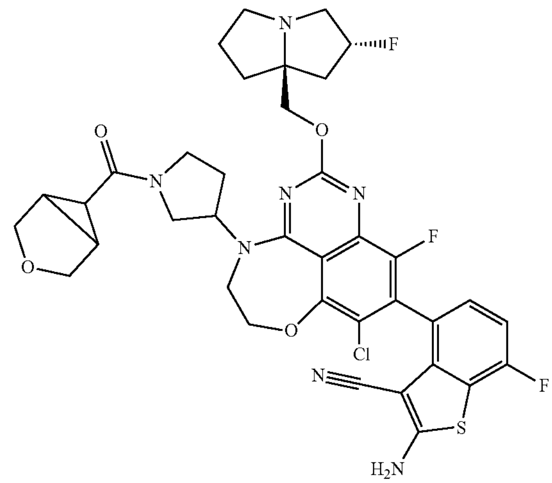 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C5C6COCC65)C3)CCO4)c12] | 4-(4-(1-(3-oxabicyclo[3.1.0]hexane-6-carbonyl)pyrrolidin-3-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 766.4 |
| 917 | 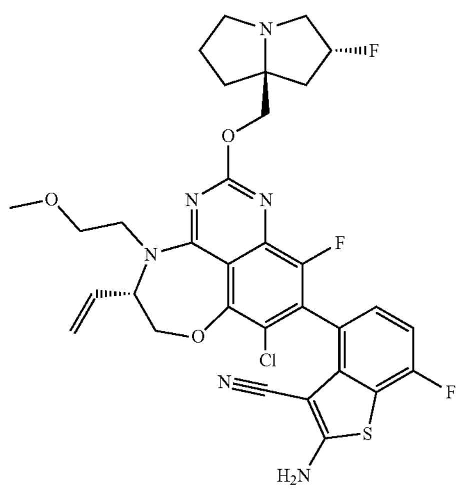 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1CCOC] | 2-amino-4-((5S)-8-chloro-10-fluoro-2-(((2R,7aS)-2-fluorotetrahydro-1H-pyrrolizin-7a(5H)-yl)methoxy)-4-(2-methoxyethyl)-5-vinyl-5,6-dihydro-4H-[1,4]oxazepino[5,6,7-de]quinazolin-9-yl)-7-fluorobenzo[b]thiophene-3-carbonitrile | 671.3 |
| 918 | 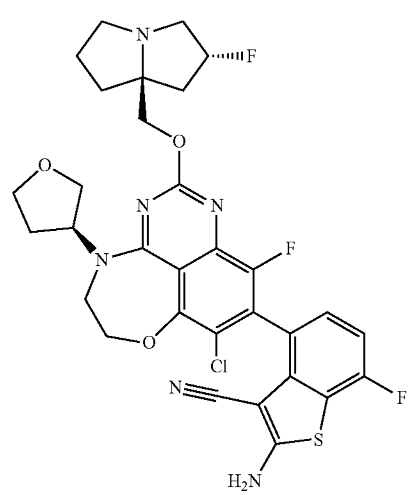 [SMILES: N#Cc1c(N)sc2c(F)ccc(-c3c(Cl)c4c5c(nc(OC[C@@]67CCCN6C[C@H](F)C7)nc5c3F)N([C@H]3CCOC3)CCO4)c12] | 2-amino-4-(8-chloro-10-fluoro-2-(((2R,7aS)-2-fluorotetrahydro-1H-pyrrolizin-7a(5H)-yl)methoxy)-4-((S)-tetrahydrofuran-3-yl)-5,6-dihydro-4H-[1,4]oxazepino[5,6,7-de]quinazolin-9-yl)-7-fluorobenzo[b]thiophene-3-carbonitrile | 657.3 |

TABLE 1-continued

| No. | Structure | Chemical Name | [M + H]+ |
|---|---|---|---|
| 919 | 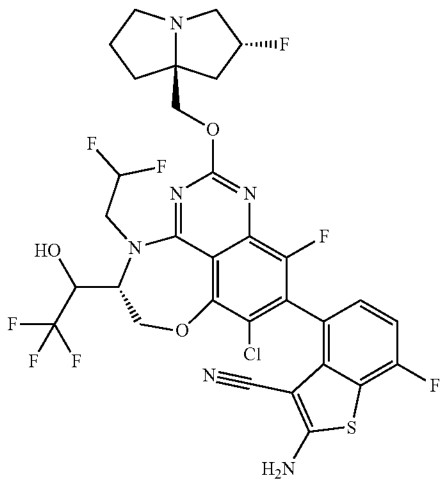 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C(O)C(F)(F)F)CO4)c12] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-(2,2,2-trifluoro-1-hydroxyethyl)-5,6-dihydro-4H-[1,4]oxazepino[5,6,7-de]quinazolin-9-yl)-7-fluorobenzo[b]thiophene-3-carbonitrile | 748.9 |
| 920 | 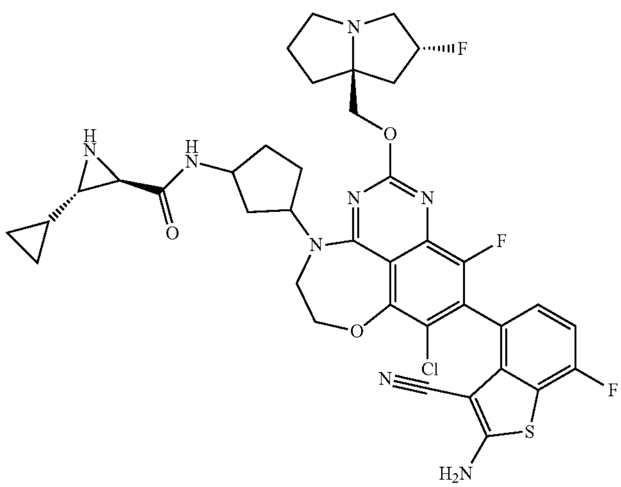 [SMILES: N#Cc1c(N)sc2c(F)ccc(-c3c(Cl)c4c5c(nc(OC[C@@]67CCCN6C[C@H](F)C7)nc5c3F)N(C3CCC(NC(=O)[C@@H]5N[C@H]5C5CC5)C3)CCO4)c12] | (2R,3S)-N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclopentyl)-3-cyclopropylaziridine-2-carboxamide | 779.4 |
| 921 | 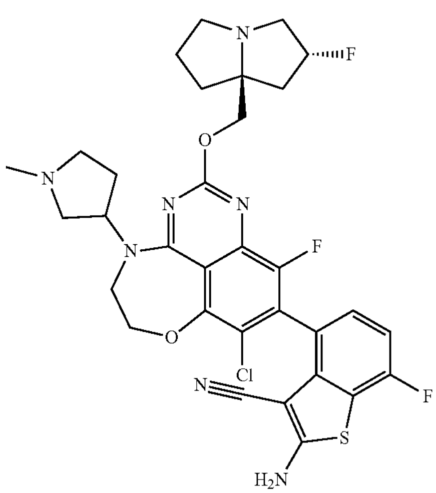 [SMILES: CN1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(1-methylpyrrolidin-3-yl)-5,6-dihydro-4H-[1,4]oxazepino[5,6,7-de]quinazolin-9-yl)-7-fluorobenzo[b]thiophene-3-carbonitrile | 670.5 |

TABLE 1-continued

| No. | Structure | Chemical Name | [M + H]+ |
|---|---|---|---|
| 922 | 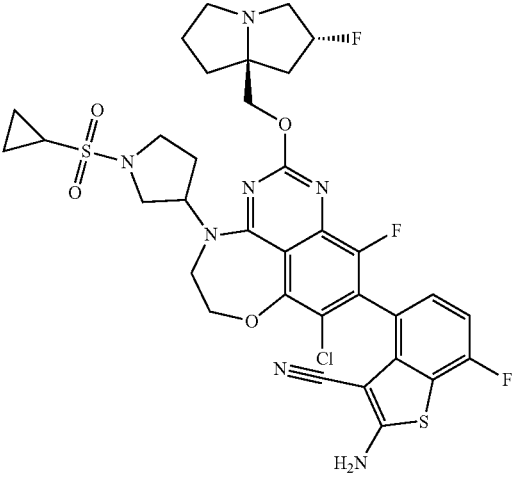 [SMILES: N#Cc1c(N)sc2c(F)ccc(-c3c(Cl)c4c5c(nc(OC[C@@]67CCCN6C[C@H](F)C7)nc5c3F)N(C3CCN(S(=O)(=O)C5CC5)C3)CCO4)c12] | 2-amino-4-(8-chloro-4-(1-(cyclopropylsulfonyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 760.5 |
| 923 | 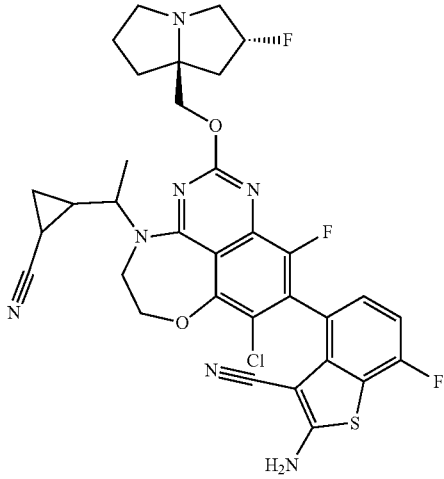 [SMILES: CC(C1CC1C#N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(1-(2-cyanocyclopropyl)ethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 679.8 |
| 924 | 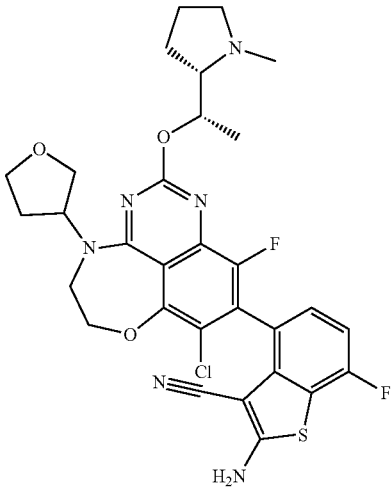 [SMILES: C[C@H](Oc1nc2c3c(c(Cl)c(-c4ccc(F)c5sc(N)c(C#N)c45)c(F)c3n1)OCCN2C1CCOC1)[C@@H]1CCCN1C] | 2-amino-4-(8-chloro-10-fluoro-2-((S)-1-((S)-1-methylpyrrolidin-2-yl)ethoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 627.2 |

TABLE 1-continued

| No. | Structure | Chemical Name | [M + H]+ |
|---|---|---|---|
| 925 | 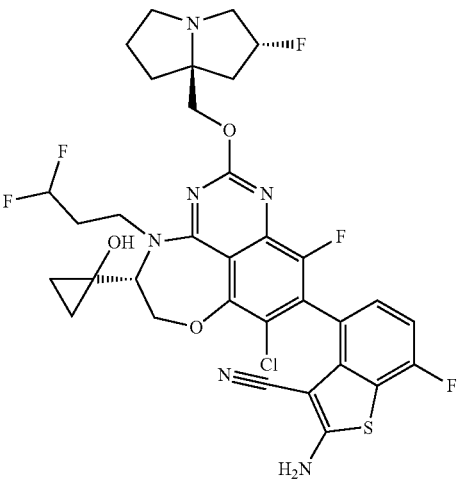 [SMILES: N#Cc1c(N)sc2c(F)ccc(-c3c(Cl)c4c5c(nc(OC[C@@]67CCCN6C[C@H](F)C7)nc5c3F)N(CCC(F)F)[C@@H](C3(O)CC3)CO4)c12] | 2-amino-4-((R)-8-chloro-4-(3,3-difluoropropyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 721 |
| 926 | 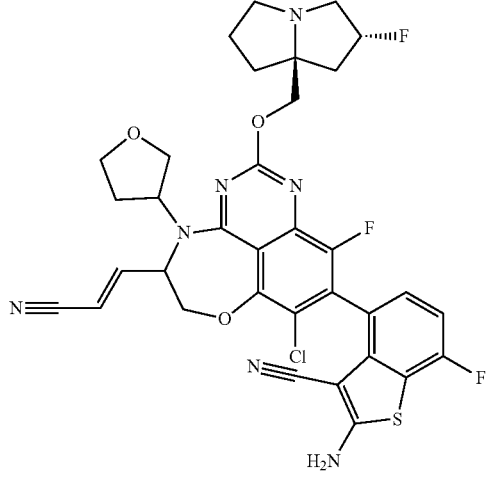 [SMILES: N#C/C=C/C1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-(8-chloro-5-((E)-2-cyanovinyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 708.1 |
| 927 | 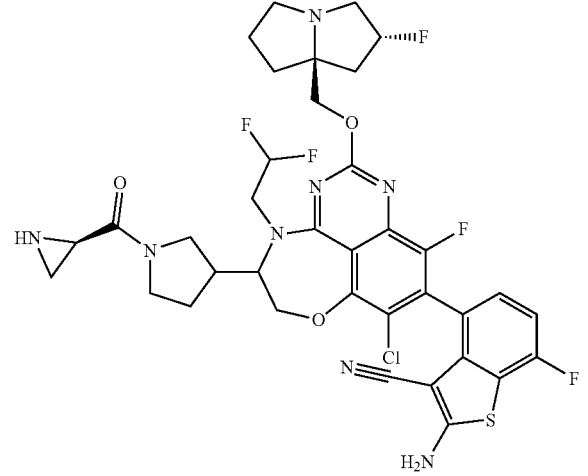 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCN(C(=O)[C@H]5CN5)C3)CO4)c12] | 2-amino-4-(5-(1-((R)-aziridine-2-carbonyl)pyrrolidin-3-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 789.1 |

TABLE 1-continued

| No. | Structure | Chemical Name | [M + H]⁺ |
|---|---|---|---|
| 928 | 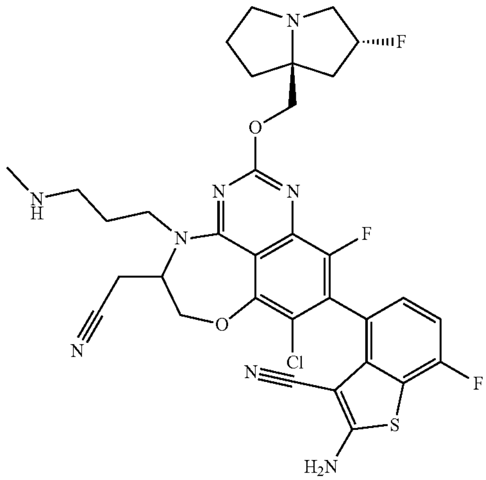 [SMILES: CNCCCN1c2nc(OC[C@@]34CCCN3C[C@H](F)C4)nc3c(F)c(-c4ccc(F)c5sc(N)c(C#N)c45)c(Cl)c(c23)OCC1CC#N] | 2-amino-4-(8-chloro-5-(cyanomethyl)-10-fluoro-2-(((2R,7aS)-2-fluorotetrahydro-1H-pyrrolizin-7a(5H)-yl)methoxy)-4-(3-(methylamino)propyl)-5,6-dihydro-4H-[1,4]oxazepino[5,6,7-de]quinazolin-9-yl)-7-fluorobenzo[b]thiophene-3-carbonitrile | 697.2 |
| 929 | 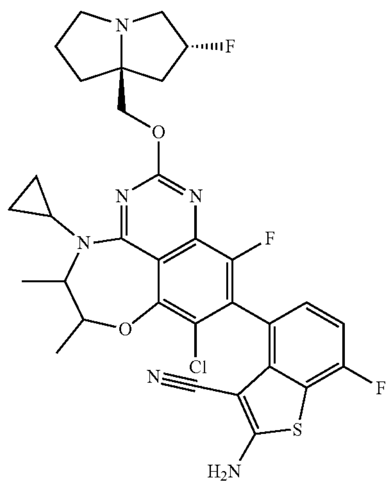 [SMILES: CC1Oc2c(Cl)c(-c3ccc(F)c4sc(N)c(C#N)c34)c(F)c3nc(OC[C@@]45CCCN4C[C@H](F)C5)nc(c23)N(C2CC2)C1C] | 2-amino-4-(8-chloro-4-cyclopropyl-10-fluoro-2-(((2R,7aS)-2-fluorotetrahydro-1H-pyrrolizin-7a(5H)-yl)methoxy)-5,6-dimethyl-5,6-dihydro-4H-[1,4]oxazepino[5,6,7-de]quinazolin-9-yl)-7-fluorobenzo[b]thiophene-3-carbonitrile | 654.9 |
| 930 | 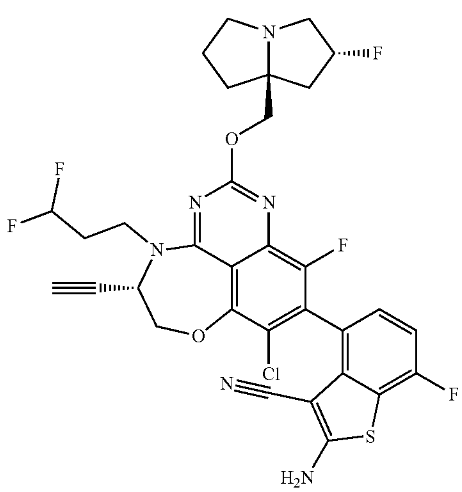 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5S)-8-chloro-4-(3,3-difluoropropyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 688.9 |

TABLE 1-continued

| No. | Structure | Chemical Name | [M + H]⁺ |
|---|---|---|---|
| 931 | 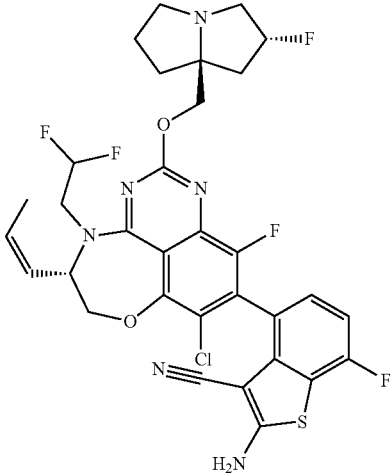 [SMILES: C/C=C\[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazolin-9-yl)-7-fluorobenzo[b]thiophene-3-carbonitrile | 690.9 |
| 932 | 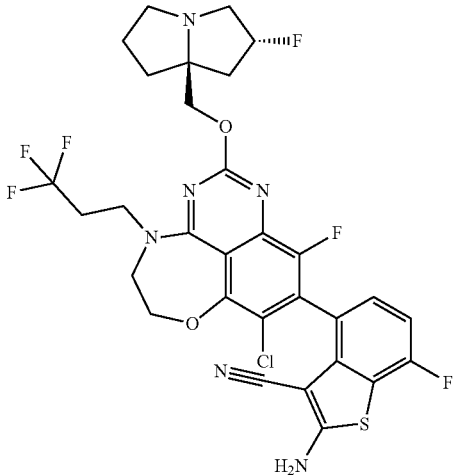 [SMILES: N#Cc1c(N)sc2c(F)ccc(-c3c(Cl)c4c5c(nc(OC[C@@]67CCCN6C[C@H](F)C7)nc5c3F)N(CCC(F)(F)F)CCO4)c12] | 2-amino-4-(8-chloro-10-fluoro-2-(((2R,7aS)-2-fluorotetrahydro-1H-pyrrolizin-7a(5H)-yl)methoxy)-4-(3,3,3-trifluoropropyl)-5,6-dihydro-4H-[1,4]oxazepino[5,6,7-de]quinazolin-9-yl)-7-fluorobenzo[b]thiophene-3-carbonitrile | 683.3 |
| 933 | 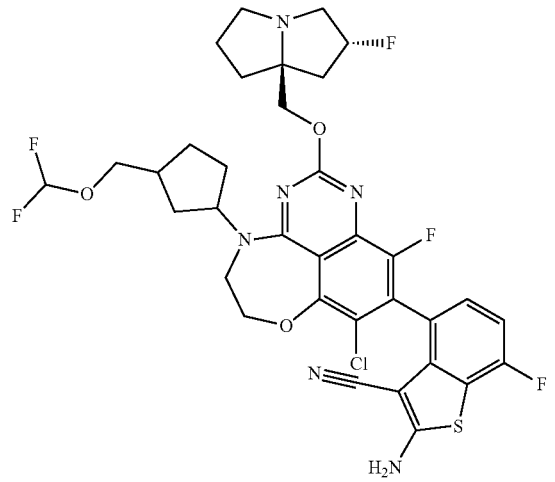 [SMILES: N#Cc1c(N)sc2c(F)ccc(-c3c(Cl)c4c5c(nc(OC[C@@]67CCCN6C[C@H](F)C7)nc5c3F)N(C3CCC(COC(F)F)C3)CCO4)c12] | 2-amino-4-(8-chloro-4-(3-((difluoromethoxy)methyl)cyclopentyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 736.3 |

TABLE 1-continued

| No. | Structure | Chemical Name | [M + H]+ |
|---|---|---|---|
| 934 | 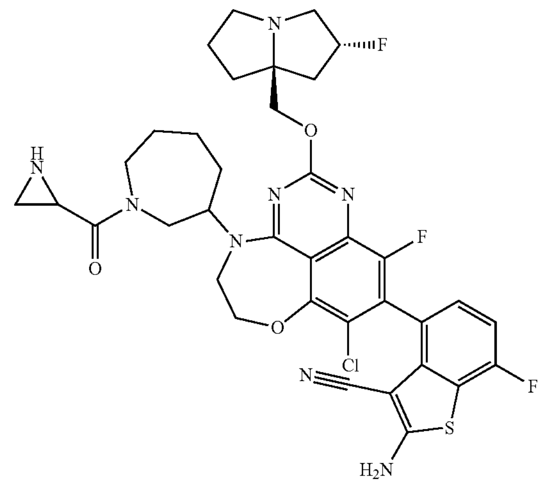 [SMILES: N#Cc1c(N)sc2c(F)ccc(-c3c(Cl)c4c5c(nc(OC[C@@]67CCCN6C[C@H](F)C7)nc5c3F)N(C3CCCCN(C(=O)C5CN5)C3)CCO4)c12] | 2-amino-4-(4-(1-(aziridine-2-carbonyl)azepan-3-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 753 |
| 935 | 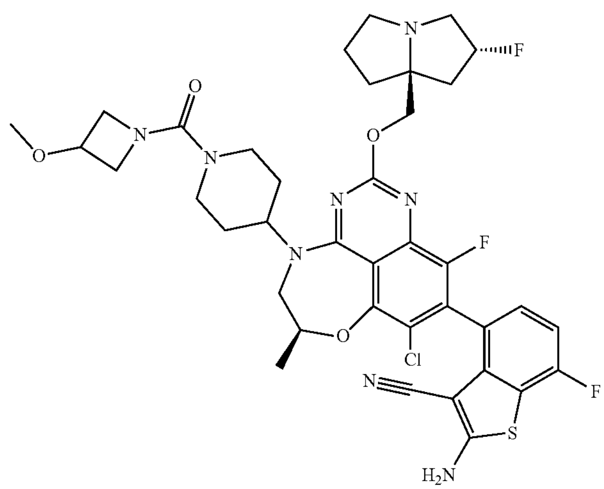 [SMILES: COC1CN(C(=O)N2CCC(N3C[C@H](C)Oc4c(Cl)c(-c5ccc(F)c6sc(N)c(C#N)c56)c(F)c5nc(OC[C@@]67CCCN6C[C@H](F)C7)nc3c45)CC2)C1] | 2-amino-4-((6S)-8-chloro-10-fluoro-2-(((2R,7aS)-2-fluorotetrahydro-1H-pyrrolizin-7a(5H)-yl)methoxy)-4-(1-(3-methoxyazetidine-1-carbonyl)piperidin-4-yl)-6-methyl-5,6-dihydro-4H-[1,4]oxazepino[5,6,7-de]quinazolin-9-yl)-7-fluorobenzo[b]thiophene-3-carbonitrile | 797.4 |
| 936 | 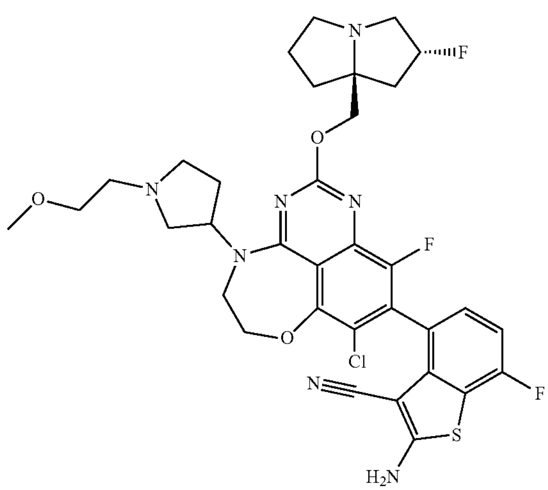 [SMILES: COCCN1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(1-(2-methoxyethyl)pyrrolidin-3-yl)-5,6-dihydro-4H-[1,4]oxazepino[5,6,7-de]quinazolin-9-yl)-7-fluorobenzo[b]thiophene-3-carbonitrile | 714.3 |

TABLE 1-continued

| No. | Structure | Chemical Name | [M + H]+ |
|---|---|---|---|
| 937 | 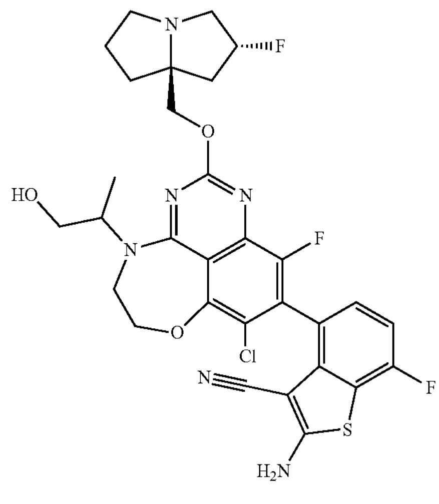 [SMILES: CC(CO)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(1-hydroxypropan-2-yl)-5,6-dihydro-4H-[1,4]oxazepino[5,6,7-de]quinazolin-9-yl)-7-fluorobenzo[b]thiophene-3-carbonitrile | 644.7 |
| 938 | 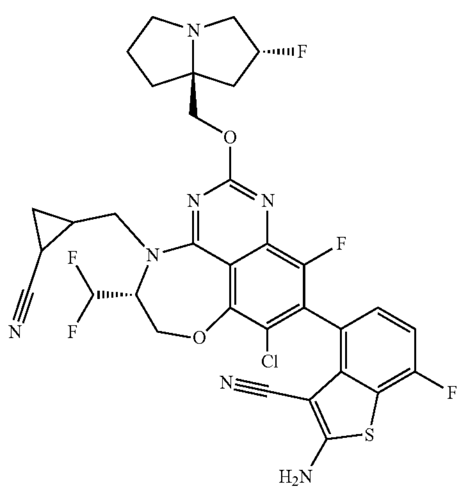 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |
| 939 | 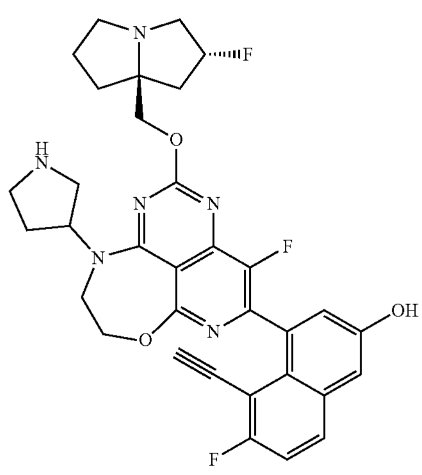 [SMILES: C#Cc1c(F)ccc2cc(O)cc(-c3nc4c5c(nc(OC[C@@]67CCCN6C[C@H](F)C7)nc5c3F)N(C3CCNC3)CCO4)c12] | 5-ethynyl-6-fluoro-4-(4-fluoro-2-(((2R,7aS)-2-fluorotetrahydro-1H-pyrrolizin-7a(5H)-yl)methoxy)-10-(pyrrolidin-3-yl)-9,10-dihydro-8H-7-oxa-1,3,6,10-tetraazacyclohepta[de]naphthalen-5-yl)naphthalen-2-ol | 616.9 |

TABLE 1-continued

| No. | Structure | Chemical Name | [M + H]+ |
|---|---|---|---|
| 940 | 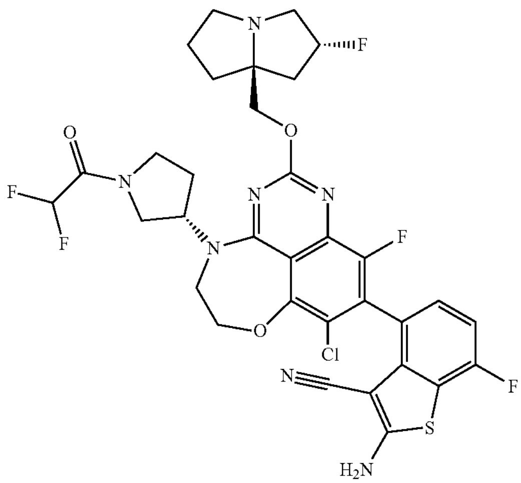 [SMILES: N#Cc1c(N)sc2c(F)ccc(-c3c(Cl)c4c5c(nc(OC[C@@]67CCCN6C[C@H](F)C7)nc5c3F)N([C@H]3CCN(C(=O)C(F)F)C3)CCO4)c12] | 2-amino-4-(8-chloro-4-((S)-1-(2,2-difluoroacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 734.2 |
| 941 | 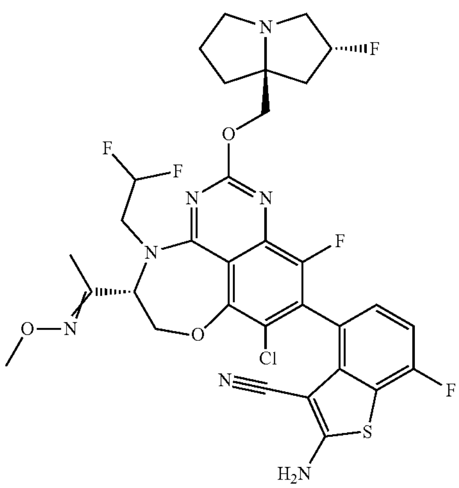 [SMILES: CON=C(C)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-(1-(methoxyimino)ethyl)-5,6-dihydro-4H-[1,4]oxazepino[5,6,7-de]quinazolin-9-yl)-7-fluorobenzo[b]thiophene-3-carbonitrile | 721.9 |
| 942 | 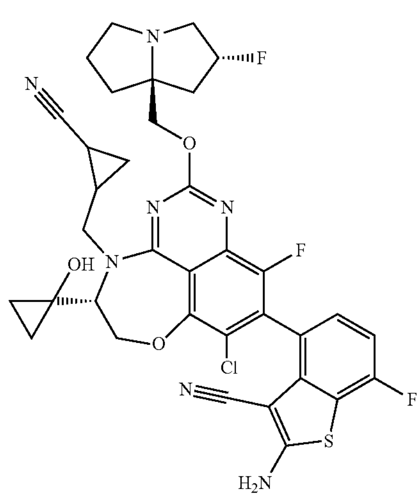 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |

TABLE 1-continued

| No. | Structure | Chemical Name | [M + H]+ |
|---|---|---|---|
| 943 | 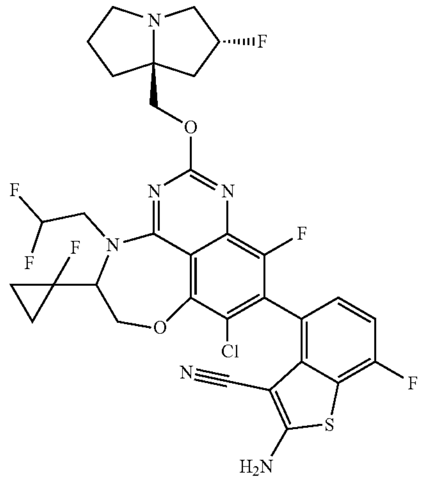 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3(F)CC3)CO4)c12] | 2-amino-4-(8-chloro-4-(2,2-difluoroethyl)-10-fluoro-5-(1-fluorocyclopropyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 709 |
| 944 | 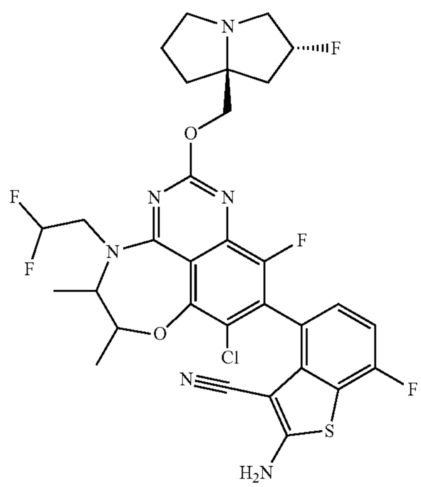 [SMILES: CC1Oc2c(Cl)c(-c3ccc(F)c4sc(N)c(C#N)c34)c(F)c3nc(OC[C@@]45CCCN4C[C@H](F)C5)nc(c23)N(CC(F)F)C1C] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5,6-dimethyl-5,6-dihydro-4H-[1,4]oxazepino[5,6,7-de]quinazolin-9-yl)-7-fluorobenzo[b]thiophene-3-carbonitrile | 679.3 |
| 945 | 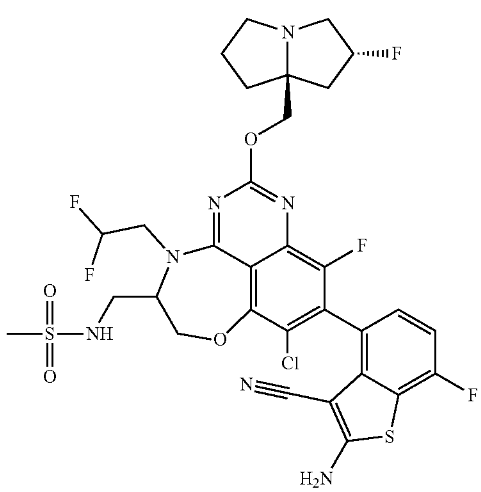 [SMILES: CS(=O)(=O)NCC1COc2c(Cl)c(-c3ccc(F)c4sc(N)c(C#N)c34)c(F)c3nc(OC[C@@]45CCCN4C[C@H](F)C5)nc(c23)N1CC(F)F] | N-((9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)methanesulfonamide | 758.3 |

TABLE 1-continued

| No. | Chemical Name | [M + H]+ |
|---|---|---|
| 946 | 2-amino-4-(8-chloro-4-((R)-1-(2,2-difluoroacetyl)pyrrolidin-3-yl)-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile | 704.4 |
| 947 | 2-amino-4-(8-chloro-4-ethyl-10-fluoro-2-methoxy-5,6-dihydro-4H-[1,4]oxazepino[5,6,7-de]quinazolin-9-yl)-7-fluorobenzo[b]thiophene-3-carbonitrile | 487.9 |
| 948 | 5-ethynyl-6-fluoro-4-(4-fluoro-2-(((2R,7aS)-2-fluorotetrahydro-1H-pyrrolizin-7a(5H)-yl)methoxy)-10-phenyl-9,10-dihydro-8H-7-oxa-1,3,6,10-tetraazacyclohepta[de]naphthalen-5-yl)naphthalen-2-ol | 623.8 |

TABLE 1-continued

| No. | Structure | Chemical Name | [M + H]+ |
|---|---|---|---|
| 949 | 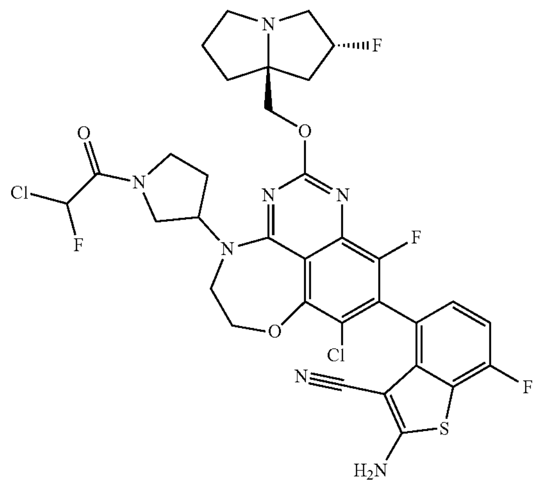 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C(F)Cl)C3)CCO4)c12] | 2-amino-4-(8-chloro-4-(1-(2-chloro-2-fluoroacetyl)pyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 750.3 |
| 950 | 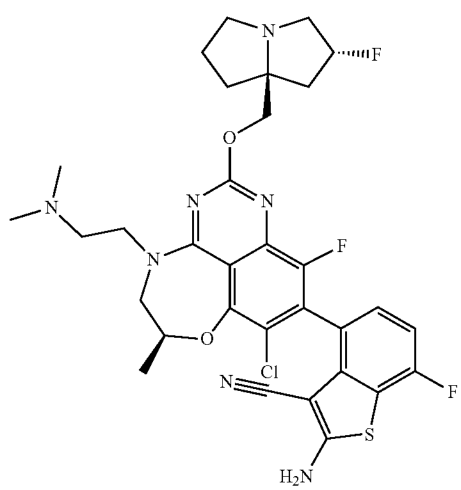 [SMILES: C[C@H]1CN(CCN(C)C)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-(2-(dimethylamino)ethyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 672.2 |
| 951 | 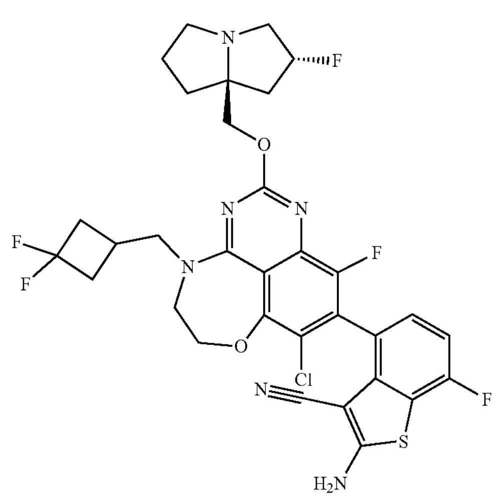 [SMILES: N#Cc1c(N)sc2c(F)ccc(-c3c(Cl)c4c5c(nc(OC[C@@]67CCCN6C[C@H](F)C7)nc5c3F)N(CC3CC(F)(F)C3)CCO4)c12] | 2-amino-4-(8-chloro-4-((3,3-difluorocyclobutyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 691.5 |

TABLE 1-continued

| No. | Structure | Chemical Name | [M + H]+ |
|---|---|---|---|
| 952 | 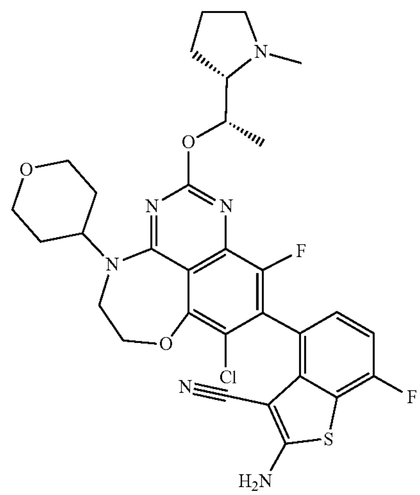 [SMILES: C[C@H](Oc1nc2c3c(c(Cl)c(-c4ccc(F)c5sc(N)c(C#N)c45)c(F)c3n1)OCCN2C1CCOCC1)[C@@H]1CCCN1C] | 2-amino-4-(8-chloro-10-fluoro-2-((S)-1-((S)-1-methylpyrrolidin-2-yl)ethoxy)-4-(tetrahydro-2H-pyran-4-yl)-5,6-dihydro-4H-[1,4]oxazepino[5,6,7-de]quinazolin-9-yl)-7-fluorobenzo[b]thiophene-3-carbonitrile | 641.2 |
| 953 | 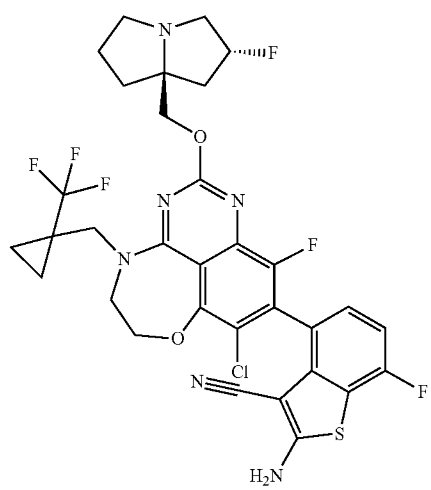 [SMILES: N#Cc1c(N)sc2c(F)ccc(-c3c(Cl)c4c5c(nc(OC[C@@]67CCCN6C[C@H](F)C7)nc5c3F)N(CC3(C(F)(F)F)CC3)CCO4)c12] | 2-amino-4-(8-chloro-10-fluoro-2-(((2R,7aS)-2-fluorotetrahydro-1H-pyrrolizin-7a(5H)-yl)methoxy)-4-((1-(trifluoromethyl)cyclopropyl)methyl)-5,6-dihydro-4H-[1,4]oxazepino[5,6,7-de]quinazolin-9-yl)-7-fluorobenzo[b]thiophene-3-carbonitrile | 709 |
| 954 | 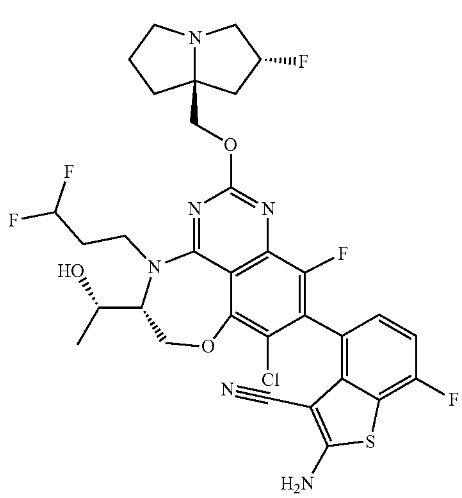 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5R)-8-chloro-4-(3,3-difluoropropyl)-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 708.9 |

TABLE 1-continued

| No. | Structure | Chemical Name | [M + H]+ |
|---|---|---|---|
| 955 | 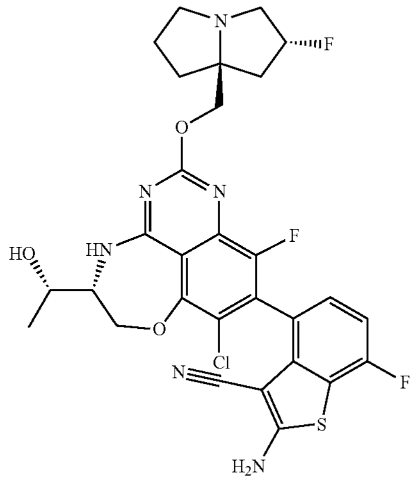 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1] | 2-amino-4-((5R)-8-chloro-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 630.9 |
| 956 | 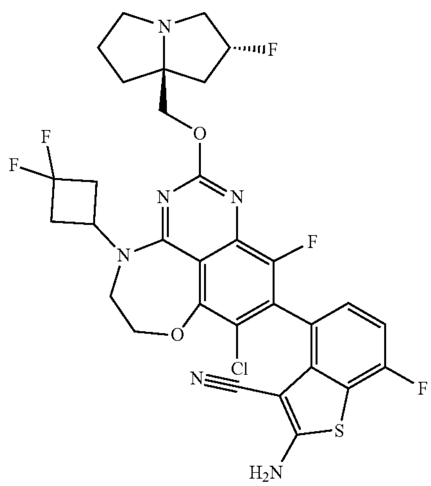 [SMILES: N#Cc1c(N)sc2c(F)ccc(-c3c(Cl)c4c5c(nc(OC[C@@]67CCCN6C[C@H](F)C7)nc5c3F)N(C3CC(F)(F)C3)CCO4)c12] | 2-amino-4-(8-chloro-4-(3,3-difluorocyclobutyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 677.3 |
| 957 | 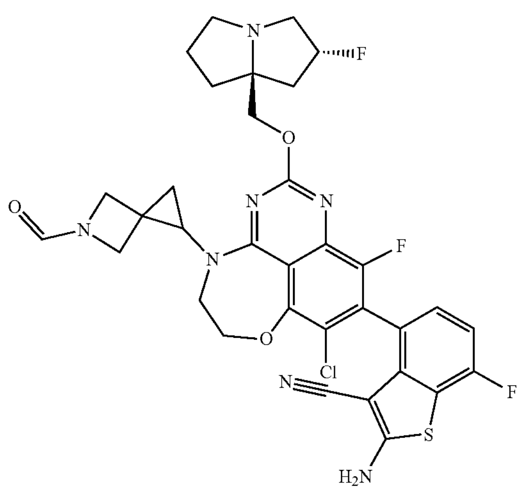 [SMILES: N#Cc1c(N)sc2c(F)ccc(-c3c(Cl)c4c5c(nc(OC[C@@]67CCCN6C[C@H](F)C7)nc5c3F)N(C3CC35CN(C=O)C5)CCO4)c12] | 2-amino-4-(8-chloro-10-fluoro-2-(((2R,7aS)-2-fluorotetrahydro-1H-pyrrolizin-7a(5H)-yl)methoxy)-4-(5-formyl-5-azaspiro[2.3]hexan-1-yl)-5,6-dihydro-4H-[1,4]oxazepino[5,6,7-de]quinazolin-9-yl)-7-fluorobenzo[b]thiophene-3-carbonitrile | 696.2 |

TABLE 1-continued

| No. | Structure | Chemical Name | [M + H]⁺ |
|---|---|---|---|
| 958 | 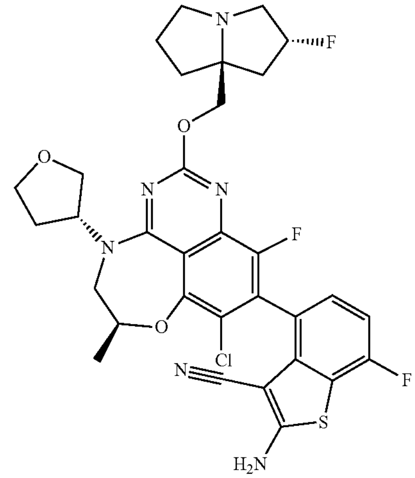 [SMILES: C[C@H]1CN([C@@H]2CCOC2)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-10-fluoro-2-(((2R,7aS)-2-fluorotetrahydro-1H-pyrrolizin-7a(5H)-yl)methoxy)-6-methyl-4-((R)-tetrahydrofuran-3-yl)-5,6-dihydro-4H-[1,4]oxazepino[5,6,7-de]quinazolin-9-yl)-7-fluorobenzo[b]thiophene-3-carbonitrile | 670.9 |
| 959 | 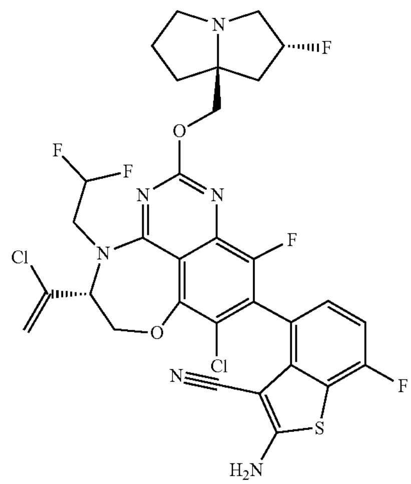 [SMILES: C=C(Cl)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-5-(1-chlorovinyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 710.8 |
| 960 | 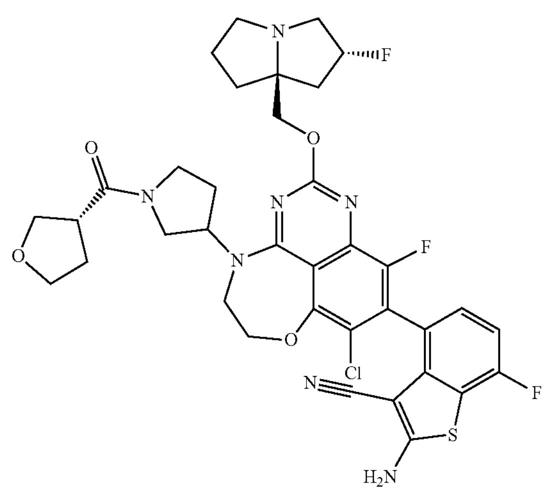 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)[C@@H]5CCOC5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-((R)-tetrahydrofuran-3-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 754.3 |

TABLE 1-continued

| No. | Structure | Chemical Name | [M + H]⁺ |
|---|---|---|---|
| 961 | 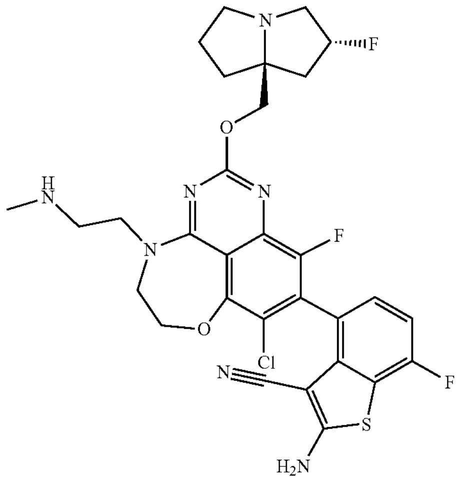 [SMILES: CNCCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(2-(methylamino)ethyl)-5,6-dihydro-4H-[1,4]oxazepino[5,6,7-de]quinazolin-9-yl)-7-fluorobenzo[b]thiophene-3-carbonitrile | 644.4 |
| 962 | 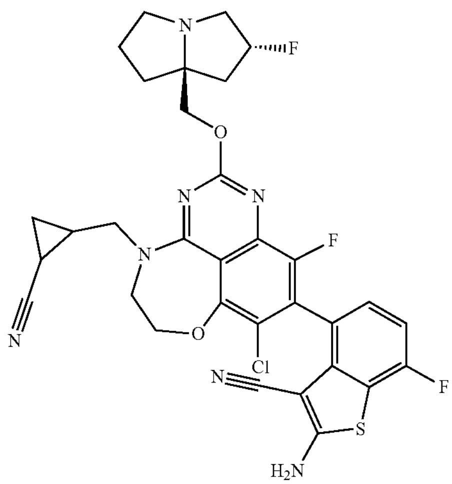 [SMILES: N#Cc1c(N)sc2c(F)ccc(-c3c(Cl)c4c5c(nc(OC[C@@]67CCCN6C[C@H](F)C7)nc5c3F)N(CC3CC3C#N)CCO4)c12] | 2-amino-4-(8-chloro-4-((2-cyanocyclopropyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 665.7 |
| 963 | 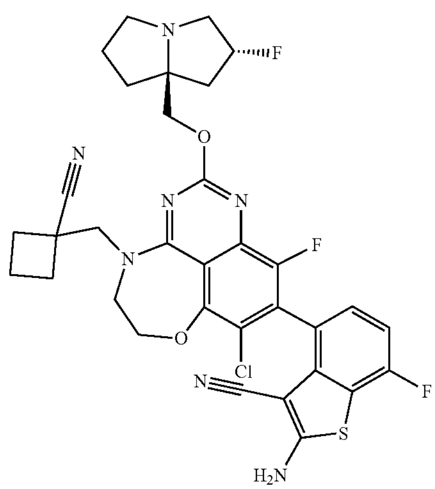 [SMILES: N#Cc1c(N)sc2c(F)ccc(-c3c(Cl)c4c5c(nc(OC[C@@]67CCCN6C[C@H](F)C7)nc5c3F)N(CC3(C#N)CCC3)CCO4)c12] | 2-amino-4-(8-chloro-4-((1-cyanocyclobutyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 680.3 |

| No. | Structure | Chemical Name | [M + H]+ |
|---|---|---|---|
| 964 | 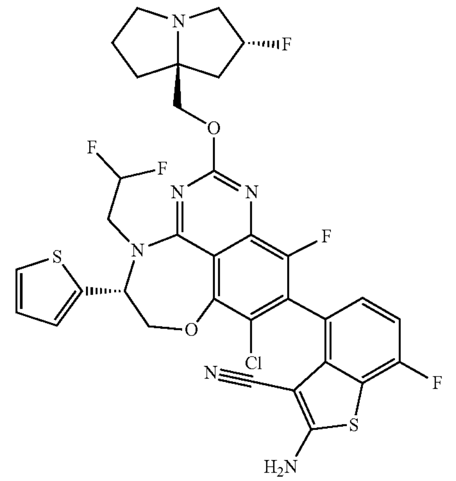 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](c3cccs3)CO4)c12] | 2-amino-4-((R)-8-chloro-4-(2,2-difluoroethyl)-10-fluoro-2-(((2R,7aS)-2-fluorotetrahydro-1H-pyrrolizin-7a(5H)-yl)methoxy)-5-(thiophen-2-yl)-5,6-dihydro-4H-[1,4]oxazepino[5,6,7-de]quinazolin-9-yl)-7-fluorobenzo[b]thiophene-3-carbonitrile | 732.8 |
| 965 | 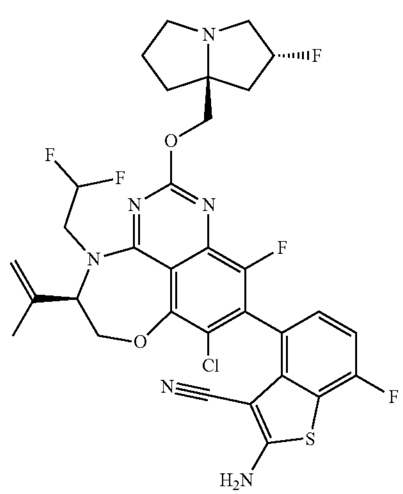 [SMILES: C=C(C)[C@@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-(prop-1-en-2-yl)-5,6-dihydro-4H-[1,4]oxazepino[5,6,7-de]quinazolin-9-yl)-7-fluorobenzo[b]thiophene-3-carbonitrile | 690.9 |
| 966 | 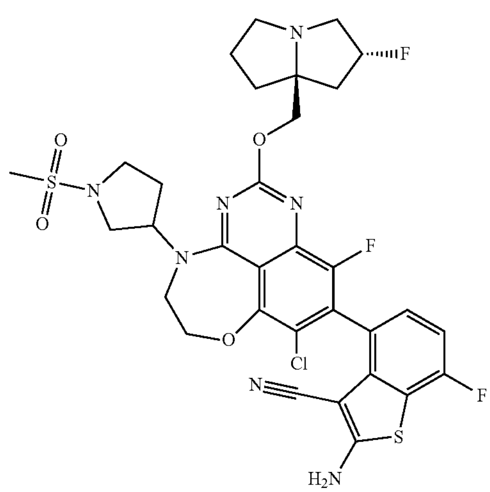 [SMILES: CS(=O)(=O)N1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(1-(methylsulfonyl)pyrrolidin-3-yl)-5,6-dihydro-4H-[1,4]oxazepino[5,6,7-de]quinazolin-9-yl)-7-fluorobenzo[b]thiophene-3-carbonitrile | 734.3 |

TABLE 1-continued

| No. | Structure | Chemical Name | [M + H]⁺ |
| --- | --- | --- | --- |
| 967 | 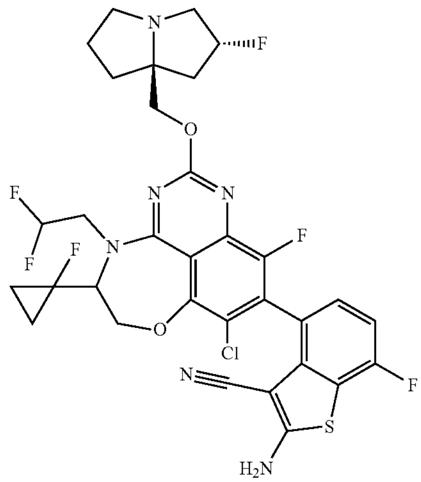 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3(F)CC3)CO4)c12] | 2-amino-4-(8-chloro-4-(2,2-difluoroethyl)-10-fluoro-5-(1-fluorocyclopropyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 708.9 |
| 968 | 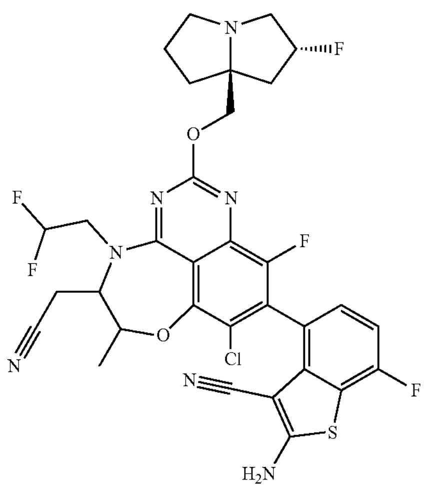 [SMILES: CC1Oc2c(Cl)c(-c3ccc(F)c4sc(N)c(C#N)c34)c(F)c3nc(OC[C@@]45CCCN4C[C@H](F)C5)nc(c23)N(CC(F)F)C1CC#N] | 2-amino-4-(8-chloro-5-(cyanomethyl)-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 703.9 |
| 969 | 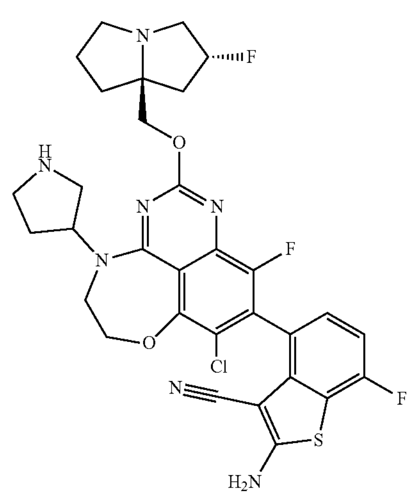 | 2-amino-4-(8-chloro-10-fluoro-2-(((2R,7aS)-2-fluorotetrahydro-1H-pyrrolizin-7a(5H)-yl)methoxy)-4-(pyrrolidin-3-yl)-5,6-dihydro-4H-[1,4]oxazepino[5,6,7-de]quinazolin-9-yl)-7-fluorobenzo[b]thiophene-3-carbonitrile | 654.3 [M − H]⁻ |

TABLE 1-continued

| No. | Structure | Chemical Name | [M + H]⁺ |
|---|---|---|---|
| 970 | 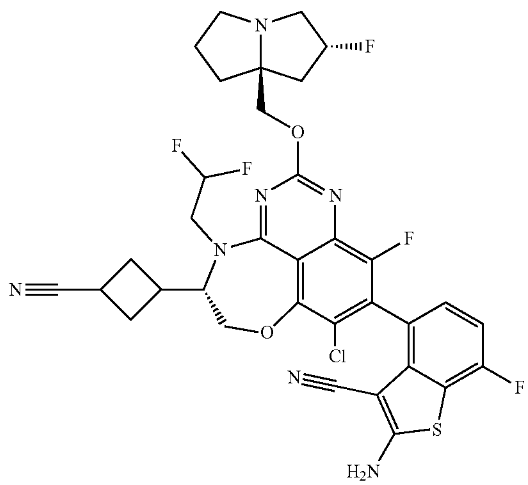 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC(C#N)C3)CO4)c12] | 2-amino-4-((S)-8-chloro-5-(3-cyanocyclobutyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 729.9 |
| 971 | 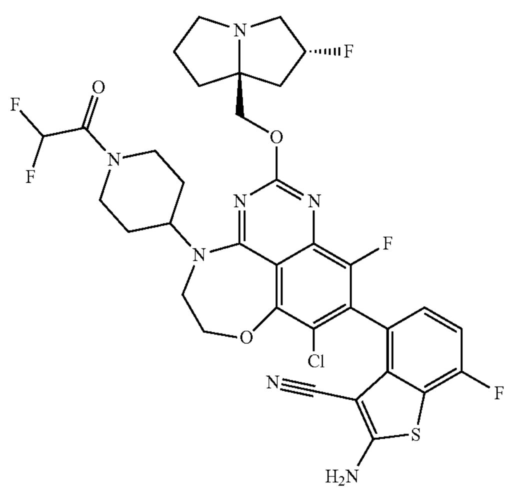 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C(F)F)CC3)CCO4)c12] | 2-amino-4-(8-chloro-4-(1-(2,2-difluoroacetyl)piperidin-4-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 748.3 |
| 972 | 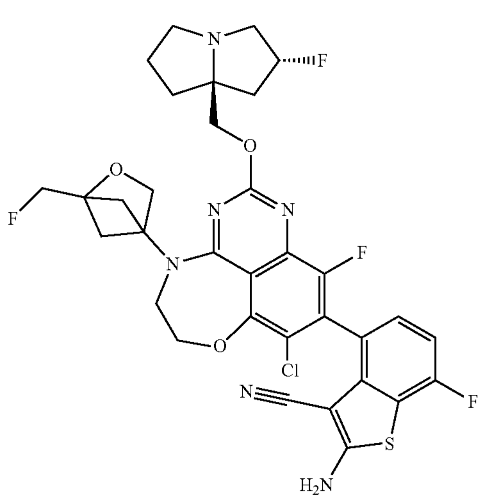 [SMILES: N#Cc1c(N)sc2c(F)ccc(-c3c(Cl)c4c5c(nc(OC[C@@]67CCCN6C[C@H](F)C7)nc5c3F)N(C35COC(CF)(C3)C5)CCO4)c12] | 2-amino-4-(8-chloro-10-fluoro-4-(1-(fluoromethyl)-2-oxabicyclo[2.1.1]hexan-4-yl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 700.8 |

TABLE 1-continued

| No. | Structure | Chemical Name | [M + H]+ |
|---|---|---|---|
| 973 | 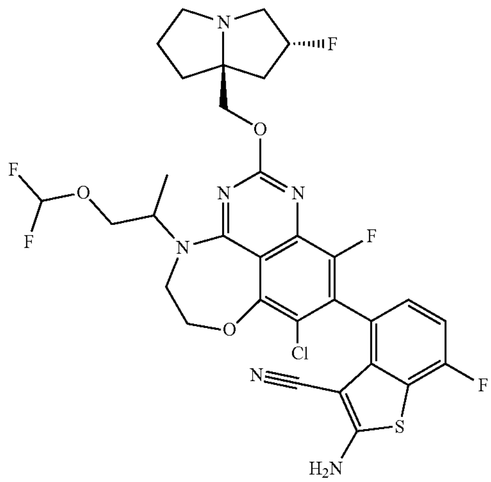 [SMILES: CC(COC(F)F)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(1-(difluoromethoxy)propan-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 694.9 |
| 974 | 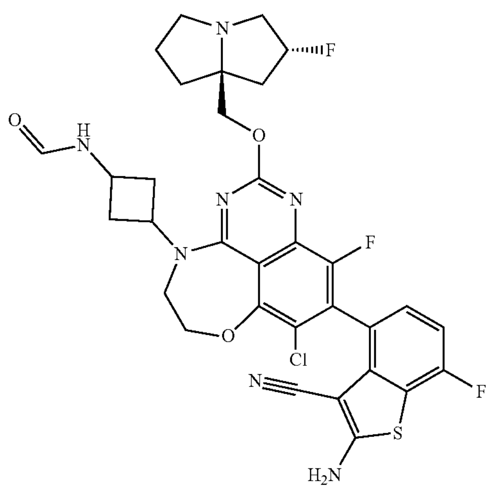 [SMILES: N#Cc1c(N)sc2c(F)ccc(-c3c(Cl)c4c5c(nc(OC[C@@]67CCCN6C[C@H](F)C7)nc5c3F)N(C3CC(NC=O)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)formamide | 684.3 |
| 975 | 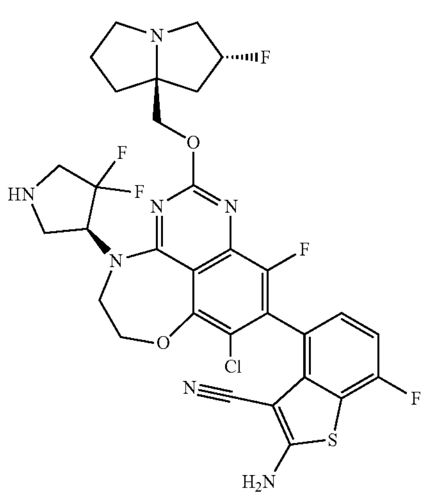 [SMILES: N#Cc1c(N)sc2c(F)ccc(-c3c(Cl)c4c5c(nc(OC[C@@]67CCCN6C[C@H](F)C7)nc5c3F)N([C@H]3CNCC3(F)F)CCO4)c12] | 2-amino-4-(8-chloro-4-((S)-4,4-difluoropyrrolidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 692.5 |

TABLE 1-continued

| No. | Chemical Name | [M + H]+ |
|---|---|---|
| 976 | N-(((5S)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)oxetane-3-carboxamide | 764.4 |
| 977 | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |
| 978 | 2-amino-4-((6S)-8-chloro-4-((1-(dimethylamino)cyclobutyl)methyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 712.3 |

TABLE 1-continued

| No. | Structure | Chemical Name | [M + H]+ |
|---|---|---|---|
| 979 | 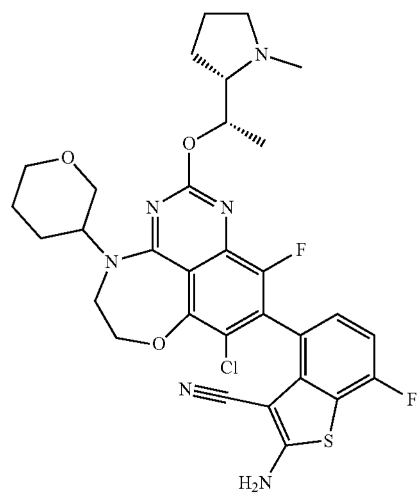 [SMILES: C[C@H](Oc1nc2c3c(c(Cl)c(-c4ccc(F)c5sc(N)c(C#N)c45)c(F)c3n1)OCCN2C1CCCOC1)[C@@H]1CCCN1C] | 2-amino-4-(8-chloro-10-fluoro-2-((S)-1-((S)-1-methylpyrrolidin-2-yl)ethoxy)-4-(tetrahydro-2H-pyran-3-yl)-5,6-dihydro-4H-[1,4]oxazepino[5,6,7-de]quinazolin-9-yl)-7-fluorobenzo[b]thiophene-3-carbonitrile | 641.3 |
| 980 | 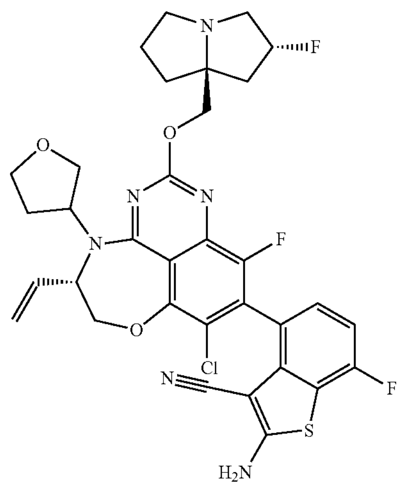 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-4-(tetrahydrofuran-3-yl)-5-vinyl-5,6-dihydro-4H-[1,4]oxazepino[5,6,7-de]quinazolin-9-yl)-7-fluorobenzo[b]thiophene-3-carbonitrile | 683 |
| 981 | 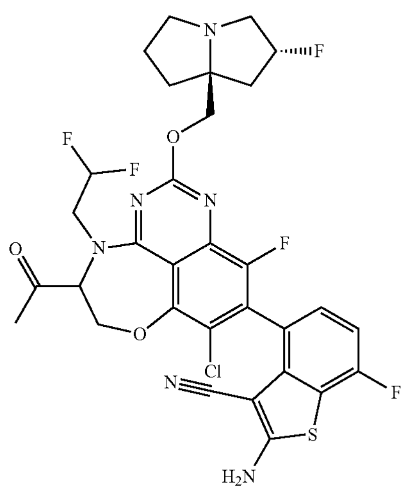 [SMILES: CC(=O)C1COc2c(Cl)c(-c3ccc(F)c4sc(N)c(C#N)c34)c(F)c3nc(OC[C@@]45CCCN4C[C@H](F)C5)nc(c23)N1CC(F)F] | 4-(5-acetyl-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 692.9 |

TABLE 1-continued

| No. | Structure | Chemical Name | [M + H]+ |
|---|---|---|---|
| 982 | 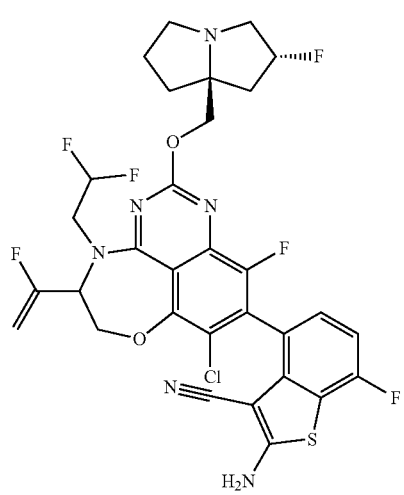 [SMILES: C=C(F)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-fluorovinyl)-5,6-dihydro-4H-[1,4]oxazepino[5,6,7-de]quinazolin-9-yl)-7-fluorobenzo[b]thiophene-3-carbonitrile | 695 |
| 983 | 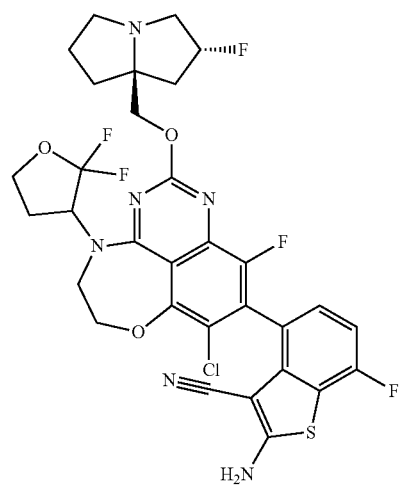 [SMILES: N#Cc1c(N)sc2c(F)ccc(-c3c(Cl)c4c5c(nc(OC[C@@]67CCCN6C[C@H](F)C7)nc5c3F)N(C3CCOC3(F)F)CCO4)c12] | 2-amino-4-(8-chloro-4-(4,4-difluorotetrahydrofuran-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 692.9 |
| 984 | 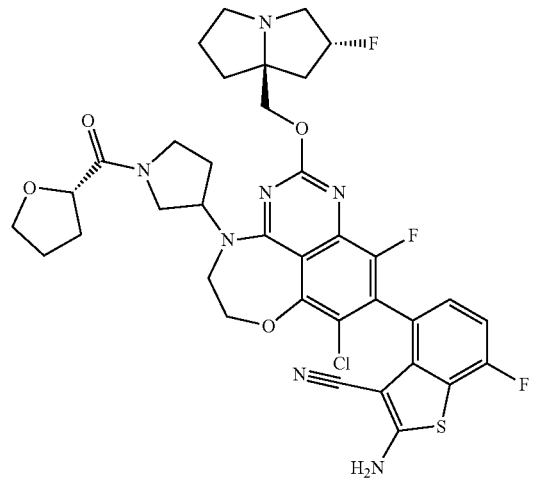 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)[C@@H]5CCCO5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-((S)-tetrahydrofuran-2-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 754.4 |

TABLE 1-continued

| No. | Structure | Chemical Name | [M + H]+ |
|---|---|---|---|
| 985 | 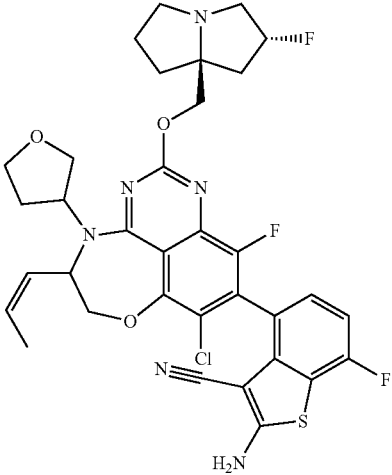 [SMILES: C/C=C\C1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-(8-chloro-10-fluoro-2-(((2R,7aS)-2-fluorotetrahydro-1H-pyrrolizin-7a(5H)-yl)methoxy)-5-((Z)-prop-1-en-1-yl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 697.1 |
| 986 | 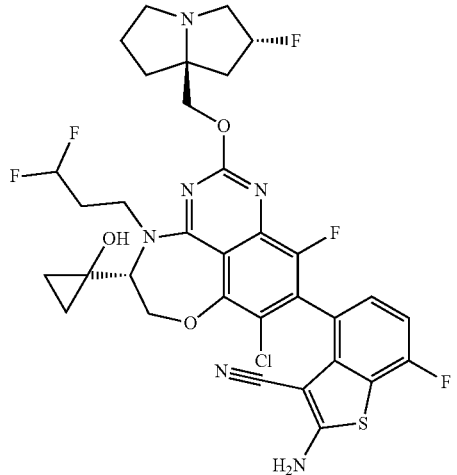 [SMILES: N#Cc1c(N)sc2c(F)ccc(-c3c(Cl)c4c5c(nc(OC[C@@]67CCCN6C[C@H](F)C7)nc5c3F)N(CCC(F)F)[C@@H](C3(O)CC3)CO4)c12] | 2-amino-4-((R)-8-chloro-4-(3,3-difluoropropyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 721 |
| 987 | 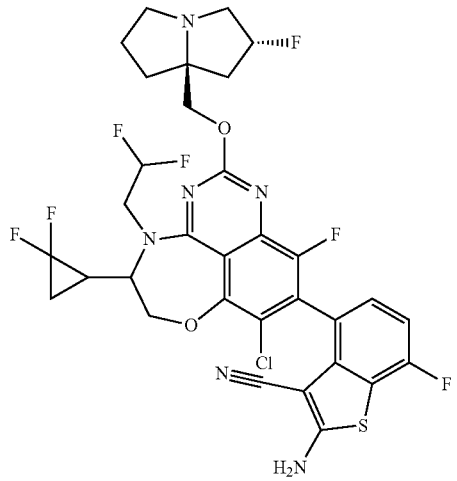 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CC3(F)F)CO4)c12] | 2-amino-4-(8-chloro-5-(2,2-difluorocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 727.4 |

TABLE 1-continued

| No. | Structure | Chemical Name | [M + H]⁺ |
|---|---|---|---|
| 988 | 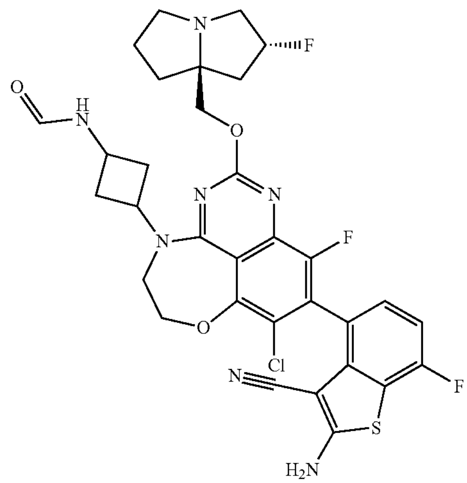 [SMILES: N#Cc1c(N)sc2c(F)ccc(-c3c(Cl)c4c5c(nc(OC[C@@]67CCCN6C[C@H](F)C7)nc5c3F)N(C3CC(NC=O)C3)CCO4)c12] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)formamide | 684.3 |
| 989 | 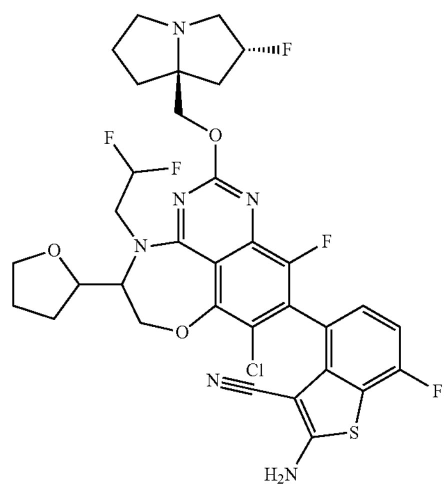 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCO3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile | 720.9 |
| 990 | 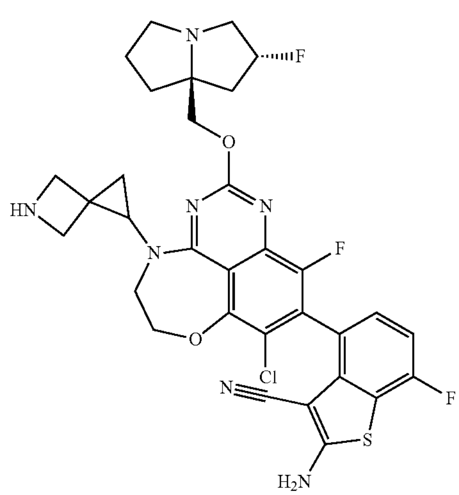 [SMILES: N#Cc1c(N)sc2c(F)ccc(-c3c(Cl)c4c5c(nc(OC[C@@]67CCCN6C[C@H](F)C7)nc5c3F)N(C3CC35CNC5)CCO4)c12] | 2-amino-4-(8-chloro-10-fluoro-2-(((2R,7aS)-2-fluorotetrahydro-1H-pyrrolizin-7a(5H)-yl)methoxy)-4-(5-azaspiro[2.3]hexan-1-yl)-5,6-dihydro-4H-[1,4]oxazepino[5,6,7-de]quinazolin-9-yl)-7-fluorobenzo[b]thiophene-3-carbonitrile | 668.2 |

TABLE 1-continued

| No. | Structure | Chemical Name | [M + H]+ |
|---|---|---|---|
| 991 | 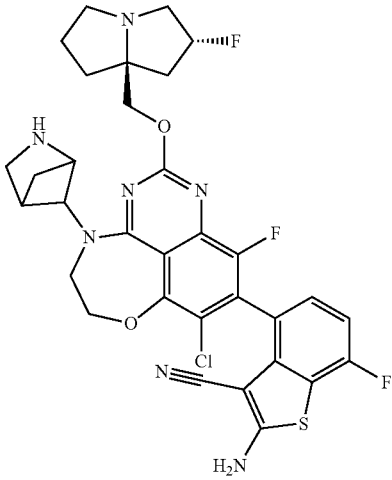 [SMILES: N#Cc1c(N)sc2c(F)ccc(-c3c(Cl)c4c5c(nc(OC[C@@]67CCCN6C[C@H](F)C7)nc5c3F)N(C3C5CNC3C5)CCO4)c12] | 4-(4-(2-azabicyclo[2.1.1]hexan-5-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 668.4 |
| 992 | 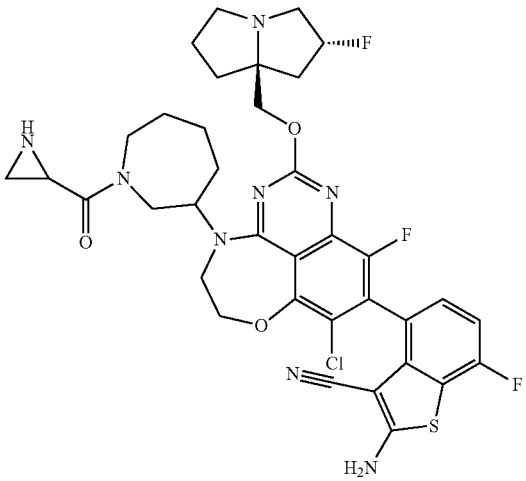 [SMILES: N#Cc1c(N)sc2c(F)ccc(-c3c(Cl)c4c5c(nc(OC[C@@]67CCCN6C[C@H](F)C7)nc5c3F)N(C3CCCCN(C(=O)C5CN5)C3)CCO4)c12] | 2-amino-4-(4-(1-(aziridine-2-carbonyl)azepan-3-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 753 |
| 993 | 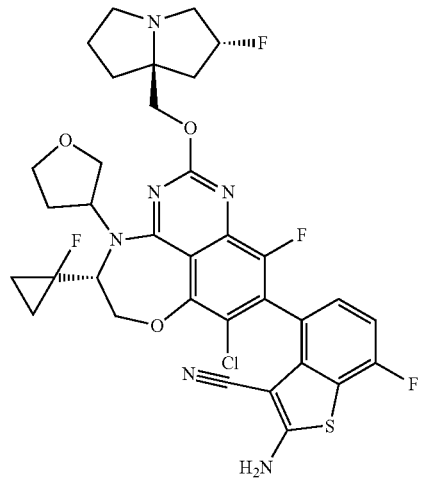 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(F)CC3)CO4)c12] | 2-amino-4-((5R)-8-chloro-10-fluoro-5-(1-fluorocyclopropyl)-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 715.4 |

TABLE 1-continued

| No. | Structure | Chemical Name | [M + H]+ |
|---|---|---|---|
| 994 | 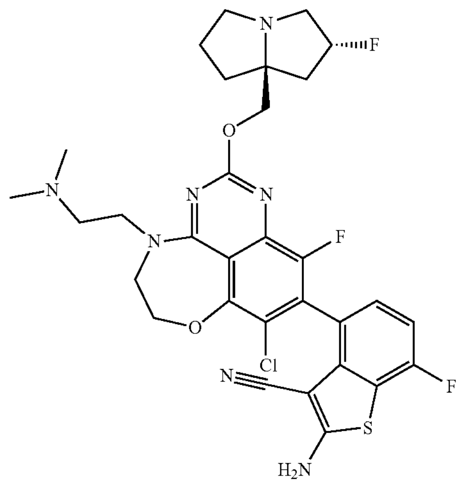 [SMILES: CN(C)CCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(2-(dimethylamino)ethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 656.4 [M − H]− |
| 995 | 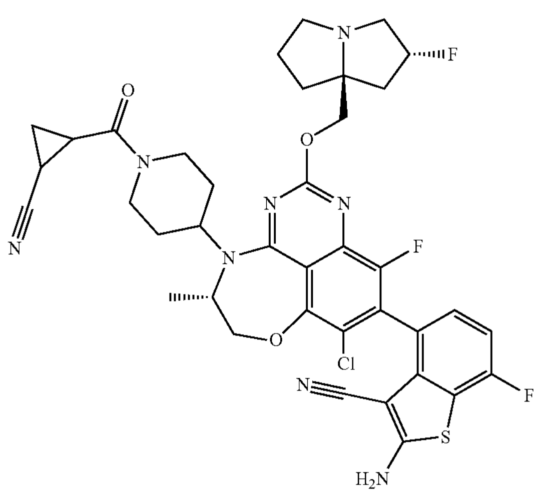 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1C1CCN(C(=O)C2CC2C#N)CC1] | 2-amino-4-((5S)-8-chloro-4-(1-(2-cyanocyclopropane-1-carbonyl)piperidin-4-yl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 777.4 |
| 996 | 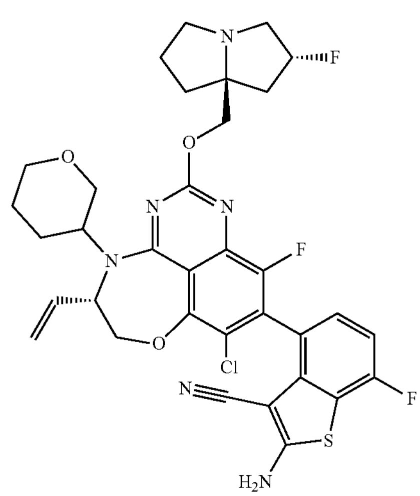 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCCOC1] | 2-amino-4-((5S)-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazolin-9-yl)-7-fluorobenzo[b]thiophene-3-carbonitrile | 696.9 |

TABLE 1-continued

| No. | Structure | Chemical Name | [M + H]⁺ |
|---|---|---|---|
| 997 | 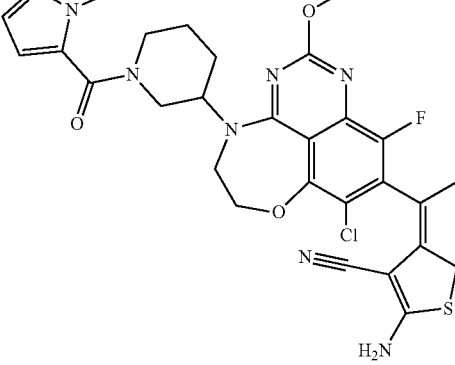 | 2-amino-4-(8-chloro-10-fluoro-2-(((2R,7aS)-2-fluorotetrahydro-1H-pyrrolizin-7a(5H)-yl)methoxy)-4-(1-(1-methyl-1H-pyrazole-5-carbonyl)piperidin-3-yl)-5,6-dihydro-4H-[1,4]oxazepino[5,6,7-de]quinazolin-9-yl)-7-fluorobenzo[b]thiophene-3-carbonitrile | 778.4 |
| 998 | 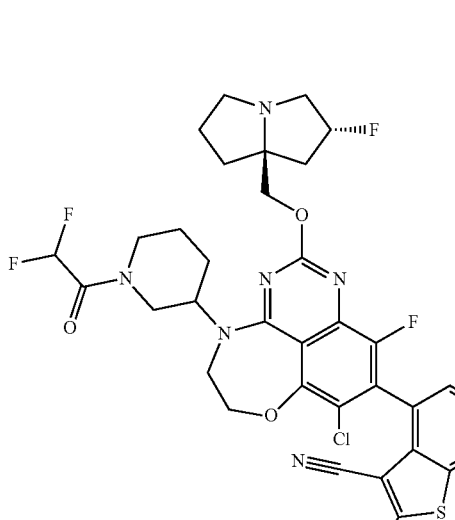 | 2-amino-4-(8-chloro-4-(1-(2,2-difluoroacetyl)piperidin-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 748.4 |
| 999 | 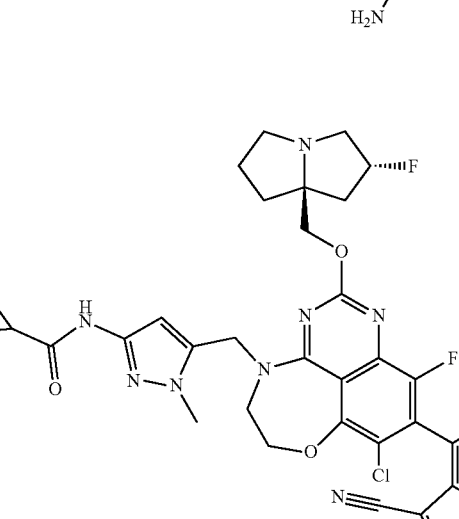 | N-(5-((9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)methyl)-1-methyl-1H-pyrazol-3-yl)aziridine-2-carboxamide | 765.3 |

TABLE 1-continued

| No. | Structure | Chemical Name | [M + H]⁺ |
|---|---|---|---|
| 1000 | 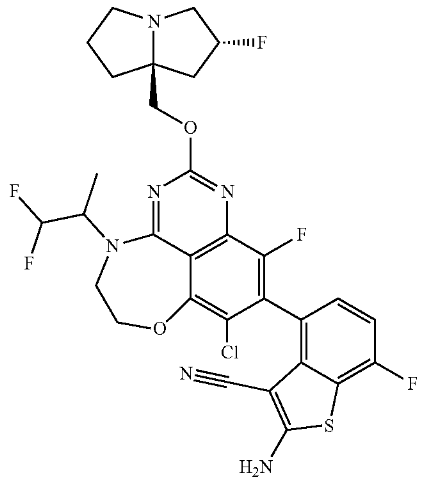 [SMILES: CC(C(F)F)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(1,1-difluoropropan-2-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 664.9 |
| 1001 | 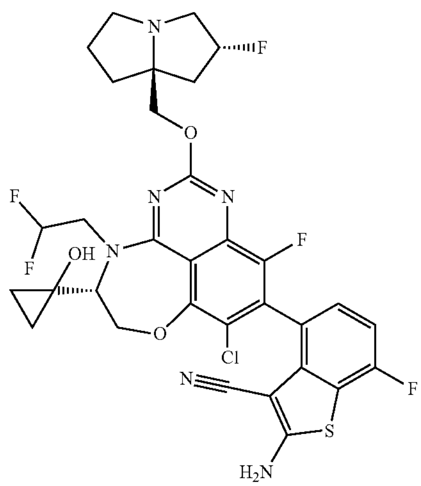 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(O)CC3)CO4)c12] | 2-amino-4-((R)-8-chloro-4-(2,2-difluoroethyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 707.3 |
| 1002 | 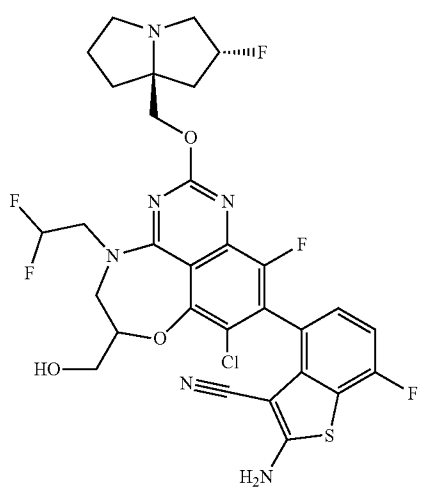 [SMILES: N#Cc1c(N)sc2c(F)ccc(-c3c(Cl)c4c5c(nc(OC[C@@]67CCCN6C[C@H](F)C7)nc5c3F)N(CC(F)F)CC(CO)O4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-6-(hydroxymethyl)-5,6-dihydro-4H-[1,4]oxazepino[5,6,7-de]quinazolin-9-yl)-7-fluorobenzo[b]thiophene-3-carbonitrile | 681 |

TABLE 1-continued

| No. | Structure | Chemical Name | [M + H]+ |
|---|---|---|---|
| 1003 | 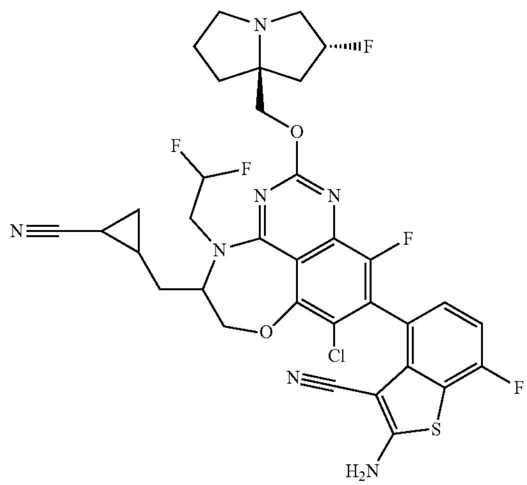 [SMILES: N#Cc1c(N)sc2c(F)ccc(-c3c(Cl)c4c5c(nc(OC[C@@]67CCCN6C[C@H](F)C7)nc5c3F)N(CC(F)F)C(CC3CC3C#N)CO4)c12] | 2-amino-4-(8-chloro-5-((2-cyanocyclopropyl)methyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 729.7 |
| 1004 | 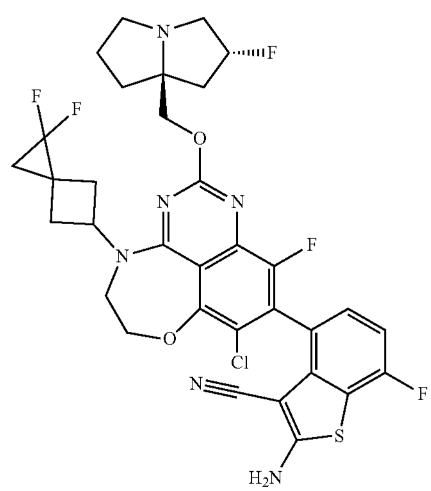 [SMILES: N#Cc1c(N)sc2c(F)ccc(-c3c(Cl)c4c5c(nc(OC[C@@]67CCCN6C[C@H](F)C7)nc5c3F)N(C3CC5(C3)CC5(F)F)CCO4)c12] | 2-amino-4-(8-chloro-4-(1,1-difluorospiro[2.3]hexan-5-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 703.2 |
| 1005 | 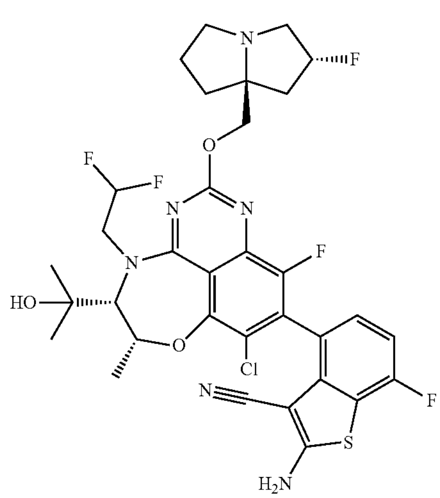 | 2-amino-4-((5R,6R)-8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropan-2-yl)-6-methyl-5,6-dihydro-4H-[1,4]oxazepino[5,6,7-de]quinazolin-9-yl)-7-fluorobenzo[b]thiophene-3-carbonitrile | 723 |

TABLE 1-continued

| No. | Structure | Chemical Name | [M + H]+ |
|---|---|---|---|
| 1006 | 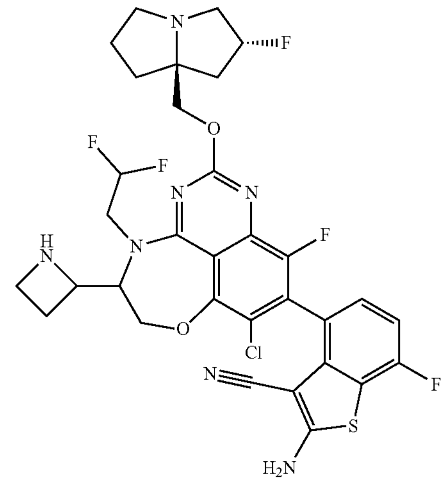 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCN3)CO4)c12] | 2-amino-4-(5-(azetidin-2-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 706.1 |
| 1007 | 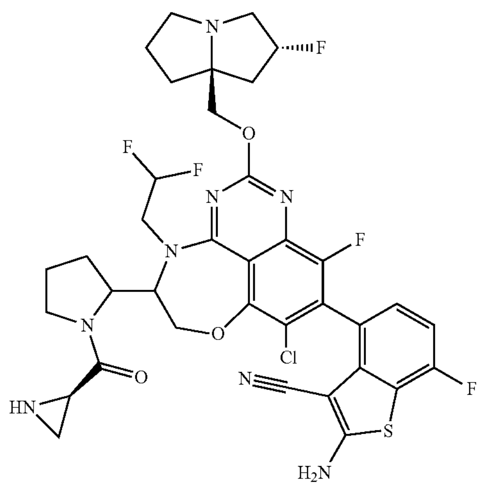 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCN3C(=O)[C@H]3CN3)CO4)c12] | 2-amino-4-(5-(1-((R)-aziridine-2-carbonyl)pyrrolidin-2-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 789 |
| 1008 | 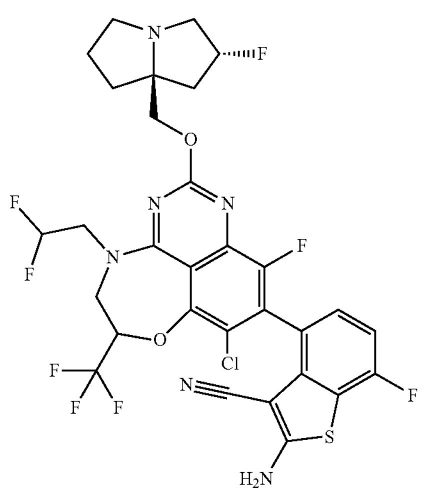 [SMILES: N#Cc1c(N)sc2c(F)ccc(-c3c(Cl)c4c5c(nc(OC[C@@]67CCCN6C[C@H](F)C7)nc5c3F)N(CC(F)F)CC(C(F)(F)F)O4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-6-(trifluoromethyl)-5,6-dihydro-4H-[1,4]oxazepino[5,6,7-de]quinazolin-9-yl)-7-fluorobenzo[b]thiophene-3-carbonitrile | 718.8 |

TABLE 1-continued

| No. | Structure | Chemical Name | [M + H]+ |
|---|---|---|---|
| 1009 | 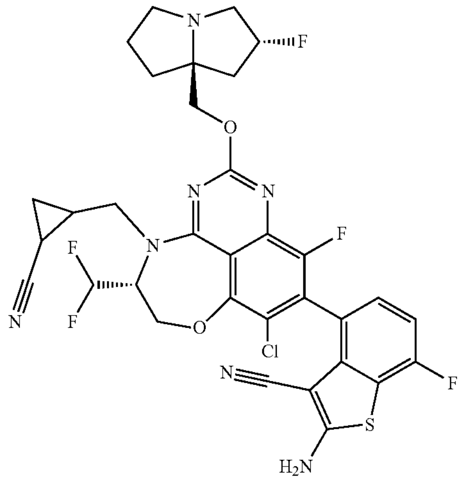 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716 |
| 1010 | 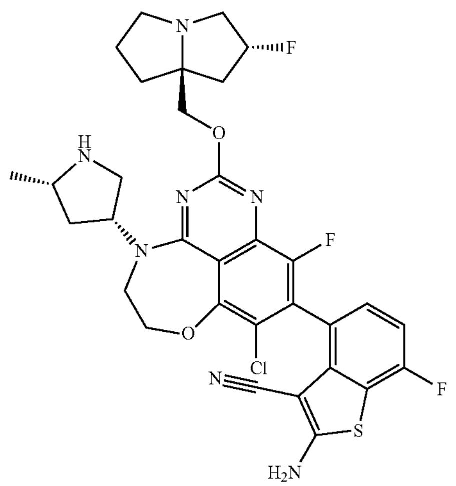 [SMILES: C[C@H]1C[C@@H](N2CCOc3c(Cl)c(-c4ccc(F)c5sc(N)c(C#N)c45)c(F)c4nc(OC[C@@]56CCCN5C[C@H](F)C6)nc2c34)CN1] | 2-amino-4-(8-chloro-10-fluoro-2-(((2R,7aS)-2-fluorotetrahydro-1H-pyrrolizin-7a(5H)-yl)methoxy)-4-((3R,5S)-5-methylpyrrolidin-3-yl)-5,6-dihydro-4H-[1,4]oxazepino[5,6,7-de]quinazolin-9-yl)-7-fluorobenzo[b]thiophene-3-carbonitrile | 670.4 |
| 1011 | 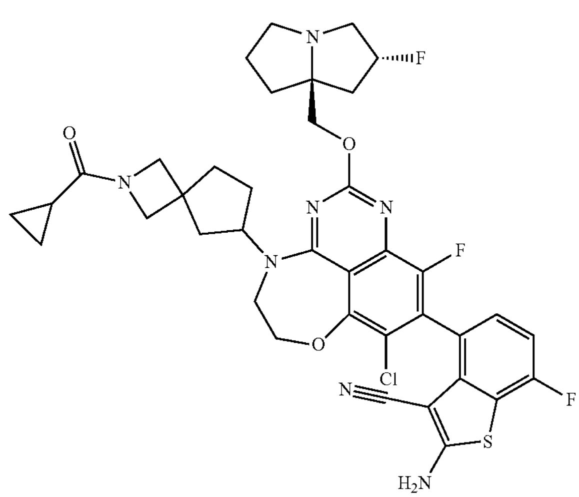 [SMILES: N#Cc1c(N)sc2c(F)ccc(-c3c(Cl)c4c5c(nc(OC[C@@]67CCCN6C[C@H](F)C7)nc5c3F)N(C3CCC5(C3)CN(C(=O)C3CC3)C5)CCO4)c12] | 2-amino-4-(8-chloro-4-(2-(cyclopropanecarbonyl)-2-azaspiro[3.4]octan-6-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 764 |

TABLE 1-continued

| No. | Structure | Chemical Name | [M + H]+ |
|---|---|---|---|
| 1012 | 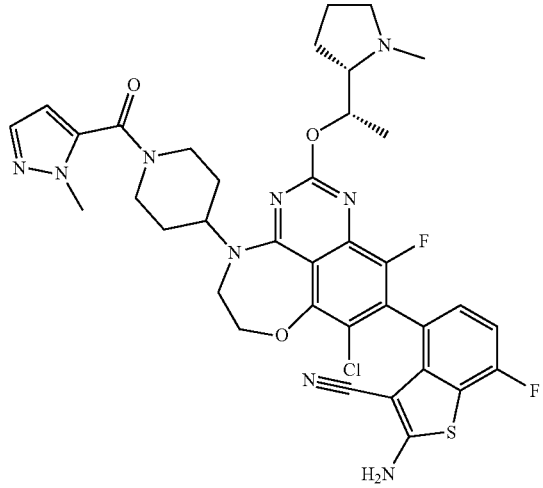 [SMILES: C[C@H](Oc1nc2c3c(c(Cl)c(-c4ccc(F)c5sc(N)c(C#N)c45)c(F)c3n1)OCCN2C1CCN(C(=O)c2ccnn2C)CC1)[C@@H]1CCCN1C] | 2-amino-4-(8-chloro-10-fluoro-4-(1-(1-methyl-1H-pyrazole-5-carbonyl)piperidin-4-yl)-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile | 748.3 |
| 1013 | 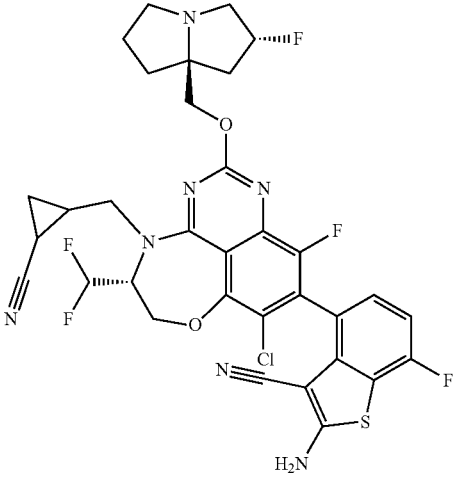 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 715.9 |
| 1014 | 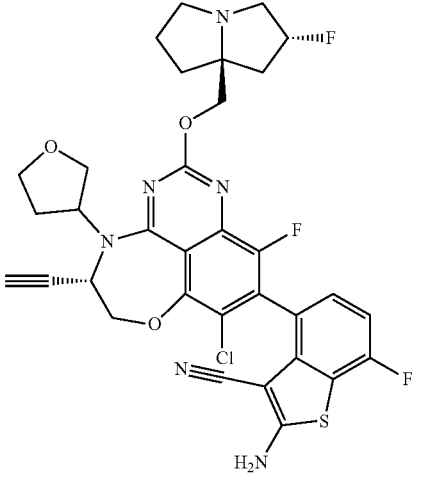 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-5-ethynyl-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 681.3 |

//TABLE 1-continued

| No. | Structure | Chemical Name | [M + H]+ |
|---|---|---|---|
| 1015 | 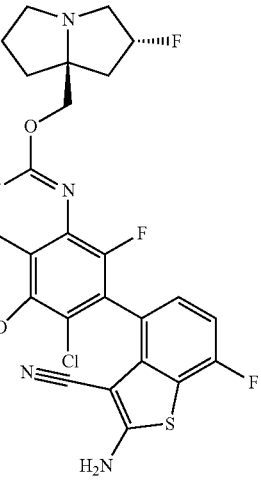 | 2-amino-4-(8-chloro-5-(cyanomethyl)-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 703.9 |
| 1016 | 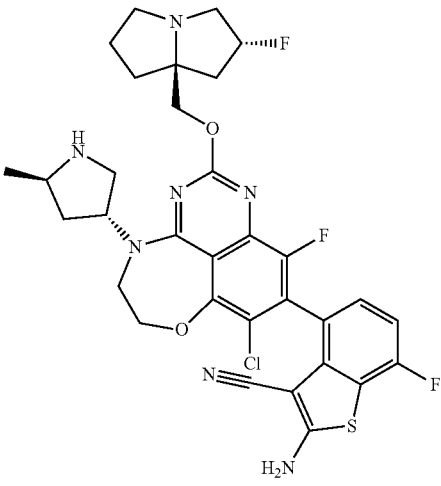 [SMILES: C[C@@H]1C[C@@H](N2CCOc3c(Cl)c(-c4ccc(F)c5sc(N)c(C#N)c45)c(F)c4nc(OC[C@@]56CCCN5C[C@H](F)C6)nc2c34)CN1] | 2-amino-4-(8-chloro-10-fluoro-2-(((2R,7aS)-2-fluorotetrahydro-1H-pyrrolizin-7a(5H)-yl)methoxy)-4-((3R,5R)-5-methylpyrrolidin-3-yl)-5,6-dihydro-4H-[1,4]oxazepino[5,6,7-de]quinazolin-9-yl)-7-fluorobenzo[b]thiophene-3-carbonitrile | 670 |
| 1017 | 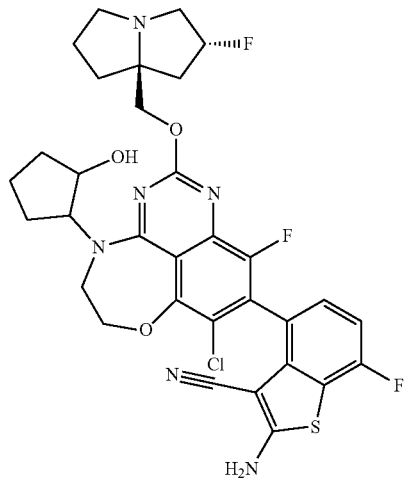 [SMILES: N#Cc1c(N)sc2c(F)ccc(-c3c(Cl)c4c5c(nc(OC[C@@]67CCCN6C[C@H](F)C7)nc5c3F)N(C3CCCC3O)CCO4)c12] | 2-amino-4-(8-chloro-10-fluoro-2-(((2R,7aS)-2-fluorotetrahydro-1H-pyrrolizin-7a(5H)-yl)methoxy)-4-(2-hydroxycyclopentyl)-5,6-dihydro-4H-[1,4]oxazepino[5,6,7-de]quinazolin-9-yl)-7-fluorobenzo[b]thiophene-3-carbonitrile | 671.1 |

TABLE 1-continued

| No. | Chemical Name | [M + H]+ |
|---|---|---|
| 1018 | N-(((5S)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-4-methyl-5,6-dihydro-4H-[1,4]oxazepino[5,6,7-de]quinazolin-5-yl)methyl)-2,2-difluoroacetamide | 708.4 |
| 1019 | 3-(5-(8-ethynyl-7-fluoro-3-hydroxynaphthalen-1-yl)-4-fluoro-2-(((2R,7aS)-2-fluorotetrahydro-1H-pyrrolizin-7a(5H)-yl)methoxy)-8,9-dihydro-10H-7-oxa-1,3,6,10-tetraazacyclohepta[de]naphthalen-10-yl)pyrrolidine-1-carbaldehyde | 644.9 |
| 1020 | 2-amino-4-(8-chloro-4-(3-(dimethylamino)propyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 672.2 |

TABLE 1-continued

| No. | Structure | Chemical Name | [M + H]+ |
|---|---|---|---|
| 1021 | 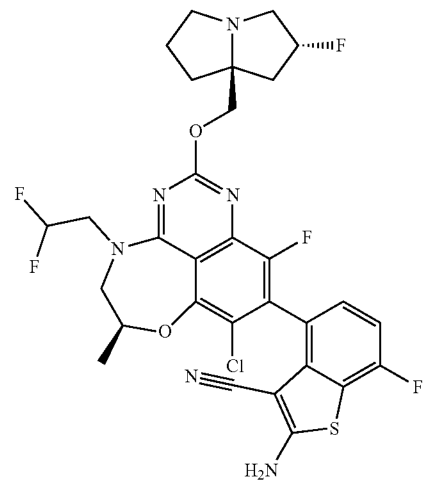 [SMILES: C[C@H]1CN(CC(F)F)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 664.9 |
| 1022 | 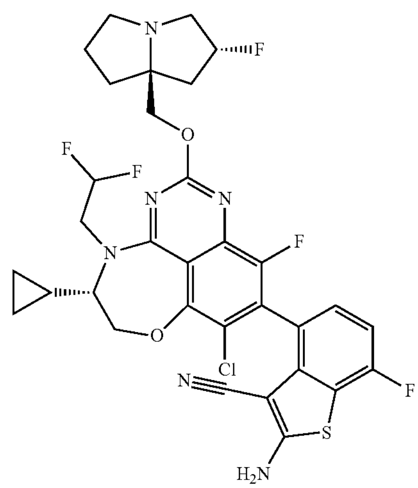 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3)CO4)c12] | 2-amino-4-((S)-8-chloro-5-cyclopropyl-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 691 |
| 1023 | 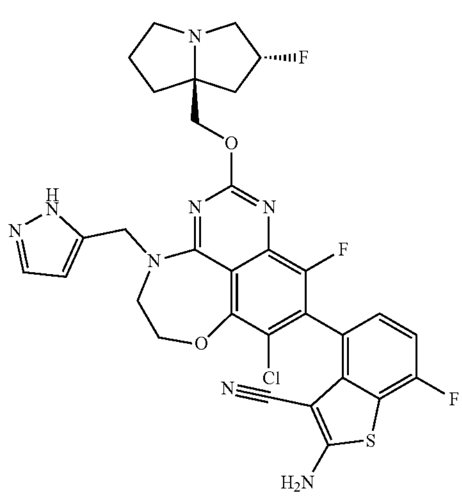 [SMILES: N#Cc1c(N)sc2c(F)ccc(-c3c(Cl)c4c5c(nc(OC[C@@]67CCCN6C[C@H](F)C7)nc5c3F)N(Cc3ccn[nH]3)CCO4)c12] | 4-(4-((1H-pyrazol-5-yl)methyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-2-amino-7-fluorobenzo[b]thiophene-3-carbonitrile | 667.3 |

TABLE 1-continued

| No. | Structure | Chemical Name | [M + H]+ |
|---|---|---|---|
| 1024 | 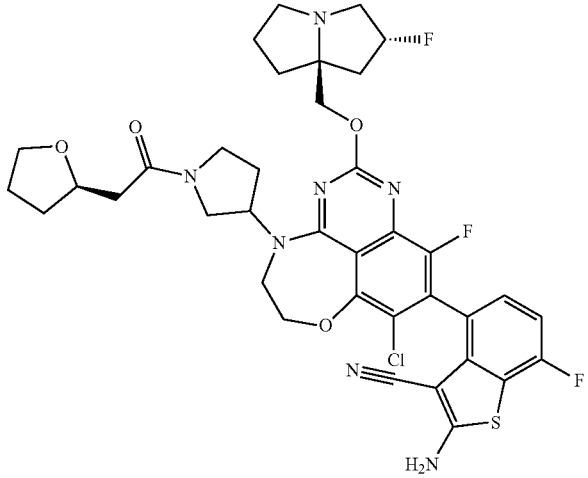 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C[C@H]5CCCO5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-(2-((R)-tetrahydrofuran-2-yl)acetyl)pyrrolidin-3-yl)-5,6-dihydro-4H-[1,4]oxazepino[5,6,7-de]quinazolin-9-yl)-7-fluorobenzo[b]thiophene-3-carbonitrile | 768.5 |
| 1025 | 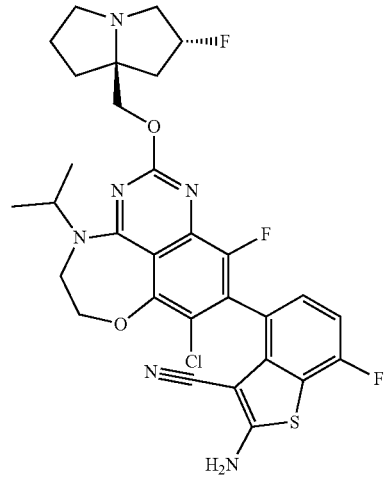 [SMILES: CC(C)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-isopropyl-5,6-dihydro-4H-[1,4]oxazepino[5,6,7-de]quinazolin-9-yl)-7-fluorobenzo[b]thiophene-3-carbonitrile | 628.8 |
| 1026 | 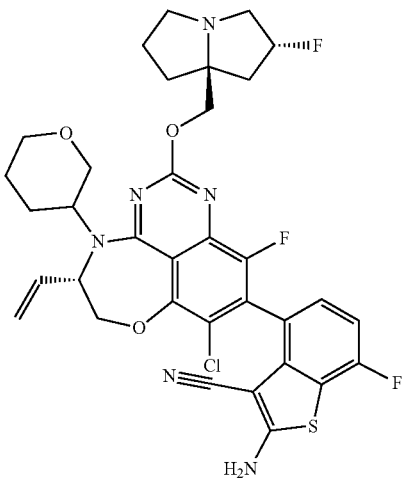 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCCOC1] | 2-amino-4-((5S)-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazolin-9-yl)-7-fluorobenzo[b]thiophene-3-carbonitrile | 696.9 |

TABLE 1-continued

| No. | Structure | Chemical Name | [M + H]+ |
|---|---|---|---|
| 1027 | 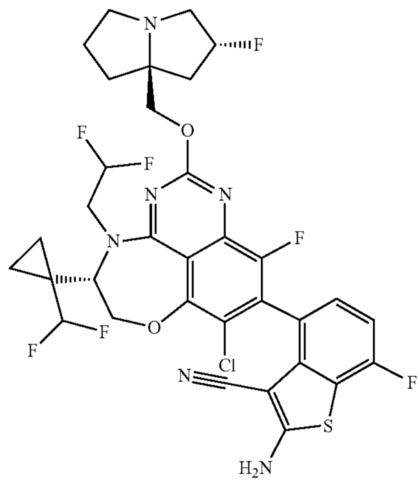 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(C(F)F)CC3)CO4)c12] | 2-amino-4-((S)-8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 741.1 |
| 1028 | 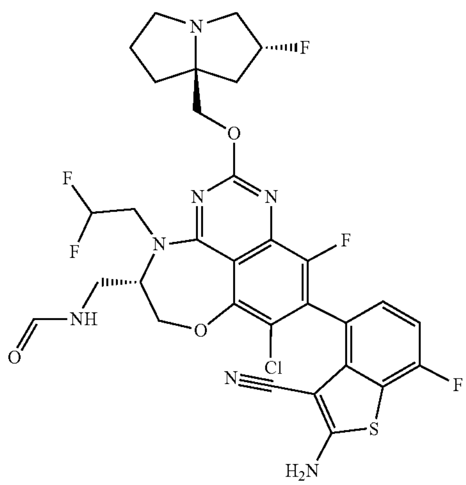 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](CNC=O)CO4)c12] | N-(((5S)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)formamide | 708.3 |
| 1029 | 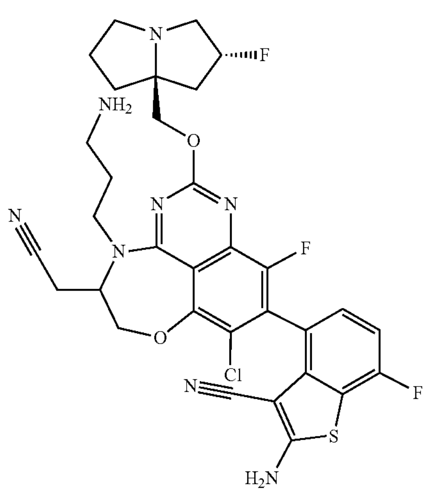 [SMILES: N#CCC1COc2c(Cl)c(-c3ccc(F)c4sc(N)c(C#N)c34)c(F)c3nc(OC[C@@]45CCCN4C[C@H](F)C5)nc(c23)N1CCCN] | 2-amino-4-(4-(3-aminopropyl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 683.2 |

TABLE 1-continued

| No. | Structure | Chemical Name | [M + H]+ |
|---|---|---|---|
| 1030 | 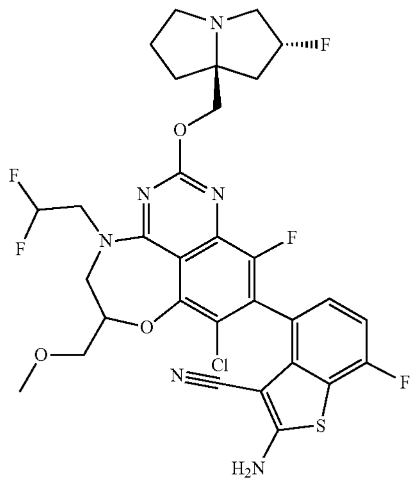 [SMILES: COCC1CN(CC(F)F)c2nc(OC[C@@]34CCCN3C[C@H](F)C4)nc3c(F)c(-c4ccc(F)c5sc(N)c(C#N)c45)c(Cl)c(c23)O1] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-6-(methoxymethyl)-5,6-dihydro-4H-[1,4]oxazepino[5,6,7-de]quinazolin-9-yl)-7-fluorobenzo[b]thiophene-3-carbonitrile | 695 |
| 1031 | 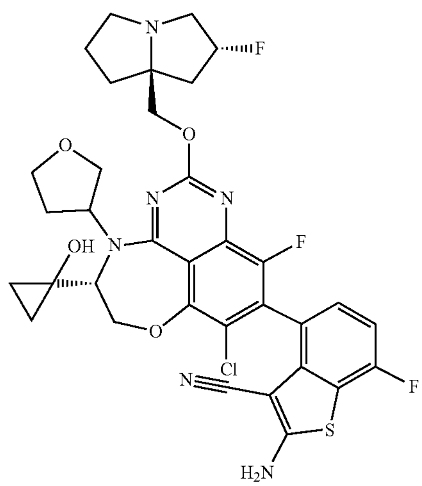 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(O)CC3)CO4)c12] | 2-amino-4-((5R)-8-chloro-10-fluoro-2-(((2R,7aS)-2-fluorotetrahydro-1H-pyrrolizin-7a(5H)-yl)methoxy)-5-(1-hydroxycyclopropyl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 713 |
| 1032 | 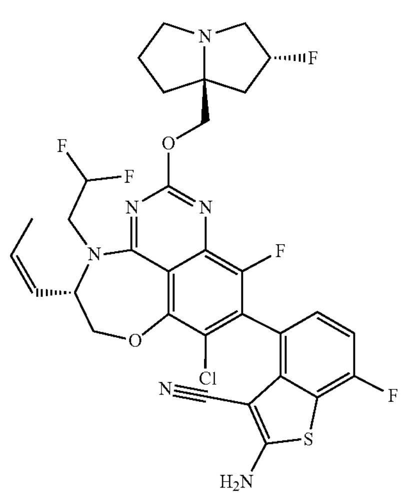 [SMILES: C/C=C\[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((Z)-prop-1-en-1-yl)-5,6-dihydro-4H-[1,4]oxazepino[5,6,7-de]quinazolin-9-yl)-7-fluorobenzo[b]thiophene-3-carbonitrile | 690.9 |

TABLE 1-continued

| No. | Structure | Chemical Name | [M + H]+ |
|---|---|---|---|
| 1033 | 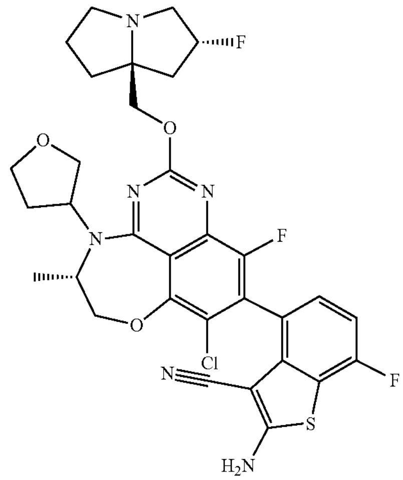 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-5-methyl-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 671.3 |
| 1034 | 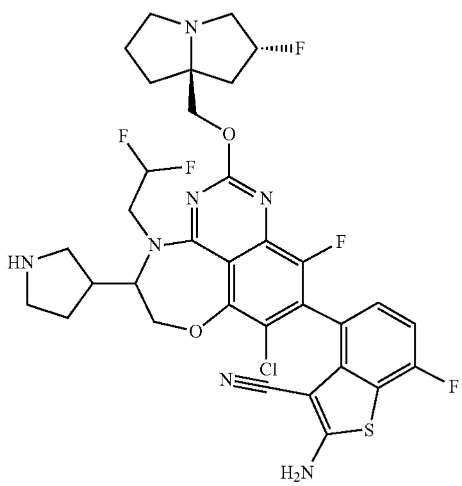 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCNC3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(pyrrolidin-3-yl)-5,6-dihydro-4H-[1,4]oxazepino[5,6,7-de]quinazolin-9-yl)-7-fluorobenzo[b]thiophene-3-carbonitrile | 720.2 |
| 1035 | 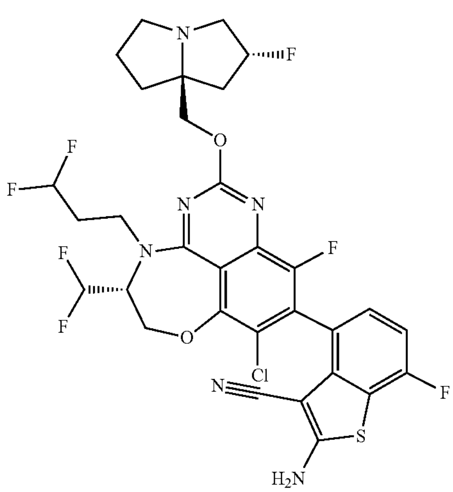 [SMILES: N#Cc1c(N)sc2c(F)ccc(-c3c(Cl)c4c5c(nc(OC[C@@]67CCCN6C[C@H](F)C7)nc5c3F)N(CCC(F)F)[C@@H](C(F)F)CO4)c12] | 2-amino-4-((R)-8-chloro-5-(difluoromethyl)-4-(3,3-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 715.3 |

TABLE 1-continued

| No. | Structure | Chemical Name | [M + H]+ |
|---|---|---|---|
| 1036 | 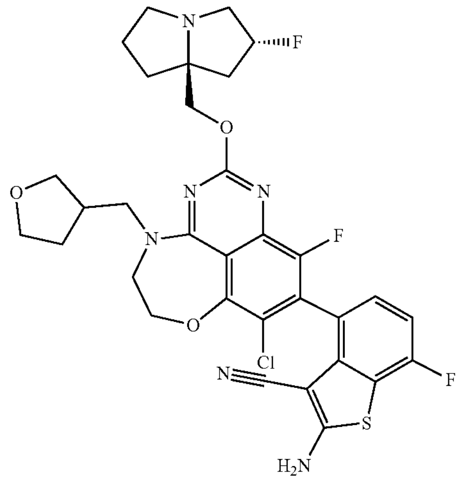 [SMILES: N#Cc1c(N)sc2c(F)ccc(-c3c(Cl)c4c5c(nc(OC[C@@]67CCCN6C[C@H](F)C7)nc5c3F)N(CC3CCOC3)CCO4)c12] | 2-amino-4-(8-chloro-10-fluoro-2-(((2R,7aS)-2-fluorotetrahydro-1H-pyrrolizin-7a(5H)-yl)methoxy)-4-((tetrahydrofuran-3-yl)methyl)-5,6-dihydro-4H-[1,4]oxazepino[5,6,7-de]quinazolin-9-yl)-7-fluorobenzo[b]thiophene-3-carbonitrile | 671.3 |
| 1037 | 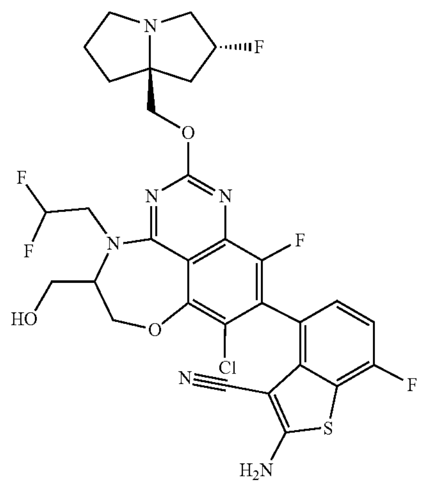 [SMILES: N#Cc1c(N)sc2c(F)ccc(-c3c(Cl)c4c5c(nc(OC[C@@]67CCCN6C[C@H](F)C7)nc5c3F)N(CC(F)F)C(CO)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(hydroxymethyl)-5,6-dihydro-4H-[1,4]oxazepino[5,6,7-de]quinazolin-9-yl)-7-fluorobenzo[b]thiophene-3-carbonitrile | 681.2 |
| 1038 | 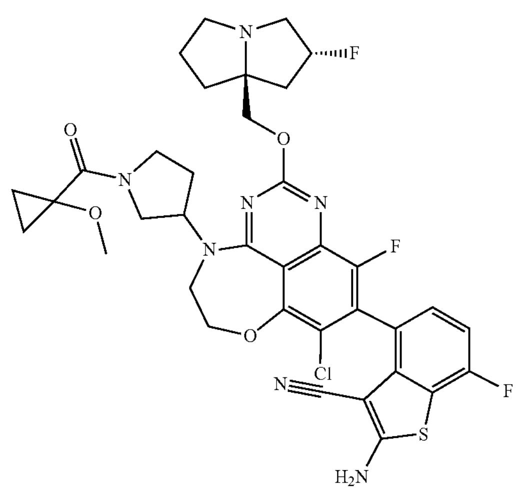 [SMILES: COC1(C(=O)N2CCC(N3CCOc4c(Cl)c(-c5ccc(F)c6sc(N)c(C#N)c56)c(F)c5nc(OC[C@@]67CCCN6C[C@H](F)C7)nc3c45)C2)CC1] | 2-amino-4-(8-chloro-10-fluoro-2-(((2R,7aS)-2-fluorotetrahydro-1H-pyrrolizin-7a(5H)-yl)methoxy)-4-(1-(1-methoxycyclopropane-1-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 754.3 |

TABLE 1-continued

| No. | Structure | Chemical Name | [M + H]⁺ |
|---|---|---|---|
| 1039 | 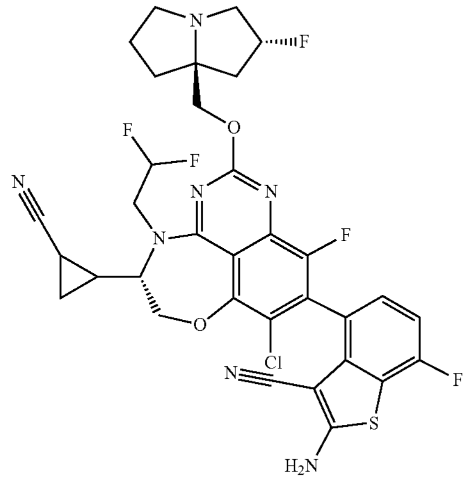 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3C#N)CO4)c12] | 2-amino-4-((5S)-8-chloro-5-(2-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 715.9 |
| 1040 | 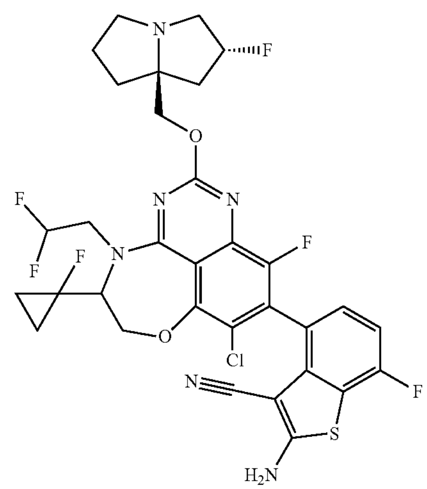 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3(F)CC3)CO4)c12] | 2-amino-4-(8-chloro-4-(2,2-difluoroethyl)-10-fluoro-5-(1-fluorocyclopropyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 709 |
| 1041 | 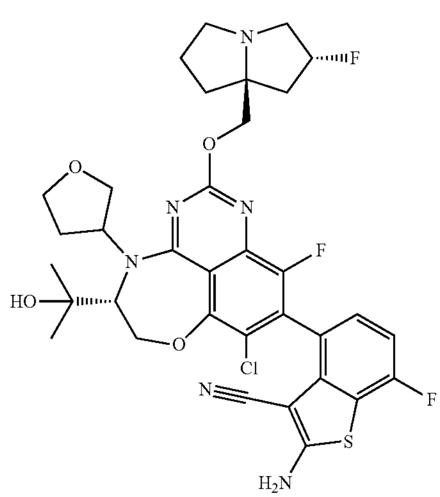 [SMILES: CC(C)(O)[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5R)-8-chloro-10-fluoro-2-(((2R,7aS)-2-fluorotetrahydro-1H-pyrrolizin-7a(5H)-yl)methoxy)-5-(2-hydroxypropan-2-yl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 715.1 |

TABLE 1-continued

| No. | Structure | Chemical Name | [M + H]+ |
|---|---|---|---|
| 1042 | 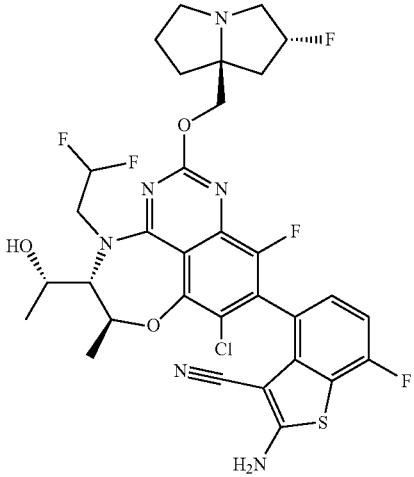 | 2-amino-4-((5S,6S)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 1043 | 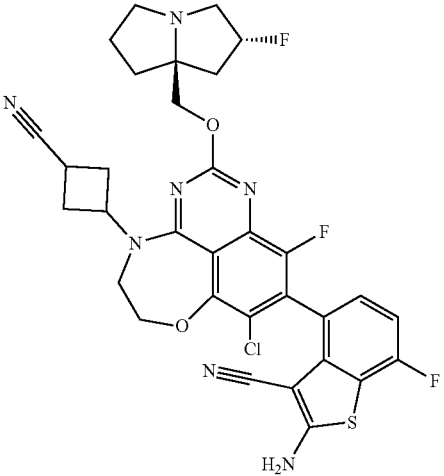 [SMILES: N#Cc1c(N)sc2c(F)ccc(-c3c(Cl)c4c5c(nc(OC[C@@]67CCCN6C[C@H](F)C7)nc5c3F)N(C3CC(C#N)C3)CCO4)c12] | 2-amino-4-(8-chloro-4-(3-cyanocyclobutyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 666.1 |
| 1044 | 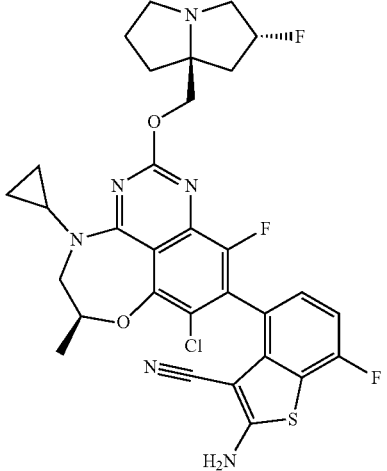 [SMILES: C[C@H]1CN(C2CC2)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-cyclopropyl-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 641.1 |

TABLE 1-continued

| No. | Structure | Chemical Name | [M + H]+ |
|---|---|---|---|
| 1045 | 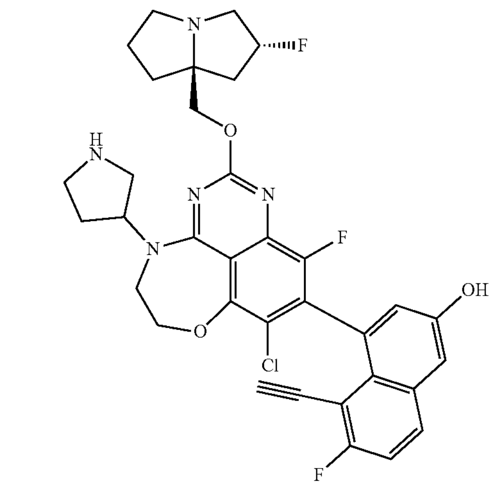 [SMILES: C#Cc1c(F)ccc2cc(O)cc(-c3c(Cl)c4c5c(nc(OC[C@@]67CCCN6C[C@H](F)C7)nc5c3F)N(C3CCNC3)CCO4)c12] | 4-(8-chloro-10-fluoro-2-(((2R,7aS)-2-fluorotetrahydro-1H-pyrrolizin-7a(5H)-yl)methoxy)-4-(pyrrolidin-3-yl)-5,6-dihydro-4H-[1,4]oxazepino[5,6,7-de]quinazolin-9-yl)-5-ethynyl-6-fluoronaphthalen-2-ol | 649.2 |
| 1046 | 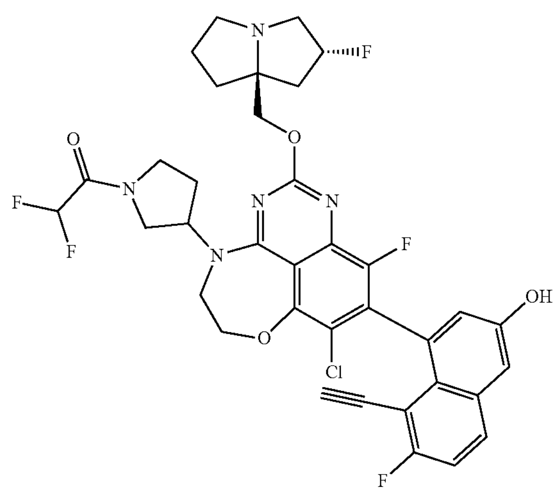 [SMILES: C#Cc1c(F)ccc2cc(O)cc(-c3c(Cl)c4c5c(nc(OC[C@@]67CCCN6C[C@H](F)C7)nc5c3F)N(C3CCN(C(=O)C(F)F)C3)CCO4)c12] | 1-(3-(8-chloro-9-(8-ethynyl-7-fluoro-3-hydroxynaphthalen-1-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)pyrrolidin-1-yl)-2,2-difluoroethan-1-one | 728.3 |
| 1047 | 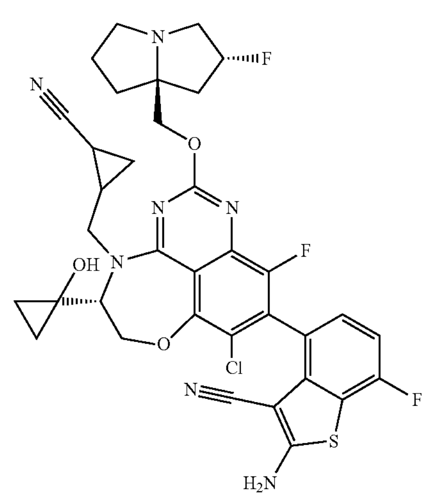 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |

TABLE 1-continued

| No. | Structure | Chemical Name | [M + H]⁺ |
|---|---|---|---|
| 1048 | 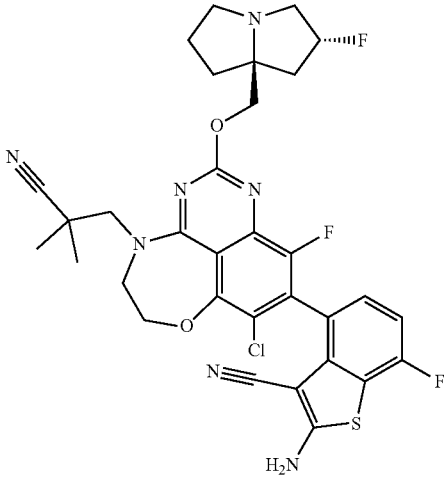 [SMILES: CC(C)(C#N)CN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(2-cyano-2-methylpropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 668.2 |
| 1049 | 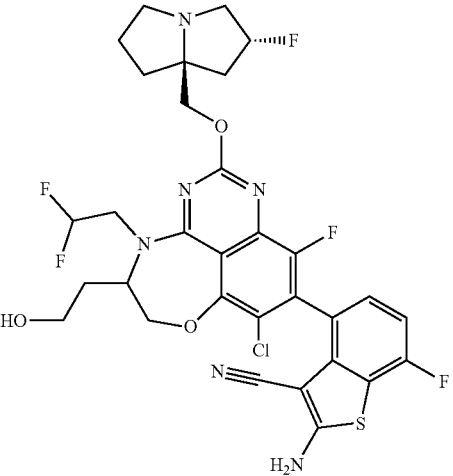 [SMILES: N#Cc1c(N)sc2c(F)ccc(-c3c(Cl)c4c5c(nc(OC[C@@]67CCCN6C[C@H](F)C7)nc5c3F)N(CC(F)F)C(CCO)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxyethyl)-5,6-dihydro-4H-[1,4]oxazepino[5,6,7-de]quinazolin-9-yl)-7-fluorobenzo[b]thiophene-3-carbonitrile | 694.8 |
| 1050 | 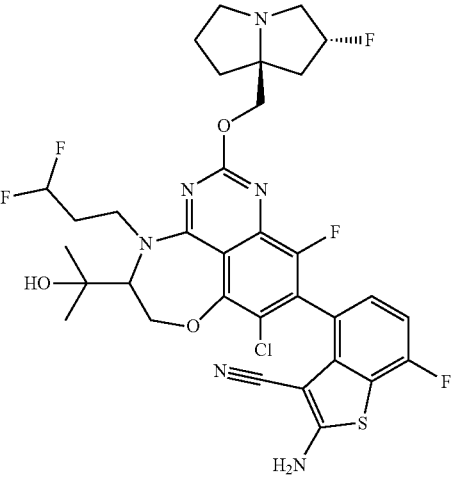 [SMILES: CC(C)(O)C1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-(8-chloro-4-(3,3-difluoropropyl)-10-fluoro-2-(((2R,7aS)-2-fluorotetrahydro-1H-pyrrolizin-7a(5H)-yl)methoxy)-5-(2-hydroxypropan-2-yl)-5,6-dihydro-4H-[1,4]oxazepino[5,6,7-de]quinazolin-9-yl)-7-fluorobenzo[b]thiophene-3-carbonitrile | 722.9 |

TABLE 1-continued

| No. | Structure | Chemical Name | [M + H]⁺ |
|---|---|---|---|
| 1051 | 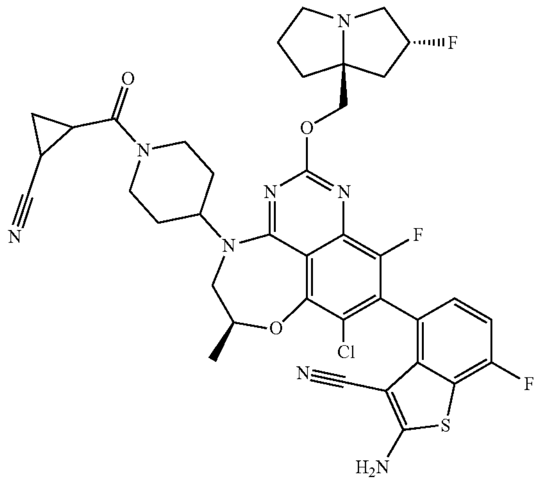 [SMILES: C[C@H]1CN(C2CCN(C(=O)C3CC3C#N)CC2)c2nc(OC[C@@]34CCCN3C[C@H](F)C4)nc3c(F)c(-c4ccc(F)c5sc(N)c(C#N)c45)c(Cl)c(c23)O1] | 2-amino-4-((6S)-8-chloro-4-(1-(2-cyanocyclopropane-1-carbonyl)piperidin-4-yl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 777.3 |
| 1052 | 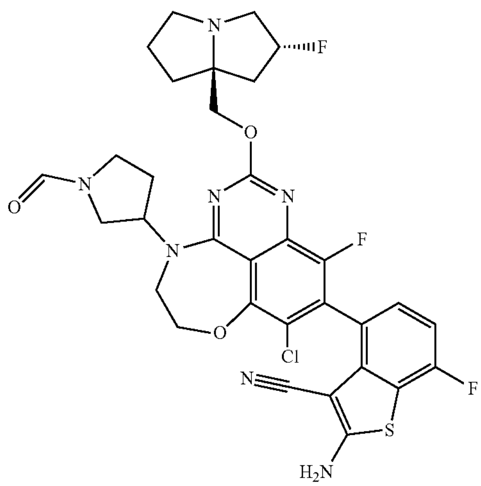 [SMILES: N#Cc1c(N)sc2c(F)ccc(-c3c(Cl)c4c5c(nc(OC[C@@]67CCCN6C[C@H](F)C7)nc5c3F)N(C3CCN(C=O)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-formylpyrrolidin-3-yl)-5,6-dihydro-4H-[1,4]oxazepino[5,6,7-de]quinazolin-9-yl)-7-fluorobenzo[b]thiophene-3-carbonitrile | 684.3 |
| 1053 | 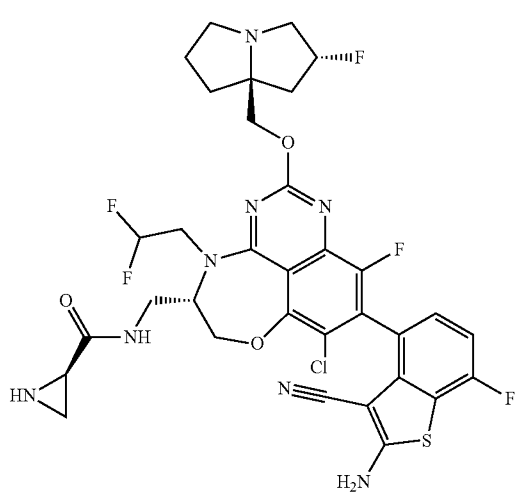 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](CNC(=O)[C@H]3CN3)CO4)c12] | (2R)-N-(((5S)-9-(2-amino-3-cyano-7-fluorobenzo[b]thiophen-4-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)aziridine-2-carboxamide | 749.3 |

TABLE 1-continued

| No. | Structure | Chemical Name | [M + H]+ |
|---|---|---|---|
| 1054 | 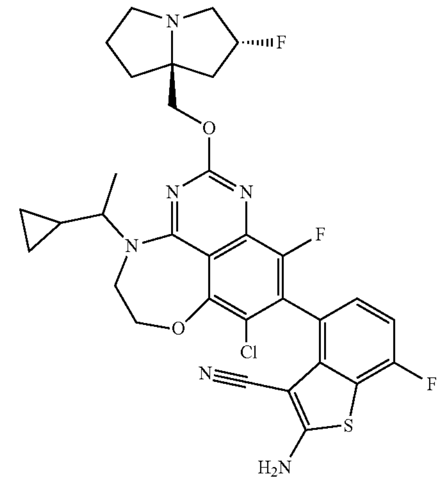 [SMILES: CC(C1CC1)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(1-cyclopropylethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 654.7 |
| 1055 | 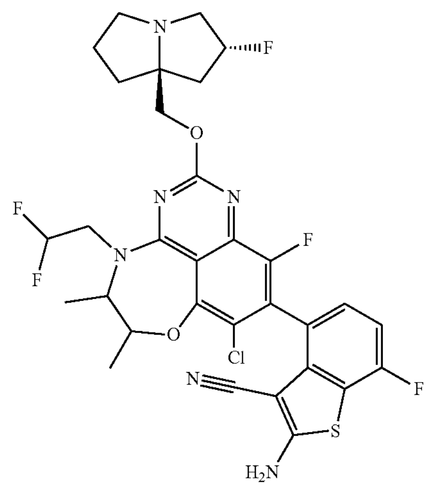 [SMILES: CC1Oc2c(Cl)c(-c3ccc(F)c4sc(N)c(C#N)c34)c(F)c3nc(OC[C@@]45CCCN4C[C@H](F)C5)nc(c23)N(CC(F)F)C1C] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5,6-dimethyl-5,6-dihydro-4H-[1,4]oxazepino[5,6,7-de]quinazolin-9-yl)-7-fluorobenzo[b]thiophene-3-carbonitrile | 678.9 |
| 1056 | 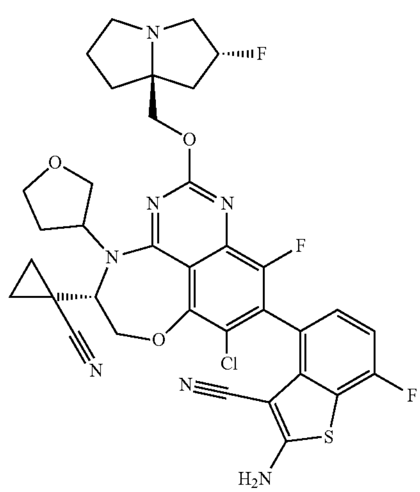 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(C#N)CC3)CO4)c12] | 2-amino-4-((5S)-8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 721.9 |

TABLE 1-continued

| No. | Structure | Chemical Name | [M + H]+ |
|---|---|---|---|
| 1057 | 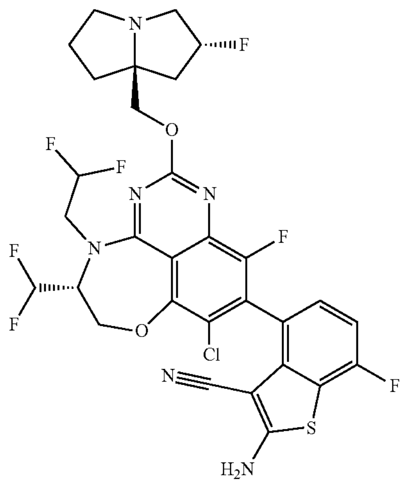 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C(F)F)CO4)c12] | 2-amino-4-((R)-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 701.3 |
| 1058 | 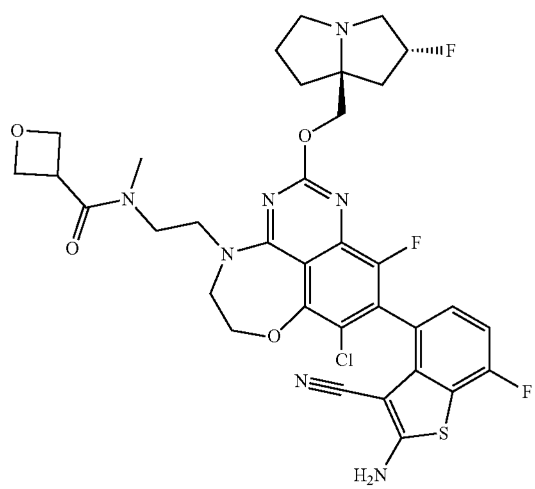 [SMILES: CN(CCN1CCOc2c(Cl)c(-c3ccc(F)c4sc(N)c(C#N)c34)c(F)c3nc(OC[C@@]45CCCN4C[C@H](F)C5)nc1c23)C(=O)C1COC1] | N-(2-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)-N-methyloxetane-3-carboxamide | 728.2 |
| 1059 | 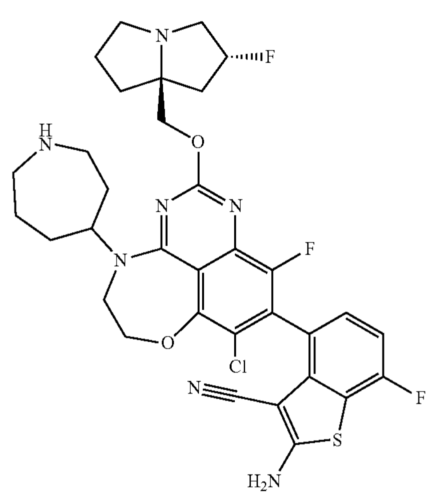 [SMILES: N#Cc1c(N)sc2c(F)ccc(-c3c(Cl)c4c5c(nc(OC[C@@]67CCCN6C[C@H](F)C7)nc5c3F)N(C3CCCNCC3)CCO4)c12] | 2-amino-4-(4-(azepan-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 684.4 |

TABLE 1-continued

| No. | Structure | Chemical Name | [M + H]⁺ |
|---|---|---|---|
| 1060 | 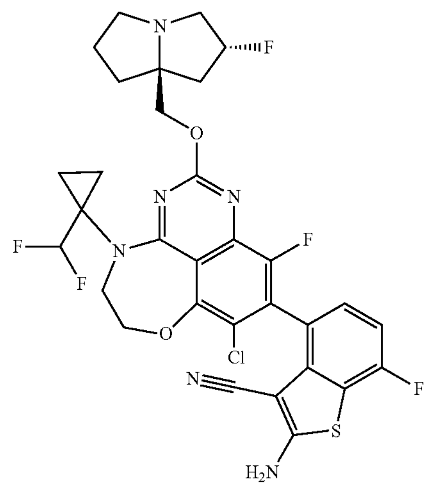 [SMILES: N#Cc1c(N)sc2c(F)ccc(-c3c(Cl)c4c5c(nc(OC[C@@]67CCCN6C[C@H](F)C7)nc5c3F)N(C3(C(F)F)CC3)CCO4)c12] | 2-amino-4-(8-chloro-4-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 677.3 |
| 1061 | 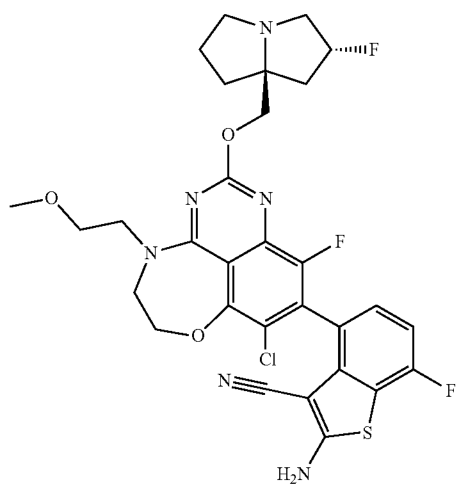 [SMILES: COCCN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-10-fluoro-2-(((2R,7aS)-2-fluorotetrahydro-1H-pyrrolizin-7a(5H)-yl)methoxy)-4-(2-methoxyethyl)-5,6-dihydro-4H-[1,4]oxazepino[5,6,7-de]quinazolin-9-yl)-7-fluorobenzo[b]thiophene-3-carbonitrile | 645.2 |
| 1062 | 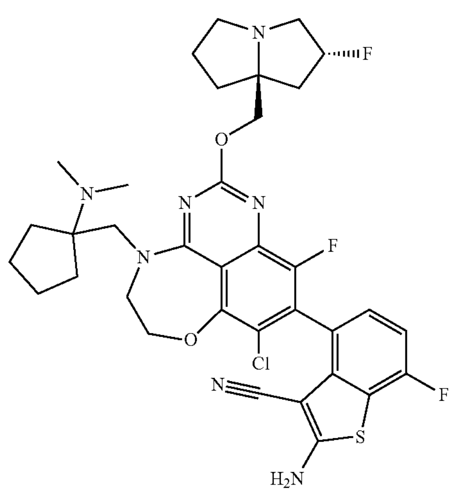 [SMILES: CN(C)C1(CN2CCOc3c(Cl)c(-c4ccc(F)c5sc(N)c(C#N)c45)c(F)c4nc(OC[C@@]56CCCN5C[C@H](F)C6)nc2c34)CCCC1] | 2-amino-4-(8-chloro-4-((1-(dimethylamino)cyclopentyl)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 712.3 |

TABLE 1-continued

| No. | Structure | Chemical Name | [M + H]+ |
|---|---|---|---|
| 1063 | 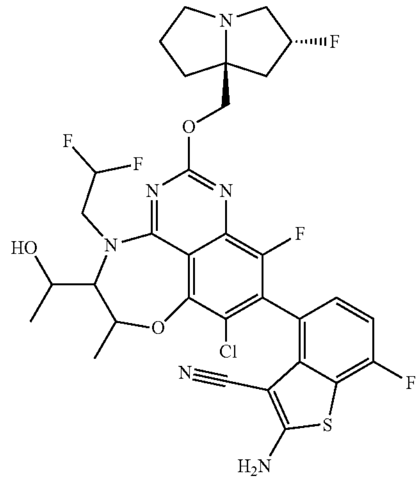 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 1064 | 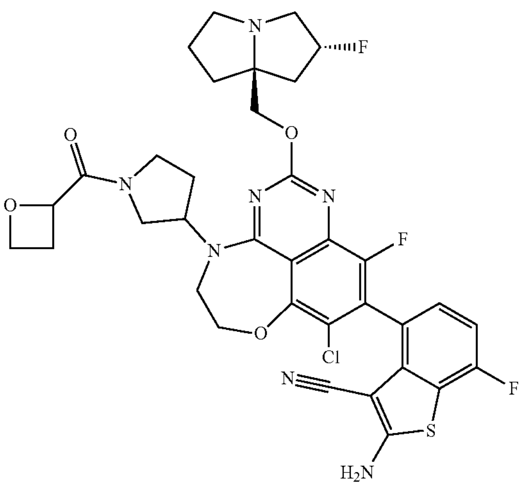 [SMILES: N#Cc1c(N)sc2c(F)ccc(-c3c(Cl)c4c5c(nc(OC[C@@]67CCCN6C[C@H](F)C7)nc5c3F)N(C3CCN(C(=O)C5CCO5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(1-(oxetane-2-carbonyl)pyrrolidin-3-yl)-5,6-dihydro-4H-[1,4]oxazepino[5,6,7-de]quinazolin-9-yl)-7-fluorobenzo[b]thiophene-3-carbonitrile | 740.3 |
| 1065 | 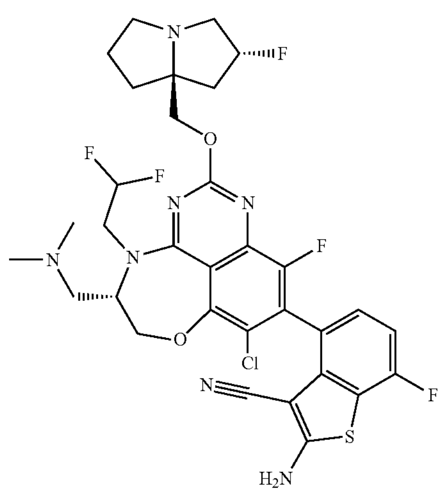 [SMILES: CN(C)C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-((dimethylamino)methyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 708.3 |

TABLE 1-continued

| No. | Structure | Chemical Name | [M + H]+ |
|---|---|---|---|
| 1066 | 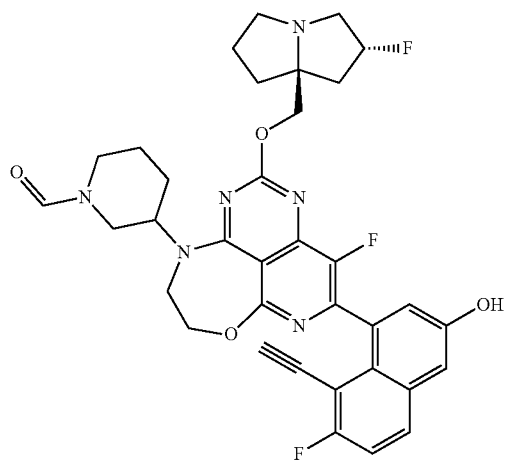 [SMILES: C#Cc1c(F)ccc2cc(O)cc(-c3nc4c5c(nc(OC[C@@]67CCCN6C[C@H](F)C7)nc5c3F)N(C3CCCN(C=O)C3)CCO4)c12] | 3-(5-(8-ethynyl-7-fluoro-3-hydroxynaphthalen-1-yl)-4-fluoro-2-(((2R,7aS)-2-fluorotetrahydro-1H-pyrrolizin-7a(5H)-yl)methoxy)-8,9-dihydro-10H-7-oxa-1,3,6,10-tetraazacyclohepta[de]naphthalen-10-yl)piperidine-1-carbaldehyde | 658.8 |
| 1067 | 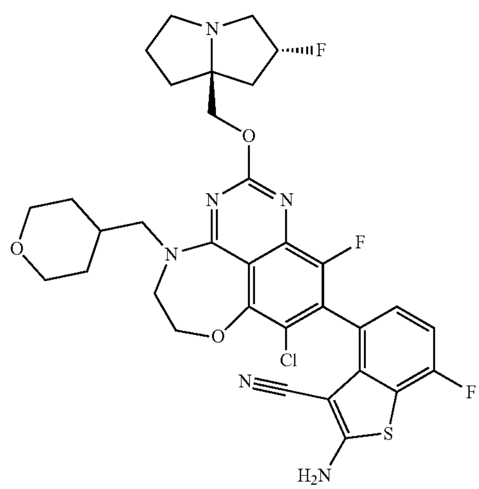 [SMILES: N#Cc1c(N)sc2c(F)ccc(-c3c(Cl)c4c5c(nc(OC[C@@]67CCCN6C[C@H](F)C7)nc5c3F)N(CC3CCOCC3)CCO4)c12] | 2-amino-4-(8-chloro-10-fluoro-2-(((2R,7aS)-2-fluorotetrahydro-1H-pyrrolizin-7a(5H)-yl)methoxy)-4-((tetrahydro-2H-pyran-4-yl)methyl)-5,6-dihydro-4H-[1,4]oxazepino[5,6,7-de]quinazolin-9-yl)-7-fluorobenzo[b]thiophene-3-carbonitrile | 685.4 |
| 1068 | 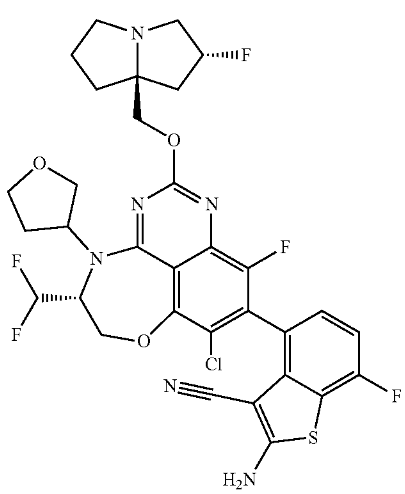 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C(F)F)CO4)c12] | 2-amino-4-((5R)-8-chloro-5-(difluoromethyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 707 |

TABLE 1-continued

| No. | Structure | Chemical Name | [M + H]+ |
|---|---|---|---|
| 1069 | 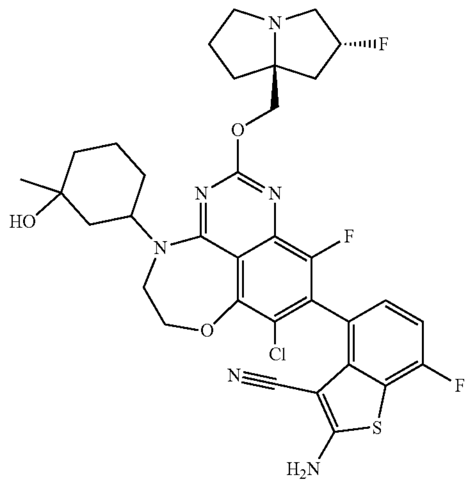 [SMILES: CC1(O)CCCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(3-hydroxy-3-methylcyclohexyl)-5,6-dihydro-4H-[1,4]oxazepino[5,6,7-de]quinazolin-9-yl)-7-fluorobenzo[b]thiophene-3-carbonitrile | 699.3 |
| 1070 | 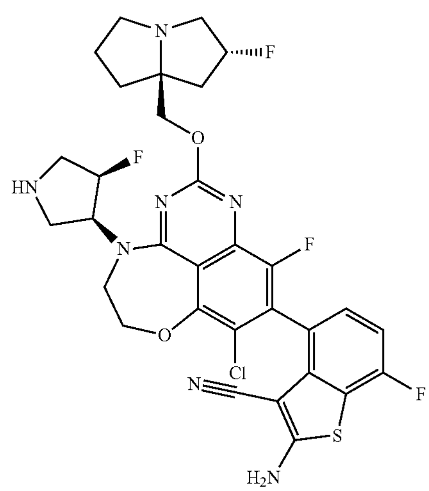 [SMILES: N#Cc1c(N)sc2c(F)ccc(-c3c(Cl)c4c5c(nc(OC[C@@]67CCCN6C[C@H](F)C7)nc5c3F)N([C@H]3CNC[C@H]3F)CCO4)c12] | 2-amino-4-(8-chloro-10-fluoro-4-((3S,4R)-4-fluoropyrrolidin-3-yl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 674 |
| 1071 | 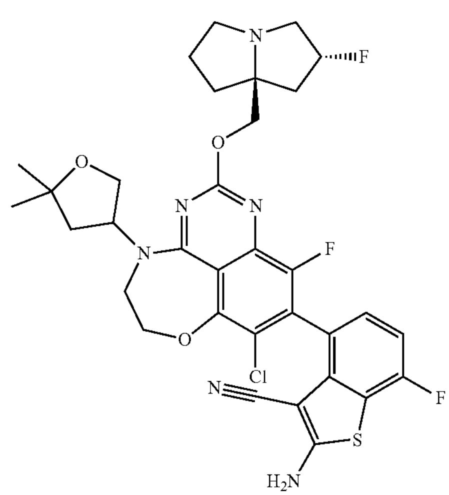 [SMILES: CC1(C)CC(N2CCOc3c(Cl)c(-c4ccc(F)c5sc(N)c(C#N)c45)c(F)c4nc(OC[C@@]56CCCN5C[C@H](F)C6)nc2c34)CO1] | 2-amino-4-(8-chloro-4-(5,5-dimethyltetrahydrofuran-3-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 685.4 |

TABLE 1-continued

| No. | Structure | Chemical Name | [M + H]+ |
|---|---|---|---|
| 1072 | 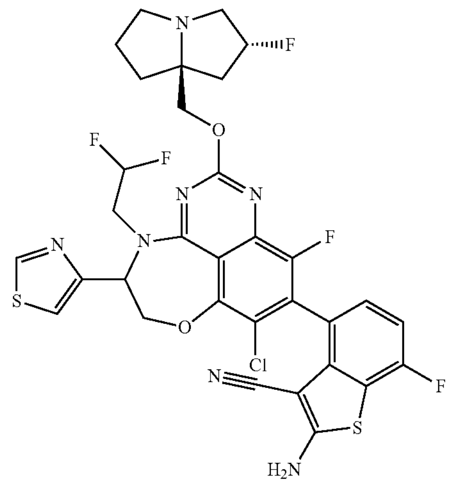 [SMILES: N#Cc1c(N)sc2c(F)ccc(-c3c(Cl)c4c5c(nc(OC[C@@]67CCCN6C[C@H](F)C7)nc5c3F)N(CC(F)F)C(c3cscn3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(thiazol-4-yl)-5,6-dihydro-4H-[1,4]oxazepino[5,6,7-de]quinazolin-9-yl)-7-fluorobenzo[b]thiophene-3-carbonitrile | 734.2 |
| 1073 | 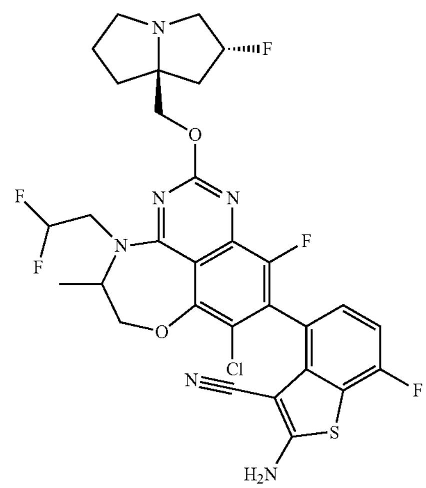 [SMILES: CC1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 664.9 |
| 1074 | 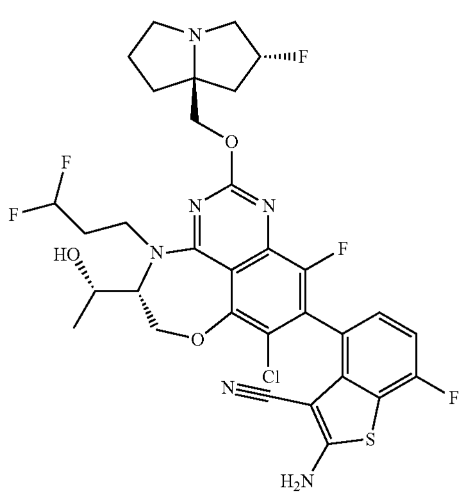 [SMILES: C[C@H](O)[C@H]1COc2c(Cl)c(-c3ccc(F)c4sc(N)c(C#N)c34)c(F)c3nc(OC[C@@]45CCCN4C[C@H](F)C5)nc(c23)N1CCC(F)F] | 2-amino-4-((5R)-8-chloro-4-(3,3-difluoropropyl)-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 708.9 |

TABLE 1-continued

| No. | Structure | Chemical Name | [M + H]⁺ |
|---|---|---|---|
| 1075 | 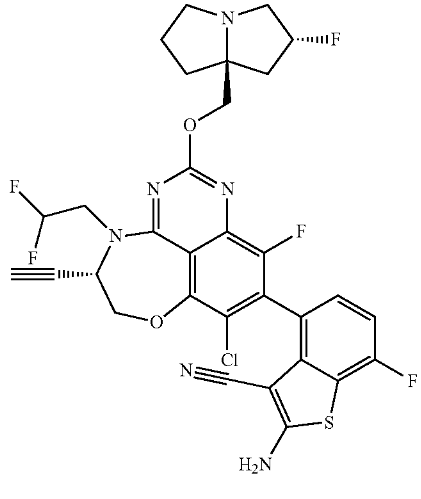 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 675 |
| 1076 | 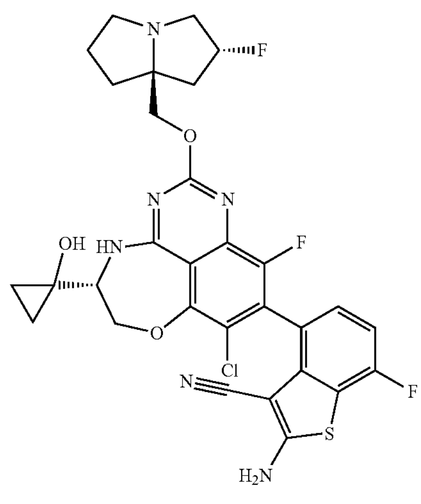 [SMILES: N#Cc1c(N)sc2c(F)ccc(-c3c(Cl)c4c5c(nc(OC[C@@]67CCCN6C[C@H](F)C7)nc5c3F)N[C@@H](C3(O)CC3)CO4)c12] | 2-amino-4-((R)-8-chloro-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 643 |
| 1077 | 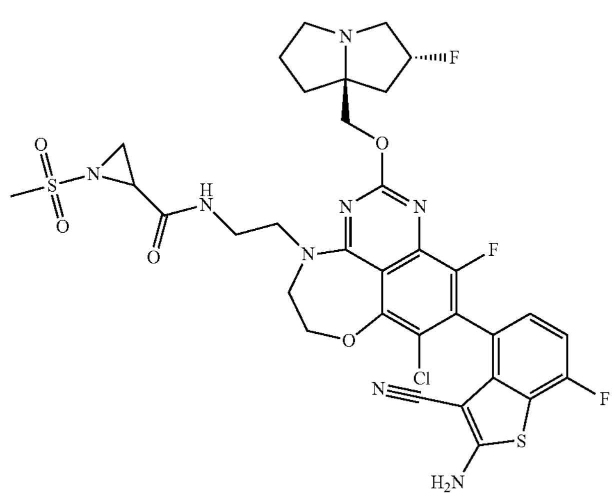 [SMILES: CS(=O)(=O)N1CC1C(=O)NCCN1CCOc2c(Cl)c(-c3ccc(F)c4sc(N)c(C#N)c34)c(F)c3nc(OC[C@@]45CCCN4C[C@H](F)C5)nc1c23] | N-(2-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)-1-(methylsulfonyl)aziridine-2-carboxamide | 777.3 |

TABLE 1-continued

| No. | Structure | Chemical Name | [M + H]⁺ |
|---|---|---|---|
| 1078 | 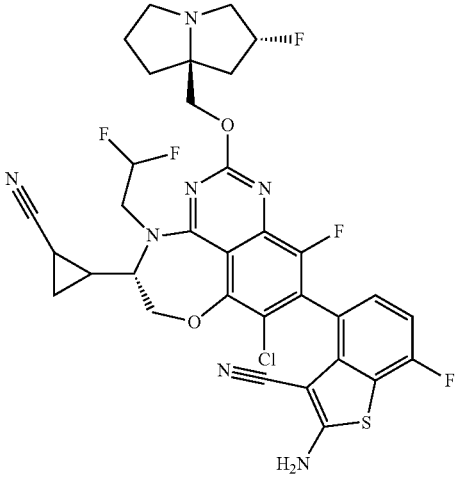 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3C#N)CO4)c12] | 2-amino-4-((5S)-8-chloro-5-(2-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 715.9 |
| 1079 | 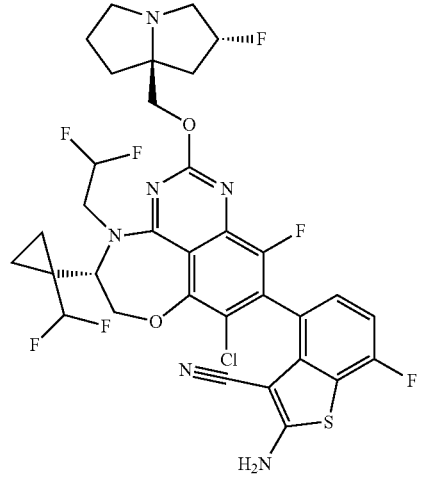 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3(C(F)F)CC3)CO4)c12] | 2-amino-4-((S)-8-chloro-4-(2,2-difluoroethyl)-5-(1-(difluoromethyl)cyclopropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 741.1 |
| 1080 | 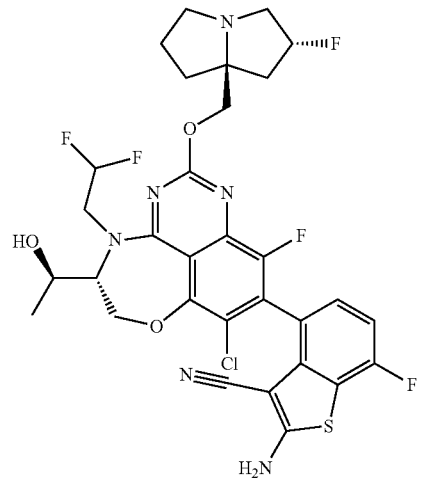 [SMILES: C[C@@H](O)[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-8-chloro-4-(2,2-difluoroethyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile | 694.9 |

TABLE 1-continued

| No. | Structure | Chemical Name | [M + H]+ |
|---|---|---|---|
| 1081 | 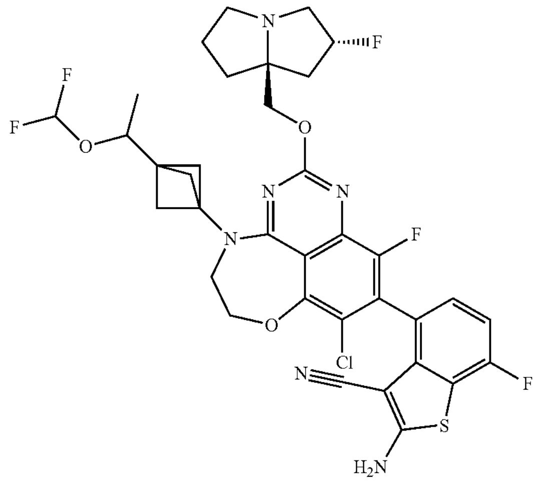 [SMILES: CC(OC(F)F)C12CC(N3CCOc4c(Cl)c(-c5ccc(F)c6sc(N)c(C#N)c56)c(F)c5nc(OC[C@@]67CCCN6C[C@H](F)C7)nc3c45)(C1)C2] | 2-amino-4-(8-chloro-4-(3-(1-(difluoromethoxy)ethyl)bicyclo[1.1.1]pentan-1-yl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 746.8 |
| 1082 | 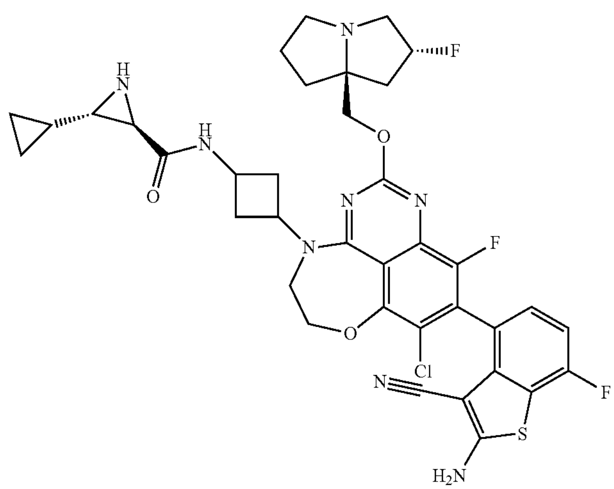 [SMILES: N#Cc1c(N)sc2c(F)ccc(-c3c(Cl)c4c5c(nc(OC[C@@]67CCCN6C[C@H](F)C7)nc5c3F)N(C3CC(NC(=O)[C@@H]5N[C@H]5C5CC5)C3)CCO4)c12] | (2R,3S)-N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)-3-cyclopropylaziridine-2-carboxamide | 765.5 |
| 1083 | 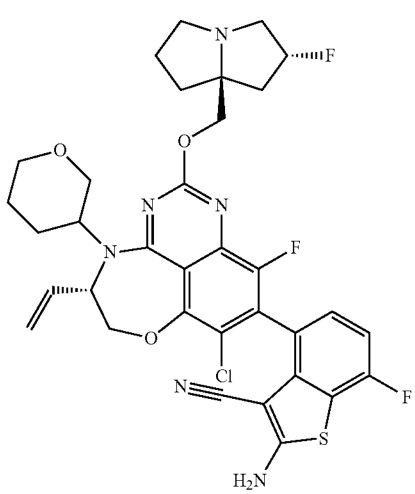 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C1CCCOC1] | 2-amino-4-((5S)-8-chloro-10-fluoro-2-(((2R,7aS)-2-fluorotetrahydro-1H-pyrrolizin-7a(5H)-yl)methoxy)-4-(tetrahydro-2H-pyran-3-yl)-5-vinyl-5,6-dihydro-4H-[1,4]oxazepino[5,6,7-de]quinazolin-9-yl)-7-fluorobenzo[b]thiophene-3-carbonitrile | 696.9 |

TABLE 1-continued

| No. | Structure | Chemical Name | [M + H]+ |
|---|---|---|---|
| 1084 | 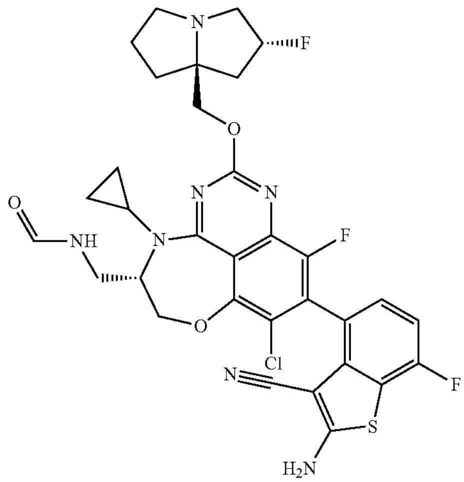 [SMILES: N#Cc1c(N)sc2c(F)ccc(-c3c(Cl)c4c5c(nc(OC[C@@]67CCCN6C[C@H](F)C7)nc5c3F)N(C3CC3)[C@@H](CNC=O)CO4)c12] | N-(((5S)-9-(2-amino-3-cyano-7-fluorobenzo[b]thiophen-4-yl)-8-chloro-4-cyclopropyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-5-yl)methyl)formamide | 684.5 |
| 1085 | 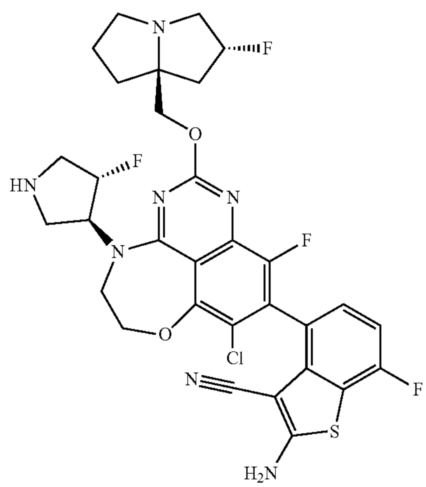 [SMILES: N#Cc1c(N)sc2c(F)ccc(-c3c(Cl)c4c5c(nc(OC[C@@]67CCCN6C[C@H](F)C7)nc5c3F)N([C@H]3CNC[C@@H]3F)CCO4)c12] | 2-amino-4-(8-chloro-10-fluoro-4-((3S,4S)-4-fluoropyrrolidin-3-yl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 672.4 |
| 1086 | 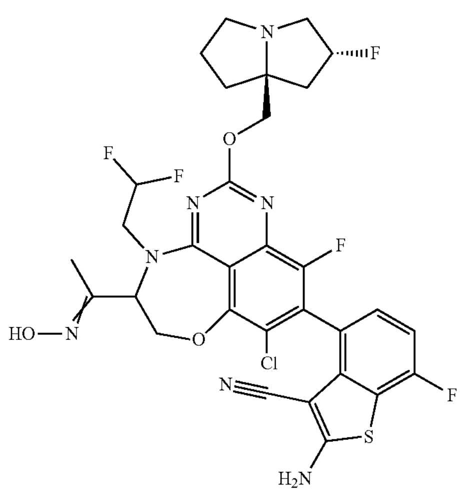 [SMILES: CC(=NO)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-(hydroxyimino)ethyl)-5,6-dihydro-4H-[1,4]oxazepino[5,6,7-de]quinazolin-9-yl)-7-fluorobenzo[b]thiophene-3-carbonitrile | 707.9 |

TABLE 1-continued

| No. | Structure | Chemical Name | [M + H]+ |
|---|---|---|---|
| 1087 | 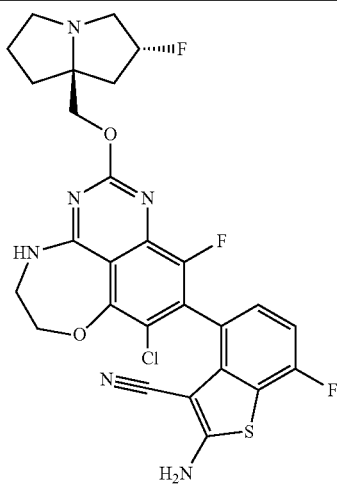 | 2-amino-4-(8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 587.3 |
| 1088 | 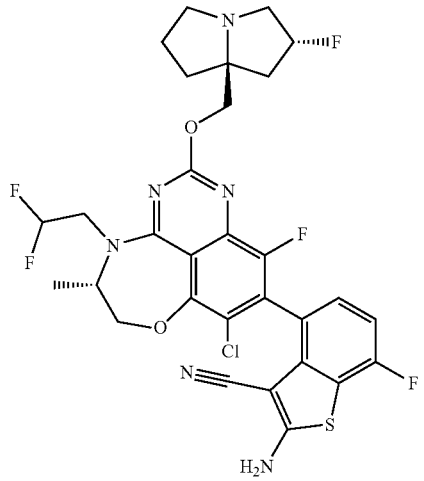 [SMILES: C[C@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile | 665 |
| 1089 | 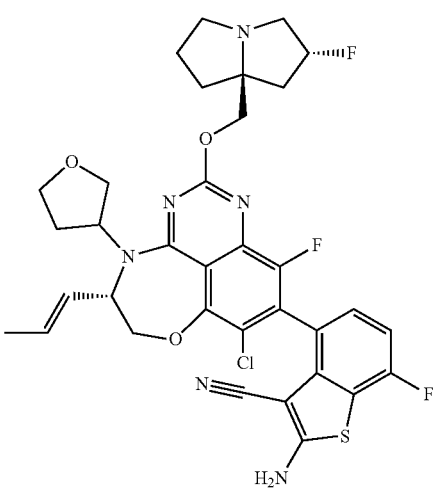 [SMILES: C/C=C/[C@H]1COc2c(Cl)c(-c3ccc(F)c4sc(N)c(C#N)c34)c(F)c3nc(OC[C@@]45CCCN4C[C@H](F)C5)nc(c23)N1C1CCOC1] | 2-amino-4-((5S)-8-chloro-10-fluoro-2-(((2R,7aS)-2-fluorotetrahydro-1H-pyrrolizin-7a(5H)-yl)methoxy)-5-((E)-prop-1-en-1-yl)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 697.3 |

TABLE 1-continued

| No. | Structure | Chemical Name | [M + H]+ |
|---|---|---|---|
| 1090 | 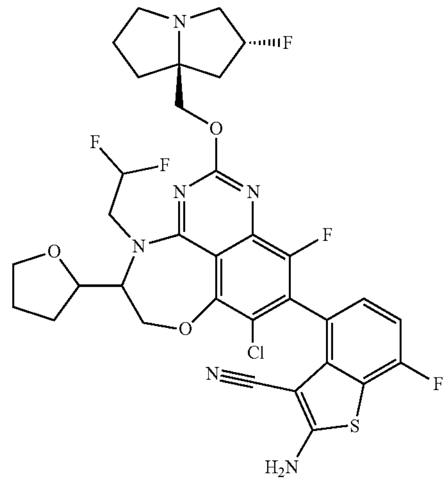 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCO3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(tetrahydrofuran-2-yl)-5,6-dihydro-4H-[1,4]oxazepino[5,6,7-de]quinazolin-9-yl)-7-fluorobenzo[b]thiophene-3-carbonitrile | 720.9 |
| 1091 | 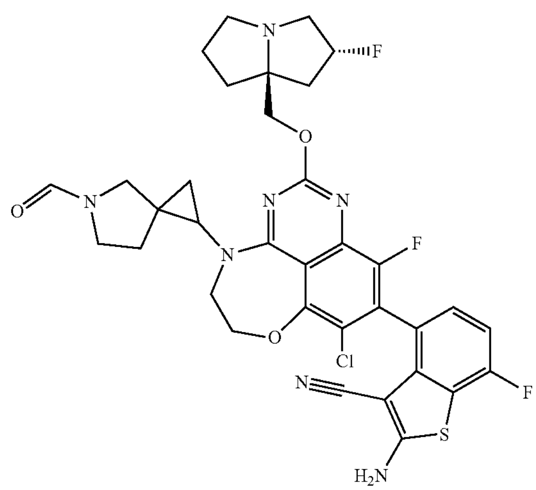 [SMILES: N#Cc1c(N)sc2c(F)ccc(-c3c(Cl)c4c5c(nc(OC[C@@]67CCCN6C[C@H](F)C7)nc5c3F)N(C3CC35CCN(C=O)C5)CCO4)c12] | 2-amino-4-(8-chloro-10-fluoro-2-(((2R,7aS)-2-fluorotetrahydro-1H-pyrrolizin-7a(5H)-yl)methoxy)-4-(5-formyl-5-azaspiro[2.4]heptan-1-yl)-5,6-dihydro-4H-[1,4]oxazepino[5,6,7-de]quinazolin-9-yl)-7-fluorobenzo[b]thiophene-3-carbonitrile | 710.2 |
| 1092 | 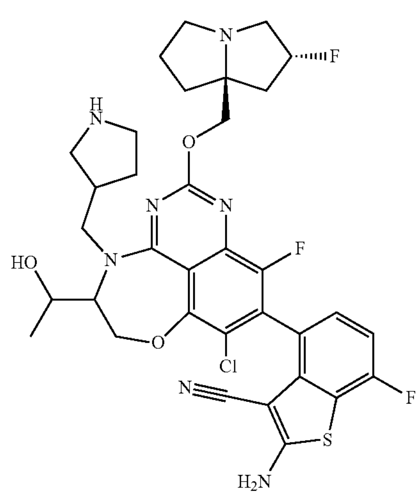 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC1CCNC1] | 2-amino-4-(8-chloro-10-fluoro-2-(((2R,7aS)-2-fluorotetrahydro-1H-pyrrolizin-7a(5H)-yl)methoxy)-5-(1-hydroxyethyl)-4-(pyrrolidin-3-ylmethyl)-5,6-dihydro-4H-[1,4]oxazepino[5,6,7-de]quinazolin-9-yl)-7-fluorobenzo[b]thiophene-3-carbonitrile | 714.3 |

TABLE 1-continued

| No. | Structure | Chemical Name | [M + H]⁺ |
|---|---|---|---|
| 1093 | 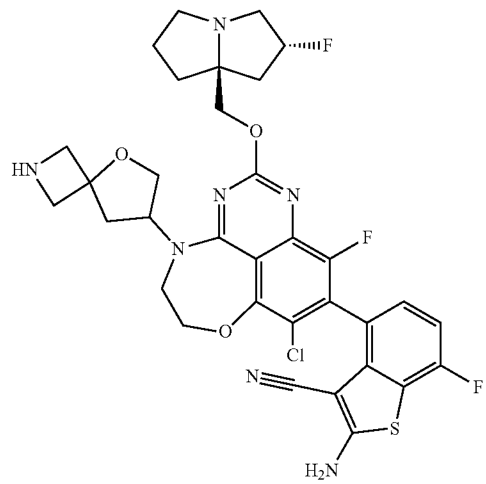 [SMILES: N#Cc1c(N)sc2c(F)ccc(-c3c(Cl)c4c5c(nc(OC[C@@]67CCCN6C[C@H](F)C7)nc5c3F)N(C3COC5(CNC5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(5-oxa-2-azaspiro[3.4]octan-7-yl)-5,6-dihydro-4H-[1,4]oxazepino[5,6,7-de]quinazolin-9-yl)-7-fluorobenzo[b]thiophene-3-carbonitrile | 698.2 |
| 1094 | 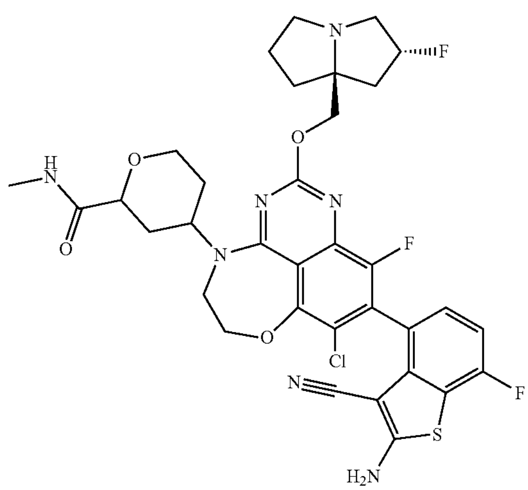 [SMILES: CNC(=O)C1CC(N2CCOc3c(Cl)c(-c4ccc(F)c5sc(N)c(C#N)c45)c(F)c4nc(OC[C@@]56CCCN5C[C@H](F)C6)nc2c34)CCO1] | 4-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N-methyltetrahydro-2H-pyran-2-carboxamide | 752.8 [M + Na]⁺ |
| 1095 | 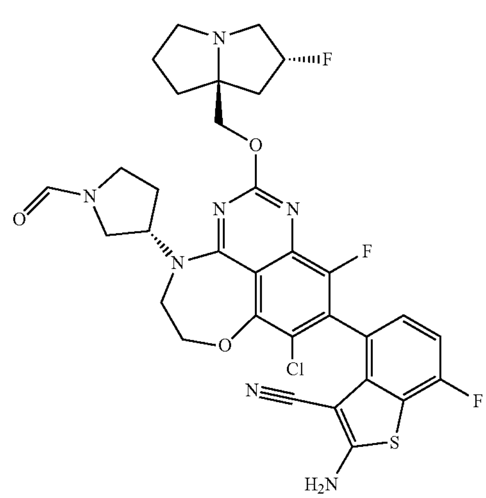 [SMILES: N#Cc1c(N)sc2c(F)ccc(-c3c(Cl)c4c5c(nc(OC[C@@]67CCCN6C[C@H](F)C7)nc5c3F)N([C@H]3CCN(C=O)C3)CCO4)c12] | 2-amino-4-(8-chloro-10-fluoro-2-(((2R,7aS)-2-fluorotetrahydro-1H-pyrrolizin-7a(5H)-yl)methoxy)-4-((S)-1-formylpyrrolidin-3-yl)-5,6-dihydro-4H-[1,4]oxazepino[5,6,7-de]quinazolin-9-yl)-7-fluorobenzo[b]thiophene-3-carbonitrile | 684.4 |

TABLE 1-continued

| No. | Structure | Chemical Name | [M + H]⁺ |
|---|---|---|---|
| 1096 | 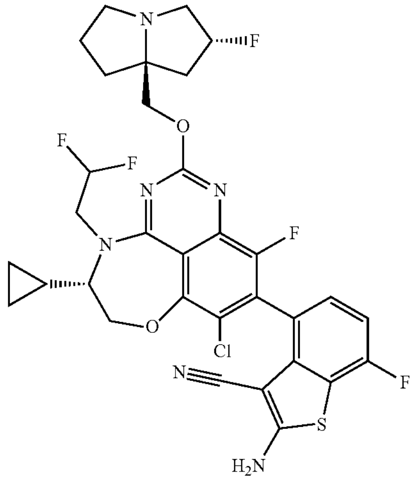 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3)CO4)c12] | 2-amino-4-((S)-8-chloro-5-cyclopropyl-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 691 |
| 1097 | 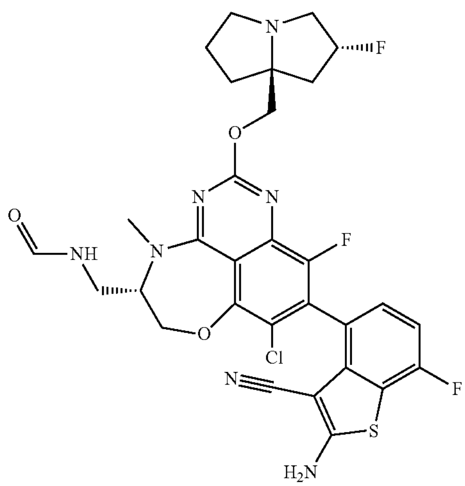 [SMILES: CN1c2nc(OC[C@@]34CCCN3C[C@H](F)C4)nc3c(F)c(-c4ccc(F)c5sc(N)c(C#N)c45)c(Cl)c(c23)OC[C@@H]1CNC=O] | N-(((5S)-9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-4-methyl-5,6-dihydro-4H-[1,4]oxazepino[5,6,7-de]quinazolin-5-yl)methyl)formamide | 658.3 |
| 1098 | 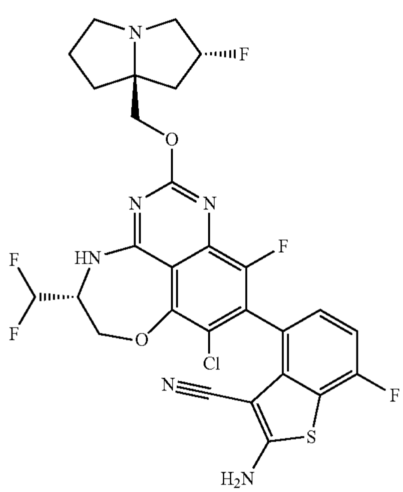 [SMILES: N#Cc1c(N)sc2c(F)ccc(-c3c(Cl)c4c5c(nc(OC[C@@]67CCCN6C[C@H](F)C7)nc5c3F)N[C@@H](C(F)F)CO4)c12] | 2-amino-4-((R)-8-chloro-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 636.9 |

TABLE 1-continued

| No. | Structure | Chemical Name | [M + H]+ |
|---|---|---|---|
| 1099 | 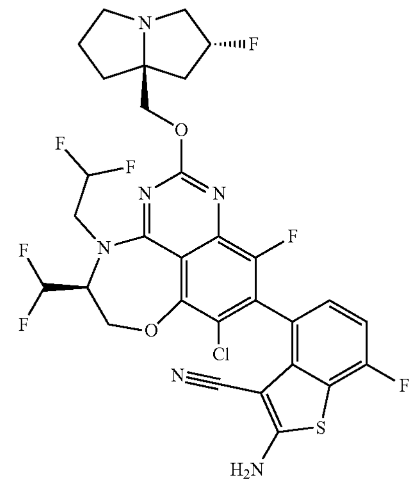 [SMILES: N#Cc1c(N)sc2c(F)ccc(-c3c(Cl)c4c5c(nc(OC[C@@]67CCCN6C[C@H](F)C7)nc5c3F)N(CC(F)F)[C@H](C(F)F)CO4)c12] | 2-amino-4-((S)-8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 701.3 |
| 1100 | 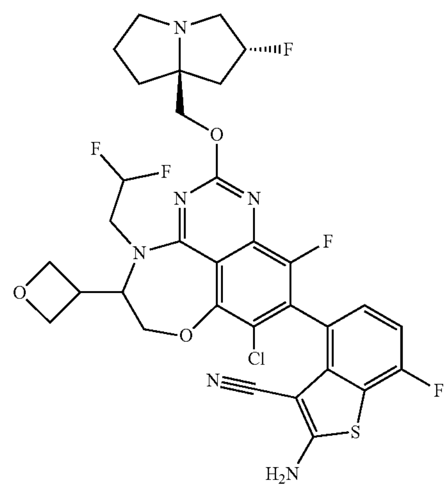 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3COC3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(oxetan-3-yl)-5,6-dihydro-4H-[1,4]oxazepino[5,6,7-de]quinazolin-9-yl)-7-fluorobenzo[b]thiophene-3-carbonitrile | 706.9 |
| 1101 | 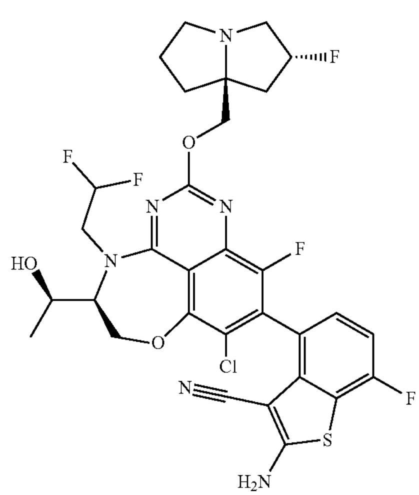 [SMILES: C[C@@H](O)[C@@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile | 694.5 |

TABLE 1-continued

| No. | Structure | Chemical Name | [M + H]⁺ |
|---|---|---|---|
| 1102 | 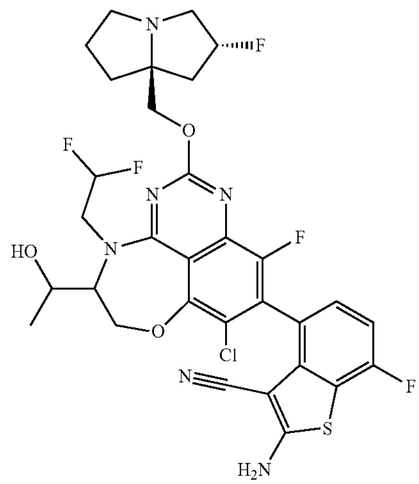 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(1-hydroxyethyl)-5,6-dihydro-4H-[1,4]oxazepino[5,6,7-de]quinazolin-9-yl)-7-fluorobenzo[b]thiophene-3-carbonitrile | 695.2 |
| 1103 | 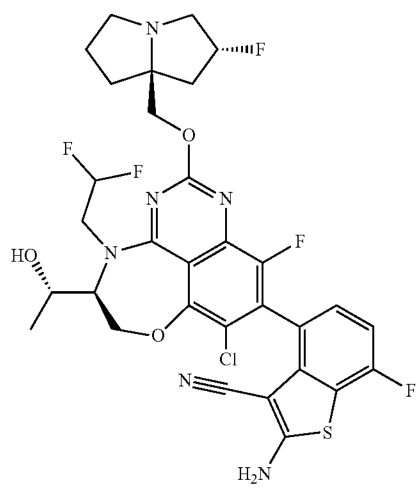 [SMILES: C[C@H](O)[C@@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-5,6-dihydro-4H-[1,4]oxazepino[5,6,7-de]quinazolin-9-yl)-7-fluorobenzo[b]thiophene-3-carbonitrile | 695.3 |
| 1104 | 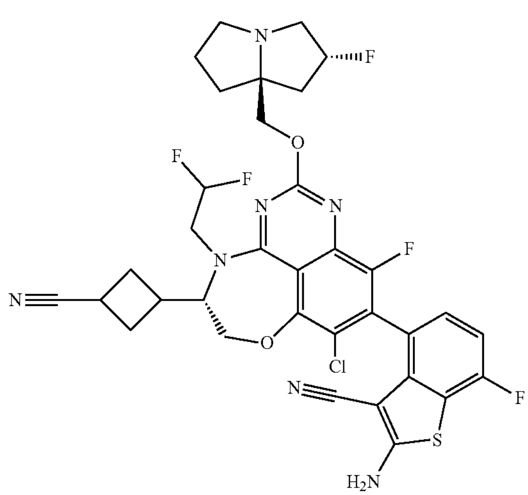 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC(C#N)C3)CO4)c12] | 2-amino-4-((S)-8-chloro-5-(3-cyanocyclobutyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 729.9 |

TABLE 1-continued

| No. | Structure | Chemical Name | [M + H]+ |
|---|---|---|---|
| 1105 | 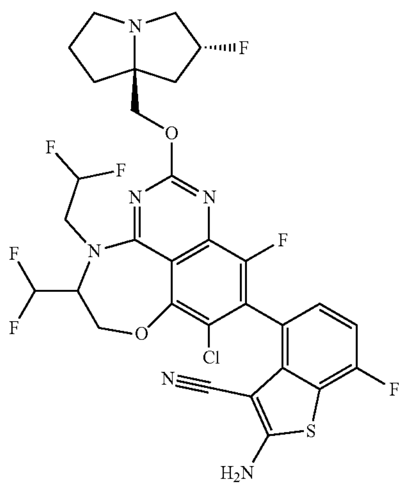 [SMILES: N#Cc1c(N)sc2c(F)ccc(-c3c(Cl)c4c5c(nc(OC[C@@]67CCCN6C[C@H](F)C7)nc5c3F)N(CC(F)F)C(C(F)F)CO4)c12] | 2-amino-4-(8-chloro-4-(2,2-difluoroethyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 700.9 |
| 1106 | 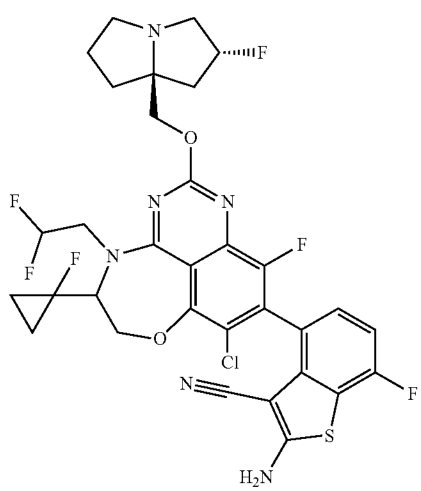 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3(F)CC3)CO4)c12] | 2-amino-4-(8-chloro-4-(2,2-difluoroethyl)-10-fluoro-5-(1-fluorocyclopropyl)-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 708.9 |
| 1107 | 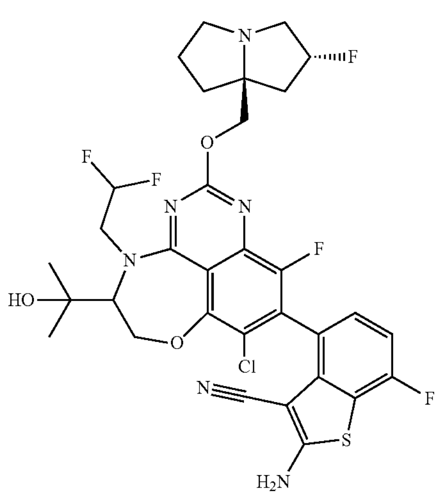 | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(2-hydroxypropan-2-yl)-5,6-dihydro-4H-[1,4]oxazepino[5,6,7-de]quinazolin-9-yl)-7-fluorobenzo[b]thiophene-3-carbonitrile | 709.3 |

TABLE 1-continued

| No. | Structure | Chemical Name | [M + H]+ |
|---|---|---|---|
| 1108 | 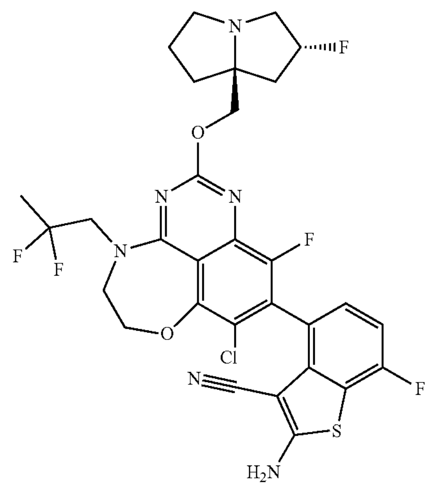 [SMILES: CC(F)(F)CN1CCOc2c(Cl)c(-c3ccc(F)c4sc(N)c(C#N)c34)c(F)c3nc(OC[C@@]45CCCN4C[C@H](F)C5)nc1c23] | 2-amino-4-(8-chloro-4-(2,2-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 665.3 |
| 1109 | 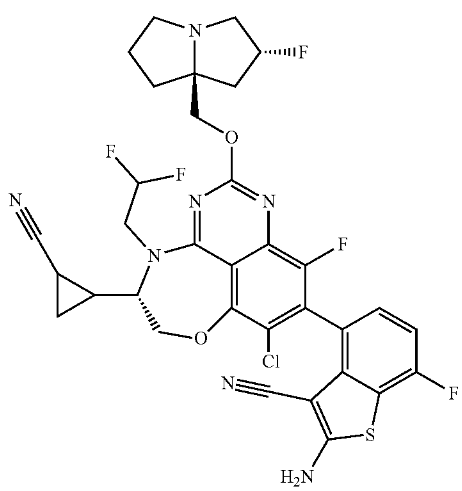 [SMILES: N#Cc1c(N)sc2c(F)ccc(-c3c(Cl)c4c5c(nc(OC[C@@]67CCCN6C[C@H](F)C7)nc5c3F)N(CC(F)F)[C@@H](C3CC3C#N)CO4)c12] | 2-amino-4-((5S)-8-chloro-5-(2-cyanocyclopropyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716.4 |
| 1110 | 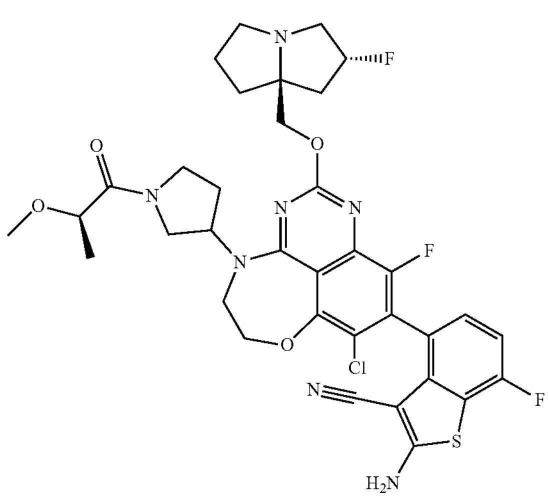 [SMILES: CO[C@H](C)C(=O)N1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(1-((R)-2-methoxypropanoyl)pyrrolidin-3-yl)-5,6-dihydro-4H-[1,4]oxazepino[5,6,7-de]quinazolin-9-yl)-7-fluorobenzo[b]thiophene-3-carbonitrile | 742.3 |

TABLE 1-continued

| No. | Structure | Chemical Name | [M + H]+ |
|---|---|---|---|
| 1111 | 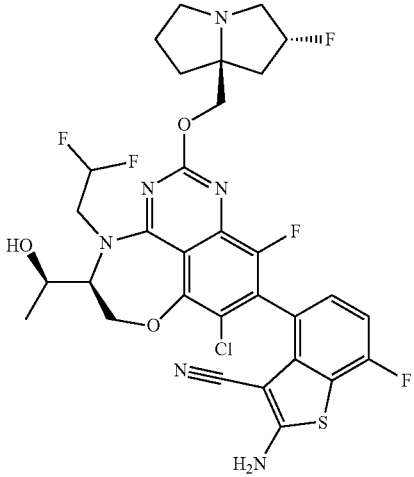 [SMILES: C[C@@H](O)[C@@H]1COc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S)-8-chloro-4-(2,2-difluoroethyl)-10-fluoro-2-(((2R,7aS)-2-fluorotetrahydro-1H-pyrrolizin-7a(5H)-yl)methoxy)-5-((R)-1-hydroxyethyl)-5,6-dihydro-4H-[1,4]oxazepino[5,6,7-de]quinazolin-9-yl)-7-fluorobenzo[b]thiophene-3-carbonitrile | 695.1 |
| 1112 | 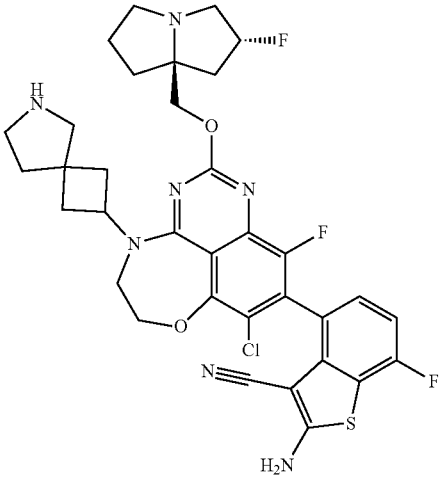 [SMILES: N#Cc1c(N)sc2c(F)ccc(-c3c(Cl)c4c5c(nc(OC[C@@]67CCCN6C[C@H](F)C7)nc5c3F)N(C3CC5(CCNC5)C3)CCO4)c12] | 2-amino-4-(8-chloro-10-fluoro-2-(((2R,7aS)-2-fluorotetrahydro-1H-pyrrolizin-7a(5H)-yl)methoxy)-4-(6-azaspiro[3.4]octan-2-yl)-5,6-dihydro-4H-[1,4]oxazepino[5,6,7-de]quinazolin-9-yl)-7-fluorobenzo[b]thiophene-3-carbonitrile | 696.2 |
| 1113 | 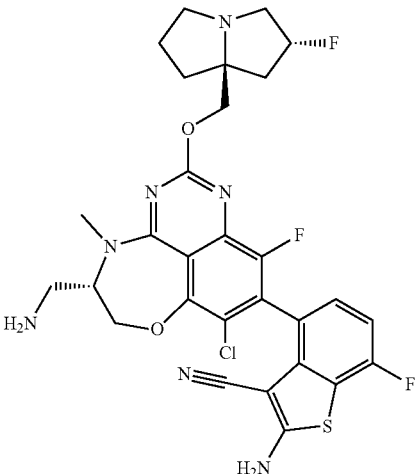 | 2-amino-4-((5S)-5-(aminomethyl)-8-chloro-10-fluoro-2-(((2R,7aS)-2-fluorotetrahydro-1H-pyrrolizin-7a(5H)-yl)methoxy)-4-methyl-5,6-dihydro-4H-[1,4]oxazepino[5,6,7-de]quinazolin-9-yl)-7-fluorobenzo[b]thiophene-3-carbonitrile | 630.3 |

TABLE 1-continued

| No. | Structure | Chemical Name | [M + H]+ |
|---|---|---|---|
| 1114 | 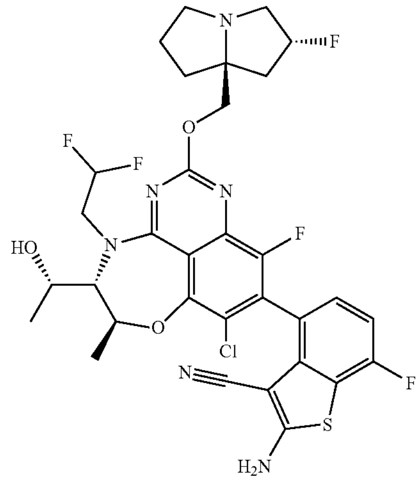 [SMILES: C[C@H](O)[C@H]1[C@H](C)Oc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5S,6S)-8-chloro-4-(2,2-difluoroethyl)-10-fluoro-2-(((2R,7aS)-2-fluorotetrahydro-1H-pyrrolizin-7a(5H)-yl)methoxy)-5-((S)-1-hydroxyethyl)-6-methyl-5,6-dihydro-4H-[1,4]oxazepino[5,6,7-de]quinazolin-9-yl)-7-fluorobenzo[b]thiophene-3-carbonitrile | 709.4 |
| 1115 | 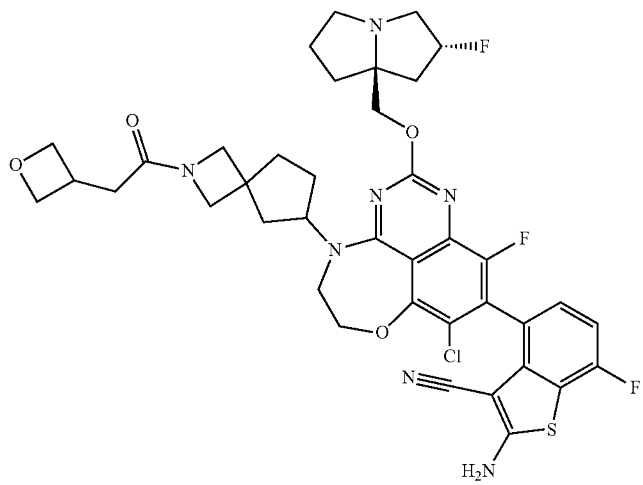 [SMILES: N#Cc1c(N)sc2c(F)ccc(-c3c(Cl)c4c5c(nc(OC[C@@]67CCCN6C[C@H](F)C7)nc5c3F)N(C3CCC5(C3)CN(C(=O)CC3COC3)C5)CCO4)c12] | 2-amino-4-(8-chloro-10-fluoro-2-(((2R,7aS)-2-fluorotetrahydro-1H-pyrrolizin-7a(5H)-yl)methoxy)-4-(2-(2-(oxetan-3-yl)acetyl)-2-azaspiro[3.4]octan-6-yl)-5,6-dihydro-4H-[1,4]oxazepino[5,6,7-de]quinazolin-9-yl)-7-fluorobenzo[b]thiophene-3-carbonitrile | 794 |
| 1116 | 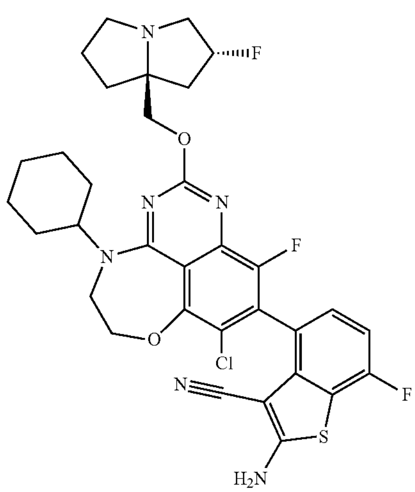 [SMILES: N#Cc1c(N)sc2c(F)ccc(-c3c(Cl)c4c5c(nc(OC[C@@]67CCCN6C[C@H](F)C7)nc5c3F)N(C3CCCCC3)CCO4)c12] | 2-amino-4-(8-chloro-4-cyclohexyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 669.3 |

TABLE 1-continued

| No. | Structure | Chemical Name | [M + H]+ |
|---|---|---|---|
| 1117 | 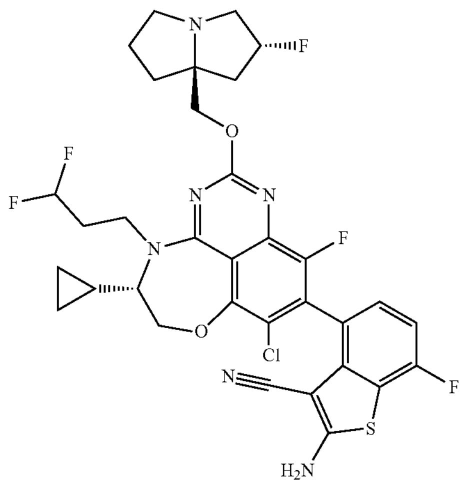 [SMILES: N#Cc1c(N)sc2c(F)ccc(-c3c(Cl)c4c5c(nc(OC[C@@]67CCCN6C[C@H](F)C7)nc5c3F)N(CCC(F)F)[C@@H](C3CC3)CO4)c12] | 2-amino-4-((S)-8-chloro-5-cyclopropyl-4-(3,3-difluoropropyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 705 |
| 1118 | 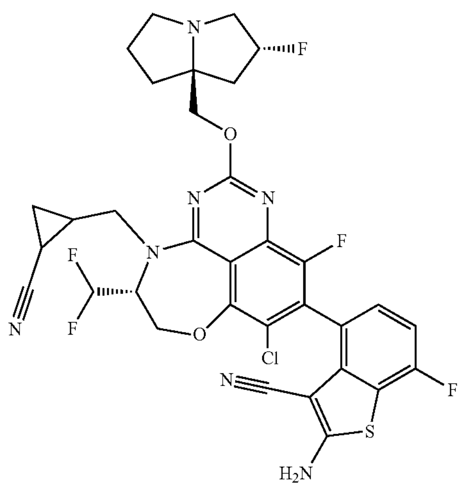 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C(F)F)CO4)c12] | 2-amino-4-((5R)-8-chloro-4-((2-cyanocyclopropyl)methyl)-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 716.4 |
| 1119 | 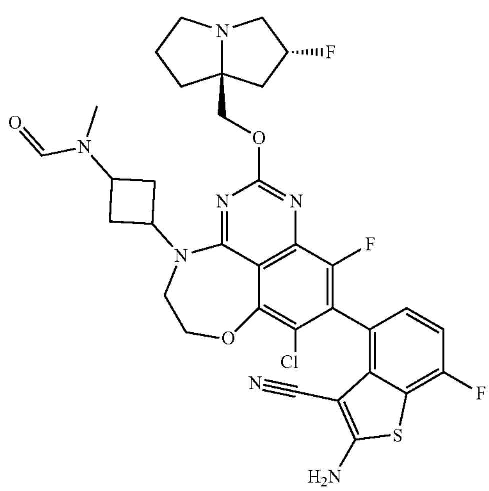 [SMILES: CN(C=O)C1CC(N2CCOc3c(Cl)c(-c4ccc(F)c5sc(N)c(C#N)c45)c(F)c4nc(OC[C@@]56CCCN5C[C@H](F)C6)nc2c34)C1] | N-(3-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)cyclobutyl)-N-methylformamide | 698.4 |

TABLE 1-continued

| No. | Structure | Chemical Name | [M + H]+ |
|---|---|---|---|
| 1120 | 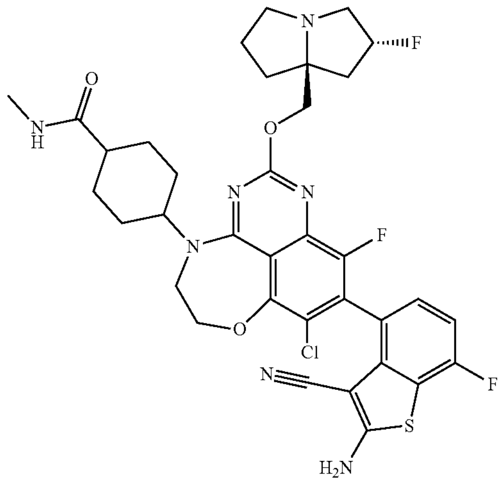 [SMILES: CNC(=O)C1CCC(N2CCOc3c(Cl)c(-c4ccc(F)c5sc(N)c(C#N)c45)c(F)c4nc(OC[C@@]56CCCN5C[C@H](F)C6)nc2c34)CC1] | 4-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)-N-methylcyclohexane-1-carboxamide | 726.3 |
| 1121 | 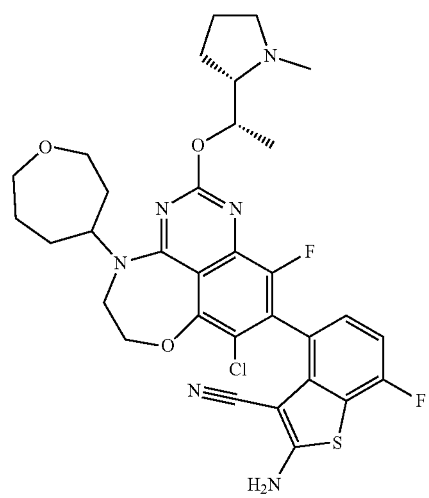 [SMILES: C[C@H](Oc1nc2c3c(c(Cl)c(-c4ccc(F)c5sc(N)c(C#N)c45)c(F)c3n1)OCCN2C1CCCOCC1)[C@@H]1CCCN1C] | 2-amino-4-(8-chloro-10-fluoro-2-((S)-1-((S)-1-methylpyrrolidin-2-yl)ethoxy)-4-(oxepan-4-yl)-5,6-dihydro-4H-[1,4]oxazepino[5,6,7-de]quinazolin-9-yl)-7-fluorobenzo[b]thiophene-3-carbonitrile | 656.4 |
| 1122 | 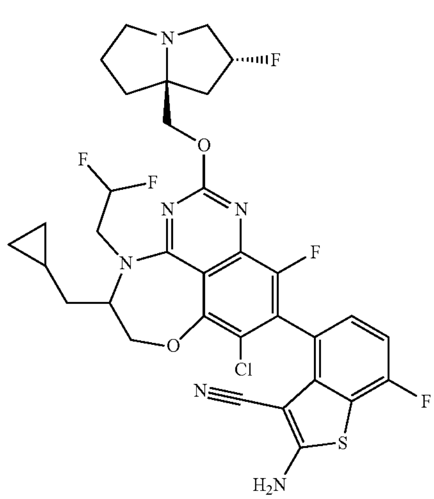 [SMILES: N#Cc1c(N)sc2c(F)ccc(-c3c(Cl)c4c5c(nc(OC[C@@]67CCCN6C[C@H](F)C7)nc5c3F)N(CC(F)F)C(CC3CC3)CO4)c12] | 2-amino-4-(8-chloro-5-(cyclopropylmethyl)-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 705 |

TABLE 1-continued

| No. | Structure | Chemical Name | [M + H]+ |
|---|---|---|---|
| 1123 | 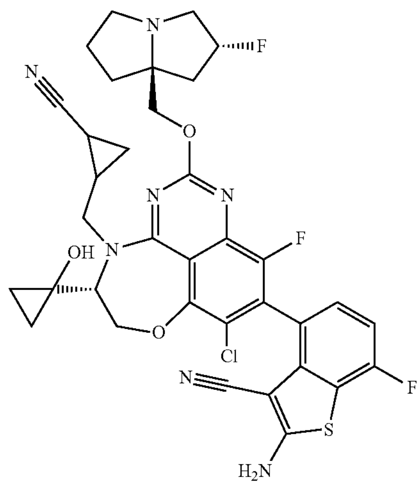 [SMILES: N#Cc1c(N)sc2c(F)ccc(-c3c(Cl)c4c5c(nc(OC[C@@]67CCCN6C[C@H](F)C7)nc5c3F)N(CC3CC3C#N)[C@@H](C3(O)CC3)CO4)c12] | 2-amino-4-((5R)-8-chloro-4-((2-cyanocyclopropyl)methyl)-10-fluoro-2-(((2R,7aS)-2-fluorotetrahydro-1H-pyrrolizin-7a(5H)-yl)methoxy)-5-(1-hydroxycyclopropyl)-5,6-dihydro-4H-[1,4]oxazepino[5,6,7-de]quinazolin-9-yl)-7-fluorobenzo[b]thiophene-3-carbonitrile | 722.4 |
| 1124 | 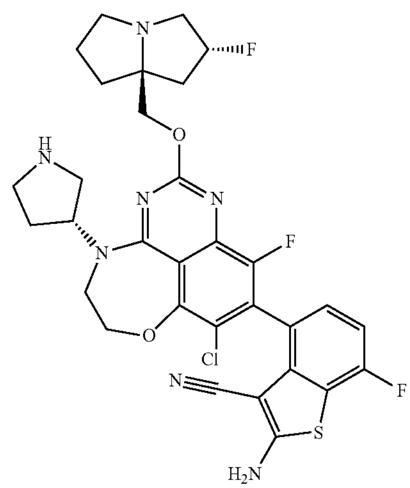 [SMILES: N#Cc1c(N)sc2c(F)ccc(-c3c(Cl)c4c5c(nc(OC[C@@]67CCCN6C[C@H](F)C7)nc5c3F)N([C@@H]3CCNC3)CCO4)c12] | 2-amino-4-(8-chloro-10-fluoro-2-(((2R,7aS)-2-fluorotetrahydro-1H-pyrrolizin-7a(5H)-yl)methoxy)-4-((R)-pyrrolidin-3-yl)-5,6-dihydro-4H-[1,4]oxazepino[5,6,7-de]quinazolin-9-yl)-7-fluorobenzo[b]thiophene-3-carbonitrile | 656.4 |
| 1125 | 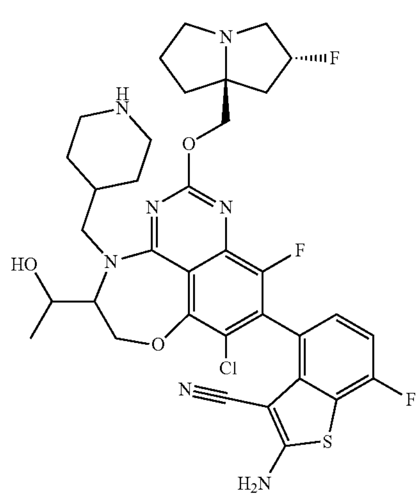 [SMILES: CC(O)C1COc2c(Cl)c(-c3ccc(F)c4sc(N)c(C#N)c34)c(F)c3nc(OC[C@@]45CCCN4C[C@H](F)C5)nc(c23)N1CC1CCNCC1] | 2-amino-4-(8-chloro-10-fluoro-2-(((2R,7aS)-2-fluorotetrahydro-1H-pyrrolizin-7a(5H)-yl)methoxy)-5-(1-hydroxyethyl)-4-(piperidin-4-ylmethyl)-5,6-dihydro-4H-[1,4]oxazepino[5,6,7-de]quinazolin-9-yl)-7-fluorobenzo[b]thiophene-3-carbonitrile | 728.3 |

TABLE 1-continued

| No. | Structure | Chemical Name | [M + H]+ |
|---|---|---|---|
| 1126 | 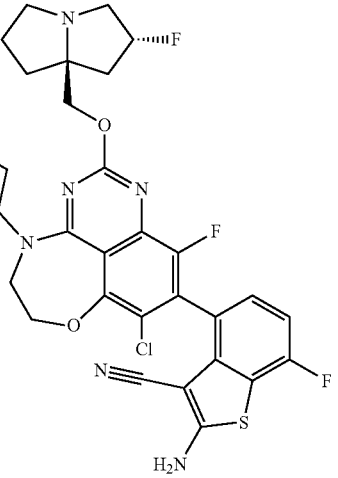 | 2-amino-4-(8-chloro-10-fluoro-2-(((2R,7aS)-2-fluorotetrahydro-1H-pyrrolizin-7a(5H)-yl)methoxy)-4-(1-(2-(oxetan-3-yl)acetyl)pyrrolidin-3-yl)-5,6-dihydro-4H-[1,4]oxazepino[5,6,7-de]quinazolin-9-yl)-7-fluorobenzo[b]thiophene-3-carbonitrile | 754.3 |
| 1127 | 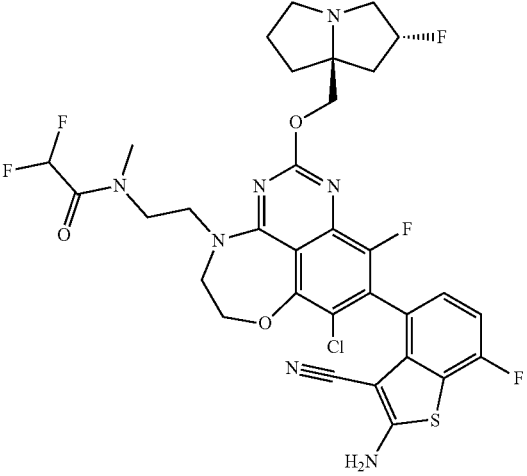 [SMILES: CN(CCN1CCOc2c(Cl)c(-c3ccc(F)c4sc(N)c(C#N)c34)c(F)c3nc(OC[C@@]45CCCN4C[C@H](F)C5)nc1c23)C(=O)C(F)F] | N-(2-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)-2,2-difluoro-N-methylacetamide | 722.3 |
| 1128 | 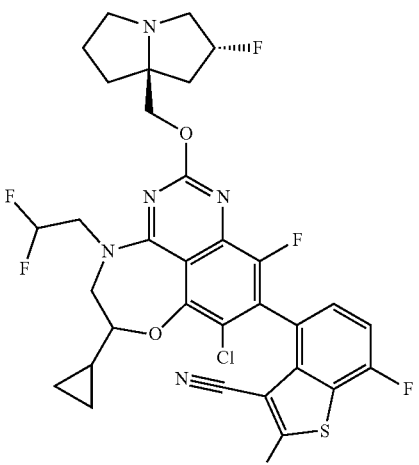 | 2-amino-4-(8-chloro-6-cyclopropyl-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 690.7 |

TABLE 1-continued

| No. | Structure | Chemical Name | [M + H]+ |
|---|---|---|---|
| 1129 | 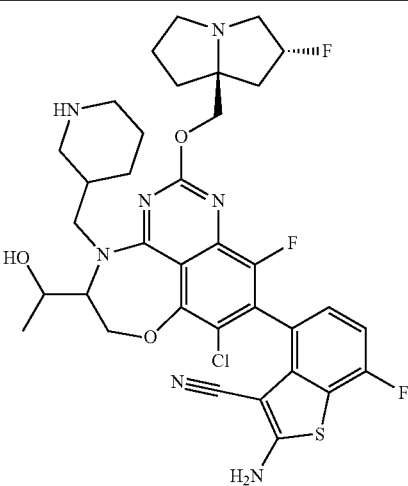 | 2-amino-4-(8-chloro-10-fluoro-2-(((2R,7aS)-2-fluorotetrahydro-1H-pyrrolizin-7a(5H)-yl)methoxy)-5-(1-hydroxyethyl)-4-(piperidin-3-ylmethyl)-5,6-dihydro-4H-[1,4]oxazepino[5,6,7-de]quinazolin-9-yl)-7-fluorobenzo[b]thiophene-3-carbonitrile | 728.2 |
| 1130 | 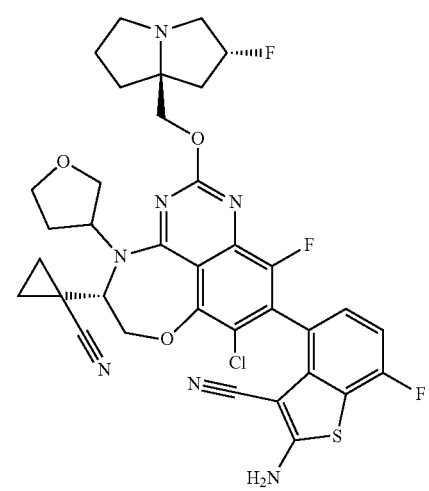 [SMILES: N#Cc1c(N)sc2c(F)ccc(-c3c(Cl)c4c5c(nc(OC[C@@]67CCCN6C[C@H](F)C7)nc5c3F)N(C3CCOC3)[C@@H](C3(C#N)CC3)CO4)c12] | 2-amino-4-((5S)-8-chloro-5-(1-cyanocyclopropyl)-10-fluoro-2-(((2R,7aS)-2-fluorotetrahydro-1H-pyrrolizin-7a(5H)-yl)methoxy)-4-(tetrahydrofuran-3-yl)-5,6-dihydro-4H-[1,4]oxazepino[5,6,7-de]quinazolin-9-yl)-7-fluorobenzo[b]thiophene-3-carbonitrile | 721.9 |
| 1131 | 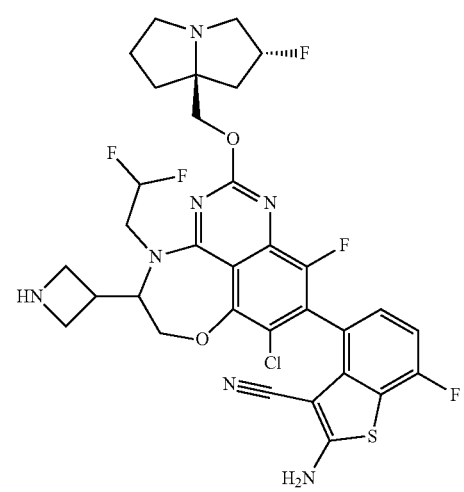 | 2-amino-4-(5-(azetidin-3-yl)-8-chloro-4-(2,2-difluoroethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile | 706.2 |

TABLE 1-continued

| No. | Structure | Chemical Name | [M + H]+ |
|---|---|---|---|
| 1132 | 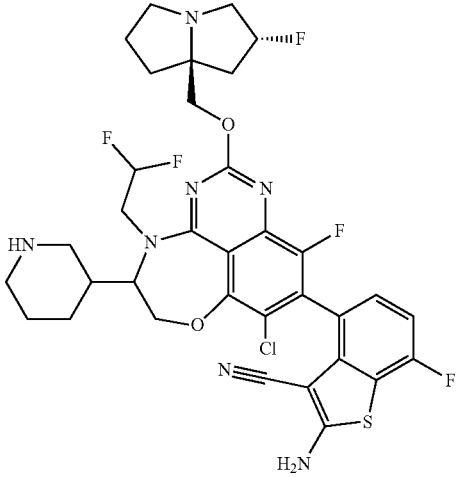 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCCNC3)CO4)c12] | 2-amino-4-(8-chloro-4-(2,2-difluoroethyl)-10-fluoro-2-(((2R,7aS)-2-fluorotetrahydro-1H-pyrrolizin-7a(5H)-yl)methoxy)-5-(piperidin-3-yl)-5,6-dihydro-4H-[1,4]oxazepino[5,6,7-de]quinazolin-9-yl)-7-fluorobenzo[b]thiophene-3-carbonitrile | 734.2 |
| 1133 | 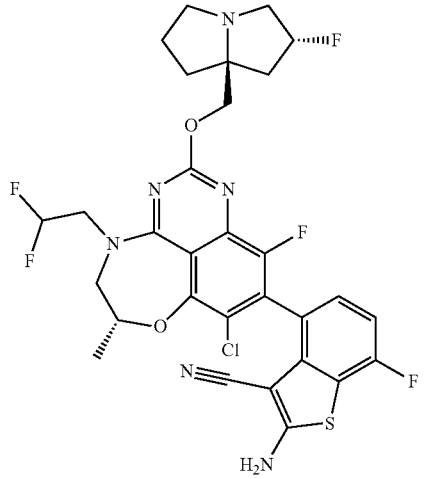 | 2-amino-4-((6R)-8-chloro-4-(2,2-difluoroethyl)-10-fluoro-2-(((2R,7aS)-2-fluorotetrahydro-1H-pyrrolizin-7a(5H)-yl)methoxy)-6-methyl-5,6-dihydro-4H-[1,4]oxazepino[5,6,7-de]quinazolin-9-yl)-7-fluorobenzo[b]thiophene-3-carbonitrile | 664.9 |
| 1134 | 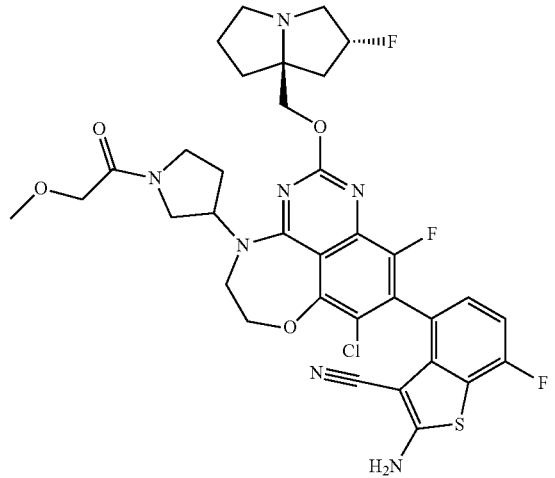 [SMILES: COCC(=O)N1CCC(N2CCOc3c(Cl)c(-c4ccc(F)c5sc(N)c(C#N)c45)c(F)c4nc(OC[C@@]56CCCN5C[C@H](F)C6)nc2c34)C1] | 2-amino-4-(8-chloro-10-fluoro-2-(((2R,7aS)-2-fluorotetrahydro-1H-pyrrolizin-7a(5H)-yl)methoxy)-4-(1-(2-methoxyacetyl)pyrrolidin-3-yl)-5,6-dihydro-4H-[1,4]oxazepino[5,6,7-de]quinazolin-9-yl)-7-fluorobenzo[b]thiophene-3-carbonitrile | 728.3 |

TABLE 1-continued

| No. | Structure | Chemical Name | [M + H]+ |
| --- | --- | --- | --- |
| 1201 | 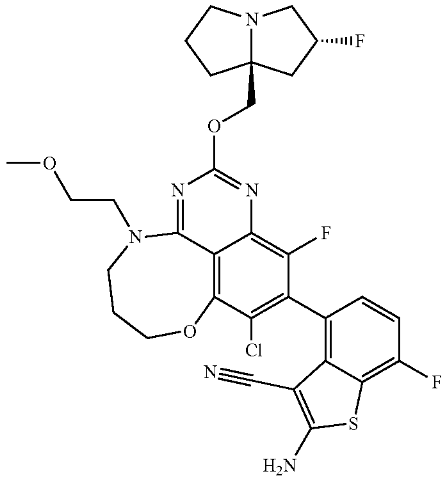 [SMILES: COCCN1CCCOc2c(Cl)c(-c3ccc(F)c4sc(N)c(C#N)c34)c(F)c3nc(OC[C@@]45CCCN4C[C@H](F)C5)nc1c23] | 2-amino-4-(9-chloro-11-fluoro-2-(((2R,7aS)-2-fluorotetrahydro-1H-pyrrolizin-7a(5H)-yl)methoxy)-4-(2-methoxyethyl)-4,5,6,7-tetrahydro-[1,5]oxazocino[4,3,2-de]quinazolin-10-yl)-7-fluorobenzo[b]thiophene-3-carbonitrile | 658.9 |
| 1202 | 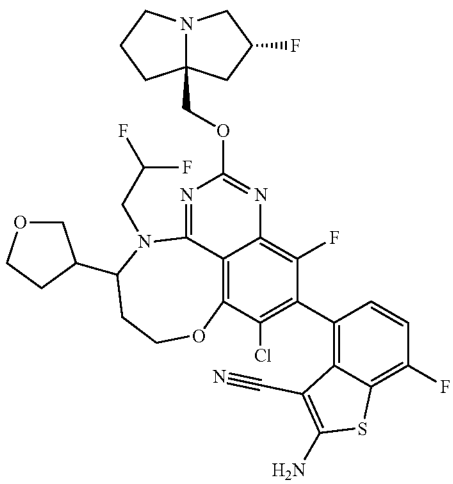 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCOC3)CCO4)c12] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-5-(tetrahydrofuran-3-yl)-4,5,6,7-tetrahydro-[1,5]oxazocino[4,3,2-de]quinazolin-10-yl)-7-fluorobenzo[b]thiophene-3-carbonitrile | 734.8 |
| 1203 | 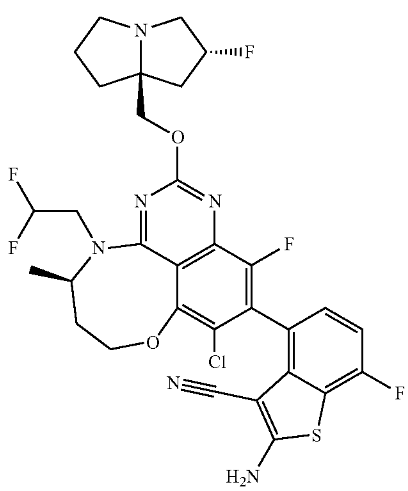 [SMILES: C[C@@H]1CCOc2c(Cl)c(-c3ccc(F)c4sc(N)c(C#N)c34)c(F)c3nc(OC[C@@]45CCCN4C[C@H](F)C5)nc(c23)N1CC(F)F] | 2-amino-4-((5R)-9-chloro-4-(2,2-difluoroethyl)-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-7-fluorobenzo[b]thiophene-3-carbonitrile | 679.1 |

TABLE 1-continued

| No. | Structure | Chemical Name | [M + H]+ |
|---|---|---|---|
| 1204 | 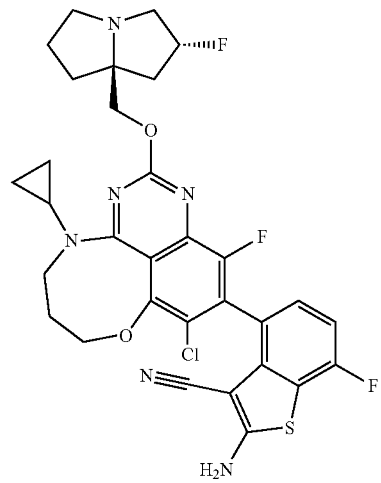 [SMILES: N#Cc1c(N)sc2c(F)ccc(-c3c(Cl)c4c5c(nc(OC[C@@]67CCCN6C[C@H](F)C7)nc5c3F)N(C3CC3)CCCO4)c12] | 2-amino-4-(9-chloro-4-cyclopropyl-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-7-fluorobenzo[b]thiophene-3-carbonitrile | 640.9 |
| 1205 | 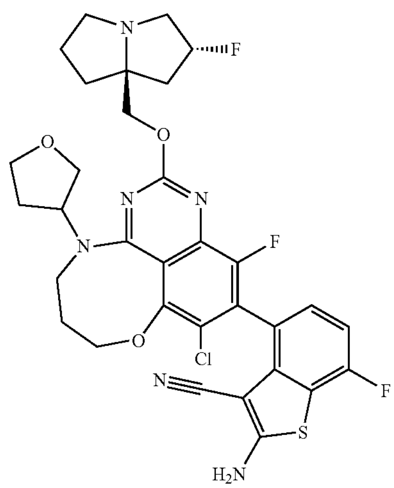 [SMILES: N#Cc1c(N)sc2c(F)ccc(-c3c(Cl)c4c5c(nc(OC[C@@]67CCCN6C[C@H](F)C7)nc5c3F)N(C3CCOC3)CCCO4)c12] | 2-amino-4-(9-chloro-11-fluoro-2-(((2R,7aS)-2-fluorotetrahydro-1H-pyrrolizin-7a(5H)-yl)methoxy)-4-(tetrahydrofuran-3-yl)-4,5,6,7-tetrahydro-[1,5]oxazocino[4,3,2-de]quinazolin-10-yl)-7-fluorobenzo[b]thiophene-3-carbonitrile | 671.3 |
| 1206 | 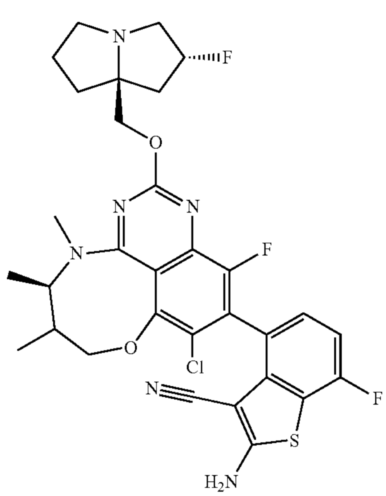 [SMILES: CC1COc2c(Cl)c(-c3ccc(F)c4sc(N)c(C#N)c34)c(F)c3nc(OC[C@@]45CCCN4C[C@H](F)C5)nc(c23)N(C)[C@@H]1C] | 2-amino-4-((5R)-9-chloro-11-fluoro-2-(((2R,7aS)-2-fluorotetrahydro-1H-pyrrolizin-7a(5H)-yl)methoxy)-4,5,6-trimethyl-4,5,6,7-tetrahydro-[1,5]oxazocino[4,3,2-de]quinazolin-10-yl)-7-fluorobenzo[b]thiophene-3-carbonitrile | 643.5 |

TABLE 1-continued

| No. | Structure | Chemical Name | [M + H]+ |
|---|---|---|---|
| 1207 | 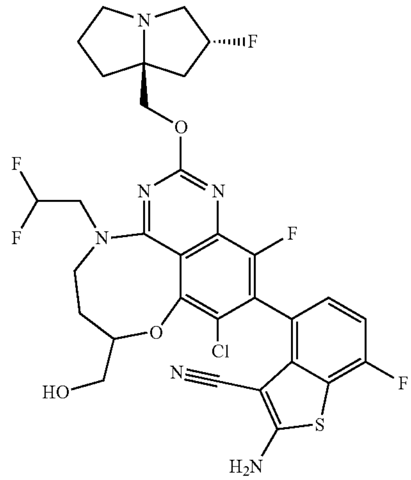 [SMILES: N#Cc1c(N)sc2c(F)ccc(-c3c(Cl)c4c5c(nc(OC[C@@]67CCCN6C[C@H](F)C7)nc5c3F)N(CC(F)F)CCC(CO)O4)c12] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-7-(hydroxymethyl)-4,5,6,7-tetrahydro-[1,5]oxazocino[4,3,2-de]quinazolin-10-yl)-7-fluorobenzo[b]thiophene-3-carbonitrile | 694.8 |
| 1208 | 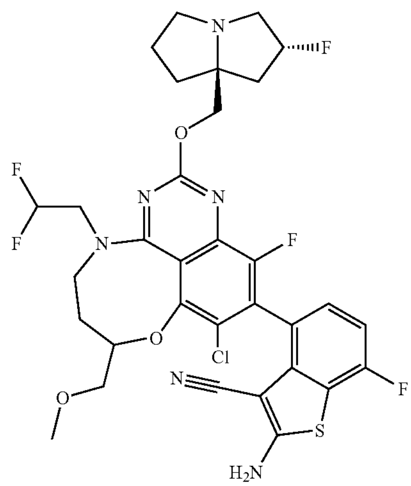 [SMILES: COCC1CCN(CC(F)F)c2nc(OC[C@@]34CCCN3C[C@H](F)C4)nc3c(F)c(-c4ccc(F)c5sc(N)c(C#N)c45)c(Cl)c(c23)O1] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-7-(methoxymethyl)-4,5,6,7-tetrahydro-[1,5]oxazocino[4,3,2-de]quinazolin-10-yl)-7-fluorobenzo[b]thiophene-3-carbonitrile | 708.8 |
| 1209 | 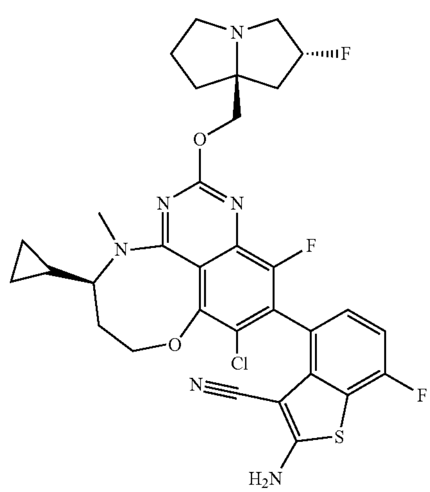 [SMILES: CN1c2nc(OC[C@@]34CCCN3C[C@H](F)C4)nc3c(F)c(-c4ccc(F)c5sc(N)c(C#N)c45)c(Cl)c(c23)OCC[C@H]1C1CC1] | 2-amino-4-((5S)-9-chloro-5-cyclopropyl-11-fluoro-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazolin-10-yl)-7-fluorobenzo[b]thiophene-3-carbonitrile | 654.9 |

TABLE 1-continued

| No. | Structure | Chemical Name | [M + H]+ |
|---|---|---|---|
| 1210 | 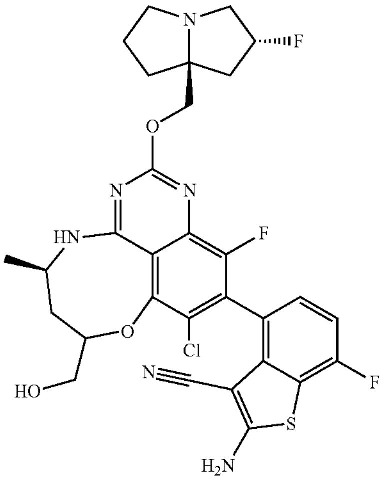 [SMILES: C[C@@H]1CC(CO)Oc2c(Cl)c(-c3ccc(F)c4sc(N)c(C#N)c34)c(F)c3nc(OC[C@@]45CCCN4C[C@H](F)C5)nc(c23)N1] | 2-amino-4-((5R)-9-chloro-11-fluoro-2-(((2R,7aS)-2-fluorotetrahydro-1H-pyrrolizin-7a(5H)-yl)methoxy)-7-(hydroxymethyl)-5-methyl-4,5,6,7-tetrahydro-[1,5]oxazocino[4,3,2-de]quinazolin-10-yl)-7-fluorobenzo[b]thiophene-3-carbonitrile | 645.1 |
| 1211 | 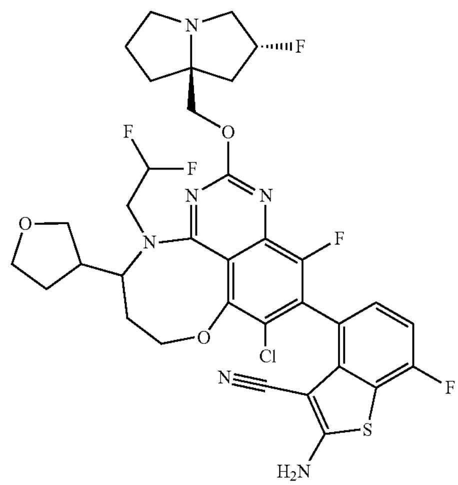 [SMILES: N#Cc1c(N)sc2c(F)ccc(-c3c(Cl)c4c5c(nc(OC[C@@]67CCCN6C[C@H](F)C7)nc5c3F)N(CC(F)F)C(C3CCOC3)CCO4)c12] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-5-(tetrahydrofuran-3-yl)-4,5,6,7-tetrahydro-[1,5]oxazocino[4,3,2-de]quinazolin-10-yl)-7-fluorobenzo[b]thiophene-3-carbonitrile | 734.8 |
| 1212 | 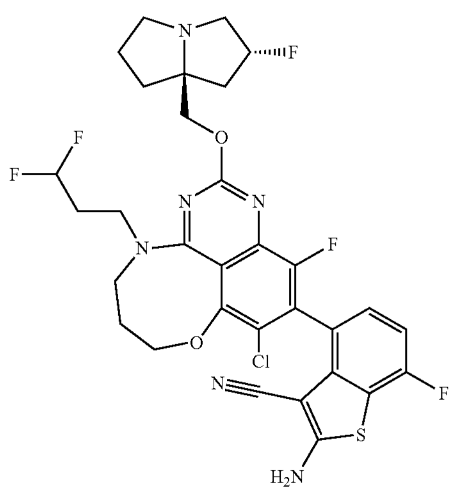 [SMILES: N#Cc1c(N)sc2c(F)ccc(-c3c(Cl)c4c5c(nc(OC[C@@]67CCCN6C[C@H](F)C7)nc5c3F)N(CCC(F)F)CCCO4)c12] | 2-amino-4-(9-chloro-4-(3,3-difluoropropyl)-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-7-fluorobenzo[b]thiophene-3-carbonitrile | 679.3 |

TABLE 1-continued

| No. | Structure | Chemical Name | [M + H]+ |
|---|---|---|---|
| 1213 | 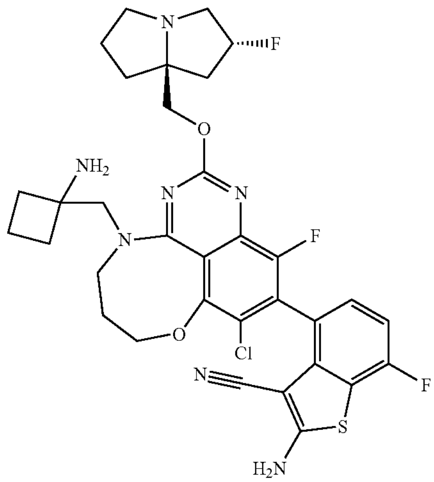 [SMILES: N#Cc1c(N)sc2c(F)ccc(-c3c(Cl)c4c5c(nc(OC[C@@]67CCCN6C[C@H](F)C7)nc5c3F)N(CC3(N)CCC3)CCCO4)c12] | 2-amino-4-(4-((1-aminocyclobutyl)methyl)-9-chloro-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-7-fluorobenzo[b]thiophene-3-carbonitrile | 684.2 |
| 1214 | 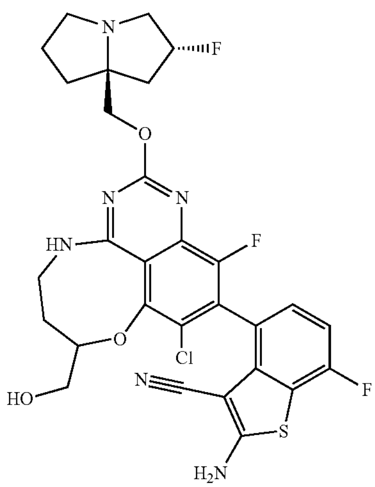 [SMILES: N#Cc1c(N)sc2c(F)ccc(-c3c(Cl)c4c5c(nc(OC[C@@]67CCCN6C[C@H](F)C7)nc5c3F)NCCC(CO)O4)c12] | 2-amino-4-(9-chloro-11-fluoro-2-(((2R,7aS)-2-fluorotetrahydro-1H-pyrrolizin-7a(5H)-yl)methoxy)-7-(hydroxymethyl)-4,5,6,7-tetrahydro-[1,5]oxazocino[4,3,2-de]quinazolin-10-yl)-7-fluorobenzo[b]thiophene-3-carbonitrile | 632.3 |
| 1215 | 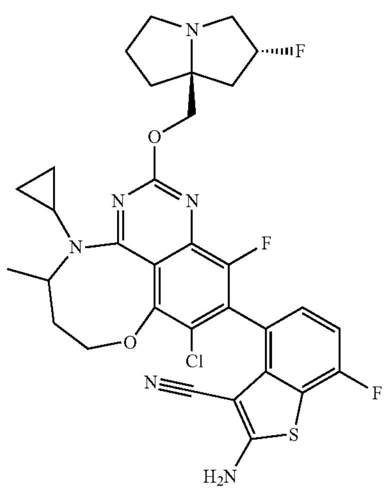 [SMILES: CC1CCOc2c(Cl)c(-c3ccc(F)c4sc(N)c(C#N)c34)c(F)c3nc(OC[C@@]45CCCN4C[C@H](F)C5)nc(c23)N1C1CC1] | 2-amino-4-(9-chloro-4-cyclopropyl-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-7-fluorobenzo[b]thiophene-3-carbonitrile | 655.2 |

TABLE 1-continued

| No. | Structure | Chemical Name | [M + H]+ |
|---|---|---|---|
| 1216 | 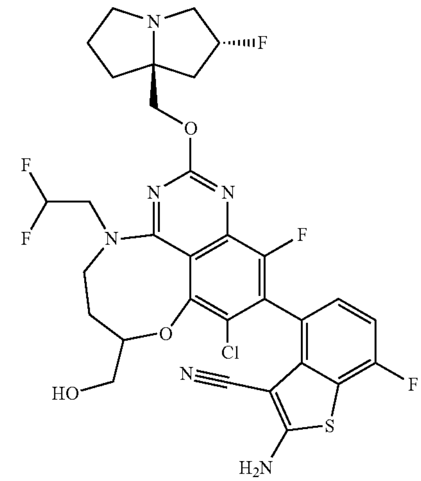 [SMILES: N#Cc1c(N)sc2c(F)ccc(-c3c(Cl)c4c5c(nc(OC[C@@]67CCCN6C[C@H](F)C7)nc5c3F)N(CC(F)F)CCC(CO)O4)c12] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-7-(hydroxymethyl)-4,5,6,7-tetrahydro-[1,5]oxazocino[4,3,2-de]quinazolin-10-yl)-7-fluorobenzo[b]thiophene-3-carbonitrile | 694.8 |
| 1217 | 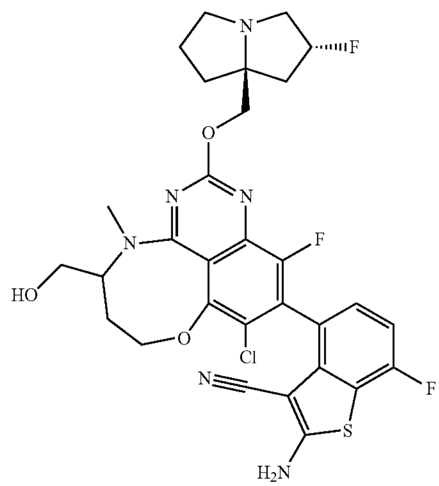 [SMILES: CN1c2nc(OC[C@@]34CCCN3C[C@H](F)C4)nc3c(F)c(-c4ccc(F)c5sc(N)c(C#N)c45)c(Cl)c(c23)OCCC1CO] | 2-amino-4-(9-chloro-11-fluoro-2-(((2R,7aS)-2-fluorotetrahydro-1H-pyrrolizin-7a(5H)-yl)methoxy)-5-(hydroxymethyl)-4-methyl-4,5,6,7-tetrahydro-[1,5]oxazocino[4,3,2-de]quinazolin-10-yl)-7-fluorobenzo[b]thiophene-3-carbonitrile | 645.3 |
| 1218 | 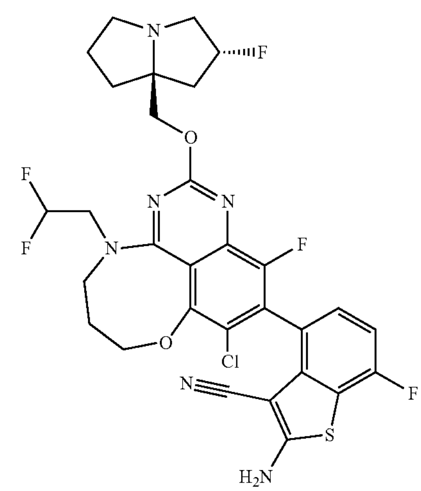 [SMILES: N#Cc1c(N)sc2c(F)ccc(-c3c(Cl)c4c5c(nc(OC[C@@]67CCCN6C[C@H](F)C7)nc5c3F)N(CC(F)F)CCCO4)c12] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-4,5,6,7-tetrahydro-[1,5]oxazocino[4,3,2-de]quinazolin-10-yl)-7-fluorobenzo[b]thiophene-3-carbonitrile | 666.4 |

TABLE 1-continued

| No. | Structure | Chemical Name | [M + H]+ |
|---|---|---|---|
| 1219 | 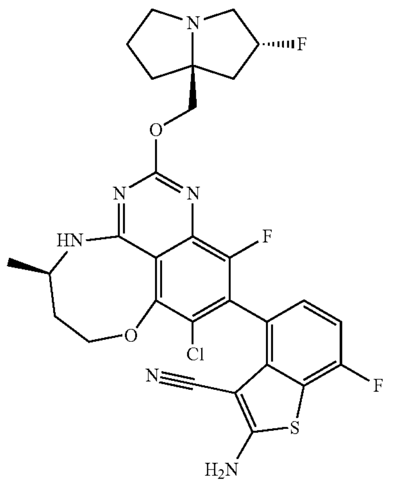 [SMILES: C[C@@H]1CCOc2c(Cl)c(-c3ccc(F)c4sc(N)c(C#N)c34)c(F)c3nc(OC[C@@]45CCCN4C[C@H](F)C5)nc(c23)N1] | 2-amino-4-((5R)-9-chloro-11-fluoro-2-(((2R,7aS)-2-fluorotetrahydro-1H-pyrrolizin-7a(5H)-yl)methoxy)-5-methyl-4,5,6,7-tetrahydro-[1,5]oxazocino[4,3,2-de]quinazolin-10-yl)-7-fluorobenzo[b]thiophene-3-carbonitrile | 614.9 |
| 1220 | 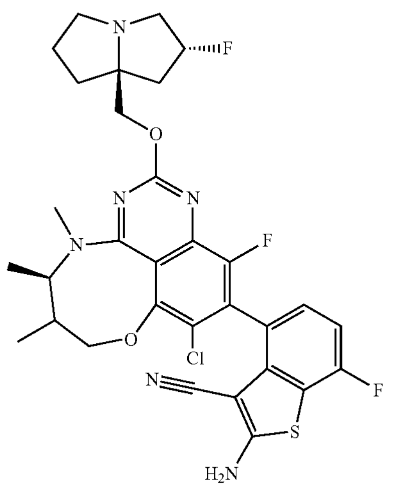 [SMILES: CC1COc2c(Cl)c(-c3ccc(F)c4sc(N)c(C#N)c34)c(F)c3nc(OC[C@@]45CCCN4C[C@H](F)C5)nc(c23)N(C)[C@@H]1C] | 2-amino-4-((5R)-9-chloro-11-fluoro-2-(((2R,7aS)-2-fluorotetrahydro-1H-pyrrolizin-7a(5H)-yl)methoxy)-4,5,6-trimethyl-4,5,6,7-tetrahydro-[1,5]oxazocino[4,3,2-de]quinazolin-10-yl)-7-fluorobenzo[b]thiophene-3-carbonitrile | 643.5 |
| 1221 | 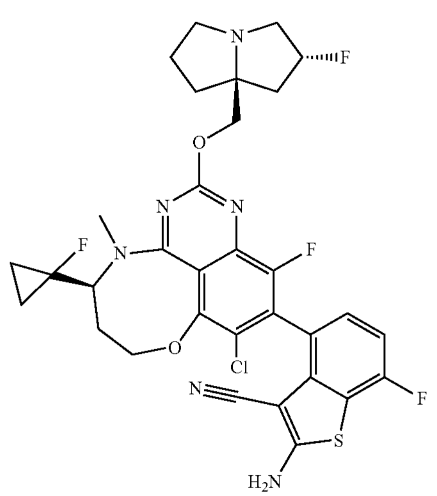 | 2-amino-4-((5S)-9-chloro-11-fluoro-5-(1-fluorocyclopropyl)-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazolin-10-yl)-7-fluorobenzo[b]thiophene-3-carbonitrile | 673 |

TABLE 1-continued

| No. | Structure | Chemical Name | [M + H]+ |
|---|---|---|---|
| 1222 | 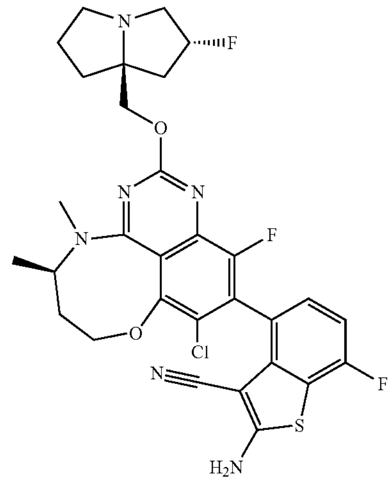 [SMILES: C[C@@H]1CCOc2c(Cl)c(-c3ccc(F)c4sc(N)c(C#N)c34)c(F)c3nc(OC[C@@]45CCCN4C[C@H](F)C5)nc(c23)N1C] | 2-amino-4-((5R)-9-chloro-11-fluoro-2-(((2R,7aS)-2-fluorotetrahydro-1H-pyrrolizin-7a(5H)-yl)methoxy)-4,5-dimethyl-4,5,6,7-tetrahydro-[1,5]oxazocino[4,3,2-de]quinazolin-10-yl)-7-fluorobenzo[b]thiophene-3-carbonitrile | 628.9 |
| 1223 | 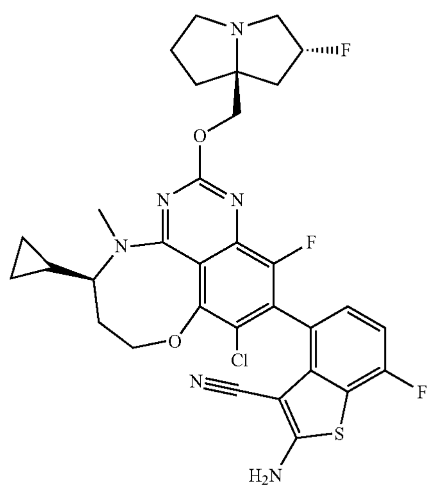 [SMILES: CN1c2nc(OC[C@@]34CCCN3C[C@H](F)C4)nc3c(F)c(-c4ccc(F)c5sc(N)c(C#N)c45)c(Cl)c(c23)OCC[C@H]1C1CC1] | 2-amino-4-((5S)-9-chloro-5-cyclopropyl-11-fluoro-2-(((2R,7aS)-2-fluorotetrahydro-1H-pyrrolizin-7a(5H)-yl)methoxy)-4-methyl-4,5,6,7-tetrahydro-[1,5]oxazocino[4,3,2-de]quinazolin-10-yl)-7-fluorobenzo[b]thiophene-3-carbonitrile | 654.9 |
| 1224 | 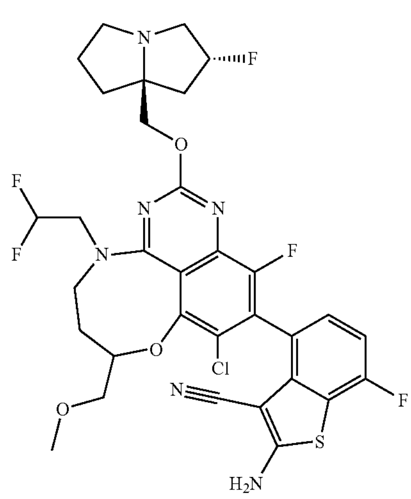 [SMILES: COCC1CCN(CC(F)F)c2nc(OC[C@@]34CCCN3C[C@H](F)C4)nc3c(F)c(-c4ccc(F)c5sc(N)c(C#N)c45)c(Cl)c(c23)O1] | 2-amino-4-(9-chloro-4-(2,2-difluoroethyl)-11-fluoro-2-(((2R,7aS)-2-fluorotetrahydro-1H-pyrrolizin-7a(5H)-yl)methoxy)-7-(methoxymethyl)-4,5,6,7-tetrahydro-[1,5]oxazocino[4,3,2-de]quinazolin-10-yl)-7-fluorobenzo[b]thiophene-3-carbonitrile | 708.8 |

TABLE 1-continued

| No. | Structure | Chemical Name | [M + H]⁺ |
|---|---|---|---|
| 1225 | 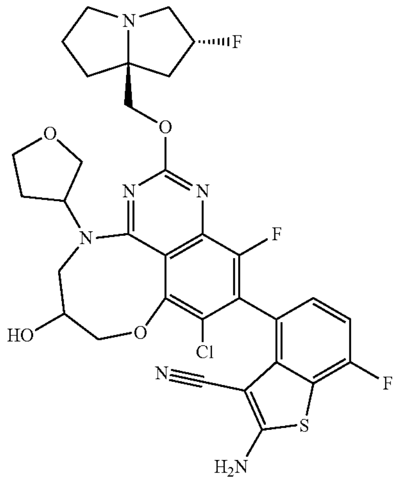 [SMILES: N#Cc1c(N)sc2c(F)ccc(-c3c(Cl)c4c5c(nc(OC[C@@]67CCCN6C[C@H](F)C7)nc5c3F)N(C3CCOC3)CC(O)CO4)c12] | 2-amino-4-(9-chloro-11-fluoro-2-(((2R,7aS)-2-fluorotetrahydro-1H-pyrrolizin-7a(5H)-yl)methoxy)-6-hydroxy-4-(tetrahydrofuran-3-yl)-4,5,6,7-tetrahydro-[1,5]oxazocino[4,3,2-de]quinazolin-10-yl)-7-fluorobenzo[b]thiophene-3-carbonitrile | 686.8 |

Compounds of Table 1 are depicted with flat, wedged, and/or hashed wedged bonds. It is understood that compounds depicted in Table 1 may encompass all possible stereoisomers, including atropisomers, of the compounds of Table 1. In some instances, the relative stereochemistry at one or more stereocenters of a compound has been determined; in some instances, the absolute stereochemistry has been determined. In some instances, a single compound number represents a mixture of stereoisomers, including atropisomers. In some instances, a single compound number represents a single stereoisomer, such as a single atropisomer. As such, it is understood that if two or more compound numbers in Table 1 are provided with the same depicted structure, then different stereoisomers or mixtures of stereoisomers of the depicted structure are represented by each compound number.

Example 2: Ras Sequences

```
    Human K-Ras Wildtype sequence
                                        (SEQ ID NO. 1)
  1 MTEYKLVVVG AGGVGKSALT IQLIQNHFVD EYDPTIEDSY RKQVVIDGET

51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12D
                                        (SEQ ID NO. 2)
  1 MTEYKLVVVG ADGVGKSALT IQLIQNHFVD EYDPTIEDSY RKQVVIDGET

51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12V
                                        (SEQ ID NO. 3)
  1 MTEYKLVVVG AVGVGKSALT IQLIQNHFVD EYDPTIEDSY RKQVVIDGET

51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12S:
                                        (SEQ ID NO. 4)
  1 MTEYKLVVVG ASGVGKSALT IQLIQNHFVD EYDPTIEDSY RKQVVIDGET

51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM
```

```
Human N-Ras wildtype
                                                      (SEQ ID NO. 5)
  1 MTEYKLVVVG AGGVGKSALT IQLIQNHFVD EYDPTIEDSY RKQVVIDGET

51 CLLDILDTAG QEEYSAMRDQ YMRTGEGFLC VFAINNSKSF ADINLYREQI

101 KRVKDSDDVP MVLVGNKCDL PTRTVDTKQA HELAKSYGIP FIETSAKTRQ

151 GVEDAFYTLV REIRQYRMKK LNSSDDGTQG CMGLPCVVM

H-Ras G12D
                                                      (SEQ ID NO. 6)
  1 MTEYKLVVVG ADGVGKSALT IQLIQNHFVD EYDPTIEDSY RKQVVIDGET

51 CLLDILDTAG QEEYSAMRDQ YMRTGEGFLC VFAINNTKSF EDIHQYREQI

101 KRVKDSDDVP MVLVGNKCDL AARTVESRQA QDLARSYGIP YIETSAKTRQ

151 GVEDAFYTLV REIRQHKLRK LNPPDESGPG CMSCKCVLS

H-Ras wildtype
                                                      (SEQ ID NO. 7)
  1 MTEYKLVVVG AGGVGKSALT IQLIQNHFVD EYDPTIEDSY RKQVVIDGET

51 CLLDILDTAG QEEYSAMRDQ YMRTGEGFLC VFAINNTKSF EDIHQYREQI

101 KRVKDSDDVP MVLVGNKCDL AARTVESRQA QDLARSYGIP YIETSAKTRQ

151 GVEDAFYTLV REIRQHKLRK LNPPDESGPG CMSCKCVLS

Human N-Ras G12D
                                                      (SEQ ID NO. 8)
  1 MTEYKLVVVG ADGVGKSALT IQLIQNHFVD EYDPTIEDSY RKQVVIDGET

51 CLLDILDTAG QEEYSAMRDQ YMRTGEGFLC VFAINNSKSF ADINLYREQI

101 KRVKDSDDVP MVLVGNKCDL PTRTVDTKQA HELAKSYGIP FIETSAKTRQ

151 GVEDAFYTLV REIRQYRMKK LNSSDDGTQG CMGLPCVVM
```

Example 3: Protein expression

DNA expression constructs encoding one or more protein sequences of interest (e.g., Kras fragments thereof, mutant variants thereof, etc.) and its corresponding DNA sequences are optimized for expression in *E. coli* and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides a N-terminal fusion of a HIS-tag to the integrated gene. To generate the final expression vectors, the expression construct of the protein of interest is cloned into any of the applied destination vectors. The expression vectors are transformed into *E. coli* strain, e.g., BL21 (DE3). Cultivation of the transformed strains for expression is performed in 10 L and 1 L fermenter. The cultures are grown, for example, in Terrific Broth media (MP Biomedicals, Kat. #1 13045032) with 200 µg/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed *E. coli* cells are harvested by centrifugation and the resulting pellet is suspended in a lysis buffer, as provided below, and lysed by passing three-times through a high pressure device. The lysate is centrifuged (49000g, 45 min, 4° C.) and the supernatant is used for further purification.

Example 4: Ras Protein Purification

A Ras (e.g., K-Ras wildtype or a mutant such as K-Ras G12S, K-Ras G12D, K-Ras G12V or K-RasG12C) construct or a variant thereof is tagged with GST. *E. coli* culture from a 10L fermenter is lysed in lysis buffer (50 mM Tris HCl 7.5, 500 mM NaCl, 1 mM DTT, 0.5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 100). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM Glutathione). The main fractions of the elution peak (monitored by OD280) are pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

Example 5: HTRF (homogenous time-resolved fluorescence) resonance energy transfer assay The ability of a compound of the present disclosure to reduce a Ras signaling output can be demonstrated by an HTRF assay. This assay can be also used to assess a selective inhibition or reduction of signaling output of a mutant Ras protein relative to a wildtype, or relative to a different mutant Ras protein. For example, the equilibrium interaction of wildtype Kras or K-Ras mutant (e.g., wildtype or a mutant thereof) with SOS1 (e.g., hSOS1) can be assessed as a proxy or an indication for a subject compound's ability to bind and inhibit Ras protein. HTRF assay detects from (i) a fluorescence resonance energy transfer (FRET) donor (e.g., anti-GST-Europium) that is bound to GST-tagged K-Ras mutant to (ii) a FRET acceptor (e.g., anti-6His-XL665) bound to a His-tagged hSOS1.

The assay buffer can contain~5 mM HEPES pH 7.4, ~150 mM NaCl, ~ 1 mM DTT, 0.05% BSA and 0.0025%(v/v) Igepal. A Ras working solution is prepared in an assay buffer containing typically a suitable amount of the protein construct (e.g., GST-tagged K-Ras mutant) and the FRET donor (e.g., antiGST-Eu(K) from Cisbio, France). A SOS1 working solution is prepared in an assay buffer containing suitable amount of the protein construct (e.g., His-hSOS1) and the FRET acceptor (e.g., anti-6His-XL665 from Cisbio, France). A suitable amount of the protein construct will depend on the range of activity or range of IC50 values being detected or under investigation. For detecting IC50 within a range of 500 nM, the protein constructs of the same range of molarity can be utilized. An inhibitor control solution is prepared in an assay buffer containing comparable amount of the FRET acceptor without the SOS1 protein.

A fixed volume of DMSO with or without test compound is transferred into a 384-well plate. Ras working solution is added to all wells of the test plate. SOS1 working solution is added to all wells except for those that are subsequently filled the inhibitor control solution. Upon incubation for about 10 minutes or longer, the fluorescence is measured with a M1000Pro plate reader (Tecan) using HTRF detection (excitation 337 nm, emission 1: 620 nm, emission 2: 665 nm). Compounds are tested in duplicates at different concentrations (for example, 10 µM, 2.5 µM, 0.63 µM, 0.16 µM, 0.04 µM, 0.01 µM test compound). The ratiometric data (i.e., emission 2 divided by emission 1) is used to calculate IC50 values against Ras using GraphPad Prism (GraphPad software). Following this general procedure, samples were tested with or without a subject compound disclosed herein including compounds exemplified in Table 1 to assess their abilities to inhibit a K-Ras mutant relative to another mutant or WT. Signaling output measured in terms of IC50 values can be obtained, a ratio of IC50 against one mutant relative to another mutant can be calculated. For instance, a selective reduction of K-Ras G12D signaling output can be evidenced by a ratio greater than one. In particular, a selective reduction of K-Ras G12D signaling relative to K-Ras WT signaling is evidenced as the ratio of IC50 (against K-Ras WT) to IC50 (against K-Ras G12D) is greater than 1. In embodiments, subject compounds exhibit an IC50 against K-Ras mutants (e.g., G12C, G12D, G12S, G1V, G13C, or G13D) less than 5 µM, such as less than 500 nM, less than 100 nM, 50 nM, 10 nM or even less. In embodiments, subject compounds exhibit an IC50 against wildtype K-Ras less than 5 µM, such as less than 500 nM, less than 100 nM, 50 nM, 10 nM or even less.

When assayed by the procedures described in Example 5, exemplary compounds of the present disclosure exhibited an IC50 against one or more K-Ras mutants (such as K-Ras G12V, K-Ras G12D, or K-Ras G12S) less than 200 nM, 150 nM, 100 nM, 10 nM, 5 nM or even less. In particular, exemplary compounds disclosed herein exhibited an IC50 against K-Ras G12D of less than about 100 nM, including without limitation compounds 601, 602, 603, 606, 607, 608, 611, 612, 613, 614, 615, 616, 617, 618, 619, 620, 621, 622, 623, 624, 625, 626, 628, 629, 630, 631, 632, 633, 636, 637, 638, 639, 640, 641, 643, 646, 647, 648, 649, 650, 652, 654, 655, 656, 657, 658, 659, 660, 661, 662, 663, 664, 665, 667, 668, 670, 672, 673, 674, 675, 676, 677, 681, 682, 684, 686, 687, 688, 689, 692, 693, 697, 698, 699, 700, 701, 702, 703, 704, 705, 706, 707, 708, 709, 713, 714, 716, 717, 718, 720, 721, 722, 723, 724, 725, 726, 727, 730, 731, 733, 734, 735, 736, 737, 738, 740, 741, 742, 745, 746, 748, 750, 751, 753, 754, 755, 757, 760, 763, 764, 765, 770, 771, 772, 773, 775, 777, 778, 781, 783, 784, 785, 787, 788, 793, 795, 796, 797, 798, 803, 807, 808, 810, 811, 812, 813, 815, 816, 817, 818, 819, 820, 821, 822, 825, 827, 828, 829, 830, 834, 835, 836, 837, 838, 839, 840, 841, 843, 844, 848, 850, 853, 854, 855, 856, 858, 859, 862, 863, 864, 867, 868, 869, 871, 874, 876, 877, 879, 880, 881, 884, 885, 887, 888, 890, 891, 892, 893, 895, 896, 897, 898, 899, 900, 901, 902, 906, 907, 908, 909, 910, 911, 913, 914, 915, 916, 917, 918, 919, 920, 921, 922, 923, 924, 928, 929, 930, 932, 934, 935, 936, 937, 938, 939, 940, 942, 943, 944, 946, 948, 949, 950, 951, 953, 954, 956, 957, 958, 960, 961, 962, 963, 966, 968, 969, 970, 971, 972, 973, 974, 977, 978, 979, 980, 981, 983, 984, 986, 987, 988, 990, 991, 992, 994, 995, 998, 999, 1000, 1002, 1008, 1010, 1011, 1012, 1013, 1014, 1015, 1016, 1017, 1018, 1019, 1020, 1021, 1022, 1023, 1024, 1025, 1028, 1029, 1030, 1031, 1032, 1034, 1035, 1037, 1038, 1041, 1042, 1043, 1044, 1048, 1049, 1050, 1051, 1052, 1053, 1054, 1055, 1057, 1058, 1059, 1060, 1061, 1062, 1064, 1066, 1067, 1068, 1069, 1070, 1071, 1073, 1074, 1075, 1076, 1077, 1078, 1080, 1082, 1084, 1085, 1087, 1088, 1091, 1092, 1093, 1094, 1095, 1097, 1105, 1108, 1109, 1110, 1112, 1113, 1115, 1116, 1119, 1120, 1123, 1124, 1125, 1126, 1127, 1128, 1129, 1131, 1133, 1134, 1201, 1203, 1205, 1206, 1207, 1209, 1212, 1213, 1214, 1215, 1216, 1217, 1218, 1219, 1220, 1222, and 1225. Further, exemplary compounds disclosed herein exhibited an IC50 against K-Ras G12S of less than about 100 nM, including without limitation compounds 601, 602, 603, 605, 606, 607, 612, 613, 614, 615, 616, 617, 618, 619, 621, 622, 623, 624, 625, 626, 627, 628, 629, 630, 631, 632, 633, 636, 637, 638, 639, 640, 641, 643, 646, 647, 648, 649, 650, 652, 654, 655, 656, 657, 658, 659, 660, 661, 663, 664, 665, 666, 667, 668, 670, 672, 673, 675, 676, 677, 679, 681, 682, 684, 686, 687, 688, 689, 693, 697, 698, 699, 700, 701, 702, 703, 704, 705, 706, 707, 708, 709, 713, 714, 716, 717, 718, 719, 720, 721, 722, 723, 724, 725, 726, 727, 730, 731, 733, 734, 735, 736, 737, 738, 740, 741, 742, 745, 746, 748, 750, 751, 753, 754, 755, 757, 760, 762, 763, 764, 765, 766, 770, 771, 772, 773, 775, 777, 778, 781, 785, 787, 788, 789, 793, 795, 796, 797, 798, 803, 807, 808, 810, 811, 812, 813, 815, 816, 817, 818, 819, 820, 821, 822, 825, 827, 828, 829, 830, 834, 835, 836, 837, 838, 839, 840, 841, 843, 844, 847, 848, 850, 853, 854, 855, 856, 858, 859, 860, 862, 863, 864, 867, 868, 869, 871, 874, 876, 877, 879, 880, 881, 884, 885, 886, 887, 888, 890, 891, 892, 893, 895, 896, 897, 898, 899, 900, 901, 902, 903, 904, 906, 907, 908, 909, 911, 913, 914, 915, 916, 917, 918, 919, 920, 921, 922, 923, 924, 928, 929, 930, 931, 932, 933, 934, 935, 936, 937, 938, 939, 940, 942, 943, 944, 945, 946, 948, 949, 950, 951, 952, 953, 954, 956, 957, 958, 960, 961, 962, 963, 966, 968, 969, 970, 971, 972, 973, 974, 977, 978, 979, 980, 981, 983, 984, 986, 987, 988, 990, 991, 992, 994, 995, 998, 999, 1000, 1002, 1009, 1010, 1011, 1012, 1013, 1014, 1015, 1016, 1017, 1018, 1019, 1020, 1021, 1022, 1023, 1024, 1025, 1028, 1029, 1030, 1031, 1032, 1034, 1035, 1037, 1038, 1041, 1042, 1043, 1044, 1048, 1049, 1050, 1051, 1052, 1053, 1054, 1055, 1057, 1058, 1059, 1060, 1061, 1062, 1064, 1066, 1067, 1068, 1069, 1070, 1071, 1073, 1074, 1075, 1076, 1077, 1078, 1080, 1081, 1082, 1084, 1085, 1087, 1088, 1091, 1092, 1093, 1094, 1095, 1097, 1099, 1105, 1108, 1109, 1110, 1112, 1113, 1115, 1116, 1119, 1120, 1121, 1123, 1124, 1125, 1126, 1127, 1128, 1129, 1130, 1131, 1133, 1134, 1201, 1203, 1205, 1206, 1207, 1209, 1212, 1213, 1214, 1215, 1216, 1217, 1218, 1219, 1220, 1221, 1222, and 1225. Further, exemplary compounds disclosed herein exhibited an IC50 against K-Ras G12V of less than about 100 nM, including without limitation compounds 601, 602, 603, 605, 606, 607, 608, 611, 612, 613, 614, 615, 616, 617, 618, 619, 621, 622, 623, 624, 625, 626, 627, 628, 629, 630, 631, 632, 633, 636, 637, 638, 639, 640, 641, 643, 646, 647, 648, 649, 650, 651, 652, 654, 655, 656, 657, 658, 659, 660, 661, 662, 663, 664, 665, 667, 668, 669, 670, 672, 673, 674, 675, 676, 677, 679, 680, 681, 682, 684, 686, 688, 689, 692, 693, 697, 698, 699, 700, 701, 702, 703, 704, 705, 706, 707, 708, 709, 713, 714, 716, 717, 718, 720, 721, 722, 723, 725, 726, 727, 729, 730, 731, 733, 734, 735, 736, 737, 738, 740, 741, 742, 745, 746, 748, 750, 751, 753, 754, 755, 757, 760, 762, 763, 764, 765, 766, 770, 771, 772, 773, 775, 777, 778, 781, 784, 785, 787, 788, 789, 793, 795, 796, 797, 798, 803, 807, 808, 810, 811, 812, 813, 815, 816, 817, 818, 819, 820, 821, 825, 827, 828, 829, 830, 834, 835, 836, 837, 838, 839, 840, 841, 843, 844, 847, 848, 850, 853, 854, 855, 856, 858, 859, 860, 862, 863, 864, 868, 869, 871, 874, 876, 877, 879, 880, 881, 884, 885, 887, 888, 890, 891, 892, 893, 895, 896, 897, 898, 899, 900, 901, 902, 903, 904, 906, 907, 908, 909, 911, 913, 914, 915, 916, 917, 918, 919, 920, 921, 922, 923, 924, 928, 929, 930, 932, 933, 934, 935, 936, 937, 938, 939, 940, 942, 943, 944, 946, 948, 949, 950, 951, 952, 954, 956, 957, 958, 960, 961, 962, 963, 966, 968, 969, 970, 971, 972, 973, 974, 977, 978, 979, 980, 981, 983, 984, 986, 987, 988, 990, 991, 992, 994, 995, 998, 999, 1000, 1002, 1004, 1008, 1009, 1010, 1011, 1012, 1013, 1014, 1015, 1016, 1017, 1018, 1019, 1020, 1021, 1022, 1023, 1024, 1025, 1028, 1029, 1030, 1031, 1032, 1035, 1037, 1038, 1041, 1042, 1043, 1044, 1048, 1049, 1050, 1051, 1052, 1053, 1054, 1055, 1057, 1058, 1059, 1060, 1061, 1062, 1064, 1066, 1067, 1068, 1069, 1070, 1071, 1073, 1074, 1075, 1076, 1077, 1078, 1080, 1081, 1082, 1084, 1085, 1087, 1088, 1091, 1092, 1093, 1094, 1095, 1097, 1099, 1108, 1109, 1110, 1111, 1112, 1113, 1115, 1116, 1119, 1120, 1121, 1123, 1124, 1125, 1126, 1127, 1128, 1129, 1130, 1131, 1133, 1134, 1201, 1203, 1205, 1206, 1207, 1209, 1210, 1212, 1213, 1214, 1215, 1216, 1217, 1218, 1219, 1220, 1221, 1222, and 1225. Further, exemplary compounds disclosed herein exhibited an IC50 against K-Ras WT of less than about 100 nM, including without limitation compounds 601, 602, 603, 605, 606, 607, 611, 612, 613, 614, 615, 616, 617, 618, 619, 620, 621, 622, 623, 624, 625, 626, 628, 629, 630, 631, 632, 633, 636, 637, 638, 639, 640, 641, 643, 646, 647, 648, 649, 650, 652, 654, 655, 656, 657, 658, 659, 660, 661, 663, 664, 665, 666, 667, 668, 669, 670, 672, 673, 674, 675, 676, 677, 679, 681, 682, 684, 686, 687, 688, 689, 692, 693, 697, 698, 699, 700, 701, 702, 703, 704, 705, 706, 707, 708, 709, 713, 714, 716, 717, 718, 719, 720, 721, 722, 723, 724, 725, 726, 727, 729, 730, 731, 733, 734, 735, 736, 737, 738, 740, 741, 742, 745, 746, 748, 750, 751, 753, 754, 755, 757, 760, 762, 763, 764, 765, 766, 770, 771, 772, 773, 775, 777, 778, 781, 785, 787, 788, 789, 793, 795, 796, 797, 798, 803, 807, 808, 810, 811, 812, 813, 815, 816, 817, 818, 819, 820, 821, 822, 825, 827, 828, 829, 830, 834, 835, 836, 837, 838, 839, 840, 841, 843, 844, 847, 848, 850, 853, 854, 855, 856, 858, 859, 860, 862, 863, 864, 867, 868, 869, 871, 874, 876, 877, 879, 880, 881, 884, 885, 886, 887, 888, 890, 891, 892, 893, 895, 896, 897, 898, 899, 900, 901, 902, 903, 904, 906, 907, 908, 909, 910, 911, 913, 914, 915, 916, 917, 918, 919, 920, 921, 922, 923, 924, 928, 929, 930, 932, 933, 934, 935, 936, 937, 938, 939, 940, 942, 943, 944, 945, 946, 948, 949, 950, 951, 952, 953, 954, 956, 957, 958, 960, 961, 962, 963, 966, 968, 969, 970, 971, 972, 973, 974, 977, 978, 979, 980, 981, 983, 984, 986, 987, 988, 990, 991, 992, 994, 995, 998, 999, 1000, 1002, 1004, 1007, 1008, 1009, 1010, 1011, 1012, 1013, 1014, 1015, 1016, 1017, 1018, 1019, 1020, 1021, 1022, 1023, 1024, 1025, 1028, 1029, 1030, 1031, 1032, 1034, 1035, 1037, 1038, 1041, 1042, 1043, 1044, 1048, 1049, 1050, 1051, 1052, 1053, 1054, 1055, 1057, 1058, 1059, 1060, 1061, 1062, 1064, 1066, 1067, 1068, 1069, 1070, 1071, 1073, 1074, 1075, 1076, 1077, 1078, 1080, 1081, 1082, 1084, 1085, 1087, 1088, 1091, 1092, 1093, 1094, 1095, 1097, 1099, 1105, 1108, 1109, 1110, 1112, 1113, 1115, 1116, 1119, 1120, 1121, 1123, 1124, 1125, 1126, 1127, 1128, 1129, 1130, 1131, 1133, 1134, 1201, 1203, 1205, 1206, 1207, 1209, 1212, 1213, 1214, 1215, 1216, 1217, 1218, 1219, 1220, 1221, 1222, and 1225.

Example 6: GTPase activity assay

The ability of any compound of the present disclosure to inhibit a Ras protein signalling can be demonstrated by a reduced GTPase activity. This assay can be also used to assess a selective inhibition of a mutant Ras protein relative to a wildtype, or relative to a different mutant Ras protein. For instance, the assay can be used to establish a subject compound's ability to selectively inhibit Kras G12D relative to wildtype, G12S relative to wildtype, Kras G12V relative to wildtype, KrasG12S relative KrasG12V, KrasG12S relative KrasG12D, KrasG12D relative KrasG12S, or KrasG12D relative KrasG12V. In particular, intrinsic and GTPase-activating protein (GAP)-stimulated GTPase activity for K-Ras construct or a mutant thereof can be measured using EnzCheck phosphate assay system (Life Technologies). For example, K-Ras WT, K-Ras D154Q mutant, K-Ras G12D mutant, K-Ras G12S mutant, and K-Ras G12D/D154Q mutant proteins (2.5 mg/ml) in buffer (20 mmol/L Tris, pH 8.0, 50 mM NaCl) is loaded with GTP at room temperature for 2 hours by exposing to exchange buffer containing EDTA. Proteins are buffer exchanged to assay buffer (30 mM Tris, pH 7.5, 1 mM DTT) and the concentration is adjusted to 2 mg/ml. GTP loading is verified by back extraction of nucleotide using 6M urea and evaluation of nucleotide peaks by HPLC using an ion-exchange column. The assay is performed in a clear 384-well plate (Costar) by combining GTP-loaded K-Ras proteins (50 mM final) with 2-amino-6-mercapto-7-methylpurine ribonucleoside (MESG) (200 mM final), and purine nucleotide phosphorylase (5 U/ml final). GTP hydrolysis is initiated by the addition of $MgCl_2$ at a working concentration of 40 mM. For GAP stimulation, Ras p21 protein activator 1 (P120GAP) can be included at 50 mM. Absorbance at 360 nm can be measured every 8 to 15 s for 1,000 s at 20° C. Samples are tested with or without a subject compound disclosed herein to assess each compound's ability to inhibit signaling of a given Ras protein (e.g., a given mutant Kras) of interest.

Example 7: Nucleotide Exchange Assay

The ability of a compound of the present disclosure to inhibit a Ras protein signaling can be demonstrated by a reduced nucleotide exchange activity. This assay can be also used to assess a selective inhibition of a mutant Ras protein relative to a wildtype, or relative to a different mutant Ras protein. For example, 250 nM or 500 nM GDP-loaded K-Ras proteins (e.g., wildtype or a mutant thereof including those mentioned in Example 35), each is incubated with different concentrations of compounds (for example ~60 μM, ~20 μM, ~6.7 UM, ~2.2 μM, ~0.7 μM, ~0.2 μM subject compound). A control reaction without subject compound is also included. SOS1 (catalytic domain) protein is added to the K-Ras protein solution. The nucleotide exchange reaction is initiated by adding fluorescent labelled GDP (Guanosine 5'-Diphosphate, BODIPY™ FL 2'-(or-3')-O—(N-(2-Aminoethyl) Urethane) to a final concentration of 0.36 u.M. Fluorescence is measured every 30 s for 70 minutes at 490 nm/515 nm (excitation/emission) in a M1000Pro plate reader (Tecan). Data is exported and analyzed to calculate an IC50 using GraphPad Prism (GraphPad Software). Sample(s) can be tested with or without a subject compound disclosed herein including compound(s) exemplified in Table 1 to assess compound's ability to inhibit K-Ras signaling or its IC50 against a given Ras protein (e.g., a given mutant K-Ras) of interest.

Example 8: Testing for Modification of Ras Protein

Test compounds are prepared as 10 mM stock solutions in DMSO (Fisher cat #BP231-100). KRAS protein (e.g., His-tagged GDP-loaded wildtype 1-169, His-tagged GDP-loaded G12C1-169, or His-tagged GDP-loaded G12D 1-169) is diluted to ~2 μM in appropriate buffer (e.g., a Hepes buffer at physiological conditions). For testing KRAS modification, compounds are diluted to 50× final test concentration in DMSO in 96-well storage plates. 1 μl of the diluted 50× compounds are added to appropriate wells in the PCR plate (Fisher cat #AB-0800). ~ 49 μl of the stock protein solution is added to each well of the 96-well PCR plate. Reactions are mixed carefully. The plate is sealed well with aluminum plate seal, and stored in drawer at room temperature for 24 hrs. 5 μl of 2% formic acid (Fisher cat #A117-50) in MilliQ $H_2O$ is then added to each well followed by mixing with a pipette. The plate is then resealed with aluminum seal and stored until mass spectrometry analysis.

The extent of covalent modification of KRAS proteins can be determined by liquid chromatography electrospray mass spectrometry analysis of the intact proteins on a Thermo Q-Exactive Plus mass spectrometer. 20 μl of sample is injected onto a bioZen 3.6 μm Intact C4 column (Phenomenex cat #00B-4767-AN) placed in a column oven set to 40° C. and separated using a suitable LC gradient from ~20% to ~60% solvent B. Solvent A isis 0.1% formic acid and solvent B is 0.1% formic acid in acetonitrile. HESI source settings are set to 40, 5 and 1 for the sheath, auxiliary and sweep gas flow, respectively. The spray voltage is 4 kV, and the capillary temperature is 320° C. S-lens RF level is 50 and auxiliary gas heater temperature is set to 200° C. The mass spectrometry is acquired using a scan range from 650 to 1750 m/z using positive polarity at a mass resolution of 70,000, AGC target of 1e6 ions and maximum injection time of 250 ms. The recorded protein mass spectrum is deconvoluted from the raw data file using Protein Deconvolution v4.0 (Thermo). The protein mass and adduct masses are exported with their peak intensities. The peak intensities for the unmodified and modified protein are used to calculate the percent covalent modification of the KRAS protein based on the following equation:

% KRAS protein modification=((KRAS-compound)/ (KRAS)+(KRAS-Compound))*100.

Example 9: Ras Cellular Assay

The ability of any compound of the present disclosure to inhibit a Ras protein signalling can be demonstrated by inhibiting growth of a given Kras mutant cells. For example, this assay can be also used to assess a selective growth inhibition of a mutant Ras protein relative to a wildtype, or relative to a different mutant Ras protein.

a. Growth of Cells with K-Ras G12C Mutation

MIA PaCa-2 (ATCC CRL-1420) and NCI-$H_{1792}$ (ATCC CRL-5895) cell lines comprise a G12C mutation and can be used to assess Ras cellular signaling in vitro, e.g., in response to a subject inhibitor compounds of the present disclosure. This cellular assay can also be used to discern selective inhibition of a subject compounds against certain types of Kras mutants, e.g., more potent inhibition against KrasG12D relative to KrasG12C mutant, by using MIA PaCa-2 (G12C driven tumor cell line) as a comparison. MIA PaCa-2 culture medium is prepared with DMEM/Ham's F12 (e.g., with stable Glutamine, 10% FCS, and 2.5% Horse Serum. NCI-$H_{1792}$ culture medium is prepared with RPMI 1640 (e.g., with stable Glutamine) and 10% FCS.

On a first day (e.g., Day 1), Softagar (Select Agar, Invitrogen, 3% in dd$H_2O$ autoclaved) is boiled and tempered at 48° C. Appropriate culture medium (i.e., medium) is tempered to 37° C. Agar (3%) is diluted 1:5 in medium (=0.6%) and 50 ml/well plated into 96 well plates (Corning, #3904), then incubated at room temperature for agar solidification. A 3% agar is diluted to 0.25% in medium (1:12 dilution) and tempered at 42° C. Cells are trypsinized, counted, and tempered at 37° C. The cells (e.g., MIA PaCa-2 at about 125-150 cells, NCI-$H_{1792}$ at about 1000 cells) are resuspended in 100 mL 0.25% Agar and plated, followed by incubation at room temperature for agar solidification. The wells are overlaid with 50 mL of the medium. Sister wells in a separate plate are plated for time zero determination. All plates are incubated overnight at 37° C. and 5% $CO_2$.

On a second day (e.g., Day 2), time zero values are measured. A 40 mL volume of Cell Titer 96 Aqueous Solution (Promega) is added to each well and incubated in the dark at 37° C. and 5% $CO_2$. Absorption can be measured at 490 nm and reference wavelength 660 nm. DMSO-prediluted test compounds are added to wells of interest, e.g., with HP Dispenser, to one or more desired concentrations (e.g., a final DMSO concentration of 0.3%).

On a tenth day (e.g., Day 10), absorption by wells treated with the test compounds and control wells are measured with, for example, Cell Titer 96 AQueous and analyzed in comparison to the time zero measurements. The IC50 values are determined using the four parameter fit. The resulting IC50 value is a measurement of the ability of the compounds herein to reduce cell growth of Ras-driven cells (e.g., tumor cell lines) in vitro and/or in vivo.

b. Growth of Cells with K-Ras G12D Mutation

ASPC-1 (ATCC CRL-1682), Panc-10.05 (ATCC CRL-2547), A427 cell lines comprise a G12D mutation and can be used to assess Ras cellular signaling in vitro, e.g., in response to the compounds herein. ASPC-1 culture medium is prepared with RPMI-1640 and 10% heat-inactivated FBS. Panc-10.05 culture medium is prepared with RPMI-1640, 10 Units/ml human recombinant insulin, and 10% FBS. A427 cell culture is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384UZ). The day after plating, cells are treated with a dilution series (e.g., a 9 point 3-fold dilution series) of the compounds herein (e.g., approximately 40 µL final volume per well). Cell viability can be monitored (e.g., approximately 5 days later) according to the manufacturer's recommended instructions, where the CellTiter-Glo reagent is added (e.g., approximately 10 µL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the compounds herein to reduce cell growth of Ras-driven cells (e.g., tumor cell lines) in vitro and/or in vivo. The IC50 values are determined using the four parameter fit. The resulting IC50 value is a measurement of the ability of the compounds herein to reduce cell growth of Ras-driven cells (e.g., tumor cell lines) in vitro and/or in vivo. The ability of one or more compounds exemplified in Table 1 to inhibit growth of one or more cell lines comprising a given Kras mutation is demonstrated utilizing the procedures described above.

When assayed by the procedures described in Example 9, exemplary compounds of the present disclosure exhibited an IC50 against one or more cell lines comprising a G12D mutation, such as GP2D, ASPC-1, Panc-10.05, and/or A427 cell lines, of less than 1 µM, 500 nM, 400 nM, 300 nM, 200 nM, 150 nM, 100 nM, 10 nM, 5 nM or even less. In particular, exemplary compounds disclosed herein exhibited an IC50 against GP2D cells of less than about 500 nM, including without limitation compounds 602, 606, 607, 612, 613, 614, 615, 617, 618, 619, 621, 622, 624, 625, 628, 633, 637, 640, 641, 647, 648, 649, 650, 654, 656, 658, 661, 663, 664, 665, 667, 668, 670, 672, 676, 681, 688, 698, 699, 700, 701, 702, 704, 705, 707, 713, 716, 717, 718, 721, 722, 723, 725, 726, 727, 730, 731, 736, 737, 738, 740, 742, 745, 748, 750, 754, 755, 757, 765, 771, 772, 775, 777, 785, 793, 795, 796, 798, 803, 807, 812, 815, 817, 818, 819, 820, 821, 825, 827, 830, 834, 835, 836, 844, 850, 853, 854, 855, 864, 868, 869, 871, 874, 876, 877, 879, 881, 884, 885, 888, 890, 891, 892, 893, 896, 899, 900, 901, 911, 914, 915, 916, 919, 921, 923, 932, 937, 938, 940, 942, 943, 944, 950, 951, 954, 957, 960, 961, 962, 966, 969, 972, 977, 980, 983, 984, 986, 988, 994, 998, 1000, 1002, 1008, 1013, 1015, 1016, 1017, 1020, 1021, 1022, 1024, 1025, 1028, 1031, 1035, 1037, 1038, 1041, 1042, 1048, 1049, 1050, 1052, 1055, 1057, 1060, 1061, 1062, 1064, 1068, 1070, 1073, 1074, 1076, 1080, 1088, 1095, 1097, 1105, 1108, 1109, 1110, 1113, 1115, 1119, 1124, 1125, 1126, 1127, 1133, 1134, 1203, 1204, 1207, 1212, 1216, 1218, 1219, 1222, and 1225.

c. Growth of Cells with K-Ras G12S Mutation

A549 (ATCC CCL-185) and LS123 (ATCC CCL-255) cell lines comprise a G12S mutation and can be used to assess Ras cellular signaling in vitro, e.g., in response to the compounds herein. A549 culture medium is prepared with RPMI-1640 and 10% heat-inactivated FBS. LS123 culture medium is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384WZ). The day after plating, cells are treated with a dilution series (e.g., a 10 point 3-fold dilution series) of the compounds herein (e.g., approximately 40 µL final volume per well). Cell viability can be monitored (e.g., approximately 6 days later) according to the manufacturer's recommended instructions, where the CellTiter-Glo reagent is added (e.g., approximately 10 µL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the compounds herein to reduce cell growth of Ras-driven cells (e.g., tumor cell lines) in vitro and/or in vivo. The ability of one or more compounds exemplified in Table 1 to inhibit growth of one or more cell lines comprising a given Kras mutation is demonstrated utilizing the procedures described above.

When assayed by the procedures described in Example 9, exemplary compounds of the present disclosure exhibited an IC50 against one or more cell lines comprising a G12S mutation, such as A549 and/or LS123 cell lines, of less than 5 µM, 4 µM, 3 µM, 2 µM, 1 µM, 500 nM, 400 nM, 300 nM, 200 nM, 150 nM, 100 nM, 50 nM or even less. In particular, exemplary compounds disclosed herein exhibited an IC50 against A549 cells of less than about 5 µM, including without limitation compounds 601, 602, 603, 605, 611, 612, 613, 615, 616, 617, 619, 621, 623, 624, 625, 626, 628, 633, 636, 637, 638, 639, 640, 641, 643, 646, 648, 649, 650, 652, 654, 655, 657, 658, 659, 660, 661, 663, 664, 665, 667, 670, 673, 675, 676, 679, 681, 682, 684, 687, 688, 693, 698, 699, 700, 701, 703, 704, 705, 708, 713, 716, 717, 718, 721, 724, 725, 726, 733, 734, 736, 737, 738, 740, 741, 742, 746, 748, 754, 755, 757, 765, 771, 777, 781, 785, 793, 795, 796, 797, 798, 803, 807, 808, 812, 813, 817, 819, 820, 825, 827, 829, 834, 835, 836, 837, 838, 839, 841, 850, 854, 855, 859, 862, 864, 868, 869, 874, 877, 880, 881, 884, 887, 888, 890, 891, 892, 893, 895, 897, 899, 900, 901, 902, 903, 904, 909, 914, 915, 916, 920, 921, 922, 923, 924, 929, 932, 933, 935, 936, 937, 940, 944, 946, 948, 949, 950, 951, 952, 954, 956, 957, 958, 960, 962, 963, 966, 969, 971, 972, 973, 974, 979, 983, 984, 988, 990, 991, 994, 995, 998, 1000, 1002, 1004, 1008, 1011, 1012, 1015, 1017, 1020, 1021, 1024, 1025, 1028, 1030, 1037, 1038, 1043, 1044, 1048, 1049, 1051, 1052, 1054, 1055, 1057, 1058, 1060, 1061, 1062, 1064, 1067, 1071, 1073, 1074, 1080, 1082, 1087, 1091, 1093, 1094, 1095, 1105, 1108, 1110, 1112, 1113, 1115, 1116, 1119, 1120, 1126, 1127, 1128, 1133, 1134, 1201, 1203, 1204, 1205, 1206, 1207, 1212, 1215, 1216, 1216, 1218, 1220, and 1225.

d. Growth of Cells with K-Ras G12V Mutation

SW620 (ATCC CCL-227) and Capan-1 (ATCC HTB-79) cell lines comprise a G12V mutation and can be used to assess Ras cellular signaling in vitro, e.g., in response to the compounds herein. SW620 culture medium is prepared with RPMI-1640 and 10% heat-inactivated FBS. Capan-1 culture medium is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384WZ). The day after plating, cells are treated with a dilution series (e.g., a 10 point 3-fold dilution series) of the compounds herein (e.g., approximately 40 µL final volume per well). Cell viability can be monitored (e.g., approximately 6 days later) according to the manufacturer's recommended instructions, where the CellTiter-Glo reagent is added (e.g., approximately 10 µL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the compounds herein to reduce cell growth of Ras-driven cells (e.g., tumor cell lines) in vitro and/or in vivo. The ability of one or more compounds exemplified in Table 1 to inhibit growth of one or more cell lines comprising a given Kras mutation is demonstrated utilizing the procedures described above.

When assayed by the procedures described in Example 9, exemplary compounds of the present disclosure exhibited an IC50 against one or more cell lines comprising a G12V mutation, such as SW620 and/or Capan-1 cell lines, of less than 5 µM, 4 µM, 3 µM, 2 µM, 1 µM, 500 nM, 400 nM, 300 nM, 200 nM, 150 nM, 100 nM, 50 nM or even less. In particular, exemplary compounds disclosed herein exhibited an IC50 against SW620 cells of less than about 5 µM, including without limitation compounds 601, 602, 603, 605, 606, 607, 611, 612, 613, 614, 615, 616, 617, 618, 619, 621, 622, 623, 624, 626, 628, 630, 632, 633, 636, 637, 638, 639, 640, 641, 643, 646, 647, 648, 649, 650, 652, 654, 655, 656, 657, 658, 659, 660, 661, 663, 664, 665, 667, 668, 670, 672, 673, 674, 675, 676, 677, 679, 681, 682, 684, 687, 688, 689, 691, 693, 697, 698, 699, 700, 701, 702, 703, 704, 705, 707, 708, 709, 713, 714, 716, 717, 718, 719, 720, 721, 722, 723, 724, 725, 726, 727, 730, 731, 733, 734, 736, 737, 738, 740, 741, 742, 745, 746, 747, 748, 750, 751, 754, 755, 757, 764, 765, 767, 770, 771, 772, 775, 777, 781, 784, 785, 793, 795, 796, 797, 798, 803, 807, 808, 810, 811, 812, 813, 815, 817, 818, 819, 820, 821, 825, 827, 829, 830, 834, 835, 836, 837, 838, 839, 841, 844, 847, 850, 853, 854, 855, 859, 862, 864, 867, 868, 869, 871, 874, 876, 877, 880, 881, 884, 885, 887, 888, 890, 891, 892, 893, 895, 896, 897, 899, 900, 901, 902, 903, 904, 907, 909, 911, 914, 915, 916, 918, 919, 920, 921, 922, 923, 924, 929, 932, 933, 935, 936, 937, 938, 940, 942, 943, 944, 945, 948, 949, 950, 951, 952, 954, 956, 957, 958, 960, 962, 963, 966, 969, 971, 972, 973, 974, 977, 978, 979, 980, 983, 984, 986, 988, 990, 992, 994, 995, 998, 1000, 1001, 1002, 1004, 1008, 1011, 1012, 1013, 1015, 1016, 1017, 1020, 1021, 1022, 1024, 1025, 1028, 1030, 1031, 1035, 1037, 1038, 1041, 1042, 1043, 1044, 1048, 1049, 1050, 1051, 1052, 1053, 1054, 1055, 1057, 1058, 1060, 1061, 1062, 1064, 1067, 1068, 1070, 1071, 1073, 1074, 1076, 1080, 1082, 1084, 1085, 1088, 1092, 1094, 1095, 1097, 1105, 1108, 1109, 1110, 1113, 1115, 1116, 1119, 1120, 1125, 1126, 1127, 1128, 1133, 1134, 1201, 1203, 1204, 1205, 1206, 1207, 1209, 1212, 1215, 1216, 1217, 1218, 1219, 1220, 1222, and 1225.

Example 10: In Vivo Ras Inhibition

The in vivo reduction in Ras signaling output by a compound of the present disclosure is determined in a mouse tumor xenograft model, such as a K-Ras G12D model utilizing cells including a KRas G12D mutant or a K-Ras G12C model utilizing cells including a KRas G12C mutant, or a K-Ras G12S model utilizing cells including a KRas G12S mutant, or a K-Ras G12V model utilizing cells including a KRas G12V mutant.

Xenograft with K-Ras G12D, G12C, or G12S Mutation

Tumor xenografts are established by administration of tumor cells with a K-Ras G12D mutation (e.g., ASPC-1 cells), a K-Ras G12C mutation (e.g., MIA PaCa-2 cells), or a K-Ras G12S mutation (e.g., A549 or LS123 cells), or a K-Ras G12V mutation (e.g., SW620 cells) into mice. Female 6-to 8-week-old athymic BALB/c nude (NCr) nu/nu mice are used for xenografts. The tumor cells (e.g., approximately $5 \times 10^6$) are harvested on the day of use and injected in growth-factor-reduced Matrigel/PBS (e.g., 50% final concentration in 100 µL). One flank is inoculated subcutaneously per mouse. Mice are monitored daily, weighed twice weekly, and caliper measurements begin when tumors become visible. For efficacy studies, animals are randomly assigned to treatment groups by an algorithm that assigns animals to groups to achieve best case distributions of mean tumor size with lowest possible standard deviation. Tumor volume can be calculated by measuring two perpendicular diameters using the following formula: $(L \times w^2)/2$, in which L and w refer to the length and width of the tumor, respectively. Percent tumor volume change can be calculated using the following formula: $(V_{final} - V_{initial})/V_{initial} \times 100$. Percent of tumor growth inhibition (% TGI) can be calculated using the following formula: % TGI=100×(1-(average $V_{final}$-$V_{initial}$ of treatment group)/(average $V_{final}$-$V_{initial}$ of control group). When tumors reach a threshold average size (e.g., approximately 200-400 mm³), mice are randomized into 3-10 mice per group and are treated with vehicle (e.g., 100% Labrasol®) or a compound disclosed herein, using, for example, a daily schedule by oral gavage. Results can be expressed as mean and standard deviation of the mean.

Example 11: Metabolic (Microsomal) Stability Assay

The metabolic stability of a test compound is assayed at 37° C. using pooled liver microsomes (mouse or human liver microsomes). An aliquot of 10 µL of 50 µM test compound is mixed with 490 µL of 0.611 mg/mL liver microsomes, then 50 µL of the mixtures are dispensed to the 96 well tubes and warmed at 37° C. for 10 minutes. The reactions are initiated by adding 50 µL of the pre-warmed NADPH regeneration system solution (add 1.2 µL solution, 240 µl solution B, mix with 10.56 ml KPBS) and then incubated at 37° C. The final incubation solution contains 100 mM potassium phosphate (pH 7.4), 1.3 mM NADP+, 3.3 mM glucose 6-phosphate, 0.4 Unit/mL of glucose 6-phosphate dehydrogenase, 3.3 mM magnesium chloride, 0.3 mg/mL liver microsomes and 0.5 µM test article. After 0, 15, 30 and 60 minutes in a shaking incubator, the reactions are terminated by adding 100 µL of acetonitrile containing 200 nM buspirone as an internal standard. All incubations are conducted in duplicate. Plates are vortexed vigorously by using Fisher Scientific microplate vortex mixer (Henry Troemner, US). Samples are then centrifuged at 3500 rpm for 10 minutes (4° C.) using Sorvall Legend XRT Centrifuge (Thermo Scientific, GE). Supernatants (40 µL) are transferred into clean 96-deep well plates. Each well is added with 160 µL of ultrapure water (Milli-Q, Millipore Corporation) with 0.1% (v/v) formic acid (Fisher Chemical), mixed thoroughly and subjected to LC/MS/MS analysis in MRM positive ionization mode.

All the samples are measured using a mass spectrometer (QTrap 5500 quadrupole/ion trap) coupled with a Shimadzu HPLC system. The HPLC system consisted of a Shimadzu series degasser, binary quaternary gradient pumps, column heater coupled to an autosampler, and a Phenomenex Gemini-NX, C18, 3.0 µm or Phenomenex Lunar, C8, 5.0 µM HPLC column (Phenomenex, Torrance, CA), and eluted with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+).

The half-life for the metabolic degradation of the test compound is calculated by plotting the time-course disappearance of the test compound during the incubation with liver microsomes. Each plot is fitted to a first-order equation for the elimination of the test compound (% remaining compound) versus time using non-linear regression (Equation 1).

$$\frac{C_t}{C_0} = e^{-kt} \qquad \text{Equation 1}$$

where $C_t$ is the mean relative substrate concentration at time t and $C_0$ is the initial concentration (0.5 µM) at time 0. Note that the area ratio of the substrate peak to an internal standard peak is proportional to the analyte concentration and is used for regression analysis to derive a value of k.

The half-life $t_{1/2}$ for metabolic (microsome) stability is derived from the test compound elimination constant k using Equation 2 below.

$$t_{1/2} = \frac{0.693}{k} \qquad \text{Equation 2}$$

Example 12: CYP2C19 Inhibition Assay

Some xenobiotics can inhibit cytochrome P450 (CYP) enzyme function, which alters their ability to metabolize drugs. Administration of a CYP inhibitor with a drug whose clearance is dependent on CYP metabolism can result in increased plasma concentrations of this concomitant drug, leading to potential toxicity. The inhibition of CYP2C19 by a test compound is assayed in human liver microsomes using S-Mephenytoin as a CYP2C19 substrate. The stock solution of the test compound or known CYP2C19 inhibitor as a positive control (10 mM) is diluted with KPBS to 40 µM. In a similar way, the stock solutions of the human liver microsomes and S-Mephenytoin are diluted with KPBS buffer. The pre-incubations are started by incubating a plate containing 25 µL human liver microsomes (final concentration of 0.2 mg/mL), 25 µL NADPH-generating system, and a 25 µL test compound (final concentration 10 µM) or the positive control for 30 min at 37±1° C. After the pre-incubation, 25 L S-Mephenytoin (final concentration 200 M) is added and incubated another 12 minutes at 37±1° C. for substrate metabolism. The reactions are terminated by addition of 100 µL of ice-cold acetonitrile containing an internal standard (buspirone). Precipitated proteins are removed by centrifugation at 3500 rpm for 10 minutes at 4° C. (Allegra 25R, Beckman Co. Fullerton, CA) and then aliquot of the supernatant is transferred to an assay plate.

All the samples are assessed using a mass spectrometer (QTrap 5500 quadrupole/ion trap) coupled with a Shimadzu HPLC system, following the manufacturer's instructions. The metabolism of S-Mephenytoin in human liver microsomes is monitored by LC/MS/MS as representative of CYP2C19 inhibitory activity. The amount of metabolite formed is assessed by the peak area ratio (metabolite/IS) and % inhibition at 10 µM is expressed as a percentage of the metabolite signal reduced compared to the control (i.e. an incubation that contained no inhibitor and represented 100% enzyme activity): % inhibition=(1−A/B)×100%, where A is the metabolite peak area ratio formed in the presence of test compound or inhibitor at 10 µM and B is the metabolite peak area ratio formed without test compound or inhibitor in the incubation.

Example 13: Mouse and Human Protein Binding Assay to Assess Free Drug Concentration This assay can be used to determine the plasma protein binding of the test compound in the plasma of human and animal species using a Rapid Equilibrium Dialysis (RED) device for equilibrium dialysis and LC-MS/MS for sample analysis. Test compound is spiked in. The stock solution of the test compound is prepared at 5 mM concentration. One µL of 5 mM working solution is added into 1000 µL plasma to achieve a final concentration of 5 µM. The spiked plasma is placed on a rocker, and gently agitated for approximately 20 minutes. A volume of 300 µL of the plasma sample containing 5 µM test compound from each species is added to designate RED device donor chambers followed by addition of 500 µL of potassium phosphate buffer to the corresponding receiver chambers in duplicate. The RED device is then sealed with sealing tape and shaken at 150 RPM for 4 hours at 37° C. Post-dialysis donor and receiver compartment samples are prepared for LC-MS/MS analysis, including spiking samples with an internal standard for the bioanalytical analysis. Warfarin and propranolol are purchased from Sigma-Aldrich (St. Louis, MO), and used as positive controls for low and high plasma protein binding, respectively.

All the samples are analyzed using an Agilent Technologies 6430 Triple Quad LC/MS system. The HPLC system consists of an Agilent 1290 Infinity Liquid Chromatograph coupled to an autosampler (Agilent 1290 Infinity LC Injector HTC), and a Phenomenex Gemini-NX, C18, 3.0 µm or Phenomenex Lunar, C8, 5.0 µM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+). The percentage of the test compound bound to plasma is calculated following Equation 3 and 4.

$$\% \text{ Free test compound} = \frac{\text{Peak ratio}\left(\frac{\text{test compound}}{\text{Internal standard}}\right), \text{ receiver compartment}}{\text{Peak ratio}\left(\frac{\text{test compound}}{\text{Internal standard}}\right), \text{ donor compartment}} * 100 \qquad \text{Equation 3}$$

$$\% \text{ Plasma protein bound test compound} = 100 - \% \text{ Free test compound} \qquad \text{Equation 4}$$

Example 14: hERG (Automated Patch-Clamp) Assay

The human ether-a-go-go related gene (hERG) encodes the voltage gated potassium channel in the heart (IKr) which is involved in cardiac repolarization. Inhibition of the hERG causes QT interval prolongation and can lead to potential fatal events in humans. It is thus important to assess hERG inhibition early in drug discovery. A hERG automated patch-clamp assay is done using a hERG CHO-$K_1$ cell line using an incubation time of 5 min. The degree of hERG inhibition (%) is obtained by measuring the tail current amplitude, which is induced by a one second test pulse to −40 mV after a two second pulse to +20 mV, before and after drug incubation (the difference current is normalized to control and multiplied by 100 to obtain the percent of inhibition). The percent hERG inhibition is measured in the presence of 10 µM test compound.

Example 15: Rat Oral Exposure (% F)

A pharmacokinetic profile for a test compound is measured by single dosing in jugular vein cannulated male Sprague-Dawley rats. Animal weights are typically over 200 grams, and animals are allowed to acclimate to their new environment for at least 3 days prior to the initiation of any studies. One set of animals is dosed intravenously (IV) with test compound (2 mg/kg in 20% HP-beta-CD or 20% Captisol, pH adjusted to ~4 by citric acid). The IV dosing solution concentration is 0.4 mg/mL test compound. Blood is sampled at 5 minutes, 15 minutes, 30 minutes, 90 minutes, 360 minutes, and 24 hours following IV dosing. Another set of animals is dosed oral (po) with test compound (10 mg/kg in 20% HP-beta-CD or 20% Captisol, pH adjusted to ~4 by citric acid). The oral dosing solution concentration is 1 mg/mL test compound. Blood is sampled at 15 minutes, 30 minutes, 90 minutes, 180 minutes, 360 minutes and 24 hours following oral (po) dosing. Blood samples (~0.2 mL/sample) is collected via the jugular vein, placed in tubes containing EDTA-K2 and stored on ice until centrifuged. The blood samples are centrifuged at approximately 6800g for 6 minutes at 2-8° C. and the resulting plasma is separated and stored frozen at approximately −80° C.

The plasma samples are analyzed using an Agilent Technologies 6430 Triple Quad LC/MS system, following the manufacturer's instructions. The analytes are detected with positive-mode electrospray ionization (ES+). A standard curve for each test compound is generated and used to measure test compound concentrations in the rat plasma samples. Based on the time course sampling, an area under the curve is calculated for the oral dose group and the intravenous dose group. Percentage rat bioavailability is calculated based on equation 5.

$$\% \, F(\text{rat}) = \frac{AUC_{po} * \text{Dose}_{IV}}{AUC_{IV} * \text{Dose}_{po}}, \quad \text{Equation 5}$$

where F is bioavailability, $AUC_{po}$ is area under curve of oral drug, $AUC_{IV}$ is area under curve of intravenous drug, $\text{Dose}_{IV}$ is the intravenous dose and $\text{Dose}_{po}$ is the oral dose.

Besides the cellular proliferation inhibitory effect and high potency in reducing K-Ras signaling, particularly signaling mediated by K-Ras mutant, compounds disclosed herein exhibit advantageous ADME and/or DMPK properties. Fine-tuned pharmacological properties are of great significance for improving efficacy and safety of K-Ras inhibitors for therapeutic clinical applications.

In some embodiments, a compound of the present disclosure exhibits at least one, two, three or more advantageous pharmacological properties. Exemplary superior DMPK properties may include but are not limited to improved metabolic stability, reduced hERG liability, decreased CYP inhibition, increased oral exposure, and decreased serum protein binding (hence increasing the amount of free and available compound circulating in a subject's blood following administration of the compound).

In some embodiments, a compound of the present disclosure exhibits suitable microsomal stability.

In some embodiments, a subject compound exhibits suitable metabolic stability as ascertained by a T½ of mouse liver microsomal metabolism greater than 10 mins, 20 mins, 30 mins, 40 mins, 50 mins, 60 mins or longer as (see Example 11 for experimental procedures). In some embodiments, a subject compound exhibits suitable metabolic stability as ascertained by a T½ of human liver microsomal metabolism greater than 10 mins, 20 mins, 30 mins, 40 mins, 50 mins, 60 mins, 100 mins, 120 mins or longer as (see Example 11 for experimental procedures). In yet some other embodiments, a T½ of at least 10 mins, 20 mins, 30 mins, 40 mins, 50 mins, 60 mins or longer is observed in both mouse and human microsomal metabolism assays.

---

The invention claimed is:

1. A compound of the formula:

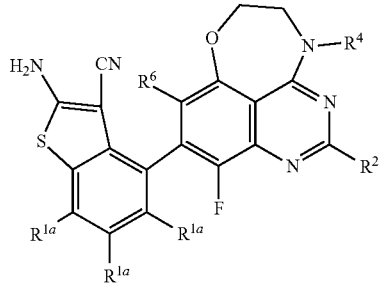

or a pharmaceutically acceptable salt or solvate thereof, wherein:

each $R^{1a}$ is independently selected from hydrogen and F;

$R^2$ is $-OR^{12a}$;

$R^{12a}$ is selected from $-CH_2-C_{3-10}$cycloalkyl and $-C(R^{12b})_2-C_{2-9}$heterocycloalkyl, wherein $-CH_2-C_{3-10}$cycloalkyl and $-C(R^{12b})_2-C_{2-9}$heterocycloalkyl are each optionally substituted with one, two, or three $R^{20l}$;

$R^6$ is selected from halogen and $C_{1-6}$haloalkyl;

$R^4$ is $-L^4-R^{4a}$;

$L^4$ is a bond or $CR4R^4$;

each $R^{4c}$ is independently selected from hydrogen, $C_{1-6}$alkyl, $C_{2-6}$alkenyl, and $C_{2-6}$alkynyl, wherein $C_{1-6}$alkyl, $C_{2-6}$alkenyl, and $C_2$-6alkynyl are each optionally substituted with one, two, or three halogen;

$R^{4a}$ is selected from $C_{3-10}$cycloalkyl, $C_{2-9}$heterocycloalkyl, $C_{6-10}$aryl, and $C_{1-9}$heteroaryl, wherein $C_{3-10}$cycloalkyl, $C_{2-9}$heterocycloalkyl, $C_{6-10}$aryl, and $C_{1-9}$heteroaryl are each optionally substituted with one, two, three, or four $R^{4b}$;

each $R^{4b}$ is independently selected from halogen,—$CH_3$,—$CN$,—$C(O)N(R^{12})(R^{13})$,—$C(O)CH_3$,—$C(O)OCH_3$,—$OH$,—$N(CH_3)_2$, and —$NH_2$;

each $R^{12}$ is independently selected from hydrogen, $C_{1-6}$alkyl, $C_{2-6}$alkenyl, and $C_{2-6}$alkynyl;

each $R^{12b}$ is independently selected from hydrogen and $C_{1-6}$alkyl;

each $R^{13}$ is independently selected from hydrogen, $C_{1-6}$alkyl, and $C_{1-6}$haloalkyl;

each $R^{201}$ is independently selected from halogen, oxo,—$OH$,—$O(C_{1-6}$alkyl), $C_{1-6}$alkyl,-$CH_2$-$C_{2-9}$heterocycloalkyl, and $=C(R^{21b})_2$, wherein $C_{1-6}$alkyl and —$CH_2$-$C_{2-9}$heterocycloalkyl are each optionally substituted with one, two, or three halogen; and each $R^{21b}$ is independently selected from hydrogen and halogen.

2. The compound of claim 1, or a pharmaceutically acceptable salt or solvate thereof, wherein $R^2$ is selected from

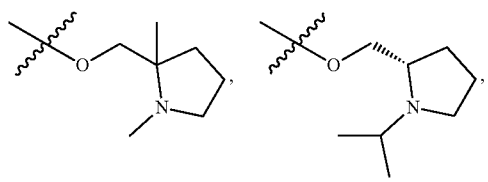

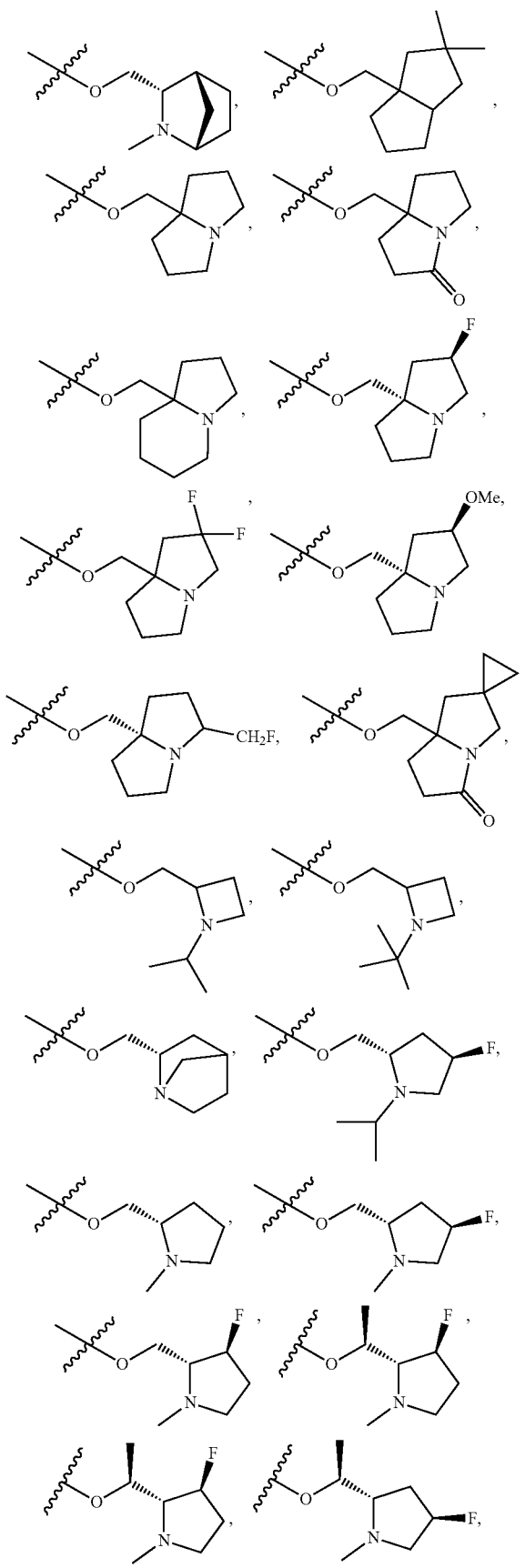
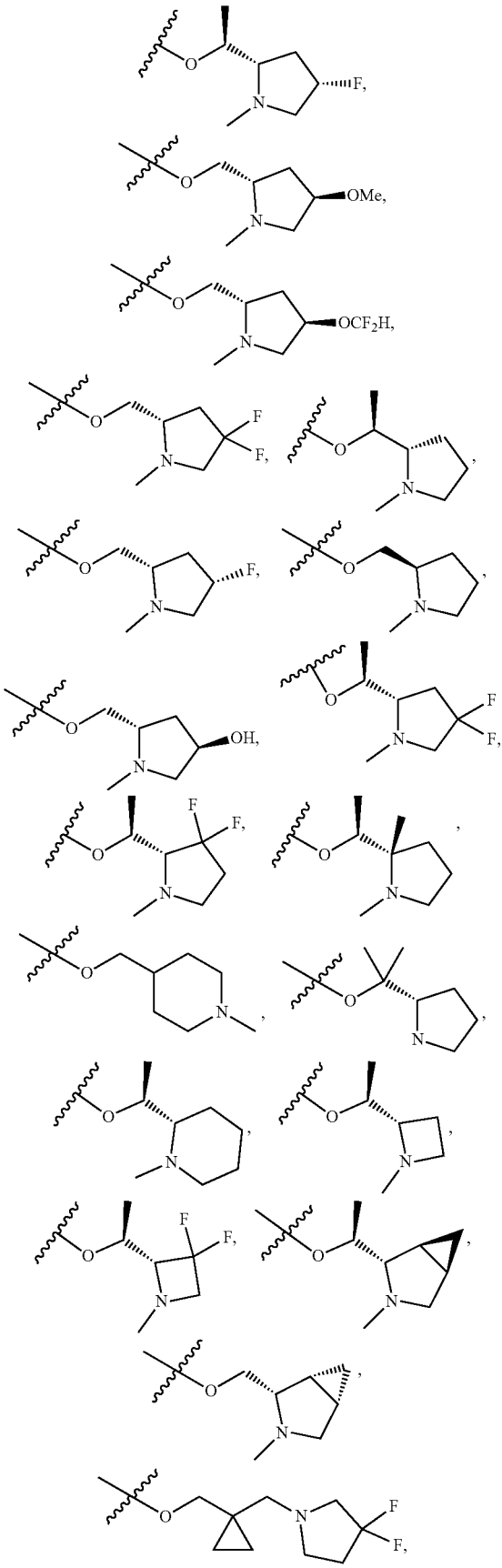

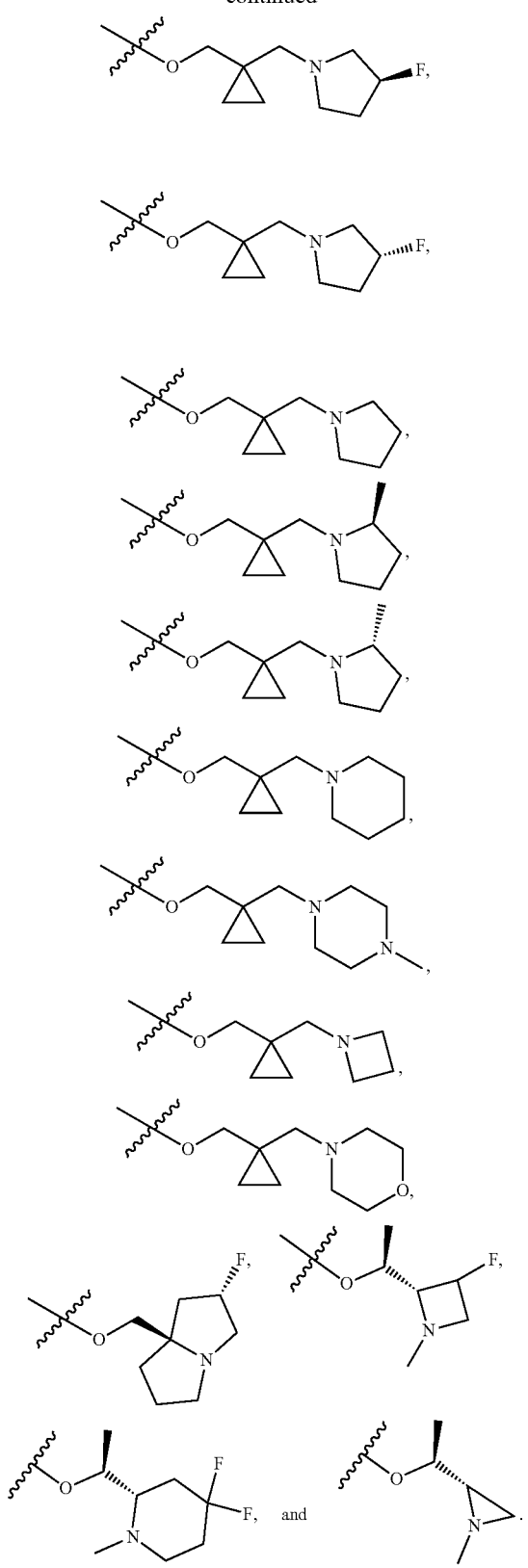

3. The compound of claim 1, or a pharmaceutically acceptable salt or solvate thereof, wherein $R^2$ is selected from 4. The compound of claim 1, or a pharmaceutically acceptable salt or solvate thereof, wherein $R^6$ is selected from —$C_1$ and —$CF_3$.

5. The compound of claim 1, or a pharmaceutically acceptable salt or solvate thereof, wherein $L^4$ is a bond.

6. The compound of claim 1, or a pharmaceutically acceptable salt or solvate thereof, wherein $R^{4a}$ is $C_{3-10}$cycloalkyl optionally substituted with one, two, three, or four $R^{4b}$.

7. The compound of claim 1, or a pharmaceutically acceptable salt or solvate thereof, wherein $R^4$ is $C_{2-9}$heterocycloalkyl optionally substituted with one, two, three, or four $R^{4b}$.

8. The compound of claim 1, or a pharmaceutically acceptable salt or solvate thereof, wherein $R^{4a}$ is $C_{6-10}$aryl optionally substituted with one, two, three, or four $R^{4b}$.

9. The compound of claim 1, or a pharmaceutically acceptable salt or solvate thereof, wherein $R^4$ is $C_{1-9}$heteroaryl optionally substituted with one, two, three, or four $R^b$.

10. The compound of claim 4, or a pharmaceutically acceptable salt or solvate thereof, wherein $R^4$ is $C_{1-9}$heteroaryl optionally substituted with one, two, three, or four $R^b$.

11. The compound of claim 9, or a pharmaceutically acceptable salt or solvate thereof, wherein $R^{4a}$ is a 6-membered heteroaryl optionally substituted with one, two, three, or four $R^{4b}$.

12. The compound of claim 9, or a pharmaceutically acceptable salt or solvate thereof, wherein $R^{4a}$ is a monocyclic 6-membered heteroaryl including at least one nitrogen atom and optionally substituted with one, two, three, or four $R^{4b}$.

13. The compound of claim 10, or a pharmaceutically acceptable salt or solvate thereof, wherein $R^{4a}$ is a monocyclic 6-membered heteroaryl including at least one nitrogen atom and optionally substituted with one, two, three, or four $R^{4b}$.

14. The compound of claim 9, or a pharmaceutically acceptable salt or solvate thereof, wherein $R^{4a}$ is a 6-membered nitrogen containing heteroaryl substituted with —$NH_2$.

15. The compound of claim 9, or a pharmaceutically acceptable salt or solvate thereof, wherein $R^4$ is selected from

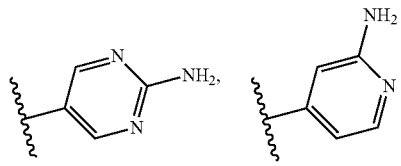

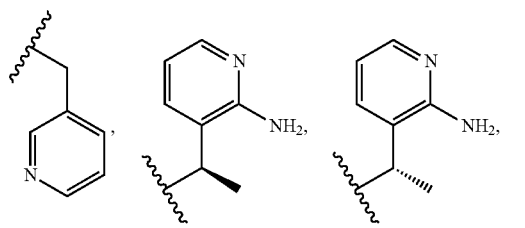

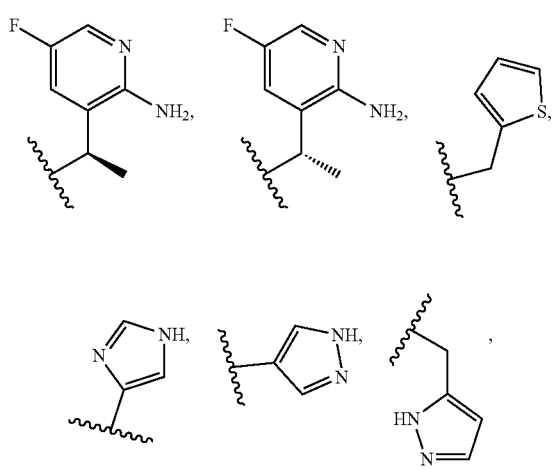

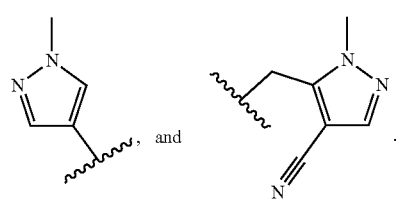

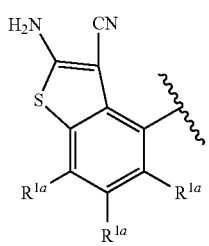, and

16. The compound of claim 1, or a pharmaceutically acceptable salt or solvate thereof, wherein

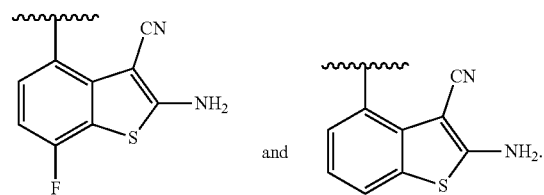

is selected from

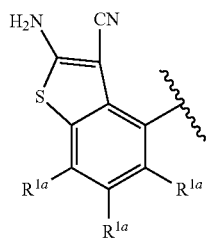

17. The compound of claim 4, or a pharmaceutically acceptable salt or solvate thereof, wherein

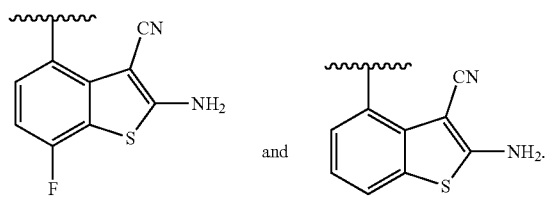 [SMILES: *c1ccc(F)c2sc(N)c(C#N)c12 ; *c1cccc2sc(N)c(C#N)c12]

is selected from

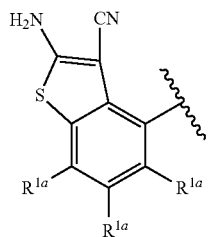

18. The compound of claim 10, or a pharmaceutically acceptable salt or solvate thereof, wherein

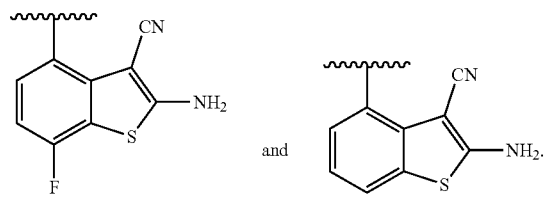 [SMILES: *c1ccc(F)c2sc(N)c(C#N)c12 ; *c1cccc2sc(N)c(C#N)c12]

is selected from and

19. The compound of claim 13, or a pharmaceutically acceptable salt or solvate thereof, wherein

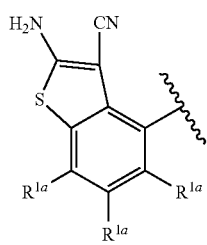
is selected from
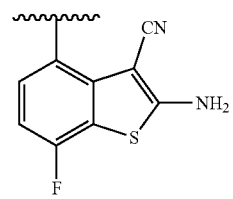 and 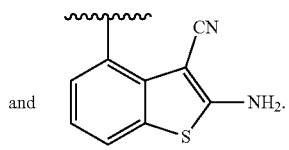
20. The compound of claim 1, wherein the compound is selected from
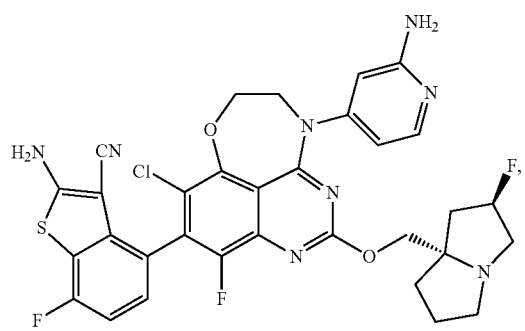
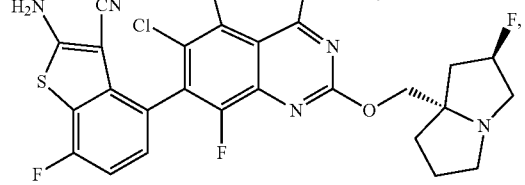
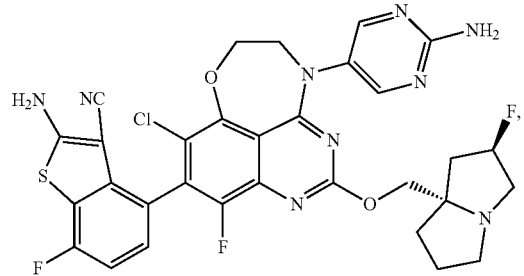
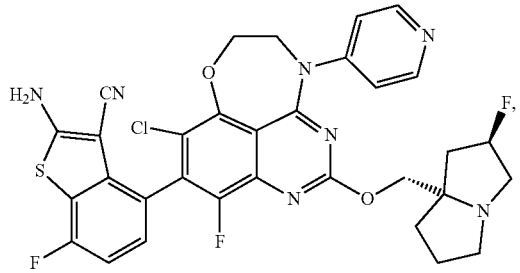
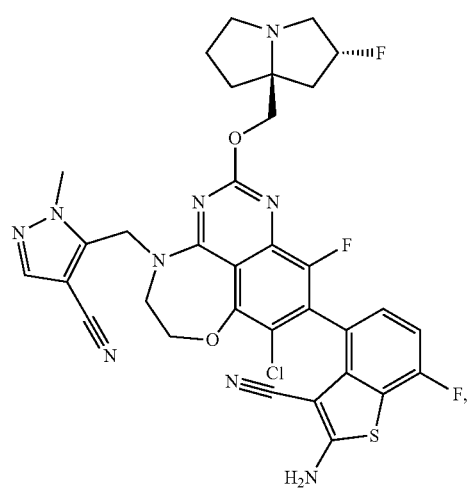
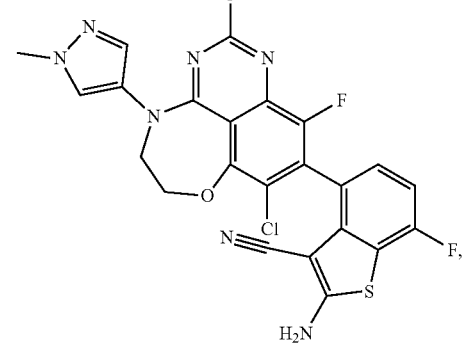

1893
-continued

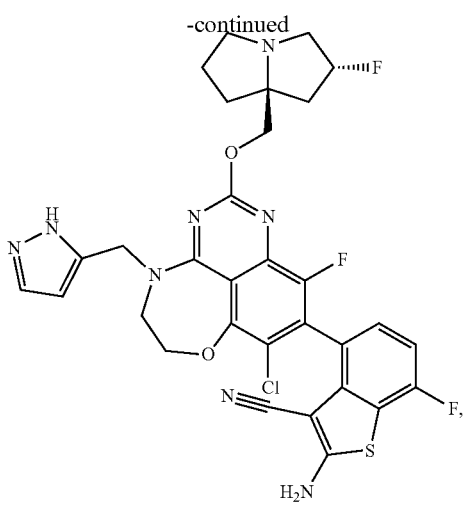

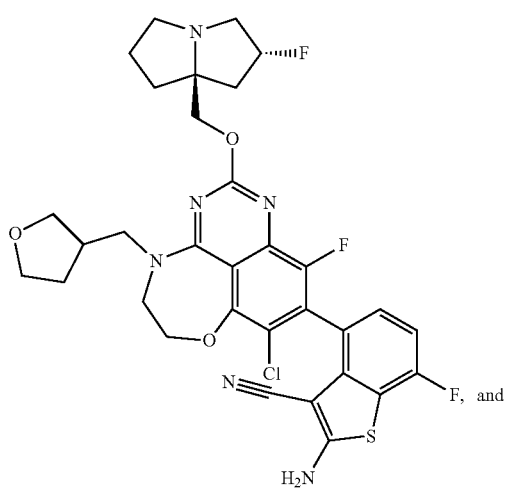

1894
-continued

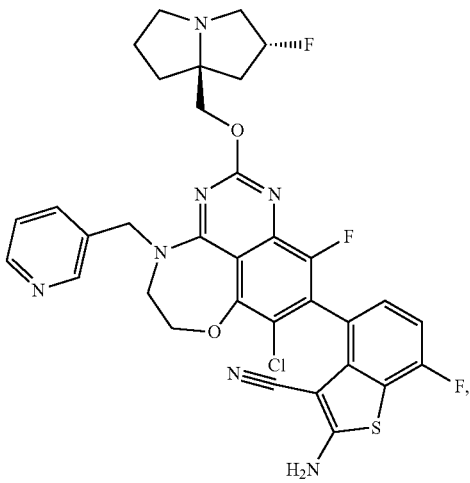

or a pharmaceutically acceptable salt or solvate thereof.

21. A pharmaceutical composition comprising a compound of claim 1, or a pharmaceutically acceptable salt or solvate thereof, and
a pharmaceutically acceptable excipient.

22. A method of treating a Ras-associated cancer in a subject in need thereof, comprising administering to the subject a therapeutically effective amount of a compound of claim 1, or a pharmaceutically acceptable salt or solvate thereof.

23. The method of claim 22, wherein the cancer is a solid tumor or a hematological cancer.

24. A method of modulating signaling output of a Ras protein, comprising contacting a Ras protein with an effective amount of a compound of claim 1, or a pharmaceutically acceptable salt or solvate thereof, thereby modulating the signaling output of the Ras protein.

25. A method of inhibiting cell growth, comprising administering an effective amount of a compound of claim 1, or a pharmaceutically acceptable salt or solvate thereof, to a cell expressing a Ras protein, thereby inhibiting growth of said cells.

* * * * *